United States Patent
Cathers et al.

(10) Patent No.: US 10,830,762 B2
(45) Date of Patent: Nov. 10, 2020

(54) COMPOSITIONS AND METHODS FOR INDUCING CONFORMATIONAL CHANGES IN CEREBLON AND OTHER E3 UBIQUITIN LIGASES

(71) Applicant: Celgene Corporation, Summit, NJ (US)

(72) Inventors: Brian E. Cathers, San Diego, CA (US); Philip Chamberlain, San Diego, CA (US); Antonia Lopez-Girona, San Diego, CA (US); Gang Lu, San Diego, CA (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 16/066,288

(22) PCT Filed: Dec. 27, 2016

(86) PCT No.: PCT/US2016/068697
§ 371 (c)(1),
(2) Date: Jun. 26, 2018

(87) PCT Pub. No.: WO2017/117118
PCT Pub. Date: Jul. 6, 2017

(65) Prior Publication Data
US 2019/0017998 A1    Jan. 17, 2019

Related U.S. Application Data

(60) Provisional application No. 62/271,864, filed on Dec. 28, 2015.

(51) Int. Cl.
| | |
|---|---|
| *A61K 38/00* | (2006.01) |
| *G01N 33/50* | (2006.01) |
| *G16B 30/00* | (2019.01) |
| *G01N 33/566* | (2006.01) |
| *C07D 401/04* | (2006.01) |
| *A61K 31/4035* | (2006.01) |
| *C07K 14/47* | (2006.01) |
| *C12N 15/62* | (2006.01) |
| *G01N 33/573* | (2006.01) |
| *A61K 38/18* | (2006.01) |

(52) U.S. Cl.
CPC ..... *G01N 33/5008* (2013.01); *A61K 31/4035* (2013.01); *A61K 38/00* (2013.01); *C07D 401/04* (2013.01); *C07K 14/4702* (2013.01); *C12N 15/62* (2013.01); *G01N 33/566* (2013.01); *G01N 33/573* (2013.01); *G16B 30/00* (2019.02); *A61K 38/18* (2013.01); *C07K 2319/95* (2013.01); *C12Y 203/02* (2013.01)

(58) Field of Classification Search
CPC .......................... A61K 38/00; G01N 33/5008
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,683,195 | A | 7/1987 | Mullis et al. |
| 4,810,643 | A | 3/1989 | Souza |
| 4,994,443 | A | 2/1991 | Folkman et al. |
| 4,999,291 | A | 3/1991 | Souza |
| 5,001,116 | A | 3/1991 | Folkman et al. |
| 5,059,595 | A | 10/1991 | Le Grazie |
| 5,073,543 | A | 12/1991 | Marshall et al. |
| 5,120,548 | A | 6/1992 | McClelland et al. |
| 5,134,127 | A | 7/1992 | Stella et al. |
| 5,229,496 | A | 7/1993 | Deeley et al. |
| 5,354,556 | A | 10/1994 | Sparks et al. |
| 5,391,485 | A | 2/1995 | Deeley et al. |
| 5,393,870 | A | 2/1995 | Deeley et al. |
| 5,441,050 | A | 8/1995 | Thurston et al. |
| 5,573,758 | A | 11/1996 | Adorante et al. |
| 5,580,755 | A | 12/1996 | Souza |
| 5,582,823 | A | 12/1996 | Souz |
| 5,591,767 | A | 1/1997 | Mohr et al. |
| 5,593,990 | A | 1/1997 | D'Amato |
| 5,629,327 | A | 5/1997 | D'Amato |
| 5,635,517 | A | 6/1997 | Muller et al. |
| 5,639,476 | A | 6/1997 | Oshlack et al. |
| 5,674,533 | A | 10/1997 | Santus et al. |

(Continued)

FOREIGN PATENT DOCUMENTS

| | | |
|---|---|---|
| EP | 2436387 A1 | 4/2012 |
| JP | H 11-504330 A | 4/1994 |

(Continued)

OTHER PUBLICATIONS

Zhu et al., 2014, Identification of cereblon-binding proteins and relationship with response and survival after IMiDs in multiple myeloma, Blood, 124(4): 536-545.*
International Search Report and Written Opinion of corresponding Interantional Patent Application No. PCT/US2016/068697 dated Apr. 21, 2017 (9 pages).

(Continued)

*Primary Examiner* — Amber D Steele
(74) *Attorney, Agent, or Firm* — Jones Day

(57) ABSTRACT

Provided herein are compositions, therapeutic methods, screening methods, computational methods and biomarkers based upon the elucidation of the interaction among cereblon, its substrates and certain compounds or agents, including small molecules, peptides, and proteins.

8 Claims, 62 Drawing Sheets

Specification includes a Sequence Listing.

(56) References Cited

U.S. PATENT DOCUMENTS

| | | |
|---|---|---|
| 5,698,579 A | 12/1997 | Muller et al. |
| 5,712,291 A | 1/1998 | D'Amato |
| 5,733,566 A | 3/1998 | Lewis |
| 5,798,368 A | 8/1998 | Muller et al. |
| 5,874,448 A | 2/1999 | Muller et al. |
| 5,877,200 A | 3/1999 | Muller |
| 5,929,117 A | 7/1999 | Muller et al. |
| 5,955,476 A | 9/1999 | Muller et al. |
| 6,071,948 A | 6/2000 | D'Amato |
| 6,114,355 A | 9/2000 | D'Amato |
| 6,207,639 B1 * | 3/2001 | Blaschuk .......... C07K 7/06 514/19.1 |
| 6,221,585 B1 * | 4/2001 | Iris .......... C12Q 1/6809 435/6.16 |
| 6,277,824 B1 * | 8/2001 | Doherty .......... A61P 25/00 514/9.3 |
| 6,281,230 B1 | 8/2001 | Muller et al. |
| 6,316,471 B1 | 11/2001 | Muller et al. |
| 6,322,962 B1 * | 11/2001 | Brown .......... C12N 9/6454 435/320.1 |
| 6,333,307 B1 * | 12/2001 | Blaschuk .......... C07K 7/06 435/7.1 |
| 6,335,349 B1 | 1/2002 | Muller et al. |
| 6,358,920 B1 * | 3/2002 | Blaschuk .......... A61P 15/00 514/19.1 |
| 6,380,239 B1 | 4/2002 | Muller et al. |
| 6,395,754 B1 | 5/2002 | Muller et al. |
| 6,403,613 B1 | 6/2002 | Man et al. |
| 6,458,810 B1 | 10/2002 | Muller et al. |
| 6,476,052 B1 | 11/2002 | Muller et al. |
| 6,555,554 B2 | 4/2003 | Muller et al. |
| 6,927,024 B2 | 8/2005 | Dodge et al. |
| 7,091,353 B2 | 8/2006 | Robarge et al. |
| 7,101,663 B2 | 9/2006 | Godfrey et al. |
| 7,122,799 B2 | 10/2006 | Hsieh et al. |
| 7,186,507 B2 | 3/2007 | Bacallo et al. |
| 7,244,759 B2 | 7/2007 | Muller et al. |
| 7,393,862 B2 | 7/2008 | Zeldis |
| 7,468,363 B2 | 12/2008 | Zeldis |
| 7,635,700 B2 | 12/2009 | Muller et al. |
| 8,143,283 B1 | 3/2012 | D'Amato |
| 9,217,743 B2 | 12/2015 | Handa |
| 9,694,015 B2 * | 7/2017 | Gandhi .......... G01N 33/57415 |
| 9,694,084 B2 * | 7/2017 | Bradner .......... C07J 43/003 |
| 10,092,555 B2 | 10/2018 | Chamberlain et al. |
| 2002/0045643 A1 | 4/2002 | Muller et al. |
| 2002/0123044 A1 * | 9/2002 | Blaschuk .......... C07K 14/705 435/6.14 |
| 2002/0146687 A1 * | 10/2002 | Blaschuk .......... C07K 14/705 435/6.14 |
| 2003/0045552 A1 | 3/2003 | Robarge et al. |
| 2003/0082166 A1 * | 5/2003 | Blaschuk .......... A61P 3/04 424/94.1 |
| 2003/0096841 A1 | 5/2003 | Robarge et al. |
| 2003/0194708 A1 * | 10/2003 | Binnerts .......... C07K 14/52 435/6.16 |
| 2004/0029832 A1 | 2/2004 | Zeldis |
| 2004/0220144 A1 | 11/2004 | Zeldis |
| 2006/0134767 A1 | 6/2006 | Bouser-Doepener et al. |
| 2006/0188475 A1 | 8/2006 | Xu et al. |
| 2006/0205787 A1 | 9/2006 | Muller et al. |
| 2007/0015194 A1 | 1/2007 | Shohat et al. |
| 2007/0049618 A1 | 3/2007 | Muller et al. |
| 2007/0065888 A1 | 3/2007 | Ring et al. |
| 2007/0128636 A1 | 6/2007 | Baker et al. |
| 2008/0051379 A1 | 2/2008 | Lerner et al. |
| 2008/0280779 A1 | 11/2008 | Shaughnessy et al. |
| 2009/0023149 A1 | 1/2009 | Knudsen |
| 2009/0075281 A1 * | 3/2009 | Hristova .......... C12N 9/93 435/6.15 |
| 2009/0142297 A1 | 6/2009 | Muller et al. |
| 2009/0148853 A1 | 6/2009 | Schafer et al. |
| 2010/0021437 A1 | 1/2010 | Isacson et al. |
| 2010/0190656 A1 | 7/2010 | Li et al. |
| 2010/0284915 A1 | 11/2010 | Dai et al. |
| 2011/0059187 A1 * | 3/2011 | Basu .......... A61P 31/10 424/649 |
| 2011/0070218 A1 | 3/2011 | Teichberg et al. |
| 2011/0070376 A1 * | 3/2011 | Wales .......... C07K 7/08 427/414 |
| 2011/0196150 A1 | 8/2011 | Man et al. |
| 2011/0200998 A1 | 8/2011 | Weichselbaum et al. |
| 2011/0223157 A1 | 9/2011 | Schafer et al. |
| 2012/0035347 A1 | 2/2012 | Yver |
| 2012/0077741 A1 | 3/2012 | Delfani et al. |
| 2012/0134969 A1 | 5/2012 | Handa et al. |
| 2012/0192297 A1 | 7/2012 | Handa et al. |
| 2012/0230983 A1 | 9/2012 | Muller et al. |
| 2012/0322073 A1 | 12/2012 | Lopez-Girona et al. |
| 2013/0177644 A1 | 7/2013 | Zeldis |
| 2013/0302323 A1 | 11/2013 | Zeldis |
| 2014/0045843 A1 | 2/2014 | Schafer et al. |
| 2014/0051591 A1 | 2/2014 | O'Donnell et al. |
| 2014/0066480 A1 | 3/2014 | Stewart et al. |
| 2014/0162282 A1 | 6/2014 | Schafer et al. |
| 2015/0051283 A1 * | 2/2015 | Batthyany Dighiero .......... A61K 31/201 514/560 |
| 2015/0224104 A1 * | 8/2015 | Gandhi .......... G01N 33/57415 514/21.1 |
| 2015/0374678 A1 | 12/2015 | Chamberlain et al. |

FOREIGN PATENT DOCUMENTS

| | | |
|---|---|---|
| JP | 2005-537257 A | 12/2005 |
| WO | WO 1993018186 A1 | 9/1993 |
| WO | WO 1998003502 A1 | 1/1998 |
| WO | WO 1998054170 A1 | 3/1998 |
| WO | WO 99/57149 * | 11/1999 .......... C07K 14/705 |
| WO | WO 2002059106 A1 | 8/2002 |
| WO | WO 2004004652 A2 | 1/2004 |
| WO | WO 2007108968 A2 | 9/2007 |
| WO | WO 2009075797 A2 | 6/2009 |
| WO | WO 2010137547 A1 | 12/2010 |
| WO | WO 2011049043 A1 | 4/2011 |
| WO | WO 2012125405 A2 | 9/2012 |
| WO | WO 2012125438 A1 | 9/2012 |
| WO | WO 2012125459 A1 | 9/2012 |
| WO | WO 2012125475 A1 | 9/2012 |
| WO | WO 2012149299 A2 | 11/2012 |
| WO | WO 2012153187 A1 | 11/2012 |
| WO | WO 2014004990 A2 | 1/2014 |
| WO | WO 2014028445 A2 | 2/2014 |
| WO | WO 2014/039960 * | 3/2014 .......... A61K 31/5377 |
| WO | WO 2015077058 A2 | 5/2015 |
| WO | WO 2015085172 A2 | 6/2015 |

OTHER PUBLICATIONS

Li et al., 2010, "A promiscuous alpha-helical motif anchors viral hijackers and substrate receptors to the CUL4-DDB1 ubiquitin ligase machinery", Nat. Struct. Mol. Biol., 17(1):105-111.

Abnova, CRBN purified MaxPab mouse polyclonal antibody (B01P), Retrieved online <http://www.abnova.com/products/products_detail.asp?catalog_id=H00051185-B01P>, retrieved on Mar. 25, 2015.

Abrahams et al., 1996, "Methods used in the structure determination of bovine mitochondrial F1 ATPase," Acta Crystallogr. D. Biol. Crystallogr., 52(Pt 1):30-42.

Adapt, 2013, Paterson Institute for Cancer Research, probests for CRBN, printed Dec. 2, 2013 (3 pages).

Aitipamula et al., 2012, "Polymorphs, salts, and cocrystals: what's in a name?," Cryst. Growth Des., 12:2147-2152.

Aizawa et al., 2011, "mRNA distribution of the thalidomide binding protein cereblon in adult mouse brain," Neurosci. Res., 69:343-347.

Akhurst, 2010, "Taking thalifomide out of rehab," Nature Med., 16(4):370-372.

Aklilu et al., 2004, "Depletion of normal B cells with rituximab as an adjunct to IL-2 therapy for renal cell carcinoma and melanoma," Annals Oncology, 15:1109-1114.

(56) References Cited

OTHER PUBLICATIONS

Altschul et al., 1997, "Gapped BLAST and PSI-BLAST: A new generation of protein database search programs," Nucleic Acid Res., 25(17):3389-3402.
Ando et al., 2006, "Efficient transfection strategy for the spatiotemporal control of gene expression in zebrafish," Mar. Biotechnol. (NY), 8(3):295-303.
Androutsellis-Theotokis et al., 2009, "Targeting neural precursors in the adult brain rescues injured dopamine neurons," Proc. Natl. Acad. Sci. USA, 106(32):13570-13575.
Angerer et al., 1985, in Genetic Engineering: Principles and Methods, Setlow and Hollaender, Eds., Plenum Press, New York, vol. 7, pp. 43-65.
Angers et al., 2006, "Molecular architecture and assembly of the DDB1-CUL4A ubiquitin ligase machinery," Nature, 443:590-593.
Anolik et al., 2007, "B cell reconstitution after rituximab treatment of lymphoma recapitulates B cell ontogeny," Clin. Immunol., 122:139-145.
Anonymous, 1989, Cancer: Principles & Practice of Oncology, Third Edition, J. B. Lippincott Co., Philadelphia, PA, pp. 1843-1847.
Ausubel et al. (eds.), 2002, Short Protocols in Molecular Biology, Fifth Edition, John Wiley and Sons, New York, Chapter 11 (31 pages).
Babin et al., 2014, "Zebrafish models of human motor neuron diseases: advantages and limitations," Prog. Neurobiol., 118:36-58.
Bartlett, 1998, "Regulation of neural stem cell differentiation in the forebrain," Immunol. Cell Biol., 76(5):414-418.
Basel-Vanagaite et al., 2006, "The CC2D1A, a member fo a new gene family with C2 domains, is involved in autosomal recessive non-syndromic mental retardation," J. Med. Genet., 43:203-210.
Basel-Vanagaite, 2007, "Genetics of autosomal recessive non-syndromic mental retardation: recent advances," Clin Genet. 72(3):167-174.
Basson, 2010, "Thalidomide's early effects," Nature Med., 16(4):372.
Bea et al., 2005, "Diffuse large B-cell lymphoma subgroups have distinct genetic profiles that influence tumor biology and improve gene-expression-based survival prediction," Blood, 106(9):3183-3190.
Becker et al., 2008, "Adult zebrafish as a model for successful central nervous system regeneration" Restorative Neurol. Neurosci., 26:71-80.
Bedford et al., 2011, "Ubiquitin-like protein conjugation and the ubiquitin-proteasome system as drug targets," Drug Discovery, 10:29-46.
Bilal et al., 2013, "Generation of a 3D model for human cereblon using comparative modeling," J. Bioinformatics Sequence Analysis, 5(1):10-15.
Bisht et al., 2011, "Brain drug delivery system: a comprehensive review on recent experimental and clinical findings," IJPSR, 2(4):792-806.
Bonnamain et al., 2012, "Neural stem/progenitor cells as promising candidates for regenerative therapy of the central nervous system," Frontiers in Cellular Neuroscience, 6(17):1-8.
Boyd et al., 2010, "High expression levels of the mammalian target of rapamycin inhibitor DEPTOR are predictive of response to thalidomide in myeloma," Leukemia & Lymphoma, 51(11):2126-2129.
Bredesen et al., 2006, "Cell death in the nervous system," Nature, 443(7113):796-802.
Bruggermann et al., 1993, "Designer mice: the production of human antibody repertoires in transgenic animals," Year Immunol., 7:33-40.
Burchiel et al., 1982, Immunopharmacokinetics of Radiolabeled Antibodies and Their Fragments, Masson Publishing, Inc., Chapter 13 (17 pages).
Burington et al., 2008, "Tumor cell gene expression changes following short-term in vivo exposure to single agent chemotherapeutics are related to survival in multiple myeloma," Clin. Cancer Res., 14(15):4821-4829.
Bustin et al., 2005, "Real-time reverse transcription PCT (qRT-PCR) and its potential use in clinical diagnosis," Clin. Sci., 109:365-379.
Cairns et al., 2011, "Regulation of cancer cell metabolism," Nature Rev., 11:85-95.
Carstensen, 1995, Drug Stability: Principles & Practices, Second Edition, Marcel Dekker, New York, NY, pp. 379-380.
Carter et al., 1981, Chemotherapy of Cancer, 2nd edition, John Wiley & Sons, New York, NY, pp. 361-367.
Cerny et al., 2002, "Advances in the treatment of non-Hodgkin's lymphoma," Ann. Oncol., 13 Suppl., 4:211-216.
Chamberlain et al., 2014, "Structure of the human Cereblon-DDB1-lenalidomide complex reveals basis for responsiveness to thalidomide analogs," Nature Struct. Mol. Biol., 21(9):803-809.
Chang et al., 2011, "What is the functional role of the thalidomide binding protein cereblon," Int. J. Biochem Mol. Biol., 2(3):287-294.
Charoenfuprasert et al., 2011, "Identification of salt-inducible kinase 3 as a novel tumor antigen associated with tumorigenesis of ovarian cancer," Oncogene, 30:3570-3584.
Charoenfuprasert et al., 2011, "Identification of salt-inducible kinase 3 as a novel tumor antigen associated with tumorigenesis of ovarian cancer," Oncogene, 30:3570-3584, Supplemental Figure 1.
Chini et al., 2007, "The JAZ family of repressors is the missing link in jasmonate signalling," Nature, 448(7154):666-671.
Chothia et al., 1998, "Structural determinants in the sequence of immunoglobulin variable domain," J. Mol. Biol., 278:457-479.
Chow et al., 2006, Pharmacological Research, "In vivo drug-response in patients with leukemic non-Hodgkin's lymphomas is associated with in vitro chemosensitivity and gene expression profiling," 53:49-61.
Christian et al., 2010, "p62 (SQSTM1) and cyclic AMP phospodiesterase-4A4 (PDE4A4) locate to a novel, reversible protein aggregate with links to autophagy and proteasome degradation pathways," Cellular Signaling, 22:1576-1596.
Clarke et al., 2002, "Changing incidence of non-Hodgkin lymphomas in the United States," Cancer, 94(7):2015-2023.
Corral et al., 1999, "Immunomodulation by thalidomide and thalidomide analogues," Ann. Rheum. Dis., 58:(Suppl I) I117-I113.
Cuoco et al., 2011, "Microarray based analysis of an inherited terminal 3p26.3 deletion, containing only the CHL1 gene, from a normal father to his two affected children," Orphanet J Rare Dis., 6:12 (6 pages).
De Graaff et al., 2001, "Matrix methods for solving protein substructures of chlorine and sulfur from anomalous data," Acta Crystallogr. D. Biol. Crystallogr., 57(Pt 12):1857-1862.
Deller et al., 2014, "Approaches to automated protein crystal harvesting", Acta Crystallogr F Struct Biol Commun., 70(Pt 2):133-155.
Drenth, 1999, "Principles of Protein X-Ray Crystallography—Chapter 1: Crystallizing a Protein," 2nd Edition, Springer-Verlag New York Inc., pp. 1-21.
Duda et al., 2011, "Structural regulation of cullin-RING ubiquitin ligase complexes", Curr Opin Struct Biol., 21(2):257-264.
Dufour-Rainfray et al., 2011, "Fetal exposure to teratogens: evidence of genes involved in autism," Neurosci Biobehav Rev., 35(5):1254-1265.
Duman et al., 2010, "Crystal structures of bacillus subtilis lon protease," J. Mol. Biol., 401(4):653-670.
Emens et al., 2001, "Chemotherapy: friend of foe to cancer vaccines," Curr. Opin. Mol. Ther., 3(1):77-84.
Emsley et al., 2010, "Features and development of Coot," Acta Crystallogr. D. Biol. Crystallogr., 66(Pt 4):486-501.
Eve et al., 2012, "Single-agent lenalidomide in relapsed/refractory mantle cell lymphoma: results from a UK phase II study suggest activity and possible gender differences," Br. J. Haematol., 159(2):154-163.
Ferraiuolo et al., "Microarray analysis of the cellular pathways involved in the adaptation to and progression of motor neuron injury in the SOD1 G93A mouse model of familial ALS," J. Neurosci., 27(34):9201-9219 (2007).
Fleisch et al., 2011, "Investigating regeneration and functional integration of CNS neurons: Lessons from zebrafish genetics and other fish species" Biochim. Biophys. Acta 1812:364-380.

(56) References Cited

OTHER PUBLICATIONS

Flemming, 2010, "Target indentification: Unravelling thalidomide teratogenicity," Nature Rev. Drug Discov., 9(5):361.
Folkman et al., 1983, "Angiogenesis inhibition and tumor regression caused by heparin or a heparin fragment in the presence of cortisone," Science, 221:719-725.
Fukuchi, 2001, "Ligand-dependent degradation of Smad3 by a ubiquitin ligase complex of ROC1 and associated proteins," Molecular Biology of The Cell, 12(5):1431-1443.
Gall et al., 1981, "Nucleic acid hybridization in cytological preparations," Methods Enzymol., 21:470-480.
Galustian et al., 2009, "Lenalidomide: a novel anticancer drug with multiple modalities," Expert Opin. Pharmacother., 10(1):125-133.
Gandhi et al., 2013, "Measuring cereblon as a biomarker of response or resistance to lenalidomide and pomalidomide requires use of standardized reagents and understanding of gene complexity," Br. J. Haematol., 164(2):233-244.
Garshasbi et al., 2008, "A defect in the TUSC3 gene is associated with autosomal recessive mental retardation," Am. J. Hum. Genetics, 82:1158-1164.
Garshasbi et al., 2010, "W8-04—Two independent mutations in the ZC3H14 gene are associated with non-syndromic autosomal recessive mental retardation," Medizinische Genetik, 22(1):83.
Genbank Accession No. NP_001166953; GI No. 291045198 (Nov. 24, 2013).
Genbank Accession No. NP_057386; GI No. 39545580 (Sep. 23, 2013).
Gerdes et al., 2014, "Emerging understanding of multiscale tumor heterogeneity," Front. Oncol., 4:1-12.
Gladman et al., 2001, Kelley's Textbook of Rheumatology, 2 Vols. 6th Edition, W. B. Saunders Company, Chapter 71, pp. 1071-1079.
Gladman, 2002, "Current concepts in psoriatic arthritis," Curr. Opin. Rheumatol., 14(4):361-366.
Gupta et al., 2001, "Adherence of Multiple Myeloma Cells to Bone Marrow Stromal Cells Up Regulates Vascular Endothelial Growth Factor Secretion: Therapeutic Applications," Leukemia, 15(12):1950-1961.
Gura, 1997, "Systems for identifying new drugs are often faulty," Science, 278:1041-1042.
Hartmann et al., 2015, "Structural dynamics of the cereblon ligand binding domain", PLoS One, 10(5):e0128342 (16 pages).
He et al., 2006, "DDB1 functions as a linker to recruit receptor WD40 proteins to CUL4-ROC1 ubiquitin ligases," Genes Dev., 20(21):2949-2954.
Heintel et al., 2011, "High Expression of the thalidomide-binding protein cereblon (CRBN) is associated with improved clinical response in patients with multiple myeloma treated with lenalidomide and dexamethasone," 53rd ASH Annual Meeting and Exposition, Abstract 2879 (Dec. 10-13, 2011).
Hernandez et al., 2011, "Thalidomide modulates mycobacterium leprae-induced NF-κB pathway and lower cytokine response," Eur. J. Pharmacol., 670:272-279.
Hernandez-Ilizalitrurri et al., 2011, Higher Response to Lenalidomide in Relapsed/Refractory Diffuse Large B-Cell lymphoma in Nongerminal Center B-Cell Like Than in Germinal Center B-Cell Like Phenotype, Cancer, pp. 5058-5066.
Higa et al., 2006, "CUL4-DDB1 ubiquitin ligase interacts with multiple WD40-repeat proteins and regulates histone methylation," Nat. Cell. Biol., 8(11):1277-1283.
Higgins et al., 2004, "A mutation in a novel ATP-dependent Lon protease gene in a kindred with mild mental retardation," Neurology 63:1927-1931.
Higgins et al., 2004, "Candidate genes for recessive non-syndromic mentalretardation on chromosome 3p (MRT2A)," Clin. Genet., 65:496-500.
Higgins et al., 2008, "Dysregulation of large-conductance Ca2+-activated K+ channel expression in nonsyndromal mental retardation due to a cereblon p.R419X mutation," Neurogenetics, 9:219-223.
Higgins et al., 2010, "Temporal and spatial mouse brain expression of cereblon, an ionic channel regulator involved in human intelligence," J. Neurogenetics, 24:18-26.
Hohberger et al., 2009, "Cereblon is expressed in the retina and binds to voltage-gated chloride channels," FEBS Lett., 583:633-637.
Hsich et al., 1998, "Review: Critical issues in gene therapy for neurologic disease," Human Gene Ther., 31:579-604.
International Prelimiary Report on Patentability (Chapter II)—English Translation posted Dec. 6, 2011 dated Jun. 22, 2010 of International Patent Application No. PCT/JP2010/058722 (published as WO 2010137547) (7 pages).
International Search Report dated Apr. 9, 2014 of International Application No. PCT/US2013/048510 (published as WO 2014004990) (7 pages).
International Search Report dated Aug. 21, 2014 of International Patent Application No. PCT/US2013/054663 (published as WO 2014028445) (5 pages).
International Search Report dated Jun. 22, 2010 of International Patent Application No. PCT/JP2010/058722 (published as WO 2010137547) (3 pages).
Ito et al., 2007, "CRBN, a mental retardation-related protein, forms a novel E3 ubiquitin ligase complex with DDB1," Dai 80 Kai The Japanese Society Taikai, Dai 30 Kai The Molecular Biology Society of Japan Nenkai Godo Taikai Koen Yoshishu, pp. 4P-1011. English machine translation attached.
Ito et al., 2010, "Identification of a primary target of thalidomide teratogenicity," Science, 327(5971):1345-1350.
Ito et al., 2010, "Identification of a primary target of thalidomide teratogenicity," Science, 327:1-28.
Ito et al., 2011, "Teratogenic effects of thalidomide: molecular mechanisms," Cell. Mol. Life Sci., 68(9):1569-1579.
Ito et al., 2012, "Deciphering the mystery of thalidomide teratogenicity," Congenital Anomalies, 52:1-7.
Jakobovits et al., 1993, "Analysis of homozygous mutant chimeric mice: deletion of the immunoglobulin heavy-chain joining region blocks B-cell development and antibody production," Proc. Natl. Acad. Sci., USA, 90:2551-2555.
Jakobovits et al., 1993, "Germ-line transmission and expression of human-derived yeast artificial chromosome," Nature, 362(6417):255-258.
Jalkanen et al., 1985, "Heparan sulfate proteoglycans from mouse mammary epithelial cells: localization on the cell surface with a monoclonal antibody," J. Cell Biol., 101(3):976-984.
Jalkanen et al., 1987, "Cell surface proteoglycan of mouse mammary epithelial cells is shed by cleavage of its matrix-binding ectodomain from its membrane-associated domain," J. Cell Biol., 105(6 Pt 2):3087-3096.
Jemal et al., 2007, "Cancer Statistics," CA Cancer J. Clin., 57:43-66.
Jo et al., 2005, "Identification and functional characterization of cereblon as a binding protein for large-conductance calcium-activated potassium channel in rat brain," J. Neurochem., 94:1212-1224.
Joachimiak, 2009, "High-throughput crystallography for structural genomics", Curr Opin Struct Biol., 19(5):573-584.
Johansson, 2007, "Regeneration and plasticity in the brain and spinal cord," J. Cereb. Blood Flow Metab., 27:1417-1430.
Jones et al., 2006, "Pharmaceutical cocrystals: an emerging approach to physical property enhancement," MRS Bulletin 31:875-879.
Kabat et al., 1971, "Attempts to locate complementarity-determining residues in the variable positions of light and heavy chains," Ann. N.Y. Acad. Sci., 190:382-393.
Kaiser, 2006, "First pass at cancer genome reveals complex landscape," Science, 313:1370.
Kallioniemi et al., 1992, "Comparative genomic hybridization for molecular cytogenetic analysis of solid tumors," Science 258:818-821.
Kamarch, 1987, "Fluorescence-activated cell sorting of hybrid and transfected cells," Methods Enzymol., 151:150-165.
Kantarci et al, 2010, "Identification of the genetic basis of nonsyndromic intellectual disability in large consanguineous families by exome sequencing," Clin. Genet., 78(Suppl. 1):L03.

(56) References Cited

OTHER PUBLICATIONS

Kim et al., 2007, "Use of absolute lymphocyte counts to predict response to chemotherapy and survival in diffuse large B-cell lymphoma," J. Clin. Oncology, ASCO Annual Meeting Proceedings Part I., 25(18S), Jun. 20 Supplement, p. 8082.
Kim et al., 2011, "Thalidomide: the tragedy of birth defects and the effective treatment of disease," Toxicological Sci., 122(1):1-6.
Kim et al., 2013, "Gene Expression Profiles for the Prediction of Progression-free Survival in Diffuse Large B Cell Lymphoma: Results of a DASL Assay," Annals of Hematology, 93(3):437-447.
Kishimoto et al. 2012, "Neuronal regeneration in zebrafish model of adult brain injury" Disease Models and Mechanisms 5:200-209.
Klyushnichenko, 2003, "Protein crystallization: from HTS to kilogram-scale", Curr Opin Drug Discov Devel., 6(6):848-854.
Knobloch et al., 2011, Apoptosis induction by thalidomide: critical for limb teratogenicity but therapeutic, Current Mol. Pharmacol., 4:26-61.
Kobayashi et al., 1998, "Overexpression of the forebrain-specific homeobox gene six3 induces rostral forebrain enlargement in zebrafish," Development, 125:2973-2982.
Kohler et al., 1975, "Continuous cultures of fused cells secreting antibody of predefined specificity," Nature, 256:495-497.
Krontiris et al., 1994, Internal Medicine, 4th edition, Elsevier Science, Chapters 71-72, pp. 699-729.
Kumar et al., 2002, "Occurrence of Multiple Myeloma in Both Donor and Recipient After Bone Marrow Transplantation." American Journal of Hematology, 71: 227-228.
Lee et al., 2010, "Cereblon binding modulates AMP-activated protein kinase function," Journal of Neurochemistry, 115(WE03-03):74.
Lee et al., 2010, "Induction of cereblon by NF-E2-related factor 2 in neuroblastoma cells exposed to hypoxia-reoxygenation," Biochem. Biophys. Res. Comm., 399:711-715.
Lee et al., 2011, "Embryopathic effects of thalidomide and its hydrolysis products in rabbit embryo culture: evidence for a prostaglandin H synthase (PHS)-dependent, reactive oxygen species (ROS)-mediated mechanism," FASEB J., 25:2468-2483.
Lee et al., 2011, "Functional modulation of AMP-activated protein kinase by cereblon," Biochimica Biophysica Acta, 1813:448-455.
Lee et al., 2011, "Resistance of CD-1 and ogg1 DNA repair-deficient mice to thalidomide and hydrolysis product embryopathies in embryo culture," Toxicological Sci., 122(1):146-156.
Lee et al., 2012, "Cereblon inhibits proteasome activity by binding to the 20S core proteasome subunit beta type 4," Biochem. Biophys. Res. Comm., 427:618-622.
Lenz et al., 2008, "Molecular subtypes of diffuse large B-cell lymphoma arise by distinct genetic pathways," Proc. Natl. Acad. Sci., USA, 105(36):13520-13525.
Lenz et al., 2008, "Oncogenic CARD11 mutations in human diffuse large B cell lymphoma," Science, 319(5870):1676-1679.
Li et al., 2009, "The RIG-I-like receptor LGP2 recognizes the termini of double-stranded RNA," J. Biol. Chem., 284(20):13881-13891.
List et al., 1990, "The myelodysplastic syndromes: biology and implications for management," J. Clin. Oncol., 8:1424-1441.
Lopez-Girona et al., 2011, "Direct Binding with Cereblon Mediates the Antiproliferative and Immunomodulatory Action of Lenalidomide and Pomalidomide," 53rd ASH Annual Meeting and Exposition, Abstract 738 (Dec. 10-13, 2011).
Lopez-Girona et al., 2011, "Direct Binding with Cereblon Mediates the Antiproliferative and Immunomodulatory Action of Lenalidomide and Pomalidomide," Blood, 118(21):Abstract 738.
Lopez-Girona et al., 2011, "Lenalidomide downregulates the cell survival factor, interferon regulatory factor-4, providing a potential mechanistic link for predicting response," Br. J. Haematol.,154(3):325-336.
Lopez-Girona et al., 2012, "Cereblon is direct protein target for immunomodulatory and antiproliferative acttivities of lenalidomide and pomalidomide," Leukemia, 26:2326-2335.

Lowe et al., 1992, "The PDE IV family of calcium-independent phosphodiesterase enzymes," Drugs of the Future, 17(9):799-807.
Lu et al., 2006, "MaxiK channel partners: Physiological Impact," Journal of Physiology, 570(1):65-72.
Lu et al., 2010, "The structural basis of 5' triphosphate double-stranded RNA recognition by RIG-I C-terminal domain," Structure, 18(8):1032-1043.
Ludwig et al., 2012, "IMWG consensus on maintenance therapy in multiple myeloma," Blood, 119(3):3003-3015.
Magavi et al., 2000, "Induction of neurogenesis in the neocortex of adult mice," Nature, 405(6789):951-955.
Mardis et al., 2009, "Recurring mutations found by sequencing an acute myeloid leukemia genome," N. Engl. J. Med., 361(11):1058-1066.
Marks et al., 1991, "By-passing immunization, human antibodies from V-gene libraries displayed on phage," J. Mol. Biol., 222(3):581-597.
Marriott et al., 2001, "Immunotherapeutic and antitumor potential of thalidomide analogues," Expert Opin. Biol. Ther., 1(4):1-8.
Martiniani et al., 2012, "Biological activity of lenalidomide and its underlying trherapeutic effects in multiple myeloma," Adv. Hematol., 2012:842945 (12 pages).
McCoy et al., 2007, "Phaser crystallographic software," J. Appl. Crystallogr., 40(Pt 4):658-674.
McPherson et al., 2014, "Introduction to protein crystallization", Acta Crystallogr F Struct Biol Commun., 70(Pt 1):2-20.
Ménard et al., 2013, Cereblon (CRBN) splicing could influence response to IMiDs : A new PCR strategy to easily detect and semi-quantify loss of the IMiDs binding domain, Blood, 122(21):3107.
Michalak et al., 2008, "Testis-derived microRNA profiles of African clawed frogs (Xenopus) and their sterile hybrids," Genomics, 91(2):158-164.
Mitchell et al., 2012, "Physical activity-associated gene expression signature in nonhuman primate motor cortex," Obesity, 20:692-698.
Mochida et al., 2004, "Genetic basis of developmental malformations of the cerebral cortex," Arch. Neurol., 61:637-640.
Muller et al., 1996, "Structural modifications of thalidomide produce analogs with enhanced tumor necrosis factor inhibitory activity," J. Med. Chem., 39(17):3238-3240.
Muller et al., 1998, "Thalidomide analogs and PDE4 inhibition," Bioorg. & Med. Chem. Lett., 8:2669-2674.
Mullis et al., 1986, "Specific enzymatic amplification of DNA in vitro: the polymerase chain reaction," Cold Spring Harbor Symp. Quant. Biol., 51:263-273.
Murshudov et al., 2011, "REFMAC5 for the refinement of macromolecular crystal structures," Acta Crystallogr. D. Biol. Crystallogr., 67(Pt 4):355-367.
Nakamura et al., 2008, "Freud-1/Akil, a Novel PDK1-interacting Protein, Functions as a Scaffold to Activate the PDK1/Akt Pathway in Epidermal Growth Factor Signaling," Mol. Cell. Biol., 28(19):5996-6009.
Nakatomi et al., 2002, "Regeneration of Hippocampal Pyramidal Neurons after Ischemic Brain Injury by Recruitment of Endogenous Neural Progenitors," Cell, 110(4):429-441.
Neben et al., 2001, "High plasma basic fibroblast growth factor concentration is associated with response to thalidomide in progressive multiple myeloma," Clin. Cancer Res., 7(9):2675-2681.
Newman et al., 1993, "Assessment of the effectiveness of animal developmental toxicity testing for human safety," Reprod. Toxicol., 7(4):359-390.
Ngo et al., 2011, "Oncogenically active MYD88 mutations in human lymphoma," Nature, 470(7332)115-119.
Ocio et al., 2014, "New drugs and novel mechanisms of action in multiple myeloma in 2013: a report from the International Myeloma Working Group (IMWG)", Leukemia, 28(3):525-542.
Offidani et al., 2008, "Serum C-reactive protein at diagnosis and response to therapy is the most powerful factor predicting outcome of multiple myeloma treated with thalidomide/anthracycline-based therapy," Clin. Lymphoma & Myeloma, 8(5):294-299.
Oliver et al., 2000, "Immune stimulation in scleroderma patients treated with thalidomide," Clin. Immunol., 97(2):109-120.
Otwinowski et al., 1997, "Processing of X-ray diffraction data collected in oscillation mode," Methods Enzymol., 276:307-326.

(56) References Cited

OTHER PUBLICATIONS

Pannu et al., 2004, "The application of multivariate statistical techniques improves single-wavelength anomalous diffraction phasing," Acta Crystallogr. D. Biol. Crystallogr., 60(Pt 1):22-27.
Pannu et al., 2011, "Recent advances in the CRANK software suite for experimental phasing," Acta Crystallogr. D.Biol. Crystallogr., 67(Pt 4):331-337.
Parman et al., 1999, "Free radical-mediated oxidative DNA damage in the mechanism of thalidomide teratogenicity," Nature Med., 5(5):582-585.
Parsons et al., 2008, "An integrated genomic analysis of human glioblastoma multiforme," Science, 321:1807-1812.
Paul (ed), 1989, Fundamental Immunology, Second Edition, Raven Press, New York, pp. 332-336.
Penichet et al., 2001, "Antibody-cytokine fusion proteins for the therapy of cancer," J. Immunol. Methods, 284:91-101.
Petroski, 2008, "The ubiquitin system, disease, and drug discovery," BMC Biochem., 9(Suppl. 1):S7.
Plückthun, 1994, The Pharmacology of Monoclonal Antibodies, vol. 113, Springer Verlag, Berlin, pp. 269-315.
Pohjola et al., 2010, "Terminal 3p deletions in two families—correlation between molecular karyotype and phenotype," American Journal of Medical Genetics, Part (2): 441-446.
Quach et al., 2010, "Mechanism of action of immunomodulatory drugs (IMiDS) in multiple myeloma," Leukemia, 24(1):22-32.
Rajadhyaksha et al., 2012, "Behavioral characterization of cereblon forebrain-specific conditional null mice: a model for human nonsyndromic intellectual disability," Behavioural Brain Res., 226:428-434.
Rajkumar, 2012, "Multiple myeloma: 2012 update on diagnosis, risk-stratification, and management," Am J Hematol., 87(1):78-88.
Rajpal et al., 2011, "A novel panel of protein biomarkers for predicting response to thalidomide-based therapy in newly diagnosed multiple myeloma patients," Proteomics, 11(8):1391-1402.
Ramsay et al., 2012, "Multiple inhibitory ligands induce impaired T-cell immunologic synapse function in chronic lymphocytic leukemia that can be blocked with lenalidomide: establishing a reversible immune evasion mechanism in human cancer," Blood, 120(7):1412-1421.
Ramsay et al., 2013, "Chronic lymphocytic leukemia cells induce defective LFA-1-directed T-cell motility by altering Rho GTPase signaling that is reversible with lenalidomide," Blood, 121(14):2704-2714.
Razek et al., 2009, "Disorders of cortical formation: MR imaging features," AJNR Am. J. Neuroradiol., 30:4-11.
Rehmann et al., 2011, "The rise, fall and subsequent triumph of thalidomide: Lessons learned in drug development," Ther Adv Hematol., 2(5):291-308.
Ren et al., 2012, "Oncogenic CUL4A determines the response to thalidomide treatment in prostate cancer," J. Mol. Med., 90(10):1121-1132.
Ripa et al., 1996, "A linear model for the pharmacokinetics of azithromycin in healthy volunteers," Chemother., 42:402-409.
Roitt et al., 1993, "Chapter 17: Tumor Immunology," Immunology, Third Edition, Mosby, St. Louis, MO, pp. 17.1-17.12.
Sadowski et al., 1993, "From atoms and bonds to three-dimensional atomic coordinates: automatic model builders", Chemical Reviews, American Chemical Society, US, 93:2567-2581.
Santana et al., 2012, "Can zebrafish be used as animal model to study Alzheimer's disease," Am. J. Neurodegener. Dis., 1(1):32-48.
Schultheiss et al., 2009, "Pharmaceutical cocrystals and their physicochemcial properties," Cryst. Growth Des., 9(6):2950-2967.
Schütt et al., 2005, "Thalidomide in combination with dexamethasone for pretreated patients with multiple myeloma: serum level of soluble interleukin-2 receptor as a predictive factor for response rate and for survival," Ann. Hematol., 84(9):594-600.
Science Daily, 2013, "How many species on Earth? About 8.7 million, new estimate says," Retrieved online <http://www.sciencedaily.com/releases/2011/08/1108323180459.htm>, retrieved on Apr. 7, 2013.
Shackelford et al., 2009, "The LKB1-AMPK pathway: metabolism and growth control in tumour suppression," Nature Rev., 9:563-575.
Shan et al., 2008, "The role of cocrystals in pharmaceutical science," Drug Discov. Today, 13(9-10):440-446.
Sheard et al., 2010, "Jasmonate perception by inositol-phosphate-potentiated COI1-JAZ co-receptor," Nature,468(7322):400-405.
Shestopalov et al., 2010, "Oligonucleotide-based tools for studying zebrafish development," Zebrafish, 7(1):31-40.
Smith, 2005, "Striving for purity: advances in protein purification", Nature Methods, 2:71-77.
Sokka et al., 2003, "MRI-guieded gas bubble enhanced ultrasound heating in in vivo rabbit thigh," Phys. Med. Biol., 48:223-241.
Stahnke et al., 2001, "Activation of apoptosis pathways in peripheral blood lymphocytes by in vivo chemotherapy," Blood, 98:3066-3073.
Staudt, 2002, "Gene expression profiling of lymphoid malignancies," Ann. Rev. Med., 53:303-318.
Stockdale, 1998, Medicine, vol. 3, Rubenstein and Federman, eds., Chapter 12, Section IV and Section X (27 pages).
Suzuki et al., 2008, "Stabe transgene expression from HSV amplicon ectors in the brain: potential involvement of immunoregulatory signals," Mol. Ther., 16(10):1727-1736.
Takada et al., 2011, "Protective effect of thalidomide against N-methyl-D-aspartate-induced retinal neurotoxicity," J Neurosci Res., 89(10):1596-604.
Tan et al., 2007, "Mechanism of auxin perception by the TIR1 ubiquitin ligase," Nature, 446(7136):640-645.
Taylor et al., 1982, "Protamine is an inhibitor of angiogenesis," Nature, 297:307-312.
Taylor et al., 1992, "A transgenic mouse that expresses a diversity of human sequence heavy and light chain immunoglobulins," Nucleic Acids Res., 20(23):6287-6295.
The Merck Manual, 17th Edition, Merck & Company, West Point, PA, pp. 448, 944-952 (1999).
Therasse et al., 2000, "New guidelines to evaluate the response to treatment in solid tumors," J. Natl. Cancer Inst., 92(3):205-216.
Thiel et al., 2012, "Small-molecule stabilization of protein-protein interactions: an underestimated concept in drug discovery?," Angew Chem. Int. Ed. Engl., 51(9):2012-2018.
Thomas et al., 2003, "Progess and problems with the use of viral vectors for gene," Nat. Rev. Genet., 4(5):346-358.
Thome et al., 2010, "Antigen receptor signaling to NF-κB via CARMA1, BCL10, and MALT1," Cold Spring Harb. Perspect. Biol., 2:a003004 (16 pages).
Tierney et al. (eds), 1998, Current Medical Diagnosis & Treatment 1998, 37th Edition, Appleton & Lange, Stamford, CT, p. 793.
Trask, 2007, "An overview of pharmaceutical cocrystals as intellectual property," Mol. Pharm., 4(3):301-309.
Vallet et al., 2012, "Update on immunomodulatory drugs (IMiDs) in hematologic and solid malignancies," Expert Opinion on Pharmacotherapy, 13(4):473-494.
Vanhook, 2010, "Thalidomide Target Identified," Sci. Signal., 3(113):ec82, abstract only.
Vippagunta et al., "Crystalline solids," Adv. Drug Del. Rev., 48:3-26 (2001).
Vishweshwar et al., 2006, "Pharmaceutical co-crystals," J. Pharm. Sci., 95(3):499-516.
Weber, 1997, "Overview of protein crystallization methods", Methods Enzymol, 276:13-22.
Wilen, 1972, Tables of Resolving Agents and Optical Resolutions, (E.L. Eliel, Ed.), University of Notre Dame Press, Notre Dame, IN, p. 268.
Wilen et al., 1977, "Strategies in optical resolutions," Tetrahedron, 33:2725-2736.
Willems, 2007, "Cognition genes on autosomes: The paradox," Clinical Genetics, 72(1):9-12.
Wilson et al., 2010, "Novel disease targets and management approaches for diffuse large B-cell lymphoma," Leukemia & Lymphoma, 51(S1):1-10.
Wu et al., 2011, "Screening and indentification of host factors interacting with UL14 of herpes simplex virus 1," Med. Microbiol. Immunol., 200:203-208.

(56) References Cited

OTHER PUBLICATIONS

Wu, 2003, "Large-Conductance Ca2+-Activated K+ Channels: Physiological Role and Pharmacology," Current medicinal Chemistry, 10(8):649-661.

Xin et al., 2008, "Primary function analysis of human mental retardation related gene CRBN," Mol. Biol. Rep., 35:251-256.

Yamazaki et al., 2011, "In vivo formation of a glutathione conjugate derived from thalidomide in humanized uPA-NOG mice," Chem Res Toxicol., 24(3):287-289.

Yang et al., 2012, "Exploiting synthetic lethality for the therapy of ABC diffuse large B cell lymphoma," Cancer Cell, 21:723-737.

Zhang et al., 2010, "PI3K/Akt signaling pathway is required for neuroprotection of thalidomide on hypoxic-ischemic cortical neurons in vitro," Brain Research, 1357:157-65.

Zhu et al., 2011, "Cereblon expression is required for the antimyeloma activity of lenalidomide and pomalidomide," Blood, 118(18):4771-4779.

Zhu et al., 2012, "Molecular mechanism of action of immune-modulaotry drugs thalidomide, lenalidomide and pomalidomide in multiple myeloma," Leukemia & Lymphoma, pp. 1-5.

\* cited by examiner

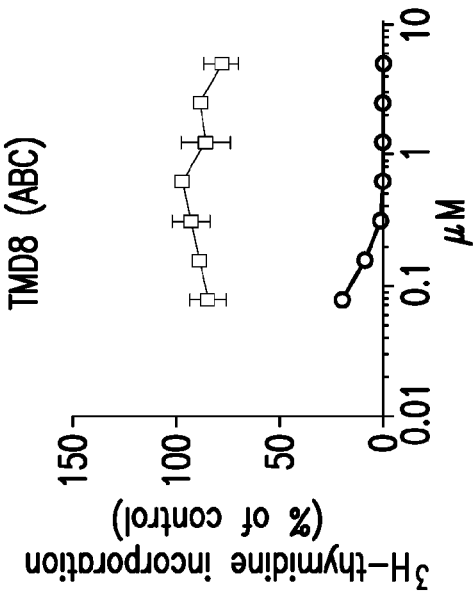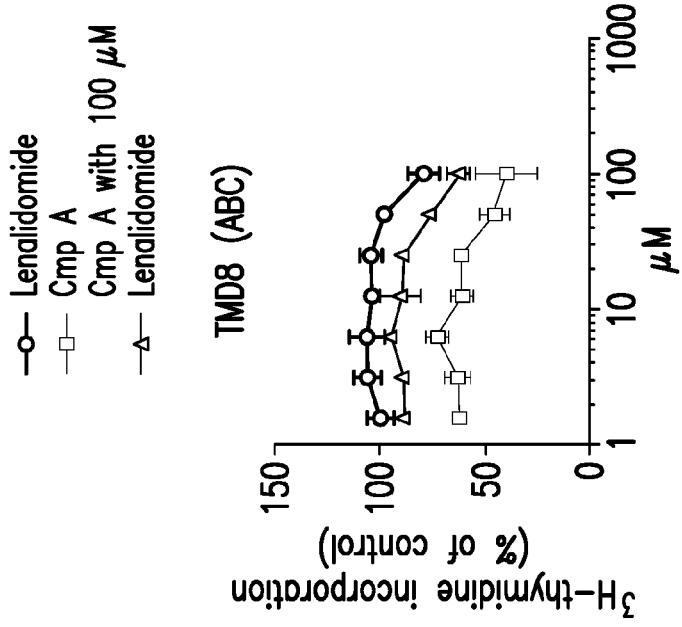
FIG. 5A

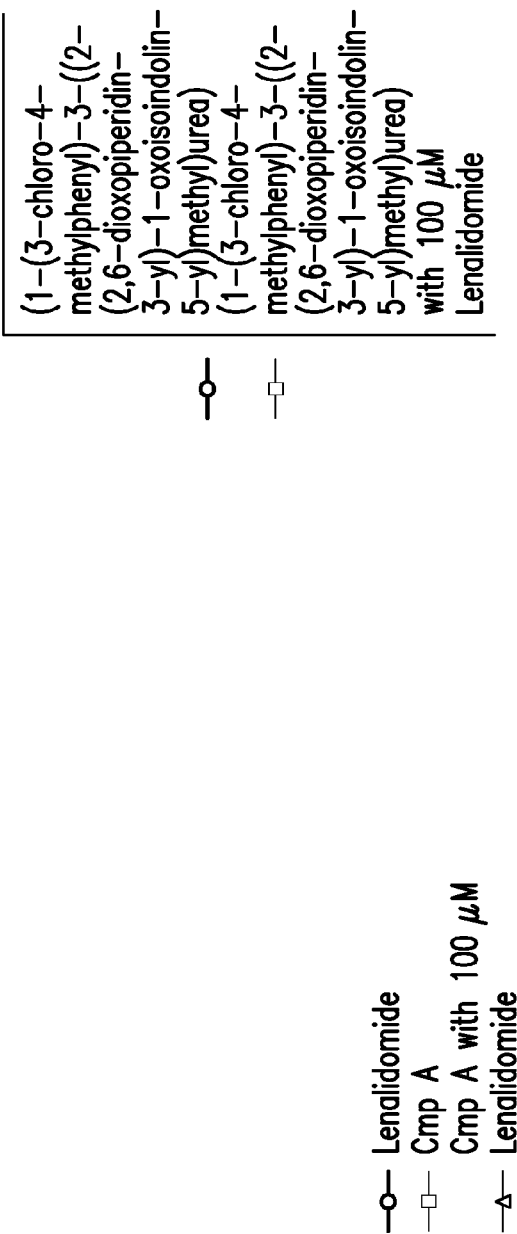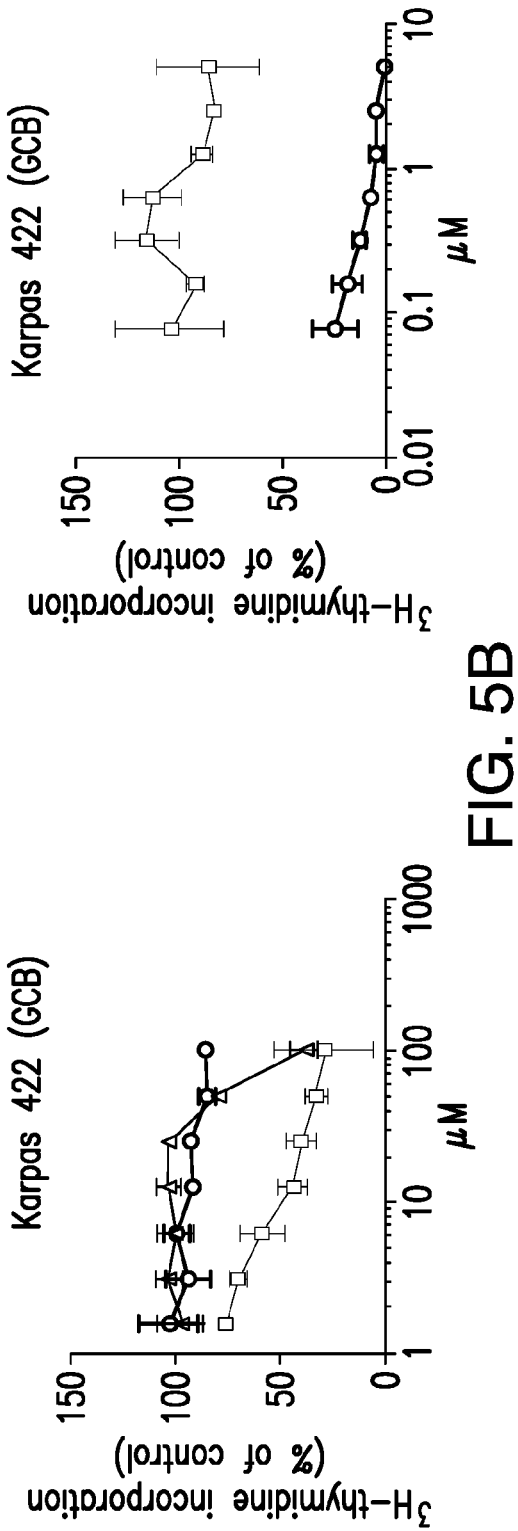
FIG. 5B

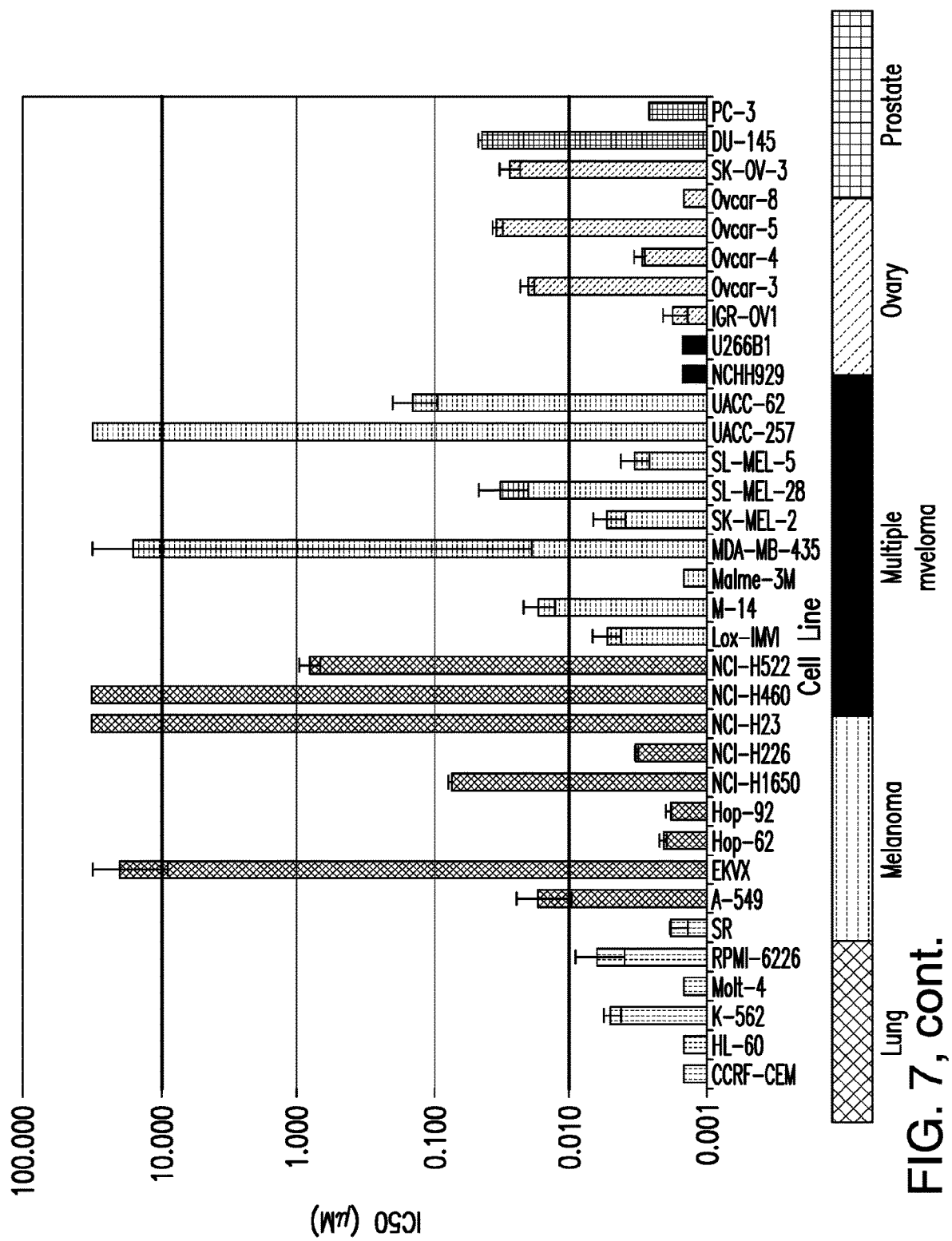
FIG. 7, cont.

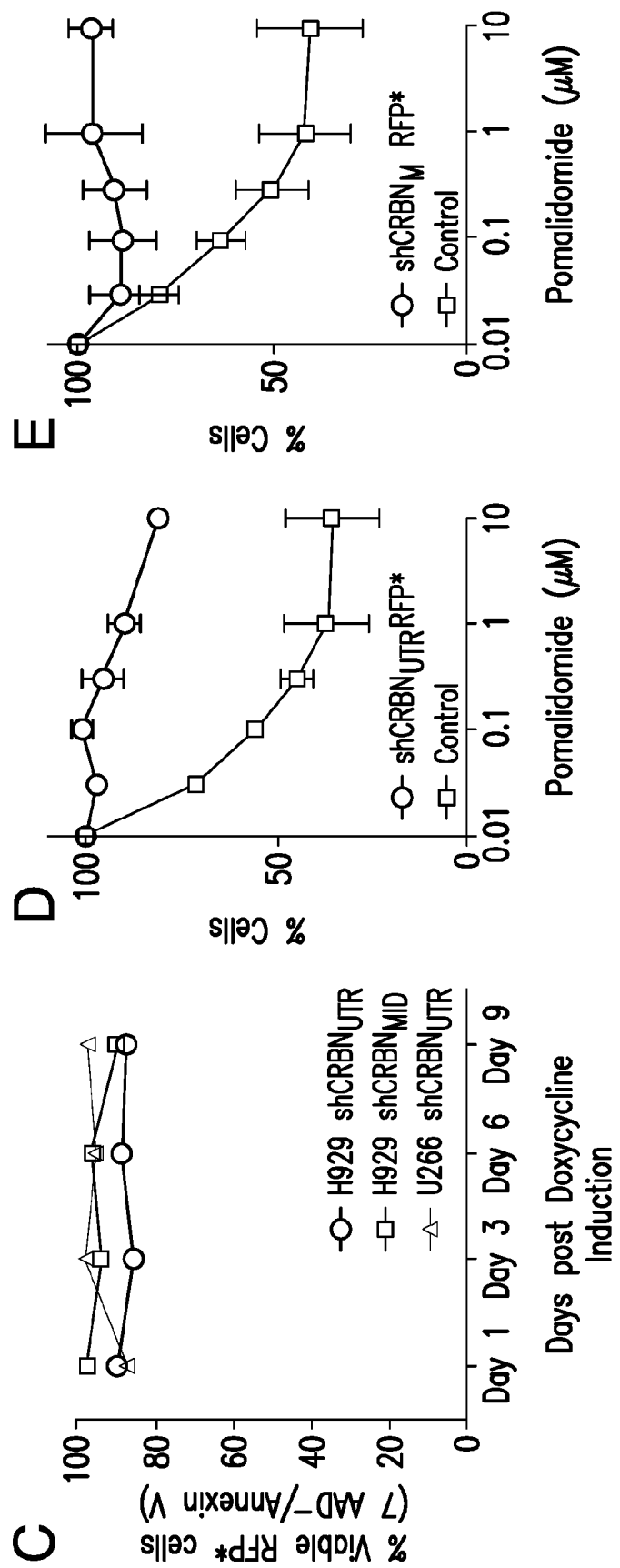
FIG. 25, cont.

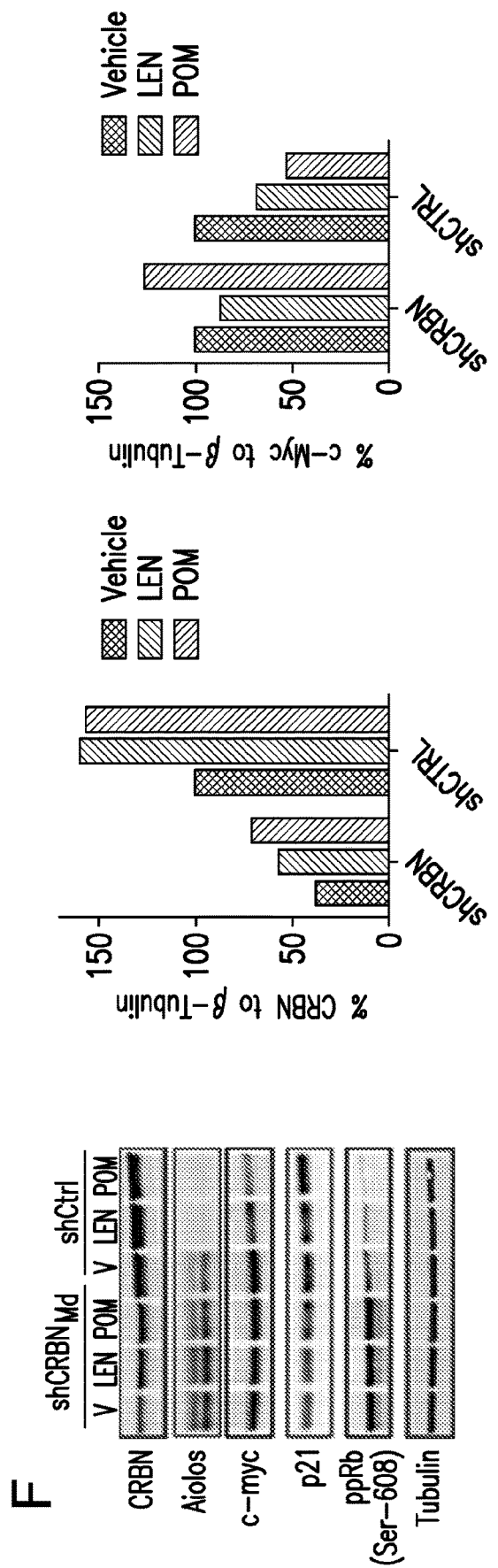
FIG. 25, cont.

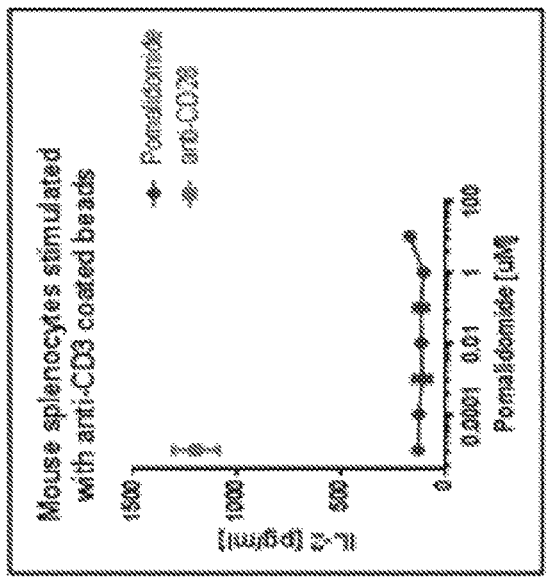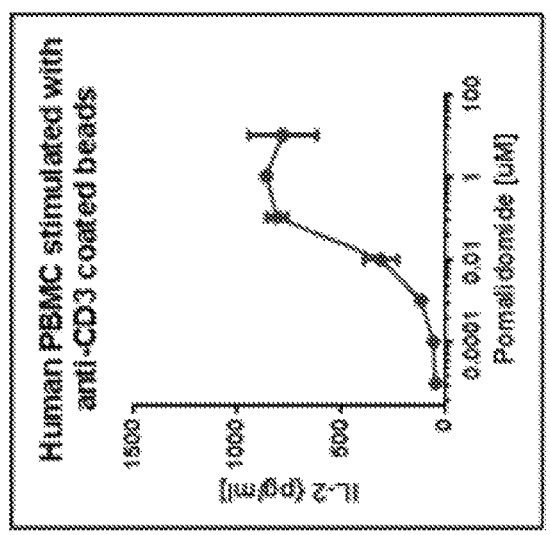
FIG. 26

A

```
hGSPT1    ------------------------------------------MDPGSGGGGGGGGGGSSSGSSS
scSUP35   MSDSNQGNNQQNYQQYSQNGNQQQGNNRYQGYQAYNAQAQPAGGYYQNYQGYSGYQQGGY
                                                    :**   . *.. ..

hGSPT1    SDSAPDCWDQADMEAPG-----PGPCGGGGSLAAAAEAQRENLSAAFSRQLNVNAKPFVPN
scSUP35   QQYNPDAGYQQQYNPQGGYQQYNPQGGYQQQFNPQGGRGNYKNFNYNNNLQGYQAGFQPQ
          .:  **.  *  :. *      . * **   .    . .: : :  :..:*:       * *:

hGSPT1    VHAAEFVPSFLRGPAAPPPP---------AGGAANNHGAGSGAGGRAAPVESSQEEQSLCEG
scSUP35   SQGMSLNDFQKQQKQAAPKPKKTLKLVSSSGIKLANATKKVGTKPAESDKKEEEKSAETK
           : .. :    :    *.** *       :... :  .* . .* :..* :...:**:* hGSPT1    SNSAVSMELSEPIVENGETEMSPEESWEHKEEISEAEPGGGSLGDGRPPEESAHEMMEEE
scSUP35   EPTKEPTKVEEPVKKEEKPVQTEEKTEEKSELPKVEDLKISESTHNTNNANVTSADALIK
          . :  . ::.**:  ::  :.   : *::  *:..*   .    :  ..  ..    : :   :

hGSPT1    EEIPKPKSVVAPPGAPKKEHVNVVFIGHVDAGKSTIGGQIMYLTGMVDKRTLEKYEREAK
scSUP35   EQEEEVDDEVVNDMFGGKDHVSLIFMGHVDAGKSTMGGNLLYLTGSVDKRTIEKYEREAK
          *:    : .. *.     *: **.:: *: *******  :  **  :****** hGSPT1    EKNRETWYLSWALDTNQEERDKGKTVEVGRAYFETEKKHFTILDAPGHKSFVPNMIGGAS
scSUP35   DAGRQGWYLSWVMDTNKEERNDGKTIEVGKAYFETEKRRYTILDAPGHKMYVSEMIGGAS
          :  .*: ***.: *:  *:. *: *: ***:::: *******   :*. :  ****** hGSPT1    QADLAVLVISARKGEFETGFEKGGQTREHAMLAKTAGVKHLIVLINKMDDPTVNWSNERY
scSUP35   QADVGVLVISARKGEYETGFERGGQTREHALLAKTQGVNKMVVVVNKMDDPTVNWSKERY
          *:.******: *:*** *  *.  **:::: *::*********:  * hGSPT1    EECKEKLVPFLKKVGFNPKKDIHFMPCSGLTGANLKEQSD--FCPWYIGLPFIPYLDNLP
scSUP35   DQCVSNVSNFLRAIGYNIKTDVVFMPVSGYSGANLKDHVDPKECPWYTGPTLLEYLDTMN
          ::* .:: ** :   *:: :*  *.* *** **  :*****:: *     **** * .:: ***.:

hGSPT1    NFNRSVDGPIRLPIVDKYKDMGTVVLGKLESGSICKGQQLVMMPNKHNVEVLGILSD-DV
scSUP35   HVDRHINAPFMLPIAAKMKDLGTIVEGKIESGHIKKGQSTLLMPNKTAVEIQNIYNETEN
          :.:* ::.*. ***. * **.  * **:**:* **  *.   ::* ****  **: .   * .:  :

hGSPT1    ETDTVAPGENLKIRLKGIEEEEILPGFILCDPNNLCHSGRTFDAQIVIIEHKSIICPGYN
scSUP35   EVDMAMCGEQVKLRIKGVEEEDISPGFVLTSPKNPIKSVTKFVAQIAIVELKSIIAAGFS
          *.*    .   **::*:*:**:***:*:* .*:*   .  :*  ***.:: * ****..:.

hGSPT1    AVLHIHTCIEEVEITALICLVDKKSGEKSKTRPRFVKQDQVCIARLRTAGTICLETFKDF
scSUP35   CVMHVHTAIEEVHIVKLLHKLEKGTNRKSKKPPAFAKKGMKVIAVLETEAPVCVETYQDY
          .*:*:*:**.****.*,*.  *:   ::* :..***. * *.*:.   ** *.* ..:*:**::*:

hGSPT1    PQMGRFTLRDEGKTIAIGKVLKLVPEKD
scSUP35   PQLGRFTLRDQGTTIAIGKIVKIAE---
          **:*******:*.:.******::*:*:.
```

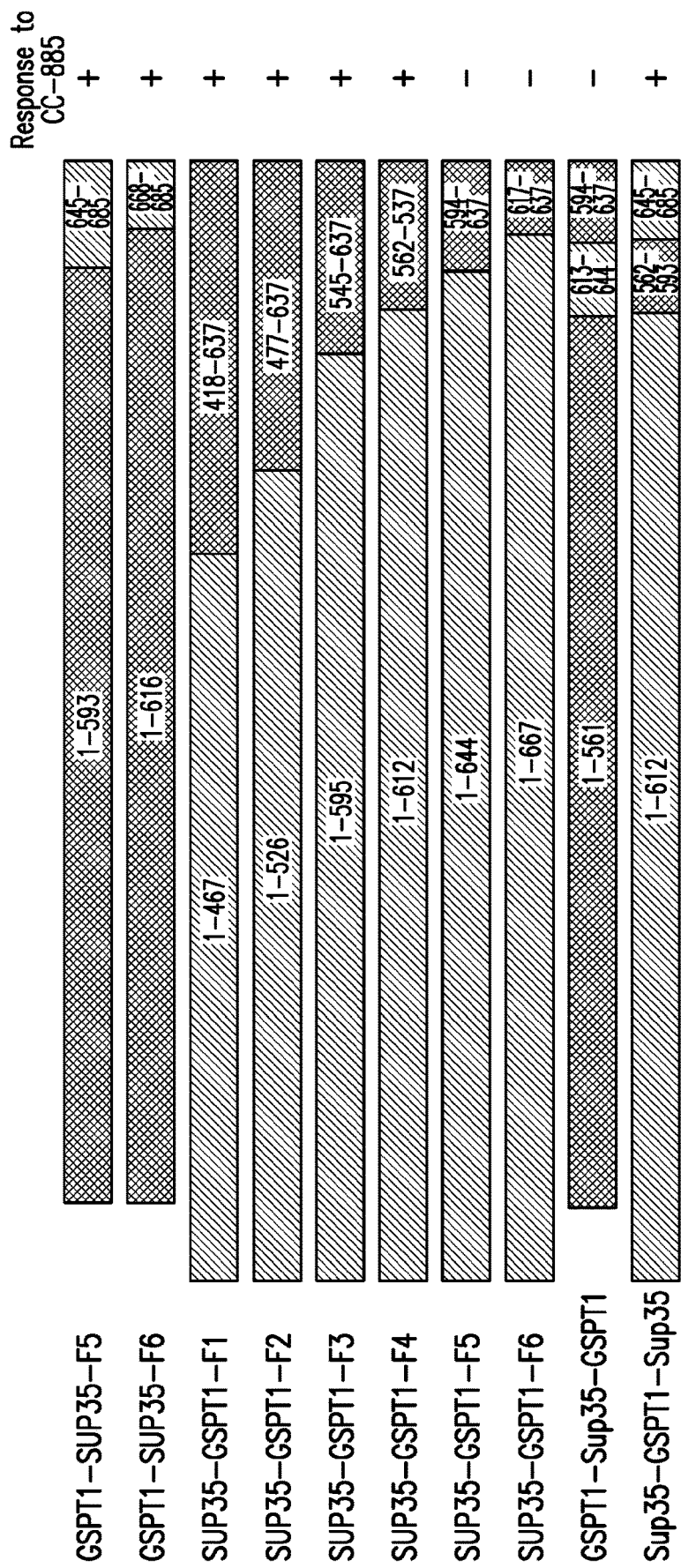
FIG. 30, cont.

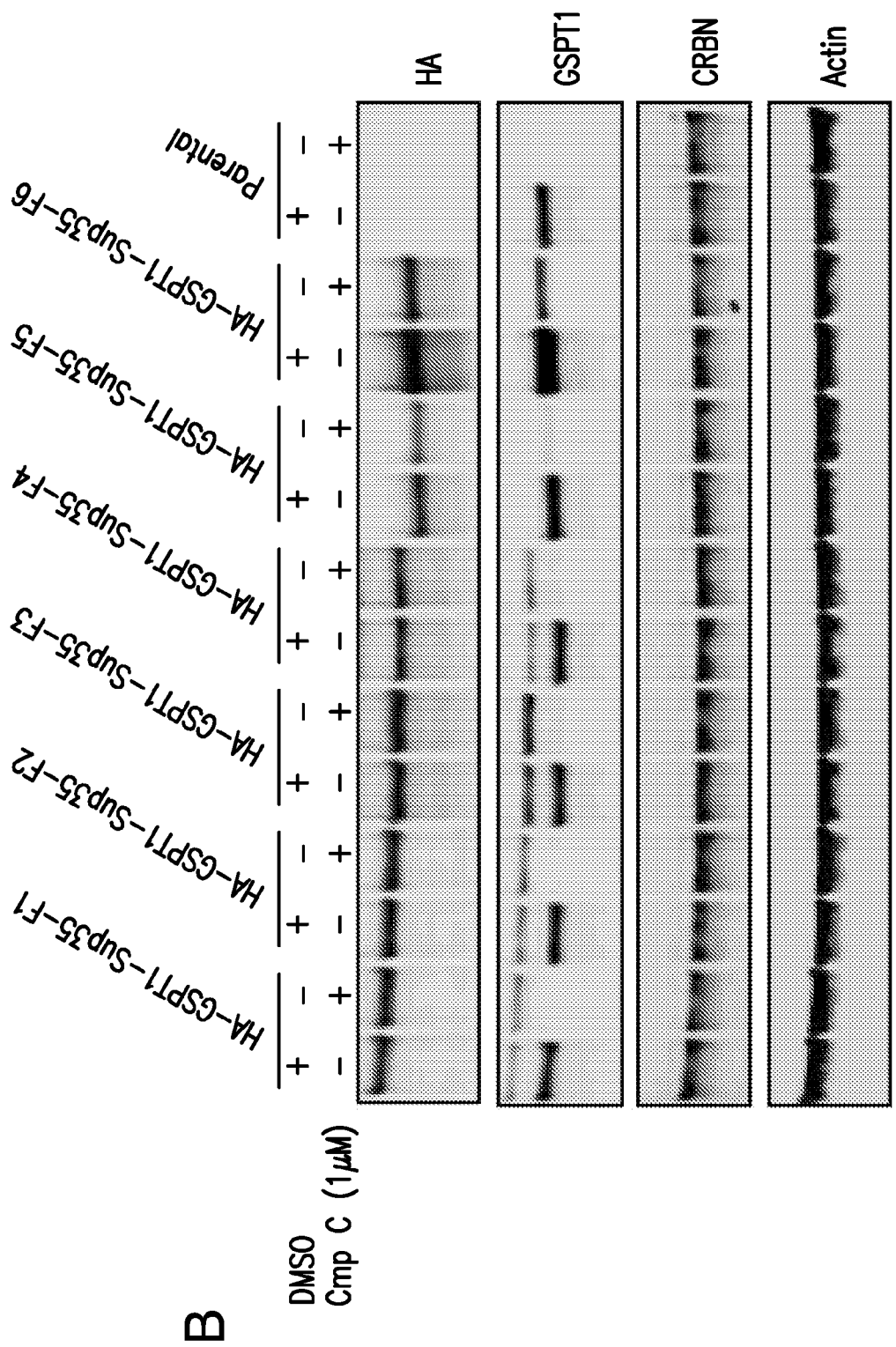
FIG. 30, cont.

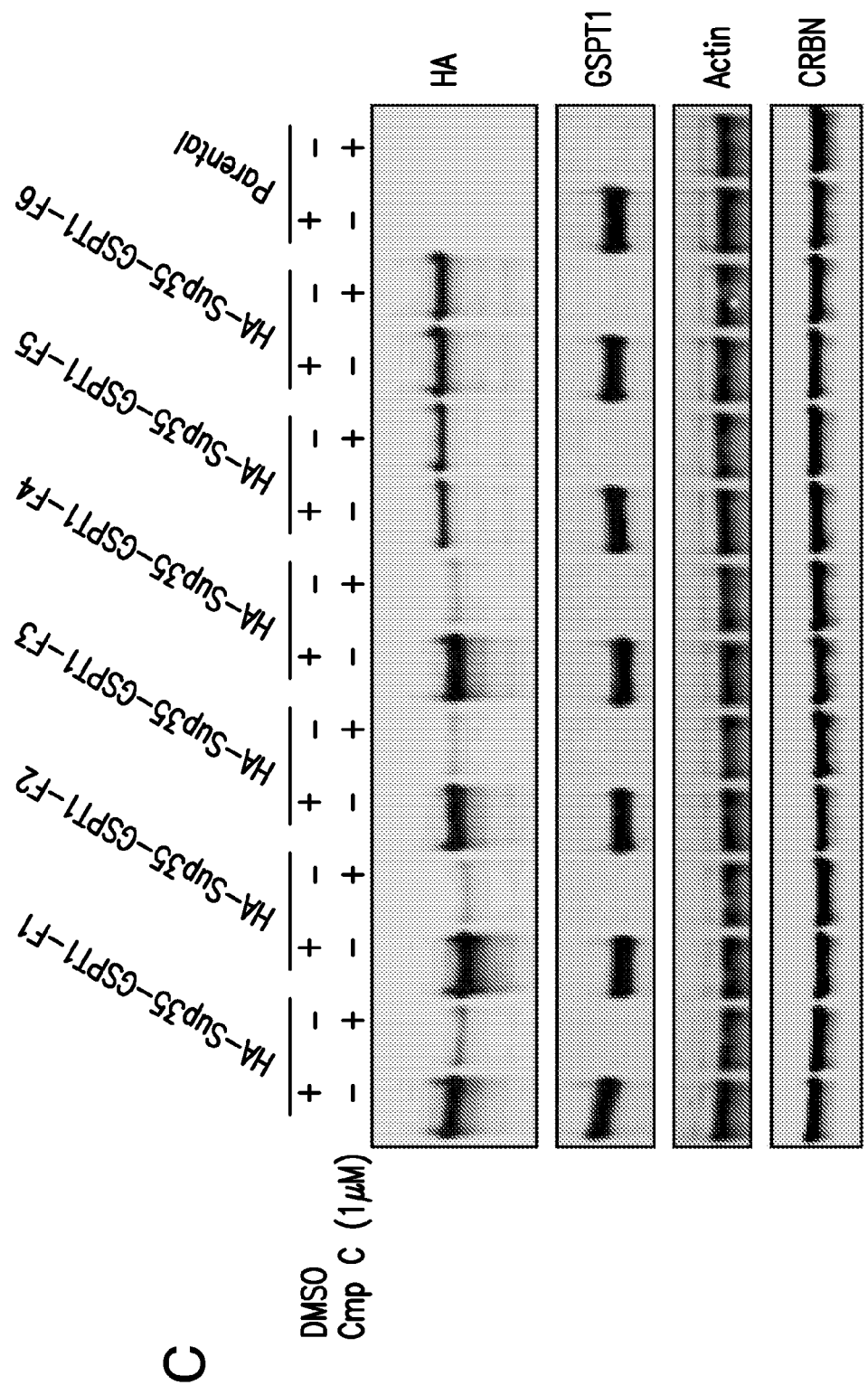
FIG. 30, cont.

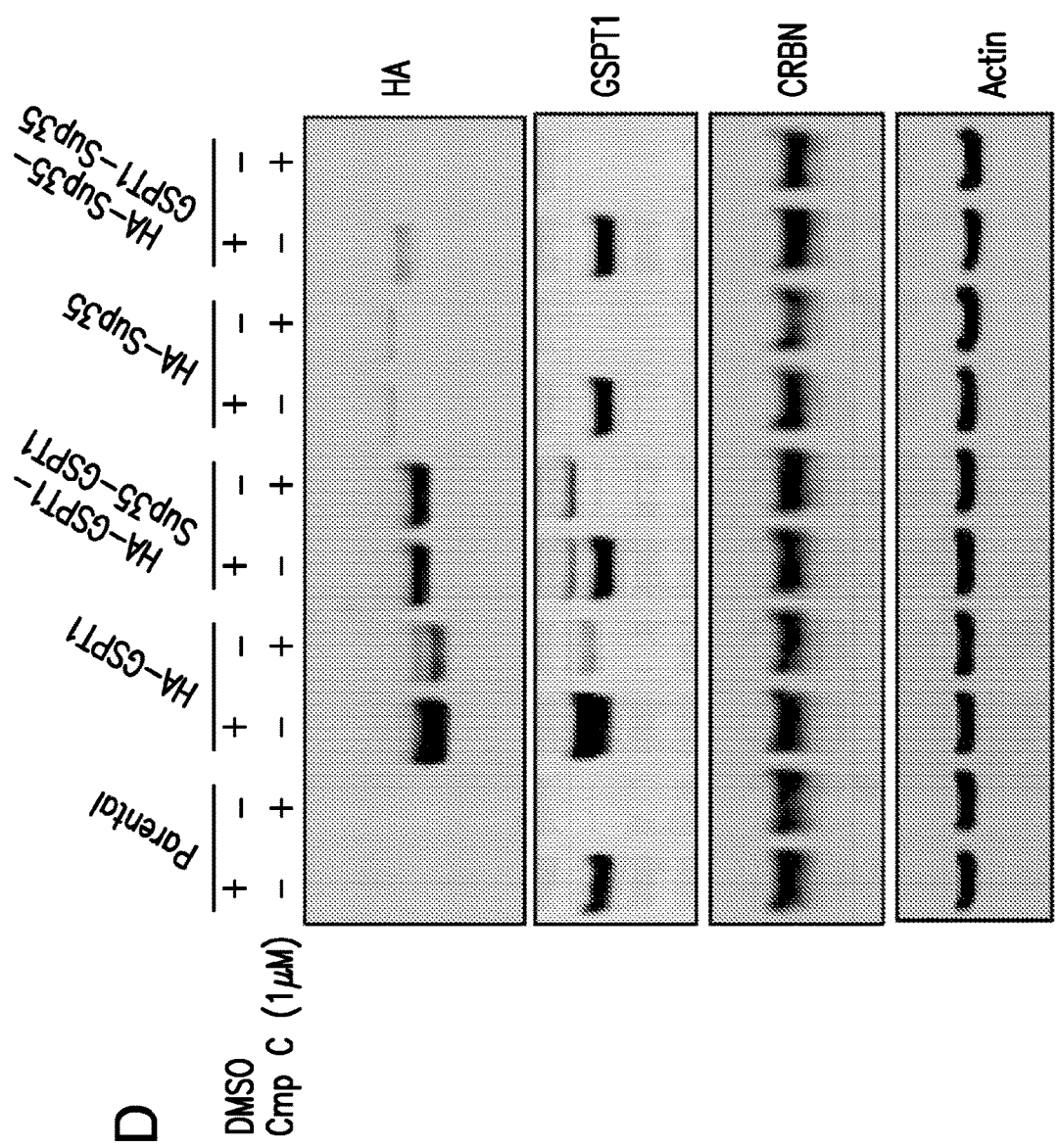
FIG. 30, cont.

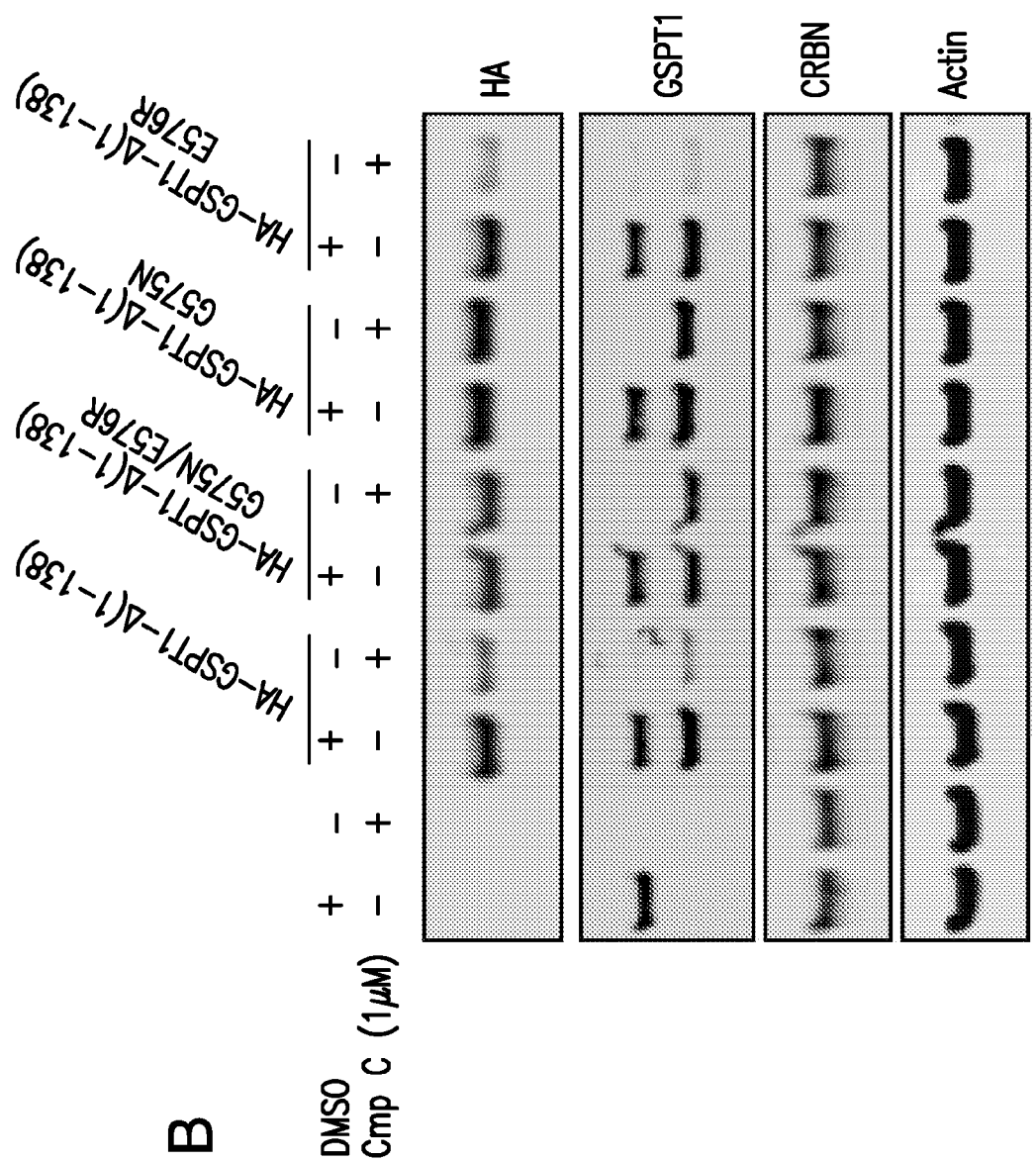
FIG. 31, cont.

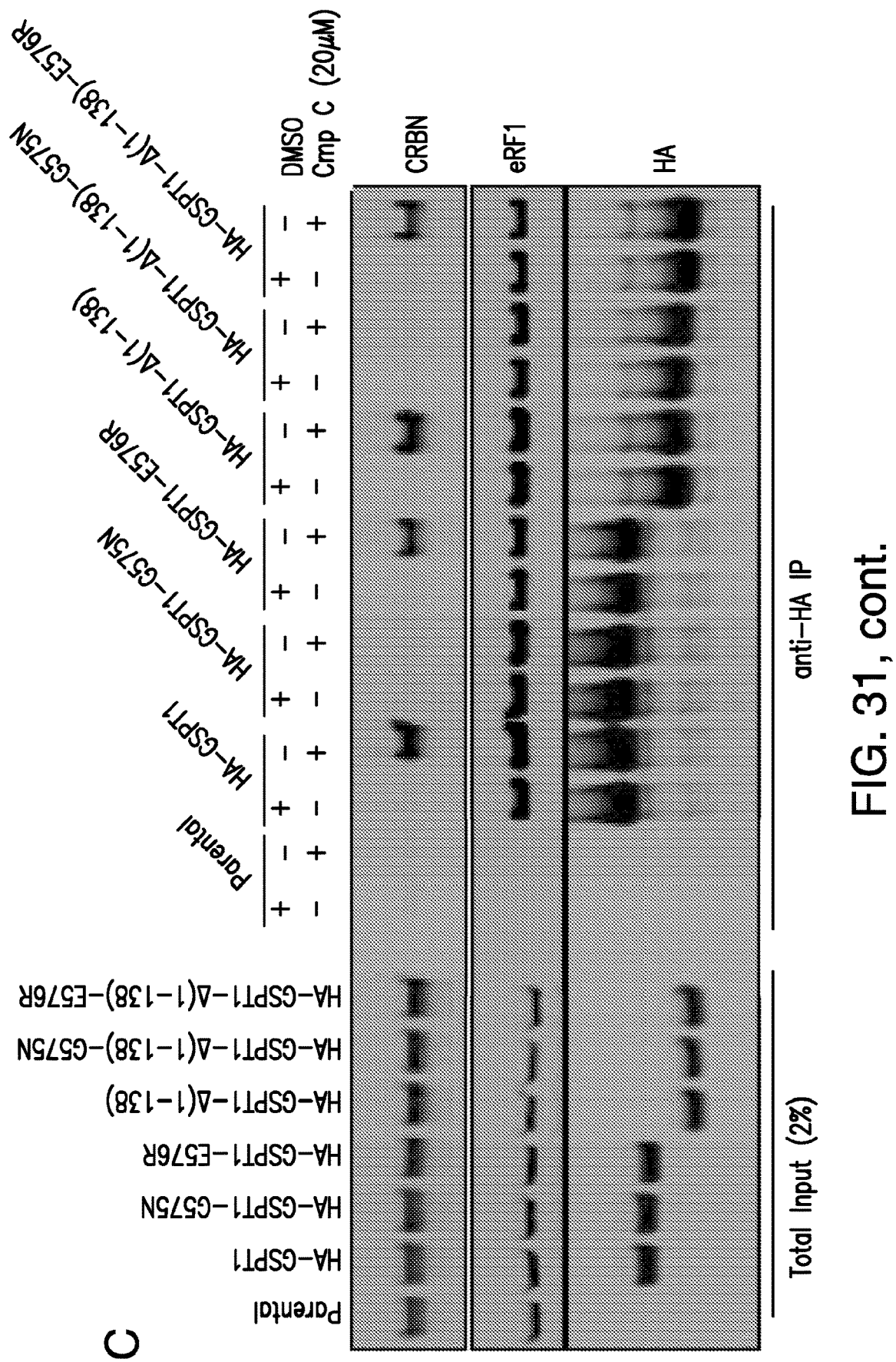
FIG. 31, cont.

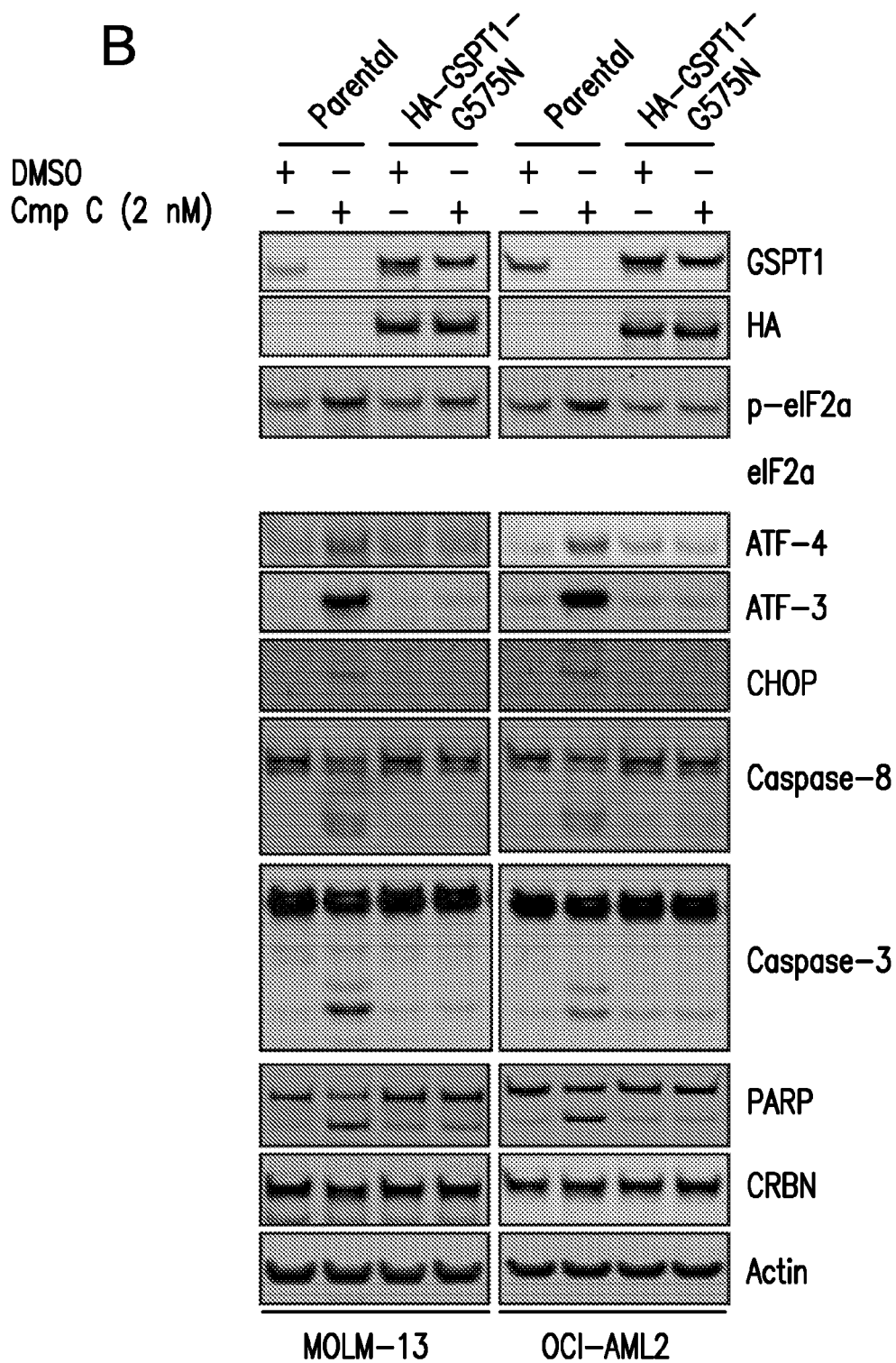
FIG. 32, cont.

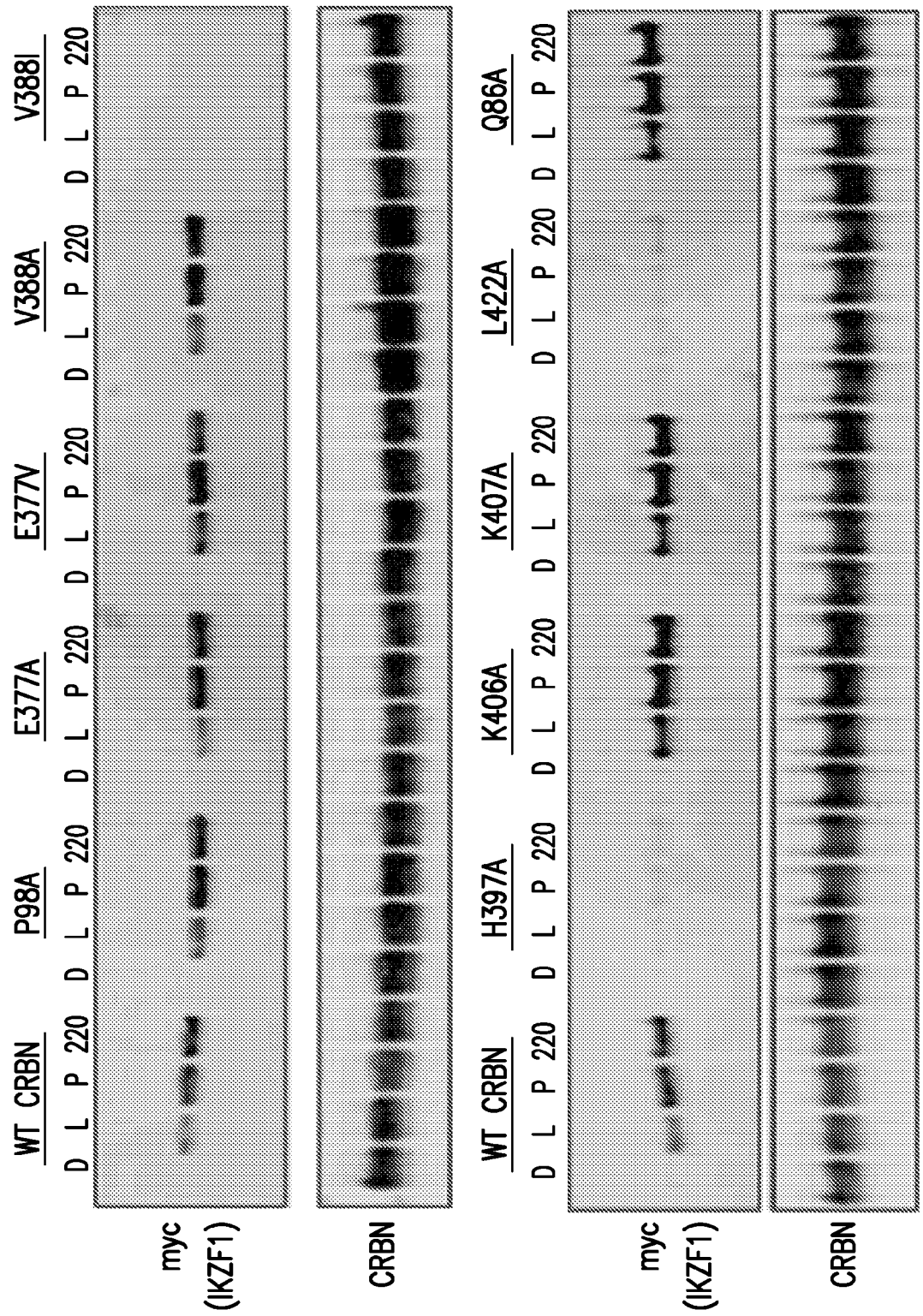
FIG. 39B con't

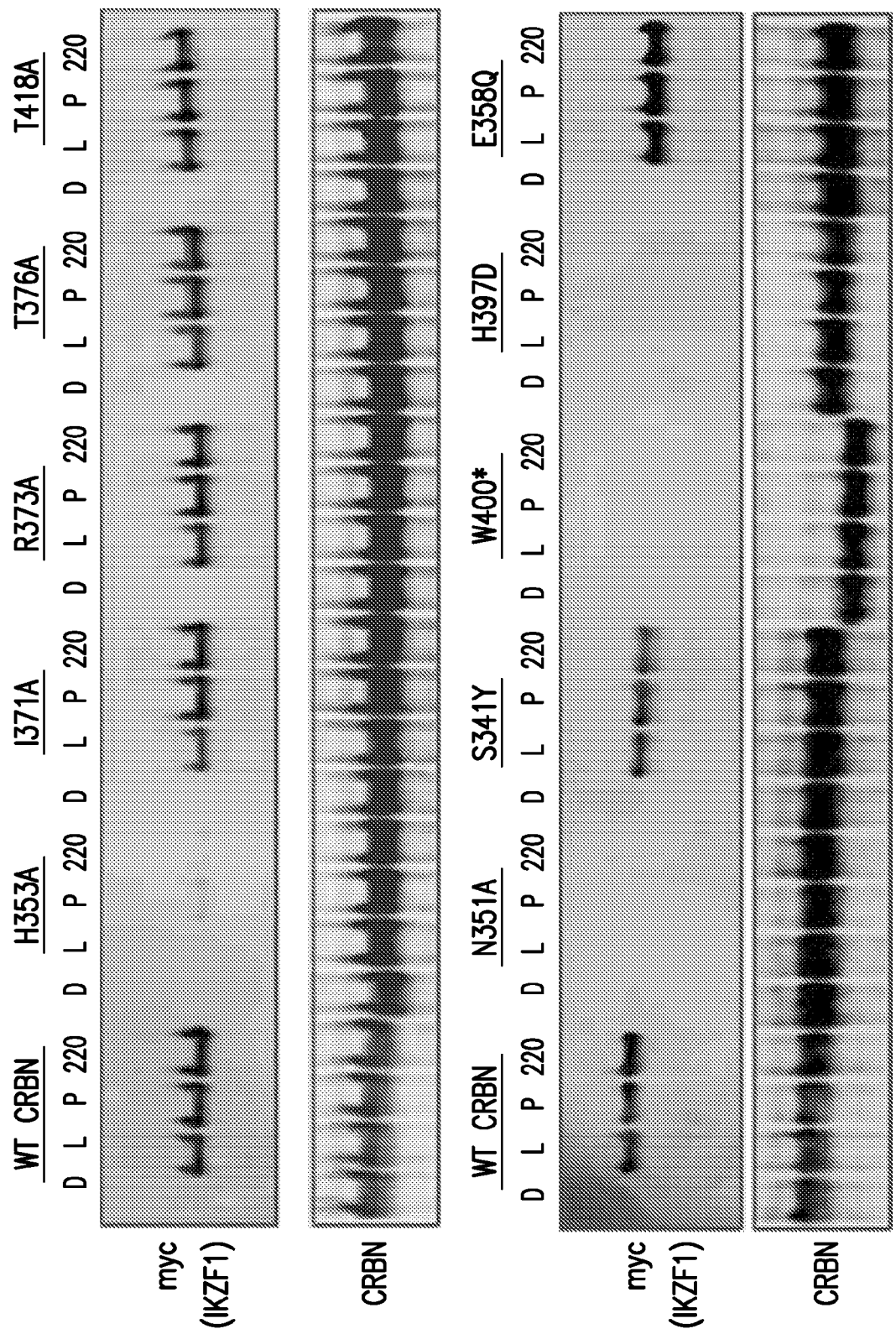
FIG. 39B con't

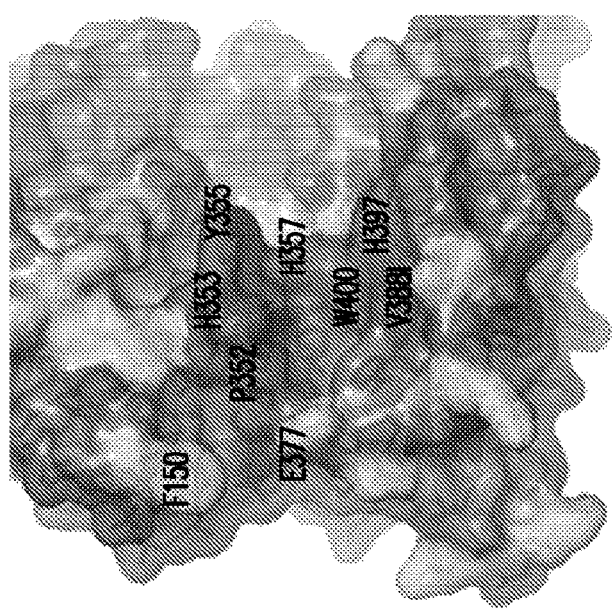
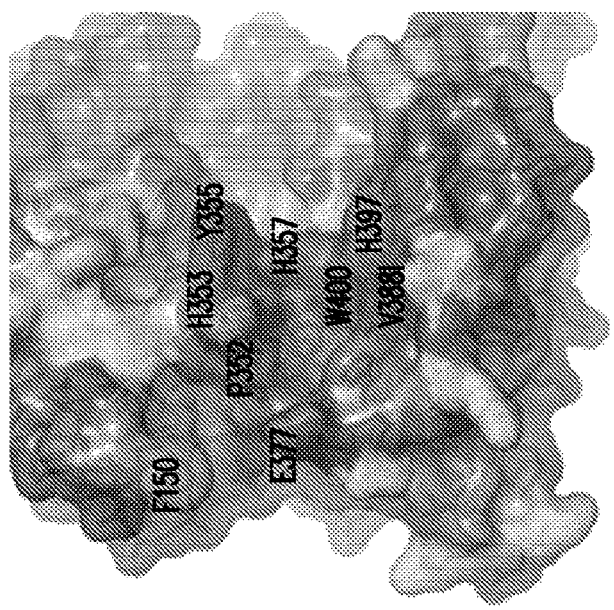
FIG. 40

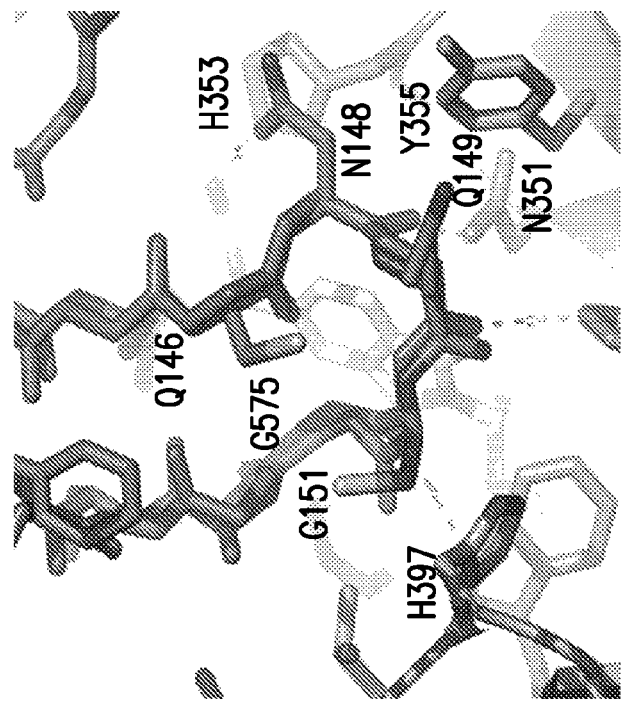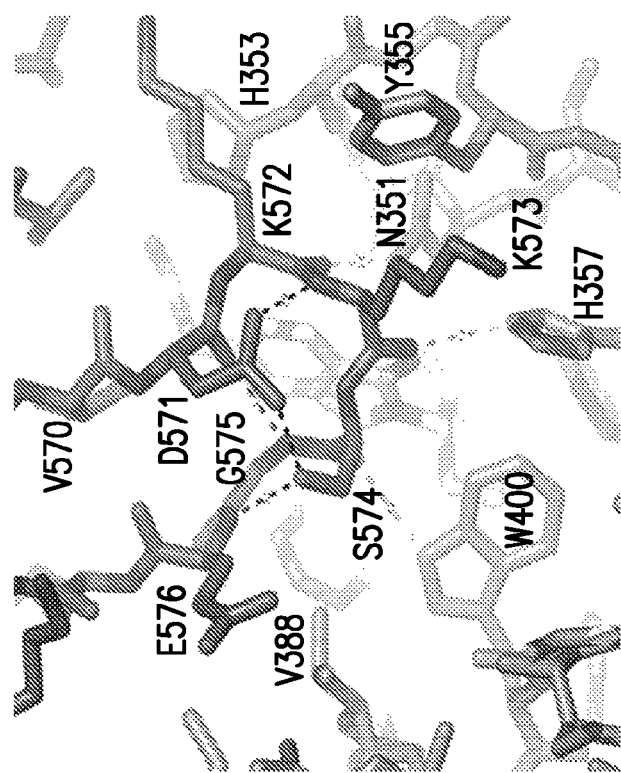
FIG. 41

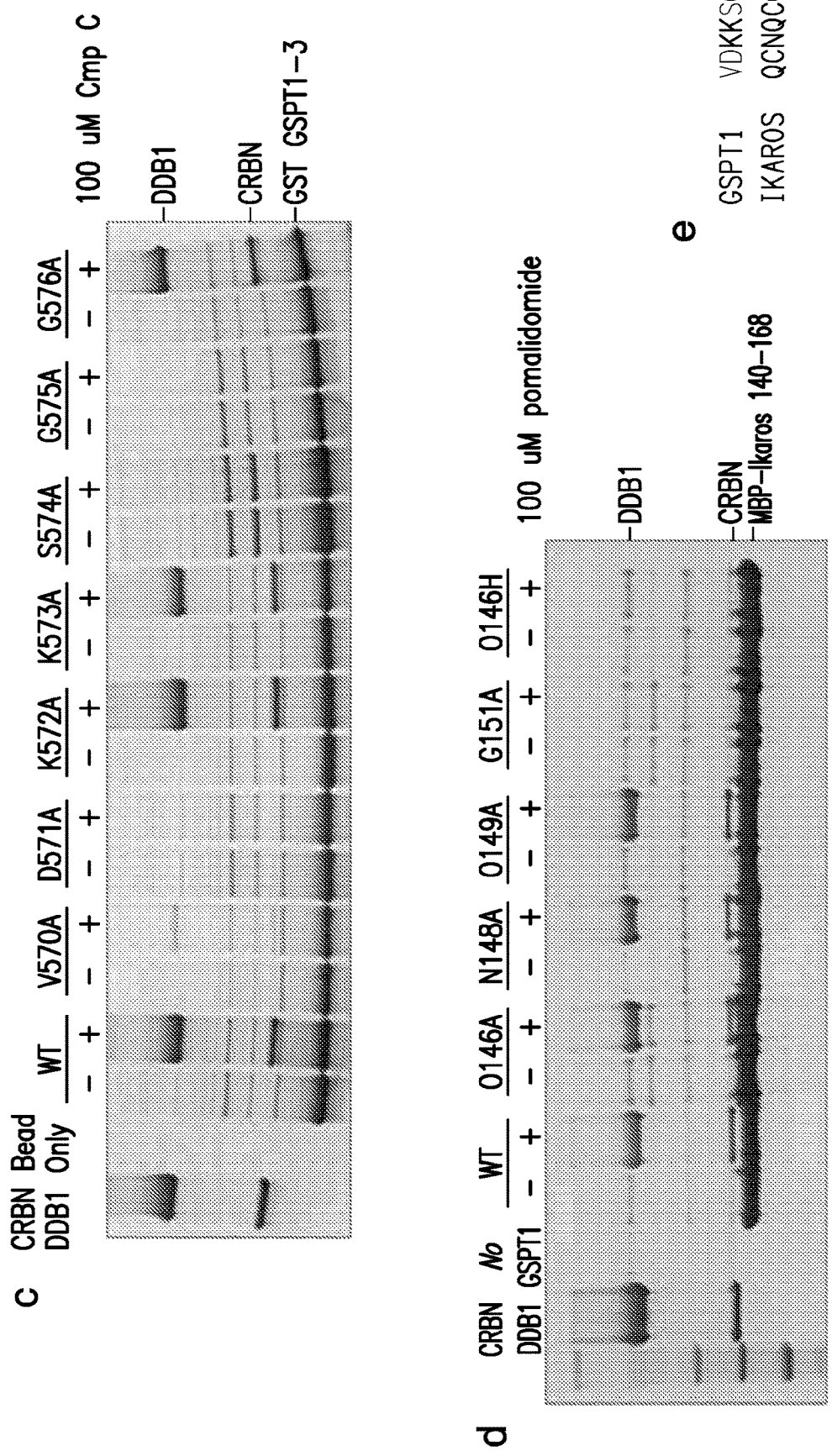
FIG. 41, cont.

COMPOSITIONS AND METHODS FOR INDUCING CONFORMATIONAL CHANGES IN CEREBLON AND OTHER E3 UBIQUITIN LIGASES

CROSS-REFERENCE TO RELATED APPLICATIONS

The present application is a U.S. National Stage Application under 35 U.S.C. § 371 of International Patent Application No. PCT/US2016/068697, filed on Dec. 27, 2016, which claims priority to U.S. Provisional Patent Application No. 62/271,864, filed Dec. 28, 2015, the entireties of which are incorporated by reference.

1. FIELD

Provided herein are compositions, therapeutic methods, screening methods, computational methods and biomarkers based upon the elucidation of the interaction among cereblon, its substrates and certain compounds or agents, including small molecules, peptides, and proteins.

REFERENCE TO SEQUENCE LISTING SUBMITTED ELECTRONICALLY

This application incorporates by reference a Substitute Sequence Listing submitted as a text file entitled "12827-980-999_SEQ_LISTING.txt" created on Feb. 11, 2020 and having a size of 17,948 bytes.

2. BACKGROUND

2.1 Cereblon

At least two isoforms of the protein cereblon (CRBN) exist, which are 442 and 441 amino acids long, respectively, and CRBN is conserved from plant to human. In humans, the CRBN gene has been identified as a candidate gene of an autosomal recessive nonsyndromic mental retardation (ARNSMR). See Higgins, J. J. et al., *Neurology*, 2004, 63:1927-1931. CRBN was initially characterized as an RGS-containing novel protein that interacted with a calcium-activated potassium channel protein (SLO1) in the rat brain, and was later shown to interact with a voltage-gated chloride channel (CIC-2) in the retina with AMPK1 and DDB1. See Jo, S. et al., *J. Neurochem*, 2005, 94:1212-1224; Hohberger B. et al., *FEBS Lett*, 2009, 583:633-637; Angers S. et al., *Nature*, 2006, 443:590-593. DDB1 was originally identified as a nucleotide excision repair protein that associates with damaged DNA binding protein 2 (DDB2). Its defective activity causes the repair defect in the patients with xeroderma pigmentosum complementation group E (XPE). DDB1 also appears to function as a component of numerous distinct DCX (DDB1-CUL4-X-box) E3 ubiquitin-protein ligase complexes which mediate the ubiquitination and subsequent proteasomal degradation of target proteins. CRBN has also been identified as a target for the development of therapeutic agents for diseases of the cerebral cortex. See WO 2010/137547 A1.

CRBN has recently been identified as a key molecular target that binds to thalidomide to cause birth defects. See Ito, T. et al., *Science*, 2010, 327:1345-1350. DDB1 was found to interact with CRBN and, thus, was indirectly associated with thalidomide. Moreover, thalidomide was able to inhibit auto-ubiquitination of CRBN in vitro, suggesting that thalidomide is an E3 ubiquitin-ligase inhibitor. Id. Importantly, this activity was inhibited by thalidomide in wild-type cells, but not in cells with mutated CRBN binding sites that prevent thalidomide binding. Id. The thalidomide binding site was mapped to a highly conserved C-terminal 104 amino acid region in CRBN. Id. Individual point mutants in CRBN, Y384A and W386A were both defective for thalidomide binding, with the double point mutant having the lowest thalidomide-binding activity. Id. A link between CRBN and the teratogenic effect of thalidomide was confirmed in animal models of zebra-fish and chick embryos. Id.

Whether binding to CRBN, the CRBN E3 ubiquitin-ligase complex, or one or more substrates of CRBN, is required for the beneficial effects of thalidomide and other drugs is yet to be established. Understanding these interactions with thalidomide and other drug targets will allow the definition of the molecular mechanisms of efficacy and/or toxicity and may lead to drugs with improved efficacy and toxicity profiles.

2.2 Compounds

Compounds for the methods provided herein comprises a group of immunomodulatory compounds, including but not limited to, thalidomide, lenalidomide and pomalidomide which have shown remarkable responses in patients with multiple myeloma, lymphoma and other hematological diseases such as myelodysplastic syndrome. See Galustian C, et al., *Expert Opin Pharmacother.*, 2009, 10:125-133. These drugs display a broad spectrum of activity, including anti-angiogenic properties, modulation of pro-inflammatory cytokines, co-stimulation of T cells, increased NK cell toxicity, direct anti-tumor effects and modulation of stem cell differentiation. For example, thalidomide and lenalidomide have emerged as important options for the treatment of multiple myeloma in newly diagnosed patients, in patients with advanced disease who have failed chemotherapy or transplantation, and in patients with relapsed or refractory multiple myeloma. Lenalidomide in combination with dexamethasone has been approved for the treatment of patients with multiple myeloma who have received at least one prior therapy. Pomalidomide may also be administered in combination with dexamethasone. U.S. Patent Publication No. 2004/0029832 A1, the disclosure of which is hereby incorporated in its entirety, discloses the treatment of multiple myeloma.

Other exemplary compounds provided herein include 3-(5-amino-2-methyl-4-oxo-4H-quinazolin-3-yl)-piperidine-2,6-dione ("Compound A"), 3-(4-((4-(morpholinomethyl)benzyl)oxy)-1-oxoisoindolin-2-yl)piperidine-2,6-dione ("Compound B"), and 1-(3-chloro-4-methylphenyl)-3-((2-(2,6-dioxopiperidin-3-yl)-1-oxoisoindolin-5-yl)methyl)urea ("Compound C"), or an enantiomer or a mixture of enantiomers thereof or a pharmaceutically acceptable salt, solvate, hydrate, co-crystal, clathrate, or polymorph thereof.

Understanding the interactions of CRBN, the CRBN E3 ubiquitin-ligase complex, or one or more substrates of CRBN with thalidomide, lenalidomide, pomalidomide and other drug targets will allow the definition of the molecular mechanisms of efficacy and/or toxicity and may lead to drugs with improved efficacy and toxicity profiles.

3. SUMMARY

We have discovered that CRBN has pluripotent potential as a drug target for the treatment of various diseases. We believe we are the first to report and understand that cereblon can be induced to undergo conformational changes by use of certain small molecules or other agents that we will call "cereblon modifying agents" (CMAs). The use of the appropriate agent leads to a distinct conformational change or other alteration in the properties of the CRBN surface, and a resulting distinct phenotypic response. Cereblon is not simply a unidimensional or monotypic protein that interacts with a single substrate. Instead, without being limited by theory, the conformational change or phenotypic response of cereblon or its pathway is dependent upon cell type and, most importantly, the CMA used to interact with cereblon or its pathway.

As such, we describe herein a variety of distinct conformational changes, surface property alterations, phenotypic responses and CMAs. We also describe treatment methods, compositions, drug screens and computational methods that exploit these discoveries.

We also describe the use of known agents as CMAs for new treatment methods. In another embodiment we disclose the use of new CMA or CMA classes based upon the conformational change, alteration in surface properties, or phenotypic response. It should be noted that these discoveries permit a plethora of methods to be used to treat diseases associated with cereblon pathway. Thus, also described herein are known or new agents as CMAs for use in methods for treating diseases.

In one aspect, provided herein is a method of identifying a test compound that induces a CRBN conformational change (e.g., within the CMA-binding pocket of the CRBN) or otherwise altering the properties of a CRBN surface. In certain embodiments, the method comprises (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a compound that induces a CRBN conformational change or otherwise alters the properties of a CRBN surface. In some embodiments, the first set of atomic coordinates and/or said second set of atomic coordinates define a CMA binding domain. In certain embodiments, the difference in atomic coordinates is determined by assessing differences in atomic distances. Also provided herein is a test compound identified by this method. In some embodiments, the test compound induces a CRBN conformational change. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein.

In certain embodiments of the various compositions and methods provided herein, the properties of the CRBN surface are altered by the placement of compound appendages.

In a second aspect, provided herein is a method of identifying a test compound that induces a CRBN conformational change (e.g., within the CMA-binding pocket of the CRBN) or otherwise altering the properties of a CRBN surface. In certain embodiments, the method comprises (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or otherwise alters the properties of a CRBN surface. In some embodiments, the first three-dimensional structure is of a CRBN that is not bound to a reference compound (also sometimes referred to as an "unbound CRBN" herein, and which is not meant to preclude the CRBN being bound to other proteins, e.g., DDB1). In some embodiments, the CRBN that is not bound to a reference compound (or unbound CRBN) has a three-dimensional structure as determined by x-ray diffraction having the atomic coordinates set forth in Table 8. Also provided herein is a test compound identified by this method. In some embodiments, the test compound induces a CRBN conformational change. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of an unbound CRBN, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In some embodiments, the first crystal structure of the unbound CRBN has a three-dimensional structure as determined by x-ray diffraction having the atomic coordinates set forth in Table 8. In certain embodiments, the conformational change or alteration is assessed by a method comprising (a) (i) obtaining a first three-dimensional structure of an unbound CRBN; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof. In a specific embodiment, the CRBN is further bound to DDB1.

In some embodiments of the various compositions and methods provided herein, the crystal structure of CRBN is a crystal structure of mouse CRBN. In some embodiments, the crystal structure of CRBN is a crystal structure of mouse CRBN that is bound to a reference compound. In other embodiments, the crystal structure of CRBN is a crystal structure of mouse CRBN that is not bound to a reference compound. In one embodiment, the crystal structure of mouse CRBN that is not bound to a reference compound has a three-dimensional structure as determined by x-ray diffraction having the atomic coordinates set forth in Table 8. In certain embodiments of the various compositions and methods provided herein, the crystal structure of CRBN is a crystal structure of human CRBN. In some embodiments, the crystal structure of CRBN is a crystal structure of human CRBN that is bound to a reference compound. In other embodiments, the crystal structure of CRBN is a crystal structure of human CRBN that is not bound to a reference compound. In certain embodiments, the CRBN is further bound to DDB1. In other embodiments of the various compositions and methods provided herein, the CMA-binding pocket of CRBN is an immunomodulatory agent-binding pocket.

In a third aspect, provided herein is a method of identifying a test compound that has a specific downstream biological activity comprising: (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a compound has the specific downstream biological activity. In some embodiments, the first crystal structure is of a CRBN that is not bound to a reference compound. In one embodiment, the crystal structure of mouse CRBN that is not bound to a reference compound has a three-dimensional structure as determined by x-ray diffraction having the atomic coordinates set forth in Table 8. In some embodiments, the first set of atomic coordinates and/or said second set of atomic coordinates define a CMA binding domain. In certain embodiments, the difference in atomic coordinates is determined by assessing differences in atomic distances. In some embodiments, the method further comprises assaying the specific biological activity. Also provided herein is a test compound identified by this method. In some embodiments, the compound induces a CRBN conformational change (e.g., within the CMA-binding pocket of the CRBN) or otherwise altering the properties of a CRBN surface. In some embodiments, the test compound induces a CRBN conformational change. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In certain embodiments, the method further comprises administering said compound to a patient, wherein said biological activity is modulated in said patient. In certain embodiments, the patient has a disease, and wherein one or more symptoms of said disease are alleviated following said administration.

In a fourth aspect, provided herein is a method of identifying a test compound that has a specific downstream biological activity comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound has the specific downstream biological activity. In some embodiments, the first three-dimensional structure is of a CRBN that is not bound to a reference compound. In one embodiment, the crystal structure of mouse CRBN that is not bound to a reference compound has a three-dimensional structure as determined by x-ray diffraction having the atomic coordinates set forth in Table 8. Also provided herein is a test compound identified by this method. In some embodiments, the test compound induces a CRBN conformational change. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments of the various methods provided herein, the three-dimensional structure is assessed using x-ray crystallography, NMR spectroscopy, dual polarization interferometry, vibrational spectroscopy, or cryo-electron microscopy. In some embodiments, the three-dimensional structure of CRBN that is not bound to a reference compound has the atomic coordinates set forth in Table 8 as determined by x-ray diffraction. In some embodiments, the CRBN is further bound to DDB1, Cul4, Roc1, or any combination thereof. In certain embodiments, the CRBN is further bound to DDB1.

In some embodiments of the various compositions and methods provided herein, the CRBN is a mouse CRBN. In certain embodiments of the various compositions and methods provided herein, CRBN is a human CRBN. In some embodiments, the CRBN is further bound to DDB1. In other embodiments of the various compositions and methods provided herein, the CMA-binding pocket of CRBN is an immunomodulatory agent-binding pocket.

In a fifth aspect, provided herein is a method of identifying a test compound that has a specific therapeutic efficacy comprising: (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a compound has the specific therapeutic efficacy. In some embodiments, the first crystal structure is of a CRBN that is not bound to a reference compound. In one embodiment, the first crystal structure of CRBN that is not bound to a reference compound has a three-dimensional structure as determined by x-ray diffraction having the atomic coordinates set forth in Table 8. In some embodiments, the first set of atomic coordinates and/or said second set of atomic coordinates define a CMA binding domain. In certain embodiments, the difference in atomic coordinates is determined by assessing differences in atomic distances. Also provided herein is a test compound identified by this method. In some embodiments, the test compound induces a CRBN conformational change. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In certain embodiments, the method further comprises administering said compound to a patient having disease, disorder or condition, wherein one or more symptoms of said disease, disorder or condition is alleviated following said administration. In some embodiments, the CRBN is further bound to DDB1, Cul4, Roc1, or any combination thereof. In certain embodiments, the CRBN is further bound to DDB1.

In a sixth aspect, provided herein is a method of identifying a test compound that has a specific downstream biological activity comprising: (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound has the specific downstream biological activity. In some embodiments, the first three-dimensional structure is of a CRBN that is not bound to a reference compound. In one embodiment, the first three-dimensional structure of CRBN that is not bound to a reference compound has the atomic coordinates set forth in Table 8 as determined by x-ray diffraction. Also provided herein is a test compound identified by this method. In some embodiments, the test compound induces a CRBN conformational change. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN that is not bound to a reference compound has the atomic coordinates set forth in Table 8 as determined by x-ray diffraction. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof. In a specific embodiment, the CRBN is further bound to DDB1.

In a seventh aspect, provided herein is a method of designing a test compound based on fit within CMA binding pocket of CRBN, comprising: (a) generating on a computer, three-dimensional structural features of a CRBN having a conformational change in the CMA binding pocket, (b) designing a test compound capable of selectively binding to said CMA binding pocket, (c) synthesizing said test compound, (d) contacting CRBN with said synthesized test compound, and (e) determining if said test compound binds to said CRBN. In certain embodiments, the conformational change occurs in a CMA binding pocket of the CRBN. In some embodiments, the conformational change is relative to a CRBN that is not bound to a reference compound. In other embodiments, the conformational change is relative to a CRBN that is bound to a reference compound.

In an eighth aspect, provided herein is a crystal of a complex comprising CRBN and a CMA, or an analog thereof. Also provided herein is a method of obtaining the crystal, comprising concentrating a purified complex of the CRBN and the CMA, or analog thereof, and obtaining the crystal. In certain embodiments, provided herein is a crystal comprising CRBN. In some embodiments, provided herein is a crystal consisting of CRBN. In certain embodiments, provided herein is a crystal of a complex comprising CRBN and DDB1. In some embodiments, provided herein is a crystal of a complex consisting of CRBN and DDB1. In certain embodiments, provided herein is a crystal of a complex comprising CRBN and a CMA, or an analog thereof. In some embodiments, provided herein is a crystal of a complex consisting of CRBN and a CMA or an analog thereof. In certain embodiments, provided herein is a crystal of a complex comprising CRBN, DDB1, and a CMA, or an analog thereof. In some embodiments, provided herein is a crystal of a complex consisting of CRBN, DDB1, and a CMA or an analog thereof. Methods of obtaining such crystals are also provided herein.

In certain embodiments, the CRBN is bound to DDB1. In some embodiments, the CRBN is bound to Cul4. In other embodiments, the CRBN is bound to Roc1. In some embodiments, the CRBN is bound to DDB1 and Cul4. In other embodiments, the CRBN is bound to DDB1 and Roc1. In yet other embodiments, the CRBN is bound to Cul4 and Roc1. In some embodiments, the CRBN is bound to DDB1, Cul4 and Roc1. In certain embodiments, CRBN that is bound to DDB1, Cul4 and/or Roc1 is a complex with DDB1, Cul4 and/or Roc1, respectively. Crystals comprising CRBN and DDB1, Cul4 and/or Roc1 are also contemplated, as are methods of obtaining such crystals.

In certain embodiments, the CMA is thalidomide. In other embodiments, the CMA is pomalidomide. In some embodiments, the CMA is Compound B. In other embodiments, the CMA is 1-(3-chloro-4-methylphenyl)-3-((2-(2,6-dioxopiperidin-3-yl)-1-oxoisoindolin-5-yl)methyl)urea (Compound C). In certain embodiments, the CMA is a thalidomide analog. In other embodiments, the CMA is a pomalidomide analog. In some embodiments, the CMA is a Compound B analog. In other embodiments, the CMA is a Compound C analog. In other embodiments, the CMA is not thalidomide. In other embodiments, the CMA is not pomalidomide. In some embodiments, the CMA is not Compound B. In other embodiments, the CMA is not Compound C. In other embodiments, the CMA is not a thalidomide analog. In other embodiments, the CMA is not a pomalidomide analog. In some embodiments, the CMA is not a Compound B analog. In other embodiments, the CMA is not a Compound C analog.

In a ninth aspect, provided herein is a crystal of a complex comprising CRBN and a test compound, wherein said crystal has a three-dimensional structure as determined by x-ray diffraction having the atomic coordinates set forth in any one of Tables 3, 4, 5, 6 or 7. In one embodiment, the crystal has a three-dimensional structure as determined by x-ray diffraction having the atomic coordinates set forth in Table 3. In another embodiment, the crystal has a three-dimensional structure as determined by x-ray diffraction having the atomic coordinates set forth in Table 4. In other embodiments, the crystal has a three-dimensional structure as determined by x-ray diffraction having the atomic coordinates set forth in Table 5. In other embodiments, the crystal has a three-dimensional structure as determined by x-ray diffraction having the atomic coordinates set forth in Table 6. In other embodiments, the complex has a three-dimensional structure as determined by x-ray diffraction having the atomic coordinates set forth in Table 7. In some embodiments, the crystal further comprises DDB1, Cul4 and/or Roc1. In a specific embodiment, the complex further comprises DDB1.

In a tenth aspect, provided herein is a crystal of a complex comprising a CRBN and a test compound, wherein said crystal has a three-dimensional structure as determined by x-ray diffraction, wherein said three-dimensional structure has the atomic coordinates set forth in any one of Tables 3, 4, 5, 6 or 7. In one embodiment, the crystal has a three-dimensional structure as determined by x-ray diffraction, wherein said three-dimensional structure has the atomic coordinates set forth in Table 3. In another embodiment, the crystal has a three-dimensional structure as determined by x-ray diffraction, wherein said three-dimensional structure has the atomic coordinates set forth in Table 4. In yet another embodiment, the crystal has a three-dimensional structure as determined by x-ray diffraction, wherein said three-dimensional structure has the atomic coordinates set forth in Table 5. In yet another embodiment, the crystal has a three-dimensional structure as determined by x-ray diffraction, wherein said three-dimensional structure has the atomic coordinates set forth in Table 6. In some embodiments, the crystal further comprises DDB1, Cul4 and/or Roc1. In a specific embodiment, the crystal further comprises DDB1. In yet another embodiment, the crystal has a three-dimensional structure as determined by x-ray diffraction, wherein said three-dimensional structure has the atomic coordinates set forth in Table 7. In some embodiments, the complex further comprises DDB1, Cul4 and/or Roc1. In a specific embodiment, the complex further comprises DDB1.

In certain embodiments of the methods provided herein a complex comprising CRBN and reference compound has a three-dimensional structure as determined by x-ray diffraction, having the atomic coordinates set forth in any one of Tables 3, 4, 5, 6 or 7. In one embodiment, the three-dimensional structure has the atomic coordinates set forth in Table 3. In another embodiment, the three-dimensional structure has the atomic coordinates set forth in Table 4. In yet another embodiment, the three-dimensional structure has the atomic coordinates set forth in Table 5. In yet another embodiment, the three-dimensional structure has the atomic coordinates set forth in Table 6. In yet another embodiment, the three-dimensional structure has the atomic coordinates set forth in Table 7. In some embodiments, the complex further comprises DDB1, Cul4 and/or Roc1. In a specific embodiment, the complex further comprises DDB1.

In an eleventh aspect, provided herein is a method of identifying a test compound that induces a specific biological activity, comprising contacting the test compound with CRBN, inducing a CRBN conformational change (e.g., within the CMA-binding pocket of the CRBN) or otherwise altering the properties of a CRBN surface, and assessing conformational change or alteration wherein conformational change or alteration is indicative of a specific biological activity. In some embodiments, the method further comprises assaying the specific biological activity. Also provided herein is a test compound identified by this method. In some embodiments, the test compound induces a CRBN conformational change. In other embodiments, the test compound induces a CRBN conformational change relative to a CRBN contacted with a reference compound. In some embodiments, the test compound induces a CRBN conformational change relative to a CRBN bound to a reference compound. In other embodiments, the test compound induces a CRBN conformational change relative to a CRBN that is not contacted with a reference compound. In one embodiment, the CRBN that is not contacted with a reference compound has a three-dimensional structure as determined by x-ray diffraction having the atomic coordinates set forth in Table 8. In some embodiments, the test compound induces a CRBN conformational change relative to an unbound CRBN. In other embodiments, the test compound alters the properties of the CRBN surface. In some embodiments, the test compound alters the properties of the CRBN surface relative to a CRBN contacted with a reference compound. In other embodiments, the test compound alters the properties of the CRBN surface relative to a CRBN bound to a reference compound. In some embodiments, the test compound alters the properties of the CRBN surface relative to a CRBN that is not contacted with a reference compound. In other embodiments, the test compound alters the properties of the CRBN surface relative to an unbound CRBN. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In certain embodiments, the method further comprises administering said compound to a patient, wherein said biological activity is modulated in said patient. In certain embodiments, the patient has a disease, and wherein one or more symptoms of said disease are alleviated following said administration. In an embodiment, the conformational change or alteration is assessed by x-ray crystallography. In another embodiment, the conformational change is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In some embodiments, the first crystal structure is of a CRBN that is not bound to a reference compound. In one embodiment, the first crystal structure of CRBN that is not bound to a reference compound has the atomic coordinates set forth in Table 8 as determined by x-ray diffraction. In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In other embodiments, the conformational change or alteration is assessed by a method comprising (a) (i) obtaining a first three-dimensional structure of CRBN that is not bound to a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN that is not bound to a reference compound has the atomic coordinates set forth in Table 8 as determined by x-ray diffraction. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof. In a specific embodiment, the CRBN is further bound to DDB1.

In a twelfth aspect, provided herein is a method of identifying a test compound that has a specific therapeutic utility, comprising contacting the test compound with CRBN, inducing a CRBN conformational change or otherwise altering the properties of the CRBN surface, and assessing the conformational change or alteration, wherein a conformational change or alteration is indicative of the specific therapeutic utility. Also provided herein is a test compound identified by this method. In some embodiments, the test compound induces a CRBN conformational change. In other embodiments, the test compound induces a CRBN conformational change relative to a CRBN contacted with a reference compound. In some embodiments, the test compound induces a CRBN conformational change relative to a CRBN bound to a reference compound. In other embodiments, the test compound induces a CRBN conformational change relative to a CRBN that is not contacted with a reference compound. In some embodiments, the test compound induces a CRBN conformational change relative to an unbound CRBN. In other embodiments, the test compound alters the properties of the CRBN surface. In some embodiments, the test compound alters the properties of the CRBN surface relative to a CRBN contacted with a reference compound. In other embodiments, the test compound alters the properties of the CRBN surface relative to a CRBN bound to a reference compound. In some embodiments, the test compound alters the properties of the CRBN surface relative to a CRBN that is not contacted with a reference compound. In other embodiments, the test compound alters the properties of the CRBN surface relative to an unbound CRBN. In one embodiment, the structure of the unbound CRBN has the atomic coordinates set forth in Table 8 as determined by x-ray diffraction. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In some embodiments, the method further comprises administering said compound to a patient having a disease, wherein one or more symptoms of said disease is alleviated following said administration. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN that is not bound to a reference compound has the atomic coordinates set forth in Table 8 as determined by x-ray diffraction. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof. In a specific embodiment, the CRBN is bound to DDB1.

In a thirteenth aspect, provided herein is a method of inducing a CRBN conformational change (e.g., within the CMA-binding pocket of the CRBN) or alteration of the properties of a CRBN surface (e.g., on an adjacent region of the protein), comprising contacting the CRBN with a compound, wherein said CRBN conformational change or alteration results in a specific biological activity. In one embodiment, the method induces a CRBN conformational change. In a specific embodiment, the CRBN conformational change is within the CMA-binding pocket of the CRBN. In one embodiment, the CRBN conformational change is relative to a CRBN that is bound to a reference compound. In one embodiment, the CRBN that is not bound to a reference compound has a three-dimensional structure as determined by x-ray diffraction having the atomic coordinates set forth in Table 8. In a certain embodiment, the CRBN conformational change is relative to an unbound CRBN. In a specific embodiment, the CRBN conformational change is relative to the CRBN prior to contact with the test compound. In another embodiment, the method induces an alteration of the properties of a CRBN surface. In a specific embodiment, the alteration of the properties of a CRBN surface are on an adjacent region of the protein. In one embodiment, the alteration of the properties of the CRBN surface is relative to a CRBN that is bound to a reference compound. In a certain embodiment, the alteration of the properties of the CRBN surface is relative to an unbound CRBN. In a specific embodiment, the alteration of the properties of the CRBN surface is relative to the CRBN prior to contact with the test compound. In some embodiments, the biological activity is a tumoricidal effect. In other embodiments, the biological activity is an apoptosis effect.

In some embodiments, the biological activity is anti-proliferation. In yet other embodiments, the biological activity is PBMC viability. In some embodiments, the biological activity is toxicity. In certain embodiments, the biological activity is substrate degradation. In one embodiments, the biological activity is Aiolos degradation. In another embodiments, the biological activity is Ikaros degradation. In other embodiments, the biological activity is an immune-mediated effect. In another embodiment, the biological activity is IL-2 induction. In some embodiments, the biological activity is IL-2 repression. In yet other embodiments, the biological activity is an effect on fetal hemoglobin (HbF). Any combination of one, two, three or more of the aforementioned biological activities is also contemplated. In certain embodiments, the biological activity is based on specific cell type categories. In other embodiments, the biological activity is based on specific tissue type categories. In yet other embodiments, the biological activity is based on solid tumors or solid tumor categories. In some embodiments, the biological activity is based on non-solid tumor categories. In some embodiments, a CRBN conformational change is induced. In other embodiments, and alteration in the properties of a CRBN surface are induced. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change (e.g., within the CMA-binding pocket of the CRBN) or alteration of the properties of a CRBN surface (e.g., on an adjacent region of the protein). In other embodiments, the conformational change or alteration is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change (e.g., within the CMA-binding pocket of the CRBN) or alteration of the properties of a CRBN surface (e.g., on an adjacent region of the protein). In one embodiment, the first three-dimensional structure of CRBN that is not bound to a reference compound has the atomic coordinates set forth in Table 8 as determined by x-ray diffraction. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof. In a specific embodiment, the CRBN is further bound to DDB1.

In a fourteenth aspect, provided herein is a method of inducing a CRBN conformational change (e.g., within the CMA-binding pocket of the CRBN) or alteration of the properties of a CRBN surface (e.g., on an adjacent region of the protein), comprising contacting the CRBN with a compound, wherein said CRBN conformational change or alteration results in a specific therapeutic utility. In one embodiment, the method induces a CRBN conformational change. In a specific embodiment, the CRBN conformational change is within the CMA-binding pocket of the CRBN. In one embodiment, the CRBN conformational change is relative to a CRBN that is bound to a reference compound. In a certain embodiment, the CRBN conformational change is relative to an unbound CRBN. In a specific embodiment, the CRBN conformational change is relative to the CRBN prior to contact with the test compound. In another embodiment, the method induces an alteration of the properties of a CRBN surface. In a specific embodiment, the alteration of the properties of a CRBN surface are on an adjacent region of the protein. In one embodiment, the alteration of the properties of the CRBN surface is relative to a CRBN that is bound to a reference compound. In a certain embodiment, the alteration of the properties of the CRBN surface is relative to an unbound CRBN. In a specific embodiment, the alteration of the properties of the CRBN surface is relative to the CRBN prior to contact with the test compound. In some embodiments, the unbound CRBN or the CRBN prior to contact with the test compound has a three-dimensional structure as determined by x-ray diffraction having the atomic coordinates set forth in Table 8. In some embodiments, the therapeutic utility is based on solid tumors or solid tumor categories. In other embodiments, the therapeutic utility is based on non-solid tumor categories. In certain embodiments, the conformational change or alteration occurs in a CMA binding pocket of the CRBN. In some embodiments, the conformational change or alteration in said CMA binding pocket has an effect on W380, W386 and/or W400 of CRBN In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change (e.g., within the CMA-binding pocket of the CRBN) or alteration of the properties of a CRBN surface (e.g., on an adjacent region of the protein). In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change (e.g., within the CMA-binding pocket of the CRBN) or alteration of the properties of a CRBN surface (e.g., on an adjacent region of the protein). In one embodiment, the first three-dimensional structure of CRBN that is not bound to a reference compound has the atomic coordinates set forth in Table 8 as determined by x-ray diffraction. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof. In a specific embodiment, the CRBN is further bound to DDB1.

In a fifteenth aspect, provided herein is a method of inducing a CRBN conformational change (e.g., within the CMA-binding pocket of the CRBN) or alteration of the properties of a CRBN surface (e.g., on an adjacent region of the protein), comprising contacting the CRBN with a test compound, wherein said CRBN conformational change or alteration results in a different substrate specificity as compared to the substrate specificity of a CRBN that is contacted with a reference compound. Also provided herein is a method of inducing a CRBN conformational change (e.g., within the CMA-binding pocket of the CRBN) or alteration of the properties of a CRBN surface (e.g., on an adjacent region of the protein), comprising contacting the CRBN with a test compound, wherein said CRBN conformational change or alteration results in a different substrate specificity as compared to the substrate specificity of an unbound CRBN (e.g., a CRBN prior to contact with the test compound). In one embodiment, the method induces a CRBN conformational change. In a specific embodiment, the CRBN conformational change is within the CMA-binding pocket of the CRBN. In one embodiment, the CRBN conformational change is relative to a CRBN that is bound to a reference compound. In a certain embodiment, the CRBN conformational change is relative to an unbound CRBN. In a specific embodiment, the CRBN conformational change is relative to the CRBN prior to contact with the test compound. In another embodiment, the method induces an alteration of the properties of a CRBN surface. In a specific embodiment, the alteration of the properties of a CRBN surface are on an adjacent region of the protein. In one embodiment, the alteration of the properties of the CRBN surface is relative to a CRBN that is bound to a reference compound. In a certain embodiment, the alteration of the properties of the CRBN surface is relative to an unbound CRBN. In a specific embodiment, the alteration of the properties of the CRBN surface is relative to the CRBN prior to contact with the test compound. In some embodiments, the unbound CRBN or the CRBN prior to contact with the test compound has a three-dimensional structure as determined by x-ray diffraction having atomic coordinates set forth in Table 8. In some embodiments, a CRBN conformational change is induced. In other embodiments, an alteration of the properties of a CRBN surface are induced. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN that is not bound to a reference compound has the atomic coordinates set forth in Table 8 as determined by x-ray diffraction. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof. In a specific embodiment, the CRBN is further bound to DDB1.

In a sixteenth aspect, provided herein is a method of inducing a CRBN conformational change (e.g., within the CMA-binding pocket of the CRBN) or alteration of the properties of a CRBN surface (e.g., on an adjacent region of the protein), comprising contacting the CRBN with a test compound. In one embodiment, the method induces a CRBN conformational change. In a specific embodiment, the CRBN conformational change is within the CMA-binding pocket of the CRBN. In one embodiment, the CRBN conformational change is relative to a CRBN that is bound to a reference compound. In a certain embodiment, the CRBN conformational change is relative to an unbound CRBN. In a specific embodiment, the CRBN conformational change is relative to the CRBN prior to contact with the test compound. In another embodiment, the method induces an alteration of the properties of a CRBN surface. In a specific embodiment, the alteration of the properties of a CRBN surface are on an adjacent region of the protein. In one embodiment, the alteration of the properties of the CRBN surface is relative to a CRBN that is bound to a reference compound. In a certain embodiment, the alteration of the properties of the CRBN surface is relative to an unbound CRBN. In a specific embodiment, the alteration of the properties of the CRBN surface is relative to the CRBN prior to contact with the test compound. In one embodiment, the unbound CRBN or the CRBN prior to contact with the test compound has a first three-dimensional structure as determined by x-ray diffraction having the atomic coordinates set forth in Table 8. In some embodiments, said CRBN conformational change or alteration comprises a conformational change (e.g., within the CMA-binding pocket of the CRBN) or alteration of the properties of a CRBN surface (e.g., on an adjacent region of the protein) that is different than the conformational change (e.g., within the CMA-binding pocket of the CRBN) or alteration of the properties of a CRBN surface (e.g., on an adjacent region of the protein) contacted with a reference compound. In some embodiments, the CRBN conformational change or alteration results in a different biological activity. In some embodiments, the CRBN conformational change or alteration results in a different therapeutic utility. In other embodiments, the CRBN conformational change or alteration results in a different substrate specificity. In some embodiments, a CRBN conformational change is induced. In other embodiments, an alteration of the properties of a CRBN surface are induced. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN that is not bound to a reference compound has the atomic coordinates set forth in Table 8 as determined by x-ray diffraction. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof. In a specific embodiment, the CRBN is further bound to DDB1.

In a seventeenth aspect, provided herein is a method of inducing a biological activity in a cell comprising CRBN, comprising contacting said cell with a test compound, wherein said compound induces a conformational change (e.g., within the CMA-binding pocket of the CRBN) or alteration of the properties of a CRBN surface (e.g., on an adjacent region of the protein) of said CRBN, and wherein said CRBN conformational change or alteration is as compared to a reference compound, and wherein the conformational change or alteration results in said biological activity. Also provided herein is a method of inducing a biological activity in a cell comprising CRBN, comprising contacting said cell with a test compound, wherein said compound induces a conformational change (e.g., within the CMA-binding pocket of the CRBN) or alteration of the properties of a CRBN surface (e.g., on an adjacent region of the protein) of said CRBN, and wherein said CRBN conformational change or alteration is as compared to an unbound CRBN (e.g., a CRBN prior to contact with the test compound), and wherein the conformational change or alteration results in said biological activity. In one embodiment, the method induces a CRBN conformational change. In a specific embodiment, the CRBN conformational change is within the CMA-binding pocket of the CRBN. In one embodiment, the CRBN conformational change is relative to a CRBN that is bound to a reference compound. In a certain embodiment, the CRBN conformational change is relative to an unbound CRBN. In a specific embodiment, the CRBN conformational change is relative to the CRBN prior to contact with the test compound. In one embodiment, the unbound CRBN or the CRBN prior to contact with the test compound has a first three-dimensional structure as determined by x-ray diffraction having the atomic coordinates set forth in Table 8. In another embodiment, the method induces an alteration of the properties of a CRBN surface. In a specific embodiment, the alteration of the properties of a CRBN surface are on an adjacent region of the protein. In one embodiment, the alteration of the properties of the CRBN surface is relative to a CRBN that is bound to a reference compound. In a certain embodiment, the alteration of the properties of the CRBN surface is relative to an unbound CRBN. In a specific embodiment, the alteration of the properties of the CRBN surface is relative to the CRBN prior to contact with the test compound. In some embodiments, the biological activity is a tumoricidal effect. In other embodiments, the biological activity is an apoptosis effect. In some embodiments, the biological activity is anti-proliferation. In yet other embodiments, the biological activity is PBMC viability. In some embodiments, the biological activity is toxicity. In certain embodiments, the biological activity is substrate degradation. In one embodiments, the biological activity is Aiolos degradation. In another embodiments, the biological activity is Ikaros degradation. In other embodiments, the biological activity is an immune-mediated effect. In another embodiment, the biological activity is IL-2 induction. In some embodiments, the biological activity is IL-2 repression. In yet other embodiments, the biological activity is a HbF effect. Any combination of one, two, three or more of the aforementioned biological activities is also contemplated. In certain embodiments, the biological activity is based on specific cell type categories. In other embodiments, the biological activity is based on specific tissue type categories. In yet other embodiments, the biological activity is based on solid tumors or solid tumor categories. In some embodiments, the biological activity is based on non-solid tumor categories. In some embodiments, a CRBN conformational change is induced. In other embodiments, an alteration of the properties of a CRBN surface are induced. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the unbound CRBN or the CRBN prior to contact with the test compound has a first three-dimensional structure as determined by x-ray diffraction having the atomic coordinates set forth in Table 8. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof. In a specific embodiment, the CRBN is further bound to DDB1.

In an eighteenth aspect, provided herein is a method of treating or alleviating one or more symptoms of a CRBN-mediated disease or disorder in a patient, comprising administering a test compound to the subject, wherein said test compound induces a conformational change (e.g., within the CMA-binding pocket of the CRBN) or alteration of the properties of a CRBN surface (e.g., on an adjacent region of the protein), and wherein said CRBN conformational change or alteration is as compared to a reference compound, and wherein said CRBN conformational change or alteration results in treatment or alleviation of one or more symptoms of said disease or disorder. Also provided herein is a method of treating or alleviating one or more symptoms of a CRBN-mediated disease or disorder in a patient, comprising administering a test compound to the subject, wherein said test compound induces a conformational change (e.g., within the CMA-binding pocket of the CRBN) or alteration of the properties of a CRBN surface (e.g., on an adjacent region of the protein), and wherein said CRBN conformational change or alteration is as compared to an unbound CRBN (e.g., a CRBN prior to contact with the test compound), and wherein said CRBN conformational change or alteration results in treatment or alleviation of one or more symptoms of said disease or disorder. In one embodiment, the method induces a CRBN conformational change. In a specific embodiment, the CRBN conformational change is within the CMA-binding pocket of the CRBN. In one embodiment, the CRBN conformational change is relative to a CRBN that is bound to a reference compound. In a certain embodiment, the CRBN conformational change is relative to an unbound CRBN. In a specific embodiment, the CRBN conformational change is relative to the CRBN prior to contact with the test compound. In one embodiment, the unbound CRBN or the CRBN prior to contact with the test compound has a first three-dimensional structure as determined by x-ray diffraction having the atomic coordinates set forth in Table 8. In another embodiment, the method induces an alteration of the properties of a CRBN surface. In a specific embodiment, the alteration of the properties of a CRBN surface are on an adjacent region of the protein. In one embodiment, the alteration of the properties of the CRBN surface is relative to a CRBN that is bound to a reference compound. In a certain embodiment, the alteration of the properties of the CRBN surface is relative to an unbound CRBN. In a specific embodiment, the alteration of the properties of the CRBN surface is relative to the CRBN prior to contact with the test compound. In certain embodiments, the disease or disorder is a cancer or tumor. In some embodiments, a CRBN conformational change is induced. In other embodiments, an alteration of the properties of a CRBN surface are induced. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first crystal structure of CRBN has a first three-dimensional structure as determined by x-ray diffraction having the atomic coordinates set forth in Table 8. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof. In a specific embodiment, the CRBN is further bound to DDB1. In some embodiments provided herein is the above-described test compound for use in a method of treating or alleviating one or more symptoms of a CRBN-mediated disease or disorder in a patient.

In a nineteenth aspect, provided herein is a composition comprising a CRBN and a test compound, wherein said CRBN has a conformational change (e.g., within the CMA-binding pocket of the CRBN) or alteration of the properties of a CRBN surface (e.g., on an adjacent region of the protein) as compared to a reference compound. Also provided herein is a composition comprising a CRBN and a test compound, wherein said CRBN has a conformational change (e.g., within the CMA-binding pocket of the CRBN) or alteration of the properties of a CRBN surface (e.g., on an adjacent region of the protein) as compared to an unbound CRBN (e.g., a CRBN prior to contact with the test compound). In one embodiment, the CRBN has a conformational change. In a specific embodiment, the CRBN conformational change is within the CMA-binding pocket of the CRBN. In another embodiment, the CRBN has an alteration of the properties of a CRBN surface. In a specific embodiment, the alteration of the properties of a CRBN surface are on an adjacent region of the protein. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN as determined by x-ray diffraction has atomic coordinates set forth in Table 8. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof. In a specific embodiment, the CRBN is further bound to DDB1.

In a twentieth aspect, provided herein is a compound that induces a CRBN conformational change (e.g., within the CMA-binding pocket of the CRBN) or alteration of the properties of a CRBN surface (e.g., on an adjacent region of the protein) upon contact with said CRBN, as compared to the conformational change or alteration as compared to a reference compound. Also provided herein is a compound that induces a CRBN conformational change (e.g., within the CMA-binding pocket of the CRBN) or alteration of the properties of a CRBN surface (e.g., on an adjacent region of the protein) upon contact with said CRBN, as compared to the conformational change or alteration as compared to an unbound CRBN (e.g., prior to contact with the compound). In one embodiment, the unbound CRBN has a three-dimensional structure as determined by x-ray diffraction having atomic coordinates set forth in Table 8. In one embodiment, the compound induces a CRBN conformational change. In a specific embodiment, the CRBN conformational change is within the CMA-binding pocket of the CRBN. In another embodiment, the compound induces an alteration of the properties of a CRBN surface. In a specific embodiment, the alteration of the properties of a CRBN surface are on an adjacent region of the protein. In some embodiments, the CRBN conformational change or alteration results in a different biological activity. In some embodiments, the CRBN conformational change or alteration results in a different therapeutic utility. In other embodiments, the CRBN conformational change or alteration results in a different substrate specificity. In some embodiments, a CRBN conformational change is induced. In other embodiments, an alteration of the properties of a CRBN surface are induced. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN that is not bound to a reference compound has the atomic coordinates set forth in Table 8 as determined by x-ray diffraction. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof. In a specific embodiment, the CRBN is further bound to DDB1.

In a twenty-first aspect, provided herein is a complex comprising a CRBN and test compound, wherein said CRBN has a conformational change (e.g., within the CMA-binding pocket of the CRBN) or alteration of the properties of a CRBN surface (e.g., on an adjacent region of the protein) as compared to a conformational change of said CRBN contacted with a reference compound. Also provided herein is a complex comprising a CRBN and test compound, wherein said CRBN has a conformational change (e.g., within the CMA-binding pocket of the CRBN) or alteration of the properties of a CRBN surface (e.g., on an adjacent region of the protein) as compared to a conformational change of an unbound CRBN (e.g., a CRBN prior to contact with the test compound). In one embodiment, the CRBN has a conformational change. In a specific embodiment, the CRBN has a conformational change within the CMA-binding pocket of the CRBN. In another embodiment, the CRBN has an alteration of the properties of a CRBN surface. In a specific embodiment, the alteration of the properties of a CRBN surface are on an adjacent region of the protein. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN that is not bound to a reference compound has a three-dimensional structure as determined by x-ray diffraction having atomic coordinates set forth in Table 8. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof. In a specific embodiment, the CRBN is further bound to DDB1.

In a twenty-second aspect, provided herein is a method of identifying a substrate ubiquitinated by a E3 ubiquitination ligase complex comprising CRBN, said method comprising: (i) contacting said CRBN with a compound that induces a conformational change (e.g., within the CMA-binding pocket of the CRBN) or alteration of the properties of a CRBN surface (e.g., on an adjacent region of the protein), wherein said CRBN conformational change or alteration results in ubiquitination of said substrate, (ii) assaying for ubiquitination of one or more substrates, and (iii) identifying said one or more ubiquitinated substrates; wherein said substrate is not ubiquitinated by said E3 ubiquitination ligase complex in the absence of said compound. Also provided is a substrate identified by this method. In some embodiments, the conformational change or alteration is as compared to the CMA binding pocket when the CRBN is contacted with a reference compound. In some embodiments, the conformational change or alteration is as compared to the CMA binding pocket of an unbound CRBN (e.g., a CRBN prior to contact with the compound that induce a conformational change or alteration of the properties of the CRBN surface). In some embodiments, a CRBN conformational change is induced. In other embodiments, an alteration of the properties of a CRBN surface are induced. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In another embodiment, the conformational change or alteration is assessed by a method comprising (a) (i) obtaining a first crystal structure of CRBN that is not bound to a reference compound (e.g., a CRBN prior to contact with the test compound), and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure CRBN that is not bound to a reference compound (e.g., a CRBN prior to contact with the test compound); (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In one embodiment, the first three-dimensional structure of CRBN that is not bound to a reference compound has a three-dimensional structure as determined by x-ray diffraction having atomic coordinates set forth in Table 8. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof. In a specific embodiment, the CRBN is further bound to DDB1.

In a twenty-third aspect, provided herein is a method of recruiting a substrate for ubiquitination by a E3 ubiquitination ligase complex comprising CRBN, said method comprising contacting said CRBN with a compound that induces a conformational change of the CRBN (e.g., within the CMA-binding pocket of the CRBN) or alteration of the properties of a CRBN surface (e.g., on an adjacent region of the protein), wherein said CRBN conformational change or alteration results in recruitment and ubiquitination of said substrate; and wherein said substrate is not ubiquitinated by said E3 ubiquitination ligase complex in the absence of said compound. In some embodiments, the induction of the conformational change or alteration is as compared of the CRBN (e.g., the CMA binding pocket of CRBN) or CRBN surface when the CRBN is contacted with a reference compound. In other embodiments, the induction of the conformational change or alteration is as compared of the CRBN (e.g., the CMA binding pocket of CRBN) or CRBN surface when the CRBN is unbound (e.g., prior to contact with the compound). In some embodiments, a CRBN conformational change is induced. In other embodiments, an alteration of the properties of a CRBN surface are induced. In certain embodiments, the conformational change or alteration occurs in a CMA binding pocket of the CRBN. In some embodiments, the conformational change or alteration in said CMA binding pocket has an effect on W380, W386 and/or W400 of CRBN In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

In certain embodiments of the various compositions and methods provided herein, the crystal comprises a full-length CRBN protein. In other embodiments of the various compositions and methods provided herein, the crystal comprises a portion of the CRBN protein. In certain embodiments, the portion of the CRBN protein is a CMA binding domain. That is, in certain embodiments provided herein, methods that comprise obtaining a crystal comprising CRBN and a compound, includes without limitation obtaining a crystal comprising a CMA binding domain (i.e., not the full-length CRBN) and a compound. In some embodiments, the crystal comprises the thalidomide binding domain (TBD) (a type of a CMA-binding domain) of human CRBN (amino acids 319-427). In other embodiments, the crystal comprises the TBD of mouse CRBN (amino acids 322-430). Crystals comprising other CMA-binding domains are also contemplated.

In other embodiments of the various compositions and methods provided herein, the three-dimensional structure comprises a full-length CRBN protein. In other embodiments of the various compositions and methods provided herein, the three-dimensional structure comprises a portion of the CRBN protein. In certain embodiments, the portion of the CRBN protein is a CMA-binding domain. That is, in certain embodiments provided herein, methods that comprise obtaining a three-dimensional structure of a complex comprising CRBN and a compound, includes without limitation obtaining a three-dimensional structure of a complex comprising a CMA binding domain (i.e., not the full-length CRBN) and a compound. In some embodiments, the crystal comprises TBD of human CRBN (amino acids 319-427). In other embodiments, the crystal comprises the TBD of mouse CRBN (amino acids 322-430). Three-dimensional structures comprising other CMA-binding domains are also contemplated.

Exemplary methods of obtaining the crystal structure, e.g., of a CRBN (or a CMA-binding domain thereof), either alone or complexed with a CMA, are provided elsewhere herein.

In certain embodiments of the various compositions and methods provided herein, the atomic coordinates are set forth in Table 3. In other embodiments of the various compositions and methods provided herein, the atomic coordinates are set forth in Table 4. In some embodiments of the various compositions and methods provided herein, the atomic coordinates are set forth in Table 5. In some embodiments of the various compositions and methods provided herein, the atomic coordinates are set forth in Table 6. In some embodiments of the various compositions and methods provided herein, the atomic coordinates are set forth in Table 7.

In certain embodiments of the various compositions and methods provided herein, the three-dimensional structure is reflected by the atomic coordinates set forth in Table 3. In other embodiments of the various compositions and methods provided herein, the three-dimensional structure is reflected by the atomic coordinates set forth in Table 4. In some embodiments of the various compositions and methods provided herein, the three-dimensional structure is reflected by the atomic coordinates set forth in Table 5. In some embodiments of the various compositions and methods provided herein, the three-dimensional structure is reflected by the atomic coordinates set forth in Table 6. In some embodiments of the various compositions and methods provided herein, the three-dimensional structure is reflected by the atomic coordinates set forth in Table 7. In some embodiments of the various compositions and methods provided herein, the three-dimensional structure is reflected by the atomic coordinates set forth in Table 8.

In certain embodiments of the various compositions and methods provided herein, the three-dimensional structure is provided in any one of the figures, including, for example, FIG. 12-18 or 20. In some embodiments of the various compositions and methods provided herein, the three-dimensional structure is provided in FIG. 12. In some embodiments of the various compositions and methods provided herein, the three-dimensional structure is provided in FIG. 13. In some embodiments of the various compositions and methods provided herein, the three-dimensional structure is provided in FIG. 14. In some embodiments of the various compositions and methods provided herein, the three-dimensional structure is provided in FIG. 15. In some embodiments of the various compositions and methods provided herein, the three-dimensional structure is provided in FIG. 16. In some embodiments of the various compositions and methods provided herein, the three-dimensional structure is provided in FIG. 17. In some embodiments of the various compositions and methods provided herein, the three-dimensional structure is provided in FIG. 18. In some embodiments of the various compositions and methods provided herein, the three-dimensional structure is provided in FIG. 20.

We further discovered that recruitment of a CRBN-associated protein (CAP) to CRBN, as well as subsequent degradation of the CAP by CRBN E3 ubiquitin ligase complex, is mediated by the CMA-induced conformational change in CRBN. The CAP recruited to CRBN depends on the specific CMA as well as a degron in the CAP. Based on the degron information, new CAPs can be identified and exploited as potential drug targets for treating various CRBN-related diseases.

As such, we describe herein a variety of degrons in a CAP, structural requirements of the degrons, and critical amino acid residues in the degrons. We also describe methods of identifying a CAP or a target of a treatment compound based on the degron information.

In a twenty-fourth aspect, provided herein is a degron in a CAP, wherein the degron is a structural degron.

In some embodiments, the structural degron comprises an α-turn. In other embodiments, the structural degron comprises a beta-hairpin.

In certain embodiments, the degron comprises 4 amino acid residues, with positions designated as i, i+1, i+2, and i+3, respectively.

In other embodiments, the degron further comprises an amino acid residue at position i−1.

In some embodiments, the amino acid residues at position i, i+1, or i+2 form hydrogen bonds with amino acid residues on CRBN. In one embodiment, the amino acid residue at position i form hydrogen bonds with amino acid residues on CRBN. In another embodiment, the amino acid residue at position i+1 form hydrogen bonds with amino acid residues on CRBN. In yet another embodiment, the amino acid residue at position i+2 form hydrogen bonds with amino acid residues on CRBN. In still another embodiment, the amino acid residues at positions i and i+1 form hydrogen bonds with amino acid residues on CRBN. In one embodiment, the amino acid residues at positions i and i+2 form hydrogen bonds with amino acid residues on CRBN. In another embodiment, the amino acid residues at positions i+1 and i+2 form hydrogen bonds with amino acid residues on CRBN. In yet another embodiment, the amino acid residues at position i, i+1, and i+2 form hydrogen bonds with amino acid residues on CRBN.

In certain embodiments, the amino acid residue at position i+3 is Glycine (G).

In some embodiments, the degron is stabilized by internal hydrogen bonds from an ASX motif and a ST motif.

In certain embodiments, the degron comprises an ASX motif that starts with Aspartic Acid (D). In other embodiments, the degron comprises an ASX motif that starts with Asparagine (N).

In some embodiments, the degron comprises a ST motif that starts with Serine (S). In other embodiments, the degron comprises a ST motif that starts with Threonine (T).

In certain embodiments, the degron comprises an amino acid sequence of [D/N]XX[S/T]G (SEQ ID NO:11), wherein X can be any amino acid residue. In one embodiment, the degron comprises an amino acid sequence of DXXSG (SEQ ID NO:12). In another embodiment, the degron comprises an amino acid sequence of NXXSG (SEQ ID NO:13). In yet another embodiment, the degron comprises an amino acid sequence of DXXTG (SEQ ID NO:14). In still another embodiment, the degron comprises an amino acid sequence of NXXTG (SEQ ID NO:15).

In some embodiments, the degron comprises an amino acid sequence of CXXCG (SEQ ID NO:16), wherein X can be any amino acid residue.

In certain embodiments, the degron comprises an amino acid sequence of NXXNG (SEQ ID NO:17), wherein X can be any amino acid residue.

In some embodiments, the CAP is a substrate of CRBN. In one embodiment, the substrate of CRBN is GSPT1. In another embodiment, the substrate of CRBN is IKZF1.

In yet another embodiment, the substrate of CRBN is CK1a.

In a twenty-fifth aspect, provided herein is a method of identifying a CAP, comprising: (a) searching a protein database for a protein comprising an amino acid sequence of a degron in a CAP; (b) testing the protein in a CRBN-binding assay or ubiquitination assay; and (c) identifying the protein as a CAP if the protein specifically binds to CRBN in the CRBN-binding assay or ubiquitination assay. In some embodiments, the method comprises testing the protein in a CRBN-binding assay. In other embodiments, the method comprises testing the protein in an ubiquitination assay.

In certain embodiments, the CAP is a substrate of CRBN.

In some embodiments, the amino acid sequence of the degron is [D/N]XX[S/T]G (SEQ ID NO:11).

In other embodiments, the amino acid sequence of the degron is CXXCG (SEQ ID NO:16).

In yet other embodiments, the amino acid sequence of the degron is NXXNG (SEQ ID NO:17).

In certain embodiments, the CRBN-binding assay is performed in the presence of a compound.

In some embodiments, the compound is a CMA.

In other embodiments, the compound is an immunomodulatory compound.

In still other embodiments, the compound is selected from the group consisting of thalidomide, lenalidomide, pomalidomide, Compound A, Compound B, Compound C, Compound D, and Compound E. In one embodiment, the compound is thalidomide. In another embodiment, the compound is lenalidomide. In yet another embodiment, the compound is pomalidomide. In still another embodiment, the compound is Compound A. In one embodiment, the compound is Compound B. In another embodiment, the compound is Compound C. In yet another embodiment, the compound is Compound D. In still another embodiment, the compound is Compound E.

In a twenty-sixth aspect, provided herein is a method of identifying a CAP, comprising: (a) searching a protein database for a protein comprising an amino acid sequence of a degron in a CAP; (b) testing the protein in a CRBN-mediated degradation assay, ubiquitination assay or proteomics experiment; and (c) identifying the protein as a CAP if the protein level decreases in the CRBN-mediated degradation assay, ubiquitination assay or proteomics experiments. In some embodiments, the method comprises testing the protein in a CRBN-mediated degradation assay. In other embodiments, the method comprises testing the protein in an ubiquitination assay. In yet other embodiments, the method comprises testing the protein in a proteomics experiment.

In certain embodiments, the CAP is a substrate of CRBN.

In some embodiments, the amino acid sequence of the degron is [D/N]XX[S/T]G (SEQ ID NO:11).

In other embodiments, the amino acid sequence of the degron is CXXCG (SEQ ID NO:16).

In yet other embodiments, the amino acid sequence of the degron is NXXNG (SEQ ID NO:17).

In certain embodiments, the CRBN-binding assay is performed in the presence of a compound.

In some embodiments, the compound is a CMA.

In other embodiments, the compound is an immunomodulatory compound.

In still other embodiments, the compound is selected from the group consisting of thalidomide, lenalidomide, pomalidomide, Compound A, Compound B, Compound C, Compound D, and Compound E. In one embodiment, the compound is thalidomide. In another embodiment, the compound is lenalidomide. In yet another embodiment, the compound is pomalidomide. In still another embodiment, the compound is Compound A. In one embodiment, the compound is Compound B. In another embodiment, the compound is Compound C. In yet another embodiment, the compound is Compound D. In still another embodiment, the compound is Compound E.

In a twenty-seventh aspect, provided herein is a method of identifying a target of a compound comprising: (a) searching a protein database for a protein comprising an amino acid sequence of a degron in a CAP; (b) testing the protein in a CRBN-binding assay or ubiquitination assay in the presence of the compound; and (c) identifying the protein as the target of the compound if the protein specifically binds to CRBN in the CRBN-binding assay or ubiquitination assay. In some embodiments, the method comprises testing the protein in a CRBN-binding assay in the presence of the compound. In other embodiments, the method comprises testing the protein in an ubiquitination assay in the presence of the compound.

In certain embodiments, the CAP is a substrate of CRBN.

In some embodiments, the amino acid sequence of the degron is [D/N]XX[S/T]G (SEQ ID NO:11).

In other embodiments, the amino acid sequence of the degron is CXXCG (SEQ ID NO:16).

In yet other embodiments, the amino acid sequence of the degron is NXXNG (SEQ ID NO:17).

In some embodiments, the compound is a CMA.

In other embodiments, the compound is an immunomodulatory compound.

In still other embodiments, the compound is selected from the group consisting of thalidomide, lenalidomide, pomalidomide, Compound A, Compound B, Compound C, Compound D, and Compound E. In one embodiment, the compound is thalidomide. In another embodiment, the compound is lenalidomide. In yet another embodiment, the compound is pomalidomide. In still another embodiment, the compound is Compound A. In one embodiment, the compound is Compound B. In another embodiment, the compound is Compound C. In yet another embodiment, the compound is Compound D. In still another embodiment, the compound is Compound E.

In a twenty-eighth aspect, provided herein is a method of identifying a target of a compound comprising: (a) searching a protein database for a protein comprising an amino acid sequence of a degron in a CAP; (b) testing the protein in a CRBN-mediated degradation assay, ubiquitination assay, or proteomics experiment in the presence of the compound; and (c) identifying the protein as the target of the compound if the protein level decreases in the CRBN-mediated degradation assay, ubiquitination assay, or proteomics experiment. In some embodiments, the method comprises testing the protein in a CRBN-mediated degradation assay in the presence of the compound. In other embodiments, the method comprises testing the protein in an ubiquitination assay in the presence of the compound. In yet other embodiments, the method comprises testing the protein in a proteomics experiment in the presence of the compound.

In certain embodiments, the CAP is a substrate of CRBN.

In some embodiments, the amino acid sequence of the degron is [D/N]XX[S/T]G (SEQ ID NO:11).

In other embodiments, the amino acid sequence of the degron is CXXCG (SEQ ID NO: 16).

In yet other embodiments, the amino acid sequence of the degron is NXXNG (SEQ ID NO:17).

In some embodiments, the compound is a CMA.

In other embodiments, the compound is an immunomodulatory compound.

In still other embodiments, the compound is selected from the group consisting of thalidomide, lenalidomide, pomalidomide, Compound A, Compound B, Compound C, Compound D, and Compound E. In one embodiment, the compound is thalidomide. In another embodiment, the compound is lenalidomide. In yet another embodiment, the compound is pomalidomide. In still another embodiment, the compound is Compound A. In one embodiment, the compound is Compound B. In another embodiment, the compound is Compound C. In yet another embodiment, the compound is Compound D. In still another embodiment, the compound is Compound E.

In a twenty-ninth aspect, provided herein is a method of identifying a CAP or a target of a compound comprising: searching for a protein that has a region of structural similarity to a degron region provided herein.

In some embodiments, provided herein is a method of identifying a CAP, comprising: (a) searching for a protein comprising a region having a similar structure of a degron in a known CAP; (b) testing the protein in a CRBN-binding assay or ubiquitination assay; and (c) identifying the protein as a CAP if the protein specifically binds to CRBN in the CRBN-binding assay or ubiquitination assay.

In other embodiments, provided herein is a method of identifying a CAP, comprising: (a) searching for a protein comprising a region having a similar structure of a degron in a known CAP; (b) testing the protein in a CRBN-mediated degradation assay, ubiquitination assay or proteomics experiment; and (c) identifying the protein as a CAP if the protein level decreases in the CRBN-mediated degradation assay, ubiquitination assay or proteomics experiment.

In yet other embodiments, provided herein is a method of identifying a target of a compound comprising: (a) searching for a protein comprising a region having a similar structure of a degron in a known CAP; (b) testing the protein in a CRBN-binding assay or ubiquitination assay in the presence of the compound; and (c) identifying the protein as the target of the compound if the protein specifically binds to CRBN in the CRBN-binding assay or ubiquitination assay.

In yet other embodiments, provided herein is a method of identifying a target of a compound comprising: (a) searching for a protein comprising a region having a similar structure of a degron in a known CAP; (b) testing the protein in a CRBN-mediated degradation assay, ubiquitination assay or proteomics experiment in the presence of the compound; and (c) identifying the protein as the target of the compound if the protein level decreases in the CRBN-mediated degradation assay, ubiquitination assay or proteomics experiment.

In some embodiments of the various methods provided herein, the method comprises computationally searching for a protein based on the structural similarity to a degron provided herein. In one embodiment, the method provided herein comprises searching for a degron or a similar structure on the surface of proteins of known structure. In another embodiment, the method provided herein comprises searching for a similar structural feature to the known degron on the surface of proteins of known structure. In yet another embodiment, the method provided herein comprises searching for a glycine on the surface of proteins of known structure.

In certain embodiments, the CAP is a substrate of CRBN.

In some embodiments, the amino acid sequence of the degron is [D/N]XX[S/T]G (SEQ ID NO:11).

In other embodiments, the amino acid sequence of the degron is CXXCG (SEQ ID NO:16).

In yet other embodiments, the amino acid sequence of the degron is NXXNG (SEQ ID NO:17).

In certain embodiments, the CRBN-binding assay is performed in the presence of a compound.

In some embodiments, the compound is a CMA.

In other embodiments, the compound is an immunomodulatory compound.

In still other embodiments, the compound is selected from the group consisting of thalidomide, lenalidomide, pomalidomide, Compound A, Compound B, Compound C, Compound D, and Compound E. In one embodiment, the compound is thalidomide. In another embodiment, the compound is lenalidomide. In yet another embodiment, the compound is pomalidomide. In still another embodiment, the compound is Compound A. In one embodiment, the compound is Compound B. In another embodiment, the compound is Compound C. In yet another embodiment, the compound is Compound D. In still another embodiment, the compound is Compound E.

In a thirtieth aspect, provided herein is a method of identifying a CAP or a target of a compound comprising: searching for a protein able to bind to a surface of CRBN adjacent to the site of ligand binding via features other than the known degron, e.g., by performing docking studies.

In some embodiments of the various methods provided herein, the method further comprises searching for proteins homologous to the proteins with the degron structure or predicted to have ability to bind CRBN.

4. BRIEF DESCRIPTION OF THE DRAWINGS

Figure 3:
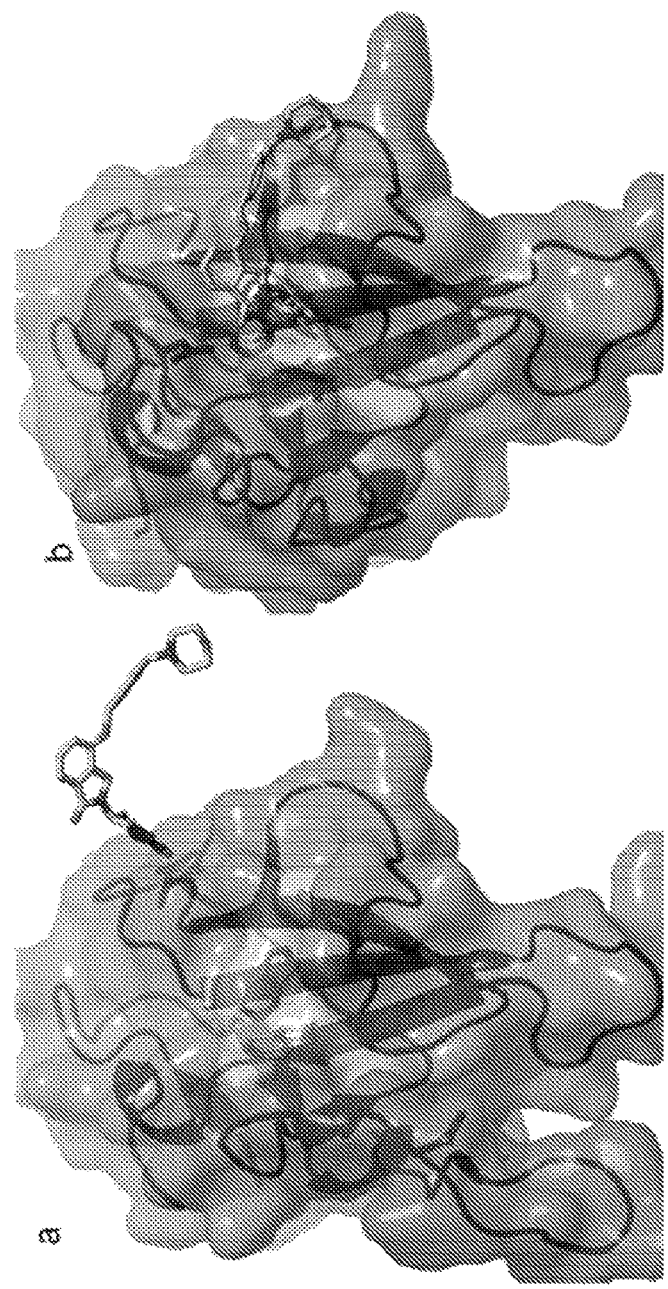

FIGS. 3A-B depicts the crystal structure of Compound B in CRBN, in which the drug can act as a "molecular glue" or bridge with a substrate, such as a CRBN-associated protein. (A) Unbound mouse CRBN prior to Compound B binding, and (B) mouse CRBN in complex with Compound B.

Figure 4:
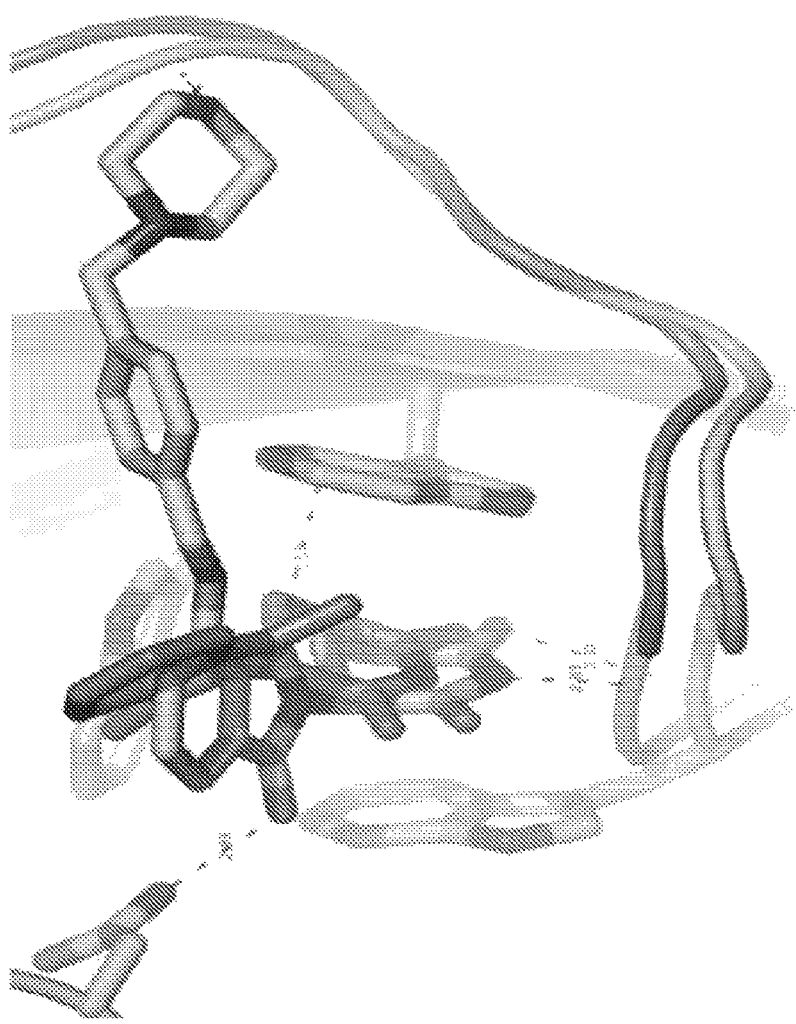

FIG. 4 depicts a complex of CRBN and Compound B or thalidomide, and a 50° rotation of "pthalimide" ring in Compound B relative to thalidomide or pomalidomide is observed.

FIGS. 5A-B depict lenalidomide competes with Compound A and Compound C for CRBN. (A) and (B) Co-treatment of lenalidomide with either Compound A or Compound C blocks the anti-proliferative effects of either drug through competition of binding to the CRBN complex in both ABC and GCB DLBCL. Co-culture of Lenalidomide with either Compound A or Compound C dampens the activity of these compounds as they target the same binding pocket with relative affinity.

Figure 6:
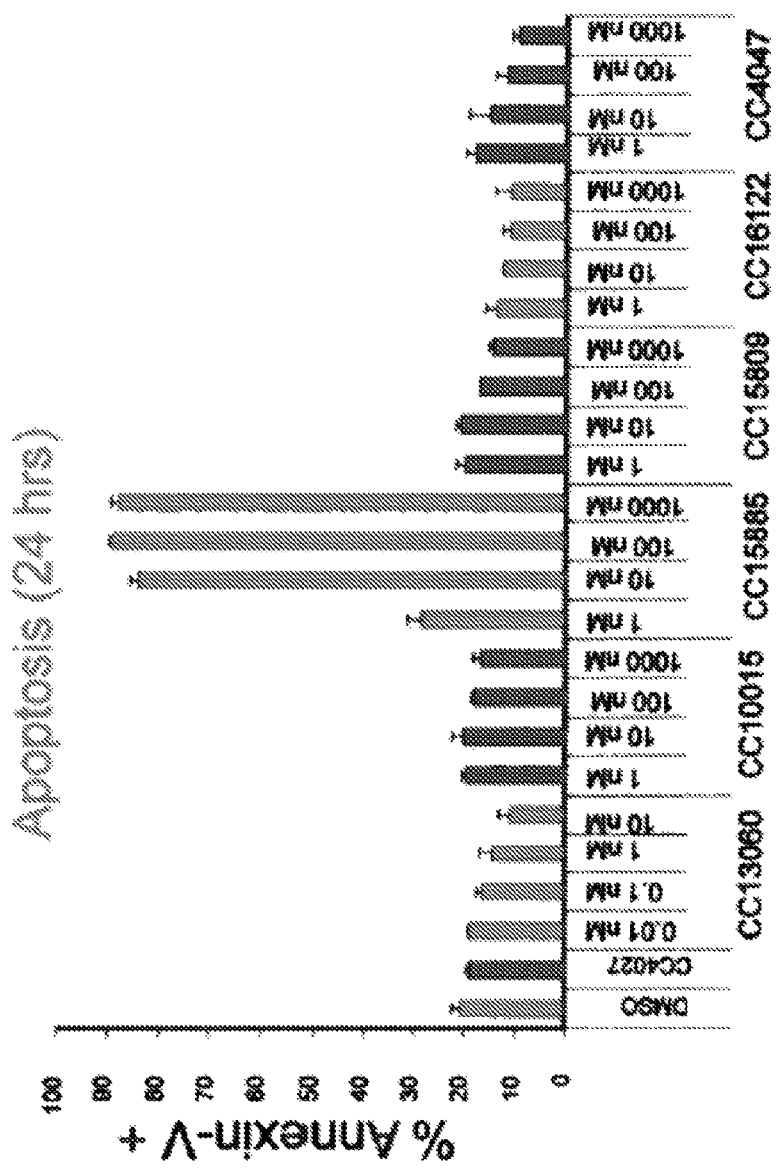

FIG. 6 shows that Compound C induced early apoptosis in the multiple myeloma (MM) cell line H929.

Figure 7:
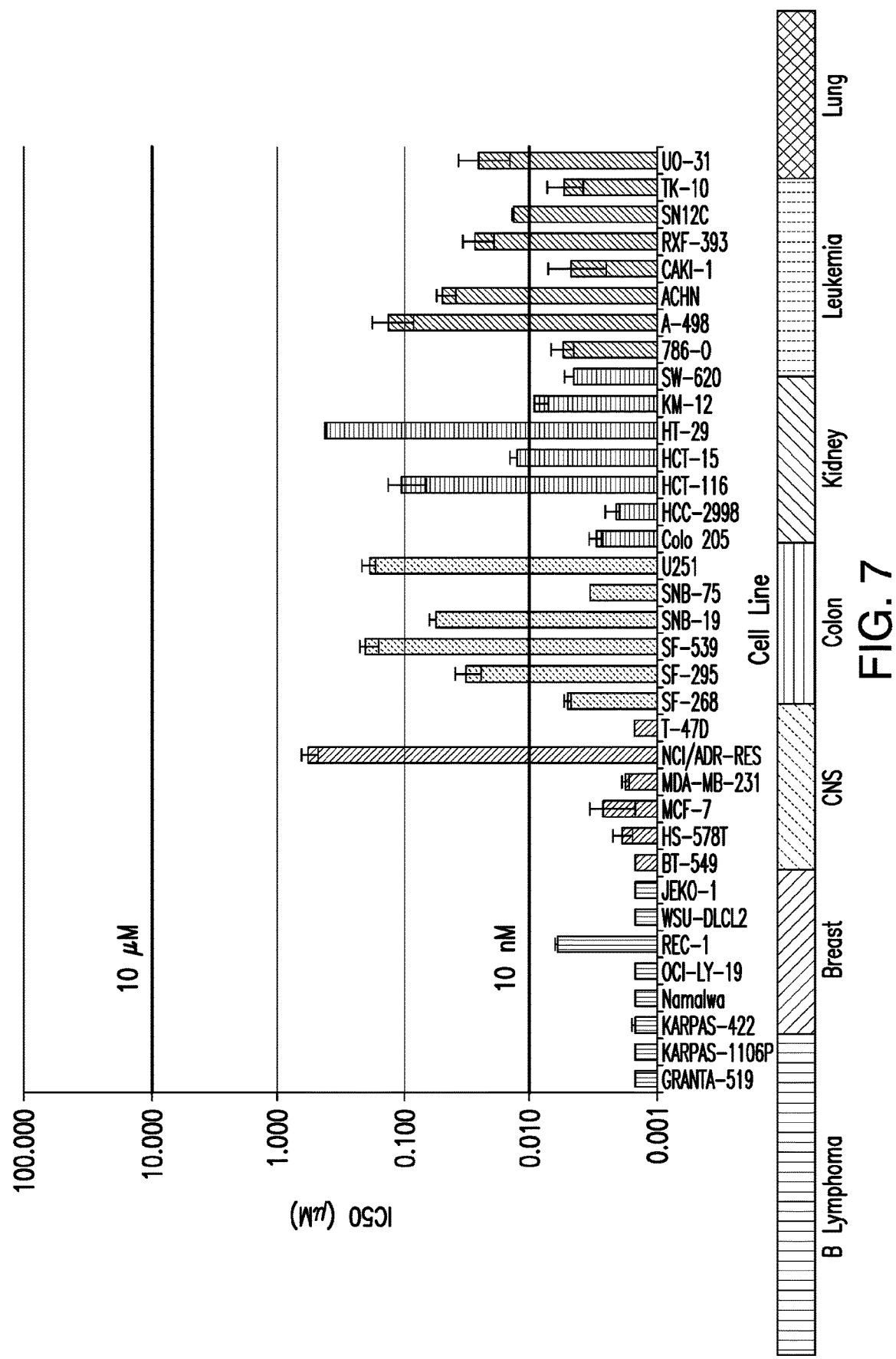

FIG. 7 shows that Compound C is potent across a panel of solid tumor lines.

Figure 8:
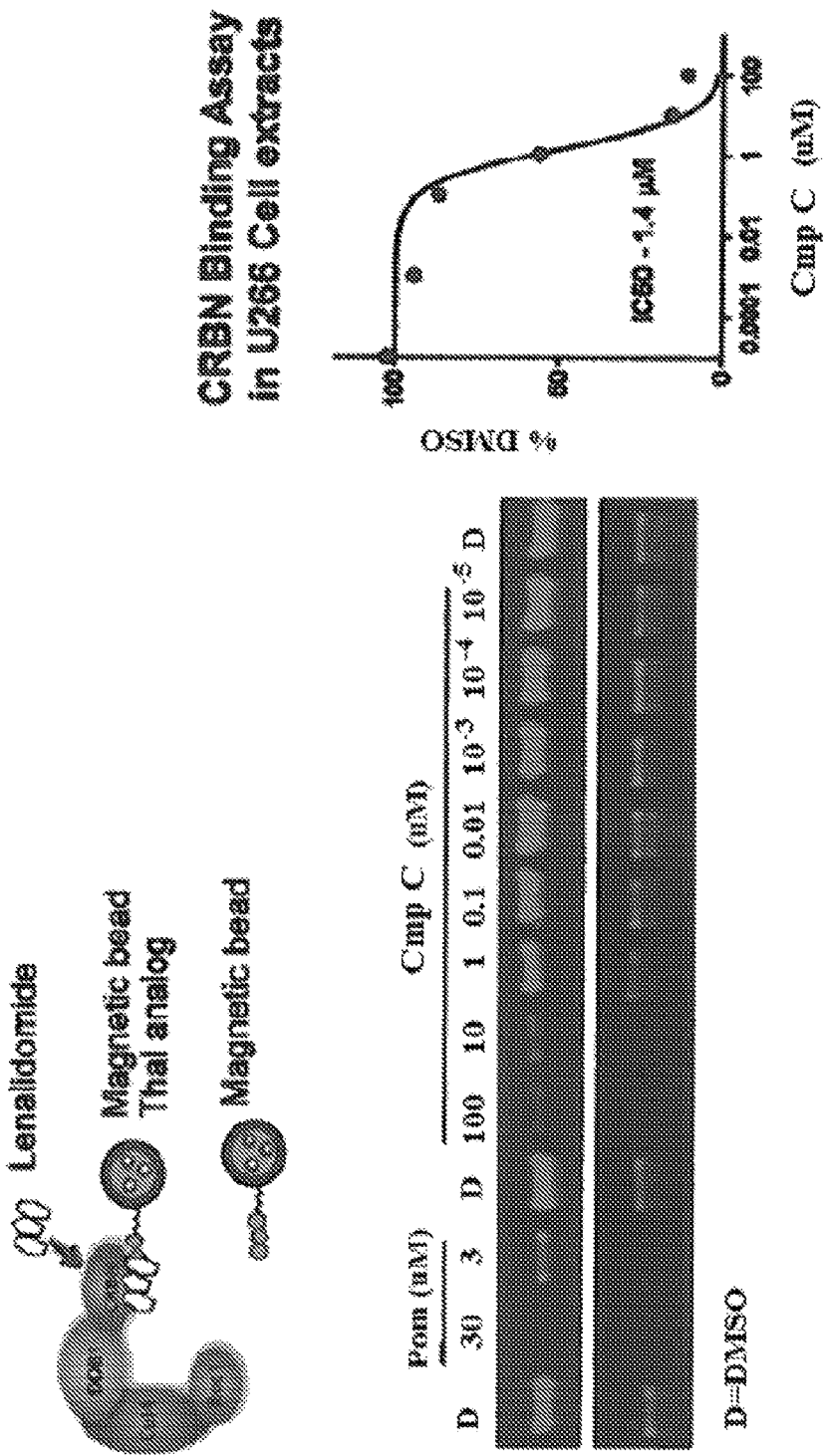

FIG. 8 shows that Compound C binds CRBN protein MM cell extracts.

Figure 9:
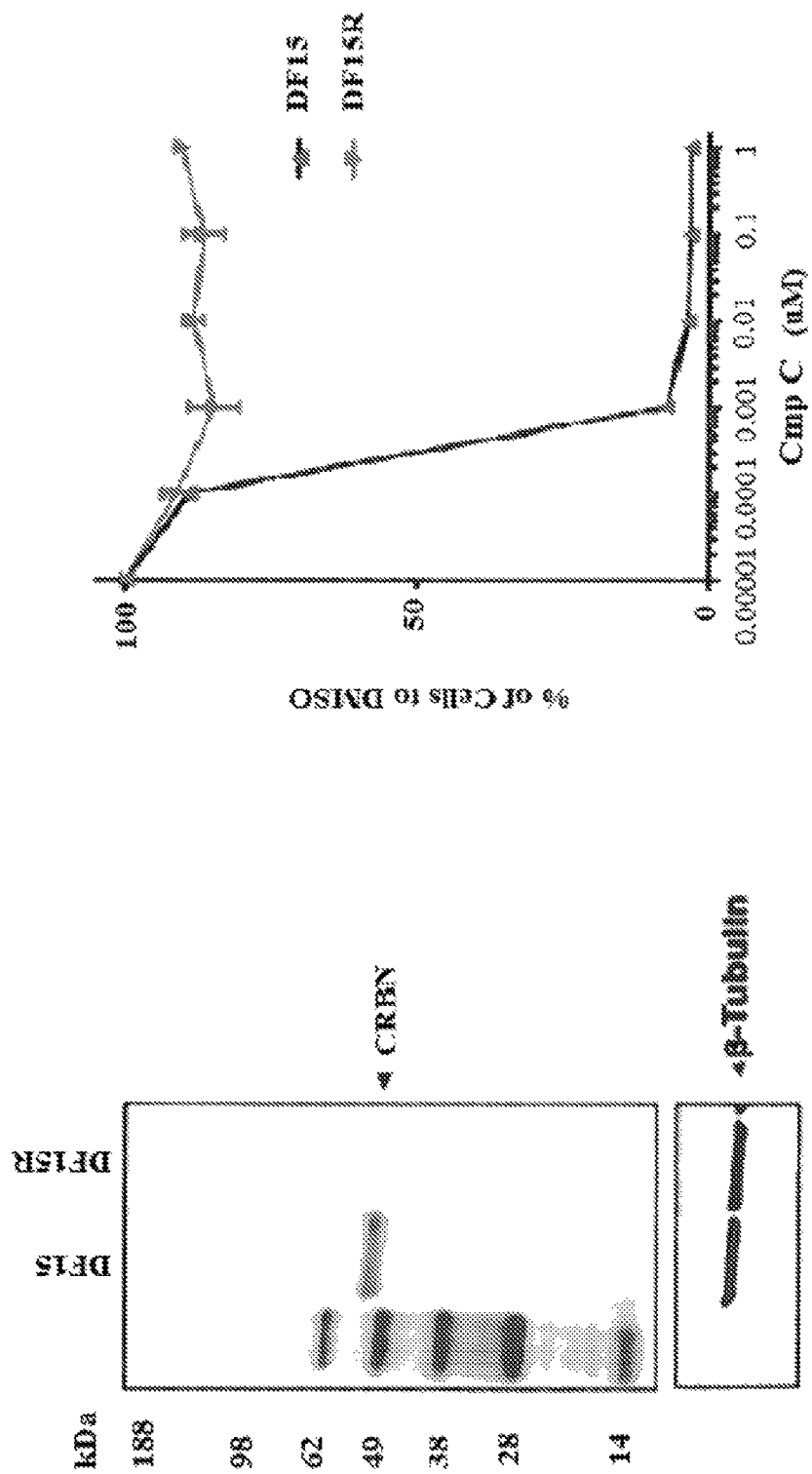

FIG. 9 shows that CRBN is required for the anti-proliferative activity of Compound C in myeloma cells.

Figure 10:
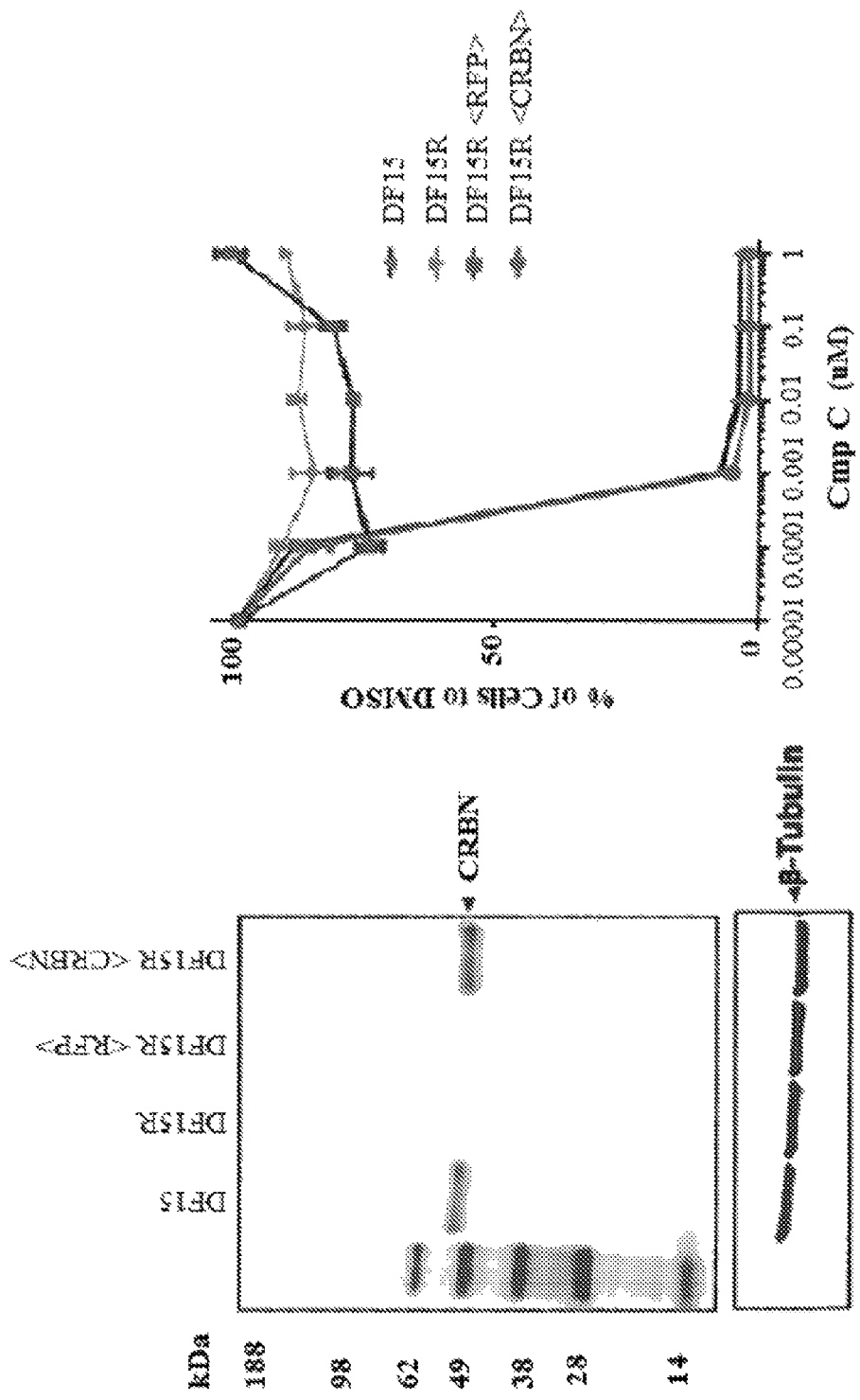

FIG. 10 shows that CRBN is required for the anti-proliferative activity of Compound C in myeloma cells.

Figure 11:
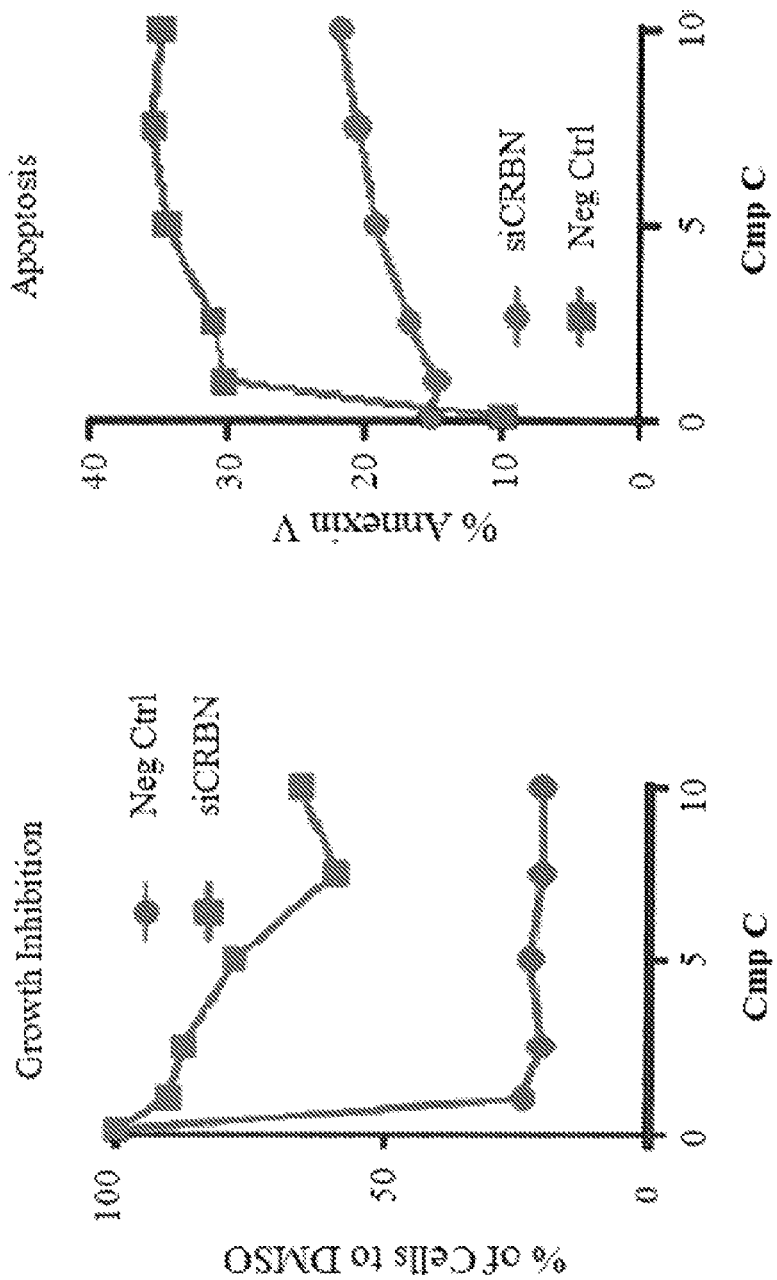

FIG. 11 shows that CRBN is required for both growth inhibition and pro-apoptotic activity of Compound C in the MDA-MB-213 breast cancer cells.

Figure 12:
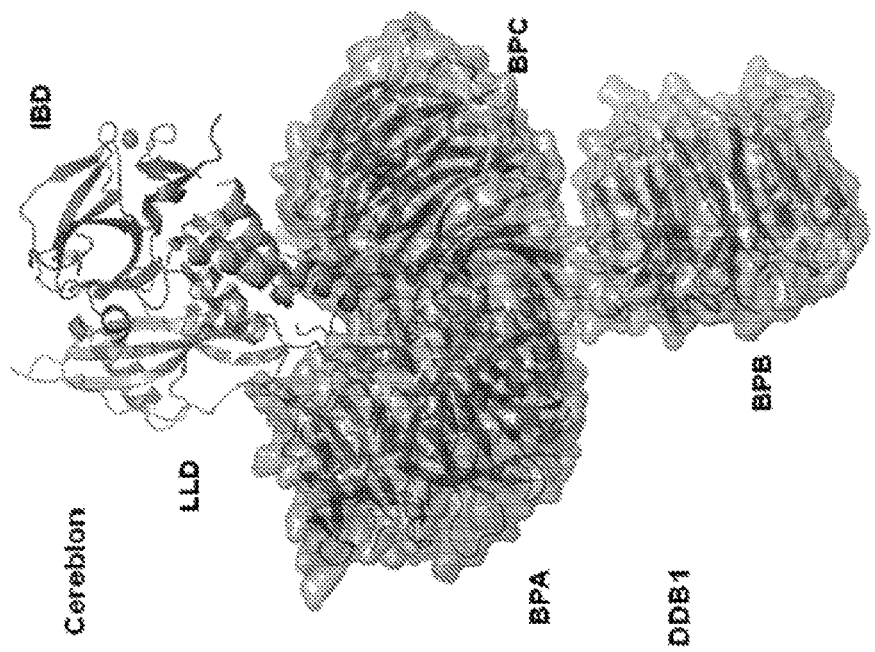

FIG. 12 shows the structure of human cereblon in complex with human DDB1. Lenalidomide binds the thalidomide binding domain (TBD; sometimes also referred to as immunomodulatory agent-binding domain (IBD) herein) (a type of CMA-binding domain) on the opposing face to the DDB1 binding motif. The Cereblon Lon-like domain (LLD) is shown in yellow. The TBD is shown in blue with the region deleted in a human polymorphism shown in red. DDB1 is shown in green with a grey surface. The DDB1 beta propeller domains are labeled BPA, BPB and BPC. Lenalidomide is shown as yellow sticks, and the zinc ion as a grey sphere.

Figure 13:
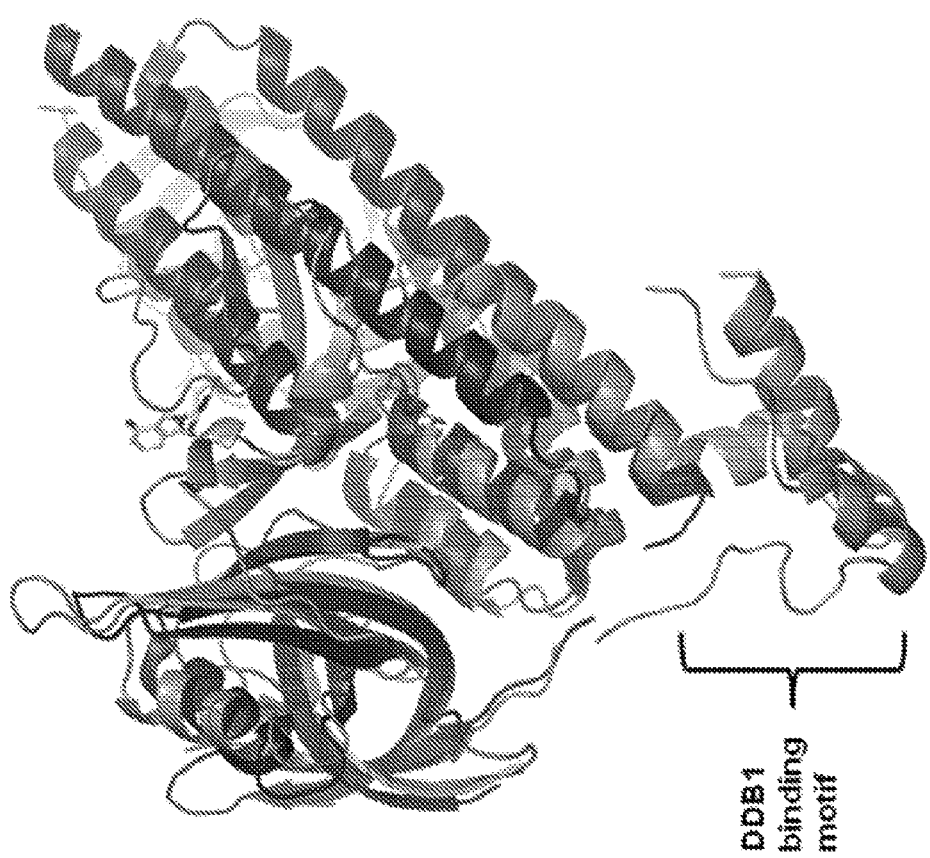

FIG. 13 shows the structural superposition of cereblon with *Bacillus subtilis* lon protease (red, PDB code 3M65). The cereblon lon-like domain (LLD) is shown in yellow and the TBD is shown in blue. The DDB1 binding motif is inserted into the LLD, while the TBD exhibits no similarity to lon protease and occurs at the C-terminus.

Figure 14:
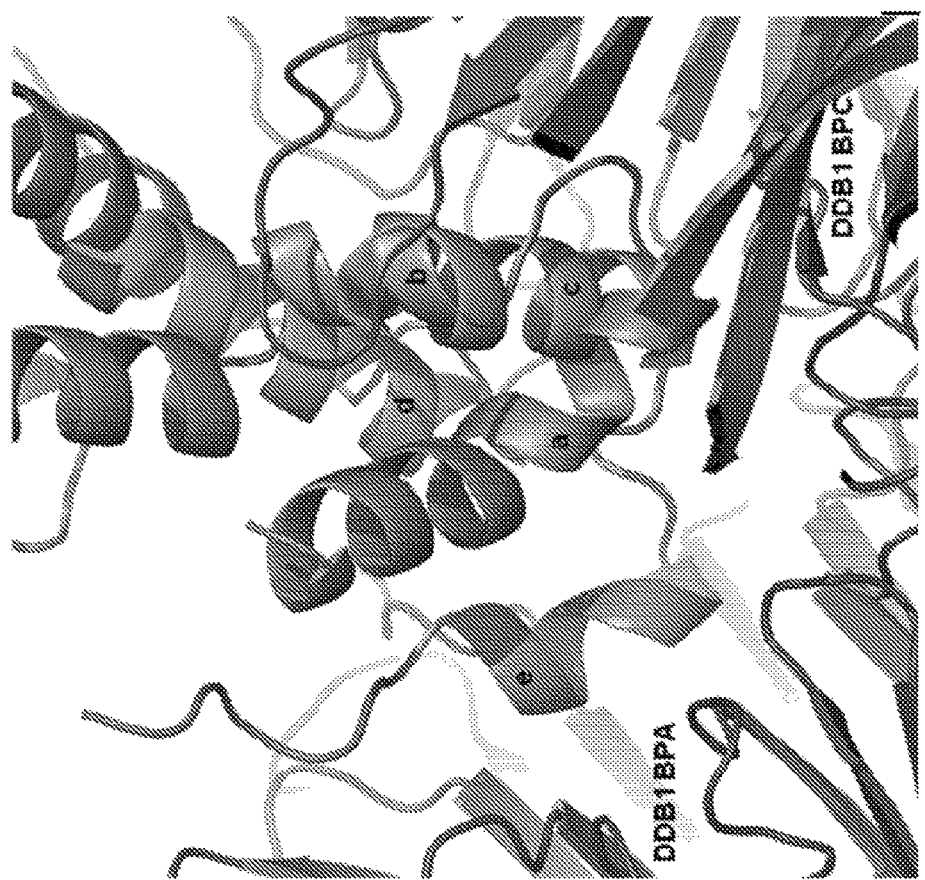

FIG. 14 shows the structural superposition of cereblon: DDB1 (yellow and green, respectively) with DDB2:DDB1 (DDB2 shown in blue, DDB1 omitted). DDB1-binding is typically mediated by a helix-turn-helix motif such as helices c and d, which interact with the DDB1 beta-propellar C (BPC) domain. CRBN makes interactions with DDB1 BPC, but also places helix e to interact with the DDB1 beta-propeller A (BDA) domain.

Figure 15:
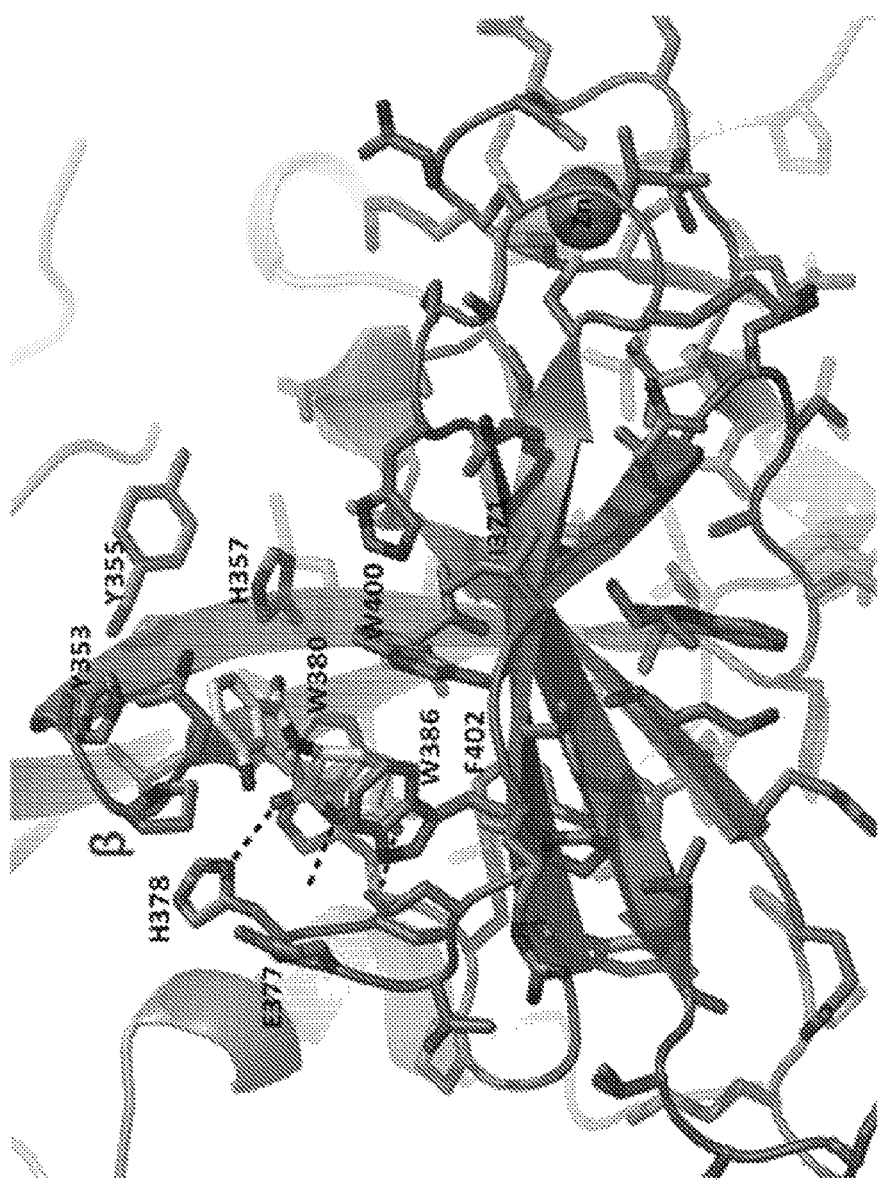

FIG. 15 shows the TBD of human cereblon. The immunomodulatory agent binding domain is shown in blue, lenalidomide is shown in yellow sticks, the Lon-like domain is shown in the background in yellow. The immunomodulatory agent binding pocket is composed of 3 tryptophan residues: W380, W386 and W400. Three hydrogen bonds between the TBD and lenalidomide are shown as a dotted line to the protein backbone at H378 and W380 and to the sidechain of H378. The zinc binding site is shown as a grey sphere, and is approximately 18 Å from lenalidomide. The beta sheet region which varies in the other structures is marked by a 'β'.

Figure 16:
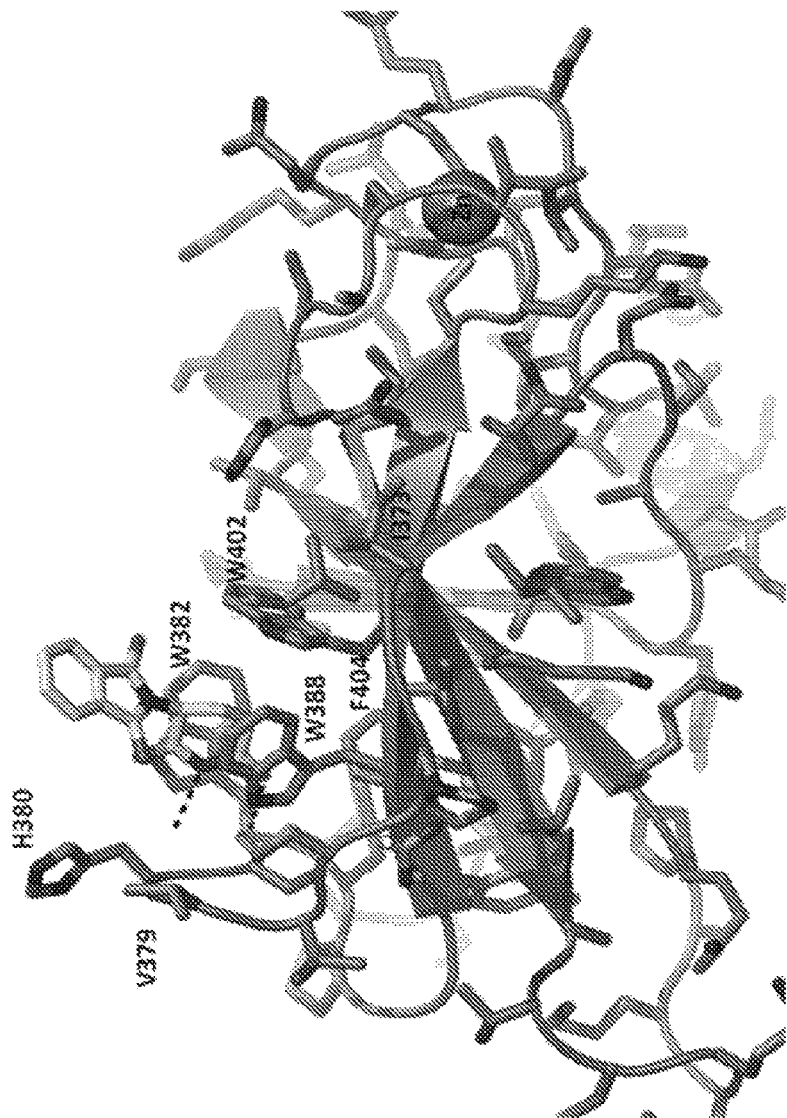

FIG. 16 shows the murine TBD in complex with thalidomide.

Figure 17:
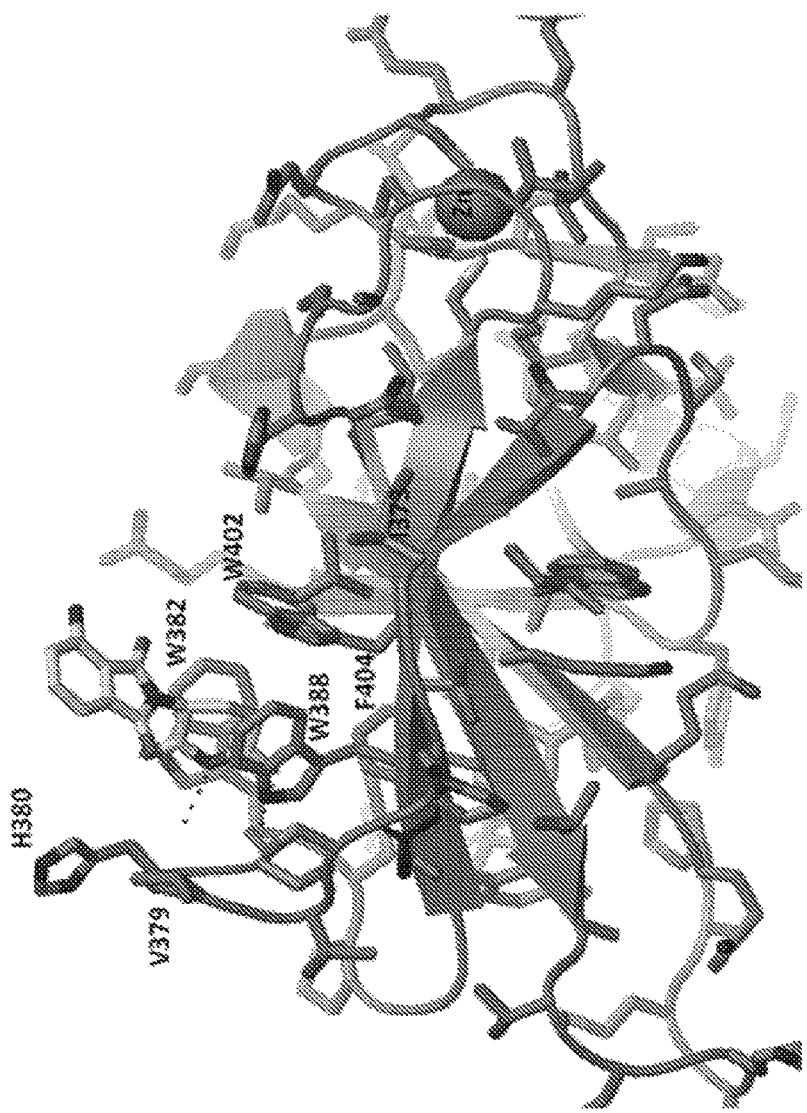

FIG. 17 shows the murine TBD in complex with pomalidomide.

Figure 18:

FIG. 18 shows the structural superposition of cereblon TBD (blue) with methionine sulfoxide reductase (green) and RIG-I (magenta).

Figure 19:
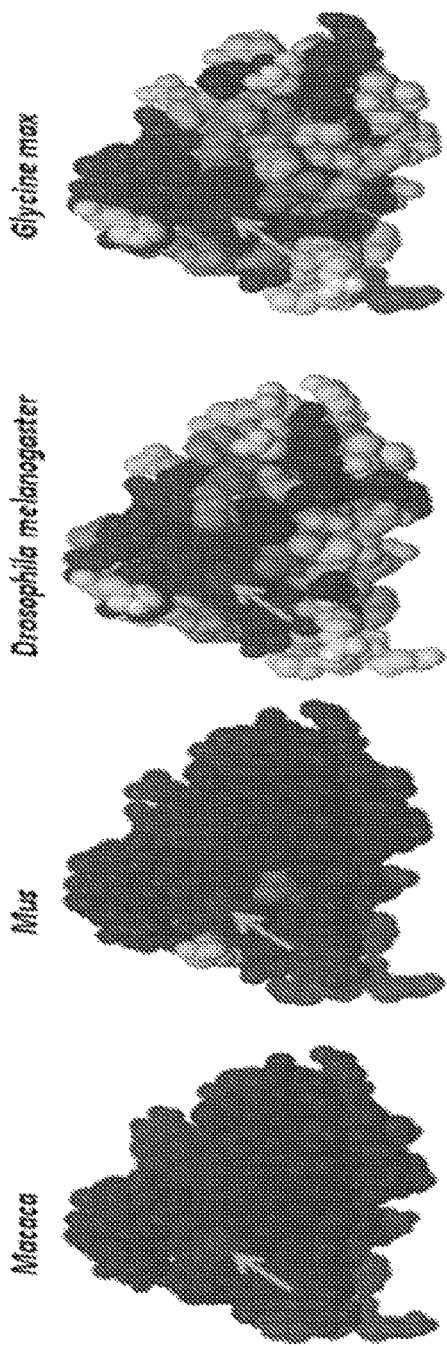

FIG. 19 shows the sequence alignment differences mapped onto the surface of the immunomodulatory agent-binding domain of cereblon. Conserved residues relative to the human protein are shown in red, conservative changes are shown in orange, nonconservative changes are shown in white. The immunomodulatory agent binding pocket is indicated by a blue arrow. Tryptophan residues directly involved in immunomodulatory agent binding are shown in bold in the sequence alignment. The immunomodulatory agent-binding pocket demonstrates extremely high conservation across plant and animal kingdoms. Homo: SEQ ID NO:1, Macaca: SEQ ID NO:1, Mus: SEQ ID NO:2, Rattus: SEQ ID NO:2, Drosophila melanogaster: SEQ ID NO:3, and Glycine max: SEQ ID NO:4.

Figure 20:
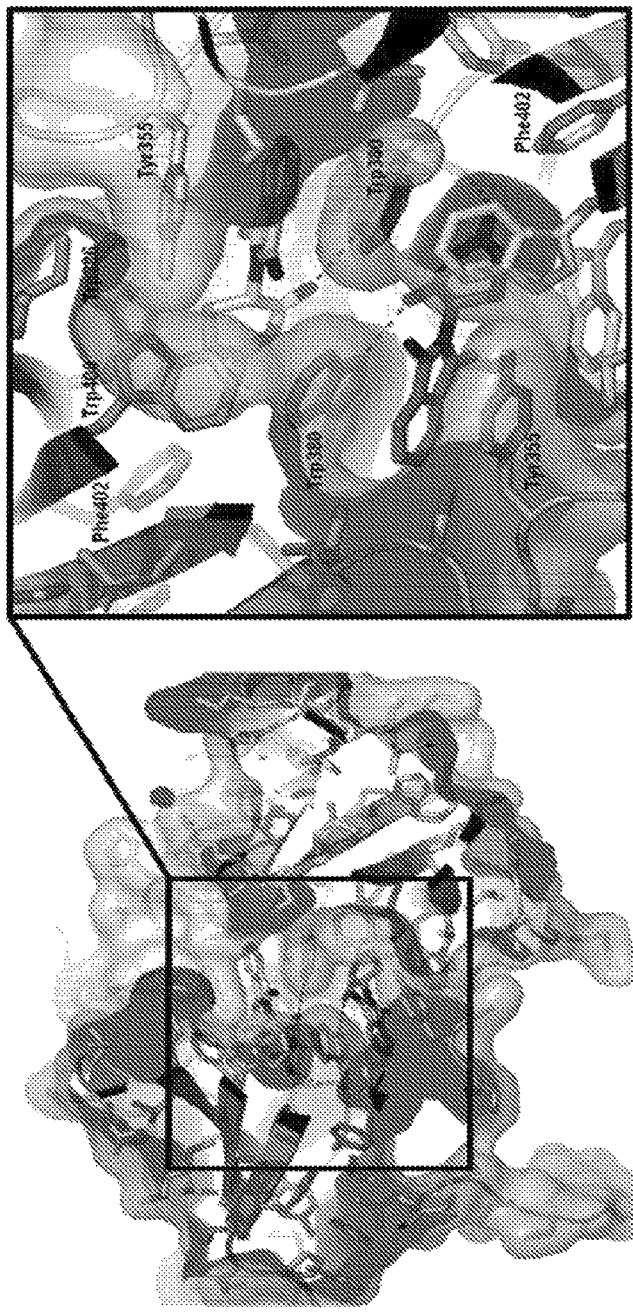

FIG. 20 shows the TBD of murine cereblon showing the crystal contacts formed between protein monomers, bridged by thalomide molecules.

Figure 21:
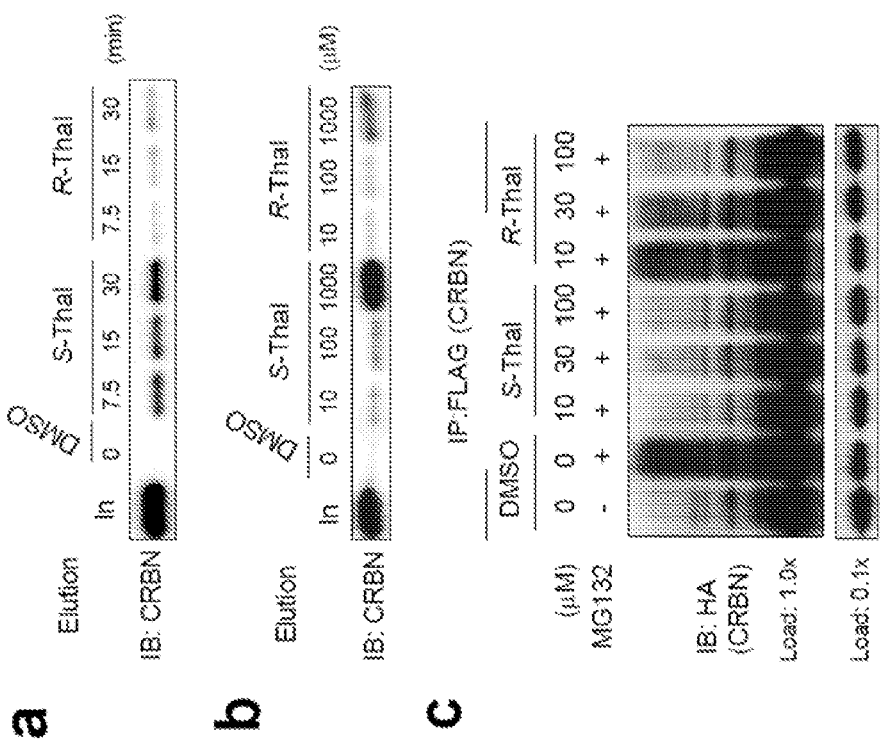

FIGS. 21A-21C shows a CRBN-binding assay with thalidomide enantiomers. (A) Competitive elution assay using thalidomide-immobilized beads coupled with racemic thalidomide. Beads were washed three times with 0.5% NP-40 lysis buffer and bound proteins were eluted with wash buffer containing 1 mM S-, R-thalidomide (S-Thal or R-Thal) or 0.1% DMSO for the indicated time. The eluate was then analyzed by SDS-PAGE and immunoblotting (IB). (B) Same as A, but eluted with a buffer solution containing the indicated concentrations of S- or R-thalidomide (S- or R-Thal). (C) Inhibitory effects of thalidomide enantiomers on auto-ubiquitylation of FH-CRBN was detected in the presence of MG132. Cells were treated with DMSO or the indicated concentrations of S- or R-thalidomide for 4 hours prior to harvesting.

Figure 22:
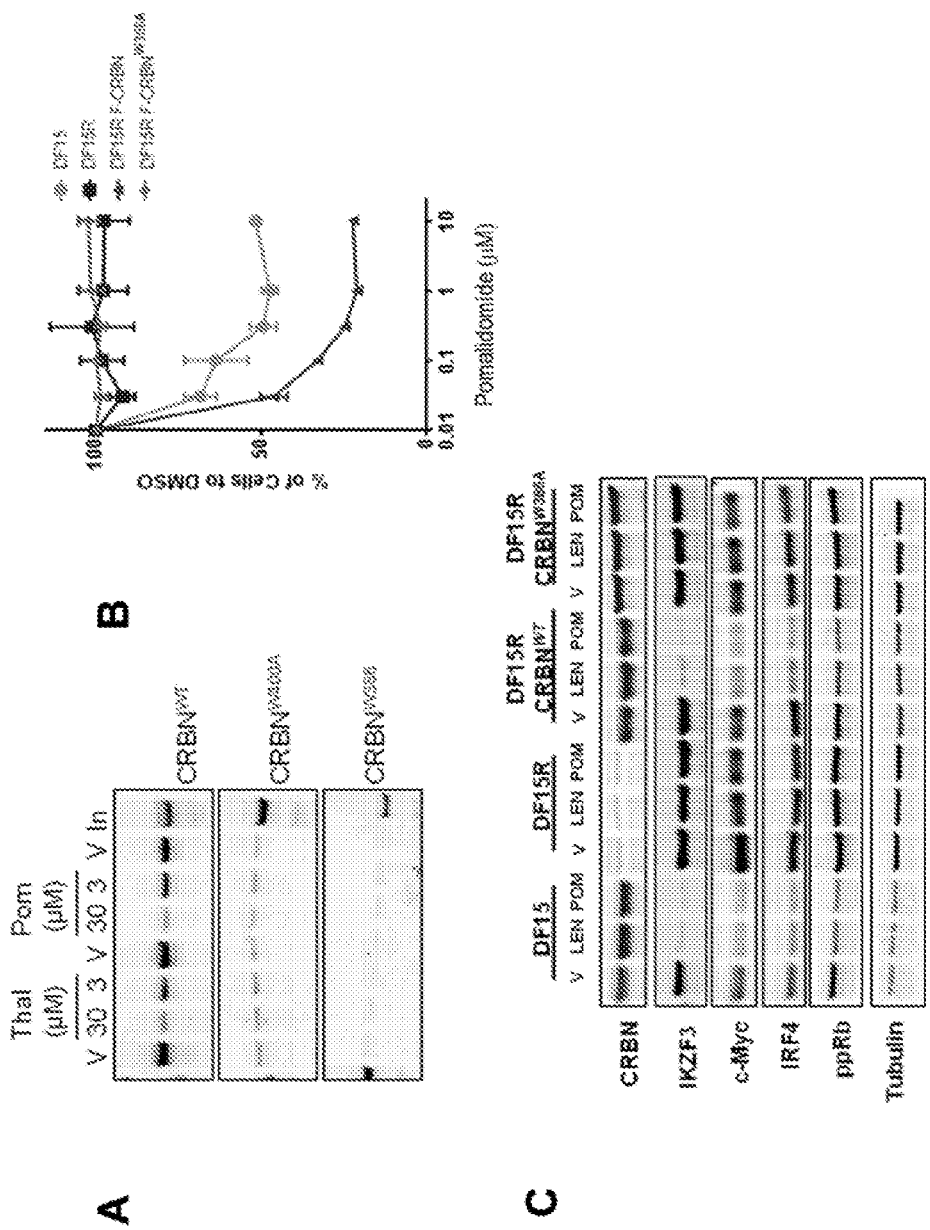

FIG. 22 shows Phylogenetically conserved tryptophan residues (W386 and W400) confer binding of CRBN to immunomodulatory agent and are required for immunomodulatory agent function in vivo. (A) Cell lines re-expressing full-length CRBN wild-type. W386A or W400A mutants were tested for the ability to bind immunomodulatory agent compounds. Assay was repeated at least three times. Representative Western blot of representative experiment is shown. (B) Cell proliferation assay of DF15 (sensitive). DF15R (resistant; $CRBN^{null}$), CRBNWT, CRBNW386A; CRBN400 cells treated with a dose response of pomalidomide. Assays were done in triplicate and error bars representative s.d. Data for each cell line was normalized to treatment with vehicle (DMSO). (C) Western blots of key downstream effectors of immunomodulatory agent resistance.

FIGS. 23A-23B shows the effects of E377V mutation on CRBN activity in vivo. (A) Cell lines re-expressing RFP or full length CRBN wild type or E377V mutant were tested for the ability of CRBN proteins to bind immunomodulatory agent compounds. Assay was repeated at least three times. Representative Western blot of representative experiment is shown. (B) Cell proliferation assay of DF15 (sensitive), DF15R (resistant; $CRBN^{null}$), $CRBN^{WT}$, $CRBN^{E377V}$ cells treated with a dose response of pomalidomide. Assays were done in triplicate and error bars represent s.d. Data for each cell line was normalized to treatment with vehicle (DMSO). The insert shows Western blots of Aiolos and β-actin.

FIGS. 24A-24D shows CRBN in lysates from DF15. (A) Immunoblot analysis of CRBN in lysates from DF15, DF15R, DF15R RFP (RFP ctrl), DF15R $CRBN^{WT}$ (CRBN wt), DF15R $CRBN^{W386A}$ and $CRBN^{W400A}$ cells. (B) CRBN analysis in DF15 and DF15R and DF15R-derived cell lines by immunohistochemistry confocal microscopy. Images were obtained using a Nikon E800 confocal microscope at a 40× magnification. CRBN signal is shown in cytoplasm and nucleus of the calls. DAPI staining identifies the nucleus of cells (darker staining). (C) Immunoblot of anti-FLAG immunoprecipitation from cell extracts using FLAG-tagged CRBN proteins. (D) Immunoblot of thalidomide analog affinity bead binding to CRBN in DF15, DF15R and DF15R $CRBN^{WT}$ cell extracts. Lane description in order (left to right): In=DF15 input prior to bead purification; V=DF15 extract control (1% DMSO preincubation); Len=DF15R extract preincubated with lenalidomide (30 μM); Pom=DF15R extract preincubated with pomalidomide (30 μM); In=DF15R $CRBN^{WT}$ input prior to bead purification; V=DF15R $CRBN^{WT}$ control (1% DMSO preincubation); Len=DF15R $CRBN^{WT}$ extract preincubated with lenalidomide (30 μM); Pom=DF15R $CRBN^{WT}$ extract preincubated with pomalidomide (30 μM) Representative immunoblot from two independent experiments with similar results are shown.

FIGS. 25A-25F show that CRBN inducible-knockdown cells had a dose and time dependent shRNA induction as measured by an increase in the percentage of RFP positive cells. (A) An inducible shRNA construct targeting CRBN or a control construct was transduced into the multiple myeloma cell lines H929 and U266. Inducible shRNA expression (marked by turbo-RFP) was monitored by flow cytometry over a period of 1 to 9 days as indicated in the histograms (Top row). Annexin V assay staining demonstrated that following induction with doxycycline treatment, CRBN inducible-knockdown did not result in cell death (A Bottom row & C). (B) CRBN protein expression was quantified by Western blotting. CRBN inducible-knockdown cells showed no significant changes in IRF4 or actin protein levels. (C) Following doxycycline treatment, CRBN inducible-knockdown in H929 and U266 cells showed no effect in viability as measured by Annexin V+7AAD staining and analyzed by flow cytometry over a period of 1-9 days. (D)-(F) After 9 days of shRNA inducible knock-down, cells were treated with increasing doses of pomalidomide and compound effect in cell viability was assayed by flow cytometry after 5 day treatment. In CRBN inducible knockdown cells, pomalidomide had reduced anti-proliferative effects compared to shControl knockdown cells. Data are shown as mean of three independent experiments±s.d.

FIG. 26 shows IL2 costimulation by pomalidomide. (A) Co-stimulation of IL2 release by pomalidomide in human PBMCs treated with anti-CD3. Data are shown as mean±s.d. (B) Costimulation of IL2 release by anti-CD28 (squares) or pomalidomide (circles) in mouse PBMC treated with anti-CD3. Data are shown as mean±s.d.

Figure 27:
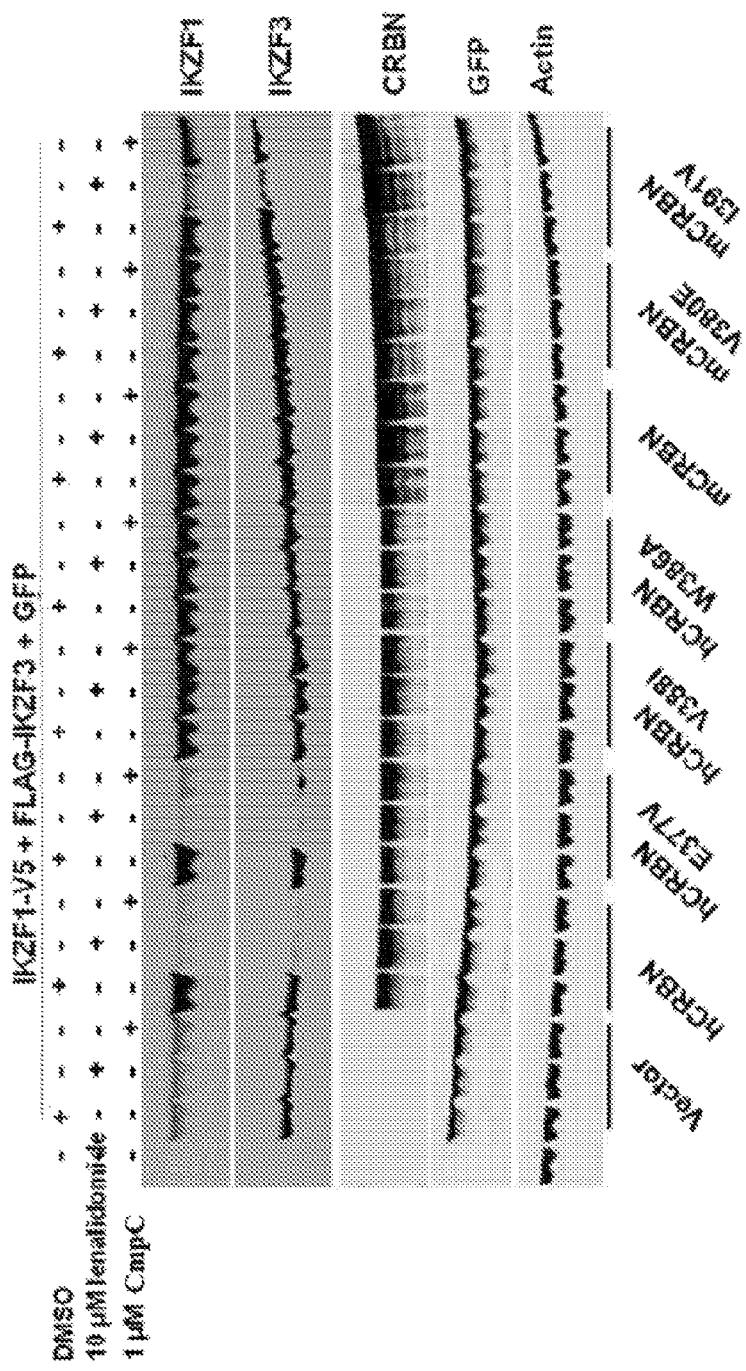

FIG. 27 shows V388 is essential for the degradation of IKZF1/3 by lenalidomide.

Figure 28:
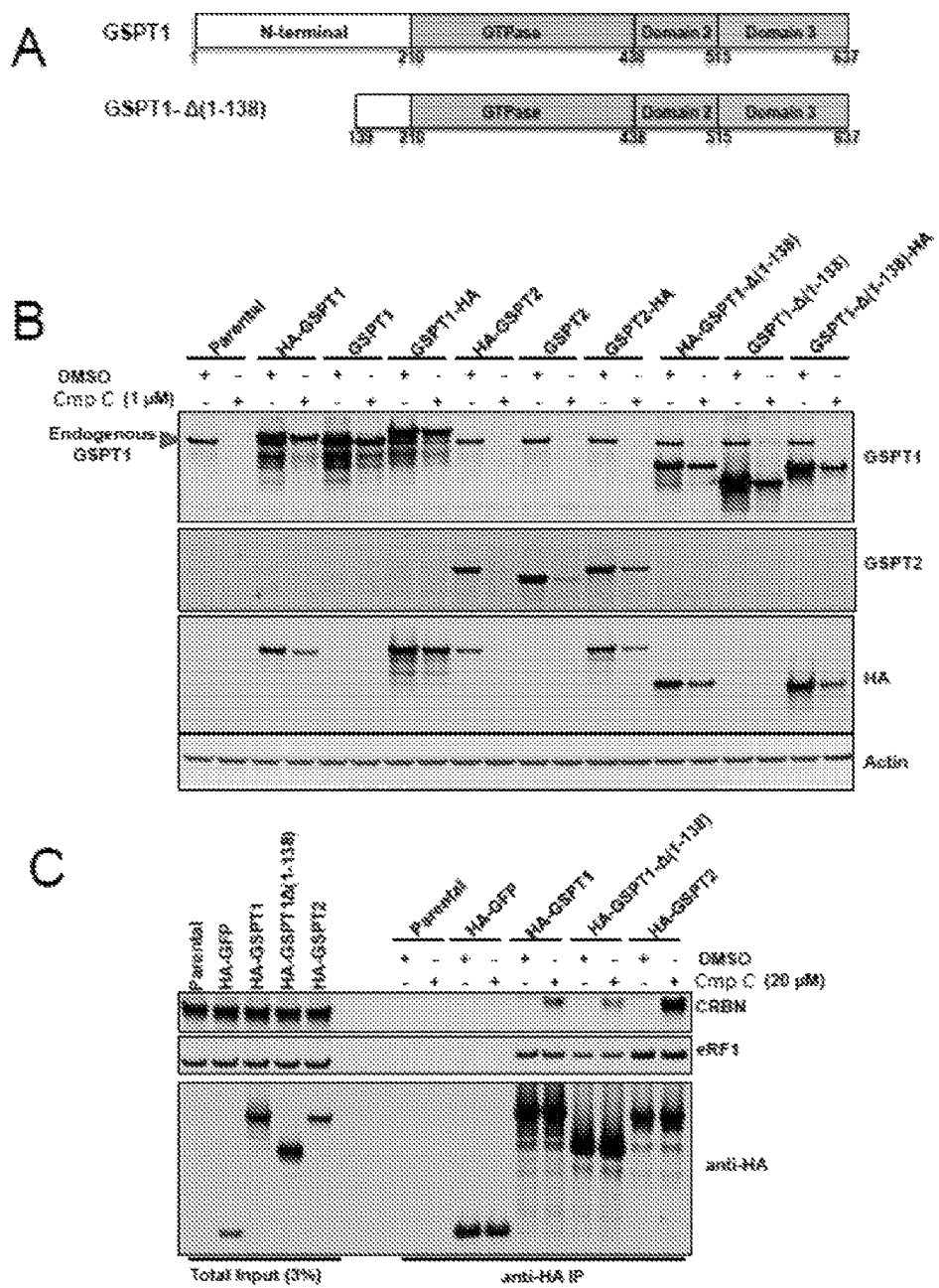

FIGS. 28A-28C show that (A) a truncation mutant of human GSPT1 lacking the N-terminal 138 amino acid residues (B) is still destabilized by Compound C in 293T HEK cells, and (C) consistent with the ability of this mutant to capture CRBN in the presence of Compound C.

Figure 29:
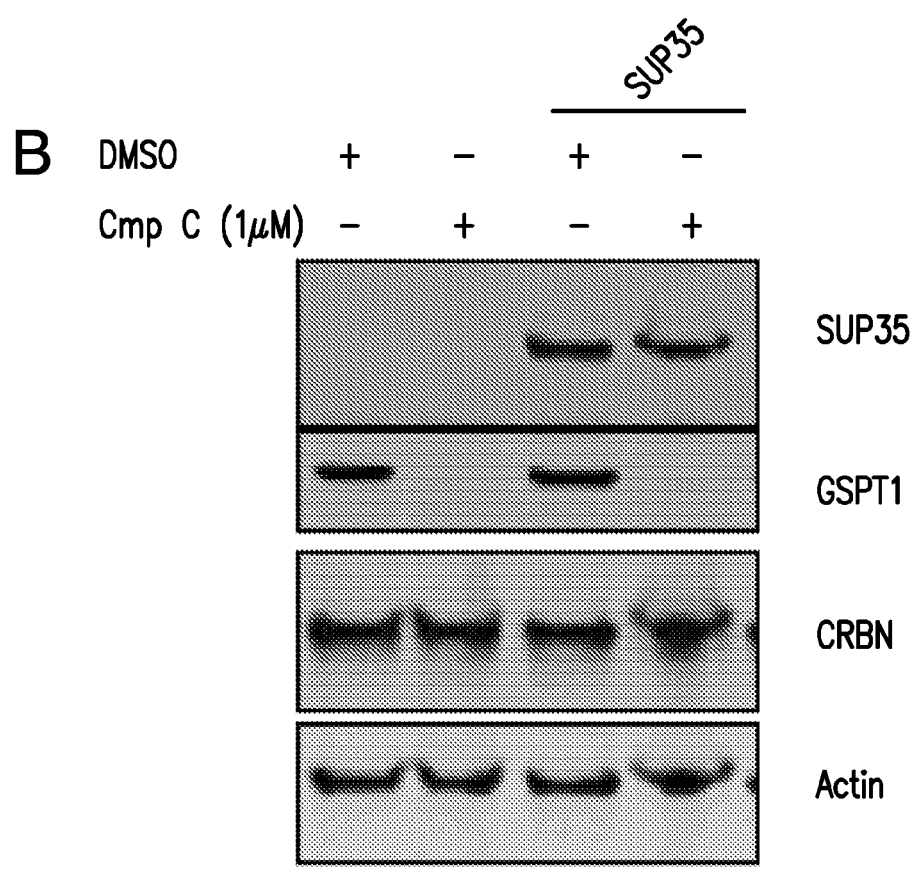

FIGS. 29A-29B show that (A) the yeast homologue SUP35 shares a high degree of sequence homology with human GSPT1, (B) but did not show any changes at the protein level in response to Compound C treatment. Human GSPT1 (hGSPT1): SEQ ID NO:5, and yeast homologue SUP35 (scSUP35): SEQ ID NO:6.

FIGS. 30A-30D show that a 32-amino acid fragment in the C-terminus of human GSPT1 (residues 562 to 593), when replaced with the corresponding region of SUP35, completely blocked the Compound C-induced degradation of GSPT1. (A) Constructs generated through domain swapping between human GSPT1 and yeast SUP35. (B-D) Western blot showing the degradation of various GSPT1 constructs in response to the Compound C treatment.

Figure 31:
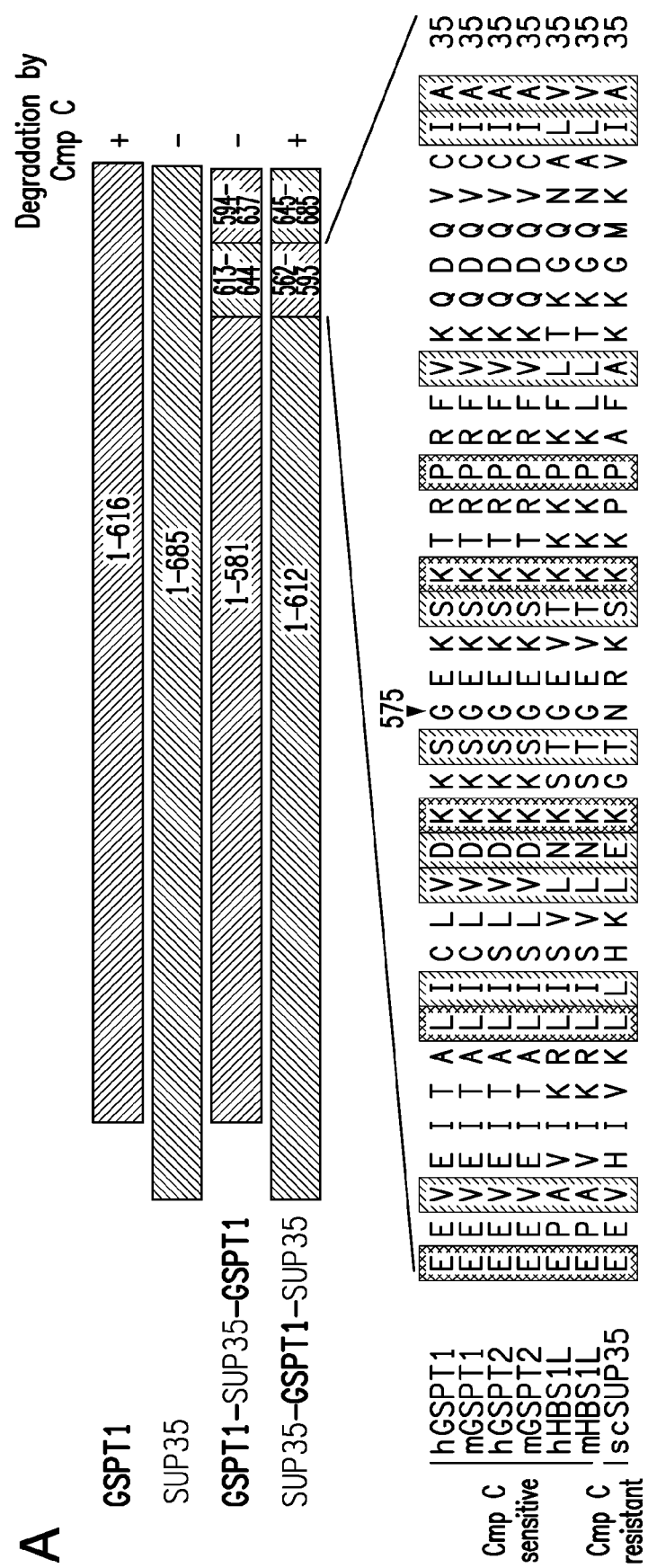

FIGS. 31A-31C show that (A) conversion of glycine 575 of human GSPT1 into the corresponding asparagine of yeast SUP35 (B) prevented the Compound C-induced degradation of GSPT1 and (C) the Compound C-induced in vitro binding of GSPT1 to CRBN. hGSPT1: SEQ ID NO:7; mGSPT1: SEQ ID NO:7; hGSPT2: SEQ ID NO:8; mGSPT2: SEQ ID NO:8; hHBS1L: SEQ ID NO:9; mHBS1L: SEQ ID NO:9; and scSUP35: SEQ ID NO:10.

Figure 32:
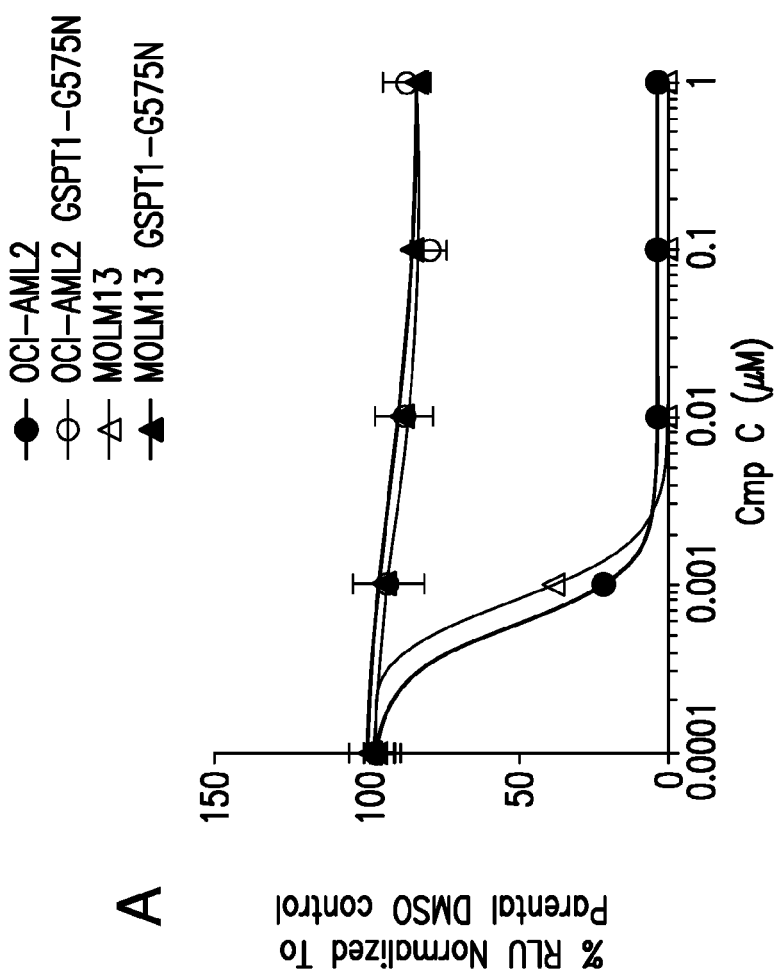

FIGS. 32A-32B show that a G575N mutation in human GSPT1 prevented (A) the Compound C-induced growth inhibition and (B) the Compound C-induced activation of ATF4 and apoptosis pathways.

FIGS. 33A-33E show a chemical structure of (A) lenalidomide, (B) pomalidomide, (C) Compound C, (D) structure of complex GSPT1-CRBN-DDB1, (E) detail of the interface between CRBN and GSPT1 with Compound C shown as sticks with carbons in yellow.

Figure 34:
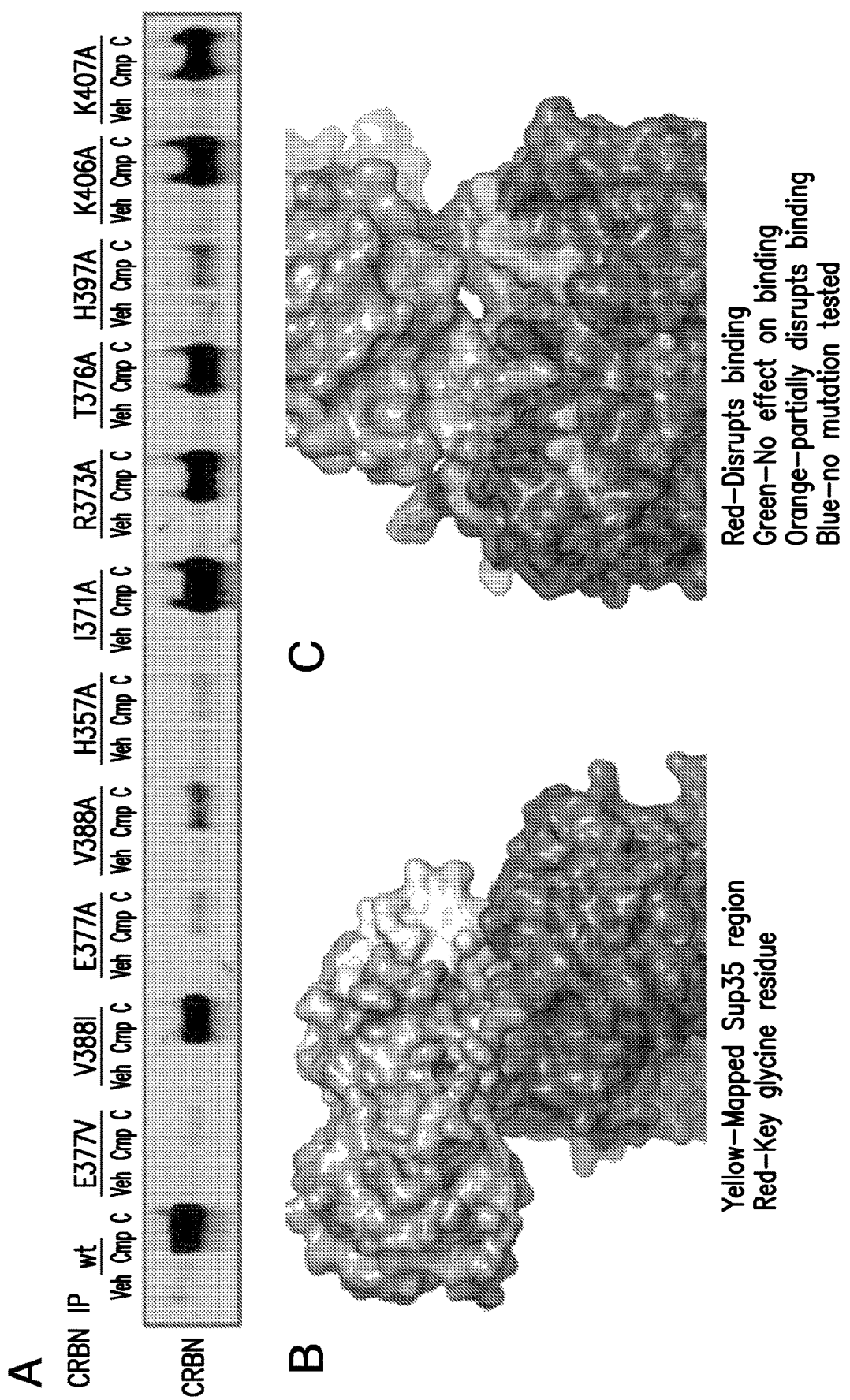

FIGS. 34A-34C show excellent agreement between structure and mutational analysis. (A) CRBN immunoprecipitation assay of various mutated forms of CRBN in the absence or presence of Compound C. (B) Structure indicating mapped SUP35 region in yellow. (C) Structure indicating positions of mutations on CRBN surface: red—disrupting binding; green—no effect on binding; orange—partially disrupting binding; and blue—no mutations tested.

FIGS. 35A-35D show the details of interaction between Compound C and CRBN-GSPT1 complex. (A) glutarimide group. (B) isoindolinone group. (C) urea group. (D) methyl-chloro-phenyl group.

Figure 36B:
Figure 36A:

FIGS. 36A-36B show non-conserved residues in red between (A) GSPT1 and GSPT2, (B) between GSPT1 and HBS1L.

Figure 37:
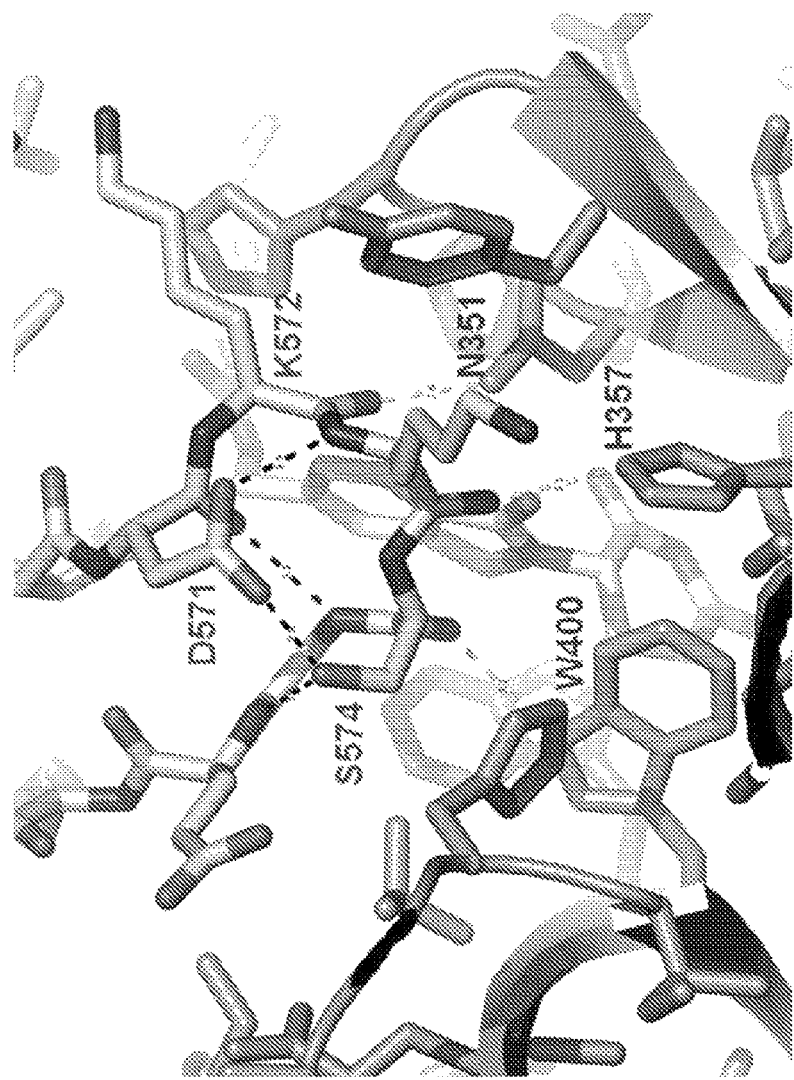

FIG. 37 shows backbone-mediated interactions between CRBN and GSPT1 in the presence of Compound C.

Figure 38:
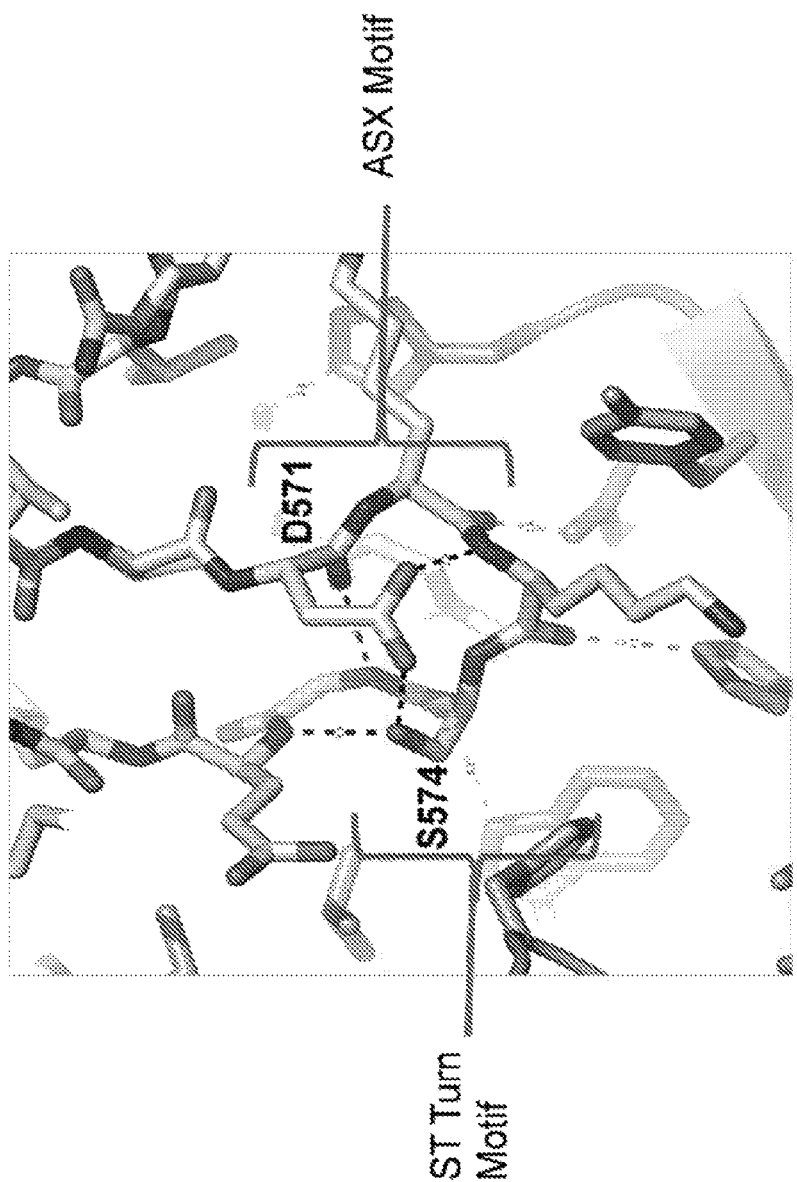

FIG. 38 shows that the key anchoring motif of GSPT1 is stabilized by internal hydrogen bonds from ASX and ST motifs.

Figure 39A:
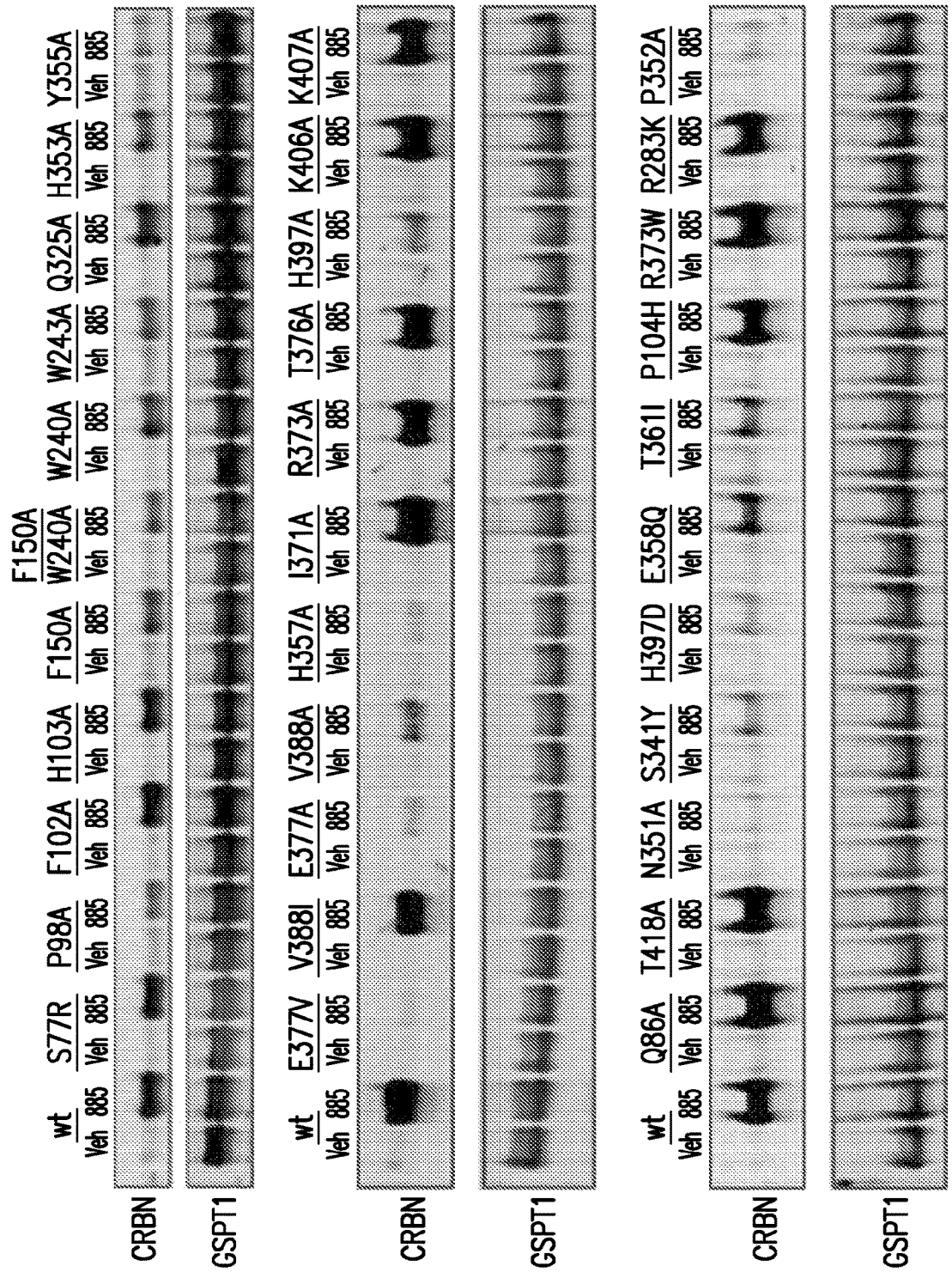
Figure 39B:
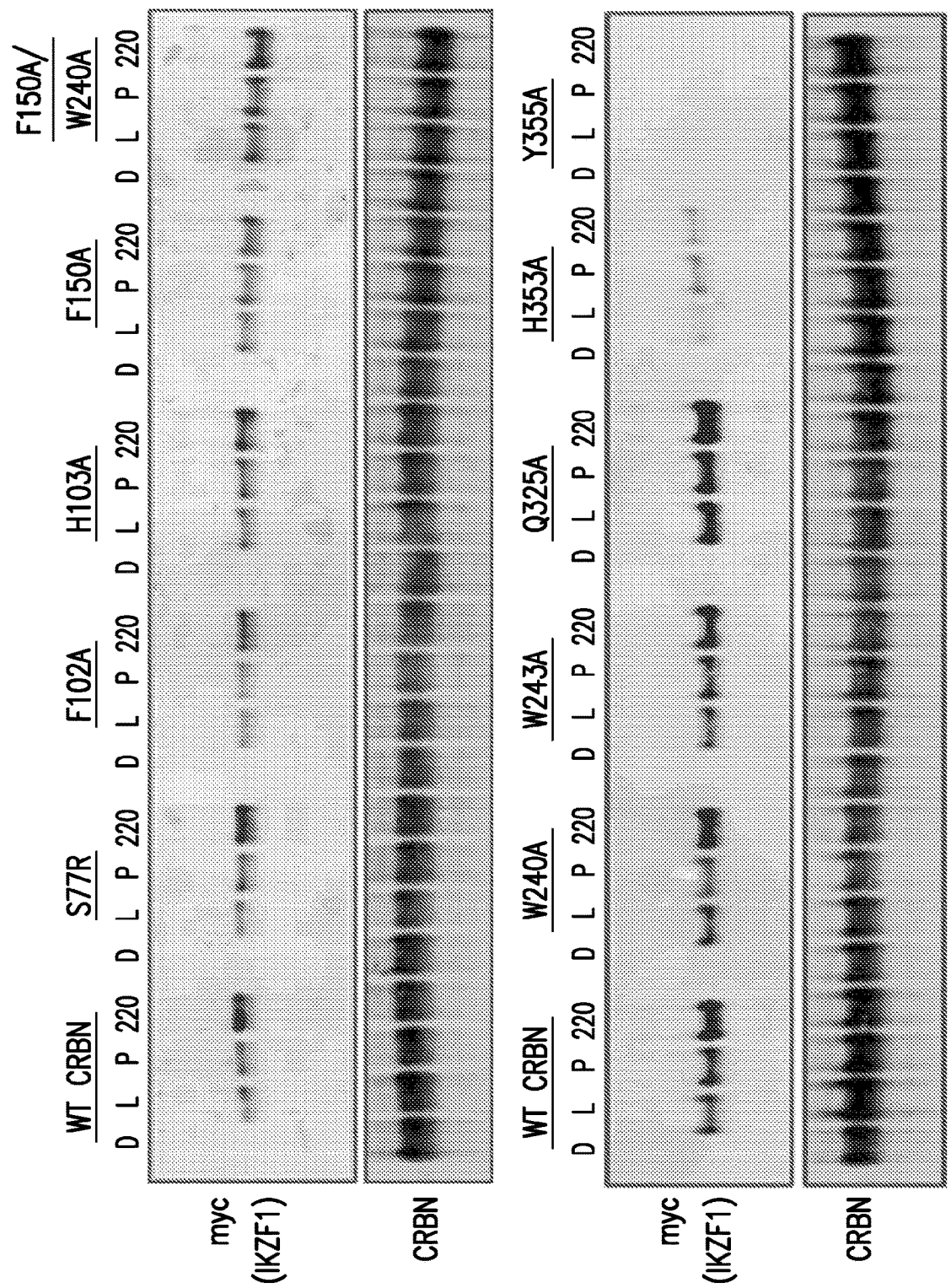

FIGS. 39A-39B show the effect of CRBN surface mutations on substrate binding. (A) Immunoprecipitation of GSPT1. (B) Immunoprecipitation of IKZF1.

FIGS. 40A-40B map the effect of mutations on CRBN surface upon substrate binding: (A) GSPT1 binding and (B) IKZF1 binding. Red—strong reduction in substrate binding; orange—some reduction; green—no effect; blue—not tested.

FIGS. 41A-41B show (A) the anchoring motif of GSPT1 (blue) bound to CRBN (green) and Compound C (yellow); (B) a model of IKZF1 (magenta) superposed upon the backnone of GSPT1 (blue); (C) immunopricipitation of CRBN-DDB1 with alanine mutations of the GSPT1 anchoring motif; (D) immunopricipitation of CRBN-DDB1 with alanine mutations of the IKZF1 anchoring motif; (E) sequence alignment of the GSPT1 anchoring motif with the putative region from IKZF1, with residues critical for binding shown to be red. The critical glycine is shown in bold.

Figure 42:
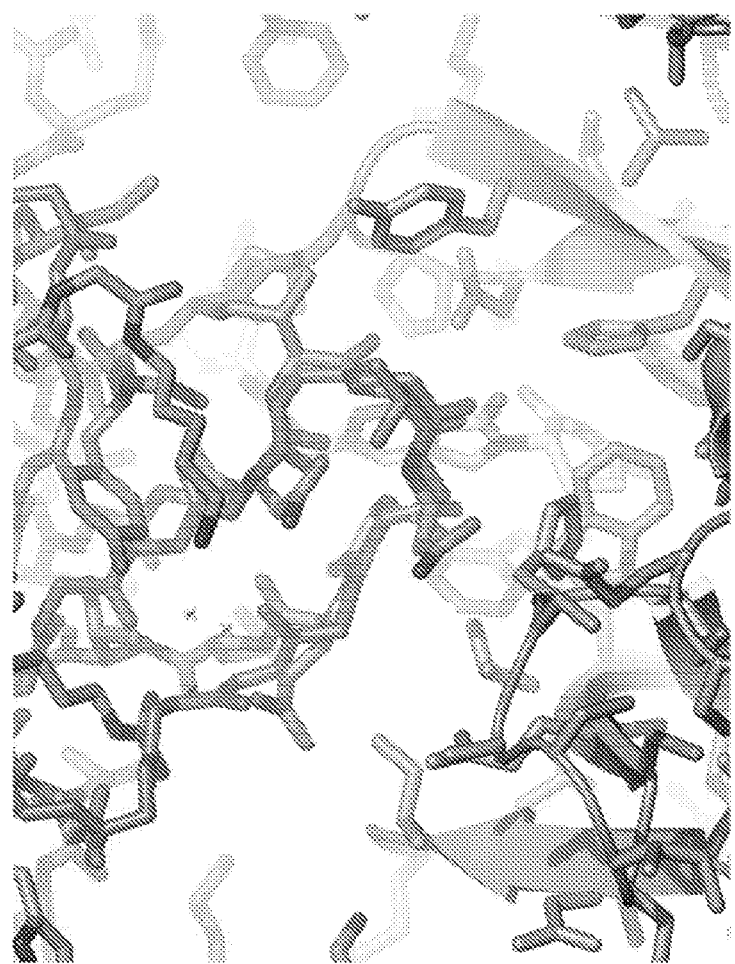

FIG. 42 shows that CRBN-CK1a complex model superposes with the anchoring motif of CRBN-GSPT1 complex.

Figure 43:
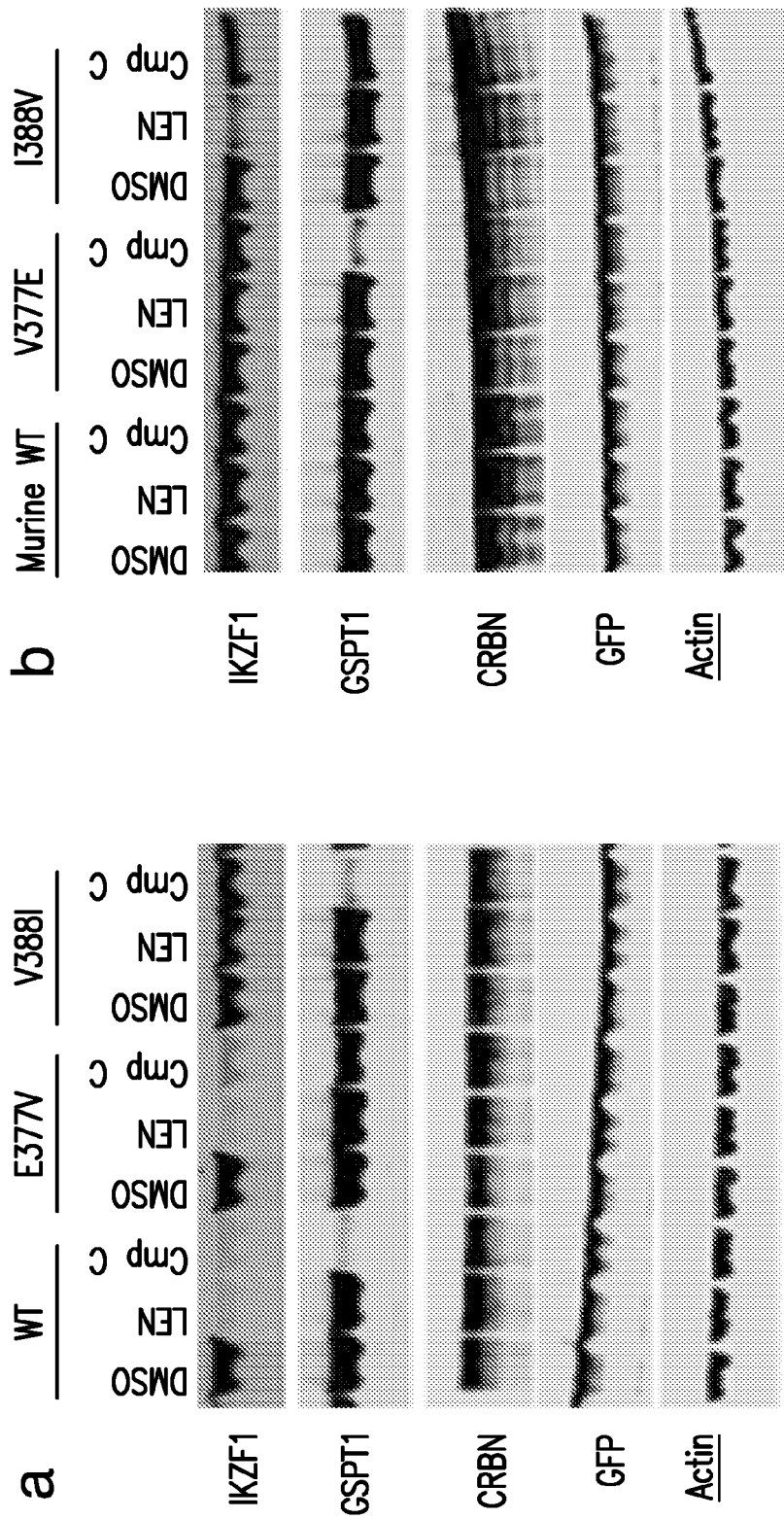

FIGS. 43A-43B show the effect of lenalidomide or Compound C on IKZF1 and GSPT1 degradation. (A) shows the effect with human CRBN. (B) shows the effect with mouse CRBN.

5. DETAILED DESCRIPTION

Figure 1:
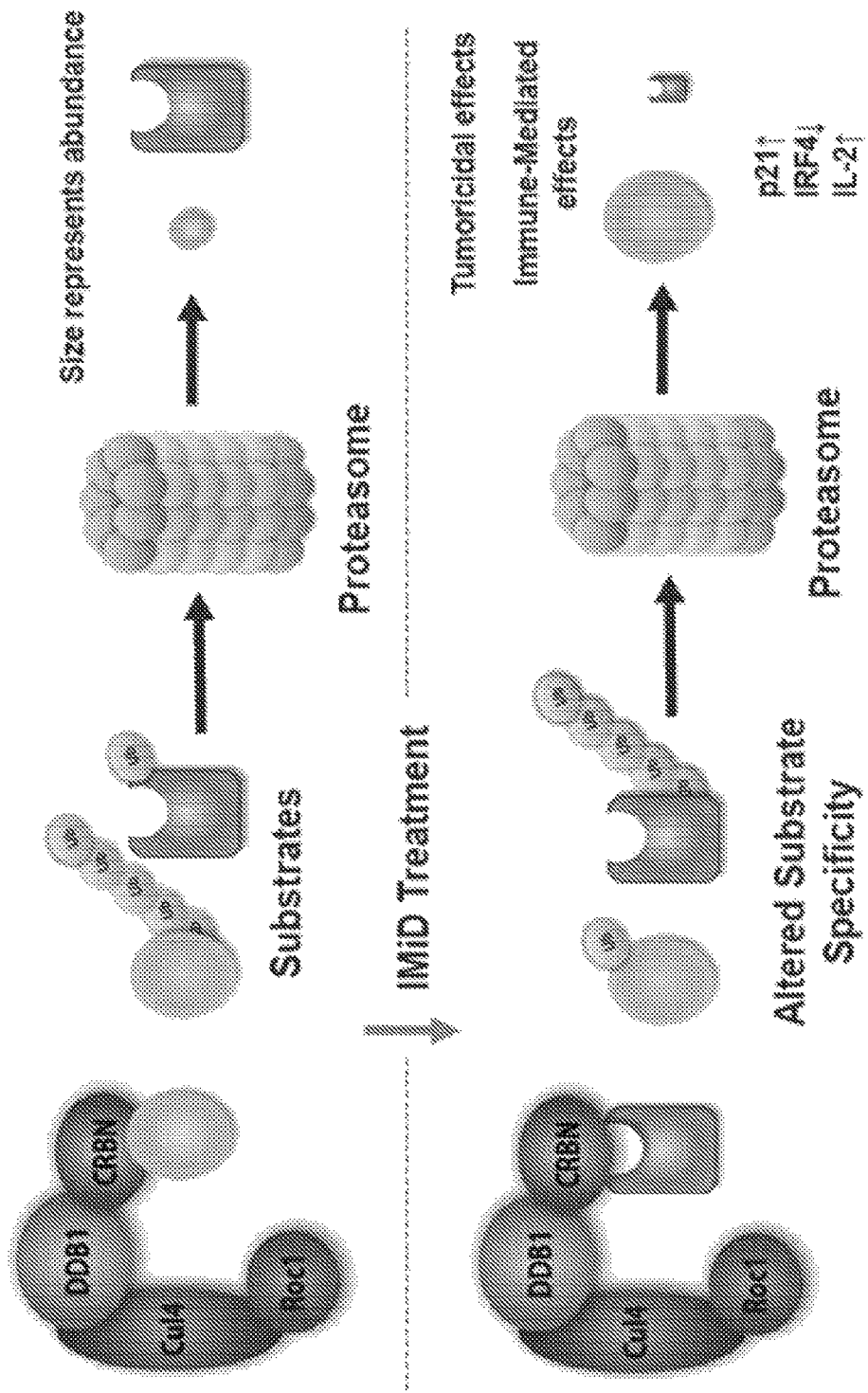
FIG. 1 depicts the differences in protein homeostasis following treatment with a CMA due to altered protein ubiquitination and degradation.

The compositions, methods and kits provided herein are based, in part, on the discovery that E3 ubiquitin ligases, including CRBN, undergo conformational changes or otherwise alter the surface, upon ligand (e.g., CMA) binding. As shown in FIG. 1, CRBN binds proteins, such as DDB1, Cul4 and Roc1 to form a E3-ubiquitan ligase complex, which serve to facilitate targeted protein ubiquitination and degradation. In the presence of a CMA, the CRBN complex has an altered binding specificity and subsequent downstream biological effects. CRBN is believed to act as a novel substrate receptor for the complex. Without wishing to be bound by theory, it is believed that this ligand-dependent E3 ubiquitin ligase (e.g., CRBN) conformational change or alteration results in different E3 ubiquitin ligase surfaces being exposed, thereby affecting the recruitment and engagement of different substrates to the E3 ubiquitin ligase complex and resulting in the downstream differential phenotypic and/or therapeutic effects. In addition, ligands (including CMAs) provide binding interactions for the various different protein substrates. In specific embodiments, the E3 ubiquitin ligase is CRBN, and the CRBN ligands include CMAs, such as Compound C, or any analog thereof.

5.1 Definitions

All patents, applications, published applications and other publications are incorporated by reference in their entirety. Unless defined otherwise, all technical and scientific terms used herein have the same meaning as is commonly understood by one of ordinary skill in the art. All patents, applications, published applications and other publications are incorporated herein by reference in their entirety. In the event that there is a plurality of definitions for a term herein, those in this section prevail unless stated otherwise.

The term "about" or "approximately" means within 20%, within 10%, and within 5% (or 1% or less) of a given value or range.

As used herein, the term "degron" refers to a sequence of amino acid in a protein, e.g., a sequence in a protein that directs the starting place of degradation.

As used herein, "administer" or "administration" refers to the act of injecting or otherwise physically delivering a substance as it exists outside the body into a patient, such as by mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

"Biological sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include but are not limited to whole blood, partially purified blood, PBMCs, tissue biopsies, and the like.

A biological marker or "biomarker" is a substance whose detection indicates a particular biological state, such as, for example, the presence of cancer. In some embodiments, biomarkers can either be determined individually, or several biomarkers can be measured simultaneously. In some embodiments, a "biomarker" indicates a change in the level of mRNA expression that may correlate with the risk or progression of a disease, or with the susceptibility of the disease to a given treatment. In some embodiments, the biomarker is a nucleic acid, such as a mRNA or cDNA. In additional embodiments, a "biomarker" indicates a change in the level of polypeptide or protein expression that may correlate with the risk, susceptibility to treatment, or progression of a disease. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

The terms "cancer" and "cancerous" refer to or describe the physiological condition in mammals that is typically characterized by unregulated cell growth. Examples of cancer include, but are not limited to, blood-borne tumors (e.g., multiple myeloma, lymphoma and leukemia), and solid tumors. Other exemplary cancers are provided elsewhere herein.

The term "capture agent," as used herein, refers to an agent that binds an mRNA or protein through an interaction that is sufficient to permit the agent to bind and concentrate the mRNA or protein from a homogeneous mixture.

The terms "cereblon" or "CRBN" and similar terms refers to the polypeptides ("polypeptides," "peptides" and "proteins" are used interchangeably herein) comprising the amino acid sequence any CRBN, such as a human CRBN protein (e.g., human CRBN isoform 1, GenBank Accession No. NP_057386; or human CRBN isoforms 2, GenBank Accession No. NP_001166953, each of which is herein incorporated by reference in its entirety), and related polypeptides, including SNP variants thereof. Related CRBN polypeptides include allelic variants (e.g., SNP variants); splice variants; fragments; derivatives; substitution, deletion, and insertion variants; fusion polypeptides; and inter-species homologs, which, in certain embodiments, retain CRBN activity and/or are sufficient to generate an anti-CRBN immune response.

As used herein, the term "cereblon-associated protein" or "CRBN-associated protein" refers to a protein that interacts with or binds to CRBN directly or indirectly. In certain embodiments, a "cereblon-associated protein" or "CRBN-associated protein" is a substrate of CRBN, for example, a protein substrate of the E3 ubiquitin ligase complex involving CRBN, or the downstream substrates thereof. In one embodiment, the CRBN-associated protein provided herein is a substrate of CRBN such as IKZF3, also known as "Aiolos," and/or IKZF1, also known as "Ikaros." In certain embodiments, a "cereblon-associated protein" or "CRBN-associated protein" is a binding protein of CRBN.

As used herein and unless otherwise indicated, the term "co-crystal" means a crystalline form that contains more than one compound in a crystal lattice. Co-crystals include crystalline molecular complexes of two or more non-volatile compounds bound together in a crystal lattice through non-ionic interactions. As used herein, co-crystals include pharmaceutical cocrystals wherein the crystalline molecular complexes containing a therapeutic compound and one or more additional non-volatile compound(s) (referred to herein as counter-molecule(s)). A counter-molecule in a pharmaceutical cocrystal is typically a non-toxic pharmaceutically acceptable molecule, such as, for example, food additives, preservatives, pharmaceutical excipients, or other APIs. In some embodiments, pharmaceutical cocrystals enhance certain physicochemical properties of drug products (e.g., solubility, dissolution rate, bioavailability and/or stability). without compromising the chemical structural integrity of the active pharmaceutical ingredient (API). See, e.g., Jones et al., "Pharmaceutical Cocrystals: An Emerging Approach to Physical Property Enhancement," *MRS Bulletin,* 2006, 31, 875-879; Trask, "An Overview of Pharmaceutical Cocrystals as Intellectual Property," *Molecular Pharmaceutics,* 2007, 4(3), 301-309; Schultheiss & Newman, "Pharmaceutical Cocrystals and Their Physicochemical Properties," *Crystal Growth & Design,* 2009, 9(6), 2950-2967; Shan & Zaworotko, "The Role of Cocrystals in Pharmaceutical Science," *Drug Discovery Today,* 2008, 13(9/10), 440-446; and Vishweshwar et al., "Pharmaceutical Co-Crystals," *J. Pharm. Sci.,* 2006, 95(3), 499-516.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C, although small regions (e.g. less than about 3 bases) of mismatch, insertion, or deleted sequence may be present.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

As used herein, the term "composition" is intended to encompass a product containing the specified ingredients (e.g., an antibody provided herein) and, optionally, in the specified amounts, as well as any product which results, directly or indirectly, from combination of the specified ingredients in, optionally, the specified amounts.

The term "cycle number" or "CT" when used herein in reference to PCR methods, refers to the PCR cycle number at which the fluorescence level passes a given set threshold level. The CT measurement can be used, for example, to approximate levels of mRNA in an original sample. The CT measurement is often used in terms of "dCT" or the "difference in the CT" score, when the CT of one nucleic acid is subtracted from the CT of another nucleic acid.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The term "effective amount" as used herein refers to the amount of a therapy (e.g., a composition provided herein) which is sufficient to reduce and/or ameliorate the severity and/or duration of a given disease, disorder or condition and/or a symptom related thereto. This term also encompasses an amount necessary for the reduction or amelioration of the advancement or progression of a given disease, disorder or condition, reduction or amelioration of the recurrence, development or onset of a given disease, disorder or condition, and/or to improve or enhance the prophylactic or therapeutic effect(s) of another therapy. In some embodiments, "effective amount" as used herein also refers to the amount of therapy provided herein to achieve a specified result.

As used herein, an "effective patient tumor response" refers to any increase in the therapeutic benefit to the patient. An "effective patient tumor response" can be, for example, a 5%, 10%, 25%, 50%, or 100% decrease in the rate of progress of the tumor. An "effective patient tumor response"

can be, for example, a 5%, 10%, 25%, 50%, or 100% decrease in the physical symptoms of a cancer. An "effective patient tumor response" can also be, for example, a 5%, 10%, 25%, 50%, 100%, 200%, or more increase in the response of the patient, as measured by any suitable means, such as gene expression, cell counts, assay results, etc.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide or a portion thereof.

The term "CRBN modifying agent" or "CMA" refers to a molecule that directly or indirectly modulating the CRBN E3 ubiquitin-ligase complex. In some embodiments, the CMA can bind directly to CRBN and induce conformational change in the CRBN protein. In other embodiments, the CMA can bind directly to other subunits in the CRBN E3 ubiquitin-ligase complex.

As used herein, the term "immunomodulatory compound" or "immunomodulatory drug" refers generally to a molecule or agent capable of altering the immune response in some way. Non-limiting examples of immunomodulatory compounds include those disclosed in Section 5.9 below.

The terms "isolated" and "purified" refer to isolation of a substance (such as mRNA, antibody or protein) such that the substance comprises a substantial portion of the sample in which it resides, i.e. greater than the substance is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

A "label" or a "detectable moiety" in reference to a nucleic acid, refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

As used herein, the terms "manage," "managing," and "management" refer to the beneficial effects that a subject derives from a therapy, which does not result in a cure of the disease, disorder or condition. In certain embodiments, a subject is administered one or more therapies to "manage" a disease, disorder or condition, or one or more symptoms thereof, so as to prevent the progression or worsening of the disease, disorder or condition.

The term "monitor," as used herein, generally refers to the overseeing, supervision, regulation, watching, tracking, or surveillance of an activity. For example, the term "monitoring the effectiveness of a compound" refers to tracking the effectiveness in treating a cancer in a patient or in a tumor cell culture. Similarly, the "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

As used herein, the term "nucleotide," nucleic acid," "nucleic acid molecule," "polynucleotide," and other similar terms are used interchangeable and include DNA, RNA, mRNA and the like.

The term "nucleic acid" or "oligonucleotide probe" refers to a nucleic acid capable of binding to a target nucleic acid of complementary sequence, such as the mRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target mRNA biomarker of interest.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, greater than about 90% by weight of one enantiomer of the compound and less than about 10% by weight of the other enantiomers of the compound, greater than about 95% by weight of one enantiomer of the compound and less than about 5% by weight of the other enantiomers of the compound, greater than about 97% by weight of one enantiomer of the compound and less than about 3% by weight of the other enantiomers of the compound, and greater than about 99% by weight of one enantiomer of the compound and less than about 1% by weight of the other enantiomers of the compound.

The terms "optional" or "optionally" as used herein means that the subsequently described event or circumstance may or may not occur, and that the description includes, without limitation, instances where said event or circumstance occurs and instances in which it does not.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

The terms "polymerase chain reaction," or "PCR," as used herein generally refers to a procedure wherein small amounts of a nucleic acid, RNA and/or DNA, are amplified as described, for example, in U.S. Pat. No. 4,683,195 to Mullis. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51: 263 (1987); Erlich, ed., PCR Technology, (Stockton Press, N Y, 1989).

As used herein the terms "polypeptide" and "protein" as used interchangeably herein, refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The amino acids making up the polypeptide may be naturally derived, or may be synthetic. The polypeptide can be purified from a biological sample.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

As used herein, the term "prophylactic agent" refers to any agent that can totally or partially inhibit the development, recurrence, onset or spread of a disease, disorder or condition and/or symptom related thereto in a subject. In certain embodiments, the term "prophylactic agent" refers to a compound provided herein. In certain other embodiments, the term "prophylactic agent" refers to an agent other than a compound provided herein. In certain embodiments, a prophylactic agent is an agent which is known to be useful to or has been or is currently being used to prevent a disease, disorder or condition and/or a symptom related thereto or impede the onset, development, progression and/or severity of a disease, disorder or condition and/or a symptom related thereto.

The term "probe" as used herein, refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

The term "refractory or resistant" refers to a circumstance where patients, even after intensive treatment, have residual cancer cells (e.g., leukemia or lymphoma cells) in their lymphatic system, blood and/or blood forming tissues (e.g., marrow).

The term "regulate" as used herein refers to controlling the activity of a molecule or biological function, such as enhancing or diminishing the activity or function.

The term "sample" as used herein relates to a material or mixture of materials, typically, although not necessarily, in fluid form, containing one or more components of interest.

The term "sensitivity" and "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least a 5%, or more, in the effectiveness of the tumor treatment.

"Sequence identity" or "identity" in the context of two nucleic acid sequences refers to the residues in the two sequences which are the same when aligned for maximum correspondence over a specified comparison window, and can take into consideration additions, deletions and substitutions.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, and greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, greater than about 70% by weight, greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term stringent assay conditions generally refers to the combination of hybridization and wash conditions.

As used herein, the terms "subject" and "patient" are used interchangeably. As used herein, a subject can be a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a disease, disorder or condition. In another embodiment, the subject is a mammal (e.g., a human) at risk of developing a disease, disorder or condition.

The term "substantial identity" or "homologous" in their various grammatical forms in the context of polynucleotides generally means that a polynucleotide comprises a sequence that has a desired identity, for example, at least 60% identity, at least 70% sequence identity, at least 80%, at least 90% and at least 95%, compared to a reference sequence. Another indication that nucleotide sequences are substantially identical is if two molecules hybridize to each other under stringent conditions.

As used herein, and unless otherwise specified, the term "therapeutically effective amount" of a compound is an amount sufficient to provide a therapeutic benefit in the treatment or management of a cancer, or to delay or minimize one or more symptoms associated with the presence of the cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent.

As used herein, the term "therapy" refers to any protocol, method and/or agent that can be used in the prevention, management, treatment and/or amelioration of a given disease, disorder or condition. In certain embodiments, the terms "therapies" and "therapy" refer to a drug therapy, biological therapy, supportive therapy, and/or other therapies useful in the prevention, management, treatment and/or amelioration of a given disease, disorder or condition known to one of skill in the art such as medical personnel.

As used herein, and unless otherwise specified, the terms "treat," "treating" and "treatment" refer to an action that occurs while a patient is suffering from the specified disease, disorder or condition. As used herein, the terms "treat," "treatment" and "treating" refer to the reduction or amelioration of the progression, severity, and/or duration of a disease, disorder or condition resulting from the administration of one or more therapies.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition. An mRNA from a patient sample can be "upregulated" when treated with a drug, as compared to a non-treated control. This upregulation can be, for example, an increase of about 5%, 10%, 20%, 30%, 40%, 50%, 60%, 70%, 90%, 100%, 200%, 300%, 500%, 1,000%, 5,000% or more of the comparative control mRNA level. Alternatively, an mRNA can be "downregulated", or expressed at a lower level, in response to administration of certain compounds or other agents. A downregulated mRNA can be, for example, present at a level of about 99%, 95%, 90%, 80%, 70%, 60%, 50%, 40%, 30%, 20%, 10%, 1% or less of the comparative control mRNA level. Similarly, the level of a polypeptide or protein biomarker from a patient sample can be increased when treated with a drug, as compared to a non-treated control. This increase can be about 5%, 10%, 20%, 30%, 40%, 50%, 60%, 70%, 90%, 100%, 200%, 300%, 500%, 1,000%, 5,000% or more of the comparative control protein level. Alternatively, the level of a protein biomarker can be decreased in response to administration of certain compounds or other agents. This decrease can be, for example, present at a level of about 99%, 95%, 90%, 80%, 70%, 60%, 50%, 40%, 30%, 20%, 10%, 1% or less of the comparative control protein level.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al. (1989) *Molecular Cloning; A Laboratory Manual* (2d ed.); D. N Glover, ed. (1985) *DNA Cloning*, Volumes I and II; M. J. Gait, ed. (1984) *Oligonucleotide Synthesis*; B. D. Hames & S J. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture; Immobilized Cells and Enzymes* (IRL Press, 1986); *Immunochemical Methods in Cell and Molecular Biology* (Academic Press, London); Scopes (1987) *Protein Purification: Principles and Practice* (2d ed.; Springer Verlag, N.Y.); and D. M. Weir and C. C. Blackwell, eds. (1986) *Handbook of Experimental Immunology*, Volumes I-IV.

5.2 Methods of Identifying Compounds

Provided herein, for example, are compositions, methods and kits for screening or otherwise identifying a compound, that binds to an E3 ubiquitin ligase. In certain embodiments, the compound induces a conformational change in the E3 ubiquitin ligase ligand binding pocket. In other embodiments, the compound alters the properties of the E3 ubiquitin ligase surface. In some embodiments of the various compositions and methods provided herein, the compound alters the E3 ubiquitin ligase surface adjacent to the E3 ubiquitin ligase ligand binding pocket. In other embodiments, the compound alters one or more surrounding loops or other surface of the E3 ubiquitin ligase ligand binding pocket. In certain embodiments, the properties of the E3 ubiquitin ligase surface are altered by the placement of compound appendages. In a specific embodiment, the compound is a CMA. In another specific embodiment, the E3 ubiquitin ligase is CRBN.

While exemplary methods provided below and elsewhere refer to CRBN conformational changes (e.g., within the CMA binding pocket) or other alterations in the properties of a CRBN surface (e.g., on an adjacent region of the protein, such as a region adjacent to the CMA-binding pocket), it is understood that CRBN is merely illustrative and that the methods provided herein can be utilized with other E3 ubiquitin ligases.

In one aspect, provided herein is a method of identifying a test compound that induces a CRBN conformational change (e.g., within the CMA-binding pocket of the CRBN) or otherwise altering the properties of a CRBN surface (e.g., on an adjacent region of the protein). In certain embodiments, the method comprises (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a compound that induces a CRBN conformational change or alteration. In some embodiments, a CRBN conformational change is induced. In other embodiments, an alteration of the properties of a CRBN surface are induced. In some embodiments, the first set of atomic coordinates and/or said second set of atomic coordinates define a CMA binding domain. In certain embodiments, the difference in atomic coordinates is determined by assessing differences in atomic distances. Also provided herein is a test compound identified by this method. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN.

In another aspect, provided herein is a method of identifying a test compound that induces a CRBN conformational change (e.g., within the CMA-binding pocket of the CRBN) or otherwise alters the properties of a CRBN surface (e.g., on an adjacent region of the protein). In certain embodiments, the method comprises (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. Also provided herein is a test compound identified by this method. In some embodiments, a CRBN conformational change is induced. In other embodiments, an alteration of the properties of a CRBN surface are induced. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof.

In another aspect, provided herein is a method of identifying a test compound that has a specific downstream biological activity comprising: (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a compound has the specific downstream biological activity. In some embodiments, the first set of atomic coordinates and/or said second set of atomic coordinates define a CMA binding domain. In certain embodiments, the difference in atomic coordinates is determined by assessing differences in atomic distances. In some embodiments, the method further comprises assaying the specific biological activity. Also provided herein is a test compound identified by this method. In certain embodiments, the method further comprises administering said compound to a patient, wherein said biological activity is modulated in said patient. In certain embodiments, the patient has a disease, and wherein one or more symptoms of said disease are alleviated following said administration. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN.

In another aspect, provided herein is a method of identifying a test compound that has a specific downstream biological activity comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound has the specific downstream biological activity. Also provided herein is a test compound identified by this method. In some embodiments, the test compound induces a CRBN conformational change. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof.

In some embodiments, the biological activity is a tumoricidal effect. In other embodiments, the biological activity is an apoptosis effect. In some embodiments, the biological activity is anti-proliferation. In yet other embodiments, the biological activity is PBMC viability. In some embodiments, the biological activity is toxicity. In certain embodiments, the biological activity is substrate degradation. In one embodiments, the biological activity is Aiolos degradation. In another embodiments, the biological activity is Ikaros degradation. In other embodiments, the biological activity is an immune-mediated effect. In another embodiment, the biological activity is IL-2 induction. In some embodiments, the biological activity is IL-2 repression. In yet other embodiments, the biological activity is a HbF effect. Any combination of one, two, three or more of the aforementioned biological activities is also contemplated. In certain embodiments, the biological activity is based on specific cell type categories. In other embodiments, the biological activity is based on specific tissue type categories. In yet other embodiments, the biological activity is based on solid tumors or solid tumor categories. In some embodiments, the biological activity is based on non-solid tumor categories.

In another aspect, provided herein is a method of identifying a test compound that has a specific therapeutic efficacy comprising: (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a compound has the specific therapeutic efficacy. In some embodiments, the first set of atomic coordinates and/or said second set of atomic coordinates define a CMA binding domain. In certain embodiments, the difference in atomic coordinates is determined by assessing differences in atomic distances. Also provided herein is a test compound identified by this method. In certain embodiments, the method further comprises administering said compound to a patient having disease, disorder or condition, wherein one or more symptoms of said disease, disorder or condition is alleviated following said administration. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN.

In another aspect, provided herein is a method of identifying a test compound that has a specific downstream therapeutic efficacy comprising: (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound has the specific downstream biological activity. Also provided herein is a test compound identified by this method. In some embodiments, the test compound induces a CRBN conformational change. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof.

5.2.1. Computer-Based Design of Compounds

Provided herein are methods of designing compounds based on fit within the CMA binding pocket of CRBN. In some embodiments, the methods are computer-based methods.

In one aspect, provided herein is a method of designing a test compound based on fit within CMA binding pocket of CRBN, comprising: (a) generating on a computer, three-dimensional structural features of a CRBN having a conformational change or alteration in the CMA binding pocket, (b) designing a test compound capable of selectively binding to said CMA binding pocket, (c) synthesizing said test compound, (d) contacting CRBN with said synthesized test compound, and (e) determining if said test compound binds to said CRBN. In certain embodiments, the conformational change or alteration occurs in a CMA binding pocket of the CRBN.

In one embodiment, the method comprises (i) generating (e.g., on a computer) a three-dimensional structural features of a CRBN having a conformational change or alteration in the CMA binding pocket, (ii) designing a compound capable of selectively binding to said CMA binding pocket, (iii) synthesizing said compound, (iv) contacting a CRBN with said synthesized compound, and (v) identifying a synthesized compound that binds to said CMA binding pocket. In certain embodiments, the CMA binding pocket conformational change or alteration of the CRBN is defined by atomic coordinates as set forth in any one of Tables 3, 4, 5, 6 or 7; or a three dimensional structure as set forth in any one of FIG. 12-18 or 20. In some embodiments, the CMA binding pocket comprises W380, W386 and/or W400. Exemplary CMA binding pockets are provided in FIGS. 12-20 and 22; and Tables 3-5. In some embodiments, the method further comprises methods provided in Example 6.10.

In certain embodiments, the test compounds are synthesized and assayed for a biological activity as provided elsewhere herein. For example, in some embodiments, the biological activity is a tumoricidal effect, apoptosis effect, anti-proliferation, increased proliferation, PBMC viability, toxicity, substrate degradation (e.g., Aiolos or Ikaros degradation), an immune-mediated effect, IL-2 induction, or IL-2 repression.

In other embodiments, the test compounds are synthesized and assayed for a therapeutic activity as provided elsewhere herein.

5.3 Crystalline CRBN

Provided herein are crystalline forms of CRBN, for example, unbound CRBN or CRBN complexed with a CMA. In one embodiment, the crystalline form has atomic coordinates as set forth in any one of Tables 3, 4, 5, 6 or 7. In some embodiments, the crystalline form has a three dimensional structure as set forth in any one of FIG. 12-18 or 20. In certain embodiments, the CRBN is complexed with (or otherwise bound to) DDB1. In other embodiments, the CRBN is complexed with (or otherwise bound to) a CMA. In certain embodiments, the CMA is thalidomide, pomalidomide or lenalidomide. In other embodiments, the CRBN is complexed with (or otherwise bound to) DDB1 and a CMA. Exemplary crystals and methods of making the crystals are provided in Example 6.10 below.

5.3.1. Crystalline CRBN—Unbound

Provided herein is a crystalline CRBN. In certain embodiments, the CRBN is further bound to DDB1, Cul4, Roc1, or any combination thereof.

In one embodiment, the CRBN has a three-dimensional structure. In certain embodiments, the three-dimensional structure is determined by x-ray diffraction. In a specific embodiment, the three-dimensional structure has the following atomic coordinates. In one embodiment, the crystalline form has atomic coordinates as set forth in any one of Tables 3, 4, 5, 6 or 7. In some embodiments, the crystalline form has a three dimensional structure as set forth in any one of FIG. 12-18 or 20. In certain embodiments, the CRBN is complexed with (or otherwise bound to) DDB1. In other embodiments, the CRBN is complexed with (or otherwise bound to) a CMA. In certain embodiments, the CMA is thalidomide, pomalidomide or lenalidomide. In other embodiments, the CRBN is complexed with (or otherwise bound to) DDB and a CMA. Exemplary crystals and methods of making the crystals are provided in Example 6.10 below.

In a specific embodiment, the crystalline form has atomic coordinates set forth in Table 4. In other embodiments, the crystalline form has atomic coordinates set forth in Table 5. In other embodiments, the crystalline form has atomic coordinates set forth in Table 6. In other embodiments, the crystalline form has atomic coordinates set forth in Table 7.

In some embodiments, the crystalline form comprises a fragment of CRBN. In other embodiments, the crystalline form comprises a fragment of CRBN, either alone or in combination with DDB1 and/or a CMA provided herein.

Also provided herein is a method to obtain a crystalline CRBN, wherein said method comprises concentrating the CRBN and obtaining a crystal using methods provided in Example 6.10 below.

5.3.2. Crystalline CRBN—Bound

Provided herein is a crystal of a complex comprising CRBN and a CMA. In one embodiment, the CMA is an immunomodulatory compound provided herein (see, e.g., Section 5.9 below). In other embodiments, the CMA is Compound C or an analog thereof. In certain embodiments, the CRBN is further bound to DDB1, Cul4, Roc1, or any combination thereof.

In one embodiment, the crystal of the complex has a three-dimensional structure. In certain embodiments, the three-dimensional structure is determined by x-ray diffraction. In one embodiment, the crystal has atomic coordinates as set forth in any one of Tables 3, 4, 5, 6 or 7. In some embodiments, the crystal has a three dimensional structure as set forth in any one of FIG. 12-18 or 20. In certain embodiments, the CRBN is complexed with (or otherwise bound to) DDB1. In other embodiments, the CRBN is complexed with (or otherwise bound to) a CMA. In certain embodiments, the CMA is thalidomide, pomalidomide or lenalidomide. In other embodiments, the CRBN is complexed with (or otherwise bound to) DDB and a CMA. Exemplary crystals and methods of making the crystals are provided in Example 6.10 below.

In one embodiment, the crystal has atomic coordinates set forth in Table 3. In a specific embodiment, the crystal has atomic coordinates set forth in Table 4. In other embodiments, the crystal has atomic coordinates set forth in Table 5. In other embodiments, the crystal has atomic coordinates set forth in Table 6. In other embodiments, the crystal has atomic coordinates set forth in Table 7.

Generally speaking, those of skill in the art will understand that the term "coordinates" or "structure coordinates" refers to Cartesian coordinates derived from mathematical equations related to the patterns obtained on diffraction of a monochromatic beam of X-rays by the atoms (scattering centers) of a polypeptide in crystal form. The diffraction data are used to calculate an electron density map of the repeating unit of the crystal. The electron density maps are then used to estimate the positions of the individual atoms of the polypeptide to construct a polypeptide model. Those of skill in the art will also understand that a set of structure coordinates for a polypeptide model is a relative set of points that define a structure in three dimensions.

Those of skill in the art understand that a set of structure coordinates determined by X-ray crystallography is approximate and not without standard error. Due to inherent limitations of the resolution of diffraction data, the positions of individual atoms in a polypeptide model are necessarily approximate. Slight variations in atomic position within a polypeptide model will have little effect on overall shape and structure of the polypeptide model. If such variations are within an acceptable standard error as compared to the original coordinates, the resulting three-dimensional shape and structure is considered to be structurally equivalent. By way of example, those skilled in the art understand that a set of structure coordinates for a given polypeptide model having a root mean square deviation of non-hydrogen atoms of less than about 1.5 Å when superimposed on the non-hydrogen atom positions of a second set of structure coordinates for a second polypeptide model are typically considered to be substantially identical or homologous.

It also is possible that an entirely different set of coordinates could define a similar or identical shape. Slight variations in structure coordinates also can be generated by mathematically manipulating the coordinates of a polypeptide model. For example, the structure coordinates set forth herein could be manipulated by crystallographic permutations of the structure coordinates, fractionalization of the structure coordinates, integer additions or subtractions to sets of the structure coordinates, inversion of the structure coordinates, or any combination thereof. Alternatively, modification in the crystal structure due to mutations, additions, substitutions, and/or deletions of amino acids, or other changes in any of the components that make up the crystal, could also account for variations in structure coordinates. If such variations are within an acceptable standard error as compared to the original coordinates, the resulting three-dimensional shape is considered to be the same as that of the unmodified crystal structure.

In some embodiments, the crystal comprises a fragment of CRBN. In other embodiments, the crystal comprises a fragment of CRBN, either alone or in combination with DDB1 and/or a CMA provided herein.

In certain embodiments, the three-dimensional structure is indicative of a conformational change or alteration in the CRBN. In some embodiments, the CRBN conformational change or alteration is as compared to an unbound CRBN. In other embodiments, the CRBN conformational change or alteration is as compared to complex comprising the CRBN and an analog of the CMA. In yet other embodiments, the CRBN conformational change or alteration is as compared to a complex comprising CRBN and a different CMA.

Also provided herein is a crystal of a complex comprising CRBN and a CMA, or an analog thereof. Also provided herein is a method of obtaining the crystal, comprising concentrating a purified complex of the CRBN and the CMA, or analog thereof, and obtaining the crystal. In certain embodiments, the method further comprises methods provided in Example 6.10 below.

Also provided herein is a crystal of a complex comprising CRBN and a compound, wherein said crystal has a three-dimensional structure as determined by x-ray diffraction having the following atomic coordinates. In one embodiment, the crystal has atomic coordinates as set forth in any one of Tables 3, 4, 5, 6 or 7. In some embodiments, the crystal has a three dimensional structure as set forth in any one of FIG. 12-18 or 20. In certain embodiments, the CRBN is complexed with (or otherwise bound to) DDB1. In other embodiments, the CRBN is complexed with (or otherwise bound to) a CMA. In certain embodiments, the CMA is thalidomide, pomalidomide or lenalidomide. In other embodiments, the CRBN is complexed with (or otherwise bound to) DDB and a CMA. Exemplary crystals and methods of making the crystals are provided in Example 6.10 below.

In one embodiment, the crystal has atomic coordinates set forth in Table 3. In a specific embodiment, the crystal has atomic coordinates set forth in Table 4. In other embodiments, the crystal has atomic coordinates set forth in Table 5. In other embodiments, the crystal has atomic coordinates set forth in Table 6. In other embodiments, the crystal has atomic coordinates set forth in Table 7.

In some embodiments, the crystal comprises a fragment of CRBN. In other embodiments, the crystal comprises a fragment of CRBN, either alone or in combination with DDB1 and/or a CMA provided herein.

Also provided herein is a crystal of a complex comprising a CRBN and a compound, wherein said crystal has a three-dimensional structure as determined by x-ray diffraction, wherein said three-dimensional structure has atomic coordinates as set forth in any one of Tables 3, 4, 5, 6 or 7 indicative of CRBN conformational change or alteration. In some embodiments, the CRBN conformational change or alteration is as compared to a complex comprising CRBN and reference compound. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN.

In certain embodiments of the various compositions and methods provided herein, the CRBN is bound to DDB1. In some embodiments, the CRBN is bound to Cul4. In other embodiments, the CRBN is bound to Roc1. In some embodiments, the CRBN is bound to DDB1 and Cul4. In other embodiments, the CRBN is bound to DDB1 and Roc1. In yet other embodiments, the CRBN is bound to Cul4 and Roc1. In some embodiments, the CRBN is bound to DDB1, Cul4 and Roc1. In certain embodiments, CRBN that is bound to DDB1, Cul4 and/or Roc1 is a complex with DDB1, Cul4 and/or Roc1, respectively.

In some embodiments of the various compositions and methods provided herein, the CMA is an immunomodulatory compound provided herein (see, e.g., Section 5.9 below). In certain embodiments, the CMA is thalidomide. In other embodiments, the CMA is pomalidomide. In some embodiments, the CMA is Compound B. In other embodiments, the CMA is Compound C. In certain embodiments, the CMA is a thalidomide analog. In other embodiments, the CMA is a pomalidomide analog. In some embodiments, the CMA is a Compound B analog. In other embodiments, the CMA is a Compound C analog. In other embodiments, the CMA is not thalidomide. In other embodiments, the CMA is not pomalidomide. In some embodiments, the CMA is not Compound B. In other embodiments, the CMA is not Compound C. In other embodiments, the CMA is not a thalidomide analog. In other embodiments, the CMA is not a pomalidomide analog. In other embodiments, the CMA is not a Compound B analog. In other embodiments, the CMA is not a Compound C analog.

Also provided herein are methods of identifying a compound that induces a CRBN conformational change (e.g., within the CMA-binding pocket of the CRBN) or otherwise alters the properties of a CRBN surface (e.g., on an adjacent region of the protein) comprising: (i) obtaining a crystal comprising a complex comprising the CRBN and the compound, (ii) determining the three-dimensional structure of the crystal by x-ray diffraction to obtain atomic coordinates, and (iii) comparing said atomic coordinates with atomic coordinates provided in any one of Tables 3, 4, 5, 6 or 7, wherein a change or shift in atomic coordinates is indicative of a compound that induces said CRBN conformational change or alteration. In certain embodiments, the atomic coordinates define the CMA binding domain. Also provided herein are compounds identified by these methods. In some embodiments, the test compound induces a CRBN conformational change or alteration. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein.

5.4 Methods of Inducing a CRBN Conformational Change or Alteration

Provided herein are methods of inducing a CRBN conformational change (e.g., within the CMA-binding pocket of the CRBN) or otherwise alters the properties of a CRBN surface (e.g., on an adjacent region of the protein), said method comprising contacting the CRBN with a CMA.

In certain embodiments, a conformational change in the CMA-binding pocket is induced. In other embodiments, an alteration in the properties of the CRBN surface is induced. In some embodiments, a CRBN surface adjacent to the CMA-binding pocket is altered. In other embodiments, one or more surrounding loops that are adjacent or otherwise surround the CMA binding pocket are altered. In certain embodiments, the properties of the CRBN surface are altered by the placement of a compound's appendages. In a specific embodiment, the compound is a CMA.

In some embodiments, the CRBN conformational change results in an altered substrate specificity, biological activity and/or therapeutic utility as compared to CRBN in the absence of the CMA. In some embodiments, the CRBN conformational change results in an altered substrate specificity, biological activity and/or therapeutic utility as compared to CRBN in the presence of a different CMA. In some embodiments, a CRBN conformational change is induced. In other embodiments, an alteration of the properties of a CRBN surface are induced.

Provided herein, in certain embodiments, is a method of inducing a CRBN conformational change (e.g., within the CMA-binding pocket of the CRBN) or otherwise alters the properties of a CRBN surface (e.g., on an adjacent region of the protein), comprising contacting the CRBN with a test compound, wherein said CRBN conformational change or alteration comprises a conformational change or alteration within the CMA binding pocket of the CRBN that is different than the conformational change or alteration within the CMA binding pocket of a CRBN contacted with a reference compound. In some embodiments, the CRBN conformational change or alteration results in a different biological activity. In some embodiments, the CRBN conformational change or alteration results in a different therapeutic utility. In other embodiments, the CRBN conformational change or alteration results in a different substrate specificity. In some embodiments, the test compound induces a CRBN conformational change or alteration. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

Also provided herein is a composition comprising a CRBN and a test compound, wherein said CRBN has a conformational change or alteration as compared to a reference compound. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

Also provided herein is a compound that induces a CRBN conformational change (e.g., within the CMA-binding pocket of the CRBN) or otherwise alters the properties of a CRBN surface (e.g., on an adjacent region of the protein) upon contact with said CRBN, as compared to the conformational change or alteration as compared to a reference compound. In some embodiments, the CRBN conformational change or alteration results in a different biological activity. In some embodiments, the CRBN conformational change or alteration results in a different therapeutic utility. In other embodiments, the CRBN conformational change or alteration results in a different substrate specificity. In some embodiments, the compound induces a CRBN conformational change or alteration. In other embodiments, the compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

Also provided herein is a complex comprising a CRBN and test compound, wherein said CRBN has a conformational change or alteration as compared to a conformational change or alteration of said CRBN contacted with a reference compound. In some embodiments, the CRBN has a conformational change or alteration. In other embodiments, the CRBN has an alteration of the properties of the CRBN surface. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

In various embodiments of the methods provided herein, the compound is a compound provided herein (see, e.g., Section 5.9 below). In other embodiments, the compound is not a compound provided herein. In various embodiments of the methods provided herein, the compound is a CMA. In certain embodiments, the CMA is thalidomide, lenalidomide, pomalidomide, 3-(5-amino-2-methyl-4-oxo-4H-quinazolin-3-yl)-piperidine-2,6-dione (Compound A) or 3-(4-((4-(morpholinomethyl)benzyl)oxy)-1-oxoisoindolin-2-yl) piperidine-2,6-dione, a stereoisomer thereof, or a pharmaceutically acceptable salt, solvate, hydrate, co-crystal, clathrate, or polymorph thereof. In certain embodiments of the methods provided herein, the CMA is not thalidomide, lenalidomide, pomalidomide, 3-(5-amino-2-methyl-4-oxo-4H-quinazolin-3-yl)-piperidine-2,6-dione (Compound A) or 3-(4-((4-(morpholinomethyl)benzyl)oxy)-1-oxoisoindolin-2-yl)piperidine-2,6-dione (Compound B), a stereoisomer thereof, or a pharmaceutically acceptable salt, solvate, hydrate, co-crystal, clathrate, or polymorph thereof. In an embodiment, the compound is lenalidomide. In another embodiment, the compound is Compound A. In some embodiments, the compound is not thalidomide. In other embodiments, the compound is not lenalidomide. In other embodiments, the compound is not Compound A. In some embodiments, the compound is not thalidomide, lenalidomide, Compound A, or any analog thereof.

In certain embodiments of the various compositions and methods provided herein, the substrate is a CRBN-associated protein.

In some embodiments, the CRBN-associated protein is Ikaros. In other embodiments, the CRBN-associated protein is Aiolos. In some embodiments, the CRBN-associated protein is Ikaros and Aiolos. In certain embodiments, the CRBN-associated protein is interferon. In other embodiments, the CRBN-associated protein is an interferon pathway protein. In some embodiments, the interferon pathway protein is interferon-induced transmembrane protein 3 (IFITM3) and/or interferon regulatory factor 7 (IRF7). In one embodiment of the methods provided herein, the CRBN-associated protein is IKZF3 (Aiolos) having a molecular weight of 58 kDa. In another embodiment of the methods provided herein, the CRBN-associated protein is IKZF3 (Aiolos) having a molecular weight of 42 kDa. Other isoforms of Ikaros and/or Aiolos are also contemplated herein. In various embodiments of the methods provided herein, the CRBN-associated protein is interferon, an interferon pathway protein, casein kinase 1, alpha 1 (CSNK1A1), or a combination thereof. In other embodiments, the CRBN-associated protein is DDB1, DDB2, GSK3B, CUL4A, CUL4B, XBP-1, FAS1, RANBP6, DUS3L, PHGDH, AMPK, IRF4 or NFκB. In various embodiments of the methods provided herein, the CRBN-associated protein is DDB1, PABPC1, HNRNPR, RPL19, SYNCRIP, H2AFX, HSPA8, ALDOA, HIST1H2AA, HSPA1A, XRCC6, RPL12, RPL18A, RPL4, HNRNPA2B1, HNRNPC, RPS2, SEC24C, RPL9, USP15, SEC24A, CTPS, ABCE1, EEF1A1, IPO5, CPSF6, KCNAB2, C7ORF42, SMC4, GNB3, H2AFZ, HIST1H1C, HIST1H1D, HIST1H1E, ACTB, CSNK2A1, CRBN, DDX21, DHX9, DNAJC1, G3BP1, HSPA1B, IGF2BP2, RPL10A, RPL13A, RPL14, RPL15, RPL21, RPL3, RPL30, RPL7, RPL7A, RPLP1, RPLP2, MYH10, ILF3, NCL, RPS13, RPS16, RPS19, RPS6, SND1, EIF2S2, HNRNPH2, UBB, EEF1G, TBL1XR1, NACA, EIF4A1, FASN, PPAT, G3BP2, TUBA1A, UBAP2L, MCM2, UAP1, TUBA1C, EIF2S1, EIF3J, PRKDC, MCM7, RPL11, TUBA1B, STAT3, PTRH2, PABPC4, PTPRC, MACF1, UBE2O, DUT, GNB2L1, NUP88, H2AFJ, SEC23B, PDXK, ACLY, ARID1A, GBE1, HSPA9, DDX17, FUBP1, FBXO21, EWSR1, IFI16, YWHAE, UBA52, COPSE, GNAS, UBE2Q1, FERMT3, NAP1L2, TPD52, VAPA, EEF1AL3, DDIT4, NEDD8, HIST1H1A, HIST1H1B, or PCM1. Other isoforms of the aforementioned CRBN-associated proteins are also contemplated herein.

In various embodiments of the methods provided herein, the CRBN-associated protein is GSPT1, GSPT2, HBS1L, IKZF1, IKZF3, CK1a, eRF1, BIP, PERK, GCN2, eIF2a, ATF4, ATF3, DDIT3, PPP1R15A, TNFRSF10B, GADD45A, TNFRSF1A, TNFRSF1B, FAS, FADD, IRE1, XBP1, SEC24D, DNAJB9, EDEM1, EDEM2, HYOU1, ATF6, HSPA5, Caspase 3, Caspase 7, Caspase 8, BID, Caspase 9, PARP, Mcl-1, and BAD. In a particular embodiment, the CAP is GSPT1. In another embodiment, the CAP is IKZF1. In yet another embodiment, the CAP is CK1a.

5.4.1. Inducing a CRBN Conformational Change to Alter Substrate Specificity

Also provided herein are methods of inducing a conformational change (e.g., within the CMA-binding pocket of the CRBN) or alteration of the properties of a CRBN surface (e.g., on an adjacent region of the protein), said method comprising contacting the CRBN with a CMA, wherein said CRBN conformational change or alteration results in an altered substrate specificity. In certain embodiments, the altered substrate specificity is as compared to a CRBN in the absence of the CMA. In other embodiments, the altered substrate specificity is as compared to a CRBN in the presence of a different CMA. In some embodiments, a CRBN conformational change or alteration is induced. In other embodiments, an alteration of the properties of a CRBN surface are induced.

In one aspect, provided herein is a method of inducing a CRBN conformational change (e.g., within the CMA-binding pocket of the CRBN) or otherwise alters the properties of a CRBN surface (e.g., on an adjacent region of the protein), comprising contacting the CRBN with a test compound, wherein said CRBN conformational change or alteration results in a different substrate specificity as compared to the substrate specificity of a CRBN that is contacted with a reference compound. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In some embodiments, a CRBN conformational change is induced. In other embodiments, an alteration of the properties of a CRBN surface are induced. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

Substrate specificity can be assessed using any method known to those in the art. In some embodiments, substrate specificity is assessed using UbiScan. In other embodiments, substrate specificity is assessed by quantitating the level of a protein or mRNA of a CRBN-associated protein as provided elsewhere herein.

5.4.2. Inducing a CRBN Conformational Change to Modulate a Biological Activity or Therapeutic Efficacy In some embodiments, CRBN conformational changes (e.g., within the CMA-binding pocket of the CRBN) or an alteration of the properties of a CRBN surface (e.g., on an adjacent region of the protein) following contact with a CMA results in an altered substrate specificity, wherein the altered substrate specificity, in turn, modulates downstream biological activity.

Provided herein are methods of inducing a CRBN conformational change (e.g., within the CMA-binding pocket of the CRBN) or otherwise alters the properties of a CRBN surface (e.g., on an adjacent region of the protein), said method comprising contacting the CRBN with a CMA, wherein said CRBN conformational change or alteration results in modulation of a biological activity in a cell or subject. In some embodiments, a CRBN conformational change is induced. In other embodiments, an alteration of the properties of a CRBN surface are induced.

In some embodiments, the conformational change or alteration occurs within the CMA binding pocket of the CRBN. In certain embodiments, the conformational change or alteration is assessed using any one of the methods provided herein. In certain embodiments, the conformational change or alteration in said CMA binding pocket has an effect on an adjacent region of the protein.

In another aspect, provided herein is a method of identifying a test compound that induces a specific biological activity, comprising contacting the test compound with CRBN, inducing a CRBN conformational change (e.g., within the CMA-binding pocket of the CRBN) or otherwise alters the properties of a CRBN surface (e.g., on an adjacent region of the protein), and assessing conformational change or alteration within the CMA-binding pocket of the CRBN, wherein conformational change or alteration is indicative of a specific biological activity. In some embodiments, the method further comprises assaying the specific biological activity. Also provided herein is a test compound identified by this method. In certain embodiments, the method further comprises administering said compound to a patient, wherein said biological activity is modulated in said patient. In certain embodiments, the patient has a disease, and wherein one or more symptoms of said disease are alleviated following said administration. In certain embodiments, the conformational change or alteration occurs in a CMA binding pocket of the CRBN. In some embodiments, the test compound induces a CRBN conformational change or alteration. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

In some embodiments, the biological activity is a tumoricidal effect. In one embodiment, the biological activity is modulation of apoptosis. In other embodiment, the biological activity is modulation of proliferation, e.g., an antiproliferative effect. In some embodiments, the biological activity is modulation of PBMC viability. In certain embodiments, the biological activity is modulation of toxicity. In other embodiments, the biological activity is substrate degradation. In certain embodiments, the biological activity is degradation of Aiolos and/or Ikaros. In certain embodiments, the biological activity is a prevention of substrate degradation. In some embodiments, the substrate is a CRBN-associated protein. In some embodiments, the biological activity is an immune-mediated effect. In certain embodiments, the biological effect is modulation of IL-2. In yet other embodiments, the biological effect is an effect on fetal hemoglobin (HbF). In some embodiments, the effect is an effect on a CRBN-associated protein.

In certain embodiments, a biological activity is observed in one cell type, but not another cell type. In a specific embodiments, the biological activity is directly correlated with an observed CRBN conformational shift in the cell type(s). In an embodiments, the CRBN conformational shift is in a CMA-binding pocket of CRBN. Such conformational shifts can be assessed using any of the various methods provided elsewhere herein.

In some embodiments, a biological activity is observed in one tissue type, but not another tissue type. In a specific embodiments, the biological activity is directly correlated with an observed CRBN conformational shift in the tissue type(s). In an embodiments, the CRBN conformational shift is in a CMA-binding pocket of CRBN. Such conformational shifts can be assessed using any of the various methods provided elsewhere herein.

In certain embodiments, a biological activity is observed in one tumor (or cancer) type, but not another tumor (or cancer) type. In a specific embodiments, the biological activity is directly correlated with an observed CRBN conformational shift in the tumor (cancer) type(s). In an embodiments, the CRBN conformational shift is in a CMA-binding pocket of CRBN. Such conformational shifts can be assessed using any of the various methods provided elsewhere herein.

In some embodiments, a biological activity is observed in a solid tumor (or cancer), but not in a non-solid tumor (or cancer) (e.g., a hematological tumor). In a specific embodiments, the biological activity is directly correlated with an observed CRBN conformational shift in the tumor(s) (or cancer(s)). In an embodiments, the CRBN conformational shift is in a CMA-binding pocket of CRBN. Such conformational shifts can be assessed using any of the various methods provided elsewhere herein.

In some embodiments, a biological activity is observed in a non-solid tumor (or cancer) (e.g., a hematological tumor), but not in a solid tumor (or cancer). In a specific embodiments, the biological activity is directly correlated with an observed CRBN conformational shift in the tumor(s) (or cancer(s)). In an embodiments, the CRBN conformational shift is in a CMA-binding pocket of CRBN. Such conformational shifts can be assessed using any of the various methods provided elsewhere herein.

In certain embodiments, the solid tumor or cancer is a breast, kidney, ovary, colon, bladder, brain, liver of prostate tumor or cancer. In some embodiments, the non-solid tumor is a blood (hematological) cancer.

In some embodiments, exemplary tumors or cancers include without limitation acute lymphoblastic leukemia, acute myeloid leukemia, Ewing's sarcoma, gestational trophoblastic carcinoma, Hodgkin's disease, non-Hodgkin's lymphoma, Burkitt's lymphoma diffuse large cell lymphoma, follicular mixed lymphoma, lymphoblastic lymphoma, rhabdomyosarcoma, testicular carcinoma, wilms's tumor, anal carcinoma, bladder carcinoma, breast carcinoma, chronic lymphocytic leukemia, chronic myelogenous leukemia, hairy cell leukemia, head and neck carcinoma, meningioma, neuro fibrosoma, angio fibrosoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, human large hepatocellular carcinoma, Kaposi's sarcoma, lung (non-small-cell) carcinoma, melanoma, pancreatic carcinoma, prostate carcinoma, soft tissue sarcoma, breast carcinoma, colorectal carcinoma (stage II), bone tumors, osteogenic sarcoma, ovarian carcinoma, uterine fibroids, testicular carcinoma, or combinations thereof.

In one aspect, provided herein is a method of inducing a biological activity in a cell comprising CRBN, comprising contacting said cell with a test compound, wherein said compound induces a conformational change (e.g., within the CMA-binding pocket of the CRBN) or alteration of the properties of a CRBN surface (e.g., on an adjacent region of the protein) of said CRBN, and wherein said CRBN conformational change or alteration is as compared to a reference compound, and wherein the conformational change or alteration results in said biological activity. In some embodiments, a CRBN conformational change or alteration is induced. In other embodiments, an alteration of the properties of a CRBN surface are induced. In some embodiments, the biological activity is a tumoricidal effect. In other embodiments, the biological activity is an apoptosis effect. In some embodiments, the biological activity is anti-proliferation. In yet other embodiments, the biological activity is PBMC viability. In some embodiments, the biological activity is toxicity. In certain embodiments, the biological activity is substrate degradation. In one embodiments, the biological activity is Aiolos degradation. In another embodiments, the biological activity is Ikaros degradation. In other embodiments, the biological activity is an immune-mediated effect. In another embodiment, the biological activity is IL-2 induction. In some embodiments, the biological activity is IL-2 repression. In yet other embodiments, the biological activity is a HbF effect. Any combination of one, two, three or more of the aforementioned biological activities is also contemplated. In certain embodiments, the biological activity is based on specific cell type categories. In other embodiments, the biological activity is based on specific tissue type categories. In yet other embodiments, the biological activity is based on solid tumors or solid tumor categories. In some embodiments, the biological activity is based on non-solid tumor categories. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In an embodiment, the conformational change or alteration is assessed by x-ray crystallography. In another embodiment, the conformational is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof. In some embodiments, the reference compound is an immunomodulatory compound provided herein.

In certain embodiments, the biological activity being modulated by the CMA has a direct effect on therapeutic utility of the CMA in a subject.

In one aspect, provided herein is a method of inducing a CRBN conformational change (e.g., within the CMA-binding pocket of the CRBN) or otherwise altering the properties of a CRBN surface (e.g., on an adjacent region of the protein), comprising contacting the CRBN with a compound, wherein said CRBN conformational change or alteration results in a specific therapeutic utility. In some embodiments, a CRBN conformational change or alteration is induced. In other embodiments, an alteration of the properties of a CRBN surface are induced. In some embodiments, the therapeutic utility is based on solid tumors or solid tumor categories. In other embodiments, the therapeutic utility is based on non-solid tumor categories. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

In another aspect, provided herein is a method of identifying a test compound that has a specific therapeutic utility, comprising contacting the test compound with CRBN, inducing a CRBN conformational change (e.g., within the CMA-binding pocket of the CRBN) or otherwise altering the properties of a CRBN surface (e.g., on an adjacent region of the protein), and assessing the conformational change or alteration within the CMA-binding pocket of the CRBN, wherein a conformational change or alteration is indicative of the specific therapeutic utility. In some embodiments, a CRBN conformational change is induced. In other embodiments, an alteration of the properties of a CRBN surface are induced. Also provided herein is a test compound identified by this method. In some embodiments, the method further comprises administering said compound to a patient having a disease, wherein one or more symptoms of said disease is alleviated following said administration. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

In certain embodiments of the methods provided herein, the contacting in step (a) is performed in vitro. In other embodiments, the contacting in step (a) is performed in vivo. In one embodiment, the CRBN is are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days.

In some embodiments of the various methods provided herein, the therapeutic utility is the management or treatment of a CRBN-associated disease, disorder or a symptom thereof. In other embodiments, the therapeutic utility is the management or treatment of a cancer or tumor, or a symptom thereof. In some embodiments, the tumor or cancer is a liver cancer, kidney cancer, acute lymphoblastic leukemia, acute myeloid leukemia, Ewing's sarcoma, gestational trophoblastic carcinoma, Hodgkin's disease, non-Hodgkin's lymphoma, Burkitt's lymphoma diffuse large cell lymphoma, follicular mixed lymphoma, lymphoblastic lymphoma, rhabdomyosarcoma, testicular carcinoma, wilms's tumor, anal carcinoma, bladder carcinoma, breast carcinoma, chronic lymphocytic leukemia, chronic myelogenous leukemia, hairy cell leukemia, head and neck carcinoma, meningioma, neuro fibrosoma, angio fibrosoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, human large hepatocellular carcinoma, Kaposi's sarcoma, lung (non-small-cell) carcinoma, melanoma, pancreatic carcinoma, prostate carcinoma, soft tissue sarcoma, breast carcinoma, colorectal carcinoma (stage II), bone tumors, osteogenic sarcoma, ovarian carcinoma, uterine fibroids, testicular carcinoma, or combinations thereof. In some embodiments, the cancer or tumor is a lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma.

In another aspect, provided herein is a method of treating or alleviating one or more symptoms of a CRBN-mediated disease or disorder in a patient, comprising administering a test compound to the subject, wherein said compound induces a conformational change or alteration of said CRBN, and wherein said CRBN conformational change or alteration is as compared to a reference compound, and wherein said CRBN conformational change or alteration results in treatment or alleviation of one or more symptoms of said disease or disorder. In certain embodiments, the disease or disorder is a cancer or tumor. In some embodiments, the test compound induces a CRBN conformational change or alteration. In other embodiments, the test compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-electron microscopy. In some embodiments, the CRBN is further bound to DDB1, Cul4, Roc1, or any combination thereof. In some embodiments provided herein is a (test) compound for use in a method of treating or alleviating one or more symptoms of a CRBN-mediated disease or disorder in a patient, wherein the method comprises administering the (test) compound to a patient, wherein said compound is as described above.

Also provided herein is a method of alleviating one or more symptoms of a CRBN-associated disease, disorder, or a symptom thereof, in a patient, comprising administering a compound to the subject, wherein said compound induces a CRBN conformational change (e.g., within the CMA-binding pocket of the CRBN) or otherwise alters the properties of a CRBN surface (e.g., on an adjacent region of the protein) in a cell of said subject. In some embodiments, a CRBN conformational change is induced. In other embodiments, an alteration of the properties of a CRBN surface are induced. In some embodiments, the CRBN conformational change or alteration is assessed using a method provided elsewhere herein. In certain embodiments, the CRBN conformational change or alteration comprises atomic coordinates as provided in any one of Tables 3-5, or FIG. 12-18 or 20. In some embodiments, the CRBN conformational change or alteration results in alleviation of one or more symptoms of said CRBN-mediated disease or disorder in the patient. In some embodiments provided herein is a compound for use in a method of alleviating one or more symptoms of a CRBN-associated disease, disorder, or a symptom thereof, in a patient, the method comprises administering a compound to the subject.

In some embodiments of the various methods provided herein, the CRBN-associated disease or disorder is a cancer or tumor. In other embodiments, the CRBN-associated disease or disorder is not a cancer or tumor. In some embodiments, the tumor or cancer is a liver cancer, kidney cancer, acute lymphoblastic leukemia, acute myeloid leukemia, Ewing's sarcoma, gestational trophoblastic carcinoma, Hodgkin's disease, non-Hodgkin's lymphoma, Burkitt's lymphoma diffuse large cell lymphoma, follicular mixed lymphoma, lymphoblastic lymphoma, rhabdomyosarcoma, testicular carcinoma, wilms's tumor, anal carcinoma, bladder carcinoma, breast carcinoma, chronic lymphocytic leukemia, chronic myelogenous leukemia, hairy cell leukemia, head and neck carcinoma, meningioma, neuro fibrosoma, angio fibrosoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, human large hepatocellular carcinoma, Kaposi's sarcoma, lung (non-small-cell) carcinoma, melanoma, pancreatic carcinoma, prostate carcinoma, soft tissue sarcoma, breast carcinoma, colorectal carcinoma (stage II), bone tumors, osteogenic sarcoma, ovarian carcinoma, uterine fibroids, testicular carcinoma, or combinations thereof. In some embodiments, the cancer or tumor is a lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma.

5.4.3. Methods of Assaying a Specific Biological Activity

In certain embodiments of the methods provided herein, the method comprises assaying a specific biological activity. In certain embodiments, the biological activity is substrate degradation. In certain embodiments, the substrate is a CRBN-associated protein. In some embodiments, the CRBN-associated protein is detected and/or quantified. In some embodiments, the methods comprises: (a) contacting the sample with a first antibody that immunospecifically binds to the CRBN-associated protein; (b) contacting the sample bound to the first antibody with a second antibody with a detectable label, wherein the second antibody immunospecifically binds to the CRBN-associated protein, and wherein the second antibody immunospecifically binds to a different epitope on CRBN-associated protein than the first antibody; (c) detecting the presence of second antibody bound to the sample; and (d) determining the protein level of the CRBN-associated protein based on the amount of detectable label in the second antibody. In one embodiment, the CRBN-associated protein is Ikaros. In another embodiment, the CRBN-associated protein is Aiolos. In yet another embodiment, the CRBN-associated protein is Ikaros and Aiolos. In yet other embodiments, the CRBN-associated protein is interferon. In other embodiments, the CRBN-associated protein is an interferon pathway protein. In other embodiments, the interferon pathway protein is interferon-induced transmembrane protein 3 (IFITM3) and/or interferon regulatory factor 7 (IRF7). In yet other embodiments, the CRBN-associated protein is casein kinase 1, alpha 1 (CSNK1A1).

In other embodiments, the method comprises: (a) obtaining RNA from the sample; (b) contacting the RNA with a primer comprising a sequence specifically binding to a sequence in the RNA to generate a first DNA molecule having a sequence complementary to said RNA; (c) amplifying the DNA corresponding to a segment of a gene encoding the CRBN-associated protein; and (d) determining the RNA level of the CRBN-associated protein based on the amount of the amplified DNA. In one embodiment, the CRBN-associated protein is Ikaros. In another embodiment, the CRBN-associated protein is Aiolos. In yet another embodiment, the CRBN-associated protein is Ikaros and Aiolos. In yet other embodiments, the CRBN-associated protein is interferon. In other embodiments, the CRBN-associated protein is an interferon pathway protein. In other embodiments, the interferon pathway protein is interferon-induced transmembrane protein 3 (IFITM3) and/or interferon regulatory factor 7 (IRF7). In yet other embodiments, the CRBN-associated protein is casein kinase 1, alpha 1 (CSNK1A1).

In certain embodiments, the CRBN-associated protein is DDB1, DDB2, GSK3B, CUL4A, CUL4B, XBP-1, FAS1, RANBP6, DUS3L, PHGDH, AMPK, IRF4 or NFκB. In certain embodiments, the CRBN-associated protein is DDB1, PABPC1, HNRNPR, RPL19, SYNCRIP, H2AFX, HSPA8, ALDOA, HIST1H2AA, HSPA1A, XRCC6, RPL12, RPL18A, RPL4, HNRNPA2B1, HNRNPC, RPS2, SEC24C, RPL9, USP15, SEC24A, CTPS, ABCE1, EEF1A1, IPO5, CPSF6, KCNAB2, C7ORF42, SMC4, GNB3, H2AFZ, HIST1H1C, HIST1H1D, HIST1H1E, ACTB, CSNK2A1, CRBN, DDX21, DHX9, DNAJC1, G3BP1, HSPA1B, IGF2BP2, RPL10A, RPL13A, RPL14, RPL15, RPL21, RPL3, RPL30, RPL7, RPL7A, RPLP1, RPLP2, MYH10, ILF3, NCL, RPS13, RPS16, RPS19, RPS6, SND1, EIF2S2, HNRNPH2, UBB, EEF1G, TBL1XR1, NACA, EIF4A1, FASN, PPAT, G3BP2, TUBA1A, UBAP2L, MCM2, UAP1, TUBA1C, EIF2S1, EIF3J, PRKDC, MCM7, RPL11, TUBA1B, STAT3, PTRH2, PABPC4, PTPRC, MACF1, UBE2O, DUT, GNB2L1, NUP88, H2AFJ, SEC23B, PDXK, ACLY, ARID1A, GBE1, HSPA9, DDX17, FUBP1, FBXO21, EWSR1, IFI16, YWHAE, UBA52, COPSE, GNAS, UBE2Q1, FERMT3, NAP1L2, TPD52, VAPA, EEF1AL3, DDIT4, NEDD8, HIST1H1A, HIST1H1B, PCM1. In some embodiments, these CRBN-associated proteins are evaluated in combination with other CRBN-associated proteins provided herein, such as Ikaros, Aiolos, interferon, an interferon pathway protein, and/or casein kinase 1, alpha 1.

In various embodiments of the methods provided herein, the CRBN-associated protein is GSPT1, GSPT2, HBS1L, IKZF1, IKZF3, CK1a, eRF1, BIP, PERK, GCN2, eIF2a, ATF4, ATF3, DDIT3, PPP1R15A, TNFRSF10B, GADD45A, TNFRSF1A, TNFRSF1B, FAS, FADD, IRE1, XBP1, SEC24D, DNAJB9, EDEM1, EDEM2, HYOU1, ATF6, HSPA5, Caspase 3, Caspase 7, Caspase 8, BID, Caspase 9, PARP, Mcl-1, and BAD. In a particular embodiment, the CAP is GSPT1. In another embodiment, the CAP is IKZF1. In yet another embodiment, the CAP is CK1a.

In certain embodiments of the various methods provided herein, the two or more of the steps are performed sequentially. In other embodiments of the methods provided herein, two or more of steps are performed in parallel (e.g., at the same time).

Exemplary assays provided herein for the methods of detecting and quantifying the protein level of CRBN-associated protein are immunoassays such as western blot analysis, and an enzyme-linked immunosorbent assay (ELISA) (e.g., a sandwich ELISA). An exemplary assay provided herein for the methods of detecting and quantifying the RNA level of a CRBN-associated protein is reverse transcription polymerase chain reaction (RT-PCR), e.g., quantitative PCR or qPCR.

5.4.4. Types of Cells

In certain embodiments, the biological activity is based on specific cell type categories. Such cells can include any type of cells, e.g., stem cells, blood cells (e.g., peripheral blood mononuclear cells), lymphocytes, B cells, T cells, monocytes, granulocytes, immune cells, or tumor or cancer cells.

For example, B cells (B lymphocytes) include plasma B cells, memory B cells, B1 cells, B2 cells, marginal-zone B cells, and follicular B cells. B cells can express immunoglobulins (antibodies, B cell receptor). In one embodiment, the cells are Karpas 422, TMD8, WSU-DLCL2, OCI-LY10, Karpas 1106P, HT, SUDHL-10, Riva, OCI-LY19, SUDHL-4, SUDHL-6, OCI-LY3, and Farage.

Specific cell populations can be obtained or assessed using a combination of commercially available antibodies (e.g., Quest Diagnostic (San Juan Capistrano, Calif.); Dako (Denmark)).

In certain embodiments, the cell line is lenalidomide-resistant WSU-DLCL2 or TMD8 cell line. In certain embodiments, the cell line is a DLBCL cell line. In some embodiments, the cell line is a ABC-DLBCL (activated B cell-like DLBCL) cell line, for example, TMD8, OCI-LY10, Riva, or OCI-LY3 cell line. In other embodiments, the cell line is a GCB-DLBCL (germinal center B cell-like DLBCL) cell line, for example, Karpas 422, WSU-DLCL2, Karpas 1106P, HT, SUDHL-10, OCI-LY19, SUDHL-4, or SUDHL-6 cell line.

In some embodiments, the number and type of cells can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used or detected in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

In one embodiment, the RNA (e.g., mRNA) or protein is purified and the presence or absence of a biomarker is measured by gene or protein expression analysis. In certain embodiments, the presence or absence of a biomarker is measured by quantitative real-time PCR (QRT-PCR), microarray, flow cytometry or immunofluorescence. In other embodiments, the presence or absence of a biomarker is measured by enzyme-linked immunosorbent assay-based methodologies (ELISA) or other similar methods known in the art.

5.4.5. Methods of Detecting mRNA Levels in a Sample

Several methods of detecting or quantitating mRNA levels are known in the art. Exemplary methods include but are not limited to northern blots, ribonuclease protection assays, PCR-based methods, and the like. The mRNA sequence, e.g., the mRNA of CRBN or CRBN-associated proteins, or a fragment thereof, can be used to prepare a probe that is at least partially complementary. The probe can then be used to detect the mRNA sequence in a sample, using any suitable assay, such as PCR-based methods, Northern blotting, a dipstick assay, and the like.

In other embodiments, a nucleic acid assay for testing for immunomodulatory activity in a biological sample can be prepared. An assay typically contains a solid support and at least one nucleic acid contacting the support, where the nucleic acid corresponds to at least a portion of an mRNA that has altered expression during an immunomodulatory treatment in a patient, such as the mRNA of CRBN or CRBN-associated proteins. The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of the mRNA in a sample. For example, an assay may be in the form of a dipstick, a membrane, a chip, a disk, a test strip, a filter, a microsphere, a slide, a multiwell plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4', 5' dichloro 2', 7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

In some embodiments, the mRNA sequences comprise at least one mRNA selected from the group consisting of the mRNA of DDB1, PABPC1, HNRNPR, RPL19, SYNCRIP, H2AFX, HSPA8, ALDOA, HIST1H2AA, HSPA1A, XRCC6, RPL12, RPL18A, RPL4, HNRNPA2B1, HNRNPC, RPS2, SEC24C, RPL9, USP15, SEC24A, CTPS, ABCE1, EEF1A1, IPO5, CPSF6, KCNAB2, C7ORF42, SMC4, GNB3, H2AFZ, HIST1H1C, HIST1H1D, HIST1H1E, ACTB, CSNK2A1, CRBN, DDX21, DHX9, DNAJC1, G3BP1, HSPA1B, IGF2BP2, RPL10A, RPL13A, RPL14, RPL15, RPL21, RPL3, RPL30, RPL7, RPL7A, RPLP1, RPLP2, MYH10, ILF3, NCL, RPS13, RPS16, RPS19, RPS6, SND1, EIF2S2, HNRNPH2, UBB, EEF1G, TBL1XR1, NACA, EIF4A1, FASN, PPAT, G3BP2, TUBA1A, UBAP2L, MCM2, UAP1, TUBA1C, EIF2S1, EIF3J, PRKDC, MCM7, RPL11, TUBA1B, STAT3, PTRH2, PABPC4, PTPRC, MACF1, UBE2O, DUT, GNB2L1, NUP88, H2AFJ, SEC23B, PDXK, ACLY, ARID1A, GBE1, HSPA9, DDX17, FUBP1, FBXO21, EWSR1, IFI16, YWHAE, UBA52, COPSE, GNAS, UBE2Q1, FERMT3, NAP1L2, TPD52, VAPA, EEF1AL3, DDIT4, NEDD8, HIST1H1A, HIST1H1B, PCM1, IKZF1, IKZF3, IFITM3, or CSNK1A1, or a fragment thereof. In one embodiment, the mRNA is Ikaros mRNA. In another embodiment, the mRNA is Aiolos mRNA. In another embodiment, the mRNA is IFITM3 mRNA. In another embodiment, the mRNA is CSNK1A1 mRNA. The nucleic acids may be present in specific, addressable locations on a solid support; each corresponding to at least a portion of mRNA sequences that are differentially expressed upon treatment of an immunomodulatory compound in a cell or a patient.

A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to follow the expression of CRBN or CRB-associated proteins. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, Real-Time Reverse Transcription-PCR (qRT-PCR) can be used for both the detection and quantification of RNA targets (Bustin, et al., 2005, *Clin. Sci.*, 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as the Applied Biosystems 7500, are available commercially, as are the reagents, such as TaqMan Sequence Detection chemistry. For example, TaqMan® Gene Expression Assays can be used, following the manufacturer's instructions. These kits are pre-formulated gene expression assays for rapid, reliable detection and quantification of human, mouse and rat mRNA transcripts. An exemplary PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the CT), the data can be analyzed, for example, using a 7500 Real-Time PCR System Sequence Detection software v1.3 using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

5.4.6. Methods of Detecting Polypeptide or Protein Levels in a Sample

Several protein detection and quantitation methods can be used to measure the level of CRBN-associated proteins. Any suitable protein quantitation method can be used. In some embodiments, antibody-based methods are used. Exemplary methods that can be used include but are not limited to immunoblotting (western blot), enzyme-linked immunosorbent assay (ELISA), immunohistochemistry, flow cytometry, cytometric bead array, mass spectroscopy, and the like. Several types of ELISA are commonly used, including direct ELISA, indirect ELISA, and sandwich ELISA. In one embodiment, the CRBN-associated protein is Ikaros. In another embodiment, the CRBN-associated protein is Aiolos. In another embodiment, the CRBN-associated protein is interferon or an interferon pathway protein. In another embodiment, the CRBN-associated protein is casein kinase 1, alpha 1.

5.5 Substrate CRBN-Modifying Agents as Bridge to Substrate

Also provided herein are methods of using CMA as a bridge or "molecular glue" between CRBN, or a CRBN complex thereof, and a substrate.

Small molecules, such as plant auxins have previously been shown to promote protein-protein interactions in ubiquitin ligases. See, e.g., Tan et al. (2007) "Mechanism of auxin perception by the TIR1 ubiquitin ligase" *Nature* 446:640-645. Auxins, such as indole-3-acetic acid (IAA), are plant hormones that control many aspects of plant growth. Recent genetic and molecular studies in *Arabidopsis* revealed a crucial intracellular auxin signaling pathway in which a ubiquitin-dependent proteolytic system has a key role in sensing and transducing the hormone signal to transcriptional programs. At the center of the signaling cascade is the ubiquitin-ligase complex, $SCF^{TIR1}$, which promotes the ubiquitin-dependent proteolysis of a family of transcriptional regulators known as Aux/IAAs in an auxin-dependent manner. TIR1, the F-box protein subunit of $SCF^{TIR1}$ functions as the true auxin receptor. It has been shown that auxin binds directly to $SCF^{TIR1}$ and promotes the interaction between TIR1 and Aux/IAAs. Using crystallographic analysis, Tan et al. showed that TIR1 has a auxin and substrate binding pocket, analogous to a three-wall room with an open ceiling. The natural auxin, IAA, binds and is tethered to the bottom of the TIR1 pocket. IAA7 degron peptide is the natural substrate and docks to the auxin-bound TIR1, enclosing the three-walled TIR1 pocket. While auxin binding does not induce significant conformational changes of the TIR1 hormone receptor, auxin does serve to enhance the substrate-binding activity of TIR1 by filling a cavity between the two proteins and extending the protein interaction interface. Upon interacting with both TIR1 and the substrate polypeptide, auxin mediates the formation of a continuous hydrophobic core among the three proteins, and acts as a "molecular glue" rather than an alosteric switch.

Jasomonites are another family of plant hormones that regulate plan growth, development and response to stress. See, e.g., Shears et al. (2010) "Jasmonate perception by inositol-phosphate-potentiated COI1-JAZ co-receptor" *Nature* 468:400-407. COI1 shares high homology with TIR1 and is an F-box protein that functions as the substrate-recruiting module of the Skp1-Cul1-F-box protein (SCF) ubiquitin E3 ligase complex. The jasmonate zim domain (JAZ) family of transcriptional repressors are $SCF^{COI1}$ substrate targets, which associate with COI1 in a hormone-dependent manner. Crystallographic studies reveals that the direct interaction of jasmonite hormones with both the COI1 and JAZ protein is another example of utilization of a "molecular glue" mechanism to enhance the substrate-binding activity of the receptor.

5.6 Substrate Recruitment by CRBN-Modifying Agents

In certain embodiments, provided herein are methods of recruiting a substrate for ubiquitination by a E3 ubiquitination ligase complex comprising CRBN. In some embodiments, the method comprises contacting a CRBN with a CMA, resulting in a three-dimensional change of the CRBN (e.g., in the CMA-binding pocket) as provided elsewhere herein. In some embodiments, the method results in a CRBN conformational change. In other embodiments, the method results in an alteration of the properties of a CRBN surface. In a specific embodiment, the CRBN conformational change or alteration results in recruitment and ubiquitination of the substrate. In certain embodiments, the substrate is not ubiquitinated by the E3 ubiquitination ligase complex in the absence of the CMA. In one embodiment, the compound induces a conformational change or alteration having atomic coordinates as set forth in any one of Tables 3, 4, 5, 6 or 7; or a three dimensional structure as set forth in any one of FIG. 12-18 or 20. In certain embodiments, the conformational change or alteration is as compared to that having atomic coordinates as set forth in any one of Tables 3, 4, 5, 6 or 7; or a three dimensional structure as set forth in any one of FIG. 12-18 or 20. In certain embodiments, an isoindolinone ring is exposed on the surface of a CRBN-CMA complex. In some embodiments, the isoindolinone ring of the CRBN-CMA complex forms part of a neomorphic interface in substrate recruitment. In certain embodiments, the unused hydrophobic and/or polar bonding potential of the CMA and adjacent protein surface alters substrate recruitment. In other embodiments, the unused hydrophobic and/or polar bonding potential of the CMA and adjacent protein surface enhances substrate recruitment.

In a one aspect, provided herein is a method of recruiting a substrate for ubiquitination by a E3 ubiquitination ligase complex comprising CRBN, said method comprising contacting said CRBN with a compound that induces a CRBN conformational change (e.g., within the CMA-binding pocket of the CRBN) or otherwise alters the properties of a CRBN surface (e.g., on an adjacent region of the protein), wherein said CRBN conformational change or alteration results in recruitment and ubiquitination of said substrate; and wherein said substrate is not ubiquitinated by said E3 ubiquitination ligase complex in the absence of said compound. In some embodiments, the conformational change or alteration is as compared to the CMA binding pocket when the CRBN is contacted with a reference compound. In some embodiments, a CRBN conformational change is induced. In other embodiments, an alteration of the properties of a CRBN surface are induced. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

In another aspect, provided herein is a method of identifying a substrate ubiquitinated by a E3 ubiquitination ligase complex comprising CRBN, said method comprising: (i) contacting said CRBN with a compound that induces a CRBN conformational change (e.g., within the CMA-binding pocket of the CRBN) or otherwise alters the properties of a CRBN surface (e.g., on an adjacent region of the protein), wherein said CRBN conformational change or alteration results in ubiquitination of said substrate, (ii) assaying for ubiquitination of one or more substrates, and (iii) identifying said one or more ubiquitinated substrates; wherein said substrate is not ubiquitinated by said E3 ubiquitination ligase complex in the absence of said compound. In some embodiments, the compound induces a CRBN conformational change or alteration. In other embodiments, the compound alters the properties of the CRBN surface. In certain embodiments, the properties of the CRBN surface are altered by the placement of compound appendages. In certain embodiments, the conformational change or alteration occurs in a CMA binding pocket of the CRBN. In some embodiments, the conformational change or alteration in said CMA binding pocket has an effect on W380, W386 and/or W400 of CRBN. In other embodiments, the conformational change or alteration in said CMA binding pocket has an effect on E377 of CRBN. In other embodiments, the conformational change or alteration in said CMA binding pocket has an effect on V388 of CRBN. In certain embodiments, the conformational change or alteration in said CMA binding pocket has an effect on an adjacent region of the protein. Also provided is a substrate identified by this method. In some embodiments, the conformational change or alteration is as compared to the CMA binding pocket when the CRBN is contacted with a reference compound. In certain embodiments, the conformational change or alteration occurs in a CMA binding pocket of the CRBN. In an embodiment, the conformational change or alteration is assessed by x-ray crystallography. In another embodiment, the conformational change or alteration is assessed by a method comprising (a) (i) obtaining a first crystal structure of CRBN and a reference compound, and (ii) determining a three-dimensional structure of the first crystal by x-ray diffraction to obtain a first set of atomic coordinates; (b) (i) obtaining a second crystal comprising CRBN and the test compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of conformational change (e.g., within the CMA-binding pocket of the CRBN) or alteration of the properties of a CRBN surface (e.g., on an adjacent region of the protein). In certain embodiments, the conformational change or alteration is assessed by a method comprising (a) (i) obtaining a first three-dimensional structure of CRBN and a reference compound; (b) (i) obtaining a second three-dimensional structure of CRBN and the test compound; and (c) comparing said first three-dimensional structure with said second three-dimensional structure; wherein a difference in the first and second three-dimensional structures is indicative of a compound that induces a CRBN conformational change or alteration. In some embodiments, the first and/or second three-dimensional structures include a CMA binding domain of the CRBN. In other embodiments, the three-dimensional structure is assessed using x-ray crystallography, NMR spectroscopy, dual polarization interferometry, vibrational spectroscopy, or cryo-elecron microscopy. In some embodiments, the CRBN is further bound to DDB1, Cul4, Roc1, or any combination thereof.

5.7 Changes in Substrate Distribution and Abundance

Also provided herein are methods of modulating the distribution pattern and/or abundance of a substrate in a cell. In some embodiments, the method comprises contacting a CRBN with a CMA, resulting in a CRBN conformational change (e.g., within the CMA-binding pocket of the CRBN) or other alteration of the properties of a CRBN surface (e.g., on an adjacent region of the protein), as provided elsewhere herein. In some embodiments, the CRBN has a conformational change. In other embodiments, the CRBN has an alteration of the properties of the CRBN surface. In a specific embodiment, the CRBN conformational change or alteration results in a modulation of the distribution pattern of a substrate in a cell. In other embodiments, the CRBN conformational change or alteration results in a modulation of the abundance of a substrate in a cell. In some embodiments, the modulation is an increase. In other embodiments, the modulation is a decrease. In certain embodiments, the substrate is a CRBN-associated protein.

5.8 Degron in Substrate and Methods for Identifying Substrates Based on Degron Information As shown in the Examples, certain region (amino acid sequence or degron) of the substrate protein is important for its binding to CRBN and for its functionality, and such degron may be shared by various CRBN substrates and compound targets. Thus, in another aspect, provided herein are a degron in the CAP, and methods for searching new substrates of CRBN and/or targets of the treatment compound based on the degron information.

In some embodiments, provided herein is a degron in a CAP, wherein the degron is a structural degron. In some embodiments, the structural degron comprises an a-turn.

In certain embodiments, the degron comprises 4 amino acid residues, with positions designated as i, i+1, i+2, and i+3, respectively. In other embodiments, the degron further comprises an amino acid residue at position i−1.

In some embodiments, the amino acid residues at position i, i+1, or i+2 form hydrogen bonds with amino acid residues on CRBN. In one embodiment, the amino acid residue at position i form hydrogen bonds with amino acid residues on CRBN. In another embodiment, the amino acid residue at position i+1 form hydrogen bonds with amino acid residues on CRBN. In yet another embodiment, the amino acid residue at position i+2 form hydrogen bonds with amino acid residues on CRBN. In still another embodiment, the amino acid residues at positions i and i+1 form hydrogen bonds with amino acid residues on CRBN. In one embodiment, the amino acid residues at positions i and i+2 form hydrogen bonds with amino acid residues on CRBN. In another embodiment, the amino acid residues at positions i+1 and i+2 form hydrogen bonds with amino acid residues on CRBN. In yet another embodiment, the amino acid residues at position i, i+1, and i+2 form hydrogen bonds with amino acid residues on CRBN.

In certain embodiments, the amino acid residue at position i+3 is Glycine (G).

In some embodiments, the degron is stabilized by internal hydrogen bonds from an ASX motif and a ST motif.

In certain embodiments, the degron comprises an ASX motif that starts with Aspartic Acid (D). In other embodiments, the degron comprises an ASX motif that starts with Asparagine (N).

In some embodiments, the degron comprises a ST motif that starts with Serine (S). In other embodiments, the degron comprises a ST motif that starts with Threonine (T).

In certain embodiments, the degron comprises an amino acid sequence of [D/N]XX[S/T]G (SEQ ID NO:11), wherein X can be any amino acid residue. In one embodiment, the degron comprises an amino acid sequence of DXXSG (SEQ ID NO:12). In another embodiment, the degron comprises an amino acid sequence of NXXSG (SEQ ID NO:13). In yet another embodiment, the degron comprises an amino acid sequence of DXXTG (SEQ ID NO:14). In still another embodiment, the degron comprises an amino acid sequence of NXXTG (SEQ ID NO:15).

In some embodiments, the degron comprises an amino acid sequence of CXXCG (SEQ ID NO:16), wherein X can be any amino acid residue. In certain embodiments, the degron comprises an amino acid sequence of NXXNG (SEQ ID NO:17), wherein X can be any amino acid residue.

In some embodiments, one or more amino acids of the degron form hydrogen bonds with one or more amino acids within amino acid residues 300-450 of CRBN. In some embodiments, one or more amino acids of the degron form hydrogen bonds with one or more amino acids within amino acid residues 350-430 of CRBN. In some embodiments, one or more amino acids of the degron form hydrogen bonds with one or more amino acids within amino acid residues 351-422 of CRBN. In some embodiments, one or more amino acids of the degron form hydrogen bonds with one or more amino acids within amino acid residues 351-357 of CRBN. In some embodiments, one or more amino acids of the degron form hydrogen bonds with one or more amino acids within amino acid residues 377-400 of CRBN. In some embodiments, the CRBN is the isoform 1 of CRBN. In other embodiments, the CRBN is the isoform 2 of the CRBN. In some embodiments, the CRBN is the human CRBN.

In some embodiments, one or more amino acids of the degron form interactions with one or more amino acids selected from a group consisting of the amino acid residues 150, 352, 353, 355, 357, 377, 380, 386, 388, 397, and 400 of isoform 1 of human CRBN. In some embodiments, the interaction is a hydrogen bond. In other embodiments, the interaction is a Van der Waals interaction.

In some embodiments, the CAP is a substrate of CRBN. In one embodiment, the substrate of CRBN is GSPT1. In another embodiment, the substrate of CRBN is IKZF1. In yet another embodiment, the substrate of CRBN is CK1a.

In another aspect, provided herein is a method of identifying a CAP, comprising: (a) searching a protein database for a protein comprising an amino acid sequence of a degron in a CAP; (b) testing the protein in a CRBN-binding assay; and (c) identifying the protein as a CAP if the protein specifically binds to CRBN in the CRBN-binding assay.

In yet another aspect, provided herein is a method of identifying a CAP, comprising: (a) searching a protein database for a protein comprising an amino acid sequence of a degron in a CAP; (b) testing the protein in a CRBN-mediated degradation assay; and (c) identifying the protein as a CAP if the protein level decreases in the CRBN-mediated degradation assay.

In yet another aspect, provided herein is a method of identifying a target of a compound comprising: (a) searching a protein database for a protein comprising an amino acid sequence of a degron in a CAP; (b) testing the protein in a CRBN-binding assay in the presence of the compound; and (c) identifying the protein as the target of the compound if the protein specifically binds to CRBN in the CRBN-binding assay.

In yet another aspect, provided herein is a method of identifying a target of a compound comprising: (a) searching a protein database for a protein comprising an amino acid sequence of a degron in a CAP; (b) testing the protein in a CRBN-mediated degradation assay in the presence of the compound; and (c) identifying the protein as the target of the compound if the protein level decreases in the CRBN-mediated degradation assay.

In yet another aspect, provided herein is a method of identifying a CAP or a target of a compound comprising: searching for a protein that has a region of structural similarity to a degron region provided herein.

In some embodiments, provided herein is a method of identifying a CAP, comprising: (a) searching for a protein comprising a region having a similar structure of a degron in a known CAP; (b) testing the protein in a CRBN-binding assay or ubiquitination assay; and (c) identifying the protein as a CAP if the protein specifically binds to CRBN in the CRBN-binding assay ubiquitination assay. In some embodiments, the method comprises testing the protein in a CRBN-binding assay. In other embodiments, the method comprises testing the protein in an ubiquitination assay.

In other embodiments, provided herein is a method of identifying a CAP, comprising: (a) searching for a protein comprising a region having a similar structure of a degron in a known CAP; (b) testing the protein in a CRBN-mediated degradation assay, ubiquitination assay or proteomics experiment; and (c) identifying the protein as a CAP if the protein level decreases in the CRBN-mediated degradation assay, ubiquitination assay or proteomics experiment. In some embodiments, the method comprises testing the protein in a CRBN-mediated degradation assay. In some embodiments, the method comprises testing the protein in an ubiquitination assay. In other embodiments, the method comprises testing the protein in a proteomics experiment.

In yet other embodiments, provided herein is a method of identifying a target of a compound comprising: (a) searching for a protein comprising a region having a similar structure of a degron in a known CAP; (b) testing the protein in a CRBN-binding assay or ubiquitination assay in the presence of the compound; and (c) identifying the protein as the target of the compound if the protein specifically binds to CRBN in the CRBN-binding assay or ubiquitination assay. In some embodiments, the method comprises testing the protein in a CRBN-binding assay. In other embodiments, the method comprises testing the protein in an ubiquitination assay.

In yet other embodiments, provided herein is a method of identifying a target of a compound comprising: (a) searching for a protein comprising a region having a similar structure of a degron in a known CAP; (b) testing the protein in a CRBN-mediated degradation assay, ubiquitination assay, or proteomics experiment in the presence of the compound; and (c) identifying the protein as the target of the compound if the protein level decreases in the CRBN-mediated degradation assay, ubiquitination assay or proteomics experiment.

In some embodiments, the method comprises testing the protein in a CRBN-mediated degradation assay in the presence of the compound. In some embodiments, the method comprises testing the protein in an ubiquitination assay in the presence of the compound. In other embodiments, the method comprises testing the protein in a proteomics experiment in the presence of the compound.

In some embodiments of the various methods provided herein, the method comprises computationally searching for a protein based on the structural similarity to a degron provided herein. In one embodiment, the method provided herein comprises searching for a degron or a similar structure on the surface of proteins of known structure. In another embodiment, the method provided herein comprises searching for a similar structural feature to the known degron on the surface of proteins of known structure. In yet another embodiment, the method provided herein comprises searching for a glycine on the surface of proteins of known structure.

In yet another aspect, provided herein is a method of identifying a CAP or a target of a compound comprising: searching for a protein able to bind to a surface of CRBN adjacent to the site of ligand binding via features other than the known degron, e.g., by performing docking studies.

In some embodiments of the various methods provided herein, the method further comprises searching for proteins homologous to the proteins with the degron structure or predicted to have ability to bind CRBN.

In certain embodiments of the various methods provided herein, the CAP is a substrate of CRBN.

In some embodiments of the various methods provided herein, the amino acid sequence of the degron is [D/N]XX[S/T]G (SEQ ID NO:11). In other embodiments, the amino acid sequence of the degron is CXXCG (SEQ ID NO:16). In yet other embodiments, the amino acid sequence of the degron is NXXNG (SEQ ID NO:17).

In some embodiments, one or more amino acids of the degron form hydrogen bonds with one or more amino acids within amino acid residues 300-450 of CRBN. In some embodiments, one or more amino acids of the degron form hydrogen bonds with one or more amino acids within amino acid residues 350-430 of CRBN. In some embodiments, one or more amino acids of the degron form hydrogen bonds with one or more amino acids within amino acid residues 351-422 of CRBN. In some embodiments, one or more amino acids of the degron form hydrogen bonds with one or more amino acids within amino acid residues 351-357 of CRBN. In some embodiments, one or more amino acids of the degron form hydrogen bonds with one or more amino acids within amino acid residues 377-400 of CRBN. In some embodiments, the CRBN is the isoform 1 of CRBN. In other embodiments, the CRBN is the isoform 2 of the CRBN. In some embodiments, the CRBN is the human CRBN.

In some embodiments, one or more amino acids of the degron form interactions with one or more amino acids selected from a group consisting of the amino acid residues 150, 352, 353, 355, 357, 377, 380, 386, 388, 397, and 400 of isoform 1 of human CRBN. In some embodiments, the interaction is a hydrogen bond. In other embodiments, the interaction is a Van der Waals interaction.

In some embodiments of the various methods provided herein, the compound is a CMA. In other embodiments of the various methods provided herein, the compound is an immunomodulatory compound. In still other embodiments of the various methods provided herein, the compound is selected from the group consisting of thalidomide, lenalidomide, pomalidomide, Compound A, Compound B, Compound C, Compound D, and Compound E. In one embodiment, the compound is thalidomide. In another embodiment, the compound is lenalidomide. In yet another embodiment, the compound is pomalidomide. In still another embodiment, the compound is Compound A. In one embodiment, the compound is Compound B. In another embodiment, the compound is Compound C. In yet another embodiment, the compound is Compound D. In still another embodiment, the compound is Compound E.

5.9 Compounds

Compounds for the methods provided herein include, but are not limited to, the immunomodulatory compounds, a group of compounds that can be useful to treat several types of human diseases, including certain cancers.

As used herein and unless otherwise indicated, the term "immunomodulatory compound" or "immunomodulatory agent" can encompass certain small organic molecules that inhibit LPS induced monocyte TNF-α, IL-1ß, IL-12, IL-6, MIP-1α, MCP-1, GM-CSF, G-CSF, and COX-2 production. Without being limited by a particular theory, one of the biological effects exerted by the immunomodulatory compounds disclosed herein is the reduction of myeloid cell TNF-α production. Immunomodulatory compounds disclosed herein may enhance the degradation of TNF-α mRNA. Further, without being limited by theory, immunomodulatory compounds disclosed herein may also be potent co-stimulators of T cells and increase cell proliferation dramatically in a dose dependent manner. Immunomodulatory compounds disclosed herein may also have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Exemplary immunomodulatory compounds provided herein include but are not limited to thalidomide, lenalidomide, pomalidomide, Compound A, Compound B, Compound C, Compound D, and Compound E.

In a specific embodiment, the compound is thalidomide.

In another specific embodiment, the compound is lenalidomide.

In yet another specific embodiment, the compound is pomalidomide.

In yet another specific embodiment, the compound is 3-(5-amino-2-methyl-4-oxo-4H-quinazolin-3-yl)-piperidine-2,6-dione ("Compound A"), which has the following structure:

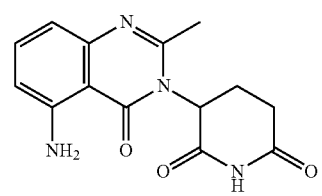

A or an enantiomer or a mixture of enantiomers thereof; or a pharmaceutically acceptable salt, solvate, hydrate, co-crystal, clathrate, or polymorph thereof.

Compound A can be prepared as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Provisional Pat. App. No. 61/451,806, filed Mar. 11, 2011, which is incorporated herein by reference in its entirety. In some embodiments, the hydrochloride salt of Compound A is used in the methods provided herein. Methods of treating, preventing and/or managing cancers and other diseases using Compound A are described in U.S. Provisional at. App. No. 61/451,995, filed Mar. 11, 2011, which is incorporated herein by reference in its entirety.

In yet another specific embodiment, the compound is 3-(4-((4-(morpholinomethyl)benzyl)oxy)-1-oxoisoindolin-2-yl)piperidine-2,6-dione ("Compound B"), which has the following structure:

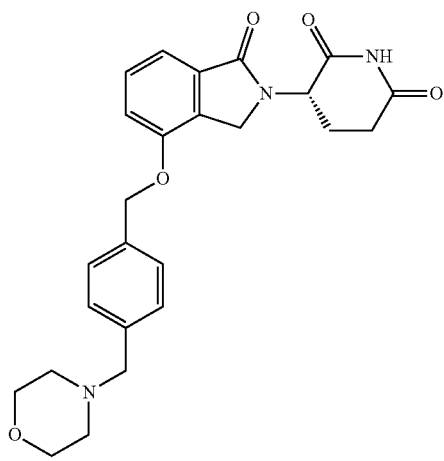

B or an enantiomer or a mixture of enantiomers thereof; or a pharmaceutically acceptable salt, solvate, hydrate, co-crystal, clathrate, or polymorph thereof.

Compound B and methods of preparing the same are described in U.S. Pat. No. 8,518,972, which is incorporated herein by reference in its entirety.

In yet another specific embodiment, the compound is 1-(3-chloro-4-methylphenyl)-3-((2-(2,6-dioxopiperidin-3-yl)-1-oxoisoindolin-5-yl)methyl)urea ("Compound C"), which has the following structure:

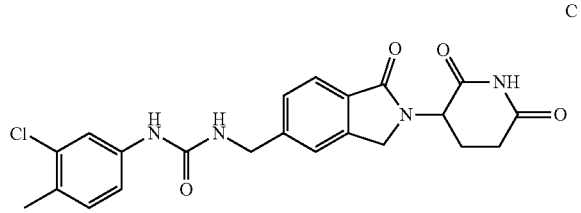 [SMILES: Cc1ccc(NC(=O)NCc2ccc3c(c2)CN(C2CCC(=O)NC2=O)C3=O)cc1Cl]

C or an enantiomer or a mixture of enantiomers thereof; or a pharmaceutically acceptable salt, solvate, hydrate, co-crystal, clathrate, or polymorph thereof. An exemplary method for preparing Compound C is illustrated in Section 6.6 below.

In yet another specific embodiment, the compound is 2-(4-chlorophenyl)-N-((2-(2,6-dioxopiperidin-3-yl)-1-oxoisoindolin-5-yl)methyl)-2,2-difluoroacetamide ("Compound D"), which has the following structure:

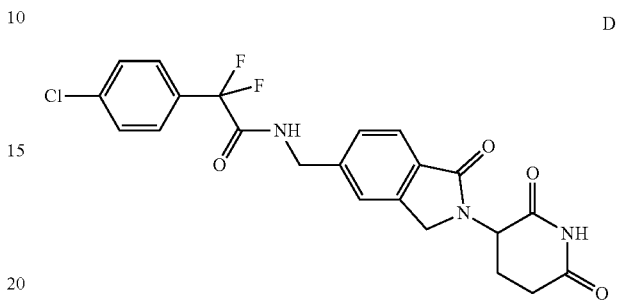

D or an enantiomer or a mixture of enantiomers thereof; or a pharmaceutically acceptable salt, solvate, hydrate, co-crystal, clathrate, or polymorph thereof.

In yet another specific embodiment, the compound is 2-(4-fluorophenyl)-N-((2-(2,6-dioxopiperidin-3-yl)-1-oxoisoindolin-5-yl)methyl)-2,2-difluoroacetamide ("Compound E"), which has the following structure:

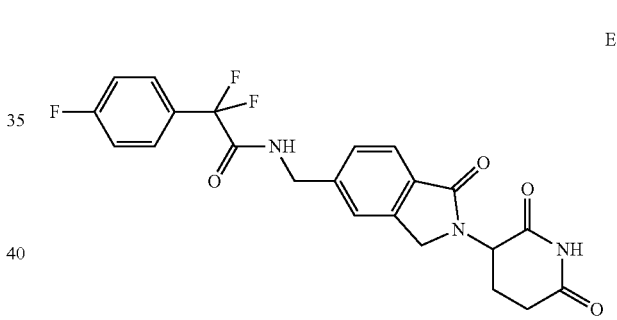

E or a pharmaceutically acceptable salt, solvate, stereoisomer, isotopologue, prodrug, hydrate, co-crystal, clathrate, or a polymorph thereof.

Compounds D and E and methods of preparing the same are described in U.S. Pat. No. 9,499,514, which is incorporated herein by reference in its entirety.

Various immunomodulatory compounds disclosed herein contain one or more chiral centers, and can exist as racemic mixtures of enantiomers or mixtures of diastereomers. Thus, also provided herein is the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

In certain embodiments of the various compositions and methods provided herein, a CMA is an immunomodulatory compound provided herein. In other embodiments, a CMA is not an immunomodulatory compound provided herein.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.10 Treatment for Patients with a CRBN-Mediated Disease

Also provided herein is a method of treating and preventing a CRBN-mediated disease, which comprises administering to a patient a compound provided herein, or an enantiomer or a mixture of enantiomers thereof, or a pharmaceutically acceptable salt, solvate, hydrate, co-crystal, clathrate, or polymorph thereof. In certain embodiments, the CRBN-mediated disease or disorder is a cancer. In certain embodiments provided herein is a compound provided herein for use in a method of treating and preventing a CRBN-mediated disease, the method comprises administering to a patient the compound, or an enantiomer or a mixture of enantiomers thereof, or a pharmaceutically acceptable salt, solvate, hydrate, co-crystal, clathrate, or polymorph thereof.

In another embodiment, provided herein is method of managing a CRBN-mediated disease, which comprises administering to a patient a compound provided herein, or an enantiomer or a mixture of enantiomers thereof, or a pharmaceutically acceptable salt, solvate, hydrate, co-crystal, clathrate, or polymorph thereof. In certain embodiments, the CRBN-mediated disease or disorder is a cancer. In certain embodiments provided herein is a compound provided herein for use in a method of managing a CRBN-mediated disease, the method comprises administering to a patient the compound, or an enantiomer or a mixture of enantiomers thereof, or a pharmaceutically acceptable salt, solvate, hydrate, co-crystal, clathrate, or polymorph thereof.

Provided herein are methods of treating or managing lymphoma, particularly non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors. In certain embodiments provided herein is a compound provided herein for use in a method of treating or managing lymphoma, particularly non-Hodgkin's lymphoma.

Also provided herein are methods of treating patients who have been previously treated for a CRBN-mediated disease or disorder (e.g., a cancer) but are non-responsive to standard therapies, as well as those who have not previously been treated. Also provided herein are methods of treating patients regardless of patient's age, although some diseases or disorders are more common in certain age groups. Also provided herein are methods of treating patients who have undergone surgery in an attempt to treat the disease or condition at issue, as well as those who have not. In some embodiments provided herein a compounds provided herein for use in methods of treating patients as mentioned above.

Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood born tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma In certain embodiments, the cancer is a blood borne tumor. In certain embodiments, the blood borne tumor is metastatic. In certain embodiments, the blood borne tumor is drug resistant. In certain embodiments, the cancer is myeloma or lymphoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In one embodiment, provided herein are methods of preventing relapsed/refractory multiple myeloma in patients with impaired renal function or a symptom thereof, comprising administering an effective amount of a compound provided herein, or an enantiomer or a mixture of enantiomers thereof, or a pharmaceutically acceptable salt, solvate, hydrate, stereoisomer, tautomer or racemic mixtures thereof to a patient at risk of having relapsed/refractory multiple myeloma with impaired renal function. In one embodiment provided herein are compounds provided herein for use in the above-mentioned methods.

In certain embodiments, provided herein are methods for treating, preventing, and/or managing relapsed/refractory multiple myeloma in patients with impaired renal function. In certain embodiments provided herein are compounds provided herein for use in methods for treating, preventing, and/or managing relapsed/refractory multiple myeloma in patients with impaired renal function.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, a therapeutically or prophylactically effective amount is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the therapeutically or prophylactically effective amount is about 0.1, about 0.2, about 0.3, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of a compound provided herein, or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.01, 0.05, 0.1, 0.2, 0.3, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.01, 0.05, 0.1, 0.2, 0.3, 0.4, 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day to patients with NHL (e.g., DLBCL). In a particular embodiment, the compound can be administered in an amount of about 10 mg/day to patients with NHL (e.g., DLBCL).

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of the compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, e.g., a compound provided herein, or an enantiomer or a mixture of enantiomers thereof, or a pharmaceutically acceptable salt, solvate, hydrate, co-crystal, clathrate, or polymorph thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the compound administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of a compound provided herein, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has been treated with anticancer therapy prior to the administration of a compound provided herein, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has developed drug resistance to the anticancer therapy.

The methods provided herein encompass treating a patient regardless of patient's age, although some diseases or disorders are more common in certain age groups. Further provided herein is a method for treating a patient who has undergone surgery in an attempt to treat the disease or condition at issue, as well in one who has not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

Depending on the disease to be treated and the subject's condition, a compound provided herein, or an enantiomer or a mixture of enantiomers thereof; or a pharmaceutically acceptable salt, solvate, hydrate, co-crystal, clathrate, or polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A compound provided herein, or an enantiomer or a mixture of enantiomers thereof; or a pharmaceutically acceptable salt, solvate, hydrate, co-crystal, clathrate, or polymorph thereof, may be formulated, alone or together, in suitable dosage unit with pharmaceutically acceptable excipients, carriers, adjuvants and vehicles, appropriate for each route of administration.

In one embodiment, a compound provided herein, or an enantiomer or a mixture of enantiomers thereof; or a pharmaceutically acceptable salt, solvate, hydrate, co-crystal, clathrate, or polymorph thereof, is administered orally. In another embodiment, a compound provided herein, or an enantiomer or a mixture of enantiomers thereof; or a pharmaceutically acceptable salt, solvate, hydrate, co-crystal, clathrate, or polymorph thereof, is administered parenterally. In yet another embodiment, a compound provided herein, or an enantiomer or a mixture of enantiomers thereof; or a pharmaceutically acceptable salt, solvate, hydrate, co-crystal, clathrate, or polymorph thereof, is administered intravenously.

A compound provided herein, or an enantiomer or a mixture of enantiomers thereof; or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MM scan and other commonly accepted evaluation modalities.

A compound provided herein, or an enantiomer or a mixture of enantiomers thereof; or a pharmaceutically acceptable salt, solvate, hydrate, co-crystal, clathrate, or polymorph thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound is administered once or more than once each day, for example, for a period of time. The term "continuous" is intended to mean that a therapeutic compound is administered daily for an uninterrupted period of at least 10 days to 52 weeks. The term "intermittent" or "intermittently" as used herein is intended to mean stopping and starting at either regular or irregular intervals. For example, intermittent administration of a compound provided herein is administration for one to six days per week, administration in cycles (e.g., daily administration for two to eight consecutive weeks, then a rest period with no administration for up to one week), or administration on alternate days. The term "cycling" as used herein is intended to mean that a therapeutic compound is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a compound provided herein, or an enantiomer or a mixture of enantiomers thereof; or a pharmaceutically acceptable salt, solvate, hydrate, co-crystal, clathrate, or polymorph thereof, is administered once a day. In another embodiment, a compound provided herein, or an enantiomer or a mixture of enantiomers thereof; or a pharmaceutically acceptable salt, solvate, hydrate, co-crystal, clathrate, or polymorph thereof, is administered twice a day. In yet another embodiment, a compound provided herein, or an enantiomer or a mixture of enantiomers thereof; or a pharmaceutically acceptable salt, solvate, hydrate, co-crystal, clathrate, or polymorph thereof, is administered three times a day. In still another embodiment, a compound provided herein, or an enantiomer or a mixture of enantiomers thereof; or a pharmaceutically acceptable salt, solvate, hydrate, co-crystal, clathrate, or polymorph thereof, is administered four times a day.

In certain embodiments, a compound provided herein, or an enantiomer or a mixture of enantiomers thereof; or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, a compound provided herein, or a pharmaceutically acceptable salt or solvate thereof, is administered once per day for one week, two weeks, three weeks, or four weeks. In one embodiment, a compound provided herein, or an enantiomer or a mixture of enantiomers thereof; or a pharmaceutically acceptable salt, solvate, hydrate, co-crystal, clathrate, or polymorph thereof, is administered once per day for one week. In another embodiment, a compound provided herein, or an enantiomer or a mixture of enantiomers thereof; or a pharmaceutically acceptable salt, solvate, hydrate, co-crystal, clathrate, or polymorph thereof, is administered once per day for two weeks. In yet another embodiment, a compound provided herein, or an enantiomer or a mixture of enantiomers thereof; or a pharmaceutically acceptable salt, solvate, hydrate, co-crystal, clathrate, or polymorph thereof, is administered once per day for three weeks. In still another embodiment, a compound provided herein, or an enantiomer or a mixture of enantiomers thereof; or a pharmaceutically acceptable salt, solvate, hydrate, co-crystal, clathrate, or polymorph thereof, is administered once per day for four weeks.

Further provided herein are methods for achieving one or more clinical endpoints associated with various hematological cancers such as AML and/or MDS comprising administering a therapeutically effective amount of the compound provided herein to a patient in need thereof.

Further provided herein are methods for increasing the overall survival (OS), complete remission rate (CRR), objective response rate (ORR), time to progression, relapse free survival (RFS), progression-free survival (PFS) event-free survival, duration of remission, duration of response, and/or time to remission/response of a patient having a hematological cancer comprising administering an effective amount of the compound provided herein. In certain embodiment, the ORR includes all responses of complete remission (CR) (i.e., morphologic leukemia-free state, morphologic CR, cytogenetic CR, molecular CR, and morphologic CR with incomplete blood recovery), and partial remission.

As used herein, Overall survival (OS) means the time from randomization in a clinical trial until death from any cause. Progression-free survival (PFS) means the time from randomization in a clinical trial until progression or death. Event-free survival (EFS) means the time from study entry until any treatment failure, including disease progression, treatment discontinuation for any reason, or death. Overall response rate (ORR) means the sum of the percentage of patients who achieve complete and partial responses. Duration of response (DoR) is the time from achieving a response until relapse or disease progression.

As used herein, "hematological cancer" includes myeloma, lymphoma and leukemia. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CML), myelodysplastic syndrome (MDS), human lymphotropic virus-type 1 (HTLV-1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma.

5.11 Combination Therapy with a Second Active Agent

A compound provided herein, or an enantiomer or a mixture of enantiomers thereof; or a pharmaceutically acceptable salt, solvate, hydrate, co-crystal, clathrate, or polymorph thereof, can also be combined or used in combination with other therapeutic agents useful in the treatment and/or prevention of cancer described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, e.g., a compound provided herein, or an enantiomer or a mixture of enantiomers thereof, or a pharmaceutically acceptable salt, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of a compound provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of a compound provided herein is independent of the route of administration of a second therapy. In one embodiment, a compound provided herein is administered orally. In another embodiment, a compound provided herein is administered intravenously. Thus, in accordance with these embodiments, a compound provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, a compound provided herein and a second therapy are administered by the same mode of administration, orally or by IV. In another embodiment, a compound provided herein is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of a compound provided herein provided herein and any optional additional active agents concurrently administered to the patient. In certain embodiments, the second active agent is oblimersen (GENASENSE®), GM-CSF, G-CSF, SCF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with melphalan and dexamethasone to patients with amyloidosis. In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, and steroids can be administered to patients with amyloidosis.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with gemcitabine and cisplatinum to patients with locally advanced or metastatic transitional cell bladder cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with temozolomide to patients with neuroendocrine tumors.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with gemcitabine to patients with recurrent or metastatic head or neck cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with gemcitabine to patients with pancreatic cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with colon cancer in combination with ARISA®, avastin, taxol, and/or taxotere.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with capecitabine and/or PLX4032 (Plexxikon) to patients with refractory colorectal cancer or patients who fail first line therapy or have poor performance in colon or rectal adenocarcinoma.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with fluorouracil, leucovorin, and irinotecan to patients with Dukes C & D colorectal cancer or to patients who have been previously treated for metastatic colorectal cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with refractory colorectal cancer in combination with capecitabine, xeloda, and/or CPT-11.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with capecitabine and irinotecan to patients with refractory colorectal cancer or to patients with unresectable or metastatic colorectal carcinoma.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered alone or in combination with interferon alpha or capecitabine to patients with unresectable or metastatic hepatocellular carcinoma; or with cisplatin and thiotepa to patients with primary or metastatic liver cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with pegylated interferon alpha to patients with Kaposi's sarcoma.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with fludarabine, carboplatin, and/or topotecan to patients with refractory or relapsed or high-risk acuted myelogenous leukemia.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with liposomal daunorubicin, topotecan and/or cytarabine to patients with unfavorable karotype acute myeloblastic leukemia.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with gemcitabine, abraxane, erlotinib, geftinib, and/or irinotecan to patients with non-small cell lung cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with carboplatin and irinotecan to patients with non-small cell lung cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered with doxetaxol to patients with non-small cell lung cancer who have been previously treated with carbo/VP 16 and radiotherapy.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with carboplatin and/or taxotere, or in combination with carboplatin, paclitaxel and/or thoracic radiotherapy to patients with non-small cell lung cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with taxotere to patients with stage IIIB or IV non-small cell lung cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with oblimersen (Genasense®) to patients with small cell lung cancer.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with ABT-737 (Abbott Laboratories) and/or obatoclax (GX15-070) to patients with lymphoma and other blood cancers.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with taxotere, IL-2, IFN, GM-CSF, PLX4032 (Plexxikon) and/or dacarbazine to patients with various types or stages of melanoma.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered alone or in combination with vinorelbine to patients with malignant mesothelioma, or stage IIIB non-small cell lung cancer with pleural implants or malignant pleural effusion mesothelioma syndrome.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with relapsed or refractory multiple myeloma in combination with doxorubicin (Doxil®), vincristine and/or dexamethasone (Decadron®).

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with various types or stages of renal cell cancer, in combination with capecitabine, IFN, tamoxifen, IL-2, GM-CSF, Celebrex®, or a combination thereof.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with various types or stages of gynecologic, uterus or soft tissue sarcoma cancer in combination with IFN, a COX-2 inhibitor such as Celebrex®, and/or sulindac.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) or an enantiomer or a mixture of enantiomers thereof, or a pharmaceutically acceptable salt, solvate, hydrate, co-crystal, clathrate, or polymorph thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, e.g., a compound provided herein, or an enantiomer or a mixture of enantiomers thereof, or a pharmaceutically acceptable salt, solvate, hydrate, co-crystal, clathrate, or polymorph thereof, alleviates or reduces adverse effects which are of such severity that it would otherwise limit the amount of anti-cancer drug.

In one embodiment, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered in combination with specific agents such as heparin, aspirin, coumadin, or G-CSF to avoid adverse effects that are associated with anti-cancer drugs such as but not limited to neutropenia or thrombocytopenia.

In one embodiment, a compound provided herein, e.g., a compound provided herein, or an enantiomer or a mixture of enantiomers thereof, or a pharmaceutically acceptable salt, solvate, hydrate, co-crystal, clathrate, or polymorph thereof, is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering a compound provided herein, or an enantiomer or a mixture of enantiomers thereof, or a pharmaceutically acceptable salt, solvate, hydrate, co-crystal, clathrate, or polymorph thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that a compound provided herein may provide additive or synergistic effects when given concurrently with conventional therapy. In certain embodiments provided herein is a compound provided herein for use in a method of treating, preventing and/or managing cancer, wherein the method comprises the above defined administration step.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. Also encompassed herein is a compound provided herein for use in a method of reducing, treating and/or preventing adverse or undesired effects associated with conventional therapy including, but not limited to, surgery, chemotherapy, radiation therapy, hormonal therapy, biological therapy and immunotherapy. A compound provided herein, e.g., a compound provided herein, or an enantiomer or a mixture of enantiomers thereof, or a pharmaceutically acceptable salt, solvate, hydrate, co-crystal, clathrate, or polymorph thereof, and other active ingredient can be administered to a patient prior to, during, or after the occurrence of the adverse effect associated with conventional therapy.

In one embodiment, a compound provided herein can be administered in an amount ranging from about 0.1 to about 150 mg, from about 1 to about 25 mg, or from about 2 to about 10 mg orally and daily alone, or in combination with a second active agent disclosed herein (see, e.g., section 5.4), prior to, during, or after the use of conventional therapy.

The following examples are offered by way of illustration, and not by way of limitation.

6. EXAMPLES

6.1 Preparation of 3-(4-amino-1-oxo-1,3-dihydro-isoindol-2-yl)-piperidine-2,6-dione (Lenalidomide)

Methyl 2-bromomethyl-3-nitrobenzoate

A stirred mixture of methyl 2-methyl-3-nitrobenzoate (14.0 g, 71.7 mmol) and N-bromosuccinimide (15.3 g, 86.1 mmol) in carbon tetrachloride (200 mL) was heated under gentle reflux for 15 hours while a 100W bulb situated 2 cm away was shining on the flask. The mixture was filtered and the solid was washed with methylene chloride (50 mL). The filtrate was washed with water (2×100 mL), brine (100 mL) and dried. The solvent was removed in vacuo and the residue was purified by flash chromatography (hexane/ethyl acetate, 8/2) to afford 19 g (96%) of the product as a yellow solid: mp 70.0-71.5° C.; 1H NMR (CDCl$_3$) δ 8.12-8.09 (dd, J=1.3 and 7.8 Hz, 1H), 7.97-7.94 (dd, J=1.3 and 8.2 Hz, 1H), 7.54 (t, J=8.0 Hz, 1H), 5.15 (s, 2H), 4.00 (s, 3H); $^{13}$C NMR (CDCl$_3$) δ 165.85, 150.58, 134.68, 132.38, 129.08, 127.80, 53.06, 22.69; HPLC, Water Nove-Pak/C18, 3.9×150 mm, 4 micron, 1 mL/min, 240 nm, 40/60 CH$_3$CN/0.1% H$_3$PO$_4$(aq) 7.27 min(98.92%); Anal. Calcd for C$_9$H$_8$NO$_4$Br: C, 39.44; H, 2.94; N, 5.11; Br, 29.15. Found: C, 39.46; H, 3.00; N, 5.00; Br, 29.11.

t-Butyl N-(1-oxo-4-nitroisoindolin-2-yl)-L-glutamine

Triethylamine (2.9 g, 28.6 mmol) was added dropwise to a stirred mixture of methyl 2-bromomethyl-3-nitrobenzoate (3.5 g, 13.0 mmol) and L-glutamine t-butyl ester hydrochloride (3.1 g, 13.0 mmol) in tetrahydrofuran (90 mL). The mixture was heated to reflux for 24 hours. To the cooled mixture was added methylene chloride (150 mL) and the mixture was washed with water (2×40 mL), brine (40 mL) and dried. The solvent was removed in vacuo and the residue was purified by flash chromatography (3% CH$_3$OH in methylene chloride) to afford 2.84 g (60%) of crude product which was used directly in the next reaction: 1H NMR (CDCl$_3$) δ 8.40 (d, J=8.1 Hz, 1H), 8.15 (d, J=7.5 Hz, 1H), 7.71 (t, J=7.8 Hz, 1H), 5.83 (s, 1H), 5.61 (s, 1H), 5.12 (d, J=19.4 Hz, 1H), 5.04-4.98 (m, 1H), 4.92 (d, J=19.4 Hz, 1H), 2.49-2.22 (m, 4H), 1.46 (s, 9H); HPLC, Waters Nova-Pak C18, 3.9×150 mm, 4 micron, 1 mL/min, 240 nm, 25/75 CH$_3$CN/0.1% H$_3$PO$_4$(aq) 6.75 min(99.94%).

N-(1-oxo-4-nitroisoindolin-2-yl)-L-glutamine

Hydrogen chloride gas was bubbled into a stirred 5° C. solution of t-butyl N-(1-oxo-4-nitro-isoindolin-2-yl)-L-glutamine (3.6 g, 9.9 mmol) in methylene chloride (60 mL) for 1 hour. The mixture was then stirred at room temperature for another hour. Ether (40 mL) was added and the resulting mixture was stirred for 30 minutes. The slurry was filtered, washed with ether and dried to afford 3.3 g of the product: 1H NMR (DMSO-d$_6$) δ 8.45 (d, J=8.1 Hz, 1H), 8.15 (d, J=7.5 Hz, 1H), 7.83 (t, J=7.9 Hz, 1H), 7.24 (s, 1H), 6.76 (s, 1H), 4.93 (s, 2H), 4.84-4.78 (dd, J=4.8 and 10.4 Hz, 1H), 2.34-2.10 (m, 4H); $^{13}$C NMR (DMSO-d$_6$) δ 173.03, 171.88, 165.96, 143.35, 137.49, 134.77, 130.10, 129.61, 126.95, 53.65, 48.13, 31.50, 24.69; Anal. Calcd for C$_{13}$H$_{13}$N$_3$O$_6$: C, 50.82; H, 4.26; N, 13.68. Found: C, 50.53; H, 4.37; N, 13.22.

(S)-3-(1-oxo-4-nitroisoindolin-2-yl)piperidine-2,6-dione

A stirred suspension mixture of N-(1-oxo-4-nitroisoindolin-2-yl)-L-glutamine (3.2 g, 10.5 mmol) in anhydrous methylene chloride (150 mL) was cooled to −40° C. with isopropanol/dry ice bath. Thionyl chloride (0.82 mL, 11.3 mmol) was added dropwise to the cooled mixture followed by pyridine (0.9 g. 11.3 mmol). After 30 min, triethylamine (1.2 g, 11.5 mmol) was added and the mixture was stirred at −30 to −40° C. for 3 hours. The mixture was poured into ice water (200 mL) and the aqueous layer was extracted with methylene chloride (40 mL). The methylene chloride solution was washed with water (2×60 mL), brine (60 mL) and dried. The solvent was removed in vacuo and the solid residue was slurried with ethyl acetate (20 mL) to give 2.2 g (75%) of the product as a white solid: mp 285° C.; 1H NMR (DMSO-d$_6$) δ: 1.04 (s, 1H), 8.49-8.45 (dd, J=0.8 and 8.2 Hz, 1H), 8.21-8.17 (dd, J=7.3 Hz, 1H), 7.84 (t, J=7.6 Hz, 1H), 5.23-5.15 (dd, J=4.9 and 13.0 Hz, 1H), 4.96 (dd, J=19.3 and 32.4 Hz, 2H), 3.00-2.85 (m, 1H), 2.64-2.49 (m, 2H), 2.08-1.98 (m, 1H); $^{13}$C NMR (DMSO-d$_6$) δ 172.79, 170.69, 165.93, 143.33, 137.40, 134.68, 130.15, 129.60, 127.02, 51.82, 48.43, 31.16. 22.23; HPLC, Waters Nove-Pak/C18, 3.9×150 mm, 4 micron, 1 mL/min, 240 nm, 20/80 CH$_3$CN/0.1% H$_3$PO$_4$(aq) 3.67 min(100%); Anal. Calcd for C$_{13}$H$_n$N$_3$O$_5$: C, 53.98; H, 3.83; N, 14.53. Found: C, 53.92; H, 3.70; N, 14.10.

3-(4-amino-1-oxo-1,3-dihydro-isoindol-2-yl)-piperidine-2,6-dione

A mixture of (S)-3-(1-oxo-4-nitroisoindolin-2-yl)piperidine-2,6-dione (1.0 g, 3.5 mmol) and 10% Pd/C (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered and dried to afford 0.46 g (51%) of the product as a white solid: mp 235.5-239° C.; $^1$H NMR (DMSO-d$_6$) δ 11.01 (s, 1H), 7.19 (t, J=7.6 Hz, 1H), 6.90 (d. J=7.3 Hz, 1H), 6.78 (d, J=7.8 Hz, 1H), 5.42 (s, 2H), 5.12 (dd. J=5.1 and 13.1 Hz, 1H), 4.17 (dd, J=17.0 and 28.8 Hz, 2H), 2.92-2.85 (m, 1H), 2.64-2.49 (m, 1H), 2.34-2.27 (m, 1H), 2.06-1.99 (m, 1H); $^{13}$C NMR (DMSO-d$_6$) δ 172.85, 171.19, 168.84, 143.58, 132.22. 128.79, 125.56, 116.37, 110.39, 51.48, 45.49, 31.20, 22.74; HPLC. Waters Nova-Pak/C18, 3.9×150 mm, 4 micron, 1 mL/min, 240 nm, 10/90 CH$_3$CN/0.1% H$_3$PO$_4$(aq) 0.96 min(100%); Chiral analysis, Daicel Chiral Pak AD, 40/60 Hexane/IPA, 6.60 min(99.42%); Anal. Calcd for C$_{13}$H$_{13}$N$_3$O$_3$: C, 60.23; H, 5.05; N, 16.21. Found: C, 59.96; H, 4.98; N, 15.84.

3-(4-Amino-1-oxo-1,3-dihydro-isoindol-2-yl)-piperidine-2,6-dione may also be prepared by methods known in the art, for example, as provided in Drugs of the Future, 2003, 28(5): 425-431, the entirety of which is incorporated by reference.

6.2 Preparation of 3-(5-amino-2-methyl-4-oxo-4H-quinazolin-3-yl)-piperidine-2,6-dione (Compound A)

To a solution of potassium hydroxide (16.1 g, 286 mmol) in water (500 mL), was added 3-nitrophthalimide (25.0 g, 130 mmol) in portion at 0° C. The suspension was stirred at 0° C. for 3 hrs, and then heated to 30° C. for 3 hrs. To the solution, was added HCl (100 mL, 6N). The resulting suspension was cooled to 0° C. for 1 hr. The suspension was filtered and washed with cold water (2×10 mL) to give 3-nitro-phthalamic acid as a white solid (24.6 g, 90% yield): $^1$H NMR (DMSO-d$_6$) δ 7.69 (brs, 1H, NHH), 7.74 (t, J=8 Hz, 1H, Ar), 7.92 (dd, J=1, 8 Hz, 1H, Ar), 8.13 (dd, J=1, 8 Hz, 1H, Ar), 8.15 (brs, 1H, NHH), 13.59 (s, 1H, OH); $^{13}$C NMR (DMSO-d$_6$) δ 125.33, 129.15, 130.25, 132.54, 136.72, 147.03, 165.90, 167.31.

To a mixture of 3-nitro-phthalamic acid (24.6 g, 117 mmol) and potassium hydroxide (6.56 g, 117 mmol) in water (118 mL), was added a mixture of bromine (6 mL), potassium hydroxide (13.2 g, 234 mmol) in water (240 mL) at 0° C., followed by addition of a solution of potassium hydroxide (19.8 g, 351 mmol) in water (350 mL). After 5 minutes at 0° C., the mixture was heated in a 100° C. oil bath for 1 hr. The reaction solution was cooled to room temperature, and then, in an ice-water bath for 30 minutes. To the mixture, a solution of HCl (240 mL, 2N) was added dropwise at 0° C., and the resulting mixture was kept for 1 hr. The suspension was filtered and washed with water (5 mL) to give 2-amino-6-nitro-benzoic acid as yellow solid (15.6 g, 73% yield): HPLC: Waters Symmetry C$_{18}$, 5 μm, 3.9×150 mm, 1 mL/min, 240 nm, CH$_3$CN/0.1% H$_3$PO$_4$, 5% grad to 95% over 5 min, 5.83 min (85%); $^1$H NMR (DMSO-d$_6$) δ 6.90 (dd, J=1, 8 Hz, 1H, Ar), 7.01 (dd, J=1, 9 Hz, 1H, Ar), 7.31 (t, J=8 Hz, 1H, Ar), 8.5-9.5 (brs, 3H, OH, NH$_2$); $^{13}$C NMR (DMSO-d$_6$) δ 105.58, 110.14, 120.07, 131.74, 149.80, 151.36, 166.30; LCMS: MH=183.

A mixture of 2-amino-6-nitro-benzoic acid (1.5 g, 8.2 mmol) in acetic anhydride (15 mL) was heated at 200° C. for 30 minutes in a microwave oven. The mixture was filtered and washed with ethyl acetate (20 mL). The filtrate was concentrated in vacuo. The solid was stirred in ether (20 mL) for 2 hrs. The suspension was filtered and washed with ether (20 mL) to give 2-methyl-5-nitro-benzo[d][1,3]oxazin-4-one as a light brown solid (1.4 g, 85% yield): HPLC: Waters Symmetry C$_{18}$, 5 μm, 3.9×150 mm, 1 mL/min, 240 nm, CH$_3$CN/0.1% H$_3$PO$_4$, 5% grad 95% in 5 min, 5.36 min (92%); $^1$H NMR (DMSO-d$_6$) δ 2.42 (s, 3H, CH$_3$), 7.79 (dd, J=1, 8 Hz, 1H, Ar), 7.93 (dd, J=1, 8 Hz, 1H, Ar), 8.06 (t, J=8 Hz, 1H, Ar); $^{13}$C NMR (DMSO-d$_6$) δ 20.87, 107.79, 121.54, 128.87, 137.19, 147.12, 148.46, 155.18, 161.78; LCMS: MH=207.

Two vials each with a suspension of 5-nitro-2-methyl-benzo[d][1,3]oxazin-4-one (0.60 g, 2.91 mmol) and 3-amino-piperidine-2,6-dione hydrogen chloride (0.48 g, 2.91 mmol) in pyridine (15 mL) were heated at 170° C. for 10 minutes in a microwave oven. The suspension was filtered and washed with pyridine (5 mL). The filtrate was concentrated in vacuo. The resulting mixture was stirred in HCl (30 mL, 1N), ethyl acetate (15 mL) and ether (15 mL) for 2 hrs. The suspension was filtered and washed with water (30 mL) and ethyl acetate (30 mL) to give a dark brown solid, which was stirred with methanol (50 mL) at room temperature overnight. The suspension was filtered and washed with methanol to give 3-(2-methyl-5-nitro-4-oxo-4H-quinazolin-3-yl)-piperidine-2,6-dione as a black solid (490 mg, 27% yield). The solid was used in the next step without further purification.

A mixture of 3-(2-methyl-5-nitro-4-oxo-4H-quinazolin-3-yl)-piperidine-2,6-dione (250 mg) and Pd(OH)$_2$ on carbon (110 mg) in DMF (40 mL) was shaken under hydrogen (50 psi) for 12 hrs. The suspension was filtered through a pad of Celite and washed with DMF (10 mL). The filtrate was concentrated in vacuo and the resulting oil was purified by flash column chromatography (silica gel, methanol/methylene chloride) to give 3-(5-amino-2-methyl-4-oxo-4H-quinazolin-3-yl)-piperidine-2,6-dione as a white solid (156 mg, 69% yield): HPLC: Waters Symmetry C$_{18}$, 5 μm, 3.9×150 mm, 1 mL/min, 240 nm, 10/90 CH$_3$CN/0.1% H$_3$PO$_4$, 3.52 min (99.9%); mp: 293-295° C.; $^1$H NMR (DMSO-d$_6$) δ 2.10-2.17 (m, 1H, CHH), 2.53 (s, 3H, CH$_3$), 2.59-2.69 (m, 2H, CH$_2$), 2.76-2.89 (m, 1H, CHH), 5.14 (dd, J=6, 11 Hz, 1H, NCH), 6.56 (d, J=8 Hz, 1H, Ar), 6.59 (d, J=8 Hz, 1H, Ar), 7.02 (s, 2H, NH$_2$), 7.36 (t, J=8 Hz, 1H, Ar), 10.98 (s, 1H, NH); $^{13}$C NMR (DMSO-d$_6$) δ 20.98, 23.14, 30.52, 55.92, 104.15, 110.48, 111.37, 134.92, 148.17, 150.55, 153.62, 162.59, 169.65, 172.57; LCMS: MH=287; Anal. Calcd. for C$_{14}$H$_{14}$N$_4$O$_3$+0.3H$_2$O: C, 57.65; H, 5.05; N, 19.21. Found: C, 57.50; H, 4.73; N, 19.00.

6.3 Unbound CRBN Crystal Structure

This example describes the preparation of a CRBN crystal. Cereblon immunomodulatory agent-binding domain can be purified as follows: The gene encoding the thalidomide binding domain (TBD) of human CRBN (amino acids 319-427) or mouse CRBN (amino acids 322-430) is codon optimized and inserted into a pGEX6P-3 vector for expression as a GST-fusion protein in *E. coli*. BL21 (DE3) Star cells transformed with either plasmid are grown to OD 0.6 in TB media supplemented with 50 μM zinc acetate, and induced with 0.5 mM IPTG for 4 hours at 37 C. Cells are resuspended in lysis buffer containing 50 mM Tris pH 7, 150 mM NaCl, 10% glycerol, 2 mM TECP, 1 mM DTT, 100 U/mL benzonase (Novagen), 1× Protease Inhibitor Cocktail-EDTA free (SD Biosciences), 0.5 mg/mL lysozyme (Sigma), and sonicated for 30 s before ultracentrifuation for 30 min at 100,000×g. GST-fused CRBN is then bound to glutathione affinity resin, washed in 50 mM Tris pH 7, 150 mM NaCl, 10% glycerol, 2 mM TCEP, 1 mM DTT, and eluted in the same buffer with the addition of 40 mM reduced glutathione. The GST tag is removed by overnight cleavage at 4 C with PreScission™ Protease (1U/mg protein, GE Healthcare). CRBN TBD is further purified with ion-exchange chromatography by diluting the cleaved protein to 75 mM NaCl usign 50 mM Tris pH 7, 2 mM TCEP and 1 mM DTT, and binding to either a Mono S column (mouse TBD) or heparin column (human TBD). Protein is eluted using a gradient from 90 mM to 1M NaCl and pooled for size exclusion chromatography. Mouse CRBN TBD can be purified by size exclusion over an S75 16/600 in 5 mM sodium acetate pH 6, 10 mM TECP, and 5 mM DTT. Human CRBN TBD can be purified over an S75 16/600 in 20 mM MES pH 6, 200 mM NaCl, 10 mM TCEP and 1 mM DTT. Either the human or the mouse protein can be concentrated to 17 mg/mL. Alternatively, residues of murine 321-429 fused to GST can be expressed in *E. coli*. Cells are lysed by sonication and the soluble fraction purified using GST-trap, ion exchange and size-exclusion chromatography. Protein can be concentrated to 28 mg/ml in 50 mM acetate buffer, pH 6.0, 1 mM DTT, 10 mM TCEP. Crystals can be obtained by sitting drop vapor diffusion by mixing the protein buffer 1:1 with and equilibrating against a mother liquor of crystallization buffer. For the mouse unbound TBD, the crystallization buffer contains 100 mM Sodium acetate pH 5, 600-800 mM Ammonium sulfate. Crystals can be grown at 4 degrees centigrade and cryoprotected by addition of 20% glycerol and frozen under liquid nitrogen.

6.4 CRBN-Drug Complex Crystal Structures

This example describes the preparation of a crystal of CRBN complexed with a second compound used to study structure-activity relationships.

A crystal of CRBN complexed with a Apo was prepared and used as a negative control. In addition, a crystal of CRBN complexed with thalidomide, pomalidomide, Compound B, or Compound C was prepared.

Figure 2:
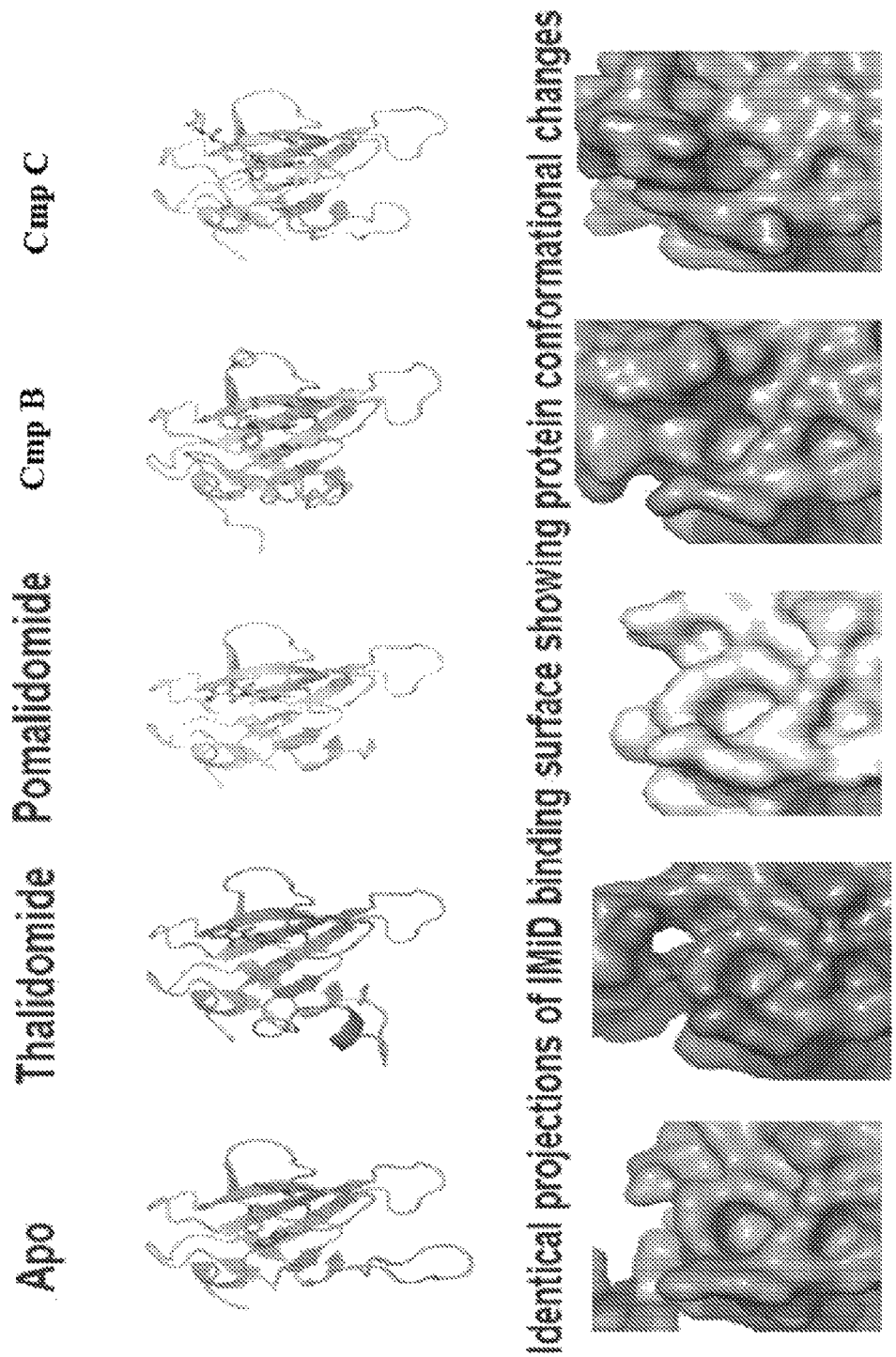
FIG. 2 depicts crystals of CRBN complexed with Apo (negative control), thalidomide, pomalidomide, Compound B, or Compound C. Identical projections of the CMA binding surfaces of CRBN show protein conformational changes.

FIG. 2 depicts identical projections of certain CMA binding surfaces of CRBN and shows protein conformational changes.

FIG. 3A depicts the crystal structure of CRBN prior to Compound B binding, and FIG. 3B depicts the crystal structure of Compound B in CRBN, in which the drug can act as a "molecular glue" or bridge with a substrate, such as a CRBN-associated protein.

FIG. 4 depicts a complex of CRBN and Compound B or thalidomide. A 50° rotation of "pthalimide" ring in Compound B relative to thalidomide or pomalidomide is observed. Such a rotation can allows for different biological effects downstream, as well as the resulting therapeutic effects.

6.5 Aiolos Degradation Assay for Identification of CMAs

The example describes an exemplary method for assaying a CRBN-mediated biological activity, and specifically Aiolos degradation.

Immunohistochemistry is performed using standard methods. For example, Immunohistochemistry is performed on the Bond-Max® automated slide stainer (Leica Microsystems) using the associated Bond Polymer Refine® Detection Kit. Four micron thick FFPE sections are deparaffinized on the instrument. Antigen retrieval is performed with Epitope Retrieval™ 2 (pH 9.0) for 20 minutes at 100° C. The slides are blocked for endogenous peroxidase activity with Peroxide Block for 5 minutes at room temperature. Sections are then incubated with rabbit polyclonal antibody to Aiolos (Santa Cruz, sc-101982) at a 1/1000 dilution for 15 minutes at room temperature, followed by incubation with HRP labeled Polymer for 8 minutes at room temperature. Enzymatic detection of anti-Aiolos antibody is accomplished with hydrogen peroxide substrate and diaminobenzidine tetrahydrochloride (DAB) chromogen at room temperature for 10 minutes. Slides are counterstained with Hematoxylin for 5 minutes at room temperature.

6.6 Production of Compound C Analogs

This example describes the production of Compound C, and analogs thereof.

1-(3-Chloro-4-methyl-phenyl)-3-[2-(2,6-dioxo-piperidin-3-yl)-1-oxo-2,3-dihydro-1H-isoindol-5-ylmethyl]-urea

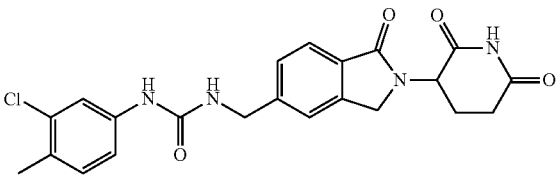 [SMILES: Cc1ccc(NC(=O)NCc2ccc3c(c2)CN(C2CCC(=O)NC2=O)C3=O)cc1Cl]

Step 1:
A mechanically stirred mixture of 4-bromo-2-methyl-benzoic acid (100 g, 465 mmol), iodomethane (95 g, 670 mmol) and sodium bicarbonate (112 g, 1340 mmol) in DMF (325 mL) was heated at 80° C. overnight. The reaction mixture was cooled to room temperature and partitioned between water (1500 mL) and 4:1 hexanes:ethyl acetate (1500 mL). The organic layer was washed with water and dried ($Na_2SO_4$). The solvent was removed under vacuum to give 110 g of 4-bromo-2-methyl-benzoic acid methyl ester as an oil, in 100% yield; $^1$H NMR (DMSO-$d_6$) δ 2.51 (s, 3H), 3.84 (s, 3H), 7.40-7.78 (m, 3H).

Step 2:
A mechanically stirred mixture of 4-bromo-2-methyl-benzoic acid methyl ester (115 g, 500 mmol), N-bromosuccinimide (90 g, 500 mmol) and AIBN (3.1 g) in acetonitrile (700 mL) was warmed over 45 minutes to a gentle reflux, and held at reflux for 21 hours. The reaction mixture was cooled to room temperature, diluted with saturated aqueous sodium bisulfite, and concentrated in vacuo. The residue was partitioned between water and 1:1 hexanes:ethyl acetate. The organic phase was washed with water, brine, and filtered through a pad of silica gel. The solvent was removed under vacuum to give an oil/solid mixture, which was digested in ether and filtered. The filtrate was chromatographed on silica gel using a hexanes-ethyl acetate gradient, eluting the product at 4:1 hexanes-ethyl acetate and providing 102 g of 4-bromo-2-bromomethyl-benzoic acid methyl ester, in 66% yield; $^1$H NMR (DMSO-$d_6$) δ 3.87 (s, 3H), 4.99 (s, 2H), 7.67-7.97 (m, 3H).

Step 3:
A mechanically stirred mixture of 4-bromo-2-bromomethyl-benzoic acid methyl ester (121 g, 390 mmol) and 3-amino-piperidine-2,6-dione hydrochloride (64.2 g, 390 mmol) in DMF (400 mL) was treated dropwise with triethylamine (98.5 g, 980 mmol) over 75 minutes. After the addition was completed, the reaction mixture was stirred at room temperature overnight. The mixture was quenched sequentially with acetic acid (50 mL), water (2500 mL) and a 1:1 mixture of ethyl acetate and hexanes (600 mL). After stirring the mixture for 20 minutes, the solid was filtered, washed with water and air dried overnight. The solid was stirred in acetic acid (200 mL) and refluxed for 2 hours. The mixture was cooled to room temperature and filtered. The solid was washed with additional acetic acid, hexanes and air dried overnight to give 25.4 g of 3-(5-bromo-1-oxo-1,3-dihydro-isoindol-2-yl)-piperidine-2,6-dione as a grey solid, in 20% yield; $^1$H NMR (DMSO-$d_6$) δ 1.97-2.04 (m, 1H), 2.32-2.46 (m, 1H), 2.56-2.63 (m, 1H), 2.85-2.97 (m, 1H), 4.34 (d, J=17.7 Hz, 1H), 4.47 (d, J=17.7 Hz, 1H), 5.11 (dd, J=13.2 Hz, J=5.1 Hz, 1H), 7.67 (d, J=8.1 Hz, 1H), 7.72 (dd, J=8.1 Hz, J=1.5 Hz, 1H), 7.89 (d, J=0.9 Hz, 1H), 11.00 (s, 1H).

Step 4:

A mechanically stirred mixture of 3-(5-bromo-1-oxo-1,3-dihydro-isoindol-2-yl)-piperidine-2,6-dione (25.2 g, 78 mmol), bis(diphenylphosphino)ferrocene (2.0 g), tris(dibenzylideneacetone)dipalladium (2.0 g) and zinc cyanide (9.4 g, 80 mmol) in DMF (300 mL) was heated to 120° C. and stirred at this temperature for 19 hours. The reaction mixture was cooled to 40° C., and another 9.4 g of zinc cyanide, 2 g of bis(diphenylphosphino)ferrocene and 2 g of tris(dibenzylideneacetone)dipalladium were added. The mixture was stirred at 120° C. for 2 hours, cooled to room temperature and quenched with water (900 mL). The solid was filtered, washed with additional water and air dried overnight. The solid was stirred in hot acetic acid (200 mL) for 20 minutes. The solid was filtered, washed with additional acetic acid, ethyl acetate and hexanes, and air dried to give 30.8 g of crude 2-(2,6-dioxo-piperidin-3-yl)-1-oxo-2,3-dihydro-1H-isoindole-5-carbonitrile as a gray solid; $^1$H NMR (DMSO-$d_6$) δ 1.99-2.06 (m, 1H), 2.35-2.45 (m, 1H), 2.57-2.63 (m, 1H), 2.86-2.98 (m, 1H), 4.42 (d, J=17.7 Hz, 1H), 4.55 (d, J=17.7 Hz, 1H), 5.15 (dd, J=13.2 Hz, J=5.1 Hz, 1H), 7.91 (d, J=7.8 Hz, 1H), 7.99 (dd, J=7.8 Hz, J=0.9 Hz, 1H), 8.16 (s, 1H), 11.03 (s, 1H).

Step 5:

A mixture of 2-(2,6-dioxo-piperidin-3-yl)-1-oxo-2,3-dihydro-1H-isoindole-5-carbonitrile (9.2 g, 34 mmol), 10% Pd-C (1.7 g) and concentrated HCl (5.3 g) in N-methylpyrrolidone (300 mL) was hydrogenated at 58 psi overnight. The crude reaction mixture was filtered through Celite, and the catalyst washed with water. The combined filtrate was concentrated in vacuo, and the product, 3-(5-aminomethyl-1-oxo-1,3-dihydro-isoindol-2-yl)-piperidine-2,6-dione hydrochloride, was isolated by fractional crystallization of the residue from isopropanol-water (1.9 g, 18%); $^1$H NMR (DMSO-$d_6$) δ 1.85-2.20 (m, 1H), 2.35-2.45 (m, 1H), 2.58-2.80 (m, 1H), 2.87-2.99 (m, 1H), 4.16 (s, 2H), 4.35 (d, J=17.5 Hz, 1H), 4.49 (d, J=17.5 Hz, 1H), 5.13 (dd, J=13.2 Hz, J=4.8 Hz, 1H), 7.63 (d, J=7.8 Hz, 1H), 7.72 (s, 1H), 7.79 (d, J=7.8 Hz, 1H), 8.43 (br, 3H), 11.01 (s, 1H).

Step 6:

A mixture of 3-(5-aminomethyl-1-oxo-1,3-dihydro-isoindol-2-yl)-piperidine-2,6-dione hydrochloride (0.50 g, 1.6 mmol), 3-chloro-4-methylphenyl isocyanate (0.27 g, 1.6 mmol) and TEA (0.32 g, 3.2 mmol) in THF (25 mL) was heated to 40° C. with stirring under $N_2$. After 3 hours, an additional portion of 3-chloro-4-methylisocyanate (0.17 g, 1.1 mmol) was added, and stirring proceeded for 2 hours. The mixture was filtered, and the filter was washed with ethyl acetate. The solid was triturated with 10 mL of 1:1 acetone-DMF and filtered. The filter was washed with acetone, and the solid was dried under vacuum, providing 430 mg of the product, in 60% yield; mp 258-260° C.; HPLC, Waters Symmetry C-18, 3.9×150 mm, 5 μm, 1 mL/min, 240 nm, 40/60 $CH_3CN$/0.1% $H_3PO_4$, 4.49 (98.75%); $^1$H NMR (DMSO-$d_6$) δ 1.90-1.96 (m, 1H), 2.16 (s, 3H), 2.25-2.39 (m, 1H), 2.50-2.55 (m, 1H), 2.78-2.91 (m, 1H), 4.24 (d, J=18.0 Hz, 1H), 4.33-4.41 (m, 3H), 5.04 (dd, J=13.5 Hz, J=4.5 Hz, 1H), 6.73 (t, J=6.0 Hz, 1H), 7.04-7.13 (m, 2H), 7.36-7.44 (m, 2H), 7.59-7.44 (m, 2H), 8.69 (s, 1H), 10.92 (s, 1H); $^{13}$C NMR (DMSO-$d_6$) δ 18.7, 22.5, 31.2, 42.8, 47.1, 51.5, 116.4, 117.6, 121.9, 122.9, 126.9, 127.4, 130.3, 131.0, 133.0, 139.6, 142.4, 144.7, 155.1, 167.9, 171.0, 172.9; Anal. Calcd for $C_{22}H_{21}ClN_4O_4$: C, 59.93; H, 4.80; N, 12.71. Found: C, 59.77; H, 4.61; N, 12.69.

6.7 CRBN is Required for the Anti-Proliferative Effect of Compound C in Hematological and Solid Tumors Lenalidomide Competes with Compound A and Compound C for CRBN TMD8 (ABC) or Karpas 422 (GCB) cells were treated with either lenalidomide; Compound A; Compound A and 100 μM lenalidomide, Compound C; or Compound C and 100 lenalidomide. Cells were cultured and cell-passaged long-term in lenalidomide or Compound A. The cells were then analyzed for proliferation using a $^3$H-thymidine incorporation assay.

FIG. 5 shows that lenalidomide competes with Compound A and Compound C for CRBN. FIG. 5A shows that co-treatment with Compound A and 10 μM lenalidomide blocks anti-proliferative effects of Compound A, though competition of binding to the CRBN complex. Likewise, FIG. 5B shows that co-treatment with Compound C and 10 μM lenalidomide blocks anti-proliferative effects of Compound C, though competition of binding to the CRBN complex. Co-culture of Lenalidomide with either Compound A or Compound C dampens the activity of these compounds as they target the same binding pocket with relative affinity.

6.8 Effect of Compound C Analogs on CRBN Substrates

This example shows the effects of Compound C analogs on CRBN substrates.

6.8.1. Compound C Induces Early Apoptosis in the MM Cell Line 11929

The multiple myeloma cell line, H929, was cultured and treated with Compound C or other CMA analogs at various concentrations from 0.01 nM to 1000 nM. Apoptosis was assessed at 24 hrs. later.

As shown in FIG. 6, Compound C induced early apoptosis in the multiple myeloma (MM) cell line H929, whereas other CMAs did not.

6.8.2. Compound C is Potent Across a Panel of Solid Tumor Lines

The potency of Compound C was assessed across a panel of tumor cell lines, including B-lymphoma, breast, CNS, colon, kidney, leukemia, lung, melanoma, multiple myeloma, ovary and prostate.

As shown in FIG. 7, Compound C is potent across a panel of tumor lines. While there was a differential cytotoxicity across the cancer cell panel, Compound C had an overall low Therapeutic Index (i.e., toxic effects at low doses). Of note, traditional immunomodulatory agents have no activity in solid tumor cell lines.

6.8.3. CRBN is Required for Anti-Proliferative Activity of Compound C in MM Cells Next, it was determined if Compound C binds CRBN in U266 multiple myeloma cells, and whether CRBN was required for Compound C activity in those cells.

As shown in FIG. 8, Compound C binds CRBN protein MM cell extracts. Immunoblot analysis of extracts prepared from U266 multiple myeloma cells and pre-incubated with vehicle DMSO (D), Pomalidomide (Pom) or Compound C at the indicated concentrations, and bound to thalidomide analog affinity beads, washed and eluted with SDS buffer as previously described (Ito et al, 2010; Lopez-Girona et al, 2012). Samples were subjected to SDS-PAGE and immunoblot analysis using anti-CRBN 65-76 (1:10,000 dilution; Red signal) and anti-DDB1 (Cell Signaling) (1:2,000 dilution; Green signal). A LI-COR Odissey system was used to quantify CRBN band density and relative amounts of CRBN were determined by averaging at least three DMSO controls and expressing CRBN in each competition sample as percent inhibition of CRBN protein relative to the averaged controls as 100% binding. Moreover, FIGS. 9 and 10 show that CRBN is required for the anti-proliferative activity of Compound C in myeloma cells. FIG. 9 shows CRBN immunoblot of extracts from DF15, DF15R shows lack of CRBN protein expression in DF15R cells. β-Tubulin immunoblot used as loading control. Cell proliferation assay of DF15 (sensitive), DF15R (resistant; CRBNnull) cells treated with a dose response of Compound C. Assays were done in triplicate and error bars represent s.d. Data for each cell line was normalized to treatment with vehicle (DMSO). FIG. 10 shows CRBN immunoblot of extracts from DF15, DF15R and DF15R cells re-expressing full length CRBN wild type (CRBNWT) or re-expressing RFP control. β-Tubulin immunoblot used as loading control. Cell proliferation assay of DF15 (sensitive), DF15R (resistant; CRBNnull), DF15R-hCRBNWT (human CRBN), DF15R-RFP cells treated with a dose response of Compound C. Data shows that re-expression of human CRBN in DF15R cells rescues Compound C anti-proliferative activity. Assays were done in triplicate and error bars represent s.d. Data for each cell line was normalized to treatment with vehicle (DMSO).

6.8.4. CRBN is Required for Anti-Proliferative Activity in Breast Cancer Cells

Breast cancer cells (MDA-MB-231) were treated with CRBN siRNA or a negative control. Compound C was added at a concentration between 0 to 100 μM, and CRBN levels were assessed at 48 hours post treatment. CRBN was significantly reduced in treated cells, as compared to a negative control receiving no siRNA (data not shown).

Compound C-mediated growth inhibition and pro-apoptotic activity were also assessed. As shown in FIG. 11, CRBN is required for both inhibition and pro-apoptotic activity of Compound C in the MDA-MB-213 breast cancer cells.

6.9 Structural Basis for Differentiated Responsiveness to Thalidomide-Class Drugs Defined by the Crystal Structure of a Lenalidomide:Human Cereblon: DDB1 Complex The ubiquitin-proteasome pathway (UPP) is the principal mechanism by which proteins become marked for degradation contributing to intracellular protein homeostasis. Dysregulation of this key protein homeostatic mechanism is implicated in the etiology of diseases including cancer, neurological conditions and metabolic diseases (Petroski et al. BMC Biochem, 2008. 9Suppl1:S7. Drugs that modulate the ubiquitin-proteasome pathway therefore have the potential to impact a wide range of biological processes and diseases including cancer. Thalidomide (THAL) and related immunomodulatory agents, such as lenalidomide (LEN) and pomalidomide (POM), have shown anticancer effects in different indications by the direct inhibition of cancer cell proliferation, modulation of the tumor microenvironment, and immunomodulation or stimulation (Ramsay et al., Blood, 2012. 120(7):1412-21; Quach et al., Leukemia, 2010. 24(1):22-32; Ramsay et al., Blood, 2013. 121(14): p. 2704-14; Eve et al, Br J Haematol., 2012. 159(2):154-63).

Cereblon (CRBN), first identified as a genetic cause of inherited autosomal recessive mental retardation, is a component of a ubiquitin E3 cullin4-ring ligase (CRL4) complex, and is the direct target of THAL and other immunomodulatory agent drugs. CRL4 ubiquitin ligases are formed by a Cullin protein (CUL4), which acts as an assembly factor that provides a scaffold for assembly of a RING-box domain protein (RBX1) and the adaptor protein Damaged DNA Binding Protein 1 (DDB1) (Angers et al., Nature, 2006. 443(7111):590-3). RBX1 is the docking site for the activated E2 protein, and DDB1 recruits substrate specificity receptors or DCAFs (DDB1-cullin4-associated-factors) to form the substrate-presenting side of the CRL4 complex (Angers et al., Nature, 2006. 443(7111):590-3; He et al., Genes Dev, 2006. 20(21):2949-54; Higa et al. Nat Cell Biol, 2006. 8(11): p. 1277-83). Roughly 60 DCAFs have been identified. These DCAFs are characterized by the presence of a WD-repeat domain (Higa et al. Nat Cell Biol, 2006. 8(11):1277-83). Biochemical and genetic evidence has shown that CRBN is a DCAF for CRL4 (Angers et al., Nature, 2006. 443(7111):590-3, Ito et al., Science, 2010. 327(5971):1345-50), and that binding of immunomodulatory agent compounds to CRBN affects CRL4CRBN ubiquitin E3 ligase activity thus mediating the anti-proliferative effects on multiple myeloma (MM) cells and the immunomodulatory effects on T cells (Ito et al., Science, 2010. 327(5971):1345-50; Lopez-Girona et al., Leukemia, 2012. 26(11):2326-35; Zhu et al., *Blood*. 2011. 118(18):4771-9).

Recently, several groups have identified the transcription factors Ikaros and Aiolos as substrates of the CRL4CRBN-immunomodulatory agent drug complex, thus explaining many of the therapeutic effects of immunomodulatory agent compounds on immune and tumor cells. These reports describe that binding of immunomodulatory agent compounds to CRBN promotes recruitment of Ikaros or Aiolos to CRL4CRBN resulting in the increased ubiquitylation and proteasomal-dependent degradation of these transcription factors in both MM and T cells. In myeloma cells, targeted knockdown of Ikaros and Aiolos mimics the decrease of the myeloma survival factor, IRF4, as well as the decrease in cell viability observed with immunomodulatory agent treatment. In T cells, Ikaros and Aiolos are known repressors of interleukin-2 (IL-2) transcription, and knockdown of either protein produces an increase in IL-2 similar to immunomodulatory agent drug treatment (Gandhi et al., Br J Haematol.; Lu et al., Science; Kronke, et al., Science, 2014. 343(6168):301-5.). These findings demonstrated that immunomodulatory agent binding confers new functionality to the CRL4CRBN complexes, raising the possibility that an immunomodulatory agent conferred neo-morphic structure is involved.

One further feature of historical and developmental importance in the pharmacology of lenalidomide and related drugs is the species specificity which these compounds exhibit. For example, it has been shown that mice and rats are insensitive to the teratogenic effects of thalidomide and lenalidomidE (Newman et al., Reprod Toxicol, 1993. 7(4): 359-90), while primates, including humans, are sensitive. Consistent with the species differences in pharmacology, we demonstrate that mouse splenocytes are resistant to the IL-2 inducing effects of pomalidomide and that in a mouse A20 cell line engineered to express human cereblon and human Aiolos, mouse Aiolos is not degraded in the presence of lenalidomide while human Aiolos is.

6.9.1. Summary

The Cul4:Rbx1:DDB1:Cereblon E3 ubiquitin ligase complex has been identified as the molecular target of a therapeutically important class of molecules known as immunomodulatory agent drugs or immunomodulatory Drugs. Immunomodulatory agent drugs directly bind Cereblon (CRBN) and in the process modulate the activity of the E3 ubiquitin ligase and the resulting stability of its client proteins. The recently described lenalidomide-mediated recruitment of the transcription factors Ikaros (IKZF1) and Aiolos (IKZF3) to the E3 complex promoting enhanced ubiquitination and degradation provides insight into the molecular basis for therapeutic activity of immunomodulatory agent drugs in multiple myeloma and other B cell malignancies.

Herein we describe the crystal structure of human CRBN bound to DDB1 and the immunomodulatory agent drug lenalidomide. CRBN binds DDB1 in the same cleft utilized by other DDB1 and Cullin Associated Factors (DCAFs); however, the interactions are non-canonical and involve more extensive interactions with both the beta-propeller A and C domains. The immunomodulatory agent binding site is comprised of a tryptophan ringed hydrophobic pocket which binds the glutarimid moiety common to lenalidomide, thalidomide, and pomalidomide. This binding conformation orients lenalidomide's isoindolinone ring towards solvent with the functional consequence of altering the substrate recognition properties of the E3 ligase.

Using structure guided point mutations and lentiviral knock-in myeloma models, we show that key immunomodulatory agent drug binding site residues are critical for drug-mediated myeloma cell antiproliferative effects. Importantly, a species specific CRBN polymorphism in rodents proximal to the lenalidomide binding site provides explanation for the long appreciated species specific responsiveness in humans and primates compared with rodents.

6.9.2. Materials and Methods
6.9.2.1 Structural Determination

Cereblon immunomodulatory agent-binding domain was purified as follows: The gene encoding the thalidomide binding domain (TBD) of human CRBN (amino acids 319-427) or mouse CRBN (amino acids 322-430) was codon optimized and inserted into a pGEX6P-3 vector for expression as a GST-fusion protein in E. coli. BL21 (DE3) Star cells transformed with either plasmid were grown to OD 0.6 in TB media supplemented with 50 µM zinc acetate, and induced with 0.5 mM IPTG for 4 hours at 37 C. Cells were resuspended in lysis buffer containing 50 mM Tris pH 7, 150 mM NaCl, 10% glycerol, 2 mM TECP, 1 mM DTT, 100 U/mL benzonase (Novagen), 1× Protease Inhibitor Cocktail-EDTA free (SD Biosciences), 0.5 mg/mL lysozyme (Sigma), and sonicated for 30 s before ultracentrifuation for 30 min at 100,000×g. GST-fused CRBN was then bound to glutathione affinity resin, washed in 50 mM Tris pH 7, 150 mM NaCl, 10% glycerol, 2 mM TCEP, 1 mM DTT, and eluted in the same buffer with the addition of 40 mM reduced glutathione. The GST tag was removed by overnight cleavage at 4 C with PreScission Protease (1U/mg protein, GE Healthcare). CRBN TBD was further purified with ion-exchange chromatography by diluting the cleaved protein to 75 mM NaCl usign 50 mM Tris pH 7, 2 mM TCEP and 1 mM DTT, and binding to either a Mono S column (mouse TBD) or heparin column (human TBD). Protein was eluted using a gradient from 90 mM to 1M NaCl and pooled for size exclusion chromatography. Mouse CRBN TBD was purified by size exclusion over an S75 16/600 in 5 mM sodium acetate pH 6, 10 mM TECP, and 5 mM DTT. Human CRBN TBD was purified over an S75 16/600 in 20 mM MES pH 6, 200 mM NaCl, 10 mM TCEP and 1 mM DTT. Either the human or the mouse protein was concentrated to 17 mg/mL.

Alternatively, residues of murine 321-429 fused to GST were expressed in E. coli. Cells were lysed by sonication and the soluble fraction purified using GST-trap, ion exchange and size-exclusion chromatography. Protein was concentration to 28 mg/ml in 50 mM acetate buffer, pH 6.0, 1 mM DTT, 10 mM TCEP. Crystals were obtained by sitting drop vapor diffusion by mixing the protein buffer 1:1 with and equilibrating against a mother liquor of crystallization buffer. For the mouse unbound TBD, the crystallization buffer contained 100 mM Sodium acetate pH 5, 600-800 mM Ammonium sulfate. Crystals were grown at 4 degrees centrigrade and cryoprotected by addition of 20% glycerol and frozen under liquid nitrogen. Human TBD crystallized in both 100 mM sodium cacodylate pH 6.5, 200 mM ammonium sulfate, and 30% PEG 8,000, and 100 mM sodium cacodylate pH 6.5, 200 mM lithium sulfate, 25% PEG 2000 MME at 4 degrees centrigrade. Crystals were cryoprotected by the addition of 20% ethylene glycol prior to freezing. Crystals of murine TBD in complex with Compound B were formed by sitting drop vapor diffusion. Compound B was added to the protein to a final concentration of 1 mM, and the protein droplet was mixed 1:1 with, and subsequently equilibrated against a reservoir solution of 100 mM MES pH 6.5, 10 mM zinc sulfate heptahydrate, 25% PEG MME 550 and incubated at 4 degrees centrigrade. Crystals were cryoprotected by addition of 20% glycerol and frozen under liquid nitrogen.

The structure of murine cereblon thal-binding domain was solved by single wavelength anomalous dispersion using intrinsically bound zinc ions. Briefly, 480 degrees of data were collected from a single crystal at 1.0A wavelength. Data were integrated and scaled using HKL2000 (Otwinowski et al., Methods in Enzymology, 1997. 276:307-326). Phasing and automated model building were performed with Crank in CCP4i, using the following subprograms: AFRO/CRUNCH2/BP3/SOLOMON/Buccaneer (Abrahams et al., Acta Crystallogr D Biol Crystallogr, 1996. 52(Pt 1): 30-42; de Graaff, R. A., et al., Acta Crystallogr D Biol Crystallogr, 2001. 57(Pt 12): 1857-62; Pannu et al., Acta Crystallogr D Biol Crystallogr, 2004. 60(Pt 1): 22-7; Pannu et al., Acta Crystallogr D Biol Crystallogr, 2011. 67(Pt 4): 331-7). Subsequent manual model building and refinement were performed using Coot and Refmac5, respectively (Murshudov et al., Acta Crystallogr D Biol Crystallogr, 2011. 67(Pt 4): 355-67; Emsley et al., Acta Crystallogr D Biol Crystallogr, 2010. 66(Pt 4): 486-501). Subsequent structures were solved by molecular replacement using Phaser (McCoy et al., J Appl Crystallogr, 2007. 40(Pt 4): 658-674).

Human CRBN (amino acids 40-442) fused to a N-terminal ZZ-6×His tag with a thrombin cleavage site and full length human DDB1 with or without a C-terminal strep-tag were co-expressed in SF9 insect cells using ESF921 medium supplemented with 50 µM zinc acetate. Cells were resuspended in 8 volumes Lysis Buffer (50 mM Tris pH 7.5, 500 mM NaCl, 10% Glycerol, 10 mM Imidazole, 1 mM TCEP) plus 1× protease inhibitor cocktail and 2,000 Units Turbo-Nuclease for 1 hour at 4° C. The lysate was centrifuged at 105,000×g for 1 hour and the supernatant was loaded to 5 mL Ni-NTA, pre-equilibrated in lysis buffer. CRBN-DDB1 was eluted using a stepwise method with Elution Buffer (50 mM Tris pH 7.5, 500 mM NaCl, 10% Glycerol, 500 mM Imidazole, 1 mM TCEP). Peak fractions were pooled and the ZZ-6×His tag was cleaved by incubation with thrombin overnight at 4 C (1 mg thrombin/100 mg target protein, Enzyme Research). Protein was subsequently diluted to 200 mM NaCl. Diluted complex was immediately applied to a HiTrap™ ANX 5 mL column (GE Lifesciences). Sample was loaded under a Tris pH 7.5 environment and changed on-column to Bis-Tris pH 6.0. Protein was eluted using a linear gradient from 200 mM to 1M NaCl. CRBN-DDB1 complex protein was polish purified by S-400 gel filtration (GE Lifesciences). Complexed protein, as identified by SDS-PAGE, was pooled and setup in crystallization or stored at −80° C. in protein buffer (10 mM MES pH 6.0, 200 mM NaCl, 5 mM TCEP). CRBN-DDB1 at 30.2 mg/ml in storage buffer consisting of 10 mM MES pH6.0, 200 mM NaCl, 5 mM TCEP, or in an alternative buffer of 10 mM HEPES pH 7, 250 mM NaCl, 3 mM TCEP. CRBN-DDB1 was crystallized by sitting drop vapor diffusion. 1 mM lenalidomide was added to the mixture of CRBN-DDB1-Lenalidomide mixed 1:1 with, and subsequently equilibrated against, a reservoir solution containing 18% (w/v) PEG 10K (Hampton Research, Aliso Viejo, Calif.) and 100 mM HEPES pH 7.5 (Hampton Research, Aliso Viejo, Calif.). Initial crystallization conditions were identified by sparse matrix screening. Co-crystals appeared in seven days and reached dimensions of 0.10 mm×0.025 mm×0.025 mm by 21 days. Before data collection, crystals were cryoprotected in the reservoir solution supplemented with 20% Ethylene glycol and frozen in liquid nitrogen. The structure of human cereblon:DDB1 was solved by molecular replacement using Phaser (McCoy et al., J Appl Crystallogr, 2007. 40(Pt 4): 658-674), with DDB1 (PDB code 3EOC) and the murine cereblon TBD as search models. Subsequent manual model building and refinement were performed using Coot and Refmac5, respectively (Murshudov et al., Acta Crystallogr D Biol Crystallogr, 2011. 67(Pt 4): 355-67; Emsley et al., Acta Crystallogr D Biol Crystallogr, 2010. 66(Pt 4): 486-501) For the human CRBN-DDB1-Compound B structure, Compound B was added to the protein at 1 mM and was mixed 1:1 with buffer containing 200 mM sodium fluoride and 20% PEG 3350 and equilibrated against a mother liquor containing the same buffer at 20 C. Crystals were cryoprotected by the addition of 20% ethylene glycol.

6.9.2.2 Cell Lines

The DF15R cell line, previously shown to lack detectable CRBN protein, was grown and cultured as previously described (Lopez-Girona et al., Leukemia, 2012. 26(11): 2326-35).

6.9.2.3 Wild-Type and Mutant CRBN Plasmids

Lentiviral expression vectors were produced in-house. Lentiviral particles were generated using HEK-293T cells and infection was done utilizing spinoculation methodology. Selection was performed 1 week after initial infection. DF15 and DF15R cells were transduce and a pool of puromycin-resistant cells selected and screened by Western blotting analysis with anti-CRBN antibody (Lopez-Girona et al., Leukemia, 2012. 26(11):2326-35). We confirmed the presence of the corresponding CRBN mutant versions by DNA genomic sequencing in all cell lines.

6.9.2.4 CRBN Short Hairpin RNA (shRNA) Constructs

Inducible shRNA constructs targeting CRBN or a control construct (Open Biosystems) were transduced using spinoculation methodology into the multiple myeloma cell lines H929 and U266. Stably transduced cells were selected with puromycin. Inducible shRNA expression (marked by RFP) was monitored by fluorescence microscopy and flow cytometry using 1 μg/mL doxycycline. CRBN protein expression was quantified by Western blotting. Cell proliferation and viability were assessed by 7AAD/flow cytometry assays.

6.9.2.5 Immunoblot and Immunohistochemistry

Western blotting was performed with antibodies to Aiolos (Santa Cruz) IRF4, c-Myc, p21, p27, and ppRb (Ser608). CRBN65 antibody was used for CRBN protein detection (Lopez-Girona et al., Leukemia, 2012. 26(11):2326-35). Cereblon immunohistochemistry (IHC) was performed on the Bond-Max® automated slide stainer (Leica Microsystems, Buffalo Grove, Ill.) using the Bond Polymer Refine® Detection system. Formalin fixed paraffin embedded (FFPE) cell pellets were sectioned at four micron thick and deparaffinized on the Bond-Max instrument. Antigen retrieval was performed with Epitope Retrieval® 2 (ER2, pH 9.0) for 20 min at 100° C. The slides were blocked for endogenous peroxidase activity with Peroxide Block for 5 minutes at room temperature. Sections were then incubated with the rabbit monoclonal antibody CRBN65 at a 1:4,000 dilution for 15 min at room temperature. Post-Primary and horseradish peroxidase (HRP) labeled Polymer were incubated at the instrument's default conditions. Antigen-antibody complex was then visualized with hydrogen peroxide substrate and diaminobenzidine tetrahydrochloride (DAB) chromogen. Slides were counterstained with hematoxylin.

6.9.2.6 Thalidomide Analog Bead Assay to Measure Compound Binding to Endogenous CRBN Coupling of thalidomide analog to FG-magnetic nanoparticle beads (Tamagawa Seiko Co. Tokyo, Japan) was carried out as described (Ito et al., Science, 2010. 327(5971):1345-50), and cell extract binding assays to these beads were performed with minor modifications. DF15, DF15R or DF15R derived cell line extracts were prepared in NP 40 lysis buffer (0.5% NP40, 50 mM Tris HCl (pH 8.0), 150 mM NaCl, 0.5 mM DTT, 0.25 mM PMSF, 1× protease inhibitor mix (Roche, Indianapolis, Ind.) at approximately 2×108 cells per ml (20 mg protein/ml). Cell debris and nucleic acids were cleared by centrifugation (14,000 rpm 30 min 4° C.). In competition experiments 0.5 ml (3-5 mg protein) aliquots of the resulting extracts were preincubated (15 min room temp.) with 5 μl DMSO (control) or 5 μl compound at varying concentrations in DMSO. Thalidomide analog-coupled beads (0.3-0.5 mg) were added to protein extracts and samples rotated (2 hours, 4° C.). Beads were washed three times with 0.5 ml NP40 buffer, and then bound proteins were eluted with SDS-PAGE sample buffer. Samples were subjected to SDS-PAGE and immunoblot analysis, performed using anti-CRBN 65-76 (Lopez-Girona et al., Leukemia, 2012. 26(11):2326-35) (1:10,000 dilution) for all studies; other antisera dilutions were DDB1 (1:2,000 dilution) or β-actin (1:10,000 dilution). In thalidomide affinity bead competition assays, a LI-COR Odessey™ system was used to quantify CRBN band density and relative amounts of CRBN were determined by averaging at least three DMSO controls and expressing CRBN in each competition sample as percent inhibition of CRBN protein relative to the averaged controls as 100% binding.

6.9.3. Results 6.9.3.1 Crystal Structure of CRBN in Complex with DDB1 and Lenalidomide The structure of CRBN reveals that CRBN is a DCAF that does not exhibit a WD-repeat architecture typical of the class. The CRBN structure (FIG. 12) reveals two distinct domains: an N-terminal Lon-like domain (LLD), and a C-terminal TBD. The structure reveals that the DDB1 and immunomodulatory agent binding sites occur on opposite sides of the cereblon surface. A human polymorphism linked to mental retardation has been found in CRBN resulting in premature truncation of CRBN at amino acid 419. The deleted region occurs within the immunomodulatory agent binding domain, with a short helical region and a β-strand removed (deleted region shown in red in FIG. 12). The deleted region occurs at the interface between the LLD and TBD, and truncation of these residues might be expected to deleteriously affect the domain structure and stability of CRBN.

The CRBN Lon-like domain (LLD) spans residues 76-318 and contains the DDB1 binding motif. Structural alignment with *Bacillus subtilis* Lon N-terminal domain yields an RMSD of 2.4 Angstroms over 165 aligned residues (FIG. 13) (Duman et al., J Mol Biol, 2010. 401(4): p. 653-70). However, as shown in FIG. 13, the DDB1 binding motif and the immunomodulatory agent binding site do not exhibit any homology with the examined Lon domains. When compared to *B. subtilis* Lon, the DDB1 binding motif appears to have been inserted into the Lon-like domain, and is composed of a series of helices between CRBN residues 188 and 248. CRBN binds between the beta propeller A (BPA) and the beta propeller C (BPC) domains of DDB1 in a similar location to other DCAFs (e.g. DDB2 or DCAF9), as well as to the viral DDB1 binding proteins Hbx and SV5V (Li et al., Nat Struct Mol Biol, 2010. 17(1): p. 105-11). However, although CRBN binds to DDB1 in the same region, the nature of the interaction with DDB1 exhibits differences compared to DDB2, SV5V or Hbx. Previously studied DCAFs position a helix-turn-helix motif in the DDB1 binding site which predominantly forms interactions with the BPC domain (FIG. 14, helices c and d) (Li et al., Nat Struct Mol Biol, 2010. 17(1): p. 105-11). CRBN interacts with DDB1 via a series of helices; however, these do not superpose with the DCAFs which have been structurally characterized (FIG. 14). In CRBN, residues 221-248 form helices which interact with the DDB1 BPC domain (helix a and b, FIG. 14). CRBN residues 191-197 also interact with DDB1 BPC in a proximal region to DDB2 (FIG. 13). However, as well as interacting with the BPC domain, CRBN also positions a helix composed of residues 198 to 209 to interact with the BPA domain of DDB1, the first example of such an interaction (helix e, FIG. 14). After the DDB1 binding motif, structural homology with the Lon domain is restored between residue 249 and 318 which form a 4-helix bundle, thus leading to the immunomodulatory agent binding domain, or thalidomide binding domain (TBD) at residues 319-428.

The TBD is located on the face of CRBN which is oriented away from the DDB1-binding site. The TBD is composed of a six-stranded antiparallel β-sheet core, with a structural zinc ion, coordinated by four cysteine residues, located ~18 Å from the immunomodulatory agent binding site (FIG. 18). The immunomodulatory agent binding pocket itself is formed by three tryptophan residues, Trp380, Trp386, and Trp400, with a phenylalanine residue at the base (Phe402) (FIG. 18). These residues form a small hydrophobic pocket (tri-Trp pocket) in which the glutarimide portion of lenalidomide is accommodated. Within the tri-Trp pocket there are two hydrogen bonds between the glutarimide ring and the protein backbone at residues His378 and Trp380 (FIG. 13), and a further hydrogen bond with the sidechain of His378. The isoindolinone ring of lenalidomide is not enclosed within the hydrophobic pocket, and instead presents on the surface of the protein interacting with a beta-turn encompassing residues 351-353 (indicated by the symbol β in FIG. 13). The carbonyl oxygen of the isoindolinone ring is oriented towards the sidechain of His357; however, the distance is slightly too long for a hydrogen bond to form (4.1 Å). Similarly, the aniline amino group of lenalidomide is oriented towards Glu377, but at a distance too great for an interaction to be made (5.5 Å).

In determining whether CMA drug interaction with CRBN may serve to alter the specificity of the Cul4 ubiquitin ligase complex by recruitment of new partners or altering the substrate affinity of its client substrates, it is intriguing that the isoindolinone ring is exposed on the surface of the CRBN-immunomodulatory agent complex, indicating that this part of the immunomodulatory agent molecule would be available to form part of a 'neomorphic' interface in substrate recruitment. In this instance, the unused hydrophobic and polar bonding potential of the immunomodulatory agent and the adjacent protein surface could play a key role in altering/enhancing binding partner recruitment.

The TBD can be expressed and purified in isolation, and we have used this system to obtain crystal structures of the murine CRBN TBD in complex with thalidomide and pomalidomide. The TBD structure was initially solved by taking advantage of the predicted zinc binding site in a single wavelength anomalous dispersion experiment at a normal synchrotron wavelength of 1.0 Å. We noted that the electron density favors the S-enantiomer of thalidomide, which was crystallized as a racemic mixture. We subsequently confirmed that S-thalidomide binds CRBN more tightly than the R-enantiomer by competition for thalidomide immobilized beads (FIG. 21) consistent with previous results using the conformationally stable R- and S-methyl-pomalidomide analogs (Lopez-Girona et al., Leukemia. 26(11):2326-35). The core features of the immunomodulatory agent binding site which interact with the glutarimide ring are well conserved between the lenalidomide, thalidomide and pomalidomide structures, with the three tryptophans providing the key interactions to the glutarimide ring. The two hydrogen bonds to His378 and Trp380 are also conserved; however, the third hydrogen bond to the sidechain of His378 is not made. There is a striking difference between the lenalidomide structure and the others: the two beta-strands composed of residues 346-363 are absent in both the thalidomide and the pomalidomide structures (FIGS. 15, 16 and 17). There are four protein-drug pairs in the asymmetric unit for both the thalidomide and pomalidomide structures. In all proteins in the asymmetric unit in the pomalidomide structure the beta-strand region is completely disordered (FIG. 17). The same is true for one protein (chain A) in the thalidomide structure (FIG. 16); however, in chains B and D the beta-strands have adopted an alternative conformation where these residues bind the phthalimide ring of thalidomide from an adjacent molecule in the asymmetric unit (FIG. 20). This reciprocal arrangement forms a dimer in the crystal lattice, with Tyr355 stacking against the accessible surface of the immunomodulatory agent. There is no evidence of dimerization in the presence or absence of immunomodulatory agent (data not shown). The change in conformation provides a substantial change in the surface of CRBN in the immunomodulatory agent binding site vicinity, with the intriguing potential to influence binding partner recruitment. The extent to which different conformations are influenced by protein truncation or the lattice environment is unknown.

The alternative substitutions on the isoindolinone/phthalimide ring provide a second potential mechanism by which to selectively recruit binding partners to the Cul4:DDB1:CRBN E3 ligase complex. Lenalidomide and pomalidomide differ from thalidomide in possessing an $NH_2$ substitution on the isoindolinone/phthalimide ring. In the lenalidomide structure this $NH_2$ moiety is oriented towards Glu377, where in the pomalidomide structure this group appears to be able to orient into either direction as the electron density supports differing orientations in the different chains in the asymmetric unit (data not shown).

We further sought to confirm that the immunomodulatory agents binding pocket is present in the absence of ligand by determining the structure of apo TBD. This structure clearly shows that the pocket can exist in a similar conformation in the absence of ligand (Table 2)

TABLE 2

Crystallographic Statistics

| Protein:<br>Ligand | CRBN:DDB1:<br>Lenalidomide | CRBN(TBD):<br>Pomalidomide | CRBN(TBD):<br>Thalidomide |
|---|---|---|---|
| Data collection site | CLS CMCF-08ID | ALS 8.2.1 | APS SER-CAT 22ID |
| Wavelength (Å) | 1.0 | 1.0 | 1.0 |
| Resolution Range (Å) | 50-3.0 (3.12-3.01)* | 50-2.0 (2.11-2.00) | 50-1.88 (1.95-1.88) |
| Spacegroup | $P2_12_12_1$ | I23 | I23 |
| Cell dimensions (Å) | 71.8 129.1 198.7 | 143.3 143.3 143.3 | 143.1 143.1 143.1 |
| Angles (deg) | 90 90 90 | 90 90 90 | 90 90 90 |
| No. of observations | 228444 | 83521 | 1750276 |
| No. of unique observations | 37313 | 25718 | 76864 |
| Completeness (%) | 98.5 (85.8)* | 92.3 (92.4) | 99.9 (100.0) |
| I/σI | 10.1 (2.6) | 10.1 (5.4) | 38.4 (6.6) |
| $R_{merge}$ (%) | 18.1 (72.3) | 9.0 (24.5) | 8.9 (59.9) |
| Refinement statistics | | | |
| $R_{work}/R_{free}$ | 20.3/27.8 | 19.7/24.0 | 18.0/22.9 |
| RMSD for bond length (Å) | 0.012 | 0.017 | 0.014 |
| RMSD for bond angles (deg) | 1.25 | 1.723 | 1.676 |

*Figures in parentheses are for the outer resolution shell.

Table 3 below sets forth the atomic coordinates for CRBN:DDB1:Lenalidomide.

Table 4 below sets forth the atomic coordinates for CRBN(TBD):Pomalidomide.

Table 5 below sets forth the atomic coordinates for CRBN(TBD): Thalidomide.

Table 6 below sets forth the atomic coordinates for CRBN: DDB1: Compound B.

Table 7 below sets forth the atomic coordinates for CRBN (TBD): Compound B.

Table 8 below sets forth the atomic coordinates for unbound CRBN-CRBN (TBD) (Apo).

| Atomic coordinates for CRBN:DDB1:Lenalidomide (Human protein) |
|---|
| HEADER    ----                                                                XX-XXX-9-  xxxx |
| COMPND    --- |
| REMARK  3 |
| REMARK  3 REFINEMENT. |
| REMARK  3    PROGRAM              :  REFMAC 5.6.0117 |
| REMARK  3    AUTHORS              : |
| REMARK  3 |
| REMARK  3    REFINEMENT TARGET    : MAXIMUM LIKELIHOOD |
| REMARK  3 |
| REMARK  3  DATA USED IN REFINEMENT. |
| REMARK  3    RESOLUTION RANGE HIGH   (ANGSTROMS) : 3.01 |
| REMARK  3    RESOLUTION RANGE LOW    (ANGSTROMS) : 50.00 |
| REMARK  3    DATA CUTOFF             (SIGMA(F)) : NONE |
| REMARK  3    COMPLETENESS FOR RANGE        (%) : 99.40 |
| REMARK  3    NUMBER OF REFLECTIONS            : 35396 |
| REMARK  3 |
| REMARK  3  FIT TO DATA USED IN REFINEMENT. |
| REMARK  3    CROSS-VALIDATION METHOD      : THROUGHOUT |
| REMARK  3    FREE R VALUE TEST SET SELECTION  : RANDOM |
| REMARK  3    R VALUE     (WORKING + TEST SET) : 0.20710 |
| REMARK  3    R VALUE            (WORKING SET) : 0.20340 |
| REMARK  3    FREE R VALUE                     : 0.27777 |
| REMARK  3    FREE R VALUE TEST SET SIZE   (%) : 5.0 |
| REMARK  3    FREE R VALUE TEST SET COUNT      : 1857 |
| REMARK  3 |
| REMARK  3  FIT IN THE HIGHEST RESOLUTION BIN. |
| REMARK  3    TOTAL NUMBER OF BINS USED           : 20 |
| REMARK  3    BIN RESOLUTION RANGE HIGH           : 3.010 |
| REMARK  3    BIN RESOLUTION RANGE LOW            : 3.088 |
| REMARK  3    REFLECTION IN BIN      (WORKING SET) : 2223 |
| REMARK  3    BIN COMPLETENESS   (WORKING+TEST) (%) : 92.95 |
| REMARK  3    BIN R VALUE           (WORKING SET) : 0.275 |
| REMARK  3    BIN FREE R VALUE SET COUNT          : 111 |
| REMARK  3    BIN FREE R VALUE                    : 0.352 |
| REMARK  3 |
| REMARK  3  NUMBER OF NON-HYDROGEN ATOMS USED IN REFINEMENT. |
| REMARK  3    ALL ATOMS           :    11099 |
| REMARK  3 |
| REMARK  3  B VALUES. |
| REMARK  3    FROM WILSON PLOT           (A**2) : NULL |
| REMARK  3    MEAN B VALUE        (OVERALL, A**2) : 30.828 |
| REMARK  3    OVERALL ANISOTROPIC B VALUE. |
| REMARK  3       B11   (A**2)   :    -1.53 |

| Atomic coordinates for CRBN:DDB1:Lenalidomide (Human protein) | | | | | | |
|---|---|---|---|---|---|---|
| REMARK 3 | B22 | (A**2) | : | 1.71 | | |
| REMARK 3 | B33 | (A**2) | : | −0.18 | | |
| REMARK 3 | B12 | (A**2) | : | 0.00 | | |
| REMARK 3 | B13 | (A**2) | : | 0.00 | | |
| REMARK 3 | B23 | (A**2) | : | 0.00 | | |
| REMARK 3 | | | | | | |
| REMARK 3 | ESTIMATED OVERALL COORDINATE ERROR. | | | | | |
| REMARK 3 | ESU BASED ON R VALUE | | | (A) : NULL | | |
| REMARK 3 | ESU BASED ON FREE R VALUE | | | (A) : 0.477 | | |
| REMARK 3 | ESU BASED ON MAXIMUM LIKELIHOOD | | | (A) : 0.336 | | |
| REMARK 3 | ESU FOR B VALUES BASED ON MAXIMUM LIKELI-HOOD | | | (A**2) : 39.724 | | |
| REMARK 3 | | | | | | |
| REMARK 3 | CORRELATION COEFFICIENTS. | | | | | |
| REMARK 3 | CORRELATION COEFFICIENT FO-FC | | : 0.917 | | | |
| REMARK 3 | CORRELATION COEFFICIENT FO-FC FREE : 0.868 | | | | | |
| REMARK 3 | | | | | | |
| REMARK 3 | RMS DEVIATIONS FROM IDEAL VALUES | | | COUNT | RMS | WEIGHT |
| REMARK 3 | BOND LENGTHS REFINED ATOMS | (A): | | 11303 ; | 0.012 ; | 0.020 |
| REMARK 3 | BOND ANGLES REFINED ATOMS | (DEGREES): | | 15349 ; | 1.252 ; | 1.961 |
| REMARK 3 | TORSION ANGLES, PERIOD 1 | (DEGREES): | | 1409 ; | 7.786 ; | 5.000 |
| REMARK 3 | TORSION ANGLES, PERIOD 2 | (DEGREES): | | 477 ; | 40.149 ; | 24.528 |
| REMARK 3 | TORSION ANGLES, PERIOD 3 | (DEGREES): | | 1873 ; | 20.308 ; | 15.000 |
| REMARK 3 | TORSION ANGLES, PERIOD 4 | (DEGREES): | | 51 ; | 21.422 ; | 15.000 |
| REMARK 3 | CHIRAL-CENTER RESTRAINTS | (A**3): | | 1785 ; | 0.086 ; | 0.200 |
| REMARK 3 | GENERAL PLANES REFINED ATOMS | (A): | | 8406 ; | 0.008 ; | 0.021 |
| REMARK 3 | | | | | | |
| REMARK 3 | ISOTROPIC THERMAL FACTOR RESTRAINTS. | | | COUNT | RMS | WEIGHT |
| REMARK 3 | | | | | | |
| REMARK 3 | NCS RESTRAINTS STATISTICS | | | | | |
| REMARK 3 | NUMBER OF NCS GROUPS | : | NULL | | | |
| REMARK 3 | | | | | | |
| REMARK 3 | TWIN DETAILS | | | | | |
| REMARK 3 | NUMBER OF TWIN DOMAIN | : | NULL | | | |
| REMARK 3 | | | | | | |
| REMARK 3 | | | | | | |
| REMARK 3 | TLS DETAILS | | | | | |
| REMARK 3 | NUMBER OF TLS GROUPS | : | 5 | | | |
| REMARK 3 | ATOM RECORD CONTAINS RESIDUAL B FACTORS ONLY | | | | | |
| REMARK 3 | | | | | | |
| REMARK 3 | TLS GROUP : 1 | | | | | |
| REMARK 3 | NUMBER OF COMPONENTS GROUP : 1 | | | | | |
| REMARK 3 | COMPONENTS | C SSSEQI TO C | | SSSEQI | | |
| REMARK 3 | RESIDUE RANGE : | A 393 | | A 708 | | |
| REMARK 3 | ORIGIN FOR THE GROUP (A) : | | −0.3068 | 15.1336 | −7.6399 | |
| REMARK 3 | T TENSOR | | | | | |
| REMARK 3 | T11: 0.1628 | T22: 0.2998 | | | | |
| REMARK 3 | T33: 0.0298 | T12: −0.1471 | | | | |
| REMARK 3 | T13: −0.0098 | T23: 0.0105 | | | | |
| REMARK 3 | L TENSOR | | | | | |
| REMARK 3 | L11: 2.6533 | L22: 2.7126 | | | | |
| REMARK 3 | L33: 2.2970 | L12: 0.8261 | | | | |
| REMARK 3 | L13: 0.1789 | L23: −0.4504 | | | | |
| REMARK 3 | S TENSOR | | | | | |
| REMARK 3 | S11: 0.1379 | S12: −0.2573 | S13: | 0.2315 | | |
| REMARK 3 | S21: 0.3045 | S22: −0.1549 | S23: | −0.0219 | | |
| REMARK 3 | S31: −0.3251 | S32: 0.4142 | S33: | 0.0170 | | |
| REMARK 3 | | | | | | |
| REMARK 3 | TLS GROUP : 2 | | | | | |
| REMARK 3 | NUMBER OF COMPONENTS GROUP : 1 | | | | | |
| REMARK 3 | COMPONENTS | C SSSEQI | TO C | SSSEQI | | |
| REMARK 3 | RESIDUE RANGE : | A 1 | | A 392 | | |
| REMARK 3 | ORIGIN FOR THE GROUP (A): | | −13.1472 | 3.8365 | −65.2475 | |
| REMARK 3 | T TENSOR | | | | | |
| REMARK 3 | T11: 0.1525 | T22: 0.1346 | | | | |
| REMARK 3 | T33: 0.1167 | T12: −0.0151 | | | | |
| REMARK 3 | T13: 0.0090 | T23: 0.0399 | | | | |
| REMARK 3 | L TENSOR | | | | | |
| REMARK 3 | L11: 0.4911 | L22: 1.1590 | | | | |
| REMARK 3 | L33: 0.6814 | L12: −0.1378 | | | | |
| REMARK 3 | L13: −0.0803 | L23: 0.3506 | | | | |
| REMARK 3 | S TENSOR | | | | | |
| REMARK 3 | S11: 0.0271 | S12: 0.0480 | S13: | −0.0068 | | |
| REMARK 3 | S21: −0.1494 | S22: −0.0207 | S23: | −0.0650 | | |
| REMARK 3 | S31: 0.0348 | S32: −0.0012 | S33: | −0.0065 | | |
| REMARK 3 | | | | | | |
| REMARK 3 | TLS GROUP : 3 | | | | | |
| REMARK 3 | NUMBER OF COMPONENTS GROUP : 1 | | | | | |

-continued

Atomic coordinates for CRBN:DDB1:Lenalidomide (Human protein)

| | | | | | | | | |
|---|---|---|---|---|---|---|---|---|
| REMARK 3 | COMPONENTS | | C | SSSEQI | TO | C | SSSEQI | |
| REMARK 3 | RESIDUE RANGE : | | A | 709 | | A | 1200 | |
| REMARK 3 | ORIGIN FOR THE GROUP (A): | | | | −21.4420 | 29.8478 | | −47.2567 |
| REMARK 3 | T TENSOR | | | | | | | |
| REMARK 3 | T11: | 0.1311 | T22: | 0.1037 | | | | |
| REMARK 3 | T33: | 0.1785 | T12: | −0.0149 | | | | |
| REMARK 3 | T13: | 0.0266 | T23: | 0.0153 | | | | |
| REMARK 3 | L TENSOR | | | | | | | |
| REMARK 3 | L11: | 0.8961 | L22: | 0.4909 | | | | |
| REMARK 3 | L33: | 0.5067 | L12: | −0.2898 | | | | |
| REMARK 3 | L13: | −0.1289 | L23: | −0.0031 | | | | |
| REMARK 3 | S TENSOR | | | | | | | |
| REMARK 3 | S11: | −0.0251 | S12: | −0.0059 | S13: | 0.0840 | | |
| REMARK 3 | S21: | 0.0400 | S22: | 0.0368 | S23: | 0.0082 | | |
| REMARK 3 | S31: | −0.0496 | S32: | −0.0305 | S33: | −0.0117 | | |
| REMARK 3 | | | | | | | | |
| REMARK 3 | TLS GROUP : 4 | | | | | | | |
| REMARK 3 | NUMBER OF COMPONENTS GROUP : 1 | | | | | | | |
| REMARK 3 | COMPONENTS | | C | SSSEQI | TO | C | SSSEQI | |
| REMARK 3 | RESIDUE RANGE : | | C | 187 | | C | 256 | |
| REMARK 3 | ORIGIN FOR THE GROUP (A): | | | | −31.3124 | 19.6121 | | −66.7413 |
| REMARK 3 | T TENSOR | | | | | | | |
| REMARK 3 | T11: | 0.2983 | T22: | 0.1909 | | | | |
| REMARK 3 | T33: | 0.1527 | T12: | 0.0117 | | | | |
| REMARK 3 | T13: | −0.0659 | T23: | 0.0171 | | | | |
| REMARK 3 | L TENSOR | | | | | | | |
| REMARK 3 | L11: | 0.3674 | L22: | 3.0198 | | | | |
| REMARK 3 | L33: | 0.7357 | L12: | −0.5710 | | | | |
| REMARK 3 | L13: | −0.2040 | L23: | −0.2416 | | | | |
| REMARK 3 | S TENSOR | | | | | | | |
| REMARK 3 | S11: | 0.1361 | S12: | 0.0628 | S13: | −0.0342 | | |
| REMARK 3 | S21: | −0.0897 | S22: | −0.0133 | S23: | 0.1583 | | |
| REMARK 3 | S31: | 0.2257 | S32: | −0.0128 | S33: | −0.1229 | | |
| REMARK 3 | | | | | | | | |
| REMARK 3 | TLS GROUP : 5 | | | | | | | |
| REMARK 3 | NUMBER OF COMPONENTS GROUP : 2 | | | | | | | |
| REMARK 3 | COMPONENTS | | C | SSSEQI | TO | C | SSSEQI | |
| REMARK 3 | RESIDUE RANGE : | | C | 1 | | C | 186 | |
| REMARK 3 | RESIDUE RANGE : | | C | 257 | | C | 500 | |
| REMARK 3 | ORIGIN FOR THE GROUP (A): | | | | −36.9305 | 47.0483 | | −87.0978 |
| REMARK 3 | T TENSOR | | | | | | | |
| REMARK 3 | T11: | 0.2231 | T22: | 0.1289 | | | | |
| REMARK 3 | T33: | 0.1194 | T12: | 0.0228 | | | | |
| REMARK 3 | T13: | −0.0118 | T23: | 0.0144 | | | | |
| REMARK 3 | L TENSOR | | | | | | | |
| REMARK 3 | L11: | 1.1260 | L22: | 0.9557 | | | | |
| REMARK 3 | L33: | 1.7495 | L12: | −0.4292 | | | | |
| REMARK 3 | L13: | 0.7316 | L23: | −0.9160 | | | | |
| REMARK 3 | S TENSOR | | | | | | | |
| REMARK 3 | S11: | −0.0115 | S12: | −0.0943 | S13: | 0.0603 | | |
| REMARK 3 | S21: | 0.0310 | S22: | −0.1114 | S23: | −0.0638 | | |
| REMARK 3 | S31: | −0.1272 | S32: | −0.0142 | S33: | 0.1229 | | |
| REMARK 3 | | | | | | | | |
| REMARK 3 | | | | | | | | |
| REMARK 3 | BULK SOLVENT MODELLING. | | | | | | | |
| REMARK 3 | METHOD USED : MASK | | | | | | | |
| REMARK 3 | PARAMETERS FOR MASK CALCULATION | | | | | | | |
| REMARK 3 | VDW PROBE RADIUS : 1.20 | | | | | | | |
| REMARK 3 | ION PROBE RADIUS : 0.80 | | | | | | | |
| REMARK 3 | SHRINKAGE RADIUS : 0.80 | | | | | | | |
| REMARK 3 | | | | | | | | |
| REMARK 3 | OTHER REFINEMENT REMARKS: | | | | | | | |
| REMARK 3 | HYDROGENS HAVE BEEN USED IF PRESENT IN THE INPUT | | | | | | | |
| REMARK 3 | U VALUES : RESIDUAL ONLY | | | | | | | |
| REMARK 3 | | | | | | | | |
| LINKR | | ALA A | 46 | | LEU A | 49 | | gap |
| LINKR | | GLN A | 93 | | SER A | 97 | | gap |
| LINKR | | GLN A | 209 | | ASN A | 211 | | gap |
| LINKR | | LYS A | 287 | | THR A | 296 | | gap |
| LINKR | | ASN A | 337 | | GLU A | 342 | | gap |
| LINKR | | GLU A | 368 | | GLN A | 372 | | gap |
| LINKR | | PRO A | 417 | | GLU A | 420 | | gap |
| LINKR | | GLU A | 535 | | VAL A | 538 | | gap |
| LINKR | | LEU A | 546 | | GLY A | 551 | | gap |
| LINKR | | LEU A | 576 | | HIS A | 578 | | gap |
| LINKR | | ASP A | 625 | | LYS A | 627 | | gap |
| LINKR | | SER A | 643 | | SER A | 645 | | gap |

-continued

| \multicolumn{9}{c}{Atomic coordinates for CRBN:DDB1:Lenalidomide (Human protein)} |

| | | | | | | | | | | |
|---|---|---|---|---|---|---|---|---|---|---|
| LINKR | | | ASP A | 744 | | THR A | 749 | | gap | |
| LINKR | | | SER A | 767 | | GLU A | 784 | | gap | |
| LINKR | | | ASP A | 980 | | GLU A | 987 | | gap | |
| LINKR | | | VAL A | 1013 | | THR A | 1024 | | gap | |
| LINKR | | | THR A | 1078 | | LYS A | 1081 | | gap | |
| LINKR | | | GLY A | 1117 | | ASP A | 1121 | | gap | |
| LINKR | | | SER C | 126 | | GLU C | 132 | | gap | |
| LINKR | | | ARG C | 172 | | GLY C | 176 | | gap | |
| LINKR | | | VAL C | 213 | | TYR C | 221 | | gap | |
| LINKR | | | ASP C | 265 | | SER C | 272 | | gap | |
| CRYST1 | 71.862 | 129.117 | | 198.677 | 90.00 | | 90.00 | 90.00 | P 21 21 21 | |
| SCALE1 | | 0.013916 | 0.000000 | | 0.000000 | | 0.00000 | | | |
| SCALE2 | | 0.000000 | 0.007745 | | 0.000000 | | 0.00000 | | | |
| SCALE3 | | 0.000000 | 0.000000 | | 0.005033 | | 0.00000 | | | |
| ATOM | 1 | N | SER A | 2 | −7.923 | 44.191 | −51.658 | 1.00 | 21.42 | N |
| ATOM | 2 | CA | SER A | 2 | −8.131 | 42.928 | −50.873 | 1.00 | 22.29 | C |
| ATOM | 3 | CB | SER A | 2 | −9.616 | 42.524 | −50.829 | 1.00 | 23.04 | C |
| ATOM | 4 | OG | SER A | 2 | −9.849 | 41.431 | −49.937 | 1.00 | 22.96 | O |
| ATOM | 5 | C | SER A | 2 | −7.266 | 41.758 | −51.369 | 1.00 | 21.69 | C |
| ATOM | 6 | O | SER A | 2 | −7.189 | 41.478 | −52.568 | 1.00 | 22.35 | O |
| ATOM | 7 | N | TYR A | 3 | −6.655 | 41.068 | −50.406 | 1.00 | 20.49 | N |
| ATOM | 8 | CA | TYR A | 3 | −5.609 | 40.085 | −50.637 | 1.00 | 18.61 | C |
| ATOM | 9 | CB | TYR A | 3 | −4.275 | 40.712 | −50.280 | 1.00 | 18.10 | C |
| ATOM | 10 | CG | TYR A | 3 | −4.027 | 42.055 | −50.906 | 1.00 | 18.01 | C |
| ATOM | 11 | CD1 | TYR A | 3 | −3.470 | 42.150 | −52.184 | 1.00 | 17.99 | C |
| ATOM | 12 | CE1 | TYR A | 3 | −3.214 | 43.380 | −52.767 | 1.00 | 17.92 | C |
| ATOM | 13 | CZ | TYR A | 3 | −3.514 | 44.537 | −52.072 | 1.00 | 17.79 | C |
| ATOM | 14 | OH | TYR A | 3 | −3.261 | 45.734 | −52.674 | 1.00 | 17.76 | O |
| ATOM | 15 | CE2 | TYR A | 3 | −4.065 | 44.480 | −50.797 | 1.00 | 17.83 | C |
| ATOM | 16 | CD2 | TYR A | 3 | −4.321 | 43.239 | −50.221 | 1.00 | 17.87 | C |
| ATOM | 17 | C | TYR A | 3 | −5.839 | 38.900 | −49.707 | 1.00 | 17.88 | C |
| ATOM | 18 | O | TYR A | 3 | −5.794 | 39.056 | −48.487 | 1.00 | 18.43 | O |
| ATOM | 19 | N | ASN A | 4 | −6.071 | 37.719 | −50.263 | 1.00 | 16.80 | N |
| ATOM | 20 | CA | ASN A | 4 | −6.498 | 36.592 | −49.443 | 1.00 | 16.25 | C |
| ATOM | 21 | CB | ASN A | 4 | −7.962 | 36.234 | −49.742 | 1.00 | 16.86 | C |
| ATOM | 22 | CG | ASN A | 4 | −8.860 | 37.457 | −49.820 | 1.00 | 17.49 | C |
| ATOM | 23 | OD1 | ASN A | 4 | −9.601 | 37.758 | −48.885 | 1.00 | 17.63 | O |
| ATOM | 24 | ND2 | ASN A | 4 | −8.782 | 38.185 | −50.937 | 1.00 | 18.31 | N |
| ATOM | 25 | C | ASN A | 4 | −5.607 | 35.356 | −49.542 | 1.00 | 15.38 | C |
| ATOM | 26 | O | ASN A | 4 | −4.938 | 35.137 | −50.559 | 1.00 | 15.70 | O |
| ATOM | 27 | N | TYR A | 5 | −5.628 | 34.551 | −48.483 | 1.00 | 13.98 | N |
| ATOM | 28 | CA | TYR A | 5 | −4.844 | 33.334 | −48.371 | 1.00 | 13.09 | C |
| ATOM | 29 | CB | TYR A | 5 | −4.060 | 33.422 | −47.057 | 1.00 | 12.98 | C |
| ATOM | 30 | CG | TYR A | 5 | −3.119 | 32.283 | −46.708 | 1.00 | 12.85 | C |
| ATOM | 31 | CD1 | TYR A | 5 | −1.776 | 32.309 | −47.089 | 1.00 | 12.66 | C |
| ATOM | 32 | CE1 | TYR A | 5 | −0.905 | 31.276 | −46.739 | 1.00 | 12.60 | C |
| ATOM | 33 | CZ | TYR A | 5 | −1.373 | 30.211 | −45.981 | 1.00 | 12.76 | C |
| ATOM | 34 | OH | TYR A | 5 | −0.544 | 29.165 | −45.629 | 1.00 | 12.48 | O |
| ATOM | 35 | CE2 | TYR A | 5 | −2.699 | 30.180 | −45.570 | 1.00 | 12.91 | C |
| ATOM | 36 | CD2 | TYR A | 5 | −3.555 | 31.216 | −45.920 | 1.00 | 12.83 | C |
| ATOM | 37 | C | TYR A | 5 | −5.817 | 32.142 | −48.389 | 1.00 | 12.75 | C |
| ATOM | 38 | O | TYR A | 5 | −6.718 | 32.060 | −47.559 | 1.00 | 12.62 | O |
| ATOM | 39 | N | VAL A | 6 | −5.675 | 31.245 | −49.364 | 1.00 | 12.53 | N |
| ATOM | 40 | CA | VAL A | 6 | −6.528 | 30.041 | −49.427 | 1.00 | 12.16 | C |
| ATOM | 41 | CB | VAL A | 6 | −7.111 | 29.740 | −50.827 | 1.00 | 12.01 | C |
| ATOM | 42 | CG1 | VAL A | 6 | −8.440 | 29.031 | −50.691 | 1.00 | 11.90 | C |
| ATOM | 43 | CG2 | VAL A | 6 | −7.288 | 30.990 | −51.653 | 1.00 | 12.31 | C |
| ATOM | 44 | C | VAL A | 6 | −5.702 | 28.833 | −49.073 | 1.00 | 12.07 | C |
| ATOM | 45 | O | VAL A | 6 | −4.670 | 28.568 | −49.694 | 1.00 | 12.04 | O |
| ATOM | 46 | N | VAL A | 7 | −6.173 | 28.079 | −48.093 | 1.00 | 12.02 | N |
| ATOM | 47 | CA | VAL A | 7 | −5.498 | 26.863 | −47.702 | 1.00 | 12.08 | C |
| ATOM | 48 | CB | VAL A | 7 | −4.578 | 27.110 | −46.494 | 1.00 | 12.20 | C |
| ATOM | 49 | CG1 | VAL A | 7 | −5.380 | 27.211 | −45.197 | 1.00 | 12.19 | C |
| ATOM | 50 | CG2 | VAL A | 7 | −3.503 | 26.036 | −46.419 | 1.00 | 12.40 | C |
| ATOM | 51 | C | VAL A | 7 | −6.512 | 25.751 | −47.424 | 1.00 | 12.19 | C |
| ATOM | 52 | O | VAL A | 7 | −7.632 | 26.022 | −46.987 | 1.00 | 12.49 | O |
| ATOM | 53 | N | THR A | 8 | −6.115 | 24.513 | −47.704 | 1.00 | 11.94 | N |
| ATOM | 54 | CA | THR A | 8 | −6.921 | 23.338 | −47.435 | 1.00 | 11.84 | C |
| ATOM | 55 | CB | THR A | 8 | −6.411 | 22.153 | −48.265 | 1.00 | 12.28 | C |
| ATOM | 56 | OG1 | THR A | 8 | −6.498 | 22.463 | −49.660 | 1.00 | 12.25 | O |
| ATOM | 57 | CG2 | THR A | 8 | −7.205 | 20.874 | −47.954 | 1.00 | 12.37 | C |
| ATOM | 58 | C | THR A | 8 | −6.830 | 22.923 | −45.970 | 1.00 | 11.59 | C |
| ATOM | 59 | O | THR A | 8 | −5.750 | 22.794 | −45.424 | 1.00 | 11.59 | O |
| ATOM | 60 | N | ALA A | 9 | −7.972 | 22.701 | −45.341 | 1.00 | 11.44 | N |
| ATOM | 61 | CA | ALA A | 9 | −7.986 | 22.193 | −43.978 | 1.00 | 11.07 | C |
| ATOM | 62 | CB | ALA A | 9 | −8.969 | 22.975 | −43.138 | 1.00 | 11.25 | C |
| ATOM | 63 | C | ALA A | 9 | −8.325 | 20.707 | −43.946 | 1.00 | 10.83 | C |

-continued

| Atomic coordinates for CRBN:DDB1:Lenalidomide (Human protein) | | | | | | | | | | |
|---|---|---|---|---|---|---|---|---|---|---|
| ATOM | 64 | O | ALA A | 9 | −7.970 | 20.018 | −43.003 | 1.00 | 10.79 | O |
| ATOM | 65 | N | GLN A | 10 | −9.046 | 20.236 | −44.963 | 1.00 | 10.58 | N |
| ATOM | 66 | CA | GLN A | 10 | −9.366 | 18.824 | −45.128 | 1.00 | 10.39 | C |
| ATOM | 67 | CB | GLN A | 10 | −10.749 | 18.509 | −44.551 | 1.00 | 10.35 | C |
| ATOM | 68 | CG | GLN A | 10 | −11.327 | 17.163 | −44.976 | 1.00 | 10.22 | C |
| ATOM | 69 | CD | GLN A | 10 | −10.452 | 16.009 | −44.547 | 1.00 | 10.19 | C |
| ATOM | 70 | OE1 | GLN A | 10 | −10.178 | 15.849 | −43.359 | 1.00 | 10.42 | O |
| ATOM | 71 | NE2 | GLN A | 10 | −9.994 | 15.203 | −45.508 | 1.00 | 9.87 | N |
| ATOM | 72 | C | GLN A | 10 | −9.337 | 18.504 | −46.615 | 1.00 | 10.53 | C |
| ATOM | 73 | O | GLN A | 10 | −10.120 | 19.056 | −47.385 | 1.00 | 10.94 | O |
| ATOM | 74 | N | LYS A | 11 | −8.430 | 17.622 | −47.022 | 1.00 | 10.37 | N |
| ATOM | 75 | CA | LYS A | 11 | −8.288 | 17.259 | −48.424 | 1.00 | 10.13 | C |
| ATOM | 76 | CB | LYS A | 11 | −7.092 | 16.342 | −48.611 | 1.00 | 10.25 | C |
| ATOM | 77 | CG | LYS A | 11 | −5.742 | 16.959 | −48.350 | 1.00 | 10.41 | C |
| ATOM | 78 | CD | LYS A | 11 | −4.705 | 15.953 | −48.785 | 1.00 | 10.73 | C |
| ATOM | 79 | CE | LYS A | 11 | −3.386 | 16.161 | −48.090 | 1.00 | 11.15 | C |
| ATOM | 80 | NZ | LYS A | 11 | −2.882 | 14.810 | −47.710 | 1.00 | 11.49 | N |
| ATOM | 81 | C | LYS A | 11 | −9.533 | 16.529 | −48.888 | 1.00 | 9.93 | C |
| ATOM | 82 | O | LYS A | 11 | −10.219 | 15.929 | −48.083 | 1.00 | 9.94 | O |
| ATOM | 83 | N | PRO A | 12 | −9.809 | 16.553 | −50.194 | 1.00 | 9.83 | N |
| ATOM | 84 | CA | PRO A | 12 | −11.014 | 15.897 | −50.738 | 1.00 | 9.94 | C |
| ATOM | 85 | CB | PRO A | 12 | −10.818 | 15.986 | −52.256 | 1.00 | 10.02 | C |
| ATOM | 86 | CG | PRO A | 12 | −9.763 | 17.026 | −52.460 | 1.00 | 10.06 | C |
| ATOM | 87 | CD | PRO A | 12 | −8.900 | 17.031 | −51.246 | 1.00 | 9.78 | C |
| ATOM | 88 | C | PRO A | 12 | −11.095 | 14.440 | −50.332 | 1.00 | 9.90 | C |
| ATOM | 89 | O | PRO A | 12 | −10.087 | 13.739 | −50.400 | 1.00 | 9.98 | O |
| ATOM | 90 | N | THR A | 13 | −12.271 | 13.985 | −49.903 | 1.00 | 10.05 | N |
| ATOM | 91 | CA | THR A | 13 | −12.422 | 12.584 | −49.438 | 1.00 | 10.17 | C |
| ATOM | 92 | CB | THR A | 13 | −13.153 | 12.464 | −48.087 | 1.00 | 9.80 | C |
| ATOM | 93 | OG1 | THR A | 13 | −14.470 | 13.013 | −48.207 | 1.00 | 9.74 | O |
| ATOM | 94 | CG2 | THR A | 13 | −12.403 | 13.188 | −47.005 | 1.00 | 9.47 | C |
| ATOM | 95 | C | THR A | 13 | −13.124 | 11.688 | −50.452 | 1.00 | 10.50 | C |
| ATOM | 96 | O | THR A | 13 | −12.867 | 10.478 | −50.486 | 1.00 | 10.93 | O |
| ATOM | 97 | N | ALA A | 14 | −14.002 | 12.271 | −51.272 | 1.00 | 10.59 | N |
| ATOM | 98 | CA | ALA A | 14 | −14.754 | 11.506 | −52.276 | 1.00 | 10.84 | C |
| ATOM | 99 | CB | ALA A | 14 | −15.799 | 12.385 | −52.914 | 1.00 | 10.95 | C |
| ATOM | 100 | C | ALA A | 14 | −13.875 | 10.845 | −53.355 | 1.00 | 10.99 | C |
| ATOM | 101 | O | ALA A | 14 | −12.929 | 11.459 | −53.837 | 1.00 | 11.15 | O |
| ATOM | 102 | N | VAL A | 15 | −14.202 | 9.607 | −53.734 | 1.00 | 11.13 | N |
| ATOM | 103 | CA | VAL A | 15 | −13.449 | 8.870 | −54.766 | 1.00 | 11.38 | C |
| ATOM | 104 | CB | VAL A | 15 | −13.386 | 7.360 | −54.447 | 1.00 | 11.25 | C |
| ATOM | 105 | CG1 | VAL A | 15 | −12.963 | 6.561 | −55.675 | 1.00 | 11.41 | C |
| ATOM | 106 | CG2 | VAL A | 15 | −12.418 | 7.111 | −53.303 | 1.00 | 11.07 | C |
| ATOM | 107 | C | VAL A | 15 | −13.947 | 9.092 | −56.215 | 1.00 | 11.67 | C |
| ATOM | 108 | O | VAL A | 15 | −15.065 | 8.742 | −56.538 | 1.00 | 12.02 | O |
| ATOM | 109 | N | ASN A | 16 | −13.092 | 9.654 | −57.072 | 0.50 | 11.92 | N |
| ATOM | 110 | CA | ASN A | 16 | −13.407 | 9.906 | −58.480 | 0.50 | 12.12 | C |
| ATOM | 111 | CB | ASN A | 16 | −12.411 | 10.891 | −59.054 | 0.50 | 12.15 | C |
| ATOM | 112 | CG | ASN A | 16 | −12.697 | 12.292 | −58.644 | 0.50 | 12.38 | C |
| ATOM | 113 | OD1 | ASN A | 16 | −12.750 | 12.611 | −57.453 | 0.50 | 12.39 | O |
| ATOM | 114 | ND2 | ASN A | 16 | −12.892 | 13.156 | −59.632 | 0.50 | 12.72 | N |
| ATOM | 115 | C | ASN A | 16 | −13.326 | 8.673 | −59.337 | 0.50 | 12.42 | C |
| ATOM | 116 | O | ASN A | 16 | −14.118 | 8.480 | −60.250 | 0.50 | 12.08 | O |
| ATOM | 117 | N | GLY A | 17 | −12.311 | 7.870 | −59.056 | 1.00 | 13.20 | N |
| ATOM | 118 | CA | GLY A | 17 | −11.928 | 6.736 | −59.890 | 1.00 | 14.55 | C |
| ATOM | 119 | C | GLY A | 17 | −11.012 | 5.806 | −59.122 | 1.00 | 15.30 | C |
| ATOM | 120 | O | GLY A | 17 | −10.434 | 6.209 | −58.115 | 1.00 | 15.79 | O |
| ATOM | 121 | N | CYS A | 18 | −10.882 | 4.566 | −59.585 | 1.00 | 15.81 | N |
| ATOM | 122 | CA | CYS A | 18 | −10.156 | 3.552 | −58.840 | 1.00 | 17.16 | C |
| ATOM | 123 | CB | CYS A | 18 | −11.029 | 2.994 | −57.700 | 1.00 | 17.76 | C |
| ATOM | 124 | SG | CYS A | 18 | −12.709 | 2.452 | −58.177 | 1.00 | 20.76 | S |
| ATOM | 125 | C | CYS A | 18 | −9.681 | 2.444 | −59.773 | 1.00 | 18.24 | C |
| ATOM | 126 | O | CYS A | 18 | −10.489 | 1.730 | −60.349 | 1.00 | 20.21 | O |
| ATOM | 127 | N | VAL A | 19 | −8.367 | 2.300 | −59.926 | 1.00 | 18.29 | N |
| ATOM | 128 | CA | VAL A | 19 | −7.780 | 1.333 | −60.878 | 1.00 | 17.71 | C |
| ATOM | 129 | CB | VAL A | 19 | −7.087 | 2.100 | −62.049 | 1.00 | 17.28 | C |
| ATOM | 130 | CG1 | VAL A | 19 | −5.701 | 2.574 | −61.650 | 1.00 | 16.84 | C |
| ATOM | 131 | CG2 | VAL A | 19 | −7.028 | 1.261 | −63.320 | 1.00 | 17.29 | C |
| ATOM | 132 | C | VAL A | 19 | −6.814 | 0.322 | −60.187 | 1.00 | 17.49 | C |
| ATOM | 133 | O | VAL A | 19 | −6.242 | 0.608 | −59.127 | 1.00 | 17.47 | O |
| ATOM | 134 | N | THR A | 20 | −6.647 | −0.859 | −60.770 | 1.00 | 17.31 | N |
| ATOM | 135 | CA | THR A | 20 | −5.632 | −1.804 | −60.276 | 1.00 | 17.57 | C |
| ATOM | 136 | CB | THR A | 20 | −6.232 | −3.101 | −59.712 | 1.00 | 17.48 | C |
| ATOM | 137 | OG1 | THR A | 20 | −7.084 | −3.694 | −60.694 | 1.00 | 17.58 | O |
| ATOM | 138 | CG2 | THR A | 20 | −7.019 | −2.828 | −58.442 | 1.00 | 17.55 | C |
| ATOM | 139 | C | THR A | 20 | −4.668 | −2.191 | −61.374 | 1.00 | 17.89 | C |
| ATOM | 140 | O | THR A | 20 | −4.873 | −1.847 | −62.537 | 1.00 | 18.11 | O |

| | | | | | | | | | |
|---|---|---|---|---|---|---|---|---|---|
| ATOM | 141 | N | GLY A | 21 | −3.623 | −2.918 | −61.001 | 1.00 | 18.04 | N |
| ATOM | 142 | CA | GLY A | 21 | −2.567 | −3.277 | −61.933 | 1.00 | 18.71 | C |
| ATOM | 143 | C | GLY A | 21 | −1.241 | −3.263 | −61.227 | 1.00 | 19.10 | C |
| ATOM | 144 | O | GLY A | 21 | −1.200 | −3.239 | −59.996 | 1.00 | 19.56 | O |
| ATOM | 145 | N | HIS A | 22 | −0.152 | −3.269 | −61.990 | 1.00 | 19.40 | N |
| ATOM | 146 | CA | HIS A | 22 | 1.170 | −3.424 | −61.381 | 1.00 | 20.26 | C |
| ATOM | 147 | CB | HIS A | 22 | 1.823 | −4.717 | −61.846 | 1.00 | 21.59 | C |
| ATOM | 148 | CG | HIS A | 22 | 0.972 | −5.933 | −61.584 | 1.00 | 23.17 | C |
| ATOM | 149 | ND1 | HIS A | 22 | −0.212 | −6.134 | −62.203 | 1.00 | 24.33 | N |
| ATOM | 150 | CE1 | HIS A | 22 | −0.768 | −7.274 | −61.751 | 1.00 | 24.58 | C |
| ATOM | 151 | NE2 | HIS A | 22 | 0.063 | −7.806 | −60.837 | 1.00 | 24.54 | N |
| ATOM | 152 | CD2 | HIS A | 22 | 1.144 | −7.002 | −60.709 | 1.00 | 23.76 | C |
| ATOM | 153 | C | HIS A | 22 | 2.037 | −2.227 | −61.591 | 1.00 | 19.84 | C |
| ATOM | 154 | O | HIS A | 22 | 2.707 | −2.086 | −62.621 | 1.00 | 20.42 | O |
| ATOM | 155 | N | PHE A | 23 | 2.033 | −1.353 | −60.590 | 1.00 | 18.33 | N |
| ATOM | 156 | CA | PHE A | 23 | 2.565 | −0.020 | −60.735 | 1.00 | 17.77 | C |
| ATOM | 157 | CB | PHE A | 23 | 1.480 | 1.004 | −60.404 | 1.00 | 17.35 | C |
| ATOM | 158 | CG | PHE A | 23 | 1.892 | 2.426 | −60.621 | 1.00 | 16.71 | C |
| ATOM | 159 | CD1 | PHE A | 23 | 2.126 | 2.905 | −61.894 | 1.00 | 16.37 | C |
| ATOM | 160 | CE1 | PHE A | 23 | 2.509 | 4.216 | −62.090 | 1.00 | 16.61 | C |
| ATOM | 161 | CZ | PHE A | 23 | 2.643 | 5.068 | −61.012 | 1.00 | 16.74 | C |
| ATOM | 162 | CE2 | PHE A | 23 | 2.401 | 4.605 | −59.735 | 1.00 | 16.88 | C |
| ATOM | 163 | CD2 | PHE A | 23 | 2.024 | 3.289 | −59.546 | 1.00 | 16.73 | C |
| ATOM | 164 | C | PHE A | 23 | 3.800 | 0.213 | −59.888 | 1.00 | 17.99 | C |
| ATOM | 165 | O | PHE A | 23 | 4.784 | 0.761 | −60.381 | 1.00 | 18.85 | O |
| ATOM | 166 | N | THR A | 24 | 3.751 | −0.189 | −58.622 | 1.00 | 18.14 | N |
| ATOM | 167 | CA | THR A | 24 | 4.893 | −0.021 | −57.719 | 1.00 | 18.89 | C |
| ATOM | 168 | CB | THR A | 24 | 4.486 | −0.155 | −56.233 | 1.00 | 18.69 | C |
| ATOM | 169 | OG1 | THR A | 24 | 3.705 | −1.340 | −56.046 | 1.00 | 18.28 | O |
| ATOM | 170 | CG2 | THR A | 24 | 3.674 | 1.035 | −55.800 | 1.00 | 18.88 | C |
| ATOM | 171 | C | THR A | 24 | 6.043 | −0.993 | −58.023 | 1.00 | 19.74 | C |
| ATOM | 172 | O | THR A | 24 | 7.164 | −0.787 | −57.566 | 1.00 | 20.39 | O |
| ATOM | 173 | N | SER A | 25 | 5.749 | −2.025 | −58.822 | 1.00 | 20.41 | N |
| ATOM | 174 | CA | SER A | 25 | 6.622 | −3.185 | −59.067 | 1.00 | 20.32 | C |
| ATOM | 175 | CB | SER A | 25 | 7.111 | −3.769 | −57.725 | 1.00 | 20.28 | C |
| ATOM | 176 | OG | SER A | 25 | 7.028 | −5.184 | −57.675 | 1.00 | 20.57 | O |
| ATOM | 177 | C | SER A | 25 | 5.806 | −4.218 | −59.873 | 1.00 | 20.44 | C |
| ATOM | 178 | O | SER A | 25 | 4.571 | −4.192 | −59.830 | 1.00 | 20.80 | O |
| ATOM | 179 | N | ALA A | 26 | 6.470 | −5.108 | −60.617 | 1.00 | 20.07 | N |
| ATOM | 180 | CA | ALA A | 26 | 5.746 | −6.166 | −61.356 | 1.00 | 20.11 | C |
| ATOM | 181 | CB | ALA A | 26 | 6.639 | −6.840 | −62.380 | 1.00 | 19.97 | C |
| ATOM | 182 | C | ALA A | 26 | 5.141 | −7.207 | −60.421 | 1.00 | 20.30 | C |
| ATOM | 183 | O | ALA A | 26 | 4.154 | −7.860 | −60.759 | 1.00 | 20.64 | O |
| ATOM | 184 | N | GLU A | 27 | 5.739 | −7.351 | −59.244 | 1.00 | 20.61 | N |
| ATOM | 185 | CA | GLU A | 27 | 5.282 | −8.313 | −58.253 | 1.00 | 20.91 | C |
| ATOM | 186 | CB | GLU A | 27 | 6.433 | −8.709 | −57.316 | 1.00 | 20.86 | C |
| ATOM | 187 | C | GLU A | 27 | 4.070 | −7.793 | −57.464 | 1.00 | 20.66 | C |
| ATOM | 188 | O | GLU A | 27 | 3.112 | −8.527 | −57.248 | 1.00 | 20.36 | O |
| ATOM | 189 | N | ASP A | 28 | 4.110 | −6.527 | −57.050 | 1.00 | 20.59 | N |
| ATOM | 190 | CA | ASP A | 28 | 3.005 | −5.933 | −56.290 | 1.00 | 20.28 | C |
| ATOM | 191 | CB | ASP A | 28 | 3.362 | −4.503 | −55.851 | 1.00 | 20.79 | C |
| ATOM | 192 | CG | ASP A | 28 | 4.696 | −4.421 | −55.103 | 1.00 | 21.97 | C |
| ATOM | 193 | OD1 | ASP A | 28 | 5.139 | −5.467 | −54.572 | 1.00 | 21.99 | O |
| ATOM | 194 | OD2 | ASP A | 28 | 5.299 | −3.307 | −55.036 | 1.00 | 22.11 | O |
| ATOM | 195 | C | ASP A | 28 | 1.717 | −5.902 | −57.120 | 1.00 | 19.66 | C |
| ATOM | 196 | O | ASP A | 28 | 1.763 | −5.825 | −58.345 | 1.00 | 19.97 | O |
| ATOM | 197 | N | LEU A | 29 | 0.572 | −5.970 | −56.452 | 1.00 | 18.76 | N |
| ATOM | 198 | CA | LEU A | 29 | −0.690 | −5.534 | −57.057 | 1.00 | 17.92 | C |
| ATOM | 199 | CB | LEU A | 29 | −1.778 | −6.607 | −56.923 | 1.00 | 18.23 | C |
| ATOM | 200 | CG | LEU A | 29 | −3.231 | −6.212 | −57.243 | 1.00 | 18.16 | C |
| ATOM | 201 | CD1 | LEU A | 29 | −3.535 | −6.226 | −58.734 | 1.00 | 17.53 | C |
| ATOM | 202 | CD2 | LEU A | 29 | −4.171 | −7.137 | −56.489 | 1.00 | 18.27 | C |
| ATOM | 203 | C | LEU A | 29 | −1.126 | −4.249 | −56.367 | 1.00 | 17.31 | C |
| ATOM | 204 | O | LEU A | 29 | −1.214 | −4.181 | −55.132 | 1.00 | 17.65 | O |
| ATOM | 205 | N | ASN A | 30 | −1.387 | −3.221 | −57.150 | 1.00 | 16.28 | N |
| ATOM | 206 | CA | ASN A | 30 | −1.701 | −1.944 | −56.557 | 1.00 | 15.87 | C |
| ATOM | 207 | CB | ASN A | 30 | −0.800 | −0.864 | −57.124 | 1.00 | 15.82 | C |
| ATOM | 208 | CG | ASN A | 30 | 0.643 | −1.116 | −56.821 | 1.00 | 15.96 | C |
| ATOM | 209 | OD1 | ASN A | 30 | 1.038 | −1.174 | −55.665 | 1.00 | 16.17 | O |
| ATOM | 210 | ND2 | ASN A | 30 | 1.437 | −1.300 | −57.855 | 1.00 | 16.26 | N |
| ATOM | 211 | C | ASN A | 30 | −3.135 | −1.552 | −56.745 | 1.00 | 15.62 | C |
| ATOM | 212 | O | ASN A | 30 | −3.783 | −1.945 | −57.710 | 1.00 | 16.26 | O |
| ATOM | 213 | N | LEU A | 31 | −3.636 | −0.772 | −55.81 | 1.00 | 14.98 | N |
| ATOM | 214 | CA | LEU A | 31 | −4.886 | −0.109 | −56.021 | 1.00 | 14.75 | C |
| ATOM | 215 | CB | LEU A | 31 | −5.848 | −0.414 | −54.869 | 1.00 | 14.48 | C |
| ATOM | 216 | CG | LEU A | 31 | −7.126 | 0.412 | −54.726 | 1.00 | 14.07 | C |
| ATOM | 217 | CD1 | LEU A | 31 | −7.984 | 0.348 | −55.983 | 1.00 | 13.99 | C |

-continued

| | | | Atomic coordinates for CRBN:DDB1:Lenalidomide (Human protein) | | | | | | |
|---|---|---|---|---|---|---|---|---|---|
| ATOM | 218 | CD2 | LEU A | 31 | −7.888 | −0.072 | −53.510 | 1.00 | 13.77 | C |
| ATOM | 219 | C | LEU A | 31 | −4.556 | 1.370 | −56.113 | 1.00 | 14.66 | C |
| ATOM | 220 | O | LEU A | 31 | −3.905 | 1.912 | −55.220 | 1.00 | 14.56 | O |
| ATOM | 221 | N | LEU A | 32 | −4.959 | 1.999 | −57.220 | 1.00 | 14.48 | N |
| ATOM | 222 | CA | LEU A | 32 | −4.801 | 3.443 | −57.397 | 1.00 | 14.27 | C |
| ATOM | 223 | CB | LEU A | 32 | −4.130 | 3.769 | −58.727 | 1.00 | 14.26 | C |
| ATOM | 224 | CG | LEU A | 32 | −2.604 | 3.758 | −58.730 | 1.00 | 14.43 | C |
| ATOM | 225 | CD1 | LEU A | 32 | −2.052 | 2.351 | −58.558 | 1.00 | 14.50 | C |
| ATOM | 226 | CD2 | LEU A | 32 | −2.104 | 4.339 | −60.032 | 1.00 | 14.66 | C |
| ATOM | 227 | C | LEU A | 32 | −6.147 | 4.131 | −57.308 | 1.00 | 13.95 | C |
| ATOM | 228 | O | LEU A | 32 | −7.060 | 3.785 | −58.047 | 1.00 | 13.86 | O |
| ATOM | 229 | N | ILE A | 33 | −6.247 | 5.104 | −56.399 | 1.00 | 13.61 | N |
| ATOM | 230 | CA | ILE A | 33 | −7.499 | 5.793 | −56.086 | 1.00 | 13.36 | C |
| ATOM | 231 | CB | ILE A | 33 | −7.874 | 5.579 | −54.609 | 1.00 | 13.17 | C |
| ATOM | 232 | CG1 | ILE A | 33 | −7.966 | 4.100 | −54.279 | 1.00 | 13.23 | C |
| ATOM | 233 | CD1 | ILE A | 33 | −8.277 | 3.831 | −52.824 | 1.00 | 13.39 | C |
| ATOM | 234 | CG2 | ILE A | 33 | −9.192 | 6.257 | −54.279 | 1.00 | 13.29 | C |
| ATOM | 235 | C | ILE A | 33 | −7.376 | 7.304 | −56.320 | 1.00 | 13.55 | C |
| ATOM | 236 | O | ILE A | 33 | −6.506 | 7.965 | −55.740 | 1.00 | 13.95 | O |
| ATOM | 237 | N | ALA A | 34 | −8.250 | 7.862 | −57.141 | 1.00 | 13.28 | N |
| ATOM | 238 | CA | ALA A | 34 | −8.242 | 9.303 | −57.338 | 1.00 | 13.46 | C |
| ATOM | 239 | CB | ALA A | 34 | −8.482 | 9.640 | −58.798 | 1.00 | 13.49 | C |
| ATOM | 240 | C | ALA A | 34 | −9.256 | 10.032 | −56.448 | 1.00 | 13.71 | C |
| ATOM | 241 | O | ALA A | 34 | −10.446 | 9.726 | −56.451 | 1.00 | 13.94 | O |
| ATOM | 242 | N | LYS A | 35 | −8.772 | 11.000 | −55.689 | 1.00 | 13.73 | N |
| ATOM | 243 | CA | LYS A | 35 | −9.634 | 11.907 | −54.974 | 1.00 | 13.74 | C |
| ATOM | 244 | CB | LYS A | 35 | −9.301 | 11.870 | −53.489 | 1.00 | 13.64 | C |
| ATOM | 245 | CG | LYS A | 35 | −9.925 | 10.690 | −52.773 | 1.00 | 13.75 | C |
| ATOM | 246 | CD | LYS A | 35 | −8.974 | 10.076 | −51.777 | 1.00 | 13.86 | C |
| ATOM | 247 | CE | LYS A | 35 | −9.725 | 9.324 | −50.698 | 1.00 | 14.04 | C |
| ATOM | 248 | NZ | LYS A | 35 | −9.243 | 9.724 | −49.347 | 1.00 | 14.20 | N |
| ATOM | 249 | C | LYS A | 35 | −9.436 | 13.305 | −55.549 | 1.00 | 14.30 | C |
| ATOM | 250 | O | LYS A | 35 | −8.653 | 14.102 | −55.011 | 1.00 | 14.27 | O |
| ATOM | 251 | N | ASN A | 36 | −10.141 | 13.582 | −56.658 | 1.00 | 14.67 | N |
| ATOM | 252 | CA | ASN A | 36 | −10.099 | 14.885 | −57.368 | 1.00 | 14.86 | C |
| ATOM | 253 | CB | ASN A | 36 | −10.785 | 15.992 | −56.550 | 1.00 | 14.52 | C |
| ATOM | 254 | CG | ASN A | 36 | −10.960 | 17.286 | −57.325 | 1.00 | 14.26 | C |
| ATOM | 255 | OD1 | ASN A | 36 | −11.093 | 17.288 | −58.540 | 1.00 | 14.27 | O |
| ATOM | 256 | ND2 | ASN A | 36 | −10.999 | 18.393 | −56.610 | 1.00 | 14.18 | N |
| ATOM | 257 | C | ASN A | 36 | −8.694 | 15.311 | −57.792 | 1.00 | 15.53 | C |
| ATOM | 258 | O | ASN A | 36 | −8.268 | 15.027 | −58.913 | 1.00 | 15.76 | O |
| ATOM | 259 | N | THR A | 37 | −7.982 | 15.997 | −56.901 | 1.00 | 16.35 | N |
| ATOM | 260 | CA | THR A | 37 | −6.615 | 16.454 | −57.187 | 1.00 | 17.25 | C |
| ATOM | 261 | CB | THR A | 37 | −6.415 | 17.944 | −56.816 | 1.00 | 16.76 | C |
| ATOM | 262 | OG1 | THR A | 37 | −6.870 | 18.166 | −55.477 | 1.00 | 17.00 | O |
| ATOM | 263 | CG2 | THR A | 37 | −7.183 | 18.833 | −57.735 | 1.00 | 15.73 | C |
| ATOM | 264 | C | THR A | 37 | −5.554 | 15.610 | −56.464 | 1.00 | 18.24 | C |
| ATOM | 265 | O | THR A | 37 | −4.379 | 15.983 | −56.417 | 1.00 | 18.84 | O |
| ATOM | 266 | N | ARG A | 38 | −5.966 | 14.476 | −55.903 | 1.00 | 19.00 | N |
| ATOM | 267 | CA | ARG A | 38 | −5.054 | 13.627 | −55.132 | 1.00 | 19.34 | C |
| ATOM | 268 | CB | ARG A | 38 | −5.478 | 13.595 | −53.668 | 1.00 | 20.22 | C |
| ATOM | 269 | CG | ARG A | 38 | −5.476 | 14.947 | −52.989 | 1.00 | 21.38 | C |
| ATOM | 270 | CD | ARG A | 38 | −4.253 | 15.072 | −52.101 | 1.00 | 23.51 | C |
| ATOM | 271 | NE | ARG A | 38 | −3.219 | 15.991 | −52.594 | 1.00 | 24.85 | N |
| ATOM | 272 | CZ | ARG A | 38 | −2.030 | 16.173 | −52.009 | 1.00 | 25.56 | C |
| ATOM | 273 | NH1 | ARG A | 38 | −1.158 | 17.028 | −52.524 | 1.00 | 26.93 | N |
| ATOM | 274 | NH2 | ARG A | 38 | −1.697 | 15.502 | −50.912 | 1.00 | 25.36 | N |
| ATOM | 275 | C | ARG A | 38 | −5.018 | 12.213 | −55.686 | 1.00 | 18.91 | C |
| ATOM | 276 | O | ARG A | 38 | −6.016 | 11.716 | −56.182 | 1.00 | 18.96 | O |
| ATOM | 277 | N | LEU A | 39 | −3.861 | 11.569 | −55.596 | 1.00 | 19.09 | N |
| ATOM | 278 | CA | LEU A | 39 | −3.708 | 10.186 | −56.030 | 1.00 | 19.20 | C |
| ATOM | 279 | CB | LEU A | 39 | −2.821 | 10.132 | −57.268 | 1.00 | 19.25 | C |
| ATOM | 280 | CG | LEU A | 39 | −2.565 | 8.776 | −57.919 | 1.00 | 19.14 | C |
| ATOM | 281 | CD1 | LEU A | 39 | −3.672 | 8.456 | −58.897 | 1.00 | 18.93 | C |
| ATOM | 282 | CD2 | LEU A | 39 | −1.230 | 8.819 | −58.639 | 1.00 | 19.57 | C |
| ATOM | 283 | C | LEU A | 39 | −3.101 | 9.334 | −54.916 | 1.00 | 19.42 | C |
| ATOM | 284 | O | LEU A | 39 | −1.944 | 9.530 | −54.550 | 1.00 | 19.82 | O |
| ATOM | 285 | N | GLU A | 40 | −3.884 | 8.399 | −54.374 | 1.00 | 19.42 | N |
| ATOM | 286 | CA | GLU A | 40 | −3.405 | 7.492 | −53.323 | 1.00 | 19.08 | C |
| ATOM | 287 | CB | GLU A | 40 | −4.510 | 7.223 | −52.288 | 1.00 | 19.78 | C |
| ATOM | 288 | CG | GLU A | 40 | −5.000 | 8.454 | −51.518 | 1.00 | 20.88 | C |
| ATOM | 289 | CD | GLU A | 40 | −6.265 | 8.201 | −50.662 | 1.00 | 21.77 | C |
| ATOM | 290 | OE1 | GLU A | 40 | −6.884 | 7.102 | −50.753 | 1.00 | 22.31 | O |
| ATOM | 291 | OE2 | GLU A | 40 | −6.648 | 9.116 | −49.884 | 1.00 | 21.32 | O |
| ATOM | 292 | C | GLU A | 40 | −2.951 | 6.179 | −53.960 | 1.00 | 18.42 | C |
| ATOM | 293 | O | GLU A | 40 | −3.660 | 5.630 | −54.814 | 1.00 | 18.54 | O |
| ATOM | 294 | N | GLU A | 40 | −1.762 | 5.705 | −53.573 | 1.00 | 17.46 | N |

-continued

| | | | Atomic coordinates for CRBN:DDB1:Lenalidomide (Human protein) | | | | | | |
|---|---|---|---|---|---|---|---|---|---|
| ATOM | 295 | CA | GLU A | 40 | −1.226 | 4.408 | −54.042 | 1.00 | 16.82 | C |
| ATOM | 296 | CB | ILE A | 41 | 0.136 | 4.537 | −54.736 | 1.00 | 16.24 | C |
| ATOM | 297 | CG1 | ILE A | 41 | 0.078 | 5.580 | −55.848 | 1.00 | 16.54 | C |
| ATOM | 298 | CD1 | ILE A | 41 | 1.427 | 6.108 | −56.287 | 1.00 | 16.67 | C |
| ATOM | 299 | CG2 | ILE A | 41 | 0.561 | 3.183 | −55.273 | 1.00 | 15.87 | C |
| ATOM | 300 | C | ILE A | 41 | −1.055 | 3.397 | −52.907 | 1.00 | 16.92 | C |
| ATOM | 301 | O | ILE A | 41 | −0.162 | 3.529 | −52.049 | 1.00 | 16.63 | O |
| ATOM | 302 | N | TYR A | 42 | −1.902 | 2.375 | −52.934 | 1.00 | 16.72 | N |
| ATOM | 303 | CA | TYR A | 42 | −1.865 | 1.293 | −51.972 | 1.00 | 16.23 | C |
| ATOM | 304 | CB | TYR A | 42 | −3.278 | 0.982 | −51.515 | 1.00 | 16.28 | C |
| ATOM | 305 | CG | TYR A | 42 | −3.962 | 2.064 | −50.724 | 1.00 | 16.19 | C |
| ATOM | 306 | CD1 | TYR A | 42 | −4.647 | 3.090 | −51.359 | 1.00 | 16.23 | C |
| ATOM | 307 | CE1 | TYR A | 42 | −5.297 | 4.067 | −50.633 | 1.00 | 16.31 | C |
| ATOM | 308 | CZ | TYR A | 42 | −5.274 | 4.016 | −49.254 | 1.00 | 16.34 | C |
| ATOM | 309 | OH | TYR A | 42 | −5.919 | 4.982 | −48.525 | 1.00 | 16.51 | O |
| ATOM | 310 | CE2 | TYR A | 42 | −4.603 | 3.009 | −48.598 | 1.00 | 16.22 | C |
| ATOM | 311 | CD2 | TYR A | 42 | −3.961 | 2.035 | −49.335 | 1.00 | 16.16 | C |
| ATOM | 312 | C | TYR A | 42 | −1.286 | 0.032 | −52.600 | 1.00 | 16.16 | C |
| ATOM | 313 | O | TYR A | 42 | −1.293 | −0.125 | −53.821 | 1.00 | 16.19 | O |
| ATOM | 314 | N | VAL A | 43 | −0.792 | −0.863 | −51.753 | 1.00 | 16.21 | N |
| ATOM | 315 | CA | VAL A | 43 | −0.483 | −2.229 | −52.152 | 1.00 | 16.58 | C |
| ATOM | 316 | CB | VAL A | 43 | 0.892 | −2.701 | −51.603 | 1.00 | 16.48 | C |
| ATOM | 317 | CG1 | VAL A | 43 | 1.083 | −4.193 | −51.820 | 1.00 | 16.14 | C |
| ATOM | 318 | CG2 | VAL A | 43 | 2.033 | −1.933 | −52.244 | 1.00 | 16.53 | C |
| ATOM | 319 | C | VAL A | 43 | −1.560 | −3.093 | −51.539 | 1.00 | 16.83 | C |
| ATOM | 320 | O | VAL A | 43 | −1.840 | −2.966 | −50.341 | 1.00 | 16.44 | O |
| ATOM | 321 | N | VAL A | 44 | −2.167 | −3.960 | −52.350 | 1.00 | 17.67 | N |
| ATOM | 322 | CA | VAL A | 44 | −3.139 | −4.952 | −51.842 | 1.00 | 19.01 | C |
| ATOM | 323 | CB | VAL A | 44 | −3.959 | −5.594 | −52.984 | 1.00 | 18.32 | C |
| ATOM | 324 | CG1 | VAL A | 44 | −5.099 | −6.409 | −52.417 | 1.00 | 18.51 | C |
| ATOM | 325 | CG2 | VAL A | 44 | −4.513 | −4.531 | −53.907 | 1.00 | 17.88 | C |
| ATOM | 326 | C | VAL A | 44 | −2.397 | −6.039 | −51.042 | 1.00 | 19.99 | C |
| ATOM | 327 | O | VAL A | 44 | −1.315 | −6.456 | −51.440 | 1.00 | 20.39 | O |
| ATOM | 328 | N | THR A | 45 | −2.956 | −6.474 | −49.913 | 1.00 | 21.50 | N |
| ATOM | 329 | CA | THR A | 45 | −2.272 | −7.447 | −49.040 | 1.00 | 23.54 | C |
| ATOM | 330 | CB | THR A | 45 | −1.721 | −6.802 | −47.745 | 1.00 | 23.33 | C |
| ATOM | 331 | OG1 | THR A | 45 | −2.680 | −5.865 | −47.230 | 1.00 | 24.12 | O |
| ATOM | 332 | CG2 | THR A | 45 | −0.394 | −6.107 | −47.993 | 1.00 | 22.47 | C |
| ATOM | 333 | C | THR A | 45 | −3.183 | −8.612 | −48.662 | 1.00 | 25.59 | C |
| ATOM | 334 | O | THR A | 45 | −3.306 | −9.563 | −49.420 | 1.00 | 28.20 | O |
| ATOM | 335 | N | ALA A | 46 | −3.809 | −8.531 | −47.486 | 1.00 | 26.36 | N |
| ATOM | 336 | CA | ALA A | 46 | −4.686 | −9.588 | −46.962 | 1.00 | 26.41 | C |
| ATOM | 337 | CB | ALA A | 46 | −4.002 | −10.952 | −47.024 | 1.00 | 25.04 | C |
| ATOM | 338 | C | ALA A | 46 | −5.078 | −9.250 | −45.524 | 1.00 | 27.07 | C |
| ATOM | 339 | O | ALA A | 46 | −4.278 | −8.681 | −44.766 | 1.00 | 27.05 | O |
| ATOM | 340 | N | LEU A | 49 | −4.930 | −3.391 | −47.266 | 1.00 | 15.89 | N |
| ATOM | 341 | CA | LEU A | 49 | −4.219 | −2.368 | −48.040 | 1.00 | 16.33 | C |
| ATOM | 342 | CB | LEU A | 49 | −5.164 | −1.269 | −48.551 | 1.00 | 16.09 | C |
| ATOM | 343 | CG | LEU A | 49 | −6.494 | −1.475 | −49.276 | 1.00 | 16.39 | C |
| ATOM | 344 | CD1 | LEU A | 49 | −7.012 | −0.116 | −49.720 | 1.00 | 16.16 | C |
| ATOM | 345 | CD2 | LEU A | 49 | −6.358 | −2.396 | −50.477 | 1.00 | 16.90 | C |
| ATOM | 346 | C | LEU A | 49 | −3.131 | −1.681 | −47.217 | 1.00 | 16.62 | C |
| ATOM | 347 | O | LEU A | 49 | −3.414 | −1.098 | −46.171 | 1.00 | 16.47 | O |
| ATOM | 348 | N | ARG A | 50 | −1.894 | −1.725 | −47.707 | 1.00 | 16.85 | N |
| ATOM | 349 | CA | ARG A | 50 | −0.827 | −0.922 | −47.142 | 1.00 | 16.87 | C |
| ATOM | 350 | CB | ARG A | 50 | 0.458 | −1.747 | −47.072 | 1.00 | 18.25 | C |
| ATOM | 351 | CG | ARG A | 50 | 1.740 | −0.961 | −46.824 | 1.00 | 19.73 | C |
| ATOM | 352 | CD | ARG A | 50 | 2.925 | −1.899 | −46.601 | 1.00 | 21.58 | C |
| ATOM | 353 | NE | ARG A | 50 | 3.240 | −2.744 | −47.765 | 1.00 | 23.27 | N |
| ATOM | 354 | CZ | ARG A | 50 | 4.012 | −2.364 | −48.791 | 1.00 | 24.85 | C |
| ATOM | 355 | NH1 | ARG A | 50 | 4.555 | −1.143 | −48.813 | 1.00 | 25.26 | N |
| ATOM | 356 | NH2 | ARG A | 50 | 4.247 | −3.202 | −49.801 | 1.00 | 24.60 | N |
| ATOM | 357 | C | ARG A | 50 | −0.653 | 0.337 | −48.004 | 1.00 | 16.33 | C |
| ATOM | 358 | O | ARG A | 50 | −0.352 | 0.233 | −49.187 | 1.00 | 15.97 | O |
| ATOM | 359 | N | PRO A | 51 | −0.895 | 1.529 | −47.420 | 1.00 | 16.03 | N |
| ATOM | 360 | CA | PRO A | 51 | −0.627 | 2.779 | −48.103 | 1.00 | 15.93 | C |
| ATOM | 361 | CB | PRO A | 51 | −1.022 | 3.836 | −47.071 | 1.00 | 15.60 | C |
| ATOM | 362 | CG | PRO A | 51 | −1.027 | 3.139 | −45.774 | 1.00 | 15.51 | C |
| ATOM | 363 | CD | PRO A | 51 | −1.512 | 1.770 | −46.108 | 1.00 | 16.07 | C |
| ATOM | 364 | C | PRO A | 51 | 0.846 | 2.889 | −48.411 | 1.00 | 16.28 | C |
| ATOM | 365 | O | PRO A | 51 | 1.665 | 2.475 | −47.605 | 1.00 | 17.49 | O |
| ATOM | 366 | N | VAL A | 52 | 1.191 | 3.436 | −49.566 | 1.00 | 16.17 | N |
| ATOM | 367 | CA | VAL A | 52 | 2.570 | 3.462 | −49.975 | 1.00 | 16.05 | C |
| ATOM | 368 | CB | VAL A | 52 | 2.783 | 2.412 | −51.057 | 1.00 | 15.96 | C |
| ATOM | 369 | CG1 | VAL A | 52 | 3.841 | 2.833 | −52.051 | 1.00 | 16.73 | C |
| ATOM | 370 | CG2 | VAL A | 52 | 3.145 | 1.104 | −50.402 | 1.00 | 16.42 | C |
| ATOM | 371 | C | VAL A | 52 | 3.032 | 4.865 | −50.390 | 1.00 | 16.75 | C |

-continued

| | | | | Atomic coordinates for CRBN:DDB1:Lenalidomide (Human protein) | | | | | |
|---|---|---|---|---|---|---|---|---|---|
| ATOM | 372 | O | VAL A | 52 | 4.129 | 5.295 | −50.029 | 1.00 | 16.63 | O |
| ATOM | 373 | N | LYS A | 53 | 2.176 | 5.583 | −51.116 | 1.00 | 17.59 | N |
| ATOM | 374 | CA | LYS A | 53 | 2.508 | 6.900 | −51.646 | 1.00 | 17.84 | C |
| ATOM | 375 | CB | LYS A | 53 | 3.426 | 6.764 | −52.851 | 1.00 | 18.04 | C |
| ATOM | 376 | CG | LYS A | 53 | 3.829 | 8.079 | −53.492 | 1.00 | 17.80 | C |
| ATOM | 377 | CD | LYS A | 53 | 4.566 | 8.948 | −52.502 | 1.00 | 17.82 | C |
| ATOM | 378 | CE | LYS A | 53 | 5.404 | 9.981 | −53.222 | 1.00 | 18.20 | C |
| ATOM | 379 | NZ | LYS A | 53 | 5.435 | 11.256 | −52.443 | 1.00 | 19.40 | N |
| ATOM | 380 | C | LYS A | 53 | 1.254 | 7.616 | −52.088 | 1.00 | 18.73 | C |
| ATOM | 381 | O | LYS A | 53 | 0.414 | 7.038 | −52.790 | 1.00 | 18.86 | O |
| ATOM | 382 | N | GLU A | 54 | 1.146 | 8.882 | −51.684 | 1.00 | 19.21 | N |
| ATOM | 383 | CA | GLU A | 54 | 0.078 | 9.779 | −52.111 | 1.00 | 18.91 | C |
| ATOM | 384 | CB | GLU A | 54 | −0.794 | 10.117 | −50.907 | 1.00 | 19.31 | C |
| ATOM | 385 | CG | GLU A | 54 | −1.981 | 11.019 | −51.205 | 1.00 | 20.85 | C |
| ATOM | 386 | CD | GLU A | 54 | −1.824 | 12.442 | −50.669 | 1.00 | 21.22 | C |
| ATOM | 387 | OE1 | GLU A | 54 | −2.856 | 13.142 | −50.561 | 1.00 | 21.48 | O |
| ATOM | 388 | OE2 | GLU A | 54 | −0.688 | 12.864 | −50.344 | 1.00 | 21.10 | O |
| ATOM | 389 | C | GLU A | 54 | 0.692 | 11.048 | −52.742 | 1.00 | 18.99 | C |
| ATOM | 390 | O | GLU A | 54 | 1.616 | 11.650 | −52.184 | 1.00 | 19.58 | O |
| ATOM | 391 | N | VAL A | 55 | 0.218 | 11.439 | −53.917 | 1.00 | 18.94 | N |
| ATOM | 392 | CA | VAL A | 55 | 0.718 | 12.673 | −54.550 | 1.00 | 19.06 | C |
| ATOM | 393 | CB | VAL A | 55 | 1.627 | 12.410 | −55.761 | 1.00 | 19.24 | C |
| ATOM | 394 | CG1 | VAL A | 55 | 2.975 | 11.864 | −55.304 | 1.00 | 19.62 | C |
| ATOM | 395 | CG2 | VAL A | 55 | 0.936 | 11.499 | −56.765 | 1.00 | 19.33 | C |
| ATOM | 396 | C | VAL A | 55 | −0.399 | 13.588 | −54.997 | 1.00 | 19.09 | C |
| ATOM | 397 | O | VAL A | 55 | −1.564 | 13.181 | −55.046 | 1.00 | 19.98 | O |
| ATOM | 398 | N | GLY A | 56 | −0.035 | 14.825 | −55.328 | 1.00 | 18.29 | N |
| ATOM | 399 | CA | GLY A | 56 | −1.011 | 15.841 | −55.698 | 1.00 | 17.00 | C |
| ATOM | 400 | C | GLY A | 56 | −0.713 | 16.402 | −57.059 | 1.00 | 16.19 | C |
| ATOM | 401 | O | GLY A | 56 | 0.404 | 16.807 | −57.339 | 1.00 | 16.18 | O |
| ATOM | 402 | N | MET A | 57 | −1.717 | 16.395 | −57.921 | 1.00 | 15.87 | N |
| ATOM | 403 | CA | MET A | 57 | −1.634 | 17.090 | −59.182 | 1.00 | 15.36 | C |
| ATOM | 404 | CB | MET A | 57 | −2.694 | 16.588 | −60.142 | 1.00 | 16.07 | C |
| ATOM | 405 | CG | MET A | 57 | −2.867 | 15.091 | −60.202 | 1.00 | 17.01 | C |
| ATOM | 406 | SD | MET A | 57 | −1.495 | 14.346 | −61.077 | 1.00 | 18.54 | S |
| ATOM | 407 | CE | MET A | 57 | −1.605 | 15.162 | −62.680 | 1.00 | 17.61 | C |
| ATOM | 408 | C | MET A | 57 | −1.935 | 18.540 | −58.931 | 1.00 | 14.64 | C |
| ATOM | 409 | O | MET A | 57 | −2.617 | 18.888 | −57.973 | 1.00 | 14.20 | O |
| ATOM | 410 | N | TYR A | 58 | −1.415 | 19.383 | −59.806 | 1.00 | 14.28 | N |
| ATOM | 411 | CA | TYR A | 58 | −2.023 | 20.671 | −60.063 | 1.00 | 13.71 | C |
| ATOM | 412 | CB | TYR A | 58 | −0.977 | 21.674 | −60.561 | 1.00 | 13.50 | C |
| ATOM | 413 | CG | TYR A | 58 | 0.118 | 22.015 | −59.579 | 1.00 | 13.16 | C |
| ATOM | 414 | CD1 | TYR A | 58 | −0.065 | 21.871 | −58.216 | 1.00 | 13.18 | C |
| ATOM | 415 | CE1 | TYR A | 58 | 0.940 | 22.200 | −57.322 | 1.00 | 13.36 | C |
| ATOM | 416 | CZ | TYR A | 58 | 2.146 | 22.691 | −57.796 | 1.00 | 13.36 | C |
| ATOM | 417 | OH | TYR A | 58 | 3.154 | 23.027 | −56.916 | 1.00 | 13.44 | O |
| ATOM | 418 | CE2 | TYR A | 58 | 2.342 | 22.859 | −59.148 | 1.00 | 13.20 | C |
| ATOM | 419 | CD2 | TYR A | 58 | 1.331 | 22.522 | −60.026 | 1.00 | 13.29 | C |
| ATOM | 420 | C | TYR A | 58 | −3.086 | 20.413 | −61.135 | 1.00 | 13.36 | C |
| ATOM | 421 | O | TYR A | 58 | −2.937 | 20.820 | −62.300 | 1.00 | 13.06 | O |
| ATOM | 422 | N | GLY A | 59 | −4.145 | 19.706 | −60.740 | 1.00 | 13.13 | N |
| ATOM | 423 | CA | GLY A | 59 | −5.161 | 19.261 | −61.690 | 1.00 | 13.12 | C |
| ATOM | 424 | C | GLY A | 59 | −6.279 | 18.400 | −61.130 | 1.00 | 13.30 | C |
| ATOM | 425 | O | GLY A | 59 | −6.064 | 17.554 | −60.247 | 1.00 | 13.50 | O |
| ATOM | 426 | N | LYS A | 60 | −7.487 | 18.622 | −61.637 | 1.00 | 13.17 | N |
| ATOM | 427 | CA | LYS A | 60 | −8.581 | 17.712 | −61.389 | 1.00 | 13.09 | C |
| ATOM | 428 | CB | LYS A | 60 | −9.909 | 18.381 | −61.714 | 1.00 | 13.32 | C |
| ATOM | 429 | CG | LYS A | 60 | −10.312 | 19.480 | −60.730 | 1.00 | 13.94 | C |
| ATOM | 430 | CD | LYS A | 60 | −11.657 | 20.123 | −61.084 | 1.00 | 14.12 | C |
| ATOM | 431 | CE | LYS A | 60 | −12.830 | 19.180 | −60.824 | 1.00 | 14.11 | C |
| ATOM | 432 | NZ | LYS A | 60 | −13.199 | 19.143 | −59.384 | 1.00 | 14.26 | N |
| ATOM | 433 | C | LYS A | 60 | −8.373 | 16.473 | −62.252 | 1.00 | 13.29 | C |
| ATOM | 434 | O | LYS A | 60 | −8.359 | 16.561 | −63.490 | 1.00 | 12.95 | O |
| ATOM | 435 | N | ILE A | 61 | −8.165 | 15.324 | −61.601 | 1.00 | 13.66 | N |
| ATOM | 436 | CA | ILE A | 61 | −8.001 | 14.052 | −62.322 | 1.00 | 14.04 | C |
| ATOM | 437 | CB | ILE A | 61 | −7.565 | 12.892 | −61.396 | 1.00 | 13.83 | C |
| ATOM | 438 | CG1 | ILE A | 61 | −6.159 | 13.138 | −60.833 | 1.00 | 13.72 | C |
| ATOM | 439 | CD1 | ILE A | 61 | −5.883 | 12.404 | −59.536 | 1.00 | 13.45 | C |
| ATOM | 440 | CG2 | ILE A | 61 | −7.643 | 11.551 | −62.122 | 1.00 | 13.61 | C |
| ATOM | 441 | C | ILE A | 61 | −9.323 | 13.703 | −62.984 | 1.00 | 14.51 | C |
| ATOM | 442 | O | ILE A | 61 | −10.333 | 13.522 | −62.299 | 1.00 | 14.52 | O |
| ATOM | 443 | N | ALA A | 62 | −9.301 | 13.637 | −64.315 | 1.00 | 14.99 | N |
| ATOM | 444 | CA | ALA A | 62 | −10.483 | 13.351 | −65.122 | 1.00 | 15.40 | C |
| ATOM | 445 | CB | ALA A | 62 | −10.713 | 14.473 | −66.114 | 1.00 | 15.29 | C |
| ATOM | 446 | C | ALA A | 62 | −10.384 | 12.004 | −65.864 | 1.00 | 16.28 | C |
| ATOM | 447 | O | ALA A | 62 | −11.405 | 11.447 | −66.277 | 1.00 | 17.15 | O |
| ATOM | 448 | N | VAL A | 63 | −9.162 | 11.508 | −66.071 | 1.00 | 16.28 | N |

-continued

| | | | Atomic coordinates for CRBN:DDB1:Lenalidomide (Human protein) | | | | | | |
|---|---|---|---|---|---|---|---|---|---|
| ATOM | 449 | CA | VAL A | 63 | −8.930 | 10.196 | −66.674 | 1.00 | 16.31 | C |
| ATOM | 450 | CB | VAL A | 63 | −8.684 | 10.286 | −68.193 | 1.00 | 15.95 | C |
| ATOM | 451 | CG1 | VAL A | 63 | −8.443 | 8.904 | −68.787 | 1.00 | 15.64 | C |
| ATOM | 452 | CG2 | VAL A | 63 | −9.838 | 10.973 | −68.896 | 1.00 | 16.07 | C |
| ATOM | 453 | C | VAL A | 63 | −7.683 | 9.601 | −66.033 | 1.00 | 17.40 | C |
| ATOM | 454 | O | VAL A | 63 | −6.681 | 10.308 | −65.843 | 1.00 | 18.75 | O |
| ATOM | 455 | N | MET A | 64 | −7.720 | 8.310 | −65.722 | 1.00 | 17.20 | N |
| ATOM | 456 | CA | MET A | 64 | −6.615 | 7.672 | −65.044 | 1.00 | 17.41 | C |
| ATOM | 457 | CB | MET A | 64 | −6.715 | 7.947 | −63.542 | 1.00 | 17.02 | C |
| ATOM | 458 | CG | MET A | 64 | −5.728 | 7.183 | −62.686 | 1.00 | 17.37 | C |
| ATOM | 459 | SD | MET A | 64 | −6.143 | 7.123 | −60.932 | 1.00 | 17.40 | S |
| ATOM | 460 | CE | MET A | 64 | −7.354 | 5.806 | −60.929 | 1.00 | 17.99 | C |
| ATOM | 461 | C | MET A | 64 | −6.638 | 6.175 | −65.354 | 1.00 | 18.36 | C |
| ATOM | 462 | O | MET A | 64 | −7.488 | 5.447 | −64.860 | 1.00 | 18.73 | O |
| ATOM | 463 | N | GLU A | 65 | −5.714 | 5.723 | −66.191 | 1.00 | 19.30 | N |
| ATOM | 464 | CA | GLU A | 65 | −5.663 | 4.323 | −66.575 | 1.00 | 20.87 | C |
| ATOM | 465 | CB | GLU A | 65 | −6.141 | 4.140 | −68.020 | 1.00 | 22.24 | C |
| ATOM | 466 | CG | GLU A | 65 | −7.640 | 4.327 | −68.226 | 1.00 | 24.79 | C |
| ATOM | 467 | CD | GLU A | 65 | −8.517 | 3.265 | −67.538 | 1.00 | 27.35 | C |
| ATOM | 468 | OE1 | GLU A | 65 | −8.029 | 2.139 | −67.205 | 1.00 | 27.72 | O |
| ATOM | 469 | OE2 | GLU A | 65 | −9.726 | 3.561 | −67.347 | 1.00 | 28.00 | O |
| ATOM | 470 | C | GLU A | 65 | −4.263 | 3.746 | −66.427 | 1.00 | 21.45 | C |
| ATOM | 471 | O | GLU A | 65 | −3.270 | 4.459 | −66.595 | 1.00 | 22.49 | O |
| ATOM | 472 | N | LEU A | 66 | −4.187 | 2.452 | −66.121 | 1.00 | 20.92 | N |
| ATOM | 473 | CA | LEU A | 66 | −2.923 | 1.742 | −66.156 | 1.00 | 21.07 | C |
| ATOM | 474 | CB | LEU A | 66 | −2.810 | 0.804 | −64.962 | 1.00 | 21.30 | C |
| ATOM | 475 | CG | LEU A | 66 | −2.585 | 1.454 | −63.595 | 1.00 | 21.62 | C |
| ATOM | 476 | CD1 | LEU A | 66 | −2.397 | 0.384 | −62.532 | 1.00 | 20.76 | C |
| ATOM | 477 | CD2 | LEU A | 66 | −1.390 | 2.402 | −63.623 | 1.00 | 21.50 | C |
| ATOM | 478 | C | LEU A | 66 | −2.762 | 0.965 | −67.463 | 1.00 | 21.33 | C |
| ATOM | 479 | O | LEU A | 66 | −3.730 | 0.423 | −67.996 | 1.00 | 21.48 | O |
| ATOM | 480 | N | PHE A | 67 | −1.538 | 0.907 | −67.976 | 1.00 | 21.23 | N |
| ATOM | 481 | CA | PHE A | 67 | −1.270 | 0.192 | −69.212 | 1.00 | 21.64 | C |
| ATOM | 482 | CB | PHE A | 67 | −1.595 | 1.086 | −70.401 | 1.00 | 21.19 | C |
| ATOM | 483 | CG | PHE A | 67 | −0.642 | 2.232 | −70.576 | 1.00 | 20.82 | C |
| ATOM | 484 | CD1 | PHE A | 67 | −0.748 | 3.372 | −69.787 | 1.00 | 20.94 | C |
| ATOM | 485 | CE1 | PHE A | 67 | 0.140 | 4.428 | −69.947 | 1.00 | 20.56 | C |
| ATOM | 486 | CZ | PHE A | 67 | 1.136 | 4.353 | −70.901 | 1.00 | 19.99 | C |
| ATOM | 487 | CE2 | PHE A | 67 | 1.249 | 3.222 | −71.691 | 1.00 | 20.14 | C |
| ATOM | 488 | CD2 | PHE A | 67 | 0.366 | 2.172 | −71.530 | 1.00 | 20.34 | C |
| ATOM | 489 | C | PHE A | 67 | 0.188 | −0.249 | −69.268 | 1.00 | 23.05 | C |
| ATOM | 490 | O | PHE A | 67 | 1.050 | 0.391 | −68.659 | 1.00 | 23.15 | O |
| ATOM | 491 | N | ARG A | 68 | 0.469 | −1.338 | −69.991 | 1.00 | 24.67 | N |
| ATOM | 492 | CA | ARG A | 68 | 1.855 | −1.792 | −70.153 | 1.00 | 26.52 | C |
| ATOM | 493 | CB | ARG A | 68 | 2.066 | −3.217 | −69.648 | 1.00 | 26.18 | C |
| ATOM | 494 | CG | ARG A | 68 | 3.529 | −3.495 | −69.327 | 1.00 | 26.87 | C |
| ATOM | 495 | CD | ARG A | 68 | 3.759 | −4.910 | −68.843 | 1.00 | 28.29 | C |
| ATOM | 496 | NE | ARG A | 68 | 3.047 | −5.195 | −67.595 | 1.00 | 29.60 | N |
| ATOM | 497 | CZ | ARG A | 68 | 3.634 | −5.558 | −66.462 | 1.00 | 29.23 | C |
| ATOM | 498 | NH1 | ARG A | 68 | 4.947 | −5.695 | −66.410 | 1.00 | 29.16 | N |
| ATOM | 499 | NH2 | ARG A | 68 | 2.902 | −5.801 | −65.385 | 1.00 | 29.71 | N |
| ATOM | 500 | C | ARG A | 68 | 2.366 | −1.690 | −71.573 | 1.00 | 28.42 | C |
| ATOM | 501 | O | ARG A | 68 | 1.977 | −2.477 | −72.425 | 1.00 | 28.33 | O |
| ATOM | 502 | N | PRO A | 69 | 3.281 | −0.742 | −71.823 | 1.00 | 31.15 | N |
| ATOM | 503 | CA | PRO A | 69 | 3.901 | −0.696 | −73.140 | 1.00 | 33.29 | C |
| ATOM | 504 | CB | PRO A | 69 | 4.782 | 0.560 | −73.077 | 1.00 | 33.00 | C |
| ATOM | 505 | CG | PRO A | 69 | 5.081 | 0.744 | −71.632 | 1.00 | 32.69 | C |
| ATOM | 506 | CD | PRO A | 69 | 3.897 | 0.209 | −70.877 | 1.00 | 32.13 | C |
| ATOM | 507 | C | PRO A | 69 | 4.758 | −1.939 | −73.368 | 1.00 | 35.12 | C |
| ATOM | 508 | O | PRO A | 69 | 5.312 | −2.487 | −72.419 | 1.00 | 36.02 | O |
| ATOM | 509 | N | LYS A | 70 | 4.843 | −2.376 | −74.622 | 1.00 | 37.95 | N |
| ATOM | 510 | CA | LYS A | 70 | 5.699 | −3.490 | −75.032 | 1.00 | 38.43 | C |
| ATOM | 511 | CB | LYS A | 70 | 5.707 | −3.580 | −76.562 | 1.00 | 40.38 | C |
| ATOM | 512 | CG | LYS A | 70 | 5.855 | −4.990 | −77.119 | 1.00 | 42.56 | C |
| ATOM | 513 | CD | LYS A | 70 | 6.124 | −4.970 | −78.624 | 1.00 | 43.16 | C |
| ATOM | 514 | CE | LYS A | 70 | 7.334 | −4.107 | −78.982 | 1.00 | 43.72 | C |
| ATOM | 515 | NZ | LYS A | 70 | 8.585 | −4.529 | −78.284 | 1.00 | 42.23 | N |
| ATOM | 516 | C | LYS A | 70 | 7.131 | −3.333 | −74.492 | 1.00 | 37.13 | C |
| ATOM | 517 | O | LYS A | 70 | 7.695 | −2.234 | −74.499 | 1.00 | 34.62 | O |
| ATOM | 518 | N | GLY A | 71 | 7.698 | −4.437 | −74.006 | 1.00 | 37.86 | N |
| ATOM | 519 | CA | GLY A | 71 | 9.049 | −4.443 | −73.458 | 1.00 | 38.73 | C |
| ATOM | 520 | C | GLY A | 71 | 9.233 | −3.420 | −72.352 | 1.00 | 40.73 | C |
| ATOM | 521 | O | GLY A | 71 | 10.205 | −2.666 | −72.343 | 1.00 | 42.01 | O |
| ATOM | 522 | N | GLU A | 72 | 8.273 | −3.374 | −71.436 | 1.00 | 41.59 | N |
| ATOM | 523 | CA | GLU A | 72 | 8.399 | −2.596 | −70.208 | 1.00 | 41.02 | C |
| ATOM | 524 | CB | GLU A | 72 | 7.412 | −1.434 | −70.201 | 1.00 | 41.92 | C |
| ATOM | 525 | CG | GLU A | 72 | 7.697 | −0.361 | −69.156 | 1.00 | 44.49 | C |

-continued

| | | | Atomic coordinates for CRBN:DDB1:Lenalidomide (Human protein) | | | | | | |
|---|---|---|---|---|---|---|---|---|---|
| ATOM | 526 | CD | GLU A | 72 | 8.362 | 0.885 | −69.729 | 1.00 | 46.15 | C |
| ATOM | 527 | OE1 | GLU A | 72 | 8.813 | 1.727 | −68.926 | 1.00 | 46.10 | O |
| ATOM | 528 | OE2 | GLU A | 72 | 8.431 | 1.035 | −70.973 | 1.00 | 47.23 | O |
| ATOM | 529 | C | GLU A | 72 | 8.129 | −3.550 | −69.043 | 1.00 | 40.25 | C |
| ATOM | 530 | O | GLU A | 72 | 7.348 | −4.501 | −69.175 | 1.00 | 39.52 | O |
| ATOM | 531 | N | SER A | 73 | 8.780 | −3.298 | −67.911 | 1.00 | 39.18 | N |
| ATOM | 532 | CA | SER A | 73 | 8.810 | −4.265 | −66.809 | 1.00 | 39.60 | C |
| ATOM | 533 | CB | SER A | 73 | 10.149 | −4.194 | −66.052 | 1.00 | 42.24 | C |
| ATOM | 534 | OG | SER A | 73 | 10.672 | −2.871 | −66.025 | 1.00 | 43.46 | O |
| ATOM | 535 | C | SER A | 73 | 7.620 | −4.179 | −65.838 | 1.00 | 38.72 | C |
| ATOM | 536 | O | SER A | 73 | 7.283 | −5.180 | −65.187 | 1.00 | 38.17 | O |
| ATOM | 537 | N | LYS A | 74 | 7.002 | −2.989 | −65.757 | 1.00 | 35.19 | N |
| ATOM | 538 | CA | LYS A | 74 | 5.819 | −2.712 | −64.923 | 1.00 | 31.04 | C |
| ATOM | 539 | CB | LYS A | 74 | 6.239 | −2.206 | −63.543 | 1.00 | 31.01 | C |
| ATOM | 540 | CG | LYS A | 74 | 7.492 | −1.358 | −63.570 | 1.00 | 31.73 | C |
| ATOM | 541 | CD | LYS A | 74 | 7.680 | −0.535 | −62.309 | 1.00 | 32.50 | C |
| ATOM | 542 | CE | LYS A | 74 | 8.567 | 0.663 | −62.631 | 1.00 | 33.98 | C |
| ATOM | 543 | NZ | LYS A | 74 | 9.203 | 1.275 | −61.436 | 1.00 | 34.98 | N |
| ATOM | 544 | C | LYS A | 74 | 4.929 | −1.674 | −65.612 | 1.00 | 29.38 | C |
| ATOM | 545 | O | LYS A | 74 | 5.381 | −0.984 | −66.522 | 1.00 | 28.62 | O |
| ATOM | 546 | N | ASP A | 75 | 3.672 | −1.557 | −65.169 | 1.00 | 27.74 | N |
| ATOM | 547 | CA | ASP A | 75 | 2.702 | −0.658 | −65.804 | 1.00 | 25.57 | C |
| ATOM | 548 | CB | ASP A | 75 | 1.298 | −0.833 | −65.211 | 1.00 | 25.78 | C |
| ATOM | 549 | CG | ASP A | 75 | 0.796 | −2.261 | −65.285 | 1.00 | 26.85 | C |
| ATOM | 550 | OD1 | ASP A | 75 | 1.487 | −3.112 | −65.888 | 1.00 | 26.71 | O |
| ATOM | 551 | OD2 | ASP A | 75 | −0.298 | −2.538 | −64.730 | 1.00 | 27.57 | O |
| ATOM | 552 | C | ASP A | 75 | 3.106 | 0.790 | −65.647 | 1.00 | 24.44 | C |
| ATOM | 553 | O | ASP A | 75 | 3.718 | 1.166 | −64.649 | 1.00 | 24.83 | O |
| ATOM | 554 | N | LEU A | 76 | 2.762 | 1.598 | −66.647 | 1.00 | 22.78 | N |
| ATOM | 555 | CA | LEU A | 76 | 2.788 | 3.052 | −66.522 | 1.00 | 20.94 | C |
| ATOM | 556 | CB | LEU A | 76 | 3.443 | 3.679 | −67.747 | 1.00 | 20.70 | C |
| ATOM | 557 | CG | LEU A | 76 | 4.871 | 3.232 | −68.065 | 1.00 | 20.35 | C |
| ATOM | 558 | CD1 | LEU A | 76 | 5.254 | 3.673 | −69.461 | 1.00 | 20.15 | C |
| ATOM | 559 | CD2 | LEU A | 76 | 5.861 | 3.774 | −67.049 | 1.00 | 20.45 | C |
| ATOM | 560 | C | LEU A | 76 | 1.358 | 3.593 | −66.323 | 1.00 | 20.28 | C |
| ATOM | 561 | O | LEU A | 76 | 0.369 | 2.859 | −66.492 | 1.00 | 20.28 | O |
| ATOM | 562 | N | LEU A | 77 | 1.257 | 4.868 | −65.951 | 1.00 | 18.91 | N |
| ATOM | 563 | CA | LEU A | 77 | −0.016 | 5.465 | −65.577 | 1.00 | 17.83 | C |
| ATOM | 564 | CB | LEU A | 77 | 0.022 | 5.871 | −64.106 | 1.00 | 17.81 | C |
| ATOM | 565 | CG | LEU A | 77 | −1.189 | 6.569 | −63.475 | 1.00 | 18.16 | C |
| ATOM | 566 | CD1 | LEU A | 77 | −2.401 | 5.654 | −63.369 | 1.00 | 17.75 | C |
| ATOM | 567 | CD2 | LEU A | 77 | −0.796 | 7.075 | −62.101 | 1.00 | 17.99 | C |
| ATOM | 568 | C | LEU A | 77 | −0.324 | 6.676 | −66.436 | 1.00 | 17.28 | C |
| ATOM | 569 | O | LEU A | 77 | 0.460 | 7.618 | −66.482 | 1.00 | 17.17 | O |
| ATOM | 570 | N | PHE A | 78 | −1.463 | 6.653 | −67.122 | 1.00 | 16.86 | N |
| ATOM | 571 | CA | PHE A | 78 | −1.908 | 7.823 | −67.881 | 1.00 | 16.56 | C |
| ATOM | 572 | CB | PHE A | 78 | −2.521 | 7.423 | −69.222 | 1.00 | 16.27 | C |
| ATOM | 573 | CG | PHE A | 78 | −3.109 | 8.580 | −69.978 | 1.00 | 16.08 | C |
| ATOM | 574 | CD1 | PHE A | 78 | −2.283 | 9.551 | −70.546 | 1.00 | 16.00 | C |
| ATOM | 575 | CE1 | PHE A | 78 | −2.823 | 10.620 | −71.240 | 1.00 | 15.79 | C |
| ATOM | 576 | CZ | PHE A | 78 | −4.202 | 10.736 | −71.369 | 1.00 | 15.77 | C |
| ATOM | 577 | CE2 | PHE A | 78 | −5.035 | 9.784 | −70.810 | 1.00 | 15.73 | C |
| ATOM | 578 | CD2 | PHE A | 78 | −4.487 | 8.712 | −70.113 | 1.00 | 15.99 | C |
| ATOM | 579 | C | PHE A | 78 | −2.912 | 8.659 | −67.098 | 1.00 | 16.28 | C |
| ATOM | 580 | O | PHE A | 78 | −3.903 | 8.133 | −66.586 | 1.00 | 16.53 | O |
| ATOM | 581 | N | PHE A | 78 | −2.651 | 9.956 | −67.003 | 1.00 | 15.55 | N |
| ATOM | 582 | CA | PHE A | 78 | −3.604 | 10.855 | −66.381 | 1.00 | 15.37 | C |
| ATOM | 580 | O | PHE A | 78 | −3.903 | 8.133 | −66.586 | 1.00 | 16.53 | O |
| ATOM | 581 | N | ILE A | 79 | −2.651 | 9.956 | −67.003 | 1.00 | 15.55 | N |
| ATOM | 582 | CA | ILE A | 79 | −3.604 | 10.855 | −66.381 | 1.00 | 15.37 | C |
| ATOM | 583 | CB | ILE A | 79 | −3.027 | 11.597 | −65.151 | 1.00 | 15.42 | C |
| ATOM | 584 | CG1 | ILE A | 79 | −2.470 | 10.620 | −64.109 | 1.00 | 15.66 | C |
| ATOM | 585 | CD1 | ILE A | 79 | −3.519 | 9.975 | −63.237 | 1.00 | 15.63 | C |
| ATOM | 586 | CG2 | ILE A | 79 | −4.087 | 12.483 | −64.516 | 1.00 | 14.95 | C |
| ATOM | 587 | C | ILE A | 79 | −3.973 | 11.892 | −67.394 | 1.00 | 15.22 | C |
| ATOM | 588 | O | ILE A | 79 | −3.116 | 12.352 | −68.154 | 1.00 | 15.76 | O |
| ATOM | 589 | N | LEU A | 80 | −5.248 | 12.258 | −67.405 | 1.00 | 14.63 | N |
| ATOM | 590 | CA | LEU A | 80 | −5.697 | 13.452 | −68.092 | 1.00 | 14.17 | C |
| ATOM | 591 | CB | LEU A | 80 | −6.605 | 13.086 | −69.257 | 1.00 | 14.25 | C |
| ATOM | 592 | CG | LEU A | 80 | −7.206 | 14.230 | −70.064 | 1.00 | 14.17 | C |
| ATOM | 593 | CD1 | LEU A | 80 | −6.189 | 14.783 | −71.053 | 1.00 | 14.21 | C |
| ATOM | 594 | CD2 | LEU A | 80 | −8.433 | 13.708 | −70.779 | 1.00 | 14.07 | C |
| ATOM | 595 | C | LEU A | 80 | −6.450 | 14.306 | −67.098 | 1.00 | 13.83 | C |
| ATOM | 596 | O | LEU A | 80 | −7.366 | 13.811 | −66.424 | 1.00 | 13.85 | O |
| ATOM | 597 | N | THR A | 81 | −6.064 | 15.577 | −66.997 | 1.00 | 13.26 | N |
| ATOM | 598 | CA | THR A | 81 | −6.741 | 16.515 | −66.094 | 1.00 | 13.11 | C |
| ATOM | 599 | CB | THR A | 81 | −5.778 | 17.579 | −65.573 | 1.00 | 13.38 | C |

-continued

| | | | | | | | | | |
|---|---|---|---|---|---|---|---|---|---|
\multicolumn{10}{c}{Atomic coordinates for CRBN:DDB1:Lenalidomide (Human protein)}

| ATOM | 600 | OG1 | THR A | 81 | −5.349 | 18.393 | −66.678 | 1.00 | 13.95 | O |
|---|---|---|---|---|---|---|---|---|---|---|
| ATOM | 601 | CG2 | THR A | 81 | −4.570 | 16.937 | −64.883 | 1.00 | 13.07 | C |
| ATOM | 602 | C | THR A | 81 | −7.902 | 17.241 | −66.780 | 1.00 | 12.73 | C |
| ATOM | 603 | O | THR A | 81 | −8.002 | 17.265 | −68.008 | 1.00 | 12.80 | O |
| ATOM | 604 | N | ALA A | 82 | −8.765 | 17.849 | −65.980 | 1.00 | 12.33 | N |
| ATOM | 605 | CA | ALA A | 82 | −9.926 | 18.548 | −66.501 | 1.00 | 12.21 | C |
| ATOM | 606 | CB | ALA A | 82 | −10.780 | 19.063 | −65.364 | 1.00 | 11.82 | C |
| ATOM | 607 | C | ALA A | 82 | −9.510 | 19.691 | −67.421 | 1.00 | 12.54 | C |
| ATOM | 608 | O | ALA A | 82 | −10.281 | 20.104 | −68.286 | 1.00 | 12.73 | O |
| ATOM | 609 | N | LYS A | 83 | −8.283 | 20.184 | −67.240 | 1.00 | 12.76 | N |
| ATOM | 610 | CA | LYS A | 83 | −7.733 | 21.256 | −68.072 | 1.00 | 12.87 | C |
| ATOM | 611 | CB | LYS A | 83 | −6.882 | 22.220 | −67.253 | 1.00 | 12.57 | C |
| ATOM | 612 | CG | LYS A | 83 | −7.712 | 23.277 | −66.563 | 1.00 | 12.27 | C |
| ATOM | 613 | CD | LYS A | 83 | −6.862 | 24.241 | −65.767 | 1.00 | 12.09 | C |
| ATOM | 614 | CE | LYS A | 83 | −7.761 | 25.176 | −64.995 | 1.00 | 12.25 | C |
| ATOM | 615 | NZ | LYS A | 83 | −7.043 | 26.375 | −64.526 | 1.00 | 12.05 | N |
| ATOM | 616 | C | LYS A | 83 | −6.936 | 20.730 | −69.243 | 1.00 | 13.50 | C |
| ATOM | 617 | O | LYS A | 83 | −6.251 | 21.495 | −69.932 | 1.00 | 13.97 | O |
| ATOM | 618 | N | TYR A | 84 | −7.038 | 19.422 | −69.468 | 1.00 | 14.00 | N |
| ATOM | 619 | CA | TYR A | 84 | −6.518 | 18.775 | −70.670 | 1.00 | 14.21 | C |
| ATOM | 620 | CB | TYR A | 84 | −6.957 | 19.525 | −71.922 | 1.00 | 14.06 | C |
| ATOM | 621 | CG | TYR A | 84 | −8.469 | 19.551 | −72.134 | 1.00 | 14.22 | C |
| ATOM | 622 | CD1 | TYR A | 84 | −9.149 | 18.401 | −72.549 | 1.00 | 14.34 | C |
| ATOM | 623 | CE1 | TYR A | 84 | −10.512 | 18.409 | −72.761 | 1.00 | 14.07 | C |
| ATOM | 624 | CZ | TYR A | 84 | −11.216 | 19.570 | −72.572 | 1.00 | 14.10 | C |
| ATOM | 625 | OH | TYR A | 84 | −12.574 | 19.531 | −72.800 | 1.00 | 14.76 | O |
| ATOM | 626 | CE2 | TYR A | 84 | −10.578 | 20.736 | −72.172 | 1.00 | 13.78 | C |
| ATOM | 627 | CD2 | TYR A | 84 | −9.212 | 20.723 | −71.955 | 1.00 | 13.80 | C |
| ATOM | 628 | C | TYR A | 84 | −5.012 | 18.632 | −70.622 | 1.00 | 14.85 | C |
| ATOM | 629 | O | TYR A | 84 | −4.355 | 18.585 | −71.655 | 1.00 | 15.24 | O |
| ATOM | 630 | N | ASN A | 85 | −4.471 | 18.555 | −69.410 | 1.00 | 15.35 | N |
| ATOM | 631 | CA | ASN A | 85 | −3.086 | 18.186 | −69.221 | 1.00 | 15.87 | C |
| ATOM | 632 | CB | ASN A | 85 | −2.579 | 18.664 | −67.866 | 1.00 | 16.36 | C |
| ATOM | 633 | CG | ASN A | 85 | −2.848 | 20.130 | −67.625 | 1.00 | 16.90 | C |
| ATOM | 634 | OD1 | ASN A | 85 | −3.724 | 20.486 | −66.833 | 1.00 | 17.34 | O |
| ATOM | 635 | ND2 | ASN A | 85 | −2.103 | 20.996 | −68.316 | 1.00 | 16.93 | N |
| ATOM | 636 | C | ASN A | 85 | −2.981 | 16.687 | −69.260 | 1.00 | 16.17 | C |
| ATOM | 637 | O | ASN A | 85 | −3.536 | 16.012 | −68.404 | 1.00 | 16.34 | O |
| ATOM | 638 | N | ALA A | 86 | −2.289 | 16.165 | −70.265 | 1.00 | 16.89 | N |
| ATOM | 639 | CA | ALA A | 86 | −1.962 | 14.743 | −70.313 | 1.00 | 17.48 | C |
| ATOM | 640 | CB | ALA A | 86 | −1.994 | 14.233 | −71.747 | 1.00 | 17.21 | C |
| ATOM | 641 | C | ALA A | 86 | −0.602 | 14.482 | −69.699 | 1.00 | 17.82 | C |
| ATOM | 642 | O | ALA A | 86 | 0.253 | 15.369 | −69.659 | 1.00 | 17.63 | O |
| ATOM | 643 | N | CYS A | 87 | −0.408 | 13.269 | −69.214 | 1.00 | 18.91 | N |
| ATOM | 644 | CA | CYS A | 87 | 0.926 | 12.804 | −68.868 | 1.00 | 20.48 | C |
| ATOM | 645 | CB | CYS A | 87 | 1.411 | 13.458 | −67.572 | 1.00 | 21.28 | C |
| ATOM | 646 | SG | CYS A | 87 | 0.420 | 13.012 | −66.133 | 1.00 | 23.89 | S |
| ATOM | 647 | C | CYS A | 87 | 0.991 | 11.280 | −68.748 | 1.00 | 21.10 | C |
| ATOM | 648 | O | CYS A | 87 | 2.205 | 10.737 | −68.883 | 1.00 | 20.33 | N |
| ATOM | 649 | N | ILE A | 88 | 2.488 | 9.361 | −68.520 | 1.00 | 19.91 | C |
| ATOM | 650 | CA | ILE A | 88 | 3.037 | 8.556 | −69.712 | 1.00 | 19.63 | C |
| ATOM | 651 | CB | ILE A | 88 | 3.037 | 8.556 | −69.712 | 1.00 | 19.63 | C |
| ATOM | 652 | CG1 | ILE A | 88 | 1.955 | 8.415 | −70.784 | 1.00 | 19.60 | C |
| ATOM | 653 | CD1 | ILE A | 88 | 2.481 | 8.083 | −72.163 | 1.00 | 19.48 | C |
| ATOM | 654 | CG2 | ILE A | 88 | 3.494 | 7.169 | −69.276 | 1.00 | 19.49 | C |
| ATOM | 655 | C | ILE A | 88 | 3.457 | 9.370 | −67.340 | 1.00 | 20.40 | C |
| ATOM | 656 | O | ILE A | 88 | 4.445 | 10.105 | −67.351 | 1.00 | 20.21 | O |
| ATOM | 657 | N | LEU A | 89 | 3.149 | 8.555 | −66.325 | 1.00 | 21.14 | N |
| ATOM | 658 | CA | LEU A | 89 | 3.863 | 8.548 | −65.037 | 1.00 | 21.61 | C |
| ATOM | 659 | CB | LEU A | 89 | 2.947 | 9.044 | −63.917 | 1.00 | 21.22 | C |
| ATOM | 660 | CG | LEU A | 89 | 2.298 | 10.413 | −64.100 | 1.00 | 21.49 | C |
| ATOM | 661 | CD1 | LEU A | 89 | 1.230 | 10.608 | −63.036 | 1.00 | 21.52 | C |
| ATOM | 662 | CD2 | LEU A | 89 | 3.316 | 11.547 | −64.080 | 1.00 | 20.93 | C |
| ATOM | 663 | C | LEU A | 89 | 4.412 | 7.177 | −64.645 | 1.00 | 22.25 | C |
| ATOM | 664 | O | LEU A | 89 | 3.797 | 6.146 | −64.921 | 1.00 | 22.05 | O |
| ATOM | 665 | N | GLU A | 90 | 5.562 | 7.189 | −63.973 | 1.00 | 23.53 | N |
| ATOM | 666 | CA | GLU A | 90 | 6.244 | 5.974 | −63.535 | 1.00 | 24.36 | C |
| ATOM | 667 | CB | GLU A | 90 | 7.516 | 5.743 | −64.371 | 1.00 | 25.04 | C |
| ATOM | 668 | CG | GLU A | 90 | 8.437 | 4.657 | −63.833 | 1.00 | 27.32 | C |
| ATOM | 669 | CD | GLU A | 90 | 9.446 | 4.123 | −64.856 | 1.00 | 29.81 | C |
| ATOM | 670 | OE1 | GLU A | 90 | 10.132 | 4.936 | −65.530 | 1.00 | 30.52 | O |
| ATOM | 671 | OE2 | GLU A | 90 | 9.579 | 2.871 | −64.960 | 1.00 | 30.18 | O |
| ATOM | 672 | C | GLU A | 90 | 6.588 | 6.086 | −62.062 | 1.00 | 24.23 | C |
| ATOM | 673 | O | GLU A | 90 | 7.006 | 7.138 | −61.594 | 1.00 | 23.97 | O |
| ATOM | 674 | N | TYR A | 91 | 6.397 | 4.992 | −61.339 | 1.00 | 25.16 | N |
| ATOM | 675 | CA | TYR A | 91 | 6.792 | 4.885 | −59.938 | 1.00 | 25.94 | C |
| ATOM | 676 | CB | TYR A | 91 | 5.949 | 3.794 | −59.280 | 1.00 | 25.62 | C |

-continued

| | | | Atomic coordinates for CRBN:DDB1:Lenalidomide (Human protein) | | | | | | |
|---|---|---|---|---|---|---|---|---|---|
| ATOM | 677 | CG | TYR A | 91 | 6.065 | 3.653 | −57.774 | 1.00 | 25.57 | C |
| ATOM | 678 | CD1 | TYR A | 91 | 6.990 | 2.785 | −57.207 | 1.00 | 25.52 | C |
| ATOM | 679 | CE1 | TYR A | 91 | 7.080 | 2.630 | −55.840 | 1.00 | 25.88 | C |
| ATOM | 680 | CZ | TYR A | 91 | 6.221 | 3.332 | −55.012 | 1.00 | 26.31 | C |
| ATOM | 681 | OH | TYR A | 91 | 6.311 | 3.178 | −53.640 | 1.00 | 26.59 | O |
| ATOM | 682 | CE2 | TYR A | 91 | 5.280 | 4.186 | −55.549 | 1.00 | 25.81 | C |
| ATOM | 683 | CD2 | TYR A | 91 | 5.200 | 4.332 | −56.923 | 1.00 | 25.80 | C |
| ATOM | 684 | C | TYR A | 91 | 8.271 | 4.522 | −59.851 | 1.00 | 27.65 | C |
| ATOM | 685 | O | TYR A | 91 | 8.771 | 3.734 | −60.657 | 1.00 | 27.72 | O |
| ATOM | 686 | N | LYS A | 92 | 8.968 | 5.099 | −58.876 | 1.00 | 30.26 | N |
| ATOM | 687 | CA | LYS A | 92 | 10.364 | 4.758 | −58.598 | 1.00 | 31.87 | C |
| ATOM | 688 | CB | LYS A | 92 | 11.303 | 5.808 | −59.195 | 1.00 | 33.60 | C |
| ATOM | 689 | CG | LYS A | 92 | 11.576 | 5.666 | −60.683 | 1.00 | 36.58 | C |
| ATOM | 690 | CD | LYS A | 92 | 12.145 | 4.291 | −61.029 | 1.00 | 39.45 | C |
| ATOM | 691 | CE | LYS A | 92 | 12.086 | 4.024 | −62.531 | 1.00 | 40.32 | C |
| ATOM | 692 | NZ | LYS A | 92 | 11.629 | 2.630 | −62.819 | 1.00 | 40.98 | N |
| ATOM | 693 | C | LYS A | 92 | 10.593 | 4.696 | −57.096 | 1.00 | 33.74 | C |
| ATOM | 694 | O | LYS A | 92 | 10.348 | 5.684 | −56.392 | 1.00 | 33.72 | O |
| ATOM | 695 | N | GLN A | 93 | 11.054 | 3.542 | −56.606 | 1.00 | 35.51 | N |
| ATOM | 696 | CA | GLN A | 93 | 11.507 | 3.407 | −55.209 | 1.00 | 35.80 | C |
| ATOM | 697 | CB | GLN A | 93 | 11.491 | 1.944 | −54.752 | 1.00 | 36.21 | C |
| ATOM | 698 | CG | GLN A | 93 | 11.582 | 1.746 | −53.241 | 1.00 | 36.09 | C |
| ATOM | 699 | CD | GLN A | 93 | 10.221 | 1.640 | −52.563 | 1.00 | 36.63 | C |
| ATOM | 700 | OE1 | GLN A | 93 | 9.197 | 2.040 | −53.123 | 1.00 | 37.34 | O |
| ATOM | 701 | NE2 | GLN A | 93 | 10.206 | 1.092 | −51.351 | 1.00 | 35.70 | N |
| ATOM | 702 | C | GLN A | 93 | 12.918 | 3.971 | −55.068 | 1.00 | 36.68 | C |
| ATOM | 703 | O | GLN A | 93 | 13.897 | 3.319 | −55.438 | 1.00 | 37.43 | O |
| ATOM | 704 | N | SER A | 97 | 13.490 | 8.811 | −51.448 | 1.00 | 29.35 | N |
| ATOM | 705 | CA | SER A | 97 | 13.044 | 7.434 | −51.272 | 1.00 | 29.85 | C |
| ATOM | 706 | CB | SER A | 97 | 12.416 | 7.236 | −49.879 | 1.00 | 30.84 | C |
| ATOM | 707 | CG | SER A | 97 | 12.771 | 5.973 | −49.324 | 1.00 | 31.74 | O |
| ATOM | 708 | C | SER A | 97 | 12.068 | 7.017 | −52.387 | 1.00 | 29.36 | C |
| ATOM | 709 | O | SER A | 97 | 12.340 | 6.042 | −53.101 | 1.00 | 28.29 | O |
| ATOM | 710 | N | ILE A | 98 | 10.947 | 7.750 | −52.531 | 1.00 | 27.91 | N |
| ATOM | 711 | CA | ILE A | 98 | 9.978 | 7.513 | −53.632 | 1.00 | 27.53 | C |
| ATOM | 712 | CB | ILE A | 98 | 8.614 | 6.971 | −53.140 | 1.00 | 26.33 | C |
| ATOM | 713 | CG1 | ILE A | 98 | 8.787 | 5.812 | −52.168 | 1.00 | 25.31 | C |
| ATOM | 714 | CD1 | ILE A | 98 | 7.518 | 5.478 | −51.426 | 1.00 | 25.67 | C |
| ATOM | 715 | CG2 | ILE A | 98 | 7.756 | 6.542 | −54.326 | 1.00 | 25.63 | C |
| ATOM | 716 | C | ILE A | 98 | 9.687 | 8.743 | −54.503 | 1.00 | 28.34 | C |
| ATOM | 717 | O | ILE A | 98 | 9.258 | 9.790 | −54.005 | 1.00 | 28.48 | O |
| ATOM | 718 | N | ASP A | 99 | 9.897 | 8.590 | −55.808 | 1.00 | 29.68 | N |
| ATOM | 719 | CA | ASP A | 99 | 9.538 | 9.620 | −56.786 | 1.00 | 30.53 | C |
| ATOM | 720 | CB | ASP A | 99 | 10.751 | 10.051 | −57.633 | 1.00 | 33.48 | C |
| ATOM | 721 | CG | ASP A | 99 | 12.007 | 10.308 | −56.809 | 1.00 | 36.29 | C |
| ATOM | 722 | OD1 | ASP A | 99 | 12.512 | 9.360 | −56.159 | 1.00 | 37.80 | O |
| ATOM | 723 | OD2 | ASP A | 99 | 12.523 | 11.451 | −56.859 | 1.00 | 37.58 | O |
| ATOM | 724 | C | ASP A | 99 | 8.481 | 9.073 | −57.739 | 1.00 | 28.89 | C |
| ATOM | 725 | O | ASP A | 99 | 8.511 | 7.892 | −58.093 | 1.00 | 29.01 | O |
| ATOM | 726 | N | ILE A | 100 | 7.554 | 9.935 | −58.153 | 1.00 | 26.65 | N |
| ATOM | 727 | CA | ILE A | 100 | 6.740 | 9.686 | −59.338 | 1.00 | 25.33 | C |
| ATOM | 728 | CB | ILE A | 100 | 5.255 | 9.975 | −59.082 | 1.00 | 24.53 | C |
| ATOM | 729 | CG1 | ILE A | 100 | 4.731 | 8.984 | −58.042 | 1.00 | 24.62 | C |
| ATOM | 730 | CD1 | ILE A | 100 | 3.291 | 9.189 | −57.641 | 1.00 | 25.31 | C |
| ATOM | 731 | CG2 | ILE A | 100 | 4.466 | 9.876 | −60.383 | 1.00 | 23.67 | C |
| ATOM | 732 | C | ILE A | 100 | 7.271 | 10.556 | −60.470 | 1.00 | 24.83 | C |
| ATOM | 733 | O | ILE A | 100 | 7.345 | 11.778 | −60.330 | 1.00 | 25.68 | O |
| ATOM | 734 | N | ILE A | 101 | 7.661 | 9.939 | −61.582 | 1.00 | 23.60 | N |
| ATOM | 735 | CA | ILE A | 101 | 8.349 | 10.696 | −62.630 | 1.00 | 23.30 | C |
| ATOM | 736 | CB | ILE A | 101 | 9.782 | 10.182 | −62.898 | 1.00 | 24.02 | C |
| ATOM | 737 | CG1 | ILE A | 101 | 9.762 | 8.803 | −63.562 | 1.00 | 24.01 | C |
| ATOM | 738 | CD1 | ILE A | 101 | 11.110 | 8.116 | −63.584 | 1.00 | 25.13 | C |
| ATOM | 739 | CG2 | ILE A | 101 | 10.601 | 10.197 | −61.605 | 1.00 | 24.71 | C |
| ATOM | 740 | C | ILE A | 101 | 7.560 | 10.831 | −63.922 | 1.00 | 22.24 | C |
| ATOM | 741 | O | ILE A | 101 | 6.741 | 9.971 | −64.249 | 1.00 | 21.69 | O |
| ATOM | 742 | N | THR A | 102 | 7.815 | 11.919 | −64.641 | 1.00 | 21.27 | N |
| ATOM | 743 | CA | THR A | 102 | 7.065 | 12.239 | −65.847 | 1.00 | 21.26 | C |
| ATOM | 744 | CB | THR A | 102 | 6.762 | 13.740 | −65.927 | 1.00 | 20.65 | C |
| ATOM | 745 | OG1 | THR A | 102 | 6.144 | 14.153 | −64.709 | 1.00 | 20.56 | O |
| ATOM | 746 | CG2 | THR A | 102 | 5.841 | 14.050 | −67.097 | 1.00 | 20.12 | C |
| ATOM | 747 | C | THR A | 102 | 7.782 | 11.775 | −67.117 | 1.00 | 21.84 | C |
| ATOM | 748 | O | THR A | 102 | 8.773 | 12.380 | −67.558 | 1.00 | 21.81 | O |
| ATOM | 749 | N | ARG A | 103 | 7.262 | 10.701 | −67.701 | 1.00 | 22.07 | N |
| ATOM | 750 | CA | ARG A | 103 | 7.815 | 10.141 | −68.920 | 1.00 | 22.65 | C |
| ATOM | 751 | CB | ARG A | 103 | 7.335 | 8.703 | −69.092 | 1.00 | 23.13 | C |
| ATOM | 752 | CG | ARG A | 103 | 7.925 | 7.755 | −68.069 | 1.00 | 24.69 | C |
| ATOM | 753 | CD | ARG A | 103 | 9.306 | 7.277 | −68.487 | 1.00 | 25.58 | C |

-continued

| | | | Atomic coordinates for CRBN:DDB1:Lenalidomide (Human protein) | | | | | | | |
|---|---|---|---|---|---|---|---|---|---|---|
| ATOM | 754 | NE | ARG A | 103 | 9.200 | 6.243 | −69.512 | 1.00 | 26.02 | N |
| ATOM | 755 | CZ | ARG A | 103 | 9.120 | 4.941 | −69.253 | 1.00 | 26.57 | C |
| ATOM | 756 | NH1 | ARG A | 103 | 9.153 | 4.496 | −68.001 | 1.00 | 26.13 | N |
| ATOM | 757 | NH2 | ARG A | 103 | 9.023 | 4.078 | −70.250 | 1.00 | 27.75 | N |
| ATOM | 758 | C | ARG A | 103 | 7.422 | 10.979 | −70.130 | 1.00 | 22.68 | C |
| ATOM | 759 | O | ARG A | 103 | 8.220 | 11.182 | −71.046 | 1.00 | 22.88 | O |
| ATOM | 760 | N | ALA A | 104 | 6.186 | 11.466 | −70.114 | 1.00 | 21.99 | N |
| ATOM | 761 | CA | ALA A | 104 | 5.613 | 12.173 | −71.234 | 1.00 | 21.21 | C |
| ATOM | 762 | CB | ALA A | 104 | 4.939 | 11.191 | −72.167 | 1.00 | 21.02 | C |
| ATOM | 763 | C | ALA A | 104 | 4.599 | 13.144 | −70.690 | 1.00 | 21.15 | C |
| ATOM | 764 | O | ALA A | 104 | 4.031 | 12.898 | −69.631 | 1.00 | 21.85 | O |
| ATOM | 765 | N | HIS A | 105 | 4.375 | 14.250 | −71.396 | 1.00 | 20.67 | N |
| ATOM | 766 | CA | HIS A | 105 | 3.324 | 15.196 | −71.016 | 1.00 | 20.08 | C |
| ATOM | 767 | CB | HIS A | 105 | 3.642 | 15.874 | −69.687 | 1.00 | 20.60 | C |
| ATOM | 768 | CG | HIS A | 105 | 4.629 | 17.006 | −69.802 | 1.00 | 21.11 | C |
| ATOM | 769 | ND1 | HIS A | 105 | 5.954 | 16.800 | −69.966 | 1.00 | 21.52 | N |
| ATOM | 770 | CE1 | HIS A | 105 | 6.583 | 17.990 | −70.036 | 1.00 | 21.81 | C |
| ATOM | 771 | NE2 | HIS A | 105 | 5.656 | 18.959 | −69.926 | 1.00 | 21.81 | N |
| ATOM | 772 | CD2 | HIS A | 105 | 4.443 | 18.387 | −69.779 | 1.00 | 21.08 | C |
| ATOM | 773 | C | HIS A | 105 | 3.083 | 16.229 | −72.065 | 1.00 | 19.22 | C |
| ATOM | 774 | O | HIS A | 105 | 3.964 | 16.542 | −72.855 | 1.00 | 19.43 | O |
| ATOM | 775 | N | GLY A | 106 | 1.879 | 16.779 | −72.060 | 1.00 | 18.30 | N |
| ATOM | 776 | CA | GLY A | 106 | 1.522 | 17.839 | −72.970 | 1.00 | 17.95 | C |
| ATOM | 777 | C | GLY A | 106 | 0.055 | 18.174 | −72.884 | 1.00 | 17.69 | C |
| ATOM | 778 | O | GLY A | 106 | −0.754 | 17.349 | −72.452 | 1.00 | 17.54 | O |
| ATOM | 779 | N | ASN A | 107 | −0.299 | 19.385 | −73.305 | 1.00 | 17.44 | N |
| ATOM | 780 | CA | ASN A | 107 | −1.686 | 19.793 | −73.251 | 1.00 | 17.36 | C |
| ATOM | 781 | CB | ASN A | 107 | −1.815 | 21.265 | −72.897 | 1.00 | 16.68 | C |
| ATOM | 782 | CG | ASN A | 107 | −3.217 | 21.618 | −72.481 | 1.00 | 16.91 | C |
| ATOM | 783 | OD1 | ASN A | 107 | −4.099 | 21.748 | −73.323 | 1.00 | 17.30 | O |
| ATOM | 784 | ND2 | ASN A | 107 | −3.446 | 21.731 | −71.174 | 1.00 | 16.82 | N |
| ATOM | 785 | C | ASN A | 107 | −2.488 | 19.445 | −74.508 | 1.00 | 17.78 | C |
| ATOM | 786 | O | ASN A | 107 | −2.256 | 20.003 | −75.571 | 1.00 | 18.44 | O |
| ATOM | 787 | N | VAL A | 108 | −3.447 | 18.535 | −74.364 | 1.00 | 18.34 | N |
| ATOM | 788 | CA | VAL A | 108 | −4.233 | 18.028 | −75.496 | 1.00 | 18.94 | C |
| ATOM | 789 | CB | VAL A | 108 | −4.666 | 16.563 | −75.274 | 1.00 | 18.38 | C |
| ATOM | 790 | CG1 | VAL A | 108 | −3.453 | 15.634 | −75.270 | 1.00 | 17.82 | C |
| ATOM | 791 | CG2 | VAL A | 108 | −5.476 | 16.436 | −73.988 | 1.00 | 18.32 | C |
| ATOM | 792 | C | VAL A | 108 | −5.475 | 18.861 | −75.836 | 1.00 | 20.41 | C |
| ATOM | 793 | O | VAL A | 108 | −6.387 | 18.376 | −76.501 | 1.00 | 20.72 | O |
| ATOM | 794 | N | GLN A | 109 | −5.514 | 20.112 | −75.391 | 1.00 | 22.38 | N |
| ATOM | 795 | CA | GLN A | 109 | −6.621 | 20.997 | −75.731 | 1.00 | 23.63 | C |
| ATOM | 796 | CB | GLN A | 109 | −6.537 | 22.285 | −74.927 | 1.00 | 24.33 | C |
| ATOM | 797 | CG | GLN A | 109 | −7.580 | 23.317 | −75.304 | 1.00 | 25.70 | C |
| ATOM | 798 | CD | GLN A | 109 | −8.071 | 24.084 | −74.106 | 1.00 | 27.11 | C |
| ATOM | 799 | OE1 | GLN A | 109 | −7.267 | 24.576 | −73.306 | 1.00 | 28.84 | O |
| ATOM | 800 | NE2 | GLN A | 109 | −9.397 | 24.178 | −73.955 | 1.00 | 26.37 | N |
| ATOM | 801 | C | GLN A | 109 | −6.643 | 21.327 | −77.223 | 1.00 | 24.51 | C |
| ATOM | 802 | O | GLN A | 109 | −5.612 | 21.277 | −77.905 | 1.00 | 23.56 | O |
| ATOM | 803 | N | ASP A | 110 | −7.836 | 21.653 | −77.712 | 1.00 | 25.74 | N |
| ATOM | 804 | CA | ASP A | 110 | −8.016 | 22.170 | −79.049 | 1.00 | 26.80 | C |
| ATOM | 805 | CB | ASP A | 110 | −8.933 | 21.248 | −79.847 | 1.00 | 26.77 | C |
| ATOM | 806 | CG | ASP A | 110 | −8.213 | 20.006 | −80.348 | 1.00 | 26.78 | C |
| ATOM | 807 | OD1 | ASP A | 110 | −6.974 | 19.920 | −80.183 | 1.00 | 26.62 | O |
| ATOM | 808 | OD2 | ASP A | 110 | −8.885 | 19.112 | −80.906 | 1.00 | 27.29 | O |
| ATOM | 809 | C | ASP A | 110 | −8.567 | 23.588 | −79.012 | 1.00 | 27.84 | C |
| ATOM | 810 | O | ASP A | 110 | −9.335 | 23.933 | −78.127 | 1.00 | 27.41 | O |
| ATOM | 811 | N | ARG A | 111 | −8.156 | 24.408 | −79.978 | 1.00 | 30.03 | N |
| ATOM | 812 | CA | ARG A | 111 | −8.589 | 25.806 | −80.044 | 1.00 | 31.12 | C |
| ATOM | 813 | CB | ARG A | 111 | −7.853 | 26.565 | −81.160 | 1.00 | 31.12 | C |
| ATOM | 814 | C | ARG A | 111 | −10.098 | 25.889 | −80.242 | 1.00 | 31.49 | C |
| ATOM | 815 | O | ARG A | 111 | −10.770 | 26.707 | −79.607 | 1.00 | 32.37 | O |
| ATOM | 816 | N | ILE A | 112 | −10.618 | 25.037 | −81.123 | 1.00 | 30.32 | N |
| ATOM | 817 | CA | ILE A | 112 | −12.046 | 24.955 | −81.378 | 1.00 | 29.53 | C |
| ATOM | 818 | CB | ILE A | 112 | −12.335 | 24.707 | −82.877 | 1.00 | 29.86 | C |
| ATOM | 819 | C | ILE A | 112 | −12.563 | 23.809 | −80.534 | 1.00 | 29.06 | C |
| ATOM | 820 | O | ILE A | 112 | −11.883 | 23.384 | −79.602 | 1.00 | 29.92 | O |
| ATOM | 821 | N | GLY A | 113 | −13.758 | 23.313 | −80.844 | 1.00 | 28.44 | N |
| ATOM | 822 | CA | GLY A | 113 | −14.264 | 22.098 | −80.211 | 1.00 | 27.59 | C |
| ATOM | 823 | C | GLY A | 113 | −15.298 | 22.316 | −79.125 | 1.00 | 27.02 | C |
| ATOM | 824 | O | GLY A | 113 | −15.002 | 22.876 | −78.071 | 1.00 | 26.48 | O |
| ATOM | 825 | N | ARG A | 114 | −16.522 | 21.873 | −79.405 | 1.00 | 27.22 | N |
| ATOM | 826 | CA | ARG A | 114 | −17.592 | 21.804 | −78.416 | 1.00 | 26.30 | C |
| ATOM | 827 | CB | ARG A | 114 | −18.965 | 21.751 | −79.110 | 1.00 | 24.56 | C |
| ATOM | 828 | C | ARG A | 114 | −17.378 | 20.538 | −77.589 | 1.00 | 26.59 | C |
| ATOM | 829 | O | ARG A | 114 | −17.428 | 19.424 | −78.141 | 1.00 | 27.58 | O |
| ATOM | 830 | N | PRO A | 115 | −17.117 | 20.694 | −76.272 | 1.00 | 25.94 | N |

-continued

| | | | Atomic coordinates for CRBN:DDB1:Lenalidomide (Human protein) | | | | | | |
|---|---|---|---|---|---|---|---|---|---|
| ATOM | 831 | CA | PRO A | 115 | −17.047 | 19.544 | −75.371 | 1.00 | 25.63 | C |
| ATOM | 832 | CB | PRO A | 115 | −17.006 | 20.189 | −73.987 | 1.00 | 24.50 | C |
| ATOM | 833 | CG | PRO A | 115 | −16.374 | 21.511 | −74.215 | 1.00 | 24.29 | C |
| ATOM | 834 | CD | PRO A | 115 | −16.873 | 21.961 | −75.558 | 1.00 | 25.32 | C |
| ATOM | 835 | C | PRO A | 115 | −18.294 | 18.679 | −75.500 | 1.00 | 26.28 | C |
| ATOM | 836 | O | PRO A | 115 | −19.405 | 19.204 | −75.539 | 1.00 | 26.09 | O |
| ATOM | 837 | N | SER A | 116 | −18.104 | 17.368 | −75.575 | 1.00 | 28.03 | N |
| ATOM | 838 | CA | SER A | 116 | −19.217 | 16.428 | −75.719 | 1.00 | 30.71 | C |
| ATOM | 839 | CB | SER A | 116 | −18.691 | 15.055 | −76.113 | 1.00 | 30.73 | C |
| ATOM | 840 | OG | SER A | 116 | −17.847 | 15.153 | −77.246 | 1.00 | 30.70 | O |
| ATOM | 841 | C | SER A | 116 | −20.087 | 16.313 | −74.465 | 1.00 | 32.58 | C |
| ATOM | 842 | O | SER A | 116 | −19.583 | 16.344 | −73.342 | 1.00 | 33.75 | O |
| ATOM | 843 | N | GLU A | 117 | −21.393 | 16.163 | −74.676 | 1.00 | 35.42 | N |
| ATOM | 844 | CA | GLU A | 117 | −22.387 | 16.139 | −73.594 | 1.00 | 36.56 | C |
| ATOM | 845 | CB | GLU A | 117 | −23.811 | 15.976 | −74.159 | 1.00 | 39.54 | C |
| ATOM | 846 | CG | GLU A | 117 | −24.151 | 16.870 | −75.345 | 1.00 | 42.64 | C |
| ATOM | 847 | CD | GLU A | 117 | −25.388 | 16.398 | −76.094 | 1.00 | 45.62 | C |
| ATOM | 848 | OE1 | GLU A | 117 | −25.231 | 15.703 | −77.135 | 1.00 | 45.00 | O |
| ATOM | 849 | OE2 | GLU A | 117 | −26.515 | 16.718 | −75.636 | 1.00 | 47.14 | O |
| ATOM | 850 | C | GLU A | 117 | −22.112 | 14.994 | −72.645 | 1.00 | 35.37 | C |
| ATOM | 851 | O | GLU A | 117 | −22.367 | 15.099 | −71.445 | 1.00 | 37.23 | O |
| ATOM | 852 | N | THR A | 118 | −21.600 | 13.897 | −73.200 | 1.00 | 34.25 | N |
| ATOM | 853 | CA | THR A | 118 | −21.293 | 12.692 | −72.429 | 1.00 | 32.66 | C |
| ATOM | 854 | CB | THR A | 118 | −21.485 | 11.424 | −73.297 | 1.00 | 33.17 | C |
| ATOM | 855 | OG1 | THR A | 118 | −22.733 | 10.809 | −72.950 | 1.00 | 33.59 | O |
| ATOM | 856 | CG2 | THR A | 118 | −20.345 | 10.411 | −73.111 | 1.00 | 32.33 | C |
| ATOM | 857 | C | THR A | 118 | −19.918 | 12.751 | −71.733 | 1.00 | 30.72 | C |
| ATOM | 858 | O | THR A | 118 | −19.463 | 11.776 | −71.142 | 1.00 | 32.67 | O |
| ATOM | 859 | N | GLY A | 119 | −19.278 | 13.912 | −71.792 | 1.00 | 28.18 | N |
| ATOM | 860 | CA | GLY A | 119 | −18.071 | 14.169 | −71.030 | 1.00 | 24.65 | C |
| ATOM | 861 | C | GLY A | 119 | −16.856 | 13.552 | −71.664 | 1.00 | 22.55 | C |
| ATOM | 862 | O | GLY A | 119 | −16.965 | 12.826 | −72.644 | 1.00 | 22.36 | O |
| ATOM | 863 | N | ILE A | 120 | −15.699 | 13.859 | −71.088 | 1.00 | 20.92 | N |
| ATOM | 864 | CA | ILE A | 120 | −14.408 | 13.296 | −71.481 | 1.00 | 19.43 | C |
| ATOM | 865 | CB | ILE A | 120 | −13.282 | 13.879 | −70.594 | 1.00 | 18.56 | C |
| ATOM | 866 | CG1 | ILE A | 120 | −13.174 | 15.402 | −70.794 | 1.00 | 17.68 | C |
| ATOM | 867 | CD1 | ILE A | 120 | −11.965 | 16.051 | −70.162 | 1.00 | 17.00 | C |
| ATOM | 868 | CG2 | ILE A | 120 | −11.968 | 13.158 | −70.855 | 1.00 | 18.71 | C |
| ATOM | 869 | C | ILE A | 120 | −14.401 | 11.766 | −71.372 | 1.00 | 19.19 | C |
| ATOM | 870 | O | ILE A | 120 | −14.990 | 11.209 | −70.450 | 1.00 | 19.37 | O |
| ATOM | 871 | N | ILE A | 121 | −13.756 | 11.097 | −72.325 | 1.00 | 18.83 | N |
| ATOM | 872 | CA | ILE A | 121 | −13.545 | 9.652 | −72.259 | 1.00 | 18.96 | C |
| ATOM | 873 | CB | ILE A | 121 | −14.552 | 8.885 | −73.131 | 1.00 | 18.80 | C |
| ATOM | 874 | CG1 | ILE A | 121 | −15.965 | 9.035 | −72.581 | 1.00 | 19.28 | C |
| ATOM | 875 | CD1 | ILE A | 121 | −17.015 | 8.237 | −73.328 | 1.00 | 19.92 | C |
| ATOM | 876 | CG2 | ILE A | 121 | −14.163 | 7.418 | −73.226 | 1.00 | 18.73 | C |
| ATOM | 877 | C | ILE A | 121 | −12.126 | 9.297 | −72.716 | 1.00 | 19.65 | C |
| ATOM | 878 | O | ILE A | 121 | −11.722 | 9.629 | −73.838 | 1.00 | 20.25 | O |
| ATOM | 879 | N | GLY A | 122 | −11.371 | 8.629 | −71.845 | 1.00 | 19.77 | N |
| ATOM | 880 | CA | GLY A | 122 | −10.027 | 8.182 | −72.181 | 1.00 | 19.74 | C |
| ATOM | 881 | C | GLY A | 122 | −10.000 | 6.676 | −72.281 | 1.00 | 20.28 | C |
| ATOM | 882 | O | GLY A | 122 | −10.538 | 5.992 | −71.420 | 1.00 | 20.81 | O |
| ATOM | 883 | N | ILE A | 123 | −9.385 | 6.158 | −73.336 | 1.00 | 20.19 | N |
| ATOM | 884 | CA | ILE A | 123 | −9.258 | 4.721 | −73.515 | 1.00 | 20.51 | C |
| ATOM | 885 | CB | ILE A | 123 | −10.386 | 4.137 | −74.394 | 1.00 | 20.75 | C |
| ATOM | 886 | CG1 | ILE A | 123 | −10.654 | 5.026 | −75.618 | 1.00 | 20.88 | C |
| ATOM | 887 | CD1 | ILE A | 123 | −11.463 | 4.358 | −76.716 | 1.00 | 20.73 | C |
| ATOM | 888 | CG2 | ILE A | 123 | −11.655 | 3.955 | −73.580 | 1.00 | 20.64 | C |
| ATOM | 889 | C | ILE A | 123 | −7.909 | 4.363 | −74.124 | 1.00 | 21.16 | C |
| ATOM | 890 | O | ILE A | 123 | −7.417 | 5.052 | −75.022 | 1.00 | 21.17 | O |
| ATOM | 891 | N | ILE A | 124 | −7.311 | 3.292 | −73.613 | 1.00 | 21.66 | N |
| ATOM | 892 | CA | ILE A | 124 | −6.063 | 2.761 | −74.145 | 1.00 | 22.44 | C |
| ATOM | 893 | CB | ILE A | 124 | −5.006 | 2.578 | −73.036 | 1.00 | 21.59 | C |
| ATOM | 894 | CG1 | ILE A | 124 | −4.737 | 3.907 | −72.343 | 1.00 | 21.81 | C |
| ATOM | 895 | CD1 | ILE A | 124 | −3.284 | 4.153 | −71.992 | 1.00 | 22.24 | C |
| ATOM | 896 | CG2 | ILE A | 124 | −3.719 | 1.994 | −73.602 | 1.00 | 21.83 | C |
| ATOM | 897 | C | ILE A | 124 | −6.358 | 1.411 | −74.784 | 1.00 | 23.88 | C |
| ATOM | 898 | O | ILE A | 124 | −7.026 | 0.581 | −74.181 | 1.00 | 24.64 | O |
| ATOM | 899 | N | ASP A | 125 | −5.874 | 1.182 | −76.001 | 1.00 | 25.36 | N |
| ATOM | 900 | CA | ASP A | 125 | −6.102 | −0.108 | −76.645 | 1.00 | 26.92 | C |
| ATOM | 901 | CB | ASP A | 125 | −5.807 | −0.034 | −78.143 | 1.00 | 27.76 | C |
| ATOM | 902 | CG | ASP A | 125 | −4.333 | −0.133 | −78.453 | 1.00 | 29.50 | C |
| ATOM | 903 | OD1 | ASP A | 125 | −3.816 | −1.269 | −78.498 | 1.00 | 28.74 | O |
| ATOM | 904 | OD2 | ASP A | 125 | −3.701 | 0.928 | −78.677 | 1.00 | 31.63 | O |
| ATOM | 905 | C | ASP A | 125 | −5.301 | −1.220 | −75.947 | 1.00 | 27.48 | C |
| ATOM | 906 | O | ASP A | 125 | −4.364 | −0.932 | −75.201 | 1.00 | 26.88 | O |
| ATOM | 907 | N | PRO A | 126 | −5.680 | −2.490 | −76.183 | 1.00 | 27.72 | N |

-continued

| | | | | Atomic coordinates for CRBN:DDB1:Lenalidomide (Human protein) | | | | | |
|---|---|---|---|---|---|---|---|---|---|
| ATOM | 908 | CA | PRO A | 126 | −5.086 | −3.637 | −75.497 | 1.00 | 28.38 | C |
| ATOM | 909 | CB | PRO A | 126 | −5.945 | −4.814 | −75.964 | 1.00 | 27.62 | C |
| ATOM | 910 | CG | PRO A | 126 | −7.179 | −4.207 | −76.528 | 1.00 | 27.56 | C |
| ATOM | 911 | CD | PRO A | 126 | −6.755 | −2.901 | −77.097 | 1.00 | 27.28 | C |
| ATOM | 912 | C | PRO A | 126 | −3.623 | −3.909 | −75.847 | 1.00 | 29.52 | C |
| ATOM | 913 | O | PRO A | 126 | −2.924 | −4.543 | −75.065 | 1.00 | 29.93 | O |
| ATOM | 914 | N | GLU A | 127 | −3.172 | −3.468 | −77.016 | 1.00 | 32.33 | N |
| ATOM | 915 | CA | GLU A | 127 | −1.782 | −3.700 | −77.442 | 1.00 | 35.39 | C |
| ATOM | 916 | CB | GLU A | 127 | −1.704 | −4.019 | −78.940 | 1.00 | 38.15 | C |
| ATOM | 917 | CG | GLU A | 127 | −2.187 | −5.408 | −79.339 | 1.00 | 43.14 | C |
| ATOM | 918 | CD | GLU A | 127 | −1.930 | −5.707 | −80.815 | 1.00 | 49.66 | C |
| ATOM | 919 | OE1 | GLU A | 127 | −2.040 | −4.767 | −81.653 | 1.00 | 53.44 | O |
| ATOM | 920 | OE2 | GLU A | 127 | −1.614 | −6.878 | −81.415 | 1.00 | 50.14 | O |
| ATOM | 921 | C | GLU A | 127 | −0.926 | −2.482 | −77.120 | 1.00 | 35.28 | C |
| ATOM | 922 | O | GLU A | 127 | 0.238 | −2.390 | −77.531 | 1.00 | 34.93 | O |
| ATOM | 923 | N | CYS A | 128 | −1.529 | −1.539 | −76.398 | 1.00 | 34.85 | N |
| ATOM | 924 | CA | CYS A | 128 | −0.870 | −0.306 | −75.981 | 1.00 | 33.48 | C |
| ATOM | 925 | CB | CYS A | 128 | 0.118 | −0.586 | −74.839 | 1.00 | 33.97 | C |
| ATOM | 926 | SG | CYS A | 128 | −0.689 | −1.172 | −73.327 | 1.00 | 36.74 | S |
| ATOM | 927 | C | CYS A | 128 | −0.192 | 0.421 | −77.133 | 1.00 | 31.45 | C |
| ATOM | 928 | O | CYS A | 128 | 0.949 | 0.851 | −77.009 | 1.00 | 32.11 | O |
| ATOM | 929 | N | ARG A | 129 | −0.902 | 0.548 | −78.252 | 1.00 | 29.95 | N |
| ATOM | 930 | CA | ARG A | 129 | −0.423 | 1.340 | −79.385 | 1.00 | 29.76 | C |
| ATOM | 931 | CB | ARG A | 129 | −1.076 | 0.903 | −80.700 | 1.00 | 29.41 | C |
| ATOM | 932 | CG | ARG A | 129 | −0.907 | −0.557 | −81.071 | 1.00 | 29.77 | C |
| ATOM | 933 | CD | ARG A | 129 | 0.546 | −0.937 | −81.265 | 1.00 | 29.84 | C |
| ATOM | 934 | NE | ARG A | 129 | 0.697 | −1.784 | −82.441 | 1.00 | 30.10 | N |
| ATOM | 935 | CZ | ARG A | 129 | 1.353 | −1.426 | −83.541 | 1.00 | 30.27 | C |
| ATOM | 936 | NH1 | ARG A | 129 | 1.947 | −0.238 | −83.620 | 1.00 | 29.24 | N |
| ATOM | 937 | NH2 | ARG A | 129 | 1.426 | −2.266 | −84.564 | 1.00 | 30.92 | N |
| ATOM | 938 | C | ARG A | 129 | −0.700 | 2.822 | −79.164 | 1.00 | 29.33 | C |
| ATOM | 939 | O | ARG A | 129 | 0.170 | 3.662 | −79.390 | 1.00 | 29.85 | O |
| ATOM | 940 | N | MET A | 130 | −1.914 | 3.138 | −78.720 | 1.00 | 28.46 | N |
| ATOM | 941 | CA | MET A | 130 | −2.327 | 4.529 | −78.568 | 1.00 | 27.35 | C |
| ATOM | 942 | CB | MET A | 130 | −3.093 | 4.968 | −79.815 | 1.00 | 27.89 | C |
| ATOM | 943 | CG | MET A | 130 | −4.457 | 4.310 | −79.934 | 1.00 | 28.31 | C |
| ATOM | 944 | SD | MET A | 130 | −5.073 | 4.307 | −81.616 | 1.00 | 28.28 | S |
| ATOM | 945 | CE | MET A | 130 | −4.170 | 2.937 | −82.313 | 1.00 | 27.53 | C |
| ATOM | 946 | C | MET A | 130 | −3.194 | 4.797 | −77.334 | 1.00 | 25.84 | C |
| ATOM | 947 | O | MET A | 130 | −3.725 | 3.882 | −76.715 | 1.00 | 25.49 | O |
| ATOM | 948 | N | ILE A | 131 | −3.319 | 6.071 | −76.995 | 1.00 | 24.20 | N |
| ATOM | 949 | CA | ILE A | 131 | −4.423 | 6.552 | −76.196 | 1.00 | 22.81 | C |
| ATOM | 950 | CB | ILE A | 131 | −3.951 | 7.635 | −75.212 | 1.00 | 22.74 | C |
| ATOM | 951 | CG1 | ILE A | 131 | −2.924 | 7.055 | −74.248 | 1.00 | 23.03 | C |
| ATOM | 952 | CD1 | ILE A | 131 | −1.809 | 8.021 | −73.925 | 1.00 | 23.81 | C |
| ATOM | 953 | CG2 | ILE A | 131 | −5.114 | 8.225 | −74.431 | 1.00 | 22.50 | C |
| ATOM | 954 | C | ILE A | 131 | −5.429 | 7.145 | −77.176 | 1.00 | 22.12 | C |
| ATOM | 955 | O | ILE A | 131 | −5.063 | 7.900 | −78.083 | 1.00 | 21.78 | O |
| ATOM | 956 | N | GLY A | 132 | −6.693 | 6.782 | −77.009 | 1.00 | 21.60 | N |
| ATOM | 957 | CA | GLY A | 132 | −7.773 | 7.393 | −77.781 | 1.00 | 21.48 | C |
| ATOM | 958 | C | GLY A | 132 | −8.553 | 8.347 | −76.902 | 1.00 | 21.27 | C |
| ATOM | 959 | O | GLY A | 132 | −9.025 | 7.965 | −75.838 | 1.00 | 22.28 | O |
| ATOM | 960 | N | LEU A | 133 | −8.680 | 9.595 | −77.329 | 1.00 | 20.88 | N |
| ATOM | 961 | CA | LEU A | 133 | −9.356 | 10.600 | −76.518 | 1.00 | 20.61 | C |
| ATOM | 962 | CB | LEU A | 133 | −8.427 | 11.759 | −76.179 | 1.00 | 20.41 | C |
| ATOM | 963 | CG | LEU A | 133 | −7.284 | 11.366 | −75.262 | 1.00 | 20.24 | C |
| ATOM | 964 | CD1 | LEU A | 133 | −6.398 | 12.567 | −74.993 | 1.00 | 20.01 | C |
| ATOM | 965 | CD2 | LEU A | 133 | −7.841 | 10.780 | −73.977 | 1.00 | 20.20 | C |
| ATOM | 966 | C | LEU A | 133 | −10.575 | 11.137 | −77.198 | 1.00 | 20.55 | C |
| ATOM | 967 | O | LEU A | 133 | −10.502 | 11.625 | −78.330 | 1.00 | 19.72 | O |
| ATOM | 968 | N | ARG A | 134 | −11.698 | 11.035 | −76.494 | 1.00 | 21.09 | N |
| ATOM | 969 | CA | ARG A | 134 | −12.923 | 11.667 | −76.915 | 1.00 | 21.89 | C |
| ATOM | 970 | CB | ARG A | 134 | −14.091 | 10.691 | −76.869 | 1.00 | 23.69 | C |
| ATOM | 971 | CG | ARG A | 134 | −15.296 | 11.114 | −77.708 | 1.00 | 25.41 | C |
| ATOM | 972 | CD | ARG A | 134 | −15.976 | 12.355 | −77.149 | 1.00 | 26.47 | C |
| ATOM | 973 | NE | ARG A | 134 | −17.392 | 12.123 | −76.905 | 1.00 | 27.92 | N |
| ATOM | 974 | CZ | ARG A | 134 | −17.894 | 11.777 | −75.723 | 1.00 | 30.38 | C |
| ATOM | 975 | NH1 | ARG A | 134 | −17.094 | 11.615 | −74.674 | 1.00 | 30.51 | N |
| ATOM | 976 | NH2 | ARG A | 134 | −19.201 | 11.597 | −75.586 | 1.00 | 32.62 | N |
| ATOM | 977 | C | ARG A | 134 | −13.184 | 12.845 | −76.015 | 1.00 | 21.60 | C |
| ATOM | 978 | O | ARG A | 134 | −13.527 | 12.681 | −74.844 | 1.00 | 21.54 | O |
| ATOM | 979 | N | LEU A | 135 | −13.003 | 14.034 | −76.584 | 1.00 | 21.32 | N |
| ATOM | 980 | CA | LEU A | 135 | −13.128 | 15.288 | −75.869 | 1.00 | 20.71 | C |
| ATOM | 981 | CB | LEU A | 135 | −11.825 | 16.066 | −75.971 | 1.00 | 19.99 | C |
| ATOM | 982 | CG | LEU A | 135 | −10.560 | 15.308 | −75.562 | 1.00 | 20.28 | C |
| ATOM | 983 | CD1 | LEU A | 135 | −9.317 | 16.112 | −75.915 | 1.00 | 20.04 | C |
| ATOM | 984 | CD2 | LEU A | 135 | −10.575 | 14.953 | −74.074 | 1.00 | 20.31 | C |

-continued

| | | | Atomic coordinates for CRBN:DDB1:Lenalidomide (Human protein) | | | | | | |
|---|---|---|---|---|---|---|---|---|---|
| ATOM | 985 | C | LEU A | 135 | −14.259 | 16.099 | −76.476 | 1.00 | 21.43 | C |
| ATOM | 986 | O | LEU A | 135 | −15.066 | 16.695 | −75.767 | 1.00 | 22.14 | O |
| ATOM | 987 | N | TYR A | 136 | −14.329 | 16.102 | −77.801 | 1.00 | 21.72 | N |
| ATOM | 988 | CA | TYR A | 136 | −15.289 | 16.930 | −78.500 | 1.00 | 21.20 | C |
| ATOM | 989 | CB | TYR A | 136 | −14.550 | 18.038 | −79.237 | 1.00 | 21.07 | C |
| ATOM | 990 | CG | TYR A | 136 | −13.502 | 18.716 | −78.379 | 1.00 | 21.35 | C |
| ATOM | 991 | CD1 | TYR A | 136 | −13.865 | 19.403 | −77.219 | 1.00 | 21.43 | C |
| ATOM | 992 | CE1 | TYR A | 136 | −12.912 | 20.022 | −76.422 | 1.00 | 21.19 | C |
| ATOM | 993 | CZ | TYR A | 136 | −11.579 | 19.963 | −76.774 | 1.00 | 20.99 | C |
| ATOM | 994 | OH | TYR A | 136 | −10.656 | 20.603 | −75.979 | 1.00 | 20.83 | O |
| ATOM | 995 | CE2 | TYR A | 136 | −11.189 | 19.286 | −77.920 | 1.00 | 21.12 | C |
| ATOM | 996 | CD2 | TYR A | 136 | −12.149 | 18.671 | −78.719 | 1.00 | 21.14 | C |
| ATOM | 997 | C | TYR A | 136 | −16.188 | 16.140 | −79.453 | 1.00 | 21.43 | C |
| ATOM | 998 | O | TYR A | 136 | −15.866 | 15.019 | −79.890 | 1.00 | 20.95 | O |
| ATOM | 999 | N | ASP A | 137 | −17.336 | 16.725 | −79.754 | 1.00 | 21.13 | N |
| ATOM | 1000 | CA | ASP A | 137 | −18.197 | 16.179 | −80.769 | 1.00 | 21.20 | C |
| ATOM | 1001 | CB | ASP A | 137 | −19.501 | 16.969 | −80.812 | 1.00 | 21.95 | C |
| ATOM | 1002 | CG | ASP A | 137 | −20.231 | 16.967 | −79.465 | 1.00 | 22.94 | C |
| ATOM | 1003 | OD1 | ASP A | 137 | −20.256 | 15.911 | −78.791 | 1.00 | 23.17 | O |
| ATOM | 1004 | OD2 | ASP A | 137 | −20.785 | 18.021 | −79.077 | 1.00 | 23.77 | O |
| ATOM | 1005 | C | ASP A | 137 | −17.459 | 16.225 | −82.105 | 1.00 | 20.61 | C |
| ATOM | 1006 | O | ASP A | 137 | −16.637 | 17.102 | −82.331 | 1.00 | 20.24 | O |
| ATOM | 1007 | N | GLY A | 138 | −17.712 | 15.243 | −82.963 | 1.00 | 20.88 | N |
| ATOM | 1008 | CA | GLY A | 138 | −17.093 | 15.197 | −84.288 | 1.00 | 20.27 | C |
| ATOM | 1009 | C | GLY A | 138 | −15.692 | 14.612 | −84.372 | 1.00 | 20.22 | C |
| ATOM | 1010 | O | GLY A | 138 | −15.341 | 14.030 | −85.384 | 1.00 | 20.94 | O |
| ATOM | 1011 | N | LEU A | 139 | −14.881 | 14.766 | −83.327 | 1.00 | 19.84 | N |
| ATOM | 1012 | CA | LEU A | 139 | −13.475 | 14.338 | −83.397 | 1.00 | 19.79 | C |
| ATOM | 1013 | CB | LEU A | 139 | −12.535 | 15.537 | −83.210 | 1.00 | 19.30 | C |
| ATOM | 1014 | CG | LEU A | 139 | −12.736 | 16.760 | −84.100 | 1.00 | 18.95 | C |
| ATOM | 1015 | CD1 | LEU A | 139 | −12.450 | 18.035 | −83.329 | 1.00 | 18.75 | C |
| ATOM | 1016 | CD2 | LEU A | 139 | −11.872 | 16.674 | −85.343 | 1.00 | 19.12 | C |
| ATOM | 1017 | C | LEU A | 139 | −13.096 | 13.219 | −82.417 | 1.00 | 20.06 | C |
| ATOM | 1018 | O | LEU A | 139 | −13.684 | 13.095 | −81.351 | 1.00 | 21.08 | O |
| ATOM | 1019 | N | PHE A | 140 | −12.099 | 12.423 | −82.790 | 1.00 | 19.98 | N |
| ATOM | 1020 | CA | PHE A | 140 | −11.536 | 11.401 | −81.922 | 1.00 | 20.61 | C |
| ATOM | 1021 | CB | PHE A | 140 | −11.926 | 10.006 | −82.431 | 1.00 | 20.82 | C |
| ATOM | 1022 | CG | PHE A | 140 | −11.423 | 8.860 | −81.574 | 1.00 | 21.15 | C |
| ATOM | 1023 | CD1 | PHE A | 140 | −12.103 | 8.478 | −80.410 | 1.00 | 21.07 | C |
| ATOM | 1024 | CE1 | PHE A | 140 | −11.651 | 7.415 | −79.632 | 1.00 | 21.03 | C |
| ATOM | 1025 | CZ | PHE A | 140 | −10.520 | 6.704 | −80.015 | 1.00 | 20.94 | C |
| ATOM | 1026 | CE2 | PHE A | 140 | −9.842 | 7.059 | −81.176 | 1.00 | 21.25 | C |
| ATOM | 1027 | CD2 | PHE A | 140 | −10.297 | 8.125 | −81.954 | 1.00 | 21.15 | C |
| ATOM | 1028 | C | PHE A | 140 | −10.022 | 11.595 | −81.935 | 1.00 | 21.36 | C |
| ATOM | 1029 | O | PHE A | 140 | −9.378 | 11.408 | −82.971 | 1.00 | 21.91 | O |
| ATOM | 1030 | N | LYS A | 141 | −9.456 | 12.004 | −80.797 | 1.00 | 21.63 | N |
| ATOM | 1031 | CA | LYS A | 141 | −8.014 | 12.298 | −80.723 | 1.00 | 21.27 | C |
| ATOM | 1032 | CB | LYS A | 141 | −7.701 | 13.369 | −79.663 | 1.00 | 20.64 | C |
| ATOM | 1033 | CG | LYS A | 141 | −6.255 | 13.874 | −79.689 | 1.00 | 19.81 | C |
| ATOM | 1034 | CD | LYS A | 141 | −6.076 | 15.179 | −78.934 | 1.00 | 19.04 | C |
| ATOM | 1035 | CE | LYS A | 141 | −7.061 | 16.225 | −79.421 | 1.00 | 18.83 | C |
| ATOM | 1036 | NZ | LYS A | 141 | −6.577 | 17.602 | −79.173 | 1.00 | 18.95 | N |
| ATOM | 1037 | C | LYS A | 141 | −7.207 | 11.031 | −80.456 | 1.00 | 21.39 | C |
| ATOM | 1038 | O | LYS A | 141 | −7.629 | 10.164 | −79.684 | 1.00 | 22.05 | O |
| ATOM | 1039 | N | VAL A | 142 | −6.047 | 10.929 | −81.098 | 1.00 | 20.50 | N |
| ATOM | 1040 | CA | VAL A | 142 | −5.207 | 9.763 | −80.950 | 1.00 | 19.90 | C |
| ATOM | 1041 | CB | VAL A | 142 | −5.192 | 8.912 | −82.250 | 1.00 | 19.53 | C |
| ATOM | 1042 | CG1 | VAL A | 142 | −3.939 | 8.065 | −82.336 | 1.00 | 19.39 | C |
| ATOM | 1043 | CG2 | VAL A | 142 | −6.431 | 8.025 | −82.338 | 1.00 | 19.31 | C |
| ATOM | 1044 | C | VAL A | 142 | −3.808 | 10.201 | −80.567 | 1.00 | 19.77 | C |
| ATOM | 1045 | O | VAL A | 142 | −3.183 | 10.985 | −81.271 | 1.00 | 19.50 | O |
| ATOM | 1046 | N | ILE A | 143 | −3.338 | 9.713 | −79.425 | 1.00 | 20.16 | N |
| ATOM | 1047 | CA | ILE A | 143 | −1.922 | 9.829 | −79.065 | 1.00 | 20.71 | C |
| ATOM | 1048 | CB | ILE A | 143 | −1.713 | 10.311 | −77.611 | 1.00 | 20.37 | C |
| ATOM | 1049 | CG1 | ILE A | 143 | −2.371 | 11.669 | −77.388 | 1.00 | 20.26 | C |
| ATOM | 1050 | CD1 | ILE A | 143 | −2.994 | 11.808 | −76.017 | 1.00 | 20.84 | C |
| ATOM | 1051 | CG2 | ILE A | 143 | −0.230 | 10.361 | −77.269 | 1.00 | 19.82 | C |
| ATOM | 1052 | C | ILE A | 143 | −1.212 | 8.477 | −79.254 | 1.00 | 21.29 | C |
| ATOM | 1053 | O | ILE A | 143 | −1.480 | 7.504 | −78.524 | 1.00 | 21.06 | O |
| ATOM | 1054 | N | PRO A | 144 | −0.312 | 8.408 | −80.248 | 1.00 | 21.45 | N |
| ATOM | 1055 | CA | PRO A | 144 | 0.581 | 7.262 | −80.351 | 1.00 | 21.51 | C |
| ATOM | 1056 | CB | PRO A | 144 | 1.389 | 7.558 | −81.619 | 1.00 | 21.19 | C |
| ATOM | 1057 | CG | PRO A | 144 | 1.149 | 9.005 | −81.921 | 1.00 | 20.88 | C |
| ATOM | 1058 | CD | PRO A | 144 | −0.222 | 9.286 | −81.426 | 1.00 | 20.81 | C |
| ATOM | 1059 | C | PRO A | 144 | 1.502 | 7.139 | −79.133 | 1.00 | 21.84 | C |
| ATOM | 1060 | O | PRO A | 144 | 2.091 | 8.121 | −78.688 | 1.00 | 21.41 | O |
| ATOM | 1061 | N | LEU A | 145 | 1.575 | 5.937 | −78.581 | 1.00 | 23.09 | N |

-continued

| | | Atomic coordinates for CRBN:DDB1:Lenalidomide (Human protein) | | | | | | | |
|---|---|---|---|---|---|---|---|---|---|
| ATOM | 1062 | CA | LEU A | 145 | 2.541 | 5.613 | −77.553 | 1.00 | 24.87 | C |
| ATOM | 1063 | CB | LEU A | 145 | 1.939 | 4.598 | −76.578 | 1.00 | 24.50 | C |
| ATOM | 1064 | CG | LEU A | 145 | 0.677 | 5.031 | −75.820 | 1.00 | 24.70 | C |
| ATOM | 1065 | CD1 | LEU A | 145 | −0.043 | 3.840 | −75.196 | 1.00 | 24.36 | C |
| ATOM | 1066 | CD2 | LEU A | 145 | 1.005 | 6.079 | −74.764 | 1.00 | 23.92 | C |
| ATOM | 1067 | C | LEU A | 145 | 3.779 | 5.036 | −78.243 | 1.00 | 27.01 | C |
| ATOM | 1068 | O | LEU A | 145 | 3.788 | 3.866 | −78.636 | 1.00 | 28.30 | O |
| ATOM | 1069 | N | ASP A | 146 | 4.814 | 5.853 | −78.421 | 1.00 | 28.58 | N |
| ATOM | 1070 | CA | ASP A | 146 | 5.942 | 5.440 | −79.259 | 1.00 | 30.41 | C |
| ATOM | 1071 | CB | ASP A | 146 | 5.989 | 6.253 | −80.565 | 1.00 | 30.94 | C |
| ATOM | 1072 | CG | ASP A | 146 | 5.371 | 5.506 | −81.746 | 1.00 | 30.83 | C |
| ATOM | 1073 | OD1 | ASP A | 146 | 5.197 | 4.271 | −81.661 | 1.00 | 31.21 | O |
| ATOM | 1074 | OD2 | ASP A | 146 | 5.068 | 6.155 | −82.767 | 1.00 | 30.98 | O |
| ATOM | 1075 | C | ASP A | 146 | 7.306 | 5.433 | −78.568 | 1.00 | 31.83 | C |
| ATOM | 1076 | O | ASP A | 146 | 8.255 | 4.802 | −79.058 | 1.00 | 32.96 | O |
| ATOM | 1077 | N | ARG A | 147 | 7.392 | 6.111 | −77.427 | 1.00 | 31.33 | N |
| ATOM | 1078 | CA | ARG A | 147 | 8.648 | 6.264 | −76.679 | 1.00 | 31.32 | C |
| ATOM | 1079 | CB | ARG A | 147 | 9.629 | 5.088 | −76.893 | 1.00 | 29.74 | C |
| ATOM | 1080 | C | ARG A | 147 | 9.271 | 7.573 | −77.096 | 1.00 | 31.10 | C |
| ATOM | 1081 | O | ARG A | 147 | 9.675 | 8.373 | −76.247 | 1.00 | 32.96 | O |
| ATOM | 1082 | N | ASP A | 148 | 9.331 | 7.799 | −78.405 | 1.00 | 30.18 | N |
| ATOM | 1083 | CA | ASP A | 148 | 9.811 | 9.064 | −78.940 | 1.00 | 29.15 | C |
| ATOM | 1084 | CB | ASP A | 148 | 10.421 | 8.872 | −80.336 | 1.00 | 28.53 | C |
| ATOM | 1085 | C | ASP A | 148 | 8.707 | 10.136 | −78.951 | 1.00 | 28.46 | C |
| ATOM | 1086 | O | ASP A | 148 | 8.907 | 11.209 | −79.502 | 1.00 | 29.93 | O |
| ATOM | 1087 | N | ASN A | 149 | 7.555 | 9.847 | −78.333 | 1.00 | 26.72 | N |
| ATOM | 1088 | CA | ASN A | 149 | 6.480 | 10.838 | −78.180 | 1.00 | 24.78 | C |
| ATOM | 1089 | CB | ASN A | 149 | 5.129 | 10.265 | −78.642 | 1.00 | 24.37 | C |
| ATOM | 1090 | CG | ASN A | 149 | 4.089 | 11.350 | −78.928 | 1.00 | 24.34 | C |
| ATOM | 1091 | OD1 | ASN A | 149 | 4.390 | 12.550 | −78.901 | 1.00 | 24.24 | O |
| ATOM | 1092 | ND2 | ASN A | 149 | 2.860 | 10.929 | −79.219 | 1.00 | 23.72 | N |
| ATOM | 1093 | C | ASN A | 149 | 6.381 | 11.384 | −76.747 | 1.00 | 24.38 | C |
| ATOM | 1094 | O | ASN A | 149 | 5.311 | 11.343 | −76.115 | 1.00 | 24.38 | O |
| ATOM | 1095 | N | LYS A | 150 | 7.500 | 11.909 | −76.248 | 1.00 | 23.61 | N |
| ATOM | 1096 | CA | LYS A | 150 | 7.567 | 12.504 | −74.912 | 1.00 | 23.02 | C |
| ATOM | 1097 | CB | LYS A | 150 | 9.016 | 12.852 | −74.551 | 1.00 | 22.42 | C |
| ATOM | 1098 | C | LYS A | 150 | 6.643 | 13.726 | −74.735 | 1.00 | 23.09 | C |
| ATOM | 1099 | O | LYS A | 150 | 6.172 | 13.992 | −73.638 | 1.00 | 23.48 | O |
| ATOM | 1100 | N | GLU A | 151 | 6.371 | 14.457 | −75.810 | 1.00 | 23.37 | N |
| ATOM | 1101 | CA | GLU A | 151 | 5.451 | 15.598 | −75.730 | 1.00 | 23.90 | C |
| ATOM | 1102 | CB | GLU A | 151 | 5.943 | 16.734 | −76.607 | 1.00 | 25.04 | C |
| ATOM | 1103 | CG | GLU A | 151 | 7.180 | 17.436 | −76.083 | 1.00 | 26.49 | C |
| ATOM | 1104 | CD | GLU A | 151 | 7.803 | 18.330 | −77.132 | 1.00 | 26.97 | C |
| ATOM | 1105 | OE1 | GLU A | 151 | 7.247 | 18.390 | −78.250 | 1.00 | 27.05 | O |
| ATOM | 1106 | OE2 | GLU A | 151 | 8.843 | 18.963 | −76.845 | 1.00 | 27.40 | O |
| ATOM | 1107 | C | GLU A | 151 | 3.976 | 15.281 | −76.065 | 1.00 | 23.62 | C |
| ATOM | 1108 | O | GLU A | 151 | 3.170 | 16.200 | −76.281 | 1.00 | 22.96 | O |
| ATOM | 1109 | N | LEU A | 152 | 3.632 | 13.990 | −76.092 | 1.00 | 22.95 | N |
| ATOM | 1110 | CA | LEU A | 152 | 2.268 | 13.520 | −76.401 | 1.00 | 22.39 | C |
| ATOM | 1111 | CB | LEU A | 152 | 1.394 | 13.507 | −75.148 | 1.00 | 22.22 | C |
| ATOM | 1112 | CG | LEU A | 152 | 1.905 | 12.665 | −73.984 | 1.00 | 22.59 | C |
| ATOM | 1113 | CD1 | LEU A | 152 | 1.112 | 13.012 | −72.739 | 1.00 | 22.49 | C |
| ATOM | 1114 | CD2 | LEU A | 152 | 1.835 | 11.172 | −74.279 | 1.00 | 21.91 | C |
| ATOM | 1115 | C | LEU A | 152 | 1.545 | 14.270 | −77.521 | 1.00 | 22.03 | C |
| ATOM | 1116 | O | LEU A | 152 | 0.338 | 14.485 | −77.441 | 1.00 | 21.60 | O |
| ATOM | 1117 | N | LYS A | 153 | 2.290 | 14.661 | −78.558 | 1.00 | 22.04 | N |
| ATOM | 1118 | CA | LYS A | 153 | 1.702 | 15.215 | −79.786 | 1.00 | 21.22 | C |
| ATOM | 1119 | CB | LYS A | 153 | 2.799 | 15.626 | −80.787 | 1.00 | 20.44 | C |
| ATOM | 1120 | C | LYS A | 153 | 0.743 | 14.170 | −80.382 | 1.00 | 20.59 | C |
| ATOM | 1121 | O | LYS A | 153 | 0.941 | 12.954 | −80.201 | 1.00 | 20.13 | O |
| ATOM | 1122 | N | ALA A | 154 | −0.303 | 14.642 | −81.062 | 1.00 | 19.71 | N |
| ATOM | 1123 | CA | ALA A | 154 | −1.429 | 13.777 | −81.408 | 1.00 | 19.13 | C |
| ATOM | 1124 | CB | ALA A | 154 | −2.411 | 13.712 | −80.235 | 1.00 | 19.68 | C |
| ATOM | 1125 | C | ALA A | 154 | −2.146 | 14.220 | −82.666 | 1.00 | 18.42 | C |
| ATOM | 1126 | O | ALA A | 154 | −1.872 | 15.279 | −83.191 | 1.00 | 18.07 | O |
| ATOM | 1127 | N | PHE A | 155 | −3.082 | 13.398 | −83.133 | 1.00 | 18.67 | N |
| ATOM | 1128 | CA | PHE A | 155 | −3.911 | 13.749 | −84.282 | 1.00 | 19.14 | C |
| ATOM | 1129 | CB | PHE A | 155 | −3.357 | 13.154 | −85.579 | 1.00 | 19.07 | C |
| ATOM | 1130 | CG | PHE A | 155 | −3.241 | 11.656 | −85.571 | 1.00 | 18.85 | C |
| ATOM | 1131 | CD1 | PHE A | 155 | −4.347 | 10.853 | −85.844 | 1.00 | 18.79 | C |
| ATOM | 1132 | CE1 | PHE A | 155 | −4.235 | 9.472 | −85.857 | 1.00 | 18.70 | C |
| ATOM | 1133 | CZ | PHE A | 155 | −3.010 | 8.880 | −85.598 | 1.00 | 18.75 | C |
| ATOM | 1134 | CE2 | PHE A | 155 | −1.900 | 9.667 | −85.329 | 1.00 | 18.66 | C |
| ATOM | 1135 | CD2 | PHE A | 155 | −2.013 | 11.045 | −85.330 | 1.00 | 18.67 | C |
| ATOM | 1136 | C | PHE A | 155 | −5.364 | 13.351 | −84.097 | 1.00 | 19.79 | C |
| ATOM | 1137 | O | PHE A | 155 | −5.663 | 12.368 | −83.408 | 1.00 | 19.82 | O |
| ATOM | 1138 | N | ASN A | 156 | −6.254 | 14.126 | −84.728 | 1.00 | 20.50 | N |

-continued

| | | | Atomic coordinates for CRBN:DDB1:Lenalidomide (Human protein) | | | | | | |
|---|---|---|---|---|---|---|---|---|---|
| ATOM | 1139 | CA | ASN A | 156 | −7.702 | 13.918 | −84.651 | 1.00 | 20.81 | C |
| ATOM | 1140 | CB | ASN A | 156 | −8.416 | 15.261 | −84.601 | 1.00 | 21.24 | C |
| ATOM | 1141 | CG | ASN A | 156 | −8.175 | 16.007 | −83.313 | 1.00 | 21.30 | C |
| ATOM | 1142 | OD1 | ASN A | 156 | −7.463 | 17.005 | −83.304 | 1.00 | 20.95 | O |
| ATOM | 1143 | ND2 | ASN A | 156 | −8.783 | 15.538 | −82.216 | 1.00 | 21.75 | N |
| ATOM | 1144 | C | ASN A | 156 | −8.239 | 13.160 | −85.845 | 1.00 | 20.58 | C |
| ATOM | 1145 | O | ASN A | 156 | −7.705 | 13.282 | −86.931 | 1.00 | 21.05 | O |
| ATOM | 1146 | N | ILE A | 157 | −9.314 | 12.404 | −85.643 | 1.00 | 20.79 | N |
| ATOM | 1147 | CA | ILE A | 157 | −10.038 | 11.755 | −86.740 | 1.00 | 21.13 | C |
| ATOM | 1148 | CB | ILE A | 157 | −9.974 | 10.214 | −86.645 | 1.00 | 21.13 | C |
| ATOM | 1149 | CG1 | ILE A | 157 | −8.531 | 9.741 | −86.396 | 1.00 | 21.40 | C |
| ATOM | 1150 | CD1 | ILE A | 157 | −8.387 | 8.253 | −86.120 | 1.00 | 21.25 | C |
| ATOM | 1151 | CG2 | ILE A | 157 | −10.545 | 9.588 | −87.909 | 1.00 | 21.33 | C |
| ATOM | 1152 | C | ILE A | 157 | −11.503 | 12.196 | −86.731 | 1.00 | 21.47 | C |
| ATOM | 1153 | O | ILE A | 157 | −12.136 | 12.207 | −85.689 | 1.00 | 21.83 | O |
| ATOM | 1154 | N | ARG A | 158 | −12.040 | 12.565 | −87.889 | 1.00 | 22.28 | N |
| ATOM | 1155 | CA | ARG A | 158 | −13.436 | 12.993 | −87.969 | 1.00 | 23.01 | C |
| ATOM | 1156 | CB | ARG A | 158 | −13.742 | 13.648 | −89.326 | 1.00 | 22.33 | C |
| ATOM | 1157 | C | ARG A | 158 | −14.387 | 11.824 | −87.689 | 1.00 | 23.89 | C |
| ATOM | 1158 | O | ARG A | 158 | −14.168 | 10.698 | −88.138 | 1.00 | 23.82 | O |
| ATOM | 1159 | N | LEU A | 159 | −15.417 | 12.100 | −86.901 | 1.00 | 25.68 | N |
| ATOM | 1160 | CA | LEU A | 159 | −16.498 | 11.154 | −86.666 | 1.00 | 27.15 | C |
| ATOM | 1161 | CB | LEU A | 159 | −16.728 | 10.926 | −85.163 | 1.00 | 26.45 | C |
| ATOM | 1162 | CG | LEU A | 159 | −15.675 | 10.080 | −84.450 | 1.00 | 26.50 | C |
| ATOM | 1163 | CD1 | LEU A | 159 | −16.187 | 9.550 | −83.124 | 1.00 | 25.90 | C |
| ATOM | 1164 | CD2 | LEU A | 159 | −15.276 | 8.929 | −85.348 | 1.00 | 26.75 | C |
| ATOM | 1165 | C | LEU A | 159 | −17.762 | 11.689 | −87.291 | 1.00 | 28.46 | C |
| ATOM | 1166 | O | LEU A | 159 | −18.191 | 12.797 | −86.979 | 1.00 | 28.72 | O |
| ATOM | 1167 | N | GLU A | 160 | −18.351 | 10.904 | −88.183 | 1.00 | 30.46 | N |
| ATOM | 1168 | CA | GLU A | 160 | −19.672 | 11.216 | −88.697 | 1.00 | 32.15 | C |
| ATOM | 1169 | CB | GLU A | 160 | −20.118 | 10.144 | −89.691 | 1.00 | 35.24 | C |
| ATOM | 1170 | CG | GLU A | 160 | −19.556 | 10.321 | −91.090 | 1.00 | 38.16 | C |
| ATOM | 1171 | CD | GLU A | 160 | −20.514 | 11.058 | −92.012 | 1.00 | 43.43 | C |
| ATOM | 1172 | OE1 | GLU A | 160 | −21.706 | 11.204 | −91.649 | 1.00 | 45.95 | O |
| ATOM | 1173 | OE2 | GLU A | 160 | −20.086 | 11.479 | −93.114 | 1.00 | 46.22 | O |
| ATOM | 1174 | C | GLU A | 160 | −20.666 | 11.357 | −87.531 | 1.00 | 31.20 | C |
| ATOM | 1175 | O | GLU A | 160 | −21.436 | 12.318 | −87.476 | 1.00 | 32.34 | O |
| ATOM | 1176 | N | GLU A | 161 | −20.606 | 10.427 | −86.584 | 1.00 | 29.59 | N |
| ATOM | 1177 | CA | GLU A | 161 | −21.498 | 10.427 | −85.428 | 1.00 | 28.98 | C |
| ATOM | 1178 | CB | GLU A | 161 | −21.559 | 9.029 | −84.813 | 1.00 | 29.63 | C |
| ATOM | 1179 | CG | GLU A | 161 | −22.089 | 7.956 | −85.755 | 1.00 | 30.27 | C |
| ATOM | 1180 | CD | GLU A | 161 | −21.113 | 7.560 | −86.859 | 1.00 | 32.69 | C |
| ATOM | 1181 | OE1 | GLU A | 161 | −19.929 | 7.970 | −86.814 | 1.00 | 33.66 | O |
| ATOM | 1182 | OE2 | GLU A | 161 | −21.533 | 6.823 | −87.783 | 1.00 | 33.80 | O |
| ATOM | 1183 | C | GLU A | 161 | −21.081 | 11.466 | −84.385 | 1.00 | 27.52 | C |
| ATOM | 1184 | O | GLU A | 161 | −19.954 | 11.460 | −83.905 | 1.00 | 27.08 | O |
| ATOM | 1185 | N | LEU A | 162 | −22.008 | 12.356 | −84.047 | 1.00 | 27.25 | N |
| ATOM | 1186 | CA | LEU A | 162 | −21.720 | 13.525 | −83.211 | 1.00 | 27.63 | C |
| ATOM | 1187 | CB | LEU A | 162 | −22.414 | 14.758 | −83.779 | 1.00 | 26.35 | C |
| ATOM | 1188 | CG | LEU A | 162 | −21.789 | 15.361 | −85.034 | 1.00 | 25.70 | C |
| ATOM | 1189 | CD1 | LEU A | 162 | −22.857 | 16.039 | −85.873 | 1.00 | 25.47 | C |
| ATOM | 1190 | CD2 | LEU A | 162 | −20.681 | 16.339 | −84.680 | 1.00 | 25.35 | C |
| ATOM | 1191 | C | LEU A | 162 | −22.121 | 13.357 | −81.748 | 1.00 | 28.97 | C |
| ATOM | 1192 | O | LEU A | 162 | −21.598 | 14.051 | −80.875 | 1.00 | 29.65 | O |
| ATOM | 1193 | N | HIS A | 163 | −23.060 | 12.447 | −81.489 | 1.00 | 29.80 | N |
| ATOM | 1194 | CA | HIS A | 163 | −23.501 | 12.154 | −80.130 | 1.00 | 28.90 | C |
| ATOM | 1195 | CB | HIS A | 163 | −25.007 | 12.377 | −79.976 | 1.00 | 31.33 | C |
| ATOM | 1196 | CG | HIS A | 163 | −25.538 | 13.534 | −80.797 | 1.00 | 35.52 | C |
| ATOM | 1197 | ND1 | HIS A | 163 | −25.051 | 14.794 | −80.684 | 1.00 | 37.41 | N |
| ATOM | 1198 | CE1 | HIS A | 163 | −25.701 | 15.604 | −81.546 | 1.00 | 36.70 | C |
| ATOM | 1199 | NE2 | HIS A | 163 | −26.607 | 14.863 | −82.213 | 1.00 | 36.79 | N |
| ATOM | 1200 | CD2 | HIS A | 163 | −26.535 | 13.584 | −81.776 | 1.00 | 35.98 | C |
| ATOM | 1201 | C | HIS A | 163 | −23.117 | 10.756 | −79.762 | 1.00 | 27.12 | C |
| ATOM | 1202 | O | HIS A | 163 | −23.924 | 9.832 | −79.834 | 1.00 | 26.20 | O |
| ATOM | 1203 | N | VAL A | 164 | −21.862 | 10.585 | −79.375 | 1.00 | 25.78 | N |
| ATOM | 1204 | CA | VAL A | 164 | −21.406 | 9.298 | −78.869 | 1.00 | 25.97 | C |
| ATOM | 1205 | CB | VAL A | 164 | −19.923 | 9.029 | −79.218 | 1.00 | 25.34 | C |
| ATOM | 1206 | CG1 | VAL A | 164 | −19.425 | 7.783 | −78.504 | 1.00 | 24.90 | C |
| ATOM | 1207 | CG2 | VAL A | 164 | −19.742 | 8.890 | −80.728 | 1.00 | 23.72 | C |
| ATOM | 1208 | C | VAL A | 164 | −21.646 | 9.195 | −77.358 | 1.00 | 25.79 | C |
| ATOM | 1209 | O | VAL A | 164 | −21.224 | 10.062 | −76.593 | 1.00 | 26.38 | O |
| ATOM | 1210 | N | ILE A | 165 | −22.345 | 8.139 | −76.950 | 1.00 | 25.75 | N |
| ATOM | 1211 | CA | ILE A | 165 | −22.632 | 7.871 | −75.541 | 1.00 | 26.20 | C |
| ATOM | 1212 | CB | ILE A | 165 | −23.836 | 6.921 | −75.380 | 1.00 | 26.83 | C |
| ATOM | 1213 | CG1 | ILE A | 165 | −24.974 | 7.289 | −76.348 | 1.00 | 27.34 | C |
| ATOM | 1214 | CD1 | ILE A | 165 | −25.973 | 8.277 | −75.791 | 1.00 | 28.90 | C |
| ATOM | 1215 | CG2 | ILE A | 165 | −24.285 | 6.854 | −73.924 | 1.00 | 26.01 | C |

-continued

| | | | | | | | | | |
|---|---|---|---|---|---|---|---|---|---|
| ATOM | 1216 | C | ILE A | 165 | −21.435 | 7.242 | −74.819 | 1.00 | 26.30 | C |
| ATOM | 1217 | O | ILE A | 165 | −21.112 | 7.630 | −73.699 | 1.00 | 27.54 | O |
| ATOM | 1218 | N | ASP A | 166 | −20.790 | 6.263 | −75.445 | 1.00 | 26.10 | N |
| ATOM | 1219 | CA | ASP A | 166 | −19.677 | 5.570 | −74.806 | 1.00 | 26.58 | C |
| ATOM | 1220 | CB | ASP A | 166 | −20.231 | 4.610 | −73.749 | 1.00 | 28.65 | C |
| ATOM | 1221 | CG | ASP A | 166 | −19.158 | 4.052 | −72.829 | 1.00 | 29.92 | C |
| ATOM | 1222 | OD1 | ASP A | 166 | −18.046 | 4.651 | −72.750 | 1.00 | 30.77 | O |
| ATOM | 1223 | OD2 | ASP A | 166 | −19.439 | 3.004 | −72.192 | 1.00 | 29.65 | O |
| ATOM | 1224 | C | ASP A | 166 | −18.780 | 4.824 | −75.812 | 1.00 | 26.18 | C |
| ATOM | 1225 | O | ASP A | 166 | −19.268 | 4.298 | −76.811 | 1.00 | 26.45 | O |
| ATOM | 1226 | N | VAL A | 167 | −17.477 | 4.768 | −75.535 | 1.00 | 24.94 | N |
| ATOM | 1227 | CA | VAL A | 167 | −16.518 | 4.128 | −76.448 | 1.00 | 23.88 | C |
| ATOM | 1228 | CB | VAL A | 167 | −15.891 | 5.161 | −77.405 | 1.00 | 23.79 | C |
| ATOM | 1229 | CG1 | VAL A | 167 | −15.296 | 6.329 | −76.623 | 1.00 | 23.13 | C |
| ATOM | 1230 | CG2 | VAL A | 167 | −14.857 | 4.493 | −78.314 | 1.00 | 23.21 | C |
| ATOM | 1231 | C | VAL A | 167 | −15.394 | 3.324 | −75.762 | 1.00 | 23.51 | C |
| ATOM | 1232 | O | VAL A | 167 | −14.845 | 3.746 | −74.733 | 1.00 | 23.65 | O |
| ATOM | 1233 | N | LYS A | 168 | −15.050 | 2.183 | −76.370 | 1.00 | 22.37 | N |
| ATOM | 1234 | CA | LYS A | 168 | −14.023 | 1.270 | −75.875 | 1.00 | 21.50 | C |
| ATOM | 1235 | CB | LYS A | 168 | −14.676 | 0.115 | −75.117 | 1.00 | 20.74 | C |
| ATOM | 1236 | CG | LYS A | 168 | −14.195 | −0.052 | −73.690 | 1.00 | 20.70 | C |
| ATOM | 1237 | CD | LYS A | 168 | −15.163 | 0.619 | −72.733 | 1.00 | 20.65 | C |
| ATOM | 1238 | CE | LYS A | 168 | −14.454 | 1.475 | −71.703 | 1.00 | 20.92 | C |
| ATOM | 1239 | NZ | LYS A | 168 | −15.309 | 1.671 | −70.497 | 1.00 | 21.35 | N |
| ATOM | 1240 | C | LYS A | 168 | −13.314 | 0.687 | −77.074 | 1.00 | 21.94 | C |
| ATOM | 1241 | O | LYS A | 168 | −13.923 | 0.546 | −78.134 | 1.00 | 23.69 | O |
| ATOM | 1242 | N | PHE A | 169 | −12.038 | 0.340 | −76.922 | 1.00 | 21.89 | N |
| ATOM | 1243 | CA | PHE A | 169 | −11.341 | −0.523 | −77.891 | 1.00 | 21.42 | C |
| ATOM | 1244 | CB | PHE A | 169 | −9.835 | −0.389 | −77.740 | 1.00 | 20.91 | C |
| ATOM | 1245 | CG | PHE A | 169 | −9.288 | 0.914 | −78.213 | 1.00 | 21.29 | C |
| ATOM | 1246 | CD1 | PHE A | 169 | −9.129 | 1.164 | −79.575 | 1.00 | 21.40 | C |
| ATOM | 1247 | CE1 | PHE A | 169 | −8.593 | 2.368 | −80.014 | 1.00 | 21.62 | C |
| ATOM | 1248 | CZ | PHE A | 169 | −8.204 | 3.333 | −79.091 | 1.00 | 21.43 | C |
| ATOM | 1249 | CE2 | PHE A | 169 | −8.346 | 3.088 | −77.732 | 1.00 | 21.34 | C |
| ATOM | 1250 | CD2 | PHE A | 169 | −8.886 | 1.887 | −77.299 | 1.00 | 21.57 | C |
| ATOM | 1251 | C | PHE A | 169 | −11.712 | −1.986 | −77.648 | 1.00 | 21.87 | C |
| ATOM | 1252 | O | PHE A | 169 | −11.936 | −2.385 | −76.506 | 1.00 | 23.56 | O |
| ATOM | 1253 | N | LEU A | 170 | −11.754 | −2.795 | −78.696 | 1.00 | 21.49 | N |
| ATOM | 1254 | CA | LEU A | 170 | −12.044 | −4.216 | −78.515 | 1.00 | 21.60 | C |
| ATOM | 1255 | CB | LEU A | 170 | −12.935 | −4.730 | −79.637 | 1.00 | 21.28 | C |
| ATOM | 1256 | CG | LEU A | 170 | −14.284 | −4.040 | −79.802 | 1.00 | 21.30 | C |
| ATOM | 1257 | CD1 | LEU A | 170 | −14.875 | −4.430 | −81.144 | 1.00 | 21.61 | C |
| ATOM | 1258 | CD2 | LEU A | 170 | −15.230 | −4.389 | −78.661 | 1.00 | 20.93 | C |
| ATOM | 1259 | C | LEU A | 170 | −10.778 | −5.052 | −78.441 | 1.00 | 22.19 | C |
| ATOM | 1260 | O | LEU A | 170 | −9.700 | −4.596 | −78.824 | 1.00 | 22.62 | O |
| ATOM | 1261 | N | TYR A | 171 | −10.917 | −6.279 | −77.946 | 1.00 | 22.88 | N |
| ATOM | 1262 | CA | TYR A | 171 | −9.821 | −7.242 | −77.945 | 1.00 | 23.91 | C |
| ATOM | 1263 | CB | TYR A | 171 | −9.836 | −8.098 | −76.679 | 1.00 | 22.49 | C |
| ATOM | 1264 | CG | TYR A | 171 | −9.645 | −7.356 | −75.384 | 1.00 | 21.77 | C |
| ATOM | 1265 | CD2 | TYR A | 171 | −8.382 | −7.194 | −74.833 | 1.00 | 21.30 | C |
| ATOM | 1266 | CE2 | TYR A | 171 | −8.209 | −6.535 | −73.633 | 1.00 | 20.92 | C |
| ATOM | 1267 | CZ | TYR A | 171 | −9.314 | −6.038 | −72.964 | 1.00 | 20.91 | C |
| ATOM | 1268 | OH | TYR A | 171 | −9.164 | −5.381 | −71.774 | 1.00 | 20.93 | O |
| ATOM | 1269 | CE1 | TYR A | 171 | −10.577 | −6.196 | −73.482 | 1.00 | 21.16 | C |
| ATOM | 1270 | CD1 | TYR A | 171 | −10.738 | −6.852 | −74.684 | 1.00 | 21.79 | C |
| ATOM | 1271 | C | TYR A | 171 | −9.915 | −8.173 | −79.149 | 1.00 | 25.86 | C |
| ATOM | 1272 | O | TYR A | 171 | −10.998 | −8.397 | −79.701 | 1.00 | 25.36 | O |
| ATOM | 1273 | N | GLY A | 172 | −8.768 | −8.728 | −79.537 | 1.00 | 28.47 | N |
| ATOM | 1274 | CA | GLY A | 172 | −8.718 | −9.801 | −80.530 | 1.00 | 30.12 | C |
| ATOM | 1275 | C | GLY A | 172 | −9.069 | −9.361 | −81.934 | 1.00 | 30.35 | C |
| ATOM | 1276 | O | GLY A | 172 | −9.875 | −10.000 | −82.610 | 1.00 | 29.19 | O |
| ATOM | 1277 | N | CYS A | 173 | −8.454 | −8.268 | −82.373 | 1.00 | 32.15 | N |
| ATOM | 1278 | CA | CYS A | 173 | −8.713 | −7.724 | −83.703 | 1.00 | 33.31 | C |
| ATOM | 1279 | CB | CYS A | 173 | −9.333 | −6.329 | −83.600 | 1.00 | 32.29 | C |
| ATOM | 1280 | SG | CYS A | 173 | −11.009 | −6.360 | −82.933 | 1.00 | 31.25 | S |
| ATOM | 1281 | C | CYS A | 173 | −7.440 | −7.677 | −84.522 | 1.00 | 34.11 | C |
| ATOM | 1282 | O | CYS A | 173 | −6.331 | −7.664 | −83.961 | 1.00 | 34.68 | O |
| ATOM | 1283 | N | GLN A | 174 | −7.597 | −7.648 | −85.846 | 1.00 | 32.89 | N |
| ATOM | 1284 | CA | GLN A | 174 | −6.444 | −7.548 | −86.733 | 1.00 | 32.00 | C |
| ATOM | 1285 | CB | GLN A | 174 | −6.803 | −8.059 | −88.128 | 1.00 | 32.72 | C |
| ATOM | 1286 | C | GLN A | 174 | −5.851 | −6.116 | −86.771 | 1.00 | 31.11 | C |
| ATOM | 1287 | O | GLN A | 174 | −4.802 | −5.885 | −87.378 | 1.00 | 31.59 | O |
| ATOM | 1288 | N | ALA A | 175 | −6.527 | −5.173 | −86.109 | 1.00 | 29.24 | N |
| ATOM | 1289 | CA | ALA A | 175 | −6.038 | −3.797 | −85.934 | 1.00 | 27.27 | C |
| ATOM | 1290 | CB | ALA A | 175 | −6.322 | −2.966 | −87.177 | 1.00 | 27.07 | C |
| ATOM | 1291 | C | ALA A | 175 | −6.737 | −3.178 | −84.730 | 1.00 | 26.41 | C |
| ATOM | 1292 | O | ALA A | 175 | −7.799 | −3.670 | −84.318 | 1.00 | 26.11 | O |

-continued

| | | | Atomic coordinates for CRBN:DDB1:Lenalidomide (Human protein) | | | | | | |
|---|---|---|---|---|---|---|---|---|---|
| ATOM | 1293 | N | PRO A | 176 | −6.152 | −2.102 | −84.150 | 1.00 | 25.35 | N |
| ATOM | 1294 | CA | PRO A | 176 | −6.882 | −1.357 | −83.118 | 1.00 | 24.40 | C |
| ATOM | 1295 | CB | PRO A | 176 | −6.013 | −0.124 | −82.909 | 1.00 | 23.94 | C |
| ATOM | 1296 | CG | PRO A | 176 | −4.634 | −0.641 | −83.133 | 1.00 | 24.18 | C |
| ATOM | 1297 | CD | PRO A | 176 | −4.740 | −1.680 | −84.221 | 1.00 | 24.68 | C |
| ATOM | 1298 | C | PRO A | 176 | −8.286 | −0.984 | −83.581 | 1.00 | 23.51 | C |
| ATOM | 1299 | O | PRO A | 176 | −8.471 | −0.495 | −84.690 | 1.00 | 22.92 | O |
| ATOM | 1300 | N | THR A | 177 | −9.266 | −1.244 | −82.729 | 1.00 | 23.65 | N |
| ATOM | 1301 | CA | THR A | 177 | −10.664 | −1.188 | −83.131 | 1.00 | 23.59 | C |
| ATOM | 1302 | CB | THR A | 177 | −11.179 | −2.610 | −83.430 | 1.00 | 22.91 | C |
| ATOM | 1303 | OG1 | THR A | 177 | −10.374 | −3.202 | −84.452 | 1.00 | 22.69 | O |
| ATOM | 1304 | CG2 | THR A | 177 | −12.621 | −2.591 | −83.874 | 1.00 | 22.98 | C |
| ATOM | 1305 | C | THR A | 177 | −11.518 | −0.575 | −82.027 | 1.00 | 23.68 | C |
| ATOM | 1306 | O | THR A | 177 | −11.515 | −1.073 | −80.899 | 1.00 | 25.01 | O |
| ATOM | 1307 | N | ILE A | 178 | −12.248 | 0.496 | −82.336 | 1.00 | 22.71 | N |
| ATOM | 1308 | CA | ILE A | 178 | −13.168 | 1.066 | −81.350 | 1.00 | 22.05 | C |
| ATOM | 1309 | CB | ILE A | 178 | −13.116 | 2.606 | −81.291 | 1.00 | 21.61 | C |
| ATOM | 1310 | CG1 | ILE A | 178 | −13.648 | 3.242 | −82.579 | 1.00 | 21.50 | C |
| ATOM | 1311 | CD1 | ILE A | 178 | −13.941 | 4.726 | −82.447 | 1.00 | 21.18 | C |
| ATOM | 1312 | CG2 | ILE A | 178 | −11.707 | 3.079 | −80.983 | 1.00 | 21.50 | C |
| ATOM | 1313 | C | ILE A | 178 | −14.604 | 0.592 | −81.540 | 1.00 | 22.74 | C |
| ATOM | 1314 | O | ILE A | 178 | −15.077 | 0.432 | −82.675 | 1.00 | 23.39 | O |
| ATOM | 1315 | N | CYS A | 179 | −15.272 | 0.333 | −80.416 | 1.00 | 22.61 | N |
| ATOM | 1316 | CA | CYS A | 179 | −16.682 | −0.031 | −80.396 | 1.00 | 22.65 | C |
| ATOM | 1317 | CB | CYS A | 179 | −16.863 | −1.407 | −79.791 | 1.00 | 22.78 | C |
| ATOM | 1318 | SG | CYS A | 179 | −18.600 | −1.853 | −79.608 | 1.00 | 24.39 | S |
| ATOM | 1319 | C | CYS A | 179 | −17.419 | 0.971 | −79.542 | 1.00 | 22.86 | C |
| ATOM | 1320 | O | CYS A | 179 | −17.073 | 1.166 | −78.385 | 1.00 | 24.43 | O |
| ATOM | 1321 | N | PHE A | 180 | −18.438 | 1.610 | −80.096 | 1.00 | 22.45 | N |
| ATOM | 1322 | CA | PHE A | 180 | −19.084 | 2.719 | −79.405 | 1.00 | 22.06 | C |
| ATOM | 1323 | CB | PHE A | 180 | −18.450 | 4.051 | −79.829 | 1.00 | 22.28 | C |
| ATOM | 1324 | CG | PHE A | 180 | −18.701 | 4.411 | −81.265 | 1.00 | 22.90 | C |
| ATOM | 1325 | CD1 | PHE A | 180 | −17.936 | 3.857 | −82.279 | 1.00 | 23.73 | C |
| ATOM | 1326 | CE1 | PHE A | 180 | −18.188 | 4.164 | −83.607 | 1.00 | 24.56 | C |
| ATOM | 1327 | CZ | PHE A | 180 | −19.204 | 5.042 | −83.929 | 1.00 | 24.67 | C |
| ATOM | 1328 | CE2 | PHE A | 180 | −19.972 | 5.598 | −82.924 | 1.00 | 23.90 | C |
| ATOM | 1329 | CD2 | PHE A | 180 | −19.719 | 5.281 | −81.605 | 1.00 | 23.21 | C |
| ATOM | 1330 | C | PHE A | 180 | −20.590 | 2.749 | −79.642 | 1.00 | 22.13 | C |
| ATOM | 1331 | O | PHE A | 180 | −21.079 | 2.354 | −80.704 | 1.00 | 22.59 | O |
| ATOM | 1332 | N | VAL A | 181 | −21.321 | 3.216 | −78.638 | 1.00 | 22.10 | N |
| ATOM | 1333 | CA | VAL A | 181 | −22.749 | 3.493 | −78.775 | 1.00 | 21.84 | C |
| ATOM | 1334 | CB | VAL A | 181 | −23.534 | 3.069 | −77.513 | 1.00 | 22.00 | C |
| ATOM | 1335 | CG1 | VAL A | 181 | −24.923 | 3.694 | −77.483 | 1.00 | 21.70 | C |
| ATOM | 1336 | CG2 | VAL A | 181 | −23.620 | 1.552 | −77.446 | 1.00 | 22.25 | C |
| ATOM | 1337 | C | VAL A | 181 | −22.943 | 4.979 | −79.081 | 1.00 | 21.27 | C |
| ATOM | 1338 | O | VAL A | 181 | −22.283 | 5.838 | −78.501 | 1.00 | 21.14 | O |
| ATOM | 1339 | N | TYR A | 182 | −23.825 | 5.262 | −80.028 | 1.00 | 21.01 | N |
| ATOM | 1340 | CA | TYR A | 182 | −24.100 | 6.618 | −80.458 | 1.00 | 20.46 | C |
| ATOM | 1341 | CB | TYR A | 182 | −23.277 | −6.960 | −81.706 | 1.00 | 19.68 | C |
| ATOM | 1342 | CG | TYR A | 182 | −23.793 | 6.325 | −82.988 | 1.00 | 19.34 | C |
| ATOM | 1343 | CD1 | TYR A | 182 | −23.398 | 5.033 | −83.365 | 1.00 | 18.95 | C |
| ATOM | 1344 | CE1 | TYR A | 182 | −23.893 | 4.453 | −84.529 | 1.00 | 18.72 | C |
| ATOM | 1345 | CZ | TYR A | 182 | −24.790 | 5.169 | −85.334 | 1.00 | 18.16 | C |
| ATOM | 1346 | OH | TYR A | 182 | −25.283 | 4.608 | −86.482 | 1.00 | 17.33 | O |
| ATOM | 1347 | CE2 | TYR A | 182 | −25.191 | 6.443 | −84.979 | 1.00 | 18.11 | C |
| ATOM | 1348 | CD2 | TYR A | 182 | −24.696 | 7.015 | −83.819 | 1.00 | 18.71 | C |
| ATOM | 1349 | C | TYR A | 182 | −25.591 | 6.725 | −80.745 | 1.00 | 20.92 | C |
| ATOM | 1350 | O | TYR A | 182 | −26.273 | 5.707 | −80.932 | 1.00 | 20.38 | O |
| ATOM | 1351 | N | GLN A | 183 | −26.092 | 7.955 | −80.765 | 1.00 | 22.25 | N |
| ATOM | 1352 | CA | GLN A | 183 | −27.485 | 8.214 | −81.089 | 1.00 | 23.44 | C |
| ATOM | 1353 | CB | GLN A | 183 | −28.243 | 8.694 | −79.863 | 1.00 | 23.57 | C |
| ATOM | 1354 | CG | GLN A | 183 | −29.746 | 8.699 | −80.071 | 1.00 | 24.41 | C |
| ATOM | 1355 | CD | GLN A | 183 | −30.487 | 9.174 | −78.857 | 1.00 | 25.18 | C |
| ATOM | 1356 | OE1 | GLN A | 183 | −30.276 | 10.288 | −78.395 | 1.00 | 26.29 | O |
| ATOM | 1357 | NE2 | GLN A | 183 | −31.357 | 8.329 | −78.320 | 1.00 | 25.99 | N |
| ATOM | 1358 | C | GLN A | 183 | −27.640 | 9.235 | −82.210 | 1.00 | 24.62 | C |
| ATOM | 1359 | O | GLN A | 183 | −26.882 | 10.217 | −82.287 | 1.00 | 24.31 | O |
| ATOM | 1360 | N | ASP A | 184 | −28.625 | 8.983 | −83.075 | 1.00 | 25.56 | N |
| ATOM | 1361 | CA | ASP A | 184 | −29.054 | 9.941 | −84.089 | 1.00 | 26.67 | C |
| ATOM | 1362 | CB | ASP A | 184 | −28.357 | 9.672 | −85.439 | 1.00 | 26.27 | C |
| ATOM | 1363 | CG | ASP A | 184 | −28.767 | 8.350 | −86.073 | 1.00 | 26.40 | C |
| ATOM | 1364 | OD1 | ASP A | 184 | −29.828 | 7.797 | −85.723 | 1.00 | 26.63 | O |
| ATOM | 1365 | OD2 | ASP A | 184 | −28.027 | 7.867 | −86.950 | 1.00 | 26.86 | O |
| ATOM | 1366 | C | ASP A | 184 | −30.586 | 9.899 | −84.192 | 1.00 | 27.86 | C |
| ATOM | 1367 | O | ASP A | 184 | −31.230 | 9.217 | −83.377 | 1.00 | 27.28 | O |
| ATOM | 1368 | N | PRO A | 185 | −31.176 | 10.631 | −85.179 | 1.00 | 29.19 | N |
| ATOM | 1369 | CA | PRO A | 185 | −32.642 | 10.710 | −85.353 | 1.00 | 29.34 | C |

-continued

| | | | | | | | | | |
|---|---|---|---|---|---|---|---|---|---|
| ATOM | 1370 | CB | PRO A | 185 | −32.791 | 11.532 | −86.632 | 1.00 | 28.78 | C |
| ATOM | 1371 | CG | PRO A | 185 | −31.624 | 12.455 | −86.584 | 1.00 | 29.42 | C |
| ATOM | 1372 | CD | PRO A | 185 | −30.490 | 11.632 | −86.025 | 1.00 | 29.03 | C |
| ATOM | 1373 | C | PRO A | 185 | −33.394 | 9.377 | −85.480 | 1.00 | 29.96 | C |
| ATOM | 1374 | O | PRO A | 185 | −34.573 | 9.317 | −85.141 | 1.00 | 30.82 | O |
| ATOM | 1375 | N | GLN A | 186 | −32.732 | 8.326 | −85.955 | 1.00 | 30.37 | N |
| ATOM | 1376 | CA | GLN A | 186 | −33.395 | 7.031 | −86.112 | 1.00 | 30.40 | C |
| ATOM | 1377 | CB | GLN A | 186 | −32.817 | 6.247 | −87.302 | 1.00 | 30.32 | C |
| ATOM | 1378 | C | GLN A | 186 | −33.348 | 6.204 | −84.828 | 1.00 | 30.46 | C |
| ATOM | 1379 | O | GLN A | 186 | −34.088 | 5.230 | −84.700 | 1.00 | 32.09 | O |
| ATOM | 1380 | N | GLY A | 187 | −32.489 | 6.599 | −83.882 | 1.00 | 29.55 | N |
| ATOM | 1381 | CA | GLY A | 187 | −32.383 | 5.918 | −82.581 | 1.00 | 28.32 | C |
| ATOM | 1382 | C | GLY A | 187 | −30.967 | 5.792 | −82.022 | 1.00 | 28.11 | C |
| ATOM | 1383 | O | GLY A | 187 | −30.111 | 6.655 | −82.265 | 1.00 | 27.13 | O |
| ATOM | 1384 | N | ARG A | 188 | −30.734 | 4.714 | −81.261 | 1.00 | 27.44 | N |
| ATOM | 1385 | CA | ARG A | 188 | −29.413 | 4.393 | −80.704 | 1.00 | 26.77 | C |
| ATOM | 1386 | CB | ARG A | 188 | −29.467 | 4.246 | −79.184 | 1.00 | 26.72 | C |
| ATOM | 1387 | CG | ARG A | 188 | −29.646 | 5.551 | −78.462 | 1.00 | 26.79 | C |
| ATOM | 1388 | CD | ARG A | 188 | −28.940 | 5.599 | −77.115 | 1.00 | 27.35 | C |
| ATOM | 1389 | NE | ARG A | 188 | −29.392 | 6.794 | −76.397 | 1.00 | 27.10 | N |
| ATOM | 1390 | CZ | ARG A | 188 | −29.238 | 7.014 | −75.101 | 1.00 | 26.63 | C |
| ATOM | 1391 | NH1 | ARG A | 188 | −28.614 | 6.134 | −74.327 | 1.00 | 26.42 | N |
| ATOM | 1392 | NH2 | ARG A | 188 | −29.718 | 8.127 | −74.583 | 1.00 | 26.87 | N |
| ATOM | 1393 | C | ARG A | 188 | −28.828 | 3.119 | −81.299 | 1.00 | 26.74 | C |
| ATOM | 1394 | O | ARG A | 188 | −29.537 | 2.119 | −81.478 | 1.00 | 25.82 | O |
| ATOM | 1395 | N | HIS A | 189 | −27.523 | 3.156 | −81.571 | 1.00 | 26.87 | N |
| ATOM | 1396 | CA | HIS A | 189 | −26.838 | 2.056 | −82.259 | 1.00 | 27.54 | C |
| ATOM | 1397 | CB | HIS A | 189 | −26.820 | 2.315 | −83.757 | 1.00 | 26.15 | C |
| ATOM | 1398 | CG | HIS A | 189 | −28.037 | 3.045 | −84.244 | 1.00 | 25.42 | C |
| ATOM | 1399 | ND1 | HIS A | 189 | −29.166 | 2.406 | −84.603 | 1.00 | 24.99 | N |
| ATOM | 1400 | CE1 | HIS A | 189 | −30.091 | 3.313 | −84.957 | 1.00 | 25.16 | C |
| ATOM | 1401 | NE2 | HIS A | 189 | −29.558 | 4.537 | −84.805 | 1.00 | 24.77 | N |
| ATOM | 1402 | CD2 | HIS A | 189 | −28.298 | 4.407 | −84.358 | 1.00 | 24.58 | C |
| ATOM | 1403 | C | HIS A | 189 | −25.437 | 1.858 | −81.772 | 1.00 | 28.85 | C |
| ATOM | 1404 | O | HIS A | 189 | −24.779 | 2.804 | −81.325 | 1.00 | 29.55 | O |
| ATOM | 1405 | N | VAL A | 190 | −24.976 | 0.615 | −81.841 | 1.00 | 28.92 | N |
| ATOM | 1406 | CA | VAL A | 190 | −23.572 | 0.314 | −81.643 | 1.00 | 28.80 | C |
| ATOM | 1407 | CB | VAL A | 190 | −23.360 | −0.959 | −80.791 | 1.00 | 29.59 | C |
| ATOM | 1408 | CG1 | VAL A | 190 | −24.178 | −2.132 | −81.324 | 1.00 | 30.15 | C |
| ATOM | 1409 | CG2 | VAL A | 190 | −21.880 | −1.318 | −80.720 | 1.00 | 29.68 | C |
| ATOM | 1410 | C | VAL A | 190 | −22.886 | −0.195 | −83.004 | 1.00 | 28.72 | C |
| ATOM | 1411 | O | VAL A | 190 | −23.442 | −0.370 | −83.953 | 1.00 | 28.34 | O |
| ATOM | 1412 | N | LYS A | 191 | −21.691 | 0.762 | −83.095 | 1.00 | 29.09 | N |
| ATOM | 1413 | CA | LYS A | 191 | −20.894 | 0.708 | −84.311 | 1.00 | 29.81 | C |
| ATOM | 1414 | CB | LYS A | 191 | −20.942 | 2.053 | −85.033 | 1.00 | 30.22 | C |
| ATOM | 1415 | CG | LYS A | 191 | −20.592 | 1.994 | −86.509 | 1.00 | 31.00 | C |
| ATOM | 1416 | CD | LYS A | 191 | −20.908 | 3.312 | −87.211 | 1.00 | 31.44 | C |
| ATOM | 1417 | CE | LYS A | 191 | −21.005 | 3.132 | −88.724 | 1.00 | 30.99 | C |
| ATOM | 1418 | NZ | LYS A | 191 | −21.571 | 4.336 | −89.387 | 1.00 | 30.24 | N |
| ATOM | 1419 | C | LYS A | 191 | −19.465 | 0.378 | −83.919 | 1.00 | 30.13 | C |
| ATOM | 1420 | O | LYS A | 191 | −19.099 | 0.471 | −82.743 | 1.00 | 30.38 | O |
| ATOM | 1421 | N | THR A | 192 | −18.672 | −0.054 | −84.891 | 1.00 | 30.43 | N |
| ATOM | 1422 | CA | THR A | 192 | −17.241 | −0.240 | −84.686 | 1.00 | 31.22 | C |
| ATOM | 1423 | CB | THR A | 192 | −16.819 | −1.726 | −84.657 | 1.00 | 31.67 | C |
| ATOM | 1424 | OG1 | THR A | 192 | −17.333 | −2.401 | −85.816 | 1.00 | 31.80 | O |
| ATOM | 1425 | CG2 | THR A | 192 | −17.314 | −2.417 | −83.391 | 1.00 | 30.89 | C |
| ATOM | 1426 | C | THR A | 192 | −16.510 | 0.428 | −85.822 | 1.00 | 31.35 | C |
| ATOM | 1427 | O | THR A | 192 | −17.030 | 0.504 | −86.938 | 1.00 | 32.20 | O |
| ATOM | 1428 | N | TYR A | 193 | −15.317 | 0.932 | −85.530 | 1.00 | 30.36 | N |
| ATOM | 1429 | CA | TYR A | 193 | −14.421 | 1.411 | −86.563 | 1.00 | 29.75 | C |
| ATOM | 1430 | CB | TYR A | 193 | −14.279 | 2.935 | −86.532 | 1.00 | 28.84 | C |
| ATOM | 1431 | CG | TYR A | 193 | −15.450 | 3.745 | −87.085 | 1.00 | 28.44 | C |
| ATOM | 1432 | CD1 | TYR A | 193 | −16.015 | 3.466 | −88.337 | 1.00 | 27.25 | C |
| ATOM | 1433 | CE1 | TYR A | 193 | −17.070 | 4.221 | −88.829 | 1.00 | 27.08 | C |
| ATOM | 1434 | CZ | TYR A | 193 | −17.559 | 5.287 | −88.075 | 1.00 | 28.17 | C |
| ATOM | 1435 | OH | TYR A | 193 | −18.602 | 6.067 | −88.524 | 1.00 | 28.24 | O |
| ATOM | 1436 | CE2 | TYR A | 193 | −17.004 | 5.589 | −86.846 | 1.00 | 28.45 | C |
| ATOM | 1437 | CD2 | TYR A | 193 | −15.954 | 4.830 | −86.364 | 1.00 | 28.37 | C |
| ATOM | 1438 | C | TYR A | 193 | −13.071 | 0.784 | −86.323 | 1.00 | 30.33 | C |
| ATOM | 1439 | O | TYR A | 193 | −12.759 | 0.375 | −85.209 | 1.00 | 31.44 | O |
| ATOM | 1440 | N | GLU A | 194 | −12.283 | 0.703 | −87.385 | 1.00 | 30.63 | N |
| ATOM | 1441 | CA | GLU A | 194 | −10.914 | 0.245 | −87.324 | 1.00 | 30.39 | C |
| ATOM | 1442 | CB | GLU A | 194 | −10.665 | −0.717 | −88.481 | 1.00 | 33.28 | C |
| ATOM | 1443 | CG | GLU A | 194 | −9.698 | −1.856 | −88.210 | 1.00 | 36.64 | C |
| ATOM | 1444 | CD | GLU A | 194 | −9.817 | −2.961 | −89.255 | 1.00 | 39.41 | C |
| ATOM | 1445 | OE1 | GLU A | 194 | −8.951 | −3.035 | −90.165 | 1.00 | 41.19 | O |
| ATOM | 1446 | OE2 | GLU A | 194 | −10.795 | −3.744 | −89.181 | 1.00 | 40.37 | O |

Atomic coordinates for CRBN:DDB1:Lenalidomide (Human protein)

-continued

| | | | Atomic coordinates for CRBN:DDB1:Lenalidomide (Human protein) | | | | | | |
|---|---|---|---|---|---|---|---|---|---|
| ATOM | 1447 | C | GLU A | 194 | −10.081 | 1.493 | −87.506 | 1.00 | 28.80 | C |
| ATOM | 1448 | O | GLU A | 194 | −10.434 | 2.365 | −88.281 | 1.00 | 28.62 | O |
| ATOM | 1449 | N | VAL A | 195 | −8.994 | 1.604 | −86.770 | 1.00 | 27.88 | N |
| ATOM | 1450 | CA | VAL A | 195 | −8.129 | 2.754 | −86.915 | 1.00 | 26.68 | C |
| ATOM | 1451 | CB | VAL A | 195 | −7.591 | 3.243 | −85.559 | 1.00 | 25.80 | C |
| ATOM | 1452 | CG1 | VAL A | 195 | −6.633 | 4.409 | −85.748 | 1.00 | 25.06 | C |
| ATOM | 1453 | CG2 | VAL A | 195 | −8.745 | 3.634 | −84.650 | 1.00 | 25.68 | C |
| ATOM | 1454 | C | VAL A | 195 | −6.987 | 2.318 | −87.782 | 1.00 | 26.77 | C |
| ATOM | 1455 | O | VAL A | 195 | −6.177 | 1.491 | −87.376 | 1.00 | 28.27 | O |
| ATOM | 1456 | N | SER A | 196 | −6.933 | 2.848 | −88.991 | 1.00 | 26.48 | N |
| ATOM | 1457 | CA | SER A | 196 | −5.819 | 2.553 | −89.869 | 1.00 | 26.51 | C |
| ATOM | 1458 | CB | SER A | 196 | −6.175 | 2.892 | −91.319 | 1.00 | 26.66 | C |
| ATOM | 1459 | OG | SER A | 196 | −5.091 | 2.631 | −92.188 | 1.00 | 27.38 | O |
| ATOM | 1460 | C | SER A | 196 | −4.586 | 3.325 | −89.396 | 1.00 | 26.37 | C |
| ATOM | 1461 | O | SER A | 196 | −4.512 | 4.543 | −89.535 | 1.00 | 26.59 | O |
| ATOM | 1462 | N | LEU A | 197 | −3.644 | 2.606 | −88.794 | 1.00 | 26.30 | N |
| ATOM | 1463 | CA | LEU A | 197 | −2.357 | 3.174 | −88.391 | 1.00 | 26.62 | C |
| ATOM | 1464 | CB | LEU A | 197 | −1.436 | 2.058 | −87.892 | 1.00 | 25.98 | C |
| ATOM | 1465 | CG | LEU A | 197 | −1.433 | 1.653 | −86.416 | 1.00 | 26.02 | C |
| ATOM | 1466 | CD1 | LEU A | 197 | −2.704 | 2.057 | −85.684 | 1.00 | 26.04 | C |
| ATOM | 1467 | CD2 | LEU A | 197 | −1.174 | 0.159 | −86.277 | 1.00 | 26.00 | C |
| ATOM | 1468 | C | LEU A | 197 | −1.665 | 3.974 | −89.518 | 1.00 | 27.51 | C |
| ATOM | 1469 | O | LEU A | 197 | −1.223 | 5.110 | −89.298 | 1.00 | 28.12 | O |
| ATOM | 1470 | N | ARG A | 198 | −1.591 | 3.382 | −90.714 | 1.00 | 26.99 | N |
| ATOM | 1471 | CA | ARG A | 198 | −0.976 | 4.019 | −91.888 | 1.00 | 27.63 | C |
| ATOM | 1472 | CB | ARG A | 198 | −0.863 | 2.978 | −93.019 | 1.00 | 27.98 | C |
| ATOM | 1473 | CG | ARG A | 198 | −0.380 | 3.447 | −94.391 | 1.00 | 26.45 | C |
| ATOM | 1474 | CD | ARG A | 198 | −1.111 | 2.639 | −81.324 | 1.00 | 30.15 | C |
| ATOM | 1475 | NE | ARG A | 198 | −0.277 | 2.268 | −96.606 | 1.00 | 26.85 | N |
| ATOM | 1476 | CZ | ARG A | 198 | −0.416 | 2.748 | −97.849 | 1.00 | 26.13 | C |
| ATOM | 1477 | NH1 | ARG A | 198 | −1.361 | 3.650 | −98.127 | 1.00 | 25.69 | N |
| ATOM | 1478 | NH2 | ARG A | 198 | 0.395 | 2.323 | −98.820 | 1.00 | 24.41 | N |
| ATOM | 1479 | C | ARG A | 198 | −1.752 | 5.268 | −92.351 | 1.00 | 28.01 | C |
| ATOM | 1480 | O | ARG A | 198 | −1.227 | 6.384 | −92.349 | 1.00 | 26.73 | O |
| ATOM | 1481 | N | GLU A | 199 | −3.011 | 5.068 | −92.720 | 1.00 | 29.48 | N |
| ATOM | 1482 | CA | GLU A | 199 | −3.837 | 6.136 | −93.273 | 1.00 | 30.76 | C |
| ATOM | 1483 | CB | GLU A | 199 | −5.058 | 5.549 | −94.013 | 1.00 | 33.00 | C |
| ATOM | 1484 | CG | GLU A | 199 | −4.718 | 4.459 | −95.036 | 1.00 | 35.57 | C |
| ATOM | 1485 | CD | GLU A | 199 | −5.941 | 3.774 | −95.657 | 1.00 | 37.42 | C |
| ATOM | 1486 | OE1 | GLU A | 199 | −7.019 | 3.734 | −95.012 | 1.00 | 37.84 | O |
| ATOM | 1487 | OE2 | GLU A | 199 | −5.813 | 3.253 | −96.797 | 1.00 | 37.41 | O |
| ATOM | 1488 | C | GLU A | 199 | −4.278 | 7.154 | −92.208 | 1.00 | 30.22 | C |
| ATOM | 1489 | O | GLU A | 199 | −4.779 | 8.224 | −92.547 | 1.00 | 31.90 | O |
| ATOM | 1490 | N | LYS A | 200 | −4.076 | 6.824 | −90.931 | 1.00 | 28.90 | N |
| ATOM | 1491 | CA | LYS A | 200 | −4.519 | 7.669 | −89.811 | 1.00 | 27.59 | C |
| ATOM | 1492 | CB | LYS A | 200 | −3.641 | 8.911 | −89.681 | 1.00 | 27.26 | C |
| ATOM | 1493 | CG | LYS A | 200 | −2.387 | 8.624 | −88.897 | 1.00 | 27.19 | C |
| ATOM | 1494 | CD | LYS A | 200 | −1.301 | 9.656 | −89.115 | 1.00 | 27.29 | C |
| ATOM | 1495 | CE | LYS A | 200 | 0.046 | 9.004 | −88.861 | 1.00 | 27.37 | C |
| ATOM | 1496 | NZ | LYS A | 200 | 0.112 | 7.658 | −89.517 | 1.00 | 26.79 | N |
| ATOM | 1497 | C | LYS A | 200 | −5.980 | 8.049 | −89.942 | 1.00 | 26.94 | C |
| ATOM | 1498 | O | LYS A | 200 | −6.346 | 9.22 | −89.882 | 1.00 | 26.83 | O |
| ATOM | 1499 | N | GLU A | 201 | −6.813 | 7.034 | −90.118 | 1.00 | 26.14 | N |
| ATOM | 1500 | CA | GLU A | 201 | −8.199 | 7.243 | −90.481 | 1.00 | 25.32 | C |
| ATOM | 1501 | CB | GLU A | 201 | −8.291 | 7.478 | −91.988 | 1.00 | 25.76 | C |
| ATOM | 1502 | CG | GLU A | 201 | −9.435 | 8.383 | −92.389 | 1.00 | 27.20 | C |
| ATOM | 1503 | CD | GLU A | 201 | −9.186 | 9.859 | −92.101 | 1.00 | 28.10 | C |
| ATOM | 1504 | OE1 | GLU A | 201 | −8.167 | 10.423 | −92.578 | 1.00 | 27.31 | O |
| ATOM | 1505 | OE2 | GLU A | 201 | −10.041 | 10.466 | −91.414 | 1.00 | 29.44 | O |
| ATOM | 1506 | C | GLU A | 201 | −9.036 | 6.039 | −90.081 | 1.00 | 23.71 | C |
| ATOM | 1507 | O | GLU A | 201 | −8.505 | 4.959 | −89.832 | 1.00 | 22.65 | O |
| ATOM | 1508 | N | PHE A | 202 | −10.345 | 6.226 | −90.008 | 1.00 | 23.07 | N |
| ATOM | 1509 | CA | PHE A | 202 | −11.218 | 5.115 | −89.686 | 1.00 | 23.55 | C |
| ATOM | 1510 | CB | PHE A | 202 | −12.539 | 5.582 | −89.074 | 1.00 | 23.46 | C |
| ATOM | 1511 | CG | PHE A | 202 | −12.420 | 6.012 | −87.647 | 1.00 | 24.09 | C |
| ATOM | 1512 | CD1 | PHE A | 202 | −11.781 | 5.196 | −86.704 | 1.00 | 24.64 | C |
| ATOM | 1513 | CE1 | PHE A | 202 | −11.667 | 5.599 | −85.380 | 1.00 | 24.17 | C |
| ATOM | 1514 | CZ | PHE A | 202 | −12.188 | 6.819 | −84.987 | 1.00 | 23.65 | C |
| ATOM | 1515 | CE2 | PHE A | 202 | −12.821 | 7.633 | −85.913 | 1.00 | 23.46 | C |
| ATOM | 1516 | CD2 | PHE A | 202 | −12.941 | 7.229 | −87.231 | 1.00 | 23.94 | C |
| ATOM | 1517 | C | PHE A | 202 | −11.471 | 4.224 | −90.887 | 1.00 | 23.84 | C |
| ATOM | 1518 | O | PHE A | 202 | −11.632 | 4.691 | −92.018 | 1.00 | 24.14 | O |
| ATOM | 1519 | N | ASN A | 203 | −11.488 | 2.929 | −90.622 | 1.00 | 24.43 | N |
| ATOM | 1520 | CA | ASN A | 203 | −11.818 | 1.942 | −91.614 | 1.00 | 25.87 | C |
| ATOM | 1521 | CB | ASN A | 203 | −10.677 | 0.926 | −91.750 | 1.00 | 26.41 | C |
| ATOM | 1522 | CG | ASN A | 203 | −9.729 | 1.245 | −92.900 | 1.00 | 27.01 | C |
| ATOM | 1523 | OD1 | ASN A | 203 | −9.238 | 2.370 | −93.044 | 1.00 | 27.27 | O |

-continued

| | | Atomic coordinates for CRBN:DDB1:Lenalidomide (Human protein) | | | | | | | | |
|---|---|---|---|---|---|---|---|---|---|---|
| ATOM | 1524 | ND2 | ASN A | 203 | −9.461 | 0.243 | −93.723 | 1.00 | 27.79 | N |
| ATOM | 1525 | C | ASN A | 203 | −13.109 | 1.249 | −91.219 | 1.00 | 26.46 | C |
| ATOM | 1526 | O | ASN A | 203 | −13.417 | 1.125 | −90.030 | 1.00 | 26.09 | O |
| ATOM | 1527 | N | LYS A | 204 | −13.877 | 0.812 | −92.210 | 1.00 | 27.50 | N |
| ATOM | 1528 | CA | LYS A | 204 | −15.061 | 0.014 | −91.928 | 1.00 | 28.53 | C |
| ATOM | 1529 | CB | LYS A | 204 | −15.606 | −0.606 | −93.216 | 1.00 | 29.27 | C |
| ATOM | 1530 | CG | LYS A | 204 | −16.958 | −1.290 | −93.067 | 1.00 | 29.82 | C |
| ATOM | 1531 | CD | LYS A | 204 | −17.241 | −2.183 | −94.264 | 1.00 | 31.19 | C |
| ATOM | 1532 | CE | LYS A | 204 | −16.315 | −3.397 | −94.291 | 1.00 | 31.96 | C |
| ATOM | 1533 | NZ | LYS A | 204 | −16.005 | −3.824 | −95.687 | 1.00 | 31.84 | N |
| ATOM | 1534 | C | LYS A | 204 | −14.714 | −1.065 | −90.885 | 1.00 | 27.82 | C |
| ATOM | 1535 | O | LYS A | 204 | −13.799 | −1.867 | −91.078 | 1.00 | 26.77 | O |
| ATOM | 1536 | N | GLY A | 205 | −15.422 | −1.044 | −89.764 | 1.00 | 27.76 | N |
| ATOM | 1537 | CA | GLY A | 205 | −15.170 | −2.000 | −88.685 | 1.00 | 28.67 | C |
| ATOM | 1538 | C | GLY A | 205 | −15.764 | −3.386 | −88.904 | 1.00 | 28.70 | C |
| ATOM | 1539 | O | GLY A | 205 | −16.508 | −3.602 | −89.866 | 1.00 | 28.44 | O |
| ATOM | 1540 | N | PRO A | 206 | −15.456 | −4.331 | −87.993 | 1.00 | 28.50 | N |
| ATOM | 1541 | CA | PRO A | 206 | −15.907 | −5.726 | −88.065 | 1.00 | 29.54 | C |
| ATOM | 1542 | CB | PRO A | 206 | −15.412 | −6.326 | −86.740 | 1.00 | 28.82 | C |
| ATOM | 1543 | CG | PRO A | 206 | −14.289 | −5.456 | −86.317 | 1.00 | 28.98 | C |
| ATOM | 1544 | CD | PRO A | 206 | −14.631 | −4.081 | −86.798 | 1.00 | 28.45 | C |
| ATOM | 1545 | C | PRO A | 206 | −17.434 | −5.914 | −88.189 | 1.00 | 31.10 | C |
| ATOM | 1546 | O | PRO A | 206 | −17.883 | −6.866 | −88.840 | 1.00 | 31.00 | O |
| ATOM | 1547 | N | TRP A | 207 | −18.208 | −5.017 | −87.570 | 1.00 | 32.66 | N |
| ATOM | 1548 | CA | TRP A | 207 | −19.661 | −5.166 | −87.439 | 1.00 | 33.85 | C |
| ATOM | 1549 | CB | TRP A | 207 | −19.989 | −6.382 | −86.582 | 1.00 | 33.95 | C |
| ATOM | 1550 | CG | TRP A | 207 | −19.161 | −6.483 | −85.316 | 1.00 | 33.72 | C |
| ATOM | 1551 | CD1 | TRP A | 207 | −17.971 | −7.181 | −85.137 | 1.00 | 33.60 | C |
| ATOM | 1552 | NE1 | TRP A | 207 | −17.508 | −7.041 | −83.852 | 1.00 | 33.99 | N |
| ATOM | 1553 | CE2 | TRP A | 207 | −18.340 | −6.271 | −83.125 | 1.00 | 33.45 | C |
| ATOM | 1554 | CD2 | TRP A | 207 | −19.441 | −5.871 | −84.009 | 1.00 | 33.98 | C |
| ATOM | 1555 | CE3 | TRP A | 207 | −20.455 | −5.061 | −83.502 | 1.00 | 34.90 | C |
| ATOM | 1556 | CZ3 | TRP A | 207 | −20.385 | −4.666 | −82.157 | 1.00 | 34.82 | C |
| ATOM | 1557 | CH2 | TRP A | 207 | −19.322 | −5.065 | −81.328 | 1.00 | 34.52 | C |
| ATOM | 1558 | CZ2 | TRP A | 207 | −18.280 | −5.875 | −81.800 | 1.00 | 33.55 | C |
| ATOM | 1559 | C | TRP A | 207 | −20.310 | −3.949 | −86.829 | 1.00 | 36.06 | C |
| ATOM | 1560 | O | TRP A | 207 | −19.630 | −3.016 | −86.393 | 1.00 | 35.38 | O |
| ATOM | 1561 | N | LYS A | 208 | −21.643 | −3.963 | −86.788 | 1.00 | 37.78 | N |
| ATOM | 1562 | CA | LYS A | 208 | −22.440 | −2.891 | −86.178 | 1.00 | 38.59 | C |
| ATOM | 1563 | CB | LYS A | 208 | −22.447 | −1.632 | −87.064 | 1.00 | 38.30 | C |
| ATOM | 1564 | CG | LYS A | 208 | −23.436 | −1.670 | −88.219 | 1.00 | 37.96 | C |
| ATOM | 1565 | CD | LYS A | 208 | −22.950 | −0.843 | −89.399 | 1.00 | 38.94 | C |
| ATOM | 1566 | CE | LYS A | 208 | −24.014 | −0.798 | −90.485 | 1.00 | 39.77 | C |
| ATOM | 1567 | NZ | LYS A | 208 | −23.473 | −1.005 | −91.857 | 1.00 | 39.49 | N |
| ATOM | 1568 | C | LYS A | 208 | −23.867 | −3.389 | −85.915 | 1.00 | 39.21 | C |
| ATOM | 1569 | O | LYS A | 208 | −24.243 | −4.471 | −86.372 | 1.00 | 38.66 | O |
| ATOM | 1570 | N | GLN A | 209 | −24.655 | −2.600 | −85.183 | 1.00 | 39.76 | N |
| ATOM | 1571 | CA | GLN A | 209 | −26.003 | −3.007 | −84.781 | 1.00 | 39.69 | C |
| ATOM | 1572 | CB | GLN A | 209 | −25.937 | −4.262 | −83.877 | 1.00 | 41.60 | C |
| ATOM | 1573 | CG | GLN A | 209 | −27.036 | −4.432 | −82.831 | 1.00 | 43.27 | C |
| ATOM | 1574 | CD | GLN A | 209 | −28.396 | −4.738 | −83.426 | 1.00 | 42.94 | C |
| ATOM | 1575 | OE1 | GLN A | 209 | −29.162 | −3.822 | −83.742 | 1.00 | 42.95 | O |
| ATOM | 1576 | NE2 | GLN A | 209 | −28.718 | −6.028 | −83.551 | 1.00 | 41.02 | N |
| ATOM | 1577 | C | GLN A | 209 | −26.749 | −1.859 | −84.114 | 1.00 | 37.69 | C |
| ATOM | 1578 | O | GLN A | 209 | −27.763 | −1.399 | −84.630 | 1.00 | 36.15 | O |
| ATOM | 1579 | N | ASN A | 211 | −30.512 | −1.432 | −84.300 | 1.00 | 31.68 | N |
| ATOM | 1580 | CA | ASN A | 211 | −30.771 | −0.409 | −83.303 | 1.00 | 32.92 | C |
| ATOM | 1581 | CB | ASN A | 211 | −32.033 | 0.381 | −83.665 | 1.00 | 31.58 | C |
| ATOM | 1582 | C | ASN A | 211 | −30.886 | −1.015 | −81.895 | 1.00 | 34.40 | C |
| ATOM | 1583 | O | ASN A | 211 | −31.819 | −1.766 | −81.615 | 1.00 | 35.72 | O |
| ATOM | 1584 | N | VAL A | 212 | −29.929 | −0.683 | −81.021 | 1.00 | 34.41 | N |
| ATOM | 1585 | CA | VAL A | 212 | −29.894 | −1.192 | −79.634 | 1.00 | 32.85 | C |
| ATOM | 1586 | CB | VAL A | 212 | −28.534 | −0.919 | −78.946 | 1.00 | 32.03 | C |
| ATOM | 1587 | CG1 | VAL A | 212 | −27.435 | −1.766 | −79.574 | 1.00 | 31.19 | C |
| ATOM | 1588 | CG2 | VAL A | 212 | −28.190 | 0.564 | −78.991 | 1.00 | 30.35 | C |
| ATOM | 1589 | C | VAL A | 212 | −31.006 | −0.603 | −78.768 | 1.00 | 32.29 | C |
| ATOM | 1590 | O | VAL A | 212 | −31.848 | 0.154 | −79.257 | 1.00 | 32.29 | O |
| ATOM | 1591 | N | GLU A | 213 | −31.003 | −0.954 | −77.482 | 1.00 | 31.61 | N |
| ATOM | 1592 | CA | GLU A | 213 | −31.993 | −0.431 | −76.541 | 1.00 | 31.40 | C |
| ATOM | 1593 | CB | GLU A | 213 | −31.747 | −0.988 | −75.144 | 1.00 | 31.73 | C |
| ATOM | 1594 | CG | GLU A | 213 | −32.941 | −0.853 | −74.222 | 1.00 | 33.60 | C |
| ATOM | 1595 | CD | GLU A | 213 | −32.563 | −0.853 | −72.751 | 1.00 | 35.20 | C |
| ATOM | 1596 | OE1 | GLU A | 213 | −31.764 | −1.724 | −72.331 | 1.00 | 35.36 | O |
| ATOM | 1597 | OE2 | GLU A | 213 | −33.080 | 0.021 | −72.014 | 1.00 | 35.65 | O |
| ATOM | 1598 | C | GLU A | 213 | −31.958 | 1.095 | −76.509 | 1.00 | 30.71 | C |
| ATOM | 1599 | O | GLU A | 213 | −30.895 | 1.698 | −76.641 | 1.00 | 31.04 | O |
| ATOM | 1600 | N | ALA A | 214 | −33.126 | 1.710 | −76.337 | 1.00 | 30.32 | N |

-continued

| | | | | | | | | | |
|---|---|---|---|---|---|---|---|---|---|
| ATOM | 1601 | CA | ALA A | 214 | −33.259 | 3.172 | −76.309 | 1.00 | 30.22 | C |
| ATOM | 1602 | CB | ALA A | 214 | −34.678 | 3.559 | −75.933 | 1.00 | 29.33 | C |
| ATOM | 1603 | C | ALA A | 214 | −32.280 | 3.852 | −75.361 | 1.00 | 31.17 | C |
| ATOM | 1604 | O | ALA A | 214 | −31.848 | 4.973 | −75.611 | 1.00 | 31.91 | O |
| ATOM | 1605 | N | GLU A | 215 | −31.929 | 3.158 | −74.283 | 1.00 | 31.76 | N |
| ATOM | 1606 | CA | GLU A | 215 | −31.313 | 3.778 | −73.127 | 1.00 | 31.10 | C |
| ATOM | 1607 | CB | GLU A | 215 | −32.266 | 3.653 | −71.943 | 1.00 | 32.49 | C |
| ATOM | 1608 | CG | GLU A | 215 | −32.093 | 4.723 | −70.880 | 1.00 | 34.34 | C |
| ATOM | 1609 | CD | GLU A | 215 | −32.505 | 6.094 | −71.352 | 1.00 | 34.85 | C |
| ATOM | 1610 | OE1 | GLU A | 215 | −31.677 | 7.028 | −71.219 | 1.00 | 36.66 | O |
| ATOM | 1611 | OE2 | GLU A | 215 | −33.648 | 6.233 | −71.847 | 1.00 | 33.85 | O |
| ATOM | 1612 | C | GLU A | 215 | −29.965 | 3.139 | −72.809 | 1.00 | 30.84 | C |
| ATOM | 1613 | O | GLU A | 215 | −29.317 | 3.473 | −71.811 | 1.00 | 30.20 | O |
| ATOM | 1614 | N | ALA A | 216 | −29.555 | 2.212 | −73.671 | 1.00 | 30.68 | N |
| ATOM | 1615 | CA | ALA A | 216 | −28.214 | 1.635 | −73.639 | 1.00 | 29.99 | C |
| ATOM | 1616 | CB | ALA A | 216 | −27.961 | 0.838 | −74.910 | 1.00 | 29.10 | C |
| ATOM | 1617 | C | ALA A | 216 | −27.189 | 2.746 | −73.506 | 1.00 | 29.69 | C |
| ATOM | 1618 | O | ALA A | 216 | −27.276 | 3.753 | −74.212 | 1.00 | 31.05 | O |
| ATOM | 1619 | N | SER A | 217 | −26.225 | 2.572 | −72.603 | 1.00 | 28.96 | N |
| ATOM | 1620 | CA | SER A | 217 | −25.233 | 3.615 | −72.361 | 1.00 | 28.67 | C |
| ATOM | 1621 | CB | SER A | 217 | −25.764 | 4.615 | −71.348 | 1.00 | 28.16 | C |
| ATOM | 1622 | OG | SER A | 217 | −36.039 | 3.976 | −70.125 | 1.00 | 27.90 | O |
| ATOM | 1623 | C | SER A | 217 | −23.851 | 3.139 | −71.929 | 1.00 | 29.31 | C |
| ATOM | 1624 | O | SER A | 217 | −22.932 | 3.938 | −71.826 | 1.00 | 30.80 | O |
| ATOM | 1625 | N | MET A | 218 | −23.683 | 1.851 | −71.674 | 1.00 | 30.27 | N |
| ATOM | 1626 | CA | MET A | 218 | −22.395 | 1.391 | −71.178 | 1.00 | 30.13 | C |
| ATOM | 1627 | CB | MET A | 218 | −22.529 | 0.872 | −69.763 | 1.00 | 32.83 | C |
| ATOM | 1628 | CG | MET A | 218 | −21.197 | 0.765 | −69.052 | 1.00 | 38.16 | C |
| ATOM | 1629 | SD | MET A | 218 | −21.312 | −0.189 | −67.529 | 1.00 | 45.93 | S |
| ATOM | 1630 | CE | MET A | 218 | −22.435 | 0.857 | −66.599 | 1.00 | 40.00 | C |
| ATOM | 1631 | C | MET A | 218 | −21.756 | 0.341 | −72.072 | 1.00 | 28.53 | C |
| ATOM | 1632 | O | MET A | 218 | −22.355 | −0.683 | −72.370 | 1.00 | 28.48 | O |
| ATOM | 1633 | N | VAL A | 219 | −20.533 | 0.607 | −72.499 | 1.00 | 26.75 | N |
| ATOM | 1634 | CA | VAL A | 219 | −19.814 | −0.330 | −73.338 | 1.00 | 25.90 | C |
| ATOM | 1635 | CB | VAL A | 219 | −19.142 | 0.374 | −74.538 | 1.00 | 26.68 | C |
| ATOM | 1636 | CG1 | VAL A | 219 | −18.560 | −0.655 | −75.501 | 1.00 | 26.66 | C |
| ATOM | 1637 | CG2 | VAL A | 219 | −20.136 | 1.267 | −75.266 | 1.00 | 26.74 | C |
| ATOM | 1638 | C | VAL A | 219 | −18.765 | −1.057 | −72.510 | 1.00 | 24.67 | C |
| ATOM | 1639 | O | VAL A | 219 | −18.037 | −0.436 | −71.737 | 1.00 | 24.45 | O |
| ATOM | 1640 | N | ILE A | 220 | −18.708 | −2.373 | −72.668 | 1.00 | 23.56 | N |
| ATOM | 1641 | CA | ILE A | 220 | −17.724 | −3.196 | −71.984 | 1.00 | 23.46 | C |
| ATOM | 1642 | CB | ILE A | 220 | −18.389 | −4.079 | −70.913 | 1.00 | 23.65 | C |
| ATOM | 1643 | CG1 | ILE A | 220 | −18.909 | −3.216 | −69.751 | 1.00 | 23.94 | C |
| ATOM | 1644 | CD1 | ILE A | 220 | −19.905 | −3.916 | −68.837 | 1.00 | 23.96 | C |
| ATOM | 1645 | CG2 | ILE A | 220 | −17.423 | −5.150 | −70.427 | 1.00 | 23.22 | C |
| ATOM | 1646 | C | ILE A | 220 | −17.038 | −4.082 | −73.010 | 1.00 | 23.66 | C |
| ATOM | 1647 | O | ILE A | 220 | −17.693 | −4.865 | −73.697 | 1.00 | 24.86 | O |
| ATOM | 1648 | N | ALA A | 221 | −15.724 | −3.954 | −73.134 | 1.00 | 23.10 | N |
| ATOM | 1649 | CA | ALA A | 221 | −14.987 | −4.787 | −74.065 | 1.00 | 23.40 | C |
| ATOM | 1650 | CB | ALA A | 221 | −13.799 | −4.033 | −74.630 | 1.00 | 22.94 | C |
| ATOM | 1651 | C | ALA A | 221 | −14.553 | −6.098 | −73.390 | 1.00 | 24.47 | C |
| ATOM | 1652 | O | ALA A | 221 | −13.815 | −6.104 | −72.393 | 1.00 | 24.74 | O |
| ATOM | 1653 | N | VAL A | 222 | −15.045 | −7.207 | −73.923 | 1.00 | 24.96 | N |
| ATOM | 1654 | CA | VAL A | 222 | −14.801 | −8.510 | −73.339 | 1.00 | 25.78 | C |
| ATOM | 1655 | CB | VAL A | 222 | −15.947 | −9.470 | −73.688 | 1.00 | 25.88 | C |
| ATOM | 1656 | CG1 | VAL A | 222 | −15.716 | −10.838 | −73.081 | 1.00 | 27.48 | C |
| ATOM | 1657 | CG2 | VAL A | 222 | −17.275 | −8.905 | −73.213 | 1.00 | 25.16 | C |
| ATOM | 1658 | C | VAL A | 222 | −13.472 | −9.032 | −73.874 | 1.00 | 27.25 | C |
| ATOM | 1659 | O | VAL A | 222 | −13.223 | −8.940 | −75.082 | 1.00 | 28.38 | O |
| ATOM | 1660 | N | PRO A | 223 | −12.600 | −9.553 | −72.983 | 1.00 | 28.37 | N |
| ATOM | 1661 | CA | PRO A | 223 | −11.277 | −10.032 | −73.387 | 1.00 | 30.57 | C |
| ATOM | 1662 | CB | PRO A | 223 | −10.579 | −10.311 | −72.050 | 1.00 | 28.69 | C |
| ATOM | 1663 | CG | PRO A | 223 | −11.289 | −9.458 | −71.077 | 1.00 | 28.92 | C |
| ATOM | 1664 | CD | PRO A | 223 | −12.718 | −9.520 | −71.518 | 1.00 | 29.13 | C |
| ATOM | 1665 | C | PRO A | 223 | −11.283 | −11.293 | −74.261 | 1.00 | 34.13 | C |
| ATOM | 1666 | O | PRO A | 223 | −12.342 | −11.788 | −74.666 | 1.00 | 33.68 | O |
| ATOM | 1667 | N | GLU A | 224 | −10.087 | −11.803 | −74.528 | 1.00 | 38.30 | N |
| ATOM | 1668 | CA | GLU A | 224 | −9.901 | −12.868 | −75.488 | 1.00 | 42.84 | C |
| ATOM | 1669 | CB | GLU A | 224 | −8.548 | −12.730 | −76.194 | 1.00 | 44.92 | C |
| ATOM | 1670 | CG | GLU A | 224 | −8.657 | −12.522 | −77.691 | 1.00 | 47.93 | C |
| ATOM | 1671 | CD | GLU A | 224 | −7.316 | −12.619 | −78.388 | 1.00 | 51.61 | C |
| ATOM | 1672 | OE1 | GLU A | 224 | −7.305 | −12.810 | −79.623 | 1.00 | 54.35 | O |
| ATOM | 1673 | OE2 | GLU A | 224 | −6.272 | −12.507 | −77.705 | 1.00 | 53.67 | O |
| ATOM | 1674 | C | GLU A | 224 | −10.049 | −14.286 | −74.961 | 1.00 | 45.23 | C |
| ATOM | 1675 | O | GLU A | 224 | −9.109 | −14.868 | −74.415 | 1.00 | 50.26 | O |
| ATOM | 1676 | N | PRO A | 225 | −11.268 | −14.796 | −74.999 | 1.00 | 45.04 | N |
| ATOM | 1677 | CA | PRO A | 225 | −11.436 | −15.922 | −75.892 | 1.00 | 42.48 | C |

Atomic coordinates for CRBN:DDB1:Lenalidomide (Human protein)

-continued

| | | | Atomic coordinates for CRBN:DDB1:Lenalidomide (Human protein) | | | | | | |
|---|---|---|---|---|---|---|---|---|---|
| ATOM | 1678 | CB | PRO A | 225 | −11.815 | −17.084 | −74.957 | 1.00 | 41.54 | C |
| ATOM | 1679 | CG | PRO A | 225 | −11.974 | −16.486 | −73.586 | 1.00 | 44.50 | C |
| ATOM | 1680 | CD | PRO A | 225 | −12.032 | −14.987 | −73.759 | 1.00 | 45.55 | C |
| ATOM | 1681 | C | PRO A | 225 | −12.585 | −15.518 | −76.814 | 1.00 | 40.96 | C |
| ATOM | 1682 | O | PRO A | 225 | −12.447 | −15.550 | −78.029 | 1.00 | 40.45 | O |
| ATOM | 1683 | N | PHE A | 226 | −13.675 | −15.046 | −76.214 | 1.00 | 40.06 | N |
| ATOM | 1684 | CA | PHE A | 226 | −14.888 | −14.695 | −76.931 | 1.00 | 39.76 | C |
| ATOM | 1685 | CB | PHE A | 226 | −16.083 | −14.667 | −75.969 | 1.00 | 43.33 | C |
| ATOM | 1686 | CG | PHE A | 226 | −16.157 | −15.861 | −75.049 | 1.00 | 47.14 | C |
| ATOM | 1687 | CD1 | PHE A | 226 | −16.045 | −17.161 | −75.549 | 1.00 | 48.45 | C |
| ATOM | 1688 | CE1 | PHE A | 226 | −16.105 | −18.260 | −74.700 | 1.00 | 49.77 | C |
| ATOM | 1689 | CZ | PHE A | 226 | −16.299 | −18.075 | −73.339 | 1.00 | 50.79 | C |
| ATOM | 1690 | CE2 | PHE A | 226 | −16.421 | −16.789 | −72.827 | 1.00 | 51.35 | C |
| ATOM | 1691 | CD2 | PHE A | 226 | −16.350 | −15.690 | −73.681 | 1.00 | 50.20 | C |
| ATOM | 1692 | C | PHE A | 226 | −14.776 | −13.365 | −77.661 | 1.00 | 37.65 | C |
| ATOM | 1693 | O | PHE A | 226 | −15.412 | −13.170 | −78.699 | 1.00 | 37.27 | O |
| ATOM | 1694 | N | GLY A | 227 | −13.966 | −12.455 | −77.118 | 1.00 | 36.18 | N |
| ATOM | 1695 | CA | GLY A | 227 | −13.897 | −11.078 | −77.612 | 1.00 | 32.64 | C |
| ATOM | 1696 | C | GLY A | 227 | −15.278 | −10.447 | −77.616 | 1.00 | 31.15 | C |
| ATOM | 1697 | O | GLY A | 227 | −16.182 | −10.898 | −76.912 | 1.00 | 31.68 | O |
| ATOM | 1698 | N | GLY A | 228 | −15.449 | −9.403 | −78.411 | 1.00 | 29.35 | N |
| ATOM | 1699 | CA | GLY A | 228 | −16.759 | −8.771 | −78.558 | 1.00 | 27.00 | C |
| ATOM | 1700 | C | GLY A | 228 | −17.058 | −7.701 | −77.531 | 1.00 | 25.20 | C |
| ATOM | 1701 | O | GLY A | 228 | −16.173 | −7.269 | −76.783 | 1.00 | 25.26 | O |
| ATOM | 1702 | N | ALA A | 229 | −18.311 | −7.266 | −77.504 | 1.00 | 23.57 | N |
| ATOM | 1703 | CA | ALA A | 229 | −18.716 | −6.191 | −76.622 | 1.00 | 22.36 | C |
| ATOM | 1704 | CB | ALA A | 229 | −18.875 | −4.903 | −77.411 | 1.00 | 21.89 | C |
| ATOM | 1705 | C | ALA A | 229 | −20.009 | −6.527 | −75.895 | 1.00 | 22.21 | C |
| ATOM | 1706 | O | ALA A | 229 | −20.910 | −7.162 | −76.459 | 1.00 | 22.38 | O |
| ATOM | 1707 | N | ILE A | 230 | −20.087 | −6.101 | −74.637 | 1.00 | 21.80 | N |
| ATOM | 1708 | CA | ILE A | 230 | −21.324 | −6.132 | −73.868 | 1.00 | 21.72 | C |
| ATOM | 1709 | CB | ILE A | 230 | −21.063 | −6.683 | −72.455 | 1.00 | 21.75 | C |
| ATOM | 1710 | CG1 | ILE A | 230 | −20.922 | −8.199 | −72.523 | 1.00 | 21.59 | C |
| ATOM | 1711 | CD1 | ILE A | 230 | −20.459 | −8.817 | −71.233 | 1.00 | 21.82 | C |
| ATOM | 1712 | CG2 | ILE A | 230 | −22.178 | −6.299 | −71.488 | 1.00 | 21.71 | C |
| ATOM | 1713 | C | ILE A | 230 | −21.888 | −4.719 | −73.792 | 1.00 | 21.79 | C |
| ATOM | 1714 | O | ILE A | 230 | −21.130 | −3.762 | −73.629 | 1.00 | 21.97 | O |
| ATOM | 1715 | N | ILE A | 231 | −23.209 | −4.590 | −73.924 | 1.00 | 21.67 | N |
| ATOM | 1716 | CA | ILE A | 231 | −23.881 | −3.293 | −73.807 | 1.00 | 22.17 | C |
| ATOM | 1717 | CB | ILE A | 231 | −24.546 | −2.845 | −75.142 | 1.00 | 21.62 | C |
| ATOM | 1718 | CG1 | ILE A | 231 | −23.565 | −2.904 | −76.321 | 1.00 | 21.68 | C |
| ATOM | 1719 | CD1 | ILE A | 231 | −22.327 | −2.039 | −76.188 | 1.00 | 21.31 | C |
| ATOM | 1720 | CG2 | ILE A | 231 | −25.125 | −1.447 | −75.015 | 1.00 | 21.49 | C |
| ATOM | 1721 | C | ILE A | 231 | −24.934 | −3.320 | −72.696 | 1.00 | 23.01 | C |
| ATOM | 1722 | O | ILE A | 231 | −25.899 | −4.072 | −72.770 | 1.00 | 23.93 | O |
| ATOM | 1723 | N | ILE A | 232 | −24.746 | −2.501 | −71.668 | 1.00 | 23.83 | N |
| ATOM | 1724 | CA | ILE A | 232 | −25.734 | −2.376 | −70.596 | 1.00 | 24.82 | C |
| ATOM | 1725 | CB | ILE A | 232 | −25.052 | −2.112 | −69.231 | 1.00 | 24.87 | C |
| ATOM | 1726 | CG1 | ILE A | 232 | −23.901 | −3.097 | −68.972 | 1.00 | 24.65 | C |
| ATOM | 1727 | CD1 | ILE A | 232 | −24.326 | −4.511 | −68.626 | 1.00 | 24.13 | C |
| ATOM | 1728 | CG2 | ILE A | 232 | −26.070 | −2.142 | −68.096 | 1.00 | 24.97 | C |
| ATOM | 1729 | C | ILE A | 232 | −26.695 | −1.223 | −70.904 | 1.00 | 26.09 | C |
| ATOM | 1730 | O | ILE A | 232 | −26.255 | −0.152 | −71.322 | 1.00 | 25.85 | O |
| ATOM | 1731 | N | GLY A | 233 | −27.997 | −1.449 | −70.694 | 1.00 | 27.62 | N |
| ATOM | 1732 | CA | GLY A | 233 | −29.029 | −0.409 | −70.855 | 1.00 | 29.52 | C |
| ATOM | 1733 | C | GLY A | 233 | −29.906 | −0.204 | −69.624 | 1.00 | 32.48 | C |
| ATOM | 1734 | O | GLY A | 233 | −29.444 | −0.321 | −68.491 | 1.00 | 33.12 | O |
| ATOM | 1735 | N | GLN A | 234 | −31.178 | 0.113 | −69.841 | 1.00 | 35.79 | N |
| ATOM | 1736 | CA | GLN A | 234 | −32.116 | 0.288 | −68.733 | 1.00 | 38.37 | C |
| ATOM | 1737 | CB | GLN A | 234 | −33.232 | 1.263 | −69.090 | 1.00 | 41.39 | C |
| ATOM | 1738 | CG | GLN A | 234 | −33.113 | 2.613 | −68.400 | 1.00 | 44.93 | C |
| ATOM | 1739 | CD | GLN A | 234 | −33.858 | 2.666 | −67.086 | 1.00 | 47.29 | C |
| ATOM | 1740 | OE1 | GLN A | 234 | −33.257 | 2.567 | −66.013 | 1.00 | 49.39 | O |
| ATOM | 1741 | NE2 | GLN A | 234 | −35.181 | 2.819 | −67.161 | 1.00 | 47.35 | N |
| ATOM | 1742 | C | GLN A | 234 | −32.704 | −1.019 | −68.263 | 1.00 | 40.13 | C |
| ATOM | 1743 | O | GLN A | 234 | −32.795 | −1.245 | −67.055 | 1.00 | 40.62 | O |
| ATOM | 1744 | N | GLU A | 235 | −33.126 | −1.871 | −69.201 | 1.00 | 41.75 | N |
| ATOM | 1745 | CA | GLU A | 235 | −33.531 | −3.234 | −68.830 | 1.00 | 43.55 | C |
| ATOM | 1746 | CB | GLU A | 235 | −35.061 | −3.418 | −68.786 | 1.00 | 47.09 | C |
| ATOM | 1747 | CG | GLU A | 235 | −35.462 | −4.694 | −68.027 | 1.00 | 49.80 | C |
| ATOM | 1748 | CD | GLU A | 235 | −36.888 | −4.696 | −67.505 | 1.00 | 52.00 | C |
| ATOM | 1749 | OE1 | GLU A | 235 | −37.633 | −5.640 | −67.845 | 1.00 | 52.60 | O |
| ATOM | 1750 | OE2 | GLU A | 235 | −37.259 | −3.774 | −66.740 | 1.00 | 52.21 | O |
| ATOM | 1751 | C | GLU A | 235 | −32.869 | −4.360 | −69.625 | 1.00 | 41.20 | C |
| ATOM | 1752 | O | GLU A | 235 | −33.101 | −5.542 | −69.341 | 1.00 | 41.06 | O |
| ATOM | 1753 | N | SER A | 236 | −32.036 | −4.014 | −70.598 | 1.00 | 36.56 | N |
| ATOM | 1754 | CA | SER A | 236 | −31.339 | −5.056 | −71.341 | 1.00 | 32.91 | C |

| | | | | | | | | | |
|---|---|---|---|---|---|---|---|---|---|
| | Atomic coordinates for CRBN:DDB1:Lenalidomide (Human protein) |
| ATOM | 1755 | CB | SER A | 236 | −31.773 | −5.108 | −72.811 | 1.00 | 32.30 | C |
| ATOM | 1756 | OG | SER A | 236 | −32.425 | −3.921 | −73.204 | 1.00 | 32.43 | O |
| ATOM | 1757 | C | SER A | 236 | −29.827 | −5.013 | −71.206 | 1.00 | 30.49 | C |
| ATOM | 1758 | O | SER A | 236 | −29.220 | −3.948 | −71.091 | 1.00 | 31.15 | O |
| ATOM | 1759 | N | ILE A | 237 | −29.244 | −6.203 | −71.185 | 1.00 | 27.70 | N |
| ATOM | 1760 | CA | ILE A | 237 | −27.811 | −6.398 | −71.239 | 1.00 | 25.90 | C |
| ATOM | 1761 | CB | ILE A | 237 | −27.313 | −7.108 | −69.957 | 1.00 | 24.12 | C |
| ATOM | 1762 | CG1 | ILE A | 237 | −27.414 | −6.155 | −68.777 | 1.00 | 23.51 | C |
| ATOM | 1763 | CD1 | ILE A | 237 | −27.319 | −6.827 | −67.436 | 1.00 | 23.62 | C |
| ATOM | 1764 | CG2 | ILE A | 237 | −25.885 | −7.594 | −70.099 | 1.00 | 23.58 | C |
| ATOM | 1765 | C | ILE A | 237 | −27.613 | −7.246 | −72.485 | 1.00 | 25.70 | C |
| ATOM | 1766 | O | ILE A | 237 | −28.253 | −8.282 | −72.630 | 1.00 | 26.10 | O |
| ATOM | 1767 | N | THR A | 238 | −26.759 | −6.789 | −73.394 | 1.00 | 26.10 | N |
| ATOM | 1768 | CA | THR A | 238 | −26.696 | −7.352 | −74.747 | 1.00 | 28.01 | C |
| ATOM | 1769 | CB | THR A | 238 | −27.337 | −6.399 | −75.794 | 1.00 | 29.62 | C |
| ATOM | 1770 | OG1 | THR A | 238 | −28.498 | −5.758 | −75.242 | 1.00 | 30.87 | O |
| ATOM | 1771 | CG2 | THR A | 238 | −27.750 | −7.167 | −77.028 | 1.00 | 30.15 | C |
| ATOM | 1772 | C | THR A | 238 | −25.263 | −7.617 | −75.174 | 1.00 | 27.71 | C |
| ATOM | 1773 | O | THR A | 238 | −24.378 | −6.804 | −74.921 | 1.00 | 29.31 | O |
| ATOM | 1774 | N | TYR A | 239 | −25.033 | −8.745 | −75.835 | 1.00 | 27.10 | N |
| ATOM | 1775 | CA | TYR A | 239 | −23.692 | −9.089 | −76.289 | 1.00 | 27.50 | C |
| ATOM | 1776 | CB | TYR A | 239 | −23.246 | −10.438 | −75.730 | 1.00 | 26.88 | C |
| ATOM | 1777 | CG | TYR A | 239 | −21.961 | −10.936 | −76.336 | 1.00 | 26.37 | C |
| ATOM | 1778 | CD1 | TYR A | 239 | −20.741 | −10.537 | −75.831 | 1.00 | 26.77 | C |
| ATOM | 1779 | CE1 | TYR A | 239 | −19.553 | −10.984 | −76.384 | 1.00 | 26.80 | C |
| ATOM | 1780 | CZ | TYR A | 239 | −19.578 | −11.835 | −77.461 | 1.00 | 26.27 | C |
| ATOM | 1781 | OH | TYR A | 239 | −18.390 | −12.268 | −78.002 | 1.00 | 25.46 | O |
| ATOM | 1782 | CE2 | TYR A | 239 | −20.784 | −12.245 | −77.990 | 1.00 | 26.75 | C |
| ATOM | 1783 | CD2 | TYR A | 239 | −21.967 | −11.797 | −77.426 | 1.00 | 26.73 | C |
| ATOM | 1784 | C | TYR A | 239 | −23.613 | −9.109 | −77.803 | 1.00 | 28.89 | C |
| ATOM | 1785 | O | TYR A | 239 | −24.563 | −9.540 | −78.470 | 1.00 | 29.54 | O |
| ATOM | 1786 | N | HIS A | 240 | −22.470 | −8.654 | −78.331 | 1.00 | 28.93 | N |
| ATOM | 1787 | CA | HIS A | 240 | −22.222 | −8.596 | −79.771 | 1.00 | 28.64 | C |
| ATOM | 1788 | CB | HIS A | 240 | −22.455 | −7.185 | −80.300 | 1.00 | 28.37 | C |
| ATOM | 1789 | CG | HIS A | 240 | −23.602 | −6.472 | −79.643 | 1.00 | 28.79 | C |
| ATOM | 1790 | ND1 | HIS A | 240 | −24.851 | −6.508 | −80.135 | 1.00 | 29.65 | N |
| ATOM | 1791 | CE1 | HIS A | 240 | −25.668 | −5.794 | −79.338 | 1.00 | 29.46 | C |
| ATOM | 1792 | NE2 | HIS A | 240 | −24.936 | −5.305 | −78.323 | 1.00 | 29.32 | N |
| ATOM | 1793 | CD2 | HIS A | 240 | −23.658 | −5.704 | −78.481 | 1.00 | 28.87 | C |
| ATOM | 1794 | C | HIS A | 240 | −20.814 | −8.990 | −80.085 | 1.00 | 29.37 | C |
| ATOM | 1795 | O | HIS A | 240 | −19.876 | −8.590 | −79.391 | 1.00 | 30.12 | O |
| ATOM | 1796 | N | ASN A | 241 | −20.660 | −9.785 | −81.137 | 1.00 | 29.55 | N |
| ATOM | 1797 | CA | ASN A | 241 | −19.370 | −10.034 | −81.782 | 1.00 | 30.91 | C |
| ATOM | 1798 | CB | ASN A | 241 | −18.509 | −11.031 | −80.995 | 1.00 | 29.37 | C |
| ATOM | 1799 | CG | ASN A | 241 | −17.085 | −11.150 | −81.542 | 1.00 | 28.87 | C |
| ATOM | 1800 | OD1 | ASN A | 241 | −16.738 | −10.558 | −82.566 | 1.00 | 28.82 | O |
| ATOM | 1801 | ND2 | ASN A | 241 | −16.248 | −11.910 | −80.843 | 1.00 | 29.00 | N |
| ATOM | 1802 | C | ASN A | 241 | −19.651 | −10.588 | −83.157 | 1.00 | 33.90 | C |
| ATOM | 1803 | O | ASN A | 241 | −20.477 | −11.499 | −83.308 | 1.00 | 36.55 | O |
| ATOM | 1804 | N | GLY A | 242 | −18.966 | −10.058 | −84.166 | 1.00 | 35.94 | N |
| ATOM | 1805 | CA | GLY A | 242 | −19.284 | −10.422 | −85.532 | 1.00 | 37.89 | C |
| ATOM | 1806 | C | GLY A | 242 | −20.793 | −10.387 | −85.585 | 1.00 | 39.80 | C |
| ATOM | 1807 | O | GLY A | 242 | −21.406 | −9.370 | −85.228 | 1.00 | 39.92 | O |
| ATOM | 1808 | N | ASP A | 243 | −21.406 | −11.507 | −85.951 | 1.00 | 41.08 | N |
| ATOM | 1809 | CA | ASP A | 243 | −22.867 | −11.538 | −86.011 | 1.00 | 43.07 | C |
| ATOM | 1810 | CB | ASP A | 243 | −23.369 | −11.639 | −87.467 | 1.00 | 45.40 | C |
| ATOM | 1811 | CG | ASP A | 243 | −23.229 | −10.298 | −88.236 | 1.00 | 49.13 | C |
| ATOM | 1812 | OD1 | ASP A | 243 | −22.105 | −9.729 | −88.302 | 1.00 | 48.25 | O |
| ATOM | 1813 | OD2 | ASP A | 243 | −24.249 | −9.809 | −88.776 | 1.00 | 50.45 | O |
| ATOM | 1814 | C | ASP A | 243 | −23.544 | −12.526 | −85.039 | 1.00 | 41.42 | C |
| ATOM | 1815 | O | ASP A | 243 | −24.722 | −12.854 | −85.189 | 1.00 | 40.42 | O |
| ATOM | 1816 | N | LYS A | 244 | −22.795 | −12.962 | −84.025 | 1.00 | 40.38 | N |
| ATOM | 1817 | CA | LYS A | 244 | −23.392 | −13.549 | −82.822 | 1.00 | 39.22 | C |
| ATOM | 1818 | CB | LYS A | 244 | −22.329 | −14.204 | −81.943 | 1.00 | 39.54 | C |
| ATOM | 1819 | CG | LYS A | 244 | −22.909 | −15.082 | −80.841 | 1.00 | 40.32 | C |
| ATOM | 1820 | CD | LYS A | 244 | −21.827 | −15.601 | −79.909 | 1.00 | 41.13 | C |
| ATOM | 1821 | CE | LYS A | 244 | −21.861 | −17.121 | −79.830 | 1.00 | 41.84 | C |
| ATOM | 1822 | NZ | LYS A | 244 | −23.246 | −17.642 | −79.641 | 1.00 | 42.76 | N |
| ATOM | 1823 | C | LYS A | 244 | −24.095 | −12.437 | −82.033 | 1.00 | 37.58 | C |
| ATOM | 1824 | O | LYS A | 244 | −23.708 | −11.267 | −82.125 | 1.00 | 37.70 | O |
| ATOM | 1825 | N | TYR A | 245 | −25.112 | −12.803 | −81.254 | 1.00 | 34.72 | N |
| ATOM | 1826 | CA | TYR A | 245 | −25.930 | −11.819 | −80.555 | 1.00 | 33.47 | C |
| ATOM | 1827 | CB | TYR A | 245 | −26.822 | −11.082 | −81.554 | 1.00 | 33.15 | C |
| ATOM | 1828 | CG | TYR A | 245 | −27.835 | −10.160 | −80.943 | 1.00 | 33.23 | C |
| ATOM | 1829 | CD1 | TYR A | 245 | −29.101 | −10.622 | −80.594 | 1.00 | 33.25 | C |
| ATOM | 1830 | CE1 | TYR A | 245 | −30.052 | −9.778 | −80.044 | 1.00 | 33.68 | C |
| ATOM | 1831 | CZ | TYR A | 245 | −29.749 | −8.445 | −79.845 | 1.00 | 34.55 | C |

-continued

| \multicolumn{10}{c}{Atomic coordinates for CRBN:DDB1:Lenalidomide (Human protein)} |

| ATOM | 1832 | OH | TYR A | 245 | −30.698 | −7.605 | −79.289 | 1.00 | 33.85 | O |
|---|---|---|---|---|---|---|---|---|---|---|
| ATOM | 1832 | OH | TYR A | 245 | −30.698 | −7.605 | −79.289 | 1.00 | 33.85 | O |
| ATOM | 1833 | CE2 | TYR A | 245 | −28.494 | −7.958 | −80.194 | 1.00 | 35.67 | C |
| ATOM | 1834 | CD2 | TYR A | 245 | −27.546 | −8.818 | −80.742 | 1.00 | 34.48 | C |
| ATOM | 1835 | C | TYR A | 245 | −26.764 | −12.450 | −79.446 | 1.00 | 33.17 | C |
| ATOM | 1836 | O | TYR A | 245 | −27.569 | −13.349 | −79.687 | 1.00 | 32.82 | O |
| ATOM | 1837 | N | LEU A | 246 | −26.555 | −11.967 | −78.225 | 1.00 | 33.25 | N |
| ATOM | 1838 | CA | LEU A | 246 | −27.256 | −12.472 | −77.46 | 1.00 | 32.52 | C |
| ATOM | 1839 | CB | LEU A | 246 | −26.275 | −13.162 | −76.096 | 1.00 | 32.21 | C |
| ATOM | 1840 | CG | LEU A | 246 | −25.865 | −14.620 | −76.369 | 1.00 | 32.65 | C |
| ATOM | 1841 | CD1 | LEU A | 246 | −25.224 | −14.834 | −77.734 | 1.00 | 33.00 | C |
| ATOM | 1842 | CD2 | LEU A | 246 | −24.914 | −15.095 | −75.283 | 1.00 | 34.04 | C |
| ATOM | 1843 | C | LEU A | 246 | −27.941 | −11.310 | −76.349 | 1.00 | 31.84 | C |
| ATOM | 1844 | O | LEU A | 246 | −27.392 | −10.208 | −76.305 | 1.00 | 32.66 | O |
| ATOM | 1845 | N | ALA A | 247 | −29.145 | −11.549 | −75.829 | 1.00 | 30.72 | N |
| ATOM | 1846 | CA | ALA A | 247 | −29.947 | −10.486 | −75.210 | 1.00 | 29.56 | C |
| ATOM | 1847 | CB | ALA A | 247 | −30.870 | −9.843 | −76.234 | 1.00 | 29.19 | C |
| ATOM | 1848 | C | ALA A | 247 | −30.753 | −10.986 | −74.024 | 1.00 | 28.47 | C |
| ATOM | 1849 | O | ALA A | 247 | −31.720 | −11.717 | −74.196 | 1.00 | 29.21 | O |
| ATOM | 1850 | N | ILE A | 248 | −30.339 | −10.603 | −72.820 | 1.00 | 27.16 | N |
| ATOM | 1851 | CA | ILE A | 248 | −31.151 | −10.836 | −71.629 | 1.00 | 26.11 | C |
| ATOM | 1852 | CB | ILE A | 248 | −30.360 | −11.485 | −70.470 | 1.00 | 25.38 | C |
| ATOM | 1853 | CG1 | ILE A | 248 | −29.053 | −10.735 | −70.225 | 1.00 | 24.83 | C |
| ATOM | 1854 | CD1 | ILE A | 248 | −28.634 | −10.745 | −68.777 | 1.00 | 24.76 | C |
| ATOM | 1855 | CG2 | ILE A | 248 | −30.126 | −12.970 | −70.738 | 1.00 | 24.96 | C |
| ATOM | 1856 | C | ILE A | 248 | −31.769 | −9.534 | −71.147 | 1.00 | 25.49 | C |
| ATOM | 1857 | O | ILE A | 248 | −31.159 | −8.464 | −71.257 | 1.00 | 25.31 | O |
| ATOM | 1858 | N | ALA A | 249 | −32.986 | −9.642 | −70.622 | 1.00 | 24.53 | N |
| ATOM | 1859 | CA | ALA A | 249 | −33.699 | −8.517 | −70.040 | 1.00 | 23.38 | C |
| ATOM | 1860 | CB | ALA A | 249 | −34.798 | −8.053 | −70.978 | 1.00 | 23.47 | C |
| ATOM | 1861 | C | ALA A | 249 | −34.279 | −8.929 | −68.691 | 1.00 | 22.58 | C |
| ATOM | 1862 | O | ALA A | 249 | −35.496 | −9.027 | −68.544 | 1.00 | 22.59 | O |
| ATOM | 1863 | N | PRO A | 250 | −33.406 | −9.165 | −67.694 | 1.00 | 22.02 | N |
| ATOM | 1864 | CA | PRO A | 250 | −33.877 | −9.706 | −66.425 | 1.00 | 21.88 | C |
| ATOM | 1865 | CB | PRO A | 250 | −32.582 | −10.102 | −65.712 | 1.00 | 21.75 | C |
| ATOM | 1866 | CG | PRO A | 250 | −31.556 | −9.168 | −66.248 | 1.00 | 21.66 | C |
| ATOM | 1867 | CD | PRO A | 250 | −31.974 | −8.806 | −67.648 | 1.00 | 22.03 | C |
| ATOM | 1868 | C | PRO A | 250 | −34.659 | −8.681 | −65.604 | 1.00 | 22.12 | C |
| ATOM | 1869 | O | PRO A | 250 | −34.466 | −7.475 | −65.774 | 1.00 | 21.78 | O |
| ATOM | 1870 | N | PRO A | 251 | −35.561 | −9.160 | −64.731 | 1.00 | 22.74 | N |
| ATOM | 1871 | CA | PRO A | 251 | −36.336 | −8.265 | −63.869 | 1.00 | 23.00 | C |
| ATOM | 1872 | CB | PRO A | 251 | −37.398 | −9.198 | −63.251 | 1.00 | 22.64 | C |
| ATOM | 1873 | CG | PRO A | 251 | −37.399 | −10.422 | −64.092 | 1.00 | 22.33 | C |
| ATOM | 1874 | CD | PRO A | 251 | −35.990 | −10.561 | −64.582 | 1.00 | 22.62 | C |
| ATOM | 1875 | C | PRO A | 251 | −35.481 | −7.650 | −62.762 | 1.00 | 23.03 | C |
| ATOM | 1876 | O | PRO A | 251 | −35.781 | −6.562 | −62.270 | 1.00 | 24.12 | O |
| ATOM | 1877 | N | ILE A | 252 | −34.418 | −8.342 | −62.382 | 1.00 | 22.49 | N |
| ATOM | 1878 | CA | ILE A | 252 | −33.638 | −7.952 | −61.222 | 1.00 | 22.44 | C |
| ATOM | 1879 | CB | ILE A | 252 | −32.761 | −9.136 | −60.741 | 1.00 | 21.90 | C |
| ATOM | 1880 | CG1 | ILE A | 252 | −32.724 | −9.198 | −59.219 | 1.00 | 21.21 | C |
| ATOM | 1881 | CD1 | ILE A | 252 | −32.179 | −10.503 | −58.707 | 1.00 | 21.87 | C |
| ATOM | 1882 | CG2 | ILE A | 252 | −31.373 | −9.125 | −61.382 | 1.00 | 21.56 | C |
| ATOM | 1883 | C | ILE A | 252 | −32.837 | −6.650 | −61.455 | 1.00 | 23.23 | C |
| ATOM | 1884 | O | ILE A | 252 | −32.334 | −6.036 | −60.503 | 1.00 | 22.56 | O |
| ATOM | 1885 | N | ILE A | 253 | −32.744 | −6.222 | −62.717 | 1.00 | 23.77 | N |
| ATOM | 1886 | CA | ILE A | 253 | −32.165 | −4.914 | −63.039 | 1.00 | 24.15 | C |
| ATOM | 1887 | CB | ILE A | 253 | −30.978 | −4.999 | −64.043 | 1.00 | 24.40 | C |
| ATOM | 1888 | CG1 | ILE A | 253 | −31.471 | −5.275 | −65.474 | 1.00 | 24.83 | C |
| ATOM | 1889 | CD1 | ILE A | 253 | −30.577 | −4.711 | −66.557 | 1.00 | 24.45 | C |
| ATOM | 1890 | CG2 | ILE A | 253 | −29.940 | −6.016 | −63.577 | 1.00 | 23.82 | C |
| ATOM | 1891 | C | ILE A | 253 | −33.213 | −3.893 | −63.512 | 1.00 | 24.41 | C |
| ATOM | 1892 | O | ILE A | 253 | −32.863 | −2.798 | −63.969 | 1.00 | 24.36 | O |
| ATOM | 1893 | N | LYS A | 254 | −34.492 | −4.244 | −63.385 | 1.00 | 25.10 | N |
| ATOM | 1894 | CA | LYS A | 254 | −35.577 | −3.327 | −63.755 | 1.00 | 26.73 | C |
| ATOM | 1895 | CB | LYS A | 254 | −36.947 | −3.994 | −63.580 | 1.00 | 26.05 | C |
| ATOM | 1896 | C | LYS A | 254 | −35.505 | −2.043 | −62.927 | 1.00 | 27.36 | C |
| ATOM | 1897 | O | LYS A | 254 | −35.529 | −0.937 | −63.467 | 1.00 | 27.10 | O |
| ATOM | 1898 | N | GLN A | 255 | −35.347 | −2.228 | −61.620 | 1.00 | 29.17 | N |
| ATOM | 1899 | CA | GLN A | 255 | −35.525 | −1.199 | −60.598 | 1.00 | 30.10 | C |
| ATOM | 1900 | CB | GLN A | 255 | −35.385 | −1.847 | −59.222 | 1.00 | 31.97 | C |
| ATOM | 1901 | CG | GLN A | 255 | −36.239 | −1.223 | −58.138 | 1.00 | 34.09 | C |
| ATOM | 1902 | CD | GLN A | 255 | −37.639 | −1.785 | −58.119 | 1.00 | 37.01 | C |
| ATOM | 1903 | OE1 | GLN A | 255 | −37.927 | −2.726 | −57.379 | 1.00 | 39.24 | O |
| ATOM | 1904 | NE2 | GLN A | 255 | −38.520 | −1.223 | −58.947 | 1.00 | 37.68 | N |
| ATOM | 1905 | C | GLN A | 255 | −34.574 | 0.001 | −60.686 | 1.00 | 30.16 | C |
| ATOM | 1906 | O | GLN A | 255 | −34.899 | 1.093 | −60.211 | 1.00 | 30.66 | O |
| ATOM | 1907 | N | SER A | 256 | −33.391 | −0.183 | −61.255 | 1.00 | 29.81 | N |
| ATOM | 1908 | CA | SER A | 256 | −32.496 | 0.963 | −61.382 | 1.00 | 29.03 | C |

-continued

| | | | | | | | | | | |
|---|---|---|---|---|---|---|---|---|---|---|
| \multicolumn{11}{c}{Atomic coordinates for CRBN:DDB1:Lenalidomide (Human protein)} |
| ATOM | 1909 | CB | SER A | 256 | −31.769 | 1.240 | −60.061 | 1.00 | 29.65 | C |
| ATOM | 1910 | OG | SER A | 256 | −31.056 | 2.476 | −60.109 | 1.00 | 30.04 | O |
| ATOM | 1911 | C | SER A | 256 | −31.528 | 0.914 | −62.569 | 1.00 | 27.68 | C |
| ATOM | 1912 | O | SER A | 256 | −31.697 | 0.105 | −63.491 | 1.00 | 27.83 | O |
| ATOM | 1913 | N | THR A | 257 | −30.543 | 1.809 | −62.543 | 1.00 | 24.58 | N |
| ATOM | 1914 | CA | THR A | 257 | −29.713 | 2.068 | −63.693 | 1.00 | 23.59 | C |
| ATOM | 1915 | CB | THR A | 257 | −29.783 | 3.552 | −64.092 | 1.00 | 23.62 | C |
| ATOM | 1916 | OG1 | THR A | 257 | −31.152 | 3.937 | −64.255 | 1.00 | 23.90 | O |
| ATOM | 1917 | CBCG2 | THR A | 257 | −29.021 | 3.821 | −65.404 | 1.00 | 23.58 | C |
| ATOM | 1918 | C | THR A | 257 | −28.284 | 1.684 | −63.391 | 1.00 | 22.84 | C |
| ATOM | 1919 | O | THR A | 257 | −27.747 | 2.040 | −62.345 | 1.00 | 23.69 | O |
| ATOM | 1920 | N | IRE A | 258 | −27.668 | 0.943 | −64.302 | 1.00 | 21.82 | N |
| ATOM | 1921 | CA | IRE A | 258 | −26.308 | 0.497 | −64.081 | 1.00 | 21.03 | C |
| ATOM | 1922 | CB | IRE A | 258 | −26.010 | −0.837 | −64.763 | 1.00 | 20.23 | C |
| ATOM | 1923 | CG1 | IRE A | 258 | −27.005 | −1.903 | −64.310 | 1.00 | 19.80 | C |
| ATOM | 1924 | CD1 | IRE A | 258 | −26.778 | −2.390 | −62.902 | 1.00 | 19.30 | C |
| ATOM | 1925 | CG2 | IRE A | 258 | −24.595 | −1.271 | −64.439 | 1.00 | 20.39 | C |
| ATOM | 1926 | C | IRE A | 258 | −25.353 | 1.554 | −64.575 | 1.00 | 21.20 | C |
| ATOM | 1927 | O | IRE A | 258 | −25.384 | 1.927 | −65.749 | 1.00 | 21.31 | O |
| ATOM | 1928 | N | VAL A | 259 | −24.502 | 2.034 | −63.670 | 1.00 | 20.66 | N |
| ATOM | 1929 | CA | VAL A | 259 | −23.665 | 3.181 | −63.961 | 1.00 | 20.05 | C |
| ATOM | 1930 | CB | VAL A | 259 | −24.055 | 4.397 | −63.128 | 1.00 | 19.86 | C |
| ATOM | 1931 | CG1 | VAL A | 259 | −25.480 | 4.805 | −63.454 | 1.00 | 19.61 | C |
| ATOM | 1932 | CG2 | VAL A | 259 | −23.871 | 4.107 | −61.644 | 1.00 | 20.06 | C |
| ATOM | 1933 | C | VAL A | 259 | −22.180 | 2.930 | −63.817 | 1.00 | 19.80 | C |
| ATOM | 1934 | O | VAL A | 259 | −21.382 | 3.675 | −64.377 | 1.00 | 21.36 | O |
| ATOM | 1935 | N | CYS A | 260 | −21.796 | 1.900 | −63.079 | 0.50 | 18.54 | N |
| ATOM | 1936 | CA | CYS A | 260 | −20.403 | 1.522 | −63.056 | 0.50 | 17.68 | C |
| ATOM | 1937 | CB | CYS A | 260 | −19.704 | 2.040 | −61.809 | 0.50 | 16.71 | C |
| ATOM | 1938 | SG | CYS A | 260 | −20.367 | 1.381 | −60.280 | 0.50 | 15.24 | S |
| ATOM | 1939 | C | CYS A | 260 | −20.275 | 0.034 | −63.164 | 0.50 | 18.06 | C |
| ATOM | 1940 | O | CYS A | 260 | −21.188 | −0.709 | −62.840 | 0.50 | 17.60 | O |
| ATOM | 1941 | N | HIS A | 261 | −19.127 | −0.391 | −63.658 | 1.00 | 19.49 | N |
| ATOM | 1942 | CA | HIS A | 261 | −18.827 | −1.799 | −63.838 | 1.00 | 20.56 | C |
| ATOM | 1943 | CB | HIS A | 261 | −19.216 | −2.248 | −65.241 | 1.00 | 20.91 | C |
| ATOM | 1944 | CG | HIS A | 261 | −18.238 | −1.812 | −66.313 | 1.00 | 21.44 | C |
| ATOM | 1945 | ND1 | HIS A | 261 | −17.066 | −2.456 | −66.535 | 1.00 | 21.54 | N |
| ATOM | 1946 | CE1 | HIS A | 261 | −16.407 | −1.856 | −67.537 | 1.00 | 21.65 | C |
| ATOM | 1947 | NE2 | HIS A | 261 | −17.157 | −0.820 | −67.965 | 1.00 | 22.55 | N |
| ATOM | 1948 | CD2 | HIS A | 261 | −18.290 | −0.765 | −67.230 | 1.00 | 21.69 | C |
| ATOM | 1949 | C | HIS A | 261 | −17.359 | −2.045 | −63.615 | 1.00 | 20.87 | C |
| ATOM | 1950 | O | HIS A | 261 | −16.582 | −1.108 | −63.495 | 1.00 | 20.12 | O |
| ATOM | 1951 | N | ASN A | 262 | −16.982 | −3.322 | −63.560 | 1.00 | 22.17 | N |
| ATOM | 1952 | CA | ASN A | 262 | −15.587 | −3.734 | −63.553 | 1.00 | 22.63 | C |
| ATOM | 1953 | CB | ASN A | 262 | −14.926 | −3.363 | −62.238 | 1.00 | 24.05 | C |
| ATOM | 1954 | CG | ASN A | 262 | −13.425 | −3.412 | −62.331 | 1.00 | 25.31 | C |
| ATOM | 1955 | OD1 | ASN A | 262 | −12.838 | −2.763 | −63.208 | 1.00 | 26.61 | O |
| ATOM | 1956 | ND2 | ASN A | 262 | −12.787 | −4.217 | −61.462 | 1.00 | 24.75 | N |
| ATOM | 1957 | C | ASN A | 262 | −15.401 | −5.225 | −63.787 | 1.00 | 22.52 | C |
| ATOM | 1958 | O | ASN A | 262 | −16.171 | −6.041 | −63.274 | 1.00 | 23.22 | O |
| ATOM | 1959 | N | ARG A | 263 | −14.357 | −5.575 | −64.535 | 1.00 | 22.27 | N |
| ATOM | 1960 | CA | ARG A | 263 | −14.015 | −6.981 | −64.810 | 1.00 | 22.10 | C |
| ATOM | 1961 | CB | ARG A | 263 | −13.013 | −7.049 | −65.950 | 1.00 | 21.45 | C |
| ATOM | 1962 | CG | ARG A | 263 | −13.027 | −8.345 | −66.716 | 1.00 | 21.94 | C |
| ATOM | 1963 | CD | ARG A | 263 | −11.711 | −8.557 | −67.437 | 1.00 | 22.51 | C |
| ATOM | 1964 | NE | ARG A | 263 | −11.210 | −7.331 | −68.045 | 1.00 | 22.37 | N |
| ATOM | 1965 | CZ | ARG A | 263 | −9.930 | −6.995 | −68.081 | 1.00 | 22.39 | C |
| ATOM | 1966 | NH1 | ARG A | 263 | −9.022 | −7.800 | −67.536 | 1.00 | 23.56 | N |
| ATOM | 1967 | NH2 | ARG A | 263 | −9.559 | −5.852 | −68.642 | 1.00 | 21.93 | N |
| ATOM | 1968 | C | ARG A | 263 | −13.439 | −7.710 | −63.589 | 1.00 | 22.33 | C |
| ATOM | 1969 | O | ARG A | 263 | −12.499 | −7.228 | −62.953 | 1.00 | 22.51 | O |
| ATOM | 1970 | N | VAL A | 264 | −13.997 | −8.875 | −63.269 | 1.00 | 22.87 | N |
| ATOM | 1971 | CA | VAL A | 264 | −13.488 | −9.679 | −62.152 | 1.00 | 23.22 | C |
| ATOM | 1972 | CB | VAL A | 264 | −14.578 | −10.590 | −61.542 | 1.00 | 22.71 | C |
| ATOM | 1973 | CG1 | VAL A | 264 | −13.980 | −11.649 | −60.625 | 1.00 | 23.11 | C |
| ATOM | 1974 | CG2 | VAL A | 264 | −15.559 | −9.746 | −60.765 | 1.00 | 22.14 | C |
| ATOM | 1975 | C | VAL A | 264 | −12.226 | −10.455 | −62.536 | 1.00 | 23.81 | C |
| ATOM | 1976 | O | VAL A | 264 | −11.202 | −10.310 | −61.897 | 1.00 | 24.52 | O |
| ATOM | 1977 | N | ASP A | 265 | −12.284 | −11.253 | −63.589 | 1.00 | 25.28 | N |
| ATOM | 1978 | CA | ASP A | 265 | −11.126 | −12.053 | −63.978 | 1.00 | 26.97 | C |
| ATOM | 1979 | CB | ASP A | 265 | −11.431 | −13.536 | −63.787 | 1.00 | 28.67 | C |
| ATOM | 1980 | CG | ASP A | 265 | −12.866 | −13.881 | −64.131 | 1.00 | 30.59 | C |
| ATOM | 1981 | OD1 | ASP A | 265 | −13.288 | −13.601 | −65.281 | 1.00 | 31.08 | O |
| ATOM | 1982 | OD2 | ASP A | 265 | −13.570 | −14.427 | −63.246 | 1.00 | 31.23 | O |
| ATOM | 1983 | C | ASP A | 265 | −10.679 | −11.762 | −65.416 | 1.00 | 27.09 | C |
| ATOM | 1984 | O | ASP A | 265 | −11.478 | −11.279 | −66.216 | 1.00 | 25.96 | O |
| ATOM | 1985 | N | PRO A | 266 | −9.390 | −12.036 | −65.737 | 1.00 | 27.64 | N |

-continued

| | | Atomic coordinates for CRBN:DDB1:Lenalidomide (Human protein) | | | | | | | |
|---|---|---|---|---|---|---|---|---|---|
| ATOM | 1986 | CA | PRO A | 266 | −8.837 | −11.839 | −67.085 | 1.00 | 27.90 | C |
| ATOM | 1987 | CB | PRO A | 266 | −7.487 | −12.581 | −67.030 | 1.00 | 27.75 | C |
| ATOM | 1988 | CG | PRO A | 266 | −7.413 | −13.227 | −65.673 | 1.00 | 26.88 | C |
| ATOM | 1989 | CD | PRO A | 266 | −8.344 | −12.466 | −64.793 | 1.00 | 26.68 | C |
| ATOM | 1990 | C | PRO A | 266 | −9.727 | −12.427 | −68.177 | 1.00 | 28.35 | C |
| ATOM | 1991 | O | PRO A | 266 | −10.073 | −11.729 | −69.120 | 1.00 | 28.99 | O |
| ATOM | 1992 | N | ASN A | 267 | −10.090 | −13.700 | −68.026 | 1.00 | 29.75 | N |
| ATOM | 1993 | CA | ASN A | 267 | −11.121 | −14.383 | −68.832 | 1.00 | 30.88 | C |
| ATOM | 1994 | CB | ASN A | 267 | −11.650 | −15.592 | −68.036 | 1.00 | 34.22 | C |
| ATOM | 1995 | CG | ASN A | 267 | −12.161 | −16.723 | −68.926 | 1.00 | 37.10 | C |
| ATOM | 1996 | OD1 | ASN A | 267 | −12.521 | −16.519 | −70.095 | 1.00 | 38.84 | O |
| ATOM | 1997 | ND2 | ASN A | 267 | −12.199 | −17.931 | −68.368 | 1.00 | 37.27 | N |
| ATOM | 1998 | C | ASN A | 267 | −12.315 | −13.514 | −69.254 | 1.00 | 29.58 | C |
| ATOM | 1999 | O | ASN A | 267 | −12.819 | −13.636 | −70.365 | 1.00 | 28.07 | O |
| ATOM | 2000 | N | GLY A | 268 | −12.771 | −12.659 | −68.341 | 1.00 | 30.47 | N |
| ATOM | 2001 | CA | GLY A | 268 | −13.976 | −11.858 | −68.534 | 1.00 | 30.23 | C |
| ATOM | 2002 | C | GLY A | 268 | −15.241 | −12.639 | −68.226 | 1.00 | 30.13 | C |
| ATOM | 2003 | O | GLY A | 268 | −16.337 | −12.207 | −68.570 | 1.00 | 29.90 | O |
| ATOM | 2004 | N | SER A | 269 | −15.088 | −13.799 | −67.590 | 1.00 | 30.83 | N |
| ATOM | 2005 | CA | SER A | 269 | −16.233 | −14.654 | −67.226 | 1.00 | 32.21 | C |
| ATOM | 2006 | CB | SER A | 269 | −15.771 | −15.883 | −66.429 | 1.00 | 33.78 | C |
| ATOM | 2007 | OG | SER A | 269 | −14.545 | −16.391 | −66.930 | 1.00 | 36.77 | O |
| ATOM | 2008 | C | SER A | 269 | −17.261 | −13.884 | −66.397 | 1.00 | 31.53 | C |
| ATOM | 2009 | O | SER A | 269 | −18.469 | −14.001 | −66.618 | 1.00 | 31.53 | O |
| ATOM | 2010 | N | ARG A | 270 | −16.760 | −13.099 | −65.447 | 1.00 | 29.82 | N |
| ATOM | 2011 | CA | ARG A | 270 | −17.595 | −12.364 | −64.527 | 1.00 | 27.38 | C |
| ATOM | 2012 | CB | ARG A | 270 | −17.397 | −12.907 | −63.116 | 1.00 | 28.98 | C |
| ATOM | 2013 | CG | ARG A | 270 | −17.948 | −14.314 | −62.904 | 1.00 | 30.93 | C |
| ATOM | 2014 | CD | ARG A | 270 | −17.467 | −14.918 | −61.590 | 1.00 | 32.35 | C |
| ATOM | 2015 | NE | ARG A | 270 | −16.005 | −14.882 | −61.497 | 1.00 | 34.54 | N |
| ATOM | 2016 | CZ | ARG A | 270 | −15.270 | −15.654 | −60.701 | 1.00 | 34.35 | C |
| ATOM | 2017 | NH1 | ARG A | 270 | −15.861 | −16.547 | −59.910 | 1.00 | 34.33 | N |
| ATOM | 2018 | NH2 | ARG A | 270 | −13.940 | −15.536 | −60.706 | 1.00 | 33.76 | N |
| ATOM | 2019 | C | ARG A | 270 | −17.303 | −10.866 | −64.560 | 1.00 | 25.26 | C |
| ATOM | 2020 | O | ARG A | 270 | −16.159 | −10.447 | −64.705 | 1.00 | 24.53 | O |
| ATOM | 2021 | N | TYR A | 271 | −18.357 | −10.071 | −64.424 | 1.00 | 23.28 | N |
| ATOM | 2022 | CA | TYR A | 271 | −18.233 | −8.634 | −64.251 | 1.00 | 21.55 | C |
| ATOM | 2023 | CB | TYR A | 271 | −18.785 | −7.917 | −65.481 | 1.00 | 22.00 | C |
| ATOM | 2024 | CG | TYR A | 271 | −17.855 | −8.012 | −66.664 | 1.00 | 22.35 | C |
| ATOM | 2025 | CD1 | TYR A | 271 | −17.912 | −9.098 | −67.528 | 1.00 | 22.24 | C |
| ATOM | 2026 | CE1 | TYR A | 271 | −17.044 | −9.198 | −68.597 | 1.00 | 22.70 | C |
| ATOM | 2027 | CZ | TYR A | 271 | −16.102 | −8.213 | −68.805 | 1.00 | 22.80 | C |
| ATOM | 2028 | OH | TYR A | 271 | −15.237 | −8.326 | −69.862 | 1.00 | 24.17 | O |
| ATOM | 2029 | CE2 | TYR A | 271 | −16.020 | −7.125 | −67.960 | 1.00 | 22.33 | C |
| ATOM | 2030 | CD2 | TYR A | 271 | −16.894 | −7.026 | −66.900 | 1.00 | 22.12 | C |
| ATOM | 2031 | C | TYR A | 271 | −18.981 | −8.200 | −63.007 | 1.00 | 20.26 | C |
| ATOM | 2032 | O | TYR A | 271 | −19.979 | −8.810 | −62.642 | 1.00 | 20.18 | O |
| ATOM | 2033 | N | LEU A | 272 | −18.485 | −7.167 | −62.336 | 1.00 | 19.08 | N |
| ATOM | 2034 | CA | LEU A | 272 | −19.249 | −6.519 | −61.269 | 1.00 | 18.06 | C |
| ATOM | 2035 | CB | LEU A | 272 | −18.339 | −6.086 | −60.125 | 1.00 | 17.47 | C |
| ATOM | 2036 | CG | LEU A | 272 | −17.752 | −7.203 | −59.262 | 1.00 | 17.40 | C |
| ATOM | 2037 | CD1 | LEU A | 272 | −16.629 | −6.694 | −58.379 | 1.00 | 17.33 | C |
| ATOM | 2038 | CD2 | LEU A | 272 | −18.818 | −7.871 | −58.409 | 1.00 | 17.74 | C |
| ATOM | 2039 | C | LEU A | 272 | −19.988 | −5.319 | −61.852 | 1.00 | 17.86 | C |
| ATOM | 2040 | O | LEU A | 272 | −19.447 | −4.625 | −62.727 | 1.00 | 17.49 | O |
| ATOM | 2041 | N | LEU A | 273 | −21.230 | −5.097 | −61.401 | 1.00 | 17.25 | N |
| ATOM | 2042 | CA | LEU A | 273 | −22.055 | −3.971 | −61.890 | 1.00 | 16.33 | C |
| ATOM | 2043 | CB | LEU A | 273 | −23.190 | −4.449 | −62.787 | 1.00 | 15.75 | C |
| ATOM | 2044 | CG | LEU A | 273 | −22.942 | −5.353 | −63.971 | 1.00 | 15.56 | C |
| ATOM | 2045 | CD1 | LEU A | 273 | −24.256 | −5.440 | −64.705 | 1.00 | 15.75 | C |
| ATOM | 2046 | CD2 | LEU A | 273 | −21.875 | −4.789 | −64.886 | 1.00 | 15.88 | C |
| ATOM | 2047 | C | LEU A | 273 | −22.674 | −3.199 | −60.759 | 1.00 | 16.01 | C |
| ATOM | 2048 | O | LEU A | 273 | −23.302 | −3.781 | −59.877 | 1.00 | 16.22 | O |
| ATOM | 2049 | N | GLY A | 274 | −22.547 | −1.881 | −60.831 | 1.00 | 16.08 | N |
| ATOM | 2050 | CA | GLY A | 274 | −23.061 | −0.975 | −59.805 | 1.00 | 16.16 | C |
| ATOM | 2051 | C | GLY A | 274 | −24.246 | −0.116 | −60.201 | 1.00 | 16.15 | C |
| ATOM | 2052 | O | GLY A | 274 | −24.188 | −0.686 | −61.129 | 1.00 | 15.77 | O |
| ATOM | 2053 | N | ASP A | 275 | −25.320 | −0.308 | −59.453 | 1.00 | 17.18 | N |
| ATOM | 2054 | CA | ASP A | 275 | −26.562 | 0.457 | −59.507 | 1.00 | 17.84 | C |
| ATOM | 2055 | CB | ASP A | 275 | −29.442 | −0.121 | −58.412 | 1.00 | 18.98 | C |
| ATOM | 2056 | CG | ASP A | 275 | −28.878 | 0.115 | −58.643 | 1.00 | 20.70 | C |
| ATOM | 2057 | OD1 | ASP A | 275 | −29.228 | 1.296 | −58.831 | 1.00 | 22.80 | O |
| ATOM | 2058 | OD2 | ASP A | 275 | −29.662 | −0.868 | −58.623 | 1.00 | 20.80 | O |
| ATOM | 2059 | C | ASP A | 275 | −26.366 | 1.936 | −59.199 | 1.00 | 17.81 | C |
| ATOM | 2060 | O | ASP A | 275 | −25.329 | 2.335 | −58.673 | 1.00 | 18.80 | O |
| ATOM | 2061 | N | MET A | 276 | −27.382 | 2.745 | −59.465 | 0.50 | 17.44 | N |
| ATOM | 2062 | CA | MET A | 276 | −27.356 | 4.152 | −59.075 | 0.50 | 17.27 | C |

-continued

| | | Atomic coordinates for CRBN:DDB1:Lenalidomide (Human protein) | | | | | | | |
|---|---|---|---|---|---|---|---|---|---|
| ATOM | 2063 | CB | MET A | 276 | −28.250 | 4.951 | −60.006 | 0.50 | 16.36 | C |
| ATOM | 2064 | CG | MET A | 276 | −27.658 | 6.265 | −60.441 | 0.50 | 15.70 | C |
| ATOM | 2065 | SD | MET A | 276 | −28.835 | 7.175 | −61.433 | 0.50 | 14.81 | S |
| ATOM | 2066 | CE | MET A | 276 | −28.872 | 6.168 | −62.893 | 0.50 | 15.21 | C |
| ATOM | 2067 | C | MET A | 276 | −27.814 | 4.351 | −57.631 | 0.50 | 17.87 | C |
| ATOM | 2068 | O | MET A | 276 | −27.789 | 5.456 | −57.111 | 0.50 | 17.37 | O |
| ATOM | 2069 | N | GLU A | 277 | −28.205 | 3.257 | −56.991 | 1.00 | 19.52 | N |
| ATOM | 2070 | CA | GLU A | 277 | −28.971 | 3.277 | −55.748 | 1.00 | 20.94 | C |
| ATOM | 2071 | CB | GLU A | 277 | −30.423 | 2.825 | −56.000 | 1.00 | 24.45 | C |
| ATOM | 2072 | CG | GLU A | 277 | −31.305 | 3.821 | −56.748 | 1.00 | 29.67 | C |
| ATOM | 2073 | CD | GLU A | 277 | −32.795 | 3.719 | −56.383 | 1.00 | 34.13 | C |
| ATOM | 2074 | OE1 | GLU A | 277 | −33.142 | 3.055 | −55.373 | 1.00 | 36.28 | O |
| ATOM | 2075 | OE2 | GLU A | 277 | −33.632 | 4.328 | −57.099 | 1.00 | 37.15 | O |
| ATOM | 2076 | C | GLU A | 277 | −28.367 | 2.353 | −54.692 | 1.00 | 19.99 | C |
| ATOM | 2077 | O | GLU A | 277 | −28.956 | 2.168 | −53.624 | 1.00 | 19.90 | O |
| ATOM | 2078 | N | GLY A | 278 | −27.222 | 1.739 | −54.995 | 1.00 | 18.39 | N |
| ATOM | 2079 | CA | GLY A | 278 | −26.498 | 0.959 | −53.991 | 1.00 | 16.63 | C |
| ATOM | 2080 | C | GLY A | 278 | −26.391 | −0.523 | −54.274 | 1.00 | 15.66 | C |
| ATOM | 2081 | O | GLY A | 278 | −25.657 | −1.236 | −53.589 | 1.00 | 15.65 | O |
| ATOM | 2082 | N | ARG A | 279 | −27.114 | −0.994 | −55.282 | 0.50 | 14.73 | N |
| ATOM | 2083 | CA | ARG A | 279 | −27.097 | −2.404 | −55.601 | 0.50 | 13.97 | C |
| ATOM | 2084 | CB | ARG A | 279 | −28.327 | −2.820 | −56.415 | 0.50 | 13.82 | C |
| ATOM | 2085 | CG | ARG A | 279 | −29.642 | −2.758 | −55.659 | 0.50 | 13.31 | C |
| ATOM | 2086 | CD | ARG A | 279 | −30.799 | −3.020 | −56.603 | 0.50 | 13.21 | C |
| ATOM | 2087 | NE | ARG A | 279 | −32.082 | −2.574 | −56.064 | 0.50 | 13.02 | N |
| ATOM | 2088 | CZ | ARG A | 279 | −32.591 | −1.360 | −56.242 | 0.50 | 12.74 | C |
| ATOM | 2089 | NH1 | ARG A | 279 | −31.921 | −0.453 | −56.938 | 0.50 | 12.79 | N |
| ATOM | 2090 | NH2 | ARG A | 279 | −33.763 | −1.050 | −55.715 | 0.50 | 12.61 | N |
| ATOM | 2091 | C | ARG A | 279 | −25.822 | −2.776 | −56.329 | 0.50 | 13.57 | C |
| ATOM | 2092 | O | ARG A | 279 | −25.312 | −2.040 | −57.165 | 0.50 | 12.94 | O |
| ATOM | 2093 | N | LEU A | 280 | −25.307 | −3.931 | −55.952 | 1.00 | 13.86 | N |
| ATOM | 2094 | CA | LEU A | 280 | −24.160 | −4.547 | −56.583 | 1.00 | 14.00 | C |
| ATOM | 2095 | CB | LEU A | 280 | −23.080 | −4.848 | −55.543 | 1.00 | 13.58 | C |
| ATOM | 2096 | CG | LEU A | 280 | −21.725 | −5.295 | −56.080 | 1.00 | 13.40 | C |
| ATOM | 2097 | CD1 | LEU A | 280 | −21.062 | −4.163 | −56.853 | 1.00 | 13.43 | C |
| ATOM | 2098 | CD2 | LEU A | 280 | −20.840 | −5.793 | −54.948 | 1.00 | 13.17 | C |
| ATOM | 2099 | C | LEU A | 280 | −24.617 | −5.837 | −57.228 | 1.00 | 14.36 | C |
| ATOM | 2100 | O | LEU A | 280 | −25.209 | −6.696 | −56.566 | 1.00 | 14.01 | O |
| ATOM | 2101 | N | PHE A | 281 | −24.358 | −5.956 | −58.526 | 1.00 | 15.23 | N |
| ATOM | 2102 | CA | PHE A | 281 | −24.741 | −7.135 | −59.286 | 1.00 | 16.35 | C |
| ATOM | 2103 | CB | PHE A | 281 | −25.488 | −6.722 | −60.539 | 1.00 | 16.26 | C |
| ATOM | 2104 | CG | PHE A | 281 | −26.836 | −6.162 | −60.277 | 1.00 | 16.10 | C |
| ATOM | 2105 | CD1 | PHE A | 281 | −27.918 | −7.009 | −60.076 | 1.00 | 15.93 | C |
| ATOM | 2106 | CE1 | PHE A | 281 | −29.169 | −6.490 | −59.839 | 1.00 | 16.55 | C |
| ATOM | 2107 | CZ | PHE A | 281 | −29.347 | −5.104 | −59.806 | 1.00 | 16.87 | C |
| ATOM | 2108 | CE2 | PHE A | 281 | −28.271 | −4.252 | −60.001 | 1.00 | 16.07 | C |
| ATOM | 2109 | CD2 | PHE A | 281 | −27.026 | −4.784 | −60.240 | 1.00 | 15.94 | C |
| ATOM | 2110 | C | PHE A | 281 | −23.524 | −7.890 | −59.734 | 1.00 | 17.57 | C |
| ATOM | 2111 | O | PHE A | 281 | −22.437 | −7.307 | −59.823 | 1.00 | 18.48 | O |
| ATOM | 2112 | N | MET A | 282 | −23.699 | −9.174 | −60.041 | 1.00 | 18.62 | N |
| ATOM | 2113 | CA | MET A | 282 | −22.721 | −9.861 | −60.863 | 1.00 | 20.18 | C |
| ATOM | 2114 | CB | MET A | 282 | −22.088 | −11.034 | −60.157 | 1.00 | 22.06 | C |
| ATOM | 2115 | CG | MET A | 282 | −21.075 | −11.740 | −61.042 | 1.00 | 24.55 | C |
| ATOM | 2116 | SD | MET A | 282 | −19.486 | −11.891 | −60.216 | 1.00 | 29.62 | S |
| ATOM | 2117 | CE | MET A | 282 | −19.873 | −13.232 | −59.071 | 1.00 | 28.21 | C |
| ATOM | 2118 | C | MET A | 282 | −23.290 | −10.316 | −62.190 | 1.00 | 20.42 | C |
| ATOM | 2119 | O | LEU A | 283 | −24.315 | −11.003 | −62.235 | 1.00 | 21.04 | O |
| ATOM | 2120 | N | LEU A | 283 | −22.603 | −9.930 | −63.263 | 1.00 | 19.87 | N |
| ATOM | 2121 | CA | LEU A | 283 | −22.898 | −10.410 | −64.590 | 1.00 | 19.74 | C |
| ATOM | 2122 | CB | LEU A | 283 | −22.758 | −9.278 | −65.601 | 1.00 | 19.63 | C |
| ATOM | 2123 | CG | LEU A | 283 | −22.985 | −9.560 | −67.084 | 1.00 | 19.24 | C |
| ATOM | 2124 | CD1 | LEU A | 283 | −24.392 | −10.071 | −67.347 | 1.00 | 18.86 | C |
| ATOM | 2125 | CD2 | LEU A | 283 | −22.696 | −8.295 | −67.876 | 1.00 | 18.90 | C |
| ATOM | 2126 | C | LEU A | 283 | −21.947 | −11.546 | −64.920 | 1.00 | 20.30 | C |
| ATOM | 2127 | O | LEU A | 283 | −20.753 | −11.467 | −64.632 | 1.00 | 20.06 | O |
| ATOM | 2128 | N | LEU A | 284 | −22.507 | −12.602 | −65.515 | 1.00 | 21.15 | N |
| ATOM | 2129 | CA | LEU A | 284 | −21.793 | −13.828 | −65.859 | 1.00 | 21.30 | C |
| ATOM | 2130 | CB | LEU A | 284 | −22.350 | −14.990 | −65.041 | 1.00 | 20.57 | C |
| ATOM | 2131 | CG | LEU A | 284 | −22.105 | −14.944 | −63.529 | 1.00 | 20.60 | C |
| ATOM | 2132 | CD1 | LEU A | 284 | −23.413 | −15.016 | −62.770 | 1.00 | 20.78 | C |
| ATOM | 2133 | CD2 | LEU A | 284 | −21.160 | −16.039 | −63.055 | 1.00 | 20.68 | C |
| ATOM | 2134 | C | LEU A | 284 | −21.965 | −14.123 | −67.349 | 1.00 | 22.46 | C |
| ATOM | 2135 | O | LEU A | 284 | −23.072 | −13.984 | −67.890 | 1.00 | 22.39 | O |
| ATOM | 2136 | N | LEU A | 285 | −20.871 | −14.510 | −68.013 | 1.00 | 23.62 | N |
| ATOM | 2137 | CA | LEU A | 285 | −20.928 | −14.980 | −69.403 | 1.00 | 24.40 | C |
| ATOM | 2138 | CB | LEU A | 285 | −19.792 | −14.403 | −70.250 | 1.00 | 24.24 | C |
| ATOM | 2139 | CG | LEU A | 285 | −19.415 | −12.916 | −70.287 | 1.00 | 24.28 | C |

-continued

| | | | Atomic coordinates for CRBN:DDB1:Lenalidomide (Human protein) | | | | | | |
|---|---|---|---|---|---|---|---|---|---|
| ATOM | 2140 | CD1 | LEU A | 285 | −18.752 | −12.604 | −71.620 | 1.00 | 24.38 | C |
| ATOM | 2141 | CD2 | LEU A | 285 | −20.599 | −11.995 | −70.064 | 1.00 | 23.90 | C |
| ATOM | 2142 | C | LEU A | 285 | −20.820 | −16.489 | −69.389 | 1.00 | 26.19 | C |
| ATOM | 2143 | O | LEU A | 285 | −19.840 | −17.036 | −68.898 | 1.00 | 27.66 | O |
| ATOM | 2144 | N | GLU A | 286 | −21.826 | −17.170 | −69.916 | 1.00 | 28.48 | N |
| ATOM | 2145 | CA | GLU A | 286 | −21.875 | −18.617 | −69.799 | 1.00 | 30.21 | C |
| ATOM | 2146 | CB | GLU A | 286 | −23.253 | −19.069 | −69.324 | 1.00 | 31.60 | C |
| ATOM | 2147 | CG | GLU A | 286 | −23.807 | −18.214 | −68.197 | 1.00 | 33.06 | C |
| ATOM | 2148 | CD | GLU A | 286 | −24.730 | −18.967 | −67.247 | 1.00 | 36.91 | C |
| ATOM | 2149 | OE1 | GLU A | 286 | −25.656 | −19.697 | −67.707 | 1.00 | 37.26 | O |
| ATOM | 2150 | OE2 | GLU A | 286 | −24.535 | −18.803 | −66.018 | 1.00 | 39.32 | O |
| ATOM | 2151 | C | GLU A | 286 | −21.463 | −19.285 | −71.110 | 1.00 | 31.63 | C |
| ATOM | 2152 | O | GLU A | 286 | −21.940 | −18.910 | −72.193 | 1.00 | 30.47 | O |
| ATOM | 2153 | N | LYS A | 287 | −20.560 | −20.266 | −70.992 | 1.00 | 33.33 | N |
| ATOM | 2154 | CA | LYS A | 287 | −19.890 | −20.902 | −72.144 | 1.00 | 33.50 | C |
| ATOM | 2155 | CB | LYS A | 287 | −18.358 | −20.882 | −71.975 | 1.00 | 34.14 | C |
| ATOM | 2156 | CG | LYS A | 287 | −17.869 | −21.006 | −70.538 | 1.00 | 36.29 | C |
| ATOM | 2157 | CD | LYS A | 287 | −16.355 | −20.876 | −70.452 | 1.00 | 38.33 | C |
| ATOM | 2158 | CE | LYS A | 287 | −15.930 | −19.829 | −69.421 | 1.00 | 40.74 | C |
| ATOM | 2159 | NZ | LYS A | 287 | −16.037 | −20.276 | −68.000 | 1.00 | 40.62 | N |
| ATOM | 2160 | C | LYS A | 287 | −20.377 | −22.319 | −72.448 | 1.00 | 31.91 | C |
| ATOM | 2161 | O | LYS A | 287 | −21.099 | −22.919 | −71.662 | 1.00 | 30.94 | O |
| ATOM | 2162 | N | THR A | 296 | −18.443 | −21.919 | −77.420 | 1.00 | 43.82 | N |
| ATOM | 2163 | CA | THR A | 296 | −18.117 | −20.643 | −76.783 | 1.00 | 46.23 | C |
| ATOM | 2164 | CB | THR A | 296 | −17.490 | −19.636 | −77.781 | 1.00 | 49.44 | C |
| ATOM | 2165 | OG1 | THR A | 296 | −18.479 | −19.195 | −78.729 | 1.00 | 49.39 | O |
| ATOM | 2166 | CG2 | THR A | 296 | −16.282 | −20.268 | −78.505 | 1.00 | 49.45 | C |
| ATOM | 2167 | C | THR A | 296 | −19.326 | −20.022 | −76.064 | 1.00 | 43.76 | C |
| ATOM | 2168 | O | THR A | 296 | −20.117 | −20.745 | −75.467 | 1.00 | 45.08 | O |
| ATOM | 2169 | N | LEU A | 297 | −19.467 | −18.695 | −76.133 | 1.00 | 41.47 | N |
| ATOM | 2170 | CA | LEU A | 297 | −20.452 | −17.954 | −75.321 | 1.00 | 40.13 | C |
| ATOM | 2171 | CB | LEU A | 297 | −20.137 | −16.453 | −75.330 | 1.00 | 40.21 | C |
| ATOM | 2172 | CG | LEU A | 297 | −21.148 | −15.489 | −74.690 | 1.00 | 41.40 | C |
| ATOM | 2173 | CD1 | LEU A | 297 | −21.487 | −15.852 | −73.249 | 1.00 | 41.17 | C |
| ATOM | 2174 | CD2 | LEU A | 297 | −20.618 | −14.068 | −74.757 | 1.00 | 41.99 | C |
| ATOM | 2175 | C | LEU A | 297 | −21.927 | −18.192 | −75.685 | 1.00 | 37.84 | C |
| ATOM | 2176 | O | LEU A | 297 | −22.367 | −17.845 | −76.777 | 1.00 | 36.20 | O |
| ATOM | 2177 | N | LYS A | 298 | −22.687 | −18.746 | −74.738 | 1.00 | 36.28 | N |
| ATOM | 2178 | CA | LYS A | 298 | −24.066 | −19.156 | −75.008 | 1.00 | 35.16 | C |
| ATOM | 2179 | CB | LYS A | 298 | −24.262 | −20.653 | −74.765 | 1.00 | 34.30 | C |
| ATOM | 2180 | CG | LYS A | 298 | −25.419 | −21.217 | −75.564 | 1.00 | 33.96 | C |
| ATOM | 2181 | CD | LYS A | 298 | −25.712 | −22.662 | −75.213 | 1.00 | 36.09 | C |
| ATOM | 2182 | CE | LYS A | 298 | −27.136 | −23.026 | −75.618 | 1.00 | 37.68 | C |
| ATOM | 2183 | NZ | LYS A | 298 | −27.512 | −22.463 | −76.949 | 1.00 | 37.27 | N |
| ATOM | 2184 | C | LYS A | 298 | −25.161 | −18.363 | −74.292 | 1.00 | 34.24 | C |
| ATOM | 2185 | O | LYS A | 298 | −26.277 | −18.275 | −74.797 | 1.00 | 35.34 | O |
| ATOM | 2186 | N | ASP A | 299 | −24.867 | −17.792 | −73.129 | 1.00 | 32.83 | N |
| ATOM | 2187 | CA | ASP A | 299 | −25.889 | −17.018 | −72.426 | 1.00 | 30.99 | C |
| ATOM | 2188 | CB | ASP A | 299 | −26.801 | −17.951 | −71.635 | 1.00 | 32.92 | C |
| ATOM | 2189 | CG | ASP A | 299 | −28.208 | −17.407 | −71.495 | 1.00 | 35.16 | C |
| ATOM | 2190 | OD1 | ASP A | 299 | −28.437 | −16.215 | −71.832 | 1.00 | 35.55 | O |
| ATOM | 2191 | OD2 | ASP A | 299 | −29.090 | −18.177 | −71.047 | 1.00 | 36.78 | O |
| ATOM | 2192 | C | ASP A | 299 | −25.319 | −15.955 | −71.507 | 1.00 | 28.47 | C |
| ATOM | 2193 | O | ASP A | 299 | −24.123 | −15.956 | −71.234 | 1.00 | 28.56 | O |
| ATOM | 2194 | N | LEU A | 300 | −26.185 | −15.047 | −71.04 | 1.00 | 25.53 | N |
| ATOM | 2195 | CA | LEU A | 300 | −25.854 | −14.114 | −69.953 | 1.00 | 23.33 | C |
| ATOM | 2196 | CB | LEU A | 300 | −25.870 | −12.669 | −70.447 | 1.00 | 23.08 | C |
| ATOM | 2197 | CG | LEU A | 300 | −25.277 | −12.383 | −71.826 | 1.00 | 23.51 | C |
| ATOM | 2198 | CD1 | LEU A | 300 | −25.648 | −10.986 | −72.294 | 1.00 | 23.70 | C |
| ATOM | 2199 | CD2 | LEU A | 300 | −23.772 | −12.581 | −71.843 | 1.00 | 21.51 | C |
| ATOM | 2200 | C | LEU A | 300 | −26.811 | −14.261 | −68.761 | 1.00 | 21.81 | C |
| ATOM | 2201 | O | LEU A | 300 | −28.010 | −14.497 | −68.949 | 1.00 | 21.78 | O |
| ATOM | 2202 | N | ARG A | 301 | −26.272 | −14.123 | −67.543 | 1.00 | 19.96 | N |
| ATOM | 2203 | CA | ARG A | 301 | −27.067 | −14.159 | −66.295 | 1.00 | 18.46 | C |
| ATOM | 2204 | CB | ARG A | 301 | −26.957 | −15.536 | −65.617 | 1.00 | 17.37 | C |
| ATOM | 2205 | C | ARG A | 301 | −26.644 | −13.055 | −65.308 | 1.00 | 17.47 | C |
| ATOM | 2206 | O | ARG A | 301 | −25.460 | −12.802 | −65.120 | 1.00 | 17.41 | O |
| ATOM | 2207 | N | VAL A | 302 | −27.608 | −12.405 | −64.675 | 1.00 | 16.69 | N |
| ATOM | 2208 | CA | VAL A | 302 | −27.286 | −11.441 | −63.621 | 1.00 | 16.35 | C |
| ATOM | 2209 | CB | VAL A | 302 | −27.999 | −10.090 | −63.822 | 1.00 | 16.15 | C |
| ATOM | 2210 | CG1 | VAL A | 302 | −27.298 | −9.009 | −63.025 | 1.00 | 16.08 | C |
| ATOM | 2211 | CG2 | VAL A | 302 | −28.031 | −9.695 | −65.286 | 1.00 | 16.38 | C |
| ATOM | 2212 | C | VAL A | 302 | −27.670 | −12.001 | −62.253 | 1.00 | 16.48 | C |
| ATOM | 2213 | O | VAL A | 302 | −28.676 | −12.702 | −62.124 | 1.00 | 16.24 | O |
| ATOM | 2214 | N | GLU A | 303 | −26.865 | −11.696 | −61.235 | 1.00 | 16.67 | N |
| ATOM | 2215 | CA | GLU A | 303 | −27.167 | −12.086 | −59.858 | 1.00 | 16.99 | C |
| ATOM | 2216 | CB | GLU A | 303 | −26.145 | −13.116 | −59.353 | 1.00 | 18.23 | C |

-continued

| | | | | Atomic coordinates for CRBN:DDB1:Lenalidomide (Human protein) | | | | | |
|---|---|---|---|---|---|---|---|---|---|
| ATOM | 2217 | CG | GLU A | 303 | −26.328 | −14.554 | −59.843 | 1.00 | 19.73 | C |
| ATOM | 2218 | CD | GLU A | 303 | −25.203 | −15.492 | −59.378 | 1.00 | 20.69 | C |
| ATOM | 2219 | OE1 | GLU A | 303 | −24.405 | −15.078 | −58.493 | 1.00 | 20.78 | O |
| ATOM | 2220 | OE2 | GLU A | 303 | −25.119 | −16.647 | −59.891 | 1.00 | 20.86 | O |
| ATOM | 2221 | C | GLU A | 303 | −27.105 | −10.842 | −58.977 | 1.00 | 16.49 | C |
| ATOM | 2222 | O | GLU A | 303 | −26.185 | −10.046 | −59.135 | 1.00 | 17.08 | O |
| ATOM | 2223 | N | LEU A | 304 | −28.057 | −10.680 | −58.051 | 1.00 | 15.41 | N |
| ATOM | 2224 | CA | LEU A | 304 | −28.024 | −9.548 | −57.102 | 1.00 | 14.71 | C |
| ATOM | 2225 | CB | LEU A | 304 | −29.445 | −9.063 | −56.731 | 1.00 | 14.17 | C |
| ATOM | 2226 | CG | LEU A | 304 | −29.630 | −8.008 | −55.618 | 1.00 | 13.57 | C |
| ATOM | 2227 | CD1 | LEU A | 304 | −28.831 | −6.756 | −55.888 | 1.00 | 13.42 | C |
| ATOM | 2228 | CD2 | LEU A | 304 | −31.090 | −7.648 | −55.411 | 1.00 | 13.48 | C |
| ATOM | 2229 | C | LEU A | 304 | −27.176 | −9.799 | −55.847 | 1.00 | 14.46 | C |
| ATOM | 2230 | O | LEU A | 304 | −27.613 | −10.434 | −54.900 | 1.00 | 14.46 | O |
| ATOM | 2231 | N | LEU A | 305 | −25.972 | −9.257 | −55.827 | 1.00 | 14.77 | N |
| ATOM | 2232 | CA | LEU A | 305 | −25.075 | −9.485 | −54.697 | 1.00 | 15.38 | C |
| ATOM | 2233 | CB | LEU A | 305 | −23.642 | −9.085 | −55.047 | 1.00 | 15.05 | C |
| ATOM | 2234 | CG | LEU A | 305 | −23.126 | −9.731 | −56.341 | 1.00 | 15.28 | C |
| ATOM | 2235 | CD1 | LEU A | 305 | −21.838 | −9.060 | −56.821 | 1.00 | 15.56 | C |
| ATOM | 2236 | CD2 | LEU A | 305 | −22.943 | −11.235 | −56.214 | 1.00 | 14.98 | C |
| ATOM | 2237 | C | LEU A | 305 | −25.521 | −8.836 | −53.387 | 1.00 | 15.94 | C |
| ATOM | 2238 | O | LEU A | 305 | −25.290 | −9.391 | −52.322 | 1.00 | 16.03 | O |
| ATOM | 2239 | N | GLY A | 306 | −26.154 | −7.666 | −53.468 | 1.00 | 16.91 | N |
| ATOM | 2240 | CA | GLY A | 306 | −26.554 | −6.917 | −52.276 | 1.00 | 17.48 | C |
| ATOM | 2241 | C | GLY A | 306 | −26.270 | −5.422 | −52.344 | 1.00 | 18.55 | C |
| ATOM | 2242 | O | GLU A | 306 | −26.099 | −4.850 | −53.425 | 1.00 | 18.02 | O |
| ATOM | 2243 | N | GLU A | 307 | −26.211 | −4.799 | −51.167 | 1.00 | 19.85 | N |
| ATOM | 2244 | CA | GLU A | 307 | −26.119 | −3.346 | −51.022 | 1.00 | 20.40 | C |
| ATOM | 2245 | CB | GLU A | 307 | −27.180 | −2.873 | −50.030 | 1.00 | 22.91 | C |
| ATOM | 2246 | CG | GLU A | 307 | −27.523 | −1.388 | −50.056 | 1.00 | 25.66 | C |
| ATOM | 2247 | CD | GLU A | 307 | −28.139 | −0.909 | −48.732 | 1.00 | 27.80 | C |
| ATOM | 2248 | OE1 | GLU A | 307 | −29.256 | −1.366 | −48.374 | 1.00 | 27.85 | O |
| ATOM | 2249 | OE2 | GLU A | 307 | −27.498 | −0.073 | −48.041 | 1.00 | 29.67 | O |
| ATOM | 2250 | C | GLU A | 307 | −24.734 | −2.940 | −50.529 | 1.00 | 20.06 | C |
| ATOM | 2251 | O | GLU A | 307 | −24.168 | −3.561 | −49.619 | 1.00 | 20.24 | O |
| ATOM | 2252 | N | THR A | 308 | −24.176 | −1.918 | −51.165 | 1.00 | 18.95 | N |
| ATOM | 2253 | CA | THR A | 308 | −22.916 | −1.328 | −50.745 | 1.00 | 17.93 | C |
| ATOM | 2254 | CB | THR A | 308 | −21.799 | −1.582 | −51.769 | 1.00 | 17.91 | C |
| ATOM | 2255 | OG1 | THR A | 308 | −22.196 | −1.068 | −53.041 | 1.00 | 18.40 | O |
| ATOM | 2256 | CG2 | THR A | 308 | −21.510 | −3.053 | −51.908 | 1.00 | 17.84 | C |
| ATOM | 2257 | C | THR A | 308 | −23.185 | 0.150 | −50.695 | 1.00 | 17.45 | C |
| ATOM | 2258 | O | THR A | 308 | −24.325 | 0.568 | −50.886 | 1.00 | 17.68 | O |
| ATOM | 2259 | N | SER A | 309 | −22.161 | 0.954 | −50.447 | 1.00 | 16.65 | N |
| ATOM | 2260 | CA | SER A | 309 | −22.315 | 2.381 | −50.637 | 1.00 | 16.44 | C |
| ATOM | 2261 | CB | SER A | 309 | −21.002 | 3.107 | −50.366 | 1.00 | 16.86 | C |
| ATOM | 2262 | OG | SER A | 309 | −20.604 | 3.008 | −49.013 | 1.00 | 17.45 | O |
| ATOM | 2263 | C | SER A | 309 | −22.692 | 2.589 | −52.097 | 1.00 | 16.11 | C |
| ATOM | 2264 | O | SER A | 309 | −22.323 | 1.787 | −52.958 | 1.00 | 16.44 | O |
| ATOM | 2265 | N | ILE A | 310 | −23.420 | 3.661 | −52.378 | 1.00 | 15.08 | N |
| ATOM | 2266 | CA | ILE A | 310 | −23.714 | 4.035 | −53.740 | 1.00 | 14.24 | C |
| ATOM | 2267 | CB | ILE A | 310 | −24.524 | 5.336 | −53.780 | 1.00 | 13.93 | C |
| ATOM | 2268 | CG1 | ILE A | 310 | −25.882 | 5.109 | −53.120 | 1.00 | 13.85 | C |
| ATOM | 2269 | CD1 | ILE A | 310 | −26.638 | 6.375 | −52.811 | 1.00 | 14.15 | C |
| ATOM | 2270 | CG2 | ILE A | 310 | −24.708 | 5.811 | −55.206 | 1.00 | 13.76 | C |
| ATOM | 2271 | C | ILE A | 310 | −22.392 | 4.192 | −54.454 | 1.00 | 14.19 | C |
| ATOM | 2272 | O | ILE A | 310 | −21.600 | 5.058 | −54.111 | 1.00 | 14.14 | O |
| ATOM | 2273 | N | ALA A | 311 | −22.137 | 3.312 | −55.415 | 1.00 | 14.61 | N |
| ATOM | 2274 | CA | ALA A | 311 | −20.820 | 3.221 | −56.052 | 1.00 | 15.20 | C |
| ATOM | 2275 | CB | ALA A | 311 | −20.561 | 1.809 | −56.553 | 1.00 | 14.73 | C |
| ATOM | 2276 | C | ALA A | 311 | −20.633 | 4.230 | −57.177 | 1.00 | 15.89 | C |
| ATOM | 2277 | O | ALA A | 311 | −21.555 | 4.509 | −57.942 | 1.00 | 16.39 | O |
| ATOM | 2278 | N | GLU A | 312 | −19.436 | 4.785 | −57.257 | 1.00 | 16.71 | N |
| ATOM | 2279 | CA | GLU A | 312 | −19.065 | 5.649 | −58.355 | 1.00 | 17.97 | C |
| ATOM | 2280 | CB | GLU A | 312 | −18.323 | 6.882 | −57.825 | 1.00 | 19.13 | C |
| ATOM | 2281 | CG | GLU A | 312 | −17.526 | 7.668 | −58.862 | 1.00 | 21.30 | C |
| ATOM | 2282 | CD | GLU A | 312 | −18.388 | 8.473 | −59.854 | 1.00 | 24.28 | C |
| ATOM | 2283 | OE1 | GLU A | 312 | −17.809 | 8.986 | −60.860 | 1.00 | 25.05 | O |
| ATOM | 2284 | OE2 | GLU A | 312 | −19.634 | 8.603 | −59.636 | 1.00 | 25.16 | O |
| ATOM | 2285 | C | GLU A | 312 | −18.159 | 4.823 | −59.239 | 1.00 | 18.29 | C |
| ATOM | 2286 | O | GLU A | 312 | −18.220 | 4.906 | −60.472 | 1.00 | 18.39 | O |
| ATOM | 2287 | N | CYS A | 313 | −17.318 | 4.014 | −58.590 | 1.00 | 18.05 | N |
| ATOM | 2288 | CA | CYS A | 313 | −16.394 | 3.149 | −59.278 | 1.00 | 17.57 | C |
| ATOM | 2289 | CB | CYS A | 313 | −15.108 | 3.922 | −59.580 | 1.00 | 18.32 | C |
| ATOM | 2290 | SG | CYS A | 313 | −13.988 | 4.192 | −58.192 | 1.00 | 20.08 | S |
| ATOM | 2291 | C | CYS A | 313 | −16.136 | 1.862 | −58.483 | 1.00 | 17.19 | C |
| ATOM | 2292 | O | CYS A | 313 | −16.161 | 1.875 | −57.261 | 1.00 | 17.58 | O |
| ATOM | 2293 | N | LEU A | 314 | −15.911 | 0.749 | −59.180 | 1.00 | 16.98 | N |

-continued

| | | | | Atomic coordinates for CRBN:DDB1:Lenalidomide (Human protein) | | | | | |
|---|---|---|---|---|---|---|---|---|---|
| ATOM | 2294 | CA | LEU A | 314 | −15.615 | −0.540 | −58.534 | 1.00 | 16.94 | C |
| ATOM | 2295 | CB | LEU A | 314 | −16.702 | −1.567 | −58.834 | 1.00 | 16.38 | C |
| ATOM | 2296 | CG | LEU A | 314 | −18.144 | −1.225 | −58.482 | 1.00 | 16.35 | C |
| ATOM | 2297 | CD1 | LEU A | 314 | −19.094 | −2.058 | −59.317 | 1.00 | 16.20 | C |
| ATOM | 2298 | CD2 | LEU A | 314 | −18.411 | −1.427 | −56.997 | 1.00 | 16.48 | C |
| ATOM | 2299 | C | LEU A | 314 | −14.305 | −1.120 | −59.008 | 1.00 | 17.76 | C |
| ATOM | 2300 | O | LEU A | 314 | −13.966 | −1.055 | −60.192 | 1.00 | 17.93 | O |
| ATOM | 2301 | N | THR A | 315 | −13.570 | −1.714 | −58.084 | 1.00 | 18.98 | N |
| ATOM | 2302 | CA | THR A | 315 | −12.379 | −2.477 | −58.445 | 1.00 | 19.73 | C |
| ATOM | 2303 | CB | THR A | 315 | −11.073 | −1.718 | −58.147 | 1.00 | 20.57 | C |
| ATOM | 2304 | OG1 | THR A | 315 | −11.262 | −0.313 | −58.368 | 1.00 | 22.30 | O |
| ATOM | 2305 | CG2 | THR A | 315 | −9.968 | −2.217 | −59.054 | 1.00 | 21.13 | C |
| ATOM | 2306 | C | THR A | 315 | −12.367 | −3.783 | −57.680 | 1.00 | 19.65 | C |
| ATOM | 2307 | O | THR A | 315 | −12.553 | −3.799 | −56.462 | 1.00 | 19.98 | O |
| ATOM | 2308 | N | TYR A | 316 | −12.185 | −4.881 | −58.399 | 1.00 | 19.77 | N |
| ATOM | 2309 | CA | TYR A | 316 | −11.939 | −6.150 | −57.759 | 1.00 | 20.09 | C |
| ATOM | 2310 | CB | TYR A | 316 | −12.334 | −7.311 | −58.665 | 1.00 | 20.79 | C |
| ATOM | 2311 | CG | TYR A | 316 | −12.034 | −8.660 | −58.061 | 1.00 | 20.79 | C |
| ATOM | 2312 | CD1 | TYR A | 316 | −12.829 | −9.169 | −57.035 | 1.00 | 20.90 | C |
| ATOM | 2313 | CE1 | TYR A | 316 | −12.565 | −10.405 | −56.473 | 1.00 | 20.88 | C |
| ATOM | 2314 | CZ | TYR A | 316 | −11.490 | −11.138 | −56.923 | 1.00 | 20.85 | C |
| ATOM | 2315 | OH | TYR A | 316 | −11.233 | −12.346 | −56.342 | 1.00 | 21.09 | O |
| ATOM | 2316 | CE2 | TYR A | 316 | −10.673 | −10.654 | −57.934 | 1.00 | 20.84 | C |
| ATOM | 2317 | CD2 | TYR A | 316 | −10.949 | −9.421 | −58.501 | 1.00 | 20.46 | C |
| ATOM | 2318 | C | TYR A | 316 | −10.470 | −6.220 | −57.472 | 1.00 | 20.16 | C |
| ATOM | 2319 | O | TYR A | 316 | −9.646 | −6.010 | −58.367 | 1.00 | 20.18 | O |
| ATOM | 2320 | N | LEU A | 317 | −10.136 | −6.523 | −56.228 | 1.00 | 20.50 | N |
| ATOM | 2321 | CA | LEU A | 317 | −8.741 | −6.643 | −55.835 | 1.00 | 21.67 | C |
| ATOM | 2322 | CB | LEU A | 317 | −8.501 | −6.001 | −54.461 | 1.00 | 19.96 | C |
| ATOM | 2323 | CG | LEU A | 317 | −9.064 | −4.580 | −54.298 | 1.00 | 18.32 | C |
| ATOM | 2324 | CD1 | LEU A | 317 | −8.866 | −4.055 | −52.887 | 1.00 | 17.64 | C |
| ATOM | 2325 | CD2 | LEU A | 317 | −8.437 | −3.646 | −55.306 | 1.00 | 18.01 | C |
| ATOM | 2326 | C | LEU A | 317 | −8.287 | −8.107 | −55.893 | 1.00 | 23.97 | C |
| ATOM | 2327 | O | LEU A | 317 | −7.634 | −8.513 | −56.853 | 1.00 | 25.60 | O |
| ATOM | 2328 | N | ASP A | 318 | −8.673 | −8.907 | −54.905 | 1.00 | 26.15 | N |
| ATOM | 2329 | CA | ASP A | 318 | −8.175 | −10.273 | −54.786 | 1.00 | 27.89 | C |
| ATOM | 2330 | CB | ASP A | 318 | −6.651 | −10.255 | −54.677 | 1.00 | 31.85 | C |
| ATOM | 2331 | CG | ASP A | 318 | −6.033 | −11.622 | −54.873 | 1.00 | 36.21 | C |
| ATOM | 2332 | OD1 | ASP A | 318 | −6.750 | −12.542 | −55.336 | 1.00 | 38.00 | O |
| ATOM | 2333 | OD2 | ASP A | 318 | −4.823 | −11.771 | −54.566 | 1.00 | 39.12 | O |
| ATOM | 2334 | C | ASP A | 318 | −8.749 | −10.962 | −53.559 | 1.00 | 27.16 | C |
| ATOM | 2335 | O | ASP A | 318 | −9.141 | −10.308 | −52.587 | 1.00 | 27.14 | O |
| ATOM | 2336 | N | ASN A | 319 | −8.769 | −12.289 | −53.590 | 1.00 | 26.03 | N |
| ATOM | 2337 | CA | ASN A | 319 | −9.372 | −13.074 | −52.513 | 1.00 | 25.13 | C |
| ATOM | 2338 | CB | ASN A | 319 | −8.481 | −13.075 | −51.247 | 1.00 | 24.82 | C |
| ATOM | 2339 | C | ASN A | 319 | −10.791 | −12.562 | −52.235 | 1.00 | 23.65 | C |
| ATOM | 2340 | O | ASN A | 319 | −11.197 | −12.361 | −51.086 | 1.00 | 23.29 | O |
| ATOM | 2341 | N | GLY A | 320 | −11.524 | −12.325 | −53.320 | 1.00 | 22.51 | N |
| ATOM | 2342 | CA | GLY A | 320 | −11.915 | −11.89 | −53.243 | 1.00 | 22.03 | C |
| ATOM | 2343 | C | GLY A | 320 | −13.154 | −10.608 | −52.479 | 1.00 | 21.70 | C |
| ATOM | 2344 | O | GLY A | 320 | −14.229 | −10.423 | −51.882 | 1.00 | 22.19 | O |
| ATOM | 2345 | N | VAL A | 321 | −12.147 | −9.727 | −52.471 | 1.00 | 20.25 | N |
| ATOM | 2346 | CA | VAL A | 321 | −12.282 | −8.404 | −51.869 | 1.00 | 18.77 | C |
| ATOM | 2347 | CB | VAL A | 321 | −11.084 | −8.040 | −50.968 | 1.00 | 18.61 | C |
| ATOM | 2348 | CG1 | VAL A | 321 | −11.092 | −6.556 | −50.601 | 1.00 | 18.45 | C |
| ATOM | 2349 | CG2 | VAL A | 321 | −11.112 | −8.886 | −49.709 | 1.00 | 18.27 | C |
| ATOM | 2350 | C | VAL A | 321 | −12.487 | −7.384 | −52.971 | 1.00 | 17.81 | C |
| ATOM | 2351 | O | VAL A | 321 | −11.892 | −7.486 | −54.035 | 1.00 | 18.14 | O |
| ATOM | 2352 | N | VAL A | 322 | −13.366 | −6.427 | −52.722 | 1.00 | 16.91 | N |
| ATOM | 2353 | CA | VAL A | 322 | −13.731 | −5.444 | −53.720 | 1.00 | 16.27 | C |
| ATOM | 2354 | CB | VAL A | 322 | −15.135 | −5.745 | −54.302 | 1.00 | 16.48 | C |
| ATOM | 2355 | CG1 | VAL A | 322 | −15.612 | −4.612 | −55.196 | 1.00 | 16.59 | C |
| ATOM | 2356 | CG2 | VAL A | 322 | −15.118 | −7.039 | −55.081 | 1.00 | 16.62 | C |
| ATOM | 2357 | C | VAL A | 322 | −13.712 | −4.045 | −53.110 | 1.00 | 15.59 | C |
| ATOM | 2358 | O | VAL A | 322 | −14.265 | −3.822 | −52.007 | 1.00 | 15.25 | O |
| ATOM | 2359 | N | PHE A | 323 | −13.081 | −3.112 | −53.828 | 1.00 | 14.63 | N |
| ATOM | 2360 | CA | PHE A | 323 | −13.120 | −1.696 | −53.462 | 1.00 | 13.97 | C |
| ATOM | 2361 | CB | PHE A | 323 | −11.805 | −0.992 | −53.787 | 1.00 | 13.44 | C |
| ATOM | 2362 | CG | PHE A | 323 | −11.804 | 0.474 | −53.439 | 1.00 | 13.46 | C |
| ATOM | 2363 | CD1 | PHE A | 323 | −11.653 | 0.892 | −52.126 | 1.00 | 13.22 | C |
| ATOM | 2364 | CE1 | PHE A | 323 | −11.650 | 2.235 | −51.806 | 1.00 | 13.00 | C |
| ATOM | 2365 | CZ | PHE A | 323 | −11.797 | 3.184 | −52.796 | 1.00 | 13.00 | C |
| ATOM | 2366 | CE2 | PHE A | 323 | −11.932 | 2.793 | −54.111 | 1.00 | 13.28 | C |
| ATOM | 2367 | CD2 | PHE A | 323 | −11.942 | 1.444 | −54.431 | 1.00 | 13.65 | C |
| ATOM | 2368 | C | PHE A | 323 | −14.281 | −0.975 | −54.139 | 1.00 | 13.78 | C |
| ATOM | 2369 | O | PHE A | 323 | −14.350 | −0.896 | −55.375 | 1.00 | 13.77 | O |
| ATOM | 2370 | N | VAL A | 324 | −15.187 | −0.451 | −53.311 | 1.00 | 13.70 | N |

-continued

| | | | Atomic coordinates for CRBN:DDB1:Lenalidomide (Human protein) | | | | | | |
|---|---|---|---|---|---|---|---|---|---|
| ATOM | 2371 | CA | VAL A | 324 | −16.321 | 0.344 | −53.763 | 1.00 | 13.58 | C |
| ATOM | 2372 | CB | VAL A | 324 | −17.598 | −0.024 | −53.006 | 1.00 | 13.44 | C |
| ATOM | 2373 | CG1 | VAL A | 324 | −18.720 | 0.917 | −53.386 | 1.00 | 13.72 | C |
| ATOM | 2374 | CG2 | VAL A | 324 | −17.999 | −1.450 | −53.309 | 1.00 | 13.60 | C |
| ATOM | 2375 | C | VAL A | 324 | −15.977 | 1.795 | −53.488 | 1.00 | 13.87 | C |
| ATOM | 2376 | O | VAL A | 324 | −15.890 | 2.220 | −52.326 | 1.00 | 13.82 | O |
| ATOM | 2377 | N | GLY A | 325 | −15.728 | 2.536 | −54.566 | 1.00 | 14.08 | N |
| ATOM | 2378 | CA | GLY A | 325 | −15.343 | 3.932 | −54.484 | 1.00 | 14.00 | C |
| ATOM | 2379 | C | GLY A | 325 | −16.615 | 4.731 | −54.515 | 1.00 | 14.50 | C |
| ATOM | 2380 | O | GLY A | 325 | −17.416 | 4.593 | −55.447 | 1.00 | 14.85 | O |
| ATOM | 2381 | N | SER A | 326 | −16.823 | 5.554 | −53.492 | 1.00 | 14.50 | N |
| ATOM | 2382 | CA | SER A | 326 | −18.060 | 6.311 | −53.389 | 1.00 | 14.64 | C |
| ATOM | 2383 | CB | SER A | 326 | −18.747 | 6.006 | −52.073 | 1.00 | 14.39 | C |
| ATOM | 2384 | OG | SER A | 326 | −20.051 | 6.535 | −52.070 | 1.00 | 14.44 | O |
| ATOM | 2385 | C | SER A | 326 | −17.851 | 7.811 | −53.530 | 1.00 | 14.80 | C |
| ATOM | 2386 | O | SER A | 326 | −16.771 | 8.322 | −53.260 | 1.00 | 15.29 | O |
| ATOM | 2387 | N | ARG A | 327 | −18.888 | 8.512 | −53.969 | 1.00 | 14.73 | N |
| ATOM | 2388 | CA | ARG A | 327 | −18.875 | 9.963 | −53.941 | 1.00 | 14.68 | C |
| ATOM | 2389 | CB | ARG A | 327 | −19.061 | 10.558 | −55.329 | 1.00 | 15.01 | C |
| ATOM | 2390 | CG | ARG A | 327 | −17.748 | 11.016 | −55.899 | 1.00 | 15.79 | C |
| ATOM | 2391 | CD | ARG A | 327 | −17.781 | 11.105 | −57.410 | 1.00 | 17.16 | C |
| ATOM | 2392 | NE | ARG A | 327 | −18.280 | 12.397 | −57.906 | 1.00 | 18.54 | N |
| ATOM | 2393 | CZ | ARG A | 327 | −17.872 | 13.595 | −57.482 | 1.00 | 17.99 | C |
| ATOM | 2394 | NH1 | ARG A | 327 | −16.986 | 13.695 | −56.510 | 1.00 | 18.16 | N |
| ATOM | 2395 | NH2 | ARG A | 327 | −18.385 | 14.691 | −58.006 | 1.00 | 17.81 | N |
| ATOM | 2396 | C | ARG A | 327 | −19.933 | 10.470 | −53.017 | 1.00 | 14.29 | C |
| ATOM | 2397 | O | ARG A | 327 | −19.716 | 11.434 | −52.302 | 1.00 | 14.55 | O |
| ATOM | 2398 | N | LEU A | 328 | −21.078 | 9.805 | −53.021 | 1.00 | 14.01 | N |
| ATOM | 2399 | CA | LEU A | 328 | −22.204 | 10.225 | −52.201 | 1.00 | 13.71 | C |
| ATOM | 2400 | CB | LEU A | 328 | −23.534 | 9.810 | −52.832 | 1.00 | 13.67 | C |
| ATOM | 2401 | CG | LEU A | 328 | −23.693 | 10.221 | −54.301 | 1.00 | 14.02 | C |
| ATOM | 2402 | CD1 | LEU A | 328 | −25.074 | 9.882 | −54.853 | 1.00 | 13.89 | C |
| ATOM | 2403 | CD2 | LEU A | 328 | −23.399 | 11.708 | −54.460 | 1.00 | 14.03 | C |
| ATOM | 2404 | C | LEU A | 328 | −22.117 | 9.710 | −50.776 | 1.00 | 13.53 | C |
| ATOM | 2405 | O | LEU A | 328 | −22.897 | 10.136 | −49.938 | 1.00 | 13.68 | O |
| ATOM | 2406 | N | GLY A | 329 | −21.171 | 8.812 | −50.495 | 1.00 | 12.98 | N |
| ATOM | 2407 | CA | GLY A | 329 | −21.106 | 8.171 | −49.188 | 1.00 | 12.98 | C |
| ATOM | 2408 | C | GLY A | 329 | −19.710 | 7.731 | −48.842 | 1.00 | 13.02 | C |
| ATOM | 2409 | O | GLY A | 329 | −18.769 | 8.147 | −49.477 | 1.00 | 13.63 | O |
| ATOM | 2410 | N | ASP A | 330 | −19.564 | 6.894 | −47.821 | 1.00 | 12.96 | N |
| ATOM | 2411 | CA | ASP A | 330 | −18.257 | 6.359 | −47.505 | 1.00 | 13.03 | C |
| ATOM | 2412 | CB | ASP A | 330 | −18.269 | 5.626 | −46.155 | 1.00 | 13.25 | C |
| ATOM | 2413 | CG | ASP A | 330 | −18.316 | 6.566 | −44.948 | 1.00 | 13.38 | C |
| ATOM | 2414 | OD1 | ASP A | 330 | −18.136 | 7.806 | −45.065 | 1.00 | 13.30 | O |
| ATOM | 2415 | OD2 | ASP A | 330 | −18.527 | 6.030 | −43.847 | 1.00 | 13.66 | O |
| ATOM | 2416 | C | ASP A | 330 | −17.873 | 5.374 | −48.582 | 1.00 | 13.02 | C |
| ATOM | 2417 | O | ASP A | 330 | −18.713 | 4.622 | −49.055 | 1.00 | 12.92 | O |
| ATOM | 2418 | N | SER A | 331 | −16.600 | 5.358 | −48.954 | 1.00 | 13.27 | N |
| ATOM | 2419 | CA | SER A | 331 | −16.090 | 4.295 | −49.808 | 1.00 | 13.58 | C |
| ATOM | 2420 | CB | SER A | 331 | −14.830 | 4.752 | −50.511 | 1.00 | 13.68 | C |
| ATOM | 2421 | OG | SER A | 331 | −15.157 | 5.797 | −51.414 | 1.00 | 13.99 | O |
| ATOM | 2422 | C | SER A | 331 | −15.849 | 3.052 | −48.974 | 1.00 | 13.79 | C |
| ATOM | 2423 | O | SER A | 331 | −15.696 | 3.145 | −47.762 | 1.00 | 14.01 | O |
| ATOM | 2424 | N | GLN A | 332 | −15.840 | 1.882 | −49.603 | 1.00 | 14.16 | N |
| ATOM | 2425 | CA | GLN A | 332 | −15.766 | 0.626 | −48.828 | 1.00 | 14.46 | C |
| ATOM | 2426 | CB | GLN A | 332 | −17.122 | −0.070 | −48.835 | 1.00 | 14.26 | C |
| ATOM | 2427 | CG | GLN A | 332 | −18.223 | 0.650 | −48.111 | 1.00 | 14.15 | C |
| ATOM | 2428 | CD | GLN A | 332 | −19.560 | 0.043 | −48.430 | 1.00 | 14.06 | C |
| ATOM | 2429 | OE1 | GLN A | 332 | −19.879 | −0.191 | −49.589 | 1.00 | 13.97 | O |
| ATOM | 2430 | NE2 | GLN A | 332 | −20.357 | −0.212 | −47.402 | 1.00 | 14.25 | N |
| ATOM | 2431 | C | GLN A | 332 | −14.736 | −0.401 | −49.288 | 1.00 | 14.57 | C |
| ATOM | 2432 | O | GLN A | 332 | −14.244 | −0.361 | −50.402 | 1.00 | 14.57 | O |
| ATOM | 2433 | N | LEU A | 333 | −14.448 | −1.345 | −48.410 | 1.00 | 15.23 | N |
| ATOM | 2434 | CA | LEU A | 333 | −13.960 | −2.640 | −48.834 | 1.00 | 16.21 | C |
| ATOM | 2435 | CB | LEU A | 333 | −12.660 | −3.001 | −48.109 | 1.00 | 15.81 | C |
| ATOM | 2436 | CG | LEU A | 333 | −11.417 | −2.272 | −48.602 | 1.00 | 15.01 | C |
| ATOM | 2437 | CD1 | LEU A | 333 | −10.214 | −2.659 | −47.772 | 1.00 | 14.79 | C |
| ATOM | 2438 | CD2 | LEU A | 333 | −11.174 | −2.583 | −50.061 | 1.00 | 14.97 | C |
| ATOM | 2439 | C | LEU A | 333 | −15.045 | −3.679 | −48.560 | 1.00 | 17.14 | C |
| ATOM | 2440 | O | LEU A | 333 | −15.527 | −3.804 | −47.438 | 1.00 | 17.36 | O |
| ATOM | 2441 | N | VAL A | 334 | −15.454 | −4.402 | −49.594 | 1.00 | 18.55 | N |
| ATOM | 2442 | CA | VAL A | 334 | −16.450 | −5.462 | −49.409 | 1.00 | 20.35 | C |
| ATOM | 2443 | CB | VAL A | 334 | −17.782 | −5.170 | −50.154 | 1.00 | 20.48 | C |
| ATOM | 2444 | CG1 | VAL A | 334 | −18.584 | −4.118 | −49.401 | 1.00 | 20.35 | C |
| ATOM | 2445 | CG2 | VAL A | 334 | −17.528 | −4.729 | −51.592 | 1.00 | 19.95 | C |
| ATOM | 2446 | C | VAL A | 334 | −15.924 | −6.856 | −49.763 | 1.00 | 21.24 | C |
| ATOM | 2447 | O | VAL A | 334 | −15.245 | −7.050 | −50.776 | 1.00 | 20.82 | O |

-continued

| \multicolumn{10}{c}{Atomic coordinates for CRBN:DDB1:Lenalidomide (Human protein)} |
| --- | --- | --- | --- | --- | --- | --- | --- | --- | --- |
| ATOM | 2448 | N | LYS A | 335 | −16.230 | −7.819 | −48.908 | 1.00 | 23.36 | N |
| ATOM | 2449 | CA | LYS A | 335 | −15.883 | −9.207 | −49.167 | 1.00 | 25.74 | C |
| ATOM | 2450 | CB | LYS A | 335 | −15.491 | −9.900 | −47.859 | 1.00 | 27.08 | C |
| ATOM | 2451 | CG | LYS A | 335 | −15.107 | −11.360 | −48.009 | 1.00 | 28.42 | C |
| ATOM | 2452 | CD | LYS A | 335 | −13.606 | −11.568 | −47.901 | 1.00 | 30.46 | C |
| ATOM | 2453 | CE | LYS A | 335 | −13.187 | −12.932 | −48.441 | 1.00 | 32.01 | C |
| ATOM | 2454 | NZ | LYS A | 335 | −14.169 | −14.018 | −48.125 | 1.00 | 33.25 | N |
| ATOM | 2455 | C | LYS A | 335 | −17.096 | −9.896 | −49.764 | 1.00 | 26.04 | C |
| ATOM | 2456 | O | LYS A | 335 | −18.167 | −9.889 | −49.151 | 1.00 | 25.19 | O |
| ATOM | 2457 | N | LEU A | 336 | −16.940 | −10.485 | −50.949 | 1.00 | 26.91 | N |
| ATOM | 2458 | CA | LEU A | 336 | −18.023 | −11.298 | −51.509 | 1.00 | 30.03 | C |
| ATOM | 2459 | CB | LEU A | 336 | −18.274 | −11.013 | −52.997 | 1.00 | 29.79 | C |
| ATOM | 2460 | CG | LEU A | 336 | −17.146 | −10.998 | −54.015 | 1.00 | 29.27 | C |
| ATOM | 2461 | CD1 | LEU A | 336 | −17.555 | −11.778 | −55.251 | 1.00 | 29.42 | C |
| ATOM | 2462 | CD2 | LEU A | 336 | −16.847 | −9.561 | −54.375 | 1.00 | 29.02 | C |
| ATOM | 2463 | C | LEU A | 336 | −17.886 | −12.803 | −51.244 | 1.00 | 31.63 | C |
| ATOM | 2464 | O | LEU A | 336 | −17.096 | −13.488 | −51.898 | 1.00 | 31.84 | O |
| ATOM | 2465 | N | ASN A | 337 | −18.685 | −13.295 | −50.290 | 1.00 | 35.08 | N |
| ATOM | 2466 | CA | ASN A | 337 | −18.662 | −14.704 | −49.843 | 1.00 | 39.02 | C |
| ATOM | 2467 | CB | ASN A | 337 | −19.124 | −14.813 | −48.378 | 1.00 | 40.63 | C |
| ATOM | 2468 | CG | ASN A | 337 | −18.176 | −14.114 | −47.398 | 1.00 | 42.42 | C |
| ATOM | 2469 | OD1 | ASN A | 337 | −16.978 | −13.950 | −47.668 | 1.00 | 43.75 | O |
| ATOM | 2470 | ND2 | ASN A | 337 | −18.711 | −13.707 | −46.245 | 1.00 | 41.47 | N |
| ATOM | 2471 | C | ASN A | 337 | −19.484 | −15.663 | −50.720 | 1.00 | 39.92 | C |
| ATOM | 2472 | O | ASN A | 337 | −19.923 | −15.306 | −51.825 | 1.00 | 40.64 | O |
| ATOM | 2473 | N | GLU A | 342 | −24.711 | −24.931 | −51.491 | 1.00 | 42.39 | N |
| ATOM | 2474 | CA | GLU A | 342 | −24.202 | −23.572 | −51.386 | 1.00 | 43.46 | C |
| ATOM | 2475 | CB | GLU A | 342 | −23.991 | −22.965 | −52.790 | 1.00 | 42.66 | C |
| ATOM | 2476 | CG | GLU A | 342 | −22.573 | −22.444 | −53.072 | 1.00 | 42.81 | C |
| ATOM | 2477 | CD | GLU A | 342 | −22.381 | −20.946 | −52.807 | 1.00 | 43.94 | C |
| ATOM | 2478 | OE1 | GLU A | 342 | −21.732 | −20.269 | −53.640 | 1.00 | 44.61 | O |
| ATOM | 2479 | OE2 | GLU A | 342 | −22.858 | −20.436 | −51.767 | 1.00 | 43.62 | O |
| ATOM | 2480 | C | GLU A | 342 | −25.149 | −22.712 | −50.524 | 1.00 | 44.50 | C |
| ATOM | 2481 | O | GLU A | 342 | −25.794 | −23.221 | −49.607 | 1.00 | 44.04 | O |
| ATOM | 2482 | N | GLN A | 343 | −25.202 | −21.411 | −50.812 | 1.00 | 47.08 | N |
| ATOM | 2483 | CA | GLN A | 343 | −26.059 | −20.457 | −50.093 | 1.00 | 45.88 | C |
| ATOM | 2484 | CB | GLN A | 343 | −25.466 | −20.105 | −48.719 | 1.00 | 48.52 | C |
| ATOM | 2485 | CG | GLN A | 343 | −24.169 | −19.290 | −48.776 | 1.00 | 53.25 | C |
| ATOM | 2486 | CD | GLN A | 343 | −23.259 | −19.513 | −47.570 | 1.00 | 53.83 | C |
| ATOM | 2487 | OE1 | GLN A | 343 | −23.630 | −19.247 | −46.431 | 1.00 | 52.35 | O |
| ATOM | 2488 | NE2 | GLN A | 343 | −22.053 | −20.029 | −47.823 | 1.00 | 52.28 | N |
| ATOM | 2489 | C | GLN A | 343 | −26.307 | −19.178 | −50.915 | 1.00 | 43.55 | C |
| ATOM | 2490 | O | GLN A | 343 | −26.913 | −18.234 | −50.415 | 1.00 | 45.41 | O |
| ATOM | 2491 | N | GLY A | 344 | −25.837 | −19.146 | −52.159 | 1.00 | 39.86 | N |
| ATOM | 2492 | CA | GLY A | 344 | −26.105 | −18.015 | −53.055 | 1.00 | 38.17 | C |
| ATOM | 2493 | C | GLY A | 344 | −25.234 | −16.797 | −52.795 | 1.00 | 37.15 | C |
| ATOM | 2494 | O | GLY A | 344 | −24.949 | −16.466 | −51.652 | 1.00 | 37.97 | O |
| ATOM | 2495 | N | SER A | 345 | −24.827 | −16.125 | −53.866 | 1.00 | 36.49 | N |
| ATOM | 2496 | CA | SER A | 345 | −23.875 | −15.012 | −53.797 | 1.00 | 35.91 | C |
| ATOM | 2497 | CB | SER A | 345 | −23.645 | −14.450 | −55.187 | 1.00 | 33.26 | C |
| ATOM | 2498 | OG | SER A | 345 | −22.904 | −15.353 | −55.965 | 1.00 | 32.43 | O |
| ATOM | 2499 | C | SER A | 345 | −24.299 | −13.880 | −52.876 | 1.00 | 37.81 | C |
| ATOM | 2500 | O | SER A | 345 | −25.406 | −13.356 | −53.005 | 1.00 | 39.29 | O |
| ATOM | 2501 | N | TYR A | 346 | −23.408 | −13.512 | −51.953 | 1.00 | 39.44 | N |
| ATOM | 2502 | CA | TYR A | 346 | −23.601 | −12.346 | −51.087 | 1.00 | 39.92 | C |
| ATOM | 2503 | CB | TYR A | 346 | −24.109 | −12.748 | −49.691 | 1.00 | 45.98 | C |
| ATOM | 2504 | CG | TYR A | 346 | −25.377 | −12.009 | −49.288 | 1.00 | 53.94 | C |
| ATOM | 2505 | CD1 | TYR A | 346 | −25.351 | −10.641 | −48.941 | 1.00 | 53.48 | C |
| ATOM | 2506 | CE1 | TYR A | 346 | −26.517 | −9.966 | −48.595 | 1.00 | 54.68 | C |
| ATOM | 2507 | CZ | TYR A | 346 | −27.734 | −10.660 | −48.591 | 1.00 | 59.40 | C |
| ATOM | 2508 | OH | TYR A | 346 | −28.904 | −10.023 | −48.247 | 1.00 | 62.09 | O |
| ATOM | 2509 | CE2 | TYR A | 346 | −27.787 | −12.008 | −48.928 | 1.00 | 59.83 | C |
| ATOM | 2510 | CD2 | TYR A | 346 | −26.618 | −12.673 | −49.278 | 1.00 | 59.01 | C |
| ATOM | 2511 | C | TYR A | 346 | −22.317 | −11.526 | −50.951 | 1.00 | 37.68 | C |
| ATOM | 2512 | O | TYR A | 346 | −21.209 | −12.041 | −51.118 | 1.00 | 37.25 | O |
| ATOM | 2513 | N | VAL A | 347 | −22.485 | −10.247 | −50.639 | 1.00 | 33.85 | N |
| ATOM | 2514 | CA | VAL A | 347 | −21.378 | −9.353 | −50.376 | 1.00 | 31.17 | C |
| ATOM | 2515 | CB | VAL A | 347 | −21.328 | −8.222 | −51.441 | 1.00 | 31.07 | C |
| ATOM | 2516 | CG1 | VAL A | 347 | −22.257 | −7.068 | −51.082 | 1.00 | 30.07 | C |
| ATOM | 2517 | CG2 | VAL A | 347 | −19.898 | −7.741 | −51.665 | 1.00 | 31.04 | C |
| ATOM | 2518 | C | VAL A | 347 | −21.529 | −8.816 | −48.942 | 1.00 | 30.11 | C |
| ATOM | 2519 | O | VAL A | 347 | −22.642 | −8.687 | −48.446 | 1.00 | 30.96 | O |
| ATOM | 2520 | N | VAL A | 348 | −20.414 | −8.549 | −48.269 | 1.00 | 28.64 | N |
| ATOM | 2521 | CA | VAL A | 348 | −20.433 | −8.050 | −46.892 | 1.00 | 27.21 | C |
| ATOM | 2522 | CB | VAL A | 348 | −20.251 | −9.197 | −45.860 | 1.00 | 26.79 | C |
| ATOM | 2523 | CG1 | VAL A | 348 | −19.221 | −8.840 | −44.793 | 1.00 | 25.64 | C |
| ATOM | 2524 | CG2 | VAL A | 348 | −21.591 | −9.559 | −45.228 | 1.00 | 26.24 | C |

-continued

| | | | Atomic coordinates for CRBN:DDB1:Lenalidomide (Human protein) | | | | | | |
|---|---|---|---|---|---|---|---|---|---|
| ATOM | 2525 | C | VAL A | 348 | −19.360 | −6.993 | −46.719 | 1.00 | 27.03 | C |
| ATOM | 2526 | O | VAL A | 348 | −18.333 | −7.032 | −47.394 | 1.00 | 27.17 | O |
| ATOM | 2527 | N | ALA A | 349 | −19.599 | −6.047 | −45.816 | 1.00 | 27.36 | N |
| ATOM | 2528 | CA | ALA A | 349 | −18.672 | −4.932 | −45.620 | 1.00 | 27.26 | C |
| ATOM | 2529 | CB | ALA A | 349 | −19.408 | −3.721 | −45.057 | 1.00 | 27.85 | C |
| ATOM | 2530 | C | ALA A | 349 | −17.525 | −5.334 | −44.714 | 1.00 | 26.24 | C |
| ATOM | 2531 | O | ALA A | 349 | −17.749 | −5.927 | −43.671 | 1.00 | 26.49 | O |
| ATOM | 2532 | N | MET A | 350 | −16.303 | −5.023 | −45.134 | 1.00 | 26.47 | N |
| ATOM | 2533 | CA | MET A | 350 | −15.088 | −5.310 | −44.360 | 1.00 | 27.68 | C |
| ATOM | 2534 | CB | MET A | 350 | −13.967 | −5.782 | −45.287 | 1.00 | 29.17 | C |
| ATOM | 2535 | CG | MET A | 350 | −14.050 | −7.224 | −45.758 | 1.00 | 31.52 | C |
| ATOM | 2536 | SD | MET A | 350 | −12.647 | −7.697 | −46.811 | 1.00 | 34.81 | S |
| ATOM | 2537 | CE | MET A | 350 | −11.228 | −7.210 | −45.812 | 1.00 | 33.90 | C |
| ATOM | 2538 | C | MET A | 350 | −14.605 | −4.046 | −43.662 | 1.00 | 27.94 | C |
| ATOM | 2539 | O | MET A | 350 | −14.371 | −4.027 | −42.446 | 1.00 | 27.69 | O |
| ATOM | 2540 | N | GLU A | 351 | −14.447 | −2.997 | −44.466 | 1.00 | 27.64 | N |
| ATOM | 2541 | CA | GLU A | 351 | −13.916 | −1.728 | −44.030 | 1.00 | 26.74 | C |
| ATOM | 2542 | CB | GLU A | 351 | −12.499 | −1.557 | −44.570 | 1.00 | 28.94 | C |
| ATOM | 2543 | CG | GLU A | 351 | −11.397 | −1.989 | −43.625 | 1.00 | 32.92 | C |
| ATOM | 2544 | CD | GLU A | 351 | −10.223 | −1.010 | −43.622 | 1.00 | 36.58 | C |
| ATOM | 2545 | OE1 | GLU A | 351 | −9.176 | −1.328 | −44.241 | 1.00 | 38.37 | O |
| ATOM | 2546 | OE2 | GLU A | 351 | −10.349 | 0.086 | −43.008 | 1.00 | 37.46 | O |
| ATOM | 2547 | C | GLU A | 351 | −14.764 | −0.574 | −44.540 | 1.00 | 25.08 | C |
| ATOM | 2548 | O | GLU A | 351 | −15.487 | −0.703 | −45.552 | 1.00 | 25.60 | O |
| ATOM | 2549 | N | THR A | 352 | −14.700 | 0.558 | −43.844 | 1.00 | 21.59 | N |
| ATOM | 2550 | CA | THR A | 352 | −15.315 | 1.810 | −44.266 | 1.00 | 18.39 | C |
| ATOM | 2551 | CB | THR A | 352 | −16.417 | 2.206 | −43.268 | 1.00 | 17.52 | C |
| ATOM | 2552 | OG1 | THR A | 352 | −17.603 | 1.493 | −43.581 | 1.00 | 16.85 | O |
| ATOM | 2553 | CG2 | THR A | 352 | −16.741 | 3.640 | −43.364 | 1.00 | 18.20 | C |
| ATOM | 2554 | C | THR A | 352 | −14.234 | 2.901 | −44.373 | 1.00 | 17.10 | C |
| ATOM | 2555 | O | THR A | 352 | −13.285 | 2.908 | −43.603 | 1.00 | 17.17 | O |
| ATOM | 2556 | N | PHE A | 353 | −14.360 | 3.800 | −45.343 | 1.00 | 16.02 | N |
| ATOM | 2557 | CA | PHE A | 353 | −13.434 | 4.931 | −45.472 | 1.00 | 14.91 | C |
| ATOM | 2558 | CB | PHE A | 353 | −12.577 | 4.838 | −46.746 | 1.00 | 15.41 | C |
| ATOM | 2559 | CG | PHE A | 353 | −11.810 | 3.553 | −46.873 | 1.00 | 16.17 | C |
| ATOM | 2560 | CD1 | PHE A | 353 | −10.584 | 3.387 | −46.223 | 1.00 | 16.20 | C |
| ATOM | 2561 | CE1 | PHE A | 353 | −9.876 | 2.192 | −46.336 | 1.00 | 16.37 | C |
| ATOM | 2562 | CZ | PHE A | 353 | −10.392 | 1.144 | −47.091 | 1.00 | 16.26 | C |
| ATOM | 2563 | CE2 | PHE A | 353 | −11.613 | 1.296 | −47.751 | 1.00 | 16.43 | C |
| ATOM | 2564 | CD2 | PHE A | 353 | −12.314 | 2.492 | −47.647 | 1.00 | 16.33 | C |
| ATOM | 2565 | C | PHE A | 353 | −14.228 | 6.214 | −45.492 | 1.00 | 13.90 | C |
| ATOM | 2566 | O | PHE A | 353 | −15.120 | 6.381 | −46.321 | 1.00 | 13.55 | O |
| ATOM | 2567 | | THR A | 354 | −13.873 | 7.129 | −44.595 | 1.00 | 13.01 | N |
| ATOM | 2568 | CA | THR A | 354 | −14.614 | 8.373 | −44.403 | 1.00 | 12.36 | C |
| ATOM | 2569 | CB | THR A | 354 | −13.956 | 9.250 | −43.325 | 1.00 | 12.24 | C |
| ATOM | 2570 | OG1 | THR A | 354 | −13.791 | 8.471 | −42.140 | 1.00 | 12.49 | O |
| ATOM | 2571 | CG2 | THR A | 354 | −14.824 | 10.426 | −42.974 | 1.00 | 12.27 | C |
| ATOM | 2572 | C | THR A | 354 | −14.790 | 9.173 | −45.675 | 1.00 | 11.86 | C |
| ATOM | 2573 | O | THR A | 354 | −13.822 | 9.458 | −46.370 | 1.00 | 11.56 | O |
| ATOM | 2574 | N | ASN A | 355 | −16.045 | 9.500 | −45.988 | 1.00 | 11.56 | N |
| ATOM | 2575 | CA | ASN A | 355 | −16.343 | 10.560 | −46.955 | 1.00 | 11.36 | C |
| ATOM | 2576 | CB | ASN A | 355 | −16.965 | 10.024 | −48.250 | 1.00 | 10.78 | C |
| ATOM | 2577 | CG | ASN A | 355 | −16.932 | 11.050 | −49.380 | 1.00 | 10.61 | C |
| ATOM | 2578 | OD1 | ASN A | 355 | −16.297 | 12.103 | −49.274 | 1.00 | 10.29 | O |
| ATOM | 2579 | ND2 | ASN A | 355 | −17.602 | 10.738 | −50.472 | 1.00 | 10.57 | N |
| ATOM | 2580 | C | ASN A | 355 | −17.209 | 11.674 | −46.373 | 1.00 | 11.54 | C |
| ATOM | 2581 | O | ASN A | 355 | −18.356 | 11.445 | −45.985 | 1.00 | 11.86 | O |
| ATOM | 2582 | N | LEU A | 356 | −16.659 | 12.883 | −46.327 | 1.00 | 11.63 | N |
| ATOM | 2583 | CA | LEU A | 356 | −17.458 | 14.059 | −45.988 | 1.00 | 11.73 | C |
| ATOM | 2584 | CB | LEU A | 356 | −16.576 | 15.193 | −45.444 | 1.00 | 11.61 | C |
| ATOM | 2585 | CG | LEU A | 356 | −15.512 | 14.842 | −44.402 | 1.00 | 11.49 | C |
| ATOM | 2586 | CD1 | LEU A | 356 | −14.839 | 16.107 | −43.924 | 1.00 | 11.62 | C |
| ATOM | 2587 | CD2 | LEU A | 356 | −16.093 | 14.089 | −43.222 | 1.00 | 11.50 | C |
| ATOM | 2588 | C | LEU A | 356 | −18.249 | 14.521 | −47.209 | 1.00 | 11.75 | C |
| ATOM | 2589 | O | LEU A | 356 | −19.248 | 15.199 | −47.067 | 1.00 | 11.78 | O |
| ATOM | 2590 | N | GLY A | 357 | −17.791 | 14.114 | −48.394 | 1.00 | 11.89 | N |
| ATOM | 2591 | CA | GLY A | 357 | −18.373 | 14.474 | −49.703 | 1.00 | 12.26 | C |
| ATOM | 2592 | C | GLY A | 357 | −19.878 | 14.465 | −49.875 | 1.00 | 12.60 | C |
| ATOM | 2593 | O | GLY A | 357 | −20.548 | 13.602 | −49.304 | 1.00 | 13.04 | O |
| ATOM | 2594 | N | PRO A | 358 | −20.363 | 15.201 | −50.895 | 1.00 | 12.77 | N |
| ATOM | 2595 | CA | PRO A | 358 | −21.027 | 16.492 | −50.849 | 1.00 | 12.46 | C |
| ATOM | 2596 | CB | PRO A | 358 | −22.404 | 16.228 | −51.491 | 1.00 | 12.58 | C |
| ATOM | 2597 | CG | PRO A | 358 | −22.556 | 14.752 | −51.522 | 1.00 | 12.56 | C |
| ATOM | 2598 | CD | PRO A | 358 | −21.135 | 14.307 | −51.775 | 1.00 | 13.01 | C |
| ATOM | 2599 | C | PRO A | 358 | −21.132 | 17.029 | −49.444 | 1.00 | 12.35 | C |
| ATOM | 2600 | O | PRO A | 358 | −21.839 | 16.460 | −48.617 | 1.00 | 12.33 | O |
| ATOM | 2601 | N | ILE A | 359 | −20.367 | 18.081 | −49.163 | 1.00 | 12.46 | N |

-continued

| \multicolumn{10}{c}{Atomic coordinates for CRBN:DDB1:Lenalidomide (Human protein)} |
|---|

| ATOM | 2602 | CA | ILE A | 359 | −20.664 | 18.943 | −48.034 | 1.00 | 12.20 | C |
|---|---|---|---|---|---|---|---|---|---|---|
| ATOM | 2603 | CB | ILE A | 359 | −19.435 | 19.640 | −47.461 | 1.00 | 11.94 | C |
| ATOM | 2604 | CG1 | ILE A | 359 | −18.414 | 18.605 | −47.033 | 1.00 | 11.88 | C |
| ATOM | 2605 | CD1 | ILE A | 359 | −17.375 | 19.126 | −46.071 | 1.00 | 12.02 | C |
| ATOM | 2606 | CG2 | ILE A | 359 | −19.841 | 20.477 | −46.260 | 1.00 | 12.09 | C |
| ATOM | 2607 | C | ILE A | 359 | −21.661 | 19.946 | −48.575 | 1.00 | 12.31 | C |
| ATOM | 2608 | O | ILE A | 359 | −21.326 | 20.843 | −49.353 | 1.00 | 12.20 | O |
| ATOM | 2609 | N | VAL A | 360 | −22.902 | 19.743 | −48.176 | 1.00 | 12.23 | N |
| ATOM | 2610 | CA | VAL A | 360 | −24.019 | 20.381 | −48.798 | 1.00 | 12.32 | C |
| ATOM | 2611 | CB | VAL A | 360 | −25.139 | 19.333 | −49.006 | 1.00 | 11.97 | C |
| ATOM | 2612 | CG1 | VAL A | 360 | −26.180 | 19.358 | −47.896 | 1.00 | 12.03 | C |
| ATOM | 2613 | CG2 | VAL A | 360 | −25.785 | 19.527 | −50.339 | 1.00 | 11.91 | C |
| ATOM | 2614 | C | VAL A | 360 | −24.428 | 21.589 | −47.950 | 1.00 | 12.82 | C |
| ATOM | 2615 | O | VAL A | 360 | −25.115 | 21.485 | −48.422 | 1.00 | 13.16 | O |
| ATOM | 2616 | N | ASP A | 361 | −23.985 | 21.590 | −46.692 | 1.00 | 13.58 | N |
| ATOM | 2617 | CA | ASP A | 361 | −24.116 | 22.711 | −45.759 | 1.00 | 14.20 | C |
| ATOM | 2618 | CB | ASP A | 361 | −25.573 | 23.023 | −45.462 | 1.00 | 15.47 | C |
| ATOM | 2619 | CG | ASP A | 361 | −25.737 | 24.174 | −44.461 | 1.00 | 17.20 | C |
| ATOM | 2620 | OD1 | ASP A | 361 | −24.907 | 24.141 | −44.467 | 1.00 | 17.38 | O |
| ATOM | 2621 | OD2 | ASP A | 361 | −26.711 | 24.108 | −43.664 | 1.00 | 18.39 | O |
| ATOM | 2622 | C | ASP A | 361 | −23.409 | 22.347 | −44.465 | 1.00 | 14.03 | C |
| ATOM | 2623 | O | ASP A | 361 | −23.262 | 21.167 | −44.163 | 1.00 | 14.11 | O |
| ATOM | 2624 | N | MET A | 362 | −22.967 | 23.353 | −43.709 | 1.00 | 13.88 | N |
| ATOM | 2625 | CA | MET A | 362 | −22.294 | 23.124 | −42.422 | 1.00 | 14.00 | C |
| ATOM | 2626 | CB | MET A | 362 | −20.795 | 22.868 | −42.628 | 1.00 | 14.03 | C |
| ATOM | 2627 | CG | MET A | 362 | −19.983 | 24.082 | −43.072 | 1.00 | 13.91 | C |
| ATOM | 2628 | SD | MET A | 362 | −18.347 | 23.594 | −43.652 | 1.00 | 13.89 | S |
| ATOM | 2629 | CE | MET A | 362 | −17.575 | 25.192 | −43.929 | 1.00 | 13.90 | C |
| ATOM | 2630 | C | MET A | 362 | −22.499 | 24.277 | −41.448 | 1.00 | 14.16 | C |
| ATOM | 2631 | O | MET A | 362 | −22.950 | 25.341 | −41.838 | 1.00 | 14.67 | O |
| ATOM | 2632 | N | CYS A | 363 | −22.175 | 24.066 | −40.181 | 1.00 | 14.45 | N |
| ATOM | 2633 | CA | CYS A | 363 | −22.151 | 25.153 | −39.212 | 1.00 | 15.06 | C |
| ATOM | 2634 | CB | CYS A | 363 | −23.507 | 25.317 | −38.546 | 1.00 | 15.06 | C |
| ATOM | 2635 | SG | CYS A | 363 | −23.849 | 24.023 | −37.338 | 1.00 | 15.23 | S |
| ATOM | 2636 | C | CYS A | 363 | −21.110 | 24.877 | −38.150 | 1.00 | 15.95 | C |
| ATOM | 2637 | O | CYS A | 363 | −20.691 | 23.730 | −37.960 | 1.00 | 15.73 | O |
| ATOM | 2638 | N | VAL A | 364 | −20.712 | 25.934 | −37.444 | 1.00 | 17.74 | N |
| ATOM | 2639 | CA | VAL A | 364 | −19.688 | 25.841 | −36.403 | 1.00 | 19.45 | C |
| ATOM | 2640 | CB | VAL A | 364 | −18.593 | 26.913 | −36.574 | 1.00 | 19.10 | C |
| ATOM | 2641 | CG1 | VAL A | 364 | −17.461 | 26.669 | −35.594 | 1.00 | 19.26 | C |
| ATOM | 2642 | CG2 | VAL A | 364 | −18.053 | 26.898 | −38.000 | 1.00 | 19.07 | C |
| ATOM | 2643 | C | VAL A | 364 | −20.278 | 25.913 | −34.999 | 1.00 | 21.05 | C |
| ATOM | 2644 | O | VAL A | 364 | −21.057 | 26.809 | −34.686 | 1.00 | 20.92 | O |
| ATOM | 2645 | N | VAL A | 365 | −19.902 | 24.936 | −34.181 | 1.00 | 23.78 | N |
| ATOM | 2646 | CA | VAL A | 365 | −20.223 | 24.891 | −32.765 | 1.00 | 26.65 | C |
| ATOM | 2647 | CB | VAL A | 365 | −20.724 | 23.491 | −32.372 | 1.00 | 27.02 | C |
| ATOM | 2648 | CG1 | VAL A | 365 | −20.709 | 23.306 | −30.859 | 1.00 | 27.17 | C |
| ATOM | 2649 | CG2 | VAL A | 365 | −22.110 | 23.244 | −32.948 | 1.00 | 26.67 | C |
| ATOM | 2650 | C | VAL A | 365 | −18.959 | 25.206 | −31.976 | 1.00 | 29.41 | C |
| ATOM | 2651 | O | VAL A | 365 | −17.920 | 24.585 | −32.202 | 1.00 | 29.13 | O |
| ATOM | 2652 | N | ASP A | 366 | −19.072 | 26.161 | −31.047 | 1.00 | 35.42 | N |
| ATOM | 2653 | CA | ASP A | 366 | −17.952 | 26.703 | −30.241 | 1.00 | 40.74 | C |
| ATOM | 2654 | CB | ASP A | 366 | −17.101 | 25.595 | −29.603 | 1.00 | 41.72 | C |
| ATOM | 2655 | CG | ASP A | 366 | −17.560 | 25.236 | −28.215 | 1.00 | 42.44 | C |
| ATOM | 2656 | OD1 | ASP A | 366 | −17.140 | 25.927 | −27.265 | 1.00 | 45.49 | O |
| ATOM | 2657 | OD2 | ASP A | 366 | −18.326 | 24.258 | −28.068 | 1.00 | 42.14 | O |
| ATOM | 2658 | C | ASP A | 366 | −17.071 | 27.658 | −31.032 | 1.00 | 45.09 | C |
| ATOM | 2659 | O | ASP A | 366 | −16.312 | 27.250 | −31.914 | 1.00 | 47.68 | O |
| ATOM | 2660 | N | LEU A | 367 | −17.175 | 28.937 | −30.713 | 1.00 | 50.28 | N |
| ATOM | 2661 | CA | LEU A | 367 | −16.324 | 29.932 | −31.342 | 1.00 | 55.43 | C |
| ATOM | 2662 | CB | LEU A | 367 | −17.149 | 30.842 | −32.269 | 1.00 | 56.79 | C |
| ATOM | 2663 | CG | LEU A | 367 | −17.680 | 30.195 | −33.564 | 1.00 | 56.43 | C |
| ATOM | 2664 | CD1 | LEU A | 367 | −18.979 | 30.830 | −34.057 | 1.00 | 54.94 | C |
| ATOM | 2665 | CD2 | LEU A | 367 | −16.619 | 30.215 | −34.660 | 1.00 | 55.26 | C |
| ATOM | 2666 | C | LEU A | 367 | −15.545 | 30.715 | −30.273 | 1.00 | 58.87 | C |
| ATOM | 2667 | O | LEU A | 367 | −15.642 | 31.945 | −30.183 | 1.00 | 59.40 | O |
| ATOM | 2668 | N | GLU A | 368 | −14.799 | 29.971 | −29.451 | 1.00 | 60.73 | N |
| ATOM | 2669 | CA | GLU A | 368 | −13.858 | 30.536 | −28.472 | 1.00 | 61.33 | C |
| ATOM | 2670 | CB | GLU A | 368 | −14.580 | 30.947 | −27.179 | 1.00 | 59.87 | C |
| ATOM | 2671 | C | GLU A | 368 | −12.725 | 29.545 | −28.157 | 1.00 | 63.08 | C |
| ATOM | 2672 | O | GLU A | 368 | −12.174 | 28.884 | −29.051 | 1.00 | 60.50 | O |
| ATOM | 2673 | N | GLN A | 372 | −12.776 | 25.451 | −27.814 | 1.00 | 51.93 | N |
| ATOM | 2674 | CA | GLN A | 372 | −12.486 | 24.211 | −28.538 | 1.00 | 50.78 | C |
| ATOM | 2675 | C | GLN A | 372 | −12.603 | 24.415 | −30.047 | 1.00 | 49.19 | C |
| ATOM | 2676 | O | GLN A | 372 | −11.594 | 24.638 | −30.730 | 1.00 | 49.67 | O |
| ATOM | 2677 | N | GLY A | 373 | −13.838 | 24.340 | −30.550 | 1.00 | 46.04 | N |
| ATOM | 2678 | CA | GLY A | 373 | −14.144 | 24.566 | −31.972 | 1.00 | 40.70 | C |

-continued

| | | | | | | | | | | |
|---|---|---|---|---|---|---|---|---|---|---|
| \multicolumn{11}{c}{Atomic coordinates for CRBN:DDB1:Lenalidomide (Human protein)} |
| ATOM | 2679 | C | GLY A | 373 | −14.478 | 23.276 | −32.697 | 1.00 | 36.55 | C |
| ATOM | 2680 | O | GLY A | 373 | −13.614 | 22.418 | −32.875 | 1.00 | 37.21 | O |
| ATOM | 2681 | N | GLN A | 374 | −15.735 | 23.113 | −33.093 | 1.00 | 32.53 | N |
| ATOM | 2682 | CA | GLN A | 374 | −16.113 | 21.924 | −33.856 | 1.00 | 29.15 | C |
| ATOM | 2683 | CB | GLN A | 374 | −16.612 | 20.793 | −32.954 | 1.00 | 29.42 | C |
| ATOM | 2684 | CG | GLN A | 374 | −18.067 | 20.897 | −32.559 | 1.00 | 31.55 | C |
| ATOM | 2685 | CD | GLN A | 374 | −18.494 | 19.816 | −31.582 | 1.00 | 33.38 | C |
| ATOM | 2686 | OE1 | GLN A | 374 | −19.673 | 19.725 | −31.211 | 1.00 | 34.04 | O |
| ATOM | 2687 | NE2 | GLN A | 374 | −17.538 | 18.996 | −31.145 | 1.00 | 33.82 | N |
| ATOM | 2688 | C | GLN A | 374 | −17.096 | 22.231 | −34.978 | 1.00 | 25.87 | C |
| ATOM | 2689 | O | GLN A | 374 | −17.948 | 23.117 | −34.866 | 1.00 | 27.88 | O |
| ATOM | 2690 | N | LEU A | 375 | −16.950 | 21.484 | −36.062 | 1.00 | 22.20 | N |
| ATOM | 2691 | CA | LEU A | 375 | −17.629 | 21.778 | −37.94 | 1.00 | 19.60 | C |
| ATOM | 2692 | CB | LEU A | 375 | −16.601 | 21.839 | −38.410 | 1.00 | 19.42 | C |
| ATOM | 2693 | CG | LEU A | 375 | −17.054 | 22.172 | −39.819 | 1.00 | 19.98 | C |
| ATOM | 2694 | CD1 | LEU A | 375 | −17.587 | 23.589 | −39.918 | 1.00 | 20.06 | C |
| ATOM | 2695 | CD2 | LEU A | 375 | −15.870 | 22.008 | −40.741 | 1.00 | 20.34 | C |
| ATOM | 2696 | C | LEU A | 375 | −18.625 | 20.676 | −37.541 | 1.00 | 18.01 | C |
| ATOM | 2697 | O | LEU A | 375 | −18.317 | 19.514 | −37.332 | 1.00 | 18.45 | O |
| ATOM | 2698 | N | VAL A | 376 | −19.838 | 21.029 | −37.940 | 1.00 | 16.28 | N |
| ATOM | 2699 | CA | VAL A | 376 | −20.850 | 20.003 | −38.205 | 1.00 | 15.45 | C |
| ATOM | 2700 | CB | VAL A | 376 | −22.082 | 20.152 | −37.278 | 1.00 | 14.93 | C |
| ATOM | 2701 | CG1 | VAL A | 376 | −23.056 | 18.993 | −37.486 | 1.00 | 14.41 | C |
| ATOM | 2702 | CG2 | VAL A | 376 | −21.655 | 20.241 | −35.825 | 1.00 | 14.44 | C |
| ATOM | 2703 | C | VAL A | 376 | −21.273 | 20.066 | −39.677 | 1.00 | 15.03 | C |
| ATOM | 2704 | O | VAL A | 376 | −21.519 | 21.156 | −40.200 | 1.00 | 15.54 | O |
| ATOM | 2705 | N | THR A | 377 | −21.343 | 18.934 | −40.367 | 1.00 | 13.94 | N |
| ATOM | 2706 | CA | THR A | 377 | −21.742 | 19.020 | −41.771 | 1.00 | 13.61 | C |
| ATOM | 2707 | CB | THR A | 377 | −20.620 | 18.625 | −42.747 | 1.00 | 13.28 | C |
| ATOM | 2708 | OG1 | THR A | 377 | −20.491 | 17.207 | −42.744 | 1.00 | 13.43 | O |
| ATOM | 2709 | CG2 | THR A | 377 | −19.306 | 19.269 | −42.387 | 1.00 | 13.05 | C |
| ATOM | 2710 | C | THR A | 377 | −22.978 | 18.211 | −42.145 | 1.00 | 13.36 | C |
| ATOM | 2711 | O | THR A | 377 | −23.268 | 17.162 | −41.545 | 1.00 | 13.22 | O |
| ATOM | 2712 | N | CYS A | 378 | −23.685 | 18.706 | −43.157 | 1.00 | 12.81 | N |
| ATOM | 2713 | CA | CYS A | 378 | −24.672 | 17.919 | −43.855 | 1.00 | 12.64 | C |
| ATOM | 2714 | CB | CYS A | 378 | −25.828 | 18.795 | −44.304 | 1.00 | 12.74 | C |
| ATOM | 2715 | SG | CYS A | 378 | −26.703 | 19.527 | −42.914 | 1.00 | 12.82 | S |
| ATOM | 2716 | C | CYS A | 378 | −23.990 | 17.270 | −45.042 | 1.00 | 12.44 | C |
| ATOM | 2717 | O | CYS A | 378 | −23.731 | 17.930 | −46.052 | 1.00 | 12.44 | O |
| ATOM | 2718 | N | SER A | 379 | −23.691 | 15.975 | −44.901 | 1.00 | 12.26 | N |
| ATOM | 2719 | CA | SER A | 379 | −22.870 | 15.228 | −45.863 | 1.00 | 11.86 | C |
| ATOM | 2720 | CB | SER A | 379 | −21.644 | 14.648 | −45.172 | 1.00 | 11.74 | C |
| ATOM | 2721 | OG | SER A | 379 | −20.775 | 15.671 | −44.734 | 1.00 | 11.56 | O |
| ATOM | 2722 | C | SER A | 379 | −23.642 | 14.109 | −46.524 | 1.00 | 11.78 | C |
| ATOM | 2723 | O | SER A | 379 | −24.519 | 13.490 | −45.912 | 1.00 | 11.93 | O |
| ATOM | 2724 | N | GLY A | 380 | −23.330 | 13.866 | −47.788 | 1.00 | 11.69 | N |
| ATOM | 2725 | CA | GLY A | 380 | −23.923 | 12.759 | −48.503 | 1.00 | 11.96 | C |
| ATOM | 2726 | C | GLY A | 380 | −25.344 | 12.964 | −48.984 | 1.00 | 12.33 | C |
| ATOM | 2727 | O | GLY A | 380 | −25.888 | 14.075 | −48.953 | 1.00 | 12.47 | O |
| ATOM | 2728 | N | ALA A | 381 | −25.954 | 11.870 | −49.426 | 1.00 | 12.52 | N |
| ATOM | 2729 | CA | ALA A | 381 | −27.173 | 11.936 | −50.220 | 1.00 | 12.63 | C |
| ATOM | 2730 | CB | ALA A | 381 | −26.833 | 12.317 | −51.659 | 1.00 | 12.47 | C |
| ATOM | 2731 | C | ALA A | 381 | −27.925 | 10.609 | −50.177 | 1.00 | 12.78 | C |
| ATOM | 2732 | O | ALA A | 381 | −27.313 | 9.541 | −50.055 | 1.00 | 12.78 | O |
| ATOM | 2733 | N | PHE A | 382 | −29.251 | 10.684 | −50.285 | 1.00 | 12.81 | N |
| ATOM | 2734 | CA | PHE A | 382 | −30.110 | 9.512 | −50.198 | 1.00 | 12.87 | C |
| ATOM | 2735 | CB | PHE A | 382 | −30.138 | 8.795 | −51.528 | 1.00 | 13.21 | C |
| ATOM | 2736 | CG | PHE A | 382 | −30.129 | 9.733 | −52.694 | 1.00 | 13.87 | C |
| ATOM | 2737 | CD1 | PHE A | 382 | −31.261 | 10.476 | −53.017 | 1.00 | 14.21 | C |
| ATOM | 2738 | CE1 | PHE A | 382 | −31.257 | 11.357 | −54.095 | 1.00 | 14.38 | C |
| ATOM | 2739 | CZ | PHE A | 382 | −30.112 | 11.510 | −54.856 | 1.00 | 14.32 | C |
| ATOM | 2740 | CE2 | PHE A | 382 | −28.971 | 10.785 | −54.539 | 1.00 | 14.43 | C |
| ATOM | 2741 | CD2 | PHE A | 382 | −28.979 | 9.908 | −53.460 | 1.00 | 14.19 | C |
| ATOM | 2742 | C | PHE A | 382 | −29.695 | 8.619 | −49.027 | 1.00 | 12.86 | C |
| ATOM | 2743 | O | PHE A | 382 | −29.614 | 9.109 | −47.907 | 1.00 | 12.94 | O |
| ATOM | 2744 | N | LYS A | 383 | −29.414 | 7.339 | −49.249 | 1.00 | 12.98 | N |
| ATOM | 2745 | CA | LYS A | 383 | −29.166 | 6.458 | −48.097 | 1.00 | 13.48 | C |
| ATOM | 2746 | CB | LYS A | 383 | −29.280 | 4.970 | −48.467 | 1.00 | 13.45 | C |
| ATOM | 2747 | CG | LYS A | 383 | −28.300 | 4.444 | −49.507 | 1.00 | 13.68 | C |
| ATOM | 2748 | CD | LYS A | 383 | −28.423 | 2.923 | −49.601 | 1.00 | 13.76 | C |
| ATOM | 2749 | CE | LYS A | 383 | −27.251 | 2.273 | −50.326 | 1.00 | 14.10 | C |
| ATOM | 2750 | NZ | LYS A | 383 | −26.025 | 2.129 | −49.492 | 1.00 | 13.74 | N |
| ATOM | 2751 | C | LYS A | 383 | −27.855 | 6.794 | −47.345 | 1.00 | 13.86 | C |
| ATOM | 2752 | O | LYS A | 383 | −27.682 | 6.461 | −46.153 | 1.00 | 14.01 | O |
| ATOM | 2753 | N | GLU A | 384 | −26.975 | 7.519 | −48.028 | 1.00 | 13.90 | N |
| ATOM | 2754 | CA | GLU A | 384 | −25.685 | 7.884 | −47.470 | 1.00 | 14.01 | C |
| ATOM | 2755 | CB | GLU A | 384 | −24.660 | 8.046 | −48.587 | 1.00 | 14.80 | C |

-continued

| Atomic coordinates for CRBN:DDB1:Lenalidomide (Human protein) | | | | | | | | | |
|---|---|---|---|---|---|---|---|---|---|
| ATOM | 2756 | CG | GLU A | 384 | −24.640 | 6.903 | −49.592 | 1.00 | 16.26 | C |
| ATOM | 2757 | CD | GLU A | 384 | −24.344 | 5.565 | −48.948 | 1.00 | 17.79 | C |
| ATOM | 2758 | OE1 | GLU A | 384 | −23.604 | 5.566 | −47.920 | 1.00 | 19.21 | O |
| ATOM | 2759 | OE2 | GLU A | 384 | −24.846 | 4.523 | −49.461 | 1.00 | 17.80 | O |
| ATOM | 2760 | C | GLU A | 384 | −25.718 | 9.134 | −46.597 | 1.00 | 13.39 | C |
| ATOM | 2761 | O | GLU A | 384 | −24.725 | 9.452 | −45.930 | 1.00 | 13.32 | O |
| ATOM | 2762 | N | GLY A | 385 | −26.848 | 9.838 | −46.594 | 1.00 | 12.81 | N |
| ATOM | 2763 | CA | GLY A | 385 | −26.974 | 11.086 | −45.840 | 1.00 | 12.23 | C |
| ATOM | 2764 | C | GLY A | 385 | −26.512 | 10.945 | −44.403 | 1.00 | 11.81 | C |
| ATOM | 2765 | O | GLY A | 385 | −26.864 | 9.986 | −43.722 | 1.00 | 12.01 | O |
| ATOM | 2766 | N | SER A | 386 | −25.701 | 11.883 | −43.940 | 1.00 | 11.43 | N |
| ATOM | 2767 | CA | SER A | 386 | −25.188 | 11.806 | −42.583 | 1.00 | 11.42 | C |
| ATOM | 2768 | CB | SER A | 386 | −23.917 | 10.928 | −42.499 | 1.00 | 11.40 | C |
| ATOM | 2769 | OG | SER A | 386 | −22.783 | 11.560 | −43.090 | 1.00 | 11.22 | O |
| ATOM | 2770 | C | SER A | 386 | −24.878 | 13.169 | −42.042 | 1.00 | 11.35 | C |
| ATOM | 2771 | O | SER A | 386 | −24.697 | 14.121 | −42.798 | 1.00 | 11.08 | O |
| ATOM | 2772 | N | LEU A | 387 | −24.812 | 13.249 | −40.720 | 1.00 | 11.52 | N |
| ATOM | 2773 | CA | LEU A | 387 | −24.147 | 14.348 | −40.074 | 1.00 | 11.92 | C |
| ATOM | 2774 | CB | LEU A | 387 | −24.886 | 14.745 | −38.800 | 1.00 | 11.64 | C |
| ATOM | 2775 | CG | LEU A | 387 | −26.249 | 15.398 | −39.073 | 1.00 | 11.59 | C |
| ATOM | 2776 | CD1 | LEU A | 387 | −26.787 | 16.104 | −37.836 | 1.00 | 11.52 | C |
| ATOM | 2777 | CD2 | LEU A | 387 | −26.186 | 16.361 | −40.257 | 1.00 | 11.39 | C |
| ATOM | 2778 | C | LEU A | 387 | −22.708 | 13.918 | −39.778 | 1.00 | 12.49 | C |
| ATOM | 2779 | O | LEU A | 387 | −22.481 | 12.778 | −39.329 | 1.00 | 12.62 | O |
| ATOM | 2800 | N | ARG A | 388 | −21.744 | 14.799 | −40.088 | 1.00 | 12.57 | N |
| ATOM | 2781 | CA | ARG A | 388 | −20.358 | 14.620 | −39.658 | 1.00 | 12.82 | C |
| ATOM | 2782 | CB | ARG A | 388 | −19.390 | 14.680 | −40.839 | 1.00 | 12.17 | C |
| ATOM | 2783 | CG | ARG A | 388 | −19.657 | 13.658 | −41.936 | 1.00 | 11.89 | C |
| ATOM | 2784 | CD | ARG A | 388 | −19.388 | 12.221 | −41.510 | 1.00 | 11.48 | C |
| ATOM | 2785 | NE | ARG A | 388 | −20.055 | 11.271 | −42.402 | 1.00 | 11.25 | N |
| ATOM | 2786 | CZ | ARG A | 388 | −19.450 | 10.291 | −43.069 | 1.00 | 11.20 | C |
| ATOM | 2787 | NH1 | ARG A | 388 | −18.152 | 10.097 | −42.953 | 1.00 | 11.41 | N |
| ATOM | 2788 | NH2 | ARG A | 388 | −20.145 | 9.491 | −43.851 | 1.00 | 11.06 | N |
| ATOM | 2789 | C | ARG A | 388 | −19.987 | 15.679 | −38.613 | 1.00 | 13.83 | C |
| ATOM | 2790 | O | ARG A | 388 | −20.147 | 16.888 | −38.858 | 1.00 | 14.32 | O |
| ATOM | 2791 | N | ILE A | 389 | −19.505 | 15.214 | −37.453 | 1.00 | 14.39 | N |
| ATOM | 2792 | CA | ILE A | 389 | −18.971 | 16.084 | −36.402 | 1.00 | 14.98 | C |
| ATOM | 2793 | CB | ILE A | 389 | −19.503 | 15.706 | −35.002 | 1.00 | 15.18 | C |
| ATOM | 2794 | CG1 | ILE A | 389 | −21.025 | 15.574 | −35.014 | 1.00 | 15.58 | C |
| ATOM | 2795 | CD1 | ILE A | 389 | −21.543 | 14.261 | −35.556 | 1.00 | 15.81 | C |
| ATOM | 2796 | CG2 | ILE A | 389 | −19.146 | 16.785 | −33.992 | 1.00 | 15.21 | C |
| ATOM | 2797 | C | ILE A | 389 | −17.452 | 15.983 | −36.402 | 1.00 | 15.10 | C |
| ATOM | 2798 | O | ILE A | 389 | −16.920 | 14.897 | −36.248 | 1.00 | 15.47 | O |
| ATOM | 2799 | N | ILE A | 390 | −16.774 | 17.117 | −36.577 | 1.00 | 15.22 | N |
| ATOM | 2800 | CA | ILE A | 390 | −15.325 | 17.165 | −36.778 | 1.00 | 15.65 | C |
| ATOM | 2801 | CB | ILE A | 390 | −14.961 | 17.774 | −38.141 | 1.00 | 15.37 | C |
| ATOM | 2802 | CG1 | ILE A | 390 | −15.519 | 16.922 | −39.262 | 1.00 | 15.72 | C |
| ATOM | 2803 | CD1 | ILE A | 390 | −15.465 | 17.588 | −40.613 | 1.00 | 16.03 | C |
| ATOM | 2804 | CG2 | ILE A | 390 | −13.456 | 17.887 | −38.291 | 1.00 | 15.48 | C |
| ATOM | 2805 | C | ILE A | 390 | −14.665 | 18.031 | −35.732 | 1.00 | 16.38 | C |
| ATOM | 2806 | O | ILE A | 390 | −14.927 | 19.241 | −35.669 | 1.00 | 16.56 | O |
| ATOM | 2807 | N | ARG A | 391 | −13.804 | 17.409 | −34.924 | 1.00 | 17.28 | N |
| ATOM | 2808 | CA | ARG A | 391 | −13.002 | 18.112 | −33.919 | 1.00 | 18.14 | C |
| ATOM | 2809 | CB | ARG A | 391 | −13.467 | 17.782 | −32.501 | 1.00 | 17.08 | C |
| ATOM | 2810 | C | ARG A | 391 | −11.529 | 17.757 | −34.090 | 1.00 | 19.50 | C |
| ATOM | 2811 | O | ARG A | 391 | −11.179 | 16.611 | −34.393 | 1.00 | 19.77 | O |
| ATOM | 2812 | N | ASN A | 392 | −10.671 | 18.758 | −33.929 | 1.00 | 20.91 | N |
| ATOM | 2813 | CA | ASN A | 392 | −9.246 | 18.538 | −33.840 | 1.00 | 21.32 | C |
| ATOM | 2814 | CB | ASN A | 392 | −8.514 | 19.817 | −34.198 | 1.00 | 21.85 | C |
| ATOM | 2815 | CG | ASN A | 392 | −7.131 | 19.561 | −34.750 | 1.00 | 23.02 | C |
| ATOM | 2816 | OD1 | ASN A | 392 | −6.730 | 18.406 | −34.968 | 1.00 | 23.84 | O |
| ATOM | 2817 | ND2 | ASN A | 392 | −6.385 | 20.640 | −34.989 | 1.00 | 23.27 | N |
| ATOM | 2818 | C | ASN A | 392 | −8.946 | 18.179 | −32.402 | 1.00 | 22.14 | C |
| ATOM | 2819 | O | ASN A | 392 | −9.557 | 18.735 | −31.493 | 1.00 | 23.15 | O |
| ATOM | 2820 | N | GLY A | 393 | −8.027 | 17.254 | −32.175 | 1.00 | 22.26 | N |
| ATOM | 2821 | CA | GLY A | 393 | −7.653 | 16.950 | −30.809 | 1.00 | 22.20 | C |
| ATOM | 2822 | C | GLY A | 393 | −6.817 | 15.714 | −30.637 | 1.00 | 22.90 | C |
| ATOM | 2823 | O | GLY A | 393 | −6.591 | 14.957 | −31.585 | 1.00 | 22.77 | O |
| ATOM | 2824 | N | ILE A | 394 | −6.342 | 15.522 | −29.413 | 1.00 | 24.16 | N |
| ATOM | 2825 | CA | ILE A | 394 | −5.660 | 14.300 | −29.041 | 1.00 | 25.52 | C |
| ATOM | 2826 | CB | ILE A | 394 | −4.648 | 14.534 | −27.908 | 1.00 | 26.49 | C |
| ATOM | 2827 | CG1 | ILE A | 394 | −3.594 | 15.555 | −28.354 | 1.00 | 27.17 | C |
| ATOM | 2828 | CD1 | ILE A | 394 | −2.612 | 15.955 | −27.273 | 1.00 | 27.75 | C |
| ATOM | 2829 | CG2 | ILE A | 394 | −3.999 | 13.215 | −27.503 | 1.00 | 26.66 | C |
| ATOM | 2830 | C | ILE A | 394 | −6.693 | 13.272 | −28.612 | 1.00 | 25.49 | C |
| ATOM | 2831 | O | ILE A | 394 | −7.428 | 13.49 | −27.654 | 1.00 | 25.29 | O |
| ATOM | 2832 | N | GLY A | 395 | −6.743 | 12.160 | −29.344 | 1.00 | 26.03 | N |

-continued

| | | | Atomic coordinates for CRBN:DDB1:Lenalidomide (Human protein) | | | | | | |
|---|---|---|---|---|---|---|---|---|---|
| ATOM | 2833 | CA | GLY A | 395 | −7.663 | 11.068 | −29.059 | 1.00 | 25.95 | C |
| ATOM | 2834 | C | GLY A | 395 | −7.143 | 10.090 | −28.019 | 1.00 | 26.92 | C |
| ATOM | 2835 | O | GLY A | 395 | −5.942 | 10.041 | −27.720 | 1.00 | 26.91 | O |
| ATOM | 2836 | N | ILE A | 396 | −8.065 | 9.314 | −27.463 | 1.00 | 27.46 | N |
| ATOM | 2837 | CA | ILE A | 396 | −7.748 | 8.306 | −26.474 | 1.00 | 27.74 | C |
| ATOM | 2838 | CB | ILE A | 396 | −8.168 | 8.770 | −25.063 | 1.00 | 27.72 | C |
| ATOM | 2839 | CG1 | ILE A | 396 | −7.121 | 9.729 | −24.511 | 1.00 | 27.93 | C |
| ATOM | 2840 | CD1 | ILE A | 396 | −7.539 | 10.460 | −23.243 | 1.00 | 28.64 | C |
| ATOM | 2841 | CG2 | ILE A | 396 | −8.351 | 7.595 | −24.111 | 1.00 | 27.95 | C |
| ATOM | 2842 | C | ILE A | 396 | −8.431 | 7.002 | −26.852 | 1.00 | 29.01 | C |
| ATOM | 2843 | O | ILE A | 396 | −9.646 | 6.939 | −26.982 | 1.00 | 28.88 | O |
| ATOM | 2844 | N | HIS A | 397 | −7.624 | 5.976 | −27.076 | 1.00 | 32.61 | N |
| ATOM | 2845 | CA | HIS A | 397 | −8.101 | 4.611 | −27.169 | 1.00 | 36.36 | C |
| ATOM | 2846 | CB | HIS A | 397 | −6.995 | 3.728 | −27.739 | 1.00 | 41.27 | C |
| ATOM | 2847 | CG | HIS A | 397 | −7.483 | 2.679 | −28.720 | 1.00 | 47.60 | C |
| ATOM | 2848 | ND1 | HIS A | 397 | −7.174 | 1.367 | −28.597 | 1.00 | 48.86 | N |
| ATOM | 2849 | CE1 | HIS A | 397 | −7.738 | 0.677 | −29.611 | 1.00 | 50.91 | C |
| ATOM | 2850 | NE2 | HIS A | 397 | −8.411 | 1.549 | −30.391 | 1.00 | 51.76 | N |
| ATOM | 2851 | CD2 | HIS A | 397 | −8.274 | 2.791 | −29.847 | 1.00 | 49.70 | C |
| ATOM | 2852 | C | HIS A | 397 | −8.482 | 4.155 | −25.780 | 1.00 | 36.75 | C |
| ATOM | 2853 | O | HIS A | 397 | −7.735 | 4.360 | −24.820 | 1.00 | 37.98 | O |
| ATOM | 2854 | N | GLU A | 398 | −9.658 | 3.559 | −25.641 | 1.00 | 36.38 | N |
| ATOM | 2855 | CA | GLU A | 398 | −10.070 | 3.023 | −24.349 | 1.00 | 35.42 | C |
| ATOM | 2856 | CB | GLU A | 398 | −11.512 | 3.385 | −24.055 | 1.00 | 36.55 | C |
| ATOM | 2857 | CG | GLU A | 398 | −11.767 | 4.878 | −24.025 | 1.00 | 38.98 | C |
| ATOM | 2858 | CD | GLU A | 398 | −13.234 | 5.197 | −23.848 | 1.00 | 40.95 | C |
| ATOM | 2859 | OE1 | GLU A | 398 | −13.686 | 6.236 | −24.393 | 1.00 | 40.78 | O |
| ATOM | 2860 | OE2 | GLU A | 398 | −13.930 | 4.395 | −23.175 | 1.00 | 41.22 | O |
| ATOM | 2861 | C | GLU A | 398 | −9.904 | 1.521 | −24.313 | 1.00 | 34.46 | C |
| ATOM | 2862 | O | GLU A | 398 | −10.301 | 0.828 | −25.240 | 1.00 | 35.34 | O |
| ATOM | 2863 | N | HIS A | 399 | −9.320 | 1.016 | −23.238 | 1.00 | 33.53 | N |
| ATOM | 2864 | CA | HIS A | 399 | −9.094 | −0.410 | −23.119 | 1.00 | 33.10 | C |
| ATOM | 2865 | CB | HIS A | 399 | −7.624 | −0.695 | −22.846 | 1.00 | 35.00 | C |
| ATOM | 2866 | CG | HIS A | 399 | −6.700 | −0.215 | −23.948 | 1.00 | 36.95 | C |
| ATOM | 2867 | ND1 | HIS A | 399 | −5.626 | 0.570 | −23.709 | 1.00 | 36.97 | N |
| ATOM | 2868 | CE1 | HIS A | 399 | −5.007 | 0.846 | −24.873 | 1.00 | 37.06 | C |
| ATOM | 2869 | NE2 | HIS A | 399 | −5.686 | 0.238 | −25.866 | 1.00 | 37.24 | N |
| ATOM | 2870 | CD2 | HIS A | 399 | −6.736 | −0.422 | −25.333 | 1.00 | 36.54 | C |
| ATOM | 2871 | C | HIS A | 399 | −9.974 | −1.032 | −22.083 | 1.00 | 32.19 | C |
| ATOM | 2872 | O | HIS A | 399 | −10.410 | −2.174 | −22.239 | 1.00 | 33.51 | O |
| ATOM | 2873 | N | ALA A | 400 | −10.260 | −0.280 | −21.022 | 1.00 | 30.92 | N |
| ATOM | 2874 | CA | ALA A | 400 | −11.107 | −0.762 | −19.928 | 1.00 | 29.60 | C |
| ATOM | 2875 | CB | ALA A | 400 | −10.252 | −1.418 | −18.848 | 1.00 | 29.40 | C |
| ATOM | 2876 | C | ALA A | 400 | −11.985 | 0.341 | −19.323 | 1.00 | 28.81 | C |
| ATOM | 2877 | O | ALA A | 400 | −11.585 | 1.504 | −19.249 | 1.00 | 29.05 | O |
| ATOM | 2878 | N | SER A | 401 | −13.179 | −0.041 | −18.885 | 1.00 | 27.59 | N |
| ATOM | 2879 | CA | SER A | 401 | −14.077 | 0.860 | −18.175 | 1.00 | 27.15 | C |
| ATOM | 2880 | CB | SER A | 401 | −15.325 | 1.111 | −19.028 | 1.00 | 26.60 | C |
| ATOM | 2881 | OG | SER A | 401 | −16.239 | 1.986 | −18.404 | 1.00 | 25.91 | O |
| ATOM | 2882 | C | SER A | 401 | −14.454 | 0.206 | −16.842 | 1.00 | 27.65 | C |
| ATOM | 2883 | O | SER A | 401 | −14.743 | −1.000 | −16.802 | 1.00 | 28.53 | O |
| ATOM | 2884 | N | ILE A | 402 | −14.421 | 0.983 | −15.752 | 1.00 | 27.24 | N |
| ATOM | 2885 | CA | ILE A | 402 | −14.922 | 0.513 | −14.445 | 1.00 | 27.38 | C |
| ATOM | 2886 | CB | ILE A | 402 | −13.795 | 0.294 | −13.397 | 1.00 | 26.88 | C |
| ATOM | 2887 | CG1 | ILE A | 402 | −12.883 | −0.865 | −13.812 | 1.00 | 26.42 | C |
| ATOM | 2888 | CD1 | ILE A | 402 | −11.638 | −1.007 | −12.964 | 1.00 | 26.59 | C |
| ATOM | 2889 | CG2 | ILE A | 402 | −14.385 | 0.030 | −12.011 | 1.00 | 25.86 | C |
| ATOM | 2890 | C | ILE A | 402 | −15.975 | 1.459 | −13.878 | 1.00 | 28.23 | C |
| ATOM | 2891 | O | ILE A | 402 | −15.735 | 2.663 | −13.734 | 1.00 | 28.77 | O |
| ATOM | 2892 | N | ASP A | 403 | −17.137 | 0.892 | −13.557 | 1.00 | 29.02 | N |
| ATOM | 2893 | CA | ASP A | 403 | −18.233 | 1.608 | −12.914 | 1.00 | 29.31 | C |
| ATOM | 2894 | CB | ASP A | 403 | −19.543 | 0.827 | −13.110 | 1.00 | 30.44 | C |
| ATOM | 2895 | CG | ASP A | 403 | −20.779 | 1.576 | −12.603 | 1.00 | 31.21 | C |
| ATOM | 2896 | OD1 | ASP A | 403 | −20.741 | 2.824 | −12.489 | 1.00 | 31.95 | O |
| ATOM | 2897 | OD2 | ASP A | 403 | −21.806 | 0.901 | −12.341 | 1.00 | 30.39 | O |
| ATOM | 2898 | C | ASP A | 403 | −17.943 | 1.841 | −11.420 | 1.00 | 29.62 | C |
| ATOM | 2899 | O | ASP A | 403 | −18.218 | 0.985 | −10.572 | 1.00 | 28.37 | O |
| ATOM | 2900 | N | LEU A | 404 | −17.365 | 3.007 | −11.127 | 1.00 | 30.69 | N |
| ATOM | 2901 | CA | LEU A | 404 | −17.207 | 3.514 | −9.765 | 1.00 | 30.58 | C |
| ATOM | 2902 | CB | LEU A | 404 | −15.779 | 3.327 | −9.278 | 1.00 | 30.29 | C |
| ATOM | 2903 | CG | LEU A | 404 | −15.496 | 2.061 | −8.493 | 1.00 | 30.93 | C |
| ATOM | 2904 | CD1 | LEU A | 404 | −14.009 | 1.978 | −8.196 | 1.00 | 31.97 | C |
| ATOM | 2905 | CD2 | LEU A | 404 | −16.296 | 2.064 | −7.204 | 1.00 | 31.00 | C |
| ATOM | 2906 | C | LEU A | 404 | −17.563 | 4.993 | −9.695 | 1.00 | 30.83 | C |
| ATOM | 2907 | O | LEU A | 404 | −16.832 | 5.832 | −10.219 | 1.00 | 30.72 | O |
| ATOM | 2908 | N | PRO A | 405 | −18.678 | 5.323 | −9.025 | 1.00 | 31.76 | N |
| ATOM | 2909 | CA | PRO A | 405 | −19.067 | 6.729 | −8.923 | 1.00 | 32.25 | C |

-continued

| | | | Atomic coordinates for CRBN:DDB1:Lenalidomide (Human protein) | | | | | | | |
|---|---|---|---|---|---|---|---|---|---|---|
| ATOM | 2910 | CB | PRO A | 405 | −20.560 | 6.648 | −8.600 | 1.00 | 31.33 | C |
| ATOM | 2911 | CG | PRO A | 405 | −20.750 | 5.305 | −7.952 | 1.00 | 31.00 | C |
| ATOM | 2912 | CD | PRO A | 405 | −19.555 | 4.444 | −8.228 | 1.00 | 30.72 | C |
| ATOM | 2913 | C | PRO A | 405 | −18.305 | 7.494 | −7.819 | 1.00 | 33.22 | C |
| ATOM | 2914 | O | PRO A | 405 | −18.006 | 6.932 | −6.759 | 1.00 | 32.71 | O |
| ATOM | 2915 | N | GLY A | 406 | −17.966 | 8.752 | −8.093 | 1.00 | 34.02 | N |
| ATOM | 2916 | CA | GLY A | 406 | −17.504 | 9.676 | −7.053 | 1.00 | 35.28 | C |
| ATOM | 2917 | C | GLY A | 406 | −16.004 | 9.817 | −6.830 | 1.00 | 36.55 | C |
| ATOM | 2918 | O | GLY A | 406 | −15.575 | 10.439 | −5.855 | 1.00 | 36.75 | O |
| ATOM | 2919 | N | ILE A | 407 | −15.201 | 9.260 | −7.730 | 1.00 | 36.77 | N |
| ATOM | 2920 | CA | ILE A | 407 | −13.745 | 9.305 | −7.590 | 1.00 | 34.79 | C |
| ATOM | 2921 | CB | ILE A | 407 | −13.061 | 8.666 | −8.809 | 1.00 | 33.85 | C |
| ATOM | 2922 | CG1 | ILE A | 407 | −13.474 | 7.198 | −8.923 | 1.00 | 33.29 | C |
| ATOM | 2923 | CD1 | ILE A | 407 | −12.978 | 6.507 | −10.174 | 1.00 | 34.35 | C |
| ATOM | 2924 | CG2 | ILE A | 407 | −11.552 | 8.809 | −8.713 | 1.00 | 34.23 | C |
| ATOM | 2925 | C | ILE A | 407 | −13.249 | 10.741 | −7.387 | 1.00 | 34.87 | C |
| ATOM | 2926 | O | ILE A | 407 | −13.648 | 11.648 | −8.114 | 1.00 | 33.88 | O |
| ATOM | 2927 | N | LYS A | 408 | −12.398 | 10.938 | −6.379 | 1.00 | 35.25 | N |
| ATOM | 2928 | CA | LYS A | 408 | −11.830 | 12.254 | −6.091 | 1.00 | 34.53 | C |
| ATOM | 2929 | CB | LYS A | 408 | −12.365 | 12.800 | −4.760 | 1.00 | 35.10 | C |
| ATOM | 2930 | CG | LYS A | 408 | −13.888 | 12.850 | −4.682 | 1.00 | 36.15 | C |
| ATOM | 2931 | CD | LYS A | 408 | −14.422 | 14.212 | −4.265 | 1.00 | 36.47 | C |
| ATOM | 2932 | CE | LYS A | 408 | −15.821 | 14.430 | −4.832 | 1.00 | 37.03 | C |
| ATOM | 2933 | NZ | LYS A | 408 | −16.021 | 15.817 | −5.348 | 1.00 | 37.17 | N |
| ATOM | 2934 | C | LYS A | 408 | −10.289 | 12.292 | −6.148 | 1.00 | 35.15 | C |
| ATOM | 2935 | O | LYS A | 408 | −9.664 | 13.296 | −5.776 | 1.00 | 35.73 | O |
| ATOM | 2936 | N | GLY A | 409 | −9.686 | 11.210 | −6.641 | 1.00 | 35.09 | N |
| ATOM | 2937 | CA | GLY A | 409 | −8.233 | 11.149 | −6.841 | 1.00 | 35.28 | C |
| ATOM | 2938 | C | GLY A | 409 | −7.744 | 9.821 | −7.392 | 1.00 | 35.85 | C |
| ATOM | 2939 | O | GLY A | 409 | −8.348 | 8.783 | −7.134 | 1.00 | 38.14 | O |
| ATOM | 2940 | N | LEU A | 410 | −6.634 | 9.858 | −8.130 | 1.00 | 35.60 | N |
| ATOM | 2941 | CA | LEU A | 410 | −6.063 | 8.673 | −8.784 | 1.00 | 35.78 | C |
| ATOM | 2942 | CB | LEU A | 410 | −6.357 | 8.725 | −10.283 | 1.00 | 36.55 | C |
| ATOM | 2943 | CG | LEU A | 410 | −7.312 | 7.706 | −10.904 | 1.00 | 38.24 | C |
| ATOM | 2944 | CD1 | LEU A | 410 | −8.590 | 7.562 | −10.098 | 1.00 | 38.03 | C |
| ATOM | 2945 | CD2 | LEU A | 410 | −7.625 | 8.088 | −12.342 | 1.00 | 37.83 | C |
| ATOM | 2946 | C | LEU A | 410 | −4.556 | 8.603 | −8.599 | 1.00 | 36.28 | C |
| ATOM | 2947 | O | LEU A | 410 | −3.857 | 9.583 | −8.856 | 1.00 | 40.41 | O |
| ATOM | 2948 | N | TRP A | 411 | −4.040 | 7.456 | −8.168 | 1.00 | 34.69 | N |
| ATOM | 2949 | CA | TRP A | 411 | −2.583 | 7.281 | −8.083 | 1.00 | 34.83 | C |
| ATOM | 2950 | CB | TRP A | 411 | −2.072 | 7.539 | −6.683 | 1.00 | 33.13 | C |
| ATOM | 2951 | CG | TRP A | 411 | −2.425 | 8.894 | −6.163 | 1.00 | 31.82 | C |
| ATOM | 2952 | CD1 | TRP A | 411 | −1.639 | 10.041 | −6.180 | 1.00 | 31.36 | C |
| ATOM | 2953 | NE1 | TRP A | 411 | −2.303 | 11.095 | −5.610 | 1.00 | 30.95 | N |
| ATOM | 2954 | CE2 | TRP A | 411 | −3.534 | 10.713 | −5.201 | 1.00 | 31.90 | C |
| ATOM | 2955 | CD2 | TRP A | 411 | −3.676 | 9.290 | −5.534 | 1.00 | 31.35 | C |
| ATOM | 2956 | CE3 | TRP A | 411 | −4.861 | 8.632 | −5.214 | 1.00 | 31.15 | C |
| ATOM | 2957 | CZ3 | TRP A | 411 | −5.881 | 9.361 | −4.585 | 1.00 | 31.63 | C |
| ATOM | 2958 | CH2 | TRP A | 411 | −5.730 | 10.728 | −4.275 | 1.00 | 31.66 | C |
| ATOM | 2959 | CZ2 | TRP A | 411 | −4.555 | 11.430 | −4.579 | 1.00 | 32.06 | C |
| ATOM | 2960 | C | TRP A | 411 | −2.110 | 5.932 | −8.525 | 1.00 | 36.41 | C |
| ATOM | 2961 | O | TRP A | 411 | −2.695 | 4.904 | −8.142 | 1.00 | 38.05 | O |
| ATOM | 2962 | N | PRO A | 412 | −1.037 | 5.910 | −9.341 | 1.00 | 34.67 | N |
| ATOM | 2963 | CA | PRO A | 412 | −0.395 | 4.673 | −9.703 | 1.00 | 34.34 | C |
| ATOM | 2964 | CB | PRO A | 412 | 0.312 | 5.029 | −10.995 | 1.00 | 33.91 | C |
| ATOM | 2965 | CG | PRO A | 412 | 0.716 | 6.438 | −10.787 | 1.00 | 34.16 | C |
| ATOM | 2966 | CD | PRO A | 412 | −0.397 | 7.061 | −9.996 | 1.00 | 34.40 | C |
| ATOM | 2967 | C | PRO A | 412 | 0.616 | 4.309 | −8.634 | 1.00 | 35.14 | C |
| ATOM | 2968 | O | PRO A | 412 | 1.103 | 5.171 | −7.899 | 1.00 | 35.07 | O |
| ATOM | 2969 | N | LEU A | 413 | 0.946 | 3.035 | −8.567 | 1.00 | 35.38 | N |
| ATOM | 2970 | CA | LEU A | 413 | 1.661 | 2.519 | −7.433 | 1.00 | 35.34 | C |
| ATOM | 2971 | CB | LEU A | 413 | 0.676 | 2.386 | −6.280 | 1.00 | 34.81 | C |
| ATOM | 2972 | CG | LEU A | 413 | 1.184 | 2.430 | −4.863 | 1.00 | 33.65 | C |
| ATOM | 2973 | CD1 | LEU A | 413 | 0.408 | 3.484 | −4.097 | 1.00 | 33.27 | C |
| ATOM | 2974 | CD2 | LEU A | 413 | 1.007 | 1.049 | −4.266 | 1.00 | 33.58 | C |
| ATOM | 2975 | C | LEU A | 413 | 2.252 | 1.169 | −7.816 | 1.00 | 36.22 | C |
| ATOM | 2976 | O | LEU A | 413 | 1.887 | 0.591 | −8.853 | 1.00 | 35.05 | O |
| ATOM | 2977 | N | ARG A | 414 | 3.159 | 0.668 | −6.981 | 1.00 | 37.14 | N |
| ATOM | 2978 | CA | ARG A | 414 | 3.967 | −0.488 | −7.345 | 1.00 | 38.28 | C |
| ATOM | 2979 | CB | ARG A | 414 | 5.327 | −0.022 | −7.850 | 1.00 | 37.85 | C |
| ATOM | 2980 | CG | ARG A | 414 | 5.919 | −0.914 | −8.915 | 1.00 | 38.86 | C |
| ATOM | 2981 | CD | ARG A | 414 | 6.918 | −0.141 | −9.756 | 1.00 | 40.63 | C |
| ATOM | 2982 | NE | ARG A | 414 | 7.916 | 0.546 | −8.936 | 1.00 | 41.65 | N |
| ATOM | 2983 | CZ | ARG A | 414 | 8.069 | 1.866 | −8.894 | 1.00 | 41.13 | C |
| ATOM | 2984 | NH1 | ARG A | 414 | 7.297 | 2.653 | −9.638 | 1.00 | 39.81 | N |
| ATOM | 2985 | NH2 | ARG A | 414 | 9.003 | 2.397 | −8.116 | 1.00 | 39.51 | N |
| ATOM | 2986 | C | ARG A | 414 | 4.124 | −1.469 | −6.194 | 1.00 | 38.44 | C |

-continued

| | | | | | | | | | | |
|---|---|---|---|---|---|---|---|---|---|---|
| | Atomic coordinates for CRBN:DDB1:Lenalidomide (Human protein) |

| | | | | | | | | | | |
|---|---|---|---|---|---|---|---|---|---|---|
| ATOM | 2987 | O | ARG A | 414 | 5.034 | −1.344 | −5.374 | 1.00 | 37.62 | O |
| ATOM | 2988 | N | SER A | 415 | 3.237 | −2.460 | −6.156 | 1.00 | 40.81 | N |
| ATOM | 2989 | CA | SER A | 415 | 3.172 | −3.420 | −5.047 | 1.00 | 42.55 | C |
| ATOM | 2990 | CB | SER A | 415 | 1.956 | −4.340 | −5.214 | 1.00 | 40.80 | C |
| ATOM | 2991 | C | SER A | 415 | 4.452 | −4.256 | −4.823 | 1.00 | 43.55 | C |
| ATOM | 2992 | O | SER A | 415 | 4.551 | −4.968 | −3.819 | 1.00 | 44.34 | O |
| ATOM | 2993 | N | ASP A | 416 | 5.424 | −4.154 | −5.738 | 1.00 | 43.67 | N |
| ATOM | 2994 | CA | ASP A | 416 | 6.619 | −5.017 | −5.714 | 1.00 | 43.70 | C |
| ATOM | 2995 | CB | ASP A | 416 | 6.254 | −6.426 | −6.209 | 1.00 | 44.69 | C |
| ATOM | 2996 | CG | ASP A | 416 | 7.378 | −7.089 | −6.977 | 1.00 | 46.96 | C |
| ATOM | 2997 | OD1 | ASP A | 416 | 8.378 | −7.519 | −6.351 | 1.00 | 48.27 | O |
| ATOM | 2998 | OD2 | ASP A | 416 | 7.253 | −7.178 | −8.216 | 1.00 | 48.64 | O |
| ATOM | 2999 | C | ASP A | 416 | 7.835 | −4.465 | −6.490 | 1.00 | 42.71 | C |
| ATOM | 3000 | O | ASP A | 416 | 7.696 | −4.038 | −7.637 | 1.00 | 44.00 | O |
| ATOM | 3001 | N | PRO A | 417 | 9.036 | −4.490 | −5.864 | 1.00 | 42.41 | N |
| ATOM | 3002 | CA | PRO A | 417 | 10.266 | −4.099 | −6.560 | 1.00 | 41.42 | C |
| ATOM | 3003 | CB | PRO A | 417 | 11.205 | −3.661 | −5.417 | 1.00 | 41.46 | C |
| ATOM | 3004 | CG | PRO A | 417 | 10.420 | −3.807 | −4.138 | 1.00 | 41.70 | C |
| ATOM | 3005 | CD | PRO A | 417 | 9.295 | −4.752 | −4.437 | 1.00 | 41.98 | C |
| ATOM | 3006 | C | PRO A | 417 | 10.882 | −5.263 | −7.334 | 1.00 | 39.94 | C |
| ATOM | 3007 | O | PRO A | 417 | 10.684 | −5.367 | −8.547 | 1.00 | 39.31 | O |
| ATOM | 3008 | N | GLU A | 420 | 9.067 | −2.698 | −10.395 | 1.00 | 40.34 | N |
| ATOM | 3009 | CA | GLU A | 420 | 9.334 | −2.932 | −11.810 | 1.00 | 43.29 | C |
| ATOM | 3010 | CB | GLU A | 420 | 9.187 | −4.443 | −12.117 | 1.00 | 46.24 | C |
| ATOM | 3011 | CG | GLU A | 420 | 8.583 | −4.850 | −13.471 | 1.00 | 49.31 | C |
| ATOM | 3012 | CD | GLU A | 420 | 9.282 | −4.262 | −14.701 | 1.00 | 50.98 | C |
| ATOM | 3013 | OE1 | GLU A | 420 | 10.482 | −3.896 | −14.618 | 1.00 | 51.24 | O |
| ATOM | 3014 | OE2 | GLU A | 420 | 8.614 | −4.172 | −15.762 | 1.00 | 50.52 | O |
| ATOM | 3015 | C | GLU A | 420 | 8.488 | −2.034 | −12.753 | 1.00 | 43.67 | C |
| ATOM | 3016 | O | GLU A | 420 | 9.034 | −1.306 | −13.586 | 1.00 | 42.76 | O |
| ATOM | 3017 | N | THR A | 421 | 7.164 | −2.102 | −12.582 | 1.00 | 44.02 | N |
| ATOM | 3018 | CA | THR A | 421 | 6.144 | −1.444 | −13.405 | 1.00 | 39.92 | C |
| ATOM | 3019 | CB | THR A | 421 | 5.824 | −2.282 | −14.659 | 1.00 | 39.53 | C |
| ATOM | 3020 | OG1 | THR A | 421 | 4.735 | −1.688 | −15.371 | 1.00 | 40.03 | O |
| ATOM | 3021 | CG2 | THR A | 421 | 5.429 | −3.712 | −14.284 | 1.00 | 38.88 | C |
| ATOM | 3022 | C | THR A | 421 | 4.894 | −1.410 | −12.531 | 1.00 | 39.49 | C |
| ATOM | 3023 | O | THR A | 421 | 4.707 | −2.308 | −11.710 | 1.00 | 41.18 | O |
| ATOM | 3024 | N | ASP A | 422 | 4.036 | −0.404 | −12.691 | 1.00 | 38.39 | N |
| ATOM | 3025 | CA | ASP A | 422 | 2.834 | −0.304 | −11.844 | 1.00 | 38.46 | C |
| ATOM | 3026 | CB | ASP A | 422 | 1.976 | 0.919 | −12.201 | 1.00 | 42.97 | C |
| ATOM | 3027 | CG | ASP A | 422 | 2.795 | 2.182 | −12.446 | 1.00 | 46.66 | C |
| ATOM | 3028 | OD1 | ASP A | 422 | 3.584 | 2.594 | −11.562 | 1.00 | 49.51 | O |
| ATOM | 3029 | OD2 | ASP A | 422 | 2.615 | 2.784 | −13.527 | 1.00 | 49.04 | O |
| ATOM | 3030 | C | ASP A | 422 | 1.966 | −1.564 | −11.926 | 1.00 | 36.45 | C |
| ATOM | 3031 | O | ASP A | 422 | 1.937 | −2.250 | −12.951 | 1.00 | 36.18 | O |
| ATOM | 3032 | N | ASP A | 423 | 1.265 | −1.862 | −10.839 | 1.00 | 35.16 | N |
| ATOM | 3033 | CA | ASP A | 423 | 0.350 | −3.005 | −10.791 | 1.00 | 35.99 | C |
| ATOM | 3034 | CB | ASP A | 423 | 1.071 | −4.260 | −10.280 | 1.00 | 37.22 | C |
| ATOM | 3035 | CG | ASP A | 423 | 1.612 | −4.099 | −8.853 | 1.00 | 39.67 | C |
| ATOM | 3036 | OD1 | ASP A | 423 | 1.628 | −2.964 | −8.321 | 1.00 | 40.84 | O |
| ATOM | 3037 | OD2 | ASP A | 423 | 2.026 | −5.117 | −8.258 | 1.00 | 42.05 | O |
| ATOM | 3038 | C | ASP A | 423 | −0.826 | −2.664 | −9.886 | 1.00 | 35.02 | C |
| ATOM | 3039 | O | ASP A | 423 | −1.732 | −3.469 | −9.669 | 1.00 | 34.40 | O |
| ATOM | 3040 | N | THR A | 424 | −0.797 | −1.449 | −9.366 | 1.00 | 33.22 | N |
| ATOM | 3041 | CA | THR A | 424 | −1.727 | −1.036 | −8.359 | 1.00 | 32.45 | C |
| ATOM | 3042 | CB | THR A | 424 | −1.027 | −0.938 | −6.991 | 1.00 | 33.57 | C |
| ATOM | 3043 | OG1 | THR A | 424 | −0.310 | −2.154 | −6.723 | 1.00 | 33.76 | O |
| ATOM | 3044 | CG2 | THR A | 424 | −2.037 | −0.665 | −5.870 | 1.00 | 33.40 | C |
| ATOM | 3045 | C | THR A | 424 | −2.254 | 0.325 | −8.736 | 1.00 | 31.79 | C |
| ATOM | 3046 | O | THR A | 424 | −1.489 | 1.241 | −9.029 | 1.00 | 32.17 | O |
| ATOM | 3047 | N | LEU A | 425 | −3.570 | 0.451 | −8.743 | 1.00 | 32.09 | N |
| ATOM | 3048 | CA | LEU A | 425 | −4.202 | 1.746 | −8.876 | 1.00 | 32.56 | C |
| ATOM | 3049 | CB | LEU A | 425 | −5.163 | 1.751 | −10.067 | 1.00 | 34.11 | C |
| ATOM | 3050 | CG | LEU A | 425 | −5.270 | 3.024 | −10.918 | 1.00 | 35.45 | C |
| ATOM | 3051 | CD1 | LEU A | 425 | −3.910 | 3.413 | −11.484 | 1.00 | 35.66 | C |
| ATOM | 3052 | CD2 | LEU A | 425 | −6.287 | 2.842 | −12.043 | 1.00 | 34.77 | C |
| ATOM | 3053 | C | LEU A | 425 | −4.936 | 2.033 | −7.576 | 1.00 | 32.00 | C |
| ATOM | 3054 | O | LEU A | 425 | −5.733 | 1.213 | −7.107 | 1.00 | 30.88 | O |
| ATOM | 3055 | N | VAL A | 426 | −4.634 | 3.179 | −6.976 | 1.00 | 32.03 | N |
| ATOM | 3056 | CA | VAL A | 426 | −5.287 | 3.591 | −5.742 | 1.00 | 33.58 | C |
| ATOM | 3057 | CB | VAL A | 426 | −4.267 | 4.021 | −4.663 | 1.00 | 32.82 | C |
| ATOM | 3058 | CG1 | VAL A | 426 | −4.976 | 4.506 | −3.409 | 1.00 | 32.75 | C |
| ATOM | 3059 | CG2 | VAL A | 426 | −3.339 | 2.870 | −4.318 | 1.00 | 31.94 | C |
| ATOM | 3060 | C | VAL A | 426 | −6.250 | 4.726 | −6.061 | 1.00 | 35.83 | C |
| ATOM | 3061 | O | VAL A | 426 | −5.873 | 5.716 | −6.687 | 1.00 | 38.22 | O |
| ATOM | 3062 | N | LEU A | 427 | −7.502 | 4.559 | −5.655 | 1.00 | 38.10 | N |
| ATOM | 3063 | CA | LEU A | 427 | −8.542 | 5.542 | −5.922 | 1.00 | 40.65 | C |

-continued

| | | | Atomic coordinates for CRBN:DDB1:Lenalidomide (Human protein) | | | | | | |
|---|---|---|---|---|---|---|---|---|---|
| ATOM | 3064 | CB | LEU A | 427 | −9.675 | 4.913 | −6.740 | 1.00 | 40.37 | C |
| ATOM | 3065 | CG | LEU A | 427 | −9.465 | 4.464 | −8.191 | 1.00 | 39.32 | C |
| ATOM | 3066 | CD1 | LEU A | 427 | −8.489 | 3.301 | −8.313 | 1.00 | 38.60 | C |
| ATOM | 3067 | CD2 | LEU A | 427 | −10.809 | 4.071 | −8.781 | 1.00 | 38.86 | C |
| ATOM | 3068 | C | LEU A | 427 | −9.090 | 6.037 | −4.595 | 1.00 | 43.19 | C |
| ATOM | 3069 | O | LEU A | 427 | −9.193 | 5.258 | −3.639 | 1.00 | 44.47 | O |
| ATOM | 3070 | N | SER A | 428 | −9.442 | 7.321 | −4.528 | 1.00 | 43.82 | N |
| ATOM | 3071 | CA | SER A | 428 | −10.066 | 7.867 | −3.317 | 1.00 | 44.71 | C |
| ATOM | 3072 | CB | SER A | 428 | −9.127 | 8.841 | −2.596 | 1.00 | 45.06 | C |
| ATOM | 3073 | OG | SER A | 428 | −8.911 | 10.010 | −3.361 | 1.00 | 48.88 | O |
| ATOM | 3074 | C | SER A | 428 | −11.439 | 8.501 | −3.570 | 1.00 | 44.08 | C |
| ATOM | 3075 | O | SER A | 428 | −11.698 | 9.064 | −4.636 | 1.00 | 45.41 | O |
| ATOM | 3076 | N | PHE A | 429 | −12.313 | 8.384 | −2.579 | 1.00 | 41.84 | N |
| ATOM | 3077 | CA | PHE A | 429 | −13.663 | 8.927 | −2.650 | 1.00 | 41.84 | C |
| ATOM | 3078 | CB | PHE A | 429 | −14.670 | 7.781 | −2.679 | 1.00 | 41.35 | C |
| ATOM | 3079 | CG | PHE A | 429 | −14.338 | 6.725 | −3.697 | 1.00 | 40.90 | C |
| ATOM | 3080 | CD1 | PHE A | 429 | −13.483 | 5.673 | −3.377 | 1.00 | 41.12 | C |
| ATOM | 3081 | CE1 | PHE A | 429 | −13.156 | 4.711 | −4.318 | 1.00 | 40.03 | C |
| ATOM | 3082 | CZ | PHE A | 429 | −13.676 | 4.792 | −5.592 | 1.00 | 38.71 | C |
| ATOM | 3083 | CE2 | PHE A | 429 | −14.523 | 5.837 | −5.924 | 1.00 | 39.89 | C |
| ATOM | 3084 | CD2 | PHE A | 429 | −14.846 | 6.800 | −4.984 | 1.00 | 39.63 | C |
| ATOM | 3085 | C | PHE A | 429 | −13.839 | 9.801 | −1.424 | 1.00 | 42.24 | C |
| ATOM | 3086 | O | PHE A | 429 | −12.900 | 9.915 | −0.635 | 1.00 | 44.62 | O |
| ATOM | 3087 | N | VAL A | 430 | −15.003 | 10.435 | −1.257 | 1.00 | 41.49 | N |
| ATOM | 3088 | CA | VAL A | 430 | −15.202 | 11.331 | −0.102 | 1.00 | 41.03 | C |
| ATOM | 3089 | CB | VAL A | 430 | −16.506 | 12.172 | −0.186 | 1.00 | 40.96 | C |
| ATOM | 3090 | CG1 | VAL A | 430 | −17.720 | 11.385 | 0.305 | 1.00 | 39.36 | C |
| ATOM | 3091 | CG2 | VAL A | 430 | −16.347 | 13.474 | 0.594 | 1.00 | 39.87 | C |
| ATOM | 3092 | C | VAL A | 430 | −15.092 | 10.560 | 1.214 | 1.00 | 40.81 | C |
| ATOM | 3093 | O | VAL A | 430 | −15.847 | 9.624 | 1.456 | 1.00 | 38.75 | O |
| ATOM | 3094 | N | GLY A | 431 | −14.106 | 10.942 | 2.028 | 1.00 | 43.03 | N |
| ATOM | 3095 | CA | GLY A | 431 | −13.725 | 10.199 | 3.233 | 1.00 | 43.58 | C |
| ATOM | 3096 | C | GLY A | 431 | −13.608 | 8.691 | 3.046 | 1.00 | 44.59 | C |
| ATOM | 3097 | O | GLY A | 431 | −14.083 | 7.928 | 3.886 | 1.00 | 45.90 | O |
| ATOM | 3098 | N | GLN A | 432 | −12.984 | 8.256 | 1.950 | 1.00 | 43.70 | N |
| ATOM | 3099 | CA | GLN A | 432 | −12.837 | 6.823 | 1.652 | 1.00 | 43.89 | C |
| ATOM | 3100 | CB | GLN A | 432 | −14.139 | 6.269 | 1.064 | 1.00 | 44.93 | C |
| ATOM | 3101 | CG | GLN A | 432 | −14.264 | 4.753 | 1.104 | 1.00 | 46.17 | C |
| ATOM | 3102 | CD | GLN A | 432 | −15.494 | 4.245 | 0.364 | 1.00 | 48.52 | C |
| ATOM | 3103 | OE1 | GLN A | 432 | −16.407 | 5.014 | 0.041 | 1.00 | 49.50 | O |
| ATOM | 3104 | NE2 | GLN A | 432 | −15.524 | 2.942 | 0.093 | 1.00 | 47.15 | N |
| ATOM | 3105 | C | GLN A | 432 | −11.675 | 6.589 | 0.683 | 1.00 | 42.93 | C |
| ATOM | 3106 | O | GLN A | 432 | −11.355 | 7.468 | −0.119 | 1.00 | 44.12 | O |
| ATOM | 3107 | N | THR A | 433 | −11.038 | 5.419 | 0.770 | 1.00 | 40.49 | N |
| ATOM | 3108 | CA | THR A | 433 | −9.978 | 5.038 | −0.178 | 1.00 | 38.78 | C |
| ATOM | 3109 | CB | THR A | 433 | −8.575 | 5.348 | 0.365 | 1.00 | 37.51 | C |
| ATOM | 3110 | OG1 | THR A | 433 | −8.507 | 6.723 | 0.750 | 1.00 | 38.64 | O |
| ATOM | 3111 | CG2 | THR A | 433 | −7.509 | 5.064 | −0.692 | 1.00 | 35.97 | C |
| ATOM | 3112 | C | THR A | 433 | −10.043 | 3.562 | −0.554 | 1.00 | 39.05 | C |
| ATOM | 3113 | O | THR A | 433 | −10.181 | 2.699 | 0.314 | 1.00 | 39.30 | O |
| ATOM | 3114 | N | ARG A | 434 | −9.946 | 3.286 | −1.852 | 1.00 | 37.60 | N |
| ATOM | 3115 | CA | ARG A | 434 | −9.956 | 1.921 | −2.361 | 1.00 | 37.75 | C |
| ATOM | 3116 | CB | ARG A | 434 | −11.213 | 1.651 | −3.203 | 1.00 | 38.56 | C |
| ATOM | 3117 | CG | ARG A | 434 | −12.553 | 1.740 | −2.478 | 1.00 | 37.10 | C |
| ATOM | 3118 | CD | ARG A | 434 | −13.591 | 0.901 | −3.218 | 1.00 | 36.00 | C |
| ATOM | 3119 | NE | ARG A | 434 | −14.928 | 1.488 | −3.233 | 1.00 | 35.26 | N |
| ATOM | 3120 | CZ | ARG A | 434 | −15.995 | 0.891 | −3.759 | 1.00 | 35.28 | C |
| ATOM | 3121 | NH1 | ARG A | 434 | −15.878 | −0.311 | −4.305 | 1.00 | 35.94 | N |
| ATOM | 3122 | NH2 | ARG A | 434 | −17.181 | 1.492 | −3.744 | 1.00 | 35.37 | N |
| ATOM | 3123 | C | ARG A | 434 | −8.713 | 1.653 | −3.208 | 1.00 | 37.45 | C |
| ATOM | 3124 | O | ARG A | 434 | −8.176 | 2.561 | −3.840 | 1.00 | 37.91 | O |
| ATOM | 3125 | N | VAL A | 435 | −8.277 | 0.396 | −3.224 | 1.00 | 37.25 | N |
| ATOM | 3126 | CA | VAL A | 435 | −7.068 | −0.017 | −3.935 | 1.00 | 37.60 | C |
| ATOM | 3127 | CB | VAL A | 435 | −5.986 | −0.538 | −2.952 | 1.00 | 37.32 | C |
| ATOM | 3128 | CG1 | VAL A | 435 | −4.748 | −1.020 | −3.701 | 1.00 | 37.26 | C |
| ATOM | 3129 | CG2 | VAL A | 435 | −5.608 | 0.51 | −1.948 | 1.00 | 37.00 | C |
| ATOM | 3130 | C | VAL A | 435 | −7.397 | −1.104 | −4.962 | 1.00 | 38.03 | C |
| ATOM | 3131 | O | VAL A | 435 | −8.049 | −2.100 | −4.635 | 1.00 | 39.22 | O |
| ATOM | 3132 | N | LEU A | 436 | −6.941 | −0.911 | −6.198 | 1.00 | 36.74 | N |
| ATOM | 3133 | CA | LEU A | 436 | −7.201 | −1.868 | −7.267 | 1.00 | 36.55 | C |
| ATOM | 3134 | CB | LEU A | 436 | −7.876 | −1.175 | −8.457 | 1.00 | 36.60 | C |
| ATOM | 3135 | CG | LEU A | 436 | −9.246 | −0.530 | −8.239 | 1.00 | 35.55 | C |
| ATOM | 3136 | CD1 | LEU A | 436 | −9.735 | 0.112 | −9.525 | 1.00 | 34.84 | C |
| ATOM | 3137 | CD2 | LEU A | 436 | −10.251 | −1.551 | −7.729 | 1.00 | 35.28 | C |
| ATOM | 3138 | C | LEU A | 436 | −5.915 | −2.521 | −7.727 | 1.00 | 36.16 | C |
| ATOM | 3139 | O | LEU A | 436 | −4.980 | −1.830 | −8.123 | 1.00 | 36.58 | O |
| ATOM | 3140 | N | MET A | 437 | −5.862 | −3.848 | −7.682 | 1.00 | 35.58 | N |

-continued

| | | | | Atomic coordinates for CRBN:DDB1:Lenalidomide (Human protein) | | | | | |
|---|---|---|---|---|---|---|---|---|---|
| ATOM | 3141 | CA | MET A | 437 | −4.694 | −4.546 | −8.206 | 1.00 | 36.20 | C |
| ATOM | 3142 | CB | MET A | 437 | −4.337 | −5.781 | −7.356 | 1.00 | 37.96 | C |
| ATOM | 3143 | CG | MET A | 437 | −4.865 | −7.118 | −7.850 | 1.00 | 40.73 | C |
| ATOM | 3144 | SD | MET A | 437 | −4.283 | −8.497 | −6.838 | 1.00 | 43.43 | S |
| ATOM | 3145 | CE | MET A | 437 | −2.599 | −8.685 | −7.433 | 1.00 | 41.94 | C |
| ATOM | 3146 | C | MET A | 437 | −4.862 | −4.875 | −9.693 | 1.00 | 34.98 | C |
| ATOM | 3147 | O | MET A | 437 | −5.966 | −5.194 | −10.151 | 1.00 | 36.42 | O |
| ATOM | 3148 | N | LEU A | 438 | −3.768 | −4.769 | −10.443 | 1.00 | 32.03 | N |
| ATOM | 3149 | CA | LEU A | 438 | −3.783 | −5.058 | −11.867 | 1.00 | 30.70 | C |
| ATOM | 3150 | CB | LEU A | 438 | −3.297 | −3.847 | −12.659 | 1.00 | 31.02 | C |
| ATOM | 3151 | CG | LEU A | 438 | −4.269 | −2.670 | −12.711 | 1.00 | 31.64 | C |
| ATOM | 3152 | CD1 | LEU A | 438 | −4.247 | −1.912 | −11.397 | 1.00 | 33.39 | C |
| ATOM | 3153 | CD2 | LEU A | 438 | −3.951 | −1.733 | −13.866 | 1.00 | 31.56 | C |
| ATOM | 3154 | C | LEU A | 438 | −2.965 | −6.292 | −12.228 | 1.00 | 29.63 | C |
| ATOM | 3155 | O | LEU A | 438 | −1.755 | −6.329 | −12.031 | 1.00 | 29.72 | O |
| ATOM | 3156 | N | ASN A | 439 | −3.645 | −7.310 | −12.734 | 1.00 | 29.32 | N |
| ATOM | 3157 | CA | ASN A | 439 | −2.989 | −8.456 | −13.344 | 1.00 | 30.36 | C |
| ATOM | 3158 | CB | ASN A | 439 | −3.388 | −9.765 | −12.654 | 1.00 | 30.83 | C |
| ATOM | 3159 | CG | ASN A | 439 | −2.353 | −10.238 | −11.647 | 1.00 | 31.42 | C |
| ATOM | 3160 | OD1 | ASN A | 439 | −1.415 | −10.962 | −11.996 | 1.00 | 30.93 | O |
| ATOM | 3161 | ND2 | ASN A | 439 | −2.524 | −9.838 | −10.385 | 1.00 | 31.31 | N |
| ATOM | 3162 | C | ASN A | 439 | −3.395 | −8.490 | −14.797 | 1.00 | 30.86 | C |
| ATOM | 3163 | O | ASN A | 439 | −4.564 | −8.705 | −15.109 | 1.00 | 31.43 | O |
| ATOM | 3164 | N | GLY A | 440 | −2.439 | −8.242 | −15.687 | 1.00 | 31.02 | N |
| ATOM | 3165 | CA | GLY A | 440 | −2.746 | −8.092 | −17.101 | 1.00 | 31.35 | C |
| ATOM | 3166 | C | GLY A | 440 | −3.891 | −7.117 | −17.309 | 1.00 | 31.67 | C |
| ATOM | 3167 | O | GLY A | 440 | −3.809 | −5.949 | −16.922 | 1.00 | 32.14 | O |
| ATOM | 3168 | N | GLU A | 441 | −4.969 | −7.608 | −17.901 | 1.00 | 32.01 | N |
| ATOM | 3169 | CA | GLU A | 441 | −6.120 | −6.778 | −18.203 | 1.00 | 33.36 | C |
| ATOM | 3170 | CB | GLU A | 441 | −6.661 | −7.101 | −19.593 | 1.00 | 34.81 | C |
| ATOM | 3171 | CG | GLU A | 441 | −6.035 | −6.313 | −20.726 | 1.00 | 36.48 | C |
| ATOM | 3172 | CD | GLU A | 441 | −6.697 | −6.606 | −22.065 | 1.00 | 39.49 | C |
| ATOM | 3173 | OE1 | GLU A | 441 | −5.960 | −6.781 | −23.054 | 1.00 | 40.89 | O |
| ATOM | 3174 | OE2 | GLU A | 441 | −7.953 | −6.670 | −22.137 | 1.00 | 40.96 | O |
| ATOM | 3175 | C | GLU A | 441 | −7.227 | −6.957 | −17.175 | 1.00 | 33.77 | C |
| ATOM | 3176 | O | GLU A | 441 | −8.321 | −6.397 | −17.326 | 1.00 | 34.90 | O |
| ATOM | 3177 | N | GLU A | 442 | −6.951 | −7.732 | −16.130 | 1.00 | 33.82 | N |
| ATOM | 3178 | CA | GLU A | 442 | −7.954 | −7.967 | −15.086 | 1.00 | 34.39 | C |
| ATOM | 3179 | CB | GLU A | 442 | −8.179 | −9.464 | −14.830 | 1.00 | 34.63 | C |
| ATOM | 3180 | CG | GLU A | 442 | −6.931 | −10.290 | −14.567 | 1.00 | 34.42 | C |
| ATOM | 3181 | CD | GLU A | 442 | −7.198 | −11.782 | −14.613 | 1.00 | 35.35 | C |
| ATOM | 3182 | OE1 | GLU A | 442 | −8.304 | −12.194 | −15.036 | 1.00 | 36.06 | O |
| ATOM | 3183 | OE2 | GLU A | 442 | −6.299 | −12.551 | −14.224 | 1.00 | 36.26 | O |
| ATOM | 3184 | C | GLU A | 442 | −7.681 | −7.206 | −13.793 | 1.00 | 34.33 | C |
| ATOM | 3185 | O | GLU A | 442 | −6.637 | −7.385 | −13.152 | 1.00 | 33.18 | O |
| ATOM | 3186 | N | VAL A | 443 | −8.628 | −6.331 | −13.445 | 1.00 | 34.44 | N |
| ATOM | 3187 | CA | VAL A | 443 | −8.535 | −5.496 | −12.254 | 1.00 | 34.09 | C |
| ATOM | 3188 | CB | VAL A | 443 | −9.061 | −4.067 | −12.509 | 1.00 | 34.50 | C |
| ATOM | 3189 | CG1 | VAL A | 443 | −8.958 | −3.214 | −11.248 | 1.00 | 34.03 | C |
| ATOM | 3190 | CG2 | VAL A | 443 | −8.307 | −3.411 | −13.659 | 1.00 | 34.27 | C |
| ATOM | 3191 | C | VAL A | 443 | −9.339 | −6.149 | −11.143 | 1.00 | 34.39 | C |
| ATOM | 3192 | O | VAL A | 443 | −10.457 | −6.628 | −11.371 | 1.00 | 33.97 | O |
| ATOM | 3193 | N | GLU A | 444 | −8.750 | −6.181 | −9.949 | 1.00 | 34.43 | N |
| ATOM | 3194 | CA | GLU A | 444 | −9.366 | −6.798 | −8.780 | 1.00 | 33.68 | C |
| ATOM | 3195 | CB | GLU A | 444 | −8.778 | −8.190 | −8.547 | 1.00 | 32.68 | C |
| ATOM | 3196 | CG | GLU A | 444 | −9.718 | −9.128 | −7.818 | 1.00 | 33.73 | C |
| ATOM | 3197 | CD | GLU A | 444 | −9.007 | −10.261 | −7.094 | 1.00 | 34.47 | C |
| ATOM | 3198 | OE1 | GLU A | 444 | −9.193 | −10.382 | −5.864 | 1.00 | 33.93 | O |
| ATOM | 3199 | OE2 | GLU A | 444 | −8.272 | −11.039 | −7.742 | 1.00 | 35.85 | O |
| ATOM | 3200 | C | GLU A | 444 | −9.125 | −5.904 | −7.564 | 1.00 | 34.06 | C |
| ATOM | 3201 | O | GLU A | 444 | −7.980 | −5.533 | −7.272 | 1.00 | 34.43 | O |
| ATOM | 3202 | N | GLU A | 445 | −10.201 | −5.538 | −6.870 | 1.00 | 34.65 | N |
| ATOM | 3203 | CA | GLU A | 445 | −10.090 | −4.697 | −5.675 | 1.00 | 35.46 | C |
| ATOM | 3204 | CB | GLU A | 445 | −11.452 | −4.149 | −5.241 | 1.00 | 35.65 | C |
| ATOM | 3205 | CG | GLU A | 445 | −11.523 | −3.778 | −3.766 | 1.00 | 36.50 | C |
| ATOM | 3206 | CD | GLU A | 445 | −12.286 | −2.493 | −3.492 | 1.00 | 37.42 | C |
| ATOM | 3207 | OE1 | GLU A | 445 | −11.874 | −1.765 | −2.550 | 1.00 | 37.33 | O |
| ATOM | 3208 | OE2 | GLU A | 445 | −13.281 | −2.210 | −4.207 | 1.00 | 35.75 | O |
| ATOM | 3209 | C | GLU A | 445 | −9.465 | −5.487 | −4.552 | 1.00 | 35.52 | C |
| ATOM | 3210 | O | GLU A | 445 | −9.795 | −6.651 | −4.360 | 1.00 | 35.94 | O |
| ATOM | 3211 | N | THR A | 446 | −8.564 | −4.851 | −3.811 | 1.00 | 36.34 | N |
| ATOM | 3212 | CA | THR A | 446 | −7.866 | −5.522 | −2.718 | 1.00 | 38.20 | C |
| ATOM | 3213 | CB | THR A | 446 | −6.520 | −6.119 | −3.205 | 1.00 | 37.81 | C |
| ATOM | 3214 | OG1 | THR A | 446 | −5.972 | −6.969 | −2.193 | 1.00 | 37.76 | O |
| ATOM | 3215 | CG2 | THR A | 446 | −5.511 | −5.024 | −3.571 | 1.00 | 37.79 | C |
| ATOM | 3216 | C | THR A | 446 | −7.688 | −4.611 | −1.487 | 1.00 | 39.68 | C |
| ATOM | 3217 | O | THR A | 446 | −8.249 | −3.513 | −1.434 | 1.00 | 40.02 | O |

-continued

| | | | | Atomic coordinates for CRBN:DDB1:Lenalidomide (Human protein) | | | | | |
|---|---|---|---|---|---|---|---|---|---|
| ATOM | 3218 | N | GLU A | 447 | −6.948 | −5.096 | −0.491 | 1.00 | 42.51 | N |
| ATOM | 3219 | CA | GLU A | 447 | −6.475 | −4.276 | 0.631 | 1.00 | 45.02 | C |
| ATOM | 3220 | CB | GLU A | 447 | −6.832 | −4.938 | 1.970 | 1.00 | 43.40 | C |
| ATOM | 3221 | C | GLU A | 447 | −4.952 | −4.074 | 0.528 | 1.00 | 47.09 | C |
| ATOM | 3222 | O | GLU A | 447 | −4.221 | −4.987 | 0.113 | 1.00 | 48.13 | O |
| ATOM | 3223 | N | LEU A | 448 | −4.476 | −2.883 | 0.882 | 1.00 | 47.03 | N |
| ATOM | 3224 | CA | LEU A | 448 | −3.037 | −2.665 | 1.015 | 1.00 | 49.45 | C |
| ATOM | 3225 | CB | LEU A | 448 | −2.583 | −1.426 | 0.232 | 1.00 | 49.54 | C |
| ATOM | 3226 | CG | LEU A | 448 | −1.073 | −1.285 | −0.031 | 1.00 | 49.09 | C |
| ATOM | 3227 | CD1 | LEU A | 448 | −0.556 | −2.430 | −0.893 | 1.00 | 48.79 | C |
| ATOM | 3228 | CD2 | LEU A | 448 | −0.749 | 0.052 | −0.681 | 1.00 | 46.81 | C |
| ATOM | 3229 | C | LEU A | 448 | −2.667 | −2.532 | 2.489 | 1.00 | 52.10 | C |
| ATOM | 3230 | O | LEU A | 448 | −3.091 | −1.582 | 3.159 | 1.00 | 56.88 | O |
| ATOM | 3231 | N | MET A | 449 | −1.891 | −3.484 | 3.002 | 1.00 | 50.26 | N |
| ATOM | 3232 | CA | MET A | 449 | −1.533 | −3.465 | 4.420 | 1.00 | 49.85 | C |
| ATOM | 3233 | CB | MET A | 449 | −0.796 | −4.743 | 4.832 | 1.00 | 51.08 | C |
| ATOM | 3234 | CG | MET A | 449 | −0.938 | −5.102 | 6.305 | 1.00 | 49.54 | C |
| ATOM | 3235 | SD | MET A | 449 | 0.157 | −6.464 | 6.765 | 1.00 | 53.97 | S |
| ATOM | 3236 | CE | MET A | 449 | −0.720 | −7.891 | 6.113 | 1.00 | 53.26 | C |
| ATOM | 3237 | C | MET A | 449 | −0.705 | −2.224 | 4.744 | 1.00 | 47.53 | C |
| ATOM | 3238 | O | MET A | 449 | 0.309 | −1.945 | 4.104 | 1.00 | 45.58 | O |
| ATOM | 3239 | N | GLY A | 450 | −1.171 | −1.470 | 5.729 | 1.00 | 46.06 | N |
| ATOM | 3240 | CA | GLY A | 450 | −0.505 | −0.246 | 6.129 | 1.00 | 44.55 | C |
| ATOM | 3241 | C | GLY A | 450 | −1.212 | 0.965 | 5.580 | 1.00 | 43.27 | C |
| ATOM | 3242 | O | GLY A | 450 | −0.939 | 2.091 | 5.990 | 1.00 | 44.47 | O |
| ATOM | 3243 | N | PHE A | 451 | −2.131 | 0.735 | 4.652 | 1.00 | 41.99 | N |
| ATOM | 3244 | CA | PHE A | 451 | −2.870 | 1.824 | 4.044 | 1.00 | 41.83 | C |
| ATOM | 3245 | CB | PHE A | 451 | −2.915 | 1.670 | 2.513 | 1.00 | 41.43 | C |
| ATOM | 3246 | CG | PHE A | 451 | −1.887 | 2.507 | 1.784 | 1.00 | 41.39 | C |
| ATOM | 3247 | CD1 | PHE A | 451 | −0.597 | 2.672 | 2.294 | 1.00 | 40.39 | C |
| ATOM | 3248 | CE1 | PHE A | 451 | 0.339 | 3.445 | 1.625 | 1.00 | 39.02 | C |
| ATOM | 3249 | CZ | PHE A | 451 | 0.002 | 4.060 | 0.430 | 1.00 | 38.89 | C |
| ATOM | 3250 | CE2 | PHE A | 451 | −1.268 | 3.908 | −0.094 | 1.00 | 40.12 | C |
| ATOM | 3251 | CD2 | PHE A | 451 | −2.207 | 3.134 | 0.581 | 1.00 | 41.71 | C |
| ATOM | 3252 | C | PHE A | 451 | −4.258 | 1.939 | 4.644 | 1.00 | 42.57 | C |
| ATOM | 3253 | O | PHE A | 451 | −5.089 | 1.039 | 4.492 | 1.00 | 43.27 | O |
| ATOM | 3254 | N | VAL A | 452 | −4.491 | 3.041 | 5.354 | 1.00 | 44.49 | N |
| ATOM | 3255 | CA | VAL A | 452 | −5.812 | 3.341 | 5.924 | 1.00 | 46.79 | C |
| ATOM | 3256 | CB | VAL A | 452 | −5.754 | 4.479 | 6.992 | 1.00 | 46.24 | C |
| ATOM | 3257 | CG1 | VAL A | 452 | −5.867 | 5.867 | 6.363 | 1.00 | 45.37 | C |
| ATOM | 3258 | CG2 | VAL A | 452 | −6.836 | 4.284 | 8.043 | 1.00 | 46.24 | C |
| ATOM | 3259 | C | VAL A | 452 | −6.825 | 3.633 | 4.807 | 1.00 | 47.28 | C |
| ATOM | 3260 | O | VAL A | 452 | −6.530 | 4.354 | 3.851 | 1.00 | 46.34 | O |
| ATOM | 3261 | N | ASP A | 453 | −8.008 | 3.043 | 4.928 | 1.00 | 50.16 | N |
| ATOM | 3262 | CA | ASP A | 453 | −9.002 | 3.083 | 3.860 | 1.00 | 52.96 | C |
| ATOM | 3263 | CB | ASP A | 453 | −9.104 | 1.696 | 3.182 | 1.00 | 58.71 | C |
| ATOM | 3264 | CG | ASP A | 453 | −7.833 | 1.332 | 2.350 | 1.00 | 63.02 | C |
| ATOM | 3265 | OD1 | ASP A | 453 | −7.400 | 2.154 | 1.504 | 1.00 | 64.18 | O |
| ATOM | 3266 | OD2 | ASP A | 453 | −7.282 | 0.214 | 2.528 | 1.00 | 61.14 | O |
| ATOM | 3267 | C | ASP A | 453 | −10.364 | 3.584 | 4.368 | 1.00 | 50.20 | C |
| ATOM | 3268 | O | ASP A | 453 | −11.413 | 3.135 | 3.913 | 1.00 | 48.99 | O |
| ATOM | 3269 | N | ASP A | 454 | −10.321 | 4.525 | 5.314 | 1.00 | 49.02 | N |
| ATOM | 3270 | CA | ASP A | 454 | −11.523 | 5.128 | 5.909 | 1.00 | 48.27 | C |
| ATOM | 3271 | CB | ASP A | 454 | −11.730 | 4.651 | 7.364 | 1.00 | 48.66 | C |
| ATOM | 3272 | CG | ASP A | 454 | −10.706 | 5.244 | 8.353 | 1.00 | 49.53 | C |
| ATOM | 3273 | OD1 | ASP A | 454 | −9.730 | 5.896 | 7.917 | 1.00 | 50.63 | O |
| ATOM | 3274 | OD2 | ASP A | 454 | −10.881 | 5.048 | 9.579 | 1.00 | 47.76 | O |
| ATOM | 3275 | C | ASP A | 454 | −11.472 | 6.656 | 5.840 | 1.00 | 46.93 | C |
| ATOM | 3276 | O | ASP A | 454 | −12.432 | 7.340 | 6.187 | 1.00 | 47.68 | O |
| ATOM | 3277 | N | GLN A | 455 | −10.328 | 7.176 | 5.418 | 1.00 | 45.28 | N |
| ATOM | 3278 | CA | GLN A | 455 | −10.178 | 8.589 | 5.134 | 1.00 | 44.72 | C |
| ATOM | 3279 | CB | GLN A | 455 | −8.882 | 9.130 | 5.755 | 1.00 | 44.77 | C |
| ATOM | 3280 | CG | GLN A | 455 | −8.786 | 9.027 | 7.270 | 1.00 | 44.22 | C |
| ATOM | 3281 | CD | GLN A | 455 | −9.670 | 10.023 | 8.014 | 1.00 | 44.12 | C |
| ATOM | 3282 | OE1 | GLN A | 455 | −10.523 | 10.693 | 7.430 | 1.00 | 43.57 | O |
| ATOM | 3283 | NE2 | GLN A | 455 | −9.469 | 10.112 | 9.318 | 1.00 | 44.24 | N |
| ATOM | 3284 | C | GLN A | 455 | −10.123 | 8.768 | 3.625 | 1.00 | 45.60 | C |
| ATOM | 3285 | O | GLN A | 455 | −9.946 | 7.799 | 2.883 | 1.00 | 47.84 | O |
| ATOM | 3286 | N | GLN A | 456 | −10.269 | 10.010 | 3.176 | 1.00 | 44.16 | N |
| ATOM | 3287 | CA | GLN A | 456 | −9.982 | 10.382 | 1.793 | 1.00 | 41.98 | C |
| ATOM | 3288 | CB | GLN A | 456 | −10.769 | 11.636 | 1.454 | 1.00 | 40.72 | C |
| ATOM | 3289 | CG | GLN A | 456 | −10.383 | 12.324 | 0.167 | 1.00 | 39.48 | C |
| ATOM | 3290 | CD | GLN A | 456 | −11.279 | 13.506 | −0.104 | 1.00 | 40.28 | C |
| ATOM | 3291 | OE1 | GLN A | 456 | −10.810 | 14.624 | −0.271 | 1.00 | 42.05 | O |
| ATOM | 3292 | NE2 | GLN A | 456 | −12.585 | 13.270 | −0.120 | 1.00 | 40.55 | N |
| ATOM | 3293 | C | GLN A | 456 | −8.478 | 10.632 | 1.620 | 1.00 | 41.23 | C |
| ATOM | 3294 | O | GLN A | 456 | −7.871 | 11.338 | 2.425 | 1.00 | 41.71 | O |

-continued

| | | | | | | | | | | |
|---|---|---|---|---|---|---|---|---|---|---|
| Atomic coordinates for CRBN:DDB1:Lenalidomide (Human protein) | | | | | | | | | | |
| ATOM | 3295 | N | THR A | 457 | −7.888 | 10.047 | 0.575 | 1.00 | 39.91 | N |
| ATOM | 3296 | CA | THR A | 457 | −6.446 | 10.179 | 0.295 | 1.00 | 39.80 | C |
| ATOM | 3297 | CB | THR A | 457 | −5.927 | 8.935 | −0.453 | 1.00 | 38.87 | C |
| ATOM | 3298 | OG1 | THR A | 457 | −5.998 | 7.798 | 0.414 | 1.00 | 37.70 | O |
| ATOM | 3299 | CG2 | THR A | 457 | −4.485 | 9.127 | −0.927 | 1.00 | 38.06 | C |
| ATOM | 3300 | C | THR A | 457 | −6.104 | 11.438 | −0.519 | 1.00 | 40.67 | C |
| ATOM | 3301 | O | THR A | 457 | −6.765 | 11.731 | −1.525 | 1.00 | 40.21 | O |
| ATOM | 3302 | N | PHE A | 458 | −5.077 | 12.173 | −0.085 | 1.00 | 41.65 | N |
| ATOM | 3303 | CA | PHE A | 458 | −4.626 | 13.374 | −0.814 | 1.00 | 44.31 | C |
| ATOM | 3304 | CB | PHE A | 458 | −4.368 | 14.550 | 0.134 | 1.00 | 49.60 | C |
| ATOM | 3305 | CG | PHE A | 458 | −5.619 | 15.282 | 0.533 | 1.00 | 55.86 | C |
| ATOM | 3306 | CD1 | PHE A | 458 | −6.425 | 15.893 | −0.435 | 1.00 | 57.18 | C |
| ATOM | 3307 | CE1 | PHE A | 458 | −7.592 | 16.558 | −0.073 | 1.00 | 59.11 | C |
| ATOM | 3308 | CZ | PHE A | 458 | −7.964 | 16.619 | 1.265 | 1.00 | 61.35 | C |
| ATOM | 3309 | CE2 | PHE A | 458 | −7.173 | 16.014 | 2.240 | 1.00 | 59.89 | C |
| ATOM | 3310 | CD2 | PHE A | 458 | −6.009 | 15.348 | 1.873 | 1.00 | 57.81 | C |
| ATOM | 3311 | C | PHE A | 458 | −3.420 | 13.128 | −1.719 | 1.00 | 42.63 | C |
| ATOM | 3312 | O | PHE A | 458 | −3.262 | 13.788 | −2.751 | 1.00 | 43.72 | O |
| ATOM | 3313 | N | PHE A | 459 | −2.566 | 12.191 | −1.322 | 1.00 | 38.14 | N |
| ATOM | 3314 | CA | PHE A | 459 | −1.523 | 11.688 | −2.192 | 1.00 | 35.19 | C |
| ATOM | 3315 | CB | PHE A | 459 | −0.287 | 12.593 | −2.195 | 1.00 | 33.44 | C |
| ATOM | 3316 | CG | PHE A | 459 | 0.909 | 11.952 | −2.842 | 1.00 | 32.80 | C |
| ATOM | 3317 | CD1 | PHE A | 459 | 1.080 | 12.003 | −4.225 | 1.00 | 31.63 | C |
| ATOM | 3318 | CE1 | PHE A | 459 | 2.159 | 11.384 | −4.832 | 1.00 | 30.73 | C |
| ATOM | 3319 | CZ | PHE A | 459 | 3.079 | 10.691 | −4.062 | 1.00 | 31.21 | C |
| ATOM | 3320 | CE2 | PHE A | 459 | 2.916 | 10.618 | −2.688 | 1.00 | 32.21 | C |
| ATOM | 3321 | CD2 | PHE A | 459 | 1.835 | 11.243 | −2.082 | 1.00 | 32.33 | C |
| ATOM | 3322 | C | PHE A | 459 | −1.106 | 10.322 | −1.726 | 1.00 | 34.61 | C |
| ATOM | 3323 | O | PHE A | 459 | −1.094 | 10.054 | −0.538 | 1.00 | 36.92 | O |
| ATOM | 3324 | N | CYS A | 460 | −0.750 | 9.459 | −2.664 | 1.00 | 34.35 | N |
| ATOM | 3325 | CA | CYS A | 460 | 0.006 | 8.269 | −2.332 | 1.00 | 35.21 | C |
| ATOM | 3326 | CB | CYS A | 460 | −0.918 | 7.095 | −2.011 | 1.00 | 37.29 | C |
| ATOM | 3327 | SG | CYS A | 460 | −1.705 | 6.355 | −3.448 | 1.00 | 42.12 | S |
| ATOM | 3328 | C | CYS A | 460 | 0.927 | 7.935 | −3.483 | 1.00 | 35.30 | C |
| ATOM | 3329 | O | CYS A | 460 | 0.798 | 8.497 | −4.570 | 1.00 | 36.13 | O |
| ATOM | 3330 | N | GLY A | 461 | 1.867 | 7.032 | −3.241 | 1.00 | 34.39 | N |
| ATOM | 3331 | CA | GLY A | 461 | 2.760 | 6.585 | −4.289 | 1.00 | 33.67 | C |
| ATOM | 3332 | C | GLY A | 461 | 4.036 | 6.018 | −3.732 | 1.00 | 33.95 | C |
| ATOM | 3333 | O | GLY A | 461 | 4.174 | 5.866 | −2.515 | 1.00 | 34.87 | O |
| ATOM | 3334 | N | ASN A | 462 | 4.968 | 5.702 | −4.632 | 1.00 | 33.09 | N |
| ATOM | 3335 | CA | ASN A | 462 | 6.248 | 5.145 | −4.256 | 1.00 | 33.16 | C |
| ATOM | 3336 | CB | ASN A | 462 | 6.888 | 4.418 | −5.433 | 1.00 | 32.11 | C |
| ATOM | 3337 | CG | ASN A | 462 | 6.097 | 3.203 | −5.870 | 1.00 | 32.20 | C |
| ATOM | 3338 | OD1 | ASN A | 462 | 6.475 | 2.067 | −5.590 | 1.00 | 31.71 | O |
| ATOM | 3339 | ND2 | ASN A | 462 | 4.993 | 3.434 | −6.567 | 1.00 | 32.99 | N |
| ATOM | 3340 | C | ASN A | 462 | 7.157 | 6.249 | −3.769 | 1.00 | 35.61 | C |
| ATOM | 3341 | O | ASN A | 462 | 7.116 | 7.365 | −4.295 | 1.00 | 34.91 | O |
| ATOM | 3342 | N | VAL A | 463 | 7.965 | 5.931 | −2.753 | 1.00 | 39.77 | N |
| ATOM | 3343 | CA | VAL A | 463 | 8.932 | 6.875 | −2.166 | 1.00 | 42.62 | C |
| ATOM | 3344 | CB | VAL A | 463 | 8.406 | 7.488 | −0.847 | 1.00 | 42.42 | C |
| ATOM | 3345 | CG1 | VAL A | 463 | 7.360 | 8.553 | −1.141 | 1.00 | 41.89 | C |
| ATOM | 3346 | CG2 | VAL A | 463 | 7.853 | 6.413 | 0.075 | 1.00 | 41.95 | C |
| ATOM | 3347 | C | VAL A | 463 | 10.333 | 6.270 | −1.951 | 1.00 | 44.89 | C |
| ATOM | 3348 | O | VAL A | 463 | 10.569 | 5.098 | −2.258 | 1.00 | 47.16 | O |
| ATOM | 3349 | N | ALA A | 464 | 11.254 | 7.076 | −1.424 | 1.00 | 46.43 | N |
| ATOM | 3350 | CA | ALA A | 464 | 12.649 | 6.652 | −1.221 | 1.00 | 48.09 | C |
| ATOM | 3351 | CB | ALA A | 464 | 13.531 | 7.856 | −0.908 | 1.00 | 48.16 | C |
| ATOM | 3352 | C | ALA A | 464 | 12.818 | 5.567 | −0.148 | 1.00 | 48.28 | C |
| ATOM | 3353 | O | ALA A | 464 | 12.032 | 5.490 | 0.803 | 1.00 | 48.89 | O |
| ATOM | 3354 | N | HIS A | 465 | 13.851 | 4.740 | −0.325 | 1.00 | 48.04 | N |
| ATOM | 3355 | CA | HIS A | 465 | 14.234 | 3.673 | 0.625 | 1.00 | 47.71 | C |
| ATOM | 3356 | CB | HIS A | 465 | 14.487 | 4.231 | 2.026 | 1.00 | 48.77 | C |
| ATOM | 3357 | CG | HIS A | 465 | 15.465 | 5.373 | 2.049 | 1.00 | 50.45 | C |
| ATOM | 3358 | ND1 | HIS A | 465 | 16.795 | 5.187 | 1.977 | 1.00 | 50.15 | N |
| ATOM | 3359 | CE1 | HIS A | 465 | 17.415 | 6.381 | 2.011 | 1.00 | 51.50 | C |
| ATOM | 3360 | NE2 | HIS A | 465 | 16.475 | 7.338 | 2.102 | 1.00 | 52.03 | N |
| ATOM | 3361 | CD2 | HIS A | 465 | 15.262 | 6.752 | 2.125 | 1.00 | 51.41 | C |
| ATOM | 3362 | C | HIS A | 465 | 13.298 | 2.491 | 0.675 | 1.00 | 45.94 | C |
| ATOM | 3363 | O | HIS A | 465 | 12.982 | 1.988 | 1.759 | 1.00 | 43.12 | O |
| ATOM | 3364 | N | GLN A | 466 | 12.872 | 2.034 | −0.508 | 1.00 | 45.45 | N |
| ATOM | 3365 | CA | GLN A | 466 | 12.072 | 0.809 | −0.674 | 1.00 | 46.22 | C |
| ATOM | 3366 | CB | GLN A | 466 | 12.853 | −0.427 | −0.200 | 1.00 | 48.54 | C |
| ATOM | 3367 | CG | GLN A | 466 | 14.201 | −0.623 | −0.876 | 1.00 | 50.97 | C |
| ATOM | 3368 | CD | GLN A | 466 | 14.080 | −0.724 | −2.381 | 1.00 | 52.63 | C |
| ATOM | 3369 | OE1 | GLN A | 466 | 13.308 | −1.535 | −2.902 | 1.00 | 55.23 | O |
| ATOM | 3370 | NE2 | GLN A | 466 | 14.836 | 0.106 | −3.092 | 1.00 | 52.56 | N |
| ATOM | 3371 | C | GLN A | 466 | 10.723 | 0.887 | 0.038 | 1.00 | 46.26 | C |

-continued

| | | | | | | | | | |
|---|---|---|---|---|---|---|---|---|---|
| \multicolumn{10}{c}{Atomic coordinates for CRBN:DDB1:Lenalidomide (Human protein)} |
| ATOM | 3372 | O | GLN A | 466 | 10.270 | −0.087 | 0.653 | 1.00 | 45.57 | O |
| ATOM | 3373 | N | GLN A | 467 | 10.080 | 2.048 | −0.058 | 1.00 | 45.98 | N |
| ATOM | 3374 | CA | GLN A | 467 | 8.913 | 2.341 | 0.769 | 1.00 | 45.22 | C |
| ATOM | 3375 | CB | GLN A | 467 | 9.289 | 3.304 | 1.922 | 1.00 | 45.41 | C |
| ATOM | 3376 | CG | GLN A | 467 | 9.929 | 2.610 | 3.128 | 1.00 | 45.81 | C |
| ATOM | 3377 | CD | GLN A | 467 | 10.679 | 3.554 | 4.067 | 1.00 | 46.80 | C |
| ATOM | 3378 | OE1 | GLN A | 467 | 11.391 | 4.466 | 3.627 | 1.00 | 47.37 | O |
| ATOM | 3379 | NE2 | GLN A | 467 | 10.540 | 3.319 | 5.373 | 1.00 | 45.24 | N |
| ATOM | 3380 | C | GLN A | 467 | 7.706 | 2.855 | −0.022 | 1.00 | 42.64 | C |
| ATOM | 3381 | O | GLN A | 467 | 7.765 | 3.020 | −1.243 | 1.00 | 40.86 | O |
| ATOM | 3382 | N | LEU A | 468 | 6.623 | 3.103 | 0.710 | 1.00 | 40.59 | N |
| ATOM | 3383 | CA | LEU A | 468 | 5.345 | 3.511 | 0.162 | 1.00 | 39.02 | C |
| ATOM | 3384 | CB | LEU A | 468 | 4.432 | 2.292 | 0.132 | 1.00 | 38.48 | C |
| ATOM | 3385 | CG | LEU A | 468 | 3.674 | 1.981 | −1.152 | 1.00 | 38.08 | C |
| ATOM | 3386 | CD1 | LEU A | 468 | 3.803 | 0.514 | −1.526 | 1.00 | 37.26 | C |
| ATOM | 3387 | CD2 | LEU A | 468 | 2.222 | 2.347 | −0.969 | 1.00 | 38.48 | C |
| ATOM | 3388 | C | LEU A | 468 | 4.772 | 4.604 | 1.076 | 1.00 | 38.80 | C |
| ATOM | 3389 | O | LEU A | 468 | 5.155 | 4.700 | 2.244 | 1.00 | 39.13 | O |
| ATOM | 3390 | N | ILE A | 469 | 3.875 | 5.438 | 0.557 | 1.00 | 38.69 | N |
| ATOM | 3391 | CA | ILE A | 469 | 3.339 | 6.547 | 1.364 | 1.00 | 40.51 | C |
| ATOM | 3392 | CB | ILE A | 469 | 4.198 | 7.833 | 1.203 | 1.00 | 40.72 | C |
| ATOM | 3393 | CG1 | ILE A | 469 | 3.862 | 8.856 | 2.296 | 1.00 | 40.12 | C |
| ATOM | 3394 | CD1 | ILE A | 469 | 4.883 | 9.965 | 2.439 | 1.00 | 41.82 | C |
| ATOM | 3395 | CG2 | ILE A | 469 | 4.037 | 8.429 | −0.193 | 1.00 | 40.40 | C |
| ATOM | 3396 | C | ILE A | 469 | 1.848 | 6.863 | 1.127 | 1.00 | 40.60 | C |
| ATOM | 3397 | O | ILE A | 469 | 1.401 | 6.930 | −0.011 | 1.00 | 41.16 | O |
| ATOM | 3398 | N | GLN A | 470 | 1.092 | 7.049 | 2.209 | 1.00 | 40.05 | N |
| ATOM | 3399 | CA | GLN A | 470 | −0.277 | 7.546 | 2.111 | 1.00 | 40.97 | C |
| ATOM | 3400 | CB | GLN A | 470 | −1.289 | 6.496 | 2.584 | 1.00 | 41.45 | C |
| ATOM | 3401 | CG | GLN A | 470 | −2.718 | 7.028 | 2.686 | 1.00 | 42.48 | C |
| ATOM | 3402 | CD | GLN A | 470 | −3.780 | 5.940 | 2.772 | 1.00 | 42.16 | C |
| ATOM | 3403 | OE1 | GLN A | 470 | −4.821 | 6.017 | 2.116 | 1.00 | 41.81 | O |
| ATOM | 3404 | NE2 | GLN A | 470 | −3.525 | 4.928 | 3.583 | 1.00 | 42.49 | N |
| ATOM | 3405 | C | GLN A | 470 | −0.457 | 8.834 | 2.906 | 1.00 | 42.34 | C |
| ATOM | 3406 | O | GLN A | 470 | −0.218 | 8.871 | 4.116 | 1.00 | 43.77 | O |
| ATOM | 3407 | N | ILE A | 471 | −0.893 | 9.886 | 2.221 | 1.00 | 42.56 | N |
| ATOM | 3408 | CA | ILE A | 471 | −1.186 | 11.158 | 2.873 | 1.00 | 43.72 | C |
| ATOM | 3409 | CB | ILE A | 471 | −0.411 | 12.334 | 2.233 | 1.00 | 41.85 | C |
| ATOM | 3410 | CG1 | ILE A | 471 | 1.100 | 12.068 | 2.281 | 1.00 | 40.87 | C |
| ATOM | 3411 | CD1 | ILE A | 471 | 1.956 | 13.143 | 1.644 | 1.00 | 41.25 | C |
| ATOM | 3412 | CG2 | ILE A | 471 | −0.753 | 13.639 | 2.937 | 1.00 | 41.97 | C |
| ATOM | 3413 | C | ILE A | 471 | −2.693 | 11.431 | 2.864 | 1.00 | 47.17 | C |
| ATOM | 3414 | O | ILE A | 471 | −3.258 | 11.850 | 1.843 | 1.00 | 47.50 | O |
| ATOM | 3415 | N | THR A | 472 | −3.336 | 11.172 | 4.005 | 1.00 | 49.76 | N |
| ATOM | 3416 | CA | THR A | 472 | −4.761 | 11.459 | 4.181 | 1.00 | 51.05 | C |
| ATOM | 3417 | CB | THR A | 472 | −5.475 | 10.380 | 5.021 | 1.00 | 51.95 | C |
| ATOM | 3418 | OG1 | THR A | 472 | −5.002 | 10.422 | 6.373 | 1.00 | 53.97 | O |
| ATOM | 3419 | CG2 | THR A | 472 | −5.246 | 9.000 | 4.439 | 1.00 | 52.95 | C |
| ATOM | 3420 | C | THR A | 472 | −4.980 | 12.817 | 4.845 | 1.00 | 52.07 | C |
| ATOM | 3421 | O | THR A | 472 | −4.029 | 13.561 | 5.092 | 1.00 | 53.60 | O |
| ATOM | 3422 | N | SER A | 473 | −6.243 | 13.134 | 5.117 | 1.00 | 53.15 | N |
| ATOM | 3423 | CA | SER A | 473 | −6.601 | 14.318 | 5.889 | 1.00 | 52.33 | C |
| ATOM | 3424 | CB | SER A | 473 | −8.114 | 14.556 | 5.845 | 1.00 | 52.39 | C |
| ATOM | 3425 | OG | SER A | 473 | −8.822 | 13.329 | 5.763 | 1.00 | 52.07 | O |
| ATOM | 3426 | C | SER A | 473 | −6.124 | 14.159 | 7.326 | 1.00 | 51.45 | C |
| ATOM | 3427 | O | SER A | 473 | −5.639 | 15.114 | 7.935 | 1.00 | 53.87 | O |
| ATOM | 3428 | N | ALA A | 474 | −6.240 | 12.941 | 7.851 | 1.00 | 48.94 | N |
| ATOM | 3429 | CA | ALA A | 474 | −5.831 | 12.651 | 9.223 | 1.00 | 47.42 | C |
| ATOM | 3430 | CB | ALA A | 474 | −6.409 | 11.322 | 9.689 | 1.00 | 46.79 | C |
| ATOM | 3431 | C | ALA A | 474 | −4.315 | 12.672 | 9.408 | 1.00 | 45.15 | C |
| ATOM | 3432 | O | ALA A | 474 | −3.801 | 13.460 | 10.195 | 1.00 | 46.18 | O |
| ATOM | 3433 | N | SER A | 475 | −3.601 | 11.816 | 8.685 | 0.50 | 42.12 | N |
| ATOM | 3434 | CA | SER A | 475 | −2.182 | 11.638 | 8.948 | 0.50 | 39.85 | C |
| ATOM | 3435 | CB | SER A | 475 | −1.974 | 10.544 | 9.997 | 0.50 | 39.67 | C |
| ATOM | 3436 | OG | SER A | 475 | −2.082 | 9.260 | 9.411 | 0.50 | 38.56 | O |
| ATOM | 3437 | C | SER A | 475 | −1.372 | 11.315 | 7.707 | 0.50 | 38.46 | C |
| ATOM | 3438 | O | SER A | 475 | −1.902 | 11.239 | 6.601 | 0.50 | 37.74 | O |
| ATOM | 3439 | N | VAL A | 476 | −0.074 | 11.135 | 7.920 | 1.00 | 37.89 | N |
| ATOM | 3440 | CA | VAL A | 476 | 0.875 | 10.797 | 6.872 | 1.00 | 38.34 | C |
| ATOM | 3441 | CB | VAL A | 476 | 1.998 | 11.851 | 6.768 | 1.00 | 36.70 | C |
| ATOM | 3442 | CG1 | VAL A | 476 | 2.936 | 11.523 | 5.622 | 1.00 | 35.88 | C |
| ATOM | 3443 | CG2 | VAL A | 476 | 1.421 | 13.254 | 6.616 | 1.00 | 36.34 | C |
| ATOM | 3444 | C | VAL A | 476 | 1.492 | 9.448 | 7.221 | 1.00 | 39.87 | C |
| ATOM | 3445 | O | VAL A | 476 | 2.114 | 9.295 | 8.276 | 1.00 | 39.70 | O |
| ATOM | 3446 | N | ARG A | 477 | 1.322 | 8.474 | 6.332 | 1.00 | 41.86 | N |
| ATOM | 3447 | CA | ARG A | 477 | 1.707 | 7.100 | 6.632 | 1.00 | 43.96 | C |
| ATOM | 3448 | CB | ARG A | 477 | 0.499 | 6.148 | 6.530 | 1.00 | 44.71 | C |

-continued

| | | | Atomic coordinates for CRBN:DDB1:Lenalidomide (Human protein) | | | | | | |
|---|---|---|---|---|---|---|---|---|---|
| ATOM | 3449 | CG | ARG A | 477 | −0.872 | 6.797 | 6.678 | 1.00 | 45.17 | C |
| ATOM | 3450 | CD | ARG A | 477 | −1.736 | 6.095 | 7.718 | 1.00 | 46.37 | C |
| ATOM | 3451 | NE | ARG A | 477 | −1.812 | 4.640 | 7.555 | 1.00 | 47.64 | N |
| ATOM | 3452 | CZ | ARG A | 477 | −1.930 | 3.783 | 8.572 | 1.00 | 48.71 | C |
| ATOM | 3453 | NH1 | ARG A | 477 | −1.965 | 4.234 | 9.818 | 1.00 | 49.09 | N |
| ATOM | 3454 | NH2 | ARG A | 477 | −1.995 | 2.474 | 8.354 | 1.00 | 47.73 | N |
| ATOM | 3455 | C | ARG A | 477 | 2.852 | 6.584 | 5.753 | 1.00 | 45.51 | C |
| ATOM | 3456 | O | ARG A | 477 | 2.659 | 6.309 | 4.564 | 1.00 | 47.30 | O |
| ATOM | 3457 | N | LEU A | 478 | 4.036 | 6.447 | 6.347 | 1.00 | 44.67 | N |
| ATOM | 3458 | CA | LEU A | 478 | 5.134 | 5.730 | 5.709 | 1.00 | 44.78 | C |
| ATOM | 3459 | CB | LEU A | 478 | 6.472 | 6.165 | 6.305 | 1.00 | 45.87 | C |
| ATOM | 3460 | CG | LEU A | 478 | 7.767 | 5.627 | 5.690 | 1.00 | 47.04 | C |
| ATOM | 3461 | CD1 | LEU A | 478 | 7.959 | 6.133 | 4.267 | 1.00 | 49.23 | C |
| ATOM | 3462 | CD2 | LEU A | 478 | 8.962 | 6.001 | 6.553 | 1.00 | 47.18 | C |
| ATOM | 3463 | C | LEU A | 478 | 4.938 | 4.221 | 5.882 | 1.00 | 45.57 | C |
| ATOM | 3464 | O | LEU A | 478 | 4.718 | 3.739 | 6.997 | 1.00 | 47.86 | O |
| ATOM | 3465 | N | VAL A | 479 | 5.000 | 3.487 | 4.773 | 1.00 | 44.87 | N |
| ATOM | 3466 | CA | VAL A | 479 | 4.809 | 2.031 | 4.771 | 1.00 | 44.31 | C |
| ATOM | 3467 | CB | VAL A | 479 | 3.529 | 1.623 | 3.998 | 1.00 | 44.19 | C |
| ATOM | 3468 | CG1 | VAL A | 479 | 3.305 | 0.119 | 4.051 | 1.00 | 43.45 | C |
| ATOM | 3469 | CG2 | VAL A | 479 | 2.308 | 2.352 | 4.537 | 1.00 | 45.17 | C |
| ATOM | 3470 | C | VAL A | 479 | 5.999 | 1.382 | 4.092 | 1.00 | 44.49 | C |
| ATOM | 3471 | O | VAL A | 479 | 6.579 | 1.964 | 3.184 | 1.00 | 46.29 | O |
| ATOM | 3472 | N | SER A | 480 | 6.357 | 0.179 | 4.525 | 1.00 | 45.99 | N |
| ATOM | 3473 | CA | SER A | 480 | 7.426 | −0.600 | 3.875 | 1.00 | 46.49 | C |
| ATOM | 3474 | CB | SER A | 480 | 8.190 | −1.458 | 4.906 | 1.00 | 45.41 | C |
| ATOM | 3475 | OG | SER A | 480 | 7.313 | −2.247 | 5.695 | 1.00 | 43.52 | O |
| ATOM | 3476 | C | SER A | 480 | 6.897 | −1.450 | 2.701 | 1.00 | 45.43 | C |
| ATOM | 3477 | O | SER A | 480 | 5.699 | −1.456 | 2.428 | 1.00 | 43.72 | O |
| ATOM | 3478 | N | GLN A | 481 | 7.797 | −2.152 | 2.013 | 1.00 | 46.97 | N |
| ATOM | 3479 | CA | GLN A | 481 | 7.432 | −2.968 | 0.852 | 1.00 | 50.05 | C |
| ATOM | 3480 | CB | GLN A | 481 | 8.371 | −2.680 | −0.320 | 1.00 | 49.01 | C |
| ATOM | 3481 | CG | GLN A | 481 | 8.068 | −1.391 | −1.064 | 1.00 | 48.30 | C |
| ATOM | 3482 | CD | GLN A | 481 | 7.014 | −1.579 | −2.127 | 1.00 | 48.18 | C |
| ATOM | 3483 | OE1 | GLN A | 481 | 5.838 | −1.761 | −1.825 | 1.00 | 49.19 | O |
| ATOM | 3484 | NE2 | GLN A | 481 | 7.433 | −1.542 | −3.386 | 1.00 | 47.73 | N |
| ATOM | 3485 | C | GLN A | 481 | 7.401 | −4.468 | 1.151 | 1.00 | 54.21 | C |
| ATOM | 3486 | O | GLN A | 481 | 6.360 | −5.113 | 1.004 | 1.00 | 55.66 | O |
| ATOM | 3487 | N | GLU A | 482 | 8.544 | −5.022 | 1.552 | 1.00 | 60.09 | N |
| ATOM | 3488 | CA | GLU A | 482 | 8.633 | −6.433 | 1.929 | 1.00 | 65.54 | C |
| ATOM | 3489 | CB | GLU A | 482 | 10.090 | −6.912 | 1.894 | 1.00 | 70.05 | C |
| ATOM | 3490 | CG | GLU A | 482 | 10.262 | −8.358 | 1.435 | 1.00 | 73.46 | C |
| ATOM | 3491 | CD | GLU A | 482 | 9.613 | −8.637 | 0.085 | 1.00 | 73.86 | C |
| ATOM | 3492 | OE1 | GLU A | 482 | 10.146 | −8.173 | −0.946 | 1.00 | 74.14 | O |
| ATOM | 3493 | OE2 | GLU A | 482 | 8.573 | −9.329 | 0.056 | 1.00 | 73.05 | O |
| ATOM | 3494 | C | GLU A | 482 | 8.008 | −6.618 | 3.317 | 1.00 | 67.11 | C |
| ATOM | 3495 | O | GLU A | 482 | 8.390 | −5.918 | 4.263 | 1.00 | 63.86 | O |
| ATOM | 3496 | N | PRO A | 483 | 7.102 | −7.614 | 3.456 | 1.00 | 69.37 | N |
| ATOM | 3497 | CA | PRO A | 483 | 5.930 | −7.529 | 4.316 | 1.00 | 69.18 | C |
| ATOM | 3498 | CB | PRO A | 483 | 6.330 | −8.420 | 5.495 | 1.00 | 69.35 | C |
| ATOM | 3499 | CG | PRO A | 483 | 7.181 | −9.492 | 4.839 | 1.00 | 69.68 | C |
| ATOM | 3500 | CD | PRO A | 483 | 7.572 | −9.008 | 3.448 | 1.00 | 68.89 | C |
| ATOM | 3501 | C | PRO A | 483 | 5.520 | −6.107 | 4.732 | 1.00 | 67.55 | C |
| ATOM | 3502 | O | PRO A | 483 | 6.143 | −5.493 | 5.605 | 1.00 | 69.42 | O |
| ATOM | 3503 | N | LYS A | 484 | 4.468 | −5.609 | 4.087 | 1.00 | 62.63 | N |
| ATOM | 3504 | CA | LYS A | 484 | 4.013 | −4.229 | 4.243 | 1.00 | 60.33 | C |
| ATOM | 3505 | CB | LYS A | 484 | 2.902 | −3.928 | 3.235 | 1.00 | 61.17 | C |
| ATOM | 3506 | CG | LYS A | 484 | 3.081 | −4.603 | 1.887 | 1.00 | 61.40 | C |
| ATOM | 3507 | CD | LYS A | 484 | 2.206 | −3.962 | 0.825 | 1.00 | 59.69 | C |
| ATOM | 3508 | CE | LYS A | 484 | 2.710 | −4.293 | −0.572 | 1.00 | 59.70 | C |
| ATOM | 3509 | NZ | LYS A | 484 | 4.047 | −3.692 | −0.856 | 1.00 | 57.22 | N |
| ATOM | 3510 | C | LYS A | 484 | 3.504 | −3.941 | 5.650 | 1.00 | 58.82 | C |
| ATOM | 3511 | O | LYS A | 484 | 2.695 | −4.693 | 6.192 | 1.00 | 58.60 | O |
| ATOM | 3512 | N | ALA A | 485 | 3.978 | −2.842 | 6.230 | 1.00 | 56.63 | N |
| ATOM | 3513 | CA | ALA A | 485 | 3.540 | −2.406 | 7.559 | 1.00 | 56.02 | C |
| ATOM | 3514 | CB | ALA A | 485 | 4.363 | −3.092 | 8.641 | 1.00 | 57.14 | C |
| ATOM | 3515 | C | ALA A | 485 | 3.650 | −0.893 | 7.697 | 1.00 | 54.62 | C |
| ATOM | 3516 | O | ALA A | 485 | 4.461 | −0.263 | 7.021 | 1.00 | 54.89 | O |
| ATOM | 3517 | N | LEU A | 486 | 2.837 | −0.316 | 8.577 | 1.00 | 53.13 | N |
| ATOM | 3518 | CA | LEU A | 486 | 2.918 | 1.112 | 8.873 | 1.00 | 52.85 | C |
| ATOM | 3519 | CB | LEU A | 486 | 1.649 | 1.574 | 9.601 | 1.00 | 54.48 | C |
| ATOM | 3520 | CG | LEU A | 486 | 1.682 | 2.926 | 10.330 | 1.00 | 55.55 | C |
| ATOM | 3521 | CD1 | LEU A | 486 | 1.587 | 4.103 | 9.365 | 1.00 | 54.60 | C |
| ATOM | 3522 | CD2 | LEU A | 486 | 0.592 | 2.987 | 11.393 | 1.00 | 55.64 | C |
| ATOM | 3523 | C | LEU A | 486 | 4.161 | 1.401 | 9.716 | 1.00 | 51.00 | C |
| ATOM | 3524 | O | LEU A | 486 | 4.091 | 1.430 | 10.942 | 1.00 | 52.35 | O |
| ATOM | 3525 | N | VAL A | 487 | 5.298 | 1.608 | 9.057 | 1.00 | 48.07 | N |

-continued

| | | Atomic coordinates for CRBN:DDB1:Lenalidomide (Human protein) | | | | | | | |
|---|---|---|---|---|---|---|---|---|---|
| ATOM | 3526 | CA | VAL A | 487 | 6.576 | 1.718 | 9.767 | 1.00 | 46.34 | C |
| ATOM | 3527 | CB | VAL A | 487 | 7.794 | 1.472 | 8.847 | 1.00 | 44.88 | C |
| ATOM | 3528 | CG1 | VAL A | 487 | 7.937 | −0.012 | 8.538 | 1.00 | 43.47 | C |
| ATOM | 3529 | CG2 | VAL A | 487 | 7.698 | 2.292 | 7.567 | 1.00 | 45.56 | C |
| ATOM | 3530 | C | VAL A | 487 | 6.720 | 3.031 | 10.539 | 1.00 | 46.92 | C |
| ATOM | 3531 | O | VAL A | 487 | 7.319 | 3.064 | 11.620 | 1.00 | 47.97 | O |
| ATOM | 3532 | N | SER A | 488 | 6.153 | 4.100 | 9.989 | 1.00 | 46.30 | N |
| ATOM | 3533 | CA | SER A | 488 | 6.154 | 5.402 | 10.644 | 1.00 | 46.22 | C |
| ATOM | 3534 | CB | SER A | 488 | 7.335 | 6.250 | 10.167 | 1.00 | 46.58 | C |
| ATOM | 3535 | OG | SER A | 488 | 8.470 | 6.060 | 10.990 | 1.00 | 46.34 | O |
| ATOM | 3536 | C | SER A | 488 | 4.865 | 6.147 | 10.373 | 1.00 | 45.99 | C |
| ATOM | 3537 | O | SER A | 488 | 4.296 | 6.048 | 9.289 | 1.00 | 45.74 | O |
| ATOM | 3538 | N | GLU A | 489 | 4.405 | 6.891 | 11.367 | 1.00 | 47.69 | N |
| ATOM | 3539 | CA | GLU A | 489 | 3.295 | 7.801 | 11.162 | 1.00 | 50.28 | C |
| ATOM | 3540 | CB | GLU A | 489 | 2.022 | 7.301 | 11.852 | 1.00 | 50.98 | C |
| ATOM | 3541 | CG | GLU A | 489 | 0.764 | 8.050 | 11.424 | 1.00 | 53.85 | C |
| ATOM | 3542 | CD | GLU A | 489 | −0.508 | 7.214 | 11.505 | 1.00 | 57.31 | C |
| ATOM | 3543 | OE1 | GLU A | 489 | −1.587 | 7.797 | 11.754 | 1.00 | 58.63 | O |
| ATOM | 3544 | OE2 | GLU A | 489 | −0.446 | 5.981 | 11.312 | 1.00 | 58.49 | O |
| ATOM | 3545 | C | GLU A | 489 | 3.656 | 9.202 | 11.628 | 1.00 | 52.15 | C |
| ATOM | 3546 | O | GLU A | 489 | 4.472 | 9.390 | 12.542 | 1.00 | 51.40 | O |
| ATOM | 3547 | N | TRP A | 490 | 3.057 | 10.181 | 10.963 | 1.00 | 53.45 | N |
| ATOM | 3548 | CA | TRP A | 490 | 3.202 | 11.571 | 11.328 | 1.00 | 55.27 | C |
| ATOM | 3549 | CB | TRP A | 490 | 4.105 | 12.275 | 10.340 | 1.00 | 54.50 | C |
| ATOM | 3550 | CG | TRP A | 490 | 4.388 | 13.707 | 10.689 | 1.00 | 55.57 | C |
| ATOM | 3551 | CD1 | TRP A | 490 | 5.524 | 14.218 | 11.305 | 1.00 | 56.92 | C |
| ATOM | 3552 | NE1 | TRP A | 490 | 5.432 | 15.580 | 11.447 | 1.00 | 57.95 | N |
| ATOM | 3553 | CE2 | TRP A | 490 | 4.263 | 16.033 | 10.947 | 1.00 | 57.40 | C |
| ATOM | 3554 | CD2 | TRP A | 490 | 3.533 | 14.871 | 10.439 | 1.00 | 56.18 | C |
| ATOM | 3555 | CE3 | TRP A | 490 | 2.283 | 15.060 | 9.866 | 1.00 | 56.86 | C |
| ATOM | 3556 | CZ3 | TRP A | 490 | 1.765 | 16.359 | 9.805 | 1.00 | 57.22 | C |
| ATOM | 3557 | CH2 | TRP A | 490 | 2.482 | 17.460 | 10.294 | 1.00 | 57.19 | C |
| ATOM | 3558 | CZ2 | TRP A | 490 | 3.745 | 17.317 | 10.876 | 1.00 | 57.88 | C |
| ATOM | 3559 | C | TRP A | 490 | 1.856 | 12.210 | 11.328 | 1.00 | 57.38 | C |
| ATOM | 3560 | O | TRP A | 490 | 1.081 | 12.052 | 10.383 | 1.00 | 58.08 | O |
| ATOM | 3561 | N | LYS A | 491 | 1.562 | 12.938 | 12.397 | 1.00 | 60.13 | N |
| ATOM | 3562 | CA | LYS A | 491 | 0.324 | 13.688 | 12.499 | 1.00 | 61.82 | C |
| ATOM | 3563 | CB | LYS A | 491 | −0.686 | 12.944 | 13.377 | 1.00 | 63.77 | C |
| ATOM | 3564 | CG | LYS A | 491 | −2.134 | 13.335 | 13.123 | 1.00 | 66.80 | C |
| ATOM | 3565 | CD | LYS A | 491 | −3.103 | 12.237 | 13.542 | 1.00 | 68.86 | C |
| ATOM | 3566 | CE | LYS A | 491 | −4.535 | 12.598 | 13.164 | 1.00 | 68.89 | C |
| ATOM | 3567 | NZ | LYS A | 491 | −5.450 | 11.421 | 13.159 | 1.00 | 68.88 | N |
| ATOM | 3568 | C | LYS A | 491 | 0.651 | 15.051 | 13.078 | 1.00 | 62.09 | C |
| ATOM | 3569 | O | LYS A | 491 | 1.706 | 15.228 | 13.696 | 1.00 | 61.56 | O |
| ATOM | 3570 | N | GLU A | 492 | −0.239 | 16.017 | 12.861 | 1.00 | 62.70 | N |
| ATOM | 3571 | CA | GLU A | 492 | −0.069 | 17.349 | 13.428 | 1.00 | 62.29 | C |
| ATOM | 3572 | CB | GLU A | 492 | −1.194 | 18.279 | 12.972 | 1.00 | 63.77 | C |
| ATOM | 3573 | CG | GLU A | 492 | −0.838 | 19.756 | 13.076 | 1.00 | 64.15 | C |
| ATOM | 3574 | CD | GLU A | 492 | −1.962 | 20.598 | 13.645 | 1.00 | 65.90 | C |
| ATOM | 3575 | OE1 | GLU A | 492 | −2.796 | 20.054 | 14.399 | 1.00 | 67.37 | O |
| ATOM | 3576 | OE2 | GLU A | 492 | −2.005 | 21.809 | 13.346 | 1.00 | 66.21 | O |
| ATOM | 3577 | C | GLU A | 492 | −0.047 | 17.270 | 14.954 | 1.00 | 60.81 | C |
| ATOM | 3578 | O | GLU A | 492 | −0.824 | 16.513 | 15.537 | 1.00 | 59.93 | O |
| ATOM | 3579 | N | PRO A | 493 | 0.865 | 18.032 | 15.600 | 1.00 | 60.19 | N |
| ATOM | 3580 | CA | PRO A | 493 | 0.913 | 18.164 | 17.056 | 1.00 | 58.70 | C |
| ATOM | 3581 | CB | PRO A | 493 | 1.816 | 19.378 | 17.253 | 1.00 | 57.99 | C |
| ATOM | 3582 | CG | PRO A | 493 | 2.790 | 19.277 | 16.126 | 1.00 | 58.14 | C |
| ATOM | 3583 | CD | PRO A | 493 | 2.050 | 18.652 | 14.968 | 1.00 | 59.51 | C |
| ATOM | 3584 | C | PRO A | 493 | −0.453 | 18.388 | 17.722 | 1.00 | 59.19 | C |
| ATOM | 3585 | O | PRO A | 493 | −0.708 | 17.822 | 18.786 | 1.00 | 60.05 | O |
| ATOM | 3586 | N | GLN A | 494 | −1.322 | 19.185 | 17.101 | 1.00 | 59.58 | N |
| ATOM | 3587 | CA | GLN A | 494 | −2.667 | 19.424 | 17.643 | 1.00 | 60.94 | C |
| ATOM | 3588 | CB | GLN A | 494 | −3.073 | 20.890 | 17.457 | 1.00 | 60.26 | C |
| ATOM | 3589 | C | GLN A | 494 | −3.743 | 18.486 | 17.066 | 1.00 | 62.53 | C |
| ATOM | 3590 | O | GLN A | 494 | −4.939 | 18.703 | 17.277 | 1.00 | 61.69 | O |
| ATOM | 3591 | N | ALA A | 495 | −3.304 | 17.448 | 16.349 | 1.00 | 64.58 | N |
| ATOM | 3592 | CA | ALA A | 495 | −4.191 | 16.424 | 15.762 | 1.00 | 65.33 | C |
| ATOM | 3593 | CB | ALA A | 495 | −4.767 | 15.519 | 16.853 | 1.00 | 63.92 | C |
| ATOM | 3594 | C | ALA A | 495 | −5.308 | 16.989 | 14.865 | 1.00 | 67.00 | C |
| ATOM | 3595 | O | ALA A | 495 | −6.460 | 16.544 | 14.936 | 1.00 | 68.46 | O |
| ATOM | 3596 | N | LYS A | 496 | −4.955 | 17.953 | 14.014 | 1.00 | 66.19 | N |
| ATOM | 3597 | CA | LYS A | 496 | −5.934 | 18.641 | 13.164 | 1.00 | 64.61 | C |
| ATOM | 3598 | CB | LYS A | 496 | −5.618 | 20.138 | 13.071 | 1.00 | 65.20 | C |
| ATOM | 3599 | CG | LYS A | 496 | −6.063 | 20.961 | 14.272 | 1.00 | 64.12 | C |
| ATOM | 3600 | CD | LYS A | 496 | −6.391 | 22.392 | 13.867 | 1.00 | 64.40 | C |
| ATOM | 3601 | CE | LYS A | 496 | −7.710 | 22.467 | 13.103 | 1.00 | 64.90 | C |
| ATOM | 3602 | NZ | LYS A | 496 | −7.916 | 23.787 | 12.444 | 1.00 | 63.91 | N |

-continued

| | | | | | | | | | | |
|---|---|---|---|---|---|---|---|---|---|---|
| ATOM | 3603 | C | LYS A | 496 | −6.036 | 18.045 | 11.760 | 1.00 | 64.34 | C |
| ATOM | 3604 | O | LYS A | 496 | −5.183 | 17.254 | 11.348 | 1.00 | 65.48 | O |
| ATOM | 3605 | N | ASN A | 497 | −7.087 | 18.445 | 11.037 | 1.00 | 62.34 | N |
| ATOM | 3606 | CA | ASN A | 497 | −7.348 | 17.998 | 9.663 | 1.00 | 58.45 | C |
| ATOM | 3607 | CB | ASN A | 497 | −8.828 | 18.216 | 9.298 | 1.00 | 56.77 | C |
| ATOM | 3608 | CG | ASN A | 497 | −9.744 | 17.125 | 9.845 | 1.00 | 56.46 | C |
| ATOM | 3609 | OD1 | ASN A | 497 | −9.463 | 16.512 | 10.876 | 1.00 | 56.68 | O |
| ATOM | 3610 | ND2 | ASN A | 497 | −10.855 | 16.885 | 9.152 | 1.00 | 54.70 | N |
| ATOM | 3611 | C | ASN A | 497 | −6.454 | 18.698 | 8.638 | 1.00 | 56.98 | C |
| ATOM | 3612 | O | ASN A | 497 | −6.468 | 19.927 | 8.535 | 1.00 | 57.10 | O |
| ATOM | 3613 | N | ILE A | 498 | −5.681 | 17.906 | 7.891 | 1.00 | 54.60 | N |
| ATOM | 3614 | CA | ILE A | 498 | −4.803 | 18.415 | 6.826 | 1.00 | 53.19 | C |
| ATOM | 3615 | CB | ILE A | 498 | −3.786 | 17.336 | 6.351 | 1.00 | 51.98 | C |
| ATOM | 3616 | CG1 | ILE A | 498 | −2.788 | 17.000 | 7.467 | 1.00 | 49.61 | C |
| ATOM | 3617 | CD1 | ILE A | 498 | −1.808 | 15.897 | 7.117 | 1.00 | 47.94 | C |
| ATOM | 3618 | CG2 | ILE A | 498 | −3.041 | 17.789 | 5.097 | 1.00 | 52.15 | C |
| ATOM | 3619 | C | ILE A | 498 | −5.634 | 18.943 | 5.646 | 1.00 | 52.27 | C |
| ATOM | 3620 | O | ILE A | 498 | −6.584 | 18.287 | 5.205 | 1.00 | 51.27 | O |
| ATOM | 3621 | N | SER A | 499 | −5.274 | 20.130 | 5.150 | 1.00 | 51.59 | N |
| ATOM | 3622 | CA | SER A | 499 | −6.035 | 20.796 | 4.081 | 1.00 | 52.00 | C |
| ATOM | 3623 | CB | SER A | 499 | −6.270 | 22.291 | 4.396 | 1.00 | 50.60 | C |
| ATOM | 3624 | OG | SER A | 499 | −5.058 | 23.025 | 4.508 | 1.00 | 48.04 | O |
| ATOM | 3625 | C | SER A | 499 | −5.452 | 20.601 | 2.670 | 1.00 | 52.90 | C |
| ATOM | 3626 | O | SER A | 499 | −6.211 | 20.485 | 1.703 | 1.00 | 55.16 | O |
| ATOM | 3627 | N | VAL A | 500 | −4.119 | 20.586 | 2.556 | 1.00 | 52.51 | N |
| ATOM | 3628 | CA | VAL A | 500 | −3.425 | 20.332 | 1.278 | 1.00 | 50.20 | C |
| ATOM | 3629 | CB | VAL A | 500 | −3.117 | 21.629 | 0.494 | 1.00 | 51.08 | C |
| ATOM | 3630 | CG1 | VAL A | 500 | −2.847 | 21.297 | −0.966 | 1.00 | 54.06 | C |
| ATOM | 3631 | CG2 | VAL A | 500 | −4.251 | 22.639 | 0.597 | 1.00 | 50.55 | C |
| ATOM | 3632 | C | VAL A | 500 | −2.099 | 19.600 | 1.504 | 1.00 | 48.27 | C |
| ATOM | 3633 | O | VAL A | 500 | −1.410 | 19.856 | 2.491 | 1.00 | 48.00 | O |
| ATOM | 3634 | N | ALA A | 501 | −1.743 | 18.705 | 0.581 | 1.00 | 47.33 | N |
| ATOM | 3635 | CA | ALA A | 501 | −0.485 | 17.943 | 0.668 | 1.00 | 49.38 | C |
| ATOM | 3636 | CB | ALA A | 501 | −0.763 | 16.511 | 1.090 | 1.00 | 47.41 | C |
| ATOM | 3637 | C | ALA A | 501 | 0.322 | 17.963 | −0.639 | 1.00 | 51.85 | C |
| ATOM | 3638 | O | ALA A | 501 | −0.229 | 18.230 | −1.711 | 1.00 | 55.82 | O |
| ATOM | 3639 | N | SER A | 502 | 1.624 | 17.678 | −0.537 | 1.00 | 51.54 | N |
| ATOM | 3640 | CA | SER A | 502 | 2.521 | 17.589 | −1.702 | 1.00 | 51.51 | C |
| ATOM | 3641 | CB | SER A | 502 | 2.912 | 18.981 | −2.201 | 1.00 | 53.38 | C |
| ATOM | 3642 | OG | SER A | 502 | 3.557 | 19.726 | −1.181 | 1.00 | 54.00 | O |
| ATOM | 3643 | C | SER A | 502 | 3.777 | 16.792 | −1.360 | 1.00 | 50.43 | C |
| ATOM | 3644 | O | SER A | 502 | 4.393 | 17.013 | −0.317 | 1.00 | 50.95 | O |
| ATOM | 3645 | N | CYS A | 503 | 4.166 | 15.881 | −2.248 | 1.00 | 48.30 | N |
| ATOM | 3646 | CA | CYS A | 503 | 5.206 | 14.911 | −1.924 | 1.00 | 48.04 | C |
| ATOM | 3647 | CB | CYS A | 503 | 4.616 | 13.816 | −1.039 | 1.00 | 45.41 | C |
| ATOM | 3648 | SG | CYS A | 503 | 5.588 | 12.305 | −1.018 | 1.00 | 45.78 | S |
| ATOM | 3649 | C | CYS A | 503 | 5.898 | 14.287 | −3.144 | 1.00 | 49.28 | C |
| ATOM | 3650 | O | CYS A | 503 | 5.268 | 13.598 | −3.944 | 1.00 | 53.69 | O |
| ATOM | 3651 | N | ASN A | 504 | 7.200 | 14.514 | −3.271 | 1.00 | 48.14 | N |
| ATOM | 3652 | CA | ASN A | 504 | 7.976 | 13.892 | −4.334 | 1.00 | 47.83 | C |
| ATOM | 3653 | CB | ASN A | 504 | 9.058 | 14.853 | −4.858 | 1.00 | 49.77 | C |
| ATOM | 3654 | CG | ASN A | 504 | 9.924 | 15.442 | −3.751 | 1.00 | 50.36 | C |
| ATOM | 3655 | OD1 | ASN A | 504 | 9.952 | 14.946 | −2.627 | 1.00 | 51.24 | O |
| ATOM | 3656 | ND2 | ASN A | 504 | 10.639 | 16.507 | −4.075 | 1.00 | 50.20 | N |
| ATOM | 3657 | C | ASN A | 504 | 8.584 | 12.555 | −3.901 | 1.00 | 48.68 | C |
| ATOM | 3658 | O | ASN A | 504 | 7.980 | 11.813 | −3.119 | 1.00 | 47.31 | O |
| ATOM | 3659 | N | SER A | 505 | 9.784 | 12.265 | −4.402 | 1.00 | 48.90 | N |
| ATOM | 3660 | CA | SER A | 505 | 10.473 | 11.010 | −4.121 | 1.00 | 49.84 | C |
| ATOM | 3661 | CB | SER A | 505 | 11.678 | 10.855 | −5.051 | 1.00 | 49.73 | C |
| ATOM | 3662 | OG | SER A | 505 | 12.035 | 9.495 | −5.204 | 1.00 | 48.86 | O |
| ATOM | 3663 | C | SER A | 505 | 10.917 | 10.904 | −2.661 | 1.00 | 52.35 | C |
| ATOM | 3664 | O | SER A | 505 | 10.938 | 9.809 | −2.094 | 1.00 | 53.28 | O |
| ATOM | 3665 | N | SER A | 506 | 11.262 | 12.045 | −2.062 | 1.00 | 54.98 | N |
| ATOM | 3666 | CA | SER A | 506 | 11.773 | 12.097 | −0.687 | 1.00 | 55.98 | C |
| ATOM | 3667 | CB | SER A | 506 | 13.234 | 12.545 | −0.671 | 1.00 | 54.37 | C |
| ATOM | 3668 | OG | SER A | 506 | 13.843 | 12.371 | −1.936 | 1.00 | 55.05 | O |
| ATOM | 3669 | C | SER A | 506 | 10.959 | 13.045 | 0.191 | 1.00 | 58.34 | C |
| ATOM | 3670 | O | SER A | 506 | 10.426 | 12.647 | 1.221 | 1.00 | 60.81 | O |
| ATOM | 3671 | N | GLN A | 507 | 10.863 | 14.300 | −0.230 | 1.00 | 59.81 | N |
| ATOM | 3672 | CA | GLN A | 507 | 10.294 | 15.359 | 0.603 | 1.00 | 61.33 | C |
| ATOM | 3673 | CB | GLN A | 507 | 10.862 | 16.711 | 0.171 | 1.00 | 62.96 | C |
| ATOM | 3674 | CG | GLN A | 507 | 12.380 | 16.791 | 0.248 | 1.00 | 62.04 | C |
| ATOM | 3675 | CD | GLN A | 507 | 12.981 | 17.544 | −0.917 | 1.00 | 61.90 | C |
| ATOM | 3676 | OE1 | GLN A | 507 | 12.754 | 17.194 | −2.077 | 1.00 | 60.65 | O |
| ATOM | 3677 | NE2 | GLN A | 507 | 13.758 | 18.582 | −0.618 | 1.00 | 60.82 | N |
| ATOM | 3678 | C | GLN A | 507 | 8.754 | 15.399 | 0.623 | 1.00 | 61.25 | C |
| ATOM | 3679 | O | GLN A | 507 | 8.090 | 15.014 | −0.345 | 1.00 | 59.65 | O |

-continued

| | | | Atomic coordinates for CRBN:DDB1:Lenalidomide (Human protein) | | | | | | |
|---|---|---|---|---|---|---|---|---|---|
| ATOM | 3680 | N | VAL A | 508 | 8.209 | 15.865 | 1.747 | 1.00 | 58.81 | N |
| ATOM | 3681 | CA | VAL A | 508 | 6.770 | 16.021 | 1.933 | 1.00 | 57.70 | C |
| ATOM | 3682 | CB | VAL A | 508 | 6.217 | 14.992 | 2.947 | 1.00 | 58.51 | C |
| ATOM | 3683 | CG1 | VAL A | 508 | 4.740 | 15.247 | 3.237 | 1.00 | 57.30 | C |
| ATOM | 3684 | CG2 | VAL A | 508 | 6.433 | 13.567 | 2.450 | 1.00 | 59.50 | C |
| ATOM | 3685 | C | VAL A | 508 | 6.495 | 17.423 | 2.462 | 1.00 | 56.84 | C |
| ATOM | 3686 | O | VAL A | 508 | 7.155 | 17.871 | 3.397 | 1.00 | 59.52 | O |
| ATOM | 3687 | N | VAL A | 509 | 5.535 | 18.118 | 1.857 | 1.00 | 54.93 | N |
| ATOM | 3688 | CA | VAL A | 509 | 5.107 | 19.426 | 2.359 | 1.00 | 54.53 | C |
| ATOM | 3689 | CB | VAL A | 509 | 5.614 | 20.603 | 1.491 | 1.00 | 53.47 | C |
| ATOM | 3690 | CG1 | VAL A | 509 | 5.102 | 21.933 | 2.032 | 1.00 | 52.06 | C |
| ATOM | 3691 | CG2 | VAL A | 509 | 7.135 | 20.613 | 1.432 | 1.00 | 53.02 | C |
| ATOM | 3692 | C | VAL A | 509 | 3.591 | 19.472 | 2.506 | 1.00 | 54.33 | C |
| ATOM | 3693 | O | VAL A | 509 | 2.854 | 19.537 | 1.521 | 1.00 | 51.21 | O |
| ATOM | 3694 | N | VAL A | 510 | 3.144 | 19.436 | 3.755 | 1.00 | 58.04 | N |
| ATOM | 3695 | CA | VAL A | 510 | 1.723 | 19.372 | 4.077 | 1.00 | 61.77 | C |
| ATOM | 3696 | CB | VAL A | 510 | 1.386 | 18.168 | 4.992 | 1.00 | 60.26 | C |
| ATOM | 3697 | CG1 | VAL A | 510 | 1.391 | 16.873 | 4.191 | 1.00 | 58.84 | C |
| ATOM | 3698 | CG2 | VAL A | 510 | 2.348 | 18.089 | 6.174 | 1.00 | 58.78 | C |
| ATOM | 3699 | C | VAL A | 510 | 1.224 | 20.664 | 4.716 | 1.00 | 64.58 | C |
| ATOM | 3700 | O | VAL A | 510 | 1.818 | 21.172 | 5.672 | 1.00 | 65.43 | O |
| ATOM | 3701 | N | ALA A | 511 | 0.131 | 21.188 | 4.172 | 1.00 | 66.78 | N |
| ATOM | 3702 | CA | ALA A | 511 | −0.506 | 22.377 | 4.711 | 1.00 | 67.46 | C |
| ATOM | 3703 | CB | ALA A | 511 | −1.033 | 23.247 | 3.584 | 1.00 | 67.71 | C |
| ATOM | 3704 | C | ALA A | 511 | −1.632 | 21.988 | 5.659 | 1.00 | 69.37 | C |
| ATOM | 3705 | O | ALA A | 511 | −2.420 | 21.080 | 5.364 | 1.00 | 67.83 | O |
| ATOM | 3706 | N | VAL A | 512 | −1.684 | 22.661 | 6.809 | 1.00 | 70.63 | N |
| ATOM | 3707 | CA | VAL A | 512 | −2.785 | 22.495 | 7.762 | 1.00 | 69.14 | C |
| ATOM | 3708 | CB | VAL A | 512 | −2.325 | 21.863 | 9.104 | 1.00 | 66.23 | C |
| ATOM | 3709 | CG1 | VAL A | 512 | −3.528 | 21.440 | 9.934 | 1.00 | 65.55 | C |
| ATOM | 3710 | CG2 | VAL A | 512 | −1.423 | 20.660 | 8.859 | 1.00 | 64.84 | C |
| ATOM | 3711 | C | VAL A | 512 | −3.480 | 23.845 | 7.988 | 1.00 | 68.59 | C |
| ATOM | 3712 | O | VAL A | 512 | −3.208 | 24.542 | 8.965 | 1.00 | 67.13 | O |
| ATOM | 3713 | N | GLY A | 513 | −4.351 | 24.210 | 7.045 | 1.00 | 70.74 | N |
| ATOM | 3714 | CA | GLY A | 513 | −5.172 | 25.421 | 7.127 | 1.00 | 68.37 | C |
| ATOM | 3715 | C | GLY A | 513 | −4.409 | 26.733 | 7.098 | 1.00 | 67.79 | C |
| ATOM | 3716 | O | GLY A | 513 | −4.441 | 27.457 | 6.103 | 1.00 | 66.74 | O |
| ATOM | 3717 | N | ARG A | 514 | −3.723 | 27.028 | 8.202 | 1.00 | 69.00 | N |
| ATOM | 3718 | CA | ARG A | 514 | −3.109 | 28.336 | 8.445 | 1.00 | 69.52 | C |
| ATOM | 3719 | CB | ARG A | 514 | −3.434 | 28.801 | 9.877 | 1.00 | 66.66 | C |
| ATOM | 3720 | CG | ARG A | 514 | −3.336 | 30.303 | 10.120 | 1.00 | 65.18 | C |
| ATOM | 3721 | CD | ARG A | 514 | −4.030 | 30.685 | 11.424 | 1.00 | 63.83 | C |
| ATOM | 3722 | NE | ARG A | 514 | −3.580 | 31.976 | 11.955 | 1.00 | 62.51 | N |
| ATOM | 3723 | CZ | ARG A | 514 | −3.949 | 32.487 | 13.134 | 1.00 | 61.32 | C |
| ATOM | 3724 | NH1 | ARG A | 514 | −4.785 | 31.828 | 13.928 | 1.00 | 60.42 | N |
| ATOM | 3725 | NH2 | ARG A | 514 | −3.479 | 33.667 | 13.524 | 1.00 | 59.28 | N |
| ATOM | 3726 | C | ARG A | 514 | −1.591 | 28.317 | 8.209 | 1.00 | 70.88 | C |
| ATOM | 3727 | O | ARG A | 514 | −1.029 | 29.275 | 7.670 | 1.00 | 69.40 | O |
| ATOM | 3728 | N | ALA A | 515 | −0.944 | 27.220 | 8.613 | 1.00 | 70.64 | N |
| ATOM | 3729 | CA | ALA A | 515 | 0.512 | 27.064 | 8.506 | 1.00 | 67.99 | C |
| ATOM | 3730 | CB | ALA A | 515 | 1.164 | 27.313 | 9.851 | 1.00 | 68.73 | C |
| ATOM | 3731 | C | ALA A | 515 | 0.881 | 25.676 | 7.988 | 1.00 | 66.45 | C |
| ATOM | 3732 | O | ALA A | 515 | 0.115 | 24.725 | 8.152 | 1.00 | 66.98 | O |
| ATOM | 3733 | N | LEU A | 516 | 2.059 | 25.561 | 7.375 | 1.00 | 64.91 | N |
| ATOM | 3734 | CA | LEU A | 516 | 2.464 | 24.319 | 6.694 | 1.00 | 62.81 | C |
| ATOM | 3735 | CB | LEU A | 516 | 2.425 | 24.488 | 5.164 | 1.00 | 62.85 | C |
| ATOM | 3736 | CG | LEU A | 516 | 2.792 | 25.822 | 4.504 | 1.00 | 61.64 | C |
| ATOM | 3737 | CD1 | LEU A | 516 | 4.293 | 25.964 | 4.344 | 1.00 | 59.47 | C |
| ATOM | 3738 | CD2 | LEU A | 516 | 2.105 | 25.940 | 3.151 | 1.00 | 62.69 | C |
| ATOM | 3739 | C | LEU A | 516 | 3.813 | 23.751 | 7.141 | 1.00 | 60.12 | C |
| ATOM | 3740 | O | LEU A | 516 | 4.736 | 24.497 | 7.474 | 1.00 | 61.15 | O |
| ATOM | 3741 | N | TYR A | 517 | 3.916 | 22.423 | 7.124 | 1.00 | 57.39 | N |
| ATOM | 3742 | CA | TYR A | 517 | 5.097 | 21.718 | 7.622 | 1.00 | 57.13 | C |
| ATOM | 3743 | CB | TYR A | 517 | 4.702 | 20.709 | 8.704 | 1.00 | 56.31 | C |
| ATOM | 3744 | CG | TYR A | 517 | 3.826 | 21.271 | 9.806 | 1.00 | 56.16 | C |
| ATOM | 3745 | CD2 | TYR A | 517 | 2.436 | 21.205 | 9.715 | 1.00 | 55.27 | C |
| ATOM | 3746 | CE2 | TYR A | 517 | 1.630 | 21.711 | 10.720 | 1.00 | 54.05 | C |
| ATOM | 3747 | CZ | TYR A | 517 | 2.209 | 22.285 | 11.837 | 1.00 | 51.62 | C |
| ATOM | 3748 | OH | TYR A | 517 | 1.396 | 22.781 | 12.821 | 1.00 | 49.86 | O |
| ATOM | 3749 | CE1 | TYR A | 517 | 3.585 | 22.361 | 11.959 | 1.00 | 51.95 | C |
| ATOM | 3750 | CD1 | TYR A | 517 | 4.387 | 21.852 | 10.950 | 1.00 | 53.89 | C |
| ATOM | 3751 | C | TYR A | 517 | 5.878 | 20.992 | 6.525 | 1.00 | 57.53 | C |
| ATOM | 3752 | O | TYR A | 517 | 5.293 | 30.399 | 5.618 | 1.00 | 57.77 | O |
| ATOM | 3753 | N | TYR A | 518 | 7.202 | 21.032 | 6.636 | 1.00 | 57.24 | N |
| ATOM | 3754 | CA | TYR A | 518 | 8.086 | 20.290 | 5.744 | 1.00 | 57.41 | C |
| ATOM | 3755 | CB | TYR A | 518 | 9.285 | 21.158 | 5.348 | 1.00 | 59.37 | C |
| ATOM | 3756 | CG | TYR A | 518 | 10.410 | 20.405 | 4.671 | 1.00 | 61.22 | C |

-continued

| | | Atomic coordinates for CRBN:DDB1:Lenalidomide (Human protein) | | | | | | | | |
|---|---|---|---|---|---|---|---|---|---|---|
| ATOM | 3757 | CD1 | TYR A | 518 | 10.246 | 19.852 | 3.397 | 1.00 | 61.96 | C |
| ATOM | 3758 | CE1 | TYR A | 518 | 11.278 | 19.165 | 2.774 | 1.00 | 62.58 | C |
| ATOM | 3759 | CZ | TYR A | 518 | 12.495 | 19.025 | 3.425 | 1.00 | 63.95 | C |
| ATOM | 3760 | OH | TYR A | 518 | 13.525 | 18.345 | 2.818 | 1.00 | 62.48 | O |
| ATOM | 3761 | CE2 | TYR A | 518 | 12.681 | 19.564 | 4.688 | 1.00 | 64.28 | C |
| ATOM | 3762 | CD2 | TYR A | 518 | 11.642 | 20.249 | 5.301 | 1.00 | 62.87 | C |
| ATOM | 3763 | C | TYR A | 518 | 8.551 | 18.985 | 6.396 | 1.00 | 56.78 | C |
| ATOM | 3764 | O | TYR A | 518 | 8.907 | 18.965 | 7.577 | 1.00 | 58.28 | O |
| ATOM | 3765 | N | LEU A | 519 | 8.541 | 17.903 | 5.620 | 1.00 | 54.27 | N |
| ATOM | 3766 | CA | LEU A | 519 | 8.902 | 16.573 | 6.115 | 1.00 | 53.09 | C |
| ATOM | 3767 | CB | LEU A | 519 | 7.642 | 15.752 | 6.397 | 1.00 | 53.58 | C |
| ATOM | 3768 | CG | LEU A | 519 | 6.867 | 15.875 | 7.716 | 1.00 | 53.00 | C |
| ATOM | 3769 | CD1 | LEU A | 519 | 5.975 | 17.110 | 7.767 | 1.00 | 52.65 | C |
| ATOM | 3770 | CD2 | LEU A | 519 | 6.027 | 14.620 | 7.885 | 1.00 | 51.44 | C |
| ATOM | 3771 | C | LEU A | 519 | 9.784 | 15.818 | 5.120 | 1.00 | 52.93 | C |
| ATOM | 3772 | O | LEU A | 519 | 9.689 | 16.032 | 3.911 | 1.00 | 51.85 | O |
| ATOM | 3773 | N | GLN A | 520 | 10.631 | 14.928 | 5.638 | 1.00 | 53.61 | N |
| ATOM | 3774 | CA | GLN A | 520 | 11.534 | 14.120 | 4.807 | 1.00 | 53.62 | C |
| ATOM | 3775 | CB | GLN A | 520 | 12.987 | 14.402 | 5.167 | 1.00 | 52.40 | C |
| ATOM | 3776 | CG | GLN A | 520 | 13.466 | 15.762 | 4.708 | 1.00 | 52.52 | C |
| ATOM | 3777 | CD | GLN A | 520 | 14.945 | 15.782 | 4.399 | 1.00 | 51.82 | C |
| ATOM | 3778 | OE1 | GLN A | 520 | 15.778 | 15.514 | 5.267 | 1.00 | 51.59 | O |
| ATOM | 3779 | NE2 | GLN A | 520 | 15.282 | 16.107 | 3.157 | 1.00 | 50.02 | N |
| ATOM | 3780 | C | GLN A | 520 | 11.260 | 12.627 | 4.941 | 1.00 | 55.81 | C |
| ATOM | 3781 | O | GLN A | 520 | 10.516 | 12.208 | 5.826 | 1.00 | 59.83 | O |
| ATOM | 3782 | N | ILE A | 521 | 11.857 | 11.829 | 4.056 | 1.00 | 55.06 | N |
| ATOM | 3783 | CA | ILE A | 521 | 11.708 | 10.371 | 4.111 | 1.00 | 54.44 | C |
| ATOM | 3784 | CB | ILE A | 521 | 10.855 | 9.807 | 2.939 | 1.00 | 54.67 | C |
| ATOM | 3785 | CG1 | ILE A | 521 | 9.433 | 10.386 | 2.976 | 1.00 | 54.63 | C |
| ATOM | 3786 | CD1 | ILE A | 521 | 8.664 | 10.261 | 1.675 | 1.00 | 51.62 | C |
| ATOM | 3787 | CG2 | ILE A | 521 | 10.797 | 8.277 | 2.989 | 1.00 | 53.85 | C |
| ATOM | 3788 | C | ILE A | 521 | 13.067 | 9.671 | 4.183 | 1.00 | 54.11 | C |
| ATOM | 3789 | O | ILE A | 521 | 13.871 | 9.731 | 3.244 | 1.00 | 52.80 | O |
| ATOM | 3790 | N | HIS A | 522 | 13.303 | 9.017 | 5.318 | 1.00 | 53.64 | N |
| ATOM | 3791 | CA | HIS A | 522 | 14.501 | 8.216 | 5.549 | 1.00 | 53.87 | C |
| ATOM | 3792 | CB | HIS A | 522 | 15.383 | 8.887 | 6.600 | 1.00 | 53.96 | C |
| ATOM | 3793 | CG | HIS A | 522 | 15.871 | 10.262 | 6.195 | 1.00 | 54.41 | C |
| ATOM | 3794 | ND1 | HIS A | 522 | 17.090 | 10.471 | 5.665 | 1.00 | 53.90 | N |
| ATOM | 3795 | CE1 | HIS A | 522 | 17.241 | 11.781 | 5.395 | 1.00 | 53.53 | C |
| ATOM | 3796 | NE2 | HIS A | 522 | 16.111 | 12.414 | 5.749 | 1.00 | 52.94 | N |
| ATOM | 3797 | CD2 | HIS A | 522 | 15.245 | 11.509 | 6.245 | 1.00 | 53.93 | C |
| ATOM | 3798 | C | HIS A | 522 | 14.068 | 6.842 | 5.992 | 1.00 | 53.83 | C |
| ATOM | 3799 | O | HIS A | 522 | 12.934 | 6.679 | 6.450 | 1.00 | 54.00 | O |
| ATOM | 3800 | N | PRO A | 523 | 14.949 | 5.822 | 5.853 | 1.00 | 53.25 | N |
| ATOM | 3801 | CA | PRO A | 523 | 14.532 | 4.454 | 6.180 | 1.00 | 52.11 | C |
| ATOM | 3802 | CB | PRO A | 523 | 15.857 | 3.695 | 6.254 | 1.00 | 51.48 | C |
| ATOM | 3803 | CG | PRO A | 523 | 16.739 | 4.417 | 5.305 | 1.00 | 52.15 | C |
| ATOM | 3804 | CD | PRO A | 523 | 16.359 | 5.870 | 5.419 | 1.00 | 53.12 | C |
| ATOM | 3805 | C | PRO A | 523 | 13.806 | 4.381 | 7.515 | 1.00 | 51.22 | C |
| ATOM | 3806 | O | PRO A | 523 | 14.285 | 4.939 | 8.500 | 1.00 | 51.50 | O |
| ATOM | 3807 | N | GLN A | 524 | 12.641 | 3.730 | 7.521 | 1.00 | 51.33 | N |
| ATOM | 3808 | CA | GLN A | 524 | 11.821 | 3.523 | 8.731 | 1.00 | 51.10 | C |
| ATOM | 3809 | CB | GLN A | 524 | 12.606 | 2.763 | 9.821 | 1.00 | 51.35 | C |
| ATOM | 3810 | CG | GLN A | 524 | 12.370 | 1.255 | 9.855 | 1.00 | 50.89 | C |
| ATOM | 3811 | CD | GLN A | 524 | 12.636 | 0.562 | 8.526 | 1.00 | 49.98 | C |
| ATOM | 3812 | OE1 | GLN A | 524 | 13.535 | 0.946 | 7.771 | 1.00 | 48.99 | O |
| ATOM | 3813 | NE2 | GLN A | 524 | 11.856 | −0.475 | 8.240 | 1.00 | 49.37 | N |
| ATOM | 3814 | C | GLN A | 524 | 11.166 | 4.773 | 9.324 | 1.00 | 50.83 | C |
| ATOM | 3815 | O | GLN A | 524 | 10.173 | 4.657 | 10.042 | 1.00 | 49.18 | O |
| ATOM | 3816 | N | GLU A | 525 | 11.711 | 5.954 | 9.026 | 1.00 | 51.79 | N |
| ATOM | 3817 | CA | GLU A | 525 | 11.243 | 7.203 | 9.645 | 1.00 | 52.88 | C |
| ATOM | 3818 | CB | GLU A | 525 | 12.258 | 7.731 | 10.681 | 1.00 | 52.98 | C |
| ATOM | 3819 | CG | GLU A | 525 | 13.634 | 8.081 | 10.115 | 1.00 | 54.73 | C |
| ATOM | 3820 | CE | GLU A | 525 | 14.325 | 9.222 | 10.853 | 1.00 | 55.57 | C |
| ATOM | 3821 | OE1 | GLU A | 525 | 13.794 | 10.355 | 10.847 | 1.00 | 56.35 | O |
| ATOM | 3822 | OE2 | GLU A | 525 | 15.419 | 8.996 | 11.414 | 1.00 | 54.61 | O |
| ATOM | 3823 | C | GLU A | 525 | 10.882 | 8.315 | 8.656 | 1.00 | 53.04 | C |
| ATOM | 3824 | O | GLU A | 525 | 11.524 | 8.485 | 7.618 | 1.00 | 51.31 | O |
| ATOM | 3825 | N | LEU A | 526 | 9.830 | 9.054 | 8.992 | 1.00 | 54.98 | N |
| ATOM | 3826 | CA | LEU A | 526 | 9.582 | 10.369 | 8.411 | 1.00 | 56.40 | C |
| ATOM | 3827 | CB | LEU A | 526 | 8.282 | 10.409 | 7.587 | 1.00 | 56.34 | C |
| ATOM | 3828 | CG | LEU A | 526 | 7.060 | 9.513 | 7.843 | 1.00 | 55.47 | C |
| ATOM | 3829 | CD1 | LEU A | 526 | 6.441 | 9.694 | 9.222 | 1.00 | 54.64 | C |
| ATOM | 3830 | CD2 | LEU A | 526 | 6.023 | 9.772 | 6.759 | 1.00 | 54.25 | C |
| ATOM | 3831 | C | LEU A | 526 | 9.553 | 11.413 | 9.521 | 1.00 | 59.02 | C |
| ATOM | 3832 | O | LEU A | 526 | 8.530 | 11.591 | 10.192 | 1.00 | 61.20 | O |
| ATOM | 3833 | N | ARG A | 527 | 10.684 | 12.080 | 9.738 | 1.00 | 58.87 | N |

-continued

| | | | Atomic coordinates for CRBN:DDB1:Lenalidomide (Human protein) | | | | | | |
|---|---|---|---|---|---|---|---|---|---|
| ATOM | 3834 | CA | ARG A | 527 | 10.754 | 13.106 | 10.773 | 1.00 | 57.45 | C |
| ATOM | 3835 | CB | ARG A | 527 | 11.986 | 12.921 | 11.676 | 1.00 | 57.43 | C |
| ATOM | 3836 | CG | ARG A | 527 | 11.689 | 12.964 | 13.181 | 1.00 | 57.48 | C |
| ATOM | 3837 | CD | ARG A | 527 | 11.089 | 11.655 | 13.707 | 1.00 | 57.53 | C |
| ATOM | 3838 | NE | ARG A | 527 | 9.637 | 11.567 | 13.493 | 1.00 | 59.21 | N |
| ATOM | 3839 | CZ | ARG A | 527 | 8.973 | 10.448 | 13.483 | 1.00 | 59.40 | C |
| ATOM | 3840 | NH1 | ARG A | 527 | 9.618 | 9.296 | 13.036 | 1.00 | 60.39 | N |
| ATOM | 3841 | NH2 | ARG A | 527 | 7.655 | 10.482 | 13.004 | 1.00 | 57.61 | N |
| ATOM | 3842 | C | ARG A | 527 | 10.707 | 14.494 | 10.154 | 1.00 | 56.24 | C |
| ATOM | 3843 | O | ARG A | 527 | 11.180 | 14.707 | 9.034 | 1.00 | 55.42 | O |
| ATOM | 3844 | N | GLN A | 528 | 10.105 | 15.424 | 10.892 | 1.00 | 56.15 | N |
| ATOM | 3845 | CA | GLN A | 528 | 9.889 | 16.795 | 10.442 | 1.00 | 56.71 | C |
| ATOM | 3846 | CB | GLN A | 528 | 9.006 | 17.518 | 11.463 | 1.00 | 55.34 | C |
| ATOM | 3847 | CG | GLN A | 528 | 8.300 | 18.752 | 10.934 | 1.00 | 55.15 | C |
| ATOM | 3848 | CD | GLN A | 528 | 7.334 | 19.343 | 11.939 | 1.00 | 55.23 | C |
| ATOM | 3849 | OE1 | GLN A | 528 | 6.575 | 18.623 | 12.589 | 1.00 | 55.39 | O |
| ATOM | 3850 | NE2 | GLN A | 528 | 7.353 | 20.665 | 12.068 | 1.00 | 55.90 | N |
| ATOM | 3851 | C | GLN A | 528 | 11.220 | 17.540 | 10.271 | 1.00 | 57.49 | C |
| ATOM | 3852 | O | GLN A | 528 | 12.283 | 17.000 | 10.587 | 1.00 | 59.51 | O |
| ATOM | 3853 | N | ILE A | 529 | 11.153 | 18.768 | 9.752 | 1.00 | 56.75 | N |
| ATOM | 3854 | CA | ILE A | 529 | 12.312 | 19.672 | 9.720 | 1.00 | 56.24 | C |
| ATOM | 3855 | CB | ILE A | 529 | 13.145 | 19.513 | 8.421 | 1.00 | 54.62 | C |
| ATOM | 3856 | CG1 | ILE A | 529 | 14.112 | 18.334 | 8.556 | 1.00 | 52.36 | C |
| ATOM | 3857 | CD1 | ILE A | 529 | 14.760 | 17.903 | 7.259 | 1.00 | 51.53 | C |
| ATOM | 3858 | CG2 | ILE A | 529 | 13.925 | 20.786 | 8.106 | 1.00 | 54.49 | C |
| ATOM | 3859 | C | ILE A | 529 | 11.906 | 21.136 | 9.971 | 1.00 | 57.63 | C |
| ATOM | 3860 | O | ILE A | 529 | 12.495 | 21.814 | 10.822 | 1.00 | 59.60 | O |
| ATOM | 3861 | N | SER A | 530 | 10.886 | 21.603 | 9.253 | 1.00 | 57.58 | N |
| ATOM | 3862 | CA | SER A | 530 | 10.455 | 22.999 | 9.341 | 1.00 | 58.22 | C |
| ATOM | 3863 | CB | SER A | 530 | 10.622 | 23.693 | 7.990 | 1.00 | 58.25 | C |
| ATOM | 3864 | OG | SER A | 530 | 11.895 | 23.434 | 7.427 | 1.00 | 58.13 | O |
| ATOM | 3865 | C | SER A | 530 | 9.010 | 23.146 | 9.818 | 1.00 | 59.25 | C |
| ATOM | 3866 | O | SER A | 530 | 8.201 | 22.231 | 9.671 | 1.00 | 59.85 | O |
| ATOM | 3867 | N | HIS A | 531 | 8.703 | 24.309 | 10.388 | 1.00 | 60.56 | N |
| ATOM | 3868 | CA | HIS A | 531 | 7.356 | 24.643 | 10.856 | 1.00 | 62.22 | C |
| ATOM | 3869 | CB | HIS A | 531 | 7.127 | 24.147 | 12.292 | 1.00 | 60.25 | C |
| ATOM | 3870 | CG | HIS A | 531 | 8.387 | 24.091 | 13.134 | 1.00 | 58.01 | C |
| ATOM | 3871 | ND1 | HIS A | 531 | 9.167 | 22.994 | 13.199 | 1.00 | 57.16 | N |
| ATOM | 3872 | CE1 | HIS A | 531 | 10.211 | 23.232 | 14.010 | 1.00 | 55.98 | C |
| ATOM | 3873 | NE2 | HIS A | 531 | 10.100 | 24.487 | 14.473 | 1.00 | 56.15 | N |
| ATOM | 3874 | CD2 | HIS A | 531 | 8.987 | 25.045 | 13.952 | 1.00 | 57.01 | C |
| ATOM | 3875 | C | HIS A | 531 | 7.159 | 26.127 | 10.760 | 1.00 | 64.89 | C |
| ATOM | 3876 | O | HIS A | 531 | 7.709 | 26.884 | 11.564 | 1.00 | 66.97 | O |
| ATOM | 3877 | N | THR A | 532 | 6.377 | 26.561 | 9.769 | 1.00 | 66.97 | N |
| ATOM | 3878 | CA | THR A | 532 | 6.242 | 27.990 | 9.459 | 1.00 | 68.99 | C |
| ATOM | 3879 | CB | THR A | 532 | 6.636 | 28.279 | 7.998 | 1.00 | 68.42 | C |
| ATOM | 3880 | OG1 | THR A | 532 | 7.472 | 27.221 | 7.517 | 1.00 | 69.92 | O |
| ATOM | 3881 | CG2 | THR A | 532 | 7.384 | 29.608 | 7.890 | 1.00 | 67.56 | C |
| ATOM | 3882 | C | THR A | 532 | 4.838 | 28.541 | 9.753 | 1.00 | 71.44 | C |
| ATOM | 3883 | O | THR A | 532 | 4.092 | 27.958 | 10.541 | 1.00 | 72.27 | O |
| ATOM | 3884 | N | GLU A | 533 | 4.501 | 29.675 | 9.133 | 1.00 | 73.26 | N |
| ATOM | 3885 | CA | GLU A | 533 | 3.215 | 30.346 | 9.344 | 1.00 | 74.57 | C |
| ATOM | 3886 | CB | GLU A | 533 | 3.275 | 31.259 | 10.581 | 1.00 | 75.29 | C |
| ATOM | 3887 | CG | GLU A | 533 | 2.116 | 31.092 | 11.563 | 1.00 | 75.10 | C |
| ATOM | 3888 | CD | GLU A | 533 | 0.748 | 31.213 | 10.911 | 1.00 | 76.06 | C |
| ATOM | 3889 | OE1 | GLU A | 533 | −0.046 | 30.252 | 11.008 | 1.00 | 74.65 | O |
| ATOM | 3890 | OE2 | GLU A | 533 | 0.468 | 32.261 | 10.292 | 1.00 | 77.25 | O |
| ATOM | 3891 | C | GLU A | 533 | 2.833 | 31.159 | 8.105 | 1.00 | 73.20 | C |
| ATOM | 3892 | O | GLU A | 533 | 3.687 | 31.811 | 7.496 | 1.00 | 71.42 | O |
| ATOM | 3893 | N | MET A | 534 | 1.551 | 31.127 | 7.745 | 1.00 | 72.95 | N |
| ATOM | 3894 | CA | MET A | 534 | 1.088 | 31.759 | 6.507 | 1.00 | 72.02 | C |
| ATOM | 3895 | CB | MET A | 534 | 0.459 | 30.715 | 5.576 | 1.00 | 71.34 | C |
| ATOM | 3896 | CG | MET A | 534 | 0.971 | 30.777 | 4.149 | 1.00 | 71.17 | C |
| ATOM | 3897 | SD | MET A | 534 | 2.732 | 30.392 | 4.058 | 1.00 | 73.00 | S |
| ATOM | 3898 | CE | MET A | 534 | 3.171 | 31.047 | 2.449 | 1.00 | 70.93 | C |
| ATOM | 3899 | C | MET A | 534 | 0.119 | 32.923 | 6.737 | 1.00 | 70.54 | C |
| ATOM | 3900 | O | MET A | 534 | −0.771 | 32.851 | 7.594 | 1.00 | 70.27 | O |
| ATOM | 3901 | N | GLU A | 535 | 0.302 | 33.987 | 2.958 | 1.00 | 67.00 | N |
| ATOM | 3902 | CA | GLU A | 535 | −0.577 | 35.153 | 6.000 | 1.00 | 64.93 | C |
| ATOM | 3903 | CB | GLU A | 535 | 0.163 | 36.397 | 5.498 | 1.00 | 62.90 | C |
| ATOM | 3904 | C | GLU A | 535 | −1.841 | 34.920 | 5.171 | 1.00 | 63.32 | C |
| ATOM | 3905 | O | GLU A | 535 | −2.674 | 34.073 | 5.503 | 1.00 | 60.76 | O |
| ATOM | 3906 | N | VAL A | 538 | −3.872 | 28.903 | 2.551 | 1.00 | 68.23 | N |
| ATOM | 3907 | CA | VAL A | 538 | −3.153 | 28.019 | 1.633 | 1.00 | 69.94 | C |
| ATOM | 3908 | CB | VAL A | 538 | −1.989 | 27.271 | 2.339 | 1.00 | 70.92 | C |
| ATOM | 3909 | CG1 | VAL A | 538 | −2.463 | 26.599 | 3.624 | 1.00 | 71.65 | C |
| ATOM | 3910 | CG2 | VAL A | 538 | −1.320 | 26.272 | 1.399 | 1.00 | 69.92 | C |

-continued

| | | | | | | | | | | |
|---|---|---|---|---|---|---|---|---|---|---|
| ATOM | 3911 | C | VAL A | 538 | −4.110 | 27.050 | 0.934 | 1.00 | 69.95 | C |
| ATOM | 3912 | O | VAL A | 538 | −4.903 | 26.364 | 1.586 | 1.00 | 70.70 | O |
| ATOM | 3913 | N | ALA A | 539 | −4.023 | 26.999 | −0.394 | 1.00 | 68.15 | N |
| ATOM | 3914 | CA | ALA A | 539 | −5.002 | 26.280 | −1.210 | 1.00 | 67.46 | C |
| ATOM | 3915 | CB | ALA A | 539 | −5.811 | 27.266 | −2.047 | 1.00 | 66.43 | C |
| ATOM | 3916 | C | ALA A | 539 | −4.404 | 25.173 | −2.098 | 1.00 | 66.14 | C |
| ATOM | 3917 | O | ALA A | 539 | −5.141 | 24.335 | −2.628 | 1.00 | 65.94 | O |
| ATOM | 3918 | N | CYS A | 540 | −3.080 | 25.176 | −2.258 | 1.00 | 64.53 | N |
| ATOM | 3919 | CA | CYS A | 540 | −2.391 | 24.176 | −3.083 | 1.00 | 62.51 | C |
| ATOM | 3920 | CB | CYS A | 540 | −2.718 | 24.381 | −4.555 | 1.00 | 62.19 | C |
| ATOM | 3921 | SG | CYS A | 540 | −2.459 | 26.081 | −5.086 | 1.00 | 63.95 | S |
| ATOM | 3922 | C | CYS A | 540 | −0.881 | 24.214 | −2.884 | 1.00 | 62.38 | C |
| ATOM | 3923 | O | CYS A | 540 | −0.316 | 25.256 | −2.532 | 1.00 | 61.78 | O |
| ATOM | 3924 | N | LEU A | 541 | −0.233 | 23.076 | −3.122 | 1.00 | 60.51 | N |
| ATOM | 3925 | CA | LEU A | 541 | 1.208 | 22.947 | −2.907 | 1.00 | 60.74 | C |
| ATOM | 3926 | CB | LEU A | 541 | 1.485 | 22.171 | −1.619 | 1.00 | 60.85 | C |
| ATOM | 3927 | CG | LEU A | 541 | 1.252 | 22.842 | −0.270 | 1.00 | 62.23 | C |
| ATOM | 3928 | CD1 | LEU A | 541 | 1.035 | 21.785 | 0.802 | 1.00 | 61.89 | C |
| ATOM | 3929 | CD2 | LEU A | 541 | 2.416 | 23.751 | 0.088 | 1.00 | 61.57 | C |
| ATOM | 3930 | C | LEU A | 541 | 1.895 | 22.244 | −4.071 | 1.00 | 59.87 | C |
| ATOM | 3931 | O | LEU A | 541 | 1.231 | 21.608 | −4.893 | 1.00 | 60.03 | O |
| ATOM | 3932 | N | ASP A | 542 | 3.224 | 22.371 | −4.133 | 1.00 | 58.60 | N |
| ATOM | 3933 | CA | ASP A | 542 | 4.053 | 21.582 | −5.054 | 1.00 | 56.91 | C |
| ATOM | 3934 | CB | ASP A | 542 | 3.874 | 22.036 | −6.501 | 1.00 | 55.92 | C |
| ATOM | 3935 | CG | ASP A | 542 | 4.322 | 20.986 | −7.484 | 1.00 | 56.55 | C |
| ATOM | 3936 | OD1 | ASP A | 542 | 5.539 | 20.898 | −7.736 | 1.00 | 58.69 | O |
| ATOM | 3937 | OD2 | ASP A | 542 | 3.465 | 20.232 | −7.985 | 1.00 | 57.48 | O |
| ATOM | 3938 | C | ASP A | 542 | 5.547 | 21.535 | −4.691 | 1.00 | 55.72 | C |
| ATOM | 3939 | O | ASP A | 542 | 6.113 | 22.501 | −4.168 | 1.00 | 55.87 | O |
| ATOM | 3940 | N | ILE A | 543 | 6.174 | 20.403 | −5.001 | 1.00 | 52.19 | N |
| ATOM | 3941 | CA | ILE A | 543 | 7.553 | 20.137 | −4.619 | 1.00 | 50.09 | C |
| ATOM | 3942 | CB | ILE A | 543 | 7.626 | 19.597 | −3.153 | 1.00 | 49.12 | C |
| ATOM | 3943 | CG1 | ILE A | 543 | 9.010 | 19.051 | −2.797 | 1.00 | 50.55 | C |
| ATOM | 3944 | CD1 | ILE A | 543 | 10.032 | 20.110 | −2.450 | 1.00 | 53.64 | C |
| ATOM | 3945 | CG2 | ILE A | 543 | 6.596 | 18.511 | −2.905 | 1.00 | 49.51 | C |
| ATOM | 3946 | C | ILE A | 543 | 8.230 | 19.200 | −5.642 | 1.00 | 50.83 | C |
| ATOM | 3947 | O | ILE A | 543 | 9.093 | 18.397 | −5.282 | 1.00 | 51.26 | O |
| ATOM | 3948 | N | THR A | 544 | 7.848 | 19.310 | −6.918 | 1.00 | 50.74 | N |
| ATOM | 3949 | CA | THR A | 544 | 8.437 | 18.450 | −7.958 | 1.00 | 51.56 | C |
| ATOM | 3950 | CB | THR A | 544 | 7.627 | 18.407 | −9.285 | 1.00 | 51.75 | C |
| ATOM | 3951 | OG1 | THR A | 544 | 6.262 | 18.775 | −9.060 | 1.00 | 54.13 | O |
| ATOM | 3952 | CG2 | THR A | 544 | 7.663 | 17.005 | −9.893 | 1.00 | 50.16 | C |
| ATOM | 3953 | C | THR A | 544 | 9.866 | 18.909 | −8.246 | 1.00 | 52.03 | C |
| ATOM | 3954 | O | THR A | 544 | 10.072 | 20.051 | −8.659 | 1.00 | 52.53 | O |
| ATOM | 3955 | N | PRO A | 545 | 10.855 | 18.016 | −8.023 | 1.00 | 51.95 | N |
| ATOM | 3956 | CA | PRO A | 545 | 12.272 | 18.357 | −8.130 | 1.00 | 52.98 | C |
| ATOM | 3957 | CB | PRO A | 545 | 12.987 | 17.097 | −7.603 | 1.00 | 53.11 | C |
| ATOM | 3958 | CG | PRO A | 545 | 11.928 | 16.253 | −6.976 | 1.00 | 51.30 | C |
| ATOM | 3959 | CD | PRO A | 545 | 10.668 | 16.593 | −7.695 | 1.00 | 51.40 | C |
| ATOM | 3960 | C | PRO A | 545 | 12.706 | 18.652 | −9.562 | 1.00 | 54.25 | C |
| ATOM | 3961 | O | PRO A | 545 | 12.408 | 17.874 | −10.469 | 1.00 | 54.97 | O |
| ATOM | 3962 | N | LEU A | 546 | 13.408 | 19.772 | −9.749 | 1.00 | 55.05 | N |
| ATOM | 3963 | CA | LEU A | 546 | 13.926 | 20.170 | −11.064 | 1.00 | 55.87 | C |
| ATOM | 3964 | CB | LEU A | 546 | 13.080 | 21.305 | −11.660 | 1.00 | 56.28 | C |
| ATOM | 3965 | CG | LEU A | 546 | 11.576 | 21.086 | −11.868 | 1.00 | 56.41 | C |
| ATOM | 3966 | CD1 | LEU A | 546 | 10.897 | 22.390 | −12.262 | 1.00 | 56.07 | C |
| ATOM | 3967 | CD2 | LEU A | 546 | 11.302 | 20.000 | −12.901 | 1.00 | 56.01 | C |
| ATOM | 3968 | C | LEU A | 546 | 15.402 | 20.590 | −10.995 | 1.00 | 55.89 | C |
| ATOM | 3969 | O | LEU A | 546 | 16.083 | 20.709 | −12.021 | 1.00 | 53.56 | O |
| ATOM | 3970 | N | GLY A | 551 | 17.976 | 14.760 | −6.588 | 1.00 | 52.89 | N |
| ATOM | 3971 | CA | GLY A | 551 | 16.779 | 14.099 | −6.074 | 1.00 | 55.06 | C |
| ATOM | 3972 | C | GLY A | 551 | 15.851 | 15.026 | −5.301 | 1.00 | 57.11 | C |
| ATOM | 3973 | O | GLY A | 551 | 14.625 | 14.975 | −5.475 | 1.00 | 54.09 | O |
| ATOM | 3974 | N | LEU A | 552 | 16.442 | 15.882 | −4.459 | 1.00 | 58.53 | N |
| ATOM | 3975 | CA | LEU A | 552 | 15.692 | 16.765 | −3.543 | 1.00 | 58.44 | C |
| ATOM | 3976 | CB | LEU A | 552 | 16.372 | 16.816 | −2.166 | 1.00 | 56.99 | C |
| ATOM | 3977 | C | LEU A | 552 | 15.495 | 18.186 | −4.082 | 1.00 | 57.67 | C |
| ATOM | 3978 | O | LEU A | 552 | 16.464 | 18.879 | −4.403 | 1.00 | 57.74 | O |
| ATOM | 3979 | N | SER A | 553 | 14.236 | 18.614 | −4.162 | 1.00 | 57.17 | N |
| ATOM | 3980 | CA | SER A | 553 | 13.896 | 19.940 | −4.669 | 1.00 | 59.39 | C |
| ATOM | 3981 | CB | SER A | 553 | 12.482 | 19.955 | −5.246 | 1.00 | 61.05 | C |
| ATOM | 3982 | OG | SER A | 553 | 12.125 | 21.255 | −5.691 | 1.00 | 61.77 | O |
| ATOM | 3983 | C | SER A | 553 | 14.009 | 21.009 | −3.593 | 1.00 | 60.58 | C |
| ATOM | 3984 | O | SER A | 553 | 13.261 | 20.986 | −2.618 | 1.00 | 59.55 | O |
| ATOM | 3985 | N | PRO A | 554 | 14.941 | 21.961 | −3.776 | 1.00 | 63.99 | N |
| ATOM | 3986 | CA | PRO A | 554 | 15.076 | 23.091 | −2.861 | 1.00 | 65.02 | C |
| ATOM | 3987 | CB | PRO A | 554 | 16.558 | 23.500 | −3.018 | 1.00 | 65.68 | C |

-continued

| | | | Atomic coordinates for CRBN:DDB1:Lenalidomide (Human protein) | | | | | | | |
|---|---|---|---|---|---|---|---|---|---|---|
| ATOM | 3988 | CG | PRO A | 554 | 17.165 | 22.529 | −3.995 | 1.00 | 65.71 | C |
| ATOM | 3989 | CD | PRO A | 554 | 16.024 | 21.952 | −4.771 | 1.00 | 64.79 | C |
| ATOM | 3990 | C | PRO A | 554 | 14.142 | 24.250 | −3.237 | 1.00 | 64.68 | C |
| ATOM | 3991 | O | PRO A | 554 | 14.497 | 25.416 | −3.074 | 1.00 | 63.80 | O |
| ATOM | 3992 | N | LEU A | 555 | 12.955 | 23.919 | −3.737 | 1.00 | 65.12 | N |
| ATOM | 3993 | CA | LEU A | 555 | 11.979 | 24.923 | −4.169 | 1.00 | 67.77 | C |
| ATOM | 3994 | CB | LEU A | 555 | 12.199 | 25.319 | −5.644 | 1.00 | 68.10 | C |
| ATOM | 3995 | CG | LEU A | 555 | 13.061 | 24.412 | −6.540 | 1.00 | 68.54 | C |
| ATOM | 3996 | CD1 | LEU A | 555 | 12.432 | 24.184 | −7.909 | 1.00 | 66.51 | C |
| ATOM | 3997 | CD2 | LEU A | 555 | 14.483 | 24.950 | −6.667 | 1.00 | 66.91 | C |
| ATOM | 3998 | C | LEU A | 555 | 10.551 | 24.424 | −3.936 | 1.00 | 68.29 | C |
| ATOM | 3999 | O | LEU A | 555 | 10.284 | 23.224 | −4.034 | 1.00 | 68.78 | O |
| ATOM | 4000 | N | CYS A | 556 | 9.643 | 25.348 | −3.623 | 1.00 | 67.63 | N |
| ATOM | 4001 | CA | CYS A | 556 | 8.290 | 24.986 | −3.209 | 1.00 | 67.14 | C |
| ATOM | 4002 | CB | CYS A | 556 | 8.237 | 24.828 | −1.694 | 1.00 | 64.14 | C |
| ATOM | 4003 | SG | CYS A | 556 | 6.676 | 24.155 | −1.107 | 1.00 | 65.33 | S |
| ATOM | 4004 | C | CYS A | 556 | 7.229 | 25.991 | −3.661 | 1.00 | 70.02 | C |
| ATOM | 4005 | O | CYS A | 556 | 7.359 | 27.193 | −3.416 | 1.00 | 70.57 | O |
| ATOM | 4006 | N | ALA A | 557 | 6.170 | 25.483 | −4.296 | 1.00 | 70.62 | N |
| ATOM | 4007 | CA | ALA A | 557 | 5.097 | 26.322 | −4.851 | 1.00 | 69.38 | C |
| ATOM | 4008 | CB | ALA A | 557 | 4.759 | 25.875 | −6.263 | 1.00 | 68.10 | C |
| ATOM | 4009 | C | ALA A | 557 | 3.839 | 26.328 | −3.980 | 1.00 | 68.85 | C |
| ATOM | 4010 | O | ALA A | 557 | 3.415 | 25.287 | −3.490 | 1.00 | 71.06 | O |
| ATOM | 4011 | N | ILE A | 558 | 3.251 | 27.509 | −3.793 | 1.00 | 68.74 | N |
| ATOM | 4012 | CA | ILE A | 558 | 2.090 | 27.676 | −2.909 | 1.00 | 69.65 | C |
| ATOM | 4013 | CB | ILE A | 558 | 2.486 | 28.312 | −1.555 | 1.00 | 68.97 | C |
| ATOM | 4014 | CG1 | ILE A | 558 | 3.970 | 28.079 | −1.230 | 1.00 | 71.38 | C |
| ATOM | 4015 | CD1 | ILE A | 558 | 4.306 | 26.715 | −0.659 | 1.00 | 72.84 | C |
| ATOM | 4016 | CG2 | ILE A | 558 | 1.554 | 27.855 | −0.435 | 1.00 | 67.12 | C |
| ATOM | 4017 | C | ILE A | 558 | 1.031 | 28.569 | −3.559 | 1.00 | 72.00 | C |
| ATOM | 4018 | O | ILE A | 558 | 1.305 | 29.230 | −4.562 | 1.00 | 73.33 | O |
| ATOM | 4019 | N | GLY A | 559 | −0.171 | 28.584 | −2.977 | 1.00 | 73.22 | N |
| ATOM | 4020 | CA | GLY A | 559 | −1.277 | 29.437 | −3.438 | 1.00 | 72.85 | C |
| ATOM | 4021 | C | GLY A | 559 | −2.266 | 29.704 | −2.317 | 1.00 | 72.86 | C |
| ATOM | 4022 | O | GLY A | 559 | −2.735 | 28.769 | −1.669 | 1.00 | 72.39 | O |
| ATOM | 4023 | N | LEU A | 560 | −2.588 | 30.977 | −2.084 | 1.00 | 72.40 | N |
| ATOM | 4024 | CA | LEU A | 560 | −3.342 | 31.364 | −0.885 | 1.00 | 71.82 | C |
| ATOM | 4025 | CB | LEU A | 560 | −2.467 | 32.219 | 0.036 | 1.00 | 71.37 | C |
| ATOM | 4026 | CG | LEU A | 560 | −0.989 | 31.868 | 0.260 | 1.00 | 71.10 | C |
| ATOM | 4027 | CD1 | LEU A | 560 | −0.426 | 32.758 | 1.354 | 1.00 | 72.05 | C |
| ATOM | 4028 | CD2 | LEU A | 560 | −0.767 | 30.407 | 0.618 | 1.00 | 69.22 | C |
| ATOM | 4029 | C | LEU A | 560 | −4.682 | 32.070 | −1.161 | 1.00 | 73.88 | C |
| ATOM | 4030 | O | LEU A | 560 | −4.975 | 32.436 | −2.300 | 1.00 | 73.14 | O |
| ATOM | 4031 | N | TRP A | 561 | −5.480 | 32.252 | −0.101 | 1.00 | 76.73 | N |
| ATOM | 4032 | CA | TRP A | 561 | −6.828 | 32.860 | −0.179 | 1.00 | 74.92 | C |
| ATOM | 4033 | CB | TRP A | 561 | −7.757 | 32.272 | 0.888 | 1.00 | 74.15 | C |
| ATOM | 4034 | CG | TRP A | 561 | −7.766 | 30.764 | 1.009 | 1.00 | 73.56 | C |
| ATOM | 4035 | CD1 | TRP A | 561 | −6.718 | 29.835 | 1.410 | 1.00 | 73.32 | C |
| ATOM | 4036 | NE1 | TRP A | 561 | −7.111 | 28.619 | 1.423 | 1.00 | 74.18 | N |
| ATOM | 4037 | CE2 | TRP A | 561 | −8.410 | 28.503 | 1.063 | 1.00 | 75.77 | C |
| ATOM | 4038 | CD3 | TRP A | 561 | −8.903 | 29.858 | 0.786 | 1.00 | 74.64 | C |
| ATOM | 4039 | CE3 | TRP A | 561 | −10.230 | 30.027 | 0.390 | 1.00 | 74.57 | C |
| ATOM | 4040 | CZ3 | TRP A | 561 | −11.044 | 28.888 | 0.271 | 1.00 | 74.51 | C |
| ATOM | 4041 | CH2 | TRP A | 561 | −10.553 | 27.598 | 0.543 | 1.00 | 74.90 | C |
| ATOM | 4042 | CZ2 | TRP A | 561 | −9.227 | 27.382 | 0.941 | 1.00 | 76.37 | C |
| ATOM | 4043 | C | TRP A | 561 | −6.802 | 34.358 | −0.006 | 1.00 | 71.88 | C |
| ATOM | 4044 | O | TRP A | 561 | −5.957 | 34.883 | 0.721 | 1.00 | 70.61 | O |
| ATOM | 4045 | N | THR A | 562 | −7.759 | 35.044 | −0.644 | 1.00 | 69.63 | N |
| ATOM | 4046 | CA | THR A | 562 | −7.886 | 36.529 | −0.639 | 1.00 | 67.90 | C |
| ATOM | 4047 | CB | THR A | 562 | −8.448 | 37.100 | 0.692 | 1.00 | 66.71 | C |
| ATOM | 4048 | OG1 | THR A | 562 | −7.546 | 36.816 | 1.768 | 1.00 | 67.43 | O |
| ATOM | 4049 | CG2 | THR A | 562 | −9.831 | 36.527 | 1.007 | 1.00 | 66.35 | C |
| ATOM | 4050 | C | THR A | 562 | −6.602 | 37.273 | −1.019 | 1.00 | 65.62 | C |
| ATOM | 4051 | O | THR A | 562 | −6.644 | 38.295 | −1.705 | 1.00 | 61.79 | O |
| ATOM | 4052 | N | ASP A | 563 | −5.473 | 36.754 | −0.545 | 1.00 | 66.79 | N |
| ATOM | 4053 | CA | ASP A | 563 | −4.147 | 37.210 | −0.944 | 1.00 | 67.72 | C |
| ATOM | 4054 | CB | ASP A | 563 | −3.099 | 36.773 | 0.097 | 1.00 | 66.65 | C |
| ATOM | 4055 | CG | ASP A | 563 | −3.584 | 36.941 | 1.552 | 1.00 | 64.29 | C |
| ATOM | 4056 | OD1 | ASP A | 563 | −4.606 | 37.622 | 1.791 | 1.00 | 62.29 | O |
| ATOM | 4057 | OD2 | ASP A | 563 | −2.932 | 36.384 | 2.462 | 1.00 | 63.83 | O |
| ATOM | 4058 | C | ASP A | 563 | −3.816 | 36.634 | −2.331 | 1.00 | 68.78 | C |
| ATOM | 4059 | O | ASP A | 563 | −2.938 | 37.144 | −3.035 | 1.00 | 67.45 | O |
| ATOM | 4060 | N | ILE A | 564 | −4.539 | 35.564 | −2.689 | 1.00 | 69.58 | N |
| ATOM | 4061 | CA | ILE A | 564 | −4.574 | 34.950 | −4.040 | 1.00 | 68.59 | C |
| ATOM | 4062 | CB | ILE A | 564 | −5.886 | 35.286 | −4.799 | 1.00 | 70.07 | C |
| ATOM | 4063 | CG1 | ILE A | 564 | −6.237 | 36.776 | −4.660 | 1.00 | 71.96 | C |
| ATOM | 4064 | CD1 | ILE A | 564 | −7.621 | 37.157 | −5.143 | 1.00 | 72.98 | C |

-continued

| \multicolumn{10}{c}{Atomic coordinates for CRBN:DDB1:Lenalidomide (Human protein)} |

| | | | | | | | | | |
|---|---|---|---|---|---|---|---|---|---|
| ATOM | 4065 | CG2 | ILE A | 564 | −7.020 | 34.397 | −4.305 | 1.00 | 71.58 | C |
| ATOM | 4066 | C | ILE A | 564 | −3.347 | 35.126 | −4.945 | 1.00 | 67.83 | C |
| ATOM | 4067 | O | ILE A | 564 | −3.391 | 35.848 | −5.947 | 1.00 | 68.49 | O |
| ATOM | 4068 | N | SER A | 565 | −2.261 | 34.446 | −4.587 | 1.00 | 67.21 | N |
| ATOM | 4069 | CA | SER A | 565 | −0.987 | 34.582 | −5.294 | 1.00 | 65.30 | C |
| ATOM | 4070 | CB | SER A | 565 | −0.120 | 35.649 | −4.614 | 1.00 | 64.58 | C |
| ATOM | 4071 | OG | SER A | 565 | 1.089 | 35.865 | −5.320 | 1.00 | 63.23 | O |
| ATOM | 4072 | C | SER A | 565 | −0.237 | 33.253 | −5.351 | 1.00 | 63.25 | C |
| ATOM | 4073 | O | SER A | 565 | −0.498 | 32.352 | −4.555 | 1.00 | 63.60 | O |
| ATOM | 4074 | N | ALA A | 566 | 0.693 | 33.144 | −6.298 | 1.00 | 60.66 | N |
| ATOM | 4075 | CA | ALA A | 566 | 1.537 | 31.961 | −6.437 | 1.00 | 60.01 | C |
| ATOM | 4076 | CB | ALA A | 566 | 1.641 | 31.565 | −7.901 | 1.00 | 59.25 | C |
| ATOM | 4077 | C | ALA A | 566 | 2.932 | 32.180 | −5.821 | 1.00 | 60.58 | C |
| ATOM | 4078 | O | ALA A | 566 | 3.876 | 32.580 | −6.508 | 1.00 | 60.17 | O |
| ATOM | 4079 | N | ARG A | 567 | 3.053 | 31.907 | −4.525 | 1.00 | 61.86 | N |
| ATOM | 4080 | CA | ARG A | 567 | 4.277 | 32.218 | −3.778 | 1.00 | 63.28 | C |
| ATOM | 4081 | CB | ARG A | 567 | 3.956 | 32.580 | −2.321 | 1.00 | 64.16 | C |
| ATOM | 4082 | CG | ARG A | 567 | 2.798 | 33.552 | −2.160 | 1.00 | 65.08 | C |
| ATOM | 4083 | CD | ARG A | 567 | 3.056 | 34.586 | −1.074 | 1.00 | 66.93 | C |
| ATOM | 4084 | NE | ARG A | 567 | 2.303 | 35.811 | −1.345 | 1.00 | 68.36 | N |
| ATOM | 4085 | CZ | ARG A | 567 | 1.241 | 36.222 | −0.657 | 1.00 | 66.99 | C |
| ATOM | 4086 | NH1 | ARG A | 567 | 0.800 | 35.524 | 0.381 | 1.00 | 65.85 | N |
| ATOM | 4087 | NH2 | ARG A | 567 | 0.625 | 37.345 | −1.003 | 1.00 | 66.55 | N |
| ATOM | 4088 | C | ARG A | 567 | 5.284 | 31.076 | −3.824 | 1.00 | 63.65 | C |
| ATOM | 4089 | O | ARG A | 567 | 4.909 | 29.902 | −3.781 | 1.00 | 64.53 | O |
| ATOM | 4090 | N | ILE A | 568 | 6.563 | 31.432 | −3.914 | 1.00 | 62.03 | N |
| ATOM | 4091 | CA | ILE A | 568 | 7.645 | 30.448 | −3.965 | 1.00 | 61.34 | C |
| ATOM | 4092 | CB | ILE A | 568 | 8.556 | 30.649 | −5.205 | 1.00 | 60.85 | C |
| ATOM | 4093 | CG1 | ILE A | 568 | 7.732 | 31.011 | −6.457 | 1.00 | 60.60 | C |
| ATOM | 4094 | CD1 | ILE A | 568 | 6.611 | 30.049 | −6.796 | 1.00 | 59.13 | C |
| ATOM | 4095 | CG2 | ILE A | 568 | 9.461 | 29.437 | −5.436 | 1.00 | 59.30 | C |
| ATOM | 4096 | C | ILE A | 568 | 8.478 | 30.552 | −2.696 | 1.00 | 61.26 | C |
| ATOM | 4097 | O | ILE A | 568 | 8.727 | 31.648 | −2.203 | 1.00 | 61.50 | O |
| ATOM | 4098 | N | LEU A | 569 | 8.905 | 29.406 | −2.173 | 1.00 | 62.27 | N |
| ATOM | 4099 | CA | LEU A | 569 | 9.634 | 29.351 | −0.908 | 1.00 | 63.14 | C |
| ATOM | 4100 | CB | LEU A | 569 | 8.707 | 28.842 | 0.207 | 1.00 | 63.19 | C |
| ATOM | 4101 | CG | LEU A | 569 | 7.871 | 29.793 | 1.089 | 1.00 | 63.28 | C |
| ATOM | 4102 | CD1 | LEU A | 569 | 7.854 | 31.249 | 0.634 | 1.00 | 62.46 | C |
| ATOM | 4103 | CD2 | LEU A | 569 | 6.449 | 29.274 | 1.256 | 1.00 | 62.48 | C |
| ATOM | 4104 | C | LEU A | 569 | 10.887 | 28.475 | −1.003 | 1.00 | 63.56 | C |
| ATOM | 4105 | O | LEU A | 569 | 10.912 | 27.485 | −1.737 | 1.00 | 53.72 | O |
| ATOM | 4106 | N | LYS A | 570 | 11.926 | 28.855 | −0.261 | 1.00 | 65.91 | N |
| ATOM | 4107 | CA | LYS A | 570 | 13.156 | 28.063 | −0.176 | 1.00 | 67.59 | C |
| ATOM | 4108 | CB | LYS A | 570 | 14.320 | 28.924 | 0.334 | 1.00 | 65.96 | C |
| ATOM | 4109 | C | LYS A | 570 | 12.947 | 26.860 | 0.743 | 1.00 | 67.61 | C |
| ATOM | 4110 | O | LYS A | 570 | 12.146 | 26.921 | 1.675 | 1.00 | 69.11 | O |
| ATOM | 4111 | N | LEU A | 571 | 13.653 | 25.763 | 0.478 | 1.00 | 66.91 | N |
| ATOM | 4112 | CA | LEU A | 571 | 13.569 | 24.603 | 1.366 | 1.00 | 66.40 | C |
| ATOM | 4113 | CB | LEU A | 571 | 13.707 | 23.279 | 0.608 | 1.00 | 65.29 | C |
| ATOM | 4114 | CG | LEU A | 571 | 12.369 | 22.538 | 0.443 | 1.00 | 65.20 | C |
| ATOM | 4115 | CD1 | LEU A | 571 | 11.610 | 22.492 | 1.762 | 1.00 | 63.29 | C |
| ATOM | 4116 | CD2 | LEU A | 571 | 11.497 | 23.166 | −0.635 | 1.00 | 65.12 | C |
| ATOM | 4117 | C | LEU A | 571 | 14.502 | 24.713 | 2.575 | 1.00 | 67.47 | C |
| ATOM | 4118 | O | LEU A | 571 | 15.364 | 25.598 | 2.605 | 1.00 | 67.13 | O |
| ATOM | 4119 | N | PRO A | 572 | 14.383 | 23.772 | 3.539 | 1.00 | 68.15 | N |
| ATOM | 4120 | CA | PRO A | 572 | 14.409 | 24.070 | 4.964 | 1.00 | 65.27 | C |
| ATOM | 4121 | CB | PRO A | 572 | 15.854 | 23.728 | 5.340 | 1.00 | 64.86 | C |
| ATOM | 4122 | CG | PRO A | 572 | 16.199 | 22.588 | 4.399 | 1.00 | 65.58 | C |
| ATOM | 4123 | CD | PRO A | 572 | 15.122 | 22.518 | 3.321 | 1.00 | 67.68 | C |
| ATOM | 4124 | C | PRO A | 572 | 13.997 | 25.492 | 5.378 | 1.00 | 64.15 | C |
| ATOM | 4125 | O | PRO A | 572 | 13.213 | 25.647 | 6.314 | 1.00 | 62.57 | O |
| ATOM | 4126 | N | SER A | 573 | 14.483 | 26.501 | 4.655 | 1.00 | 64.76 | N |
| ATOM | 4127 | CA | SER A | 573 | 14.306 | 27.919 | 5.006 | 1.00 | 63.80 | C |
| ATOM | 4128 | CB | SER A | 573 | 15.165 | 28.798 | 4.085 | 1.00 | 64.08 | C |
| ATOM | 4129 | OG | SER A | 573 | 16.518 | 28.367 | 4.071 | 1.00 | 62.60 | O |
| ATOM | 4130 | C | SER A | 573 | 12.853 | 28.429 | 5.020 | 1.00 | 63.12 | C |
| ATOM | 4131 | O | SER A | 573 | 12.404 | 28.983 | 6.022 | 1.00 | 62.60 | O |
| ATOM | 4132 | N | PHE A | 574 | 12.140 | 28.251 | 3.907 | 1.00 | 63.78 | N |
| ATOM | 4133 | CA | PHE A | 574 | 10.770 | 28.776 | 3.727 | 1.00 | 65.03 | C |
| ATOM | 4134 | CB | PHE A | 574 | 9.859 | 28.402 | 4.915 | 1.00 | 66.02 | C |
| ATOM | 4135 | CG | PHE A | 574 | 9.109 | 27.106 | 4.733 | 1.00 | 69.32 | C |
| ATOM | 4136 | CD1 | PHE A | 574 | 8.121 | 26.984 | 3.758 | 1.00 | 70.59 | C |
| ATOM | 4137 | CE1 | PHE A | 574 | 7.425 | 25.793 | 3.592 | 1.00 | 69.79 | C |
| ATOM | 4138 | CZ | PHE A | 574 | 7.694 | 24.712 | 4.415 | 1.00 | 69.92 | C |
| ATOM | 4139 | CE2 | PHE A | 574 | 8.663 | 24.822 | 5.398 | 1.00 | 70.47 | C |
| ATOM | 4140 | CD2 | PHE A | 574 | 9.366 | 26.014 | 5.555 | 1.00 | 71.21 | C |
| ATOM | 4141 | C | PHE A | 574 | 10.687 | 30.290 | 3.438 | 1.00 | 64.39 | C |

-continued

| | | | | | | | | | | |
|---|---|---|---|---|---|---|---|---|---|---|
| \multicolumn{11}{l}{Atomic coordinates for CRBN:DDB1:Lenalidomide (Human protein)} |
| ATOM | 4142 | O | PHE A | 574 | 9.596 | 30.866 | 3.453 | 1.00 | 64.83 | O |
| ATOM | 4143 | N | GLU A | 575 | 11.825 | 30.924 | 3.150 | 1.00 | 62.43 | N |
| ATOM | 4144 | CA | GLU A | 575 | 11.890 | 32.391 | 3.043 | 1.00 | 59.93 | C |
| ATOM | 4145 | CB | GLU A | 575 | 13.102 | 32.938 | 3.818 | 1.00 | 56.80 | C |
| ATOM | 4146 | C | GLU A | 575 | 11.899 | 32.912 | 1.599 | 1.00 | 58.61 | C |
| ATOM | 4147 | O | GLU A | 575 | 12.966 | 33.059 | 0.997 | 1.00 | 60.05 | O |
| ATOM | 4148 | N | LEU A | 576 | 10.707 | 33.199 | 1.066 | 1.00 | 55.48 | N |
| ATOM | 4149 | CA | LEU A | 576 | 10.519 | 33.779 | −0.285 | 1.00 | 52.03 | C |
| ATOM | 4150 | CB | LEU A | 576 | 10.104 | 35.252 | −0.194 | 1.00 | 49.71 | C |
| ATOM | 4151 | C | LEU A | 576 | 11.720 | 33.624 | −1.224 | 1.00 | 50.10 | C |
| ATOM | 4152 | O | LEU A | 576 | 11.649 | 32.936 | −2.242 | 1.00 | 45.83 | O |
| ATOM | 4153 | N | HIS A | 578 | 10.973 | 34.275 | −4.322 | 1.00 | 59.80 | N |
| ATOM | 4154 | CA | HIS A | 578 | 10.271 | 35.437 | −4.872 | 1.00 | 62.12 | C |
| ATOM | 4155 | CB | HIS A | 578 | 10.523 | 35.556 | −6.385 | 1.00 | 60.64 | C |
| ATOM | 4156 | C | HIS A | 578 | 8.792 | 35.382 | −4.583 | 1.00 | 63.71 | C |
| ATOM | 4157 | O | HIS A | 578 | 8.383 | 34.925 | −3.514 | 1.00 | 64.70 | O |
| ATOM | 4158 | N | LYS A | 579 | 7.988 | 35.861 | −5.535 | 1.00 | 65.10 | N |
| ATOM | 4159 | CA | LYS A | 579 | 6.527 | 35.961 | −5.409 | 1.00 | 65.96 | C |
| ATOM | 4160 | CB | LYS A | 579 | 6.151 | 36.836 | −4.196 | 1.00 | 64.52 | C |
| ATOM | 4161 | CG | LYS A | 579 | 4.657 | 37.102 | −4.006 | 1.00 | 63.26 | C |
| ATOM | 4162 | CD | LYS A | 579 | 4.288 | 38.500 | −4.491 | 1.00 | 63.21 | C |
| ATOM | 4163 | CE | LYS A | 579 | 2.784 | 38.722 | −4.483 | 1.00 | 62.85 | C |
| ATOM | 4164 | NZ | LYS A | 579 | 2.247 | 38.999 | −3.123 | 1.00 | 61.93 | N |
| ATOM | 4165 | C | LYS A | 579 | 5.970 | 36.552 | −6.711 | 1.00 | 68.93 | C |
| ATOM | 4166 | O | LYS A | 579 | 6.714 | 37.160 | −7.485 | 1.00 | 71.13 | O |
| ATOM | 4167 | N | GLU A | 580 | 4.675 | 36.349 | −6.964 | 1.00 | 70.88 | N |
| ATOM | 4168 | CA | GLU A | 580 | 3.991 | 36.993 | −8.091 | 1.00 | 71.52 | C |
| ATOM | 4169 | CB | GLU A | 580 | 4.330 | 36.296 | −9.415 | 1.00 | 69.11 | C |
| ATOM | 4170 | CG | GLU A | 580 | 4.613 | 37.253 | −10.568 | 1.00 | 67.57 | C |
| ATOM | 4171 | CD | GLU A | 580 | 3.412 | 38.105 | −10.945 | 1.00 | 67.36 | C |
| ATOM | 4172 | OE1 | GLU A | 580 | 2.321 | 37.536 | −11.180 | 1.00 | 67.88 | O |
| ATOM | 4173 | OE2 | GLU A | 580 | 3.562 | 39.345 | −11.012 | 1.00 | 64.86 | O |
| ATOM | 4174 | C | GLU A | 580 | 2.475 | 37.041 | −7.877 | 1.00 | 73.94 | C |
| ATOM | 4175 | O | GLU A | 580 | 1.814 | 36.003 | −7.849 | 1.00 | 74.23 | O |
| ATOM | 4176 | N | MET A | 581 | 1.941 | 38.254 | −7.728 | 1.00 | 77.32 | N |
| ATOM | 4177 | CA | MET A | 581 | 0.508 | 38.474 | −7.479 | 1.00 | 77.88 | C |
| ATOM | 4178 | CB | MET A | 581 | 0.268 | 39.905 | −6.965 | 1.00 | 78.72 | C |
| ATOM | 4179 | CG | MET A | 581 | −1.191 | 40.279 | −6.701 | 1.00 | 78.75 | C |
| ATOM | 4180 | SD | MET A | 581 | −1.921 | 39.553 | −5.216 | 1.00 | 80.51 | S |
| ATOM | 4181 | CE | MET A | 581 | −1.202 | 40.567 | −3.923 | 1.00 | 77.01 | C |
| ATOM | 4182 | C | MET A | 581 | −0.335 | 38.203 | −8.724 | 1.00 | 77.76 | C |
| ATOM | 4183 | O | MET A | 581 | 0.091 | 38.470 | −9.849 | 1.00 | 75.28 | O |
| ATOM | 4184 | N | LEU A | 582 | −1.534 | 37.671 | −8.508 | 1.00 | 79.63 | N |
| ATOM | 4185 | CA | LEU A | 582 | −2.457 | 37.388 | −9.599 | 1.00 | 81.54 | C |
| ATOM | 4186 | CB | LEU A | 582 | −2.736 | 35.889 | −9.680 | 1.00 | 82.08 | C |
| ATOM | 4187 | CG | LEU A | 582 | −3.121 | 35.359 | −11.061 | 1.00 | 83.87 | C |
| ATOM | 4188 | CD2 | LEU A | 582 | −4.632 | 35.351 | −11.238 | 1.00 | 84.78 | C |
| ATOM | 4189 | CD1 | LEU A | 582 | −2.550 | 33.964 | −11.255 | 1.00 | 84.53 | C |
| ATOM | 4190 | C | LEU A | 582 | −3.763 | 38.169 | −9.462 | 1.00 | 83.25 | C |
| ATOM | 4191 | O | LEU A | 582 | −4.420 | 38.470 | −10.463 | 1.00 | 84.51 | O |
| ATOM | 4192 | N | GLY A | 583 | −4.133 | 38.490 | −8.222 | 1.00 | 83.84 | N |
| ATOM | 4193 | CA | GLY A | 583 | −5.353 | 39.249 | −7.942 | 1.00 | 80.13 | C |
| ATOM | 4194 | C | GLY A | 583 | −6.616 | 38.497 | −8.318 | 1.00 | 77.33 | C |
| ATOM | 4195 | O | GLY A | 583 | −6.620 | 37.266 | −8.380 | 1.00 | 76.42 | O |
| ATOM | 4196 | N | GLY A | 583 | −7.684 | 39.244 | −8.586 | 1.00 | 74.70 | N |
| ATOM | 4197 | CA | GLY A | 583 | −8.991 | 38.659 | −8.865 | 1.00 | 71.05 | C |
| ATOM | 4198 | C | GLY A | 583 | −9.788 | 38.490 | −7.586 | 1.00 | 69.71 | C |
| ATOM | 4199 | O | GLY A | 583 | −9.693 | 39.316 | −6.678 | 1.00 | 69.93 | O |
| ATOM | 4200 | N | GLU A | 585 | −10.565 | 37.411 | −7.511 | 1.00 | 68.75 | N |
| ATOM | 4201 | CA | GLU A | 585 | −11.403 | 37.123 | −6.336 | 1.00 | 67.27 | C |
| ATOM | 4202 | CB | GLU A | 585 | −12.764 | 37.818 | −6.465 | 1.00 | 64.95 | C |
| ATOM | 4203 | CG | GLU A | 585 | −13.651 | 37.255 | −7.569 | 1.00 | 62.95 | C |
| ATOM | 4204 | CD | GLU A | 585 | −14.747 | 38.211 | −7.990 | 1.00 | 61.44 | C |
| ATOM | 4205 | OE1 | GLU A | 585 | −15.291 | 38.924 | −7.120 | 1.00 | 61.86 | O |
| ATOM | 4206 | OE2 | GLU A | 585 | −15.068 | 38.245 | −9.196 | 1.00 | 59.79 | O |
| ATOM | 4207 | C | GLU A | 585 | −11.598 | 35.620 | −6.111 | 1.00 | 66.99 | C |
| ATOM | 4208 | O | GLU A | 585 | −12.237 | 35.207 | −5.139 | 1.00 | 65.40 | O |
| ATOM | 4209 | N | ILE A | 586 | −11.053 | 34.815 | −7.021 | 1.00 | 68.42 | N |
| ATOM | 4210 | CA | ILE A | 586 | −11.181 | 33.359 | −6.961 | 1.00 | 69.09 | C |
| ATOM | 4211 | CB | ILE A | 586 | −11.635 | 32.751 | −8.312 | 1.00 | 68.97 | C |
| ATOM | 4212 | CG1 | ILE A | 586 | −12.461 | 33.755 | −9.135 | 1.00 | 69.17 | C |
| ATOM | 4213 | CD1 | ILE A | 586 | −11.663 | 34.530 | −10.167 | 1.00 | 67.72 | C |
| ATOM | 4214 | CG2 | ILE A | 586 | −12.436 | 31.476 | −8.078 | 1.00 | 69.04 | C |
| ATOM | 4215 | C | ILE A | 586 | −9.859 | 32.722 | −6.533 | 1.00 | 69.94 | C |
| ATOM | 4216 | O | ILE A | 586 | −8.783 | 33.179 | −6.923 | 1.00 | 68.83 | O |
| ATOM | 4217 | N | ILE A | 587 | −9.953 | 31.670 | −5.724 | 1.00 | 70.34 | N |
| ATOM | 4218 | CA | ILE A | 587 | −8.777 | 30.968 | −5.208 | 1.00 | 70.28 | C |

-continued

| | | | | | | | | | | |
|---|---|---|---|---|---|---|---|---|---|---|
| | Atomic coordinates for CRBN:DDB1:Lenalidomide (Human protein) |

| ATOM | 4219 | CB  | ILE A | 587 | −9.073  | 30.266 | −3.861  | 1.00 | 69.93 | C |
| ---- | ---- | --- | ----- | --- | ------- | ------ | ------- | ---- | ----- | - |
| ATOM | 4220 | CG1 | ILE A | 587 | −10.497 | 29.681 | −3.828  | 1.00 | 69.57 | C |
| ATOM | 4221 | CD1 | ILE A | 587 | −10.598 | 28.222 | −4.237  | 1.00 | 68.74 | C |
| ATOM | 4222 | CG2 | ILE A | 587 | −8.879  | 31.238 | −2.712  | 1.00 | 69.02 | C |
| ATOM | 4223 | C   | ILE A | 587 | −8.203  | 29.961 | −6.213  | 1.00 | 72.59 | C |
| ATOM | 4224 | O   | ILE A | 587 | −8.962  | 29.316 | −6.948  | 1.00 | 73.40 | O |
| ATOM | 4225 | N   | PRO A | 588 | −6.857  | 29.833 | −6.260  | 1.00 | 72.77 | N |
| ATOM | 4226 | CA  | PRO A | 588 | −6.227  | 28.832 | −7.126  | 1.00 | 70.85 | C |
| ATOM | 4227 | CB  | PRO A | 588 | −4.744  | 29.218 | −7.095  | 1.00 | 69.48 | C |
| ATOM | 4228 | CG  | PRO A | 588 | −4.564  | 29.970 | −5.823  | 1.00 | 70.26 | C |
| ATOM | 4229 | CD  | PRO A | 588 | −5.860  | 30.689 | −5.586  | 1.00 | 71.84 | C |
| ATOM | 4230 | C   | PRO A | 588 | −6.425  | 27.419 | −6.587  | 1.00 | 70.35 | C |
| ATOM | 4231 | O   | PRO A | 588 | −6.349  | 27.203 | −5.373  | 1.00 | 69.44 | O |
| ATOM | 4232 | N   | ARG A | 589 | −6.690  | 26.473 | −7.486  | 1.00 | 69.73 | N |
| ATOM | 4233 | CA  | ARG A | 589 | −6.936  | 25.083 | −7.097  | 1.00 | 68.14 | C |
| ATOM | 4234 | CB  | ARG A | 589 | −8.124  | 24.502 | −7.874  | 1.00 | 66.40 | C |
| ATOM | 4235 | C   | ARG A | 589 | −5.695  | 24.201 | −7.267  | 1.00 | 66.17 | C |
| ATOM | 4236 | O   | ARG A | 589 | −5.389  | 23.386 | −6.390  | 1.00 | 67.29 | O |
| ATOM | 4237 | N   | SER A | 590 | −4.987  | 24.377 | −8.387  | 1.00 | 61.80 | N |
| ATOM | 4238 | CA  | SER A | 590 | −3.818  | 23.557 | −8.723  | 1.00 | 57.55 | C |
| ATOM | 4239 | CB  | SER A | 590 | −4.105  | 22.696 | −9.952  | 1.00 | 55.40 | C |
| ATOM | 4240 | C   | SER A | 590 | −2.568  | 24.390 | −8.976  | 1.00 | 56.70 | C |
| ATOM | 4241 | O   | SER A | 590 | −2.645  | 25.497 | −9.515  | 1.00 | 56.61 | O |
| ATOM | 4242 | N   | ILE A | 591 | −1.418  | 23.840 | −8.590  | 1.00 | 55.56 | N |
| ATOM | 4243 | CA  | ILE A | 591 | −0.118  | 24.462 | −8.854  | 1.00 | 54.61 | C |
| ATOM | 4244 | CB  | ILE A | 591 | 0.307   | 25.421 | −7.711  | 1.00 | 54.49 | C |
| ATOM | 4245 | CG1 | ILE A | 591 | 1.309   | 26.465 | −8.219  | 1.00 | 55.18 | C |
| ATOM | 4246 | CD1 | ILE A | 591 | 1.179   | 27.821 | −7.552  | 1.00 | 55.59 | C |
| ATOM | 4247 | CG2 | ILE A | 591 | 0.842   | 24.655 | −6.506  | 1.00 | 53.91 | C |
| ATOM | 4248 | C   | ILE A | 591 | 0.955   | 23.400 | −9.128  | 1.00 | 54.72 | C |
| ATOM | 4249 | O   | ILE A | 591 | 0.957   | 22.335 | −8.507  | 1.00 | 53.04 | O |
| ATOM | 4250 | N   | LEU A | 592 | 1.854   | 23.692 | −10.068 | 1.00 | 56.48 | N |
| ATOM | 4251 | CA  | LEU A | 592 | 2.846   | 22.718 | −10.521 | 1.00 | 55.47 | C |
| ATOM | 4252 | CB  | LEU A | 592 | 2.233   | 21.807 | −11.592 | 1.00 | 54.38 | C |
| ATOM | 4253 | CG  | LEU A | 592 | 3.038   | 20.616 | −12.118 | 1.00 | 54.72 | C |
| ATOM | 4254 | CD1 | LEU A | 592 | 3.288   | 19.572 | −11.038 | 1.00 | 53.46 | C |
| ATOM | 4255 | CD2 | LEU A | 592 | 2.322   | 19.994 | −13.307 | 1.00 | 55.60 | C |
| ATOM | 4256 | C   | LEU A | 592 | 4.106   | 23.378 | −11.063 | 1.00 | 56.68 | C |
| ATOM | 4257 | O   | LEU A | 592 | 4.029   | 24.314 | −11.854 | 1.00 | 56.99 | O |
| ATOM | 4258 | N   | MET A | 593 | 5.261   | 22.885 | −10.620 | 1.00 | 61.05 | N |
| ATOM | 4259 | CA  | MET A | 593 | 6.560   | 23.240 | −11.206 | 1.00 | 63.54 | C |
| ATOM | 4260 | CB  | MET A | 593 | 7.626   | 23.386 | −10.117 | 1.00 | 61.61 | C |
| ATOM | 4261 | CG  | MET A | 593 | 7.343   | 24.455 | −9.078  | 1.00 | 60.16 | C |
| ATOM | 4262 | SD  | MET A | 593 | 8.647   | 24.561 | −7.837  | 1.00 | 59.21 | S |
| ATOM | 4263 | CE  | MET A | 593 | 8.576   | 22.925 | −7.107  | 1.00 | 59.55 | C |
| ATOM | 4264 | C   | MET A | 593 | 6.980   | 22.132 | −12.171 | 1.00 | 67.94 | C |
| ATOM | 4265 | O   | MET A | 593 | 7.040   | 20.960 | −11.782 | 1.00 | 71.78 | O |
| ATOM | 4266 | N   | THR A | 594 | 7.282   | 22.497 | −13.418 | 1.00 | 69.11 | N |
| ATOM | 4267 | CA  | THR A | 594 | 7.512   | 21.503 | −14.478 | 1.00 | 67.56 | C |
| ATOM | 4268 | CB  | THR A | 594 | 6.174   | 21.066 | −15.105 | 1.00 | 65.01 | C |
| ATOM | 4269 | OG1 | THR A | 594 | 6.413   | 20.080 | −16.112 | 1.00 | 67.70 | O |
| ATOM | 4270 | CG2 | THR A | 594 | 5.451   | 22.255 | −15.716 | 1.00 | 64.19 | C |
| ATOM | 4271 | C   | THR A | 594 | 8.502   | 21.970 | −15.569 | 1.00 | 68.59 | C |
| ATOM | 4272 | O   | THR A | 594 | 8.767   | 23.167 | −15.692 | 1.00 | 70.03 | O |
| ATOM | 4273 | N   | THR A | 595 | 9.031   | 21.026 | −16.357 | 1.00 | 68.56 | N |
| ATOM | 4274 | CA  | THR A | 595 | 10.099  | 21.324 | −17.336 | 1.00 | 68.61 | C |
| ATOM | 4275 | CB  | THR A | 595 | 11.497  | 20.885 | −16.811 | 1.00 | 69.03 | C |
| ATOM | 4276 | OG1 | THR A | 595 | 12.501  | 21.207 | −17.779 | 1.00 | 71.98 | O |
| ATOM | 4277 | CG2 | THR A | 595 | 11.549  | 19.382 | −16.514 | 1.00 | 69.92 | C |
| ATOM | 4278 | C   | THR A | 595 | 9.867   | 20.806 | −18.778 | 1.00 | 69.19 | C |
| ATOM | 4279 | O   | THR A | 595 | 9.798   | 19.597 | −19.013 | 1.00 | 71.35 | O |
| ATOM | 4280 | N   | PHE A | 596 | 9.767   | 21.729 | −19.735 | 1.00 | 69.13 | N |
| ATOM | 4281 | CA  | PHE A | 596 | 9.600   | 21.371 | −21.150 | 1.00 | 70.62 | C |
| ATOM | 4282 | CB  | PHE A | 596 | 8.410   | 22.108 | −21.762 | 1.00 | 70.98 | C |
| ATOM | 4283 | CG  | PHE A | 596 | 7.097   | 21.813 | −21.096 | 1.00 | 70.07 | C |
| ATOM | 4284 | CD1 | PHE A | 596 | 6.578   | 20.522 | −21.081 | 1.00 | 69.26 | C |
| ATOM | 4285 | CE1 | PHE A | 596 | 5.359   | 20.255 | −20.476 | 1.00 | 68.82 | C |
| ATOM | 4286 | CZ  | PHE A | 596 | 4.637   | 21.284 | −19.889 | 1.00 | 68.86 | C |
| ATOM | 4287 | CE2 | PHE A | 596 | 5.138   | 22.577 | −19.908 | 1.00 | 69.10 | C |
| ATOM | 4288 | CD2 | PHE A | 596 | 6.358   | 22.838 | −20.513 | 1.00 | 69.51 | C |
| ATOM | 4289 | C   | PHE A | 596 | 10.850  | 21.677 | −21.973 | 1.00 | 73.15 | C |
| ATOM | 4290 | O   | PHE A | 596 | 11.480  | 22.722 | −21.785 | 1.00 | 75.41 | O |
| ATOM | 4291 | N   | GLU A | 597 | 11.168  | 20.783 | −22.915 | 1.00 | 75.03 | N |
| ATOM | 4292 | CA  | GLU A | 597 | 12.426  | 20.822 | −23.692 | 1.00 | 77.32 | C |
| ATOM | 4293 | CB  | GLU A | 597 | 12.493  | 22.050 | −24.616 | 1.00 | 74.76 | C |
| ATOM | 4294 | C   | GLU A | 597 | 13.646  | 20.739 | −22.757 | 1.00 | 78.47 | C |
| ATOM | 4295 | O   | GLU A | 597 | 14.200  | 19.655 | −22.543 | 1.00 | 79.84 | O |

-continued

| | | | | Atomic coordinates for CRBN:DDB1:Lenalidomide (Human protein) | | | | | |
|---|---|---|---|---|---|---|---|---|---|
| ATOM | 4296 | N | SER A | 598 | 14.053 | 21.883 | −22.210 | 1.00 | 75.61 | N |
| ATOM | 4297 | CA | SER A | 598 | 14.938 | 21.925 | −21.043 | 1.00 | 71.35 | C |
| ATOM | 4298 | CB | SER A | 598 | 16.406 | 21.779 | −21.446 | 1.00 | 69.45 | C |
| ATOM | 4299 | OG | SER A | 598 | 17.159 | 21.231 | −20.378 | 1.00 | 66.21 | O |
| ATOM | 4300 | C | SER A | 598 | 14.709 | 23.217 | −20.256 | 1.00 | 69.68 | C |
| ATOM | 4301 | O | SER A | 598 | 15.417 | 23.510 | −19.289 | 1.00 | 68.95 | O |
| ATOM | 4302 | N | SER A | 599 | 13.710 | 23.980 | −20.690 | 1.00 | 68.29 | N |
| ATOM | 4303 | CA | SER A | 599 | 13.282 | 25.186 | −20.001 | 1.00 | 66.34 | C |
| ATOM | 4304 | CB | SER A | 599 | 12.608 | 26.138 | −20.990 | 1.00 | 65.17 | C |
| ATOM | 4305 | OG | SER A | 599 | 12.289 | 27.367 | −20.370 | 1.00 | 64.04 | O |
| ATOM | 4306 | C | SER A | 599 | 12.324 | 24.819 | −18.868 | 1.00 | 65.93 | C |
| ATOM | 4307 | O | SER A | 599 | 11.638 | 23.801 | −18.932 | 1.00 | 65.40 | O |
| ATOM | 4308 | N | HIS A | 600 | 12.285 | 25.654 | −17.833 | 1.00 | 67.95 | N |
| ATOM | 4309 | CA | HIS A | 600 | 11.471 | 25.392 | −16.647 | 1.00 | 66.67 | C |
| ATOM | 4310 | CB | HIS A | 600 | 12.334 | 25.424 | −15.386 | 1.00 | 67.33 | C |
| ATOM | 4311 | CG | HIS A | 600 | 13.474 | 24.425 | −15.389 | 1.00 | 69.16 | C |
| ATOM | 4312 | ND1 | HIS A | 600 | 13.398 | 23.236 | −14.763 | 1.00 | 71.11 | N |
| ATOM | 4313 | CE1 | HIS A | 600 | 14.558 | 22.567 | −14.926 | 1.00 | 71.28 | C |
| ATOM | 4314 | NE2 | HIS A | 600 | 15.382 | 23.334 | −15.657 | 1.00 | 69.63 | N |
| ATOM | 4315 | CD2 | HIS A | 600 | 14.749 | 24.489 | −15.957 | 1.00 | 69.81 | C |
| ATOM | 4316 | C | HIS A | 600 | 10.351 | 35.388 | −16.517 | 1.00 | 66.58 | C |
| ATOM | 4317 | O | HIS A | 600 | 10.526 | 27.578 | −16.804 | 1.00 | 66.18 | O |
| ATOM | 4318 | N | TYR A | 601 | 9.188 | 25.908 | −16.075 | 1.00 | 65.05 | N |
| ATOM | 4319 | CA | TYR A | 601 | 8.031 | 26.772 | −15.822 | 1.00 | 63.98 | C |
| ATOM | 4320 | CB | TYR A | 601 | 6.997 | 26.656 | −16.953 | 1.00 | 63.15 | C |
| ATOM | 4321 | CG | TYR A | 601 | 7.540 | 26.773 | −18.365 | 1.00 | 63.90 | C |
| ATOM | 4322 | CD1 | TYR A | 601 | 8.088 | 25.667 | −19.014 | 1.00 | 63.91 | C |
| ATOM | 4323 | CE1 | TYR A | 601 | 8.567 | 25.763 | −20.312 | 1.00 | 65.42 | C |
| ATOM | 4324 | CZ | TYR A | 601 | 8.493 | 26.974 | −20.987 | 1.00 | 64.31 | C |
| ATOM | 4325 | OH | TYR A | 601 | 8.974 | 27.053 | −22.273 | 1.00 | 63.83 | O |
| ATOM | 4326 | CE2 | TYR A | 601 | 7.943 | 25.087 | −20.371 | 1.00 | 63.19 | C |
| ATOM | 4327 | CD2 | TYR A | 601 | 7.467 | 27.981 | −19.069 | 1.00 | 64.37 | C |
| ATOM | 4328 | C | TYR A | 601 | 7.345 | 26.473 | −14.476 | 1.00 | 63.36 | C |
| ATOM | 4329 | O | TYR A | 601 | 7.620 | 25.461 | −13.822 | 1.00 | 61.88 | O |
| ATOM | 4330 | N | LEU A | 602 | 6.461 | 27.380 | −14.069 | 1.00 | 62.23 | N |
| ATOM | 4331 | CA | LEU A | 602 | 5.516 | 27.129 | −12.988 | 1.00 | 59.95 | C |
| ATOM | 4332 | CB | LEU A | 602 | 5.765 | 28.074 | −11.810 | 1.00 | 58.82 | C |
| ATOM | 4333 | CG | LEU A | 602 | 4.883 | 27.909 | −10.565 | 1.00 | 57.23 | C |
| ATOM | 4334 | CD1 | LEU A | 602 | 5.740 | 27.917 | −9.314 | 1.00 | 57.18 | C |
| ATOM | 4335 | CD2 | LEU A | 602 | 3.794 | 28.969 | −10.484 | 1.00 | 54.84 | C |
| ATOM | 4336 | C | LEU A | 602 | 4.108 | 27.318 | −13.537 | 1.00 | 60.34 | C |
| ATOM | 4337 | O | LEU A | 602 | 3.853 | 28.243 | −14.315 | 1.00 | 61.54 | O |
| ATOM | 4338 | N | LEU A | 603 | 3.202 | 26.433 | −13.138 | 1.00 | 58.73 | N |
| ATOM | 4339 | CA | LEU A | 603 | 1.838 | 26.436 | −13.648 | 1.00 | 57.98 | C |
| ATOM | 4340 | CB | LEU A | 603 | 1.536 | 25.113 | −14.357 | 1.00 | 54.86 | C |
| ATOM | 4341 | CG | LEU A | 603 | 1.766 | 24.922 | −15.859 | 1.00 | 53.01 | C |
| ATOM | 4342 | CD1 | LEU A | 603 | 2.950 | 25.713 | −16.395 | 1.00 | 53.86 | C |
| ATOM | 4343 | CD2 | LEU A | 603 | 1.927 | 23.441 | −16.167 | 1.00 | 52.30 | C |
| ATOM | 4344 | C | LEU A | 603 | 0.854 | 26.638 | −12.513 | 1.00 | 60.02 | C |
| ATOM | 4345 | O | LEU A | 603 | 0.914 | 25.941 | −11.499 | 1.00 | 61.24 | O |
| ATOM | 4346 | N | CYS A | 604 | −0.054 | 27.593 | −12.679 | 1.00 | 60.60 | N |
| ATOM | 4347 | CA | CYS A | 604 | −1.113 | 27.771 | −11.704 | 1.00 | 61.22 | C |
| ATOM | 4348 | CB | CYS A | 604 | −0.869 | 28.995 | −10.834 | 1.00 | 61.19 | C |
| ATOM | 4349 | SG | CYS A | 604 | −1.884 | 28.959 | −9.344 | 1.00 | 63.18 | S |
| ATOM | 4350 | C | CYS A | 604 | −2.471 | 27.859 | −12.364 | 1.00 | 61.65 | C |
| ATOM | 4351 | O | CYS A | 604 | −2.698 | 28.705 | −13.232 | 1.00 | 62.46 | O |
| ATOM | 4352 | N | ALA A | 605 | −3.368 | 26.973 | −11.936 | 1.00 | 61.34 | N |
| ATOM | 4353 | CA | ALA A | 605 | −4.711 | 26.882 | −12.490 | 1.00 | 61.95 | C |
| ATOM | 4354 | CB | ALA A | 605 | −5.020 | 25.450 | −12.882 | 1.00 | 60.03 | C |
| ATOM | 4355 | C | ALA A | 605 | −5.752 | 27.411 | −11.508 | 1.00 | 63.59 | C |
| ATOM | 4356 | O | ALA A | 605 | −5.702 | 27.111 | −10.310 | 1.00 | 63.42 | O |
| ATOM | 4357 | N | LEU A | 606 | −6.699 | 28.187 | −12.031 | 1.00 | 65.82 | N |
| ATOM | 4358 | CA | LEU A | 606 | −7.676 | 28.899 | −11.209 | 1.00 | 66.77 | C |
| ATOM | 4359 | CB | LEU A | 606 | −7.903 | 30.308 | −11.761 | 1.00 | 66.19 | C |
| ATOM | 4360 | CG | LEU A | 606 | −7.113 | 31.412 | −11.051 | 1.00 | 67.42 | C |
| ATOM | 4361 | CD1 | LEU A | 606 | −6.693 | 32.515 | −12.014 | 1.00 | 66.37 | C |
| ATOM | 4362 | CD2 | LEU A | 606 | −7.915 | 31.975 | −9.885 | 1.00 | 66.45 | C |
| ATOM | 4363 | C | LEU A | 606 | −9.010 | 28.177 | −11.028 | 1.00 | 68.51 | C |
| ATOM | 4364 | O | LEU A | 606 | −9.400 | 27.341 | −11.847 | 1.00 | 68.09 | O |
| ATOM | 4365 | N | GLY A | 607 | −9.701 | 28.519 | −9.939 | 1.00 | 71.96 | N |
| ATOM | 4366 | CA | GLY A | 607 | −11.006 | 27.947 | −9.608 | 1.00 | 73.26 | C |
| ATOM | 4367 | C | GLY A | 607 | −12.146 | 28.444 | −10.482 | 1.00 | 74.18 | C |
| ATOM | 4368 | O | GLY A | 607 | −13.277 | 27.959 | −10.367 | 1.00 | 73.69 | O |
| ATOM | 4369 | N | ASP A | 608 | −11.853 | 29.419 | −11.347 | 1.00 | 74.26 | N |
| ATOM | 4370 | CA | ASP A | 608 | −12.821 | 29.900 | −12.342 | 1.00 | 71.92 | C |
| ATOM | 4371 | CB | ASP A | 608 | −12.807 | 31.442 | −12.460 | 1.00 | 72.61 | C |
| ATOM | 4372 | CG | ASP A | 608 | −11.639 | 31.978 | −13.296 | 1.00 | 72.81 | C |

-continued

| | | Atomic coordinates for CRBN:DDB1:Lenalidomide (Human protein) | | | | | | | |
|---|---|---|---|---|---|---|---|---|---|
| ATOM | 4373 | OD1 | ASP A | 608 | −11.007 | 31.205 | −14.050 | 1.00 | 71.22 | O |
| ATOM | 4374 | OD2 | ASP A | 608 | −11.363 | 33.196 | −13.201 | 1.00 | 72.14 | O |
| ATOM | 4375 | C | ASP A | 608 | −12.599 | 29.238 | −13.697 | 1.00 | 66.42 | C |
| ATOM | 4376 | O | ASP A | 608 | −13.448 | 29.322 | −14.580 | 1.00 | 64.21 | O |
| ATOM | 4377 | N | GLY A | 609 | −11.444 | 28.596 | −13.846 | 1.00 | 63.74 | N |
| ATOM | 4378 | CA | GLY A | 609 | −11.096 | 27.891 | −15.071 | 1.00 | 63.96 | C |
| ATOM | 4379 | C | GLY A | 609 | −9.889 | 28.460 | −15.786 | 1.00 | 62.89 | C |
| ATOM | 4380 | O | GLY A | 609 | −9.501 | 27.979 | −16.853 | 1.00 | 62.47 | O |
| ATOM | 4381 | N | ALA A | 610 | −9.289 | 29.489 | −15.200 | 1.00 | 63.41 | N |
| ATOM | 4382 | CA | ALA A | 610 | −8.144 | 30.137 | −15.816 | 1.00 | 64.55 | C |
| ATOM | 4383 | CB | ALA A | 610 | −7.984 | 31.556 | −15.289 | 1.00 | 65.67 | C |
| ATOM | 4384 | C | ALA A | 610 | −6.877 | 29.332 | −15.590 | 1.00 | 63.40 | C |
| ATOM | 4385 | O | ALA A | 610 | −6.809 | 28.494 | −14.697 | 1.00 | 61.36 | O |
| ATOM | 4386 | N | LEU A | 611 | −5.881 | 29.583 | −16.427 | 1.00 | 66.48 | N |
| ATOM | 4387 | CA | LEU A | 611 | −4.560 | 29.007 | −16.250 | 1.00 | 70.18 | C |
| ATOM | 4388 | CB | LEU A | 611 | −4.383 | 27.757 | −17.133 | 1.00 | 70.35 | C |
| ATOM | 4389 | CG | LEU A | 611 | −3.078 | 26.932 | −17.178 | 1.00 | 71.17 | C |
| ATOM | 4390 | CD1 | LEU A | 611 | −2.067 | 27.530 | −18.147 | 1.00 | 71.17 | C |
| ATOM | 4391 | CD2 | LEU A | 611 | −2.440 | 26.701 | −15.810 | 1.00 | 70.73 | C |
| ATOM | 4392 | C | LEU A | 611 | −3.506 | 30.065 | −16.555 | 1.00 | 71.48 | C |
| ATOM | 4393 | O | LEU A | 611 | −3.559 | 30.739 | −17.591 | 1.00 | 69.86 | O |
| ATOM | 4394 | N | PHE A | 612 | −2.596 | 30.216 | −15.625 | 1.00 | 73.95 | N |
| ATOM | 4395 | CA | PHE A | 612 | −1.438 | 31.110 | −15.794 | 1.00 | 77.88 | C |
| ATOM | 4396 | CB | PHE A | 612 | −1.355 | 32.094 | −14.624 | 1.00 | 83.00 | C |
| ATOM | 4397 | CG | PHE A | 612 | −2.279 | 33.273 | −14.755 | 1.00 | 88.89 | C |
| ATOM | 4398 | CD2 | PHE A | 612 | −1.789 | 34.513 | −15.154 | 1.00 | 90.61 | C |
| ATOM | 4399 | CE2 | PHE A | 612 | −2.638 | 35.605 | −15.279 | 1.00 | 92.18 | C |
| ATOM | 4400 | CZ | PHE A | 612 | −3.991 | 35.466 | −15.000 | 1.00 | 92.00 | C |
| ATOM | 4401 | CE1 | PHE A | 612 | −4.493 | 34.235 | −14.613 | 1.00 | 93.06 | C |
| ATOM | 4402 | CD1 | PHE A | 612 | −3.640 | 33.146 | −14.487 | 1.00 | 91.87 | C |
| ATOM | 4403 | C | PHE A | 612 | −0.165 | 30.289 | −15.877 | 1.00 | 77.24 | C |
| ATOM | 4404 | O | PHE A | 612 | −0.001 | 29.314 | −15.138 | 1.00 | 79.37 | O |
| ATOM | 4405 | N | TYR A | 613 | 0.725 | 30.668 | −16.790 | 1.00 | 74.62 | N |
| ATOM | 4406 | CA | TYR A | 613 | 2.035 | 30.027 | −16.887 | 1.00 | 73.06 | C |
| ATOM | 4407 | CB | TYR A | 613 | 2.121 | 29.060 | −18.082 | 1.00 | 71.88 | C |
| ATOM | 4408 | CG | TYR A | 613 | 1.778 | 29.630 | −19.452 | 1.00 | 72.39 | C |
| ATOM | 4409 | CD1 | TYR A | 613 | 0.472 | 30.018 | −19.772 | 1.00 | 72.34 | C |
| ATOM | 4410 | CE1 | TYR A | 613 | 0.157 | 30.517 | −21.031 | 1.00 | 71.61 | C |
| ATOM | 4411 | CZ | TYR A | 613 | 1.150 | 30.615 | −21.996 | 1.00 | 71.37 | C |
| ATOM | 4412 | OH | TYR A | 613 | 0.847 | 31.104 | −23.245 | 1.00 | 68.39 | O |
| ATOM | 4413 | CE2 | TYR A | 613 | 2.445 | 30.221 | −21.711 | 1.00 | 72.78 | C |
| ATOM | 4414 | CD2 | TYR A | 613 | 2.752 | 29.724 | −20.449 | 1.00 | 73.26 | C |
| ATOM | 4415 | C | TYR A | 613 | 3.184 | 31.035 | −16.871 | 1.00 | 72.63 | C |
| ATOM | 4416 | O | TYR A | 613 | 3.345 | 31.837 | −17.794 | 1.00 | 72.78 | O |
| ATOM | 4417 | N | PHE A | 614 | 3.959 | 30.993 | −15.791 | 1.00 | 70.95 | N |
| ATOM | 4418 | CA | PHE A | 614 | 5.091 | 31.885 | −15.602 | 1.00 | 69.51 | C |
| ATOM | 4419 | CB | PHE A | 614 | 5.138 | 32.385 | −14.153 | 1.00 | 69.52 | C |
| ATOM | 4420 | CG | PHE A | 614 | 3.968 | 33.251 | −13.764 | 1.00 | 71.10 | C |
| ATOM | 4421 | CD1 | PHE A | 614 | 3.954 | 34.613 | −14.073 | 1.00 | 70.94 | C |
| ATOM | 4422 | CE1 | PHE A | 614 | 2.878 | 35.416 | −13.714 | 1.00 | 69.57 | C |
| ATOM | 4423 | CZ | PHE A | 614 | 1.804 | 34.864 | −13.031 | 1.00 | 69.87 | C |
| ATOM | 4424 | CE2 | PHE A | 614 | 1.806 | 33.511 | −12.711 | 1.00 | 70.23 | C |
| ATOM | 4425 | CD2 | PHE A | 614 | 2.884 | 32.712 | −13.074 | 1.00 | 70.37 | C |
| ATOM | 4426 | C | PHE A | 614 | 6.399 | 31.180 | −15.945 | 1.00 | 70.03 | C |
| ATOM | 4427 | O | PHE A | 614 | 6.508 | 29.958 | −15.813 | 1.00 | 69.62 | O |
| ATOM | 4428 | N | GLY A | 615 | 7.383 | 31.954 | −16.400 | 1.00 | 69.84 | N |
| ATOM | 4429 | CA | GLY A | 615 | 8.754 | 31.466 | −16.538 | 1.00 | 70.06 | C |
| ATOM | 4430 | C | GLY A | 615 | 9.368 | 31.324 | −15.158 | 1.00 | 71.25 | C |
| ATOM | 4431 | O | GLY A | 615 | 8.904 | 31.946 | −14.203 | 1.00 | 72.04 | O |
| ATOM | 4432 | N | LEU A | 616 | 10.410 | 30.508 | −15.042 | 1.00 | 71.99 | N |
| ATOM | 4433 | CA | LEU A | 616 | 10.981 | 30.215 | −13.729 | 1.00 | 72.48 | C |
| ATOM | 4434 | CB | LEU A | 616 | 10.649 | 28.776 | −13.327 | 1.00 | 70.89 | C |
| ATOM | 4435 | CG | LEU A | 616 | 10.504 | 28.479 | −11.831 | 1.00 | 70.86 | C |
| ATOM | 4436 | CD1 | LEU A | 616 | 9.820 | 29.620 | −11.087 | 1.00 | 70.64 | C |
| ATOM | 4437 | CD2 | LEU A | 616 | 9.751 | 27.174 | −11.630 | 1.00 | 70.21 | C |
| ATOM | 4438 | C | LEU A | 616 | 12.488 | 30.469 | −13.624 | 1.00 | 75.56 | C |
| ATOM | 4439 | O | LEU A | 616 | 13.181 | 30.618 | −14.636 | 1.00 | 78.52 | O |
| ATOM | 4440 | N | ASN A | 617 | 12.978 | 30.548 | −12.389 | 1.00 | 75.23 | N |
| ATOM | 4441 | CA | ASN A | 617 | 14.410 | 30.602 | −12.125 | 1.00 | 74.47 | C |
| ATOM | 4442 | CB | ASN A | 617 | 14.818 | 31.975 | −11.594 | 1.00 | 71.77 | C |
| ATOM | 4443 | C | ASN A | 617 | 14.808 | 29.492 | −11.158 | 1.00 | 74.32 | C |
| ATOM | 4444 | O | ASN A | 617 | 14.541 | 29.576 | −9.956 | 1.00 | 72.37 | O |
| ATOM | 4445 | N | ILE A | 618 | 15.428 | 28.449 | −11.710 | 1.00 | 75.26 | N |
| ATOM | 4446 | CA | ILE A | 618 | 15.826 | 27.237 | −10.969 | 1.00 | 73.42 | C |
| ATOM | 4447 | CB | ILE A | 618 | 16.638 | 26.258 | −11.860 | 1.00 | 71.23 | C |
| ATOM | 4448 | CG1 | ILE A | 618 | 17.329 | 26.992 | −13.030 | 1.00 | 69.60 | C |
| ATOM | 4449 | CD1 | ILE A | 618 | 18.632 | 27.691 | −12.686 | 1.00 | 64.62 | C |

-continued

| | | Atomic coordinates for CRBN:DDB1:Lenalidomide (Human protein) | | | | | | | |
|---|---|---|---|---|---|---|---|---|---|
| ATOM | 4450 | CG2 | ILE A | 618 | 15.736 | 25.153 | −12.384 | 1.00 | 69.29 | C |
| ATOM | 4451 | C | ILE A | 618 | 16.605 | 27.489 | −9.672 | 1.00 | 74.01 | C |
| ATOM | 4452 | O | ILE A | 618 | 16.380 | 26.807 | −8.668 | 1.00 | 71.27 | O |
| ATOM | 4453 | N | GLU A | 619 | 17.516 | 28.464 | −9.710 | 1.00 | 72.73 | N |
| ATOM | 4454 | CA | GLU A | 619 | 18.335 | 28.823 | −8.554 | 1.00 | 69.74 | C |
| ATOM | 4455 | CB | GLU A | 619 | 19.809 | 28.932 | −8.959 | 1.00 | 68.90 | C |
| ATOM | 4456 | C | GLU A | 619 | 17.861 | 30.127 | −7.908 | 1.00 | 68.32 | C |
| ATOM | 4457 | O | THR A | 619 | 17.920 | 30.276 | −6.686 | 1.00 | 66.49 | O |
| ATOM | 4458 | N | THR A | 620 | 17.388 | 31.062 | −8.733 | 1.00 | 67.72 | N |
| ATOM | 4459 | CA | THR A | 620 | 16.944 | 32.377 | −8.259 | 1.00 | 64.65 | C |
| ATOM | 4460 | CB | THR A | 620 | 16.940 | 33.422 | −9.393 | 1.00 | 62.51 | C |
| ATOM | 4461 | C | THR A | 620 | 15.567 | 32.326 | −7.594 | 1.00 | 63.53 | C |
| ATOM | 4462 | O | THR A | 620 | 15.444 | 32.625 | −6.407 | 1.00 | 62.95 | O |
| ATOM | 4463 | N | GLY A | 621 | 14.540 | 31.956 | −8.363 | 1.00 | 62.70 | N |
| ATOM | 4464 | CA | GLY A | 621 | 13.178 | 31.811 | −7.838 | 1.00 | 60.61 | C |
| ATOM | 4465 | C | GLY A | 621 | 12.129 | 32.797 | −8.343 | 1.00 | 60.22 | C |
| ATOM | 4466 | O | GLY A | 621 | 10.956 | 32.697 | −7.977 | 1.00 | 58.25 | O |
| ATOM | 4467 | N | LEU A | 623 | 12.543 | 33.749 | −9.179 | 1.00 | 61.52 | N |
| ATOM | 4468 | CA | LEU A | 623 | 11.630 | 34.776 | −9.695 | 1.00 | 60.19 | C |
| ATOM | 4469 | CB | LEU A | 623 | 12.400 | 36.054 | −10.057 | 1.00 | 60.10 | C |
| ATOM | 4470 | C | LEU A | 623 | 10.828 | 34.259 | −10.892 | 1.00 | 58.73 | C |
| ATOM | 4471 | O | LEU A | 623 | 11.283 | 33.365 | −11.608 | 1.00 | 59.23 | O |
| ATOM | 4472 | N | LEU A | 623 | 9.636 | 34.819 | −11.097 | 1.00 | 57.65 | N |
| ATOM | 4473 | CA | LEU A | 623 | 8.730 | 34.355 | −12.160 | 1.00 | 58.00 | C |
| ATOM | 4474 | CB | LEU A | 623 | 7.504 | 33.646 | −11.563 | 1.00 | 56.81 | C |
| ATOM | 4475 | C | LEU A | 623 | 8.298 | 35.467 | −13.129 | 1.00 | 56.78 | C |
| ATOM | 4476 | O | LEU A | 623 | 8.132 | 36.621 | −12.733 | 1.00 | 56.28 | O |
| ATOM | 4477 | N | SER A | 624 | 8.100 | 35.098 | −14.394 | 1.00 | 56.30 | N |
| ATOM | 4478 | CA | SER A | 624 | 7.840 | 36.067 | −15.460 | 1.00 | 55.15 | C |
| ATOM | 4479 | CB | SER A | 624 | 9.143 | 36.395 | −16.184 | 1.00 | 54.13 | C |
| ATOM | 4480 | OG | SER A | 624 | 9.729 | 35.214 | −16.702 | 1.00 | 52.98 | O |
| ATOM | 4481 | C | SER A | 624 | 6.800 | 35.592 | −16.483 | 1.00 | 55.31 | C |
| ATOM | 4482 | O | SER A | 624 | 6.771 | 34.415 | −16.857 | 1.00 | 55.35 | O |
| ATOM | 4483 | N | ASP A | 625 | 5.967 | 36.533 | −16.937 | 1.00 | 54.14 | N |
| ATOM | 4484 | CA | ASP A | 625 | 4.999 | 36.327 | −18.033 | 1.00 | 50.79 | C |
| ATOM | 4485 | CB | ASP A | 625 | 5.651 | 35.624 | −19.229 | 1.00 | 51.15 | C |
| ATOM | 4486 | CG | ASP A | 625 | 6.993 | 36.248 | −19.613 | 1.00 | 53.05 | C |
| ATOM | 4487 | OD1 | ASP A | 625 | 7.120 | 37.496 | −19.577 | 1.00 | 51.81 | O |
| ATOM | 4488 | OD2 | ASP A | 625 | 7.926 | 35.483 | −19.937 | 1.00 | 53.80 | O |
| ATOM | 4489 | C | ASP A | 625 | 3.723 | 35.619 | −17.604 | 1.00 | 47.71 | C |
| ATOM | 4490 | O | ASP A | 625 | 2.731 | 36.270 | −17.274 | 1.00 | 44.04 | O |
| ATOM | 4491 | N | LYS A | 627 | 1.443 | 35.803 | −20.117 | 1.00 | 60.53 | N |
| ATOM | 4492 | CA | LYS A | 627 | 1.209 | 34.412 | −20.495 | 1.00 | 63.89 | C |
| ATOM | 4493 | CB | LYS A | 627 | 2.501 | 33.599 | −20.354 | 1.00 | 62.91 | C |
| ATOM | 4494 | C | LYS A | 627 | 0.048 | 33.769 | −19.702 | 1.00 | 65.61 | C |
| ATOM | 4495 | O | LYS A | 627 | 0.235 | 33.256 | −18.589 | 1.00 | 65.15 | O |
| ATOM | 4496 | N | LYS A | 628 | −1.145 | 33.804 | −20.296 | 1.00 | 66.68 | N |
| ATOM | 4497 | CA | LYS A | 628 | −2.379 | 33.318 | −19.660 | 1.00 | 66.88 | C |
| ATOM | 4498 | CB | LYS A | 628 | −3.083 | 34.474 | −18.928 | 1.00 | 64.93 | C |
| ATOM | 4499 | CG | LYS A | 628 | −4.567 | 34.656 | −19.230 | 1.00 | 63.02 | C |
| ATOM | 4500 | CD | LYS A | 628 | −5.441 | 34.195 | −18.080 | 1.00 | 62.61 | C |
| ATOM | 4501 | CE | LYS A | 628 | −6.744 | 34.976 | −18.052 | 1.00 | 61.98 | C |
| ATOM | 4502 | NZ | LYS A | 628 | −7.276 | 35.137 | −16.670 | 1.00 | 61.13 | N |
| ATOM | 4503 | C | LYS A | 628 | −3.310 | 32.668 | −20.687 | 1.00 | 68.01 | C |
| ATOM | 4504 | O | LYS A | 628 | −3.241 | 32.981 | −21.882 | 1.00 | 67.62 | O |
| ATOM | 4505 | N | VAL A | 629 | −4.170 | 31.764 | −20.213 | 1.00 | 67.42 | N |
| ATOM | 4506 | CA | VAL A | 629 | −5.157 | 31.088 | −21.065 | 1.00 | 67.85 | C |
| ATOM | 4507 | CB | VAL A | 629 | −4.495 | 30.004 | −21.968 | 1.00 | 68.50 | C |
| ATOM | 4508 | CG1 | VAL A | 629 | −3.602 | 29.071 | −21.159 | 1.00 | 68.26 | C |
| ATOM | 4509 | CG2 | VAL A | 629 | −5.537 | 29.224 | −22.764 | 1.00 | 69.93 | C |
| ATOM | 4510 | C | VAL A | 629 | −6.302 | 30.500 | −20.230 | 1.00 | 67.66 | C |
| ATOM | 4511 | O | VAL A | 629 | −6.070 | 29.974 | −19.140 | 1.00 | 70.23 | O |
| ATOM | 4512 | N | THR A | 630 | −7.534 | 30.613 | −20.731 | 1.00 | 65.48 | N |
| ATOM | 4513 | CA | THR A | 630 | −8.694 | 29.978 | −20.085 | 1.00 | 64.98 | C |
| ATOM | 4514 | CB | THR A | 630 | −9.927 | 30.911 | −20.018 | 1.00 | 64.27 | C |
| ATOM | 4515 | OG1 | THR A | 630 | −10.504 | 31.052 | −21.320 | 1.00 | 64.80 | O |
| ATOM | 4516 | CG2 | THR A | 630 | −9.550 | 32.289 | −19.470 | 1.00 | 62.75 | C |
| ATOM | 4517 | C | THR A | 630 | −9.061 | 28.656 | −20.779 | 1.00 | 63.77 | C |
| ATOM | 4518 | O | THR A | 630 | −8.891 | 28.511 | −21.989 | 1.00 | 60.51 | O |
| ATOM | 4519 | N | LEU A | 631 | −9.562 | 27.698 | −20.000 | 1.00 | 64.92 | N |
| ATOM | 4520 | CA | LEU A | 631 | −9.756 | 26.327 | −20.482 | 1.00 | 65.71 | C |
| ATOM | 4521 | CB | LEU A | 631 | −8.714 | 25.396 | −19.850 | 1.00 | 62.96 | C |
| ATOM | 4522 | CG | LEU A | 631 | −7.304 | 25.942 | −19.583 | 1.00 | 60.76 | C |
| ATOM | 4523 | CD1 | LEU A | 631 | −6.571 | 25.057 | −18.590 | 1.00 | 60.24 | C |
| ATOM | 4524 | CD2 | LEU A | 631 | −6.500 | 26.097 | −20.867 | 1.00 | 59.81 | C |
| ATOM | 4525 | C | LEU A | 631 | −11.168 | 25.778 | −20.224 | 1.00 | 69.30 | C |
| ATOM | 4526 | O | LEU A | 631 | −11.658 | 24.930 | −20.973 | 1.00 | 70.69 | O |

-continued

| | | | | | | | | | | |
|---|---|---|---|---|---|---|---|---|---|---|
{colspan="11"}Atomic coordinates for CRBN:DDB1:Lenalidomide (Human protein)

| ATOM | 4527 | N | GLY A | 632 | −11.809 | 26.252 | −19.159 | 1.00 | 69.62 | O |
| ATOM | 4528 | CA | GLY A | 632 | −13.153 | 25.806 | −18.803 | 1.00 | 74.19 | C |
| ATOM | 4529 | C | GLY A | 632 | −13.480 | 26.109 | −17.356 | 1.00 | 77.98 | C |
| ATOM | 4530 | O | GLY A | 632 | −12.683 | 25.817 | −16.464 | 1.00 | 79.57 | O |
| ATOM | 4531 | N | THR A | 633 | −14.675 | 26.658 | −17.131 | 1.00 | 80.62 | N |
| ATOM | 4532 | CA | THR A | 633 | −15.079 | 27.228 | −15.830 | 1.00 | 82.84 | C |
| ATOM | 4533 | CB | THR A | 633 | −16.518 | 27.792 | −15.864 | 1.00 | 83.85 | C |
| ATOM | 4534 | OG1 | THR A | 633 | −17.425 | 26.772 | −16.301 | 1.00 | 84.83 | O |
| ATOM | 4535 | CG2 | THR A | 633 | −16.611 | 29.015 | −16.789 | 1.00 | 81.85 | C |
| ATOM | 4536 | C | THR A | 633 | −14.939 | 26.318 | −14.606 | 1.00 | 84.24 | C |
| ATOM | 4537 | O | THR A | 633 | −14.722 | 26.808 | −13.492 | 1.00 | 84.69 | O |
| ATOM | 4538 | N | GLN A | 634 | −15.085 | 25.007 | −14.806 | 1.00 | 83.04 | N |
| ATOM | 4539 | CA | GLN A | 634 | −14.820 | 24.035 | −13.745 | 1.00 | 80.21 | C |
| ATOM | 4540 | CB | GLN A | 634 | −15.358 | 22.649 | −14.120 | 1.00 | 76.41 | C |
| ATOM | 4541 | C | GLN A | 634 | −13.309 | 23.987 | −13.447 | 1.00 | 78.80 | C |
| ATOM | 4542 | O | GLN A | 634 | −12.498 | 23.837 | −14.371 | 1.00 | 77.07 | O |
| ATOM | 4543 | N | PRO A | 635 | −12.931 | 24.146 | −12.157 | 1.00 | 76.37 | N |
| ATOM | 4544 | CA | PRO A | 635 | −11.540 | 24.178 | −11.684 | 1.00 | 74.01 | C |
| ATOM | 4545 | CB | PRO A | 635 | −11.686 | 23.955 | −10.177 | 1.00 | 76.16 | C |
| ATOM | 4546 | CG | PRO A | 635 | −12.994 | 24.584 | −9.847 | 1.00 | 76.06 | C |
| ATOM | 4547 | CD | PRO A | 635 | −13.882 | 24.388 | −11.052 | 1.00 | 76.79 | C |
| ATOM | 4548 | C | PRO A | 635 | −10.638 | 23.100 | −12.298 | 1.00 | 70.56 | C |
| ATOM | 4549 | O | PRO A | 635 | −11.057 | 21.952 | −12.469 | 1.00 | 71.18 | O |
| ATOM | 4550 | N | THR A | 636 | −9.403 | 23.484 | −12.602 | 1.00 | 65.20 | N |
| ATOM | 4551 | CA | THR A | 636 | −8.468 | 22.640 | −13.339 | 1.00 | 61.67 | C |
| ATOM | 4552 | CB | THR A | 636 | −7.629 | 23.488 | −14.318 | 1.00 | 62.18 | C |
| ATOM | 4553 | OG1 | THR A | 636 | −8.396 | 24.619 | −14.758 | 1.00 | 63.11 | O |
| ATOM | 4554 | CG2 | THR A | 636 | −7.185 | 22.667 | −15.524 | 1.00 | 59.51 | C |
| ATOM | 4555 | C | THR A | 636 | −7.529 | 21.891 | −12.391 | 1.00 | 59.20 | C |
| ATOM | 4556 | O | THR A | 636 | −7.184 | 22.404 | −11.328 | 1.00 | 59.98 | O |
| ATOM | 4557 | N | VAL A | 637 | −7.128 | 20.679 | −12.786 | 1.00 | 56.20 | N |
| ATOM | 4558 | CA | VAL A | 637 | −6.172 | 19.849 | −12.024 | 1.00 | 53.28 | C |
| ATOM | 4559 | CB | VAL A | 637 | −6.874 | 18.620 | −11.381 | 1.00 | 50.32 | C |
| ATOM | 4560 | CG1 | VAL A | 637 | −5.881 | 17.740 | −10.634 | 1.00 | 48.48 | C |
| ATOM | 4561 | CG2 | VAL A | 637 | −7.988 | 19.066 | −10.446 | 1.00 | 49.37 | C |
| ATOM | 4562 | C | VAL A | 637 | −5.018 | 19.399 | −12.945 | 1.00 | 52.78 | C |
| ATOM | 4563 | O | VAL A | 637 | −5.255 | 18.989 | −14.085 | 1.00 | 53.36 | O |
| ATOM | 4564 | N | LEU A | 638 | −3.779 | 19.475 | −12.456 | 1.00 | 49.78 | N |
| ATOM | 4565 | CA | LEU A | 638 | −2.610 | 19.184 | −13.294 | 1.00 | 48.60 | C |
| ATOM | 4566 | CB | LEU A | 638 | −1.669 | 20.386 | −13.345 | 1.00 | 49.05 | C |
| ATOM | 4567 | CG | LEU A | 638 | −2.284 | 21.783 | −13.404 | 1.00 | 49.76 | C |
| ATOM | 4568 | CD1 | LEU A | 638 | −1.267 | 22.802 | −12.914 | 1.00 | 49.58 | C |
| ATOM | 4569 | CD2 | LEU A | 638 | −2.793 | 22.124 | −14.801 | 1.00 | 48.13 | C |
| ATOM | 4570 | C | LEU A | 638 | −1.823 | 17.968 | −12.833 | 1.00 | 48.45 | C |
| ATOM | 4571 | O | LEU A | 638 | −1.516 | 17.831 | −11.655 | 1.00 | 50.58 | O |
| ATOM | 4572 | N | ARG A | 639 | −1.491 | 17.093 | −13.778 | 1.00 | 49.22 | N |
| ATOM | 4573 | CA | ARG A | 639 | −0.609 | 15.956 | −13.516 | 1.00 | 47.90 | C |
| ATOM | 4574 | CB | ARG A | 639 | −1.389 | 14.627 | −13.460 | 1.00 | 50.04 | C |
| ATOM | 4575 | CG | ARG A | 639 | −2.135 | 14.375 | −12.152 | 1.00 | 55.11 | C |
| ATOM | 4576 | CD | ARG A | 639 | −1.212 | 13.989 | −11.003 | 1.00 | 56.65 | C |
| ATOM | 4577 | NE | ARG A | 639 | −0.810 | 12.577 | −11.032 | 1.00 | 61.56 | N |
| ATOM | 4578 | CZ | ARG A | 639 | −1.285 | 11.630 | −10.213 | 1.00 | 62.96 | C |
| ATOM | 4579 | NH1 | ARG A | 639 | −2.195 | 11.918 | −9.290 | 1.00 | 63.23 | N |
| ATOM | 4580 | NH2 | ARG A | 639 | −0.844 | 10.385 | −10.310 | 1.00 | 61.04 | N |
| ATOM | 4581 | C | ARG A | 639 | 0.495 | 15.871 | −14.557 | 1.00 | 44.29 | C |
| ATOM | 4582 | O | ARG A | 639 | 0.343 | 16.331 | −15.687 | 1.00 | 41.78 | O |
| ATOM | 4583 | N | THR A | 640 | 1.609 | 15.277 | −14.157 | 1.00 | 42.30 | N |
| ATOM | 4584 | CA | THR A | 640 | 2.721 | 15.047 | −15.048 | 1.00 | 41.95 | C |
| ATOM | 4585 | CB | THR A | 640 | 4.042 | 15.082 | −14.256 | 1.00 | 42.92 | C |
| ATOM | 4586 | OG1 | THR A | 640 | 4.186 | 16.368 | −13.641 | 1.00 | 43.48 | O |
| ATOM | 4587 | CG2 | THR A | 640 | 5.250 | 14.816 | −15.162 | 1.00 | 44.34 | C |
| ATOM | 4588 | C | THR A | 640 | 2.537 | 13.695 | −15.717 | 1.00 | 40.35 | C |
| ATOM | 4589 | O | THR A | 640 | 1.846 | 12.842 | −15.189 | 1.00 | 39.51 | O |
| ATOM | 4590 | N | PHE A | 641 | 3.122 | 13.526 | −16.899 | 1.00 | 41.35 | N |
| ATOM | 4591 | CA | PHE A | 641 | 3.334 | 12.202 | −17.488 | 1.00 | 41.73 | C |
| ATOM | 4592 | CB | PHE A | 641 | 2.030 | 11.592 | −17.992 | 1.00 | 39.26 | C |
| ATOM | 4593 | CG | PHE A | 641 | 1.426 | 12.316 | −19.152 | 1.00 | 39.05 | C |
| ATOM | 4594 | CD1 | PHE A | 641 | 0.842 | 13.573 | −18.983 | 1.00 | 39.26 | C |
| ATOM | 4595 | CE1 | PHE A | 641 | 0.271 | 14.238 | −20.057 | 1.00 | 38.29 | C |
| ATOM | 4596 | CZ | PHE A | 641 | 0.268 | 13.645 | −21.311 | 1.00 | 37.77 | C |
| ATOM | 4597 | CE2 | PHE A | 641 | 0.838 | 12.394 | −21.488 | 1.00 | 37.99 | C |
| ATOM | 4598 | CD2 | PHE A | 641 | 1.410 | 11.733 | −20.412 | 1.00 | 37.82 | C |
| ATOM | 4599 | C | PHE A | 641 | 4.385 | 12.228 | −18.599 | 1.00 | 44.69 | C |
| ATOM | 4600 | O | PHE A | 641 | 4.634 | 13.272 | −19.217 | 1.00 | 43.37 | O |
| ATOM | 4601 | N | ARG A | 642 | 5.001 | 11.074 | −18.841 | 1.00 | 47.15 | N |
| ATOM | 4602 | CA | ARG A | 642 | 6.055 | 10.973 | −19.829 | 1.00 | 49.19 | C |
| ATOM | 4603 | CB | ARG A | 642 | 7.202 | 10.083 | −19.322 | 1.00 | 51.52 | C |

-continued

| Atomic coordinates for CRBN:DDB1:Lenalidomide (Human protein) | | | | | | | | | |
|---|---|---|---|---|---|---|---|---|---|
| ATOM | 4604 | CG | ARG A | 642 | 8.236 | 10.829 | −18.478 | 1.00 | 55.31 | C |
| ATOM | 4605 | CD | ARG A | 642 | 9.663 | 10.402 | −18.830 | 1.00 | 60.61 | C |
| ATOM | 4606 | NE | ARG A | 642 | 10.666 | 11.466 | −18.641 | 1.00 | 60.77 | N |
| ATOM | 4607 | CZ | ARG A | 642 | 11.591 | 11.488 | −17.676 | 1.00 | 58.54 | C |
| ATOM | 4608 | NH1 | ARG A | 642 | 11.669 | 10.510 | −16.783 | 1.00 | 55.92 | N |
| ATOM | 4609 | NH2 | ARG A | 642 | 12.446 | 12.498 | −17.605 | 1.00 | 58.06 | N |
| ATOM | 4610 | C | ARG A | 642 | 5.526 | 10.500 | −21.182 | 1.00 | 49.76 | C |
| ATOM | 4611 | O | ARG A | 642 | 4.832 | 9.484 | −21.259 | 1.00 | 48.46 | O |
| ATOM | 4612 | N | SER A | 643 | 5.843 | 11.272 | −22.228 | 1.00 | 51.04 | N |
| ATOM | 4613 | CA | SER A | 643 | 5.563 | 10.935 | −23.636 | 1.00 | 53.50 | C |
| ATOM | 4614 | CB | SER A | 643 | 4.086 | 10.588 | −23.865 | 1.00 | 54.34 | C |
| ATOM | 4615 | C | SER A | 643 | 5.953 | 12.102 | −24.538 | 1.00 | 55.44 | C |
| ATOM | 4616 | O | SER A | 643 | 7.121 | 12.270 | −24.888 | 1.00 | 58.95 | O |
| ATOM | 4617 | N | SER A | 645 | 9.458 | 10.222 | −24.406 | 1.00 | 53.63 | N |
| ATOM | 4618 | CA | SER A | 645 | 10.765 | 10.513 | −23.810 | 1.00 | 56.71 | C |
| ATOM | 4619 | CB | SER A | 645 | 11.808 | 10.777 | −24.902 | 1.00 | 54.28 | C |
| ATOM | 4620 | C | SER A | 645 | 10.724 | 11.685 | −22.809 | 1.00 | 57.78 | C |
| ATOM | 4621 | O | SER A | 645 | 11.261 | 11.586 | −21.697 | 1.00 | 58.46 | O |
| ATOM | 4622 | N | THR A | 646 | 10.077 | 12.779 | −23.210 | 1.00 | 56.83 | N |
| ATOM | 4623 | CA | THR A | 646 | 10.015 | 14.009 | −22.410 | 1.00 | 54.49 | C |
| ATOM | 4624 | CB | THR A | 646 | 10.002 | 15.253 | −23.330 | 1.00 | 53.55 | C |
| ATOM | 4625 | OG1 | THR A | 646 | 10.221 | 16.428 | −22.546 | 1.00 | 56.63 | O |
| ATOM | 4626 | CG2 | THR A | 646 | 8.681 | 15.373 | −24.115 | 1.00 | 51.15 | O |
| ATOM | 4627 | C | THR A | 646 | 8.834 | 14.007 | −21.404 | 1.00 | 53.23 | C |
| ATOM | 4628 | O | THR A | 646 | 8.233 | 12.962 | −21.174 | 1.00 | 54.41 | O |
| ATOM | 4629 | N | THR A | 647 | 8.524 | 15.157 | −20.799 | 1.00 | 50.27 | N |
| ATOM | 4630 | CA | THR A | 647 | 7.373 | 15.273 | −19.882 | 1.00 | 49.42 | C |
| ATOM | 4631 | CB | THR A | 647 | 7.794 | 15.709 | −18.464 | 1.00 | 50.84 | C |
| ATOM | 4632 | OG1 | THR A | 647 | 8.999 | 16.482 | −18.537 | 1.00 | 54.95 | O |
| ATOM | 4633 | CG2 | THR A | 647 | 8.031 | 14.496 | −17.580 | 1.00 | 52.38 | C |
| ATOM | 4634 | C | THR A | 647 | 6.273 | 16.220 | −20.371 | 1.00 | 48.16 | C |
| ATOM | 4635 | O | THR A | 647 | 6.541 | 17.342 | −20.789 | 1.00 | 48.31 | O |
| ATOM | 4636 | N | ASN A | 648 | 5.030 | 15.751 | −20.316 | 1.00 | 47.79 | N |
| ATOM | 4637 | CA | ASN A | 648 | 3.868 | 16.577 | −20.646 | 1.00 | 46.43 | C |
| ATOM | 4638 | CB | ASN A | 648 | 3.125 | 16.018 | −21.873 | 1.00 | 47.29 | C |
| ATOM | 4639 | CG | ASN A | 648 | 3.900 | 16.197 | −23.182 | 1.00 | 49.78 | C |
| ATOM | 4640 | OD1 | ASN A | 648 | 5.120 | 16.390 | −23.195 | 1.00 | 50.61 | O |
| ATOM | 4641 | ND2 | ASN A | 648 | 3.183 | 16.115 | −24.297 | 1.00 | 49.50 | N |
| ATOM | 4642 | C | ASN A | 648 | 2.921 | 16.697 | −19.439 | 1.00 | 45.51 | C |
| ATOM | 4643 | O | ASN A | 648 | 3.113 | 16.017 | −18.413 | 1.00 | 43.38 | O |
| ATOM | 4644 | N | VAL A | 649 | 1.912 | 17.565 | −19.561 | 1.00 | 42.59 | N |
| ATOM | 4645 | CA | VAL A | 649 | 0.968 | 17.822 | −18.467 | 1.00 | 40.76 | C |
| ATOM | 4646 | CB | VAL A | 649 | 1.169 | 19.230 | −17.856 | 1.00 | 40.69 | C |
| ATOM | 4647 | CG1 | VAL A | 649 | 0.119 | 19.515 | −16.788 | 1.00 | 41.78 | C |
| ATOM | 4648 | CG2 | VAL A | 649 | 2.566 | 19.370 | −17.268 | 1.00 | 40.43 | C |
| ATOM | 4649 | C | VAL A | 649 | −0.491 | 17.655 | −18.899 | 1.00 | 38.73 | C |
| ATOM | 4650 | O | VAL A | 649 | −0.920 | 18.228 | −19.888 | 1.00 | 39.84 | O |
| ATOM | 4651 | N | PHE A | 650 | −1.246 | 16.868 | −18.142 | 1.00 | 37.60 | N |
| ATOM | 4652 | CA | PHE A | 650 | −2.670 | 16.677 | −18.401 | 1.00 | 36.68 | C |
| ATOM | 4653 | CB | PHE A | 650 | −3.077 | 15.242 | −18.085 | 1.00 | 35.18 | C |
| ATOM | 4654 | CG | PHE A | 650 | −4.253 | 14.748 | −18.875 | 1.00 | 33.59 | C |
| ATOM | 4655 | CD1 | PHE A | 650 | −5.556 | 15.113 | −18.526 | 1.00 | 34.08 | C |
| ATOM | 4656 | CE1 | PHE A | 650 | −6.650 | 14.641 | −19.255 | 1.00 | 33.62 | C |
| ATOM | 4657 | CZ | PHE A | 650 | −6.446 | 13.787 | −20.336 | 1.00 | 33.91 | C |
| ATOM | 4658 | CE2 | PHE A | 650 | −5.148 | 13.407 | −20.686 | 1.00 | 33.69 | C |
| ATOM | 4659 | CD2 | PHE A | 650 | −4.064 | 13.885 | −19.957 | 1.00 | 32.94 | C |
| ATOM | 4660 | C | PHE A | 650 | −3.459 | 17.615 | −17.518 | 1.00 | 37.39 | C |
| ATOM | 4661 | O | PHE A | 650 | −3.218 | 17.694 | −16.313 | 1.00 | 36.64 | O |
| ATOM | 4662 | N | ALA A | 651 | −4.414 | 18.312 | −18.122 | 1.00 | 39.09 | N |
| ATOM | 4663 | CA | ALA A | 651 | −5.225 | 19.291 | −17.411 | 1.00 | 40.70 | C |
| ATOM | 4664 | CB | ALA A | 651 | −5.019 | 20.677 | −18.003 | 1.00 | 40.70 | C |
| ATOM | 4665 | C | ALA A | 651 | −6.699 | 18.910 | −17.425 | 1.00 | 41.92 | C |
| ATOM | 4666 | O | ALA A | 651 | −7.345 | 18.919 | −18.467 | 1.00 | 42.06 | O |
| ATOM | 4667 | N | CYS A | 652 | −7.226 | 18.587 | −16.253 | 1.00 | 46.12 | N |
| ATOM | 4668 | CA | CYS A | 652 | −8.602 | 18.139 | −16.137 | 1.00 | 50.41 | C |
| ATOM | 4669 | CB | CYS A | 652 | −8.723 | 17.070 | −15.053 | 1.00 | 50.37 | C |
| ATOM | 4670 | SG | CYS A | 652 | −7.703 | 15.611 | −15.357 | 1.00 | 51.52 | S |
| ATOM | 4671 | C | CYS A | 652 | −9.557 | 19.295 | −15.858 | 1.00 | 54.45 | C |
| ATOM | 4672 | O | CYS A | 652 | −9.328 | 20.100 | −14.955 | 1.00 | 54.85 | O |
| ATOM | 4673 | N | SER A | 653 | −10.612 | 19.367 | −16.666 | 1.00 | 58.85 | N |
| ATOM | 4674 | CA | SER A | 653 | −11.737 | 20.279 | −16.469 | 1.00 | 60.94 | C |
| ATOM | 4675 | CB | SER A | 653 | −11.340 | 21.729 | −16.783 | 1.00 | 61.90 | C |
| ATOM | 4676 | OG | SER A | 653 | −10.811 | 21.846 | −18.092 | 1.00 | 63.69 | O |
| ATOM | 4677 | C | SER A | 653 | −12.880 | 19.816 | −17.375 | 1.00 | 63.64 | C |
| ATOM | 4678 | O | SER A | 653 | −12.907 | 18.660 | −17.803 | 1.00 | 63.83 | O |
| ATOM | 4679 | N | ASP A | 654 | −13.821 | 20.712 | −17.663 | 1.00 | 66.74 | N |
| ATOM | 4680 | CA | ASP A | 654 | −14.897 | 20.425 | −18.616 | 1.00 | 68.74 | C |

-continued

| Atomic coordinates for CRBN:DDB1:Lenalidomide (Human protein) | | | | | | | | | |
|---|---|---|---|---|---|---|---|---|---|
| ATOM | 4681 | CB | ASP A | 654 | −16.003 | 21.484 | −18.526 | 1.00 | 75.91 | C |
| ATOM | 4682 | CG | ASP A | 654 | −15.452 | 22.905 | −18.444 | 1.00 | 83.99 | C |
| ATOM | 4683 | OD1 | ASP A | 654 | −14.788 | 23.240 | −17.430 | 1.00 | 84.86 | O |
| ATOM | 4684 | OD2 | ASP A | 654 | −15.695 | 23.687 | −19.392 | 1.00 | 84.83 | O |
| ATOM | 4685 | C | ASP A | 654 | −14.346 | 20.341 | −20.038 | 1.00 | 67.13 | C |
| ATOM | 4686 | O | ASP A | 654 | −15.040 | 19.906 | −20.962 | 1.00 | 66.04 | O |
| ATOM | 4687 | N | ARG A | 655 | −13.096 | 20.777 | −20.194 | 1.00 | 63.77 | N |
| ATOM | 4688 | CA | ARG A | 655 | −12.339 | 20.611 | −21.429 | 1.00 | 58.42 | C |
| ATOM | 4689 | CB | ARG A | 655 | −12.306 | 21.921 | −22.229 | 1.00 | 56.45 | C |
| ATOM | 4690 | C | ARG A | 655 | −10.926 | 20.124 | −21.082 | 1.00 | 52.64 | C |
| ATOM | 4691 | O | ARG A | 655 | −10.068 | 20.921 | −20.701 | 1.00 | 54.43 | O |
| ATOM | 4692 | N | PRO A | 656 | −10.694 | 18.802 | −21.178 | 1.00 | 48.11 | N |
| ATOM | 4693 | CA | PRO A | 656 | −9.391 | 18.220 | −20.848 | 1.00 | 46.19 | C |
| ATOM | 4694 | CB | PRO A | 656 | −9.666 | 16.714 | −20.858 | 1.00 | 45.52 | C |
| ATOM | 4695 | CG | PRO A | 656 | −10.836 | 16.544 | −21.764 | 1.00 | 46.54 | C |
| ATOM | 4696 | CD | PRO A | 656 | −11.669 | 17.780 | −21.603 | 1.00 | 47.27 | C |
| ATOM | 4697 | C | PRO A | 656 | −8.329 | 18.581 | −21.883 | 1.00 | 45.12 | C |
| ATOM | 4698 | O | PRO A | 656 | −8.584 | 18.495 | −23.080 | 1.00 | 47.73 | O |
| ATOM | 4699 | N | THR A | 657 | −7.147 | 18.968 | −21.420 | 1.00 | 42.60 | N |
| ATOM | 4700 | CA | THR A | 657 | −6.123 | 19.542 | −22.285 | 1.00 | 43.04 | C |
| ATOM | 4701 | CB | THR A | 657 | −6.037 | 21.061 | −22.058 | 1.00 | 42.92 | C |
| ATOM | 4702 | OG1 | THR A | 657 | −7.354 | 21.596 | −21.905 | 1.00 | 43.45 | O |
| ATOM | 4703 | CG2 | THR A | 657 | −5.354 | 21.754 | −23.208 | 1.00 | 43.14 | C |
| ATOM | 4704 | C | THR A | 657 | −4.753 | 18.939 | −21.991 | 1.00 | 44.49 | C |
| ATOM | 4705 | O | THR A | 657 | −4.414 | 18.691 | −20.835 | 1.00 | 45.58 | O |
| ATOM | 4706 | N | VAL A | 658 | −3.968 | 18.696 | −23.036 | 1.00 | 46.22 | N |
| ATOM | 4707 | CA | VAL A | 658 | −2.560 | 18.314 | −22.872 | 1.00 | 46.46 | C |
| ATOM | 4708 | CB | VAL A | 658 | −2.167 | 17.142 | −23.800 | 1.00 | 45.20 | C |
| ATOM | 4709 | CG1 | VAL A | 658 | −0.678 | 16.846 | −23.714 | 1.00 | 44.11 | C |
| ATOM | 4710 | CG2 | VAL A | 658 | −2.968 | 15.892 | −23.464 | 1.00 | 44.44 | C |
| ATOM | 4711 | C | VAL A | 658 | −1.701 | 19.535 | −23.177 | 1.00 | 48.08 | C |
| ATOM | 4712 | O | VAL A | 658 | −2.038 | 20.321 | −24.057 | 1.00 | 51.92 | O |
| ATOM | 4713 | N | ILE A | 659 | −0.607 | 19.707 | −22.441 | 1.00 | 49.43 | N |
| ATOM | 4714 | CA | ILE A | 659 | 0.304 | 20.833 | −22.672 | 1.00 | 53.38 | C |
| ATOM | 4715 | CB | ILE A | 659 | 0.376 | 21.776 | −21.440 | 1.00 | 50.33 | C |
| ATOM | 4716 | CG1 | ILE A | 659 | −1.010 | 21.934 | −20.789 | 1.00 | 47.99 | C |
| ATOM | 4717 | CD1 | ILE A | 659 | −1.042 | 22.788 | −19.536 | 1.00 | 46.40 | C |
| ATOM | 4718 | CG2 | ILE A | 659 | 0.942 | 23.130 | −21.840 | 1.00 | 49.05 | C |
| ATOM | 4719 | C | ILE A | 659 | 1.699 | 20.309 | −23.033 | 1.00 | 59.15 | C |
| ATOM | 4720 | O | ILE A | 659 | 2.199 | 19.392 | −22.377 | 1.00 | 62.41 | O |
| ATOM | 4721 | N | TYR A | 660 | 2.314 | 20.865 | −24.082 | 1.00 | 64.32 | N |
| ATOM | 4722 | CA | TYR A | 660 | 3.678 | 20.454 | −24.475 | 1.00 | 70.36 | C |
| ATOM | 4723 | CB | TYR A | 660 | 3.661 | 19.156 | −25.312 | 1.00 | 72.28 | C |
| ATOM | 4724 | CG | TYR A | 660 | 2.716 | 19.117 | −26.517 | 1.00 | 75.56 | C |
| ATOM | 4725 | CD1 | TYR A | 660 | 2.662 | 20.167 | −27.445 | 1.00 | 75.17 | C |
| ATOM | 4726 | CE1 | TYR A | 660 | 1.816 | 20.111 | −28.545 | 1.00 | 76.72 | C |
| ATOM | 4727 | CZ | TYR A | 660 | 1.021 | 18.983 | −28.741 | 1.00 | 79.21 | C |
| ATOM | 4728 | OH | TYR A | 660 | 0.169 | 18.905 | −29.826 | 1.00 | 77.30 | O |
| ATOM | 4729 | CE2 | TYR A | 660 | 1.073 | 17.926 | −27.848 | 1.00 | 78.10 | C |
| ATOM | 4730 | CD2 | TYR A | 660 | 1.919 | 17.995 | −26.752 | 1.00 | 76.67 | C |
| ATOM | 4731 | C | TYR A | 660 | 4.525 | 21.538 | −25.170 | 1.00 | 75.26 | C |
| ATOM | 4732 | O | TYR A | 660 | 4.423 | 22.725 | −24.845 | 1.00 | 74.87 | O |
| ATOM | 4733 | N | SER A | 661 | 5.387 | 21.088 | −26.091 | 1.00 | 80.59 | N |
| ATOM | 4734 | CA | SER A | 661 | 6.148 | 21.935 | −27.033 | 1.00 | 84.17 | C |
| ATOM | 4735 | CB | SER A | 661 | 5.444 | 23.267 | −27.322 | 1.00 | 84.69 | C |
| ATOM | 4736 | OG | SER A | 661 | 6.090 | 23.982 | −28.362 | 1.00 | 83.02 | O |
| ATOM | 4737 | C | SER A | 661 | 7.612 | 22.147 | −26.650 | 1.00 | 86.37 | C |
| ATOM | 4738 | O | SER A | 661 | 7.919 | 22.743 | −25.610 | 1.00 | 83.83 | O |
| ATOM | 4739 | N | SER A | 662 | 8.503 | 21.658 | −27.517 | 1.00 | 91.23 | N |
| ATOM | 4740 | CA | SER A | 662 | 9.955 | 21.763 | −27.324 | 1.00 | 93.53 | C |
| ATOM | 4741 | CB | SER A | 662 | 10.656 | 20.458 | −27.731 | 1.00 | 90.57 | C |
| ATOM | 4742 | C | SER A | 662 | 10.569 | 22.939 | −28.088 | 1.00 | 94.09 | C |
| ATOM | 4743 | O | SER A | 662 | 11.634 | 23.436 | −27.704 | 1.00 | 94.76 | O |
| ATOM | 4744 | N | ASN A | 663 | 9.898 | 23.375 | −29.162 | 1.00 | 92.49 | N |
| ATOM | 4745 | CA | ASN A | 663 | 10.353 | 24.512 | −29.990 | 1.00 | 89.11 | C |
| ATOM | 4746 | CB | ASN A | 663 | 9.309 | 24.877 | −31.066 | 1.00 | 85.95 | C |
| ATOM | 4747 | CG | ASN A | 663 | 7.883 | 24.900 | −30.525 | 1.00 | 84.18 | C |
| ATOM | 4748 | OD1 | ASN A | 663 | 7.063 | 24.037 | −30.858 | 1.00 | 80.29 | O |
| ATOM | 4749 | ND2 | ASN A | 663 | 7.580 | 25.891 | −29.688 | 1.00 | 82.91 | N |
| ATOM | 4750 | C | ASN A | 663 | 10.745 | 25.746 | −29.171 | 1.00 | 88.17 | C |
| ATOM | 4751 | O | ASN A | 663 | 11.545 | 26.579 | −29.637 | 1.00 | 86.49 | O |
| ATOM | 4752 | N | HIS A | 664 | 10.137 | 25.851 | −27.972 | 1.00 | 87.54 | N |
| ATOM | 4753 | CA | HIS A | 664 | 10.550 | 26.766 | −26.873 | 1.00 | 85.25 | C |
| ATOM | 4754 | CB | HIS A | 664 | 11.851 | 27.535 | −27.167 | 1.00 | 84.45 | C |
| ATOM | 4755 | CG | HIS A | 664 | 13.109 | 26.688 | −27.041 | 1.00 | 82.87 | C |
| ATOM | 4756 | ND1 | HIS A | 664 | 14.106 | 26.727 | −27.952 | 1.00 | 81.32 | N |
| ATOM | 4757 | CE1 | HIS A | 664 | 15.081 | 25.872 | −27.588 | 1.00 | 78.56 | C |

-continued

| | | Atomic coordinates for CRBN:DDB1:Lenalidomide (Human protein) | | | | | | | |
|---|---|---|---|---|---|---|---|---|---|
| ATOM | 4758 | NE2 | HIS A | 664 | 14.707 | 25.278 | −26.441 | 1.00 | 79.35 | N |
| ATOM | 4759 | CD2 | HIS A | 664 | 13.496 | 25.755 | −26.074 | 1.00 | 81.56 | C |
| ATOM | 4760 | C | HIS A | 664 | 9.431 | 27.687 | −26.434 | 1.00 | 83.20 | C |
| ATOM | 4761 | O | HIS A | 664 | 9.661 | 28.698 | −25.764 | 1.00 | 81.99 | O |
| ATOM | 4762 | N | LYS A | 665 | 8.206 | 27.327 | −26.810 | 1.00 | 82.52 | N |
| ATOM | 4763 | CA | LYS A | 665 | 6.994 | 27.981 | −26.316 | 1.00 | 80.96 | C |
| ATOM | 4764 | CB | LYS A | 665 | 6.383 | 28.872 | −27.403 | 1.00 | 76.52 | C |
| ATOM | 4765 | C | LYS A | 665 | 5.984 | 26.916 | −25.853 | 1.00 | 81.86 | C |
| ATOM | 4766 | O | LYS A | 665 | 5.993 | 25.791 | −26.357 | 1.00 | 83.02 | O |
| ATOM | 4767 | N | LEU A | 666 | 5.135 | 27.266 | −24.884 | 1.00 | 78.82 | N |
| ATOM | 4768 | CA | LEU A | 666 | 4.082 | 26.361 | −24.400 | 1.00 | 73.06 | C |
| ATOM | 4769 | CB | LEU A | 666 | 3.722 | 26.665 | −22.937 | 1.00 | 68.19 | C |
| ATOM | 4770 | C | LEU A | 666 | 2.840 | 26.425 | −25.309 | 1.00 | 70.23 | C |
| ATOM | 4771 | O | LEU A | 666 | 2.540 | 27.472 | −25.896 | 1.00 | 67.04 | O |
| ATOM | 4772 | N | VAL A | 667 | 2.131 | 25.299 | −25.420 | 1.00 | 68.43 | N |
| ATOM | 4773 | CA | VAL A | 667 | 1.070 | 25.127 | −26.423 | 1.00 | 67.65 | C |
| ATOM | 4774 | CB | VAL A | 667 | 1.573 | 24.260 | −27.616 | 1.00 | 66.94 | C |
| ATOM | 4775 | CG1 | VAL A | 667 | 0.420 | 23.699 | −28.437 | 1.00 | 64.65 | C |
| ATOM | 4776 | CG2 | VAL A | 667 | 2.511 | 25.063 | −28.507 | 1.00 | 67.24 | C |
| ATOM | 4777 | C | VAL A | 667 | −0.216 | 24.529 | −25.838 | 1.00 | 66.29 | C |
| ATOM | 4778 | O | VAL A | 667 | −0.176 | 23.570 | −25.066 | 1.00 | 68.25 | O |
| ATOM | 4779 | N | PHE A | 668 | −1.352 | 25.111 | −26.211 | 1.00 | 64.63 | N |
| ATOM | 4780 | CA | PHE A | 668 | −2.657 | 24.512 | −25.931 | 1.00 | 63.59 | C |
| ATOM | 4781 | CB | PHE A | 668 | −3.781 | 25.573 | −25.981 | 1.00 | 67.92 | C |
| ATOM | 4782 | CG | PHE A | 668 | −3.884 | 26.330 | −27.301 | 1.00 | 66.96 | C |
| ATOM | 4783 | CD1 | PHE A | 668 | −4.729 | 25.879 | −28.323 | 1.00 | 64.80 | C |
| ATOM | 4784 | CE1 | PHE A | 668 | −4.834 | 26.574 | −29.523 | 1.00 | 62.89 | C |
| ATOM | 4785 | CZ | PHE A | 668 | −4.111 | 27.742 | −29.709 | 1.00 | 63.30 | C |
| ATOM | 4786 | CE2 | PHE A | 668 | −3.280 | 28.215 | −28.698 | 1.00 | 64.40 | C |
| ATOM | 4787 | CD2 | PHE A | 668 | −3.173 | 27.518 | −27.502 | 1.00 | 63.95 | C |
| ATOM | 4788 | C | PHE A | 668 | −2.955 | 23.353 | −26.893 | 1.00 | 60.16 | C |
| ATOM | 4789 | O | PHE A | 668 | −2.564 | 23.396 | −28.065 | 1.00 | 60.90 | O |
| ATOM | 4790 | N | SER A | 669 | −3.644 | 22.326 | −26.392 | 1.00 | 52.83 | N |
| ATOM | 4791 | CA | SER A | 669 | −4.082 | 21.191 | −27.213 | 1.00 | 48.07 | C |
| ATOM | 4792 | CB | SER A | 669 | −2.911 | 20.253 | −27.525 | 1.00 | 47.04 | C |
| ATOM | 4793 | C | SER A | 669 | −5.219 | 20.415 | −26.548 | 1.00 | 45.71 | C |
| ATOM | 4794 | O | SER A | 669 | −5.004 | 19.699 | −25.564 | 1.00 | 45.09 | O |
| ATOM | 4795 | N | ASN A | 670 | −6.427 | 20.564 | −27.091 | 1.00 | 42.81 | N |
| ATOM | 4796 | CA | ASN A | 670 | −7.610 | 19.858 | −26.579 | 1.00 | 40.81 | C |
| ATOM | 4797 | CB | ASN A | 670 | −8.916 | 20.434 | −27.168 | 1.00 | 38.99 | C |
| ATOM | 4798 | CG | ASN A | 670 | −8.749 | 20.988 | −28.580 | 1.00 | 39.42 | C |
| ATOM | 4799 | OD1 | ASN A | 670 | −9.418 | 21.949 | −28.962 | 1.00 | 39.03 | O |
| ATOM | 4800 | ND2 | ASN A | 670 | −7.871 | 20.378 | −29.363 | 1.00 | 40.63 | N |
| ATOM | 4801 | C | ASN A | 670 | −7.554 | 18.320 | −26.715 | 1.00 | 40.39 | C |
| ATOM | 4802 | O | ASN A | 670 | −6.900 | 17.786 | −27.620 | 1.00 | 40.49 | O |
| ATOM | 4803 | N | VAL A | 671 | −8.213 | 17.628 | −25.782 | 1.00 | 38.99 | N |
| ATOM | 4804 | CA | VAL A | 671 | −8.315 | 16.165 | −25.784 | 1.00 | 38.43 | C |
| ATOM | 4805 | CB | VAL A | 671 | −7.986 | 15.557 | −24.392 | 1.00 | 38.78 | C |
| ATOM | 4806 | CG1 | VAL A | 671 | −8.155 | 14.041 | −24.387 | 1.00 | 38.12 | C |
| ATOM | 4807 | CG2 | VAL A | 671 | −6.573 | 15.908 | −23.968 | 1.00 | 40.18 | C |
| ATOM | 4808 | C | VAL A | 671 | −9.734 | 15.758 | −26.191 | 1.00 | 38.66 | C |
| ATOM | 4809 | O | VAL A | 671 | −10.718 | 16.264 | −25.645 | 1.00 | 40.20 | O |
| ATOM | 4810 | N | ASN A | 672 | −9.826 | 14.843 | −27.149 | 1.00 | 36.66 | N |
| ATOM | 4811 | CA | ASN A | 672 | −11.095 | 14.301 | −27.617 | 1.00 | 36.47 | C |
| ATOM | 4812 | CB | ASN A | 672 | −10.843 | 13.582 | −28.967 | 1.00 | 37.91 | C |
| ATOM | 4813 | CG | ASN A | 672 | −11.877 | 12.516 | −29.298 | 1.00 | 39.85 | C |
| ATOM | 4814 | OD1 | ASN A | 672 | −12.802 | 12.756 | −30.081 | 1.00 | 39.61 | O |
| ATOM | 4815 | ND2 | ASN A | 672 | −11.701 | 11.314 | −28.730 | 1.00 | 39.91 | N |
| ATOM | 4816 | C | ASN A | 672 | −11.844 | 13.445 | −26.542 | 1.00 | 35.47 | C |
| ATOM | 4817 | O | ASN A | 672 | −11.981 | 12.219 | −26.668 | 1.00 | 33.39 | O |
| ATOM | 4818 | N | LEU A | 673 | −12.320 | 14.121 | −25.488 | 1.00 | 35.73 | N |
| ATOM | 4819 | CA | LEU A | 673 | −13.094 | 13.492 | −24.382 | 1.00 | 38.09 | C |
| ATOM | 4820 | CB | LEU A | 673 | −12.167 | 12.840 | −23.341 | 1.00 | 36.67 | C |
| ATOM | 4821 | CG | LEU A | 673 | −11.728 | 11.400 | −23.570 | 1.00 | 34.61 | C |
| ATOM | 4822 | CD1 | LEU A | 673 | −10.896 | 10.924 | −22.400 | 1.00 | 34.85 | C |
| ATOM | 4823 | CD2 | LEU A | 673 | −12.932 | 10.505 | −23.775 | 1.00 | 33.76 | C |
| ATOM | 4824 | C | LEU A | 673 | −14.021 | 14.475 | −23.663 | 1.00 | 38.77 | C |
| ATOM | 4825 | O | LEU A | 673 | −13.702 | 15.659 | −23.542 | 1.00 | 38.71 | O |
| ATOM | 4826 | N | LYS A | 674 | −15.143 | 13.964 | −23.154 | 1.00 | 41.33 | N |
| ATOM | 4827 | CA | LYS A | 674 | −16.209 | 14.812 | −22.591 | 1.00 | 44.82 | C |
| ATOM | 4828 | CB | LYS A | 674 | −17.496 | 14.011 | −22.323 | 1.00 | 42.74 | C |
| ATOM | 4829 | C | LYS A | 674 | −15.752 | 15.569 | −21.341 | 1.00 | 47.34 | C |
| ATOM | 4830 | O | LYS A | 674 | −15.469 | 16.765 | −21.409 | 1.00 | 52.89 | O |
| ATOM | 4831 | N | GLU A | 675 | −15.675 | 14.884 | −20.207 | 1.00 | 46.33 | N |
| ATOM | 4832 | CA | GLU A | 675 | −15.235 | 15.528 | −18.978 | 1.00 | 45.98 | C |
| ATOM | 4833 | CB | GLU A | 675 | −16.429 | 16.110 | −18.190 | 1.00 | 48.08 | C |
| ATOM | 4834 | CG | GLU A | 675 | −16.141 | 16.416 | −16.718 | 1.00 | 50.71 | C |

-continued

| | | Atomic coordinates for CRBN:DDB1:Lenalidomide (Human protein) | | | | | | | |
|---|---|---|---|---|---|---|---|---|---|
| ATOM | 4835 | CD | GLU A | 675 | −16.934 | 17.598 | −16.174 | 1.00 | 52.57 | C |
| ATOM | 4836 | OE1 | GLU A | 675 | −17.859 | 17.388 | −15.356 | 1.00 | 53.34 | O |
| ATOM | 4837 | OE2 | GLU A | 675 | −16.627 | 18.745 | −16.558 | 1.00 | 54.17 | O |
| ATOM | 4838 | C | GLU A | 675 | −14.435 | 14.551 | −18.138 | 1.00 | 45.20 | C |
| ATOM | 4839 | O | GLU A | 675 | −14.929 | 13.494 | −17.747 | 1.00 | 48.88 | O |
| ATOM | 4840 | N | VAL A | 676 | −13.185 | 14.897 | −17.888 | 1.00 | 40.85 | N |
| ATOM | 4841 | CA | VAL A | 676 | −12.350 | 14.110 | −17.019 | 1.00 | 38.56 | C |
| ATOM | 4842 | CB | VAL A | 676 | −11.007 | 13.774 | −17.691 | 1.00 | 36.84 | C |
| ATOM | 4843 | CG1 | VAL A | 676 | −10.357 | 12.577 | −17.020 | 1.00 | 35.48 | C |
| ATOM | 4844 | CG2 | VAL A | 676 | −11.207 | 13.499 | −19.171 | 1.00 | 36.61 | C |
| ATOM | 4845 | C | VAL A | 676 | −12.110 | 14.965 | −15.795 | 1.00 | 39.62 | C |
| ATOM | 4846 | O | VAL A | 676 | −11.660 | 16.109 | −15.918 | 1.00 | 39.77 | O |
| ATOM | 4847 | N | ASN A | 677 | −12.433 | 14.426 | −14.619 | 1.00 | 40.65 | N |
| ATOM | 4848 | CA | ASN A | 677 | −12.183 | 15.130 | −13.351 | 1.00 | 40.85 | C |
| ATOM | 4849 | CB | ASN A | 677 | −13.202 | 14.731 | −12.282 | 1.00 | 41.27 | C |
| ATOM | 4850 | CG | ASN A | 677 | −14.621 | 14.680 | −12.819 | 1.00 | 44.66 | C |
| ATOM | 4851 | OD1 | ASN A | 677 | −14.944 | 15.324 | −13.822 | 1.00 | 46.76 | O |
| ATOM | 4852 | ND2 | ASN A | 677 | −15.480 | 13.908 | −12.155 | 1.00 | 43.83 | N |
| ATOM | 4853 | C | ASN A | 677 | −10.768 | 14.900 | −12.836 | 1.00 | 40.42 | C |
| ATOM | 4854 | O | ASN A | 677 | −10.171 | 15.802 | −12.246 | 1.00 | 40.82 | O |
| ATOM | 4855 | N | TYR A | 678 | −10.243 | 13.693 | −13.066 | 1.00 | 39.24 | N |
| ATOM | 4856 | CA | TYR A | 678 | −8.924 | 13.291 | −12.572 | 1.00 | 39.34 | C |
| ATOM | 4857 | CB | TYR A | 678 | −9.056 | 12.579 | −11.227 | 1.00 | 39.52 | C |
| ATOM | 4858 | CG | TYR A | 678 | −9.601 | 13.451 | −10.136 | 1.00 | 40.60 | C |
| ATOM | 4859 | CD1 | TYR A | 678 | −8.762 | 14.303 | −9.415 | 1.00 | 41.02 | C |
| ATOM | 4860 | CE1 | TYR A | 678 | −9.258 | 15.116 | −8.410 | 1.00 | 41.91 | C |
| ATOM | 4861 | CZ | TYR A | 678 | −10.617 | 15.088 | −8.116 | 1.00 | 42.99 | C |
| ATOM | 4862 | OH | TYR A | 678 | −11.118 | 15.894 | −7.114 | 1.00 | 42.80 | O |
| ATOM | 4863 | CE2 | TYR A | 678 | −11.474 | 14.254 | −8.827 | 1.00 | 43.33 | C |
| ATOM | 4864 | CD2 | TYR A | 678 | −10.961 | 13.439 | −9.827 | 1.00 | 41.46 | C |
| ATOM | 4865 | C | TYR A | 678 | −8.208 | 12.359 | −13.530 | 1.00 | 39.03 | C |
| ATOM | 4866 | O | TYR A | 678 | −8.836 | 11.507 | −14.159 | 1.00 | 40.39 | O |
| ATOM | 4867 | N | MET A | 679 | −6.889 | 12.504 | −13.624 | 1.00 | 38.15 | N |
| ATOM | 4868 | CA | MET A | 679 | −6.078 | 11.530 | −14.349 | 1.00 | 37.06 | C |
| ATOM | 4869 | CB | MET A | 679 | −5.849 | 11.967 | −15.797 | 1.00 | 37.34 | C |
| ATOM | 4870 | CG | MET A | 679 | −4.726 | 12.970 | −15.995 | 1.00 | 39.48 | C |
| ATOM | 4871 | SD | MET A | 679 | −3.075 | 12.260 | −16.223 | 1.00 | 44.39 | S |
| ATOM | 4872 | CE | MET A | 679 | −3.411 | 10.956 | −17.392 | 1.00 | 41.47 | C |
| ATOM | 4873 | C | MET A | 679 | −4.754 | 11.228 | −13.657 | 1.00 | 36.61 | C |
| ATOM | 4874 | O | MET A | 679 | −4.320 | 11.962 | −12.765 | 1.00 | 36.77 | O |
| ATOM | 4875 | N | CYS A | 680 | −4.134 | 10.129 | −14.081 | 1.00 | 36.02 | N |
| ATOM | 4876 | CA | CYS A | 680 | −2.794 | 9.734 | −13.655 | 1.00 | 34.56 | C |
| ATOM | 4877 | CB | CYS A | 680 | −2.854 | 9.012 | −12.313 | 1.00 | 36.18 | C |
| ATOM | 4878 | SG | CYS A | 680 | −3.274 | 7.267 | −12.445 | 1.00 | 37.17 | S |
| ATOM | 4879 | C | CYS A | 680 | −2.196 | 8.808 | −14.708 | 1.00 | 32.58 | C |
| ATOM | 4880 | O | CYS A | 680 | −2.936 | 8.186 | −15.482 | 1.00 | 32.68 | O |
| ATOM | 4881 | N | PRO A | 681 | −0.860 | 8.724 | −14.764 | 1.00 | 30.87 | N |
| ATOM | 4882 | CA | PRO A | 681 | −0.211 | 7.785 | −15.685 | 1.00 | 30.89 | C |
| ATOM | 4883 | CB | PRO A | 681 | 1.225 | 8.282 | −15.748 | 1.00 | 29.96 | C |
| ATOM | 4884 | CG | PRO A | 681 | 1.416 | 9.070 | −14.505 | 1.00 | 30.43 | C |
| ATOM | 4885 | CD | PRO A | 681 | 0.093 | 9.659 | −14.151 | 1.00 | 30.58 | C |
| ATOM | 4886 | C | PRO A | 681 | −0.256 | 6.357 | −15.161 | 1.00 | 31.71 | C |
| ATOM | 4887 | O | PRO A | 681 | −0.321 | 6.147 | −13.949 | 1.00 | 32.99 | O |
| ATOM | 4888 | N | LEU A | 682 | −0.250 | 5.385 | −16.068 | 1.00 | 31.61 | N |
| ATOM | 4889 | CA | LEU A | 682 | −0.307 | 3.978 | −15.677 | 1.00 | 32.18 | C |
| ATOM | 4890 | CB | LEU A | 682 | −1.750 | 3.474 | −15.584 | 1.00 | 32.10 | C |
| ATOM | 4891 | CG | LEU A | 682 | −1.936 | 2.005 | −15.188 | 1.00 | 32.39 | C |
| ATOM | 4892 | CD1 | LEU A | 682 | −1.361 | 1.723 | −13.804 | 1.00 | 33.60 | C |
| ATOM | 4893 | CD2 | LEU A | 682 | −3.401 | 1.606 | −15.241 | 1.00 | 32.38 | C |
| ATOM | 4894 | C | LEU A | 682 | 0.472 | 3.128 | −16.645 | 1.00 | 33.07 | C |
| ATOM | 4895 | O | LEU A | 682 | 0.166 | 3.083 | −17.835 | 1.00 | 34.33 | O |
| ATOM | 4896 | N | ASN A | 683 | 1.488 | 2.457 | −16.119 | 1.00 | 33.59 | N |
| ATOM | 4897 | CA | ASN A | 683 | 2.361 | 1.623 | −16.913 | 1.00 | 33.83 | C |
| ATOM | 4898 | CB | ASN A | 683 | 3.765 | 2.233 | −16.958 | 1.00 | 34.36 | C |
| ATOM | 4899 | CG | ASN A | 683 | 4.760 | 1.384 | −17.735 | 1.00 | 35.28 | C |
| ATOM | 4900 | OD1 | ASN A | 683 | 4.406 | 0.682 | −18.696 | 1.00 | 35.68 | O |
| ATOM | 4901 | ND2 | ASN A | 683 | 6.022 | 1.457 | −17.328 | 1.00 | 34.06 | N |
| ATOM | 4902 | C | ASN A | 683 | 2.374 | 0.231 | −16.314 | 1.00 | 33.22 | C |
| ATOM | 4903 | O | ASN A | 683 | 2.927 | 0.014 | −15.247 | 1.00 | 32.70 | O |
| ATOM | 4904 | N | SER A | 684 | 1.748 | −0.706 | −17.012 | 1.00 | 34.52 | N |
| ATOM | 4905 | CA | SER A | 684 | 1.508 | −2.032 | −16.468 | 1.00 | 35.84 | C |
| ATOM | 4906 | CB | SER A | 684 | 0.041 | −2.168 | −16.089 | 1.00 | 35.28 | C |
| ATOM | 4907 | CG | SER A | 684 | −0.430 | −0.947 | −15.562 | 1.00 | 36.05 | O |
| ATOM | 4908 | C | SER A | 684 | 1.880 | −3.151 | −17.426 | 1.00 | 37.13 | C |
| ATOM | 4909 | O | SER A | 684 | 2.014 | −2.946 | −18.638 | 1.00 | 35.79 | O |
| ATOM | 4910 | N | ASP A | 685 | 2.036 | −4.341 | −16.853 | 1.00 | 40.41 | N |
| ATOM | 4911 | CA | ASP A | 685 | 2.179 | −5.586 | −17.610 | 1.00 | 41.45 | C |

| | | Atomic coordinates for CRBN:DDB1:Lenalidomide (Human protein) | | | | | | | |
|---|---|---|---|---|---|---|---|---|---|
| ATOM | 4912 | CB | ASP A | 685 | 2.348 | −6.778 | −16.655 | 1.00 | 43.80 | C |
| ATOM | 4913 | CG | ASP A | 685 | 1.358 | −6.747 | −15.489 | 1.00 | 48.23 | C |
| ATOM | 4914 | OD1 | ASP A | 685 | 1.363 | −5.763 | −14.702 | 1.00 | 48.65 | O |
| ATOM | 4915 | OD2 | ASP A | 685 | 0.575 | −7.715 | −15.360 | 1.00 | 51.26 | O |
| ATOM | 4916 | C | ASP A | 685 | 0.978 | −5.801 | −18.530 | 1.00 | 39.37 | C |
| ATOM | 4917 | O | ASP A | 685 | 1.042 | −6.576 | −19.477 | 1.00 | 39.72 | O |
| ATOM | 4918 | N | GLY A | 686 | −0.111 | −5.096 | −18.251 | 1.00 | 38.14 | N |
| ATOM | 4919 | CA | GLY A | 686 | −1.288 | −5.148 | −19.103 | 1.00 | 37.01 | C |
| ATOM | 4920 | C | GLY A | 686 | −1.537 | −3.877 | −19.890 | 1.00 | 35.11 | C |
| ATOM | 4921 | O | GLY A | 686 | −2.053 | −3.923 | −21.005 | 1.00 | 34.76 | O |
| ATOM | 4922 | N | TYR A | 687 | −1.177 | −2.739 | −19.304 | 1.00 | 33.93 | N |
| ATOM | 4923 | CA | TYR A | 687 | −1.489 | −1.453 | −19.899 | 1.00 | 32.40 | C |
| ATOM | 4924 | CB | TYR A | 687 | −2.609 | −0.787 | −19.116 | 1.00 | 32.37 | C |
| ATOM | 4925 | CG | TYR A | 687 | −3.858 | −1.630 | −19.002 | 1.00 | 33.25 | C |
| ATOM | 4926 | CD1 | TYR A | 687 | −4.593 | −1.989 | −20.135 | 1.00 | 33.26 | C |
| ATOM | 4927 | CE1 | TYR A | 687 | −5.744 | −2.757 | −20.030 | 1.00 | 34.00 | C |
| ATOM | 4928 | CZ | TYR A | 687 | −6.179 | −3.168 | −18.775 | 1.00 | 34.63 | C |
| ATOM | 4929 | OH | TYR A | 687 | −7.321 | −3.921 | −18.650 | 1.00 | 36.40 | O |
| ATOM | 4930 | CE2 | TYR A | 687 | −5.472 | −2.824 | −17.641 | 1.00 | 34.31 | C |
| ATOM | 4931 | CD2 | TYR A | 687 | −4.316 | −2.060 | −17.757 | 1.00 | 34.42 | C |
| ATOM | 4932 | C | TYR A | 687 | −0.272 | −0.547 | −19.961 | 1.00 | 31.31 | C |
| ATOM | 4933 | O | TYR A | 687 | −0.157 | 0.380 | −19.170 | 1.00 | 31.11 | O |
| ATOM | 4934 | N | PRO A | 688 | 0.633 | −0.804 | −20.923 | 1.00 | 31.06 | N |
| ATOM | 4935 | CA | PRO A | 688 | 1.935 | −0.145 | −20.963 | 1.00 | 31.51 | C |
| ATOM | 4936 | CB | PRO A | 688 | 2.752 | −1.018 | −21.930 | 1.00 | 30.81 | C |
| ATOM | 4937 | CG | PRO A | 688 | 1.823 | −2.068 | −22.444 | 1.00 | 30.72 | C |
| ATOM | 4938 | CD | PRO A | 688 | 0.428 | −1.653 | −22.102 | 1.00 | 30.68 | C |
| ATOM | 4939 | C | PRO A | 688 | 1.829 | 1.264 | −21.500 | 1.00 | 31.45 | C |
| ATOM | 4940 | O | PRO A | 688 | 1.146 | 1.484 | −22.495 | 1.00 | 29.70 | O |
| ATOM | 4941 | N | ASP A | 689 | 2.501 | 2.203 | −20.833 | 1.00 | 33.61 | N |
| ATOM | 4942 | CA | ASP A | 689 | 2.479 | 3.631 | −21.209 | 1.00 | 36.33 | C |
| ATOM | 4943 | CB | ASP A | 689 | 3.293 | 3.880 | −22.498 | 1.00 | 36.44 | C |
| ATOM | 4944 | CG | ASP A | 689 | 4.697 | 3.279 | −22.439 | 1.00 | 37.59 | C |
| ATOM | 4945 | OD2 | ASP A | 689 | 4.866 | 2.109 | −22.841 | 1.00 | 38.23 | O |
| ATOM | 4946 | OD1 | ASP A | 689 | 5.634 | 3.972 | −21.992 | 1.00 | 38.63 | O |
| ATOM | 4947 | C | ASP A | 689 | 1.037 | 4.164 | −21.359 | 1.00 | 36.59 | C |
| ATOM | 4948 | O | ASP A | 689 | 0.749 | 5.026 | −22.216 | 1.00 | 36.92 | O |
| ATOM | 4949 | N | SER A | 690 | 0.139 | 3.643 | −20.526 | 1.00 | 34.12 | N |
| ATOM | 4950 | CA | SER A | 690 | −1.267 | 3.975 | −20.630 | 1.00 | 34.11 | C |
| ATOM | 4951 | CB | SER A | 690 | −2.125 | 2.731 | −20.426 | 1.00 | 34.83 | C |
| ATOM | 4952 | OG | SER A | 690 | −1.908 | 1.796 | −21.463 | 1.00 | 37.22 | O |
| ATOM | 4953 | C | SER A | 690 | −1.673 | 5.051 | −19.644 | 1.00 | 34.54 | C |
| ATOM | 4954 | O | SER A | 690 | −0.827 | 5.674 | −18.991 | 1.00 | 36.34 | O |
| ATOM | 4955 | N | LEU A | 691 | −2.984 | 5.234 | −19.524 | 1.00 | 33.71 | N |
| ATOM | 4956 | CA | LEU A | 691 | −3.576 | 6.317 | −18.770 | 1.00 | 32.55 | C |
| ATOM | 4957 | CB | LEU A | 691 | −4.174 | 7.301 | −19.757 | 1.00 | 32.54 | C |
| ATOM | 4958 | CG | LEU A | 691 | −3.673 | 8.721 | −19.660 | 1.00 | 33.63 | C |
| ATOM | 4959 | CD1 | LEU A | 691 | −2.151 | 8.717 | −19.586 | 1.00 | 35.64 | C |
| ATOM | 4960 | CD2 | LEU A | 691 | −4.170 | 9.522 | −20.851 | 1.00 | 33.02 | C |
| ATOM | 4961 | C | LEU A | 691 | −4.701 | 5.764 | −17.913 | 1.00 | 33.00 | C |
| ATOM | 4962 | O | LEU A | 691 | −5.316 | 4.754 | −18.267 | 1.00 | 34.02 | O |
| ATOM | 4963 | N | ALA A | 692 | −4.987 | 6.430 | −16.800 | 1.00 | 31.36 | N |
| ATOM | 4964 | CA | ALA A | 692 | −6.208 | 6.160 | −16.054 | 1.00 | 29.83 | C |
| ATOM | 4965 | CB | ALA A | 692 | −5.877 | 5.634 | −14.676 | 1.00 | 30.19 | C |
| ATOM | 4966 | C | ALA A | 692 | −7.020 | 7.436 | −15.956 | 1.00 | 29.73 | C |
| ATOM | 4967 | O | ALA A | 692 | −6.570 | 8.406 | −15.373 | 1.00 | 30.45 | O |
| ATOM | 4968 | N | LEU A | 693 | −8.208 | 7.439 | −16.548 | 1.00 | 30.65 | N |
| ATOM | 4969 | CA | LEU A | 693 | −9.083 | 8.616 | −16.543 | 1.00 | 31.90 | C |
| ATOM | 4970 | CB | LEU A | 693 | −9.588 | 8.925 | −17.959 | 1.00 | 33.46 | C |
| ATOM | 4971 | CG | LEU A | 693 | −8.662 | 9.360 | −19.103 | 1.00 | 34.64 | C |
| ATOM | 4972 | CD1 | LEU A | 693 | −7.834 | 10.594 | −18.755 | 1.00 | 34.88 | C |
| ATOM | 4973 | CD2 | LEU A | 693 | −7.769 | 8.213 | −19.558 | 1.00 | 36.11 | C |
| ATOM | 4974 | C | LEU A | 693 | −10.292 | 8.383 | −15.650 | 1.00 | 32.05 | C |
| ATOM | 4975 | O | LEU A | 693 | −10.978 | 7.366 | −15.778 | 1.00 | 32.24 | O |
| ATOM | 4976 | N | ALA A | 694 | −10.567 | 9.324 | −14.754 | 1.00 | 31.83 | N |
| ATOM | 4977 | CA | ALA A | 694 | −11.754 | 9.222 | −13.901 | 1.00 | 31.80 | C |
| ATOM | 4978 | CB | ALA A | 694 | −11.370 | 9.008 | −12.444 | 1.00 | 31.84 | C |
| ATOM | 4979 | C | ALA A | 694 | −12.646 | 10.435 | −14.033 | 1.00 | 31.43 | C |
| ATOM | 4980 | O | ALA A | 694 | −12.192 | 11.578 | −13.917 | 1.00 | 30.62 | O |
| ATOM | 4981 | N | ASN A | 695 | −13.917 | 10.182 | −14.297 | 1.00 | 31.42 | N |
| ATOM | 4982 | CA | ASN A | 695 | −14.906 | 11.218 | −14.165 | 1.00 | 32.81 | C |
| ATOM | 4983 | CB | ASN A | 695 | −15.655 | 11.452 | −15.485 | 1.00 | 31.83 | C |
| ATOM | 4984 | CG | ASN A | 695 | −16.587 | 10.313 | −15.865 | 1.00 | 31.90 | C |
| ATOM | 4985 | OD1 | ASN A | 695 | −16.950 | 9.452 | −15.048 | 1.00 | 32.18 | O |
| ATOM | 4986 | ND2 | ASN A | 695 | −17.007 | 10.323 | −17.118 | 1.00 | 31.46 | N |
| ATOM | 4987 | C | ASN A | 695 | −15.840 | 10.940 | −12.990 | 1.00 | 34.94 | C |
| ATOM | 4988 | O | ASN A | 695 | −15.455 | 10.268 | −12.020 | 1.00 | 35.07 | O |

-continued

| Atomic coordinates for CRBN:DDB1:Lenalidomide (Human protein) | | | | | | | | | |
|---|---|---|---|---|---|---|---|---|---|
| ATOM | 4989 | N | ASN A | 696 | −17.065 | 11.447 | −13.087 | 1.00 | 37.17 | N |
| ATOM | 4990 | CA | ASN A | 696 | −18.014 | 11.378 | −11.993 | 1.00 | 38.25 | C |
| ATOM | 4991 | CB | ASN A | 696 | −19.134 | 12.396 | −12.180 | 1.00 | 40.39 | C |
| ATOM | 4992 | CG | ASN A | 696 | −18.853 | 13.685 | −11.447 | 1.00 | 42.20 | C |
| ATOM | 4993 | OD1 | ASN A | 696 | −18.609 | 14.727 | −12.058 | 1.00 | 43.14 | O |
| ATOM | 4994 | ND2 | ASN A | 696 | −18.838 | 13.610 | −10.120 | 1.00 | 44.02 | N |
| ATOM | 4995 | C | ASN A | 696 | −18.566 | 10.005 | −11.704 | 1.00 | 37.80 | C |
| ATOM | 4996 | O | ASN A | 696 | −18.850 | 9.692 | −10.547 | 1.00 | 38.84 | O |
| ATOM | 4997 | N | SER A | 697 | −18.703 | 9.175 | −12.735 | 1.00 | 36.76 | N |
| ATOM | 4998 | CA | SER A | 697 | −19.219 | 7.824 | −12.506 | 1.00 | 36.76 | C |
| ATOM | 4999 | CB | SER A | 697 | −20.702 | 7.705 | −12.911 | 1.00 | 36.57 | C |
| ATOM | 5000 | OG | SER A | 697 | −20.889 | 7.854 | −14.305 | 1.00 | 36.73 | O |
| ATOM | 5001 | C | SER A | 697 | −18.372 | 6.665 | −13.061 | 1.00 | 36.12 | C |
| ATOM | 5002 | O | SER A | 697 | −18.704 | 5.498 | −12.820 | 1.00 | 36.34 | O |
| ATOM | 5003 | N | THR A | 698 | −17.267 | 6.974 | −13.751 | 1.00 | 33.66 | N |
| ATOM | 5004 | CA | THR A | 698 | −16.439 | 5.923 | −14.356 | 1.00 | 32.53 | C |
| ATOM | 5005 | CB | THR A | 698 | −16.803 | 5.747 | −15.836 | 1.00 | 32.48 | C |
| ATOM | 5006 | OG1 | THR A | 698 | −18.225 | 5.771 | −15.977 | 1.00 | 33.25 | O |
| ATOM | 5007 | CG2 | THR A | 698 | −16.278 | 4.430 | −16.368 | 1.00 | 32.34 | C |
| ATOM | 5008 | C | THR A | 698 | −14.923 | 6.136 | −14.253 | 1.00 | 32.41 | C |
| ATOM | 5009 | O | THR A | 698 | −14.438 | 7.256 | −14.392 | 1.00 | 34.00 | O |
| ATOM | 5010 | N | LEU A | 699 | −14.178 | 5.056 | −14.010 | 1.00 | 31.82 | N |
| ATOM | 5011 | CA | LEU A | 699 | −12.719 | 5.062 | −14.230 | 1.00 | 30.87 | C |
| ATOM | 5012 | CB | LEU A | 699 | −11.949 | 4.350 | −13.100 | 1.00 | 31.18 | C |
| ATOM | 5013 | C | LEU A | 699 | −12.452 | 4.380 | −15.555 | 1.00 | 29.03 | C |
| ATOM | 5014 | O | LEU A | 699 | −13.046 | 3.341 | −15.846 | 1.00 | 28.63 | O |
| ATOM | 5015 | N | THR A | 700 | −11.585 | 4.986 | −16.367 | 1.00 | 28.29 | N |
| ATOM | 5016 | CA | THR A | 700 | −11.205 | 4.435 | −17.679 | 1.00 | 27.38 | C |
| ATOM | 5017 | CB | THR A | 700 | −11.656 | 5.327 | −18.877 | 1.00 | 27.04 | C |
| ATOM | 5018 | OG1 | THR A | 700 | −12.926 | 5.932 | −18.614 | 1.00 | 27.05 | O |
| ATOM | 5019 | CG2 | THR A | 700 | −11.784 | 4.503 | −20.140 | 1.00 | 27.30 | C |
| ATOM | 5020 | C | THR A | 700 | −9.689 | 4.278 | −17.735 | 1.00 | 26.68 | C |
| ATOM | 5021 | O | THR A | 700 | −8.954 | 5.171 | −17.292 | 1.00 | 25.83 | O |
| ATOM | 5022 | N | ILE A | 701 | −9.229 | 3.138 | −18.259 | 1.00 | 25.67 | N |
| ATOM | 5023 | CA | ILE A | 701 | −7.809 | 2.929 | −18.533 | 1.00 | 25.26 | C |
| ATOM | 5024 | CB | ILE A | 701 | −7.296 | 1.623 | −17.905 | 1.00 | 25.47 | C |
| ATOM | 5025 | CG1 | ILE A | 701 | −7.429 | 1.700 | −16.376 | 1.00 | 26.75 | C |
| ATOM | 5026 | CD1 | ILE A | 701 | −6.982 | 0.464 | −15.609 | 1.00 | 27.48 | C |
| ATOM | 5027 | CG2 | ILE A | 701 | −5.854 | 1.364 | −18.316 | 1.00 | 24.87 | C |
| ATOM | 5028 | C | ILE A | 701 | −7.572 | 2.929 | −20.030 | 1.00 | 24.71 | C |
| ATOM | 5029 | O | ILE A | 701 | −8.194 | 2.160 | −20.750 | 1.00 | 24.32 | O |
| ATOM | 5030 | N | GLY A | 702 | −6.687 | 3.803 | −20.505 | 1.00 | 25.58 | N |
| ATOM | 5031 | CA | GLY A | 702 | −6.463 | 3.934 | −21.955 | 1.00 | 28.01 | C |
| ATOM | 5032 | C | GLY A | 702 | −5.050 | 4.280 | −22.390 | 1.00 | 29.39 | C |
| ATOM | 5033 | O | GLY A | 702 | −4.298 | 4.877 | −21.627 | 1.00 | 30.37 | O |
| ATOM | 5034 | N | THR A | 703 | −4.678 | 3.870 | −23.608 | 1.00 | 30.52 | N |
| ATOM | 5035 | CA | THR A | 703 | −3.474 | 4.400 | −24.278 | 1.00 | 31.06 | C |
| ATOM | 5036 | CB | THR A | 703 | −2.864 | 3.405 | −25.283 | 1.00 | 28.99 | C |
| ATOM | 5037 | C | THR A | 703 | −3.831 | 5.719 | −24.974 | 1.00 | 31.54 | C |
| ATOM | 5038 | O | THR A | 703 | −4.997 | 6.052 | −25.121 | 1.00 | 31.64 | O |
| ATOM | 5039 | N | ILE A | 704 | −2.835 | 6.482 | −25.384 | 1.00 | 33.23 | N |
| ATOM | 5040 | CA | ILE A | 704 | −3.100 | 7.833 | −25.860 | 1.00 | 35.09 | C |
| ATOM | 5041 | CB | ILE A | 704 | −2.762 | 8.863 | −24.761 | 1.00 | 34.91 | C |
| ATOM | 5042 | CG1 | ILE A | 704 | −2.698 | 10.286 | −25.323 | 1.00 | 34.69 | C |
| ATOM | 5043 | CD1 | ILE A | 704 | −2.731 | 11.368 | −24.258 | 1.00 | 33.31 | C |
| ATOM | 5044 | CG2 | ILE A | 704 | −1.477 | 8.464 | −24.032 | 1.00 | 36.26 | C |
| ATOM | 5045 | C | ILE A | 704 | −2.339 | 8.106 | −27.153 | 1.00 | 37.31 | C |
| ATOM | 5046 | O | ILE A | 704 | −1.122 | 7.950 | −27.192 | 1.00 | 38.69 | O |
| ATOM | 5047 | N | ASP A | 705 | −3.070 | 8.467 | −28.212 | 1.00 | 38.52 | N |
| ATOM | 5048 | CA | ASP A | 705 | −2.487 | 8.874 | −29.489 | 1.00 | 40.13 | C |
| ATOM | 5049 | CB | ASP A | 705 | −3.534 | 9.619 | −30.314 | 1.00 | 42.73 | C |
| ATOM | 5050 | CG | ASP A | 705 | −4.311 | 8.712 | −31.253 | 1.00 | 45.89 | C |
| ATOM | 5051 | OD1 | ASP A | 705 | −3.707 | 8.157 | −32.205 | 1.00 | 48.35 | O |
| ATOM | 5052 | OD2 | ASP A | 705 | −5.542 | 8.595 | −31.067 | 1.00 | 46.21 | O |
| ATOM | 5053 | C | ASP A | 705 | −1.299 | 9.812 | −29.268 | 1.00 | 42.29 | C |
| ATOM | 5054 | O | ASP A | 705 | −1.363 | 10.716 | −28.423 | 1.00 | 42.76 | O |
| ATOM | 5055 | N | GLU A | 706 | −0.219 | 9.605 | −30.020 | 1.00 | 43.67 | N |
| ATOM | 5056 | CA | GLU A | 706 | 0.963 | 10.475 | −29.908 | 1.00 | 45.79 | C |
| ATOM | 5057 | CB | GLU A | 706 | 2.194 | 9.828 | −30.563 | 1.00 | 46.67 | C |
| ATOM | 5058 | C | GLU A | 706 | 0.702 | 11.882 | −30.485 | 1.00 | 45.70 | C |
| ATOM | 5059 | O | GLU A | 706 | 0.869 | 12.884 | −29.785 | 1.00 | 45.52 | O |
| ATOM | 5060 | N | ILE A | 707 | 0.269 | 11.931 | −31.748 | 1.00 | 45.11 | N |
| ATOM | 5061 | CA | ILE A | 707 | −0.050 | 13.183 | −32.462 | 1.00 | 44.00 | C |
| ATOM | 5062 | CB | ILE A | 707 | 0.398 | 13.110 | −33.947 | 1.00 | 42.49 | C |
| ATOM | 5063 | CG1 | ILE A | 707 | 0.152 | 11.696 | −34.505 | 1.00 | 40.72 | C |
| ATOM | 5064 | CD1 | ILE A | 707 | 0.803 | 11.405 | −35.835 | 1.00 | 39.67 | C |
| ATOM | 5065 | CG2 | ILE A | 707 | 1.845 | 13.562 | −34.091 | 1.00 | 42.82 | C |

-continued

| \multicolumn{10}{c|}{Atomic coordinates for CRBN:DDB1:Lenalidomide (Human protein)} |

| ATOM | 5066 | C | ILE A | 707 | −1.545 | 13.527 | −32.451 | 1.00 | 43.94 | C |
|------|------|------|-------|-----|--------|--------|---------|------|-------|---|
| ATOM | 5067 | O | ILE A | 707 | −2.397 | 12.642 | −32.327 | 1.00 | 43.61 | O |
| ATOM | 5068 | N | GLN A | 708 | −1.853 | 14.816 | −32.608 | 1.00 | 43.70 | N |
| ATOM | 5069 | CA | GLN A | 708 | −3.221 | 15.261 | −32.879 | 1.00 | 42.42 | C |
| ATOM | 5070 | CB | GLN A | 708 | −3.311 | 16.794 | −32.910 | 1.00 | 43.71 | C |
| ATOM | 5071 | CG | GLN A | 708 | −3.151 | 17.461 | −31.547 | 1.00 | 47.33 | C |
| ATOM | 5072 | CD | GLN A | 708 | −3.709 | 18.881 | −31.497 | 1.00 | 48.95 | C |
| ATOM | 5073 | OE1 | GLN A | 708 | −3.256 | 19.763 | −32.223 | 1.00 | 48.82 | O |
| ATOM | 5074 | NE2 | GLN A | 708 | −4.683 | 19.109 | −30.612 | 1.00 | 50.04 | N |
| ATOM | 5075 | C | GLN A | 708 | −3.720 | 14.666 | −34.201 | 1.00 | 41.42 | C |
| ATOM | 5076 | O | GLN A | 708 | −2.948 | 14.076 | −34.960 | 1.00 | 42.27 | O |
| ATOM | 5077 | N | LYS A | 709 | −5.013 | 14.821 | −34.466 | 1.00 | 39.19 | N |
| ATOM | 5078 | CA | LYS A | 709 | −5.658 | 14.222 | −35.631 | 1.00 | 34.64 | C |
| ATOM | 5079 | CB | LYS A | 709 | −5.709 | 12.693 | −35.476 | 1.00 | 36.61 | C |
| ATOM | 5080 | CG | LYS A | 709 | −5.948 | 11.927 | −36.764 | 1.00 | 38.57 | C |
| ATOM | 5081 | CD | LYS A | 709 | −6.075 | 10.429 | −36.526 | 1.00 | 39.66 | C |
| ATOM | 5082 | CE | LYS A | 709 | −6.115 | 9.666 | −37.849 | 1.00 | 41.22 | C |
| ATOM | 5083 | NZ | LYS A | 709 | −4.928 | 9.953 | −38.717 | 1.00 | 39.87 | N |
| ATOM | 5084 | C | LYS A | 709 | −7.066 | 14.789 | −35.705 | 1.00 | 31.13 | C |
| ATOM | 5085 | O | LYS A | 709 | −7.488 | 15.516 | −34.795 | 1.00 | 30.31 | O |
| ATOM | 5086 | N | LEU A | 710 | −7.782 | 14.473 | −36.786 | 1.00 | 27.12 | N |
| ATOM | 5087 | CA | LEU A | 710 | −9.173 | 14.894 | −36.956 | 1.00 | 23.55 | C |
| ATOM | 5088 | CB | LEU A | 710 | −9.454 | 15.292 | −38.400 | 1.00 | 22.74 | C |
| ATOM | 5089 | CG | LEU A | 710 | −9.112 | 16.695 | −38.876 | 1.00 | 22.36 | C |
| ATOM | 5090 | CD1 | LEU A | 710 | −9.868 | 16.956 | −40.173 | 1.00 | 22.06 | C |
| ATOM | 5091 | CD2 | LEU A | 710 | −9.488 | 17.723 | −37.830 | 1.00 | 22.50 | C |
| ATOM | 5092 | C | LEU A | 710 | −10.140 | 13.807 | −36.557 | 1.00 | 21.29 | C |
| ATOM | 5093 | O | LEU A | 710 | −10.171 | 12.748 | −37.155 | 1.00 | 21.27 | O |
| ATOM | 5094 | N | HIS A | 711 | −10.957 | 14.079 | −35.563 | 1.00 | 19.47 | N |
| ATOM | 5095 | CA | HIS A | 711 | −11.869 | 13.074 | −35.096 | 1.00 | 18.74 | C |
| ATOM | 5096 | CB | HIS A | 711 | −11.843 | 13.028 | −33.570 | 1.00 | 19.32 | C |
| ATOM | 5097 | CG | HIS A | 711 | −10.519 | 12.552 | −33.026 | 1.00 | 20.32 | C |
| ATOM | 5098 | ND1 | HIS A | 711 | −9.444 | 13.353 | −32.944 | 1.00 | 20.66 | N |
| ATOM | 5099 | CE1 | HIS A | 711 | −8.389 | 12.645 | −32.485 | 1.00 | 20.72 | C |
| ATOM | 5100 | NE2 | HIS A | 711 | −8.791 | 11.381 | −32.288 | 1.00 | 20.87 | N |
| ATOM | 5101 | CD2 | HIS A | 711 | −10.094 | 11.282 | −32.623 | 1.00 | 20.80 | C |
| ATOM | 5102 | C | HIS A | 711 | −13.225 | 13.300 | −35.668 | 1.00 | 17.84 | C |
| ATOM | 5103 | O | HIS A | 711 | −13.898 | 14.260 | −35.323 | 1.00 | 17.77 | O |
| ATOM | 5104 | N | ILE A | 712 | −13.629 | 12.433 | −36.590 | 1.00 | 17.23 | N |
| ATOM | 5105 | CA | ILE A | 712 | −14.937 | 12.577 | −37.237 | 1.00 | 16.75 | C |
| ATOM | 5106 | CB | ILE A | 712 | −14.844 | 12.452 | −38.776 | 1.00 | 16.67 | C |
| ATOM | 5107 | CG1 | ILE A | 712 | −13.748 | 13.355 | −39.328 | 1.00 | 16.81 | C |
| ATOM | 5108 | CD1 | ILE A | 712 | −13.157 | 12.859 | −40.629 | 1.00 | 17.08 | C |
| ATOM | 5109 | CG2 | ILE A | 712 | −16.155 | 12.860 | −39.428 | 1.00 | 16.87 | C |
| ATOM | 5110 | C | ILE A | 712 | −15.947 | 11.572 | −36.684 | 1.00 | 16.21 | C |
| ATOM | 5111 | O | ILE A | 712 | −15.713 | 10.373 | −36.736 | 1.00 | 16.64 | O |
| ATOM | 5112 | N | ARG A | 713 | −17.053 | 12.076 | −36.141 | 1.00 | 15.67 | N |
| ATOM | 5113 | CA | ARG A | 713 | −18.161 | 11.249 | −35.648 | 1.00 | 15.37 | C |
| ATOM | 5114 | CB | ARG A | 713 | −18.775 | 11.900 | −34.403 | 1.00 | 15.64 | C |
| ATOM | 5115 | CG | ARG A | 713 | −19.453 | 10.962 | −33.431 | 1.00 | 15.90 | C |
| ATOM | 5116 | CD | ARG A | 713 | −20.947 | 10.895 | −33.664 | 1.00 | 16.99 | C |
| ATOM | 5117 | NE | ARG A | 713 | −21.584 | 9.754 | −32.976 | 1.00 | 18.10 | N |
| ATOM | 5118 | CZ | ARG A | 713 | −21.983 | 9.759 | −31.700 | 1.00 | 18.29 | C |
| ATOM | 5119 | NH1 | ARG A | 713 | −21.814 | 10.843 | −30.941 | 1.00 | 18.69 | N |
| ATOM | 5120 | NH2 | ARG A | 713 | −22.546 | 8.680 | −31.177 | 1.00 | 17.89 | N |
| ATOM | 5121 | C | ARG A | 713 | −19.200 | 11.210 | −36.752 | 1.00 | 15.05 | C |
| ATOM | 5122 | O | ARG A | 713 | −19.515 | 12.249 | −37.327 | 1.00 | 15.50 | O |
| ATOM | 5123 | N | THR A | 714 | −19.736 | 10.038 | −37.066 | 1.00 | 14.09 | N |
| ATOM | 5124 | CA | THR A | 714 | −20.731 | 9.967 | −38.122 | 1.00 | 13.51 | C |
| ATOM | 5125 | CB | THR A | 714 | −20.303 | 9.000 | −39.215 | 1.00 | 13.64 | C |
| ATOM | 5126 | OG1 | THR A | 714 | −19.082 | 9.474 | −39.791 | 1.00 | 13.91 | O |
| ATOM | 5127 | CG2 | THR A | 714 | −21.376 | 8.883 | −40.303 | 1.00 | 13.57 | C |
| ATOM | 5128 | C | THR A | 714 | −22.114 | 9.618 | −37.616 | 1.00 | 13.32 | C |
| ATOM | 5129 | O | THR A | 714 | −22.302 | 8.609 | −36.952 | 1.00 | 13.47 | O |
| ATOM | 5130 | N | VAL A | 715 | −23.079 | 10.477 | −37.918 | 1.00 | 13.10 | N |
| ATOM | 5131 | CA | VAL A | 715 | −24.463 | 10.234 | −37.553 | 1.00 | 12.89 | C |
| ATOM | 5132 | CB | VAL A | 715 | −25.066 | 11.451 | −36.831 | 1.00 | 12.97 | C |
| ATOM | 5133 | CG1 | VAL A | 715 | −26.447 | 11.135 | −36.285 | 1.00 | 13.09 | C |
| ATOM | 5134 | CG2 | VAL A | 715 | −24.157 | 11.898 | −35.704 | 1.00 | 13.11 | C |
| ATOM | 5135 | C | VAL A | 715 | −25.271 | 9.894 | −38.814 | 1.00 | 12.94 | C |
| ATOM | 5136 | O | VAL A | 715 | −25.829 | 10.793 | −39.459 | 1.00 | 12.68 | O |
| ATOM | 5137 | N | PRO A | 716 | −25.315 | 8.587 | −39.187 | 1.00 | 12.88 | N |
| ATOM | 5138 | CA | PRO A | 716 | −26.088 | 8.174 | −40.354 | 1.00 | 12.39 | C |
| ATOM | 5139 | CB | PRO A | 716 | −26.058 | 6.648 | −40.259 | 1.00 | 12.33 | C |
| ATOM | 5140 | CG | PRO A | 716 | −24.805 | 6.341 | −39.520 | 1.00 | 12.38 | C |
| ATOM | 5141 | CD | PRO A | 716 | −24.691 | 7.430 | −38.509 | 1.00 | 12.59 | C |
| ATOM | 5142 | C | PRO A | 716 | −27.509 | 8.650 | −40.192 | 1.00 | 12.29 | C |

-continued

| | | | | Atomic coordinates for CRBN:DDB1:Lenalidomide (Human protein) | | | | | |
|---|---|---|---|---|---|---|---|---|---|
| ATOM | 5143 | O | PRO A | 716 | −28.075 | 8.489 | −39.098 | 1.00 | 12.26 | O |
| ATOM | 5144 | N | LEU A | 717 | −28.076 | 9.233 | −41.255 | 1.00 | 11.98 | N |
| ATOM | 5145 | CA | LEU A | 717 | −29.507 | 9.618 | −41.281 | 1.00 | 11.73 | C |
| ATOM | 5146 | CB | LEU A | 717 | −29.673 | 11.098 | −41.609 | 1.00 | 11.17 | C |
| ATOM | 5147 | CG | LEU A | 717 | −29.070 | 12.161 | −40.714 | 1.00 | 10.80 | C |
| ATOM | 5148 | CD1 | LEU A | 717 | −28.987 | 13.452 | −41.507 | 1.00 | 10.59 | C |
| ATOM | 5149 | CD2 | LEU A | 717 | −29.881 | 12.339 | −39.441 | 1.00 | 10.70 | C |
| ATOM | 5150 | C | LEU A | 717 | −30.372 | 8.811 | −42.258 | 1.00 | 11.91 | C |
| ATOM | 5151 | O | LEU A | 717 | −31.601 | 8.834 | −42.163 | 1.00 | 12.27 | O |
| ATOM | 5152 | N | TYR A | 718 | −29.735 | 8.134 | −43.211 | 1.00 | 12.13 | N |
| ATOM | 5153 | CA | TYR A | 718 | −30.436 | 7.347 | −44.251 | 1.00 | 12.39 | C |
| ATOM | 5154 | CB | TYR A | 718 | −31.108 | 6.112 | −43.642 | 1.00 | 11.98 | C |
| ATOM | 5155 | CG | TYR A | 718 | −30.153 | 5.326 | −42.786 | 1.00 | 11.70 | C |
| ATOM | 5156 | CD1 | TYR A | 718 | −29.004 | 4.766 | −43.336 | 1.00 | 11.90 | C |
| ATOM | 5157 | CE1 | TYR A | 718 | −28.101 | 4.063 | −42.559 | 1.00 | 11.71 | C |
| ATOM | 5158 | CZ | TYR A | 718 | −28.341 | 3.922 | −41.223 | 1.00 | 11.57 | C |
| ATOM | 5159 | OH | TYR A | 718 | −27.452 | 3.224 | −40.471 | 1.00 | 11.65 | O |
| ATOM | 5160 | CE2 | TYR A | 718 | −29.467 | 4.471 | −40.645 | 1.00 | 11.58 | C |
| ATOM | 5161 | CD2 | TYR A | 718 | −30.361 | 5.179 | −41.427 | 1.00 | 11.55 | C |
| ATOM | 5162 | C | TYR A | 718 | −31.411 | 8.168 | −45.103 | 1.00 | 12.88 | C |
| ATOM | 5163 | O | TYR A | 718 | −32.361 | 7.626 | −45.676 | 1.00 | 13.25 | O |
| ATOM | 5164 | N | GLU A | 719 | −31.158 | 9.480 | −45.166 | 1.00 | 13.19 | N |
| ATOM | 5165 | CA | GLU A | 719 | −31.836 | 10.407 | −46.081 | 1.00 | 13.39 | C |
| ATOM | 5166 | CB | GLU A | 719 | −33.200 | 10.843 | −45.547 | 1.00 | 14.01 | C |
| ATOM | 5167 | CG | GLU A | 719 | −33.322 | 10.773 | −44.044 | 1.00 | 15.49 | C |
| ATOM | 5168 | CD | GLU A | 719 | −34.540 | 11.503 | −43.514 | 1.00 | 16.67 | C |
| ATOM | 5169 | OE1 | GLU A | 719 | −34.461 | 12.738 | −43.380 | 1.00 | 17.60 | O |
| ATOM | 5170 | OE2 | GLU A | 719 | −35.562 | 10.844 | −43.202 | 1.00 | 17.18 | O |
| ATOM | 5171 | C | GLU A | 719 | −30.944 | 11.618 | −46.305 | 1.00 | 13.18 | C |
| ATOM | 5172 | O | GLU A | 719 | −29.973 | 11.818 | −45.580 | 1.00 | 12.93 | O |
| ATOM | 5173 | N | SER A | 720 | −31.276 | 12.420 | −47.313 | 1.00 | 13.03 | N |
| ATOM | 5174 | CA | SER A | 720 | −30.535 | 13.639 | −47.618 | 1.00 | 12.98 | C |
| ATOM | 5175 | CB | SER A | 720 | −30.942 | 14.148 | −48.994 | 1.00 | 12.94 | C |
| ATOM | 5176 | OG | SER A | 720 | −30.637 | 13.212 | −49.993 | 1.00 | 13.21 | O |
| ATOM | 5177 | C | SER A | 720 | −30.740 | 14.771 | −46.595 | 1.00 | 13.16 | C |
| ATOM | 5178 | O | SER A | 720 | −31.831 | 15.341 | −46.526 | 1.00 | 13.27 | O |
| ATOM | 5179 | N | PRO A | 721 | −29.690 | 15.117 | −45.812 | 1.00 | 13.35 | N |
| ATOM | 5180 | CA | PRO A | 721 | −29.703 | 16.367 | −45.030 | 1.00 | 13.50 | C |
| ATOM | 5181 | CB | PRO A | 721 | −28.528 | 16.192 | −44.076 | 1.00 | 13.38 | C |
| ATOM | 5182 | CG | PRO A | 721 | −27.582 | 15.327 | −44.841 | 1.00 | 13.63 | C |
| ATOM | 5183 | CD | PRO A | 721 | −28.458 | 14.347 | −45.574 | 1.00 | 13.39 | C |
| ATOM | 5184 | C | PRO A | 721 | −29.438 | 17.552 | −45.935 | 1.00 | 13.75 | C |
| ATOM | 5185 | O | PRO A | 721 | −28.632 | 17.455 | −46.854 | 1.00 | 13.80 | O |
| ATOM | 5186 | N | ARG A | 722 | −30.103 | 18.668 | −45.677 | 1.00 | 14.29 | N |
| ATOM | 5187 | CA | ARG A | 722 | −30.073 | 19.777 | −46.621 | 1.00 | 14.56 | C |
| ATOM | 5188 | CB | ARG A | 722 | −31.421 | 19.927 | −47.301 | 1.00 | 14.97 | C |
| ATOM | 5189 | CG | ARG A | 722 | −31.768 | 18.775 | −48.236 | 1.00 | 15.21 | C |
| ATOM | 5190 | CD | ARG A | 722 | −31.609 | 19.217 | −49.672 | 1.00 | 15.75 | C |
| ATOM | 5191 | NE | ARG A | 722 | −30.300 | 18.884 | −50.232 | 1.00 | 15.88 | N |
| ATOM | 5192 | CZ | ARG A | 722 | −29.635 | 19.642 | −51.109 | 1.00 | 15.99 | C |
| ATOM | 5193 | NH1 | ARG A | 722 | −28.472 | 19.228 | −51.587 | 1.00 | 15.81 | N |
| ATOM | 5194 | NH2 | ARG A | 722 | −30.120 | 20.817 | −51.505 | 1.00 | 16.01 | N |
| ATOM | 5195 | C | ARG A | 722 | −29.645 | 21.077 | −45.992 | 1.00 | 14.53 | C |
| ATOM | 5196 | O | ARG A | 722 | −28.922 | 21.848 | −46.618 | 1.00 | 15.17 | O |
| ATOM | 5197 | N | LYS A | 723 | −30.085 | 21.330 | −44.765 | 1.00 | 14.10 | N |
| ATOM | 5198 | CA | LYS A | 723 | −29.576 | 22.470 | −43.991 | 1.00 | 13.80 | C |
| ATOM | 5199 | CB | LYS A | 723 | −30.492 | 23.701 | −44.102 | 1.00 | 14.05 | C |
| ATOM | 5200 | CG | LYS A | 723 | −30.836 | 24.143 | −45.513 | 1.00 | 14.08 | C |
| ATOM | 5201 | CD | LYS A | 723 | −29.706 | 24.904 | −46.177 | 1.00 | 14.24 | C |
| ATOM | 5202 | CE | LYS A | 723 | −29.832 | 24.744 | −47.683 | 1.00 | 14.56 | C |
| ATOM | 5203 | NZ | LYS A | 723 | −29.195 | 25.861 | −48.428 | 1.00 | 14.90 | N |
| ATOM | 5204 | C | LYS A | 723 | −29.427 | 22.097 | −42.535 | 1.00 | 13.21 | C |
| ATOM | 5205 | O | LYS A | 723 | −30.096 | 21.193 | −42.047 | 1.00 | 12.64 | O |
| ATOM | 5206 | N | ILE A | 724 | −28.546 | 22.811 | −41.850 | 1.00 | 13.11 | N |
| ATOM | 5207 | CA | ILE A | 724 | −28.280 | 22.581 | −40.441 | 1.00 | 13.39 | C |
| ATOM | 5208 | CB | ILE A | 724 | −26.982 | 21.745 | −40.193 | 1.00 | 13.25 | C |
| ATOM | 5209 | CG1 | ILE A | 724 | −26.857 | 21.399 | −38.702 | 1.00 | 13.09 | C |
| ATOM | 5210 | CD1 | ILE A | 724 | −26.178 | 20.092 | −38.393 | 1.00 | 13.04 | C |
| ATOM | 5211 | CG2 | ILE A | 724 | −25.732 | 22.483 | −40.681 | 1.00 | 12.67 | C |
| ATOM | 5212 | C | ILE A | 724 | −28.107 | 23.933 | −39.829 | 1.00 | 13.51 | C |
| ATOM | 5213 | O | ILE A | 724 | −27.620 | 24.824 | −40.491 | 1.00 | 13.82 | O |
| ATOM | 5214 | N | CYS A | 725 | −28.516 | 24.089 | −38.579 | 0.50 | 13.89 | N |
| ATOM | 5215 | CA | CYS A | 725 | −28.166 | 25.262 | −37.812 | 0.50 | 14.54 | C |
| ATOM | 5216 | CB | CYS A | 725 | −29.159 | 26.391 | −38.048 | 0.50 | 14.32 | C |
| ATOM | 5217 | SG | CYS A | 725 | −30.786 | 26.044 | −37.371 | 0.50 | 14.65 | S |
| ATOM | 5218 | C | CYS A | 725 | −28.178 | 24.814 | −36.380 | 0.50 | 15.23 | C |
| ATOM | 5219 | O | CYS A | 725 | −28.763 | 23.788 | −36.061 | 0.50 | 15.14 | O |

-continued

| | | | | | | | | | |
|---|---|---|---|---|---|---|---|---|---|
| ATOM | 5220 | N | TYR A | 726 | −27.518 | 25.570 | −35.517 | 1.00 | 16.68 | N |
| ATOM | 5221 | CA | TYR A | 726 | −27.259 | 25.110 | −34.156 | 1.00 | 18.93 | C |
| ATOM | 5222 | CB | TYR A | 726 | −25.737 | 25.015 | −33.893 | 1.00 | 19.94 | C |
| ATOM | 5223 | CG | TYR A | 726 | −25.363 | 24.880 | −32.425 | 1.00 | 20.43 | C |
| ATOM | 5224 | CD1 | TYR A | 726 | −25.911 | 23.867 | −31.635 | 1.00 | 20.76 | C |
| ATOM | 5225 | CE1 | TYR A | 726 | −25.592 | 23.752 | −30.298 | 1.00 | 21.62 | C |
| ATOM | 5226 | CZ | TYR A | 726 | −24.703 | 24.649 | −29.729 | 1.00 | 22.23 | C |
| ATOM | 5227 | OH | TYR A | 726 | −24.381 | 24.527 | −28.393 | 1.00 | 23.06 | O |
| ATOM | 5228 | CE2 | TYR A | 726 | −24.137 | 25.654 | −30.494 | 1.00 | 21.58 | C |
| ATOM | 5229 | CD2 | TYR A | 726 | −24.470 | 25.764 | −31.832 | 1.00 | 20.62 | C |
| ATOM | 5230 | C | TYR A | 726 | −27.938 | 25.966 | −33.087 | 1.00 | 20.27 | C |
| ATOM | 5231 | O | TYR A | 726 | −27.612 | 27.141 | −32.922 | 1.00 | 22.38 | O |
| ATOM | 5232 | N | GLN A | 727 | −28.854 | 25.370 | −32.336 | 1.00 | 20.29 | N |
| ATOM | 5233 | CA | GLN A | 727 | −29.546 | 26.107 | −31.309 | 1.00 | 21.59 | C |
| ATOM | 5234 | CB | GLN A | 727 | −31.033 | 25.810 | −31.384 | 1.00 | 21.73 | C |
| ATOM | 5235 | CG | GLN A | 727 | −31.883 | 26.600 | −30.412 | 1.00 | 21.86 | C |
| ATOM | 5236 | CD | GLN A | 727 | −33.333 | 26.606 | −30.819 | 1.00 | 22.56 | C |
| ATOM | 5237 | OE1 | GLN A | 727 | −34.196 | 26.169 | −30.066 | 1.00 | 23.65 | O |
| ATOM | 5238 | NE2 | GLN A | 727 | −33.611 | 27.085 | −32.030 | 1.00 | 22.67 | N |
| ATOM | 5239 | C | GLN A | 727 | −28.987 | 25.784 | −29.921 | 1.00 | 22.92 | C |
| ATOM | 5240 | O | GLN A | 727 | −29.370 | 24.782 | −29.313 | 1.00 | 22.86 | O |
| ATOM | 5241 | N | GLU A | 728 | −28.100 | 26.655 | −29.425 | 1.00 | 24.59 | N |
| ATOM | 5242 | CA | GLU A | 728 | −27.363 | 26.428 | −28.164 | 1.00 | 25.62 | C |
| ATOM | 5243 | CB | GLU A | 728 | −26.223 | 27.460 | −27.991 | 1.00 | 28.61 | C |
| ATOM | 5244 | CG | GLU A | 728 | −25.398 | 27.313 | −26.702 | 1.00 | 31.97 | C |
| ATOM | 5245 | CD | GLU A | 728 | −24.412 | 28.461 | −26.458 | 1.00 | 34.77 | C |
| ATOM | 5246 | OE1 | GLU A | 728 | −23.221 | 28.176 | −26.200 | 1.00 | 36.35 | O |
| ATOM | 5247 | OE2 | GLU A | 728 | −24.819 | 29.649 | −26.504 | 1.00 | 36.57 | O |
| ATOM | 5248 | C | GLU A | 728 | −28.218 | 26.325 | −26.884 | 1.00 | 24.43 | C |
| ATOM | 5249 | O | GLU A | 728 | −27.884 | 25.545 | −26.001 | 1.00 | 24.11 | O |
| ATOM | 5250 | N | VAL A | 729 | −29.303 | 27.094 | −26.773 | 1.00 | 23.94 | N |
| ATOM | 5251 | CA | VAL A | 729 | −30.138 | 27.030 | −25.546 | 1.00 | 23.79 | C |
| ATOM | 5252 | CB | VAL A | 729 | −31.088 | 28.246 | −25.353 | 1.00 | 22.54 | C |
| ATOM | 5253 | CG1 | VAL A | 729 | −30.308 | 29.547 | −25.429 | 1.00 | 22.29 | C |
| ATOM | 5254 | CG2 | VAL A | 729 | −32.240 | 28.232 | −26.343 | 1.00 | 21.71 | C |
| ATOM | 5255 | C | VAL A | 729 | −30.916 | 25.718 | −25.445 | 1.00 | 23.93 | C |
| ATOM | 5256 | O | VAL A | 729 | −31.151 | 25.203 | −24.350 | 1.00 | 23.86 | O |
| ATOM | 5257 | N | SER A | 730 | −31.286 | 25.174 | −26.597 | 1.00 | 23.82 | N |
| ATOM | 5258 | CA | SER A | 730 | −31.977 | 23.903 | −26.658 | 1.00 | 23.48 | C |
| ATOM | 5259 | CB | SER A | 730 | −32.913 | 23.875 | −27.861 | 1.00 | 23.78 | C |
| ATOM | 5260 | OG | SER A | 730 | −33.808 | 24.966 | −27.835 | 1.00 | 24.47 | O |
| ATOM | 5261 | C | SER A | 730 | −30.963 | 22.792 | −26.782 | 1.00 | 23.19 | C |
| ATOM | 5262 | O | SER A | 730 | −31.327 | 21.622 | −26.878 | 1.00 | 23.92 | O |
| ATOM | 5263 | N | GLN A | 731 | −29.689 | 23.172 | −26.805 | 1.00 | 23.00 | N |
| ATOM | 5264 | CA | GLN A | 731 | −28.572 | 22.236 | −26.951 | 1.00 | 23.28 | C |
| ATOM | 5265 | CB | GLN A | 731 | −28.208 | 21.644 | −25.604 | 1.00 | 25.10 | C |
| ATOM | 5266 | CG | GLN A | 731 | −27.274 | 22.521 | −24.791 | 1.00 | 27.27 | C |
| ATOM | 5267 | CD | GLN A | 731 | −26.589 | 21.733 | −23.700 | 1.00 | 29.32 | C |
| ATOM | 5268 | OE1 | GLN A | 731 | −27.238 | 20.945 | −22.984 | 1.00 | 30.44 | O |
| ATOM | 5269 | NE2 | GLN A | 731 | −25.263 | 21.906 | −23.579 | 1.00 | 28.98 | N |
| ATOM | 5270 | C | GLN A | 731 | −28.817 | 21.129 | −27.970 | 1.00 | 22.34 | C |
| ATOM | 5271 | O | GLN A | 731 | −28.662 | 19.950 | −27.668 | 1.00 | 22.14 | O |
| ATOM | 5272 | N | CYS A | 732 | −29.186 | 21.530 | −29.183 | 1.00 | 21.71 | N |
| ATOM | 5273 | CA | CYS A | 732 | −29.569 | 20.606 | −30.236 | 1.00 | 20.83 | C |
| ATOM | 5274 | CB | CYS A | 732 | −30.998 | 20.148 | −30.009 | 1.00 | 22.67 | C |
| ATOM | 5275 | SG | CYS A | 732 | −32.163 | 21.487 | −30.318 | 1.00 | 26.86 | S |
| ATOM | 5276 | C | CYS A | 732 | −29.498 | 21.316 | −31.574 | 1.00 | 19.20 | C |
| ATOM | 5277 | O | CYS A | 732 | −29.538 | 22.538 | −31.626 | 1.00 | 19.48 | O |
| ATOM | 5278 | N | PHE A | 733 | −29.422 | 20.537 | −32.649 | 1.00 | 17.53 | N |
| ATOM | 5279 | CA | PHE A | 733 | −29.338 | 21.052 | −34.015 | 1.00 | 16.09 | C |
| ATOM | 5280 | CB | PHE A | 733 | −28.348 | 20.222 | −34.829 | 1.00 | 15.38 | C |
| ATOM | 5281 | CG | PHE A | 733 | −26.942 | 20.291 | −34.344 | 1.00 | 14.79 | C |
| ATOM | 5282 | CD1 | PHE A | 733 | −26.080 | 21.271 | −34.825 | 1.00 | 14.52 | C |
| ATOM | 5283 | CE1 | PHE A | 733 | −24.771 | 21.343 | −34.378 | 1.00 | 14.56 | C |
| ATOM | 5284 | CZ | PHE A | 733 | −24.304 | 20.410 | −33.464 | 1.00 | 14.64 | C |
| ATOM | 5285 | CE2 | PHE A | 733 | −25.154 | 19.416 | −32.988 | 1.00 | 14.63 | C |
| ATOM | 5286 | CD2 | PHE A | 733 | −26.466 | 19.360 | −33.428 | 1.00 | 14.59 | C |
| ATOM | 5287 | C | PHE A | 733 | −30.677 | 20.929 | −34.716 | 1.00 | 15.65 | C |
| ATOM | 5288 | O | PHE A | 733 | −31.422 | 19.975 | −34.487 | 1.00 | 15.98 | O |
| ATOM | 5289 | N | GLY A | 734 | −30.966 | 21.877 | −35.599 | 1.00 | 15.01 | N |
| ATOM | 5290 | CA | GLY A | 734 | −32.084 | 21.734 | −36.533 | 1.00 | 14.17 | C |
| ATOM | 5291 | C | GLY A | 734 | −31.542 | 21.368 | −37.895 | 1.00 | 13.34 | C |
| ATOM | 5292 | O | GLY A | 734 | −30.617 | 22.025 | −38.383 | 1.00 | 12.85 | O |
| ATOM | 5293 | N | VAL A | 735 | −32.098 | 20.315 | −38.496 | 1.00 | 13.03 | N |
| ATOM | 5294 | CA | VAL A | 735 | −31.652 | 19.844 | −39.815 | 1.00 | 13.20 | C |
| ATOM | 5295 | CB | VAL A | 735 | −30.863 | 18.512 | −39.738 | 1.00 | 13.27 | C |
| ATOM | 5296 | CG1 | VAL A | 735 | −30.629 | 17.935 | −41.129 | 1.00 | 13.13 | C |

Atomic coordinates for CRBN:DDB1:Lenalidomide (Human protein)

-continued

| | | Atomic coordinates for CRBN:DDB1:Lenalidomide (Human protein) | | | | | | | |
|---|---|---|---|---|---|---|---|---|---|
| ATOM | 5297 | CG2 | VAL A | 735 | −29.528 | 18.716 | −39.051 | 1.00 | 13.53 | C |
| ATOM | 5298 | C | VAL A | 735 | −32.807 | 19.667 | −40.781 | 1.00 | 13.28 | C |
| ATOM | 5299 | O | VAL A | 735 | −33.682 | 18.826 | −40.559 | 1.00 | 13.28 | O |
| ATOM | 5300 | N | LEU A | 736 | −32.813 | 20.456 | −41.853 | 1.00 | 13.56 | N |
| ATOM | 5301 | CA | LEU A | 736 | −33.764 | 20.227 | −42.941 | 1.00 | 13.99 | C |
| ATOM | 5302 | CB | LEU A | 736 | −33.836 | 21.414 | −43.889 | 1.00 | 13.62 | C |
| ATOM | 5303 | CG | LEU A | 736 | −34.366 | 22.718 | −43.314 | 1.00 | 13.78 | C |
| ATOM | 5304 | CD1 | LEU A | 736 | −34.606 | 23.702 | −44.459 | 1.00 | 13.47 | C |
| ATOM | 5305 | CD2 | LEU A | 736 | −35.633 | 22.484 | −42.486 | 1.00 | 13.58 | C |
| ATOM | 5306 | C | LEU A | 736 | −33.319 | 19.008 | −43.707 | 1.00 | 14.56 | C |
| ATOM | 5307 | O | LEU A | 736 | −32.151 | 18.899 | −44.092 | 1.00 | 14.79 | O |
| ATOM | 5308 | N | SER A | 737 | −34.238 | 18.080 | −43.922 | 1.00 | 15.21 | C |
| ATOM | 5309 | CA | SER A | 737 | −33.892 | 16.865 | −44.644 | 1.00 | 15.82 | C |
| ATOM | 5310 | CB | SER A | 737 | −33.429 | 15.774 | −43.677 | 1.00 | 15.69 | C |
| ATOM | 5311 | OG | SER A | 737 | −34.511 | 15.315 | −42.892 | 1.00 | 15.93 | O |
| ATOM | 5312 | C | SER A | 737 | −35.057 | 16.362 | −45.455 | 1.00 | 16.32 | C |
| ATOM | 5313 | O | SER A | 737 | −36.217 | 16.567 | −45.080 | 1.00 | 16.42 | O |
| ATOM | 5314 | N | SER A | 738 | −34.739 | 15.684 | −46.555 | 1.00 | 16.73 | N |
| ATOM | 5315 | CA | SER A | 738 | −35.757 | 15.102 | −47.415 | 1.00 | 17.27 | C |
| ATOM | 5316 | CB | SER A | 738 | −35.815 | 15.831 | −48.768 | 1.00 | 16.85 | C |
| ATOM | 5317 | OG | SER A | 738 | −34.932 | 15.254 | −49.707 | 1.00 | 17.00 | O |
| ATOM | 5318 | C | SER A | 738 | −35.527 | 13.601 | −47.587 | 1.00 | 17.82 | C |
| ATOM | 5319 | O | SER A | 738 | −34.412 | 13.122 | −47.401 | 1.00 | 17.81 | O |
| ATOM | 5320 | N | ARG A | 739 | −36.597 | 12.870 | −47.909 | 1.00 | 18.65 | N |
| ATOM | 5321 | CA | ARG A | 739 | −36.524 | 11.447 | −48.213 | 1.00 | 19.11 | C |
| ATOM | 5322 | CB | ARG A | 739 | −36.996 | 10.608 | −47.034 | 1.00 | 19.00 | C |
| ATOM | 5323 | CG | ARG A | 739 | −38.494 | 10.591 | −46.824 | 1.00 | 19.52 | C |
| ATOM | 5324 | CD | ARG A | 739 | −38.895 | 9.734 | −45.629 | 1.00 | 19.94 | C |
| ATOM | 5325 | NE | ARG A | 739 | −40.348 | 9.689 | −45.489 | 1.00 | 20.17 | N |
| ATOM | 5326 | CZ | ARG A | 739 | −41.043 | 10.484 | −44.684 | 1.00 | 20.34 | C |
| ATOM | 5327 | NH1 | ARG A | 739 | −40.424 | 11.371 | −43.922 | 1.00 | 20.68 | N |
| ATOM | 5328 | NH2 | ARG A | 739 | −42.358 | 10.387 | −44.632 | 1.00 | 20.43 | N |
| ATOM | 5329 | C | ARG A | 739 | −37.355 | 11.145 | −49.434 | 1.00 | 20.30 | C |
| ATOM | 5330 | O | ARG A | 739 | −38.263 | 11.898 | −49.771 | 1.00 | 20.80 | O |
| ATOM | 5331 | N | ILE A | 740 | −37.029 | 10.044 | −50.103 | 1.00 | 22.13 | N |
| ATOM | 5332 | CA | ILE A | 740 | −37.730 | 9.615 | −51.311 | 1.00 | 23.03 | C |
| ATOM | 5333 | CB | ILE A | 740 | −36.746 | 9.077 | −52.362 | 1.00 | 22.78 | C |
| ATOM | 5334 | CG1 | ILE A | 740 | −35.677 | 10.126 | −52.701 | 1.00 | 22.26 | C |
| ATOM | 5335 | CD1 | ILE A | 740 | −36.090 | 11.131 | −53.746 | 1.00 | 22.28 | C |
| ATOM | 5336 | CG2 | ILE A | 740 | −37.492 | 8.553 | −53.586 | 1.00 | 22.76 | C |
| ATOM | 5337 | C | ILE A | 740 | −38.708 | 8.497 | −50.992 | 1.00 | 24.70 | C |
| ATOM | 5338 | O | ILE A | 740 | −38.303 | 7.400 | −50.582 | 1.00 | 23.66 | O |
| ATOM | 5339 | N | GLU A | 741 | −39.994 | 8.785 | −51.185 | 1.00 | 27.67 | N |
| ATOM | 5340 | CA | GLU A | 741 | −41.034 | 7.753 | −51.165 | 1.00 | 29.16 | C |
| ATOM | 5341 | CB | GLU A | 741 | −42.160 | 8.124 | −50.203 | 1.00 | 29.84 | C |
| ATOM | 5342 | CG | GLU A | 741 | −41.665 | 8.357 | −48.785 | 1.00 | 32.49 | C |
| ATOM | 5343 | CD | GLU A | 741 | −42.772 | 8.392 | −47.742 | 1.00 | 35.05 | C |
| ATOM | 5344 | OE1 | GLU A | 741 | −43.949 | 8.634 | −48.104 | 1.00 | 37.17 | O |
| ATOM | 5345 | OE2 | GLU A | 741 | −42.459 | 8.181 | −46.545 | 1.00 | 35.10 | O |
| ATOM | 5346 | C | GLU A | 741 | −41.556 | 7.502 | −52.580 | 1.00 | 29.50 | C |
| ATOM | 5347 | O | GLU A | 741 | −41.397 | 8.330 | −53.469 | 1.00 | 27.34 | O |
| ATOM | 5348 | N | VAL A | 742 | −42.148 | 6.334 | −52.779 | 1.00 | 33.40 | N |
| ATOM | 5349 | CA | VAL A | 742 | −42.640 | 5.916 | −54.091 | 1.00 | 36.20 | C |
| ATOM | 5350 | CB | VAL A | 742 | −41.829 | 4.699 | −54.619 | 1.00 | 35.91 | C |
| ATOM | 5351 | CG1 | VAL A | 742 | −42.283 | 3.402 | −53.959 | 1.00 | 35.74 | C |
| ATOM | 5352 | CG2 | VAL A | 742 | −41.885 | 4.610 | −56.142 | 1.00 | 35.57 | C |
| ATOM | 5353 | C | VAL A | 742 | −44.147 | 5.628 | −53.984 | 1.00 | 38.17 | C |
| ATOM | 5354 | O | VAL A | 742 | −44.628 | 5.235 | −52.911 | 1.00 | 39.07 | O |
| ATOM | 5355 | N | GLN A | 743 | −44.880 | 5.843 | −55.085 | 1.00 | 39.88 | N |
| ATOM | 5356 | CA | GLN A | 743 | −46.365 | 5.842 | −55.083 | 1.00 | 40.98 | C |
| ATOM | 5357 | CB | GLN A | 743 | −46.921 | 6.345 | −56.423 | 1.00 | 39.53 | C |
| ATOM | 5358 | C | GLN A | 743 | −47.022 | 4.507 | −54.732 | 1.00 | 42.56 | C |
| ATOM | 5359 | O | GLN A | 743 | −46.596 | 3.443 | −55.217 | 1.00 | 40.91 | O |
| ATOM | 5360 | N | ASP A | 744 | −48.059 | 4.601 | −53.884 | 1.00 | 44.50 | N |
| ATOM | 5361 | CA | ASP A | 744 | −48.977 | 3.493 | −53.514 | 1.00 | 45.42 | C |
| ATOM | 5362 | CB | ASP A | 744 | −50.338 | 3.640 | −54.221 | 1.00 | 42.55 | C |
| ATOM | 5363 | C | ASP A | 744 | −48.417 | 2.087 | −53.729 | 1.00 | 46.16 | C |
| ATOM | 5364 | O | ASP A | 744 | −47.492 | 1.667 | −53.032 | 1.00 | 46.48 | O |
| ATOM | 5365 | N | THR A | 749 | −48.662 | 6.015 | −50.734 | 1.00 | 41.78 | N |
| ATOM | 5366 | CA | THR A | 749 | −47.269 | 6.491 | −50.692 | 1.00 | 43.23 | C |
| ATOM | 5367 | CB | THR A | 749 | −47.181 | 8.034 | −50.764 | 1.00 | 42.51 | C |
| ATOM | 5368 | OG1 | THR A | 749 | −45.810 | 8.426 | −50.902 | 1.00 | 41.58 | O |
| ATOM | 5369 | CG2 | THR A | 749 | −47.789 | 8.689 | −49.517 | 1.00 | 42.01 | C |
| ATOM | 5370 | C | THR A | 749 | −46.457 | 5.955 | −49.489 | 1.00 | 42.37 | C |
| ATOM | 5371 | O | THR A | 749 | −46.910 | 6.011 | −48.337 | 1.00 | 43.30 | O |
| ATOM | 5372 | N | THR A | 750 | −45.254 | 5.448 | −49.770 | 1.00 | 40.16 | N |
| ATOM | 5373 | CA | THR A | 750 | −44.487 | 4.666 | −48.787 | 1.00 | 37.81 | C |

-continued

| \multicolumn{10}{c}{Atomic coordinates for CRBN:DDB1:Lenalidomide (Human protein)} |

| ATOM | 5374 | CB | THR A | 750 | −44.881 | 3.179 | −48.834 | 1.00 | 37.56 | C |
|------|------|-----|-------|-----|---------|--------|---------|------|-------|---|
| ATOM | 5375 | OG1 | THR A | 750 | −44.938 | 2.755 | −50.200 | 1.00 | 37.23 | O |
| ATOM | 5376 | CG2 | THR A | 750 | −46.249 | 2.948 | −48.172 | 1.00 | 37.47 | C |
| ATOM | 5377 | C | THR A | 750 | −42.967 | 4.770 | −48.967 | 1.00 | 35.58 | C |
| ATOM | 5378 | O | THR A | 750 | −42.465 | 4.850 | −50.087 | 1.00 | 36.98 | O |
| ATOM | 5379 | N | ALA A | 751 | −42.249 | 4.741 | −47.849 | 1.00 | 32.07 | N |
| ATOM | 5380 | CA | ALA A | 751 | −40.798 | 4.889 | −47.825 | 1.00 | 29.83 | C |
| ATOM | 5381 | CB | ALA A | 751 | −40.355 | 5.197 | −46.408 | 1.00 | 30.36 | C |
| ATOM | 5382 | C | ALA A | 751 | −40.011 | 3.683 | −48.378 | 1.00 | 28.53 | C |
| ATOM | 5383 | O | ALA A | 751 | −40.531 | 2.568 | −48.460 | 1.00 | 28.72 | O |
| ATOM | 5384 | N | LEU A | 752 | −38.744 | 3.918 | −48.730 | 1.00 | 26.56 | N |
| ATOM | 5385 | CA | LEU A | 752 | −37.843 | 2.862 | −49.230 | 1.00 | 24.67 | C |
| ATOM | 5386 | CB | LEU A | 752 | −36.889 | 3.419 | −50.292 | 1.00 | 24.64 | C |
| ATOM | 5387 | CG | LEU A | 752 | −37.390 | 3.973 | −51.626 | 1.00 | 24.30 | C |
| ATOM | 5388 | CD1 | LEU A | 752 | −36.372 | 4.973 | −52.160 | 1.00 | 24.15 | C |
| ATOM | 5389 | CD2 | LEU A | 752 | −37.645 | 2.865 | −52.636 | 1.00 | 23.77 | C |
| ATOM | 5390 | C | LEU A | 752 | −37.012 | 2.187 | −48.126 | 1.00 | 23.57 | C |
| ATOM | 5391 | O | LEU A | 752 | −36.431 | 1.126 | −48.349 | 1.00 | 23.20 | O |
| ATOM | 5392 | N | ARG A | 753 | −36.937 | 2.817 | −46.954 | 1.00 | 22.42 | N |
| ATOM | 5393 | CA | ARG A | 753 | −36.257 | 2.247 | −45.793 | 1.00 | 21.16 | C |
| ATOM | 5394 | CB | ARG A | 753 | −34.762 | 2.062 | −46.085 | 1.00 | 22.55 | C |
| ATOM | 5395 | CG | ARG A | 753 | −33.865 | 3.256 | −45.743 | 1.00 | 23.23 | C |
| ATOM | 5396 | CD | ARG A | 753 | −32.699 | 3.397 | −46.708 | 1.00 | 23.42 | C |
| ATOM | 5397 | NE | ARG A | 753 | −33.139 | 4.030 | −47.954 | 1.00 | 24.35 | N |
| ATOM | 5398 | CZ | ARG A | 753 | −32.948 | 3.525 | −49.175 | 1.00 | 24.75 | C |
| ATOM | 5399 | NH1 | ARG A | 753 | −32.281 | 2.371 | −49.346 | 1.00 | 24.18 | N |
| ATOM | 5400 | NH2 | ARG A | 753 | −33.412 | 4.190 | −50.230 | 1.00 | 24.19 | N |
| ATOM | 5401 | C | ARG A | 753 | −36.457 | 3.159 | −44.585 | 1.00 | 20.22 | C |
| ATOM | 5402 | O | ARG A | 753 | −36.834 | 4.327 | −44.744 | 1.00 | 20.29 | O |
| ATOM | 5403 | N | PRO A | 754 | −36.216 | 2.636 | −43.367 | 1.00 | 19.27 | N |
| ATOM | 5404 | CA | PRO A | 754 | −36.228 | 3.487 | −42.171 | 1.00 | 18.60 | C |
| ATOM | 5405 | CB | PRO A | 754 | −35.830 | 2.525 | −41.044 | 1.00 | 18.45 | C |
| ATOM | 5406 | CG | PRO A | 754 | −35.445 | 1.250 | −41.710 | 1.00 | 18.53 | C |
| ATOM | 5407 | CD | PRO A | 754 | −36.160 | 1.216 | −43.013 | 1.00 | 18.80 | C |
| ATOM | 5408 | C | PRO A | 754 | −35.247 | 4.664 | −42.266 | 1.00 | 17.97 | C |
| ATOM | 5409 | O | PRO A | 754 | −34.109 | 4.493 | −42.688 | 1.00 | 17.97 | O |
| ATOM | 5410 | N | SER A | 755 | −35.710 | 5.851 | −41.896 | 1.00 | 17.49 | N |
| ATOM | 5411 | CA | SER A | 755 | −34.927 | 7.078 | −42.027 | 1.00 | 17.03 | C |
| ATOM | 5412 | CB | SER A | 755 | −35.615 | 8.052 | −42.999 | 1.00 | 17.20 | C |
| ATOM | 5413 | OG | SER A | 755 | −35.400 | 7.738 | −44.364 | 1.00 | 17.53 | O |
| ATOM | 5414 | C | SER A | 755 | −34.893 | 7.750 | −40.692 | 1.00 | 16.31 | C |
| ATOM | 5415 | O | SER A | 755 | −35.738 | 7.494 | −39.859 | 1.00 | 15.90 | O |
| ATOM | 5416 | N | ALA A | 756 | −33.940 | 8.654 | −40.514 | 1.00 | 16.35 | N |
| ATOM | 5417 | CA | ALA A | 756 | −33.998 | 9.641 | −39.438 | 1.00 | 16.46 | C |
| ATOM | 5418 | CB | ALA A | 756 | −33.071 | 10.799 | −39.743 | 1.00 | 15.87 | C |
| ATOM | 5419 | C | ALA A | 756 | −35.420 | 10.159 | −39.230 | 1.00 | 16.75 | C |
| ATOM | 5420 | O | ALA A | 756 | −35.957 | 10.082 | −38.131 | 1.00 | 16.44 | O |
| ATOM | 5421 | N | SER A | 757 | −36.029 | 10.662 | −40.303 | 1.00 | 17.31 | N |
| ATOM | 5422 | CA | SER A | 757 | −37.319 | 11.338 | −40.214 | 1.00 | 17.41 | C |
| ATOM | 5423 | CB | SER A | 757 | −37.544 | 12.234 | −41.431 | 1.00 | 17.06 | C |
| ATOM | 5424 | OG | SER A | 757 | −37.846 | 11.464 | −42.589 | 1.00 | 17.43 | O |
| ATOM | 5425 | C | SER A | 757 | −38.497 | 10.396 | −40.051 | 1.00 | 18.05 | C |
| ATOM | 5426 | O | SER A | 757 | −39.620 | 10.857 | −39.901 | 1.00 | 19.13 | O |
| ATOM | 5427 | N | THR A | 758 | −38.263 | 9.089 | −40.108 | 1.00 | 18.40 | N |
| ATOM | 5428 | CA | THR A | 758 | −39.346 | 8.125 | −39.898 | 1.00 | 18.94 | C |
| ATOM | 5429 | CB | THR A | 758 | −39.461 | 7.107 | −41.062 | 1.00 | 18.59 | C |
| ATOM | 5430 | OG1 | THR A | 758 | −38.284 | 6.292 | −41.135 | 1.00 | 18.62 | O |
| ATOM | 5431 | CG2 | THR A | 758 | −39.672 | 7.811 | −42.387 | 1.00 | 18.36 | C |
| ATOM | 5432 | C | THR A | 758 | −39.185 | 7.395 | −38.552 | 1.00 | 20.10 | C |
| ATOM | 5433 | O | THR A | 758 | −39.964 | 6.502 | −38.208 | 1.00 | 19.68 | O |
| ATOM | 5434 | N | GLN A | 759 | −38.165 | 7.801 | −37.800 | 1.00 | 21.50 | N |
| ATOM | 5435 | CA | GLN A | 759 | −37.742 | 7.102 | −36.597 | 1.00 | 22.17 | C |
| ATOM | 5436 | CB | GLN A | 759 | −36.492 | 6.275 | −36.873 | 1.00 | 23.10 | C |
| ATOM | 5437 | CG | GLN A | 759 | −36.631 | 5.154 | −37.879 | 1.00 | 24.95 | C |
| ATOM | 5438 | CD | GLN A | 759 | −35.324 | 4.378 | −37.997 | 1.00 | 28.18 | C |
| ATOM | 5439 | OE1 | GLN A | 759 | −34.481 | 4.649 | −38.874 | 1.00 | 30.07 | O |
| ATOM | 5440 | NE2 | GLN A | 759 | −35.121 | 3.435 | −37.078 | 1.00 | 30.04 | N |
| ATOM | 5441 | C | GLN A | 759 | −37.425 | 8.083 | −35.472 | 1.00 | 22.05 | C |
| ATOM | 5442 | O | GLN A | 759 | −36.685 | 7.753 | −34.550 | 1.00 | 23.27 | O |
| ATOM | 5443 | N | ALA A | 760 | −37.969 | 9.288 | −35.550 | 1.00 | 21.25 | N |
| ATOM | 5444 | CA | ALA A | 760 | −37.848 | 10.239 | −34.462 | 1.00 | 20.79 | C |
| ATOM | 5445 | CB | ALA A | 760 | −38.364 | 11.597 | −34.895 | 1.00 | 20.68 | C |
| ATOM | 5446 | C | ALA A | 760 | −38.643 | 9.738 | −33.267 | 1.00 | 21.10 | C |
| ATOM | 5447 | O | ALA A | 760 | −39.576 | 8.948 | −33.421 | 1.00 | 20.50 | O |
| ATOM | 5448 | N | LEU A | 761 | −38.270 | 10.203 | −32.076 | 1.00 | 21.64 | N |
| ATOM | 5449 | CA | LEU A | 761 | −39.007 | 9.884 | −30.862 | 1.00 | 21.84 | C |
| ATOM | 5450 | CB | LEU A | 761 | −38.256 | 10.379 | −29.626 | 1.00 | 22.29 | C |

-continued

| | | Atomic coordinates for CRBN:DDB1:Lenalidomide (Human protein) | | | | | | | |
|---|---|---|---|---|---|---|---|---|---|
| ATOM | 5451 | CG | LEU A | 761 | −37.509 | 9.308 | −28.831 | 1.00 | 22.54 | C |
| ATOM | 5452 | CD1 | LEU A | 761 | −36.212 | 8.880 | −29.517 | 1.00 | 22.80 | C |
| ATOM | 5453 | CD2 | LEU A | 761 | −37.234 | 9.804 | −27.424 | 1.00 | 22.70 | C |
| ATOM | 5454 | C | LEU A | 761 | −40.416 | 10.463 | −30.921 | 1.00 | 22.06 | C |
| ATOM | 5455 | O | LEU A | 761 | −41.390 | 9.715 | −30.963 | 1.00 | 23.19 | O |
| ATOM | 5456 | N | SER A | 762 | −40.517 | 11.790 | −30.921 | 1.00 | 21.68 | N |
| ATOM | 5457 | CA | SER A | 762 | −41.784 | 12.473 | −31.154 | 1.00 | 21.20 | C |
| ATOM | 5458 | CB | SER A | 762 | −41.960 | 13.641 | −30.177 | 1.00 | 19.64 | C |
| ATOM | 5459 | C | SER A | 762 | −41.789 | 12.961 | −32.606 | 1.00 | 21.82 | C |
| ATOM | 5460 | O | SER A | 762 | −40.725 | 13.288 | −33.168 | 1.00 | 22.47 | O |
| ATOM | 5461 | N | SER A | 763 | −42.962 | 12.987 | −33.233 | 1.00 | 21.22 | N |
| ATOM | 5462 | CA | SER A | 763 | −43.052 | 13.558 | −34.567 | 1.00 | 21.12 | C |
| ATOM | 5463 | CB | SER A | 763 | −42.814 | 12.493 | −35.630 | 1.00 | 20.88 | C |
| ATOM | 5464 | OG | SER A | 763 | −43.929 | 11.649 | −35.754 | 1.00 | 20.83 | O |
| ATOM | 5465 | C | SER A | 763 | −44.369 | 14.283 | −34.797 | 1.00 | 21.79 | C |
| ATOM | 5466 | O | SER A | 763 | −45.383 | 13.921 | −34.228 | 1.00 | 22.49 | O |
| ATOM | 5467 | N | SER A | 764 | −44.339 | 15.318 | −35.624 | 1.00 | 22.51 | N |
| ATOM | 5468 | CA | SER A | 764 | −45.536 | 16.074 | −35.951 | 1.00 | 23.15 | C |
| ATOM | 5469 | CB | SER A | 764 | −45.469 | 17.477 | −35.349 | 1.00 | 22.96 | C |
| ATOM | 5470 | OG | SER A | 764 | −44.376 | 18.219 | −35.873 | 1.00 | 22.46 | O |
| ATOM | 5471 | C | SER A | 764 | −45.704 | 16.161 | −37.457 | 1.00 | 24.58 | C |
| ATOM | 5472 | O | SER A | 764 | −44.909 | 15.613 | −38.221 | 1.00 | 24.76 | O |
| ATOM | 5473 | N | VAL A | 765 | −46.741 | 16.869 | −37.877 | 1.00 | 26.21 | N |
| ATOM | 5474 | CA | VAL A | 765 | −47.068 | 17.007 | −39.283 | 1.00 | 27.84 | C |
| ATOM | 5475 | CB | VAL A | 765 | −48.013 | 15.862 | −39.723 | 1.00 | 27.54 | C |
| ATOM | 5476 | CG1 | VAL A | 765 | −49.396 | 16.034 | −39.109 | 1.00 | 27.88 | C |
| ATOM | 5477 | CG2 | VAL A | 765 | −48.096 | 15.774 | −41.240 | 1.00 | 28.29 | C |
| ATOM | 5478 | C | VAL A | 765 | −47.704 | 18.389 | −39.511 | 1.00 | 29.38 | C |
| ATOM | 5479 | O | VAL A | 765 | −48.000 | 19.107 | −38.547 | 1.00 | 29.42 | O |
| ATOM | 5480 | N | SER A | 766 | −47.903 | 18.772 | −40.769 | 1.00 | 30.32 | N |
| ATOM | 5481 | CA | SER A | 766 | −48.663 | 19.984 | −41.048 | 1.00 | 31.64 | C |
| ATOM | 5482 | CB | SER A | 766 | −47.952 | 20.859 | −42.078 | 1.00 | 31.06 | C |
| ATOM | 5483 | OG | SER A | 766 | −46.720 | 21.345 | −41.553 | 1.00 | 29.41 | O |
| ATOM | 5484 | C | SER A | 766 | −50.118 | 19.685 | −41.432 | 1.00 | 33.69 | C |
| ATOM | 5485 | O | SER A | 766 | −51.013 | 20.461 | −41.095 | 1.00 | 35.49 | O |
| ATOM | 5486 | N | SER A | 767 | −50.351 | 18.557 | −42.109 | 1.00 | 35.39 | N |
| ATOM | 5487 | CA | SER A | 767 | −51.716 | 18.046 | −42.387 | 1.00 | 37.19 | C |
| ATOM | 5488 | CB | SER A | 767 | −52.218 | 17.191 | −41.201 | 1.00 | 38.29 | C |
| ATOM | 5489 | OG | SER A | 767 | −53.305 | 16.346 | −41.565 | 1.00 | 39.19 | O |
| ATOM | 5490 | C | SER A | 767 | −52.729 | 19.165 | −42.743 | 1.00 | 38.06 | C |
| ATOM | 5491 | O | SER A | 767 | −53.958 | 18.988 | −42.677 | 1.00 | 38.73 | O |
| ATOM | 5492 | N | GLU A | 784 | −43.142 | 6.228 | −59.466 | 1.00 | 41.57 | N |
| ATOM | 5493 | CA | GLU A | 784 | −43.087 | 7.684 | −59.395 | 1.00 | 40.70 | C |
| ATOM | 5494 | CB | GLU A | 784 | −44.464 | 8.301 | −59.681 | 1.00 | 40.97 | C |
| ATOM | 5495 | C | GLU A | 784 | −42.575 | 8.118 | −58.022 | 1.00 | 39.92 | C |
| ATOM | 5496 | O | GLU A | 784 | −43.294 | 8.024 | −57.014 | 1.00 | 38.64 | O |
| ATOM | 5497 | N | GLU A | 785 | −41.322 | 8.576 | −57.992 | 1.00 | 37.68 | N |
| ATOM | 5498 | CA | GLU A | 785 | −40.689 | 9.033 | −56.758 | 1.00 | 35.31 | C |
| ATOM | 5499 | CB | GLU A | 785 | −39.159 | 9.006 | −56.899 | 1.00 | 35.23 | C |
| ATOM | 5500 | CG | GLU A | 785 | −38.583 | 7.590 | −56.998 | 1.00 | 37.67 | C |
| ATOM | 5501 | CD | GLU A | 785 | −37.072 | 7.541 | −57.276 | 1.00 | 40.55 | C |
| ATOM | 5502 | OE1 | GLU A | 785 | −36.568 | 8.400 | −58.037 | 1.00 | 41.73 | O |
| ATOM | 5503 | OE2 | GLU A | 785 | −36.379 | 6.627 | −56.748 | 1.00 | 39.64 | O |
| ATOM | 5504 | C | GLU A | 785 | −41.215 | 10.421 | −56.334 | 1.00 | 33.29 | C |
| ATOM | 5505 | O | GLU A | 785 | −41.583 | 11.233 | −57.166 | 1.00 | 34.08 | O |
| ATOM | 5506 | N | VAL A | 786 | −41.298 | 10.660 | −55.031 | 1.00 | 30.24 | N |
| ATOM | 5507 | CA | VAL A | 786 | −41.653 | 11.976 | −54.503 | 1.00 | 27.03 | C |
| ATOM | 5508 | CB | VAL A | 786 | −43.124 | 12.021 | −53.996 | 1.00 | 26.83 | C |
| ATOM | 5509 | CG1 | VAL A | 786 | −43.351 | 11.030 | −52.860 | 1.00 | 26.32 | C |
| ATOM | 5510 | CG2 | VAL A | 786 | −43.533 | 13.440 | −53.584 | 1.00 | 27.05 | C |
| ATOM | 5511 | C | VAL A | 786 | −40.649 | 12.388 | −53.416 | 1.00 | 24.87 | C |
| ATOM | 5512 | O | VAL A | 786 | −39.833 | 11.585 | −52.967 | 1.00 | 24.67 | O |
| ATOM | 5513 | N | GLU A | 787 | −40.702 | 13.644 | −53.016 | 1.00 | 22.84 | N |
| ATOM | 5514 | CA | GLU A | 787 | −39.798 | 14.153 | −52.020 | 1.00 | 22.20 | C |
| ATOM | 5515 | CB | GLU A | 787 | −39.069 | 15.368 | −52.574 | 1.00 | 23.80 | C |
| ATOM | 5516 | CG | GLU A | 787 | −37.618 | 15.469 | −52.175 | 1.00 | 26.07 | C |
| ATOM | 5517 | CD | GLU A | 787 | −36.795 | 16.184 | −53.227 | 1.00 | 28.70 | C |
| ATOM | 5518 | OE1 | GLU A | 787 | −36.140 | 17.204 | −52.899 | 1.00 | 30.04 | O |
| ATOM | 5519 | OE2 | GLU A | 787 | −36.806 | 15.730 | −54.396 | 1.00 | 31.22 | O |
| ATOM | 5520 | C | GLU A | 787 | −40.616 | 14.557 | −50.812 | 1.00 | 20.38 | C |
| ATOM | 5521 | O | GLU A | 787 | −41.578 | 15.314 | −50.938 | 1.00 | 20.98 | O |
| ATOM | 5522 | N | VAL A | 788 | −40.250 | 14.043 | −49.645 | 1.00 | 17.81 | N |
| ATOM | 5523 | CA | VAL A | 788 | −40.904 | 14.439 | −48.414 | 1.00 | 15.98 | C |
| ATOM | 5524 | CB | VAL A | 788 | −41.475 | 13.234 | −47.683 | 1.00 | 15.68 | C |
| ATOM | 5525 | CG1 | VAL A | 788 | −42.051 | 13.659 | −46.347 | 1.00 | 15.27 | C |
| ATOM | 5526 | CG2 | VAL A | 788 | −42.528 | 12.568 | −48.545 | 1.00 | 15.93 | C |
| ATOM | 5527 | C | VAL A | 788 | −39.912 | 15.142 | −47.516 | 1.00 | 15.20 | C |

-continued

| | | | | Atomic coordinates for CRBN:DDB1:Lenalidomide (Human protein) | | | | | |
|---|---|---|---|---|---|---|---|---|---|
| ATOM | 5528 | O | VAL A | 788 | −38.945 | 14.529 | −47.068 | 1.00 | 14.89 | O |
| ATOM | 5529 | N | HIS A | 789 | −40.170 | 16.425 | −47.248 | 1.00 | 14.29 | N |
| ATOM | 5530 | CA | HIS A | 789 | −39.254 | 17.276 | −46.504 | 1.00 | 13.48 | C |
| ATOM | 5531 | CB | HIS A | 789 | −39.267 | 18.664 | −47.101 | 1.00 | 13.72 | C |
| ATOM | 5532 | CG | HIS A | 789 | −38.496 | 18.779 | −48.403 | 1.00 | 14.13 | C |
| ATOM | 5533 | ND1 | HIS A | 789 | −37.511 | 19.686 | −48.588 | 1.00 | 14.27 | N |
| ATOM | 5534 | CE1 | HIS A | 789 | −37.009 | 19.555 | −49.831 | 1.00 | 14.18 | C |
| ATOM | 5535 | NE2 | HIS A | 789 | −37.664 | 18.560 | −50.443 | 1.00 | 14.11 | N |
| ATOM | 5536 | CD2 | HIS A | 789 | −38.591 | 18.060 | −49.595 | 1.00 | 14.18 | C |
| ATOM | 5537 | C | HIS A | 789 | −39.589 | 17.327 | −45.042 | 1.00 | 12.95 | C |
| ATOM | 5538 | O | HIS A | 789 | −40.746 | 17.364 | −44.672 | 1.00 | 12.67 | O |
| ATOM | 5539 | N | ASN A | 790 | −38.569 | 17.298 | −44.192 | 1.00 | 12.77 | N |
| ATOM | 5540 | CA | ASN A | 790 | −38.768 | 17.383 | −42.749 | 1.00 | 12.61 | C |
| ATOM | 5541 | CB | ASN A | 790 | −38.605 | 16.024 | −42.074 | 1.00 | 12.95 | C |
| ATOM | 5542 | CG | ASN A | 790 | −39.360 | 14.920 | −42.781 | 1.00 | 13.49 | C |
| ATOM | 5543 | OD1 | ASN A | 790 | −40.445 | 14.499 | −42.340 | 1.00 | 13.30 | O |
| ATOM | 5544 | ND2 | ASN A | 790 | −38.774 | 14.416 | −43.880 | 1.00 | 13.71 | N |
| ATOM | 5545 | C | ASN A | 790 | −37.797 | 18.328 | −42.094 | 1.00 | 12.47 | C |
| ATOM | 5546 | O | ASN A | 790 | −36.745 | 18.646 | −42.657 | 1.00 | 12.44 | O |
| ATOM | 5547 | N | LEU A | 791 | −38.161 | 18.772 | −40.892 | 1.00 | 12.35 | N |
| ATOM | 5548 | CA | LEU A | 791 | −37.240 | 19.439 | −39.973 | 1.00 | 12.01 | C |
| ATOM | 5549 | CB | LEU A | 791 | −37.880 | 20.707 | −39.379 | 1.00 | 11.42 | C |
| ATOM | 5550 | CG | LEU A | 791 | −37.173 | 21.431 | −38.225 | 1.00 | 11.03 | C |
| ATOM | 5551 | CD1 | LEU A | 791 | −35.715 | 21.747 | −38.539 | 1.00 | 11.06 | C |
| ATOM | 5552 | CD2 | LEU A | 791 | −37.914 | 22.692 | −37.855 | 1.00 | 10.65 | C |
| ATOM | 5553 | C | LEU A | 791 | −36.922 | 18.435 | −38.877 | 1.00 | 12.16 | C |
| ATOM | 5554 | O | LEU A | 791 | −37.821 | 17.956 | −38.199 | 1.00 | 12.38 | O |
| ATOM | 5555 | N | LEU A | 792 | −35.652 | 18.098 | −38.721 | 1.00 | 12.36 | N |
| ATOM | 5556 | CA | LEU A | 792 | −35.253 | 17.174 | −37.677 | 1.00 | 12.76 | C |
| ATOM | 5557 | CB | LEU A | 792 | −34.156 | 16.242 | −38.178 | 1.00 | 12.47 | C |
| ATOM | 5558 | CG | LEU A | 792 | −34.416 | 15.483 | −39.467 | 1.00 | 12.38 | C |
| ATOM | 5559 | CD1 | LEU A | 792 | −33.168 | 14.725 | −39.881 | 1.00 | 12.39 | C |
| ATOM | 5560 | CD2 | LEU A | 792 | −35.603 | 14.551 | −39.314 | 1.00 | 12.47 | C |
| ATOM | 5561 | C | LEU A | 792 | −34.724 | 17.963 | −36.506 | 1.00 | 13.33 | C |
| ATOM | 5562 | O | LEU A | 792 | −34.097 | 19.007 | −36.687 | 1.00 | 13.72 | O |
| ATOM | 5563 | N | ILE A | 793 | −34.954 | 17.465 | −35.300 | 1.00 | 13.77 | N |
| ATOM | 5564 | CA | ILE A | 793 | −34.327 | 18.063 | −34.130 | 1.00 | 14.19 | C |
| ATOM | 5565 | CB | ILE A | 793 | −35.366 | 18.576 | −33.091 | 1.00 | 13.93 | C |
| ATOM | 5566 | CG1 | ILE A | 793 | −36.360 | 19.564 | −33.729 | 1.00 | 13.75 | C |
| ATOM | 5567 | CD1 | ILE A | 793 | −35.759 | 20.816 | −34.332 | 1.00 | 13.29 | C |
| ATOM | 5568 | CG2 | ILE A | 793 | −34.675 | 19.224 | −31.908 | 1.00 | 14.24 | C |
| ATOM | 5569 | C | ILE A | 793 | −33.359 | 17.046 | −33.539 | 1.00 | 14.70 | C |
| ATOM | 5570 | O | ILE A | 793 | −33.758 | 16.103 | −32.864 | 1.00 | 15.05 | O |
| ATOM | 5571 | N | ILE A | 794 | −32.081 | 17.230 | −33.827 | 1.00 | 15.48 | N |
| ATOM | 5572 | CA | ILE A | 794 | −31.060 | 16.288 | −33.392 | 1.00 | 16.33 | C |
| ATOM | 5573 | CB | ILE A | 794 | −30.045 | 15.999 | −34.528 | 1.00 | 15.67 | C |
| ATOM | 5574 | CG1 | ILE A | 794 | −30.701 | 15.148 | −35.599 | 1.00 | 15.09 | C |
| ATOM | 5575 | CD1 | ILE A | 794 | −30.330 | 15.595 | −36.981 | 1.00 | 15.46 | C |
| ATOM | 5576 | CG2 | ILE A | 794 | −28.829 | 15.255 | −34.013 | 1.00 | 15.63 | C |
| ATOM | 5577 | C | ILE A | 794 | −30.364 | 16.783 | −32.126 | 1.00 | 17.23 | C |
| ATOM | 5578 | O | ILE A | 794 | −29.845 | 17.893 | −32.098 | 1.00 | 17.02 | O |
| ATOM | 5579 | N | ASP A | 795 | −30.374 | 15.939 | −31.090 | 1.00 | 18.72 | N |
| ATOM | 5580 | CA | ASP A | 795 | −29.690 | 16.205 | −29.816 | 1.00 | 20.14 | C |
| ATOM | 5581 | CB | ASP A | 795 | −29.927 | 15.057 | −28.835 | 1.00 | 21.72 | C |
| ATOM | 5582 | CG | ASP A | 795 | −29.580 | 15.435 | −27.402 | 1.00 | 22.75 | C |
| ATOM | 5583 | OD2 | ASP A | 795 | −28.413 | 15.214 | −26.986 | 1.00 | 22.78 | O |
| ATOM | 5584 | OD1 | ASP A | 795 | −30.476 | 15.981 | −26.711 | 1.00 | 22.89 | O |
| ATOM | 5585 | C | ASP A | 795 | −28.193 | 16.380 | −29.986 | 1.00 | 20.15 | C |
| ATOM | 5586 | O | ASP A | 795 | −27.554 | 15.615 | −30.693 | 1.00 | 20.76 | O |
| ATOM | 5587 | N | GLN A | 796 | −27.629 | 17.364 | −29.305 | 1.00 | 20.40 | N |
| ATOM | 5588 | CA | GLN A | 796 | −26.246 | 17.748 | −29.558 | 1.00 | 21.18 | C |
| ATOM | 5589 | CB | GLN A | 796 | −26.052 | 19.217 | −29.205 | 1.00 | 21.56 | C |
| ATOM | 5590 | CG | GLN A | 796 | −24.810 | 19.571 | −28.430 | 1.00 | 22.65 | C |
| ATOM | 5591 | CD | GLN A | 796 | −25.107 | 20.620 | −27.389 | 1.00 | 23.85 | C |
| ATOM | 5592 | OE1 | GLN A | 796 | −25.289 | 20.295 | −26.221 | 1.00 | 24.92 | O |
| ATOM | 5593 | NE2 | GLN A | 796 | −25.196 | 21.886 | −27.808 | 1.00 | 23.84 | N |
| ATOM | 5594 | C | GLN A | 796 | −25.208 | 16.822 | −28.898 | 1.00 | 21.38 | C |
| ATOM | 5595 | O | GLN A | 796 | −24.065 | 16.719 | −29.362 | 1.00 | 21.04 | O |
| ATOM | 5596 | N | HIS A | 797 | −25.623 | 16.114 | −27.852 | 1.00 | 21.63 | N |
| ATOM | 5597 | CA | HIS A | 797 | −24.715 | 15.213 | −27.145 | 1.00 | 21.67 | C |
| ATOM | 5598 | CB | HIS A | 797 | −24.876 | 15.335 | −25.625 | 1.00 | 22.76 | C |
| ATOM | 5599 | CG | HIS A | 797 | −24.572 | 16.729 | −25.103 | 1.00 | 24.06 | C |
| ATOM | 5600 | ND1 | HIS A | 797 | −23.340 | 17.299 | −25.215 | 1.00 | 24.32 | N |
| ATOM | 5601 | CE1 | HIS A | 797 | −23.375 | 18.544 | −24.697 | 1.00 | 24.67 | C |
| ATOM | 5602 | NE2 | HIS A | 797 | −24.633 | 18.780 | −24.255 | 1.00 | 24.64 | N |
| ATOM | 5603 | CD2 | HIS A | 797 | −24.396 | 17.687 | −24.499 | 1.00 | 24.07 | C |
| ATOM | 5604 | C | HIS A | 797 | −24.829 | 13.805 | −27.612 | 1.00 | 21.06 | C |

-continued

| Atomic coordinates for CRBN:DDB1:Lenalidomide (Human protein) | | | | | | | | | | |
|---|---|---|---|---|---|---|---|---|---|---|
| ATOM | 5605 | O | HIS A | 797 | −23.823 | 13.179 | −27.894 | 1.00 | 21.65 | O |
| ATOM | 5606 | N | THR A | 798 | −26.052 | 13.309 | −27.758 | 1.00 | 20.61 | N |
| ATOM | 5607 | CA | THR A | 798 | −26.269 | 11.910 | −28.111 | 1.00 | 20.24 | C |
| ATOM | 5608 | CB | THR A | 798 | −27.384 | 11.276 | −27.262 | 1.00 | 19.85 | C |
| ATOM | 5609 | OG1 | THR A | 798 | −28.650 | 11.839 | −27.627 | 1.00 | 19.74 | O |
| ATOM | 5610 | CG2 | THR A | 798 | −27.127 | 11.507 | −25.794 | 1.00 | 20.40 | C |
| ATOM | 5611 | C | THR A | 798 | −26.618 | 11.669 | −29.574 | 1.00 | 20.39 | C |
| ATOM | 5612 | O | THR A | 798 | −26.752 | 10.521 | −29.986 | 1.00 | 21.57 | O |
| ATOM | 5613 | N | PHE A | 799 | −26.796 | 12.740 | −30.343 | 1.00 | 19.98 | N |
| ATOM | 5614 | CA | PHE A | 799 | −27.235 | 12.654 | −31.757 | 1.00 | 19.58 | C |
| ATOM | 5615 | CB | PHE A | 799 | −26.067 | 12.332 | −32.661 | 1.00 | 19.49 | C |
| ATOM | 5616 | CG | PHE A | 799 | −24.960 | 13.311 | −32.538 | 1.00 | 20.17 | C |
| ATOM | 5617 | CD1 | PHE A | 799 | −25.088 | 14.588 | −33.066 | 1.00 | 20.34 | C |
| ATOM | 5618 | CE1 | PHE A | 799 | −24.059 | 15.506 | −32.955 | 1.00 | 20.49 | C |
| ATOM | 5619 | CZ | PHE A | 799 | −22.897 | 15.160 | −32.281 | 1.00 | 20.70 | C |
| ATOM | 5620 | CE2 | PHE A | 799 | −22.761 | 13.889 | −31.738 | 1.00 | 20.84 | C |
| ATOM | 5621 | CD2 | PHE A | 799 | −23.797 | 12.977 | −31.858 | 1.00 | 20.85 | C |
| ATOM | 5622 | C | PHE A | 799 | −28.463 | 11.784 | −32.049 | 1.00 | 19.23 | C |
| ATOM | 5623 | O | PHE A | 799 | −28.666 | 11.302 | −33.170 | 1.00 | 18.58 | O |
| ATOM | 5624 | N | GLU A | 800 | −29.264 | 11.589 | −31.008 | 1.00 | 19.22 | N |
| ATOM | 5625 | CA | GLU A | 800 | −30.609 | 11.092 | −31.119 | 1.00 | 19.08 | C |
| ATOM | 5626 | CB | GLU A | 800 | −31.216 | 11.065 | −29.736 | 1.00 | 20.51 | C |
| ATOM | 5627 | CG | GLU A | 800 | −31.280 | 9.716 | −29.057 | 1.00 | 22.43 | C |
| ATOM | 5628 | CD | GLU A | 800 | −32.335 | 9.734 | −27.969 | 1.00 | 23.81 | C |
| ATOM | 5629 | OE1 | GLU A | 800 | −32.151 | 10.502 | −26.990 | 1.00 | 24.65 | O |
| ATOM | 5630 | OE2 | GLU A | 800 | −33.367 | 9.028 | −28.113 | 1.00 | 24.24 | O |
| ATOM | 5631 | C | GLU A | 800 | −31.451 | 12.038 | −31.966 | 1.00 | 18.33 | C |
| ATOM | 5632 | O | GLU A | 800 | −31.307 | 13.275 | −31.875 | 1.00 | 17.53 | O |
| ATOM | 5633 | N | VAL A | 801 | −32.343 | 11.457 | −32.769 | 1.00 | 17.31 | N |
| ATOM | 5634 | CA | VAL A | 801 | −33.360 | 12.235 | −33.488 | 1.00 | 16.37 | C |
| ATOM | 5635 | CB | VAL A | 801 | −33.796 | 11.554 | −34.799 | 1.00 | 15.84 | C |
| ATOM | 5636 | CG1 | VAL A | 801 | −34.686 | 12.479 | −35.613 | 1.00 | 15.70 | C |
| ATOM | 5637 | CG2 | VAL A | 801 | −32.586 | 11.144 | −35.607 | 1.00 | 15.73 | C |
| ATOM | 5638 | C | VAL A | 801 | −34.570 | 12.448 | −32.580 | 1.00 | 16.04 | C |
| ATOM | 5639 | O | VAL A | 801 | −35.458 | 11.590 | −32.489 | 1.00 | 15.98 | O |
| ATOM | 5640 | N | LEU A | 802 | −34.590 | 13.598 | −31.910 | 1.00 | 15.73 | N |
| ATOM | 5641 | CA | LEU A | 802 | −35.589 | 13.891 | −30.874 | 1.00 | 15.79 | C |
| ATOM | 5642 | CB | LEU A | 802 | −35.133 | 15.067 | −29.989 | 1.00 | 15.71 | C |
| ATOM | 5643 | CG | LEU A | 802 | −33.882 | 14.829 | −29.122 | 1.00 | 15.76 | C |
| ATOM | 5644 | CD1 | LEU A | 802 | −33.325 | 16.128 | −28.541 | 1.00 | 15.62 | C |
| ATOM | 5645 | CD2 | LEU A | 802 | −34.136 | 13.777 | −28.040 | 1.00 | 15.47 | C |
| ATOM | 5646 | C | LEU A | 802 | −36.986 | 14.151 | −31.430 | 1.00 | 15.66 | C |
| ATOM | 5647 | O | LEU A | 802 | −37.992 | 13.734 | −30.828 | 1.00 | 15.64 | O |
| ATOM | 5648 | N | HIS A | 803 | −37.036 | 14.831 | −32.576 | 1.00 | 15.27 | N |
| ATOM | 5649 | CA | HIS A | 803 | −38.299 | 15.168 | −33.234 | 1.00 | 15.01 | C |
| ATOM | 5650 | CB | HIS A | 803 | −38.880 | 16.442 | −32.642 | 1.00 | 14.86 | C |
| ATOM | 5651 | CG | HIS A | 803 | −40.301 | 16.695 | −33.039 | 1.00 | 14.92 | C |
| ATOM | 5652 | ND1 | HIS A | 803 | −41.338 | 16.295 | −32.292 | 1.00 | 15.04 | N |
| ATOM | 5653 | CE1 | HIS A | 803 | −42.491 | 16.655 | −32.891 | 1.00 | 14.90 | C |
| ATOM | 5654 | NE2 | HIS A | 803 | −42.189 | 17.282 | −34.025 | 1.00 | 14.99 | N |
| ATOM | 5655 | CD2 | HIS A | 803 | −40.841 | 17.325 | −34.151 | 1.00 | 15.24 | C |
| ATOM | 5656 | C | HIS A | 803 | −38.175 | 15.315 | −34.741 | 1.00 | 14.86 | C |
| ATOM | 5657 | O | HIS A | 803 | −37.126 | 15.760 | −35.273 | 1.00 | 14.43 | O |
| ATOM | 5658 | N | ALA A | 804 | −39.250 | 14.938 | −35.440 | 1.00 | 14.11 | N |
| ATOM | 5659 | CA | ALA A | 804 | −39.367 | 15.186 | −36.865 | 1.00 | 13.24 | C |
| ATOM | 5660 | CB | ALA A | 804 | −39.214 | 13.898 | −37.651 | 1.00 | 13.03 | C |
| ATOM | 5661 | C | ALA A | 804 | −40.694 | 15.855 | −37.172 | 1.00 | 12.85 | C |
| ATOM | 5662 | O | ALA A | 804 | −41.745 | 15.311 | −36.900 | 1.00 | 12.98 | O |
| ATOM | 5663 | N | HIS A | 805 | −40.640 | 17.067 | −37.695 | 1.00 | 12.59 | N |
| ATOM | 5664 | CA | HIS A | 805 | −41.816 | 17.674 | −38.279 | 1.00 | 12.55 | C |
| ATOM | 5665 | CB | HIS A | 805 | −41.844 | 19.174 | −38.002 | 1.00 | 12.52 | C |
| ATOM | 5666 | CG | HIS A | 805 | −43.030 | 19.871 | −38.602 | 1.00 | 12.48 | C |
| ATOM | 5667 | ND1 | HIS A | 805 | −44.148 | 20.104 | −37.910 | 1.00 | 12.57 | N |
| ATOM | 5668 | CE1 | HIS A | 805 | −45.049 | 20.714 | −38.707 | 1.00 | 12.63 | C |
| ATOM | 5669 | NE2 | HIS A | 805 | −44.502 | 20.862 | −39.920 | 1.00 | 12.64 | N |
| ATOM | 5670 | CD2 | HIS A | 805 | −43.256 | 20.352 | −39.893 | 1.00 | 12.56 | C |
| ATOM | 5671 | C | HIS A | 805 | −41.813 | 17.398 | −39.762 | 1.00 | 12.35 | C |
| ATOM | 5672 | O | HIS A | 805 | −40.778 | 17.485 | −40.404 | 1.00 | 12.45 | O |
| ATOM | 5673 | N | GLN A | 806 | −42.965 | 17.050 | −40.316 | 1.00 | 12.16 | N |
| ATOM | 5674 | CA | GLN A | 806 | −43.064 | 16.782 | −41.745 | 1.00 | 12.39 | C |
| ATOM | 5675 | CB | GLN A | 806 | −43.680 | 15.408 | −41.980 | 1.00 | 12.00 | C |
| ATOM | 5676 | CG | GLN A | 806 | −44.019 | 15.127 | −43.427 | 1.00 | 11.97 | C |
| ATOM | 5677 | CD | GLN A | 806 | −44.332 | 13.671 | −43.683 | 1.00 | 12.07 | C |
| ATOM | 5678 | OE1 | GLN A | 806 | −43.500 | 12.782 | −43.456 | 1.00 | 12.17 | O |
| ATOM | 5679 | NE2 | GLN A | 806 | −45.521 | 13.417 | −44.186 | 1.00 | 11.99 | N |
| ATOM | 5680 | C | GLN A | 806 | −43.878 | 17.873 | −42.452 | 1.00 | 12.92 | C |
| ATOM | 5681 | O | GLN A | 806 | −45.013 | 18.173 | −42.051 | 1.00 | 13.58 | O |

-continued

| | | | Atomic coordinates for CRBN:DDB1:Lenalidomide (Human protein) | | | | | | |
|---|---|---|---|---|---|---|---|---|---|
| ATOM | 5682 | N | PHE A | 807 | −43.313 | 18.473 | −43.496 | 1.00 | 12.93 | N |
| ATOM | 5683 | CA | PHE A | 807 | −43.999 | 19.570 | −44.175 | 1.00 | 13.34 | C |
| ATOM | 5684 | CB | PHE A | 807 | −43.013 | 20.450 | −44.945 | 1.00 | 13.00 | C |
| ATOM | 5685 | CG | PHE A | 807 | −42.062 | 21.171 | −44.059 | 1.00 | 12.64 | C |
| ATOM | 5686 | CD1 | PHE A | 807 | −42.468 | 22.312 | −43.375 | 1.00 | 12.49 | C |
| ATOM | 5687 | CE1 | PHE A | 807 | −41.602 | 22.966 | −42.525 | 1.00 | 12.43 | C |
| ATOM | 5688 | CZ | PHE A | 807 | −40.317 | 22.471 | −42.344 | 1.00 | 12.55 | C |
| ATOM | 5689 | CE2 | PHE A | 807 | −39.905 | 21.327 | −43.012 | 1.00 | 12.42 | C |
| ATOM | 5690 | CD2 | PHE A | 807 | −40.777 | 20.683 | −43.863 | 1.00 | 12.45 | C |
| ATOM | 5691 | C | PHE A | 807 | −45.113 | 19.063 | −45.076 | 1.00 | 14.06 | C |
| ATOM | 5692 | O | PHE A | 807 | −45.314 | 17.849 | −45.205 | 1.00 | 14.23 | O |
| ATOM | 5693 | N | LEU A | 808 | −45.839 | 19.997 | −45.685 | 1.00 | 14.58 | N |
| ATOM | 5694 | CA | LEU A | 808 | −46.978 | 19.658 | −46.527 | 1.00 | 15.34 | C |
| ATOM | 5695 | CB | LEU A | 808 | −47.784 | 20.918 | −46.856 | 1.00 | 15.73 | C |
| ATOM | 5696 | CG | LEU A | 808 | −48.617 | 21.479 | −45.685 | 1.00 | 15.84 | C |
| ATOM | 5697 | CD1 | LEU A | 808 | −48.924 | 22.962 | −45.886 | 1.00 | 15.45 | C |
| ATOM | 5698 | CD2 | LEU A | 808 | −49.889 | 20.664 | −45.469 | 1.00 | 15.32 | C |
| ATOM | 5699 | C | LEU A | 808 | −46.593 | 18.882 | −47.799 | 1.00 | 15.65 | C |
| ATOM | 5700 | O | LEU A | 808 | −45.484 | 19.028 | −48.311 | 1.00 | 15.56 | O |
| ATOM | 5701 | N | GLN A | 809 | −47.507 | 18.027 | −48.271 | 1.00 | 16.10 | N |
| ATOM | 5702 | CA | GLN A | 809 | −47.302 | 17.277 | −49.507 | 1.00 | 16.44 | C |
| ATOM | 5703 | CB | GLN A | 809 | −48.590 | 16.539 | −49.908 | 1.00 | 16.24 | C |
| ATOM | 5704 | C | GLN A | 809 | −46.869 | 18.288 | −50.568 | 1.00 | 16.78 | C |
| ATOM | 5705 | O | GLN A | 809 | −47.356 | 19.416 | −50.564 | 1.00 | 17.95 | O |
| ATOM | 5706 | N | ASN A | 810 | −45.914 | 17.923 | −51.420 | 1.00 | 16.49 | N |
| ATOM | 5707 | CA | ASN A | 810 | −45.319 | 18.878 | −52.386 | 1.00 | 16.89 | C |
| ATOM | 5708 | CB | ASN A | 810 | −46.297 | 19.193 | −53.529 | 1.00 | 16.78 | C |
| ATOM | 5709 | CG | ASN A | 810 | −46.473 | 18.029 | −54.481 | 1.00 | 17.06 | C |
| ATOM | 5710 | OD1 | ASN A | 810 | −47.588 | 17.624 | −54.754 | 1.00 | 17.08 | O |
| ATOM | 5711 | ND2 | ASN A | 810 | −45.364 | 17.475 | −54.982 | 1.00 | 17.28 | N |
| ATOM | 5712 | C | ASN A | 810 | −44.689 | 20.190 | −51.840 | 1.00 | 17.15 | C |
| ATOM | 5713 | O | ASN A | 810 | −44.234 | 21.036 | −52.624 | 1.00 | 17.44 | O |
| ATOM | 5714 | N | GLU A | 811 | −44.657 | 20.361 | −50.519 | 1.00 | 16.97 | N |
| ATOM | 5715 | CA | GLU A | 811 | −43.968 | 21.499 | −49.918 | 1.00 | 16.72 | C |
| ATOM | 5716 | CB | GLU A | 811 | −44.500 | 21.798 | −48.524 | 1.00 | 16.95 | C |
| ATOM | 5717 | CG | GLU A | 811 | −43.774 | 22.924 | −47.810 | 1.00 | 17.03 | C |
| ATOM | 5718 | CD | GLU A | 811 | −44.604 | 23.541 | −46.701 | 1.00 | 17.59 | C |
| ATOM | 5719 | OE1 | GLU A | 811 | −45.160 | 22.775 | −45.878 | 1.00 | 17.93 | O |
| ATOM | 5720 | OE2 | GLU A | 811 | −44.705 | 24.791 | −46.650 | 1.00 | 17.41 | O |
| ATOM | 5721 | C | GLU A | 811 | −42.492 | 21.218 | −49.824 | 1.00 | 16.91 | C |
| ATOM | 5722 | O | GLU A | 811 | −42.065 | 20.242 | −49.199 | 1.00 | 17.30 | O |
| ATOM | 5723 | N | TYR A | 812 | −41.710 | 22.105 | −50.417 | 1.00 | 16.96 | N |
| ATOM | 5724 | CA | TYR A | 812 | −40.267 | 21.984 | −50.451 | 1.00 | 16.43 | C |
| ATOM | 5725 | CB | TYR A | 812 | −39.805 | 22.383 | −51.834 | 1.00 | 16.95 | C |
| ATOM | 5726 | CG | TYR A | 812 | −38.496 | 21.795 | −52.249 | 1.00 | 18.12 | C |
| ATOM | 5727 | CD1 | TYR A | 812 | −37.296 | 22.410 | −51.871 | 1.00 | 18.37 | C |
| ATOM | 5728 | CE1 | TYR A | 812 | −36.070 | 21.895 | −52.268 | 1.00 | 19.11 | C |
| ATOM | 5729 | CZ | TYR A | 812 | −36.026 | 20.734 | −53.051 | 1.00 | 19.47 | C |
| ATOM | 5730 | OH | TYR A | 812 | −34.771 | 20.249 | −53.422 | 1.00 | 19.50 | O |
| ATOM | 5731 | CE2 | TYR A | 812 | −37.220 | 20.095 | −53.442 | 1.00 | 18.84 | C |
| ATOM | 5732 | CD2 | TYR A | 812 | −38.441 | 20.630 | −53.047 | 1.00 | 18.11 | C |
| ATOM | 5733 | C | TYR A | 812 | −39.668 | 22.910 | −49.416 | 1.00 | 15.57 | C |
| ATOM | 5734 | O | TYR A | 812 | −40.003 | 24.074 | −49.388 | 1.00 | 15.85 | O |
| ATOM | 5735 | N | ALA A | 813 | −38.800 | 22.393 | −48.556 | 1.00 | 15.02 | N |
| ATOM | 5736 | CA | ALA A | 813 | −38.180 | 23.201 | −47.504 | 1.00 | 14.69 | C |
| ATOM | 5737 | CB | ALA A | 813 | −38.024 | 22.383 | −46.244 | 1.00 | 14.41 | C |
| ATOM | 5738 | C | ALA A | 813 | −36.825 | 23.685 | −47.976 | 1.00 | 14.89 | C |
| ATOM | 5739 | O | ALA A | 813 | −35.939 | 22.874 | −48.208 | 1.00 | 15.70 | O |
| ATOM | 5740 | N | LEU A | 814 | −36.659 | 24.998 | −48.106 | 1.00 | 14.62 | N |
| ATOM | 5741 | CA | LEU A | 814 | −35.493 | 25.574 | −48.781 | 1.00 | 14.53 | C |
| ATOM | 5742 | CB | LEU A | 814 | −35.933 | 26.658 | −49.766 | 1.00 | 14.51 | C |
| ATOM | 5743 | CG | LEU A | 814 | −36.497 | 26.221 | −51.114 | 1.00 | 14.54 | C |
| ATOM | 5744 | CD1 | LEU A | 814 | −37.030 | 27.432 | −51.847 | 1.00 | 14.47 | C |
| ATOM | 5745 | CD2 | LEU A | 814 | −35.446 | 25.508 | −51.954 | 1.00 | 14.72 | C |
| ATOM | 5746 | C | LEU A | 814 | −34.428 | 26.174 | −47.877 | 1.00 | 14.67 | C |
| ATOM | 5747 | O | LEU A | 814 | −33.241 | 26.092 | −48.185 | 1.00 | 14.88 | O |
| ATOM | 5748 | N | SER A | 815 | −34.852 | 26.829 | −46.802 | 1.00 | 14.65 | N |
| ATOM | 5749 | CA | SER A | 815 | −33.937 | 27.575 | −45.944 | 1.00 | 14.57 | C |
| ATOM | 5750 | CB | SER A | 815 | −33.940 | 29.054 | −46.317 | 1.00 | 14.41 | C |
| ATOM | 5751 | OG | SER A | 815 | −35.220 | 29.605 | −46.144 | 1.00 | 14.08 | O |
| ATOM | 5752 | C | SER A | 815 | −34.322 | 27.414 | −44.489 | 1.00 | 14.78 | C |
| ATOM | 5753 | O | SER A | 815 | −35.466 | 27.084 | −44.178 | 1.00 | 15.03 | O |
| ATOM | 5754 | N | LEU A | 816 | −33.361 | 27.675 | −43.606 | 1.00 | 14.67 | N |
| ATOM | 5755 | CA | LEU A | 816 | −33.493 | 27.412 | −42.178 | 1.00 | 14.37 | C |
| ATOM | 5756 | CB | LEU A | 816 | −33.028 | 25.982 | −41.883 | 1.00 | 14.39 | C |
| ATOM | 5757 | CG | LEU A | 816 | −32.747 | 25.493 | −40.461 | 1.00 | 14.28 | C |
| ATOM | 5758 | CD1 | LEU A | 816 | −34.025 | 25.206 | −39.687 | 1.00 | 14.44 | C |

-continued

| Atomic coordinates for CRBN:DDB1:Lenalidomide (Human protein) | | | | | | | | | |
|---|---|---|---|---|---|---|---|---|---|
| ATOM | 5759 | CD2 | LEU A | 816 | −31.926 | 24.235 | −40.576 | 1.00 | 14.34 | C |
| ATOM | 5760 | C | LEU A | 816 | −32.644 | 28.410 | −41.402 | 1.00 | 14.41 | C |
| ATOM | 5761 | O | LEU A | 816 | −31.620 | 28.883 | −41.887 | 1.00 | 14.97 | O |
| ATOM | 5762 | N | VAL A | 817 | −33.053 | 28.719 | −40.187 | 1.00 | 14.25 | N |
| ATOM | 5763 | CA | VAL A | 817 | −32.347 | 29.706 | −39.390 | 1.00 | 14.51 | C |
| ATOM | 5764 | CB | VAL A | 817 | −32.620 | 31.141 | −39.924 | 1.00 | 14.25 | C |
| ATOM | 5765 | CG1 | VAL A | 817 | −34.101 | 31.348 | −40.194 | 1.00 | 14.49 | C |
| ATOM | 5766 | CG2 | VAL A | 817 | −32.115 | 32.203 | −38.976 | 1.00 | 14.20 | C |
| ATOM | 5767 | C | VAL A | 817 | −32.772 | 29.517 | −37.934 | 1.00 | 14.60 | C |
| ATOM | 5768 | O | VAL A | 817 | −33.892 | 29.089 | −37.674 | 1.00 | 14.78 | O |
| ATOM | 5769 | N | SER A | 818 | −31.872 | 29.789 | −36.995 | 1.00 | 14.77 | N |
| ATOM | 5770 | CA | SER A | 818 | −32.212 | 29.742 | −35.578 | 1.00 | 15.44 | C |
| ATOM | 5771 | CB | SER A | 818 | −31.407 | 28.648 | −34.878 | 1.00 | 15.24 | C |
| ATOM | 5772 | OG | SER A | 818 | −31.482 | 28.754 | −33.467 | 1.00 | 15.22 | O |
| ATOM | 5773 | C | SER A | 818 | −31.917 | 31.100 | −34.959 | 1.00 | 16.19 | C |
| ATOM | 5774 | O | SER A | 818 | −30.803 | 31.600 | −35.074 | 1.00 | 17.01 | O |
| ATOM | 5775 | N | CYS A | 819 | −32.893 | 31.711 | −34.304 | 1.00 | 16.69 | N |
| ATOM | 5776 | CA | CYS A | 819 | −32.654 | 33.050 | −33.783 | 1.00 | 17.57 | C |
| ATOM | 5777 | CB | CYS A | 819 | −32.422 | 34.014 | −34.945 | 1.00 | 17.85 | C |
| ATOM | 5778 | SG | CYS A | 819 | −33.805 | 34.115 | −36.108 | 1.00 | 17.92 | S |
| ATOM | 5779 | C | CYS A | 819 | −33.718 | 33.626 | −32.843 | 1.00 | 18.34 | C |
| ATOM | 5780 | O | CYS A | 819 | −34.837 | 33.108 | −32.732 | 1.00 | 18.14 | O |
| ATOM | 5781 | N | LYS A | 820 | −33.317 | 34.695 | −32.153 | 1.00 | 19.17 | N |
| ATOM | 5782 | CA | LYS A | 820 | −34.207 | 35.557 | −31.393 | 1.00 | 19.93 | C |
| ATOM | 5783 | CB | LYS A | 820 | −33.437 | 36.229 | −30.262 | 1.00 | 20.62 | C |
| ATOM | 5784 | CG | LYS A | 820 | −33.155 | 35.361 | −29.054 | 1.00 | 21.29 | C |
| ATOM | 5785 | CD | LYS A | 820 | −32.085 | 36.027 | −28.207 | 1.00 | 22.63 | C |
| ATOM | 5786 | CE | LYS A | 820 | −32.441 | 36.008 | −26.729 | 1.00 | 24.71 | C |
| ATOM | 5787 | NZ | LYS A | 820 | −32.479 | 34.614 | −26.180 | 1.00 | 27.50 | N |
| ATOM | 5788 | C | LYS A | 820 | −34.688 | 36.642 | −32.336 | 1.00 | 20.03 | C |
| ATOM | 5789 | O | LYS A | 820 | −33.964 | 37.014 | −33.266 | 1.00 | 20.25 | O |
| ATOM | 5790 | N | LEU A | 821 | −35.898 | 37.152 | −32.097 | 1.00 | 19.84 | N |
| ATOM | 5791 | CA | LEU A | 821 | −36.451 | 38.264 | −32.886 | 1.00 | 19.60 | C |
| ATOM | 5792 | CB | LEU A | 821 | −37.470 | 37.764 | −33.907 | 1.00 | 18.61 | C |
| ATOM | 5793 | CG | LEU A | 821 | −36.988 | 36.951 | −35.101 | 1.00 | 18.52 | C |
| ATOM | 5794 | CD1 | LEU A | 821 | −38.167 | 36.412 | −35.892 | 1.00 | 18.28 | C |
| ATOM | 5795 | CD2 | LEU A | 821 | −36.075 | 37.781 | −35.995 | 1.00 | 18.80 | C |
| ATOM | 5796 | C | LEU A | 821 | −37.114 | 39.296 | −31.993 | 1.00 | 20.43 | C |
| ATOM | 5797 | O | LEU A | 821 | −37.744 | 38.955 | −30.984 | 1.00 | 21.13 | O |
| ATOM | 5798 | N | GLY A | 822 | −36.979 | 40.560 | −32.365 | 1.00 | 20.99 | N |
| ATOM | 5799 | CA | GLY A | 822 | −37.623 | 41.637 | −31.626 | 1.00 | 21.94 | C |
| ATOM | 5800 | C | GLY A | 822 | −37.318 | 41.580 | −30.146 | 1.00 | 22.32 | C |
| ATOM | 5801 | O | GLY A | 822 | −36.158 | 41.482 | −29.753 | 1.00 | 22.59 | O |
| ATOM | 5802 | N | LYS A | 823 | −38.373 | 41.617 | −29.338 | 1.00 | 22.96 | N |
| ATOM | 5803 | CA | LYS A | 823 | −38.271 | 41.652 | −27.881 | 1.00 | 23.50 | C |
| ATOM | 5804 | CB | LYS A | 823 | −39.138 | 42.788 | −27.337 | 1.00 | 24.39 | C |
| ATOM | 5805 | CG | LYS A | 823 | −38.675 | 44.169 | −27.760 | 1.00 | 25.56 | C |
| ATOM | 5806 | CD | LYS A | 823 | −39.602 | 45.259 | −27.251 | 1.00 | 26.76 | C |
| ATOM | 5807 | CE | LYS A | 823 | −38.924 | 46.619 | −27.366 | 1.00 | 28.25 | C |
| ATOM | 5808 | NZ | LYS A | 823 | −39.875 | 47.703 | −27.751 | 1.00 | 28.96 | N |
| ATOM | 5809 | C | LYS A | 823 | −38.689 | 40.324 | −27.238 | 1.00 | 23.70 | C |
| ATOM | 5810 | O | LYS A | 823 | −39.034 | 40.277 | −26.058 | 1.00 | 24.02 | O |
| ATOM | 5811 | N | ASP A | 824 | −38.646 | 39.253 | −28.022 | 1.00 | 23.38 | N |
| ATOM | 5812 | CA | ASP A | 824 | −39.113 | 37.942 | −27.599 | 1.00 | 22.56 | C |
| ATOM | 5813 | CB | ASP A | 824 | −39.669 | 37.211 | −28.822 | 1.00 | 23.15 | C |
| ATOM | 5814 | OG | ASP A | 824 | −40.546 | 36.023 | −28.466 | 1.00 | 23.23 | C |
| ATOM | 5815 | OD1 | ASP A | 824 | −40.192 | 35.234 | −27.549 | 1.00 | 23.21 | O |
| ATOM | 5816 | OD2 | ASP A | 824 | −41.584 | 35.863 | −29.148 | 1.00 | 22.57 | O |
| ATOM | 5817 | C | ASP A | 824 | −37.924 | 37.180 | −27.048 | 1.00 | 22.46 | C |
| ATOM | 5818 | O | ASP A | 824 | −36.919 | 37.025 | −27.753 | 1.00 | 22.85 | O |
| ATOM | 5819 | N | PRO A | 825 | −38.022 | 36.690 | −25.791 | 1.00 | 22.18 | N |
| ATOM | 5820 | CA | PRO A | 825 | −36.864 | 36.016 | −25.190 | 1.00 | 22.07 | C |
| ATOM | 5821 | CB | PRO A | 825 | −37.272 | 35.867 | −23.716 | 1.00 | 21.00 | C |
| ATOM | 5822 | CG | PRO A | 825 | −38.751 | 35.806 | −23.743 | 1.00 | 20.92 | C |
| ATOM | 5823 | CD | PRO A | 825 | −39.181 | 36.700 | −24.877 | 1.00 | 21.85 | C |
| ATOM | 5824 | C | PRO A | 825 | −36.546 | 34.647 | −25.830 | 1.00 | 22.24 | C |
| ATOM | 5825 | O | PRO A | 825 | −35.424 | 34.147 | −25.692 | 1.00 | 22.46 | O |
| ATOM | 5826 | N | ASN A | 826 | −37.515 | 34.066 | −26.533 | 1.00 | 22.21 | N |
| ATOM | 5827 | CA | ASN A | 826 | −37.352 | 32.738 | −27.120 | 1.00 | 22.84 | C |
| ATOM | 5828 | CB | ASN A | 826 | −38.692 | 32.222 | −27.637 | 1.00 | 23.71 | C |
| ATOM | 5829 | CG | ASN A | 826 | −39.740 | 32.098 | −26.548 | 1.00 | 24.28 | C |
| ATOM | 5830 | OD1 | ASN A | 826 | −39.537 | 32.525 | −25.409 | 1.00 | 24.42 | O |
| ATOM | 5831 | ND2 | ASN A | 826 | −40.878 | 31.504 | −26.902 | 1.00 | 24.56 | N |
| ATOM | 5832 | C | ASN A | 826 | −36.356 | 32.684 | −28.263 | 1.00 | 22.55 | C |
| ATOM | 5833 | O | ASN A | 826 | −36.101 | 33.685 | −28.926 | 1.00 | 23.50 | O |
| ATOM | 5834 | N | THR A | 827 | −35.791 | 31.506 | −28.488 | 1.00 | 22.30 | N |
| ATOM | 5835 | CA | THR A | 827 | −35.084 | 31.227 | −29.737 | 1.00 | 21.97 | C |

-continued

| | | Atomic coordinates for CRBN:DDB1:Lenalidomide (Human protein) | | | | | | | |
|---|---|---|---|---|---|---|---|---|---|
| ATOM | 5836 | CB | THR A | 827 | −33.686 | 30.586 | −29.515 | 1.00 | 22.06 | C |
| ATOM | 5837 | OG1 | THR A | 827 | −32.882 | 31.446 | −28.700 | 1.00 | 23.06 | O |
| ATOM | 5838 | CG2 | THR A | 827 | −32.959 | 30.391 | −30.837 | 1.00 | 21.38 | C |
| ATOM | 5839 | C | THR A | 827 | −35.962 | 30.307 | −30.572 | 1.00 | 21.02 | C |
| ATOM | 5840 | O | THR A | 827 | −36.590 | 29.381 | −30.048 | 1.00 | 20.90 | O |
| ATOM | 5841 | N | TYR A | 828 | −36.002 | 30.569 | −31.871 | 1.00 | 19.72 | N |
| ATOM | 5842 | CA | TYR A | 828 | −36.860 | 29.826 | −32.759 | 1.00 | 18.62 | C |
| ATOM | 5843 | CB | TYR A | 828 | −37.883 | 30.773 | −33.359 | 1.00 | 19.31 | C |
| ATOM | 5844 | CG | TYR A | 828 | −38.772 | 31.434 | −32.343 | 1.00 | 19.91 | C |
| ATOM | 5845 | CD1 | TYR A | 828 | −39.820 | 30.733 | −31.746 | 1.00 | 20.68 | C |
| ATOM | 5846 | CE1 | TYR A | 828 | −40.648 | 31.333 | −30.813 | 1.00 | 21.11 | C |
| ATOM | 5847 | CZ | TYR A | 828 | −40.439 | 32.653 | −30.475 | 1.00 | 21.38 | C |
| ATOM | 5848 | OH | TYR A | 828 | −41.265 | 33.250 | −29.560 | 1.00 | 22.22 | O |
| ATOM | 5849 | CE2 | TYR A | 828 | −39.409 | 33.373 | −31.056 | 1.00 | 21.26 | C |
| ATOM | 5850 | CD2 | TYR A | 828 | −38.583 | 32.757 | −31.987 | 1.00 | 20.43 | C |
| ATOM | 5851 | C | TYR A | 828 | −36.081 | 29.168 | −33.874 | 1.00 | 17.53 | C |
| ATOM | 5852 | O | TYR A | 828 | −35.023 | 29.663 | −34.270 | 1.00 | 17.29 | O |
| ATOM | 5853 | N | PHE A | 829 | −36.599 | 28.044 | −34.370 | 1.00 | 16.29 | N |
| ATOM | 5854 | CA | PHE A | 829 | −36.197 | 27.529 | −35.676 | 1.00 | 15.10 | C |
| ATOM | 5855 | CB | PHE A | 829 | −36.248 | 26.008 | −35.735 | 1.00 | 14.95 | C |
| ATOM | 5856 | CG | PHE A | 829 | −35.180 | 25.339 | −34.931 | 1.00 | 15.22 | C |
| ATOM | 5857 | CD1 | PHE A | 829 | −33.854 | 25.343 | −35.367 | 1.00 | 15.37 | C |
| ATOM | 5858 | CE1 | PHE A | 829 | −32.862 | 24.730 | −34.618 | 1.00 | 15.26 | C |
| ATOM | 5859 | CZ | PHE A | 829 | −33.195 | 24.101 | −33.421 | 1.00 | 15.48 | C |
| ATOM | 5860 | CE2 | PHE A | 829 | −34.506 | 24.089 | −32.979 | 1.00 | 15.16 | C |
| ATOM | 5861 | CD2 | PHE A | 829 | −35.489 | 24.707 | −33.730 | 1.00 | 15.11 | C |
| ATOM | 5862 | C | PHE A | 829 | −37.177 | 28.102 | −36.647 | 1.00 | 14.47 | C |
| ATOM | 5863 | O | PHE A | 829 | −38.369 | 28.156 | −36.360 | 1.00 | 14.47 | O |
| ATOM | 5864 | N | ILE A | 830 | −36.675 | 28.548 | −37.788 | 1.00 | 14.04 | N |
| ATOM | 5865 | CA | ILE A | 830 | −37.483 | 29.277 | −38.758 | 1.00 | 13.93 | C |
| ATOM | 5866 | CB | ILE A | 830 | −37.158 | 30.795 | −38.698 | 1.00 | 13.78 | C |
| ATOM | 5867 | CG1 | ILE A | 830 | −37.472 | 31.360 | −37.312 | 1.00 | 13.54 | C |
| ATOM | 5868 | CD1 | ILE A | 830 | −37.182 | 32.832 | −37.176 | 1.00 | 13.54 | C |
| ATOM | 5869 | CG2 | ILE A | 830 | −37.924 | 31.566 | −39.757 | 1.00 | 13.74 | C |
| ATOM | 5870 | C | ILE A | 830 | −37.222 | 28.719 | −40.161 | 1.00 | 13.85 | C |
| ATOM | 5871 | O | ILE A | 830 | −36.129 | 28.877 | −40.688 | 1.00 | 14.49 | O |
| ATOM | 5872 | N | VAL A | 831 | −38.213 | 28.059 | −40.759 | 1.00 | 13.48 | N |
| ATOM | 5873 | CA | VAL A | 831 | −38.019 | 27.401 | −42.062 | 1.00 | 13.13 | C |
| ATOM | 5874 | CB | VAL A | 831 | −38.638 | 25.986 | −42.111 | 1.00 | 13.02 | C |
| ATOM | 5875 | CG1 | VAL A | 831 | −38.430 | 25.350 | −43.482 | 1.00 | 12.54 | C |
| ATOM | 5876 | CG2 | VAL A | 831 | −38.068 | 25.100 | −41.007 | 1.00 | 13.06 | C |
| ATOM | 5877 | C | VAL A | 831 | −38.648 | 28.194 | −43.172 | 1.00 | 13.15 | C |
| ATOM | 5878 | O | VAL A | 831 | −39.764 | 28.691 | −43.018 | 1.00 | 13.30 | O |
| ATOM | 5879 | N | GLY A | 832 | −37.944 | 28.282 | −44.299 | 1.00 | 13.17 | N |
| ATOM | 5880 | CA | GLY A | 832 | −38.483 | 28.889 | −45.515 | 1.00 | 13.30 | C |
| ATOM | 5881 | C | GLY A | 832 | −38.822 | 27.815 | −46.525 | 1.00 | 13.27 | C |
| ATOM | 5882 | O | GLY A | 832 | −37.974 | 27.018 | −46.876 | 1.00 | 13.41 | O |
| ATOM | 5883 | N | THR A | 833 | −40.068 | 27.780 | −46.985 | 1.00 | 13.41 | N |
| ATOM | 5884 | CA | THR A | 833 | −40.509 | 26.721 | −47.895 | 1.00 | 13.64 | C |
| ATOM | 5885 | CB | THR A | 833 | −41.745 | 25.993 | −47.359 | 1.00 | 13.53 | C |
| ATOM | 5886 | OG1 | THR A | 833 | −42.902 | 26.799 | −47.608 | 1.00 | 13.58 | O |
| ATOM | 5887 | CG2 | THR A | 833 | −41.610 | 25.693 | −45.872 | 1.00 | 13.26 | C |
| ATOM | 5888 | C | THR A | 833 | −40.892 | 27.275 | −49.252 | 1.00 | 13.89 | C |
| ATOM | 5889 | O | THR A | 833 | −40.839 | 28.483 | −49.457 | 1.00 | 14.34 | O |
| ATOM | 5890 | N | ALA A | 834 | −41.282 | 26.388 | −50.169 | 1.00 | 13.92 | N |
| ATOM | 5891 | CA | ALA A | 834 | −41.874 | 26.774 | −51.447 | 1.00 | 14.49 | C |
| ATOM | 5892 | CB | ALA A | 834 | −40.811 | 27.031 | −52.480 | 1.00 | 14.65 | C |
| ATOM | 5893 | C | ALA A | 834 | −42.741 | 25.652 | −51.903 | 1.00 | 15.22 | C |
| ATOM | 5894 | O | ALA A | 834 | −42.435 | 24.508 | −51.643 | 1.00 | 15.69 | O |
| ATOM | 5895 | N | MET A | 835 | −43.838 | 25.978 | −52.571 | 1.00 | 16.65 | N |
| ATOM | 5896 | CA | MET A | 835 | −44.747 | 24.969 | −53.094 | 1.00 | 17.69 | C |
| ATOM | 5897 | CB | MET A | 835 | −46.174 | 25.497 | −53.132 | 1.00 | 18.63 | C |
| ATOM | 5898 | CG | MET A | 835 | −46.883 | 25.416 | −51.804 | 1.00 | 19.98 | C |
| ATOM | 5899 | SD | MET A | 835 | −47.081 | 23.720 | −51.208 | 1.00 | 22.02 | S |
| ATOM | 5900 | CE | MET A | 835 | −46.739 | 24.064 | −49.486 | 1.00 | 20.65 | C |
| ATOM | 5901 | C | MET A | 835 | −44.318 | 24.579 | −54.490 | 1.00 | 18.17 | C |
| ATOM | 5902 | O | MET A | 835 | −44.325 | 25.415 | −55.402 | 1.00 | 18.56 | O |
| ATOM | 5903 | N | VAL A | 836 | −43.965 | 23.312 | −54.661 | 1.00 | 18.27 | N |
| ATOM | 5904 | CA | VAL A | 836 | −43.425 | 22.858 | −55.925 | 1.00 | 19.17 | C |
| ATOM | 5905 | CB | VAL A | 836 | −42.120 | 22.091 | −55.726 | 1.00 | 18.73 | C |
| ATOM | 5906 | CG1 | VAL A | 836 | −41.572 | 21.626 | −57.064 | 1.00 | 18.56 | C |
| ATOM | 5907 | CG2 | VAL A | 836 | −41.116 | 22.973 | −55.013 | 1.00 | 18.31 | C |
| ATOM | 5908 | C | VAL A | 836 | −44.399 | 21.988 | −56.683 | 1.00 | 20.28 | C |
| ATOM | 5909 | O | VAL A | 836 | −44.726 | 20.892 | −56.244 | 1.00 | 20.81 | O |
| ATOM | 5910 | N | TYR A | 837 | −44.854 | 22.479 | −57.828 | 1.00 | 21.89 | N |
| ATOM | 5911 | CA | TYR A | 837 | −45.688 | 21.681 | −58.714 | 1.00 | 23.55 | C |
| ATOM | 5912 | CB | TYR A | 837 | −47.029 | 22.366 | −58.967 | 1.00 | 23.66 | C |

-continued

| | | Atomic coordinates for CRBN:DDB1:Lenalidomide (Human protein) | | | | | | | |
|---|---|---|---|---|---|---|---|---|---|
| ATOM | 5913 | CG | TYR A | 837 | −47.863 | 22.472 | −57.715 | 1.00 | 23.82 | C |
| ATOM | 5914 | CD1 | TYR A | 837 | −48.475 | 21.349 | −57.169 | 1.00 | 23.68 | C |
| ATOM | 5915 | CE1 | TYR A | 837 | −49.224 | 21.431 | −56.012 | 1.00 | 23.88 | C |
| ATOM | 5916 | CZ | TYR A | 837 | −49.371 | 22.646 | −55.384 | 1.00 | 24.81 | C |
| ATOM | 5917 | OH | TYR A | 837 | −50.124 | 22.735 | −54.230 | 1.00 | 26.02 | O |
| ATOM | 5918 | CE2 | TYR A | 837 | −48.772 | 23.782 | −55.907 | 1.00 | 25.07 | C |
| ATOM | 5919 | CD2 | TYR A | 837 | −48.019 | 23.688 | −57.064 | 1.00 | 24.32 | C |
| ATOM | 5920 | C | TYR A | 837 | −44.965 | 21.409 | −60.013 | 1.00 | 25.06 | C |
| ATOM | 5921 | O | TYR A | 837 | −44.210 | 22.252 | −60.483 | 1.00 | 26.00 | O |
| ATOM | 5922 | N | PRO A | 838 | −45.170 | 20.212 | −60.583 | 1.00 | 26.38 | N |
| ATOM | 5923 | CA | PRO A | 838 | −44.587 | 19.839 | −61.879 | 1.00 | 28.36 | C |
| ATOM | 5924 | CB | PRO A | 838 | −44.995 | 18.371 | −62.030 | 1.00 | 27.95 | C |
| ATOM | 5925 | CG | PRO A | 838 | −45.241 | 17.901 | −60.635 | 1.00 | 26.88 | C |
| ATOM | 5926 | CD | PRO A | 838 | −45.836 | 19.073 | −59.934 | 1.00 | 26.11 | C |
| ATOM | 5927 | C | PRO A | 838 | −45.118 | 20.667 | −63.068 | 1.00 | 30.43 | C |
| ATOM | 5928 | O | PRO A | 838 | −44.360 | 20.989 | −63.980 | 1.00 | 29.96 | O |
| ATOM | 5929 | N | GLU A | 839 | −46.404 | 21.005 | −63.049 | 1.00 | 34.21 | N |
| ATOM | 5930 | CA | GLU A | 839 | −47.031 | 21.775 | −64.129 | 1.00 | 37.52 | C |
| ATOM | 5931 | CB | GLU A | 839 | −48.563 | 21.694 | −64.039 | 1.00 | 40.23 | C |
| ATOM | 5932 | CG | GLU A | 839 | −49.118 | 20.308 | −63.714 | 1.00 | 42.52 | C |
| ATOM | 5933 | CD | GLU A | 839 | −49.312 | 20.089 | −62.219 | 1.00 | 43.36 | C |
| ATOM | 5934 | OE1 | GLU A | 839 | −48.412 | 20.464 | −61.431 | 1.00 | 41.74 | O |
| ATOM | 5935 | OE2 | GLU A | 839 | −50.372 | 19.543 | −61.830 | 1.00 | 44.58 | O |
| ATOM | 5936 | C | GLU A | 839 | −46.605 | 23.238 | −64.086 | 1.00 | 38.03 | C |
| ATOM | 5937 | O | GLU A | 839 | −46.546 | 23.915 | −65.110 | 1.00 | 39.38 | O |
| ATOM | 5938 | N | GLU A | 840 | −46.313 | 23.717 | −62.889 | 1.00 | 38.16 | N |
| ATOM | 5939 | CA | GLU A | 840 | −45.997 | 25.103 | −62.674 | 1.00 | 38.37 | C |
| ATOM | 5940 | CB | GLU A | 840 | −46.708 | 25.571 | −61.395 | 1.00 | 44.04 | C |
| ATOM | 5941 | CG | GLU A | 840 | −46.404 | 26.982 | −60.913 | 1.00 | 50.48 | C |
| ATOM | 5942 | CD | GLU A | 840 | −46.446 | 27.099 | −59.388 | 1.00 | 55.97 | C |
| ATOM | 5943 | OE1 | GLU A | 840 | −45.631 | 26.428 | −58.705 | 1.00 | 58.23 | O |
| ATOM | 5944 | OE2 | GLU A | 840 | −47.287 | 27.869 | −58.867 | 1.00 | 58.66 | O |
| ATOM | 5945 | C | GLU A | 840 | −44.476 | 25.231 | −62.579 | 1.00 | 36.02 | C |
| ATOM | 5946 | O | GLU A | 840 | −43.867 | 24.741 | −61.635 | 1.00 | 35.67 | O |
| ATOM | 5947 | N | ALA A | 841 | −43.872 | 25.873 | −63.578 | 1.00 | 33.36 | N |
| ATOM | 5948 | CA | ALA A | 841 | −42.428 | 26.106 | −63.610 | 1.00 | 31.35 | C |
| ATOM | 5949 | CB | ALA A | 841 | −42.009 | 26.645 | −64.965 | 1.00 | 30.55 | C |
| ATOM | 5950 | C | ALA A | 841 | −41.937 | 27.037 | −62.507 | 1.00 | 31.54 | C |
| ATOM | 5951 | O | ALA A | 841 | −40.943 | 26.737 | −61.847 | 1.00 | 31.65 | O |
| ATOM | 5952 | N | GLU A | 842 | −42.627 | 28.164 | −62.320 | 1.00 | 31.70 | N |
| ATOM | 5953 | CA | GLU A | 842 | −42.178 | 29.221 | −61.403 | 1.00 | 31.94 | C |
| ATOM | 5954 | CB | GLU A | 842 | −42.353 | 30.591 | −62.049 | 1.00 | 35.00 | C |
| ATOM | 5955 | CG | GLU A | 842 | −41.577 | 30.765 | −63.335 | 1.00 | 39.59 | C |
| ATOM | 5956 | CD | GLU A | 842 | −40.954 | 32.140 | −63.456 | 1.00 | 42.67 | C |
| ATOM | 5957 | OE1 | GLU A | 842 | −41.697 | 33.092 | −63.792 | 1.00 | 44.57 | O |
| ATOM | 5958 | OE2 | GLU A | 842 | −39.722 | 32.262 | −63.220 | 1.00 | 43.98 | O |
| ATOM | 5959 | C | GLU A | 842 | −42.921 | 29.206 | −60.075 | 1.00 | 30.30 | C |
| ATOM | 5960 | O | GLU A | 842 | −44.147 | 29.241 | −60.058 | 1.00 | 31.43 | O |
| ATOM | 5961 | N | PRO A | 843 | −42.184 | 29.182 | −58.952 | 1.00 | 28.49 | N |
| ATOM | 5962 | CA | PRO A | 843 | −42.830 | 29.129 | −57.640 | 1.00 | 27.77 | C |
| ATOM | 5963 | CB | PRO A | 843 | −41.649 | 29.087 | −56.665 | 1.00 | 26.96 | C |
| ATOM | 5964 | CG | PRO A | 843 | −40.497 | 29.653 | −57.422 | 1.00 | 26.55 | C |
| ATOM | 5965 | CD | PRO A | 843 | −40.717 | 29.241 | −58.842 | 1.00 | 27.88 | C |
| ATOM | 5966 | C | PRO A | 843 | −43.739 | 30.345 | −57.373 | 1.00 | 27.58 | C |
| ATOM | 5967 | O | PRO A | 843 | −43.303 | 31.499 | −57.504 | 1.00 | 27.11 | O |
| ATOM | 5968 | N | LYS A | 844 | −44.997 | 30.072 | −57.020 | 1.00 | 27.44 | N |
| ATOM | 5969 | CA | LYS A | 844 | −46.002 | 31.123 | −56.804 | 1.00 | 25.89 | C |
| ATOM | 5970 | CB | LYS A | 844 | −47.177 | 30.980 | −57.785 | 1.00 | 26.93 | C |
| ATOM | 5971 | CG | LYS A | 844 | −46.845 | 31.287 | −59.242 | 1.00 | 29.52 | C |
| ATOM | 5972 | CD | LYS A | 844 | −46.272 | 32.700 | −59.437 | 1.00 | 32.04 | C |
| ATOM | 5973 | CE | LYS A | 844 | −46.153 | 33.091 | −60.915 | 1.00 | 32.36 | C |
| ATOM | 5974 | NZ | LYS A | 844 | −47.488 | 33.250 | −61.580 | 1.00 | 32.31 | N |
| ATOM | 5975 | C | LYS A | 844 | −46.524 | 31.182 | −55.368 | 1.00 | 24.20 | C |
| ATOM | 5976 | O | LYS A | 844 | −47.281 | 32.087 | −55.031 | 1.00 | 24.21 | O |
| ATOM | 5977 | N | GLN A | 845 | −46.127 | 30.225 | −54.529 | 1.00 | 22.46 | N |
| ATOM | 5978 | CA | GLN A | 845 | −46.493 | 30.258 | −53.109 | 1.00 | 21.27 | C |
| ATOM | 5979 | CB | GLN A | 845 | −47.929 | 29.778 | −52.882 | 1.00 | 22.22 | C |
| ATOM | 5980 | CG | GLN A | 845 | −48.238 | 28.472 | −53.566 | 1.00 | 24.19 | C |
| ATOM | 5981 | CD | GLN A | 845 | −49.571 | 27.885 | −53.162 | 1.00 | 26.04 | C |
| ATOM | 5982 | OE1 | GLN A | 845 | −49.937 | 27.876 | −51.975 | 1.00 | 27.58 | O |
| ATOM | 5983 | NE2 | GLN A | 845 | −50.302 | 27.357 | −54.147 | 1.00 | 26.79 | N |
| ATOM | 5984 | C | GLN A | 845 | −45.518 | 29.511 | −52.202 | 1.00 | 19.73 | C |
| ATOM | 5985 | O | GLN A | 845 | −44.909 | 28.533 | −52.608 | 1.00 | 19.32 | O |
| ATOM | 5986 | N | GLY A | 846 | −45.381 | 29.998 | −50.972 | 1.00 | 18.27 | N |
| ATOM | 5987 | CA | GLY A | 846 | −44.487 | 29.417 | −49.995 | 1.00 | 17.03 | C |
| ATOM | 5988 | C | GLY A | 846 | −44.770 | 29.955 | −48.606 | 1.00 | 16.57 | C |
| ATOM | 5989 | O | GLY A | 846 | −45.492 | 30.941 | −48.445 | 1.00 | 16.36 | O |

-continued

| | | Atomic coordinates for CRBN:DDB1:Lenalidomide (Human protein) | | | | | | | |
|---|---|---|---|---|---|---|---|---|---|
| ATOM | 5990 | N | ARG A | 847 | −44.195 | 29.298 | −47.601 | 1.00 | 15.75 | N |
| ATOM | 5991 | CA | ARG A | 847 | −44.403 | 29.670 | −46.208 | 1.00 | 15.15 | C |
| ATOM | 5992 | CB | ARG A | 847 | −44.888 | 28.472 | −45.402 | 1.00 | 15.30 | C |
| ATOM | 5993 | CG | ARG A | 847 | −46.331 | 28.094 | −45.607 | 1.00 | 15.89 | C |
| ATOM | 5994 | CD | ARG A | 847 | −46.815 | 27.273 | −44.424 | 1.00 | 16.02 | C |
| ATOM | 5995 | NE | ARG A | 847 | −46.301 | 25.912 | −44.454 | 1.00 | 15.95 | N |
| ATOM | 5996 | CZ | ARG A | 847 | −46.400 | 25.056 | −43.448 | 1.00 | 15.83 | C |
| ATOM | 5997 | NH1 | ARG A | 847 | −46.979 | 25.419 | −42.313 | 1.00 | 15.80 | N |
| ATOM | 5998 | NH2 | ARG A | 847 | −45.901 | 23.838 | −43.572 | 1.00 | 15.99 | N |
| ATOM | 5999 | C | ARG A | 847 | −43.112 | 30.112 | −45.564 | 1.00 | 14.66 | C |
| ATOM | 6000 | O | ARG A | 847 | −42.023 | 29.737 | −46.006 | 1.00 | 14.62 | O |
| ATOM | 6001 | N | ILE A | 848 | −43.250 | 30.902 | −44.505 | 1.00 | 14.02 | N |
| ATOM | 6002 | CA | ILE A | 848 | −42.232 | 31.018 | −43.479 | 1.00 | 13.33 | C |
| ATOM | 6003 | CB | ILE A | 848 | −41.739 | 32.464 | −43.311 | 1.00 | 12.75 | C |
| ATOM | 6004 | CG1 | ILE A | 848 | −41.166 | 32.967 | −44.635 | 1.00 | 12.39 | C |
| ATOM | 6005 | CD1 | ILE A | 848 | −40.986 | 34.458 | −44.690 | 1.00 | 12.60 | C |
| ATOM | 6006 | CG2 | ILE A | 848 | −40.702 | 32.559 | −42.202 | 1.00 | 12.28 | C |
| ATOM | 6007 | C | ILE A | 848 | −42.897 | 30.501 | −42.221 | 1.00 | 13.32 | C |
| ATOM | 6008 | O | ILE A | 848 | −43.954 | 30.994 | −41.831 | 1.00 | 13.34 | O |
| ATOM | 6009 | N | VAL A | 849 | −42.310 | 29.461 | −41.639 | 1.00 | 13.55 | N |
| ATOM | 6010 | CA | VAL A | 849 | −42.873 | 28.803 | −40.464 | 1.00 | 13.94 | C |
| ATOM | 6011 | CB | VAL A | 849 | −42.991 | 27.266 | −40.636 | 1.00 | 13.95 | C |
| ATOM | 6012 | CG1 | VAL A | 849 | −43.987 | 26.706 | −39.644 | 1.00 | 14.14 | C |
| ATOM | 6013 | CG2 | VAL A | 849 | −43.428 | 26.887 | −42.034 | 1.00 | 14.08 | C |
| ATOM | 6014 | C | VAL A | 849 | −41.959 | 29.064 | −39.284 | 1.00 | 14.24 | C |
| ATOM | 6015 | O | VAL A | 849 | −40.746 | 28.880 | −39.385 | 1.00 | 14.53 | O |
| ATOM | 6016 | N | VAL A | 850 | −42.531 | 29.478 | −38.162 | 1.00 | 14.52 | N |
| ATOM | 6017 | CA | VAL A | 850 | −41.725 | 29.729 | −36.974 | 1.00 | 15.00 | C |
| ATOM | 6018 | CB | VAL A | 850 | −41.944 | 31.148 | −36.401 | 1.00 | 14.87 | C |
| ATOM | 6019 | CG1 | VAL A | 850 | −41.060 | 31.362 | −35.182 | 1.00 | 14.82 | C |
| ATOM | 6020 | CG2 | VAL A | 850 | −41.681 | 32.214 | −37.465 | 1.00 | 14.43 | C |
| ATOM | 6021 | C | VAL A | 850 | −42.025 | 28.669 | −35.930 | 1.00 | 15.50 | C |
| ATOM | 6022 | O | VAL A | 850 | −43.137 | 28.596 | −35.400 | 1.00 | 15.93 | O |
| ATOM | 6023 | N | PHE A | 851 | −41.033 | 27.828 | −35.660 | 1.00 | 15.88 | N |
| ATOM | 6024 | CA | PHE A | 851 | −41.196 | 26.720 | −34.732 | 1.00 | 16.16 | C |
| ATOM | 6025 | CB | PHE A | 851 | −40.574 | 25.449 | −35.294 | 1.00 | 15.51 | C |
| ATOM | 6026 | CG | PHE A | 851 | −41.290 | 24.872 | −36.472 | 1.00 | 14.84 | C |
| ATOM | 6027 | CD1 | PHE A | 851 | −42.495 | 24.230 | −36.317 | 1.00 | 14.75 | C |
| ATOM | 6028 | CE1 | PHE A | 851 | −43.140 | 23.674 | −37.401 | 1.00 | 14.91 | C |
| ATOM | 6029 | CZ | PHE A | 851 | −42.563 | 23.734 | −38.656 | 1.00 | 14.81 | C |
| ATOM | 6030 | CE2 | PHE A | 851 | −41.353 | 24.371 | −38.821 | 1.00 | 14.80 | C |
| ATOM | 6031 | CD2 | PHE A | 851 | −40.721 | 24.926 | −37.728 | 1.00 | 14.72 | C |
| ATOM | 6032 | C | PHE A | 851 | −40.476 | 27.035 | −33.446 | 1.00 | 17.05 | C |
| ATOM | 6033 | O | PHE A | 851 | −39.466 | 27.750 | −33.450 | 1.00 | 17.12 | O |
| ATOM | 6034 | N | GLN A | 852 | −40.971 | 26.468 | −32.351 | 1.00 | 18.36 | N |
| ATOM | 6035 | CA | GLN A | 852 | −40.227 | 26.480 | −31.099 | 1.00 | 19.72 | C |
| ATOM | 6036 | CB | GLN A | 852 | −40.814 | 27.485 | −30.122 | 1.00 | 19.96 | C |
| ATOM | 6037 | CG | GLN A | 852 | −39.873 | 27.770 | −28.967 | 1.00 | 20.21 | C |
| ATOM | 6038 | CD | GLN A | 852 | −40.597 | 28.126 | −27.689 | 1.00 | 20.57 | C |
| ATOM | 6039 | OE1 | GLN A | 852 | −41.767 | 28.553 | −27.700 | 1.00 | 20.03 | O |
| ATOM | 6040 | NE2 | GLN A | 852 | −39.902 | 27.958 | −26.568 | 1.00 | 20.70 | N |
| ATOM | 6041 | C | GLN A | 852 | −40.109 | 25.107 | −30.439 | 1.00 | 20.20 | C |
| ATOM | 6042 | O | GLN A | 852 | −41.099 | 24.394 | −30.266 | 1.00 | 19.60 | O |
| ATOM | 6043 | N | TYR A | 853 | −38.877 | 24.760 | −30.081 | 1.00 | 21.60 | N |
| ATOM | 6044 | CA | TYR A | 853 | −38.570 | 23.497 | −29.430 | 1.00 | 23.71 | C |
| ATOM | 6045 | CB | TYR A | 853 | −37.305 | 22.859 | −30.025 | 1.00 | 23.98 | C |
| ATOM | 6046 | CG | TYR A | 853 | −36.928 | 21.536 | −29.393 | 1.00 | 24.62 | C |
| ATOM | 6047 | CD1 | TYR A | 853 | −37.569 | 20.345 | −29.763 | 1.00 | 24.78 | C |
| ATOM | 6048 | CE1 | TYR A | 853 | −37.233 | 19.137 | −29.178 | 1.00 | 24.28 | C |
| ATOM | 6049 | CZ | TYR A | 853 | −36.239 | 19.107 | −28.211 | 1.00 | 25.55 | C |
| ATOM | 6050 | OH | TYR A | 853 | −35.876 | 17.919 | −27.602 | 1.00 | 26.22 | O |
| ATOM | 6051 | CE2 | TYR A | 853 | −35.591 | 20.272 | −27.833 | 1.00 | 25.72 | C |
| ATOM | 6052 | CD2 | TYR A | 853 | −35.937 | 21.473 | −28.422 | 1.00 | 25.11 | C |
| ATOM | 6053 | C | TYR A | 853 | −38.444 | 23.672 | −27.914 | 1.00 | 25.55 | C |
| ATOM | 6054 | O | TYR A | 853 | −37.380 | 24.040 | −27.375 | 1.00 | 25.10 | O |
| ATOM | 6055 | N | SER A | 854 | −39.562 | 23.422 | −27.245 | 1.00 | 27.82 | N |
| ATOM | 6056 | CA | SER A | 854 | −39.627 | 23.377 | −25.797 | 1.00 | 29.56 | C |
| ATOM | 6057 | CB | SER A | 854 | −40.540 | 24.480 | −25.286 | 1.00 | 30.67 | C |
| ATOM | 6058 | OG | SER A | 854 | −41.754 | 24.481 | −26.017 | 1.00 | 32.24 | O |
| ATOM | 6059 | C | SER A | 854 | −40.161 | 22.008 | −25.369 | 1.00 | 31.09 | C |
| ATOM | 6060 | O | SER A | 854 | −40.861 | 21.321 | −26.146 | 1.00 | 29.93 | O |
| ATOM | 6061 | N | ASP A | 855 | −39.842 | 21.629 | −24.128 | 1.00 | 32.11 | N |
| ATOM | 6062 | CA | ASP A | 855 | −40.039 | 20.262 | −23.652 | 1.00 | 32.05 | C |
| ATOM | 6063 | CB | ASP A | 855 | −41.536 | 19.946 | −23.449 | 1.00 | 31.95 | C |
| ATOM | 6064 | C | ASP A | 855 | −39.383 | 19.294 | −24.649 | 1.00 | 31.91 | C |
| ATOM | 6065 | O | ASP A | 855 | −38.193 | 19.428 | −24.975 | 1.00 | 30.70 | O |
| ATOM | 6066 | N | GLY A | 856 | −40.160 | 18.338 | −25.141 | 1.00 | 31.56 | N |

-continued

| | | | | | Atomic coordinates for CRBN:DDB1:Lenalidomide (Human protein) | | | | |
|---|---|---|---|---|---|---|---|---|---|
| ATOM | 6067 | CA | GLY A | 856 | −39.661 | 17.405 | −26.129 | 1.00 | 31.97 | C |
| ATOM | 6068 | C | GLY A | 856 | −40.421 | 17.623 | −27.407 | 1.00 | 31.90 | C |
| ATOM | 6069 | O | GLY A | 856 | −40.420 | 16.778 | −28.302 | 1.00 | 32.02 | O |
| ATOM | 6070 | N | LYS A | 857 | −41.075 | 18.772 | −27.496 | 1.00 | 32.14 | N |
| ATOM | 6071 | CA | LYS A | 857 | −41.992 | 19.009 | −28.602 | 1.00 | 31.89 | C |
| ATOM | 6072 | CB | LYS A | 857 | −43.454 | 19.082 | −28.096 | 1.00 | 31.97 | C |
| ATOM | 6073 | C | LYS A | 857 | −41.633 | 20.218 | −29.484 | 1.00 | 29.52 | C |
| ATOM | 6074 | O | LYS A | 857 | −41.096 | 21.231 | −29.018 | 1.00 | 27.92 | O |
| ATOM | 6075 | N | LEU A | 858 | −41.926 | 20.070 | −30.767 | 1.00 | 27.13 | N |
| ATOM | 6076 | CA | LEU A | 858 | −41.909 | 21.164 | −31.686 | 1.00 | 26.97 | C |
| ATOM | 6077 | CB | LEU A | 858 | −41.410 | 20.672 | −33.034 | 1.00 | 25.10 | C |
| ATOM | 6078 | CG | LEU A | 858 | −40.520 | 21.599 | −33.854 | 1.00 | 24.17 | C |
| ATOM | 6079 | CD1 | LEU A | 858 | −39.439 | 22.260 | −33.009 | 1.00 | 23.42 | C |
| ATOM | 6080 | CD2 | LEU A | 858 | −39.894 | 20.782 | −34.967 | 1.00 | 24.01 | C |
| ATOM | 6081 | C | LEU A | 858 | −43.328 | 21.730 | −31.811 | 1.00 | 28.62 | C |
| ATOM | 6082 | O | LEU A | 858 | −44.271 | 21.002 | −32.161 | 1.00 | 30.00 | O |
| ATOM | 6083 | N | GLN A | 859 | −43.475 | 23.020 | −31.499 | 1.00 | 28.52 | N |
| ATOM | 6084 | CA | GLN A | 859 | −44.747 | 23.740 | −31.657 | 1.00 | 27.23 | C |
| ATOM | 6085 | CB | GLN A | 859 | −45.042 | 24.594 | −30.411 | 1.00 | 29.33 | C |
| ATOM | 6086 | CG | GLN A | 859 | −45.044 | 23.844 | −29.084 | 1.00 | 31.42 | C |
| ATOM | 6087 | CD | GLN A | 859 | −46.309 | 23.026 | −28.872 | 1.00 | 33.73 | C |
| ATOM | 6088 | OE1 | GLN A | 859 | −46.257 | 21.794 | −28.764 | 1.00 | 35.00 | O |
| ATOM | 6089 | NE2 | GLN A | 859 | −47.458 | 23.707 | −28.820 | 1.00 | 34.00 | N |
| ATOM | 6090 | C | GLN A | 859 | −44.654 | 24.661 | −32.868 | 1.00 | 25.15 | C |
| ATOM | 6091 | O | GLN A | 859 | −43.581 | 25.193 | −33.152 | 1.00 | 25.81 | O |
| ATOM | 6092 | N | THR A | 860 | −45.764 | 24.858 | −33.582 | 1.00 | 22.39 | N |
| ATOM | 6093 | CA | THR A | 860 | −45.809 | 25.892 | −34.619 | 1.00 | 19.82 | C |
| ATOM | 6094 | CB | THR A | 860 | −46.701 | 25.516 | −35.814 | 1.00 | 19.12 | C |
| ATOM | 6095 | OG1 | THR A | 860 | −46.196 | 24.326 | −34.427 | 1.00 | 19.32 | O |
| ATOM | 6096 | CG2 | THR A | 860 | −46.694 | 26.626 | −36.851 | 1.00 | 18.62 | C |
| ATOM | 6097 | C | THR A | 860 | −46.283 | 27.189 | −33.998 | 1.00 | 18.91 | C |
| ATOM | 6098 | O | THR A | 860 | −47.459 | 27.329 | −33.631 | 1.00 | 19.01 | O |
| ATOM | 6099 | N | VAL A | 861 | −45.360 | 28.136 | −33.871 | 1.00 | 17.46 | N |
| ATOM | 6100 | CA | VAL A | 861 | −45.664 | 29.403 | −33.235 | 1.00 | 16.79 | C |
| ATOM | 6101 | CB | VAL A | 861 | −44.439 | 29.972 | −32.487 | 1.00 | 16.93 | C |
| ATOM | 6102 | CG1 | VAL A | 861 | −44.720 | 31.373 | −31.976 | 1.00 | 17.32 | C |
| ATOM | 6103 | CG2 | VAL A | 861 | −44.043 | 29.065 | −31.330 | 1.00 | 16.70 | C |
| ATOM | 6104 | C | VAL A | 861 | −46.250 | 30.425 | −34.208 | 1.00 | 16.48 | C |
| ATOM | 6105 | O | VAL A | 861 | −47.020 | 31.274 | −33.798 | 1.00 | 16.64 | O |
| ATOM | 6106 | N | ALA A | 862 | −45.894 | 30.345 | −35.492 | 1.00 | 16.59 | N |
| ATOM | 6107 | CA | ALA A | 862 | −46.434 | 31.266 | −36.508 | 1.00 | 16.55 | C |
| ATOM | 6108 | CB | ALA A | 862 | −45.920 | 32.687 | −36.279 | 1.00 | 16.32 | C |
| ATOM | 6109 | C | ALA A | 862 | −46.166 | 30.833 | −37.952 | 1.00 | 16.68 | C |
| ATOM | 6110 | O | ALA A | 862 | −45.181 | 30.168 | −38.236 | 1.00 | 16.40 | O |
| ATOM | 6111 | N | ALA A | 862 | −47.064 | 31.230 | −38.848 | 1.00 | 17.56 | N |
| ATOM | 6112 | CA | ALA A | 862 | −46.902 | 31.072 | −40.283 | 1.00 | 18.51 | C |
| ATOM | 6113 | CB | ALA A | 862 | −48.113 | 30.354 | −40.857 | 1.00 | 19.75 | C |
| ATOM | 6114 | CG | ALA A | 862 | −48.079 | 28.842 | −40.792 | 1.00 | 21.83 | C |
| ATOM | 6115 | CD | ALA A | 862 | −49.250 | 28.213 | −41.540 | 1.00 | 23.51 | C |
| ATOM | 6116 | OE1 | ALA A | 862 | −48.992 | 27.346 | −42.415 | 1.00 | 24.07 | O |
| ATOM | 6117 | OE2 | ALA A | 862 | −50.424 | 28.597 | −41.271 | 1.00 | 23.91 | O |
| ATOM | 6118 | C | ALA A | 862 | −46.851 | 32.447 | −40.944 | 1.00 | 19.06 | C |
| ATOM | 6119 | O | GLU A | 863 | −47.348 | 33.435 | −40.383 | 1.00 | 19.83 | O |
| ATOM | 6120 | N | LYS A | 864 | −46.278 | 32.510 | −42.145 | 1.00 | 18.69 | N |
| ATOM | 6121 | CA | LYS A | 864 | −46.487 | 33.654 | −43.048 | 1.00 | 18.78 | C |
| ATOM | 6122 | CB | LYS A | 864 | −45.409 | 34.732 | −42.856 | 1.00 | 18.55 | C |
| ATOM | 6123 | CG | LYS A | 864 | −45.952 | 36.081 | −42.416 | 1.00 | 18.28 | C |
| ATOM | 6124 | CD | LYS A | 864 | −46.052 | 37.043 | −43.591 | 1.00 | 18.14 | C |
| ATOM | 6125 | CE | LYS A | 864 | −47.168 | 38.065 | −43.430 | 1.00 | 18.12 | C |
| ATOM | 6126 | NZ | LYS A | 864 | −47.546 | 38.323 | −42.015 | 1.00 | 18.59 | N |
| ATOM | 6127 | C | LYS A | 864 | −46.514 | 33.174 | −44.490 | 1.00 | 18.80 | C |
| ATOM | 6128 | O | LYS A | 864 | −45.516 | 32.653 | −44.991 | 1.00 | 19.34 | O |
| ATOM | 6129 | N | GLU A | 865 | −47.660 | 33.300 | −45.153 | 1.00 | 18.25 | N |
| ATOM | 6130 | CA | GLU A | 865 | −47.719 | 32.898 | −46.549 | 1.00 | 17.72 | C |
| ATOM | 6131 | CB | GLU A | 865 | −49.124 | 32.479 | −46.977 | 1.00 | 18.02 | C |
| ATOM | 6132 | CG | GLU A | 865 | −49.443 | 31.036 | −46.570 | 1.00 | 18.92 | C |
| ATOM | 6133 | CD | GLU A | 865 | −49.220 | 29.979 | −47.678 | 1.00 | 19.66 | C |
| ATOM | 6134 | OE1 | GLU A | 865 | −49.230 | 28.761 | −47.339 | 1.00 | 19.80 | O |
| ATOM | 6135 | OE2 | GLU A | 865 | −49.057 | 30.339 | −48.882 | 1.00 | 19.47 | O |
| ATOM | 6136 | C | GLU A | 865 | −47.133 | 33.999 | −47.394 | 1.00 | 17.27 | C |
| ATOM | 6137 | O | GLU A | 865 | −47.114 | 35.149 | −46.993 | 1.00 | 18.15 | O |
| ATOM | 6138 | N | VAL A | 866 | −46.590 | 33.634 | −48.537 | 1.00 | 16.73 | N |
| ATOM | 6139 | CA | VAL A | 866 | −45.681 | 34.491 | −49.268 | 1.00 | 16.17 | C |
| ATOM | 6140 | CB | VAL A | 866 | −44.231 | 34.187 | −48.838 | 1.00 | 16.30 | C |
| ATOM | 6141 | CG1 | VAL A | 866 | −43.260 | 34.663 | −49.882 | 1.00 | 16.93 | C |
| ATOM | 6142 | CG2 | VAL A | 866 | −43.902 | 34.819 | −47.494 | 1.00 | 16.26 | C |
| ATOM | 6143 | C | VAL A | 866 | −45.885 | 34.101 | −50.722 | 1.00 | 16.06 | C |

-continued

| | | | | | | | | | |
|---|---|---|---|---|---|---|---|---|---|
| | Atomic coordinates for CRBN:DDB1:Lenalidomide (Human protein) |

| | | | | | | | | | |
|---|---|---|---|---|---|---|---|---|---|
| ATOM | 6144 | O | VAL A | 866 | −45.994 | 32.920 | −51.024 | 1.00 | 16.42 | O |
| ATOM | 6145 | N | LYS A | 867 | −45.970 | 35.069 | −51.626 | 1.00 | 15.94 | N |
| ATOM | 6146 | CA | LYS A | 867 | −46.364 | 34.744 | −52.999 | 1.00 | 15.86 | C |
| ATOM | 6147 | CB | LYS A | 867 | −47.088 | 35.914 | −53.675 | 1.00 | 15.25 | C |
| ATOM | 6148 | C | LYS A | 867 | −45.161 | 34.286 | −53.814 | 1.00 | 16.01 | C |
| ATOM | 6149 | O | LYS A | 867 | −44.887 | 34.841 | −54.879 | 1.00 | 16.36 | O |
| ATOM | 6150 | N | GLY A | 868 | −44.449 | 33.275 | −53.305 | 1.00 | 15.49 | N |
| ATOM | 6151 | CA | GLY A | 868 | −43.309 | 32.690 | −53.996 | 1.00 | 15.45 | C |
| ATOM | 6152 | C | GLY A | 868 | −42.417 | 31.871 | −53.083 | 1.00 | 15.82 | C |
| ATOM | 6153 | O | GLY A | 868 | −42.809 | 31.531 | −51.960 | 1.00 | 15.79 | O |
| ATOM | 6154 | N | ALA A | 869 | −41.208 | 31.563 | −53.564 | 1.00 | 16.01 | N |
| ATOM | 6155 | CA | ALA A | 869 | −40.247 | 30.721 | −52.834 | 1.00 | 15.79 | C |
| ATOM | 6156 | CB | ALA A | 869 | −39.318 | 30.023 | −53.809 | 1.00 | 15.94 | C |
| ATOM | 6157 | C | ALA A | 869 | −39.430 | 31.522 | −51.833 | 1.00 | 15.79 | C |
| ATOM | 6158 | O | ALA A | 869 | −39.037 | 32.663 | −52.111 | 1.00 | 15.90 | O |
| ATOM | 6159 | N | VAL A | 870 | −39.166 | 30.920 | −50.676 | 1.00 | 15.35 | N |
| ATOM | 6160 | CA | VAL A | 870 | −38.319 | 31.548 | −49.664 | 1.00 | 14.82 | C |
| ATOM | 6161 | CB | VAL A | 870 | −38.820 | 31.298 | −48.228 | 1.00 | 14.64 | C |
| ATOM | 6162 | CG1 | VAL A | 870 | −38.094 | 32.204 | −47.249 | 1.00 | 14.60 | C |
| ATOM | 6163 | CG2 | VAL A | 870 | −40.310 | 31.548 | −48.137 | 1.00 | 14.99 | C |
| ATOM | 6164 | C | VAL A | 870 | −36.945 | 30.953 | −49.790 | 1.00 | 14.56 | C |
| ATOM | 6165 | O | VAL A | 870 | −36.597 | 30.052 | −49.027 | 1.00 | 14.77 | O |
| ATOM | 6166 | N | TYR A | 871 | −36.171 | 31.453 | −50.755 | 1.00 | 14.30 | N |
| ATOM | 6167 | CA | TYR A | 871 | −34.838 | 30.921 | −51.048 | 1.00 | 14.32 | C |
| ATOM | 6168 | CB | TYR A | 871 | −34.255 | 31.518 | −52.338 | 1.00 | 14.19 | C |
| ATOM | 6169 | CG | TYR A | 871 | −35.026 | 31.193 | −53.599 | 1.00 | 14.01 | C |
| ATOM | 6170 | CD1 | TYR A | 871 | −35.224 | 29.872 | −53.999 | 1.00 | 14.01 | C |
| ATOM | 6171 | CE1 | TYR A | 871 | −35.934 | 29.565 | −55.146 | 1.00 | 14.17 | C |
| ATOM | 6172 | CZ | TYR A | 871 | −36.441 | 30.586 | −55.924 | 1.00 | 14.58 | C |
| ATOM | 6173 | OH | TYR A | 871 | −37.141 | 30.285 | −57.081 | 1.00 | 14.78 | O |
| ATOM | 6174 | CE2 | TYR A | 871 | −39.247 | 31.911 | −55.549 | 1.00 | 14.76 | C |
| ATOM | 6175 | CD2 | TYR A | 871 | −35.539 | 32.202 | −54.396 | 1.00 | 14.12 | C |
| ATOM | 6176 | C | TYR A | 871 | −33.851 | 31.099 | −49.903 | 1.00 | 14.64 | C |
| ATOM | 6177 | O | TYR A | 871 | −33.111 | 30.192 | −49.600 | 1.00 | 15.77 | O |
| ATOM | 6178 | N | SER A | 872 | −33.847 | 32.255 | −49.258 | 1.00 | 14.94 | N |
| ATOM | 6179 | CA | SER A | 872 | −32.833 | 32.559 | −48.250 | 1.00 | 15.03 | C |
| ATOM | 6180 | CB | SER A | 872 | −31.726 | 33.437 | −48.847 | 1.00 | 15.37 | C |
| ATOM | 6181 | OG | SER A | 872 | −30.672 | 32.662 | −49.415 | 1.00 | 16.09 | O |
| ATOM | 6182 | C | SER A | 872 | −33.452 | 33.292 | −47.092 | 1.00 | 15.16 | C |
| ATOM | 6183 | O | SER A | 872 | −34.473 | 33.953 | −47.240 | 1.00 | 15.75 | O |
| ATOM | 6184 | N | MET A | 873 | −32.828 | 33.171 | −45.933 | 1.00 | 14.86 | N |
| ATOM | 6185 | CA | MET A | 873 | −33.234 | 33.898 | −44.760 | 1.00 | 14.39 | C |
| ATOM | 6186 | CB | MET A | 873 | −34.198 | 33.069 | −43.940 | 1.00 | 14.22 | C |
| ATOM | 6187 | CG | MET A | 873 | −35.631 | 33.089 | −44.435 | 1.00 | 14.28 | C |
| ATOM | 6188 | SD | MET A | 873 | −36.769 | 32.483 | −43.170 | 1.00 | 14.34 | S |
| ATOM | 6189 | CE | MET A | 873 | −36.397 | 30.738 | −43.128 | 1.00 | 14.06 | C |
| ATOM | 6190 | C | MET A | 873 | −31.992 | 34.188 | −43.944 | 1.00 | 14.67 | C |
| ATOM | 6191 | O | MET A | 873 | −31.103 | 33.351 | −43.847 | 1.00 | 14.85 | O |
| ATOM | 6192 | N | VAL A | 874 | −31.917 | 35.390 | −43.389 | 1.00 | 14.86 | N |
| ATOM | 6193 | CA | VAL A | 874 | −30.857 | 35.756 | −42.470 | 1.00 | 15.32 | C |
| ATOM | 6194 | CB | VAL A | 874 | −29.661 | 36.441 | −43.189 | 1.00 | 15.14 | C |
| ATOM | 6195 | CG1 | VAL A | 874 | −30.111 | 37.193 | −44.415 | 1.00 | 15.33 | C |
| ATOM | 6196 | CG2 | VAL A | 874 | −28.921 | 37.390 | −42.258 | 1.00 | 15.37 | C |
| ATOM | 6197 | C | VAL A | 874 | −31.459 | 36.646 | −41.389 | 1.00 | 15.99 | C |
| ATOM | 6198 | O | VAL A | 874 | −32.275 | 37.508 | −41.679 | 1.00 | 15.91 | O |
| ATOM | 6199 | N | GLU A | 875 | −31.081 | 36.405 | −40.138 | 1.00 | 17.16 | N |
| ATOM | 6200 | CA | GLU A | 875 | −31.553 | 37.219 | −39.025 | 1.00 | 17.94 | C |
| ATOM | 6201 | CB | GLU A | 875 | −31.256 | 36.500 | −37.698 | 1.00 | 18.13 | C |
| ATOM | 6202 | CG | GLU A | 875 | −31.589 | 37.298 | −36.451 | 1.00 | 19.31 | C |
| ATOM | 6203 | CD | GLU A | 875 | −30.455 | 38.221 | −36.023 | 1.00 | 20.48 | C |
| ATOM | 6204 | OE1 | GLU A | 875 | −29.276 | 37.811 | −36.144 | 1.00 | 21.11 | O |
| ATOM | 6205 | OE2 | GLU A | 875 | −30.735 | 39.357 | −35.562 | 1.00 | 21.41 | O |
| ATOM | 6206 | C | GLU A | 875 | −30.865 | 38.586 | −39.119 | 1.00 | 18.20 | C |
| ATOM | 6207 | O | GLU A | 875 | −29.652 | 38.648 | −39.238 | 1.00 | 18.93 | O |
| ATOM | 6208 | N | PHE A | 876 | −31.631 | 39.673 | −39.081 | 1.00 | 18.34 | N |
| ATOM | 6209 | CA | PHE A | 876 | −31.096 | 40.993 | −39.441 | 1.00 | 18.84 | C |
| ATOM | 6210 | CB | PHE A | 876 | −31.546 | 41.345 | −40.871 | 1.00 | 18.30 | C |
| ATOM | 6211 | CG | PHE A | 876 | −31.019 | 42.655 | −41.388 | 1.00 | 18.57 | C |
| ATOM | 6212 | CD1 | PHE A | 876 | −29.737 | 42.749 | −41.913 | 1.00 | 18.90 | C |
| ATOM | 6213 | CE1 | PHE A | 876 | −29.250 | 43.959 | −42.408 | 1.00 | 18.87 | C |
| ATOM | 6214 | CZ | PHE A | 876 | −30.054 | 45.082 | −42.389 | 1.00 | 18.68 | C |
| ATOM | 6215 | CE2 | PHE A | 876 | −31.342 | 44.999 | −41.876 | 1.00 | 18.57 | C |
| ATOM | 6216 | CD2 | PHE A | 876 | −31.820 | 43.794 | −41.387 | 1.00 | 18.61 | C |
| ATOM | 6217 | C | PHE A | 876 | −31.457 | 42.100 | −38.416 | 1.00 | 19.67 | C |
| ATOM | 6218 | O | PHE A | 876 | −32.474 | 42.791 | −38.545 | 1.00 | 19.85 | O |
| ATOM | 6219 | N | ASN A | 877 | −30.608 | 42.254 | −37.402 | 1.00 | 20.32 | N |
| ATOM | 6220 | CA | ASN A | 877 | −30.802 | 43.251 | −36.328 | 1.00 | 20.68 | C |

-continued

| | | Atomic coordinates for CRBN:DDB1:Lenalidomide (Human protein) | | | | | | | |
|---|---|---|---|---|---|---|---|---|---|
| ATOM | 6221 | CB | ASN A | 877 | −30.671 | 44.687 | −36.867 | 1.00 | 21.74 | C |
| ATOM | 6222 | CG | ASN A | 877 | −29.333 | 44.946 | −37.538 | 1.00 | 23.18 | C |
| ATOM | 6223 | OD1 | ASN A | 877 | −28.284 | 44.515 | −37.053 | 1.00 | 24.06 | O |
| ATOM | 6224 | ND2 | ASN A | 877 | −29.362 | 45.666 | −38.661 | 1.00 | 23.89 | N |
| ATOM | 6225 | C | ASN A | 877 | −32.107 | 43.082 | −35.527 | 1.00 | 19.97 | C |
| ATOM | 6226 | O | ASN A | 877 | −32.793 | 44.057 | −35.207 | 1.00 | 20.02 | O |
| ATOM | 6227 | N | GLY A | 878 | −32.435 | 41.838 | −35.199 | 1.00 | 18.87 | N |
| ATOM | 6228 | CA | GLY A | 878 | −33.661 | 41.546 | −34.483 | 1.00 | 17.41 | C |
| ATOM | 6229 | C | GLY A | 878 | −34.854 | 41.438 | −35.404 | 1.00 | 16.56 | C |
| ATOM | 6230 | O | GLY A | 878 | −35.960 | 41.145 | −34.961 | 1.00 | 16.75 | O |
| ATOM | 6231 | N | LYS A | 879 | −34.638 | 41.673 | −36.691 | 1.00 | 16.01 | N |
| ATOM | 6232 | CA | LYS A | 879 | −35.701 | 41.502 | −37.684 | 1.00 | 15.34 | C |
| ATOM | 6233 | CB | LYS A | 879 | −35.863 | 42.768 | −38.527 | 1.00 | 15.33 | C |
| ATOM | 6234 | CG | LYS A | 879 | −35.791 | 44.053 | −37.726 | 1.00 | 15.23 | C |
| ATOM | 6235 | CD | LYS A | 879 | −36.216 | 45.234 | −38.560 | 1.00 | 15.63 | C |
| ATOM | 6236 | CE | LYS A | 879 | −35.563 | 46.519 | −38.072 | 1.00 | 16.14 | C |
| ATOM | 6237 | NZ | LYS A | 879 | −36.464 | 47.693 | −38.286 | 1.00 | 16.72 | N |
| ATOM | 6238 | C | LYS A | 879 | −35.347 | 40.320 | −38.562 | 1.00 | 14.81 | C |
| ATOM | 6239 | O | LYS A | 879 | −34.222 | 39.821 | −38.501 | 1.00 | 15.06 | O |
| ATOM | 6240 | N | LEU A | 880 | −36.298 | 39.862 | −39.372 | 1.00 | 14.12 | N |
| ATOM | 6241 | CA | LEU A | 880 | −36.039 | 38.742 | −40.277 | 1.00 | 13.58 | C |
| ATOM | 6242 | CB | LEU A | 880 | −37.090 | 37.654 | −40.115 | 1.00 | 13.32 | C |
| ATOM | 6243 | CG | LEU A | 880 | −36.855 | 36.335 | −40.837 | 1.00 | 13.28 | C |
| ATOM | 6244 | CD1 | LEU A | 880 | −35.807 | 35.522 | −40.103 | 1.00 | 13.41 | C |
| ATOM | 6245 | CD2 | LEU A | 880 | −38.150 | 32.557 | −40.932 | 1.00 | 13.17 | C |
| ATOM | 6246 | C | LEU A | 880 | −35.968 | 39.199 | −41.727 | 1.00 | 13.42 | C |
| ATOM | 6247 | O | LEU A | 880 | −36.889 | 39.825 | −42.242 | 1.00 | 13.50 | O |
| ATOM | 6248 | N | LEU A | 881 | −34.851 | 38.887 | −42.365 | 1.00 | 13.30 | N |
| ATOM | 6249 | CA | LEU A | 881 | −34.600 | 39.270 | −43.725 | 1.00 | 13.45 | C |
| ATOM | 6250 | CB | LEU A | 881 | −33.198 | 39.848 | −43.849 | 1.00 | 13.45 | C |
| ATOM | 6251 | CG | LEU A | 881 | −32.787 | 40.620 | −45.104 | 1.00 | 13.67 | C |
| ATOM | 6252 | CD1 | LEU A | 881 | −33.792 | 41.702 | −45.479 | 1.00 | 13.62 | C |
| ATOM | 6253 | CD2 | LEU A | 881 | −31.394 | 41.221 | −44.918 | 1.00 | 13.76 | C |
| ATOM | 6254 | C | LEU A | 881 | −34.736 | 38.019 | −44.552 | 1.00 | 13.87 | C |
| ATOM | 6255 | O | LEU A | 881 | −34.050 | 37.034 | −44.310 | 1.00 | 13.86 | O |
| ATOM | 6256 | N | ALA A | 882 | −35.653 | 38.062 | −45.516 | 1.00 | 14.49 | N |
| ATOM | 6257 | CA | ALA A | 882 | −35.995 | 36.911 | −46.342 | 1.00 | 14.46 | C |
| ATOM | 6258 | CB | ALA A | 882 | −37.376 | 36.390 | −45.989 | 1.00 | 14.50 | C |
| ATOM | 6259 | C | ALA A | 882 | −35.987 | 37.344 | −47.763 | 1.00 | 14.68 | C |
| ATOM | 6260 | O | ALA A | 882 | −36.498 | 38.403 | −48.087 | 1.00 | 14.52 | O |
| ATOM | 6261 | N | SER A | 883 | −35.401 | 36.518 | −48.612 | 1.00 | 15.72 | N |
| ATOM | 6262 | CA | SER A | 883 | −35.453 | 36.730 | −50.044 | 1.00 | 16.80 | C |
| ATOM | 6263 | CB | SER A | 883 | −34.091 | 36.456 | −50.678 | 1.00 | 17.05 | C |
| ATOM | 6264 | OG | SER A | 883 | −33.835 | 35.069 | −50.773 | 1.00 | 16.98 | O |
| ATOM | 6265 | C | SER A | 883 | −36.510 | 35.804 | −50.620 | 1.00 | 17.41 | C |
| ATOM | 6266 | O | SER A | 883 | −36.413 | 34.584 | −50.474 | 1.00 | 17.48 | O |
| ATOM | 6267 | N | ILE A | 884 | −37.528 | 36.401 | −51.241 | 1.00 | 18.05 | N |
| ATOM | 6268 | CA | ILE A | 884 | −38.632 | 35.666 | −51.858 | 1.00 | 18.69 | C |
| ATOM | 6269 | CB | ILE A | 884 | −39.964 | 36.009 | −51.207 | 1.00 | 18.68 | C |
| ATOM | 6270 | CG1 | ILE A | 884 | −39.858 | 35.848 | −49.682 | 1.00 | 19.18 | C |
| ATOM | 6271 | CD1 | ILE A | 884 | −40.834 | 36.715 | −48.907 | 1.00 | 19.36 | C |
| ATOM | 6272 | CG2 | ILE A | 884 | −41.065 | 35.175 | −51.842 | 1.00 | 17.71 | C |
| ATOM | 6273 | C | ILE A | 884 | −38.761 | 35.979 | −53.342 | 1.00 | 19.52 | C |
| ATOM | 6274 | O | ILE A | 884 | −38.956 | 37.139 | −53.738 | 1.00 | 19.60 | O |
| ATOM | 6275 | N | ASN A | 885 | −38.707 | 34.921 | −54.148 | 1.00 | 20.36 | N |
| ATOM | 6276 | CA | ASN A | 885 | −38.455 | 35.028 | −55.586 | 1.00 | 20.32 | C |
| ATOM | 6277 | CB | ASN A | 885 | −39.753 | 35.193 | −56.393 | 1.00 | 20.59 | C |
| ATOM | 6278 | CG | ASN A | 885 | −40.620 | 33.929 | −56.364 | 1.00 | 21.61 | C |
| ATOM | 6279 | OD1 | ASN A | 885 | −40.107 | 32.798 | −56.372 | 1.00 | 22.03 | O |
| ATOM | 6280 | ND2 | ASN A | 885 | −41.936 | 34.114 | −56.318 | 1.00 | 21.07 | N |
| ATOM | 6281 | C | ASN A | 885 | −37.415 | 36.097 | −55.869 | 1.00 | 20.10 | C |
| ATOM | 6282 | O | ASN A | 885 | −36.254 | 35.941 | −55.473 | 1.00 | 20.00 | O |
| ATOM | 6283 | N | SER A | 886 | −37.822 | 37.185 | −56.512 | 1.00 | 19.72 | N |
| ATOM | 6284 | CA | SER A | 886 | −36.886 | 38.239 | −56.874 | 1.00 | 19.27 | C |
| ATOM | 6285 | CB | SER A | 886 | −37.020 | 38.572 | −58.346 | 1.00 | 19.09 | C |
| ATOM | 6286 | OG | SER A | 886 | −38.314 | 39.070 | −58.613 | 1.00 | 19.98 | O |
| ATOM | 6287 | C | SER A | 886 | −37.132 | 39.469 | −56.019 | 1.00 | 19.37 | C |
| ATOM | 6288 | O | SER A | 886 | −36.973 | 40.611 | −56.478 | 1.00 | 19.53 | O |
| ATOM | 6289 | N | THR A | 887 | −37.531 | 39.220 | −54.772 | 1.00 | 19.12 | N |
| ATOM | 6290 | CA | THR A | 887 | −37.837 | 40.274 | −53.813 | 1.00 | 18.61 | C |
| ATOM | 6291 | CB | THR A | 887 | −39.352 | 40.337 | −53.514 | 1.00 | 18.48 | C |
| ATOM | 6292 | OG1 | THR A | 887 | −40.026 | 40.885 | −54.650 | 1.00 | 18.74 | O |
| ATOM | 6293 | CG2 | THR A | 887 | −39.649 | 41.229 | −52.330 | 1.00 | 18.65 | C |
| ATOM | 6294 | C | THR A | 887 | −37.058 | 40.020 | −52.544 | 1.00 | 18.12 | C |
| ATOM | 6295 | O | THR A | 887 | −36.906 | 38.876 | −52.132 | 1.00 | 18.21 | O |
| ATOM | 6296 | N | VAL A | 888 | −36.538 | 41.088 | −51.950 | 1.00 | 17.77 | N |
| ATOM | 6297 | CA | VAL A | 888 | −35.946 | 41.016 | −50.618 | 1.00 | 17.71 | C |

-continued

| | | | Atomic coordinates for CRBN:DDB1:Lenalidomide (Human protein) | | | | | | |
|---|---|---|---|---|---|---|---|---|---|
| ATOM | 6298 | CB | VAL A | 888 | −34.512 | 41.598 | −50.581 | 1.00 | 18.13 | C |
| ATOM | 6299 | CG1 | VAL A | 888 | −33.995 | 41.691 | −49.154 | 1.00 | 18.02 | C |
| ATOM | 6300 | CG2 | VAL A | 888 | −33.569 | 40.738 | −51.412 | 1.00 | 18.14 | C |
| ATOM | 6301 | C | VAL A | 888 | −36.875 | 41.734 | −49.645 | 1.00 | 17.36 | C |
| ATOM | 6302 | O | VAL A | 888 | −37.309 | 42.846 | −49.898 | 1.00 | 17.71 | O |
| ATOM | 6303 | N | ARG A | 889 | −37.183 | 41.075 | −48.537 | 1.00 | 17.20 | N |
| ATOM | 6304 | CA | ARG A | 889 | −38.275 | 41.487 | −47.667 | 1.00 | 16.90 | C |
| ATOM | 6305 | CB | ARG A | 889 | −39.477 | 40.566 | −47.909 | 1.00 | 17.07 | C |
| ATOM | 6306 | CG | ARG A | 889 | −40.735 | 40.929 | −47.150 | 1.00 | 17.58 | C |
| ATOM | 6307 | CD | ARG A | 889 | −41.952 | 40.302 | −47.801 | 1.00 | 18.12 | C |
| ATOM | 6308 | NE | ARG A | 889 | −41.972 | 40.503 | −49.252 | 1.00 | 18.75 | N |
| ATOM | 6309 | CZ | ARG A | 889 | −42.761 | 39.828 | −50.095 | 1.00 | 18.84 | C |
| ATOM | 6310 | NH1 | ARG A | 889 | −43.607 | 38.918 | −49.647 | 1.00 | 18.44 | N |
| ATOM | 6311 | NH2 | ARG A | 889 | −42.703 | 40.093 | −51.396 | 1.00 | 19.11 | N |
| ATOM | 6312 | C | ARG A | 889 | −37.836 | 41.414 | −46.211 | 1.00 | 16.41 | C |
| ATOM | 6313 | O | ARG A | 889 | −37.237 | 40.422 | −45.775 | 1.00 | 15.81 | O |
| ATOM | 6314 | N | LEU A | 890 | −38.133 | 42.467 | −45.462 | 1.00 | 16.00 | N |
| ATOM | 6315 | CA | LEU A | 890 | −37.735 | 42.532 | −44.071 | 1.00 | 16.25 | C |
| ATOM | 6316 | CB | LEU A | 890 | −36.936 | 43.808 | −43.818 | 1.00 | 16.26 | C |
| ATOM | 6317 | CG | LEU A | 890 | −36.307 | 44.014 | −42.438 | 1.00 | 16.53 | C |
| ATOM | 6318 | CD1 | LEU A | 890 | −35.339 | 42.887 | −42.098 | 1.00 | 16.40 | C |
| ATOM | 6319 | CD2 | LEU A | 890 | −35.614 | 45.374 | −42.369 | 1.00 | 16.61 | C |
| ATOM | 6320 | C | LEU A | 890 | −38.967 | 42.471 | −43.185 | 1.00 | 16.53 | C |
| ATOM | 6321 | O | LEU A | 890 | −39.934 | 43.170 | −43.435 | 1.00 | 16.79 | O |
| ATOM | 6322 | N | TYR A | 891 | −38.922 | 41.634 | −42.151 | 1.00 | 16.83 | N |
| ATOM | 6323 | CA | TYR A | 891 | −40.093 | 41.353 | −41.306 | 1.00 | 16.82 | C |
| ATOM | 6324 | CB | TYR A | 891 | −40.389 | 39.845 | −41.309 | 1.00 | 16.58 | C |
| ATOM | 6325 | CG | TYR A | 891 | −40.942 | 39.316 | −42.621 | 1.00 | 16.48 | C |
| ATOM | 6326 | CD1 | TYR A | 891 | −42.275 | 39.540 | −42.981 | 1.00 | 16.57 | C |
| ATOM | 6327 | CE1 | TYR A | 891 | −42.791 | 39.062 | −44.168 | 1.00 | 16.35 | C |
| ATOM | 6328 | CZ | TYR A | 891 | −41.979 | 38.347 | −45.016 | 1.00 | 16.63 | C |
| ATOM | 6329 | OH | TYR A | 891 | −42.495 | 37.875 | −46.197 | 1.00 | 16.85 | O |
| ATOM | 6330 | CE2 | TYR A | 891 | −40.655 | 38.106 | −44.689 | 1.00 | 16.65 | C |
| ATOM | 6331 | CD2 | TYR A | 891 | −40.144 | 38.589 | −43.493 | 1.00 | 16.42 | C |
| ATOM | 6332 | C | TYR A | 891 | −39.826 | 41.789 | −39.884 | 1.00 | 17.09 | C |
| ATOM | 6333 | O | TYR A | 891 | −38.736 | 41.532 | −39.371 | 1.00 | 17.71 | O |
| ATOM | 6334 | N | GLU A | 892 | −40.800 | 42.442 | −39.244 | 1.00 | 17.35 | N |
| ATOM | 6335 | CA | GLU A | 892 | −40.727 | 42.724 | −37.792 | 1.00 | 17.65 | C |
| ATOM | 6336 | CB | GLU A | 892 | −41.206 | 44.143 | −37.457 | 1.00 | 18.74 | C |
| ATOM | 6337 | CG | GLU A | 892 | −40.108 | 45.206 | −37.533 | 1.00 | 20.80 | C |
| ATOM | 6338 | CD | GLU A | 892 | −40.602 | 46.623 | −37.194 | 1.00 | 22.45 | C |
| ATOM | 6339 | OE1 | GLU A | 892 | −40.709 | 46.975 | −35.989 | 1.00 | 22.80 | O |
| ATOM | 6340 | OE2 | GLU A | 892 | −40.869 | 47.404 | −38.138 | 1.00 | 23.46 | O |
| ATOM | 6341 | C | GLU A | 892 | −41.510 | 41.679 | −36.990 | 1.00 | 17.03 | C |
| ATOM | 6342 | O | GLU A | 892 | −42.537 | 41.184 | −37.447 | 1.00 | 16.91 | O |
| ATOM | 6343 | N | TRP A | 893 | −41.009 | 41.340 | −35.806 | 1.00 | 16.58 | N |
| ATOM | 6344 | CA | TRP A | 893 | −41.624 | 40.332 | −34.950 | 1.00 | 16.49 | C |
| ATOM | 6345 | CB | TRP A | 893 | −40.546 | 39.423 | −34.394 | 1.00 | 16.33 | C |
| ATOM | 6346 | CG | TRP A | 893 | −41.040 | 38.239 | −33.592 | 1.00 | 16.06 | C |
| ATOM | 6347 | CD1 | TRP A | 893 | −40.755 | 37.937 | −32.265 | 1.00 | 15.88 | C |
| ATOM | 6348 | NE1 | TRP A | 893 | −41.363 | 36.770 | −31.887 | 1.00 | 15.87 | N |
| ATOM | 6349 | CE2 | TRP A | 893 | −42.062 | 36.245 | −32.911 | 1.00 | 16.00 | C |
| ATOM | 6350 | CD2 | TRP A | 893 | −41.890 | 37.140 | −34.056 | 1.00 | 16.02 | C |
| ATOM | 6351 | CE3 | TRP A | 893 | −42.519 | 36.827 | −35.260 | 1.00 | 16.25 | C |
| ATOM | 6352 | CZ3 | TRP A | 893 | −43.290 | 35.664 | −35.327 | 1.00 | 16.26 | C |
| ATOM | 6353 | CH2 | TRP A | 893 | −43.446 | 34.819 | −34.214 | 1.00 | 16.36 | C |
| ATOM | 6354 | CZ2 | TRP A | 893 | −42.830 | 35.094 | −32.987 | 1.00 | 16.22 | C |
| ATOM | 6355 | C | TRP A | 893 | −42.366 | 40.995 | −33.830 | 1.00 | 17.01 | C |
| ATOM | 6356 | O | TRP A | 893 | −41.759 | 41.490 | −32.884 | 1.00 | 17.17 | O |
| ATOM | 6357 | N | THR A | 894 | −43.692 | 40.997 | −33.926 | 1.00 | 17.68 | N |
| ATOM | 6358 | CA | THR A | 894 | −44.548 | 41.765 | −33.019 | 1.00 | 18.58 | C |
| ATOM | 6359 | CB | THR A | 894 | −45.905 | 42.064 | −33.674 | 1.00 | 18.22 | C |
| ATOM | 6360 | OG1 | THR A | 894 | −46.649 | 40.850 | −33.792 | 1.00 | 18.43 | O |
| ATOM | 6361 | CG2 | THR A | 894 | −45.713 | 42.650 | −35.057 | 1.00 | 18.19 | C |
| ATOM | 6362 | C | THR A | 894 | −44.777 | 41.045 | −31.677 | 1.00 | 19.68 | C |
| ATOM | 6363 | O | THR A | 894 | −44.288 | 39.932 | −31.462 | 1.00 | 19.77 | O |
| ATOM | 6364 | N | THR A | 895 | −45.513 | 41.683 | −30.772 | 1.00 | 20.47 | N |
| ATOM | 6365 | CA | THR A | 895 | −45.857 | 41.031 | −29.513 | 1.00 | 21.49 | C |
| ATOM | 6366 | CB | THR A | 895 | −46.065 | 42.037 | −28.354 | 1.00 | 21.98 | C |
| ATOM | 6367 | OG1 | THR A | 895 | −47.124 | 42.948 | −28.687 | 1.00 | 22.01 | O |
| ATOM | 6368 | CG2 | THR A | 895 | −44.759 | 42.809 | −28.030 | 1.00 | 21.43 | C |
| ATOM | 6369 | C | THR A | 895 | −47.105 | 40.167 | −29.685 | 1.00 | 21.83 | C |
| ATOM | 6370 | O | THR A | 895 | −47.398 | 39.310 | −28.853 | 1.00 | 22.31 | O |
| ATOM | 6371 | N | GLU A | 896 | −47.841 | 40.398 | −30.766 | 1.00 | 22.28 | N |
| ATOM | 6372 | CA | GLU A | 896 | −48.968 | 39.538 | −31.110 | 1.00 | 22.72 | C |
| ATOM | 6373 | CB | GLU A | 896 | −49.851 | 40.186 | −32.189 | 1.00 | 22.55 | C |
| ATOM | 6374 | C | GLU A | 896 | −48.409 | 38.199 | −31.581 | 1.00 | 23.10 | C |

-continued

| | | | | | | | | | |
|---|---|---|---|---|---|---|---|---|---|
| Atomic coordinates for CRBN:DDB1:Lenalidomide (Human protein) | | | | | | | | | |
| ATOM | 6375 | O | GLU A | 896 | −49.162 | 37.256 | −31.847 | 1.00 | 23.13 | O |
| ATOM | 6376 | N | LYS A | 897 | −47.075 | 38.133 | −31.650 | 1.00 | 23.63 | N |
| ATOM | 6377 | CA | LYS A | 897 | −46.324 | 36.933 | −32.058 | 1.00 | 24.67 | C |
| ATOM | 6378 | CB | LYS A | 897 | −46.574 | 35.767 | −31.088 | 1.00 | 23.88 | C |
| ATOM | 6379 | CG | LYS A | 897 | −45.329 | 34.958 | −30.756 | 1.00 | 23.49 | C |
| ATOM | 6380 | CD | LYS A | 897 | −45.302 | 34.458 | −29.313 | 1.00 | 23.13 | C |
| ATOM | 6381 | CE | LYS A | 897 | −44.833 | 35.558 | −28.374 | 1.00 | 23.60 | C |
| ATOM | 6382 | NZ | LYS A | 897 | −44.503 | 35.039 | −27.019 | 1.00 | 24.01 | N |
| ATOM | 6383 | C | LYS A | 897 | −46.580 | 36.568 | −33.545 | 1.00 | 25.81 | C |
| ATOM | 6384 | O | LYS A | 897 | −46.935 | 35.431 | −33.892 | 1.00 | 25.41 | O |
| ATOM | 6385 | N | GLU A | 898 | −46.381 | 37.570 | −34.403 | 1.00 | 26.30 | N |
| ATOM | 6386 | CA | GLU A | 898 | −46.616 | 37.461 | −35.822 | 1.00 | 27.13 | C |
| ATOM | 6387 | CB | GLU A | 898 | −47.990 | 38.056 | −36.172 | 1.00 | 30.59 | C |
| ATOM | 6388 | CG | GLU A | 898 | −48.918 | 37.135 | −36.972 | 1.00 | 35.94 | C |
| ATOM | 6389 | CD | GLU A | 898 | −48.433 | 36.849 | −38.412 | 1.00 | 41.31 | C |
| ATOM | 6390 | OE1 | GLU A | 898 | −47.466 | 36.049 | −38.589 | 1.00 | 40.98 | O |
| ATOM | 6391 | OE2 | GLU A | 898 | −49.039 | 37.402 | −39.377 | 1.00 | 41.89 | O |
| ATOM | 6392 | C | GLU A | 898 | −45.498 | 38.227 | −36.530 | 1.00 | 25.32 | C |
| ATOM | 6393 | O | GLU A | 898 | −44.866 | 39.090 | −35.928 | 1.00 | 23.86 | O |
| ATOM | 6394 | N | LEU A | 899 | −45.239 | 37.865 | −37.790 | 1.00 | 24.76 | N |
| ATOM | 6395 | CA | LEU A | 899 | −44.238 | 38.517 | −38.641 | 1.00 | 24.01 | C |
| ATOM | 6396 | CB | LEU A | 899 | −43.544 | 37.504 | −39.552 | 1.00 | 22.22 | C |
| ATOM | 6397 | CG | LEU A | 899 | −42.512 | 36.524 | −39.022 | 1.00 | 21.35 | C |
| ATOM | 6398 | CD1 | LEU A | 899 | −42.298 | 35.403 | −40.026 | 1.00 | 21.07 | C |
| ATOM | 6399 | CD2 | LEU A | 899 | −41.211 | 37.247 | −38.762 | 1.00 | 21.37 | C |
| ATOM | 6400 | C | LEU A | 899 | −44.950 | 39.512 | −39.519 | 1.00 | 25.43 | C |
| ATOM | 6401 | O | LEU A | 899 | −45.770 | 39.120 | −40.349 | 1.00 | 26.96 | O |
| ATOM | 6402 | N | ARG A | 900 | −44.624 | 40.791 | −39.355 | 1.00 | 25.97 | N |
| ATOM | 6403 | CA | ARG A | 900 | −45.360 | 41.882 | −39.998 | 1.00 | 26.03 | C |
| ATOM | 6404 | CB | ARG A | 900 | −46.022 | 42.757 | −38.896 | 1.00 | 27.98 | C |
| ATOM | 6405 | CG | ARG A | 900 | −46.954 | 43.901 | −39.331 | 1.00 | 31.45 | C |
| ATOM | 6406 | CD | ARG A | 900 | −48.448 | 43.537 | −39.491 | 1.00 | 34.20 | C |
| ATOM | 6407 | NE | ARG A | 900 | −49.036 | 42.779 | −38.372 | 1.00 | 35.31 | N |
| ATOM | 6408 | CZ | ARG A | 900 | −49.384 | 41.487 | −38.424 | 1.00 | 35.67 | C |
| ATOM | 6409 | NH1 | ARG A | 900 | −49.216 | 40.786 | −39.542 | 1.00 | 36.08 | N |
| ATOM | 6410 | NH2 | ARG A | 900 | −49.904 | 40.888 | −37.354 | 1.00 | 35.17 | N |
| ATOM | 6411 | C | ARG A | 900 | −44.389 | 42.665 | −40.925 | 1.00 | 24.45 | C |
| ATOM | 6412 | O | ARG A | 900 | −43.506 | 43.375 | −40.445 | 1.00 | 24.91 | O |
| ATOM | 6413 | N | THR A | 901 | −44.546 | 42.485 | −42.242 | 1.00 | 22.09 | N |
| ATOM | 6414 | CA | THR A | 901 | −43.694 | 43.097 | −43.275 | 1.00 | 20.24 | C |
| ATOM | 6415 | CB | THR A | 901 | −44.339 | 43.006 | −44.671 | 1.00 | 19.55 | C |
| ATOM | 6416 | OG1 | THR A | 901 | −44.862 | 41.702 | −44.878 | 1.00 | 19.98 | O |
| ATOM | 6417 | CG2 | THR A | 901 | −43.334 | 43.293 | −45.764 | 1.00 | 19.67 | C |
| ATOM | 6418 | C | THR A | 901 | −43.426 | 44.570 | −43.034 | 1.00 | 20.28 | C |
| ATOM | 6419 | O | THR A | 901 | −44.354 | 45.371 | −43.023 | 1.00 | 20.42 | O |
| ATOM | 6420 | N | GLU A | 902 | −42.153 | 44.925 | −42.862 | 1.00 | 20.49 | N |
| ATOM | 6421 | CA | GLU A | 902 | −41.758 | 46.317 | −42.717 | 1.00 | 20.35 | C |
| ATOM | 6422 | CB | GLU A | 902 | −40.547 | 46.488 | −41.801 | 1.00 | 20.52 | C |
| ATOM | 6423 | CG | GLU A | 902 | −40.178 | 47.954 | −41.575 | 1.00 | 20.98 | C |
| ATOM | 6424 | CD | GLU A | 902 | −38.758 | 48.165 | −41.046 | 1.00 | 21.77 | C |
| ATOM | 6425 | OE1 | GLU A | 902 | −38.151 | 47.206 | −40.514 | 1.00 | 22.18 | O |
| ATOM | 6426 | OE2 | GLU A | 902 | −38.244 | 49.305 | −41.152 | 1.00 | 21.77 | O |
| ATOM | 6427 | C | GLU A | 902 | −41.472 | 46.920 | −44.068 | 1.00 | 20.48 | C |
| ATOM | 6428 | O | GLU A | 902 | −41.912 | 48.036 | −44.334 | 1.00 | 21.13 | O |
| ATOM | 6429 | N | CYS A | 903 | −40.731 | 46.198 | −44.912 | 1.00 | 20.24 | N |
| ATOM | 6430 | CA | CYS A | 903 | −40.402 | 46.684 | −46.259 | 1.00 | 20.66 | C |
| ATOM | 6431 | CB | CYS A | 903 | −39.445 | 47.869 | −46.212 | 1.00 | 20.57 | C |
| ATOM | 6432 | SG | CYS A | 903 | −37.782 | 47.452 | −45.668 | 1.00 | 21.54 | S |
| ATOM | 6433 | C | CYS A | 903 | −39.881 | 45.613 | −47.217 | 1.00 | 21.58 | C |
| ATOM | 6434 | O | CYS A | 903 | −39.724 | 44.442 | −46.853 | 1.00 | 22.64 | O |
| ATOM | 6435 | N | ASN A | 904 | −39.576 | 46.043 | −48.435 | 1.00 | 21.65 | N |
| ATOM | 6436 | CA | ASN A | 904 | −39.694 | 45.196 | −49.593 | 1.00 | 21.99 | C |
| ATOM | 6437 | CB | ASN A | 904 | −41.166 | 45.191 | −49.986 | 1.00 | 22.04 | C |
| ATOM | 6438 | CG | ASN A | 904 | −41.515 | 44.087 | −50.945 | 1.00 | 22.86 | C |
| ATOM | 6439 | OD1 | ASN A | 904 | −41.738 | 42.937 | −50.541 | 1.00 | 22.71 | O |
| ATOM | 6440 | ND2 | ASN A | 904 | −41.603 | 44.431 | −52.229 | 1.00 | 23.05 | N |
| ATOM | 6441 | C | ASN A | 904 | −38.879 | 45.789 | −50.726 | 1.00 | 23.02 | C |
| ATOM | 6442 | O | ASN A | 904 | −39.012 | 46.967 | −51.013 | 1.00 | 24.75 | O |
| ATOM | 6443 | N | HIS A | 905 | −38.041 | 44.986 | −51.379 | 1.00 | 23.95 | N |
| ATOM | 6444 | CA | HIS A | 905 | −37.214 | 45.485 | −52.489 | 1.00 | 24.08 | C |
| ATOM | 6445 | CB | HIS A | 905 | −35.794 | 45.764 | −52.024 | 1.00 | 24.63 | C |
| ATOM | 6446 | CG | HIS A | 905 | −35.008 | 46.646 | −52.968 | 1.00 | 25.31 | C |
| ATOM | 6447 | ND1 | HIS A | 905 | −34.040 | 46.165 | −53.777 | 1.00 | 25.28 | N |
| ATOM | 6448 | CE1 | HIS A | 905 | −33.510 | 47.178 | −54.493 | 1.00 | 25.54 | C |
| ATOM | 6449 | NE2 | HIS A | 905 | −34.146 | 48.314 | −54.143 | 1.00 | 25.75 | N |
| ATOM | 6450 | CD2 | HIS A | 905 | −35.076 | 48.023 | −53.208 | 1.00 | 25.43 | C |
| ATOM | 6451 | C | HIS A | 905 | −37.195 | 44.571 | −53.675 | 1.00 | 23.79 | C |

| | | | | | -continued | | | | |
|---|---|---|---|---|---|---|---|---|---|
| Atomic coordinates for CRBN:DDB1:Lenalidomide (Human protein) | | | | | | | | | |
| ATOM | 6452 | O | HIS A | 905 | −36.843 | 43.402 | −53.564 | 1.00 | 23.89 | O |
| ATOM | 6453 | N | TYR A | 906 | −37.571 | 45.110 | −54.828 | 1.00 | 24.09 | N |
| ATOM | 6454 | CA | TYR A | 906 | −37.627 | 44.344 | −56.070 | 1.00 | 24.63 | C |
| ATOM | 6455 | CB | TYR A | 906 | −38.769 | 44.847 | −56.944 | 1.00 | 25.38 | C |
| ATOM | 6456 | CG | TYR A | 906 | −40.118 | 44.854 | −56.270 | 1.00 | 26.41 | C |
| ATOM | 6457 | CD1 | TYR A | 906 | −40.861 | 43.675 | −56.143 | 1.00 | 26.94 | C |
| ATOM | 6458 | CE1 | TYR A | 906 | −42.104 | 43.671 | −55.536 | 1.00 | 28.09 | C |
| ATOM | 6459 | CZ | TYR A | 906 | −42.629 | 44.864 | −55.057 | 1.00 | 28.94 | C |
| ATOM | 6460 | OH | TYR A | 906 | −43.870 | 44.864 | −54.453 | 1.00 | 30.01 | O |
| ATOM | 6461 | CE2 | TYR A | 906 | −41.912 | 46.050 | −55.178 | 1.00 | 28.05 | C |
| ATOM | 6462 | CD2 | TYR A | 906 | −40.667 | 46.039 | −55.781 | 1.00 | 26.63 | C |
| ATOM | 6463 | C | TYR A | 906 | −36.330 | 44.492 | −56.840 | 1.00 | 24.21 | C |
| ATOM | 6464 | O | TYR A | 906 | −35.773 | 45.580 | −56.905 | 1.00 | 25.09 | O |
| ATOM | 6465 | N | ASN A | 907 | −35.861 | 43.410 | −57.445 | 1.00 | 22.99 | N |
| ATOM | 6466 | CA | ASN A | 907 | −34.583 | 43.437 | −58.123 | 1.00 | 22.83 | C |
| ATOM | 6467 | CB | ASN A | 907 | −33.573 | 42.525 | −57.397 | 1.00 | 23.30 | C |
| ATOM | 6468 | CG | ASN A | 907 | −33.578 | 42.703 | −55.874 | 1.00 | 23.07 | C |
| ATOM | 6469 | OD1 | ASN A | 907 | −33.465 | 43.819 | −55.361 | 1.00 | 23.20 | O |
| ATOM | 6470 | ND2 | ASN A | 907 | −33.692 | 41.590 | −55.149 | 1.00 | 22.71 | N |
| ATOM | 6471 | C | ASN A | 907 | −34.755 | 42.967 | −59.552 | 1.00 | 23.33 | C |
| ATOM | 6472 | O | ASN A | 907 | −35.815 | 42.455 | −59.908 | 1.00 | 23.56 | O |
| ATOM | 6473 | N | ASN A | 908 | −33.708 | 43.133 | −60.364 | 1.00 | 24.13 | N |
| ATOM | 6474 | CA | ASN A | 908 | −33.625 | 42.540 | −61.719 | 1.00 | 24.04 | C |
| ATOM | 6475 | CB | ASN A | 908 | −32.570 | 43.264 | −62.525 | 1.00 | 24.76 | C |
| ATOM | 6476 | CG | ASN A | 908 | −32.828 | 44.724 | −62.604 | 1.00 | 27.19 | C |
| ATOM | 6477 | OD1 | ASN A | 908 | −31.916 | 45.537 | −62.443 | 1.00 | 29.04 | O |
| ATOM | 6478 | ND2 | ASN A | 908 | −34.091 | 45.087 | −62.838 | 1.00 | 27.98 | N |
| ATOM | 6479 | C | ASN A | 908 | −33.252 | 41.060 | −61.737 | 1.00 | 23.61 | C |
| ATOM | 6480 | O | ASN A | 908 | −33.055 | 40.468 | −62.807 | 1.00 | 23.65 | O |
| ATOM | 6481 | N | ILE A | 909 | −33.114 | 40.480 | −60.553 | 1.00 | 22.41 | N |
| ATOM | 6482 | CA | ILE A | 909 | −32.536 | 39.167 | −60.405 | 1.00 | 22.04 | C |
| ATOM | 6483 | CB | ILE A | 909 | −31.027 | 39.227 | −60.088 | 1.00 | 21.03 | C |
| ATOM | 6484 | CG1 | ILE A | 909 | −30.750 | 40.195 | −58.945 | 1.00 | 20.08 | C |
| ATOM | 6485 | CD1 | ILE A | 909 | −29.529 | 39.844 | −58.152 | 1.00 | 20.02 | C |
| ATOM | 6486 | CG2 | ILE A | 909 | −30.239 | 39.616 | −61.324 | 1.00 | 21.43 | C |
| ATOM | 6487 | C | ILE A | 909 | −33.245 | 38.468 | −59.276 | 1.00 | 22.47 | C |
| ATOM | 6488 | O | ILE A | 909 | −33.775 | 39.114 | −58.372 | 1.00 | 22.85 | O |
| ATOM | 6489 | N | MET A | 910 | −33.253 | 37.147 | −59.331 | 1.00 | 22.52 | N |
| ATOM | 6490 | CA | MET A | 910 | −33.905 | 36.371 | −58.319 | 1.00 | 23.20 | C |
| ATOM | 6491 | CB | MET A | 910 | −34.227 | 34.996 | −58.876 | 1.00 | 25.81 | C |
| ATOM | 6492 | CG | MET A | 910 | −34.409 | 33.908 | −57.835 | 1.00 | 29.32 | C |
| ATOM | 6493 | SD | MET A | 910 | −34.334 | 32.291 | −58.629 | 1.00 | 35.22 | S |
| ATOM | 6494 | CE | MET A | 910 | −35.155 | 32.681 | −60.191 | 1.00 | 31.75 | C |
| ATOM | 6495 | C | MET A | 910 | −32.979 | 36.294 | −57.114 | 1.00 | 22.33 | C |
| ATOM | 6496 | O | MET A | 910 | −31.869 | 35.789 | −57.209 | 1.00 | 23.39 | O |
| ATOM | 6497 | N | ALA A | 911 | −33.423 | 36.816 | −55.983 | 1.00 | 20.90 | N |
| ATOM | 6498 | CA | ALA A | 911 | −32.588 | 36.817 | −54.791 | 1.00 | 19.92 | C |
| ATOM | 6499 | CB | ALA A | 911 | −33.184 | 37.733 | −53.741 | 1.00 | 19.82 | C |
| ATOM | 6500 | C | ALA A | 911 | −32.344 | 35.402 | −54.226 | 1.00 | 19.23 | C |
| ATOM | 6501 | O | ALA A | 911 | −32.993 | 34.987 | −53.253 | 1.00 | 18.64 | O |
| ATOM | 6502 | N | LEU A | 912 | −31.421 | 34.668 | −54.858 | 1.00 | 18.33 | N |
| ATOM | 6503 | CA | LEU A | 912 | −31.011 | 33.336 | −54.393 | 1.00 | 17.58 | C |
| ATOM | 6504 | CB | LEU A | 912 | −30.129 | 32.637 | −55.420 | 1.00 | 17.42 | C |
| ATOM | 6505 | CG | LEU A | 912 | −30.671 | 31.507 | −56.284 | 1.00 | 17.74 | C |
| ATOM | 6506 | CD1 | LEU A | 912 | −29.510 | 30.605 | −56.676 | 1.00 | 17.19 | C |
| ATOM | 6507 | CD2 | LEU A | 912 | −31.744 | 30.693 | −55.578 | 1.00 | 17.62 | C |
| ATOM | 6508 | C | LEU A | 912 | −30.223 | 33.435 | −53.106 | 1.00 | 17.16 | C |
| ATOM | 6509 | O | LEU A | 912 | −30.537 | 32.761 | −52.124 | 1.00 | 17.62 | O |
| ATOM | 6510 | N | TYR A | 913 | −29.197 | 34.282 | −53.121 | 1.00 | 16.25 | N |
| ATOM | 6511 | CA | TYR A | 913 | −28.253 | 34.378 | −52.019 | 1.00 | 15.58 | C |
| ATOM | 6512 | CB | TYR A | 913 | −26.837 | 34.384 | −52.555 | 1.00 | 14.89 | C |
| ATOM | 6513 | CG | TYR A | 913 | −26.491 | 33.172 | −53.365 | 1.00 | 14.41 | C |
| ATOM | 6514 | CD1 | TYR A | 913 | −26.161 | 31.978 | −52.747 | 1.00 | 13.89 | C |
| ATOM | 6515 | CE1 | TYR A | 913 | −25.814 | 30.864 | −53.486 | 1.00 | 13.66 | C |
| ATOM | 6516 | CZ | TYR A | 913 | −25.795 | 30.935 | −54.860 | 1.00 | 13.75 | C |
| ATOM | 6517 | OH | TYR A | 913 | −25.475 | 29.824 | −55.578 | 1.00 | 13.46 | O |
| ATOM | 6518 | CE2 | TYR A | 913 | −26.113 | 32.114 | −55.513 | 1.00 | 14.22 | C |
| ATOM | 6519 | CD2 | TYR A | 913 | −26.467 | 33.227 | −54.763 | 1.00 | 14.52 | C |
| ATOM | 6520 | C | TYR A | 913 | −28.466 | 35.623 | −51.194 | 1.00 | 15.43 | C |
| ATOM | 6521 | O | TYR A | 913 | −28.671 | 36.707 | −51.734 | 1.00 | 15.90 | O |
| ATOM | 6522 | N | LEU A | 914 | −28.425 | 35.460 | −49.882 | 1.00 | 15.17 | N |
| ATOM | 6523 | CA | LEU A | 914 | −28.577 | 36.568 | −48.975 | 1.00 | 15.69 | C |
| ATOM | 6524 | CB | LEU A | 914 | −29.955 | 36.565 | −48.330 | 1.00 | 15.79 | C |
| ATOM | 6525 | CG | LEU A | 914 | −30.979 | 37.622 | −48.709 | 1.00 | 15.92 | C |
| ATOM | 6526 | CD1 | LEU A | 914 | −31.989 | 37.768 | −47.583 | 1.00 | 15.73 | C |
| ATOM | 6527 | CD2 | LEU A | 914 | −30.288 | 38.948 | −48.961 | 1.00 | 16.28 | C |
| ATOM | 6528 | C | LEU A | 914 | −27.549 | 36.437 | −47.898 | 1.00 | 16.34 | C |

-continued

| | | | | Atomic coordinates for CRBN:DDB1:Lenalidomide (Human protein) | | | | | |
|---|---|---|---|---|---|---|---|---|---|
| ATOM | 6529 | O | LEU A | 914 | −27.436 | 35.387 | −47.269 | 1.00 | 16.79 | O |
| ATOM | 6530 | N | LYS A | 915 | −26.781 | 37.500 | −47.696 | 1.00 | 16.99 | N |
| ATOM | 6531 | CA | LYS A | 915 | −25.812 | 37.569 | −46.608 | 1.00 | 17.29 | C |
| ATOM | 6532 | CB | LYS A | 915 | −24.427 | 37.106 | −47.080 | 1.00 | 17.36 | C |
| ATOM | 6533 | CG | LYS A | 915 | −24.354 | 35.681 | −47.637 | 1.00 | 17.31 | C |
| ATOM | 6534 | CD | LYS A | 915 | −24.739 | 34.630 | −46.605 | 1.00 | 17.57 | C |
| ATOM | 6535 | CE | LYS A | 915 | −24.187 | 33.250 | −46.949 | 1.00 | 17.81 | C |
| ATOM | 6536 | NZ | LYS A | 915 | −22.750 | 33.079 | −46.541 | 1.00 | 17.47 | N |
| ATOM | 6537 | C | LYS A | 915 | −25.777 | 39.013 | −46.093 | 1.00 | 17.36 | C |
| ATOM | 6538 | O | LYS A | 915 | −26.077 | 39.946 | −46.837 | 1.00 | 16.98 | O |
| ATOM | 6539 | N | THR A | 916 | −25.451 | 39.194 | −44.817 | 1.00 | 17.73 | N |
| ATOM | 6540 | CA | THR A | 916 | −25.489 | 40.521 | −44.224 | 1.00 | 18.65 | C |
| ATOM | 6541 | CB | THR A | 916 | −26.778 | 40.760 | −43.425 | 1.00 | 18.65 | C |
| ATOM | 6542 | OG1 | THR A | 916 | −26.740 | 39.980 | −42.227 | 1.00 | 19.21 | O |
| ATOM | 6543 | CG2 | THR A | 916 | −28.002 | 40.380 | −44.233 | 1.00 | 18.47 | C |
| ATOM | 6544 | C | THR A | 916 | −24.331 | 40.769 | −43.279 | 1.00 | 19.49 | C |
| ATOM | 6545 | O | THR A | 916 | −23.892 | 39.859 | −42.576 | 1.00 | 19.80 | O |
| ATOM | 6546 | N | LYS A | 917 | −23.849 | 42.011 | −43.279 | 1.00 | 20.39 | N |
| ATOM | 6547 | CA | LYS A | 917 | −22.972 | 42.525 | −42.235 | 1.00 | 21.24 | C |
| ATOM | 6548 | CB | LYS A | 917 | −21.522 | 42.611 | −42.712 | 1.00 | 20.85 | C |
| ATOM | 6549 | CG | LYS A | 917 | −20.568 | 43.057 | −41.618 | 1.00 | 21.10 | C |
| ATOM | 6550 | CD | LYS A | 917 | −19.157 | 43.326 | −42.113 | 1.00 | 21.45 | C |
| ATOM | 6551 | CE | LYS A | 917 | −18.205 | 43.376 | −40.924 | 1.00 | 21.80 | C |
| ATOM | 6552 | NZ | LYS A | 917 | −16.945 | 44.116 | −41.213 | 1.00 | 22.54 | N |
| ATOM | 6553 | C | LYS A | 917 | −23.468 | 43.917 | −41.810 | 1.00 | 22.70 | C |
| ATOM | 6554 | O | LYS A | 917 | −23.575 | 44.834 | −42.645 | 1.00 | 23.05 | O |
| ATOM | 6555 | N | GLY A | 918 | −23.763 | 44.069 | −40.516 | 1.00 | 22.74 | N |
| ATOM | 6556 | CA | GLY A | 918 | −24.237 | 45.329 | −39.980 | 1.00 | 22.09 | C |
| ATOM | 6557 | C | GLY A | 918 | −25.526 | 45.689 | −40.669 | 1.00 | 23.04 | C |
| ATOM | 6558 | O | GLY A | 918 | −26.546 | 45.013 | −40.491 | 1.00 | 23.41 | O |
| ATOM | 6559 | N | ASP A | 919 | −25.476 | 46.738 | −41.482 | 1.00 | 23.64 | N |
| ATOM | 6560 | CA | ASP A | 919 | −26.657 | 47.209 | −42.180 | 1.00 | 24.44 | C |
| ATOM | 6561 | CB | ASP A | 919 | −26.895 | 48.695 | −41.913 | 1.00 | 25.73 | C |
| ATOM | 6562 | CG | ASP A | 919 | −28.077 | 48.937 | −40.979 | 1.00 | 27.71 | C |
| ATOM | 6563 | OD1 | ASP A | 919 | −28.497 | 47.982 | −40.275 | 1.00 | 28.90 | O |
| ATOM | 6564 | OD2 | ASP A | 919 | −28.594 | 50.082 | −40.952 | 1.00 | 28.45 | O |
| ATOM | 6565 | C | ASP A | 919 | −26.585 | 46.935 | −43.658 | 1.00 | 24.44 | C |
| ATOM | 6566 | O | ASP A | 919 | −27.500 | 47.274 | −44.400 | 1.00 | 24.92 | O |
| ATOM | 6567 | N | PHE A | 920 | −25.494 | 46.311 | −44.083 | 1.00 | 25.35 | N |
| ATOM | 6568 | CA | PHE A | 920 | −25.289 | 45.972 | −45.494 | 1.00 | 25.43 | C |
| ATOM | 6569 | CB | PHE A | 920 | −23.796 | 46.017 | −45.857 | 1.00 | 26.24 | C |
| ATOM | 6570 | CG | PHE A | 920 | −23.225 | 47.405 | −45.885 | 1.00 | 27.78 | C |
| ATOM | 6571 | CD1 | PHE A | 920 | −22.947 | 48.086 | −44.704 | 1.00 | 28.09 | C |
| ATOM | 6572 | CE1 | PHE A | 920 | −22.436 | 49.379 | −44.728 | 1.00 | 28.88 | C |
| ATOM | 6573 | CZ | PHE A | 920 | −22.182 | 50.007 | −45.941 | 1.00 | 29.19 | C |
| ATOM | 6574 | CE2 | PHE A | 920 | −22.449 | 49.342 | −47.129 | 1.00 | 30.49 | C |
| ATOM | 6575 | CD2 | PHE A | 920 | −22.970 | 48.043 | −47.097 | 1.00 | 30.23 | C |
| ATOM | 6576 | C | PHE A | 920 | −25.901 | 44.611 | −45.832 | 1.00 | 24.33 | C |
| ATOM | 6577 | O | PHE A | 920 | −25.903 | 43.691 | −45.004 | 1.00 | 23.33 | O |
| ATOM | 6578 | N | ILE A | 921 | −26.437 | 44.506 | −47.046 | 1.00 | 23.25 | N |
| ATOM | 6579 | CA | ILE A | 921 | −27.041 | 43.273 | −47.527 | 1.00 | 22.68 | C |
| ATOM | 6580 | CB | ILE A | 921 | −28.580 | 43.406 | −47.581 | 1.00 | 22.82 | C |
| ATOM | 6581 | CG1 | ILE A | 921 | −29.168 | 43.373 | −46.176 | 1.00 | 22.71 | C |
| ATOM | 6582 | CD1 | ILE A | 921 | −30.288 | 44.371 | −45.980 | 1.00 | 23.23 | C |
| ATOM | 6583 | CG2 | ILE A | 921 | −29.206 | 42.286 | −48.389 | 1.00 | 22.94 | C |
| ATOM | 6584 | C | ILE A | 921 | −26.470 | 42.886 | −48.899 | 1.00 | 22.26 | C |
| ATOM | 6585 | O | LEU A | 922 | −26.465 | 43.692 | −49.840 | 1.00 | 22.19 | O |
| ATOM | 6586 | N | LEU A | 922 | −25.976 | 41.656 | −48.992 | 1.00 | 21.51 | N |
| ATOM | 6587 | CA | LEU A | 922 | −25.531 | 41.091 | −50.254 | 1.00 | 21.58 | C |
| ATOM | 6588 | CB | LEU A | 922 | −24.272 | 40.280 | −50.054 | 1.00 | 21.28 | C |
| ATOM | 6589 | CG | LEU A | 922 | −23.661 | 39.843 | −51.369 | 1.00 | 21.46 | C |
| ATOM | 6590 | CD1 | LEU A | 922 | −22.583 | 40.836 | −51.739 | 1.00 | 22.30 | C |
| ATOM | 6591 | CD2 | LEU A | 922 | −23.074 | 38.451 | −51.255 | 1.00 | 21.41 | C |
| ATOM | 6592 | C | LEU A | 922 | −26.600 | 40.189 | −50.844 | 1.00 | 22.33 | C |
| ATOM | 6593 | O | LEU A | 922 | −27.030 | 39.230 | −50.208 | 1.00 | 22.40 | O |
| ATOM | 6594 | N | VAL A | 923 | −27.015 | 40.506 | −52.068 | 1.00 | 23.48 | N |
| ATOM | 6595 | CA | VAL A | 923 | −28.078 | 39.783 | −52.784 | 1.00 | 23.23 | C |
| ATOM | 6596 | CB | VAL A | 923 | −29.214 | 40.737 | −53.187 | 1.00 | 23.45 | C |
| ATOM | 6597 | CG1 | VAL A | 923 | −30.238 | 40.007 | −54.041 | 1.00 | 23.38 | C |
| ATOM | 6598 | CG2 | VAL A | 923 | −29.853 | 41.363 | −51.952 | 1.00 | 23.15 | C |
| ATOM | 6599 | C | VAL A | 923 | −27.498 | 39.214 | −54.063 | 1.00 | 23.21 | C |
| ATOM | 6600 | O | VAL A | 923 | −26.841 | 39.932 | −54.810 | 1.00 | 24.87 | O |
| ATOM | 6601 | N | GLY A | 924 | −27.738 | 37.936 | −54.328 | 1.00 | 22.78 | N |
| ATOM | 6602 | CA | GLY A | 924 | −27.123 | 37.277 | −55.487 | 1.00 | 21.53 | C |
| ATOM | 6603 | C | GLY A | 924 | −28.006 | 36.210 | −56.083 | 1.00 | 20.65 | C |
| ATOM | 6604 | O | GLY A | 924 | −28.924 | 35.723 | −55.422 | 1.00 | 20.93 | O |
| ATOM | 6605 | N | ASP A | 925 | −27.732 | 35.851 | −57.334 | 1.00 | 19.50 | N |

-continued

| | | | Atomic coordinates for CRBN:DDB1:Lenalidomide (Human protein) | | | | | | |
|---|---|---|---|---|---|---|---|---|---|
| ATOM | 6606 | CA  | ASP A | 925 | −28.463 | 34.785 | −58.005 | 1.00 | 18.45 | C |
| ATOM | 6607 | CB  | ASP A | 925 | −29.391 | 35.364 | −59.071 | 1.00 | 18.54 | C |
| ATOM | 6608 | CG  | ASP A | 925 | −28.646 | 35.929 | −60.258 | 1.00 | 18.84 | C |
| ATOM | 6609 | OD1 | ASP A | 925 | −27.428 | 36.197 | −60.157 | 1.00 | 19.03 | O |
| ATOM | 6610 | OD2 | ASP A | 925 | −29.289 | 36.108 | −61.307 | 1.00 | 19.11 | O |
| ATOM | 6611 | C   | ASP A | 925 | −27.542 | 33.740 | −58.616 | 1.00 | 17.66 | C |
| ATOM | 6612 | O   | ASP A | 925 | −26.331 | 33.910 | −58.635 | 1.00 | 16.88 | O |
| ATOM | 6613 | N   | LEU A | 926 | −28.141 | 32.673 | −59.143 | 1.00 | 17.72 | N |
| ATOM | 6614 | CA  | LEU A | 926 | −27.403 | 31.558 | −59.733 | 1.00 | 17.53 | C |
| ATOM | 6615 | CB  | LEU A | 926 | −28.368 | 30.536 | −60.329 | 1.00 | 17.45 | C |
| ATOM | 6616 | CG  | LEU A | 926 | −27.791 | 29.146 | −60.649 | 1.00 | 18.04 | C |
| ATOM | 6617 | CD1 | LEU A | 926 | −27.321 | 28.445 | −59.381 | 1.00 | 18.47 | C |
| ATOM | 6618 | CD2 | LEU A | 926 | −28.769 | 28.254 | −61.406 | 1.00 | 17.82 | C |
| ATOM | 6619 | C   | LEU A | 926 | −26.444 | 32.037 | −60.801 | 1.00 | 17.83 | C |
| ATOM | 6620 | O   | LEU A | 926 | −25.432 | 31.400 | −61.081 | 1.00 | 18.38 | O |
| ATOM | 6621 | N   | MET A | 927 | −26.754 | 33.187 | −61.371 | 1.00 | 18.34 | N |
| ATOM | 6622 | CA  | MET A | 927 | −26.098 | 33.659 | −62.560 | 1.00 | 18.37 | C |
| ATOM | 6623 | CB  | MET A | 927 | −27.115 | 34.357 | −63.443 | 1.00 | 19.07 | C |
| ATOM | 6624 | CG  | MET A | 927 | −26.752 | 34.314 | −64.907 | 1.00 | 20.61 | C |
| ATOM | 6625 | SD  | MET A | 927 | −27.528 | 32.982 | −65.827 | 1.00 | 21.69 | S |
| ATOM | 6626 | CE  | MET A | 927 | −26.511 | 33.036 | −67.296 | 1.00 | 20.80 | C |
| ATOM | 6627 | C   | MET A | 927 | −24.945 | 34.589 | −62.229 | 1.00 | 18.32 | C |
| ATOM | 6628 | O   | MET A | 927 | −24.219 | 35.014 | −63.115 | 1.00 | 18.39 | O |
| ATOM | 6629 | N   | ARG A | 928 | −24.773 | 34.910 | −60.955 | 1.00 | 18.88 | N |
| ATOM | 6630 | CA  | ARG A | 928 | −23.568 | 35.614 | −60.516 | 1.00 | 19.96 | C |
| ATOM | 6631 | CB  | ARG A | 928 | −22.374 | 35.122 | −61.348 | 1.00 | 20.04 | C |
| ATOM | 6632 | CG  | ARG A | 928 | −21.201 | 36.049 | −61.518 | 1.00 | 21.18 | C |
| ATOM | 6633 | CD  | ARG A | 928 | −20.285 | 35.982 | −60.335 | 1.00 | 21.77 | C |
| ATOM | 6634 | NE  | ARG A | 928 | −18.989 | 36.568 | −60.636 | 1.00 | 23.88 | N |
| ATOM | 6635 | CZ  | ARG A | 928 | −18.758 | 37.871 | −60.827 | 1.00 | 26.00 | C |
| ATOM | 6636 | NH1 | ARG A | 928 | −19.753 | 38.772 | −60.793 | 1.00 | 25.61 | N |
| ATOM | 6637 | NH2 | ARG A | 928 | −17.512 | 38.276 | −61.056 | 1.00 | 27.34 | N |
| ATOM | 6638 | C   | ARG A | 928 | −23.738 | 37.149 | −60.512 | 1.00 | 20.62 | C |
| ATOM | 6639 | O   | ARG A | 928 | −22.797 | 37.914 | −60.273 | 1.00 | 20.94 | O |
| ATOM | 6640 | N   | SER A | 929 | −24.962 | 37.590 | −60.743 | 1.00 | 21.01 | N |
| ATOM | 6641 | CA  | SER A | 929 | −25.310 | 38.970 | −60.496 | 1.00 | 21.66 | C |
| ATOM | 6642 | CB  | SER A | 929 | −26.672 | 39.277 | −61.103 | 1.00 | 21.86 | C |
| ATOM | 6643 | OG  | SER A | 929 | −26.788 | 38.671 | −62.378 | 1.00 | 22.71 | O |
| ATOM | 6644 | C   | SER A | 929 | −25.316 | 39.230 | −58.981 | 1.00 | 22.35 | C |
| ATOM | 6645 | O   | SER A | 929 | −25.978 | 38.516 | −58.211 | 1.00 | 22.31 | O |
| ATOM | 6646 | N   | VAL A | 930 | −24.551 | 40.234 | −58.558 | 1.00 | 22.59 | N |
| ATOM | 6647 | CA  | VAL A | 930 | −24.544 | 40.659 | −57.162 | 1.00 | 22.64 | C |
| ATOM | 6648 | CB  | VAL A | 930 | −23.187 | 40.396 | −56.472 | 1.00 | 22.07 | C |
| ATOM | 6649 | CG1 | VAL A | 930 | −22.788 | 38.936 | −56.630 | 1.00 | 21.96 | C |
| ATOM | 6650 | CG2 | VAL A | 930 | −22.106 | 41.295 | −57.037 | 1.00 | 22.34 | C |
| ATOM | 6651 | C   | VAL A | 930 | −25.006 | 42.109 | −56.981 | 1.00 | 23.49 | C |
| ATOM | 6652 | O   | VAL A | 930 | −24.750 | 42.991 | −57.819 | 1.00 | 23.27 | O |
| ATOM | 6653 | N   | LEU A | 931 | −25.713 | 42.330 | −55.882 | 1.00 | 24.46 | N |
| ATOM | 6654 | CA  | LEU A | 931 | −26.268 | 43.623 | −55.538 | 1.00 | 25.20 | C |
| ATOM | 6655 | CB  | LEU A | 931 | −27.785 | 43.594 | −55.687 | 1.00 | 25.68 | C |
| ATOM | 6656 | CG  | LEU A | 931 | −28.440 | 44.266 | −56.886 | 1.00 | 26.44 | C |
| ATOM | 6657 | CD1 | LEU A | 931 | −28.029 | 43.633 | −58.207 | 1.00 | 27.72 | C |
| ATOM | 6658 | CD2 | LEU A | 931 | −29.944 | 44.194 | −56.712 | 1.00 | 27.28 | C |
| ATOM | 6659 | C   | LEU A | 931 | −25.934 | 43.892 | −54.090 | 1.00 | 26.48 | C |
| ATOM | 6660 | O   | LEU A | 931 | −26.167 | 43.036 | −53.222 | 1.00 | 27.04 | O |
| ATOM | 6661 | N   | LEU A | 932 | −25.378 | 45.071 | −53.822 | 1.00 | 26.60 | N |
| ATOM | 6662 | CA  | LEU A | 932 | −25.193 | 45.509 | −52.454 | 1.00 | 26.57 | C |
| ATOM | 6663 | CB  | LEU A | 932 | −23.833 | 46.193 | −52.276 | 1.00 | 27.14 | C |
| ATOM | 6664 | CG  | LEU A | 932 | −23.375 | 46.330 | −50.813 | 1.00 | 28.96 | C |
| ATOM | 6665 | CD1 | LEU A | 932 | −23.324 | 44.988 | −50.076 | 1.00 | 28.76 | C |
| ATOM | 6666 | CD2 | LEU A | 932 | −22.040 | 47.049 | −50.705 | 1.00 | 29.26 | C |
| ATOM | 6667 | C   | LEU A | 932 | −26.364 | 46.423 | −52.056 | 1.00 | 26.31 | C |
| ATOM | 6668 | O   | LEU A | 932 | −26.755 | 47.295 | −52.823 | 1.00 | 26.28 | O |
| ATOM | 6669 | N   | LEU A | 933 | −26.937 | 46.195 | −50.873 | 1.00 | 25.63 | N |
| ATOM | 6670 | CA  | LEU A | 933 | −28.072 | 46.995 | −50.387 | 1.00 | 24.73 | C |
| ATOM | 6671 | CB  | LEU A | 933 | −29.357 | 46.167 | −50.413 | 1.00 | 24.34 | C |
| ATOM | 6672 | CG  | LEU A | 933 | −29.939 | 45.734 | −51.752 | 1.00 | 23.96 | C |
| ATOM | 6673 | CD1 | LEU A | 933 | −30.902 | 44.592 | −51.512 | 1.00 | 23.57 | C |
| ATOM | 6674 | CD2 | LEU A | 933 | −30.647 | 46.878 | −52.440 | 1.00 | 24.14 | C |
| ATOM | 6675 | C   | LEU A | 933 | −27.860 | 47.552 | −48.973 | 1.00 | 24.49 | C |
| ATOM | 6676 | O   | LEU A | 933 | −27.155 | 46.945 | −48.152 | 1.00 | 25.10 | O |
| ATOM | 6677 | N   | ALA A | 934 | −28.499 | 48.688 | −48.687 | 1.00 | 23.11 | N |
| ATOM | 6678 | CA  | ALA A | 934 | −28.379 | 49.344 | −47.388 | 1.00 | 22.73 | C |
| ATOM | 6679 | CB  | ALA A | 934 | −27.597 | 50.636 | −47.528 | 1.00 | 22.50 | C |
| ATOM | 6680 | C   | ALA A | 934 | −29.736 | 49.626 | −46.747 | 1.00 | 23.17 | C |
| ATOM | 6681 | O   | ALA A | 934 | −30.504 | 50.463 | −47.240 | 1.00 | 23.97 | O |
| ATOM | 6682 | N   | TYR A | 935 | −30.028 | 48.936 | −45.645 | 1.00 | 22.76 | N |

-continued

| | | | Atomic coordinates for CRBN:DDB1:Lenalidomide (Human protein) | | | | | | |
|---|---|---|---|---|---|---|---|---|---|
| ATOM | 6683 | CA | TYR A | 935 | −31.217 | 49.232 | −44.873 | 1.00 | 22.22 | C |
| ATOM | 6684 | CB | TYR A | 935 | −31.430 | 48.225 | −43.750 | 1.00 | 21.84 | C |
| ATOM | 6685 | CG | TYR A | 935 | −32.592 | 48.600 | −42.859 | 1.00 | 21.26 | C |
| ATOM | 6686 | CD1 | TYR A | 935 | −33.884 | 48.680 | −43.376 | 1.00 | 21.48 | C |
| ATOM | 6687 | CE1 | TYR A | 935 | −34.956 | 49.039 | −42.584 | 1.00 | 21.38 | C |
| ATOM | 6688 | CZ | TYR A | 935 | −34.749 | 49.320 | −41.246 | 1.00 | 21.34 | C |
| ATOM | 6689 | OH | TYR A | 935 | −35.829 | 49.677 | −40.471 | 1.00 | 21.19 | O |
| ATOM | 6690 | CE2 | TYR A | 935 | −33.475 | 49.245 | −40.704 | 1.00 | 21.02 | C |
| ATOM | 6691 | CD2 | TYR A | 935 | −32.403 | 48.893 | −41.515 | 1.00 | 20.94 | C |
| ATOM | 6692 | C | TYR A | 935 | −31.036 | 50.593 | −44.262 | 1.00 | 23.03 | C |
| ATOM | 6693 | O | TYR A | 935 | −30.080 | 50.825 | −43.526 | 1.00 | 24.50 | O |
| ATOM | 6694 | N | LYS A | 936 | −31.961 | 51.492 | −44.562 | 1.00 | 23.14 | N |
| ATOM | 6695 | CA | LYS A | 936 | −31.917 | 52.846 | −44.042 | 1.00 | 22.71 | C |
| ATOM | 6696 | CB | LYS A | 936 | −32.132 | 53.843 | −45.184 | 1.00 | 23.45 | C |
| ATOM | 6697 | CG | LYS A | 936 | −31.118 | 53.694 | −46.319 | 1.00 | 23.33 | C |
| ATOM | 6698 | CD | LYS A | 936 | −29.686 | 53.814 | −45.803 | 1.00 | 23.15 | C |
| ATOM | 6699 | CE | LYS A | 936 | −28.892 | 54.849 | −46.589 | 1.00 | 22.99 | C |
| ATOM | 6700 | NZ | LYS A | 936 | −29.630 | 56.133 | −46.729 | 1.00 | 22.36 | N |
| ATOM | 6701 | C | LYS A | 936 | −32.948 | 53.016 | −42.925 | 1.00 | 22.21 | C |
| ATOM | 6702 | O | LYS A | 936 | −34.135 | 53.198 | −43.190 | 1.00 | 21.75 | O |
| ATOM | 6703 | N | PRO A | 937 | −32.492 | 52.928 | −41.663 | 1.00 | 22.32 | N |
| ATOM | 6704 | CA | PRO A | 937 | −33.393 | 52.901 | −40.515 | 1.00 | 22.69 | C |
| ATOM | 6705 | CB | PRO A | 937 | −32.433 | 52.890 | −39.319 | 1.00 | 22.54 | C |
| ATOM | 6706 | CG | PRO A | 937 | −31.213 | 52.214 | −39.841 | 1.00 | 22.25 | C |
| ATOM | 6707 | CD | PRO A | 937 | −31.088 | 52.720 | −41.254 | 1.00 | 22.34 | C |
| ATOM | 6708 | C | PRO A | 937 | −34.335 | 54.093 | −40.448 | 1.00 | 23.45 | C |
| ATOM | 6709 | O | PRO A | 937 | −35.483 | 53.930 | −40.072 | 1.00 | 24.66 | O |
| ATOM | 6710 | N | MET A | 938 | −33.854 | 55.275 | −40.819 | 1.00 | 24.67 | N |
| ATOM | 6711 | CA | MET A | 938 | −34.657 | 56.495 | −40.792 | 1.00 | 25.32 | C |
| ATOM | 6712 | CB | MET A | 938 | −33.748 | 57.719 | −40.793 | 1.00 | 25.66 | C |
| ATOM | 6713 | CG | MET A | 938 | −32.969 | 57.932 | −39.507 | 1.00 | 26.09 | C |
| ATOM | 6714 | SD | MET A | 938 | −32.032 | 59.477 | −39.564 | 1.00 | 28.44 | S |
| ATOM | 6715 | CE | MET A | 938 | −30.734 | 59.068 | −40.739 | 1.00 | 28.03 | C |
| ATOM | 6716 | C | MET A | 938 | −35.638 | 56.577 | −41.962 | 1.00 | 25.82 | C |
| ATOM | 6717 | O | MET A | 938 | −36.542 | 57.412 | −41.967 | 1.00 | 25.83 | O |
| ATOM | 6718 | N | GLU A | 939 | −35.449 | 55.707 | −42.949 | 1.00 | 27.54 | N |
| ATOM | 6719 | CA | GLU A | 939 | −36.294 | 55.651 | −44.134 | 1.00 | 28.84 | C |
| ATOM | 6720 | CB | GLU A | 939 | −35.429 | 55.564 | −45.384 | 1.00 | 32.21 | C |
| ATOM | 6721 | CG | GLU A | 939 | −35.221 | 56.849 | −46.171 | 1.00 | 36.05 | C |
| ATOM | 6722 | CD | GLU A | 939 | −34.341 | 56.624 | −47.412 | 1.00 | 40.07 | C |
| ATOM | 6723 | OE1 | GLU A | 939 | −33.702 | 57.592 | −47.887 | 1.00 | 42.86 | O |
| ATOM | 6724 | OE2 | GLU A | 939 | −34.275 | 55.474 | −47.916 | 1.00 | 40.86 | O |
| ATOM | 6725 | C | GLU A | 939 | −37.246 | 54.452 | −44.113 | 1.00 | 28.14 | C |
| ATOM | 6726 | O | GLU A | 939 | −38.250 | 54.470 | −44.806 | 1.00 | 29.23 | O |
| ATOM | 6727 | N | GLY A | 940 | −36.917 | 53.411 | −43.347 | 1.00 | 27.07 | N |
| ATOM | 6728 | CA | GLY A | 940 | −37.735 | 52.188 | −43.264 | 1.00 | 27.09 | C |
| ATOM | 6729 | C | GLY A | 940 | −37.777 | 51.439 | −44.582 | 1.00 | 27.90 | C |
| ATOM | 6730 | O | GLY A | 940 | −38.832 | 50.989 | −45.026 | 1.00 | 27.05 | O |
| ATOM | 6731 | N | ASN A | 941 | −36.600 | 51.244 | −45.160 | 1.00 | 29.83 | N |
| ATOM | 6732 | CA | ASN A | 941 | −36.436 | 51.240 | −46.599 | 1.00 | 30.69 | C |
| ATOM | 6733 | CB | ASN A | 941 | −36.381 | 52.698 | −47.034 | 1.00 | 34.15 | C |
| ATOM | 6734 | CG | ASN A | 941 | −37.044 | 52.941 | −48.357 | 1.00 | 37.19 | C |
| ATOM | 6735 | OD1 | ASN A | 941 | −37.507 | 52.005 | −49.013 | 1.00 | 41.81 | O |
| ATOM | 6736 | ND2 | ASN A | 941 | −37.101 | 54.210 | −48.765 | 1.00 | 36.07 | N |
| ATOM | 6737 | C | ASN A | 941 | −35.120 | 50.613 | −46.996 | 1.00 | 29.48 | C |
| ATOM | 6738 | O | ASN A | 941 | −34.217 | 50.504 | −46.182 | 1.00 | 30.19 | O |
| ATOM | 6739 | N | PHE A | 942 | −34.995 | 50.222 | −48.255 | 1.00 | 28.70 | N |
| ATOM | 6740 | CA | PHE A | 942 | −33.703 | 49.772 | −48.773 | 1.00 | 28.48 | C |
| ATOM | 6741 | CB | PHE A | 942 | −33.803 | 48.388 | −49.414 | 1.00 | 28.27 | C |
| ATOM | 6742 | CG | PHE A | 942 | −34.078 | 47.289 | −48.440 | 1.00 | 27.77 | C |
| ATOM | 6743 | CD1 | PHE A | 942 | −33.126 | 46.921 | −47.504 | 1.00 | 28.16 | C |
| ATOM | 6744 | CE1 | PHE A | 942 | −33.377 | 45.899 | −46.601 | 1.00 | 28.68 | C |
| ATOM | 6745 | CZ | PHE A | 942 | −34.586 | 45.227 | −49.635 | 1.00 | 28.53 | C |
| ATOM | 6746 | CE2 | PHE A | 942 | −35.540 | 45.584 | −47.574 | 1.00 | 28.49 | C |
| ATOM | 6747 | CD2 | PHE A | 942 | −35.284 | 46.610 | −48.469 | 1.00 | 27.76 | C |
| ATOM | 6748 | C | PHE A | 942 | −33.166 | 50.751 | −49.788 | 1.00 | 28.04 | C |
| ATOM | 6749 | O | PHE A | 942 | −33.914 | 51.545 | −50.346 | 1.00 | 29.19 | O |
| ATOM | 6750 | N | GLU A | 943 | −31.865 | 50.680 | −50.023 | 1.00 | 28.27 | N |
| ATOM | 6751 | CA | GLU A | 943 | −31.195 | 51.536 | −50.989 | 1.00 | 29.79 | C |
| ATOM | 6752 | CB | GLU A | 943 | −30.579 | 52.722 | −50.253 | 1.00 | 30.41 | C |
| ATOM | 6753 | CG | GLU A | 943 | −29.990 | 53.810 | −51.123 | 1.00 | 32.01 | C |
| ATOM | 6754 | CD | GLU A | 943 | −29.054 | 54.720 | −50.338 | 1.00 | 34.90 | C |
| ATOM | 6755 | OE1 | GLU A | 943 | −28.136 | 54.200 | −49.661 | 1.00 | 35.66 | O |
| ATOM | 6756 | OE2 | GLU A | 943 | −29.224 | 55.961 | −50.393 | 1.00 | 36.77 | O |
| ATOM | 6757 | C | GLU A | 943 | −30.111 | 50.699 | −51.668 | 1.00 | 30.23 | C |
| ATOM | 6758 | O | GLU A | 943 | −29.282 | 50.107 | −50.978 | 1.00 | 31.09 | O |
| ATOM | 6759 | N | GLU A | 944 | −30.134 | 50.604 | −53.001 | 1.00 | 29.96 | N |

-continued

| | | | Atomic coordinates for CRBN:DDB1:Lenalidomide (Human protein) | | | | | | |
|---|---|---|---|---|---|---|---|---|---|
| ATOM | 6760 | CA | GLU A | 944 | −29.090 | 49.855 | −53.715 | 1.00 | 29.58 | C |
| ATOM | 6761 | CB | GLU A | 944 | −29.546 | 49.347 | −55.093 | 1.00 | 32.65 | C |
| ATOM | 6762 | CG | GLU A | 944 | −30.490 | 50.270 | −55.860 | 1.00 | 37.83 | C |
| ATOM | 6763 | CD | GLU A | 944 | −31.437 | 49.516 | −56.799 | 1.00 | 40.89 | C |
| ATOM | 6764 | OE1 | GLU A | 944 | −31.033 | 48.455 | −57.352 | 1.00 | 44.05 | O |
| ATOM | 6765 | OE2 | GLU A | 944 | −32.590 | 49.988 | −56.983 | 1.00 | 39.42 | O |
| ATOM | 6766 | C | GLU A | 944 | −27.829 | 50.680 | −53.809 | 1.00 | 27.24 | C |
| ATOM | 6767 | O | GLU A | 944 | −27.869 | 51.816 | −54.248 | 1.00 | 27.45 | O |
| ATOM | 6768 | N | ILE A | 945 | −26.722 | 50.097 | −53.363 | 1.00 | 25.34 | N |
| ATOM | 6769 | CA | ILE A | 945 | −25.448 | 50.793 | −53.213 | 1.00 | 24.83 | C |
| ATOM | 6770 | CB | ILE A | 945 | −24.723 | 50.360 | −51.912 | 1.00 | 24.93 | C |
| ATOM | 6771 | CG1 | ILE A | 945 | −25.575 | 50.685 | −50.680 | 1.00 | 24.76 | C |
| ATOM | 6772 | CD1 | ILE A | 945 | −26.262 | 52.037 | −50.728 | 1.00 | 24.36 | C |
| ATOM | 6773 | CG2 | ILE A | 945 | −23.337 | 50.994 | −51.803 | 1.00 | 24.67 | C |
| ATOM | 6774 | C | ILE A | 945 | −24.538 | 50.526 | −54.406 | 1.00 | 24.45 | C |
| ATOM | 6775 | O | ILE A | 945 | −24.013 | 51.461 | −55.020 | 1.00 | 23.81 | O |
| ATOM | 6776 | N | ALA A | 946 | −24.346 | 49.243 | −54.708 | 1.00 | 24.31 | N |
| ATOM | 6777 | CA | ALA A | 946 | −23.527 | 48.812 | −55.832 | 1.00 | 24.15 | C |
| ATOM | 6778 | CB | ALA A | 946 | −22.112 | 48.506 | −55.380 | 1.00 | 22.95 | C |
| ATOM | 6779 | C | ALA A | 946 | −24.142 | 47.610 | −56.512 | 1.00 | 23.68 | C |
| ATOM | 6780 | O | ALA A | 946 | −25.081 | 47.024 | −56.015 | 1.00 | 23.04 | O |
| ATOM | 6781 | N | ARG A | 947 | −23.577 | 47.228 | −57.641 | 1.00 | 25.66 | N |
| ATOM | 6782 | CA | ARG A | 947 | −24.206 | 46.277 | −58.527 | 1.00 | 28.28 | C |
| ATOM | 6783 | CB | ARG A | 947 | −25.339 | 46.997 | −59.271 | 1.00 | 29.13 | C |
| ATOM | 6784 | CG | ARG A | 947 | −25.768 | 46.398 | −60.594 | 1.00 | 30.25 | C |
| ATOM | 6785 | CD | ARG A | 947 | −26.981 | 47.123 | −61.145 | 1.00 | 30.68 | C |
| ATOM | 6786 | NE | ARG A | 947 | −28.212 | 46.614 | −60.552 | 1.00 | 31.87 | N |
| ATOM | 6787 | CZ | ARG A | 947 | −29.401 | 46.615 | −61.153 | 1.00 | 32.55 | C |
| ATOM | 6788 | NH1 | ARG A | 947 | −29.540 | 47.101 | −62.386 | 1.00 | 32.31 | N |
| ATOM | 6789 | NH2 | ARG A | 947 | −30.459 | 46.120 | −60.517 | 1.00 | 33.09 | N |
| ATOM | 6790 | C | ARG A | 947 | −23.150 | 45.766 | −59.495 | 1.00 | 30.36 | C |
| ATOM | 6791 | O | ARG A | 947 | −22.247 | 46.508 | −59.878 | 1.00 | 31.84 | O |
| ATOM | 6792 | N | ASP A | 948 | −23.241 | 44.497 | −59.872 | 1.00 | 32.63 | N |
| ATOM | 6793 | CA | ASP A | 948 | −22.357 | 43.960 | −60.900 | 1.00 | 34.07 | C |
| ATOM | 6794 | CB | ASP A | 948 | −21.032 | 43.530 | −60.299 | 1.00 | 35.05 | C |
| ATOM | 6795 | CG | ASP A | 948 | −20.007 | 43.199 | −61.353 | 1.00 | 38.19 | C |
| ATOM | 6796 | OD1 | ASP A | 948 | −20.155 | 43.663 | −62.514 | 1.00 | 38.25 | O |
| ATOM | 6797 | OD2 | ASP A | 948 | −19.046 | 42.474 | −61.019 | 1.00 | 40.73 | O |
| ATOM | 6798 | C | ASP A | 948 | −22.972 | 42.791 | −61.644 | 1.00 | 35.34 | C |
| ATOM | 6799 | O | ASP A | 948 | −23.247 | 41.755 | −61.054 | 1.00 | 38.44 | O |
| ATOM | 6800 | N | PHE A | 949 | −23.163 | 42.949 | −62.947 | 1.00 | 35.40 | N |
| ATOM | 6801 | CA | PHE A | 949 | −23.783 | 41.908 | −63.754 | 1.00 | 34.37 | C |
| ATOM | 6802 | CB | PHE A | 949 | −24.966 | 42.470 | −64.553 | 1.00 | 36.98 | C |
| ATOM | 6803 | CG | PHE A | 949 | −26.232 | 42.587 | −63.754 | 1.00 | 39.96 | C |
| ATOM | 6804 | CD1 | PHE A | 949 | −26.329 | 43.490 | −62.690 | 1.00 | 41.30 | C |
| ATOM | 6805 | CE1 | PHE A | 949 | −27.498 | 43.591 | −61.942 | 1.00 | 41.22 | C |
| ATOM | 6806 | CZ | PHE A | 949 | −28.590 | 42.796 | −62.258 | 1.00 | 41.28 | C |
| ATOM | 6807 | CE2 | PHE A | 949 | −28.508 | 41.898 | −63.319 | 1.00 | 41.45 | C |
| ATOM | 6808 | CD2 | PHE A | 949 | −27.335 | 41.796 | −64.060 | 1.00 | 41.23 | C |
| ATOM | 6809 | C | PHE A | 949 | −22.759 | 41.274 | −64.677 | 1.00 | 32.31 | C |
| ATOM | 6810 | O | PHE A | 949 | −22.621 | 41.669 | −65.829 | 1.00 | 35.79 | O |
| ATOM | 6811 | N | ASN A | 950 | −22.048 | 40.283 | −64.161 | 1.00 | 28.49 | N |
| ATOM | 6812 | CA | ASN A | 950 | −21.034 | 39.576 | −64.924 | 1.00 | 26.20 | C |
| ATOM | 6813 | CB | ASN A | 950 | −19.669 | 39.843 | −64.305 | 1.00 | 25.65 | C |
| ATOM | 6814 | CG | ASN A | 950 | −18.537 | 39.343 | −65.150 | 1.00 | 24.84 | C |
| ATOM | 6815 | OD1 | ASN A | 950 | −17.396 | 39.715 | −64.925 | 1.00 | 25.34 | O |
| ATOM | 6816 | ND2 | ASN A | 950 | −18.838 | 38.498 | −66.128 | 1.00 | 24.40 | N |
| ATOM | 6817 | C | ASN A | 950 | −21.332 | 38.071 | −64.975 | 1.00 | 24.85 | C |
| ATOM | 6818 | O | ASN A | 950 | −20.913 | 37.314 | −64.109 | 1.00 | 25.87 | O |
| ATOM | 6819 | N | PRO A | 951 | −22.018 | 37.631 | −66.022 | 1.00 | 23.18 | N |
| ATOM | 6820 | CA | PRO A | 951 | −22.725 | 36.356 | −66.023 | 1.00 | 22.24 | C |
| ATOM | 6821 | CB | PRO A | 951 | −23.494 | 36.388 | −67.358 | 1.00 | 23.09 | C |
| ATOM | 6822 | CG | PRO A | 951 | −23.331 | 37.772 | −67.908 | 1.00 | 22.64 | C |
| ATOM | 6823 | CD | PRO A | 951 | −22.054 | 38.281 | −67.337 | 1.00 | 22.82 | C |
| ATOM | 6824 | C | PRO A | 951 | −21.864 | 35.087 | −65.951 | 1.00 | 21.01 | C |
| ATOM | 6825 | O | PRO A | 951 | −21.310 | 34.664 | −66.956 | 1.00 | 21.07 | O |
| ATOM | 6826 | N | ASN A | 952 | −21.798 | 34.468 | −64.776 | 1.00 | 20.03 | N |
| ATOM | 6827 | CA | ASN A | 952 | −21.258 | 33.102 | −64.624 | 1.00 | 18.90 | C |
| ATOM | 6828 | CB | ASN A | 952 | −19.796 | 33.169 | −64.190 | 1.00 | 18.81 | C |
| ATOM | 6829 | CG | ASN A | 952 | −19.032 | 31.900 | −64.505 | 1.00 | 18.94 | C |
| ATOM | 6830 | OD1 | ASN A | 952 | −19.384 | 31.160 | −65.424 | 1.00 | 19.17 | O |
| ATOM | 6831 | ND2 | ASN A | 952 | −17.967 | 31.650 | −63.757 | 1.00 | 18.75 | N |
| ATOM | 6832 | C | ASN A | 952 | −22.069 | 32.308 | −63.593 | 1.00 | 18.00 | C |
| ATOM | 6833 | O | ASN A | 952 | −22.599 | 32.898 | −62.672 | 1.00 | 18.28 | O |
| ATOM | 6834 | N | TRP A | 953 | −22.182 | 30.988 | −63.734 | 1.00 | 17.13 | N |
| ATOM | 6835 | CA | TRP A | 953 | −22.813 | 30.173 | −62.670 | 1.00 | 16.35 | C |
| ATOM | 6836 | CB | TRP A | 953 | −22.704 | 28.679 | −62.956 | 1.00 | 16.51 | C |

-continued

| | | Atomic coordinates for CRBN:DDB1:Lenalidomide (Human protein) | | | | | | | |
|---|---|---|---|---|---|---|---|---|---|
| ATOM | 6837 | CG | TRP A | 953 | −23.293 | 28.266 | −64.260 | 1.00 | 16.65 | C |
| ATOM | 6838 | CD1 | TRP A | 953 | −22.710 | 27.477 | −65.240 | 1.00 | 16.64 | C |
| ATOM | 6839 | NE1 | TRP A | 953 | −23.555 | 27.337 | −66.320 | 1.00 | 17.21 | N |
| ATOM | 6840 | CE2 | TRP A | 953 | −24.710 | 28.017 | −66.114 | 1.00 | 17.23 | C |
| ATOM | 6841 | CD2 | TRP A | 953 | −24.607 | 28.649 | −64.797 | 1.00 | 17.33 | C |
| ATOM | 6842 | CE3 | TRP A | 953 | −25.671 | 29.441 | −64.333 | 1.00 | 17.03 | C |
| ATOM | 6843 | CZ3 | TRP A | 953 | −26.787 | 29.593 | −65.149 | 1.00 | 16.90 | C |
| ATOM | 6844 | CH2 | TRP A | 953 | −26.864 | 28.972 | −66.409 | 1.00 | 17.16 | C |
| ATOM | 6845 | CZ2 | TRP A | 953 | −25.827 | 28.170 | −66.911 | 1.00 | 17.21 | C |
| ATOM | 6846 | C | TRP A | 953 | −22.130 | 30.446 | −61.377 | 1.00 | 16.09 | C |
| ATOM | 6847 | O | TRP A | 953 | −20.907 | 30.351 | −61.298 | 1.00 | 16.48 | O |
| ATOM | 6848 | N | MET A | 954 | −22.898 | 30.786 | −60.348 | 1.00 | 15.42 | N |
| ATOM | 6849 | CA | MET A | 954 | −22.338 | 31.085 | −59.034 | 1.00 | 14.79 | C |
| ATOM | 6850 | CB | MET A | 954 | −22.587 | 32.543 | −58.681 | 1.00 | 15.51 | C |
| ATOM | 6851 | CG | MET A | 954 | −22.050 | 32.961 | −57.320 | 1.00 | 16.55 | C |
| ATOM | 6852 | SD | MET A | 954 | −22.202 | 34.723 | −56.965 | 1.00 | 17.23 | S |
| ATOM | 6853 | CE | MET A | 954 | −23.900 | 34.829 | −56.419 | 1.00 | 17.22 | C |
| ATOM | 6854 | C | MET A | 954 | −22.986 | 30.181 | −58.003 | 1.00 | 14.29 | C |
| ATOM | 6855 | O | MET A | 954 | −24.206 | 30.014 | −58.021 | 1.00 | 14.53 | O |
| ATOM | 6856 | N | SER A | 955 | −22.184 | 29.627 | −57.088 | 1.00 | 13.42 | N |
| ATOM | 6857 | CA | SER A | 955 | −22.657 | 28.568 | −56.188 | 1.00 | 12.67 | C |
| ATOM | 6858 | CB | SER A | 955 | −21.810 | 27.318 | −56.364 | 1.00 | 12.33 | C |
| ATOM | 6859 | OG | SER A | 955 | −20.510 | 27.499 | −55.846 | 1.00 | 12.20 | O |
| ATOM | 6860 | C | SER A | 955 | −22.747 | 28.915 | −54.706 | 1.00 | 12.55 | C |
| ATOM | 6861 | O | SER A | 955 | −23.382 | 28.193 | −53.932 | 1.00 | 12.48 | O |
| ATOM | 6862 | N | ALA A | 956 | −22.126 | 30.022 | −54.315 | 1.00 | 12.71 | N |
| ATOM | 6863 | CA | ALA A | 956 | −21.998 | 30.392 | −52.903 | 1.00 | 13.19 | C |
| ATOM | 6864 | CB | ALA A | 956 | −21.110 | 29.387 | −52.170 | 1.00 | 12.88 | C |
| ATOM | 6865 | C | ALA A | 956 | −21.387 | 31.784 | −52.820 | 1.00 | 13.75 | C |
| ATOM | 6866 | O | ALA A | 956 | −20.524 | 32.120 | −53.624 | 1.00 | 14.46 | O |
| ATOM | 6867 | N | VAL A | 957 | −21.834 | 32.596 | −51.865 | 1.00 | 14.16 | N |
| ATOM | 6868 | CA | VAL A | 957 | −21.198 | 33.883 | −51.593 | 1.00 | 14.52 | C |
| ATOM | 6869 | CB | VAL A | 957 | −21.952 | 35.086 | −52.201 | 1.00 | 14.45 | C |
| ATOM | 6870 | CG1 | VAL A | 957 | −21.527 | 35.332 | −53.629 | 1.00 | 14.51 | C |
| ATOM | 6871 | CG2 | VAL A | 957 | −23.452 | 34.909 | −52.108 | 1.00 | 14.56 | C |
| ATOM | 6872 | C | VAL A | 957 | −21.045 | 34.121 | −50.104 | 1.00 | 15.29 | C |
| ATOM | 6873 | O | VAL A | 957 | −21.762 | 33.539 | −49.296 | 1.00 | 15.11 | O |
| ATOM | 6874 | N | GLU A | 958 | −20.101 | 34.987 | −49.750 | 1.00 | 16.68 | N |
| ATOM | 6875 | CA | GLU A | 958 | −19.910 | 35.416 | −48.368 | 1.00 | 17.64 | C |
| ATOM | 6876 | CB | GLU A | 958 | −18.928 | 34.464 | −47.663 | 1.00 | 18.77 | C |
| ATOM | 6877 | CG | GLU A | 958 | −18.753 | 34.685 | −46.168 | 1.00 | 20.40 | C |
| ATOM | 6878 | CD | GLU A | 958 | −20.070 | 34.661 | −45.416 | 1.00 | 22.43 | C |
| ATOM | 6879 | OE1 | GLU A | 958 | −20.768 | 35.707 | −45.382 | 1.00 | 23.45 | O |
| ATOM | 6880 | OE2 | GLU A | 958 | −20.403 | 33.598 | −44.845 | 1.00 | 23.72 | O |
| ATOM | 6881 | C | GLU A | 958 | −19.406 | 36.867 | −48.318 | 1.00 | 17.46 | C |
| ATOM | 6882 | O | GLU A | 958 | −18.697 | 37.314 | −49.220 | 1.00 | 17.47 | O |
| ATOM | 6883 | N | ILE A | 959 | −19.766 | 37.598 | −47.270 | 1.00 | 17.26 | N |
| ATOM | 6884 | CA | ILE A | 959 | −19.159 | 38.906 | −47.031 | 1.00 | 17.62 | C |
| ATOM | 6885 | CB | ILE A | 959 | −20.129 | 39.859 | −46.307 | 1.00 | 17.18 | C |
| ATOM | 6886 | CG1 | ILE A | 959 | −21.294 | 40.223 | −47.225 | 1.00 | 17.01 | C |
| ATOM | 6887 | CD1 | ILE A | 959 | −22.568 | 40.548 | −46.480 | 1.00 | 16.69 | C |
| ATOM | 6888 | CG2 | ILE A | 959 | −19.412 | 41.109 | −45.820 | 1.00 | 17.03 | C |
| ATOM | 6889 | C | ILE A | 959 | −17.862 | 38.759 | −46.237 | 1.00 | 18.38 | C |
| ATOM | 6890 | O | ILE A | 959 | −17.842 | 38.139 | −45.172 | 1.00 | 18.29 | O |
| ATOM | 6891 | N | LEU A | 960 | −16.780 | 39.327 | −46.762 | 1.00 | 19.76 | N |
| ATOM | 6892 | CA | LEU A | 960 | −15.497 | 39.311 | −46.067 | 1.00 | 21.31 | C |
| ATOM | 6893 | CB | LEU A | 960 | −14.336 | 39.353 | −47.057 | 1.00 | 20.27 | C |
| ATOM | 6894 | CG | LEU A | 960 | −14.258 | 38.145 | −48.012 | 1.00 | 20.65 | C |
| ATOM | 6895 | CD1 | LEU A | 960 | −13.410 | 38.450 | −49.247 | 1.00 | 20.78 | C |
| ATOM | 6896 | CD2 | LEU A | 960 | −13.799 | 36.858 | −47.334 | 1.00 | 19.82 | C |
| ATOM | 6897 | C | LEU A | 960 | −15.421 | 40.460 | −45.071 | 1.00 | 23.67 | C |
| ATOM | 6898 | O | LEU A | 960 | −15.059 | 40.264 | −43.905 | 1.00 | 24.12 | O |
| ATOM | 6899 | N | ASP A | 961 | −15.779 | 41.652 | −45.544 | 1.00 | 26.36 | N |
| ATOM | 6900 | CA | ASP A | 961 | −15.912 | 42.850 | −44.710 | 1.00 | 29.29 | C |
| ATOM | 6901 | CB | ASP A | 961 | −14.539 | 43.408 | −44.329 | 1.00 | 28.44 | C |
| ATOM | 6902 | CG | ASP A | 961 | −13.719 | 43.821 | −45.528 | 1.00 | 28.29 | C |
| ATOM | 6903 | OD1 | ASP A | 961 | −14.289 | 44.231 | −46.559 | 1.00 | 28.05 | O |
| ATOM | 6904 | OD2 | ASP A | 961 | −12.482 | 43.745 | −45.431 | 1.00 | 30.07 | O |
| ATOM | 6905 | C | ASP A | 961 | −16.755 | 43.911 | −45.437 | 1.00 | 32.84 | C |
| ATOM | 6906 | O | ASP A | 961 | −17.248 | 43.671 | −46.545 | 1.00 | 33.42 | O |
| ATOM | 6907 | N | ASP A | 962 | −16.904 | 45.086 | −44.830 | 1.00 | 37.38 | N |
| ATOM | 6908 | CA | ASP A | 962 | −17.824 | 46.104 | −45.350 | 1.00 | 41.78 | C |
| ATOM | 6909 | CB | ASP A | 962 | −17.621 | 47.446 | −44.632 | 1.00 | 47.69 | C |
| ATOM | 6910 | CG | ASP A | 962 | −17.996 | 47.390 | −43.159 | 1.00 | 52.16 | C |
| ATOM | 6911 | OD1 | ASP A | 962 | −19.082 | 46.857 | −42.841 | 1.00 | 55.78 | O |
| ATOM | 6912 | OD2 | ASP A | 962 | −17.207 | 47.889 | −42.321 | 1.00 | 55.28 | O |
| ATOM | 6913 | C | ASP A | 962 | −17.695 | 46.306 | −46.860 | 1.00 | 41.28 | C |

-continued

| | | | | Atomic coordinates for CRBN:DDB1:Lenalidomide (Human protein) | | | | | |
|---|---|---|---|---|---|---|---|---|---|
| ATOM | 6914 | O    | ASP A | 962 | −18.670 | 46.686 | −47.528 | 1.00 | 42.72 | O |
| ATOM | 6915 | N    | ASP A | 963 | −16.498 | 46.037 | −47.386 | 1.00 | 37.28 | N |
| ATOM | 6916 | CA   | ASP A | 963 | −16.142 | 46.430 | −48.741 | 1.00 | 35.39 | C |
| ATOM | 6917 | CB   | ASP A | 963 | −14.945 | 47.381 | −48.695 | 1.00 | 37.38 | C |
| ATOM | 6918 | CG   | ASP A | 963 | −15.293 | 48.748 | −48.096 | 1.00 | 40.19 | C |
| ATOM | 6919 | OD1  | ASP A | 963 | −16.415 | 48.930 | −47.558 | 1.00 | 39.44 | O |
| ATOM | 6920 | OD2  | ASP A | 963 | −14.428 | 49.653 | −48.172 | 1.00 | 42.07 | O |
| ATOM | 6921 | C    | ASP A | 963 | −15.844 | 45.268 | −49.691 | 1.00 | 33.05 | C |
| ATOM | 6922 | O    | ASP A | 963 | −15.689 | 45.476 | −50.891 | 1.00 | 33.27 | O |
| ATOM | 6923 | N    | ASN A | 964 | −15.775 | 44.051 | −49.161 | 1.00 | 30.23 | N |
| ATOM | 6924 | CA   | ASN A | 964 | −15.324 | 42.895 | −49.938 | 1.00 | 27.04 | C |
| ATOM | 6925 | CB   | ASN A | 964 | −13.904 | 42.509 | −49.531 | 1.00 | 26.79 | C |
| ATOM | 6926 | CG   | ASN A | 964 | −12.889 | 43.553 | −49.926 | 1.00 | 27.11 | C |
| ATOM | 6927 | OD1  | ASN A | 964 | −12.423 | 43.590 | −51.063 | 1.00 | 26.37 | O |
| ATOM | 6928 | ND2  | ASN A | 964 | −12.541 | 44.414 | −48.985 | 1.00 | 28.41 | N |
| ATOM | 6929 | C    | ASN A | 964 | −16.238 | 41.680 | −49.847 | 1.00 | 25.01 | C |
| ATOM | 6930 | O    | ASN A | 964 | −16.671 | 41.304 | −48.759 | 1.00 | 23.81 | O |
| ATOM | 6931 | N    | PHE A | 965 | −16.504 | 41.068 | −51.003 | 1.00 | 23.74 | N |
| ATOM | 6932 | CA   | PHE A | 965 | −17.397 | 39.911 | −51.112 | 1.00 | 22.39 | C |
| ATOM | 6933 | CB   | PHE A | 965 | −18.699 | 40.322 | −51.793 | 1.00 | 23.12 | C |
| ATOM | 6934 | CG   | PHE A | 965 | −19.157 | 41.668 | −51.369 | 1.00 | 25.54 | C |
| ATOM | 6935 | CD1  | PHE A | 965 | −19.563 | 41.895 | −50.049 | 1.00 | 26.63 | C |
| ATOM | 6936 | CE1  | PHE A | 965 | −19.939 | 43.166 | −49.619 | 1.00 | 27.30 | C |
| ATOM | 6937 | CZ   | PHE A | 965 | −19.891 | 44.229 | −50.504 | 1.00 | 27.51 | C |
| ATOM | 6938 | CE2  | PHE A | 965 | −19.469 | 44.021 | −51.813 | 1.00 | 28.00 | C |
| ATOM | 6939 | CD2  | PHE A | 965 | −19.093 | 42.745 | −52.239 | 1.00 | 27.17 | C |
| ATOM | 6940 | C    | PHE A | 965 | −16.733 | 38.734 | −51.813 | 1.00 | 21.25 | C |
| ATOM | 6941 | O    | PHE A | 965 | −16.151 | 38.871 | −52.885 | 1.00 | 20.88 | O |
| ATOM | 6942 | N    | LEU A | 966 | −16.793 | 37.581 | −51.165 | 1.00 | 19.92 | N |
| ATOM | 6943 | CA   | LEU A | 966 | −16.251 | 36.352 | −51.715 | 1.00 | 19.36 | C |
| ATOM | 6944 | CB   | LEU A | 966 | −15.593 | 35.536 | −50.594 | 1.00 | 18.94 | C |
| ATOM | 6945 | CG   | LEU A | 966 | −14.939 | 34.175 | −50.850 | 1.00 | 18.35 | C |
| ATOM | 6946 | CD1  | LEU A | 966 | −13.694 | 34.333 | −51.706 | 1.00 | 18.03 | C |
| ATOM | 6947 | CD2  | LEU A | 966 | −14.609 | 33.500 | −49.522 | 1.00 | 17.68 | C |
| ATOM | 6948 | C    | LEU A | 966 | −17.371 | 35.551 | −52.399 | 1.00 | 17.00 | C |
| ATOM | 6949 | O    | LEU A | 966 | −18.534 | 35.601 | −51.988 | 1.00 | 18.59 | O |
| ATOM | 6950 | N    | GLY A | 967 | −17.014 | 34.831 | −53.454 | 1.00 | 18.15 | N |
| ATOM | 6951 | CA   | GLY A | 967 | −17.979 | 34.051 | −54.191 | 1.00 | 17.47 | C |
| ATOM | 6952 | C    | GLY A | 967 | −17.282 | 32.907 | −54.875 | 1.00 | 17.97 | C |
| ATOM | 6953 | O    | GLY A | 967 | −16.090 | 33.009 | −55.228 | 1.00 | 18.24 | O |
| ATOM | 6954 | N    | ALA A | 968 | −18.006 | 31.800 | −55.039 | 1.00 | 17.44 | N |
| ATOM | 6955 | CA   | ALA A | 968 | −17.522 | 30.679 | −55.828 | 1.00 | 16.50 | C |
| ATOM | 6956 | CB   | ALA A | 968 | −17.704 | 29.385 | −55.069 | 1.00 | 16.12 | C |
| ATOM | 6957 | C    | ALA A | 968 | −18.293 | 30.659 | −57.138 | 1.00 | 16.33 | C |
| ATOM | 6958 | O    | ALA A | 968 | −19.509 | 30.834 | −57.146 | 1.00 | 15.94 | O |
| ATOM | 6959 | N    | GLU A | 969 | −17.578 | 30.477 | −58.243 | 1.00 | 16.45 | N |
| ATOM | 6960 | CA   | GLU A | 969 | −18.173 | 30.604 | −59.567 | 1.00 | 17.06 | C |
| ATOM | 6961 | CB   | GLU A | 969 | −18.087 | 32.049 | −60.075 | 1.00 | 17.66 | C |
| ATOM | 6962 | CG   | GLU A | 969 | −16.715 | 32.440 | −60.581 | 1.00 | 19.21 | C |
| ATOM | 6963 | CD   | GLU A | 969 | −16.730 | 33.753 | −61.331 | 1.00 | 21.25 | C |
| ATOM | 6964 | OE1  | GLU A | 969 | −17.526 | 33.887 | −62.285 | 1.00 | 23.17 | O |
| ATOM | 6965 | OE2  | GLU A | 969 | −15.944 | 34.661 | −60.979 | 1.00 | 22.19 | O |
| ATOM | 6966 | C    | GLU A | 969 | −17.584 | 29.626 | −60.589 | 1.00 | 16.72 | C |
| ATOM | 6967 | O    | GLU A | 969 | −16.528 | 29.054 | −60.380 | 1.00 | 16.82 | O |
| ATOM | 6968 | N    | ASN A | 970 | −18.261 | 29.495 | −61.721 | 1.00 | 16.53 | N |
| ATOM | 6969 | CA   | ASN A | 970 | −18.125 | 28.327 | −62.571 | 1.00 | 16.26 | C |
| ATOM | 6970 | CB   | ASN A | 970 | −19.012 | 28.421 | −63.801 | 1.00 | 16.41 | C |
| ATOM | 6971 | CG   | ASN A | 970 | −18.720 | 27.320 | −64.795 | 1.00 | 15.70 | C |
| ATOM | 6972 | OD1  | ASN A | 970 | −19.137 | 26.166 | −64.609 | 1.00 | 14.95 | O |
| ATOM | 6973 | ND2  | ASN A | 970 | −17.957 | 27.659 | −65.833 | 1.00 | 15.35 | N |
| ATOM | 6974 | C    | ASN A | 970 | −16.750 | 27.947 | −63.028 | 1.00 | 16.12 | C |
| ATOM | 6975 | O    | ASN A | 970 | −15.956 | 28.793 | −63.443 | 1.00 | 15.97 | O |
| ATOM | 6976 | N    | ALA A | 971 | −16.565 | 26.625 | −63.063 | 1.00 | 16.22 | N |
| ATOM | 6977 | CA   | ALA A | 971 | −15.301 | 25.933 | −63.313 | 1.00 | 15.20 | C |
| ATOM | 6978 | CB   | ALA A | 971 | −14.630 | 26.415 | −64.587 | 1.00 | 14.98 | C |
| ATOM | 6979 | C    | ALA A | 971 | −14.421 | 26.102 | −62.072 | 1.00 | 14.81 | C |
| ATOM | 6980 | O    | ALA A | 971 | −13.229 | 26.453 | −62.164 | 1.00 | 14.85 | O |
| ATOM | 6981 | N    | PHE A | 972 | −15.054 | 25.886 | −60.911 | 1.00 | 13.69 | N |
| ATOM | 6982 | CA   | PHE A | 972 | −14.353 | 25.702 | −59.653 | 1.00 | 13.44 | C |
| ATOM | 6983 | CB   | PHE A | 972 | −13.558 | 24.385 | −59.700 | 1.00 | 13.44 | C |
| ATOM | 6984 | CG   | PHE A | 972 | −14.306 | 23.259 | −60.356 | 1.00 | 13.59 | C |
| ATOM | 6985 | CD1  | PHE A | 972 | −15.323 | 22.578 | −59.670 | 1.00 | 13.71 | C |
| ATOM | 6986 | CE1  | PHE A | 972 | −16.032 | 21.556 | −60.293 | 1.00 | 13.50 | C |
| ATOM | 6987 | CZ   | PHE A | 972 | −15.737 | 21.211 | −61.604 | 1.00 | 13.12 | C |
| ATOM | 6988 | CE2  | PHE A | 972 | −14.742 | 21.876 | −62.290 | 1.00 | 13.01 | C |
| ATOM | 6989 | CD2  | PHE A | 972 | −14.030 | 22.892 | −61.671 | 1.00 | 13.29 | C |
| ATOM | 6990 | C    | PHE A | 972 | −13.446 | 26.878 | −59.308 | 1.00 | 13.44 | C |

-continued

| | | | | | | | | | | |
|---|---|---|---|---|---|---|---|---|---|---|
| \multicolumn{11}{c}{Atomic coordinates for CRBN:DDB1:Lenalidomide (Human protein)} |
| ATOM | 6991 | O | PHE A | 972 | −12.290 | 26.691 | −58.896 | 1.00 | 13.68 | O |
| ATOM | 6992 | N | ASN A | 973 | −13.966 | 28.089 | −59.483 | 1.00 | 13.14 | N |
| ATOM | 6993 | CA | ASN A | 973 | −13.190 | 29.297 | −59.263 | 1.00 | 13.46 | C |
| ATOM | 6994 | CB | ASN A | 973 | −13.321 | 30.230 | −60.462 | 1.00 | 13.58 | C |
| ATOM | 6995 | CG | ASN A | 973 | −12.662 | 29.685 | −61.701 | 1.00 | 13.45 | C |
| ATOM | 6996 | OD1 | ASN A | 973 | −11.444 | 29.590 | −61.777 | 1.00 | 13.51 | O |
| ATOM | 6997 | ND2 | ASN A | 973 | −13.467 | 29.342 | −62.690 | 1.00 | 13.54 | N |
| ATOM | 6998 | C | ASN A | 973 | −13.644 | 30.039 | −58.028 | 1.00 | 13.80 | C |
| ATOM | 6999 | O | ASN A | 973 | −14.777 | 29.867 | −57.585 | 1.00 | 14.14 | O |
| ATOM | 7000 | N | LEU A | 974 | −12.766 | 30.870 | −57.475 | 1.00 | 14.33 | N |
| ATOM | 7001 | CA | LEU A | 974 | −13.169 | 31.851 | −56.467 | 1.00 | 15.24 | C |
| ATOM | 7002 | CB | LEU A | 974 | −12.382 | 31.676 | −55.170 | 1.00 | 14.97 | C |
| ATOM | 7003 | CG | LEU A | 974 | −12.587 | 30.411 | −54.325 | 1.00 | 15.19 | C |
| ATOM | 7004 | CD1 | LEU A | 974 | −11.813 | 30.583 | −53.034 | 1.00 | 15.68 | C |
| ATOM | 7005 | CD2 | LEU A | 974 | −14.041 | 30.123 | −53.986 | 1.00 | 15.10 | C |
| ATOM | 7006 | C | LEU A | 974 | −12.942 | 33.248 | −57.007 | 1.00 | 16.18 | C |
| ATOM | 7007 | O | LEU A | 974 | −11.934 | 33.501 | −57.673 | 1.00 | 16.91 | O |
| ATOM | 7008 | N | PHE A | 975 | −13.880 | 34.154 | −56.733 | 1.00 | 16.84 | N |
| ATOM | 7009 | CA | PHE A | 975 | −13.703 | 35.579 | −57.048 | 1.00 | 16.66 | C |
| ATOM | 7010 | CB | PHE A | 975 | −14.609 | 35.977 | −58.204 | 1.00 | 16.45 | C |
| ATOM | 7011 | CG | PHE A | 975 | −16.058 | 36.067 | −57.830 | 1.00 | 16.23 | C |
| ATOM | 7012 | CD1 | PHE A | 975 | −16.845 | 34.924 | −57.767 | 1.00 | 15.96 | C |
| ATOM | 7013 | CE1 | PHE A | 975 | −18.176 | 35.001 | −57.413 | 1.00 | 15.74 | C |
| ATOM | 7014 | CZ | PHE A | 975 | −18.735 | 36.230 | −57.125 | 1.00 | 16.01 | C |
| ATOM | 7015 | CE2 | PHE A | 975 | −17.963 | 37.381 | −57.178 | 1.00 | 16.00 | C |
| ATOM | 7016 | CD2 | PHE A | 975 | −16.635 | 37.298 | −57.532 | 1.00 | 16.06 | C |
| ATOM | 7017 | C | PHE A | 975 | −13.967 | 36.477 | −55.839 | 1.00 | 17.04 | C |
| ATOM | 7018 | O | PHE A | 975 | −14.696 | 36.108 | −54.919 | 1.00 | 16.74 | O |
| ATOM | 7019 | N | VAL A | 976 | −13.370 | 37.659 | −55.843 | 1.00 | 18.62 | N |
| ATOM | 7020 | CA | VAL A | 976 | −13.620 | 38.645 | −54.786 | 1.00 | 20.31 | C |
| ATOM | 7021 | CB | VAL A | 976 | −12.424 | 38.798 | −53.826 | 1.00 | 19.18 | C |
| ATOM | 7022 | CG1 | VAL A | 976 | −12.669 | 39.930 | −52.857 | 1.00 | 19.25 | C |
| ATOM | 7023 | CG2 | VAL A | 976 | −12.194 | 37.516 | −53.053 | 1.00 | 18.93 | C |
| ATOM | 7024 | C | VAL A | 976 | −13.977 | 39.992 | −55.397 | 1.00 | 22.40 | C |
| ATOM | 7025 | O | VAL A | 976 | −13.220 | 40.519 | −56.206 | 1.00 | 22.82 | O |
| ATOM | 7026 | N | CYS A | 977 | −15.145 | 40.523 | −55.015 | 1.00 | 25.58 | N |
| ATOM | 7027 | CA | CYS A | 977 | −15.614 | 41.857 | −55.435 | 1.00 | 27.37 | C |
| ATOM | 7028 | CB | CYS A | 977 | −17.094 | 41.831 | −55.771 | 1.00 | 29.74 | C |
| ATOM | 7029 | SG | CYS A | 977 | −17.455 | 41.015 | −57.328 | 1.00 | 37.92 | S |
| ATOM | 7030 | C | CYS A | 977 | −15.396 | 42.886 | −54.347 | 1.00 | 27.13 | C |
| ATOM | 7031 | O | CYS A | 977 | −15.599 | 42.602 | −53.160 | 1.00 | 25.64 | O |
| ATOM | 7032 | N | GLN A | 978 | −15.009 | 44.089 | −54.766 | 1.00 | 27.34 | N |
| ATOM | 7033 | CA | GLN A | 978 | −14.658 | 45.154 | −53.839 | 1.00 | 28.01 | C |
| ATOM | 7034 | CB | GLN A | 978 | −13.196 | 45.519 | −54.010 | 1.00 | 27.04 | C |
| ATOM | 7035 | CG | GLN A | 978 | −12.688 | 46.464 | −52.951 | 1.00 | 27.17 | C |
| ATOM | 7036 | CD | GLN A | 978 | −11.200 | 46.379 | −52.792 | 1.00 | 27.25 | C |
| ATOM | 7037 | OE1 | GLN A | 978 | −10.444 | 47.017 | −53.533 | 1.00 | 27.30 | O |
| ATOM | 7038 | NE2 | GLN A | 978 | −10.758 | 45.592 | −51.811 | 1.00 | 27.46 | N |
| ATOM | 7039 | C | GLN A | 978 | −15.518 | 46.375 | −54.064 | 1.00 | 29.10 | C |
| ATOM | 7040 | O | GLN A | 978 | −15.728 | 46.774 | −55.209 | 1.00 | 30.07 | O |
| ATOM | 7041 | N | LYS A | 979 | −15.997 | 46.982 | −52.980 | 1.00 | 31.40 | N |
| ATOM | 7042 | CA | LYS A | 979 | −16.932 | 48.105 | −53.098 | 1.00 | 35.73 | C |
| ATOM | 7043 | CB | LYS A | 979 | −17.533 | 48.521 | −51.755 | 1.00 | 35.66 | C |
| ATOM | 7044 | CG | LYS A | 979 | −18.562 | 49.638 | −51.887 | 1.00 | 34.94 | C |
| ATOM | 7045 | CD | LYS A | 979 | −19.457 | 49.731 | −50.663 | 1.00 | 36.72 | C |
| ATOM | 7046 | CE | LYS A | 979 | −18.733 | 50.314 | −49.458 | 1.00 | 38.29 | C |
| ATOM | 7047 | NZ | LYS A | 979 | −19.157 | 49.613 | −48.215 | 1.00 | 39.80 | N |
| ATOM | 7048 | C | LYS A | 979 | −16.322 | 49.306 | −53.791 | 1.00 | 38.84 | C |
| ATOM | 7049 | O | LYS A | 979 | −16.877 | 49.793 | −54.778 | 1.00 | 40.20 | O |
| ATOM | 7050 | N | ASP A | 980 | −15.187 | 49.780 | −53.280 | 1.00 | 42.54 | N |
| ATOM | 7051 | CA | ASP A | 980 | −14.507 | 50.920 | −53.895 | 1.00 | 47.50 | C |
| ATOM | 7052 | CB | ASP A | 980 | −13.518 | 51.577 | −52.921 | 1.00 | 50.94 | C |
| ATOM | 7053 | CG | ASP A | 980 | −12.902 | 52.850 | −53.486 | 1.00 | 51.41 | C |
| ATOM | 7054 | OD1 | ASP A | 980 | −13.617 | 53.596 | −54.192 | 1.00 | 51.63 | O |
| ATOM | 7055 | OD2 | ASP A | 980 | −11.702 | 53.096 | −53.234 | 1.00 | 51.75 | O |
| ATOM | 7056 | C | ASP A | 980 | −13.806 | 50.525 | −55.199 | 1.00 | 47.76 | C |
| ATOM | 7057 | O | ASP A | 980 | −14.082 | 51.098 | −56.256 | 1.00 | 47.25 | O |
| ATOM | 7058 | N | GLU A | 987 | −22.391 | 59.114 | −57.781 | 1.00 | 50.94 | N |
| ATOM | 7059 | CA | GLU A | 987 | −21.253 | 58.695 | −58.598 | 1.00 | 53.30 | C |
| ATOM | 7060 | CB | GLU A | 987 | −19.967 | 58.684 | −57.741 | 1.00 | 50.19 | C |
| ATOM | 7061 | CG | GLU A | 987 | −18.685 | 58.279 | −58.469 | 1.00 | 48.14 | C |
| ATOM | 7062 | CD | GLU A | 987 | −18.003 | 59.425 | −59.202 | 1.00 | 46.73 | C |
| ATOM | 7063 | OE1 | GLU A | 987 | −17.170 | 60.121 | −58.576 | 1.00 | 44.82 | O |
| ATOM | 7064 | OE2 | GLU A | 987 | −18.277 | 59.606 | −60.410 | 1.00 | 44.01 | O |
| ATOM | 7065 | C | GLU A | 987 | −21.516 | 57.317 | −59.232 | 1.00 | 54.62 | C |
| ATOM | 7066 | O | GLU A | 987 | −22.473 | 56.633 | −58.865 | 1.00 | 52.82 | O |
| ATOM | 7067 | N | GLU A | 988 | −20.699 | 56.949 | −60.220 | 1.00 | 59.20 | N |

-continued

| | | | Atomic coordinates for CRBN:DDB1:Lenalidomide (Human protein) | | | | | | |
|---|---|---|---|---|---|---|---|---|---|
| ATOM | 7068 | CA | GLU A | 988 | −20.551 | 55.547 | −60.627 | 1.00 | 61.23 | C |
| ATOM | 7069 | CB | GLU A | 988 | −20.503 | 55.355 | −62.153 | 1.00 | 65.99 | C |
| ATOM | 7070 | CG | GLU A | 988 | −19.953 | 56.529 | −62.957 | 1.00 | 71.51 | C |
| ATOM | 7071 | CD | GLU A | 988 | −21.040 | 57.488 | −63.423 | 1.00 | 73.08 | C |
| ATOM | 7072 | OE1 | GLU A | 988 | −21.855 | 57.935 | −62.580 | 1.00 | 74.74 | O |
| ATOM | 7073 | OE2 | GLU A | 988 | −21.074 | 57.801 | −64.636 | 1.00 | 71.07 | O |
| ATOM | 7074 | C | GLU A | 988 | −19.333 | 54.944 | −59.928 | 1.00 | 58.79 | C |
| ATOM | 7075 | O | GLU A | 988 | −18.178 | 55.235 | −60.252 | 1.00 | 57.68 | O |
| ATOM | 7076 | N | ARG A | 989 | −19.657 | 54.055 | −58.997 | 1.00 | 57.25 | N |
| ATOM | 7077 | CA | ARG A | 989 | −18.866 | 53.650 | −57.828 | 1.00 | 54.18 | C |
| ATOM | 7078 | CB | ARG A | 989 | −18.313 | 54.848 | −57.039 | 1.00 | 54.68 | C |
| ATOM | 7079 | CG | ARG A | 989 | −16.973 | 55.371 | −57.567 | 1.00 | 57.70 | C |
| ATOM | 7080 | CD | ARG A | 989 | −15.827 | 55.353 | −56.552 | 1.00 | 58.41 | C |
| ATOM | 7081 | NE | ARG A | 989 | −15.817 | 56.545 | −55.688 | 1.00 | 56.87 | N |
| ATOM | 7082 | CZ | ARG A | 989 | −14.726 | 57.114 | −55.170 | 1.00 | 54.65 | C |
| ATOM | 7083 | NH1 | ARG A | 989 | −13.516 | 56.627 | −55.427 | 1.00 | 54.41 | N |
| ATOM | 7084 | NH2 | ARG A | 989 | −14.847 | 58.183 | −54.395 | 1.00 | 52.34 | N |
| ATOM | 7085 | C | ARG A | 989 | −19.977 | 52.911 | −57.068 | 1.00 | 50.71 | C |
| ATOM | 7086 | O | ARG A | 989 | −19.809 | 52.414 | −55.946 | 1.00 | 48.06 | O |
| ATOM | 7087 | N | GLN A | 990 | −21.139 | 52.912 | −57.728 | 1.00 | 46.34 | N |
| ATOM | 7088 | CA | GLN A | 990 | −22.150 | 51.876 | −57.636 | 1.00 | 43.05 | C |
| ATOM | 7089 | CB | GLN A | 990 | −23.452 | 52.373 | −58.261 | 1.00 | 42.71 | C |
| ATOM | 7090 | CG | GLN A | 990 | −23.868 | 53.774 | −57.847 | 1.00 | 44.27 | C |
| ATOM | 7091 | CD | GLN A | 990 | −24.955 | 54.353 | −58.732 | 1.00 | 43.49 | C |
| ATOM | 7092 | OE1 | GLN A | 990 | −25.163 | 53.900 | −59.856 | 1.00 | 44.09 | O |
| ATOM | 7093 | NE2 | GLN A | 990 | −25.649 | 55.364 | −58.231 | 1.00 | 42.99 | N |
| ATOM | 7094 | C | GLN A | 990 | −21.668 | 50.657 | −58.432 | 1.00 | 42.42 | C |
| ATOM | 7095 | O | GLN A | 990 | −22.410 | 49.697 | −58.642 | 1.00 | 40.42 | O |
| ATOM | 7096 | N | HIS A | 991 | −20.424 | 50.720 | −58.897 | 1.00 | 44.01 | N |
| ATOM | 7097 | CA | HIS A | 991 | −19.834 | 49.652 | −59.681 | 1.00 | 43.53 | C |
| ATOM | 7098 | CB | HIS A | 991 | −19.163 | 50.216 | −60.939 | 1.00 | 52.55 | C |
| ATOM | 7099 | CG | HIS A | 991 | −18.509 | 49.159 | −61.811 | 1.00 | 61.81 | C |
| ATOM | 7100 | ND1 | HIS A | 991 | −19.218 | 48.354 | −62.635 | 1.00 | 63.55 | N |
| ATOM | 7101 | CE1 | HIS A | 991 | −18.376 | 47.511 | −63.269 | 1.00 | 65.96 | C |
| ATOM | 7102 | NE2 | HIS A | 991 | −17.122 | 47.778 | −62.853 | 1.00 | 67.19 | N |
| ATOM | 7103 | CD2 | HIS A | 991 | −17.166 | 48.785 | −61.953 | 1.00 | 64.96 | C |
| ATOM | 7104 | C | HIS A | 991 | −18.854 | 48.891 | −58.850 | 1.00 | 37.28 | C |
| ATOM | 7105 | O | HIS A | 991 | −17.961 | 49.476 | −58.245 | 1.00 | 35.32 | O |
| ATOM | 7106 | N | LEU A | 992 | −19.018 | 47.575 | −58.810 | 1.00 | 32.54 | N |
| ATOM | 7107 | CA | LEU A | 992 | −18.117 | 46.718 | −58.043 | 1.00 | 30.74 | C |
| ATOM | 7108 | CB | LEU A | 992 | −18.873 | 45.527 | −57.447 | 1.00 | 28.09 | C |
| ATOM | 7109 | CG | LEU A | 992 | −19.900 | 45.838 | −56.356 | 1.00 | 27.16 | C |
| ATOM | 7110 | CD1 | LEU A | 992 | −20.564 | 44.567 | −55.855 | 1.00 | 26.90 | C |
| ATOM | 7111 | CD2 | LEU A | 992 | −19.284 | 46.593 | −55.191 | 1.00 | 26.51 | C |
| ATOM | 7112 | C | LEU A | 992 | −16.912 | 46.247 | −58.867 | 1.00 | 30.25 | C |
| ATOM | 7113 | O | LEU A | 992 | −17.049 | 45.878 | −60.036 | 1.00 | 30.30 | O |
| ATOM | 7114 | N | GLN A | 993 | −15.737 | 46.266 | −58.246 | 1.00 | 30.06 | N |
| ATOM | 7115 | CA | GLN A | 993 | −14.495 | 45.924 | −58.931 | 1.00 | 30.79 | C |
| ATOM | 7116 | CB | GLN A | 993 | −13.422 | 46.974 | −58.637 | 1.00 | 34.35 | C |
| ATOM | 7117 | CG | GLN A | 993 | −13.506 | 48.210 | −59.526 | 1.00 | 38.35 | C |
| ATOM | 7118 | CD | GLN A | 993 | −12.700 | 48.058 | −60.803 | 1.00 | 41.94 | C |
| ATOM | 7119 | OE1 | GLN A | 993 | −11.467 | 47.996 | −60.764 | 1.00 | 43.55 | O |
| ATOM | 7120 | NE2 | GLN A | 993 | −13.393 | 47.990 | −61.948 | 1.00 | 43.48 | N |
| ATOM | 7121 | C | GLN A | 993 | −13.992 | 44.520 | −58.587 | 1.00 | 29.34 | C |
| ATOM | 7122 | O | GLN A | 993 | −14.024 | 44.093 | −57.428 | 1.00 | 30.11 | O |
| ATOM | 7123 | N | GLU A | 994 | −13.527 | 43.812 | −59.605 | 1.00 | 26.76 | N |
| ATOM | 7124 | CA | GLU A | 994 | −13.116 | 42.429 | −59.457 | 1.00 | 25.56 | C |
| ATOM | 7125 | CB | GLU A | 994 | −13.357 | 41.681 | −60.774 | 1.00 | 27.70 | C |
| ATOM | 7126 | CG | GLU A | 994 | −13.478 | 40.174 | −60.626 | 1.00 | 30.10 | C |
| ATOM | 7127 | CD | GLU A | 994 | −14.043 | 39.492 | −61.865 | 1.00 | 31.75 | C |
| ATOM | 7128 | OE1 | GLU A | 994 | −13.563 | 39.788 | −62.987 | 1.00 | 33.36 | O |
| ATOM | 7129 | OE2 | GLU A | 994 | −14.950 | 38.636 | −61.710 | 1.00 | 31.93 | O |
| ATOM | 7130 | C | GLU A | 994 | −11.643 | 42.357 | −59.048 | 1.00 | 23.21 | C |
| ATOM | 7131 | O | GLU A | 994 | −10.764 | 42.386 | −59.898 | 1.00 | 22.85 | O |
| ATOM | 7132 | N | VAL A | 995 | −11.386 | 42.250 | −57.745 | 1.00 | 20.91 | N |
| ATOM | 7133 | CA | VAL A | 995 | −10.026 | 42.363 | −57.210 | 1.00 | 18.71 | C |
| ATOM | 7134 | CB | VAL A | 995 | −9.976 | 43.206 | −55.930 | 1.00 | 17.73 | C |
| ATOM | 7135 | CG1 | VAL A | 995 | −10.435 | 44.616 | −56.224 | 1.00 | 17.40 | C |
| ATOM | 7136 | CG2 | VAL A | 995 | −10.807 | 42.575 | −54.834 | 1.00 | 17.53 | C |
| ATOM | 7137 | C | VAL A | 995 | −9.294 | 41.056 | −56.948 | 1.00 | 18.14 | C |
| ATOM | 7138 | O | VAL A | 995 | −8.125 | 41.077 | −56.568 | 1.00 | 18.46 | O |
| ATOM | 7139 | N | GLY A | 996 | −9.963 | 39.923 | −57.140 | 1.00 | 17.33 | N |
| ATOM | 7140 | CA | GLY A | 996 | −9.320 | 38.631 | −56.912 | 1.00 | 16.20 | C |
| ATOM | 7141 | C | GLY A | 996 | −9.964 | 37.502 | −57.674 | 1.00 | 15.74 | C |
| ATOM | 7142 | O | GLY A | 996 | −11.177 | 37.354 | −57.645 | 1.00 | 16.19 | O |
| ATOM | 7143 | N | LEU A | 997 | −9.152 | 36.720 | −58.378 | 1.00 | 15.36 | N |
| ATOM | 7144 | CA | LEU A | 997 | −9.608 | 35.479 | −59.016 | 1.00 | 15.14 | C |

-continued

| Atomic coordinates for CRBN:DDB1:Lenalidomide (Human protein) | | | | | | | | | |
|---|---|---|---|---|---|---|---|---|---|
| ATOM | 7145 | CB | LEU A | 997 | −9.653 | 35.626 | −60.544 | 1.00 | 15.66 | C |
| ATOM | 7146 | CG | LEU A | 997 | −10.241 | 36.882 | −61.213 | 1.00 | 16.14 | C |
| ATOM | 7147 | CD1 | LEU A | 997 | −10.220 | 36.745 | −62.730 | 1.00 | 16.33 | C |
| ATOM | 7148 | CD2 | LEU A | 997 | −11.661 | 37.184 | −60.747 | 1.00 | 16.52 | C |
| ATOM | 7149 | C | LEU A | 997 | −8.660 | 34.337 | −58.637 | 1.00 | 14.69 | C |
| ATOM | 7150 | O | LEU A | 997 | −7.465 | 34.575 | −58.414 | 1.00 | 14.95 | O |
| ATOM | 7151 | N | PHE A | 998 | −9.180 | 33.108 | −58.582 | 1.00 | 13.81 | N |
| ATOM | 7152 | CA | PHE A | 998 | −8.385 | 31.928 | −58.227 | 1.00 | 13.32 | C |
| ATOM | 7153 | CB | PHE A | 998 | −8.227 | 31.872 | −56.717 | 1.00 | 13.40 | C |
| ATOM | 7154 | CG | PHE A | 998 | −7.219 | 30.867 | −56.230 | 1.00 | 13.51 | C |
| ATOM | 7155 | CD1 | PHE A | 998 | −5.865 | 30.999 | −56.546 | 1.00 | 13.31 | C |
| ATOM | 7156 | CE1 | PHE A | 998 | −4.936 | 30.091 | −56.077 | 1.00 | 13.10 | C |
| ATOM | 7157 | CZ | PHE A | 998 | −5.342 | 29.050 | −55.261 | 1.00 | 13.32 | C |
| ATOM | 7158 | CE2 | PHE A | 998 | −6.683 | 28.906 | −54.927 | 1.00 | 16.45 | C |
| ATOM | 7159 | CD2 | PHE A | 998 | −7.615 | 29.815 | −55.406 | 1.00 | 13.45 | C |
| ATOM | 7160 | C | PHE A | 998 | −9.106 | 30.682 | −58.671 | 1.00 | 13.25 | C |
| ATOM | 7161 | O | PHE A | 998 | −10.275 | 30.515 | −58.358 | 1.00 | 13.56 | O |
| ATOM | 7162 | N | HIS A | 999 | −8.433 | 29.798 | −59.400 | 1.00 | 13.21 | N |
| ATOM | 7163 | CA | HIS A | 999 | −9.045 | 28.507 | −59.733 | 1.00 | 12.90 | C |
| ATOM | 7164 | CB | HIS A | 999 | −8.454 | 27.923 | −61.001 | 1.00 | 13.24 | C |
| ATOM | 7165 | CG | HIS A | 999 | −9.203 | 26.717 | −61.500 | 1.00 | 13.99 | C |
| ATOM | 7166 | ND1 | HIS A | 999 | −8.762 | 25.449 | −61.310 | 1.00 | 14.10 | N |
| ATOM | 7167 | CE1 | HIS A | 999 | −9.648 | 24.580 | −61.858 | 1.00 | 14.00 | C |
| ATOM | 7168 | NE2 | HIS A | 999 | −10.673 | 25.297 | −62.378 | 1.00 | 14.00 | N |
| ATOM | 7169 | CD2 | HIS A | 999 | −10.434 | 26.611 | −62.176 | 1.00 | 14.01 | C |
| ATOM | 7170 | C | HIS A | 999 | −8.831 | 27.554 | −58.612 | 1.00 | 12.62 | C |
| ATOM | 7171 | O | HIS A | 999 | −7.721 | 27.057 | −58.443 | 1.00 | 12.81 | O |
| ATOM | 7172 | N | LEU A | 1000 | −9.879 | 27.277 | −57.834 | 1.00 | 12.17 | N |
| ATOM | 7173 | CA | LEU A | 1000 | −9.750 | 26.430 | −56.629 | 1.00 | 11.82 | C |
| ATOM | 7174 | CB | LEU A | 1000 | −10.908 | 26.668 | −55.657 | 1.00 | 11.69 | C |
| ATOM | 7175 | CG | LEU A | 1000 | −10.911 | 25.912 | −54.320 | 1.00 | 11.54 | C |
| ATOM | 7176 | CD1 | LEU A | 1000 | −9.652 | 26.169 | −53.523 | 1.00 | 11.61 | C |
| ATOM | 7177 | CD2 | LEU A | 1000 | −12.108 | 26.307 | −53.490 | 1.00 | 11.48 | C |
| ATOM | 7178 | C | LEU A | 1000 | −9.611 | 24.935 | −56.914 | 1.00 | 11.63 | C |
| ATOM | 7179 | O | LEU A | 1000 | −8.790 | 24.279 | −56.317 | 1.00 | 11.37 | O |
| ATOM | 7180 | N | GLY A | 1001 | −10.415 | 24.399 | −57.822 | 1.00 | 11.74 | N |
| ATOM | 7181 | CA | GLY A | 1001 | −10.391 | 22.955 | −58.105 | 1.00 | 11.73 | C |
| ATOM | 7182 | C | GLY A | 1001 | −11.505 | 22.198 | −57.396 | 1.00 | 11.74 | C |
| ATOM | 7183 | O | GLY A | 1001 | −11.635 | 20.980 | −57.551 | 1.00 | 11.56 | O |
| ATOM | 7184 | N | GLU A | 1002 | −12.300 | 22.935 | −56.617 | 1.00 | 11.67 | N |
| ATOM | 7185 | CA | GLU A | 1002 | −13.474 | 22.409 | −55.934 | 1.00 | 11.64 | C |
| ATOM | 7186 | CB | GLU A | 1002 | −13.256 | 22.446 | −54.418 | 1.00 | 11.84 | C |
| ATOM | 7187 | CG | GLU A | 1002 | −12.072 | 21.630 | −53.916 | 1.00 | 12.27 | C |
| ATOM | 7188 | CD | GLU A | 1002 | −12.255 | 20.130 | −54.122 | 1.00 | 12.96 | C |
| ATOM | 7189 | OE1 | GLU A | 1002 | −13.422 | 19.669 | −54.304 | 1.00 | 13.31 | O |
| ATOM | 7190 | OE2 | GLU A | 1002 | −11.231 | 19.403 | −54.098 | 1.00 | 12.87 | O |
| ATOM | 7191 | C | GLU A | 1002 | −14.755 | 23.190 | −56.306 | 1.00 | 11.54 | C |
| ATOM | 7192 | O | GLU A | 1002 | −14.687 | 24.302 | −56.832 | 1.00 | 11.57 | O |
| ATOM | 7193 | N | PHE A | 1003 | −15.918 | 22.592 | −56.041 | 1.00 | 11.14 | N |
| ATOM | 7194 | CA | PHE A | 1003 | −17.198 | 23.272 | −56.180 | 1.00 | 10.64 | C |
| ATOM | 7195 | CB | PHE A | 1003 | −18.207 | 22.351 | −56.869 | 1.00 | 10.51 | C |
| ATOM | 7196 | CG | PHE A | 1003 | −19.549 | 22.994 | −57.170 | 1.00 | 10.36 | C |
| ATOM | 7197 | CD1 | PHE A | 1003 | −20.521 | 23.133 | −56.180 | 1.00 | 10.21 | C |
| ATOM | 7198 | CE1 | PHE A | 1003 | −21.758 | 23.691 | −56.462 | 1.00 | 9.97 | C |
| ATOM | 7199 | CZ | PHE A | 1003 | −22.050 | 24.106 | −57.741 | 1.00 | 9.98 | C |
| ATOM | 7200 | CE2 | PHE A | 1003 | −21.105 | 23.958 | −58.744 | 1.00 | 10.11 | C |
| ATOM | 7201 | CD2 | PHE A | 1003 | −19.863 | 23.405 | −58.460 | 1.00 | 10.25 | C |
| ATOM | 7202 | C | PHE A | 1003 | −17.643 | 23.576 | −54.773 | 1.00 | 10.51 | C |
| ATOM | 7203 | O | PHE A | 1003 | −17.958 | 22.669 | −54.010 | 1.00 | 10.77 | O |
| ATOM | 7204 | N | VAL A | 1004 | −17.632 | 24.849 | −54.412 | 1.00 | 10.44 | N |
| ATOM | 7205 | CA | VAL A | 1004 | −17.988 | 25.272 | −53.053 | 1.00 | 10.48 | C |
| ATOM | 7206 | CB | VAL A | 1004 | −17.333 | 26.639 | −52.678 | 1.00 | 10.22 | C |
| ATOM | 7207 | CG1 | VAL A | 1004 | −17.918 | 27.206 | −51.392 | 1.00 | 10.13 | C |
| ATOM | 7208 | CG2 | VAL A | 1004 | −15.830 | 26.492 | −52.548 | 1.00 | 10.09 | C |
| ATOM | 7209 | C | VAL A | 1004 | −19.509 | 25.359 | −52.923 | 1.00 | 10.60 | C |
| ATOM | 7210 | O | VAL A | 1004 | −20.155 | 26.046 | −53.716 | 1.00 | 10.80 | O |
| ATOM | 7211 | N | ASN A | 1005 | −20.069 | 24.676 | −51.924 | 1.00 | 10.41 | N |
| ATOM | 7212 | CA | ASN A | 1005 | −21.487 | 24.798 | −51.630 | 1.00 | 10.52 | C |
| ATOM | 7213 | CB | ASN A | 1005 | −22.092 | 23.442 | −51.250 | 1.00 | 10.59 | C |
| ATOM | 7214 | CG | ASN A | 1005 | −22.273 | 22.533 | −52.443 | 1.00 | 10.68 | C |
| ATOM | 7215 | OD1 | ASN A | 1005 | −22.656 | 22.988 | −53.514 | 1.00 | 11.13 | O |
| ATOM | 7216 | ND2 | ASN A | 1005 | −22.008 | 21.244 | −52.268 | 1.00 | 10.46 | N |
| ATOM | 7217 | C | ASN A | 1005 | −21.781 | 25.821 | −50.542 | 1.00 | 10.60 | C |
| ATOM | 7218 | O | ASN A | 1005 | −22.826 | 26.476 | −50.568 | 1.00 | 10.47 | O |
| ATOM | 7219 | N | VAL A | 1006 | −20.863 | 25.964 | −49.593 | 1.00 | 10.80 | N |
| ATOM | 7220 | CA | VAL A | 1006 | −21.164 | 26.696 | −48.354 | 1.00 | 11.27 | C |
| ATOM | 7221 | CB | VAL A | 1006 | −21.793 | 25.772 | −47.280 | 1.00 | 10.96 | C |

-continued

| | | | Atomic coordinates for CRBN:DDB1:Lenalidomide (Human protein) | | | | | | |
|---|---|---|---|---|---|---|---|---|---|
| ATOM | 7222 | CG1 | VAL A | 1006 | −21.024 | 24.462 | −47.170 | 1.00 | 11.00 | C |
| ATOM | 7223 | CG2 | VAL A | 1006 | −21.855 | 26.458 | −45.933 | 1.00 | 10.77 | C |
| ATOM | 7224 | C | VAL A | 1006 | −19.946 | 27.413 | −47.781 | 1.00 | 11.78 | C |
| ATOM | 7225 | O | VAL A | 1006 | −18.866 | 26.843 | −47.679 | 1.00 | 11.76 | O |
| ATOM | 7226 | N | PHE A | 1007 | −20.143 | 28.681 | −47.449 | 1.00 | 12.58 | N |
| ATOM | 7227 | CA | PHE A | 1007 | −19.152 | 29.494 | −46.773 | 1.00 | 13.45 | C |
| ATOM | 7228 | CB | PHE A | 1007 | −19.001 | 30.855 | −47.472 | 1.00 | 12.55 | C |
| ATOM | 7229 | CG | PHE A | 1007 | −18.266 | 30.809 | −48.784 | 1.00 | 11.95 | C |
| ATOM | 7230 | CD1 | PHE A | 1007 | −16.919 | 30.421 | −48.844 | 1.00 | 11.87 | C |
| ATOM | 7231 | CE1 | PHE A | 1007 | −16.237 | 30.390 | −50.054 | 1.00 | 11.49 | C |
| ATOM | 7232 | CZ | PHE A | 1007 | −16.887 | 30.779 | −51.216 | 1.00 | 11.37 | C |
| ATOM | 7233 | CE2 | PHE A | 1007 | −18.217 | 31.183 | −51.169 | 1.00 | 11.43 | C |
| ATOM | 7234 | CD2 | PHE A | 1007 | −18.897 | 31.202 | −49.958 | 1.00 | 11.57 | C |
| ATOM | 7235 | C | PHE A | 1007 | −19.701 | 29.747 | −45.381 | 1.00 | 14.86 | C |
| ATOM | 7236 | O | PHE A | 1007 | −20.901 | 29.991 | −45.218 | 1.00 | 14.93 | O |
| ATOM | 7237 | N | CYS A | 1008 | −18.839 | 29.717 | −44.377 | 1.00 | 16.84 | N |
| ATOM | 7238 | CA | CYS A | 1008 | −19.220 | 30.269 | −43.091 | 1.00 | 18.70 | C |
| ATOM | 7239 | CB | CYS A | 1008 | −20.041 | 29.272 | −42.289 | 1.00 | 19.72 | C |
| ATOM | 7240 | SG | CYS A | 1008 | −19.068 | 27.939 | −41.585 | 1.00 | 22.87 | S |
| ATOM | 7241 | C | CYS A | 1008 | −18.048 | 30.782 | −42.281 | 1.00 | 19.58 | C |
| ATOM | 7242 | O | CYS A | 1008 | −16.959 | 30.235 | −42.321 | 1.00 | 18.72 | O |
| ATOM | 7243 | N | HIS A | 1009 | −18.305 | 31.864 | −41.561 | 1.00 | 22.07 | N |
| ATOM | 7244 | CA | HIS A | 1009 | −17.361 | 32.456 | −40.639 | 1.00 | 24.60 | C |
| ATOM | 7245 | CB | HIS A | 1009 | −17.924 | 33.774 | −40.146 | 1.00 | 24.69 | C |
| ATOM | 7246 | CG | HIS A | 1009 | −18.026 | 34.819 | −41.235 | 1.00 | 25.38 | C |
| ATOM | 7247 | ND1 | HIS A | 1009 | −17.049 | 35.722 | −41.470 | 1.00 | 26.09 | N |
| ATOM | 7248 | CE1 | HIS A | 1009 | −17.389 | 36.487 | −42.518 | 1.00 | 25.87 | C |
| ATOM | 7249 | NE2 | HIS A | 1009 | −18.579 | 36.064 | −42.971 | 1.00 | 25.80 | N |
| ATOM | 7250 | CD2 | HIS A | 1009 | −18.996 | 35.033 | −42.205 | 1.00 | 25.50 | C |
| ATOM | 7251 | C | HIS A | 1009 | −17.121 | 31.506 | −39.520 | 1.00 | 27.52 | C |
| ATOM | 7252 | O | HIS A | 1009 | −18.061 | 30.888 | −39.029 | 1.00 | 28.52 | O |
| ATOM | 7253 | N | GLY A | 1010 | −15.861 | 31.330 | −39.130 | 1.00 | 32.03 | N |
| ATOM | 7254 | CA | GLY A | 1010 | −15.520 | 30.289 | −38.155 | 1.00 | 37.59 | C |
| ATOM | 7255 | C | GLY A | 1010 | −14.139 | 30.372 | −37.530 | 1.00 | 43.77 | C |
| ATOM | 7256 | O | GLY A | 1010 | −13.410 | 31.345 | −37.735 | 1.00 | 45.27 | O |
| ATOM | 7257 | N | SER A | 1011 | −13.792 | 29.345 | −36.747 | 1.00 | 47.42 | N |
| ATOM | 7258 | CA | SER A | 1011 | −12.465 | 29.235 | −36.134 | 1.00 | 48.77 | C |
| ATOM | 7259 | CB | SER A | 1011 | −12.392 | 30.061 | −34.839 | 1.00 | 49.73 | C |
| ATOM | 7260 | OG | SER A | 1011 | −11.207 | 29.774 | −34.110 | 1.00 | 50.58 | O |
| ATOM | 7261 | C | SER A | 1011 | −12.033 | 27.770 | −35.901 | 1.00 | 50.52 | C |
| ATOM | 7262 | O | SER A | 1011 | −12.531 | 27.089 | −34.987 | 1.00 | 50.03 | O |
| ATOM | 7263 | N | LEU A | 1012 | −11.107 | 27.305 | −36.750 | 1.00 | 50.32 | N |
| ATOM | 7264 | CA | LEU A | 1012 | −10.468 | 25.981 | −36.617 | 1.00 | 47.73 | C |
| ATOM | 7265 | CB | LEU A | 1012 | −9.709 | 25.593 | −37.911 | 1.00 | 42.40 | C |
| ATOM | 7266 | CG | LEU A | 1012 | −10.390 | 25.477 | −39.287 | 1.00 | 37.21 | C |
| ATOM | 7267 | CD1 | LEU A | 1012 | −9.428 | 24.943 | −40.320 | 1.00 | 32.24 | C |
| ATOM | 7268 | CD2 | LEU A | 1012 | −11.636 | 24.609 | −39.251 | 1.00 | 35.27 | C |
| ATOM | 7269 | C | LEU A | 1012 | −9.464 | 25.985 | −35.477 | 1.00 | 48.84 | C |
| ATOM | 7270 | O | LEU A | 1012 | −9.409 | 25.039 | −34.687 | 1.00 | 49.57 | O |
| ATOM | 7271 | N | VAL A | 1013 | −8.735 | 27.103 | −35.379 | 1.00 | 50.31 | N |
| ATOM | 7272 | CA | VAL A | 1013 | −7.367 | 27.200 | −34.826 | 1.00 | 49.45 | C |
| ATOM | 7273 | CB | VAL A | 1013 | −7.283 | 27.168 | −33.278 | 1.00 | 50.72 | C |
| ATOM | 7274 | CG1 | VAL A | 1013 | −5.962 | 27.791 | −32.829 | 1.00 | 52.64 | C |
| ATOM | 7275 | CG2 | VAL A | 1013 | −8.454 | 27.911 | −32.642 | 1.00 | 51.09 | C |
| ATOM | 7276 | C | VAL A | 1013 | −6.412 | 26.177 | −35.456 | 1.00 | 49.86 | C |
| ATOM | 7277 | O | VAL A | 1013 | −6.564 | 24.964 | −35.277 | 1.00 | 49.98 | O |
| ATOM | 7278 | N | THR A | 1024 | −2.434 | 37.070 | −40.728 | 1.00 | 37.70 | N |
| ATOM | 7279 | CA | THR A | 1024 | −3.728 | 36.698 | −41.328 | 1.00 | 37.51 | C |
| ATOM | 7280 | CB | THR A | 1024 | −3.850 | 35.169 | −41.546 | 1.00 | 35.58 | C |
| ATOM | 7281 | OG1 | THR A | 1024 | −4.004 | 34.511 | −40.287 | 1.00 | 35.93 | O |
| ATOM | 7282 | CG2 | THR A | 1024 | −2.626 | 34.616 | −42.247 | 1.00 | 33.94 | C |
| ATOM | 7283 | C | THR A | 1024 | −4.931 | 37.198 | −40.503 | 1.00 | 37.68 | C |
| ATOM | 7284 | O | THR A | 1024 | −4.955 | 37.057 | −39.285 | 1.00 | 38.63 | O |
| ATOM | 7285 | N | GLN A | 1025 | −5.930 | 37.764 | −41.175 | 1.00 | 38.15 | N |
| ATOM | 7286 | CA | GLN A | 1025 | −7.051 | 38.423 | −40.492 | 1.00 | 39.94 | C |
| ATOM | 7287 | CB | GLN A | 1025 | −6.994 | 39.934 | −40.745 | 1.00 | 41.20 | C |
| ATOM | 7288 | CG | GLN A | 1025 | −5.702 | 40.587 | −40.266 | 1.00 | 43.85 | C |
| ATOM | 7289 | CD | GLN A | 1025 | −4.947 | 41.318 | −41.368 | 1.00 | 44.62 | C |
| ATOM | 7290 | OE1 | GLN A | 1025 | −5.536 | 41.774 | −42.352 | 1.00 | 45.82 | O |
| ATOM | 7291 | NE2 | GLN A | 1025 | −3.633 | 41.430 | −41.206 | 1.00 | 43.50 | N |
| ATOM | 7292 | C | GLN A | 1025 | −8.442 | 37.858 | −40.876 | 1.00 | 40.58 | C |
| ATOM | 7293 | O | GLN A | 1025 | −8.776 | 37.729 | −42.075 | 1.00 | 40.34 | O |
| ATOM | 7294 | N | GLY A | 1026 | −9.244 | 37.531 | −39.855 | 1.00 | 37.54 | N |
| ATOM | 7295 | CA | GLY A | 1026 | −10.586 | 36.978 | −40.065 | 1.00 | 34.95 | C |
| ATOM | 7296 | C | GLY A | 1026 | −10.501 | 35.512 | −40.428 | 1.00 | 33.44 | C |
| ATOM | 7297 | O | GLY A | 1026 | −9.429 | 34.919 | −40.333 | 1.00 | 36.78 | O |
| ATOM | 7298 | N | SER A | 1027 | −11.617 | 34.913 | −40.840 | 1.00 | 29.21 | N |

-continued

| | | | | Atomic coordinates for CRBN:DDB1:Lenalidomide (Human protein) | | | | | |
|---|---|---|---|---|---|---|---|---|---|
| ATOM | 7299 | CA | SER A | 1027 | −11.621 | 33.491 | −41.172 | 1.00 | 26.30 | C |
| ATOM | 7300 | CB | SER A | 1027 | −11.234 | 32.658 | −39.942 | 1.00 | 26.03 | C |
| ATOM | 7301 | OG | SER A | 1027 | −11.586 | 31.299 | −40.117 | 1.00 | 26.59 | O |
| ATOM | 7302 | C | SER A | 1027 | −12.952 | 33.008 | −41.752 | 1.00 | 24.66 | C |
| ATOM | 7303 | O | SER A | 1027 | −13.970 | 32.957 | −41.059 | 1.00 | 25.58 | O |
| ATOM | 7304 | N | VAL A | 1028 | −12.933 | 32.649 | −43.028 | 1.00 | 22.39 | N |
| ATOM | 7305 | CA | VAL A | 1028 | −14.085 | 32.040 | −43.672 | 1.00 | 20.83 | C |
| ATOM | 7306 | CB | VAL A | 1028 | −14.479 | 32.789 | −44.950 | 1.00 | 20.47 | C |
| ATOM | 7307 | CG1 | VAL A | 1028 | −15.621 | 32.070 | −45.645 | 1.00 | 20.07 | C |
| ATOM | 7308 | CG2 | VAL A | 1028 | −14.854 | 34.225 | −44.629 | 1.00 | 20.67 | C |
| ATOM | 7309 | C | VAL A | 1028 | −13.740 | 30.613 | −44.056 | 1.00 | 20.06 | C |
| ATOM | 7310 | O | VAL A | 1028 | −12.726 | 30.370 | −44.716 | 1.00 | 20.31 | O |
| ATOM | 7311 | N | LEU A | 1029 | −14.579 | 29.671 | −43.637 | 1.00 | 18.57 | N |
| ATOM | 7312 | CA | LEU A | 1029 | −14.413 | 28.271 | −44.006 | 1.00 | 16.82 | C |
| ATOM | 7313 | CB | LEU A | 1029 | −14.729 | 27.362 | −42.827 | 1.00 | 16.77 | C |
| ATOM | 7314 | CG | LEU A | 1029 | −14.146 | 27.721 | −41.471 | 1.00 | 16.92 | C |
| ATOM | 7315 | CD1 | LEU A | 1029 | −14.977 | 27.130 | −40.347 | 1.00 | 16.97 | C |
| ATOM | 7316 | CD2 | LEU A | 1029 | −12.714 | 27.251 | −41.390 | 1.00 | 17.64 | C |
| ATOM | 7317 | C | LEU A | 1029 | −15.361 | 27.952 | −45.138 | 1.00 | 15.79 | C |
| ATOM | 7318 | O | LEU A | 1029 | −16.423 | 28.567 | −45.256 | 1.00 | 15.52 | O |
| ATOM | 7319 | N | PHE A | 1030 | −14.970 | 27.001 | −45.981 | 1.00 | 14.78 | N |
| ATOM | 7320 | CA | PHE A | 1030 | −15.858 | 26.516 | −47.027 | 1.00 | 13.92 | C |
| ATOM | 7321 | CB | PHE A | 1030 | −15.558 | 27.146 | −48.397 | 1.00 | 13.46 | C |
| ATOM | 7322 | CG | PHE A | 1030 | −14.166 | 26.881 | −48.919 | 1.00 | 13.51 | C |
| ATOM | 7323 | CD1 | PHE A | 1030 | −13.874 | 25.707 | −49.620 | 1.00 | 13.29 | C |
| ATOM | 7324 | CE1 | PHE A | 1030 | −12.605 | 25.482 | −50.116 | 1.00 | 13.18 | C |
| ATOM | 7325 | CZ | PHE A | 1030 | −11.616 | 26.437 | −49.943 | 1.00 | 13.16 | C |
| ATOM | 7326 | CE2 | PHE A | 1030 | −11.893 | 27.617 | −49.275 | 1.00 | 13.10 | C |
| ATOM | 7327 | CD2 | PHE A | 1030 | −13.160 | 27.841 | −48.776 | 1.00 | 13.31 | C |
| ATOM | 7328 | C | PHE A | 1030 | −15.922 | 25.005 | −47.101 | 1.00 | 13.46 | C |
| ATOM | 7329 | O | PHE A | 1030 | −14.934 | 24.320 | −46.856 | 1.00 | 13.53 | O |
| ATOM | 7330 | N | GLY A | 1031 | −17.114 | 24.503 | −47.393 | 1.00 | 13.09 | N |
| ATOM | 7331 | CA | GLY A | 1031 | −17.323 | 23.090 | −47.650 | 1.00 | 12.94 | C |
| ATOM | 7332 | C | GLY A | 1031 | −17.711 | 22.847 | −49.097 | 1.00 | 12.84 | C |
| ATOM | 7333 | O | GLY A | 1031 | −18.229 | 23.727 | −49.789 | 1.00 | 12.90 | O |
| ATOM | 7334 | N | THR A | 1032 | −17.526 | 21.618 | −49.536 | 1.00 | 12.78 | N |
| ATOM | 7335 | CA | THR A | 1032 | −17.328 | 21.362 | −50.933 | 1.00 | 12.29 | C |
| ATOM | 7336 | CB | THR A | 1032 | −15.836 | 21.403 | −51.162 | 1.00 | 12.33 | C |
| ATOM | 7337 | OG1 | THR A | 1032 | −15.571 | 22.321 | −52.202 | 1.00 | 13.25 | O |
| ATOM | 7338 | CG2 | THR A | 1032 | −15.272 | 20.059 | −51.462 | 1.00 | 12.33 | C |
| ATOM | 7339 | C | THR A | 1032 | −17.945 | 20.036 | −51.394 | 1.00 | 12.18 | C |
| ATOM | 7340 | O | THR A | 1032 | −18.226 | 19.154 | −50.583 | 1.00 | 12.06 | O |
| ATOM | 7341 | N | VAL A | 1033 | −18.178 | 19.915 | −52.694 | 1.00 | 12.17 | N |
| ATOM | 7342 | CA | VAL A | 1033 | −18.793 | 18.716 | −53.272 | 1.00 | 12.34 | C |
| ATOM | 7343 | CB | VAL A | 1033 | −19.080 | 18.909 | −54.779 | 1.00 | 12.00 | C |
| ATOM | 7344 | CG1 | VAL A | 1033 | −19.368 | 17.589 | −55.455 | 1.00 | 11.90 | C |
| ATOM | 7345 | CG2 | VAL A | 1033 | −20.236 | 19.862 | −54.984 | 1.00 | 11.82 | C |
| ATOM | 7346 | C | VAL A | 1033 | −17.943 | 17.456 | −53.049 | 1.00 | 12.85 | C |
| ATOM | 7347 | O | VAL A | 1033 | −18.470 | 16.404 | −52.691 | 1.00 | 13.39 | O |
| ATOM | 7348 | N | ASN A | 1034 | −16.634 | 17.563 | −53.272 | 1.00 | 13.29 | N |
| ATOM | 7349 | CA | ASN A | 1034 | −15.714 | 16.443 | −53.094 | 1.00 | 13.53 | C |
| ATOM | 7350 | CB | ASN A | 1034 | −14.409 | 16.717 | −53.832 | 1.00 | 14.09 | C |
| ATOM | 7351 | CG | ASN A | 1034 | −14.580 | 16.698 | −55.330 | 1.00 | 14.92 | C |
| ATOM | 7352 | OD1 | ASN A | 1034 | −14.093 | 17.574 | −56.038 | 1.00 | 15.77 | O |
| ATOM | 7353 | ND2 | ASN A | 1034 | −15.281 | 15.703 | −55.823 | 1.00 | 15.14 | N |
| ATOM | 7354 | C | ASN A | 1034 | −15.415 | 16.155 | −51.636 | 1.00 | 13.65 | C |
| ATOM | 7355 | O | ASN A | 1034 | −14.677 | 15.229 | −51.321 | 1.00 | 13.70 | O |
| ATOM | 7356 | N | GLY A | 1035 | −15.968 | 16.966 | −50.745 | 1.00 | 14.03 | N |
| ATOM | 7357 | CA | GLY A | 1035 | −15.749 | 16.785 | −49.313 | 1.00 | 14.79 | C |
| ATOM | 7358 | C | GLY A | 1035 | −14.474 | 17.405 | −48.763 | 1.00 | 15.43 | C |
| ATOM | 7359 | O | GLY A | 1035 | −13.975 | 16.986 | −47.708 | 1.00 | 15.90 | O |
| ATOM | 7360 | N | MET A | 1036 | −13.957 | 18.415 | −49.458 | 1.00 | 15.28 | N |
| ATOM | 7361 | CA | MET A | 1036 | −12.799 | 19.158 | −48.995 | 1.00 | 15.06 | C |
| ATOM | 7362 | CB | MET A | 1036 | −12.005 | 19.642 | −50.206 | 1.00 | 15.97 | C |
| ATOM | 7363 | CG | MET A | 1036 | −10.759 | 20.461 | −49.921 | 1.00 | 16.53 | C |
| ATOM | 7364 | SD | MET A | 1036 | −11.088 | 22.231 | −49.952 | 1.00 | 17.60 | S |
| ATOM | 7365 | CE | MET A | 1036 | −9.452 | 22.855 | −50.322 | 1.00 | 16.67 | C |
| ATOM | 7366 | C | MET A | 1036 | −13.290 | 20.325 | −48.162 | 1.00 | 14.83 | C |
| ATOM | 7367 | O | MET A | 1036 | −14.312 | 20.930 | −48.474 | 1.00 | 15.15 | O |
| ATOM | 7368 | N | ILE A | 1037 | −12.590 | 20.609 | −47.072 | 1.00 | 14.46 | N |
| ATOM | 7369 | CA | ILE A | 1037 | −12.873 | 21.791 | −46.258 | 1.00 | 14.00 | C |
| ATOM | 7370 | CB | ILE A | 1037 | −13.110 | 21.471 | −44.768 | 1.00 | 13.38 | C |
| ATOM | 7371 | CG1 | ILE A | 1037 | −14.227 | 20.458 | −44.625 | 1.00 | 13.06 | C |
| ATOM | 7372 | CD1 | ILE A | 1037 | −14.350 | 19.892 | −43.236 | 1.00 | 13.12 | C |
| ATOM | 7373 | CG2 | ILE A | 1037 | −13.480 | 22.733 | −44.001 | 1.00 | 13.26 | C |
| ATOM | 7374 | C | ILE A | 1037 | −11.690 | 22.725 | −46.394 | 1.00 | 14.31 | C |
| ATOM | 7375 | O | ILE A | 1037 | −10.521 | 22.298 | −46.303 | 1.00 | 13.93 | O |

-continued

| | | | | Atomic coordinates for CRBN:DDB1:Lenalidomide (Human protein) | | | | | |
|---|---|---|---|---|---|---|---|---|---|
| ATOM | 7376 | N    | GLY A | 1038 | −12.002 | 23.999 | −46.628 | 1.00 | 14.48 | N |
| ATOM | 7377 | CA   | GLY A | 1038 | −10.983 | 24.997 | −46.870 | 1.00 | 14.69 | C |
| ATOM | 7378 | C    | GLY A | 1038 | −11.093 | 26.171 | −45.940 | 1.00 | 14.98 | C |
| ATOM | 7379 | O    | GLY A | 1038 | −12.063 | 26.307 | −45.193 | 1.00 | 15.00 | O |
| ATOM | 7380 | N    | LEU A | 1039 | −10.086 | 27.028 | −45.995 | 1.00 | 15.27 | N |
| ATOM | 7381 | CA   | LEU A | 1039 | −10.071 | 28.228 | −45.206 | 1.00 | 15.70 | C |
| ATOM | 7382 | CB   | LEU A | 1039 | −9.165  | 28.025 | −44.017 | 1.00 | 16.05 | C |
| ATOM | 7383 | CG   | LEU A | 1039 | −9.277  | 29.035 | −42.900 | 1.00 | 16.50 | C |
| ATOM | 7384 | CD1  | LEU A | 1039 | −9.068  | 28.302 | −41.589 | 1.00 | 17.12 | C |
| ATOM | 7385 | CD2  | LEU A | 1039 | −8.238  | 30.134 | −43.097 | 1.00 | 16.80 | C |
| ATOM | 7386 | C    | LEU A | 1039 | −9.598  | 29.399 | −46.049 | 1.00 | 15.83 | C |
| ATOM | 7387 | O    | LEU A | 1039 | −8.668  | 29.273 | −46.845 | 1.00 | 16.01 | O |
| ATOM | 7388 | N    | VAL A | 1040 | −10.264 | 30.532 | −45.885 | 1.00 | 15.95 | N |
| ATOM | 7389 | CA   | VAL A | 1040 | −9.884  | 31.757 | −46.573 | 1.00 | 16.10 | C |
| ATOM | 7390 | CB   | VAL A | 1040 | −10.957 | 32.215 | −47.591 | 1.00 | 15.48 | C |
| ATOM | 7391 | CG1  | VAL A | 1040 | −10.583 | 33.548 | −48.197 | 1.00 | 15.28 | C |
| ATOM | 7392 | CG2  | VAL A | 1040 | −11.121 | 31.191 | −48.697 | 1.00 | 15.36 | C |
| ATOM | 7393 | C    | VAL A | 1040 | −9.677  | 32.830 | −45.520 | 1.00 | 16.79 | C |
| ATOM | 7394 | O    | VAL A | 1040 | −10.490 | 32.987 | −44.608 | 1.00 | 16.96 | O |
| ATOM | 7395 | N    | THR A | 1041 | −8.575  | 33.553 | −45.629 | 1.00 | 17.75 | N |
| ATOM | 7396 | CA   | THR A | 1041 | −8.330  | 34.653 | −44.721 | 1.00 | 19.00 | C |
| ATOM | 7397 | CB   | THR A | 1041 | −7.616  | 34.203 | −43.438 | 1.00 | 19.37 | C |
| ATOM | 7398 | OG1  | THR A | 1041 | −7.448  | 35.337 | −42.584 | 1.00 | 19.82 | O |
| ATOM | 7399 | CG2  | THR A | 1041 | −6.243  | 33.587 | −43.755 | 1.00 | 19.71 | C |
| ATOM | 7400 | C    | THR A | 1041 | −7.583  | 35.809 | −45.371 | 1.00 | 19.73 | C |
| ATOM | 7401 | O    | THR A | 1041 | −6.896  | 35.647 | −46.378 | 1.00 | 19.63 | O |
| ATOM | 7402 | N    | SER A | 1042 | −7.731  | 36.980 | −44.775 | 1.00 | 20.63 | N |
| ATOM | 7403 | CA   | SER A | 1042 | −7.195  | 38.179 | −45.349 | 1.00 | 21.56 | C |
| ATOM | 7404 | CB   | SER A | 1042 | −8.034  | 39.380 | −44.930 | 1.00 | 23.04 | C |
| ATOM | 7405 | OG   | SER A | 1042 | −9.186  | 39.492 | −45.758 | 1.00 | 25.52 | O |
| ATOM | 7406 | C    | SER A | 1042 | −5.740  | 38.375 | −44.970 | 1.00 | 21.98 | C |
| ATOM | 7407 | O    | SER A | 1042 | −5.305  | 37.997 | −43.874 | 1.00 | 22.57 | O |
| ATOM | 7408 | N    | LEU A | 1043 | −4.992  | 38.971 | −45.896 | 1.00 | 21.35 | N |
| ATOM | 7409 | CA   | LEU A | 1043 | −3.600  | 39.309 | −45.683 | 1.00 | 20.71 | C |
| ATOM | 7410 | CB   | LEU A | 1043 | −2.718  | 38.542 | −46.661 | 1.00 | 20.24 | C |
| ATOM | 7411 | CG   | LEU A | 1043 | −2.503  | 37.078 | −46.342 | 1.00 | 19.60 | C |
| ATOM | 7412 | CD1  | LEU A | 1043 | −1.702  | 36.423 | −47.444 | 1.00 | 19.02 | C |
| ATOM | 7413 | CD2  | LEU A | 1043 | −1.781  | 36.988 | −45.015 | 1.00 | 20.28 | C |
| ATOM | 7414 | C    | LEU A | 1043 | −3.405  | 40.773 | −45.921 | 1.00 | 20.46 | C |
| ATOM | 7415 | O    | LEU A | 1043 | −4.033  | 41.341 | −46.813 | 1.00 | 19.78 | O |
| ATOM | 7416 | N    | SER A | 1044 | −2.518  | 41.380 | −45.142 | 1.00 | 21.18 | N |
| ATOM | 7417 | CA   | SER A | 1044 | −2.103  | 42.749 | −45.418 | 1.00 | 22.26 | C |
| ATOM | 7418 | CB   | SER A | 1044 | −1.366  | 43.377 | −44.218 | 1.00 | 22.31 | C |
| ATOM | 7419 | OG   | SER A | 1044 | −0.062  | 42.847 | −44.051 | 1.00 | 23.08 | O |
| ATOM | 7420 | C    | SER A | 1044 | −1.256  | 42.784 | −46.696 | 1.00 | 22.71 | C |
| ATOM | 7421 | O    | SER A | 1044 | −0.546  | 41.817 | −47.014 | 1.00 | 23.63 | O |
| ATOM | 7422 | N    | GLU A | 1045 | −1.368  | 43.887 | −47.430 | 1.00 | 22.78 | N |
| ATOM | 7423 | CA   | GLU A | 1045 | −0.648  | 44.115 | −48.688 | 1.00 | 23.19 | C |
| ATOM | 7424 | CB   | GLU A | 1045 | −0.802  | 45.582 | −49.072 | 1.00 | 25.08 | C |
| ATOM | 7425 | CG   | GLU A | 1045 | −0.262  | 45.977 | −50.435 | 1.00 | 26.53 | C |
| ATOM | 7426 | CD   | GLU A | 1045 | −0.539  | 47.439 | −50.759 | 1.00 | 28.39 | C |
| ATOM | 7427 | OE1  | GLU A | 1045 | −1.064  | 48.175 | −49.878 | 1.00 | 28.76 | O |
| ATOM | 7428 | OE2  | GLU A | 1045 | −0.237  | 47.850 | −51.905 | 1.00 | 29.16 | O |
| ATOM | 7429 | C    | GLU A | 1045 | 0.837   | 43.743 | −48.630 | 1.00 | 22.69 | C |
| ATOM | 7430 | O    | GLU A | 1045 | 1.407   | 43.275 | −49.621 | 1.00 | 22.42 | O |
| ATOM | 7431 | N    | SER A | 1046 | 1.457   | 43.966 | −47.473 | 1.00 | 22.05 | N |
| ATOM | 7432 | CA   | SER A | 1046 | 2.858   | 43.605 | −47.255 | 1.00 | 21.30 | C |
| ATOM | 7433 | CB   | SER A | 1046 | 3.327   | 44.070 | −45.867 | 1.00 | 21.15 | C |
| ATOM | 7434 | OG   | SER A | 1046 | 4.709   | 43.807 | −45.658 | 1.00 | 20.79 | O |
| ATOM | 7435 | C    | SER A | 1046 | 3.061   | 42.099 | −47.413 | 1.00 | 20.95 | C |
| ATOM | 7436 | O    | SER A | 1046 | 3.939   | 41.655 | −48.163 | 1.00 | 20.73 | O |
| ATOM | 7437 | N    | TRP A | 1047 | 2.236   | 41.320 | −46.715 | 1.00 | 20.48 | N |
| ATOM | 7438 | CA   | TRP A | 1047 | 2.322   | 39.861 | −46.770 | 1.00 | 20.22 | C |
| ATOM | 7439 | CB   | TRP A | 1047 | 1.490   | 39.251 | −45.666 | 1.00 | 21.44 | C |
| ATOM | 7440 | CG   | TRP A | 1047 | 2.135   | 39.411 | −44.325 | 1.00 | 22.63 | C |
| ATOM | 7441 | CD1  | TRP A | 1047 | 1.859   | 40.371 | −43.361 | 1.00 | 23.04 | C |
| ATOM | 7442 | NE1  | TRP A | 1047 | 2.650   | 40.191 | −42.256 | 1.00 | 22.87 | N |
| ATOM | 7443 | CE2  | TRP A | 1047 | 3.474   | 39.146 | −42.429 | 1.00 | 23.10 | C |
| ATOM | 7444 | CD2  | TRP A | 1047 | 3.194   | 38.591 | −43.753 | 1.00 | 23.24 | C |
| ATOM | 7445 | CE3  | TRP A | 1047 | 3.915   | 37.492 | −44.188 | 1.00 | 24.16 | C |
| ATOM | 7446 | CZ3  | TRP A | 1047 | 4.896   | 36.958 | −43.336 | 1.00 | 24.22 | C |
| ATOM | 7447 | CH2  | TRP A | 1047 | 5.149   | 37.508 | −42.071 | 1.00 | 24.12 | C |
| ATOM | 7448 | CZ2  | TRP A | 1047 | 4.443   | 38.613 | −41.597 | 1.00 | 23.81 | C |
| ATOM | 7449 | C    | TRP A | 1047 | 1.946   | 39.265 | −48.109 | 1.00 | 18.75 | C |
| ATOM | 7450 | O    | TRP A | 1047 | 2.561   | 38.293 | −45.572 | 1.00 | 17.70 | O |
| ATOM | 7451 | N    | TYR A | 1048 | 0.936   | 39.834 | −48.749 | 1.00 | 17.41 | N |
| ATOM | 7452 | CA   | TYR A | 1048 | 0.581   | 39.371 | −50.074 | 1.00 | 16.70 | C |

-continued

| | | | Atomic coordinates for CRBN:DDB1:Lenalidomide (Human protein) | | | | | | |
|---|---|---|---|---|---|---|---|---|---|
| ATOM | 7453 | CB | TYR A | 1048 | −0.681 | 40.057 | −50.583 | 1.00 | 15.37 | C |
| ATOM | 7454 | CG | TYR A | 1048 | −1.003 | 39.697 | −51.998 | 1.00 | 14.74 | C |
| ATOM | 7455 | CD1 | TYR A | 1048 | −1.614 | 38.485 | −52.305 | 1.00 | 14.50 | C |
| ATOM | 7456 | CE1 | TYR A | 1048 | −1.917 | 38.140 | −53.616 | 1.00 | 14.15 | C |
| ATOM | 7457 | CZ | TYR A | 1048 | −1.594 | 39.010 | −54.637 | 1.00 | 14.05 | C |
| ATOM | 7458 | OH | TYR A | 1048 | −1.883 | 38.674 | −55.939 | 1.00 | 13.68 | O |
| ATOM | 7459 | CE2 | TYR A | 1048 | −0.981 | 40.222 | −54.354 | 1.00 | 14.29 | C |
| ATOM | 7460 | CD2 | TYR A | 1048 | −0.684 | 40.555 | −53.042 | 1.00 | 14.46 | C |
| ATOM | 7461 | C | TYR A | 1048 | 1.763 | 39.520 | −51.059 | 1.00 | 16.86 | C |
| ATOM | 7462 | O | TYR A | 1048 | 2.093 | 38.578 | −51.791 | 1.00 | 16.84 | O |
| ATOM | 7463 | N | ASN A | 1049 | 2.407 | 40.688 | −51.063 | 1.00 | 16.82 | N |
| ATOM | 7464 | CA | ASN A | 1049 | 3.565 | 40.888 | −51.923 | 1.00 | 16.88 | C |
| ATOM | 7465 | CB | ASN A | 1049 | 4.060 | 42.330 | −51.866 | 1.00 | 17.43 | C |
| ATOM | 7466 | CG | ASN A | 1049 | 3.096 | 43.314 | −52.527 | 1.00 | 18.23 | C |
| ATOM | 7467 | OD1 | ASN A | 1049 | 2.470 | 43.018 | −53.550 | 1.00 | 18.17 | O |
| ATOM | 7468 | ND2 | ASN A | 1049 | 2.993 | 44.510 | −51.949 | 1.00 | 18.78 | N |
| ATOM | 7469 | C | ASN A | 1049 | 4.688 | 39.889 | −51.612 | 1.00 | 16.62 | C |
| ATOM | 7470 | O | ASN A | 1049 | 5.228 | 39.252 | −52.526 | 1.00 | 16.61 | O |
| ATOM | 7471 | N | LEU A | 1050 | 5.001 | 39.718 | −50.326 | 1.00 | 16.13 | N |
| ATOM | 7472 | CA | LEU A | 1050 | 6.021 | 38.746 | −49.910 | 1.00 | 15.60 | C |
| ATOM | 7473 | CB | LEU A | 1050 | 6.216 | 38.729 | −48.388 | 1.00 | 15.22 | C |
| ATOM | 7474 | CG | LEU A | 1050 | 7.148 | 37.641 | −47.827 | 1.00 | 14.82 | C |
| ATOM | 7475 | CD1 | LEU A | 1050 | 8.605 | 37.858 | −48.222 | 1.00 | 14.42 | C |
| ATOM | 7476 | CD2 | LEU A | 1050 | 7.019 | 37.596 | −46.316 | 1.00 | 14.94 | C |
| ATOM | 7477 | C | LEU A | 1050 | 5.695 | 37.345 | −50.385 | 1.00 | 15.45 | C |
| ATOM | 7478 | O | LEU A | 1050 | 6.548 | 36.672 | −50.956 | 1.00 | 15.35 | O |
| ATOM | 7479 | N | LEU A | 1051 | 4.460 | 36.909 | −50.142 | 1.00 | 15.42 | N |
| ATOM | 7480 | CA | LEU A | 1051 | 4.075 | 35.539 | −50.449 | 1.00 | 15.24 | C |
| ATOM | 7481 | CB | LEU A | 1051 | 2.834 | 35.103 | −49.658 | 1.00 | 14.68 | C |
| ATOM | 7482 | CG | LEU A | 1051 | 3.031 | 34.927 | −48.137 | 1.00 | 14.22 | C |
| ATOM | 7483 | CD1 | LEU A | 1051 | 1.712 | 34.839 | −47.393 | 1.00 | 14.01 | C |
| ATOM | 7484 | CD2 | LEU A | 1051 | 3.893 | 33.729 | −47.801 | 1.00 | 13.79 | C |
| ATOM | 7485 | C | LEU A | 1051 | 3.929 | 35.312 | −51.946 | 1.00 | 15.68 | C |
| ATOM | 7486 | O | LEU A | 1051 | 4.203 | 34.216 | −52.430 | 1.00 | 15.93 | O |
| ATOM | 7487 | N | LEU A | 1052 | 3.560 | 36.358 | −52.686 | 1.00 | 16.42 | N |
| ATOM | 7488 | CA | LEU A | 1052 | 3.513 | 36.271 | −54.150 | 1.00 | 17.17 | C |
| ATOM | 7489 | CB | LEU A | 1052 | 2.877 | 37.527 | −54.769 | 1.00 | 16.72 | C |
| ATOM | 7490 | CG | LEU A | 1052 | 1.900 | 37.349 | −55.953 | 1.00 | 16.37 | C |
| ATOM | 7491 | CD1 | LEU A | 1052 | 1.320 | 38.694 | −56.332 | 1.00 | 16.35 | C |
| ATOM | 7492 | CD2 | LEU A | 1052 | 2.520 | 36.705 | −57.186 | 1.00 | 16.47 | C |
| ATOM | 7493 | C | LEU A | 1052 | 4.908 | 35.992 | −54.756 | 1.00 | 18.11 | C |
| ATOM | 7494 | O | LEU A | 1052 | 5.049 | 35.129 | −55.631 | 1.00 | 17.33 | O |
| ATOM | 7495 | N | ASP A | 1053 | 5.923 | 36.725 | −54.288 | 1.00 | 19.86 | N |
| ATOM | 7496 | CA | ASP A | 1053 | 7.311 | 36.444 | −54.656 | 1.00 | 21.89 | C |
| ATOM | 7497 | CB | ASP A | 1053 | 8.266 | 37.254 | −53.792 | 1.00 | 24.04 | C |
| ATOM | 7498 | CG | ASP A | 1053 | 8.560 | 38.627 | −54.358 | 1.00 | 26.14 | C |
| ATOM | 7499 | OD1 | ASP A | 1053 | 7.598 | 39.317 | −54.780 | 1.00 | 26.90 | O |
| ATOM | 7500 | OD2 | ASP A | 1053 | 9.758 | 39.023 | −54.348 | 1.00 | 26.86 | O |
| ATOM | 7501 | C | ASP A | 1053 | 7.607 | 34.979 | −54.411 | 1.00 | 22.42 | C |
| ATOM | 7502 | O | ASP A | 1053 | 8.084 | 34.257 | −55.292 | 1.00 | 22.95 | O |
| ATOM | 7503 | N | MET A | 1054 | 7.294 | 34.547 | −53.198 | 1.00 | 22.76 | N |
| ATOM | 7504 | CA | MET A | 1054 | 7.636 | 33.232 | −52.734 | 1.00 | 22.58 | C |
| ATOM | 7505 | CB | MET A | 1054 | 7.198 | 33.080 | −51.307 | 1.00 | 23.58 | C |
| ATOM | 7506 | CG | MET A | 1054 | 8.057 | 32.105 | −50.557 | 1.00 | 25.65 | C |
| ATOM | 7507 | SD | MET A | 1054 | 7.670 | 32.223 | −48.813 | 1.00 | 28.01 | S |
| ATOM | 7508 | CE | MET A | 1054 | 7.950 | 30.511 | −48.333 | 1.00 | 26.01 | C |
| ATOM | 7509 | C | MET A | 1054 | 7.028 | 32.137 | −53.585 | 1.00 | 22.18 | C |
| ATOM | 7510 | O | MET A | 1054 | 7.731 | 31.206 | −53.977 | 1.00 | 22.45 | O |
| ATOM | 7511 | N | GLN A | 1055 | 5.734 | 32.250 | −53.881 | 1.00 | 21.35 | N |
| ATOM | 7512 | CA | GLN A | 1055 | 5.074 | 31.303 | −54.783 | 1.00 | 21.28 | C |
| ATOM | 7513 | CB | GLN A | 1055 | 3.646 | 31.737 | −55.099 | 1.00 | 20.49 | C |
| ATOM | 7514 | CG | GLN A | 1055 | 2.651 | 31.348 | −54.020 | 1.00 | 19.91 | C |
| ATOM | 7515 | CD | GLN A | 1055 | 1.217 | 31.686 | −54.377 | 1.00 | 20.07 | C |
| ATOM | 7516 | OE1 | GLN A | 1055 | 0.944 | 32.426 | −55.324 | 1.00 | 20.18 | O |
| ATOM | 7517 | NE2 | GLN A | 1055 | 0.293 | 31.159 | −53.605 | 1.00 | 19.48 | N |
| ATOM | 7518 | C | GLN A | 1055 | 5.859 | 31.101 | −56.074 | 1.00 | 21.67 | C |
| ATOM | 7519 | O | GLN A | 1055 | 6.111 | 29.969 | −56.491 | 1.00 | 21.44 | O |
| ATOM | 7520 | N | ASN A | 1056 | 6.275 | 32.207 | −56.676 | 1.00 | 22.47 | N |
| ATOM | 7521 | CA | ASN A | 1056 | 6.963 | 32.173 | −57.952 | 1.00 | 23.29 | C |
| ATOM | 7522 | CB | ASN A | 1056 | 7.133 | 33.579 | −58.505 | 1.00 | 24.08 | C |
| ATOM | 7523 | CG | ASN A | 1056 | 5.817 | 34.281 | −58.739 | 1.00 | 25.17 | C |
| ATOM | 7524 | OD1 | ASN A | 1056 | 5.790 | 35.315 | −59.387 | 1.00 | 27.55 | O |
| ATOM | 7525 | ND2 | ASN A | 1056 | 4.720 | 33.733 | −58.209 | 1.00 | 25.07 | N |
| ATOM | 7526 | C | ASN A | 1056 | 8.321 | 31.515 | −57.842 | 1.00 | 23.55 | C |
| ATOM | 7527 | O | ASN A | 1056 | 8.757 | 30.816 | −58.762 | 1.00 | 24.11 | O |
| ATOM | 7528 | N | ARG A | 1057 | 8.999 | 31.745 | −56.726 | 1.00 | 22.71 | N |
| ATOM | 7529 | CA | ARG A | 1057 | 10.302 | 31.164 | −56.552 | 1.00 | 22.43 | C |

-continued

| | | Atomic coordinates for CRBN:DDB1:Lenalidomide (Human protein) | | | | | | | |
|---|---|---|---|---|---|---|---|---|---|
| ATOM | 7530 | CB | ARG A | 1057 | 11.131 | 31.994 | −55.588 | 1.00 | 23.48 | C |
| ATOM | 7531 | CG | ARG A | 1057 | 11.492 | 33.344 | −56.173 | 1.00 | 25.45 | C |
| ATOM | 7532 | CD | ARG A | 1057 | 12.110 | 34.303 | −55.163 | 1.00 | 28.25 | C |
| ATOM | 7533 | NE | ARG A | 1057 | 12.019 | 35.686 | −55.647 | 1.00 | 30.38 | N |
| ATOM | 7534 | CZ | ARG A | 1057 | 12.974 | 36.316 | −56.334 | 1.00 | 31.48 | C |
| ATOM | 7535 | NH1 | ARG A | 1057 | 14.128 | 35.711 | −56.609 | 1.00 | 32.14 | N |
| ATOM | 7536 | NH2 | ARG A | 1057 | 12.776 | 37.560 | −56.745 | 1.00 | 32.02 | N |
| ATOM | 7537 | C | ARG A | 1057 | 10.172 | 29.704 | −56.138 | 1.00 | 21.97 | C |
| ATOM | 7538 | O | ARG A | 1057 | 10.958 | 28.868 | −56.573 | 1.00 | 21.88 | O |
| ATOM | 7539 | N | LEU A | 1058 | 9.147 | 29.387 | −55.344 | 1.00 | 21.27 | N |
| ATOM | 7540 | CA | LEU A | 1058 | 8.825 | 27.985 | −55.034 | 1.00 | 20.74 | C |
| ATOM | 7541 | CB | LEU A | 1058 | 7.737 | 27.870 | −53.964 | 1.00 | 20.54 | C |
| ATOM | 7542 | CG | LEU A | 1058 | 8.105 | 27.734 | −52.480 | 1.00 | 20.25 | C |
| ATOM | 7543 | CD1 | LEU A | 1058 | 6.830 | 27.842 | −51.651 | 1.00 | 20.25 | C |
| ATOM | 7544 | CD2 | LEU A | 1058 | 8.868 | 26.453 | −52.151 | 1.00 | 19.29 | C |
| ATOM | 7545 | C | LEU A | 1058 | 8.390 | 27.198 | −56.269 | 1.00 | 20.41 | C |
| ATOM | 7546 | O | LEU A | 1058 | 8.598 | 25.985 | −56.343 | 1.00 | 20.45 | O |
| ATOM | 7547 | N | ASN A | 1059 | 7.780 | 27.878 | −57.235 | 1.00 | 19.62 | N |
| ATOM | 7548 | CA | ASN A | 1059 | 7.406 | 27.211 | −58.470 | 1.00 | 19.09 | C |
| ATOM | 7549 | CB | ASN A | 1059 | 6.413 | 28.031 | −59.272 | 1.00 | 18.30 | C |
| ATOM | 7550 | CG | ASN A | 1059 | 5.060 | 28.121 | −58.590 | 1.00 | 17.84 | C |
| ATOM | 7551 | OD1 | ASN A | 1059 | 4.619 | 27.184 | −57.932 | 1.00 | 17.18 | O |
| ATOM | 7552 | ND2 | ASN A | 1059 | 4.399 | 29.258 | −58.740 | 1.00 | 18.08 | N |
| ATOM | 7553 | C | ASN A | 1059 | 8.586 | 26.740 | −59.314 | 1.00 | 19.40 | C |
| ATOM | 7554 | O | ASN A | 1059 | 8.503 | 25.700 | −59.942 | 1.00 | 20.17 | O |
| ATOM | 7555 | N | LYS A | 1060 | 9.690 | 27.480 | −59.284 | 1.00 | 19.72 | N |
| ATOM | 7556 | CA | LYS A | 1060 | 10.910 | 27.095 | −60.003 | 1.00 | 20.03 | C |
| ATOM | 7557 | CB | LYS A | 1060 | 11.927 | 28.234 | −59.973 | 1.00 | 19.98 | C |
| ATOM | 7558 | CG | LYS A | 1060 | 11.444 | 29.551 | −60.553 | 1.00 | 20.50 | C |
| ATOM | 7559 | CD | LYS A | 1060 | 12.581 | 30.558 | −60.621 | 1.00 | 21.29 | C |
| ATOM | 7560 | CE | LYS A | 1060 | 12.237 | 31.741 | −61.517 | 1.00 | 22.12 | C |
| ATOM | 7561 | NZ | LYS A | 1060 | 11.562 | 32.828 | −60.754 | 1.00 | 23.27 | N |
| ATOM | 7562 | C | LYS A | 1060 | 11.554 | 25.827 | −59.416 | 1.00 | 20.68 | C |
| ATOM | 7563 | O | LYS A | 1060 | 12.178 | 25.034 | −60.130 | 1.00 | 20.26 | O |
| ATOM | 7564 | N | VAL A | 1061 | 11.385 | 25.645 | −58.113 | 1.00 | 21.47 | N |
| ATOM | 7565 | CA | VAL A | 1061 | 12.057 | 24.588 | −57.374 | 1.00 | 22.39 | C |
| ATOM | 7566 | CB | VAL A | 1061 | 12.450 | 25.103 | −55.970 | 1.00 | 22.69 | C |
| ATOM | 7567 | CG1 | VAL A | 1061 | 12.772 | 23.960 | −55.022 | 1.00 | 23.52 | C |
| ATOM | 7568 | CG2 | VAL A | 1061 | 13.628 | 26.052 | −56.070 | 1.00 | 23.00 | C |
| ATOM | 7569 | C | VAL A | 1061 | 11.249 | 23.272 | −57.284 | 1.00 | 23.41 | C |
| ATOM | 7570 | O | VAL A | 1061 | 11.803 | 22.190 | −57.473 | 1.00 | 23.89 | O |
| ATOM | 7571 | N | ILE A | 1062 | 9.951 | 23.362 | −56.996 | 1.00 | 24.06 | N |
| ATOM | 7572 | CA | ILE A | 1062 | 9.141 | 22.161 | −56.743 | 1.00 | 24.77 | C |
| ATOM | 7573 | CB | ILE A | 1062 | 7.836 | 22.497 | −55.998 | 1.00 | 23.31 | C |
| ATOM | 7574 | CG1 | ILE A | 1062 | 8.162 | 22.951 | −54.575 | 1.00 | 22.64 | C |
| ATOM | 7575 | CD1 | ILE A | 1062 | 7.002 | 23.566 | −53.841 | 1.00 | 22.21 | C |
| ATOM | 7576 | CG2 | ILE A | 1062 | 6.906 | 21.294 | −55.995 | 1.00 | 22.19 | C |
| ATOM | 7577 | C | ILE A | 1062 | 8.803 | 21.411 | −58.021 | 1.00 | 26.59 | C |
| ATOM | 7578 | O | ILE A | 1062 | 8.440 | 22.030 | −59.025 | 1.00 | 27.80 | O |
| ATOM | 7579 | N | LYS A | 1063 | 8.929 | 20.081 | −57.973 | 1.00 | 27.74 | N |
| ATOM | 7580 | CA | LYS A | 1063 | 8.562 | 19.207 | −59.098 | 1.00 | 28.21 | C |
| ATOM | 7581 | CB | LYS A | 1063 | 9.413 | 17.907 | −59.107 | 1.00 | 29.80 | C |
| ATOM | 7582 | CG | LYS A | 1063 | 8.757 | 16.723 | −59.842 | 1.00 | 32.05 | C |
| ATOM | 7583 | CD | LYS A | 1063 | 9.704 | 15.920 | −60.753 | 1.00 | 31.74 | C |
| ATOM | 7584 | CE | LYS A | 1063 | 9.006 | 15.443 | −62.040 | 1.00 | 30.05 | C |
| ATOM | 7585 | NZ | LYS A | 1063 | 7.657 | 14.820 | −61.848 | 1.00 | 27.71 | N |
| ATOM | 7586 | C | LYS A | 1063 | 7.071 | 18.890 | −59.036 | 1.00 | 26.78 | C |
| ATOM | 7587 | O | LYS A | 1063 | 6.591 | 18.395 | −58.025 | 1.00 | 27.60 | O |
| ATOM | 7588 | N | SER A | 1064 | 6.342 | 19.189 | −60.110 | 1.00 | 25.12 | N |
| ATOM | 7589 | CA | SER A | 1064 | 4.903 | 18.909 | −60.149 | 1.00 | 23.81 | C |
| ATOM | 7590 | CB | SER A | 1064 | 4.112 | 20.124 | −60.634 | 1.00 | 22.63 | C |
| ATOM | 7591 | OG | SER A | 1064 | 3.884 | 20.069 | −62.027 | 1.00 | 21.91 | O |
| ATOM | 7592 | C | SER A | 1064 | 4.623 | 17.696 | −61.029 | 1.00 | 23.38 | C |
| ATOM | 7593 | O | SER A | 1064 | 5.255 | 17.531 | −62.079 | 1.00 | 23.01 | O |
| ATOM | 7594 | N | VAL A | 1065 | 3.651 | 16.878 | −60.619 | 1.00 | 22.64 | N |
| ATOM | 7595 | CA | VAL A | 1065 | 3.551 | 15.505 | −61.115 | 1.00 | 22.14 | C |
| ATOM | 7596 | CB | VAL A | 1065 | 2.503 | 14.663 | −61.357 | 1.00 | 21.13 | C |
| ATOM | 7597 | CG1 | VAL A | 1065 | 2.010 | 13.495 | −61.192 | 1.00 | 20.60 | C |
| ATOM | 7598 | CG2 | VAL A | 1065 | 3.122 | 14.134 | −59.077 | 1.00 | 20.61 | C |
| ATOM | 7599 | C | VAL A | 1065 | 3.507 | 15.337 | −62.642 | 1.00 | 23.08 | C |
| ATOM | 7600 | O | VAL A | 1065 | 4.386 | 14.676 | −63.208 | 1.00 | 24.48 | O |
| ATOM | 7601 | N | GLY A | 1066 | 2.533 | 15.936 | −63.318 | 1.00 | 22.54 | N |
| ATOM | 7602 | CA | GLY A | 1066 | 2.489 | 15.820 | −64.787 | 1.00 | 21.43 | C |
| ATOM | 7603 | C | GLY A | 1066 | 3.274 | 16.919 | −65.490 | 1.00 | 20.83 | C |
| ATOM | 7604 | O | GLY A | 1066 | 3.009 | 17.230 | −66.667 | 1.00 | 20.98 | O |
| ATOM | 7605 | N | LYS A | 1067 | 4.236 | 17.504 | −64.768 | 1.00 | 19.54 | N |
| ATOM | 7606 | CA | LYS A | 1067 | 4.927 | 18.731 | −65.195 | 1.00 | 18.80 | C |

| Atomic coordinates for CRBN:DDB1:Lenalidomide (Human protein) | | | | | | | | | |
|---|---|---|---|---|---|---|---|---|---|
| ATOM | 7607 | CB | LYS A | 1067 | 5.982 | 18.439 | −66.277 | 1.00 | 18.99 | C |
| ATOM | 7608 | CG | LYS A | 1067 | 7.220 | 17.722 | −65.753 | 1.00 | 19.21 | C |
| ATOM | 7609 | CD | LYS A | 1067 | 8.162 | 17.333 | −66.877 | 1.00 | 19.52 | C |
| ATOM | 7610 | CE | LYS A | 1067 | 9.531 | 16.971 | −66.320 | 1.00 | 20.16 | C |
| ATOM | 7611 | NZ | LYS A | 1067 | 10.346 | 16.156 | −67.269 | 1.00 | 20.47 | N |
| ATOM | 7612 | C | LYS A | 1067 | 3.958 | 19.840 | −65.637 | 1.00 | 17.84 | C |
| ATOM | 7613 | O | LYS A | 1067 | 4.125 | 20.438 | −66.687 | 1.00 | 17.47 | O |
| ATOM | 7614 | N | ILE A | 1068 | 2.943 | 20.092 | −64.820 | 1.00 | 17.12 | N |
| ATOM | 7615 | CA | ILE A | 1068 | 2.005 | 21.181 | −65.055 | 1.00 | 16.72 | C |
| ATOM | 7616 | CB | ILE A | 1068 | 0.568 | 20.776 | −64.668 | 1.00 | 16.45 | C |
| ATOM | 7617 | CG1 | ILE A | 1068 | 0.216 | 19.420 | −65.282 | 1.00 | 16.00 | C |
| ATOM | 7618 | CD1 | ILE A | 1068 | −1.107 | 18.870 | −64.805 | 1.00 | 16.20 | C |
| ATOM | 7619 | CG2 | ILE A | 1068 | −0.431 | 21.861 | −65.072 | 1.00 | 16.13 | C |
| ATOM | 7620 | C | ILE A | 1068 | 2.403 | 22.410 | −64.251 | 1.00 | 16.65 | C |
| ATOM | 7621 | O | ILE A | 1068 | 2.661 | 22.326 | −63.060 | 1.00 | 16.36 | O |
| ATOM | 7622 | N | GLU A | 1069 | 2.436 | 23.552 | −64.916 | 1.00 | 17.16 | N |
| ATOM | 7623 | CA | GLU A | 1069 | 2.786 | 24.805 | −64.281 | 1.00 | 17.77 | C |
| ATOM | 7624 | CB | GLU A | 1069 | 2.972 | 25.871 | −65.355 | 1.00 | 19.98 | C |
| ATOM | 7625 | CG | GLU A | 1069 | 4.204 | 25.675 | −66.223 | 1.00 | 23.06 | C |
| ATOM | 7626 | CD | GLU A | 1069 | 5.385 | 26.529 | −65.774 | 1.00 | 26.20 | C |
| ATOM | 7627 | OE1 | GLU A | 1069 | 5.823 | 26.391 | −64.596 | 1.00 | 26.45 | O |
| ATOM | 7628 | OE2 | GLU A | 1069 | 5.871 | 27.350 | −66.611 | 1.00 | 28.65 | O |
| ATOM | 7629 | C | GLU A | 1069 | 1.721 | 25.265 | −63.266 | 1.00 | 17.00 | C |
| ATOM | 7630 | O | GLU A | 1069 | 0.553 | 25.479 | −63.634 | 1.00 | 17.06 | O |
| ATOM | 7631 | N | HIS A | 1070 | 2.124 | 25.431 | −61.998 | 1.00 | 15.25 | N |
| ATOM | 7632 | CA | HIS A | 1070 | 1.249 | 25.996 | −60.967 | 1.00 | 13.96 | C |
| ATOM | 7633 | CB | HIS A | 1070 | 2.063 | 26.456 | −59.769 | 1.00 | 13.83 | C |
| ATOM | 7634 | CG | HIS A | 1070 | 1.226 | 26.966 | −58.624 | 1.00 | 13.78 | C |
| ATOM | 7635 | ND1 | HIS A | 1070 | 0.983 | 28.281 | −58.431 | 1.00 | 13.79 | N |
| ATOM | 7636 | CE1 | HIS A | 1070 | 0.189 | 28.434 | −57.353 | 1.00 | 13.71 | C |
| ATOM | 7637 | NE2 | HIS A | 1070 | −0.085 | 27.211 | −56.858 | 1.00 | 13.74 | N |
| ATOM | 7638 | CD2 | HIS A | 1070 | 0.540 | 26.284 | −57.614 | 1.00 | 13.56 | C |
| ATOM | 7639 | C | HIS A | 1070 | 0.395 | 27.123 | −61.484 | 1.00 | 13.43 | C |
| ATOM | 7640 | O | HIS A | 1070 | −0.801 | 27.164 | −61.247 | 1.00 | 12.80 | O |
| ATOM | 7641 | N | SER A | 1071 | 1.013 | 28.035 | −62.221 | 1.00 | 13.43 | N |
| ATOM | 7642 | CA | SER A | 1071 | 0.320 | 29.176 | −62.818 | 1.00 | 13.53 | C |
| ATOM | 7643 | CB | SER A | 1071 | 1.301 | 29.982 | −63.639 | 1.00 | 13.24 | C |
| ATOM | 7644 | OG | SER A | 1071 | 1.520 | 31.197 | −62.986 | 1.00 | 13.47 | O |
| ATOM | 7645 | C | SER A | 1071 | −0.863 | 28.806 | −63.704 | 1.00 | 13.62 | C |
| ATOM | 7646 | O | SER A | 1071 | −1.892 | 29.499 | −63.741 | 1.00 | 13.34 | O |
| ATOM | 7647 | N | PHE A | 1072 | −0.687 | 27.722 | −64.442 | 1.00 | 13.62 | N |
| ATOM | 7648 | CA | PHE A | 1072 | −1.690 | 27.270 | −65.358 | 1.00 | 13.70 | C |
| ATOM | 7649 | CB | PHE A | 1072 | −1.090 | 26.219 | −66.292 | 1.00 | 13.71 | C |
| ATOM | 7650 | CG | PHE A | 1072 | −2.081 | 25.597 | −67.197 | 1.00 | 13.67 | C |
| ATOM | 7651 | CD1 | PHE A | 1072 | −2.587 | 26.309 | −68.275 | 1.00 | 13.50 | C |
| ATOM | 7652 | CE1 | PHE A | 1072 | −3.531 | 25.738 | −69.111 | 1.00 | 13.91 | C |
| ATOM | 7653 | CZ | PHE A | 1072 | −3.974 | 24.439 | −68.877 | 1.00 | 14.23 | C |
| ATOM | 7654 | CE2 | PHE A | 1072 | −3.475 | 23.718 | −67.794 | 1.00 | 14.21 | C |
| ATOM | 7655 | CD2 | PHE A | 1072 | −2.533 | 24.301 | −66.958 | 1.00 | 13.81 | C |
| ATOM | 7656 | C | PHE A | 1072 | −2.859 | 26.707 | −64.559 | 1.00 | 13.78 | C |
| ATOM | 7657 | O | PHE A | 1072 | −4.021 | 26.957 | −64.884 | 1.00 | 14.11 | O |
| ATOM | 7658 | N | TRP A | 1073 | −2.525 | 25.977 | −63.495 | 1.00 | 13.55 | N |
| ATOM | 7659 | CA | TRP A | 1073 | −3.493 | 25.356 | −62.591 | 1.00 | 13.20 | C |
| ATOM | 7660 | CB | TRP A | 1073 | −2.729 | 24.497 | −61.584 | 1.00 | 12.86 | C |
| ATOM | 7661 | CG | TRP A | 1073 | −3.488 | 23.958 | −60.388 | 1.00 | 12.64 | C |
| ATOM | 7662 | CD1 | TRP A | 1073 | −3.093 | 24.003 | −59.041 | 1.00 | 12.50 | C |
| ATOM | 7663 | NE1 | TRP A | 1073 | −4.018 | 23.382 | −58.232 | 1.00 | 12.25 | N |
| ATOM | 7664 | CE2 | TRP A | 1073 | −5.042 | 22.892 | −58.977 | 1.00 | 12.39 | C |
| ATOM | 7665 | CD2 | TRP A | 1073 | −4.758 | 23.221 | −60.385 | 1.00 | 12.38 | C |
| ATOM | 7666 | CE3 | TRP A | 1073 | −5.664 | 22.840 | −61.357 | 1.00 | 12.09 | C |
| ATOM | 7667 | CZ3 | TRP A | 1073 | −6.816 | 22.148 | −60.962 | 1.00 | 11.82 | C |
| ATOM | 7668 | CH2 | TRP A | 1073 | −7.067 | 21.841 | −59.628 | 1.00 | 11.94 | C |
| ATOM | 7669 | CZ2 | TRP A | 1073 | −6.187 | 22.206 | −58.605 | 1.00 | 12.22 | C |
| ATOM | 7670 | C | TRP A | 1073 | −4.373 | 26.380 | −61.927 | 1.00 | 13.32 | C |
| ATOM | 7671 | O | TRP A | 1073 | −5.589 | 26.300 | −62.029 | 1.00 | 13.33 | O |
| ATOM | 7672 | N | ARG A | 1074 | −3.771 | 27.387 | −61.296 | 1.00 | 13.77 | N |
| ATOM | 7673 | CA | ARG A | 1074 | −4.530 | 28.365 | −60.502 | 1.00 | 14.41 | C |
| ATOM | 7674 | CB | ARG A | 1074 | −3.655 | 28.986 | −59.415 | 1.00 | 14.02 | C |
| ATOM | 7675 | CG | ARG A | 1074 | −3.224 | 28.008 | −58.336 | 1.00 | 13.84 | C |
| ATOM | 7676 | CD | ARG A | 1074 | −4.353 | 27.064 | −57.955 | 1.00 | 13.55 | C |
| ATOM | 7677 | NE | ARG A | 1074 | −4.079 | 26.430 | −56.673 | 1.00 | 13.40 | N |
| ATOM | 7678 | CZ | ARG A | 1074 | −4.977 | 25.779 | −55.954 | 1.00 | 12.99 | C |
| ATOM | 7679 | NH1 | ARG A | 1074 | −6.222 | 25.669 | −56.381 | 1.00 | 13.08 | N |
| ATOM | 7680 | NH2 | ARG A | 1074 | −4.629 | 25.254 | −54.804 | 1.00 | 12.88 | N |
| ATOM | 7681 | C | ARG A | 1074 | −5.216 | 29.458 | −61.318 | 1.00 | 15.26 | C |
| ATOM | 7682 | O | ARG A | 1074 | −6.027 | 30.234 | −60.781 | 1.00 | 14.96 | O |
| ATOM | 7683 | N | SER A | 1075 | −4.893 | 29.497 | −62.610 | 1.00 | 16.29 | N |

-continued

| | | | | | | | | | |
|---|---|---|---|---|---|---|---|---|---|
| \multicolumn{10}{l}{Atomic coordinates for CRBN:DDB1:Lenalidomide (Human protein)} |

| ATOM | 7684 | CA | SER A | 1075 | −5.442 | 30.454 | −63.531 | 1.00 | 17.54 | C |
|---|---|---|---|---|---|---|---|---|---|---|
| ATOM | 7685 | CB | SER A | 1075 | −4.833 | 30.208 | −64.895 | 1.00 | 17.91 | C |
| ATOM | 7686 | OG | SER A | 1075 | −4.316 | 31.406 | −65.446 | 1.00 | 19.24 | O |
| ATOM | 7687 | C | SER A | 1075 | −6.960 | 30.294 | −63.595 | 1.00 | 18.86 | C |
| ATOM | 7688 | O | SER A | 1075 | −7.463 | 29.203 | −63.850 | 1.00 | 19.53 | O |
| ATOM | 7689 | N | PHE A | 1076 | −7.686 | 31.375 | −63.315 | 1.00 | 20.22 | N |
| ATOM | 7690 | CA | PHE A | 1076 | −9.146 | 31.400 | −63.422 | 1.00 | 21.15 | C |
| ATOM | 7691 | CB | PHE A | 1076 | −9.630 | 32.840 | −63.212 | 1.00 | 21.10 | C |
| ATOM | 7692 | CG | PHE A | 1076 | −11.116 | 33.041 | −63.398 | 1.00 | 21.25 | C |
| ATOM | 7693 | CD1 | PHE A | 1076 | −11.696 | 33.006 | −64.679 | 1.00 | 20.92 | C |
| ATOM | 7694 | CE1 | PHE A | 1076 | −13.058 | 33.217 | −64.850 | 1.00 | 20.26 | C |
| ATOM | 7695 | CZ | PHE A | 1076 | −13.856 | 33.492 | −63.743 | 1.00 | 20.61 | C |
| ATOM | 7696 | CE2 | PHE A | 1076 | −13.296 | 33.544 | −62.468 | 1.00 | 20.56 | C |
| ATOM | 7697 | CD2 | PHE A | 1076 | −11.934 | 33.334 | −62.299 | 1.00 | 20.90 | C |
| ATOM | 7698 | C | PHE A | 1076 | −9.568 | 30.845 | −64.790 | 1.00 | 22.49 | C |
| ATOM | 7699 | O | PHE A | 1076 | −9.033 | 31.255 | −65.830 | 1.00 | 22.71 | O |
| ATOM | 7700 | N | HIS A | 1077 | −10.524 | 29.917 | −64.783 | 1.00 | 24.61 | N |
| ATOM | 7701 | CA | HIS A | 1077 | −10.825 | 29.070 | −65.960 | 1.00 | 26.47 | C |
| ATOM | 7702 | CB | HIS A | 1077 | −10.183 | 27.689 | −65.754 | 1.00 | 28.32 | C |
| ATOM | 7703 | CG | HIS A | 1077 | −10.555 | 26.660 | −66.811 | 1.00 | 30.35 | C |
| ATOM | 7704 | ND1 | HIS A | 1077 | −10.239 | 26.808 | −68.124 | 1.00 | 31.52 | N |
| ATOM | 7705 | CE1 | HIS A | 1077 | −10.688 | 25.741 | −68.816 | 1.00 | 31.37 | C |
| ATOM | 7706 | NE2 | HIS A | 1077 | −11.283 | 24.900 | −67.947 | 1.00 | 31.98 | N |
| ATOM | 7707 | CD2 | HIS A | 1077 | −11.215 | 25.433 | −66.703 | 1.00 | 30.85 | C |
| ATOM | 7708 | C | HIS A | 1077 | −12.297 | 28.904 | −66.263 | 1.00 | 26.24 | C |
| ATOM | 7709 | O | HIS A | 1077 | −13.103 | 28.715 | −65.366 | 1.00 | 24.84 | O |
| ATOM | 7710 | N | THR A | 1078 | −12.661 | 28.963 | −67.538 | 1.00 | 28.55 | N |
| ATOM | 7711 | CA | THR A | 1078 | −14.008 | 28.521 | −67.961 | 1.00 | 30.31 | C |
| ATOM | 7712 | CB | THR A | 1078 | −14.979 | 29.705 | −68.229 | 1.00 | 30.23 | C |
| ATOM | 7713 | OG1 | THR A | 1078 | −14.536 | 30.468 | −69.360 | 1.00 | 31.54 | O |
| ATOM | 7714 | CG2 | THR A | 1078 | −15.078 | 30.608 | −67.009 | 1.00 | 29.60 | C |
| ATOM | 7715 | C | THR A | 1078 | −14.017 | 27.521 | −69.144 | 1.00 | 30.30 | C |
| ATOM | 7716 | O | THR A | 1078 | −13.104 | 27.499 | −69.981 | 1.00 | 29.83 | O |
| ATOM | 7717 | N | LYS A | 1081 | −12.811 | 30.972 | −71.684 | 1.00 | 50.00 | N |
| ATOM | 7718 | CA | LYS A | 1081 | −11.960 | 32.028 | −71.127 | 1.00 | 48.46 | C |
| ATOM | 7719 | CB | LYS A | 1081 | −12.810 | 33.140 | −70.490 | 1.00 | 45.99 | C |
| ATOM | 7720 | C | LYS A | 1081 | −10.940 | 31.494 | −70.110 | 1.00 | 48.69 | C |
| ATOM | 7721 | O | LYS A | 1081 | −11.222 | 30.539 | −69.357 | 1.00 | 46.95 | O |
| ATOM | 7722 | N | THR A | 1082 | −9.754 | 32.118 | −70.111 | 1.00 | 46.37 | N |
| ATOM | 7723 | CA | THR A | 1082 | −8.695 | 31.857 | −69.118 | 1.00 | 42.00 | C |
| ATOM | 7724 | CB | THR A | 1082 | −7.761 | 30.700 | −69.553 | 1.00 | 42.10 | C |
| ATOM | 7725 | OG1 | THR A | 1082 | −8.368 | 29.449 | −69.192 | 1.00 | 43.06 | O |
| ATOM | 7726 | CG2 | THR A | 1082 | −6.366 | 30.803 | −68.895 | 1.00 | 39.48 | C |
| ATOM | 7727 | C | THR A | 1082 | −7.904 | 33.128 | −68.824 | 1.00 | 39.27 | C |
| ATOM | 7728 | O | THR A | 1082 | −7.475 | 33.830 | −69.741 | 1.00 | 39.77 | O |
| ATOM | 7729 | N | GLU A | 1083 | −7.748 | 33.423 | −67.535 | 1.00 | 36.33 | N |
| ATOM | 7730 | CA | GLU A | 1083 | −7.011 | 34.598 | −67.061 | 1.00 | 32.57 | C |
| ATOM | 7731 | CB | GLU A | 1083 | −7.975 | 35.692 | −66.608 | 1.00 | 34.84 | C |
| ATOM | 7732 | CG | GLU A | 1083 | −7.475 | 33.830 | −69.741 | 1.00 | 39.77 | C |
| ATOM | 7733 | CD | GLU A | 1083 | −9.562 | 37.552 | −67.190 | 1.00 | 40.78 | C |
| ATOM | 7734 | OE1 | GLU A | 1083 | −9.477 | 37.978 | −66.015 | 1.00 | 41.65 | O |
| ATOM | 7735 | OE2 | GLU A | 1083 | −10.509 | 37.853 | −67.951 | 1.00 | 43.01 | O |
| ATOM | 7736 | C | GLU A | 1083 | −6.151 | 34.195 | −65.880 | 1.00 | 28.26 | C |
| ATOM | 7737 | O | GLU A | 1083 | −6.506 | 33.279 | −65.137 | 1.00 | 27.38 | O |
| ATOM | 7738 | N | PRO A | 1084 | −5.022 | 34.884 | −65.686 | 1.00 | 25.81 | N |
| ATOM | 7739 | CA | PRO A | 1084 | −4.139 | 34.542 | −64.562 | 1.00 | 24.29 | C |
| ATOM | 7740 | CB | PRO A | 1084 | −2.961 | 35.497 | −64.735 | 1.00 | 23.94 | C |
| ATOM | 7741 | CG | PRO A | 1084 | −2.986 | 35.861 | −66.180 | 1.00 | 24.84 | C |
| ATOM | 7742 | CD | PRO A | 1084 | −4.431 | 35.905 | −66.560 | 1.00 | 25.20 | C |
| ATOM | 7743 | C | PRO A | 1084 | −4.802 | 34.752 | −63.199 | 1.00 | 22.30 | C |
| ATOM | 7744 | O | PRO A | 1084 | −5.676 | 35.612 | −63.058 | 1.00 | 22.29 | O |
| ATOM | 7745 | N | ALA A | 1085 | −4.395 | 33.946 | −62.218 | 1.00 | 20.07 | N |
| ATOM | 7746 | CA | ALA A | 1085 | −4.841 | 34.103 | −60.834 | 1.00 | 18.00 | C |
| ATOM | 7747 | CB | ALA A | 1085 | −4.247 | 33.012 | −59.952 | 1.00 | 17.35 | C |
| ATOM | 7748 | C | ALA A | 1085 | −4.438 | 35.472 | −60.324 | 1.00 | 16.99 | C |
| ATOM | 7749 | O | ALA A | 1085 | −3.501 | 36.101 | −60.833 | 1.00 | 16.01 | O |
| ATOM | 7750 | N | THR A | 1086 | −5.153 | 35.942 | −59.319 | 1.00 | 16.23 | N |
| ATOM | 7751 | CA | THR A | 1086 | −4.863 | 37.252 | −58.780 | 1.00 | 15.67 | C |
| ATOM | 7752 | CB | THR A | 1086 | −5.203 | 38.357 | −59.808 | 1.00 | 15.86 | C |
| ATOM | 7753 | OG1 | THR A | 1086 | −4.428 | 39.521 | −59.516 | 1.00 | 16.98 | O |
| ATOM | 7754 | CG2 | THR A | 1086 | −6.704 | 38.700 | −59.834 | 1.00 | 16.00 | C |
| ATOM | 7755 | C | THR A | 1086 | −5.514 | 37.485 | −57.418 | 1.00 | 14.86 | C |
| ATOM | 7756 | O | THR A | 1086 | −6.603 | 36.983 | −57.147 | 1.00 | 14.60 | O |
| ATOM | 7757 | N | GLY A | 1087 | −4.812 | 38.200 | −56.547 | 1.00 | 14.27 | N |
| ATOM | 7758 | CA | GLY A | 1087 | −5.324 | 38.507 | −55.206 | 1.00 | 14.16 | C |
| ATOM | 7759 | C | GLY A | 1087 | −5.567 | 37.306 | −54.313 | 1.00 | 13.99 | C |
| ATOM | 7760 | O | GLY A | 1087 | −6.234 | 37.408 | −53.287 | 1.00 | 14.22 | O |

-continued

| | | | | | Atomic coordinates for CRBN:DDB1:Lenalidomide (Human protein) | | | | |
|---|---|---|---|---|---|---|---|---|---|
| ATOM | 7761 | N | PHE A | 1088 | −5.041 | 36.158 | −54.714 | 1.00 | 13.92 | N |
| ATOM | 7762 | CA | PHE A | 1088 | −5.155 | 34.944 | −53.919 | 1.00 | 13.90 | C |
| ATOM | 7763 | CB | PHE A | 1088 | −6.135 | 33.955 | −54.572 | 1.00 | 13.94 | C |
| ATOM | 7764 | CG | PHE A | 1088 | −7.568 | 34.201 | −54.228 | 1.00 | 13.75 | C |
| ATOM | 7765 | CD1 | PHE A | 1088 | −8.103 | 33.707 | −53.052 | 1.00 | 13.70 | C |
| ATOM | 7766 | CE1 | PHE A | 1088 | −9.431 | 33.931 | −52.726 | 1.00 | 13.78 | C |
| ATOM | 7767 | CZ | PHE A | 1088 | −10.244 | 34.652 | −53.586 | 1.00 | 13.89 | C |
| ATOM | 7768 | CE2 | PHE A | 1088 | −9.722 | 35.151 | −54.767 | 1.00 | 13.85 | C |
| ATOM | 7769 | CD2 | PHE A | 1088 | −8.387 | 34.924 | −55.083 | 1.00 | 13.84 | C |
| ATOM | 7770 | C | PHE A | 1088 | −3.799 | 34.277 | −53.781 | 1.00 | 13.60 | C |
| ATOM | 7771 | O | PHE A | 1088 | −3.061 | 34.170 | −54.765 | 1.00 | 13.27 | O |
| ATOM | 7772 | N | ILE A | 1089 | −3.494 | 33.816 | −52.568 | 1.00 | 13.32 | N |
| ATOM | 7773 | CA | ILE A | 1089 | −2.296 | 33.024 | −52.316 | 1.00 | 13.36 | C |
| ATOM | 7774 | CB | ILE A | 1089 | −1.454 | 33.649 | −51.207 | 1.00 | 13.27 | C |
| ATOM | 7775 | CG1 | ILE A | 1089 | −0.780 | 34.898 | −51.750 | 1.00 | 13.50 | C |
| ATOM | 7776 | CD1 | ILE A | 1089 | −0.442 | 35.893 | −50.673 | 1.00 | 13.99 | C |
| ATOM | 7777 | CG2 | ILE A | 1089 | −0.424 | 32.659 | −50.688 | 1.00 | 13.15 | C |
| ATOM | 7778 | C | ILE A | 1089 | −2.615 | 31.565 | −51.983 | 1.00 | 13.33 | C |
| ATOM | 7779 | O | ILE A | 1089 | −3.377 | 31.275 | −51.048 | 1.00 | 13.25 | O |
| ATOM | 7780 | N | ASP A | 1090 | −2.036 | 30.659 | −52.770 | 1.00 | 13.07 | N |
| ATOM | 7781 | CA | ASP A | 1090 | −2.194 | 29.232 | −52.567 | 1.00 | 13.03 | C |
| ATOM | 7782 | CB | ASP A | 1090 | −1.807 | 28.450 | −53.823 | 1.00 | 13.15 | C |
| ATOM | 7783 | CG | ASP A | 1090 | −2.032 | 26.966 | −53.668 | 1.00 | 13.56 | C |
| ATOM | 7784 | OD1 | ASP A | 1090 | −2.856 | 26.593 | −52.814 | 1.00 | 14.57 | O |
| ATOM | 7785 | OD2 | ASP A | 1090 | −1.395 | 26.161 | −54.367 | 1.00 | 13.45 | O |
| ATOM | 7786 | C | ASP A | 1090 | −1.358 | 28.773 | −51.380 | 1.00 | 13.07 | C |
| ATOM | 7787 | O | ASP A | 1090 | −0.195 | 28.405 | −51.530 | 1.00 | 13.24 | O |
| ATOM | 7788 | N | GLY A | 1091 | −1.969 | 28.789 | −50.201 | 1.00 | 13.03 | N |
| ATOM | 7789 | CA | GLY A | 1091 | −1.316 | 28.374 | −48.973 | 1.00 | 12.82 | C |
| ATOM | 7790 | C | GLY A | 1091 | −0.897 | 26.928 | −49.027 | 1.00 | 13.00 | C |
| ATOM | 7791 | O | GLY A | 1091 | 0.024 | 26.526 | −48.321 | 1.00 | 13.01 | O |
| ATOM | 7792 | N | ASP A | 1092 | −1.577 | 26.136 | −49.857 | 1.00 | 13.20 | N |
| ATOM | 7793 | CA | ASP A | 1092 | −1.174 | 24.756 | −50.073 | 1.00 | 13.39 | C |
| ATOM | 7794 | CB | ASP A | 1092 | −2.124 | 24.048 | −51.032 | 1.00 | 14.10 | C |
| ATOM | 7795 | CG | ASP A | 1092 | −3.322 | 23.415 | −50.320 | 1.00 | 14.70 | C |
| ATOM | 7796 | OD1 | ASP A | 1092 | −3.625 | 23.819 | −49.183 | 1.00 | 15.73 | O |
| ATOM | 7797 | OD2 | ASP A | 1092 | −3.961 | 22.506 | −50.890 | 1.00 | 14.40 | O |
| ATOM | 7798 | C | ASP A | 1092 | 0.229 | 24.751 | −50.631 | 1.00 | 13.56 | C |
| ATOM | 7799 | O | ASP A | 1092 | 1.083 | 23.998 | −50.160 | 1.00 | 14.03 | O |
| ATOM | 7800 | N | LEU A | 1093 | 0.480 | 25.620 | −51.611 | 1.00 | 13.43 | N |
| ATOM | 7801 | CA | LEU A | 1093 | 1.827 | 25.800 | −52.161 | 1.00 | 13.17 | C |
| ATOM | 7802 | CB | LEU A | 1093 | 1.796 | 26.633 | −53.441 | 1.00 | 13.01 | C |
| ATOM | 7803 | CG | LEU A | 1093 | 3.165 | 26.961 | −54.042 | 1.00 | 12.83 | C |
| ATOM | 7804 | CD1 | LEU A | 1093 | 3.905 | 25.696 | −54.450 | 1.00 | 12.79 | C |
| ATOM | 7805 | CD2 | LEU A | 1093 | 3.000 | 27.915 | −55.212 | 1.00 | 12.93 | C |
| ATOM | 7806 | C | LEU A | 1093 | 2.833 | 26.403 | −51.171 | 1.00 | 13.13 | C |
| ATOM | 7807 | O | LEU A | 1093 | 3.953 | 25.896 | −51.042 | 1.00 | 13.44 | O |
| ATOM | 7808 | N | ILE A | 1094 | 2.455 | 27.494 | −50.504 | 1.00 | 12.71 | N |
| ATOM | 7809 | CA | ILE A | 1094 | 3.342 | 28.118 | −49.517 | 1.00 | 12.54 | C |
| ATOM | 7810 | CB | ILE A | 1094 | 2.702 | 29.365 | −48.864 | 1.00 | 12.27 | C |
| ATOM | 7811 | CG1 | ILE A | 1094 | 2.521 | 30.483 | −49.896 | 1.00 | 12.12 | C |
| ATOM | 7812 | CD1 | ILE A | 1094 | 3.805 | 31.059 | −50.439 | 1.00 | 12.14 | C |
| ATOM | 7813 | CG2 | ILE A | 1094 | 3.520 | 29.849 | −47.671 | 1.00 | 12.20 | C |
| ATOM | 7814 | C | ILE A | 1094 | 3.814 | 27.124 | −48.447 | 1.00 | 12.62 | C |
| ATOM | 7815 | O | ILE A | 1094 | 4.988 | 27.087 | −48.113 | 1.00 | 12.21 | O |
| ATOM | 7816 | N | GLU A | 1095 | 2.905 | 26.294 | −47.945 | 1.00 | 13.23 | N |
| ATOM | 7817 | CA | GLU A | 1095 | 3.242 | 25.380 | −46.853 | 1.00 | 13.72 | C |
| ATOM | 7818 | CB | GLU A | 1095 | 1.986 | 24.801 | −46.194 | 1.00 | 14.72 | C |
| ATOM | 7819 | CG | GLU A | 1095 | 1.428 | 25.768 | −45.152 | 1.00 | 16.66 | C |
| ATOM | 7820 | CD | GLU A | 1095 | −0.005 | 25.477 | −44.690 | 1.00 | 17.88 | C |
| ATOM | 7821 | OE1 | GLU A | 1095 | −0.378 | 24.272 | −44.602 | 1.00 | 18.12 | O |
| ATOM | 7822 | OE2 | GLU A | 1095 | −0.745 | 26.473 | −44.394 | 1.00 | 17.82 | O |
| ATOM | 7823 | C | GLU A | 1095 | 4.252 | 24.309 | −47.224 | 1.00 | 13.12 | C |
| ATOM | 7824 | O | GLU A | 1095 | 5.001 | 23.850 | −46.373 | 1.00 | 12.96 | O |
| ATOM | 7825 | N | SER A | 1096 | 4.301 | 23.941 | −48.497 | 1.00 | 12.84 | N |
| ATOM | 7826 | CA | SER A | 1096 | 5.295 | 22.985 | −48.957 | 1.00 | 12.86 | C |
| ATOM | 7827 | CB | SER A | 1096 | 4.978 | 22.519 | −50.370 | 1.00 | 12.91 | C |
| ATOM | 7828 | OG | SER A | 1096 | 5.208 | 23.552 | −51.299 | 1.00 | 13.20 | O |
| ATOM | 7829 | C | SER A | 1096 | 6.742 | 23.511 | −48.866 | 1.00 | 12.94 | C |
| ATOM | 7830 | O | SER A | 1096 | 7.686 | 22.730 | −48.916 | 1.00 | 13.08 | O |
| ATOM | 7831 | N | PHE A | 1097 | 6.916 | 24.822 | −48.711 | 1.00 | 13.02 | N |
| ATOM | 7832 | CA | PHE A | 1097 | 8.240 | 25.392 | −48.428 | 1.00 | 13.13 | C |
| ATOM | 7833 | CB | PHE A | 1097 | 8.140 | 26.867 | −48.015 | 1.00 | 12.88 | C |
| ATOM | 7834 | CG | PHE A | 1097 | 9.434 | 27.459 | −47.522 | 1.00 | 12.76 | C |
| ATOM | 7835 | CD1 | PHE A | 1097 | 10.425 | 27.855 | −48.413 | 1.00 | 12.87 | C |
| ATOM | 7836 | CE1 | PHE A | 1097 | 11.614 | 28.406 | −47.961 | 1.00 | 12.55 | C |
| ATOM | 7837 | CZ | PHE A | 1097 | 11.819 | 28.575 | −46.603 | 1.00 | 12.62 | C |

-continued

| Atomic coordinates for CRBN:DDB1:Lenalidomide (Human protein) | | | | | | | | | |
|---|---|---|---|---|---|---|---|---|---|
| ATOM | 7838 | CE2 | PHE A | 1097 | 10.845 | 28.186 | −45.705 | 1.00 | 12.63 | C |
| ATOM | 7839 | CD2 | PHE A | 1097 | 9.659 | 27.635 | −46.166 | 1.00 | 12.69 | C |
| ATOM | 7840 | C | PHE A | 1097 | 8.980 | 24.609 | −47.360 | 1.00 | 13.53 | C |
| ATOM | 7841 | O | PHE A | 1097 | 10.201 | 24.517 | −47.406 | 1.00 | 13.79 | O |
| ATOM | 7842 | N | LEU A | 1098 | 8.239 | 24.044 | −46.406 | 1.00 | 14.27 | N |
| ATOM | 7843 | CA | LEU A | 1098 | 8.829 | 23.348 | −45.253 | 1.00 | 15.01 | C |
| ATOM | 7844 | CB | LEU A | 1098 | 7.796 | 23.143 | −44.156 | 1.00 | 14.51 | C |
| ATOM | 7845 | CG | LEU A | 1098 | 7.249 | 24.433 | −43.581 | 1.00 | 14.60 | C |
| ATOM | 7846 | CD1 | LEU A | 1098 | 5.979 | 24.141 | −42.797 | 1.00 | 14.79 | C |
| ATOM | 7847 | CD2 | LEU A | 1098 | 8.299 | 25.140 | −42.732 | 1.00 | 14.37 | C |
| ATOM | 7848 | C | LEU A | 1098 | 9.445 | 22.007 | −45.619 | 1.00 | 15.80 | C |
| ATOM | 7849 | O | LEU A | 1098 | 10.334 | 21.509 | −44.927 | 1.00 | 16.53 | O |
| ATOM | 7850 | N | ASP A | 1099 | 8.992 | 21.435 | −46.718 | 1.00 | 16.18 | N |
| ATOM | 7851 | CA | ASP A | 1099 | 9.408 | 20.113 | −47.059 | 1.00 | 17.20 | C |
| ATOM | 7852 | CB | ASP A | 1099 | 8.190 | 19.305 | −47.543 | 1.00 | 18.36 | C |
| ATOM | 7853 | CG | ASP A | 1099 | 7.124 | 19.102 | −46.412 | 1.00 | 19.84 | C |
| ATOM | 7854 | OD1 | ASP A | 1099 | 7.521 | 18.793 | −45.252 | 1.00 | 20.26 | O |
| ATOM | 7855 | OD2 | ASP A | 1099 | 5.897 | 19.262 | −46.672 | 1.00 | 19.98 | O |
| ATOM | 7856 | C | ASP A | 1099 | 10.610 | 20.079 | −48.025 | 1.00 | 17.56 | C |
| ATOM | 7857 | O | ASP A | 1099 | 11.192 | 19.026 | −48.236 | 1.00 | 18.09 | O |
| ATOM | 7858 | N | ILE A | 1100 | 11.010 | 21.224 | −48.578 | 1.00 | 17.87 | N |
| ATOM | 7859 | CA | ILE A | 1100 | 12.160 | 21.264 | −49.509 | 1.00 | 18.52 | C |
| ATOM | 7860 | CB | ILE A | 1100 | 12.091 | 22.441 | −50.535 | 1.00 | 18.36 | C |
| ATOM | 7861 | CG1 | ILE A | 1100 | 12.307 | 23.802 | −49.856 | 1.00 | 18.11 | C |
| ATOM | 7862 | CD1 | ILE A | 1100 | 12.196 | 24.991 | −50.786 | 1.00 | 18.22 | C |
| ATOM | 7863 | CG2 | ILE A | 1100 | 10.787 | 22.414 | −51.327 | 1.00 | 18.01 | C |
| ATOM | 7864 | C | ILE A | 1100 | 13.509 | 21.260 | −48.764 | 1.00 | 19.48 | C |
| ATOM | 7865 | O | ILE A | 1100 | 13.559 | 21.529 | −47.562 | 1.00 | 19.64 | O |
| ATOM | 7866 | N | SER A | 1101 | 14.594 | 20.957 | −49.485 | 1.00 | 20.72 | N |
| ATOM | 7867 | CA | SER A | 1101 | 15.931 | 20.813 | −48.878 | 1.00 | 21.82 | C |
| ATOM | 7868 | CB | SER A | 1101 | 16.897 | 20.103 | −49.835 | 1.00 | 22.16 | C |
| ATOM | 7869 | OG | SER A | 1101 | 17.446 | 21.001 | −50.781 | 1.00 | 22.13 | O |
| ATOM | 7870 | C | SER A | 1101 | 16.521 | 22.154 | −48.474 | 1.00 | 22.33 | C |
| ATOM | 7871 | O | SER A | 1101 | 16.295 | 23.155 | −49.140 | 1.00 | 23.44 | O |
| ATOM | 7872 | N | ARG A | 1102 | 17.304 | 22.163 | −47.403 | 1.00 | 22.61 | N |
| ATOM | 7873 | CA | ARG A | 1102 | 17.886 | 23.404 | −46.891 | 1.00 | 23.06 | C |
| ATOM | 7874 | CB | ARG A | 1102 | 18.915 | 23.111 | −45.784 | 1.00 | 23.77 | C |
| ATOM | 7875 | CG | ARG A | 1102 | 19.447 | 24.339 | −45.073 | 1.00 | 24.58 | C |
| ATOM | 7876 | CD | ARG A | 1102 | 18.475 | 24.840 | −44.023 | 1.00 | 26.60 | C |
| ATOM | 7877 | NE | ARG A | 1102 | 19.027 | 25.975 | −43.284 | 1.00 | 28.86 | N |
| ATOM | 7878 | CZ | ARG A | 1102 | 18.423 | 26.593 | −42.263 | 1.00 | 29.92 | C |
| ATOM | 7879 | NH1 | ARG A | 1102 | 17.221 | 26.190 | −41.827 | 1.00 | 28.81 | N |
| ATOM | 7880 | NH2 | ARG A | 1102 | 19.030 | 27.625 | −41.674 | 1.00 | 29.84 | N |
| ATOM | 7881 | C | ARG A | 1102 | 18.470 | 24.308 | −47.998 | 1.00 | 22.56 | C |
| ATOM | 7882 | O | ARG A | 1102 | 18.228 | 25.512 | −47.986 | 1.00 | 21.25 | O |
| ATOM | 7883 | N | PRO A | 1103 | 19.241 | 23.730 | −48.953 | 1.00 | 23.49 | N |
| ATOM | 7884 | CA | PRO A | 1103 | 19.748 | 24.564 | −50.066 | 1.00 | 24.07 | C |
| ATOM | 7885 | CB | PRO A | 1103 | 20.631 | 23.600 | −50.877 | 1.00 | 23.98 | C |
| ATOM | 7886 | CG | PRO A | 1103 | 20.407 | 22.239 | −50.294 | 1.00 | 23.89 | C |
| ATOM | 7887 | CD | PRO A | 1103 | 19.939 | 22.431 | −48.890 | 1.00 | 23.33 | C |
| ATOM | 7888 | C | PRO A | 1103 | 18.655 | 25.165 | −50.956 | 1.00 | 24.11 | C |
| ATOM | 7889 | O | PRO A | 1103 | 18.807 | 26.287 | −51.450 | 1.00 | 24.52 | O |
| ATOM | 7890 | N | LYS A | 1104 | 17.572 | 24.421 | −51.153 | 1.00 | 23.77 | N |
| ATOM | 7891 | CA | LYS A | 1104 | 16.439 | 24.911 | −51.915 | 1.00 | 23.95 | C |
| ATOM | 7892 | CB | LYS A | 1104 | 15.508 | 23.758 | −52.300 | 1.00 | 25.24 | C |
| ATOM | 7893 | CG | LYS A | 1104 | 16.138 | 22.658 | −53.153 | 1.00 | 26.74 | C |
| ATOM | 7894 | CD | LYS A | 1104 | 16.899 | 23.196 | −54.360 | 1.00 | 28.54 | C |
| ATOM | 7895 | CE | LYS A | 1104 | 16.038 | 23.303 | −55.611 | 1.00 | 29.55 | C |
| ATOM | 7896 | NZ | LYS A | 1104 | 16.594 | 24.290 | −56.593 | 1.00 | 29.88 | N |
| ATOM | 7897 | C | LYS A | 1104 | 15.666 | 26.012 | −51.169 | 1.00 | 23.61 | C |
| ATOM | 7898 | O | LYS A | 1104 | 15.230 | 26.979 | −51.788 | 1.00 | 23.72 | O |
| ATOM | 7899 | N | MET A | 1105 | 15.495 | 25.860 | −49.850 | 1.00 | 23.37 | N |
| ATOM | 7900 | CA | MET A | 1105 | 14.924 | 26.920 | −49.008 | 1.00 | 23.10 | C |
| ATOM | 7901 | CB | MET A | 1105 | 14.958 | 26.559 | −47.527 | 1.00 | 21.94 | C |
| ATOM | 7902 | CG | MET A | 1105 | 14.052 | 25.426 | −47.095 | 1.00 | 21.99 | C |
| ATOM | 7903 | SD | MET A | 1105 | 13.826 | 25.385 | −45.300 | 1.00 | 21.66 | S |
| ATOM | 7904 | CE | MET A | 1105 | 14.050 | 23.630 | −44.980 | 1.00 | 22.82 | C |
| ATOM | 7905 | C | MET A | 1105 | 15.687 | 28.215 | −49.202 | 1.00 | 24.47 | C |
| ATOM | 7906 | O | MET A | 1105 | 15.086 | 29.274 | −49.343 | 1.00 | 24.93 | O |
| ATOM | 7907 | N | GLN A | 1106 | 17.016 | 28.136 | −49.209 | 1.00 | 26.69 | N |
| ATOM | 7908 | CA | GLN A | 1106 | 17.810 | 29.344 | −49.378 | 1.00 | 28.53 | C |
| ATOM | 7909 | CB | GLN A | 1106 | 19.228 | 29.198 | −48.876 | 1.00 | 30.06 | C |
| ATOM | 7910 | CG | GLN A | 1106 | 19.782 | 30.549 | −48.458 | 1.00 | 32.31 | C |
| ATOM | 7911 | CD | GLN A | 1106 | 19.431 | 30.894 | −47.017 | 1.00 | 35.13 | C |
| ATOM | 7912 | OE1 | GLN A | 1106 | 19.403 | 30.010 | −46.151 | 1.00 | 36.66 | O |
| ATOM | 7913 | NE2 | GLN A | 1106 | 19.186 | 32.182 | −46.744 | 1.00 | 34.65 | N |
| ATOM | 7914 | C | GLN A | 1106 | 17.833 | 29.834 | −50.802 | 1.00 | 29.07 | C |

| | | | | | | | | | | |
|---|---|---|---|---|---|---|---|---|---|---|
| ATOM | 7915 | O | GLN A | 1106 | 17.791 | 31.043 | −51.031 | 1.00 | 29.68 | O |
| ATOM | 7916 | N | GLU A | 1107 | 17.903 | 28.902 | −51.753 | 1.00 | 29.17 | N |
| ATOM | 7917 | CA | GLU A | 1107 | 17.797 | 29.238 | −53.166 | 1.00 | 29.07 | C |
| ATOM | 7918 | CB | GLU A | 1107 | 17.391 | 28.021 | −53.979 | 1.00 | 29.83 | C |
| ATOM | 7919 | CG | GLU A | 1107 | 17.581 | 28.188 | −55.474 | 1.00 | 31.51 | C |
| ATOM | 7920 | CD | GLU A | 1107 | 18.381 | 27.047 | −56.080 | 1.00 | 33.82 | C |
| ATOM | 7921 | OE1 | GLU A | 1107 | 18.473 | 26.990 | −57.321 | 1.00 | 35.18 | O |
| ATOM | 7922 | OE2 | GLU A | 1107 | 18.934 | 26.207 | −55.321 | 1.00 | 35.03 | O |
| ATOM | 7923 | C | GLU A | 1107 | 16.780 | 30.335 | −53.371 | 1.00 | 28.97 | C |
| ATOM | 7924 | O | GLU A | 1107 | 17.083 | 31.364 | −53.970 | 1.00 | 28.72 | O |
| ATOM | 7925 | N | ASN A | 1108 | 15.585 | 30.135 | −52.827 | 1.00 | 29.56 | N |
| ATOM | 7926 | CA | ASN A | 1108 | 14.468 | 30.991 | −53.170 | 1.00 | 30.95 | C |
| ATOM | 7927 | CB | ASN A | 1108 | 13.296 | 30.150 | −53.684 | 1.00 | 31.87 | C |
| ATOM | 7928 | CG | ASN A | 1108 | 12.616 | 29.372 | −52.593 | 1.00 | 32.21 | C |
| ATOM | 7929 | OD1 | ASN A | 1108 | 11.979 | 29.949 | −51.707 | 1.00 | 32.45 | O |
| ATOM | 7930 | ND2 | ASN A | 1108 | 12.724 | 28.047 | −52.660 | 1.00 | 33.01 | N |
| ATOM | 7931 | C | ASN A | 1108 | 14.020 | 32.040 | −52.139 | 1.00 | 30.66 | C |
| ATOM | 7932 | O | ASN A | 1108 | 13.052 | 32.759 | −52.370 | 1.00 | 30.82 | O |
| ATOM | 7933 | N | VAL A | 1109 | 14.726 | 32.150 | −51.021 | 1.00 | 30.93 | N |
| ATOM | 7934 | CA | VAL A | 1109 | 14.584 | 33.350 | −50.182 | 1.00 | 31.54 | C |
| ATOM | 7935 | CB | VAL A | 1109 | 14.549 | 33.027 | −48.669 | 1.00 | 31.14 | C |
| ATOM | 7936 | CG1 | VAL A | 1109 | 13.386 | 32.100 | −48.362 | 1.00 | 31.01 | C |
| ATOM | 7937 | CG2 | VAL A | 1109 | 15.858 | 32.410 | −48.195 | 1.00 | 30.93 | C |
| ATOM | 7938 | C | VAL A | 1109 | 15.675 | 34.377 | −50.513 | 1.00 | 32.25 | C |
| ATOM | 7939 | O | VAL A | 1109 | 15.884 | 35.330 | −49.775 | 1.00 | 32.10 | O |
| ATOM | 7940 | N | ALA A | 1110 | 16.339 | 34.169 | −51.654 | 1.00 | 34.69 | N |
| ATOM | 7941 | CA | ALA A | 1110 | 17.505 | 34.952 | −52.089 | 1.00 | 34.94 | C |
| ATOM | 7942 | CB | ALA A | 1110 | 18.108 | 34.345 | −53.349 | 1.00 | 33.53 | C |
| ATOM | 7943 | C | ALA A | 1110 | 17.193 | 36.420 | −52.314 | 1.00 | 35.64 | C |
| ATOM | 7944 | O | ALA A | 1110 | 17.962 | 37.288 | −51.924 | 1.00 | 34.43 | O |
| ATOM | 7945 | N | ASN A | 1111 | 16.063 | 36.694 | −52.948 | 1.00 | 39.84 | N |
| ATOM | 7946 | CA | ASN A | 1111 | 15.674 | 38.072 | −53.225 | 1.00 | 44.48 | C |
| ATOM | 7947 | CB | ASN A | 1111 | 15.724 | 38.353 | −54.739 | 1.00 | 46.42 | C |
| ATOM | 7948 | CG | ASN A | 1111 | 17.063 | 37.971 | −55.367 | 1.00 | 46.69 | C |
| ATOM | 7949 | OD1 | ASN A | 1111 | 17.161 | 36.972 | −56.086 | 1.00 | 46.01 | O |
| ATOM | 7950 | ND2 | ASN A | 1111 | 18.102 | 38.762 | −55.089 | 1.00 | 46.02 | N |
| ATOM | 7951 | C | ASN A | 1111 | 14.302 | 38.421 | −52.623 | 1.00 | 45.28 | C |
| ATOM | 7952 | O | ASN A | 1111 | 13.378 | 38.839 | −53.331 | 1.00 | 47.23 | O |
| ATOM | 7953 | N | LEU A | 1112 | 14.180 | 38.240 | −51.310 | 1.00 | 43.07 | N |
| ATOM | 7954 | CA | LEU A | 1112 | 12.941 | 38.545 | −50.612 | 1.00 | 43.33 | C |
| ATOM | 7955 | CB | LEU A | 1112 | 12.303 | 37.271 | −50.050 | 1.00 | 43.37 | C |
| ATOM | 7956 | CG | LEU A | 1112 | 12.011 | 36.107 | −50.994 | 1.00 | 44.43 | C |
| ATOM | 7957 | CD1 | LEU A | 1112 | 11.229 | 35.027 | −50.261 | 1.00 | 43.36 | C |
| ATOM | 7958 | CD2 | LEU A | 1112 | 11.252 | 36.578 | −52.227 | 1.00 | 44.79 | C |
| ATOM | 7959 | C | LEU A | 1112 | 13.150 | 39.559 | −49.490 | 1.00 | 43.56 | C |
| ATOM | 7960 | O | LEU A | 1112 | 13.993 | 39.360 | −49.609 | 1.00 | 42.72 | O |
| ATOM | 7961 | N | GLN A | 1113 | 12.377 | 40.643 | −49.526 | 1.00 | 43.01 | N |
| ATOM | 7962 | CA | GLN A | 1113 | 12.413 | 41.632 | −48.465 | 1.00 | 43.86 | C |
| ATOM | 7963 | CB | GLN A | 1113 | 12.104 | 43.031 | −49.007 | 1.00 | 44.44 | C |
| ATOM | 7964 | C | GLN A | 1113 | 11.427 | 41.246 | −47.381 | 1.00 | 45.26 | C |
| ATOM | 7965 | O | GLN A | 1113 | 10.228 | 41.152 | −47.631 | 1.00 | 47.72 | O |
| ATOM | 7966 | N | TYR A | 1114 | 11.952 | 40.995 | −46.185 | 1.00 | 47.45 | N |
| ATOM | 7967 | CA | TYR A | 1114 | 11.151 | 40.715 | −44.990 | 1.00 | 49.79 | C |
| ATOM | 7968 | CB | TYR A | 1114 | 11.989 | 39.887 | −44.016 | 1.00 | 48.00 | C |
| ATOM | 7969 | CG | TYR A | 1114 | 11.224 | 39.175 | −42.934 | 1.00 | 46.89 | C |
| ATOM | 7970 | CD1 | TYR A | 1114 | 9.951 | 38.679 | −43.166 | 1.00 | 48.38 | C |
| ATOM | 7971 | CE1 | TYR A | 1114 | 9.248 | 38.015 | −42.173 | 1.00 | 49.62 | C |
| ATOM | 7972 | CZ | TYR A | 1114 | 9.830 | 37.820 | −40.932 | 1.00 | 50.14 | C |
| ATOM | 7973 | OH | TYR A | 1114 | 9.127 | 37.149 | −39.949 | 1.00 | 49.58 | O |
| ATOM | 7974 | CE2 | TYR A | 1114 | 11.108 | 38.295 | −40.681 | 1.00 | 49.30 | C |
| ATOM | 7975 | CD2 | TYR A | 1114 | 11.795 | 38.964 | −41.682 | 1.00 | 47.69 | C |
| ATOM | 7976 | C | TYR A | 1114 | 10.759 | 42.054 | −44.363 | 1.00 | 52.62 | C |
| ATOM | 7977 | O | TYR A | 1114 | 11.312 | 43.087 | −44.745 | 1.00 | 54.36 | O |
| ATOM | 7978 | N | ASP A | 1115 | 9.827 | 42.057 | −43.408 | 1.00 | 55.08 | N |
| ATOM | 7979 | CA | ASP A | 1115 | 9.374 | 43.339 | −42.840 | 1.00 | 60.05 | C |
| ATOM | 7980 | CB | ASP A | 1115 | 8.011 | 43.755 | −43.405 | 1.00 | 61.79 | C |
| ATOM | 7981 | CG | ASP A | 1115 | 8.127 | 44.878 | −44.425 | 1.00 | 61.82 | C |
| ATOM | 7982 | OD1 | ASP A | 1115 | 9.021 | 44.809 | −45.298 | 1.00 | 61.29 | O |
| ATOM | 7983 | OD2 | ASP A | 1115 | 7.333 | 45.839 | −44.347 | 1.00 | 62.41 | O |
| ATOM | 7984 | C | ASP A | 1115 | 9.452 | 43.579 | −41.320 | 1.00 | 61.89 | C |
| ATOM | 7985 | O | ASP A | 1115 | 8.662 | 43.037 | −40.539 | 1.00 | 61.75 | O |
| ATOM | 7986 | N | ASP A | 1116 | 10.415 | 44.425 | −40.940 | 1.00 | 64.53 | N |
| ATOM | 7987 | CA | ASP A | 1116 | 10.607 | 44.908 | −39.565 | 1.00 | 64.30 | C |
| ATOM | 7988 | CB | ASP A | 1116 | 11.718 | 44.110 | −38.851 | 1.00 | 66.15 | C |
| ATOM | 7989 | CG | ASP A | 1116 | 11.177 | 43.122 | −37.805 | 1.00 | 66.69 | C |
| ATOM | 7990 | OD1 | ASP A | 1116 | 10.062 | 42.569 | −37.979 | 1.00 | 67.25 | O |
| ATOM | 7991 | OD2 | ASP A | 1116 | 11.892 | 42.892 | −36.804 | 1.00 | 64.93 | O |

-continued

| \multicolumn{10}{|c|}{Atomic coordinates for CRBN:DDB1:Lenalidomide (Human protein)} |

| | | | | | | | | | |
|---|---|---|---|---|---|---|---|---|---|
| ATOM | 7992 | C | ASP A | 1116 | 10.947 | 46.414 | −39.563 | 1.00 | 61.66 | C |
| ATOM | 7993 | O | ASP A | 1116 | 12.063 | 46.814 | −39.926 | 1.00 | 57.08 | O |
| ATOM | 7994 | N | GLY A | 1117 | 9.977 | 47.238 | −39.165 | 1.00 | 58.28 | N |
| ATOM | 7995 | CA | GLY A | 1117 | 10.180 | 48.679 | −39.069 | 1.00 | 54.36 | C |
| ATOM | 7996 | C | GLY A | 1117 | 10.401 | 49.316 | −40.424 | 1.00 | 51.59 | C |
| ATOM | 7997 | O | GLY A | 1117 | 9.603 | 49.129 | −41.339 | 1.00 | 49.18 | O |
| ATOM | 7998 | N | ASP A | 1121 | 13.226 | 47.049 | −43.825 | 1.00 | 35.24 | N |
| ATOM | 7999 | CA | ASP A | 1121 | 13.222 | 45.764 | −44.518 | 1.00 | 37.39 | C |
| ATOM | 8000 | CB | ASP A | 1121 | 12.649 | 45.929 | −45.930 | 1.00 | 36.73 | C |
| ATOM | 8001 | C | ASP A | 1121 | 14.626 | 45.131 | −44.584 | 1.00 | 38.64 | C |
| ATOM | 8002 | O | ASP A | 1121 | 15.639 | 45.853 | −44.598 | 1.00 | 38.44 | O |
| ATOM | 8003 | N | LEU A | 1122 | 14.683 | 43.791 | −44.621 | 1.00 | 36.90 | N |
| ATOM | 8004 | CA | LEU A | 1122 | 15.961 | 43.059 | −44.809 | 1.00 | 34.92 | C |
| ATOM | 8005 | CB | LEU A | 1122 | 16.611 | 42.674 | −43.453 | 1.00 | 35.42 | C |
| ATOM | 8006 | CG | LEU A | 1122 | 15.861 | 41.845 | −42.384 | 1.00 | 36.68 | C |
| ATOM | 8007 | CD1 | LEU A | 1122 | 16.166 | 40.348 | −42.483 | 1.00 | 34.54 | C |
| ATOM | 8008 | CD2 | LEU A | 1122 | 16.157 | 42.358 | −40.973 | 1.00 | 36.18 | C |
| ATOM | 8009 | C | LEU A | 1122 | 15.850 | 41.833 | −45.740 | 1.00 | 33.36 | C |
| ATOM | 8010 | O | LEU A | 1122 | 14.786 | 41.215 | −45.850 | 1.00 | 32.98 | O |
| ATOM | 8011 | N | ILE A | 1123 | 16.952 | 41.504 | −46.414 | 1.00 | 31.32 | N |
| ATOM | 8012 | CA | ILE A | 1123 | 17.055 | 40.272 | −47.185 | 1.00 | 30.27 | C |
| ATOM | 8013 | CB | ILE A | 1123 | 18.469 | 40.074 | −47.769 | 1.00 | 28.91 | C |
| ATOM | 8014 | C | ILE A | 1123 | 16.701 | 39.102 | −46.267 | 1.00 | 30.80 | C |
| ATOM | 8015 | O | ILE A | 1123 | 17.352 | 38.890 | −45.239 | 1.00 | 31.07 | O |
| ATOM | 8016 | N | LYS A | 1124 | 15.652 | 38.367 | −46.631 | 1.00 | 29.94 | N |
| ATOM | 8017 | CA | LYS A | 1124 | 15.095 | 37.325 | −45.779 | 1.00 | 29.34 | C |
| ATOM | 8018 | CB | LYS A | 1124 | 13.719 | 36.917 | −46.289 | 1.00 | 28.86 | C |
| ATOM | 8019 | C | LYS A | 1124 | 15.974 | 36.083 | −45.646 | 1.00 | 29.80 | C |
| ATOM | 8020 | O | LYS A | 1124 | 16.542 | 35.604 | −46.625 | 1.00 | 29.08 | O |
| ATOM | 8021 | N | VAL A | 1125 | 16.057 | 35.567 | −44.419 | 1.00 | 31.05 | N |
| ATOM | 8022 | CA | VAL A | 1125 | 16.703 | 34.283 | −44.123 | 1.00 | 31.13 | C |
| ATOM | 8023 | CB | VAL A | 1125 | 17.363 | 34.280 | −42.731 | 1.00 | 31.02 | C |
| ATOM | 8024 | CG1 | VAL A | 1125 | 18.504 | 33.270 | −42.694 | 1.00 | 32.28 | C |
| ATOM | 8025 | CG2 | VAL A | 1125 | 17.857 | 35.669 | −42.355 | 1.00 | 31.26 | C |
| ATOM | 8026 | C | VAL A | 1125 | 15.703 | 33.125 | −44.132 | 1.00 | 31.51 | C |
| ATOM | 8027 | O | VAL A | 1125 | 14.536 | 33.285 | −43.762 | 1.00 | 31.00 | O |
| ATOM | 8028 | N | VAL A | 1126 | 16.183 | 31.954 | −44.535 | 1.00 | 32.43 | N |
| ATOM | 8029 | CA | VAL A | 1126 | 15.442 | 30.699 | −44.410 | 1.00 | 32.71 | C |
| ATOM | 8030 | CB | VAL A | 1126 | 16.373 | 29.497 | −44.553 | 1.00 | 34.38 | C |
| ATOM | 8031 | CG1 | VAL A | 1126 | 16.560 | 29.158 | −46.015 | 1.00 | 35.81 | C |
| ATOM | 8032 | CG2 | VAL A | 1126 | 17.712 | 29.762 | −43.862 | 1.00 | 35.74 | C |
| ATOM | 8033 | C | VAL A | 1126 | 14.720 | 30.513 | −43.087 | 1.00 | 33.45 | C |
| ATOM | 8034 | O | VAL A | 1126 | 13.639 | 29.929 | −43.059 | 1.00 | 33.37 | O |
| ATOM | 8035 | N | ASP A | 1127 | 15.330 | 30.983 | −41.993 | 1.00 | 34.65 | N |
| ATOM | 8036 | CA | ASP A | 1127 | 14.759 | 30.815 | −40.650 | 1.00 | 34.53 | C |
| ATOM | 8037 | CB | ASP A | 1127 | 15.837 | 30.956 | −39.572 | 1.00 | 35.66 | C |
| ATOM | 8038 | CG | ASP A | 1127 | 16.758 | 29.733 | −39.490 | 1.00 | 37.34 | C |
| ATOM | 8039 | OD1 | ASP A | 1127 | 16.329 | 28.606 | −39.840 | 1.00 | 38.78 | O |
| ATOM | 8040 | OD2 | ASP A | 1127 | 17.917 | 29.898 | −39.057 | 1.00 | 37.96 | O |
| ATOM | 8041 | C | ASP A | 1127 | 13.606 | 31.776 | −40.398 | 1.00 | 33.55 | C |
| ATOM | 8042 | O | ASP A | 1127 | 12.640 | 31.421 | −39.725 | 1.00 | 33.15 | O |
| ATOM | 8043 | N | ASP A | 1128 | 13.712 | 32.985 | −40.952 | 1.00 | 33.41 | N |
| ATOM | 8044 | CA | ASP A | 1128 | 12.623 | 33.965 | −40.929 | 1.00 | 33.99 | C |
| ATOM | 8045 | CB | ASP A | 1128 | 13.025 | 35.280 | −41.621 | 1.00 | 36.13 | C |
| ATOM | 8046 | CG | ASP A | 1128 | 14.397 | 35.794 | −41.189 | 1.00 | 38.22 | C |
| ATOM | 8047 | OD1 | ASP A | 1128 | 15.065 | 35.148 | −40.347 | 1.00 | 39.05 | O |
| ATOM | 8048 | OD2 | ASP A | 1128 | 14.814 | 36.852 | −41.711 | 1.00 | 38.99 | O |
| ATOM | 8049 | C | ASP A | 1128 | 11.420 | 33.391 | −41.654 | 1.00 | 33.18 | C |
| ATOM | 8050 | O | ASP A | 1128 | 10.282 | 33.595 | −41.245 | 1.00 | 33.63 | O |
| ATOM | 8051 | N | LEU A | 1129 | 11.677 | 32.684 | −42.749 | 1.00 | 31.19 | N |
| ATOM | 8052 | CA | LEU A | 1129 | 10.604 | 32.044 | −43.485 | 1.00 | 29.48 | C |
| ATOM | 8053 | CB | LEU A | 1129 | 11.006 | 31.750 | −44.935 | 1.00 | 28.06 | C |
| ATOM | 8054 | CG | LEU A | 1129 | 10.536 | 32.776 | −45.969 | 1.00 | 28.24 | C |
| ATOM | 8055 | CD1 | LEU A | 1129 | 9.044 | 33.052 | −45.842 | 1.00 | 28.22 | C |
| ATOM | 8056 | CD2 | LEU A | 1129 | 11.314 | 34.075 | −45.849 | 1.00 | 28.37 | C |
| ATOM | 8057 | C | LEU A | 1129 | 10.082 | 30.796 | −42.793 | 1.00 | 29.30 | C |
| ATOM | 8058 | O | LEU A | 1129 | 8.871 | 30.623 | −42.700 | 1.00 | 30.12 | O |
| ATOM | 8059 | N | ILE A | 1130 | 10.979 | 29.937 | −42.301 | 1.00 | 28.24 | N |
| ATOM | 8060 | CA | ILE A | 1130 | 10.555 | 28.702 | −41.630 | 1.00 | 28.27 | C |
| ATOM | 8061 | CB | ILE A | 1130 | 11.739 | 27.842 | −41.130 | 1.00 | 27.18 | C |
| ATOM | 8062 | CG1 | ILE A | 1130 | 12.495 | 27.233 | −42.318 | 1.00 | 27.17 | C |
| ATOM | 8063 | CD1 | ILE A | 1130 | 13.891 | 26.728 | −41.995 | 1.00 | 26.98 | C |
| ATOM | 8064 | CG2 | ILE A | 1130 | 11.248 | 26.730 | −40.208 | 1.00 | 25.72 | C |
| ATOM | 8065 | C | ILE A | 1130 | 9.600 | 29.021 | −40.480 | 1.00 | 29.73 | C |
| ATOM | 8066 | O | ILE A | 1130 | 8.621 | 28.302 | −40.265 | 1.00 | 30.47 | O |
| ATOM | 8067 | N | LYS A | 1131 | 9.862 | 30.114 | −39.764 | 1.00 | 30.44 | N |
| ATOM | 8068 | CA | LYS A | 1131 | 8.957 | 30.525 | −38.699 | 1.00 | 30.89 | C |

-continued

| | | | Atomic coordinates for CRBN:DDB1:Lenalidomide (Human protein) | | | | | | |
|---|---|---|---|---|---|---|---|---|---|
| ATOM | 8069 | CB | LYS A | 1131 | 9.648 | 31.414 | −37.640 | 1.00 | 33.65 | C |
| ATOM | 8070 | CG | LYS A | 1131 | 9.946 | 32.849 | −38.056 | 1.00 | 36.37 | C |
| ATOM | 8071 | CD | LYS A | 1131 | 9.416 | 33.857 | −37.036 | 1.00 | 38.25 | C |
| ATOM | 8072 | CE | LYS A | 1131 | 10.467 | 34.898 | −36.645 | 1.00 | 40.47 | C |
| ATOM | 8073 | NZ | LYS A | 1131 | 11.155 | 35.550 | −37.803 | 1.00 | 41.69 | N |
| ATOM | 8074 | C | LYS A | 1131 | 7.668 | 31.150 | −39.246 | 1.00 | 28.92 | C |
| ATOM | 8075 | O | LYS A | 1131 | 6.591 | 30.902 | −38.711 | 1.00 | 29.52 | O |
| ATOM | 8076 | N | VAL A | 1132 | 7.774 | 31.927 | −40.319 | 1.00 | 26.67 | N |
| ATOM | 8077 | CA | VAL A | 1132 | 6.595 | 32.527 | −40.934 | 1.00 | 25.75 | C |
| ATOM | 8078 | CB | VAL A | 1132 | 6.969 | 33.479 | −42.076 | 1.00 | 24.80 | C |
| ATOM | 8079 | CG1 | VAL A | 1132 | 5.770 | 33.756 | −42.971 | 1.00 | 23.95 | C |
| ATOM | 8080 | CG2 | VAL A | 1132 | 7.508 | 34.773 | −41.510 | 1.00 | 25.50 | C |
| ATOM | 8081 | C | VAL A | 1132 | 5.608 | 31.469 | −41.432 | 1.00 | 26.28 | C |
| ATOM | 8082 | O | VAL A | 1132 | 4.423 | 31.535 | −41.118 | 1.00 | 27.07 | O |
| ATOM | 8083 | N | VAL A | 1133 | 6.102 | 30.493 | −42.189 | 1.00 | 26.12 | N |
| ATOM | 8084 | CA | VAL A | 1133 | 5.260 | 29.442 | −42.761 | 1.00 | 26.19 | C |
| ATOM | 8085 | CB | VAL A | 1133 | 6.042 | 28.588 | −43.783 | 1.00 | 25.61 | C |
| ATOM | 8086 | CG1 | VAL A | 1133 | 5.165 | 27.502 | −44.381 | 1.00 | 24.34 | C |
| ATOM | 8087 | CG2 | VAL A | 1133 | 6.593 | 29.469 | −44.891 | 1.00 | 25.52 | C |
| ATOM | 8088 | C | VAL A | 1133 | 4.659 | 28.549 | −41.677 | 1.00 | 27.44 | C |
| ATOM | 8089 | O | VAL A | 1133 | 3.546 | 28.050 | −41.828 | 1.00 | 27.63 | O |
| ATOM | 8090 | N | GLU A | 1134 | 5.387 | 28.363 | −40.578 | 1.00 | 28.67 | N |
| ATOM | 8091 | CA | GLU A | 1134 | 4.909 | 27.505 | −39.496 | 1.00 | 29.89 | C |
| ATOM | 8092 | CB | GLU A | 1134 | 6.054 | 27.057 | −38.590 | 1.00 | 30.16 | C |
| ATOM | 8093 | CG | GLU A | 1134 | 6.801 | 25.848 | −39.130 | 1.00 | 31.12 | C |
| ATOM | 8094 | CD | GLU A | 1134 | 8.034 | 25.486 | −38.314 | 1.00 | 32.63 | C |
| ATOM | 8095 | OE1 | GLU A | 1134 | 8.208 | 26.049 | −37.207 | 1.00 | 33.70 | O |
| ATOM | 8096 | OE2 | GLU A | 1134 | 8.831 | 24.629 | −38.777 | 1.00 | 32.49 | O |
| ATOM | 8097 | C | GLU A | 1134 | 3.780 | 28.137 | −38.693 | 1.00 | 30.17 | C |
| ATOM | 8098 | O | GLU A | 1134 | 2.848 | 27.443 | −38.296 | 1.00 | 30.84 | O |
| ATOM | 8099 | N | GLU A | 1135 | 3.866 | 29.448 | −38.459 | 1.00 | 30.85 | N |
| ATOM | 8100 | CA | GLU A | 1135 | 2.744 | 30.210 | −37.890 | 1.00 | 31.71 | C |
| ATOM | 8101 | CB | GLU A | 1135 | 3.038 | 31.720 | −37.860 | 1.00 | 35.83 | C |
| ATOM | 8102 | CG | GLU A | 1135 | 3.960 | 32.216 | −36.749 | 1.00 | 40.31 | C |
| ATOM | 8103 | CD | GLU A | 1135 | 3.983 | 33.746 | −36.654 | 1.00 | 43.59 | C |
| ATOM | 8104 | OE1 | GLU A | 1135 | 5.081 | 34.349 | −36.792 | 1.00 | 44.96 | O |
| ATOM | 8105 | OE2 | GLU A | 1135 | 2.897 | 34.349 | −36.448 | 1.00 | 43.50 | O |
| ATOM | 8106 | C | GLU A | 1135 | 1.535 | 29.991 | −38.775 | 1.00 | 29.30 | C |
| ATOM | 8107 | O | GLU A | 1135 | 0.402 | 29.949 | −38.302 | 1.00 | 29.05 | O |
| ATOM | 8108 | N | LEU A | 1136 | 1.798 | 29.873 | −40.072 | 1.00 | 27.09 | N |
| ATOM | 8109 | CA | LEU A | 1136 | 0.755 | 29.781 | −41.064 | 1.00 | 25.16 | C |
| ATOM | 8110 | CB | LEU A | 1136 | 1.296 | 30.108 | −42.459 | 1.00 | 23.82 | C |
| ATOM | 8111 | CG | LEU A | 1136 | 1.486 | 31.574 | −42.855 | 1.00 | 22.95 | C |
| ATOM | 8112 | CD1 | LEU A | 1136 | 2.167 | 31.681 | −44.202 | 1.00 | 23.04 | C |
| ATOM | 8113 | CD2 | LEU A | 1136 | 0.163 | 32.302 | −42.919 | 1.00 | 23.27 | C |
| ATOM | 8114 | C | LEU A | 1136 | 0.116 | 28.411 | −41.036 | 1.00 | 24.58 | C |
| ATOM | 8115 | O | LEU A | 1136 | −1.077 | 28.291 | −41.229 | 1.00 | 24.72 | O |
| ATOM | 8116 | N | THR A | 1137 | 0.899 | 27.376 | −40.775 | 1.00 | 24.38 | N |
| ATOM | 8117 | CA | THR A | 1137 | 0.337 | 26.031 | −40.736 | 1.00 | 24.79 | C |
| ATOM | 8118 | CB | THR A | 1137 | 1.422 | 24.915 | −40.701 | 1.00 | 25.24 | C |
| ATOM | 8119 | OG1 | THR A | 1137 | 2.255 | 25.059 | −39.535 | 1.00 | 25.74 | O |
| ATOM | 8120 | CG2 | THR A | 1137 | 2.281 | 24.936 | −41.964 | 1.00 | 23.91 | C |
| ATOM | 8121 | C | THR A | 1137 | −0.598 | 25.886 | −39.540 | 1.00 | 24.49 | C |
| ATOM | 8122 | O | THR A | 1137 | −1.504 | 25.050 | −39.548 | 1.00 | 24.70 | O |
| ATOM | 8123 | N | ARG A | 1138 | −0.383 | 26.723 | −38.528 | 1.00 | 24.29 | N |
| ATOM | 8124 | CA | ARG A | 1138 | −1.089 | 26.611 | −37.249 | 1.00 | 24.50 | C |
| ATOM | 8125 | CB | ARG A | 1138 | −0.285 | 27.287 | −36.131 | 1.00 | 25.68 | C |
| ATOM | 8126 | CG | ARG A | 1138 | 0.926 | 26.504 | −35.666 | 1.00 | 26.62 | C |
| ATOM | 8127 | CD | ARG A | 1138 | 1.556 | 27.144 | −34.436 | 1.00 | 28.39 | C |
| ATOM | 8128 | NE | ARG A | 1138 | 3.017 | 27.016 | −34.489 | 1.00 | 30.69 | N |
| ATOM | 8129 | CZ | ARG A | 1138 | 3.876 | 28.036 | −34.564 | 1.00 | 31.14 | C |
| ATOM | 8130 | NH1 | ARG A | 1138 | 3.451 | 29.305 | −34.557 | 1.00 | 30.58 | N |
| ATOM | 8131 | NH2 | ARG A | 1138 | 5.177 | 27.780 | −34.634 | 1.00 | 31.67 | N |
| ATOM | 8132 | C | ARG A | 1138 | −2.506 | 27.180 | −37.269 | 1.00 | 23.56 | C |
| ATOM | 8133 | O | ARG A | 1138 | −3.223 | 27.076 | −36.284 | 1.00 | 22.92 | O |
| ATOM | 8134 | N | ILE A | 1139 | −2.898 | 27.785 | −38.385 | 1.00 | 23.69 | N |
| ATOM | 8135 | CA | ILE A | 1139 | −4.239 | 28.369 | −38.519 | 1.00 | 23.36 | C |
| ATOM | 8136 | CB | ILE A | 1139 | −4.254 | 29.666 | −39.385 | 1.00 | 23.04 | C |
| ATOM | 8137 | CG1 | ILE A | 1139 | −4.110 | 29.342 | −40.879 | 1.00 | 22.37 | C |
| ATOM | 8138 | CD1 | ILE A | 1139 | −4.149 | 30.562 | −41.761 | 1.00 | 22.81 | C |
| ATOM | 8139 | CG2 | ILE A | 1139 | −3.215 | 30.666 | −38.893 | 1.00 | 22.81 | C |
| ATOM | 8140 | C | ILE A | 1139 | −5.279 | 27.384 | −39.064 | 1.00 | 23.61 | C |
| ATOM | 8141 | O | ILE A | 1139 | −6.461 | 27.737 | −39.166 | 1.00 | 24.82 | O |
| ATOM | 8142 | N | HIS A | 1140 | −4.848 | 26.177 | −39.439 | 1.00 | 22.36 | N |
| ATOM | 8143 | CA | HIS A | 1140 | −5.789 | 25.133 | −39.834 | 1.00 | 22.01 | C |
| ATOM | 8144 | CB | HIS A | 1140 | −5.977 | 25.086 | −41.342 | 1.00 | 22.33 | C |
| ATOM | 8145 | CG | HIS A | 1140 | −4.733 | 24.702 | −42.103 | 1.00 | 22.62 | C |

-continued

| | | Atomic coordinates for CRBN:DDB1:Lenalidomide (Human protein) | | | | | | |
|---|---|---|---|---|---|---|---|---|
| ATOM | 8146 | ND1 | HIS A | 1140 | −3.874 | 25.617 | −42.595 | 1.00 | 21.92 | N |
| ATOM | 8147 | CE1 | HIS A | 1140 | −2.868 | 24.986 | −43.217 | 1.00 | 21.24 | C |
| ATOM | 8148 | NE2 | HIS A | 1140 | −3.083 | 23.662 | −43.133 | 1.00 | 21.58 | N |
| ATOM | 8149 | CD2 | HIS A | 1140 | −4.222 | 23.450 | −42.457 | 1.00 | 21.97 | C |
| ATOM | 8150 | C | HIS A | 1140 | −5.358 | 23.812 | −39.335 | 1.00 | 21.94 | C |
| ATOM | 8151 | O | HIS A | 1140 | −4.251 | 23.681 | −38.841 | 1.00 | 22.02 | O |
| ATOM | 8152 | N | TRP A | 1141 | −6.237 | 22.818 | −39.460 | 1.00 | 22.67 | N |
| ATOM | 8153 | CA | TRP A | 1141 | −5.944 | 21.454 | −39.024 | 1.00 | 23.30 | C |
| ATOM | 8154 | CB | TRP A | 1141 | −7.163 | 20.547 | −39.178 | 1.00 | 22.86 | C |
| ATOM | 8155 | CG | TRP A | 1141 | −8.425 | 21.008 | −38.485 | 1.00 | 22.47 | C |
| ATOM | 8156 | CD1 | TRP A | 1141 | −8.545 | 21.577 | −37.220 | 1.00 | 22.94 | C |
| ATOM | 8157 | NE1 | TRP A | 1141 | −9.865 | 21.842 | −36.920 | 1.00 | 23.01 | N |
| ATOM | 8158 | CE2 | TRP A | 1141 | −10.665 | 21.457 | −37.931 | 1.00 | 22.54 | C |
| ATOM | 8159 | CD2 | TRP A | 1141 | −9.799 | 20.906 | −38.985 | 1.00 | 22.22 | C |
| ATOM | 8160 | CE3 | TRP A | 1141 | −10.378 | 20.440 | −40.156 | 1.00 | 20.03 | C |
| ATOM | 8161 | CZ3 | TRP A | 1141 | −11.771 | 20.520 | −40.520 | 1.00 | 22.14 | C |
| ATOM | 8162 | CH2 | TRP A | 1141 | −12.578 | 21.060 | −39.274 | 1.00 | 22.30 | C |
| ATOM | 8163 | CZ2 | TRP A | 1141 | −12.038 | 21.529 | −38.071 | 1.00 | 22.30 | C |
| ATOM | 8164 | C | TRP A | 1141 | −4.838 | 20.914 | −39.863 | 1.00 | 24.67 | C |
| ATOM | 8165 | O | TRP A | 1141 | −4.781 | 21.186 | −41.076 | 1.00 | 24.33 | O |
| ATOM | 8166 | N | SER A | 1142 | −3.944 | 20.149 | −39.239 | 1.00 | 25.79 | N |
| ATOM | 8167 | CA | SER A | 1142 | −2.829 | 19.541 | −39.965 | 1.00 | 27.12 | C |
| ATOM | 8168 | CB | SER A | 1142 | −1.668 | 19.254 | −39.025 | 1.00 | 28.15 | C |
| ATOM | 8169 | OG | SER A | 1142 | −2.147 | 19.068 | −37.709 | 1.00 | 30.18 | O |
| ATOM | 8170 | C | SER A | 1142 | −3.275 | 18.279 | −40.708 | 1.00 | 27.63 | C |
| ATOM | 8171 | O | SER A | 1142 | −4.279 | 17.657 | −40.349 | 1.00 | 28.45 | O |
| ATOM | 8172 | N | HIS A | 1143 | −2.541 | 17.921 | −41.757 | 1.00 | 26.92 | N |
| ATOM | 8173 | CA | HIS A | 1143 | −2.928 | 16.810 | −42.617 | 1.00 | 25.89 | C |
| ATOM | 8174 | CB | HIS A | 1143 | −2.536 | 17.108 | −44.063 | 1.00 | 26.01 | C |
| ATOM | 8175 | CG | HIS A | 1143 | −3.166 | 18.366 | −44.608 | 1.00 | 27.02 | C |
| ATOM | 8176 | ND1 | HIS A | 1143 | −4.501 | 18.488 | −44.802 | 1.00 | 27.30 | N |
| ATOM | 8177 | CE1 | HIS A | 1143 | −4.777 | 19.723 | −45.283 | 1.00 | 27.26 | C |
| ATOM | 8178 | NE2 | HIS A | 1143 | −3.613 | 20.397 | −45.393 | 1.00 | 28.18 | N |
| ATOM | 8179 | CD2 | HIS A | 1143 | −2.600 | 19.592 | −44.982 | 1.00 | 28.02 | C |
| ATOM | 8180 | C | HIS A | 1143 | −2.349 | 15.505 | −42.147 | 1.00 | 25.45 | C |
| ATOM | 8181 | O | HIS A | 1143 | −1.208 | 15.459 | −41.692 | 1.00 | 26.78 | O |
| ATOM | 8182 | N | PRO A | 1144 | −3.128 | 14.417 | −42.242 | 1.00 | 25.11 | N |
| ATOM | 8183 | CA | PRO A | 1144 | −2.606 | 13.109 | −41.837 | 1.00 | 24.85 | C |
| ATOM | 8184 | CB | PRO A | 1144 | −3.808 | 12.162 | −42.015 | 1.00 | 25.46 | C |
| ATOM | 8185 | CG | PRO A | 1144 | −4.975 | 13.001 | −42.430 | 1.00 | 25.28 | C |
| ATOM | 8186 | CD | PRO A | 1144 | −4.448 | 14.324 | −42.889 | 1.00 | 25.38 | C |
| ATOM | 8187 | C | PRO A | 1144 | −1.513 | 12.663 | −42.773 | 1.00 | 24.34 | C |
| ATOM | 8188 | O | PRO A | 1144 | −1.622 | 12.869 | −43.975 | 1.00 | 24.88 | O |
| ATOM | 8189 | N | GLN A | 1145 | −0.472 | 12.050 | −42.235 | 1.00 | 24.27 | N |
| ATOM | 8190 | CA | GLN A | 1145 | 0.518 | 11.377 | −43.068 | 1.00 | 24.84 | C |
| ATOM | 8191 | CB | GLN A | 1145 | 1.717 | 10.964 | −42.220 | 1.00 | 26.10 | C |
| ATOM | 8192 | CG | GLN A | 1145 | 2.992 | 10.756 | −43.008 | 1.00 | 28.40 | C |
| ATOM | 8193 | CD | GLN A | 1145 | 3.901 | 9.743 | −42.351 | 1.00 | 30.36 | C |
| ATOM | 8194 | OE1 | GLN A | 1145 | 3.866 | 8.550 | −42.675 | 1.00 | 31.06 | O |
| ATOM | 8195 | NE2 | GLN A | 1145 | 4.710 | 10.206 | −41.405 | 1.00 | 31.51 | N |
| ATOM | 8196 | C | GLN A | 1145 | −0.108 | 10.146 | −43.746 | 1.00 | 24.10 | C |
| ATOM | 8197 | O | GLN A | 1145 | −0.851 | 9.399 | −43.128 | 1.00 | 24.36 | O |
| ATOM | 8198 | N | PHE A | 1146 | 0.175 | 9.942 | −45.022 | 1.00 | 23.96 | N |
| ATOM | 8199 | CA | PHE A | 1146 | −0.385 | 8.782 | −45.725 | 1.00 | 23.80 | C |
| ATOM | 8200 | CB | PHE A | 1146 | −0.501 | 9.056 | −47.227 | 1.00 | 22.20 | C |
| ATOM | 8201 | CG | PHE A | 1146 | −1.195 | 7.972 | −47.987 | 1.00 | 20.64 | C |
| ATOM | 8202 | CD1 | PHE A | 1146 | −2.569 | 7.812 | −47.892 | 1.00 | 19.55 | C |
| ATOM | 8203 | CE1 | PHE A | 1146 | −3.212 | 6.810 | −48.593 | 1.00 | 19.02 | C |
| ATOM | 8204 | CZ | PHE A | 1146 | −2.481 | 5.945 | −49.399 | 1.00 | 19.23 | C |
| ATOM | 8205 | CE2 | PHE A | 1146 | −1.104 | 6.097 | −49.514 | 1.00 | 19.47 | C |
| ATOM | 8206 | CD2 | PHE A | 1146 | −0.467 | 7.105 | −48.806 | 1.00 | 20.29 | C |
| ATOM | 8207 | C | PHE A | 1146 | 0.433 | 7.519 | −45.462 | 1.00 | 24.43 | C |
| ATOM | 8208 | O | PHE A | 1146 | −0.128 | 6.472 | −45.185 | 1.00 | 24.15 | O |
| ATOM | 8209 | N | GLU A | 1147 | 1.757 | 7.648 | −45.574 | 1.00 | 26.02 | N |
| ATOM | 8210 | CA | GLU A | 1147 | 2.768 | 6.618 | −45.237 | 1.00 | 26.41 | C |
| ATOM | 8211 | CB | GLU A | 1147 | 2.248 | 5.186 | −45.385 | 1.00 | 25.97 | C |
| ATOM | 8212 | C | GLU A | 1147 | 3.970 | 6.831 | −46.155 | 1.00 | 27.03 | C |
| ATOM | 8213 | O | GLU A | 1147 | 4.076 | 7.873 | −46.823 | 1.00 | 27.12 | O |
| ATOM | 8214 | N | ASN C | 48 | −55.408 | 33.311 | −97.767 | 1.00 | 40.91 | N |
| ATOM | 8215 | CA | ASN C | 48 | −54.139 | 33.875 | −97.222 | 1.00 | 42.84 | C |
| ATOM | 8216 | CB | ASN C | 48 | −53.429 | 32.877 | −96.284 | 1.00 | 39.39 | C |
| ATOM | 8217 | CG | ASN C | 48 | −53.839 | 33.042 | −94.823 | 1.00 | 38.00 | C |
| ATOM | 8218 | OD1 | ASN C | 48 | −53.083 | 33.568 | −94.007 | 1.00 | 35.62 | O |
| ATOM | 8219 | ND2 | ASN C | 48 | −55.040 | 32.591 | −94.492 | 1.00 | 38.12 | N |
| ATOM | 8220 | C | ASN C | 48 | −53.188 | 34.389 | −98.308 | 1.00 | 46.84 | C |
| ATOM | 8221 | O | ASN C | 48 | −53.537 | 34.420 | −99.498 | 1.00 | 47.20 | O |
| ATOM | 8222 | N | PHE C | 49 | −51.996 | 34.806 | −97.874 | 1.00 | 50.66 | N |

-continued

| | | | Atomic coordinates for CRBN:DDB1:Lenalidomide (Human protein) | | | | | | |
|---|---|---|---|---|---|---|---|---|---|
| ATOM | 8223 | CA  | PHE C | 49 | −51.008 | 35.475 | −98.724  | 1.00 | 50.09 | C |
| ATOM | 8224 | CB  | PHE C | 49 | −51.167 | 37.016 | −98.609  | 1.00 | 49.42 | C |
| ATOM | 8225 | CG  | PHE C | 49 | −50.104 | 37.713 | −97.779  | 1.00 | 48.77 | C |
| ATOM | 8226 | CD1 | PHE C | 49 | −49.775 | 37.281 | −96.500  | 1.00 | 47.83 | C |
| ATOM | 8227 | CE1 | PHE C | 49 | −48.795 | 37.935 | −95.760  | 1.00 | 47.57 | C |
| ATOM | 8228 | CZ  | PHE C | 49 | −48.158 | 39.055 | −96.273  | 1.00 | 47.51 | C |
| ATOM | 8229 | CE2 | PHE C | 49 | −48.491 | 39.516 | −97.536  | 1.00 | 47.94 | C |
| ATOM | 8230 | CD2 | PHE C | 49 | −49.460 | 38.850 | −98.279  | 1.00 | 49.84 | C |
| ATOM | 8231 | C   | PHE C | 49 | −49.593 | 34.970 | −98.382  | 1.00 | 51.55 | C |
| ATOM | 8232 | O   | PHE C | 49 | −49.401 | 34.261 | −97.377  | 1.00 | 51.51 | O |
| ATOM | 8233 | N   | ASP C | 50 | −48.616 | 35.317 | −99.220  | 1.00 | 51.27 | N |
| ATOM | 8234 | CA  | ASP C | 50 | −47.261 | 34.758 | −99.115  | 1.00 | 50.17 | C |
| ATOM | 8235 | CB  | ASP C | 50 | −46.541 | 34.879 | −100.465 | 1.00 | 50.24 | C |
| ATOM | 8236 | CG  | ASP C | 50 | −45.435 | 33.861 | −100.633 | 1.00 | 51.15 | C |
| ATOM | 8237 | OD1 | ASP C | 50 | −45.740 | 32.652 | −100.734 | 1.00 | 52.59 | O |
| ATOM | 8238 | OD2 | ASP C | 50 | −44.259 | 34.271 | −100.685 | 1.00 | 51.52 | O |
| ATOM | 8239 | C   | ASP C | 50 | −46.443 | 35.415 | −97.995  | 1.00 | 48.23 | C |
| ATOM | 8240 | O   | ASP C | 50 | −45.980 | 36.549 | −98.139  | 1.00 | 49.81 | O |
| ATOM | 8241 | N   | THR C | 51 | −46.255 | 34.693 | −96.890  | 1.00 | 45.50 | N |
| ATOM | 8242 | CA  | THR C | 51 | −45.641 | 35.267 | −95.675  | 1.00 | 44.95 | C |
| ATOM | 8243 | CB  | THR C | 51 | −45.946 | 34.419 | −94.415  | 1.00 | 43.31 | C |
| ATOM | 8244 | OG1 | THR C | 51 | −45.321 | 33.135 | −94.525  | 1.00 | 44.12 | O |
| ATOM | 8245 | CG2 | THR C | 51 | −47.444 | 34.248 | −94.235  | 1.00 | 41.89 | C |
| ATOM | 8246 | C   | THR C | 51 | −44.126 | 35.566 | −95.758  | 1.00 | 44.81 | C |
| ATOM | 8247 | O   | THR C | 51 | −43.565 | 36.219 | −94.867  | 1.00 | 43.82 | O |
| ATOM | 8248 | N   | SER C | 52 | −43.478 | 35.104 | −96.828  | 1.00 | 45.02 | N |
| ATOM | 8249 | CA  | SER C | 52 | −42.055 | 35.379 | −97.052  | 1.00 | 44.99 | C |
| ATOM | 8250 | CB  | SER C | 52 | −41.395 | 34.222 | −97.800  | 1.00 | 43.01 | C |
| ATOM | 8251 | OG  | SER C | 52 | −41.596 | 34.354 | −99.194  | 1.00 | 41.72 | O |
| ATOM | 8252 | C   | SER C | 52 | −41.824 | 36.698 | −97.814  | 1.00 | 45.94 | C |
| ATOM | 8253 | O   | SER C | 52 | −40.684 | 37.178 | −97.922  | 1.00 | 47.52 | O |
| ATOM | 8254 | N   | LEU C | 53 | −42.909 | 37.273 | −98.333  | 1.00 | 43.31 | N |
| ATOM | 8255 | CA  | LEU C | 53 | −42.842 | 38.513 | −99.098  | 1.00 | 41.76 | C |
| ATOM | 8256 | CB  | LEU C | 53 | −44.171 | 38.779 | −99.829  | 1.00 | 42.36 | C |
| ATOM | 8257 | C   | LEU C | 53 | −42.387 | 39.749 | −98.293  | 1.00 | 40.35 | C |
| ATOM | 8258 | O   | LEU C | 53 | −41.580 | 40.527 | −98.795  | 1.00 | 41.07 | O |
| ATOM | 8259 | N   | PRO C | 54 | −42.900 | 39.942 | −97.053  | 1.00 | 39.36 | N |
| ATOM | 8260 | CA  | PRO C | 54 | −42.531 | 41.171 | −96.346  | 1.00 | 38.48 | C |
| ATOM | 8261 | CB  | PRO C | 54 | −43.415 | 41.147 | −95.094  | 1.00 | 38.37 | C |
| ATOM | 8262 | CG  | PRO C | 54 | −44.535 | 40.228 | −95.423  | 1.00 | 39.84 | C |
| ATOM | 8263 | CD  | PRO C | 54 | −43.922 | 39.184 | −96.307  | 1.00 | 40.87 | C |
| ATOM | 8264 | C   | PRO C | 54 | −41.067 | 41.231 | −95.943  | 1.00 | 39.10 | C |
| ATOM | 8265 | O   | PRO C | 54 | −40.507 | 42.315 | −95.861  | 1.00 | 41.57 | O |
| ATOM | 8266 | N   | THR C | 55 | −40.445 | 40.080 | −95.706  | 1.00 | 40.09 | N |
| ATOM | 8267 | CA  | THR C | 55 | −39.035 | 40.046 | −95.271  | 1.00 | 39.55 | C |
| ATOM | 8268 | CB  | THR C | 55 | −38.713 | 38.777 | −94.418  | 1.00 | 40.00 | C |
| ATOM | 8269 | OG1 | THR C | 55 | −37.426 | 38.916 | 93.790   | 1.00 | 37.92 | O |
| ATOM | 8270 | CG2 | THR C | 55 | −38.760 | 37.494 | −95.267  | 1.00 | 38.32 | C |
| ATOM | 8271 | C   | THR C | 55 | −38.025 | 40.225 | −96.425  | 1.00 | 37.57 | C |
| ATOM | 8272 | O   | THR C | 55 | −36.846 | 40.526 | −96.186  | 1.00 | 38.59 | O |
| ATOM | 8273 | N   | SER C | 56 | −38.497 | 40.044 | −97.661  | 1.00 | 35.25 | N |
| ATOM | 8274 | CA  | SER C | 56 | −37.677 | 40.264 | −98.861  | 1.00 | 33.65 | C |
| ATOM | 8275 | CB  | SER C | 56 | −38.051 | 39.269 | −99.962  | 1.00 | 33.12 | C |
| ATOM | 8276 | OG  | SER C | 56 | −39.389 | 39.468 | −100.367 | 1.00 | 32.78 | O |
| ATOM | 8277 | C   | SER C | 56 | −37.742 | 41.709 | −99.400  | 1.00 | 31.71 | C |
| ATOM | 8278 | O   | SER C | 56 | −37.073 | 42.033 | −100.376 | 1.00 | 32.12 | O |
| ATOM | 8279 | N   | HIS C | 57 | −38.558 | 42.554 | −98.766  | 1.00 | 30.10 | N |
| ATOM | 8280 | CA  | HIS C | 57 | −38.565 | 44.009 | −99.002  | 1.00 | 28.86 | C |
| ATOM | 8281 | CB  | HIS C | 57 | −37.305 | 44.653 | −98.426  | 1.00 | 28.33 | C |
| ATOM | 8282 | CG  | HIS C | 57 | −37.177 | 44.504 | −96.931  | 1.00 | 27.92 | C |
| ATOM | 8283 | ND1 | HIS C | 57 | −37.923 | 45.208 | −96.072  | 1.00 | 27.40 | N |
| ATOM | 8284 | CE1 | HIS C | 57 | −37.600 | 44.866 | −94.816  | 1.00 | 27.91 | C |
| ATOM | 8285 | NE2 | HIS C | 57 | −36.635 | 43.942 | −94.871  | 1.00 | 28.17 | N |
| ATOM | 8286 | CD2 | HIS C | 57 | −36.347 | 43.697 | −96.159  | 1.00 | 28.18 | C |
| ATOM | 8287 | C   | HIS C | 57 | −38.734 | 44.395 | −100.442 | 1.00 | 27.94 | C |
| ATOM | 8288 | O   | HIS C | 57 | −38.009 | 45.246 | −100.961 | 1.00 | 27.51 | O |
| ATOM | 8289 | N   | THR C | 58 | −39.713 | 43.780 | −101.090 | 1.00 | 27.09 | N |
| ATOM | 8290 | CA  | THR C | 58 | −39.888 | 43.908 | −102.525 | 1.00 | 27.76 | C |
| ATOM | 8291 | CB  | THR C | 58 | −41.006 | 42.972 | −103.032 | 1.00 | 28.09 | C |
| ATOM | 8292 | OG1 | THR C | 58 | −42.215 | 43.254 | −102.326 | 1.00 | 29.15 | O |
| ATOM | 8293 | CG2 | THR C | 58 | −40.641 | 41.504 | −102.808 | 1.00 | 27.65 | C |
| ATOM | 8294 | C   | THR C | 58 | −40.170 | 45.360 | −102.949 | 1.00 | 28.51 | C |
| ATOM | 8295 | O   | THR C | 58 | −39.881 | 45.748 | −104.094 | 1.00 | 28.40 | O |
| ATOM | 8296 | N   | TYR C | 59 | −40.711 | 46.150 | −102.015 | 1.00 | 27.85 | N |
| ATOM | 8297 | CA  | TYR C | 59 | −41.034 | 47.566 | −102.230 | 1.00 | 27.90 | C |
| ATOM | 8298 | CB  | TYR C | 59 | −41.785 | 48.103 | −101.019 | 1.00 | 27.30 | C |
| ATOM | 8299 | CG  | TYR C | 59 | −40.934 | 48.130 | −99.765  | 1.00 | 27.52 | C |

-continued

| | | | Atomic coordinates for CRBN:DDB1:Lenalidomide (Human protein) | | | | | | |
|---|---|---|---|---|---|---|---|---|---|
| ATOM | 8300 | CD1 | TYR C | 59 | −40.152 | 49.245 | −99.440 | 1.00 | 26.39 | C |
| ATOM | 8301 | CE1 | TYR C | 59 | −39.360 | 49.250 | −98.302 | 1.00 | 27.25 | C |
| ATOM | 8302 | CZ | TYR C | 59 | −39.347 | 48.130 | −97.461 | 1.00 | 28.31 | C |
| ATOM | 8303 | OH | TYR C | 59 | −38.584 | 48.096 | −96.307 | 1.00 | 28.36 | O |
| ATOM | 8304 | CE2 | TYR C | 59 | −40.111 | 47.021 | −97.770 | 1.00 | 28.27 | C |
| ATOM | 8305 | CD2 | TYR C | 59 | −40.894 | 47.025 | −98.913 | 1.00 | 28.11 | C |
| ATOM | 8306 | C | TYR C | 59 | −39.804 | 48.456 | −102.474 | 1.00 | 29.86 | C |
| ATOM | 8307 | O | TYR C | 59 | −39.946 | 49.667 | −102.687 | 1.00 | 30.37 | O |
| ATOM | 8308 | N | LEU C | 60 | −38.607 | 47.865 | −102.401 | 1.00 | 32.45 | N |
| ATOM | 8309 | CA | LEU C | 60 | −37.341 | 48.583 | −102.594 | 1.00 | 34.04 | C |
| ATOM | 8310 | CB | LEU C | 60 | −36.234 | 47.974 | −101.730 | 1.00 | 32.88 | C |
| ATOM | 8311 | CG | LEU C | 60 | −36.009 | 48.441 | −100.289 | 1.00 | 32.37 | C |
| ATOM | 8312 | CD1 | LEU C | 60 | −35.394 | 47.319 | −99.472 | 1.00 | 32.04 | C |
| ATOM | 8313 | CD2 | LEU C | 60 | −35.104 | 49.658 | −100.242 | 1.00 | 32.19 | C |
| ATOM | 8314 | C | LEU C | 60 | −36.912 | 48.565 | −104.061 | 1.00 | 38.02 | C |
| ATOM | 8315 | O | LEU C | 60 | −36.187 | 49.460 | −104.512 | 1.00 | 40.11 | O |
| ATOM | 8316 | N | GLY C | 61 | −37.343 | 47.539 | −104.797 | 1.00 | 39.84 | N |
| ATOM | 8317 | CA | GLY C | 61 | −37.122 | 47.483 | −106.238 | 1.00 | 42.08 | C |
| ATOM | 8318 | C | GLY C | 61 | −36.459 | 46.218 | −106.742 | 1.00 | 46.03 | C |
| ATOM | 8319 | O | GLY C | 61 | −36.185 | 45.295 | −105.972 | 1.00 | 45.00 | O |
| ATOM | 8320 | N | ALA C | 62 | −36.191 | 46.210 | −108.049 | 1.00 | 50.43 | N |
| ATOM | 8321 | CA | ALA C | 62 | −35.628 | 45.071 | −108.792 | 1.00 | 53.17 | C |
| ATOM | 8322 | CB | ALA C | 62 | −34.852 | 45.562 | −110.019 | 1.00 | 52.14 | C |
| ATOM | 8323 | C | ALA C | 62 | −34.799 | 44.064 | −107.974 | 1.00 | 54.39 | C |
| ATOM | 8324 | O | ALA C | 62 | −35.366 | 43.211 | −107.286 | 1.00 | 54.82 | O |
| ATOM | 8325 | N | ASP C | 63 | −33.471 | 44.147 | −108.069 | 1.00 | 56.92 | N |
| ATOM | 8326 | CA | ASP C | 63 | −32.586 | 43.127 | −107.477 | 1.00 | 59.41 | C |
| ATOM | 8327 | CB | ASP C | 63 | −32.403 | 41.939 | −108.435 | 1.00 | 58.55 | C |
| ATOM | 8328 | C | ASP C | 63 | −31.225 | 43.685 | −107.062 | 1.00 | 58.37 | C |
| ATOM | 8329 | O | ASP C | 63 | −30.595 | 44.446 | −107.812 | 1.00 | 57.32 | O |
| ATOM | 8330 | N | MET C | 64 | −30.774 | 43.278 | −105.875 | 1.00 | 55.30 | N |
| ATOM | 8331 | CA | MET C | 64 | −29.567 | 43.832 | −105.259 | 1.00 | 54.32 | C |
| ATOM | 8332 | CB | MET C | 64 | −29.862 | 44.262 | −103.814 | 1.00 | 52.60 | C |
| ATOM | 8333 | CG | MET C | 64 | −31.114 | 45.125 | −103.671 | 1.00 | 52.32 | C |
| ATOM | 8334 | SD | MET C | 64 | −31.292 | 45.970 | −102.081 | 1.00 | 50.83 | S |
| ATOM | 8335 | CE | MET C | 64 | −32.872 | 46.771 | −102.320 | 1.00 | 49.66 | C |
| ATOM | 8336 | C | MET C | 64 | −28.387 | 42.857 | −105.298 | 1.00 | 54.43 | C |
| ATOM | 8337 | O | MET C | 64 | −28.561 | 41.665 | −105.046 | 1.00 | 55.10 | O |
| ATOM | 8338 | N | GLU C | 65 | −27.196 | 43.368 | −105.627 | 1.00 | 54.41 | N |
| ATOM | 8339 | CA | GLU C | 65 | −25.953 | 42.582 | −105.563 | 1.00 | 53.12 | C |
| ATOM | 8340 | CB | GLU C | 65 | −24.752 | 43.427 | −106.004 | 1.00 | 50.75 | C |
| ATOM | 8341 | C | GLU C | 65 | −25.742 | 42.069 | −104.139 | 1.00 | 54.15 | C |
| ATOM | 8342 | O | GLU C | 65 | −25.888 | 42.825 | −103.180 | 1.00 | 55.22 | O |
| ATOM | 8343 | N | GLU C | 66 | −25.416 | 40.785 | −103.999 | 1.00 | 55.16 | N |
| ATOM | 8344 | CA | GLU C | 66 | −25.337 | 40.156 | −102.671 | 1.00 | 52.95 | C |
| ATOM | 8345 | CB | GLU C | 66 | −26.154 | 38.862 | −102.627 | 1.00 | 52.21 | C |
| ATOM | 8346 | CG | GLU C | 66 | −27.509 | 38.967 | −103.304 | 1.00 | 53.69 | C |
| ATOM | 8347 | CD | GLU C | 66 | −28.582 | 38.167 | −102.601 | 1.00 | 55.90 | C |
| ATOM | 8348 | OE1 | GLU C | 66 | −28.870 | 37.037 | −103.053 | 1.00 | 55.95 | O |
| ATOM | 8349 | OE2 | GLU C | 66 | −29.136 | 38.669 | −101.594 | 1.00 | 57.68 | O |
| ATOM | 8350 | C | GLU C | 66 | −23.901 | 39.890 | −102.238 | 1.00 | 52.01 | C |
| ATOM | 8351 | O | GLU C | 66 | −23.049 | 39.573 | −103.063 | 1.00 | 52.32 | O |
| ATOM | 8352 | N | PHE C | 67 | −23.643 | 40.023 | −100.939 | 1.00 | 52.66 | N |
| ATOM | 8353 | CA | PHE C | 67 | −22.306 | 39.822 | −100.396 | 1.00 | 54.50 | C |
| ATOM | 8354 | CB | PHE C | 67 | −21.724 | 41.143 | −99.888 | 1.00 | 54.48 | C |
| ATOM | 8355 | CG | PHE C | 67 | −21.525 | 42.170 | −100.967 | 1.00 | 56.05 | C |
| ATOM | 8356 | CD1 | PHE C | 67 | −20.561 | 41.984 | −101.958 | 1.00 | 56.74 | C |
| ATOM | 8357 | CE1 | PHE C | 67 | −20.381 | 42.926 | −102.959 | 1.00 | 56.98 | C |
| ATOM | 8358 | CZ | PHE C | 67 | −21.163 | 44.072 | −102.977 | 1.00 | 56.67 | C |
| ATOM | 8359 | CE2 | PHE C | 67 | −22.123 | 44.272 | −101.996 | 1.00 | 55.95 | C |
| ATOM | 8360 | CD2 | PHE C | 67 | −22.302 | 43.325 | −100.998 | 1.00 | 55.94 | C |
| ATOM | 8361 | C | PHE C | 67 | −22.304 | 38.784 | −99.287 | 1.00 | 57.38 | C |
| ATOM | 8362 | O | PHE C | 67 | −23.044 | 38.919 | −98.305 | 1.00 | 58.95 | O |
| ATOM | 8363 | N | HIS C | 68 | −21.476 | 37.748 | −99.458 | 1.00 | 58.27 | N |
| ATOM | 8364 | CA | HIS C | 68 | −21.325 | 36.679 | −98.464 | 1.00 | 57.39 | C |
| ATOM | 8365 | CB | HIS C | 68 | −20.694 | 35.444 | −99.099 | 1.00 | 56.41 | C |
| ATOM | 8366 | C | HIS C | 68 | −20.527 | 37.160 | −97.273 | 1.00 | 56.98 | C |
| ATOM | 8367 | O | HIS C | 68 | −19.295 | 37.248 | −97.316 | 1.00 | 54.86 | O |
| ATOM | 8368 | N | GLY C | 69 | −21.238 | 37.479 | −96.196 | 1.00 | 57.27 | N |
| ATOM | 8369 | CA | GLY C | 69 | −20.667 | 38.232 | −95.079 | 1.00 | 55.51 | C |
| ATOM | 8370 | C | GLY C | 69 | −19.787 | 37.461 | −94.114 | 1.00 | 54.69 | C |
| ATOM | 8371 | O | GLY C | 69 | −20.258 | 36.570 | −93.392 | 1.00 | 53.58 | O |
| ATOM | 8372 | N | ARG C | 70 | −18.506 | 37.820 | −94.089 | 1.00 | 52.20 | N |
| ATOM | 8373 | CA | ARG C | 70 | −17.578 | 37.261 | −93.117 | 1.00 | 50.97 | C |
| ATOM | 8374 | CB | ARG C | 70 | −16.280 | 36.786 | −93.790 | 1.00 | 54.50 | C |
| ATOM | 8375 | CG | ARG C | 70 | −16.473 | 35.979 | −95.071 | 1.00 | 56.51 | C |
| ATOM | 8376 | CD | ARG C | 70 | −15.149 | 35.471 | −95.626 | 1.00 | 59.46 | C |

-continued

| | | | | Atomic coordinates for CRBN:DDB1:Lenalidomide (Human protein) | | | | | |
|---|---|---|---|---|---|---|---|---|---|
| ATOM | 8377 | NE | ARG C | 70 | −14.806 | 34.154 | −95.086 | 1.00 | 64.81 | N |
| ATOM | 8378 | CZ | ARG C | 70 | −14.048 | 33.940 | −94.005 | 1.00 | 66.91 | C |
| ATOM | 8379 | NH1 | ARG C | 70 | −13.524 | 34.961 | −93.329 | 1.00 | 68.47 | N |
| ATOM | 8380 | NH2 | ARG C | 70 | −13.810 | 32.696 | −93.596 | 1.00 | 64.63 | N |
| ATOM | 8381 | C | ARG C | 70 | −17.302 | 38.303 | −92.032 | 1.00 | 48.28 | C |
| ATOM | 8382 | O | ARG C | 70 | −18.105 | 38.465 | −91.124 | 1.00 | 48.50 | O |
| ATOM | 8383 | N | THR C | 71 | −16.189 | 39.026 | −92.165 | 1.00 | 48.43 | N |
| ATOM | 8384 | CA | THR C | 71 | −15.677 | 39.987 | −91.149 | 1.00 | 49.20 | C |
| ATOM | 8385 | CB | THR C | 71 | −15.370 | 41.396 | −91.758 | 1.00 | 47.69 | C |
| ATOM | 8386 | OG1 | THR C | 71 | −15.215 | 42.369 | −90.709 | 1.00 | 43.60 | O |
| ATOM | 8387 | CG2 | THR C | 71 | −16.475 | 41.846 | −92.732 | 1.00 | 47.02 | C |
| ATOM | 8388 | C | THR C | 71 | −16.429 | 40.115 | −89.795 | 1.00 | 49.59 | C |
| ATOM | 8389 | O | THR C | 71 | −17.460 | 40.797 | −89.695 | 1.00 | 40.33 | O |
| ATOM | 8390 | N | LEU C | 72 | −15.891 | 39.432 | −88.776 | 1.00 | 47.99 | N |
| ATOM | 8391 | CA | LEU C | 72 | −16.270 | 39.628 | −87.370 | 1.00 | 47.25 | C |
| ATOM | 8392 | CB | LEU C | 72 | −16.737 | 38.313 | −86.729 | 1.00 | 46.30 | C |
| ATOM | 8393 | CG | LEU C | 72 | −18.165 | 37.785 | −86.960 | 1.00 | 45.56 | C |
| ATOM | 8394 | CD1 | LEU C | 72 | −18.357 | 36.441 | −86.263 | 1.00 | 42.17 | C |
| ATOM | 8395 | CD2 | LEU C | 72 | −19.235 | 38.784 | −86.525 | 1.00 | 44.00 | C |
| ATOM | 8396 | C | LEU C | 72 | −15.075 | 40.178 | −86.593 | 1.00 | 47.20 | C |
| ATOM | 8397 | O | LEU C | 72 | −13.928 | 39.924 | −86.959 | 1.00 | 49.59 | O |
| ATOM | 8398 | N | HIS C | 73 | −15.343 | 40.922 | −85.523 | 1.00 | 46.24 | N |
| ATOM | 8399 | CA | HIS C | 73 | −14.284 | 41.543 | −84.720 | 1.00 | 46.89 | C |
| ATOM | 8400 | CB | HIS C | 73 | −14.554 | 43.039 | −84.548 | 1.00 | 47.59 | C |
| ATOM | 8401 | CG | HIS C | 73 | −14.571 | 43.814 | −85.849 | 1.00 | 48.07 | C |
| ATOM | 8402 | ND1 | HIS C | 73 | −13.624 | 44.716 | −86.168 | 1.00 | 48.75 | N |
| ATOM | 8403 | CE1 | HIS C | 73 | −13.890 | 45.240 | −87.382 | 1.00 | 48.07 | C |
| ATOM | 8404 | NE2 | HIS C | 73 | −15.012 | 44.669 | −87.845 | 1.00 | 48.06 | N |
| ATOM | 8405 | CD2 | HIS C | 73 | −15.461 | 43.784 | −86.924 | 1.00 | 48.45 | C |
| ATOM | 8406 | C | HIS C | 73 | −14.185 | 40.867 | −83.382 | 1.00 | 45.92 | C |
| ATOM | 8407 | O | HIS C | 73 | −15.183 | 40.748 | −82.681 | 1.00 | 44.78 | O |
| ATOM | 8408 | N | ASP C | 74 | −12.984 | 40.415 | −83.012 | 1.00 | 47.57 | N |
| ATOM | 8409 | CA | ASP C | 74 | −12.818 | 39.600 | −81.792 | 1.00 | 48.34 | C |
| ATOM | 8410 | CB | ASP C | 74 | −11.510 | 38.766 | −81.781 | 1.00 | 48.15 | C |
| ATOM | 8411 | CG | ASP C | 74 | −10.245 | 39.605 | −82.009 | 1.00 | 49.95 | C |
| ATOM | 8412 | OD1 | ASP C | 74 | −10.344 | 40.737 | −82.534 | 1.00 | 52.10 | O |
| ATOM | 8413 | OD2 | ASP C | 74 | −9.139 | 39.111 | −81.680 | 1.00 | 47.80 | O |
| ATOM | 8414 | C | ASP C | 74 | −13.033 | 40.362 | −80.488 | 1.00 | 48.96 | C |
| ATOM | 8415 | O | ASP C | 74 | −12.909 | 41.589 | −80.441 | 1.00 | 47.43 | O |
| ATOM | 8416 | N | ASP C | 75 | −13.359 | 39.611 | −79.438 | 1.00 | 51.08 | N |
| ATOM | 8417 | CA | ASP C | 75 | −13.953 | 40.156 | −78.215 | 1.00 | 52.40 | C |
| ATOM | 8418 | CB | ASP C | 75 | −14.342 | 39.019 | −77.264 | 1.00 | 52.50 | C |
| ATOM | 8419 | CG | ASP C | 75 | −15.570 | 38.257 | −77.732 | 1.00 | 52.35 | C |
| ATOM | 8420 | OD1 | ASP C | 75 | −16.543 | 38.893 | −78.204 | 1.00 | 51.16 | O |
| ATOM | 8421 | OD2 | ASP C | 75 | −15.568 | 37.015 | −77.605 | 1.00 | 54.33 | O |
| ATOM | 8422 | C | ASP C | 75 | −13.130 | 41.204 | −77.470 | 1.00 | 52.85 | C |
| ATOM | 8423 | O | ASP C | 75 | −11.901 | 41.164 | −77.472 | 1.00 | 52.46 | O |
| ATOM | 8424 | N | ASP C | 76 | −13.850 | 42.136 | −76.839 | 1.00 | 54.53 | N |
| ATOM | 8425 | CA | ASP C | 76 | −13.295 | 43.221 | −76.004 | 1.00 | 53.76 | C |
| ATOM | 8426 | CB | ASP C | 76 | −12.544 | 42.675 | −74.780 | 1.00 | 55.56 | C |
| ATOM | 8427 | CG | ASP C | 76 | −13.463 | 41.955 | −73.804 | 1.00 | 58.08 | C |
| ATOM | 8428 | OD2 | ASP C | 76 | −13.803 | 42.545 | −72.755 | 1.00 | 58.30 | O |
| ATOM | 8429 | OD1 | ASP C | 76 | −13.853 | 40.801 | −74.088 | 1.00 | 59.22 | O |
| ATOM | 8430 | C | ASP C | 76 | −12.456 | 44.251 | −76.754 | 1.00 | 51.64 | C |
| ATOM | 8431 | O | ASP C | 76 | −12.004 | 45.226 | −76.156 | 1.00 | 51.64 | O |
| ATOM | 8432 | N | SER C | 77 | −12.301 | 44.061 | −78.064 | 1.00 | 50.44 | N |
| ATOM | 8433 | CA | SER C | 77 | −11.459 | 44.929 | −78.894 | 1.00 | 50.16 | C |
| ATOM | 8434 | CB | SER C | 77 | −11.391 | 44.389 | −80.318 | 1.00 | 50.52 | C |
| ATOM | 8435 | OG | SER C | 77 | −10.620 | 45.252 | −81.134 | 1.00 | 54.29 | O |
| ATOM | 8436 | C | SER C | 77 | −11.918 | 46.388 | −78.928 | 1.00 | 49.81 | C |
| ATOM | 8437 | O | SER C | 77 | −13.042 | 46.699 | −78.532 | 1.00 | 51.81 | O |
| ATOM | 8438 | N | CYS C | 78 | −11.038 | 47.273 | −79.399 | 1.00 | 47.65 | N |
| ATOM | 8439 | CA | CYS C | 78 | −11.400 | 48.670 | −79.655 | 1.00 | 46.02 | C |
| ATOM | 8440 | CB | CYS C | 78 | −10.479 | 49.639 | −78.920 | 1.00 | 49.52 | C |
| ATOM | 8441 | SG | CYS C | 78 | −10.865 | 49.775 | −77.158 | 1.00 | 59.25 | S |
| ATOM | 8442 | C | CYS C | 78 | −11.398 | 48.957 | −81.138 | 1.00 | 42.86 | C |
| ATOM | 8443 | O | CYS C | 78 | −10.356 | 48.906 | −81.793 | 1.00 | 41.91 | O |
| ATOM | 8444 | N | GLN C | 79 | −12.587 | 49.244 | −81.658 | 1.00 | 40.17 | N |
| ATOM | 8445 | CA | GLN C | 79 | −12.786 | 49.484 | −83.076 | 1.00 | 37.66 | C |
| ATOM | 8446 | CB | GLN C | 79 | −13.766 | 48.470 | −83.663 | 1.00 | 36.38 | C |
| ATOM | 8447 | SG | GLN C | 79 | −13.253 | 47.038 | −83.667 | 1.00 | 36.49 | C |
| ATOM | 8448 | C | GLN C | 79 | −11.980 | 46.869 | −84.470 | 1.00 | 35.97 | C |
| ATOM | 8449 | O | GLN C | 79 | −11.936 | 47.169 | −85.669 | 1.00 | 35.60 | O |
| ATOM | 8450 | N | GLN C | 79 | −10.937 | 46.382 | −83.815 | 1.00 | 35.58 | N |
| ATOM | 8451 | C | GLN C | 79 | −13.303 | 50.885 | −83.319 | 1.00 | 36.80 | C |
| ATOM | 8452 | O | GLN C | 79 | −14.006 | 51.454 | −82.484 | 1.00 | 37.73 | O |
| ATOM | 8453 | N | VAL C | 80 | −12.929 | 51.440 | −84.464 | 1.00 | 35.52 | N |

-continued

| | | Atomic coordinates for CRBN:DDB1:Lenalidomide (Human protein) | | | | | | | |
|---|---|---|---|---|---|---|---|---|---|
| ATOM | 8454 | CA | VAL C | 80 | −13.492 | 52.690 | −84.941 | 1.00 | 33.70 | C |
| ATOM | 8455 | CB | VAL C | 80 | −12.381 | 53.711 | −85.285 | 1.00 | 32.73 | C |
| ATOM | 8456 | CG1 | VAL C | 80 | −12.919 | 54.846 | −86.150 | 1.00 | 32.80 | C |
| ATOM | 8457 | CG2 | VAL C | 80 | −11.750 | 54.256 | −84.009 | 1.00 | 31.43 | C |
| ATOM | 8458 | C | VAL C | 80 | −14.380 | 52.365 | −86.144 | 1.00 | 32.83 | C |
| ATOM | 8459 | O | VAL C | 80 | −13.911 | 51.825 | −87.150 | 1.00 | 32.58 | O |
| ATOM | 8460 | N | ILE C | 81 | −15.672 | 52.656 | −86.012 | 1.00 | 32.51 | N |
| ATOM | 8461 | CA | ILE C | 81 | −16.655 | 52.357 | −87.068 | 1.00 | 32.66 | C |
| ATOM | 8462 | CB | ILE C | 81 | −17.672 | 51.274 | −86.625 | 1.00 | 31.62 | C |
| ATOM | 8463 | CG1 | ILE C | 81 | −16.989 | 50.179 | −85.814 | 1.00 | 31.54 | C |
| ATOM | 8464 | CD1 | ILE C | 81 | −17.950 | 49.306 | −85.047 | 1.00 | 31.94 | C |
| ATOM | 8465 | CG2 | ILE C | 81 | −18.355 | 50.659 | −87.832 | 1.00 | 31.39 | C |
| ATOM | 8466 | C | ILE C | 81 | −17.433 | 53.617 | −87.474 | 1.00 | 32.78 | C |
| ATOM | 8467 | O | ILE C | 81 | −17.749 | 54.453 | −86.622 | 1.00 | 33.15 | O |
| ATOM | 8468 | N | PRO C | 82 | −17.737 | 53.763 | −88.779 | 1.00 | 32.81 | N |
| ATOM | 8469 | CA | PRO C | 82 | −18.646 | 54.835 | −89.209 | 1.00 | 32.86 | C |
| ATOM | 8470 | CB | PRO C | 82 | −18.718 | 54.645 | −90.733 | 1.00 | 32.78 | C |
| ATOM | 8471 | CG | PRO C | 82 | −18.244 | 53.239 | −90.975 | 1.00 | 32.91 | C |
| ATOM | 8472 | CD | PRO C | 82 | −17.193 | 53.019 | −89.930 | 1.00 | 32.48 | C |
| ATOM | 8473 | C | PRO C | 82 | −20.043 | 54.687 | −88.602 | 1.00 | 31.92 | C |
| ATOM | 8474 | O | PRO C | 82 | −20.536 | 53.571 | −88.459 | 1.00 | 31.91 | O |
| ATOM | 8475 | N | VAL C | 83 | −20.652 | 55.810 | −88.238 | 1.00 | 31.55 | N |
| ATOM | 8476 | CA | VAL C | 83 | −22.044 | 55.850 | −87.820 | 1.00 | 32.34 | C |
| ATOM | 8477 | CB | VAL C | 83 | −22.197 | 56.544 | −86.457 | 1.00 | 32.37 | C |
| ATOM | 8478 | CG1 | VAL C | 83 | −23.666 | 56.755 | −86.111 | 1.00 | 31.90 | C |
| ATOM | 8479 | CG2 | VAL C | 83 | −21.491 | 55.748 | −85.370 | 1.00 | 32.81 | C |
| ATOM | 8480 | C | VAL C | 83 | −22.820 | 56.639 | −88.853 | 1.00 | 34.24 | C |
| ATOM | 8481 | O | VAL C | 83 | −22.450 | 57.773 | −89.180 | 1.00 | 35.46 | O |
| ATOM | 8482 | N | LEU C | 84 | −23.893 | 56.054 | −89.374 | 1.00 | 36.25 | N |
| ATOM | 8483 | CA | LEU C | 84 | −24.703 | 56.748 | −90.375 | 1.00 | 39.49 | C |
| ATOM | 8484 | CB | LEU C | 84 | −25.508 | 55.755 | −91.216 | 1.00 | 40.36 | C |
| ATOM | 8485 | CG | LEU C | 84 | −24.822 | 54.828 | −92.223 | 1.00 | 39.79 | C |
| ATOM | 8486 | CD1 | LEU C | 84 | −25.824 | 54.523 | −93.321 | 1.00 | 39.35 | C |
| ATOM | 8487 | CD2 | LEU C | 84 | −23.540 | 55.403 | −92.817 | 1.00 | 39.54 | C |
| ATOM | 8488 | C | LEU C | 84 | −25.640 | 57.789 | −89.753 | 1.00 | 41.47 | C |
| ATOM | 8489 | O | LEU C | 84 | −26.301 | 57.501 | −88.752 | 1.00 | 41.38 | O |
| ATOM | 8490 | N | PRO C | 85 | −25.703 | 59.001 | −90.353 | 1.00 | 44.30 | N |
| ATOM | 8491 | CA | PRO C | 85 | −26.596 | 60.098 | −89.923 | 1.00 | 46.25 | C |
| ATOM | 8492 | CB | PRO C | 85 | −26.252 | 61.241 | −90.894 | 1.00 | 45.46 | C |
| ATOM | 8493 | CG | PRO C | 85 | −24.933 | 60.887 | −91.476 | 1.00 | 45.49 | C |
| ATOM | 8494 | CD | PRO C | 85 | −24.898 | 59.389 | −91.524 | 1.00 | 45.11 | C |
| ATOM | 8495 | C | PRO C | 85 | −28.087 | 59.762 | −90.062 | 1.00 | 48.12 | C |
| ATOM | 8496 | O | PRO C | 85 | −28.484 | 59.078 | −91.012 | 1.00 | 49.21 | O |
| ATOM | 8497 | N | GLN C | 86 | −28.896 | 60.250 | −89.119 | 1.00 | 48.69 | N |
| ATOM | 8498 | CA | GLN C | 86 | −30.367 | 60.123 | −89.172 | 1.00 | 49.36 | C |
| ATOM | 8499 | CB | GLN C | 86 | −30.948 | 60.841 | −90.399 | 1.00 | 51.10 | C |
| ATOM | 8500 | CG | GLN C | 86 | −30.607 | 62.316 | −90.486 | 1.00 | 53.96 | C |
| ATOM | 8501 | CD | GLN C | 86 | −30.135 | 62.709 | −91.871 | 1.00 | 57.88 | C |
| ATOM | 8502 | OE1 | GLN C | 86 | −29.172 | 63.467 | −92.015 | 1.00 | 60.52 | O |
| ATOM | 8503 | NE2 | GLN C | 86 | −30.800 | 62.183 | −92.904 | 1.00 | 56.82 | N |
| ATOM | 8504 | C | GLN C | 86 | −30.878 | 58.682 | −89.116 | 1.00 | 47.33 | C |
| ATOM | 8505 | O | GLN C | 86 | −32.064 | 58.426 | −89.326 | 1.00 | 46.93 | O |
| ATOM | 8506 | N | VAL C | 87 | −29.985 | 57.741 | −88.847 | 1.00 | 46.99 | N |
| ATOM | 8507 | CA | VAL C | 87 | −30.416 | 56.400 | −88.509 | 1.00 | 48.31 | C |
| ATOM | 8508 | CB | VAL C | 87 | −29.360 | 55.326 | −88.857 | 1.00 | 48.85 | C |
| ATOM | 8509 | CG1 | VAL C | 87 | −29.812 | 53.952 | −88.378 | 1.00 | 49.43 | C |
| ATOM | 8510 | CG2 | VAL C | 87 | −29.106 | 55.293 | −90.355 | 1.00 | 49.29 | C |
| ATOM | 8511 | C | VAL C | 87 | −30.749 | 56.388 | −87.021 | 1.00 | 48.65 | C |
| ATOM | 8512 | O | VAL C | 87 | −29.887 | 56.634 | −86.172 | 1.00 | 48.40 | O |
| ATOM | 8513 | N | MET C | 88 | −32.022 | 56.155 | −86.726 | 1.00 | 49.63 | N |
| ATOM | 8514 | CA | MET C | 88 | −32.494 | 55.989 | −85.362 | 1.00 | 50.44 | C |
| ATOM | 8515 | CB | MET C | 88 | −33.556 | 57.042 | −85.008 | 1.00 | 52.67 | C |
| ATOM | 8516 | CG | MET C | 88 | −33.175 | 58.483 | −85.321 | 1.00 | 57.19 | C |
| ATOM | 8517 | SD | MET C | 88 | −31.978 | 59.218 | −84.179 | 1.00 | 62.30 | S |
| ATOM | 8518 | CE | MET C | 88 | −31.746 | 60.841 | −84.924 | 1.00 | 60.71 | C |
| ATOM | 8519 | C | MET C | 88 | −33.095 | 54.594 | −85.245 | 1.00 | 49.60 | C |
| ATOM | 8520 | O | MET C | 88 | −33.981 | 54.227 | −86.027 | 1.00 | 50.22 | O |
| ATOM | 8521 | N | MET C | 89 | −32.579 | 53.813 | −84.298 | 1.00 | 46.72 | N |
| ATOM | 8522 | CA | MET C | 89 | −33.185 | 52.541 | −83.893 | 1.00 | 46.94 | C |
| ATOM | 8523 | CB | MET C | 89 | −33.848 | 51.801 | −85.066 | 1.00 | 48.19 | C |
| ATOM | 8524 | CG | MET C | 89 | −32.898 | 51.017 | −85.952 | 1.00 | 48.58 | C |
| ATOM | 8525 | SD | MET C | 89 | −33.741 | 49.657 | −86.774 | 1.00 | 50.63 | S |
| ATOM | 8526 | CE | MET C | 89 | −34.024 | 48.535 | −85.413 | 1.00 | 49.84 | C |
| ATOM | 8527 | C | MET C | 89 | −32.186 | 51.631 | −83.200 | 1.00 | 45.40 | C |
| ATOM | 8528 | O | MET C | 89 | −31.007 | 51.614 | −83.541 | 1.00 | 46.11 | O |
| ATOM | 8529 | N | ILE C | 90 | −32.673 | 50.875 | −82.225 | 1.00 | 43.10 | N |
| ATOM | 8530 | CA | ILE C | 90 | −31.851 | 49.904 | −81.529 | 1.00 | 41.54 | C |

-continued

| | | | Atomic coordinates for CRBN:DDB1:Lenalidomide (Human protein) | | | | | | |
|---|---|---|---|---|---|---|---|---|---|
| ATOM | 8531 | CB | ILE C | 90 | −32.348 | 49.668 | −80.082 | 1.00 | 41.55 | C |
| ATOM | 8532 | CG1 | ILE C | 90 | −32.304 | 50.973 | −79.279 | 1.00 | 42.36 | C |
| ATOM | 8533 | CD1 | ILE C | 90 | −33.529 | 51.854 | −79.442 | 1.00 | 43.41 | C |
| ATOM | 8534 | CG2 | ILE C | 90 | −31.512 | 48.609 | −79.382 | 1.00 | 40.51 | C |
| ATOM | 8535 | C | ILE C | 90 | −31.870 | 48.620 | −82.348 | 1.00 | 39.60 | C |
| ATOM | 8536 | O | ILE C | 90 | −32.909 | 47.986 | −82.501 | 1.00 | 41.67 | O |
| ATOM | 8537 | N | LEU C | 91 | −30.717 | 48.260 | −82.892 | 1.00 | 36.47 | N |
| ATOM | 8538 | CA | LEU C | 91 | −30.624 | 47.153 | −83.831 | 1.00 | 35.24 | C |
| ATOM | 8539 | CB | LEU C | 91 | −29.780 | 47.591 | −85.035 | 1.00 | 34.60 | C |
| ATOM | 8540 | CG | LEU C | 91 | −29.450 | 46.756 | −86.271 | 1.00 | 33.80 | C |
| ATOM | 8541 | CD1 | LEU C | 91 | −28.042 | 46.204 | −86.154 | 1.00 | 33.17 | C |
| ATOM | 8542 | CD2 | LEU C | 91 | −30.475 | 45.671 | −86.564 | 1.00 | 33.43 | C |
| ATOM | 8543 | C | LEU C | 91 | −30.052 | 45.914 | −83.132 | 1.00 | 36.11 | C |
| ATOM | 8544 | O | LEU C | 91 | −29.052 | 45.992 | −82.413 | 1.00 | 39.89 | O |
| ATOM | 8545 | N | ILE C | 92 | −30.707 | 44.777 | −83.326 | 1.00 | 33.21 | N |
| ATOM | 8546 | CA | ILE C | 92 | −30.378 | 43.560 | −82.603 | 1.00 | 30.24 | C |
| ATOM | 8547 | CB | ILE C | 92 | −31.671 | 42.904 | −82.060 | 1.00 | 30.06 | C |
| ATOM | 8548 | CG1 | ILE C | 92 | −32.304 | 43.832 | −81.022 | 1.00 | 30.22 | C |
| ATOM | 8549 | CD1 | ILE C | 92 | −33.796 | 43.669 | −80.865 | 1.00 | 30.47 | C |
| ATOM | 8550 | CG2 | ILE C | 92 | −31.410 | 41.535 | −81.432 | 1.00 | 30.01 | C |
| ATOM | 8551 | C | ILE C | 92 | −29.594 | 42.627 | −83.521 | 1.00 | 29.15 | C |
| ATOM | 8552 | O | ILE C | 92 | −29.911 | 42.516 | −84.700 | 1.00 | 27.90 | O |
| ATOM | 8553 | N | PRO C | 93 | −28.538 | 41.979 | −82.992 | 1.00 | 29.20 | N |
| ATOM | 8554 | CA | PRO C | 93 | −27.841 | 40.941 | −83.753 | 1.00 | 29.00 | C |
| ATOM | 8555 | CB | PRO C | 93 | −27.068 | 40.183 | −82.674 | 1.00 | 28.97 | C |
| ATOM | 8556 | CG | PRO C | 93 | −26.763 | 41.222 | −81.656 | 1.00 | 29.19 | C |
| ATOM | 8557 | CD | PRO C | 93 | −27.891 | 42.225 | −81.689 | 1.00 | 29.52 | C |
| ATOM | 8558 | C | PRO C | 93 | −28.812 | 40.001 | −84.465 | 1.00 | 28.65 | C |
| ATOM | 8559 | O | PRO C | 93 | −29.724 | 39.454 | −83.834 | 1.00 | 28.36 | O |
| ATOM | 8560 | N | GLY C | 94 | −28.630 | 39.852 | −85.775 | 1.00 | 28.42 | N |
| ATOM | 8561 | CA | GLY C | 94 | −29.461 | 38.958 | −86.583 | 1.00 | 28.00 | C |
| ATOM | 8562 | C | GLY C | 94 | −30.690 | 39.613 | −87.184 | 1.00 | 27.59 | C |
| ATOM | 8563 | O | GLY C | 94 | −31.316 | 39.053 | −88.072 | 1.00 | 27.01 | O |
| ATOM | 8564 | N | GLN C | 95 | −31.046 | 40.793 | −86.681 | 1.00 | 28.15 | N |
| ATOM | 8565 | CA | GLN C | 95 | −32.199 | 41.537 | −87.176 | 1.00 | 28.34 | C |
| ATOM | 8566 | CB | GLN C | 95 | −32.576 | 42.658 | −86.206 | 1.00 | 28.24 | C |
| ATOM | 8567 | CG | GLN C | 95 | −33.965 | 43.251 | −86.403 | 1.00 | 28.38 | C |
| ATOM | 8568 | CD | GLN C | 95 | −34.318 | 44.351 | −85.396 | 1.00 | 28.34 | C |
| ATOM | 8569 | OE1 | GLN C | 95 | −35.468 | 44.790 | −85.332 | 1.00 | 29.15 | O |
| ATOM | 8570 | NE2 | GLN C | 95 | −33.340 | 44.797 | −84.614 | 1.00 | 27.40 | N |
| ATOM | 8571 | C | GLN C | 95 | −31.826 | 42.119 | −88.515 | 1.00 | 29.86 | C |
| ATOM | 8572 | O | GLN C | 95 | −30.661 | 42.414 | −88.781 | 1.00 | 31.52 | O |
| ATOM | 8573 | N | THR C | 96 | −32.807 | 42.277 | −89.377 | 1.00 | 30.47 | N |
| ATOM | 8574 | CA | THR C | 96 | −32.517 | 42.777 | −90.689 | 1.00 | 30.40 | C |
| ATOM | 8575 | CB | THR C | 96 | −33.226 | 41.908 | −91.742 | 1.00 | 30.74 | C |
| ATOM | 8576 | OG1 | THR C | 96 | −32.317 | 41.622 | −92.810 | 1.00 | 32.25 | O |
| ATOM | 8577 | CG2 | THR C | 96 | −34.523 | 42.558 | −92.265 | 1.00 | 32.34 | C |
| ATOM | 8578 | C | THR C | 96 | −32.851 | 44.282 | −90.742 | 1.00 | 30.48 | C |
| ATOM | 8579 | O | THR C | 96 | −33.789 | 44.731 | −90.073 | 1.00 | 32.69 | O |
| ATOM | 8580 | N | LEU C | 97 | −32.063 | 45.059 | −91.485 | 1.00 | 28.56 | N |
| ATOM | 8581 | CA | LEU C | 97 | −32.244 | 46.508 | −91.535 | 1.00 | 27.45 | C |
| ATOM | 8582 | CB | LEU C | 97 | −31.191 | 47.202 | −90.671 | 1.00 | 27.25 | C |
| ATOM | 8583 | OG1 | LEU C | 97 | −31.188 | 48.738 | −90.646 | 1.00 | 27.16 | C |
| ATOM | 8584 | CD1 | LEU C | 97 | −32.492 | 49.277 | −90.087 | 1.00 | 27.40 | C |
| ATOM | 8585 | CD2 | LEU C | 97 | −30.008 | 49.289 | −89.860 | 1.00 | 26.55 | C |
| ATOM | 8586 | C | LEU C | 97 | −32.181 | 47.052 | −92.959 | 1.00 | 27.79 | C |
| ATOM | 8587 | O | LEU C | 97 | −31.124 | 47.016 | −93.583 | 1.00 | 28.86 | O |
| ATOM | 8588 | N | PRO C | 98 | −33.310 | 47.571 | −93.482 | 1.00 | 27.51 | N |
| ATOM | 8589 | CA | PRO C | 98 | −33.285 | 48.137 | −94.827 | 1.00 | 26.97 | C |
| ATOM | 8590 | CB | PRO C | 98 | −34.661 | 47.770 | −95.370 | 1.00 | 26.42 | C |
| ATOM | 8591 | CG | PRO C | 98 | −35.545 | 47.702 | −94.154 | 1.00 | 26.82 | C |
| ATOM | 8592 | CD | PRO C | 98 | −34.675 | 47.572 | −92.925 | 1.00 | 27.20 | C |
| ATOM | 8593 | C | PRO C | 98 | −33.105 | 49.656 | −94.781 | 1.00 | 27.08 | C |
| ATOM | 8594 | O | PRO C | 98 | −33.591 | 50.304 | −93.856 | 1.00 | 27.67 | O |
| ATOM | 8595 | N | LEU C | 99 | −32.398 | 50.212 | −95.759 | 1.00 | 26.93 | N |
| ATOM | 8596 | CA | LEU C | 99 | −32.100 | 51.645 | −95.768 | 1.00 | 26.96 | C |
| ATOM | 8597 | CB | LEU C | 99 | −30.690 | 51.922 | −95.219 | 1.00 | 26.12 | C |
| ATOM | 8598 | CG | LEU C | 99 | −30.315 | 51.598 | −93.765 | 1.00 | 25.67 | C |
| ATOM | 8599 | CD1 | LEU C | 99 | −28.900 | 52.075 | −93.471 | 1.00 | 24.67 | C |
| ATOM | 8600 | CD2 | LEU C | 99 | −31.292 | 52.206 | −92.764 | 1.00 | 25.87 | C |
| ATOM | 8601 | C | LEU C | 99 | −32.247 | 52.264 | −97.159 | 1.00 | 27.43 | C |
| ATOM | 8602 | O | LEU C | 99 | −32.173 | 51.567 | −98.170 | 1.00 | 27.81 | O |
| ATOM | 8603 | N | GLN C | 100 | −32.466 | 53.577 | −97.192 | 1.00 | 27.30 | N |
| ATOM | 8604 | CA | GLN C | 100 | −32.544 | 54.338 | −98.434 | 1.00 | 26.51 | C |
| ATOM | 8605 | CB | GLN C | 100 | −33.993 | 54.558 | −98.856 | 1.00 | 26.96 | C |
| ATOM | 8606 | CG | GLN C | 100 | −34.689 | 53.306 | −99.343 | 1.00 | 28.55 | C |
| ATOM | 8607 | CD | GLN C | 100 | −35.862 | 53.607 | −100.243 | 1.00 | 29.42 | C |

-continued

| | | | | Atomic coordinates for CRBN:DDB1:Lenalidomide (Human protein) | | | | | |
|---|---|---|---|---|---|---|---|---|---|
| ATOM | 8608 | OE1 | GLN C | 100 | −35.713 | 54.251 | −101.280 | 1.00 | 30.57 | O |
| ATOM | 8609 | NE2 | GLN C | 100 | −37.040 | 53.129 | −99.859 | 1.00 | 30.28 | N |
| ATOM | 8610 | C | GLN C | 100 | −31.870 | 55.671 | −98.224 | 1.00 | 26.03 | C |
| ATOM | 8611 | O | GLN C | 100 | −32.316 | 56.484 | −97.410 | 1.00 | 25.18 | O |
| ATOM | 8612 | N | LEU C | 101 | −30.798 | 55.901 | −98.968 | 1.00 | 26.45 | N |
| ATOM | 8613 | CA | LEU C | 101 | −29.941 | 57.057 | −98.722 | 1.00 | 27.97 | C |
| ATOM | 8614 | CB | LEU C | 101 | −28.505 | 56.593 | −98.436 | 1.00 | 27.99 | C |
| ATOM | 8615 | CG | LEU C | 101 | −28.368 | 55.382 | −97.500 | 1.00 | 27.16 | C |
| ATOM | 8616 | CD1 | LEU C | 101 | −27.138 | 54.572 | −97.859 | 1.00 | 27.13 | C |
| ATOM | 8617 | CD2 | LEU C | 101 | −28.370 | 55.755 | −96.024 | 1.00 | 26.08 | C |
| ATOM | 8618 | C | LEU C | 101 | −29.974 | 58.062 | −99.871 | 1.00 | 28.06 | C |
| ATOM | 8619 | O | LEU C | 101 | −29.915 | 57.679 | −101.038 | 1.00 | 27.13 | O |
| ATOM | 8620 | N | PHE C | 102 | −30.072 | 59.346 | −99.537 | 1.00 | 29.69 | N |
| ATOM | 8621 | CA | PHE C | 102 | −30.167 | 60.378 | −100.575 | 1.00 | 33.44 | C |
| ATOM | 8622 | CB | PHE C | 102 | −31.535 | 61.077 | −100.557 | 1.00 | 32.33 | C |
| ATOM | 8623 | CG | PHE C | 102 | −32.701 | 60.125 | −100.490 | 1.00 | 32.63 | C |
| ATOM | 8624 | CD1 | PHE C | 102 | −33.177 | 59.500 | −101.644 | 1.00 | 32.65 | C |
| ATOM | 8625 | CE1 | PHE C | 102 | −34.244 | 58.612 | −101.588 | 1.00 | 31.50 | C |
| ATOM | 8626 | CZ | PHE C | 102 | −34.847 | 58.344 | −100.373 | 1.00 | 31.64 | C |
| ATOM | 8627 | CE2 | PHE C | 102 | −34.381 | 58.954 | −99.213 | 1.00 | 31.37 | C |
| ATOM | 8628 | CD2 | PHE C | 102 | −33.316 | 59.837 | −99.272 | 1.00 | 31.86 | C |
| ATOM | 8629 | C | PHE C | 102 | −29.032 | 61.391 | −100.511 | 1.00 | 35.80 | C |
| ATOM | 8630 | O | PHE C | 102 | −28.613 | 61.919 | −101.542 | 1.00 | 35.10 | O |
| ATOM | 8631 | N | HIS C | 103 | −28.536 | 61.658 | −99.307 | 1.00 | 38.94 | N |
| ATOM | 8632 | CA | HIS C | 103 | −27.487 | 62.655 | −99.137 | 1.00 | 43.09 | C |
| ATOM | 8633 | CB | HIS C | 103 | −27.397 | 63.118 | −97.689 | 1.00 | 48.26 | C |
| ATOM | 8634 | CG | HIS C | 103 | −28.585 | 63.936 | −97.251 | 1.00 | 53.46 | C |
| ATOM | 8635 | ND1 | HIS C | 103 | −29.495 | 63.479 | −96.365 | 1.00 | 55.09 | N |
| ATOM | 8636 | CE1 | HIS C | 103 | −30.450 | 64.413 | −96.185 | 1.00 | 55.96 | C |
| ATOM | 8637 | NE2 | HIS C | 103 | −30.157 | 65.467 | −96.969 | 1.00 | 57.55 | N |
| ATOM | 8638 | CD2 | HIS C | 103 | −29.016 | 65.205 | −97.643 | 1.00 | 54.72 | C |
| ATOM | 8639 | C | HIS C | 103 | −26.175 | 62.137 | −99.618 | 1.00 | 41.95 | C |
| ATOM | 8640 | O | HIS C | 103 | −25.804 | 61.014 | −99.293 | 1.00 | 42.13 | O |
| ATOM | 8641 | N | PRO C | 104 | −25.463 | 62.937 | −100.434 | 1.00 | 41.99 | N |
| ATOM | 8642 | CA | PRO C | 104 | −24.143 | 62.520 | −100.919 | 1.00 | 41.37 | C |
| ATOM | 8643 | CB | PRO C | 104 | −23.622 | 63.759 | −101.665 | 1.00 | 40.76 | C |
| ATOM | 8644 | CG | PRO C | 104 | −24.603 | 64.860 | −101.382 | 1.00 | 41.34 | C |
| ATOM | 8645 | CD | PRO C | 104 | −25.898 | 64.206 | −101.041 | 1.00 | 40.84 | C |
| ATOM | 8646 | C | PRO C | 104 | −23.221 | 62.140 | −99.759 | 1.00 | 41.48 | C |
| ATOM | 8647 | O | PRO C | 104 | −22.396 | 61.236 | −99.897 | 1.00 | 39.63 | O |
| ATOM | 8648 | N | GLN C | 105 | −23.390 | 62.830 | −98.628 | 1.00 | 43.46 | N |
| ATOM | 8649 | CA | GLN C | 105 | −22.747 | 62.483 | −97.358 | 1.00 | 44.79 | C |
| ATOM | 8650 | CB | GLN C | 105 | −23.425 | 63.240 | −96.206 | 1.00 | 46.42 | C |
| ATOM | 8651 | CG | GLN C | 105 | −23.398 | 64.754 | −96.325 | 1.00 | 48.08 | C |
| ATOM | 8652 | CD | GLN C | 105 | −22.015 | 65.325 | −96.087 | 1.00 | 49.62 | C |
| ATOM | 8653 | OE1 | GLN C | 105 | −21.210 | 64.751 | −95.340 | 1.00 | 50.45 | O |
| ATOM | 8654 | NE2 | GLN C | 105 | −21.725 | 66.460 | −96.724 | 1.00 | 48.01 | N |
| ATOM | 8655 | C | GLN C | 105 | −22.837 | 60.972 | −97.097 | 1.00 | 45.62 | C |
| ATOM | 8656 | O | GLN C | 105 | −21.815 | 60.274 | −97.063 | 1.00 | 46.32 | O |
| ATOM | 8657 | N | GLU C | 106 | −24.073 | 60.491 | −96.921 | 1.00 | 44.15 | N |
| ATOM | 8658 | CA | GLU C | 106 | −24.382 | 59.074 | −95.731 | 1.00 | 41.32 | C |
| ATOM | 8659 | CB | GLU C | 106 | −25.896 | 58.875 | −96.596 | 1.00 | 40.29 | C |
| ATOM | 8660 | CG | GLU C | 106 | −26.559 | 59.649 | −95.465 | 1.00 | 39.99 | C |
| ATOM | 8661 | CD | GLU C | 106 | −28.049 | 59.849 | −95.688 | 1.00 | 40.26 | C |
| ATOM | 8662 | OE1 | GLU C | 106 | −28.532 | 59.557 | −96.803 | 1.00 | 41.69 | O |
| ATOM | 8663 | OE2 | GLU C | 106 | −28.743 | 60.310 | −94.754 | 1.00 | 39.61 | O |
| ATOM | 8664 | C | GLU C | 106 | −23.870 | 58.235 | −97.902 | 1.00 | 41.34 | C |
| ATOM | 8665 | O | GLU C | 106 | −23.121 | 57.276 | −97.704 | 1.00 | 42.99 | O |
| ATOM | 8666 | N | VAL C | 107 | −24.269 | 58.622 | −99.115 | 1.00 | 39.66 | N |
| ATOM | 8667 | CA | VAL C | 107 | −23.972 | 57.877 | −100.347 | 1.00 | 38.41 | C |
| ATOM | 8668 | CB | VAL C | 107 | −24.639 | 58.548 | −101.585 | 1.00 | 37.86 | C |
| ATOM | 8669 | CG1 | VAL C | 107 | −24.131 | 57.961 | −102.890 | 1.00 | 37.14 | C |
| ATOM | 8670 | CG2 | VAL C | 107 | −26.154 | 58.412 | −101.514 | 1.00 | 37.14 | C |
| ATOM | 8671 | C | VAL C | 107 | −22.466 | 57.643 | −100.557 | 1.00 | 38.26 | C |
| ATOM | 8672 | O | VAL C | 107 | −22.068 | 56.676 | −101.207 | 1.00 | 38.57 | O |
| ATOM | 8673 | N | SER C | 108 | −21.635 | 58.519 | −99.994 | 1.00 | 37.54 | N |
| ATOM | 8674 | CA | SER C | 108 | −20.190 | 58.290 | −99.968 | 1.00 | 37.77 | C |
| ATOM | 8675 | CB | SER C | 108 | −19.438 | 59.580 | −99.638 | 1.00 | 39.12 | C |
| ATOM | 8676 | OG | SER C | 108 | −19.795 | 60.612 | −100.533 | 1.00 | 40.65 | O |
| ATOM | 8677 | C | SER C | 108 | −19.807 | 57.198 | −98.965 | 1.00 | 37.43 | C |
| ATOM | 8678 | O | SER C | 108 | −19.113 | 56.237 | −99.325 | 1.00 | 37.40 | O |
| ATOM | 8679 | N | MET C | 109 | −20.272 | 57.345 | −97.719 | 1.00 | 35.59 | N |
| ATOM | 8680 | CA | MET C | 109 | −19.930 | 56.425 | −96.628 | 1.00 | 34.79 | C |
| ATOM | 8681 | CB | MET C | 109 | −20.690 | 56.790 | −95.348 | 1.00 | 34.81 | C |
| ATOM | 8682 | C | MET C | 109 | −20.170 | 54.957 | −96.978 | 1.00 | 34.43 | C |
| ATOM | 8683 | O | MET C | 109 | −19.394 | 54.090 | −96.589 | 1.00 | 35.20 | O |
| ATOM | 8684 | N | VAL C | 110 | −21.239 | 54.691 | −97.722 | 1.00 | 33.61 | N |

Atomic coordinates for CRBN:DDB1:Lenalidomide (Human protein)

| ATOM | 8685 | CA | VAL C | 110 | −21.621 | 53.325 | −98.086 | 1.00 | 32.92 | C |
| --- | --- | --- | --- | --- | --- | --- | --- | --- | --- | --- |
| ATOM | 8686 | CB | VAL C | 110 | −23.141 | 53.231 | −98.367 | 1.00 | 31.39 | C |
| ATOM | 8687 | CG1 | VAL C | 110 | −23.561 | 51.794 | −98.634 | 1.00 | 30.90 | C |
| ATOM | 8688 | CG2 | VAL C | 110 | −23.924 | 53.796 | −97.198 | 1.00 | 30.43 | C |
| ATOM | 8689 | C | VAL C | 110 | −20.812 | 52.831 | −99.292 | 1.00 | 33.25 | C |
| ATOM | 8690 | O | VAL C | 110 | −20.216 | 51.749 | −99.259 | 1.00 | 31.84 | O |
| ATOM | 8691 | N | ARG C | 111 | −20.799 | 53.641 | −100.350 | 1.00 | 34.78 | N |
| ATOM | 8692 | CA | ARG C | 111 | −20.051 | 53.351 | −101.566 | 1.00 | 36.02 | C |
| ATOM | 8693 | CB | ARG C | 111 | −19.971 | 54.606 | −102.434 | 1.00 | 36.55 | C |
| ATOM | 8694 | CG | ARG C | 111 | −19.657 | 54.362 | −103.901 | 1.00 | 36.77 | C |
| ATOM | 8695 | CD | ARG C | 111 | −19.758 | 55.660 | −104.685 | 1.00 | 36.42 | C |
| ATOM | 8696 | NE | ARG C | 111 | −21.122 | 55.943 | −105.128 | 1.00 | 36.80 | N |
| ATOM | 8697 | CZ | ARG C | 111 | −21.556 | 57.144 | −105.512 | 1.00 | 37.60 | C |
| ATOM | 8698 | NH1 | ARG C | 111 | −20.743 | 58.194 | −105.487 | 1.00 | 37.77 | N |
| ATOM | 8699 | NH2 | ARG C | 111 | −22.811 | 57.303 | −105.915 | 1.00 | 36.75 | N |
| ATOM | 8700 | C | ARG C | 111 | −18.655 | 52.853 | −101.215 | 1.00 | 37.05 | C |
| ATOM | 8701 | O | ARG C | 111 | −18.160 | 51.903 | −101.826 | 1.00 | 37.08 | O |
| ATOM | 8702 | N | ASN C | 112 | −18.049 | 53.481 | −100.206 | 1.00 | 38.08 | N |
| ATOM | 8703 | CA | ASN C | 112 | −16.736 | 53.076 | −99.699 | 1.00 | 40.02 | C |
| ATOM | 8704 | CB | ASN C | 112 | −15.988 | 54.270 | −99.096 | 1.00 | 41.72 | C |
| ATOM | 8705 | CG | ASN C | 112 | −15.295 | 55.120 | −100.152 | 1.00 | 42.80 | C |
| ATOM | 8706 | OD1 | ASN C | 112 | −15.923 | 55.580 | −101.115 | 1.00 | 42.33 | O |
| ATOM | 8707 | ND2 | ASN C | 112 | −13.991 | 55.339 | −99.971 | 1.00 | 42.91 | N |
| ATOM | 8708 | C | ASN C | 112 | −16.755 | 51.907 | −98.711 | 1.00 | 39.75 | C |
| ATOM | 8709 | O | ASN C | 112 | −15.795 | 51.144 | −98.638 | 1.00 | 40.53 | O |
| ATOM | 8710 | N | LEU C | 113 | −17.836 | 51.767 | −97.950 | 1.00 | 39.68 | N |
| ATOM | 8711 | CA | LEU C | 113 | −18.003 | 50.601 | −97.075 | 1.00 | 39.46 | C |
| ATOM | 8712 | CB | LEU C | 113 | −19.331 | 50.672 | −96.319 | 1.00 | 38.50 | C |
| ATOM | 8713 | CG | LEU C | 113 | −19.385 | 51.040 | −94.836 | 1.00 | 38.16 | C |
| ATOM | 8714 | CD1 | LEU C | 113 | −18.147 | 51.783 | −94.350 | 1.00 | 38.15 | C |
| ATOM | 8715 | CD2 | LEU C | 113 | −20.647 | 51.845 | −94.576 | 1.00 | 38.78 | C |
| ATOM | 8716 | C | LEU C | 113 | −17.940 | 49.308 | −97.877 | 1.00 | 40.48 | C |
| ATOM | 8717 | O | LEU C | 113 | −17.356 | 48.324 | −97.422 | 1.00 | 39.85 | O |
| ATOM | 8718 | N | ILE C | 114 | −18.539 | 49.330 | −99.072 | 1.00 | 41.91 | N |
| ATOM | 8719 | CA | ILE C | 114 | −18.600 | 48.168 | −99.959 | 1.00 | 43.17 | C |
| ATOM | 8720 | CB | ILE C | 114 | −19.279 | 48.513 | −101.294 | 1.00 | 43.42 | C |
| ATOM | 8721 | CG1 | ILE C | 114 | −20.686 | 49.084 | −101.066 | 1.00 | 43.54 | C |
| ATOM | 8722 | CD1 | ILE C | 114 | −21.669 | 48.122 | −100.425 | 1.00 | 44.57 | C |
| ATOM | 8723 | CG2 | ILE C | 114 | −19.295 | 47.297 | −102.210 | 1.00 | 44.62 | C |
| ATOM | 8724 | C | ILE C | 114 | −17.213 | 47.600 | −100.243 | 1.00 | 45.69 | C |
| ATOM | 8725 | O | ILE C | 114 | −16.956 | 46.415 | −100.001 | 1.00 | 48.31 | O |
| ATOM | 8726 | N | GLN C | 115 | −16.320 | 48.439 | −100.766 | 1.00 | 46.36 | N |
| ATOM | 8727 | CA | GLN C | 115 | −14.928 | 48.051 | −100.885 | 1.00 | 46.86 | C |
| ATOM | 8728 | CB | GLN C | 115 | −14.131 | 49.030 | −101.771 | 1.00 | 47.82 | C |
| ATOM | 8729 | CG | GLN C | 115 | −14.851 | 49.574 | −103.011 | 1.00 | 50.21 | C |
| ATOM | 8730 | CD | GLN C | 115 | −15.155 | 48.523 | −104.078 | 1.00 | 50.48 | C |
| ATOM | 8731 | OE1 | GLN C | 115 | −16.237 | 48.527 | −104.669 | 1.00 | 50.88 | O |
| ATOM | 8732 | NE2 | GLN C | 115 | −14.205 | 47.624 | −104.329 | 1.00 | 49.47 | N |
| ATOM | 8733 | C | GLN C | 115 | −14.371 | 48.042 | −99.465 | 1.00 | 47.81 | C |
| ATOM | 8734 | O | GLN C | 115 | −13.908 | 49.075 | −98.978 | 1.00 | 49.86 | O |
| ATOM | 8735 | N | LYS C | 116 | −14.474 | 46.893 | −98.785 | 1.00 | 45.30 | N |
| ATOM | 8736 | CA | LYS C | 116 | −13.889 | 46.703 | −97.445 | 1.00 | 42.66 | C |
| ATOM | 8737 | CB | LYS C | 116 | −13.435 | 48.040 | −96.832 | 1.00 | 41.26 | C |
| ATOM | 8738 | C | LYS C | 116 | −14.801 | 45.980 | −96.455 | 1.00 | 41.25 | C |
| ATOM | 8739 | O | LYS C | 116 | −15.328 | 44.901 | −96.734 | 1.00 | 39.67 | O |
| ATOM | 8740 | N | ASP C | 117 | −14.957 | 46.614 | −95.294 | 1.00 | 41.25 | N |
| ATOM | 8741 | CA | ASP C | 117 | −15.666 | 46.095 | −94.126 | 1.00 | 40.39 | C |
| ATOM | 8742 | CB | ASP C | 117 | −15.621 | 47.157 | −93.018 | 1.00 | 41.17 | C |
| ATOM | 8743 | CG | ASP C | 117 | −15.280 | 46.580 | −91.674 | 1.00 | 41.70 | C |
| ATOM | 8744 | OD1 | ASP C | 117 | −14.361 | 45.738 | −91.605 | 1.00 | 42.14 | O |
| ATOM | 8745 | OD2 | ASP C | 117 | −15.916 | 46.983 | −90.681 | 1.00 | 42.34 | O |
| ATOM | 8746 | C | ASP C | 117 | −17.124 | 45.756 | −94.406 | 1.00 | 38.57 | C |
| ATOM | 8747 | O | ASP C | 117 | −17.633 | 44.734 | −93.933 | 1.00 | 38.11 | O |
| ATOM | 8748 | N | ARG C | 118 | −17.783 | 46.636 | −95.165 | 1.00 | 36.88 | N |
| ATOM | 8749 | CA | ARG C | 118 | −19.240 | 46.615 | −95.394 | 1.00 | 35.49 | C |
| ATOM | 8750 | CB | ARG C | 118 | −19.681 | 45.363 | −96.162 | 1.00 | 36.51 | C |
| ATOM | 8751 | CG | ARG C | 118 | −18.880 | 45.086 | −97.426 | 1.00 | 38.55 | C |
| ATOM | 8752 | CD | ARG C | 118 | −19.545 | 44.020 | −98.276 | 1.00 | 41.03 | C |
| ATOM | 8753 | NE | ARG C | 118 | −20.128 | 42.966 | −97.452 | 1.00 | 43.54 | N |
| ATOM | 8754 | CZ | ARG C | 118 | −19.554 | 41.794 | −97.206 | 1.00 | 45.75 | C |
| ATOM | 8755 | NH1 | ARG C | 118 | −18.372 | 41.498 | −97.736 | 1.00 | 47.47 | N |
| ATOM | 8756 | NH2 | ARG C | 118 | −20.173 | 40.909 | −96.437 | 1.00 | 46.95 | N |
| ATOM | 8757 | C | ARG C | 118 | −20.067 | 46.792 | −94.116 | 1.00 | 33.13 | C |
| ATOM | 8758 | O | ARG C | 118 | −21.292 | 46.671 | −94.143 | 1.00 | 31.84 | O |
| ATOM | 8759 | N | THR C | 119 | −19.392 | 47.084 | −93.004 | 1.00 | 31.69 | N |
| ATOM | 8760 | CA | THR C | 119 | −20.077 | 47.266 | −91.726 | 1.00 | 30.26 | C |
| ATOM | 8761 | CB | THR C | 119 | −19.660 | 46.235 | −90.624 | 1.00 | 30.53 | C |

-continued

| | | | Atomic coordinates for CRBN:DDB1:Lenalidomide (Human protein) | | | | | | |
|---|---|---|---|---|---|---|---|---|---|
| ATOM | 8762 | OG1 | THR C | 119 | −18.729 | 46.826 | −89.717 | 1.00 | 31.51 | O |
| ATOM | 8763 | CG2 | THR C | 119 | −19.037 | 44.974 | −91.208 | 1.00 | 31.29 | C |
| ATOM | 8764 | C | THR C | 119 | −19.934 | 48.691 | −91.210 | 1.00 | 28.53 | C |
| ATOM | 8765 | O | THR C | 119 | −18.861 | 49.296 | −91.287 | 1.00 | 27.14 | O |
| ATOM | 8766 | N | PHE C | 120 | −21.053 | 49.206 | −90.703 | 1.00 | 27.60 | N |
| ATOM | 8767 | CA | PHE C | 120 | −21.149 | 50.507 | −90.049 | 1.00 | 26.17 | C |
| ATOM | 8768 | CB | PHE C | 120 | −22.032 | 51.443 | −90.879 | 1.00 | 26.07 | C |
| ATOM | 8769 | CG | PHE C | 120 | −23.397 | 50.877 | −91.190 | 1.00 | 26.24 | C |
| ATOM | 8770 | CD1 | PHE C | 120 | −23.573 | 49.978 | −92.247 | 1.00 | 25.85 | C |
| ATOM | 8771 | CE1 | PHE C | 120 | −24.823 | 49.447 | −92.527 | 1.00 | 25.60 | C |
| ATOM | 8772 | CZ | PHE C | 120 | −25.918 | 49.820 | −91.756 | 1.00 | 25.57 | C |
| ATOM | 8773 | CE2 | PHE C | 120 | −25.759 | 50.714 | −90.704 | 1.00 | 25.27 | C |
| ATOM | 8774 | CD2 | PHE C | 120 | −24.509 | 51.237 | −90.422 | 1.00 | 25.34 | C |
| ATOM | 8775 | C | PHE C | 120 | −21.760 | 50.264 | −88.667 | 1.00 | 25.30 | C |
| ATOM | 8776 | O | PHE C | 120 | −22.143 | 49.138 | −88.352 | 1.00 | 24.86 | O |
| ATOM | 8777 | N | ALA C | 121 | −21.852 | 51.311 | −87.850 | 1.00 | 24.92 | N |
| ATOM | 8778 | CA | ALA C | 121 | −22.345 | 51.191 | −86.473 | 1.00 | 24.65 | C |
| ATOM | 8779 | CB | ALA C | 121 | −21.350 | 51.813 | −85.507 | 1.00 | 24.77 | C |
| ATOM | 8780 | C | ALA C | 121 | −23.728 | 51.816 | −86.278 | 1.00 | 24.74 | C |
| ATOM | 8781 | O | ALA C | 121 | −23.986 | 52.925 | −86.738 | 1.00 | 24.49 | O |
| ATOM | 8782 | N | VAL C | 122 | −24.615 | 51.096 | −85.596 | 1.00 | 25.32 | N |
| ATOM | 8783 | CA | VAL C | 122 | −25.926 | 51.634 | −85.237 | 1.00 | 26.25 | C |
| ATOM | 8784 | CB | VAL C | 122 | −27.081 | 50.715 | −85.680 | 1.00 | 25.92 | C |
| ATOM | 8785 | CG1 | VAL C | 122 | −28.417 | 51.378 | −85.406 | 1.00 | 26.44 | C |
| ATOM | 8786 | CG2 | VAL C | 122 | −26.972 | 50.385 | −87.157 | 1.00 | 26.11 | C |
| ATOM | 8787 | C | VAL C | 122 | −25.982 | 51.848 | −83.727 | 1.00 | 27.59 | C |
| ATOM | 8788 | O | VAL C | 122 | −25.592 | 50.972 | −82.951 | 1.00 | 27.24 | O |
| ATOM | 8789 | N | LEU C | 123 | −26.474 | 53.018 | −83.324 | 1.00 | 29.25 | N |
| ATOM | 8790 | CA | LEU C | 123 | −26.419 | 53.444 | −81.931 | 1.00 | 30.82 | C |
| ATOM | 8791 | CB | LEU C | 123 | −25.783 | 54.832 | −81.820 | 1.00 | 29.51 | C |
| ATOM | 8792 | CG | LEU C | 123 | −24.360 | 55.018 | −82.336 | 1.00 | 29.07 | C |
| ATOM | 8793 | CD1 | LEU C | 123 | −23.845 | 56.394 | −81.947 | 1.00 | 29.20 | C |
| ATOM | 8794 | CD2 | LEU C | 123 | −23.435 | 53.933 | −81.808 | 1.00 | 28.50 | C |
| ATOM | 8795 | C | LEU C | 123 | −27.782 | 53.465 | −81.261 | 1.00 | 33.34 | C |
| ATOM | 8796 | O | LEU C | 123 | −28.766 | 53.932 | −81.840 | 1.00 | 34.19 | O |
| ATOM | 8797 | N | ALA C | 124 | −27.825 | 52.959 | −80.032 | 1.00 | 35.85 | N |
| ATOM | 8798 | CA | ALA C | 124 | −28.987 | 53.103 | −79.171 | 1.00 | 38.62 | C |
| ATOM | 8799 | CB | ALA C | 124 | −29.035 | 51.968 | −78.155 | 1.00 | 38.02 | C |
| ATOM | 8800 | C | ALA C | 124 | −28.875 | 54.446 | −78.466 | 1.00 | 40.53 | C |
| ATOM | 8801 | O | ALA C | 124 | −27.964 | 54.644 | −77.666 | 1.00 | 44.94 | O |
| ATOM | 8802 | N | TYR C | 125 | −29.780 | 55.374 | −78.769 | 1.00 | 41.40 | N |
| ATOM | 8803 | CA | TYR C | 125 | −29.725 | 56.709 | −78.160 | 1.00 | 42.30 | C |
| ATOM | 8804 | CB | TYR C | 125 | −30.151 | 57.799 | −79.152 | 1.00 | 40.91 | C |
| ATOM | 8805 | CG | TYR C | 125 | −29.217 | 57.965 | −80.331 | 1.00 | 40.53 | C |
| ATOM | 8806 | CD1 | TYR C | 125 | −27.931 | 58.491 | −80.161 | 1.00 | 39.84 | C |
| ATOM | 8807 | CE1 | TYR C | 125 | −27.066 | 58.640 | −81.240 | 1.00 | 38.90 | C |
| ATOM | 8808 | CZ | TYR C | 125 | −27.484 | 58.267 | −82.513 | 1.00 | 38.48 | C |
| ATOM | 8809 | OH | TYR C | 125 | −26.631 | 58.418 | −83.580 | 1.00 | 36.52 | O |
| ATOM | 8810 | CE2 | TYR C | 125 | −28.758 | 57.747 | −82.711 | 1.00 | 39.63 | C |
| ATOM | 8811 | CD2 | TYR C | 125 | −29.617 | 57.599 | −81.624 | 1.00 | 40.31 | C |
| ATOM | 8812 | C | TYR C | 125 | −30.533 | 56.812 | −76.859 | 1.00 | 44.58 | C |
| ATOM | 8813 | O | TYR C | 125 | −31.759 | 56.627 | −75.855 | 1.00 | 44.83 | O |
| ATOM | 8814 | N | SER C | 126 | −29.826 | 57.102 | −75.761 | 1.00 | 45.59 | N |
| ATOM | 8815 | CA | SER C | 126 | −30.431 | 57.302 | −74.436 | 1.00 | 43.75 | C |
| ATOM | 8816 | CB | SER C | 126 | −29.397 | 57.050 | −73.333 | 1.00 | 41.82 | C |
| ATOM | 8817 | C | SER C | 126 | −31.004 | 58.712 | −74.303 | 1.00 | 42.91 | C |
| ATOM | 8818 | O | SER C | 126 | −30.502 | 59.659 | −74.914 | 1.00 | 42.27 | O |
| ATOM | 8819 | N | GLU C | 132 | −26.021 | 61.137 | −75.343 | 1.00 | 43.59 | N |
| ATOM | 8820 | CA | GLU C | 132 | −26.690 | 60.542 | −76.504 | 1.00 | 45.97 | C |
| ATOM | 8821 | CB | GLU C | 132 | −26.101 | 61.083 | −77.818 | 1.00 | 44.64 | C |
| ATOM | 8822 | C | GLU C | 132 | −26.729 | 58.987 | −76.500 | 1.00 | 48.41 | C |
| ATOM | 8823 | O | GLU C | 132 | −27.804 | 58.398 | −76.355 | 1.00 | 49.32 | O |
| ATOM | 8824 | N | ALA C | 133 | −25.575 | 58.328 | −76.654 | 1.00 | 46.65 | N |
| ATOM | 8825 | CA | ALA C | 133 | −25.551 | 56.863 | −76.792 | 1.00 | 43.70 | C |
| ATOM | 8826 | CB | ALA C | 133 | −25.494 | 56.477 | −78.260 | 1.00 | 43.89 | C |
| ATOM | 8827 | C | ALA C | 133 | −24.426 | 56.169 | −76.016 | 1.00 | 43.42 | C |
| ATOM | 8828 | O | ALA C | 133 | −23.261 | 56.563 | −76.103 | 1.00 | 44.48 | O |
| ATOM | 8829 | N | GLN C | 134 | −24.787 | 55.125 | −75.269 | 1.00 | 42.44 | N |
| ATOM | 8830 | CA | GLN C | 134 | −23.823 | 54.343 | −74.483 | 1.00 | 41.41 | C |
| ATOM | 8831 | CB | GLN C | 134 | −24.371 | 54.054 | −73.074 | 1.00 | 42.23 | C |
| ATOM | 8832 | CG | GLN C | 134 | −24.166 | 55.157 | −72.038 | 1.00 | 43.70 | C |
| ATOM | 8833 | CD | GLN C | 134 | −24.993 | 56.416 | −72.303 | 1.00 | 45.10 | C |
| ATOM | 8834 | OE1 | GLN C | 134 | −26.127 | 56.355 | −72.800 | 1.00 | 43.96 | O |
| ATOM | 8835 | NE2 | GLN C | 134 | −24.424 | 57.571 | −71.960 | 1.00 | 45.83 | N |
| ATOM | 8836 | C | GLN C | 134 | −23.469 | 53.021 | −75.171 | 1.00 | 40.10 | C |
| ATOM | 8837 | O | GLN C | 134 | −22.362 | 52.501 | −75.003 | 1.00 | 39.00 | O |
| ATOM | 8838 | N | PHE C | 135 | −24.422 | 52.482 | −75.933 | 1.00 | 38.05 | N |

-continued

| | | | | | | | | | | |
|---|---|---|---|---|---|---|---|---|---|---|
| \multicolumn{11}{|c|}{Atomic coordinates for CRBN:DDB1:Lenalidomide (Human protein)} |
| ATOM | 8839 | CA | PHE C | 135 | −24.280 | 51.166 | −76.558 | 1.00 | 36.00 | C |
| ATOM | 8840 | CB | PHE C | 135 | −25.036 | 50.103 | −75.744 | 1.00 | 36.42 | C |
| ATOM | 8841 | CG | PHE C | 135 | −24.577 | 49.966 | −74.320 | 1.00 | 36.89 | C |
| ATOM | 8842 | CD1 | PHE C | 135 | −23.482 | 49.164 | −73.999 | 1.00 | 38.10 | C |
| ATOM | 8843 | CE1 | PHE C | 135 | −23.070 | 49.018 | −72.679 | 1.00 | 38.43 | C |
| ATOM | 8844 | CZ | PHE C | 135 | −23.763 | 49.668 | −71.663 | 1.00 | 38.57 | C |
| ATOM | 8845 | CE2 | PHE C | 135 | −24.861 | 50.462 | −71.970 | 1.00 | 37.56 | C |
| ATOM | 8846 | CD2 | PHE C | 135 | −25.268 | 50.600 | −73.290 | 1.00 | 37.27 | C |
| ATOM | 8847 | C | PHE C | 135 | −24.818 | 51.155 | −77.996 | 1.00 | 34.21 | C |
| ATOM | 8848 | O | PHE C | 135 | −25.520 | 52.085 | −78.412 | 1.00 | 32.64 | O |
| ATOM | 8849 | N | GLY C | 136 | −24.507 | 50.087 | −78.734 | 1.00 | 32.17 | N |
| ATOM | 8850 | CA | GLY C | 136 | −25.071 | 49.871 | −80.067 | 1.00 | 31.45 | C |
| ATOM | 8851 | C | GLY C | 136 | −24.712 | 48.529 | −80.685 | 1.00 | 31.15 | C |
| ATOM | 8852 | O | GLY C | 136 | −24.252 | 47.618 | −79.994 | 1.00 | 31.58 | O |
| ATOM | 8853 | N | THR C | 137 | −24.921 | 48.403 | −81.993 | 1.00 | 30.40 | N |
| ATOM | 8854 | CA | THR C | 137 | −24.688 | 47.131 | −82.692 | 1.00 | 29.35 | C |
| ATOM | 8855 | CB | THR C | 137 | −25.987 | 46.296 | −82.776 | 1.00 | 29.68 | C |
| ATOM | 8856 | OG1 | THR C | 137 | −26.523 | 46.114 | −81.460 | 1.00 | 29.16 | O |
| ATOM | 8857 | CG2 | THR C | 137 | −25.732 | 44.925 | −83.391 | 1.00 | 29.83 | C |
| ATOM | 8858 | C | THR C | 137 | −24.084 | 47.328 | −84.096 | 1.00 | 28.10 | C |
| ATOM | 8859 | O | THR C | 137 | −24.502 | 48.215 | −84.844 | 1.00 | 26.91 | O |
| ATOM | 8860 | N | THR C | 138 | −23.084 | 46.516 | −84.434 | 1.00 | 26.94 | N |
| ATOM | 8861 | CA | THR C | 138 | −22.524 | 46.544 | −85.785 | 1.00 | 26.21 | C |
| ATOM | 8862 | CB | THR C | 138 | −21.148 | 45.822 | −85.915 | 1.00 | 25.19 | C |
| ATOM | 8863 | OG1 | THR C | 138 | −21.306 | 44.398 | −85.863 | 1.00 | 24.21 | O |
| ATOM | 8864 | CG2 | THR C | 138 | −20.203 | 46.261 | −84.816 | 1.00 | 25.25 | C |
| ATOM | 8865 | C | THR C | 138 | −23.543 | 45.967 | −86.753 | 1.00 | 26.12 | C |
| ATOM | 8866 | O | THR C | 138 | −24.200 | 44.972 | −86.461 | 1.00 | 26.31 | O |
| ATOM | 8867 | N | ALA C | 139 | −23.706 | 46.632 | −87.880 | 1.00 | 26.13 | N |
| ATOM | 8868 | CA | ALA C | 139 | −24.556 | 46.135 | −88.932 | 1.00 | 26.60 | C |
| ATOM | 8869 | CB | ALA C | 139 | −24.763 | 47.043 | −89.118 | 1.00 | 25.88 | C |
| ATOM | 8870 | C | ALA C | 139 | −23.714 | 46.050 | −90.198 | 1.00 | 27.70 | C |
| ATOM | 8871 | O | ALA C | 139 | −23.032 | 47.008 | −90.579 | 1.00 | 28.28 | O |
| ATOM | 8872 | N | GLU C | 140 | −23.758 | 44.882 | −90.827 | 1.00 | 28.49 | N |
| ATOM | 8873 | CA | GLU C | 140 | −22.934 | 44.545 | −91.978 | 1.00 | 29.34 | C |
| ATOM | 8874 | CB | GLU C | 140 | −22.323 | 43.172 | −91.727 | 1.00 | 31.67 | C |
| ATOM | 8875 | CG | GLU C | 140 | −21.433 | 42.603 | −92.817 | 1.00 | 34.37 | C |
| ATOM | 8876 | CD | GLU C | 140 | −20.921 | 41.219 | −92.444 | 1.00 | 36.96 | C |
| ATOM | 8877 | OE1 | GLU C | 140 | −19.697 | 41.071 | −92.186 | 1.00 | 38.02 | O |
| ATOM | 8878 | OE2 | GLU C | 140 | −21.757 | 40.286 | −92.371 | 1.00 | 37.76 | O |
| ATOM | 8879 | C | GLU C | 140 | −23.821 | 44.484 | −93.206 | 1.00 | 29.21 | C |
| ATOM | 8880 | O | GLU C | 140 | −24.877 | 43.851 | −93.176 | 1.00 | 29.56 | O |
| ATOM | 8881 | N | ILE C | 141 | −23.408 | 45.144 | −94.283 | 1.00 | 28.81 | N |
| ATOM | 8882 | CA | ILE C | 141 | −24.227 | 45.178 | −95.495 | 1.00 | 29.73 | C |
| ATOM | 8883 | CB | ILE C | 141 | −23.852 | 46.353 | −96.429 | 1.00 | 30.46 | C |
| ATOM | 8884 | CG1 | ILE C | 141 | −24.121 | 47.701 | −95.734 | 1.00 | 30.28 | C |
| ATOM | 8885 | CD1 | ILE C | 141 | −23.317 | 48.862 | −96.293 | 1.00 | 29.75 | C |
| ATOM | 8886 | CG2 | ILE C | 141 | −24.619 | 46.253 | −97.752 | 1.00 | 30.54 | C |
| ATOM | 8887 | C | ILE C | 141 | −24.134 | 43.858 | −96.255 | 1.00 | 30.00 | C |
| ATOM | 8888 | O | ILE C | 141 | −23.038 | 43.427 | −96.623 | 1.00 | 29.80 | O |
| ATOM | 8889 | N | TYR C | 142 | −25.283 | 43.221 | −96.482 | 1.00 | 30.40 | N |
| ATOM | 8890 | CA | TYR C | 142 | −25.323 | 41.957 | −97.218 | 1.00 | 31.32 | C |
| ATOM | 8891 | CB | TYR C | 142 | −26.014 | 40.862 | −96.398 | 1.00 | 29.57 | C |
| ATOM | 8892 | CG | TYR C | 142 | −27.506 | 41.004 | −96.187 | 1.00 | 28.51 | C |
| ATOM | 8893 | CD1 | TYR C | 142 | −28.406 | 40.748 | −97.220 | 1.00 | 27.98 | C |
| ATOM | 8894 | CE1 | TYR C | 142 | −29.779 | 40.856 | −97.020 | 1.00 | 28.15 | C |
| ATOM | 8895 | CZ | TYR C | 142 | −30.272 | 41.188 | −95.759 | 1.00 | 28.12 | C |
| ATOM | 8896 | OH | TYR C | 142 | −31.625 | 41.281 | −95.563 | 1.00 | 26.63 | O |
| ATOM | 8897 | CE2 | TYR C | 142 | −29.399 | 41.430 | −94.709 | 1.00 | 28.61 | C |
| ATOM | 8898 | CD2 | TYR C | 142 | −28.023 | 41.332 | −94.927 | 1.00 | 28.82 | C |
| ATOM | 8899 | C | TYR C | 142 | −25.901 | 42.058 | −98.640 | 1.00 | 33.15 | C |
| ATOM | 8900 | O | TYR C | 142 | −25.771 | 41.128 | −99.438 | 1.00 | 33.72 | O |
| ATOM | 8901 | N | ALA C | 143 | −26.535 | 43.191 | −98.937 | 1.00 | 35.54 | N |
| ATOM | 8902 | CA | ALA C | 143 | −27.049 | 43.497 | −100.278 | 1.00 | 36.57 | C |
| ATOM | 8903 | CB | ALA C | 143 | −28.355 | 42.761 | −100.550 | 1.00 | 36.21 | C |
| ATOM | 8904 | C | ALA C | 143 | −27.221 | 45.010 | −100.464 | 1.00 | 36.90 | C |
| ATOM | 8905 | O | ALA C | 143 | −27.482 | 45.746 | −99.507 | 1.00 | 35.45 | O |
| ATOM | 8906 | N | TYR C | 144 | −27.081 | 45.454 | −101.710 | 1.00 | 38.42 | N |
| ATOM | 8907 | CA | TYR C | 144 | −26.893 | 46.862 | −102.028 | 1.00 | 40.42 | C |
| ATOM | 8908 | CB | TYR C | 144 | −25.449 | 47.278 | −101.657 | 1.00 | 43.46 | C |
| ATOM | 8909 | CG | TYR C | 144 | −24.820 | 48.338 | −102.536 | 1.00 | 47.25 | C |
| ATOM | 8910 | CD1 | TYR C | 144 | −24.117 | 47.987 | −103.693 | 1.00 | 48.36 | C |
| ATOM | 8911 | CE1 | TYR C | 144 | −23.545 | 48.953 | −104.508 | 1.00 | 51.79 | C |
| ATOM | 8912 | CZ | TYR C | 144 | −23.657 | 50.300 | −104.161 | 1.00 | 53.84 | C |
| ATOM | 8913 | OH | TYR C | 144 | −23.090 | 51.273 | −104.973 | 1.00 | 55.41 | O |
| ATOM | 8914 | CE2 | TYR C | 144 | −24.336 | 50.670 | −103.006 | 1.00 | 52.20 | C |
| ATOM | 8915 | CD2 | TYR C | 144 | −24.908 | 49.691 | −102.202 | 1.00 | 50.07 | C |

-continued

| | | | | | | | | | | |
|---|---|---|---|---|---|---|---|---|---|---|
| \multicolumn{11}{l}{Atomic coordinates for CRBN:DDB1:Lenalidomide (Human protein)} |
| ATOM | 8916 | C | TYR C | 144 | −27.205 | 47.117 | −103.507 | 1.00 | 39.96 | C |
| ATOM | 8917 | O | TYR C | 144 | −26.762 | 46.370 | −104.375 | 1.00 | 38.42 | O |
| ATOM | 8918 | N | ARG C | 145 | −28.001 | 48.150 | −103.779 | 1.00 | 42.11 | N |
| ATOM | 8919 | CA | ARG C | 145 | −28.187 | 48.659 | −105.146 | 1.00 | 43.87 | C |
| ATOM | 8920 | CB | ARG C | 145 | −29.554 | 48.272 | −105.721 | 1.00 | 46.02 | C |
| ATOM | 8921 | CG | ARG C | 145 | −29.481 | 47.611 | −107.099 | 1.00 | 50.21 | C |
| ATOM | 8922 | CD | ARG C | 145 | −30.379 | 48.242 | −108.173 | 1.00 | 54.66 | C |
| ATOM | 8923 | NE | ARG C | 145 | −31.570 | 48.930 | −107.658 | 1.00 | 57.11 | N |
| ATOM | 8924 | CZ | ARG C | 145 | −32.703 | 48.334 | −107.289 | 1.00 | 57.24 | C |
| ATOM | 8925 | NH1 | ARG C | 145 | −33.711 | 49.069 | −106.835 | 1.00 | 58.20 | N |
| ATOM | 8926 | NH2 | ARG C | 145 | −32.830 | 47.012 | −107.353 | 1.00 | 57.69 | N |
| ATOM | 8927 | C | ARG C | 145 | −28.031 | 50.177 | −105.161 | 1.00 | 43.43 | C |
| ATOM | 8928 | O | ARG C | 145 | −28.531 | 50.871 | −104.267 | 1.00 | 43.07 | O |
| ATOM | 8929 | N | GLU C | 146 | −27.319 | 50.683 | −106.166 | 1.00 | 43.36 | N |
| ATOM | 8930 | CA | GLU C | 146 | −27.093 | 52.117 | −106.310 | 1.00 | 45.09 | C |
| ATOM | 8931 | CB | GLU C | 146 | −25.593 | 52.449 | −106.293 | 1.00 | 43.95 | C |
| ATOM | 8932 | C | GLU C | 146 | −27.720 | 52.609 | −107.602 | 1.00 | 46.46 | C |
| ATOM | 8933 | O | GLU C | 146 | −27.135 | 52.459 | −108.681 | 1.00 | 49.04 | O |
| ATOM | 8934 | N | GLU C | 147 | −28.916 | 53.183 | −107.496 | 1.00 | 46.21 | N |
| ATOM | 8935 | CA | GLU C | 147 | −29.553 | 53.804 | −408.652 | 1.00 | 44.75 | C |
| ATOM | 8936 | CB | GLU C | 147 | −31.065 | 53.514 | −108.709 | 1.00 | 45.96 | C |
| ATOM | 8937 | CG | GLU C | 147 | −31.924 | 54.199 | −107.658 | 1.00 | 45.13 | C |
| ATOM | 8938 | CD | GLU C | 147 | −33.232 | 53.467 | −107.419 | 1.00 | 46.42 | C |
| ATOM | 8939 | OE1 | GLU C | 147 | −33.192 | 52.220 | −107.276 | 1.00 | 47.50 | O |
| ATOM | 8940 | OE2 | GLU C | 147 | −34.295 | 54.131 | −107.363 | 1.00 | 43.58 | O |
| ATOM | 8941 | C | GLU C | 147 | −29.248 | 55.295 | −108.750 | 1.00 | 41.87 | C |
| ATOM | 8942 | O | GLU C | 147 | −29.404 | 56.047 | −107.788 | 1.00 | 38.52 | O |
| ATOM | 8943 | N | GLN C | 148 | −28.759 | 55.687 | −109.920 | 1.00 | 41.20 | N |
| ATOM | 8944 | CA | GLN C | 148 | −28.613 | 57.081 | −110.277 | 1.00 | 40.39 | C |
| ATOM | 8945 | CB | GLN C | 148 | −27.132 | 57.519 | −110.269 | 1.00 | 41.12 | C |
| ATOM | 8946 | CG | GLN C | 148 | −26.246 | 56.980 | −111.385 | 1.00 | 43.11 | C |
| ATOM | 8947 | CD | GLN C | 148 | −25.808 | 55.547 | −111.168 | 1.00 | 44.36 | C |
| ATOM | 8948 | OE1 | GLN C | 148 | −24.765 | 55.291 | −110.562 | 1.00 | 45.19 | O |
| ATOM | 8949 | NE2 | GLN C | 148 | −26.601 | 54.601 | −111.665 | 1.00 | 44.28 | N |
| ATOM | 8950 | C | GLN C | 148 | −29.320 | 57.313 | −111.616 | 1.00 | 39.24 | C |
| ATOM | 8951 | O | GLN C | 148 | −28.692 | 57.519 | −112.650 | 1.00 | 38.85 | O |
| ATOM | 8952 | N | ASP C | 149 | −30.648 | 57.235 | −111.571 | 1.00 | 39.67 | N |
| ATOM | 8953 | CA | ASP C | 149 | −31.502 | 57.436 | −112.743 | 1.00 | 40.69 | C |
| ATOM | 8954 | CB | ASP C | 149 | −32.517 | 56.292 | −112.895 | 1.00 | 43.61 | C |
| ATOM | 8955 | CG | ASP C | 149 | −31.979 | 54.952 | −112.386 | 1.00 | 49.87 | C |
| ATOM | 8956 | OD1 | ASP C | 149 | −30.794 | 54.620 | −112.650 | 1.00 | 52.14 | O |
| ATOM | 8957 | OD2 | ASP C | 149 | −32.743 | 54.231 | −111.705 | 1.00 | 52.17 | O |
| ATOM | 8958 | C | ASP C | 149 | −32.217 | 58.772 | −112.600 | 1.00 | 38.92 | C |
| ATOM | 8959 | O | ASP C | 149 | −32.661 | 59.134 | −111.502 | 1.00 | 37.90 | O |
| ATOM | 8960 | N | PHE C | 150 | −32.327 | 59.493 | −113.718 | 1.00 | 36.69 | N |
| ATOM | 8961 | CA | PHE C | 150 | −32.687 | 60.917 | −113.728 | 1.00 | 35.46 | C |
| ATOM | 8962 | CB | PHE C | 150 | −34.036 | 61.169 | −113.042 | 1.00 | 33.39 | C |
| ATOM | 8963 | CG | PHE C | 150 | −35.157 | 60.334 | −113.583 | 1.00 | 33.19 | C |
| ATOM | 8964 | CD1 | PHE C | 150 | −35.706 | 60.603 | −114.834 | 1.00 | 33.45 | C |
| ATOM | 8965 | CE1 | PHE C | 150 | −36.742 | 59.823 | −115.335 | 1.00 | 33.27 | C |
| ATOM | 8966 | CZ | PHE C | 150 | −37.246 | 58.768 | −114.583 | 1.00 | 32.45 | C |
| ATOM | 8967 | CE2 | PHE C | 150 | −36.716 | 58.497 | −113.335 | 1.00 | 32.32 | C |
| ATOM | 8968 | CD2 | PHE C | 150 | −35.677 | 59.278 | −112.839 | 1.00 | 33.23 | C |
| ATOM | 8969 | C | PHE C | 150 | −31.575 | 61.770 | −113.097 | 1.00 | 36.25 | C |
| ATOM | 8970 | O | PHE C | 150 | −31.767 | 62.957 | −112.814 | 1.00 | 36.43 | O |
| ATOM | 8971 | N | GLY C | 151 | −30.409 | 61.155 | −112.893 | 1.00 | 36.58 | N |
| ATOM | 8972 | CA | GLY C | 151 | −29.270 | 61.811 | −112.246 | 1.00 | 34.90 | C |
| ATOM | 8973 | C | GLY C | 151 | −29.448 | 62.044 | −110.755 | 1.00 | 33.84 | C |
| ATOM | 8974 | O | GLY C | 151 | −28.720 | 62.848 | −110.160 | 1.00 | 33.30 | O |
| ATOM | 8975 | N | ILE C | 152 | −30.429 | 61.363 | −110.160 | 1.00 | 32.13 | N |
| ATOM | 8976 | CA | ILE C | 152 | −30.637 | 61.406 | −108.721 | 1.00 | 31.89 | C |
| ATOM | 8977 | CB | ILE C | 152 | −32.127 | 61.493 | −108.345 | 1.00 | 30.79 | C |
| ATOM | 8978 | CG1 | ILE C | 152 | −32.856 | 62.548 | −109.186 | 1.00 | 30.30 | C |
| ATOM | 8979 | CD1 | ILE C | 152 | −34.352 | 62.622 | −108.930 | 1.00 | 29.31 | C |
| ATOM | 8980 | CG2 | ILE C | 152 | −32.278 | 61.755 | −106.849 | 1.00 | 30.35 | C |
| ATOM | 8981 | C | ILE C | 152 | −30.091 | 60.116 | −108.135 | 1.00 | 33.80 | C |
| ATOM | 8982 | O | ILE C | 152 | −30.605 | 59.035 | −108.439 | 1.00 | 35.82 | O |
| ATOM | 8983 | N | GLU C | 153 | −29.063 | 60.232 | −107.290 | 1.00 | 34.84 | N |
| ATOM | 8984 | CA | GLU C | 153 | −28.411 | 59.065 | −106.684 | 1.00 | 34.79 | C |
| ATOM | 8985 | CB | GLU C | 153 | −26.949 | 59.353 | −106.363 | 1.00 | 36.31 | C |
| ATOM | 8986 | CG | GLU C | 153 | −26.131 | 59.739 | −107.582 | 1.00 | 39.82 | C |
| ATOM | 8987 | CD | GLU C | 153 | −24.649 | 59.825 | −107.290 | 1.00 | 43.37 | C |
| ATOM | 8988 | OE1 | GLU C | 153 | −24.243 | 59.583 | −106.123 | 1.00 | 44.85 | O |
| ATOM | 8989 | OE2 | GLU C | 153 | −23.889 | 60.137 | −108.234 | 1.00 | 44.61 | O |
| ATOM | 8990 | C | GLU C | 153 | −29.134 | 58.595 | −105.438 | 1.00 | 33.65 | C |
| ATOM | 8991 | O | GLU C | 153 | −29.287 | 59.343 | −104.476 | 1.00 | 33.56 | O |
| ATOM | 8992 | N | ILE C | 154 | −29.604 | 57.355 | −105.483 | 1.00 | 32.43 | N |

-continued

| | | Atomic coordinates for CRBN:DDB1:Lenalidomide (Human protein) | | | | | | | |
|---|---|---|---|---|---|---|---|---|---|
| ATOM | 8993 | CA | ILE C | 154 | −30.215 | 56.718 | −104.337 | 1.00 | 31.76 | C |
| ATOM | 8994 | CB | ILE C | 154 | −31.673 | 56.273 | −104.623 | 1.00 | 32.87 | C |
| ATOM | 8995 | CG1 | ILE C | 154 | −32.435 | 57.308 | −105.488 | 1.00 | 32.76 | C |
| ATOM | 8996 | CD1 | ILE C | 154 | −32.728 | 58.639 | −104.826 | 1.00 | 32.18 | C |
| ATOM | 8997 | CG2 | ILE C | 154 | −32.405 | 55.880 | −103.330 | 1.00 | 32.47 | C |
| ATOM | 8998 | C | ILE C | 154 | −29.398 | 55.479 | −104.034 | 1.00 | 31.39 | C |
| ATOM | 8999 | O | ILE C | 154 | −28.976 | 54.764 | −104.941 | 1.00 | 31.52 | O |
| ATOM | 9000 | N | VAL C | 155 | −29.164 | 55.235 | −102.755 | 1.00 | 31.41 | N |
| ATOM | 9001 | CA | VAL C | 155 | −28.539 | 53.995 | −102.324 | 1.00 | 30.94 | C |
| ATOM | 9002 | CB | VAL C | 155 | −27.162 | 54.241 | −101.667 | 1.00 | 31.31 | C |
| ATOM | 9003 | CG1 | VAL C | 155 | −26.637 | 52.973 | −101.007 | 1.00 | 31.08 | C |
| ATOM | 9004 | CG2 | VAL C | 155 | −26.166 | 54.747 | −102.707 | 1.00 | 30.96 | C |
| ATOM | 9005 | C | VAL C | 155 | −29.484 | 53.242 | −101.394 | 1.00 | 30.09 | C |
| ATOM | 9006 | O | VAL C | 155 | −29.902 | 53.759 | −100.354 | 1.00 | 29.69 | O |
| ATOM | 9007 | N | LYS C | 156 | −29.840 | 52.031 | −101.808 | 1.00 | 29.50 | N |
| ATOM | 9008 | CA | LYS C | 156 | −30.680 | 51.150 | −101.014 | 1.00 | 29.58 | C |
| ATOM | 9009 | CB | LYS C | 156 | −31.859 | 50.642 | −101.845 | 1.00 | 30.39 | C |
| ATOM | 9010 | CG | LYS C | 156 | −32.816 | 51.732 | −102.324 | 1.00 | 31.48 | C |
| ATOM | 9011 | CD | LYS C | 156 | −33.488 | 51.348 | −103.640 | 1.00 | 31.80 | C |
| ATOM | 9012 | CE | LYS C | 156 | −34.680 | 52.240 | −103.951 | 1.00 | 32.18 | C |
| ATOM | 9013 | NZ | LYS C | 156 | −35.867 | 51.951 | −103.089 | 1.00 | 32.74 | N |
| ATOM | 9014 | C | LYS C | 156 | −29.823 | 49.984 | −100.546 | 1.00 | 29.44 | C |
| ATOM | 9015 | O | LYS C | 156 | −29.136 | 49.355 | −101.356 | 1.00 | 29.69 | O |
| ATOM | 9016 | N | VAL C | 157 | −29.831 | 49.725 | −99.238 | 1.00 | 28.28 | N |
| ATOM | 9017 | CA | VAL C | 157 | −29.036 | 48.637 | −98.667 | 1.00 | 27.93 | C |
| ATOM | 9018 | CB | VAL C | 157 | −27.736 | 49.131 | −97.955 | 1.00 | 27.95 | C |
| ATOM | 9019 | CG1 | VAL C | 157 | −26.861 | 49.935 | −98.903 | 1.00 | 28.20 | C |
| ATOM | 9020 | CG2 | VAL C | 157 | −28.043 | 49.940 | −96.703 | 1.00 | 27.87 | C |
| ATOM | 9021 | C | VAL C | 157 | −29.849 | 47.797 | −97.700 | 1.00 | 27.58 | C |
| ATOM | 9022 | O | VAL C | 157 | −30.767 | 48.299 | −97.052 | 1.00 | 27.79 | O |
| ATOM | 9023 | N | LYS C | 158 | −29.506 | 46.514 | −97.615 | 1.00 | 27.25 | N |
| ATOM | 9024 | CA | LYS C | 158 | −30.030 | 45.636 | −96.570 | 1.00 | 26.00 | C |
| ATOM | 9025 | CB | LYS C | 158 | −30.719 | 44.415 | −97.169 | 1.00 | 25.56 | C |
| ATOM | 9026 | CG | LYS C | 158 | −31.850 | 44.722 | −98.128 | 1.00 | 25.25 | C |
| ATOM | 9027 | CD | LYS C | 158 | −32.649 | 43.464 | −98.379 | 1.00 | 25.10 | C |
| ATOM | 9028 | CE | LYS C | 158 | −33.308 | 43.465 | −99.740 | 1.00 | 24.37 | C |
| ATOM | 9029 | NZ | LYS C | 158 | −34.052 | 42.187 | −99.868 | 1.00 | 24.08 | N |
| ATOM | 9030 | C | LYS C | 158 | −28.880 | 45.183 | −95.694 | 1.00 | 25.47 | C |
| ATOM | 9031 | O | LYS C | 158 | −28.013 | 44.438 | −96.141 | 1.00 | 25.56 | O |
| ATOM | 9032 | N | ALA C | 159 | −28.863 | 45.656 | −94.454 | 1.00 | 25.65 | N |
| ATOM | 9033 | CA | ALA C | 159 | −27.842 | 45.259 | −93.479 | 1.00 | 25.33 | C |
| ATOM | 9034 | CB | ALA C | 159 | −27.205 | 46.486 | −92.830 | 1.00 | 24.64 | C |
| ATOM | 9035 | C | ALA C | 159 | −28.420 | 44.317 | −92.416 | 1.00 | 24.69 | C |
| ATOM | 9036 | O | ALA C | 159 | −29.635 | 44.219 | −92.246 | 1.00 | 24.05 | O |
| ATOM | 9037 | N | ILE C | 160 | −27.530 | 43.630 | −91.711 | 1.00 | 24.44 | N |
| ATOM | 9038 | CA | ILE C | 160 | −27.908 | 42.685 | −90.672 | 1.00 | 24.38 | C |
| ATOM | 9039 | CB | ILE C | 160 | −27.667 | 41.226 | −91.141 | 1.00 | 25.17 | C |
| ATOM | 9040 | CG1 | ILE C | 160 | −27.806 | 40.234 | −89.978 | 1.00 | 25.46 | C |
| ATOM | 9041 | CD1 | ILE C | 160 | −28.914 | 39.228 | −90.175 | 1.00 | 25.97 | C |
| ATOM | 9042 | CG2 | ILE C | 160 | −26.309 | 41.073 | −91.825 | 1.00 | 25.25 | C |
| ATOM | 9043 | C | ILE C | 160 | −27.089 | 42.995 | −89.421 | 1.00 | 23.89 | C |
| ATOM | 9044 | O | ILE C | 160 | −25.867 | 43.085 | −89.489 | 1.00 | 24.71 | O |
| ATOM | 9045 | N | GLY C | 161 | −27.755 | 43.182 | −88.287 | 1.00 | 23.07 | N |
| ATOM | 9046 | CA | GLY C | 161 | −27.051 | 43.395 | −87.026 | 1.00 | 23.38 | C |
| ATOM | 9047 | C | GLY C | 161 | −26.129 | 42.248 | −86.647 | 1.00 | 23.57 | C |
| ATOM | 9048 | O | GLY C | 161 | −26.519 | 41.089 | −86.703 | 1.00 | 23.90 | O |
| ATOM | 9049 | N | ARG C | 162 | −24.905 | 42.571 | −86.249 | 1.00 | 24.16 | N |
| ATOM | 9050 | CA | ARG C | 162 | −23.898 | 41.545 | −85.976 | 1.00 | 25.00 | C |
| ATOM | 9051 | CB | ARG C | 162 | −22.720 | 41.685 | −86.948 | 1.00 | 26.49 | C |
| ATOM | 9052 | CG | ARG C | 162 | −23.026 | 41.282 | −88.388 | 1.00 | 27.30 | C |
| ATOM | 9053 | CD | ARG C | 162 | −22.703 | 39.815 | −88.624 | 1.00 | 29.10 | C |
| ATOM | 9054 | NE | ARG C | 162 | −23.898 | 38.998 | −88.825 | 1.00 | 29.73 | N |
| ATOM | 9055 | CZ | ARG C | 162 | −24.210 | 38.399 | −89.975 | 1.00 | 30.39 | C |
| ATOM | 9056 | NH1 | ARG C | 162 | −23.421 | 38.513 | −91.043 | 1.00 | 29.87 | N |
| ATOM | 9057 | NH2 | ARG C | 162 | −25.314 | 37.677 | −90.060 | 1.00 | 31.06 | N |
| ATOM | 9058 | C | ARG C | 162 | −23.401 | 41.521 | −84.523 | 1.00 | 24.40 | C |
| ATOM | 9059 | O | ARG C | 162 | −23.617 | 40.549 | −83.807 | 1.00 | 23.65 | O |
| ATOM | 9060 | N | GLN C | 163 | −22.750 | 42.591 | −84.087 | 1.00 | 24.57 | N |
| ATOM | 9061 | CA | GLN C | 163 | −22.120 | 42.595 | −82.766 | 1.00 | 25.63 | C |
| ATOM | 9062 | CB | GLN C | 163 | −20.609 | 42.605 | −82.914 | 1.00 | 25.11 | C |
| ATOM | 9063 | CG | GLN C | 163 | −20.078 | 41.415 | −83.667 | 1.00 | 25.11 | C |
| ATOM | 9064 | CD | GLN C | 163 | −18.585 | 41.347 | −83.603 | 1.00 | 25.26 | C |
| ATOM | 9065 | OE1 | GLN C | 163 | −17.903 | 41.573 | −84.600 | 1.00 | 26.94 | O |
| ATOM | 9066 | NE2 | GLN C | 163 | −18.059 | 41.054 | −82.425 | 1.00 | 25.03 | N |
| ATOM | 9067 | C | GLN C | 163 | −22.541 | 43.738 | −81.849 | 1.00 | 26.46 | C |
| ATOM | 9068 | O | GLN C | 163 | −22.758 | 44.870 | −82.295 | 1.00 | 26.85 | O |
| ATOM | 9069 | N | ARG C | 164 | −22.626 | 43.445 | −80.558 | 1.00 | 26.40 | N |

-continued

| | | | | Atomic coordinates for CRBN:DDB1:Lenalidomide (Human protein) | | | | | |
|---|---|---|---|---|---|---|---|---|---|
| ATOM | 9070 | CA | ARG C | 164 | −22.943 | 44.477 | −79.583 | 1.00 | 27.25 | C |
| ATOM | 9071 | CB | ARG C | 164 | −23.707 | 43.881 | −78.406 | 1.00 | 26.39 | C |
| ATOM | 9072 | CG | ARG C | 164 | −24.895 | 43.028 | −78.810 | 1.00 | 25.56 | C |
| ATOM | 9073 | CD | ARG C | 164 | −25.554 | 42.384 | −77.603 | 1.00 | 26.18 | C |
| ATOM | 9074 | NE | ARG C | 164 | −24.654 | 41.491 | −76.882 | 1.00 | 26.53 | N |
| ATOM | 9075 | CZ | ARG C | 164 | −24.062 | 41.787 | −75.727 | 1.00 | 27.04 | C |
| ATOM | 9076 | NH1 | ARG C | 164 | −24.270 | 42.959 | −75.140 | 1.00 | 26.44 | N |
| ATOM | 9077 | NH2 | ARG C | 164 | −23.254 | 40.904 | −75.155 | 1.00 | 27.72 | N |
| ATOM | 9078 | C | ARG C | 164 | −21.667 | 45.175 | −79.105 | 1.00 | 28.26 | C |
| ATOM | 9079 | O | ARG C | 164 | −20.620 | 44.543 | −78.936 | 1.00 | 28.97 | O |
| ATOM | 9080 | N | PHE C | 165 | −21.747 | 46.482 | −78.895 | 1.00 | 29.29 | N |
| ATOM | 9081 | CA | PHE C | 165 | −20.581 | 47.226 | −78.435 | 1.00 | 30.05 | C |
| ATOM | 9082 | CB | PHE C | 165 | −19.810 | 47.827 | −79.614 | 1.00 | 29.79 | C |
| ATOM | 9083 | CG | PHE C | 165 | −20.638 | 48.708 | −80.510 | 1.00 | 29.73 | C |
| ATOM | 9084 | CD1 | PHE C | 165 | −21.121 | 49.934 | −80.065 | 1.00 | 29.67 | C |
| ATOM | 9085 | CE1 | PHE C | 165 | −21.872 | 50.747 | −80.894 | 1.00 | 29.44 | C |
| ATOM | 9086 | CZ | PHE C | 165 | −22.146 | 50.351 | −82.187 | 1.00 | 29.09 | C |
| ATOM | 9087 | CE2 | PHE C | 165 | −21.661 | 49.141 | −82.649 | 1.00 | 29.88 | C |
| ATOM | 9088 | CD2 | PHE C | 165 | −20.908 | 48.327 | −81.814 | 1.00 | 30.04 | C |
| ATOM | 9089 | C | PHE C | 165 | −20.903 | 48.299 | −77.407 | 1.00 | 30.89 | C |
| ATOM | 9090 | O | PHE C | 165 | −22.033 | 48.791 | −77.334 | 1.00 | 31.38 | O |
| ATOM | 9091 | N | LYS C | 166 | −19.886 | 48.640 | −76.620 | 1.00 | 32.19 | N |
| ATOM | 9092 | CA | LYS C | 166 | −19.914 | 49.730 | −75.648 | 1.00 | 33.48 | C |
| ATOM | 9093 | CB | LYS C | 166 | −19.151 | 49.285 | −74.391 | 1.00 | 34.00 | C |
| ATOM | 9094 | CG | LYS C | 166 | −18.925 | 50.319 | −73.298 | 1.00 | 35.23 | C |
| ATOM | 9095 | CD | LYS C | 166 | −17.575 | 50.062 | −72.624 | 1.00 | 36.59 | C |
| ATOM | 9096 | CE | LYS C | 166 | −17.667 | 49.955 | −71.102 | 1.00 | 36.25 | C |
| ATOM | 9097 | NZ | LYS C | 166 | −17.831 | 51.270 | −70.431 | 1.00 | 36.47 | N |
| ATOM | 9098 | C | LYS C | 166 | −19.246 | 50.954 | −76.302 | 1.00 | 34.69 | C |
| ATOM | 9099 | O | LYS C | 166 | −18.168 | 50.844 | −76.903 | 1.00 | 34.97 | O |
| ATOM | 9100 | N | VAL C | 167 | −19.903 | 52.107 | −76.215 | 1.00 | 35.40 | N |
| ATOM | 9101 | CA | VAL C | 167 | −19.360 | 53.345 | −76.776 | 1.00 | 35.13 | C |
| ATOM | 9102 | CB | VAL C | 167 | −20.466 | 54.414 | −76.986 | 1.00 | 35.52 | C |
| ATOM | 9103 | CG1 | VAL C | 167 | −19.868 | 55.762 | −77.384 | 1.00 | 34.46 | C |
| ATOM | 9104 | CG2 | VAL C | 167 | −21.484 | 53.942 | −78.018 | 1.00 | 34.56 | C |
| ATOM | 9105 | C | VAL C | 167 | −18.292 | 53.885 | −75.838 | 1.00 | 34.38 | C |
| ATOM | 9106 | O | VAL C | 167 | −18.495 | 53.932 | −74.635 | 1.00 | 33.43 | O |
| ATOM | 9107 | N | LEU C | 168 | −17.150 | 54.268 | −76.392 | 1.00 | 35.94 | N |
| ATOM | 9108 | CA | LEU C | 168 | −16.124 | 54.947 | −75.614 | 1.00 | 37.92 | C |
| ATOM | 9109 | CB | LEU C | 168 | −14.759 | 54.283 | −75.805 | 1.00 | 37.39 | C |
| ATOM | 9110 | CG | LEU C | 168 | −14.734 | 52.759 | −75.598 | 1.00 | 36.53 | C |
| ATOM | 9111 | CD1 | LEU C | 168 | −13.527 | 52.134 | −76.275 | 1.00 | 36.10 | C |
| ATOM | 9112 | CD2 | LEU C | 168 | −14.782 | 52.370 | −74.126 | 1.00 | 36.84 | C |
| ATOM | 9113 | C | LEU C | 168 | −16.116 | 56.441 | −75.955 | 1.00 | 40.12 | C |
| ATOM | 9114 | O | LEU C | 168 | −16.571 | 57.247 | −75.146 | 1.00 | 41.66 | O |
| ATOM | 9115 | N | GLU C | 169 | −15.648 | 56.810 | −77.149 | 1.00 | 41.72 | N |
| ATOM | 9116 | CA | GLU C | 169 | −15.775 | 58.202 | −77.611 | 1.00 | 43.81 | C |
| ATOM | 9117 | CB | GLU C | 169 | −14.410 | 58.903 | −77.707 | 1.00 | 45.99 | C |
| ATOM | 9118 | CG | GLU C | 169 | −14.503 | 60.430 | −77.655 | 1.00 | 48.51 | C |
| ATOM | 9119 | CD | GLU C | 169 | −13.290 | 61.139 | −78.246 | 1.00 | 50.65 | C |
| ATOM | 9120 | OE1 | GLU C | 169 | −12.150 | 60.804 | −77.856 | 1.00 | 53.21 | O |
| ATOM | 9121 | OE2 | GLU C | 169 | −13.474 | 62.047 | −79.090 | 1.00 | 49.34 | O |
| ATOM | 9122 | C | GLU C | 169 | −16.536 | 58.342 | −78.932 | 1.00 | 44.72 | C |
| ATOM | 9123 | O | GLU C | 169 | −16.589 | 57.413 | −79.741 | 1.00 | 44.57 | O |
| ATOM | 9124 | N | LEU C | 170 | −17.112 | 59.524 | −79.136 | 1.00 | 46.40 | N |
| ATOM | 9125 | CA | LEU C | 170 | −17.861 | 59.848 | −80.348 | 1.00 | 47.12 | C |
| ATOM | 9126 | CB | LEU C | 170 | −19.354 | 59.899 | −80.037 | 1.00 | 45.61 | C |
| ATOM | 9127 | CG | LEU C | 170 | −20.232 | 58.898 | −80.767 | 1.00 | 44.60 | C |
| ATOM | 9128 | CD1 | LEU C | 170 | −21.443 | 58.565 | −79.912 | 1.00 | 44.62 | C |
| ATOM | 9129 | CD2 | LEU C | 170 | −20.644 | 59.474 | −82.119 | 1.00 | 44.18 | C |
| ATOM | 9130 | C | LEU C | 170 | −17.417 | 61.172 | −80.976 | 1.00 | 48.21 | C |
| ATOM | 9131 | O | LEU C | 170 | −17.845 | 62.247 | −80.545 | 1.00 | 47.65 | O |
| ATOM | 9132 | N | GLU C | 171 | −16.569 | 61.083 | −82.001 | 1.00 | 50.90 | N |
| ATOM | 9133 | CA | GLU C | 171 | −16.040 | 62.272 | −82.693 | 1.00 | 52.69 | C |
| ATOM | 9134 | CB | GLU C | 171 | −14.488 | 62.267 | −82.715 | 1.00 | 53.99 | C |
| ATOM | 9135 | CG | GLU C | 171 | −13.819 | 61.165 | −83.549 | 1.00 | 53.64 | C |
| ATOM | 9136 | CD | GLU C | 171 | −13.494 | 59.893 | −82.765 | 1.00 | 53.43 | C |
| ATOM | 9137 | OE1 | GLU C | 171 | −14.242 | 59.531 | −81.828 | 1.00 | 54.53 | O |
| ATOM | 9138 | OE2 | GLU C | 171 | −12.489 | 59.232 | −83.104 | 1.00 | 52.39 | O |
| ATOM | 9139 | C | GLU C | 171 | −16.638 | 62.471 | −84.103 | 1.00 | 52.83 | C |
| ATOM | 9140 | O | GLU C | 171 | −17.198 | 61.531 | −84.691 | 1.00 | 52.05 | O |
| ATOM | 9141 | N | ARG C | 172 | −16.528 | 63.698 | −84.623 | 1.00 | 52.92 | N |
| ATOM | 9142 | CA | ARG C | 172 | −17.066 | 64.053 | −85.948 | 1.00 | 51.11 | C |
| ATOM | 9143 | CB | ARG C | 172 | −18.264 | 65.006 | −85.825 | 1.00 | 50.87 | C |
| ATOM | 9144 | CG | ARG C | 172 | −19.466 | 64.419 | −85.090 | 1.00 | 52.76 | C |
| ATOM | 9145 | CD | ARG C | 172 | −20.525 | 65.463 | −84.750 | 1.00 | 53.58 | C |
| ATOM | 9146 | NE | ARG C | 172 | −19.957 | 66.682 | −84.163 | 1.00 | 55.14 | N |

-continued

| Atomic coordinates for CRBN:DDB1:Lenalidomide (Human protein) | | | | | | | | | |
|---|---|---|---|---|---|---|---|---|---|
| ATOM | 9147 | CZ | ARG C | 172 | −20.139 | 67.914 | −84.643 | 1.00 | 55.64 | C |
| ATOM | 9148 | NH1 | ARG C | 172 | −20.898 | 68.117 | −85.716 | 1.00 | 56.60 | N |
| ATOM | 9149 | NH2 | ARG C | 172 | −19.573 | 68.954 | −84.042 | 1.00 | 54.00 | N |
| ATOM | 9150 | C | ARG C | 172 | −15.995 | 64.673 | −86.835 | 1.00 | 48.04 | C |
| ATOM | 9151 | O | ARG C | 172 | −16.096 | 64.633 | −88.058 | 1.00 | 45.64 | O |
| ATOM | 9152 | N | GLY C | 176 | −20.324 | 65.745 | −92.321 | 1.00 | 49.15 | N |
| ATOM | 9153 | CA | ILE C | 177 | −21.169 | 65.507 | −91.148 | 1.00 | 51.24 | C |
| ATOM | 9154 | C | ILE C | 177 | −21.411 | 64.033 | −90.836 | 1.00 | 51.21 | C |
| ATOM | 9155 | O | ILE C | 177 | −22.501 | 63.654 | −90.398 | 1.00 | 50.27 | O |
| ATOM | 9156 | N | ILE C | 177 | −20.396 | 63.202 | −91.069 | 1.00 | 50.57 | N |
| ATOM | 9157 | CA | ILE C | 177 | −20.480 | 61.771 | −90.772 | 1.00 | 50.37 | C |
| ATOM | 9158 | CB | ILE C | 177 | −19.938 | 60.890 | −91.934 | 1.00 | 50.71 | C |
| ATOM | 9159 | CG1 | ILE C | 177 | −20.515 | 61.339 | −93.287 | 1.00 | 50.99 | C |
| ATOM | 9160 | CD1 | ILE C | 177 | −22.010 | 61.129 | −93.452 | 1.00 | 50.09 | C |
| ATOM | 9161 | CG2 | ILE C | 177 | −20.226 | 59.407 | −91.692 | 1.00 | 49.96 | C |
| ATOM | 9162 | C | ILE C | 177 | −19.723 | 61.477 | −89.481 | 1.00 | 49.33 | C |
| ATOM | 9163 | O | ILE C | 177 | −18.657 | 62.046 | −89.230 | 1.00 | 48.56 | O |
| ATOM | 9164 | N | GLN C | 178 | −20.293 | 60.596 | −88.663 | 1.00 | 48.61 | N |
| ATOM | 9165 | CA | GLN C | 178 | −19.725 | 60.263 | −87.364 | 1.00 | 47.75 | C |
| ATOM | 9166 | CB | GLN C | 178 | −20.835 | 60.038 | −86.332 | 1.00 | 48.09 | C |
| ATOM | 9167 | CG | GLN C | 178 | −21.364 | 61.307 | −85.680 | 1.00 | 48.01 | C |
| ATOM | 9168 | CD | GLN C | 178 | −22.824 | 61.194 | −85.274 | 1.00 | 47.73 | C |
| ATOM | 9169 | OE1 | GLN C | 178 | −23.429 | 60.123 | −85.366 | 1.00 | 46.07 | O |
| ATOM | 9170 | NE2 | GLN C | 178 | −23.399 | 62.307 | −84.828 | 1.00 | 48.06 | N |
| ATOM | 9171 | C | GLN C | 178 | −18.838 | 59.031 | −87.444 | 1.00 | 46.30 | C |
| ATOM | 9172 | O | GLN C | 178 | −19.084 | 58.123 | −88.236 | 1.00 | 45.88 | O |
| ATOM | 9173 | N | GLN C | 179 | −17.789 | 59.023 | −86.632 | 1.00 | 44.53 | N |
| ATOM | 9174 | CA | GLN C | 179 | −17.014 | 57.823 | −86.415 | 1.00 | 43.23 | C |
| ATOM | 9175 | CB | GLN C | 179 | −15.599 | 57.955 | −86.988 | 1.00 | 43.21 | C |
| ATOM | 9176 | CG | GLN C | 179 | −15.579 | 58.171 | −88.500 | 1.00 | 44.69 | C |
| ATOM | 9177 | CD | GLN C | 179 | −14.678 | 57.193 | −89.248 | 1.00 | 45.70 | C |
| ATOM | 9178 | OE1 | GLN C | 179 | −14.749 | 55.979 | −89.047 | 1.00 | 46.32 | O |
| ATOM | 9179 | NE2 | GLN C | 179 | −13.844 | 57.721 | −90.138 | 1.00 | 45.48 | N |
| ATOM | 9180 | C | GLN C | 179 | −17.008 | 57.548 | −84.921 | 1.00 | 43.10 | C |
| ATOM | 9181 | O | GLN C | 179 | −16.769 | 58.458 | −84.120 | 1.00 | 42.92 | O |
| ATOM | 9182 | N | ALA C | 180 | −17.313 | 56.300 | −84.553 | 1.00 | 41.97 | N |
| ATOM | 9183 | CA | ALA C | 180 | −17.444 | 55.901 | −83.150 | 1.00 | 40.29 | C |
| ATOM | 9184 | CB | ALA C | 180 | −18.802 | 55.260 | −82.902 | 1.00 | 39.36 | C |
| ATOM | 9185 | C | ALA C | 180 | −16.316 | 54.983 | −82.665 | 1.00 | 39.26 | C |
| ATOM | 9186 | O | ALA C | 180 | −16.019 | 53.950 | −83.285 | 1.00 | 35.43 | O |
| ATOM | 9187 | N | LYS C | 181 | −15.686 | 55.397 | −81.561 | 1.00 | 39.95 | N |
| ATOM | 9188 | CA | LYS C | 181 | −14.758 | 54.552 | −80.804 | 1.00 | 40.09 | C |
| ATOM | 9189 | CB | LYS C | 181 | −13.837 | 55.402 | −79.923 | 1.00 | 39.76 | C |
| ATOM | 9190 | CG | LYS C | 181 | −13.090 | 54.615 | −78.859 | 1.00 | 39.65 | C |
| ATOM | 9191 | CD | LYS C | 181 | −11.591 | 54.811 | −78.975 | 1.00 | 40.94 | C |
| ATOM | 9192 | CE | LYS C | 181 | −11.007 | 53.864 | −80.008 | 1.00 | 41.69 | C |
| ATOM | 9193 | NZ | LYS C | 181 | −9.990 | 54.543 | −80.858 | 1.00 | 42.44 | N |
| ATOM | 9194 | C | LYS C | 181 | −15.559 | 53.554 | −79.965 | 1.00 | 40.17 | C |
| ATOM | 9195 | O | LYS C | 181 | −16.403 | 53.942 | −79.150 | 1.00 | 40.86 | O |
| ATOM | 9196 | N | VAL C | 182 | −15.277 | 52.271 | −80.161 | 1.00 | 38.75 | N |
| ATOM | 9197 | CA | VAL C | 182 | −16.205 | 51.224 | −79.777 | 1.00 | 37.12 | C |
| ATOM | 9198 | CB | VAL C | 182 | −17.132 | 50.906 | −80.976 | 1.00 | 36.68 | C |
| ATOM | 9199 | CG1 | VAL C | 182 | −17.315 | 49.412 | −81.197 | 1.00 | 35.97 | C |
| ATOM | 9200 | CG2 | VAL C | 182 | −18.456 | 51.635 | −80.813 | 1.00 | 36.78 | C |
| ATOM | 9201 | C | VAL C | 182 | −15.495 | 49.981 | −79.259 | 1.00 | 36.86 | C |
| ATOM | 9202 | O | VAL C | 182 | −14.634 | 49.426 | −79.941 | 1.00 | 38.01 | O |
| ATOM | 9203 | N | GLN C | 183 | −15.844 | 49.566 | −78.040 | 1.00 | 36.65 | N |
| ATOM | 9204 | CA | GLN C | 183 | −15.348 | 48.298 | −77.473 | 1.00 | 36.94 | C |
| ATOM | 9205 | CB | GLN C | 183 | −14.973 | 48.448 | −75.987 | 1.00 | 36.31 | C |
| ATOM | 9206 | C | GLN C | 183 | −16.364 | 47.160 | −77.671 | 1.00 | 36.22 | C |
| ATOM | 9207 | O | GLN C | 183 | −17.496 | 47.224 | −77.173 | 1.00 | 35.00 | O |
| ATOM | 9208 | N | ILE C | 184 | −15.961 | 46.131 | −78.413 | 1.00 | 35.08 | N |
| ATOM | 9209 | CA | ILE C | 184 | −16.834 | 44.983 | −78.657 | 1.00 | 34.76 | C |
| ATOM | 9210 | CB | ILE C | 184 | −16.176 | 43.945 | −79.598 | 1.00 | 33.98 | C |
| ATOM | 9211 | CG1 | ILE C | 184 | −15.836 | 44.571 | −80.965 | 1.00 | 33.22 | C |
| ATOM | 9212 | CD1 | ILE C | 184 | −17.026 | 45.073 | −81.762 | 1.00 | 32.20 | C |
| ATOM | 9213 | CG2 | ILE C | 184 | −17.068 | 42.718 | −79.753 | 1.00 | 33.18 | C |
| ATOM | 9214 | C | ILE C | 184 | −17.242 | 44.306 | −77.344 | 1.00 | 25.47 | C |
| ATOM | 9215 | O | ILE C | 184 | −16.394 | 44.026 | −76.477 | 1.00 | 35.62 | O |
| ATOM | 9216 | N | LEU C | 185 | −18.542 | 44.060 | −77.187 | 1.00 | 34.36 | N |
| ATOM | 9217 | CA | LEU C | 185 | −19.016 | 43.268 | −76.051 | 1.00 | 33.04 | C |
| ATOM | 9218 | CB | LEU C | 185 | −20.361 | 43.773 | −75.532 | 1.00 | 30.76 | C |
| ATOM | 9219 | CG | LEU C | 185 | −20.406 | 45.235 | −75.088 | 1.00 | 29.65 | C |
| ATOM | 9220 | CD1 | LEU C | 185 | −21.827 | 45.632 | −74.724 | 1.00 | 29.29 | C |
| ATOM | 9221 | CD2 | LEU C | 185 | −19.437 | 45.526 | −73.947 | 1.00 | 28.76 | C |
| ATOM | 9222 | C | LEU C | 185 | −19.089 | 41.798 | −76.447 | 1.00 | 33.63 | C |
| ATOM | 9223 | O | LEU C | 185 | −19.683 | 41.458 | −77.469 | 1.00 | 34.03 | O |

-continued

| | | | | Atomic coordinates for CRBN:DDB1:Lenalidomide (Human protein) | | | | | |
|---|---|---|---|---|---|---|---|---|---|
| ATOM | 9224 | N | PRO C | 186 | −18.451 | 40.926 | −75.652 | 1.00 | 34.23 | N |
| ATOM | 9225 | CA | PRO C | 186 | −18.408 | 39.485 | −75.905 | 1.00 | 34.38 | C |
| ATOM | 9226 | CB | PRO C | 186 | −17.405 | 38.988 | −74.857 | 1.00 | 35.52 | C |
| ATOM | 9227 | CG | PRO C | 186 | −17.492 | 39.981 | −73.743 | 1.00 | 34.59 | C |
| ATOM | 9228 | CD | PRO C | 186 | −17.712 | 41.296 | −74.429 | 1.00 | 34.50 | C |
| ATOM | 9229 | C | PRO C | 186 | −19.761 | 38.790 | −75.690 | 1.00 | 33.47 | C |
| ATOM | 9230 | O | PRO C | 186 | −20.477 | 39.118 | −74.733 | 1.00 | 34.19 | O |
| ATOM | 9231 | N | GLU C | 187 | −20.107 | 37.840 | −76.563 | 1.00 | 31.35 | N |
| ATOM | 9232 | CA | GLU C | 187 | −21.272 | 36.982 | −76.311 | 1.00 | 30.42 | C |
| ATOM | 9233 | CB | GLU C | 187 | −21.802 | 36.334 | −77.586 | 1.00 | 30.44 | C |
| ATOM | 9234 | CG | GLU C | 187 | −23.054 | 35.488 | −77.376 | 1.00 | 29.89 | C |
| ATOM | 9235 | CD | GLU C | 187 | −24.313 | 36.317 | −77.192 | 1.00 | 30.44 | C |
| ATOM | 9236 | OE1 | GLU C | 187 | −24.320 | 37.505 | −77.598 | 1.00 | 30.04 | O |
| ATOM | 9237 | OE2 | GLU C | 187 | −25.303 | 35.774 | −76.648 | 1.00 | 30.77 | O |
| ATOM | 9238 | C | GLU C | 187 | −20.908 | 35.915 | −75.294 | 1.00 | 30.11 | C |
| ATOM | 9239 | O | GLU C | 187 | −20.077 | 35.033 | −75.564 | 1.00 | 30.06 | O |
| ATOM | 9240 | N | CYS C | 188 | −21.537 | 36.006 | −74.127 | 1.00 | 28.63 | N |
| ATOM | 9241 | CA | CYS C | 188 | −21.168 | 35.204 | −72.983 | 1.00 | 26.93 | C |
| ATOM | 9242 | CB | CYS C | 188 | −21.512 | 35.968 | −71.714 | 1.00 | 28.99 | C |
| ATOM | 9243 | SG | CYS C | 188 | −21.877 | 34.930 | −70.289 | 1.00 | 34.68 | S |
| ATOM | 9244 | C | CYS C | 188 | −21.846 | 33.840 | −73.036 | 1.00 | 24.92 | C |
| ATOM | 9245 | O | CYS C | 188 | −23.052 | 33.729 | −72.857 | 1.00 | 23.99 | O |
| ATOM | 9246 | N | VAL C | 189 | −21.057 | 32.807 | −73.318 | 1.00 | 23.98 | N |
| ATOM | 9247 | CA | VAL C | 189 | −21.579 | 31.443 | −73.492 | 1.00 | 23.07 | C |
| ATOM | 9248 | CB | VAL C | 189 | −21.122 | 30.798 | −74.824 | 1.00 | 22.52 | C |
| ATOM | 9249 | CG1 | VAL C | 189 | −21.564 | 31.643 | −76.008 | 1.00 | 21.63 | C |
| ATOM | 9250 | CG2 | VAL C | 189 | −19.612 | 30.592 | −74.851 | 1.00 | 23.26 | C |
| ATOM | 9251 | C | VAL C | 189 | −21.200 | 30.547 | −72.315 | 1.00 | 22.77 | C |
| ATOM | 9252 | O | VAL C | 189 | −20.024 | 30.478 | −71.917 | 1.00 | 23.03 | O |
| ATOM | 9253 | N | LEU C | 190 | −22.199 | 29.875 | −71.746 | 1.00 | 21.77 | N |
| ATOM | 9254 | CA | LEU C | 190 | −21.979 | 29.056 | −70.557 | 1.00 | 21.26 | C |
| ATOM | 9255 | CB | LEU C | 190 | −22.724 | 29.634 | −69.347 | 1.00 | 20.89 | C |
| ATOM | 9256 | CG | LEU C | 190 | −22.598 | 31.141 | −69.113 | 1.00 | 20.79 | C |
| ATOM | 9257 | CD1 | LEU C | 190 | −23.528 | 31.577 | −67.999 | 1.00 | 20.74 | C |
| ATOM | 9258 | CD2 | LEU C | 190 | −21.164 | 31.537 | −68.807 | 1.00 | 21.18 | C |
| ATOM | 9259 | C | LEU C | 190 | −22.406 | 27.617 | −70.794 | 1.00 | 20.89 | C |
| ATOM | 9260 | O | LEU C | 190 | −23.376 | 27.380 | −71.509 | 1.00 | 21.01 | O |
| ATOM | 9261 | N | PRO C | 191 | −21.682 | 26.650 | −70.189 | 1.00 | 20.38 | N |
| ATOM | 9262 | CA | PRO C | 191 | −22.109 | 25.255 | −70.195 | 1.00 | 20.44 | C |
| ATOM | 9263 | CB | PRO C | 191 | −20.981 | 24.551 | −69.447 | 1.00 | 20.07 | C |
| ATOM | 9264 | CG | PRO C | 191 | −20.402 | 25.599 | −68.566 | 1.00 | 19.92 | C |
| ATOM | 9265 | CD | PRO C | 191 | −20.469 | 26.847 | −69.377 | 1.00 | 20.04 | C |
| ATOM | 9266 | C | PRO C | 191 | −23.426 | 25.127 | −69.431 | 1.00 | 20.86 | C |
| ATOM | 9267 | O | PRO C | 191 | −23.985 | 26.147 | −69.026 | 1.00 | 21.55 | O |
| ATOM | 9268 | N | SER C | 192 | −23.932 | 23.910 | −69.241 | 1.00 | 21.13 | N |
| ATOM | 9269 | CA | SER C | 192 | −25.111 | 23.727 | −68.394 | 1.00 | 22.07 | C |
| ATOM | 9270 | CB | SER C | 192 | −25.664 | 22.315 | −68.525 | 1.00 | 22.98 | C |
| ATOM | 9271 | OG | SER C | 192 | −24.936 | 21.422 | −67.685 | 1.00 | 24.06 | O |
| ATOM | 9272 | C | SER C | 192 | −24.719 | 23.982 | −66.941 | 1.00 | 22.43 | C |
| ATOM | 9273 | O | SER C | 192 | −23.532 | 23.915 | −66.591 | 1.00 | 22.77 | O |
| ATOM | 9274 | N | THR C | 193 | −25.703 | 24.245 | −66.085 | 1.00 | 22.61 | N |
| ATOM | 9275 | CA | THR C | 193 | −25.416 | 24.386 | −64.660 | 1.00 | 23.04 | C |
| ATOM | 9276 | CB | THR C | 193 | −26.633 | 24.792 | −63.808 | 1.00 | 23.22 | C |
| ATOM | 9277 | OG1 | THR C | 193 | −27.727 | 25.222 | −64.630 | 1.00 | 23.73 | O |
| ATOM | 9278 | CG2 | THR C | 193 | −26.226 | 25.905 | −62.879 | 1.00 | 23.65 | C |
| ATOM | 9279 | C | THR C | 193 | −24.838 | 23.113 | −64.050 | 1.00 | 22.96 | C |
| ATOM | 9280 | O | THR C | 193 | −24.161 | 23.172 | −63.022 | 1.00 | 23.90 | O |
| ATOM | 9281 | N | MET C | 194 | −25.095 | 21.974 | −64.685 | 1.00 | 21.65 | N |
| ATOM | 9282 | CA | MET C | 194 | −24.715 | 20.684 | −64.121 | 1.00 | 20.83 | C |
| ATOM | 9283 | CB | MET C | 194 | −25.774 | 19.642 | −64.458 | 1.00 | 20.93 | C |
| ATOM | 9284 | CG | MET C | 194 | −27.157 | 19.991 | −63.933 | 1.00 | 20.79 | C |
| ATOM | 9285 | SD | MET C | 194 | −27.328 | 19.717 | −62.159 | 1.00 | 21.07 | S |
| ATOM | 9286 | CE | MET C | 194 | −26.579 | 21.191 | −61.449 | 1.00 | 20.41 | C |
| ATOM | 9287 | C | MET C | 194 | −23.339 | 20.190 | −64.543 | 1.00 | 20.40 | C |
| ATOM | 9288 | O | MET C | 194 | −22.687 | 19.459 | −63.809 | 1.00 | 20.13 | O |
| ATOM | 9289 | N | SER C | 195 | −22.901 | 20.587 | −65.730 | 1.00 | 20.58 | N |
| ATOM | 9290 | CA | SER C | 195 | −21.594 | 20.181 | −66.259 | 1.00 | 20.71 | C |
| ATOM | 9291 | CB | SER C | 195 | −21.293 | 20.977 | −67.535 | 1.00 | 20.64 | C |
| ATOM | 9292 | OG | SER C | 195 | −20.819 | 22.280 | −67.216 | 1.00 | 20.72 | O |
| ATOM | 9293 | C | SER C | 195 | −20.417 | 20.328 | −65.265 | 1.00 | 20.41 | C |
| ATOM | 9294 | O | SER C | 195 | −19.372 | 19.739 | −65.460 | 1.00 | 20.38 | O |
| ATOM | 9295 | N | ALA C | 196 | −20.594 | 21.131 | −64.221 | 1.00 | 20.87 | N |
| ATOM | 9296 | CA | ALA C | 196 | −19.528 | 21.426 | −63.257 | 1.00 | 21.28 | C |
| ATOM | 9297 | CB | ALA C | 196 | −19.689 | 22.843 | −62.713 | 1.00 | 20.99 | C |
| ATOM | 9298 | C | ALA C | 196 | −19.529 | 20.426 | −62.107 | 1.00 | 21.99 | C |
| ATOM | 9299 | O | ALA C | 196 | −18.483 | 20.076 | −61.553 | 1.00 | 22.06 | O |
| ATOM | 9300 | N | VAL C | 197 | −20.720 | 19.960 | −61.761 | 1.00 | 21.96 | N |

-continued

| Atomic coordinates for CRBN:DDB1:Lenalidomide (Human protein) | | | | | | | | | |
|---|---|---|---|---|---|---|---|---|---|
| ATOM | 9301 | CA  | VAL C | 197 | −20.927 | 19.189 | −60.562 | 1.00 | 21.08 | C |
| ATOM | 9302 | CB  | VAL C | 197 | −21.996 | 19.895 | −59.724 | 1.00 | 20.64 | C |
| ATOM | 9303 | CG1 | VAL C | 197 | −23.376 | 19.302 | −59.981 | 1.00 | 20.66 | C |
| ATOM | 9304 | CG2 | VAL C | 197 | −21.627 | 19.867 | −58.258 | 1.00 | 20.68 | C |
| ATOM | 9305 | C   | VAL C | 197 | −21.331 | 17.740 | −60.893 | 1.00 | 21.43 | C |
| ATOM | 9306 | O   | VAL C | 197 | −21.561 | 16.926 | −59.986 | 1.00 | 21.30 | O |
| ATOM | 9307 | N   | GLN C | 198 | −21.389 | 17.431 | −62.196 | 1.00 | 21.62 | N |
| ATOM | 9308 | CA  | GLN C | 198 | −21.889 | 16.153 | −62.704 | 1.00 | 22.27 | C |
| ATOM | 9309 | CB  | GLN C | 198 | −22.066 | 16.191 | −64.228 | 1.00 | 23.74 | C |
| ATOM | 9310 | CG  | GLN C | 198 | −22.623 | 14.893 | −64.834 | 1.00 | 24.62 | C |
| ATOM | 9311 | CD  | GLN C | 198 | −24.145 | 14.787 | −64.716 | 1.00 | 25.83 | C |
| ATOM | 9312 | OE1 | GLN C | 198 | −24.880 | 15.663 | −65.205 | 1.00 | 27.24 | O |
| ATOM | 9313 | NE2 | GLN C | 198 | −24.627 | 13.721 | −64.065 | 1.00 | 24.33 | N |
| ATOM | 9314 | C   | GLN C | 198 | −20.974 | 15.010 | −62.374 | 1.00 | 22.08 | C |
| ATOM | 9315 | O   | GLN C | 198 | −19.788 | 15.045 | −62.689 | 1.00 | 22.03 | O |
| ATOM | 9316 | N   | LEU C | 199 | −21.543 | 13.980 | −61.765 | 1.00 | 22.36 | N |
| ATOM | 9317 | CA  | LEU C | 199 | −20.817 | 12.746 | −61.507 | 1.00 | 23.03 | C |
| ATOM | 9318 | CB  | LEU C | 199 | −21.706 | 11.753 | −60.746 | 1.00 | 22.68 | C |
| ATOM | 9319 | CG  | LEU C | 199 | −21.706 | 11.705 | −59.208 | 1.00 | 22.15 | C |
| ATOM | 9320 | CD1 | LEU C | 199 | −21.228 | 12.994 | −58.554 | 1.00 | 20.88 | C |
| ATOM | 9321 | CD2 | LEU C | 199 | −23.096 | 11.326 | −58.711 | 1.00 | 21.73 | C |
| ATOM | 9322 | C   | LEU C | 199 | −20.358 | 12.139 | −62.824 | 1.00 | 23.39 | C |
| ATOM | 9323 | O   | LEU C | 199 | −21.142 | 12.040 | −63.764 | 1.00 | 23.49 | O |
| ATOM | 9324 | N   | GLU C | 200 | −19.083 | 11.759 | −62.888 | 1.00 | 24.15 | N |
| ATOM | 9325 | CA  | GLU C | 200 | −18.523 | 11.071 | −64.048 | 1.00 | 25.01 | C |
| ATOM | 9326 | CB  | GLU C | 200 | −17.073 | 10.675 | −63.770 | 1.00 | 27.34 | C |
| ATOM | 9327 | CG  | GLU C | 200 | −16.042 | 11.632 | −64.333 | 1.00 | 30.38 | C |
| ATOM | 9328 | CD  | GLU C | 200 | −14.933 | 11.959 | −63.341 | 1.00 | 32.53 | C |
| ATOM | 9329 | OE1 | GLU C | 200 | −15.130 | 12.882 | −62.513 | 1.00 | 32.87 | O |
| ATOM | 9330 | OE2 | GLU C | 200 | −13.858 | 11.308 | −63.401 | 1.00 | 33.82 | O |
| ATOM | 9331 | C   | GLU C | 200 | −19.327 | 9.829  | −64.444 | 1.00 | 24.25 | C |
| ATOM | 9332 | O   | GLU C | 200 | −19.522 | 9.565  | −65.626 | 1.00 | 23.76 | O |
| ATOM | 9333 | N   | SER C | 201 | −19.788 | 9.070  | −63.453 | 1.00 | 23.80 | N |
| ATOM | 9334 | CA  | SER C | 201 | −20.521 | 7.830  | −63.711 | 1.00 | 24.17 | C |
| ATOM | 9335 | CB  | SER C | 201 | −20.784 | 7.086  | −62.402 | 1.00 | 24.00 | C |
| ATOM | 9336 | OG  | SER C | 201 | −21.361 | 7.952  | −61.444 | 1.00 | 24.53 | O |
| ATOM | 9337 | C   | SER C | 201 | −21.841 | 8.030  | −64.491 | 1.00 | 24.32 | C |
| ATOM | 9338 | O   | SER C | 201 | −22.279 | 7.131  | −65.234 | 1.00 | 24.55 | O |
| ATOM | 9339 | N   | LEU C | 202 | −22.456 | 9.204  | −64.327 | 1.00 | 23.37 | N |
| ATOM | 9340 | CA  | LEU C | 202 | −23.756 | 9.491  | −64.933 | 1.00 | 22.52 | C |
| ATOM | 9341 | CB  | LEU C | 202 | −24.641 | 10.294 | −63.977 | 1.00 | 22.04 | C |
| ATOM | 9342 | CG  | LEU C | 202 | −24.808 | 9.908  | −62.509 | 1.00 | 21.63 | C |
| ATOM | 9343 | CD1 | LEU C | 202 | −25.641 | 10.967 | −61.806 | 1.00 | 21.05 | C |
| ATOM | 9344 | CD2 | LEU C | 202 | −25.444 | 8.536  | −62.349 | 1.00 | 21.34 | C |
| ATOM | 9345 | C   | LEU C | 202 | −23.630 | 10.248 | −66.241 | 1.00 | 22.37 | C |
| ATOM | 9346 | O   | LEU C | 202 | −24.631 | 10.587 | −66.857 | 1.00 | 22.79 | O |
| ATOM | 9347 | N   | ASN C | 203 | −22.405 | 10.541 | −66.650 | 1.00 | 22.67 | N |
| ATOM | 9348 | CA  | ASN C | 203 | −22.164 | 11.131 | −67.960 | 1.00 | 23.88 | C |
| ATOM | 9349 | CB  | ASN C | 203 | −20.665 | 11.161 | −68.257 | 1.00 | 22.53 | C |
| ATOM | 9350 | CG  | ASN C | 203 | −19.966 | 12.331 | −67.615 | 1.00 | 21.37 | C |
| ATOM | 9351 | OD1 | ASN C | 203 | −18.760 | 12.303 | −67.405 | 1.00 | 20.80 | O |
| ATOM | 9352 | ND2 | ASN C | 203 | −20.720 | 13.372 | −67.307 | 1.00 | 21.55 | N |
| ATOM | 9353 | C   | ASN C | 203 | −22.898 | 10.375 | −69.076 | 1.00 | 26.04 | C |
| ATOM | 9354 | O   | ASN C | 203 | −23.499 | 10.983 | −69.972 | 1.00 | 26.30 | O |
| ATOM | 9355 | N   | LYS C | 204 | −22.859 | 9.044  | −68.989 | 1.00 | 28.41 | N |
| ATOM | 9356 | CA  | LYS C | 204 | −23.413 | 8.153  | −70.012 | 1.00 | 29.77 | C |
| ATOM | 9357 | CB  | LYS C | 204 | −23.100 | 6.693  | −69.661 | 1.00 | 30.77 | C |
| ATOM | 9358 | CG  | LYS C | 204 | −21.631 | 6.434  | −69.349 | 1.00 | 32.76 | C |
| ATOM | 9359 | CD  | LYS C | 204 | −21.333 | 4.961  | −69.074 | 1.00 | 33.49 | C |
| ATOM | 9360 | CE  | LYS C | 204 | −21.648 | 4.559  | −67.640 | 1.00 | 33.32 | C |
| ATOM | 9361 | NZ  | LYS C | 204 | −23.113 | 4.359  | −67.458 | 1.00 | 34.55 | N |
| ATOM | 9362 | C   | LYS C | 204 | −24.921 | 8.338  | −70.220 | 1.00 | 29.95 | C |
| ATOM | 9363 | O   | LYS C | 204 | −25.475 | 7.894  | −71.223 | 1.00 | 30.63 | O |
| ATOM | 9364 | N   | CYS C | 205 | −25.579 | 9.000  | −69.278 | 1.00 | 29.93 | N |
| ATOM | 9365 | CA  | CYS C | 205 | −27.025 | 9.137  | −69.324 | 1.00 | 30.55 | C |
| ATOM | 9366 | CB  | CYS C | 205 | −27.628 | 8.771  | −67.977 | 1.00 | 30.39 | C |
| ATOM | 9367 | SG  | CYS C | 205 | −26.915 | 7.269  | −67.293 | 1.00 | 31.81 | S |
| ATOM | 9368 | C   | CYS C | 205 | −27.450 | 10.537 | −69.705 | 1.00 | 31.15 | C |
| ATOM | 9369 | O   | CYS C | 205 | −28.651 | 10.833 | −69.736 | 1.00 | 31.36 | O |
| ATOM | 9370 | N   | GLN C | 206 | −26.470 | 11.392 | −70.001 | 1.00 | 31.36 | N |
| ATOM | 9371 | CA  | GLN C | 206 | −26.741 | 12.807 | −70.222 | 1.00 | 31.39 | C |
| ATOM | 9372 | CB  | GLN C | 206 | −25.485 | 13.669 | −70.034 | 1.00 | 31.08 | C |
| ATOM | 9373 | CG  | GLN C | 206 | −25.205 | 14.048 | −68.577 | 1.00 | 32.12 | C |
| ATOM | 9374 | CD  | GLN C | 206 | −26.385 | 14.756 | −67.886 | 1.00 | 33.35 | C |
| ATOM | 9375 | OE1 | GLN C | 206 | −27.460 | 14.173 | −67.714 | 1.00 | 34.34 | O |
| ATOM | 9376 | NE2 | GLN C | 206 | −26.176 | 16.010 | −67.468 | 1.00 | 32.07 | N |
| ATOM | 9377 | C   | GLN C | 206 | −27.438 | 13.068 | −71.548 | 1.00 | 31.87 | C |

-continued

| | | | Atomic coordinates for CRBN:DDB1:Lenalidomide (Human protein) | | | | | | |
|---|---|---|---|---|---|---|---|---|---|
| ATOM | 9378 | O | GLN C | 206 | −28.205 | 14.026 | −71.669 | 1.00 | 32.96 | O |
| ATOM | 9379 | N | ILE C | 207 | −27.196 | 12.199 | −72.528 | 1.00 | 32.18 | N |
| ATOM | 9380 | CA | ILE C | 207 | −27.991 | 12.199 | −73.758 | 1.00 | 32.08 | C |
| ATOM | 9381 | CB | ILE C | 207 | −27.202 | 11.651 | −74.967 | 1.00 | 30.95 | C |
| ATOM | 9382 | CG1 | ILE C | 207 | −26.096 | 12.641 | −75.356 | 1.00 | 21.20 | C |
| ATOM | 9383 | CD1 | ILE C | 207 | −24.981 | 12.048 | −76.199 | 1.00 | 31.52 | C |
| ATOM | 9384 | CG2 | ILE C | 207 | −28.126 | 11.417 | −76.157 | 1.00 | 29.68 | C |
| ATOM | 9385 | C | ILE C | 207 | −29.281 | 11.415 | −73.542 | 1.00 | 32.22 | C |
| ATOM | 9386 | O | ILE C | 207 | −29.255 | 10.321 | −72.993 | 1.00 | 31.30 | O |
| ATOM | 9387 | N | PHE C | 208 | −30.399 | 11.999 | −73.969 | 1.00 | 34.27 | N |
| ATOM | 9388 | CA | PHE C | 208 | −31.717 | 11.372 | −73.855 | 1.00 | 36.28 | C |
| ATOM | 9389 | CB | PHE C | 208 | −32.709 | 12.356 | −73.233 | 1.00 | 38.45 | C |
| ATOM | 9390 | CG | PHE C | 208 | −32.226 | 12.990 | −71.966 | 1.00 | 41.26 | C |
| ATOM | 9391 | CD1 | PHE C | 208 | −31.605 | 12.224 | −70.971 | 1.00 | 42.83 | C |
| ATOM | 9392 | CE1 | PHE C | 208 | −31.170 | 12.812 | −69.785 | 1.00 | 44.02 | C |
| ATOM | 9393 | CZ | PHE C | 208 | −31.365 | 14.173 | −69.576 | 1.00 | 43.88 | C |
| ATOM | 9394 | CE2 | PHE C | 208 | −31.994 | 14.942 | −70.553 | 1.00 | 44.27 | C |
| ATOM | 9395 | CD2 | PHE C | 208 | −32.421 | 14.350 | −71.741 | 1.00 | 42.65 | C |
| ATOM | 9396 | C | PHE C | 208 | −32.279 | 10.896 | −75.204 | 1.00 | 36.09 | C |
| ATOM | 9397 | O | PHE C | 208 | −31.917 | 11.430 | −76.252 | 1.00 | 33.65 | O |
| ATOM | 9398 | N | PRO C | 209 | −33.178 | 9.889 | −75.175 | 1.00 | 37.08 | N |
| ATOM | 9399 | CA | PRO C | 209 | −34.035 | 9.607 | −76.328 | 1.00 | 38.05 | C |
| ATOM | 9400 | CB | PRO C | 209 | −34.944 | 8.484 | −75.823 | 1.00 | 37.29 | C |
| ATOM | 9401 | CG | PRO C | 209 | −34.177 | 7.834 | −74.731 | 1.00 | 37.21 | C |
| ATOM | 9402 | CD | PRO C | 209 | −33.403 | 8.934 | −74.073 | 1.00 | 37.17 | C |
| ATOM | 9403 | C | PRO C | 209 | −34.875 | 10.841 | −76.670 | 1.00 | 39.98 | C |
| ATOM | 9404 | O | PRO C | 209 | −35.470 | 11.448 | −75.771 | 1.00 | 41.36 | O |
| ATOM | 9405 | N | SER C | 210 | −34.918 | 11.207 | −77.949 | 1.00 | 40.34 | N |
| ATOM | 9406 | CA | SER C | 210 | −35.511 | 12.478 | −78.361 | 1.00 | 42.06 | C |
| ATOM | 9407 | CB | SER C | 210 | −35.150 | 12.798 | −79.810 | 1.00 | 42.46 | C |
| ATOM | 9408 | OG | SER C | 210 | −35.202 | 11.632 | −80.606 | 1.00 | 44.76 | O |
| ATOM | 9409 | C | SER C | 210 | −37.023 | 12.559 | −78.133 | 1.00 | 43.61 | C |
| ATOM | 9410 | O | SER C | 210 | −37.715 | 11.546 | −78.095 | 1.00 | 44.00 | O |
| ATOM | 9411 | N | LYS C | 211 | −37.513 | 13.784 | −77.969 | 1.00 | 47.83 | N |
| ATOM | 9412 | CA | LYS C | 211 | −38.909 | 14.059 | −77.605 | 1.00 | 51.30 | C |
| ATOM | 9413 | CB | LYS C | 211 | −39.069 | 15.529 | −77.150 | 1.00 | 51.58 | C |
| ATOM | 9414 | CG | LYS C | 211 | −38.272 | 16.543 | −77.974 | 1.00 | 51.85 | C |
| ATOM | 9415 | CD | LYS C | 211 | −37.751 | 17.689 | −77.112 | 1.00 | 53.24 | C |
| ATOM | 9416 | CE | LYS C | 211 | −36.335 | 18.114 | −77.510 | 1.00 | 52.78 | C |
| ATOM | 9417 | NZ | LYS C | 211 | −35.724 | 19.108 | −76.573 | 1.00 | 47.88 | N |
| ATOM | 9418 | C | LYS C | 211 | −39.881 | 13.747 | −78.741 | 1.00 | 53.32 | C |
| ATOM | 9419 | O | LYS C | 211 | −39.659 | 14.186 | −79.876 | 1.00 | 55.48 | O |
| ATOM | 9420 | N | PRO C | 212 | −40.955 | 12.978 | −78.444 | 1.00 | 54.57 | N |
| ATOM | 9421 | CA | PRO C | 212 | −42.053 | 12.783 | −79.407 | 1.00 | 55.36 | C |
| ATOM | 9422 | CB | PRO C | 212 | −43.045 | 11.905 | −78.635 | 1.00 | 55.16 | C |
| ATOM | 9423 | CG | PRO C | 212 | −42.200 | 11.161 | −77.657 | 1.00 | 54.18 | C |
| ATOM | 9424 | CD | PRO C | 212 | −41.108 | 12.115 | −77.255 | 1.00 | 54.02 | C |
| ATOM | 9425 | C | PRO C | 212 | −42.704 | 14.113 | −79.812 | 1.00 | 54.85 | C |
| ATOM | 9426 | O | PRO C | 212 | −42.675 | 15.077 | −79.039 | 1.00 | 54.21 | O |
| ATOM | 9427 | N | VAL C | 213 | −43.278 | 14.160 | −81.014 | 1.00 | 55.16 | N |
| ATOM | 9428 | CA | VAL C | 213 | −43.784 | 15.421 | −81.586 | 1.00 | 55.48 | C |
| ATOM | 9429 | CB | VAL C | 213 | −43.693 | 15.445 | −83.137 | 1.00 | 53.71 | C |
| ATOM | 9430 | CG1 | VAL C | 213 | −42.283 | 15.809 | −83.582 | 1.00 | 51.13 | C |
| ATOM | 9431 | CG2 | VAL C | 213 | −44.136 | 14.115 | −83.742 | 1.00 | 52.69 | C |
| ATOM | 9432 | C | VAL C | 213 | −45.193 | 15.825 | −81.112 | 1.00 | 56.11 | C |
| ATOM | 9433 | O | VAL C | 213 | −46.142 | 15.038 | −81.155 | 1.00 | 55.14 | O |
| ATOM | 9434 | N | TYR C | 221 | −44.941 | 17.855 | −70.831 | 1.00 | 59.00 | N |
| ATOM | 9435 | CA | TYR C | 221 | −45.662 | 16.772 | −70.167 | 1.00 | 59.89 | C |
| ATOM | 9436 | CB | TYR C | 221 | −46.533 | 15.986 | −71.168 | 1.00 | 64.56 | C |
| ATOM | 9437 | CG | TYR C | 221 | −45.911 | 15.733 | −72.534 | 1.00 | 67.38 | C |
| ATOM | 9438 | CD1 | TYR C | 221 | −45.634 | 16.794 | −73.413 | 1.00 | 66.88 | C |
| ATOM | 9439 | CE1 | TYR C | 221 | −45.079 | 16.565 | −74.662 | 1.00 | 67.09 | C |
| ATOM | 9440 | CZ | TYR C | 221 | −44.814 | 15.259 | −75.061 | 1.00 | 69.42 | C |
| ATOM | 9441 | OH | TYR C | 221 | −44.268 | 15.027 | −76.301 | 1.00 | 70.32 | O |
| ATOM | 9442 | CE2 | TYR C | 221 | −45.092 | 14.189 | −74.220 | 1.00 | 68.40 | C |
| ATOM | 9443 | CD2 | TYR C | 221 | −45.642 | 14.429 | −72.968 | 1.00 | 67.91 | C |
| ATOM | 9444 | C | TYR C | 221 | −44.716 | 15.852 | −69.378 | 1.00 | 58.43 | C |
| ATOM | 9445 | O | TYR C | 221 | −43.841 | 16.342 | −68.648 | 1.00 | 59.17 | O |
| ATOM | 9446 | N | LYS C | 222 | −44.900 | 14.532 | −69.512 | 1.00 | 53.69 | N |
| ATOM | 9447 | CA | LYS C | 222 | −44.057 | 13.545 | −68.813 | 1.00 | 47.25 | C |
| ATOM | 9448 | CB | LYS C | 222 | −44.617 | 12.110 | −68.910 | 1.00 | 45.93 | C |
| ATOM | 9449 | CG | LYS C | 222 | −45.339 | 11.775 | −70.209 | 1.00 | 49.11 | C |
| ATOM | 9450 | CD | LYS C | 222 | −44.429 | 11.130 | −71.248 | 1.00 | 49.94 | C |
| ATOM | 9451 | CE | LYS C | 222 | −44.539 | 9.612 | −71.231 | 1.00 | 49.87 | C |
| ATOM | 9452 | NZ | LYS C | 222 | −43.450 | 8.988 | −72.029 | 1.00 | 48.94 | N |
| ATOM | 9453 | C | LYS C | 222 | −42.609 | 13.607 | −69.283 | 1.00 | 44.03 | C |
| ATOM | 9454 | O | LYS C | 222 | −41.689 | 13.523 | −68.465 | 1.00 | 43.95 | O |

-continued

| | | | Atomic coordinates for CRBN:DDB1:Lenalidomide (Human protein) | | | | | | |
|---|---|---|---|---|---|---|---|---|---|
| ATOM | 9455 | N | TRP C | 223 | −42.413 | 13.794 | −70.590 | 1.00 | 39.58 | N |
| ATOM | 9456 | CA | TRP C | 223 | −41.070 | 13.898 | −71.161 | 1.00 | 34.76 | C |
| ATOM | 9457 | CB | TRP C | 223 | −41.109 | 14.061 | −72.679 | 1.00 | 33.31 | C |
| ATOM | 9458 | CG | TRP C | 223 | −39.738 | 13.892 | −73.290 | 1.00 | 33.47 | C |
| ATOM | 9459 | CD1 | TRP C | 223 | −39.158 | 12.717 | −73.773 | 1.00 | 33.76 | C |
| ATOM | 9460 | NE1 | TRP C | 223 | −37.875 | 12.949 | −74.220 | 1.00 | 33.13 | N |
| ATOM | 9461 | CE2 | TRP C | 223 | −37.540 | 14.250 | −74.056 | 1.00 | 32.70 | C |
| ATOM | 9462 | CD2 | TRP C | 223 | −38.698 | 14.923 | −73.449 | 1.00 | 33.19 | C |
| ATOM | 9463 | CE3 | TRP C | 223 | −38.614 | 16.284 | −73.161 | 1.00 | 32.27 | C |
| ATOM | 9464 | CZ3 | TRP C | 223 | −37.429 | 16.955 | −73.465 | 1.00 | 32.08 | C |
| ATOM | 9465 | CH2 | TRP C | 223 | −36.337 | 16.292 | −74.050 | 1.00 | 32.16 | C |
| ATOM | 9466 | CZ2 | TRP C | 223 | −36.374 | 14.928 | −74.356 | 1.00 | 32.22 | C |
| ATOM | 9467 | C | TRP C | 223 | −40.266 | 15.003 | −70.525 | 1.00 | 33.33 | C |
| ATOM | 9468 | O | TRP C | 223 | −39.067 | 14.849 | −70.302 | 1.00 | 32.25 | O |
| ATOM | 9469 | N | TRP C | 224 | −40.917 | 16.124 | −70.218 | 1.00 | 32.00 | N |
| ATOM | 9470 | CA | TRP C | 224 | −40.240 | 17.248 | −69.570 | 1.00 | 30.09 | C |
| ATOM | 9471 | CB | TRP C | 224 | −40.963 | 18.566 | −69.840 | 1.00 | 28.89 | C |
| ATOM | 9472 | CG | TRP C | 224 | −40.704 | 19.028 | −71.242 | 1.00 | 28.27 | C |
| ATOM | 9473 | CD1 | TRP C | 224 | −41.482 | 18.787 | −72.369 | 1.00 | 28.15 | C |
| ATOM | 9474 | NE1 | TRP C | 224 | −40.898 | 19.330 | −73.491 | 1.00 | 28.05 | N |
| ATOM | 9475 | CE2 | TRP C | 224 | −39.722 | 19.916 | −73.181 | 1.00 | 27.70 | C |
| ATOM | 9476 | CD2 | TRP C | 224 | −39.527 | 19.751 | −71.735 | 1.00 | 27.51 | C |
| ATOM | 9477 | CE3 | TRP C | 224 | −38.382 | 20.265 | −71.147 | 1.00 | 26.49 | C |
| ATOM | 9478 | CZ3 | TRP C | 224 | −37.458 | 20.927 | −71.960 | 1.00 | 26.25 | C |
| ATOM | 9479 | CH2 | TRP C | 224 | −37.667 | 21.083 | −73.342 | 1.00 | 26.32 | C |
| ATOM | 9480 | CZ2 | TRP C | 224 | −38.799 | 20.577 | −73.978 | 1.00 | 26.87 | C |
| ATOM | 9481 | C | TRP C | 224 | −40.033 | 17.026 | −68.109 | 1.00 | 29.90 | C |
| ATOM | 9482 | O | TRP C | 224 | −39.049 | 17.503 | −67.539 | 1.00 | 29.30 | O |
| ATOM | 9483 | N | GLN C | 225 | −40.945 | 16.290 | −67.483 | 1.00 | 30.10 | N |
| ATOM | 9484 | CA | GLN C | 225 | −40.754 | 15.916 | −66.094 | 1.00 | 30.63 | C |
| ATOM | 9485 | CB | GLN C | 225 | −42.043 | 15.382 | −65.483 | 1.00 | 34.32 | C |
| ATOM | 9486 | CG | GLN C | 225 | −43.091 | 16.462 | −65.225 | 1.00 | 39.23 | C |
| ATOM | 9487 | CD | GLN C | 225 | −44.379 | 15.896 | −64.646 | 1.00 | 42.45 | C |
| ATOM | 9488 | OE1 | GLN C | 225 | −44.377 | 14.805 | −64.054 | 1.00 | 44.71 | O |
| ATOM | 9489 | NE2 | GLN C | 225 | −45.492 | 16.628 | −64.817 | 1.00 | 41.85 | N |
| ATOM | 9490 | C | GLN C | 225 | −39.639 | 14.894 | −66.020 | 1.00 | 28.76 | C |
| ATOM | 9491 | O | GLN C | 225 | −38.820 | 14.927 | −65.097 | 1.00 | 28.26 | O |
| ATOM | 9492 | N | LYS C | 226 | −39.596 | 14.014 | −67.023 | 1.00 | 26.92 | N |
| ATOM | 9493 | CA | LYS C | 226 | −38.505 | 13.060 | −67.196 | 1.00 | 25.64 | C |
| ATOM | 9494 | CB | LYS C | 226 | −38.824 | 12.094 | −68.340 | 1.00 | 25.24 | C |
| ATOM | 9495 | C | LYS C | 226 | −37.159 | 13.774 | −67.432 | 1.00 | 24.58 | C |
| ATOM | 9496 | O | LYS C | 226 | −36.182 | 13.539 | −66.704 | 1.00 | 23.90 | O |
| ATOM | 9497 | N | TYR C | 227 | −37.130 | 14.641 | −68.446 | 1.00 | 23.65 | N |
| ATOM | 9498 | CA | TYR C | 227 | −35.978 | 15.498 | −68.760 | 1.00 | 22.85 | C |
| ATOM | 9499 | CB | TYR C | 227 | −36.397 | 16.557 | −69.780 | 1.00 | 23.05 | C |
| ATOM | 9500 | CG | TYR C | 227 | −35.350 | 17.605 | −70.113 | 1.00 | 22.92 | C |
| ATOM | 9501 | CD1 | TYR C | 227 | −34.471 | 17.422 | −71.176 | 1.00 | 23.07 | C |
| ATOM | 9502 | CE1 | TYR C | 227 | −33.532 | 18.377 | −71.501 | 1.00 | 22.62 | C |
| ATOM | 9503 | CZ | TYR C | 227 | −33.465 | 19.541 | −70.765 | 1.00 | 22.94 | C |
| ATOM | 9504 | OH | TYR C | 227 | −32.520 | 20.485 | −71.091 | 1.00 | 23.68 | O |
| ATOM | 9505 | CE2 | TYR C | 227 | −34.329 | 19.761 | −69.705 | 1.00 | 22.85 | C |
| ATOM | 9506 | CD2 | TYR C | 227 | −35.272 | 18.799 | −69.392 | 1.00 | 23.00 | C |
| ATOM | 9507 | C | TYR C | 227 | −35.412 | 16.183 | −67.516 | 1.00 | 22.51 | C |
| ATOM | 9508 | O | TYR C | 227 | −34.200 | 16.130 | −67.266 | 1.00 | 22.61 | O |
| ATOM | 9509 | N | GLN C | 228 | −36.292 | 16.827 | −66.748 | 1.00 | 21.29 | N |
| ATOM | 9510 | CA | GLN C | 228 | −35.888 | 17.531 | −65.539 | 1.00 | 20.54 | C |
| ATOM | 9511 | CB | GLN C | 228 | −37.064 | 18.288 | −64.912 | 1.00 | 19.85 | C |
| ATOM | 9512 | CG | GLN C | 228 | −36.623 | 19.442 | −64.019 | 1.00 | 19.47 | C |
| ATOM | 9513 | CD | GLN C | 228 | −37.608 | 19.772 | −62.913 | 1.00 | 19.25 | C |
| ATOM | 9514 | OE1 | GLN C | 228 | −38.152 | 20.885 | −62.858 | 1.00 | 18.74 | O |
| ATOM | 9515 | NE2 | GLN C | 228 | −37.830 | 18.815 | −62.009 | 1.00 | 19.20 | N |
| ATOM | 9516 | C | GLN C | 228 | −35.257 | 16.597 | −64.503 | 1.00 | 20.68 | C |
| ATOM | 9517 | O | GLN C | 228 | −34.262 | 16.966 | −63.874 | 1.00 | 20.83 | O |
| ATOM | 9518 | N | ARG C | 229 | −35.835 | 15.400 | −64.333 | 1.00 | 19.94 | N |
| ATOM | 9519 | CA | ARG C | 229 | −35.366 | 14.450 | −63.321 | 1.00 | 19.49 | C |
| ATOM | 9520 | CB | ARG C | 229 | −36.360 | 13.291 | −63.114 | 1.00 | 19.04 | C |
| ATOM | 9521 | C | ARG C | 229 | −33.981 | 13.905 | −63.649 | 1.00 | 19.38 | C |
| ATOM | 9522 | O | ARG C | 229 | −33.166 | 13.702 | −62.733 | 1.00 | 19.62 | O |
| ATOM | 9523 | N | ARG C | 230 | −33.716 | 13.681 | −64.942 | 1.00 | 18.55 | N |
| ATOM | 9524 | CA | ARG C | 230 | −32.462 | 13.046 | −65.374 | 1.00 | 18.27 | C |
| ATOM | 9525 | CB | ARG C | 230 | −32.667 | 12.127 | −66.589 | 1.00 | 17.93 | C |
| ATOM | 9526 | C | ARG C | 230 | −31.332 | 14.044 | −65.635 | 1.00 | 18.00 | C |
| ATOM | 9527 | O | ARG C | 230 | −30.191 | 13.793 | −65.260 | 1.00 | 18.43 | O |
| ATOM | 9528 | N | LYS C | 231 | −31.644 | 15.168 | −66.270 | 1.00 | 17.44 | N |
| ATOM | 9529 | CA | LYS C | 231 | −30.624 | 16.174 | −66.572 | 1.00 | 17.13 | C |
| ATOM | 9530 | CB | LYS C | 231 | −31.167 | 17.209 | −67.555 | 1.00 | 16.73 | C |
| ATOM | 9531 | CG | LYS C | 231 | −30.385 | 18.504 | −67.610 | 1.00 | 16.10 | C |

| | | | | | | | | | | |
|---|---|---|---|---|---|---|---|---|---|---|
| ATOM | 9532 | CD | LYS C | 231 | −30.494 | 19.057 | −69.003 | 1.00 | 16.58 | C |
| ATOM | 9533 | CE | LYS C | 231 | −29.450 | 20.108 | −69.301 | 1.00 | 16.81 | C |
| ATOM | 9534 | NZ | LYS C | 231 | −29.463 | 20.333 | −70.771 | 1.00 | 16.80 | N |
| ATOM | 9535 | C | LYS C | 231 | −30.088 | 16.862 | −65.312 | 1.00 | 16.84 | C |
| ATOM | 9536 | O | LYS C | 231 | −28.890 | 17.103 | −65.189 | 1.00 | 17.01 | O |
| ATOM | 9537 | N | PHE C | 232 | −30.981 | 17.164 | −64.380 | 1.00 | 16.39 | N |
| ATOM | 9538 | CA | PHE C | 232 | −30.620 | 17.920 | −63.199 | 1.00 | 16.04 | C |
| ATOM | 9539 | CB | PHE C | 232 | −31.635 | 19.018 | −62.975 | 1.00 | 15.93 | C |
| ATOM | 9540 | CG | PHE C | 232 | −31.623 | 20.042 | −64.049 | 1.00 | 16.07 | C |
| ATOM | 9541 | CD1 | PHE C | 232 | −30.554 | 20.916 | −64.168 | 1.00 | 15.99 | C |
| ATOM | 9542 | CE1 | PHE C | 232 | −30.523 | 21.862 | −65.168 | 1.00 | 16.20 | C |
| ATOM | 9543 | CZ | PHE C | 232 | −31.569 | 21.935 | −66.077 | 1.00 | 16.59 | C |
| ATOM | 9544 | CE2 | PHE C | 232 | −32.647 | 21.067 | −65.972 | 1.00 | 16.48 | C |
| ATOM | 9545 | CD2 | PHE C | 232 | −32.665 | 20.121 | −64.959 | 1.00 | 16.27 | C |
| ATOM | 9546 | C | PHE C | 232 | −30.491 | 17.056 | −61.964 | 1.00 | 15.98 | C |
| ATOM | 9547 | O | PHE C | 232 | −30.621 | 17.534 | −60.843 | 1.00 | 16.07 | O |
| ATOM | 9548 | N | HIS C | 233 | −30.214 | 15.780 | −62.179 | 1.00 | 15.70 | N |
| ATOM | 9549 | CA | HIS C | 233 | −30.095 | 14.840 | −61.095 | 1.00 | 15.74 | C |
| ATOM | 9550 | CB | HIS C | 233 | −29.733 | 13.477 | −61.629 | 1.00 | 15.16 | C |
| ATOM | 9551 | CG | HIS C | 233 | −29.676 | 12.432 | −60.575 | 1.00 | 14.81 | C |
| ATOM | 9552 | ND1 | HIS C | 233 | −28.529 | 11.911 | −60.153 | 1.00 | 15.17 | N |
| ATOM | 9553 | CE1 | HIS C | 233 | −28.778 | 11.006 | −59.187 | 1.00 | 15.24 | C |
| ATOM | 9554 | NE2 | HIS C | 233 | −30.097 | 10.969 | −58.988 | 1.00 | 14.89 | N |
| ATOM | 9555 | CD2 | HIS C | 233 | −30.682 | 11.837 | −59.825 | 1.00 | 14.75 | C |
| ATOM | 9556 | C | HIS C | 233 | −29.088 | 15.268 | −60.067 | 1.00 | 16.45 | C |
| ATOM | 9557 | O | HIS C | 233 | −29.369 | 15.259 | −58.857 | 1.00 | 16.75 | O |
| ATOM | 9558 | N | CYS C | 234 | −27.912 | 15.678 | −60.533 | 1.00 | 17.12 | N |
| ATOM | 9559 | CA | CYS C | 234 | −26.808 | 16.017 | −59.639 | 1.00 | 17.27 | C |
| ATOM | 9560 | CB | CYS C | 234 | −25.501 | 16.019 | −60.410 | 1.00 | 18.17 | C |
| ATOM | 9561 | SG | CYS C | 234 | −25.002 | 14.356 | −60.882 | 1.00 | 19.89 | S |
| ATOM | 9562 | C | CYS C | 234 | −26.979 | 17.329 | −58.868 | 1.00 | 17.09 | C |
| ATOM | 9563 | O | CYS C | 234 | −26.016 | 17.833 | −58.281 | 1.00 | 17.38 | O |
| ATOM | 9564 | N | ALA C | 235 | −28.199 | 17.874 | −58.856 | 1.00 | 16.24 | N |
| ATOM | 9565 | CA | ALA C | 235 | −28.517 | 18.993 | −57.979 | 1.00 | 15.55 | C |
| ATOM | 9566 | CB | ALA C | 235 | −29.946 | 19.449 | −58.182 | 1.00 | 15.36 | C |
| ATOM | 9567 | C | ALA C | 235 | −28.298 | 18.567 | −56.536 | 1.00 | 15.51 | C |
| ATOM | 9568 | O | ALA C | 235 | −27.913 | 19.375 | −55.697 | 1.00 | 15.38 | O |
| ATOM | 9569 | N | ASN C | 236 | −28.518 | 17.284 | −56.260 | 1.00 | 15.24 | N |
| ATOM | 9570 | CA | ASN C | 236 | −28.387 | 16.758 | −54.919 | 1.00 | 15.04 | C |
| ATOM | 9571 | CB | ASN C | 236 | −28.747 | 15.290 | −54.907 | 1.00 | 16.24 | C |
| ATOM | 9572 | CG | ASN C | 236 | −30.231 | 15.063 | −55.141 | 1.00 | 17.51 | C |
| ATOM | 9573 | OD1 | ASN C | 236 | −30.716 | 15.171 | −56.277 | 1.00 | 17.96 | O |
| ATOM | 9574 | ND2 | ASN C | 236 | −30.967 | 14.741 | −54.064 | 1.00 | 17.56 | N |
| ATOM | 9575 | C | ASN C | 236 | −27.019 | 16.963 | −54.311 | 1.00 | 14.35 | C |
| ATOM | 9576 | O | ASN C | 236 | −26.873 | 16.907 | −53.088 | 1.00 | 13.84 | O |
| ATOM | 9577 | N | LEU C | 237 | −26.038 | 17.226 | −55.181 | 1.00 | 13.77 | N |
| ATOM | 9578 | CA | LEU C | 237 | −24.639 | 17.470 | −54.813 | 1.00 | 13.22 | C |
| ATOM | 9579 | CB | LEU C | 237 | −23.739 | 17.143 | −56.003 | 1.00 | 13.30 | C |
| ATOM | 9580 | CG | LEU C | 237 | −23.536 | 15.682 | −56.428 | 1.00 | 13.70 | C |
| ATOM | 9581 | CD1 | LEU C | 237 | −22.236 | 15.115 | −55.884 | 1.00 | 13.92 | C |
| ATOM | 9582 | CD2 | LEU C | 237 | −24.695 | 14.779 | −56.028 | 1.00 | 13.79 | C |
| ATOM | 9583 | C | LEU C | 237 | −24.440 | 18.928 | −54.424 | 1.00 | 12.92 | C |
| ATOM | 9584 | O | LEU C | 237 | −23.435 | 19.306 | −53.811 | 1.00 | 12.49 | O |
| ATOM | 9585 | N | THR C | 238 | −25.421 | 19.742 | −54.799 | 1.00 | 12.76 | N |
| ATOM | 9586 | CA | THR C | 238 | −25.362 | 21.176 | −54.644 | 1.00 | 12.24 | C |
| ATOM | 9587 | CB | THR C | 238 | −25.613 | 21.886 | −56.000 | 1.00 | 12.07 | C |
| ATOM | 9588 | OG1 | THR C | 238 | −27.015 | 22.071 | −56.220 | 1.00 | 11.66 | O |
| ATOM | 9589 | CG2 | THR C | 238 | −25.037 | 21.079 | −57.163 | 1.00 | 11.99 | C |
| ATOM | 9590 | C | THR C | 238 | −26.401 | 21.577 | −53.618 | 1.00 | 12.19 | C |
| ATOM | 9591 | O | THR C | 238 | −27.017 | 20.740 | −52.988 | 1.00 | 11.84 | O |
| ATOM | 9592 | N | SER C | 239 | −26.616 | 22.867 | −53.468 | 1.00 | 12.91 | N |
| ATOM | 9593 | CA | SER C | 239 | −27.517 | 23.362 | −52.442 | 1.00 | 13.54 | C |
| ATOM | 9594 | CB | SER C | 239 | −26.807 | 24.431 | −51.608 | 1.00 | 13.54 | C |
| ATOM | 9595 | OG | SER C | 239 | −26.062 | 25.269 | −52.467 | 1.00 | 13.80 | O |
| ATOM | 9596 | C | SER C | 239 | −28.846 | 23.892 | −53.000 | 1.00 | 13.78 | C |
| ATOM | 9597 | O | SER C | 239 | −29.552 | 24.631 | −52.314 | 1.00 | 14.37 | O |
| ATOM | 9598 | N | TRP C | 240 | −29.197 | 23.504 | −54.222 | 1.00 | 13.87 | N |
| ATOM | 9599 | CA | TRP C | 240 | −30.508 | 23.847 | −54.776 | 1.00 | 14.36 | C |
| ATOM | 9600 | CB | TRP C | 240 | −30.435 | 25.135 | −55.600 | 1.00 | 14.43 | C |
| ATOM | 9601 | CG | TRP C | 240 | −30.622 | 26.315 | −54.689 | 1.00 | 14.97 | C |
| ATOM | 9602 | CD1 | TRP C | 240 | −31.744 | 26.625 | −53.897 | 1.00 | 15.12 | C |
| ATOM | 9603 | NE1 | TRP C | 240 | −31.523 | 27.754 | −53.136 | 1.00 | 14.78 | N |
| ATOM | 9604 | CE2 | TRP C | 240 | −30.296 | 28.226 | −53.358 | 1.00 | 14.80 | C |
| ATOM | 9605 | CD2 | TRP C | 240 | −29.645 | 27.329 | −54.358 | 1.00 | 15.07 | C |
| ATOM | 9606 | CE3 | TRP C | 240 | −28.354 | 27.592 | −54.762 | 1.00 | 15.05 | C |
| ATOM | 9607 | CZ3 | TRP C | 240 | −27.714 | 28.694 | −54.210 | 1.00 | 15.22 | C |
| ATOM | 9608 | CH2 | TRP C | 240 | −28.357 | 29.538 | −53.272 | 1.00 | 15.30 | C |

-continued

| | | | Atomic coordinates for CRBN:DDB1:Lenalidomide (Human protein) | | | | | | |
|---|---|---|---|---|---|---|---|---|---|
| ATOM | 9609 | CZ2 | TRP C | 240 | −29.662 | 29.311 | −52.834 | 1.00 | 14.82 | C |
| ATOM | 9610 | C | TRP C | 240 | −31.270 | 22.725 | −55.473 | 1.00 | 14.75 | C |
| ATOM | 9611 | O | TRP C | 240 | −30.704 | 21.673 | −55.790 | 1.00 | 14.98 | O |
| ATOM | 9612 | N | PRO C | 241 | −32.577 | 22.928 | −55.704 | 1.00 | 14.83 | N |
| ATOM | 9613 | CA | PRO C | 241 | −33.408 | 21.896 | −56.289 | 1.00 | 15.37 | C |
| ATOM | 9614 | CB | PRO C | 241 | −34.823 | 22.336 | −55.900 | 1.00 | 15.45 | C |
| ATOM | 9615 | CG | PRO C | 241 | −34.677 | 23.547 | −55.042 | 1.00 | 15.05 | C |
| ATOM | 9616 | CD | PRO C | 241 | −33.363 | 24.124 | −55.395 | 1.00 | 14.77 | C |
| ATOM | 9617 | C | PRO C | 241 | −33.315 | 21.825 | −57.816 | 1.00 | 15.97 | C |
| ATOM | 9618 | O | PRO C | 241 | −32.891 | 22.794 | −58.458 | 1.00 | 16.18 | O |
| ATOM | 9619 | N | ARG C | 242 | −33.738 | 20.684 | −58.376 | 1.00 | 16.47 | N |
| ATOM | 9620 | CA | ARG C | 242 | −33.867 | 20.484 | −59.831 | 1.00 | 16.39 | C |
| ATOM | 9621 | CB | ARG C | 242 | −34.557 | 19.145 | −60.129 | 1.00 | 17.50 | C |
| ATOM | 9622 | CG | ARG C | 242 | −33.621 | 17.945 | −60.005 | 1.00 | 19.59 | C |
| ATOM | 9623 | CD | ARG C | 242 | −34.281 | 16.589 | −60.293 | 1.00 | 20.79 | C |
| ATOM | 9624 | NE | ARG C | 242 | −34.739 | 15.950 | −59.064 | 1.00 | 21.38 | N |
| ATOM | 9625 | CZ | ARG C | 242 | −36.010 | 15.910 | −58.666 | 1.00 | 22.16 | C |
| ATOM | 9626 | NH1 | ARG C | 242 | −36.974 | 16.454 | −59.422 | 1.00 | 21.68 | N |
| ATOM | 9627 | NH2 | ARG C | 242 | −36.318 | 15.314 | −57.508 | 1.00 | 22.31 | N |
| ATOM | 9628 | C | ARG C | 242 | −34.626 | 21.613 | −60.518 | 1.00 | 15.80 | C |
| ATOM | 9629 | O | ARG C | 242 | −34.194 | 22.107 | −61.556 | 1.00 | 15.63 | O |
| ATOM | 9630 | N | TRP C | 243 | −35.747 | 22.027 | −59.920 | 1.00 | 15.28 | N |
| ATOM | 9631 | CA | TRP C | 243 | −36.653 | 23.014 | −60.523 | 1.00 | 14.41 | C |
| ATOM | 9632 | CB | TRP C | 243 | −38.016 | 23.022 | −59.830 | 1.00 | 14.04 | C |
| ATOM | 9633 | CG | TRP C | 243 | −37.972 | 23.197 | −58.327 | 1.00 | 13.76 | C |
| ATOM | 9634 | CD1 | TRP C | 243 | −37.986 | 22.194 | −57.358 | 1.00 | 13.71 | C |
| ATOM | 9635 | NE1 | TRP C | 243 | −37.949 | 22.729 | −56.090 | 1.00 | 13.52 | N |
| ATOM | 9636 | CE2 | TRP C | 243 | −37.914 | 24.079 | −56.142 | 1.00 | 13.61 | C |
| ATOM | 9637 | CD2 | TRP C | 243 | −37.935 | 24.457 | −57.570 | 1.00 | 13.56 | C |
| ATOM | 9638 | CE3 | TRP C | 243 | −37.898 | 25.802 | −57.910 | 1.00 | 13.33 | C |
| ATOM | 9639 | CZ3 | TRP C | 243 | −37.848 | 26.751 | −56.872 | 1.00 | 13.50 | C |
| ATOM | 9640 | CH2 | TRP C | 243 | −37.840 | 26.368 | −55.508 | 1.00 | 13.27 | C |
| ATOM | 9641 | CZ2 | TRP C | 243 | −37.868 | 25.030 | −55.121 | 1.00 | 13.27 | C |
| ATOM | 9642 | C | TRP C | 243 | −36.086 | 24.400 | −60.577 | 1.00 | 14.17 | C |
| ATOM | 9643 | O | TRP C | 243 | −36.615 | 25.261 | −61.283 | 1.00 | 14.00 | O |
| ATOM | 9644 | N | LEU C | 244 | −35.008 | 24.639 | −59.835 | 1.00 | 14.04 | N |
| ATOM | 9645 | CA | LEU C | 244 | −34.320 | 25.929 | −59.911 | 1.00 | 13.86 | C |
| ATOM | 9646 | CB | LEU C | 244 | −33.543 | 26.226 | −58.635 | 1.00 | 13.41 | C |
| ATOM | 9647 | CG | LEU C | 244 | −32.777 | 27.524 | −58.799 | 1.00 | 13.43 | C |
| ATOM | 9648 | CD1 | LEU C | 244 | −33.691 | 28.732 | −58.656 | 1.00 | 13.62 | C |
| ATOM | 9649 | CD2 | LEU C | 244 | −31.649 | 27.576 | −57.799 | 1.00 | 13.99 | C |
| ATOM | 9650 | C | LEU C | 244 | −33.375 | 25.936 | −61.100 | 1.00 | 13.72 | C |
| ATOM | 9651 | O | LEU C | 244 | −33.461 | 26.784 | −61.998 | 1.00 | 13.30 | O |
| ATOM | 9652 | N | TYR C | 245 | −32.470 | 24.969 | −61.098 | 1.00 | 13.66 | N |
| ATOM | 9653 | CA | TYR C | 245 | −31.561 | 24.807 | −62.194 | 1.00 | 13.81 | C |
| ATOM | 9654 | CB | TYR C | 245 | −30.733 | 23.549 | −61.974 | 1.00 | 13.45 | C |
| ATOM | 9655 | CG | TYR C | 245 | −29.740 | 23.687 | −60.833 | 1.00 | 13.26 | C |
| ATOM | 9656 | CD1 | TYR C | 245 | −28.661 | 24.570 | −60.926 | 1.00 | 13.35 | C |
| ATOM | 9657 | CE1 | TYR C | 245 | −27.745 | 24.708 | −59.894 | 1.00 | 13.08 | C |
| ATOM | 9658 | CZ | TYR C | 245 | −27.894 | 23.951 | −58.741 | 1.00 | 13.02 | C |
| ATOM | 9659 | OH | TYR C | 245 | −26.979 | 24.089 | −57.720 | 1.00 | 12.49 | O |
| ATOM | 9660 | CE2 | TYR C | 245 | −28.962 | 23.068 | −58.618 | 1.00 | 13.05 | C |
| ATOM | 9661 | CD2 | TYR C | 245 | −29.876 | 22.941 | −59.662 | 1.00 | 13.18 | C |
| ATOM | 9662 | C | TYR C | 245 | −32.349 | 24.788 | −63.517 | 1.00 | 14.28 | C |
| ATOM | 9663 | O | TYR C | 245 | −31.842 | 25.184 | −64.587 | 1.00 | 14.77 | O |
| ATOM | 9664 | N | SER C | 246 | −33.610 | 24.377 | −63.418 | 1.00 | 14.31 | N |
| ATOM | 9665 | CA | SER C | 246 | −34.500 | 24.298 | −64.559 | 1.00 | 14.22 | C |
| ATOM | 9666 | CB | SER C | 246 | −35.797 | 23.587 | −64.173 | 1.00 | 13.89 | C |
| ATOM | 9667 | OG | SER C | 246 | −36.412 | 23.020 | −65.307 | 1.00 | 13.72 | O |
| ATOM | 9668 | C | SER C | 246 | −34.787 | 25.685 | −65.099 | 1.00 | 14.49 | C |
| ATOM | 9669 | O | SER C | 246 | −34.832 | 25.877 | −66.310 | 1.00 | 15.32 | O |
| ATOM | 9670 | N | LEU C | 247 | −34.945 | 26.656 | −64.199 | 1.00 | 14.48 | N |
| ATOM | 9671 | CA | LEU C | 247 | −35.226 | 28.050 | −64.577 | 1.00 | 14.24 | C |
| ATOM | 9672 | CB | LEU C | 247 | −35.737 | 28.833 | −63.366 | 1.00 | 13.64 | C |
| ATOM | 9673 | CG | LEU C | 247 | −37.092 | 28.452 | −62.796 | 1.00 | 13.35 | C |
| ATOM | 9674 | CD1 | LEU C | 247 | −37.291 | 29.071 | −61.423 | 1.00 | 13.05 | C |
| ATOM | 9675 | CD2 | LEU C | 247 | −38.197 | 28.878 | −63.750 | 1.00 | 13.39 | C |
| ATOM | 9676 | C | LEU C | 247 | −34.026 | 28.787 | −65.211 | 1.00 | 14.53 | C |
| ATOM | 9677 | O | LEU C | 247 | −34.141 | 29.952 | −65.559 | 1.00 | 14.26 | O |
| ATOM | 9678 | N | TYR C | 248 | −32.880 | 28.112 | −65.337 | 1.00 | 15.31 | N |
| ATOM | 9679 | CA | TYR C | 248 | −31.717 | 28.659 | −66.068 | 1.00 | 15.94 | C |
| ATOM | 9680 | CB | TYR C | 248 | −30.542 | 28.940 | −65.121 | 1.00 | 15.63 | C |
| ATOM | 9681 | CG | TYR C | 248 | −30.849 | 29.992 | −64.083 | 1.00 | 15.54 | C |
| ATOM | 9682 | CD1 | TYR C | 248 | −31.443 | 29.638 | −62.863 | 1.00 | 15.64 | C |
| ATOM | 9683 | CE1 | TYR C | 248 | −31.741 | 30.597 | −61.904 | 1.00 | 15.61 | C |
| ATOM | 9684 | CZ | TYR C | 248 | −31.452 | 31.933 | −62.164 | 1.00 | 15.76 | C |
| ATOM | 9685 | OH | TYR C | 248 | −31.752 | 32.875 | −61.205 | 1.00 | 16.10 | O |

-continued

| | | | Atomic coordinates for CRBN:DDB1:Lenalidomide (Human protein) | | | | | | |
|---|---|---|---|---|---|---|---|---|---|
| ATOM | 9686 | CE2 | TYR C | 248 | −30.872 | 32.315 | −63.377 | 1.00 | 15.49 | C |
| ATOM | 9687 | CD2 | TYR C | 248 | −30.572 | 31.345 | −64.324 | 1.00 | 15.32 | C |
| ATOM | 9688 | C | TYR C | 248 | −31.267 | 27.776 | −67.235 | 1.00 | 16.39 | C |
| ATOM | 9689 | O | TYR C | 248 | −30.182 | 27.967 | −67.776 | 1.00 | 16.44 | O |
| ATOM | 9690 | N | ASP C | 249 | −32.126 | 26.834 | −67.623 | 1.00 | 17.22 | N |
| ATOM | 9691 | CA | ASP C | 249 | −31.821 | 25.829 | −68.636 | 1.00 | 17.95 | C |
| ATOM | 9692 | CB | ASP C | 249 | −32.470 | 24.484 | −68.251 | 1.00 | 18.52 | C |
| ATOM | 9693 | CG | ASP C | 249 | −32.268 | 23.385 | −69.313 | 1.00 | 19.28 | C |
| ATOM | 9694 | OD1 | ASP C | 249 | −31.108 | 23.000 | −69.608 | 1.00 | 19.43 | O |
| ATOM | 9695 | OD2 | ASP C | 249 | −33.288 | 22.883 | −69.840 | 1.00 | 19.76 | O |
| ATOM | 9696 | C | ASP C | 249 | −32.323 | 26.302 | −69.989 | 1.00 | 18.51 | C |
| ATOM | 9697 | O | ASP C | 249 | −33.539 | 26.350 | −70.236 | 1.00 | 18.94 | O |
| ATOM | 9698 | N | ALA C | 250 | −31.381 | 26.646 | −70.867 | 1.00 | 18.92 | N |
| ATOM | 9699 | CA | ALA C | 250 | −31.695 | 27.197 | −72.191 | 1.00 | 18.61 | C |
| ATOM | 9700 | CB | ALA C | 250 | −30.439 | 27.345 | −73.021 | 1.00 | 18.15 | C |
| ATOM | 9701 | C | ALA C | 250 | −32.723 | 26.371 | −72.934 | 1.00 | 18.91 | C |
| ATOM | 9702 | O | ALA C | 250 | −33.625 | 26.911 | −73.544 | 1.00 | 19.22 | O |
| ATOM | 9703 | N | GLU C | 251 | −32.597 | 25.056 | −72.861 | 1.00 | 19.84 | N |
| ATOM | 9704 | CA | GLU C | 251 | −33.498 | 24.183 | −73.589 | 1.00 | 20.75 | C |
| ATOM | 9705 | CB | GLU C | 251 | −33.020 | 22.724 | −73.521 | 1.00 | 23.28 | C |
| ATOM | 9706 | CG | GLU C | 251 | −31.496 | 22.564 | −73.421 | 1.00 | 27.05 | C |
| ATOM | 9707 | CD | GLU C | 251 | −30.774 | 22.680 | −74.769 | 1.00 | 31.07 | C |
| ATOM | 9708 | OE1 | GLU C | 251 | −30.755 | 21.684 | −75.532 | 1.00 | 32.67 | O |
| ATOM | 9709 | OE2 | GLU C | 251 | −30.197 | 23.760 | −75.065 | 1.00 | 33.25 | O |
| ATOM | 9710 | C | GLU C | 251 | −34.931 | 24.365 | −73.069 | 1.00 | 19.50 | C |
| ATOM | 9711 | O | GLU C | 251 | −35.874 | 24.484 | −73.856 | 1.00 | 19.11 | O |
| ATOM | 9712 | N | THR C | 252 | −35.085 | 24.444 | −71.749 | 1.00 | 18.54 | N |
| ATOM | 9713 | CA | THR C | 252 | −36.422 | 24.604 | −71.144 | 1.00 | 17.88 | C |
| ATOM | 9714 | CB | THR C | 252 | −36.409 | 24.460 | −69.603 | 1.00 | 17.24 | C |
| ATOM | 9715 | OG1 | THR C | 252 | −35.565 | 23.375 | −69.227 | 1.00 | 17.52 | O |
| ATOM | 9716 | CG2 | THR C | 252 | −37.797 | 24.190 | −69.088 | 1.00 | 16.72 | C |
| ATOM | 9717 | C | THR C | 252 | −37.046 | 24.946 | −71.511 | 1.00 | 17.19 | C |
| ATOM | 9718 | O | THR C | 252 | −38.150 | 25.995 | −72.044 | 1.00 | 16.64 | O |
| ATOM | 9719 | N | LEU C | 253 | −36.316 | 27.017 | −71.220 | 1.00 | 16.69 | N |
| ATOM | 9720 | CA | LEU C | 253 | −36.774 | 28.366 | −71.440 | 1.00 | 16.60 | C |
| ATOM | 9721 | CB | LEU C | 253 | −35.640 | 29.334 | −71.124 | 1.00 | 16.32 | C |
| ATOM | 9722 | CG | LEU C | 253 | −36.300 | 29.533 | −69.646 | 1.00 | 16.12 | C |
| ATOM | 9723 | CD1 | LEU C | 253 | −33.814 | 29.765 | −69.482 | 1.00 | 15.93 | C |
| ATOM | 9724 | CD2 | LEU C | 253 | −36.100 | 30.666 | −69.028 | 1.00 | 15.72 | C |
| ATOM | 9725 | C | LEU C | 253 | −37.243 | 28.542 | −72.877 | 1.00 | 17.32 | C |
| ATOM | 9726 | O | LEU C | 253 | −38.340 | 29.048 | −73.124 | 1.00 | 17.03 | O |
| ATOM | 9727 | N | MET C | 254 | −36.410 | 28.092 | −73.819 | 1.00 | 18.59 | N |
| ATOM | 9728 | CA | MET C | 254 | −36.699 | 28.163 | −75.255 | 1.00 | 19.27 | C |
| ATOM | 9729 | CB | MET C | 254 | −35.587 | 27.480 | −76.067 | 1.00 | 19.24 | C |
| ATOM | 9730 | CG | MET C | 254 | −34.286 | 28.272 | −76.206 | 1.00 | 19.30 | C |
| ATOM | 9731 | SD | MET C | 254 | −33.130 | 27.598 | −77.442 | 1.00 | 19.82 | S |
| ATOM | 9732 | CE | MET C | 254 | −32.451 | 26.173 | −76.599 | 1.00 | 19.99 | C |
| ATOM | 9733 | C | MET C | 254 | −38.057 | 27.526 | −75.563 | 1.00 | 20.03 | C |
| ATOM | 9734 | O | MET C | 254 | −38.853 | 28.077 | −76.328 | 1.00 | 19.99 | O |
| ATOM | 9735 | N | ASP C | 255 | −38.311 | 26.378 | −74.938 | 1.00 | 21.37 | N |
| ATOM | 9736 | CA | ASP C | 255 | −39.577 | 25.662 | −75.062 | 1.00 | 22.36 | C |
| ATOM | 9737 | CB | ASP C | 255 | −39.485 | 24.311 | −74.359 | 1.00 | 23.47 | C |
| ATOM | 9738 | CG | ASP C | 255 | −40.677 | 23.430 | −74.648 | 1.00 | 24.95 | C |
| ATOM | 9739 | OD1 | ASP C | 255 | −40.781 | 22.920 | −75.788 | 1.00 | 25.85 | O |
| ATOM | 9740 | OD2 | ASP C | 255 | −41.512 | 23.249 | −73.735 | 1.00 | 26.09 | O |
| ATOM | 9741 | C | ASP C | 255 | −40.759 | 26.457 | −74.505 | 1.00 | 22.49 | C |
| ATOM | 9742 | O | ASP C | 255 | −41.803 | 26.562 | −75.150 | 1.00 | 23.31 | O |
| ATOM | 9743 | N | ARG C | 256 | −40.594 | 27.015 | −73.312 | 1.00 | 22.59 | N |
| ATOM | 9744 | CA | ARG C | 256 | −41.629 | 27.856 | −72.707 | 1.00 | 22.81 | C |
| ATOM | 9745 | CB | ARG C | 256 | −41.210 | 28.310 | −71.300 | 1.00 | 21.46 | C |
| ATOM | 9746 | CG | ARG C | 256 | −41.274 | 27.216 | −70.241 | 1.00 | 20.00 | C |
| ATOM | 9747 | CD | ARG C | 256 | −40.560 | 27.616 | −68.968 | 1.00 | 19.62 | C |
| ATOM | 9748 | NE | ARG C | 256 | −41.235 | 28.712 | −68.276 | 1.00 | 19.78 | N |
| ATOM | 9749 | CZ | ARG C | 256 | −40.641 | 29.564 | −67.442 | 1.00 | 19.72 | C |
| ATOM | 9750 | NH1 | ARG C | 256 | −39.338 | 29.471 | −67.189 | 1.00 | 19.89 | N |
| ATOM | 9751 | NH2 | ARG C | 256 | −41.347 | 30.532 | −66.880 | 1.00 | 19.30 | N |
| ATOM | 9752 | C | ARG C | 256 | −41.947 | 29.059 | −73.598 | 1.00 | 24.00 | C |
| ATOM | 9753 | O | ARG C | 256 | −43.108 | 29.470 | −73.709 | 1.00 | 24.22 | O |
| ATOM | 9754 | N | ILE C | 257 | −40.912 | 29.607 | −74.238 | 1.00 | 25.25 | N |
| ATOM | 9755 | CA | ILE C | 257 | −41.085 | 30.713 | −75.182 | 1.00 | 26.82 | C |
| ATOM | 9756 | CB | ILE C | 257 | −39.745 | 31.427 | −75.515 | 1.00 | 26.81 | C |
| ATOM | 9757 | CG1 | ILE C | 257 | −39.202 | 32.161 | −74.284 | 1.00 | 26.51 | C |
| ATOM | 9758 | CD1 | ILE C | 257 | −37.727 | 32.502 | −74.373 | 1.00 | 26.76 | C |
| ATOM | 9759 | CG2 | ILE C | 257 | −39.916 | 32.440 | −76.637 | 1.00 | 26.25 | C |
| ATOM | 9760 | C | ILE C | 257 | −41.792 | 30.232 | −76.448 | 1.00 | 27.92 | C |
| ATOM | 9761 | O | ILE C | 257 | −42.727 | 30.875 | −76.909 | 1.00 | 28.42 | O |
| ATOM | 9762 | N | LYS C | 258 | −41.363 | 29.089 | −76.987 | 1.00 | 29.78 | N |

-continued

| | | | | Atomic coordinates for CRBN:DDB1:Lenalidomide (Human protein) | | | | | |
|---|---|---|---|---|---|---|---|---|---|
| ATOM | 9763 | CA | LYS C | 258 | −42.007 | 28.504 | −78.175 | 1.00 | 31.23 | C |
| ATOM | 9764 | CB | LYS C | 258 | −41.534 | 27.073 | −78.435 | 1.00 | 32.04 | C |
| ATOM | 9765 | CG | LYS C | 258 | −40.271 | 26.986 | −79.273 | 1.00 | 34.19 | C |
| ATOM | 9766 | CD | LYS C | 258 | −39.868 | 25.541 | −79.530 | 1.00 | 35.74 | C |
| ATOM | 9767 | CE | LYS C | 258 | −38.447 | 25.462 | −80.076 | 1.00 | 37.80 | C |
| ATOM | 9768 | NZ | LYS C | 258 | −38.015 | 24.063 | −80.362 | 1.00 | 37.95 | N |
| ATOM | 9769 | C | LYS C | 258 | −43.522 | 28.529 | −78.072 | 1.00 | 31.54 | C |
| ATOM | 9770 | O | LYS C | 258 | −44.201 | 29.025 | −78.975 | 1.00 | 32.23 | O |
| ATOM | 9771 | N | LYS C | 259 | −44.045 | 28.018 | −76.960 | 1.00 | 30.87 | N |
| ATOM | 9772 | CA | LYS C | 259 | −45.492 | 27.925 | −76.760 | 1.00 | 31.43 | C |
| ATOM | 9773 | CB | LYS C | 259 | −45.806 | 27.233 | −75.430 | 1.00 | 30.41 | C |
| ATOM | 9774 | CG | LYS C | 259 | −45.522 | 25.745 | −75.505 | 1.00 | 30.13 | C |
| ATOM | 9775 | CD | LYS C | 259 | −45.284 | 25.114 | −74.152 | 1.00 | 29.96 | C |
| ATOM | 9776 | CE | LYS C | 259 | −44.817 | 23.679 | −74.330 | 1.00 | 29.65 | C |
| ATOM | 9777 | NZ | LYS C | 259 | −45.363 | 22.796 | −73.266 | 1.00 | 29.97 | N |
| ATOM | 9778 | C | LYS C | 259 | −46.239 | 29.259 | −76.912 | 1.00 | 32.03 | C |
| ATOM | 9779 | O | LYS C | 259 | −47.315 | 29.305 | −77.509 | 1.00 | 32.66 | O |
| ATOM | 9780 | N | GLN C | 260 | −45.659 | 30.339 | −76.398 | 1.00 | 32.93 | N |
| ATOM | 9781 | CA | GLN C | 260 | −46.230 | 31.669 | −76.594 | 1.00 | 33.87 | C |
| ATOM | 9782 | CB | GLN C | 260 | −45.521 | 32.717 | −75.723 | 1.00 | 35.69 | C |
| ATOM | 9783 | CG | GLN C | 260 | −45.012 | 32.211 | −74.375 | 1.00 | 36.79 | C |
| ATOM | 9784 | CD | GLN C | 260 | −45.875 | 32.641 | −73.200 | 1.00 | 37.13 | C |
| ATOM | 9785 | OE1 | GLN C | 260 | −45.495 | 33.524 | −72.423 | 1.00 | 36.68 | O |
| ATOM | 9786 | NE2 | GLN C | 260 | −47.038 | 32.017 | −73.061 | 1.00 | 37.51 | N |
| ATOM | 9787 | C | GLN C | 260 | −46.135 | 32.050 | −78.073 | 1.00 | 32.94 | C |
| ATOM | 9788 | O | GLN C | 260 | −47.116 | 32.455 | −78.672 | 1.00 | 33.48 | O |
| ATOM | 9789 | N | LEU C | 261 | −44.953 | 31.882 | −78.658 | 1.00 | 33.21 | N |
| ATOM | 9790 | CA | LEU C | 261 | −44.726 | 32.185 | −80.074 | 1.00 | 34.64 | C |
| ATOM | 9791 | CB | LEU C | 261 | −43.258 | 31.939 | −80.446 | 1.00 | 33.70 | C |
| ATOM | 9792 | CG | LEU C | 261 | −42.121 | 32.765 | −79.842 | 1.00 | 32.36 | C |
| ATOM | 9793 | CD1 | LEU C | 261 | −40.802 | 32.215 | −80.334 | 1.00 | 32.19 | C |
| ATOM | 9794 | CD2 | LEU C | 261 | −42.229 | 34.229 | −80.222 | 1.00 | 32.93 | C |
| ATOM | 9795 | C | LEU C | 261 | −45.633 | 31.368 | −81.007 | 1.00 | 36.22 | C |
| ATOM | 9796 | O | LEU C | 261 | −45.859 | 31.751 | −82.161 | 1.00 | 35.31 | O |
| ATOM | 9797 | N | ARG C | 262 | −46.130 | 30.243 | −80.490 | 1.00 | 38.64 | N |
| ATOM | 9798 | CA | ARG C | 262 | −47.024 | 29.337 | −81.209 | 1.00 | 41.28 | C |
| ATOM | 9799 | CB | ARG C | 262 | −47.115 | 28.000 | −80.460 | 1.00 | 44.98 | C |
| ATOM | 9800 | CG | ARG C | 262 | −47.739 | 26.837 | −81.230 | 1.00 | 46.98 | C |
| ATOM | 9801 | CD | ARG C | 262 | −47.233 | 25.483 | −80.723 | 1.00 | 48.56 | C |
| ATOM | 9802 | NE | ARG C | 262 | −45.783 | 25.478 | −80.476 | 1.00 | 51.46 | N |
| ATOM | 9803 | CZ | ARG C | 262 | −44.841 | 25.459 | −81.425 | 1.00 | 52.29 | C |
| ATOM | 9804 | NH1 | ARG C | 262 | −45.174 | 25.437 | −82.712 | 1.00 | 52.70 | N |
| ATOM | 9805 | NH2 | ARG C | 262 | −43.557 | 25.465 | −81.085 | 1.00 | 51.44 | N |
| ATOM | 9806 | C | ARG C | 262 | −48.411 | 29.942 | −81.344 | 1.00 | 42.20 | C |
| ATOM | 9807 | O | ARG C | 262 | −49.129 | 29.646 | −82.303 | 1.00 | 43.35 | O |
| ATOM | 9808 | N | GLU C | 263 | −48.790 | 30.787 | −80.386 | 1.00 | 44.06 | N |
| ATOM | 9809 | CA | GLU C | 263 | −50.077 | 31.477 | −80.447 | 1.00 | 47.87 | C |
| ATOM | 9810 | CB | GLU C | 263 | −50.515 | 31.940 | −79.049 | 1.00 | 51.09 | C |
| ATOM | 9811 | CG | GLU C | 263 | −50.085 | 33.349 | −78.671 | 1.00 | 57.28 | C |
| ATOM | 9812 | CD | GLU C | 263 | −49.610 | 33.457 | −77.232 | 1.00 | 64.07 | C |
| ATOM | 9813 | OE1 | GLU C | 263 | −50.136 | 32.711 | −76.369 | 1.00 | 68.03 | O |
| ATOM | 9814 | OE2 | GLU C | 263 | −48.701 | 34.285 | −76.969 | 1.00 | 63.80 | O |
| ATOM | 9815 | C | GLU C | 263 | −50.073 | 32.627 | −81.485 | 1.00 | 47.88 | C |
| ATOM | 9816 | O | GLU C | 263 | −51.080 | 33.311 | −81.680 | 1.00 | 48.06 | O |
| ATOM | 9817 | N | TRP C | 264 | −48.929 | 32.817 | −82.146 | 1.00 | 49.24 | N |
| ATOM | 9818 | CA | TRP C | 264 | −48.797 | 33.751 | −83.274 | 1.00 | 48.11 | C |
| ATOM | 9819 | CB | TRP C | 264 | −47.637 | 34.729 | −83.037 | 1.00 | 46.73 | C |
| ATOM | 9820 | CG | TRP C | 264 | −47.756 | 35.484 | −81.715 | 1.00 | 46.62 | C |
| ATOM | 9821 | CD1 | TRP C | 264 | −48.915 | 35.706 | −80.964 | 1.00 | 47.65 | C |
| ATOM | 9822 | NE1 | TRP C | 264 | −48.641 | 36.433 | −79.826 | 1.00 | 45.58 | N |
| ATOM | 9823 | CE2 | TRP C | 264 | −47.336 | 36.748 | −79.765 | 1.00 | 44.69 | C |
| ATOM | 9824 | CD2 | TRP C | 264 | −46.690 | 36.168 | −80.957 | 1.00 | 45.87 | C |
| ATOM | 9825 | CE3 | TRP C | 264 | −45.319 | 36.346 | −81.133 | 1.00 | 46.07 | C |
| ATOM | 9826 | CZ3 | TRP C | 264 | −44.608 | 37.076 | −80.161 | 1.00 | 44.78 | C |
| ATOM | 9827 | CH2 | TRP C | 264 | −45.246 | 37.618 | −79.031 | 1.00 | 44.28 | C |
| ATOM | 9828 | CZ2 | TRP C | 264 | −46.623 | 37.464 | −78.814 | 1.00 | 44.82 | C |
| ATOM | 9829 | C | TRP C | 264 | −48.702 | 33.025 | −84.611 | 1.00 | 49.12 | C |
| ATOM | 9830 | O | TRP C | 264 | −48.659 | 33.662 | −85.665 | 1.00 | 47.87 | O |
| ATOM | 9831 | N | ASP C | 265 | −48.661 | 31.681 | −84.559 | 1.00 | 50.74 | N |
| ATOM | 9832 | CA | ASP C | 265 | −49.059 | 30.797 | −85.681 | 1.00 | 49.67 | C |
| ATOM | 9833 | CB | ASP C | 265 | −48.275 | 29.467 | −85.680 | 1.00 | 48.64 | C |
| ATOM | 9834 | CG | ASP C | 265 | −48.916 | 28.381 | −86.605 | 1.00 | 49.22 | C |
| ATOM | 9835 | OD1 | ASP C | 265 | −48.708 | 28.434 | −87.846 | 1.00 | 46.85 | O |
| ATOM | 9836 | OD2 | ASP C | 265 | −49.616 | 27.472 | −86.085 | 1.00 | 45.67 | O |
| ATOM | 9837 | C | ASP C | 265 | −50.554 | 30.491 | −85.564 | 1.00 | 49.03 | C |
| ATOM | 9838 | O | ASP C | 265 | −51.273 | 30.445 | −86.563 | 1.00 | 47.68 | O |
| ATOM | 9839 | N | SER C | 272 | −38.088 | 24.850 | −88.261 | 1.00 | 40.77 | N |

-continued

| | | Atomic coordinates for CRBN:DDB1:Lenalidomide (Human protein) | | | | | | | |
|---|---|---|---|---|---|---|---|---|---|
| ATOM | 9840 | CA | SER C | 272 | −38.825 | 25.753 | −87.381 | 1.00 | 41.58 | C |
| ATOM | 9841 | CB | SER C | 272 | −39.150 | 25.056 | −86.044 | 1.00 | 41.18 | C |
| ATOM | 9842 | OG | SER C | 272 | −40.444 | 24.475 | −86.058 | 1.00 | 39.55 | O |
| ATOM | 9843 | C | SER C | 272 | −38.092 | 27.095 | −87.156 | 1.00 | 41.72 | C |
| ATOM | 9844 | O | SER C | 272 | −38.293 | 28.049 | −87.912 | 1.00 | 42.23 | O |
| ATOM | 9845 | N | LEU C | 273 | −37.259 | 27.151 | −86.107 | 1.00 | 39.80 | N |
| ATOM | 9846 | CA | LEU C | 273 | −36.482 | 28.352 | −85.717 | 1.00 | 36.44 | C |
| ATOM | 9847 | CB | LEU C | 273 | −37.188 | 29.151 | −84.597 | 1.00 | 35.60 | C |
| ATOM | 9848 | CG | LEU C | 273 | −38.664 | 28.934 | −84.237 | 1.00 | 34.87 | C |
| ATOM | 9849 | CD1 | LEU C | 273 | −38.810 | 27.805 | −83.218 | 1.00 | 34.17 | C |
| ATOM | 9850 | CD2 | LEU C | 273 | −39.264 | 30.220 | −83.697 | 1.00 | 34.18 | C |
| ATOM | 9851 | C | LEU C | 273 | −35.087 | 27.890 | −85.248 | 1.00 | 34.15 | C |
| ATOM | 9852 | O | LEU C | 273 | −34.795 | 26.694 | −85.280 | 1.00 | 33.39 | O |
| ATOM | 9853 | N | PRO C | 274 | −34.218 | 28.823 | −84.811 | 1.00 | 32.84 | N |
| ATOM | 9854 | CA | PRO C | 274 | −32.879 | 28.353 | −84.450 | 1.00 | 32.66 | C |
| ATOM | 9855 | CB | PRO C | 274 | −32.121 | 29.646 | −84.129 | 1.00 | 32.26 | C |
| ATOM | 9856 | CG | PRO C | 274 | −32.931 | 30.753 | −84.728 | 1.00 | 31.84 | C |
| ATOM | 9857 | CD | PRO C | 274 | −34.348 | 30.284 | −84.655 | 1.00 | 32.75 | C |
| ATOM | 9858 | C | PRO C | 274 | −32.884 | 27.417 | −83.234 | 1.00 | 33.21 | C |
| ATOM | 9859 | O | PRO C | 274 | −33.785 | 27.492 | −82.385 | 1.00 | 32.41 | O |
| ATOM | 9860 | N | SER C | 275 | −31.891 | 26.528 | −83.178 | 1.00 | 33.75 | N |
| ATOM | 9861 | CA | SER C | 275 | −31.737 | 25.572 | −82.075 | 1.00 | 32.87 | C |
| ATOM | 9862 | CB | SER C | 275 | −31.299 | 24.203 | −82.598 | 1.00 | 33.74 | C |
| ATOM | 9863 | OG | SER C | 275 | −32.142 | 23.765 | −83.653 | 1.00 | 35.23 | O |
| ATOM | 9864 | C | SER C | 275 | −30.713 | 26.093 | −81.080 | 1.00 | 31.88 | C |
| ATOM | 9865 | O | SER C | 275 | −30.799 | 25.805 | −79.881 | 1.00 | 32.38 | O |
| ATOM | 9866 | N | ASN C | 276 | −29.744 | 26.850 | −81.597 | 1.00 | 30.05 | N |
| ATOM | 9867 | CA | ASN C | 276 | −28.781 | 27.569 | −80.782 | 1.00 | 29.46 | C |
| ATOM | 9868 | CB | ASN C | 276 | −27.686 | 28.172 | −81.664 | 1.00 | 30.73 | C |
| ATOM | 9869 | CG | ASN C | 276 | −26.553 | 28.789 | −80.858 | 1.00 | 31.97 | C |
| ATOM | 9870 | OD1 | ASN C | 276 | −26.780 | 29.553 | −79.919 | 1.00 | 32.94 | O |
| ATOM | 9871 | ND2 | ASN C | 276 | −25.319 | 28.458 | −81.227 | 1.00 | 32.30 | N |
| ATOM | 9872 | C | ASN C | 276 | −29.467 | 28.677 | −79.993 | 1.00 | 29.22 | C |
| ATOM | 9873 | O | ASN C | 276 | −30.107 | 29.563 | −80.584 | 1.00 | 29.70 | O |
| ATOM | 9874 | N | PRO C | 277 | −29.327 | 28.639 | −78.653 | 1.00 | 27.66 | N |
| ATOM | 9875 | CA | PRO C | 277 | −29.951 | 29.615 | −77.748 | 1.00 | 26.72 | C |
| ATOM | 9876 | CB | PRO C | 277 | −29.406 | 29.220 | −76.366 | 1.00 | 26.44 | C |
| ATOM | 9877 | CG | PRO C | 277 | −29.009 | 27.797 | −76.512 | 1.00 | 26.49 | C |
| ATOM | 9878 | CD | PRO C | 277 | −28.538 | 27.635 | −77.923 | 1.00 | 26.78 | C |
| ATOM | 9879 | C | PRO C | 277 | −29.603 | 31.075 | −78.072 | 1.00 | 25.35 | C |
| ATOM | 9880 | O | PRO C | 277 | −30.472 | 31.933 | −77.972 | 1.00 | 24.83 | O |
| ATOM | 9881 | N | ILE C | 278 | −28.351 | 31.345 | −78.444 | 1.00 | 24.57 | N |
| ATOM | 9882 | CA | ILE C | 278 | −27.930 | 32.694 | −78.846 | 1.00 | 25.01 | C |
| ATOM | 9883 | CB | ILE C | 278 | −26.464 | 32.724 | −79.342 | 1.00 | 24.99 | C |
| ATOM | 9884 | CG1 | ILE C | 278 | −25.498 | 32.298 | −78.238 | 1.00 | 24.76 | C |
| ATOM | 9885 | CD1 | ILE C | 278 | −24.143 | 31.872 | −78.760 | 1.00 | 24.60 | C |
| ATOM | 9886 | CG2 | ILE C | 278 | −26.098 | 34.108 | −79.859 | 1.00 | 25.15 | C |
| ATOM | 9887 | C | ILE C | 278 | −28.829 | 33.242 | −79.959 | 1.00 | 25.04 | C |
| ATOM | 9888 | O | ILE C | 278 | −29.382 | 34.333 | −79.844 | 1.00 | 24.34 | O |
| ATOM | 9889 | N | ASP C | 279 | −28.976 | 32.471 | −81.031 | 1.00 | 25.63 | N |
| ATOM | 9890 | CA | ASP C | 279 | −29.787 | 32.892 | −82.160 | 1.00 | 26.77 | C |
| ATOM | 9891 | CB | ASP C | 279 | −29.721 | 31.851 | −83.269 | 1.00 | 27.30 | C |
| ATOM | 9892 | CG | ASP C | 279 | −28.349 | 31.736 | −83.871 | 1.00 | 28.23 | C |
| ATOM | 9893 | OD1 | ASP C | 279 | −27.719 | 32.791 | −84.147 | 1.00 | 28.37 | O |
| ATOM | 9894 | OD2 | ASP C | 279 | −27.904 | 30.588 | −84.076 | 1.00 | 28.99 | O |
| ATOM | 9895 | C | ASP C | 279 | −31.229 | 33.105 | −81.737 | 1.00 | 26.45 | C |
| ATOM | 9896 | O | ASP C | 279 | −31.829 | 34.145 | −81.997 | 1.00 | 26.30 | O |
| ATOM | 9897 | N | PHE C | 280 | −31.768 | 32.100 | −81.070 | 1.00 | 27.14 | N |
| ATOM | 9898 | CA | PHE C | 280 | −33.154 | 32.093 | −80.663 | 1.00 | 26.89 | C |
| ATOM | 9899 | CB | PHE C | 280 | −33.428 | 30.839 | −79.835 | 1.00 | 27.45 | C |
| ATOM | 9900 | CG | PHE C | 280 | −34.869 | 30.623 | −79.524 | 1.00 | 28.05 | C |
| ATOM | 9901 | CD1 | PHE C | 280 | −35.472 | 31.289 | −78.460 | 1.00 | 27.72 | C |
| ATOM | 9902 | CE1 | PHE C | 280 | −36.810 | 31.084 | −78.167 | 1.00 | 27.94 | C |
| ATOM | 9903 | CZ | PHE C | 280 | −37.562 | 30.204 | −78.934 | 1.00 | 28.04 | C |
| ATOM | 9904 | CE2 | PHE C | 280 | −36.973 | 29.532 | −79.993 | 1.00 | 28.81 | C |
| ATOM | 9905 | CD2 | PHE C | 280 | −35.631 | 29.740 | −80.285 | 1.00 | 28.63 | C |
| ATOM | 9906 | C | PHE C | 280 | −33.461 | 33.344 | −79.864 | 1.00 | 26.11 | C |
| ATOM | 9907 | O | PHE C | 280 | −34.428 | 34.032 | −80.146 | 1.00 | 26.03 | O |
| ATOM | 9908 | N | SER C | 281 | −32.602 | 33.646 | −78.892 | 1.00 | 26.07 | N |
| ATOM | 9909 | CA | SER C | 281 | −32.819 | 34.754 | −77.962 | 1.00 | 25.48 | C |
| ATOM | 9910 | CB | SER C | 281 | −31.774 | 34.734 | −76.850 | 1.00 | 25.03 | C |
| ATOM | 9911 | OG | SER C | 281 | −30.494 | 35.048 | −77.360 | 1.00 | 24.63 | O |
| ATOM | 9912 | C | SER C | 281 | −32.805 | 36.096 | −78.666 | 1.00 | 24.70 | C |
| ATOM | 9913 | O | SER C | 281 | −33.548 | 36.996 | −78.296 | 1.00 | 24.25 | O |
| ATOM | 9914 | N | TYR C | 282 | −31.964 | 36.210 | −79.689 | 1.00 | 25.19 | N |
| ATOM | 9915 | CA | TYR C | 282 | −31.899 | 37.410 | −80.543 | 1.00 | 26.07 | C |
| ATOM | 9916 | CB | TYR C | 282 | −30.561 | 37.464 | −81.288 | 1.00 | 24.52 | C |

-continued

| | | | Atomic coordinates for CRBN:DDB1:Lenalidomide (Human protein) | | | | | | |
|---|---|---|---|---|---|---|---|---|---|
| ATOM | 9917 | CG | TYR C | 282 | −29.406 | 37.882 | −80.422 | 1.00 | 24.02 | C |
| ATOM | 9918 | CD1 | TYR C | 282 | −29.531 | 38.953 | −79.536 | 1.00 | 24.03 | C |
| ATOM | 9919 | CE1 | TYR C | 282 | −28.472 | 39.350 | −78.743 | 1.00 | 23.57 | C |
| ATOM | 9920 | CZ | TYR C | 282 | −27.267 | 38.679 | −78.825 | 1.00 | 23.46 | C |
| ATOM | 9921 | OH | TYR C | 282 | −26.216 | 39.083 | −78.025 | 1.00 | 24.10 | O |
| ATOM | 9922 | CE2 | TYR C | 282 | −27.115 | 37.612 | −79.695 | 1.00 | 23.40 | C |
| ATOM | 9923 | CD2 | TYR C | 282 | −28.180 | 37.223 | −80.491 | 1.00 | 23.56 | C |
| ATOM | 9924 | C | TYR C | 282 | −33.067 | 37.558 | −81.545 | 1.00 | 27.06 | C |
| ATOM | 9925 | O | TYR C | 282 | −33.466 | 38.686 | −81.882 | 1.00 | 27.49 | O |
| ATOM | 9926 | N | ARG C | 283 | −33.588 | 36.425 | −82.022 | 1.00 | 27.46 | N |
| ATOM | 9927 | CA | ARG C | 283 | −34.729 | 36.410 | −82.928 | 1.00 | 28.87 | C |
| ATOM | 9928 | CB | ARG C | 283 | −34.890 | 35.034 | −83.557 | 1.00 | 30.00 | C |
| ATOM | 9929 | CG | ARG C | 283 | −36.146 | 34.846 | −84.390 | 1.00 | 32.61 | C |
| ATOM | 9930 | CD | ARG C | 283 | −35.867 | 34.874 | −85.889 | 1.00 | 36.71 | C |
| ATOM | 9931 | NE | ARG C | 283 | −36.430 | 33.684 | −86.541 | 1.00 | 39.75 | N |
| ATOM | 9932 | CZ | ARG C | 283 | −35.709 | 32.760 | −87.185 | 1.00 | 43.26 | C |
| ATOM | 9933 | NH1 | ARG C | 283 | −36.313 | 31.704 | −87.724 | 1.00 | 45.47 | N |
| ATOM | 9934 | NH2 | ARG C | 283 | −34.385 | 32.890 | −87.307 | 1.00 | 42.99 | N |
| ATOM | 9935 | C | ARG C | 283 | −36.029 | 36.848 | −82.231 | 1.00 | 30.12 | C |
| ATOM | 9936 | O | ARG C | 283 | −36.828 | 37.591 | −82.814 | 1.00 | 31.39 | O |
| ATOM | 9937 | N | VAL C | 284 | −36.252 | 36.401 | −80.993 | 1.00 | 29.48 | N |
| ATOM | 9938 | CA | VAL C | 284 | −37.460 | 36.822 | −80.281 | 1.00 | 28.39 | C |
| ATOM | 9939 | CB | VAL C | 284 | −37.990 | 35.789 | −79.242 | 1.00 | 28.16 | C |
| ATOM | 9940 | CG1 | VAL C | 284 | −37.629 | 34.363 | −79.644 | 1.00 | 26.88 | C |
| ATOM | 9941 | CG2 | VAL C | 284 | −37.524 | 36.108 | −77.828 | 1.00 | 27.84 | C |
| ATOM | 9942 | C | VAL C | 284 | −37.273 | 38.196 | −79.665 | 1.00 | 28.39 | C |
| ATOM | 9943 | O | VAL C | 284 | −38.252 | 38.892 | −79.399 | 1.00 | 29.42 | O |
| ATOM | 9944 | N | ALA C | 285 | −36.018 | 38.587 | −79.453 | 1.00 | 27.76 | N |
| ATOM | 9945 | CA | ALA C | 285 | −35.708 | 39.926 | −78.993 | 1.00 | 28.24 | C |
| ATOM | 9946 | CB | ALA C | 285 | −34.216 | 40.081 | −78.815 | 1.00 | 28.14 | C |
| ATOM | 9947 | C | ALA C | 285 | −36.238 | 40.972 | −79.983 | 1.00 | 29.97 | C |
| ATOM | 9948 | O | ALA C | 285 | −36.834 | 41.983 | −79.583 | 1.00 | 30.58 | O |
| ATOM | 9949 | N | ALA C | 286 | −36.025 | 40.718 | −81.274 | 1.00 | 30.69 | N |
| ATOM | 9950 | CA | ALA C | 286 | −36.448 | 41.637 | −82.327 | 1.00 | 31.68 | C |
| ATOM | 9951 | CB | ALA C | 286 | −35.699 | 41.330 | −83.616 | 1.00 | 30.93 | C |
| ATOM | 9952 | C | ALA C | 286 | −37.977 | 41.636 | −82.555 | 1.00 | 33.39 | C |
| ATOM | 9953 | O | ALA C | 286 | −38.528 | 42.597 | −83.087 | 1.00 | 34.59 | O |
| ATOM | 9954 | N | CYS C | 287 | −38.644 | 40.556 | −82.150 | 1.00 | 34.85 | N |
| ATOM | 9955 | CA | CYS C | 287 | −40.098 | 40.439 | −82.244 | 1.00 | 35.87 | C |
| ATOM | 9956 | CB | CYS C | 287 | −40.529 | 38.986 | −82.079 | 1.00 | 37.35 | C |
| ATOM | 9957 | SG | CYS C | 287 | −40.231 | 37.965 | −83.518 | 1.00 | 43.15 | S |
| ATOM | 9958 | C | CYS C | 287 | −40.821 | 41.253 | −81.184 | 1.00 | 36.43 | C |
| ATOM | 9959 | O | CYS C | 287 | −41.879 | 41.824 | −81.452 | 1.00 | 37.84 | O |
| ATOM | 9960 | N | LEU C | 288 | −40.276 | 41.267 | −79.971 | 1.00 | 35.03 | N |
| ATOM | 9961 | CA | LEU C | 288 | −40.991 | 41.819 | −78.836 | 1.00 | 35.07 | C |
| ATOM | 9962 | CB | LEU C | 288 | −40.237 | 41.545 | −77.545 | 1.00 | 34.67 | C |
| ATOM | 9963 | CG | LEU C | 288 | −40.311 | 40.153 | −76.947 | 1.00 | 35.16 | C |
| ATOM | 9964 | CD1 | LEU C | 288 | −39.866 | 40.248 | −75.495 | 1.00 | 35.61 | C |
| ATOM | 9965 | CD2 | LEU C | 288 | −41.713 | 39.564 | −77.056 | 1.00 | 35.42 | C |
| ATOM | 9966 | C | LEU C | 288 | −41.216 | 43.312 | −78.976 | 1.00 | 35.84 | C |
| ATOM | 9967 | O | LEU C | 288 | −40.243 | 44.062 | −79.061 | 1.00 | 36.33 | O |
| ATOM | 9968 | N | PRO C | 289 | −42.501 | 43.745 | −79.006 | 1.00 | 36.70 | N |
| ATOM | 9969 | CA | PRO C | 289 | −42.866 | 45.157 | −79.014 | 1.00 | 36.03 | C |
| ATOM | 9970 | CB | PRO C | 289 | −44.295 | 45.137 | −78.500 | 1.00 | 35.97 | C |
| ATOM | 9971 | CG | PRO C | 289 | −44.848 | 43.871 | −79.077 | 1.00 | 35.67 | C |
| ATOM | 9972 | CD | PRO C | 289 | −43.699 | 42.890 | −79.160 | 1.00 | 36.35 | C |
| ATOM | 9973 | C | PRO C | 289 | −41.951 | 46.016 | −78.139 | 1.00 | 37.10 | C |
| ATOM | 9974 | O | PRO C | 289 | −41.009 | 46.593 | −78.676 | 1.00 | 40.90 | O |
| ATOM | 9975 | N | ILE C | 290 | −42.191 | 46.086 | −76.828 | 1.00 | 34.72 | N |
| ATOM | 9976 | CA | ILE C | 290 | −41.410 | 46.967 | −75.901 | 1.00 | 34.74 | C |
| ATOM | 9977 | CB | ILE C | 290 | −40.328 | 46.195 | −75.105 | 1.00 | 34.13 | C |
| ATOM | 9978 | CG1 | ILE C | 290 | −39.263 | 45.599 | −76.022 | 1.00 | 34.54 | C |
| ATOM | 9979 | CD1 | ILE C | 290 | −38.103 | 44.973 | −75.273 | 1.00 | 33.13 | C |
| ATOM | 9980 | CG2 | ILE C | 290 | −40.966 | 45.120 | −74.245 | 1.00 | 34.73 | C |
| ATOM | 9981 | C | ILE C | 290 | −40.836 | 48.316 | −76.419 | 1.00 | 35.35 | C |
| ATOM | 9982 | O | ILE C | 290 | −40.934 | 48.662 | −77.601 | 1.00 | 35.02 | O |
| ATOM | 9983 | N | ASP C | 291 | −40.255 | 49.093 | −75.513 | 1.00 | 35.99 | N |
| ATOM | 9984 | CA | ASP C | 291 | −39.918 | 50.481 | −75.825 | 1.00 | 37.77 | C |
| ATOM | 9985 | CB | ASP C | 291 | −40.776 | 51.429 | −74.986 | 1.00 | 39.91 | C |
| ATOM | 9986 | CG | ASP C | 291 | −40.505 | 51.293 | −73.510 | 1.00 | 43.06 | C |
| ATOM | 9987 | OD1 | ASP C | 291 | −39.509 | 51.887 | −73.043 | 1.00 | 44.32 | O |
| ATOM | 9988 | OD2 | ASP C | 291 | −41.274 | 50.579 | −72.822 | 1.00 | 45.28 | O |
| ATOM | 9989 | C | ASP C | 291 | −38.432 | 50.813 | −75.662 | 1.00 | 37.24 | C |
| ATOM | 9990 | O | ASP C | 291 | −37.696 | 50.123 | −74.953 | 1.00 | 36.37 | O |
| ATOM | 9991 | N | ASP C | 292 | −38.015 | 51.896 | −76.311 | 1.00 | 37.32 | N |
| ATOM | 9992 | CA | ASP C | 292 | −36.608 | 52.286 | −76.383 | 1.00 | 38.14 | C |
| ATOM | 9993 | CB | ASP C | 292 | −36.464 | 53.716 | −76.946 | 1.00 | 36.56 | C |

| | | | | | -continued | | | | |
|---|---|---|---|---|---|---|---|---|---|
| Atomic coordinates for CRBN:DDB1:Lenalidomide (Human protein) | | | | | | | | | |
| ATOM | 9994 | C | ASP C | 292 | −35.815 | 52.105 | −75.068 | 1.00 | 38.37 | C |
| ATOM | 9995 | O | ASP C | 292 | −34.622 | 51.799 | −75.108 | 1.00 | 38.28 | O |
| ATOM | 9996 | N | VAL C | 293 | −36.464 | 52.276 | −73.915 | 1.00 | 37.99 | N |
| ATOM | 9997 | CA | VAL C | 293 | −35.745 | 52.122 | −72.635 | 1.00 | 38.63 | C |
| ATOM | 9998 | CB | VAL C | 293 | −36.333 | 52.988 | −71.472 | 1.00 | 38.57 | C |
| ATOM | 9999 | CG1 | VAL C | 293 | −37.749 | 52.562 | −71.100 | 1.00 | 38.29 | C |
| ATOM | 10000 | CG2 | VAL C | 293 | −35.423 | 52.942 | −70.245 | 1.00 | 36.68 | C |
| ATOM | 10001 | C | VAL C | 293 | −35.542 | 50.656 | −72.225 | 1.00 | 38.06 | C |
| ATOM | 10002 | O | VAL C | 293 | −34.486 | 50.304 | −71.700 | 1.00 | 37.75 | O |
| ATOM | 10003 | N | LEU C | 294 | −36.550 | 49.816 | −72.467 | 1.00 | 37.06 | N |
| ATOM | 10004 | CA | LEU C | 294 | −36.437 | 48.381 | −72.213 | 1.00 | 36.27 | C |
| ATOM | 10005 | CB | LEU C | 294 | −37.814 | 47.716 | −72.156 | 1.00 | 36.41 | C |
| ATOM | 10006 | CG | LEU C | 294 | −38.719 | 47.862 | −70.932 | 1.00 | 36.58 | C |
| ATOM | 10007 | CD1 | LEU C | 294 | −40.001 | 47.085 | −71.182 | 1.00 | 36.16 | C |
| ATOM | 10008 | CD2 | LEU C | 294 | −38.047 | 47.391 | −69.646 | 1.00 | 35.78 | C |
| ATOM | 10009 | C | LEU C | 294 | −35.576 | 47.676 | −73.268 | 1.00 | 36.41 | C |
| ATOM | 10010 | O | LEU C | 294 | −34.881 | 46.705 | −72.949 | 1.00 | 35.36 | O |
| ATOM | 10011 | N | ARG C | 295 | −35.634 | 48.152 | −74.518 | 1.00 | 35.14 | N |
| ATOM | 10012 | CA | ARG C | 295 | −34.827 | 47.574 | −75.597 | 1.00 | 34.94 | C |
| ATOM | 10013 | CB | ARG C | 295 | −35.191 | 48.163 | −76.969 | 1.00 | 35.66 | C |
| ATOM | 10014 | CG | ARG C | 295 | −34.992 | 47.226 | −78.168 | 1.00 | 35.06 | C |
| ATOM | 10015 | CD | ARG C | 295 | −36.229 | 46.344 | −78.378 | 1.00 | 37.48 | C |
| ATOM | 10016 | NE | ARG C | 295 | −36.537 | 45.924 | −79.761 | 1.00 | 36.88 | N |
| ATOM | 10017 | CZ | ARG C | 295 | −35.851 | 46.254 | −80.855 | 1.00 | 36.22 | C |
| ATOM | 10018 | NH1 | ARG C | 295 | −34.772 | 47.021 | −80.782 | 1.00 | 35.37 | N |
| ATOM | 10019 | NH2 | ARG C | 295 | −36.245 | 45.797 | −82.034 | 1.00 | 35.21 | N |
| ATOM | 10020 | C | ARG C | 295 | −33.336 | 47.741 | −75.329 | 1.00 | 34.76 | C |
| ATOM | 10021 | O | ARG C | 295 | −32.547 | 46.870 | −75.679 | 1.00 | 37.11 | O |
| ATOM | 10022 | N | ILE C | 296 | −32.950 | 48.847 | −74.699 | 1.00 | 33.40 | N |
| ATOM | 10023 | CA | ILE C | 296 | −31.546 | 49.065 | −74.352 | 1.00 | 34.38 | C |
| ATOM | 10024 | CB | ILE C | 296 | −31.262 | 50.534 | −73.955 | 1.00 | 33.46 | C |
| ATOM | 10025 | CG1 | ILE C | 296 | −31.535 | 51.464 | −75.143 | 1.00 | 33.50 | C |
| ATOM | 10026 | CD1 | ILE C | 296 | −31.491 | 52.944 | −74.816 | 1.00 | 34.05 | C |
| ATOM | 10027 | CG2 | ILE C | 296 | −29.822 | 50.704 | −73.475 | 1.00 | 32.80 | C |
| ATOM | 10028 | C | ILE C | 296 | −31.074 | 48.080 | −73.267 | 1.00 | 35.96 | C |
| ATOM | 10029 | O | ILE C | 296 | −29.898 | 47.683 | −73.244 | 1.00 | 36.60 | O |
| ATOM | 10030 | N | GLN C | 297 | −32.001 | 47.670 | −72.399 | 1.00 | 36.43 | N |
| ATOM | 10031 | CA | GLN C | 297 | −31.728 | 46.672 | −71.360 | 1.00 | 37.07 | C |
| ATOM | 10032 | CB | GLN C | 297 | −32.917 | 46.518 | −70.415 | 1.00 | 39.07 | C |
| ATOM | 10033 | CG | GLN C | 297 | −33.566 | 47.823 | −69.995 | 1.00 | 40.39 | C |
| ATOM | 10034 | CD | GLN C | 297 | −32.981 | 48.395 | −68.727 | 1.00 | 40.49 | C |
| ATOM | 10035 | OE1 | GLN C | 297 | −33.653 | 48.444 | −67.700 | 1.00 | 40.70 | O |
| ATOM | 10036 | NE2 | GLN C | 297 | −31.727 | 48.836 | −68.790 | 1.00 | 41.16 | N |
| ATOM | 10037 | C | GLN C | 297 | −31.348 | 45.304 | −71.926 | 1.00 | 37.03 | C |
| ATOM | 10038 | O | GLN C | 297 | −30.287 | 44.786 | −71.591 | 1.00 | 37.89 | O |
| ATOM | 10039 | N | LEU C | 298 | −32.196 | 44.712 | −72.774 | 1.00 | 36.05 | N |
| ATOM | 10040 | CA | LEU C | 298 | −31.860 | 43.402 | −73.357 | 1.00 | 35.64 | C |
| ATOM | 10041 | CB | LEU C | 298 | −32.933 | 42.866 | −74.305 | 1.00 | 36.93 | C |
| ATOM | 10042 | CG | LEU C | 298 | −34.401 | 43.177 | −74.149 | 1.00 | 37.23 | C |
| ATOM | 10043 | CD1 | LEU C | 298 | −34.699 | 44.324 | −75.091 | 1.00 | 38.13 | C |
| ATOM | 10044 | CD2 | LEU C | 298 | −35.217 | 41.954 | −74.529 | 1.00 | 36.79 | C |
| ATOM | 10045 | C | LEU C | 298 | −30.566 | 43.484 | −74.130 | 1.00 | 34.52 | C |
| ATOM | 10046 | O | LEU C | 298 | −29.747 | 42.567 | −74.087 | 1.00 | 33.95 | O |
| ATOM | 10047 | N | LEU C | 299 | −30.410 | 44.581 | −74.863 | 1.00 | 33.13 | N |
| ATOM | 10048 | CA | LEU C | 299 | −29.192 | 44.847 | −75.600 | 1.00 | 31.13 | C |
| ATOM | 10049 | CB | LEU C | 299 | −29.306 | 46.174 | −76.352 | 1.00 | 30.94 | C |
| ATOM | 10050 | CG | LEU C | 299 | −28.741 | 46.171 | −77.774 | 1.00 | 30.82 | C |
| ATOM | 10051 | CD1 | LEU C | 299 | −27.316 | 46.693 | −77.815 | 1.00 | 29.78 | C |
| ATOM | 10052 | CD2 | LEU C | 299 | −28.844 | 44.784 | −78.409 | 1.00 | 31.72 | C |
| ATOM | 10053 | C | LEU C | 299 | −27.977 | 44.833 | −74.670 | 1.00 | 28.89 | C |
| ATOM | 10054 | O | LEU C | 299 | −26.945 | 44.259 | −75.011 | 1.00 | 27.64 | O |
| ATOM | 10055 | N | LYS C | 300 | −28.123 | 45.440 | −73.492 | 1.00 | 27.65 | N |
| ATOM | 10056 | CA | LYS C | 300 | −27.107 | 45.370 | −72.444 | 1.00 | 27.32 | C |
| ATOM | 10057 | CB | LYS C | 300 | −27.504 | 46.232 | −71.242 | 1.00 | 28.97 | C |
| ATOM | 10058 | CG | LYS C | 300 | −27.272 | 47.728 | −71.388 | 1.00 | 30.72 | C |
| ATOM | 10059 | CD | LYS C | 300 | −27.310 | 48.413 | −70.023 | 1.00 | 32.19 | C |
| ATOM | 10060 | CE | LYS C | 300 | −27.893 | 49.822 | −70.121 | 1.00 | 33.84 | C |
| ATOM | 10061 | NZ | LYS C | 300 | −27.718 | 50.643 | −68.882 | 1.00 | 33.39 | N |
| ATOM | 10062 | C | LYS C | 300 | −26.821 | 43.934 | −71.961 | 1.00 | 25.72 | C |
| ATOM | 10063 | O | LYS C | 300 | −25.726 | 43.663 | −71.465 | 1.00 | 25.16 | O |
| ATOM | 10064 | N | ILE C | 301 | −27.801 | 43.033 | −72.097 | 1.00 | 24.42 | N |
| ATOM | 10065 | CA | ILE C | 301 | −27.667 | 41.637 | −71.630 | 1.00 | 23.75 | C |
| ATOM | 10066 | CB | ILE C | 301 | −29.024 | 40.897 | −71.577 | 1.00 | 23.63 | C |
| ATOM | 10067 | CG1 | ILE C | 301 | −29.974 | 41.562 | −70.579 | 1.00 | 23.57 | C |
| ATOM | 10068 | CD1 | ILE C | 301 | −31.429 | 41.168 | −70.756 | 1.00 | 23.28 | C |
| ATOM | 10069 | CG2 | ILE C | 301 | −28.825 | 39.432 | −71.209 | 1.00 | 23.63 | C |
| ATOM | 10070 | C | ILE C | 301 | −26.689 | 40.828 | −72.486 | 1.00 | 23.44 | C |

-continued

| Atomic coordinates for CRBN:DDB1:Lenalidomide (Human protein) | | | | | | | | | |
|---|---|---|---|---|---|---|---|---|---|
| ATOM | 10071 | O | ILE C | 301 | −26.796 | 40.787 | −73.721 | 1.00 | 23.47 | O |
| ATOM | 10072 | N | GLY C | 302 | −25.745 | 40.172 | −71.817 | 1.00 | 23.28 | N |
| ATOM | 10073 | CA | GLY C | 302 | −24.673 | 39.453 | −72.511 | 1.00 | 22.91 | C |
| ATOM | 10074 | C | GLY C | 302 | −24.914 | 37.970 | −72.678 | 1.00 | 21.86 | C |
| ATOM | 10075 | O | GLY C | 302 | −24.290 | 37.323 | −73.512 | 1.00 | 21.82 | O |
| ATOM | 10076 | N | SER C | 303 | −25.824 | 37.433 | −71.881 | 1.00 | 21.13 | N |
| ATOM | 10077 | CA | SER C | 303 | −26.053 | 36.012 | −71.863 | 1.00 | 20.93 | C |
| ATOM | 10078 | CB | SER C | 303 | −26.044 | 35.500 | −70.427 | 1.00 | 20.48 | C |
| ATOM | 10079 | OG | SER C | 303 | −26.274 | 34.107 | −70.406 | 1.00 | 20.30 | O |
| ATOM | 10080 | C | SER C | 303 | −27.356 | 35.604 | −72.554 | 1.00 | 21.36 | C |
| ATOM | 10081 | O | SER C | 303 | −28.402 | 36.243 | −72.382 | 1.00 | 21.74 | O |
| ATOM | 10082 | N | ALA C | 304 | −27.279 | 34.517 | −73.320 | 1.00 | 21.06 | N |
| ATOM | 10083 | CA | ALA C | 304 | −28.448 | 33.898 | −73.918 | 1.00 | 19.98 | C |
| ATOM | 10084 | CB | ALA C | 304 | −28.052 | 32.647 | −74.687 | 1.00 | 19.81 | C |
| ATOM | 10085 | C | ALA C | 304 | −29.477 | 33.567 | −72.852 | 1.00 | 19.86 | C |
| ATOM | 10086 | O | ALA C | 304 | −30.647 | 33.863 | −73.036 | 1.00 | 20.67 | O |
| ATOM | 10087 | N | ILE C | 305 | −29.035 | 32.971 | −71.737 | 1.00 | 19.24 | N |
| ATOM | 10088 | CA | ILE C | 305 | −29.942 | 32.514 | −70.671 | 1.00 | 18.55 | C |
| ATOM | 10089 | CB | ILE C | 305 | −29.201 | 31.781 | −69.515 | 1.00 | 18.58 | C |
| ATOM | 10090 | CG1 | ILE C | 305 | −28.263 | 30.669 | −70.024 | 1.00 | 18.40 | C |
| ATOM | 10091 | CD1 | ILE C | 305 | −28.941 | 29.551 | −70.784 | 1.00 | 18.48 | C |
| ATOM | 10092 | CG2 | ILE C | 305 | −30.191 | 31.270 | −68.486 | 1.00 | 18.36 | C |
| ATOM | 10093 | C | ILE C | 305 | −30.707 | 33.683 | −70.072 | 1.00 | 18.36 | C |
| ATOM | 10094 | O | ILE C | 305 | −31.922 | 33.622 | −69.937 | 1.00 | 17.96 | O |
| ATOM | 10095 | N | GLN C | 306 | −29.983 | 34.738 | −69.707 | 1.00 | 18.57 | N |
| ATOM | 10096 | CA | GLN C | 306 | −30.591 | 35.951 | −69.156 | 1.00 | 19.27 | C |
| ATOM | 10097 | CB | GLN C | 306 | −29.517 | 36.894 | −68.615 | 1.00 | 19.46 | C |
| ATOM | 10098 | CG | GLN C | 306 | −28.913 | 36.454 | −67.284 | 1.00 | 19.54 | C |
| ATOM | 10099 | CD | GLN C | 306 | −27.729 | 37.305 | −66.849 | 1.00 | 19.08 | C |
| ATOM | 10100 | OE1 | GLN C | 306 | −26.943 | 37.777 | −67.678 | 1.00 | 19.16 | O |
| ATOM | 10101 | NE2 | GLN C | 306 | −27.588 | 37.493 | −65.540 | 1.00 | 18.86 | N |
| ATOM | 10102 | C | GLN C | 306 | −31.448 | 36.684 | −70.189 | 1.00 | 19.90 | C |
| ATOM | 10103 | O | GLN C | 306 | −32.373 | 37.406 | −69.830 | 1.00 | 20.22 | O |
| ATOM | 10104 | N | ARG C | 307 | −31.123 | 36.503 | −71.468 | 1.00 | 20.23 | N |
| ATOM | 10105 | CA | ARG C | 307 | −31.916 | 37.046 | −72.554 | 1.00 | 20.21 | C |
| ATOM | 10106 | CB | ARG C | 307 | −31.145 | 36.958 | −73.876 | 1.00 | 20.52 | C |
| ATOM | 10107 | CG | ARG C | 307 | −31.461 | 38.075 | −74.861 | 1.00 | 20.90 | C |
| ATOM | 10108 | CD | ARG C | 307 | −30.519 | 38.089 | −76.056 | 1.00 | 20.92 | C |
| ATOM | 10109 | NE | ARG C | 307 | −29.161 | 38.498 | −75.702 | 1.00 | 20.95 | N |
| ATOM | 10110 | CZ | ARG C | 307 | −28.068 | 37.758 | −75.902 | 1.00 | 21.30 | C |
| ATOM | 10111 | NH1 | ARG C | 307 | −28.159 | 36.559 | −76.476 | 1.00 | 20.76 | N |
| ATOM | 10112 | NH2 | ARG C | 307 | −26.871 | 38.229 | −75.550 | 1.00 | 21.22 | N |
| ATOM | 10113 | C | ARG C | 307 | −33.265 | 36.319 | −72.635 | 1.00 | 20.37 | C |
| ATOM | 10114 | O | ARG C | 307 | −34.316 | 36.955 | −72.576 | 1.00 | 21.50 | O |
| ATOM | 10115 | N | LEU C | 308 | −33.227 | 34.992 | −72.737 | 1.00 | 20.23 | N |
| ATOM | 10116 | CA | LEU C | 308 | −34.438 | 34.155 | −72.759 | 1.00 | 20.32 | C |
| ATOM | 10117 | CB | LEU C | 308 | −34.073 | 32.673 | −72.881 | 1.00 | 20.70 | C |
| ATOM | 10118 | CG | LEU C | 308 | −33.268 | 32.244 | −74.099 | 1.00 | 21.09 | C |
| ATOM | 10119 | CD1 | LEU C | 308 | −32.603 | 30.903 | −73.864 | 1.00 | 20.67 | C |
| ATOM | 10120 | CD2 | LEU C | 308 | −34.166 | 32.199 | −75.323 | 1.00 | 22.13 | C |
| ATOM | 10121 | C | LEU C | 308 | −35.320 | 34.336 | −71.532 | 1.00 | 20.13 | C |
| ATOM | 10122 | O | LEU C | 308 | −36.537 | 34.437 | −71.659 | 1.00 | 20.52 | O |
| ATOM | 10123 | N | ARG C | 309 | −34.706 | 34.345 | −70.349 | 1.00 | 19.90 | N |
| ATOM | 10124 | CA | ARG C | 309 | −35.425 | 34.553 | −69.090 | 1.00 | 20.13 | C |
| ATOM | 10125 | CB | ARG C | 309 | −34.459 | 34.526 | −67.896 | 1.00 | 18.99 | C |
| ATOM | 10126 | CG | ARG C | 309 | −34.095 | 33.148 | −67.380 | 1.00 | 17.70 | C |
| ATOM | 10127 | CD | ARG C | 309 | −33.274 | 33.233 | −66.101 | 1.00 | 17.13 | C |
| ATOM | 10128 | NE | ARG C | 309 | −33.974 | 33.925 | −65.023 | 1.00 | 16.78 | N |
| ATOM | 10129 | CZ | ARG C | 309 | −34.872 | 33.362 | −64.214 | 1.00 | 17.20 | C |
| ATOM | 10130 | NH1 | ARG C | 309 | −35.456 | 34.079 | −63.266 | 1.00 | 17.64 | N |
| ATOM | 10131 | NH2 | ARG C | 309 | −35.204 | 32.083 | −64.343 | 1.00 | 17.19 | N |
| ATOM | 10132 | C | ARG C | 309 | −36.165 | 35.887 | −69.116 | 1.00 | 21.15 | C |
| ATOM | 10133 | O | ARG C | 309 | −37.388 | 35.933 | −69.096 | 1.00 | 21.36 | O |
| ATOM | 10134 | N | CYS C | 310 | −35.408 | 36.971 | −69.178 | 1.00 | 22.99 | N |
| ATOM | 10135 | CA | CYS C | 310 | −35.973 | 38.305 | −69.264 | 1.00 | 25.31 | C |
| ATOM | 10136 | CB | CYS C | 310 | −34.865 | 39.311 | −69.532 | 1.00 | 26.45 | C |
| ATOM | 10137 | SG | CYS C | 310 | −35.488 | 40.836 | −70.235 | 1.00 | 31.22 | S |
| ATOM | 10138 | C | CYS C | 310 | −37.061 | 38.420 | −70.337 | 1.00 | 25.64 | C |
| ATOM | 10139 | O | CYS C | 310 | −38.079 | 39.073 | −70.129 | 1.00 | 26.48 | O |
| ATOM | 10140 | N | GLU C | 311 | −36.832 | 37.787 | −71.481 | 1.00 | 26.35 | N |
| ATOM | 10141 | CA | GLU C | 311 | −37.833 | 37.706 | −72.553 | 1.00 | 26.99 | C |
| ATOM | 10142 | CB | GLU C | 311 | −37.230 | 37.072 | −73.804 | 1.00 | 28.74 | C |
| ATOM | 10143 | CG | GLU C | 311 | −36.550 | 38.082 | −74.711 | 1.00 | 30.40 | C |
| ATOM | 10144 | CD | GLU C | 311 | −35.443 | 37.470 | −75.536 | 1.00 | 32.39 | C |
| ATOM | 10145 | OE1 | GLU C | 311 | −34.517 | 38.220 | −75.927 | 1.00 | 32.28 | O |
| ATOM | 10146 | OE2 | GLU C | 311 | −35.500 | 36.239 | −75.788 | 1.00 | 33.97 | O |
| ATOM | 10147 | C | GLU C | 311 | −39.126 | 36.985 | −72.184 | 1.00 | 25.49 | C |

-continued

| | | | | | | | | | |
|---|---|---|---|---|---|---|---|---|---|
| | Atomic coordinates for CRBN:DDB1:Lenalidomide (Human protein) |

| | | | | | | | | | |
|---|---|---|---|---|---|---|---|---|---|
| ATOM | 10148 | O | GLU | C | 311 | −40.193 | 37.396 | −72.603 | 1.00 | 25.23 | O |
| ATOM | 10149 | N | LEU | C | 312 | −39.030 | 35.897 | −71.431 | 1.00 | 24.86 | N |
| ATOM | 10150 | CA | LEU | C | 312 | −40.230 | 35.243 | −70.909 | 1.00 | 24.74 | C |
| ATOM | 10151 | CB | LEU | C | 312 | −39.899 | 33.952 | −70.159 | 1.00 | 23.78 | C |
| ATOM | 10152 | CG | LEU | C | 312 | −40.150 | 32.627 | −70.872 | 1.00 | 23.40 | C |
| ATOM | 10153 | CD1 | LEU | C | 312 | −39.717 | 31.508 | −69.953 | 1.00 | 23.33 | C |
| ATOM | 10154 | CD2 | LEU | C | 312 | −41.603 | 32.441 | −71.284 | 1.00 | 22.97 | C |
| ATOM | 10155 | C | LEU | C | 312 | −40.998 | 36.168 | −69.992 | 1.00 | 24.49 | C |
| ATOM | 10156 | O | LEU | C | 312 | −42.216 | 36.217 | −70.043 | 1.00 | 25.14 | O |
| ATOM | 10157 | N | ASP | C | 313 | −40.271 | 36.896 | −69.154 | 1.00 | 24.85 | N |
| ATOM | 10158 | CA | ASP | C | 313 | −40.867 | 37.842 | −68.223 | 1.00 | 26.03 | C |
| ATOM | 10159 | CB | ASP | C | 313 | −39.764 | 38.598 | −67.491 | 1.00 | 26.34 | C |
| ATOM | 10160 | CG | ASP | C | 313 | −40.217 | 39.140 | −66.176 | 1.00 | 26.52 | C |
| ATOM | 10161 | OD1 | ASP | C | 313 | −40.949 | 40.145 | −66.161 | 1.00 | 27.11 | O |
| ATOM | 10162 | OD2 | ASP | C | 313 | −39.827 | 38.564 | −65.148 | 1.00 | 27.32 | O |
| ATOM | 10163 | C | ASP | C | 313 | −41.794 | 38.832 | −68.945 | 1.00 | 26.70 | C |
| ATOM | 10164 | O | ASP | C | 313 | −42.977 | 38.955 | −68.606 | 1.00 | 26.90 | O |
| ATOM | 10165 | N | ILE | C | 314 | −41.252 | 39.517 | −69.948 | 1.00 | 26.55 | N |
| ATOM | 10166 | CA | ILE | C | 314 | −42.011 | 40.486 | −70.725 | 1.00 | 27.26 | C |
| ATOM | 10167 | CB | ILE | C | 314 | −41.133 | 41.135 | −71.811 | 1.00 | 26.78 | C |
| ATOM | 10168 | CG1 | ILE | C | 314 | −40.254 | 42.222 | −71.190 | 1.00 | 26.02 | C |
| ATOM | 10169 | CD1 | ILE | C | 314 | −38.883 | 42.325 | −71.818 | 1.00 | 25.58 | C |
| ATOM | 10170 | CG2 | ILE | C | 314 | −41.992 | 41.714 | −72.928 | 1.00 | 27.03 | C |
| ATOM | 10171 | C | ILE | C | 314 | −43.279 | 39.883 | −71.341 | 1.00 | 28.45 | C |
| ATOM | 10172 | O | ILE | C | 314 | −44.343 | 40.503 | −71.295 | 1.00 | 29.63 | O |
| ATOM | 10173 | N | MET | C | 315 | −43.162 | 38.674 | −71.894 | 1.00 | 28.95 | N |
| ATOM | 10174 | CA | MET | C | 315 | −44.286 | 37.985 | −72.539 | 1.00 | 29.61 | C |
| ATOM | 10175 | CB | MET | C | 315 | −43.816 | 36.724 | −73.255 | 1.00 | 30.58 | C |
| ATOM | 10176 | CG | MET | C | 315 | −43.066 | 37.003 | −74.546 | 1.00 | 31.00 | C |
| ATOM | 10177 | SD | MET | C | 315 | −42.417 | 35.497 | −75.288 | 1.00 | 30.79 | S |
| ATOM | 10178 | CE | MET | C | 315 | −40.876 | 36.143 | −75.920 | 1.00 | 31.83 | C |
| ATOM | 10179 | C | MET | C | 315 | −45.427 | 37.645 | −71.588 | 1.00 | 29.96 | C |
| ATOM | 10180 | O | MET | C | 315 | −46.585 | 37.631 | −71.995 | 1.00 | 30.79 | O |
| ATOM | 10181 | N | ASN | C | 316 | −45.101 | 37.367 | −70.329 | 1.00 | 30.06 | N |
| ATOM | 10182 | CA | ASN | C | 316 | −46.127 | 37.206 | −69.304 | 1.00 | 30.44 | C |
| ATOM | 10183 | CB | ASN | C | 316 | −45.617 | 36.350 | −68.144 | 1.00 | 29.69 | C |
| ATOM | 10184 | CG | ASN | C | 316 | −44.856 | 35.123 | −68.609 | 1.00 | 29.04 | C |
| ATOM | 10185 | OD1 | ASN | C | 316 | −45.088 | 34.611 | −69.705 | 1.00 | 28.78 | O |
| ATOM | 10186 | ND2 | ASN | C | 316 | −43.932 | 34.648 | −67.776 | 1.00 | 28.93 | N |
| ATOM | 10187 | C | ASN | C | 316 | −46.615 | 38.554 | −68.784 | 1.00 | 31.74 | C |
| ATOM | 10188 | O | ASN | C | 316 | −47.818 | 38.791 | −68.719 | 1.00 | 32.40 | O |
| ATOM | 10189 | N | LYS | C | 317 | −45.675 | 39.445 | −68.453 | 1.00 | 33.15 | N |
| ATOM | 10190 | CA | LYS | C | 317 | −45.988 | 40.683 | −67.731 | 1.00 | 34.23 | C |
| ATOM | 10191 | CB | LYS | C | 317 | −44.776 | 41.153 | −66.900 | 1.00 | 32.44 | C |
| ATOM | 10192 | C | LYS | C | 317 | −46.558 | 41.839 | −68.583 | 1.00 | 36.18 | C |
| ATOM | 10193 | O | LYS | C | 317 | −47.017 | 42.832 | −68.031 | 1.00 | 37.68 | O |
| ATOM | 10194 | N | CYS | C | 318 | −46.560 | 41.713 | −69.909 | 1.00 | 37.88 | N |
| ATOM | 10195 | CA | CYS | C | 318 | −46.960 | 42.846 | −70.763 | 1.00 | 38.72 | C |
| ATOM | 10196 | CB | CYS | C | 318 | −45.746 | 43.384 | −71.518 | 1.00 | 39.19 | C |
| ATOM | 10197 | SG | CYS | C | 318 | −44.485 | 44.100 | −70.444 | 1.00 | 41.50 | S |
| ATOM | 10198 | C | CYS | C | 318 | −48.116 | 42.577 | −71.740 | 1.00 | 39.26 | C |
| ATOM | 10199 | O | CYS | C | 318 | −47.918 | 42.556 | −72.960 | 1.00 | 40.67 | O |
| ATOM | 10200 | N | THR | C | 319 | −49.324 | 42.423 | −71.207 | 1.00 | 38.30 | N |
| ATOM | 10201 | CA | THR | C | 319 | −50.478 | 42.049 | −72.035 | 1.00 | 37.99 | C |
| ATOM | 10202 | CB | THR | C | 319 | −51.581 | 41.372 | −71.203 | 1.00 | 38.81 | C |
| ATOM | 10203 | OG1 | THR | C | 319 | −52.170 | 42.329 | −70.312 | 1.00 | 39.89 | O |
| ATOM | 10204 | CG2 | THR | C | 319 | −51.001 | 40.204 | −70.409 | 1.00 | 40.26 | C |
| ATOM | 10205 | C | THR | C | 319 | −51.099 | 43.174 | −72.896 | 1.00 | 37.48 | C |
| ATOM | 10206 | O | THR | C | 319 | −51.687 | 42.890 | −73.946 | 1.00 | 37.41 | O |
| ATOM | 10207 | N | SER | C | 320 | −50.981 | 44.431 | −72.461 | 1.00 | 35.49 | N |
| ATOM | 10208 | CA | SER | C | 320 | −51.559 | 45.561 | −73.210 | 1.00 | 32.94 | C |
| ATOM | 10209 | CB | SER | C | 320 | −52.553 | 46.331 | −72.342 | 1.00 | 31.59 | C |
| ATOM | 10210 | OG | SER | C | 320 | −51.914 | 47.378 | −71.648 | 1.00 | 31.98 | O |
| ATOM | 10211 | C | SER | C | 320 | −50.499 | 46.507 | −73.822 | 1.00 | 32.42 | C |
| ATOM | 10212 | O | SER | C | 320 | −49.314 | 46.432 | −73.476 | 1.00 | 32.80 | O |
| ATOM | 10213 | N | LEU | C | 321 | −50.941 | 47.382 | −74.734 | 1.00 | 30.81 | N |
| ATOM | 10214 | CA | LEU | C | 321 | −50.062 | 48.300 | −75.473 | 1.00 | 28.89 | C |
| ATOM | 10215 | CB | LEU | C | 321 | −49.645 | 47.669 | −76.802 | 1.00 | 28.75 | C |
| ATOM | 10216 | CG | LEU | C | 321 | −48.589 | 46.561 | −76.788 | 1.00 | 28.35 | C |
| ATOM | 10217 | CD1 | LEU | C | 321 | −48.677 | 45.748 | −78.067 | 1.00 | 28.82 | C |
| ATOM | 10218 | CD2 | LEU | C | 321 | −47.187 | 47.118 | −76.609 | 1.00 | 27.54 | C |
| ATOM | 10219 | C | LEU | C | 321 | −50.761 | 49.627 | −75.745 | 1.00 | 28.02 | C |
| ATOM | 10220 | O | LEU | C | 321 | −51.854 | 49.640 | −76.303 | 1.00 | 27.49 | O |
| ATOM | 10221 | N | CYS | C | 322 | −50.199 | 50.812 | −75.419 | 1.00 | 28.00 | N |
| ATOM | 10222 | CA | CYS | C | 322 | −50.929 | 52.143 | −75.567 | 1.00 | 27.86 | C |
| ATOM | 10223 | CB | CYS | C | 322 | −51.485 | 52.598 | −74.220 | 1.00 | 28.61 | C |
| ATOM | 10224 | SG | CYS | C | 322 | −51.570 | 51.417 | −72.879 | 1.00 | 29.62 | S |

-continued

| | | | Atomic coordinates for CRBN:DDB1:Lenalidomide (Human protein) | | | | | | |
|---|---|---|---|---|---|---|---|---|---|
| ATOM | 10225 | C | CYS C | 322 | −50.269 | 53.419 | −76.203 | 1.00 | 27.28 | C |
| ATOM | 10226 | O | CYS C | 322 | −49.110 | 53.368 | −76.437 | 1.00 | 27.58 | O |
| ATOM | 10227 | O | CYS C | 323 | −49.014 | 54.729 | −75.263 | 1.00 | 30.00 | O |
| ATOM | 10228 | N | CYS C | 323 | −51.010 | 54.459 | −76.543 | 1.00 | 30.00 | N |
| ATOM | 10229 | CA | CYS C | 323 | −50.249 | 55.511 | −77.146 | 1.00 | 30.00 | C |
| ATOM | 10230 | C | CYS C | 323 | −49.039 | 55.460 | −76.252 | 1.00 | 30.00 | C |
| ATOM | 10231 | CB | CYS C | 323 | −50.885 | 56.872 | −77.051 | 1.00 | 20.00 | C |
| ATOM | 10232 | SG | CYS C | 323 | −49.691 | 58.075 | −77.649 | 1.00 | 20.00 | S |
| ATOM | 10233 | N | LYS C | 324 | −48.028 | 56.226 | −76.591 | 1.00 | 28.55 | N |
| ATOM | 10234 | CA | LYS C | 324 | −46.840 | 56.257 | −75.770 | 1.00 | 28.81 | C |
| ATOM | 10235 | CB | LYS C | 324 | −45.628 | 56.075 | −76.630 | 1.00 | 30.57 | C |
| ATOM | 10236 | CG | LYS C | 324 | −44.475 | 55.416 | −75.919 | 1.00 | 32.15 | C |
| ATOM | 10237 | CD | LYS C | 324 | −43.337 | 56.369 | −75.729 | 1.00 | 33.14 | C |
| ATOM | 10238 | CE | LYS C | 324 | −42.094 | 55.607 | −75.403 | 1.00 | 34.39 | C |
| ATOM | 10239 | NZ | LYS C | 324 | −41.941 | 54.532 | −76.413 | 1.00 | 37.31 | N |
| ATOM | 10240 | C | LYS C | 324 | −46.811 | 57.625 | −75.221 | 1.00 | 28.84 | C |
| ATOM | 10241 | O | LYS C | 324 | −46.538 | 57.849 | −74.068 | 1.00 | 28.50 | O |
| ATOM | 10242 | N | GLN C | 325 | −47.097 | 58.566 | −76.099 | 1.00 | 28.91 | N |
| ATOM | 10243 | CA | GLN C | 325 | −47.386 | 59.908 | −75.720 | 1.00 | 29.27 | C |
| ATOM | 10244 | CB | GLN C | 325 | −47.964 | 60.651 | −76.892 | 1.00 | 29.31 | C |
| ATOM | 10245 | CG | GLN C | 325 | −48.329 | 62.077 | −76.578 | 1.00 | 30.12 | C |
| ATOM | 10246 | CD | GLN C | 325 | −47.121 | 62.932 | −76.399 | 1.00 | 30.82 | C |
| ATOM | 10247 | OE1 | GLN C | 325 | −46.041 | 62.584 | −76.831 | 1.00 | 32.09 | O |
| ATOM | 10248 | NE2 | GLN C | 325 | −47.295 | 64.051 | −75.756 | 1.00 | 30.42 | N |
| ATOM | 10249 | C | GLN C | 325 | −48.421 | 59.689 | −74.677 | 1.00 | 29.77 | C |
| ATOM | 10250 | O | GLN C | 325 | −48.343 | 58.704 | −74.000 | 1.00 | 31.34 | O |
| ATOM | 10251 | O | CYS C | 326 | −50.813 | 58.254 | −74.443 | 1.00 | 30.00 | O |
| ATOM | 10252 | N | CYS C | 326 | −49.376 | 60.622 | −74.552 | 1.00 | 30.00 | N |
| ATOM | 10253 | CA | CYS C | 326 | −50.516 | 60.461 | −73.649 | 1.00 | 30.00 | C |
| ATOM | 10254 | C | CYS C | 326 | −50.590 | 58.979 | −73.482 | 1.00 | 30.00 | C |
| ATOM | 10255 | CB | CYS C | 326 | −51.807 | 61.021 | −74.265 | 1.00 | 20.00 | C |
| ATOM | 10256 | SG | CYS C | 326 | −53.080 | 59.832 | −74.782 | 1.00 | 20.00 | S |
| ATOM | 10257 | N | GLN C | 327 | −50.344 | 58.493 | −72.285 | 1.00 | 33.71 | N |
| ATOM | 10258 | CA | GLN C | 327 | −49.940 | 57.119 | −72.213 | 1.00 | 35.17 | C |
| ATOM | 10259 | CB | GLN C | 327 | −48.576 | 57.051 | −71.543 | 1.00 | 35.36 | C |
| ATOM | 10260 | CG | GLN C | 327 | −48.613 | 57.030 | −70.042 | 1.00 | 35.93 | C |
| ATOM | 10261 | CD | GLN C | 327 | −47.304 | 57.405 | −69.443 | 1.00 | 37.72 | C |
| ATOM | 10262 | OE1 | GLN C | 327 | −46.651 | 58.307 | −69.915 | 1.00 | 39.64 | O |
| ATOM | 10263 | NE2 | GLN C | 327 | −46.911 | 56.716 | −68.400 | 1.00 | 37.96 | N |
| ATOM | 10264 | C | GLN C | 327 | −50.836 | 56.102 | −71.564 | 1.00 | 36.84 | C |
| ATOM | 10265 | O | GLN C | 327 | −50.459 | 54.961 | −71.485 | 1.00 | 38.04 | O |
| ATOM | 10266 | N | GLU C | 328 | −51.993 | 56.499 | −71.079 | 1.00 | 38.65 | N |
| ATOM | 10267 | CA | GLU C | 328 | −52.828 | 55.571 | −70.341 | 1.00 | 40.08 | C |
| ATOM | 10268 | CB | GLU C | 328 | −53.379 | 56.225 | −69.069 | 1.00 | 42.82 | C |
| ATOM | 10269 | CG | GLU C | 328 | −52.335 | 56.504 | −67.990 | 1.00 | 44.75 | C |
| ATOM | 10270 | CD | GLU C | 328 | −52.049 | 55.307 | −67.105 | 1.00 | 46.60 | C |
| ATOM | 10271 | OE1 | GLU C | 328 | −50.866 | 55.031 | −66.859 | 1.00 | 47.60 | O |
| ATOM | 10272 | OE2 | GLU C | 328 | −52.996 | 54.638 | −66.650 | 1.00 | 47.01 | O |
| ATOM | 10273 | C | GLU C | 328 | −53.934 | 55.044 | −71.215 | 1.00 | 38.58 | C |
| ATOM | 10274 | O | GLU C | 328 | −55.000 | 54.719 | −70.755 | 1.00 | 39.47 | O |
| ATOM | 10275 | N | THR C | 329 | −53.636 | 54.933 | −72.492 | 1.00 | 37.05 | N |
| ATOM | 10276 | CA | THR C | 329 | −54.638 | 54.654 | −73.538 | 1.00 | 35.59 | C |
| ATOM | 10277 | CB | THR C | 329 | −54.863 | 55.893 | −74.440 | 1.00 | 35.01 | C |
| ATOM | 10278 | OG1 | THR C | 329 | −55.454 | 56.942 | −73.656 | 1.00 | 34.92 | O |
| ATOM | 10279 | CG2 | THR C | 329 | −55.772 | 55.558 | −75.637 | 1.00 | 33.48 | C |
| ATOM | 10280 | C | THR C | 329 | −54.349 | 53.391 | −74.373 | 1.00 | 34.31 | C |
| ATOM | 10281 | O | THR C | 329 | −53.374 | 53.338 | −75.120 | 1.00 | 34.17 | O |
| ATOM | 10282 | N | GLU C | 330 | −55.234 | 52.399 | −74.256 | 1.00 | 32.74 | N |
| ATOM | 10283 | CA | GLU C | 330 | −55.038 | 51.070 | −74.852 | 1.00 | 31.44 | C |
| ATOM | 10284 | CB | GLU C | 330 | −55.945 | 50.054 | −74.160 | 1.00 | 32.33 | C |
| ATOM | 10285 | CG | GLU C | 330 | −55.767 | 48.626 | −74.642 | 1.00 | 33.30 | C |
| ATOM | 10286 | CD | GLU C | 330 | −56.359 | 47.609 | −73.687 | 1.00 | 33.72 | C |
| ATOM | 10287 | OE1 | GLU C | 330 | −55.567 | 46.890 | −73.048 | 1.00 | 33.81 | O |
| ATOM | 10288 | OE2 | GLU C | 330 | −57.608 | 47.535 | −73.566 | 1.00 | 33.76 | O |
| ATOM | 10289 | C | GLU C | 330 | −55.266 | 51.021 | −76.360 | 1.00 | 29.81 | C |
| ATOM | 10290 | O | GLU C | 330 | −56.343 | 51.358 | −76.843 | 1.00 | 29.73 | O |
| ATOM | 10291 | N | ILE C | 331 | −54.248 | 50.583 | −77.095 | 1.00 | 28.55 | N |
| ATOM | 10292 | CA | ILE C | 331 | −54.343 | 50.467 | −78.552 | 1.00 | 28.42 | C |
| ATOM | 10293 | CB | ILE C | 331 | −53.049 | 50.955 | −79.280 | 1.00 | 28.07 | C |
| ATOM | 10294 | CG1 | ILE C | 331 | −52.582 | 52.331 | −78.766 | 1.00 | 28.27 | C |
| ATOM | 10295 | CD1 | ILE C | 331 | −53.463 | 53.516 | −79.141 | 1.00 | 28.42 | C |
| ATOM | 10296 | CG2 | ILE C | 331 | −53.231 | 50.970 | −80.798 | 1.00 | 27.94 | C |
| ATOM | 10297 | C | ILE C | 331 | −54.679 | 49.023 | −78.942 | 1.00 | 28.11 | C |
| ATOM | 10298 | O | ILE C | 331 | −55.602 | 48.781 | −79.722 | 1.00 | 27.74 | O |
| ATOM | 10299 | N | THR C | 332 | −53.937 | 48.071 | −78.383 | 1.00 | 28.31 | N |
| ATOM | 10300 | CA | THR C | 332 | −54.138 | 46.654 | −78.682 | 1.00 | 29.06 | C |
| ATOM | 10301 | CB | THR C | 332 | −53.504 | 46.270 | −80.044 | 1.00 | 29.15 | C |

-continued

| \multicolumn{9}{|c|}{Atomic coordinates for CRBN:DDB1:Lenalidomide (Human protein)} |

| ATOM | 10302 | OG1 | THR C | 332 | −53.924 | 44.954 | −80.422 | 1.00 | 30.59 | O |
|------|-------|-----|-------|-----|---------|--------|---------|------|-------|---|
| ATOM | 10303 | CG2 | THR C | 332 | −51.979 | 46.323 | −79.987 | 1.00 | 29.46 | C |
| ATOM | 10304 | C | THR C | 332 | −53.649 | 45.740 | −77.535 | 1.00 | 29.20 | C |
| ATOM | 10305 | O | THR C | 332 | −53.127 | 46.221 | −76.528 | 1.00 | 28.24 | O |
| ATOM | 10306 | N | THR C | 333 | −53.848 | 44.432 | −77.683 | 1.00 | 30.52 | N |
| ATOM | 10307 | CA | THR C | 333 | −53.397 | 43.465 | −76.673 | 1.00 | 32.61 | C |
| ATOM | 10308 | CB | THR C | 333 | −54.568 | 42.827 | −75.873 | 1.00 | 31.18 | C |
| ATOM | 10309 | OG1 | THR C | 333 | −55.584 | 42.356 | −76.770 | 1.00 | 30.23 | O |
| ATOM | 10310 | CG2 | THR C | 333 | −55.167 | 43.828 | −74.906 | 1.00 | 30.69 | C |
| ATOM | 10311 | C | THR C | 333 | −52.524 | 42.358 | −77.265 | 1.00 | 34.87 | C |
| ATOM | 10312 | O | THR C | 333 | −52.358 | 42.262 | −78.489 | 1.00 | 34.02 | O |
| ATOM | 10313 | N | LYS C | 334 | −51.961 | 41.540 | −76.371 | 1.00 | 36.51 | N |
| ATOM | 10314 | CA | LYS C | 334 | −51.210 | 40.348 | −76.736 | 1.00 | 37.13 | C |
| ATOM | 10315 | CB | LYS C | 334 | −50.842 | 39.555 | −75.478 | 1.00 | 38.57 | C |
| ATOM | 10316 | CG | LYS C | 334 | −50.070 | 38.267 | −75.729 | 1.00 | 39.10 | C |
| ATOM | 10317 | CD | LYS C | 334 | −49.551 | 37.657 | −74.429 | 1.00 | 39.18 | C |
| ATOM | 10318 | CE | LYS C | 334 | −48.358 | 36.747 | −74.699 | 1.00 | 39.28 | C |
| ATOM | 10319 | NZ | LYS C | 334 | −47.892 | 36.022 | −73.490 | 1.00 | 38.25 | N |
| ATOM | 10320 | C | LYS C | 334 | −52.060 | 39.496 | −77.650 | 1.00 | 37.78 | C |
| ATOM | 10321 | O | LYS C | 334 | −51.610 | 39.094 | −78.725 | 1.00 | 38.45 | O |
| ATOM | 10322 | N | ASN C | 335 | −53.301 | 39.252 | −77.226 | 1.00 | 37.48 | N |
| ATOM | 10323 | CA | ASN C | 335 | −54.260 | 38.467 | −78.003 | 1.00 | 38.20 | C |
| ATOM | 10324 | CB | ASN C | 335 | −55.683 | 38.708 | −77.493 | 1.00 | 39.97 | C |
| ATOM | 10325 | CG | ASN C | 335 | −55.892 | 38.217 | −76.077 | 1.00 | 40.91 | C |
| ATOM | 10326 | OD1 | ASN C | 335 | −56.974 | 38.392 | −75.510 | 1.00 | 41.71 | O |
| ATOM | 10327 | ND2 | ASN C | 335 | −54.865 | 37.597 | −75.496 | 1.00 | 39.92 | N |
| ATOM | 10328 | C | ASN C | 335 | −54.224 | 38.739 | −79.506 | 1.00 | 37.45 | C |
| ATOM | 10329 | O | ASN C | 335 | −54.407 | 37.823 | −80.306 | 1.00 | 38.02 | O |
| ATOM | 10330 | N | GLU C | 336 | −53.982 | 39.995 | −79.882 | 1.00 | 36.22 | N |
| ATOM | 10331 | CA | GLU C | 336 | −54.143 | 40.423 | −81.274 | 1.00 | 35.67 | C |
| ATOM | 10332 | CB | GLU C | 336 | −54.736 | 41.827 | −81.335 | 1.00 | 37.40 | C |
| ATOM | 10333 | CG | GLU C | 336 | −56.005 | 41.993 | −80.503 | 1.00 | 41.69 | C |
| ATOM | 10334 | CD | GLU C | 336 | −57.188 | 41.141 | −80.975 | 1.00 | 43.76 | C |
| ATOM | 10335 | OE1 | GLU C | 336 | −58.269 | 41.249 | −80.348 | 1.00 | 45.56 | O |
| ATOM | 10336 | OE2 | GLU C | 336 | −57.057 | 40.376 | −81.965 | 1.00 | 44.52 | O |
| ATOM | 10337 | C | GLU C | 336 | −52.887 | 40.317 | −82.138 | 1.00 | 32.73 | C |
| ATOM | 10338 | O | GLU C | 336 | −52.972 | 40.335 | −83.364 | 1.00 | 31.22 | O |
| ATOM | 10339 | N | ILE C | 337 | −51.733 | 40.197 | −81.493 | 1.00 | 31.40 | N |
| ATOM | 10340 | CA | ILE C | 337 | −50.459 | 40.092 | −82.196 | 1.00 | 31.48 | C |
| ATOM | 10341 | CB | ILE C | 337 | −49.252 | 40.134 | −81.221 | 1.00 | 30.92 | C |
| ATOM | 10342 | CG1 | ILE C | 337 | −49.192 | 41.468 | −80.484 | 1.00 | 30.27 | C |
| ATOM | 10343 | CD1 | ILE C | 337 | −48.276 | 41.453 | −79.285 | 1.00 | 30.16 | C |
| ATOM | 10344 | CG2 | ILE C | 337 | −47.940 | 39.898 | −81.956 | 1.00 | 30.13 | C |
| ATOM | 10345 | C | ILE C | 337 | −50.405 | 38.806 | −83.017 | 1.00 | 32.03 | C |
| ATOM | 10346 | O | ILE C | 337 | −50.673 | 37.711 | −82.503 | 1.00 | 32.55 | O |
| ATOM | 10347 | N | PHE C | 338 | −50.068 | 38.950 | −84.295 | 1.00 | 31.24 | N |
| ATOM | 10348 | CA | PHE C | 338 | −49.843 | 37.803 | −85.156 | 1.00 | 31.26 | C |
| ATOM | 10349 | CB | PHE C | 338 | −51.139 | 37.423 | −85.889 | 1.00 | 29.91 | C |
| ATOM | 10350 | CG | PHE C | 338 | −51.416 | 38.249 | −87.103 | 1.00 | 29.35 | C |
| ATOM | 10351 | CD1 | PHE C | 338 | −51.610 | 39.620 | −87.003 | 1.00 | 29.62 | C |
| ATOM | 10352 | CE1 | PHE C | 338 | −51.849 | 40.384 | −88.133 | 1.00 | 29.58 | C |
| ATOM | 10353 | CZ | PHE C | 338 | −51.911 | 39.779 | −89.375 | 1.00 | 29.65 | C |
| ATOM | 10354 | CE2 | PHE C | 338 | −51.727 | 38.412 | −89.487 | 1.00 | 29.61 | C |
| ATOM | 10355 | CD2 | PHE C | 338 | −51.477 | 37.656 | −88.354 | 1.00 | 29.42 | C |
| ATOM | 10356 | C | PHE C | 338 | −48.688 | 38.085 | −86.131 | 1.00 | 31.80 | C |
| ATOM | 10357 | O | PHE C | 338 | −48.403 | 39.246 | −86.455 | 1.00 | 30.79 | O |
| ATOM | 10358 | N | SER C | 339 | −48.023 | 37.019 | −86.575 | 1.00 | 32.10 | N |
| ATOM | 10359 | CA | SER C | 339 | −46.869 | 37.124 | −87.463 | 1.00 | 31.91 | C |
| ATOM | 10360 | CB | SER C | 339 | −45.873 | 35.998 | −87.188 | 1.00 | 31.13 | C |
| ATOM | 10361 | OG | SER C | 339 | −45.839 | 35.703 | −85.801 | 1.00 | 32.80 | O |
| ATOM | 10362 | C | SER C | 339 | −47.316 | 37.061 | −88.901 | 1.00 | 32.38 | C |
| ATOM | 10363 | O | SER C | 339 | −47.450 | 35.989 | −89.469 | 1.00 | 32.27 | O |
| ATOM | 10364 | N | LEU C | 340 | −47.556 | 38.219 | −89.493 | 1.00 | 34.71 | N |
| ATOM | 10365 | CA | LEU C | 340 | −47.859 | 38.274 | −90.908 | 1.00 | 35.52 | C |
| ATOM | 10366 | CB | LEU C | 340 | −48.348 | 39.662 | −91.299 | 1.00 | 35.93 | C |
| ATOM | 10367 | CG | LEU C | 340 | −49.641 | 39.766 | −92.106 | 1.00 | 36.00 | C |
| ATOM | 10368 | CD1 | LEU C | 340 | −49.574 | 40.991 | −93.003 | 1.00 | 35.67 | C |
| ATOM | 10369 | CD2 | LEU C | 340 | −49.928 | 38.510 | −92.917 | 1.00 | 35.09 | C |
| ATOM | 10370 | C | LEU C | 340 | −46.588 | 37.947 | −91.662 | 1.00 | 36.98 | C |
| ATOM | 10371 | O | LEU C | 340 | −46.620 | 37.231 | −92.658 | 1.00 | 39.23 | O |
| ATOM | 10372 | N | SER C | 341 | −45.468 | 38.474 | −91.171 | 1.00 | 37.68 | N |
| ATOM | 10373 | CA | SER C | 341 | −44.161 | 38.147 | −91.712 | 1.00 | 37.80 | C |
| ATOM | 10374 | CB | SER C | 341 | −43.172 | 39.297 | −91.482 | 1.00 | 38.13 | C |
| ATOM | 10375 | OG | SER C | 341 | −41.822 | 38.877 | −91.638 | 1.00 | 37.74 | O |
| ATOM | 10376 | C | SER C | 341 | −43.647 | 36.885 | −91.058 | 1.00 | 38.72 | C |
| ATOM | 10377 | O | SER C | 341 | −43.706 | 36.741 | −89.830 | 1.00 | 38.63 | O |
| ATOM | 10378 | N | LEU C | 342 | −43.165 | 35.973 | −91.899 | 1.00 | 40.54 | N |

-continued

| | | | | Atomic coordinates for CRBN:DDB1:Lenalidomide (Human protein) | | | | | |
|---|---|---|---|---|---|---|---|---|---|
| ATOM | 10379 | CA | LEU C | 342 | −42.340 | 34.835 | −91.486 | 1.00 | 43.39 | C |
| ATOM | 10380 | CB | LEU C | 342 | −41.423 | 34.430 | −92.647 | 1.00 | 44.01 | C |
| ATOM | 10381 | CG | LEU C | 342 | −41.111 | 32.959 | −92.938 | 1.00 | 44.26 | C |
| ATOM | 10382 | CD1 | LEU C | 342 | −40.377 | 32.869 | −94.269 | 1.00 | 43.78 | C |
| ATOM | 10383 | CD2 | LEU C | 342 | −40.311 | 32.287 | −91.822 | 1.00 | 44.08 | C |
| ATOM | 10384 | C | LEU C | 342 | −41.481 | 35.143 | −90.245 | 1.00 | 45.31 | C |
| ATOM | 10385 | O | LEU C | 342 | −41.512 | 34.399 | −89.260 | 1.00 | 44.98 | O |
| ATOM | 10386 | N | CYS C | 343 | −40.733 | 36.247 | −90.300 | 1.00 | 46.18 | N |
| ATOM | 10387 | CA | CYS C | 343 | −39.808 | 36.643 | −89.230 | 1.00 | 46.90 | C |
| ATOM | 10388 | CB | CYS C | 343 | −39.038 | 37.880 | −89.655 | 1.00 | 49.16 | C |
| ATOM | 10389 | SG | CYS C | 343 | −38.070 | 37.582 | −91.138 | 1.00 | 57.66 | S |
| ATOM | 10390 | C | CYS C | 343 | −40.445 | 36.900 | −87.867 | 1.00 | 45.38 | C |
| ATOM | 10391 | O | CYS C | 343 | −39.741 | 36.955 | −86.855 | 1.00 | 43.57 | O |
| ATOM | 10392 | N | GLY C | 344 | −41.765 | 37.076 | −87.846 | 1.00 | 44.02 | N |
| ATOM | 10393 | CA | GLY C | 344 | −42.484 | 37.366 | −86.606 | 1.00 | 40.38 | C |
| ATOM | 10394 | C | GLY C | 344 | −43.482 | 38.510 | −86.673 | 1.00 | 36.50 | C |
| ATOM | 10395 | O | GLY C | 344 | −43.802 | 39.008 | −87.752 | 1.00 | 38.19 | O |
| ATOM | 10396 | N | PRO C | 345 | −44.000 | 38.922 | −85.511 | 1.00 | 33.82 | N |
| ATOM | 10397 | CA | PRO C | 345 | −44.947 | 40.027 | −85.425 | 1.00 | 33.17 | C |
| ATOM | 10398 | CB | PRO C | 345 | −45.425 | 39.964 | −83.974 | 1.00 | 32.76 | C |
| ATOM | 10399 | CG | PRO C | 345 | −44.343 | 39.254 | −83.242 | 1.00 | 34.07 | C |
| ATOM | 10400 | CD | PRO C | 345 | −43.830 | 38.243 | −84.216 | 1.00 | 34.07 | C |
| ATOM | 10401 | C | PRO C | 345 | −44.317 | 41.386 | −85.692 | 1.00 | 32.34 | C |
| ATOM | 10402 | O | PRO C | 345 | −45.032 | 42.373 | −85.824 | 1.00 | 30.68 | O |
| ATOM | 10403 | N | MET C | 346 | −42.990 | 41.432 | −85.766 | 1.00 | 32.93 | N |
| ATOM | 10404 | CA | MET C | 346 | −42.282 | 42.700 | −85.925 | 1.00 | 33.39 | C |
| ATOM | 10405 | CB | MET C | 346 | −42.016 | 43.346 | −84.566 | 1.00 | 32.96 | C |
| ATOM | 10406 | CG | MET C | 346 | −41.696 | 44.824 | −84.642 | 1.00 | 33.63 | C |
| ATOM | 10407 | SD | MET C | 346 | −41.946 | 45.666 | −83.069 | 1.00 | 34.92 | S |
| ATOM | 10408 | CE | MET C | 346 | −40.604 | 44.977 | −82.111 | 1.00 | 34.80 | C |
| ATOM | 10409 | C | MET C | 346 | −40.986 | 42.586 | −86.735 | 1.00 | 33.84 | C |
| ATOM | 10410 | O | MET C | 346 | −40.181 | 41.663 | −86.537 | 1.00 | 35.08 | O |
| ATOM | 10411 | N | ALA C | 347 | −40.821 | 43.532 | −87.663 | 1.00 | 32.32 | N |
| ATOM | 10412 | CA | ALA C | 347 | −39.629 | 43.664 | −88.497 | 1.00 | 29.12 | C |
| ATOM | 10413 | CB | ALA C | 347 | −39.805 | 42.900 | −89.798 | 1.00 | 28.73 | C |
| ATOM | 10414 | C | ALA C | 347 | −39.416 | 45.142 | −88.765 | 1.00 | 27.16 | C |
| ATOM | 10415 | O | ALA C | 347 | −40.289 | 45.949 | −88.481 | 1.00 | 26.54 | O |
| ATOM | 10416 | N | ALA C | 348 | −38.249 | 45.503 | −89.283 | 1.00 | 27.20 | N |
| ATOM | 10417 | CA | ALA C | 348 | −37.982 | 46.895 | −89.638 | 1.00 | 27.50 | C |
| ATOM | 10418 | CB | ALA C | 348 | −36.568 | 47.296 | −89.245 | 1.00 | 27.43 | C |
| ATOM | 10419 | C | ALA C | 348 | −38.239 | 47.166 | −91.127 | 1.00 | 27.44 | C |
| ATOM | 10420 | O | ALA C | 348 | −37.817 | 46.399 | −91.999 | 1.00 | 27.69 | N |
| ATOM | 10421 | N | TYR C | 349 | −38.934 | 48.266 | −91.399 | 1.00 | 27.16 | N |
| ATOM | 10422 | CA | TYR C | 349 | −39.247 | 48.659 | −92.757 | 1.00 | 27.05 | C |
| ATOM | 10423 | CB | TYR C | 349 | −40.728 | 48.435 | −93.023 | 1.00 | 27.71 | C |
| ATOM | 10424 | CG | TYR C | 349 | −41.197 | 47.020 | −92.752 | 1.00 | 28.88 | C |
| ATOM | 10425 | CD1 | TYR C | 349 | −40.981 | 46.005 | −93.689 | 1.00 | 28.96 | C |
| ATOM | 10426 | CE1 | TYR C | 349 | −41.412 | 44.711 | −93.454 | 1.00 | 28.30 | C |
| ATOM | 10427 | CZ | TYR C | 349 | −42.078 | 44.412 | −92.274 | 1.00 | 28.78 | C |
| ATOM | 10428 | OH | TYR C | 349 | −42.499 | 43.113 | −92.053 | 1.00 | 29.31 | O |
| ATOM | 10429 | CE2 | TYR C | 349 | −42.316 | 45.402 | −91.328 | 1.00 | 28.21 | C |
| ATOM | 10430 | CD2 | TYR C | 349 | −41.874 | 46.696 | −91.570 | 1.00 | 28.25 | C |
| ATOM | 10431 | C | TYR C | 349 | −38.887 | 50.125 | −92.975 | 1.00 | 26.87 | C |
| ATOM | 10432 | O | TYR C | 349 | −39.060 | 50.944 | −92.065 | 1.00 | 26.43 | O |
| ATOM | 10433 | N | VAL C | 350 | −38.373 | 50.446 | −94.168 | 1.00 | 26.11 | N |
| ATOM | 10434 | CA | VAL C | 350 | −38.085 | 51.833 | −94.546 | 1.00 | 26.68 | C |
| ATOM | 10435 | CB | VAL C | 350 | −36.881 | 51.972 | −95.510 | 1.00 | 27.48 | C |
| ATOM | 10436 | CG1 | VAL C | 350 | −35.754 | 52.785 | −94.894 | 1.00 | 27.76 | C |
| ATOM | 10437 | CG2 | VAL C | 350 | −36.413 | 50.627 | −96.037 | 1.00 | 28.18 | C |
| ATOM | 10438 | C | VAL C | 350 | −39.250 | 52.461 | −95.276 | 1.00 | 26.91 | C |
| ATOM | 10439 | O | VAL C | 350 | −39.904 | 51.808 | −96.086 | 1.00 | 26.80 | O |
| ATOM | 10440 | N | ASN C | 351 | −39.484 | 53.744 | −95.022 | 1.00 | 26.97 | N |
| ATOM | 10441 | CA | ASN C | 351 | −40.415 | 54.501 | −95.839 | 1.00 | 27.90 | C |
| ATOM | 10442 | CB | ASN C | 351 | −41.217 | 55.490 | −94.985 | 1.00 | 28.15 | C |
| ATOM | 10443 | CG | ASN C | 351 | −40.381 | 56.640 | −94.459 | 1.00 | 27.29 | C |
| ATOM | 10444 | OD1 | ASN C | 351 | −39.291 | 56.938 | −94.961 | 1.00 | 26.27 | O |
| ATOM | 10445 | ND2 | ASN C | 351 | −40.901 | 57.301 | −93.439 | 1.00 | 26.94 | N |
| ATOM | 10446 | C | ASN C | 351 | −39.685 | 55.194 | −96.988 | 1.00 | 29.01 | C |
| ATOM | 10447 | O | ASN C | 351 | −38.474 | 55.025 | −97.133 | 1.00 | 29.86 | O |
| ATOM | 10448 | N | PRO C | 352 | −40.415 | 55.978 | −97.810 | 1.00 | 29.88 | N |
| ATOM | 10449 | CA | PRO C | 352 | −39.808 | 56.566 | −99.000 | 1.00 | 30.10 | C |
| ATOM | 10450 | CB | PRO C | 352 | −41.011 | 57.142 | −99.749 | 1.00 | 29.21 | C |
| ATOM | 10451 | CG | PRO C | 352 | −42.188 | 56.393 | −99.218 | 1.00 | 28.50 | C |
| ATOM | 10452 | CD | PRO C | 352 | −41.866 | 56.232 | −97.777 | 1.00 | 29.02 | C |
| ATOM | 10453 | C | PRO C | 352 | −38.772 | 57.661 | −98.708 | 1.00 | 31.67 | C |
| ATOM | 10454 | O | PRO C | 352 | −37.851 | 57.855 | −99.503 | 1.00 | 32.87 | O |
| ATOM | 10455 | N | HIS C | 353 | −38.918 | 58.369 | −97.590 | 1.00 | 32.77 | N |

-continued

| | | | | | Atomic coordinates for CRBN:DDB1:Lenalidomide (Human protein) | | | | |
|---|---|---|---|---|---|---|---|---|---|
| ATOM | 10456 | CA | HIS C | 353 | −37.946 | 59.404 | −97.216 | 1.00 | 33.72 | C |
| ATOM | 10457 | CB | HIS C | 353 | −38.599 | 60.537 | −96.417 | 1.00 | 35.44 | C |
| ATOM | 10458 | CG | HIS C | 353 | −39.852 | 61.106 | −97.056 | 1.00 | 38.40 | C |
| ATOM | 10459 | ND1 | HIS C | 353 | −40.058 | 61.104 | −98.391 | 1.00 | 39.95 | N |
| ATOM | 10460 | CE1 | HIS C | 353 | −41.250 | 61.680 | −98.664 | 1.00 | 40.46 | C |
| ATOM | 10461 | NE2 | HIS C | 353 | −41.804 | 62.064 | −97.500 | 1.00 | 40.61 | N |
| ATOM | 10462 | CD2 | HIS C | 353 | −40.970 | 61.725 | −96.487 | 1.00 | 40.14 | C |
| ATOM | 10463 | C | HIS C | 353 | −36.776 | 58.827 | −96.463 | 1.00 | 33.50 | C |
| ATOM | 10464 | O | HIS C | 353 | −35.946 | 59.565 | −95.924 | 1.00 | 33.28 | O |
| ATOM | 10465 | N | GLY C | 354 | −36.705 | 57.497 | −96.415 | 1.00 | 33.28 | N |
| ATOM | 10466 | CA | GLY C | 354 | −35.577 | 56.793 | −95.810 | 1.00 | 33.10 | C |
| ATOM | 10467 | C | GLY C | 354 | −35.653 | 56.577 | −94.310 | 1.00 | 32.71 | C |
| ATOM | 10468 | O | GLY C | 354 | −34.667 | 56.177 | −93.696 | 1.00 | 31.57 | O |
| ATOM | 10469 | N | TYR C | 355 | −36.823 | 56.831 | −93.724 | 1.00 | 33.97 | N |
| ATOM | 10470 | CA | TYR C | 355 | −37.036 | 56.667 | −92.280 | 1.00 | 34.69 | C |
| ATOM | 10471 | CB | TYR C | 355 | −38.036 | 57.715 | −91.778 | 1.00 | 37.28 | C |
| ATOM | 10472 | CG | TYR C | 355 | −38.183 | 57.728 | −90.279 | 1.00 | 42.96 | C |
| ATOM | 10473 | CD1 | TYR C | 355 | −38.981 | 56.775 | −89.631 | 1.00 | 44.82 | C |
| ATOM | 10474 | CE1 | TYR C | 355 | −39.114 | 56.763 | −88.247 | 1.00 | 48.40 | C |
| ATOM | 10475 | CZ | TYR C | 355 | −38.450 | 57.714 | −87.484 | 1.00 | 50.11 | C |
| ATOM | 10476 | OH | TYR C | 355 | −38.610 | 57.681 | −86.112 | 1.00 | 52.38 | O |
| ATOM | 10477 | CE2 | TYR C | 355 | −37.650 | 58.678 | −88.100 | 1.00 | 48.33 | C |
| ATOM | 10478 | CD2 | TYR C | 355 | −37.521 | 58.682 | −89.492 | 1.00 | 45.58 | C |
| ATOM | 10479 | C | TYR C | 355 | −37.467 | 55.224 | −91.882 | 1.00 | 33.90 | C |
| ATOM | 10480 | O | TYR C | 355 | −38.316 | 54.606 | −92.537 | 1.00 | 35.81 | O |
| ATOM | 10481 | N | VAL C | 356 | −36.888 | 54.697 | −90.809 | 1.00 | 30.43 | N |
| ATOM | 10482 | CA | VAL C | 356 | −37.075 | 53.293 | −90.456 | 1.00 | 29.32 | C |
| ATOM | 10483 | CB | VAL C | 356 | −35.741 | 52.688 | −89.999 | 1.00 | 27.63 | C |
| ATOM | 10484 | CG1 | VAL C | 356 | −35.947 | 51.361 | −89.287 | 1.00 | 28.21 | C |
| ATOM | 10485 | CG2 | VAL C | 356 | −34.822 | 52.516 | −91.192 | 1.00 | 27.01 | C |
| ATOM | 10486 | C | VAL C | 356 | −38.193 | 53.041 | −89.415 | 1.00 | 31.40 | C |
| ATOM | 10487 | O | VAL C | 356 | −38.264 | 53.723 | −88.389 | 1.00 | 32.81 | O |
| ATOM | 10488 | N | HIS C | 357 | −39.065 | 52.064 | −89.688 | 1.00 | 32.30 | N |
| ATOM | 10489 | CA | HIS C | 357 | −40.176 | 51.722 | −88.774 | 1.00 | 32.20 | C |
| ATOM | 10490 | CB | HIS C | 357 | −41.529 | 52.147 | −89.346 | 1.00 | 32.68 | C |
| ATOM | 10491 | CG | HIS C | 357 | −41.739 | 53.628 | −89.386 | 1.00 | 32.55 | C |
| ATOM | 10492 | ND1 | HIS C | 357 | −42.012 | 54.345 | −88.288 | 1.00 | 32.45 | N |
| ATOM | 10493 | CE1 | HIS C | 357 | −42.158 | 55.638 | −88.623 | 1.00 | 33.55 | C |
| ATOM | 10494 | NE2 | HIS C | 357 | −41.977 | 55.747 | −89.948 | 1.00 | 33.97 | N |
| ATOM | 10495 | CD2 | HIS C | 357 | −41.725 | 54.524 | −90.451 | 1.00 | 33.08 | C |
| ATOM | 10496 | C | HIS C | 357 | −40.248 | 50.259 | −88.473 | 1.00 | 32.01 | C |
| ATOM | 10497 | O | HIS C | 357 | −40.483 | 49.438 | −89.365 | 1.00 | 31.26 | O |
| ATOM | 10498 | N | GLU C | 358 | −40.076 | 49.923 | −87.201 | 1.00 | 32.29 | N |
| ATOM | 10499 | CA | GLU C | 358 | −40.326 | 48.569 | −86.736 | 1.00 | 31.97 | C |
| ATOM | 10500 | CB | GLU C | 358 | −39.530 | 48.279 | −85.466 | 1.00 | 31.92 | C |
| ATOM | 10501 | CG | GLU C | 358 | −38.069 | 48.660 | −85.568 | 1.00 | 33.28 | C |
| ATOM | 10502 | CD | GLU C | 358 | −37.276 | 48.182 | −84.381 | 1.00 | 35.29 | C |
| ATOM | 10503 | OE1 | GLU C | 358 | −36.868 | 47.002 | −84.394 | 1.00 | 37.09 | O |
| ATOM | 10504 | OE2 | GLU C | 358 | −37.055 | 48.982 | −83.442 | 1.00 | 35.36 | O |
| ATOM | 10505 | C | GLU C | 358 | −41.821 | 48.442 | −86.480 | 1.00 | 31.24 | C |
| ATOM | 10506 | O | GLU C | 358 | −42.326 | 48.874 | −85.427 | 1.00 | 31.08 | O |
| ATOM | 10507 | N | THR C | 359 | −42.545 | 47.895 | −87.455 | 1.00 | 29.38 | N |
| ATOM | 10508 | CA | THR C | 359 | −44.003 | 47.848 | −87.334 | 1.00 | 28.07 | C |
| ATOM | 10509 | CB | THR C | 359 | −44.752 | 48.381 | −88.596 | 1.00 | 27.94 | C |
| ATOM | 10510 | OG1 | THR C | 359 | −45.150 | 47.305 | −89.442 | 1.00 | 28.73 | O |
| ATOM | 10511 | CG2 | THR C | 359 | −43.872 | 49.324 | −89.393 | 1.00 | 28.08 | C |
| ATOM | 10512 | C | THR C | 359 | −44.468 | 46.467 | −86.879 | 1.00 | 26.94 | C |
| ATOM | 10513 | O | THR C | 359 | −43.905 | 45.442 | −87.278 | 1.00 | 26.51 | O |
| ATOM | 10514 | N | LEU C | 360 | −45.473 | 46.474 | −86.004 | 1.00 | 25.71 | N |
| ATOM | 10515 | CA | LEU C | 360 | −46.022 | 45.280 | −85.379 | 1.00 | 24.53 | C |
| ATOM | 10516 | CB | LEU C | 360 | −46.115 | 45.497 | −83.862 | 1.00 | 24.04 | C |
| ATOM | 10517 | CG | LEU C | 360 | −46.906 | 44.509 | −82.999 | 1.00 | 23.67 | C |
| ATOM | 10518 | CD1 | LEU C | 360 | −46.065 | 43.278 | −82.707 | 1.00 | 24.04 | C |
| ATOM | 10519 | CD2 | LEU C | 360 | −47.354 | 45.169 | −81.705 | 1.00 | 23.41 | C |
| ATOM | 10520 | C | LEU C | 360 | −47.404 | 44.984 | −85.948 | 1.00 | 24.21 | C |
| ATOM | 10521 | O | LEU C | 360 | −48.301 | 45.827 | −85.870 | 1.00 | 24.41 | O |
| ATOM | 10522 | N | THR C | 361 | −47.579 | 43.790 | −86.514 | 1.00 | 23.92 | N |
| ATOM | 10523 | CA | THR C | 361 | −48.870 | 43.397 | −87.084 | 1.00 | 23.85 | C |
| ATOM | 10524 | CB | THR C | 361 | −48.729 | 42.357 | −88.212 | 1.00 | 23.69 | C |
| ATOM | 10525 | OG1 | THR C | 361 | −47.794 | 41.344 | −87.823 | 1.00 | 24.01 | O |
| ATOM | 10526 | CG2 | THR C | 361 | −48.246 | 43.019 | −89.485 | 1.00 | 24.12 | C |
| ATOM | 10527 | C | THR C | 361 | −49.809 | 42.856 | −86.022 | 1.00 | 24.06 | C |
| ATOM | 10528 | O | THR C | 361 | −49.494 | 41.876 | −85.340 | 1.00 | 23.84 | O |
| ATOM | 10529 | N | VAL C | 362 | −50.959 | 43.510 | −85.880 | 1.00 | 24.37 | N |
| ATOM | 10530 | CA | VAL C | 362 | −52.024 | 43.017 | −85.017 | 1.00 | 25.30 | C |
| ATOM | 10531 | CB | VAL C | 362 | −52.234 | 43.910 | −83.768 | 1.00 | 25.94 | C |
| ATOM | 10532 | CG1 | VAL C | 362 | −51.020 | 43.856 | −82.842 | 1.00 | 25.96 | C |

-continued

| | | | Atomic coordinates for CRBN:DDB1:Lenalidomide (Human protein) | | | | | | |
|---|---|---|---|---|---|---|---|---|---|
| ATOM | 10533 | CG2 | VAL C | 362 | −52.584 | 45.342 | −84.157 | 1.00 | 25.68 | C |
| ATOM | 10534 | C | VAL C | 362 | −53.331 | 42.896 | −85.788 | 1.00 | 25.90 | C |
| ATOM | 10535 | O | VAL C | 362 | −53.508 | 43.563 | −86.808 | 1.00 | 26.82 | O |
| ATOM | 10536 | N | TYR C | 363 | −54.237 | 42.044 | −85.302 | 1.00 | 27.09 | N |
| ATOM | 10537 | CA | TYR C | 363 | −55.584 | 41.901 | −85.881 | 1.00 | 28.27 | C |
| ATOM | 10538 | CB | TYR C | 363 | −56.253 | 40.626 | −85.390 | 1.00 | 29.21 | C |
| ATOM | 10539 | CG | TYR C | 363 | −55.636 | 39.351 | −85.887 | 1.00 | 30.08 | C |
| ATOM | 10540 | CD1 | TYR C | 363 | −55.544 | 39.077 | −87.254 | 1.00 | 30.49 | C |
| ATOM | 10541 | CE1 | TYR C | 363 | −54.990 | 37.891 | −87.710 | 1.00 | 31.12 | C |
| ATOM | 10542 | CZ | TYR C | 363 | −54.539 | 36.951 | −86.790 | 1.00 | 31.84 | C |
| ATOM | 10543 | OH | TYR C | 363 | −53.991 | 35.764 | −87.214 | 1.00 | 32.13 | O |
| ATOM | 10544 | CE2 | TYR C | 363 | −54.633 | 37.198 | −85.432 | 1.00 | 32.27 | C |
| ATOM | 10545 | CD2 | TYR C | 363 | −55.182 | 38.392 | −84.989 | 1.00 | 31.16 | C |
| ATOM | 10546 | C | TYR C | 363 | −56.506 | 43.074 | −85.564 | 1.00 | 28.66 | C |
| ATOM | 10547 | O | TYR C | 363 | −57.041 | 43.701 | −86.472 | 1.00 | 29.23 | O |
| ATOM | 10548 | N | LYS C | 364 | −56.709 | 43.328 | −84.270 | 1.00 | 29.45 | N |
| ATOM | 10549 | CA | LYS C | 364 | −57.552 | 44.424 | −83.771 | 1.00 | 30.16 | C |
| ATOM | 10550 | CB | LYS C | 364 | −58.527 | 43.918 | −82.693 | 1.00 | 31.84 | C |
| ATOM | 10551 | CG | LYS C | 364 | −59.956 | 43.644 | −83.144 | 1.00 | 32.80 | C |
| ATOM | 10552 | CD | LYS C | 364 | −60.188 | 42.167 | −83.445 | 1.00 | 33.71 | C |
| ATOM | 10553 | CE | LYS C | 364 | −61.333 | 41.585 | −82.619 | 1.00 | 34.51 | C |
| ATOM | 10554 | NZ | LYS C | 364 | −62.535 | 42.470 | −82.549 | 1.00 | 35.90 | N |
| ATOM | 10555 | C | LYS C | 364 | −56.724 | 45.562 | −83.166 | 1.00 | 29.61 | C |
| ATOM | 10556 | O | LYS C | 364 | −55.652 | 45.337 | −82.593 | 1.00 | 29.16 | O |
| ATOM | 10557 | N | ALA C | 365 | −57.249 | 46.781 | −83.287 | 1.00 | 28.84 | N |
| ATOM | 10558 | CA | ALA C | 365 | −56.656 | 47.963 | −82.673 | 1.00 | 27.41 | C |
| ATOM | 10559 | CB | ALA C | 365 | −55.609 | 48.581 | −83.584 | 1.00 | 27.30 | C |
| ATOM | 10560 | C | ALA C | 365 | −57.735 | 48.978 | −82.330 | 1.00 | 26.97 | C |
| ATOM | 10561 | O | ALA C | 365 | −58.511 | 49.410 | −83.190 | 1.00 | 26.92 | O |
| ATOM | 10562 | N | SER C | 366 | −57.770 | 49.362 | −81.065 | 1.00 | 26.43 | N |
| ATOM | 10563 | CA | SER C | 366 | −58.808 | 50.240 | −80.565 | 1.00 | 26.51 | C |
| ATOM | 10564 | CB | SER C | 366 | −59.233 | 49.776 | −79.173 | 1.00 | 27.33 | C |
| ATOM | 10565 | OG | SER C | 366 | −59.448 | 48.373 | −79.168 | 1.00 | 28.88 | O |
| ATOM | 10566 | C | SER C | 366 | −58.372 | 51.707 | −80.530 | 1.00 | 25.73 | C |
| ATOM | 10567 | O | SER C | 366 | −57.177 | 52.012 | −80.608 | 1.00 | 25.80 | O |
| ATOM | 10568 | N | ASN C | 367 | −59.362 | 52.600 | −80.420 | 1.00 | 24.57 | N |
| ATOM | 10569 | CA | ASN C | 367 | −59.156 | 54.047 | −80.238 | 1.00 | 23.02 | C |
| ATOM | 10570 | CB | ASN C | 367 | −58.712 | 54.378 | −78.802 | 1.00 | 22.99 | C |
| ATOM | 10571 | CG | ASN C | 367 | −59.408 | 53.531 | −77.763 | 1.00 | 22.84 | C |
| ATOM | 10572 | OD1 | ASN C | 367 | −58.844 | 52.554 | −77.276 | 1.00 | 23.01 | O |
| ATOM | 10573 | ND2 | ASN C | 367 | −60.640 | 53.891 | −77.426 | 1.00 | 22.29 | N |
| ATOM | 10574 | C | ASN C | 367 | −58.178 | 54.677 | −81.221 | 1.00 | 21.97 | C |
| ATOM | 10575 | O | ASN C | 367 | −57.268 | 55.394 | −80.813 | 1.00 | 22.08 | O |
| ATOM | 10576 | N | LEU C | 368 | −58.359 | 54.404 | −82.508 | 1.00 | 20.84 | N |
| ATOM | 10577 | CA | LEU C | 368 | −57.565 | 55.069 | −83.541 | 1.00 | 19.91 | C |
| ATOM | 10578 | CB | LEU C | 368 | −56.617 | 54.078 | −84.236 | 1.00 | 19.47 | C |
| ATOM | 10579 | CG | LEU C | 368 | −55.562 | 53.382 | −83.359 | 1.00 | 19.30 | C |
| ATOM | 10580 | CD1 | LEU C | 368 | −54.953 | 52.201 | −84.087 | 1.00 | 18.97 | C |
| ATOM | 10581 | CD2 | LEU C | 368 | −56.473 | 54.329 | −82.877 | 1.00 | 18.79 | C |
| ATOM | 10582 | C | LEU C | 368 | −58.447 | 55.797 | −84.555 | 1.00 | 19.53 | C |
| ATOM | 10583 | O | LEU C | 368 | −59.595 | 55.421 | −84.786 | 1.00 | 19.57 | O |
| ATOM | 10584 | N | ASN C | 369 | −57.909 | 56.858 | −85.139 | 1.00 | 19.40 | N |
| ATOM | 10585 | CA | ASN C | 369 | −58.584 | 57.555 | −86.226 | 1.00 | 19.63 | C |
| ATOM | 10586 | CB | ASN C | 369 | −58.770 | 59.031 | −85.894 | 1.00 | 19.34 | C |
| ATOM | 10587 | CG | ASN C | 369 | −59.623 | 59.246 | −84.676 | 1.00 | 19.08 | C |
| ATOM | 10588 | OD1 | ASN C | 369 | −60.677 | 58.625 | −84.518 | 1.00 | 18.93 | O |
| ATOM | 10589 | ND2 | ASN C | 369 | −59.179 | 60.142 | −83.805 | 1.00 | 19.48 | N |
| ATOM | 10590 | C | ASN C | 369 | −57.789 | 57.427 | −87.505 | 1.00 | 19.56 | C |
| ATOM | 10591 | O | ASN C | 369 | −56.556 | 57.409 | −87.465 | 1.00 | 19.77 | O |
| ATOM | 10592 | N | LEU C | 370 | −58.497 | 57.348 | −88.631 | 1.00 | 19.37 | N |
| ATOM | 10593 | CA | LEU C | 370 | −57.866 | 57.153 | −89.935 | 1.00 | 19.79 | C |
| ATOM | 10594 | CB | LEU C | 370 | −58.388 | 55.868 | −90.588 | 1.00 | 18.90 | C |
| ATOM | 10595 | CG | LEU C | 370 | −58.449 | 54.639 | −89.660 | 1.00 | 18.33 | C |
| ATOM | 10596 | CD1 | LEU C | 370 | −59.367 | 53.550 | −90.204 | 1.00 | 17.58 | C |
| ATOM | 10597 | CD2 | LEU C | 370 | −57.059 | 54.091 | −89.351 | 1.00 | 17.97 | C |
| ATOM | 10598 | C | LEU C | 370 | −58.071 | 58.372 | −90.845 | 1.00 | 20.82 | C |
| ATOM | 10599 | O | LEU C | 370 | −59.199 | 58.847 | −91.015 | 1.00 | 20.66 | O |
| ATOM | 10600 | N | ILE C | 371 | −56.971 | 58.896 | −91.387 | 1.00 | 22.07 | N |
| ATOM | 10601 | CA | ILE C | 371 | −57.014 | 60.082 | −92.252 | 1.00 | 24.28 | C |
| ATOM | 10602 | CB | ILE C | 371 | −56.358 | 61.340 | −91.596 | 1.00 | 25.12 | C |
| ATOM | 10603 | CG1 | ILE C | 371 | −54.863 | 61.122 | −91.306 | 1.00 | 25.59 | C |
| ATOM | 10604 | CD1 | ILE C | 371 | −53.936 | 61.577 | −92.418 | 1.00 | 25.85 | C |
| ATOM | 10605 | CG2 | ILE C | 371 | −57.117 | 61.783 | −90.342 | 1.00 | 24.41 | C |
| ATOM | 10606 | C | ILE C | 371 | −56.386 | 59.804 | −93.620 | 1.00 | 25.93 | C |
| ATOM | 10607 | O | ILE C | 371 | −55.495 | 58.955 | −93.747 | 1.00 | 27.08 | O |
| ATOM | 10608 | N | GLY C | 372 | −56.847 | 60.519 | −94.642 | 1.00 | 26.96 | N |
| ATOM | 10609 | CA | GLY C | 372 | −56.378 | 60.277 | −96.004 | 1.00 | 28.86 | C |

-continued

| | | | | | | | | | |
|---|---|---|---|---|---|---|---|---|---|
| | Atomic coordinates for CRBN:DDB1:Lenalidomide (Human protein) |

| | | | | | | | | | |
|---|---|---|---|---|---|---|---|---|---|
| ATOM | 10610 | C | GLY | C | 372 | −56.985 | 59.028 | −96.627 | 1.00 | 30.00 | C |
| ATOM | 10611 | O | GLY | C | 372 | −57.900 | 58.415 | −96.059 | 1.00 | 29.29 | O |
| ATOM | 10612 | N | ARG | C | 373 | −56.456 | 58.648 | −97.791 | 1.00 | 31.35 | N |
| ATOM | 10613 | CA | ARG | C | 373 | −57.042 | 57.604 | −98.620 | 1.00 | 32.80 | C |
| ATOM | 10614 | CB | ARG | C | 373 | −57.135 | 58.106 | −100.058 | 1.00 | 36.06 | C |
| ATOM | 10615 | CG | ARG | C | 373 | −58.443 | 57.802 | −100.768 | 1.00 | 39.89 | C |
| ATOM | 10616 | CD | ARG | C | 373 | −58.316 | 58.066 | −102.268 | 1.00 | 42.07 | C |
| ATOM | 10617 | NE | ARG | C | 373 | −57.800 | 56.895 | −102.985 | 1.00 | 44.79 | N |
| ATOM | 10618 | CZ | ARG | C | 373 | −58.521 | 56.127 | −103.804 | 1.00 | 45.67 | C |
| ATOM | 10619 | NH1 | ARG | C | 373 | −57.957 | 55.077 | −104.395 | 1.00 | 44.79 | N |
| ATOM | 10620 | NH2 | ARG | C | 373 | −59.802 | 56.407 | −104.044 | 1.00 | 45.23 | N |
| ATOM | 10621 | C | ARG | C | 373 | −56.158 | 56.364 | −98.572 | 1.00 | 32.66 | C |
| ATOM | 10622 | O | ARG | C | 373 | −54.927 | 56.486 | −98.611 | 1.00 | 32.01 | O |
| ATOM | 10623 | N | PRO | C | 374 | −56.772 | 55.159 | −98.477 | 1.00 | 32.71 | N |
| ATOM | 10624 | CA | PRO | C | 374 | −55.966 | 53.925 | −98.497 | 1.00 | 32.13 | C |
| ATOM | 10625 | CB | PRO | C | 374 | −57.022 | 52.812 | −98.515 | 1.00 | 31.20 | C |
| ATOM | 10626 | CG | PRO | C | 374 | −58.195 | 53.420 | −97.820 | 1.00 | 30.94 | C |
| ATOM | 10627 | CD | PRO | C | 374 | −58.201 | 54.871 | −98.241 | 1.00 | 31.76 | C |
| ATOM | 10628 | C | PRO | C | 374 | −55.070 | 53.866 | −99.737 | 1.00 | 32.34 | C |
| ATOM | 10629 | O | PRO | C | 374 | −55.530 | 54.143 | −100.849 | 1.00 | 32.78 | O |
| ATOM | 10630 | N | SER | C | 375 | −53.797 | 53.542 | −99.527 | 1.00 | 31.71 | N |
| ATOM | 10631 | CA | SER | C | 375 | −52.791 | 53.601 | −100.582 | 1.00 | 30.15 | C |
| ATOM | 10632 | CB | SER | C | 375 | −51.961 | 54.874 | −100.429 | 1.00 | 30.26 | C |
| ATOM | 10633 | OG | SER | C | 375 | −50.830 | 54.862 | −101.281 | 1.00 | 30.88 | O |
| ATOM | 10634 | C | SER | C | 375 | −51.883 | 52.370 | −100.556 | 1.00 | 29.43 | C |
| ATOM | 10635 | O | SER | C | 375 | −51.508 | 51.899 | −99.488 | 1.00 | 28.84 | O |
| ATOM | 10636 | N | THR | C | 376 | −51.546 | 51.856 | −101.739 | 1.00 | 28.48 | N |
| ATOM | 10637 | CA | THR | C | 376 | −50.613 | 50.736 | −101.881 | 1.00 | 27.27 | C |
| ATOM | 10638 | CB | THR | C | 376 | −51.040 | 49.798 | −103.014 | 1.00 | 24.95 | C |
| ATOM | 10639 | OG1 | THR | C | 376 | −51.017 | 50.522 | −104.238 | 1.00 | 23.33 | O |
| ATOM | 10640 | CG2 | THR | C | 376 | −52.424 | 49.274 | −102.780 | 1.00 | 23.82 | C |
| ATOM | 10641 | C | THR | C | 376 | −49.201 | 51.247 | −102.184 | 1.00 | 28.37 | C |
| ATOM | 10642 | O | THR | C | 376 | −48.225 | 50.485 | −102.163 | 1.00 | 28.70 | O |
| ATOM | 10643 | N | GLU | C | 377 | −49.114 | 52.540 | −102.481 | 1.00 | 29.94 | N |
| ATOM | 10644 | CA | GLU | C | 377 | −47.854 | 53.234 | −102.735 | 1.00 | 31.69 | C |
| ATOM | 10645 | CB | GLU | C | 377 | −48.126 | 54.737 | −102.774 | 1.00 | 33.99 | C |
| ATOM | 10646 | CG | GLU | C | 377 | −47.120 | 55.566 | −103.541 | 1.00 | 38.01 | C |
| ATOM | 10647 | CD | GLU | C | 377 | −47.642 | 56.967 | −103.878 | 1.00 | 43.36 | C |
| ATOM | 10648 | OE1 | GLU | C | 377 | −48.866 | 57.122 | −104.150 | 1.00 | 45.65 | O |
| ATOM | 10649 | OE2 | GLU | C | 377 | −46.819 | 57.920 | −103.887 | 1.00 | 45.18 | O |
| ATOM | 10650 | C | GLU | C | 377 | −46.786 | 52.907 | −101.676 | 1.00 | 31.03 | C |
| ATOM | 10651 | O | GLU | C | 377 | −46.911 | 53.288 | −100.515 | 1.00 | 30.52 | O |
| ATOM | 10652 | N | HIS | C | 378 | −45.754 | 52.175 | −102.090 | 1.00 | 30.76 | N |
| ATOM | 10653 | CA | HIS | C | 378 | −44.604 | 51.856 | −101.238 | 1.00 | 30.21 | C |
| ATOM | 10654 | CB | HIS | C | 378 | −43.903 | 53.144 | −100.774 | 1.00 | 31.11 | C |
| ATOM | 10655 | CG | HIS | C | 378 | −42.454 | 52.955 | −100.362 | 1.00 | 31.85 | C |
| ATOM | 10656 | ND1 | HIS | C | 378 | −42.066 | 52.919 | −99.074 | 1.00 | 32.07 | N |
| ATOM | 10657 | CE1 | HIS | C | 378 | −40.727 | 52.758 | −99.011 | 1.00 | 31.67 | C |
| ATOM | 10658 | NE2 | HIS | C | 378 | −40.256 | 52.695 | −100.266 | 1.00 | 31.92 | N |
| ATOM | 10659 | CD2 | HIS | C | 378 | −41.291 | 52.815 | −101.125 | 1.00 | 32.55 | C |
| ATOM | 10660 | C | HIS | C | 378 | −45.000 | 51.001 | −100.067 | 1.00 | 29.68 | C |
| ATOM | 10661 | O | HIS | C | 378 | −44.337 | 51.017 | −99.032 | 1.00 | 31.57 | O |
| ATOM | 10662 | N | SER | C | 379 | −46.079 | 50.235 | −100.220 | 1.00 | 28.49 | N |
| ATOM | 10663 | CA | SER | C | 379 | −46.575 | 49.371 | −99.135 | 1.00 | 27.29 | C |
| ATOM | 10664 | CB | SER | C | 379 | −47.971 | 48.838 | −99.447 | 1.00 | 26.54 | C |
| ATOM | 10665 | OG | SER | C | 379 | −48.225 | 47.660 | −98.708 | 1.00 | 25.40 | O |
| ATOM | 10666 | C | SER | C | 379 | −45.656 | 48.197 | −98.817 | 1.00 | 26.95 | C |
| ATOM | 10667 | O | SER | C | 379 | −45.233 | 47.462 | −99.711 | 1.00 | 28.52 | O |
| ATOM | 10668 | N | TRP | C | 380 | −45.385 | 48.010 | −97.532 | 1.00 | 25.98 | N |
| ATOM | 10669 | CA | TRP | C | 380 | −44.525 | 46.928 | −97.060 | 1.00 | 25.57 | C |
| ATOM | 10670 | CB | TRP | C | 380 | −44.028 | 47.230 | −95.642 | 1.00 | 25.56 | C |
| ATOM | 10671 | CG | TRP | C | 380 | −43.357 | 48.583 | −95.532 | 1.00 | 25.28 | C |
| ATOM | 10672 | CD1 | TRP | C | 380 | −42.506 | 49.182 | −96.451 | 1.00 | 25.01 | C |
| ATOM | 10673 | NE1 | TRP | C | 380 | −42.107 | 50.412 | −96.017 | 1.00 | 24.70 | N |
| ATOM | 10674 | CE2 | TRP | C | 380 | −42.642 | 50.692 | −94.821 | 1.00 | 24.72 | C |
| ATOM | 10675 | CD2 | TRP | C | 380 | −43.471 | 49.550 | −94.443 | 1.00 | 25.05 | C |
| ATOM | 10676 | CE3 | TRP | C | 380 | −44.153 | 49.586 | −93.239 | 1.00 | 25.17 | C |
| ATOM | 10677 | CZ3 | TRP | C | 380 | −44.012 | 50.716 | −92.431 | 1.00 | 25.22 | C |
| ATOM | 10678 | CH2 | TRP | C | 380 | −43.205 | 51.796 | −92.810 | 1.00 | 25.01 | C |
| ATOM | 10679 | CZ2 | TRP | C | 380 | −42.511 | 51.803 | −94.016 | 1.00 | 24.76 | C |
| ATOM | 10680 | C | TRP | C | 380 | −45.185 | 45.579 | −97.114 | 1.00 | 25.27 | C |
| ATOM | 10681 | O | TRP | C | 380 | −44.546 | 44.561 | −96.872 | 1.00 | 24.64 | O |
| ATOM | 10682 | N | PHE | C | 381 | −46.474 | 45.558 | −97.433 | 1.00 | 26.22 | N |
| ATOM | 10683 | CA | PHE | C | 381 | −47.229 | 44.307 | −97.527 | 1.00 | 26.50 | C |
| ATOM | 10684 | CB | PHE | C | 381 | −48.246 | 44.199 | −96.387 | 1.00 | 25.82 | C |
| ATOM | 10685 | CG | PHE | C | 381 | −47.628 | 44.285 | −95.025 | 1.00 | 26.00 | C |
| ATOM | 10686 | CD1 | PHE | C | 381 | −46.986 | 43.182 | −94.465 | 1.00 | 26.58 | C |

-continued

| Atomic coordinates for CRBN:DDB1:Lenalidomide (Human protein) | | | | | | | | | |
|---|---|---|---|---|---|---|---|---|---|
| ATOM | 10687 | CE1 | PHE C | 381 | −46.400 | 43.260 | −93.216 | 1.00 | 26.43 | C |
| ATOM | 10688 | CZ | PHE C | 381 | −46.448 | 44.452 | −92.511 | 1.00 | 26.23 | C |
| ATOM | 10689 | CE2 | PHE C | 381 | −47.081 | 45.555 | −93.062 | 1.00 | 26.05 | C |
| ATOM | 10690 | CD2 | PHE C | 381 | −47.665 | 45.468 | −94.311 | 1.00 | 25.88 | C |
| ATOM | 10691 | C | PHE C | 381 | −47.928 | 44.198 | −98.875 | 1.00 | 26.97 | C |
| ATOM | 10692 | O | PHE C | 381 | −49.091 | 44.585 | −98.995 | 1.00 | 27.72 | O |
| ATOM | 10693 | N | PRO C | 382 | −47.218 | 43.675 | −99.899 | 1.00 | 27.09 | N |
| ATOM | 10694 | CA | PRO C | 382 | −47.826 | 43.553 | −101.227 | 1.00 | 26.40 | C |
| ATOM | 10695 | CB | PRO C | 382 | −46.841 | 42.669 | −102.005 | 1.00 | 26.79 | C |
| ATOM | 10696 | CG | PRO C | 382 | −45.557 | 42.755 | −101.257 | 1.00 | 27.82 | C |
| ATOM | 10697 | CD | PRO C | 382 | −45.900 | 43.014 | −99.820 | 1.00 | 27.53 | C |
| ATOM | 10698 | C | PRO C | 382 | −49.168 | 42.861 | −101.105 | 1.00 | 26.11 | C |
| ATOM | 10699 | O | PRO C | 382 | −49.261 | 41.767 | −100.531 | 1.00 | 25.37 | O |
| ATOM | 10700 | N | GLY C | 383 | −50.205 | 43.521 | −101.610 | 1.00 | 26.70 | N |
| ATOM | 10701 | CA | GLY C | 383 | −51.568 | 43.020 | −101.507 | 1.00 | 26.64 | C |
| ATOM | 10702 | C | GLY C | 383 | −52.434 | 43.924 | −100.666 | 1.00 | 26.98 | C |
| ATOM | 10703 | O | GLY C | 383 | −53.661 | 43.924 | −100.811 | 1.00 | 28.25 | O |
| ATOM | 10704 | N | TYR C | 384 | −51.789 | 44.710 | −99.799 | 1.00 | 27.12 | N |
| ATOM | 10705 | CA | TYR C | 384 | −52.484 | 45.613 | −98.878 | 1.00 | 26.44 | C |
| ATOM | 10706 | CB | TYR C | 384 | −52.121 | 45.265 | −97.431 | 1.00 | 26.85 | C |
| ATOM | 10707 | CG | TYR C | 384 | −52.609 | 43.890 | −97.040 | 1.00 | 27.90 | C |
| ATOM | 10708 | CD1 | TYR C | 384 | −53.934 | 43.686 | −96.667 | 1.00 | 28.21 | C |
| ATOM | 10709 | CE1 | TYR C | 384 | −54.401 | 42.431 | −96.333 | 1.00 | 28.83 | C |
| ATOM | 10710 | CZ | TYR C | 384 | −53.538 | 41.350 | −96.371 | 1.00 | 29.60 | C |
| ATOM | 10711 | OH | TYR C | 384 | −54.008 | 40.103 | −96.034 | 1.00 | 30.66 | O |
| ATOM | 10712 | CE2 | TYR C | 384 | −52.212 | 41.517 | −96.741 | 1.00 | 29.10 | C |
| ATOM | 10713 | CD2 | TYR C | 384 | −51.757 | 42.783 | −97.082 | 1.00 | 28.57 | C |
| ATOM | 10714 | C | TYR C | 384 | −52.261 | 47.101 | −99.165 | 1.00 | 25.94 | C |
| ATOM | 10715 | O | TYR C | 384 | −51.221 | 47.492 | −99.710 | 1.00 | 26.36 | O |
| ATOM | 10716 | N | ALA C | 385 | −53.264 | 47.913 | −98.830 | 1.00 | 25.24 | N |
| ATOM | 10717 | CA | ALA C | 385 | −53.145 | 49.374 | −98.836 | 1.00 | 24.98 | C |
| ATOM | 10718 | CB | ALA C | 385 | −54.306 | 50.005 | −99.584 | 1.00 | 24.99 | C |
| ATOM | 10719 | C | ALA C | 385 | −53.082 | 49.918 | −97.407 | 1.00 | 24.92 | C |
| ATOM | 10720 | O | ALA C | 385 | −53.767 | 49.410 | −96.512 | 1.00 | 24.46 | O |
| ATOM | 10721 | N | TRP C | 386 | −52.269 | 50.961 | −97.208 | 1.00 | 25.24 | N |
| ATOM | 10722 | CA | TRP C | 386 | −52.079 | 51.587 | −95.886 | 1.00 | 24.58 | C |
| ATOM | 10723 | CB | TRP C | 386 | −50.593 | 51.738 | −95.548 | 1.00 | 24.60 | C |
| ATOM | 10724 | CG | TRP C | 386 | −49.804 | 52.456 | −96.605 | 1.00 | 25.04 | C |
| ATOM | 10725 | CD1 | TRP C | 386 | −49.049 | 51.890 | −97.616 | 1.00 | 25.20 | C |
| ATOM | 10726 | NE1 | TRP C | 386 | −48.478 | 52.862 | −98.399 | 1.00 | 25.72 | N |
| ATOM | 10727 | CE2 | TRP C | 386 | −48.817 | 54.097 | −97.961 | 1.00 | 25.52 | C |
| ATOM | 10728 | CD2 | TRP C | 386 | −49.673 | 53.915 | −96.797 | 1.0 | 25.69 | C |
| ATOM | 10729 | CE3 | TRP C | 386 | −50.158 | 55.047 | −96.131 | 1.00 | 25.67 | C |
| ATOM | 10730 | CZ3 | TRP C | 386 | −49.813 | 56.312 | −96.620 | 1.00 | 24.69 | C |
| ATOM | 10731 | CH2 | TRP C | 386 | −48.987 | 56.463 | −97.738 | 1.00 | 25.02 | C |
| ATOM | 10732 | CZ2 | TRP C | 386 | −48.472 | 55.358 | −98.431 | 1.00 | 25.62 | C |
| ATOM | 10733 | C | TRP C | 386 | −52.804 | 52.902 | −95.719 | 1.00 | 24.02 | C |
| ATOM | 10734 | O | TRP C | 386 | −52.861 | 53.736 | −96.640 | 1.00 | 23.62 | O |
| ATOM | 10735 | N | THR C | 387 | −53.397 | 53.074 | −94.539 | 1.00 | 23.40 | N |
| ATOM | 10736 | CA | THR C | 387 | −54.011 | 54.339 | −94.147 | 1.00 | 23.26 | C |
| ATOM | 10737 | CB | THR C | 387 | −55.552 | 54.258 | −94.007 | 1.00 | 23.30 | C |
| ATOM | 10738 | OG1 | THR C | 387 | −56.131 | 53.665 | −95.178 | 1.00 | 23.65 | O |
| ATOM | 10739 | CG2 | THR C | 387 | −56.149 | 55.644 | −93.808 | 1.00 | 23.15 | C |
| ATOM | 10740 | C | THR C | 387 | −53.422 | 54.717 | −92.808 | 1.00 | 22.72 | C |
| ATOM | 10741 | O | THR C | 387 | −53.299 | 53.873 | −91.915 | 1.00 | 22.46 | O |
| ATOM | 10742 | N | VAL C | 388 | −53.047 | 55.987 | −92.690 | 1.00 | 22.21 | N |
| ATOM | 10743 | CA | VAL C | 388 | −52.463 | 56.528 | −91.475 | 1.00 | 21.65 | C |
| ATOM | 10744 | CB | VAL C | 388 | −51.947 | 57.972 | −91.713 | 1.00 | 21.69 | C |
| ATOM | 10745 | CG1 | VAL C | 388 | −51.613 | 58.682 | −90.409 | 1.00 | 21.73 | C |
| ATOM | 10746 | CG2 | VAL C | 388 | −50.731 | 57.952 | −92.635 | 1.00 | 21.77 | C |
| ATOM | 10747 | C | VAL C | 388 | −53.497 | 56.456 | −90.347 | 1.00 | 21.44 | C |
| ATOM | 10748 | O | VAL C | 388 | −54.672 | 56.763 | −90.552 | 1.00 | 21.51 | O |
| ATOM | 10749 | N | ALA C | 389 | −53.054 | 56.001 | −89.179 | 1.00 | 20.82 | N |
| ATOM | 10750 | CA | ALA C | 389 | −53.901 | 55.892 | −88.007 | 1.00 | 20.61 | C |
| ATOM | 10751 | CB | ALA C | 389 | −53.967 | 54.442 | −87.557 | 1.00 | 20.77 | C |
| ATOM | 10752 | C | ALA C | 389 | −53.276 | 56.742 | −86.922 | 1.00 | 20.96 | C |
| ATOM | 10753 | O | ALA C | 389 | −52.043 | 56.786 | −86.839 | 1.00 | 21.40 | O |
| ATOM | 10754 | N | GLN C | 390 | −54.092 | 57.397 | −86.081 | 1.00 | 20.76 | N |
| ATOM | 10755 | CA | GLN C | 390 | −53.524 | 58.115 | −84.917 | 1.00 | 20.94 | C |
| ATOM | 10756 | CB | GLN C | 390 | −53.147 | 59.550 | −85.293 | 1.00 | 20.81 | C |
| ATOM | 10757 | CG | GLN C | 390 | −54.302 | 60.435 | −85.708 | 1.00 | 21.03 | C |
| ATOM | 10758 | CD | GLN C | 390 | −53.903 | 61.417 | −86.795 | 1.00 | 20.90 | C |
| ATOM | 10759 | OE1 | GLN C | 390 | −53.188 | 61.062 | −87.727 | 1.00 | 20.56 | O |
| ATOM | 10760 | NE2 | GLN C | 390 | −54.369 | 62.654 | −86.681 | 1.00 | 20.73 | N |
| ATOM | 10761 | C | GLN C | 390 | −54.281 | 58.073 | −83.571 | 1.00 | 21.07 | C |
| ATOM | 10762 | O | GLN C | 390 | −55.494 | 57.898 | −83.544 | 1.00 | 21.22 | O |
| ATOM | 10763 | N | CYS C | 391 | −53.529 | 58.283 | −82.493 | 1.00 | 21.48 | N |

-continued

| | | | Atomic coordinates for CRBN:DDB1:Lenalidomide (Human protein) | | | | | | |
|---|---|---|---|---|---|---|---|---|---|
| ATOM | 10764 | CA  | CYS C | 391 | −54.071 | 58.341 | −81.142 | 1.00 | 21.88 | C |
| ATOM | 10765 | CB  | CYS C | 391 | −52.994 | 58.798 | −80.155 | 1.00 | 23.62 | C |
| ATOM | 10766 | SG  | CYS C | 391 | −53.251 | 58.235 | −78.456 | 1.00 | 24.16 | S |
| ATOM | 10767 | C   | CYS C | 391 | −55.283 | 59.259 | −81.052 | 1.00 | 21.54 | C |
| ATOM | 10768 | O   | CYS C | 391 | −55.161 | 60.484 | −81.033 | 1.00 | 21.45 | O |
| ATOM | 10769 | N   | LYS C | 392 | −56.453 | 58.638 | −80.995 | 1.00 | 21.02 | N |
| ATOM | 10770 | CA  | LYS C | 392 | −57.739 | 59.335 | −80.860 | 1.00 | 20.07 | C |
| ATOM | 10771 | CB  | LYS C | 392 | −58.810 | 58.309 | −80.452 | 1.00 | 20.00 | C |
| ATOM | 10772 | CG  | LYS C | 392 | −60.146 | 58.873 | −79.999 | 1.00 | 20.67 | C |
| ATOM | 10773 | CD  | LYS C | 392 | −60.707 | 58.099 | −78.804 | 1.00 | 21.00 | C |
| ATOM | 10774 | CE  | LYS C | 392 | −61.403 | 56.808 | −79.222 | 1.00 | 20.98 | C |
| ATOM | 10775 | NZ  | LYS C | 392 | −61.934 | 56.071 | −78.048 | 1.00 | 20.32 | N |
| ATOM | 10776 | C   | LYS C | 392 | −57.696 | 60.527 | −79.868 | 1.00 | 19.59 | C |
| ATOM | 10777 | O   | LYS C | 392 | −58.312 | 61.564 | −80.116 | 1.00 | 19.54 | O |
| ATOM | 10778 | N   | ILE C | 393 | −56.969 | 60.368 | −78.759 | 1.00 | 18.72 | N |
| ATOM | 10779 | CA  | ILE C | 393 | −56.805 | 61.425 | −77.757 | 1.00 | 18.31 | C |
| ATOM | 10780 | CB  | ILE C | 393 | −56.440 | 60.841 | −76.359 | 1.00 | 17.23 | C |
| ATOM | 10781 | CG1 | ILE C | 393 | −57.417 | 59.738 | −75.914 | 1.00 | 16.62 | C |
| ATOM | 10782 | CD1 | ILE C | 393 | −58.888 | 60.078 | −76.034 | 1.00 | 16.59 | C |
| ATOM | 10783 | CG2 | ILE C | 393 | −56.297 | 61.941 | −75.315 | 1.00 | 16.87 | C |
| ATOM | 10784 | C   | ILE C | 393 | −55.685 | 62.362 | −78.197 | 1.00 | 19.08 | C |
| ATOM | 10785 | O   | ILE C | 393 | −55.843 | 63.574 | −78.244 | 1.00 | 19.38 | O |
| ATOM | 10786 | N   | CYS C | 394 | −54.520 | 61.818 | −78.533 | 1.00 | 20.70 | N |
| ATOM | 10787 | CA  | CYS C | 394 | −53.347 | 62.673 | −78.770 | 1.00 | 21.35 | C |
| ATOM | 10788 | CB  | CYS C | 394 | −52.188 | 62.275 | −77.839 | 1.00 | 22.80 | C |
| ATOM | 10789 | SG  | CYS C | 394 | −50.953 | 61.146 | −78.509 | 1.00 | 23.92 | S |
| ATOM | 10790 | C   | CYS C | 394 | −52.857 | 62.892 | −80.220 | 1.00 | 21.21 | C |
| ATOM | 10791 | O   | CYS C | 394 | −51.894 | 63.630 | −80.432 | 1.00 | 21.16 | O |
| ATOM | 10792 | N   | ALA C | 395 | −53.505 | 62.287 | −81.216 | 1.00 | 20.74 | N |
| ATOM | 10793 | CA  | ALA C | 395 | −53.177 | 62.630 | −82.596 | 1.00 | 20.39 | C |
| ATOM | 10794 | CB  | ALA C | 395 | −53.272 | 64.130 | −82.838 | 1.00 | 20.57 | C |
| ATOM | 10795 | C   | ALA C | 395 | −51.787 | 62.099 | −82.932 | 1.00 | 19.77 | C |
| ATOM | 10796 | O   | ALA C | 395 | −51.366 | 62.147 | −84.087 | 1.00 | 19.25 | O |
| ATOM | 10797 | N   | SER C | 396 | −51.097 | 61.596 | −81.914 | 1.00 | 19.91 | N |
| ATOM | 10798 | CA  | SER C | 396 | −49.774 | 61.009 | −82.077 | 1.00 | 20.17 | C |
| ATOM | 10799 | CB  | SER C | 396 | −49.218 | 60.548 | −80.724 | 1.00 | 20.10 | C |
| ATOM | 10800 | OG  | SER C | 396 | −48.308 | 59.474 | −80.860 | 1.00 | 20.63 | O |
| ATOM | 10801 | C   | SER C | 396 | −49.856 | 59.845 | −83.043 | 1.00 | 20.44 | C |
| ATOM | 10802 | O   | SER C | 396 | −50.426 | 58.808 | −82.731 | 1.00 | 21.13 | O |
| ATOM | 10803 | N   | HIS C | 397 | −49.275 | 60.031 | −84.218 | 1.00 | 20.97 | N |
| ATOM | 10804 | CA  | HIS C | 397 | −49.300 | 59.035 | −85.262 | 1.00 | 21.61 | C |
| ATOM | 10805 | CB  | HIS C | 397 | −48.510 | 59.544 | −86.462 | 1.00 | 22.55 | C |
| ATOM | 10806 | CG  | HIS C | 397 | −48.269 | 58.501 | −87.506 | 1.00 | 23.83 | C |
| ATOM | 10807 | ND1 | HIS C | 397 | −47.035 | 58.102 | −87.852 | 1.00 | 24.43 | N |
| ATOM | 10808 | CE1 | HIS C | 397 | −47.129 | 57.135 | −88.779 | 1.00 | 25.57 | C |
| ATOM | 10809 | NE2 | HIS C | 397 | −48.436 | 56.912 | −89.021 | 1.00 | 25.65 | N |
| ATOM | 10810 | CD2 | HIS C | 397 | −49.162 | 57.729 | −88.249 | 1.00 | 24.44 | C |
| ATOM | 10811 | C   | HIS C | 397 | −48.795 | 57.683 | −84.769 | 1.00 | 22.20 | C |
| ATOM | 10812 | O   | HIS C | 397 | −47.591 | 57.487 | −84.549 | 1.00 | 22.16 | O |
| ATOM | 10813 | N   | ILE C | 398 | −49.727 | 56.742 | −84.591 | 1.00 | 22.21 | N |
| ATOM | 10814 | CA  | ILE C | 398 | −49.447 | 55.449 | −83.944 | 1.00 | 21.94 | C |
| ATOM | 10815 | CB  | ILE C | 398 | −50.674 | 54.960 | −83.118 | 1.00 | 21.28 | C |
| ATOM | 10816 | CG1 | ILE C | 398 | −50.987 | 55.913 | −81.947 | 1.00 | 21.45 | C |
| ATOM | 10817 | CD1 | ILE C | 398 | −49.957 | 55.979 | −80.839 | 1.00 | 21.66 | C |
| ATOM | 10818 | CG2 | ILE C | 398 | −50.510 | 53.525 | −82.638 | 1.00 | 20.78 | C |
| ATOM | 10819 | C   | ILE C | 398 | −49.026 | 54.359 | −84.942 | 1.00 | 22.75 | C |
| ATOM | 10820 | O   | ILE C | 398 | −48.460 | 53.342 | −84.545 | 1.00 | 23.32 | O |
| ATOM | 10821 | N   | GLY C | 399 | −49.305 | 54.560 | −86.231 | 1.00 | 22.76 | N |
| ATOM | 10822 | CA  | GLY C | 399 | −49.054 | 53.510 | −87.222 | 1.00 | 22.66 | C |
| ATOM | 10823 | C   | GLY C | 399 | −49.995 | 53.551 | −88.411 | 1.00 | 23.04 | C |
| ATOM | 10824 | O   | GLY C | 399 | −50.291 | 54.629 | −88.941 | 1.00 | 23.19 | O |
| ATOM | 10825 | N   | TRP C | 400 | −50.459 | 52.373 | −88.836 | 1.00 | 23.20 | N |
| ATOM | 10826 | CA  | TRP C | 400 | −51.282 | 52.238 | −90.050 | 1.00 | 23.42 | C |
| ATOM | 10827 | CB  | TRP C | 400 | −50.400 | 52.022 | −91.291 | 1.00 | 23.86 | C |
| ATOM | 10828 | CG  | TRP C | 400 | −49.297 | 53.040 | −91.465 | 1.00 | 23.58 | C |
| ATOM | 10829 | CD1 | TRP C | 400 | −49.366 | 54.267 | −92.119 | 1.00 | 23.51 | C |
| ATOM | 10830 | NE1 | TRP C | 400 | −48.162 | 54.916 | −92.066 | 1.00 | 23.68 | N |
| ATOM | 10831 | CE2 | TRP C | 400 | −47.255 | 54.181 | −91.388 | 1.00 | 23.56 | C |
| ATOM | 10832 | CD2 | TRP C | 400 | −47.925 | 52.944 | −90.976 | 1.00 | 23.38 | C |
| ATOM | 10833 | CE3 | TRP C | 400 | −47.209 | 51.995 | −90.261 | 1.00 | 23.30 | C |
| ATOM | 10834 | CZ3 | TRP C | 400 | −45.870 | 52.259 | −89.962 | 1.00 | 23.92 | C |
| ATOM | 10835 | CH2 | TRP C | 400 | −45.242 | 53.451 | −90.375 | 1.00 | 23.81 | C |
| ATOM | 10836 | CZ2 | TRP C | 400 | −45.926 | 54.433 | −91.090 | 1.00 | 23.62 | C |
| ATOM | 10837 | C   | TRP C | 400 | −52.273 | 51.111 | −89.988 | 1.00 | 23.35 | C |
| ATOM | 10838 | O   | TRP C | 400 | −51.991 | 50.047 | −89.417 | 1.00 | 22.27 | O |
| ATOM | 10839 | N   | LYS C | 401 | −53.435 | 51.335 | −90.604 | 1.00 | 23.79 | N |
| ATOM | 10840 | CA  | LYS C | 401 | −54.363 | 50.252 | −90.937 | 1.00 | 24.46 | C |

-continued

| | | | | | | | | | | |
|---|---|---|---|---|---|---|---|---|---|---|
| ATOM | 10841 | CB | LYS C | 401 | −55.816 | 50.688 | −90.780 | 1.00 | 24.09 | C |
| ATOM | 10842 | CG | LYS C | 401 | −56.803 | 49.611 | −91.196 | 1.00 | 23.23 | C |
| ATOM | 10843 | CD | LYS C | 401 | −58.244 | 50.012 | −90.948 | 1.00 | 22.72 | C |
| ATOM | 10844 | CE | LYS C | 401 | −59.140 | 48.794 | −91.043 | 1.00 | 22.41 | C |
| ATOM | 10845 | NZ | LYS C | 401 | −60.526 | 49.070 | −90.600 | 1.00 | 22.50 | N |
| ATOM | 10846 | C | LYS C | 401 | −54.137 | 49.777 | −92.368 | 1.00 | 25.20 | C |
| ATOM | 10847 | O | LYS C | 401 | −54.076 | 50.579 | −93.306 | 1.00 | 24.71 | O |
| ATOM | 10848 | N | PHE C | 402 | −54.015 | 48.466 | −92.527 | 1.00 | 26.71 | N |
| ATOM | 10849 | CA | PHE C | 402 | −53.828 | 47.878 | −93.844 | 1.00 | 27.68 | C |
| ATOM | 10850 | CB | PHE C | 402 | −52.655 | 46.896 | −93.855 | 1.00 | 28.40 | C |
| ATOM | 10851 | CG | PHE C | 402 | −51.303 | 47.552 | −93.753 | 1.00 | 29.07 | C |
| ATOM | 10852 | CD2 | PHE C | 402 | −50.578 | 47.866 | −94.902 | 1.00 | 29.82 | C |
| ATOM | 10853 | CE2 | PHE C | 402 | −49.323 | 48.460 | −94.810 | 1.00 | 29.71 | C |
| ATOM | 10854 | CZ | PHE C | 402 | −48.780 | 48.748 | −93.565 | 1.00 | 29.24 | C |
| ATOM | 10855 | CE1 | PHE C | 402 | −49.490 | 48.438 | −92.413 | 1.00 | 28.84 | C |
| ATOM | 10856 | CD1 | PHE C | 402 | −50.741 | 47.841 | −92.510 | 1.00 | 28.82 | C |
| ATOM | 10857 | C | PHE C | 402 | −55.101 | 47.168 | −94.251 | 1.00 | 27.64 | C |
| ATOM | 10858 | O | PHE C | 402 | −55.692 | 46.433 | −93.459 | 1.00 | 27.81 | O |
| ATOM | 10859 | N | THR C | 403 | −55.527 | 47.411 | −95.484 | 1.00 | 27.40 | N |
| ATOM | 10860 | CA | THR C | 403 | −56.710 | 46.771 | −96.026 | 1.00 | 27.27 | C |
| ATOM | 10861 | CB | THR C | 403 | −57.783 | 47.805 | −96.394 | 1.00 | 26.67 | C |
| ATOM | 10862 | OG1 | THR C | 403 | −57.175 | 48.886 | −97.109 | 1.00 | 26.59 | O |
| ATOM | 10863 | CG2 | THR C | 403 | −58.445 | 48.342 | −95.144 | 1.00 | 25.92 | C |
| ATOM | 10864 | C | THR C | 403 | −56.321 | 45.994 | −97.265 | 1.00 | 27.96 | C |
| ATOM | 10865 | O | THR C | 403 | −55.388 | 46.375 | −97.970 | 1.00 | 28.37 | O |
| ATOM | 10866 | N | ALA C | 404 | −57.022 | 44.890 | −97.515 | 1.00 | 28.74 | N |
| ATOM | 10867 | CA | ALA C | 404 | −56.804 | 44.091 | −98.709 | 1.00 | 28.90 | C |
| ATOM | 10868 | CB | ALA C | 404 | −57.426 | 42.722 | −98.534 | 1.00 | 28.84 | C |
| ATOM | 10869 | C | ALA C | 404 | −57.387 | 44.791 | −99.934 | 1.00 | 30.60 | C |
| ATOM | 10870 | O | ALA C | 404 | −58.324 | 45.606 | −99.820 | 1.00 | 29.71 | O |
| ATOM | 10871 | N | THR C | 405 | −56.808 | 44.490 | −101.098 | 1.00 | 32.77 | N |
| ATOM | 10872 | CA | THR C | 405 | −57.319 | 44.975 | −102.392 | 1.00 | 34.13 | C |
| ATOM | 10873 | CB | THR C | 405 | −56.211 | 45.638 | −103.241 | 1.00 | 32.82 | C |
| ATOM | 10874 | OG1 | THR C | 405 | −54.926 | 45.276 | −102.721 | 1.00 | 30.39 | O |
| ATOM | 10875 | CG2 | THR C | 405 | −56.355 | 47.171 | −103.222 | 1.00 | 32.92 | C |
| ATOM | 10876 | C | THR C | 405 | −58.009 | 43.861 | −103.193 | 1.00 | 35.64 | C |
| ATOM | 10877 | O | THR C | 405 | −58.655 | 44.121 | −104.203 | 1.00 | 35.44 | O |
| ATOM | 10878 | N | LYS C | 406 | −57.864 | 42.626 | −102.723 | 1.00 | 38.71 | N |
| ATOM | 10879 | CA | LYS C | 406 | −58.526 | 41.477 | −103.326 | 1.00 | 43.17 | C |
| ATOM | 10880 | CB | LYS C | 406 | −57.499 | 40.407 | −103.723 | 1.00 | 47.20 | C |
| ATOM | 10881 | CG | LYS C | 406 | −56.657 | 40.703 | −104.961 | 1.00 | 48.72 | C |
| ATOM | 10882 | CD | LYS C | 406 | −55.541 | 39.668 | −105.101 | 1.00 | 49.63 | C |
| ATOM | 10883 | CE | LYS C | 406 | −54.635 | 39.945 | −106.293 | 1.00 | 50.26 | C |
| ATOM | 10884 | NZ | LYS C | 406 | −55.316 | 39.665 | −107.589 | 1.00 | 50.93 | N |
| ATOM | 10885 | C | LYS C | 406 | −59.527 | 40.875 | −102.340 | 1.00 | 44.23 | C |
| ATOM | 10886 | O | LYS C | 406 | −59.270 | 40.828 | −101.133 | 1.00 | 44.55 | O |
| ATOM | 10887 | N | LYS C | 407 | −60.658 | 40.404 | −102.863 | 1.00 | 45.17 | N |
| ATOM | 10888 | CA | LYS C | 407 | −61.727 | 39.848 | −102.036 | 1.00 | 45.67 | C |
| ATOM | 10889 | CB | LYS C | 407 | −63.088 | 40.024 | −102.728 | 1.00 | 47.68 | C |
| ATOM | 10890 | CG | LYS C | 407 | −63.931 | 41.185 | −102.199 | 1.00 | 49.68 | C |
| ATOM | 10891 | CD | LYS C | 407 | −64.295 | 41.019 | −100.719 | 1.00 | 51.04 | C |
| ATOM | 10892 | CE | LYS C | 407 | −65.264 | 39.861 | −100.481 | 1.00 | 51.28 | C |
| ATOM | 10893 | NZ | LYS C | 407 | −65.171 | 39.333 | −99.090 | 1.00 | 50.49 | N |
| ATOM | 10894 | C | LYS C | 407 | −61.500 | 38.381 | −101.664 | 1.00 | 45.25 | C |
| ATOM | 10895 | O | LYS C | 407 | −62.369 | 37.742 | −101.071 | 1.00 | 44.78 | O |
| ATOM | 10896 | N | ASP C | 408 | −60.326 | 37.861 | −102.006 | 1.00 | 45.55 | N |
| ATOM | 10897 | CA | ASP C | 408 | −60.000 | 36.452 | −101.789 | 1.00 | 46.17 | C |
| ATOM | 10898 | CB | ASP C | 408 | −59.590 | 35.799 | −103.117 | 1.00 | 47.92 | C |
| ATOM | 10899 | CG | ASP C | 408 | −58.441 | 36.542 | −103.811 | 1.00 | 50.72 | C |
| ATOM | 10900 | OD1 | ASP C | 408 | −58.569 | 37.767 | −104.043 | 1.00 | 49.75 | O |
| ATOM | 10901 | OD2 | ASP C | 408 | −57.410 | 35.901 | −104.127 | 1.00 | 51.05 | O |
| ATOM | 10902 | C | ASP C | 408 | −58.885 | 36.294 | −100.754 | 1.00 | 45.25 | C |
| ATOM | 10903 | O | ASP C | 408 | −58.552 | 35.184 | −100.353 | 1.00 | 44.45 | O |
| ATOM | 10904 | N | MET C | 409 | −58.317 | 37.420 | −100.332 | 1.00 | 46.02 | N |
| ATOM | 10905 | CA | MET C | 409 | −57.178 | 37.446 | −99.418 | 1.00 | 45.36 | C |
| ATOM | 10906 | CB | MET C | 409 | −56.454 | 38.782 | −99.541 | 1.00 | 44.14 | C |
| ATOM | 10907 | CG | MET C | 409 | −55.603 | 38.905 | −100.783 | 1.00 | 44.40 | C |
| ATOM | 10908 | SD | MET C | 409 | −54.746 | 40.485 | −100.854 | 1.00 | 45.71 | S |
| ATOM | 10909 | CE | MET C | 409 | −53.161 | 39.955 | −101.511 | 1.00 | 44.45 | C |
| ATOM | 10910 | C | MET C | 409 | −57.618 | 37.274 | −97.978 | 1.00 | 46.56 | C |
| ATOM | 10911 | O | MET C | 409 | −58.655 | 37.815 | −97.574 | 1.00 | 47.61 | O |
| ATOM | 10912 | N | SER C | 410 | −56.826 | 36.541 | −97.195 | 1.00 | 45.59 | N |
| ATOM | 10913 | CA | SER C | 410 | −57.057 | 36.479 | −95.748 | 1.00 | 43.55 | C |
| ATOM | 10914 | CB | SER C | 410 | −56.977 | 35.056 | −95.221 | 1.00 | 42.41 | C |
| ATOM | 10915 | OG | SER C | 410 | −57.771 | 34.940 | −94.058 | 1.00 | 43.14 | O |
| ATOM | 10916 | C | SER C | 410 | −56.134 | 37.441 | −94.983 | 1.00 | 43.24 | C |
| ATOM | 10917 | O | SER C | 410 | −55.052 | 37.784 | −95.476 | 1.00 | 42.29 | O |

-continued

| | | | | | | | | | |
|---|---|---|---|---|---|---|---|---|---|
| ATOM | 10918 | N | PRO C | 411 | −56.494 | 37.759 | −93.721 | 1.00 | 42.22 | N |
| ATOM | 10919 | CA | PRO C | 411 | −56.727 | 39.095 | −93.201 | 1.00 | 39.59 | C |
| ATOM | 10920 | CB | PRO C | 411 | −55.355 | 39.482 | −92.646 | 1.00 | 39.42 | C |
| ATOM | 10921 | CG | PRO C | 411 | −54.715 | 38.164 | −92.294 | 1.00 | 40.84 | C |
| ATOM | 10922 | CD | PRO C | 411 | −55.638 | 37.051 | −92.764 | 1.00 | 42.23 | C |
| ATOM | 10923 | C | PRO C | 411 | −57.235 | 40.087 | −94.251 | 1.00 | 38.13 | C |
| ATOM | 10924 | O | PRO C | 411 | −56.478 | 40.515 | −95.124 | 1.00 | 38.17 | O |
| ATOM | 10925 | N | GLN C | 412 | −58.520 | 40.432 | −94.174 | 1.00 | 36.11 | N |
| ATOM | 10926 | CA | GLN C | 412 | −59.075 | 41.491 | −95.022 | 1.00 | 34.08 | C |
| ATOM | 10927 | CB | GLN C | 412 | −60.604 | 41.394 | −95.115 | 1.00 | 32.51 | C |
| ATOM | 10928 | CG | GLN C | 412 | −61.083 | 40.457 | −96.221 | 1.00 | 32.05 | C |
| ATOM | 10929 | CD | GLN C | 412 | −60.680 | 40.918 | −97.628 | 1.00 | 31.67 | C |
| ATOM | 10930 | OE1 | GLN C | 412 | −61.300 | 41.817 | −98.205 | 1.00 | 30.90 | O |
| ATOM | 10931 | NE2 | GLN C | 412 | −59.649 | 40.282 | −98.193 | 1.00 | 30.63 | N |
| ATOM | 10932 | C | GLN C | 412 | −58.607 | 42.872 | −94.553 | 1.00 | 33.05 | C |
| ATOM | 10933 | O | GLN C | 412 | −58.502 | 43.816 | −95.343 | 1.00 | 32.50 | O |
| ATOM | 10934 | N | LYS C | 413 | −58.318 | 42.967 | −93.259 | 1.00 | 32.05 | N |
| ATOM | 10935 | CA | LYS C | 413 | −57.598 | 44.099 | −92.690 | 1.00 | 30.72 | C |
| ATOM | 10936 | CB | LYS C | 413 | −58.562 | 45.214 | −92.262 | 1.00 | 29.67 | C |
| ATOM | 10937 | CG | LYS C | 413 | −59.205 | 45.037 | −90.894 | 1.00 | 29.94 | C |
| ATOM | 10938 | CD | LYS C | 413 | −60.456 | 44.178 | −90.956 | 1.00 | 31.98 | C |
| ATOM | 10939 | CE | LYS C | 413 | −60.160 | 42.721 | −90.619 | 1.00 | 33.11 | C |
| ATOM | 10940 | NZ | LYS C | 413 | −61.178 | 41.794 | −91.194 | 1.00 | 34.69 | N |
| ATOM | 10941 | C | LYS C | 413 | −56.738 | 43.632 | −91.510 | 1.00 | 30.14 | C |
| ATOM | 10942 | O | LYS C | 413 | −56.966 | 42.566 | −90.939 | 1.00 | 30.32 | O |
| ATOM | 10943 | N | PHE C | 414 | −55.725 | 44.422 | −91.185 | 1.00 | 29.43 | N |
| ATOM | 10944 | CA | PHE C | 414 | −54.949 | 44.248 | −89.966 | 1.00 | 29.84 | C |
| ATOM | 10945 | CB | PHE C | 414 | −53.873 | 43.162 | −90.126 | 1.00 | 30.59 | C |
| ATOM | 10946 | CG | PHE C | 414 | −52.790 | 43.514 | −91.108 | 1.00 | 31.07 | C |
| ATOM | 10947 | CD1 | PHE C | 414 | −52.936 | 43.223 | −92.458 | 1.00 | 30.91 | C |
| ATOM | 10948 | CE1 | PHE C | 414 | −51.945 | 43.553 | −93.366 | 1.00 | 31.64 | C |
| ATOM | 10949 | CZ | PHE C | 414 | −50.785 | 44.173 | −92.930 | 1.00 | 31.60 | C |
| ATOM | 10950 | CE2 | PHE C | 414 | −50.625 | 44.466 | −91.588 | 1.00 | 31.81 | C |
| ATOM | 10951 | CD2 | PHE C | 414 | −51.623 | 44.139 | −90.682 | 1.00 | 31.37 | C |
| ATOM | 10952 | C | PHE C | 414 | −54.305 | 45.589 | −89.668 | 1.00 | 29.80 | C |
| ATOM | 10953 | O | PHE C | 414 | −54.223 | 46.454 | −90.555 | 1.00 | 29.64 | O |
| ATOM | 10954 | N | TRP C | 415 | −53.850 | 45.765 | −88.432 | 1.00 | 28.78 | N |
| ATOM | 10955 | CA | TRP C | 415 | −53.170 | 46.998 | −88.064 | 1.00 | 28.14 | C |
| ATOM | 10956 | CB | TRP C | 415 | −53.774 | 47.619 | −86.801 | 1.00 | 29.01 | C |
| ATOM | 10957 | CG | TRP C | 415 | −55.005 | 48.485 | −87.056 | 1.00 | 29.70 | C |
| ATOM | 10958 | CD1 | TRP C | 415 | −55.046 | 49.858 | −87.354 | 1.00 | 29.56 | C |
| ATOM | 10959 | NE1 | TRP C | 415 | −56.342 | 50.290 | −87.513 | 1.00 | 29.12 | N |
| ATOM | 10960 | CE2 | TRP C | 415 | −57.204 | 49.267 | −87.339 | 1.00 | 29.99 | C |
| ATOM | 10961 | CD2 | TRP C | 415 | −56.404 | 48.063 | −87.041 | 1.00 | 29.10 | C |
| ATOM | 10962 | CE3 | TRP C | 415 | −57.051 | 46.860 | −86.821 | 1.00 | 29.53 | C |
| ATOM | 10963 | CZ3 | TRP C | 415 | −58.452 | 46.831 | −86.884 | 1.00 | 31.48 | C |
| ATOM | 10964 | CH2 | TRP C | 415 | −59.205 | 47.990 | −87.170 | 1.00 | 32.68 | C |
| ATOM | 10965 | CZ2 | TRP C | 415 | −58.590 | 49.232 | −87.405 | 1.00 | 31.47 | C |
| ATOM | 10966 | C | TRP C | 415 | −51.692 | 46.805 | −87.938 | 1.00 | 26.85 | C |
| ATOM | 10967 | O | TRP C | 415 | −51.225 | 45.785 | −87.426 | 1.00 | 26.36 | O |
| ATOM | 10968 | N | GLY C | 416 | −50.947 | 47.781 | −88.450 | 1.00 | 26.11 | N |
| ATOM | 10969 | CA | GLY C | 416 | −49.492 | 47.806 | −88.341 | 1.00 | 24.91 | C |
| ATOM | 10970 | C | GLY C | 416 | −49.093 | 48.970 | −87.463 | 1.00 | 23.86 | C |
| ATOM | 10971 | O | GLY C | 416 | −49.324 | 50.131 | −87.805 | 1.00 | 23.87 | O |
| ATOM | 10972 | N | LEU C | 417 | −48.512 | 48.659 | −86.316 | 1.00 | 22.91 | N |
| ATOM | 10973 | CA | LEU C | 417 | −48.267 | 49.665 | −85.311 | 1.00 | 22.85 | C |
| ATOM | 10974 | CB | LEU C | 417 | −48.923 | 49.256 | −84.002 | 1.00 | 22.05 | C |
| ATOM | 10975 | CG | LEU C | 417 | −50.410 | 48.905 | −84.089 | 1.00 | 21.54 | C |
| ATOM | 10976 | CD1 | LEU C | 417 | −50.899 | 48.334 | −82.771 | 1.00 | 20.93 | C |
| ATOM | 10977 | CD2 | LEU C | 417 | −51.243 | 50.108 | −84.514 | 1.00 | 21.03 | C |
| ATOM | 10978 | C | LEU C | 417 | −46.784 | 49.869 | −85.119 | 1.00 | 23.87 | C |
| ATOM | 10979 | O | LEU C | 417 | −46.047 | 48.926 | −84.847 | 1.00 | 24.49 | O |
| ATOM | 10980 | N | THR C | 418 | −46.338 | 51.106 | −85.279 | 1.00 | 25.14 | N |
| ATOM | 10981 | CA | THR C | 418 | −44.925 | 51.401 | −85.123 | 1.00 | 25.89 | C |
| ATOM | 10982 | CB | THR C | 418 | −44.490 | 52.700 | −85.859 | 1.00 | 27.18 | C |
| ATOM | 10983 | OG1 | THR C | 418 | −43.135 | 53.018 | −85.507 | 1.00 | 28.92 | O |
| ATOM | 10984 | CG2 | THR C | 418 | −45.402 | 53.880 | −85.515 | 1.00 | 27.26 | C |
| ATOM | 10985 | C | THR C | 418 | −44.512 | 51.374 | −83.649 | 1.00 | 24.74 | C |
| ATOM | 10986 | O | THR C | 418 | −45.136 | 51.997 | −82.799 | 1.00 | 23.05 | O |
| ATOM | 10987 | N | ARG C | 419 | −43.453 | 50.616 | −83.389 | 1.00 | 25.11 | N |
| ATOM | 10988 | CA | ARG C | 419 | −42.970 | 50.286 | −82.054 | 1.00 | 25.49 | C |
| ATOM | 10989 | CB | ARG C | 419 | −41.810 | 49.307 | −82.196 | 1.00 | 25.54 | C |
| ATOM | 10990 | CG | ARG C | 419 | −41.188 | 48.824 | −80.815 | 1.00 | 26.51 | C |
| ATOM | 10991 | CD | ARG C | 419 | −39.758 | 48.375 | −81.165 | 1.00 | 28.45 | C |
| ATOM | 10992 | NE | ARG C | 419 | −38.791 | 49.480 | −81.162 | 1.00 | 29.09 | N |
| ATOM | 10993 | CZ | ARG C | 419 | −38.300 | 50.050 | −80.058 | 1.00 | 30.69 | C |
| ATOM | 10994 | NH1 | ARG C | 419 | −37.422 | 51.044 | −80.154 | 1.00 | 31.68 | N |

Atomic coordinates for CRBN:DDB1:Lenalidomide (Human protein)

-continued

| | | | | Atomic coordinates for CRBN:DDB1:Lenalidomide (Human protein) | | | | | |
|---|---|---|---|---|---|---|---|---|---|
| ATOM | 10995 | NH2 | ARG C | 419 | −38.694 | 49.642 | −78.852 | 1.00 | 30.69 | N |
| ATOM | 10996 | C | ARG C | 419 | −42.559 | 51.504 | −81.207 | 1.00 | 26.18 | C |
| ATOM | 10997 | O | ARG C | 419 | −42.719 | 51.503 | −79.986 | 1.00 | 27.26 | O |
| ATOM | 10998 | N | SER C | 420 | −42.049 | 52.546 | −81.847 | 1.00 | 26.70 | N |
| ATOM | 10999 | CA | SER C | 420 | −41.657 | 53.750 | −81.121 | 1.00 | 27.14 | C |
| ATOM | 11000 | CB | SER C | 420 | −40.787 | 54.630 | −81.996 | 1.00 | 28.41 | C |
| ATOM | 11001 | OG | SER C | 420 | −41.527 | 55.041 | −83.130 | 1.00 | 32.16 | O |
| ATOM | 11002 | C | SER C | 420 | −42.866 | 54.547 | −80.646 | 1.00 | 27.05 | C |
| ATOM | 11003 | O | SER C | 420 | −42.735 | 55.458 | −79.830 | 1.00 | 27.62 | O |
| ATOM | 11004 | N | ALA C | 421 | −44.040 | 54.204 | −81.162 | 1.00 | 27.34 | N |
| ATOM | 11005 | CA | ALA C | 421 | −45.274 | 54.878 | −80.777 | 1.00 | 27.16 | C |
| ATOM | 11006 | CB | ALA C | 421 | −46.208 | 54.991 | −81.968 | 1.00 | 26.54 | C |
| ATOM | 11007 | C | ALA C | 421 | −45.989 | 54.195 | −79.610 | 1.00 | 28.17 | C |
| ATOM | 11008 | O | ALA C | 421 | −46.995 | 54.723 | −79.117 | 1.00 | 29.31 | O |
| ATOM | 11009 | N | LEU C | 422 | −45.476 | 53.043 | −79.160 | 1.00 | 27.26 | N |
| ATOM | 11010 | CA | LEU C | 422 | −46.175 | 52.233 | −78.147 | 1.00 | 27.01 | C |
| ATOM | 11011 | CB | LEU C | 422 | −46.448 | 50.821 | −78.673 | 1.00 | 26.12 | C |
| ATOM | 11012 | CG | LEU C | 422 | −47.114 | 50.591 | −80.033 | 1.00 | 25.82 | C |
| ATOM | 11013 | CD1 | LEU C | 422 | −46.909 | 49.145 | −80.478 | 1.00 | 25.98 | C |
| ATOM | 11014 | CD2 | LEU C | 422 | −48.593 | 50.943 | −80.014 | 1.00 | 25.16 | C |
| ATOM | 11015 | C | LEU C | 422 | −45.470 | 52.147 | −76.779 | 1.00 | 28.04 | C |
| ATOM | 11016 | O | LEU C | 422 | −44.248 | 52.316 | −76.676 | 1.00 | 29.23 | O |
| ATOM | 11017 | N | LEU C | 423 | −46.261 | 51.883 | −75.737 | 1.00 | 27.88 | N |
| ATOM | 11018 | CA | LEU C | 423 | −45.753 | 51.624 | −74.389 | 1.00 | 28.03 | C |
| ATOM | 11019 | CB | LEU C | 423 | −46.060 | 52.795 | −73.450 | 1.00 | 26.84 | C |
| ATOM | 11020 | CG | LEU C | 423 | −45.070 | 53.239 | −72.365 | 1.00 | 26.34 | C |
| ATOM | 11021 | CD1 | LEU C | 423 | −45.815 | 53.961 | −71.259 | 1.00 | 26.27 | C |
| ATOM | 11022 | CD2 | LEU C | 423 | −44.250 | 52.106 | −71.774 | 1.00 | 26.60 | C |
| ATOM | 11023 | C | LEU C | 423 | −46.436 | 50.362 | −73.859 | 1.00 | 29.34 | C |
| ATOM | 11024 | O | LEU C | 423 | −47.650 | 50.360 | −73.639 | 1.00 | 29.98 | O |
| ATOM | 11025 | N | PRO C | 424 | −45.668 | 49.276 | −73.675 | 1.00 | 30.36 | N |
| ATOM | 11026 | CA | PRO C | 424 | −46.239 | 48.064 | −73.102 | 1.00 | 31.37 | C |
| ATOM | 11027 | CB | PRO C | 424 | −45.080 | 47.066 | −73.177 | 1.00 | 31.26 | C |
| ATOM | 11028 | CG | PRO C | 424 | −43.852 | 47.919 | −73.212 | 1.00 | 31.24 | C |
| ATOM | 11029 | CD | PRO C | 424 | −44.257 | 49.088 | −74.051 | 1.00 | 30.70 | C |
| ATOM | 11030 | C | PRO C | 424 | −46.663 | 48.290 | −71.655 | 1.00 | 32.48 | C |
| ATOM | 11031 | O | PRO C | 424 | −45.967 | 48.970 | −70.904 | 1.00 | 32.43 | O |
| ATOM | 11032 | N | THR C | 425 | −47.813 | 47.747 | −71.280 | 1.00 | 34.69 | N |
| ATOM | 11033 | CA | THR C | 425 | −48.317 | 47.930 | −69.935 | 1.00 | 37.50 | C |
| ATOM | 11034 | CB | THR C | 425 | −49.548 | 48.881 | −69.886 | 1.00 | 38.16 | C |
| ATOM | 11035 | OG1 | THR C | 425 | −49.276 | 50.071 | −70.632 | 1.00 | 37.03 | O |
| ATOM | 11036 | CG2 | THR C | 425 | −49.892 | 49.279 | −68.435 | 1.00 | 38.92 | C |
| ATOM | 11037 | C | THR C | 425 | −48.649 | 46.592 | −69.296 | 1.00 | 39.57 | C |
| ATOM | 11038 | O | THR C | 425 | −49.005 | 45.625 | −69.983 | 1.00 | 37.46 | O |
| ATOM | 11039 | N | ILE C | 426 | −48.473 | 46.553 | −67.937 | 1.00 | 43.46 | N |
| ATOM | 11040 | CA | ILE C | 426 | −48.937 | 45.468 | −67.121 | 1.00 | 45.95 | C |
| ATOM | 11041 | CB | ILE C | 426 | −47.798 | 44.921 | −66.194 | 1.00 | 46.03 | C |
| ATOM | 11042 | CG1 | ILE C | 426 | −48.335 | 44.390 | −64.852 | 1.00 | 45.69 | C |
| ATOM | 11043 | CD1 | ILE C | 426 | −48.686 | 42.916 | −64.857 | 1.00 | 46.22 | C |
| ATOM | 11044 | CG2 | ILE C | 426 | −46.689 | 45.950 | −66.000 | 1.00 | 45.70 | C |
| ATOM | 11045 | C | ILE C | 426 | −50.162 | 45.989 | −66.359 | 1.00 | 48.33 | C |
| ATOM | 11046 | O | ILE C | 426 | −50.023 | 46.625 | −65.303 | 1.00 | 49.38 | O |
| ATOM | 11047 | N | PRO C | 427 | −51.369 | 45.731 | −66.915 | 1.00 | 50.24 | N |
| ATOM | 11048 | CA | PRO C | 427 | −52.650 | 46.315 | −66.482 | 1.00 | 50.66 | C |
| ATOM | 11049 | CB | PRO C | 427 | −53.656 | 45.712 | −67.466 | 1.00 | 50.44 | C |
| ATOM | 11050 | CG | PRO C | 427 | −53.038 | 44.418 | −67.883 | 1.00 | 49.52 | C |
| ATOM | 11051 | CD | PRO C | 427 | −51.568 | 44.706 | −67.960 | 1.00 | 49.41 | C |
| ATOM | 11052 | C | PRO C | 427 | −53.038 | 45.942 | −65.052 | 1.00 | 51.88 | C |
| ATOM | 11053 | O | PRO C | 427 | −52.543 | 44.944 | −64.523 | 1.00 | 50.60 | O |
| ATOM | 11054 | N | ASP C | 428 | −53.933 | 46.743 | −64.463 | 1.00 | 54.14 | N |
| ATOM | 11055 | CA | ASP C | 428 | −54.423 | 46.607 | −63.075 | 1.00 | 54.72 | C |
| ATOM | 11056 | CB | ASP C | 428 | −54.090 | 45.241 | −62.450 | 1.00 | 57.03 | C |
| ATOM | 11057 | CG | ASP C | 428 | −54.903 | 44.095 | −63.050 | 1.00 | 57.54 | C |
| ATOM | 11058 | OD1 | ASP C | 428 | −55.606 | 44.309 | −64.064 | 1.00 | 57.45 | O |
| ATOM | 11059 | OD2 | ASP C | 428 | −54.821 | 42.971 | −62.507 | 1.00 | 58.01 | O |
| ATOM | 11060 | C | ASP C | 428 | −53.878 | 47.722 | −62.198 | 1.00 | 54.29 | C |
| ATOM | 11061 | O | ASP C | 428 | −54.622 | 48.608 | −61.782 | 1.00 | 55.54 | O |
| ATOM | 11062 | ZN | ZN C | 1 | −52.468 | 59.031 | −77.507 | 1.00 | 81.35 | ZN |
| ATOM | 11063 | O1 | MOL B | 1 | −44.038 | 55.904 | −93.534 | 1.00 | 40.49 | O |
| ATOM | 11064 | C2 | MOL B | 1 | −44.496 | 56.170 | −94.644 | 1.00 | 39.14 | C |
| ATOM | 11065 | C6 | MOL B | 1 | −44.445 | 57.434 | −95.230 | 1.00 | 39.50 | C |
| ATOM | 11066 | C9 | MOL B | 1 | −43.947 | 58.660 | −94.800 | 1.00 | 39.12 | C |
| ATOM | 11067 | C12 | MOL B | 1 | −44.036 | 59.772 | −95.633 | 1.00 | 37.74 | C |
| ATOM | 11068 | C13 | MOL B | 1 | −44.621 | 59.663 | −96.893 | 1.00 | 37.56 | C |
| ATOM | 11069 | C10 | MOL B | 1 | −45.118 | 58.439 | −97.325 | 1.00 | 37.83 | C |
| ATOM | 11070 | N3 | MOL B | 1 | −45.677 | 58.322 | −98.524 | 1.00 | 39.22 | N |
| ATOM | 11071 | C7 | MOL B | 1 | −45.025 | 57.339 | −96.487 | 1.00 | 38.40 | C |

-continued

Atomic coordinates for CRBN:DDB1:Lenalidomide (Human protein)

| ATOM | 11072 | C3  | MOL B | 1  | −45.482 | 55.904  | −96.711  | 1.00 | 37.69 | C |
|------|-------|-----|-------|----|---------|---------|----------|------|-------|---|
| ATOM | 11073 | N1  | MOL B | 1  | −45.054 | 55.274  | −95.456  | 1.00 | 38.23 | N |
| ATOM | 11074 | C1  | MOL B | 1  | −45.250 | 53.859  | −95.112  | 1.00 | 37.99 | C |
| ATOM | 11075 | C5  | MOL B | 1  | −46.746 | 53.568  | −94.971  | 1.00 | 37.76 | C |
| ATOM | 11076 | C8  | MOL B | 1  | −46.973 | 52.088  | −94.675  | 1.00 | 38.45 | C |
| ATOM | 11077 | C11 | MOL B | 1  | −46.309 | 51.222  | −95.747  | 1.00 | 39.26 | C |
| ATOM | 11078 | O3  | MOL B | 1  | −46.773 | 50.114  | −95.999  | 1.00 | 40.19 | O |
| ATOM | 11079 | N2  | MOL B | 1  | −45.181 | 51.685  | −96.448  | 1.00 | 38.85 | N |
| ATOM | 11080 | C4  | MOL B | 1  | −44.631 | 52.952  | −96.184  | 1.00 | 37.61 | C |
| ATOM | 11081 | O2  | MOL B | 1  | −43.634 | 53.323  | −96.799  | 1.00 | 36.34 | O |
| ATOM | 11082 | O   | HOH D | 1  | 2.391   | 18.476  | −57.850  | 1.00 | 17.05 | O |
| ATOM | 11083 | O   | HOH D | 2  | −12.951 | 15.067  | −62.591  | 1.00 | 15.90 | O |
| ATOM | 11084 | O   | HOH D | 3  | −7.873  | −10.205 | −73.836  | 1.00 | 19.74 | O |
| ATOM | 11085 | O   | HOH D | 4  | −15.937 | 14.727  | −33.157  | 1.00 | 16.16 | O |
| ATOM | 11086 | O   | HOH D | 5  | 1.714   | 7.665   | −7.104   | 1.00 | 39.27 | O |
| ATOM | 11087 | O   | HOH D | 6  | −25.723 | 27.363  | −36.461  | 1.00 | 14.97 | O |
| ATOM | 11088 | O   | HOH D | 7  | −32.441 | 2.389   | −42.642  | 1.00 | 22.10 | O |
| ATOM | 11089 | O   | HOH D | 8  | −32.137 | 7.614   | −37.522  | 1.00 | 20.66 | O |
| ATOM | 11090 | O   | HOH D | 9  | −48.718 | 17.406  | −35.548  | 1.00 | 38.21 | O |
| ATOM | 11091 | O   | HOH D | 10 | −48.302 | 27.267  | −49.470  | 1.00 | 24.08 | O |
| ATOM | 11092 | O   | HOH D | 11 | −37.013 | 28.815  | −26.871  | 1.00 | 20.05 | O |
| ATOM | 11093 | O   | HOH D | 12 | −60.235 | 51.997  | −84.012  | 1.00 | 17.67 | O |
| ATOM | 11094 | O   | HOH D | 13 | −58.438 | 45.605  | −79.491  | 1.00 | 30.89 | O |
| ATOM | 11095 | O   | HOH D | 14 | −22.402 | 45.556  | −63.957  | 1.00 | 28.50 | O |
| ATOM | 11096 | O   | HOH D | 15 | −43.075 | 24.840  | −58.945  | 1.00 | 18.58 | O |
| ATOM | 11097 | O   | HOH D | 16 | −48.921 | 52.096  | −105.880 | 1.00 | 22.47 | O |
| ATOM | 11098 | O   | HOH D | 17 | −55.483 | 51.292  | −103.346 | 1.00 | 40.75 | O |
| ATOM | 11099 | O   | HOH D | 18 | −58.085 | 49.218  | −99.665  | 1.00 | 41.57 | O |
| END  |       |     |       |    |         |         |          |      |       |   |

TABLE 4

Atomic coordinates for CRBN(TBD):Pomalidomide (Murine protein)

```
HEADER    ----                                                      XX-XXX-XX    xxxx
COMPND    ---
REMARK  3
REMARK  3  REFINEMENT.
REMARK  3    PROGRAM     :  REFMAC 5.6.0117
REMARK  3    AUTHORS     :
REMARK  3
REMARK  3      REFINEMENT TARGET : MAXIMUM LIKELIHOOD
REMARK  3
REMARK  3    DATA USED IN REFINEMENT.
REMARK  3      RESOLUTION RANGE HIGH (ANGSTROMS)     :   2.00
REMARK  3      RESOLUTION RANGE LOW (ANGSTROMS)      :   30.00
REMARK  3      DATA CUTOFF            (SIGMA(F))     :   NONE
REMARK  3      COMPLETENESS FOR RANGE        (%)     :   91.37
REMARK  3      NUMBER OF REFLECTIONS                 :   28750
REMARK  3
REMARK  3    FIT TO DATA USED IN REFINEMENT.
REMARK  3      CROSS-VALIDATION METHOD               :   THROUGHOUT
REMARK  3      FREE R VALUE TEST SET SELECTION       :   RANDOM
REMARK  3      R VALUE      (WORKING + TEST SET)     :   0.19883
REMARK  3      R VALUE           (WORKING SET)       :   0.19655
REMARK  3      FREE R VALUE                          :   0.24000
REMARK  3      FREE R VALUE TEST SET SIZE    (%)     :   5.1
REMARK  3      FREE R VALUE TEST SET COUNT           :   1536
REMARK  3
REMARK  3    FIT IN THE HIGHEST RESOLUTION BIN.
REMARK  3      TOTAL NUMBER OF BINS USED             :   20
REMARK  3      BIN RESOLUTION RANGE HIGH             :   2.000
REMARK  3      BIN RESOLUTION RANGE LOW              :   2.052
REMARK  3      REFLECTION IN BIN      (WORKING SET)  :   2036
REMARK  3      BIN COMPLETENESS (WORKING + TEST) (%) :   91.32
REMARK  3      BIN R VALUE            (WORKING SET)  :   0.198
REMARK  3      BIN FREE R VALUE SET COUNT            :   111
REMARK  3      BIN FREE R VALUE                      :   0.244
REMARK  3
REMARK  3    NUMBER OF NON-HYDROGEN ATOMS USED IN REFINEMENT.
REMARK  3      ALL ATOMS               :      3157
REMARK  3
REMARK  3    B VALUES.
REMARK  3      FROM WILSON PLOT           (A**2) : NULL
REMARK  3      MEAN B VALUE      (OVERALL, A**2) : 22.876
```

TABLE 4-continued

Atomic coordinates for CRBN(TBD):Pomalidomide (Murine protein)

```
REMARK 3    OVERALL ANISOTROPIC B VALUE.
REMARK 3      B11 (A**2) : NULL
REMARK 3      B22 (A**2) : NULL
REMARK 3      B33 (A**2) : NULL
REMARK 3      B12 (A**2) : NULL
REMARK 3      B13 (A**2) : NULL
REMARK 3      B23 (A**2) : NULL
REMARK 3
REMARK 3    ESTIMATED OVERALL COORDINATE ERROR.
REMARK 3      ESU BASED ON R VALUE                          (A):   0.182
REMARK 3      ESU BASED ON FREE R VALUE                     (A):   0.167
REMARK 3      ESU BASED ON MAXIMUM LIKELIHOOD               (A):   0.105
REMARK 3      ESU FOR B VALUES BASED ON MAXIMUM LIKELIHOOD (A**2): 6.738
REMARK 3
REMARK 3    CORRELATION COEFFICIENTS.
REMARK 3      CORRELATION COEFFICIENT FO-FC       :   0.947
REMARK 3      CORRELATION COEFFICIENT FO-FC FREE  :   0.930
REMARK 3
REMARK 3    RMS DEVIATIONS FROM IDEAL VALUES          COUNT    RMS     WEIGHT
REMARK 3      BOND LENGTHS REFINED ATOMS        (A):  3057 ;  0.017 ;  0.019
REMARK 3      BOND ANGLES REFINED ATOMS    (DEGREES): 4163 ;  1.723 ;  1.931
REMARK 3      TORSION ANGLES, PERIOD 1     (DEGREES):  356 ; 17.202 ;  5.000
REMARK 3      TORSION ANGLES, PERIOD 2     (DEGREES):  105 ; 41.339 ; 23.905
REMARK 3      TORSION ANGLES, PERIOD 3     (DEGREES):  516 ; 15.489 ; 15.000
REMARK 3      TORSION ANGLES, PERIOD 4     (DEGREES):    8 ; 12.460 ; 15.000
REMARK 3      CHIRAL-CENTER RESTRAINTS        (A**3):  465 ;  0.112 ;  0.200
REMARK 3      GENERAL PLANES REFINED ATOMS      (A): 2184 ;  0.019 ;  0.021
REMARK 3
REMARK 3    ISOTROPIC THERMAL FACTOR RESTRAINTS.   COUNT    RMS    WEIGHT
REMARK 3
REMARK 3    NCS RESTRAINTS STATISTICS
REMARK 3      NCS TYPE: LOCAL
REMARK 3      NUMBER OF DIFFERENT NCS PAIRS : 6
REMARK 3      GROUP  CHAIN1      RANGE    CHAIN2      RANGE  COUNT   RMS    WEIGHT
REMARK 3        1      D     321   426      A      321   426   129   0.06    0.05
REMARK 3        2      D     321   425      B      321   425   123   0.07    0.05
REMARK 3        3      D     321   425      C      321   425   120   0.07    0.05
REMARK 3        4      A     321   425      B      321   425   127   0.06    0.05
REMARK 3        5      A     321   425      C      321   425   125   0.07    0.05
REMARK 3        6      B     321   427      C      321   427   127   0.07    0.05
REMARK 3
REMARK 3    TWIN DETAILS
REMARK 3      NUMBER OF TWIN DOMAINS : NULL
REMARK 3
REMARK 3
REMARK 3    TLS DETAILS
REMARK 3      NUMBER OF TLS GROUPS : 4
REMARK 3      ATOM RECORD CONTAINS RESIDUAL B FACTORS ONLY
REMARK 3
REMARK 3      TLS GROUP : 1
REMARK 3        NUMBER OF COMPONENTS GROUP : 1
REMARK 3        COMPONENTS      C   SSSEQI    TO     C   SSSEQI
REMARK 3        RESIDUE RANGE :  D    -10            D    9999
REMARK 3        ORIGIN FOR THE GROUP (A):   -54.6488   -43.2246   -9.1355
REMARK 3        T TENSOR
REMARK 3          T11:    0.0449   T22:    0.0609
REMARK 3          T33:    0.0451   T12:    0.0214
REMARK 3          T13:   -0.0017   T23:   -0.0302
REMARK 3        L TENSOR
REMARK 3          L11:    1.8641   L22:    1.0729
REMARK 3          L33:    1.3703   L12:   -0.9776
REMARK 3          L13:   -0.3315   L23:    0.4284
REMARK 3        S TENSOR
REMARK 3          S11:    0.0326   S12:   -0.0774   S13:    0.0790
REMARK 3          S21:   -0.0715   S22:    0.1331   S23:   -0.0656
REMARK 3          S31:   -0.0229   S32:    0.0512   S33:   -0.1657
REMARK 3
REMARK 3      TLS GROUP : 2
REMARK 3        NUMBER OF COMPONENTS GROUP : 1
REMARK 3        COMPONENTS      C   SSSEQI    TO     C   SSSEQI
REMARK 3        RESIDUE RANGE :  A    -10            A    9999
REMARK 3        ORIGIN FOR THE GROUP (A):   -43.1674   -61.8511   -17.2067
REMARK 3        T TENSOR
REMARK 3          T11:    0.0961   T22:    0.0577
REMARK 3          T33:    0.0433   T12:    0.0667
REMARK 3          T13:   -0.0355   T23:   -0.0218
REMARK 3        L TENSOR
REMARK 3          L11:    1.2102   L22:    1.0632
```

TABLE 4-continued

Atomic coordinates for CRBN(TBD):Pomalidomide (Murine protein)

```
REMARK  3          L33:    1.6053    L12:   -0.7697
REMARK  3          L13:    0.6016    L23:    0.1378
REMARK  3         S TENSOR
REMARK  3          S11:    0.1405    S12:    0.0556    S13:   -0.0495
REMARK  3          S21:   -0.1257    S22:   -0.0515    S23:   -0.0591
REMARK  3          S31:    0.0855    S32:    0.1366    S33:   -0.0890
REMARK  3
REMARK  3       TLS GROUP : 3
REMARK  3         NUMBER OF COMPONENTS GROUP : 1
REMARK  3         COMPONENTS       C    SSSEQI      TO      C    SSSEQI
REMARK  3         RESIDUE RANGE :   B    -10              B    9999
REMARK  3         ORIGIN FOR THE GROUP (A):   -62.7105   -54.8717   -27.4066
REMARK  3         T TENSOR
REMARK  3          T11:    0.0935    T22:    0.0782
REMARK  3          T33:    0.1060    T12:    0.0354
REMARK  3          T13:   -0.0780    T23:   -0.0561
REMARK  3         L TENSOR
REMARK  3          L11:    0.9704    L22:    1.3670
REMARK  3          L33:    1.8001    L12:   -0.0106
REMARK  3          L13:    0.5310    L23:    0.1324
REMARK  3         S TENSOR
REMARK  3          S11:    0.0495    S12:    0.2002    S13:   -0.0722
REMARK  3          S21:   -0.1607    S22:   -0.0989    S23:    0.2555
REMARK  3          S31:    0.1626    S32:    0.1066    S33:    0.0493
REMARK  3
REMARK  3       TLS GROUP : 4
REMARK  3         NUMBER OF COMPONENTS GROUP : 1
REMARK  3         COMPONENTS       C    SSSEQI      TO      C    SSSEQI
REMARK  3         RESIDUE RANGE :   C    -10              C    9999
REMARK  3         ORIGIN FOR THE GROUP (A):   -81.9343   -54.7508   -42.6687
REMARK  3         T TENSOR
REMARK  3          T11:    0.0489    T22:    0.1203
REMARK  3          T33:    0.1222    T12:    0.0048
REMARK  3          T13:   -0.0491    T23:    0.0798
REMARK  3         L TENSOR
REMARK  3          L11:    1.8956    L22:    2.6463
REMARK  3          L33:    2.0505    L12:   -0.0976
REMARK  3          L13:    1.1206    L23:    0.0699
REMARK  3         S TENSOR
REMARK  3          S11:   -0.0783    S12:   -0.1677    S13:   -0.1032
REMARK  3          S21:    0.0919    S22:    0.0341    S23:   -0.2101
REMARK  3          S31:    0.0414    S32:    0.1410    S33:    0.0442
REMARK  3
REMARK  3
REMARK  3       BULK SOLVENT MODELLING.
REMARK  3          METHOD USED  :   MASK
REMARK  3          PARAMETERS FOR MASK CALCULATION
REMARK  3          VDW PROBE RADIUS    :   1.20
REMARK  3          ION PROBE RADIUS    :   0.80
REMARK  3          SHRINKAGE RADIUS    :   0.80
REMARK  3
REMARK  3       OTHER REFINEMENT REMARKS:
REMARK  3       HYDROGENS HAVE BEEN USED IF PRESENT IN THE INPUT
REMARK  3       U VALUES       : RESIDUAL ONLY
REMARK  3
LINKR             SER D 343                 GLU D 360                           gap
LINKR             SER B 343                 GLU B 360                           gap
LINKR             SER A 343                 GLU A 360                           gap
LINKR             SER C 343                 GLU C 360                           gap
CRYST1    143.340  143.340  143.340  90.00  90.00  90.00 I 2 3
SCALE1      0.006976  0.000000  0.000000     0.00000
SCALE2      0.000000  0.006976  0.000000     0.00000
SCALE3      0.000000  0.000000  0.006976     0.00000
ATOM      1  N    THR  D  321     -67.228  -55.990   -7.326  1.00  34.39       N
ATOM      2  CA   THR  D  321     -65.794  -55.577   -7.541  1.00  28.56       C
ATOM      3  CB   THR  D  321     -65.154  -56.313   -8.776  1.00  21.71       C
ATOM      4  OG1  THR  D  321     -65.621  -55.728  -10.020  1.00  23.33       O
ATOM      5  CG2  THR  D  321     -65.359  -57.851   -8.761  1.00  29.98       C
ATOM      6  C    THR  D  321     -65.626  -54.020   -7.761  1.00  19.04       C
ATOM      7  O    THR  D  321     -64.506  -53.508   -7.689  1.00  17.84       O
ATOM      8  N    SER  D  322     -66.714  -53.296   -8.068  1.00  15.19       N
ATOM      9  CA   SER  D  322     -66.606  -51.868   -8.513  1.00  15.95       C
ATOM     10  CB   SER  D  322     -67.923  -51.336   -9.092  1.00  16.65       C
ATOM     11  OG   SER  D  322     -68.149  -51.941  -10.292  1.00  22.67       O
ATOM     12  C    SER  D  322     -66.300  -50.931   -7.407  1.00  18.04       C
ATOM     13  O    SER  D  322     -66.973  -50.972   -6.414  1.00  16.58       O
ATOM     14  N    LEU  D  323     -65.392  -49.998   -7.644  1.00  11.36       N
ATOM     15  CA   LEU  D  323     -65.082  -48.939   -6.703  1.00  14.58       C
```

TABLE 4-continued

Atomic coordinates for CRBN(TBD):Pomalidomide (Murine protein)

| ATOM | 16 | CB | LEU | D | 323 | −63.570 | −48.975 | −6.316 | 1.00 | 10.60 | C |
| --- | --- | --- | --- | --- | --- | --- | --- | --- | --- | --- | --- |
| ATOM | 17 | CG | LEU | D | 323 | −63.134 | −50.273 | −5.588 | 1.00 | 14.95 | C |
| ATOM | 18 | CD1 | LEU | D | 323 | −61.628 | −50.484 | −5.478 | 1.00 | 13.48 | C |
| ATOM | 19 | CD2 | LEU | D | 323 | −63.699 | −50.250 | −4.194 | 1.00 | 16.93 | C |
| ATOM | 20 | C | LEU | D | 323 | −65.440 | −47.634 | −7.403 | 1.00 | 13.90 | C |
| ATOM | 21 | O | LEU | D | 323 | −64.820 | −47.277 | −8.398 | 1.00 | 11.28 | O |
| ATOM | 22 | N | CYS | D | 324 | −66.489 | −46.978 | −6.920 | 1.00 | 11.58 | N |
| ATOM | 23 | CA | CYS | D | 324 | −67.056 | −45.788 | −7.573 | 1.00 | 11.54 | C |
| ATOM | 24 | CB | CYS | D | 324 | −68.576 | −45.946 | −7.584 | 1.00 | 13.24 | C |
| ATOM | 25 | SG | CYS | D | 324 | −69.106 | −47.222 | −8.759 | 1.00 | 16.00 | S |
| ATOM | 26 | C | CYS | D | 324 | −66.713 | −44.525 | −6.808 | 1.00 | 12.36 | C |
| ATOM | 27 | O | CYS | D | 324 | −66.486 | −44.582 | −5.571 | 1.00 | 11.42 | O |
| ATOM | 28 | N | CYS | D | 325 | −66.776 | −43.382 | −7.504 | 1.00 | 10.46 | N |
| ATOM | 29 | CA | CYS | D | 325 | −66.578 | −42.076 | −6.895 | 1.00 | 11.76 | C |
| ATOM | 30 | CB | CYS | D | 325 | −66.806 | −40.983 | −7.959 | 1.00 | 11.15 | C |
| ATOM | 31 | SG | CYS | D | 325 | −66.789 | −39.334 | −7.236 | 1.00 | 13.37 | S |
| ATOM | 32 | C | CYS | D | 325 | −67.662 | −41.936 | −5.815 | 1.00 | 13.27 | C |
| ATOM | 33 | O | CYS | D | 325 | −68.865 | −42.139 | −6.090 | 1.00 | 12.84 | O |
| ATOM | 34 | N | LYS | D | 326 | −67.261 | −41.646 | −4.598 | 1.00 | 13.45 | N |
| ATOM | 35 | CA | LYS | D | 326 | −68.205 | −41.572 | −3.458 | 1.00 | 11.68 | C |
| ATOM | 36 | CB | LYS | D | 326 | −67.419 | −41.408 | −2.128 | 1.00 | 14.37 | C |
| ATOM | 37 | CG | LYS | D | 326 | −68.258 | −41.217 | −0.849 | 1.00 | 17.62 | C |
| ATOM | 38 | CD | LYS | D | 326 | −67.415 | −41.302 | 0.456 | 1.00 | 16.62 | C |
| ATOM | 39 | CE | LYS | D | 326 | −66.623 | −40.004 | 0.786 | 1.00 | 32.11 | C |
| ATOM | 40 | NZ | LYS | D | 326 | −65.750 | −40.018 | 2.070 | 1.00 | 22.31 | N |
| ATOM | 41 | C | LYS | D | 326 | −69.206 | −40.414 | −3.614 | 1.00 | 12.19 | C |
| ATOM | 42 | O | LYS | D | 326 | −70.404 | −40.520 | −3.237 | 1.00 | 12.26 | O |
| ATOM | 43 | N | GLN | D | 327 | −68.721 | −39.339 | −4.184 | 1.00 | 11.39 | N |
| ATOM | 44 | CA | GLN | D | 327 | −69.498 | −38.143 | −4.369 | 1.00 | 13.99 | C |
| ATOM | 45 | CB | GLN | D | 327 | −68.590 | −36.948 | −4.774 | 1.00 | 14.69 | C |
| ATOM | 46 | CG | GLN | D | 327 | −69.369 | −35.644 | −5.044 | 1.00 | 14.75 | C |
| ATOM | 47 | CD | GLN | D | 327 | −70.212 | −35.266 | −3.836 | 1.00 | 19.02 | C |
| ATOM | 48 | OE1 | GLN | D | 327 | −69.704 | −35.243 | −2.720 | 1.00 | 19.40 | O |
| ATOM | 49 | NE2 | GLN | D | 327 | −71.541 | −35.040 | −4.042 | 1.00 | 14.58 | N |
| ATOM | 50 | C | GLN | D | 327 | −70.634 | −38.336 | −5.373 | 1.00 | 12.45 | C |
| ATOM | 51 | O | GLN | D | 327 | −71.796 | −38.133 | −5.006 | 1.00 | 14.23 | O |
| ATOM | 52 | N | CYS | D | 328 | −70.333 | −38.586 | −6.663 | 1.00 | 12.20 | N |
| ATOM | 53 | CA | CYS | D | 328 | −71.446 | −38.674 | −7.710 | 1.00 | 13.02 | C |
| ATOM | 54 | CB | CYS | D | 328 | −70.942 | −38.252 | −9.110 | 1.00 | 10.26 | C |
| ATOM | 55 | SG | CYS | D | 328 | −69.589 | −39.316 | −9.751 | 1.00 | 11.74 | S |
| ATOM | 56 | C | CYS | D | 328 | −72.062 | −40.085 | −7.766 | 1.00 | 12.49 | C |
| ATOM | 57 | O | CYS | D | 328 | −73.070 | −40.327 | −8.444 | 1.00 | 11.53 | O |
| ATOM | 58 | N | GLN | D | 329 | −71.387 | −41.021 | −7.102 | 1.00 | 12.62 | N |
| ATOM | 59 | CA | GLN | D | 329 | −71.913 | −42.368 | −6.786 | 1.00 | 16.74 | C |
| ATOM | 60 | CB | GLN | D | 329 | −73.328 | −42.277 | −6.137 | 1.00 | 16.32 | C |
| ATOM | 61 | CG | GLN | D | 329 | −73.315 | −41.478 | −4.828 | 1.00 | 15.01 | C |
| ATOM | 62 | CD | GLN | D | 329 | −74.694 | −41.340 | −4.201 | 1.00 | 20.72 | C |
| ATOM | 63 | OE1 | GLN | D | 329 | −75.464 | −42.290 | −4.192 | 1.00 | 20.99 | O |
| ATOM | 64 | NE2 | GLN | D | 329 | −75.042 | −40.124 | −3.747 | 1.00 | 24.15 | N |
| ATOM | 65 | C | GLN | D | 329 | −71.930 | −43.314 | −7.955 | 1.00 | 18.94 | C |
| ATOM | 66 | O | GLN | D | 329 | −71.707 | −44.512 | −7.781 | 1.00 | 21.46 | O |
| ATOM | 67 | N | GLU | D | 330 | −72.168 | −42.799 | −9.158 | 1.00 | 14.80 | N |
| ATOM | 68 | CA | AGLU | D | 330 | −72.496 | −43.677 | −10.261 | 0.50 | 18.10 | C |
| ATOM | 69 | CA | BGLU | D | 330 | −72.501 | −43.634 | −10.310 | 0.50 | 16.38 | C |
| ATOM | 70 | CB | AGLU | D | 330 | −73.682 | −43.112 | −11.079 | 0.50 | 22.68 | C |
| ATOM | 71 | CB | BGLU | D | 330 | −73.547 | −42.926 | −11.195 | 0.50 | 17.07 | C |
| ATOM | 72 | CG | AGLU | D | 330 | −74.877 | −42.576 | −10.267 | 0.50 | 23.78 | C |
| ATOM | 73 | CG | BGLU | D | 330 | −72.942 | −41.929 | −12.180 | 0.50 | 13.97 | C |
| ATOM | 74 | CD | AGLU | D | 330 | −75.530 | −43.636 | −9.387 | 0.50 | 29.20 | C |
| ATOM | 75 | CD | BGLU | D | 330 | −73.963 | −41.151 | −12.985 | 0.50 | 17.67 | C |
| ATOM | 76 | OE1 | AGLU | D | 330 | −75.262 | −44.831 | −9.615 | 0.50 | 31.28 | O |
| ATOM | 77 | OE1 | BGLU | D | 330 | −75.138 | −41.551 | −13.041 | 0.50 | 14.73 | O |
| ATOM | 78 | OE2 | AGLU | D | 330 | −76.322 | −43.279 | −8.470 | 0.50 | 27.78 | O |
| ATOM | 79 | OE2 | BGLU | D | 330 | −73.586 | −40.117 | −13.549 | 0.50 | 17.61 | O |
| ATOM | 80 | C | GLU | D | 330 | −71.267 | −43.935 | −11.167 | 1.00 | 18.98 | C |
| ATOM | 81 | O | GLU | D | 330 | −71.291 | −44.816 | −12.043 | 1.00 | 15.50 | O |
| ATOM | 82 | N | THR | D | 331 | −70.198 | −43.174 | −10.959 | 1.00 | 15.79 | N |
| ATOM | 83 | CA | THR | D | 331 | −69.018 | −43.257 | −11.827 | 1.00 | 13.14 | C |
| ATOM | 84 | CB | THR | D | 331 | −68.355 | −41.860 | −11.996 | 1.00 | 14.10 | C |
| ATOM | 85 | OG1 | THR | D | 331 | −69.328 | −40.916 | −12.486 | 1.00 | 16.15 | O |
| ATOM | 86 | CG2 | THR | D | 331 | −67.130 | −41.876 | −12.976 | 1.00 | 9.86 | C |
| ATOM | 87 | C | THR | D | 331 | −67.997 | −44.258 | −11.259 | 1.00 | 13.51 | C |
| ATOM | 88 | O | THR | D | 331 | −67.382 | −44.038 | −10.178 | 1.00 | 11.35 | O |
| ATOM | 89 | N | GLU | D | 332 | −67.731 | −45.313 | −12.024 | 1.00 | 11.11 | N |
| ATOM | 90 | CA | GLU | D | 332 | −66.712 | −46.269 | −11.592 | 1.00 | 12.74 | C |
| ATOM | 91 | CB | GLU | D | 332 | −66.878 | −47.605 | −12.313 | 1.00 | 11.85 | C |
| ATOM | 92 | CG | GLU | D | 332 | −65.921 | −48.686 | −11.777 | 1.00 | 15.26 | C |
| ATOM | 93 | CD | GLU | D | 332 | −66.108 | −49.983 | −12.549 | 1.00 | 15.98 | C |

TABLE 4-continued

Atomic coordinates for CRBN(TBD):Pomalidomide (Murine protein)

| ATOM | 94 | OE1 | GLU | D | 332 | −67.063 | −50.728 | −12.267 | 1.00 | 15.76 | O |
|---|---|---|---|---|---|---|---|---|---|---|---|
| ATOM | 95 | OE2 | GLU | D | 332 | −65.378 | −50.175 | −13.504 | 1.00 | 14.09 | O |
| ATOM | 96 | C | GLU | D | 332 | −65.332 | −45.716 | −11.882 | 1.00 | 13.41 | C |
| ATOM | 97 | O | GLU | D | 332 | −65.076 | −45.269 | −12.990 | 1.00 | 9.76 | O |
| ATOM | 98 | N | ILE | D | 333 | −64.440 | −45.805 | −10.886 | 1.00 | 11.09 | N |
| ATOM | 99 | CA | ILE | D | 333 | −63.029 | −45.359 | −11.037 | 1.00 | 10.48 | C |
| ATOM | 100 | CB | ILE | D | 333 | −62.618 | −44.490 | −9.809 | 1.00 | 11.79 | C |
| ATOM | 101 | CG1 | ILE | D | 333 | −63.653 | −43.356 | −9.631 | 1.00 | 11.10 | C |
| ATOM | 102 | CD1 | ILE | D | 333 | −63.750 | −42.417 | −10.859 | 1.00 | 9.78 | C |
| ATOM | 103 | CG2 | ILE | D | 333 | −61.213 | −43.908 | −9.974 | 1.00 | 10.75 | C |
| ATOM | 104 | C | ILE | D | 333 | −62.095 | −46.546 | −11.189 | 1.00 | 9.32 | C |
| ATOM | 105 | O | ILE | D | 333 | −61.179 | −46.513 | −11.985 | 1.00 | 11.67 | O |
| ATOM | 106 | N | THR | D | 334 | −62.332 | −47.619 | −10.451 | 1.00 | 11.43 | N |
| ATOM | 107 | CA | THR | D | 334 | −61.461 | −48.809 | −10.650 | 1.00 | 13.43 | C |
| ATOM | 108 | CB | THR | D | 334 | −60.072 | −48.626 | −9.953 | 1.00 | 13.67 | C |
| ATOM | 109 | OG1 | THR | D | 334 | −59.168 | −49.627 | −10.417 | 1.00 | 12.55 | O |
| ATOM | 110 | CG2 | THR | D | 334 | −60.178 | −48.708 | −8.394 | 1.00 | 13.54 | C |
| ATOM | 111 | C | THR | D | 334 | −62.224 | −50.014 | −10.172 | 1.00 | 12.78 | C |
| ATOM | 112 | O | THR | D | 334 | −63.422 | −49.891 | −9.877 | 1.00 | 10.19 | O |
| ATOM | 113 | N | THR | D | 335 | −61.572 | −51.185 | −10.140 | 1.00 | 11.03 | N |
| ATOM | 114 | CA | THR | D | 335 | −62.191 | −52.389 | −9.579 | 1.00 | 10.78 | C |
| ATOM | 115 | CB | THR | D | 335 | −62.618 | −53.405 | −10.675 | 1.00 | 11.10 | C |
| ATOM | 116 | OG1 | THR | D | 335 | −61.469 | −54.087 | −11.182 | 1.00 | 11.10 | O |
| ATOM | 117 | CG2 | THR | D | 335 | −63.369 | −52.710 | −11.849 | 1.00 | 11.42 | C |
| ATOM | 118 | C | THR | D | 335 | −61.168 | −53.075 | −8.684 | 1.00 | 11.76 | C |
| ATOM | 119 | O | THR | D | 335 | −59.942 | −52.872 | −8.849 | 1.00 | 11.57 | O |
| ATOM | 120 | N | LYS | D | 336 | −61.632 | −53.892 | −7.753 | 1.00 | 11.47 | N |
| ATOM | 121 | CA | LYS | D | 336 | −60.722 | −54.607 | −6.865 | 1.00 | 13.75 | C |
| ATOM | 122 | CB | LYS | D | 336 | −61.521 | −55.503 | −5.909 | 1.00 | 20.64 | C |
| ATOM | 123 | CG | LYS | D | 336 | −62.227 | −54.735 | −4.812 | 1.00 | 30.62 | C |
| ATOM | 124 | CD | LYS | D | 336 | −62.903 | −55.698 | −3.826 | 1.00 | 33.50 | C |
| ATOM | 125 | CE | LYS | D | 336 | −63.747 | −54.950 | −2.795 | 1.00 | 35.38 | C |
| ATOM | 126 | NZ | LYS | D | 336 | −64.601 | −55.948 | −2.077 | 1.00 | 39.43 | N |
| ATOM | 127 | C | LYS | D | 336 | −59.764 | −55.475 | −7.622 | 1.00 | 13.56 | C |
| ATOM | 128 | O | LYS | D | 336 | −58.722 | −55.830 | −7.105 | 1.00 | 14.30 | O |
| ATOM | 129 | N | ASN | D | 337 | −60.130 | −55.867 | −8.848 | 1.00 | 11.55 | N |
| ATOM | 130 | CA | ASN | D | 337 | −59.265 | −56.749 | −9.637 | 1.00 | 12.27 | C |
| ATOM | 131 | CB | ASN | D | 337 | −59.978 | −57.212 | −10.931 | 1.00 | 12.51 | C |
| ATOM | 132 | CG | ASN | D | 337 | −61.178 | −58.053 | −10.643 | 1.00 | 19.58 | C |
| ATOM | 133 | OD1 | ASN | D | 337 | −62.313 | −57.694 | −10.963 | 1.00 | 21.91 | O |
| ATOM | 134 | ND2 | ASN | D | 337 | −60.948 | −59.159 | −9.999 | 1.00 | 19.26 | N |
| ATOM | 135 | C | ASN | D | 337 | −57.984 | −56.054 | −10.007 | 1.00 | 13.06 | C |
| ATOM | 136 | O | ASN | D | 337 | −57.025 | −56.698 | −10.335 | 1.00 | 12.99 | O |
| ATOM | 137 | N | GLU | D | 338 | −57.989 | −54.716 | −9.978 | 1.00 | 12.28 | N |
| ATOM | 138 | CA | GLU | D | 338 | −56.825 | −53.923 | −10.425 | 1.00 | 14.52 | C |
| ATOM | 139 | CB | GLU | D | 338 | −57.262 | −52.638 | −11.176 | 1.00 | 10.20 | C |
| ATOM | 140 | CG | GLU | D | 338 | −58.194 | −52.913 | −12.333 | 1.00 | 11.30 | C |
| ATOM | 141 | CD | GLU | D | 338 | −57.585 | −53.853 | −13.357 | 1.00 | 13.59 | C |
| ATOM | 142 | OE1 | GLU | D | 338 | −56.401 | −53.686 | −13.714 | 1.00 | 13.97 | O |
| ATOM | 143 | OE2 | GLU | D | 338 | −58.299 | −54.774 | −13.804 | 1.00 | 17.16 | O |
| ATOM | 144 | C | GLU | D | 338 | −55.854 | −53.578 | −9.316 | 1.00 | 13.62 | C |
| ATOM | 145 | O | GLU | D | 338 | −54.803 | −52.977 | −9.587 | 1.00 | 12.34 | O |
| ATOM | 146 | N | ILE | D | 339 | −56.146 | −54.025 | −8.086 | 1.00 | 11.79 | N |
| ATOM | 147 | CA | ILE | D | 339 | −55.329 | −53.601 | −6.912 | 1.00 | 14.46 | C |
| ATOM | 148 | CB | ILE | D | 339 | −56.104 | −53.87 | −5.570 | 1.00 | 14.63 | C |
| ATOM | 149 | CG1 | ILE | D | 339 | −57.371 | −52.992 | −5.435 | 1.00 | 13.29 | C |
| ATOM | 150 | CD1 | ILE | D | 339 | −58.263 | −53.446 | −4.282 | 1.00 | 17.57 | C |
| ATOM | 151 | CG2 | ILE | D | 339 | −55.196 | −53.842 | −4.344 | 1.00 | 11.80 | C |
| ATOM | 152 | C | ILE | D | 339 | −54.033 | −54.428 | −6.963 | 1.00 | 12.36 | C |
| ATOM | 153 | O | ILE | D | 339 | −54.077 | −55.613 | −7.307 | 1.00 | 9.97 | O |
| ATOM | 154 | N | PHE | D | 340 | −52.893 | −53.811 | −6.636 | 1.00 | 9.98 | N |
| ATOM | 155 | CA | PHE | D | 340 | −51.621 | −54.530 | −6.521 | 1.00 | 12.72 | C |
| ATOM | 156 | CB | PHE | D | 340 | −50.850 | −54.600 | −7.886 | 1.00 | 11.78 | C |
| ATOM | 157 | CG | PHE | D | 340 | −50.178 | −53.300 | −8.274 | 1.00 | 11.81 | C |
| ATOM | 158 | CD1 | PHE | D | 340 | −48.777 | −53.133 | −8.123 | 1.00 | 12.97 | C |
| ATOM | 159 | CE1 | PHE | D | 340 | −48.182 | −51.900 | −8.442 | 1.00 | 12.13 | C |
| ATOM | 160 | CZ | PHE | D | 340 | −48.989 | −50.824 | −8.873 | 1.00 | 11.11 | C |
| ATOM | 161 | CE2 | PHE | D | 340 | −50.342 | −50.994 | −9.071 | 1.00 | 11.64 | C |
| ATOM | 162 | CD2 | PHE | D | 340 | −50.949 | −52.210 | −8.762 | 1.00 | 10.10 | C |
| ATOM | 163 | C | PHE | D | 340 | −50.809 | −53.795 | −5.449 | 1.00 | 16.76 | C |
| ATOM | 164 | O | PHE | D | 340 | −51.210 | −52.719 | −5.012 | 1.00 | 16.33 | O |
| ATOM | 165 | N | SER | D | 341 | −49.671 | −54.368 | −5.058 | 1.00 | 18.59 | N |
| ATOM | 166 | CA | SER | D | 341 | −48.870 | −53.838 | −3.970 | 1.00 | 18.62 | C |
| ATOM | 167 | CB | SER | D | 341 | −48.740 | −54.877 | −2.868 | 1.00 | 26.20 | C |
| ATOM | 168 | OG | SER | D | 341 | −48.024 | −54.372 | −1.746 | 1.00 | 34.73 | O |
| ATOM | 169 | C | SER | D | 341 | −47.522 | −53.421 | −4.522 | 1.00 | 17.47 | C |
| ATOM | 170 | O | SER | D | 341 | −46.761 | −54.248 | −4.971 | 1.00 | 15.83 | O |
| ATOM | 171 | N | LEU | D | 342 | −47.247 | −52.107 | −4.524 | 1.00 | 18.98 | N |

TABLE 4-continued

Atomic coordinates for CRBN(TBD):Pomalidomide (Murine protein)

| ATOM | 172 | CA | LEU | D | 342 | −45.927 | −51.606 | −4.985 | 1.00 | 24.10 | C |
|---|---|---|---|---|---|---|---|---|---|---|---|
| ATOM | 173 | CB | LEU | D | 342 | −46.033 | −50.156 | −5.478 | 1.00 | 24.70 | C |
| ATOM | 174 | CG | LEU | D | 342 | −45.454 | −49.626 | −6.779 | 1.00 | 30.75 | C |
| ATOM | 175 | CD1 | LEU | D | 342 | −44.729 | −48.330 | −6.525 | 1.00 | 27.48 | C |
| ATOM | 176 | CD2 | LEU | D | 342 | −44.501 | −50.609 | −7.434 | 1.00 | 34.18 | C |
| ATOM | 177 | C | LEU | D | 342 | −44.888 | −51.734 | −3.840 | 1.00 | 34.50 | C |
| ATOM | 178 | O | LEU | D | 342 | −43.752 | −52.165 | −4.082 | 1.00 | 30.45 | O |
| ATOM | 179 | N | SER | D | 343 | −45.291 | −51.417 | −2.596 | 1.00 | 30.56 | N |
| ATOM | 180 | CA | SER | D | 343 | −44.440 | −51.658 | −1.399 | 1.00 | 62.05 | C |
| ATOM | 181 | CB | SER | D | 343 | −45.222 | −51.403 | −0.088 | 1.00 | 55.95 | C |
| ATOM | 182 | OG | SER | D | 343 | −46.316 | −52.295 | 0.049 | 1.00 | 59.16 | O |
| ATOM | 183 | C | SER | D | 343 | −43.802 | −53.066 | −1.381 | 1.00 | 74.57 | C |
| ATOM | 184 | O | SER | D | 343 | −43.159 | −53.475 | −0.406 | 1.00 | 80.57 | O |
| ATOM | 185 | N | GLU | D | 360 | −54.707 | −46.012 | 3.496 | 1.00 | 32.78 | N |
| ATOM | 186 | CA | GLU | D | 360 | −55.229 | −44.691 | 3.067 | 1.00 | 41.60 | C |
| ATOM | 187 | CB | GLU | D | 360 | −54.466 | −43.536 | 3.771 | 1.00 | 47.05 | C |
| ATOM | 188 | CG | GLU | D | 360 | −54.686 | −42.127 | 3.193 | 1.00 | 55.26 | C |
| ATOM | 189 | CD | GLU | D | 360 | −55.669 | −41.257 | 3.987 | 1.00 | 65.56 | C |
| ATOM | 190 | OE1 | GLU | D | 360 | −56.577 | −40.656 | 3.369 | 1.00 | 70.43 | O |
| ATOM | 191 | OE2 | GLU | D | 360 | −55.521 | −41.145 | 5.219 | 1.00 | 43.69 | O |
| ATOM | 192 | C | GLU | D | 360 | −55.242 | −44.524 | 1.517 | 1.00 | 35.47 | C |
| ATOM | 193 | O | GLU | D | 360 | −56.235 | −44.012 | 0.944 | 1.00 | 24.22 | O |
| ATOM | 194 | N | THR | D | 361 | −54.156 | −44.978 | 0.863 | 1.00 | 25.92 | N |
| ATOM | 195 | CA | THR | D | 361 | −53.985 | −44.859 | −0.620 | 1.00 | 27.67 | C |
| ATOM | 196 | CB | THR | D | 361 | −52.744 | −44.010 | −0.996 | 1.00 | 30.46 | C |
| ATOM | 197 | OG1 | THR | D | 361 | −52.879 | −42.680 | −0.453 | 1.00 | 35.07 | O |
| ATOM | 198 | CG2 | THR | D | 361 | −52.615 | −43.922 | −2.509 | 1.00 | 26.94 | C |
| ATOM | 199 | C | THR | D | 361 | −53.896 | −46.231 | −1.329 | 1.00 | 20.63 | C |
| ATOM | 200 | O | THR | D | 361 | −52.977 | −46.991 | −1.112 | 1.00 | 25.53 | O |
| ATOM | 201 | N | LEU | D | 362 | −54.871 | −46.519 | −2.171 | 1.00 | 18.65 | N |
| ATOM | 202 | CA | LEU | D | 362 | −54.986 | −47.780 | −2.849 | 1.00 | 16.05 | C |
| ATOM | 203 | CB | LEU | D | 362 | −56.474 | −48.000 | −3.165 | 1.00 | 17.05 | C |
| ATOM | 204 | CG | LEU | D | 362 | −56.921 | −49.338 | −3.730 | 1.00 | 18.27 | C |
| ATOM | 205 | CD1 | LEU | D | 362 | −56.930 | −50.361 | −2.592 | 1.00 | 19.21 | C |
| ATOM | 206 | CD2 | LEU | D | 362 | −58.318 | −49.184 | −4.304 | 1.00 | 23.17 | C |
| ATOM | 207 | C | LEU | D | 362 | −54.190 | −47.676 | −4.157 | 1.00 | 18.06 | C |
| ATOM | 208 | O | LEU | D | 362 | −54.278 | −46.664 | −4.835 | 1.00 | 16.54 | O |
| ATOM | 209 | N | THR | D | 363 | −53.373 | −48.675 | −4.491 | 1.00 | 12.90 | N |
| ATOM | 210 | CA | THR | D | 363 | −52.659 | −48.615 | −5.773 | 1.00 | 13.43 | C |
| ATOM | 211 | CB | THR | D | 363 | −51.131 | −48.823 | −5.599 | 1.00 | 16.84 | C |
| ATOM | 212 | OG1 | THR | D | 363 | −50.882 | −50.071 | −4.902 | 1.00 | 15.09 | O |
| ATOM | 213 | CG2 | THR | D | 363 | −50.510 | −47.656 | −4.790 | 1.00 | 18.98 | C |
| ATOM | 214 | C | THR | D | 363 | −53.272 | −49.632 | −6.749 | 1.00 | 13.28 | C |
| ATOM | 215 | O | THR | D | 363 | −53.441 | −50.809 | −6.396 | 1.00 | 11.09 | O |
| ATOM | 216 | N | VAL | D | 364 | −53.619 | −49.177 | −7.959 | 1.00 | 10.26 | N |
| ATOM | 217 | CA | VAL | D | 364 | −54.248 | −50.061 | −8.969 | 1.00 | 9.75 | C |
| ATOM | 218 | CB | VAL | D | 364 | −55.775 | −49.758 | −9.137 | 1.00 | 9.30 | C |
| ATOM | 219 | CG1 | VAL | D | 364 | −56.525 | −50.033 | −7.832 | 1.00 | 10.55 | C |
| ATOM | 220 | CG2 | VAL | D | 364 | −56.003 | −48.314 | −9.566 | 1.00 | 9.33 | C |
| ATOM | 221 | C | VAL | D | 364 | −53.564 | −49.913 | −10.312 | 1.00 | 9.78 | C |
| ATOM | 222 | O | VAL | D | 364 | −53.021 | −48.813 | −10.616 | 1.00 | 9.01 | O |
| ATOM | 223 | N | TYR | D | 365 | −53.534 | −51.004 | −11.124 | 1.00 | 8.58 | N |
| ATOM | 224 | CA | TYR | D | 365 | −52.859 | −50.920 | −12.419 | 1.00 | 9.67 | C |
| ATOM | 225 | CB | TYR | D | 365 | −52.721 | −52.334 | −13.056 | 1.00 | 9.61 | C |
| ATOM | 226 | CG | TYR | D | 365 | −51.674 | −53.174 | −12.436 | 1.00 | 12.91 | C |
| ATOM | 227 | CD1 | TYR | D | 365 | −50.299 | −52.807 | −12.530 | 1.00 | 11.67 | C |
| ATOM | 228 | CE1 | TYR | D | 365 | −49.291 | −53.625 | −12.013 | 1.00 | 10.11 | C |
| ATOM | 229 | CZ | TYR | D | 365 | −49.642 | −54.753 | −11.351 | 1.00 | 12.37 | C |
| ATOM | 230 | OH | TYR | D | 365 | −48.657 | −55.515 | −10.825 | 1.00 | 11.48 | O |
| ATOM | 231 | CE2 | TYR | D | 365 | −50.976 | −55.178 | −11.267 | 1.00 | 10.77 | C |
| ATOM | 232 | CD2 | TYR | D | 365 | −52.002 | −54.371 | −11.781 | 1.00 | 11.08 | C |
| ATOM | 233 | C | TYR | D | 365 | −53.651 | −50.074 | −13.421 | 1.00 | 9.56 | C |
| ATOM | 234 | O | TYR | D | 365 | −53.083 | −49.500 | −14.355 | 1.00 | 11.17 | O |
| ATOM | 235 | N | LYS | D | 366 | −54.977 | −50.081 | −13.265 | 1.00 | 9.37 | N |
| ATOM | 236 | CA | LYS | D | 366 | −55.884 | −49.466 | −14.253 | 1.00 | 11.01 | C |
| ATOM | 237 | CB | LYS | D | 366 | −56.496 | −50.574 | −15.118 | 1.00 | 9.42 | C |
| ATOM | 238 | CG | LYS | D | 366 | −55.502 | −51.172 | −16.109 | 1.00 | 11.57 | C |
| ATOM | 239 | CD | LYS | D | 366 | −55.507 | −50.363 | −17.402 | 1.00 | 11.80 | C |
| ATOM | 240 | CE | LYS | D | 366 | −54.295 | −50.744 | −18.254 | 1.00 | 17.68 | C |
| ATOM | 241 | NZ | LYS | D | 366 | −54.182 | −49.886 | −19.458 | 1.00 | 12.69 | N |
| ATOM | 242 | C | LYS | D | 366 | −57.020 | −48.717 | −13.540 | 1.00 | 10.84 | C |
| ATOM | 243 | O | LYS | D | 366 | −57.528 | −49.177 | −12.476 | 1.00 | 11.53 | O |
| ATOM | 244 | N | ALA | D | 367 | −57.452 | −47.621 | −14.148 | 1.00 | 9.83 | N |
| ATOM | 245 | CA | ALA | D | 367 | −58.578 | −46.809 | −13.632 | 1.00 | 12.18 | C |
| ATOM | 246 | CB | ALA | D | 367 | −58.052 | −45.679 | −12.724 | 1.00 | 12.33 | C |
| ATOM | 247 | C | ALA | D | 367 | −59.314 | −46.202 | −14.813 | 1.00 | 9.51 | C |
| ATOM | 248 | O | ALA | D | 367 | −58.770 | −46.157 | −15.954 | 1.00 | 11.57 | O |
| ATOM | 249 | N | SER | D | 368 | −60.519 | −45.690 | −14.554 | 1.00 | 9.41 | N |

TABLE 4-continued

Atomic coordinates for CRBN(TBD):Pomalidomide (Murine protein)

| ATOM | 250 | CA | SER | D | 368 | −61.313 | −45.117 | −15.629 | 1.00 | 9.57 | C |
|---|---|---|---|---|---|---|---|---|---|---|---|
| ATOM | 251 | CB | SER | D | 368 | −62.385 | −46.171 | −16.031 | 1.00 | 8.79 | C |
| ATOM | 252 | OG | SER | D | 368 | −63.123 | −46.538 | −14.882 | 1.00 | 11.07 | O |
| ATOM | 253 | C | SER | D | 368 | −62.043 | −43.867 | −15.153 | 1.00 | 9.50 | C |
| ATOM | 254 | O | SER | D | 368 | −62.219 | −43.659 | −13.905 | 1.00 | 9.81 | O |
| ATOM | 255 | N | ASN | D | 369 | −62.495 | −43.071 | −16.097 | 1.00 | 8.82 | N |
| ATOM | 256 | CA | ASN | D | 369 | −63.364 | −41.933 | −15.809 | 1.00 | 11.14 | C |
| ATOM | 257 | CB | ASN | D | 369 | −64.677 | −42.444 | −15.170 | 1.00 | 10.35 | C |
| ATOM | 258 | CG | ASN | D | 369 | −65.455 | −43.372 | −16.114 | 1.00 | 16.33 | C |
| ATOM | 259 | OD1 | ASN | D | 369 | −65.974 | −44.410 | −15.713 | 1.00 | 14.22 | O |
| ATOM | 260 | ND2 | ASN | D | 369 | −65.483 | −43.021 | −17.355 | 1.00 | 12.04 | N |
| ATOM | 261 | C | ASN | D | 369 | −62.675 | −40.879 | −14.933 | 1.00 | 14.38 | C |
| ATOM | 262 | O | ASN | D | 369 | −63.326 | −40.131 | −14.212 | 1.00 | 12.97 | O |
| ATOM | 263 | N | LEU | D | 370 | −61.357 | −40.799 | −15.028 | 1.00 | 10.49 | N |
| ATOM | 264 | CA | LEU | D | 370 | −60.624 | −39.752 | −14.319 | 1.00 | 12.42 | C |
| ATOM | 265 | CB | LEU | D | 370 | −59.444 | −40.380 | −13.567 | 1.00 | 10.40 | C |
| ATOM | 266 | CG | LEU | D | 370 | −59.813 | −41.251 | −12.353 | 1.00 | 11.12 | C |
| ATOM | 267 | CD1 | LEU | D | 370 | −58.565 | −41.969 | −11.803 | 1.00 | 10.26 | C |
| ATOM | 268 | CD2 | LEU | D | 370 | −60.449 | −40.356 | −11.272 | 1.00 | 12.03 | C |
| ATOM | 269 | C | LEU | D | 370 | −60.083 | −38.750 | −15.350 | 1.00 | 12.72 | C |
| ATOM | 270 | O | LEU | D | 370 | −59.600 | −39.166 | −16.434 | 1.00 | 13.55 | O |
| ATOM | 271 | N | ASN | D | 371 | −60.161 | −37.470 | −15.037 | 1.00 | 13.32 | N |
| ATOM | 272 | CA | ASN | D | 371 | −59.398 | −36.416 | −15.780 | 1.00 | 16.00 | C |
| ATOM | 273 | CB | ASN | D | 371 | −60.249 | −35.146 | −15.900 | 1.00 | 17.19 | C |
| ATOM | 274 | CG | ASN | D | 371 | −61.394 | −35.304 | −16.897 | 1.00 | 19.75 | C |
| ATOM | 275 | OD1 | ASN | D | 371 | −61.273 | −36.039 | −17.886 | 1.00 | 22.73 | O |
| ATOM | 276 | ND2 | ASN | D | 371 | −62.507 | −34.658 | −16.621 | 1.00 | 17.09 | N |
| ATOM | 277 | C | ASN | D | 371 | −58.075 | −36.076 | −15.103 | 1.00 | 16.05 | C |
| ATOM | 278 | O | ASN | D | 371 | −58.012 | −35.898 | −13.887 | 1.00 | 17.20 | O |
| ATOM | 279 | N | LEU | D | 372 | −57.039 | −35.877 | −15.891 | 1.00 | 14.64 | N |
| ATOM | 280 | CA | LEU | D | 372 | −55.723 | −35.510 | −15.341 | 1.00 | 16.60 | C |
| ATOM | 281 | CB | LEU | D | 372 | −54.587 | −36.181 | −16.153 | 1.00 | 18.56 | C |
| ATOM | 282 | CG | LEU | D | 372 | −54.554 | −37.722 | −16.216 | 1.00 | 24.16 | C |
| ATOM | 283 | CD1 | LEU | D | 372 | −53.493 | −38.171 | −17.248 | 1.00 | 20.65 | C |
| ATOM | 284 | CD2 | LEU | D | 372 | −54.313 | −38.418 | −14.860 | 1.00 | 19.93 | C |
| ATOM | 285 | C | LEU | D | 372 | −55.578 | −34.009 | −15.370 | 1.00 | 21.79 | C |
| ATOM | 286 | O | LEU | D | 372 | −55.874 | −33.377 | −16.380 | 1.00 | 21.71 | O |
| ATOM | 287 | N | ILE | D | 373 | −55.136 | −33.439 | −14.255 | 1.00 | 20.03 | N |
| ATOM | 288 | CA | ILE | D | 373 | −54.923 | −31.992 | −14.150 | 1.00 | 23.81 | C |
| ATOM | 289 | CB | ILE | D | 373 | −55.562 | −31.407 | −12.875 | 1.00 | 20.77 | C |
| ATOM | 290 | CG1 | ILE | D | 373 | −57.059 | −31.749 | −12.811 | 1.00 | 22.49 | C |
| ATOM | 291 | CD1 | ILE | D | 373 | −57.861 | −31.134 | −13.949 | 1.00 | 25.68 | C |
| ATOM | 292 | CG2 | ILE | D | 373 | −55.304 | −29.894 | −12.792 | 1.00 | 21.65 | C |
| ATOM | 293 | C | ILE | D | 373 | −53.438 | −31.669 | −14.090 | 1.00 | 28.50 | C |
| ATOM | 294 | O | ILE | D | 373 | −52.736 | −32.079 | −13.130 | 1.00 | 23.54 | O |
| ATOM | 295 | N | GLY | D | 374 | −52.956 | −30.930 | −15.088 | 1.00 | 26.30 | N |
| ATOM | 296 | CA | GLY | D | 374 | −51.577 | −30.417 | −15.055 | 1.00 | 26.84 | C |
| ATOM | 297 | C | GLY | D | 374 | −50.579 | −31.394 | −15.627 | 1.00 | 27.07 | C |
| ATOM | 298 | O | GLY | D | 374 | −50.960 | −32.312 | −16.334 | 1.00 | 24.33 | O |
| ATOM | 299 | N | ARG | D | 375 | −49.302 | −31.204 | −15.289 | 1.00 | 23.42 | N |
| ATOM | 300 | CA | ARG | D | 375 | −48.184 | −32.025 | −15.801 | 1.00 | 26.07 | C |
| ATOM | 301 | CB | ARG | D | 375 | −47.092 | −31.109 | −16.393 | 1.00 | 28.25 | C |
| ATOM | 302 | CG | ARG | D | 375 | −47.624 | −30.103 | −17.423 | 1.00 | 35.44 | C |
| ATOM | 303 | CD | ARG | D | 375 | −46.785 | −28.828 | −17.518 | 1.00 | 42.70 | C |
| ATOM | 304 | NE | ARG | D | 375 | −45.343 | −29.082 | −17.567 | 1.00 | 47.46 | N |
| ATOM | 305 | CZ | ARG | D | 375 | −44.522 | −28.970 | −16.523 | 1.00 | 49.67 | C |
| ATOM | 306 | NH1 | ARG | D | 375 | −44.991 | −28.606 | −15.337 | 1.00 | 50.71 | N |
| ATOM | 307 | NH2 | ARG | D | 375 | −43.230 | −29.222 | −16.664 | 1.00 | 59.40 | N |
| ATOM | 308 | C | ARG | D | 375 | −47.579 | −32.818 | −14.647 | 1.00 | 20.41 | C |
| ATOM | 309 | O | ARG | D | 375 | −47.659 | −32.383 | −13.513 | 1.00 | 21.68 | O |
| ATOM | 310 | N | PRO | D | 376 | −46.929 | −33.960 | −14.940 | 1.00 | 21.94 | N |
| ATOM | 311 | CA | PRO | D | 376 | −46.292 | −34.755 | −13.895 | 1.00 | 20.77 | C |
| ATOM | 312 | CB | PRO | D | 376 | −45.560 | −35.835 | −14.682 | 1.00 | 25.05 | C |
| ATOM | 313 | CG | PRO | D | 376 | −46.333 | −35.941 | −15.962 | 1.00 | 29.14 | C |
| ATOM | 314 | CD | PRO | D | 376 | −46.654 | −34.512 | −16.273 | 1.00 | 22.40 | C |
| ATOM | 315 | C | PRO | D | 376 | −45.285 | −33.973 | −13.068 | 1.00 | 21.95 | C |
| ATOM | 316 | O | PRO | D | 376 | −44.611 | −33.105 | −13.596 | 1.00 | 20.20 | O |
| ATOM | 317 | N | SER | D | 377 | −45.187 | −34.297 | −11.779 | 1.00 | 18.40 | N |
| ATOM | 318 | CA | SER | D | 377 | −44.141 | −33.726 | −10.910 | 1.00 | 19.62 | C |
| ATOM | 319 | CB | SER | D | 377 | −44.740 | −32.600 | −10.009 | 1.00 | 18.99 | C |
| ATOM | 320 | OG | SER | D | 377 | −43.835 | −32.242 | −8.957 | 1.00 | 22.29 | O |
| ATOM | 321 | C | SER | D | 377 | −43.560 | −34.836 | −10.043 | 1.00 | 17.21 | C |
| ATOM | 322 | O | SER | D | 377 | −44.312 | −35.720 | −9.573 | 1.00 | 15.64 | O |
| ATOM | 323 | N | THR | D | 378 | −42.251 | −34.783 | −9.796 | 1.00 | 13.61 | N |
| ATOM | 324 | CA | THR | D | 378 | −41.634 | −35.693 | −8.810 | 1.00 | 16.90 | C |
| ATOM | 325 | CB | THR | D | 378 | −40.196 | −36.078 | −9.156 | 1.00 | 14.97 | C |
| ATOM | 326 | OG1 | THR | D | 378 | −39.428 | −34.896 | −9.299 | 1.00 | 14.71 | O |
| ATOM | 327 | CG2 | THR | D | 378 | −40.133 | −36.877 | −10.444 | 1.00 | 15.92 | C |

TABLE 4-continued

Atomic coordinates for CRBN(TBD):Pomalidomide (Murine protein)

| ATOM | 328 | C | THR | D | 378 | −41.559 | −35.078 | −7.399 | 1.00 | 14.84 | C |
| --- | --- | --- | --- | --- | --- | --- | --- | --- | --- | --- | --- |
| ATOM | 329 | O | THR | D | 378 | −41.094 | −35.741 | −6.482 | 1.00 | 15.16 | O |
| ATOM | 330 | N | VAL | D | 379 | −41.964 | −33.813 | −7.268 | 1.00 | 13.54 | N |
| ATOM | 331 | CA | VAL | D | 379 | −41.884 | −33.050 | −6.006 | 1.00 | 15.88 | C |
| ATOM | 332 | CB | VAL | D | 379 | −42.508 | −31.650 | −6.234 | 1.00 | 18.76 | C |
| ATOM | 333 | CG1 | VAL | D | 379 | −42.925 | −30.976 | −4.947 | 1.00 | 23.06 | C |
| ATOM | 334 | CG2 | VAL | D | 379 | −41.537 | −30.771 | −7.023 | 1.00 | 22.47 | C |
| ATOM | 335 | C | VAL | D | 379 | −42.623 | −33.828 | −4.876 | 1.00 | 16.58 | C |
| ATOM | 336 | O | VAL | D | 379 | −43.767 | −34.147 | −5.028 | 1.00 | 16.14 | O |
| ATOM | 337 | N | HIS | D | 380 | −41.921 | −34.202 | −3.805 | 1.00 | 12.95 | N |
| ATOM | 338 | CA | HIS | D | 380 | −42.518 | −34.987 | −2.696 | 1.00 | 14.86 | C |
| ATOM | 339 | CB | HIS | D | 380 | −43.564 | −34.154 | −1.900 | 1.00 | 13.67 | C |
| ATOM | 340 | CG | HIS | D | 380 | −43.044 | −32.832 | −1.374 | 1.00 | 14.41 | C |
| ATOM | 341 | ND1 | HIS | D | 380 | −41.952 | −32.739 | −0.595 | 1.00 | 14.59 | N |
| ATOM | 342 | CE1 | HIS | D | 380 | −41.704 | −31.445 | −0.330 | 1.00 | 13.72 | C |
| ATOM | 343 | NE2 | HIS | D | 380 | −42.687 | −30.713 | −0.894 | 1.00 | 12.95 | N |
| ATOM | 344 | CD2 | HIS | D | 380 | −43.512 | −31.527 | −1.551 | 1.00 | 14.45 | C |
| ATOM | 345 | C | HIS | D | 380 | −43.172 | −36.307 | −3.105 | 1.00 | 15.09 | C |
| ATOM | 346 | O | HIS | D | 380 | −44.098 | −36.787 | −2.399 | 1.00 | 18.61 | O |
| ATOM | 347 | N | SER | D | 381 | −42.760 | −36.910 | −4.235 | 1.00 | 16.93 | N |
| ATOM | 348 | CA | SER | D | 381 | −43.444 | −38.142 | −4.706 | 1.00 | 16.00 | C |
| ATOM | 349 | CB | SER | D | 381 | −42.788 | −38.721 | −5.960 | 1.00 | 19.80 | C |
| ATOM | 350 | OG | SER | D | 381 | −43.404 | −39.969 | −6.285 | 1.00 | 17.26 | O |
| ATOM | 351 | C | SER | D | 381 | −43.479 | −39.235 | −3.630 | 1.00 | 19.44 | C |
| ATOM | 352 | O | SER | D | 381 | −42.419 | −39.567 | −3.027 | 1.00 | 14.52 | O |
| ATOM | 353 | N | TRP | D | 382 | −44.664 | −39.805 | −3.369 | 1.00 | 12.85 | N |
| ATOM | 354 | CA | TRP | D | 382 | −44.713 | −40.957 | −2.441 | 1.00 | 16.94 | C |
| ATOM | 355 | CB | TRP | D | 382 | −46.131 | −41.281 | −1.999 | 1.00 | 18.71 | C |
| ATOM | 356 | CG | TRP | D | 382 | −46.805 | −40.122 | −1.347 | 1.00 | 17.72 | C |
| ATOM | 357 | CD1 | TRP | D | 382 | −46.232 | −39.158 | −0.479 | 1.00 | 22.58 | C |
| ATOM | 358 | NE1 | TRP | D | 382 | −47.178 | −38.219 | −0.097 | 1.00 | 15.78 | N |
| ATOM | 359 | CE2 | TRP | D | 382 | −48.371 | −38.494 | −0.716 | 1.00 | 16.33 | C |
| ATOM | 360 | CD2 | TRP | D | 382 | −48.174 | −39.705 | −1.539 | 1.00 | 16.25 | C |
| ATOM | 361 | CE3 | TRP | D | 382 | −49.244 | −40.201 | −2.275 | 1.00 | 21.53 | C |
| ATOM | 362 | CZ3 | TRP | D | 382 | −50.463 | −39.537 | −2.217 | 1.00 | 15.17 | C |
| ATOM | 363 | CH2 | TRP | D | 382 | −50.642 | −38.391 | −1.421 | 1.00 | 19.34 | C |
| ATOM | 364 | CZ2 | TRP | D | 382 | −49.580 | −37.839 | −0.666 | 1.00 | 17.34 | C |
| ATOM | 365 | C | TRP | D | 382 | −44.058 | −42.218 | −2.935 | 1.00 | 19.12 | C |
| ATOM | 366 | O | TRP | D | 382 | −43.856 | −43.147 | −2.149 | 1.00 | 16.44 | O |
| ATOM | 367 | N | PHE | D | 383 | −43.786 | −42.288 | −4.245 | 1.00 | 18.15 | N |
| ATOM | 368 | CA | PHE | D | 383 | −43.213 | −43.515 | −4.879 | 1.00 | 16.37 | C |
| ATOM | 369 | CB | PHE | D | 383 | −44.294 | −44.188 | −5.782 | 1.00 | 14.45 | C |
| ATOM | 370 | CG | PHE | D | 383 | −45.514 | −44.634 | −5.014 | 1.00 | 20.08 | C |
| ATOM | 371 | CD1 | PHE | D | 383 | −45.492 | −45.811 | −4.260 | 1.00 | 21.79 | C |
| ATOM | 372 | CE1 | PHE | D | 383 | −46.621 | −46.233 | −3.562 | 1.00 | 26.15 | C |
| ATOM | 373 | CZ | PHE | D | 383 | −47.778 | −45.448 | −3.572 | 1.00 | 18.25 | C |
| ATOM | 374 | CE2 | PHE | D | 383 | −47.812 | −44.276 | −4.317 | 1.00 | 17.32 | C |
| ATOM | 375 | CD2 | PHE | D | 383 | −46.674 | −43.860 | −5.009 | 1.00 | 14.38 | C |
| ATOM | 376 | C | PHE | D | 383 | −41.933 | −43.159 | −5.656 | 1.00 | 18.80 | C |
| ATOM | 377 | O | PHE | D | 383 | −41.985 | −42.850 | −6.851 | 1.00 | 17.18 | O |
| ATOM | 378 | N | PRO | D | 384 | −40.765 | −43.168 | −4.972 | 1.00 | 19.77 | N |
| ATOM | 379 | CA | PRO | D | 384 | −39.516 | −42.830 | −5.731 | 1.00 | 20.37 | C |
| ATOM | 380 | CB | PRO | D | 384 | −38.369 | −43.220 | −4.759 | 1.00 | 21.23 | C |
| ATOM | 381 | CG | PRO | D | 384 | −39.007 | −43.126 | −3.401 | 1.00 | 24.39 | C |
| ATOM | 382 | CD | PRO | D | 384 | −40.471 | −43.593 | −3.588 | 1.00 | 16.66 | C |
| ATOM | 383 | C | PRO | D | 384 | −39.377 | −43.489 | −7.100 | 1.00 | 17.34 | C |
| ATOM | 384 | O | PRO | D | 384 | −39.722 | −44.660 | −7.290 | 1.00 | 20.17 | O |
| ATOM | 385 | N | GLY | D | 385 | −38.958 | −42.701 | −8.082 | 1.00 | 14.40 | N |
| ATOM | 386 | CA | GLY | D | 385 | −38.925 | −43.184 | −9.454 | 1.00 | 17.24 | C |
| ATOM | 387 | C | GLY | D | 385 | −40.200 | −42.918 | −10.243 | 1.00 | 16.61 | C |
| ATOM | 388 | O | GLY | D | 385 | −40.267 | −43.218 | −11.462 | 1.00 | 15.88 | O |
| ATOM | 389 | N | TYR | D | 386 | −41.232 | −42.424 | −9.553 | 1.00 | 13.80 | N |
| ATOM | 390 | CA | TYR | D | 386 | −42.472 | −42.005 | −10.233 | 1.00 | 16.51 | C |
| ATOM | 391 | CB | TYR | D | 386 | −43.683 | −42.863 | −9.768 | 1.00 | 13.91 | C |
| ATOM | 392 | CG | TYR | D | 386 | −43.611 | −44.357 | −10.112 | 1.00 | 14.66 | C |
| ATOM | 393 | CD1 | TYR | D | 386 | −44.196 | −44.849 | −11.288 | 1.00 | 12.37 | C |
| ATOM | 394 | CE1 | TYR | D | 386 | −44.139 | −46.200 | −11.605 | 1.00 | 13.28 | C |
| ATOM | 395 | CZ | TYR | D | 386 | −43.497 | −47.092 | −10.741 | 1.00 | 13.00 | C |
| ATOM | 396 | OH | TYR | D | 386 | −43.452 | −48.430 | −11.098 | 1.00 | 11.38 | O |
| ATOM | 397 | CE2 | TYR | D | 386 | −42.920 | −46.641 | −9.560 | 1.00 | 12.98 | C |
| ATOM | 398 | CD2 | TYR | D | 386 | −42.996 | −45.285 | −9.240 | 1.00 | 14.44 | C |
| ATOM | 399 | C | TYR | D | 386 | −42.780 | −40.514 | −9.987 | 1.00 | 16.12 | C |
| ATOM | 400 | O | TYR | D | 386 | −42.433 | −39.953 | −8.966 | 1.00 | 12.28 | O |
| ATOM | 401 | N | ALA | D | 387 | −43.482 | −39.911 | −10.927 | 1.00 | 16.31 | N |
| ATOM | 402 | CA | ALA | D | 387 | −43.942 | −38.564 | −10.808 | 1.00 | 14.82 | C |
| ATOM | 403 | CB | ALA | D | 387 | −43.564 | −37.771 | −12.076 | 1.00 | 14.59 | C |
| ATOM | 404 | C | ALA | D | 387 | −45.449 | −38.707 | −10.713 | 1.00 | 18.68 | C |
| ATOM | 405 | O | ALA | D | 387 | −46.016 | −39.750 | −11.110 | 1.00 | 15.78 | O |

TABLE 4-continued

Atomic coordinates for CRBN(TBD):Pomalidomide (Murine protein)

| ATOM | 406 | N   | TRP | D | 388 | −46.105 | −37.673 | −10.221 | 1.00 | 14.36 | N |
|------|-----|-----|-----|---|-----|---------|---------|---------|------|-------|---|
| ATOM | 407 | CA  | TRP | D | 388 | −47.556 | −37.721 | −10.006 | 1.00 | 16.10 | C |
| ATOM | 408 | CB  | TRP | D | 388 | −47.877 | −37.612 | −8.527  | 1.00 | 13.99 | C |
| ATOM | 409 | CG  | TRP | D | 388 | −47.227 | −36.455 | −7.832  | 1.00 | 14.45 | C |
| ATOM | 410 | CD1 | TRP | D | 388 | −46.022 | −36.447 | −7.136  | 1.00 | 14.72 | C |
| ATOM | 411 | NE1 | TRP | D | 388 | −45.768 | −35.170 | −6.630  | 1.00 | 13.85 | N |
| ATOM | 412 | CE2 | TRP | D | 388 | −46.765 | −34.311 | −6.977  | 1.00 | 14.16 | C |
| ATOM | 413 | CD2 | TRP | D | 388 | −47.734 | −35.065 | −7.760  | 1.00 | 12.99 | C |
| ATOM | 414 | CE3 | TRP | D | 388 | −48.885 | −34.416 | −8.231  | 1.00 | 13.59 | C |
| ATOM | 415 | CZ3 | TRP | D | 388 | −49.045 | −33.030 | −7.951  | 1.00 | 22.02 | C |
| ATOM | 416 | CH2 | TRP | D | 388 | −48.091 | −32.315 | −7.212  | 1.00 | 17.37 | C |
| ATOM | 417 | CZ2 | TRP | D | 388 | −46.936 | −32.936 | −6.695  | 1.00 | 17.87 | C |
| ATOM | 418 | C   | TRP | D | 388 | −48.293 | −36.667 | −10.780 | 1.00 | 16.70 | C |
| ATOM | 419 | O   | TRP | D | 388 | −47.760 | −35.579 | −11.058 | 1.00 | 15.47 | O |
| ATOM | 420 | N   | THR | D | 389 | −49.517 | −36.994 | −11.168 | 1.00 | 15.71 | N |
| ATOM | 421 | CA  | THR | D | 389 | −50.413 | −36.016 | −11.793 | 1.00 | 17.50 | C |
| ATOM | 422 | CB  | THR | D | 389 | −50.614 | −36.319 | −13.315 | 1.00 | 17.16 | C |
| ATOM | 423 | OG1 | THR | D | 389 | −49.345 | −36.323 | −13.949 | 1.00 | 17.93 | O |
| ATOM | 424 | CG2 | THR | D | 389 | −51.453 | −35.261 | −13.992 | 1.00 | 14.92 | C |
| ATOM | 425 | C   | THR | D | 389 | −51.747 | −36.120 | −11.055 | 1.00 | 16.97 | C |
| ATOM | 426 | O   | THR | D | 389 | −52.271 | −37.225 | −10.892 | 1.00 | 14.38 | O |
| ATOM | 427 | N   | ILE | D | 390 | −52.313 | −34.986 | −10.647 | 1.00 | 13.44 | N |
| ATOM | 428 | CA  | ILE | D | 390 | −53.672 | −35.024 | −9.996  | 1.00 | 13.01 | C |
| ATOM | 429 | CB  | ILE | D | 390 | −54.094 | −33.589 | −9.577  | 1.00 | 15.37 | C |
| ATOM | 430 | CG1 | ILE | D | 390 | −53.148 | −33.081 | −8.496  | 1.00 | 21.58 | C |
| ATOM | 431 | CD1 | ILE | D | 390 | −53.299 | −31.578 | −8.181  | 1.00 | 28.38 | C |
| ATOM | 432 | CG2 | ILE | D | 390 | −55.555 | −33.551 | −9.123  | 1.00 | 16.44 | C |
| ATOM | 433 | C   | ILE | D | 390 | −54.715 | −35.631 | −10.917 | 1.00 | 12.38 | C |
| ATOM | 434 | O   | ILE | D | 390 | −54.710 | −35.330 | −12.155 | 1.00 | 12.79 | O |
| ATOM | 435 | N   | ALA | D | 391 | −55.601 | −36.476 | −10.338 | 1.00 | 11.93 | N |
| ATOM | 436 | CA  | ALA | D | 391 | −56.627 | −37.195 | −11.067 | 1.00 | 13.20 | C |
| ATOM | 437 | CB  | ALA | D | 391 | −56.324 | −38.720 | −11.053 | 1.00 | 13.08 | C |
| ATOM | 438 | C   | ALA | D | 391 | −57.986 | −36.940 | −10.425 | 1.00 | 14.34 | C |
| ATOM | 439 | O   | ALA | D | 391 | −58.203 | −37.218 | −9.229  | 1.00 | 13.65 | O |
| ATOM | 440 | N   | GLN | D | 392 | −58.903 | −36.405 | −11.196 | 1.00 | 13.27 | N |
| ATOM | 441 | CA  | GLN | D | 392 | −60.202 | −36.125 | −10.636 | 1.00 | 14.78 | C |
| ATOM | 442 | CB  | GLN | D | 392 | −60.417 | −34.603 | −10.536 | 1.00 | 19.61 | C |
| ATOM | 443 | CG  | GLN | D | 392 | −60.409 | −33.910 | −11.873 | 1.00 | 19.31 | C |
| ATOM | 444 | CD  | GLN | D | 392 | −60.611 | −32.399 | −11.720 | 1.00 | 28.10 | C |
| ATOM | 445 | OE1 | GLN | D | 392 | −59.922 | −31.739 | −10.936 | 1.00 | 22.08 | O |
| ATOM | 446 | NE2 | GLN | D | 392 | −61.533 | −31.853 | −12.494 | 1.00 | 18.99 | N |
| ATOM | 447 | C   | GLN | D | 392 | −61.331 | −36.757 | −11.443 | 1.00 | 13.09 | C |
| ATOM | 448 | O   | GLN | D | 392 | −61.203 | −37.004 | −12.666 | 1.00 | 10.48 | O |
| ATOM | 449 | N   | CYS | D | 393 | −62.439 | −37.022 | −10.761 | 1.00 | 12.28 | N |
| ATOM | 450 | CA  | CYS | D | 393 | −63.614 | −37.677 | −11.380 | 1.00 | 10.15 | C |
| ATOM | 451 | CB  | CYS | D | 393 | −64.750 | −37.834 | −10.342 | 1.00 | 10.86 | C |
| ATOM | 452 | SG  | CYS | D | 393 | −66.264 | −38.512 | −11.101 | 1.00 | 13.50 | S |
| ATOM | 453 | C   | CYS | D | 393 | −64.112 | −36.828 | −12.553 | 1.00 | 11.97 | C |
| ATOM | 454 | O   | CYS | D | 393 | −64.240 | −35.579 | −12.403 | 1.00 | 11.58 | O |
| ATOM | 455 | N   | LYS | D | 394 | −64.314 | −37.462 | −13.719 | 1.00 | 11.31 | N |
| ATOM | 456 | CA  | LYS | D | 394 | −64.747 | −36.758 | −14.945 | 1.00 | 12.98 | C |
| ATOM | 457 | CB  | LYS | D | 394 | −64.691 | −37.695 | −16.154 | 1.00 | 15.77 | C |
| ATOM | 458 | CG  | LYS | D | 394 | −65.781 | −38.795 | −16.224 | 1.00 | 13.41 | C |
| ATOM | 459 | CD  | LYS | D | 394 | −65.790 | −39.401 | −17.643 | 1.00 | 15.91 | C |
| ATOM | 460 | CE  | LYS | D | 394 | −67.089 | −40.162 | −17.963 | 1.00 | 19.30 | C |
| ATOM | 461 | NZ  | LYS | D | 394 | −66.792 | −41.211 | −19.000 | 1.00 | 22.82 | N |
| ATOM | 462 | C   | LYS | D | 394 | −66.148 | −36.182 | −14.810 | 1.00 | 12.21 | C |
| ATOM | 463 | O   | LYS | D | 394 | −66.501 | −35.251 | −15.512 | 1.00 | 10.78 | O |
| ATOM | 464 | N   | ILE | D | 395 | −66.967 | −36.770 | −13.931 | 1.00 | 10.39 | N |
| ATOM | 465 | CA  | ILE | D | 395 | −68.327 | −36.251 | −13.732 | 1.00 | 12.82 | C |
| ATOM | 466 | CB  | ILE | D | 395 | −69.330 | −37.377 | −13.326 | 1.00 | 15.03 | C |
| ATOM | 467 | CG1 | ILE | D | 395 | −69.500 | −38.462 | −14.442 | 1.00 | 12.89 | C |
| ATOM | 468 | CD1 | ILE | D | 395 | −69.999 | −37.977 | −15.819 | 1.00 | 18.63 | C |
| ATOM | 469 | CG2 | ILE | D | 395 | −70.661 | −36.774 | −12.855 | 1.00 | 12.67 | C |
| ATOM | 470 | C   | ILE | D | 395 | −68.430 | −35.072 | −12.695 | 1.00 | 15.23 | C |
| ATOM | 471 | O   | ILE | D | 395 | −69.015 | −33.986 | −13.011 | 1.00 | 14.48 | O |
| ATOM | 472 | N   | CYS | D | 396 | −67.884 | −35.266 | −11.474 | 1.00 | 11.74 | N |
| ATOM | 473 | CA  | CYS | D | 396 | −68.110 | −34.286 | −10.406 | 1.00 | 12.31 | C |
| ATOM | 474 | CB  | CYS | D | 396 | −68.708 | −34.950 | −9.180  | 1.00 | 14.41 | C |
| ATOM | 475 | SG  | CYS | D | 396 | −67.536 | −36.079 | −8.380  | 1.00 | 13.68 | S |
| ATOM | 476 | C   | CYS | D | 396 | −66.887 | −33.466 | −10.025 | 1.00 | 14.18 | C |
| ATOM | 477 | O   | CYS | D | 396 | −66.975 | −32.588 | −9.143  | 1.00 | 14.91 | O |
| ATOM | 478 | N   | ALA | D | 397 | −65.780 | −33.744 | −10.717 | 1.00 | 13.71 | N |
| ATOM | 479 | CA  | ALA | D | 397 | −64.472 | −33.122 | −10.494 | 1.00 | 13.23 | C |
| ATOM | 480 | CB  | ALA | D | 397 | −64.498 | −31.612 | −10.832 | 1.00 | 16.60 | C |
| ATOM | 481 | C   | ALA | D | 397 | −63.880 | −33.379 | −9.085  | 1.00 | 12.71 | C |
| ATOM | 482 | O   | ALA | D | 397 | −62.928 | −32.715 | −8.714  | 1.00 | 13.85 | O |
| ATOM | 483 | N   | SER | D | 398 | −64.412 | −34.346 | −8.317  | 1.00 | 10.48 | N |

TABLE 4-continued

Atomic coordinates for CRBN(TBD):Pomalidomide (Murine protein)

| ATOM | 484 | CA | SER | D | 398 | −63.847 | −34.664 | −7.006 | 1.00 | 12.91 | C |
|---|---|---|---|---|---|---|---|---|---|---|---|
| ATOM | 485 | CB | SER | D | 398 | −64.680 | −35.706 | −6.236 | 1.00 | 15.08 | C |
| ATOM | 486 | OG | SER | D | 398 | −66.017 | −35.188 | −6.062 | 1.00 | 17.86 | O |
| ATOM | 487 | C | SER | D | 398 | −62.489 | −35.201 | −7.239 | 1.00 | 16.45 | C |
| ATOM | 488 | O | SER | D | 398 | −62.288 | −36.017 | −8.163 | 1.00 | 15.23 | O |
| ATOM | 489 | N | HIS | D | 399 | −61.547 | −34.791 | −6.398 | 1.00 | 16.26 | N |
| ATOM | 490 | CA | HIS | D | 399 | −60.148 | −35.277 | −6.523 | 1.00 | 20.34 | C |
| ATOM | 491 | CB | HIS | D | 399 | −59.169 | −34.342 | −5.772 | 1.00 | 28.30 | C |
| ATOM | 492 | CG | HIS | D | 399 | −58.841 | −33.039 | −6.510 | 1.00 | 38.19 | C |
| ATOM | 493 | ND1 | HIS | D | 399 | −59.751 | −32.360 | −7.256 | 1.00 | 45.02 | N |
| ATOM | 494 | CE1 | HIS | D | 399 | −59.171 | −31.243 | −7.762 | 1.00 | 36.88 | C |
| ATOM | 495 | NE2 | HIS | D | 399 | −57.900 | −31.193 | −7.320 | 1.00 | 35.80 | N |
| ATOM | 496 | CD2 | HIS | D | 399 | −57.661 | −32.274 | −6.545 | 1.00 | 37.39 | C |
| ATOM | 497 | C | HIS | D | 399 | −60.058 | −36.672 | −5.984 | 1.00 | 18.25 | C |
| ATOM | 498 | O | HIS | D | 399 | −60.261 | −36.897 | −4.795 | 1.00 | 22.04 | O |
| ATOM | 499 | N | ILE | D | 400 | −59.807 | −37.652 | −6.844 | 1.00 | 18.94 | N |
| ATOM | 500 | CA | ILE | D | 400 | −59.835 | −39.041 | −6.370 | 1.00 | 14.15 | C |
| ATOM | 501 | CB | ILE | D | 400 | −60.411 | −40.039 | −7.429 | 1.00 | 14.33 | C |
| ATOM | 502 | CG1 | ILE | D | 400 | −61.800 | −39.564 | −7.918 | 1.00 | 20.52 | C |
| ATOM | 503 | CD1 | ILE | D | 400 | −62.771 | −39.184 | −6.830 | 1.00 | 17.91 | C |
| ATOM | 504 | CG2 | ILE | D | 400 | −60.253 | −41.458 | −6.822 | 1.00 | 13.75 | C |
| ATOM | 505 | C | ILE | D | 400 | −58.439 | −39.507 | −5.949 | 1.00 | 12.55 | C |
| ATOM | 506 | O | ILE | D | 400 | −58.318 | −40.312 | −5.034 | 1.00 | 14.22 | O |
| ATOM | 507 | N | GLY | D | 401 | −57.400 | −38.986 | −6.612 | 1.00 | 11.62 | N |
| ATOM | 508 | CA | GLY | D | 401 | −56.030 | −39.454 | −6.402 | 1.00 | 11.50 | C |
| ATOM | 509 | C | GLY | D | 401 | −55.055 | −38.874 | −7.406 | 1.00 | 12.10 | C |
| ATOM | 510 | O | GLY | D | 401 | −55.165 | −37.688 | −7.809 | 1.00 | 13.31 | O |
| ATOM | 511 | N | TRP | D | 402 | −54.118 | −39.721 | −7.845 | 1.00 | 12.21 | N |
| ATOM | 512 | CA | TRP | D | 402 | −53.027 | −39.284 | −8.747 | 1.00 | 14.33 | C |
| ATOM | 513 | CB | TRP | D | 402 | −51.753 | −38.930 | −7.924 | 1.00 | 12.12 | C |
| ATOM | 514 | CG | TRP | D | 402 | −52.026 | −37.893 | −6.859 | 1.00 | 14.51 | C |
| ATOM | 515 | CD1 | TRP | D | 402 | −51.772 | −36.518 | −6.936 | 1.00 | 12.75 | C |
| ATOM | 516 | NE1 | TRP | D | 402 | −52.190 | −35.887 | −5.783 | 1.00 | 16.72 | N |
| ATOM | 517 | CE2 | TRP | D | 402 | −52.682 | −36.794 | −4.882 | 1.00 | 16.89 | C |
| ATOM | 518 | CD2 | TRP | D | 402 | −52.590 | −38.114 | −5.510 | 1.00 | 16.55 | C |
| ATOM | 519 | CE3 | TRP | D | 402 | −53.058 | −39.239 | −4.804 | 1.00 | 14.20 | C |
| ATOM | 520 | CZ3 | TRP | D | 402 | −53.570 | −39.052 | −3.492 | 1.00 | 17.10 | C |
| ATOM | 521 | CH2 | TRP | D | 402 | −53.665 | −37.760 | −2.904 | 1.00 | 17.46 | C |
| ATOM | 522 | CZ2 | TRP | D | 402 | −53.214 | −36.613 | −3.574 | 1.00 | 16.25 | C |
| ATOM | 523 | C | TRP | D | 402 | −52.688 | −40.398 | −9.686 | 1.00 | 14.30 | C |
| ATOM | 524 | O | TRP | D | 402 | −52.759 | −41.616 | −9.317 | 1.00 | 13.52 | O |
| ATOM | 525 | N | LYS | D | 403 | −52.320 | −40.026 | −10.902 | 1.00 | 13.72 | N |
| ATOM | 526 | CA | LYS | D | 403 | −51.659 | −40.951 | −11.795 | 1.00 | 13.75 | C |
| ATOM | 527 | CB | LYS | D | 403 | −51.870 | −40.567 | −13.260 | 1.00 | 13.23 | C |
| ATOM | 528 | CG | LYS | D | 403 | −51.555 | −41.728 | −14.207 | 1.00 | 17.06 | C |
| ATOM | 529 | CD | LYS | D | 403 | −51.597 | −41.281 | −15.667 | 1.00 | 21.80 | C |
| ATOM | 530 | CE | LYS | D | 403 | −51.571 | −42.491 | −16.614 | 1.00 | 24.70 | C |
| ATOM | 531 | NZ | LYS | D | 403 | −51.547 | −41.943 | −17.977 | 1.00 | 32.68 | N |
| ATOM | 532 | C | LYS | D | 403 | −50.168 | −40.918 | −11.501 | 1.00 | 19.68 | C |
| ATOM | 533 | O | LYS | D | 403 | −49.583 | −39.824 | −11.444 | 1.00 | 17.80 | O |
| ATOM | 534 | N | PHE | D | 404 | −49.551 | −42.101 | −11.339 | 1.00 | 12.41 | N |
| ATOM | 535 | CA | PHE | D | 404 | −48.106 | −42.191 | −11.158 | 1.00 | 12.80 | C |
| ATOM | 536 | CB | PHE | D | 404 | −47.786 | −43.092 | −9.972 | 1.00 | 10.89 | C |
| ATOM | 537 | CG | PHE | D | 404 | −48.022 | −42.397 | −8.646 | 1.00 | 14.98 | C |
| ATOM | 538 | CD1 | PHE | D | 404 | −47.022 | −41.571 | −8.097 | 1.00 | 11.97 | C |
| ATOM | 539 | CE1 | PHE | D | 404 | −47.255 | −40.840 | −6.933 | 1.00 | 13.58 | C |
| ATOM | 540 | CZ | PHE | D | 404 | −48.465 | −40.954 | −6.274 | 1.00 | 12.79 | C |
| ATOM | 541 | CE2 | PHE | D | 404 | −49.477 | −41.760 | −6.780 | 1.00 | 11.25 | C |
| ATOM | 542 | CD2 | PHE | D | 404 | −49.259 | −42.493 | −7.983 | 1.00 | 12.73 | C |
| ATOM | 543 | C | PHE | D | 404 | −47.448 | −42.693 | −12.428 | 1.00 | 13.53 | C |
| ATOM | 544 | O | PHE | D | 404 | −47.875 | −43.728 | −12.981 | 1.00 | 11.57 | O |
| ATOM | 545 | N | THR | D | 405 | −46.451 | −41.959 | −12.914 | 1.00 | 14.12 | N |
| ATOM | 546 | CA | THR | D | 405 | −45.799 | −42.277 | −14.227 | 1.00 | 13.80 | C |
| ATOM | 547 | CB | THR | D | 405 | −46.046 | −41.130 | −15.278 | 1.00 | 14.98 | C |
| ATOM | 548 | OG1 | THR | D | 405 | −45.873 | −39.869 | −14.652 | 1.00 | 17.13 | O |
| ATOM | 549 | CG2 | THR | D | 405 | −47.504 | −41.145 | −15.785 | 1.00 | 14.03 | C |
| ATOM | 550 | C | THR | D | 405 | −44.296 | −42.477 | −14.002 | 1.00 | 15.75 | C |
| ATOM | 551 | O | THR | D | 405 | −43.697 | −41.667 | −13.306 | 1.00 | 16.13 | O |
| ATOM | 552 | N | ALA | D | 406 | −43.714 | −43.602 | −14.489 | 1.00 | 14.07 | N |
| ATOM | 553 | CA | ALA | D | 406 | −42.297 | −43.939 | −14.220 | 1.00 | 17.74 | C |
| ATOM | 554 | CB | ALA | D | 406 | −41.928 | −45.309 | −14.809 | 1.00 | 16.49 | C |
| ATOM | 555 | C | ALA | D | 406 | −41.399 | −42.891 | −14.831 | 1.00 | 19.95 | C |
| ATOM | 556 | O | ALA | D | 406 | −41.658 | −42.438 | −15.922 | 1.00 | 19.78 | O |
| ATOM | 557 | N | THR | D | 407 | −40.334 | −42.519 | −14.124 | 1.00 | 20.93 | N |
| ATOM | 558 | CA | THR | D | 407 | −39.333 | −41.648 | −14.700 | 1.00 | 25.90 | C |
| ATOM | 559 | CB | THR | D | 407 | −38.660 | −40.737 | −13.651 | 1.00 | 23.99 | C |
| ATOM | 560 | OG1 | THR | D | 407 | −38.099 | −41.540 | −12.591 | 1.00 | 29.96 | O |
| ATOM | 561 | CG2 | THR | D | 407 | −39.673 | −39.751 | −13.083 | 1.00 | 28.37 | C |

TABLE 4-continued

Atomic coordinates for CRBN(TBD):Pomalidomide (Murine protein)

| ATOM | 562 | C | THR | D | 407 | −38.260 | −42.403 | −15.509 | 1.00 | 26.09 | C |
|------|-----|---|-----|---|-----|---------|---------|---------|------|-------|---|
| ATOM | 563 | O | THR | D | 407 | −37.468 | −41.774 | −16.160 | 1.00 | 27.79 | O |
| ATOM | 564 | N | LYS | D | 408 | −38.242 | −43.738 | −15.452 | 1.00 | 23.82 | N |
| ATOM | 565 | CA | LYS | D | 408 | −37.262 | −44.544 | −16.225 | 1.00 | 33.72 | C |
| ATOM | 566 | CB | LYS | D | 408 | −36.107 | −45.077 | −15.338 | 1.00 | 27.05 | C |
| ATOM | 567 | CG | LYS | D | 408 | −35.019 | −44.057 | −14.975 | 1.00 | 34.91 | C |
| ATOM | 568 | CD | LYS | D | 408 | −35.351 | −43.247 | −13.721 | 1.00 | 53.00 | C |
| ATOM | 569 | CE | LYS | D | 408 | −34.497 | −41.977 | −13.588 | 1.00 | 58.35 | C |
| ATOM | 570 | NZ | LYS | D | 408 | −33.578 | −42.012 | −12.413 | 1.00 | 58.21 | N |
| ATOM | 571 | C | LYS | D | 408 | −37.949 | −45.702 | −16.946 | 1.00 | 31.36 | C |
| ATOM | 572 | O | LYS | D | 408 | −38.909 | −46.274 | −16.437 | 1.00 | 18.42 | O |
| ATOM | 573 | N | LYS | D | 409 | −37.424 | −46.074 | −18.110 | 1.00 | 20.95 | N |
| ATOM | 574 | CA | LYS | D | 409 | −38.009 | −47.119 | −18.897 | 1.00 | 24.98 | C |
| ATOM | 575 | CB | LYS | D | 409 | −37.386 | −47.158 | −20.322 | 1.00 | 24.45 | C |
| ATOM | 576 | CG | LYS | D | 409 | −37.767 | −45.989 | −21.216 | 1.00 | 42.36 | C |
| ATOM | 577 | CD | LYS | D | 409 | −39.167 | −46.137 | −21.778 | 1.00 | 43.75 | C |
| ATOM | 578 | CE | LYS | D | 409 | −39.283 | −45.378 | −23.091 | 1.00 | 57.30 | C |
| ATOM | 579 | NZ | LYS | D | 409 | −40.108 | −46.142 | −24.066 | 1.00 | 69.61 | N |
| ATOM | 580 | C | LYS | D | 409 | −37.973 | −48.531 | −18.282 | 1.00 | 19.48 | C |
| ATOM | 581 | O | LYS | D | 409 | −38.757 | −49.382 | −18.685 | 1.00 | 27.02 | O |
| ATOM | 582 | N | ASP | D | 410 | −37.043 | −48.824 | −17.388 | 1.00 | 25.16 | N |
| ATOM | 583 | CA | ASP | D | 410 | −36.886 | −50.250 | −16.999 | 1.00 | 33.61 | C |
| ATOM | 584 | CB | ASP | D | 410 | −35.421 | −50.602 | −16.754 | 1.00 | 43.22 | C |
| ATOM | 585 | CG | ASP | D | 410 | −34.850 | −49.865 | −15.585 | 1.00 | 41.26 | C |
| ATOM | 586 | OD1 | ASP | D | 410 | −35.440 | −48.837 | −15.200 | 1.00 | 52.35 | O |
| ATOM | 587 | OD2 | ASP | D | 410 | −33.829 | −50.317 | −15.028 | 1.00 | 55.02 | O |
| ATOM | 588 | C | ASP | D | 410 | −37.742 | −50.647 | −15.784 | 1.00 | 43.76 | C |
| ATOM | 589 | O | ASP | D | 410 | −37.664 | −51.808 | −15.311 | 1.00 | 34.74 | O |
| ATOM | 590 | N | MET | D | 411 | −38.525 | −49.675 | −15.271 | 1.00 | 27.98 | N |
| ATOM | 591 | CA | MET | D | 411 | −39.476 | −49.906 | −14.186 | 1.00 | 28.95 | C |
| ATOM | 592 | CB | MET | D | 411 | −39.822 | −48.579 | −13.502 | 1.00 | 19.24 | C |
| ATOM | 593 | CG | MET | D | 411 | −38.592 | −48.060 | −12.784 | 1.00 | 32.01 | C |
| ATOM | 594 | SD | MET | D | 411 | −38.948 | −46.691 | −11.714 | 1.00 | 43.30 | S |
| ATOM | 595 | CE | MET | D | 411 | −38.939 | −45.425 | −12.935 | 1.00 | 25.93 | C |
| ATOM | 596 | C | MET | D | 411 | −40.772 | −50.599 | −14.638 | 1.00 | 30.56 | C |
| ATOM | 597 | O | MET | D | 411 | −41.159 | −50.510 | −15.801 | 1.00 | 28.13 | O |
| ATOM | 598 | N | SER | D | 412 | −41.414 | −51.308 | −13.702 | 1.00 | 23.78 | N |
| ATOM | 599 | CA | SER | D | 412 | −42.721 | −51.934 | −13.933 | 1.00 | 19.87 | C |
| ATOM | 600 | CB | SER | D | 412 | −42.600 | −53.434 | −14.274 | 1.00 | 18.60 | C |
| ATOM | 601 | OG | SER | D | 412 | −41.819 | −54.083 | −13.274 | 1.00 | 25.54 | O |
| ATOM | 602 | C | SER | D | 412 | −43.535 | −51.646 | −12.681 | 1.00 | 17.08 | C |
| ATOM | 603 | O | SER | D | 412 | −43.016 | −51.863 | −11.582 | 1.00 | 15.66 | O |
| ATOM | 604 | N | PRO | D | 413 | −44.861 | −51.558 | −12.852 | 1.00 | 15.88 | N |
| ATOM | 605 | CA | PRO | D | 413 | −45.453 | −50.858 | −14.029 | 1.00 | 12.57 | C |
| ATOM | 606 | CB | PRO | D | 413 | −46.926 | −50.750 | −13.630 | 1.00 | 13.13 | C |
| ATOM | 607 | CG | PRO | D | 413 | −46.844 | −50.396 | −12.162 | 1.00 | 8.99 | C |
| ATOM | 608 | CD | PRO | D | 413 | −45.659 | −51.266 | −11.631 | 1.00 | 12.57 | C |
| ATOM | 609 | C | PRO | D | 413 | −44.849 | −49.490 | −14.460 | 1.00 | 12.70 | C |
| ATOM | 610 | O | PRO | D | 413 | −44.348 | −48.745 | −13.629 | 1.00 | 12.74 | O |
| ATOM | 611 | N | GLN | D | 414 | −44.905 | −49.172 | −15.743 | 1.00 | 10.28 | N |
| ATOM | 612 | CA | GLN | D | 414 | −44.562 | −47.802 | −16.203 | 1.00 | 11.82 | C |
| ATOM | 613 | CB | GLN | D | 414 | −44.552 | −47.757 | −17.762 | 1.00 | 13.32 | C |
| ATOM | 614 | CG | GLN | D | 414 | −43.277 | −48.370 | −18.366 | 1.00 | 16.28 | C |
| ATOM | 615 | CD | GLN | D | 414 | −42.056 | −47.572 | −17.976 | 1.00 | 19.40 | C |
| ATOM | 616 | OE1 | GLN | D | 414 | −41.250 | −48.002 | −17.155 | 1.00 | 22.54 | O |
| ATOM | 617 | NE2 | GLN | D | 414 | −41.952 | −46.386 | −18.501 | 1.00 | 13.79 | N |
| ATOM | 618 | C | GLN | D | 414 | −45.533 | −46.726 | −15.666 | 1.00 | 11.67 | C |
| ATOM | 619 | O | GLN | D | 414 | −45.207 | −45.520 | −15.620 | 1.00 | 15.09 | O |
| ATOM | 620 | N | LYS | D | 415 | −46.754 | −47.130 | −15.364 | 1.00 | 10.81 | N |
| ATOM | 621 | CA | LYS | D | 415 | −47.663 | −46.251 | −14.656 | 1.00 | 14.56 | C |
| ATOM | 622 | CB | LYS | D | 415 | −48.381 | −45.281 | −15.649 | 1.00 | 15.93 | C |
| ATOM | 623 | CG | LYS | D | 415 | −49.558 | −45.883 | −16.417 | 1.00 | 18.43 | C |
| ATOM | 624 | CD | LYS | D | 415 | −49.107 | −46.989 | −17.348 | 1.00 | 26.76 | C |
| ATOM | 625 | CE | LYS | D | 415 | −49.854 | −47.053 | −18.695 | 1.00 | 22.81 | C |
| ATOM | 626 | NZ | LYS | D | 415 | −49.364 | −48.250 | −19.424 | 1.00 | 20.62 | N |
| ATOM | 627 | C | LYS | D | 415 | −48.647 | −47.035 | −13.794 | 1.00 | 11.11 | C |
| ATOM | 628 | O | LYS | D | 415 | −48.846 | −48.258 | −13.999 | 1.00 | 9.89 | O |
| ATOM | 629 | N | PHE | D | 416 | −49.249 | −46.341 | −12.818 | 1.00 | 9.25 | N |
| ATOM | 630 | CA | PHE | D | 416 | −50.319 | −46.902 | −12.020 | 1.00 | 9.48 | C |
| ATOM | 631 | CB | PHE | D | 416 | −49.781 | −47.812 | −10.895 | 1.00 | 10.39 | C |
| ATOM | 632 | CG | PHE | D | 416 | −48.910 | −47.103 | −9.895 | 1.00 | 9.70 | C |
| ATOM | 633 | CD1 | PHE | D | 416 | −49.411 | −46.683 | −8.672 | 1.00 | 10.81 | C |
| ATOM | 634 | CE1 | PHE | D | 416 | −48.610 | −46.062 | −7.727 | 1.00 | 12.49 | C |
| ATOM | 635 | CZ | PHE | D | 416 | −47.272 | −45.869 | −7.985 | 1.00 | 11.76 | C |
| ATOM | 636 | CE2 | PHE | D | 416 | −46.738 | −46.297 | −9.188 | 1.00 | 9.84 | C |
| ATOM | 637 | CD2 | PHE | D | 416 | −47.536 | −46.917 | −10.148 | 1.00 | 11.10 | C |
| ATOM | 638 | C | PHE | D | 416 | −51.095 | −45.738 | −11.426 | 1.00 | 9.90 | C |
| ATOM | 639 | O | PHE | D | 416 | −50.799 | −44.596 | −11.692 | 1.00 | 11.81 | O |

TABLE 4-continued

Atomic coordinates for CRBN(TBD):Pomalidomide (Murine protein)

| ATOM | 640 | N | TRP | D | 417 | −52.096 | −46.037 | −10.622 | 1.00 | 8.82 | N |
|---|---|---|---|---|---|---|---|---|---|---|---|
| ATOM | 641 | CA | TRP | D | 417 | −52.835 | −44.966 | −9.969 | 1.00 | 10.98 | C |
| ATOM | 642 | CB | TRP | D | 417 | −54.311 | −45.065 | −10.401 | 1.00 | 11.08 | C |
| ATOM | 643 | CG | TRP | D | 417 | −54.486 | −44.973 | −11.903 | 1.00 | 11.12 | C |
| ATOM | 644 | CD1 | TRP | D | 417 | −54.392 | −45.999 | −12.841 | 1.00 | 11.61 | C |
| ATOM | 645 | NE1 | TRP | D | 417 | −54.629 | −45.508 | −14.126 | 1.00 | 11.51 | N |
| ATOM | 646 | CE2 | TRP | D | 417 | −54.863 | −44.187 | −14.086 | 1.00 | 12.88 | C |
| ATOM | 647 | CD2 | TRP | D | 417 | −54.789 | −43.769 | −12.681 | 1.00 | 11.63 | C |
| ATOM | 648 | CE3 | TRP | D | 417 | −54.989 | −42.423 | −12.360 | 1.00 | 13.96 | C |
| ATOM | 649 | CZ3 | TRP | D | 417 | −55.227 | −41.520 | −13.420 | 1.00 | 13.17 | C |
| ATOM | 650 | CH2 | TRP | D | 417 | −55.320 | −41.968 | −14.759 | 1.00 | 15.26 | C |
| ATOM | 651 | CZ2 | TRP | D | 417 | −55.142 | −43.305 | −15.102 | 1.00 | 15.07 | C |
| ATOM | 652 | C | TRP | D | 417 | −52.765 | −45.116 | −8.475 | 1.00 | 8.85 | C |
| ATOM | 653 | O | TRP | D | 417 | −52.977 | −46.224 | −7.963 | 1.00 | 8.82 | O |
| ATOM | 654 | N | GLY | D | 418 | −52.638 | −44.012 | −7.748 | 1.00 | 8.91 | N |
| ATOM | 655 | CA | GLY | D | 418 | −52.798 | −44.115 | −6.286 | 1.00 | 10.88 | C |
| ATOM | 656 | C | GLY | D | 418 | −54.085 | −43.340 | −5.919 | 1.00 | 11.70 | C |
| ATOM | 657 | O | GLY | D | 418 | −54.182 | −42.151 | −6.214 | 1.00 | 12.23 | O |
| ATOM | 658 | N | LEU | D | 419 | −55.065 | −44.020 | −5.328 | 1.00 | 12.48 | N |
| ATOM | 659 | CA | LEU | D | 419 | −56.418 | −43.452 | −5.157 | 1.00 | 9.88 | C |
| ATOM | 660 | CB | LEU | D | 419 | −57.482 | −44.334 | −5.877 | 1.00 | 11.17 | C |
| ATOM | 661 | CG | LEU | D | 419 | −57.224 | −44.649 | −7.379 | 1.00 | 12.93 | C |
| ATOM | 662 | CD1 | LEU | D | 419 | −58.244 | −45.652 | −7.962 | 1.00 | 15.74 | C |
| ATOM | 663 | CD2 | LEU | D | 419 | −57.242 | −43.342 | −8.201 | 1.00 | 11.98 | C |
| ATOM | 664 | C | LEU | D | 419 | −56.701 | −43.366 | −3.656 | 1.00 | 10.95 | C |
| ATOM | 665 | O | LEU | D | 419 | −56.374 | −44.288 | −2.891 | 1.00 | 12.49 | O |
| ATOM | 666 | N | THR | D | 420 | −57.225 | −42.229 | −3.227 | 1.00 | 12.35 | N |
| ATOM | 667 | CA | THR | D | 420 | −57.615 | −42.012 | −1.806 | 1.00 | 14.78 | C |
| ATOM | 668 | CB | THR | D | 420 | −57.917 | −40.511 | −1.607 | 1.00 | 17.24 | C |
| ATOM | 669 | OG1 | THR | D | 420 | −56.748 | −39.799 | −2.020 | 1.00 | 14.00 | O |
| ATOM | 670 | CG2 | THR | D | 420 | −58.311 | −40.158 | −0.098 | 1.00 | 13.66 | C |
| ATOM | 671 | C | THR | D | 420 | −58.834 | −42.877 | −1.508 | 1.00 | 14.19 | C |
| ATOM | 672 | O | THR | D | 420 | −59.866 | −42.733 | −2.161 | 1.00 | 13.73 | O |
| ATOM | 673 | N | ARG | D | 421 | −58.679 | −43.852 | −0.602 | 1.00 | 12.36 | N |
| ATOM | 674 | CA | ARG | D | 421 | −59.736 | −44.849 | −0.345 | 1.00 | 17.09 | C |
| ATOM | 675 | CB | ARG | D | 421 | −59.353 | −45.826 | 0.790 | 1.00 | 22.23 | C |
| ATOM | 676 | CG | ARG | D | 421 | −58.414 | −46.946 | 0.426 | 1.00 | 30.22 | C |
| ATOM | 677 | CD | ARG | D | 421 | −57.848 | −47.604 | 1.715 | 1.00 | 30.57 | C |
| ATOM | 678 | NE | ARG | D | 421 | −56.626 | −48.369 | 1.444 | 1.00 | 36.36 | N |
| ATOM | 679 | CZ | ARG | D | 421 | −56.620 | −49.592 | 0.910 | 1.00 | 44.87 | C |
| ATOM | 680 | NH1 | ARG | D | 421 | −57.772 | −50.188 | 0.593 | 1.00 | 51.21 | N |
| ATOM | 681 | NH2 | ARG | D | 421 | −55.470 | −50.222 | 0.690 | 1.00 | 40.12 | N |
| ATOM | 682 | C | ARG | D | 421 | −61.024 | −44.213 | 0.083 | 1.00 | 16.52 | C |
| ATOM | 683 | O | ARG | D | 421 | −62.096 | −44.713 | −0.251 | 1.00 | 14.73 | O |
| ATOM | 684 | N | SER | D | 422 | −60.930 | −43.143 | 0.874 | 1.00 | 12.14 | N |
| ATOM | 685 | CA | SER | D | 422 | −62.167 | −42.530 | 1.408 | 1.00 | 16.31 | C |
| ATOM | 686 | CB | SER | D | 422 | −61.834 | −41.558 | 2.561 | 1.00 | 20.51 | C |
| ATOM | 687 | OG | SER | D | 422 | −60.991 | −40.527 | 2.063 | 1.00 | 15.45 | O |
| ATOM | 688 | C | SER | D | 422 | −62.939 | −41.789 | 0.322 | 1.00 | 15.91 | C |
| ATOM | 689 | O | SER | D | 422 | −64.092 | −41.374 | 0.533 | 1.00 | 13.62 | O |
| ATOM | 690 | N | ALA | D | 423 | −62.307 | −41.600 | −0.841 | 1.00 | 13.42 | N |
| ATOM | 691 | CA | ALA | D | 423 | −62.986 | −40.952 | −1.978 | 1.00 | 13.14 | C |
| ATOM | 692 | CB | ALA | D | 423 | −61.980 | −40.216 | −2.838 | 1.00 | 12.90 | C |
| ATOM | 693 | C | ALA | D | 423 | −63.752 | −41.963 | −2.820 | 1.00 | 12.91 | C |
| ATOM | 694 | O | ALA | D | 423 | −64.359 | −41.604 | −3.822 | 1.00 | 12.81 | O |
| ATOM | 695 | N | LEU | D | 424 | −63.695 | −43.246 | −2.440 | 1.00 | 14.18 | N |
| ATOM | 696 | CA | LEU | D | 424 | −64.398 | −44.308 | −3.186 | 1.00 | 11.87 | C |
| ATOM | 697 | CB | LEU | D | 424 | −63.380 | −45.343 | −3.697 | 1.00 | 12.17 | C |
| ATOM | 698 | CG | LEU | D | 424 | −62.251 | −44.765 | −4.601 | 1.00 | 14.29 | C |
| ATOM | 699 | CD1 | LEU | D | 424 | −61.072 | −45.768 | −4.712 | 1.00 | 14.19 | C |
| ATOM | 700 | CD2 | LEU | D | 424 | −62.773 | −44.377 | −5.987 | 1.00 | 13.76 | C |
| ATOM | 701 | C | LEU | D | 424 | −65.467 | −45.009 | −2.327 | 1.00 | 13.48 | C |
| ATOM | 702 | O | LEU | D | 424 | −65.328 | −45.088 | −1.126 | 1.00 | 13.98 | O |
| ATOM | 703 | N | LEU | D | 425 | −66.460 | −45.617 | −2.977 | 1.00 | 14.90 | N |
| ATOM | 704 | CA | LEU | D | 425 | −67.433 | −46.462 | −2.276 | 1.00 | 22.54 | C |
| ATOM | 705 | CB | LEU | D | 425 | −68.842 | −45.890 | −2.406 | 1.00 | 25.83 | C |
| ATOM | 706 | CG | LEU | D | 425 | −69.508 | −45.054 | −1.287 | 1.00 | 28.41 | C |
| ATOM | 707 | CD1 | LEU | D | 425 | −70.840 | −44.603 | −1.848 | 1.00 | 25.53 | C |
| ATOM | 708 | CD2 | LEU | D | 425 | −69.736 | −45.900 | −0.046 | 1.00 | 30.31 | C |
| ATOM | 709 | C | LEU | D | 425 | −67.367 | −47.842 | −2.919 | 1.00 | 25.71 | C |
| ATOM | 710 | O | LEU | D | 425 | −67.271 | −47.894 | −4.152 | 1.00 | 22.50 | O |
| ATOM | 711 | N | PRO | D | 426 | −67.775 | −48.885 | −2.159 | 1.00 | 33.18 | N |
| ATOM | 712 | CA | PRO | D | 426 | −67.053 | −50.013 | −1.618 | 1.00 | 48.92 | C |
| ATOM | 713 | CB | PRO | D | 426 | −67.388 | −51.141 | −2.594 | 1.00 | 41.81 | C |
| ATOM | 714 | CG | PRO | D | 426 | −68.695 | −50.699 | −3.246 | 1.00 | 43.68 | C |
| ATOM | 715 | CD | PRO | D | 426 | −69.083 | −49.381 | −2.616 | 1.00 | 43.50 | C |
| ATOM | 716 | C | PRO | D | 426 | −65.578 | −49.716 | −1.515 | 1.00 | 49.77 | C |
| ATOM | 717 | O | PRO | D | 426 | −65.226 | −48.678 | −0.959 | 1.00 | 40.20 | O |

TABLE 4-continued

Atomic coordinates for CRBN(TBD):Pomalidomide (Murine protein)

| ATOM | 718 | N | THR | A | 321 | −54.675 | −62.915 | −3.216 | 1.00 | 36.85 | N |
|---|---|---|---|---|---|---|---|---|---|---|---|
| ATOM | 719 | CA | THR | A | 321 | −54.397 | −62.908 | −4.703 | 1.00 | 33.70 | C |
| ATOM | 720 | CB | THR | A | 321 | −55.257 | −61.851 | −5.445 | 1.00 | 33.79 | C |
| ATOM | 721 | OG1 | THR | A | 321 | −54.707 | −60.531 | −5.240 | 1.00 | 38.82 | C |
| ATOM | 722 | CG2 | THR | A | 321 | −56.731 | −61.893 | −4.983 | 1.00 | 47.72 | C |
| ATOM | 723 | C | THR | A | 321 | −52.899 | −62.704 | −5.079 | 1.00 | 27.23 | C |
| ATOM | 724 | O | THR | A | 321 | −52.533 | −62.920 | −6.229 | 1.00 | 22.14 | O |
| ATOM | 725 | N | SER | A | 322 | −52.070 | −62.241 | −4.134 | 1.00 | 18.61 | N |
| ATOM | 726 | CA | SER | A | 322 | −50.683 | −61.830 | −4.462 | 1.00 | 23.51 | C |
| ATOM | 727 | CB | SER | A | 322 | −50.059 | −61.094 | −3.272 | 1.00 | 24.88 | C |
| ATOM | 728 | OG | SER | A | 322 | −50.807 | −59.930 | −3.043 | 1.00 | 27.19 | O |
| ATOM | 729 | C | SER | A | 322 | −49.722 | −62.967 | −4.879 | 1.00 | 22.97 | C |
| ATOM | 730 | O | SER | A | 322 | −49.666 | −64.008 | −4.218 | 1.00 | 24.02 | O |
| ATOM | 731 | N | LEU | A | 323 | −48.928 | −62.740 | −5.932 | 1.00 | 15.40 | N |
| ATOM | 732 | CA | LEU | A | 323 | −47.818 | −63.645 | −6.258 | 1.00 | 13.14 | C |
| ATOM | 733 | CB | LEU | A | 323 | −47.912 | −64.160 | −7.706 | 1.00 | 14.81 | C |
| ATOM | 734 | CG | LEU | A | 323 | −49.188 | −65.044 | −7.954 | 1.00 | 15.73 | C |
| ATOM | 735 | CD1 | LEU | A | 323 | −49.508 | −65.254 | −9.423 | 1.00 | 21.00 | C |
| ATOM | 736 | CD2 | LEU | A | 323 | −49.098 | −66.394 | −7.248 | 1.00 | 20.79 | C |
| ATOM | 737 | C | LEU | A | 323 | −46.528 | −62.901 | −6.044 | 1.00 | 14.34 | C |
| ATOM | 738 | O | LEU | A | 323 | −46.253 | −61.935 | −6.750 | 1.00 | 13.90 | O |
| ATOM | 739 | N | CYS | A | 324 | −45.753 | −63.356 | −5.044 | 1.00 | 13.99 | N |
| ATOM | 740 | CA | CYS | A | 324 | −44.564 | −62.669 | −4.600 | 1.00 | 16.60 | C |
| ATOM | 741 | CB | CYS | A | 324 | −44.591 | −62.550 | −3.052 | 1.00 | 16.43 | C |
| ATOM | 742 | SG | CYS | A | 324 | −45.903 | −61.421 | −2.455 | 1.00 | 20.16 | S |
| ATOM | 743 | C | CYS | A | 324 | −43.303 | −63.409 | −5.072 | 1.00 | 13.72 | C |
| ATOM | 744 | O | CYS | A | 324 | −43.348 | −64.620 | −5.320 | 1.00 | 13.21 | O |
| ATOM | 745 | N | CYS | A | 325 | −42.196 | −62.669 | −5.207 | 1.00 | 13.65 | N |
| ATOM | 746 | CA | CYS | A | 325 | −40.893 | −63.235 | −5.425 | 1.00 | 13.55 | C |
| ATOM | 747 | CB | CYS | A | 325 | −39.805 | −62.154 | −5.330 | 1.00 | 16.01 | C |
| ATOM | 748 | SG | CYS | A | 325 | −38.111 | −62.791 | −5.478 | 1.00 | 16.92 | S |
| ATOM | 749 | C | CYS | A | 325 | −40.624 | −64.313 | −4.377 | 1.00 | 12.56 | C |
| ATOM | 750 | O | CYS | A | 325 | −40.712 | −64.079 | −3.191 | 1.00 | 13.54 | O |
| ATOM | 751 | N | LYS | A | 326 | −40.308 | −65.501 | −4.818 | 1.00 | 12.78 | N |
| ATOM | 752 | CA | LYS | A | 326 | −40.080 | −66.574 | −3.869 | 1.00 | 13.61 | C |
| ATOM | 753 | CB | LYS | A | 326 | −40.075 | −67.933 | −4.601 | 1.00 | 16.71 | C |
| ATOM | 754 | CG | LYS | A | 326 | −40.005 | −69.119 | −3.623 | 1.00 | 20.49 | C |
| ATOM | 755 | CD | LYS | A | 326 | −40.928 | −70.266 | −4.045 | 1.00 | 24.76 | C |
| ATOM | 756 | CE | LYS | A | 326 | −40.134 | −71.373 | −4.660 | 1.00 | 27.96 | C |
| ATOM | 757 | NZ | LYS | A | 326 | −40.985 | −72.307 | −5.455 | 1.00 | 36.68 | N |
| ATOM | 758 | C | LYS | A | 326 | −38.784 | −66.389 | −3.042 | 1.00 | 13.57 | C |
| ATOM | 759 | O | LYS | A | 326 | −38.703 | −66.815 | −1.860 | 1.00 | 14.01 | O |
| ATOM | 760 | N | GLN | A | 327 | −37.757 | −65.810 | −3.676 | 1.00 | 14.76 | N |
| ATOM | 761 | CA | GLN | A | 327 | −36.497 | −65.614 | −3.027 | 1.00 | 17.02 | C |
| ATOM | 762 | CB | GLN | A | 327 | −35.411 | −65.233 | −4.034 | 1.00 | 17.41 | C |
| ATOM | 763 | CG | GLN | A | 327 | −34.077 | −64.947 | −3.352 | 1.00 | 15.71 | C |
| ATOM | 764 | CD | GLN | A | 327 | −32.976 | −64.766 | −4.348 | 1.00 | 21.33 | C |
| ATOM | 765 | OE1 | GLN | A | 327 | −33.053 | −65.294 | −5.440 | 1.00 | 20.60 | O |
| ATOM | 766 | NE2 | GLN | A | 327 | −31.943 | −64.019 | −3.983 | 1.00 | 19.63 | N |
| ATOM | 767 | C | GLN | A | 327 | −36.585 | −64.580 | −1.883 | 1.00 | 14.71 | C |
| ATOM | 768 | O | GLN | A | 327 | −36.260 | −64.910 | −0.742 | 1.00 | 12.39 | O |
| ATOM | 769 | N | CYS | A | 328 | −37.033 | −63.346 | −2.177 | 1.00 | 13.05 | N |
| ATOM | 770 | CA | CYS | A | 328 | −37.057 | −62.319 | −1.133 | 1.00 | 12.85 | C |
| ATOM | 771 | CB | CYS | A | 328 | −36.652 | −60.933 | −1.667 | 1.00 | 10.68 | C |
| ATOM | 772 | SG | CYS | A | 328 | −37.896 | −60.256 | −2.776 | 1.00 | 14.55 | S |
| ATOM | 773 | C | CYS | A | 328 | −38.430 | −62.273 | −0.374 | 1.00 | 14.31 | C |
| ATOM | 774 | O | CYS | A | 328 | −38.576 | −61.541 | 0.619 | 1.00 | 13.89 | O |
| ATOM | 775 | N | GLN | A | 329 | −39.426 | −63.029 | −0.862 | 1.00 | 15.72 | N |
| ATOM | 776 | CA | GLN | A | 329 | −40.730 | −63.255 | −0.139 | 1.00 | 15.02 | C |
| ATOM | 777 | CB | GLN | A | 329 | −40.515 | −63.846 | 1.270 | 1.00 | 14.54 | C |
| ATOM | 778 | CG | GLN | A | 329 | −39.514 | −65.025 | 1.259 | 1.00 | 18.55 | C |
| ATOM | 779 | CD | GLN | A | 329 | −39.554 | −65.872 | 2.516 | 1.00 | 20.90 | C |
| ATOM | 780 | OE1 | GLN | A | 329 | −39.833 | −67.056 | 2.457 | 1.00 | 19.96 | O |
| ATOM | 781 | NE2 | GLN | A | 329 | −39.276 | −65.264 | 3.657 | 1.00 | 15.75 | N |
| ATOM | 782 | C | GLN | A | 329 | −41.701 | −62.091 | −0.045 | 1.00 | 19.78 | C |
| ATOM | 783 | O | GLN | A | 329 | −42.900 | −62.278 | −0.187 | 1.00 | 22.09 | O |
| ATOM | 784 | N | GLU | A | 330 | −41.186 | −60.904 | 0.206 | 1.00 | 16.66 | N |
| ATOM | 785 | CA | GLU | A | 330 | −41.989 | −59.773 | 0.570 | 1.00 | 19.80 | C |
| ATOM | 786 | CB | GLU | A | 330 | −41.181 | −58.860 | 1.476 | 1.00 | 21.82 | C |
| ATOM | 787 | CG | GLU | A | 330 | −40.763 | −59.534 | 2.772 | 1.00 | 30.49 | C |
| ATOM | 788 | CD | GLU | A | 330 | −41.918 | −60.221 | 3.470 | 1.00 | 42.30 | C |
| ATOM | 789 | OE1 | GLU | A | 330 | −41.888 | −61.474 | 3.606 | 1.00 | 59.27 | O |
| ATOM | 790 | OE2 | GLU | A | 330 | −42.857 | −59.501 | 3.878 | 1.00 | 47.44 | O |
| ATOM | 791 | C | GLU | A | 330 | −42.464 | −58.970 | −0.662 | 1.00 | 25.10 | C |
| ATOM | 792 | O | GLU | A | 330 | −43.399 | −58.175 | −0.554 | 1.00 | 19.27 | O |
| ATOM | 793 | N | THR | A | 331 | −41.808 | −59.190 | −1.807 | 1.00 | 15.88 | N |
| ATOM | 794 | CA | THR | A | 331 | −41.965 | −58.341 | −2.958 | 1.00 | 16.40 | C |
| ATOM | 795 | CB | THR | A | 331 | −40.612 | −58.191 | −3.701 | 1.00 | 16.06 | C |

TABLE 4-continued

Atomic coordinates for CRBN(TBD):Pomalidomide (Murine protein)

| ATOM | 796 | OG1 | THR | A | 331 | −39.677 | −57.571 | −2.812 | 1.00 | 16.10 | O |
|---|---|---|---|---|---|---|---|---|---|---|---|
| ATOM | 797 | CG2 | THR | A | 331 | −40.751 | −57.282 | −4.997 | 1.00 | 15.45 | C |
| ATOM | 798 | C | THR | A | 331 | −43.023 | −58.935 | −3.880 | 1.00 | 17.58 | C |
| ATOM | 799 | O | THR | A | 331 | −42.834 | −60.040 | −4.420 | 1.00 | 12.69 | O |
| ATOM | 800 | N | GLU | A | 332 | −44.138 | −58.218 | −4.048 | 1.00 | 14.65 | N |
| ATOM | 801 | CA | GLU | A | 332 | −45.223 | −58.692 | −4.969 | 1.00 | 14.25 | C |
| ATOM | 802 | CB | GLU | A | 332 | −46.583 | −57.979 | −4.685 | 1.00 | 12.96 | C |
| ATOM | 803 | CG | GLU | A | 332 | −47.698 | −58.473 | −5.599 | 1.00 | 13.58 | C |
| ATOM | 804 | CD | GLU | A | 332 | −49.044 | −57.755 | −5.360 | 1.00 | 15.93 | C |
| ATOM | 805 | OE1 | GLU | A | 332 | −49.720 | −58.044 | −4.354 | 1.00 | 14.18 | O |
| ATOM | 806 | OE2 | GLU | A | 332 | −49.399 | −56.882 | −6.170 | 1.00 | 16.23 | O |
| ATOM | 807 | C | GLU | A | 332 | −44.813 | −58.519 | −6.423 | 1.00 | 12.55 | C |
| ATOM | 808 | O | GLU | A | 332 | −44.369 | −57.446 | −6.785 | 1.00 | 18.26 | O |
| ATOM | 809 | N | ILE | A | 333 | −44.971 | −59.569 | −7.248 | 1.00 | 11.77 | N |
| ATOM | 810 | CA | ILE | A | 333 | −44.617 | −59.488 | −8.682 | 1.00 | 12.66 | C |
| ATOM | 811 | CB | ILE | A | 333 | −43.724 | −60.681 | −9.143 | 1.00 | 12.54 | C |
| ATOM | 812 | CG1 | ILE | A | 333 | −42.439 | −60.800 | −8.262 | 1.00 | 11.27 | C |
| ATOM | 813 | CD1 | ILE | A | 333 | −41.594 | −59.510 | −8.215 | 1.00 | 15.65 | C |
| ATOM | 814 | CG2 | ILE | A | 333 | −43.337 | −60.517 | −10.620 | 1.00 | 10.92 | C |
| ATOM | 815 | C | ILE | A | 333 | −45.850 | −59.349 | −9.581 | 1.00 | 13.02 | C |
| ATOM | 816 | O | ILE | A | 333 | −45.856 | −58.590 | −10.548 | 1.00 | 16.03 | O |
| ATOM | 817 | N | THR | A | 334 | −46.917 | −60.043 | −9.220 | 1.00 | 11.83 | N |
| ATOM | 818 | CA | THR | A | 334 | −48.164 | −59.925 | −9.950 | 1.00 | 14.76 | C |
| ATOM | 819 | CB | THR | A | 334 | −48.082 | −60.686 | −11.310 | 1.00 | 14.72 | C |
| ATOM | 820 | OG1 | THR | A | 334 | −49.186 | −60.308 | −12.136 | 1.00 | 14.23 | O |
| ATOM | 821 | CG2 | THR | A | 334 | −48.057 | −62.226 | −11.112 | 1.00 | 15.10 | C |
| ATOM | 822 | C | THR | A | 334 | −49.328 | −60.413 | −9.053 | 1.00 | 12.35 | C |
| ATOM | 823 | O | THR | A | 334 | −49.129 | −60.640 | −7.848 | 1.00 | 15.14 | O |
| ATOM | 824 | N | THR | A | 335 | −50.534 | −60.535 | −9.621 | 1.00 | 12.76 | N |
| ATOM | 825 | CA | THR | A | 335 | −51.662 | −61.054 | −8.867 | 1.00 | 13.14 | C |
| ATOM | 826 | CB | THR | A | 335 | −52.692 | −59.967 | −8.437 | 1.00 | 14.35 | C |
| ATOM | 827 | OG1 | THR | A | 335 | −53.497 | −59.558 | −9.575 | 1.00 | 12.57 | O |
| ATOM | 828 | CG2 | THR | A | 335 | −51.994 | −58.788 | −7.779 | 1.00 | 15.81 | C |
| ATOM | 829 | C | THR | A | 335 | −52.364 | −62.035 | −9.762 | 1.00 | 11.61 | C |
| ATOM | 830 | O | THR | A | 335 | −52.243 | −61.959 | −10.963 | 1.00 | 13.44 | O |
| ATOM | 831 | N | LYS | A | 336 | −53.106 | −62.947 | −9.183 | 1.00 | 14.01 | N |
| ATOM | 832 | CA | LYS | A | 336 | −53.911 | −63.897 | −9.953 | 1.00 | 14.50 | C |
| ATOM | 833 | CB | LYS | A | 336 | −54.656 | −64.854 | −9.014 | 1.00 | 19.90 | C |
| ATOM | 834 | CG | LYS | A | 336 | −53.720 | −65.873 | −8.361 | 1.00 | 26.48 | C |
| ATOM | 835 | CD | LYS | A | 336 | −54.439 | −66.632 | −7.243 | 1.00 | 32.77 | C |
| ATOM | 836 | CE | LYS | A | 336 | −53.882 | −68.024 | −7.019 | 1.00 | 39.91 | C |
| ATOM | 837 | NZ | LYS | A | 336 | −54.353 | −68.537 | −5.695 | 1.00 | 36.31 | N |
| ATOM | 838 | C | LYS | A | 336 | −54.909 | −63.230 | −10.836 | 1.00 | 17.46 | C |
| ATOM | 839 | O | LYS | A | 336 | −55.318 | −63.807 | −11.837 | 1.00 | 13.79 | O |
| ATOM | 840 | N | ASN | A | 337 | −55.311 | −62.009 | −10.488 | 1.00 | 13.63 | N |
| ATOM | 841 | CA | ASN | A | 337 | −56.242 | −61.259 | −11.353 | 1.00 | 13.98 | C |
| ATOM | 842 | CB | ASN | A | 337 | −56.684 | −59.930 | −10.701 | 1.00 | 16.05 | C |
| ATOM | 843 | CG | ASN | A | 337 | −57.407 | −60.156 | −9.362 | 1.00 | 20.84 | C |
| ATOM | 844 | OD1 | ASN | A | 337 | −57.010 | −59.636 | −8.335 | 1.00 | 24.54 | O |
| ATOM | 845 | ND2 | ASN | A | 337 | −58.441 | −60.958 | −9.387 | 1.00 | 26.88 | N |
| ATOM | 846 | C | ASN | A | 337 | −55.651 | −60.957 | −12.703 | 1.00 | 13.05 | C |
| ATOM | 847 | O | ASN | A | 337 | −56.401 | −60.739 | −13.667 | 1.00 | 13.64 | O |
| ATOM | 848 | N | GLU | A | 338 | −54.323 | −60.936 | −12.794 | 1.00 | 11.64 | N |
| ATOM | 849 | CA | GLU | A | 338 | −53.629 | −60.552 | −14.110 | 1.00 | 15.66 | C |
| ATOM | 850 | CB | GLU | A | 338 | −52.310 | −59.784 | −13.870 | 1.00 | 13.78 | C |
| ATOM | 851 | CG | GLU | A | 338 | −52.500 | −58.495 | −13.043 | 1.00 | 16.21 | C |
| ATOM | 852 | CD | GLU | A | 338 | −53.585 | −57.598 | −13.601 | 1.00 | 14.33 | C |
| ATOM | 853 | OE1 | GLU | A | 338 | −53.554 | −57.273 | −14.787 | 1.00 | 15.02 | O |
| ATOM | 854 | OE2 | GLU | A | 338 | −54.471 | −57.182 | −12.835 | 1.00 | 26.40 | O |
| ATOM | 855 | C | GLU | A | 338 | −53.404 | −61.709 | −15.088 | 1.00 | 12.62 | C |
| ATOM | 856 | O | GLU | A | 338 | −53.037 | −61.510 | −16.266 | 1.00 | 13.51 | O |
| ATOM | 857 | N | ILE | A | 339 | −53.714 | −62.906 | −14.620 | 1.00 | 14.65 | N |
| ATOM | 858 | CA | ILE | A | 339 | −53.491 | −64.117 | −15.398 | 1.00 | 16.57 | C |
| ATOM | 859 | CB | ILE | A | 339 | −53.714 | −65.420 | −14.538 | 1.00 | 15.59 | C |
| ATOM | 860 | CG1 | ILE | A | 339 | −52.624 | −65.560 | −13.490 | 1.00 | 19.56 | C |
| ATOM | 861 | CD1 | ILE | A | 339 | −53.024 | −66.465 | −12.337 | 1.00 | 22.71 | C |
| ATOM | 862 | CG2 | ILE | A | 339 | −53.696 | −66.687 | −15.429 | 1.00 | 15.60 | C |
| ATOM | 863 | C | ILE | A | 339 | −54.389 | −64.105 | −16.635 | 1.00 | 15.12 | C |
| ATOM | 864 | O | ILE | A | 339 | −55.655 | −63.807 | −16.577 | 1.00 | 11.90 | O |
| ATOM | 865 | N | PHE | A | 340 | −53.769 | −64.397 | −17.786 | 1.00 | 15.90 | N |
| ATOM | 866 | CA | PHE | A | 340 | −54.581 | −64.653 | −18.999 | 1.00 | 14.56 | C |
| ATOM | 867 | CB | PHE | A | 340 | −54.710 | −63.384 | −19.879 | 1.00 | 14.02 | C |
| ATOM | 868 | CG | PHE | A | 340 | −53.483 | −63.084 | −20.674 | 1.00 | 13.78 | C |
| ATOM | 869 | CD1 | PHE | A | 340 | −53.437 | −63.369 | −22.033 | 1.00 | 15.21 | C |
| ATOM | 870 | CE1 | PHE | A | 340 | −52.284 | −63.136 | −22.770 | 1.00 | 15.91 | C |
| ATOM | 871 | CZ | PHE | A | 340 | −51.160 | −62.574 | −22.143 | 1.00 | 13.81 | C |
| ATOM | 872 | CE2 | PHE | A | 340 | −51.196 | −62.263 | −20.783 | 1.00 | 13.46 | C |
| ATOM | 873 | CD2 | PHE | A | 340 | −52.346 | −62.506 | −20.051 | 1.00 | 13.30 | C |

TABLE 4-continued

Atomic coordinates for CRBN(TBD):Pomalidomide (Murine protein)

| ATOM | 874 | C   | PHE | A | 340 | −53.995 | −65.806 | −19.810 | 1.00 | 20.90 | C |
|------|-----|-----|-----|---|-----|---------|---------|---------|------|-------|---|
| ATOM | 875 | O   | PHE | A | 340 | −52.857 | −66.238 | −19.545 | 1.00 | 17.46 | O |
| ATOM | 876 | N   | SER | A | 341 | −54.731 | −66.248 | −20.849 | 1.00 | 18.94 | N |
| ATOM | 877 | CA  | SER | A | 341 | −54.293 | −67.399 | −21.636 | 1.00 | 21.94 | C |
| ATOM | 878 | CB  | SER | A | 341 | −55.365 | −68.482 | −21.564 | 1.00 | 23.78 | C |
| ATOM | 879 | OG  | SER | A | 341 | −54.825 | −69.697 | −21.998 | 1.00 | 38.10 | O |
| ATOM | 880 | C   | SER | A | 341 | −53.938 | −67.073 | −23.114 | 1.00 | 20.34 | C |
| ATOM | 881 | O   | SER | A | 341 | −54.829 | −66.768 | −23.912 | 1.00 | 16.51 | O |
| ATOM | 882 | N   | LEU | A | 342 | −52.648 | −67.163 | −23.467 | 1.00 | 21.10 | N |
| ATOM | 883 | CA  | LEU | A | 342 | −52.153 | −66.752 | −24.817 | 1.00 | 26.95 | C |
| ATOM | 884 | CB  | LEU | A | 342 | −50.691 | −66.195 | −24.749 | 1.00 | 29.01 | C |
| ATOM | 885 | CG  | LEU | A | 342 | −49.887 | −65.440 | −25.846 | 1.00 | 23.73 | C |
| ATOM | 886 | CD1 | LEU | A | 342 | −49.886 | −66.097 | −27.202 | 1.00 | 31.08 | C |
| ATOM | 887 | CD2 | LEU | A | 342 | −50.360 | −63.992 | −26.000 | 1.00 | 36.25 | C |
| ATOM | 888 | C   | LEU | A | 342 | −52.314 | −67.921 | −25.814 | 1.00 | 40.02 | C |
| ATOM | 889 | O   | LEU | A | 342 | −52.954 | −67.757 | −26.868 | 1.00 | 30.34 | O |
| ATOM | 890 | N   | SER | A | 343 | −51.810 | −69.117 | −25.466 | 1.00 | 40.03 | N |
| ATOM | 891 | CA  | SER | A | 343 | −52.131 | −70.316 | −26.283 | 1.00 | 58.91 | C |
| ATOM | 892 | CB  | SER | A | 343 | −51.365 | −71.595 | −25.836 | 1.00 | 71.75 | C |
| ATOM | 893 | OG  | SER | A | 343 | −51.146 | −71.659 | −24.432 | 1.00 | 52.52 | O |
| ATOM | 894 | C   | SER | A | 343 | −53.655 | −70.553 | −26.438 | 1.00 | 57.13 | C |
| ATOM | 895 | O   | SER | A | 343 | −54.284 | −71.305 | −25.691 | 1.00 | 46.48 | O |
| ATOM | 896 | N   | GLU | A | 360 | −45.643 | −74.374 | −16.390 | 1.00 | 32.49 | N |
| ATOM | 897 | CA  | GLU | A | 360 | −44.281 | −73.886 | −16.134 | 1.00 | 44.51 | C |
| ATOM | 898 | CB  | GLU | A | 360 | −43.293 | −74.490 | −17.143 | 1.00 | 49.59 | C |
| ATOM | 899 | CG  | GLU | A | 360 | −41.848 | −73.979 | −17.027 | 1.00 | 63.54 | C |
| ATOM | 900 | CD  | GLU | A | 360 | −40.905 | −74.941 | −16.300 | 1.00 | 83.86 | C |
| ATOM | 901 | OE1 | GLU | A | 360 | −40.491 | −74.620 | −15.158 | 1.00 | 82.15 | O |
| ATOM | 902 | OE2 | GLU | A | 360 | −40.561 | −76.006 | −16.879 | 1.00 | 74.40 | O |
| ATOM | 903 | C   | GLU | A | 360 | −44.179 | −72.336 | −16.160 | 1.00 | 45.72 | C |
| ATOM | 904 | O   | GLU | A | 360 | −43.478 | −71.744 | −15.300 | 1.00 | 27.45 | O |
| ATOM | 905 | N   | THR | A | 361 | −44.841 | −71.714 | −17.161 | 1.00 | 26.30 | N |
| ATOM | 906 | CA  | THR | A | 361 | −44.734 | −70.252 | −17.442 | 1.00 | 23.56 | C |
| ATOM | 907 | CB  | THR | A | 361 | −44.079 | −69.944 | −18.823 | 1.00 | 30.86 | C |
| ATOM | 908 | OG1 | THR | A | 361 | −42.711 | −70.375 | −18.825 | 1.00 | 39.56 | O |
| ATOM | 909 | CG2 | THR | A | 361 | −44.101 | −68.468 | −19.096 | 1.00 | 23.76 | C |
| ATOM | 910 | C   | THR | A | 361 | −46.121 | −69.588 | −17.351 | 1.00 | 20.65 | C |
| ATOM | 911 | O   | THR | A | 361 | −47.022 | −69.889 | −18.089 | 1.00 | 23.89 | O |
| ATOM | 912 | N   | LEU | A | 362 | −46.282 | −68.726 | −16.385 | 1.00 | 19.26 | N |
| ATOM | 913 | CA  | LEU | A | 362 | −47.532 | −68.103 | −16.127 | 1.00 | 17.14 | C |
| ATOM | 914 | CB  | LEU | A | 362 | −47.576 | −67.736 | −14.619 | 1.00 | 18.46 | C |
| ATOM | 915 | CG  | LEU | A | 362 | −48.853 | −67.155 | −14.042 | 1.00 | 25.29 | C |
| ATOM | 916 | CD1 | LEU | A | 362 | −49.979 | −68.162 | −14.175 | 1.00 | 27.14 | C |
| ATOM | 917 | CD2 | LEU | A | 362 | −48.657 | −66.729 | −12.582 | 1.00 | 21.45 | C |
| ATOM | 918 | C   | LEU | A | 362 | −47.503 | −66.834 | −17.012 | 1.00 | 19.54 | C |
| ATOM | 919 | O   | LEU | A | 362 | −46.512 | −66.109 | −17.011 | 1.00 | 19.91 | O |
| ATOM | 920 | N   | THR | A | 363 | −48.573 | −66.576 | −17.758 | 1.00 | 16.23 | N |
| ATOM | 921 | CA  | THR | A | 363 | −48.656 | −65.321 | −18.553 | 1.00 | 12.37 | C |
| ATOM | 922 | CB  | THR | A | 363 | −49.024 | −65.598 | −20.021 | 1.00 | 15.86 | C |
| ATOM | 923 | OG1 | THR | A | 363 | −50.262 | −66.335 | −20.083 | 1.00 | 16.26 | O |
| ATOM | 924 | CG2 | THR | A | 363 | −47.946 | −66.412 | −20.692 | 1.00 | 14.26 | C |
| ATOM | 925 | C   | THR | A | 363 | −49.625 | −64.348 | −17.890 | 1.00 | 13.81 | C |
| ATOM | 926 | O   | THR | A | 363 | −50.767 | −64.710 | −17.544 | 1.00 | 14.48 | O |
| ATOM | 927 | N   | VAL | A | 364 | −49.147 | −63.136 | −17.608 | 1.00 | 13.67 | N |
| ATOM | 928 | CA  | VAL | A | 364 | −49.996 | −62.123 | −16.965 | 1.00 | 11.58 | C |
| ATOM | 929 | CB  | VAL | A | 364 | −49.609 | −61.876 | −15.481 | 1.00 | 10.46 | C |
| ATOM | 930 | CG1 | VAL | A | 364 | −49.882 | −63.113 | −14.620 | 1.00 | 12.05 | C |
| ATOM | 931 | CG2 | VAL | A | 364 | −48.163 | −61.360 | −15.351 | 1.00 | 9.62  | C |
| ATOM | 932 | C   | VAL | A | 364 | −49.922 | −60.783 | −17.745 | 1.00 | 14.58 | C |
| ATOM | 933 | O   | VAL | A | 364 | −48.872 | −60.454 | −18.397 | 1.00 | 14.22 | O |
| ATOM | 934 | N   | TYR | A | 365 | −51.018 | −59.996 | −17.691 | 1.00 | 14.02 | N |
| ATOM | 935 | CA  | TYR | A | 365 | −51.040 | −58.742 | −18.430 | 1.00 | 12.36 | C |
| ATOM | 936 | CB  | TYR | A | 365 | −52.453 | −58.221 | −18.480 | 1.00 | 10.79 | C |
| ATOM | 937 | CG  | TYR | A | 365 | −53.413 | −58.936 | −19.425 | 1.00 | 12.06 | C |
| ATOM | 938 | CD1 | TYR | A | 365 | −53.169 | −58.977 | −20.809 | 1.00 | 9.91  | C |
| ATOM | 939 | CE1 | TYR | A | 365 | −54.065 | −59.550 | −21.682 | 1.00 | 12.14 | C |
| ATOM | 940 | CZ  | TYR | A | 365 | −55.217 | −60.134 | −21.172 | 1.00 | 14.62 | C |
| ATOM | 941 | OH  | TYR | A | 365 | −56.106 | −60.737 | −22.053 | 1.00 | 18.44 | O |
| ATOM | 942 | CE2 | TYR | A | 365 | −55.485 | −60.134 | −19.805 | 1.00 | 12.56 | C |
| ATOM | 943 | CD2 | TYR | A | 365 | −54.571 | −59.536 | −18.931 | 1.00 | 11.47 | C |
| ATOM | 944 | C   | TYR | A | 365 | −50.155 | −57.660 | −17.752 | 1.00 | 12.68 | C |
| ATOM | 945 | O   | TYR | A | 365 | −49.651 | −56.761 | −18.401 | 1.00 | 13.36 | O |
| ATOM | 946 | N   | LYS | A | 366 | −50.056 | −57.718 | −16.424 | 1.00 | 13.78 | N |
| ATOM | 947 | CA  | LYS | A | 366 | −49.429 | −56.657 | −15.657 | 1.00 | 13.39 | C |
| ATOM | 948 | CB  | LYS | A | 366 | −50.504 | −55.745 | −14.989 | 1.00 | 10.99 | C |
| ATOM | 949 | CG  | LYS | A | 366 | −51.286 | −54.841 | −15.996 | 1.00 | 13.26 | C |
| ATOM | 950 | CD  | LYS | A | 366 | −50.398 | −53.644 | −16.206 | 1.00 | 13.36 | C |
| ATOM | 951 | CE  | LYS | A | 366 | −50.722 | −52.698 | −17.307 | 1.00 | 26.30 | C |

TABLE 4-continued

Atomic coordinates for CRBN(TBD):Pomalidomide (Murine protein)

| ATOM | 952 | NZ | LYS | A | 366 | −49.661 | −51.630 | −17.091 | 1.00 | 18.54 | N |
|---|---|---|---|---|---|---|---|---|---|---|---|
| ATOM | 953 | C | LYS | A | 366 | −48.563 | −57.305 | −14.583 | 1.00 | 12.66 | C |
| ATOM | 954 | O | LYS | A | 366 | −48.929 | −58.361 | −14.024 | 1.00 | 14.23 | O |
| ATOM | 955 | N | ALA | A | 367 | −47.462 | −56.629 | −14.242 | 1.00 | 12.60 | N |
| ATOM | 956 | CA | ALA | A | 367 | −46.569 | −57.062 | −13.141 | 1.00 | 13.11 | C |
| ATOM | 957 | CB | ALA | A | 367 | −45.498 | −58.052 | −13.657 | 1.00 | 11.85 | C |
| ATOM | 958 | C | ALA | A | 367 | −45.922 | −55.850 | −12.515 | 1.00 | 11.70 | C |
| ATOM | 959 | O | ALA | A | 367 | −45.972 | −54.755 | −13.090 | 1.00 | 15.34 | O |
| ATOM | 960 | N | SER | A | 368 | −45.309 | −56.038 | −11.337 | 1.00 | 13.49 | N |
| ATOM | 961 | CA | SER | A | 368 | −44.741 | −54.941 | −10.599 | 1.00 | 15.33 | C |
| ATOM | 962 | CB | SER | A | 368 | −45.691 | −54.568 | −9.461 | 1.00 | 12.80 | C |
| ATOM | 963 | OG | SER | A | 368 | −45.979 | −55.712 | −8.613 | 1.00 | 14.96 | O |
| ATOM | 964 | C | SER | A | 368 | −43.394 | −55.294 | −10.028 | 1.00 | 17.57 | C |
| ATOM | 965 | O | SER | A | 368 | −43.087 | −56.509 | −9.751 | 1.00 | 12.24 | O |
| ATOM | 966 | N | ASN | A | 369 | −42.594 | −54.273 | −9.752 | 1.00 | 14.28 | N |
| ATOM | 967 | CA | ASN | A | 369 | −41.326 | −54.509 | −9.008 | 1.00 | 16.30 | C |
| ATOM | 968 | CB | ASN | A | 369 | −41.594 | −55.094 | −7.607 | 1.00 | 14.64 | C |
| ATOM | 969 | CG | ASN | A | 369 | −42.520 | −54.205 | −6.756 | 1.00 | 22.27 | C |
| ATOM | 970 | OD1 | ASN | A | 369 | −43.479 | −54.686 | −6.138 | 1.00 | 22.99 | O |
| ATOM | 971 | ND2 | ASN | A | 369 | −42.233 | −52.924 | −6.719 | 1.00 | 21.01 | N |
| ATOM | 972 | C | ASN | A | 369 | −40.286 | −55.358 | −9.735 | 1.00 | 18.98 | C |
| ATOM | 973 | O | ASN | A | 369 | −39.487 | −56.083 | −9.110 | 1.00 | 14.50 | O |
| ATOM | 974 | N | LEU | A | 370 | −40.273 | −55.239 | −11.051 | 1.00 | 16.99 | N |
| ATOM | 975 | CA | LEU | A | 370 | −39.294 | −55.949 | −11.869 | 1.00 | 12.55 | C |
| ATOM | 976 | CB | LEU | A | 370 | −40.006 | −56.834 | −12.901 | 1.00 | 10.81 | C |
| ATOM | 977 | CG | LEU | A | 370 | −40.747 | −58.106 | −12.387 | 1.00 | 12.87 | C |
| ATOM | 978 | CD1 | LEU | A | 370 | −41.670 | −58.681 | −13.421 | 1.00 | 12.43 | C |
| ATOM | 979 | CD2 | LEU | A | 370 | −39.766 | −59.207 | −11.944 | 1.00 | 12.43 | C |
| ATOM | 980 | C | LEU | A | 370 | −38.423 | −54.956 | −12.610 | 1.00 | 16.72 | C |
| ATOM | 981 | O | LEU | A | 370 | −38.922 | −53.905 | −13.052 | 1.00 | 17.43 | O |
| ATOM | 982 | N | ASN | A | 371 | −37.139 | −55.304 | −12.766 | 1.00 | 14.26 | N |
| ATOM | 983 | CA | ASN | A | 371 | −36.161 | −54.592 | −13.622 | 1.00 | 18.25 | C |
| ATOM | 984 | CB | ASN | A | 371 | −34.777 | −54.482 | −12.909 | 1.00 | 20.24 | C |
| ATOM | 985 | CG | ASN | A | 371 | −34.777 | −53.504 | −11.774 | 1.00 | 24.61 | C |
| ATOM | 986 | OD1 | ASN | A | 371 | −35.582 | −52.586 | −11.736 | 1.00 | 27.12 | O |
| ATOM | 987 | ND2 | ASN | A | 371 | −33.886 | −53.711 | −10.825 | 1.00 | 22.97 | N |
| ATOM | 988 | C | ASN | A | 371 | −35.906 | −55.405 | −14.879 | 1.00 | 17.19 | C |
| ATOM | 989 | O | ASN | A | 371 | −35.697 | −56.616 | −14.815 | 1.00 | 20.36 | O |
| ATOM | 990 | N | LEU | A | 372 | −35.844 | −54.703 | −16.003 | 1.00 | 19.89 | N |
| ATOM | 991 | CA | LEU | A | 372 | −35.594 | −55.278 | −17.302 | 1.00 | 22.70 | C |
| ATOM | 992 | CB | LEU | A | 372 | −36.326 | −54.454 | −18.371 | 1.00 | 23.01 | C |
| ATOM | 993 | CG | LEU | A | 372 | −37.851 | −54.502 | −18.211 | 1.00 | 28.06 | C |
| ATOM | 994 | CD1 | LEU | A | 372 | −38.586 | −53.484 | −19.101 | 1.00 | 23.53 | C |
| ATOM | 995 | CD2 | LEU | A | 372 | −38.309 | −55.944 | −18.422 | 1.00 | 23.50 | C |
| ATOM | 996 | C | LEU | A | 372 | −34.110 | −55.228 | −17.531 | 1.00 | 24.23 | C |
| ATOM | 997 | O | LEU | A | 372 | −33.490 | −54.191 | −17.322 | 1.00 | 23.34 | O |
| ATOM | 998 | N | ILE | A | 373 | −33.536 | −56.368 | −17.912 | 1.00 | 23.65 | N |
| ATOM | 999 | CA | ILE | A | 373 | −32.117 | −56.473 | −18.189 | 1.00 | 25.47 | C |
| ATOM | 1000 | CB | ILE | A | 373 | −31.475 | −57.717 | −17.493 | 1.00 | 25.23 | C |
| ATOM | 1001 | CG1 | ILE | A | 373 | −31.792 | −57.742 | −15.991 | 1.00 | 27.87 | C |
| ATOM | 1002 | CD1 | ILE | A | 373 | −31.115 | −56.644 | −15.192 | 1.00 | 30.17 | C |
| ATOM | 1003 | CG2 | ILE | A | 373 | −29.964 | −57.798 | −17.774 | 1.00 | 20.63 | C |
| ATOM | 1004 | C | ILE | A | 373 | −31.927 | −56.631 | −19.694 | 1.00 | 30.64 | C |
| ATOM | 1005 | O | ILE | A | 373 | −32.381 | −57.622 | −20.281 | 1.00 | 25.80 | O |
| ATOM | 1006 | N | GLY | A | 374 | −31.241 | −55.667 | −20.310 | 1.00 | 40.08 | N |
| ATOM | 1007 | CA | GLY | A | 374 | −30.862 | −55.750 | −21.727 | 1.00 | 29.77 | C |
| ATOM | 1008 | C | GLY | A | 374 | −31.978 | −55.364 | −22.671 | 1.00 | 33.77 | C |
| ATOM | 1009 | O | GLY | A | 374 | −32.931 | −54.638 | −22.288 | 1.00 | 30.25 | O |
| ATOM | 1010 | N | ARG | A | 375 | −31.869 | −55.871 | −23.904 | 1.00 | 31.87 | N |
| ATOM | 1011 | CA | ARG | A | 375 | −32.721 | −55.456 | −25.024 | 1.00 | 35.43 | C |
| ATOM | 1012 | CB | ARG | A | 375 | −31.873 | −54.887 | −26.186 | 1.00 | 40.72 | C |
| ATOM | 1013 | CG | ARG | A | 375 | −30.503 | −54.349 | −25.778 | 1.00 | 49.60 | C |
| ATOM | 1014 | CD | ARG | A | 375 | −29.985 | −53.249 | −26.710 | 1.00 | 56.13 | C |
| ATOM | 1015 | NE | ARG | A | 375 | −30.302 | −53.452 | −28.130 | 1.00 | 56.53 | N |
| ATOM | 1016 | CZ | ARG | A | 375 | −29.766 | −54.398 | −28.908 | 1.00 | 66.94 | C |
| ATOM | 1017 | NH1 | ARG | A | 375 | −28.890 | −55.272 | −28.412 | 1.00 | 57.97 | N |
| ATOM | 1018 | NH2 | ARG | A | 375 | −30.125 | −54.484 | −30.186 | 1.00 | 65.01 | N |
| ATOM | 1019 | C | ARG | A | 375 | −33.524 | −56.651 | −25.509 | 1.00 | 22.72 | C |
| ATOM | 1020 | O | ARG | A | 375 | −33.083 | −57.789 | −25.381 | 1.00 | 23.47 | O |
| ATOM | 1021 | N | PRO | A | 376 | −34.712 | −56.404 | −26.055 | 1.00 | 27.17 | N |
| ATOM | 1022 | CA | PRO | A | 376 | −35.521 | −57.566 | −26.460 | 1.00 | 23.38 | C |
| ATOM | 1023 | CB | PRO | A | 376 | −36.763 | −56.924 | −27.084 | 1.00 | 26.07 | C |
| ATOM | 1024 | CG | PRO | A | 376 | −36.740 | −55.460 | −26.661 | 1.00 | 25.82 | C |
| ATOM | 1025 | CD | PRO | A | 376 | −35.290 | −55.127 | −26.523 | 1.00 | 24.80 | C |
| ATOM | 1026 | C | PRO | A | 376 | −34.791 | −58.473 | −27.499 | 1.00 | 26.42 | C |
| ATOM | 1027 | O | PRO | A | 376 | −34.043 | −57.976 | −28.335 | 1.00 | 23.49 | O |
| ATOM | 1028 | N | SER | A | 377 | −35.023 | −59.781 | −27.440 | 1.00 | 20.17 | N |
| ATOM | 1029 | CA | SER | A | 377 | −34.551 | −60.701 | −28.500 | 1.00 | 16.85 | C |

TABLE 4-continued

Atomic coordinates for CRBN(TBD):Pomalidomide (Murine protein)

| ATOM | 1030 | CB  | SER | A | 377 | −33.404 | −61.574 | −27.980 | 1.00 | 16.67 | C |
| ---- | ---- | --- | --- | - | --- | ------- | ------- | ------- | ---- | ----- | - |
| ATOM | 1031 | OG  | SER | A | 377 | −33.128 | −62.581 | −28.919 | 1.00 | 19.77 | O |
| ATOM | 1032 | C   | SER | A | 377 | −35.707 | −61.620 | −28.924 | 1.00 | 19.59 | C |
| ATOM | 1033 | O   | SER | A | 377 | −36.581 | −61.943 | −28.110 | 1.00 | 18.18 | O |
| ATOM | 1034 | N   | THR | A | 378 | −35.698 | −62.072 | −30.167 | 1.00 | 15.70 | N |
| ATOM | 1035 | CA  | THR | A | 378 | −36.683 | −63.049 | −30.614 | 1.00 | 15.97 | C |
| ATOM | 1036 | CB  | THR | A | 378 | −37.269 | −62.661 | −31.965 | 1.00 | 14.40 | C |
| ATOM | 1037 | OG1 | THR | A | 378 | −36.208 | −62.595 | −32.909 | 1.00 | 13.75 | O |
| ATOM | 1038 | CG2 | THR | A | 378 | −37.942 | −61.270 | −31.897 | 1.00 | 12.82 | C |
| ATOM | 1039 | C   | THR | A | 378 | −36.053 | −64.472 | −30.708 | 1.00 | 14.84 | C |
| ATOM | 1040 | O   | THR | A | 378 | −36.718 | −65.416 | −31.076 | 1.00 | 15.16 | O |
| ATOM | 1041 | N   | VAL | A | 379 | −34.799 | −64.618 | −30.305 | 1.00 | 18.35 | N |
| ATOM | 1042 | CA  | VAL | A | 379 | −34.134 | −65.921 | −30.365 | 1.00 | 18.94 | C |
| ATOM | 1043 | CB  | VAL | A | 379 | −32.648 | −65.844 | −29.923 | 1.00 | 24.44 | C |
| ATOM | 1044 | CG1 | VAL | A | 379 | −31.998 | −67.211 | −30.040 | 1.00 | 24.06 | C |
| ATOM | 1045 | CG2 | VAL | A | 379 | −31.874 | −64.822 | −30.753 | 1.00 | 26.63 | C |
| ATOM | 1046 | C   | VAL | A | 379 | −34.871 | −66.938 | −29.470 | 1.00 | 16.61 | C |
| ATOM | 1047 | O   | VAL | A | 379 | −35.082 | −66.681 | −28.274 | 1.00 | 13.91 | O |
| ATOM | 1048 | N   | HIS | A | 380 | −35.278 | −68.062 | −30.067 | 1.00 | 12.50 | N |
| ATOM | 1049 | CA  | HIS | A | 380 | −35.976 | −69.131 | −29.354 | 1.00 | 16.25 | C |
| ATOM | 1050 | CB  | HIS | A | 380 | −35.040 | −69.790 | −28.313 | 1.00 | 16.87 | C |
| ATOM | 1051 | CG  | HIS | A | 380 | −33.830 | −70.429 | −28.923 | 1.00 | 16.97 | C |
| ATOM | 1052 | ND1 | HIS | A | 380 | −33.915 | −71.281 | −29.960 | 1.00 | 18.68 | N |
| ATOM | 1053 | CE1 | HIS | A | 380 | −32.664 | −71.662 | −30.319 | 1.00 | 15.19 | C |
| ATOM | 1054 | NE2 | HIS | A | 380 | −31.796 | −71.063 | −29.497 | 1.00 | 13.72 | N |
| ATOM | 1055 | CD2 | HIS | A | 380 | −32.472 | −70.288 | −28.632 | 1.00 | 15.25 | C |
| ATOM | 1056 | C   | HIS | A | 380 | −37.230 | −68.686 | −28.654 | 1.00 | 14.99 | C |
| ATOM | 1057 | O   | HIS | A | 380 | −37.635 | −69.304 | −27.656 | 1.00 | 14.35 | O |
| ATOM | 1058 | N   | SER | A | 381 | −37.879 | −67.626 | −29.147 | 1.00 | 17.91 | N |
| ATOM | 1059 | CA  | SER | A | 381 | −39.014 | −67.082 | −28.390 | 1.00 | 16.58 | C |
| ATOM | 1060 | CB  | SER | A | 381 | −39.629 | −65.870 | −29.088 | 1.00 | 15.40 | C |
| ATOM | 1061 | OG  | SER | A | 381 | −40.754 | −65.415 | −28.287 | 1.00 | 15.19 | O |
| ATOM | 1062 | C   | SER | A | 381 | −40.105 | −68.158 | −28.237 | 1.00 | 19.84 | C |
| ATOM | 1063 | O   | SER | A | 381 | −40.519 | −68.779 | −29.231 | 1.00 | 18.86 | O |
| ATOM | 1064 | N   | TRP | A | 382 | −40.582 | −68.372 | −27.014 | 1.00 | 14.81 | N |
| ATOM | 1065 | CA  | TRP | A | 382 | −41.701 | −69.323 | −26.781 | 1.00 | 15.49 | C |
| ATOM | 1066 | CB  | TRP | A | 382 | −41.851 | −69.648 | −25.293 | 1.00 | 14.77 | C |
| ATOM | 1067 | CG  | TRP | A | 382 | −40.588 | −70.187 | −24.692 | 1.00 | 14.91 | C |
| ATOM | 1068 | CD1 | TRP | A | 382 | −39.669 | −71.066 | −25.293 | 1.00 | 18.26 | C |
| ATOM | 1069 | NE1 | TRP | A | 382 | −38.594 | −71.319 | −24.439 | 1.00 | 12.13 | N |
| ATOM | 1070 | CE2 | TRP | A | 382 | −38.762 | −70.665 | −23.270 | 1.00 | 17.46 | C |
| ATOM | 1071 | CD2 | TRP | A | 382 | −40.036 | −69.915 | −23.358 | 1.00 | 14.44 | C |
| ATOM | 1072 | CE3 | TRP | A | 382 | −40.423 | −69.134 | −22.288 | 1.00 | 14.70 | C |
| ATOM | 1073 | CZ3 | TRP | A | 382 | −39.606 | −69.119 | −21.135 | 1.00 | 13.89 | C |
| ATOM | 1074 | CH2 | TRP | A | 382 | −38.414 | −69.852 | −21.063 | 1.00 | 20.20 | C |
| ATOM | 1075 | CZ2 | TRP | A | 382 | −37.976 | −70.649 | −22.131 | 1.00 | 19.45 | C |
| ATOM | 1076 | C   | TRP | A | 382 | −42.999 | −68.836 | −27.308 | 1.00 | 18.88 | C |
| ATOM | 1077 | O   | TRP | A | 382 | −43.952 | −69.597 | −27.394 | 1.00 | 18.02 | O |
| ATOM | 1078 | N   | PHE | A | 383 | −43.070 | −67.553 | −27.663 | 1.00 | 16.56 | N |
| ATOM | 1079 | CA  | PHE | A | 383 | −44.327 | −66.979 | −28.167 | 1.00 | 19.34 | C |
| ATOM | 1080 | CB  | PHE | A | 383 | −44.910 | −65.992 | −27.108 | 1.00 | 17.83 | C |
| ATOM | 1081 | CG  | PHE | A | 383 | −45.151 | −66.647 | −25.789 | 1.00 | 18.66 | C |
| ATOM | 1082 | CD1 | PHE | A | 383 | −46.258 | −67.476 | −25.602 | 1.00 | 20.02 | C |
| ATOM | 1083 | CE1 | PHE | A | 383 | −46.478 | −68.076 | −24.364 | 1.00 | 20.48 | C |
| ATOM | 1084 | CZ  | PHE | A | 383 | −45.582 | −67.883 | −23.330 | 1.00 | 17.66 | C |
| ATOM | 1085 | CE2 | PHE | A | 383 | −44.471 | −67.081 | −23.520 | 1.00 | 19.65 | C |
| ATOM | 1086 | CD2 | PHE | A | 383 | −44.261 | −66.464 | −24.729 | 1.00 | 16.13 | C |
| ATOM | 1087 | C   | PHE | A | 383 | −44.127 | −66.331 | −29.521 | 1.00 | 18.27 | C |
| ATOM | 1088 | O   | PHE | A | 383 | −43.732 | −65.158 | −29.603 | 1.00 | 16.82 | O |
| ATOM | 1089 | N   | PRO | A | 384 | −44.372 | −67.091 | −30.607 | 1.00 | 18.52 | N |
| ATOM | 1090 | CA  | PRO | A | 384 | −44.084 | −66.500 | −31.928 | 1.00 | 19.97 | C |
| ATOM | 1091 | CB  | PRO | A | 384 | −44.671 | −67.532 | −32.916 | 1.00 | 24.72 | C |
| ATOM | 1092 | CG  | PRO | A | 384 | −44.550 | −68.839 | −32.179 | 1.00 | 26.06 | C |
| ATOM | 1093 | CD  | PRO | A | 384 | −44.801 | −68.505 | −30.712 | 1.00 | 23.38 | C |
| ATOM | 1094 | C   | PRO | A | 384 | −44.703 | −65.138 | −32.118 | 1.00 | 19.26 | C |
| ATOM | 1095 | O   | PRO | A | 384 | −45.880 | −64.904 | −31.764 | 1.00 | 21.43 | O |
| ATOM | 1096 | N   | GLY | A | 385 | −43.915 | −64.199 | −32.611 | 1.00 | 17.34 | N |
| ATOM | 1097 | CA  | GLY | A | 385 | −44.446 | −62.856 | −32.775 | 1.00 | 16.74 | C |
| ATOM | 1098 | C   | GLY | A | 385 | −44.047 | −61.926 | −31.651 | 1.00 | 17.50 | C |
| ATOM | 1099 | O   | GLY | A | 385 | −44.235 | −60.711 | −31.760 | 1.00 | 20.19 | O |
| ATOM | 1100 | N   | TYR | A | 386 | −43.470 | −62.468 | −30.582 | 1.00 | 14.44 | N |
| ATOM | 1101 | CA  | TYR | A | 386 | −43.026 | −61.630 | −29.453 | 1.00 | 17.66 | C |
| ATOM | 1102 | CB  | TYR | A | 386 | −43.762 | −62.008 | −28.135 | 1.00 | 14.77 | C |
| ATOM | 1103 | CG  | TYR | A | 386 | −45.239 | −61.680 | −28.080 | 1.00 | 13.34 | C |
| ATOM | 1104 | CD1 | TYR | A | 386 | −45.678 | −60.448 | −27.549 | 1.00 | 16.21 | C |
| ATOM | 1105 | CE1 | TYR | A | 386 | −47.035 | −60.132 | −27.482 | 1.00 | 14.94 | C |
| ATOM | 1106 | CZ  | TYR | A | 386 | −47.966 | −61.076 | −27.932 | 1.00 | 12.65 | C |
| ATOM | 1107 | OH  | TYR | A | 386 | −49.285 | −60.725 | −27.892 | 1.00 | 17.80 | O |

TABLE 4-continued

Atomic coordinates for CRBN(TBD):Pomalidomide (Murine protein)

| ATOM | 1108 | CE2 | TYR | A | 386 | −47.569 | −62.287 | −28.491 | 1.00 | 15.41 | C |
|---|---|---|---|---|---|---|---|---|---|---|---|
| ATOM | 1109 | CD2 | TYR | A | 386 | −46.207 | −62.614 | −28.517 | 1.00 | 14.24 | C |
| ATOM | 1110 | C | TYR | A | 386 | −41.520 | −61.776 | −29.219 | 1.00 | 17.85 | C |
| ATOM | 1111 | O | TYR | A | 386 | −40.938 | −62.851 | −29.484 | 1.00 | 13.88 | O |
| ATOM | 1112 | N | ALA | A | 387 | −40.911 | −60.716 | −28.692 | 1.00 | 14.42 | N |
| ATOM | 1113 | CA | ALA | A | 387 | −39.511 | −60.732 | −28.316 | 1.00 | 15.38 | C |
| ATOM | 1114 | CB | ALA | A | 387 | −38.811 | −59.468 | −28.835 | 1.00 | 16.52 | C |
| ATOM | 1115 | C | ALA | A | 387 | −39.497 | −60.766 | −26.774 | 1.00 | 16.71 | C |
| ATOM | 1116 | O | ALA | A | 387 | −40.475 | −60.395 | −26.152 | 1.00 | 17.57 | O |
| ATOM | 1117 | N | TRP | A | 388 | −38.401 | −61.225 | −26.165 | 1.00 | 18.28 | N |
| ATOM | 1118 | CA | TRP | A | 388 | −38.337 | −61.362 | −24.689 | 1.00 | 17.97 | C |
| ATOM | 1119 | CB | TRP | A | 388 | −38.132 | −62.833 | −24.265 | 1.00 | 15.76 | C |
| ATOM | 1120 | CG | TRP | A | 388 | −36.982 | −63.504 | −24.964 | 1.00 | 15.78 | C |
| ATOM | 1121 | CD1 | TRP | A | 388 | −37.037 | −64.300 | −26.119 | 1.00 | 14.89 | C |
| ATOM | 1122 | NE1 | TRP | A | 388 | −35.756 | −64.772 | −26.447 | 1.00 | 15.14 | N |
| ATOM | 1123 | CE2 | TRP | A | 388 | −34.844 | −64.310 | −25.558 | 1.00 | 15.16 | C |
| ATOM | 1124 | CD2 | TRP | A | 388 | −35.572 | −63.497 | −24.563 | 1.00 | 14.26 | C |
| ATOM | 1125 | CE3 | TRP | A | 388 | −34.855 | −62.911 | −23.521 | 1.00 | 19.41 | C |
| ATOM | 1126 | CZ3 | TRP | A | 388 | −33.461 | −63.131 | −23.444 | 1.00 | 17.01 | C |
| ATOM | 1127 | CH2 | TRP | A | 388 | −32.786 | −63.917 | −24.404 | 1.00 | 17.22 | C |
| ATOM | 1128 | CZ2 | TRP | A | 388 | −33.464 | −64.509 | −25.483 | 1.00 | 18.47 | C |
| ATOM | 1129 | C | TRP | A | 388 | −37.236 | −60.505 | −24.145 | 1.00 | 18.56 | C |
| ATOM | 1130 | O | TRP | A | 388 | −36.283 | −60.232 | −24.835 | 1.00 | 21.53 | O |
| ATOM | 1131 | N | THR | A | 389 | −37.418 | −60.005 | −22.922 | 1.00 | 19.67 | N |
| ATOM | 1132 | CA | THR | A | 389 | −36.392 | −59.249 | −22.210 | 1.00 | 17.49 | C |
| ATOM | 1133 | CB | THR | A | 389 | −36.783 | −57.783 | −22.113 | 1.00 | 17.05 | C |
| ATOM | 1134 | OG1 | THR | A | 389 | −37.002 | −57.255 | −23.435 | 1.00 | 22.08 | O |
| ATOM | 1135 | CG2 | THR | A | 389 | −35.727 | −56.992 | −21.409 | 1.00 | 20.15 | C |
| ATOM | 1136 | C | THR | A | 389 | −36.389 | −59.844 | −20.802 | 1.00 | 19.83 | C |
| ATOM | 1137 | O | THR | A | 389 | −37.456 | −60.041 | −20.208 | 1.00 | 18.79 | O |
| ATOM | 1138 | N | ILE | A | 390 | −35.208 | −60.205 | −20.298 | 1.00 | 19.22 | N |
| ATOM | 1139 | CA | ILE | A | 390 | −35.083 | −60.760 | −18.962 | 1.00 | 17.37 | C |
| ATOM | 1140 | CB | ILE | A | 390 | −33.593 | −61.143 | −18.664 | 1.00 | 19.28 | C |
| ATOM | 1141 | CG1 | ILE | A | 390 | −33.228 | −62.410 | −19.480 | 1.00 | 18.85 | C |
| ATOM | 1142 | CD1 | ILE | A | 390 | −31.828 | −62.958 | −19.263 | 1.00 | 23.45 | C |
| ATOM | 1143 | CG2 | ILE | A | 390 | −33.354 | −61.349 | −17.174 | 1.00 | 14.98 | C |
| ATOM | 1144 | C | ILE | A | 390 | −35.650 | −59.790 | −17.945 | 1.00 | 13.73 | C |
| ATOM | 1145 | O | ILE | A | 390 | −35.416 | −58.597 | −18.031 | 1.00 | 14.66 | O |
| ATOM | 1146 | N | ALA | A | 391 | −36.414 | −60.321 | −16.997 | 1.00 | 15.70 | N |
| ATOM | 1147 | CA | ALA | A | 391 | −37.033 | −59.535 | −15.917 | 1.00 | 18.19 | C |
| ATOM | 1148 | CB | ALA | A | 391 | −38.555 | −59.566 | −16.009 | 1.00 | 15.92 | C |
| ATOM | 1149 | C | ALA | A | 391 | −36.629 | −60.101 | −14.575 | 1.00 | 17.96 | C |
| ATOM | 1150 | O | ALA | A | 391 | −36.987 | −61.248 | −14.243 | 1.00 | 15.71 | O |
| ATOM | 1151 | N | GLN | A | 392 | −36.005 | −59.260 | −13.758 | 1.00 | 14.21 | N |
| ATOM | 1152 | CA | GLN | A | 392 | −35.609 | −59.713 | −12.440 | 1.00 | 16.77 | C |
| ATOM | 1153 | CB | GLN | A | 392 | −34.078 | −59.727 | −12.343 | 1.00 | 19.87 | C |
| ATOM | 1154 | CG | GLN | A | 392 | −33.447 | −58.344 | −12.426 | 1.00 | 19.94 | C |
| ATOM | 1155 | CD | GLN | A | 392 | −31.910 | −58.414 | −12.400 | 1.00 | 26.36 | C |
| ATOM | 1156 | OE1 | GLN | A | 392 | −31.299 | −59.308 | −12.998 | 1.00 | 19.49 | O |
| ATOM | 1157 | NE2 | GLN | A | 392 | −31.297 | −57.483 | −11.705 | 1.00 | 24.80 | N |
| ATOM | 1158 | C | GLN | A | 392 | −36.235 | −58.883 | −11.316 | 1.00 | 16.98 | C |
| ATOM | 1159 | O | GLN | A | 392 | −36.581 | −57.674 | −11.499 | 1.00 | 16.93 | O |
| ATOM | 1160 | N | CYS | A | 393 | −36.411 | −59.508 | −10.158 | 1.00 | 13.99 | N |
| ATOM | 1161 | CA | CYS | A | 393 | −37.019 | −58.802 | −9.012 | 1.00 | 14.50 | C |
| ATOM | 1162 | CB | CYS | A | 393 | −37.076 | −59.758 | −7.808 | 1.00 | 13.21 | C |
| ATOM | 1163 | SG | CYS | A | 393 | −37.495 | −58.995 | −6.243 | 1.00 | 12.92 | S |
| ATOM | 1164 | C | CYS | A | 393 | −36.135 | −57.580 | −8.690 | 1.00 | 15.38 | C |
| ATOM | 1165 | O | CYS | A | 393 | −34.908 | −57.687 | −8.625 | 1.00 | 16.45 | O |
| ATOM | 1166 | N | LYS | A | 394 | −36.748 | −56.411 | −8.504 | 1.00 | 15.64 | N |
| ATOM | 1167 | CA | LYS | A | 394 | −35.959 | −55.216 | −8.263 | 1.00 | 19.52 | C |
| ATOM | 1168 | CB | LYS | A | 394 | −36.811 | −53.942 | −8.432 | 1.00 | 20.04 | C |
| ATOM | 1169 | CG | LYS | A | 394 | −37.774 | −53.659 | −7.306 | 1.00 | 29.57 | C |
| ATOM | 1170 | CD | LYS | A | 394 | −38.365 | −52.237 | −7.449 | 1.00 | 41.91 | C |
| ATOM | 1171 | CE | LYS | A | 394 | −38.830 | −51.660 | −6.107 | 1.00 | 45.12 | C |
| ATOM | 1172 | NZ | LYS | A | 394 | −40.309 | −51.715 | −5.894 | 1.00 | 38.32 | N |
| ATOM | 1173 | C | LYS | A | 394 | −35.304 | −55.244 | −6.856 | 1.00 | 17.29 | C |
| ATOM | 1174 | O | LYS | A | 394 | −34.442 | −54.420 | −6.569 | 1.00 | 14.97 | O |
| ATOM | 1175 | N | ILE | A | 395 | −35.765 | −56.150 | −5.980 | 1.00 | 13.67 | N |
| ATOM | 1176 | CA | ILE | A | 395 | −35.288 | −56.175 | −4.602 | 1.00 | 14.65 | C |
| ATOM | 1177 | CB | ILE | A | 395 | −36.443 | −56.463 | −3.602 | 1.00 | 14.46 | C |
| ATOM | 1178 | CG1 | ILE | A | 395 | −37.460 | −55.282 | −3.603 | 1.00 | 14.67 | C |
| ATOM | 1179 | CD1 | ILE | A | 395 | −36.916 | −54.025 | −2.915 | 1.00 | 23.87 | C |
| ATOM | 1180 | CG2 | ILE | A | 395 | −35.887 | −56.718 | −2.183 | 1.00 | 19.10 | C |
| ATOM | 1181 | C | ILE | A | 395 | −34.111 | −57.137 | −4.409 | 1.00 | 19.30 | C |
| ATOM | 1182 | O | ILE | A | 395 | −33.122 | −56.774 | −3.760 | 1.00 | 20.69 | O |
| ATOM | 1183 | N | CYS | A | 396 | −34.198 | −58.343 | −4.987 | 1.00 | 14.04 | N |
| ATOM | 1184 | CA | CYS | A | 396 | −33.184 | −59.342 | −4.762 | 1.00 | 13.83 | C |
| ATOM | 1185 | CB | CYS | A | 396 | −33.764 | −60.481 | −3.933 | 1.00 | 14.67 | C |

TABLE 4-continued

Atomic coordinates for CRBN(TBD):Pomalidomide (Murine protein)

| ATOM | 1186 | SG | CYS | A | 396 | −34.794 | −61.550 | −4.945 | 1.00 | 14.64 | S |
|---|---|---|---|---|---|---|---|---|---|---|---|
| ATOM | 1187 | C | CYS | A | 396 | −32.530 | −59.830 | −6.058 | 1.00 | 14.71 | C |
| ATOM | 1188 | O | CYS | A | 396 | −31.572 | −60.584 | −6.018 | 1.00 | 15.61 | O |
| ATOM | 1189 | N | ALA | A | 397 | −33.024 | −59.336 | −7.196 | 1.00 | 13.70 | N |
| ATOM | 1190 | CA | ALA | A | 397 | −32.498 | −59.667 | −8.532 | 1.00 | 12.82 | C |
| ATOM | 1191 | CB | ALA | A | 397 | −31.031 | −59.243 | −8.692 | 1.00 | 15.74 | C |
| ATOM | 1192 | C | ALA | A | 397 | −32.715 | −61.136 | −8.965 | 1.00 | 13.16 | C |
| ATOM | 1193 | O | ALA | A | 397 | −32.079 | −61.614 | −9.929 | 1.00 | 13.19 | O |
| ATOM | 1194 | N | SER | A | 398 | −33.594 | −61.842 | −8.271 | 1.00 | 12.64 | N |
| ATOM | 1195 | CA | SER | A | 398 | −33.997 | −63.185 | −8.715 | 1.00 | 16.04 | C |
| ATOM | 1196 | CB | SER | A | 398 | −35.083 | −63.743 | −7.758 | 1.00 | 17.35 | C |
| ATOM | 1197 | OG | SER | A | 398 | −35.610 | −64.966 | −8.243 | 1.00 | 18.64 | O |
| ATOM | 1198 | C | SER | A | 398 | −34.555 | −63.098 | −10.161 | 1.00 | 17.37 | C |
| ATOM | 1199 | O | SER | A | 398 | −35.362 | −62.204 | −10.479 | 1.00 | 13.68 | O |
| ATOM | 1200 | N | HIS | A | 399 | −34.158 | −64.024 | −11.033 | 1.00 | 18.11 | N |
| ATOM | 1201 | CA | HIS | A | 399 | −34.697 | −64.049 | −12.405 | 1.00 | 25.35 | C |
| ATOM | 1202 | CB | HIS | A | 399 | −33.760 | −64.829 | −13.353 | 1.00 | 32.41 | C |
| ATOM | 1203 | CG | HIS | A | 399 | −32.486 | −64.075 | −13.718 | 1.00 | 40.12 | C |
| ATOM | 1204 | ND1 | HIS | A | 399 | −31.730 | −63.421 | −12.799 | 1.00 | 49.50 | N |
| ATOM | 1205 | CE1 | HIS | A | 399 | −30.681 | −62.830 | −13.418 | 1.00 | 57.52 | C |
| ATOM | 1206 | NE2 | HIS | A | 399 | −30.762 | −63.103 | −14.734 | 1.00 | 51.93 | N |
| ATOM | 1207 | CD2 | HIS | A | 399 | −31.856 | −63.875 | −14.954 | 1.00 | 46.42 | C |
| ATOM | 1208 | C | HIS | A | 399 | −36.095 | −64.630 | −12.367 | 1.00 | 21.09 | C |
| ATOM | 1209 | O | HIS | A | 399 | −36.264 | −65.808 | −12.223 | 1.00 | 21.71 | O |
| ATOM | 1210 | N | ILE | A | 400 | −37.120 | −63.793 | −12.470 | 1.00 | 18.37 | N |
| ATOM | 1211 | CA | ILE | A | 400 | −38.482 | −64.281 | −12.251 | 1.00 | 16.01 | C |
| ATOM | 1212 | CB | ILE | A | 400 | −39.415 | −63.176 | −11.680 | 1.00 | 17.40 | C |
| ATOM | 1213 | CG1 | ILE | A | 400 | −38.760 | −62.526 | −10.474 | 1.00 | 18.29 | C |
| ATOM | 1214 | CD1 | ILE | A | 400 | −38.686 | −63.436 | −9.288 | 1.00 | 18.42 | C |
| ATOM | 1215 | CG2 | ILE | A | 400 | −40.862 | −63.726 | −11.418 | 1.00 | 11.98 | C |
| ATOM | 1216 | C | ILE | A | 400 | −39.066 | −64.762 | −13.589 | 1.00 | 17.64 | C |
| ATOM | 1217 | O | ILE | A | 400 | −39.883 | −65.705 | −13.599 | 1.00 | 14.38 | O |
| ATOM | 1218 | N | GLY | A | 401 | −38.680 | −64.078 | −14.681 | 1.00 | 13.14 | N |
| ATOM | 1219 | CA | GLY | A | 401 | −39.159 | −64.407 | −16.055 | 1.00 | 12.65 | C |
| ATOM | 1220 | C | GLY | A | 401 | −38.731 | −63.382 | −17.091 | 1.00 | 14.46 | C |
| ATOM | 1221 | O | GLY | A | 401 | −37.570 | −62.915 | −17.107 | 1.00 | 14.36 | O |
| ATOM | 1222 | N | TRP | A | 402 | −39.669 | −63.021 | −17.964 | 1.00 | 12.19 | N |
| ATOM | 1223 | CA | TRP | A | 402 | −39.391 | −62.188 | −19.134 | 1.00 | 18.04 | C |
| ATOM | 1224 | CB | TRP | A | 402 | −39.149 | −63.081 | −20.384 | 1.00 | 14.45 | C |
| ATOM | 1225 | CG | TRP | A | 402 | −38.043 | −64.080 | −20.144 | 1.00 | 14.71 | C |
| ATOM | 1226 | CD1 | TRP | A | 402 | −36.705 | −63.937 | −20.460 | 1.00 | 16.61 | C |
| ATOM | 1227 | NE1 | TRP | A | 402 | −35.991 | −65.033 | −20.047 | 1.00 | 15.86 | N |
| ATOM | 1228 | CE2 | TRP | A | 402 | −36.802 | −65.933 | −19.444 | 1.00 | 16.72 | C |
| ATOM | 1229 | CD2 | TRP | A | 402 | −38.144 | −65.387 | −19.478 | 1.00 | 16.48 | C |
| ATOM | 1230 | CE3 | TRP | A | 402 | −39.195 | −66.127 | −18.910 | 1.00 | 18.92 | C |
| ATOM | 1231 | CZ3 | TRP | A | 402 | −38.899 | −67.370 | −18.330 | 1.00 | 19.68 | C |
| ATOM | 1232 | CH2 | TRP | A | 402 | −37.589 | −67.886 | −18.324 | 1.00 | 20.14 | C |
| ATOM | 1233 | CZ2 | TRP | A | 402 | −36.519 | −67.177 | −18.882 | 1.00 | 20.08 | C |
| ATOM | 1234 | C | TRP | A | 402 | −40.562 | −61.283 | −19.403 | 1.00 | 14.88 | C |
| ATOM | 1235 | O | TRP | A | 402 | −41.718 | −61.644 | −19.136 | 1.00 | 17.92 | O |
| ATOM | 1236 | N | LYS | A | 403 | −40.266 | −60.095 | −19.904 | 1.00 | 14.10 | N |
| ATOM | 1237 | CA | LYS | A | 403 | −41.273 | −59.239 | −20.523 | 1.00 | 16.30 | C |
| ATOM | 1238 | CB | LYS | A | 403 | −40.853 | −57.786 | −20.400 | 1.00 | 17.15 | C |
| ATOM | 1239 | CG | LYS | A | 403 | −41.971 | −56.782 | −20.679 | 1.00 | 18.91 | C |
| ATOM | 1240 | CD | LYS | A | 403 | −41.451 | −55.357 | −20.842 | 1.00 | 25.96 | C |
| ATOM | 1241 | CE | LYS | A | 403 | −42.623 | −54.372 | −20.750 | 1.00 | 30.89 | C |
| ATOM | 1242 | NZ | LYS | A | 403 | −42.109 | −52.984 | −20.720 | 1.00 | 28.14 | N |
| ATOM | 1243 | C | LYS | A | 403 | −41.318 | −59.646 | −21.999 | 1.00 | 16.99 | C |
| ATOM | 1244 | O | LYS | A | 403 | −40.270 | −59.725 | −22.637 | 1.00 | 17.42 | O |
| ATOM | 1245 | N | PHE | A | 404 | −42.515 | −59.932 | −22.516 | 1.00 | 14.00 | N |
| ATOM | 1246 | CA | PHE | A | 404 | −42.711 | −60.267 | −23.910 | 1.00 | 13.50 | C |
| ATOM | 1247 | CB | PHE | A | 404 | −43.584 | −61.535 | −24.087 | 1.00 | 13.33 | C |
| ATOM | 1248 | CG | PHE | A | 404 | −42.843 | −62.812 | −23.809 | 1.00 | 12.31 | C |
| ATOM | 1249 | CD1 | PHE | A | 404 | −42.048 | −63.415 | −24.810 | 1.00 | 14.09 | C |
| ATOM | 1250 | CE1 | PHE | A | 404 | −41.308 | −64.598 | −24.524 | 1.00 | 16.37 | C |
| ATOM | 1251 | CZ | PHE | A | 404 | −41.342 | −65.165 | −23.239 | 1.00 | 15.21 | C |
| ATOM | 1252 | CE2 | PHE | A | 404 | −42.092 | −64.554 | −22.223 | 1.00 | 12.03 | C |
| ATOM | 1253 | CD2 | PHE | A | 404 | −42.842 | −63.383 | −22.498 | 1.00 | 12.03 | C |
| ATOM | 1254 | C | PHE | A | 404 | −43.332 | −59.082 | −24.623 | 1.00 | 16.14 | C |
| ATOM | 1255 | O | PHE | A | 404 | −44.305 | −58.534 | −24.150 | 1.00 | 16.05 | O |
| ATOM | 1256 | N | THR | A | 405 | −42.707 | −58.640 | −25.715 | 1.00 | 15.96 | N |
| ATOM | 1257 | CA | THR | A | 405 | −43.198 | −57.466 | −26.454 | 1.00 | 16.34 | C |
| ATOM | 1258 | CB | THR | A | 405 | −42.172 | −56.330 | −26.432 | 1.00 | 19.77 | C |
| ATOM | 1259 | OG1 | THR | A | 405 | −40.869 | −56.883 | −26.644 | 1.00 | 22.44 | O |
| ATOM | 1260 | CG2 | THR | A | 405 | −42.181 | −55.642 | −25.059 | 1.00 | 24.07 | C |
| ATOM | 1261 | C | THR | A | 405 | −43.479 | −57.867 | −27.910 | 1.00 | 19.59 | C |
| ATOM | 1262 | O | THR | A | 405 | −42.666 | −58.542 | −28.546 | 1.00 | 18.75 | O |
| ATOM | 1263 | N | ALA | A | 406 | −44.646 | −57.470 | −28.411 | 1.00 | 17.50 | N |

TABLE 4-continued

Atomic coordinates for CRBN(TBD):Pomalidomide (Murine protein)

| ATOM | 1264 | CA | ALA | A | 406 | −45.119 | −57.836 | −29.734 | 1.00 | 17.88 | C |
|---|---|---|---|---|---|---|---|---|---|---|---|
| ATOM | 1265 | CB | ALA | A | 406 | −46.565 | −57.353 | −29.919 | 1.00 | 15.89 | C |
| ATOM | 1266 | C | ALA | A | 406 | −44.229 | −57.181 | −30.784 | 1.00 | 19.22 | C |
| ATOM | 1267 | O | ALA | A | 406 | −43.913 | −56.035 | −30.644 | 1.00 | 16.64 | O |
| ATOM | 1268 | N | THR | A | 407 | −43.816 | −57.924 | −31.821 | 1.00 | 18.73 | N |
| ATOM | 1269 | CA | THR | A | 407 | −43.056 | −57.321 | −32.919 | 1.00 | 18.40 | C |
| ATOM | 1270 | CB | THR | A | 407 | −42.168 | −58.351 | −33.638 | 1.00 | 22.40 | C |
| ATOM | 1271 | OG1 | THR | A | 407 | −42.999 | −59.417 | −34.108 | 1.00 | 22.23 | O |
| ATOM | 1272 | CG2 | THR | A | 407 | −41.142 | −58.893 | −32.723 | 1.00 | 17.33 | C |
| ATOM | 1273 | C | THR | A | 407 | −43.937 | −56.634 | −33.984 | 1.00 | 25.13 | C |
| ATOM | 1274 | O | THR | A | 407 | −43.425 | −55.847 | −34.781 | 1.00 | 27.79 | O |
| ATOM | 1275 | N | LYS | A | 408 | −45.237 | −56.956 | −34.027 | 1.00 | 23.64 | N |
| ATOM | 1276 | CA | LYS | A | 408 | −46.195 | −56.289 | −34.937 | 1.00 | 27.76 | C |
| ATOM | 1277 | CB | LYS | A | 408 | −46.800 | −57.289 | −35.941 | 1.00 | 32.50 | C |
| ATOM | 1278 | CG | LYS | A | 408 | −45.810 | −57.843 | −36.965 | 1.00 | 39.28 | C |
| ATOM | 1279 | CD | LYS | A | 408 | −46.185 | −59.248 | −37.414 | 1.00 | 52.03 | C |
| ATOM | 1280 | CE | LYS | A | 408 | −46.850 | −59.275 | −38.784 | 1.00 | 49.43 | C |
| ATOM | 1281 | NZ | LYS | A | 408 | −48.242 | −58.743 | −38.745 | 1.00 | 53.48 | N |
| ATOM | 1282 | C | LYS | A | 408 | −47.322 | −55.557 | −34.183 | 1.00 | 28.58 | C |
| ATOM | 1283 | O | LYS | A | 408 | −47.872 | −56.063 | −33.179 | 1.00 | 20.88 | O |
| ATOM | 1284 | N | LYS | A | 409 | −47.708 | −54.397 | −34.708 | 1.00 | 21.40 | N |
| ATOM | 1285 | CA | LYS | A | 409 | −48.651 | −53.535 | −34.028 | 1.00 | 24.82 | C |
| ATOM | 1286 | CB | LYS | A | 409 | −48.628 | −52.139 | −34.646 | 1.00 | 29.84 | C |
| ATOM | 1287 | CG | LYS | A | 409 | −47.344 | −51.364 | −34.352 | 1.00 | 46.09 | C |
| ATOM | 1288 | CD | LYS | A | 409 | −47.648 | −49.919 | −33.965 | 1.00 | 48.46 | C |
| ATOM | 1289 | CE | LYS | A | 409 | −46.821 | −48.926 | −34.776 | 1.00 | 62.40 | C |
| ATOM | 1290 | NZ | LYS | A | 409 | −45.356 | −49.065 | −34.529 | 1.00 | 68.67 | N |
| ATOM | 1291 | C | LYS | A | 409 | −50.083 | −54.085 | −34.001 | 1.00 | 20.47 | C |
| ATOM | 1292 | O | LYS | A | 409 | −50.878 | −53.670 | −33.175 | 1.00 | 22.28 | O |
| ATOM | 1293 | N | ASP | A | 410 | −50.408 | −55.024 | −34.883 | 1.00 | 19.43 | N |
| ATOM | 1294 | CA | ASP | A | 410 | −51.781 | −55.566 | −34.924 | 1.00 | 25.03 | C |
| ATOM | 1295 | CB | ASP | A | 410 | −52.167 | −56.011 | −36.349 | 1.00 | 27.05 | C |
| ATOM | 1296 | CG | ASP | A | 410 | −51.265 | −57.127 | −36.894 | 1.00 | 37.79 | C |
| ATOM | 1297 | OD1 | ASP | A | 410 | −50.301 | −57.535 | −36.218 | 1.00 | 53.46 | O |
| ATOM | 1298 | OD2 | ASP | A | 410 | −51.524 | −57.607 | −38.006 | 1.00 | 42.24 | O |
| ATOM | 1299 | C | ASP | A | 410 | −52.043 | −56.700 | −33.917 | 1.00 | 21.12 | C |
| ATOM | 1300 | O | ASP | A | 410 | −53.138 | −57.263 | −33.873 | 1.00 | 25.62 | O |
| ATOM | 1301 | N | MET | A | 411 | −51.034 | −57.055 | −33.127 | 1.00 | 21.32 | N |
| ATOM | 1302 | CA | MET | A | 411 | −51.183 | −58.116 | −32.116 | 1.00 | 23.21 | C |
| ATOM | 1303 | CB | MET | A | 411 | −49.822 | −58.747 | −31.851 | 1.00 | 18.74 | C |
| ATOM | 1304 | CG | MET | A | 411 | −49.227 | −59.295 | −33.124 | 1.00 | 23.21 | C |
| ATOM | 1305 | SD | MET | A | 411 | −47.764 | −60.215 | −32.684 | 1.00 | 27.39 | S |
| ATOM | 1306 | CE | MET | A | 411 | −46.446 | −59.149 | −33.164 | 1.00 | 23.85 | C |
| ATOM | 1307 | C | MET | A | 411 | −51.784 | −57.607 | −30.794 | 1.00 | 19.87 | C |
| ATOM | 1308 | O | MET | A | 411 | −51.713 | −56.403 | −30.486 | 1.00 | 20.22 | O |
| ATOM | 1309 | N | SER | A | 412 | −52.405 | −58.502 | −30.024 | 1.00 | 16.83 | N |
| ATOM | 1310 | CA | SER | A | 412 | −52.854 | −58.127 | −28.666 | 1.00 | 19.04 | C |
| ATOM | 1311 | CB | SER | A | 412 | −54.354 | −57.793 | −28.612 | 1.00 | 19.35 | C |
| ATOM | 1312 | OG | SER | A | 412 | −55.128 | −58.890 | −29.067 | 1.00 | 19.95 | O |
| ATOM | 1313 | C | SER | A | 412 | −52.459 | −59.266 | −27.731 | 1.00 | 16.67 | C |
| ATOM | 1314 | O | SER | A | 412 | −52.666 | −60.437 | −28.130 | 1.00 | 17.24 | O |
| ATOM | 1315 | N | PRO | A | 413 | −52.336 | −58.953 | −26.424 | 1.00 | 13.18 | N |
| ATOM | 1316 | CA | PRO | A | 413 | −51.617 | −57.729 | −25.960 | 1.00 | 15.23 | C |
| ATOM | 1317 | CB | PRO | A | 413 | −51.320 | −58.032 | −24.481 | 1.00 | 14.93 | C |
| ATOM | 1318 | CG | PRO | A | 413 | −51.089 | −59.522 | −24.453 | 1.00 | 13.07 | C |
| ATOM | 1319 | CD | PRO | A | 413 | −51.910 | −60.138 | −25.605 | 1.00 | 11.36 | C |
| ATOM | 1320 | C | PRO | A | 413 | −50.349 | −57.333 | −26.702 | 1.00 | 14.82 | C |
| ATOM | 1321 | O | PRO | A | 413 | −49.639 | −58.188 | −27.174 | 1.00 | 16.68 | O |
| ATOM | 1322 | N | GLN | A | 414 | −50.052 | −56.032 | −26.746 | 1.00 | 13.59 | N |
| ATOM | 1323 | CA | GLN | A | 414 | −48.750 | −55.555 | −27.217 | 1.00 | 17.30 | C |
| ATOM | 1324 | CB | GLN | A | 414 | −48.769 | −54.031 | −27.440 | 1.00 | 20.46 | C |
| ATOM | 1325 | CG | GLN | A | 414 | −49.522 | −53.599 | −28.720 | 1.00 | 15.19 | C |
| ATOM | 1326 | CD | GLN | A | 414 | −48.791 | −54.074 | −29.979 | 1.00 | 17.58 | C |
| ATOM | 1327 | OE1 | GLN | A | 414 | −49.239 | −54.981 | −30.703 | 1.00 | 20.26 | O |
| ATOM | 1328 | NE2 | GLN | A | 414 | −47.647 | −53.508 | −30.202 | 1.00 | 16.26 | N |
| ATOM | 1329 | C | GLN | A | 414 | −47.576 | −55.972 | −26.311 | 1.00 | 16.74 | C |
| ATOM | 1330 | O | GLN | A | 414 | −46.423 | −56.091 | −26.764 | 1.00 | 18.40 | O |
| ATOM | 1331 | N | LYS | A | 415 | −47.859 | −56.197 | −25.027 | 1.00 | 18.31 | N |
| ATOM | 1332 | CA | LYS | A | 415 | −46.860 | −56.743 | −24.130 | 1.00 | 18.39 | C |
| ATOM | 1333 | CB | LYS | A | 415 | −45.905 | −55.635 | −23.559 | 1.00 | 22.73 | C |
| ATOM | 1334 | CG | LYS | A | 415 | −46.502 | −54.706 | −22.523 | 1.00 | 19.40 | C |
| ATOM | 1335 | CD | LYS | A | 415 | −46.352 | −55.249 | −21.077 | 1.00 | 26.70 | C |
| ATOM | 1336 | CE | LYS | A | 415 | −47.327 | −54.495 | −20.148 | 1.00 | 22.76 | C |
| ATOM | 1337 | NZ | LYS | A | 415 | −47.747 | −53.243 | −20.781 | 1.00 | 23.26 | N |
| ATOM | 1338 | C | LYS | A | 415 | −47.537 | −57.573 | −23.034 | 1.00 | 13.21 | C |
| ATOM | 1339 | O | LYS | A | 415 | −48.729 | −57.408 | −22.755 | 1.00 | 10.23 | O |
| ATOM | 1340 | N | PHE | A | 416 | −46.799 | −58.523 | −22.505 | 1.00 | 11.61 | N |
| ATOM | 1341 | CA | PHE | A | 416 | −47.244 | −59.267 | −21.333 | 1.00 | 12.74 | C |

TABLE 4-continued

Atomic coordinates for CRBN(TBD):Pomalidomide (Murine protein)

| ATOM | 1342 | CB | PHE | A | 416 | −48.214 | −60.453 | −21.671 | 1.00 | 12.29 | C |
|------|------|-----|-----|---|-----|---------|---------|---------|------|-------|---|
| ATOM | 1343 | CG | PHE | A | 416 | −47.590 | −61.535 | −22.534 | 1.00 | 14.03 | C |
| ATOM | 1344 | CD1 | PHE | A | 416 | −47.044 | −62.683 | −21.963 | 1.00 | 11.00 | C |
| ATOM | 1345 | CE1 | PHE | A | 416 | −46.453 | −63.677 | −22.750 | 1.00 | 13.79 | C |
| ATOM | 1346 | CZ | PHE | A | 416 | −46.358 | −63.526 | −24.128 | 1.00 | 16.73 | C |
| ATOM | 1347 | CE2 | PHE | A | 416 | −46.881 | −62.388 | −24.729 | 1.00 | 15.15 | C |
| ATOM | 1348 | CD2 | PHE | A | 416 | −47.506 | −61.379 | −23.930 | 1.00 | 14.19 | C |
| ATOM | 1349 | C | PHE | A | 416 | −45.969 | −59.755 | −20.607 | 1.00 | 14.10 | C |
| ATOM | 1350 | O | PHE | A | 416 | −44.851 | −59.455 | −21.025 | 1.00 | 14.39 | O |
| ATOM | 1351 | N | TRP | A | 417 | −46.166 | −60.372 | −19.450 | 1.00 | 14.54 | N |
| ATOM | 1352 | CA | TRP | A | 417 | −45.080 | −60.976 | −18.707 | 1.00 | 14.28 | C |
| ATOM | 1353 | CB | TRP | A | 417 | −45.028 | −60.431 | −17.261 | 1.00 | 14.42 | C |
| ATOM | 1354 | CG | TRP | A | 417 | −44.951 | −58.914 | −17.226 | 1.00 | 13.79 | C |
| ATOM | 1355 | CD1 | TRP | A | 417 | −46.012 | −58.004 | −17.351 | 1.00 | 16.30 | C |
| ATOM | 1356 | NE1 | TRP | A | 417 | −45.540 | −56.709 | −17.289 | 1.00 | 14.75 | N |
| ATOM | 1357 | CE2 | TRP | A | 417 | −44.203 | −56.697 | −17.104 | 1.00 | 15.15 | C |
| ATOM | 1358 | CD2 | TRP | A | 417 | −43.755 | −58.088 | −17.052 | 1.00 | 11.55 | C |
| ATOM | 1359 | CE3 | TRP | A | 417 | −42.394 | −58.358 | −16.945 | 1.00 | 11.45 | C |
| ATOM | 1360 | CZ3 | TRP | A | 417 | −41.513 | −57.306 | −16.826 | 1.00 | 15.81 | C |
| ATOM | 1361 | CH2 | TRP | A | 417 | −41.966 | −55.946 | −16.837 | 1.00 | 14.85 | C |
| ATOM | 1362 | CZ2 | TRP | A | 417 | −43.308 | −55.627 | −17.025 | 1.00 | 16.31 | C |
| ATOM | 1363 | C | TRP | A | 417 | −45.232 | −62.461 | −18.712 | 1.00 | 13.11 | C |
| ATOM | 1364 | O | TRP | A | 417 | −46.285 | −62.995 | −18.385 | 1.00 | 14.99 | O |
| ATOM | 1365 | N | GLY | A | 418 | −44.166 | −63.160 | −19.055 | 1.00 | 13.45 | N |
| ATOM | 1366 | CA | GLY | A | 418 | −44.159 | −64.603 | −18.858 | 1.00 | 10.80 | C |
| ATOM | 1367 | C | GLY | A | 418 | −43.286 | −64.954 | −17.654 | 1.00 | 12.58 | C |
| ATOM | 1368 | O | GLY | A | 418 | −42.072 | −64.723 | −17.655 | 1.00 | 13.15 | O |
| ATOM | 1369 | N | LEU | A | 419 | −43.883 | −65.551 | −16.643 | 1.00 | 11.11 | N |
| ATOM | 1370 | CA | LEU | A | 419 | −43.179 | −65.666 | −15.360 | 1.00 | 12.41 | C |
| ATOM | 1371 | CB | LEU | A | 419 | −43.931 | −64.862 | −14.256 | 1.00 | 11.30 | C |
| ATOM | 1372 | CG | LEU | A | 419 | −44.231 | −63.346 | −14.510 | 1.00 | 11.74 | C |
| ATOM | 1373 | CD1 | LEU | A | 419 | −45.115 | −62.735 | −13.386 | 1.00 | 14.81 | C |
| ATOM | 1374 | CD2 | LEU | A | 419 | −42.946 | −62.531 | −14.571 | 1.00 | 13.02 | C |
| ATOM | 1375 | C | LEU | A | 419 | −42.991 | −67.136 | −14.975 | 1.00 | 13.87 | C |
| ATOM | 1376 | O | LEU | A | 419 | −43.896 | −67.951 | −15.119 | 1.00 | 15.45 | O |
| ATOM | 1377 | N | THR | A | 420 | −41.807 | −67.490 | −14.525 | 1.00 | 15.12 | N |
| ATOM | 1378 | CA | THR | A | 420 | −41.585 | −68.881 | −14.080 | 1.00 | 15.23 | C |
| ATOM | 1379 | CB | THR | A | 420 | −40.085 | −69.120 | −13.917 | 1.00 | 18.49 | C |
| ATOM | 1380 | OG1 | THR | A | 420 | −39.446 | −68.724 | −15.142 | 1.00 | 15.51 | O |
| ATOM | 1381 | CG2 | THR | A | 420 | −39.818 | −70.609 | −13.604 | 1.00 | 18.00 | C |
| ATOM | 1382 | C | THR | A | 420 | −42.339 | −69.166 | −12.777 | 1.00 | 17.79 | C |
| ATOM | 1383 | O | THR | A | 420 | −42.063 | −68.507 | −11.734 | 1.00 | 16.83 | O |
| ATOM | 1384 | N | ARG | A | 421 | −43.301 | −70.117 | −12.810 | 1.00 | 13.41 | N |
| ATOM | 1385 | CA | ARG | A | 421 | −44.232 | −70.286 | −11.664 | 1.00 | 17.69 | C |
| ATOM | 1386 | CB | ARG | A | 421 | −45.220 | −71.433 | −11.890 | 1.00 | 22.23 | C |
| ATOM | 1387 | CG | ARG | A | 421 | −46.292 | −71.179 | −12.897 | 1.00 | 31.08 | C |
| ATOM | 1388 | CD | ARG | A | 421 | −47.075 | −72.459 | −13.197 | 1.00 | 41.71 | C |
| ATOM | 1389 | NE | ARG | A | 421 | −48.203 | −72.193 | −14.089 | 1.00 | 42.91 | N |
| ATOM | 1390 | CZ | ARG | A | 421 | −49.461 | −72.013 | −13.684 | 1.00 | 51.48 | C |
| ATOM | 1391 | NH1 | ARG | A | 421 | −49.775 | −72.099 | −12.395 | 1.00 | 48.96 | N |
| ATOM | 1392 | NH2 | ARG | A | 421 | −50.411 | −71.764 | −14.575 | 1.00 | 47.16 | N |
| ATOM | 1393 | C | ARG | A | 421 | −43.452 | −70.627 | −10.389 | 1.00 | 18.11 | C |
| ATOM | 1394 | O | ARG | A | 421 | −43.872 | −70.294 | −9.275 | 1.00 | 20.48 | O |
| ATOM | 1395 | N | SER | A | 422 | −42.360 | −71.371 | −10.549 | 1.00 | 17.48 | N |
| ATOM | 1396 | CA | SER | A | 422 | −41.601 | −71.869 | −9.384 | 1.00 | 19.10 | C |
| ATOM | 1397 | CB | SER | A | 422 | −40.757 | −73.098 | −9.778 | 1.00 | 18.85 | C |
| ATOM | 1398 | OG | SER | A | 422 | −39.712 | −72.731 | −10.659 | 1.00 | 29.04 | O |
| ATOM | 1399 | C | SER | A | 422 | −40.744 | −70.761 | −8.755 | 1.00 | 18.22 | C |
| ATOM | 1400 | O | SER | A | 422 | −40.231 | −70.933 | −7.658 | 1.00 | 16.37 | O |
| ATOM | 1401 | N | ALA | A | 423 | −40.645 | −69.600 | −9.420 | 1.00 | 14.40 | N |
| ATOM | 1402 | CA | ALA | A | 423 | −39.974 | −68.412 | −8.827 | 1.00 | 14.17 | C |
| ATOM | 1403 | CB | ALA | A | 423 | −39.237 | −67.612 | −9.920 | 1.00 | 16.41 | C |
| ATOM | 1404 | C | ALA | A | 423 | −40.936 | −67.491 | −8.063 | 1.00 | 13.31 | C |
| ATOM | 1405 | O | ALA | A | 423 | −40.542 | −66.430 | −7.595 | 1.00 | 13.94 | O |
| ATOM | 1406 | N | LEU | A | 424 | −42.187 | −67.893 | −7.940 | 1.00 | 12.23 | N |
| ATOM | 1407 | CA | LEU | A | 424 | −43.195 | −67.081 | −7.242 | 1.00 | 13.18 | C |
| ATOM | 1408 | CB | LEU | A | 424 | −44.336 | −66.728 | −8.207 | 1.00 | 12.82 | C |
| ATOM | 1409 | CG | LEU | A | 424 | −43.987 | −65.811 | −9.380 | 1.00 | 14.65 | C |
| ATOM | 1410 | CD1 | LEU | A | 424 | −45.189 | −65.723 | −10.333 | 1.00 | 17.24 | C |
| ATOM | 1411 | CD2 | LEU | A | 424 | −43.713 | −64.395 | −8.839 | 1.00 | 18.67 | C |
| ATOM | 1412 | C | LEU | A | 424 | −43.752 | −67.875 | −6.074 | 1.00 | 16.98 | C |
| ATOM | 1413 | O | LEU | A | 424 | −43.751 | −69.123 | −6.091 | 1.00 | 16.48 | O |
| ATOM | 1414 | N | LEU | A | 425 | −44.216 | −67.176 | −5.069 | 1.00 | 14.07 | N |
| ATOM | 1415 | CA | LEU | A | 425 | −44.803 | −67.809 | −3.906 | 1.00 | 21.99 | C |
| ATOM | 1416 | CB | LEU | A | 425 | −44.232 | −67.138 | −2.665 | 1.00 | 21.97 | C |
| ATOM | 1417 | CG | LEU | A | 425 | −43.608 | −67.814 | −1.472 | 1.00 | 31.87 | C |
| ATOM | 1418 | CD1 | LEU | A | 425 | −43.468 | −66.716 | −0.422 | 1.00 | 20.48 | C |
| ATOM | 1419 | CD2 | LEU | A | 425 | −44.389 | −69.033 | −0.964 | 1.00 | 31.12 | C |

TABLE 4-continued

Atomic coordinates for CRBN(TBD):Pomalidomide (Murine protein)

| ATOM | 1420 | C   | LEU | A | 425 | −46.377 | −67.652 | −4.010  | 1.00 | 34.82 | C |
|------|------|-----|-----|---|-----|---------|---------|---------|------|-------|---|
| ATOM | 1421 | O   | LEU | A | 425 | −46.850 | −66.703 | −4.622  | 1.00 | 38.21 | O |
| ATOM | 1422 | N   | PRO | A | 426 | −47.164 | −68.496 | −3.298  | 1.00 | 41.26 | N |
| ATOM | 1423 | CA  | PRO | A | 426 | −48.220 | −69.302 | −3.850  | 1.00 | 44.73 | C |
| ATOM | 1424 | CB  | PRO | A | 426 | −49.415 | −68.334 | −3.860  | 1.00 | 38.18 | C |
| ATOM | 1425 | CG  | PRO | A | 426 | −49.134 | −67.404 | −2.690  | 1.00 | 50.70 | C |
| ATOM | 1426 | CD  | PRO | A | 426 | −47.735 | −67.745 | −2.166  | 1.00 | 63.24 | C |
| ATOM | 1427 | C   | PRO | A | 426 | −47.871 | −69.792 | −5.238  | 1.00 | 54.85 | C |
| ATOM | 1428 | O   | PRO | A | 426 | −46.919 | −70.554 | −5.368  | 1.00 | 49.22 | O |
| ATOM | 1429 | N   | THR | B | 321 | −63.112 | −67.864 | −14.901 | 1.00 | 33.78 | N |
| ATOM | 1430 | CA  | THR | B | 321 | −63.075 | −66.430 | −15.388 | 1.00 | 31.09 | C |
| ATOM | 1431 | CB  | THR | B | 321 | −61.978 | −65.597 | −14.690 | 1.00 | 28.86 | C |
| ATOM | 1432 | OG1 | THR | B | 321 | −60.710 | −66.148 | −15.012 | 1.00 | 30.56 | O |
| ATOM | 1433 | CG2 | THR | B | 321 | −62.179 | −65.466 | −13.138 | 1.00 | 26.79 | C |
| ATOM | 1434 | C   | THR | B | 321 | −62.843 | −66.243 | −16.930 | 1.00 | 27.83 | C |
| ATOM | 1435 | O   | THR | B | 321 | −62.911 | −65.125 | −17.415 | 1.00 | 28.51 | O |
| ATOM | 1436 | N   | SER | B | 322 | −62.525 | −67.294 | −17.681 | 1.00 | 24.96 | N |
| ATOM | 1437 | CA  | SER | B | 322 | −62.224 | −67.092 | −19.119 | 1.00 | 22.39 | C |
| ATOM | 1438 | CB  | SER | B | 322 | −61.481 | −68.277 | −19.706 | 1.00 | 21.11 | C |
| ATOM | 1439 | OG  | SER | B | 322 | −60.230 | −68.354 | −19.125 | 1.00 | 25.01 | O |
| ATOM | 1440 | C   | SER | B | 322 | −63.437 | −66.756 | −19.998 | 1.00 | 24.86 | C |
| ATOM | 1441 | O   | SER | B | 322 | −64.502 | −67.367 | −19.877 | 1.00 | 22.17 | O |
| ATOM | 1442 | N   | LEU | B | 323 | −63.244 | −65.805 | −20.908 | 1.00 | 21.57 | N |
| ATOM | 1443 | CA  | LEU | B | 323 | −64.214 | −65.466 | −21.921 | 1.00 | 19.66 | C |
| ATOM | 1444 | CB  | LEU | B | 323 | −64.615 | −63.993 | −21.788 | 1.00 | 17.99 | C |
| ATOM | 1445 | CG  | LEU | B | 323 | −65.210 | −63.555 | −20.442 | 1.00 | 18.68 | C |
| ATOM | 1446 | CD1 | LEU | B | 323 | −65.404 | −62.051 | −20.416 | 1.00 | 21.42 | C |
| ATOM | 1447 | CD2 | LEU | B | 323 | −66.561 | −64.221 | −20.268 | 1.00 | 27.45 | C |
| ATOM | 1448 | C   | LEU | B | 323 | −63.599 | −65.749 | −23.294 | 1.00 | 18.51 | C |
| ATOM | 1449 | O   | LEU | B | 323 | −62.585 | −65.155 | −23.671 | 1.00 | 16.79 | O |
| ATOM | 1450 | N   | CYS | B | 324 | −64.180 | −66.712 | −24.001 | 1.00 | 22.68 | N |
| ATOM | 1451 | CA  | CYS | B | 324 | −63.598 | −67.231 | −25.232 | 1.00 | 19.29 | C |
| ATOM | 1452 | CB  | CYS | B | 324 | −63.475 | −68.767 | −25.167 | 1.00 | 20.03 | C |
| ATOM | 1453 | SG  | CYS | B | 324 | −62.230 | −69.313 | −23.967 | 1.00 | 23.16 | S |
| ATOM | 1454 | C   | CYS | B | 324 | −64.400 | −66.823 | −26.449 | 1.00 | 20.35 | C |
| ATOM | 1455 | O   | CYS | B | 324 | −65.613 | −66.568 | −26.353 | 1.00 | 21.65 | O |
| ATOM | 1456 | N   | CYS | B | 325 | −63.726 | −66.780 | −27.599 | 1.00 | 16.20 | N |
| ATOM | 1457 | CA  | CYS | B | 325 | −64.403 | −66.646 | −28.865 | 1.00 | 21.02 | C |
| ATOM | 1458 | CB  | CYS | B | 325 | −63.383 | −66.747 | −30.006 | 1.00 | 16.21 | C |
| ATOM | 1459 | SG  | CYS | B | 325 | −64.155 | −66.812 | −31.626 | 1.00 | 21.06 | S |
| ATOM | 1460 | C   | CYS | B | 325 | −65.497 | −67.747 | −28.995 | 1.00 | 19.82 | C |
| ATOM | 1461 | O   | CYS | B | 325 | −65.228 | −68.938 | −28.817 | 1.00 | 20.13 | O |
| ATOM | 1462 | N   | LYS | B | 326 | −66.723 | −67.329 | −29.296 | 1.00 | 24.90 | N |
| ATOM | 1463 | CA  | LYS | B | 326 | −67.845 | −68.259 | −29.435 | 1.00 | 23.55 | C |
| ATOM | 1464 | CB  | LYS | B | 326 | −69.154 | −67.477 | −29.564 | 1.00 | 26.30 | C |
| ATOM | 1465 | CG  | LYS | B | 326 | −70.423 | −68.318 | −29.483 | 1.00 | 31.03 | C |
| ATOM | 1466 | CD  | LYS | B | 326 | −71.680 | −67.456 | −29.644 | 1.00 | 32.09 | C |
| ATOM | 1467 | CE  | LYS | B | 326 | −71.884 | −66.999 | −31.093 | 1.00 | 39.28 | C |
| ATOM | 1468 | NZ  | LYS | B | 326 | −73.207 | −66.332 | −31.311 | 1.00 | 47.98 | N |
| ATOM | 1469 | C   | LYS | B | 326 | −67.649 | −69.199 | −30.645 | 1.00 | 24.85 | C |
| ATOM | 1470 | O   | LYS | B | 326 | −68.044 | −70.380 | −30.603 | 1.00 | 23.29 | O |
| ATOM | 1471 | N   | GLN | B | 327 | −67.012 | −68.689 | −31.703 | 1.00 | 22.42 | N |
| ATOM | 1472 | CA  | GLN | B | 327 | −66.855 | −69.467 | −32.956 | 1.00 | 19.74 | C |
| ATOM | 1473 | CB  | GLN | B | 327 | −66.511 | −68.551 | −34.138 | 1.00 | 17.78 | C |
| ATOM | 1474 | CG  | GLN | B | 327 | −66.322 | −69.254 | −35.491 | 1.00 | 17.05 | C |
| ATOM | 1475 | CD  | GLN | B | 327 | −67.529 | −70.079 | −35.918 | 1.00 | 21.82 | C |
| ATOM | 1476 | OE1 | GLN | B | 327 | −68.672 | −69.634 | −35.790 | 1.00 | 19.63 | O |
| ATOM | 1477 | NE2 | GLN | B | 327 | −67.277 | −71.296 | −36.450 | 1.00 | 14.70 | N |
| ATOM | 1478 | C   | GLN | B | 327 | −65.844 | −70.621 | −32.820 | 1.00 | 19.32 | C |
| ATOM | 1479 | O   | GLN | B | 327 | −66.217 | −71.782 | −32.987 | 1.00 | 19.00 | C |
| ATOM | 1480 | N   | CYS | B | 328 | −64.579 | −70.319 | −32.501 | 1.00 | 15.97 | N |
| ATOM | 1481 | CA  | CYS | B | 328 | −63.535 | −71.365 | −32.484 | 1.00 | 21.42 | C |
| ATOM | 1482 | CB  | CYS | B | 328 | −62.164 | −70.816 | −32.947 | 1.00 | 17.46 | C |
| ATOM | 1483 | SG  | CYS | B | 328 | −61.540 | −69.481 | −31.860 | 1.00 | 22.43 | S |
| ATOM | 1484 | C   | CYS | B | 328 | −63.448 | −71.988 | −31.095 | 1.00 | 21.34 | C |
| ATOM | 1485 | O   | CYS | B | 328 | −62.766 | −73.006 | −30.890 | 1.00 | 20.25 | O |
| ATOM | 1486 | N   | GLN | B | 329 | −64.162 | −71.386 | −30.141 | 1.00 | 18.79 | N |
| ATOM | 1487 | CA  | GLN | B | 329 | −64.326 | −71.976 | −28.812 | 1.00 | 20.39 | C |
| ATOM | 1488 | CB  | GLN | B | 329 | −65.034 | −73.368 | −28.888 | 1.00 | 23.80 | C |
| ATOM | 1489 | CG  | GLN | B | 329 | −66.229 | −73.470 | −29.868 | 1.00 | 22.53 | C |
| ATOM | 1490 | CD  | GLN | B | 329 | −67.041 | −74.761 | −29.717 | 1.00 | 25.79 | C |
| ATOM | 1491 | OE1 | GLN | B | 329 | −67.162 | −75.297 | −28.622 | 1.00 | 36.92 | O |
| ATOM | 1492 | NE2 | GLN | B | 329 | −67.565 | −75.281 | −30.829 | 1.00 | 22.75 | N |
| ATOM | 1493 | C   | GLN | B | 329 | −63.000 | −72.057 | −27.980 | 1.00 | 22.95 | C |
| ATOM | 1494 | O   | GLN | B | 329 | −63.053 | −71.996 | −26.761 | 1.00 | 31.05 | O |
| ATOM | 1495 | N   | GLU | B | 330 | −61.833 | −72.134 | −28.640 | 1.00 | 26.57 | N |
| ATOM | 1496 | CA  | GLU | B | 330 | −60.514 | −72.430 | −27.965 | 1.00 | 30.50 | C |
| ATOM | 1497 | CB  | GLU | B | 330 | −59.518 | −73.062 | −28.946 | 1.00 | 30.59 | C |

TABLE 4-continued

Atomic coordinates for CRBN(TBD):Pomalidomide (Murine protein)

| ATOM | 1498 | CG | GLU | B | 330 | −59.786 | −74.520 | −29.335 | 1.00 | 50.82 | C |
|---|---|---|---|---|---|---|---|---|---|---|---|
| ATOM | 1499 | CD | GLU | B | 330 | −59.003 | −75.523 | −28.489 | 1.00 | 54.24 | C |
| ATOM | 1500 | OE1 | GLU | B | 330 | −59.541 | −75.974 | −27.453 | 1.00 | 64.12 | O |
| ATOM | 1501 | OE2 | GLU | B | 330 | −57.860 | −75.880 | −28.867 | 1.00 | 54.69 | O |
| ATOM | 1502 | C | GLU | B | 330 | −59.811 | −71.182 | −27.417 | 1.00 | 33.57 | C |
| ATOM | 1503 | O | GLU | B | 330 | −58.982 | −71.250 | −26.499 | 1.00 | 29.81 | O |
| ATOM | 1504 | N | THR | B | 331 | −60.081 | −70.067 | −28.052 | 1.00 | 20.02 | N |
| ATOM | 1505 | CA | THR | B | 331 | −59.249 | −68.918 | −27.922 | 1.00 | 23.19 | C |
| ATOM | 1506 | CB | THR | B | 331 | −59.133 | −68.233 | −29.298 | 1.00 | 24.77 | C |
| ATOM | 1507 | OG1 | THR | B | 331 | −58.719 | −69.211 | −30.263 | 1.00 | 20.05 | O |
| ATOM | 1508 | CG2 | THR | B | 331 | −58.163 | −67.086 | −29.280 | 1.00 | 15.31 | C |
| ATOM | 1509 | C | THR | B | 331 | −59.831 | −67.975 | −26.886 | 1.00 | 19.71 | C |
| ATOM | 1510 | O | THR | B | 331 | −60.967 | −67.444 | −27.047 | 1.00 | 16.61 | O |
| ATOM | 1511 | N | GLU | B | 332 | −59.052 | −67.752 | −25.828 | 1.00 | 16.82 | N |
| ATOM | 1512 | CA | GLU | B | 332 | −59.419 | −66.809 | −24.796 | 1.00 | 17.31 | C |
| ATOM | 1513 | CB | GLU | B | 332 | −58.542 | −66.999 | −23.525 | 1.00 | 19.58 | C |
| ATOM | 1514 | CG | GLU | B | 332 | −59.045 | −66.164 | −22.375 | 1.00 | 17.83 | C |
| ATOM | 1515 | CD | GLU | B | 332 | −58.159 | −66.232 | −21.163 | 1.00 | 20.67 | C |
| ATOM | 1516 | OE1 | GLU | B | 332 | −58.291 | −67.201 | −20.407 | 1.00 | 18.15 | O |
| ATOM | 1517 | OE2 | GLU | B | 332 | −57.330 | −65.318 | −20.976 | 1.00 | 17.34 | O |
| ATOM | 1518 | C | GLU | B | 332 | −59.298 | −65.383 | −25.325 | 1.00 | 19.08 | C |
| ATOM | 1519 | O | GLU | B | 332 | −58.251 | −65.022 | −25.850 | 1.00 | 21.14 | O |
| ATOM | 1520 | N | ILE | B | 333 | −60.349 | −64.566 | −25.175 | 1.00 | 14.52 | N |
| ATOM | 1521 | CA | ILE | B | 333 | −60.245 | −63.162 | −25.639 | 1.00 | 15.24 | C |
| ATOM | 1522 | CB | ILE | B | 333 | −61.426 | −62.759 | −26.536 | 1.00 | 13.05 | C |
| ATOM | 1523 | CG1 | ILE | B | 333 | −61.528 | −63.737 | −27.743 | 1.00 | 17.07 | C |
| ATOM | 1524 | CD1 | ILE | B | 333 | −60.466 | −63.562 | −28.793 | 1.00 | 13.55 | C |
| ATOM | 1525 | CG2 | ILE | B | 333 | −61.342 | −61.271 | −26.927 | 1.00 | 12.30 | C |
| ATOM | 1526 | C | ILE | B | 333 | −60.065 | −62.165 | −24.489 | 1.00 | 17.36 | C |
| ATOM | 1527 | O | ILE | B | 333 | −59.322 | −61.177 | −24.616 | 1.00 | 17.79 | O |
| ATOM | 1528 | N | THR | B | 334 | −60.723 | −62.436 | −23.363 | 1.00 | 16.75 | N |
| ATOM | 1529 | CA | THR | B | 334 | −60.455 | −61.642 | −22.150 | 1.00 | 16.99 | C |
| ATOM | 1530 | CB | THR | B | 334 | −61.175 | −60.282 | −22.242 | 1.00 | 15.74 | C |
| ATOM | 1531 | OG1 | THR | B | 334 | −60.687 | −59.411 | −21.224 | 1.00 | 23.64 | O |
| ATOM | 1532 | CG2 | THR | B | 334 | −62.657 | −60.463 | −22.131 | 1.00 | 14.47 | C |
| ATOM | 1533 | C | THR | B | 334 | −60.836 | −62.480 | −20.909 | 1.00 | 15.10 | C |
| ATOM | 1534 | O | THR | B | 334 | −61.151 | −63.674 | −21.037 | 1.00 | 13.65 | O |
| ATOM | 1535 | N | THR | B | 335 | −60.770 | −61.892 | −19.722 | 1.00 | 14.71 | N |
| ATOM | 1536 | CA | THR | B | 335 | −61.224 | −62.576 | −18.555 | 1.00 | 16.76 | C |
| ATOM | 1537 | CB | THR | B | 335 | −60.026 | −62.971 | −17.673 | 1.00 | 16.28 | C |
| ATOM | 1538 | OG1 | THR | B | 335 | −59.527 | −61.792 | −17.031 | 1.00 | 20.59 | O |
| ATOM | 1539 | CG2 | THR | B | 335 | −58.931 | −63.586 | −18.513 | 1.00 | 17.06 | C |
| ATOM | 1540 | C | THR | B | 335 | −62.156 | −61.674 | −17.771 | 1.00 | 16.29 | C |
| ATOM | 1541 | O | THR | B | 335 | −62.139 | −60.455 | −17.961 | 1.00 | 15.47 | O |
| ATOM | 1542 | N | LYS | B | 336 | −62.968 | −62.254 | −16.892 | 1.00 | 15.80 | N |
| ATOM | 1543 | CA | LYS | B | 336 | −63.872 | −61.446 | −16.048 | 1.00 | 21.89 | C |
| ATOM | 1544 | CB | LYS | B | 336 | −64.715 | −62.330 | −15.141 | 1.00 | 20.64 | C |
| ATOM | 1545 | CG | LYS | B | 336 | −65.813 | −63.096 | −15.864 | 1.00 | 28.57 | C |
| ATOM | 1546 | CD | LYS | B | 336 | −66.834 | −63.608 | −14.846 | 1.00 | 27.84 | C |
| ATOM | 1547 | CE | LYS | B | 336 | −68.199 | −63.863 | −15.483 | 1.00 | 40.86 | C |
| ATOM | 1548 | NZ | LYS | B | 336 | −68.961 | −64.844 | −14.650 | 1.00 | 33.79 | N |
| ATOM | 1549 | C | LYS | B | 336 | −63.111 | −60.439 | −15.198 | 1.00 | 16.16 | C |
| ATOM | 1550 | O | LYS | B | 336 | −63.661 | −59.410 | −14.804 | 1.00 | 16.06 | O |
| ATOM | 1551 | N | ASN | B | 337 | −61.854 | −60.759 | −14.879 | 1.00 | 14.67 | N |
| ATOM | 1552 | CA | ASN | B | 337 | −61.006 | −59.830 | −14.097 | 1.00 | 17.91 | C |
| ATOM | 1553 | CB | ASN | B | 337 | −59.654 | −60.466 | −13.780 | 1.00 | 15.75 | C |
| ATOM | 1554 | CG | ASN | B | 337 | −59.788 | −61.754 | −13.009 | 1.00 | 22.24 | C |
| ATOM | 1555 | OD1 | ASN | B | 337 | −59.355 | −62.790 | −13.457 | 1.00 | 26.50 | O |
| ATOM | 1556 | ND2 | ASN | B | 337 | −60.403 | −61.687 | −11.851 | 1.00 | 34.77 | N |
| ATOM | 1557 | C | ASN | B | 337 | −60.783 | −58.492 | −14.796 | 1.00 | 15.80 | C |
| ATOM | 1558 | O | ASN | B | 337 | −60.522 | −57.495 | −14.146 | 1.00 | 15.11 | O |
| ATOM | 1559 | N | GLU | B | 338 | −60.847 | −58.494 | −16.135 | 1.00 | 16.19 | N |
| ATOM | 1560 | CA | GLU | B | 338 | −60.552 | −57.299 | −16.908 | 1.00 | 15.10 | C |
| ATOM | 1561 | CB | GLU | B | 338 | −59.921 | −57.632 | −18.270 | 1.00 | 12.81 | C |
| ATOM | 1562 | CG | GLU | B | 338 | −58.644 | −58.423 | −18.153 | 1.00 | 15.49 | C |
| ATOM | 1563 | CD | GLU | B | 338 | −57.668 | −57.767 | −17.194 | 1.00 | 22.76 | C |
| ATOM | 1564 | OE1 | GLU | B | 338 | −57.431 | −56.551 | −17.299 | 1.00 | 18.21 | O |
| ATOM | 1565 | OE2 | GLU | B | 338 | −57.147 | −58.472 | −16.326 | 1.00 | 24.45 | O |
| ATOM | 1566 | C | GLU | B | 338 | −61.737 | −56.372 | −17.127 | 1.00 | 16.48 | C |
| ATOM | 1567 | O | GLU | B | 338 | −61.555 | −55.267 | −17.656 | 1.00 | 16.22 | O |
| ATOM | 1568 | N | ILE | B | 339 | −62.939 | −56.811 | −16.734 | 1.00 | 15.07 | N |
| ATOM | 1569 | CA | ILE | B | 339 | −64.160 | −56.004 | −16.969 | 1.00 | 17.10 | C |
| ATOM | 1570 | CB | ILE | B | 339 | −64.456 | −56.823 | −16.669 | 1.00 | 23.04 | C |
| ATOM | 1571 | CG1 | ILE | B | 339 | −65.586 | −58.054 | −17.617 | 1.00 | 23.48 | C |
| ATOM | 1572 | CD1 | ILE | B | 339 | −66.528 | −59.156 | −17.092 | 1.00 | 20.03 | C |
| ATOM | 1573 | CG2 | ILE | B | 339 | −66.711 | −55.917 | −16.754 | 1.00 | 19.16 | C |
| ATOM | 1574 | C | ILE | B | 339 | −64.150 | −54.762 | −16.109 | 1.00 | 18.73 | C |
| ATOM | 1575 | O | ILE | B | 339 | −63.706 | −54.811 | −14.934 | 1.00 | 17.53 | O |

TABLE 4-continued

Atomic coordinates for CRBN(TBD):Pomalidomide (Murine protein)

| ATOM | 1576 | N | PHE | B | 340 | −64.628 | −53.645 | −16.692 | 1.00 | 11.72 | N |
|---|---|---|---|---|---|---|---|---|---|---|---|
| ATOM | 1577 | CA | PHE | B | 340 | −64.810 | −52.406 | −16.010 | 1.00 | 16.33 | C |
| ATOM | 1578 | CB | PHE | B | 340 | −63.548 | −51.493 | −16.034 | 1.00 | 13.18 | C |
| ATOM | 1579 | CG | PHE | B | 340 | −63.303 | −50.823 | −17.348 | 1.00 | 15.25 | C |
| ATOM | 1580 | CD1 | PHE | B | 340 | −63.510 | −49.455 | −17.479 | 1.00 | 13.45 | C |
| ATOM | 1581 | CE1 | PHE | B | 340 | −63.272 | −48.798 | −18.694 | 1.00 | 12.40 | C |
| ATOM | 1582 | CZ | PHE | B | 340 | −62.799 | −49.516 | −19.797 | 1.00 | 9.99 | C |
| ATOM | 1583 | CE2 | PHE | B | 340 | −62.533 | −50.901 | −19.680 | 1.00 | 11.53 | C |
| ATOM | 1584 | CD2 | PHE | B | 340 | −62.778 | −51.553 | −18.468 | 1.00 | 12.25 | C |
| ATOM | 1585 | C | PHE | B | 340 | −65.987 | −51.686 | −16.673 | 1.00 | 16.55 | C |
| ATOM | 1586 | O | PHE | B | 340 | −66.451 | −52.083 | −17.781 | 1.00 | 15.69 | O |
| ATOM | 1587 | N | SER | B | 341 | −66.430 | −50.627 | −16.026 | 1.00 | 15.87 | N |
| ATOM | 1588 | CA | SER | B | 341 | −67.627 | −49.896 | −16.474 | 1.00 | 18.61 | C |
| ATOM | 1589 | CB | SER | B | 341 | −68.703 | −49.887 | −15.389 | 1.00 | 23.05 | C |
| ATOM | 1590 | OG | SER | B | 341 | −69.958 | −49.458 | −15.936 | 1.00 | 26.64 | O |
| ATOM | 1591 | C | SER | B | 341 | −67.295 | −48.496 | −16.884 | 1.00 | 18.03 | C |
| ATOM | 1592 | O | SER | B | 341 | −67.003 | −47.650 | −16.051 | 1.00 | 21.76 | O |
| ATOM | 1593 | N | LEU | B | 342 | −67.257 | −48.268 | −18.200 | 1.00 | 25.29 | N |
| ATOM | 1594 | CA | LEU | B | 342 | −66.943 | −46.952 | −18.766 | 1.00 | 23.64 | C |
| ATOM | 1595 | CB | LEU | B | 342 | −66.494 | −47.069 | −20.251 | 1.00 | 28.34 | C |
| ATOM | 1596 | CG | LEU | B | 342 | −65.626 | −46.023 | −20.981 | 1.00 | 28.10 | C |
| ATOM | 1597 | CD1 | LEU | B | 342 | −66.397 | −44.772 | −21.307 | 1.00 | 30.47 | C |
| ATOM | 1598 | CD2 | LEU | B | 342 | −64.405 | −45.646 | −20.146 | 1.00 | 35.50 | C |
| ATOM | 1599 | C | LEU | B | 342 | −68.126 | −46.013 | −18.583 | 1.00 | 29.99 | C |
| ATOM | 1600 | O | LEU | B | 342 | −67.967 | −44.889 | −18.046 | 1.00 | 25.51 | O |
| ATOM | 1601 | N | SER | B | 343 | −69.328 | −46.483 | −18.945 | 1.00 | 28.47 | N |
| ATOM | 1602 | CA | SER | B | 343 | −70.510 | −45.602 | −18.994 | 1.00 | 39.38 | C |
| ATOM | 1603 | CB | SER | B | 343 | −71.711 | −46.304 | −19.676 | 1.00 | 43.93 | C |
| ATOM | 1604 | OG | SER | B | 343 | −71.699 | −47.691 | −19.422 | 1.00 | 40.39 | O |
| ATOM | 1605 | C | SER | B | 343 | −70.919 | −44.900 | −17.658 | 1.00 | 41.75 | C |
| ATOM | 1606 | O | SER | B | 343 | −71.705 | −45.423 | −16.855 | 1.00 | 35.22 | O |
| ATOM | 1607 | N | GLU | B | 360 | −74.896 | −55.104 | −23.982 | 1.00 | 32.15 | N |
| ATOM | 1608 | CA | GLU | B | 360 | −74.565 | −55.568 | −25.345 | 1.00 | 40.50 | C |
| ATOM | 1609 | CB | GLU | B | 360 | −75.210 | −54.647 | −26.398 | 1.00 | 42.12 | C |
| ATOM | 1610 | CG | GLU | B | 360 | −74.822 | −54.947 | −27.844 | 1.00 | 42.69 | C |
| ATOM | 1611 | CD | GLU | B | 360 | −75.585 | −56.117 | −28.434 | 1.00 | 48.38 | C |
| ATOM | 1612 | OE1 | GLU | B | 360 | −75.164 | −56.625 | −29.497 | 1.00 | 60.27 | O |
| ATOM | 1613 | OE2 | GLU | B | 360 | −76.598 | −56.536 | −27.839 | 1.00 | 61.10 | O |
| ATOM | 1614 | C | GLU | B | 360 | −73.054 | −55.643 | −25.598 | 1.00 | 39.19 | C |
| ATOM | 1615 | O | GLU | B | 360 | −72.555 | −56.586 | −26.271 | 1.00 | 26.18 | O |
| ATOM | 1616 | N | THR | B | 361 | −72.356 | −54.607 | −25.123 | 1.00 | 26.11 | N |
| ATOM | 1617 | CA | THR | B | 361 | −70.917 | −54.413 | −25.355 | 1.00 | 30.60 | C |
| ATOM | 1618 | CB | THR | B | 361 | −70.628 | −53.059 | −26.040 | 1.00 | 38.10 | C |
| ATOM | 1619 | OG1 | THR | B | 361 | −71.157 | −53.093 | −27.370 | 1.00 | 55.54 | O |
| ATOM | 1620 | CG2 | THR | B | 361 | −69.125 | −52.773 | −26.111 | 1.00 | 28.78 | C |
| ATOM | 1621 | C | THR | B | 361 | −70.201 | −54.458 | −24.013 | 1.00 | 24.67 | C |
| ATOM | 1622 | O | THR | B | 361 | −70.417 | −53.620 | −23.177 | 1.00 | 26.55 | O |
| ATOM | 1623 | N | LEU | B | 362 | −69.384 | −55.470 | −23.821 | 1.00 | 19.02 | N |
| ATOM | 1624 | CA | LEU | B | 362 | −68.602 | −55.638 | −22.612 | 1.00 | 16.98 | C |
| ATOM | 1625 | CB | LEU | B | 362 | −68.219 | −57.109 | −22.546 | 1.00 | 17.61 | C |
| ATOM | 1626 | CG | LEU | B | 362 | −67.577 | −57.688 | −21.312 | 1.00 | 22.51 | C |
| ATOM | 1627 | CD1 | LEU | B | 362 | −68.528 | −57.625 | −20.123 | 1.00 | 18.25 | C |
| ATOM | 1628 | CD2 | LEU | B | 362 | −67.165 | −59.114 | −21.647 | 1.00 | 21.01 | C |
| ATOM | 1629 | C | LEU | B | 362 | −67.339 | −54.757 | −22.750 | 1.00 | 16.19 | C |
| ATOM | 1630 | O | LEU | B | 362 | −66.675 | −54.780 | −23.788 | 1.00 | 17.80 | O |
| ATOM | 1631 | N | THR | B | 363 | −66.986 | −53.989 | −21.727 | 1.00 | 15.48 | N |
| ATOM | 1632 | CA | THR | B | 363 | −65.724 | −53.230 | −21.828 | 1.00 | 13.14 | C |
| ATOM | 1633 | CB | THR | B | 363 | −65.952 | −51.711 | −21.636 | 1.00 | 13.68 | C |
| ATOM | 1634 | OG1 | THR | B | 363 | −66.562 | −54.488 | −20.359 | 1.00 | 15.25 | O |
| ATOM | 1635 | CG2 | THR | B | 363 | −66.880 | −51.169 | −22.740 | 1.00 | 15.60 | C |
| ATOM | 1636 | C | THR | B | 363 | −64.665 | −53.785 | −20.889 | 1.00 | 15.29 | C |
| ATOM | 1637 | O | THR | B | 363 | −64.928 | −54.019 | −19.666 | 1.00 | 13.39 | O |
| ATOM | 1638 | N | VAL | B | 364 | −63.470 | −53.985 | −21.431 | 1.00 | 11.88 | N |
| ATOM | 1639 | CA | VAL | B | 364 | −62.397 | −54.633 | −20.669 | 1.00 | 12.70 | C |
| ATOM | 1640 | CB | VAL | B | 364 | −62.222 | −56.157 | −21.031 | 1.00 | 14.95 | C |
| ATOM | 1641 | CG1 | VAL | B | 364 | −63.465 | −56.991 | −20.646 | 1.00 | 14.46 | C |
| ATOM | 1642 | CG2 | VAL | B | 364 | −61.801 | −56.385 | −22.501 | 1.00 | 11.34 | C |
| ATOM | 1643 | C | VAL | B | 364 | −61.116 | −53.868 | −20.870 | 1.00 | 13.19 | C |
| ATOM | 1644 | O | VAL | B | 364 | −60.913 | −53.230 | −21.942 | 1.00 | 10.72 | O |
| ATOM | 1645 | N | TYR | B | 365 | −60.249 | −53.875 | −19.834 | 1.00 | 12.47 | N |
| ATOM | 1646 | CA | TYR | B | 365 | −59.029 | −53.088 | −19.900 | 1.00 | 11.95 | C |
| ATOM | 1647 | CB | TYR | B | 365 | −58.393 | −52.934 | −18.478 | 1.00 | 10.06 | C |
| ATOM | 1648 | CG | TYR | B | 365 | −59.068 | −51.902 | −17.566 | 1.00 | 9.95 | C |
| ATOM | 1649 | CD1 | TYR | B | 365 | −59.117 | −50.551 | −17.921 | 1.00 | 9.17 | C |
| ATOM | 1650 | CE1 | TYR | B | 365 | −59.706 | −49.610 | −17.076 | 1.00 | 10.71 | C |
| ATOM | 1651 | CZ | TYR | B | 365 | −60.241 | −50.039 | −15.861 | 1.00 | 12.14 | C |
| ATOM | 1652 | OH | TYR | B | 365 | −60.815 | −49.124 | −15.007 | 1.00 | 10.17 | O |
| ATOM | 1653 | CE2 | TYR | B | 365 | −60.194 | −51.390 | −15.499 | 1.00 | 10.44 | C |

TABLE 4-continued

Atomic coordinates for CRBN(TBD):Pomalidomide (Murine protein)

| ATOM | 1654 | CD2 | TYR | B | 365 | −59.622 | −52.297 | −16.367 | 1.00 | 9.33 | C |
|---|---|---|---|---|---|---|---|---|---|---|---|
| ATOM | 1655 | C | TYR | B | 365 | −57.997 | −53.745 | −20.838 | 1.00 | 12.87 | C |
| ATOM | 1656 | O | TYR | B | 365 | −57.152 | −53.062 | −21.430 | 1.00 | 13.23 | O |
| ATOM | 1657 | N | LYS | B | 366 | −58.064 | −55.076 | −20.943 | 1.00 | 10.50 | N |
| ATOM | 1658 | CA | LYS | B | 366 | −57.044 | −55.842 | −21.588 | 1.00 | 12.58 | C |
| ATOM | 1659 | CB | LYS | B | 366 | −56.060 | −56.412 | −20.513 | 1.00 | 12.47 | C |
| ATOM | 1660 | CG | LYS | B | 366 | −55.114 | −55.400 | −19.901 | 1.00 | 13.02 | C |
| ATOM | 1661 | CD | LYS | B | 366 | −53.955 | −55.298 | −20.920 | 1.00 | 17.19 | C |
| ATOM | 1662 | CE | LYS | B | 366 | −52.989 | −54.194 | −20.639 | 1.00 | 22.40 | C |
| ATOM | 1663 | NZ | LYS | B | 366 | −52.022 | −54.148 | −21.770 | 1.00 | 11.57 | N |
| ATOM | 1664 | C | LYS | B | 366 | −57.716 | −57.024 | −22.293 | 1.00 | 11.90 | C |
| ATOM | 1665 | O | LYS | B | 366 | −58.726 | −57.577 | −21.808 | 1.00 | 14.08 | O |
| ATOM | 1666 | N | ALA | B | 367 | −57.139 | −57.434 | −23.404 | 1.00 | 11.40 | N |
| ATOM | 1667 | CA | ALA | B | 367 | −57.693 | −58.571 | −24.164 | 1.00 | 12.16 | C |
| ATOM | 1668 | CB | ALA | B | 367 | −58.746 | −58.076 | −25.162 | 1.00 | 12.10 | C |
| ATOM | 1669 | C | ALA | B | 367 | −56.549 | −59.250 | −24.873 | 1.00 | 12.33 | C |
| ATOM | 1670 | O | ALA | B | 367 | −55.424 | −58.709 | −24.930 | 1.00 | 11.65 | O |
| ATOM | 1671 | N | SER | B | 368 | −56.812 | −60.440 | −25.427 | 1.00 | 12.83 | N |
| ATOM | 1672 | CA | SER | B | 368 | −55.744 | −61.223 | −26.019 | 1.00 | 15.64 | C |
| ATOM | 1673 | CB | SER | B | 368 | −55.277 | −62.283 | −25.002 | 1.00 | 14.92 | C |
| ATOM | 1674 | OG | SER | B | 368 | −56.375 | −63.056 | −24.552 | 1.00 | 14.79 | O |
| ATOM | 1675 | C | SER | B | 368 | −56.208 | −61.939 | −27.289 | 1.00 | 16.06 | C |
| ATOM | 1676 | O | SER | B | 368 | −57.434 | −62.190 | −27.475 | 1.00 | 15.79 | O |
| ATOM | 1677 | N | ASN | B | 369 | −55.243 | −62.283 | −28.143 | 1.00 | 15.87 | N |
| ATOM | 1678 | CA | ASN | B | 369 | −55.503 | −63.156 | −29.288 | 1.00 | 19.46 | C |
| ATOM | 1679 | CB | ASN | B | 369 | −56.080 | −64.473 | −28.803 | 1.00 | 15.83 | C |
| ATOM | 1680 | CG | ASN | B | 369 | −55.154 | −65.200 | −27.867 | 1.00 | 20.08 | C |
| ATOM | 1681 | OD1 | ASN | B | 369 | −55.593 | −65.737 | −26.873 | 1.00 | 24.87 | O |
| ATOM | 1682 | ND2 | ASN | B | 369 | −53.872 | −65.225 | −28.184 | 1.00 | 15.96 | N |
| ATOM | 1683 | C | ASN | B | 369 | −56.473 | −62.503 | −30.284 | 1.00 | 20.41 | C |
| ATOM | 1684 | O | ASN | B | 369 | −57.215 | −63.198 | −31.016 | 1.00 | 20.86 | O |
| ATOM | 1685 | N | LEU | B | 370 | −56.477 | −61.166 | −30.280 | 1.00 | 17.87 | N |
| ATOM | 1686 | CA | LEU | B | 370 | −57.196 | −60.381 | −31.304 | 1.00 | 20.24 | C |
| ATOM | 1687 | CB | LEU | B | 370 | −58.031 | −59.259 | −30.660 | 1.00 | 17.03 | C |
| ATOM | 1688 | CG | LEU | B | 370 | −59.210 | −59.705 | −29.784 | 1.00 | 19.14 | C |
| ATOM | 1689 | CD1 | LEU | B | 370 | −59.676 | −58.552 | −28.860 | 1.00 | 17.00 | C |
| ATOM | 1690 | CD2 | LEU | B | 370 | −60.370 | −60.220 | −30.642 | 1.00 | 15.59 | C |
| ATOM | 1691 | C | LEU | B | 370 | −56.226 | −59.817 | −32.338 | 1.00 | 18.63 | C |
| ATOM | 1692 | O | LEU | B | 370 | −55.111 | −59.397 | −31.984 | 1.00 | 16.57 | O |
| ATOM | 1693 | N | ASN | B | 371 | −56.637 | −59.881 | −33.616 | 1.00 | 19.09 | N |
| ATOM | 1694 | CA | ASN | B | 371 | −56.005 | −59.098 | −34.733 | 1.00 | 24.20 | C |
| ATOM | 1695 | CB | ASN | B | 371 | −56.069 | −59.866 | −36.081 | 1.00 | 26.07 | C |
| ATOM | 1696 | CG | ASN | B | 371 | −54.844 | −60.701 | −36.343 | 1.00 | 37.87 | C |
| ATOM | 1697 | OD1 | ASN | B | 371 | −54.942 | −61.906 | −36.610 | 1.00 | 40.52 | O |
| ATOM | 1698 | ND2 | ASN | B | 371 | −53.674 | −60.068 | −36.287 | 1.00 | 49.08 | N |
| ATOM | 1699 | C | ASN | B | 371 | −56.743 | −57.793 | −34.967 | 1.00 | 26.33 | C |
| ATOM | 1700 | O | ASN | B | 371 | −57.987 | −57.800 | −35.061 | 1.00 | 21.32 | O |
| ATOM | 1701 | N | LEU | B | 372 | −55.975 | −56.714 | −35.151 | 1.00 | 19.03 | N |
| ATOM | 1702 | CA | LEU | B | 372 | −56.516 | −55.388 | −35.479 | 1.00 | 21.23 | C |
| ATOM | 1703 | CB | LEU | B | 372 | −55.669 | −54.255 | −34.842 | 1.00 | 15.54 | C |
| ATOM | 1704 | CG | LEU | B | 372 | −55.629 | −54.317 | −33.309 | 1.00 | 20.87 | C |
| ATOM | 1705 | CD1 | LEU | B | 372 | −54.508 | −53.457 | −32.742 | 1.00 | 18.28 | C |
| ATOM | 1706 | CD2 | LEU | B | 372 | −56.984 | −53.987 | −32.686 | 1.00 | 20.53 | C |
| ATOM | 1707 | C | LEU | B | 372 | −56.517 | −55.215 | −36.963 | 1.00 | 21.31 | C |
| ATOM | 1708 | O | LEU | B | 372 | −55.472 | −55.377 | −37.603 | 1.00 | 21.11 | O |
| ATOM | 1709 | N | ILE | B | 373 | −57.682 | −54.845 | −37.499 | 1.00 | 21.66 | N |
| ATOM | 1710 | CA | ILE | B | 373 | −57.879 | −54.654 | −38.950 | 1.00 | 23.75 | C |
| ATOM | 1711 | CB | ILE | B | 373 | −59.223 | −55.238 | −39.403 | 1.00 | 23.03 | C |
| ATOM | 1712 | CG1 | ILE | B | 373 | −59.311 | −56.738 | −39.086 | 1.00 | 25.33 | C |
| ATOM | 1713 | CD1 | ILE | B | 373 | −58.223 | −57.565 | −39.748 | 1.00 | 32.29 | C |
| ATOM | 1714 | CG2 | ILE | B | 373 | −59.476 | −54.951 | −40.892 | 1.00 | 26.69 | C |
| ATOM | 1715 | C | ILE | B | 373 | −57.996 | −53.164 | −39.160 | 1.00 | 28.35 | C |
| ATOM | 1716 | O | ILE | B | 373 | −58.913 | −52.544 | −38.615 | 1.00 | 25.31 | O |
| ATOM | 1717 | N | GLY | B | 374 | −57.086 | −52.575 | −39.929 | 1.00 | 27.91 | N |
| ATOM | 1718 | CA | GLY | B | 374 | −57.239 | −51.159 | −40.312 | 1.00 | 31.00 | C |
| ATOM | 1719 | C | GLY | B | 374 | −56.656 | −50.157 | −39.322 | 1.00 | 36.32 | C |
| ATOM | 1720 | O | GLY | B | 374 | −55.905 | −50.514 | −38.417 | 1.00 | 32.64 | O |
| ATOM | 1721 | N | ARG | B | 375 | −56.987 | −48.890 | −39.517 | 1.00 | 36.50 | N |
| ATOM | 1722 | CA | ARG | B | 375 | −56.502 | −47.829 | −38.643 | 1.00 | 37.55 | C |
| ATOM | 1723 | CB | ARG | B | 375 | −55.740 | −46.764 | −39.454 | 1.00 | 43.97 | C |
| ATOM | 1724 | CG | ARG | B | 375 | −56.126 | −46.700 | −40.929 | 1.00 | 54.49 | C |
| ATOM | 1725 | CD | ARG | B | 375 | −54.992 | −46.194 | −41.805 | 1.00 | 57.39 | C |
| ATOM | 1726 | NE | ARG | B | 375 | −54.383 | −44.969 | −41.279 | 1.00 | 76.97 | N |
| ATOM | 1727 | CZ | ARG | B | 375 | −54.863 | −43.738 | −41.462 | 1.00 | 75.86 | C |
| ATOM | 1728 | NH1 | ARG | B | 375 | −55.980 | −43.541 | −42.160 | 1.00 | 82.58 | N |
| ATOM | 1729 | NH2 | ARG | B | 375 | −54.222 | −42.701 | −40.942 | 1.00 | 58.97 | N |
| ATOM | 1730 | C | ARG | B | 375 | −57.668 | −47.224 | −37.843 | 1.00 | 27.00 | C |
| ATOM | 1731 | O | ARG | B | 375 | −58.827 | −47.398 | −38.209 | 1.00 | 30.03 | O |

TABLE 4-continued

Atomic coordinates for CRBN(TBD):Pomalidomide (Murine protein)

| ATOM | 1732 | N | PRO | B | 376 | −57.368 | −46.558 | −36.727 | 1.00 | 29.10 | N |
|---|---|---|---|---|---|---|---|---|---|---|---|
| ATOM | 1733 | CA | PRO | B | 376 | −58.428 | −45.966 | −35.869 | 1.00 | 26.59 | C |
| ATOM | 1734 | CB | PRO | B | 376 | −57.623 | −45.149 | −34.861 | 1.00 | 25.76 | C |
| ATOM | 1735 | CG | PRO | B | 376 | −56.320 | −45.906 | −34.736 | 1.00 | 29.31 | C |
| ATOM | 1736 | CD | PRO | B | 376 | −56.034 | −46.483 | −36.101 | 1.00 | 28.59 | C |
| ATOM | 1737 | C | PRO | B | 376 | −59.425 | −45.045 | −36.619 | 1.00 | 24.43 | C |
| ATOM | 1738 | O | PRO | B | 376 | −59.012 | −44.338 | −37.517 | 1.00 | 27.57 | O |
| ATOM | 1739 | N | SER | B | 377 | −60.713 | −45.065 | −36.262 | 1.00 | 18.50 | N |
| ATOM | 1740 | CA | SER | B | 377 | −61.681 | −44.033 | −36.774 | 1.00 | 18.67 | C |
| ATOM | 1741 | CB | SER | B | 377 | −62.628 | −44.612 | −37.862 | 1.00 | 18.16 | C |
| ATOM | 1742 | OG | SER | B | 377 | −63.670 | −43.675 | −38.178 | 1.00 | 19.72 | O |
| ATOM | 1743 | C | SER | B | 377 | −62.528 | −43.491 | −35.637 | 1.00 | 16.08 | C |
| ATOM | 1744 | O | SER | B | 377 | −62.887 | −44.219 | −34.730 | 1.00 | 16.76 | O |
| ATOM | 1745 | N | THR | B | 378 | −62.925 | −42.244 | −35.711 | 1.00 | 12.90 | N |
| ATOM | 1746 | CA | THR | B | 378 | −63.819 | −41.745 | −34.698 | 1.00 | 13.73 | C |
| ATOM | 1747 | CB | THR | B | 378 | −63.420 | −40.332 | −34.265 | 1.00 | 14.94 | C |
| ATOM | 1748 | OG1 | THR | B | 378 | −63.411 | −39.537 | −35.415 | 1.00 | 15.24 | O |
| ATOM | 1749 | CG2 | THR | B | 378 | −61.966 | −40.317 | −33.644 | 1.00 | 12.79 | C |
| ATOM | 1750 | C | THR | B | 378 | −65.280 | −41.722 | −35.171 | 1.00 | 18.42 | C |
| ATOM | 1751 | O | THR | B | 378 | −66.167 | −41.337 | −34.412 | 1.00 | 16.86 | O |
| ATOM | 1752 | N | VAL | B | 379 | −65.522 | −42.103 | −36.421 | 1.00 | 17.21 | N |
| ATOM | 1753 | CA | VAL | B | 379 | −66.856 | −41.915 | −37.018 | 1.00 | 20.80 | C |
| ATOM | 1754 | CB | VAL | B | 379 | −66.828 | −42.179 | −38.535 | 1.00 | 22.27 | C |
| ATOM | 1755 | CG1 | VAL | B | 379 | −68.188 | −41.849 | −39.168 | 1.00 | 18.88 | C |
| ATOM | 1756 | CG2 | VAL | B | 379 | −65.733 | −41.310 | −39.179 | 1.00 | 27.51 | C |
| ATOM | 1757 | C | VAL | B | 379 | −67.845 | −42.838 | −36.325 | 1.00 | 16.02 | C |
| ATOM | 1758 | O | VAL | B | 379 | −67.561 | −44.013 | −36.149 | 1.00 | 15.55 | O |
| ATOM | 1759 | N | HIS | B | 380 | −68.963 | −42.283 | −35.861 | 1.00 | 15.24 | N |
| ATOM | 1760 | CA | HIS | B | 380 | −69.986 | −43.064 | −35.127 | 1.00 | 15.62 | C |
| ATOM | 1761 | CB | HIS | B | 380 | −70.677 | −44.067 | −36.058 | 1.00 | 15.16 | C |
| ATOM | 1762 | CG | HIS | B | 380 | −71.195 | −43.423 | −37.332 | 1.00 | 17.94 | C |
| ATOM | 1763 | ND1 | HIS | B | 380 | −71.902 | −42.258 | −37.320 | 1.00 | 16.30 | N |
| ATOM | 1764 | CE1 | HIS | B | 380 | −72.175 | −41.905 | −38.586 | 1.00 | 19.92 | C |
| ATOM | 1765 | NE2 | HIS | B | 380 | −71.630 | −42.824 | −39.402 | 1.00 | 15.57 | N |
| ATOM | 1766 | CD2 | HIS | B | 380 | −71.006 | −43.757 | −38.661 | 1.00 | 15.75 | C |
| ATOM | 1767 | C | HIS | B | 380 | −69.443 | −43.777 | −33.906 | 1.00 | 18.74 | C |
| ATOM | 1768 | O | HIS | B | 380 | −70.040 | −44.764 | −33.444 | 1.00 | 18.02 | O |
| ATOM | 1769 | N | SER | B | 381 | −68.350 | −43.266 | −33.319 | 1.00 | 16.32 | N |
| ATOM | 1770 | CA | SER | B | 381 | −67.821 | −43.931 | −32.107 | 1.00 | 17.67 | C |
| ATOM | 1771 | CB | SER | B | 381 | −66.573 | −43.227 | −31.567 | 1.00 | 19.31 | C |
| ATOM | 1772 | OG | SER | B | 381 | −66.156 | −43.939 | −30.400 | 1.00 | 20.33 | O |
| ATOM | 1773 | C | SER | B | 381 | −68.900 | −44.026 | −30.984 | 1.00 | 15.41 | C |
| ATOM | 1774 | O | SER | B | 381 | −69.533 | −43.040 | −30.648 | 1.00 | 17.37 | O |
| ATOM | 1775 | N | TRP | B | 382 | −69.086 | −45.202 | −30.406 | 1.00 | 13.57 | N |
| ATOM | 1776 | CA | TRP | B | 382 | −70.024 | −45.347 | −29.290 | 1.00 | 16.72 | C |
| ATOM | 1777 | CB | TRP | B | 382 | −70.325 | −46.822 | −29.042 | 1.00 | 18.77 | C |
| ATOM | 1778 | CG | TRP | B | 382 | −70.944 | −47.508 | −30.247 | 1.00 | 18.00 | C |
| ATOM | 1779 | CD1 | TRP | B | 382 | −71.869 | −46.953 | −31.167 | 1.00 | 20.24 | C |
| ATOM | 1780 | NE1 | TRP | B | 382 | −72.219 | −47.879 | −32.123 | 1.00 | 20.52 | N |
| ATOM | 1781 | CE2 | TRP | B | 382 | −71.572 | −49.056 | −31.889 | 1.00 | 18.52 | C |
| ATOM | 1782 | CD2 | TRP | B | 382 | −70.747 | −48.872 | −30.675 | 1.00 | 17.19 | C |
| ATOM | 1783 | CE3 | TRP | B | 382 | −69.977 | −49.945 | −30.212 | 1.00 | 16.96 | C |
| ATOM | 1784 | CZ3 | TRP | B | 382 | −70.050 | −51.162 | −30.908 | 1.00 | 16.35 | C |
| ATOM | 1785 | CH2 | TRP | B | 382 | −70.841 | −51.313 | −32.073 | 1.00 | 19.62 | C |
| ATOM | 1786 | CZ2 | TRP | B | 382 | −71.624 | −50.260 | −32.570 | 1.00 | 21.06 | C |
| ATOM | 1787 | C | TRP | B | 382 | −69.505 | −44.726 | −28.014 | 1.00 | 18.47 | C |
| ATOM | 1788 | O | TRP | B | 382 | −70.272 | −44.519 | −27.060 | 1.00 | 20.72 | O |
| ATOM | 1789 | N | PHE | B | 383 | −68.215 | −44.399 | −27.979 | 1.00 | 15.41 | N |
| ATOM | 1790 | CA | PHE | B | 383 | −67.601 | −43.842 | −26.728 | 1.00 | 16.33 | C |
| ATOM | 1791 | CB | PHE | B | 383 | −66.632 | −44.840 | −26.112 | 1.00 | 14.32 | C |
| ATOM | 1792 | CG | PHE | B | 383 | −67.259 | −46.178 | −25.795 | 1.00 | 14.32 | C |
| ATOM | 1793 | CD1 | PHE | B | 383 | −67.936 | −46.377 | −24.588 | 1.00 | 18.40 | C |
| ATOM | 1794 | CE1 | PHE | B | 383 | −68.513 | −47.605 | −24.291 | 1.00 | 17.95 | C |
| ATOM | 1795 | CZ | PHE | B | 383 | −68.377 | −48.666 | −25.198 | 1.00 | 20.05 | C |
| ATOM | 1796 | CE2 | PHE | B | 383 | −67.659 | −48.479 | −26.388 | 1.00 | 17.26 | C |
| ATOM | 1797 | CD2 | PHE | B | 383 | −67.112 | −47.242 | −26.668 | 1.00 | 15.03 | C |
| ATOM | 1798 | C | PHE | B | 383 | −66.904 | −42.530 | −27.061 | 1.00 | 19.09 | C |
| ATOM | 1799 | O | PHE | B | 383 | −65.771 | −42.534 | −27.517 | 1.00 | 17.94 | O |
| ATOM | 1800 | N | PRO | B | 384 | −67.631 | −41.400 | −26.924 | 1.00 | 23.97 | N |
| ATOM | 1801 | CA | PRO | B | 384 | −67.092 | −40.129 | −27.341 | 1.00 | 22.32 | C |
| ATOM | 1802 | CB | PRO | B | 384 | −68.148 | −39.120 | −26.826 | 1.00 | 29.25 | C |
| ATOM | 1803 | CG | PRO | B | 384 | −69.435 | −39.893 | −26.888 | 1.00 | 27.44 | C |
| ATOM | 1804 | CD | PRO | B | 384 | −69.038 | −41.282 | −26.462 | 1.00 | 26.09 | C |
| ATOM | 1805 | C | PRO | B | 384 | −65.732 | −39.884 | −26.690 | 1.00 | 20.88 | C |
| ATOM | 1806 | O | PRO | B | 384 | −65.531 | −40.205 | −25.500 | 1.00 | 18.24 | O |
| ATOM | 1807 | N | GLY | B | 385 | −64.806 | −39.351 | −27.483 | 1.00 | 18.55 | N |
| ATOM | 1808 | CA | GLY | B | 385 | −63.431 | −39.156 | −27.072 | 1.00 | 16.13 | C |
| ATOM | 1809 | C | GLY | B | 385 | −62.544 | −40.331 | −27.435 | 1.00 | 18.13 | C |

TABLE 4-continued

| | | | | | | | | | | | |
|---|---|---|---|---|---|---|---|---|---|---|---|
| | Atomic coordinates for CRBN(TBD):Pomalidomide (Murine protein) |

| ATOM | 1810 | O | GLY | B | 385 | −61.323 | −40.247 | −27.247 | 1.00 | 17.52 | O |
| ATOM | 1811 | N | TYR | B | 386 | −63.122 | −41.425 | −28.001 | 1.00 | 13.55 | N |
| ATOM | 1812 | CA | TYR | B | 386 | −62.306 | −42.590 | −28.380 | 1.00 | 15.15 | C |
| ATOM | 1813 | CB | TYR | B | 386 | −62.639 | −43.848 | −27.532 | 1.00 | 14.09 | C |
| ATOM | 1814 | CG | TYR | B | 386 | −62.267 | −43.775 | −26.049 | 1.00 | 13.52 | C |
| ATOM | 1815 | CD1 | TYR | B | 386 | −61.013 | −44.211 | −25.602 | 1.00 | 13.02 | C |
| ATOM | 1816 | CE1 | TYR | B | 386 | −60.673 | −44.146 | −24.259 | 1.00 | 11.97 | C |
| ATOM | 1817 | CZ | TYR | B | 386 | −61.584 | −43.648 | −23.355 | 1.00 | 13.23 | C |
| ATOM | 1818 | OH | TYR | B | 386 | −61.222 | −43.608 | −22.033 | 1.00 | 15.62 | O |
| ATOM | 1819 | CE2 | TYR | B | 386 | −62.843 | −43.222 | −23.750 | 1.00 | 13.31 | C |
| ATOM | 1820 | CD2 | TYR | B | 386 | −63.176 | −43.275 | −25.099 | 1.00 | 14.59 | C |
| ATOM | 1821 | C | TYR | B | 386 | −62.480 | −42.916 | −29.867 | 1.00 | 18.68 | C |
| ATOM | 1822 | O | TYR | B | 386 | −63.568 | −42.710 | −30.420 | 1.00 | 15.92 | O |
| ATOM | 1823 | N | ALA | B | 387 | −61.401 | −43.395 | −30.502 | 1.00 | 18.13 | N |
| ATOM | 1824 | CA | ALA | B | 387 | −61.457 | −43.939 | −31.871 | 1.00 | 18.94 | C |
| ATOM | 1825 | CB | ALA | B | 387 | −60.231 | −43.490 | −32.657 | 1.00 | 17.27 | C |
| ATOM | 1826 | C | ALA | B | 387 | −61.534 | −45.467 | −31.793 | 1.00 | 19.79 | C |
| ATOM | 1827 | O | ALA | B | 387 | −61.060 | −46.026 | −30.836 | 1.00 | 19.52 | O |
| ATOM | 1828 | N | TRP | B | 388 | −62.148 | −46.137 | −32.780 | 1.00 | 16.53 | N |
| ATOM | 1829 | CA | TRP | B | 388 | −62.231 | −47.606 | −32.786 | 1.00 | 17.90 | C |
| ATOM | 1830 | CB | TRP | B | 388 | −63.683 | −48.084 | −32.921 | 1.00 | 15.82 | C |
| ATOM | 1831 | CG | TRP | B | 388 | −64.431 | −47.437 | −34.090 | 1.00 | 15.10 | C |
| ATOM | 1832 | CD1 | TRP | B | 388 | −65.223 | −46.310 | −34.049 | 1.00 | 17.19 | C |
| ATOM | 1833 | NE1 | TRP | B | 388 | −65.741 | −46.024 | −35.309 | 1.00 | 17.72 | N |
| ATOM | 1834 | CE2 | TRP | B | 388 | −65.306 | −46.921 | −36.216 | 1.00 | 18.04 | C |
| ATOM | 1835 | CD2 | TRP | B | 388 | −64.465 | −47.875 | −35.507 | 1.00 | 16.49 | C |
| ATOM | 1836 | CE3 | TRP | B | 388 | −63.907 | −48.951 | −36.225 | 1.00 | 19.33 | C |
| ATOM | 1837 | CZ3 | TRP | B | 388 | −64.181 | −49.047 | −37.620 | 1.00 | 22.48 | C |
| ATOM | 1838 | CH2 | TRP | B | 388 | −64.990 | −48.101 | −38.272 | 1.00 | 19.40 | C |
| ATOM | 1839 | CZ2 | TRP | B | 388 | −65.584 | −47.039 | −37.588 | 1.00 | 18.40 | C |
| ATOM | 1840 | C | TRP | B | 388 | −61.430 | −48.3194 | −33.918 | 1.00 | 16.80 | C |
| ATOM | 1841 | O | TRP | B | 388 | −61.216 | −47.544 | −34.934 | 1.00 | 17.91 | O |
| ATOM | 1842 | N | THR | B | 389 | −60.972 | −49.428 | −33.719 | 1.00 | 15.59 | N |
| ATOM | 1843 | CA | THR | B | 389 | −60.308 | −50.259 | −34.740 | 1.00 | 17.23 | C |
| ATOM | 1844 | CB | THR | B | 389 | −58.800 | −50.393 | −34.425 | 1.00 | 17.76 | C |
| ATOM | 1845 | OG1 | THR | B | 389 | −58.200 | −49.079 | −34.352 | 1.00 | 16.72 | O |
| ATOM | 1846 | CG2 | THR | B | 389 | −58.067 | −51.286 | −35.465 | 1.00 | 22.12 | C |
| ATOM | 1847 | C | THR | B | 389 | −60.935 | −51.659 | −34.609 | 1.00 | 18.46 | C |
| ATOM | 1848 | O | THR | B | 389 | −61.019 | −52.181 | −33.509 | 1.00 | 15.15 | O |
| ATOM | 1849 | N | ILE | B | 390 | −61.427 | −52.236 | −35.716 | 1.00 | 15.53 | N |
| ATOM | 1850 | CA | ILE | B | 390 | −62.040 | −53.567 | −35.690 | 1.00 | 16.52 | C |
| ATOM | 1851 | CB | ILE | B | 390 | −62.497 | −54.034 | −37.113 | 1.00 | 18.17 | C |
| ATOM | 1852 | CG1 | ILE | B | 390 | −63.598 | −53.100 | −37.657 | 1.00 | 17.97 | C |
| ATOM | 1853 | CD1 | ILE | B | 390 | −63.883 | −53.294 | −39.166 | 1.00 | 19.51 | C |
| ATOM | 1854 | CG2 | ILE | B | 390 | −63.022 | −55.452 | −37.055 | 1.00 | 18.30 | C |
| ATOM | 1855 | C | ILE | B | 390 | −61.080 | −54.603 | −35.120 | 1.00 | 14.85 | C |
| ATOM | 1856 | O | ILE | B | 390 | −59.880 | −54.589 | −35.450 | 1.00 | 15.32 | O |
| ATOM | 1857 | N | ALA | B | 391 | −61.591 | −55.490 | −34.255 | 1.00 | 12.98 | N |
| ATOM | 1858 | CA | ALA | B | 391 | −60.735 | −56.512 | −33.630 | 1.00 | 15.31 | C |
| ATOM | 1859 | CB | ALA | B | 391 | −60.539 | −56.241 | −32.109 | 1.00 | 12.99 | C |
| ATOM | 1860 | C | ALA | B | 391 | −61.385 | −57.882 | −33.874 | 1.00 | 15.53 | C |
| ATOM | 1861 | O | ALA | B | 391 | −62.569 | −58.124 | −33.516 | 1.00 | 17.70 | O |
| ATOM | 1862 | N | GLN | B | 392 | −60.623 | −58.763 | −34.501 | 1.00 | 18.76 | N |
| ATOM | 1863 | CA | GLN | B | 392 | −61.102 | −60.112 | −34.828 | 1.00 | 20.41 | C |
| ATOM | 1864 | CB | GLN | B | 392 | −61.094 | −60.315 | −36.361 | 1.00 | 19.67 | C |
| ATOM | 1865 | CG | GLN | B | 392 | −59.702 | −60.157 | −36.978 | 1.00 | 19.70 | C |
| ATOM | 1866 | CD | GLN | B | 392 | −59.663 | −60.426 | −38.484 | 1.00 | 29.11 | C |
| ATOM | 1867 | OE1 | GLN | B | 392 | −60.694 | −60.503 | −39.147 | 1.00 | 31.58 | O |
| ATOM | 1868 | NE2 | GLN | B | 392 | −58.468 | −60.557 | −39.019 | 1.00 | 29.79 | N |
| ATOM | 1869 | C | GLN | B | 392 | −60.256 | −61.223 | −34.155 | 1.00 | 20.19 | C |
| ATOM | 1870 | O | GLN | B | 392 | −59.051 | −61.089 | −33.995 | 1.00 | 22.80 | O |
| ATOM | 1871 | N | CYS | B | 393 | −60.890 | −62.356 | −33.853 | 1.00 | 19.02 | N |
| ATOM | 1872 | CA | CYS | B | 393 | −60.165 | −63.510 | −33.354 | 1.00 | 19.57 | C |
| ATOM | 1873 | CB | CYS | B | 393 | −61.126 | −64.683 | −33.180 | 1.00 | 21.00 | C |
| ATOM | 1874 | SG | CYS | B | 393 | −60.330 | −66.166 | −32.549 | 1.00 | 22.30 | S |
| ATOM | 1875 | C | CYS | B | 393 | −59.034 | −63.884 | −34.325 | 1.00 | 20.02 | C |
| ATOM | 1876 | O | CYS | B | 393 | −59.289 | −64.083 | −35.515 | 1.00 | 24.83 | O |
| ATOM | 1877 | N | LYS | B | 394 | −57.807 | −63.967 | −33.813 | 1.00 | 20.06 | N |
| ATOM | 1878 | CA | LYS | B | 394 | −56.634 | −64.377 | −34.592 | 1.00 | 19.72 | C |
| ATOM | 1879 | CB | LYS | B | 394 | −55.341 | −64.216 | −33.777 | 1.00 | 18.32 | C |
| ATOM | 1880 | CG | LYS | B | 394 | −55.039 | −65.385 | −32.838 | 1.00 | 16.36 | C |
| ATOM | 1881 | CD | LYS | B | 394 | −53.772 | −65.188 | −32.028 | 1.00 | 18.08 | C |
| ATOM | 1882 | CE | LYS | B | 394 | −53.405 | −66.457 | −31.278 | 1.00 | 16.92 | C |
| ATOM | 1883 | NZ | LYS | B | 394 | −52.266 | −66.110 | −30.408 | 1.00 | 21.47 | N |
| ATOM | 1884 | C | LYS | B | 394 | −56.724 | −65.822 | −35.157 | 1.00 | 18.13 | C |
| ATOM | 1885 | O | LYS | B | 394 | −56.075 | −66.123 | −36.167 | 1.00 | 12.90 | O |
| ATOM | 1886 | N | ILE | B | 395 | −57.511 | −66.688 | −34.517 | 1.00 | 15.63 | N |
| ATOM | 1887 | CA | ILE | B | 395 | −57.695 | −68.077 | −35.011 | 1.00 | 21.55 | C |

TABLE 4-continued

Atomic coordinates for CRBN(TBD):Pomalidomide (Murine protein)

| ATOM | 1888 | CB | ILE | B | 395 | −58.005 | −69.099 | −33.857 | 1.00 | 19.97 | C |
|---|---|---|---|---|---|---|---|---|---|---|---|
| ATOM | 1889 | CG1 | ILE | B | 395 | −56.825 | −69.232 | −32.856 | 1.00 | 20.90 | C |
| ATOM | 1890 | CD1 | ILE | B | 395 | −55.541 | −69.833 | −33.405 | 1.00 | 23.87 | C |
| ATOM | 1891 | CG2 | ILE | B | 395 | −58.464 | −70.460 | −34.410 | 1.00 | 22.20 | C |
| ATOM | 1892 | C | ILE | B | 395 | −58.775 | −68.219 | −36.137 | 1.00 | 19.25 | C |
| ATOM | 1893 | O | ILE | B | 395 | −58.557 | −68.868 | −37.148 | 1.00 | 21.59 | O |
| ATOM | 1894 | N | CYS | B | 396 | −59.944 | −67.651 | −35.928 | 1.00 | 21.06 | N |
| ATOM | 1895 | CA | CYS | B | 396 | −61.058 | −67.925 | −36.827 | 1.00 | 18.45 | C |
| ATOM | 1896 | CB | CYS | B | 396 | −62.204 | −68.608 | −36.062 | 1.00 | 19.51 | C |
| ATOM | 1897 | SG | CYS | B | 396 | −63.158 | −67.498 | −34.999 | 1.00 | 15.41 | S |
| ATOM | 1898 | C | CYS | B | 396 | −61.547 | −66.684 | −37.538 | 1.00 | 15.72 | C |
| ATOM | 1899 | O | CYS | B | 396 | −62.482 | −66.756 | −38.345 | 1.00 | 18.77 | O |
| ATOM | 1900 | N | ALA | B | 397 | −60.888 | −65.556 | −37.274 | 1.00 | 18.08 | N |
| ATOM | 1901 | CA | ALA | B | 397 | −61.233 | −64.227 | −37.861 | 1.00 | 17.44 | C |
| ATOM | 1902 | CB | ALA | B | 397 | −60.887 | −64.160 | −39.352 | 1.00 | 20.70 | C |
| ATOM | 1903 | C | ALA | B | 397 | −62.661 | −63.729 | −37.597 | 1.00 | 21.08 | C |
| ATOM | 1904 | O | ALA | B | 397 | −63.096 | −62.741 | −38.199 | 1.00 | 23.11 | O |
| ATOM | 1905 | N | SER | B | 398 | −63.367 | −64.374 | −36.661 | 1.00 | 19.81 | N |
| ATOM | 1906 | CA | SER | B | 398 | −64.669 | −63.889 | −36.218 | 1.00 | 20.23 | C |
| ATOM | 1907 | CB | SER | B | 398 | −65.286 | −64.872 | −35.216 | 1.00 | 23.35 | C |
| ATOM | 1908 | OG | SER | B | 398 | −66.388 | −64.306 | −34.505 | 1.00 | 32.78 | O |
| ATOM | 1909 | C | SER | B | 398 | −64.523 | −62.476 | −35.612 | 1.00 | 21.34 | C |
| ATOM | 1910 | O | SER | B | 398 | −63.582 | −62.213 | −34.848 | 1.00 | 16.15 | O |
| ATOM | 1911 | N | HIS | B | 399 | −65.405 | −61.552 | −36.007 | 1.00 | 20.25 | N |
| ATOM | 1912 | CA | HIS | B | 399 | −65.327 | −60.141 | −35.525 | 1.00 | 20.47 | C |
| ATOM | 1913 | CB | HIS | B | 399 | −66.172 | −59.200 | −36.401 | 1.00 | 24.87 | C |
| ATOM | 1914 | CG | HIS | B | 399 | −65.501 | −58.780 | −37.735 | 1.00 | 28.78 | C |
| ATOM | 1915 | ND1 | HIS | B | 399 | −64.658 | −59.592 | −38.440 | 1.00 | 32.93 | N |
| ATOM | 1916 | CE1 | HIS | B | 399 | −64.248 | −58.952 | −39.564 | 1.00 | 25.71 | C |
| ATOM | 1917 | NE2 | HIS | B | 399 | −64.842 | −57.774 | −39.603 | 1.00 | 32.33 | N |
| ATOM | 1918 | CD2 | HIS | B | 399 | −65.662 | −57.598 | −38.496 | 1.00 | 28.84 | C |
| ATOM | 1919 | C | HIS | B | 399 | −65.784 | −60.083 | −34.091 | 1.00 | 20.30 | C |
| ATOM | 1920 | O | HIS | B | 399 | −66.959 | −60.271 | −33.792 | 1.00 | 22.11 | O |
| ATOM | 1921 | N | ILE | B | 400 | −64.863 | −59.582 | −33.163 | 1.00 | 19.61 | N |
| ATOM | 1922 | CA | ILE | B | 400 | −65.266 | −59.899 | −31.759 | 1.00 | 21.86 | C |
| ATOM | 1923 | CB | ILE | B | 400 | −64.165 | −60.512 | −30.849 | 1.00 | 22.15 | C |
| ATOM | 1924 | CG1 | ILE | B | 400 | −63.665 | −61.850 | −31.422 | 1.00 | 26.77 | C |
| ATOM | 1925 | CD1 | ILE | B | 400 | −64.653 | −63.002 | −31.362 | 1.00 | 26.26 | C |
| ATOM | 1926 | CG2 | ILE | B | 400 | −64.662 | −60.632 | −29.408 | 1.00 | 20.54 | C |
| ATOM | 1927 | C | ILE | B | 400 | −65.686 | −58.535 | −31.241 | 1.00 | 16.33 | C |
| ATOM | 1928 | O | ILE | B | 400 | −66.556 | −58.423 | −30.380 | 1.00 | 19.94 | O |
| ATOM | 1929 | N | GLY | B | 401 | −65.034 | −57.500 | −31.735 | 1.00 | 16.07 | N |
| ATOM | 1930 | CA | GLY | B | 401 | −65.278 | −56.180 | −31.212 | 1.00 | 17.87 | C |
| ATOM | 1931 | C | GLY | B | 401 | −64.356 | −55.146 | −31.790 | 1.00 | 16.14 | C |
| ATOM | 1932 | O | GLY | B | 401 | −64.092 | −55.137 | −32.989 | 1.00 | 14.44 | O |
| ATOM | 1933 | N | TRP | B | 402 | −63.893 | −54.250 | −30.922 | 1.00 | 12.81 | N |
| ATOM | 1934 | CA | TRP | B | 402 | −63.101 | −53.115 | −31.323 | 1.00 | 14.87 | C |
| ATOM | 1935 | CB | TRP | B | 402 | −63.997 | −51.863 | −31.616 | 1.00 | 14.12 | C |
| ATOM | 1936 | CG | TRP | B | 402 | −65.021 | −52.110 | −32.658 | 1.00 | 17.28 | C |
| ATOM | 1937 | CD1 | TRP | B | 402 | −64.908 | −51.878 | −34.035 | 1.00 | 14.79 | C |
| ATOM | 1938 | NE1 | TRP | B | 402 | −66.031 | −52.309 | −34.686 | 1.00 | 19.82 | N |
| ATOM | 1939 | CE2 | TRP | B | 402 | −66.914 | −52.852 | −33.798 | 1.00 | 20.82 | C |
| ATOM | 1940 | CD2 | TRP | B | 402 | −66.309 | −52.755 | −32.474 | 1.00 | 20.27 | C |
| ATOM | 1941 | CE3 | TRP | B | 402 | −67.005 | −53.253 | −31.369 | 1.00 | 20.96 | C |
| ATOM | 1942 | CZ3 | TRP | B | 402 | −68.260 | −53.808 | −31.583 | 1.00 | 19.60 | C |
| ATOM | 1943 | CH2 | TRP | B | 402 | −68.823 | −53.883 | −32.863 | 1.00 | 21.29 | C |
| ATOM | 1944 | CZ2 | TRP | B | 402 | −68.163 | −53.404 | −33.993 | 1.00 | 21.16 | C |
| ATOM | 1945 | C | TRP | B | 402 | −62.137 | −52.763 | −30.206 | 1.00 | 13.18 | C |
| ATOM | 1946 | O | TRP | B | 402 | −62.463 | −52.896 | −28.999 | 1.00 | 15.35 | O |
| ATOM | 1947 | N | LYS | B | 403 | −60.974 | −52.288 | −30.611 | 1.00 | 12.95 | N |
| ATOM | 1948 | CA | LYS | B | 403 | −60.040 | −51.619 | −29.720 | 1.00 | 13.69 | C |
| ATOM | 1949 | CB | LYS | B | 403 | −58.637 | −51.810 | −30.221 | 1.00 | 16.76 | C |
| ATOM | 1950 | CG | LYS | B | 403 | −57.611 | −51.355 | −29.225 | 1.00 | 17.41 | C |
| ATOM | 1951 | CD | LYS | B | 403 | −56.218 | −51.457 | −29.815 | 1.00 | 21.23 | C |
| ATOM | 1952 | CE | LYS | B | 403 | −55.179 | −51.201 | −28.718 | 1.00 | 30.54 | C |
| ATOM | 1953 | NZ | LYS | B | 403 | −53.800 | −51.226 | −29.288 | 1.00 | 28.03 | N |
| ATOM | 1954 | C | LYS | B | 403 | −60.348 | −50.141 | −29.757 | 1.00 | 14.38 | C |
| ATOM | 1955 | O | LYS | B | 403 | −60.469 | −49.547 | −30.865 | 1.00 | 14.57 | O |
| ATOM | 1956 | N | PHE | B | 404 | −60.558 | −49.553 | −28.574 | 1.00 | 13.76 | N |
| ATOM | 1957 | CA | PHE | B | 404 | −60.849 | −48.112 | −28.477 | 1.00 | 11.64 | C |
| ATOM | 1958 | CB | PHE | B | 404 | −62.092 | −47.858 | −27.593 | 1.00 | 10.58 | C |
| ATOM | 1959 | CG | PHE | B | 404 | −63.408 | −48.223 | −28.255 | 1.00 | 9.84 | C |
| ATOM | 1960 | CD1 | PHE | B | 404 | −64.081 | −47.295 | −29.068 | 1.00 | 12.16 | C |
| ATOM | 1961 | CE1 | PHE | B | 404 | −65.307 | −47.621 | −29.687 | 1.00 | 14.45 | C |
| ATOM | 1962 | CZ | PHE | B | 404 | −65.868 | −48.887 | −29.515 | 1.00 | 16.97 | C |
| ATOM | 1963 | CE2 | PHE | B | 404 | −65.223 | −49.826 | −28.701 | 1.00 | 10.79 | C |
| ATOM | 1964 | CD2 | PHE | B | 404 | −64.003 | −49.491 | −28.050 | 1.00 | 10.33 | C |
| ATOM | 1965 | C | PHE | B | 404 | −59.609 | −47.394 | −27.934 | 1.00 | 13.86 | C |

TABLE 4-continued

Atomic coordinates for CRBN(TBD):Pomalidomide (Murine protein)

| ATOM | 1966 | O   | PHE | B | 404 | −59.067 | −47.780 | −26.881 | 1.00 | 13.54 | O |
|------|------|-----|-----|---|-----|---------|---------|---------|------|-------|---|
| ATOM | 1967 | N   | THR | B | 405 | −59.168 | −46.365 | −28.651 | 1.00 | 14.47 | N |
| ATOM | 1968 | CA  | THR | B | 405 | −58.007 | −45.563 | −28.282 | 1.00 | 14.84 | C |
| ATOM | 1969 | CB  | THR | B | 405 | −56.930 | −45.655 | −29.382 | 1.00 | 18.43 | C |
| ATOM | 1970 | OG1 | THR | B | 405 | −57.570 | −45.517 | −30.635 | 1.00 | 16.61 | O |
| ATOM | 1971 | CG2 | THR | B | 405 | −56.290 | −47.077 | −29.365 | 1.00 | 21.24 | C |
| ATOM | 1972 | C   | THR | B | 405 | −58.405 | −44.102 | −28.075 | 1.00 | 14.32 | C |
| ATOM | 1973 | O   | THR | B | 405 | −59.160 | −43.520 | −28.857 | 1.00 | 15.36 | O |
| ATOM | 1974 | N   | ALA | B | 406 | −57.870 | −43.504 | −27.035 | 1.00 | 15.35 | N |
| ATOM | 1975 | CA  | ALA | B | 406 | −58.290 | −42.180 | −26.599 | 1.00 | 16.76 | C |
| ATOM | 1976 | CB  | ALA | B | 406 | −57.716 | −41.899 | −25.201 | 1.00 | 16.59 | C |
| ATOM | 1977 | C   | ALA | B | 406 | −57.757 | −41.169 | −27.616 | 1.00 | 17.96 | C |
| ATOM | 1978 | O   | ALA | B | 406 | −56.626 | −41.300 | −28.084 | 1.00 | 18.28 | O |
| ATOM | 1979 | N   | THR | B | 407 | −58.569 | −40.172 | −27.968 | 1.00 | 20.39 | N |
| ATOM | 1980 | CA  | THR | B | 407 | −58.090 | −39.097 | −28.884 | 1.00 | 24.31 | C |
| ATOM | 1981 | CB  | THR | B | 407 | −59.224 | −38.512 | −29.773 | 1.00 | 24.51 | C |
| ATOM | 1982 | OG1 | THR | B | 407 | −60.266 | −38.018 | −28.929 | 1.00 | 26.36 | O |
| ATOM | 1983 | CG2 | THR | B | 407 | −59.793 | −39.589 | −30.659 | 1.00 | 26.30 | C |
| ATOM | 1984 | C   | THR | B | 407 | −57.363 | −37.959 | −28.141 | 1.00 | 29.72 | C |
| ATOM | 1985 | O   | THR | B | 407 | −56.695 | −37.166 | −28.785 | 1.00 | 31.71 | O |
| ATOM | 1986 | N   | LYS | B | 408 | −57.492 | −37.894 | −26.804 | 1.00 | 26.17 | N |
| ATOM | 1987 | CA  | LYS | B | 408 | −56.868 | −36.817 | −25.952 | 1.00 | 29.08 | C |
| ATOM | 1988 | CB  | LYS | B | 408 | −57.945 | −35.921 | −25.301 | 1.00 | 28.98 | C |
| ATOM | 1989 | CG  | LYS | B | 408 | −58.539 | −34.802 | −26.139 | 1.00 | 41.20 | C |
| ATOM | 1990 | CD  | LYS | B | 408 | −59.972 | −34.533 | −25.677 | 1.00 | 45.11 | C |
| ATOM | 1991 | CE  | LYS | B | 408 | −60.332 | −33.056 | −25.611 | 1.00 | 45.63 | C |
| ATOM | 1992 | NZ  | LYS | B | 408 | −59.736 | −32.379 | −24.414 | 1.00 | 43.58 | N |
| ATOM | 1993 | C   | LYS | B | 408 | −56.037 | −37.470 | −24.819 | 1.00 | 29.18 | C |
| ATOM | 1994 | O   | LYS | B | 408 | −56.420 | −38.509 | −24.297 | 1.00 | 19.21 | O |
| ATOM | 1995 | N   | LYS | B | 409 | −54.944 | −36.836 | −24.397 | 1.00 | 20.60 | N |
| ATOM | 1996 | CA  | LYS | B | 409 | −54.025 | −37.479 | −23.439 | 1.00 | 24.77 | C |
| ATOM | 1997 | CB  | LYS | B | 409 | −52.662 | −36.745 | −23.389 | 1.00 | 31.30 | C |
| ATOM | 1998 | CG  | LYS | B | 409 | −51.836 | −36.782 | −24.681 | 1.00 | 46.02 | C |
| ATOM | 1999 | CD  | LYS | B | 409 | −51.176 | −38.139 | −24.923 | 1.00 | 49.56 | C |
| ATOM | 2000 | CE  | LYS | B | 409 | −49.847 | −37.975 | −25.646 | 1.00 | 51.63 | C |
| ATOM | 2001 | NZ  | LYS | B | 409 | −48.832 | −38.962 | −25.185 | 1.00 | 62.60 | N |
| ATOM | 2002 | C   | LYS | B | 409 | −54.590 | −37.511 | −22.023 | 1.00 | 21.47 | C |
| ATOM | 2003 | O   | LYS | B | 409 | −54.129 | −38.279 | −21.202 | 1.00 | 21.08 | O |
| ATOM | 2004 | N   | ASP | B | 410 | −55.547 | −36.640 | −21.719 | 1.00 | 25.31 | N |
| ATOM | 2005 | CA  | ASP | B | 410 | −55.948 | −36.455 | −20.299 | 1.00 | 29.10 | C |
| ATOM | 2006 | CB  | ASP | B | 410 | −56.297 | −34.978 | −20.028 | 1.00 | 33.62 | C |
| ATOM | 2007 | CG  | ASP | B | 410 | −57.653 | −34.577 | −20.585 | 1.00 | 40.02 | C |
| ATOM | 2008 | OD1 | ASP | B | 410 | −58.155 | −35.236 | −21.536 | 1.00 | 47.35 | O |
| ATOM | 2009 | OD2 | ASP | B | 410 | −58.233 | −33.616 | −20.045 | 1.00 | 49.30 | O |
| ATOM | 2010 | C   | ASP | B | 410 | −57.067 | −37.442 | −19.809 | 1.00 | 34.82 | C |
| ATOM | 2011 | O   | ASP | B | 410 | −57.489 | −37.421 | −18.626 | 1.00 | 35.70 | O |
| ATOM | 2012 | N   | MET | B | 411 | −57.530 | −38.286 | −20.739 | 1.00 | 26.70 | N |
| ATOM | 2013 | CA  | MET | B | 411 | −58.584 | −39.274 | −20.510 | 1.00 | 24.05 | C |
| ATOM | 2014 | CB  | MET | B | 411 | −59.237 | −39.654 | −21.855 | 1.00 | 17.20 | C |
| ATOM | 2015 | CG  | MET | B | 411 | −60.070 | −38.504 | −22.378 | 1.00 | 34.35 | C |
| ATOM | 2016 | SD  | MET | B | 411 | −60.976 | −38.897 | −23.854 | 1.00 | 41.84 | S |
| ATOM | 2017 | CE  | MET | B | 411 | −59.753 | −38.728 | −25.116 | 1.00 | 35.00 | C |
| ATOM | 2018 | C   | MET | B | 411 | −58.039 | −40.535 | −19.855 | 1.00 | 17.85 | C |
| ATOM | 2019 | O   | MET | B | 411 | −56.845 | −40.853 | −19.997 | 1.00 | 15.52 | O |
| ATOM | 2020 | N   | SER | B | 412 | −58.912 | −41.278 | −19.157 | 1.00 | 15.11 | N |
| ATOM | 2021 | CA  | SER | B | 412 | −58.504 | −42.594 | −18.652 | 1.00 | 15.31 | C |
| ATOM | 2022 | CB  | SER | B | 412 | −58.084 | −42.521 | −17.179 | 1.00 | 16.71 | C |
| ATOM | 2023 | OG  | SER | B | 412 | −59.151 | −41.959 | −16.435 | 1.00 | 23.31 | O |
| ATOM | 2024 | C   | SER | B | 412 | −59.655 | −43.563 | −18.973 | 1.00 | 13.44 | C |
| ATOM | 2025 | O   | SER | B | 412 | −60.817 | −43.204 | −18.697 | 1.00 | 17.40 | O |
| ATOM | 2026 | N   | PRO | B | 413 | −59.332 | −44.847 | −19.117 | 1.00 | 10.84 | N |
| ATOM | 2027 | CA  | PRO | B | 413 | −58.133 | −45.357 | −19.761 | 1.00 | 11.77 | C |
| ATOM | 2028 | CB  | PRO | B | 413 | −58.413 | −46.872 | −19.866 | 1.00 | 13.65 | C |
| ATOM | 2029 | CG  | PRO | B | 413 | −59.905 | −46.914 | −20.137 | 1.00 | 12.35 | C |
| ATOM | 2030 | CD  | PRO | B | 413 | −60.464 | −45.793 | −19.272 | 1.00 | 12.44 | C |
| ATOM | 2031 | C   | PRO | B | 413 | −57.774 | −44.740 | −21.092 | 1.00 | 12.24 | C |
| ATOM | 2032 | O   | PRO | B | 413 | −58.648 | −44.246 | −21.812 | 1.00 | 14.30 | O |
| ATOM | 2033 | N   | GLN | B | 414 | −56.506 | −44.747 | −21.420 | 1.00 | 11.17 | N |
| ATOM | 2034 | CA  | GLN | B | 414 | −56.120 | −44.301 | −22.767 | 1.00 | 13.27 | C |
| ATOM | 2035 | CB  | GLN | B | 414 | −54.614 | −44.069 | −22.841 | 1.00 | 15.40 | C |
| ATOM | 2036 | CG  | GLN | B | 414 | −54.160 | −42.747 | −22.221 | 1.00 | 14.10 | C |
| ATOM | 2037 | CD  | GLN | B | 414 | −54.693 | −41.558 | −22.994 | 1.00 | 18.35 | C |
| ATOM | 2038 | OE1 | GLN | B | 414 | −55.586 | −40.819 | −22.546 | 1.00 | 20.00 | O |
| ATOM | 2039 | NE2 | GLN | B | 414 | −54.195 | −41.398 | −24.161 | 1.00 | 12.41 | N |
| ATOM | 2040 | C   | GLN | B | 414 | −56.527 | −45.323 | −23.848 | 1.00 | 14.48 | C |
| ATOM | 2041 | O   | GLN | B | 414 | −56.590 | −44.995 | −25.024 | 1.00 | 14.59 | O |
| ATOM | 2042 | N   | LYS | B | 415 | −56.738 | −46.580 | −23.460 | 1.00 | 14.53 | N |
| ATOM | 2043 | CA  | LYS | B | 415 | −57.175 | −47.611 | −24.412 | 1.00 | 17.31 | C |

TABLE 4-continued

Atomic coordinates for CRBN(TBD):Pomalidomide (Murine protein)

| ATOM | 2044 | CB | LYS | B | 415 | −55.987 | −48.330 | −25.110 | 1.00 | 23.52 | C |
|---|---|---|---|---|---|---|---|---|---|---|---|
| ATOM | 2045 | CG | LYS | B | 415 | −55.256 | −49.356 | −24.243 | 1.00 | 40.74 | C |
| ATOM | 2046 | CD | LYS | B | 415 | −53.820 | −49.626 | −24.737 | 1.00 | 39.00 | C |
| ATOM | 2047 | CE | LYS | B | 415 | −52.897 | −50.020 | −23.594 | 1.00 | 32.11 | C |
| ATOM | 2048 | NZ | LYS | B | 415 | −52.701 | −48.939 | −22.525 | 1.00 | 26.56 | N |
| ATOM | 2049 | C | LYS | B | 415 | −58.003 | −48.599 | −23.689 | 1.00 | 13.15 | C |
| ATOM | 2050 | O | LYS | B | 415 | −57.815 | −48.779 | −22.501 | 1.00 | 10.43 | O |
| ATOM | 2051 | N | PHE | B | 416 | −58.932 | −49.234 | −24.406 | 1.00 | 10.99 | N |
| ATOM | 2052 | CA | PHE | B | 416 | −59.677 | −50.352 | −23.876 | 1.00 | 10.40 | C |
| ATOM | 2053 | CB | PHE | B | 416 | −60.753 | −49.882 | −22.812 | 1.00 | 9.75 | C |
| ATOM | 2054 | CG | PHE | B | 416 | −61.895 | −49.088 | −23.401 | 1.00 | 9.21 | C |
| ATOM | 2055 | CD1 | PHE | B | 416 | −63.093 | −49.739 | −23.831 | 1.00 | 10.57 | C |
| ATOM | 2056 | CE1 | PHE | B | 416 | −64.128 | −49.031 | −24.430 | 1.00 | 10.35 | C |
| ATOM | 2057 | CZ | PHE | B | 416 | −64.045 | −47.625 | −24.564 | 1.00 | 12.50 | C |
| ATOM | 2058 | CE2 | PHE | B | 416 | −62.885 | −46.954 | −24.155 | 1.00 | 8.92 | C |
| ATOM | 2059 | CD2 | PHE | B | 416 | −61.807 | −47.683 | −23.549 | 1.00 | 10.68 | C |
| ATOM | 2060 | C | PHE | B | 416 | −60.318 | −51.160 | −25.050 | 1.00 | 12.88 | C |
| ATOM | 2061 | O | PHE | B | 416 | −60.111 | −50.846 | −26.219 | 1.00 | 13.90 | O |
| ATOM | 2062 | N | TRP | B | 417 | −60.987 | −52.261 | −24.705 | 1.00 | 13.08 | N |
| ATOM | 2063 | CA | TRP | B | 417 | −61.687 | −53.112 | −25.666 | 1.00 | 13.85 | C |
| ATOM | 2064 | CB | TRP | B | 417 | −61.141 | −54.552 | −25.639 | 1.00 | 13.48 | C |
| ATOM | 2065 | CG | TRP | B | 417 | −59.620 | −54.608 | −25.784 | 1.00 | 14.05 | C |
| ATOM | 2066 | CD1 | TRP | B | 417 | −58.672 | −54.422 | −24.788 | 1.00 | 13.47 | C |
| ATOM | 2067 | NE1 | TRP | B | 417 | −57.423 | −54.499 | −25.293 | 1.00 | 14.55 | N |
| ATOM | 2068 | CE2 | TRP | B | 417 | −57.470 | −54.750 | −26.363 | 1.00 | 13.61 | C |
| ATOM | 2069 | CD2 | TRP | B | 417 | −58.858 | −54.797 | −27.012 | 1.00 | 12.44 | C |
| ATOM | 2070 | CE3 | TRP | B | 417 | −59.206 | −55.068 | −28.362 | 1.00 | 13.69 | C |
| ATOM | 2071 | CZ3 | TRP | B | 417 | −58.182 | −55.257 | −29.273 | 1.00 | 19.69 | C |
| ATOM | 2072 | CH2 | TRP | B | 417 | −56.832 | −55.254 | −28.861 | 1.00 | 14.18 | C |
| ATOM | 2073 | CZ2 | TRP | B | 417 | −56.459 | −54.986 | −27.532 | 1.00 | 12.37 | C |
| ATOM | 2074 | C | TRP | B | 417 | −63.180 | −53.092 | −25.441 | 1.00 | 14.18 | C |
| ATOM | 2075 | O | TRP | B | 417 | −63.659 | −53.217 | −24.304 | 1.00 | 16.51 | O |
| ATOM | 2076 | N | GLY | B | 418 | −63.937 | −52.910 | −26.523 | 1.00 | 16.17 | N |
| ATOM | 2077 | CA | GLY | B | 418 | −65.396 | −53.083 | −26.452 | 1.00 | 16.33 | C |
| ATOM | 2078 | C | GLY | B | 418 | −65.728 | −54.368 | −27.187 | 1.00 | 20.32 | C |
| ATOM | 2079 | O | GLY | B | 418 | −65.492 | −54.466 | −28.411 | 1.00 | 17.26 | O |
| ATOM | 2080 | N | LEU | B | 419 | −66.219 | −55.366 | −26.450 | 1.00 | 17.26 | N |
| ATOM | 2081 | CA | LEU | B | 419 | −66.427 | −56.708 | −27.019 | 1.00 | 14.96 | C |
| ATOM | 2082 | CB | LEU | B | 419 | −65.711 | −57.785 | −26.140 | 1.00 | 14.51 | C |
| ATOM | 2083 | CG | LEU | B | 419 | −64.180 | −57.669 | −25.998 | 1.00 | 18.66 | C |
| ATOM | 2084 | CD1 | LEU | B | 419 | −63.556 | −58.787 | −25.169 | 1.00 | 18.93 | C |
| ATOM | 2085 | CD2 | LEU | B | 419 | −63.451 | −57.518 | −27.339 | 1.00 | 15.37 | C |
| ATOM | 2086 | C | LEU | B | 419 | −67.916 | −57.024 | −27.108 | 1.00 | 17.49 | C |
| ATOM | 2087 | O | LEU | B | 419 | −68.699 | −56.758 | −26.168 | 1.00 | 21.46 | O |
| ATOM | 2088 | N | THR | B | 420 | −68.338 | −57.542 | −28.254 | 1.00 | 17.17 | N |
| ATOM | 2089 | CA | THR | B | 420 | −69.732 | −58.020 | −28.398 | 1.00 | 18.52 | C |
| ATOM | 2090 | CB | THR | B | 420 | −70.032 | −58.310 | −29.854 | 1.00 | 20.38 | C |
| ATOM | 2091 | OG1 | THR | B | 420 | −69.730 | −57.117 | −30.606 | 1.00 | 18.00 | O |
| ATOM | 2092 | CG2 | THR | B | 420 | −71.538 | −58.737 | −30.036 | 1.00 | 19.04 | C |
| ATOM | 2093 | C | THR | B | 420 | −69.993 | −59.249 | −27.529 | 1.00 | 16.35 | C |
| ATOM | 2094 | O | THR | B | 420 | −69.338 | −60.271 | −27.697 | 1.00 | 19.67 | O |
| ATOM | 2095 | N | ARG | B | 421 | −70.899 | −59.120 | −26.548 | 1.00 | 16.93 | N |
| ATOM | 2096 | CA | ARG | B | 421 | −71.164 | −60.206 | −25.577 | 1.00 | 18.81 | C |
| ATOM | 2097 | CB | ARG | B | 421 | −72.268 | −59.826 | −24.577 | 1.00 | 24.60 | C |
| ATOM | 2098 | CG | ARG | B | 421 | −71.821 | −58.931 | −23.437 | 1.00 | 30.60 | C |
| ATOM | 2099 | CD | ARG | B | 421 | −73.021 | −58.413 | −22.643 | 1.00 | 44.49 | C |
| ATOM | 2100 | NE | ARG | B | 421 | −72.679 | −57.216 | −21.870 | 1.00 | 47.25 | N |
| ATOM | 2101 | CZ | ARG | B | 421 | −72.379 | −57.215 | −20.575 | 1.00 | 46.85 | C |
| ATOM | 2102 | NH1 | ARG | B | 421 | −72.392 | −58.349 | −19.885 | 1.00 | 44.56 | N |
| ATOM | 2103 | NH2 | ARG | B | 421 | −72.061 | −56.077 | −19.972 | 1.00 | 47.36 | N |
| ATOM | 2104 | C | ARG | B | 421 | −71.609 | −61.463 | −26.299 | 1.00 | 16.85 | C |
| ATOM | 2105 | O | ARG | B | 421 | −71.316 | −62.546 | −25.852 | 1.00 | 16.59 | O |
| ATOM | 2106 | N | SER | B | 422 | −72.334 | −61.299 | −27.403 | 1.00 | 18.31 | N |
| ATOM | 2107 | CA | SER | B | 422 | −72.869 | −62.464 | −28.121 | 1.00 | 18.55 | C |
| ATOM | 2108 | CB | SER | B | 422 | −74.081 | −62.105 | −28.987 | 1.00 | 20.38 | C |
| ATOM | 2109 | OG | SER | B | 422 | −73.737 | −61.243 | −30.075 | 1.00 | 23.74 | O |
| ATOM | 2110 | C | SER | B | 422 | −71.798 | −63.189 | −28.927 | 1.00 | 19.31 | C |
| ATOM | 2111 | O | SER | B | 422 | −72.034 | −64.284 | −29.382 | 1.00 | 23.34 | O |
| ATOM | 2112 | N | ALA | B | 423 | −70.608 | −62.589 | −29.060 | 1.00 | 16.02 | N |
| ATOM | 2113 | CA | ALA | B | 423 | −69.474 | −63.220 | −29.779 | 1.00 | 19.92 | C |
| ATOM | 2114 | CB | ALA | B | 423 | −68.702 | −62.171 | −30.574 | 1.00 | 18.55 | C |
| ATOM | 2115 | C | ALA | B | 423 | −68.524 | −63.995 | −28.836 | 1.00 | 19.44 | C |
| ATOM | 2116 | O | ALA | B | 423 | −67.477 | −64.478 | −29.266 | 1.00 | 17.26 | O |
| ATOM | 2117 | N | LEU | B | 424 | −68.909 | −64.095 | −27.554 | 1.00 | 22.12 | N |
| ATOM | 2118 | CA | LEU | B | 424 | −68.095 | −64.754 | −26.491 | 1.00 | 23.35 | C |
| ATOM | 2119 | CB | LEU | B | 424 | −67.556 | −63.704 | −25.505 | 1.00 | 17.68 | C |
| ATOM | 2120 | CG | LEU | B | 424 | −66.679 | −62.549 | −26.041 | 1.00 | 24.01 | C |
| ATOM | 2121 | CD1 | LEU | B | 424 | −66.498 | −61.410 | −25.012 | 1.00 | 17.33 | C |

TABLE 4-continued

Atomic coordinates for CRBN(TBD):Pomalidomide (Murine protein)

| ATOM | 2122 | CD2 | LEU | B | 424 | −65.329 | −63.073 | −26.519 | 1.00 | 23.03 | C |
|------|------|-----|-----|---|-----|---------|---------|---------|------|-------|---|
| ATOM | 2123 | C | LEU | B | 424 | −68.896 | −65.833 | −25.703 | 1.00 | 23.59 | C |
| ATOM | 2124 | O | LEU | B | 424 | −70.105 | −65.704 | −25.530 | 1.00 | 21.33 | O |
| ATOM | 2125 | N | LEU | B | 425 | −68.201 | −66.844 | −25.186 | 1.00 | 25.46 | N |
| ATOM | 2126 | CA | LEU | B | 425 | −68.837 | −67.906 | −24.386 | 1.00 | 40.40 | C |
| ATOM | 2127 | CB | LEU | B | 425 | −68.614 | −69.305 | −24.981 | 1.00 | 33.88 | C |
| ATOM | 2128 | CG | LEU | B | 425 | −69.588 | −69.714 | −26.127 | 1.00 | 37.90 | C |
| ATOM | 2129 | CD1 | LEU | B | 425 | −69.444 | −71.187 | −26.510 | 1.00 | 32.69 | C |
| ATOM | 2130 | CD2 | LEU | B | 425 | −71.058 | −69.369 | −25.851 | 1.00 | 33.19 | C |
| ATOM | 2131 | C | LEU | B | 425 | −68.376 | −67.856 | −22.942 | 1.00 | 41.07 | C |
| ATOM | 2132 | O | LEU | B | 425 | −67.202 | −67.560 | −22.694 | 1.00 | 30.97 | O |
| ATOM | 2133 | N | PRO | B | 426 | −69.215 | −68.395 | −22.026 | 1.00 | 51.06 | N |
| ATOM | 2134 | CA | PRO | B | 426 | −69.893 | −67.749 | −20.943 | 1.00 | 56.21 | C |
| ATOM | 2135 | CB | PRO | B | 426 | −68.813 | −67.724 | −19.855 | 1.00 | 55.03 | C |
| ATOM | 2136 | CG | PRO | B | 426 | −68.159 | −68.089 | −20.054 | 1.00 | 54.92 | C |
| ATOM | 2137 | CD | PRO | B | 426 | −68.569 | −69.589 | −21.459 | 1.00 | 66.24 | C |
| ATOM | 2138 | C | PRO | B | 426 | −70.592 | −66.396 | −21.222 | 1.00 | 71.60 | C |
| ATOM | 2139 | O | PRO | B | 426 | −70.422 | −65.785 | −22.294 | 1.00 | 54.58 | O |
| ATOM | 2140 | N | THR | B | 427 | −71.397 | −65.973 | −20.242 | 1.00 | 89.60 | N |
| ATOM | 2141 | CA | THR | B | 427 | −72.420 | −64.935 | −20.401 | 1.00 | 77.65 | C |
| ATOM | 2142 | CB | THR | B | 427 | −73.814 | −65.586 | −20.589 | 1.00 | 69.12 | C |
| ATOM | 2143 | OG1 | THR | B | 427 | −73.809 | −66.395 | −21.776 | 1.00 | 60.00 | O |
| ATOM | 2144 | CG2 | THR | B | 427 | −74.933 | −64.530 | −20.683 | 1.00 | 65.95 | C |
| ATOM | 2145 | C | THR | B | 427 | −72.441 | −64.012 | −19.172 | 1.00 | 81.95 | C |
| ATOM | 2146 | O | THR | B | 427 | −72.431 | −62.783 | −19.294 | 1.00 | 65.36 | O |
| ATOM | 2147 | N | THR | C | 321 | −81.163 | −67.769 | −55.070 | 1.00 | 46.98 | N |
| ATOM | 2148 | CA | THR | C | 321 | −80.836 | −66.347 | −54.733 | 1.00 | 42.28 | C |
| ATOM | 2149 | CB | THR | C | 321 | −81.543 | −65.351 | −55.684 | 1.00 | 37.36 | C |
| ATOM | 2150 | OG1 | THR | C | 321 | −82.953 | −65.596 | −55.664 | 1.00 | 42.28 | O |
| ATOM | 2151 | CG2 | THR | C | 321 | −80.998 | −65.434 | −57.126 | 1.00 | 42.25 | C |
| ATOM | 2152 | C | THR | C | 321 | −81.211 | −65.956 | −53.292 | 1.00 | 33.29 | C |
| ATOM | 2153 | O | THR | C | 321 | −81.079 | −64.783 | −52.923 | 1.00 | 29.40 | O |
| ATOM | 2154 | N | SER | C | 322 | −81.683 | −66.930 | −52.503 | 1.00 | 29.39 | N |
| ATOM | 2155 | CA | SER | C | 322 | −82.173 | −66.709 | −51.142 | 1.00 | 23.65 | C |
| ATOM | 2156 | CB | SER | C | 322 | −82.999 | −67.894 | −50.681 | 1.00 | 25.25 | C |
| ATOM | 2157 | OG | SER | C | 322 | −84.127 | −68.022 | −51.510 | 1.00 | 33.84 | O |
| ATOM | 2158 | C | SER | C | 322 | −81.080 | −66.471 | −50.125 | 1.00 | 29.14 | C |
| ATOM | 2159 | O | SER | C | 322 | −80.048 | −67.114 | −50.172 | 1.00 | 25.03 | O |
| ATOM | 2160 | N | LEU | C | 323 | −81.322 | −65.544 | −49.195 | 1.00 | 26.40 | N |
| ATOM | 2161 | CA | LEU | C | 323 | −80.403 | −65.309 | −48.065 | 1.00 | 22.98 | C |
| ATOM | 2162 | CB | LEU | C | 323 | −79.781 | −63.884 | −48.103 | 1.00 | 18.13 | C |
| ATOM | 2163 | CG | LEU | C | 323 | −78.945 | −63.489 | −49.361 | 1.00 | 23.01 | C |
| ATOM | 2164 | CD1 | LEU | C | 323 | −78.737 | −61.981 | −49.492 | 1.00 | 17.98 | C |
| ATOM | 2165 | CD2 | LEU | C | 323 | −77.588 | −64.171 | −49.407 | 1.00 | 20.81 | C |
| ATOM | 2166 | C | LEU | C | 323 | −81.193 | −65.563 | −46.797 | 1.00 | 23.86 | C |
| ATOM | 2167 | O | LEU | C | 323 | −82.283 | −64.990 | −46.595 | 1.00 | 18.07 | O |
| ATOM | 2168 | N | CYS | C | 324 | −80.666 | −66.483 | −45.980 | 1.00 | 21.54 | N |
| ATOM | 2169 | CA | CYS | C | 324 | −81.371 | −67.085 | −44.862 | 1.00 | 20.05 | C |
| ATOM | 2170 | CB | CYS | C | 324 | −81.509 | −68.631 | −45.051 | 1.00 | 20.12 | C |
| ATOM | 2171 | SG | CYS | C | 324 | −82.543 | −69.144 | −46.460 | 1.00 | 27.33 | S |
| ATOM | 2172 | C | CYS | C | 324 | −80.590 | −66.791 | −43.589 | 1.00 | 23.55 | C |
| ATOM | 2173 | O | CYS | C | 324 | −79.366 | −66.586 | −43.617 | 1.00 | 18.04 | O |
| ATOM | 2174 | N | CYS | C | 325 | −81.310 | −66.761 | −42.479 | 1.00 | 17.94 | N |
| ATOM | 2175 | CA | CYS | C | 325 | −80.722 | −66.617 | −41.151 | 1.00 | 20.92 | C |
| ATOM | 2176 | CB | CYS | C | 325 | −81.855 | −66.707 | −40.105 | 1.00 | 19.55 | C |
| ATOM | 2177 | SG | CYS | C | 325 | −81.339 | −66.979 | −38.396 | 1.00 | 18.34 | S |
| ATOM | 2178 | C | CYS | C | 325 | −79.653 | −67.721 | −40.907 | 1.00 | 24.37 | C |
| ATOM | 2179 | O | CYS | C | 325 | −79.906 | −68.924 | −41.117 | 1.00 | 19.12 | O |
| ATOM | 2180 | N | LYS | C | 326 | −78.443 | −67.312 | −40.558 | 1.00 | 24.15 | N |
| ATOM | 2181 | CA | LYS | C | 326 | −77.371 | −68.297 | −40.405 | 1.00 | 26.10 | C |
| ATOM | 2182 | CB | LYS | C | 326 | −75.973 | −67.662 | −40.433 | 1.00 | 24.93 | C |
| ATOM | 2183 | CG | LYS | C | 326 | −74.836 | −68.701 | −40.469 | 1.00 | 24.58 | C |
| ATOM | 2184 | CD | LYS | C | 326 | −73.473 | −68.047 | −40.514 | 1.00 | 26.62 | C |
| ATOM | 2185 | CE | LYS | C | 326 | −72.941 | −67.813 | −39.104 | 1.00 | 38.73 | C |
| ATOM | 2186 | NZ | LYS | C | 326 | −71.982 | −66.675 | −39.005 | 1.00 | 40.49 | N |
| ATOM | 2187 | C | LYS | C | 326 | −77.555 | −69.137 | −39.123 | 1.00 | 29.54 | C |
| ATOM | 2188 | O | LYS | C | 326 | −77.177 | −70.308 | −39.089 | 1.00 | 21.61 | O |
| ATOM | 2189 | N | GLN | C | 327 | −78.124 | −68.519 | −38.084 | 1.00 | 25.41 | N |
| ATOM | 2190 | CA | GLN | C | 327 | −78.401 | −69.211 | −36.848 | 1.00 | 22.49 | C |
| ATOM | 2191 | CB | GLN | C | 327 | −78.957 | −68.265 | −35.806 | 1.00 | 24.53 | C |
| ATOM | 2192 | CG | GLN | C | 327 | −79.069 | −68.951 | −34.431 | 1.00 | 22.84 | C |
| ATOM | 2193 | CD | GLN | C | 327 | −78.801 | −68.012 | −33.289 | 1.00 | 22.97 | C |
| ATOM | 2194 | OE1 | GLN | C | 327 | −77.658 | −67.811 | −32.914 | 1.00 | 35.53 | O |
| ATOM | 2195 | NE2 | GLN | C | 327 | −79.851 | −67.427 | −32.732 | 1.00 | 16.95 | N |
| ATOM | 2196 | C | GLN | C | 327 | −79.329 | −70.419 | −37.002 | 1.00 | 21.89 | C |
| ATOM | 2197 | O | GLN | C | 327 | −78.950 | −71.540 | −36.605 | 1.00 | 16.38 | O |
| ATOM | 2198 | N | CYS | C | 328 | −80.540 | −70.201 | −37.549 | 1.00 | 14.98 | N |
| ATOM | 2199 | CA | CYS | C | 328 | −81.527 | −71.273 | −37.644 | 1.00 | 19.22 | C |

TABLE 4-continued

Atomic coordinates for CRBN(TBD):Pomalidomide (Murine protein)

| ATOM | 2200 | CB | CYS | C | 328 | −82.887 | −70.835 | −37.066 | 1.00 | 25.65 | C |
|---|---|---|---|---|---|---|---|---|---|---|---|
| ATOM | 2201 | SG | CYS | C | 328 | −83.827 | −69.631 | −38.049 | 1.00 | 21.74 | S |
| ATOM | 2202 | C | CYS | C | 328 | −81.715 | −71.936 | −39.019 | 1.00 | 21.58 | C |
| ATOM | 2203 | O | CYS | C | 328 | −82.304 | −73.017 | −39.089 | 1.00 | 22.23 | O |
| ATOM | 2204 | N | GLN | C | 329 | −81.256 | −71.288 | −40.096 | 1.00 | 20.04 | N |
| ATOM | 2205 | CA | GLN | C | 329 | −81.562 | −71.723 | −41.516 | 1.00 | 21.99 | C |
| ATOM | 2206 | CB | GLN | C | 329 | −80.689 | −72.917 | −41.948 | 1.00 | 25.27 | C |
| ATOM | 2207 | CG | GLN | C | 329 | −79.180 | −72.689 | −41.918 | 1.00 | 30.77 | C |
| ATOM | 2208 | CD | GLN | C | 329 | −78.394 | −73.954 | −42.272 | 1.00 | 33.68 | C |
| ATOM | 2209 | OE1 | GLN | C | 329 | −78.519 | −74.495 | −43.375 | 1.00 | 30.38 | O |
| ATOM | 2210 | NE2 | GLN | C | 329 | −77.592 | −74.423 | −41.342 | 1.00 | 25.06 | N |
| ATOM | 2211 | C | GLN | C | 329 | −83.040 | −72.023 | −41.887 | 1.00 | 25.06 | C |
| ATOM | 2212 | O | GLN | C | 329 | −83.308 | −72.631 | −42.910 | 1.00 | 27.35 | O |
| ATOM | 2213 | N | GLN | C | 329 | −83.990 | −71.363 | −41.056 | 1.00 | 26.36 | N |
| ATOM | 2214 | CA | GLU | C | 330 | −85.396 | −71.863 | −41.359 | 1.00 | 24.07 | C |
| ATOM | 2215 | CB | GLU | C | 330 | −86.243 | −71.703 | −40.104 | 1.00 | 27.75 | C |
| ATOM | 2216 | CG | GLU | C | 330 | −86.080 | −72.794 | −39.080 | 1.00 | 31.44 | C |
| ATOM | 2217 | CD | GLU | C | 330 | −87.357 | −73.576 | −38.881 | 1.00 | 45.20 | C |
| ATOM | 2218 | OE1 | GLU | C | 330 | −87.653 | −74.442 | −39.729 | 1.00 | 60.72 | O |
| ATOM | 2219 | OE2 | GLU | C | 330 | −88.058 | −73.332 | −37.874 | 1.00 | 44.35 | O |
| ATOM | 2220 | C | GLU | C | 330 | −85.858 | −70.785 | −42.291 | 1.00 | 26.46 | C |
| ATOM | 2221 | O | GLU | C | 330 | −86.682 | −71.019 | −43.162 | 1.00 | 22.85 | O |
| ATOM | 2222 | N | THR | C | 331 | −85.350 | −69.586 | −42.061 | 1.00 | 22.12 | N |
| ATOM | 2223 | CA | THR | C | 331 | −86.007 | −68.375 | −42.536 | 1.00 | 27.33 | C |
| ATOM | 2224 | CB | THR | C | 331 | −86.116 | −67.374 | −41.382 | 1.00 | 27.69 | C |
| ATOM | 2225 | OG1 | THR | C | 331 | −85.152 | −67.723 | −40.378 | 1.00 | 46.96 | O |
| ATOM | 2226 | CG2 | THR | C | 331 | −87.506 | −67.428 | −40.774 | 1.00 | 28.75 | C |
| ATOM | 2227 | C | THR | C | 331 | −85.263 | −67.697 | −43.666 | 1.00 | 21.21 | C |
| ATOM | 2228 | O | THR | C | 331 | −84.121 | −67.316 | −43.491 | 1.00 | 25.87 | O |
| ATOM | 2229 | N | GLU | C | 332 | −85.922 | −67.503 | −44.810 | 1.00 | 23.34 | N |
| ATOM | 2230 | CA | GLU | C | 332 | −85.435 | −66.548 | −45.818 | 1.00 | 21.62 | C |
| ATOM | 2231 | CB | GLU | C | 332 | −86.175 | −66.705 | −47.149 | 1.00 | 29.24 | C |
| ATOM | 2232 | CG | GLU | C | 332 | −85.475 | −66.033 | −48.320 | 1.00 | 22.09 | C |
| ATOM | 2233 | CD | GLU | C | 332 | −86.297 | −66.037 | −49.572 | 1.00 | 24.57 | C |
| ATOM | 2234 | OE1 | GLU | C | 332 | −86.188 | −66.985 | −50.373 | 1.00 | 20.93 | O |
| ATOM | 2235 | OE2 | GLU | C | 332 | −87.081 | −65.085 | −49.757 | 1.00 | 22.95 | O |
| ATOM | 2236 | C | GLU | C | 332 | −85.610 | −65.106 | −45.287 | 1.00 | 20.74 | C |
| ATOM | 2237 | O | GLU | C | 332 | −86.700 | −64.744 | −44.845 | 1.00 | 19.53 | O |
| ATOM | 2238 | N | ILE | C | 333 | −84.529 | −64.322 | −45.297 | 1.00 | 17.32 | N |
| ATOM | 2239 | CA | ILE | C | 333 | −84.564 | −62.924 | −44.780 | 1.00 | 19.51 | C |
| ATOM | 2240 | CB | ILE | C | 333 | −83.338 | −62.623 | −43.841 | 1.00 | 16.82 | C |
| ATOM | 2241 | CG1 | ILE | C | 333 | −83.321 | −63.521 | −42.593 | 1.00 | 19.39 | C |
| ATOM | 2242 | CD1 | ILE | C | 333 | −84.625 | −63.569 | −41.794 | 1.00 | 15.23 | C |
| ATOM | 2243 | CG2 | ILE | C | 333 | −83.303 | −61.181 | −43.364 | 1.00 | 15.68 | C |
| ATOM | 2244 | C | ILE | C | 333 | −84.641 | −61.931 | −45.960 | 1.00 | 19.54 | C |
| ATOM | 2245 | O | ILE | C | 333 | −85.355 | −60.913 | −45.907 | 1.00 | 21.47 | O |
| ATOM | 2246 | N | THR | C | 334 | −83.940 | −62.252 | −47.039 | 1.00 | 17.14 | N |
| ATOM | 2247 | CA | THR | C | 334 | −83.993 | −61.440 | −48.237 | 1.00 | 23.08 | C |
| ATOM | 2248 | CB | THR | C | 334 | −83.208 | −60.117 | −48.052 | 1.00 | 22.90 | C |
| ATOM | 2249 | OG1 | THR | C | 334 | −83.578 | −59.189 | −49.103 | 1.00 | 21.85 | O |
| ATOM | 2250 | CG2 | THR | C | 334 | −81.722 | −60.385 | −48.052 | 1.00 | 16.89 | C |
| ATOM | 2251 | C | THR | C | 334 | −83.513 | −62.257 | −49.462 | 1.00 | 26.72 | C |
| ATOM | 2252 | O | THR | C | 334 | −83.274 | −63.456 | −49.348 | 1.00 | 23.46 | O |
| ATOM | 2253 | N | THR | C | 335 | −83.436 | −61.627 | −50.632 | 1.00 | 20.32 | N |
| ATOM | 2254 | CA | THR | C | 335 | −82.870 | −62.287 | −51.805 | 1.00 | 22.95 | C |
| ATOM | 2255 | CB | THR | C | 335 | −83.965 | −62.677 | −52.828 | 1.00 | 17.83 | C |
| ATOM | 2256 | OG1 | THR | C | 335 | −84.351 | −61.523 | −53.575 | 1.00 | 18.96 | O |
| ATOM | 2257 | CG2 | THR | C | 335 | −85.189 | −63.250 | −52.125 | 1.00 | 22.92 | C |
| ATOM | 2258 | C | THR | C | 335 | −81.861 | −61.351 | −52.478 | 1.00 | 20.83 | C |
| ATOM | 2259 | O | THR | C | 335 | −81.930 | −60.142 | −52.293 | 1.00 | 25.75 | O |
| ATOM | 2260 | N | LYS | C | 336 | −80.951 | −61.896 | −53.272 | 1.00 | 21.32 | N |
| ATOM | 2261 | CA | LYS | C | 336 | −79.993 | −61.067 | −54.003 | 1.00 | 20.05 | C |
| ATOM | 2262 | CB | LYS | C | 336 | −79.017 | −61.916 | −54.830 | 1.00 | 20.79 | C |
| ATOM | 2263 | CG | LYS | C | 336 | −78.329 | −63.030 | −54.057 | 1.00 | 32.46 | C |
| ATOM | 2264 | CD | LYS | C | 336 | −77.133 | −63.556 | −54.839 | 1.00 | 29.11 | C |
| ATOM | 2265 | CE | LYS | C | 336 | −76.706 | −64.932 | −54.347 | 1.00 | 36.46 | C |
| ATOM | 2266 | NZ | LYS | C | 336 | −75.465 | −65.353 | −55.056 | 1.00 | 30.66 | N |
| ATOM | 2267 | C | LYS | C | 336 | −80.661 | −60.048 | −54.918 | 1.00 | 21.28 | C |
| ATOM | 2268 | O | LYS | C | 336 | −80.046 | −59.062 | −55.261 | 1.00 | 21.73 | O |
| ATOM | 2269 | N | ASN | C | 337 | −81.916 | −60.295 | −55.321 | 1.00 | 21.93 | N |
| ATOM | 2270 | CA | ASN | C | 337 | −82.666 | −59.342 | −56.141 | 1.00 | 21.42 | C |
| ATOM | 2271 | CB | ASN | C | 337 | −83.996 | −59.956 | −56.574 | 1.00 | 22.86 | C |
| ATOM | 2272 | CG | ASN | C | 337 | −83.798 | −61.137 | −57.482 | 1.00 | 32.77 | C |
| ATOM | 2273 | OD1 | ASN | C | 337 | −84.306 | −62.233 | −57.230 | 1.00 | 32.91 | O |
| ATOM | 2274 | ND2 | ASN | C | 337 | −83.010 | −60.933 | −58.528 | 1.00 | 28.14 | N |
| ATOM | 2275 | C | ASN | C | 337 | −82.921 | −58.012 | −55.468 | 1.00 | 20.11 | C |
| ATOM | 2276 | O | ASN | C | 337 | −83.025 | −56.991 | −56.118 | 1.00 | 25.16 | O |
| ATOM | 2277 | N | GLU | C | 338 | −82.996 | −58.032 | −54.151 | 1.00 | 23.05 | N |

TABLE 4-continued

Atomic coordinates for CRBN(TBD):Pomalidomide (Murine protein)

| ATOM | 2278 | CA | GLU | C | 338 | −83.342 | −56.850 | −53.383 | 1.00 | 20.08 | C |
|---|---|---|---|---|---|---|---|---|---|---|---|
| ATOM | 2279 | CB | GLU | C | 338 | −84.132 | −57.246 | −52.126 | 1.00 | 19.55 | C |
| ATOM | 2280 | CG | GLU | C | 338 | −85.419 | −58.008 | −52.395 | 1.00 | 21.56 | C |
| ATOM | 2281 | CD | GLU | C | 338 | −86.372 | −57.270 | −53.317 | 1.00 | 20.95 | C |
| ATOM | 2282 | OE1 | GLU | C | 338 | −86.465 | −56.039 | −53.249 | 1.00 | 21.12 | O |
| ATOM | 2283 | OE2 | GLU | C | 338 | −87.036 | −57.929 | −54.121 | 1.00 | 33.16 | O |
| ATOM | 2284 | C | GLU | C | 338 | −82.148 | −55.956 | −53.053 | 1.00 | 21.96 | C |
| ATOM | 2285 | O | GLU | C | 338 | −82.324 | −54.841 | −52.549 | 1.00 | 18.35 | O |
| ATOM | 2286 | N | ILE | C | 339 | −80.935 | −56.437 | −53.348 | 1.00 | 20.77 | N |
| ATOM | 2287 | CA | ILE | C | 339 | −79.720 | −55.693 | −53.020 | 1.00 | 22.43 | C |
| ATOM | 2288 | CB | ILE | C | 339 | −78.451 | −56.537 | −53.343 | 1.00 | 24.21 | C |
| ATOM | 2289 | CG1 | ILE | C | 339 | −78.423 | −57.817 | −52.492 | 1.00 | 19.19 | C |
| ATOM | 2290 | CD1 | ILE | C | 339 | −77.307 | −58.792 | −52.904 | 1.00 | 23.39 | C |
| ATOM | 2291 | CG2 | ILE | C | 339 | −77.180 | −55.693 | −53.208 | 1.00 | 22.16 | C |
| ATOM | 2292 | C | ILE | C | 339 | −79.645 | −54.411 | −53.806 | 1.00 | 17.81 | C |
| ATOM | 2293 | O | ILE | C | 339 | −79.860 | −54.399 | −55.028 | 1.00 | 18.79 | O |
| ATOM | 2294 | N | PHE | C | 340 | −79.341 | −53.320 | −53.118 | 1.00 | 16.84 | N |
| ATOM | 2295 | CA | PHE | C | 340 | −78.978 | −52.075 | −53.797 | 1.00 | 16.78 | C |
| ATOM | 2296 | CB | PHE | C | 340 | −80.213 | −51.114 | −53.964 | 1.00 | 18.21 | C |
| ATOM | 2297 | CG | PHE | C | 340 | −80.638 | −50.460 | −52.676 | 1.00 | 14.94 | C |
| ATOM | 2298 | CD1 | PHE | C | 340 | −80.350 | −49.117 | −52.437 | 1.00 | 13.68 | C |
| ATOM | 2299 | CE1 | PHE | C | 340 | −80.678 | −48.532 | −51.219 | 1.00 | 14.56 | C |
| ATOM | 2300 | CZ | PHE | C | 340 | −81.254 | −49.299 | −50.210 | 1.00 | 10.73 | C |
| ATOM | 2301 | CE2 | PHE | C | 340 | −81.535 | −50.617 | −50.437 | 1.00 | 17.87 | C |
| ATOM | 2302 | CD2 | PHE | C | 340 | −81.196 | −51.210 | −51.665 | 1.00 | 16.15 | C |
| ATOM | 2303 | C | PHE | C | 340 | −77.861 | −51.435 | −52.979 | 1.00 | 19.88 | C |
| ATOM | 2304 | O | PHE | C | 340 | −77.474 | −51.947 | −51.907 | 1.00 | 21.42 | O |
| ATOM | 2305 | N | SER | C | 341 | −77.309 | −50.346 | −53.479 | 1.00 | 22.94 | N |
| ATOM | 2306 | CA | SER | C | 341 | −76.117 | −49.775 | −52.854 | 1.00 | 24.27 | C |
| ATOM | 2307 | CB | SER | C | 341 | −74.885 | −49.980 | −53.741 | 1.00 | 30.70 | C |
| ATOM | 2308 | OG | SER | C | 341 | −73.724 | −49.384 | −53.163 | 1.00 | 29.81 | O |
| ATOM | 2309 | C | SER | C | 341 | −76.339 | −48.299 | −52.632 | 1.00 | 21.45 | C |
| ATOM | 2310 | O | SER | C | 341 | −76.660 | −47.582 | −53.578 | 1.00 | 20.90 | O |
| ATOM | 2311 | N | LEU | C | 342 | −76.218 | −47.876 | −51.370 | 1.00 | 20.39 | N |
| ATOM | 2312 | CA | LEU | C | 342 | −76.174 | −46.450 | −50.978 | 1.00 | 23.25 | C |
| ATOM | 2313 | CB | LEU | C | 342 | −76.891 | −46.225 | −49.640 | 1.00 | 20.02 | C |
| ATOM | 2314 | CG | LEU | C | 342 | −78.415 | −46.143 | −49.587 | 1.00 | 22.57 | C |
| ATOM | 2315 | CD1 | LEU | C | 342 | −78.901 | −45.641 | −48.231 | 1.00 | 28.56 | C |
| ATOM | 2316 | CD2 | LEU | C | 342 | −78.911 | −45.217 | −50.711 | 1.00 | 23.97 | C |
| ATOM | 2317 | C | LEU | C | 342 | −74.739 | −45.834 | −50.905 | 1.00 | 22.83 | C |
| ATOM | 2318 | O | LEU | C | 342 | −74.587 | −44.691 | −50.491 | 1.00 | 23.02 | O |
| ATOM | 2319 | N | SER | C | 343 | −73.706 | −46.574 | −51.299 | 1.00 | 24.57 | N |
| ATOM | 2320 | CA | SER | C | 343 | −72.330 | −46.033 | −51.163 | 1.00 | 32.35 | C |
| ATOM | 2321 | CB | SER | C | 343 | −71.375 | −47.099 | −50.636 | 1.00 | 30.10 | C |
| ATOM | 2322 | OG | SER | C | 343 | −71.230 | −48.126 | −51.571 | 1.00 | 30.70 | O |
| ATOM | 2323 | C | SER | C | 343 | −71.773 | −45.365 | −52.440 | 1.00 | 33.73 | C |
| ATOM | 2324 | O | SER | C | 343 | −72.296 | −45.571 | −53.547 | 1.00 | 27.11 | O |
| ATOM | 2325 | N | GLU | C | 360 | −69.602 | −55.743 | −45.543 | 1.00 | 52.55 | N |
| ATOM | 2326 | CA | GLU | C | 360 | −69.920 | −55.803 | −44.113 | 1.00 | 54.23 | C |
| ATOM | 2327 | CB | GLU | C | 360 | −69.177 | −54.686 | −43.358 | 1.00 | 54.41 | C |
| ATOM | 2328 | CG | GLU | C | 360 | −69.204 | −54.811 | −41.839 | 1.00 | 65.60 | C |
| ATOM | 2329 | CD | GLU | C | 360 | −68.200 | −55.822 | −41.307 | 1.00 | 77.62 | C |
| ATOM | 2330 | OE1 | GLU | C | 360 | −68.633 | −56.918 | −40.884 | 1.00 | 91.65 | O |
| ATOM | 2331 | OE2 | GLU | C | 360 | −66.981 | −55.526 | −41.312 | 1.00 | 73.51 | O |
| ATOM | 2332 | C | GLU | C | 360 | −71.438 | −55.701 | −43.877 | 1.00 | 51.43 | C |
| ATOM | 2333 | O | GLU | C | 360 | −72.052 | −56.602 | −43.228 | 1.00 | 31.76 | O |
| ATOM | 2334 | N | THR | C | 361 | −72.014 | −54.598 | −44.389 | 1.00 | 35.39 | N |
| ATOM | 2335 | CA | THR | C | 361 | −73.442 | −54.297 | −44.272 | 1.00 | 38.84 | C |
| ATOM | 2336 | CB | THR | C | 361 | −73.726 | −52.967 | −43.519 | 1.00 | 40.66 | C |
| ATOM | 2337 | OG1 | THR | C | 361 | −73.217 | −53.056 | −42.188 | 1.00 | 42.81 | O |
| ATOM | 2338 | CG2 | THR | C | 361 | −75.243 | −52.698 | −43.429 | 1.00 | 34.48 | C |
| ATOM | 2339 | C | THR | C | 361 | −74.103 | −54.290 | −45.648 | 1.00 | 30.09 | C |
| ATOM | 2340 | O | THR | C | 361 | −73.856 | −53.444 | −46.473 | 1.00 | 32.36 | O |
| ATOM | 2341 | N | LEU | C | 362 | −74.936 | −55.289 | −45.853 | 1.00 | 25.52 | N |
| ATOM | 2342 | CA | LEU | C | 362 | −75.671 | −55.498 | −47.044 | 1.00 | 22.31 | C |
| ATOM | 2343 | CB | LEU | C | 362 | −76.041 | −56.965 | −47.088 | 1.00 | 18.41 | C |
| ATOM | 2344 | CG | LEU | C | 362 | −76.738 | −57.429 | −48.347 | 1.00 | 24.88 | C |
| ATOM | 2345 | CD1 | LEU | C | 362 | −75.722 | −57.567 | −49.465 | 1.00 | 23.94 | C |
| ATOM | 2346 | CD2 | LEU | C | 362 | −77.410 | −58.755 | −48.068 | 1.00 | 26.77 | C |
| ATOM | 2347 | C | LEU | C | 362 | −76.946 | −54.638 | −46.974 | 1.00 | 23.71 | C |
| ATOM | 2348 | O | LEU | C | 362 | −77.624 | −54.621 | −54.960 | 1.00 | 20.35 | O |
| ATOM | 2349 | N | THR | C | 363 | −77.244 | −53.893 | −48.022 | 1.00 | 22.76 | N |
| ATOM | 2350 | CA | THR | C | 363 | −78.470 | −53.075 | −47.999 | 1.00 | 21.61 | C |
| ATOM | 2351 | CB | THR | C | 363 | −78.211 | −51.560 | −48.165 | 1.00 | 19.73 | C |
| ATOM | 2352 | OG1 | THR | C | 363 | −77.405 | −51.336 | −49.320 | 1.00 | 19.98 | O |
| ATOM | 2353 | CG2 | THR | C | 363 | −77.502 | −50.979 | −46.955 | 1.00 | 23.36 | C |
| ATOM | 2354 | C | THR | C | 363 | −79.465 | −53.564 | −49.043 | 1.00 | 20.00 | C |
| ATOM | 2355 | O | THR | C | 363 | −79.127 | −53.722 | −50.232 | 1.00 | 20.90 | O |

TABLE 4-continued

Atomic coordinates for CRBN(TBD):Pomalidomide (Murine protein)

| ATOM | 2356 | N | VAL | C | 364 | −80.677 | −53.836 | −48.579 | 1.00 | 17.53 | N |
|---|---|---|---|---|---|---|---|---|---|---|---|
| ATOM | 2357 | CA | VAL | C | 364 | −81.724 | −54.363 | −49.431 | 1.00 | 14.26 | C |
| ATOM | 2358 | CB | VAL | C | 364 | −82.019 | −55.877 | −49.167 | 1.00 | 15.57 | C |
| ATOM | 2359 | CG1 | VAL | C | 364 | −80.830 | −56.741 | −49.572 | 1.00 | 13.04 | C |
| ATOM | 2360 | CG2 | VAL | C | 364 | −82.479 | −56.132 | −47.725 | 1.00 | 13.21 | C |
| ATOM | 2361 | C | VAL | C | 364 | −83.029 | −53.560 | −49.307 | 1.00 | 15.93 | C |
| ATOM | 2362 | O | VAL | C | 364 | −83.374 | −53.021 | −48.222 | 1.00 | 13.02 | O |
| ATOM | 2363 | N | TYR | C | 365 | −83.780 | −53.496 | −50.422 | 1.00 | 14.42 | N |
| ATOM | 2364 | CA | TYR | C | 365 | −85.057 | −52.749 | −50.434 | 1.00 | 13.84 | C |
| ATOM | 2365 | CB | TYR | C | 365 | −85.570 | −52.636 | −51.891 | 1.00 | 13.70 | C |
| ATOM | 2366 | CG | TYR | C | 365 | −84.847 | −51.572 | −52.738 | 1.00 | 13.42 | C |
| ATOM | 2367 | CD1 | TYR | C | 365 | −84.859 | −50.240 | −52.343 | 1.00 | 13.91 | C |
| ATOM | 2368 | CE1 | TYR | C | 365 | −84.253 | −49.252 | −53.104 | 1.00 | 16.10 | C |
| ATOM | 2369 | CZ | TYR | C | 365 | −83.591 | −49.599 | −54.254 | 1.00 | 17.40 | C |
| ATOM | 2370 | OH | TYR | C | 365 | −83.001 | −48.595 | −54.952 | 1.00 | 19.12 | O |
| ATOM | 2371 | CE2 | TYR | C | 365 | −83.569 | −50.915 | −54.704 | 1.00 | 17.41 | C |
| ATOM | 2372 | CD2 | TYR | C | 365 | −84.187 | −51.904 | −53.932 | 1.00 | 15.14 | C |
| ATOM | 2373 | C | TYR | C | 365 | −86.144 | −53.414 | −49.577 | 1.00 | 15.35 | C |
| ATOM | 2374 | O | TYR | C | 365 | −87.091 | −52.748 | −49.088 | 1.00 | 13.64 | O |
| ATOM | 2375 | N | LYS | C | 366 | −86.073 | −54.745 | −49.541 | 1.00 | 14.25 | N |
| ATOM | 2376 | CA | LYS | C | 366 | −87.127 | −55.597 | −49.043 | 1.00 | 14.23 | C |
| ATOM | 2377 | CB | LYS | C | 366 | −87.974 | −56.154 | −50.210 | 1.00 | 12.69 | C |
| ATOM | 2378 | CG | LYS | C | 366 | −88.869 | −55.089 | −50.842 | 1.00 | 16.11 | C |
| ATOM | 2379 | CD | LYS | C | 366 | −90.141 | −54.986 | −50.014 | 1.00 | 19.06 | C |
| ATOM | 2380 | CE | LYS | C | 366 | −90.783 | −53.645 | −50.166 | 1.00 | 21.60 | C |
| ATOM | 2381 | NZ | LYS | C | 366 | −92.145 | −53.618 | −49.494 | 1.00 | 18.72 | N |
| ATOM | 2382 | C | LYS | C | 366 | −86.517 | −56.747 | −48.278 | 1.00 | 14.08 | C |
| ATOM | 2383 | O | LYS | C | 366 | −85.521 | −57.306 | −48.704 | 1.00 | 16.75 | O |
| ATOM | 2384 | N | ALA | C | 367 | −87.166 | −57.118 | −47.174 | 1.00 | 14.13 | N |
| ATOM | 2385 | CA | ALA | C | 367 | −86.789 | −58.295 | −46.373 | 1.00 | 19.06 | C |
| ATOM | 2386 | CB | ALA | C | 367 | −85.816 | −57.902 | −45.270 | 1.00 | 23.22 | C |
| ATOM | 2387 | C | ALA | C | 367 | −88.052 | −58.931 | −45.782 | 1.00 | 15.78 | C |
| ATOM | 2388 | O | ALA | C | 367 | −89.171 | −58.371 | −45.893 | 1.00 | 16.35 | O |
| ATOM | 2389 | N | SER | C | 368 | −87.883 | −60.082 | −45.139 | 1.00 | 25.21 | N |
| ATOM | 2390 | CA | SER | C | 368 | −89.003 | −60.861 | −44.644 | 1.00 | 16.87 | C |
| ATOM | 2391 | CB | SER | C | 368 | −89.459 | −61.801 | −45.748 | 1.00 | 20.22 | C |
| ATOM | 2392 | OG | SER | C | 368 | −88.378 | −62.647 | −46.127 | 1.00 | 21.26 | O |
| ATOM | 2393 | C | SER | C | 368 | −88.627 | −61.659 | −43.412 | 1.00 | 18.86 | C |
| ATOM | 2394 | O | SER | C | 368 | −87.450 | −61.900 | −43.159 | 1.00 | 17.15 | O |
| ATOM | 2395 | N | ASN | C | 369 | −89.628 | −62.071 | −42.632 | 1.00 | 20.30 | N |
| ATOM | 2396 | CA | ASN | C | 369 | −89.397 | −62.937 | −41.486 | 1.00 | 18.43 | C |
| ATOM | 2397 | CB | ASN | C | 369 | −88.708 | −64.237 | −41.918 | 1.00 | 16.49 | C |
| ATOM | 2398 | CG | ASN | C | 369 | −89.627 | −65.182 | −42.652 | 1.00 | 23.70 | C |
| ATOM | 2399 | OD1 | ASN | C | 369 | −89.246 | −65.762 | −43.671 | 1.00 | 31.98 | O |
| ATOM | 2400 | ND2 | ASN | C | 369 | −90.816 | −65.372 | −42.136 | 1.00 | 20.80 | N |
| ATOM | 2401 | C | ASN | C | 369 | −88.515 | −62.242 | −40.421 | 1.00 | 25.29 | C |
| ATOM | 2402 | O | ASN | C | 369 | −87.869 | −62.905 | −39.616 | 1.00 | 23.47 | O |
| ATOM | 2403 | N | LEU | C | 370 | −88.496 | −60.919 | −40.417 | 1.00 | 23.30 | N |
| ATOM | 2404 | CA | LEU | C | 370 | −87.835 | −60.186 | −39.339 | 1.00 | 20.41 | C |
| ATOM | 2405 | CB | LEU | C | 370 | −86.930 | −59.096 | −39.922 | 1.00 | 20.05 | C |
| ATOM | 2406 | CG | LEU | C | 370 | −85.600 | −59.478 | −40.564 | 1.00 | 21.32 | C |
| ATOM | 2407 | CD1 | LEU | C | 370 | −84.956 | −58.253 | −41.231 | 1.00 | 21.83 | C |
| ATOM | 2408 | CD2 | LEU | C | 370 | −84.703 | −59.997 | −39.469 | 1.00 | 19.90 | C |
| ATOM | 2409 | C | LEU | C | 370 | −88.866 | −59.545 | −38.414 | 1.00 | 19.73 | C |
| ATOM | 2410 | O | LEU | C | 370 | −89.894 | −59.044 | −38.859 | 1.00 | 16.55 | O |
| ATOM | 2411 | N | ASN | C | 371 | −88.578 | −59.587 | −37.111 | 1.00 | 21.86 | N |
| ATOM | 2412 | CA | ASN | C | 371 | −89.297 | −58.817 | −36.086 | 1.00 | 20.75 | C |
| ATOM | 2413 | CB | ASN | C | 371 | −89.453 | −59.650 | −34.786 | 1.00 | 27.32 | C |
| ATOM | 2414 | CG | ASN | C | 371 | −90.630 | −60.615 | −34.835 | 1.00 | 27.97 | C |
| ATOM | 2415 | OD1 | ASN | C | 371 | −90.525 | −61.755 | −34.385 | 1.00 | 33.05 | O |
| ATOM | 2416 | ND2 | ASN | C | 371 | −91.743 | −60.168 | −35.380 | 1.00 | 30.46 | N |
| ATOM | 2417 | C | ASN | C | 371 | −88.532 | −57.563 | −35.704 | 1.00 | 22.41 | C |
| ATOM | 2418 | O | ASN | C | 371 | −87.308 | −57.611 | −35.490 | 1.00 | 20.00 | O |
| ATOM | 2419 | N | LEU | C | 372 | −89.270 | −56.479 | −35.536 | 1.00 | 22.71 | N |
| ATOM | 2420 | CA | LEU | C | 372 | −88.691 | −55.189 | −35.185 | 1.00 | 22.26 | C |
| ATOM | 2421 | CB | LEU | C | 372 | −89.479 | −54.047 | −35.861 | 1.00 | 22.35 | C |
| ATOM | 2422 | CG | LEU | C | 372 | −89.420 | −54.049 | −37.410 | 1.00 | 26.74 | C |
| ATOM | 2423 | CD1 | LEU | C | 372 | −90.387 | −53.036 | −38.002 | 1.00 | 27.24 | C |
| ATOM | 2424 | CD2 | LEU | C | 372 | −87.984 | −53.851 | −37.940 | 1.00 | 21.45 | C |
| ATOM | 2425 | C | LEU | C | 372 | −88.709 | −55.053 | −33.678 | 1.00 | 25.61 | C |
| ATOM | 2426 | O | LEU | C | 372 | −89.715 | −55.368 | −33.041 | 1.00 | 26.85 | O |
| ATOM | 2427 | N | ILE | C | 373 | −87.588 | −54.599 | −33.108 | 1.00 | 27.10 | N |
| ATOM | 2428 | CA | ILE | C | 373 | −87.426 | −54.479 | −31.651 | 1.00 | 32.55 | C |
| ATOM | 2429 | CB | ILE | C | 373 | −86.147 | −55.223 | −31.152 | 1.00 | 29.41 | C |
| ATOM | 2430 | CG1 | ILE | C | 373 | −86.133 | −56.670 | −31.639 | 1.00 | 32.76 | C |
| ATOM | 2431 | CD1 | ILE | C | 373 | −87.284 | −57.505 | −31.127 | 1.00 | 35.55 | C |
| ATOM | 2432 | CG2 | ILE | C | 373 | −86.042 | −55.185 | −29.628 | 1.00 | 27.88 | C |
| ATOM | 2433 | C | ILE | C | 373 | −87.293 | −53.020 | −31.255 | 1.00 | 33.85 | C |

TABLE 4-continued

Atomic coordinates for CRBN(TBD):Pomalidomide (Murine protein)

| ATOM | 2434 | O | ILE | C | 373 | −86.313 | −52.386 | −31.615 | 1.00 | 35.67 | O |
|------|------|------|-----|---|-----|---------|---------|---------|------|-------|---|
| ATOM | 2435 | N | GLY | C | 374 | −88.255 | −52.504 | −30.490 | 1.00 | 30.51 | N |
| ATOM | 2436 | CA | GLY | C | 374 | −88.189 | −51.127 | −29.994 | 1.00 | 27.83 | C |
| ATOM | 2437 | C | GLY | C | 374 | −88.641 | −50.100 | −31.028 | 1.00 | 36.00 | C |
| ATOM | 2438 | O | GLY | C | 374 | −89.362 | −50.430 | −32.003 | 1.00 | 33.60 | O |
| ATOM | 2439 | N | ARG | C | 375 | −88.222 | −48.855 | −30.828 | 1.00 | 29.88 | N |
| ATOM | 2440 | CA | ARG | C | 375 | −88.601 | −47.757 | −31.729 | 1.00 | 41.32 | C |
| ATOM | 2441 | CB | ARG | C | 375 | −89.312 | −46.624 | −30.957 | 1.00 | 47.07 | C |
| ATOM | 2442 | CG | ARG | C | 375 | −90.166 | −47.051 | −29.762 | 1.00 | 56.68 | C |
| ATOM | 2443 | CD | ARG | C | 375 | −90.523 | −45.851 | −28.878 | 1.00 | 64.81 | C |
| ATOM | 2444 | NE | ARG | C | 375 | −89.341 | −45.063 | −28.502 | 1.00 | 67.63 | N |
| ATOM | 2445 | CZ | ARG | C | 375 | −88.776 | −45.061 | −27.296 | 1.00 | 64.13 | C |
| ATOM | 2446 | NH1 | ARG | C | 375 | −89.289 | −45.791 | −26.312 | 1.00 | 69.74 | N |
| ATOM | 2447 | NH2 | ARG | C | 375 | −87.699 | −44.316 | −27.069 | 1.00 | 57.83 | N |
| ATOM | 2448 | C | ARG | C | 375 | −87.364 | −47.180 | −32.445 | 1.00 | 34.00 | C |
| ATOM | 2449 | O | ARG | C | 375 | −86.248 | −47.274 | −31.928 | 1.00 | 33.86 | O |
| ATOM | 2450 | N | PRO | C | 376 | −87.575 | −46.543 | −33.611 | 1.00 | 32.65 | N |
| ATOM | 2451 | CA | PRO | C | 376 | −86.536 | −45.888 | −34.385 | 1.00 | 27.25 | C |
| ATOM | 2452 | CB | PRO | C | 376 | −87.331 | −45.036 | −35.348 | 1.00 | 26.79 | C |
| ATOM | 2453 | CG | PRO | C | 376 | −88.530 | −45.865 | −35.632 | 1.00 | 27.98 | C |
| ATOM | 2454 | CD | PRO | C | 376 | −88.852 | −46.576 | −34.352 | 1.00 | 29.06 | C |
| ATOM | 2455 | C | PRO | C | 376 | −85.641 | −44.993 | −33.567 | 1.00 | 24.98 | C |
| ATOM | 2456 | O | PRO | C | 376 | −86.117 | −44.268 | −32.698 | 1.00 | 24.04 | O |
| ATOM | 2457 | N | SER | C | 377 | −84.346 | −45.034 | −33.867 | 1.00 | 20.29 | N |
| ATOM | 2458 | CA | SER | C | 377 | −83.385 | −44.058 | −33.324 | 1.00 | 17.43 | C |
| ATOM | 2459 | CB | SER | C | 377 | −82.593 | −44.726 | −32.188 | 1.00 | 19.24 | C |
| ATOM | 2460 | OG | SER | C | 377 | −81.515 | −43.906 | −31.790 | 1.00 | 20.33 | O |
| ATOM | 2461 | C | SER | C | 377 | −82.400 | −43.579 | −34.426 | 1.00 | 16.89 | C |
| ATOM | 2462 | O | SER | C | 377 | −82.010 | −44.365 | −35.287 | 1.00 | 17.47 | O |
| ATOM | 2463 | N | THR | C | 378 | −81.986 | −42.314 | −34.370 | 1.00 | 13.71 | N |
| ATOM | 2464 | CA | THR | C | 378 | −80.940 | −41.763 | −35.234 | 1.00 | 14.26 | C |
| ATOM | 2465 | CB | THR | C | 378 | −81.258 | −40.312 | −35.651 | 1.00 | 15.80 | C |
| ATOM | 2466 | OG1 | THR | C | 378 | −81.414 | −39.538 | −34.469 | 1.00 | 16.41 | O |
| ATOM | 2467 | CG2 | THR | C | 378 | −82.560 | −40.244 | −36.431 | 1.00 | 15.94 | C |
| ATOM | 2468 | C | THR | C | 378 | −79.568 | −41.750 | −34.508 | 1.00 | 16.21 | C |
| ATOM | 2469 | O | THR | C | 378 | −78.565 | −41.337 | −35.082 | 1.00 | 14.59 | O |
| ATOM | 2470 | N | VAL | C | 379 | −79.514 | −42.267 | −33.273 | 1.00 | 17.42 | N |
| ATOM | 2471 | CA | VAL | C | 379 | −78.262 | −42.231 | −32.513 | 1.00 | 17.78 | C |
| ATOM | 2472 | CB | VAL | C | 379 | −78.462 | −42.728 | −31.058 | 1.00 | 21.09 | C |
| ATOM | 2473 | CG1 | VAL | C | 379 | −77.131 | −43.110 | −30.429 | 1.00 | 22.33 | C |
| ATOM | 2474 | CG2 | VAL | C | 379 | −79.161 | −41.659 | −30.203 | 1.00 | 22.27 | C |
| ATOM | 2475 | C | VAL | C | 379 | −77.197 | −43.073 | −33.242 | 1.00 | 17.74 | C |
| ATOM | 2476 | O | VAL | C | 379 | −77.437 | −44.244 | −33.558 | 1.00 | 20.55 | O |
| ATOM | 2477 | N | HIS | C | 380 | −76.074 | −42.444 | −33.580 | 1.00 | 15.18 | N |
| ATOM | 2478 | CA | HIS | C | 380 | −74.972 | −43.091 | −34.313 | 1.00 | 16.42 | C |
| ATOM | 2479 | CB | HIS | C | 380 | −74.261 | −44.132 | −33.439 | 1.00 | 14.16 | C |
| ATOM | 2480 | CG | HIS | C | 380 | −73.736 | −43.572 | −32.141 | 1.00 | 14.82 | C |
| ATOM | 2481 | ND1 | HIS | C | 380 | −72.964 | −42.466 | −32.091 | 1.00 | 15.11 | N |
| ATOM | 2482 | CE1 | HIS | C | 380 | −72.646 | −42.207 | −30.825 | 1.00 | 14.35 | C |
| ATOM | 2483 | NE2 | HIS | C | 380 | −73.224 | −43.142 | −30.052 | 1.00 | 14.28 | N |
| ATOM | 2484 | CD2 | HIS | C | 380 | −73.893 | −44.000 | −30.832 | 1.00 | 13.71 | C |
| ATOM | 2485 | C | HIS | C | 380 | −75.375 | −43.713 | −35.640 | 1.00 | 16.83 | C |
| ATOM | 2486 | O | HIS | C | 380 | −74.740 | −44.647 | −36.111 | 1.00 | 16.57 | O |
| ATOM | 2487 | N | SER | C | 381 | −76.419 | −43.195 | −36.269 | 1.00 | 18.32 | N |
| ATOM | 2488 | CA | SER | C | 381 | −76.891 | −43.794 | −37.495 | 1.00 | 16.78 | C |
| ATOM | 2489 | CB | SER | C | 381 | −78.035 | −42.978 | −38.085 | 1.00 | 18.69 | C |
| ATOM | 2490 | OG | SER | C | 381 | −78.510 | −43.648 | −39.237 | 1.00 | 18.08 | O |
| ATOM | 2491 | C | SER | C | 381 | −75.783 | −43.953 | −38.565 | 1.00 | 15.20 | C |
| ATOM | 2492 | O | SER | C | 381 | −75.097 | −42.971 | −38.932 | 1.00 | 15.38 | O |
| ATOM | 2493 | N | TRP | C | 382 | −75.651 | −45.168 | −39.099 | 1.00 | 12.21 | N |
| ATOM | 2494 | CA | TRP | C | 382 | −74.695 | −45.412 | −40.183 | 1.00 | 15.15 | C |
| ATOM | 2495 | CB | TRP | C | 382 | −74.434 | −46.905 | −40.339 | 1.00 | 16.24 | C |
| ATOM | 2496 | CG | TRP | C | 382 | −73.870 | −47.552 | −39.118 | 1.00 | 17.49 | C |
| ATOM | 2497 | CD1 | TRP | C | 382 | −73.011 | −46.985 | −38.162 | 1.00 | 19.24 | C |
| ATOM | 2498 | NE1 | TRP | C | 382 | −72.714 | −47.892 | −37.196 | 1.00 | 20.42 | N |
| ATOM | 2499 | CE2 | TRP | C | 382 | −73.332 | −49.067 | −37.431 | 1.00 | 21.54 | C |
| ATOM | 2500 | CD2 | TRP | C | 382 | −74.068 | −48.926 | −38.676 | 1.00 | 19.62 | C |
| ATOM | 2501 | CE3 | TRP | C | 382 | −74.809 | −50.009 | −39.151 | 1.00 | 22.96 | C |
| ATOM | 2502 | CZ3 | TRP | C | 382 | −74.783 | −51.204 | −38.417 | 1.00 | 22.86 | C |
| ATOM | 2503 | CH2 | TRP | C | 382 | −74.027 | −51.329 | −37.241 | 1.00 | 29.27 | C |
| ATOM | 2504 | CZ2 | TRP | C | 382 | −73.296 | −50.264 | −36.723 | 1.00 | 23.34 | C |
| ATOM | 2505 | C | TRP | C | 382 | −75.121 | −44.800 | −41.523 | 1.00 | 17.69 | C |
| ATOM | 2506 | O | TRP | C | 382 | −74.291 | −44.653 | −42.439 | 1.00 | 21.22 | O |
| ATOM | 2507 | N | PHE | C | 383 | −76.388 | −44.406 | −41.642 | 1.00 | 15.13 | N |
| ATOM | 2508 | CA | PHE | C | 383 | −76.892 | −43.767 | −42.891 | 1.00 | 17.40 | C |
| ATOM | 2509 | CB | PHE | C | 383 | −77.830 | −44.722 | −43.645 | 1.00 | 15.15 | C |
| ATOM | 2510 | CG | PHE | C | 383 | −77.191 | −46.004 | −44.044 | 1.00 | 15.57 | C |
| ATOM | 2511 | CD1 | PHE | C | 383 | −76.392 | −46.065 | −45.194 | 1.00 | 17.30 | C |

TABLE 4-continued

Atomic coordinates for CRBN(TBD):Pomalidomide (Murine protein)

| ATOM | 2512 | CE1 | PHE | C | 383 | −75.772 | −47.244 | −45.554 | 1.00 | 18.74 | C |
|---|---|---|---|---|---|---|---|---|---|---|---|
| ATOM | 2513 | CZ | PHE | C | 383 | −75.935 | −48.373 | −44.768 | 1.00 | 22.69 | C |
| ATOM | 2514 | CE2 | PHE | C | 383 | −76.713 | −48.322 | −43.612 | 1.00 | 16.16 | C |
| ATOM | 2515 | CD2 | PHE | C | 383 | −77.320 | −47.140 | −43.245 | 1.00 | 14.21 | C |
| ATOM | 2516 | C | PHE | C | 383 | −77.584 | −42.437 | −42.593 | 1.00 | 16.90 | C |
| ATOM | 2517 | O | PHE | C | 383 | −78.775 | −42.409 | −42.226 | 1.00 | 19.70 | O |
| ATOM | 2518 | N | PRO | C | 384 | −76.833 | −41.323 | −42.694 | 1.00 | 19.16 | N |
| ATOM | 2519 | CA | PRO | C | 384 | −77.364 | −40.000 | −42.343 | 1.00 | 21.35 | C |
| ATOM | 2520 | CB | PRO | C | 384 | −76.280 | −39.043 | −42.863 | 1.00 | 25.42 | C |
| ATOM | 2521 | CG | PRO | C | 384 | −75.025 | −39.831 | −42.729 | 1.00 | 24.79 | C |
| ATOM | 2522 | CD | PRO | C | 384 | −75.386 | −41.279 | −42.975 | 1.00 | 19.81 | C |
| ATOM | 2523 | C | PRO | C | 384 | −78.704 | −39.724 | −43.020 | 1.00 | 24.37 | C |
| ATOM | 2524 | O | PRO | C | 384 | −78.862 | −40.020 | −44.209 | 1.00 | 27.93 | O |
| ATOM | 2525 | N | GLY | C | 385 | −79.669 | −39.215 | −42.246 | 1.00 | 22.67 | N |
| ATOM | 2526 | CA | GLY | C | 385 | −81.032 | −39.029 | −42.713 | 1.00 | 24.78 | C |
| ATOM | 2527 | C | GLY | C | 385 | −81.988 | −40.192 | −42.400 | 1.00 | 21.92 | C |
| ATOM | 2528 | O | GLY | C | 385 | −83.167 | −40.063 | −42.584 | 1.00 | 24.00 | O |
| ATOM | 2529 | N | TYR | C | 386 | −81.471 | −41.323 | −41.927 | 1.00 | 16.94 | N |
| ATOM | 2530 | CA | TYR | C | 386 | −82.298 | −42.461 | −41.564 | 1.00 | 16.82 | C |
| ATOM | 2531 | CB | TYR | C | 386 | −81.820 | −43.717 | −42.327 | 1.00 | 14.65 | C |
| ATOM | 2532 | CG | TYR | C | 386 | −82.097 | −43.646 | −43.829 | 1.00 | 16.35 | C |
| ATOM | 2533 | CD1 | TYR | C | 386 | −83.316 | −44.111 | −44.353 | 1.00 | 17.04 | C |
| ATOM | 2534 | CE1 | TYR | C | 386 | −83.604 | −44.008 | −45.731 | 1.00 | 16.61 | C |
| ATOM | 2535 | CZ | TYR | C | 386 | −82.650 | −43.497 | −46.590 | 1.00 | 16.13 | C |
| ATOM | 2536 | OH | TYR | C | 386 | −82.933 | −43.447 | −47.940 | 1.00 | 19.45 | O |
| ATOM | 2537 | CE2 | TYR | C | 386 | −81.432 | −43.014 | −46.095 | 1.00 | 16.85 | C |
| ATOM | 2538 | CD2 | TYR | C | 386 | −81.153 | −43.106 | −44.721 | 1.00 | 15.17 | C |
| ATOM | 2539 | C | TYR | C | 386 | −82.193 | −42.743 | −40.068 | 1.00 | 19.03 | C |
| ATOM | 2540 | O | TYR | C | 386 | −81.150 | −42.510 | −39.478 | 1.00 | 15.89 | O |
| ATOM | 2541 | N | ALA | C | 387 | −83.276 | −43.269 | −39.484 | 1.00 | 17.66 | N |
| ATOM | 2542 | CA | ALA | C | 387 | −83.258 | −43.803 | −38.134 | 1.00 | 18.44 | C |
| ATOM | 2543 | CB | ALA | C | 387 | −84.507 | −43.353 | −37.400 | 1.00 | 19.84 | C |
| ATOM | 2544 | C | ALA | C | 387 | −83.185 | −45.341 | −38.208 | 1.00 | 17.79 | C |
| ATOM | 2545 | O | ALA | C | 387 | −83.553 | −45.907 | −39.210 | 1.00 | 20.57 | O |
| ATOM | 2546 | N | TRP | C | 388 | −82.703 | −46.017 | −37.161 | 1.00 | 14.28 | N |
| ATOM | 2547 | CA | TRP | C | 388 | −82.644 | −47.497 | −37.185 | 1.00 | 17.54 | C |
| ATOM | 2548 | CB | TRP | C | 388 | −81.205 | −47.982 | −37.011 | 1.00 | 17.30 | C |
| ATOM | 2549 | CG | TRP | C | 388 | −80.515 | −47.438 | −35.790 | 1.00 | 17.52 | C |
| ATOM | 2550 | CD1 | TRP | C | 388 | −79.680 | −46.319 | −35.714 | 1.00 | 17.47 | C |
| ATOM | 2551 | NE1 | TRP | C | 388 | −79.220 | −46.146 | −34.423 | 1.00 | 20.00 | N |
| ATOM | 2552 | CE2 | TRP | C | 388 | −79.725 | −47.096 | −33.598 | 1.00 | 21.83 | C |
| ATOM | 2553 | CD2 | TRP | C | 388 | −80.566 | −47.976 | −34.419 | 1.00 | 19.49 | C |
| ATOM | 2554 | CE3 | TRP | C | 388 | −81.214 | −49.052 | −33.811 | 1.00 | 20.29 | C |
| ATOM | 2555 | CZ3 | TRP | C | 388 | −81.002 | −49.274 | −32.420 | 1.00 | 22.79 | C |
| ATOM | 2556 | CH2 | TRP | C | 388 | −80.204 | −48.405 | −31.651 | 1.00 | 23.47 | C |
| ATOM | 2557 | CZ2 | TRP | C | 388 | −79.531 | −47.317 | −32.228 | 1.00 | 21.03 | C |
| ATOM | 2558 | C | TRP | C | 388 | −83.534 | −48.170 | −36.155 | 1.00 | 20.00 | C |
| ATOM | 2559 | O | TRP | C | 388 | −83.771 | −47.624 | −35.097 | 1.00 | 21.86 | O |
| ATOM | 2560 | N | THR | C | 389 | −84.023 | −49.370 | −36.478 | 1.00 | 22.70 | N |
| ATOM | 2561 | CA | THR | C | 389 | −84.696 | −50.244 | −35.510 | 1.00 | 17.72 | C |
| ATOM | 2562 | CB | THR | C | 389 | −86.216 | −50.337 | −35.823 | 1.00 | 21.51 | C |
| ATOM | 2563 | OG1 | THR | C | 389 | −86.741 | −49.025 | −35.994 | 1.00 | 21.64 | O |
| ATOM | 2564 | CG2 | THR | C | 389 | −86.978 | −51.002 | −34.645 | 1.00 | 21.45 | C |
| ATOM | 2565 | C | THR | C | 389 | 84.111 | −51.648 | −35.617 | 1.00 | 21.06 | C |
| ATOM | 2566 | O | THR | C | 389 | −84.000 | −52.175 | −36.712 | 1.00 | 21.49 | O |
| ATOM | 2567 | N | ILE | C | 390 | −83.702 | −52.245 | −34.480 | 1.00 | 17.91 | N |
| ATOM | 2568 | CA | ILE | C | 390 | −83.173 | −53.598 | −34.486 | 1.00 | 15.81 | C |
| ATOM | 2569 | CB | ILE | C | 390 | −82.809 | −54.079 | −33.075 | 1.00 | 16.95 | C |
| ATOM | 2570 | CG1 | ILE | C | 390 | −81.583 | −53.312 | −32.571 | 1.00 | 18.71 | C |
| ATOM | 2571 | CD1 | ILE | C | 390 | −81.213 | −53.618 | −31.126 | 1.00 | 22.31 | C |
| ATOM | 2572 | CG2 | ILE | C | 390 | −82.523 | −55.583 | −33.082 | 1.00 | 21.05 | C |
| ATOM | 2573 | C | ILE | C | 390 | −84.182 | −54.543 | −35.104 | 1.00 | 18.48 | C |
| ATOM | 2574 | O | ILE | C | 390 | −85.401 | −54.465 | −34.802 | 1.00 | 16.48 | O |
| ATOM | 2575 | N | ALA | C | 391 | −83.672 | −55.401 | −35.992 | 1.00 | 17.19 | N |
| ATOM | 2576 | CA | ALA | C | 391 | −84.461 | −56.421 | −36.674 | 1.00 | 18.85 | C |
| ATOM | 2577 | CB | ALA | C | 391 | −84.469 | −56.153 | −38.165 | 1.00 | 16.11 | C |
| ATOM | 2578 | C | ALA | C | 391 | −83.831 | −57.803 | −36.382 | 1.00 | 24.01 | C |
| ATOM | 2579 | O | ALA | C | 391 | −82.645 | −58.040 | −36.695 | 1.00 | 20.74 | O |
| ATOM | 2580 | N | GLN | C | 392 | −84.610 | −58.707 | −35.786 | 1.00 | 22.43 | N |
| ATOM | 2581 | CA | GLN | C | 392 | −84.100 | −60.077 | −35.492 | 1.00 | 19.30 | C |
| ATOM | 2582 | CB | GLN | C | 392 | −84.066 | −60.285 | −33.985 | 1.00 | 20.48 | C |
| ATOM | 2583 | CG | GLN | C | 392 | −85.361 | −59.855 | −33.340 | 1.00 | 30.13 | C |
| ATOM | 2584 | CD | GLN | C | 392 | −85.460 | −60.267 | −31.909 | 1.00 | 32.28 | C |
| ATOM | 2585 | OE1 | GLN | C | 392 | −84.658 | −59.843 | −31.088 | 1.00 | 31.46 | O |
| ATOM | 2586 | NE2 | GLN | C | 392 | −86.471 | −61.088 | −31.588 | 1.00 | 30.56 | N |
| ATOM | 2587 | C | GLN | C | 392 | −84.953 | −61.159 | −36.181 | 1.00 | 20.20 | C |
| ATOM | 2588 | O | GLN | C | 392 | −86.156 | −60.937 | −36.460 | 1.00 | 22.04 | O |
| ATOM | 2589 | N | CYS | C | 393 | −84.355 | −62.312 | −36.459 | 1.00 | 20.74 | N |

TABLE 4-continued

Atomic coordinates for CRBN(TBD):Pomalidomide (Murine protein)

| ATOM | 2590 | CA | CYS | C | 393 | −85.120 | −63.426 | −37.033 | 1.00 | 21.19 | C |
|---|---|---|---|---|---|---|---|---|---|---|---|
| ATOM | 2591 | CB | CYS | C | 393 | −84.230 | −64.638 | −37.288 | 1.00 | 15.44 | C |
| ATOM | 2592 | SG | CYS | C | 393 | −85.130 | −66.142 | −37.709 | 1.00 | 20.71 | S |
| ATOM | 2593 | C | CYS | C | 393 | −86.349 | −63.803 | −36.160 | 1.00 | 22.32 | C |
| ATOM | 2594 | O | CYS | C | 393 | −86.258 | −63.875 | −34.924 | 1.00 | 22.98 | O |
| ATOM | 2595 | N | LYS | C | 394 | −87.496 | −63.997 | −36.813 | 1.00 | 17.78 | N |
| ATOM | 2596 | CA | LYS | C | 394 | −88.732 | −64.185 | −36.098 | 1.00 | 20.23 | C |
| ATOM | 2597 | CB | LYS | C | 394 | −89.934 | −63.980 | −37.012 | 1.00 | 22.55 | C |
| ATOM | 2598 | CG | LYS | C | 394 | −90.334 | −65.216 | −37.796 | 1.00 | 22.60 | C |
| ATOM | 2599 | CD | LYS | C | 394 | −91.494 | −64.901 | −38.719 | 1.00 | 29.41 | C |
| ATOM | 2600 | CE | LYS | C | 394 | −92.236 | −66.164 | −39.109 | 1.00 | 28.29 | C |
| ATOM | 2601 | NZ | LYS | C | 394 | −93.010 | −65.901 | −40.356 | 1.00 | 35.11 | N |
| ATOM | 2602 | C | LYS | C | 394 | −88.784 | −65.562 | −35.450 | 1.00 | 20.60 | C |
| ATOM | 2603 | O | LYS | C | 394 | −89.586 | −65.768 | −34.549 | 1.00 | 19.59 | O |
| ATOM | 2604 | N | ILE | C | 395 | −87.938 | −66.495 | −35.920 | 1.00 | 19.55 | N |
| ATOM | 2605 | CA | ILE | C | 395 | −87.909 | −67.865 | −35.391 | 1.00 | 20.31 | C |
| ATOM | 2606 | CB | ILE | C | 395 | −87.597 | −68.930 | −36.497 | 1.00 | 19.34 | C |
| ATOM | 2607 | CG1 | ILE | C | 395 | −88.668 | −68.937 | −37.605 | 1.00 | 19.02 | C |
| ATOM | 2608 | CD1 | ILE | C | 395 | −90.075 | −69.306 | −37.152 | 1.00 | 18.51 | C |
| ATOM | 2609 | CG2 | ILE | C | 395 | −87.432 | −70.319 | −35.882 | 1.00 | 21.79 | C |
| ATOM | 2610 | C | ILE | C | 395 | −86.936 | −68.027 | −34.215 | 1.00 | 23.66 | C |
| ATOM | 2611 | O | ILE | C | 395 | −87.311 | −68.538 | −33.176 | 1.00 | 22.28 | O |
| ATOM | 2612 | N | CYS | C | 396 | −85.681 | −67.611 | −34.391 | 1.00 | 23.48 | N |
| ATOM | 2613 | CA | CYS | C | 396 | −84.651 | −67.877 | −33.396 | 1.00 | 19.94 | C |
| ATOM | 2614 | CB | CYS | C | 396 | −83.462 | −68.539 | −34.073 | 1.00 | 21.17 | C |
| ATOM | 2615 | SG | CYS | C | 396 | −82.484 | −67.368 | −35.033 | 1.00 | 24.74 | S |
| ATOM | 2616 | C | CYS | C | 396 | −84.192 | −66.595 | −32.672 | 1.00 | 20.15 | C |
| ATOM | 2617 | O | CYS | C | 396 | −83.437 | −66.669 | −31.738 | 1.00 | 20.54 | O |
| ATOM | 2618 | N | ALA | C | 397 | −84.644 | −65.416 | −33.138 | 1.00 | 23.65 | N |
| ATOM | 2619 | CA | ALA | C | 397 | −84.264 | −64.113 | −32.546 | 1.00 | 17.06 | C |
| ATOM | 2620 | CB | ALA | C | 397 | −84.537 | −64.076 | −31.035 | 1.00 | 17.73 | C |
| ATOM | 2621 | C | ALA | C | 397 | −82.826 | −63.674 | −32.837 | 1.00 | 18.41 | C |
| ATOM | 2622 | O | ALA | C | 397 | −82.342 | −62.742 | −32.204 | 1.00 | 17.41 | O |
| ATOM | 2623 | N | SER | C | 398 | −82.135 | −64.337 | −33.778 | 1.00 | 18.48 | N |
| ATOM | 2624 | CA | SER | C | 398 | −80.791 | −63.894 | −34.175 | 1.00 | 20.01 | C |
| ATOM | 2625 | CB | SER | C | 398 | −80.247 | −64.776 | −35.292 | 1.00 | 22.26 | C |
| ATOM | 2626 | OG | SER | C | 398 | −79.016 | −64.291 | −35.796 | 1.00 | 24.14 | O |
| ATOM | 2627 | C | SER | C | 398 | −80.872 | −62.442 | −34.657 | 1.00 | 21.26 | C |
| ATOM | 2628 | O | SER | C | 398 | −81.728 | −62.110 | −35.477 | 1.00 | 20.78 | O |
| ATOM | 2629 | N | HIS | C | 399 | −80.012 | −61.581 | −34.118 | 1.00 | 21.72 | N |
| ATOM | 2630 | CA | HIS | C | 399 | −79.884 | −60.189 | −34.580 | 1.00 | 28.14 | C |
| ATOM | 2631 | CB | HIS | C | 399 | −78.938 | −59.420 | −33.665 | 1.00 | 28.20 | C |
| ATOM | 2632 | CG | HIS | C | 399 | −79.591 | −58.841 | −32.424 | 1.00 | 40.47 | C |
| ATOM | 2633 | ND1 | HIS | C | 399 | −80.492 | −59.521 | −31.681 | 1.00 | 44.65 | N |
| ATOM | 2634 | CE1 | HIS | C | 399 | −80.881 | −58.760 | −30.636 | 1.00 | 39.75 | C |
| ATOM | 2635 | NE2 | HIS | C | 399 | −80.223 | −57.591 | −30.702 | 1.00 | 51.18 | N |
| ATOM | 2636 | CD2 | HIS | C | 399 | −79.414 | −57.606 | −31.788 | 1.00 | 41.14 | C |
| ATOM | 2637 | C | HIS | C | 399 | −79.337 | −60.168 | −35.999 | 1.00 | 27.46 | C |
| ATOM | 2638 | O | HIS | C | 399 | −78.131 | −60.292 | −36.206 | 1.00 | 24.27 | O |
| ATOM | 2639 | N | ILE | C | 400 | −80.203 | −60.036 | −36.992 | 1.00 | 22.61 | N |
| ATOM | 2640 | CA | ILE | C | 400 | −79.754 | −60.068 | −38.394 | 1.00 | 22.27 | C |
| ATOM | 2641 | CB | ILE | C | 400 | −80.842 | −60.666 | −39.334 | 1.00 | 19.99 | C |
| ATOM | 2642 | CG1 | ILE | C | 400 | −81.257 | −62.082 | −38.869 | 1.00 | 17.08 | C |
| ATOM | 2643 | CD1 | ILE | C | 400 | −80.203 | −63.115 | −39.062 | 1.00 | 23.14 | C |
| ATOM | 2644 | CG2 | ILE | C | 400 | −80.386 | −60.666 | −40.807 | 1.00 | 16.43 | C |
| ATOM | 2645 | C | ILE | C | 400 | −79.325 | −58.669 | −38.878 | 1.00 | 23.99 | C |
| ATOM | 2646 | O | ILE | C | 400 | −78.390 | −58.542 | −39.683 | 1.00 | 21.37 | O |
| ATOM | 2647 | N | GLY | C | 401 | −80.008 | −57.623 | −38.401 | 1.00 | 19.95 | N |
| ATOM | 2648 | CA | GLY | C | 401 | −79.636 | −56.263 | −38.802 | 1.00 | 18.21 | C |
| ATOM | 2649 | C | GLY | C | 401 | −80.531 | −55.174 | −38.281 | 1.00 | 18.71 | C |
| ATOM | 2650 | O | GLY | C | 401 | −80.907 | −55.191 | −37.122 | 1.00 | 19.32 | O |
| ATOM | 2651 | N | TRP | C | 402 | −80.888 | −54.225 | −39.164 | 1.00 | 17.44 | N |
| ATOM | 2652 | CA | TRP | C | 402 | −81.726 | −53.078 | −38.800 | 1.00 | 19.31 | C |
| ATOM | 2653 | CB | TRP | C | 402 | −80.865 | −51.862 | −38.399 | 1.00 | 20.18 | C |
| ATOM | 2654 | CG | TRP | C | 402 | −79.877 | −52.174 | −37.289 | 1.00 | 22.67 | C |
| ATOM | 2655 | CD1 | TRP | C | 402 | −80.022 | −51.940 | −35.933 | 1.00 | 22.20 | C |
| ATOM | 2656 | NE1 | TRP | C | 402 | −78.907 | −52.382 | −35.236 | 1.00 | 20.05 | N |
| ATOM | 2657 | CE2 | TRP | C | 402 | −78.004 | −52.923 | −36.074 | 1.00 | 18.73 | C |
| ATOM | 2658 | CD2 | TRP | C | 402 | −78.560 | −52.815 | −37.432 | 1.00 | 24.01 | C |
| ATOM | 2659 | CE3 | TRP | C | 402 | −77.817 | −53.316 | −38.520 | 1.00 | 22.95 | C |
| ATOM | 2660 | CZ3 | TRP | C | 402 | −76.550 | −53.909 | −38.248 | 1.00 | 25.71 | C |
| ATOM | 2661 | CH2 | TRP | C | 402 | −76.044 | −53.994 | −36.930 | 1.00 | 22.33 | C |
| ATOM | 2662 | CZ2 | TRP | C | 402 | −76.756 | −53.491 | −35.824 | 1.00 | 22.36 | C |
| ATOM | 2663 | C | TRP | C | 402 | −82.674 | −52.660 | −39.920 | 1.00 | 16.44 | C |
| ATOM | 2664 | O | TRP | C | 402 | −82.382 | −52.831 | −41.096 | 1.00 | 16.58 | O |
| ATOM | 2665 | N | LYS | C | 403 | −83.809 | −52.106 | −39.544 | 1.00 | 15.91 | N |
| ATOM | 2666 | CA | LYS | C | 403 | −84.644 | −51.400 | −40.496 | 1.00 | 15.23 | C |
| ATOM | 2667 | CB | LYS | C | 403 | −86.111 | −51.534 | −40.149 | 1.00 | 14.73 | C |

TABLE 4-continued

Atomic coordinates for CRBN(TBD):Pomalidomide (Murine protein)

| ATOM | 2668 | CG | LYS | C | 403 | −87.053 | −51.126 | −41.296 | 1.00 | 17.67 | C |
|------|------|-----|-----|---|-----|---------|---------|---------|------|-------|---|
| ATOM | 2669 | CD | LYS | C | 403 | −88.510 | −51.063 | −40.785 | 1.00 | 19.67 | C |
| ATOM | 2670 | CE | LYS | C | 403 | −89.540 | −51.066 | −41.936 | 1.00 | 26.44 | C |
| ATOM | 2671 | NZ | LYS | C | 403 | −90.902 | −50.808 | −41.380 | 1.00 | 25.88 | N |
| ATOM | 2672 | C | LYS | C | 403 | −84.240 | −49.961 | −40.385 | 1.00 | 15.48 | C |
| ATOM | 2673 | O | LYS | C | 403 | −84.160 | −49.427 | −39.264 | 1.00 | 16.39 | O |
| ATOM | 2674 | N | PHE | C | 404 | −83.992 | −49.334 | −41.537 | 1.00 | 14.03 | N |
| ATOM | 2675 | CA | PHE | C | 404 | −83.636 | −47.911 | −41.590 | 1.00 | 14.56 | C |
| ATOM | 2676 | CB | PHE | C | 404 | −82.363 | −47.709 | −42.431 | 1.00 | 15.79 | C |
| ATOM | 2677 | CG | PHE | C | 404 | −81.085 | −48.126 | −41.697 | 1.00 | 14.77 | C |
| ATOM | 2678 | CD1 | PHE | C | 404 | −80.438 | −47.220 | −40.848 | 1.00 | 11.92 | C |
| ATOM | 2679 | CE1 | PHE | C | 404 | −79.269 | −47.597 | −40.134 | 1.00 | 16.30 | C |
| ATOM | 2680 | CZ | PHE | C | 404 | −78.740 | −48.862 | −40.289 | 1.00 | 14.09 | C |
| ATOM | 2681 | CE2 | PHE | C | 404 | −79.356 | −49.804 | −41.147 | 1.00 | 11.55 | C |
| ATOM | 2682 | CD2 | PHE | C | 404 | −80.535 | −49.433 | −41.855 | 1.00 | 15.05 | C |
| ATOM | 2683 | C | PHE | C | 404 | −84.803 | −47.142 | −42.168 | 1.00 | 16.74 | C |
| ATOM | 2684 | O | PHE | C | 404 | −85.342 | −47.531 | −43.202 | 1.00 | 17.23 | O |
| ATOM | 2685 | N | THR | C | 405 | −85.234 | −46.085 | −41.479 | 1.00 | 16.28 | N |
| ATOM | 2686 | CA | THR | C | 405 | −86.417 | −45.367 | −41.928 | 1.00 | 15.17 | C |
| ATOM | 2687 | CB | THR | C | 405 | −87.571 | −45.555 | −40.914 | 1.00 | 19.34 | C |
| ATOM | 2688 | OG1 | THR | C | 405 | −87.073 | −45.359 | −39.590 | 1.00 | 18.94 | O |
| ATOM | 2689 | CG2 | THR | C | 405 | −88.141 | −46.980 | −41.007 | 1.00 | 20.52 | C |
| ATOM | 2690 | C | THR | C | 405 | −86.064 | −43.904 | −42.078 | 1.00 | 17.51 | C |
| ATOM | 2691 | O | THR | C | 405 | −85.376 | −43.345 | −41.220 | 1.00 | 14.48 | O |
| ATOM | 2692 | N | ALA | C | 406 | −86.519 | −43.285 | −43.174 | 1.00 | 15.65 | N |
| ATOM | 2693 | CA | ALA | C | 406 | −86.117 | −41.919 | −43.531 | 1.00 | 18.73 | C |
| ATOM | 2694 | CB | ALA | C | 406 | −86.602 | −41.565 | −44.952 | 1.00 | 15.25 | C |
| ATOM | 2695 | C | ALA | C | 406 | −86.665 | −40.923 | −42.534 | 1.00 | 19.11 | C |
| ATOM | 2696 | O | ALA | C | 406 | −87.776 | −41.069 | −42.088 | 1.00 | 18.20 | O |
| ATOM | 2697 | N | THR | C | 407 | −85.861 | −39.919 | −42.167 | 1.00 | 23.17 | N |
| ATOM | 2698 | CA | THR | C | 407 | −86.357 | −38.856 | −41.288 | 1.00 | 24.24 | C |
| ATOM | 2699 | CB | THR | C | 407 | −85.270 | −38.259 | −40.353 | 1.00 | 21.03 | C |
| ATOM | 2700 | OG1 | THR | C | 407 | −84.222 | −37.724 | −41.147 | 1.00 | 22.96 | O |
| ATOM | 2701 | CG2 | THR | C | 407 | −84.685 | −39.308 | −39.404 | 1.00 | 23.12 | C |
| ATOM | 2702 | C | THR | C | 407 | −87.075 | −37.728 | −42.051 | 1.00 | 28.02 | C |
| ATOM | 2703 | O | THR | C | 407 | −87.787 | −36.963 | −41.435 | 1.00 | 30.92 | O |
| ATOM | 2704 | N | LYS | C | 408 | −86.889 | −37.659 | −43.379 | 1.00 | 28.82 | N |
| ATOM | 2705 | CA | LYS | C | 408 | −87.485 | −36.616 | −44.269 | 1.00 | 34.36 | C |
| ATOM | 2706 | CB | LYS | C | 408 | −86.393 | −35.691 | −44.847 | 1.00 | 37.71 | C |
| ATOM | 2707 | CG | LYS | C | 408 | −85.845 | −34.627 | −43.887 | 1.00 | 44.88 | C |
| ATOM | 2708 | CD | LYS | C | 408 | −84.372 | −34.285 | −44.146 | 1.00 | 48.56 | C |
| ATOM | 2709 | CE | LYS | C | 408 | −84.177 | −33.276 | −45.276 | 1.00 | 58.37 | C |
| ATOM | 2710 | NZ | LYS | C | 408 | −84.135 | −33.931 | −46.621 | 1.00 | 59.71 | N |
| ATOM | 2711 | C | LYS | C | 408 | −88.262 | −37.265 | −45.434 | 1.00 | 34.70 | C |
| ATOM | 2712 | O | LYS | C | 408 | −87.899 | −38.337 | −45.917 | 1.00 | 27.93 | O |
| ATOM | 2713 | N | LYS | C | 409 | −89.323 | −36.615 | −45.904 | 1.00 | 31.77 | N |
| ATOM | 2714 | CA | LYS | C | 409 | −90.167 | −37.249 | −46.893 | 1.00 | 29.16 | C |
| ATOM | 2715 | CB | LYS | C | 409 | −91.583 | −36.634 | −46.907 | 1.00 | 41.65 | C |
| ATOM | 2716 | CG | LYS | C | 409 | −92.459 | −37.029 | −45.720 | 1.00 | 52.57 | C |
| ATOM | 2717 | CD | LYS | C | 409 | −92.489 | −38.541 | −45.486 | 1.00 | 58.96 | C |
| ATOM | 2718 | CE | LYS | C | 409 | −93.518 | −38.926 | −44.430 | 1.00 | 61.73 | C |
| ATOM | 2719 | NZ | LYS | C | 409 | −94.888 | −38.473 | −44.820 | 1.00 | 70.37 | N |
| ATOM | 2720 | C | LYS | C | 409 | −89.558 | −37.227 | −48.297 | 1.00 | 26.22 | C |
| ATOM | 2721 | O | LYS | C | 409 | −89.974 | −37.990 | −49.147 | 1.00 | 23.12 | O |
| ATOM | 2722 | N | ASP | C | 410 | −88.587 | −36.355 | −48.536 | 1.00 | 26.03 | N |
| ATOM | 2723 | CA | ASP | C | 410 | −88.039 | −36.173 | −49.901 | 1.00 | 32.66 | C |
| ATOM | 2724 | CB | ASP | C | 410 | −87.531 | −34.726 | −50.112 | 1.00 | 36.81 | C |
| ATOM | 2725 | CG | ASP | C | 410 | −86.335 | −34.358 | −49.191 | 1.00 | 48.97 | C |
| ATOM | 2726 | OD1 | ASP | C | 410 | −85.842 | −35.210 | −48.402 | 1.00 | 40.68 | O |
| ATOM | 2727 | OD2 | ASP | C | 410 | −85.881 | −33.197 | −49.279 | 1.00 | 48.67 | O |
| ATOM | 2728 | C | ASP | C | 410 | −86.947 | −37.197 | −50.306 | 1.00 | 36.36 | C |
| ATOM | 2729 | O | ASP | C | 410 | −86.488 | −37.191 | −51.464 | 1.00 | 30.60 | O |
| ATOM | 2730 | N | MET | C | 411 | −86.533 | −38.038 | −49.343 | 1.00 | 27.26 | N |
| ATOM | 2731 | CA | MET | C | 411 | −85.516 | −39.093 | −49.552 | 1.00 | 27.50 | C |
| ATOM | 2732 | CB | MET | C | 411 | −84.897 | −39.517 | −48.192 | 1.00 | 20.14 | C |
| ATOM | 2733 | CG | MET | C | 411 | −84.070 | −38.385 | −47.589 | 1.00 | 34.07 | C |
| ATOM | 2734 | SD | MET | C | 411 | −83.332 | −38.664 | −45.967 | 1.00 | 39.57 | S |
| ATOM | 2735 | CE | MET | C | 411 | −84.751 | −38.700 | −44.911 | 1.00 | 26.88 | C |
| ATOM | 2736 | C | MET | C | 411 | −86.083 | −40.333 | −50.276 | 1.00 | 27.01 | C |
| ATOM | 2737 | O | MET | C | 411 | −87.274 | −40.627 | −50.198 | 1.00 | 20.36 | O |
| ATOM | 2738 | N | SER | C | 412 | −85.216 | −41.058 | −50.973 | 1.00 | 22.03 | N |
| ATOM | 2739 | CA | SER | C | 412 | −85.595 | −42.349 | −51.537 | 1.00 | 19.59 | C |
| ATOM | 2740 | CB | SER | C | 412 | −85.782 | −42.280 | −53.032 | 1.00 | 19.83 | C |
| ATOM | 2741 | OG | SER | C | 412 | −84.763 | −41.465 | −53.592 | 1.00 | 25.16 | O |
| ATOM | 2742 | C | SER | C | 412 | −84.461 | −43.256 | −51.120 | 1.00 | 20.43 | C |
| ATOM | 2743 | O | SER | C | 412 | −83.290 | −42.830 | −51.270 | 1.00 | 16.79 | O |
| ATOM | 2744 | N | PRO | C | 413 | −84.758 | −44.564 | −51.045 | 1.00 | 15.16 | N |
| ATOM | 2745 | CA | PRO | C | 413 | −85.936 | −45.093 | −50.394 | 1.00 | 16.63 | C |

TABLE 4-continued

Atomic coordinates for CRBN(TBD):Pomalidomide (Murine protein)

| ATOM | 2746 | CB | PRO | C | 413 | −85.644 | −46.608 | −50.301 | 1.00 | 13.23 | C |
|------|------|-----|-----|---|-----|---------|---------|---------|------|-------|---|
| ATOM | 2747 | CG | PRO | C | 413 | −84.187 | −46.660 | −50.082 | 1.00 | 14.85 | C |
| ATOM | 2748 | CD | PRO | C | 413 | −83.592 | −45.437 | −50.799 | 1.00 | 12.35 | C |
| ATOM | 2749 | C | PRO | C | 413 | −86.361 | −44.491 | −49.091 | 1.00 | 17.58 | C |
| ATOM | 2750 | O | PRO | C | 413 | −85.520 | −44.078 | −48.306 | 1.00 | 18.78 | O |
| ATOM | 2751 | N | GLN | C | 414 | −87.669 | −44.465 | −48.841 | 1.00 | 14.24 | N |
| ATOM | 2752 | CA | GLN | C | 414 | −88.154 | −44.057 | −47.528 | 1.00 | 14.72 | C |
| ATOM | 2753 | CB | GLN | C | 414 | −89.675 | −43.831 | −47.575 | 1.00 | 21.18 | C |
| ATOM | 2754 | CG | GLN | C | 414 | −90.067 | −42.483 | −48.210 | 1.00 | 16.33 | C |
| ATOM | 2755 | CD | GLN | C | 414 | −89.579 | −41.324 | −47.348 | 1.00 | 21.34 | C |
| ATOM | 2756 | OE1 | GLN | C | 414 | −88.690 | −40.569 | −47.471 | 1.00 | 25.26 | O |
| ATOM | 2757 | NE2 | GLN | C | 414 | −90.121 | −41.214 | −46.149 | 1.00 | 16.87 | N |
| ATOM | 2758 | C | GLN | C | 414 | −87.762 | −45.052 | −46.424 | 1.00 | 13.47 | C |
| ATOM | 2759 | O | GLN | C | 414 | −87.766 | −44.713 | −45.251 | 1.00 | 13.39 | O |
| ATOM | 2760 | N | LYS | C | 415 | −87.425 | −46.281 | −46.818 | 1.00 | 12.81 | N |
| ATOM | 2761 | CA | LYS | C | 415 | −87.047 | −47.316 | −45.887 | 1.00 | 17.27 | C |
| ATOM | 2762 | CB | LYS | C | 415 | −88.289 | −47.969 | −45.200 | 1.00 | 27.39 | C |
| ATOM | 2763 | CG | LYS | C | 415 | −88.907 | −49.132 | −45.918 | 1.00 | 31.26 | C |
| ATOM | 2764 | CD | LYS | C | 415 | −90.397 | −49.203 | −45.631 | 1.00 | 40.02 | C |
| ATOM | 2765 | CE | LYS | C | 415 | −91.174 | −49.680 | −46.845 | 1.00 | 31.36 | C |
| ATOM | 2766 | NZ | LYS | C | 415 | −91.738 | −48.555 | −47.698 | 1.00 | 26.51 | N |
| ATOM | 2767 | C | LYS | C | 415 | −86.202 | −48.348 | −46.638 | 1.00 | 15.30 | C |
| ATOM | 2768 | O | LYS | C | 415 | −86.316 | −48.482 | −47.880 | 1.00 | 14.31 | O |
| ATOM | 2769 | N | PHE | C | 416 | −85.323 | −49.018 | −45.897 | 1.00 | 13.65 | N |
| ATOM | 2770 | CA | PHE | C | 416 | −84.531 | −50.141 | −46.413 | 1.00 | 15.39 | C |
| ATOM | 2771 | CB | PHE | C | 416 | −83.387 | −49.656 | −47.344 | 1.00 | 15.59 | C |
| ATOM | 2772 | CG | PHE | C | 416 | −82.271 | −48.919 | −46.628 | 1.00 | 16.24 | C |
| ATOM | 2773 | CD1 | PHE | C | 416 | −81.099 | −49.595 | −46.218 | 1.00 | 14.04 | C |
| ATOM | 2774 | CE1 | PHE | C | 416 | −80.082 | −48.917 | −45.561 | 1.00 | 14.00 | C |
| ATOM | 2775 | CZ | PHE | C | 416 | −80.209 | −47.575 | −45.293 | 1.00 | 13.70 | C |
| ATOM | 2776 | CE2 | PHE | C | 416 | −81.336 | −46.880 | −45.694 | 1.00 | 11.81 | C |
| ATOM | 2777 | CD2 | PHE | C | 416 | −82.372 | −47.547 | −46.361 | 1.00 | 15.66 | C |
| ATOM | 2778 | C | PHE | C | 416 | −84.005 | −50.943 | −45.223 | 1.00 | 14.79 | C |
| ATOM | 2779 | O | PHE | C | 416 | −84.293 | −50.597 | −44.063 | 1.00 | 18.25 | O |
| ATOM | 2780 | N | TRP | C | 417 | −83.346 | −52.057 | −45.513 | 1.00 | 12.82 | N |
| ATOM | 2781 | CA | TRP | C | 417 | −82.753 | −52.922 | −44.501 | 1.00 | 16.09 | C |
| ATOM | 2782 | CB | TRP | C | 417 | −83.332 | −54.370 | −44.545 | 1.00 | 15.43 | C |
| ATOM | 2783 | CG | TRP | C | 417 | −84.842 | −54.390 | −44.515 | 1.00 | 13.85 | C |
| ATOM | 2784 | CD1 | TRP | C | 417 | −85.704 | −54.208 | −45.579 | 1.00 | 16.56 | C |
| ATOM | 2785 | NE1 | TRP | C | 417 | −87.009 | −54.284 | −45.164 | 1.00 | 20.24 | N |
| ATOM | 2786 | CE2 | TRP | C | 417 | −87.068 | −54.521 | −43.830 | 1.00 | 19.94 | C |
| ATOM | 2787 | CD2 | TRP | C | 417 | −85.701 | −54.595 | −43.350 | 1.00 | 16.94 | C |
| ATOM | 2788 | CE3 | TRP | C | 417 | −85.471 | −54.829 | −42.004 | 1.00 | 17.63 | C |
| ATOM | 2789 | CZ3 | TRP | C | 417 | −86.563 | −54.992 | −41.150 | 1.00 | 16.62 | C |
| ATOM | 2790 | CH2 | TRP | C | 417 | −87.878 | −54.912 | −41.621 | 1.00 | 18.24 | C |
| ATOM | 2791 | CZ2 | TRP | C | 417 | −88.163 | −54.666 | −42.975 | 1.00 | 20.48 | C |
| ATOM | 2792 | C | TRP | C | 417 | −81.265 | −52.953 | −44.638 | 1.00 | 18.16 | C |
| ATOM | 2793 | O | TRP | C | 417 | −80.720 | −53.149 | −45.731 | 1.00 | 20.68 | O |
| ATOM | 2794 | N | GLY | C | 418 | −80.588 | −52.768 | −43.514 | 1.00 | 15.54 | N |
| ATOM | 2795 | CA | GLY | C | 418 | −79.139 | −52.996 | −43.460 | 1.00 | 19.03 | C |
| ATOM | 2796 | C | GLY | C | 418 | −78.935 | −54.289 | −42.693 | 1.00 | 15.90 | C |
| ATOM | 2797 | O | GLY | C | 418 | −79.321 | −54.390 | −41.516 | 1.00 | 14.11 | O |
| ATOM | 2798 | N | LEU | C | 419 | −78.413 | −55.291 | −43.391 | 1.00 | 17.31 | N |
| ATOM | 2799 | CA | LEU | C | 419 | −78.292 | −56.641 | −42.840 | 1.00 | 19.06 | C |
| ATOM | 2800 | CB | LEU | C | 419 | −79.000 | −57.661 | −43.777 | 1.00 | 17.16 | C |
| ATOM | 2801 | CG | LEU | C | 419 | −80.480 | −57.343 | −44.085 | 1.00 | 18.47 | C |
| ATOM | 2802 | CD1 | LEU | C | 419 | −81.105 | −58.334 | −45.062 | 1.00 | 20.53 | C |
| ATOM | 2803 | CD2 | LEU | C | 419 | −81.304 | −57.258 | −42.793 | 1.00 | 18.86 | C |
| ATOM | 2804 | C | LEU | C | 419 | −76.781 | −57.013 | −42.598 | 1.00 | 20.83 | C |
| ATOM | 2805 | O | LEU | C | 419 | −75.894 | −56.709 | −43.412 | 1.00 | 21.07 | O |
| ATOM | 2806 | N | THR | C | 420 | −76.502 | −57.662 | −41.474 | 1.00 | 22.24 | N |
| ATOM | 2807 | CA | THR | C | 420 | −75.119 | −58.099 | −41.172 | 1.00 | 21.28 | C |
| ATOM | 2808 | CB | THR | C | 420 | −74.935 | −58.384 | −39.665 | 1.00 | 22.15 | C |
| ATOM | 2809 | OG1 | THR | C | 420 | −75.288 | −57.206 | −38.933 | 1.00 | 21.18 | O |
| ATOM | 2810 | CG2 | THR | C | 420 | −73.468 | −58.760 | −39.315 | 1.00 | 25.70 | C |
| ATOM | 2811 | C | THR | C | 420 | −74.863 | −59.312 | −42.006 | 1.00 | 17.49 | C |
| ATOM | 2812 | O | THR | C | 420 | −75.555 | −60.293 | −41.864 | 1.00 | 19.47 | O |
| ATOM | 2813 | N | ARG | C | 421 | −73.902 | −59.221 | −42.929 | 1.00 | 16.40 | N |
| ATOM | 2814 | CA | ARG | C | 421 | −73.645 | −60.311 | −43.884 | 1.00 | 22.27 | C |
| ATOM | 2815 | CB | ARG | C | 421 | −72.481 | −59.993 | −44.803 | 1.00 | 22.53 | C |
| ATOM | 2816 | CG | ARG | C | 421 | −72.879 | −59.341 | −46.098 | 1.00 | 29.03 | C |
| ATOM | 2817 | CD | ARG | C | 421 | −71.623 | −58.991 | −46.899 | 1.00 | 38.94 | C |
| ATOM | 2818 | NE | ARG | C | 421 | −71.919 | −58.145 | −48.051 | 1.00 | 44.04 | N |
| ATOM | 2819 | CZ | ARG | C | 421 | −71.983 | −58.581 | −49.306 | 1.00 | 44.92 | C |
| ATOM | 2820 | NH1 | ARG | C | 421 | −71.752 | −59.863 | −49.594 | 1.00 | 50.35 | N |
| ATOM | 2821 | NH2 | ARG | C | 421 | −72.266 | −57.728 | −50.276 | 1.00 | 45.31 | N |
| ATOM | 2822 | C | ARG | C | 421 | −73.312 | −61.617 | −43.188 | 1.00 | 20.53 | C |
| ATOM | 2823 | O | ARG | C | 421 | −73.675 | −62.682 | −43.684 | 1.00 | 19.34 | O |

TABLE 4-continued

Atomic coordinates for CRBN(TBD):Pomalidomide (Murine protein)

| ATOM | 2824 | N | SER | C | 422 | −72.615 | −61.532 | −42.052 | 1.00 | 19.89 | N |
|---|---|---|---|---|---|---|---|---|---|---|---|
| ATOM | 2825 | CA | SER | C | 422 | −72.101 | −62.726 | −41.412 | 1.00 | 21.25 | C |
| ATOM | 2826 | CB | SER | C | 422 | −70.952 | −62.397 | −40.441 | 1.00 | 22.28 | C |
| ATOM | 2827 | OG | SER | C | 422 | −71.392 | −61.587 | −39.355 | 1.00 | 23.24 | O |
| ATOM | 2828 | C | SER | C | 422 | −73.265 | −63.425 | −40.709 | 1.00 | 26.68 | C |
| ATOM | 2829 | O | SER | C | 422 | −73.121 | −64.557 | −40.217 | 1.00 | 26.13 | O |
| ATOM | 2830 | N | ALA | C | 423 | −74.427 | −62.754 | −40.680 | 1.00 | 20.09 | N |
| ATOM | 2831 | CA | ALA | C | 423 | −75.600 | −63.319 | −40.034 | 1.00 | 22.85 | C |
| ATOM | 2832 | CB | ALA | C | 423 | −76.373 | −62.248 | −39.254 | 1.00 | 20.19 | C |
| ATOM | 2833 | C | ALA | C | 423 | −76.503 | −64.027 | −41.026 | 1.00 | 20.26 | C |
| ATOM | 2834 | O | ALA | C | 423 | −77.602 | −64.437 | −40.678 | 1.00 | 19.34 | O |
| ATOM | 2835 | N | LEU | C | 424 | −76.030 | −64.196 | −42.256 | 1.00 | 18.13 | N |
| ATOM | 2836 | CA | LEU | C | 424 | −76.859 | −64.803 | −43.308 | 1.00 | 19.56 | C |
| ATOM | 2837 | CB | LEU | C | 424 | −77.266 | −63.740 | −44.343 | 1.00 | 20.60 | C |
| ATOM | 2838 | CG | LEU | C | 424 | −78.143 | −62.550 | −43.936 | 1.00 | 20.34 | C |
| ATOM | 2839 | CD1 | LEU | C | 424 | −78.203 | −61.482 | −45.054 | 1.00 | 19.36 | C |
| ATOM | 2840 | CD2 | LEU | C | 424 | −79.530 | −63.018 | −43.543 | 1.00 | 21.80 | C |
| ATOM | 2841 | C | LEU | C | 424 | −76.084 | −65.917 | −44.011 | 1.00 | 24.43 | C |
| ATOM | 2842 | O | LEU | C | 424 | −74.866 | −65.827 | −44.109 | 1.00 | 23.18 | O |
| ATOM | 2843 | N | LEU | C | 425 | −76.785 | −66.943 | −44.510 | 1.00 | 25.17 | N |
| ATOM | 2844 | CA | LEU | C | 425 | −76.167 | −68.016 | −45.339 | 1.00 | 33.88 | C |
| ATOM | 2845 | CB | LEU | C | 425 | −76.579 | −69.428 | −44.864 | 1.00 | 30.99 | C |
| ATOM | 2846 | CG | LEU | C | 425 | −75.602 | −70.309 | −44.053 | 1.00 | 36.36 | C |
| ATOM | 2847 | CD1 | LEU | C | 425 | −76.026 | −71.768 | −44.169 | 1.00 | 32.35 | C |
| ATOM | 2848 | CD2 | LEU | C | 425 | −74.142 | −70.153 | −44.465 | 1.00 | 26.75 | C |
| ATOM | 2849 | C | LEU | C | 425 | −76.429 | −67.841 | −46.861 | 1.00 | 43.24 | C |
| ATOM | 2850 | O | LEU | C | 425 | −77.442 | −67.256 | −47.238 | 1.00 | 44.94 | O |
| ATOM | 2851 | N | PRO | C | 426 | −75.647 | −68.566 | −47.708 | 1.00 | 63.22 | N |
| ATOM | 2852 | CA | PRO | C | 426 | −74.702 | −68.070 | −48.683 | 1.00 | 54.32 | C |
| ATOM | 2853 | CB | PRO | C | 426 | −75.608 | −67.764 | −49.874 | 1.00 | 49.23 | C |
| ATOM | 2854 | CG | PRO | C | 426 | −76.642 | −68.885 | −49.793 | 1.00 | 54.01 | C |
| ATOM | 2855 | CD | PRO | C | 426 | −76.513 | −69.528 | −48.407 | 1.00 | 62.25 | C |
| ATOM | 2856 | C | PRO | C | 426 | −73.830 | −66.886 | −48.210 | 1.00 | 63.22 | C |
| ATOM | 2857 | O | PRO | C | 426 | −73.786 | −66.592 | −47.020 | 1.00 | 56.35 | O |
| ATOM | 2858 | N | THR | C | 427 | −73.099 | −66.262 | −49.133 | 1.00 | 84.63 | N |
| ATOM | 2859 | CA | THR | C | 427 | −72.073 | −65.264 | −48.780 | 1.00 | 77.10 | C |
| ATOM | 2860 | CB | THR | C | 427 | −70.645 | −65.857 | −48.915 | 1.00 | 67.64 | C |
| ATOM | 2861 | OG1 | THR | C | 427 | −70.595 | −67.137 | −48.272 | 1.00 | 65.52 | O |
| ATOM | 2862 | CG2 | THR | C | 427 | −69.586 | −64.936 | −48.284 | 1.00 | 57.97 | C |
| ATOM | 2863 | C | THR | C | 427 | −72.200 | −64.004 | −49.643 | 1.00 | 79.60 | C |
| ATOM | 2864 | O | THR | C | 427 | −71.996 | −62.882 | −49.169 | 1.00 | 75.88 | O |
| ATOM | 2865 | O4 | SO4 | E | 1 | −54.723 | −44.990 | −18.711 | 1.00 | 34.87 | O |
| ATOM | 2866 | S | SO4 | E | 1 | −53.926 | −46.019 | −19.445 | 1.00 | 30.33 | S |
| ATOM | 2867 | O1 | SO4 | E | 1 | −52.667 | −45.226 | −19.497 | 1.00 | 40.69 | O |
| ATOM | 2868 | O2 | SO4 | E | 1 | −54.494 | −46.521 | −20.711 | 1.00 | 37.83 | O |
| ATOM | 2869 | O3 | SO4 | E | 1 | −53.762 | −47.313 | −18.685 | 1.00 | 27.49 | O |
| ATOM | 2870 | O4 | SO4 | E | 2 | −51.527 | −50.153 | −19.351 | 1.00 | 28.72 | O |
| ATOM | 2871 | S | SO4 | E | 2 | −51.025 | −50.912 | −20.507 | 1.00 | 28.44 | S |
| ATOM | 2872 | O1 | SO4 | E | 2 | −50.193 | −50.041 | −21.305 | 1.00 | 31.03 | O |
| ATOM | 2873 | O2 | SO4 | E | 2 | −52.120 | −51.432 | −21.333 | 1.00 | 26.16 | O |
| ATOM | 2874 | O3 | SO4 | E | 2 | −50.189 | −52.060 | −20.032 | 1.00 | 36.16 | O |
| ATOM | 2875 | O4 | SO4 | E | 3 | −45.929 | −50.344 | −17.864 | 1.00 | 36.74 | O |
| ATOM | 2876 | S | SO4 | E | 3 | −45.906 | −51.755 | −18.032 | 1.00 | 37.79 | S |
| ATOM | 2877 | O1 | SO4 | E | 3 | −45.165 | −52.128 | −19.289 | 1.00 | 36.69 | O |
| ATOM | 2878 | O2 | SO4 | E | 3 | −47.343 | −52.087 | −18.010 | 1.00 | 36.35 | O |
| ATOM | 2879 | O3 | SO4 | E | 3 | −45.071 | −52.414 | −17.008 | 1.00 | 32.89 | O |
| ATOM | 2880 | O4 | SO4 | E | 4 | −53.189 | −53.605 | −24.266 | 1.00 | 25.07 | O |
| ATOM | 2881 | S | SO4 | E | 4 | −52.543 | −53.562 | −25.609 | 1.00 | 29.75 | S |
| ATOM | 2882 | O1 | SO4 | E | 4 | −52.690 | −52.307 | −26.353 | 1.00 | 31.43 | O |
| ATOM | 2883 | O2 | SO4 | E | 4 | −53.119 | −54.654 | −26.453 | 1.00 | 30.96 | O |
| ATOM | 2884 | O3 | SO4 | E | 4 | −51.141 | −53.819 | −25.399 | 1.00 | 35.91 | O |
| ATOM | 2885 | O4 | SO4 | E | 5 | −89.973 | −45.891 | −49.829 | 1.00 | 49.41 | O |
| ATOM | 2886 | S | SO4 | E | 5 | −90.034 | −45.443 | −51.227 | 1.00 | 37.09 | S |
| ATOM | 2887 | O1 | SO4 | E | 5 | −88.890 | −44.623 | −51.635 | 1.00 | 38.19 | O |
| ATOM | 2888 | O2 | SO4 | E | 5 | −91.168 | −44.526 | −51.511 | 1.00 | 32.01 | O |
| ATOM | 2889 | O3 | SO4 | E | 5 | −90.041 | −46.709 | −52.003 | 1.00 | 29.16 | O |
| ATOM | 2890 | O4 | SO4 | E | 6 | −93.866 | −50.074 | −49.055 | 0.33 | 20.68 | O |
| ATOM | 2891 | S | SO4 | E | 6 | −92.762 | −50.233 | −50.044 | 0.33 | 21.45 | S |
| ATOM | 2892 | O1 | SO4 | E | 6 | −92.281 | −48.910 | −50.439 | 0.50 | 34.02 | O |
| ATOM | 2893 | O2 | SO4 | E | 6 | −93.220 | −50.982 | −51.213 | 0.50 | 23.08 | O |
| ATOM | 2894 | O3 | SO4 | E | 6 | −91.592 | −50.923 | −49.480 | 0.50 | 23.75 | O |
| ATOM | 2895 | O4 | SO4 | E | 7 | −38.497 | −35.089 | 1.178 | 1.00 | 71.25 | O |
| ATOM | 2896 | S | SO4 | E | 7 | −39.233 | −35.117 | −0.107 | 1.00 | 66.22 | S |
| ATOM | 2897 | O1 | SO4 | E | 7 | −38.459 | −34.457 | −1.177 | 1.00 | 57.19 | O |
| ATOM | 2898 | O2 | SO4 | E | 7 | −40.518 | −34.397 | 0.034 | 1.00 | 56.79 | O |
| ATOM | 2899 | O3 | SO4 | E | 7 | −39.496 | −36.525 | −0.455 | 1.00 | 58.08 | O |
| ATOM | 2900 | O4 | SO4 | E | 8 | −72.907 | −38.605 | −33.750 | 1.00 | 59.22 | O |
| ATOM | 2901 | S | SO4 | E | 8 | −72.391 | −39.680 | −34.641 | 1.00 | 69.73 | S |

TABLE 4-continued

Atomic coordinates for CRBN(TBD):Pomalidomide (Murine protein)

| ATOM | 2902 | O1 | SO4 | E | 8 | −71.128 | −39.280 | −35.293 | 1.00 | 71.09 | O |
|---|---|---|---|---|---|---|---|---|---|---|---|
| ATOM | 2903 | O2 | SO4 | E | 8 | −73.339 | −39.990 | −35.730 | 1.00 | 71.11 | O |
| ATOM | 2904 | O3 | SO4 | E | 8 | −72.188 | −40.888 | −33.811 | 1.00 | 57.92 | O |
| ATOM | 2905 | ZN | ZN | F | 1 | −37.031 | −60.796 | −4.821 | 1.00 | 21.11 | ZN |
| ATOM | 2906 | ZN | ZN | F | 2 | −62.197 | −67.575 | −32.859 | 1.00 | 34.85 | ZN |
| ATOM | 2907 | ZN | ZN | F | 3 | −83.278 | −67.696 | −37.358 | 1.00 | 39.65 | ZN |
| ATOM | 2908 | ZN | ZN | F | 4 | −67.622 | −38.280 | −9.187 | 1.00 | 18.91 | ZN |
| ATOM | 2909 | O2 | MOL | G | 1 | −34.200 | −69.411 | −20.877 | 1.00 | 27.56 | O |
| ATOM | 2910 | C3 | MOL | G | 1 | −33.576 | −69.176 | −21.908 | 1.00 | 36.52 | C |
| ATOM | 2911 | C7 | MOL | G | 1 | −32.221 | −69.428 | −22.134 | 1.00 | 33.94 | C |
| ATOM | 2912 | C10 | MOL | G | 1 | −31.201 | −69.975 | −21.356 | 1.00 | 43.15 | C |
| ATOM | 2913 | N3 | MOL | G | 1 | −31.457 | −70.383 | −20.108 | 1.00 | 38.82 | N |
| ATOM | 2914 | C13 | MOL | G | 1 | −29.917 | −70.097 | −21.889 | 1.00 | 35.85 | C |
| ATOM | 2915 | C12 | MOL | G | 1 | −29.660 | −69.675 | −23.196 | 1.00 | 38.37 | C |
| ATOM | 2916 | C9 | MOL | G | 1 | −30.685 | −69.125 | −23.972 | 1.00 | 40.85 | C |
| ATOM | 2917 | C6 | MOL | G | 1 | −31.966 | −69.007 | −23.435 | 1.00 | 35.10 | C |
| ATOM | 2918 | C2 | MOL | G | 1 | −33.183 | −68.522 | −23.928 | 1.00 | 36.53 | C |
| ATOM | 2919 | O1 | MOL | G | 1 | −33.362 | −68.060 | −25.052 | 1.00 | 35.98 | O |
| ATOM | 2920 | N1 | MOL | G | 1 | −34.116 | −68.632 | −22.985 | 1.00 | 36.13 | N |
| ATOM | 2921 | C1 | MOL | G | 1 | −35.541 | −68.279 | −23.090 | 1.00 | 33.12 | C |
| ATOM | 2922 | C5 | MOL | G | 1 | −35.820 | −66.773 | −23.072 | 1.00 | 27.50 | C |
| ATOM | 2923 | C8 | MOL | G | 1 | −37.351 | −66.569 | −23.137 | 1.00 | 26.34 | C |
| ATOM | 2924 | C11 | MOL | G | 1 | −37.942 | −67.284 | −24.368 | 1.00 | 34.06 | C |
| ATOM | 2925 | O4 | MOL | G | 1 | −38.958 | −66.857 | −24.914 | 1.00 | 24.63 | O |
| ATOM | 2926 | N2 | MOL | G | 1 | −37.303 | −68.411 | −24.913 | 1.00 | 24.70 | N |
| ATOM | 2927 | C4 | MOL | G | 1 | −36.149 | −68.941 | −24.337 | 1.00 | 34.50 | C |
| ATOM | 2928 | O3 | MOL | G | 1 | −35.632 | −69.951 | −24.829 | 1.00 | 28.91 | O |
| ATOM | 2929 | O2 | MOL | H | 1 | −70.412 | −51.591 | −36.451 | 1.00 | 34.85 | O |
| ATOM | 2930 | C3 | MOL | H | 1 | −70.148 | −50.572 | −37.091 | 1.00 | 33.52 | C |
| ATOM | 2931 | C7 | MOL | H | 1 | −70.413 | −50.373 | −38.445 | 1.00 | 44.01 | C |
| ATOM | 2932 | C10 | MOL | H | 1 | −70.987 | −51.161 | −39.437 | 1.00 | 44.10 | C |
| ATOM | 2933 | N3 | MOL | H | 1 | −71.413 | −52.388 | −39.153 | 1.00 | 49.44 | N |
| ATOM | 2934 | C13 | MOL | H | 1 | −71.109 | −50.657 | −40.730 | 1.00 | 42.96 | C |
| ATOM | 2935 | C12 | MOL | H | 1 | −70.660 | −49.370 | −41.023 | 1.00 | 48.49 | C |
| ATOM | 2936 | C9 | MOL | H | 1 | −70.089 | −48.581 | −40.027 | 1.00 | 40.03 | C |
| ATOM | 2937 | C6 | MOL | H | 1 | −69.967 | −49.088 | −38.740 | 1.00 | 39.17 | C |
| ATOM | 2938 | C2 | MOL | H | 1 | −69.454 | −48.571 | −37.553 | 1.00 | 37.80 | C |
| ATOM | 2939 | O1 | MOL | H | 1 | −68.974 | −47.448 | −37.429 | 1.00 | 39.09 | O |
| ATOM | 2940 | N1 | MOL | H | 1 | −69.573 | −49.482 | −36.587 | 1.00 | 32.80 | N |
| ATOM | 2941 | C1 | MOL | H | 1 | −69.184 | −49.332 | −35.177 | 1.00 | 26.39 | C |
| ATOM | 2942 | C5 | MOL | H | 1 | −67.676 | −49.236 | −34.973 | 1.00 | 27.10 | C |
| ATOM | 2943 | C8 | MOL | H | 1 | −67.386 | −49.108 | −33.468 | 1.00 | 26.29 | C |
| ATOM | 2944 | C11 | MOL | H | 1 | −68.167 | −47.913 | −32.865 | 1.00 | 34.99 | C |
| ATOM | 2945 | O4 | MOL | H | 1 | −67.742 | −47.318 | −31.879 | 1.00 | 24.22 | O |
| ATOM | 2946 | N2 | MOL | H | 1 | −69.361 | −47.473 | −33.450 | 1.00 | 27.76 | N |
| ATOM | 2947 | C4 | MOL | H | 1 | −69.893 | −48.117 | −34.567 | 1.00 | 32.09 | C |
| ATOM | 2948 | O3 | MOL | H | 1 | −70.950 | −47.709 | −35.049 | 1.00 | 34.63 | O |
| ATOM | 2949 | O2 | MOL | I | 1 | −76.040 | −47.643 | −32.032 | 1.00 | 37.97 | O |
| ATOM | 2950 | C3 | MOL | I | 1 | −75.540 | −48.769 | −31.955 | 1.00 | 44.24 | C |
| ATOM | 2951 | C7 | MOL | I | 1 | −75.026 | −49.356 | −30.798 | 1.00 | 40.46 | C |
| ATOM | 2952 | C10 | MOL | I | 1 | −74.907 | −48.934 | −29.478 | 1.00 | 46.25 | C |
| ATOM | 2953 | N3 | MOL | I | 1 | −75.341 | −47.730 | −29.121 | 1.00 | 49.70 | N |
| ATOM | 2954 | C13 | MOL | I | 1 | −74.328 | −49.781 | −28.532 | 1.00 | 49.75 | C |
| ATOM | 2955 | C12 | MOL | I | 1 | −73.867 | −51.046 | −28.909 | 1.00 | 43.94 | C |
| ATOM | 2956 | C9 | MOL | I | 1 | −73.986 | −51.474 | −30.230 | 1.00 | 37.98 | C |
| ATOM | 2957 | C6 | MOL | I | 1 | −74.570 | −50.621 | −31.170 | 1.00 | 50.63 | C |
| ATOM | 2958 | C2 | MOL | I | 1 | −74.831 | −50.734 | −32.530 | 1.00 | 31.69 | C |
| ATOM | 2959 | O1 | MOL | I | 1 | −74.567 | −51.710 | −33.226 | 1.00 | 37.63 | O |
| ATOM | 2960 | N1 | MOL | I | 1 | −75.426 | −49.629 | −32.962 | 1.00 | 38.07 | N |
| ATOM | 2961 | C1 | MOL | I | 1 | −75.793 | −49.383 | −34.361 | 1.00 | 32.47 | C |
| ATOM | 2962 | C5 | MOL | I | 1 | −77.282 | −49.343 | −34.659 | 1.00 | 32.69 | C |
| ATOM | 2963 | C8 | MOL | I | 1 | −77.459 | −49.145 | −36.182 | 1.00 | 24.85 | C |
| ATOM | 2964 | C11 | MOL | I | 1 | −76.729 | −47.885 | −36.648 | 1.00 | 32.62 | C |
| ATOM | 2965 | O4 | MOL | I | 1 | −77.127 | −47.254 | −37.626 | 1.00 | 31.31 | O |
| ATOM | 2966 | N2 | MOL | I | 1 | −75.611 | −47.417 | −35.947 | 1.00 | 35.82 | N |
| ATOM | 2967 | C4 | MOL | I | 1 | −75.124 | −48.101 | −34.830 | 1.00 | 36.64 | C |
| ATOM | 2968 | O3 | MOL | I | 1 | −74.144 | −47.667 | −34.226 | 1.00 | 37.07 | O |
| ATOM | 2969 | O2 | MOL | J | 1 | −51.166 | −33.977 | −1.714 | 1.00 | 26.79 | O |
| ATOM | 2970 | C3 | MOL | J | 1 | −50.182 | −33.313 | −2.043 | 1.00 | 35.16 | C |
| ATOM | 2971 | C7 | MOL | J | 1 | −50.003 | −31.940 | −1.839 | 1.00 | 34.70 | C |
| ATOM | 2972 | C10 | MOL | J | 1 | −50.775 | −30.390 | −1.260 | 1.00 | 47.54 | C |
| ATOM | 2973 | N3 | MOL | J | 1 | −51.973 | −31.201 | −0.748 | 1.00 | 44.74 | N |
| ATOM | 2974 | C13 | MOL | J | 1 | −50.285 | −29.627 | −1.215 | 1.00 | 43.00 | C |
| ATOM | 2975 | C12 | MOL | J | 1 | −49.030 | −29.327 | −1.748 | 1.00 | 46.18 | C |
| ATOM | 2976 | C9 | MOL | J | 1 | −48.259 | −30.334 | −2.326 | 1.00 | 43.91 | C |
| ATOM | 2977 | C6 | MOL | J | 1 | −48.750 | −31.637 | −2.363 | 1.00 | 38.39 | C |
| ATOM | 2978 | C2 | MOL | J | 1 | −48.239 | −32.834 | −2.860 | 1.00 | 38.93 | C |
| ATOM | 2979 | O1 | MOL | J | 1 | −47.149 | −32.962 | −3.403 | 1.00 | 33.84 | O |

TABLE 4-continued

Atomic coordinates for CRBN(TBD):Pomalidomide (Murine protein)

| ATOM | 2980 | N1  | MOL | J | 1  | −49.116 | −33.811 | −2.665  | 1.00 | 33.72 | N |
|------|------|-----|-----|---|----|---------|---------|---------|------|-------|---|
| ATOM | 2981 | C1  | MOL | J | 1  | −48.931 | −35.230 | −3.014  | 1.00 | 30.72 | C |
| ATOM | 2982 | C5  | MOL | J | 1  | −48.985 | −35.480 | −4.524  | 1.00 | 30.17 | C |
| ATOM | 2983 | C8  | MOL | J | 1  | −48.785 | −36.983 | −4.775  | 1.00 | 26.35 | C |
| ATOM | 2894 | C11 | MOL | J | 1  | −47.442 | −37.432 | −4.172  | 1.00 | 25.72 | C |
| ATOM | 2985 | O4  | MOL | J | 1  | −46.806 | −38.375 | −4.643  | 1.00 | 25.05 | O |
| ATOM | 2986 | N2  | MOL | J | 1  | −46.914 | −36.775 | −3.064  | 1.00 | 25.10 | N |
| ATOM | 2987 | C4  | MOL | J | 1  | −47.589 | −35.729 | −2.449  | 1.00 | 32.42 | C |
| ATOM | 2988 | O3  | MOL | J | 1  | −47.067 | −35.184 | −1.474  | 1.00 | 28.67 | O |
| ATOM | 2989 | O   | HOH | L | 1  | −55.998 | −46.780 | −16.632 | 1.00 | 16.83 | O |
| ATOM | 2990 | O   | HOH | L | 2  | −56.662 | −50.434 | −20.736 | 1.00 | 22.13 | O |
| ATOM | 2991 | O   | HOH | L | 3  | −57.457 | −62.815 | −22.052 | 1.00 | 22.58 | O |
| ATOM | 2292 | O   | HOH | L | 4  | −50.618 | −49.881 | −15.145 | 1.00 | 17.57 | O |
| ATOM | 2993 | O   | HOH | L | 5  | −62.861 | −49.113 | −13.580 | 1.00 | 14.78 | O |
| ATOM | 2994 | O   | HOH | L | 6  | −87.525 | −50.331 | −49.601 | 1.00 | 26.21 | O |
| ATOM | 2995 | O   | HOH | L | 7  | −50.314 | −56.170 | −20.940 | 1.00 | 19.17 | O |
| ATOM | 2996 | O   | HOH | L | 8  | −80.691 | −48.641 | −56.456 | 1.00 | 26.94 | O |
| ATOM | 2997 | O   | HOH | L | 9  | −87.823 | −46.397 | −53.706 | 1.00 | 25.56 | O |
| ATOM | 2998 | O   | HOH | L | 10 | −46.766 | −54.212 | −15.948 | 1.00 | 19.85 | O |
| ATOM | 2999 | O   | HOH | L | 11 | −54.689 | −56.062 | −24.289 | 1.00 | 23.71 | O |
| ATOM | 3000 | O   | HOH | L | 12 | −52.966 | −46.978 | −15.788 | 1.00 | 38.48 | O |
| ATOM | 3001 | O   | HOH | L | 13 | −70.006 | −44.488 | −54.878 | 1.00 | 37.18 | O |
| ATOM | 3002 | O   | HOH | L | 14 | −86.569 | −56.779 | −56.779 | 0.33 | 28.69 | O |
| ATOM | 3003 | O   | HOH | L | 15 | −48.350 | −56.993 | −8.676  | 1.00 | 17.51 | O |
| ATOM | 3004 | O   | HOH | L | 16 | −68.984 | −42.767 | −19.765 | 1.00 | 32.38 | O |
| ATOM | 3005 | O   | HOH | L | 17 | −68.766 | −45.836 | −14.618 | 1.00 | 21.41 | O |
| ATOM | 3006 | O   | HOH | L | 18 | −65.146 | −38.900 | −4.467  | 1.00 | 18.16 | O |
| ATOM | 3007 | O   | HOH | L | 19 | −68.794 | −50.045 | −19.943 | 1.00 | 19.10 | O |
| ATOM | 3008 | O   | HOH | L | 20 | −41.638 | −50.487 | −9.646  | 1.00 | 33.30 | O |
| ATOM | 3009 | O   | HOH | L | 21 | −55.593 | −52.942 | −23.585 | 1.00 | 32.75 | O |
| ATOM | 3010 | O   | HOH | L | 22 | −68.516 | −37.192 | −1.213  | 1.00 | 22.05 | O |
| ATOM | 3011 | O   | HOH | L | 23 | −66.402 | −41.857 | −23.656 | 1.00 | 30.19 | O |
| ATOM | 3012 | O   | HOH | L | 24 | −48.949 | −50.259 | −3.117  | 1.00 | 20.76 | O |
| ATOM | 3013 | O   | HOH | L | 25 | −59.009 | −39.873 | 3.409   | 1.00 | 42.32 | O |
| ATOM | 3014 | O   | HOH | L | 26 | −45.918 | −30.169 | −4.736  | 1.00 | 46.91 | O |
| ATOM | 3015 | O   | HOH | L | 27 | −53.478 | −54.143 | −29.145 | 1.00 | 31.57 | O |
| ATOM | 3016 | O   | HOH | L | 28 | −45.909 | −43.969 | −18.007 | 1.00 | 32.99 | O |
| ATOM | 3017 | O   | HOH | L | 29 | −51.066 | −32.431 | −11.268 | 1.00 | 24.78 | O |
| ATOM | 3018 | O   | HOH | L | 30 | −42.216 | −73.166 | −12.977 | 1.00 | 37.86 | O |
| ATOM | 3019 | O   | HOH | L | 31 | −72.079 | −41.347 | −1.326  | 1.00 | 22.25 | O |
| ATOM | 3020 | O   | HOH | L | 32 | −54.117 | −56.765 | −9.916  | 1.00 | 22.66 | O |
| ATOM | 3021 | O   | HOH | L | 33 | −66.620 | −39.520 | −32.360 | 1.00 | 32.68 | O |
| ATOM | 3022 | O   | HOH | L | 34 | −70.408 | −47.023 | −16.690 | 1.00 | 39.78 | O |
| ATOM | 3023 | O   | HOH | L | 35 | −50.740 | −68.469 | −21.748 | 1.00 | 23.44 | O |
| ATOM | 3024 | O   | HOH | L | 36 | −51.584 | −68.740 | −28.925 | 1.00 | 39.50 | O |
| ATOM | 3025 | O   | HOH | L | 38 | −48.263 | −36.102 | −27.104 | 1.00 | 57.58 | O |
| ATOM | 3026 | O   | HOH | L | 39 | −58.423 | −42.724 | 2.518   | 1.00 | 29.07 | O |
| ATOM | 3027 | O   | HOH | L | 40 | −53.892 | −50.012 | −31.849 | 1.00 | 41.54 | O |
| ATOM | 3028 | O   | HOH | L | 41 | −47.670 | −65.760 | −29.776 | 1.00 | 31.59 | O |
| ATOM | 3029 | O   | HOH | L | 42 | −49.846 | −54.290 | −23.795 | 1.00 | 28.15 | O |
| ATOM | 3030 | O   | HOH | L | 43 | −47.985 | −49.554 | −17.319 | 1.00 | 25.72 | O |
| ATOM | 3031 | O   | HOH | L | 44 | −61.111 | −54.780 | −13.858 | 1.00 | 24.25 | O |
| ATOM | 3032 | O   | HOH | L | 45 | −48.006 | −38.612 | −13.475 | 1.00 | 27.50 | O |
| ATOM | 3033 | O   | HOH | L | 46 | −56.939 | −67.279 | −18.170 | 1.00 | 26.47 | O |
| ATOM | 3034 | O   | HOH | L | 47 | −54.216 | −65.125 | −3.060  | 1.00 | 44.65 | O |
| ATOM | 3035 | O   | HOH | L | 48 | −41.288 | −46.688 | −5.936  | 1.00 | 29.34 | O |
| ATOM | 3036 | O   | HOH | L | 49 | −54.648 | −41.941 | −18.547 | 1.00 | 34.86 | O |
| ATOM | 3037 | O   | HOH | L | 51 | −54.304 | −45.291 | −26.731 | 1.00 | 32.28 | O |
| ATOM | 3038 | O   | HOH | L | 52 | −31.964 | −45.046 | −12.913 | 1.00 | 50.59 | O |
| ATOM | 3039 | O   | HOH | L | 53 | −39.705 | −51.924 | −10.982 | 1.00 | 29.79 | O |
| ATOM | 3040 | O   | HOH | L | 54 | −51.979 | −56.736 | −3.857  | 1.00 | 27.27 | O |
| ATOM | 3041 | O   | HOH | L | 55 | −73.920 | −44.260 | −45.398 | 1.00 | 48.40 | O |
| ATOM | 3042 | O   | HOH | L | 56 | −73.014 | −46.304 | −14.894 | 1.00 | 49.60 | O |
| ATOM | 3043 | O   | HOH | L | 57 | −40.895 | −63.873 | −32.083 | 1.00 | 26.43 | O |
| ATOM | 3044 | O   | HOH | L | 58 | −79.228 | −56.277 | −35.237 | 1.00 | 32.93 | O |
| ATOM | 3045 | O   | HOH | L | 59 | −58.554 | −47.824 | −31.954 | 1.00 | 23.44 | O |
| ATOM | 3046 | O   | HOH | L | 61 | −48.750 | −55.157 | −37.860 | 1.00 | 44.89 | O |
| ATOM | 3047 | O   | HOH | L | 62 | −66.361 | −56.331 | −34.426 | 1.00 | 31.05 | O |
| ATOM | 3048 | O   | HOH | L | 63 | −41.194 | −31.862 | −11.284 | 1.00 | 43.11 | O |
| ATOM | 3049 | O   | HOH | L | 64 | −39.461 | −57.916 | −24.583 | 1.00 | 29.48 | O |
| ATOM | 3050 | O   | HOH | L | 65 | −73.595 | −37.914 | −3.101  | 1.00 | 32.42 | O |
| ATOM | 3051 | O   | HOH | L | 66 | −67.508 | −62.007 | −37.869 | 1.00 | 37.16 | O |
| ATOM | 3052 | O   | HOH | L | 67 | −57.878 | −57.181 | −5.043  | 1.00 | 26.23 | O |
| ATOM | 3053 | O   | HOH | L | 68 | −72.613 | −47.621 | −11.983 | 1.00 | 48.77 | O |
| ATOM | 3054 | O   | HOH | L | 69 | −30.921 | −56.088 | −6.315  | 1.00 | 41.67 | O |
| ATOM | 3055 | O   | HOH | L | 70 | −54.655 | −52.405 | −1.180  | 1.00 | 36.06 | O |
| ATOM | 3056 | O   | HOH | L | 71 | −58.796 | −48.586 | −41.581 | 1.00 | 44.72 | O |
| ATOM | 3057 | O   | HOH | L | 72 | −65.399 | −67.585 | −16.007 | 1.00 | 49.35 | O |

TABLE 4-continued

Atomic coordinates for CRBN(TBD):Pomalidomide (Murine protein)

| ATOM | 3058 | O | HOH | L | 74 | −41.681 | −50.450 | −3.778 | 1.00 | 40.39 | O |
|---|---|---|---|---|---|---|---|---|---|---|---|
| ATOM | 3059 | O | HOH | L | 75 | −82.168 | −54.170 | −56.506 | 1.00 | 35.36 | O |
| ATOM | 3060 | O | HOH | L | 76 | −71.740 | −53.589 | −35.005 | 1.00 | 41.35 | O |
| ATOM | 3061 | O | HOH | L | 77 | −73.389 | −60.629 | −20.406 | 1.00 | 65.00 | O |
| ATOM | 3062 | O | HOH | L | 78 | −47.960 | −43.267 | −18.897 | 1.00 | 37.35 | O |
| ATOM | 3063 | O | HOH | L | 79 | −39.379 | −66.297 | −32.756 | 1.00 | 30.34 | O |
| ATOM | 3064 | O | HOH | L | 80 | −78.068 | −55.318 | −33.205 | 1.00 | 40.39 | O |
| ATOM | 3065 | O | HOH | L | 81 | −57.063 | −57.327 | −13.895 | 1.00 | 21.99 | O |
| ATOM | 3066 | O | HOH | L | 82 | −55.365 | −55.336 | −15.755 | 1.00 | 20.36 | O |
| ATOM | 3067 | O | HOH | L | 83 | −67.023 | −65.067 | −31.961 | 1.00 | 33.22 | O |
| ATOM | 3068 | O | HOH | L | 85 | −35.520 | −64.612 | −16.134 | 1.00 | 34.96 | O |
| ATOM | 3069 | O | HOH | L | 86 | −68.461 | −57.366 | −33.035 | 1.00 | 35.10 | O |
| ATOM | 3070 | O | HOH | L | 87 | −73.400 | −55.363 | −38.890 | 1.00 | 44.25 | O |
| ATOM | 3071 | O | HOH | L | 88 | −66.947 | −52.024 | −37.561 | 1.00 | 38.14 | O |
| ATOM | 3072 | O | HOH | L | 90 | −61.619 | −40.178 | −18.597 | 1.00 | 29.35 | O |
| ATOM | 3073 | O | HOH | L | 91 | −51.419 | −62.600 | −29.502 | 1.00 | 33.22 | O |
| ATOM | 3074 | O | HOH | L | 92 | −37.856 | −39.688 | −10.228 | 1.00 | 40.42 | O |
| ATOM | 3075 | O | HOH | L | 93 | −86.112 | −47.545 | −37.999 | 1.00 | 29.15 | O |
| ATOM | 3076 | O | HOH | L | 94 | −62.880 | −41.964 | −20.114 | 1.00 | 33.78 | O |
| ATOM | 3077 | O | HOH | L | 95 | −65.313 | −40.867 | −21.154 | 1.00 | 35.39 | O |
| ATOM | 3078 | O | HOH | L | 96 | −69.416 | −54.581 | −8.419 | 1.00 | 32.62 | O |
| ATOM | 3079 | O | HOH | L | 97 | −75.300 | −59.197 | −30.841 | 1.00 | 54.15 | O |
| ATOM | 3080 | O | HOH | L | 98 | −65.831 | −58.654 | −13.239 | 1.00 | 31.44 | O |
| ATOM | 3081 | O | HOH | L | 100 | −70.424 | −33.186 | −15.560 | 1.00 | 33.39 | O |
| ATOM | 3082 | O | HOH | L | 101 | −44.643 | −55.547 | −3.013 | 1.00 | 28.01 | O |
| ATOM | 3083 | O | HOH | L | 102 | −46.432 | −53.101 | −37.062 | 1.00 | 42.42 | O |
| ATOM | 3084 | O | HOH | L | 103 | −70.364 | −54.480 | −10.693 | 1.00 | 39.13 | O |
| ATOM | 3085 | O | HOH | L | 104 | −31.478 | −67.848 | −26.883 | 1.00 | 48.60 | O |
| ATOM | 3086 | O | HOH | L | 105 | −40.414 | −70.438 | −17.098 | 1.00 | 35.54 | O |
| ATOM | 3087 | O | HOH | L | 107 | −63.118 | −62.722 | −12.135 | 1.00 | 40.48 | O |
| ATOM | 3088 | O | HOH | L | 108 | −50.731 | −39.550 | −18.176 | 1.00 | 50.25 | O |
| ATOM | 3089 | O | HOH | L | 109 | −37.743 | −65.752 | −7.100 | 1.00 | 26.28 | O |
| ATOM | 3090 | O | HOH | L | 111 | −54.285 | −72.272 | −28.250 | 1.00 | 47.18 | O |
| ATOM | 3091 | O | HOH | L | 112 | −39.326 | −74.029 | −13.072 | 1.00 | 47.17 | O |
| ATOM | 3092 | O | HOH | L | 113 | −54.743 | −40.472 | −0.259 | 1.00 | 30.05 | O |
| ATOM | 3093 | O | HOH | L | 114 | −86.348 | −75.737 | −43.976 | 1.00 | 54.17 | O |
| ATOM | 3094 | O | HOH | L | 115 | −67.070 | −48.290 | 0.624 | 1.00 | 52.78 | O |
| ATOM | 3095 | O | HOH | L | 116 | −41.314 | −62.221 | −34.289 | 1.00 | 42.38 | O |
| ATOM | 3096 | O | HOH | L | 117 | −47.339 | −69.859 | −27.729 | 1.00 | 50.42 | O |
| ATOM | 3097 | O | HOH | L | 118 | −55.943 | −64.679 | −1.086 | 1.00 | 51.95 | O |
| ATOM | 3098 | O | HOH | L | 119 | −36.936 | −68.180 | −6.143 | 1.00 | 26.78 | O |
| ATOM | 3099 | O | HOH | L | 120 | −39.365 | −60.321 | −35.436 | 1.00 | 47.69 | O |
| ATOM | 3100 | O | HOH | L | 121 | −56.768 | −62.719 | 0.272 | 1.00 | 38.13 | O |
| ATOM | 3101 | O | HOH | L | 122 | −51.787 | −33.032 | −5.129 | 1.00 | 36.07 | O |
| ATOM | 3102 | O | HOH | L | 123 | −56.231 | −35.993 | −5.765 | 1.00 | 30.83 | O |
| ATOM | 3103 | O | HOH | L | 124 | −40.242 | −68.209 | −0.005 | 1.00 | 30.45 | O |
| ATOM | 3104 | O | HOH | L | 125 | −57.016 | −37.559 | −3.217 | 1.00 | 27.01 | O |
| ATOM | 3105 | O | HOH | L | 126 | −56.879 | −61.381 | −16.376 | 1.00 | 24.94 | O |
| ATOM | 3106 | O | HOH | L | 127 | −56.342 | −35.508 | −1.199 | 1.00 | 43.91 | O |
| ATOM | 3107 | O | HOH | L | 128 | −68.368 | −53.928 | −18.982 | 1.00 | 31.58 | O |
| ATOM | 3108 | O | HOH | L | 129 | −62.786 | −47.406 | −0.550 | 1.00 | 28.32 | O |
| ATOM | 3109 | O | HOH | L | 130 | −69.999 | −55.296 | −17.499 | 1.00 | 38.41 | O |
| ATOM | 3110 | O | HOH | L | 131 | −75.671 | −53.931 | −50.478 | 1.00 | 37.36 | O |
| ATOM | 3111 | O | HOH | L | 132 | −46.115 | −56.050 | −0.755 | 1.00 | 42.66 | O |
| ATOM | 3112 | O | HOH | L | 133 | −50.828 | −68.384 | −17.490 | 1.00 | 39.60 | O |
| ATOM | 3113 | O | HOH | L | 134 | −74.987 | −45.384 | −54.535 | 1.00 | 29.72 | O |
| ATOM | 3114 | O | HOH | L | 135 | −64.661 | −45.243 | 1.729 | 1.00 | 39.44 | O |
| ATOM | 3115 | O | HOH | L | 136 | −81.295 | −41.740 | −49.705 | 1.00 | 30.27 | O |
| ATOM | 3116 | O | HOH | L | 137 | −55.673 | −58.104 | −7.014 | 1.00 | 32.53 | O |
| ATOM | 3117 | O | HOH | L | 138 | −63.905 | −56.458 | −12.710 | 1.00 | 30.10 | O |
| ATOM | 3118 | O | HOH | L | 139 | −31.190 | −57.977 | −28.665 | 1.00 | 43.45 | O |
| ATOM | 3119 | O | HOH | L | 140 | −39.876 | −39.749 | −8.199 | 1.00 | 27.49 | O |
| ATOM | 3120 | O | HOH | L | 141 | −56.589 | −68.929 | −25.262 | 1.00 | 37.89 | O |
| ATOM | 3121 | O | HOH | L | 142 | −42.270 | −52.387 | −17.773 | 1.00 | 32.52 | O |
| ATOM | 3122 | O | HOH | L | 143 | −69.361 | −40.450 | −31.496 | 1.00 | 32.62 | O |
| ATOM | 3123 | O | HOH | L | 144 | −52.911 | −62.032 | −1.169 | 1.00 | 39.62 | O |
| ATOM | 3124 | O | HOH | L | 145 | −64.485 | −40.022 | −30.570 | 1.00 | 30.56 | O |
| ATOM | 3125 | O | HOH | L | 146 | −40.173 | −55.926 | −0.786 | 1.00 | 29.73 | O |
| ATOM | 3126 | O | HOH | L | 147 | −91.725 | −39.677 | −50.031 | 1.00 | 42.43 | O |
| ATOM | 3127 | O | HOH | L | 148 | −83.022 | −40.758 | −31.882 | 1.00 | 39.88 | O |
| ATOM | 3128 | O | HOH | L | 149 | −29.384 | −71.387 | −29.309 | 1.00 | 46.26 | O |
| ATOM | 3129 | O | HOH | L | 150 | −33.094 | −65.936 | −20.202 | 1.00 | 45.04 | O |
| ATOM | 3130 | O | HOH | L | 151 | −70.060 | −72.294 | −29.785 | 1.00 | 32.81 | O |
| ATOM | 3131 | O | HOH | L | 152 | −49.652 | −36.909 | −16.537 | 1.00 | 42.75 | O |
| ATOM | 3132 | O | HOH | L | 153 | −37.015 | −67.403 | −14.818 | 1.00 | 32.50 | O |
| ATOM | 3133 | O | HOH | L | 154 | −32.607 | −52.859 | −14.840 | 1.00 | 38.65 | O |
| ATOM | 3134 | O | HOH | L | 155 | −74.055 | −63.198 | −46.721 | 1.00 | 46.56 | O |
| ATOM | 3135 | O | HOH | L | 156 | −70.883 | −58.870 | −41.837 | 1.00 | 48.30 | O |

TABLE 4-continued

Atomic coordinates for CRBN(TBD):Pomalidomide (Murine protein)

| ATOM | 3136 | O | HOH | L | 157 | −48.307 | −32.834 | −11.109 | 1.00 | 31.32 | O |
|---|---|---|---|---|---|---|---|---|---|---|---|
| ATOM | 3137 | O | HOH | L | 158 | −46.437 | −69.854 | −8.165 | 1.00 | 38.79 | O |
| ATOM | 3138 | O | HOH | L | 159 | −32.484 | −66.271 | −10.245 | 1.00 | 30.51 | O |
| ATOM | 3139 | O | HOH | L | 160 | −73.974 | −58.768 | −27.568 | 1.00 | 43.88 | O |
| ATOM | 3140 | O | HOH | L | 161 | −75.864 | −60.065 | −25.979 | 1.00 | 47.84 | O |
| ATOM | 3141 | O | HOH | L | 162 | −67.335 | −53.177 | −13.731 | 1.00 | 32.22 | O |
| ATOM | 3142 | O | HOH | L | 163 | −62.473 | −38.200 | −30.448 | 1.00 | 35.09 | O |
| ATOM | 3143 | O | HOH | L | 164 | −65.673 | −32.093 | −14.729 | 1.00 | 41.89 | O |
| ATOM | 3144 | O | HOH | L | 165 | −62.402 | −32.999 | −4.269 | 1.00 | 26.95 | O |
| ATOM | 3145 | O | HOH | L | 166 | −73.108 | −38.320 | −0.555 | 1.00 | 29.99 | O |
| ATOM | 3146 | O | HOH | L | 167 | −65.889 | −37.667 | −2.033 | 1.00 | 30.57 | O |
| ATOM | 3147 | O | HOH | L | 168 | −67.916 | −32.091 | −2.460 | 1.00 | 39.98 | O |
| ATOM | 3148 | O | HOH | L | 169 | −69.724 | −33.316 | −0.530 | 1.00 | 38.04 | O |
| ATOM | 3149 | O | HOH | L | 170 | −55.430 | −49.098 | −33.848 | 1.00 | 44.42 | O |
| ATOM | 3150 | O | HOH | L | 171 | −61.069 | −51.087 | −38.110 | 1.00 | 36.65 | O |
| ATOM | 3151 | O | HOH | L | 172 | −75.354 | −49.720 | −49.526 | 1.00 | 33.61 | O |
| ATOM | 3152 | O | HOH | L | 173 | −78.168 | −52.308 | −31.917 | 1.00 | 47.08 | O |
| ATOM | 3153 | O | HOH | L | 174 | −67.475 | −55.441 | −36.645 | 1.00 | 40.30 | O |
| ATOM | 3154 | O | HOH | L | 175 | −62.020 | −42.247 | −40.422 | 1.00 | 42.03 | O |
| ATOM | 3155 | O | HOH | L | 176 | −52.158 | −62.111 | −33.880 | 1.00 | 34.20 | O |
| ATOM | 3156 | O | HOH | L | 177 | −78.108 | −65.351 | −37.979 | 1.00 | 31.57 | O |
| ATOM | 3157 | O | HOH | L | 178 | −87.311 | −66.886 | −52.634 | 1.00 | 36.20 | O |

TABLE 5

Atomic coordinates for CRBN(TBD):Thalidomide (Murine protein)

```
HEADER      ----                                                             XX-XXX-9-    xxxx
COMPND      ---
REMARK      3
REMARK      3     REFINEMENT.
REMARK      3       PROGRAM     :   REFMAC 5.6.0117
REMARK      3       AUTHORS     :
REMARK      3
REMARK      3        REFINEMENT TARGET : MAXIMUM LIKELIHOOD
REMARK      3
REMARK      3     DATA USED IN REFINEMENT.
REMARK      3        RESOLUTION RANGE HIGH (ANGSTROMS)  :       1.88
REMARK      3        RESOLUTION RANGE LOW  (ANGSTROMS)  :      50.00
REMARK      3        DATA CUTOFF            (SIGMA(F))  :       NONE
REMARK      3        COMPLETENESS FOR RANGE        (%)  :      99.94
REMARK      3        NUMBER OF REFLECTIONS              :      37584
REMARK      3
REMARK      3     FIT TO DATA USED IN REFINEMENT.
REMARK      3        CROSS-VALIDATION METHOD            :   THROUGHOUT
REMARK      3        FREE R VALUE TEST SET SELECTION    :   RANDOM
REMARK      3        R VALUE     (WORKING + TEST SET)   :     0.18197
REMARK      3        R VALUE            (WORKING SET)   :     0.17955
REMARK      3        FREE R VALUE                       :     0.22867
REMARK      3        FREE R VALUE TEST SET SIZE    (%)  :        5.0
REMARK      3        FREE R VALUE TEST SET COUNT        :       1983
REMARK      3
REMARK      3     FIT IN THE HIGHEST RESOLUTION BIN.
REMARK      3        TOTAL NUMBER OF BINS USED              :         20
REMARK      3        BIN RESOLUTION RANGE HIGH              :      1.882
REMARK      3        BIN RESOLUTION RANGE LOW               :      1.931
REMARK      3        REFLECTION IN BIN     (WORKING SET)    :       2673
REMARK      3        BIN COMPLETENESS (WORKING+TEST) (%)    :      99.96
REMARK      3        BIN R VALUE           (WORKING SET)    :      0.272
REMARK      3        BIN FREE R VALUE SET COUNT             :        137
REMARK      3        BIN FREE R VALUE                       :      0.368
REMARK      3
REMARK      3     NUMBER OF NON-HYDROGEN ATOMS USED IN REFINEMENT.
REMARK      3        ALL ATOMS            :          3576
REMARK      3
REMARK      3     B VALUES.
REMARK      3        FROM WILSON PLOT            (A**2) : NULL
REMARK      3        MEAN B VALUE        (OVERALL, A**2) : 29.871
REMARK      3        OVERALL ANISOTROPIC B VALUE.
REMARK      3         B11 (A**2) : NULL
REMARK      3         B22 (A**2) : NULL
REMARK      3         B33 (A**2) : NULL
REMARK      3         B12 (A**2) : NULL
REMARK      3         B13 (A**2) : NULL
REMARK      3         B23 (A**2) : NULL
```

TABLE 5-continued

Atomic coordinates for CRBN(TBD):Thalidomide (Murine protein)

| | | | | | | | |
|---|---|---|---|---|---|---|---|
| REMARK | 3 | | | | | | |
| REMARK | 3 | ESTIMATED OVERALL COORDINATE ERROR. | | | | | |
| REMARK | 3 | ESU BASED ON R VALUE | | (A): | 0.135 | | |
| REMARK | 3 | ESU BASED ON FREE R VALUE | | (A): | 0.135 | | |
| REMARK | 3 | ESU BASED ON MAXIMUM LIKELIHOOD | | (A): | 0.091 | | |
| REMARK | 3 | ESU FOR B VALUES BASED ON MAXIMUM LIKELIHOOD | | (A**2): | 3.062 | | |
| REMARK | 3 | | | | | | |
| REMARK | 3 | CORRELATION COEFFICIENTS. | | | | | |
| REMARK | 3 | CORRELATION COEFFICIENT FO-FC | | : | 0.963 | | |
| REMARK | 3 | CORRELATION COEFFICIENT FO-FC FREE | | : | 0.940 | | |
| REMARK | 3 | | | | | | |
| REMARK | 3 | RMS DEVIATIONS FROM IDEAL VALUES | | | COUNT | RMS | WEIGHT |
| REMARK | 3 | BOND LENGTHS REFINED ATOMS | | (A): | 3289 | ; 0.014 | ; 0.020 |
| REMARK | 3 | BOND ANGLES REFINED ATOMS | | (DEGREES): | 4483 | ; 1.676 | ; 1.974 |
| REMARK | 3 | TORSION ANGLES, PERIOD 1 | | (DEGREES): | 389 | ; 17.405 | ; 5.000 |
| REMARK | 3 | TORSION ANGLES, PERIOD 2 | | (DEGREES): | 112 | ; 39.373 | ; 23.661 |
| REMARK | 3 | TORSION ANGLES, PERIOD 3 | | (DEGREES): | 544 | ; 15.190 | ; 15.000 |
| REMARK | 3 | TORSION ANGLES, PERIOD 4 | | (DEGREES): | 8 | ; 19.411 | ; 15.000 |
| REMARK | 3 | CHIRAL-CENTER RESTRAINTS | | (A**3): | 504 | ; 0.097 | ; 0.200 |
| REMARK | 3 | GENERAL PLANES REFINED ATOMS | | (A): | 2372 | ; 0.018 | ; 0.021 |
| REMARK | 3 | | | | | | |
| REMARK | 3 | ISOTROPIC THERMAL FACTOR RESTRAINTS. | | | COUNT | RMS | WEIGHT |
| REMARK | 3 | | | | | | |
| REMARK | 3 | NCS RESTRAINTS STATISTICS | | | | | |
| REMARK | 3 | NUMBER OF NCS GROUPS : NULL | | | | | |
| REMARK | 3 | | | | | | |
| REMARK | 3 | TWIN DETAILS | | | | | |
| REMARK | 3 | NUMBER OF TWIN DOMAINS : NULL | | | | | |
| REMARK | 3 | | | | | | |
| REMARK | 3 | | | | | | |
| REMARK | 3 | TLS DETAILS | | | | | |
| REMARK | 3 | NUMBER OF TLS GROUPS : 4 | | | | | |
| REMARK | 3 | ATOM RECORD CONTAINS RESIDUAL B FACTORS ONLY | | | | | |
| REMARK | 3 | | | | | | |
| REMARK | 3 | TLS GROUP : 1 | | | | | |
| REMARK | 3 | NUMBER OF COMPONENTS GROUP : 1 | | | | | |
| REMARK | 3 | COMPONENTS C SSSEQI TO C SSSEQI | | | | | |
| REMARK | 3 | RESIDUE RANGE : A 1 A 112 | | | | | |
| REMARK | 3 | ORIGIN FOR THE GROUP (A): 0.0000 0.0000 0.0000 | | | | | |
| REMARK | 3 | T TENSOR | | | | | |
| REMARK | 3 | T11: 0.0000 T22: 0.0000 | | | | | |
| REMARK | 3 | T33: 0.0000 T12: 0.0000 | | | | | |
| REMARK | 3 | T13: 0.0000 T23: 0.0000 | | | | | |
| REMARK | 3 | L TENSOR | | | | | |
| REMARK | 3 | L11: 0.0000 L22: 0.0000 | | | | | |
| REMARK | 3 | L33: 0.0000 L12: 0.0000 | | | | | |
| REMARK | 3 | L13: 0.0000 L23: 0.0000 | | | | | |
| REMARK | 3 | S TENSOR | | | | | |
| REMARK | 3 | S11: 0.0000 S12: 0.0000 S13: 0.0000 | | | | | |
| REMARK | 3 | S21: 0.0000 S22: 0.0000 S23: 0.0000 | | | | | |
| REMARK | 3 | S31: 0.0000 S32: 0.0000 S33: 0.0000 | | | | | |
| REMARK | 3 | | | | | | |
| REMARK | 3 | TLS GROUP : 2 | | | | | |
| REMARK | 3 | NUMBER OF COMPONENTS GROUP : 1 | | | | | |
| REMARK | 3 | COMPONENTS C SSSEQI TO C SSSEQI | | | | | |
| REMARK | 3 | RESIDUE RANGE : B 1 B 112 | | | | | |
| REMARK | 3 | ORIGIN FOR THE GROUP (A): 0.0000 0.0000 0.0000 | | | | | |
| REMARK | 3 | T TENSOR | | | | | |
| REMARK | 3 | T11: 0.0000 T22: 0.0000 | | | | | |
| REMARK | 3 | T33: 0.0000 T12: 0.0000 | | | | | |
| REMARK | 3 | T13: 0.0000 T23: 0.0000 | | | | | |
| REMARK | 3 | L TENSOR | | | | | |
| REMARK | 3 | L11: 0.0000 L22: 0.0000 | | | | | |
| REMARK | 3 | L33: 0.0000 L12: 0.0000 | | | | | |
| REMARK | 3 | L13: 0.0000 L23: 0.0000 | | | | | |
| REMARK | 3 | S TENSOR | | | | | |
| REMARK | 3 | S11: 0.0000 S12: 0.0000 S13: 0.0000 | | | | | |
| REMARK | 3 | S21: 0.0000 S22: 0.0000 S23: 0.0000 | | | | | |
| REMARK | 3 | S31: 0.0000 S32: 0.0000 S33: 0.0000 | | | | | |
| REMARK | 3 | | | | | | |
| REMARK | 3 | TLS GROUP : 3 | | | | | |
| REMARK | 3 | NUMBER OF COMPONENTS GROUP : 1 | | | | | |
| REMARK | 3 | COMPONENTS C SSSEQI TO C SSSEQI | | | | | |
| REMARK | 3 | RESIDUE RANGE : C 1 C 112 | | | | | |
| REMARK | 3 | ORIGIN FOR THE GROUP (A): 0.0000 0.0000 0.0000 | | | | | |
| REMARK | 3 | T TENSOR | | | | | |
| REMARK | 3 | T11: 0.0000 T22: 0.0000 | | | | | |
| REMARK | 3 | T33: 0.0000 T12: 0.0000 | | | | | |

TABLE 5-continued

Atomic coordinates for CRBN(TBD):Thalidomide (Murine protein)

| | | | | | | | | | | |
|---|---|---|---|---|---|---|---|---|---|---|
| REMARK | 3 | | T13: | 0.0000 | | T23: | 0.0000 | | | |
| REMARK | 3 | | L TENSOR | | | | | | | |
| REMARK | 3 | | L11: | 0.0000 | | L22: | 0.0000 | | | |
| REMARK | 3 | | L33: | 0.0000 | | L12: | 0.0000 | | | |
| REMARK | 3 | | L13: | 0.0000 | | L23: | 0.0000 | | | |
| REMARK | 3 | | S TENSOR | | | | | | | |
| REMARK | 3 | | S11: | 0.0000 | | S12: | 0.0000 | S13: | 0.0000 | |
| REMARK | 3 | | S21: | 0.0000 | | S22: | 0.0000 | S23: | 0.0000 | |
| REMARK | 3 | | S31: | 0.0000 | | S32: | 0.0000 | S33: | 0.0000 | |
| REMARK | 3 | | | | | | | | | |
| REMARK | 3 | | TLS GROUP : 4 | | | | | | | |
| REMARK | 3 | | NUMBER OF COMPONENTS GROUP : 1 | | | | | | | |
| REMARK | 3 | | COMPONENTS | | C | SSSEQI | TO | C | SSSEQI | |
| REMARK | 3 | | RESIDUE RANGE : | | D | 1 | | D | 112 | |
| REMARK | 3 | | ORIGIN FOR THE GROUP (A): | | 0.0000 | 0.0000 | 0.0000 | | | |
| REMARK | 3 | | T TENSOR | | | | | | | |
| REMARK | 3 | | T11: | 0.0000 | | T22: | 0.0000 | | | |
| REMARK | 3 | | T33: | 0.0000 | | T12: | 0.0000 | | | |
| REMARK | 3 | | T13: | 0.0000 | | T23: | 0.0000 | | | |
| REMARK | 3 | | L TENSOR | | | | | | | |
| REMARK | 3 | | L11: | 0.0000 | | L22: | 0.0000 | | | |
| REMARK | 3 | | L33: | 0.0000 | | L12: | 0.0000 | | | |
| REMARK | 3 | | L13: | 0.0000 | | L23: | 0.0000 | | | |
| REMARK | 3 | | S TENSOR | | | | | | | |
| REMARK | 3 | | S11: | 0.0000 | | S12: | 0.0000 | S13: | 0.0000 | |
| REMARK | 3 | | S21: | 0.0000 | | S22: | 0.0000 | S23: | 0.0000 | |
| REMARK | 3 | | S31: | 0.0000 | | S32: | 0.0000 | S33: | 0.0000 | |
| REMARK | 3 | | | | | | | | | |
| REMARK | 3 | | BULK SOLVENT MODELLING. | | | | | | | |
| REMARK | 3 | | METHOD USED : MASK | | | | | | | |
| REMARK | 3 | | PARAMETERS FOR MASK CALCULATION | | | | | | | |
| REMARK | 3 | | VDW PROBE RADIUS | | | : 1.20 | | | | |
| REMARK | 3 | | ION PROBE RADIUS | | | : 0.80 | | | | |
| REMARK | 3 | | SHRINKAGE RADIUS | | | : 0.80 | | | | |
| REMARK | 3 | | | | | | | | | |
| REMARK | 3 | | OTHER REFINEMENT REMARKS: | | | | | | | |
| REMARK | 3 | | HYDROGENS HAVE BEEN USED IF PRESENT IN THE INPUT | | | | | | | |
| REMARK | 3 | | U VALUES : REFINED INDIVIDUALLY | | | | | | | |
| REMARK | 3 | | | | | | | | | |
| LINKR | | | SER | C | 341 | | VAL | C | 356 | gap |
| LINKR | | | LEU | A | 342 | | GLU | A | 358 | gap |
| LINKR | | | MET | B | 346 | | GLY | B | 354 | gap |
| LINKR | | | MET | B | 346 | | VAL | B | 356 | gap |
| CRYST1 | | 143.146 | 143.146 | 143.146 | 90.00 | 90.00 | 90.00 I 2 3 | | | |
| SCALE1 | | 0.006986 | 0.000000 | 0.000000 | 0.00000 | | | | | |
| SCALE2 | | 0.000000 | 0.006986 | 0.000000 | 0.00000 | | | | | |
| SCALE3 | | 0.000000 | 0.000000 | 0.006986 | 0.00000 | | | | | |
| ATOM | 1 | N | SER | C | 320 | 17.597 | −9.098 | −70.900 | 1.00 | 54.44 N |
| ATOM | 2 | CA | SER | C | 320 | 17.270 | −7.667 | −70.570 | 1.00 | 61.42 C |
| ATOM | 3 | CB | SER | C | 320 | 15.980 | −7.215 | −71.268 | 1.00 | 54.67 C |
| ATOM | 4 | OG | SER | C | 320 | 14.906 | −8.081 | −70.964 | 1.00 | 67.19 O |
| ATOM | 5 | C | SER | C | 320 | 17.182 | −7.407 | −69.061 | 1.00 | 46.80 C |
| ATOM | 6 | O | SER | C | 320 | 17.150 | −6.249 | −68.624 | 1.00 | 51.56 O |
| ATOM | 7 | N | THR | C | 321 | 17.132 | −8.479 | −68.270 | 1.00 | 48.55 N |
| ATOM | 8 | CA | THR | C | 321 | 17.339 | −8.355 | −66.824 | 1.00 | 38.24 C |
| ATOM | 9 | CB | THR | C | 321 | 16.324 | −9.180 | −66.022 | 1.00 | 44.93 C |
| ATOM | 10 | OG1 | THR | C | 321 | 16.562 | −10.576 | −66.240 | 1.00 | 37.55 O |
| ATOM | 11 | CG2 | THR | C | 321 | 14.887 | −8.822 | −66.433 | 1.00 | 51.06 C |
| ATOM | 12 | C | THR | C | 321 | 18.766 | −8.777 | −66.447 | 1.00 | 31.37 C |
| ATOM | 13 | O | THR | C | 321 | 19.137 | −8.744 | −65.271 | 1.00 | 27.93 O |
| ATOM | 14 | N | SER | C | 322 | 19.568 | −9.143 | −67.451 | 1.00 | 24.52 N |
| ATOM | 15 | CA | SER | C | 322 | 20.959 | −9.608 | −67.210 | 1.00 | 24.43 C |
| ATOM | 16 | CB | SER | C | 322 | 21.514 | −10.301 | −68.451 | 1.00 | 31.13 C |
| ATOM | 17 | OG | SER | C | 322 | 21.087 | −11.642 | −68.509 | 1.00 | 43.36 O |
| ATOM | 18 | C | SER | C | 322 | 21.900 | −8.475 | −66.799 | 1.00 | 27.14 C |
| ATOM | 19 | O | SER | C | 322 | 21.917 | −7.418 | −67.421 | 1.00 | 25.75 O |
| ATOM | 20 | N | LEU | C | 323 | 22.672 | −8.691 | −65.736 | 1.00 | 20.00 N |
| ATOM | 21 | CA | LEU | C | 323 | 23.754 | −7.764 | −65.388 | 1.00 | 17.36 C |
| ATOM | 22 | CB | LEU | C | 323 | 23.652 | −7.351 | −63.909 | 1.00 | 21.16 C |
| ATOM | 23 | CG | LEU | C | 323 | 22.389 | −6.507 | −63.611 | 1.00 | 24.94 C |
| ATOM | 24 | CD1 | LEU | C | 323 | 22.153 | −6.341 | −62.123 | 1.00 | 28.25 C |
| ATOM | 25 | CD2 | LEU | C | 323 | 22.527 | −5.149 | −64.258 | 1.00 | 31.31 C |
| ATOM | 26 | C | LEU | C | 323 | 25.045 | −8.490 | −65.626 | 1.00 | 18.00 C |
| ATOM | 27 | O | LEU | C | 323 | 25.357 | −9.433 | −64.909 | 1.00 | 17.30 O |
| ATOM | 28 | N | CYS | C | 324 | 25.792 | −8.081 | −66.650 | 1.00 | 19.62 N |
| ATOM | 29 | CA | CYS | C | 324 | 27.017 | −8.804 | −67.029 | 1.00 | 20.33 C |
| ATOM | 30 | CB | CYS | C | 324 | 27.055 | −9.000 | −68.563 | 1.00 | 23.96 C |

TABLE 5-continued

Atomic coordinates for CRBN(TBD):Thalidomide (Murine protein)

| ATOM | 31 | SG | CYS | C | 324 | 25.715 | −10.038 | −69.191 | 1.00 | 28.05 | S |
| ATOM | 32 | C | CYS | C | 324 | 28.301 | −8.100 | −66.561 | 1.00 | 18.86 | C |
| ATOM | 33 | O | CYS | C | 324 | 28.301 | −6.917 | −66.268 | 1.00 | 20.71 | O |
| ATOM | 34 | N | CYS | C | 325 | 29.398 | −8.860 | −66.504 | 1.00 | 18.63 | N |
| ATOM | 35 | CA | CYS | C | 325 | 30.723 | −8.304 | −66.242 | 1.00 | 18.73 | C |
| ATOM | 36 | CB | CYS | C | 325 | 31.774 | −9.415 | −66.340 | 1.00 | 17.56 | C |
| ATOM | 37 | SG | CYS | C | 325 | 33.479 | −8.819 | −66.186 | 1.00 | 18.80 | S |
| ATOM | 38 | C | CYS | C | 325 | 31.004 | −7.219 | −67.280 | 1.00 | 19.89 | C |
| ATOM | 39 | O | CYS | C | 325 | 30.831 | −7.432 | −68.486 | 1.00 | 19.77 | O |
| ATOM | 40 | N | LYS | C | 326 | 31.399 | −6.047 | −66.828 | 1.00 | 18.98 | N |
| ATOM | 41 | CA | LYS | C | 326 | 31.578 | −4.935 | −67.749 | 1.00 | 22.19 | C |
| ATOM | 42 | CB | LYS | C | 326 | 31.645 | −3.624 | −66.986 | 1.00 | 21.31 | C |
| ATOM | 43 | CG | LYS | C | 326 | 32.193 | −2.468 | −67.810 | 1.00 | 33.23 | C |
| ATOM | 44 | CD | LYS | C | 326 | 31.073 | −1.555 | −68.226 | 1.00 | 40.67 | C |
| ATOM | 45 | CE | LYS | C | 326 | 30.631 | −0.711 | −67.062 | 1.00 | 35.42 | C |
| ATOM | 46 | NZ | LYS | C | 326 | 31.773 | 0.079 | −66.530 | 1.00 | 55.41 | N |
| ATOM | 47 | C | LYS | C | 326 | 32.862 | −5.112 | −68.594 | 1.00 | 20.48 | C |
| ATOM | 48 | O | LYS | C | 326 | 32.924 | −4.704 | −69.777 | 1.00 | 22.64 | O |
| ATOM | 49 | N | GLN | C | 327 | 33.847 | −5.728 | −67.996 | 1.00 | 18.81 | N |
| ATOM | 50 | CA | GLN | C | 327 | 35.125 | −5.942 | −68.643 | 1.00 | 18.22 | C |
| ATOM | 51 | CB | GLN | C | 327 | 36.186 | −6.383 | −67.628 | 1.00 | 19.20 | C |
| ATOM | 52 | CG | GLN | C | 327 | 37.539 | −6.701 | −68.266 | 1.00 | 22.08 | C |
| ATOM | 53 | CD | GLN | C | 327 | 38.656 | −6.854 | −67.265 | 1.00 | 23.05 | C |
| ATOM | 54 | OE1 | GLN | C | 327 | 39.629 | −7.564 | −67.511 | 1.00 | 26.41 | O |
| ATOM | 55 | NE2 | GLN | C | 327 | 38.525 | −6.208 | −66.140 | 1.00 | 19.54 | N |
| ATOM | 56 | C | GLN | C | 327 | 34.991 | −6.956 | −69.792 | 1.00 | 19.41 | C |
| ATOM | 57 | O | GLN | C | 327 | 35.380 | −6.656 | −70.911 | 1.00 | 19.39 | O |
| ATOM | 58 | N | CYS | C | 328 | 34.452 | −8.154 | −69.511 | 1.00 | 18.40 | N |
| ATOM | 59 | CA | CYS | C | 328 | 34.422 | −9.186 | −70.546 | 1.00 | 19.45 | C |
| ATOM | 60 | CB | CYS | C | 328 | 34.836 | −10.566 | −70.005 | 1.00 | 20.93 | C |
| ATOM | 61 | SG | CYS | C | 328 | 33.592 | −11.299 | −68.890 | 1.00 | 21.47 | S |
| ATOM | 62 | C | CYS | C | 328 | 33.102 | −9.223 | −71.267 | 1.00 | 18.26 | C |
| ATOM | 63 | O | CYS | C | 328 | 32.943 | −9.979 | −72.236 | 1.00 | 20.79 | O |
| ATOM | 64 | N | GLN | C | 329 | 32.143 | −8.388 | −70.815 | 1.00 | 19.25 | N |
| ATOM | 65 | CA | GLN | C | 329 | 30.858 | −8.167 | −71.519 | 1.00 | 23.13 | C |
| ATOM | 66 | CB | GLN | C | 329 | 31.082 | −7.600 | −72.927 | 1.00 | 23.28 | C |
| ATOM | 67 | CG | GLN | C | 329 | 32.155 | −6.509 | −72.959 | 1.00 | 25.65 | C |
| ATOM | 68 | CD | GLN | C | 329 | 32.065 | −5.642 | −74.179 | 1.00 | 30.51 | C |
| ATOM | 69 | OE1 | GLN | C | 329 | 31.866 | −4.445 | −74.069 | 1.00 | 28.81 | O |
| ATOM | 70 | NE2 | GLN | C | 329 | 32.215 | −6.245 | −75.366 | 1.00 | 25.71 | N |
| ATOM | 71 | C | GLN | C | 329 | 29.874 | −9.345 | −71.606 | 1.00 | 26.68 | C |
| ATOM | 72 | O | GLN | C | 329 | 28.663 | −9.143 | −71.460 | 1.00 | 27.94 | O |
| ATOM | 73 | N | GLU | C | 330 | 30.376 | −10.544 | −71.900 | 1.00 | 24.20 | N |
| ATOM | 74 | CA | GLU | C | 330 | 29.505 | −11.670 | −72.247 | 1.00 | 26.72 | C |
| ATOM | 75 | CB | GLU | C | 330 | 30.189 | −12.594 | −73.249 | 1.00 | 27.74 | C |
| ATOM | 76 | CG | GLU | C | 330 | 30.699 | −11.899 | −74.513 | 1.00 | 34.59 | C |
| ATOM | 77 | CD | GLU | C | 330 | 29.593 | −11.220 | −75.293 | 1.00 | 45.62 | C |
| ATOM | 78 | OE1 | GLU | C | 330 | 28.599 | −11.894 | −75.604 | 1.00 | 49.20 | O |
| ATOM | 79 | OE2 | GLU | C | 330 | 29.720 | −10.005 | −75.600 | 1.00 | 62.00 | O |
| ATOM | 80 | C | GLU | C | 330 | 29.095 | −12.496 | −71.007 | 1.00 | 32.53 | C |
| ATOM | 81 | O | GLU | C | 330 | 28.172 | −13.296 | −71.073 | 1.00 | 26.39 | O |
| ATOM | 82 | N | THR | C | 331 | 29.807 | −12.308 | −69.894 | 1.00 | 22.19 | N |
| ATOM | 83 | CA | THR | C | 331 | 29.644 | −13.175 | −68.743 | 1.00 | 21.66 | C |
| ATOM | 84 | CB | THR | C | 331 | 30.979 | −13.320 | −67.995 | 1.00 | 20.37 | C |
| ATOM | 85 | OG1 | THR | C | 331 | 31.978 | −13.822 | −68.895 | 1.00 | 21.34 | O |
| ATOM | 86 | CG2 | THR | C | 331 | 30.846 | −14.283 | −66.759 | 1.00 | 20.48 | C |
| ATOM | 87 | C | THR | C | 331 | 28.570 | −12.579 | −67.802 | 1.00 | 21.67 | C |
| ATOM | 88 | O | THR | C | 331 | 28.771 | −11.510 | −67.234 | 1.00 | 20.43 | O |
| ATOM | 89 | N | GLU | C | 332 | 27.444 | −13.288 | −67.620 | 1.00 | 20.52 | N |
| ATOM | 90 | CA | GLU | C | 332 | 26.369 | −12.778 | −66.724 | 1.00 | 20.77 | C |
| ATOM | 91 | CB | GLU | C | 332 | 25.017 | −13.480 | −66.977 | 1.00 | 20.27 | C |
| ATOM | 92 | CG | GLU | C | 332 | 23.882 | −12.937 | −66.124 | 1.00 | 19.05 | C |
| ATOM | 93 | CD | GLU | C | 332 | 22.596 | −13.725 | −66.305 | 1.00 | 20.91 | C |
| ATOM | 94 | OE1 | GLU | C | 332 | 21.899 | −13.477 | −67.285 | 1.00 | 23.36 | O |
| ATOM | 95 | OE2 | GLU | C | 332 | 22.317 | −14.608 | −65.483 | 1.00 | 26.39 | O |
| ATOM | 96 | C | GLU | C | 332 | 26.792 | −13.004 | −65.276 | 1.00 | 18.32 | C |
| ATOM | 97 | O | GLU | C | 332 | 27.275 | −14.091 | −64.925 | 1.00 | 21.92 | O |
| ATOM | 98 | N | ILE | C | 333 | 26.635 | −11.980 | −64.448 | 1.00 | 16.21 | N |
| ATOM | 99 | CA | ILE | C | 333 | 27.008 | −12.108 | −63.025 | 1.00 | 15.97 | C |
| ATOM | 100 | CB | ILE | C | 333 | 27.890 | −10.936 | −62.553 | 1.00 | 16.96 | C |
| ATOM | 101 | CG1 | ILE | C | 333 | 29.195 | −10.858 | −63.404 | 1.00 | 17.65 | C |
| ATOM | 102 | CD1 | ILE | C | 333 | 30.082 | −12.105 | −63.306 | 1.00 | 20.60 | C |
| ATOM | 103 | CG2 | ILE | C | 333 | 28.207 | −11.071 | −61.046 | 1.00 | 16.94 | C |
| ATOM | 104 | C | ILE | C | 333 | 25.758 | −12.235 | −62.118 | 1.00 | 16.60 | C |
| ATOM | 105 | O | ILE | C | 333 | 25.751 | −12.999 | −61.159 | 1.00 | 17.83 | O |
| ATOM | 106 | N | THR | C | 334 | 24.737 | −11.468 | −62.420 | 1.00 | 16.91 | N |
| ATOM | 107 | CA | THR | C | 334 | 23.470 | −11.584 | −61.701 | 1.00 | 19.13 | C |
| ATOM | 108 | CB | THR | C | 334 | 23.504 | −10.825 | −60.327 | 1.00 | 22.14 | C |

TABLE 5-continued

Atomic coordinates for CRBN(TBD):Thalidomide (Murine protein)

| ATOM | 109 | OG1 | THR | C | 334 | 22.406 | −11.259 | −59.500 | 1.00 | 18.82 | O |
|---|---|---|---|---|---|---|---|---|---|---|---|
| ATOM | 110 | CG2 | THR | C | 334 | 23.436 | −9.298 | −60.521 | 1.00 | 17.18 | C |
| ATOM | 111 | C | THR | C | 334 | 22.333 | −11.118 | −62.609 | 1.00 | 20.17 | C |
| ATOM | 112 | O | THR | C | 334 | 22.562 | −10.830 | −63.794 | 1.00 | 19.33 | O |
| ATOM | 113 | N | THR | C | 335 | 21.104 | −11.106 | −62.090 | 1.00 | 17.83 | N |
| ATOM | 114 | CA | THR | C | 335 | 19.993 | −10.526 | −62.812 | 1.00 | 17.87 | C |
| ATOM | 115 | CB | THR | C | 335 | 18.938 | −11.589 | −63.235 | 1.00 | 19.93 | C |
| ATOM | 116 | OG1 | THR | C | 335 | 18.197 | −12.018 | −62.079 | 1.00 | 21.12 | O |
| ATOM | 117 | CG2 | THR | C | 335 | 19.607 | −12.791 | −63.907 | 1.00 | 19.48 | C |
| ATOM | 118 | C | THR | C | 335 | 19.309 | −9.526 | −61.932 | 1.00 | 16.53 | C |
| ATOM | 119 | O | THR | C | 335 | 19.430 | −9.567 | −60.705 | 1.00 | 17.74 | O |
| ATOM | 120 | N | LYS | C | 336 | 18.515 | −8.670 | −62.545 | 1.00 | 19.33 | N |
| ATOM | 121 | CA | LYS | C | 336 | 17.754 | −7.693 | −61.794 | 1.00 | 20.73 | C |
| ATOM | 122 | CB | LYS | C | 336 | 17.016 | −6.767 | −62.746 | 1.00 | 26.49 | C |
| ATOM | 123 | CG | LYS | C | 336 | 17.923 | −5.803 | −63.493 | 1.00 | 38.49 | C |
| ATOM | 124 | CD | LYS | C | 336 | 17.092 | −4.813 | −64.303 | 1.00 | 40.78 | C |
| ATOM | 125 | CE | LYS | C | 336 | 17.974 | −3.943 | −65.188 | 1.00 | 52.95 | C |
| ATOM | 126 | NZ | LYS | C | 336 | 17.150 | −3.107 | −66.113 | 1.00 | 44.22 | N |
| ATOM | 127 | C | LYS | C | 336 | 16.748 | −8.362 | −60.884 | 1.00 | 22.29 | C |
| ATOM | 128 | O | LYS | C | 336 | 16.337 | −7.776 | −59.892 | 1.00 | 18.74 | O |
| ATOM | 129 | N | ASN | C | 337 | 16.311 | −9.572 | −61.246 | 1.00 | 18.70 | N |
| ATOM | 130 | CA | ASN | C | 337 | 15.382 | −10.329 | −60.372 | 1.00 | 20.84 | C |
| ATOM | 131 | CB | ASN | C | 337 | 14.928 | −11.661 | −61.030 | 1.00 | 19.37 | C |
| ATOM | 132 | C3 | ASN | C | 337 | 14.181 | −11.439 | −62.324 | 1.00 | 28.00 | C |
| ATOM | 133 | OD1 | ASN | C | 337 | 14.574 | −11.945 | −63.371 | 1.00 | 28.85 | O |
| ATOM | 134 | ND2 | ASN | C | 337 | 13.139 | −10.631 | −62.272 | 1.00 | 36.13 | N |
| ATOM | 135 | C | ASN | C | 337 | 15.945 | −10.629 | −59.001 | 1.00 | 19.79 | C |
| ATOM | 136 | O | ASN | C | 337 | 15.183 | −10.888 | −58.074 | 1.00 | 20.01 | O |
| ATOM | 137 | N | GLU | C | 338 | 17.275 | −10.604 | −58.860 | 1.00 | 16.75 | N |
| ATOM | 138 | CA | GLU | C | 338 | 17.931 | −11.039 | −57.580 | 1.00 | 17.47 | C |
| ATOM | 139 | CB | GLU | C | 338 | 19.243 | −11.808 | −57.841 | 1.00 | 17.88 | C |
| ATOM | 140 | CG | GLU | C | 338 | 19.078 | −13.098 | −58.632 | 1.00 | 21.61 | C |
| ATOM | 141 | CD | GLU | C | 338 | 18.037 | −14.040 | −58.027 | 1.00 | 22.61 | C |
| ATOM | 142 | OE1 | GLU | C | 338 | 18.033 | −14.253 | −56.784 | 1.00 | 22.22 | O |
| ATOM | 143 | OE2 | GLU | C | 338 | 17.225 | −14.574 | −58.808 | 1.00 | 32.25 | O |
| ATOM | 144 | C | GLU | C | 338 | 18.184 | −9.879 | −56.592 | 1.00 | 15.17 | C |
| ATOM | 145 | O | GLU | C | 338 | 18.589 | −10.095 | −55.433 | 1.00 | 16.49 | O |
| ATOM | 146 | N | ILE | C | 339 | 17.889 | −8.669 | −57.041 | 1.00 | 16.22 | N |
| ATOM | 147 | CA | ILE | C | 339 | 18.150 | −7.464 | −56.253 | 1.00 | 16.63 | C |
| ATOM | 148 | CB | ILE | C | 339 | 17.934 | −6.180 | −57.111 | 1.00 | 17.56 | C |
| ATOM | 149 | CG1 | ILE | C | 339 | 18.984 | −6.123 | −58.230 | 1.00 | 21.04 | C |
| ATOM | 150 | CD1 | ILE | C | 339 | 18.666 | −5.066 | −59.289 | 1.00 | 21.66 | C |
| ATOM | 151 | CG2 | ILE | C | 339 | 17.980 | −4.921 | −56.237 | 1.00 | 20.81 | C |
| ATOM | 152 | C | ILE | C | 339 | 17.249 | −7.414 | −55.015 | 1.00 | 20.59 | C |
| ATOM | 153 | O | ILE | C | 339 | 16.028 | −7.720 | −55.082 | 1.00 | 18.80 | O |
| ATOM | 154 | N | PHE | C | 340 | 17.842 | −7.039 | −53.890 | 1.00 | 19.91 | N |
| ATOM | 155 | CA | PHE | C | 340 | 17.051 | −6.776 | −52.697 | 1.00 | 20.71 | C |
| ATOM | 156 | CB | PHE | C | 340 | 16.912 | −8.057 | −51.844 | 1.00 | 16.57 | C |
| ATOM | 157 | CG | PHE | C | 340 | 18.137 | −8.399 | −51.056 | 1.00 | 17.66 | C |
| ATOM | 158 | CD2 | PHE | C | 340 | 18.183 | −8.159 | −49.688 | 1.00 | 16.76 | C |
| ATOM | 159 | CE2 | PHE | C | 340 | 19.317 | −8.437 | −48.951 | 1.00 | 18.55 | C |
| ATOM | 160 | CZ | PHE | C | 340 | 20.425 | −9.028 | −49.565 | 1.00 | 18.92 | C |
| ATOM | 161 | CE1 | PHE | C | 340 | 20.392 | −9.302 | −50.932 | 1.00 | 16.51 | C |
| ATOM | 162 | CD1 | PHE | C | 340 | 19.260 | −9.006 | −51.677 | 1.00 | 15.31 | C |
| ATOM | 163 | C | PHE | C | 340 | 17.658 | −5.664 | −51.870 | 1.00 | 22.75 | C |
| ATOM | 164 | O | PHE | C | 340 | 18.821 | −5.284 | −52.070 | 1.00 | 19.45 | O |
| ATOM | 165 | N | SER | C | 341 | 16.896 | −5.210 | −50.879 | 1.00 | 22.32 | N |
| ATOM | 166 | CA | SER | C | 341 | 17.342 | −4.112 | −50.030 | 1.00 | 28.31 | C |
| ATOM | 167 | CB | SER | C | 341 | 16.282 | −3.011 | −49.993 | 1.00 | 30.08 | C |
| ATOM | 168 | OG | SER | C | 341 | 16.663 | −2.008 | −49.060 | 1.00 | 42.42 | O |
| ATOM | 169 | C | SER | C | 341 | 17.686 | −4.575 | −48.617 | 1.00 | 24.33 | C |
| ATOM | 170 | O | SER | C | 341 | 16.802 | −4.956 | −47.836 | 1.00 | 25.15 | O |
| ATOM | 171 | N | LEU | C | 342 | 18.965 | −4.528 | −48.271 | 1.00 | 25.48 | N |
| ATOM | 172 | CA | LEU | C | 342 | 19.360 | −4.873 | −46.909 | 1.00 | 29.14 | C |
| ATOM | 173 | CB | LEU | C | 342 | 20.764 | −5.472 | −46.873 | 1.00 | 33.26 | C |
| ATOM | 174 | CG | LEU | C | 342 | 21.197 | −6.085 | −45.533 | 1.00 | 35.08 | C |
| ATOM | 175 | CD1 | LEU | C | 342 | 20.476 | −7.401 | −45.263 | 1.00 | 38.20 | C |
| ATOM | 176 | CD2 | LEU | C | 342 | 22.691 | −6.314 | −45.519 | 1.00 | 37.13 | C |
| ATOM | 177 | C | LEU | C | 342 | 19.233 | −3.674 | −45.954 | 1.00 | 37.44 | C |
| ATOM | 178 | O | LEU | C | 342 | 19.712 | −2.569 | −46.247 | 1.00 | 36.54 | O |
| ATOM | 179 | N | SER | C | 343 | 18.544 | −3.906 | −44.836 | 1.00 | 29.22 | N |
| ATOM | 180 | CA | SER | C | 343 | 18.332 | −2.918 | −43.753 | 1.00 | 42.84 | C |
| ATOM | 181 | CB | SER | C | 343 | 19.636 | −2.274 | −43.297 | 1.00 | 39.94 | C |
| ATOM | 182 | OG | SER | C | 343 | 20.300 | −3.169 | −42.452 | 1.00 | 45.11 | O |
| ATOM | 183 | C | SER | C | 343 | 17.270 | −1.885 | −44.047 | 1.00 | 53.89 | C |
| ATOM | 184 | O | SER | C | 343 | 16.134 | −2.030 | −43.595 | 1.00 | 46.67 | O |
| ATOM | 185 | N | VAL | C | 358 | 25.784 | 3.683 | −50.724 | 1.00 | 86.16 | N |
| ATOM | 186 | CA | VAL | C | 358 | 25.429 | 2.329 | −51.159 | 1.00 | 91.37 | C |

TABLE 5-continued

Atomic coordinates for CRBN(TBD):Thalidomide (Murine protein)

| ATOM | 187 | CB | VAL | C | 358 | 24.913 | 1.439 | −49.993 | 1.00 | 90.88 | C |
|---|---|---|---|---|---|---|---|---|---|---|---|
| ATOM | 188 | CG1 | VAL | C | 358 | 25.871 | 0.281 | −49.740 | 1.00 | 77.39 | C |
| ATOM | 189 | CG2 | VAL | C | 358 | 24.695 | 2.258 | −48.726 | 1.00 | 88.00 | C |
| ATOM | 190 | C | VAL | C | 358 | 24.430 | 2.322 | −52.323 | 1.00 | 92.23 | C |
| ATOM | 191 | O | VAL | C | 358 | 23.639 | 1.391 | −52.473 | 1.00 | 95.73 | O |
| ATOM | 192 | N | HIS | C | 359 | 24.462 | 3.384 | −53.123 | 1.00 | 89.82 | N |
| ATOM | 193 | CA | HIS | C | 359 | 24.024 | 3.324 | −54.512 | 1.00 | 79.39 | C |
| ATOM | 194 | CB | HIS | C | 359 | 23.828 | 4.738 | −55.047 | 1.00 | 91.89 | C |
| ATOM | 195 | CG | HIS | C | 359 | 22.714 | 4.866 | −56.059 | 1.00 | 100.08 | C |
| ATOM | 196 | ND1 | HIS | C | 359 | 21.653 | 5.680 | −55.870 | 1.00 | 109.22 | N |
| ATOM | 197 | CE1 | HIS | C | 359 | 20.831 | 5.598 | −56.933 | 1.00 | 105.11 | C |
| ATOM | 198 | NE2 | HIS | C | 359 | 21.367 | 4.735 | −57.810 | 1.00 | 106.55 | N |
| ATOM | 199 | CD2 | HIS | C | 359 | 22.530 | 4.267 | −57.306 | 1.00 | 99.77 | C |
| ATOM | 200 | C | HIS | C | 359 | 25.134 | 2.643 | −55.267 | 1.00 | 69.78 | C |
| ATOM | 201 | O | HIS | C | 359 | 24.899 | 1.850 | −56.185 | 1.00 | 72.62 | O |
| ATOM | 202 | N | GLU | C | 360 | 26.361 | 2.947 | −54.844 | 1.00 | 68.81 | N |
| ATOM | 203 | CA | GLU | C | 360 | 27.590 | 2.275 | −55.284 | 1.00 | 62.20 | C |
| ATOM | 204 | CB | GLU | C | 360 | 28.717 | 2.551 | −54.273 | 1.00 | 69.01 | C |
| ATOM | 205 | CG | GLU | C | 360 | 29.032 | 4.018 | −54.034 | 1.00 | 102.39 | C |
| ATOM | 206 | CD | GLU | C | 360 | 30.397 | 4.406 | −54.560 | 1.00 | 110.02 | C |
| ATOM | 207 | OE1 | GLU | C | 360 | 31.240 | 4.851 | −53.750 | 1.00 | 115.50 | O |
| ATOM | 208 | OE2 | GLU | C | 360 | 30.635 | 4.245 | −55.778 | 1.00 | 108.55 | O |
| ATOM | 209 | C | GLU | C | 360 | 27.448 | 0.758 | −55.410 | 1.00 | 56.41 | C |
| ATOM | 210 | O | GLU | C | 360 | 28.046 | 0.139 | −56.305 | 1.00 | 33.37 | O |
| ATOM | 211 | N | THR | C | 361 | 26.726 | 0.159 | −54.462 | 1.00 | 43.79 | N |
| ATOM | 212 | CA | THR | C | 361 | 26.789 | −1.289 | −54.248 | 1.00 | 36.57 | C |
| ATOM | 213 | CB | THR | C | 361 | 27.462 | −1.640 | −52.898 | 1.00 | 43.48 | C |
| ATOM | 214 | OG1 | THR | C | 361 | 28.765 | −1.043 | −52.847 | 1.00 | 55.08 | O |
| ATOM | 215 | CG2 | THR | C | 361 | 27.618 | −3.165 | −52.747 | 1.00 | 34.71 | C |
| ATOM | 216 | C | THR | C | 361 | 25.399 | −1.933 | −54.364 | 1.00 | 31.72 | C |
| ATOM | 217 | O | THR | C | 361 | 24.476 | −1.584 | −53.642 | 1.00 | 34.30 | O |
| ATOM | 218 | N | LEU | C | 362 | 25.265 | −2.841 | −55.323 | 1.00 | 28.72 | N |
| ATOM | 219 | CA | LEU | C | 362 | 24.049 | −3.581 | −55.523 | 1.00 | 24.86 | C |
| ATOM | 220 | CB | LEU | C | 362 | 23.982 | −4.026 | −56.977 | 1.00 | 24.76 | C |
| ATOM | 221 | CG | LEU | C | 362 | 22.644 | −4.428 | −57.549 | 1.00 | 32.95 | C |
| ATOM | 222 | CD1 | LEU | C | 362 | 21.670 | −3.242 | −57.520 | 1.00 | 33.14 | C |
| ATOM | 223 | CD2 | LEU | C | 362 | 22.865 | −4.898 | −58.973 | 1.00 | 32.38 | C |
| ATOM | 224 | C | LEU | C | 362 | 24.098 | −4.811 | −54.623 | 1.00 | 26.07 | C |
| ATOM | 225 | O | LEU | C | 362 | 25.104 | −5.510 | −54.592 | 1.00 | 24.45 | O |
| ATOM | 226 | N | THR | C | 363 | 23.012 | −5.101 | −53.918 | 1.00 | 18.38 | N |
| ATOM | 227 | CA | THR | C | 363 | 22.984 | −6.329 | −53.107 | 1.00 | 16.32 | C |
| ATOM | 228 | CB | THR | C | 363 | 22.617 | −6.056 | −51.638 | 1.00 | 21.09 | C |
| ATOM | 229 | OG1 | THR | C | 363 | 21.375 | −5.358 | −51.571 | 1.00 | 20.47 | O |
| ATOM | 230 | CG2 | THR | C | 363 | 23.731 | −5.225 | −50.935 | 1.00 | 20.12 | C |
| ATOM | 231 | C | THR | C | 363 | 21.989 | −7.273 | −53.742 | 1.00 | 18.41 | C |
| ATOM | 232 | O | THR | C | 363 | 20.849 | −6.887 | −54.023 | 1.00 | 18.88 | O |
| ATOM | 233 | N | VAL | C | 364 | 22.440 | −8.489 | −54.035 | 1.00 | 14.94 | N |
| ATOM | 234 | CA | VAL | C | 364 | 21.594 | −9.473 | −54.727 | 1.00 | 13.40 | C |
| ATOM | 235 | CB | VAL | C | 364 | 22.039 | −9.701 | −56.200 | 1.00 | 12.25 | C |
| ATOM | 236 | CG1 | VAL | C | 364 | 21.771 | −8.460 | −57.071 | 1.00 | 17.35 | C |
| ATOM | 237 | CG2 | VAL | C | 364 | 23.527 | −10.107 | −56.248 | 1.00 | 15.31 | C |
| ATOM | 238 | C | VAL | C | 364 | 21.667 | −10.818 | −53.966 | 1.00 | 13.21 | C |
| ATOM | 239 | O | VAL | C | 364 | 22.674 | −11.136 | −53.326 | 1.00 | 13.05 | O |
| ATOM | 240 | N | TYR | C | 365 | 20.569 | −11.587 | −53.992 | 1.00 | 17.09 | N |
| ATOM | 241 | CA | TYR | C | 365 | 20.549 | −12.854 | −53.259 | 1.00 | 15.55 | C |
| ATOM | 242 | CB | TYR | C | 365 | 19.133 | −13.392 | −53.241 | 1.00 | 16.73 | C |
| ATOM | 243 | CG | TYR | C | 365 | 18.200 | −12.661 | −52.307 | 1.00 | 15.97 | C |
| ATOM | 244 | CD1 | TYR | C | 365 | 18.424 | −12.659 | −50.927 | 1.00 | 15.06 | C |
| ATOM | 245 | CE1 | TYR | C | 365 | 17.539 | −12.050 | −50.061 | 1.00 | 15.79 | C |
| ATOM | 246 | CZ | TYR | C | 365 | 16.403 | −11.438 | −50.557 | 1.00 | 17.61 | C |
| ATOM | 247 | OH | TYR | C | 365 | 15.513 | −10.830 | −49.665 | 1.00 | 18.59 | O |
| ATOM | 248 | CE2 | TYR | C | 365 | 16.137 | −11.429 | −51.929 | 1.00 | 17.31 | C |
| ATOM | 249 | CD2 | TYR | C | 365 | 17.027 | −12.059 | −52.796 | 1.00 | 16.54 | C |
| ATOM | 250 | C | TYR | C | 365 | 21.453 | −13.919 | −53.918 | 1.00 | 16.38 | C |
| ATOM | 251 | O | TYR | C | 365 | 21.998 | −14.797 | −53.245 | 1.00 | 15.40 | O |
| ATOM | 252 | N | LYS | C | 366 | 21.556 | −13.849 | −55.243 | 1.00 | 14.22 | N |
| ATOM | 253 | CA | LYS | C | 366 | 22.203 | −14.903 | −56.022 | 1.00 | 14.39 | C |
| ATOM | 254 | CB | LYS | C | 366 | 21.146 | −15.801 | −56.695 | 1.00 | 15.32 | C |
| ATOM | 255 | CG | LYS | C | 366 | 20.304 | −16.680 | −55.738 | 1.00 | 18.29 | C |
| ATOM | 256 | CD | LYS | C | 366 | 21.231 | −17.638 | −55.023 | 1.00 | 21.75 | C |
| ATOM | 257 | CE | LYS | C | 366 | 20.706 | −19.036 | −54.851 | 1.00 | 32.92 | C |
| ATOM | 258 | NZ | LYS | C | 366 | 21.855 | −19.979 | −54.530 | 1.00 | 22.76 | N |
| ATOM | 259 | C | LYS | C | 366 | 23.059 | −14.264 | −57.109 | 1.00 | 15.89 | C |
| ATOM | 260 | O | LYS | C | 366 | 22.677 | −13.232 | −57.686 | 1.00 | 17.96 | O |
| ATOM | 261 | N | ALA | C | 367 | 24.133 | −14.953 | −57.468 | 1.00 | 15.52 | N |
| ATOM | 262 | CA | ALA | C | 367 | 25.041 | −14.500 | −58.553 | 1.00 | 17.29 | C |
| ATOM | 263 | CB | ALA | C | 367 | 26.087 | −13.531 | −58.005 | 1.00 | 17.16 | C |
| ATOM | 264 | C | ALA | C | 367 | 25.711 | −15.734 | −59.164 | 1.00 | 16.23 | C |

TABLE 5-continued

Atomic coordinates for CRBN(TBD):Thalidomide (Murine protein)

| ATOM | 265 | O | ALA | C | 367 | 25.606 | −16.850 | −58.615 | 1.00 | 18.42 | O |
|---|---|---|---|---|---|---|---|---|---|---|---|
| ATOM | 266 | N | SER | C | 368 | 26.327 | −15.550 | −60.322 | 1.00 | 18.54 | N |
| ATOM | 267 | CA | SER | C | 368 | 26.842 | −16.652 | −61.125 | 1.00 | 18.67 | C |
| ATOM | 268 | CB | SER | C | 368 | 25.883 | −16.938 | −62.301 | 1.00 | 16.89 | C |
| ATOM | 269 | OG | SER | C | 368 | 25.588 | −15.770 | −63.080 | 1.00 | 24.00 | O |
| ATOM | 270 | C | SER | C | 368 | 28.198 | −16.282 | −61.677 | 1.00 | 18.19 | C |
| ATOM | 271 | O | SER | C | 368 | 28.477 | −15.087 | −61.908 | 1.00 | 14.64 | O |
| ATOM | 272 | N | ASN | C | 369 | 29.026 | −17.292 | −61.941 | 1.00 | 16.45 | N |
| ATOM | 273 | CA | ASN | C | 369 | 30.264 | −17.077 | −62.739 | 1.00 | 18.06 | C |
| ATOM | 274 | CB | ASN | C | 369 | 29.941 | −16.415 | −64.128 | 1.00 | 17.86 | C |
| ATOM | 275 | CG | ASN | C | 369 | 28.926 | −17.219 | −64.958 | 1.00 | 21.13 | C |
| ATOM | 276 | OD1 | ASN | C | 369 | 27.973 | −16.655 | −65.522 | 1.00 | 24.07 | O |
| ATOM | 277 | ND2 | ASN | C | 369 | 29.090 | −18.518 | −64.986 | 1.00 | 20.73 | N |
| ATOM | 278 | C | ASN | C | 369 | 31.285 | −16.224 | −61.979 | 1.00 | 20.08 | C |
| ATOM | 279 | O | ASN | C | 369 | 32.055 | −15.496 | −62.589 | 1.00 | 20.43 | O |
| ATOM | 280 | N | LEU | C | 370 | 31.249 | −16.294 | −60.640 | 1.00 | 19.32 | N |
| ATOM | 281 | CA | LEU | C | 370 | 32.252 | −15.649 | −59.789 | 1.00 | 16.66 | C |
| ATOM | 282 | CB | LEU | C | 370 | 31.567 | −14.766 | −58.707 | 1.00 | 15.97 | C |
| ATOM | 283 | CG | LEU | C | 370 | 30.788 | −13.562 | −59.246 | 1.00 | 17.67 | C |
| ATOM | 284 | CD1 | LEU | C | 370 | 29.921 | −12.945 | −58.139 | 1.00 | 17.82 | C |
| ATOM | 285 | CD2 | LEU | C | 370 | 31.765 | −12.493 | −59.774 | 1.00 | 17.13 | C |
| ATOM | 286 | C | LEU | C | 370 | 33.134 | −16.684 | −59.124 | 1.00 | 22.04 | C |
| ATOM | 287 | O | LEU | C | 370 | 32.664 | −17.765 | −58.750 | 1.00 | 27.66 | O |
| ATOM | 288 | N | ASN | C | 371 | 34.425 | −16.359 | −59.011 | 1.00 | 19.95 | N |
| ATOM | 289 | CA | ASN | C | 371 | 35.391 | −17.098 | −58.191 | 1.00 | 22.48 | C |
| ATOM | 290 | CB | ASN | C | 371 | 36.744 | −17.219 | −58.942 | 1.00 | 23.38 | C |
| ATOM | 291 | CG | ASN | C | 371 | 36.716 | −18.257 | −60.034 | 1.00 | 34.72 | C |
| ATOM | 292 | OD1 | ASN | C | 371 | 35.928 | −19.200 | −59.992 | 1.00 | 40.19 | O |
| ATOM | 293 | ND2 | ASN | C | 371 | 37.580 | −18.090 | −61.027 | 1.00 | 29.69 | N |
| ATOM | 294 | C | ASN | C | 371 | 35.646 | −16.343 | −56.871 | 1.00 | 21.29 | C |
| ATOM | 295 | O | ASN | C | 371 | 35.836 | −15.137 | −56.872 | 1.00 | 24.39 | O |
| ATOM | 296 | N | LEU | C | 372 | 35.690 | −17.079 | −55.765 | 1.00 | 24.84 | N |
| ATOM | 297 | CA | LEU | C | 372 | 35.943 | −16.502 | −54.464 | 1.00 | 25.98 | C |
| ATOM | 298 | CB | LEU | C | 372 | 35.178 | −17.273 | −53.371 | 1.00 | 28.82 | C |
| ATOM | 299 | CG | LEU | C | 372 | 33.653 | −17.377 | −53.543 | 1.00 | 29.97 | C |
| ATOM | 300 | CD1 | LEU | C | 372 | 33.015 | −18.146 | −52.385 | 1.00 | 28.60 | C |
| ATOM | 301 | CD2 | LEU | C | 372 | 33.042 | −15.996 | −53.667 | 1.00 | 22.27 | C |
| ATOM | 302 | C | LEU | C | 372 | 37.432 | −16.552 | −54.183 | 1.00 | 31.79 | C |
| ATOM | 303 | O | LEU | C | 372 | 38.061 | −17.570 | −54.391 | 1.00 | 29.23 | O |
| ATOM | 304 | N | ILE | C | 373 | 37.977 | −15.430 | −53.714 | 1.00 | 28.88 | N |
| ATOM | 305 | CA | ILE | C | 373 | 39.404 | −15.305 | −53.392 | 1.00 | 28.43 | C |
| ATOM | 306 | CB | ILE | C | 373 | 39.999 | −14.023 | −54.008 | 1.00 | 30.57 | C |
| ATOM | 307 | CG1 | ILE | C | 373 | 39.787 | −13.997 | −55.519 | 1.00 | 34.72 | C |
| ATOM | 308 | CD1 | ILE | C | 373 | 40.451 | −15.155 | −56.247 | 1.00 | 35.61 | C |
| ATOM | 309 | CG2 | ILE | C | 373 | 41.483 | −13.878 | −53.643 | 1.00 | 35.44 | C |
| ATOM | 310 | C | ILE | C | 373 | 39.549 | −15.196 | −51.891 | 1.00 | 32.83 | C |
| ATOM | 311 | O | ILE | C | 373 | 38.996 | −14.273 | −51.282 | 1.00 | 26.95 | O |
| ATOM | 312 | N | GLY | C | 374 | 40.282 | −16.128 | −51.285 | 1.00 | 38.01 | N |
| ATOM | 313 | CA | GLY | C | 374 | 40.625 | −16.018 | −49.858 | 1.00 | 37.48 | C |
| ATOM | 314 | C | GLY | C | 374 | 39.531 | −16.492 | −48.926 | 1.00 | 43.62 | C |
| ATOM | 315 | O | GLY | C | 374 | 38.617 | −17.227 | −49.338 | 1.00 | 39.66 | O |
| ATOM | 316 | N | ARG | C | 375 | 39.619 | −16.053 | −47.668 | 1.00 | 39.28 | N |
| ATOM | 317 | CA | ARG | C | 375 | 38.692 | −16.453 | −46.607 | 1.00 | 40.63 | C |
| ATOM | 318 | CB | ARG | C | 375 | 39.469 | −17.059 | −45.436 | 1.00 | 47.66 | C |
| ATOM | 319 | CG | ARG | C | 375 | 40.051 | −18.435 | −45.710 | 1.00 | 60.28 | C |
| ATOM | 320 | CD | ARG | C | 375 | 41.210 | −18.749 | −44.766 | 1.00 | 70.29 | C |
| ATOM | 321 | NE | ARG | C | 375 | 40.897 | −18.438 | −43.368 | 1.00 | 91.51 | N |
| ATOM | 322 | CZ | ARG | C | 375 | 41.534 | −17.523 | −42.633 | 1.00 | 89.00 | C |
| ATOM | 323 | NH1 | ARG | C | 375 | 42.540 | −16.826 | −43.148 | 1.00 | 90.40 | N |
| ATOM | 324 | NH2 | ARG | C | 375 | 41.168 | −17.313 | −41.376 | 1.00 | 89.65 | N |
| ATOM | 325 | C | ARG | C | 375 | 37.904 | −15.232 | −46.123 | 1.00 | 26.99 | C |
| ATOM | 326 | O | ARG | C | 375 | 38.380 | −14.111 | −46.263 | 1.00 | 34.28 | O |
| ATOM | 327 | N | PRO | C | 376 | 36.697 | −15.443 | −45.538 | 1.00 | 29.33 | N |
| ATOM | 328 | CA | PRO | C | 376 | 35.893 | −14.276 | −45.127 | 1.00 | 28.39 | C |
| ATOM | 329 | CB | PRO | C | 376 | 34.609 | −14.908 | −44.560 | 1.00 | 28.84 | C |
| ATOM | 330 | CG | PRO | C | 376 | 34.587 | −16.316 | −45.096 | 1.00 | 34.04 | C |
| ATOM | 331 | CD | PRO | C | 376 | 36.028 | −16.712 | −45.195 | 1.00 | 30.00 | C |
| ATOM | 332 | C | PRO | C | 376 | 36.588 | −13.448 | −44.039 | 1.00 | 39.15 | C |
| ATOM | 333 | O | PRO | C | 376 | 37.254 | −14.015 | −43.153 | 1.00 | 35.18 | O |
| ATOM | 334 | N | SER | C | 377 | 36.392 | −12.132 | −44.085 | 1.00 | 27.68 | N |
| ATOM | 335 | CA | SER | C | 377 | 36.922 | −11.223 | −43.075 | 1.00 | 26.47 | C |
| ATOM | 336 | CB | SER | C | 377 | 38.149 | −10.498 | −43.632 | 1.00 | 31.82 | C |
| ATOM | 337 | OG | SER | C | 377 | 38.432 | −9.324 | −42.893 | 1.00 | 29.34 | O |
| ATOM | 338 | C | SER | C | 377 | 35.846 | −10.217 | −42.671 | 1.00 | 27.05 | C |
| ATOM | 339 | O | SER | C | 377 | 35.015 | −9.838 | −43.481 | 1.00 | 23.93 | O |
| ATOM | 340 | N | THR | C | 378 | 35.838 | −9.794 | −41.413 | 1.00 | 21.03 | N |
| ATOM | 341 | CA | THR | C | 378 | 34.877 | −8.768 | −40.993 | 1.00 | 19.97 | C |
| ATOM | 342 | CB | THR | C | 378 | 34.255 | −9.084 | −39.619 | 1.00 | 24.98 | C |

TABLE 5-continued

Atomic coordinates for CRBN(TBD):Thalidomide (Murine protein)

| ATOM | 343 | OG1 | THR | C | 378 | 35.301 | −9.216 | −38.657 | 1.00 | 25.97 | O |
|------|-----|-----|-----|---|-----|--------|--------|---------|------|-------|---|
| ATOM | 344 | CG2 | THR | C | 378 | 33.455 | −10.394 | −39.664 | 1.00 | 26.12 | C |
| ATOM | 345 | C | THR | C | 378 | 35.522 | −7.347 | −40.947 | 1.00 | 20.90 | C |
| ATOM | 346 | O | THR | C | 378 | 34.844 | −6.346 | −40.646 | 1.00 | 23.19 | O |
| ATOM | 347 | N | VAL | C | 379 | 36.802 | −7.268 | −41.292 | 1.00 | 29.55 | N |
| ATOM | 348 | CA | VAL | C | 379 | 37.517 | −5.988 | −41.266 | 1.00 | 27.57 | C |
| ATOM | 349 | CB | VAL | C | 379 | 39.010 | −6.147 | −41.685 | 1.00 | 32.26 | C |
| ATOM | 350 | CG1 | VAL | C | 379 | 39.740 | −4.814 | −41.552 | 1.00 | 37.63 | C |
| ATOM | 351 | CG2 | VAL | C | 379 | 39.706 | −7.210 | −40.844 | 1.00 | 35.13 | C |
| ATOM | 352 | C | VAL | C | 379 | 36.824 | −4.956 | −42.155 | 1.00 | 27.11 | C |
| ATOM | 353 | O | VAL | C | 379 | 36.672 | −5.165 | −43.368 | 1.00 | 23.80 | O |
| ATOM | 354 | N | HIS | C | 380 | 36.368 | −3.856 | −41.539 | 1.00 | 19.68 | N |
| ATOM | 355 | CA | HIS | C | 380 | 35.716 | −2.773 | −42.249 | 1.00 | 22.71 | C |
| ATOM | 356 | CB | HIS | C | 380 | 36.652 | −2.168 | −43.325 | 1.00 | 29.21 | C |
| ATOM | 357 | CG | HIS | C | 380 | 37.922 | −1.579 | −42.772 | 1.00 | 30.06 | C |
| ATOM | 358 | ND1 | HIS | C | 380 | 37.925 | −0.644 | −41.798 | 1.00 | 33.02 | N |
| ATOM | 359 | CE1 | HIS | C | 380 | 39.192 | −0.300 | −41.520 | 1.00 | 28.04 | C |
| ATOM | 360 | NE2 | HIS | C | 380 | 39.997 | −0.992 | −42.334 | 1.00 | 36.34 | N |
| ATOM | 361 | CD2 | HIS | C | 380 | 39.243 | −1.766 | −43.141 | 1.00 | 30.10 | C |
| ATOM | 362 | C | HIS | C | 380 | 34.429 | −3.177 | −42.933 | 1.00 | 25.03 | C |
| ATOM | 363 | O | HIS | C | 380 | 33.987 | −2.498 | −43.851 | 1.00 | 19.83 | O |
| ATOM | 364 | N | SER | C | 381 | 33.798 | −4.256 | −42.493 | 1.00 | 23.92 | N |
| ATOM | 365 | CA | SER | C | 381 | 32.653 | −4.749 | −43.248 | 1.00 | 22.02 | C |
| ATOM | 366 | CB | SER | C | 381 | 32.065 | −5.998 | −42.606 | 1.00 | 22.11 | C |
| ATOM | 367 | OG | SER | C | 381 | 30.857 | −6.314 | −43.291 | 1.00 | 22.36 | O |
| ATOM | 368 | C | SER | C | 381 | 31.584 | −3.685 | −43.347 | 1.00 | 22.58 | C |
| ATOM | 369 | O | SER | C | 381 | 31.201 | −3.081 | −42.334 | 1.00 | 23.86 | O |
| ATOM | 370 | N | TRP | C | 382 | 31.083 | −3.449 | −44.559 | 1.00 | 18.69 | N |
| ATOM | 371 | CA | TRP | C | 382 | 30.009 | −2.480 | −44.769 | 1.00 | 19.17 | C |
| ATOM | 372 | CB | TRP | C | 382 | 29.876 | −2.136 | −46.253 | 1.00 | 23.55 | C |
| ATOM | 373 | CG | TRP | C | 382 | 31.160 | −1.629 | −46.861 | 1.00 | 25.91 | C |
| ATOM | 374 | CD1 | TRP | C | 382 | 32.104 | −0.768 | −46.268 | 1.00 | 28.49 | C |
| ATOM | 375 | NE1 | TRP | C | 382 | 33.156 | −0.510 | −47.148 | 1.00 | 20.57 | N |
| ATOM | 376 | CE2 | TRP | C | 382 | 32.935 | −1.147 | −48.347 | 1.00 | 23.75 | C |
| ATOM | 377 | CD2 | TRP | C | 382 | 31.658 | −1.874 | −48.229 | 1.00 | 22.75 | C |
| ATOM | 378 | CE3 | TRP | C | 382 | 31.214 | −2.641 | −49.311 | 1.00 | 21.62 | C |
| ATOM | 379 | CZ3 | TRP | C | 382 | 31.991 | −2.647 | −50.503 | 1.00 | 23.46 | C |
| ATOM | 380 | CH2 | TRP | C | 382 | 33.210 | −1.940 | −50.592 | 1.00 | 24.17 | C |
| ATOM | 381 | CZ2 | TRP | C | 382 | 33.699 | −1.167 | −49.523 | 1.00 | 23.73 | C |
| ATOM | 382 | C | TRP | C | 382 | 28.674 | −2.913 | −44.243 | 1.00 | 22.73 | C |
| ATOM | 383 | O | TRP | C | 382 | 27.775 | −2.108 | −44.108 | 1.00 | 22.47 | O |
| ATOM | 384 | N | PHE | C | 383 | 28.513 | −4.203 | −43.991 | 1.00 | 21.47 | N |
| ATOM | 385 | CA | PHE | C | 383 | 27.224 | −4.722 | −43.511 | 1.00 | 21.44 | C |
| ATOM | 386 | CB | PHE | C | 383 | 26.616 | −5.670 | −44.561 | 1.00 | 21.53 | C |
| ATOM | 387 | CG | PHE | C | 383 | 26.430 | −5.024 | −45.903 | 1.00 | 20.41 | C |
| ATOM | 388 | CD1 | PHE | C | 383 | 25.357 | −4.169 | −46.138 | 1.00 | 24.94 | C |
| ATOM | 389 | CE1 | PHE | C | 383 | 25.181 | −3.573 | −47.384 | 1.00 | 25.58 | C |
| ATOM | 390 | CZ | PHE | C | 383 | 26.100 | −3.811 | −48.407 | 1.00 | 20.60 | C |
| ATOM | 391 | CE2 | PHE | C | 383 | 27.182 | −4.657 | −48.181 | 1.00 | 20.71 | C |
| ATOM | 392 | CD2 | PHE | C | 383 | 27.346 | −5.254 | −46.935 | 1.00 | 19.68 | C |
| ATOM | 393 | C | PHE | C | 383 | 27.450 | −5.425 | −42.208 | 1.00 | 21.12 | C |
| ATOM | 394 | O | PHE | C | 383 | 27.885 | −6.565 | −42.187 | 1.00 | 19.43 | O |
| ATOM | 395 | N | PRO | C | 384 | 27.242 | −4.707 | −41.095 | 1.00 | 25.20 | N |
| ATOM | 396 | CA | PRO | C | 384 | 27.595 | −5.237 | −39.769 | 1.00 | 28.08 | C |
| ATOM | 397 | CB | PRO | C | 384 | 26.990 | −4.197 | −38.809 | 1.00 | 35.10 | C |
| ATOM | 398 | CG | PRO | C | 384 | 26.923 | −2.935 | −39.614 | 1.00 | 41.19 | C |
| ATOM | 399 | CD | PRO | C | 384 | 26.607 | −3.376 | −41.018 | 1.00 | 30.91 | C |
| ATOM | 400 | C | PRO | C | 384 | 26.944 | −6.607 | −39.545 | 1.00 | 23.83 | C |
| ATOM | 401 | O | PRO | C | 384 | 25.768 | −6.785 | −39.883 | 1.00 | 23.90 | O |
| ATOM | 402 | N | GLY | C | 385 | 27.713 | −7.570 | −39.040 | 1.00 | 22.22 | N |
| ATOM | 403 | CA | GLY | C | 385 | 27.192 | −8.907 | −38.812 | 1.00 | 22.64 | C |
| ATOM | 404 | C | GLY | C | 385 | 27.518 | −9.836 | −39.961 | 1.00 | 23.19 | C |
| ATOM | 405 | O | GLY | C | 385 | 27.335 | −11.049 | −39.859 | 1.00 | 26.77 | O |
| ATOM | 406 | N | TYR | C | 386 | 28.014 | −9.275 | −41.065 | 1.00 | 22.07 | N |
| ATOM | 407 | CA | TYR | C | 386 | 28.491 | −10.109 | −42.188 | 1.00 | 19.16 | C |
| ATOM | 408 | CB | TYR | C | 386 | 27.788 | −9.715 | −43.503 | 1.00 | 19.95 | C |
| ATOM | 409 | CG | TYR | C | 386 | 26.316 | −10.026 | −43.551 | 1.00 | 18.86 | C |
| ATOM | 410 | CD1 | TYR | C | 386 | 25.849 | −11.262 | −44.073 | 1.00 | 21.60 | C |
| ATOM | 411 | CE1 | TYR | C | 386 | 24.483 | −11.557 | −44.116 | 1.00 | 18.03 | C |
| ATOM | 412 | CZ | TYR | C | 386 | 23.562 | −10.591 | −43.669 | 1.00 | 18.64 | C |
| ATOM | 413 | OH | TYR | C | 386 | 22.189 | −10.834 | −43.729 | 1.00 | 20.48 | O |
| ATOM | 414 | CE2 | TYR | C | 386 | 24.008 | −9.363 | −43.186 | 1.00 | 22.90 | C |
| ATOM | 415 | CD2 | TYR | C | 386 | 25.384 | −9.087 | −43.148 | 1.00 | 18.77 | C |
| ATOM | 416 | C | TYR | C | 386 | 29.987 | −9.937 | −42.376 | 1.00 | 22.75 | C |
| ATOM | 417 | O | TYR | C | 386 | 30.534 | −8.832 | −42.120 | 1.00 | 20.44 | O |
| ATOM | 418 | N | ALA | C | 387 | 30.631 | −11.018 | −42.826 | 1.00 | 20.30 | N |
| ATOM | 419 | CA | ALA | C | 387 | 32.013 | −11.008 | −43.301 | 1.00 | 22.78 | C |
| ATOM | 420 | CB | ALA | C | 387 | 32.757 | −12.240 | −42.796 | 1.00 | 25.12 | C |

TABLE 5-continued

Atomic coordinates for CRBN(TBD):Thalidomide (Murine protein)

| ATOM | 421 | C | ALA | C | 387 | 31.996 | −11.010 | −44.815 | 1.00 | 29.58 | C |
| --- | --- | --- | --- | --- | --- | --- | --- | --- | --- | --- | --- |
| ATOM | 422 | O | ALA | C | 387 | 31.002 | −11.440 | −45.425 | 1.00 | 23.99 | O |
| ATOM | 423 | N | TRP | C | 388 | 33.090 | −10.539 | −45.423 | 1.00 | 23.42 | N |
| ATOM | 424 | CA | TRP | C | 388 | 33.192 | −10.455 | −46.895 | 1.00 | 22.06 | C |
| ATOM | 425 | CB | TRP | C | 388 | 33.402 | −9.008 | −47.348 | 1.00 | 22.97 | C |
| ATOM | 426 | CG | TRP | C | 388 | 34.554 | −8.327 | −46.667 | 1.00 | 23.36 | C |
| ATOM | 427 | CD1 | TRP | C | 388 | 34.505 | −7.526 | −45.536 | 1.00 | 23.59 | C |
| ATOM | 428 | NE1 | TRP | C | 388 | 35.762 | −7.056 | −45.222 | 1.00 | 23.73 | N |
| ATOM | 429 | CE2 | TRP | C | 388 | 36.685 | −7.570 | −46.067 | 1.00 | 25.57 | C |
| ATOM | 430 | CD2 | TRP | C | 388 | 35.966 | −8.374 | −47.050 | 1.00 | 19.60 | C |
| ATOM | 431 | CE3 | TRP | C | 388 | 36.676 | −8.986 | −48.064 | 1.00 | 24.93 | C |
| ATOM | 432 | CZ3 | TRP | C | 388 | 38.067 | −8.805 | −48.117 | 1.00 | 31.33 | C |
| ATOM | 433 | CH2 | TRP | C | 388 | 38.740 | −8.008 | −47.167 | 1.00 | 25.05 | C |
| ATOM | 434 | CZ2 | TRP | C | 388 | 38.058 | −7.388 | −46.126 | 1.00 | 24.37 | C |
| ATOM | 435 | C | TRP | C | 388 | 34.292 | −11.325 | −47.431 | 1.00 | 23.80 | C |
| ATOM | 436 | O | TRP | C | 388 | 35.247 | −11.622 | −46.739 | 1.00 | 22.67 | O |
| ATOM | 437 | N | THR | C | 389 | 34.131 | −11.761 | −48.674 | 1.00 | 22.64 | N |
| ATOM | 438 | CA | THR | C | 389 | 35.137 | −12.527 | −49.390 | 1.00 | 23.15 | C |
| ATOM | 439 | CB | THR | C | 389 | 34.732 | −14.019 | −49.489 | 1.00 | 28.55 | C |
| ATOM | 440 | OG1 | THR | C | 389 | 34.575 | −14.589 | −48.166 | 1.00 | 25.21 | O |
| ATOM | 441 | CG2 | THR | C | 389 | 35.759 | −14.822 | −50.287 | 1.00 | 23.81 | C |
| ATOM | 442 | C | THR | C | 389 | 35.160 | −11.927 | −50.797 | 1.00 | 23.75 | C |
| ATOM | 443 | O | THR | C | 389 | 34.104 | −11.714 | −51.398 | 1.00 | 22.93 | O |
| ATOM | 444 | N | ILE | C | 390 | 36.348 | −11.611 | −51.310 | 1.00 | 22.61 | N |
| ATOM | 445 | CA | ILE | C | 390 | 36.446 | −11.025 | −52.649 | 1.00 | 20.60 | C |
| ATOM | 446 | CB | ILE | C | 390 | 37.918 | −10.671 | −53.009 | 1.00 | 23.72 | C |
| ATOM | 447 | CG1 | ILE | C | 390 | 38.433 | −9.540 | −52.085 | 1.00 | 25.88 | C |
| ATOM | 448 | CD1 | ILE | C | 390 | 39.952 | −9.430 | −52.036 | 1.00 | 30.43 | C |
| ATOM | 449 | CG2 | ILE | C | 390 | 38.018 | −10.266 | −54.482 | 1.00 | 23.92 | C |
| ATOM | 450 | C | ILE | C | 390 | 35.880 | −11.956 | −53.703 | 1.00 | 17.74 | C |
| ATOM | 451 | O | ILE | C | 390 | 36.131 | −13.151 | −53.661 | 1.00 | 19.14 | O |
| ATOM | 452 | N | ALA | C | 391 | 35.110 | −11.401 | −54.643 | 1.00 | 19.74 | N |
| ATOM | 453 | CA | ALA | C | 391 | 34.482 | −12.190 | −55.733 | 1.00 | 21.05 | C |
| ATOM | 454 | CB | ALA | C | 391 | 32.972 | −12.198 | −55.600 | 1.00 | 19.87 | C |
| ATOM | 455 | C | ALA | C | 391 | 34.863 | −11.593 | −57.066 | 1.00 | 21.71 | C |
| ATOM | 456 | O | ALA | C | 391 | 34.534 | −10.431 | −57.357 | 1.00 | 19.97 | O |
| ATOM | 457 | N | GLN | C | 392 | 35.506 | −12.405 | −57.903 | 1.00 | 19.87 | N |
| ATOM | 458 | CA | GLN | C | 392 | 35.940 | −11.920 | −59.197 | 1.00 | 20.86 | C |
| ATOM | 459 | CB | GLN | C | 392 | 37.464 | −11.885 | −59.260 | 1.00 | 23.28 | C |
| ATOM | 460 | CG | GLN | C | 392 | 38.133 | −13.225 | −59.075 | 1.00 | 25.86 | C |
| ATOM | 461 | CD | GLN | C | 392 | 39.660 | −13.128 | −59.140 | 1.00 | 32.26 | C |
| ATOM | 462 | OE1 | GLN | C | 392 | 40.282 | −12.260 | −58.490 | 1.00 | 26.90 | O |
| ATOM | 463 | NE2 | GLN | C | 392 | 40.272 | −14.030 | −59.894 | 1.00 | 27.93 | N |
| ATOM | 464 | C | GLN | C | 392 | 35.352 | −12.737 | −60.348 | 1.00 | 17.85 | C |
| ATOM | 465 | O | GLN | C | 392 | 34.990 | −13.910 | −60.181 | 1.00 | 16.88 | O |
| ATOM | 466 | N | CYS | C | 393 | 35.240 | −12.118 | −61.513 | 1.00 | 19.45 | N |
| ATOM | 467 | CA | CYS | C | 393 | 34.659 | −12.797 | −62.658 | 1.00 | 19.09 | C |
| ATOM | 468 | CB | CYS | C | 393 | 34.573 | −11.821 | −63.866 | 1.00 | 18.54 | C |
| ATOM | 469 | SG | CYS | C | 393 | 34.104 | −12.614 | −65.405 | 1.00 | 19.35 | S |
| ATOM | 470 | C | CYS | C | 393 | 35.477 | −14.044 | −62.998 | 1.00 | 20.04 | C |
| ATOM | 471 | O | CYS | C | 393 | 36.710 | −14.014 | −63.015 | 1.00 | 18.58 | O |
| ATOM | 472 | N | LYS | C | 394 | 34.787 | −15.157 | −63.253 | 1.00 | 17.98 | N |
| ATOM | 473 | CA | LYS | C | 394 | 35.438 | −16.424 | −63.541 | 1.00 | 23.56 | C |
| ATOM | 474 | CB | LYS | C | 394 | 34.364 | −17.532 | −63.548 | 1.00 | 27.76 | C |
| ATOM | 475 | CG | LYS | C | 394 | 34.845 | −18.958 | −63.613 | 1.00 | 41.83 | C |
| ATOM | 476 | CD | LYS | C | 394 | 33.660 | −19.891 | −63.908 | 1.00 | 47.55 | C |
| ATOM | 477 | CE | LYS | C | 394 | 32.862 | −19.442 | −65.137 | 1.00 | 41.86 | C |
| ATOM | 478 | NZ | LYS | C | 394 | 31.606 | −20.233 | −65.363 | 1.00 | 43.14 | N |
| ATOM | 479 | C | LYS | C | 394 | 36.180 | −16.400 | −64.892 | 1.00 | 22.67 | C |
| ATOM | 480 | O | LYS | C | 394 | 37.080 | −17.202 | −65.116 | 1.00 | 21.73 | O |
| ATOM | 481 | N | ILE | C | 395 | 35.790 | −15.478 | −65.769 | 1.00 | 17.90 | N |
| ATOM | 482 | CA | ILE | C | 395 | 36.266 | −15.458 | −67.157 | 1.00 | 20.16 | C |
| ATOM | 483 | CB | ILE | C | 395 | 35.092 | −15.143 | −68.126 | 1.00 | 22.32 | C |
| ATOM | 484 | CG1 | ILE | C | 395 | 34.020 | −16.257 | −68.058 | 1.00 | 24.88 | C |
| ATOM | 485 | CD1 | ILE | C | 395 | 34.525 | −17.646 | −68.359 | 1.00 | 33.56 | C |
| ATOM | 486 | CG2 | ILE | C | 395 | 35.570 | −14.943 | −69.572 | 1.00 | 27.19 | C |
| ATOM | 487 | C | ILE | C | 395 | 37.442 | −14.482 | −67.372 | 1.00 | 21.30 | C |
| ATOM | 488 | O | ILE | C | 395 | 38.374 | −14.792 | −68.120 | 1.00 | 24.85 | O |
| ATOM | 489 | N | CYS | C | 396 | 37.406 | −13.319 | −66.710 | 1.00 | 20.00 | N |
| ATOM | 490 | CA | CYS | C | 396 | 38.417 | −12.260 | −66.938 | 1.00 | 20.82 | C |
| ATOM | 491 | CB | CYS | C | 396 | 37.798 | −11.084 | −67.726 | 1.00 | 19.94 | C |
| ATOM | 492 | SG | CYS | C | 396 | 36.779 | −9.967 | −66.712 | 1.00 | 20.32 | S |
| ATOM | 493 | C | CYS | C | 396 | 39.088 | −11.762 | −65.643 | 1.00 | 22.88 | C |
| ATOM | 494 | O | CYS | C | 396 | 39.968 | −10.914 | −65.684 | 1.00 | 19.43 | O |
| ATOM | 495 | N | ALA | C | 397 | 38.662 | −12.306 | −64.510 | 1.00 | 19.88 | N |
| ATOM | 496 | CA | ALA | C | 397 | 39.176 | −11.925 | −63.172 | 1.00 | 21.30 | C |
| ATOM | 497 | CB | ALA | C | 397 | 40.659 | −12.315 | −62.996 | 1.00 | 22.89 | C |
| ATOM | 498 | C | ALA | C | 397 | 38.927 | −10.466 | −62.728 | 1.00 | 19.34 | C |

TABLE 5-continued

Atomic coordinates for CRBN(TBD):Thalidomide (Murine protein)

| ATOM | 499 | O   | ALA | C | 397 | 39.516 | −10.023 | −61.741 | 1.00 | 21.70 | O |
| --- | --- | --- | --- | --- | --- | --- | --- | --- | --- | --- | --- |
| ATOM | 500 | N   | SER | C | 398 | 38.025 | −9.757  | −63.400 | 1.00 | 18.04 | N |
| ATOM | 501 | CA  | SER | C | 398 | 37.579 | −8.438  | −62.920 | 1.00 | 23.45 | C |
| ATOM | 502 | CB  | SER | C | 398 | 36.543 | −7.840  | −63.857 | 1.00 | 21.51 | C |
| ATOM | 503 | OG  | SER | C | 398 | 36.076 | −6.608  | −63.341 | 1.00 | 23.91 | O |
| ATOM | 504 | C   | SER | C | 398 | 36.999 | −8.544  | −61.487 | 1.00 | 24.26 | C |
| ATOM | 505 | O   | SER | C | 398 | 36.226 | −9.429  | −61.204 | 1.00 | 19.04 | O |
| ATOM | 506 | N   | HIS | C | 399 | 37.407 | −7.647  | −60.599 | 1.00 | 21.06 | N |
| ATOM | 507 | CA  | HIS | C | 399 | 36.880 | −7.621  | −59.230 | 1.00 | 25.19 | C |
| ATOM | 508 | CB  | HIS | C | 399 | 37.830 | −6.845  | −58.303 | 1.00 | 29.97 | C |
| ATOM | 509 | CG  | HIS | C | 399 | 39.092 | −7.597  | −57.962 | 1.00 | 41.61 | C |
| ATOM | 510 | ND1 | HIS | C | 399 | 39.824 | −8.266  | −58.897 | 1.00 | 52.11 | N |
| ATOM | 511 | CE1 | HIS | C | 399 | 40.886 | −8.848  | −58.300 | 1.00 | 50.81 | C |
| ATOM | 512 | NE2 | HIS | C | 399 | 40.839 | −8.557  | −56.984 | 1.00 | 55.23 | N |
| ATOM | 513 | CD2 | HIS | C | 399 | 39.750 | −7.784  | −56.742 | 1.00 | 45.49 | C |
| ATOM | 514 | C   | HIS | C | 399 | 35.516 | −7.011  | −59.235 | 1.00 | 22.54 | C |
| ATOM | 515 | O   | HIS | C | 399 | 35.367 | −5.810  | −59.369 | 1.00 | 27.75 | O |
| ATOM | 516 | N   | ILE | C | 400 | 34.484 | −7.842  | −59.166 | 1.00 | 19.81 | N |
| ATOM | 517 | CA  | ILE | C | 400 | 33.158 | −7.334  | −59.359 | 1.00 | 18.67 | C |
| ATOM | 518 | CB  | ILE | C | 400 | 32.291 | −8.317  | −60.151 | 1.00 | 24.31 | C |
| ATOM | 519 | CG1 | ILE | C | 400 | 32.836 | −8.386  | −61.594 | 1.00 | 26.52 | C |
| ATOM | 520 | CD1 | ILE | C | 400 | 32.688 | −9.737  | −62.197 | 1.00 | 36.38 | C |
| ATOM | 521 | CG2 | ILE | C | 400 | 30.843 | −7.847  | −60.194 | 1.00 | 23.19 | C |
| ATOM | 522 | C   | ILE | C | 400 | 32.518 | −6.936  | −58.025 | 1.00 | 19.05 | C |
| ATOM | 523 | O   | ILE | C | 400 | 31.734 | −6.001  | −57.982 | 1.00 | 20.48 | O |
| ATOM | 524 | N   | GLY | C | 401 | 32.897 | −7.619  | −56.955 | 1.00 | 19.04 | N |
| ATOM | 525 | CA  | GLY | C | 401 | 32.429 | −7.264  | −55.592 | 1.00 | 17.46 | C |
| ATOM | 526 | C   | GLY | C | 401 | 32.840 | −8.296  | −54.568 | 1.00 | 20.64 | C |
| ATOM | 527 | O   | GLY | C | 401 | 33.973 | −8.783  | −54.588 | 1.00 | 18.56 | O |
| ATOM | 528 | N   | TRP | C | 402 | 31.890 | −8.661  | −53.680 | 1.00 | 16.67 | N |
| ATOM | 529 | CA  | TRP | C | 402 | 32.162 | −9.552  | −52.547 | 1.00 | 18.77 | C |
| ATOM | 530 | CB  | TRP | C | 402 | 32.456 | −8.725  | −51.273 | 1.00 | 17.10 | C |
| ATOM | 531 | CG  | TRP | C | 402 | 33.579 | −7.724  | −51.486 | 1.00 | 18.87 | C |
| ATOM | 532 | CD1 | TRP | C | 402 | 34.927 | −7.887  | −51.170 | 1.00 | 19.24 | C |
| ATOM | 533 | NE1 | TRP | C | 402 | 35.653 | −6.796  | −51.582 | 1.00 | 21.70 | N |
| ATOM | 534 | CE2 | TRP | C | 402 | 34.836 | −5.873  | −52.154 | 1.00 | 20.62 | C |
| ATOM | 535 | CD2 | TRP | C | 402 | 33.487 | −6.414  | −52.123 | 1.00 | 17.20 | C |
| ATOM | 536 | CE3 | TRP | C | 402 | 32.439 | −5.661  | −52.680 | 1.00 | 19.43 | C |
| ATOM | 537 | CZ3 | TRP | C | 402 | 32.744 | −4.408  | −53.245 | 1.00 | 21.99 | C |
| ATOM | 538 | CH2 | TRP | C | 402 | 34.052 | −3.897  | −53.225 | 1.00 | 21.39 | C |
| ATOM | 539 | CZ2 | TRP | C | 402 | 35.122 | −4.628  | −52.702 | 1.00 | 20.52 | C |
| ATOM | 540 | C   | TRP | C | 402 | 31.000 | −10.459 | −52.270 | 1.00 | 17.94 | C |
| ATOM | 541 | O   | TRP | C | 402 | 29.849 | −10.077 | −52.475 | 1.00 | 18.07 | O |
| ATOM | 542 | N   | LYS | C | 403 | 31.286 | −11.641 | −51.739 | 1.00 | 18.13 | N |
| ATOM | 543 | CA  | LYS | C | 403 | 30.236 | −12.459 | −51.130 | 1.00 | 16.95 | C |
| ATOM | 544 | CB  | LYS | C | 403 | 30.569 | −13.920 | −51.273 | 1.00 | 18.86 | C |
| ATOM | 545 | CG  | LYS | C | 403 | 29.489 | −14.897 | −50.782 | 1.00 | 22.97 | C |
| ATOM | 546 | CD  | LYS | C | 403 | 29.997 | −16.361 | −50.914 | 1.00 | 23.46 | C |
| ATOM | 547 | CE  | LYS | C | 403 | 28.848 | −17.393 | −50.801 | 1.00 | 28.58 | C |
| ATOM | 548 | NZ  | LYS | C | 403 | 29.373 | −18.801 | −50.910 | 1.00 | 29.32 | N |
| ATOM | 549 | C   | LYS | C | 403 | 30.205 | −12.083 | −49.655 | 1.00 | 18.92 | C |
| ATOM | 550 | O   | LYS | C | 403 | 31.241 | −12.073 | −49.003 | 1.00 | 20.66 | O |
| ATOM | 551 | N   | PHE | C | 404 | 29.025 | −11.762 | −49.150 | 1.00 | 16.91 | N |
| ATOM | 552 | CA  | PHE | C | 404 | 28.840 | −11.459 | −47.751 | 1.00 | 16.49 | C |
| ATOM | 553 | CB  | PHE | C | 404 | 27.987 | −10.196 | −47.598 | 1.00 | 16.81 | C |
| ATOM | 554 | CG  | PHE | C | 404 | 28.759 | −8.930  | −47.859 | 1.00 | 19.51 | C |
| ATOM | 555 | CD1 | PHE | C | 404 | 29.562 | −8.366  | −46.848 | 1.00 | 20.30 | C |
| ATOM | 556 | CE1 | PHE | C | 404 | 30.311 | −7.195  | −47.094 | 1.00 | 18.87 | C |
| ATOM | 557 | CZ  | PHE | C | 404 | 30.286 | −6.616  | −43.353 | 1.00 | 18.27 | C |
| ATOM | 558 | CE2 | PHE | C | 404 | 29.505 | −7.192  | −49.378 | 1.00 | 18.70 | C |
| ATOM | 559 | CD2 | PHE | C | 404 | 28.752 | −8.336  | −49.130 | 1.00 | 18.09 | C |
| ATOM | 560 | C   | PHE | C | 404 | 28.179 | −12.619 | −47.053 | 1.00 | 21.35 | C |
| ATOM | 561 | O   | PHE | C | 404 | 27.173 | −13.108 | −47.525 | 1.00 | 19.54 | O |
| ATOM | 562 | N   | THR | C | 405 | 28.790 | −13.100 | −45.966 | 1.00 | 17.15 | N |
| ATOM | 563 | CA  | THR | C | 405 | 28.253 | −14.252 | −45.217 | 1.00 | 19.24 | C |
| ATOM | 564 | CB  | THR | C | 405 | 29.225 | −15.467 | −45.263 | 1.00 | 23.03 | C |
| ATOM | 565 | OG1 | THR | C | 405 | 30.565 | −15.033 | −44.985 | 1.00 | 24.85 | O |
| ATOM | 566 | CG2 | THR | C | 405 | 29.185 | −16.138 | −46.643 | 1.00 | 24.42 | C |
| ATOM | 567 | C   | THR | C | 405 | 27.989 | −13.886 | −43.753 | 1.00 | 26.02 | C |
| ATOM | 568 | O   | THR | C | 405 | 28.837 | −13.247 | −43.115 | 1.00 | 20.95 | O |
| ATOM | 569 | N   | ALA | C | 406 | 26.822 | −14.301 | −43.228 | 1.00 | 22.39 | N |
| ATOM | 570 | CA  | ALA | C | 406 | 26.368 | −13.939 | −41.867 | 1.00 | 21.73 | C |
| ATOM | 571 | CB  | ALA | C | 406 | 24.938 | −14.456 | −41.645 | 1.00 | 19.03 | C |
| ATOM | 572 | C   | ALA | C | 406 | 27.296 | −14.572 | −40.840 | 1.00 | 24.62 | C |
| ATOM | 573 | O   | ALA | C | 406 | 27.635 | −15.733 | −40.968 | 1.00 | 22.12 | O |
| ATOM | 574 | N   | THR | C | 407 | 27.689 | −13.808 | −39.813 | 1.00 | 23.76 | N |
| ATOM | 575 | CA  | THR | C | 407 | 28.450 | −14.369 | −38.700 | 1.00 | 26.36 | C |
| ATOM | 576 | CB  | THR | C | 407 | 29.275 | −13.287 | −37.981 | 1.00 | 25.54 | C |

TABLE 5-continued

Atomic coordinates for CRBN(TBD):Thalidomide (Murine protein)

| ATOM | 577 | OG1 | THR | C | 407 | 28.393 | −12.261 | −37.548 | 1.00 | 24.00 | O |
| --- | --- | --- | --- | --- | --- | --- | --- | --- | --- | --- | --- |
| ATOM | 578 | CG2 | THR | C | 407 | 30.320 | −12.688 | −38.921 | 1.00 | 26.73 | C |
| ATOM | 579 | C | THR | C | 407 | 27.565 | −15.069 | −37.646 | 1.00 | 28.21 | C |
| ATOM | 580 | O | THR | C | 407 | 28.080 | −15.804 | −36.813 | 1.00 | 31.23 | O |
| ATOM | 581 | N | LYS | C | 408 | 26.249 | −14.819 | −37.677 | 1.00 | 29.81 | N |
| ATOM | 582 | CA | LYS | C | 408 | 25.294 | −15.479 | −36.740 | 1.00 | 30.93 | C |
| ATOM | 583 | CB | LYS | C | 408 | 24.672 | −14.460 | −35.776 | 1.00 | 30.17 | C |
| ATOM | 584 | CG | LYS | C | 408 | 25.642 | −13.846 | −34.750 | 1.00 | 40.43 | C |
| ATOM | 585 | CD | LYS | C | 408 | 26.527 | −14.894 | −34.057 | 1.00 | 49.28 | C |
| ATOM | 586 | CE | LYS | C | 408 | 25.775 | −15.671 | −32.974 | 1.00 | 61.81 | C |
| ATOM | 587 | NZ | LYS | C | 408 | 26.354 | −15.481 | −31.613 | 1.00 | 73.95 | N |
| ATOM | 588 | C | LYS | C | 408 | 24.180 | −16.212 | −37.479 | 1.00 | 31.23 | C |
| ATOM | 589 | O | LYS | C | 408 | 23.667 | −15.723 | −38.489 | 1.00 | 24.35 | O |
| ATOM | 590 | N | LYS | C | 409 | 23.775 | −17.357 | −36.944 | 1.00 | 29.82 | N |
| ATOM | 591 | CA | LYS | C | 409 | 22.792 | −18.221 | −37.602 | 1.00 | 30.44 | C |
| ATOM | 592 | CB | LYS | C | 409 | 22.754 | −19.590 | −36.923 | 1.00 | 41.17 | C |
| ATOM | 593 | CG | LYS | C | 409 | 24.120 | −20.235 | −36.715 | 1.00 | 52.84 | C |
| ATOM | 594 | CD | LYS | C | 409 | 24.343 | −21.420 | −37.634 | 1.00 | 51.99 | C |
| ATOM | 595 | CE | LYS | C | 409 | 24.663 | −20.968 | −39.044 | 1.00 | 49.47 | C |
| ATOM | 596 | NZ | LYS | C | 409 | 24.404 | −22.062 | −40.012 | 1.00 | 64.48 | N |
| ATOM | 597 | C | LYS | C | 409 | 21.396 | −17.640 | −37.643 | 1.00 | 26.60 | C |
| ATOM | 598 | O | LYS | C | 409 | 20.559 | −18.083 | −38.440 | 1.00 | 29.24 | O |
| ATOM | 599 | N | ASP | C | 410 | 21.111 | −16.663 | −36.786 | 1.00 | 24.16 | N |
| ATOM | 600 | CA | ASP | C | 410 | 19.737 | −16.101 | −36.726 | 1.00 | 28.97 | C |
| ATOM | 601 | CB | ASP | C | 410 | 19.386 | −15.652 | −35.291 | 1.00 | 36.10 | C |
| ATOM | 602 | CG | ASP | C | 410 | 20.260 | −14.478 | −34.803 | 1.00 | 50.41 | C |
| ATOM | 603 | OD1 | ASP | C | 410 | 21.246 | −14.118 | −35.494 | 1.00 | 52.57 | O |
| ATOM | 604 | OD2 | ASP | C | 410 | 19.953 | −13.914 | −33.731 | 1.00 | 59.08 | O |
| ATOM | 605 | C | ASP | C | 410 | 19.447 | −14.974 | −37.755 | 1.00 | 29.67 | C |
| ATOM | 606 | O | ASP | C | 410 | 18.320 | −14.463 | −37.825 | 1.00 | 30.30 | O |
| ATOM | 607 | N | MET | C | 411 | 20.459 | −14.590 | −38.546 | 1.00 | 22.42 | N |
| ATOM | 608 | CA | MET | C | 411 | 20.297 | −13.530 | −39.565 | 1.00 | 24.51 | C |
| ATOM | 609 | CB | MET | C | 411 | 21.646 | −12.864 | −39.835 | 1.00 | 25.24 | C |
| ATOM | 610 | CG | MET | C | 411 | 22.235 | −12.210 | −38.578 | 1.00 | 28.71 | C |
| ATOM | 611 | SD | MET | C | 411 | 23.976 | −11.852 | −38.825 | 1.00 | 27.69 | S |
| ATOM | 612 | CE | MET | C | 411 | 23.819 | −10.572 | −40.083 | 1.00 | 28.09 | C |
| ATOM | 613 | C | MET | C | 411 | 19.691 | −14.032 | −40.910 | 1.00 | 19.94 | C |
| ATOM | 614 | O | MET | C | 411 | 19.848 | −15.198 | −41.275 | 1.00 | 22.66 | O |
| ATOM | 615 | N | SER | C | 412 | 19.002 | −13.146 | −41.616 | 1.00 | 19.30 | N |
| ATOM | 616 | CA | SER | C | 412 | 18.581 | −13.434 | −42.985 | 1.00 | 21.53 | C |
| ATOM | 617 | CB | SER | C | 412 | 17.070 | −13.755 | −43.090 | 1.00 | 23.43 | C |
| ATOM | 618 | OG | SER | C | 412 | 16.266 | −12.675 | −42.707 | 1.00 | 25.81 | O |
| ATOM | 619 | C | SER | C | 412 | 19.037 | −12.343 | −43.933 | 1.00 | 22.36 | C |
| ATOM | 620 | O | SER | C | 412 | 18.874 | −11.164 | −43.600 | 1.00 | 19.15 | O |
| ATOM | 621 | N | PRO | C | 413 | 19.174 | −12.700 | −45.220 | 1.00 | 19.34 | N |
| ATOM | 622 | CA | PRO | C | 413 | 19.897 | −13.867 | −45.702 | 1.00 | 18.19 | C |
| ATOM | 623 | CB | PRO | C | 413 | 20.169 | −13.524 | −47.170 | 1.00 | 20.62 | C |
| ATOM | 624 | CG | PRO | C | 413 | 20.428 | −12.049 | −47.133 | 1.00 | 20.02 | C |
| ATOM | 625 | CD | PRO | C | 413 | 19.526 | −11.496 | −46.018 | 1.00 | 19.00 | C |
| ATOM | 626 | C | PRO | C | 413 | 21.161 | −14.229 | −44.980 | 1.00 | 19.66 | C |
| ATOM | 627 | O | PRO | C | 413 | 21.871 | −13.343 | −44.477 | 1.00 | 18.72 | O |
| ATOM | 628 | N | GLN | C | 414 | 21.460 | −15.530 | −44.952 | 1.00 | 17.84 | N |
| ATOM | 629 | CA | GLN | C | 414 | 22.714 | −16.019 | −44.415 | 1.00 | 18.92 | C |
| ATOM | 630 | CB | GLN | C | 414 | 22.674 | −17.559 | −44.251 | 1.00 | 22.91 | C |
| ATOM | 631 | CG | GLN | C | 414 | 21.942 | −18.013 | −42.971 | 1.00 | 22.25 | C |
| ATOM | 632 | CD | GLN | C | 414 | 22.702 | −17.596 | −41.718 | 1.00 | 21.57 | C |
| ATOM | 633 | OE1 | GLN | C | 414 | 22.292 | −16.687 | −40.978 | 1.00 | 24.32 | O |
| ATOM | 634 | NE2 | GLN | C | 414 | 23.807 | −18.207 | −41.514 | 1.00 | 17.55 | N |
| ATOM | 635 | C | GLN | C | 414 | 23.880 | −15.617 | −45.325 | 1.00 | 20.42 | C |
| ATOM | 636 | O | GLN | C | 414 | 25.029 | −15.627 | −44.907 | 1.00 | 19.54 | O |
| ATOM | 637 | N | LYS | C | 415 | 23.580 | −15.330 | −46.587 | 1.00 | 17.15 | N |
| ATOM | 638 | CA | LYS | C | 415 | 24.607 | −14.837 | −47.502 | 1.00 | 20.13 | C |
| ATOM | 639 | CB | LYS | C | 415 | 25.524 | −15.968 | −48.033 | 1.00 | 28.49 | C |
| ATOM | 640 | CG | LYS | C | 415 | 24.997 | −16.768 | −49.202 | 1.00 | 29.92 | C |
| ATOM | 641 | CD | LYS | C | 415 | 25.210 | −16.048 | −50.534 | 1.00 | 23.94 | C |
| ATOM | 642 | CE | LYS | C | 415 | 24.598 | −16.837 | −51.667 | 1.00 | 32.53 | C |
| ATOM | 643 | NZ | LYS | C | 415 | 23.775 | −17.966 | −51.145 | 1.00 | 24.42 | N |
| ATOM | 644 | C | LYS | C | 415 | 23.982 | −14.040 | −48.614 | 1.00 | 17.08 | C |
| ATOM | 645 | O | LYS | C | 415 | 22.807 | −14.210 | −48.934 | 1.00 | 15.14 | O |
| ATOM | 646 | N | PHE | C | 416 | 24.757 | −13.120 | −49.173 | 1.00 | 15.09 | N |
| ATOM | 647 | CA | PHE | C | 416 | 24.302 | −12.371 | −50.332 | 1.00 | 14.01 | C |
| ATOM | 648 | CB | PHE | C | 416 | 23.323 | −11.233 | −49.936 | 1.00 | 14.25 | C |
| ATOM | 649 | CG | PHE | C | 416 | 23.941 | −10.160 | −49.092 | 1.00 | 17.62 | C |
| ATOM | 650 | CD2 | PHE | C | 416 | 24.520 | −9.016 | −49.690 | 1.00 | 16.75 | C |
| ATOM | 651 | CE2 | PHE | C | 416 | 25.121 | −8.038 | −48.898 | 1.00 | 15.95 | C |
| ATOM | 652 | CZ | PHE | C | 416 | 25.155 | −8.166 | −47.506 | 1.00 | 17.92 | C |
| ATOM | 653 | CE1 | PHE | C | 416 | 24.598 | −9.276 | −46.901 | 1.00 | 19.40 | C |
| ATOM | 654 | CD1 | PHE | C | 416 | 24.004 | −10.289 | −47.696 | 1.00 | 18.32 | C |

TABLE 5-continued

Atomic coordinates for CRBN(TBD):Thalidomide (Murine protein)

| ATOM | 655 | C | PHE | C | 416 | 25.565 | −11.854 | −51.039 | 1.00 | 14.42 | C |
|---|---|---|---|---|---|---|---|---|---|---|---|
| ATOM | 656 | O | PHE | C | 416 | 26.688 | −12.146 | −50.604 | 1.00 | 16.22 | O |
| ATOM | 657 | N | TRP | C | 417 | 25.378 | −11.209 | −52.161 | 1.00 | 15.71 | N |
| ATOM | 658 | CA | TRP | C | 417 | 26.493 | −10.641 | −52.897 | 1.00 | 15.70 | C |
| ATOM | 659 | CB | TRP | C | 417 | 26.488 | −11.186 | −54.339 | 1.00 | 17.05 | C |
| ATOM | 660 | CG | TRP | C | 417 | 26.539 | −12.704 | −54.391 | 1.00 | 15.37 | C |
| ATOM | 661 | CD1 | TRP | C | 417 | 25.463 | −13.599 | −54.295 | 1.00 | 16.48 | C |
| ATOM | 662 | NE1 | TRP | C | 417 | 25.910 | −14.902 | −54.342 | 1.00 | 17.26 | N |
| ATOM | 663 | CE2 | TRP | C | 417 | 27.263 | −14.930 | −54.492 | 1.00 | 17.73 | C |
| ATOM | 664 | CD2 | TRP | C | 417 | 27.729 | −13.544 | −54.511 | 1.00 | 14.96 | C |
| ATOM | 665 | CE3 | TRP | C | 417 | 29.090 | −13.292 | −54.645 | 1.00 | 15.98 | C |
| ATOM | 666 | CZ3 | TRP | C | 417 | 29.956 | −14.360 | −54.752 | 1.00 | 17.30 | C |
| ATOM | 667 | CH2 | TRP | C | 417 | 29.482 | −15.700 | −54.739 | 1.00 | 18.29 | C |
| ATOM | 668 | CZ2 | TRP | C | 417 | 28.129 | −15.994 | −54.590 | 1.00 | 17.76 | C |
| ATOM | 669 | C | TRP | C | 417 | 26.376 | −9.153 | −52.902 | 1.00 | 16.99 | C |
| ATOM | 670 | O | TRP | C | 417 | 25.328 | −8.621 | −53.214 | 1.00 | 17.97 | O |
| ATOM | 671 | N | GLY | C | 418 | 27.458 | −8.461 | −52.557 | 1.00 | 18.07 | N |
| ATOM | 672 | CA | GLY | C | 418 | 27.504 | −7.005 | −52.736 | 1.00 | 15.90 | C |
| ATOM | 673 | C | GLY | C | 418 | 28.404 | −6.681 | −53.930 | 1.00 | 17.29 | C |
| ATOM | 674 | O | GLY | C | 418 | 29.602 | −6.999 | −53.927 | 1.00 | 18.19 | O |
| ATOM | 675 | N | LEU | C | 419 | 27.814 | −6.126 | −54.964 | 1.00 | 16.90 | N |
| ATOM | 676 | CA | LEU | C | 419 | 28.512 | −5.984 | −56.235 | 1.00 | 18.19 | C |
| ATOM | 677 | CB | LEU | C | 419 | 27.727 | −6.670 | −57.360 | 1.00 | 18.51 | C |
| ATOM | 678 | CG | LEU | C | 419 | 27.373 | −8.152 | −57.100 | 1.00 | 15.00 | C |
| ATOM | 679 | CD1 | LEU | C | 419 | 26.518 | −8.685 | −58.276 | 1.00 | 22.36 | C |
| ATOM | 680 | CD2 | LEU | C | 419 | 28.638 | −8.998 | −56.948 | 1.00 | 18.73 | C |
| ATOM | 681 | C | LEU | C | 419 | 28.693 | −4.513 | −56.547 | 1.00 | 19.38 | C |
| ATOM | 682 | O | LEU | C | 419 | 27.799 | −3.700 | −56.322 | 1.00 | 20.12 | O |
| ATOM | 683 | N | THR | C | 420 | 29.860 | −4.184 | −57.079 | 1.00 | 20.93 | N |
| ATOM | 684 | CA | THR | C | 420 | 30.126 | −2.798 | −57.508 | 1.00 | 21.16 | C |
| ATOM | 685 | CB | THR | C | 420 | 31.626 | −2.601 | −57.689 | 1.00 | 20.72 | C |
| ATOM | 686 | OG1 | THR | C | 420 | 32.267 | −2.919 | −56.460 | 1.00 | 21.86 | O |
| ATOM | 687 | CG2 | THR | C | 420 | 31.941 | −1.142 | −58.061 | 1.00 | 25.37 | C |
| ATOM | 688 | C | THR | C | 420 | 29.384 | −2.496 | −58.792 | 1.00 | 18.26 | C |
| ATOM | 689 | O | THR | C | 420 | 29.657 | −3.118 | −59.827 | 1.00 | 20.69 | O |
| ATOM | 690 | N | ARG | C | 421 | 28.425 | −1.562 | −58.734 | 1.00 | 18.70 | N |
| ATOM | 691 | CA | ARG | C | 421 | 27.495 | −1.329 | −59.842 | 1.00 | 24.01 | C |
| ATOM | 692 | CB | ARG | C | 421 | 26.450 | −0.272 | −59.453 | 1.00 | 24.40 | C |
| ATOM | 693 | CG | ARG | C | 421 | 25.344 | −0.063 | −60.487 | 1.00 | 29.73 | C |
| ATOM | 694 | CD | ARG | C | 421 | 24.643 | −1.373 | −60.859 | 1.00 | 40.72 | C |
| ATOM | 695 | NE | ARG | C | 421 | 23.762 | −1.234 | −62.020 | 1.00 | 43.02 | N |
| ATOM | 696 | CZ | ARG | C | 421 | 24.160 | −1.331 | −63.288 | 1.00 | 44.26 | C |
| ATOM | 697 | NH1 | ARG | C | 421 | 23.282 | −1.182 | −64.267 | 1.00 | 51.63 | N |
| ATOM | 698 | NH2 | ARG | C | 421 | 25.435 | −1.571 | −63.578 | 1.00 | 37.17 | N |
| ATOM | 699 | C | ARG | C | 421 | 28.224 | −0.927 | −61.142 | 1.00 | 23.35 | C |
| ATOM | 700 | O | ARG | C | 421 | 27.842 | −1.322 | −62.246 | 1.00 | 21.27 | O |
| ATOM | 701 | N | SER | C | 422 | 29.294 | −0.169 | −60.998 | 1.00 | 25.80 | N |
| ATOM | 702 | CA | SER | C | 422 | 30.024 | 0.303 | −62.169 | 1.00 | 25.90 | C |
| ATOM | 703 | CB | SER | C | 422 | 30.898 | 1.501 | −61.785 | 1.00 | 26.05 | C |
| ATOM | 704 | OG | SER | C | 422 | 31.809 | 1.122 | −60.780 | 1.00 | 27.22 | O |
| ATOM | 705 | C | SER | C | 422 | 30.877 | −0.814 | −62.793 | 1.00 | 24.71 | C |
| ATOM | 706 | O | SER | C | 422 | 31.435 | −0.629 | −63.873 | 1.00 | 24.39 | O |
| ATOM | 707 | N | ALA | C | 423 | 31.003 | −1.955 | −62.103 | 1.00 | 19.01 | N |
| ATOM | 708 | CA | ALA | C | 423 | 31.690 | −3.120 | −62.679 | 1.00 | 22.75 | C |
| ATOM | 709 | CB | ALA | C | 423 | 32.421 | −3.930 | −61.583 | 1.00 | 22.48 | C |
| ATOM | 710 | C | ALA | C | 423 | 30.735 | −4.009 | −63.505 | 1.00 | 22.65 | C |
| ATOM | 711 | O | ALA | C | 423 | 31.144 | −5.036 | −64.076 | 1.00 | 22.56 | O |
| ATOM | 712 | N | LEU | C | 424 | 29.470 | −3.609 | −63.584 | 1.00 | 19.91 | N |
| ATOM | 713 | CA | LEU | C | 424 | 28.470 | −4.380 | −64.309 | 1.00 | 20.15 | C |
| ATOM | 714 | CB | LEU | C | 424 | 27.345 | −4.849 | −63.365 | 1.00 | 20.70 | C |
| ATOM | 715 | CG | LEU | C | 424 | 27.798 | −5.765 | −62.210 | 1.00 | 21.77 | C |
| ATOM | 716 | CD1 | LEU | C | 424 | 26.661 | −5.860 | −61.188 | 1.00 | 22.15 | C |
| ATOM | 717 | CD2 | LEU | C | 424 | 28.145 | −7.152 | −62.719 | 1.00 | 20.26 | C |
| ATOM | 718 | C | LEU | C | 424 | 27.866 | −3.624 | −65.455 | 1.00 | 24.37 | C |
| ATOM | 719 | O | LEU | C | 424 | 27.809 | −2.387 | −65.443 | 1.00 | 23.14 | O |
| ATOM | 720 | N | LEU | C | 425 | 27.317 | −4.386 | −66.389 | 1.00 | 24.58 | N |
| ATOM | 721 | CA | LEU | C | 425 | 26.871 | −3.873 | −67.650 | 1.00 | 28.23 | C |
| ATOM | 722 | CB | LEU | C | 425 | 27.747 | −4.461 | −68.760 | 1.00 | 33.87 | C |
| ATOM | 723 | CG | LEU | C | 425 | 27.622 | −3.891 | −70.155 | 1.00 | 43.65 | C |
| ATOM | 724 | CD1 | LEU | C | 425 | 28.279 | −2.516 | −70.204 | 1.00 | 36.35 | C |
| ATOM | 725 | CD2 | LEU | C | 425 | 28.254 | −4.868 | −71.148 | 1.00 | 30.51 | C |
| ATOM | 726 | C | LEU | C | 425 | 25.385 | −4.138 | −67.976 | 1.00 | 46.90 | C |
| ATOM | 727 | O | LEU | C | 425 | 25.026 | −5.251 | −68.379 | 1.00 | 57.13 | O |
| ATOM | 728 | N | PRO | C | 426 | 24.515 | −3.188 | −67.612 | 1.00 | 36.98 | N |
| ATOM | 729 | CA | PRO | C | 426 | 24.072 | −2.174 | −68.552 | 1.00 | 49.43 | C |
| ATOM | 730 | CB | PRO | C | 426 | 22.532 | −2.216 | −68.434 | 1.00 | 43.05 | C |
| ATOM | 731 | CG | PRO | C | 426 | 22.234 | −3.445 | −67.638 | 1.00 | 47.02 | C |
| ATOM | 732 | CD | PRO | C | 426 | 23.413 | −3.577 | −66.731 | 1.00 | 61.94 | C |

TABLE 5-continued

Atomic coordinates for CRBN(TBD):Thalidomide (Murine protein)

| ATOM | 733 | C | PRO | C | 426 | 24.632 | −0.823 | −68.063 | 1.00 | 67.43 | C |
|---|---|---|---|---|---|---|---|---|---|---|---|
| ATOM | 734 | O | PRO | C | 426 | 25.051 | −0.715 | −66.893 | 1.00 | 58.16 | O |
| ATOM | 735 | N | THR | C | 427 | 24.659 | 0.174 | −68.952 | 1.00 | 78.64 | N |
| ATOM | 736 | CA | THR | C | 427 | 25.321 | 1.477 | −68.704 | 1.00 | 73.20 | C |
| ATOM | 737 | CB | THR | C | 427 | 24.547 | 2.648 | −69.376 | 1.00 | 83.46 | C |
| ATOM | 738 | OG1 | THR | C | 427 | 24.019 | 2.219 | −70.641 | 1.00 | 82.68 | O |
| ATOM | 739 | CG2 | THR | C | 427 | 25.465 | 3.859 | −69.596 | 1.00 | 75.73 | C |
| ATOM | 740 | C | THR | C | 427 | 25.573 | 1.783 | −67.219 | 1.00 | 69.85 | C |
| ATOM | 741 | O | THR | C | 427 | 24.930 | 2.651 | −66.625 | 1.00 | 72.74 | O |
| ATOM | 742 | N | THR | A | 321 | 4.551 | −15.893 | −65.318 | 1.00 | 40.43 | N |
| ATOM | 743 | CA | THR | A | 321 | 5.957 | −16.283 | −64.916 | 1.00 | 35.08 | C |
| ATOM | 744 | CB | THR | A | 321 | 6.662 | −15.217 | −64.026 | 1.00 | 40.21 | C |
| ATOM | 745 | OG1 | THR | A | 321 | 6.151 | −15.287 | −62.681 | 1.00 | 36.05 | O |
| ATOM | 746 | CG2 | THR | A | 321 | 6.511 | −13.784 | −64.607 | 1.00 | 45.57 | C |
| ATOM | 747 | C | THR | A | 321 | 6.086 | −17.660 | −64.202 | 1.00 | 26.92 | C |
| ATOM | 748 | O | THR | A | 321 | 7.182 | −18.122 | −64.015 | 1.00 | 21.10 | O |
| ATOM | 749 | N | SER | A | 322 | 4.966 | −18.271 | −63.787 | 1.00 | 22.22 | N |
| ATOM | 750 | CA | ASER | A | 322 | 4.980 | −19.619 | −63.228 | 0.50 | 20.83 | C |
| ATOM | 751 | CA | BSER | A | 322 | 4.979 | −19.642 | −63.240 | 0.50 | 20.81 | C |
| ATOM | 752 | CB | ASER | A | 322 | 3.603 | −19.944 | −62.624 | 0.50 | 23.57 | C |
| ATOM | 753 | CB | BSER | A | 322 | 3.606 | −20.013 | −62.662 | 0.50 | 23.10 | C |
| ATOM | 754 | OG | ASER | A | 322 | 3.576 | −21.241 | −62.093 | 0.50 | 20.43 | O |
| ATOM | 755 | OG | BSER | A | 322 | 3.461 | −19.505 | −61.365 | 0.50 | 20.90 | O |
| ATOM | 756 | C | SER | A | 322 | 5.337 | −20.661 | −64.298 | 1.00 | 22.53 | C |
| ATOM | 757 | O | SER | A | 322 | 4.727 | −20.695 | −65.374 | 1.00 | 24.80 | O |
| ATOM | 758 | N | LEU | A | 323 | 6.296 | −21.522 | −63.999 | 1.00 | 16.02 | N |
| ATOM | 759 | CA | LEU | A | 323 | 6.610 | −22.635 | −64.897 | 1.00 | 18.17 | C |
| ATOM | 760 | CB | LEU | A | 323 | 8.082 | −22.610 | −65.355 | 1.00 | 19.53 | C |
| ATOM | 761 | CG | LEU | A | 323 | 8.522 | −21.321 | −66.100 | 1.00 | 21.51 | C |
| ATOM | 762 | CD1 | LEU | A | 323 | 10.038 | −21.185 | −66.165 | 1.00 | 22.36 | C |
| ATOM | 763 | CD2 | LEU | A | 323 | 7.972 | −21.344 | −67.487 | 1.00 | 24.81 | C |
| ATOM | 764 | C | LEU | A | 323 | 6.239 | −23.963 | −64.241 | 1.00 | 18.39 | C |
| ATOM | 765 | O | LEU | A | 323 | 6.885 | −24.396 | −63.264 | 1.00 | 16.27 | O |
| ATOM | 766 | N | CYS | A | 324 | 5.183 | −24.593 | −64.761 | 1.00 | 16.53 | N |
| ATOM | 767 | CA | CYS | A | 324 | 4.579 | −25.796 | −64.126 | 1.00 | 17.38 | C |
| ATOM | 768 | CB | CYS | A | 324 | 3.057 | −25.648 | −64.099 | 1.00 | 21.85 | C |
| ATOM | 769 | SG | CYS | A | 324 | 2.560 | −24.369 | −62.948 | 1.00 | 24.08 | S |
| ATOM | 770 | C | CYS | A | 324 | 4.934 | −27.063 | −64.877 | 1.00 | 18.86 | C |
| ATOM | 771 | O | CYS | A | 324 | 5.230 | −27.015 | −66.074 | 1.00 | 17.93 | O |
| ATOM | 772 | N | CYS | A | 325 | 4.936 | −28.190 | −64.164 | 1.00 | 14.36 | N |
| ATOM | 773 | CA | CYS | A | 325 | 5.081 | −29.506 | −64.786 | 1.00 | 17.37 | C |
| ATOM | 774 | CB | CYS | A | 325 | 4.883 | −30.614 | −63.735 | 1.00 | 15.30 | C |
| ATOM | 775 | SG | CYS | A | 325 | 4.948 | −32.271 | −64.439 | 1.00 | 17.23 | S |
| ATOM | 776 | C | CYS | A | 325 | 4.002 | −29.629 | −65.879 | 1.00 | 18.91 | C |
| ATOM | 777 | O | CYS | A | 325 | 2.796 | −29.473 | −65.605 | 1.00 | 15.89 | O |
| ATOM | 778 | N | LYS | A | 326 | 4.424 | −29.942 | −67.092 | 1.00 | 17.65 | N |
| ATOM | 779 | CA | LYS | A | 326 | 3.494 | −30.047 | −68.241 | 1.00 | 19.82 | C |
| ATOM | 780 | CB | LYS | A | 326 | 4.308 | −30.252 | −69.552 | 1.00 | 21.78 | C |
| ATOM | 781 | CG | LYS | A | 326 | 3.455 | −30.439 | −70.820 | 1.00 | 27.83 | C |
| ATOM | 782 | CD | LYS | A | 326 | 4.306 | −30.420 | −72.113 | 1.00 | 21.59 | C |
| ATOM | 783 | CE | LYS | A | 326 | 5.133 | −31.707 | −72.261 | 1.00 | 33.76 | C |
| ATOM | 784 | NZ | LYS | A | 326 | 5.957 | −31.770 | −73.533 | 1.00 | 26.41 | N |
| ATOM | 785 | C | LYS | A | 326 | 2.482 | −31.224 | −68.056 | 1.00 | 21.44 | C |
| ATOM | 786 | O | LYS | A | 326 | 1.307 | −31.137 | −68.469 | 1.00 | 20.61 | O |
| ATOM | 787 | N | GLN | A | 327 | 2.957 | −32.290 | −67.431 | 1.00 | 17.27 | N |
| ATOM | 788 | CA | GLN | A | 327 | 2.209 | −33.507 | −67.259 | 1.00 | 20.63 | C |
| ATOM | 789 | CB | GLN | A | 327 | 3.140 | −34.661 | −66.835 | 1.00 | 19.02 | C |
| ATOM | 790 | CG | GLN | A | 327 | 2.402 | −35.976 | −66.562 | 1.00 | 19.78 | C |
| ATOM | 791 | CD | GLN | A | 327 | 1.568 | −36.397 | −67.748 | 1.00 | 24.09 | C |
| ATOM | 792 | OE1 | GLN | A | 327 | 2.065 | −36.435 | −68.865 | 1.00 | 23.94 | O |
| ATOM | 793 | NE2 | GLN | A | 327 | 0.290 | −36.713 | −67.514 | 1.00 | 22.24 | N |
| ATOM | 794 | C | GLN | A | 327 | 1.073 | −33.350 | −66.263 | 1.00 | 22.86 | C |
| ATOM | 795 | O | GLN | A | 327 | −0.083 | −33.491 | −66.629 | 1.00 | 19.94 | O |
| ATOM | 796 | N | CYS | A | 328 | 1.391 | −33.075 | −64.994 | 1.00 | 18.52 | N |
| ATOM | 797 | CA | CYS | A | 328 | 0.302 | −32.929 | −63.962 | 1.00 | 20.13 | C |
| ATOM | 798 | CB | CYS | A | 328 | 0.795 | −33.348 | −62.562 | 1.00 | 17.71 | C |
| ATOM | 799 | SG | CYS | A | 328 | 2.103 | −32.303 | −61.880 | 1.00 | 18.05 | S |
| ATOM | 800 | C | CYS | A | 328 | −0.317 | −31.535 | −63.932 | 1.00 | 21.52 | C |
| ATOM | 801 | O | CYS | A | 328 | −1.331 | −31.313 | −63.267 | 1.00 | 18.91 | O |
| ATOM | 802 | N | GLN | A | 329 | 0.311 | −30.594 | −64.652 | 1.00 | 17.87 | N |
| ATOM | 803 | CA | GLN | A | 329 | −0.242 | −29.243 | −64.918 | 1.00 | 21.29 | C |
| ATOM | 804 | CB | GLN | A | 329 | −1.667 | −29.332 | −65.562 | 1.00 | 21.81 | C |
| ATOM | 805 | CG | GLN | A | 329 | −1.680 | −30.200 | −66.809 | 1.00 | 20.31 | C |
| ATOM | 806 | CD | GLN | A | 329 | −3.074 | −30.352 | −67.423 | 1.00 | 24.94 | C |
| ATOM | 807 | OE1 | GLN | A | 329 | −3.462 | −31.435 | −67.849 | 1.00 | 31.31 | O |
| ATOM | 808 | NE2 | GLN | A | 329 | −3.826 | −29.283 | −67.429 | 1.00 | 27.47 | N |
| ATOM | 809 | C | GLN | A | 329 | −0.242 | −28.276 | −63.727 | 1.00 | 23.05 | C |
| ATOM | 810 | O | GLN | A | 329 | 0.013 | −27.081 | −63.897 | 1.00 | 27.20 | O |

TABLE 5-continued

Atomic coordinates for CRBN(TBD):Thalidomide (Murine protein)

| ATOM | 811 | N | GLU | A | 330 | −0.492 | −28.792 | −62.526 | 1.00 | 22.09 | N |
|---|---|---|---|---|---|---|---|---|---|---|---|
| ATOM | 812 | CA | GLU | A | 330 | −0.784 | −27.957 | −61.354 | 1.00 | 23.02 | C |
| ATOM | 813 | CB | GLU | A | 330 | −1.774 | −28.703 | −60.422 | 1.00 | 25.71 | C |
| ATOM | 814 | CG | GLU | A | 330 | −1.185 | −29.996 | −59.814 | 1.00 | 29.94 | C |
| ATOM | 815 | CD | GLU | A | 330 | −2.152 | −30.756 | −58.900 | 1.00 | 43.29 | C |
| ATOM | 816 | OE1 | GLU | A | 330 | −1.780 | −31.868 | −58.409 | 1.00 | 38.45 | O |
| ATOM | 817 | OE2 | GLU | A | 330 | −3.280 | −30.263 | −58.682 | 1.00 | 47.09 | O |
| ATOM | 818 | C | GLU | A | 330 | 0.481 | −27.630 | −60.530 | 1.00 | 24.14 | C |
| ATOM | 819 | O | GLU | A | 330 | 0.473 | −26.737 | −59.691 | 1.00 | 26.86 | O |
| ATOM | 820 | N | THR | A | 331 | 1.531 | −28.406 | −60.723 | 1.00 | 20.99 | N |
| ATOM | 821 | CA | THR | A | 331 | 2.680 | −28.355 | −59.816 | 1.00 | 16.99 | C |
| ATOM | 822 | CB | THR | A | 331 | 3.328 | −29.763 | −59.685 | 1.00 | 20.62 | C |
| ATOM | 823 | OG1 | THR | A | 331 | 2.320 | −30.714 | −59.261 | 1.00 | 22.37 | O |
| ATOM | 824 | CG2 | THR | A | 331 | 4.459 | −29.760 | −58.679 | 1.00 | 18.91 | C |
| ATOM | 825 | C | THR | A | 331 | 3.702 | −27.368 | −60.383 | 1.00 | 19.75 | C |
| ATOM | 826 | O | THR | A | 331 | 4.257 | −27.593 | −61.461 | 1.00 | 16.32 | O |
| ATOM | 827 | N | GLU | A | 332 | 3.964 | −26.294 | −59.655 | 1.00 | 16.74 | N |
| ATOM | 828 | CA | GLU | A | 332 | 4.926 | −25.315 | −60.131 | 1.00 | 15.89 | C |
| ATOM | 829 | CB | GLU | A | 332 | 4.728 | −23.977 | −59.441 | 1.00 | 20.69 | C |
| ATOM | 830 | CG | GLU | A | 332 | 5.675 | −22.891 | −59.976 | 1.00 | 20.54 | C |
| ATOM | 831 | CD | GLU | A | 332 | 5.504 | −21.578 | −59.238 | 1.00 | 21.74 | C |
| ATOM | 832 | OE1 | GLU | A | 332 | 4.552 | −20.819 | −59.570 | 1.00 | 22.95 | O |
| ATOM | 833 | OE2 | GLU | A | 332 | 6.296 | −21.334 | −58.305 | 1.00 | 21.04 | O |
| ATOM | 834 | C | GLU | A | 332 | 6.324 | −25.832 | −59.842 | 1.00 | 17.94 | C |
| ATOM | 835 | O | GLU | A | 332 | 6.620 | −26.316 | −58.714 | 1.00 | 13.91 | O |
| ATOM | 836 | N | ILE | A | 333 | 7.192 | −25.729 | −60.828 | 1.00 | 13.85 | N |
| ATOM | 837 | CA | ILE | A | 333 | 8.535 | −26.218 | −60.644 | 1.00 | 14.17 | C |
| ATOM | 838 | CB | ILE | A | 333 | 8.973 | −27.127 | −61.824 | 1.00 | 13.98 | C |
| ATOM | 839 | CG1 | ILE | A | 333 | 8.042 | −28.366 | −61.958 | 1.00 | 16.52 | C |
| ATOM | 840 | CD1 | ILE | A | 333 | 8.007 | −29.258 | −60.701 | 1.00 | 16.65 | C |
| ATOM | 841 | CG2 | ILE | A | 333 | 10.398 | −27.580 | −61.618 | 1.00 | 14.79 | C |
| ATOM | 842 | C | ILE | A | 333 | 9.512 | −25.052 | −60.493 | 1.00 | 16.43 | C |
| ATOM | 843 | O | ILE | A | 333 | 10.466 | −25.137 | −59.754 | 1.00 | 16.72 | O |
| ATOM | 844 | N | THR | A | 334 | 9.299 | −23.985 | −61.236 | 1.00 | 18.04 | N |
| ATOM | 845 | CA | THR | A | 334 | 10.163 | −22.794 | −61.057 | 1.00 | 18.02 | C |
| ATOM | 846 | CB | THR | A | 334 | 11.560 | −22.975 | −61.759 | 1.00 | 19.08 | C |
| ATOM | 847 | OG1 | THR | A | 334 | 12.452 | −21.942 | −61.322 | 1.00 | 17.19 | O |
| ATOM | 848 | CG2 | THR | A | 334 | 11.424 | −22.890 | −63.282 | 1.00 | 17.72 | C |
| ATOM | 849 | C | THR | A | 334 | 9.411 | −21.574 | −61.560 | 1.00 | 17.69 | C |
| ATOM | 850 | O | THR | A | 334 | 8.191 | −21.661 | −61.874 | 1.00 | 15.70 | O |
| ATOM | 851 | N | THR | A | 335 | 10.077 | −20.418 | −61.552 | 1.00 | 18.19 | N |
| ATOM | 852 | CA | THR | A | 335 | 9.504 | −19.215 | −62.107 | 1.00 | 17.81 | C |
| ATOM | 853 | CB | THR | A | 335 | 9.118 | −18.184 | −61.001 | 1.00 | 19.86 | C |
| ATOM | 854 | OG1 | THR | A | 335 | 10.299 | −17.548 | −60.507 | 1.00 | 20.96 | O |
| ATOM | 855 | CG2 | THR | A | 335 | 8.364 | −18.859 | −59.842 | 1.00 | 18.72 | C |
| ATOM | 856 | C | THR | A | 335 | 10.507 | −18.558 | −63.056 | 1.00 | 18.93 | C |
| ATOM | 857 | O | THR | A | 335 | 11.718 | −18.769 | −62.955 | 1.00 | 17.73 | O |
| ATOM | 858 | N | LYS | A | 336 | 10.000 | −17.749 | −63.969 | 1.00 | 17.52 | N |
| ATOM | 859 | CA | LYS | A | 336 | 10.877 | −17.054 | −64.887 | 1.00 | 20.23 | C |
| ATOM | 860 | CB | LYS | A | 336 | 10.056 | −16.251 | −65.886 | 1.00 | 24.57 | C |
| ATOM | 861 | CG | LYS | A | 336 | 9.315 | −17.096 | −66.900 | 1.00 | 34.21 | C |
| ATOM | 862 | CD | LYS | A | 336 | 8.522 | −16.200 | −67.851 | 1.00 | 39.66 | C |
| ATOM | 863 | CE | LYS | A | 336 | 8.113 | −16.955 | −69.112 | 1.00 | 39.73 | C |
| ATOM | 864 | NZ | LYS | A | 336 | 7.286 | −16.092 | −69.994 | 1.00 | 50.40 | N |
| ATOM | 865 | C | LYS | A | 336 | 11.860 | −16.132 | −64.152 | 1.00 | 19.64 | C |
| ATOM | 866 | O | LYS | A | 336 | 12.921 | −15.776 | −64.690 | 1.00 | 18.58 | O |
| ATOM | 867 | N | ASN | A | 337 | 11.507 | −15.734 | −62.929 | 1.00 | 18.00 | N |
| ATOM | 868 | CA | ASN | A | 337 | 12.379 | −14.870 | −62.136 | 1.00 | 16.43 | C |
| ATOM | 869 | CB | ASN | A | 337 | 11.670 | −14.398 | −60.849 | 1.00 | 20.21 | C |
| ATOM | 870 | CG | ASN | A | 337 | 10.456 | −13.587 | −61.137 | 1.00 | 27.33 | C |
| ATOM | 871 | OD1 | ASN | A | 337 | 9.341 | −13.995 | −60.840 | 1.00 | 34.10 | O |
| ATOM | 872 | ND2 | ASN | A | 337 | 10.651 | −12.458 | −61.750 | 1.00 | 30.05 | N |
| ATOM | 873 | C | ASN | A | 337 | 13.654 | −15.541 | −61.751 | 1.00 | 16.44 | C |
| ATOM | 874 | O | ASN | A | 337 | 14.613 | −14.872 | −61.402 | 1.00 | 18.69 | O |
| ATOM | 875 | N | GLU | A | 338 | 13.670 | −16.882 | −61.774 | 1.00 | 14.36 | N |
| ATOM | 876 | CA | GLU | A | 338 | 14.827 | −17.616 | −61.313 | 1.00 | 14.66 | C |
| ATOM | 877 | CB | GLU | A | 338 | 14.412 | −18.905 | −60.583 | 1.00 | 15.42 | C |
| ATOM | 878 | CG | GLU | A | 338 | 13.512 | −18.667 | −59.386 | 1.00 | 16.28 | C |
| ATOM | 879 | CD | GLU | A | 338 | 14.143 | −17.734 | −58.364 | 1.00 | 24.39 | C |
| ATOM | 880 | OE1 | GLU | A | 338 | 15.359 | −17.876 | −58.072 | 1.00 | 21.18 | O |
| ATOM | 881 | OE2 | GLU | A | 338 | 13.435 | −16.829 | −57.872 | 1.00 | 28.39 | O |
| ATOM | 882 | C | GLU | A | 338 | 15.815 | −17.953 | −62.434 | 1.00 | 15.18 | C |
| ATOM | 883 | O | GLU | A | 338 | 16.868 | −18.560 | −62.170 | 1.00 | 14.91 | O |
| ATOM | 884 | N | ILE | A | 339 | 15.497 | −17.550 | −63.665 | 1.00 | 14.51 | N |
| ATOM | 885 | CA | ILE | A | 339 | 16.351 | −17.929 | −64.828 | 1.00 | 15.89 | C |
| ATOM | 886 | CB | ILE | A | 339 | 15.611 | −17.655 | −66.171 | 1.00 | 18.62 | C |
| ATOM | 887 | CG1 | ILE | A | 339 | 14.398 | −18.598 | −66.317 | 1.00 | 17.98 | C |
| ATOM | 888 | CD1 | ILE | A | 339 | 13.378 | −18.137 | −67.361 | 1.00 | 21.22 | C |

TABLE 5-continued

Atomic coordinates for CRBN(TBD):Thalidomide (Murine protein)

| ATOM | 889 | CG2 | ILE | A | 339 | 16.573 | −17.768 | −67.371 | 1.00 | 16.54 | C |
|------|-----|-----|-----|---|-----|--------|---------|---------|------|-------|---|
| ATOM | 890 | C | ILE | A | 339 | 17.665 | −17.145 | −64.771 | 1.00 | 17.67 | C |
| ATOM | 891 | O | ILE | A | 339 | 17.655 | −15.956 | −64.495 | 1.00 | 16.43 | O |
| ATOM | 892 | N | PHE | A | 340 | 18.788 | −17.805 | −65.058 | 1.00 | 16.24 | N |
| ATOM | 893 | CA | PHE | A | 340 | 20.076 | −17.092 | −65.178 | 1.00 | 17.14 | C |
| ATOM | 894 | CB | PHE | A | 340 | 20.831 | −17.067 | −63.829 | 1.00 | 14.44 | C |
| ATOM | 895 | CG | PHE | A | 340 | 21.468 | −18.362 | −63.470 | 1.00 | 17.90 | C |
| ATOM | 896 | CD2 | PHE | A | 340 | 22.848 | −18.543 | −63.613 | 1.00 | 17.59 | C |
| ATOM | 897 | CE2 | PHE | A | 340 | 23.442 | −19.772 | −63.316 | 1.00 | 15.90 | C |
| ATOM | 898 | CZ | PHE | A | 340 | 22.657 | −20.840 | −62.840 | 1.00 | 17.74 | C |
| ATOM | 899 | CE1 | PHE | A | 340 | 21.281 | −20.664 | −62.680 | 1.00 | 15.22 | C |
| ATOM | 900 | CD1 | PHE | A | 340 | 20.691 | −19.442 | −62.977 | 1.00 | 17.65 | C |
| ATOM | 901 | C | PHE | A | 340 | 20.906 | −17.797 | −66.238 | 1.00 | 21.57 | C |
| ATOM | 902 | O | PHE | A | 340 | 20.539 | −18.867 | −66.694 | 1.00 | 18.80 | O |
| ATOM | 903 | N | SER | A | 341 | 22.025 | −17.193 | −66.609 | 1.00 | 20.31 | N |
| ATOM | 904 | CA | SER | A | 341 | 22.884 | −17.736 | −67.662 | 1.00 | 23.83 | C |
| ATOM | 905 | CB | SER | A | 341 | 23.020 | −16.719 | −68.802 | 1.00 | 32.15 | C |
| ATOM | 906 | OG | SER | A | 341 | 23.983 | −17.134 | −69.770 | 1.00 | 40.08 | O |
| ATOM | 907 | C | SER | A | 341 | 24.245 | −18.128 | −67.090 | 1.00 | 25.00 | C |
| ATOM | 908 | O | SER | A | 341 | 25.009 | −17.273 | −66.634 | 1.00 | 24.73 | O |
| ATOM | 909 | N | LEU | A | 342 | 24.520 | −19.439 | −67.058 | 1.00 | 23.54 | N |
| ATOM | 910 | CA | LEU | A | 342 | 25.846 | −19.936 | −66.661 | 1.00 | 28.00 | C |
| ATOM | 911 | CB | LEU | A | 342 | 25.760 | −21.407 | −66.224 | 1.00 | 25.89 | C |
| ATOM | 912 | CG | LEU | A | 342 | 26.376 | −21.963 | −64.932 | 1.00 | 38.88 | C |
| ATOM | 913 | CD1 | LEU | A | 342 | 26.759 | −23.424 | −65.109 | 1.00 | 33.04 | C |
| ATOM | 914 | CD2 | LEU | A | 342 | 27.577 | −21.187 | −64.452 | 1.00 | 37.66 | C |
| ATOM | 915 | C | LEU | A | 342 | 26.790 | −19.797 | −67.876 | 1.00 | 32.97 | C |
| ATOM | 916 | O | LEU | A | 342 | 26.406 | −20.106 | −69.018 | 1.00 | 33.19 | O |
| ATOM | 917 | N | SER | A | 343 | 28.000 | −19.303 | −67.654 | 1.00 | 33.59 | N |
| ATOM | 918 | CA | SER | A | 343 | 28.960 | −19.184 | −68.768 | 1.00 | 36.09 | C |
| ATOM | 919 | CB | SER | A | 343 | 30.112 | −18.237 | −68.418 | 1.00 | 47.49 | C |
| ATOM | 920 | OG | SER | A | 343 | 30.925 | −17.990 | −69.561 | 1.00 | 47.59 | O |
| ATOM | 921 | C | SER | A | 343 | 29.477 | −20.582 | −69.124 | 1.00 | 39.94 | C |
| ATOM | 922 | O | SER | A | 343 | 29.945 | −21.327 | −68.241 | 1.00 | 39.31 | O |
| ATOM | 923 | N | LEU | A | 344 | 29.343 | −20.943 | −70.402 | 1.00 | 41.77 | N |
| ATOM | 924 | CA | LEU | A | 344 | 29.561 | −22.321 | −70.869 | 1.00 | 60.36 | C |
| ATOM | 925 | CB | LEU | A | 344 | 28.345 | −22.829 | −71.675 | 1.00 | 63.72 | C |
| ATOM | 926 | CG | LEU | A | 344 | 27.198 | −23.540 | −70.926 | 1.00 | 63.73 | C |
| ATOM | 927 | CD1 | LEU | A | 344 | 26.115 | −22.561 | −70.503 | 1.00 | 57.76 | C |
| ATOM | 928 | CD2 | LEU | A | 344 | 26.594 | −24.653 | −71.777 | 1.00 | 59.87 | C |
| ATOM | 929 | C | LEU | A | 344 | 30.825 | −22.426 | −71.709 | 1.00 | 60.83 | C |
| ATOM | 930 | O | LEU | A | 344 | 31.926 | −22.220 | −71.209 | 1.00 | 58.36 | O |
| ATOM | 931 | N | GLU | A | 360 | 15.572 | −26.816 | −75.530 | 1.00 | 54.54 | N |
| ATOM | 932 | CA | GLU | A | 360 | 16.834 | −26.886 | −74.818 | 1.00 | 40.63 | C |
| ATOM | 933 | CB | GLU | A | 360 | 17.692 | −25.669 | −75.147 | 1.00 | 38.50 | C |
| ATOM | 934 | CG | GLU | A | 360 | 16.953 | −24.347 | −75.030 | 1.00 | 44.38 | C |
| ATOM | 935 | CD | GLU | A | 360 | 17.629 | −23.222 | −75.799 | 1.00 | 59.24 | C |
| ATOM | 936 | OE1 | GLU | A | 360 | 16.906 | −22.327 | −76.290 | 1.00 | 61.79 | O |
| ATOM | 937 | OE2 | GLU | A | 360 | 18.878 | −23.228 | −75.912 | 1.00 | 58.29 | O |
| ATOM | 938 | C | GLU | A | 360 | 16.655 | −27.007 | −73.283 | 1.00 | 38.18 | C |
| ATOM | 939 | O | GLU | A | 360 | 15.652 | −27.604 | −72.783 | 1.00 | 26.68 | O |
| ATOM | 940 | N | THR | A | 361 | 17.625 | −26.441 | −72.556 | 1.00 | 27.62 | N |
| ATOM | 941 | CA | THR | A | 361 | 17.752 | −26.621 | −71.076 | 1.00 | 32.19 | C |
| ATOM | 942 | CB | THR | A | 361 | 19.050 | −27.375 | −70.711 | 1.00 | 34.38 | C |
| ATOM | 943 | OG1 | THR | A | 361 | 19.014 | −28.701 | −71.259 | 1.00 | 41.61 | O |
| ATOM | 944 | CG2 | THR | A | 361 | 19.243 | −27.458 | −69.166 | 1.00 | 29.62 | C |
| ATOM | 945 | C | THR | A | 361 | 17.736 | −25.254 | −70.354 | 1.00 | 28.82 | C |
| ATOM | 946 | O | THR | A | 361 | 18.591 | −24.396 | −70.588 | 1.00 | 32.86 | O |
| ATOM | 947 | N | LEU | A | 362 | 16.754 | −25.058 | −69.490 | 1.00 | 19.76 | N |
| ATOM | 948 | CA | LEU | A | 362 | 16.607 | −23.793 | −68.784 | 1.00 | 21.13 | C |
| ATOM | 949 | CB | LEU | A | 362 | 15.131 | −23.617 | −68.431 | 1.00 | 23.70 | C |
| ATOM | 950 | CG | LEU | A | 362 | 14.687 | −22.281 | −67.883 | 1.00 | 27.97 | C |
| ATOM | 951 | CD1 | LEU | A | 362 | 14.705 | −21.241 | −68.991 | 1.00 | 25.88 | C |
| ATOM | 952 | CD2 | LEU | A | 362 | 13.276 | −22.445 | −67.337 | 1.00 | 33.42 | C |
| ATOM | 953 | C | LEU | A | 362 | 17.424 | −23.892 | −67.499 | 1.00 | 23.41 | C |
| ATOM | 954 | O | LEU | A | 362 | 17.295 | −24.874 | −66.801 | 1.00 | 20.60 | O |
| ATOM | 955 | N | THR | A | 363 | 18.265 | −22.889 | −67.176 | 1.00 | 17.96 | N |
| ATOM | 956 | CA | THR | A | 363 | 19.014 | −22.961 | −65.901 | 1.00 | 15.19 | C |
| ATOM | 957 | CB | THR | A | 363 | 20.538 | −22.726 | −66.072 | 1.00 | 18.99 | C |
| ATOM | 958 | OG1 | THR | A | 363 | 20.756 | −21.498 | −66.799 | 1.00 | 18.79 | O |
| ATOM | 959 | CG2 | THR | A | 363 | 21.197 | −23.931 | −66.850 | 1.00 | 23.58 | C |
| ATOM | 960 | C | THR | A | 363 | 18.447 | −21.918 | −64.954 | 1.00 | 15.28 | C |
| ATOM | 961 | O | THR | A | 363 | 18.296 | −20.751 | −65.342 | 1.00 | 15.07 | O |
| ATOM | 962 | N | VAL | A | 364 | 18.061 | −22.370 | −63.754 | 1.00 | 16.66 | N |
| ATOM | 963 | CA | VAL | A | 364 | 17.416 | −21.511 | −62.740 | 1.00 | 15.74 | C |
| ATOM | 964 | CB | VAL | A | 364 | 15.881 | −21.816 | −62.556 | 1.00 | 13.40 | C |
| ATOM | 965 | CG1 | VAL | A | 364 | 15.082 | −21.387 | −63.766 | 1.00 | 16.27 | C |
| ATOM | 966 | CG2 | VAL | A | 364 | 15.612 | −23.285 | −62.214 | 1.00 | 13.58 | C |

TABLE 5-continued

Atomic coordinates for CRBN(TBD):Thalidomide (Murine protein)

| ATOM | 967  | C   | VAL | A | 364 | 18.105 | −21.689 | −61.392 | 1.00 | 12.50 | C |
| ATOM | 968  | O   | VAL | A | 364 | 18.622 | −22.788 | −61.064 | 1.00 | 13.58 | O |
| ATOM | 969  | N   | TYR | A | 365 | 18.091 | −20.625 | −60.589 | 1.00 | 12.72 | N |
| ATOM | 970  | CA  | TYR | A | 365 | 18.767 | −20.633 | −59.306 | 1.00 | 14.10 | C |
| ATOM | 971  | CB  | TYR | A | 365 | 18.817 | −19.212 | −58.737 | 1.00 | 14.22 | C |
| ATOM | 972  | CG  | TYR | A | 365 | 19.899 | −18.354 | −59.313 | 1.00 | 17.51 | C |
| ATOM | 973  | CD1 | TYR | A | 365 | 21.257 | −18.730 | −59.208 | 1.00 | 15.39 | C |
| ATOM | 974  | CE1 | TYR | A | 365 | 22.267 | −17.910 | −59.714 | 1.00 | 16.21 | C |
| ATOM | 975  | CZ  | TYR | A | 365 | 21.927 | −16.726 | −60.321 | 1.00 | 18.33 | C |
| ATOM | 976  | OH  | TYR | A | 365 | 22.920 | −15.924 | −60.831 | 1.00 | 19.92 | O |
| ATOM | 977  | CE2 | TYR | A | 365 | 20.613 | −16.319 | −60.408 | 1.00 | 17.25 | C |
| ATOM | 978  | CD2 | TYR | A | 365 | 19.590 | −17.152 | −59.928 | 1.00 | 15.49 | C |
| ATOM | 979  | C   | TYR | A | 365 | 18.027 | −21.514 | −58.298 | 1.00 | 13.68 | C |
| ATOM | 980  | O   | TYR | A | 365 | 18.636 | −22.096 | −57.390 | 1.00 | 14.00 | O |
| ATOM | 981  | N   | LYS | A | 366 | 16.701 | −21.540 | −58.442 | 1.00 | 14.64 | N |
| ATOM | 982  | CA  | LYS | A | 366 | 15.813 | −22.158 | −57.461 | 1.00 | 15.00 | C |
| ATOM | 983  | CB  | LYS | A | 366 | 15.182 | −21.070 | −56.571 | 1.00 | 15.61 | C |
| ATOM | 984  | CG  | LYS | A | 366 | 16.174 | −20.386 | −55.621 | 1.00 | 17.78 | C |
| ATOM | 985  | CD  | LYS | A | 366 | 16.349 | −21.258 | −54.390 | 1.00 | 17.98 | C |
| ATOM | 986  | CE  | LYS | A | 366 | 17.312 | −20.672 | −53.386 | 1.00 | 22.69 | C |
| ATOM | 987  | NZ  | LYS | A | 366 | 17.399 | −21.604 | −52.240 | 1.00 | 18.28 | N |
| ATOM | 988  | C   | LYS | A | 366 | 14.693 | −22.903 | −58.174 | 1.00 | 12.15 | C |
| ATOM | 989  | O   | LYS | A | 366 | 14.206 | −22.458 | −59.235 | 1.00 | 14.93 | O |
| ATOM | 990  | N   | ALA | A | 367 | 14.220 | −23.977 | −57.548 | 1.00 | 13.21 | N |
| ATOM | 991  | CA  | ALA | A | 367 | 13.081 | −24.755 | −58.057 | 1.00 | 14.40 | C |
| ATOM | 992  | CB  | ALA | A | 367 | 13.559 | −25.833 | −59.049 | 1.00 | 14.70 | C |
| ATOM | 993  | C   | ALA | A | 367 | 12.373 | −25.419 | −56.886 | 1.00 | 12.95 | C |
| ATOM | 994  | O   | ALA | A | 367 | 12.929 | −25.503 | −55.758 | 1.00 | 17.70 | O |
| ATOM | 995  | N   | SER | A | 368 | 11.180 | −25.919 | −57.145 | 1.00 | 14.33 | N |
| ATOM | 996  | CA  | SER | A | 368 | 10.317 | −26.439 | −56.067 | 1.00 | 15.19 | C |
| ATOM | 997  | CB  | SER | A | 368 | 9.220  | −25.394 | −55.730 | 1.00 | 14.05 | C |
| ATOM | 998  | OG  | SER | A | 368 | 8.512  | −25.019 | −56.909 | 1.00 | 19.52 | O |
| ATOM | 999  | C   | SER | A | 368 | 9.637  | −27.722 | −56.558 | 1.00 | 14.51 | C |
| ATOM | 1000 | O   | SER | A | 368 | 9.480  | −27.925 | −57.785 | 1.00 | 13.03 | O |
| ATOM | 1001 | N   | ASN | A | 369 | 9.200  | −28.550 | −55.610 | 1.00 | 14.24 | N |
| ATOM | 1002 | CA  | ASN | A | 369 | 8.319  | −29.679 | −55.909 | 1.00 | 15.26 | C |
| ATOM | 1003 | CB  | ASN | A | 369 | 7.018  | −29.180 | −56.549 | 1.00 | 13.90 | C |
| ATOM | 1004 | CG  | ASN | A | 369 | 6.245  | −28.226 | −55.622 | 1.00 | 19.57 | C |
| ATOM | 1005 | OD1 | ASN | A | 369 | 5.741  | −27.178 | −56.047 | 1.00 | 21.87 | O |
| ATOM | 1006 | ND2 | ASN | A | 369 | 6.207  | −28.563 | −54.347 | 1.00 | 17.45 | N |
| ATOM | 1007 | C   | ASN | A | 369 | 9.000  | −30.743 | −56.767 | 1.00 | 18.36 | C |
| ATOM | 1008 | O   | ASN | A | 369 | 8.337  | −31.496 | −57.505 | 1.00 | 18.33 | O |
| ATOM | 1009 | N   | LEU | A | 370 | 10.309 | −30.851 | −56.608 | 1.00 | 15.47 | N |
| ATOM | 1010 | CA  | LEU | A | 370 | 11.077 | −31.893 | −57.259 | 1.00 | 17.84 | C |
| ATOM | 1011 | CB  | LEU | A | 370 | 12.217 | −31.280 | −58.085 | 1.00 | 15.67 | C |
| ATOM | 1012 | CG  | LEU | A | 370 | 11.822 | −30.431 | −59.300 | 1.00 | 16.95 | C |
| ATOM | 1013 | CD1 | LEU | A | 370 | 13.039 | −29.687 | −59.845 | 1.00 | 18.12 | C |
| ATOM | 1014 | CD2 | LEU | A | 370 | 11.231 | −31.288 | −60.408 | 1.00 | 16.77 | C |
| ATOM | 1015 | C   | LEU | A | 370 | 11.645 | −32.827 | −56.220 | 1.00 | 21.02 | C |
| ATOM | 1016 | O   | LEU | A | 370 | 12.073 | −32.391 | −55.140 | 1.00 | 21.26 | O |
| ATOM | 1017 | N   | ASN | A | 371 | 11.650 | −34.106 | −56.554 | 1.00 | 18.65 | N |
| ATOM | 1018 | CA  | ASN | A | 371 | 12.345 | −35.124 | −55.786 | 1.00 | 19.11 | C |
| ATOM | 1019 | CB  | ASN | A | 371 | 11.456 | −36.378 | −55.660 | 1.00 | 20.40 | C |
| ATOM | 1020 | CG  | ASN | A | 371 | 10.301 | −36.176 | −54.702 | 1.00 | 25.22 | C |
| ATOM | 1021 | OD1 | ASN | A | 371 | 10.409 | −35.415 | −53.724 | 1.00 | 32.27 | O |
| ATOM | 1022 | ND2 | ASN | A | 371 | 9.184  | −36.841 | −54.973 | 1.00 | 27.28 | N |
| ATOM | 1023 | C   | ASN | A | 371 | 13.608 | −35.504 | −56.480 | 1.00 | 19.60 | C |
| ATOM | 1024 | O   | ASN | A | 371 | 13.627 | −35.676 | −57.692 | 1.00 | 20.13 | O |
| ATOM | 1025 | N   | LEU | A | 372 | 14.671 | −35.670 | −55.711 | 1.00 | 19.95 | N |
| ATOM | 1026 | CA  | LEU | A | 372 | 15.972 | −36.041 | −56.266 | 1.00 | 20.70 | C |
| ATOM | 1027 | CB  | LEU | A | 372 | 17.095 | −35.384 | −55.469 | 1.00 | 26.05 | C |
| ATOM | 1028 | CG  | LEU | A | 372 | 17.112 | −33.836 | −55.401 | 1.00 | 28.71 | C |
| ATOM | 1029 | CD1 | LEU | A | 372 | 18.169 | −33.369 | −54.398 | 1.00 | 37.57 | C |
| ATOM | 1030 | CD2 | LEU | A | 372 | 17.371 | −33.203 | −56.763 | 1.00 | 28.90 | C |
| ATOM | 1031 | C   | LEU | A | 372 | 16.127 | −37.540 | −56.218 | 1.00 | 27.21 | C |
| ATOM | 1032 | O   | LEU | A | 372 | 15.786 | −38.172 | −55.207 | 1.00 | 22.80 | O |
| ATOM | 1033 | N   | ILE | A | 373 | 16.661 | −38.105 | −57.298 | 1.00 | 23.66 | N |
| ATOM | 1034 | CA  | ILE | A | 373 | 16.835 | −39.539 | −57.410 | 1.00 | 26.08 | C |
| ATOM | 1035 | CB  | ILE | A | 373 | 16.175 | −40.081 | −58.693 | 1.00 | 29.06 | C |
| ATOM | 1036 | CG1 | ILE | A | 373 | 14.693 | −39.687 | −58.754 | 1.00 | 26.65 | C |
| ATOM | 1037 | CD1 | ILE | A | 373 | 13.858 | −40.236 | −57.606 | 1.00 | 25.01 | C |
| ATOM | 1038 | CG2 | ILE | A | 373 | 16.323 | −41.608 | −58.781 | 1.00 | 31.87 | C |
| ATOM | 1039 | C   | ILE | A | 373 | 18.327 | −39.863 | −57.465 | 1.00 | 29.50 | C |
| ATOM | 1040 | O   | ILE | A | 373 | 19.039 | −39.386 | −58.361 | 1.00 | 27.45 | O |
| ATOM | 1041 | N   | GLY | A | 374 | 18.798 | −40.662 | −56.507 | 1.00 | 33.07 | N |
| ATOM | 1042 | CA  | GLY | A | 374 | 20.178 | −41.136 | −56.533 | 1.00 | 33.62 | C |
| ATOM | 1043 | C   | GLY | A | 374 | 21.157 | −40.100 | −56.033 | 1.00 | 35.52 | C |
| ATOM | 1044 | O   | GLY | A | 374 | 20.773 | −39.168 | −55.316 | 1.00 | 34.59 | O |

TABLE 5-continued

Atomic coordinates for CRBN(TBD):Thalidomide (Murine protein)

| ATOM | 1045 | N | ARG | A | 375 | 22.429 | −40.247 | −56.435 | 1.00 | 31.82 | N |
|---|---|---|---|---|---|---|---|---|---|---|---|
| ATOM | 1046 | CA | ARG | A | 375 | 23.540 | −39.471 | −55.859 | 1.00 | 32.45 | C |
| ATOM | 1047 | CB | ARG | A | 375 | 24.585 | −40.405 | −55.217 | 1.00 | 37.47 | C |
| ATOM | 1048 | CG | ARG | A | 375 | 24.003 | −41.494 | −54.300 | 1.00 | 47.10 | C |
| ATOM | 1049 | CD | ARG | A | 375 | 25.049 | −42.109 | −53.370 | 1.00 | 52.40 | C |
| ATOM | 1050 | NE | ARG | A | 375 | 26.408 | −41.612 | −53.628 | 1.00 | 77.74 | N |
| ATOM | 1051 | CZ | ARG | A | 375 | 27.255 | −42.132 | −54.519 | 1.00 | 75.83 | C |
| ATOM | 1052 | NH1 | ARG | A | 375 | 26.899 | −43.175 | −55.262 | 1.00 | 69.90 | N |
| ATOM | 1053 | NH2 | ARG | A | 375 | 28.457 | −41.595 | −54.676 | 1.00 | 81.71 | N |
| ATOM | 1054 | C | ARG | A | 375 | 24.198 | −38.668 | −56.966 | 1.00 | 30.05 | C |
| ATOM | 1055 | O | ARG | A | 375 | 24.100 | −39.043 | −58.132 | 1.00 | 30.89 | O |
| ATOM | 1056 | N | PRO | A | 376 | 24.880 | −37.561 | −56.619 | 1.00 | 25.07 | N |
| ATOM | 1057 | CA | PRO | A | 376 | 25.445 | −36.742 | −57.711 | 1.00 | 23.23 | C |
| ATOM | 1053 | CB | PRO | A | 376 | 26.062 | −35.542 | −56.972 | 1.00 | 25.63 | C |
| ATOM | 1059 | CG | PRO | A | 376 | 25.348 | −35.500 | −55.653 | 1.00 | 31.07 | C |
| ATOM | 1060 | CD | PRO | A | 376 | 25.091 | −36.936 | −55.300 | 1.00 | 31.31 | C |
| ATOM | 1061 | C | PRO | A | 376 | 26.494 | −37.477 | −58.553 | 1.00 | 27.82 | C |
| ATOM | 1062 | O | PRO | A | 376 | 27.211 | −38.334 | −58.034 | 1.00 | 33.45 | O |
| ATOM | 1063 | N | SER | A | 377 | 26.548 | −37.169 | −59.850 | 1.00 | 24.06 | N |
| ATOM | 1064 | CA | SER | A | 377 | 27.555 | −37.751 | −60.746 | 1.00 | 24.41 | C |
| ATOM | 1065 | CB | SER | A | 377 | 26.933 | −38.851 | −61.642 | 1.00 | 24.09 | C |
| ATOM | 1066 | OG | SER | A | 377 | 27.849 | −39.241 | −62.686 | 1.00 | 28.67 | O |
| ATOM | 1067 | C | SER | A | 377 | 28.152 | −36.679 | −61.617 | 1.00 | 25.29 | C |
| ATOM | 1068 | O | SER | A | 377 | 27.441 | −35.761 | −62.089 | 1.00 | 24.22 | O |
| ATOM | 1069 | N | THR | A | 378 | 29.444 | −36.787 | −61.887 | 1.00 | 21.39 | N |
| ATOM | 1070 | CA | THR | A | 378 | 30.069 | −35.875 | −62.848 | 1.00 | 22.60 | C |
| ATOM | 1071 | CB | THR | A | 378 | 31.495 | −35.499 | −62.411 | 1.00 | 28.47 | C |
| ATOM | 1072 | OG1 | THR | A | 378 | 32.250 | −36.696 | −62.263 | 1.00 | 26.46 | O |
| ATOM | 1073 | CG2 | THR | A | 378 | 31.467 | −34.772 | −61.077 | 1.00 | 25.64 | C |
| ATOM | 1074 | C | THR | A | 378 | 30.156 | −36.442 | −64.267 | 1.00 | 20.34 | C |
| ATOM | 1075 | O | THR | A | 378 | 30.633 | −35.751 | −65.181 | 1.00 | 23.40 | O |
| ATOM | 1076 | N | VAL | A | 379 | 29.734 | −37.699 | −64.443 | 1.00 | 25.52 | N |
| ATOM | 1077 | CA | VAL | A | 379 | 29.851 | −38.369 | −65.738 | 1.00 | 26.25 | C |
| ATOM | 1078 | CB | VAL | A | 379 | 29.410 | −39.853 | −65.656 | 1.00 | 25.49 | C |
| ATOM | 1079 | CG1 | VAL | A | 379 | 29.529 | −40.512 | −67.021 | 1.00 | 36.68 | C |
| ATOM | 1080 | CG2 | VAL | A | 379 | 30.271 | −40.599 | −64.649 | 1.00 | 32.31 | C |
| ATOM | 1081 | C | VAL | A | 379 | 29.041 | −37.635 | −66.806 | 1.00 | 24.36 | C |
| ATOM | 1082 | O | VAL | A | 379 | 27.870 | −37.394 | −66.623 | 1.00 | 27.01 | O |
| ATOM | 1083 | N | HIS | A | 380 | 29.693 | −37.260 | −67.900 | 1.00 | 21.88 | N |
| ATOM | 1084 | CA | HIS | A | 380 | 29.053 | −36.523 | −69.009 | 1.00 | 26.88 | C |
| ATOM | 1085 | CB | HIS | A | 380 | 27.998 | −37.406 | −69.743 | 1.00 | 25.41 | C |
| ATOM | 1086 | CG | HIS | A | 380 | 28.561 | −38.701 | −70.313 | 1.00 | 27.07 | C |
| ATOM | 1087 | ND1 | HIS | A | 380 | 29.619 | −38.727 | −71.168 | 1.00 | 30.51 | N |
| ATOM | 1088 | CE1 | HIS | A | 380 | 29.888 | −40.005 | −71.499 | 1.00 | 27.87 | C |
| ATOM | 1089 | NE2 | HIS | A | 380 | 29.011 | −40.801 | −70.859 | 1.00 | 27.67 | N |
| ATOM | 1090 | CD2 | HIS | A | 380 | 28.164 | −40.033 | −70.140 | 1.00 | 27.53 | C |
| ATOM | 1091 | C | HIS | A | 380 | 28.436 | −35.166 | −68.641 | 1.00 | 25.06 | C |
| ATOM | 1092 | O | HIS | A | 380 | 27.648 | −34.615 | −69.414 | 1.00 | 23.98 | O |
| ATOM | 1093 | N | SER | A | 381 | 28.782 | −34.617 | −67.473 | 1.00 | 25.37 | N |
| ATOM | 1094 | CA | SER | A | 381 | 28.188 | −33.314 | −67.045 | 1.00 | 23.77 | C |
| ATOM | 1095 | CB | SER | A | 381 | 28.864 | −32.775 | −65.791 | 1.00 | 25.06 | C |
| ATOM | 1096 | OG | SER | A | 381 | 28.205 | −31.577 | −65.394 | 1.00 | 21.03 | O |
| ATOM | 1097 | C | SER | A | 381 | 28.231 | −32.249 | −68.117 | 1.00 | 21.38 | C |
| ATOM | 1098 | O | SER | A | 381 | 29.288 | −31.959 | −68.684 | 1.00 | 21.51 | O |
| ATOM | 1099 | N | TRP | A | 382 | 27.084 | −31.630 | −68.386 | 1.00 | 18.44 | N |
| ATOM | 1100 | CA | TRP | A | 382 | 27.026 | −30.557 | −69.347 | 1.00 | 20.60 | C |
| ATOM | 1101 | CB | TRP | A | 382 | 25.608 | −30.281 | −69.796 | 1.00 | 23.63 | C |
| ATOM | 1102 | CG | TRP | A | 382 | 24.904 | −31.474 | −70.389 | 1.00 | 23.49 | C |
| ATOM | 1103 | CD1 | TRP | A | 382 | 25.452 | −32.460 | −71.216 | 1.00 | 26.82 | C |
| ATOM | 1104 | NE1 | TRP | A | 382 | 24.489 | −33.401 | −71.555 | 1.00 | 21.24 | N |
| ATOM | 1105 | CE2 | TRP | A | 382 | 23.296 | −33.094 | −70.940 | 1.00 | 22.49 | C |
| ATOM | 1106 | CD2 | TRP | A | 382 | 23.501 | −31.851 | −70.197 | 1.00 | 24.48 | C |
| ATOM | 1107 | CE3 | TRP | A | 382 | 22.427 | −31.306 | −69.476 | 1.00 | 26.68 | C |
| ATOM | 1108 | CZ3 | TRP | A | 382 | 21.187 | −31.967 | −69.513 | 1.00 | 22.77 | C |
| ATOM | 1109 | CH2 | TRP | A | 382 | 21.005 | −33.145 | −70.267 | 1.00 | 24.87 | C |
| ATOM | 1110 | CZ2 | TRP | A | 382 | 22.065 | −33.737 | −70.974 | 1.00 | 27.21 | C |
| ATOM | 1111 | C | TRP | A | 382 | 27.621 | −29.293 | −68.832 | 1.00 | 22.03 | C |
| ATOM | 1112 | O | TRP | A | 382 | 27.810 | −28.362 | −69.593 | 1.00 | 22.11 | O |
| ATOM | 1113 | N | PHE | A | 383 | 27.845 | −29.235 | −67.522 | 1.00 | 22.34 | N |
| ATOM | 1114 | CA | PHE | A | 383 | 28.417 | −28.009 | −66.868 | 1.00 | 20.86 | C |
| ATOM | 1115 | CB | PHE | A | 383 | 27.347 | −27.327 | −65.992 | 1.00 | 19.63 | C |
| ATOM | 1116 | CG | PHE | A | 383 | 26.107 | −26.956 | −66.754 | 1.00 | 20.66 | C |
| ATOM | 1117 | CD1 | PHE | A | 383 | 26.113 | −25.895 | −67.624 | 1.00 | 22.70 | C |
| ATOM | 1118 | CE1 | PHE | A | 383 | 24.969 | −25.558 | −68.345 | 1.00 | 33.06 | C |
| ATOM | 1119 | CZ | PHE | A | 383 | 23.813 | −26.325 | −68.216 | 1.00 | 25.51 | C |
| ATOM | 1120 | CE2 | PHE | A | 383 | 23.817 | −27.418 | −67.367 | 1.00 | 22.05 | C |
| ATOM | 1121 | CD2 | PHE | A | 383 | 24.953 | −27.732 | −66.649 | 1.00 | 19.30 | C |
| ATOM | 1122 | C | PHE | A | 383 | 29.657 | −28.378 | −66.059 | 1.00 | 19.37 | C |

TABLE 5-continued

Atomic coordinates for CRBN(TBD):Thalidomide (Murine protein)

| ATOM | 1123 | O | PHE | A | 333 | 29.573 | −28.720 | −64.903 | 1.00 | 20.96 | O |
|---|---|---|---|---|---|---|---|---|---|---|---|
| ATOM | 1124 | N | PRO | A | 384 | 30.828 | −28.703 | −66.703 | 1.00 | 26.97 | N |
| ATOM | 1125 | CA | PRO | A | 384 | 32.078 | −28.795 | −66.056 | 1.00 | 30.77 | C |
| ATOM | 1126 | CB | PRO | A | 334 | 33.167 | −28.354 | −67.060 | 1.00 | 30.95 | C |
| ATOM | 1127 | CG | PRO | A | 384 | 32.479 | −28.385 | −68.372 | 1.00 | 37.59 | C |
| ATOM | 1128 | CD | PRO | A | 384 | 31.032 | −27.986 | −68.120 | 1.00 | 26.71 | C |
| ATOM | 1129 | C | PRO | A | 384 | 32.276 | −28.100 | −64.719 | 1.00 | 25.39 | C |
| ATOM | 1130 | O | PRO | A | 384 | 32.042 | −26.910 | −64.613 | 1.00 | 27.70 | O |
| ATOM | 1131 | N | GLY | A | 335 | 32.637 | −28.856 | −63.695 | 1.00 | 24.10 | N |
| ATOM | 1132 | CA | GLY | A | 385 | 32.723 | −28.301 | −62.375 | 1.00 | 28.87 | C |
| ATOM | 1133 | C | GLY | A | 385 | 31.483 | −28.583 | −61.548 | 1.00 | 28.15 | C |
| ATOM | 1134 | O | GLY | A | 385 | 31.479 | −28.356 | −60.341 | 1.00 | 25.07 | O |
| ATOM | 1135 | N | TYR | A | 386 | 30.412 | −29.063 | −62.206 | 1.00 | 23.50 | N |
| ATOM | 1136 | CA | TYR | A | 386 | 29.186 | −29.473 | −61.494 | 1.00 | 22.79 | C |
| ATOM | 1137 | CB | TYR | A | 386 | 27.987 | −28.644 | −61.986 | 1.00 | 20.38 | C |
| ATOM | 1138 | CG | TYR | A | 386 | 28.071 | −27.185 | −61.612 | 1.00 | 20.82 | C |
| ATOM | 1139 | CD2 | TYR | A | 336 | 27.472 | −26.716 | −60.440 | 1.00 | 19.55 | C |
| ATOM | 1140 | CE2 | TYR | A | 386 | 27.546 | −25.369 | −60.086 | 1.00 | 19.57 | C |
| ATOM | 1141 | CZ | TYR | A | 386 | 28.216 | −24.474 | −60.907 | 1.00 | 21.35 | C |
| ATOM | 1142 | OH | TYR | A | 386 | 28.271 | −23.134 | −60.535 | 1.00 | 18.04 | O |
| ATOM | 1143 | CE1 | TYR | A | 386 | 28.810 | −24.910 | −62.094 | 1.00 | 17.74 | C |
| ATOM | 1144 | CD1 | TYR | A | 386 | 28.728 | −26.260 | −62.440 | 1.00 | 21.38 | C |
| ATOM | 1145 | C | TYR | A | 386 | 28.891 | −30.951 | −61.715 | 1.00 | 20.73 | C |
| ATOM | 1146 | O | TYR | A | 386 | 29.187 | −31.494 | −62.772 | 1.00 | 21.44 | O |
| ATOM | 1147 | N | ALA | A | 387 | 28.337 | −31.583 | −60.701 | 1.00 | 22.51 | N |
| ATOM | 1148 | CA | ALA | A | 387 | 27.762 | −32.907 | −60.830 | 1.00 | 22.36 | C |
| ATOM | 1149 | CB | ALA | A | 387 | 28.143 | −33.757 | −59.637 | 1.00 | 22.23 | C |
| ATOM | 1150 | C | ALA | A | 387 | 26.239 | −32.784 | −60.938 | 1.00 | 23.77 | C |
| ATOM | 1151 | O | ALA | A | 387 | 25.665 | −31.756 | −60.579 | 1.00 | 23.94 | O |
| ATOM | 1152 | N | TRP | A | 388 | 25.601 | −33.834 | −61.433 | 1.00 | 20.85 | N |
| ATOM | 1153 | CA | TRP | A | 388 | 24.161 | −33.837 | −61.653 | 1.00 | 21.29 | C |
| ATOM | 1154 | CB | TRP | A | 388 | 23.848 | −33.926 | −63.159 | 1.00 | 22.82 | C |
| ATOM | 1155 | CG | TRP | A | 388 | 24.459 | −35.129 | −63.834 | 1.00 | 20.86 | C |
| ATOM | 1156 | CD1 | TRP | A | 388 | 25.650 | −35.185 | −64.552 | 1.00 | 21.27 | C |
| ATOM | 1157 | NE1 | TRP | A | 388 | 25.862 | −36.460 | −65.039 | 1.00 | 21.02 | N |
| ATOM | 1158 | CE2 | TRP | A | 388 | 24.874 | −37.289 | −64.625 | 1.00 | 20.94 | C |
| ATOM | 1159 | CD2 | TRP | A | 388 | 23.927 | −36.483 | −63.856 | 1.00 | 20.92 | C |
| ATOM | 1160 | CE3 | TRP | A | 388 | 22.791 | −37.093 | −63.328 | 1.00 | 21.07 | C |
| ATOM | 1161 | CZ3 | TRP | A | 388 | 22.584 | −38.464 | −63.579 | 1.00 | 29.65 | C |
| ATOM | 1162 | CH2 | TRP | A | 388 | 23.510 | −39.216 | −64.325 | 1.00 | 24.57 | C |
| ATOM | 1163 | CZ2 | TRP | A | 388 | 24.669 | −38.637 | −64.865 | 1.00 | 26.17 | C |
| ATOM | 1164 | C | TRP | A | 388 | 23.463 | −34.907 | −60.863 | 1.00 | 24.28 | C |
| ATOM | 1165 | O | TRP | A | 388 | 24.049 | −35.968 | −60.511 | 1.00 | 22.04 | O |
| ATOM | 1166 | N | THR | A | 389 | 22.219 | −34.617 | −60.512 | 1.00 | 22.74 | N |
| ATOM | 1167 | CA | THR | A | 389 | 21.341 | −35.561 | −59.861 | 1.00 | 18.08 | C |
| ATOM | 1168 | CB | THR | A | 389 | 21.155 | −35.214 | −58.356 | 1.00 | 22.84 | C |
| ATOM | 1169 | OG1 | THR | A | 389 | 22.448 | −35.158 | −57.705 | 1.00 | 25.75 | O |
| ATOM | 1170 | CG2 | THR | A | 389 | 20.307 | −36.246 | −57.663 | 1.00 | 20.09 | C |
| ATOM | 1171 | C | THR | A | 389 | 19.998 | −35.465 | −60.609 | 1.00 | 18.87 | C |
| ATOM | 1172 | O | THR | A | 389 | 19.503 | −34.360 | −60.863 | 1.00 | 17.08 | O |
| ATOM | 1173 | N | ILE | A | 390 | 19.424 | −36.607 | −60.988 | 1.00 | 16.95 | N |
| ATOM | 1174 | CA | ILE | A | 390 | 18.071 | −36.577 | −61.618 | 1.00 | 18.27 | C |
| ATOM | 1175 | CB | ILE | A | 390 | 17.637 | −37.992 | −62.078 | 1.00 | 23.37 | C |
| ATOM | 1176 | CG1 | ILE | A | 390 | 18.577 | −38.492 | −63.183 | 1.00 | 23.70 | C |
| ATOM | 1177 | CD1 | ILE | A | 390 | 18.560 | −40.019 | −63.336 | 1.00 | 33.13 | C |
| ATOM | 1178 | CG2 | ILE | A | 390 | 16.193 | −37.991 | −62.562 | 1.00 | 23.33 | C |
| ATOM | 1179 | C | ILE | A | 390 | 17.007 | −35.936 | −60.691 | 1.00 | 16.79 | C |
| ATOM | 1180 | O | ILE | A | 390 | 16.956 | −36.231 | −59.470 | 1.00 | 16.80 | O |
| ATOM | 1181 | N | ALA | A | 391 | 16.148 | −35.089 | −61.280 | 1.00 | 17.09 | N |
| ATOM | 1182 | CA | ALA | A | 391 | 15.091 | −34.386 | −60.542 | 1.00 | 18.29 | C |
| ATOM | 1183 | CB | ALA | A | 391 | 15.376 | −32.872 | −60.521 | 1.00 | 17.09 | C |
| ATOM | 1184 | C | ALA | A | 391 | 13.750 | −34.663 | −61.214 | 1.00 | 19.96 | C |
| ATOM | 1185 | O | ALA | A | 391 | 13.593 | −34.428 | −62.412 | 1.00 | 17.86 | O |
| ATOM | 1186 | N | GLN | A | 392 | 12.806 | −35.219 | −60.465 | 1.00 | 16.58 | N |
| ATOM | 1187 | CA | GLN | A | 392 | 11.501 | −35.546 | −61.034 | 1.00 | 17.64 | C |
| ATOM | 1188 | CB | GLN | A | 392 | 11.273 | −37.057 | −61.035 | 1.00 | 24.45 | C |
| ATOM | 1189 | CG | GLN | A | 392 | 11.366 | −37.712 | −59.683 | 1.00 | 24.08 | C |
| ATOM | 1190 | CD | GLN | A | 392 | 11.135 | −39.230 | −59.775 | 1.00 | 32.39 | C |
| ATOM | 1191 | OE1 | GLN | A | 392 | 11.665 | −39.903 | −60.657 | 1.00 | 28.38 | O |
| ATOM | 1192 | NE2 | GLN | A | 392 | 10.347 | −39.752 | −58.871 | 1.00 | 33.11 | N |
| ATOM | 1193 | C | GLN | A | 392 | 10.386 | −34.872 | −60.267 | 1.00 | 15.18 | C |
| ATOM | 1194 | O | GLN | A | 392 | 10.527 | −34.584 | −59.068 | 1.00 | 14.91 | O |
| ATOM | 1195 | N | CYS | A | 393 | 9.276 | −34.627 | −60.948 | 1.00 | 13.31 | N |
| ATOM | 1196 | CA | CYS | A | 393 | 8.103 | −33.991 | −60.319 | 1.00 | 15.19 | C |
| ATOM | 1197 | CB | CYS | A | 393 | 6.943 | −33.848 | −61.336 | 1.00 | 14.35 | C |
| ATOM | 1198 | SG | CYS | A | 393 | 5.435 | −33.133 | −60.584 | 1.00 | 16.09 | S |
| ATOM | 1199 | C | CYS | A | 393 | 7.629 | −34.818 | −59.116 | 1.00 | 18.29 | C |
| ATOM | 1200 | O | CYS | A | 393 | 7.474 | −36.023 | −59.230 | 1.00 | 16.38 | O |

TABLE 5-continued

Atomic coordinates for CRBN(TBD):Thalidomide (Murine protein)

| ATOM | 1201 | N | LYS | A | 394 | 7.400 | −34.159 | −57.973 | 1.00 | 15.55 | N |
| ATOM | 1202 | CA | LYS | A | 394 | 6.950 | −34.866 | −56.742 | 1.00 | 18.48 | C |
| ATOM | 1203 | CB | LYS | A | 394 | 7.007 | −33.949 | −55.520 | 1.00 | 18.74 | C |
| ATOM | 1204 | CG | LYS | A | 394 | 5.807 | −33.003 | −55.367 | 1.00 | 19.82 | C |
| ATOM | 1205 | CD | LYS | A | 394 | 5.871 | −32.240 | −54.036 | 1.00 | 23.50 | C |
| ATOM | 1206 | CE | LYS | A | 394 | 4.638 | −31.347 | −53.846 | 1.00 | 24.76 | C |
| ATOM | 1207 | NZ | LYS | A | 394 | 4.742 | −30.437 | −52.642 | 1.00 | 25.38 | N |
| ATOM | 1208 | C | LYS | A | 394 | 5.565 | −35.480 | −56.865 | 1.00 | 17.86 | C |
| ATOM | 1209 | O | LYS | A | 394 | 5.257 | −36.433 | −56.159 | 1.00 | 19.63 | O |
| ATOM | 1210 | N | ILE | A | 395 | 4.735 | −34.927 | −57.754 | 1.00 | 17.80 | N |
| ATOM | 1211 | CA | ILE | A | 395 | 3.358 | −35.409 | −57.947 | 1.00 | 20.98 | C |
| ATOM | 1212 | CB | ILE | A | 395 | 2.408 | −34.284 | −58.397 | 1.00 | 20.30 | C |
| ATOM | 1213 | CG1 | ILE | A | 395 | 2.338 | −33.152 | −57.341 | 1.00 | 21.67 | C |
| ATOM | 1214 | CD1 | ILE | A | 395 | 1.867 | −33.568 | −55.961 | 1.00 | 28.19 | C |
| ATOM | 1215 | CG2 | ILE | A | 395 | 1.024 | −34.849 | −58.748 | 1.00 | 22.86 | C |
| ATOM | 1216 | C | ILE | A | 395 | 3.265 | −36.578 | −58.951 | 1.00 | 23.60 | C |
| ATOM | 1217 | O | ILE | A | 395 | 2.767 | −37.650 | −58.609 | 1.00 | 24.21 | O |
| ATOM | 1218 | N | CYS | A | 396 | 3.824 | −36.390 | −60.152 | 1.00 | 16.52 | N |
| ATOM | 1219 | CA | CYS | A | 396 | 3.610 | −37.329 | −61.250 | 1.00 | 14.91 | C |
| ATOM | 1220 | CB | CYS | A | 396 | 3.020 | −36.610 | −62.452 | 1.00 | 19.18 | C |
| ATOM | 1221 | SG | CYS | A | 396 | 4.212 | −35.527 | −63.306 | 1.00 | 17.12 | S |
| ATOM | 1222 | C | CYS | A | 396 | 4.836 | −38.152 | −61.653 | 1.00 | 19.70 | C |
| ATOM | 1223 | O | CYS | A | 396 | 4.747 | −39.029 | −62.545 | 1.00 | 18.60 | O |
| ATOM | 1224 | N | ALA | A | 397 | 5.962 | −37.895 | −60.960 | 1.00 | 18.51 | N |
| ATOM | 1225 | CA | ALA | A | 397 | 7.253 | −38.527 | −61.225 | 1.00 | 18.99 | C |
| ATOM | 1226 | CB | ALA | A | 397 | 7.222 | −40.038 | −60.907 | 1.00 | 21.26 | C |
| ATOM | 1227 | C | ALA | A | 397 | 7.832 | −38.273 | −62.613 | 1.00 | 17.09 | C |
| ATOM | 1228 | O | ALA | A | 397 | 8.748 | −38.957 | −63.026 | 1.00 | 17.46 | O |
| ATOM | 1229 | N | SER | A | 398 | 7.310 | −37.303 | −63.342 | 1.00 | 16.46 | N |
| ATOM | 1230 | CA | SER | A | 398 | 7.904 | −36.964 | −64.642 | 1.00 | 17.70 | C |
| ATOM | 1231 | CB | SER | A | 398 | 7.061 | −35.926 | −65.384 | 1.00 | 20.22 | C |
| ATOM | 1232 | OG | SER | A | 398 | 5.807 | −36.483 | −65.729 | 1.00 | 27.61 | O |
| ATOM | 1233 | C | SER | A | 398 | 9.306 | −36.414 | −64.447 | 1.00 | 21.04 | C |
| ATOM | 1234 | O | SER | A | 398 | 9.542 | −35.611 | −63.548 | 1.00 | 18.56 | O |
| ATOM | 1235 | N | HIS | A | 399 | 10.229 | −36.824 | −65.305 | 1.00 | 20.73 | N |
| ATOM | 1236 | CA | HIS | A | 399 | 11.618 | −36.356 | −65.214 | 1.00 | 23.98 | C |
| ATOM | 1237 | CB | HIS | A | 399 | 12.552 | −37.301 | −65.980 | 1.00 | 26.36 | C |
| ATOM | 1238 | CG | HIS | A | 399 | 12.905 | −38.558 | −65.222 | 1.00 | 38.61 | C |
| ATOM | 1239 | ND1 | HIS | A | 399 | 12.082 | −39.114 | −64.298 | 1.00 | 37.93 | N |
| ATOM | 1240 | CE1 | HIS | A | 399 | 12.651 | −40.224 | −63.803 | 1.00 | 35.70 | C |
| ATOM | 1241 | NE2 | HIS | A | 399 | 13.837 | −40.394 | −64.411 | 1.00 | 38.97 | N |
| ATOM | 1242 | CD2 | HIS | A | 399 | 14.025 | −39.388 | −65.293 | 1.00 | 37.44 | C |
| ATOM | 1243 | C | HIS | A | 399 | 11.692 | −34.962 | −65.775 | 1.00 | 23.95 | C |
| ATOM | 1244 | O | HIS | A | 399 | 11.474 | −34.758 | −66.958 | 1.00 | 26.60 | O |
| ATOM | 1245 | N | ILE | A | 400 | 11.943 | −33.976 | −64.917 | 1.00 | 17.27 | N |
| ATOM | 1246 | CA | ILE | A | 400 | 11.912 | −32.570 | −65.360 | 1.00 | 17.27 | C |
| ATOM | 1247 | CB | ILE | A | 400 | 11.344 | −31.628 | −64.252 | 1.00 | 19.92 | C |
| ATOM | 1248 | CG1 | ILE | A | 400 | 10.029 | −32.185 | −63.717 | 1.00 | 23.37 | C |
| ATOM | 1249 | CD1 | ILE | A | 400 | 8.992 | −32.393 | −64.791 | 1.00 | 22.30 | C |
| ATOM | 1250 | CG2 | ILE | A | 400 | 11.112 | −30.193 | −64.805 | 1.00 | 16.32 | C |
| ATOM | 1251 | C | ILE | A | 400 | 13.325 | −32.081 | −65.751 | 1.00 | 15.70 | C |
| ATOM | 1252 | O | ILE | A | 400 | 13.477 | −31.209 | −66.608 | 1.00 | 16.12 | O |
| ATOM | 1253 | N | GLY | A | 401 | 14.338 | −32.618 | −65.084 | 1.00 | 17.30 | N |
| ATOM | 1254 | CA | GLY | A | 401 | 15.707 | −32.124 | −65.280 | 1.00 | 16.35 | C |
| ATOM | 1255 | C | GLY | A | 401 | 16.649 | −32.656 | −64.242 | 1.00 | 17.80 | C |
| ATOM | 1256 | O | GLY | A | 401 | 16.549 | −33.825 | −63.825 | 1.00 | 18.07 | O |
| ATOM | 1257 | N | TRP | A | 402 | 17.607 | −31.813 | −63.836 | 1.00 | 15.87 | N |
| ATOM | 1258 | CA | TRP | A | 402 | 18.672 | −32.244 | −62.939 | 1.00 | 14.10 | C |
| ATOM | 1259 | CB | TRP | A | 402 | 19.949 | −32.590 | −63.735 | 1.00 | 16.11 | C |
| ATOM | 1260 | CG | TRP | A | 402 | 19.710 | −33.668 | −64.748 | 1.00 | 17.78 | C |
| ATOM | 1261 | CD1 | TRP | A | 402 | 19.912 | −35.028 | −64.588 | 1.00 | 17.21 | C |
| ATOM | 1262 | NE1 | TRP | A | 402 | 19.526 | −35.709 | −65.716 | 1.00 | 20.74 | N |
| ATOM | 1263 | CE2 | TRP | A | 402 | 19.081 | −34.839 | −66.655 | 1.00 | 19.99 | C |
| ATOM | 1264 | CD2 | TRP | A | 402 | 19.161 | −33.506 | −66.080 | 1.00 | 18.31 | C |
| ATOM | 1265 | CE3 | TRP | A | 402 | 18.730 | −32.417 | −66.831 | 1.00 | 19.19 | C |
| ATOM | 1266 | CZ3 | TRP | A | 402 | 18.216 | −32.655 | −68.120 | 1.00 | 22.55 | C |
| ATOM | 1267 | CH2 | TRP | A | 402 | 18.127 | −33.961 | −68.640 | 1.00 | 20.63 | C |
| ATOM | 1268 | CZ2 | TRP | A | 402 | 18.561 | −35.066 | −67.920 | 1.00 | 23.58 | C |
| ATOM | 1269 | C | TRP | A | 402 | 19.019 | −31.130 | −62.004 | 1.00 | 15.12 | C |
| ATOM | 1270 | O | TRP | A | 402 | 18.966 | −29.957 | −62.383 | 1.00 | 15.21 | O |
| ATOM | 1271 | N | LYS | A | 403 | 19.375 | −31.494 | −60.785 | 1.00 | 17.30 | N |
| ATOM | 1272 | CA | LYS | A | 403 | 20.052 | −30.576 | −59.875 | 1.00 | 15.95 | C |
| ATOM | 1273 | CB | LYS | A | 403 | 19.773 | −30.939 | −58.442 | 1.00 | 19.03 | C |
| ATOM | 1274 | CG | LYS | A | 403 | 20.163 | −29.836 | −57.442 | 1.00 | 21.17 | C |
| ATOM | 1275 | CD | LYS | A | 403 | 20.084 | −30.380 | −56.012 | 1.00 | 22.22 | C |
| ATOM | 1276 | CE | LYS | A | 403 | 20.025 | −29.262 | −54.973 | 1.00 | 30.25 | C |
| ATOM | 1277 | NZ | LYS | A | 403 | 20.272 | −29.871 | −53.635 | 1.00 | 40.26 | N |
| ATOM | 1278 | C | LYS | A | 403 | 21.561 | −30.655 | −60.121 | 1.00 | 19.31 | C |

TABLE 5-continued

Atomic coordinates for CRBN(TBD):Thalidomide (Murine protein)

| ATOM | 1279 | O | LYS | A | 403 | 22.151 | −31.748 | −60.123 | 1.00 | 21.01 | O |
|------|------|------|-----|---|-----|--------|---------|---------|------|-------|---|
| ATOM | 1280 | N | PHE | A | 404 | 22.174 | −29.505 | −60.335 | 1.00 | 14.51 | N |
| ATOM | 1281 | CA | PHE | A | 404 | 23.620 | −29.439 | −60.555 | 1.00 | 16.13 | C |
| ATOM | 1282 | CB | PHE | A | 404 | 23.927 | −28.551 | −61.739 | 1.00 | 16.01 | C |
| ATOM | 1283 | CG | PHE | A | 404 | 23.694 | −29.231 | −63.059 | 1.00 | 20.17 | C |
| ATOM | 1284 | CD1 | PHE | A | 404 | 24.676 | −30.083 | −63.567 | 1.00 | 18.44 | C |
| ATOM | 1285 | CE1 | PHE | A | 404 | 24.441 | −30.796 | −64.778 | 1.00 | 20.09 | C |
| ATOM | 1286 | CZ | PHE | A | 404 | 23.224 | −30.649 | −65.446 | 1.00 | 17.78 | C |
| ATOM | 1287 | CE2 | PHE | A | 404 | 22.218 | −29.833 | −64.910 | 1.00 | 16.13 | C |
| ATOM | 1288 | CD2 | PHE | A | 404 | 22.462 | −29.103 | −63.724 | 1.00 | 15.93 | C |
| ATOM | 1289 | C | PHE | A | 404 | 24.257 | −28.882 | −59.301 | 1.00 | 19.95 | C |
| ATOM | 1290 | O | PHE | A | 404 | 23.831 | −27.831 | −58.805 | 1.00 | 17.09 | O |
| ATOM | 1291 | N | THR | A | 405 | 25.231 | −29.609 | −58.764 | 1.00 | 17.32 | N |
| ATOM | 1292 | CA | THR | A | 405 | 25.909 | −29.215 | −57.525 | 1.00 | 20.07 | C |
| ATOM | 1293 | CB | THR | A | 405 | 25.658 | −30.281 | −56.434 | 1.00 | 23.95 | C |
| ATOM | 1294 | OG1 | THR | A | 405 | 25.926 | −31.585 | −56.977 | 1.00 | 28.20 | O |
| ATOM | 1295 | CG2 | THR | A | 405 | 24.142 | −30.270 | −55.973 | 1.00 | 25.69 | C |
| ATOM | 1296 | C | THR | A | 405 | 27.435 | −29.017 | −57.762 | 1.00 | 23.38 | C |
| ATOM | 1297 | O | THR | A | 405 | 28.080 | −29.831 | −58.447 | 1.00 | 22.36 | O |
| ATOM | 1298 | N | ALA | A | 406 | 27.986 | −27.898 | −57.262 | 1.00 | 21.03 | N |
| ATOM | 1299 | CA | ALA | A | 406 | 29.404 | −27.538 | −57.519 | 1.00 | 23.57 | C |
| ATOM | 1300 | CB | ALA | A | 406 | 29.710 | −26.147 | −56.932 | 1.00 | 22.59 | C |
| ATOM | 1301 | C | ALA | A | 406 | 30.333 | −28.568 | −56.907 | 1.00 | 24.15 | C |
| ATOM | 1302 | O | ALA | A | 406 | 30.087 | −29.038 | −55.833 | 1.00 | 25.53 | O |
| ATOM | 1303 | N | THR | A | 407 | 31.402 | −28.922 | −57.609 | 1.00 | 28.23 | N |
| ATOM | 1304 | CA | THR | A | 407 | 32.384 | −29.843 | −57.039 | 1.00 | 29.91 | C |
| ATOM | 1305 | CB | THR | A | 407 | 33.084 | −30.689 | −58.128 | 1.00 | 25.99 | C |
| ATOM | 1306 | OG1 | THR | A | 407 | 33.745 | −29.819 | −59.059 | 1.00 | 28.89 | O |
| ATOM | 1307 | CG2 | THR | A | 407 | 32.066 | −31.527 | −58.874 | 1.00 | 26.23 | C |
| ATOM | 1308 | C | THR | A | 407 | 33.435 | −29.101 | −56.177 | 1.00 | 36.18 | C |
| ATOM | 1309 | O | THR | A | 407 | 34.094 | −29.717 | −55.370 | 1.00 | 34.56 | O |
| ATOM | 1310 | N | LYS | A | 408 | 33.558 | −27.780 | −56.352 | 1.00 | 29.09 | N |
| ATOM | 1311 | CA | LYS | A | 408 | 34.460 | −26.958 | −55.515 | 1.00 | 37.57 | C |
| ATOM | 1312 | CB | LYS | A | 408 | 35.575 | −26.332 | −56.369 | 1.00 | 34.23 | C |
| ATOM | 1313 | CG | LYS | A | 408 | 36.430 | −27.332 | −57.146 | 1.00 | 39.89 | C |
| ATOM | 1314 | CD | LYS | A | 408 | 37.785 | −26.732 | −57.514 | 1.00 | 49.23 | C |
| ATOM | 1315 | CE | LYS | A | 408 | 37.652 | −25.438 | −58.312 | 1.00 | 55.68 | C |
| ATOM | 1316 | NZ | LYS | A | 408 | 37.440 | −25.692 | −59.765 | 1.00 | 54.21 | N |
| ATOM | 1317 | C | LYS | A | 408 | 33.722 | −25.836 | −54.780 | 1.00 | 34.85 | C |
| ATOM | 1318 | O | LYS | A | 408 | 32.818 | −25.197 | −55.333 | 1.00 | 25.69 | O |
| ATOM | 1319 | N | LYS | A | 409 | 34.176 | −25.524 | −53.573 | 1.00 | 31.99 | N |
| ATOM | 1320 | CA | LYS | A | 409 | 33.569 | −24.451 | −52.792 | 1.00 | 26.25 | C |
| ATOM | 1321 | CB | LYS | A | 409 | 34.125 | −24.443 | −51.350 | 1.00 | 32.85 | C |
| ATOM | 1322 | CG | LYS | A | 409 | 33.475 | −25.462 | −50.426 | 1.00 | 40.79 | C |
| ATOM | 1323 | CD | LYS | A | 409 | 32.471 | −24.806 | −49.499 | 1.00 | 50.12 | C |
| ATOM | 1324 | CE | LYS | A | 409 | 31.959 | −25.792 | −48.455 | 1.00 | 55.36 | C |
| ATOM | 1325 | NZ | LYS | A | 409 | 30.861 | −26.650 | −48.998 | 1.00 | 53.81 | N |
| ATOM | 1326 | C | LYS | A | 409 | 33.687 | −23.054 | −53.409 | 1.00 | 24.07 | C |
| ATOM | 1327 | O | LYS | A | 409 | 32.896 | −22.166 | −53.088 | 1.00 | 29.10 | O |
| ATOM | 1328 | N | ASP | A | 410 | 34.683 | −22.820 | −54.245 | 1.00 | 26.10 | N |
| ATOM | 1329 | CA | ASP | A | 410 | 34.947 | −21.411 | −54.633 | 1.00 | 31.13 | C |
| ATOM | 1330 | CB | ASP | A | 410 | 36.424 | −21.194 | −54.985 | 1.00 | 43.91 | C |
| ATOM | 1331 | CG | ASP | A | 410 | 36.894 | −22.092 | −56.120 | 1.00 | 46.43 | C |
| ATOM | 1332 | OD1 | ASP | A | 410 | 36.042 | −22.719 | −56.793 | 1.00 | 47.71 | O |
| ATOM | 1333 | OD2 | ASP | A | 410 | 38.118 | −22.160 | −56.347 | 1.00 | 62.90 | O |
| ATOM | 1334 | C | ASP | A | 410 | 34.038 | −20.932 | −55.782 | 1.00 | 34.75 | C |
| ATOM | 1335 | O | ASP | A | 410 | 34.136 | −19.780 | −56.226 | 1.00 | 33.89 | O |
| ATOM | 1336 | N | MET | A | 411 | 33.156 | −21.833 | −56.247 | 1.00 | 30.59 | N |
| ATOM | 1337 | CA | MET | A | 411 | 32.273 | −21.580 | −57.393 | 1.00 | 31.59 | C |
| ATOM | 1338 | CB | MET | A | 411 | 31.923 | −22.917 | −58.078 | 1.00 | 25.09 | C |
| ATOM | 1339 | CG | MET | A | 411 | 33.155 | −23.553 | −58.683 | 1.00 | 38.34 | C |
| ATOM | 1340 | SD | MET | A | 411 | 32.886 | −25.110 | −59.523 | 1.00 | 35.70 | S |
| ATOM | 1341 | CE | MET | A | 411 | 32.345 | −26.148 | −58.205 | 1.00 | 40.76 | C |
| ATOM | 1342 | C | MET | A | 411 | 30.986 | −20.865 | −56.983 | 1.00 | 29.05 | C |
| ATOM | 1343 | O | MET | A | 411 | 30.542 | −20.984 | −55.849 | 1.00 | 24.90 | O |
| ATOM | 1344 | N | SER | A | 412 | 30.412 | −20.101 | −57.912 | 1.00 | 26.31 | N |
| ATOM | 1345 | CA | SER | A | 412 | 29.044 | −19.577 | −57.756 | 1.00 | 23.18 | C |
| ATOM | 1346 | CB | SER | A | 412 | 29.028 | −18.075 | −57.478 | 1.00 | 25.95 | C |
| ATOM | 1347 | OG | SER | A | 412 | 29.735 | −17.356 | −58.485 | 1.00 | 33.06 | O |
| ATOM | 1348 | C | SER | A | 412 | 28.228 | −19.940 | −58.981 | 1.00 | 18.92 | C |
| ATOM | 1349 | O | SER | A | 412 | 28.699 | −19.686 | −60.092 | 1.00 | 19.11 | O |
| ATOM | 1350 | N | PRO | A | 413 | 26.914 | −20.050 | −58.790 | 1.00 | 19.00 | N |
| ATOM | 1351 | CA | PRO | A | 413 | 26.284 | −20.718 | −57.630 | 1.00 | 16.35 | C |
| ATOM | 1352 | CB | PRO | A | 413 | 24.795 | −20.776 | −58.039 | 1.00 | 16.81 | C |
| ATOM | 1353 | CG | PRO | A | 413 | 24.848 | −21.037 | −59.512 | 1.00 | 15.99 | C |
| ATOM | 1354 | CD | PRO | A | 413 | 26.143 | −20.319 | −60.032 | 1.00 | 15.71 | C |
| ATOM | 1355 | C | PRO | A | 413 | 26.826 | −22.093 | −57.201 | 1.00 | 17.48 | C |
| ATOM | 1356 | O | PRO | A | 413 | 27.332 | −22.842 | −58.016 | 1.00 | 17.78 | O |

TABLE 5-continued

Atomic coordinates for CRBN(TBD):Thalidomide (Murine protein)

| ATOM | 1357 | N | GLN | A | 414 | 26.698 | −22.419 | −55.924 | 1.00 | 16.45 | N |
|---|---|---|---|---|---|---|---|---|---|---|---|
| ATOM | 1358 | CA | GLN | A | 414 | 27.085 | −23.757 | −55.452 | 1.00 | 16.16 | C |
| ATOM | 1359 | CB | GLN | A | 414 | 27.118 | −23.771 | −53.908 | 1.00 | 20.14 | C |
| ATOM | 1360 | CG | GLN | A | 414 | 28.411 | −23.115 | −53.370 | 1.00 | 17.68 | C |
| ATOM | 1361 | CD | GLN | A | 414 | 29.612 | −23.952 | −53.711 | 1.00 | 19.82 | C |
| ATOM | 1362 | OE1 | GLN | A | 414 | 30.433 | −23.588 | −54.569 | 1.00 | 24.32 | O |
| ATOM | 1363 | NE2 | GLN | A | 414 | 29.682 | −25.106 | −53.121 | 1.00 | 17.48 | N |
| ATOM | 1364 | C | GLN | A | 414 | 26.123 | −24.845 | −55.986 | 1.00 | 15.39 | C |
| ATOM | 1365 | O | GLN | A | 414 | 26.474 | −26.043 | −56.031 | 1.00 | 19.71 | O |
| ATOM | 1366 | N | LYS | A | 415 | 24.926 | −24.425 | −56.374 | 1.00 | 15.24 | N |
| ATOM | 1367 | CA | LYS | A | 415 | 24.011 | −25.317 | −57.068 | 1.00 | 17.66 | C |
| ATOM | 1368 | CB | LYS | A | 415 | 23.345 | −26.277 | −56.088 | 1.00 | 19.03 | C |
| ATOM | 1369 | CG | LYS | A | 415 | 22.389 | −25.609 | −55.129 | 1.00 | 23.48 | C |
| ATOM | 1370 | CD | LYS | A | 415 | 21.026 | −25.483 | −55.779 | 1.00 | 29.23 | C |
| ATOM | 1371 | CE | LYS | A | 415 | 19.980 | −25.059 | −54.757 | 1.00 | 36.87 | C |
| ATOM | 1372 | NZ | LYS | A | 415 | 20.289 | −23.745 | −54.117 | 1.00 | 34.89 | N |
| ATOM | 1373 | C | LYS | A | 415 | 22.996 | −24.562 | −57.903 | 1.00 | 14.85 | C |
| ATOM | 1374 | O | LYS | A | 415 | 22.779 | −23.344 | −57.721 | 1.00 | 14.11 | O |
| ATOM | 1375 | N | PHE | A | 416 | 22.423 | −25.260 | −58.882 | 1.00 | 14.03 | N |
| ATOM | 1376 | CA | PHE | A | 416 | 21.351 | −24.676 | −59.668 | 1.00 | 12.36 | C |
| ATOM | 1377 | CB | PHE | A | 416 | 21.887 | −23.714 | −60.771 | 1.00 | 14.50 | C |
| ATOM | 1378 | CG | PHE | A | 416 | 22.752 | −24.396 | −61.806 | 1.00 | 14.79 | C |
| ATOM | 1379 | CD2 | PHE | A | 416 | 22.197 | −24.879 | −62.992 | 1.00 | 17.15 | C |
| ATOM | 1380 | CE2 | PHE | A | 416 | 22.996 | −25.493 | −63.946 | 1.00 | 17.56 | C |
| ATOM | 1381 | CZ | PHE | A | 416 | 24.343 | −25.665 | −63.713 | 1.00 | 20.09 | C |
| ATOM | 1382 | CE1 | PHE | A | 416 | 24.916 | −25.203 | −62.519 | 1.00 | 16.98 | C |
| ATOM | 1383 | CD1 | PHE | A | 416 | 24.116 | −24.588 | −61.574 | 1.00 | 18.98 | C |
| ATOM | 1384 | C | PHE | A | 416 | 20.600 | −25.853 | −60.264 | 1.00 | 12.59 | C |
| ATOM | 1385 | O | PHE | A | 416 | 20.925 | −27.009 | −59.979 | 1.00 | 15.60 | O |
| ATOM | 1386 | N | TRP | A | 417 | 19.574 | −25.559 | −61.035 | 1.00 | 14.09 | N |
| ATOM | 1387 | CA | TRP | A | 417 | 18.785 | −26.607 | −61.686 | 1.00 | 13.27 | C |
| ATOM | 1388 | CB | TRP | A | 417 | 17.335 | −26.496 | −61.243 | 1.00 | 14.58 | C |
| ATOM | 1389 | CG | TRP | A | 417 | 17.171 | −26.569 | −59.755 | 1.00 | 14.33 | C |
| ATOM | 1390 | CD1 | TRP | A | 417 | 17.294 | −25.515 | −58.823 | 1.00 | 14.78 | C |
| ATOM | 1391 | NE1 | TRP | A | 417 | 17.125 | −25.987 | −57.546 | 1.00 | 16.20 | N |
| ATOM | 1392 | CE2 | TRP | A | 417 | 16.851 | −27.315 | −57.570 | 1.00 | 17.92 | C |
| ATOM | 1393 | CD2 | TRP | A | 417 | 16.899 | −27.747 | −58.975 | 1.00 | 16.73 | C |
| ATOM | 1394 | CE3 | TRP | A | 417 | 16.682 | −29.099 | −59.284 | 1.00 | 17.17 | C |
| ATOM | 1395 | CZ3 | TRP | A | 417 | 16.418 | −29.994 | −58.234 | 1.00 | 22.73 | C |
| ATOM | 1396 | CH2 | TRP | A | 417 | 16.373 | −29.556 | −56.882 | 1.00 | 21.81 | C |
| ATOM | 1397 | CZ2 | TRP | A | 417 | 16.590 | −28.199 | −56.535 | 1.00 | 19.90 | C |
| ATOM | 1398 | C | TRP | A | 417 | 18.844 | −26.414 | −63.164 | 1.00 | 14.40 | C |
| ATOM | 1399 | O | TRP | A | 417 | 18.699 | −25.294 | −63.647 | 1.00 | 16.44 | O |
| ATOM | 1400 | N | GLY | A | 418 | 18.989 | −27.525 | −63.902 | 1.00 | 13.65 | N |
| ATOM | 1401 | CA | GLY | A | 418 | 18.917 | −27.497 | −65.376 | 1.00 | 14.90 | C |
| ATOM | 1402 | C | GLY | A | 418 | 17.683 | −28.297 | −65.778 | 1.00 | 14.31 | C |
| ATOM | 1403 | O | GLY | A | 418 | 17.579 | −29.475 | −65.468 | 1.00 | 16.37 | O |
| ATOM | 1404 | N | LEU | A | 419 | 16.717 | −27.614 | −66.366 | 1.00 | 16.42 | N |
| ATOM | 1405 | CA | LEU | A | 419 | 15.388 | −28.178 | −66.578 | 1.00 | 13.55 | C |
| ATOM | 1406 | CB | LEU | A | 419 | 14.322 | −27.333 | −65.896 | 1.00 | 15.25 | C |
| ATOM | 1407 | CG | LEU | A | 419 | 14.547 | −27.012 | −64.404 | 1.00 | 15.95 | C |
| ATOM | 1408 | CD1 | LEU | A | 419 | 13.413 | −26.117 | −63.922 | 1.00 | 18.96 | C |
| ATOM | 1409 | CD2 | LEU | A | 419 | 14.600 | −28.300 | −63.584 | 1.00 | 15.01 | C |
| ATOM | 1410 | C | LEU | A | 419 | 15.092 | −28.252 | −68.059 | 1.00 | 15.68 | C |
| ATOM | 1411 | O | LEU | A | 419 | 15.370 | −27.329 | −68.809 | 1.00 | 15.62 | O |
| ATOM | 1412 | N | THR | A | 420 | 14.532 | −29.373 | −68.467 | 1.00 | 18.21 | N |
| ATOM | 1413 | CA | THR | A | 420 | 14.182 | −29.592 | −69.885 | 1.00 | 17.19 | C |
| ATOM | 1414 | CB | THR | A | 420 | 13.827 | −31.079 | −70.074 | 1.00 | 16.08 | C |
| ATOM | 1415 | OG1 | THR | A | 420 | 14.934 | −31.854 | −69.645 | 1.00 | 17.97 | O |
| ATOM | 1416 | CG2 | THR | A | 420 | 13.519 | −31.411 | −71.576 | 1.00 | 21.47 | C |
| ATOM | 1417 | C | THR | A | 420 | 12.978 | −28.751 | −70.186 | 1.00 | 15.49 | C |
| ATOM | 1418 | O | THR | A | 420 | 11.923 | −28.970 | −69.610 | 1.00 | 17.29 | O |
| ATOM | 1419 | N | ARG | A | 421 | 13.116 | −27.790 | −71.105 | 1.00 | 14.83 | N |
| ATOM | 1420 | CA | ARG | A | 421 | 12.081 | −26.763 | −71.312 | 1.00 | 20.90 | C |
| ATOM | 1421 | CB | ARG | A | 421 | 12.505 | −25.763 | −72.394 | 1.00 | 25.72 | C |
| ATOM | 1422 | CG | ARG | A | 421 | 13.530 | −24.738 | −71.955 | 1.00 | 35.74 | C |
| ATOM | 1423 | CD | ARG | A | 421 | 13.908 | −23.816 | −73.127 | 1.00 | 47.49 | C |
| ATOM | 1424 | NE | ARG | A | 421 | 15.140 | −23.066 | −72.854 | 1.00 | 49.32 | N |
| ATOM | 1425 | CZ | ARG | A | 421 | 15.185 | −21.771 | −72.554 | 1.00 | 59.92 | C |
| ATOM | 1426 | NH1 | ARG | A | 421 | 14.064 | −21.051 | −72.511 | 1.00 | 66.35 | N |
| ATOM | 1427 | NH2 | ARG | A | 421 | 16.358 | −21.187 | −72.309 | 1.00 | 55.67 | N |
| ATOM | 1428 | C | ARG | A | 421 | 10.749 | −27.388 | −71.744 | 1.00 | 19.86 | C |
| ATOM | 1429 | O | ARG | A | 421 | 9.684 | −26.887 | −71.421 | 1.00 | 17.71 | O |
| ATOM | 1430 | N | SER | A | 422 | 10.834 | −28.477 | −72.494 | 1.00 | 17.52 | N |
| ATOM | 1431 | CA | SER | A | 422 | 9.622 | −29.081 | −73.047 | 1.00 | 22.34 | C |
| ATOM | 1432 | CB | SER | A | 422 | 9.972 | −30.022 | −74.214 | 1.00 | 23.06 | C |
| ATOM | 1433 | OG | SER | A | 422 | 10.776 | −31.082 | −73.767 | 1.00 | 23.61 | O |
| ATOM | 1434 | C | SER | A | 422 | 8.832 | −29.825 | −71.968 | 1.00 | 19.92 | C |

TABLE 5-continued

Atomic coordinates for CRBN(TBD):Thalidomide (Murine protein)

| ATOM | 1435 | O   | SER | A | 422 | 7.699  | −30.237 | −72.209 | 1.00 | 21.55 | O |
|------|------|-----|-----|---|-----|--------|---------|---------|------|-------|---|
| ATOM | 1436 | N   | ALA | A | 423 | 9.454  | −30.027 | −70.787 | 1.00 | 18.29 | N |
| ATOM | 1437 | CA  | ALA | A | 423 | 8.777  | −30.667 | −69.645 | 1.00 | 17.59 | C |
| ATOM | 1438 | CB  | ALA | A | 423 | 9.783  | −31.363 | −68.726 | 1.00 | 17.38 | C |
| ATOM | 1439 | C   | ALA | A | 423 | 7.940  | −29.675 | −68.847 | 1.00 | 17.51 | C |
| ATOM | 1440 | O   | ALA | A | 423 | 7.285  | −30.051 | −67.856 | 1.00 | 16.65 | O |
| ATOM | 1441 | N   | LEU | A | 424 | 7.982  | −28.405 | −69.251 | 1.00 | 14.88 | N |
| ATOM | 1442 | CA  | LEU | A | 424 | 7.302  | −27.332 | −68.517 | 1.00 | 16.25 | C |
| ATOM | 1443 | CB  | LEU | A | 424 | 8.327  | −26.333 | −67.974 | 1.00 | 15.98 | C |
| ATOM | 1444 | CG  | LEU | A | 424 | 9.431  | −26.917 | −67.082 | 1.00 | 19.37 | C |
| ATOM | 1445 | CD1 | LEU | A | 424 | 10.536 | −25.873 | −66.914 | 1.00 | 22.31 | C |
| ATOM | 1446 | CD2 | LEU | A | 424 | 8.859  | −27.347 | −65.714 | 1.00 | 19.49 | C |
| ATOM | 1447 | C   | LEU | A | 424 | 6.255  | −26.597 | −69.356 | 1.00 | 20.91 | C |
| ATOM | 1448 | O   | LEU | A | 424 | 6.382  | −26.498 | −70.589 | 1.00 | 18.67 | O |
| ATOM | 1449 | N   | LEU | A | 425 | 5.259  | −26.025 | −68.669 | 1.00 | 20.30 | N |
| ATOM | 1450 | CA  | LEU | A | 425 | 4.191  | −25.232 | −69.319 | 1.00 | 24.52 | C |
| ATOM | 1451 | CB  | LEU | A | 425 | 2.832  | −25.809 | −68.954 | 1.00 | 31.62 | C |
| ATOM | 1452 | CG  | LEU | A | 425 | 1.754  | −26.121 | −69.989 | 1.00 | 49.01 | C |
| ATOM | 1453 | CD1 | LEU | A | 425 | 2.319  | −26.800 | −71.229 | 1.00 | 41.11 | C |
| ATOM | 1454 | CD2 | LEU | A | 425 | 0.693  | −26.994 | −69.326 | 1.00 | 37.22 | C |
| ATOM | 1455 | C   | LEU | A | 425 | 4.320  | −23.817 | −68.779 | 1.00 | 31.26 | C |
| ATOM | 1456 | O   | LEU | A | 425 | 4.498  | −23.673 | −67.554 | 1.00 | 26.55 | O |
| ATOM | 1457 | N   | PRO | A | 426 | 3.829  | −22.831 | −69.571 | 1.00 | 38.63 | N |
| ATOM | 1458 | CA  | PRO | A | 426 | 4.472  | −22.132 | −70.665 | 1.00 | 44.78 | C |
| ATOM | 1459 | CB  | PRO | A | 426 | 4.778  | −20.753 | −70.066 | 1.00 | 39.91 | C |
| ATOM | 1460 | CG  | PRO | A | 426 | 3.697  | −20.563 | −69.031 | 1.00 | 47.03 | C |
| ATOM | 1461 | CD  | PRO | A | 426 | 2.972  | −21.886 | −68.836 | 1.00 | 47.91 | C |
| ATOM | 1462 | C   | PRO | A | 426 | 5.713  | −22.854 | −71.207 | 1.00 | 32.51 | C |
| ATOM | 1463 | O   | PRO | A | 426 | 6.730  | −22.941 | −70.518 | 1.00 | 45.29 | O |
| ATOM | 1464 | N   | THR | B | 321 | 67.510 | −54.988 | −61.608 | 1.00 | 50.15 | N |
| ATOM | 1465 | CA  | THR | B | 321 | 66.120 | −54.688 | −62.057 | 1.00 | 45.53 | C |
| ATOM | 1466 | CB  | THR | B | 321 | 65.100 | −55.503 | −61.254 | 1.00 | 47.96 | C |
| ATOM | 1467 | OG1 | THR | B | 321 | 65.342 | −55.316 | −59.859 | 1.00 | 46.61 | O |
| ATOM | 1468 | CG2 | THR | B | 321 | 65.181 | −57.010 | −61.607 | 1.00 | 53.71 | C |
| ATOM | 1469 | C   | THR | B | 321 | 65.799 | −53.188 | −61.895 | 1.00 | 39.43 | C |
| ATOM | 1470 | O   | THR | B | 321 | 64.657 | −52.773 | −62.075 | 1.00 | 34.49 | O |
| ATOM | 1471 | N   | SER | B | 322 | 66.823 | −52.391 | −61.581 | 1.00 | 36.88 | N |
| ATOM | 1472 | CA  | SER | B | 322 | 66.637 | −51.033 | −61.064 | 1.00 | 29.11 | C |
| ATOM | 1473 | CB  | SER | B | 322 | 67.823 | −50.617 | −60.177 | 1.00 | 36.22 | C |
| ATOM | 1474 | OG  | SER | B | 322 | 67.703 | −51.173 | −58.884 | 1.00 | 43.63 | O |
| ATOM | 1475 | C   | SER | B | 322 | 66.438 | −49.999 | −62.147 | 1.00 | 30.62 | C |
| ATOM | 1476 | O   | SER | B | 322 | 67.098 | −50.025 | −63.172 | 1.00 | 29.43 | O |
| ATOM | 1477 | N   | LEU | B | 323 | 65.499 | −49.091 | −61.914 | 1.00 | 26.36 | N |
| ATOM | 1478 | CA  | LEU | B | 323 | 65.290 | −47.953 | −62.808 | 1.00 | 27.16 | C |
| ATOM | 1479 | CB  | LEU | B | 323 | 63.846 | −47.929 | −63.337 | 1.00 | 24.04 | C |
| ATOM | 1480 | CG  | LEU | B | 323 | 63.403 | −49.230 | −64.057 | 1.00 | 28.53 | C |
| ATOM | 1481 | CD1 | LEU | B | 323 | 61.917 | −49.184 | −64.406 | 1.00 | 28.53 | C |
| ATOM | 1482 | CD2 | LEU | B | 323 | 64.224 | −49.482 | −65.305 | 1.00 | 28.81 | C |
| ATOM | 1483 | C   | LEU | B | 323 | 65.605 | −46.706 | −62.016 | 1.00 | 24.54 | C |
| ATOM | 1484 | O   | LEU | B | 323 | 64.988 | −46.443 | −60.976 | 1.00 | 23.32 | O |
| ATOM | 1485 | N   | CYS | B | 324 | 66.595 | −45.953 | −62.494 | 1.00 | 23.12 | N |
| ATOM | 1486 | CA  | CYS | B | 324 | 67.134 | −44.818 | −61.774 | 1.00 | 22.61 | C |
| ATOM | 1487 | CB  | CYS | B | 324 | 68.659 | −44.989 | −61.582 | 1.00 | 25.17 | C |
| ATOM | 1488 | SG  | CYS | B | 324 | 69.079 | −46.490 | −60.692 | 1.00 | 34.87 | S |
| ATOM | 1489 | C   | CYS | B | 324 | 66.864 | −43.544 | −62.523 | 1.00 | 24.14 | C |
| ATOM | 1490 | O   | CYS | B | 324 | 66.644 | −43.563 | −63.732 | 1.00 | 23.60 | O |
| ATOM | 1491 | N   | CYS | B | 325 | 66.818 | −42.440 | −61.789 | 1.00 | 21.75 | N |
| ATOM | 1492 | CA  | CYS | B | 325 | 66.672 | −41.106 | −62.384 | 1.00 | 24.00 | C |
| ATOM | 1493 | CB  | CYS | B | 325 | 66.868 | −40.054 | −61.298 | 1.00 | 26.44 | C |
| ATOM | 1494 | SG  | CYS | B | 325 | 66.820 | −38.357 | −61.899 | 1.00 | 23.82 | S |
| ATOM | 1495 | C   | CYS | B | 325 | 67.733 | −40.898 | −63.467 | 1.00 | 26.57 | C |
| ATOM | 1496 | O   | CYS | B | 325 | 68.918 | −41.069 | −63.209 | 1.00 | 29.43 | O |
| ATOM | 1497 | N   | LYS | B | 326 | 67.318 | −40.575 | −64.682 | 1.00 | 24.89 | N |
| ATOM | 1498 | CA  | LYS | B | 326 | 68.298 | −40.492 | −65.766 | 1.00 | 32.55 | C |
| ATOM | 1499 | CB  | LYS | B | 326 | 67.627 | −40.522 | −67.130 | 1.00 | 29.78 | C |
| ATOM | 1500 | CG  | LYS | B | 326 | 68.610 | −40.427 | −68.307 | 1.00 | 33.05 | C |
| ATOM | 1501 | CD  | LYS | B | 326 | 67.896 | −40.593 | −69.626 | 1.00 | 37.12 | C |
| ATOM | 1502 | CE  | LYS | B | 326 | 67.481 | −39.246 | −70.192 | 1.00 | 49.68 | C |
| ATOM | 1503 | NZ  | LYS | B | 326 | 66.570 | −39.387 | −71.373 | 1.00 | 57.66 | N |
| ATOM | 1504 | C   | LYS | B | 326 | 69.149 | −39.228 | −65.607 | 1.00 | 33.07 | C |
| ATOM | 1505 | O   | LYS | B | 326 | 70.324 | −39.221 | −65.946 | 1.00 | 31.21 | O |
| ATOM | 1506 | N   | GLN | B | 327 | 68.538 | −38.183 | −65.060 | 1.00 | 30.41 | N |
| ATOM | 1507 | CA  | GLN | B | 327 | 69.207 | −36.897 | −64.880 | 1.00 | 32.29 | C |
| ATOM | 1508 | CB  | GLN | B | 327 | 68.226 | −35.832 | −64.421 | 1.00 | 30.48 | C |
| ATOM | 1509 | CG  | GLN | B | 327 | 68.890 | −34.503 | −64.072 | 1.00 | 37.69 | C |
| ATOM | 1510 | CD  | GLN | B | 327 | 67.985 | −33.318 | −64.282 | 1.00 | 34.33 | C |
| ATOM | 1511 | OE1 | GLN | B | 327 | 67.464 | −32.744 | −63.338 | 1.00 | 41.08 | O |
| ATOM | 1512 | NE2 | GLN | B | 327 | 67.809 | −32.938 | −65.519 | 1.00 | 37.96 | N |

TABLE 5-continued

Atomic coordinates for CRBN(TBD):Thalidomide (Murine protein)

| ATOM | 1513 | C | GLN | B | 327 | 70.414 | −36.963 | −63.937 | 1.00 | 37.97 | C |
|---|---|---|---|---|---|---|---|---|---|---|---|
| ATOM | 1514 | O | GLN | B | 327 | 71.521 | −36.586 | −64.336 | 1.00 | 27.33 | O |
| ATOM | 1515 | N | CYS | B | 328 | 70.206 | −37.452 | −62.704 | 1.00 | 28.79 | N |
| ATOM | 1516 | CA | CYS | B | 328 | 71.290 | −37.465 | −61.688 | 1.00 | 29.66 | C |
| ATOM | 1517 | CB | CYS | B | 328 | 70.839 | −36.801 | −60.384 | 1.00 | 35.67 | C |
| ATOM | 1518 | SG | CYS | B | 328 | 69.660 | −37.749 | −59.343 | 1.00 | 28.53 | S |
| ATOM | 1519 | C | CYS | B | 328 | 71.897 | −38.855 | −61.436 | 1.00 | 34.59 | C |
| ATOM | 1520 | O | CYS | B | 328 | 72.986 | −38.970 | −60.874 | 1.00 | 33.18 | O |
| ATOM | 1521 | N | GLN | B | 329 | 71.193 | −39.901 | −61.870 | 1.00 | 29.14 | N |
| ATOM | 1522 | CA | GLN | B | 329 | 71.597 | −41.306 | −61.623 | 1.00 | 29.80 | C |
| ATOM | 1523 | CB | GLN | B | 329 | 72.766 | −41.727 | −62.527 | 1.00 | 33.43 | C |
| ATOM | 1524 | CG | GLN | B | 329 | 72.418 | −41.827 | −63.997 | 1.00 | 41.84 | C |
| ATOM | 1525 | CD | GLN | B | 329 | 73.593 | −42.298 | −64.827 | 1.00 | 44.44 | C |
| ATOM | 1526 | OE1 | GLN | B | 329 | 74.238 | −41.508 | −65.496 | 1.00 | 47.55 | O |
| ATOM | 1527 | NE2 | GLN | B | 329 | 73.897 | −43.592 | −64.751 | 1.00 | 38.10 | N |
| ATOM | 1528 | C | GLN | B | 329 | 71.906 | −41.671 | −60.167 | 1.00 | 26.74 | C |
| ATOM | 1529 | O | GLN | B | 329 | 72.498 | −42.715 | −59.900 | 1.00 | 30.24 | O |
| ATOM | 1530 | N | GLU | B | 330 | 71.480 | −40.843 | −59.233 | 1.00 | 24.72 | N |
| ATOM | 1531 | CA | GLU | B | 330 | 71.726 | −41.109 | −57.816 | 1.00 | 27.80 | C |
| ATOM | 1532 | CB | GLU | B | 330 | 71.675 | −39.819 | −57.013 | 1.00 | 26.00 | C |
| ATOM | 1533 | CG | GLU | B | 330 | 72.851 | −38.875 | −57.257 | 1.00 | 32.21 | C |
| ATOM | 1534 | CD | GLU | B | 330 | 74.040 | −39.132 | −56.341 | 1.00 | 43.50 | C |
| ATOM | 1535 | OE1 | GLU | B | 330 | 73.977 | −40.057 | −55.487 | 1.00 | 40.85 | O |
| ATOM | 1536 | OE2 | GLU | B | 330 | 75.055 | −38.403 | −56.480 | 1.00 | 39.44 | O |
| ATOM | 1537 | C | GLU | B | 330 | 70.676 | −42.057 | −57.252 | 1.00 | 32.46 | C |
| ATOM | 1538 | O | GLU | B | 330 | 70.978 | −42.896 | −56.398 | 1.00 | 27.68 | O |
| ATOM | 1539 | N | THR | B | 331 | 69.442 | −41.885 | −57.707 | 1.00 | 28.07 | N |
| ATOM | 1540 | CA | THR | B | 331 | 68.285 | −42.473 | −57.031 | 1.00 | 28.91 | C |
| ATOM | 1541 | CB | THR | B | 331 | 67.175 | −41.424 | −56.829 | 1.00 | 26.85 | C |
| ATOM | 1542 | OG1 | THR | B | 331 | 66.976 | −40.698 | −58.052 | 1.00 | 29.33 | O |
| ATOM | 1543 | CG2 | THR | B | 331 | 67.513 | −40.467 | −55.698 | 1.00 | 30.16 | C |
| ATOM | 1544 | C | THR | B | 331 | 67.674 | −43.616 | −57.826 | 1.00 | 27.23 | C |
| ATOM | 1545 | O | THR | B | 331 | 67.367 | −43.458 | −59.015 | 1.00 | 22.40 | O |
| ATOM | 1546 | N | GLU | B | 332 | 67.456 | −44.755 | −57.167 | 1.00 | 26.47 | N |
| ATOM | 1547 | CA | GLU | B | 332 | 66.530 | −45.756 | −57.697 | 1.00 | 22.73 | C |
| ATOM | 1548 | CB | GLU | B | 332 | 66.698 | −47.100 | −56.970 | 1.00 | 29.49 | C |
| ATOM | 1549 | CG | GLU | B | 332 | 66.030 | −48.267 | −57.684 | 1.00 | 24.21 | C |
| ATOM | 1550 | CD | GLU | B | 332 | 66.017 | −49.520 | −56.846 | 1.00 | 29.84 | C |
| ATOM | 1551 | OE1 | GLU | B | 332 | 66.925 | −50.362 | −57.021 | 1.00 | 30.98 | O |
| ATOM | 1552 | OE2 | GLU | B | 332 | 65.116 | −49.656 | −56.001 | 1.00 | 28.42 | O |
| ATOM | 1553 | C | GLU | a | 332 | 65.105 | −45.236 | −57.521 | 1.00 | 22.22 | C |
| ATOM | 1554 | O | GLU | B | 332 | 64.710 | −44.827 | −56.424 | 1.00 | 19.31 | O |
| ATOM | 1555 | N | ILE | B | 333 | 64.340 | −45.240 | −58.610 | 1.00 | 22.08 | N |
| ATOM | 1556 | CA | ILE | B | 333 | 62.947 | −44.770 | −58.570 | 1.00 | 19.15 | C |
| ATOM | 1557 | CB | ILE | B | 333 | 62.649 | −43.847 | −59.787 | 1.00 | 22.55 | C |
| ATOM | 1558 | CG1 | ILE | B | 333 | 63.606 | −42.651 | −59.779 | 1.00 | 23.08 | C |
| ATOM | 1559 | CD1 | ILE | B | 333 | 63.485 | −41.765 | −58.537 | 1.00 | 21.33 | C |
| ATOM | 1560 | CG2 | ILE | B | 333 | 61.201 | −43.355 | −59.763 | 1.00 | 21.98 | C |
| ATOM | 1561 | C | ILE | B | 333 | 61.941 | −45.952 | −58.526 | 1.00 | 18.07 | C |
| ATOM | 1562 | O | ILE | B | 333 | 60.940 | −45.879 | −57.822 | 1.00 | 17.92 | O |
| ATOM | 1563 | N | THR | B | 334 | 62.209 | −46.997 | −59.303 | 1.00 | 18.22 | N |
| ATOM | 1564 | CA | THR | B | 334 | 61.469 | −48.281 | −59.200 | 1.00 | 24.81 | C |
| ATOM | 1565 | CB | THR | B | 334 | 60.305 | −48.442 | −60.216 | 1.00 | 30.63 | C |
| ATOM | 1566 | OG1 | THR | B | 334 | 60.203 | −47.329 | −61.108 | 1.00 | 38.29 | O |
| ATOM | 1567 | CG2 | THR | B | 334 | 59.032 | −48.780 | −59.544 | 1.00 | 18.71 | C |
| ATOM | 1568 | C | THR | B | 334 | 62.333 | −49.419 | −59.601 | 1.00 | 21.83 | C |
| ATOM | 1569 | O | THR | B | 334 | 63.541 | −49.266 | −59.839 | 1.00 | 24.25 | O |
| ATOM | 1570 | N | THR | B | 335 | 61.676 | −50.568 | −59.776 | 1.00 | 19.42 | N |
| ATOM | 1571 | CA | THR | B | 335 | 62.307 | −51.751 | −60.309 | 1.00 | 23.17 | C |
| ATOM | 1572 | CB | THR | B | 335 | 62.603 | −52.772 | −59.205 | 1.00 | 26.92 | C |
| ATOM | 1573 | OG1 | THR | B | 335 | 61.383 | −53.416 | −58.816 | 1.00 | 24.69 | O |
| ATOM | 1574 | CG2 | THR | B | 335 | 63.266 | −52.084 | −57.954 | 1.00 | 23.55 | C |
| ATOM | 1575 | C | THR | B | 335 | 61.360 | −52.400 | −61.305 | 1.00 | 22.11 | C |
| ATOM | 1576 | O | THR | B | 335 | 60.134 | −52.212 | −61.232 | 1.00 | 22.40 | O |
| ATOM | 1577 | N | LYS | B | 336 | 61.910 | −53.203 | −62.196 | 1.00 | 24.64 | N |
| ATOM | 1578 | CA | LYS | B | 336 | 61.093 | −53.912 | −63.173 | 1.00 | 30.13 | C |
| ATOM | 1579 | CB | LYS | B | 336 | 61.959 | −54.729 | −64.126 | 1.00 | 30.69 | C |
| ATOM | 1580 | CG | LYS | B | 336 | 62.911 | −53.903 | −64.979 | 1.00 | 36.55 | C |
| ATOM | 1581 | CD | LYS | B | 336 | 63.489 | −54.756 | −66.098 | 1.00 | 38.79 | C |
| ATOM | 1582 | CE | LYS | B | 336 | 64.540 | −54.007 | −66.908 | 1.00 | 50.00 | C |
| ATOM | 1583 | NZ | LYS | B | 336 | 65.172 | −54.919 | −67.907 | 1.00 | 48.46 | N |
| ATOM | 1584 | C | LYS | B | 336 | 60.065 | −54.827 | −62.502 | 1.00 | 27.48 | C |
| ATOM | 1585 | O | LYS | B | 336 | 59.062 | −55.161 | −63.110 | 1.00 | 22.14 | O |
| ATOM | 1586 | N | ASN | B | 337 | 60.314 | −55.221 | −61.243 | 1.00 | 25.94 | N |
| ATOM | 1587 | CA | ASN | B | 337 | 59.374 | −56.092 | −60.521 | 1.00 | 24.82 | C |
| ATOM | 1588 | CB | ASN | B | 337 | 59.987 | −56.581 | −59.200 | 1.00 | 21.33 | C |
| ATOM | 1589 | CG | ASN | B | 337 | 61.192 | −57.472 | −59.419 | 1.00 | 33.06 | C |
| ATOM | 1590 | OD1 | ASN | B | 337 | 62.280 | −57.204 | −58.920 | 1.00 | 36.10 | O |

TABLE 5-continued

Atomic coordinates for CRBN(TBD):Thalidomide (Murine protein)

| | | | | | | | | | | | |
|---|---|---|---|---|---|---|---|---|---|---|---|
| ATOM | 1591 | ND2 | ASN | B | 337 | 61.014 | −58.492 | −60.204 | 1.00 | 31.21 | N |
| ATOM | 1592 | C | ASN | B | 337 | 58.045 | −55.416 | −60.241 | 1.00 | 23.32 | C |
| ATOM | 1593 | O | ASN | B | 337 | 57.024 | −56.083 | −60.045 | 1.00 | 24.76 | O |
| ATOM | 1594 | N | GLU | B | 338 | 58.055 | −54.091 | −60.202 | 1.00 | 20.06 | N |
| ATOM | 1595 | CA | GLU | B | 338 | 56.863 | −53.335 | −59.859 | 1.00 | 19.51 | C |
| ATOM | 1596 | CB | GLU | B | 338 | 57.234 | −52.044 | −59.096 | 1.00 | 22.47 | C |
| ATOM | 1597 | CG | GLU | B | 338 | 57.997 | −52.294 | −57.797 | 1.00 | 23.74 | C |
| ATOM | 1598 | CD | GLU | B | 338 | 57.300 | −53.302 | −56.897 | 1.00 | 30.38 | C |
| ATOM | 1599 | OE1 | GLU | B | 338 | 56.066 | −53.214 | −56.710 | 1.00 | 26.60 | O |
| ATOM | 1600 | OE2 | GLU | B | 338 | 57.987 | −54.174 | −56.359 | 1.00 | 40.84 | O |
| ATOM | 1601 | C | GLU | B | 338 | 55.973 | −52.987 | −61.067 | 1.00 | 18.40 | C |
| ATOM | 1602 | O | GLU | B | 338 | 54.909 | −52.417 | −60.902 | 1.00 | 17.39 | O |
| ATOM | 1603 | N | ILE | B | 339 | 56.440 | −53.294 | −62.271 | 1.00 | 20.06 | N |
| ATOM | 1604 | CA | ILE | B | 339 | 55.715 | −52.907 | −63.480 | 1.00 | 18.96 | C |
| ATOM | 1605 | CB | ILE | B | 339 | 56.563 | −53.177 | −64.737 | 1.00 | 22.28 | C |
| ATOM | 1606 | CG1 | ILE | B | 339 | 57.792 | −52.254 | −64.759 | 1.00 | 18.17 | C |
| ATOM | 1607 | CD1 | ILE | B | 339 | 58.772 | −52.593 | −65.892 | 1.00 | 25.04 | C |
| ATOM | 1608 | CG2 | ILE | B | 339 | 55.713 | −53.006 | −66.010 | 1.00 | 24.94 | C |
| ATOM | 1609 | C | ILE | B | 339 | 54.387 | −53.675 | −63.609 | 1.00 | 20.85 | C |
| ATOM | 1610 | O | ILE | B | 339 | 54.338 | −54.876 | −63.384 | 1.00 | 23.21 | O |
| ATOM | 1611 | N | PHE | B | 340 | 53.318 | −52.961 | −63.927 | 1.00 | 18.09 | N |
| ATOM | 1612 | CA | PHE | B | 340 | 52.050 | −53.613 | −64.293 | 1.00 | 19.52 | C |
| ATOM | 1613 | CB | PHE | B | 340 | 51.119 | −53.750 | −63.043 | 1.00 | 20.09 | C |
| ATOM | 1614 | CG | PHE | B | 340 | 50.470 | −52.463 | −62.622 | 1.00 | 19.49 | C |
| ATOM | 1615 | CD2 | PHE | B | 340 | 49.106 | −52.250 | −62.857 | 1.00 | 16.21 | C |
| ATOM | 1616 | CE2 | PHE | B | 340 | 48.497 | −51.056 | −62.510 | 1.00 | 16.48 | C |
| ATOM | 1617 | CZ | PHE | B | 340 | 49.235 | −50.030 | −61.934 | 1.00 | 20.44 | C |
| ATOM | 1618 | CE1 | PHE | B | 340 | 50.610 | −50.210 | −61.710 | 1.00 | 21.71 | C |
| ATOM | 1619 | CD1 | PHE | B | 340 | 51.221 | −51.422 | −62.055 | 1.00 | 18.66 | C |
| ATOM | 1620 | C | PHE | B | 340 | 51.400 | −52.826 | −65.405 | 1.00 | 24.86 | C |
| ATOM | 1621 | O | PHE | B | 340 | 51.911 | −51.767 | −65.816 | 1.00 | 21.71 | O |
| ATOM | 1622 | N | SER | B | 341 | 50.286 | −53.330 | −65.922 | 1.00 | 25.72 | N |
| ATOM | 1623 | CA | SER | B | 341 | 49.679 | −52.695 | −67.078 | 1.00 | 26.83 | C |
| ATOM | 1624 | CB | SER | B | 341 | 49.925 | −53.519 | −68.341 | 1.00 | 30.87 | C |
| ATOM | 1625 | OG | SER | B | 341 | 49.374 | −52.858 | −69.475 | 1.00 | 31.98 | O |
| ATOM | 1626 | C | SER | B | 341 | 48.201 | −52.449 | −66.884 | 1.00 | 25.33 | C |
| ATOM | 1627 | O | SER | B | 341 | 47.450 | −53.356 | −66.524 | 1.00 | 29.73 | O |
| ATOM | 1628 | N | LEU | B | 342 | 47.800 | −51.207 | −67.084 | 1.00 | 23.60 | N |
| ATOM | 1629 | CA | LEU | B | 342 | 46.399 | −50.827 | −67.091 | 1.00 | 26.62 | C |
| ATOM | 1630 | CB | LEU | B | 342 | 46.249 | −49.467 | −66.434 | 1.00 | 30.73 | C |
| ATOM | 1631 | CG | LEU | B | 342 | 45.538 | −49.332 | −65.096 | 1.00 | 32.89 | C |
| ATOM | 1632 | CD1 | LEU | B | 342 | 45.436 | −50.642 | −64.319 | 1.00 | 33.84 | C |
| ATOM | 1633 | CD2 | LEU | B | 342 | 46.164 | −48.221 | −64.268 | 1.00 | 37.00 | C |
| ATOM | 1634 | C | LEU | B | 342 | 45.784 | −50.795 | −68.531 | 1.00 | 32.15 | C |
| ATOM | 1635 | O | LEU | B | 342 | 44.602 | −50.535 | −68.697 | 1.00 | 31.92 | O |
| ATOM | 1636 | N | SER | B | 343 | 46.599 | −51.033 | −69.545 | 1.00 | 29.79 | N |
| ATOM | 1637 | CA | SER | B | 343 | 46.090 | −51.055 | −70.920 | 1.00 | 34.22 | C |
| ATOM | 1638 | CB | SER | B | 343 | 47.208 | −50.772 | −71.907 | 1.00 | 33.17 | C |
| ATOM | 1639 | OG | SER | B | 343 | 48.152 | −51.817 | −71.903 | 1.00 | 42.82 | O |
| ATOM | 1640 | C | SER | B | 343 | 45.380 | −52.383 | −71.248 | 1.00 | 35.37 | C |
| ATOM | 1641 | O | SER | B | 343 | 45.751 | −53.456 | −70.746 | 1.00 | 24.05 | O |
| ATOM | 1642 | N | LEU | B | 344 | 44.339 | −52.304 | −72.061 | 1.00 | 35.22 | N |
| ATOM | 1643 | CA | LEU | B | 344 | 43.537 | −53.502 | −72.362 | 1.00 | 34.17 | C |
| ATOM | 1644 | CB | LEU | B | 344 | 42.087 | −53.119 | −72.684 | 1.00 | 34.64 | C |
| ATOM | 1645 | CG | LEU | B | 344 | 41.375 | −52.330 | −71.565 | 1.00 | 36.65 | C |
| ATOM | 1646 | CD1 | LEU | B | 344 | 39.920 | −52.044 | −71.908 | 1.00 | 35.55 | C |
| ATOM | 1647 | CD2 | LEU | B | 344 | 41.486 | −53.023 | −70.196 | 1.00 | 34.02 | C |
| ATOM | 1648 | C | LEU | B | 344 | 44.187 | −54.321 | −73.472 | 1.00 | 38.45 | C |
| ATOM | 1649 | O | LEU | B | 344 | 44.837 | −53.761 | −74.374 | 1.00 | 39.44 | O |
| ATOM | 1650 | N | CYS | B | 345 | 44.065 | −55.645 | −73.375 | 1.00 | 36.57 | N |
| ATOM | 1651 | CA | CYS | B | 345 | 44.767 | −56.569 | −74.285 | 1.00 | 42.35 | C |
| ATOM | 1652 | CB | CYS | B | 345 | 45.367 | −57.760 | −73.510 | 1.00 | 41.87 | C |
| ATOM | 1653 | SG | CYS | B | 345 | 46.163 | −57.352 | −71.914 | 1.00 | 51.52 | S |
| ATOM | 1654 | C | CYS | B | 345 | 43.890 | −57.067 | −75.461 | 1.00 | 49.69 | C |
| ATOM | 1655 | O | CYS | B | 345 | 44.379 | −57.775 | −76.348 | 1.00 | 53.67 | O |
| ATOM | 1656 | N | GLY | B | 346 | 42.610 | −56.681 | −75.467 | 1.00 | 48.13 | N |
| ATOM | 1657 | CA | GLY | B | 346 | 41.664 | −57.096 | −76.528 | 1.00 | 47.69 | C |
| ATOM | 1658 | C | GLY | B | 346 | 41.101 | −55.939 | −77.370 | 1.00 | 48.54 | C |
| ATOM | 1659 | O | GLY | B | 346 | 41.584 | −54.798 | −77.279 | 1.00 | 44.60 | O |
| ATOM | 1660 | N | PRO | B | 347 | 40.047 | −56.219 | −78.180 | 1.00 | 49.78 | N |
| ATOM | 1661 | CA | PRO | B | 347 | 39.484 | −55.230 | −79.123 | 1.00 | 44.60 | C |
| ATOM | 1662 | CB | PRO | B | 347 | 38.247 | −55.951 | −79.702 | 1.00 | 45.79 | C |
| ATOM | 1663 | CG | PRO | B | 347 | 38.509 | −57.398 | −79.487 | 1.00 | 44.52 | C |
| ATOM | 1664 | CD | PRO | B | 347 | 39.294 | −57.485 | −78.203 | 1.00 | 43.09 | C |
| ATOM | 1665 | C | PRO | B | 347 | 39.061 | −53.907 | −78.458 | 1.00 | 49.17 | C |
| ATOM | 1666 | O | PRO | B | 347 | 39.048 | −52.866 | −79.119 | 1.00 | 48.51 | O |
| ATOM | 1667 | N | MET | B | 348 | 38.725 | −53.953 | −77.167 | 1.00 | 42.16 | N |
| ATOM | 1668 | CA | MET | B | 348 | 38.362 | −52.744 | −76.414 | 1.00 | 55.36 | C |

TABLE 5-continued

Atomic coordinates for CRBN(TBD):Thalidomide (Murine protein)

| ATOM | 1669 | CB | MET | B | 348 | 37.900 | −53.105 | −75.000 | 1.00 | 47.21 | C |
|---|---|---|---|---|---|---|---|---|---|---|---|
| ATOM | 1670 | CG | MET | B | 348 | 36.677 | −54.003 | −74.953 | 1.00 | 63.11 | C |
| ATOM | 1671 | SD | MET | B | 348 | 35.389 | −53.356 | −73.877 | 1.00 | 82.63 | S |
| ATOM | 1672 | CE | MET | B | 348 | 34.473 | −52.336 | −75.041 | 1.00 | 75.27 | C |
| ATOM | 1673 | C | MET | B | 348 | 39.500 | −51.704 | −76.348 | 1.00 | 48.70 | C |
| ATOM | 1674 | O | MET | B | 348 | 40.674 | −52.034 | −76.545 | 1.00 | 47.54 | O |
| ATOM | 1675 | N | GLY | B | 356 | 48.931 | −42.541 | −79.352 | 1.00 | 63.03 | N |
| ATOM | 1676 | CA | GLY | B | 356 | 50.309 | −42.762 | −79.779 | 1.00 | 71.69 | C |
| ATOM | 1677 | C | GLY | B | 356 | 51.305 | −42.690 | −78.635 | 1.00 | 75.51 | C |
| ATOM | 1678 | O | GLY | B | 356 | 52.508 | −42.502 | −78.852 | 1.00 | 71.05 | O |
| ATOM | 1679 | N | TYR | B | 357 | 50.797 | −42.823 | −77.411 | 1.00 | 70.15 | N |
| ATOM | 1680 | CA | TYR | B | 357 | 51.641 | −42.961 | −76.221 | 1.00 | 64.86 | C |
| ATOM | 1681 | CB | TYR | B | 357 | 51.143 | −42.034 | −75.102 | 1.00 | 53.46 | C |
| ATOM | 1682 | CG | TYR | B | 357 | 51.532 | −40.584 | −75.329 | 1.00 | 40.26 | C |
| ATOM | 1683 | CD1 | TYR | B | 357 | 52.782 | −40.116 | −74.936 | 1.00 | 41.69 | C |
| ATOM | 1684 | CE1 | TYR | B | 357 | 53.162 | −38.796 | −75.155 | 1.00 | 44.87 | C |
| ATOM | 1685 | CZ | TYR | B | 357 | 52.277 | −37.918 | −75.789 | 1.00 | 36.22 | C |
| ATOM | 1686 | OH | TYR | B | 357 | 52.668 | −36.620 | −76.005 | 1.00 | 35.67 | O |
| ATOM | 1687 | CE2 | TYR | B | 357 | 51.030 | −38.360 | −76.204 | 1.00 | 37.32 | C |
| ATOM | 1688 | CD2 | TYR | B | 357 | 50.667 | −39.693 | −75.990 | 1.00 | 34.35 | C |
| ATOM | 1689 | C | TYR | B | 357 | 51.702 | −44.435 | −75.786 | 1.00 | 80.45 | C |
| ATOM | 1690 | O | TYR | B | 357 | 51.891 | −44.764 | −74.595 | 1.00 | 53.74 | O |
| ATOM | 1691 | N | VAL | B | 358 | 51.566 | −45.303 | −76.795 | 1.00 | 89.75 | N |
| ATOM | 1692 | CA | VAL | B | 358 | 51.647 | −46.763 | −76.676 | 1.00 | 81.56 | C |
| ATOM | 1693 | CB | VAL | B | 358 | 52.154 | −47.397 | −78.007 | 1.00 | 81.45 | C |
| ATOM | 1694 | CG2 | VAL | B | 358 | 51.595 | −46.635 | −79.220 | 1.00 | 52.77 | C |
| ATOM | 1695 | CG1 | VAL | B | 358 | 51.794 | −48.879 | −78.073 | 1.00 | 74.26 | C |
| ATOM | 1696 | C | VAL | B | 358 | 52.491 | −47.253 | −75.484 | 1.00 | 82.83 | C |
| ATOM | 1697 | O | VAL | B | 358 | 52.010 | −48.040 | −74.665 | 1.00 | 72.88 | O |
| ATOM | 1698 | N | HIS | B | 359 | 53.736 | −46.774 | −75.385 | 1.00 | 80.53 | N |
| ATOM | 1699 | CA | HIS | B | 359 | 54.603 | −47.100 | −74.245 | 1.00 | 67.40 | C |
| ATOM | 1700 | CB | HIS | B | 359 | 55.380 | −48.396 | −74.498 | 1.00 | 74.36 | C |
| ATOM | 1701 | CG | HIS | B | 359 | 55.713 | −48.639 | −75.957 | 1.00 | 109.23 | C |
| ATOM | 1702 | ND1 | HIS | B | 359 | 56.345 | −47.723 | −76.723 | 1.00 | 111.85 | N |
| ATOM | 1703 | CE1 | HIS | B | 359 | 56.503 | −48.213 | −77.967 | 1.00 | 114.31 | C |
| ATOM | 1704 | NE2 | HIS | B | 359 | 55.979 | −49.449 | −77.999 | 1.00 | 115.36 | N |
| ATOM | 1705 | CD2 | HIS | B | 359 | 55.484 | −49.746 | −76.778 | 1.00 | 108.09 | C |
| ATOM | 1706 | C | HIS | B | 359 | 55.543 | −45.978 | −73.875 | 1.00 | 66.12 | C |
| ATOM | 1707 | O | HIS | B | 359 | 56.745 | −46.183 | −73.749 | 1.00 | 81.42 | O |
| ATOM | 1708 | N | GLU | B | 360 | 54.997 | −44.781 | −73.687 | 1.00 | 66.19 | N |
| ATOM | 1709 | CA | GLU | B | 360 | 55.780 | −43.634 | −73.198 | 1.00 | 60.10 | C |
| ATOM | 1710 | CB | GLU | B | 360 | 55.187 | −42.339 | −73.731 | 1.00 | 59.59 | C |
| ATOM | 1711 | CG | GLU | B | 360 | 56.219 | −41.334 | −74.221 | 1.00 | 69.87 | C |
| ATOM | 1712 | CD | GLU | B | 360 | 56.584 | −41.543 | −75.681 | 1.00 | 80.44 | C |
| ATOM | 1713 | OE1 | GLU | B | 360 | 57.798 | −41.568 | −75.989 | 1.00 | 89.35 | O |
| ATOM | 1714 | OE2 | GLU | B | 360 | 55.657 | −41.683 | −76.523 | 1.00 | 69.85 | O |
| ATOM | 1715 | C | GLU | B | 360 | 55.780 | −43.599 | −71.659 | 1.00 | 59.46 | C |
| ATOM | 1716 | O | GLU | B | 360 | 56.629 | −42.909 | −71.015 | 1.00 | 33.01 | O |
| ATOM | 1717 | N | THR | B | 361 | 54.816 | −44.323 | −71.080 | 1.00 | 46.42 | N |
| ATOM | 1718 | CA | THR | B | 361 | 54.509 | −44.230 | −69.653 | 1.00 | 49.04 | C |
| ATOM | 1719 | CB | THR | B | 361 | 53.128 | −43.564 | −69.392 | 1.00 | 52.32 | C |
| ATOM | 1720 | OG1 | THR | B | 361 | 53.110 | −42.257 | −69.976 | 1.00 | 75.08 | O |
| ATOM | 1721 | CG2 | THR | B | 361 | 52.840 | −43.434 | −67.880 | 1.00 | 43.73 | C |
| ATOM | 1722 | C | THR | B | 361 | 54.550 | −45.616 | −69.048 | 1.00 | 40.27 | C |
| ATOM | 1723 | O | THR | B | 361 | 53.838 | −46.515 | −69.469 | 1.00 | 33.11 | O |
| ATOM | 1724 | N | LEU | B | 362 | 55.797 | −45.797 | −68.122 | 1.00 | 35.08 | N |
| ATOM | 1725 | CA | LEU | B | 362 | 55.558 | −46.998 | −67.380 | 1.00 | 30.03 | C |
| ATOM | 1726 | CB | LEU | B | 362 | 56.991 | −47.162 | −66.876 | 1.00 | 27.65 | C |
| ATOM | 1727 | CG | LEU | B | 362 | 57.352 | −48.572 | −66.491 | 1.00 | 33.81 | C |
| ATOM | 1728 | CD1 | LEU | B | 362 | 57.477 | −49.446 | −67.730 | 1.00 | 38.59 | C |
| ATOM | 1729 | CD2 | LEU | B | 362 | 58.655 | −48.559 | −65.709 | 1.00 | 47.77 | C |
| ATOM | 1730 | C | LEU | B | 362 | 54.618 | −46.830 | −66.198 | 1.00 | 29.49 | C |
| ATOM | 1731 | O | LEU | B | 362 | 54.650 | −45.806 | −65.545 | 1.00 | 28.13 | O |
| ATOM | 1732 | N | THR | B | 363 | 53.752 | −47.804 | −65.937 | 1.00 | 23.26 | N |
| ATOM | 1733 | CA | THR | B | 363 | 52.994 | −47.762 | −64.687 | 1.00 | 20.27 | C |
| ATOM | 1734 | CB | THR | B | 363 | 51.465 | −47.984 | −64.900 | 1.00 | 21.87 | C |
| ATOM | 1735 | OG1 | THR | B | 363 | 51.278 | −49.143 | −65.699 | 1.00 | 25.84 | O |
| ATOM | 1736 | CG2 | THR | B | 363 | 50.845 | −46.800 | −65.628 | 1.00 | 25.43 | C |
| ATOM | 1737 | C | THR | B | 363 | 53.561 | −48.818 | −63.719 | 1.00 | 17.27 | C |
| ATOM | 1738 | O | THR | B | 363 | 53.835 | −49.966 | −64.114 | 1.00 | 21.02 | O |
| ATOM | 1739 | N | VAL | B | 364 | 53.763 | −48.409 | −62.472 | 1.00 | 18.20 | N |
| ATOM | 1740 | CA | VAL | B | 364 | 54.317 | −49.306 | −61.443 | 1.00 | 16.03 | C |
| ATOM | 1741 | CB | VAL | B | 364 | 55.846 | −49.000 | −61.164 | 1.00 | 17.93 | C |
| ATOM | 1742 | CG1 | VAL | B | 364 | 56.685 | −49.372 | −62.410 | 1.00 | 17.30 | C |
| ATOM | 1743 | CG2 | VAL | B | 364 | 56.115 | −47.640 | −60.635 | 1.00 | 16.12 | C |
| ATOM | 1744 | C | VAL | B | 364 | 53.520 | −49.197 | −60.158 | 1.00 | 13.99 | C |
| ATOM | 1745 | O | VAL | B | 364 | 52.955 | −48.135 | −59.853 | 1.00 | 14.95 | O |
| ATOM | 1746 | N | TYR | B | 365 | 53.497 | −50.299 | −59.379 | 1.00 | 15.27 | N |

TABLE 5-continued

Atomic coordinates for CRBN(TBD):Thalidomide (Murine protein)

| ATOM | 1747 | CA | TYR | B | 365 | 52.726 | −50.335 | −58.132 | 1.00 | 15.27 | C |
|---|---|---|---|---|---|---|---|---|---|---|---|
| ATOM | 1748 | CB | TYR | B | 365 | 52.594 | −51.798 | −57.635 | 1.00 | 15.22 | C |
| ATOM | 1749 | CG | TYR | B | 365 | 51.527 | −52.602 | −58.396 | 1.00 | 16.64 | C |
| ATOM | 1750 | CD1 | TYR | B | 365 | 50.210 | −52.176 | −58.427 | 1.00 | 16.82 | C |
| ATOM | 1751 | CE1 | TYR | B | 365 | 49.215 | −52.930 | −59.094 | 1.00 | 18.58 | C |
| ATOM | 1752 | CZ | TYR | B | 365 | 49.568 | −54.092 | −59.732 | 1.00 | 20.21 | C |
| ATOM | 1753 | OH | TYR | B | 365 | 48.596 | −54.847 | −60.364 | 1.00 | 22.48 | O |
| ATOM | 1754 | CE2 | TYR | B | 365 | 50.870 | −54.547 | −59.692 | 1.00 | 18.91 | C |
| ATOM | 1755 | CD2 | TYR | B | 365 | 51.844 | −53.798 | −59.024 | 1.00 | 17.45 | C |
| ATOM | 1756 | C | TYR | B | 365 | 53.367 | −49.479 | −57.048 | 1.00 | 14.92 | C |
| ATOM | 1757 | O | TYR | B | 365 | 52.683 | −48.951 | −56.154 | 1.00 | 16.09 | O |
| ATOM | 1758 | N | LYS | B | 366 | 54.684 | −49.431 | −57.099 | 1.00 | 16.31 | N |
| ATOM | 1759 | CA | LYS | B | 366 | 55.491 | −48.888 | −56.041 | 1.00 | 16.02 | C |
| ATOM | 1760 | CB | LYS | B | 366 | 56.013 | −50.034 | −55.148 | 1.00 | 16.03 | C |
| ATOM | 1761 | CG | LYS | B | 366 | 54.941 | −50.708 | −54.293 | 1.00 | 15.69 | C |
| ATOM | 1762 | CD | LYS | B | 366 | 54.623 | −49.785 | −53.126 | 1.00 | 19.34 | C |
| ATOM | 1763 | CE | LYS | B | 366 | 53.671 | −50.394 | −52.140 | 1.00 | 29.43 | C |
| ATOM | 1764 | NZ | LYS | B | 366 | 53.463 | −49.421 | −51.012 | 1.00 | 25.44 | N |
| ATOM | 1765 | C | LYS | B | 366 | 56.679 | −48.138 | −56.638 | 1.00 | 15.70 | C |
| ATOM | 1766 | O | LYS | B | 366 | 57.276 | −48.593 | −57.622 | 1.00 | 17.11 | O |
| ATOM | 1767 | N | ALA | B | 367 | 57.056 | −47.041 | −55.968 | 1.00 | 17.02 | N |
| ATOM | 1768 | CA | ALA | B | 367 | 58.229 | −46.234 | −56.353 | 1.00 | 19.37 | C |
| ATOM | 1769 | CB | ALA | B | 367 | 57.825 | −45.121 | −57.313 | 1.00 | 18.65 | C |
| ATOM | 1770 | C | ALA | B | 367 | 58.857 | −45.638 | −55.119 | 1.00 | 18.92 | C |
| ATOM | 1771 | O | ALA | B | 367 | 58.261 | −45.644 | −54.007 | 1.00 | 19.36 | O |
| ATOM | 1772 | N | SER | B | 368 | 60.053 | −45.087 | −55.304 | 1.00 | 19.37 | N |
| ATOM | 1773 | CA | SER | B | 368 | 60.830 | −44.567 | −54.199 | 1.00 | 18.94 | C |
| ATOM | 1774 | CB | SER | B | 368 | 61.826 | −45.640 | −53.736 | 1.00 | 18.13 | C |
| ATOM | 1775 | OG | SER | B | 368 | 62.722 | −45.985 | −54.789 | 1.00 | 23.37 | O |
| ATOM | 1776 | C | SER | B | 368 | 61.582 | −43.292 | −54.615 | 1.00 | 18.59 | C |
| ATOM | 1777 | O | SER | B | 368 | 61.783 | −43.020 | −55.833 | 1.00 | 19.06 | O |
| ATOM | 1778 | N | ASN | B | 369 | 61.989 | −42.511 | −53.614 | 1.00 | 20.63 | N |
| ATOM | 1779 | CA | ASN | B | 369 | 62.876 | −41.382 | −53.839 | 1.00 | 20.71 | C |
| ATOM | 1780 | CB | ASN | B | 369 | 64.166 | −41.843 | −54.529 | 1.00 | 19.23 | C |
| ATOM | 1781 | CG | ASN | B | 369 | 65.078 | −42.643 | −53.602 | 1.00 | 29.83 | C |
| ATOM | 1782 | OD1 | ASN | B | 369 | 65.663 | −43.660 | −53.995 | 1.00 | 34.23 | O |
| ATOM | 1783 | ND2 | ASN | B | 369 | 65.182 | −42.204 | −52.379 | 1.00 | 23.95 | N |
| ATOM | 1784 | C | ASN | B | 369 | 62.205 | −40.277 | −54.670 | 1.00 | 25.05 | C |
| ATOM | 1785 | O | ASN | B | 369 | 62.885 | −39.464 | −55.286 | 1.00 | 28.63 | O |
| ATOM | 1786 | N | LEU | B | 370 | 60.874 | −40.249 | −54.663 | 1.00 | 26.36 | N |
| ATOM | 1787 | CA | LEU | B | 370 | 60.132 | −39.181 | −55.312 | 1.00 | 24.68 | C |
| ATOM | 1788 | CB | LEU | B | 370 | 59.050 | −39.757 | −56.237 | 1.00 | 24.27 | C |
| ATOM | 1789 | CG | LEU | B | 370 | 59.539 | −40.516 | −57.460 | 1.00 | 19.62 | C |
| ATOM | 1790 | CD1 | LEU | B | 370 | 58.316 | −41.163 | −58.129 | 1.00 | 23.24 | C |
| ATOM | 1791 | CD2 | LEU | B | 370 | 60.243 | −39.576 | −58.442 | 1.00 | 21.56 | C |
| ATOM | 1792 | C | LEU | B | 370 | 59.476 | −38.284 | −54.283 | 1.00 | 26.74 | C |
| ATOM | 1793 | O | LEU | B | 370 | 58.915 | −38.756 | −53.297 | 1.00 | 26.36 | O |
| ATOM | 1794 | N | ASN | B | 371 | 59.542 | −36.982 | −54.526 | 1.00 | 26.56 | N |
| ATOM | 1795 | CA | ASN | B | 371 | 58.792 | −36.013 | −53.767 | 1.00 | 24.89 | C |
| ATOM | 1796 | CB | ASN | B | 371 | 59.643 | −34.761 | −53.507 | 1.00 | 33.82 | C |
| ATOM | 1797 | CG | ASN | B | 371 | 60.528 | −34.896 | −52.277 | 1.00 | 43.42 | C |
| ATOM | 1798 | OD1 | ASN | B | 371 | 60.119 | −35.457 | −51.257 | 1.00 | 49.45 | O |
| ATOM | 1799 | ND2 | ASN | B | 371 | 61.746 | −34.377 | −52.368 | 1.00 | 38.40 | N |
| ATOM | 1800 | C | ASN | B | 371 | 57.545 | −35.608 | −54.531 | 1.00 | 24.46 | C |
| ATOM | 1801 | O | ASN | B | 371 | 57.600 | −35.365 | −55.744 | 1.00 | 21.96 | O |
| ATOM | 1802 | N | LEU | B | 372 | 56.431 | −35.505 | −53.810 | 1.00 | 24.82 | N |
| ATOM | 1803 | CA | LEU | B | 372 | 55.156 | −35.104 | −54.408 | 1.00 | 25.02 | C |
| ATOM | 1804 | CB | LEU | B | 372 | 53.994 | −35.765 | −53.673 | 1.00 | 25.54 | C |
| ATOM | 1805 | CG | LEU | B | 372 | 53.983 | −37.287 | −53.670 | 1.00 | 29.40 | C |
| ATOM | 1806 | CD1 | LEU | B | 372 | 52.802 | −37.773 | −52.838 | 1.00 | 32.39 | C |
| ATOM | 1807 | CD2 | LEU | B | 372 | 53.926 | −37.839 | −55.092 | 1.00 | 27.68 | C |
| ATOM | 1808 | C | LEU | B | 372 | 55.007 | −33.601 | −54.323 | 1.00 | 31.80 | C |
| ATOM | 1809 | O | LEU | B | 372 | 55.315 | −33.004 | −53.283 | 1.00 | 27.90 | O |
| ATOM | 1810 | N | ILE | B | 373 | 54.501 | −33.000 | −55.403 | 1.00 | 29.23 | N |
| ATOM | 1811 | CA | ILE | B | 373 | 54.336 | −31.542 | −55.515 | 1.00 | 34.49 | C |
| ATOM | 1812 | CB | ILE | B | 373 | 54.970 | −30.999 | −56.844 | 1.00 | 36.77 | C |
| ATOM | 1813 | CG1 | ILE | B | 373 | 56.355 | −31.586 | −57.080 | 1.00 | 34.94 | C |
| ATOM | 1814 | CD1 | ILE | B | 373 | 57.371 | −31.204 | −56.035 | 1.00 | 42.02 | C |
| ATOM | 1815 | CG2 | ILE | B | 373 | 55.024 | −29.475 | −56.836 | 1.00 | 42.71 | C |
| ATOM | 1816 | C | ILE | B | 373 | 52.854 | −31.215 | −55.552 | 1.00 | 35.04 | C |
| ATOM | 1817 | O | ILE | B | 373 | 52.129 | −31.735 | −56.393 | 1.00 | 33.44 | O |
| ATOM | 1818 | N | GLY | B | 374 | 52.397 | −30.355 | −54.646 | 1.00 | 35.66 | N |
| ATOM | 1819 | CA | GLY | B | 374 | 51.001 | −29.918 | −54.669 | 1.00 | 38.32 | C |
| ATOM | 1820 | C | GLY | B | 374 | 50.012 | −31.004 | −54.252 | 1.00 | 45.77 | C |
| ATOM | 1821 | O | GLY | B | 374 | 50.302 | −31.833 | −53.365 | 1.00 | 38.22 | O |
| ATOM | 1822 | N | ARG | B | 375 | 48.854 | −31.010 | −54.906 | 1.00 | 36.94 | N |
| ATOM | 1823 | CA | ARG | B | 375 | 47.719 | −31.820 | −54.483 | 1.00 | 42.99 | C |
| ATOM | 1824 | CB | ARG | B | 375 | 46.681 | −30.933 | −53.782 | 1.00 | 49.49 | C |

TABLE 5-continued

Atomic coordinates for CRBN(TBD):Thalidomide (Murine protein)

| ATOM | 1825 | CG | ARG | B | 375 | 47.138 | −30.354 | −52.442 | 1.00 | 63.58 | C |
|---|---|---|---|---|---|---|---|---|---|---|---|
| ATOM | 1826 | CD | ARG | B | 375 | 46.374 | −29.083 | −52.077 | 1.00 | 75.38 | C |
| ATOM | 1827 | NE | ARG | B | 375 | 44.920 | −29.268 | −52.133 | 1.00 | 86.36 | N |
| ATOM | 1828 | CZ | ARG | B | 375 | 44.138 | −28.820 | −53.116 | 1.00 | 83.29 | C |
| ATOM | 1829 | NH1 | ARG | B | 375 | 44.657 | −28.143 | −54.137 | 1.00 | 84.63 | N |
| ATOM | 1830 | NH2 | ARG | B | 375 | 42.832 | −29.049 | −53.078 | 1.00 | 81.05 | N |
| ATOM | 1831 | C | ARG | B | 375 | 47.082 | −32.482 | −55.689 | 1.00 | 31.24 | C |
| ATOM | 1832 | O | ARG | B | 375 | 47.186 | −31.964 | −56.794 | 1.00 | 37.99 | O |
| ATOM | 1833 | N | PRO | B | 376 | 46.357 | −33.594 | −55.478 | 1.00 | 31.59 | N |
| ATOM | 1834 | CA | PRO | B | 376 | 45.809 | −34.325 | −56.613 | 1.00 | 29.94 | C |
| ATOM | 1835 | CB | PRO | B | 376 | 45.043 | −35.467 | −55.942 | 1.00 | 32.72 | C |
| ATOM | 1836 | CG | PRO | B | 376 | 45.799 | −35.722 | −54.681 | 1.00 | 26.98 | C |
| ATOM | 1837 | CD | PRO | B | 376 | 46.174 | −34.342 | −54.213 | 1.00 | 31.89 | C |
| ATOM | 1838 | C | PRO | B | 376 | 44.858 | −33.508 | −57.474 | 1.00 | 32.16 | C |
| ATOM | 1839 | O | PRO | B | 376 | 44.032 | −32.763 | −56.955 | 1.00 | 32.07 | O |
| ATOM | 1840 | N | SER | B | 377 | 44.930 | −33.719 | −58.781 | 1.00 | 27.14 | N |
| ATOM | 1841 | CA | SER | B | 377 | 43.961 | −33.142 | −59.716 | 1.00 | 25.64 | C |
| ATOM | 1842 | CB | SER | B | 377 | 44.646 | −32.000 | −60.504 | 1.00 | 29.29 | C |
| ATOM | 1843 | OG | SER | B | 377 | 43.916 | −31.657 | −61.655 | 1.00 | 26.64 | O |
| ATOM | 1844 | C | SER | B | 377 | 43.468 | −34.214 | −60.676 | 1.00 | 23.23 | C |
| ATOM | 1845 | O | SER | B | 377 | 44.216 | −35.103 | −61.035 | 1.00 | 28.92 | O |
| ATOM | 1846 | N | THR | B | 378 | 42.209 | −34.123 | −61.105 | 1.00 | 22.77 | N |
| ATOM | 1847 | CA | THR | B | 378 | 41.674 | −35.013 | −62.148 | 1.00 | 23.90 | C |
| ATOM | 1848 | CB | THR | B | 378 | 40.229 | −35.459 | −61.849 | 1.00 | 31.81 | C |
| ATOM | 1849 | OG1 | THR | B | 378 | 39.424 | −34.305 | −61.638 | 1.00 | 30.11 | O |
| ATOM | 1850 | CG2 | THR | B | 378 | 40.173 | −36.349 | −60.614 | 1.00 | 26.71 | C |
| ATOM | 1851 | C | THR | B | 378 | 41.674 | −34.360 | −63.541 | 1.00 | 23.70 | C |
| ATOM | 1852 | O | THR | B | 378 | 41.319 | −34.994 | −64.540 | 1.00 | 22.07 | O |
| ATOM | 1853 | N | VAL | B | 379 | 42.139 | −33.125 | −63.615 | 1.00 | 25.93 | N |
| ATOM | 1854 | CA | VAL | B | 379 | 42.142 | −32.395 | −64.889 | 1.00 | 25.41 | C |
| ATOM | 1855 | CB | VAL | B | 379 | 42.594 | −30.926 | −64.673 | 1.00 | 28.55 | C |
| ATOM | 1856 | CG1 | VAL | B | 379 | 42.661 | −30.181 | −66.001 | 1.00 | 35.39 | C |
| ATOM | 1857 | CG2 | VAL | B | 379 | 41.656 | −30.206 | −63.688 | 1.00 | 30.31 | C |
| ATOM | 1858 | C | VAL | B | 379 | 43.037 | −33.105 | −65.925 | 1.00 | 23.26 | C |
| ATOM | 1859 | O | VAL | B | 379 | 44.223 | −33.386 | −65.653 | 1.00 | 25.38 | O |
| ATOM | 1860 | N | HIS | B | 380 | 42.459 | −33.447 | −67.077 | 1.00 | 20.20 | N |
| ATOM | 1861 | CA | HIS | B | 380 | 43.187 | −34.132 | −68.185 | 1.00 | 25.05 | C |
| ATOM | 1862 | CB | HIS | B | 380 | 44.353 | −33.274 | −68.713 | 1.00 | 23.09 | C |
| ATOM | 1863 | CG | HIS | B | 380 | 43.963 | −31.857 | −69.099 | 1.00 | 26.55 | C |
| ATOM | 1864 | ND1 | HIS | B | 380 | 42.912 | −31.581 | −69.898 | 1.00 | 29.63 | N |
| ATOM | 1865 | CE1 | HIS | B | 380 | 42.822 | −30.238 | −70.078 | 1.00 | 24.85 | C |
| ATOM | 1866 | NE2 | HIS | B | 380 | 43.827 | −29.661 | −69.398 | 1.00 | 25.66 | N |
| ATOM | 1867 | CD2 | HIS | B | 380 | 44.555 | −30.627 | −68.788 | 1.00 | 25.94 | C |
| ATOM | 1868 | C | HIS | B | 380 | 43.740 | −35.499 | −67.807 | 1.00 | 23.87 | C |
| ATOM | 1869 | O | HIS | B | 380 | 44.638 | −36.004 | −68.471 | 1.00 | 19.89 | O |
| ATOM | 1870 | N | SER | B | 381 | 43.215 | −36.119 | −66.759 | 1.00 | 27.13 | N |
| ATOM | 1871 | CA | SER | B | 381 | 43.830 | −37.365 | −66.285 | 1.00 | 21.54 | C |
| ATOM | 1872 | CB | SER | B | 381 | 43.131 | −37.898 | −65.036 | 1.00 | 26.12 | C |
| ATOM | 1873 | OG | SER | B | 381 | 43.723 | −39.137 | −64.656 | 1.00 | 27.41 | O |
| ATOM | 1874 | C | SER | B | 381 | 43.914 | −38.451 | −67.361 | 1.00 | 19.95 | C |
| ATOM | 1875 | O | SER | B | 381 | 42.920 | −38.801 | −68.014 | 1.00 | 25.35 | O |
| ATOM | 1876 | N | TRP | B | 382 | 45.099 | −39.001 | −67.528 | 1.00 | 17.98 | N |
| ATOM | 1877 | CA | TRP | B | 382 | 45.320 | −40.052 | −68.483 | 1.00 | 20.29 | C |
| ATOM | 1878 | CB | TRP | B | 382 | 46.806 | −40.220 | −68.752 | 1.00 | 21.35 | C |
| ATOM | 1879 | CG | TRP | B | 382 | 47.434 | −38.964 | −69.246 | 1.00 | 24.47 | C |
| ATOM | 1880 | CD1 | TRP | B | 382 | 46.842 | −37.986 | −70.057 | 1.00 | 21.06 | C |
| ATOM | 1881 | NE1 | TRP | B | 382 | 47.738 | −36.984 | −70.328 | 1.00 | 23.04 | N |
| ATOM | 1882 | CE2 | TRP | B | 382 | 48.929 | −37.237 | −69.716 | 1.00 | 24.13 | C |
| ATOM | 1883 | CD2 | TRP | B | 382 | 48.794 | −38.510 | −69.017 | 1.00 | 24.12 | C |
| ATOM | 1884 | CE3 | TRP | B | 382 | 49.892 | −39.016 | −68.312 | 1.00 | 26.14 | C |
| ATOM | 1885 | CZ3 | TRP | B | 382 | 51.083 | −38.277 | −68.314 | 1.00 | 26.99 | C |
| ATOM | 1886 | CH2 | TRP | B | 382 | 51.188 | −37.051 | −68.991 | 1.00 | 31.26 | C |
| ATOM | 1887 | CZ2 | TRP | B | 382 | 50.114 | −36.506 | −69.701 | 1.00 | 26.83 | C |
| ATOM | 1888 | C | TRP | B | 382 | 44.731 | −41.376 | −68.079 | 1.00 | 22.92 | C |
| ATOM | 1889 | O | TRP | B | 382 | 44.714 | −42.309 | −68.875 | 1.00 | 25.45 | O |
| ATOM | 1890 | N | PHE | B | 383 | 44.283 | −41.478 | −66.832 | 1.00 | 22.28 | N |
| ATOM | 1891 | CA | PHE | B | 383 | 43.734 | −42.745 | −66.318 | 1.00 | 24.17 | C |
| ATOM | 1892 | CB | PHE | B | 383 | 44.723 | −43.411 | −65.335 | 1.00 | 20.51 | C |
| ATOM | 1893 | CG | PHE | B | 383 | 46.015 | −43.807 | −65.959 | 1.00 | 20.63 | C |
| ATOM | 1894 | CD1 | PHE | B | 383 | 46.103 | −44.959 | −66.733 | 1.00 | 20.80 | C |
| ATOM | 1895 | CE1 | PHE | B | 383 | 47.303 | −45.330 | −67.333 | 1.00 | 25.81 | C |
| ATOM | 1896 | CZ | PHE | B | 383 | 48.425 | −44.535 | −67.185 | 1.00 | 26.22 | C |
| ATOM | 1897 | CE2 | PHE | B | 383 | 48.351 | −43.351 | −66.445 | 1.00 | 23.89 | C |
| ATOM | 1898 | CD2 | PHE | B | 383 | 47.141 | −42.989 | −65.841 | 1.00 | 20.32 | C |
| ATOM | 1899 | C | PHE | B | 383 | 42.425 | −42.425 | −65.642 | 1.00 | 25.14 | C |
| ATOM | 1900 | O | PHE | B | 383 | 42.399 | −41.993 | −64.476 | 1.00 | 23.05 | O |
| ATOM | 1901 | N | PRO | B | 384 | 41.322 | −42.514 | −66.405 | 1.00 | 25.62 | N |
| ATOM | 1902 | CA | PRO | B | 384 | 40.034 | −42.087 | −65.872 | 1.00 | 29.68 | C |

TABLE 5-continued

Atomic coordinates for CRBN(TBD):Thalidomide (Murine protein)

| ATOM | 1903 | CB | PRO | B | 384 | 39.066 | −42.447 | −66.999 | 1.00 | 39.89 | C |
|---|---|---|---|---|---|---|---|---|---|---|---|
| ATOM | 1904 | CG | PRO | B | 384 | 39.894 | −42.273 | −68.235 | 1.00 | 39.35 | C |
| ATOM | 1905 | CD | PRO | B | 384 | 41.259 | −42.788 | −67.854 | 1.00 | 32.11 | C |
| ATOM | 1906 | C | PRO | B | 384 | 39.698 | −42.835 | −64.591 | 1.00 | 27.51 | C |
| ATOM | 1907 | O | PRO | B | 384 | 39.950 | −44.033 | −64.493 | 1.00 | 30.82 | O |
| ATOM | 1908 | N | GLY | B | 385 | 39.226 | −42.106 | −63.594 | 1.00 | 23.60 | N |
| ATOM | 1909 | CA | GLY | B | 385 | 39.005 | −42.658 | −62.280 | 1.00 | 28.07 | C |
| ATOM | 1910 | C | GLY | B | 385 | 40.113 | −42.318 | −61.303 | 1.00 | 31.07 | C |
| ATOM | 1911 | O | GLY | B | 385 | 39.958 | −42.517 | −60.097 | 1.00 | 30.97 | O |
| ATOM | 1912 | N | TYR | B | 386 | 41.231 | −41.794 | −61.821 | 1.00 | 25.77 | N |
| ATOM | 1913 | CA | TYR | B | 386 | 42.369 | −41.389 | −60.980 | 1.00 | 23.05 | C |
| ATOM | 1914 | CB | TYR | B | 386 | 43.619 | −42.171 | −61.365 | 1.00 | 21.82 | C |
| ATOM | 1915 | CG | TYR | B | 386 | 43.533 | −43.670 | −61.067 | 1.00 | 19.56 | C |
| ATOM | 1916 | CD2 | TYR | B | 386 | 44.003 | −44.193 | −59.841 | 1.00 | 24.10 | C |
| ATOM | 1917 | CE2 | TYR | B | 386 | 43.898 | −45.566 | −59.556 | 1.00 | 19.69 | C |
| ATOM | 1918 | CZ | TYR | B | 386 | 43.384 | −46.430 | −60.539 | 1.00 | 22.41 | C |
| ATOM | 1919 | OH | TYR | B | 386 | 43.320 | −47.801 | −60.318 | 1.00 | 19.99 | O |
| ATOM | 1920 | CE1 | TYR | B | 386 | 42.930 | −45.923 | −61.759 | 1.00 | 22.45 | C |
| ATOM | 1921 | CD1 | TYR | B | 386 | 43.020 | −44.549 | −62.010 | 1.00 | 21.07 | C |
| ATOM | 1922 | C | TYR | B | 386 | 42.696 | −39.902 | −61.085 | 1.00 | 25.43 | C |
| ATOM | 1923 | O | TYR | B | 386 | 42.521 | −39.285 | −62.136 | 1.00 | 22.35 | O |
| ATOM | 1924 | N | ALA | B | 387 | 43.212 | −39.363 | −59.990 | 1.00 | 24.74 | N |
| ATOM | 1925 | CA | ALA | B | 387 | 43.769 | −38.046 | −59.949 | 1.00 | 25.37 | C |
| ATOM | 1926 | CB | ALA | B | 387 | 43.312 | −37.339 | −58.681 | 1.00 | 24.07 | C |
| ATOM | 1927 | C | ALA | B | 387 | 45.284 | −38.168 | −59.979 | 1.00 | 26.78 | C |
| ATOM | 1928 | O | ALA | B | 387 | 45.826 | −39.205 | −59.625 | 1.00 | 27.99 | O |
| ATOM | 1929 | N | TRP | B | 388 | 45.974 | −37.110 | −60.403 | 1.00 | 22.43 | N |
| ATOM | 1930 | CA | TRP | B | 388 | 47.441 | −37.133 | −60.485 | 1.00 | 19.83 | C |
| ATOM | 1931 | CB | TRP | B | 388 | 47.902 | −36.943 | −61.937 | 1.00 | 21.42 | C |
| ATOM | 1932 | CG | TRP | B | 388 | 47.366 | −35.689 | −62.576 | 1.00 | 23.56 | C |
| ATOM | 1933 | CD1 | TRP | B | 388 | 46.229 | −35.571 | −63.382 | 1.00 | 23.07 | C |
| ATOM | 1934 | NE1 | TRP | B | 388 | 46.045 | −34.245 | −63.773 | 1.00 | 24.16 | N |
| ATOM | 1935 | CE2 | TRP | B | 388 | 47.003 | −33.449 | −63.247 | 1.00 | 25.32 | C |
| ATOM | 1936 | CD2 | TRP | B | 388 | 47.909 | −34.314 | −62.471 | 1.00 | 23.01 | C |
| ATOM | 1937 | CE3 | TRP | B | 388 | 48.993 | −33.737 | −61.818 | 1.00 | 22.08 | C |
| ATOM | 1938 | CZ3 | TRP | B | 388 | 49.202 | −32.338 | −61.947 | 1.00 | 27.14 | C |
| ATOM | 1939 | CH2 | TRP | B | 388 | 48.316 | −31.528 | −62.706 | 1.00 | 25.60 | C |
| ATOM | 1940 | CZ2 | TRP | B | 388 | 47.219 | −32.079 | −63.380 | 1.00 | 24.52 | C |
| ATOM | 1941 | C | TRP | B | 388 | 48.065 | −36.083 | −59.617 | 1.00 | 20.56 | C |
| ATOM | 1942 | O | TRP | B | 388 | 47.480 | −34.999 | −59.396 | 1.00 | 24.79 | O |
| ATOM | 1943 | N | THR | B | 389 | 49.256 | −36.391 | −59.110 | 1.00 | 23.53 | N |
| ATOM | 1944 | CA | THR | B | 389 | 50.100 | −35.439 | −58.390 | 1.00 | 24.50 | C |
| ATOM | 1945 | CB | THR | B | 389 | 50.169 | −35.771 | −56.878 | 1.00 | 26.86 | C |
| ATOM | 1946 | OG1 | THR | B | 389 | 48.851 | −35.822 | −56.334 | 1.00 | 21.82 | O |
| ATOM | 1947 | CG2 | THR | B | 389 | 50.993 | −34.715 | −56.133 | 1.00 | 26.94 | C |
| ATOM | 1948 | C | THR | B | 389 | 51.518 | −35.557 | −58.946 | 1.00 | 23.47 | C |
| ATOM | 1949 | O | THR | B | 389 | 52.059 | −36.655 | −59.037 | 1.00 | 21.83 | O |
| ATOM | 1950 | N | ILE | B | 390 | 52.125 | −34.419 | −59.306 | 1.00 | 22.88 | N |
| ATOM | 1951 | CA | ILE | B | 390 | 53.466 | −34.409 | −59.871 | 1.00 | 19.71 | C |
| ATOM | 1952 | CB | ILE | B | 390 | 53.928 | −32.967 | −60.219 | 1.00 | 21.20 | C |
| ATOM | 1953 | CG1 | ILE | B | 390 | 53.165 | −32.442 | −61.451 | 1.00 | 24.92 | C |
| ATOM | 1954 | CD1 | ILE | B | 390 | 53.365 | −30.953 | −61.740 | 1.00 | 27.35 | C |
| ATOM | 1955 | CG2 | ILE | B | 390 | 55.431 | −32.939 | −60.450 | 1.00 | 24.54 | C |
| ATOM | 1956 | C | ILE | B | 390 | 54.491 | −35.060 | −58.917 | 1.00 | 20.69 | C |
| ATOM | 1957 | O | ILE | B | 390 | 54.498 | −34.787 | −57.699 | 1.00 | 22.22 | O |
| ATOM | 1958 | N | ALA | B | 391 | 55.342 | −35.899 | −59.479 | 1.00 | 18.66 | N |
| ATOM | 1959 | CA | ALA | B | 391 | 56.384 | −36.571 | −58.704 | 1.00 | 22.41 | C |
| ATOM | 1960 | CB | ALA | B | 391 | 56.117 | −38.083 | −58.648 | 1.00 | 19.22 | C |
| ATOM | 1961 | C | ALA | B | 391 | 57.753 | −36.281 | −59.318 | 1.00 | 21.16 | C |
| ATOM | 1962 | O | ALA | B | 391 | 57.992 | −36.566 | −60.494 | 1.00 | 24.34 | O |
| ATOM | 1963 | N | GLN | B | 392 | 58.663 | −35.745 | −58.510 | 1.00 | 24.72 | N |
| ATOM | 1964 | CA | GLN | B | 392 | 60.021 | −35.468 | −58.974 | 1.00 | 20.61 | C |
| ATOM | 1965 | CB | GLN | B | 392 | 60.227 | −33.946 | −59.034 | 1.00 | 29.01 | C |
| ATOM | 1966 | CG | GLN | B | 392 | 60.180 | −33.277 | −57.674 | 1.00 | 30.75 | C |
| ATOM | 1967 | CD | GLN | B | 392 | 60.248 | −31.760 | −57.760 | 1.00 | 43.21 | C |
| ATOM | 1968 | OE1 | GLN | B | 392 | 59.787 | −31.155 | −58.729 | 1.00 | 34.94 | O |
| ATOM | 1969 | NE2 | GLN | B | 392 | 60.811 | −31.142 | −56.731 | 1.00 | 45.60 | N |
| ATOM | 1970 | C | GLN | B | 392 | 61.113 | −36.123 | −58.099 | 1.00 | 23.41 | C |
| ATOM | 1971 | O | GLN | B | 392 | 60.889 | −36.393 | −56.922 | 1.00 | 25.37 | O |
| ATOM | 1972 | N | CYS | B | 393 | 62.281 | −36.388 | −58.695 | 1.00 | 23.20 | N |
| ATOM | 1973 | CA | CYS | B | 393 | 63.419 | −36.977 | −57.981 | 1.00 | 24.77 | C |
| ATOM | 1974 | CB | CYS | B | 393 | 64.638 | −37.063 | −58.922 | 1.00 | 22.66 | C |
| ATOM | 1975 | SG | CYS | B | 393 | 66.185 | −37.610 | −58.175 | 1.00 | 25.31 | S |
| ATOM | 1976 | C | CYS | B | 393 | 63.754 | −36.154 | −56.732 | 1.00 | 27.61 | C |
| ATOM | 1977 | O | CYS | B | 393 | 63.827 | −34.925 | −56.789 | 1.00 | 27.15 | O |
| ATOM | 1978 | N | LYS | B | 394 | 63.911 | −36.815 | −55.595 | 1.00 | 19.95 | N |
| ATOM | 1979 | CA | LYS | B | 394 | 64.166 | −36.076 | −54.371 | 1.00 | 23.60 | C |
| ATOM | 1980 | CB | LYS | B | 394 | 63.973 | −36.938 | −53.137 | 1.00 | 26.08 | C |

TABLE 5-continued

Atomic coordinates for CRBN(TBD):Thalidomide (Murine protein)

| ATOM | 1981 | CG | LYS | B | 394 | 65.127 | −37.887 | −52.857 | 1.00 | 25.52 | C |
|---|---|---|---|---|---|---|---|---|---|---|---|
| ATOM | 1982 | CD | LYS | B | 394 | 64.981 | −38.488 | −51.474 | 1.00 | 35.48 | C |
| ATOM | 1983 | CE | LYS | B | 394 | 66.248 | −39.208 | −51.071 | 1.00 | 39.32 | C |
| ATOM | 1984 | NZ | LYS | B | 394 | 65.926 | −40.438 | −50.293 | 1.00 | 45.39 | N |
| ATOM | 1985 | C | LYS | B | 394 | 65.558 | −35.422 | −54.355 | 1.00 | 28.58 | C |
| ATOM | 1986 | O | LYS | B | 394 | 65.781 | −34.496 | −53.586 | 1.00 | 28.00 | O |
| ATOM | 1987 | N | ILE | B | 395 | 66.466 | −35.900 | −55.211 | 1.00 | 25.13 | N |
| ATOM | 1988 | CA | ILE | B | 395 | 67.850 | −35.377 | −55.276 | 1.00 | 32.87 | C |
| ATOM | 1989 | CB | ILE | B | 395 | 68.898 | −36.498 | −55.606 | 1.00 | 29.09 | C |
| ATOM | 1990 | CG1 | ILE | B | 395 | 69.046 | −37.468 | −54.430 | 1.00 | 25.99 | C |
| ATOM | 1991 | CD1 | ILE | B | 395 | 69.050 | −36.804 | −53.057 | 1.00 | 31.34 | C |
| ATOM | 1992 | CG2 | ILE | B | 395 | 70.266 | −35.909 | −55.988 | 1.00 | 33.04 | C |
| ATOM | 1993 | C | ILE | B | 395 | 67.977 | −34.179 | −56.229 | 1.00 | 35.20 | C |
| ATOM | 1994 | O | ILE | B | 395 | 68.404 | −33.112 | −55.817 | 1.00 | 37.26 | O |
| ATOM | 1995 | N | CYS | B | 396 | 67.557 | −34.345 | −57.483 | 1.00 | 32.30 | N |
| ATOM | 1996 | CA | CYS | B | 396 | 67.816 | −33.336 | −58.514 | 1.00 | 26.52 | C |
| ATOM | 1997 | CB | CYS | B | 396 | 68.564 | −33.963 | −59.678 | 1.00 | 32.72 | C |
| ATOM | 1998 | SG | CYS | B | 396 | 67.496 | −34.951 | −60.756 | 1.00 | 26.64 | S |
| ATOM | 1999 | C | CYS | B | 396 | 66.562 | −32.623 | −59.017 | 1.00 | 34.67 | C |
| ATOM | 2000 | O | CYS | B | 396 | 66.651 | −31.716 | −59.841 | 1.00 | 30.77 | O |
| ATOM | 2001 | N | ALA | B | 397 | 65.394 | −33.059 | −58.533 | 1.00 | 30.00 | N |
| ATOM | 2002 | CA | ALA | B | 397 | 64.099 | −32.457 | −58.864 | 1.00 | 25.27 | C |
| ATOM | 2003 | CB | ALA | B | 397 | 64.056 | −30.966 | −58.510 | 1.00 | 28.66 | C |
| ATOM | 2004 | C | ALA | B | 397 | 63.645 | −32.691 | −60.306 | 1.00 | 26.11 | C |
| ATOM | 2005 | O | ALA | B | 397 | 62.715 | −32.051 | −60.766 | 1.00 | 27.15 | O |
| ATOM | 2006 | N | SER | B | 398 | 64.295 | −33.617 | −61.007 | 1.00 | 25.27 | N |
| ATOM | 2007 | CA | SER | B | 398 | 63.823 | −34.015 | −62.321 | 1.00 | 28.85 | C |
| ATOM | 2008 | CB | SER | B | 398 | 64.699 | −35.101 | −62.890 | 1.00 | 28.47 | C |
| ATOM | 2009 | OG | SER | B | 398 | 64.122 | −35.645 | −64.063 | 1.00 | 31.63 | O |
| ATOM | 2010 | C | SER | B | 398 | 62.370 | −34.497 | −62.233 | 1.00 | 33.13 | C |
| ATOM | 2011 | O | SER | B | 398 | 61.991 | −35.214 | −61.300 | 1.00 | 26.97 | O |
| ATOM | 2012 | N | HIS | B | 399 | 61.556 | −34.054 | −63.174 | 1.00 | 26.79 | N |
| ATOM | 2013 | CA | HIS | B | 399 | 60.158 | −34.440 | −63.227 | 1.00 | 29.56 | C |
| ATOM | 2014 | CB | HIS | B | 399 | 59.371 | −33.430 | −64.067 | 1.00 | 31.35 | C |
| ATOM | 2015 | CG | HIS | B | 399 | 58.965 | −32.194 | −63.302 | 1.00 | 43.04 | C |
| ATOM | 2016 | ND1 | HIS | B | 399 | 59.667 | −31.727 | −62.243 | 1.00 | 51.35 | N |
| ATOM | 2017 | CE1 | HIS | B | 399 | 59.066 | −30.627 | −61.757 | 1.00 | 41.17 | C |
| ATOM | 2018 | NE2 | HIS | B | 399 | 57.987 | −30.376 | −62.508 | 1.00 | 52.23 | N |
| ATOM | 2019 | CD2 | HIS | B | 399 | 57.890 | −31.326 | −63.469 | 1.00 | 47.63 | C |
| ATOM | 2020 | C | HIS | B | 399 | 60.064 | −35.809 | −63.813 | 1.00 | 26.09 | C |
| ATOM | 2021 | O | HIS | B | 399 | 60.208 | −35.996 | −65.009 | 1.00 | 26.83 | O |
| ATOM | 2022 | N | ILE | B | 400 | 59.874 | −36.803 | −62.972 | 1.00 | 20.13 | N |
| ATOM | 2023 | CA | ILE | B | 400 | 59.993 | −38.173 | −63.442 | 1.00 | 22.22 | C |
| ATOM | 2024 | CB | ILE | B | 400 | 60.723 | −39.048 | −62.406 | 1.00 | 20.67 | C |
| ATOM | 2025 | CG1 | ILE | B | 400 | 62.212 | −38.660 | −62.365 | 1.00 | 23.93 | C |
| ATOM | 2026 | CD1 | ILE | B | 400 | 62.947 | −39.221 | −61.193 | 1.00 | 30.82 | C |
| ATOM | 2027 | CG2 | ILE | B | 400 | 60.604 | −40.526 | −62.744 | 1.00 | 19.31 | C |
| ATOM | 2028 | C | ILE | B | 400 | 58.628 | −38.761 | −63.804 | 1.00 | 19.11 | C |
| ATOM | 2029 | O | ILE | B | 400 | 58.519 | −39.591 | −64.716 | 1.00 | 21.52 | O |
| ATOM | 2030 | N | GLY | B | 401 | 57.603 | −38.350 | −63.087 | 1.00 | 22.40 | N |
| ATOM | 2031 | CA | GLY | B | 401 | 56.221 | −38.828 | −63.402 | 1.00 | 25.38 | C |
| ATOM | 2032 | C | GLY | B | 401 | 55.164 | −38.245 | −62.498 | 1.00 | 21.84 | C |
| ATOM | 2033 | O | GLY | B | 401 | 55.206 | −37.053 | −62.160 | 1.00 | 21.94 | O |
| ATOM | 2034 | N | TRP | B | 402 | 54.211 | −39.106 | −62.078 | 1.00 | 18.17 | N |
| ATOM | 2035 | CA | TRP | B | 402 | 53.068 | −38.705 | −61.289 | 1.00 | 17.97 | C |
| ATOM | 2036 | CB | TRP | B | 402 | 51.854 | −38.359 | −62.193 | 1.00 | 20.77 | C |
| ATOM | 2037 | CG | TRP | B | 402 | 52.148 | −37.254 | −63.195 | 1.00 | 19.94 | C |
| ATOM | 2038 | CD1 | TRP | B | 402 | 51.911 | −35.901 | −63.040 | 1.00 | 23.19 | C |
| ATOM | 2039 | NE1 | TRP | B | 402 | 52.356 | −35.182 | −64.165 | 1.00 | 22.03 | N |
| ATOM | 2040 | CE2 | TRP | B | 402 | 52.908 | −36.023 | −65.056 | 1.00 | 19.85 | C |
| ATOM | 2041 | CD2 | TRP | B | 402 | 52.800 | −37.388 | −64.496 | 1.00 | 21.91 | C |
| ATOM | 2042 | CE3 | TRP | B | 402 | 53.300 | −38.468 | −65.238 | 1.00 | 20.75 | C |
| ATOM | 2043 | CZ3 | TRP | B | 402 | 53.923 | −38.201 | −66.471 | 1.00 | 26.36 | C |
| ATOM | 2044 | CH2 | TRP | B | 402 | 54.002 | −36.889 | −66.993 | 1.00 | 23.65 | C |
| ATOM | 2045 | CZ2 | TRP | B | 402 | 53.484 | −35.776 | −66.298 | 1.00 | 22.87 | C |
| ATOM | 2046 | C | TRP | B | 402 | 52.637 | −39.844 | −60.402 | 1.00 | 19.19 | C |
| ATOM | 2047 | O | TRP | B | 402 | 52.729 | −41.013 | −60.778 | 1.00 | 16.56 | O |
| ATOM | 2048 | N | LYS | B | 403 | 52.109 | −39.499 | −59.251 | 1.00 | 17.80 | N |
| ATOM | 2049 | CA | LYS | B | 403 | 51.378 | −40.483 | −58.447 | 1.00 | 22.47 | C |
| ATOM | 2050 | CB | LYS | B | 403 | 51.545 | −40.192 | −56.978 | 1.00 | 19.11 | C |
| ATOM | 2051 | CG | LYS | B | 403 | 51.000 | −41.301 | −56.057 | 1.00 | 24.56 | C |
| ATOM | 2052 | CD | LYS | B | 403 | 50.951 | −40.811 | −54.608 | 1.00 | 29.24 | C |
| ATOM | 2053 | CE | LYS | B | 403 | 50.879 | −41.970 | −53.618 | 1.00 | 34.86 | C |
| ATOM | 2054 | NZ | LYS | B | 403 | 50.945 | −41.502 | −52.204 | 1.00 | 41.33 | N |
| ATOM | 2055 | C | LYS | B | 403 | 49.918 | −40.392 | −58.824 | 1.00 | 17.70 | C |
| ATOM | 2056 | O | LYS | B | 403 | 49.337 | −39.300 | −58.837 | 1.00 | 21.56 | O |
| ATOM | 2057 | N | PHE | B | 404 | 49.330 | −41.525 | −59.184 | 1.00 | 19.40 | N |
| ATOM | 2056 | CA | PHE | B | 404 | 47.900 | −41.546 | −59.496 | 1.00 | 19.48 | C |

TABLE 5-continued

Atomic coordinates for CRBN(TBD):Thalidomide (Murine protein)

| ATOM | 2059 | CB | PHE | B | 404 | 47.654 | −42.330 | −60.764 | 1.00 | 21.50 | C |
|---|---|---|---|---|---|---|---|---|---|---|---|
| ATOM | 2060 | CG | PHE | B | 404 | 48.033 | −41.577 | −61.997 | 1.00 | 19.10 | C |
| ATOM | 2061 | CD1 | PHE | B | 404 | 47.132 | −40.665 | −62.572 | 1.00 | 19.05 | C |
| ATOM | 2062 | CE1 | PHE | B | 404 | 47.500 | −39.929 | −63.720 | 1.00 | 21.95 | C |
| ATOM | 2063 | CZ | PHE | B | 404 | 48.760 | −40.098 | −64.278 | 1.00 | 20.72 | C |
| ATOM | 2064 | CE2 | PHE | B | 404 | 49.665 | −41.015 | −63.720 | 1.00 | 20.35 | C |
| ATOM | 2065 | CD2 | PHE | B | 404 | 49.302 | −41.747 | −62.580 | 1.00 | 18.57 | C |
| ATOM | 2066 | C | PHE | B | 404 | 47.131 | −42.148 | −58.350 | 1.00 | 22.07 | C |
| ATOM | 2067 | O | PHE | B | 404 | 47.514 | −43.171 | −57.846 | 1.00 | 20.40 | O |
| ATOM | 2068 | N | THR | B | 405 | 46.068 | −41.475 | −57.922 | 1.00 | 22.63 | N |
| ATOM | 2069 | CA | THR | B | 405 | 45.309 | −41.921 | −56.760 | 1.00 | 21.98 | C |
| ATOM | 2070 | CB | THR | B | 405 | 45.491 | −40.938 | −55.582 | 1.00 | 28.44 | C |
| ATOM | 2071 | OG1 | THR | B | 405 | 45.236 | −39.595 | −56.031 | 1.00 | 28.02 | O |
| ATOM | 2072 | CG2 | THR | B | 405 | 46.936 | −41.031 | −55.019 | 1.00 | 27.07 | C |
| ATOM | 2073 | C | THR | B | 405 | 43.836 | −42.050 | −57.140 | 1.00 | 23.88 | C |
| ATOM | 2074 | O | THR | B | 405 | 43.290 | −41.168 | −57.829 | 1.00 | 21.85 | O |
| ATOM | 2075 | N | ALA | B | 406 | 43.189 | −43.155 | −56.709 | 1.00 | 21.65 | N |
| ATOM | 2076 | CA | ALA | B | 406 | 41.806 | −43.453 | −57.144 | 1.00 | 21.78 | C |
| ATOM | 2077 | CB | ALA | B | 406 | 41.422 | −44.916 | −56.823 | 1.00 | 22.43 | C |
| ATOM | 2078 | C | ALA | B | 406 | 40.798 | −42.492 | −56.543 | 1.00 | 19.96 | C |
| ATOM | 2079 | O | ALA | B | 406 | 40.925 | −42.086 | −55.421 | 1.00 | 28.14 | O |
| ATOM | 2080 | N | THR | B | 407 | 39.803 | −42.110 | −57.328 | 1.00 | 23.19 | N |
| ATOM | 2081 | CA | THR | B | 407 | 38.781 | −41.206 | −56.841 | 1.00 | 28.46 | C |
| ATOM | 2082 | CB | THR | B | 407 | 38.201 | −40.351 | −57.986 | 1.00 | 30.35 | C |
| ATOM | 2083 | OG1 | THR | B | 407 | 37.621 | −41.212 | −58.978 | 1.00 | 33.67 | O |
| ATOM | 2084 | CG2 | THR | B | 407 | 39.309 | −39.511 | −58.641 | 1.00 | 30.01 | C |
| ATOM | 2085 | C | THR | B | 407 | 37.644 | −41.986 | −56.151 | 1.00 | 31.47 | C |
| ATOM | 2086 | O | THR | B | 407 | 36.855 | −41.408 | −55.416 | 1.00 | 33.47 | O |
| ATOM | 2087 | N | LYS | B | 408 | 37.587 | −43.299 | −56.390 | 1.00 | 32.31 | N |
| ATOM | 2088 | CA | LYS | B | 408 | 36.543 | −44.186 | −55.804 | 1.00 | 35.44 | C |
| ATOM | 2089 | CB | LYS | B | 408 | 35.633 | −44.750 | −56.909 | 1.00 | 37.65 | C |
| ATOM | 2090 | CG | LYS | B | 408 | 34.717 | −43.734 | −57.595 | 1.00 | 47.66 | C |
| ATOM | 2091 | CD | LYS | B | 408 | 33.609 | −43.223 | −56.667 | 1.00 | 65.18 | C |
| ATOM | 2092 | CE | LYS | B | 408 | 32.782 | −44.358 | −56.048 | 1.00 | 66.05 | C |
| ATOM | 2093 | NZ | LYS | B | 408 | 32.197 | −45.275 | −57.070 | 1.00 | 63.73 | N |
| ATOM | 2094 | C | LYS | B | 408 | 37.208 | −45.354 | −55.057 | 1.00 | 35.52 | C |
| ATOM | 2095 | O | LYS | B | 408 | 38.211 | −45.894 | −55.513 | 1.00 | 27.55 | O |
| ATOM | 2096 | N | LYS | B | 409 | 36.614 | −45.772 | −53.947 | 1.00 | 35.54 | N |
| ATOM | 2097 | CA | LYS | B | 409 | 37.224 | −46.790 | −53.103 | 1.00 | 32.09 | C |
| ATOM | 2098 | CB | LYS | B | 409 | 36.707 | −46.687 | −51.658 | 1.00 | 38.15 | C |
| ATOM | 2099 | CG | LYS | B | 409 | 36.929 | −45.313 | −50.983 | 1.00 | 48.59 | C |
| ATOM | 2100 | CD | LYS | B | 409 | 38.413 | −44.890 | −50.910 | 1.00 | 58.61 | C |
| ATOM | 2101 | CE | LYS | B | 409 | 38.719 | −43.598 | −51.711 | 1.00 | 55.96 | C |
| ATOM | 2102 | NZ | LYS | B | 409 | 39.614 | −43.765 | −52.928 | 1.00 | 32.94 | N |
| ATOM | 2103 | C | LYS | B | 409 | 37.111 | −48.225 | −53.668 | 1.00 | 31.39 | C |
| ATOM | 2104 | O | LYS | B | 409 | 37.875 | −49.110 | −53.277 | 1.00 | 31.57 | O |
| ATOM | 2105 | N | ASP | B | 410 | 36.220 | −48.440 | −54.633 | 1.00 | 33.50 | N |
| ATOM | 2106 | CA | ASP | B | 410 | 36.055 | −49.787 | −55.226 | 1.00 | 34.27 | C |
| ATOM | 2107 | CB | ASP | B | 410 | 34.600 | −50.016 | −55.668 | 1.00 | 43.97 | C |
| ATOM | 2108 | CG | ASP | B | 410 | 34.141 | −49.037 | −56.763 | 1.00 | 51.07 | C |
| ATOM | 2109 | OD1 | ASP | B | 410 | 34.940 | −48.178 | −57.219 | 1.00 | 45.00 | O |
| ATOM | 2110 | OD2 | ASP | B | 410 | 32.968 | −49.144 | −57.174 | 1.00 | 50.95 | O |
| ATOM | 2111 | C | ASP | B | 410 | 37.034 | −50.119 | −56.376 | 1.00 | 37.51 | C |
| ATOM | 2112 | O | ASP | B | 410 | 36.965 | −51.192 | −56.969 | 1.00 | 40.14 | O |
| ATOM | 2113 | N | MET | B | 411 | 37.923 | −49.181 | −56.691 | 1.00 | 33.37 | N |
| ATOM | 2114 | CA | MET | B | 411 | 38.947 | −49.374 | −57.735 | 1.00 | 30.15 | C |
| ATOM | 2115 | CB | MET | B | 411 | 39.375 | −47.980 | −58.307 | 1.00 | 21.71 | C |
| ATOM | 2116 | CG | MET | B | 411 | 38.208 | −47.331 | −59.054 | 1.00 | 35.80 | C |
| ATOM | 2117 | SD | MET | B | 411 | 38.504 | −45.709 | −59.780 | 1.00 | 36.76 | S |
| ATOM | 2118 | CE | MET | B | 411 | 38.578 | −44.655 | −58.375 | 1.00 | 30.18 | C |
| ATOM | 2119 | C | MET | B | 411 | 40.158 | −50.141 | −57.173 | 1.00 | 29.10 | C |
| ATOM | 2120 | O | MET | B | 411 | 40.427 | −50.092 | −55.980 | 1.00 | 25.37 | O |
| ATOM | 2121 | N | SER | B | 412 | 40.843 | −50.897 | −58.027 | 1.00 | 30.07 | N |
| ATOM | 2122 | CA | SER | B | 412 | 42.167 | −51.416 | −57.678 | 1.00 | 26.45 | C |
| ATOM | 2123 | CB | SER | B | 412 | 42.163 | −52.926 | −57.501 | 1.00 | 27.50 | C |
| ATOM | 2124 | OG | SER | B | 412 | 41.512 | −53.527 | −58.594 | 1.00 | 31.67 | O |
| ATOM | 2125 | C | SER | B | 412 | 43.104 | −50.979 | −58.795 | 1.00 | 25.60 | C |
| ATOM | 2126 | O | SER | B | 412 | 42.745 | −51.157 | −59.958 | 1.00 | 23.85 | O |
| ATOM | 2127 | N | PRO | B | 413 | 44.393 | −50.881 | −58.473 | 1.00 | 21.41 | N |
| ATOM | 2128 | CA | PRO | B | 413 | 44.883 | −50.222 | −57.289 | 1.00 | 19.98 | C |
| ATOM | 2129 | CB | PRO | B | 413 | 46.396 | −50.108 | −57.558 | 1.00 | 20.19 | C |
| ATOM | 2130 | CG | PRO | B | 413 | 46.478 | −49.910 | −59.013 | 1.00 | 20.26 | C |
| ATOM | 2131 | CD | PRO | B | 413 | 45.251 | −50.562 | −59.638 | 1.00 | 19.68 | C |
| ATOM | 2132 | C | PRO | B | 413 | 44.306 | −48.915 | −56.895 | 1.00 | 22.23 | C |
| ATOM | 2133 | O | PRO | B | 413 | 43.914 | −48.105 | −57.746 | 1.00 | 23.82 | O |
| ATOM | 2134 | N | GLN | B | 414 | 44.332 | −48.661 | −55.593 | 1.00 | 16.67 | N |
| ATOM | 2135 | CA | GLN | B | 414 | 43.927 | −47.397 | −55.078 | 1.00 | 18.64 | C |
| ATOM | 2136 | CB | GLN | B | 414 | 43.727 | −47.465 | −53.558 | 1.00 | 21.07 | C |

TABLE 5-continued

Atomic coordinates for CRBN(TBD):Thalidomide (Murine protein)

| ATOM | 2137 | CG  | GLN | B | 414 | 42.360 | −48.072 | −53.131 | 1.00 | 20.88 | C |
| ATOM | 2138 | CD  | GLN | B | 414 | 41.196 | −47.200 | −53.634 | 1.00 | 20.83 | C |
| ATOM | 2139 | OE1 | GLN | B | 414 | 40.420 | −47.564 | −54.536 | 1.00 | 28.56 | O |
| ATOM | 2140 | NE2 | GLN | B | 414 | 41.096 | −46.038 | −53.052 | 1.00 | 22.14 | N |
| ATOM | 2141 | C   | GLN | B | 414 | 44.943 | −46.306 | −55.457 | 1.00 | 18.17 | C |
| ATOM | 2142 | O   | GLN | B | 414 | 44.624 | −45.137 | −55.422 | 1.00 | 20.82 | O |
| ATOM | 2143 | N   | LYS | B | 415 | 46.157 | −46.726 | −55.780 | 1.00 | 18.50 | N |
| ATOM | 2144 | CA  | LYS | B | 415 | 47.218 | −45.806 | −56.187 | 1.00 | 20.24 | C |
| ATOM | 2145 | CB  | LYS | B | 415 | 47.776 | −44.996 | −54.998 | 1.00 | 25.82 | C |
| ATOM | 2146 | CG  | LYS | B | 415 | 48.725 | −45.715 | −54.106 | 1.00 | 34.82 | C |
| ATOM | 2147 | CD  | LYS | B | 415 | 50.132 | −45.625 | −54.666 | 1.00 | 29.51 | C |
| ATOM | 2148 | CE  | LYS | B | 415 | 51.058 | −46.526 | −53.859 | 1.00 | 35.54 | C |
| ATOM | 2149 | NZ  | LYS | B | 415 | 52.349 | −46.704 | −54.594 | 1.00 | 26.80 | N |
| ATOM | 2150 | C   | LYS | B | 415 | 48.285 | −46.517 | −56.963 | 1.00 | 18.95 | C |
| ATOM | 2151 | O   | LYS | B | 415 | 48.458 | −47.741 | −56.846 | 1.00 | 17.81 | O |
| ATOM | 2152 | N   | PHE | B | 416 | 48.945 | −45.773 | −57.852 | 1.00 | 19.20 | N |
| ATOM | 2153 | CA  | PHE | B | 416 | 50.093 | −46.310 | −58.623 | 1.00 | 16.41 | C |
| ATOM | 2154 | CB  | PHE | B | 416 | 49.631 | −47.216 | −59.784 | 1.00 | 16.68 | C |
| ATOM | 2155 | CG  | PHE | B | 416 | 48.860 | −46.494 | −60.864 | 1.00 | 17.67 | C |
| ATOM | 2156 | CD2 | PHE | B | 416 | 49.519 | −46.024 | −62.010 | 1.00 | 18.03 | C |
| ATOM | 2157 | CE2 | PHE | B | 416 | 48.817 | −45.402 | −63.029 | 1.00 | 17.05 | C |
| ATOM | 2158 | CZ  | PHE | B | 416 | 47.455 | −45.149 | −62.877 | 1.00 | 19.28 | C |
| ATOM | 2159 | CE1 | PHE | B | 416 | 46.782 | −45.615 | −61.752 | 1.00 | 20.02 | C |
| ATOM | 2160 | CD1 | PHE | B | 416 | 47.484 | −46.272 | −60.741 | 1.00 | 19.52 | C |
| ATOM | 2161 | C   | PHE | B | 416 | 50.909 | −45.127 | −59.129 | 1.00 | 14.06 | C |
| ATOM | 2162 | O   | PHE | B | 416 | 50.555 | −43.975 | −58.847 | 1.00 | 19.21 | O |
| ATOM | 2163 | N   | TRP | B | 417 | 52.009 | −45.410 | −59.813 | 1.00 | 16.50 | N |
| ATOM | 2164 | CA  | TRP | B | 417 | 52.871 | −44.341 | −60.367 | 1.00 | 19.40 | C |
| ATOM | 2165 | CB  | TRP | B | 417 | 54.288 | −44.461 | −59.824 | 1.00 | 16.84 | C |
| ATOM | 2166 | CG  | TRP | B | 417 | 54.305 | −44.441 | −58.305 | 1.00 | 17.04 | C |
| ATOM | 2167 | CD1 | TRP | B | 417 | 54.069 | −45.512 | −57.439 | 1.00 | 18.41 | C |
| ATOM | 2168 | NE1 | TRP | B | 417 | 54.161 | −45.102 | −56.124 | 1.00 | 20.34 | N |
| ATOM | 2169 | CE2 | TRP | B | 417 | 54.435 | −43.757 | −56.083 | 1.00 | 23.03 | C |
| ATOM | 2170 | CD2 | TRP | B | 417 | 54.523 | −43.291 | −57.467 | 1.00 | 19.05 | C |
| ATOM | 2171 | CE3 | TRP | B | 417 | 54.826 | −41.940 | −57.716 | 1.00 | 18.50 | C |
| ATOM | 2172 | CZ3 | TRP | B | 417 | 54.985 | −41.075 | −56.626 | 1.00 | 21.97 | C |
| ATOM | 2173 | CH2 | TRP | B | 417 | 54.879 | −41.539 | −55.298 | 1.00 | 23.62 | C |
| ATOM | 2174 | CZ2 | TRP | B | 417 | 54.603 | −42.898 | −55.004 | 1.00 | 22.75 | C |
| ATOM | 2175 | C   | TRP | B | 417 | 52.911 | −44.479 | −61.833 | 1.00 | 21.48 | C |
| ATOM | 2176 | O   | TRP | B | 417 | 53.107 | −45.590 | −62.349 | 1.00 | 19.86 | O |
| ATOM | 2177 | N   | GLY | B | 418 | 52.716 | −43.357 | −62.535 | 1.00 | 21.50 | N |
| ATOM | 2178 | CA  | GLY | B | 418 | 52.894 | −43.355 | −63.988 | 1.00 | 22.82 | C |
| ATOM | 2179 | C   | GLY | B | 418 | 54.175 | −42.600 | −64.237 | 1.00 | 22.57 | C |
| ATOM | 2180 | O   | GLY | B | 418 | 54.285 | −41.433 | −63.840 | 1.00 | 22.33 | O |
| ATOM | 2181 | N   | LEU | B | 419 | 55.163 | −43.267 | −64.825 | 1.00 | 18.90 | N |
| ATOM | 2182 | CA  | LEU | B | 419 | 56.510 | −42.673 | −64.906 | 1.00 | 18.11 | C |
| ATOM | 2183 | CB  | LEU | B | 419 | 57.560 | −43.552 | −64.185 | 1.00 | 18.20 | C |
| ATOM | 2184 | CG  | LEU | B | 419 | 57.233 | −43.892 | −62.708 | 1.00 | 17.73 | C |
| ATOM | 2185 | CD1 | LEU | B | 419 | 58.261 | −44.872 | −62.171 | 1.00 | 22.72 | C |
| ATOM | 2186 | CD2 | LEU | B | 419 | 57.198 | −42.639 | −61.821 | 1.00 | 18.32 | C |
| ATOM | 2187 | C   | LEU | B | 419 | 56.908 | −42.455 | −66.362 | 1.00 | 20.23 | C |
| ATOM | 2188 | O   | LEU | B | 419 | 56.676 | −43.309 | −67.219 | 1.00 | 24.57 | O |
| ATOM | 2189 | N   | THR | B | 420 | 57.578 | −41.336 | −66.621 | 1.00 | 22.71 | N |
| ATOM | 2190 | CA  | THR | B | 420 | 58.031 | −41.043 | −67.974 | 1.00 | 23.72 | C |
| ATOM | 2191 | CB  | THR | B | 420 | 58.313 | −39.541 | −68.149 | 1.00 | 22.08 | C |
| ATOM | 2192 | OG1 | THR | B | 420 | 57.126 | −38.824 | −67.824 | 1.00 | 23.21 | O |
| ATOM | 2193 | CG2 | THR | B | 420 | 58.704 | −39.237 | −69.607 | 1.00 | 24.82 | C |
| ATOM | 2194 | C   | THR | B | 420 | 59.234 | −41.880 | −68.307 | 1.00 | 22.37 | C |
| ATOM | 2195 | O   | THR | B | 420 | 60.303 | −41.730 | −67.693 | 1.00 | 24.14 | O |
| ATOM | 2196 | N   | ARG | B | 421 | 59.069 | −42.810 | −69.247 | 1.00 | 21.72 | N |
| ATOM | 2197 | CA  | ARG | B | 421 | 60.124 | −43.792 | −69.511 | 1.00 | 27.49 | C |
| ATOM | 2198 | CB  | ARG | B | 421 | 59.752 | −44.714 | −70.650 | 1.00 | 29.41 | C |
| ATOM | 2199 | CG  | ARG | B | 421 | 58.946 | −45.913 | −70.252 | 1.00 | 35.70 | C |
| ATOM | 2200 | CD  | ARG | B | 421 | 58.671 | −46.773 | −71.474 | 1.00 | 41.16 | C |
| ATOM | 2201 | NE  | ARG | B | 421 | 57.613 | −47.735 | −71.219 | 1.00 | 55.06 | N |
| ATOM | 2202 | CZ  | ARG | B | 421 | 57.727 | −49.045 | −71.403 | 1.00 | 66.07 | C |
| ATOM | 2203 | NH1 | ARG | B | 421 | 58.859 | −49.561 | −71.868 | 1.00 | 72.67 | N |
| ATOM | 2204 | NH2 | ARG | B | 421 | 56.697 | −49.838 | −71.140 | 1.00 | 75.15 | N |
| ATOM | 2205 | C   | ARG | B | 421 | 61.449 | −43.113 | −69.868 | 1.00 | 29.60 | C |
| ATOM | 2206 | O   | ARG | B | 421 | 62.520 | −43.628 | −69.544 | 1.00 | 23.60 | O |
| ATOM | 2207 | N   | SER | B | 422 | 61.362 | −41.970 | −70.559 | 1.00 | 29.08 | N |
| ATOM | 2208 | CA  | SER | B | 422 | 62.559 | −41.286 | −71.027 | 1.00 | 30.42 | C |
| ATOM | 2209 | CB  | SER | B | 422 | 62.232 | −40.289 | −72.158 | 1.00 | 28.03 | C |
| ATOM | 2210 | OG  | SER | B | 422 | 61.377 | −39.255 | −71.726 | 1.00 | 35.09 | O |
| ATOM | 2211 | C   | SER | B | 422 | 63.281 | −40.595 | −69.878 | 1.00 | 31.76 | C |
| ATOM | 2212 | O   | SER | B | 422 | 64.412 | −40.199 | −70.036 | 1.00 | 30.97 | O |
| ATOM | 2213 | N   | ALA | B | 423 | 62.624 | −40.500 | −68.702 | 1.00 | 23.51 | N |
| ATOM | 2214 | CA  | ALA | B | 423 | 63.254 | −39.929 | −67.505 | 1.00 | 23.73 | C |

TABLE 5-continued

Atomic coordinates for CRBN(TBD):Thalidomide (Murine protein)

| ATOM | 2215 | CB  | ALA | B | 423 | 62.236 | −39.137 | −66.686 | 1.00 | 24.71 | C |
|------|------|-----|-----|---|-----|--------|---------|---------|------|-------|---|
| ATOM | 2216 | C   | ALA | B | 423 | 63.995 | −40.944 | −66.614 | 1.00 | 23.11 | C |
| ATOM | 2217 | O   | ALA | B | 423 | 64.493 | −40.584 | −65.549 | 1.00 | 22.70 | O |
| ATOM | 2218 | N   | LEU | B | 424 | 64.078 | −42.192 | −67.066 | 1.00 | 23.23 | N |
| ATOM | 2219 | CA  | LEU | B | 424 | 64.720 | −43.263 | −66.298 | 1.00 | 21.80 | C |
| ATOM | 2220 | CB  | LEU | B | 424 | 63.680 | −44.331 | −65.891 | 1.00 | 23.22 | C |
| ATOM | 2221 | CG  | LEU | B | 424 | 62.499 | −43.818 | −65.049 | 1.00 | 20.38 | C |
| ATOM | 2222 | CD1 | LEU | B | 424 | 61.370 | −44.844 | −65.013 | 1.00 | 24.99 | C |
| ATOM | 2223 | CD2 | LEU | B | 424 | 62.951 | −43.441 | −63.634 | 1.00 | 21.85 | C |
| ATOM | 2224 | C   | LEU | B | 424 | 65.810 | −43.918 | −67.113 | 1.00 | 27.47 | C |
| ATOM | 2225 | O   | LEU | B | 424 | 65.751 | −43.908 | −68.345 | 1.00 | 29.56 | O |
| ATOM | 2226 | N   | LEU | B | 425 | 66.784 | −44.517 | −66.416 | 1.00 | 29.62 | N |
| ATOM | 2227 | CA  | LEU | B | 425 | 67.863 | −45.284 | −67.043 | 1.00 | 35.64 | C |
| ATOM | 2228 | CB  | LEU | B | 425 | 69.214 | −44.716 | −66.653 | 1.00 | 36.39 | C |
| ATOM | 2229 | CG  | LEU | B | 425 | 70.221 | −44.498 | −67.783 | 1.00 | 48.35 | C |
| ATOM | 2230 | CD1 | LEU | B | 425 | 69.553 | −43.945 | −69.041 | 1.00 | 44.47 | C |
| ATOM | 2231 | CD2 | LEU | B | 425 | 71.308 | −43.554 | −67.297 | 1.00 | 48.49 | C |
| ATOM | 2232 | C   | LEU | B | 425 | 67.773 | −46.742 | −66.615 | 1.00 | 42.74 | C |
| ATOM | 2233 | O   | LEU | B | 425 | 67.237 | −47.014 | −65.558 | 1.00 | 43.56 | O |
| ATOM | 2234 | N   | PRO | B | 426 | 68.532 | −47.632 | −67.296 | 1.00 | 56.39 | N |
| ATOM | 2235 | CA  | PRO | B | 426 | 67.955 | −48.535 | −68.250 | 1.00 | 49.52 | C |
| ATOM | 2236 | CB  | PRO | B | 426 | 67.596 | −49.736 | −67.386 | 1.00 | 49.11 | C |
| ATOM | 2237 | CG  | PRO | B | 426 | 68.725 | −49.762 | −66.354 | 1.00 | 47.03 | C |
| ATOM | 2238 | CD  | PRO | B | 426 | 69.431 | −48.396 | −66.424 | 1.00 | 62.58 | C |
| ATOM | 2239 | C   | PRO | B | 426 | 66.762 | −47.901 | −68.955 | 1.00 | 57.15 | C |
| ATOM | 2240 | O   | PRO | B | 426 | 65.754 | −47.569 | −68.323 | 1.00 | 44.27 | O |
| ATOM | 2241 | N   | THR | B | 427 | 66.913 | −47.680 | −70.254 | 1.00 | 60.10 | N |
| ATOM | 2242 | CA  | THR | B | 427 | 66.055 | −46.754 | −70.968 | 1.00 | 64.18 | C |
| ATOM | 2243 | CB  | THR | B | 427 | 66.752 | −45.366 | −71.114 | 1.00 | 71.13 | C |
| ATOM | 2244 | OG1 | THR | B | 427 | 65.770 | −44.317 | −71.233 | 1.00 | 52.24 | O |
| ATOM | 2245 | CG2 | THR | B | 427 | 67.724 | −45.346 | −72.311 | 1.00 | 58.56 | C |
| ATOM | 2246 | C   | THR | B | 427 | 65.656 | −47.319 | −72.336 | 1.00 | 76.11 | C |
| ATOM | 2247 | O   | THR | B | 427 | 65.371 | −48.513 | −72.465 | 1.00 | 75.97 | O |
| ATOM | 2248 | N   | THR | D | 321 | 67.953 | −14.879 | −79.916 | 1.00 | 44.44 | N |
| ATOM | 2249 | CA  | THR | D | 321 | 66.490 | −15.242 | −79.994 | 1.00 | 39.62 | C |
| ATOM | 2250 | CB  | THR | D | 321 | 65.714 | −14.372 | −81.008 | 1.00 | 41.63 | C |
| ATOM | 2251 | OG1 | THR | D | 321 | 66.212 | −14.609 | −82.320 | 1.00 | 45.50 | O |
| ATOM | 2252 | CG2 | THR | D | 321 | 65.804 | −12.871 | −80.664 | 1.00 | 49.40 | C |
| ATOM | 2253 | C   | THR | D | 321 | 66.228 | −16.721 | −80.355 | 1.00 | 33.66 | C |
| ATOM | 2254 | O   | THR | D | 321 | 65.101 | −17.154 | −80.357 | 1.00 | 27.86 | O |
| ATOM | 2255 | N   | SER | D | 322 | 67.268 | −17.485 | −80.662 | 1.00 | 28.46 | N |
| ATOM | 2256 | CA  | SER | D | 322 | 67.068 | −18.900 | −81.008 | 1.00 | 30.21 | C |
| ATOM | 2257 | CB  | SER | D | 322 | 68.297 | −19.449 | −81.697 | 1.00 | 27.30 | C |
| ATOM | 2258 | OG  | SER | D | 322 | 68.479 | −18.814 | −82.931 | 1.00 | 34.80 | O |
| ATOM | 2259 | C   | SER | D | 322 | 66.718 | −19.765 | −79.796 | 1.00 | 29.25 | C |
| ATOM | 2260 | O   | SER | D | 322 | 67.366 | −19.677 | −78.751 | 1.00 | 28.20 | O |
| ATOM | 2261 | N   | LEU | D | 323 | 65.687 | −20.607 | −79.940 | 1.00 | 25.22 | N |
| ATOM | 2262 | CA  | LEU | D | 323 | 65.379 | −21.626 | −78.929 | 1.00 | 22.92 | C |
| ATOM | 2263 | CB  | LEU | D | 323 | 63.920 | −21.545 | −78.466 | 1.00 | 19.72 | C |
| ATOM | 2264 | CG  | LEU | D | 323 | 63.493 | −20.156 | −77.949 | 1.00 | 28.78 | C |
| ATOM | 2265 | CD1 | LEU | D | 323 | 62.035 | −20.148 | −77.553 | 1.00 | 30.40 | C |
| ATOM | 2266 | CD2 | LEU | D | 323 | 64.346 | −19.694 | −76.781 | 1.00 | 33.30 | C |
| ATOM | 2267 | C   | LEU | D | 323 | 65.683 | −23.002 | −79.490 | 1.00 | 23.34 | C |
| ATOM | 2268 | O   | LEU | D | 323 | 65.066 | −23.429 | −80.458 | 1.00 | 24.04 | O |
| ATOM | 2269 | N   | CYS | D | 324 | 66.656 | −23.677 | −78.884 | 1.00 | 25.44 | N |
| ATOM | 2270 | CA  | CYS | D | 324 | 67.222 | −24.907 | −79.436 | 1.00 | 25.51 | C |
| ATOM | 2271 | CB  | CYS | D | 324 | 68.754 | −24.799 | −79.453 | 1.00 | 23.78 | C |
| ATOM | 2272 | SG  | CYS | D | 324 | 69.309 | −23.636 | −80.701 | 1.00 | 32.31 | S |
| ATOM | 2273 | C   | CYS | D | 324 | 66.837 | −26.134 | −78.649 | 1.00 | 21.89 | C |
| ATOM | 2274 | O   | CYS | D | 324 | 66.594 | −26.057 | −77.442 | 1.00 | 23.78 | O |
| ATOM | 2275 | N   | CYS | D | 325 | 66.823 | −27.276 | −79.324 | 1.00 | 19.89 | N |
| ATOM | 2276 | CA  | CYS | D | 325 | 66.635 | −28.546 | −78.645 | 1.00 | 23.67 | C |
| ATOM | 2277 | CB  | CYS | D | 325 | 66.755 | −29.697 | −79.654 | 1.00 | 18.79 | C |
| ATOM | 2278 | SG  | CYS | D | 325 | 66.731 | −31.343 | −78.903 | 1.00 | 23.84 | S |
| ATOM | 2279 | C   | CYS | D | 325 | 67.689 | −28.693 | −77.518 | 1.00 | 26.11 | C |
| ATOM | 2280 | O   | CYS | D | 325 | 68.884 | −28.610 | −77.769 | 1.00 | 27.69 | O |
| ATOM | 2281 | N   | LYS | D | 326 | 67.236 | −28.929 | −76.290 | 1.00 | 25.67 | N |
| ATOM | 2282 | CA  | LYS | D | 326 | 68.162 | −29.078 | −75.151 | 1.00 | 24.80 | C |
| ATOM | 2283 | CB  | LYS | D | 326 | 67.385 | −29.235 | −73.856 | 1.00 | 28.45 | C |
| ATOM | 2284 | CG  | LYS | D | 326 | 68.255 | −29.277 | −72.603 | 1.00 | 29.89 | C |
| ATOM | 2285 | CD  | LYS | D | 326 | 67.404 | −29.350 | −71.343 | 1.00 | 31.48 | C |
| ATOM | 2286 | CE  | LYS | D | 326 | 66.716 | −30.702 | −71.213 | 1.00 | 43.44 | C |
| ATOM | 2287 | NZ  | LYS | D | 326 | 66.101 | −30.908 | −69.864 | 1.00 | 56.07 | N |
| ATOM | 2288 | C   | LYS | D | 326 | 69.120 | −30.267 | −75.335 | 1.00 | 29.95 | C |
| ATOM | 2289 | O   | LYS | D | 326 | 70.288 | −30.197 | −74.942 | 1.00 | 28.84 | O |
| ATOM | 2290 | N   | GLN | D | 327 | 68.634 | −31.330 | −75.961 | 1.00 | 24.61 | N |
| ATOM | 2291 | CA  | GLN | D | 327 | 69.411 | −32.598 | −76.081 | 1.00 | 29.81 | C |
| ATOM | 2292 | CB  | GLN | D | 327 | 68.488 | −33.795 | −76.367 | 1.00 | 25.61 | C |

TABLE 5-continued

Atomic coordinates for CRBN(TBD):Thalidomide (Murine protein)

| ATOM | 2293 | CG | GLN | D | 327 | 69.194 | −35.046 | −76.892 | 1.00 | 35.40 | C |
|------|------|------|-----|---|-----|--------|---------|---------|------|-------|---|
| ATOM | 2294 | CD | GLN | D | 327 | 70.008 | −35.742 | −75.822 | 1.00 | 44.68 | C |
| ATOM | 2295 | OE1 | GLN | D | 327 | 69.738 | −35.583 | −74.630 | 1.00 | 35.09 | O |
| ATOM | 2296 | NE2 | GLN | D | 327 | 71.029 | −36.508 | −76.240 | 1.00 | 40.17 | N |
| ATOM | 2297 | C | GLN | D | 327 | 70.542 | −32.540 | −77.114 | 1.00 | 33.25 | C |
| ATOM | 2298 | O | GLN | D | 327 | 71.669 | −32.899 | −76.808 | 1.00 | 27.19 | O |
| ATOM | 2299 | N | CYS | D | 328 | 70.239 | −32.134 | −78.347 | 1.00 | 27.64 | N |
| ATOM | 2300 | CA | CYS | D | 328 | 71.279 | −32.080 | −79.368 | 1.00 | 30.83 | C |
| ATOM | 2301 | CB | CYS | D | 328 | 70.766 | −32.574 | −80.720 | 1.00 | 33.24 | C |
| ATOM | 2302 | SG | CYS | D | 328 | 69.439 | −31.547 | −81.421 | 1.00 | 27.36 | S |
| ATOM | 2303 | C | CYS | D | 328 | 71.915 | −30.692 | −79.469 | 1.00 | 27.65 | C |
| ATOM | 2304 | O | CYS | D | 328 | 72.922 | −30.516 | −80.155 | 1.00 | 29.26 | O |
| ATOM | 2305 | N | GLN | D | 329 | 71.337 | −29.726 | −78.758 | 1.00 | 24.10 | N |
| ATOM | 2306 | CA | GLN | D | 329 | 71.948 | −28.408 | −78.521 | 1.00 | 27.95 | C |
| ATOM | 2307 | CB | GLN | D | 329 | 73.332 | −28.549 | −77.843 | 1.00 | 31.61 | C |
| ATOM | 2308 | CG | GLN | D | 329 | 73.307 | −29.476 | −76.620 | 1.00 | 28.22 | C |
| ATOM | 2309 | CD | GLN | D | 329 | 74.666 | −29.638 | −75.948 | 1.00 | 39.75 | C |
| ATOM | 2310 | OE1 | GLN | D | 329 | 75.308 | −28.659 | −75.569 | 1.00 | 36.77 | O |
| ATOM | 2311 | NE2 | GLN | D | 329 | 75.095 | −30.883 | −75.780 | 1.00 | 42.28 | N |
| ATOM | 2312 | C | GLN | D | 329 | 72.018 | −27.461 | −79.743 | 1.00 | 29.87 | C |
| ATOM | 2313 | O | GLN | D | 329 | 71.900 | −26.246 | −79.588 | 1.00 | 43.02 | O |
| ATOM | 2314 | N | GLU | D | 330 | 72.143 | −28.024 | −80.935 | 1.00 | 29.98 | N |
| ATOM | 2315 | CA | GLU | D | 330 | 72.464 | −27.255 | −82.132 | 1.00 | 40.03 | C |
| ATOM | 2316 | CB | GLU | D | 330 | 73.475 | −28.015 | −83.004 | 1.00 | 46.93 | C |
| ATOM | 2317 | CG | GLU | D | 330 | 74.854 | −28.177 | −82.375 | 1.00 | 61.31 | C |
| ATOM | 2318 | CD | GLU | D | 330 | 75.483 | −26.849 | −82.009 | 1.00 | 71.59 | C |
| ATOM | 2319 | OE1 | GLU | D | 330 | 75.537 | −26.528 | −80.800 | 1.00 | 74.82 | O |
| ATOM | 2320 | OE2 | GLU | D | 330 | 75.901 | −26.115 | −82.932 | 1.00 | 84.62 | O |
| ATOM | 2321 | C | GLU | D | 330 | 71.233 | −26.936 | −82.976 | 1.00 | 36.38 | C |
| ATOM | 2322 | O | GLU | D | 330 | 71.265 | −26.028 | −83.815 | 1.00 | 34.33 | O |
| ATOM | 2323 | N | THR | D | 331 | 70.175 | −27.703 | −82.782 | 1.00 | 27.07 | N |
| ATOM | 2324 | CA | THR | D | 331 | 69.036 | −27.665 | −83.694 | 1.00 | 26.59 | C |
| ATOM | 2325 | CB | THR | D | 331 | 68.374 | −29.045 | −83.785 | 1.00 | 30.74 | C |
| ATOM | 2326 | OG1 | THR | D | 331 | 69.347 | −30.004 | −84.252 | 1.00 | 31.83 | O |
| ATOM | 2327 | CG2 | THR | D | 331 | 67.191 | −29.025 | −84.732 | 1.00 | 23.43 | C |
| ATOM | 2328 | C | THR | D | 331 | 68.044 | −26.636 | −83.185 | 1.00 | 26.22 | C |
| ATOM | 2329 | O | THR | D | 331 | 67.502 | −26.763 | −82.069 | 1.00 | 20.96 | O |
| ATOM | 2330 | N | GLU | D | 332 | 67.812 | −25.609 | −83.992 | 1.00 | 21.63 | N |
| ATOM | 2331 | CA | GLU | D | 332 | 66.864 | −24.563 | −83.633 | 1.00 | 22.42 | C |
| ATOM | 2332 | CB | GLU | D | 332 | 67.072 | −23.322 | −84.508 | 1.00 | 23.45 | C |
| ATOM | 2333 | CG | GLU | D | 332 | 66.102 | −22.208 | −84.131 | 1.00 | 24.23 | C |
| ATOM | 2334 | CD | GLU | D | 332 | 66.234 | −21.014 | −85.022 | 1.00 | 28.65 | C |
| ATOM | 2335 | OE1 | GLU | D | 332 | 67.171 | −20.229 | −84.813 | 1.00 | 25.99 | O |
| ATOM | 2336 | OE2 | GLU | D | 332 | 65.396 | −20.875 | −85.924 | 1.00 | 24.99 | O |
| ATOM | 2337 | C | GLU | D | 332 | 65.432 | −25.071 | −83.797 | 1.00 | 21.70 | C |
| ATOM | 2338 | O | GLU | D | 332 | 65.072 | −25.599 | −84.857 | 1.00 | 24.48 | O |
| ATOM | 2339 | N | ILE | D | 333 | 64.618 | −24.923 | −82.753 | 1.00 | 16.36 | N |
| ATOM | 2340 | CA | ILE | D | 333 | 63.216 | −25.408 | −82.838 | 1.00 | 16.17 | C |
| ATOM | 2341 | CB | ILE | D | 333 | 62.793 | −26.196 | −81.594 | 1.00 | 17.10 | C |
| ATOM | 2342 | CG1 | ILE | D | 333 | 63.751 | −27.384 | −81.383 | 1.00 | 20.80 | C |
| ATOM | 2343 | CD1 | ILE | D | 333 | 63.748 | −28.384 | −82.536 | 1.00 | 17.38 | C |
| ATOM | 2344 | CG2 | ILE | D | 333 | 61.336 | −26.656 | −81.729 | 1.00 | 17.71 | C |
| ATOM | 2345 | C | ILE | D | 333 | 62.222 | −24.270 | −83.074 | 1.00 | 18.22 | C |
| ATOM | 2346 | O | ILE | D | 333 | 61.250 | −24.436 | −83.813 | 1.00 | 18.73 | O |
| ATOM | 2347 | N | THR | D | 334 | 62.449 | −23.150 | −82.408 | 1.00 | 20.52 | N |
| ATOM | 2348 | CA | THR | D | 334 | 61.643 | −21.931 | −82.659 | 1.00 | 21.42 | C |
| ATOM | 2349 | CB | THR | D | 334 | 60.296 | −21.945 | −81.878 | 1.00 | 21.16 | C |
| ATOM | 2350 | OG1 | THR | D | 334 | 59.470 | −20.838 | −82.304 | 1.00 | 21.42 | O |
| ATOM | 2351 | CG2 | THR | D | 334 | 60.540 | −21.840 | −80.395 | 1.00 | 18.90 | C |
| ATOM | 2352 | C | THR | D | 334 | 62.496 | −20.717 | −82.317 | 1.00 | 21.10 | C |
| ATOM | 2353 | O | THR | D | 334 | 63.682 | −20.858 | −82.028 | 1.00 | 19.46 | O |
| ATOM | 2354 | N | THR | D | 335 | 61.921 | −19.529 | −82.405 | 1.00 | 19.83 | N |
| ATOM | 2355 | CA | THR | D | 335 | 62.616 | −18.352 | −81.969 | 1.00 | 23.05 | C |
| ATOM | 2356 | CB | THR | D | 335 | 62.988 | −17.452 | −83.153 | 1.00 | 22.99 | C |
| ATOM | 2357 | OG1 | THR | D | 335 | 61.812 | −16.844 | −83.660 | 1.00 | 26.04 | O |
| ATOM | 2358 | CG2 | THR | D | 335 | 63.651 | −18.256 | −84.272 | 1.00 | 24.90 | C |
| ATOM | 2359 | C | THR | D | 335 | 61.744 | −17.564 | −81.003 | 1.00 | 21.50 | C |
| ATOM | 2360 | O | THR | D | 335 | 60.492 | −17.721 | −80.976 | 1.00 | 20.48 | O |
| ATOM | 2361 | N | LYS | D | 336 | 62.368 | −16.691 | −80.232 | 1.00 | 19.92 | N |
| ATOM | 2362 | CA | LYS | D | 336 | 61.586 | −15.802 | −79.342 | 1.00 | 22.50 | C |
| ATOM | 2363 | CB | LYS | D | 336 | 62.503 | −14.888 | −78.548 | 1.00 | 22.50 | C |
| ATOM | 2364 | CG | LYS | D | 336 | 63.178 | −15.542 | −77.349 | 1.00 | 32.98 | C |
| ATOM | 2365 | CD | LYS | D | 336 | 64.027 | −14.507 | −76.621 | 1.00 | 32.46 | C |
| ATOM | 2366 | CE | LYS | D | 336 | 64.581 | −15.052 | −75.321 | 1.00 | 42.54 | C |
| ATOM | 2367 | NZ | LYS | D | 336 | 65.145 | −13.950 | −74.506 | 1.00 | 47.55 | N |
| ATOM | 2368 | C | LYS | D | 336 | 60.537 | −14.964 | −80.114 | 1.00 | 20.92 | C |
| ATOM | 2369 | O | LYS | D | 336 | 59.489 | −14.613 | −79.567 | 1.00 | 18.93 | O |
| ATOM | 2370 | N | ASN | D | 337 | 60.822 | −14.641 | −81.372 | 1.00 | 17.68 | N |

TABLE 5-continued

Atomic coordinates for CRBN(TBD):Thalidomide (Murine protein)

| ATOM | 2371 | CA | ASN | D | 337 | 59.892 | −13.849 | −82.177 | 1.00 | 21.09 | C |
|---|---|---|---|---|---|---|---|---|---|---|---|
| ATOM | 2372 | CB | ASN | D | 337 | 60.540 | −13.435 | −83.497 | 1.00 | 19.30 | C |
| ATOM | 2373 | CG | ASN | D | 337 | 61.855 | −12.703 | −83.290 | 1.00 | 32.88 | C |
| ATOM | 2374 | OD1 | ASN | D | 337 | 62.919 | −13.201 | −83.655 | 1.00 | 38.62 | O |
| ATOM | 2375 | ND2 | ASN | D | 337 | 61.797 | −11.572 | −82.618 | 1.00 | 32.56 | N |
| ATOM | 2376 | C | ASN | D | 337 | 58.553 | −14.559 | −82.448 | 1.00 | 19.23 | C |
| ATOM | 2377 | O | ASN | D | 337 | 57.565 | −13.918 | −82.805 | 1.00 | 17.93 | O |
| ATOM | 2378 | N | GLU | D | 338 | 58.540 | −15.880 | −82.312 | 1.00 | 16.14 | N |
| ATOM | 2379 | CA | GLU | D | 338 | 57.346 | −16.678 | −82.630 | 1.00 | 16.54 | C |
| ATOM | 2380 | CB | GLU | D | 338 | 57.743 | −18.046 | −83.234 | 1.00 | 21.08 | C |
| ATOM | 2381 | CG | GLU | D | 338 | 58.497 | −17.934 | −84.552 | 1.00 | 21.82 | C |
| ATOM | 2382 | CD | GLU | D | 338 | 57.808 | −16.994 | −85.526 | 1.00 | 28.91 | C |
| ATOM | 2383 | OE1 | GLU | D | 338 | 56.576 | −17.126 | −85.728 | 1.00 | 24.73 | O |
| ATOM | 2384 | OE2 | GLU | D | 338 | 58.496 | −16.123 | −86.090 | 1.00 | 34.64 | O |
| ATOM | 2385 | C | GLU | D | 338 | 56.429 | −16.872 | −81.442 | 1.00 | 17.76 | C |
| ATOM | 2386 | O | GLU | D | 338 | 55.300 | −17.345 | −81.587 | 1.00 | 16.91 | O |
| ATOM | 2387 | N | ILE | D | 339 | 56.880 | −16.440 | −80.270 | 1.00 | 18.50 | N |
| ATOM | 2388 | CA | ILE | D | 339 | 56.131 | −16.659 | −79.035 | 1.00 | 17.47 | C |
| ATOM | 2389 | CB | ILE | D | 339 | 56.983 | −16.291 | −77.792 | 1.00 | 19.50 | C |
| ATOM | 2390 | CG1 | ILE | D | 339 | 58.180 | −17.257 | −77.657 | 1.00 | 20.60 | C |
| ATOM | 2391 | CD1 | ILE | D | 339 | 59.169 | −16.849 | −76.562 | 1.00 | 21.66 | C |
| ATOM | 2392 | CG2 | ILE | D | 339 | 56.126 | −16.311 | −76.537 | 1.00 | 20.45 | C |
| ATOM | 2393 | C | ILE | D | 339 | 54.838 | −15.832 | −78.992 | 1.00 | 18.80 | C |
| ATOM | 2394 | O | ILE | D | 339 | 54.835 | −14.644 | −79.351 | 1.00 | 17.55 | O |
| ATOM | 2395 | N | PHE | D | 340 | 53.743 | −16.464 | −78.577 | 1.00 | 14.25 | N |
| ATOM | 2396 | CA | PHE | D | 340 | 52.483 | −15.735 | −78.373 | 1.00 | 18.16 | C |
| ATOM | 2397 | CB | PHE | D | 340 | 51.594 | −15.734 | −79.655 | 1.00 | 14.54 | C |
| ATOM | 2398 | CG | PHE | D | 340 | 50.872 | −17.032 | −79.914 | 1.00 | 16.30 | C |
| ATOM | 2399 | CD2 | PHE | D | 340 | 49.497 | −17.147 | −79.675 | 1.00 | 17.44 | C |
| ATOM | 2400 | CE2 | PHE | D | 340 | 48.815 | −18.342 | −79.926 | 1.00 | 17.02 | C |
| ATOM | 2401 | CZ | PHE | D | 340 | 49.509 | −19.464 | −80.427 | 1.00 | 20.18 | C |
| ATOM | 2402 | CE1 | PHE | D | 340 | 50.881 | −19.358 | −80.714 | 1.00 | 15.15 | C |
| ATOM | 2403 | CD1 | PHE | D | 340 | 51.567 | −18.169 | −80.438 | 1.00 | 16.03 | C |
| ATOM | 2404 | C | PHE | D | 340 | 51.766 | −16.347 | −77.206 | 1.00 | 20.74 | C |
| ATOM | 2405 | O | PHE | D | 340 | 52.199 | −17.383 | −76.692 | 1.00 | 19.13 | O |
| ATOM | 2406 | N | SER | D | 341 | 50.691 | −15.695 | −76.756 | 1.00 | 19.60 | N |
| ATOM | 2407 | CA | SER | D | 341 | 49.922 | −16.213 | −75.619 | 1.00 | 23.90 | C |
| ATOM | 2408 | CB | SER | D | 341 | 49.864 | −15.170 | −74.495 | 1.00 | 27.38 | C |
| ATOM | 2409 | OG | SER | D | 341 | 49.295 | −15.727 | −73.316 | 1.00 | 35.12 | O |
| ATOM | 2410 | C | SER | D | 341 | 48.542 | −16.648 | −76.027 | 1.00 | 22.50 | C |
| ATOM | 2411 | O | SER | D | 341 | 47.650 | −15.842 | −76.184 | 1.00 | 25.37 | O |
| ATOM | 2412 | N | LEU | D | 342 | 48.391 | −17.937 | −76.286 | 1.00 | 25.13 | N |
| ATOM | 2413 | CA | LEU | D | 342 | 47.095 | −18.505 | −76.597 | 1.00 | 24.94 | C |
| ATOM | 2414 | CB | LEU | D | 342 | 47.248 | −19.963 | −77.072 | 1.00 | 25.61 | C |
| ATOM | 2415 | CG | LEU | D | 342 | 46.045 | −20.630 | −77.755 | 1.00 | 31.69 | C |
| ATOM | 2416 | CD1 | LEU | D | 342 | 44.980 | −21.046 | −76.754 | 1.00 | 32.58 | C |
| ATOM | 2417 | CD2 | LEU | D | 342 | 45.448 | −19.691 | −78.793 | 1.00 | 34.18 | C |
| ATOM | 2418 | C | LEU | D | 342 | 46.251 | −18.440 | −75.334 | 1.00 | 29.27 | C |
| ATOM | 2419 | O | LEU | D | 342 | 45.120 | −17.918 | −75.346 | 1.00 | 23.49 | O |
| ATOM | 2420 | N | SER | D | 343 | 46.824 | −18.928 | −74.228 | 1.00 | 28.36 | N |
| ATOM | 2421 | CA | ASER | D | 343 | 46.144 | −18.902 | −72.949 | 0.50 | 30.32 | C |
| ATOM | 2422 | CA | BSER | D | 343 | 46.155 | −18.901 | −72.937 | 0.50 | 29.33 | C |
| ATOM | 2423 | CB | ASER | D | 343 | 46.865 | −19.803 | −71.937 | 0.50 | 31.29 | C |
| ATOM | 2424 | CB | BSER | D | 343 | 46.896 | −19.788 | −71.915 | 0.50 | 28.18 | C |
| ATOM | 2425 | OG | ASER | D | 343 | 48.130 | −19.263 | −71.611 | 0.50 | 29.93 | O |
| ATOM | 2426 | OG | BSER | D | 343 | 47.057 | −21.106 | −72.399 | 0.50 | 23.67 | O |
| ATOM | 2427 | C | SER | D | 343 | 46.099 | −17.471 | −72.423 | 1.00 | 33.93 | C |
| ATOM | 2428 | O | SER | D | 343 | 47.004 | −16.672 | −72.691 | 1.00 | 31.24 | O |
| ATOM | 2429 | N | LEU | D | 344 | 45.043 | −17.155 | −71.682 | 1.00 | 29.96 | N |
| ATOM | 2430 | CA | LEU | D | 344 | 44.870 | −15.825 | −71.090 | 1.00 | 35.32 | C |
| ATOM | 2431 | CB | LEU | D | 344 | 43.574 | −15.767 | −70.271 | 1.00 | 35.61 | C |
| ATOM | 2432 | CG | LEU | D | 344 | 42.285 | −16.016 | −71.070 | 1.00 | 50.21 | C |
| ATOM | 2433 | CD1 | LEU | D | 344 | 41.083 | −15.968 | −70.144 | 1.00 | 52.66 | C |
| ATOM | 2434 | CD2 | LEU | D | 344 | 42.120 | −15.041 | −72.237 | 1.00 | 39.69 | C |
| ATOM | 2435 | C | LEU | D | 344 | 46.042 | −15.401 | −70.213 | 1.00 | 40.17 | C |
| ATOM | 2436 | O | LEU | D | 344 | 46.648 | −16.233 | −69.502 | 1.00 | 33.33 | O |
| ATOM | 2437 | N | CYS | D | 345 | 46.310 | −14.092 | −70.234 | 1.00 | 46.57 | N |
| ATOM | 2438 | CA | CYS | D | 345 | 47.419 | −13.465 | −69.508 | 1.00 | 54.22 | C |
| ATOM | 2439 | CB | CYS | D | 345 | 48.094 | −12.396 | −70.392 | 1.00 | 54.37 | C |
| ATOM | 2440 | SG | CYS | D | 345 | 47.985 | −12.684 | −72.182 | 1.00 | 58.02 | S |
| ATOM | 2441 | C | CYS | D | 345 | 46.905 | −12.795 | −68.231 | 1.00 | 61.31 | C |
| ATOM | 2442 | O | CYS | D | 345 | 45.689 | −12.747 | −67.986 | 1.00 | 53.83 | O |
| ATOM | 2443 | N | GLY | D | 346 | 47.832 | −12.259 | −67.434 | 1.00 | 61.51 | N |
| ATOM | 2444 | CA | GLY | D | 346 | 47.478 | −11.492 | −66.231 | 1.00 | 56.35 | C |
| ATOM | 2445 | C | GLY | D | 346 | 46.978 | −12.357 | −65.079 | 1.00 | 54.40 | C |
| ATOM | 2446 | O | GLY | D | 346 | 47.476 | −13.476 | −64.870 | 1.00 | 54.53 | O |
| ATOM | 2447 | N | PRO | D | 347 | 45.995 | −11.837 | −64.307 | 1.00 | 45.88 | N |
| ATOM | 2448 | CA | PRO | D | 347 | 45.462 | −12.549 | −63.128 | 1.00 | 46.75 | C |

TABLE 5-continued

Atomic coordinates for CRBN(TBD):Thalidomide (Murine protein)

| ATOM | 2449 | CB | PRO | D | 347 | 44.562 | −11.492 | −62.449 | 1.00 | 45.71 | C |
| ATOM | 2450 | CG | PRO | D | 347 | 45.040 | −10.173 | −62.984 | 1.00 | 49.98 | C |
| ATOM | 2451 | CD | PRO | D | 347 | 45.492 | −10.450 | −64.389 | 1.00 | 50.19 | C |
| ATOM | 2452 | C | PRO | D | 347 | 44.656 | −13.826 | −63.466 | 1.00 | 43.50 | C |
| ATOM | 2453 | O | PRO | D | 347 | 44.261 | −14.554 | −62.559 | 1.00 | 54.05 | O |
| ATOM | 2454 | N | MET | D | 348 | 44.414 | −14.079 | −64.759 | 1.00 | 36.05 | N |
| ATOM | 2455 | CA | MET | D | 348 | 43.774 | −15.327 | −65.193 | 1.00 | 39.70 | C |
| ATOM | 2456 | CB | MET | D | 348 | 42.900 | −15.097 | −66.425 | 1.00 | 40.80 | C |
| ATOM | 2457 | CG | MET | D | 348 | 41.527 | −14.504 | −66.099 | 1.00 | 36.76 | C |
| ATOM | 2458 | SD | MET | D | 348 | 40.487 | −15.594 | −65.099 | 1.00 | 39.12 | S |
| ATOM | 2459 | CE | MET | D | 348 | 40.536 | −17.091 | −66.102 | 1.00 | 40.07 | C |
| ATOM | 2460 | C | MET | D | 348 | 44.765 | −16.477 | −65.442 | 1.00 | 37.01 | C |
| ATOM | 2461 | O | MET | D | 348 | 44.362 | −17.636 | −65.479 | 1.00 | 38.01 | O |
| ATOM | 2462 | N | ALA | D | 349 | 46.052 | −16.146 | −65.602 | 1.00 | 40.94 | N |
| ATOM | 2463 | CA | ALA | D | 349 | 47.106 | −17.163 | −65.881 | 1.00 | 53.94 | C |
| ATOM | 2464 | CB | ALA | D | 349 | 48.487 | −16.512 | −65.917 | 1.00 | 47.04 | C |
| ATOM | 2465 | C | ALA | D | 349 | 47.083 | −18.346 | −64.881 | 1.00 | 58.15 | C |
| ATOM | 2466 | O | ALA | D | 349 | 47.228 | −19.520 | −65.273 | 1.00 | 46.82 | O |
| ATOM | 2467 | N | ALA | D | 350 | 46.859 | −18.023 | −63.603 | 1.00 | 57.24 | N |
| ATOM | 2468 | CA | ALA | D | 350 | 46.805 | −19.015 | −62.530 | 1.00 | 52.59 | C |
| ATOM | 2469 | CB | ALA | D | 350 | 46.872 | −18.319 | −61.167 | 1.00 | 48.28 | C |
| ATOM | 2470 | C | ALA | D | 350 | 45.565 | −19.931 | −62.617 | 1.00 | 57.05 | C |
| ATOM | 2471 | O | ALA | D | 350 | 45.547 | −21.021 | −62.039 | 1.00 | 46.40 | O |
| ATOM | 2472 | N | TYR | D | 351 | 44.539 | −19.490 | −63.348 | 1.00 | 48.21 | N |
| ATOM | 2473 | CA | TYR | D | 351 | 43.288 | −20.250 | −63.450 | 1.00 | 47.97 | C |
| ATOM | 2474 | CB | TYR | D | 351 | 42.085 | −19.308 | −63.421 | 1.00 | 53.85 | C |
| ATOM | 2475 | CG | TYR | D | 351 | 41.795 | −18.780 | −62.047 | 1.00 | 48.98 | C |
| ATOM | 2476 | CD2 | TYR | D | 351 | 40.910 | −19.451 | −61.194 | 1.00 | 50.32 | C |
| ATOM | 2477 | CE2 | TYR | D | 351 | 40.658 | −18.978 | −59.915 | 1.00 | 50.03 | C |
| ATOM | 2478 | CZ | TYR | D | 351 | 41.306 | −17.820 | −59.477 | 1.00 | 53.88 | C |
| ATOM | 2479 | OH | TYR | D | 351 | 41.069 | −17.338 | −58.222 | 1.00 | 61.26 | O |
| ATOM | 2480 | CE1 | TYR | D | 351 | 42.195 | −17.149 | −60.301 | 1.00 | 50.73 | C |
| ATOM | 2481 | CD1 | TYR | D | 351 | 42.434 | −17.630 | −61.575 | 1.00 | 49.23 | C |
| ATOM | 2482 | C | TYR | D | 351 | 43.206 | −21.152 | −64.678 | 1.00 | 54.85 | C |
| ATOM | 2483 | O | TYR | D | 351 | 42.379 | −22.068 | −64.733 | 1.00 | 63.23 | O |
| ATOM | 2484 | N | VAL | D | 352 | 44.051 | −20.887 | −65.665 | 1.00 | 47.99 | N |
| ATOM | 2485 | CA | VAL | D | 352 | 43.874 | −21.496 | −66.989 | 1.00 | 45.26 | C |
| ATOM | 2486 | CB | VAL | D | 352 | 44.149 | −20.479 | −68.160 | 1.00 | 38.21 | C |
| ATOM | 2487 | CG1 | VAL | D | 352 | 43.183 | −19.294 | −68.075 | 1.00 | 36.70 | C |
| ATOM | 2488 | CG2 | VAL | D | 352 | 45.584 | −19.981 | −68.135 | 1.00 | 38.85 | C |
| ATOM | 2489 | C | VAL | D | 352 | 44.647 | −22.840 | −67.142 | 1.00 | 38.08 | C |
| ATOM | 2490 | O | VAL | D | 352 | 44.361 | −23.622 | −68.051 | 1.00 | 41.25 | O |
| ATOM | 2491 | N | ASN | D | 353 | 45.586 | −23.110 | −66.227 | 1.00 | 33.57 | N |
| ATOM | 2492 | CA | ASN | D | 353 | 46.250 | −24.448 | −66.155 | 1.00 | 37.20 | C |
| ATOM | 2493 | CB | ASN | D | 353 | 47.678 | −24.391 | −66.708 | 1.00 | 43.06 | C |
| ATOM | 2494 | CG | ASN | D | 353 | 47.717 | −24.339 | −68.221 | 1.00 | 42.18 | C |
| ATOM | 2495 | OD1 | ASN | D | 353 | 47.416 | −25.324 | −68.903 | 1.00 | 38.05 | O |
| ATOM | 2496 | ND2 | ASN | D | 353 | 48.093 | −23.192 | −68.755 | 1.00 | 38.82 | N |
| ATOM | 2497 | C | ASN | D | 353 | 46.289 | −24.941 | −64.714 | 1.00 | 43.29 | C |
| ATOM | 2498 | O | ASN | D | 353 | 46.186 | −24.121 | −63.785 | 1.00 | 41.95 | O |
| ATOM | 2499 | N | PRO | D | 354 | 46.463 | −26.275 | −64.511 | 1.00 | 47.24 | N |
| ATOM | 2500 | CA | PRO | D | 354 | 46.615 | −26.790 | −63.134 | 1.00 | 46.91 | C |
| ATOM | 2501 | CB | PRO | D | 354 | 46.833 | −28.306 | −63.333 | 1.00 | 40.94 | C |
| ATOM | 2502 | CG | PRO | D | 354 | 46.448 | −28.598 | −64.748 | 1.00 | 44.08 | C |
| ATOM | 2503 | CD | PRO | D | 354 | 46.659 | −27.333 | −65.525 | 1.00 | 46.85 | C |
| ATOM | 2504 | C | PRO | D | 354 | 47.842 | −26.174 | −62.464 | 1.00 | 45.55 | C |
| ATOM | 2505 | O | PRO | D | 354 | 48.786 | −25.777 | −63.152 | 1.00 | 39.56 | O |
| ATOM | 2506 | N | HIS | D | 355 | 47.829 | −26.079 | −61.134 | 1.00 | 45.30 | N |
| ATOM | 2507 | CA | HIS | D | 355 | 49.045 | −25.721 | −60.403 | 1.00 | 45.87 | C |
| ATOM | 2508 | CB | HIS | D | 355 | 48.789 | −25.685 | −58.900 | 1.00 | 49.39 | C |
| ATOM | 2509 | CG | HIS | D | 355 | 47.640 | −24.783 | −58.499 | 1.00 | 71.56 | C |
| ATOM | 2510 | ND1 | HIS | D | 355 | 47.389 | −23.605 | −59.113 | 1.00 | 80.15 | N |
| ATOM | 2511 | CE1 | HIS | D | 355 | 46.310 | −23.028 | −58.549 | 1.00 | 77.53 | C |
| ATOM | 2512 | NE2 | HIS | D | 355 | 45.870 | −23.831 | −57.567 | 1.00 | 79.81 | N |
| ATOM | 2513 | CD2 | HIS | D | 355 | 46.666 | −24.922 | −57.506 | 1.00 | 78.62 | C |
| ATOM | 2514 | C | HIS | D | 355 | 50.120 | −26.723 | −60.740 | 1.00 | 44.54 | C |
| ATOM | 2515 | O | HIS | D | 355 | 49.828 | −27.923 | −60.930 | 1.00 | 33.48 | O |
| ATOM | 2516 | N | GLY | D | 356 | 51.359 | −26.239 | −60.857 | 1.00 | 37.58 | N |
| ATOM | 2517 | CA | GLY | D | 356 | 52.482 | −27.058 | −61.322 | 1.00 | 40.85 | C |
| ATOM | 2518 | C | GLY | D | 356 | 52.776 | −26.852 | −62.808 | 1.00 | 38.27 | C |
| ATOM | 2519 | O | GLY | D | 356 | 53.879 | −27.122 | −63.262 | 1.00 | 38.29 | O |
| ATOM | 2520 | N | TYR | D | 357 | 51.784 | −26.370 | −63.561 | 1.00 | 31.59 | N |
| ATOM | 2521 | CA | TYR | D | 357 | 51.902 | −26.289 | −65.033 | 1.00 | 35.46 | C |
| ATOM | 2522 | CB | TYR | D | 357 | 51.007 | −27.336 | −65.703 | 1.00 | 32.29 | C |
| ATOM | 2523 | CG | TYR | D | 357 | 51.494 | −28.757 | −65.507 | 1.00 | 28.76 | C |
| ATOM | 2524 | CD1 | TYR | D | 357 | 52.816 | −29.104 | −65.791 | 1.00 | 33.11 | C |
| ATOM | 2525 | CE1 | TYR | D | 357 | 53.278 | −30.410 | −65.607 | 1.00 | 30.23 | C |
| ATOM | 2526 | CZ | TYR | D | 357 | 52.407 | −31.378 | −65.148 | 1.00 | 29.53 | C |

TABLE 5-continued

Atomic coordinates for CRBN(TBD):Thalidomide (Murine protein)

| ATOM | 2527 | OH | TYR | D | 357 | 52.882 | −32.673 | −64.972 | 1.00 | 29.44 | O |
|---|---|---|---|---|---|---|---|---|---|---|---|
| ATOM | 2528 | CE2 | TYR | D | 357 | 51.089 | −31.067 | −64.872 | 1.00 | 26.99 | C |
| ATOM | 2529 | CD2 | TYR | D | 357 | 50.635 | −29.756 | −65.043 | 1.00 | 26.63 | C |
| ATOM | 2530 | C | TYR | D | 357 | 51.616 | −24.909 | −65.635 | 1.00 | 43.94 | C |
| ATOM | 2531 | O | TYR | D | 357 | 51.441 | −24.778 | −66.871 | 1.00 | 37.75 | O |
| ATOM | 2532 | N | VAL | D | 358 | 51.581 | −23.885 | −64.787 | 1.00 | 38.84 | N |
| ATOM | 2533 | CA | VAL | D | 358 | 51.235 | −22.529 | −65.247 | 1.00 | 43.50 | C |
| ATOM | 2534 | CB | VAL | D | 358 | 51.033 | −21.528 | −64.072 | 1.00 | 51.57 | C |
| ATOM | 2535 | CG1 | VAL | D | 358 | 49.913 | −22.004 | −63.138 | 1.00 | 45.44 | C |
| ATOM | 2536 | CG2 | VAL | D | 358 | 52.336 | −21.316 | −63.306 | 1.00 | 52.19 | C |
| ATOM | 2537 | C | VAL | D | 358 | 52.251 | −21.991 | −66.275 | 1.00 | 47.53 | C |
| ATOM | 2538 | O | VAL | D | 358 | 51.880 | −21.235 | −67.172 | 1.00 | 52.85 | O |
| ATOM | 2539 | N | HIS | D | 359 | 53.512 | −22.422 | −66.162 | 1.00 | 44.52 | N |
| ATOM | 2540 | CA | HIS | D | 359 | 54.570 | −21.985 | −67.076 | 1.00 | 43.78 | C |
| ATOM | 2541 | CB | HIS | D | 359 | 55.583 | −21.106 | −66.334 | 1.00 | 65.42 | C |
| ATOM | 2542 | CG | HIS | D | 359 | 55.198 | −19.644 | −66.278 | 1.00 | 82.70 | C |
| ATOM | 2543 | ND1 | HIS | D | 359 | 54.295 | −19.161 | −65.395 | 1.00 | 97.15 | N |
| ATOM | 2544 | CE1 | HIS | D | 359 | 54.151 | −17.835 | −65.582 | 1.00 | 89.11 | C |
| ATOM | 2545 | NE2 | HIS | D | 359 | 54.965 | −17.463 | −66.584 | 1.00 | 102.06 | N |
| ATOM | 2546 | CD2 | HIS | D | 359 | 55.625 | −18.553 | −67.039 | 1.00 | 88.79 | C |
| ATOM | 2547 | C | HIS | D | 359 | 55.275 | −23.147 | −67.731 | 1.00 | 40.22 | C |
| ATOM | 2548 | O | HIS | D | 359 | 56.483 | −23.111 | −67.947 | 1.00 | 45.51 | O |
| ATOM | 2549 | N | GLU | D | 360 | 54.528 | −24.189 | −68.063 | 1.00 | 27.08 | N |
| ATOM | 2550 | CA | GLU | D | 360 | 55.139 | −25.443 | −68.521 | 1.00 | 27.32 | C |
| ATOM | 2551 | CB | GLU | D | 360 | 54.210 | −26.614 | −68.172 | 1.00 | 31.37 | C |
| ATOM | 2552 | CG | GLU | D | 360 | 54.595 | −27.945 | −68.805 | 1.00 | 34.63 | C |
| ATOM | 2553 | CD | GLU | D | 360 | 55.817 | −28.559 | −68.147 | 1.00 | 41.93 | C |
| ATOM | 2554 | OE1 | GLU | D | 360 | 56.415 | −29.484 | −68.736 | 1.00 | 39.25 | O |
| ATOM | 2555 | OE2 | GLU | D | 360 | 56.182 | −28.108 | −67.044 | 1.00 | 38.61 | O |
| ATOM | 2556 | C | GLU | D | 360 | 55.387 | −25.420 | −70.038 | 1.00 | 28.74 | C |
| ATOM | 2557 | O | GLU | D | 360 | 56.405 | −25.971 | −70.541 | 1.00 | 24.80 | O |
| ATOM | 2558 | N | THR | D | 361 | 54.424 | −24.833 | −70.757 | 1.00 | 23.58 | N |
| ATOM | 2559 | CA | THR | D | 361 | 54.328 | −24.964 | −72.216 | 1.00 | 29.66 | C |
| ATOM | 2560 | CB | THR | D | 361 | 52.956 | −25.523 | −72.644 | 1.00 | 36.08 | C |
| ATOM | 2561 | OG1 | THR | D | 361 | 52.742 | −26.789 | −72.017 | 1.00 | 38.33 | O |
| ATOM | 2562 | CG2 | THR | D | 361 | 52.893 | −25.715 | −74.156 | 1.00 | 33.81 | C |
| ATOM | 2563 | C | THR | D | 361 | 54.520 | −23.590 | −72.853 | 1.00 | 30.62 | C |
| ATOM | 2564 | O | THR | D | 361 | 53.910 | −22.612 | −72.429 | 1.00 | 29.15 | O |
| ATOM | 2565 | N | LEU | D | 362 | 55.415 | −23.514 | −73.825 | 1.00 | 22.36 | N |
| ATOM | 2566 | CA | LEU | D | 362 | 55.586 | −22.312 | −74.604 | 1.00 | 20.47 | C |
| ATOM | 2567 | CB | LEU | D | 362 | 57.065 | −22.186 | −74.968 | 1.00 | 22.09 | C |
| ATOM | 2568 | CG | LEU | D | 362 | 57.572 | −20.894 | −75.560 | 1.00 | 26.95 | C |
| ATOM | 2569 | CD1 | LEU | D | 362 | 57.651 | −19.787 | −74.516 | 1.00 | 25.81 | C |
| ATOM | 2570 | CD2 | LEU | D | 362 | 58.945 | −21.158 | −76.176 | 1.00 | 29.27 | C |
| ATOM | 2571 | C | LEU | D | 362 | 54.712 | −22.459 | −75.859 | 1.00 | 21.04 | C |
| ATOM | 2572 | O | LEU | D | 362 | 54.736 | −23.506 | −76.495 | 1.00 | 19.78 | O |
| ATOM | 2573 | N | THR | D | 363 | 53.904 | −21.447 | −76.199 | 1.00 | 16.67 | N |
| ATOM | 2574 | CA | THR | D | 363 | 53.126 | −21.527 | −77.450 | 1.00 | 15.97 | C |
| ATOM | 2575 | CB | THR | D | 363 | 51.609 | −21.246 | −77.279 | 1.00 | 18.24 | C |
| ATOM | 2576 | OG1 | THR | D | 363 | 51.420 | −19.993 | −76.625 | 1.00 | 16.20 | O |
| ATOM | 2577 | CG2 | THR | D | 363 | 50.955 | −22.366 | −76.474 | 1.00 | 17.89 | C |
| ATOM | 2578 | C | THR | D | 363 | 53.715 | −20.596 | −78.503 | 1.00 | 16.58 | C |
| ATOM | 2579 | O | THR | D | 363 | 53.979 | −19.417 | −78.232 | 1.00 | 15.75 | O |
| ATOM | 2580 | N | VAL | D | 364 | 53.996 | −21.161 | −79.670 | 1.00 | 13.70 | N |
| ATOM | 2581 | CA | VAL | D | 364 | 54.587 | −20.387 | −80.772 | 1.00 | 16.04 | C |
| ATOM | 2582 | CB | VAL | D | 364 | 56.089 | −20.741 | −80.988 | 1.00 | 15.95 | C |
| ATOM | 2583 | CG1 | VAL | D | 364 | 56.897 | −20.448 | −79.721 | 1.00 | 15.03 | C |
| ATOM | 2584 | CG2 | VAL | D | 364 | 56.270 | −22.203 | −81.384 | 1.00 | 14.84 | C |
| ATOM | 2585 | C | VAL | D | 364 | 53.792 | −20.600 | −82.062 | 1.00 | 13.81 | C |
| ATOM | 2586 | O | VAL | D | 364 | 53.202 | −21.687 | −82.287 | 1.00 | 12.28 | O |
| ATOM | 2587 | N | TYR | D | 365 | 53.810 | −19.579 | −82.938 | 1.00 | 15.53 | N |
| ATOM | 2588 | CA | TYR | D | 365 | 53.052 | −19.662 | −84.210 | 1.00 | 13.43 | C |
| ATOM | 2589 | CB | TYR | D | 365 | 52.924 | −18.280 | −84.849 | 1.00 | 12.13 | C |
| ATOM | 2590 | CG | TYR | D | 365 | 51.901 | −17.385 | −84.178 | 1.00 | 14.12 | C |
| ATOM | 2591 | CD1 | TYR | D | 365 | 50.544 | −17.768 | −84.110 | 1.00 | 13.77 | C |
| ATOM | 2592 | CE1 | TYR | D | 365 | 49.583 | −16.926 | −83.512 | 1.00 | 15.10 | C |
| ATOM | 2593 | CZ | TYR | D | 365 | 49.991 | −15.687 | −82.984 | 1.00 | 15.49 | C |
| ATOM | 2594 | OH | TYR | D | 365 | 49.053 | −14.874 | −82.375 | 1.00 | 17.24 | O |
| ATOM | 2595 | CE2 | TYR | D | 365 | 51.329 | −15.292 | −83.029 | 1.00 | 15.81 | C |
| ATOM | 2596 | CD2 | TYR | D | 365 | 52.285 | −16.159 | −83.623 | 1.00 | 14.04 | C |
| ATOM | 2597 | C | TYR | D | 365 | 53.751 | −20.598 | −85.186 | 1.00 | 14.61 | C |
| ATOM | 2598 | O | TYR | D | 365 | 53.100 | −21.239 | −86.010 | 1.00 | 15.23 | O |
| ATOM | 2599 | N | LYS | D | 366 | 55.079 | −20.683 | −85.073 | 1.00 | 14.91 | N |
| ATOM | 2600 | CA | LYS | D | 366 | 55.887 | −21.352 | −86.074 | 1.00 | 14.82 | C |
| ATOM | 2601 | CB | LYS | D | 366 | 56.450 | −20.314 | −87.095 | 1.00 | 16.70 | C |
| ATOM | 2602 | CG | LYS | D | 366 | 55.437 | −19.735 | −88.084 | 1.00 | 15.41 | C |
| ATOM | 2603 | CD | LYS | D | 366 | 55.220 | −20.782 | −89.186 | 1.00 | 19.20 | C |
| ATOM | 2604 | CE | LYS | D | 366 | 54.120 | −20.437 | −90.153 | 1.00 | 22.48 | C |

TABLE 5-continued

Atomic coordinates for CRBN(TBD):Thalidomide (Murine protein)

| ATOM | 2605 | NZ | LYS | D | 366 | 54.054 | −21.571 | −91.138 | 1.00 | 15.78 | N |
|---|---|---|---|---|---|---|---|---|---|---|---|
| ATOM | 2606 | C | LYS | D | 366 | 57.072 | −22.039 | −85.389 | 1.00 | 14.61 | C |
| ATOM | 2607 | O | LYS | D | 366 | 57.672 | −21.493 | −84.455 | 1.00 | 16.82 | O |
| ATOM | 2608 | N | ALA | D | 367 | 57.449 | −23.187 | −85.915 | 1.00 | 14.78 | N |
| ATOM | 2609 | CA | ALA | D | 367 | 58.594 | −23.932 | −85.397 | 1.00 | 14.44 | C |
| ATOM | 2610 | CB | ALA | D | 367 | 58.136 | −24.894 | −84.279 | 1.00 | 14.74 | C |
| ATOM | 2611 | C | ALA | D | 367 | 59.243 | −24.692 | −86.554 | 1.00 | 16.81 | C |
| ATOM | 2612 | O | ALA | D | 367 | 58.651 | −24.822 | −87.656 | 1.00 | 17.10 | O |
| ATOM | 2613 | N | SER | D | 368 | 60.451 | −25.187 | −86.317 | 1.00 | 18.43 | N |
| ATOM | 2614 | CA | SER | D | 368 | 61.260 | −25.769 | −87.382 | 1.00 | 20.30 | C |
| ATOM | 2615 | CB | SER | D | 368 | 62.302 | −24.752 | −87.867 | 1.00 | 19.50 | C |
| ATOM | 2616 | OG | SER | D | 368 | 63.108 | −24.309 | −86.799 | 1.00 | 23.02 | O |
| ATOM | 2617 | C | SER | D | 368 | 61.964 | −27.030 | −86.888 | 1.00 | 16.89 | C |
| ATOM | 2618 | O | SER | D | 368 | 62.204 | −27.189 | −85.663 | 1.00 | 19.11 | O |
| ATOM | 2619 | N | ASN | D | 369 | 62.311 | −27.915 | −87.826 | 1.00 | 18.18 | N |
| ATOM | 2620 | CA | ASN | D | 369 | 63.184 | −29.042 | −87.511 | 1.00 | 20.92 | C |
| ATOM | 2621 | CB | ASN | D | 369 | 64.490 | −28.539 | −86.867 | 1.00 | 17.47 | C |
| ATOM | 2622 | CG | ASN | D | 369 | 65.242 | −27.569 | −87.763 | 1.00 | 23.77 | C |
| ATOM | 2623 | OD1 | ASN | D | 369 | 65.672 | −26.505 | −87.320 | 1.00 | 27.54 | O |
| ATOM | 2624 | ND2 | ASN | D | 369 | 65.356 | −27.914 | −89.032 | 1.00 | 20.46 | N |
| ATOM | 2625 | C | ASN | D | 369 | 62.512 | −30.017 | −86.559 | 1.00 | 24.80 | C |
| ATOM | 2626 | O | ASN | D | 369 | 63.189 | −30.723 | −85.792 | 1.00 | 25.89 | O |
| ATOM | 2627 | N | LEU | D | 370 | 61.186 | −30.019 | −86.578 | 1.00 | 22.54 | N |
| ATOM | 2628 | CA | LEU | D | 370 | 60.407 | −31.016 | −85.867 | 1.00 | 23.88 | C |
| ATOM | 2629 | CB | LEU | D | 370 | 59.256 | −30.351 | −85.073 | 1.00 | 21.84 | C |
| ATOM | 2630 | CG | LEU | D | 370 | 59.675 | −29.438 | −83.921 | 1.00 | 20.70 | C |
| ATOM | 2631 | CD1 | LEU | D | 370 | 58.484 | −28.623 | −83.428 | 1.00 | 17.93 | C |
| ATOM | 2632 | CD2 | LEU | D | 370 | 60.274 | −30.264 | −82.780 | 1.00 | 20.54 | C |
| ATOM | 2633 | C | LEU | D | 370 | 59.840 | −32.012 | −86.855 | 1.00 | 24.81 | C |
| ATOM | 2634 | O | LEU | D | 370 | 59.453 | −31.667 | −87.978 | 1.00 | 25.01 | O |
| ATOM | 2635 | N | ASN | D | 371 | 59.785 | −33.254 | −86.415 | 1.00 | 22.93 | N |
| ATOM | 2636 | CA | ASN | D | 371 | 59.143 | −34.298 | −87.144 | 1.00 | 23.87 | C |
| ATOM | 2637 | CB | ASN | D | 371 | 60.106 | −35.481 | −87.255 | 1.00 | 30.34 | C |
| ATOM | 2638 | CG | ASN | D | 371 | 59.485 | −36.667 | −87.924 | 1.00 | 39.88 | C |
| ATOM | 2639 | OD1 | ASN | D | 371 | 59.054 | −36.593 | −89.081 | 1.00 | 46.83 | O |
| ATOM | 2640 | ND2 | ASN | D | 371 | 59.425 | −37.774 | −87.209 | 1.00 | 36.27 | N |
| ATOM | 2641 | C | ASN | D | 371 | 57.855 | −34.718 | −86.400 | 1.00 | 22.49 | C |
| ATOM | 2642 | O | ASN | D | 371 | 57.880 | −34.907 | −85.183 | 1.00 | 24.35 | O |
| ATOM | 2643 | N | LEU | D | 372 | 56.753 | −34.839 | −87.141 | 1.00 | 21.33 | N |
| ATOM | 2644 | CA | LEU | D | 372 | 55.467 | −35.233 | −86.584 | 1.00 | 25.52 | C |
| ATOM | 2645 | CB | LEU | D | 372 | 54.321 | −34.605 | −87.391 | 1.00 | 25.63 | C |
| ATOM | 2646 | CG | LEU | D | 372 | 54.361 | −33.071 | −87.496 | 1.00 | 24.98 | C |
| ATOM | 2647 | CD1 | LEU | D | 372 | 53.250 | −32.590 | −88.396 | 1.00 | 24.11 | C |
| ATOM | 2648 | CD2 | LEU | D | 372 | 54.244 | −32.424 | −86.106 | 1.00 | 22.99 | C |
| ATOM | 2649 | C | LEU | D | 372 | 55.304 | −36.742 | −86.549 | 1.00 | 26.66 | C |
| ATOM | 2650 | O | LEU | D | 372 | 55.524 | −37.412 | −87.548 | 1.00 | 26.61 | O |
| ATOM | 2651 | N | ILE | D | 373 | 54.868 | −37.253 | −85.399 | 1.00 | 25.93 | N |
| ATOM | 2652 | CA | ILE | D | 373 | 54.582 | −38.667 | −85.218 | 1.00 | 31.55 | C |
| ATOM | 2653 | CB | ILE | D | 373 | 55.196 | −39.172 | −83.905 | 1.00 | 31.48 | C |
| ATOM | 2654 | CG1 | ILE | D | 373 | 56.703 | −38.984 | −83.945 | 1.00 | 36.34 | C |
| ATOM | 2655 | CD1 | ILE | D | 373 | 57.321 | −39.470 | −85.244 | 1.00 | 39.69 | C |
| ATOM | 2656 | CG2 | ILE | D | 373 | 54.823 | −40.638 | −83.659 | 1.00 | 37.28 | C |
| ATOM | 2657 | C | ILE | D | 373 | 53.086 | −38.860 | −85.125 | 1.00 | 33.17 | C |
| ATOM | 2658 | O | ILE | D | 373 | 52.442 | −38.242 | −84.286 | 1.00 | 27.63 | O |
| ATOM | 2659 | N | GLY | D | 374 | 52.529 | −39.697 | −85.993 | 1.00 | 36.46 | N |
| ATOM | 2660 | CA | GLY | D | 374 | 51.115 | −40.081 | −85.880 | 1.00 | 39.38 | C |
| ATOM | 2661 | C | GLY | D | 374 | 50.116 | −39.071 | −86.431 | 1.00 | 37.90 | C |
| ATOM | 2662 | O | GLY | D | 374 | 50.466 | −38.190 | −87.226 | 1.00 | 35.72 | O |
| ATOM | 2663 | N | ARG | D | 375 | 48.865 | −39.212 | −86.008 | 1.00 | 35.66 | N |
| ATOM | 2664 | CA | ARG | D | 375 | 47.764 | −38.390 | −86.512 | 1.00 | 39.72 | C |
| ATOM | 2665 | CB | ARG | D | 375 | 46.665 | −39.284 | −87.091 | 1.00 | 45.20 | C |
| ATOM | 2666 | CG | ARG | D | 375 | 47.051 | −39.986 | −88.388 | 1.00 | 55.76 | C |
| ATOM | 2667 | CD | ARG | D | 375 | 46.609 | −41.445 | −88.393 | 1.00 | 65.22 | C |
| ATOM | 2668 | NE | ARG | D | 375 | 45.216 | −41.611 | −87.980 | 1.00 | 74.97 | N |
| ATOM | 2669 | CZ | ARG | D | 375 | 44.167 | −41.517 | −88.797 | 1.00 | 81.23 | C |
| ATOM | 2670 | NH1 | ARG | D | 375 | 44.340 | −41.257 | −90.087 | 1.00 | 79.15 | N |
| ATOM | 2671 | NH2 | ARG | D | 375 | 42.940 | −41.686 | −88.321 | 1.00 | 79.81 | N |
| ATOM | 2672 | C | ARG | D | 375 | 47.214 | −37.543 | −85.364 | 1.00 | 32.34 | C |
| ATOM | 2673 | O | ARG | D | 375 | 47.450 | −37.866 | −84.186 | 1.00 | 31.73 | O |
| ATOM | 2674 | N | PRO | D | 376 | 46.499 | −36.441 | −85.681 | 1.00 | 32.50 | N |
| ATOM | 2675 | CA | PRO | D | 376 | 46.017 | −35.605 | −84.555 | 1.00 | 27.40 | C |
| ATOM | 2676 | CB | PRO | D | 376 | 45.261 | −34.473 | −85.262 | 1.00 | 32.97 | C |
| ATOM | 2677 | CG | PRO | D | 376 | 45.906 | −34.376 | −86.609 | 1.00 | 36.81 | C |
| ATOM | 2678 | CD | PRO | D | 376 | 46.307 | −35.780 | −86.987 | 1.00 | 32.39 | C |
| ATOM | 2679 | C | PRO | D | 376 | 45.067 | −36.363 | −83.616 | 1.00 | 27.51 | C |
| ATOM | 2680 | O | PRO | D | 376 | 44.326 | −37.224 | −84.056 | 1.00 | 32.39 | O |
| ATOM | 2681 | N | SER | D | 377 | 45.073 | −36.012 | −82.342 | 1.00 | 22.19 | N |
| ATOM | 2682 | CA | SER | D | 377 | 44.061 | −36.492 | −81.432 | 1.00 | 24.19 | C |

TABLE 5-continued

Atomic coordinates for CRBN(TBD):Thalidomide (Murine protein)

| ATOM | 2683 | CB | SER | D | 377 | 44.642 | −37.593 | −80.518 | 1.00 | 26.97 | C |
|---|---|---|---|---|---|---|---|---|---|---|---|
| ATOM | 2684 | OG | SER | D | 377 | 43.698 | −37.944 | −79.521 | 1.00 | 26.58 | O |
| ATOM | 2685 | C | SER | D | 377 | 43.550 | −35.351 | −80.584 | 1.00 | 23.68 | C |
| ATOM | 2686 | O | SER | D | 377 | 44.317 | −34.441 | −80.234 | 1.00 | 21.53 | O |
| ATOM | 2687 | N | THR | D | 378 | 42.271 | −35.410 | −80.204 | 1.00 | 19.26 | N |
| ATOM | 2688 | CA | THR | D | 378 | 41.705 | −34.397 | −79.301 | 1.00 | 21.51 | C |
| ATOM | 2689 | CB | THR | D | 378 | 40.257 | −34.006 | −79.692 | 1.00 | 28.98 | C |
| ATOM | 2690 | OG1 | THR | D | 378 | 39.474 | −35.186 | −79.785 | 1.00 | 28.60 | O |
| ATOM | 2691 | CG2 | THR | D | 378 | 40.229 | −33.298 | −81.059 | 1.00 | 26.30 | C |
| ATOM | 2692 | C | THR | D | 378 | 41.677 | −34.886 | −77.859 | 1.00 | 22.90 | C |
| ATOM | 2693 | O | THR | D | 378 | 41.363 | −34.119 | −76.957 | 1.00 | 22.50 | O |
| ATOM | 2694 | N | VAL | D | 379 | 42.011 | −36.162 | −77.651 | 1.00 | 24.01 | N |
| ATOM | 2695 | CA | VAL | D | 379 | 41.910 | −36.763 | −76.315 | 1.00 | 24.88 | C |
| ATOM | 2696 | CB | VAL | D | 379 | 42.232 | −38.282 | −76.366 | 1.00 | 26.77 | C |
| ATOM | 2697 | CG1 | VAL | D | 379 | 41.924 | −38.929 | −75.020 | 1.00 | 30.28 | C |
| ATOM | 2698 | CG2 | VAL | D | 379 | 41.420 | −38.961 | −77.483 | 1.00 | 30.55 | C |
| ATOM | 2699 | C | VAL | D | 379 | 42.851 | −36.059 | −75.345 | 1.00 | 21.36 | C |
| ATOM | 2700 | O | VAL | D | 379 | 44.052 | −35.946 | −75.619 | 1.00 | 23.03 | O |
| ATOM | 2701 | N | HIS | D | 380 | 42.302 | −35.601 | −74.209 | 1.00 | 20.07 | N |
| ATOM | 2702 | CA | HIS | D | 380 | 43.053 | −34.884 | −73.156 | 1.00 | 23.59 | C |
| ATOM | 2703 | CB | HIS | D | 380 | 44.130 | −35.769 | −72.478 | 1.00 | 21.22 | C |
| ATOM | 2704 | CG | HIS | D | 380 | 43.659 | −37.163 | −72.110 | 1.00 | 29.25 | C |
| ATOM | 2705 | ND1 | HIS | D | 380 | 42.624 | −37.386 | −71.282 | 1.00 | 33.10 | N |
| ATOM | 2706 | CE1 | HIS | D | 380 | 42.449 | −38.713 | −71.121 | 1.00 | 26.61 | C |
| ATOM | 2707 | NE2 | HIS | D | 380 | 43.397 | −39.345 | −71.822 | 1.00 | 30.44 | N |
| ATOM | 2708 | CD2 | HIS | D | 380 | 44.165 | −38.421 | −72.451 | 1.00 | 32.96 | C |
| ATOM | 2709 | C | HIS | D | 380 | 43.735 | −33.611 | −73.629 | 1.00 | 26.08 | C |
| ATOM | 2710 | O | HIS | D | 380 | 44.682 | −33.152 | −72.989 | 1.00 | 20.61 | O |
| ATOM | 2711 | N | SER | D | 381 | 43.255 | −33.006 | −74.715 | 1.00 | 24.43 | N |
| ATOM | 2712 | CA | SER | D | 381 | 43.917 | −31.802 | −75.216 | 1.00 | 21.29 | C |
| ATOM | 2713 | CB | SER | D | 381 | 43.274 | −31.290 | −76.505 | 1.00 | 24.58 | C |
| ATOM | 2714 | OG | SER | D | 381 | 43.976 | −30.118 | −76.959 | 1.00 | 24.41 | O |
| ATOM | 2715 | C | SER | D | 381 | 44.030 | −30.671 | −74.168 | 1.00 | 18.56 | C |
| ATOM | 2716 | O | SER | D | 381 | 43.038 | −30.283 | −73.513 | 1.00 | 20.72 | O |
| ATOM | 2717 | N | TRP | D | 382 | 45.217 | −30.099 | −74.056 | 1.00 | 16.61 | N |
| ATOM | 2718 | CA | TRP | D | 382 | 45.439 | −28.979 | −73.139 | 1.00 | 18.86 | C |
| ATOM | 2719 | CB | TRP | D | 382 | 46.919 | −28.831 | −72.790 | 1.00 | 24.08 | C |
| ATOM | 2720 | CG | TRP | D | 382 | 47.498 | −30.064 | −72.142 | 1.00 | 25.00 | C |
| ATOM | 2721 | CD1 | TRP | D | 382 | 46.837 | −30.979 | −71.308 | 1.00 | 23.24 | C |
| ATOM | 2722 | NE1 | TRP | D | 382 | 47.710 | −31.991 | −70.905 | 1.00 | 25.16 | N |
| ATOM | 2723 | CE2 | TRP | D | 382 | 48.949 | −31.776 | −71.436 | 1.00 | 21.93 | C |
| ATOM | 2724 | CD2 | TRP | D | 382 | 48.873 | −30.544 | −72.241 | 1.00 | 24.42 | C |
| ATOM | 2725 | CE3 | TRP | D | 382 | 50.019 | −30.085 | −72.877 | 1.00 | 26.05 | C |
| ATOM | 2726 | CZ3 | TRP | D | 382 | 51.203 | −30.831 | −72.751 | 1.00 | 27.58 | C |
| ATOM | 2727 | CH2 | TRP | D | 382 | 51.251 | −32.016 | −71.983 | 1.00 | 29.29 | C |
| ATOM | 2728 | CZ2 | TRP | D | 382 | 50.130 | −32.499 | −71.305 | 1.00 | 26.50 | C |
| ATOM | 2729 | C | TRP | D | 382 | 44.919 | −27.670 | −73.671 | 1.00 | 23.15 | C |
| ATOM | 2730 | O | TRP | D | 382 | 44.885 | −26.667 | −72.945 | 1.00 | 22.81 | O |
| ATOM | 2731 | N | PHE | D | 383 | 44.539 | −27.664 | −74.947 | 1.00 | 18.80 | N |
| ATOM | 2732 | CA | PHE | D | 383 | 43.985 | −26.458 | −75.590 | 1.00 | 21.89 | C |
| ATOM | 2733 | CB | PHE | D | 383 | 45.002 | −25.888 | −76.601 | 1.00 | 18.94 | C |
| ATOM | 2734 | CG | PHE | D | 383 | 46.294 | −25.453 | −75.965 | 1.00 | 18.29 | C |
| ATOM | 2735 | CD1 | PHE | D | 383 | 46.383 | −24.232 | −75.291 | 1.00 | 21.99 | C |
| ATOM | 2736 | CE1 | PHE | D | 383 | 47.582 | −23.829 | −74.679 | 1.00 | 23.29 | C |
| ATOM | 2737 | CZ | PHE | D | 383 | 48.711 | −24.643 | −74.756 | 1.00 | 22.42 | C |
| ATOM | 2738 | CE2 | PHE | D | 383 | 48.626 | −25.872 | −75.404 | 1.00 | 21.97 | C |
| ATOM | 2739 | CD2 | PHE | D | 383 | 47.431 | −26.272 | −76.016 | 1.00 | 18.10 | C |
| ATOM | 2740 | C | PHE | D | 383 | 42.659 | −26.807 | −76.253 | 1.00 | 20.33 | C |
| ATOM | 2741 | O | PHE | D | 383 | 42.621 | −27.267 | −77.379 | 1.00 | 19.52 | O |
| ATOM | 2742 | N | PRO | D | 384 | 41.551 | −26.655 | −75.506 | 1.00 | 24.45 | N |
| ATOM | 2743 | CA | PRO | D | 384 | 40.237 | −27.104 | −75.968 | 1.00 | 25.86 | C |
| ATOM | 2744 | CB | PRO | D | 384 | 39.286 | −26.541 | −74.890 | 1.00 | 33.13 | C |
| ATOM | 2745 | CG | PRO | D | 384 | 40.137 | −26.480 | −73.659 | 1.00 | 36.86 | C |
| ATOM | 2746 | CD | PRO | D | 384 | 41.486 | −26.036 | −74.165 | 1.00 | 27.74 | C |
| ATOM | 2747 | C | PRO | D | 384 | 39.919 | −26.472 | −77.318 | 1.00 | 23.10 | C |
| ATOM | 2748 | O | PRO | D | 384 | 40.217 | −25.298 | −77.526 | 1.00 | 26.74 | O |
| ATOM | 2749 | N | GLY | D | 385 | 39.410 | −27.273 | −78.247 | 1.00 | 23.86 | N |
| ATOM | 2750 | CA | GLY | D | 385 | 39.190 | −26.821 | −79.618 | 1.00 | 20.87 | C |
| ATOM | 2751 | C | GLY | D | 385 | 40.309 | −27.189 | −80.557 | 1.00 | 19.55 | C |
| ATOM | 2752 | O | GLY | D | 385 | 40.168 | −27.041 | −81.755 | 1.00 | 23.34 | O |
| ATOM | 2753 | N | TYR | D | 386 | 41.445 | −27.660 | −80.007 | 1.00 | 20.31 | N |
| ATOM | 2754 | CA | TYR | D | 386 | 42.586 | −28.134 | −80.827 | 1.00 | 18.04 | C |
| ATOM | 2755 | CB | TYR | D | 386 | 43.843 | −27.348 | −80.493 | 1.00 | 17.22 | C |
| ATOM | 2756 | CG | TYR | D | 336 | 43.759 | −25.886 | −80.888 | 1.00 | 16.50 | C |
| ATOM | 2757 | CD2 | TYR | D | 386 | 44.173 | −25.472 | −82.140 | 1.00 | 18.88 | C |
| ATOM | 2758 | CE2 | TYR | D | 386 | 44.097 | −24.121 | −82.519 | 1.00 | 16.81 | C |
| ATOM | 2759 | CZ | TYR | D | 386 | 43.602 | −23.181 | −81.629 | 1.00 | 17.04 | C |
| ATOM | 2760 | OH | TYR | D | 386 | 43.526 | −21.837 | −82.018 | 1.00 | 19.56 | O |

TABLE 5-continued

Atomic coordinates for CRBN(TBD):Thalidomide (Murine protein)

| ATOM | 2761 | CE1 | TYR | D | 386 | 43.177 | −23.560 | −80.360 | 1.00 | 17.79 | C |
|---|---|---|---|---|---|---|---|---|---|---|---|
| ATOM | 2762 | CD1 | TYR | D | 386 | 43.258 | −24.924 | −79.994 | 1.00 | 18.35 | C |
| ATOM | 2763 | C | TYR | D | 386 | 42.879 | −29.605 | −80.586 | 1.00 | 19.53 | C |
| ATOM | 2764 | O | TYR | D | 336 | 42.698 | −30.105 | −79.467 | 1.00 | 19.82 | O |
| ATOM | 2765 | N | ALA | D | 387 | 43.329 | −30.275 | −81.638 | 1.00 | 17.74 | N |
| ATOM | 2766 | CA | ALA | D | 387 | 43.877 | −31.632 | −81.562 | 1.00 | 20.43 | C |
| ATOM | 2767 | CB | ALA | D | 387 | 43.397 | −32.442 | −82.745 | 1.00 | 16.82 | C |
| ATOM | 2768 | C | ALA | D | 387 | 45.411 | −31.545 | −81.553 | 1.00 | 20.36 | C |
| ATOM | 2769 | O | ALA | D | 387 | 45.972 | −30.549 | −82.006 | 1.00 | 19.86 | O |
| ATOM | 2770 | N | TRP | D | 388 | 46.089 | −32.553 | −80.987 | 1.00 | 19.70 | N |
| ATOM | 2771 | CA | TRP | D | 388 | 47.558 | −32.524 | −80.886 | 1.00 | 18.19 | C |
| ATOM | 2772 | CB | TRP | D | 338 | 48.022 | −32.599 | −79.426 | 1.00 | 20.16 | C |
| ATOM | 2773 | CG | TRP | D | 388 | 47.357 | −33.718 | −78.650 | 1.00 | 21.18 | C |
| ATOM | 2774 | CD1 | TRP | D | 388 | 46.235 | −33.626 | −77.857 | 1.00 | 19.17 | C |
| ATOM | 2775 | NE1 | TRP | D | 388 | 45.919 | −34.867 | −77.309 | 1.00 | 25.77 | N |
| ATOM | 2776 | CE2 | TRP | D | 388 | 46.779 | −35.812 | −77.737 | 1.00 | 22.02 | C |
| ATOM | 2777 | CD2 | TRP | D | 388 | 47.747 | −35.148 | −78.605 | 1.00 | 24.52 | C |
| ATOM | 2778 | CE3 | TRP | D | 388 | 48.791 | −35.900 | −79.155 | 1.00 | 22.55 | C |
| ATOM | 2779 | CZ3 | TRP | D | 388 | 48.853 | −37.280 | −78.861 | 1.00 | 27.56 | C |
| ATOM | 2780 | CH2 | TRP | D | 388 | 47.892 | −37.896 | −78.021 | 1.00 | 27.40 | C |
| ATOM | 2781 | CZ2 | TRP | D | 388 | 46.854 | −37.172 | −77.440 | 1.00 | 22.96 | C |
| ATOM | 2782 | C | TRP | D | 388 | 48.157 | −33.648 | −81.660 | 1.00 | 19.88 | C |
| ATOM | 2783 | O | TRP | D | 388 | 47.525 | −34.699 | −81.836 | 1.00 | 20.05 | O |
| ATOM | 2784 | N | THR | D | 389 | 49.362 | −33.410 | −82.183 | 1.00 | 20.25 | N |
| ATOM | 2785 | CA | THR | D | 389 | 50.188 | −34.437 | −82.821 | 1.00 | 20.61 | C |
| ATOM | 2786 | CB | THR | D | 389 | 50.304 | −34.183 | −84.353 | 1.00 | 23.30 | C |
| ATOM | 2787 | OG1 | THR | D | 389 | 48.991 | −34.110 | −84.950 | 1.00 | 21.65 | O |
| ATOM | 2788 | CG2 | THR | D | 389 | 51.111 | −35.320 | −85.052 | 1.00 | 25.38 | C |
| ATOM | 2789 | C | THR | D | 389 | 51.593 | −34.333 | −82.175 | 1.00 | 20.88 | C |
| ATOM | 2790 | O | THR | D | 389 | 52.158 | −33.256 | −82.098 | 1.00 | 19.77 | O |
| ATOM | 2791 | N | ILE | D | 390 | 52.169 | −35.457 | −81.730 | 1.00 | 20.43 | N |
| ATOM | 2792 | CA | ILE | D | 390 | 53.483 | −35.413 | −81.073 | 1.00 | 18.66 | C |
| ATOM | 2793 | CB | ILE | D | 390 | 53.935 | −36.817 | −80.566 | 1.00 | 21.69 | C |
| ATOM | 2794 | CG1 | ILE | D | 390 | 53.078 | −37.251 | −79.366 | 1.00 | 22.22 | C |
| ATOM | 2795 | CD1 | ILE | D | 390 | 53.070 | −38.773 | −79.188 | 1.00 | 27.82 | C |
| ATOM | 2796 | CG2 | ILE | D | 390 | 55.384 | −36.795 | −80.141 | 1.00 | 22.82 | C |
| ATOM | 2797 | C | ILE | D | 390 | 54.539 | −34.885 | −82.038 | 1.00 | 17.90 | C |
| ATOM | 2798 | O | ILE | D | 390 | 54.549 | −35.256 | −83.228 | 1.00 | 18.74 | O |
| ATOM | 2799 | N | ALA | D | 391 | 55.399 | −34.010 | −81.524 | 1.00 | 16.82 | N |
| ATOM | 2800 | CA | ALA | D | 391 | 56.467 | −33.386 | −82.327 | 1.00 | 20.59 | C |
| ATOM | 2801 | CB | ALA | D | 391 | 56.221 | −31.865 | −82.438 | 1.00 | 20.63 | C |
| ATOM | 2802 | C | ALA | D | 391 | 57.838 | −33.662 | −81.698 | 1.00 | 20.11 | C |
| ATOM | 2803 | O | ALA | D | 391 | 58.111 | −33.250 | −80.557 | 1.00 | 21.13 | O |
| ATOM | 2804 | N | GLN | D | 392 | 58.713 | −34.337 | −82.456 | 1.00 | 20.43 | N |
| ATOM | 2805 | CA | GLN | D | 392 | 60.048 | −34.667 | −81.977 | 1.00 | 22.86 | C |
| ATOM | 2806 | CB | GLN | D | 392 | 60.292 | −36.192 | −82.076 | 1.00 | 21.97 | C |
| ATOM | 2807 | CG | GLN | D | 392 | 60.155 | −36.738 | −83.484 | 1.00 | 27.05 | C |
| ATOM | 2808 | CD | GLN | D | 392 | 60.535 | −38.210 | −83.597 | 1.00 | 36.97 | C |
| ATOM | 2809 | OE1 | GLN | D | 392 | 61.045 | −38.815 | −82.651 | 1.00 | 35.40 | O |
| ATOM | 2810 | NE2 | GLN | D | 392 | 60.276 | −38.787 | −84.747 | 1.00 | 32.21 | N |
| ATOM | 2811 | C | GLN | D | 392 | 61.098 | −33.931 | −82.796 | 1.00 | 19.30 | C |
| ATOM | 2812 | O | GLN | D | 392 | 60.871 | −33.620 | −83.945 | 1.00 | 20.51 | O |
| ATOM | 2813 | N | CYS | D | 393 | 62.251 | −33.679 | −82.180 | 1.00 | 19.60 | N |
| ATOM | 2814 | CA | CYS | D | 393 | 63.410 | −33.116 | −82.863 | 1.00 | 24.38 | C |
| ATOM | 2815 | CB | CYS | D | 393 | 64.582 | −32.989 | −81.879 | 1.00 | 21.32 | C |
| ATOM | 2816 | SG | CYS | D | 393 | 66.117 | −32.301 | −82.593 | 1.00 | 22.90 | S |
| ATOM | 2817 | C | CYS | D | 393 | 63.781 | −34.059 | −84.013 | 1.00 | 23.15 | C |
| ATOM | 2818 | O | CYS | D | 393 | 63.925 | −35.248 | −83.802 | 1.00 | 25.53 | O |
| ATOM | 2819 | N | LYS | D | 394 | 63.911 | −33.534 | −85.220 | 1.00 | 20.51 | N |
| ATOM | 2820 | CA | LYS | D | 394 | 64.245 | −34.399 | −86.356 | 1.00 | 26.63 | C |
| ATOM | 2821 | CB | LYS | D | 394 | 64.053 | −33.679 | −87.690 | 1.00 | 22.99 | C |
| ATOM | 2822 | CG | LYS | D | 394 | 65.219 | −32.758 | −88.057 | 1.00 | 26.05 | C |
| ATOM | 2823 | CD | LYS | D | 394 | 64.929 | −31.954 | −89.321 | 1.00 | 32.45 | C |
| ATOM | 2824 | CE | LYS | D | 394 | 66.165 | −31.181 | −89.765 | 1.00 | 34.37 | C |
| ATOM | 2825 | NZ | LYS | D | 394 | 65.814 | −30.211 | −90.828 | 1.00 | 32.51 | N |
| ATOM | 2826 | C | LYS | D | 394 | 65.687 | −34.947 | −86.247 | 1.00 | 24.31 | C |
| ATOM | 2827 | O | LYS | D | 394 | 66.012 | −35.965 | −86.880 | 1.00 | 27.33 | O |
| ATOM | 2828 | N | ILE | D | 395 | 66.535 | −34.250 | −85.481 | 1.00 | 22.07 | N |
| ATOM | 2829 | CA | ILE | D | 395 | 67.954 | −34.646 | −85.329 | 1.00 | 30.16 | C |
| ATOM | 2830 | CB | ILE | D | 395 | 68.880 | −33.463 | −84.944 | 1.00 | 32.13 | C |
| ATOM | 2831 | CG1 | ILE | D | 395 | 69.018 | −32.449 | −86.096 | 1.00 | 32.56 | C |
| ATOM | 2832 | CD1 | ILE | D | 395 | 69.165 | −33.047 | −87.473 | 1.00 | 33.80 | C |
| ATOM | 2833 | CG2 | ILE | D | 395 | 70.263 | −33.958 | −84.490 | 1.00 | 30.13 | C |
| ATOM | 2834 | C | ILE | D | 395 | 68.117 | −35.777 | −84.310 | 1.00 | 32.39 | C |
| ATOM | 2835 | O | ILE | D | 395 | 68.687 | −36.812 | −84.618 | 1.00 | 31.83 | O |
| ATOM | 2836 | N | CYS | D | 396 | 67.591 | −35.580 | −83.111 | 1.00 | 22.91 | N |
| ATOM | 2837 | CA | CYS | D | 396 | 67.875 | −36.486 | −81.989 | 1.00 | 24.90 | C |
| ATOM | 2838 | CB | CYS | D | 396 | 68.540 | −35.710 | −80.849 | 1.00 | 26.29 | C |

TABLE 5-continued

Atomic coordinates for CRBN(TBD):Thalidomide (Murine protein)

| ATOM | 2839 | SG | CYS | D | 396 | 67.392 | −34.667 | −79.902 | 1.00 | 26.29 | S |
|---|---|---|---|---|---|---|---|---|---|---|---|
| ATOM | 2840 | C | CYS | D | 396 | 66.639 | −37.254 | −81.475 | 1.00 | 26.23 | C |
| ATOM | 2841 | O | CYS | D | 396 | 66.746 | −38.040 | −80.534 | 1.00 | 29.29 | O |
| ATOM | 2842 | N | ALA | D | 397 | 65.470 | −36.992 | −82.071 | 1.00 | 22.61 | N |
| ATOM | 2843 | CA | ALA | D | 397 | 64.201 | −37.677 | −81.709 | 1.00 | 25.29 | C |
| ATOM | 2844 | CB | ALA | D | 397 | 64.328 | −39.203 | −81.848 | 1.00 | 25.44 | C |
| ATOM | 2845 | C | ALA | D | 397 | 63.662 | −37.305 | −80.330 | 1.00 | 25.97 | C |
| ATOM | 2846 | O | ALA | D | 397 | 62.674 | −37.871 | −79.882 | 1.00 | 25.29 | O |
| ATOM | 2847 | N | SER | D | 398 | 64.281 | −36.329 | −79.678 | 1.00 | 20.06 | N |
| ATOM | 2848 | CA | SER | D | 398 | 63.770 | −35.863 | −78.387 | 1.00 | 25.85 | C |
| ATOM | 2849 | CB | SER | D | 398 | 64.682 | −34.776 | −77.817 | 1.00 | 26.83 | C |
| ATOM | 2850 | OG | SER | D | 398 | 64.119 | −34.158 | −76.673 | 1.00 | 43.29 | O |
| ATOM | 2851 | C | SER | D | 398 | 62.339 | −35.335 | −78.569 | 1.00 | 24.41 | C |
| ATOM | 2852 | O | SER | D | 398 | 62.070 | −34.595 | −79.514 | 1.00 | 22.42 | O |
| ATOM | 2853 | N | HIS | D | 399 | 61.411 | −35.796 | −77.725 | 1.00 | 22.73 | N |
| ATOM | 2854 | CA | HIS | D | 399 | 60.027 | −35.284 | −77.746 | 1.00 | 25.25 | C |
| ATOM | 2855 | CB | HIS | D | 399 | 59.090 | −36.183 | −76.938 | 1.00 | 25.16 | C |
| ATOM | 2856 | CG | HIS | D | 399 | 58.789 | −37.515 | −77.592 | 1.00 | 29.41 | C |
| ATOM | 2857 | ND1 | HIS | D | 399 | 59.657 | −38.141 | −78.423 | 1.00 | 42.10 | N |
| ATOM | 2858 | CE1 | HIS | D | 399 | 59.126 | −39.316 | −78.823 | 1.00 | 32.43 | C |
| ATOM | 2859 | NE2 | HIS | D | 399 | 57.922 | −39.447 | −78.249 | 1.00 | 38.99 | N |
| ATOM | 2860 | CD2 | HIS | D | 399 | 57.685 | −38.364 | −77.473 | 1.00 | 30.44 | C |
| ATOM | 2861 | C | HIS | D | 399 | 59.979 | −33.866 | −77.218 | 1.00 | 26.07 | C |
| ATOM | 2862 | O | HIS | D | 399 | 60.175 | −33.624 | −76.026 | 1.00 | 26.52 | O |
| ATOM | 2863 | N | ILE | D | 400 | 59.700 | −32.912 | −78.101 | 1.00 | 18.90 | N |
| ATOM | 2864 | CA | ILE | D | 400 | 59.814 | −31.492 | −77.755 | 1.00 | 21.18 | C |
| ATOM | 2865 | CB | ILE | D | 400 | 60.427 | −30.671 | −78.916 | 1.00 | 22.02 | C |
| ATOM | 2866 | CG1 | ILE | D | 400 | 61.814 | −31.213 | −79.280 | 1.00 | 26.01 | C |
| ATOM | 2867 | CD1 | ILE | D | 400 | 62.851 | −30.915 | −78.247 | 1.00 | 24.92 | C |
| ATOM | 2868 | CG2 | ILE | D | 400 | 60.554 | −29.183 | −78.541 | 1.00 | 20.07 | C |
| ATOM | 2869 | C | ILE | D | 400 | 58.462 | −30.880 | −77.394 | 1.00 | 19.50 | C |
| ATOM | 2870 | O | ILE | D | 400 | 58.392 | −29.961 | −76.573 | 1.00 | 22.64 | O |
| ATOM | 2871 | N | GLY | D | 401 | 57.412 | −31.381 | −78.019 | 1.00 | 20.88 | N |
| ATOM | 2872 | CA | GLY | D | 401 | 56.065 | −30.843 | −77.787 | 1.00 | 20.61 | C |
| ATOM | 2873 | C | GLY | D | 401 | 55.094 | −31.405 | −78.756 | 1.00 | 21.00 | C |
| ATOM | 2874 | O | GLY | D | 401 | 55.157 | −32.587 | −79.080 | 1.00 | 20.04 | O |
| ATOM | 2875 | N | TRP | D | 402 | 54.159 | −30.558 | −79.212 | 1.00 | 18.09 | N |
| ATOM | 2876 | CA | TRP | D | 402 | 53.078 | −30.991 | −80.069 | 1.00 | 17.38 | C |
| ATOM | 2877 | CB | TRP | D | 402 | 51.787 | −31.276 | −79.257 | 1.00 | 16.14 | C |
| ATOM | 2878 | CG | TRP | D | 402 | 52.008 | −32.297 | −78.200 | 1.00 | 18.15 | C |
| ATOM | 2879 | CD1 | TRP | D | 402 | 51.756 | −33.677 | −78.286 | 1.00 | 19.91 | C |
| ATOM | 2880 | NE1 | TRP | D | 402 | 52.167 | −34.313 | −77.129 | 1.00 | 19.11 | N |
| ATOM | 2881 | CE2 | TRP | D | 402 | 52.717 | −33.402 | −76.263 | 1.00 | 20.02 | C |
| ATOM | 2882 | CD2 | TRP | D | 402 | 52.678 | −32.095 | −76.923 | 1.00 | 17.68 | C |
| ATOM | 2883 | CE3 | TRP | D | 402 | 53.191 | −30.991 | −76.260 | 1.00 | 19.50 | C |
| ATOM | 2884 | CZ3 | TRP | D | 402 | 53.745 | −31.174 | −74.980 | 1.00 | 23.62 | C |
| ATOM | 2885 | CH2 | TRP | D | 402 | 53.787 | −32.446 | −74.374 | 1.00 | 23.72 | C |
| ATOM | 2886 | CZ2 | TRP | D | 402 | 53.261 | −33.573 | −75.000 | 1.00 | 21.22 | C |
| ATOM | 2887 | C | TRP | D | 402 | 52.747 | −29.932 | −81.048 | 1.00 | 16.27 | C |
| ATOM | 2888 | O | TRP | D | 402 | 52.825 | −28.729 | −80.732 | 1.00 | 16.67 | O |
| ATOM | 2889 | N | LYS | D | 403 | 52.282 | −30.354 | −82.200 | 1.00 | 17.19 | N |
| ATOM | 2890 | CA | LYS | D | 403 | 51.580 | −29.444 | −83.110 | 1.00 | 18.61 | C |
| ATOM | 2891 | CB | LYS | D | 403 | 51.747 | −29.906 | −84.534 | 1.00 | 19.86 | C |
| ATOM | 2892 | CG | LYS | D | 403 | 51.145 | −28.943 | −85.534 | 1.00 | 22.36 | C |
| ATOM | 2893 | CD | LYS | D | 403 | 51.345 | −29.462 | −86.962 | 1.00 | 23.16 | C |
| ATOM | 2894 | CE | LYS | D | 403 | 51.176 | −28.334 | −87.968 | 1.00 | 30.55 | C |
| ATOM | 2895 | NZ | LYS | D | 403 | 51.137 | −28.881 | −89.362 | 1.00 | 43.90 | N |
| ATOM | 2896 | C | LYS | D | 403 | 50.107 | −29.450 | −82.767 | 1.00 | 18.59 | C |
| ATOM | 2897 | O | LYS | D | 403 | 49.512 | −30.511 | −82.660 | 1.00 | 19.04 | O |
| ATOM | 2898 | N | PHE | D | 404 | 49.518 | −28.263 | −82.583 | 1.00 | 15.85 | N |
| ATOM | 2899 | CA | PHE | D | 404 | 48.099 | −28.178 | −82.265 | 1.00 | 15.88 | C |
| ATOM | 2900 | CB | PHE | D | 404 | 47.846 | −27.268 | −81.039 | 1.00 | 15.01 | C |
| ATOM | 2901 | CG | PHE | D | 404 | 48.173 | −27.943 | −79.722 | 1.00 | 14.42 | C |
| ATOM | 2902 | CD1 | PHE | D | 404 | 47.250 | −28.799 | −79.119 | 1.00 | 17.09 | C |
| ATOM | 2903 | CE1 | PHE | D | 404 | 47.550 | −29.454 | −77.920 | 1.00 | 16.70 | C |
| ATOM | 2904 | CZ | PHE | D | 404 | 48.807 | −29.283 | −77.345 | 1.00 | 16.21 | C |
| ATOM | 2905 | CE2 | PHE | D | 404 | 49.760 | −28.466 | −77.962 | 1.00 | 15.82 | C |
| ATOM | 2906 | CD2 | PHE | D | 404 | 49.438 | −27.801 | −79.151 | 1.00 | 15.87 | C |
| ATOM | 2907 | C | PHE | D | 404 | 47.365 | −27.655 | −83.486 | 1.00 | 18.10 | C |
| ATOM | 2908 | O | PHE | D | 404 | 47.786 | −26.652 | −84.082 | 1.00 | 18.76 | O |
| ATOM | 2909 | N | THR | D | 405 | 46.293 | −28.346 | −83.872 | 1.00 | 17.48 | N |
| ATOM | 2910 | CA | THR | D | 405 | 45.537 | −27.995 | −85.077 | 1.00 | 19.83 | C |
| ATOM | 2911 | CB | THR | D | 405 | 45.701 | −29.076 | −86.157 | 1.00 | 22.66 | C |
| ATOM | 2912 | OG1 | THR | D | 405 | 45.506 | −30.366 | −85.553 | 1.00 | 23.05 | O |
| ATOM | 2913 | CG2 | THR | D | 405 | 47.127 | −29.010 | −86.766 | 1.00 | 22.52 | C |
| ATOM | 2914 | C | THR | D | 405 | 44.053 | −27.823 | −84.734 | 1.00 | 20.90 | C |
| ATOM | 2915 | O | THR | D | 405 | 43.482 | −28.622 | −83.984 | 1.00 | 19.38 | O |
| ATOM | 2916 | N | ALA | D | 406 | 43.451 | −26.742 | −85.251 | 1.00 | 18.26 | N |

TABLE 5-continued

Atomic coordinates for CRBN(TBD):Thalidomide (Murine protein)

| ATOM | 2917 | CA | ALA | D | 406 | 42.106 | −26.340 | −84.864 | 1.00 | 18.56 | C |
|---|---|---|---|---|---|---|---|---|---|---|---|
| ATOM | 2918 | CB | ALA | D | 406 | 41.778 | −24.955 | −85.466 | 1.00 | 19.38 | C |
| ATOM | 2919 | C | ALA | D | 406 | 41.106 | −27.376 | −85.353 | 1.00 | 18.61 | C |
| ATOM | 2920 | O | ALA | D | 406 | 41.244 | −27.899 | −86.457 | 1.00 | 23.36 | O |
| ATOM | 2921 | N | THR | D | 407 | 40.098 | −27.667 | −84.542 | 1.00 | 21.85 | N |
| ATOM | 2922 | CA | THR | D | 407 | 39.047 | −28.594 | −84.974 | 1.00 | 22.97 | C |
| ATOM | 2923 | CB | THR | D | 407 | 38.429 | −29.381 | −83.786 | 1.00 | 21.80 | C |
| ATOM | 2924 | OG1 | THR | D | 407 | 37.845 | −28.469 | −82.849 | 1.00 | 25.70 | O |
| ATOM | 2925 | CG2 | THR | D | 407 | 39.519 | −30.175 | −83.051 | 1.00 | 22.40 | C |
| ATOM | 2926 | C | THR | D | 407 | 37.948 | −27.853 | −85.776 | 1.00 | 32.49 | C |
| ATOM | 2927 | O | THR | D | 407 | 37.209 | −28.480 | −86.492 | 1.00 | 30.54 | O |
| ATOM | 2928 | N | LYS | D | 408 | 37.880 | −26.513 | −85.654 | 1.00 | 25.87 | N |
| ATOM | 2929 | CA | LYS | D | 408 | 36.832 | −25.701 | −86.364 | 1.00 | 28.10 | C |
| ATOM | 2930 | CB | LYS | D | 408 | 35.870 | −25.048 | −85.355 | 1.00 | 32.89 | C |
| ATOM | 2931 | CG | LYS | D | 408 | 34.970 | −25.994 | −84.585 | 1.00 | 36.35 | C |
| ATOM | 2932 | CD | LYS | D | 408 | 34.202 | −25.257 | −83.497 | 1.00 | 48.16 | C |
| ATOM | 2933 | CE | LYS | D | 408 | 32.762 | −24.959 | −83.914 | 1.00 | 63.50 | C |
| ATOM | 2934 | NZ | LYS | D | 408 | 32.634 | −23.746 | −84.770 | 1.00 | 52.08 | N |
| ATOM | 2935 | C | LYS | D | 408 | 37.522 | −24.588 | −87.181 | 1.00 | 30.24 | C |
| ATOM | 2936 | O | LYS | D | 408 | 38.502 | −24.005 | −86.728 | 1.00 | 22.47 | O |
| ATOM | 2937 | N | LYS | D | 409 | 36.963 | −24.258 | −88.338 | 1.00 | 26.45 | N |
| ATOM | 2938 | CA | LYS | D | 409 | 37.560 | −23.270 | −89.245 | 1.00 | 26.90 | C |
| ATOM | 2939 | CB | LYS | D | 409 | 36.853 | −23.310 | −90.605 | 1.00 | 37.47 | C |
| ATOM | 2940 | CG | LYS | D | 409 | 36.642 | −24.707 | −91.166 | 1.00 | 56.31 | C |
| ATOM | 2941 | CD | LYS | D | 409 | 37.459 | −24.950 | −92.422 | 1.00 | 62.22 | C |
| ATOM | 2942 | CE | LYS | D | 409 | 36.731 | −25.917 | −93.350 | 1.00 | 70.53 | C |
| ATOM | 2943 | NZ | LYS | D | 409 | 37.416 | −26.054 | −94.662 | 1.00 | 75.31 | N |
| ATOM | 2944 | C | LYS | D | 409 | 37.509 | −21.828 | −88.696 | 1.00 | 24.58 | C |
| ATOM | 2945 | O | LYS | D | 409 | 38.265 | −20.966 | −89.135 | 1.00 | 28.14 | O |
| ATOM | 2946 | N | ASP | D | 410 | 36.628 | −21.570 | −87.748 | 1.00 | 28.01 | N |
| ATOM | 2947 | CA | ASP | D | 410 | 36.371 | −20.172 | −87.340 | 1.00 | 36.30 | C |
| ATOM | 2948 | CB | ASP | D | 410 | 34.898 | −19.976 | −86.963 | 1.00 | 39.17 | C |
| ATOM | 2949 | CG | ASP | D | 410 | 34.518 | −20.716 | −85.688 | 1.00 | 55.66 | C |
| ATOM | 2950 | OD1 | ASP | D | 410 | 35.157 | −21.754 | −85.375 | 1.00 | 51.51 | O |
| ATOM | 2951 | OD2 | ASP | D | 410 | 33.593 | −20.249 | −84.988 | 1.00 | 61.91 | O |
| ATOM | 2952 | C | ASP | D | 410 | 37.306 | −19.706 | −86.202 | 1.00 | 36.47 | C |
| ATOM | 2953 | O | ASP | D | 410 | 37.162 | −18.592 | −85.685 | 1.00 | 39.80 | O |
| ATOM | 2954 | N | MET | D | 411 | 38.252 | −20.579 | −85.824 | 1.00 | 31.09 | N |
| ATOM | 2955 | CA | MET | D | 411 | 39.228 | −20.315 | −84.748 | 1.00 | 27.12 | C |
| ATOM | 2956 | CB | MET | D | 411 | 39.606 | −21.648 | −84.053 | 1.00 | 20.71 | C |
| ATOM | 2957 | CG | MET | D | 411 | 38.462 | −22.248 | −83.261 | 1.00 | 33.06 | C |
| ATOM | 2958 | SD | MET | D | 411 | 38.885 | −23.835 | −82.490 | 1.00 | 38.53 | S |
| ATOM | 2959 | CE | MET | D | 411 | 38.689 | −25.017 | −83.757 | 1.00 | 31.10 | C |
| ATOM | 2960 | C | MET | D | 411 | 40.504 | −19.665 | −85.302 | 1.00 | 20.43 | C |
| ATOM | 2961 | O | MET | D | 411 | 40.856 | −19.867 | −86.470 | 1.00 | 20.88 | O |
| ATOM | 2962 | N | SER | D | 412 | 41.224 | −18.927 | −84.452 | 1.00 | 20.52 | N |
| ATOM | 2963 | CA | SER | D | 412 | 42.574 | −18.472 | −84.801 | 1.00 | 19.80 | C |
| ATOM | 2964 | CB | SER | D | 412 | 42.598 | −16.993 | −85.229 | 1.00 | 20.35 | C |
| ATOM | 2965 | OG | SER | D | 412 | 42.148 | −16.141 | −84.152 | 1.00 | 23.08 | O |
| ATOM | 2966 | C | SER | D | 412 | 43.485 | −18.768 | −83.605 | 1.00 | 19.45 | C |
| ATOM | 2967 | O | SER | D | 412 | 43.076 | −18.495 | −82.454 | 1.00 | 17.91 | O |
| ATOM | 2968 | N | PRO | D | 413 | 44.788 | −18.912 | −83.876 | 1.00 | 16.20 | N |
| ATOM | 2969 | CA | PRO | D | 413 | 45.291 | −19.597 | −85.050 | 1.00 | 16.92 | C |
| ATOM | 2970 | CB | PRO | D | 413 | 46.813 | −19.674 | −84.771 | 1.00 | 14.98 | C |
| ATOM | 2971 | CG | PRO | D | 413 | 46.867 | −19.942 | −83.312 | 1.00 | 16.17 | C |
| ATOM | 2972 | CD | PRO | D | 413 | 45.665 | −19.185 | −82.703 | 1.00 | 15.30 | C |
| ATOM | 2973 | C | PRO | D | 413 | 44.695 | −20.960 | −85.366 | 1.00 | 16.13 | C |
| ATOM | 2974 | O | PRO | D | 413 | 44.231 | −21.667 | −84.470 | 1.00 | 17.90 | O |
| ATOM | 2975 | N | GLN | D | 414 | 44.681 | −21.305 | −86.648 | 1.00 | 15.27 | N |
| ATOM | 2976 | CA | GLN | D | 414 | 44.269 | −22.633 | −87.052 | 1.00 | 15.54 | C |
| ATOM | 2977 | CB | GLN | D | 414 | 44.021 | −22.669 | −88.553 | 1.00 | 18.13 | C |
| ATOM | 2978 | CG | GLN | D | 414 | 42.676 | −22.057 | −88.954 | 1.00 | 19.04 | C |
| ATOM | 2979 | CD | GLN | D | 414 | 41.508 | −22.881 | −88.469 | 1.00 | 18.67 | C |
| ATOM | 2980 | OE1 | GLN | D | 414 | 40.749 | −22.474 | −87.590 | 1.00 | 24.03 | O |
| ATOM | 2981 | NE2 | GLN | D | 414 | 41.388 | −24.058 | −89.000 | 1.00 | 14.78 | N |
| ATOM | 2982 | C | GLN | D | 414 | 45.316 | −23.707 | −86.658 | 1.00 | 18.36 | C |
| ATOM | 2983 | O | GLN | D | 414 | 45.002 | −24.892 | −86.593 | 1.00 | 19.98 | O |
| ATOM | 2984 | N | LYS | D | 415 | 46.549 | −23.284 | −86.423 | 1.00 | 15.11 | N |
| ATOM | 2985 | CA | LYS | D | 415 | 47.615 | −24.200 | −85.961 | 1.00 | 18.74 | C |
| ATOM | 2986 | CB | LYS | D | 415 | 48.321 | −24.936 | −87.143 | 1.00 | 24.21 | C |
| ATOM | 2987 | CG | LYS | D | 415 | 49.397 | −24.109 | −87.835 | 1.00 | 37.45 | C |
| ATOM | 2988 | CD | LYS | D | 415 | 49.753 | −24.667 | −89.199 | 1.00 | 42.17 | C |
| ATOM | 2989 | CE | LYS | D | 415 | 50.241 | −23.566 | −90.120 | 1.00 | 35.40 | C |
| ATOM | 2990 | NZ | LYS | D | 415 | 49.120 | −22.642 | −90.526 | 1.00 | 39.35 | N |
| ATOM | 2991 | C | LYS | D | 415 | 48.613 | −23.440 | −85.157 | 1.00 | 17.77 | C |
| ATOM | 2992 | O | LYS | D | 415 | 48.801 | −22.237 | −85.359 | 1.00 | 16.36 | O |
| ATOM | 2993 | N | PHE | D | 416 | 49.265 | −24.137 | −84.224 | 1.00 | 15.39 | N |
| ATOM | 2994 | CA | PHE | D | 416 | 50.367 | −23.587 | −83.499 | 1.00 | 13.97 | C |

TABLE 5-continued

Atomic coordinates for CRBN(TBD):Thalidomide (Murine protein)

| ATOM | 2995 | CB | PHE | D | 416 | 49.906 | −22.538 | −82.432 | 1.00 | 13.98 | C |
| ATOM | 2996 | CG | PHE | D | 416 | 49.113 | −23.119 | −81.306 | 1.00 | 13.20 | C |
| ATOM | 2997 | CD2 | PHE | D | 416 | 49.755 | −23.504 | −80.123 | 1.00 | 15.38 | C |
| ATOM | 2998 | CE2 | PHE | D | 416 | 49.029 | −24.072 | −79.075 | 1.00 | 16.53 | C |
| ATOM | 2999 | CZ | PHE | D | 416 | 47.651 | −24.254 | −79.196 | 1.00 | 17.32 | C |
| ATOM | 3000 | CE1 | PHE | D | 416 | 46.995 | −23.893 | −80.375 | 1.00 | 16.12 | C |
| ATOM | 3001 | CD1 | PHE | D | 416 | 47.726 | −23.325 | −81.425 | 1.00 | 16.37 | C |
| ATOM | 3002 | C | PHE | D | 416 | 51.126 | −24.759 | −82.862 | 1.00 | 14.27 | C |
| ATOM | 3003 | O | PHE | D | 416 | 50.735 | −25.902 | −83.039 | 1.00 | 15.95 | O |
| ATOM | 3004 | N | TRP | D | 417 | 52.236 | −24.445 | −82.197 | 1.00 | 15.15 | N |
| ATOM | 3005 | CA | TRP | D | 417 | 53.061 | −25.453 | −81.512 | 1.00 | 15.27 | C |
| ATOM | 3006 | CB | TRP | D | 417 | 54.498 | −25.364 | −82.024 | 1.00 | 15.46 | C |
| ATOM | 3007 | CG | TRP | D | 417 | 54.574 | −25.549 | −83.513 | 1.00 | 17.45 | C |
| ATOM | 3008 | CD1 | TRP | D | 417 | 54.397 | −24.560 | −84.514 | 1.00 | 17.65 | C |
| ATOM | 3009 | NE1 | TRP | D | 417 | 54.476 | −25.121 | −85.765 | 1.00 | 17.37 | N |
| ATOM | 3010 | CE2 | TRP | D | 417 | 54.723 | −26.465 | −85.671 | 1.00 | 21.95 | C |
| ATOM | 3011 | CD2 | TRP | D | 417 | 54.770 | −26.803 | −84.239 | 1.00 | 18.57 | C |
| ATOM | 3012 | CE3 | TRP | D | 417 | 55.027 | −28.135 | −83.857 | 1.00 | 19.07 | C |
| ATOM | 3013 | CZ3 | TRP | D | 417 | 55.203 | −29.102 | −84.867 | 1.00 | 20.47 | C |
| ATOM | 3014 | CH2 | TRP | D | 417 | 55.174 | −28.749 | −86.247 | 1.00 | 18.03 | C |
| ATOM | 3015 | CZ2 | TRP | D | 417 | 54.903 | −27.429 | −86.669 | 1.00 | 19.17 | C |
| ATOM | 3016 | C | TRP | D | 417 | 53.036 | −25.216 | −80.048 | 1.00 | 17.19 | C |
| ATOM | 3017 | O | TRP | D | 417 | 53.240 | −24.089 | −79.583 | 1.00 | 17.21 | O |
| ATOM | 3018 | N | GLY | D | 418 | 52.828 | −26.281 | −79.288 | 1.00 | 15.50 | N |
| ATOM | 3019 | CA | GLY | D | 418 | 52.968 | −26.191 | −77.839 | 1.00 | 17.14 | C |
| ATOM | 3020 | C | GLY | D | 418 | 54.210 | −26.945 | −77.460 | 1.00 | 20.96 | C |
| ATOM | 3021 | O | GLY | D | 418 | 54.272 | −28.139 | −77.645 | 1.00 | 18.76 | O |
| ATOM | 3022 | N | LEU | D | 419 | 55.205 | −26.232 | −76.952 | 1.00 | 17.38 | N |
| ATOM | 3023 | CA | LEU | D | 419 | 56.532 | −26.826 | −76.722 | 1.00 | 17.67 | C |
| ATOM | 3024 | CB | LEU | D | 419 | 57.605 | −26.031 | −77.436 | 1.00 | 17.99 | C |
| ATOM | 3025 | CG | LEU | D | 419 | 57.414 | −25.837 | −78.932 | 1.00 | 21.22 | C |
| ATOM | 3026 | CD1 | LEU | D | 419 | 58.557 | −25.003 | −79.458 | 1.00 | 21.28 | C |
| ATOM | 3027 | CD2 | LEU | D | 419 | 57.297 | −27.193 | −79.664 | 1.00 | 16.10 | C |
| ATOM | 3028 | C | LEU | D | 419 | 56.855 | −26.865 | −75.240 | 1.00 | 20.53 | C |
| ATOM | 3029 | O | LEU | D | 419 | 56.672 | −25.866 | −74.509 | 1.00 | 21.57 | O |
| ATOM | 3030 | N | THR | D | 420 | 57.386 | −28.000 | −74.793 | 1.00 | 20.09 | N |
| ATOM | 3031 | CA | THR | D | 420 | 57.776 | −28.125 | −73.392 | 1.00 | 19.54 | C |
| ATOM | 3032 | CB | THR | D | 420 | 58.056 | −29.600 | −73.053 | 1.00 | 20.93 | C |
| ATOM | 3033 | OG1 | THR | D | 420 | 56.896 | −30.364 | −73.371 | 1.00 | 21.41 | O |
| ATOM | 3034 | CG2 | THR | D | 420 | 58.401 | −29.767 | −71.565 | 1.00 | 18.81 | C |
| ATOM | 3035 | C | THR | D | 420 | 59.013 | −27.292 | −73.140 | 1.00 | 19.42 | C |
| ATOM | 3036 | O | THR | D | 420 | 60.060 | −27.543 | −73.742 | 1.00 | 21.87 | O |
| ATOM | 3037 | N | ARG | D | 421 | 58.891 | −26.287 | −72.256 | 1.00 | 19.64 | N |
| ATOM | 3038 | CA | ARG | D | 421 | 59.970 | −25.320 | −72.011 | 1.00 | 22.01 | C |
| ATOM | 3039 | CB | ARG | D | 421 | 59.574 | −24.319 | −70.937 | 1.00 | 28.17 | C |
| ATOM | 3040 | CG | ARG | D | 421 | 58.809 | −23.137 | −71.455 | 1.00 | 42.45 | C |
| ATOM | 3041 | CD | ARG | D | 421 | 58.322 | −22.288 | −70.303 | 1.00 | 48.21 | C |
| ATOM | 3042 | NE | ARG | D | 421 | 57.077 | −21.627 | −70.645 | 1.00 | 49.13 | N |
| ATOM | 3043 | CZ | ARG | D | 421 | 56.950 | −20.317 | −70.792 | 1.00 | 57.75 | C |
| ATOM | 3044 | NH1 | ARG | D | 421 | 57.994 | −19.527 | −70.595 | 1.00 | 48.98 | N |
| ATOM | 3045 | NH2 | ARG | D | 421 | 55.772 | −19.795 | −71.111 | 1.00 | 56.93 | N |
| ATOM | 3046 | C | ARG | D | 421 | 61.246 | −26.010 | −71.583 | 1.00 | 22.68 | C |
| ATOM | 3047 | O | ARG | D | 421 | 62.319 | −25.613 | −71.996 | 1.00 | 24.46 | O |
| ATOM | 3048 | N | SER | D | 422 | 61.110 | −27.049 | −70.752 | 1.00 | 25.59 | N |
| ATOM | 3049 | CA | SER | D | 422 | 62.278 | −27.791 | −70.229 | 1.00 | 26.45 | C |
| ATOM | 3050 | CB | SER | D | 422 | 61.864 | −28.719 | −69.063 | 1.00 | 23.58 | C |
| ATOM | 3051 | OG | SER | D | 422 | 61.032 | −29.789 | −69.505 | 1.00 | 30.45 | O |
| ATOM | 3052 | C | SER | D | 422 | 63.032 | −28.581 | −71.313 | 1.00 | 24.74 | C |
| ATOM | 3053 | O | SER | D | 422 | 64.146 | −29.042 | −71.084 | 1.00 | 27.42 | O |
| ATOM | 3054 | N | ALA | D | 423 | 62.417 | −28.727 | −72.495 | 1.00 | 25.27 | N |
| ATOM | 3055 | CA | ALA | D | 423 | 63.039 | −29.420 | −73.621 | 1.00 | 24.37 | C |
| ATOM | 3056 | CB | ALA | D | 423 | 61.980 | −30.120 | −74.487 | 1.00 | 23.85 | C |
| ATOM | 3057 | C | ALA | D | 423 | 63.885 | −28.474 | −74.481 | 1.00 | 23.06 | C |
| ATOM | 3058 | O | ALA | D | 423 | 64.510 | −28.906 | −75.443 | 1.00 | 21.86 | O |
| ATOM | 3059 | N | LEU | D | 424 | 63.846 | −27.179 | −74.173 | 1.00 | 23.19 | N |
| ATOM | 3060 | CA | LEU | D | 424 | 64.551 | −26.179 | −74.976 | 1.00 | 25.64 | C |
| ATOM | 3061 | CB | LEU | D | 424 | 63.578 | −25.115 | −75.495 | 1.00 | 19.70 | C |
| ATOM | 3062 | CG | LEU | D | 424 | 62.394 | −25.660 | −76.338 | 1.00 | 25.58 | C |
| ATOM | 3063 | CD1 | LEU | D | 424 | 61.387 | −24.553 | −76.624 | 1.00 | 24.39 | C |
| ATOM | 3064 | CD2 | LEU | D | 424 | 62.882 | −26.313 | −77.638 | 1.00 | 25.84 | C |
| ATOM | 3065 | C | LEU | D | 424 | 65.645 | −25.485 | −74.180 | 1.00 | 25.22 | C |
| ATOM | 3066 | O | LEU | D | 424 | 65.543 | −25.346 | −72.967 | 1.00 | 28.72 | O |
| ATOM | 3067 | N | LEU | D | 425 | 66.657 | −25.001 | −74.885 | 1.00 | 25.53 | N |
| ATOM | 3068 | CA | LEU | D | 425 | 67.682 | −24.158 | −74.280 | 1.00 | 32.98 | C |
| ATOM | 3069 | CB | LEU | D | 425 | 69.071 | −24.752 | −74.471 | 1.00 | 35.32 | C |
| ATOM | 3070 | CG | LEU | D | 425 | 69.450 | −25.808 | −73.446 | 1.00 | 42.29 | C |
| ATOM | 3071 | CD1 | LEU | D | 425 | 70.929 | −26.112 | −73.572 | 1.00 | 42.56 | C |
| ATOM | 3072 | CD2 | LEU | D | 425 | 69.095 | −25.346 | −72.042 | 1.00 | 45.77 | C |

TABLE 5-continued

Atomic coordinates for CRBN(TBD):Thalidomide (Murine protein)

| ATOM | 3073 | C | LEU | D | 425 | 67.629 | −22.788 | −74.877 | 1.00 | 40.87 | C |
| ATOM | 3074 | O | LEU | D | 425 | 67.349 | −22.668 | −76.088 | 1.00 | 33.25 | O |
| ATOM | 3075 | N | PRO | D | 426 | 68.212 | −21.810 | −74.155 | 1.00 | 45.89 | N |
| ATOM | 3076 | CA | PRO | D | 426 | 67.610 | −20.786 | −73.349 | 1.00 | 57.87 | C |
| ATOM | 3077 | CB | PRO | D | 426 | 67.331 | −19.679 | −74.380 | 1.00 | 53.21 | C |
| ATOM | 3078 | CG | PRO | D | 426 | 68.497 | −19.824 | −75.359 | 1.00 | 54.74 | C |
| ATOM | 3079 | CD | PRO | D | 426 | 69.193 | −21.159 | −75.038 | 1.00 | 67.18 | C |
| ATOM | 3080 | C | PRO | D | 426 | 66.365 | −21.192 | −72.512 | 1.00 | 58.45 | C |
| ATOM | 3081 | O | PRO | D | 426 | 65.411 | −21.780 | −73.041 | 1.00 | 48.30 | O |
| ATOM | 3082 | N | THR | D | 427 | 66.441 | −20.925 | −71.198 | 1.00 | 66.40 | N |
| ATOM | 3083 | CA | THR | D | 427 | 65.263 | −20.854 | −70.308 | 1.00 | 67.80 | C |
| ATOM | 3084 | CB | THR | D | 427 | 65.635 | −21.203 | −68.848 | 1.00 | 60.74 | C |
| ATOM | 3085 | OG1 | THR | D | 427 | 66.376 | −22.426 | −68.822 | 1.00 | 58.02 | O |
| ATOM | 3086 | CG2 | THR | D | 427 | 64.381 | −21.351 | −67.979 | 1.00 | 50.29 | C |
| ATOM | 3087 | C | THR | D | 427 | 64.662 | −19.438 | −70.333 | 1.00 | 71.52 | C |
| ATOM | 3088 | O | THR | D | 427 | 63.487 | −19.234 | −70.000 | 1.00 | 76.83 | O |
| ATOM | 3089 | ZN | ZN | E | 1 | 67.618 | −37.228 | −59.988 | 1.00 | 27.99 | ZN |
| ATOM | 3090 | ZN | ZN | E | 2 | 67.487 | −32.570 | −80.846 | 1.00 | 25.78 | ZN |
| ATOM | 3091 | ZN | ZN | E | 3 | 4.097 | −33.368 | −62.459 | 1.00 | 18.39 | ZN |
| ATOM | 3092 | ZN | ZN | E | 4 | 34.532 | −10.753 | −66.813 | 1.00 | 20.66 | ZN |
| ATOM | 3093 | O4 | SO4 | F | 1 | 53.568 | −24.050 | −89.945 | 1.00 | 27.02 | O |
| ATOM | 3094 | S | SO4 | F | 1 | 53.601 | −25.374 | −90.617 | 1.00 | 28.11 | S |
| ATOM | 3095 | O1 | SO4 | F | 1 | 53.923 | −25.053 | −92.001 | 1.00 | 32.61 | O |
| ATOM | 3096 | O2 | SO4 | F | 1 | 52.338 | −26.140 | −90.510 | 1.00 | 27.60 | O |
| ATOM | 3097 | O3 | SO4 | F | 1 | 54.655 | −26.234 | −90.020 | 1.00 | 27.04 | O |
| ATOM | 3098 | O4 | SO4 | F | 2 | 50.231 | −19.037 | −91.853 | 1.00 | 34.18 | O |
| ATOM | 3099 | S | SO4 | F | 2 | 50.876 | −20.322 | −92.143 | 1.00 | 26.17 | S |
| ATOM | 3100 | O1 | SO4 | F | 2 | 52.110 | −20.082 | −92.935 | 1.00 | 37.87 | O |
| ATOM | 3101 | O2 | SO4 | F | 2 | 49.990 | −21.173 | −92.931 | 1.00 | 30.99 | O |
| ATOM | 3102 | O3 | SO4 | F | 2 | 51.220 | −21.044 | −90.914 | 1.00 | 29.76 | O |
| ATOM | 3103 | O4 | SO4 | F | 3 | 45.129 | −18.809 | −88.412 | 1.00 | 28.56 | O |
| ATOM | 3104 | S | SO4 | F | 3 | 46.195 | −19.365 | −89.235 | 1.00 | 32.81 | S |
| ATOM | 3105 | O1 | SO4 | F | 3 | 47.348 | −18.420 | −89.377 | 1.00 | 28.73 | O |
| ATOM | 3106 | O2 | SO4 | F | 3 | 45.551 | −19.636 | −90.540 | 1.00 | 49.07 | O |
| ATOM | 3107 | O3 | SO4 | F | 3 | 46.830 | −20.580 | −88.652 | 1.00 | 35.57 | O |
| ATOM | 3108 | O4 | SO4 | F | 4 | 26.417 | −19.462 | −52.350 | 1.00 | 33.03 | O |
| ATOM | 3109 | S | SO4 | F | 4 | 25.795 | −19.828 | −53.661 | 1.00 | 31.11 | S |
| ATOM | 3110 | O1 | SO4 | F | 4 | 26.701 | −19.259 | −54.691 | 1.00 | 31.40 | O |
| ATOM | 3111 | O2 | SO4 | F | 4 | 24.383 | −19.360 | −53.762 | 1.00 | 30.81 | O |
| ATOM | 3112 | O3 | SO4 | F | 4 | 25.697 | −21.229 | −53.808 | 1.00 | 33.31 | O |
| ATOM | 3113 | O4 | SO4 | F | 5 | 32.829 | −35.024 | −71.669 | 1.00 | 57.21 | O |
| ATOM | 3114 | S | SO4 | F | 5 | 32.284 | −36.387 | −71.587 | 1.00 | 60.38 | S |
| ATOM | 3115 | O1 | SO4 | F | 5 | 32.659 | −37.161 | −72.786 | 1.00 | 47.81 | O |
| ATOM | 3116 | O2 | SO4 | F | 5 | 30.815 | −36.320 | −71.522 | 1.00 | 58.23 | O |
| ATOM | 3117 | O3 | SO4 | F | 5 | 32.793 | −37.041 | −70.361 | 1.00 | 51.17 | O |
| ATOM | 3118 | O4 | SO4 | F | 6 | 54.372 | −44.362 | −51.667 | 1.00 | 32.99 | O |
| ATOM | 3119 | S | SO4 | F | 6 | 53.289 | −45.242 | −51.226 | 1.00 | 32.65 | S |
| ATOM | 3120 | O1 | SO4 | F | 6 | 53.288 | −46.499 | −52.033 | 1.00 | 28.49 | O |
| ATOM | 3121 | O2 | SO4 | F | 6 | 52.026 | −44.469 | −51.301 | 1.00 | 35.40 | O |
| ATOM | 3122 | O3 | SO4 | F | 6 | 53.486 | −45.666 | −49.862 | 1.00 | 40.91 | O |
| ATOM | 3123 | O4 | SO4 | F | 7 | 49.141 | −49.576 | −49.719 | 0.33 | 24.16 | O |
| ATOM | 3124 | S | SO4 | F | 7 | 50.191 | −50.555 | −50.043 | 0.33 | 22.72 | S |
| ATOM | 3125 | O1 | SO4 | F | 7 | 51.120 | −50.733 | −48.908 | 0.50 | 26.94 | O |
| ATOM | 3126 | O2 | SO4 | F | 7 | 50.930 | −50.091 | −51.228 | 0.50 | 31.15 | O |
| ATOM | 3127 | O3 | SO4 | F | 7 | 49.597 | −51.873 | −50.348 | 0.50 | 28.00 | O |
| ATOM | 3128 | O4 | SO4 | F | 8 | 39.942 | −33.808 | −68.999 | 1.00 | 80.40 | O |
| ATOM | 3129 | S | SO4 | F | 8 | 39.983 | −33.670 | −70.474 | 1.00 | 72.31 | S |
| ATOM | 3130 | O1 | SO4 | F | 8 | 41.339 | −33.212 | −70.905 | 1.00 | 54.52 | O |
| ATOM | 3131 | O2 | SO4 | F | 8 | 38.978 | −32.671 | −70.880 | 1.00 | 67.79 | O |
| ATOM | 3132 | O3 | SO4 | F | 8 | 39.656 | −34.972 | −71.101 | 1.00 | 57.24 | O |
| ATOM | 3133 | O1 | tha | G | 1 | 32.649 | −4.810 | −46.725 | 1.00 | 20.74 | O |
| ATOM | 3134 | C4 | tha | G | 1 | 33.736 | −4.493 | −47.208 | 1.00 | 23.72 | C |
| ATOM | 3135 | N1 | tha | G | 1 | 34.439 | −3.448 | −46.705 | 1.00 | 23.58 | N |
| ATOM | 3136 | C5 | tha | G | 1 | 35.492 | −2.884 | −47.320 | 1.00 | 27.69 | C |
| ATOM | 3137 | O2 | tha | G | 1 | 35.998 | −1.826 | −46.907 | 1.00 | 23.56 | O |
| ATOM | 3138 | C3 | tha | G | 1 | 34.313 | −5.273 | −48.385 | 1.00 | 21.17 | C |
| ATOM | 3139 | C2 | tha | G | 1 | 35.822 | −5.074 | −48.482 | 1.00 | 22.99 | C |
| ATOM | 3140 | C1 | tha | G | 1 | 36.047 | −3.586 | −48.549 | 1.00 | 23.94 | C |
| ATOM | 3141 | N | tha | G | 1 | 37.469 | −3.212 | −48.651 | 1.00 | 33.94 | N |
| ATOM | 3142 | C6 | tha | G | 1 | 38.045 | −2.668 | −49.734 | 1.00 | 25.81 | C |
| ATOM | 3143 | O3 | tha | G | 1 | 37.260 | −2.381 | −50.923 | 1.00 | 25.24 | O |
| ATOM | 3144 | C | tha | G | 1 | 38.458 | −3.251 | −47.772 | 1.00 | 30.12 | C |
| ATOM | 3145 | O | tha | G | 1 | 38.304 | −3.806 | −46.444 | 1.00 | 26.85 | O |
| ATOM | 3146 | C12 | tha | G | 1 | 39.752 | −2.707 | −48.258 | 1.00 | 33.22 | C |
| ATOM | 3147 | C11 | tha | G | 1 | 41.013 | −2.561 | −47.675 | 1.00 | 37.87 | C |
| ATOM | 3148 | C10 | tha | G | 1 | 42.014 | −1.972 | −48.458 | 1.00 | 32.82 | C |
| ATOM | 3149 | C9 | tha | G | 1 | 41.737 | −1.564 | −49.775 | 1.00 | 31.86 | C |
| ATOM | 3150 | C8 | tha | G | 1 | 40.457 | −1.729 | −50.339 | 1.00 | 33.36 | C |

TABLE 5-continued

Atomic coordinates for CRBN(TBD):Thalidomide (Murine protein)

| ATOM | 3151 | C7  | tha | G | 1  | 39.484 | −2.312  | −49.541 | 1.00 | 31.31 | C |
|------|------|-----|-----|---|----|--------|---------|---------|------|-------|---|
| ATOM | 3152 | O1  | tha | H | 1  | 47.266 | −37.534 | −66.093 | 1.00 | 21.69 | O |
| ATOM | 3153 | C4  | tha | H | 1  | 47.832 | −36.498 | −66.403 | 1.00 | 23.28 | C |
| ATOM | 3154 | N1  | tha | H | 1  | 47.418 | −35.791 | −67.471 | 1.00 | 24.07 | N |
| ATOM | 3155 | C5  | tha | H | 1  | 48.038 | −34.697 | −67.946 | 1.00 | 25.82 | C |
| ATOM | 3156 | O2  | tha | H | 1  | 47.583 | −34.121 | −68.956 | 1.00 | 23.16 | O |
| ATOM | 3157 | C3  | tha | H | 1  | 49.005 | −36.000 | −65.601 | 1.00 | 19.27 | C |
| ATOM | 3158 | C2  | tha | H | 1  | 49.179 | −34.474 | −65.735 | 1.00 | 22.11 | C |
| ATOM | 3159 | C1  | tha | H | 1  | 49.293 | −34.204 | −67.222 | 1.00 | 25.56 | C |
| ATOM | 3160 | N   | tha | H | 1  | 49.513 | −32.791 | −67.594 | 1.00 | 27.31 | N |
| ATOM | 3161 | C6  | tha | H | 1  | 50.591 | −32.281 | −68.200 | 1.00 | 21.40 | C |
| ATOM | 3162 | O3  | tha | H | 1  | 51.755 | −33.075 | −68.500 | 1.00 | 22.54 | O |
| ATOM | 3163 | C   | tha | H | 1  | 48.664 | −31.743 | −67.531 | 1.00 | 23.73 | C |
| ATOM | 3164 | O   | tha | H | 1  | 47.327 | −31.806 | −66.943 | 1.00 | 24.82 | O |
| ATOM | 3165 | C12 | tha | H | 1  | 49.203 | −30.492 | −68.117 | 1.00 | 21.03 | C |
| ATOM | 3166 | C11 | tha | H | 1  | 48.684 | −29.198 | −68.256 | 1.00 | 25.42 | C |
| ATOM | 3167 | C10 | tha | H | 1  | 49.530 | −28.263 | −68.892 | 1.00 | 24.97 | C |
| ATOM | 3168 | C9  | tha | H | 1  | 50.830 | −28.634 | −69.335 | 1.00 | 23.71 | C |
| ATOM | 3169 | C8  | tha | H | 1  | 51.332 | −29.952 | −69.185 | 1.00 | 21.01 | C |
| ATOM | 3170 | C7  | tha | H | 1  | 50.478 | −30.849 | −68.556 | 1.00 | 23.19 | C |
| ATOM | 3171 | O1  | tha | I | 1  | 47.337 | −31.704 | −75.372 | 1.00 | 17.69 | O |
| ATOM | 3172 | C4  | tha | I | 1  | 47.886 | −32.674 | −74.932 | 1.00 | 22.81 | C |
| ATOM | 3173 | N1  | tha | I | 1  | 47.416 | −33.311 | −73.831 | 1.00 | 20.72 | N |
| ATOM | 3174 | C5  | tha | I | 1  | 48.035 | −34.360 | −73.273 | 1.00 | 22.00 | C |
| ATOM | 3175 | O2  | tha | I | 1  | 47.585 | −34.857 | −72.231 | 1.00 | 24.61 | O |
| ATOM | 3176 | C3  | tha | I | 1  | 49.124 | −33.205 | −75.627 | 1.00 | 20.77 | C |
| ATOM | 3177 | C2  | tha | I | 1  | 49.281 | −34.709 | −75.419 | 1.00 | 22.13 | C |
| ATOM | 3178 | C1  | tha | I | 1  | 49.305 | −34.900 | −73.916 | 1.00 | 23.16 | C |
| ATOM | 3179 | N   | tha | I | 1  | 49.465 | −36.310 | −73.512 | 1.00 | 28.08 | N |
| ATOM | 3180 | C6  | tha | I | 1  | 50.538 | −36.859 | −72.935 | 1.00 | 25.51 | C |
| ATOM | 3181 | O3  | tha | I | 1  | 51.733 | −36.112 | −72.648 | 1.00 | 25.38 | O |
| ATOM | 3182 | C   | tha | I | 1  | 48.595 | −37.325 | −73.536 | 1.00 | 27.27 | C |
| ATOM | 3183 | O   | tha | I | 1  | 47.256 | −37.214 | −74.073 | 1.00 | 24.97 | O |
| ATOM | 3184 | C12 | tha | I | 1  | 49.114 | −38.586 | −72.942 | 1.00 | 28.92 | C |
| ATOM | 3185 | C11 | tha | I | 1  | 48.580 | −39.847 | −72.752 | 1.00 | 28.01 | C |
| ATOM | 3186 | C10 | tha | I | 1  | 49.425 | −40.783 | −72.129 | 1.00 | 33.52 | C |
| ATOM | 3187 | C9  | tha | I | 1  | 50.749 | −40.458 | −71.733 | 1.00 | 30.84 | C |
| ATOM | 3188 | C8  | tha | I | 1  | 51.256 | −39.167 | −71.928 | 1.00 | 25.90 | C |
| ATOM | 3189 | C7  | tha | I | 1  | 50.400 | −38.272 | −72.560 | 1.00 | 24.13 | C |
| ATOM | 3190 | O1  | tha | J | 1  | 24.801 | −33.124 | −67.097 | 1.00 | 20.37 | O |
| ATOM | 3191 | C4  | tha | J | 1  | 24.183 | −34.100 | −67.526 | 1.00 | 22.00 | C |
| ATOM | 3192 | N1  | tha | J | 1  | 24.716 | −34.860 | −68.490 | 1.00 | 22.11 | N |
| ATOM | 3193 | C5  | tha | J | 1  | 24.068 | −35.818 | −69.151 | 1.00 | 25.13 | C |
| ATOM | 3194 | O2  | tha | J | 1  | 24.555 | −36.342 | −70.149 | 1.00 | 24.55 | O |
| ATOM | 3195 | C3  | tha | J | 1  | 22.816 | −34.486 | −66.967 | 1.00 | 20.11 | C |
| ATOM | 3196 | C2  | tha | J | 1  | 22.595 | −35.985 | −67.165 | 1.00 | 23.98 | C |
| ATOM | 3197 | C1  | tha | J | 1  | 22.708 | −36.249 | −68.657 | 1.00 | 25.08 | C |
| ATOM | 3198 | N   | tha | J | 1  | 22.518 | −37.687 | −69.024 | 1.00 | 26.77 | N |
| ATOM | 3199 | C6  | tha | J | 1  | 21.454 | −38.222 | −69.614 | 1.00 | 26.80 | C |
| ATOM | 3200 | O3  | tha | J | 1  | 20.327 | −37.391 | −69.949 | 1.00 | 25.74 | O |
| ATOM | 3201 | C   | tha | J | 1  | 23.338 | −38.734 | −68.909 | 1.00 | 27.97 | C |
| ATOM | 3202 | O   | tha | J | 1  | 24.653 | −38.642 | −68.325 | 1.00 | 30.49 | O |
| ATOM | 3203 | C12 | tha | J | 1  | 22.799 | −40.010 | −69.459 | 1.00 | 27.99 | C |
| ATOM | 3204 | C11 | tha | J | 1  | 23.300 | −41.301 | −69.548 | 1.00 | 32.96 | C |
| ATOM | 3205 | C10 | tha | J | 1  | 22.471 | −42.266 | −70.154 | 1.00 | 37.29 | C |
| ATOM | 3206 | C9  | tha | J | 1  | 21.192 | −41.923 | −70.640 | 1.00 | 31.51 | C |
| ATOM | 3207 | C8  | tha | J | 1  | 20.713 | −40.608 | −70.525 | 1.00 | 34.99 | C |
| ATOM | 3208 | C7  | tha | J | 1  | 21.563 | −39.671 | −69.932 | 1.00 | 29.61 | C |
| ATOM | 3209 | O   | HOH | L | 1  | 15.687 | −24.868 | −55.044 | 1.00 | 18.53 | O |
| ATOM | 3210 | O   | HOH | L | 2  | 50.141 | −49.492 | −55.581 | 1.00 | 18.42 | O |
| ATOM | 3211 | O   | HOH | L | 3  | 16.276 | −16.194 | −55.792 | 1.00 | 25.79 | O |
| ATOM | 3212 | O   | HOH | L | 4  | 24.719 | −17.416 | −55.839 | 1.00 | 18.80 | O |
| ATOM | 3213 | O   | HOH | L | 5  | 56.042 | −24.139 | −88.387 | 1.00 | 23.26 | O |
| ATOM | 3214 | O   | HOH | L | 6  | 52.369 | −23.781 | −61.646 | 1.00 | 54.74 | O |
| ATOM | 3215 | O   | HOH | L | 7  | 55.535 | −46.365 | −53.456 | 1.00 | 22.16 | O |
| ATOM | 3216 | O   | HOH | L | 8  | 8.828  | −22.635 | −58.171 | 1.00 | 18.50 | O |
| ATOM | 3217 | O   | HOH | L | 9  | 14.988 | −21.145 | −51.047 | 1.00 | 17.77 | O |
| ATOM | 3218 | O   | HOH | L | 10 | 62.602 | −48.505 | −56.129 | 1.00 | 24.86 | O |
| ATOM | 3219 | O   | HOH | L | 11 | 65.001 | −31.563 | −76.089 | 1.00 | 25.53 | O |
| ATOM | 3220 | O   | HOH | L | 12 | 14.130 | −8.733  | −49.754 | 1.00 | 21.34 | O |
| ATOM | 3221 | O   | HOH | L | 13 | 23.119 | −14.548 | −62.918 | 1.00 | 20.40 | O |
| ATOM | 3222 | O   | HOH | L | 14 | 21.210 | −15.286 | −50.733 | 1.00 | 17.30 | O |
| ATOM | 3223 | O   | HOH | L | 15 | 57.259 | −13.554 | −86.198 | 1.00 | 25.37 | O |
| ATOM | 3224 | O   | HOH | L | 16 | 24.956 | −18.321 | −34.540 | 1.00 | 38.12 | O |
| ATOM | 3225 | O   | HOH | L | 19 | 47.754 | −31.698 | −84.578 | 1.00 | 22.45 | O |
| ATOM | 3226 | O   | HOH | L | 20 | 21.030 | −21.563 | −56.566 | 1.00 | 19.08 | O |
| ATOM | 3227 | O   | HOH | L | 21 | 71.002 | −29.362 | −86.145 | 1.00 | 36.25 | O |
| ATOM | 3228 | O   | HOH | L | 22 | 23.857 | −32.982 | −58.161 | 1.00 | 23.66 | O |

TABLE 5-continued

Atomic coordinates for CRBN(TBD):Thalidomide (Murine protein)

| ATOM | 3229 | O | HOH | L | 23 | 2.875 | −25.757 | −57.166 | 1.00 | 20.01 | O |
|---|---|---|---|---|---|---|---|---|---|---|---|
| ATOM | 3230 | O | HOH | L | 24 | 32.192 | −13.968 | −47.044 | 1.00 | 25.63 | O |
| ATOM | 3231 | O | HOH | L | 26 | 49.912 | −19.759 | −74.422 | 1.00 | 19.54 | O |
| ATOM | 3232 | O | HOH | L | 27 | 13.373 | −28.885 | −74.194 | 1.00 | 27.49 | O |
| ATOM | 3233 | O | HOH | L | 29 | 48.198 | −32.174 | −59.017 | 1.00 | 29.19 | O |
| ATOM | 3234 | O | HOH | L | 30 | 31.596 | −3.197 | −71.615 | 1.00 | 29.34 | O |
| ATOM | 3235 | O | HOH | L | 31 | 29.564 | 1.563 | −58.456 | 1.00 | 31.73 | O |
| ATOM | 3236 | O | HOH | L | 32 | 56.721 | −56.721 | −56.721 | 0.33 | 21.07 | O |
| ATOM | 3237 | O | HOH | L | 33 | 34.576 | −4.582 | −56.622 | 1.00 | 32.80 | O |
| ATOM | 3238 | O | HOH | L | 34 | 52.739 | −23.483 | −87.327 | 1.00 | 35.47 | O |
| ATOM | 3239 | O | HOH | L | 35 | 50.819 | −31.948 | −58.772 | 1.00 | 24.57 | O |
| ATOM | 3240 | O | HOH | L | 36 | 52.449 | −22.563 | −94.386 | 1.00 | 45.59 | O |
| ATOM | 3241 | O | HOH | L | 37 | 56.155 | −34.208 | −76.897 | 1.00 | 24.73 | O |
| ATOM | 3242 | O | HOH | L | 38 | 58.601 | −27.291 | −69.075 | 1.00 | 26.55 | O |
| ATOM | 3243 | O | HOH | L | 39 | 39.518 | −32.027 | −76.439 | 1.00 | 27.86 | O |
| ATOM | 3244 | O | HOH | L | 40 | 20.804 | −3.252 | −50.008 | 1.00 | 22.31 | O |
| ATOM | 3245 | O | HOH | L | 41 | 19.819 | −38.478 | −66.567 | 1.00 | 38.71 | O |
| ATOM | 3246 | O | HOH | L | 42 | 35.862 | −6.990 | −55.363 | 1.00 | 29.01 | O |
| ATOM | 3247 | O | HOH | L | 43 | 23.403 | −38.735 | −60.658 | 1.00 | 32.76 | O |
| ATOM | 3248 | O | HOH | L | 44 | 56.335 | −35.307 | −63.878 | 1.00 | 23.02 | O |
| ATOM | 3249 | O | HOH | L | 45 | 20.683 | −39.095 | −60.510 | 1.00 | 23.74 | O |
| ATOM | 3250 | O | HOH | L | 46 | 47.508 | −38.125 | −57.069 | 1.00 | 30.14 | O |
| ATOM | 3251 | O | HOH | L | 47 | 33.932 | −5.710 | −64.561 | 1.00 | 25.29 | O |
| ATOM | 3252 | O | HOH | L | 48 | 31.829 | −31.634 | −63.627 | 1.00 | 29.57 | O |
| ATOM | 3253 | O | HOH | L | 49 | 6.581 | −32.724 | −67.282 | 1.00 | 16.81 | O |
| ATOM | 3254 | O | HOH | L | 50 | 55.424 | −36.395 | −75.847 | 1.00 | 29.00 | O |
| ATOM | 3255 | O | HOH | L | 52 | 53.938 | −18.795 | −74.751 | 1.00 | 22.50 | O |
| ATOM | 3256 | O | HOH | L | 53 | 29.550 | −19.261 | −53.836 | 1.00 | 28.96 | O |
| ATOM | 3257 | O | HOH | L | 54 | 38.663 | −5.963 | −51.096 | 1.00 | 36.07 | O |
| ATOM | 3258 | O | HOH | L | 55 | 30.627 | −7.838 | −39.456 | 1.00 | 30.12 | O |
| ATOM | 3259 | O | HOH | L | 56 | 62.560 | −58.143 | −63.161 | 1.00 | 40.85 | O |
| ATOM | 3260 | O | HOH | L | 57 | 22.691 | −21.161 | −68.558 | 1.00 | 21.56 | O |
| ATOM | 3261 | O | HOH | L | 58 | 32.005 | −19.832 | −60.629 | 1.00 | 24.94 | O |
| ATOM | 3262 | O | HOH | L | 59 | 50.865 | −37.985 | −81.995 | 1.00 | 30.20 | O |
| ATOM | 3263 | O | HOH | L | 60 | 57.411 | −32.713 | −74.573 | 1.00 | 27.14 | O |
| ATOM | 3264 | O | HOH | L | 62 | 65.431 | −37.990 | −65.124 | 1.00 | 26.53 | O |
| ATOM | 3265 | O | HOH | L | 63 | 15.410 | −35.574 | −65.857 | 1.00 | 26.67 | O |
| ATOM | 3266 | O | HOH | L | 64 | 22.259 | −23.786 | −52.561 | 1.00 | 27.79 | O |
| ATOM | 3267 | O | HOH | L | 65 | −0.586 | −30.232 | −70.323 | 1.00 | 23.86 | O |
| ATOM | 3268 | O | HOH | L | 66 | 30.833 | −38.965 | −60.588 | 1.00 | 38.45 | O |
| ATOM | 3269 | O | HOH | L | 67 | 38.890 | −27.652 | −90.787 | 1.00 | 43.26 | O |
| ATOM | 3270 | O | HOH | L | 68 | 14.621 | −34.144 | −68.435 | 1.00 | 27.37 | O |
| ATOM | 3271 | O | HOH | L | 69 | 55.315 | −32.985 | −64.970 | 1.00 | 32.04 | O |
| ATOM | 3272 | O | HOH | L | 70 | 39.917 | −5.867 | −64.037 | 1.00 | 37.19 | O |
| ATOM | 3273 | O | HOH | L | 71 | 59.042 | −30.597 | −67.840 | 1.00 | 49.83 | O |
| ATOM | 3274 | O | HOH | L | 72 | 39.956 | −30.167 | −78.435 | 1.00 | 26.40 | O |
| ATOM | 3275 | O | HOH | L | 73 | 38.715 | −12.185 | −49.915 | 1.00 | 26.98 | O |
| ATOM | 3276 | O | HOH | L | 74 | 34.733 | −25.884 | −89.162 | 1.00 | 44.84 | O |
| ATOM | 3277 | O | HOH | L | 75 | 14.793 | −10.253 | −55.318 | 1.00 | 25.87 | O |
| ATOM | 3278 | O | HOH | L | 76 | 43.257 | −19.289 | −71.654 | 1.00 | 35.85 | O |
| ATOM | 3279 | O | HOH | L | 77 | 54.191 | −29.019 | −89.699 | 1.00 | 26.10 | O |
| ATOM | 3280 | O | HOH | L | 78 | 56.049 | −35.127 | −73.022 | 1.00 | 40.71 | O |
| ATOM | 3281 | O | HOH | L | 79 | 53.602 | −50.162 | −67.499 | 1.00 | 25.66 | O |
| ATOM | 3282 | O | HOH | L | 81 | 19.392 | −5.729 | −67.548 | 1.00 | 50.36 | O |
| ATOM | 3283 | O | HOH | L | 82 | 48.086 | −37.600 | −81.927 | 1.00 | 33.03 | O |
| ATOM | 3284 | O | HOH | L | 83 | 33.928 | −23.343 | −87.740 | 1.00 | 43.29 | O |
| ATOM | 3285 | O | HOH | L | 84 | 45.337 | −54.283 | −68.061 | 1.00 | 24.25 | O |
| ATOM | 3286 | O | HOH | L | 85 | 40.008 | −26.253 | −88.773 | 1.00 | 32.15 | O |
| ATOM | 3287 | O | HOH | L | 86 | 62.007 | −37.583 | −75.462 | 1.00 | 30.26 | O |
| ATOM | 3288 | O | HOH | L | 87 | 26.924 | −15.979 | −68.699 | 1.00 | 22.27 | O |
| ATOM | 3289 | O | HOH | L | 88 | 54.758 | −54.758 | −54.758 | 0.33 | 29.36 | O |
| ATOM | 3290 | O | HOH | L | 89 | 4.211 | −18.498 | −58.358 | 1.00 | 29.69 | O |
| ATOM | 3291 | O | HOH | L | 90 | 19.606 | −14.751 | −67.753 | 1.00 | 25.57 | O |
| ATOM | 3292 | O | HOH | L | 91 | 55.344 | −17.358 | −73.069 | 1.00 | 39.29 | O |
| ATOM | 3293 | O | HOH | L | 92 | 15.205 | −2.801 | −46.301 | 1.00 | 27.99 | O |
| ATOM | 3294 | O | HOH | L | 94 | 62.815 | −11.784 | −80.085 | 1.00 | 48.21 | O |
| ATOM | 3295 | O | HOH | L | 95 | 67.361 | −18.113 | −86.396 | 1.00 | 29.05 | O |
| ATOM | 3296 | O | HOH | L | 96 | 16.186 | −37.729 | −66.798 | 1.00 | 29.22 | O |
| ATOM | 3297 | O | HOH | L | 97 | 16.017 | −13.618 | −64.796 | 1.00 | 31.48 | O |
| ATOM | 3298 | O | HOH | L | 98 | 8.144 | −38.224 | −57.733 | 1.00 | 31.35 | O |
| ATOM | 3299 | O | HOH | L | 99 | 55.048 | −51.828 | −69.233 | 1.00 | 37.02 | O |
| ATOM | 3300 | O | HOH | L | 100 | 69.818 | −53.683 | −61.252 | 1.00 | 48.96 | O |
| ATOM | 3301 | O | HOH | L | 101 | 66.240 | −27.453 | −70.201 | 1.00 | 44.37 | O |
| ATOM | 3302 | O | HOH | L | 102 | 31.341 | −16.062 | −42.771 | 1.00 | 38.42 | O |
| ATOM | 3303 | O | HOH | L | 103 | 72.208 | −29.557 | −72.934 | 1.00 | 33.19 | O |
| ATOM | 3304 | O | HOH | L | 104 | 23.266 | −42.575 | −57.325 | 1.00 | 46.63 | O |
| ATOM | 3305 | O | HOH | L | 105 | 25.859 | −27.605 | −53.579 | 1.00 | 34.86 | O |
| ATOM | 3306 | O | HOH | L | 106 | 70.231 | −16.418 | −80.824 | 1.00 | 42.25 | O |

TABLE 5-continued

Atomic coordinates for CRBN(TBD):Thalidomide (Murine protein)

| ATOM | 3307 | O | HOH | L | 107 | 58.669 | −13.001 | −77.376 | 1.00 | 32.45 | O |
| --- | --- | --- | --- | --- | --- | --- | --- | --- | --- | --- | --- |
| ATOM | 3308 | O | HOH | L | 109 | 40.445 | −38.004 | −67.661 | 1.00 | 37.07 | O |
| ATOM | 3309 | O | HOH | L | 110 | 17.351 | −14.704 | −61.888 | 1.00 | 24.50 | O |
| ATOM | 3310 | O | HOH | L | 111 | 2.094 | −17.036 | −63.913 | 1.00 | 38.85 | O |
| ATOM | 3311 | O | HOH | L | 112 | 33.007 | 0.435 | −69.383 | 1.00 | 47.08 | O |
| ATOM | 3312 | O | HOH | L | 113 | 38.233 | −11.754 | −47.081 | 1.00 | 29.21 | O |
| ATOM | 3313 | O | HOH | L | 114 | 30.240 | −20.982 | −62.176 | 1.00 | 33.07 | O |
| ATOM | 3314 | O | HOH | L | 115 | 59.000 | −41.676 | −72.417 | 1.00 | 38.40 | O |
| ATOM | 3315 | O | HOH | L | 116 | 19.994 | −18.861 | −69.408 | 1.00 | 32.79 | O |
| ATOM | 3316 | O | HOH | L | 117 | 27.959 | −32.428 | −55.745 | 1.00 | 31.40 | O |
| ATOM | 3317 | O | HOH | L | 118 | 41.831 | −45.805 | −65.492 | 1.00 | 37.37 | O |
| ATOM | 3318 | O | HOH | L | 119 | 39.227 | −5.519 | −61.376 | 1.00 | 26.62 | O |
| ATOM | 3319 | O | HOH | L | 120 | 43.399 | −31.422 | −86.723 | 1.00 | 41.65 | O |
| ATOM | 3320 | O | HOH | L | 121 | 40.759 | −31.942 | −59.751 | 1.00 | 33.49 | O |
| ATOM | 3321 | O | HOH | L | 122 | 38.990 | −18.743 | −56.566 | 1.00 | 37.57 | O |
| ATOM | 3322 | O | HOH | L | 124 | 34.180 | −28.803 | −83.172 | 1.00 | 66.36 | O |
| ATOM | 3323 | O | HOH | L | 125 | 22.157 | −34.743 | −55.043 | 1.00 | 36.26 | O |
| ATOM | 3324 | O | HOH | L | 126 | 23.554 | −28.381 | −52.885 | 1.00 | 36.67 | O |
| ATOM | 3325 | O | HOH | L | 127 | 49.603 | −49.326 | −67.804 | 1.00 | 30.26 | O |
| ATOM | 3326 | O | HOH | L | 128 | 49.184 | −33.675 | −87.620 | 1.00 | 40.57 | O |
| ATOM | 3327 | O | HOH | L | 129 | 46.134 | −24.500 | −91.071 | 1.00 | 54.77 | O |
| ATOM | 3328 | O | HOH | L | 131 | 34.363 | −21.085 | −61.021 | 1.00 | 39.28 | O |
| ATOM | 3329 | O | HOH | L | 132 | 5.001 | −18.000 | −67.452 | 1.00 | 48.23 | O |
| ATOM | 3330 | O | HOH | L | 133 | 41.393 | −51.695 | −53.867 | 1.00 | 33.74 | O |
| ATOM | 3331 | O | HOH | L | 134 | 57.460 | −36.666 | −66.273 | 1.00 | 26.39 | O |
| ATOM | 3332 | O | HOH | L | 135 | 54.206 | −56.313 | −60.809 | 1.00 | 30.48 | O |
| ATOM | 3333 | O | HOH | L | 136 | 56.422 | −12.436 | −79.243 | 1.00 | 26.12 | O |
| ATOM | 3334 | O | HOH | L | 137 | 32.210 | −2.412 | −75.847 | 1.00 | 36.07 | O |
| ATOM | 3335 | O | HOH | L | 138 | −1.794 | −33.617 | −68.497 | 1.00 | 31.48 | O |
| ATOM | 3336 | O | HOH | L | 139 | 19.335 | −1.722 | −55.280 | 1.00 | 39.05 | O |
| ATOM | 3337 | O | HOH | L | 140 | 31.331 | −15.482 | −70.862 | 1.00 | 29.93 | O |
| ATOM | 3338 | O | HOH | L | 141 | 9.905 | −31.642 | −53.142 | 1.00 | 27.94 | O |
| ATOM | 3339 | O | HOH | L | 142 | 8.821 | −24.376 | −71.208 | 1.00 | 29.89 | O |
| ATOM | 3340 | O | HOH | L | 143 | 63.042 | −46.222 | −69.149 | 1.00 | 38.30 | O |
| ATOM | 3341 | O | HOH | L | 144 | 17.345 | −42.282 | −55.006 | 1.00 | 44.34 | O |
| ATOM | 3342 | O | HOH | L | 145 | 55.020 | −38.474 | −69.945 | 1.00 | 34.61 | O |
| ATOM | 3343 | O | HOH | L | 146 | 18.450 | −20.692 | −68.957 | 1.00 | 30.72 | O |
| ATOM | 3344 | O | HOH | L | 147 | 42.077 | −23.300 | −76.781 | 1.00 | 32.86 | O |
| ATOM | 3345 | O | HOH | L | 148 | 58.625 | −39.090 | −81.652 | 1.00 | 60.70 | O |
| ATOM | 3346 | O | HOH | L | 149 | 51.531 | −24.281 | −69.517 | 1.00 | 34.26 | O |
| ATOM | 3347 | O | HOH | L | 151 | 45.150 | −26.535 | −89.054 | 1.00 | 34.72 | O |
| ATOM | 3348 | O | HOH | L | 152 | 31.499 | −19.040 | −49.210 | 1.00 | 38.16 | O |
| ATOM | 3349 | O | HOH | L | 153 | 37.891 | −6.083 | −54.755 | 1.00 | 33.57 | O |
| ATOM | 3350 | O | HOH | L | 154 | 66.988 | −52.671 | −55.719 | 1.00 | 30.81 | O |
| ATOM | 3351 | O | HOH | L | 155 | 45.069 | −27.121 | −68.805 | 1.00 | 40.12 | O |
| ATOM | 3352 | O | HOH | L | 156 | 3.210 | −14.373 | −61.150 | 1.00 | 38.71 | O |
| ATOM | 3353 | O | HOH | L | 157 | 39.664 | −3.492 | −58.805 | 1.00 | 45.72 | O |
| ATOM | 3354 | O | HOH | L | 159 | 53.595 | −54.245 | −69.104 | 1.00 | 43.37 | O |
| ATOM | 3355 | O | HOH | L | 160 | 54.828 | −13.631 | −82.091 | 1.00 | 26.33 | O |
| ATOM | 3356 | O | HOH | L | 161 | 20.814 | −25.479 | −74.702 | 1.00 | 58.61 | O |
| ATOM | 3357 | O | HOH | L | 163 | 19.228 | −25.990 | −77.787 | 1.00 | 48.48 | O |
| ATOM | 3358 | O | HOH | L | 164 | 67.264 | −15.888 | −77.412 | 1.00 | 48.33 | O |
| ATOM | 3359 | O | HOH | L | 165 | 42.006 | −18.352 | −88.476 | 1.00 | 33.63 | O |
| ATOM | 3360 | O | HOH | L | 166 | 25.933 | −17.844 | −39.812 | 1.00 | 31.78 | O |
| ATOM | 3361 | O | HOH | L | 167 | 37.206 | −24.371 | −53.780 | 1.00 | 39.40 | O |
| ATOM | 3362 | O | HOH | L | 168 | 37.999 | −11.068 | −39.807 | 1.00 | 42.75 | O |
| ATOM | 3363 | O | HOH | L | 169 | 73.344 | −30.963 | −82.523 | 1.00 | 40.49 | O |
| ATOM | 3364 | O | HOH | L | 170 | 36.362 | −26.893 | −52.369 | 1.00 | 36.87 | O |
| ATOM | 3365 | O | HOH | L | 171 | 62.308 | −32.498 | −65.409 | 1.00 | 37.46 | O |
| ATOM | 3366 | O | HOH | L | 172 | 17.254 | −31.252 | −71.362 | 1.00 | 33.43 | O |
| ATOM | 3367 | O | HOH | L | 173 | 40.001 | −39.056 | −63.160 | 1.00 | 31.88 | O |
| ATOM | 3368 | O | HOH | L | 174 | 49.625 | −34.552 | −52.605 | 1.00 | 44.94 | O |
| ATOM | 3369 | O | HOH | L | 176 | 20.609 | −3.320 | −53.976 | 1.00 | 31.97 | O |
| ATOM | 3370 | O | HOH | L | 177 | 39.607 | −36.067 | −73.555 | 1.00 | 39.96 | O |
| ATOM | 3371 | O | HOH | L | 179 | 40.911 | −37.582 | −81.155 | 1.00 | 42.56 | O |
| ATOM | 3372 | O | HOH | L | 180 | 32.366 | −5.642 | −39.007 | 1.00 | 37.50 | O |
| ATOM | 3373 | O | HOH | L | 181 | 38.412 | −18.866 | −63.601 | 1.00 | 46.78 | O |
| ATOM | 3374 | O | HOH | L | 183 | 23.962 | −5.949 | −41.743 | 1.00 | 38.92 | O |
| ATOM | 3375 | O | HOH | L | 184 | 38.101 | −18.926 | −51.774 | 1.00 | 42.05 | O |
| ATOM | 3376 | O | HOH | L | 185 | 33.742 | −17.263 | −48.603 | 1.00 | 40.25 | O |
| ATOM | 3377 | O | HOH | L | 186 | 61.142 | −31.392 | −90.072 | 1.00 | 28.73 | O |
| ATOM | 3378 | O | HOH | L | 187 | 37.584 | −16.568 | −42.204 | 1.00 | 53.14 | O |
| ATOM | 3379 | O | HOH | L | 189 | 40.534 | −31.244 | −73.750 | 1.00 | 32.02 | O |
| ATOM | 3380 | O | HOH | L | 190 | 13.600 | −39.173 | −54.119 | 1.00 | 40.73 | O |
| ATOM | 3381 | O | HOH | L | 192 | 48.744 | −41.484 | −84.299 | 1.00 | 40.90 | O |
| ATOM | 3382 | O | HOH | L | 193 | 30.427 | −24.885 | −65.755 | 1.00 | 35.31 | O |
| ATOM | 3383 | O | HOH | L | 194 | 31.790 | −3.373 | −39.852 | 1.00 | 35.52 | O |
| ATOM | 3384 | O | HOH | L | 195 | 39.482 | −49.661 | −51.476 | 1.00 | 43.93 | O |

TABLE 5-continued

Atomic coordinates for CRBN(TBD):Thalidomide (Murine protein)

| ATOM | 3385 | O | HOH | L | 197 | 67.361 | −52.465 | −64.836 | 1.00 | 43.12 | O |
| ATOM | 3386 | O | HOH | L | 198 | 3.320 | −34.365 | −70.523 | 1.00 | 31.27 | O |
| ATOM | 3387 | O | HOH | L | 199 | 37.825 | −39.366 | −61.254 | 1.00 | 43.02 | O |
| ATOM | 3388 | O | HOH | L | 200 | 38.849 | −36.273 | −77.550 | 1.00 | 42.21 | O |
| ATOM | 3389 | O | HOH | L | 201 | 65.151 | −25.188 | −70.176 | 1.00 | 37.38 | O |
| ATOM | 3390 | O | HOH | L | 203 | 18.713 | −38.229 | −53.728 | 1.00 | 49.01 | O |
| ATOM | 3391 | O | HOH | L | 206 | 34.839 | −22.018 | −82.723 | 1.00 | 50.80 | O |
| ATOM | 3392 | O | HOH | L | 207 | 42.650 | −25.189 | −90.764 | 1.00 | 44.63 | O |
| ATOM | 3393 | O | HOH | L | 208 | 4.356 | −15.540 | −63.217 | 1.00 | 38.03 | O |
| ATOM | 3394 | O | HOH | L | 209 | 43.320 | −38.463 | −54.937 | 1.00 | 44.13 | O |
| ATOM | 3395 | O | HOH | L | 211 | 76.029 | −28.331 | −85.901 | 1.00 | 57.13 | O |
| ATOM | 3396 | O | HOH | L | 212 | 56.366 | −26.141 | −65.497 | 1.00 | 39.95 | O |
| ATOM | 3397 | O | HOH | L | 213 | 9.305 | −38.562 | −67.431 | 1.00 | 36.28 | O |
| ATOM | 3398 | O | HOH | L | 214 | 13.767 | −7.728 | −63.610 | 1.00 | 42.90 | O |
| ATOM | 3399 | O | HOH | L | 215 | 41.452 | −36.154 | −70.496 | 1.00 | 37.07 | O |
| ATOM | 3400 | O | HOH | L | 216 | 38.839 | −15.497 | −61.917 | 1.00 | 33.52 | O |
| ATOM | 3401 | O | HOH | L | 217 | 1.308 | −33.231 | −72.057 | 1.00 | 36.29 | O |
| ATOM | 3402 | O | HOH | L | 219 | 49.869 | −31.383 | −89.375 | 1.00 | 44.40 | O |
| ATOM | 3403 | O | HOH | L | 220 | 61.475 | −49.641 | −72.537 | 1.00 | 50.76 | O |
| ATOM | 3404 | O | HOH | L | 221 | 61.166 | −39.487 | −51.137 | 1.00 | 33.15 | O |
| ATOM | 3405 | O | HOH | L | 223 | 21.276 | −36.732 | −53.795 | 1.00 | 48.63 | O |
| ATOM | 3406 | O | HOH | L | 224 | 30.813 | −21.851 | −51.107 | 1.00 | 47.68 | O |
| ATOM | 3407 | O | HOH | L | 225 | 48.521 | −21.025 | −67.416 | 1.00 | 50.19 | O |
| ATOM | 3408 | O | HOH | L | 226 | 18.429 | −24.372 | −56.098 | 1.00 | 39.59 | O |
| ATOM | 3409 | O | HOH | L | 227 | 53.694 | −41.460 | −87.578 | 1.00 | 38.29 | O |
| ATOM | 3410 | O | HOH | L | 228 | 13.969 | −14.370 | −66.634 | 1.00 | 34.12 | O |
| ATOM | 3411 | O | HOH | L | 229 | 40.230 | −11.784 | −41.009 | 1.00 | 49.09 | O |
| ATOM | 3412 | O | HOH | L | 230 | 6.830 | −21.656 | −74.018 | 1.00 | 50.79 | O |
| ATOM | 3413 | O | HOH | L | 231 | 6.370 | −30.440 | −50.445 | 1.00 | 35.75 | O |
| ATOM | 3414 | O | HOH | L | 233 | 47.555 | −29.458 | −60.157 | 1.00 | 35.84 | O |
| ATOM | 3415 | O | HOH | L | 234 | 67.711 | −55.008 | −63.991 | 1.00 | 39.36 | O |
| ATOM | 3416 | O | HOH | L | 235 | 18.254 | −37.505 | −71.346 | 1.00 | 39.21 | O |
| ATOM | 3417 | O | HOH | L | 236 | 50.344 | −27.293 | −92.014 | 1.00 | 47.07 | O |
| ATOM | 3418 | O | HOH | L | 237 | 14.476 | −14.568 | −69.530 | 1.00 | 52.40 | O |
| ATOM | 3419 | O | HOH | L | 238 | 24.003 | −41.225 | −61.832 | 1.00 | 35.95 | O |
| ATOM | 3420 | O | HOH | L | 239 | 62.939 | −22.994 | −72.369 | 1.00 | 37.23 | O |
| ATOM | 3421 | O | HOH | L | 240 | 15.132 | −36.153 | −70.002 | 1.00 | 37.73 | O |
| ATOM | 3422 | O | HOH | L | 241 | 37.454 | −1.305 | −53.238 | 1.00 | 38.09 | O |
| ATOM | 3423 | O | HOH | L | 242 | 17.252 | −19.234 | −70.577 | 1.00 | 40.42 | O |
| ATOM | 3424 | O | HOH | L | 243 | 1.304 | −38.421 | −56.467 | 1.00 | 31.41 | O |
| ATOM | 3425 | O | HOH | L | 244 | 8.930 | −34.037 | −51.990 | 1.00 | 37.56 | O |
| ATOM | 3426 | O | HOH | L | 245 | 8.559 | −29.551 | −51.831 | 1.00 | 40.49 | O |
| ATOM | 3427 | O | HOH | L | 246 | 35.787 | −20.582 | −51.226 | 1.00 | 43.29 | O |
| ATOM | 3428 | O | HOH | L | 247 | 34.824 | −3.225 | −65.250 | 1.00 | 31.64 | O |
| ATOM | 3429 | O | HOH | L | 248 | 22.672 | −16.662 | −34.081 | 1.00 | 46.02 | O |
| ATOM | 3430 | O | HOH | L | 249 | 75.262 | −40.190 | −59.792 | 1.00 | 41.19 | O |
| ATOM | 3431 | O | HOH | L | 250 | 22.962 | 0.248 | −57.829 | 1.00 | 40.96 | O |
| ATOM | 3432 | O | HOH | L | 251 | 25.981 | 0.591 | −71.688 | 0.50 | 24.89 | O |
| ATOM | 3433 | O | HOH | L | 252 | 63.706 | −56.018 | −57.061 | 1.00 | 30.50 | O |
| ATOM | 3434 | O | HOH | L | 253 | 54.040 | −33.292 | −69.581 | 1.00 | 41.72 | O |
| ATOM | 3435 | O | HOH | L | 254 | 31.642 | −1.034 | −54.424 | 1.00 | 40.44 | O |
| ATOM | 3436 | O | HOH | L | 255 | 31.894 | −32.875 | −68.582 | 1.00 | 38.12 | O |
| ATOM | 3437 | O | HOH | L | 256 | 64.430 | −30.335 | −93.014 | 1.00 | 36.75 | O |
| ATOM | 3438 | O | HOH | L | 257 | 51.606 | −48.445 | −47.516 | 1.00 | 35.56 | O |
| ATOM | 3439 | O | HOH | L | 258 | 14.775 | −5.738 | −59.449 | 1.00 | 41.76 | O |
| ATOM | 3440 | O | HOH | L | 259 | 41.671 | −49.537 | −61.972 | 1.00 | 37.02 | O |
| ATOM | 3441 | O | HOH | L | 260 | 31.930 | −51.902 | −57.220 | 1.00 | 41.09 | O |
| ATOM | 3442 | O | HOH | L | 318 | 40.656 | −10.643 | −46.436 | 1.00 | 48.66 | O |
| ATOM | 3443 | O | HOH | L | 319 | 36.632 | −32.374 | −81.505 | 1.00 | 43.88 | O |
| ATOM | 3444 | O | HOH | L | 320 | 68.355 | −33.475 | −72.601 | 1.00 | 39.03 | O |
| ATOM | 3445 | O | HOH | L | 321 | 20.142 | −19.865 | −40.472 | 1.00 | 43.62 | O |
| ATOM | 3446 | O | HOH | L | 322 | 55.509 | −21.896 | −63.050 | 1.00 | 61.99 | O |
| ATOM | 3447 | O | HOH | L | 323 | 44.019 | −45.006 | −69.659 | 1.00 | 41.56 | O |
| ATOM | 3448 | O | HOH | L | 324 | 48.406 | −28.659 | −56.758 | 1.00 | 35.63 | O |
| ATOM | 3449 | O | HOH | L | 325 | 22.016 | −11.423 | −35.128 | 1.00 | 42.67 | O |
| ATOM | 3450 | O | HOH | L | 328 | 38.454 | −17.463 | −69.431 | 1.00 | 42.17 | O |
| ATOM | 3451 | O | HOH | L | 329 | 61.742 | −31.652 | −71.038 | 1.00 | 44.53 | O |
| ATOM | 3452 | O | HOH | L | 330 | 42.263 | −40.186 | −81.271 | 1.00 | 48.24 | O |
| ATOM | 3453 | O | HOH | L | 331 | 49.976 | −26.005 | −71.185 | 1.00 | 47.01 | O |
| ATOM | 3454 | O | HOH | L | 333 | 26.720 | −18.070 | −44.965 | 1.00 | 47.61 | O |
| ATOM | 3455 | O | HOH | L | 335 | 43.194 | −28.288 | −88.825 | 1.00 | 55.66 | O |
| ATOM | 3456 | O | HOH | L | 336 | 66.480 | −36.523 | −76.859 | 1.00 | 58.80 | O |
| ATOM | 3457 | O | HOH | L | 337 | 35.490 | −19.711 | −90.764 | 1.00 | 47.63 | O |
| ATOM | 3458 | O | HOH | L | 338 | 39.878 | −37.252 | −65.509 | 1.00 | 46.45 | O |
| ATOM | 3459 | O | HOH | L | 340 | 62.966 | −32.900 | −55.399 | 1.00 | 37.54 | O |
| ATOM | 3460 | O | HOH | L | 341 | 31.868 | −4.880 | −77.701 | 1.00 | 39.79 | O |
| ATOM | 3461 | O | HOH | L | 342 | 36.203 | −3.882 | −61.128 | 1.00 | 39.23 | O |
| ATOM | 3462 | O | HOH | L | 343 | 42.685 | −0.657 | −42.764 | 1.00 | 43.15 | O |

TABLE 5-continued

Atomic coordinates for CRBN(TBD):Thalidomide (Murine protein)

| ATOM | 3463 | O | HOH | L | 344 | 40.818 | −5.215 | −45.096 | 1.00 | 56.07 | O |
|---|---|---|---|---|---|---|---|---|---|---|---|
| ATOM | 3464 | O | HOH | L | 346 | 66.722 | −22.108 | −81.794 | 1.00 | 56.72 | O |
| ATOM | 3465 | O | HOH | L | 348 | 55.966 | −41.575 | −79.472 | 1.00 | 49.96 | O |
| ATOM | 3466 | O | HOH | L | 349 | 44.585 | −60.475 | −75.365 | 1.00 | 48.56 | O |
| ATOM | 3467 | O | HOH | L | 350 | 28.321 | −18.140 | −42.798 | 1.00 | 48.85 | O |
| ATOM | 3468 | O | HOH | L | 351 | 36.711 | −12.525 | −69.413 | 1.00 | 62.02 | O |
| ATOM | 3469 | O | HOH | L | 352 | 23.475 | −1.669 | −44.351 | 1.00 | 50.11 | O |
| ATOM | 3470 | O | HOH | L | 353 | 32.683 | −34.482 | −74.566 | 1.00 | 42.64 | O |
| ATOM | 3471 | O | HOH | L | 354 | 42.598 | −42.479 | −53.181 | 1.00 | 54.04 | O |
| ATOM | 3472 | O | HOH | L | 355 | 45.226 | −27.496 | −59.852 | 1.00 | 56.54 | O |
| ATOM | 3473 | O | HOH | L | 356 | 48.705 | −23.071 | −71.479 | 1.00 | 42.28 | O |
| ATOM | 3474 | O | HOH | L | 357 | 64.200 | −40.843 | −48.240 | 1.00 | 47.71 | O |
| ATOM | 3475 | O | HOH | L | 358 | 42.462 | −57.325 | −79.655 | 1.00 | 55.02 | O |
| ATOM | 3476 | O | HOH | L | 359 | 61.857 | −37.082 | −49.618 | 1.00 | 43.95 | O |
| ATOM | 3477 | O | HOH | L | 360 | 69.801 | −49.760 | −56.992 | 1.00 | 35.21 | O |
| ATOM | 3478 | O | HOH | L | 361 | 25.528 | −14.672 | −70.983 | 1.00 | 47.17 | O |
| ATOM | 3479 | O | HOH | L | 362 | 9.448 | −41.468 | −63.620 | 1.00 | 45.28 | O |
| ATOM | 3480 | O | HOH | L | 364 | 40.318 | −20.441 | −66.053 | 1.00 | 56.41 | O |
| ATOM | 3481 | O | HOH | L | 365 | 7.020 | −26.697 | −73.127 | 1.00 | 44.25 | O |
| ATOM | 3482 | O | HOH | L | 367 | 48.565 | −24.330 | −92.755 | 1.00 | 46.91 | O |
| ATOM | 3483 | O | HOH | L | 368 | 54.933 | −30.591 | −71.122 | 1.00 | 39.83 | O |
| ATOM | 3484 | O | HOH | L | 369 | 47.106 | −24.178 | −95.234 | 1.00 | 60.27 | O |
| ATOM | 3485 | O | HOH | L | 370 | 35.148 | −33.345 | −60.155 | 1.00 | 36.82 | O |
| ATOM | 3486 | O | HOH | L | 371 | 64.203 | −11.806 | −73.783 | 1.00 | 46.01 | O |
| ATOM | 3487 | O | HOH | L | 372 | 2.006 | −14.612 | −65.015 | 1.00 | 51.51 | O |
| ATOM | 3488 | O | HOH | L | 373 | 65.637 | −36.074 | −74.556 | 1.00 | 50.95 | O |
| ATOM | 3489 | O | HOH | L | 374 | 59.802 | −38.574 | −74.031 | 1.00 | 50.58 | O |
| ATOM | 3490 | O | HOH | L | 375 | 13.879 | −38.462 | −61.263 | 1.00 | 85.18 | O |
| ATOM | 3491 | O | HOH | L | 376 | 61.763 | −34.002 | −90.900 | 1.00 | 39.47 | O |
| ATOM | 3492 | O | HOH | L | 378 | 40.289 | −13.680 | −42.954 | 1.00 | 45.75 | O |
| ATOM | 3493 | O | HOH | L | 379 | 33.129 | −28.516 | −51.743 | 1.00 | 64.82 | O |
| ATOM | 3494 | O | HOH | L | 382 | 42.921 | −25.366 | −65.742 | 1.00 | 57.36 | O |
| ATOM | 3495 | O | HOH | L | 383 | 42.791 | −19.175 | −74.336 | 1.00 | 43.59 | O |
| ATOM | 3496 | O | HOH | L | 384 | 53.243 | −34.346 | −84.660 | 1.00 | 63.91 | O |
| ATOM | 3497 | O | HOH | L | 385 | 25.954 | 8.497 | −50.232 | 1.00 | 53.53 | O |
| ATOM | 3498 | O | HOH | L | 388 | 59.804 | −31.394 | −53.029 | 1.00 | 65.02 | O |
| ATOM | 3499 | O | HOH | L | 389 | 50.780 | −22.230 | −72.760 | 1.00 | 33.62 | O |
| ATOM | 3500 | O | HOH | L | 390 | 26.340 | −3.601 | −60.202 | 1.00 | 64.75 | O |
| ATOM | 3501 | O | HOH | L | 391 | 28.129 | −25.852 | −51.071 | 1.00 | 46.50 | O |
| ATOM | 3502 | O | HOH | L | 393 | 14.154 | −7.292 | −57.036 | 1.00 | 36.09 | O |
| ATOM | 3503 | O | HOH | L | 397 | 37.422 | −20.224 | −46.867 | 1.00 | 69.67 | O |
| ATOM | 3504 | O | HOH | L | 398 | 37.165 | −35.258 | −81.376 | 1.00 | 44.63 | O |
| ATOM | 3505 | O | HOH | L | 400 | 22.752 | −7.309 | −70.576 | 1.00 | 53.33 | O |
| ATOM | 3506 | O | HOH | L | 401 | 63.020 | −10.241 | −71.323 | 1.00 | 57.90 | O |
| ATOM | 3507 | O | HOH | L | 402 | 47.411 | −48.771 | −53.710 | 1.00 | 41.80 | O |
| ATOM | 3508 | O | HOH | L | 403 | 25.259 | −18.469 | −61.248 | 1.00 | 52.14 | O |
| ATOM | 3509 | O | HOH | L | 406 | 27.197 | −40.973 | −58.632 | 1.00 | 47.94 | O |
| ATOM | 3510 | O | HOH | L | 407 | 19.218 | −2.737 | −68.050 | 1.00 | 80.35 | O |
| ATOM | 3511 | O | HOH | L | 408 | 34.045 | −37.292 | −60.300 | 1.00 | 48.46 | O |
| ATOM | 3512 | O | HOH | L | 409 | 38.079 | −14.004 | −48.990 | 1.00 | 57.05 | O |
| ATOM | 3513 | O | HOH | L | 410 | 68.493 | −23.786 | −69.129 | 1.00 | 57.46 | O |
| ATOM | 3514 | O | HOH | L | 412 | 35.863 | −27.309 | −81.341 | 1.00 | 57.62 | O |
| ATOM | 3515 | O | HOH | L | 413 | 43.397 | −38.381 | −88.954 | 1.00 | 59.21 | O |
| ATOM | 3516 | O | HOH | L | 414 | 29.038 | −25.674 | −69.827 | 1.00 | 50.18 | O |
| ATOM | 3517 | O | HOH | L | 415 | 38.214 | −20.548 | −62.410 | 1.00 | 47.80 | O |
| ATOM | 3518 | O | HOH | L | 416 | 38.066 | −58.766 | −76.704 | 1.00 | 108.60 | O |
| ATOM | 3519 | O | HOH | L | 417 | 40.397 | −19.342 | −70.694 | 1.00 | 50.29 | O |
| ATOM | 3520 | O | HOH | L | 418 | 18.178 | −21.139 | −78.978 | 1.00 | 51.89 | O |
| ATOM | 3521 | O | HOH | L | 420 | 24.201 | −9.978 | −36.105 | 1.00 | 54.93 | O |
| ATOM | 3522 | O | HOH | L | 421 | 34.155 | −34.691 | −58.438 | 1.00 | 43.66 | O |
| ATOM | 3523 | O | HOH | L | 422 | 48.926 | −11.244 | −62.863 | 1.00 | 59.34 | O |
| ATOM | 3524 | O | HOH | L | 423 | 66.056 | −32.537 | −73.870 | 1.00 | 41.33 | O |
| ATOM | 3525 | O | HOH | L | 424 | 12.775 | −11.201 | −65.750 | 1.00 | 58.59 | O |
| ATOM | 3526 | O | HOH | L | 425 | 50.865 | −34.999 | −61.675 | 1.00 | 48.86 | O |
| ATOM | 3527 | O | HOH | L | 427 | 36.098 | −18.817 | −49.819 | 1.00 | 55.72 | O |
| ATOM | 3528 | O | HOH | L | 428 | 42.444 | −11.260 | −57.047 | 1.00 | 48.82 | O |
| ATOM | 3529 | O | HOH | L | 429 | 19.126 | −4.696 | −70.541 | 1.00 | 60.29 | O |
| ATOM | 3530 | O | HOH | L | 430 | 44.422 | −20.507 | −59.266 | 1.00 | 58.82 | O |
| ATOM | 3531 | O | HOH | L | 434 | 41.488 | −44.139 | −70.800 | 1.00 | 45.75 | O |
| ATOM | 3532 | O | HOH | L | 435 | 37.748 | −20.285 | −58.136 | 1.00 | 69.72 | O |
| ATOM | 3533 | O | HOH | L | 436 | 6.736 | −37.548 | −54.063 | 1.00 | 51.47 | O |
| ATOM | 3534 | O | HOH | L | 437 | 40.302 | −20.411 | −90.763 | 1.00 | 48.84 | O |
| ATOM | 3535 | O | HOH | L | 438 | 51.936 | −14.318 | −74.016 | 1.00 | 63.98 | O |
| ATOM | 3536 | O | HOH | L | 439 | 35.775 | −42.192 | −51.221 | 1.00 | 68.50 | O |
| ATOM | 3537 | O | HOH | L | 440 | 31.059 | −22.571 | −64.147 | 1.00 | 41.43 | O |
| ATOM | 3538 | O | HOH | L | 441 | 38.952 | −22.237 | −59.564 | 1.00 | 66.15 | O |
| ATOM | 3539 | O | HOH | L | 443 | 21.653 | −21.658 | −41.663 | 1.00 | 55.01 | O |
| ATOM | 3540 | O | HOH | L | 444 | 45.934 | −37.282 | −89.854 | 1.00 | 77.52 | O |

TABLE 5-continued

Atomic coordinates for CRBN(TBD):Thalidomide (Murine protein)

| ATOM | 3541 | O | HOH | L | 445 | 49.404 | −22.222 | −95.458 | 1.00 | 46.52 | O |
|---|---|---|---|---|---|---|---|---|---|---|---|
| ATOM | 3542 | O | HOH | L | 447 | 36.141 | −17.190 | −48.065 | 1.00 | 76.63 | O |
| ATOM | 3543 | O | HOH | L | 448 | 43.357 | −8.198 | −66.460 | 1.00 | 44.89 | O |
| ATOM | 3544 | O | HOH | L | 450 | 26.356 | −38.679 | −52.157 | 1.00 | 60.56 | O |
| ATOM | 3545 | O | HOH | L | 451 | 29.155 | −44.336 | −52.040 | 1.00 | 63.24 | O |
| ATOM | 3546 | O | HOH | L | 452 | 12.995 | −12.330 | −68.262 | 1.00 | 47.16 | O |
| ATOM | 3547 | O | HOH | L | 453 | 25.708 | −7.592 | −35.823 | 1.00 | 55.17 | O |
| ATOM | 3548 | O | HOH | L | 456 | 39.290 | −48.097 | −78.072 | 1.00 | 44.75 | O |
| ATOM | 3549 | O | HOH | L | 457 | 39.633 | −46.097 | −75.983 | 1.00 | 55.61 | O |
| ATOM | 3550 | O | HOH | L | 458 | 44.789 | −55.609 | −78.400 | 1.00 | 53.98 | O |
| ATOM | 3551 | O | HOH | L | 459 | 42.624 | −5.991 | −47.762 | 1.00 | 47.34 | O |
| ATOM | 3552 | O | HOH | L | 460 | 27.298 | −19.154 | −47.330 | 1.00 | 49.15 | O |
| ATOM | 3553 | O | HOH | L | 461 | 37.021 | −18.360 | −71.526 | 1.00 | 37.33 | O |
| ATOM | 3554 | O | HOH | L | 462 | 65.590 | −31.078 | −55.377 | 1.00 | 47.85 | O |
| ATOM | 3555 | O | HOH | L | 463 | 33.060 | −15.229 | −40.224 | 1.00 | 50.46 | O |
| ATOM | 3556 | O | HOH | L | 464 | 24.892 | −20.182 | −48.125 | 1.00 | 43.16 | O |
| ATOM | 3557 | O | HOH | L | 465 | 29.460 | −41.184 | −60.394 | 1.00 | 53.06 | O |
| ATOM | 3558 | O | HOH | L | 466 | 37.928 | −19.983 | −92.336 | 1.00 | 51.84 | O |
| ATOM | 3559 | O | HOH | L | 467 | 63.218 | −10.543 | −75.851 | 1.00 | 43.94 | O |
| ATOM | 3560 | O | HOH | L | 469 | 25.231 | −42.054 | −59.855 | 1.00 | 53.14 | O |
| ATOM | 3561 | O | HOH | L | 470 | 64.008 | −10.820 | −78.548 | 1.00 | 53.06 | O |
| ATOM | 3562 | O | HOH | L | 471 | 47.546 | −40.121 | −80.753 | 1.00 | 44.37 | O |
| ATOM | 3563 | O | HOH | L | 472 | 51.031 | −40.891 | −81.788 | 1.00 | 51.25 | O |
| ATOM | 3564 | O | HOH | L | 473 | 45.074 | −43.805 | −52.942 | 1.00 | 44.56 | O |
| ATOM | 3565 | O | HOH | L | 474 | 47.261 | −42.514 | −51.929 | 1.00 | 51.34 | O |
| ATOM | 3566 | O | HOH | L | 475 | 31.206 | −27.290 | −53.325 | 1.00 | 43.72 | O |
| ATOM | 3567 | O | HOH | L | 476 | 27.504 | −20.579 | −50.009 | 1.00 | 42.93 | O |
| ATOM | 3568 | O | HOH | L | 477 | 33.038 | −20.830 | −49.848 | 1.00 | 41.85 | O |
| ATOM | 3569 | O | HOH | L | 478 | 34.566 | −17.368 | −41.666 | 1.00 | 61.85 | O |
| ATOM | 3570 | O | HOH | L | 479 | 40.793 | −8.591 | −44.126 | 1.00 | 39.32 | O |
| ATOM | 3571 | O | HOH | L | 480 | 47.451 | −25.402 | −71.374 | 1.00 | 36.75 | O |
| ATOM | 3572 | O | HOH | L | 481 | 42.703 | −22.365 | −74.608 | 1.00 | 40.31 | O |
| ATOM | 3573 | O | HOH | L | 482 | 27.821 | 0.433 | −65.034 | 1.00 | 37.12 | O |
| ATOM | 3574 | O | HOH | L | 483 | 53.711 | −35.490 | −71.518 | 1.00 | 47.76 | O |
| ATOM | 3575 | O | HOH | L | 484 | 60.386 | −43.312 | −74.062 | 1.00 | 43.55 | O |
| ATOM | 3576 | O | HOH | L | 485 | 55.953 | −28.281 | −61.541 | 1.00 | 50.31 | O |
| END | | | | | | | | | | | |

TABLE 6

Atomic coordinates for CRBN:DDB1: Compound B (Human protein)

```
HEADER      ----                                                    xx-xxx-xx xxxx
COMPND      ---
REMARK      3
REMARK      3       REFINEMENT.
REMARK      3       PROGRAM               : REFMAC 5.8.0107
REMARK      3       AUTHORS               : MURSHUDOV, SKUBAK, LEBEDEV, PANNU,
REMARK      3                               STEINER, NICHOLLS, WINN, LONG, VAGIN
REMARK      3
REMARK      3       REFINEMENT TARGET : MAXIMUM LIKELIHOOD
REMARK      3
REMARK      3       DATA USED IN REFINEMENT.
REMARK      3       RESOLUTION RANGE HIGH (ANGSTROMS)              : 3.05
REMARK      3       RESOLUTION RANGE LOW (ANGSTROMS)               : 50.01
REMARK      3       DATA CUTOFF (SIGMA(F))                         : NONE
REMARK      3       COMPLETENESS FOR RANGE (%)                     : 99.88
REMARK      3       NUMBER OF REFLECTIONS                          : 44722
REMARK      3
REMARK      3       FIT TO DATA USED IN REFINEMENT.
REMARK      3       CROSS-VALIDATION METHOD                        : THROUGHOUT
REMARK      3       FREE R VALUE TEST SET SELECTION                : RANDOM
REMARK      3       R VALUE (WORKING + TEST SET)                   : 0.19939
REMARK      3       R VALUE (WORKING SET)                          : 0.19552
REMARK      3       FREE R VALUE                                   : 0.27388
REMARK      3       FREE R VALUE TEST SET SIZE (%)                 : 5.0
REMARK      3       FREE R VALUE TEST SET COUNT                    : 2360
REMARK      3
REMARK      3       FIT IN THE HIGHEST RESOLUTION BIN.
REMARK      3       TOTAL NUMBER OF BINS USED                      : 20
REMARK      3       BIN RESOLUTION RANGE HIGH                      : 3.050
REMARK      3       BIN RESOLUTION RANGE LOW                       : 3.129
REMARK      3       REFLECTION IN BIN (WORKING SET)                : 3217
REMARK      3       BIN COMPLETENESS (WORKING + TEST) (%)          : 99.24
REMARK      3       BIN R VALUE (WORKING SET)                      : 0.338
```

TABLE 6-continued

Atomic coordinates for CRBN:DDB1: Compound B (Human protein)

| | | | | | | |
|---|---|---|---|---|---|---|
| REMARK | 3 | BIN FREE R VALUE SET COUNT | : 170 | | | |
| REMARK | 3 | BIN FREE R VALUE | : 0.367 | | | |
| REMARK | 3 | | | | | |
| REMARK | 3 | NUMBER OF NON-HYDROGEN ATOMS USED IN REFINEMENT. | | | | |
| REMARK | 3 | ALL ATOMS : 11203 | | | | |
| REMARK | 3 | | | | | |
| REMARK | 3 | B VALUES. | | | | |
| REMARK | 3 | FROM WILSON PLOT (A**2) | : NULL | | | |
| REMARK | 3 | MEAN B VALUE (OVERALL, A**2) | : 66.267 | | | |
| REMARK | 3 | OVERALL ANISOTROPIC B VALUE. | | | | |
| REMARK | 3 | B11 (A**2) : −1.58 | | | | |
| REMARK | 3 | B22 (A**2) :  0.92 | | | | |
| REMARK | 3 | B33 (A**2) :  0.66 | | | | |
| REMARK | 3 | B12 (A**2) :  0.00 | | | | |
| REMARK | 3 | B13 (A**2) :  0.00 | | | | |
| REMARK | 3 | B23 (A**2) :  0.00 | | | | |
| REMARK | 3 | | | | | |
| REMARK | 3 | ESTIMATED OVERALL COORDINATE ERROR. | | | | |
| REMARK | 3 | ESU BASED ON R VALUE (A) | | : NULL | | |
| REMARK | 3 | ESU BASED ON FREE R VALUE (A) | | : 0.425 | | |
| REMARK | 3 | ESU BASED ON MAXIMUM LIKELIHOOD (A) | | : 0.318 | | |
| REMARK | 3 | ESU FOR B VALUES BASED ON MAXIMUM LIKELIHOOD (A**2) | | : 37.619 | | |
| REMARK | 3 | | | | | |
| REMARK | 3 | CORRELATION COEFFICIENTS. | | | | |
| REMARK | 3 | CORRELATION COEFFICIENT FO-FC | : 0.932 | | | |
| REMARK | 3 | CORRELATION COEFFICIENT FO-FC FREE | : 0.889 | | | |
| REMARK | 3 | | | | | |
| REMARK | 3 | RMS DEVIATIONS FROM IDEAL VALUES | COUNT | RMS | WEIGHT | |
| REMARK | 3 | BOND LENGTHS REFINED ATOMS (A): | 11426 ; | 0.018 ; | 0.019 | |
| REMARK | 3 | BOND LENGTHS OTHERS (A): | 10793 ; | 0.002 ; | 0.020 | |
| REMARK | 3 | BOND ANGLES REFINED ATOMS (DEGREES): | 15525 ; | 2.170 ; | 1.960 | |
| REMARK | 3 | BOND ANGLES OTHERS (DEGREES): | 24721 ; | 1.198 ; | 2.998 | |
| REMARK | 3 | TORSION ANGLES, PERIOD 1 (DEGREES): | 1438 ; | 10.001 ; | 5.000 | |
| REMARK | 3 | TORSION ANGLES, PERIOD 2 (DEGREES): | 479 ; | 38.842 ; | 24.509 | |
| REMARK | 3 | TORSION ANGLES, PERIOD 3 (DEGREES): | 1885 ; | 21.358 ; | 15.000 | |
| REMARK | 3 | TORSION ANGLES, PERIOD 4 (DEGREES): | 54 ; | 21.493 ; | 15.000 | |
| REMARK | 3 | CHIRAL-CENTER RESTRAINTS (A**3): | 1806 ; | 0.120 ; | 0.200 | |
| REMARK | 3 | GENERAL PLANES REFINED ATOMS (A): | 12897 ; | 0.010 ; | 0.021 | |
| REMARK | 3 | GENERAL PLANES OTHERS (A): | 2546 ; | 0.002 ; | 0.020 | |
| REMARK | 3 | | | | | |
| REMARK | 3 | ISOTROPIC THERMAL FACTOR RESTRAINTS. | COUNT | RMS | WEIGHT | |
| REMARK | 3 | MAIN-CHAIN BOND REFINED ATOMS (A**2): | 5800 ; | 4.224 ; | 6.618 | |
| REMARK | 3 | MAIN-CHAIN BOND OTHER ATOMS (A**2): | 5799 ; | 4.220 ; | 6.618 | |
| REMARK | 3 | MAIN-CHAIN ANGLE REFINED ATOMS (A**2): | 7222 ; | 6.795 ; | 9.915 | |
| REMARK | 3 | MAIN-CHAIN ANGLE OTHER ATOMS (A**2) : | 7223 ; | 6.795 ; | 9.915 | |
| REMARK | 3 | SIDE-CHAIN BOND REFINED ATOMS (A**2): | 5626 ; | 4.335 ; | 7.005 | |
| REMARK | 3 | SIDE-CHAIN BOND OTHER ATOMS (A**2) : | 5625 ; | 4.335 ; | 7.005 | |
| REMARK | 3 | SIDE-CHAIN ANGLE OTHER ATOMS (A**2) : | 8304 ; | 7.018 ; | 10.352 | |
| REMARK | 3 | LONG RANGE B REFINED ATOMS (A**2) : | 11997 ; | 10.042 ; | 51.862 | |
| REMARK | 3 | LONG RANGE B OTHER ATOMS (A**2) : | 11998 ; | 10.042 ; | 51.863 | |
| REMARK | 3 | | | | | |
| REMARK | 3 | NCS RESTRAINTS STATISTICS | | | | |
| REMARK | 3 | NUMBER OF NCS GROUPS : NULL | | | | |
| REMARK | 3 | | | | | |
| REMARK | 3 | TWIN DETAILS | | | | |
| REMARK | 3 | NUMBER OF TWIN DOMAINS : NULL | | | | |
| REMARK | 3 | | | | | |
| REMARK | 3 | TLS DETAILS | | | | |
| REMARK | 3 | NUMBER OF TLS GROUPS : 4 | | | | |
| REMARK | 3 | ATOM RECORD CONTAINS RESIDUAL B FACTORS ONLY | | | | |
| REMARK | 3 | | | | | |
| REMARK | 3 | TLS GROUP : 1 | | | | |
| REMARK | 3 | NUMBER OF COMPONENTS GROUP : 1 | | | | |
| REMARK | 3 | COMPONENTS C SSSEQI TO C SSSEQI | | | | |
| REMARK | 3 | RESIDUE RANGE : C 249 C 500 | | | | |
| REMARK | 3 | ORIGIN FOR THE GROUP (A): 33.3654 41.9729 −41.4237 | | | | |
| REMARK | 3 | T TENSOR | | | | |
| REMARK | 3 | T11:  0.1446 | T22:  0.0795 | | | |
| REMARK | 3 | T33:  0.0393 | T12: −0.0516 | | | |
| REMARK | 3 | T13:  0.0063 | T23:  0.0170 | | | |
| REMARK | 3 | L TENSOR | | | | |
| REMARK | 3 | L11:  0.7796 | L22:  0.8042 | | | |
| REMARK | 3 | L33:  0.5164 | L12:  0.4556 | | | |
| REMARK | 3 | L13: −0.5729 | L23: −0.5351 | | | |
| REMARK | 3 | S TENSOR | | | | |
| REMARK | 3 | S11: −0.0778 | S12:  0.1035 | S13:  0.0076 | | |
| REMARK | 3 | S21:  0.0089 | S22:  0.0384 | S23: −0.0762 | | |

TABLE 6-continued

Atomic coordinates for CRBN:DDB1: Compound B (Human protein)

| | | | | | |
|---|---|---|---|---|---|
| REMARK | 3 | S31: 0.0871 | S32: −0.0718 | S33: 0.0395 | |
| REMARK | 3 | | | | |
| REMARK | 3 | TLS GROUP : 2 | | | |
| REMARK | 3 | NUMBER OF COMPONENTS GROUP : 1 | | | |
| REMARK | 3 | COMPONENTS C SSSEQI TO C SSSEQI | | | |
| REMARK | 3 | RESIDUE RANGE : C 1 C 186 | | | |
| REMARK | 3 | ORIGIN FOR THE GROUP (A): 36.5549 48.4341 −20.4615 | | | |
| REMARK | 3 | T TENSOR | | | |
| REMARK | 3 | T11: 0.1568 | T22: 0.0389 | | |
| REMARK | 3 | T33: 0.0846 | T12: −0.0032 | | |
| REMARK | 3 | T13: −0.0522 | T23: −0.0273 | | |
| REMARK | 3 | L TENSOR | | | |
| REMARK | 3 | L11: 0.8462 | L22: 0.1050 | | |
| REMARK | 3 | L33: 1.7469 | L12: 0.2400 | | |
| REMARK | 3 | L13: −0.6199 | L23: −0.3871 | | |
| REMARK | 3 | S TENSOR | | | |
| REMARK | 3 | S11: −0.0249 | S12: −0.1579 | S13: 0.1794 | |
| REMARK | 3 | S21: −0.0033 | S22: −0.0303 | S23: 0.0248 | |
| REMARK | 3 | S31: 0.0092 | S32: 0.0825 | S33: 0.0551 | |
| REMARK | 3 | | | | |
| REMARK | 3 | TLS GROUP : 3 | | | |
| REMARK | 3 | NUMBER OF COMPONENTS GROUP : 1 | | | |
| REMARK | 3 | COMPONENTS          C SSSEQI TO C SSSEQI | | | |
| REMARK | 3 | RESIDUE RANGE : A 392 A 709 | | | |
| REMARK | 3 | ORIGIN FOR THE GROUP (A): −51.9624 12.4713 −21.7463 | | | |
| REMARK | 3 | T TENSOR | | | |
| REMARK | 3 | T11: 0.1123 | T22: 0.0568 | | |
| REMARK | 3 | T33: 0.1861 | T12: 0.0446 | | |
| REMARK | 3 | T13: 0.0023 | T23: −0.0742 | | |
| REMARK | 3 | L TENSOR | | | |
| REMARK | 3 | L11: 0.9429 | L22: 0.7862 | | |
| REMARK | 3 | L33: 0.6826 | L12: −0.0382 | | |
| REMARK | 3 | L13: 0.5800 | L23: −0.1420 | | |
| REMARK | 3 | S TENSOR | | | |
| REMARK | 3 | S11: −0.2064 | S12: −0.0720 | S13: 0.1271 | |
| REMARK | 3 | S21: 0.0658 | S22: −0.0429 | S23: 0.1679 | |
| REMARK | 3 | S31: −0.0799 | S32: −0.0980 | S33: 0.2493 | |
| REMARK | 3 | | | | |
| REMARK | 3 | TLS GROUP : 4 | | | |
| REMARK | 3 | NUMBER OF COMPONENTS GROUP : 2 | | | |
| REMARK | 3 | COMPONENTS C SSSEQI TO C SSSEQI | | | |
| REMARK | 3 | RESIDUE RANGE : A 1 A 391 | | | |
| REMARK | 3 | RESIDUE RANGE : A 710 A 1200 | | | |
| REMARK | 3 | ORIGIN FOR THE GROUP (A): −1.7398 16.1076 −23.5039 | | | |
| REMARK | 3 | T TENSOR | | | |
| REMARK | 3 | T11: 0.1786 | T22: 0.0449 | | |
| REMARK | 3 | T33: 0.0159 | T12: −0.0188 | | |
| REMARK | 3 | T13: 0.0281 | T23: −0.0203 | | |
| REMARK | 3 | L TENSOR | | | |
| REMARK | 3 | L11: 0.2717 | L22: 0.3466 | | |
| REMARK | 3 | L33: 0.4327 | L12: 0.0020 | | |
| REMARK | 3 | L13: 0.0605 | L23: 0.0146 | | |
| REMARK | 3 | S TENSOR | | | |
| REMARK | 3 | S11: −0.0545 | S12: −0.0318 | S13: −0.0054 | |
| REMARK | 3 | S21: −0.0789 | S22: 0.0717 | S23: −0.0222 | |
| REMARK | 3 | S31: 0.0079 | S32: 0.0666 | S33: −0.0172 | |
| REMARK | 3 | | | | |
| REMARK | 3 | | | | |
| REMARK | 3 | BULK SOLVENT MODELLING. | | | |
| REMARK | 3 | METHOD USED : MASK | | | |
| REMARK | 3 | PARAMETERS FOR MASK CALCULATION | | | |
| REMARK | 3 | VDW PROBE RADIUS              : 1.20 | | | |
| REMARK | 3 | ION PROBE RADIUS              : 0.80 | | | |
| REMARK | 3 | SHRINKAGE RADIUS              : 0.80 | | | |
| REMARK | 3 | | | | |
| REMARK | 3 | OTHER REFINEMENT REMARKS: | | | |
| REMARK | 3 | HYDROGENS HAVE BEEN ADDED IN THE RIDING POSITIONS | | | |
| REMARK | 3 | U VALUES : RESIDUAL ONLY | | | |
| REMARK | 3 | | | | |
| LINKR | | GLN A 209 | ASN A 211 | | gap |
| LINKR | | LYS A 287 | THR A 296 | | gap |
| LINKR | | LEU A 546 | GLY A 551 | | gap |
| LINKR | | ASP A 744 | THR A 749 | | gap |
| LINKR | | LYS A 769 | GLU A 784 | | gap |
| LINKR | | ASP A 980 | GLU A 987 | | gap |
| LINKR | | MET A 1014 | THR A 1024 | | gap |
| LINKR | | THR A 1078 | LYS A 1081 | | gap |
| LINKR | | ASP A 1116 | LYS A 1121 | | gap |

TABLE 6-continued

Atomic coordinates for CRBN:DDB1: Compound B (Human protein)

| | | | | | | | | | |
|---|---|---|---|---|---|---|---|---|---|
| LINKR | | | SER C 126 | | GLU C 132 | | gap | | |
| LINKR | | | VAL C 213 | | SER C 220 | | gap | | |
| LINKR | | | ASP C 265 | | ASP C 270 | | gap | | |
| LINKR | | | ARG A 391 | | ILE A 707 | | gap | | |
| LINKR | | | ALA A 46 | | LEU A 49 | | gap | | |
| LINKR | | | GLN A 93 | | SER A 97 | | gap | | |
| LINKR | | | ASN A 337 | | GLU A 342 | | gap | | |
| LINKR | | | GLU A 368 | | GLN A 372 | | gap | | |
| LINKR | | | ARG A 391 | | LEU A 710 | | gap | | |
| LINKR | | | SER A 767 | | GLU A 784 | | gap | | |
| LINKR | | | VAL A 1013 | | THR A1024 | | gap | | |
| LINKR | | | PRO A 417 | | GLU A 420 | | gap | | |
| LINKR | | | HIS A 536 | | VAL A 538 | | gap | | |
| LINKR | | | GLU A 535 | | VAL A 538 | | gap | | |
| LINKR | | | LEU A 560 | | THR A 562 | | gap | | |
| LINKR | | | LEU A 576 | | HIS A 578 | | gap | | |
| LINKR | | | GLY A 584 | | ILE A 586 | | gap | | |
| LINKR | | | SER A 643 | | SER A 645 | | gap | | |
| LINKR | | | SER A 661 | | ASN A 663 | | gap | | |
| LINKR | | | ASP A 625 | | LYS A 627 | | gap | | |
| LINKR | | | ASP C 265 | | SER C 272 | | gap | | |
| LINKR | | | THR C 172 | | GLY C 176 | | gap | | |
| SSBOND | | 1 | CYS A 18 | | CYS A 313 | | | | |
| SSBOND | | 2 | CYS C 323 | | CYS C 326 | | | | |
| SSBOND | | 3 | CYS C 326 | | CYS C 391 | | | | |
| SSBOND | | 4 | CYS C 326 | | CYS C 394 | | | | |
| CRYST1 | 111.029 | | 126.886 | 172.487 | 90.00 | 90.00 | 90.00 P 21 | 21 21 | |
| SCALE1 | 0.009007 | | 0.000000 | 0.000000 | 0.00000 | | | | |
| SCALE2 | 0.000000 | | 0.007881 | 0.000000 | 0.00000 | | | | |
| SCALE3 | 0.000000 | | 0.000000 | 0.005798 | 0.00000 | | | | |
| ATOM | 1 | N | SER A | 2 | −10.005 | 42.968 | −18.390 | 1.00 | 84.59 N |
| ATOM | 2 | CA | SER A | 2 | −10.680 | 41.660 | −18.759 | 1.00 | 84.02 C |
| ATOM | 3 | CB | SER A | 2 | −10.098 | 40.978 | −20.050 | 1.00 | 80.59 C |
| ATOM | 4 | OG | SER A | 2 | −11.107 | 40.512 | −20.977 | 1.00 | 68.86 O |
| ATOM | 5 | C | SER A | 2 | −10.680 | 40.705 | −17.540 | 1.00 | 77.34 C |
| ATOM | 6 | O | SER A | 2 | −9.765 | 40.653 | −16.724 | 1.00 | 68.49 O |
| ATOM | 7 | N | TYR A | 3 | −11.782 | 39.985 | −17.463 | 1.00 | 73.95 N |
| ATOM | 8 | CA | TYR A | 3 | −12.165 | 39.195 | −16.352 | 1.00 | 68.46 C |
| ATOM | 9 | CB | TYR A | 3 | −13.255 | 39.929 | −15.615 | 1.00 | 71.81 C |
| ATOM | 10 | CG | TYR A | 3 | −12.847 | 41.291 | −15.165 | 1.00 | 75.50 C |
| ATOM | 11 | CD1 | TYR A | 3 | −11.744 | 41.461 | −14.330 | 1.00 | 78.09 C |
| ATOM | 12 | CE1 | TYR A | 3 | −11.378 | 42.721 | −13.905 | 1.00 | 83.18 C |
| ATOM | 13 | CZ | TYR A | 3 | −12.115 | 43.828 | −14.324 | 1.00 | 81.80 C |
| ATOM | 14 | OH | TYR A | 3 | −11.784 | 45.088 | −13.895 | 1.00 | 83.08 O |
| ATOM | 15 | CE2 | TYR A | 3 | −13.209 | 43.673 | −15.145 | 1.00 | 78.84 C |
| ATOM | 16 | CD2 | TYR A | 3 | −13.573 | 42.412 | −15.554 | 1.00 | 76.19 C |
| ATOM | 17 | C | TYR A | 3 | −12.734 | 37.917 | −16.932 | 1.00 | 61.62 C |
| ATOM | 18 | O | TYR A | 3 | −13.895 | 37.851 | −17.355 | 1.00 | 52.94 O |
| ATOM | 19 | N | ASN A | 4 | −11.902 | 36.901 | −16.976 | 1.00 | 57.85 N |
| ATOM | 20 | CA | ASN A | 4 | −12.321 | 35.666 | −17.563 | 1.00 | 55.67 C |
| ATOM | 21 | CB | ASN A | 4 | −11.317 | 35.325 | −18.628 | 1.00 | 57.30 C |
| ATOM | 22 | CG | ASN A | 4 | −11.151 | 36.492 | −19.603 | 1.00 | 62.49 C |
| ATOM | 23 | OD1 | ASN A | 4 | −12.040 | 36.782 | −20.436 | 1.00 | 66.61 O |
| ATOM | 24 | ND2 | ASN A | 4 | −10.050 | 37.214 | −19.457 | 1.00 | 64.50 N |
| ATOM | 25 | C | ASN A | 4 | −12.599 | 34.578 | −16.529 | 1.00 | 52.23 C |
| ATOM | 26 | O | ASN A | 4 | −12.102 | 34.646 | −15.364 | 1.00 | 48.64 O |
| ATOM | 27 | N | TYR A | 5 | −13.485 | 33.653 | −16.949 | 1.00 | 49.26 N |
| ATOM | 28 | CA | TYR A | 5 | −13.885 | 32.446 | −16.211 | 1.00 | 46.57 C |
| ATOM | 29 | CB | TYR A | 5 | −15.356 | 32.526 | −16.020 | 1.00 | 42.94 C |
| ATOM | 30 | CG | TYR A | 5 | −16.033 | 31.410 | −15.286 | 1.00 | 45.14 C |
| ATOM | 31 | CD1 | TYR A | 5 | −16.548 | 30.337 | −15.963 | 1.00 | 47.98 C |
| ATOM | 32 | CE1 | TYR A | 5 | −17.264 | 29.328 | −15.291 | 1.00 | 50.62 C |
| ATOM | 33 | CZ | TYR A | 5 | −17.487 | 29.396 | −13.934 | 1.00 | 47.26 C |
| ATOM | 34 | OH | TYR A | 5 | −18.186 | 28.367 | −13.354 | 1.00 | 48.08 O |
| ATOM | 35 | CE2 | TYR A | 5 | −16.990 | 30.463 | −13.235 | 1.00 | 45.13 C |
| ATOM | 36 | CD2 | TYR A | 5 | −16.268 | 31.466 | −13.911 | 1.00 | 45.20 C |
| ATOM | 37 | C | TYR A | 5 | −13.508 | 31.200 | −17.040 | 1.00 | 47.62 C |
| ATOM | 38 | O | TYR A | 5 | −13.928 | 31.103 | −18.188 | 1.00 | 47.74 O |
| ATOM | 39 | N | VAL A | 6 | −12.673 | 30.293 | −16.495 | 1.00 | 48.08 N |
| ATOM | 40 | CA | VAL A | 6 | −12.357 | 29.004 | −17.167 | 1.00 | 46.07 C |
| ATOM | 41 | CB | VAL A | 6 | −10.878 | 28.681 | −17.307 | 1.00 | 44.74 C |
| ATOM | 42 | CG1 | VAL A | 6 | −10.662 | 27.785 | −18.497 | 1.00 | 43.45 C |
| ATOM | 43 | CG2 | VAL A | 6 | −10.111 | 29.929 | −17.495 | 1.00 | 49.07 C |
| ATOM | 44 | C | VAL A | 6 | −12.848 | 27.813 | −16.404 | 1.00 | 46.12 C |
| ATOM | 45 | O | VAL A | 6 | −12.553 | 27.621 | −15.205 | 1.00 | 48.25 O |
| ATOM | 46 | N | VAL A | 7 | −13.448 | 26.934 | −17.175 | 1.00 | 44.72 N |
| ATOM | 47 | CA | VAL A | 7 | −14.034 | 25.743 | −16.655 | 1.00 | 44.24 C |
| ATOM | 48 | CB | VAL A | 7 | −15.521 | 25.973 | −16.450 | 1.00 | 45.37 C |

TABLE 6-continued

Atomic coordinates for CRBN:DDB1: Compound B (Human protein)

| ATOM | 49 | CG1 | VAL A | 7 | −16.233 | 26.282 | −17.781 | 1.00 | 45.99 | C |
|---|---|---|---|---|---|---|---|---|---|---|
| ATOM | 50 | CG2 | VAL A | 7 | −16.140 | 24.770 | −15.768 | 1.00 | 45.70 | C |
| ATOM | 51 | C | VAL A | 7 | −13.828 | 24.547 | −17.595 | 1.00 | 41.83 | C |
| ATOM | 52 | O | VAL A | 7 | −13.747 | 24.688 | −18.845 | 1.00 | 37.16 | O |
| ATOM | 53 | N | THR A | 8 | −13.779 | 23.380 | −16.961 | 1.00 | 37.39 | N |
| ATOM | 54 | CA | THR A | 8 | −13.697 | 22.157 | −17.662 | 1.00 | 35.46 | C |
| ATOM | 55 | CB | THR A | 8 | −13.181 | 21.093 | −16.748 | 1.00 | 36.27 | C |
| ATOM | 56 | OG1 | THR A | 8 | −11.813 | 21.332 | −16.485 | 1.00 | 34.13 | O |
| ATOM | 57 | CG2 | THR A | 8 | −13.309 | 19.719 | −17.392 | 1.00 | 39.98 | C |
| ATOM | 58 | C | THR A | 8 | −15.048 | 21.721 | −18.163 | 1.00 | 35.87 | C |
| ATOM | 59 | O | THR A | 8 | −15.974 | 21.614 | −17.435 | 1.00 | 39.59 | O |
| ATOM | 60 | N | ALA A | 9 | −15.145 | 21.437 | −19.440 | 1.00 | 37.76 | N |
| ATOM | 61 | CA | ALA A | 9 | −16.332 | 20.833 | −20.020 | 1.00 | 35.23 | C |
| ATOM | 62 | CB | ALA A | 9 | −16.547 | 21.348 | −21.430 | 1.00 | 35.30 | C |
| ATOM | 63 | C | ALA A | 9 | −16.129 | 19.360 | −20.066 | 1.00 | 35.17 | C |
| ATOM | 64 | O | ALA A | 9 | −17.093 | 18.630 | −20.056 | 1.00 | 34.48 | O |
| ATOM | 65 | N | GLN A | 10 | −14.886 | 18.916 | −20.217 | 1.00 | 35.76 | N |
| ATOM | 66 | CA | GLN A | 10 | −14.626 | 17.509 | −20.344 | 1.00 | 37.64 | C |
| ATOM | 67 | CB | GLN A | 10 | −14.782 | 17.125 | −21.811 | 1.00 | 39.11 | C |
| ATOM | 68 | CG | GLN A | 10 | −14.144 | 15.810 | −22.211 | 1.00 | 40.34 | C |
| ATOM | 69 | CD | GLN A | 10 | −14.767 | 14.636 | −21.506 | 1.00 | 41.11 | C |
| ATOM | 70 | OE1 | GLN A | 10 | −15.990 | 14.462 | −21.537 | 1.00 | 42.09 | O |
| ATOM | 71 | NE2 | GLN A | 10 | −13.938 | 13.816 | −20.881 | 1.00 | 39.93 | N |
| ATOM | 72 | C | GLN A | 10 | −13.255 | 17.204 | −19.825 | 1.00 | 36.43 | C |
| ATOM | 73 | O | GLN A | 10 | −12.280 | 17.662 | −20.376 | 1.00 | 36.13 | O |
| ATOM | 74 | N | LYS A | 11 | −13.180 | 16.398 | −18.778 | 1.00 | 37.80 | N |
| ATOM | 75 | CA | LYS A | 11 | −11.900 | 16.197 | −18.065 | 1.00 | 38.32 | C |
| ATOM | 76 | CB | LYS A | 11 | −12.082 | 15.375 | −16.800 | 1.00 | 39.91 | C |
| ATOM | 77 | CG | LYS A | 11 | −13.334 | 15.538 | −15.953 | 1.00 | 40.69 | C |
| ATOM | 78 | CD | LYS A | 11 | −13.025 | 14.736 | −14.700 | 1.00 | 43.83 | C |
| ATOM | 79 | CE | LYS A | 11 | −14.176 | 14.656 | −13.730 | 1.00 | 48.32 | C |
| ATOM | 80 | NZ | LYS A | 11 | −13.924 | 13.619 | −12.717 | 1.00 | 49.18 | N |
| ATOM | 81 | C | LYS A | 11 | −10.941 | 15.413 | −18.953 | 1.00 | 37.06 | C |
| ATOM | 82 | O | LYS A | 11 | −11.377 | 14.631 | −19.798 | 1.00 | 38.42 | O |
| ATOM | 83 | N | PRO A | 12 | −9.650 | 15.571 | −18.760 | 1.00 | 33.78 | N |
| ATOM | 84 | CA | PRO A | 12 | −8.765 | 14.870 | −19.653 | 1.00 | 35.08 | C |
| ATOM | 85 | CB | PRO A | 12 | −7.406 | 15.212 | −19.113 | 1.00 | 34.44 | C |
| ATOM | 86 | CG | PRO A | 12 | −7.647 | 15.285 | −17.680 | 1.00 | 34.64 | C |
| ATOM | 87 | CD | PRO A | 12 | −8.971 | 15.938 | −17.541 | 1.00 | 34.11 | C |
| ATOM | 88 | C | PRO A | 12 | −8.943 | 13.367 | −19.615 | 1.00 | 36.15 | C |
| ATOM | 89 | O | PRO A | 12 | −9.142 | 12.778 | −18.521 | 1.00 | 37.55 | O |
| ATOM | 90 | N | THR A | 13 | −8.896 | 12.773 | −20.811 | 1.00 | 36.27 | N |
| ATOM | 91 | CA | THR A | 13 | −9.132 | 11.333 | −21.018 | 1.00 | 35.76 | C |
| ATOM | 92 | CB | THR A | 13 | −10.047 | 11.109 | −22.200 | 1.00 | 35.92 | C |
| ATOM | 93 | OG1 | THR A | 13 | −9.438 | 11.700 | −23.355 | 1.00 | 38.97 | O |
| ATOM | 94 | CG2 | THR A | 13 | −11.418 | 11.772 | −21.974 | 1.00 | 34.88 | C |
| ATOM | 95 | C | THR A | 13 | −7.886 | 10.543 | −21.275 | 1.00 | 35.29 | C |
| ATOM | 96 | O | THR A | 13 | −7.846 | 9.386 | −20.994 | 1.00 | 39.16 | O |
| ATOM | 97 | N | ALA A | 14 | −6.869 | 11.140 | −21.843 | 1.00 | 36.74 | N |
| ATOM | 98 | CA | ALA A | 14 | −5.603 | 10.442 | −22.029 | 1.00 | 39.22 | C |
| ATOM | 99 | CB | ALA A | 14 | −4.619 | 11.411 | −22.649 | 1.00 | 41.48 | C |
| ATOM | 100 | C | ALA A | 14 | −4.984 | 9.855 | −20.758 | 1.00 | 38.94 | C |
| ATOM | 101 | O | ALA A | 14 | −4.860 | 10.531 | −19.765 | 1.00 | 44.16 | O |
| ATOM | 102 | N | VAL A | 15 | −4.539 | 8.619 | −20.813 | 1.00 | 38.42 | N |
| ATOM | 103 | CA | VAL A | 15 | −3.978 | 7.954 | −19.642 | 1.00 | 37.06 | C |
| ATOM | 104 | CB | VAL A | 15 | −4.170 | 6.429 | −19.693 | 1.00 | 35.55 | C |
| ATOM | 105 | CG1 | VAL A | 15 | −3.238 | 5.738 | −18.714 | 1.00 | 36.66 | C |
| ATOM | 106 | CG2 | VAL A | 15 | −5.609 | 6.057 | −19.376 | 1.00 | 34.82 | C |
| ATOM | 107 | C | VAL A | 15 | −2.523 | 8.166 | −19.687 | 1.00 | 37.80 | C |
| ATOM | 108 | O | VAL A | 15 | −1.949 | 7.979 | −20.693 | 1.00 | 40.33 | O |
| ATOM | 109 | N | ASN A | 16 | −1.903 | 8.452 | −18.566 | 1.00 | 40.97 | N |
| ATOM | 110 | CA | ASN A | 16 | −0.459 | 8.573 | −18.515 | 1.00 | 40.13 | C |
| ATOM | 111 | CB | ASN A | 16 | −0.080 | 10.056 | −18.431 | 1.00 | 44.35 | C |
| ATOM | 112 | CG | ASN A | 16 | −0.672 | 10.772 | −17.225 | 1.00 | 44.80 | C |
| ATOM | 113 | OD1 | ASN A | 16 | −1.826 | 11.218 | −17.240 | 1.00 | 51.01 | O |
| ATOM | 114 | ND2 | ASN A | 16 | 0.123 | 10.923 | −16.208 | 1.00 | 42.58 | N |
| ATOM | 115 | C | ASN A | 16 | 0.189 | 7.791 | −17.406 | 1.00 | 37.75 | C |
| ATOM | 116 | O | ASN A | 16 | 1.364 | 7.857 | −17.258 | 1.00 | 37.18 | O |
| ATOM | 117 | N | GLY A | 17 | −0.548 | 7.033 | −16.624 | 1.00 | 38.59 | N |
| ATOM | 118 | CA | GLY A | 17 | 0.087 | 6.065 | −15.710 | 1.00 | 39.54 | C |
| ATOM | 119 | C | GLY A | 17 | −0.914 | 5.038 | −15.268 | 1.00 | 38.90 | C |
| ATOM | 120 | O | GLY A | 17 | −2.124 | 5.259 | −15.266 | 1.00 | 38.60 | O |
| ATOM | 121 | N | CYS A | 18 | −0.433 | 3.880 | −14.930 | 1.00 | 40.51 | N |
| ATOM | 122 | CA | CYS A | 18 | −1.355 | 2.813 | −14.554 | 1.00 | 43.49 | C |
| ATOM | 123 | CB | CYS A | 18 | −1.912 | 2.059 | −15.775 | 1.00 | 43.52 | C |
| ATOM | 124 | SG | CYS A | 18 | −0.742 | 1.558 | −17.087 | 1.00 | 53.82 | S |
| ATOM | 125 | C | CYS A | 18 | −0.555 | 1.948 | −13.633 | 1.00 | 45.19 | C |
| ATOM | 126 | O | CYS A | 18 | 0.468 | 1.435 | −14.030 | 1.00 | 51.75 | O |

TABLE 6-continued

Atomic coordinates for CRBN:DDB1: Compound B (Human protein)

| ATOM | 127 | N | VAL A | 19 | −0.935 | 1.857 | −12.376 | 1.00 | 44.40 | N |
|---|---|---|---|---|---|---|---|---|---|---|
| ATOM | 128 | CA | VAL A | 19 | −0.222 | 0.975 | −11.487 | 1.00 | 46.98 | C |
| ATOM | 129 | CB | VAL A | 19 | 0.442 | 1.843 | −10.440 | 1.00 | 49.42 | C |
| ATOM | 130 | CG1 | VAL A | 19 | −0.443 | 1.981 | −9.210 | 1.00 | 49.10 | C |
| ATOM | 131 | CG2 | VAL A | 19 | 1.807 | 1.292 | −10.093 | 1.00 | 55.84 | C |
| ATOM | 132 | C | VAL A | 19 | −1.191 | −0.066 | −10.899 | 1.00 | 45.76 | C |
| ATOM | 133 | O | VAL A | 19 | −2.410 | 0.162 | −10.916 | 1.00 | 45.49 | O |
| ATOM | 134 | N | THR A | 20 | −0.697 | −1.208 | −10.410 | 1.00 | 44.39 | N |
| ATOM | 135 | CA | THR A | 20 | −1.601 | −2.080 | −9.551 | 1.00 | 44.15 | C |
| ATOM | 136 | CB | THR A | 20 | −2.044 | −3.444 | −10.140 | 1.00 | 42.52 | C |
| ATOM | 137 | OG1 | THR A | 20 | −0.967 | −4.068 | −10.840 | 1.00 | 39.92 | O |
| ATOM | 138 | CG2 | THR A | 20 | −3.189 | −3.226 | −11.085 | 1.00 | 44.71 | C |
| ATOM | 139 | C | THR A | 20 | −1.061 | −2.356 | −8.205 | 1.00 | 42.58 | C |
| ATOM | 140 | O | THR A | 20 | 0.111 | −2.109 | −7.950 | 1.00 | 39.44 | O |
| ATOM | 141 | N | GLY A | 21 | −1.938 | −2.804 | −7.323 | 1.00 | 45.46 | N |
| ATOM | 142 | CA | GLY A | 21 | −1.585 | −3.083 | −5.956 | 1.00 | 50.92 | C |
| ATOM | 143 | C | GLY A | 21 | −2.814 | −3.159 | −5.090 | 1.00 | 54.49 | C |
| ATOM | 144 | O | GLY A | 21 | −3.915 | −3.221 | −5.593 | 1.00 | 54.79 | O |
| ATOM | 145 | N | HIS A | 22 | −2.617 | −3.163 | −3.782 | 1.00 | 55.62 | N |
| ATOM | 146 | CA | HIS A | 22 | −3.710 | −3.223 | −2.841 | 1.00 | 57.07 | C |
| ATOM | 147 | CB | HIS A | 22 | −3.482 | −4.417 | −1.959 | 1.00 | 56.33 | C |
| ATOM | 148 | CG | HIS A | 22 | −3.095 | −5.633 | −2.728 | 1.00 | 57.50 | C |
| ATOM | 149 | ND1 | HIS A | 22 | −1.791 | −5.926 | −3.038 | 1.00 | 55.59 | N |
| ATOM | 150 | CE1 | HIS A | 22 | −1.748 | −7.037 | −3.742 | 1.00 | 57.44 | C |
| ATOM | 151 | NE2 | HIS A | 22 | −2.980 | −7.471 | −3.905 | 1.00 | 61.30 | N |
| ATOM | 152 | CD2 | HIS A | 22 | −3.843 | −6.606 | −3.288 | 1.00 | 57.01 | C |
| ATOM | 153 | C | HIS A | 22 | −3.692 | −1.944 | −2.056 | 1.00 | 61.31 | C |
| ATOM | 154 | O | HIS A | 22 | −2.839 | −1.736 | −1.215 | 1.00 | 67.92 | O |
| ATOM | 155 | N | PHE A | 23 | −4.662 | −1.099 | −2.361 | 1.00 | 57.84 | N |
| ATOM | 156 | CA | PHE A | 23 | −4.797 | 0.229 | −1.826 | 1.00 | 54.40 | C |
| ATOM | 157 | CB | PHE A | 23 | −4.869 | 1.125 | −3.052 | 1.00 | 51.67 | C |
| ATOM | 158 | CG | PHE A | 23 | −4.812 | 2.580 | −2.776 | 1.00 | 47.77 | C |
| ATOM | 159 | CD1 | PHE A | 23 | −3.777 | 3.123 | −2.088 | 1.00 | 51.37 | C |
| ATOM | 160 | CE1 | PHE A | 23 | −3.722 | 4.468 | −1.858 | 1.00 | 50.75 | C |
| ATOM | 161 | CZ | PHE A | 23 | −4.696 | 5.278 | −2.345 | 1.00 | 47.09 | C |
| ATOM | 162 | CE2 | PHE A | 23 | −5.721 | 4.745 | −3.049 | 1.00 | 47.31 | C |
| ATOM | 163 | CD2 | PHE A | 23 | −5.767 | 3.403 | −3.270 | 1.00 | 46.08 | C |
| ATOM | 164 | C | PHE A | 23 | −6.041 | 0.411 | −1.008 | 1.00 | 54.06 | C |
| ATOM | 165 | O | PHE A | 23 | −6.023 | 0.981 | 0.057 | 1.00 | 57.62 | O |
| ATOM | 166 | N | THR A | 24 | −7.133 | −0.075 | −1.549 | 1.00 | 51.51 | N |
| ATOM | 167 | CA | THR A | 24 | −8.451 | 0.016 | −0.928 | 1.00 | 54.42 | C |
| ATOM | 168 | CB | THR A | 24 | −9.599 | −0.360 | −1.883 | 1.00 | 53.56 | C |
| ATOM | 169 | OG1 | THR A | 24 | −9.423 | −1.679 | −2.375 | 1.00 | 54.48 | O |
| ATOM | 170 | CG2 | THR A | 24 | −9.678 | 0.544 | −3.051 | 1.00 | 55.64 | C |
| ATOM | 171 | C | THR A | 24 | −8.560 | −0.915 | 0.278 | 1.00 | 61.90 | C |
| ATOM | 172 | O | THR A | 24 | −9.071 | −0.526 | 1.326 | 1.00 | 66.84 | O |
| ATOM | 173 | N | SER A | 25 | −8.104 | −2.153 | 0.105 | 1.00 | 63.86 | N |
| ATOM | 174 | CA | SER A | 25 | −7.987 | −3.120 | 1.185 | 1.00 | 59.57 | C |
| ATOM | 175 | CB | SER A | 25 | −9.259 | −3.978 | 1.256 | 1.00 | 57.48 | C |
| ATOM | 176 | OG | SER A | 25 | −9.060 | −5.284 | 0.771 | 1.00 | 56.66 | O |
| ATOM | 177 | C | SER A | 25 | −6.758 | −3.940 | 0.865 | 1.00 | 59.31 | C |
| ATOM | 178 | O | SER A | 25 | −6.319 | −3.878 | −0.257 | 1.00 | 64.84 | O |
| ATOM | 179 | N | ALA A | 26 | −6.184 | −4.682 | 1.817 | 1.00 | 60.38 | N |
| ATOM | 180 | CA | ALA A | 26 | −5.119 | −5.672 | 1.477 | 1.00 | 58.27 | C |
| ATOM | 181 | CB | ALA A | 26 | −4.361 | −6.142 | 2.701 | 1.00 | 57.76 | C |
| ATOM | 182 | C | ALA A | 26 | −5.694 | −6.869 | 0.756 | 1.00 | 56.16 | C |
| ATOM | 183 | O | ALA A | 26 | −5.011 | −7.471 | −0.053 | 1.00 | 50.43 | O |
| ATOM | 184 | N | GLU A | 27 | −6.943 | −7.207 | 1.089 | 1.00 | 59.21 | N |
| ATOM | 185 | CA | GLU A | 27 | −7.636 | −8.367 | 0.545 | 1.00 | 60.96 | C |
| ATOM | 186 | CB | GLU A | 27 | −8.688 | −8.896 | 1.592 | 1.00 | 56.04 | C |
| ATOM | 187 | C | GLU A | 27 | −8.151 | −8.053 | −0.927 | 1.00 | 62.67 | C |
| ATOM | 188 | O | GLU A | 27 | −8.305 | −8.966 | −1.725 | 1.00 | 64.25 | O |
| ATOM | 189 | N | ASP A | 28 | −8.322 | −6.769 | −1.295 | 1.00 | 68.07 | N |
| ATOM | 190 | CA | ASP A | 28 | −8.676 | −6.296 | −2.696 | 1.00 | 64.97 | C |
| ATOM | 191 | CB | ASP A | 28 | −9.342 | −4.896 | −2.655 | 1.00 | 70.98 | C |
| ATOM | 192 | CG | ASP A | 28 | −10.809 | −4.909 | −2.160 | 1.00 | 81.59 | C |
| ATOM | 193 | OD1 | ASP A | 28 | −11.519 | −5.936 | −2.365 | 1.00 | 88.28 | O |
| ATOM | 194 | OD2 | ASP A | 28 | −11.257 | −3.860 | −1.592 | 1.00 | 82.95 | O |
| ATOM | 195 | C | ASP A | 28 | −7.490 | −6.101 | −3.649 | 1.00 | 59.18 | C |
| ATOM | 196 | O | ASP A | 28 | −6.414 | −5.701 | −3.223 | 1.00 | 56.48 | O |
| ATOM | 197 | N | LEU A | 29 | −7.707 | −6.324 | −4.947 | 1.00 | 56.71 | N |
| ATOM | 198 | CA | LEU A | 29 | −6.738 | −5.920 | −5.998 | 1.00 | 57.16 | C |
| ATOM | 199 | CB | LEU A | 29 | −6.425 | −7.079 | −6.947 | 1.00 | 57.01 | C |
| ATOM | 200 | CG | LEU A | 29 | −5.559 | −6.793 | −8.210 | 1.00 | 58.50 | C |
| ATOM | 201 | CD1 | LEU A | 29 | −4.074 | −6.769 | −7.858 | 1.00 | 59.51 | C |
| ATOM | 202 | CD2 | LEU A | 29 | −5.806 | −7.767 | −9.360 | 1.00 | 57.56 | C |
| ATOM | 203 | C | LEU A | 29 | −7.229 | −4.683 | −6.823 | 1.00 | 58.74 | C |
| ATOM | 204 | O | LEU A | 29 | −8.267 | −4.728 | −7.521 | 1.00 | 63.17 | O |

TABLE 6-continued

Atomic coordinates for CRBN:DDB1: Compound B (Human protein)

| ATOM | 205 | N | ASN A | 30 | −6.466 | −3.614 | −6.815 | 1.00 | 53.74 | N |
|---|---|---|---|---|---|---|---|---|---|---|
| ATOM | 206 | CA | ASN A | 30 | −6.923 | −2.502 | −7.588 | 1.00 | 51.53 | C |
| ATOM | 207 | CB | ASN A | 30 | −7.267 | −1.274 | −6.739 | 1.00 | 49.39 | C |
| ATOM | 208 | CG | ASN A | 30 | −7.347 | −1.560 | −5.277 | 1.00 | 48.46 | C |
| ATOM | 209 | OD1 | ASN A | 30 | −6.392 | −1.988 | −4.688 | 1.00 | 46.09 | O |
| ATOM | 210 | ND2 | ASN A | 30 | −8.476 | −1.293 | −4.684 | 1.00 | 47.58 | N |
| ATOM | 211 | C | ASN A | 30 | −5.965 | −2.055 | −8.636 | 1.00 | 53.94 | C |
| ATOM | 212 | O | ASN A | 30 | −4.783 | −2.276 | −8.564 | 1.00 | 54.39 | O |
| ATOM | 213 | N | LEU A | 31 | −6.558 | −1.431 | −9.629 | 1.00 | 54.06 | N |
| ATOM | 214 | CA | LEU A | 31 | −5.914 | −0.716 | −10.755 | 1.00 | 50.28 | C |
| ATOM | 215 | CB | LEU A | 31 | −6.591 | −1.108 | −12.074 | 1.00 | 47.02 | C |
| ATOM | 216 | CG | LEU A | 31 | −6.142 | −0.333 | −13.309 | 1.00 | 47.50 | C |
| ATOM | 217 | CD1 | LEU A | 31 | −4.646 | −0.514 | −13.546 | 1.00 | 48.13 | C |
| ATOM | 218 | CD2 | LEU A | 31 | −6.940 | −0.767 | −14.512 | 1.00 | 46.65 | C |
| ATOM | 219 | C | LEU A | 31 | −6.067 | 0.822 | −10.507 | 1.00 | 48.29 | C |
| ATOM | 220 | O | LEU A | 31 | −7.167 | 1.312 | −10.426 | 1.00 | 47.24 | O |
| ATOM | 221 | N | LEU A | 32 | −4.976 | 1.557 | −10.356 | 1.00 | 45.68 | N |
| ATOM | 222 | CA | LEU A | 32 | −5.051 | 3.001 | −10.249 | 1.00 | 46.81 | C |
| ATOM | 223 | CB | LEU A | 32 | −4.159 | 3.518 | −9.118 | 1.00 | 46.95 | C |
| ATOM | 224 | CG | LEU A | 32 | −4.677 | 3.443 | −7.694 | 1.00 | 44.05 | C |
| ATOM | 225 | CD1 | LEU A | 32 | −5.199 | 2.070 | −7.389 | 1.00 | 45.61 | C |
| ATOM | 226 | CD2 | LEU A | 32 | −3.514 | 3.750 | −6.808 | 1.00 | 43.43 | C |
| ATOM | 227 | C | LEU A | 32 | −4.572 | 3.587 | −11.562 | 1.00 | 47.78 | C |
| ATOM | 228 | O | LEU A | 32 | −3.585 | 3.109 | −12.116 | 1.00 | 49.17 | O |
| ATOM | 229 | N | ILE A | 33 | −5.249 | 4.632 | −12.032 | 1.00 | 45.97 | N |
| ATOM | 230 | CA | ILE A | 33 | −4.977 | 5.205 | −13.323 | 1.00 | 43.78 | C |
| ATOM | 231 | CB | ILE A | 33 | −6.131 | 4.975 | −14.290 | 1.00 | 43.88 | C |
| ATOM | 232 | CG1 | ILE A | 33 | −6.379 | 3.515 | −14.465 | 1.00 | 44.63 | C |
| ATOM | 233 | CD1 | ILE A | 33 | −7.532 | 3.296 | −15.405 | 1.00 | 46.56 | C |
| ATOM | 234 | CG2 | ILE A | 33 | −5.817 | 5.491 | −15.686 | 1.00 | 44.67 | C |
| ATOM | 235 | C | ILE A | 33 | −4.863 | 6.684 | −13.170 | 1.00 | 43.69 | C |
| ATOM | 236 | O | ILE A | 33 | −5.692 | 7.316 | −12.535 | 1.00 | 46.07 | O |
| ATOM | 237 | N | ALA A | 34 | −3.892 | 7.257 | −13.842 | 1.00 | 42.80 | N |
| ATOM | 238 | CA | ALA A | 34 | −3.683 | 8.674 | −13.817 | 1.00 | 44.29 | C |
| ATOM | 239 | CB | ALA A | 34 | −2.251 | 8.957 | −13.479 | 1.00 | 46.42 | C |
| ATOM | 240 | C | ALA A | 34 | −4.018 | 9.293 | −15.151 | 1.00 | 45.93 | C |
| ATOM | 241 | O | ALA A | 34 | −3.613 | 8.820 | −16.171 | 1.00 | 48.30 | O |
| ATOM | 242 | N | LYS A | 35 | −4.771 | 10.368 | −15.133 | 1.00 | 43.83 | N |
| ATOM | 243 | CA | LYS A | 35 | −5.129 | 11.050 | −16.337 | 1.00 | 40.65 | C |
| ATOM | 244 | CB | LYS A | 35 | −6.599 | 10.877 | −16.577 | 1.00 | 40.87 | C |
| ATOM | 245 | CG | LYS A | 35 | −6.978 | 9.473 | −16.930 | 1.00 | 43.41 | C |
| ATOM | 246 | CD | LYS A | 35 | −8.446 | 9.434 | −17.230 | 1.00 | 45.09 | C |
| ATOM | 247 | CE | LYS A | 35 | −8.926 | 8.056 | −17.569 | 1.00 | 45.60 | C |
| ATOM | 248 | NZ | LYS A | 35 | −10.335 | 8.139 | −18.004 | 1.00 | 47.53 | N |
| ATOM | 249 | C | LYS A | 35 | −4.799 | 12.493 | −16.092 | 1.00 | 40.40 | C |
| ATOM | 250 | O | LYS A | 35 | −5.659 | 13.324 | −15.964 | 1.00 | 42.60 | O |
| ATOM | 251 | N | ASN A | 36 | −3.519 | 12.787 | −16.035 | 1.00 | 37.09 | N |
| ATOM | 252 | CA | ASN A | 36 | −3.093 | 14.127 | −15.763 | 1.00 | 36.27 | C |
| ATOM | 253 | CB | ASN A | 36 | −3.755 | 15.081 | −16.727 | 1.00 | 35.86 | C |
| ATOM | 254 | CG | ASN A | 36 | −3.013 | 16.362 | −16.848 | 1.00 | 37.24 | C |
| ATOM | 255 | OD1 | ASN A | 36 | −1.909 | 16.476 | −16.379 | 1.00 | 37.08 | O |
| ATOM | 256 | ND2 | ASN A | 36 | −3.616 | 17.329 | −17.481 | 1.00 | 37.78 | N |
| ATOM | 257 | C | ASN A | 36 | −3.400 | 14.481 | −14.329 | 1.00 | 37.89 | C |
| ATOM | 258 | O | ASN A | 36 | −2.707 | 14.054 | −13.445 | 1.00 | 40.16 | O |
| ATOM | 259 | N | THR A | 37 | −4.417 | 15.293 | −14.106 | 1.00 | 38.17 | N |
| ATOM | 260 | CA | THR A | 37 | −4.806 | 15.738 | −12.798 | 1.00 | 40.11 | C |
| ATOM | 261 | CB | THR A | 37 | −5.428 | 17.114 | −12.888 | 1.00 | 41.86 | C |
| ATOM | 262 | OG1 | THR A | 37 | −6.662 | 17.017 | −13.565 | 1.00 | 42.82 | O |
| ATOM | 263 | CG2 | THR A | 37 | −4.589 | 18.006 | −13.662 | 1.00 | 43.11 | C |
| ATOM | 264 | C | THR A | 37 | −5.842 | 14.883 | −12.128 | 1.00 | 41.82 | C |
| ATOM | 265 | O | THR A | 37 | −6.227 | 15.170 | −11.034 | 1.00 | 41.39 | O |
| ATOM | 266 | N | ARG A | 38 | −6.308 | 13.842 | −12.781 | 1.00 | 39.83 | N |
| ATOM | 267 | CA | ARG A | 38 | −7.318 | 13.001 | −12.210 | 1.00 | 38.83 | C |
| ATOM | 268 | CB | ARG A | 38 | −8.414 | 12.739 | −13.208 | 1.00 | 41.00 | C |
| ATOM | 269 | CG | ARG A | 38 | −8.831 | 13.938 | −13.992 | 1.00 | 41.76 | C |
| ATOM | 270 | CD | ARG A | 38 | −9.426 | 14.964 | −13.086 | 1.00 | 44.75 | C |
| ATOM | 271 | NE | ARG A | 38 | −10.597 | 14.444 | −12.432 | 1.00 | 49.28 | N |
| ATOM | 272 | CZ | ARG A | 38 | −11.237 | 15.074 | −11.472 | 1.00 | 48.98 | C |
| ATOM | 273 | NH1 | ARG A | 38 | −10.819 | 16.237 | −11.064 | 1.00 | 53.26 | N |
| ATOM | 274 | NH2 | ARG A | 38 | −12.298 | 14.542 | −10.933 | 1.00 | 48.71 | N |
| ATOM | 275 | C | ARG A | 38 | −6.741 | 11.696 | −11.870 | 1.00 | 38.00 | C |
| ATOM | 276 | O | ARG A | 38 | −5.896 | 11.215 | −12.554 | 1.00 | 35.90 | O |
| ATOM | 277 | N | LEU A | 39 | −7.201 | 11.118 | −10.786 | 1.00 | 40.06 | N |
| ATOM | 278 | CA | LEU A | 39 | −6.750 | 9.792 | −10.375 | 1.00 | 41.84 | C |
| ATOM | 279 | CB | LEU A | 39 | −5.927 | 9.873 | −9.105 | 1.00 | 43.12 | C |
| ATOM | 280 | CG | LEU A | 39 | −5.725 | 8.587 | −8.301 | 1.00 | 46.34 | C |
| ATOM | 281 | CD1 | LEU A | 39 | −4.813 | 7.662 | −9.040 | 1.00 | 49.46 | C |
| ATOM | 282 | CD2 | LEU A | 39 | −5.104 | 8.811 | −6.939 | 1.00 | 48.22 | C |

TABLE 6-continued

Atomic coordinates for CRBN:DDB1: Compound B (Human protein)

| ATOM | 283 | C   | LEU A | 39 | −8.002  | 8.972   | −10.169 | 1.00 | 41.92 | C |
|------|-----|-----|-------|----|---------|---------|---------|------|-------|---|
| ATOM | 284 | O   | LEU A | 39 | −8.756  | 9.308   | −9.305  | 1.00 | 38.88 | O |
| ATOM | 285 | N   | GLU A | 40 | −8.217  | 7.950   | −11.016 | 1.00 | 44.57 | N |
| ATOM | 286 | CA  | GLU A | 40 | −9.313  | 6.998   | −10.912 | 1.00 | 45.38 | C |
| ATOM | 287 | CB  | GLU A | 40 | −9.805  | 6.507   | −12.280 | 1.00 | 50.07 | C |
| ATOM | 288 | CG  | GLU A | 40 | −10.120 | 7.598   | −13.287 | 1.00 | 57.71 | C |
| ATOM | 289 | CD  | GLU A | 40 | −10.523 | 7.134   | −14.710 | 1.00 | 67.78 | C |
| ATOM | 290 | OE1 | GLU A | 40 | −9.991  | 6.138   | −15.364 | 1.00 | 68.04 | O |
| ATOM | 291 | OE2 | GLU A | 40 | −11.419 | 7.850   | −15.202 | 1.00 | 74.59 | O |
| ATOM | 292 | C   | GLU A | 40 | −8.733  | 5.812   | −10.173 | 1.00 | 44.48 | C |
| ATOM | 293 | O   | GLU A | 40 | −7.561  | 5.489   | −10.377 | 1.00 | 41.61 | O |
| ATOM | 294 | N   | ILE A | 41 | −9.573  | 5.187   | −9.338  | 1.00 | 42.45 | N |
| ATOM | 295 | CA  | ILE A | 41 | −9.291  | 3.967   | −8.604  | 1.00 | 41.53 | C |
| ATOM | 296 | CB  | ILE A | 41 | −9.347  | 4.196   | −7.103  | 1.00 | 43.60 | C |
| ATOM | 297 | CG1 | ILE A | 41 | −8.354  | 5.297   | −6.679  | 1.00 | 45.83 | C |
| ATOM | 298 | CD1 | ILE A | 41 | −8.530  | 5.784   | −5.235  | 1.00 | 45.22 | C |
| ATOM | 299 | CG2 | ILE A | 41 | −9.158  | 2.855   | −6.383  | 1.00 | 43.64 | C |
| ATOM | 300 | C   | ILE A | 41 | −10.375 | 2.926   | −8.799  | 1.00 | 41.93 | C |
| ATOM | 301 | O   | ILE A | 41 | −11.482 | 3.055   | −8.261  | 1.00 | 42.01 | O |
| ATOM | 302 | N   | TYR A | 42 | −10.029 | 1.838   | −9.475  | 1.00 | 43.54 | N |
| ATOM | 303 | CA  | TYR A | 42 | −10.921 | 0.658   | −9.603  | 1.00 | 41.62 | C |
| ATOM | 304 | CB  | TYR A | 42 | −10.939 | 0.156   | −11.023 | 1.00 | 38.45 | C |
| ATOM | 305 | CG  | TYR A | 42 | −11.274 | 1.171   | −12.010 | 1.00 | 37.06 | C |
| ATOM | 306 | CD1 | TYR A | 42 | −10.316 | 2.002   | −12.480 | 1.00 | 38.41 | C |
| ATOM | 307 | CE1 | TYR A | 42 | −10.599 | 2.945   | −13.447 | 1.00 | 39.71 | C |
| ATOM | 308 | CZ  | TYR A | 42 | −11.863 | 3.046   | −13.949 | 1.00 | 39.45 | C |
| ATOM | 309 | OH  | TYR A | 42 | −12.092 | 4.007   | −14.901 | 1.00 | 45.31 | O |
| ATOM | 310 | CE2 | TYR A | 42 | −12.849 | 2.206   | −13.501 | 1.00 | 37.36 | C |
| ATOM | 311 | CD2 | TYR A | 42 | −12.543 | 1.268   | −12.539 | 1.00 | 36.89 | C |
| ATOM | 312 | C   | TYR A | 42 | −10.498 | −0.528  | −8.698  | 1.00 | 41.55 | C |
| ATOM | 313 | O   | TYR A | 42 | −9.376  | −0.579  | −8.201  | 1.00 | 36.79 | O |
| ATOM | 314 | N   | VAL A | 43 | −11.434 | −1.461  | −8.515  | 1.00 | 45.04 | N |
| ATOM | 315 | CA  | VAL A | 43 | −11.160 | −2.801  | −8.013  | 1.00 | 50.19 | C |
| ATOM | 316 | CB  | VAL A | 43 | −12.189 | −3.241  | −6.956  | 1.00 | 53.38 | C |
| ATOM | 317 | CG1 | VAL A | 43 | −11.959 | −4.707  | −6.556  | 1.00 | 54.50 | C |
| ATOM | 318 | CG2 | VAL A | 43 | −12.110 | −2.336  | −5.732  | 1.00 | 54.66 | C |
| ATOM | 319 | C   | VAL A | 43 | −11.301 | −3.771  | −9.163  | 1.00 | 51.12 | C |
| ATOM | 320 | O   | VAL A | 43 | −12.323 | −3.763  | −9.866  | 1.00 | 53.29 | O |
| ATOM | 321 | N   | VAL A | 44 | −10.299 | −4.618  | −9.334  | 1.00 | 52.42 | N |
| ATOM | 322 | CA  | VAL A | 44 | −10.370 | −5.680  | −10.346 | 1.00 | 58.09 | C |
| ATOM | 323 | CB  | VAL A | 44 | −8.981  | −6.354  | −10.556 | 1.00 | 57.94 | C |
| ATOM | 324 | CG1 | VAL A | 44 | −9.112  | −7.584  | −11.421 | 1.00 | 59.05 | C |
| ATOM | 325 | CG2 | VAL A | 44 | −7.967  | −5.398  | −11.173 | 1.00 | 56.40 | C |
| ATOM | 326 | C   | VAL A | 44 | −11.391 | −6.741  | −9.896  | 1.00 | 59.01 | C |
| ATOM | 327 | O   | VAL A | 44 | −11.396 | −7.131  | −8.734  | 1.00 | 54.04 | O |
| ATOM | 328 | N   | THR A | 45 | −12.246 | −7.184  | −10.816 | 1.00 | 65.90 | N |
| ATOM | 329 | CA  | THR A | 45 | −13.176 | −8.324  | −10.590 | 1.00 | 71.66 | C |
| ATOM | 330 | CB  | THR A | 45 | −14.672 | −7.851  | −10.641 | 1.00 | 71.96 | C |
| ATOM | 331 | OG1 | THR A | 45 | −15.022 | −7.321  | −11.938 | 1.00 | 64.98 | O |
| ATOM | 332 | CG2 | THR A | 45 | −14.956 | −6.778  | −9.551  | 1.00 | 73.02 | C |
| ATOM | 333 | C   | THR A | 45 | −12.944 | −9.422  | −11.648 | 1.00 | 73.92 | C |
| ATOM | 334 | O   | THR A | 45 | −12.219 | −9.206  | −12.598 | 1.00 | 77.65 | O |
| ATOM | 335 | N   | ALA A | 46 | −13.561 | −10.587 | −11.520 | 1.00 | 80.17 | N |
| ATOM | 336 | CA  | ALA A | 46 | −13.721 | −11.436 | −12.724 | 1.00 | 86.24 | C |
| ATOM | 337 | CB  | ALA A | 46 | −14.284 | −12.818 | −12.401 | 1.00 | 83.20 | C |
| ATOM | 338 | C   | ALA A | 46 | −14.611 | −10.702 | −13.749 | 1.00 | 87.72 | C |
| ATOM | 339 | O   | ALA A | 46 | −14.206 | −10.503 | −14.890 | 1.00 | 90.98 | O |
| ATOM | 340 | N   | GLU A | 47 | −15.792 | −10.261 | −13.316 | 1.00 | 89.49 | N |
| ATOM | 341 | CA  | GLU A | 47 | −16.701 | −9.465  | −14.156 | 1.00 | 90.43 | C |
| ATOM | 342 | CB  | GLU A | 47 | −17.893 | −8.987  | −13.284 | 1.00 | 88.71 | C |
| ATOM | 343 | C   | GLU A | 47 | −16.011 | −8.291  | −14.993 | 1.00 | 88.98 | C |
| ATOM | 344 | O   | GLU A | 47 | −16.504 | −7.938  | −16.066 | 1.00 | 81.51 | O |
| ATOM | 345 | N   | GLY A | 48 | −14.879 | −7.736  | −14.518 | 1.00 | 85.76 | N |
| ATOM | 346 | CA  | GLY A | 48 | −14.080 | −6.714  | −15.246 | 1.00 | 81.62 | C |
| ATOM | 347 | C   | GLY A | 48 | −13.445 | −5.680  | −14.298 | 1.00 | 78.10 | C |
| ATOM | 348 | O   | GLY A | 48 | −12.698 | −6.059  | −13.379 | 1.00 | 77.53 | O |
| ATOM | 349 | N   | LEU A | 49 | −13.727 | −4.383  | −14.494 | 1.00 | 68.51 | N |
| ATOM | 350 | CA  | LEU A | 49 | −13.249 | −3.336  | −13.545 | 1.00 | 63.27 | C |
| ATOM | 351 | CB  | LEU A | 49 | −12.455 | −2.271  | −14.294 | 1.00 | 59.90 | C |
| ATOM | 352 | CG  | LEU A | 49 | −11.110 | −2.629  | −14.905 | 1.00 | 58.85 | C |
| ATOM | 353 | CD1 | LEU A | 49 | −10.583 | −1.417  | −15.642 | 1.00 | 59.12 | C |
| ATOM | 354 | CD2 | LEU A | 49 | −10.100 | −3.047  | −13.853 | 1.00 | 59.16 | C |
| ATOM | 355 | C   | LEU A | 49 | −14.361 | −2.620  | −12.771 | 1.00 | 60.19 | C |
| ATOM | 356 | O   | LEU A | 49 | −15.175 | −1.940  | −13.381 | 1.00 | 56.21 | O |
| ATOM | 357 | N   | ARG A | 50 | −14.369 | −2.716  | −11.436 | 1.00 | 61.26 | N |
| ATOM | 358 | CA  | ARG A | 50 | −15.347 | −1.953  | −10.605 | 1.00 | 60.73 | C |
| ATOM | 359 | CB  | ARG A | 50 | −15.777 | −2.697  | −9.334  | 1.00 | 65.22 | C |
| ATOM | 360 | CG  | ARG A | 50 | −17.053 | −2.113  | −8.685  | 1.00 | 69.70 | C |

TABLE 6-continued

Atomic coordinates for CRBN:DDB1: Compound B (Human protein)

| ATOM | 361 | CD | ARG A | 50 | −17.830 | −3.126 | −7.816 | 1.00 | 71.57 | C |
|---|---|---|---|---|---|---|---|---|---|---|
| ATOM | 362 | NE | ARG A | 50 | −16.955 | −3.992 | −6.991 | 1.00 | 74.61 | N |
| ATOM | 363 | CZ | ARG A | 50 | −16.271 | −3.600 | −5.895 | 1.00 | 75.28 | C |
| ATOM | 364 | NH1 | ARG A | 50 | −16.331 | −2.340 | −5.436 | 1.00 | 75.08 | N |
| ATOM | 365 | NH2 | ARG A | 50 | −15.505 | −4.475 | −5.237 | 1.00 | 71.43 | N |
| ATOM | 366 | C | ARG A | 50 | −14.775 | −0.615 | −10.184 | 1.00 | 56.25 | C |
| ATOM | 367 | O | ARG A | 50 | −13.807 | −0.580 | −9.431 | 1.00 | 51.30 | O |
| ATOM | 368 | N | PRO A | 51 | −15.341 | 0.477 | −10.657 | 1.00 | 53.20 | N |
| ATOM | 369 | CA | PRO A | 51 | −14.854 | 1.792 | −10.309 | 1.00 | 53.44 | C |
| ATOM | 370 | CB | PRO A | 51 | −15.740 | 2.665 | −11.142 | 1.00 | 50.63 | C |
| ATOM | 371 | CG | PRO A | 51 | −17.037 | 1.990 | −11.049 | 1.00 | 49.90 | C |
| ATOM | 372 | CD | PRO A | 51 | −16.773 | 0.527 | −10.932 | 1.00 | 52.19 | C |
| ATOM | 373 | C | PRO A | 51 | −15.179 | 2.035 | −8.878 | 1.00 | 52.86 | C |
| ATOM | 374 | O | PRO A | 51 | −16.243 | 1.657 | −8.485 | 1.00 | 55.49 | O |
| ATOM | 375 | N | VAL A | 52 | −14.300 | 2.651 | −8.111 | 1.00 | 53.63 | N |
| ATOM | 376 | CA | VAL A | 52 | −14.582 | 2.885 | −6.713 | 1.00 | 51.53 | C |
| ATOM | 377 | CB | VAL A | 52 | −13.606 | 2.064 | −5.873 | 1.00 | 49.44 | C |
| ATOM | 378 | CG1 | VAL A | 52 | −13.616 | 2.451 | −4.417 | 1.00 | 51.21 | C |
| ATOM | 379 | CG2 | VAL A | 52 | −13.975 | 0.619 | −5.981 | 1.00 | 51.50 | C |
| ATOM | 380 | C | VAL A | 52 | −14.554 | 4.347 | −6.302 | 1.00 | 52.93 | C |
| ATOM | 381 | O | VAL A | 52 | −15.473 | 4.838 | −5.686 | 1.00 | 54.55 | O |
| ATOM | 382 | N | LYS A | 53 | −13.471 | 5.023 | −6.614 | 1.00 | 50.17 | N |
| ATOM | 383 | CA | LYS A | 53 | −13.346 | 6.400 | −6.256 | 1.00 | 45.90 | C |
| ATOM | 384 | CB | LYS A | 53 | −12.685 | 6.467 | −4.893 | 1.00 | 47.97 | C |
| ATOM | 385 | CG | LYS A | 53 | −12.451 | 7.845 | −4.310 | 1.00 | 51.37 | C |
| ATOM | 386 | CD | LYS A | 53 | −13.734 | 8.489 | −3.856 | 1.00 | 50.93 | C |
| ATOM | 387 | CE | LYS A | 53 | −13.483 | 9.798 | −3.160 | 1.00 | 51.75 | C |
| ATOM | 388 | NZ | LYS A | 53 | −14.783 | 10.384 | −2.776 | 1.00 | 54.36 | N |
| ATOM | 389 | C | LYS A | 53 | −12.515 | 7.126 | −7.262 | 1.00 | 46.86 | C |
| ATOM | 390 | O | LYS A | 53 | −11.514 | 6.646 | −7.681 | 1.00 | 45.60 | O |
| ATOM | 391 | N | GLU A | 54 | −12.939 | 8.313 | −7.624 | 1.00 | 45.96 | N |
| ATOM | 392 | CA | GLU A | 54 | −12.207 | 9.179 | −8.499 | 1.00 | 44.79 | C |
| ATOM | 393 | CB | GLU A | 54 | −12.991 | 9.244 | −9.802 | 1.00 | 46.24 | C |
| ATOM | 394 | CG | GLU A | 54 | −12.244 | 9.722 | −11.042 | 1.00 | 47.42 | C |
| ATOM | 395 | CD | GLU A | 54 | −12.343 | 11.194 | −11.269 | 1.00 | 48.07 | C |
| ATOM | 396 | OE1 | GLU A | 54 | −11.714 | 11.711 | −12.228 | 1.00 | 51.06 | O |
| ATOM | 397 | OE2 | GLU A | 54 | −13.044 | 11.835 | −10.469 | 1.00 | 51.51 | O |
| ATOM | 398 | C | GLU A | 54 | −11.997 | 10.569 | −7.857 | 1.00 | 44.13 | C |
| ATOM | 399 | O | GLU A | 54 | −12.816 | 11.045 | −7.103 | 1.00 | 49.02 | O |
| ATOM | 400 | N | VAL A | 55 | −10.872 | 11.203 | −8.146 | 1.00 | 45.67 | N |
| ATOM | 401 | CA | VAL A | 55 | −10.499 | 12.489 | −7.555 | 1.00 | 44.91 | C |
| ATOM | 402 | CB | VAL A | 55 | −9.737 | 12.382 | −6.206 | 1.00 | 41.77 | C |
| ATOM | 403 | CG1 | VAL A | 55 | −10.610 | 11.698 | −5.174 | 1.00 | 40.41 | C |
| ATOM | 404 | CG2 | VAL A | 55 | −8.384 | 11.683 | −6.375 | 1.00 | 41.94 | C |
| ATOM | 405 | C | VAL A | 55 | −9.588 | 13.266 | −8.438 | 1.00 | 44.68 | C |
| ATOM | 406 | O | VAL A | 55 | −8.776 | 12.689 | −9.129 | 1.00 | 51.52 | O |
| ATOM | 407 | N | GLY A | 56 | −9.717 | 14.579 | −8.347 | 1.00 | 44.93 | N |
| ATOM | 408 | CA | GLY A | 56 | −8.743 | 15.514 | −8.828 | 1.00 | 44.77 | C |
| ATOM | 409 | C | GLY A | 56 | −7.590 | 15.771 | −7.838 | 1.00 | 44.25 | C |
| ATOM | 410 | O | GLY A | 56 | −7.665 | 15.473 | −6.637 | 1.00 | 38.93 | O |
| ATOM | 411 | N | MET A | 57 | −6.493 | 16.290 | −8.404 | 1.00 | 46.35 | N |
| ATOM | 412 | CA | MET A | 57 | −5.432 | 16.979 | −7.673 | 1.00 | 45.06 | C |
| ATOM | 413 | CB | MET A | 57 | −4.143 | 16.171 | −7.654 | 1.00 | 45.30 | C |
| ATOM | 414 | CG | MET A | 57 | −4.354 | 14.869 | −6.929 | 1.00 | 45.32 | C |
| ATOM | 415 | SD | MET A | 57 | −2.856 | 13.935 | −6.744 | 1.00 | 56.85 | S |
| ATOM | 416 | CE | MET A | 57 | −1.599 | 15.123 | −6.263 | 1.00 | 53.91 | C |
| ATOM | 417 | C | MET A | 57 | −5.255 | 18.337 | −8.318 | 1.00 | 42.08 | C |
| ATOM | 418 | O | MET A | 57 | −5.836 | 18.628 | −9.346 | 1.00 | 39.26 | O |
| ATOM | 419 | N | TYR A | 58 | −4.532 | 19.172 | −7.614 | 1.00 | 42.61 | N |
| ATOM | 420 | CA | TYR A | 58 | −4.183 | 20.489 | −8.055 | 1.00 | 43.63 | C |
| ATOM | 421 | CB | TYR A | 58 | −4.306 | 21.394 | −6.873 | 1.00 | 45.17 | C |
| ATOM | 422 | CG | TYR A | 58 | −5.703 | 21.788 | −6.424 | 1.00 | 44.09 | C |
| ATOM | 423 | CD1 | TYR A | 58 | −6.807 | 21.735 | −7.228 | 1.00 | 40.68 | C |
| ATOM | 424 | CE1 | TYR A | 58 | −8.038 | 22.174 | −6.756 | 1.00 | 42.09 | C |
| ATOM | 425 | CZ | TYR A | 58 | −8.154 | 22.687 | −5.483 | 1.00 | 43.38 | C |
| ATOM | 426 | OH | TYR A | 58 | −9.313 | 23.184 | −4.901 | 1.00 | 46.14 | O |
| ATOM | 427 | CE2 | TYR A | 58 | −7.069 | 22.751 | −4.708 | 1.00 | 43.26 | C |
| ATOM | 428 | CD2 | TYR A | 58 | −5.865 | 22.313 | −5.164 | 1.00 | 44.52 | C |
| ATOM | 429 | C | TYR A | 58 | −2.732 | 20.371 | −8.500 | 1.00 | 44.78 | C |
| ATOM | 430 | O | TYR A | 58 | −1.780 | 20.961 | −7.929 | 1.00 | 41.17 | O |
| ATOM | 431 | N | GLY A | 59 | −2.574 | 19.543 | −9.521 | 1.00 | 43.33 | N |
| ATOM | 432 | CA | GLY A | 59 | −1.271 | 19.082 | −9.879 | 1.00 | 42.99 | C |
| ATOM | 433 | C | GLY A | 59 | −1.419 | 18.194 | −11.069 | 1.00 | 42.48 | C |
| ATOM | 434 | O | GLY A | 59 | −2.458 | 17.537 | −11.226 | 1.00 | 46.28 | O |
| ATOM | 435 | N | LYS A | 60 | −0.380 | 18.196 | −11.905 | 1.00 | 41.06 | N |
| ATOM | 436 | CA | LYS A | 60 | −0.159 | 17.192 | −12.969 | 1.00 | 38.02 | C |
| ATOM | 437 | CB | LYS A | 60 | 0.693 | 17.785 | −14.129 | 1.00 | 39.06 | C |
| ATOM | 438 | CG | LYS A | 60 | −0.081 | 18.804 | −14.991 | 1.00 | 42.64 | C |

TABLE 6-continued

Atomic coordinates for CRBN:DDB1: Compound B (Human protein)

| ATOM | 439 | CD | LYS A | 60 | 0.721 | 19.595 | −16.015 | 1.00 | 43.37 | C |
|---|---|---|---|---|---|---|---|---|---|---|
| ATOM | 440 | CE | LYS A | 60 | 1.277 | 18.673 | −17.071 | 1.00 | 45.61 | C |
| ATOM | 441 | NZ | LYS A | 60 | 0.218 | 18.058 | −17.914 | 1.00 | 47.23 | N |
| ATOM | 442 | C | LYS A | 60 | 0.535 | 15.952 | −12.390 | 1.00 | 35.34 | C |
| ATOM | 443 | O | LYS A | 60 | 1.707 | 15.979 | −12.090 | 1.00 | 30.00 | O |
| ATOM | 444 | N | ILE A | 61 | −0.180 | 14.852 | −12.247 | 1.00 | 36.68 | N |
| ATOM | 445 | CA | ILE A | 61 | 0.469 | 13.650 | −11.726 | 1.00 | 39.94 | C |
| ATOM | 446 | CB | ILE A | 61 | −0.460 | 12.437 | −11.705 | 1.00 | 40.19 | C |
| ATOM | 447 | CG1 | ILE A | 61 | −1.564 | 12.643 | −10.682 | 1.00 | 42.02 | C |
| ATOM | 448 | CD1 | ILE A | 61 | −2.739 | 11.747 | −10.940 | 1.00 | 45.07 | C |
| ATOM | 449 | CG2 | ILE A | 61 | 0.317 | 11.218 | −11.253 | 1.00 | 40.57 | C |
| ATOM | 450 | C | ILE A | 61 | 1.649 | 13.268 | −12.574 | 1.00 | 40.25 | C |
| ATOM | 451 | O | ILE A | 61 | 1.451 | 13.026 | −13.698 | 1.00 | 40.97 | O |
| ATOM | 452 | N | ALA A | 62 | 2.854 | 13.200 | −12.029 | 1.00 | 43.18 | N |
| ATOM | 453 | CA | ALA A | 62 | 4.078 | 12.866 | −12.821 | 1.00 | 43.52 | C |
| ATOM | 454 | CB | ALA A | 62 | 5.054 | 14.031 | −12.778 | 1.00 | 42.94 | C |
| ATOM | 455 | C | ALA A | 62 | 4.795 | 11.572 | −12.360 | 1.00 | 43.09 | C |
| ATOM | 456 | O | ALA A | 62 | 5.452 | 10.931 | −13.134 | 1.00 | 50.11 | O |
| ATOM | 457 | N | VAL A | 63 | 4.717 | 11.238 | −11.092 | 1.00 | 42.12 | N |
| ATOM | 458 | CA | VAL A | 63 | 5.059 | 9.926 | −10.558 | 1.00 | 40.46 | C |
| ATOM | 459 | CB | VAL A | 63 | 6.220 | 10.039 | −9.562 | 1.00 | 39.90 | C |
| ATOM | 460 | CG1 | VAL A | 63 | 6.772 | 8.692 | −9.232 | 1.00 | 40.37 | C |
| ATOM | 461 | CG2 | VAL A | 63 | 7.346 | 10.867 | −10.131 | 1.00 | 41.18 | C |
| ATOM | 462 | C | VAL A | 63 | 3.840 | 9.384 | −9.786 | 1.00 | 42.70 | C |
| ATOM | 463 | O | VAL A | 63 | 3.113 | 10.105 | −9.064 | 1.00 | 42.57 | O |
| ATOM | 464 | N | MET A | 64 | 3.628 | 8.094 | −9.907 | 1.00 | 45.17 | N |
| ATOM | 465 | CA | MET A | 64 | 2.542 | 7.463 | −9.182 | 1.00 | 46.69 | C |
| ATOM | 466 | CB | MET A | 64 | 1.297 | 7.427 | −10.048 | 1.00 | 46.50 | C |
| ATOM | 467 | CG | MET A | 64 | 0.245 | 6.497 | −9.510 | 1.00 | 47.97 | C |
| ATOM | 468 | SD | MET A | 64 | −1.340 | 6.924 | −10.164 | 1.00 | 53.90 | S |
| ATOM | 469 | CE | MET A | 64 | −1.281 | 5.954 | −11.669 | 1.00 | 55.11 | C |
| ATOM | 470 | C | MET A | 64 | 2.943 | 6.055 | −8.825 | 1.00 | 46.95 | C |
| ATOM | 471 | O | MET A | 64 | 2.932 | 5.204 | −9.713 | 1.00 | 51.01 | O |
| ATOM | 472 | N | GLU A | 65 | 3.285 | 5.800 | −7.568 | 1.00 | 45.00 | N |
| ATOM | 473 | CA | GLU A | 65 | 3.741 | 4.471 | −7.210 | 1.00 | 51.09 | C |
| ATOM | 474 | CB | GLU A | 65 | 5.272 | 4.446 | −7.072 | 1.00 | 58.26 | C |
| ATOM | 475 | CG | GLU A | 65 | 6.052 | 4.774 | −8.359 | 1.00 | 61.79 | C |
| ATOM | 476 | CD | GLU A | 65 | 5.847 | 3.744 | −9.459 | 1.00 | 68.45 | C |
| ATOM | 477 | OE1 | GLU A | 65 | 5.349 | 2.601 | −9.164 | 1.00 | 68.61 | O |
| ATOM | 478 | OE2 | GLU A | 65 | 6.181 | 4.097 | −10.622 | 1.00 | 75.47 | O |
| ATOM | 479 | C | GLU A | 65 | 3.137 | 3.988 | −5.943 | 1.00 | 47.13 | C |
| ATOM | 480 | O | GLU A | 65 | 3.046 | 4.755 | −5.020 | 1.00 | 48.02 | O |
| ATOM | 481 | N | LEU A | 66 | 2.764 | 2.708 | −5.896 | 1.00 | 46.57 | N |
| ATOM | 482 | CA | LEU A | 66 | 2.233 | 2.084 | −4.670 | 1.00 | 46.42 | C |
| ATOM | 483 | CB | LEU A | 66 | 1.148 | 1.073 | −4.982 | 1.00 | 42.76 | C |
| ATOM | 484 | CG | LEU A | 66 | −0.251 | 1.666 | −5.184 | 1.00 | 41.69 | C |
| ATOM | 485 | CD1 | LEU A | 66 | −1.139 | 0.535 | −5.691 | 1.00 | 41.51 | C |
| ATOM | 486 | CD2 | LEU A | 66 | −0.881 | 2.320 | −3.940 | 1.00 | 40.68 | C |
| ATOM | 487 | C | LEU A | 66 | 3.332 | 1.411 | −3.870 | 1.00 | 49.67 | C |
| ATOM | 488 | O | LEU A | 66 | 4.264 | 0.875 | −4.431 | 1.00 | 54.17 | O |
| ATOM | 489 | N | PHE A | 67 | 3.232 | 1.470 | −2.555 | 1.00 | 53.28 | N |
| ATOM | 490 | CA | PHE A | 67 | 4.234 | 0.863 | −1.678 | 1.00 | 57.57 | C |
| ATOM | 491 | CB | PHE A | 67 | 5.455 | 1.787 | −1.521 | 1.00 | 53.47 | C |
| ATOM | 492 | CG | PHE A | 67 | 5.187 | 2.978 | −0.690 | 1.00 | 54.40 | C |
| ATOM | 493 | CD1 | PHE A | 67 | 4.447 | 4.030 | −1.189 | 1.00 | 54.73 | C |
| ATOM | 494 | CE1 | PHE A | 67 | 4.166 | 5.143 | −0.393 | 1.00 | 55.50 | C |
| ATOM | 495 | CZ | PHE A | 67 | 4.623 | 5.206 | 0.911 | 1.00 | 52.99 | C |
| ATOM | 496 | CE2 | PHE A | 67 | 5.342 | 4.138 | 1.424 | 1.00 | 54.32 | C |
| ATOM | 497 | CD2 | PHE A | 67 | 5.614 | 3.033 | 0.630 | 1.00 | 55.90 | C |
| ATOM | 498 | C | PHE A | 67 | 3.580 | 0.506 | −0.337 | 1.00 | 64.11 | C |
| ATOM | 499 | O | PHE A | 67 | 2.493 | 1.003 | −0.029 | 1.00 | 70.80 | O |
| ATOM | 500 | N | ARG A | 68 | 4.213 | −0.382 | 0.429 | 1.00 | 70.32 | N |
| ATOM | 501 | CA | ARG A | 68 | 3.699 | −0.806 | 1.747 | 1.00 | 73.36 | C |
| ATOM | 502 | CB | ARG A | 68 | 3.125 | −2.233 | 1.701 | 1.00 | 69.89 | C |
| ATOM | 503 | CG | ARG A | 68 | 1.896 | −2.352 | 2.552 | 1.00 | 70.81 | C |
| ATOM | 504 | CD | ARG A | 68 | 1.497 | −3.783 | 2.837 | 1.00 | 75.39 | C |
| ATOM | 505 | NE | ARG A | 68 | 0.436 | −4.272 | 1.952 | 1.00 | 75.87 | N |
| ATOM | 506 | CZ | ARG A | 68 | −0.332 | −5.333 | 2.203 | 1.00 | 81.34 | C |
| ATOM | 507 | NH1 | ARG A | 68 | −0.198 | −6.025 | 3.340 | 1.00 | 89.34 | N |
| ATOM | 508 | NH2 | ARG A | 68 | −1.258 | −5.715 | 1.321 | 1.00 | 83.00 | N |
| ATOM | 509 | C | ARG A | 68 | 4.846 | −0.740 | 2.743 | 1.00 | 79.30 | C |
| ATOM | 510 | O | ARG A | 68 | 5.662 | −1.645 | 2.765 | 1.00 | 77.42 | O |
| ATOM | 511 | N | PRO A | 69 | 4.929 | 0.336 | 3.559 | 1.00 | 88.44 | N |
| ATOM | 512 | CA | PRO A | 69 | 6.031 | 0.347 | 4.527 | 1.00 | 91.63 | C |
| ATOM | 513 | CB | PRO A | 69 | 6.054 | 1.795 | 5.033 | 1.00 | 92.01 | C |
| ATOM | 514 | CG | PRO A | 69 | 4.653 | 2.281 | 4.851 | 1.00 | 92.58 | C |
| ATOM | 515 | CD | PRO A | 69 | 4.023 | 1.487 | 3.735 | 1.00 | 89.40 | C |
| ATOM | 516 | C | PRO A | 69 | 5.773 | −0.683 | 5.648 | 1.00 | 95.91 | C |

TABLE 6-continued

Atomic coordinates for CRBN:DDB1: Compound B (Human protein)

| ATOM | 517 | O | PRO A | 69 | 4.626 | −1.172 | 5.800 | 1.00 | 90.29 | O |
|---|---|---|---|---|---|---|---|---|---|---|
| ATOM | 518 | N | LYS A | 70 | 6.832 | −1.012 | 6.400 | 1.00 | 94.87 | N |
| ATOM | 519 | CA | LYS A | 70 | 6.796 | −2.148 | 7.310 | 1.00 | 93.51 | C |
| ATOM | 520 | CB | LYS A | 70 | 8.117 | −2.328 | 8.047 | 1.00 | 101.05 | C |
| ATOM | 521 | CG | LYS A | 70 | 8.349 | −3.777 | 8.490 | 1.00 | 108.47 | C |
| ATOM | 522 | CD | LYS A | 70 | 9.128 | −4.606 | 7.458 | 1.00 | 113.18 | C |
| ATOM | 523 | CE | LYS A | 70 | 10.492 | −4.005 | 7.065 | 1.00 | 112.45 | C |
| ATOM | 524 | NZ | LYS A | 70 | 11.216 | −3.227 | 8.130 | 1.00 | 108.58 | N |
| ATOM | 525 | C | LYS A | 70 | 5.707 | −1.904 | 8.308 | 1.00 | 84.14 | C |
| ATOM | 526 | O | LYS A | 70 | 5.696 | −0.834 | 8.925 | 1.00 | 73.15 | O |
| ATOM | 527 | N | GLY A | 71 | 4.786 | −2.868 | 8.418 | 1.00 | 80.46 | N |
| ATOM | 528 | CA | GLY A | 71 | 3.658 | −2.781 | 9.356 | 1.00 | 85.28 | C |
| ATOM | 529 | C | GLY A | 71 | 2.569 | −1.757 | 8.999 | 1.00 | 88.33 | C |
| ATOM | 530 | O | GLY A | 71 | 2.281 | −0.797 | 9.742 | 1.00 | 83.75 | O |
| ATOM | 531 | N | GLU A | 72 | 1.971 | −1.963 | 7.833 | 1.00 | 85.73 | N |
| ATOM | 532 | CA | GLU A | 72 | 0.797 | −1.232 | 7.418 | 1.00 | 74.93 | C |
| ATOM | 533 | CB | GLU A | 72 | 1.186 | −0.169 | 6.401 | 1.00 | 80.05 | C |
| ATOM | 534 | CG | GLU A | 72 | 0.200 | 1.009 | 6.333 | 1.00 | 82.89 | C |
| ATOM | 535 | CD | GLU A | 72 | 0.618 | 2.200 | 7.188 | 1.00 | 78.44 | C |
| ATOM | 536 | OE1 | GLU A | 72 | −0.252 | 3.031 | 7.501 | 1.00 | 71.65 | O |
| ATOM | 537 | OE2 | GLU A | 72 | 1.812 | 2.336 | 7.537 | 1.00 | 75.09 | O |
| ATOM | 538 | C | GLU A | 72 | −0.152 | −2.261 | 6.814 | 1.00 | 67.28 | C |
| ATOM | 539 | O | GLU A | 72 | 0.251 | −3.144 | 6.049 | 1.00 | 63.08 | O |
| ATOM | 540 | N | SER A | 73 | −1.417 | −2.176 | 7.176 | 1.00 | 65.73 | N |
| ATOM | 541 | CA | SER A | 73 | −2.366 | −3.210 | 6.777 | 1.00 | 65.10 | C |
| ATOM | 542 | CB | SER A | 73 | −3.763 | −2.962 | 7.381 | 1.00 | 63.49 | C |
| ATOM | 543 | OG | SER A | 73 | −4.375 | −1.772 | 6.913 | 1.00 | 62.76 | O |
| ATOM | 544 | C | SER A | 73 | −2.408 | −3.324 | 5.266 | 1.00 | 66.51 | C |
| ATOM | 545 | O | SER A | 73 | −2.382 | −4.435 | 4.751 | 1.00 | 67.26 | O |
| ATOM | 546 | N | LYS A | 74 | −2.372 | −2.162 | 4.595 | 1.00 | 68.69 | N |
| ATOM | 547 | CA | LYS A | 74 | −2.539 | −2.026 | 3.150 | 1.00 | 69.16 | C |
| ATOM | 548 | CB | LYS A | 74 | −3.974 | −1.582 | 2.841 | 1.00 | 71.88 | C |
| ATOM | 549 | CG | LYS A | 74 | −4.421 | −0.331 | 3.572 | 1.00 | 75.71 | C |
| ATOM | 550 | CD | LYS A | 74 | −5.870 | 0.008 | 3.241 | 1.00 | 76.35 | C |
| ATOM | 551 | CE | LYS A | 74 | −6.317 | 1.175 | 4.098 | 1.00 | 79.39 | C |
| ATOM | 552 | NZ | LYS A | 74 | −7.777 | 1.077 | 4.316 | 1.00 | 83.89 | N |
| ATOM | 553 | C | LYS A | 74 | −1.517 | −1.051 | 2.543 | 1.00 | 66.10 | C |
| ATOM | 554 | O | LYS A | 74 | −0.760 | −0.443 | 3.304 | 1.00 | 65.87 | O |
| ATOM | 555 | N | ASP A | 75 | −1.501 | −0.930 | 1.192 | 1.00 | 61.66 | N |
| ATOM | 556 | CA | ASP A | 75 | −0.564 | −0.058 | 0.450 | 1.00 | 57.96 | C |
| ATOM | 557 | CB | ASP A | 75 | −0.405 | −0.397 | −1.050 | 1.00 | 60.78 | C |
| ATOM | 558 | CG | ASP A | 75 | 0.112 | −1.839 | −1.358 | 1.00 | 63.67 | C |
| ATOM | 559 | OD1 | ASP A | 75 | 0.624 | −2.548 | −0.466 | 1.00 | 71.08 | O |
| ATOM | 560 | OD2 | ASP A | 75 | 0.025 | −2.248 | −2.561 | 1.00 | 63.14 | O |
| ATOM | 561 | C | ASP A | 75 | −0.961 | 1.430 | 0.506 | 1.00 | 56.34 | C |
| ATOM | 562 | O | ASP A | 75 | −2.155 | 1.819 | 0.631 | 1.00 | 55.47 | O |
| ATOM | 563 | N | LEU A | 76 | 0.080 | 2.248 | 0.424 | 1.00 | 52.98 | N |
| ATOM | 564 | CA | LEU A | 76 | −0.029 | 3.681 | 0.368 | 1.00 | 52.58 | C |
| ATOM | 565 | CB | LEU A | 76 | 0.851 | 4.382 | 1.409 | 1.00 | 52.31 | C |
| ATOM | 566 | CG | LEU A | 76 | 0.615 | 4.107 | 2.894 | 1.00 | 50.59 | C |
| ATOM | 567 | CD1 | LEU A | 76 | 1.521 | 4.971 | 3.783 | 1.00 | 49.79 | C |
| ATOM | 568 | CD2 | LEU A | 76 | −0.838 | 4.368 | 3.181 | 1.00 | 50.85 | C |
| ATOM | 569 | C | LEU A | 76 | 0.499 | 4.049 | −0.977 | 1.00 | 52.74 | C |
| ATOM | 570 | O | LEU A | 76 | 1.319 | 3.318 | −1.562 | 1.00 | 49.73 | O |
| ATOM | 571 | N | LEU A | 77 | 0.063 | 5.223 | −1.423 | 1.00 | 50.81 | N |
| ATOM | 572 | CA | LEU A | 77 | 0.317 | 5.693 | −2.765 | 1.00 | 46.41 | C |
| ATOM | 573 | CB | LEU A | 77 | −1.025 | 6.068 | −3.375 | 1.00 | 42.83 | C |
| ATOM | 574 | CG | LEU A | 77 | −0.975 | 6.668 | −4.761 | 1.00 | 41.39 | C |
| ATOM | 575 | CD1 | LEU A | 77 | −0.340 | 5.706 | −5.712 | 1.00 | 40.64 | C |
| ATOM | 576 | CD2 | LEU A | 77 | −2.377 | 7.009 | −5.213 | 1.00 | 42.14 | C |
| ATOM | 577 | C | LEU A | 77 | 1.277 | 6.877 | −2.693 | 1.00 | 46.13 | C |
| ATOM | 578 | O | LEU A | 77 | 1.040 | 7.809 | −1.949 | 1.00 | 48.37 | O |
| ATOM | 579 | N | PHE A | 78 | 2.385 | 6.825 | −3.412 | 1.00 | 46.03 | N |
| ATOM | 580 | CA | PHE A | 78 | 3.219 | 8.010 | −3.563 | 1.00 | 48.98 | C |
| ATOM | 581 | CB | PHE A | 78 | 4.684 | 7.669 | −3.614 | 1.00 | 49.04 | C |
| ATOM | 582 | CG | PHE A | 78 | 5.564 | 8.852 | −3.848 | 1.00 | 47.89 | C |
| ATOM | 583 | CD1 | PHE A | 78 | 5.640 | 9.839 | −2.930 | 1.00 | 48.10 | C |
| ATOM | 584 | CE1 | PHE A | 78 | 6.454 | 10.925 | −3.123 | 1.00 | 50.75 | C |
| ATOM | 585 | CE | PHE A | 78 | 7.227 | 11.022 | −4.256 | 1.00 | 52.95 | C |
| ATOM | 586 | CE2 | PHE A | 78 | 7.170 | 10.024 | −5.186 | 1.00 | 52.94 | C |
| ATOM | 587 | CD2 | PHE A | 78 | 6.324 | 8.947 | −4.980 | 1.00 | 51.27 | C |
| ATOM | 588 | C | PHE A | 78 | 2.893 | 8.693 | −4.857 | 1.00 | 49.56 | C |
| ATOM | 589 | O | PHE A | 78 | 2.834 | 8.018 | −5.870 | 1.00 | 52.68 | O |
| ATOM | 590 | N | ILE A | 79 | 2.755 | 10.018 | −4.824 | 1.00 | 47.61 | N |
| ATOM | 591 | CA | ILE A | 79 | 2.542 | 10.778 | −6.027 | 1.00 | 48.61 | C |
| ATOM | 592 | CB | ILE A | 79 | 1.055 | 11.144 | −6.175 | 1.00 | 49.48 | C |
| ATOM | 593 | CG1 | ILE A | 79 | 0.317 | 9.932 | −6.744 | 1.00 | 48.54 | C |
| ATOM | 594 | CD1 | ILE A | 79 | −1.106 | 10.229 | −7.140 | 1.00 | 49.32 | C |

TABLE 6-continued

Atomic coordinates for CRBN:DDB1: Compound B (Human protein)

| ATOM | 595 | CG2 | ILE A | 79 | 0.823 | 12.439 | −6.996 | 1.00 | 48.93 | C |
|---|---|---|---|---|---|---|---|---|---|---|
| ATOM | 596 | C | ILE A | 79 | 3.387 | 12.001 | −5.985 | 1.00 | 48.96 | C |
| ATOM | 597 | O | ILE A | 79 | 3.487 | 12.660 | −4.943 | 1.00 | 55.42 | O |
| ATOM | 598 | N | LEU A | 80 | 3.970 | 12.325 | −7.125 | 1.00 | 45.74 | N |
| ATOM | 599 | CA | LEU A | 80 | 4.684 | 13.583 | −7.263 | 1.00 | 44.77 | C |
| ATOM | 600 | CB | LEU A | 80 | 6.156 | 13.297 | −7.536 | 1.00 | 46.90 | C |
| ATOM | 601 | CG | LEU A | 80 | 7.053 | 14.517 | −7.731 | 1.00 | 46.50 | C |
| ATOM | 602 | CD1 | LEU A | 80 | 6.983 | 15.454 | −6.532 | 1.00 | 46.17 | C |
| ATOM | 603 | CD2 | LEU A | 80 | 8.469 | 14.044 | −7.971 | 1.00 | 45.49 | C |
| ATOM | 604 | C | LEU A | 80 | 4.127 | 14.332 | −8.429 | 1.00 | 39.83 | C |
| ATOM | 605 | O | LEU A | 80 | 4.019 | 13.763 | −9.509 | 1.00 | 33.78 | O |
| ATOM | 606 | N | THR A | 81 | 3.815 | 15.604 | −8.252 | 1.00 | 38.58 | N |
| ATOM | 607 | CA | THR A | 81 | 3.324 | 16.363 | −9.416 | 1.00 | 42.56 | C |
| ATOM | 608 | CB | THR A | 81 | 2.413 | 17.517 | −9.095 | 1.00 | 39.67 | C |
| ATOM | 609 | OG1 | THR A | 81 | 3.238 | 18.519 | −8.509 | 1.00 | 42.48 | O |
| ATOM | 610 | CG2 | THR A | 81 | 1.324 | 17.073 | −8.221 | 1.00 | 39.53 | C |
| ATOM | 611 | C | THR A | 81 | 4.465 | 17.013 | −10.189 | 1.00 | 43.50 | C |
| ATOM | 612 | O | THR A | 81 | 5.603 | 16.938 | −9.778 | 1.00 | 44.79 | O |
| ATOM | 613 | N | ALA A | 82 | 4.111 | 17.678 | −11.286 | 1.00 | 42.70 | N |
| ATOM | 614 | CA | ALA A | 82 | 5.048 | 18.416 | −12.090 | 1.00 | 42.67 | C |
| ATOM | 615 | CB | ALA A | 82 | 4.460 | 18.786 | −13.435 | 1.00 | 42.68 | C |
| ATOM | 616 | C | ALA A | 82 | 5.546 | 19.647 | −11.412 | 1.00 | 40.95 | C |
| ATOM | 617 | O | ALA A | 82 | 6.643 | 20.059 | −11.692 | 1.00 | 44.78 | O |
| ATOM | 618 | N | LYS A | 83 | 4.797 | 20.246 | −10.521 | 1.00 | 39.76 | N |
| ATOM | 619 | CA | LYS A | 83 | 5.407 | 21.360 | −9.770 | 1.00 | 40.13 | C |
| ATOM | 620 | CB | LYS A | 83 | 4.384 | 22.426 | −9.430 | 1.00 | 37.50 | C |
| ATOM | 621 | CG | LYS A | 83 | 3.971 | 23.205 | −10.619 | 1.00 | 35.06 | C |
| ATOM | 622 | CD | LYS A | 83 | 2.843 | 24.098 | −10.237 | 1.00 | 36.05 | C |
| ATOM | 623 | CE | LYS A | 83 | 2.259 | 24.679 | −11.509 | 1.00 | 39.90 | C |
| ATOM | 624 | NZ | LYS A | 83 | 1.616 | 26.040 | −11.417 | 1.00 | 43.43 | N |
| ATOM | 625 | C | LYS A | 83 | 6.189 | 20.930 | −8.525 | 1.00 | 42.19 | C |
| ATOM | 626 | O | LYS A | 83 | 6.609 | 21.775 | −7.722 | 1.00 | 43.28 | O |
| ATOM | 627 | N | TYR A | 84 | 6.431 | 19.626 | −8.408 | 1.00 | 44.89 | N |
| ATOM | 628 | CA | TYR A | 84 | 7.270 | 19.034 | −7.354 | 1.00 | 45.59 | C |
| ATOM | 629 | CB | TYR A | 84 | 8.685 | 19.669 | −7.273 | 1.00 | 45.95 | C |
| ATOM | 630 | CG | TYR A | 84 | 9.437 | 19.780 | −8.627 | 1.00 | 47.28 | C |
| ATOM | 631 | CD1 | TYR A | 84 | 10.181 | 18.719 | −9.102 | 1.00 | 47.85 | C |
| ATOM | 632 | CE1 | TYR A | 84 | 10.863 | 18.798 | −10.295 | 1.00 | 49.95 | C |
| ATOM | 633 | CZ | TYR A | 84 | 10.837 | 19.953 | −11.032 | 1.00 | 49.71 | C |
| ATOM | 634 | OH | TYR A | 84 | 11.537 | 19.930 | −12.203 | 1.00 | 56.17 | O |
| ATOM | 635 | CE2 | TYR A | 84 | 10.137 | 21.048 | −10.598 | 1.00 | 45.99 | C |
| ATOM | 636 | CD2 | TYR A | 84 | 9.439 | 20.963 | −9.391 | 1.00 | 46.69 | C |
| ATOM | 637 | C | TYR A | 84 | 6.520 | 18.993 | −6.017 | 1.00 | 45.78 | C |
| ATOM | 638 | O | TYR A | 84 | 7.123 | 18.950 | −4.985 | 1.00 | 42.36 | O |
| ATOM | 639 | N | ASN A | 85 | 5.188 | 18.940 | −6.093 | 1.00 | 49.82 | N |
| ATOM | 640 | CA | ASN A | 85 | 4.303 | 18.491 | −4.994 | 1.00 | 50.13 | C |
| ATOM | 641 | CB | ASN A | 85 | 2.845 | 18.774 | −5.373 | 1.00 | 48.18 | C |
| ATOM | 642 | CG | ASN A | 85 | 2.591 | 20.257 | −5.599 | 1.00 | 51.30 | C |
| ATOM | 643 | OD1 | ASN A | 85 | 2.227 | 20.704 | −6.701 | 1.00 | 50.99 | O |
| ATOM | 644 | ND2 | ASN A | 85 | 2.839 | 21.046 | −4.552 | 1.00 | 52.99 | N |
| ATOM | 645 | C | ASN A | 85 | 4.437 | 16.999 | −4.701 | 1.00 | 52.15 | C |
| ATOM | 646 | O | ASN A | 85 | 4.003 | 16.157 | −5.488 | 1.00 | 57.59 | O |
| ATOM | 647 | N | ALA A | 86 | 5.055 | 16.647 | −3.589 | 1.00 | 54.10 | N |
| ATOM | 648 | CA | ALA A | 86 | 5.056 | 15.236 | −3.153 | 1.00 | 54.19 | C |
| ATOM | 649 | CB | ALA A | 86 | 6.375 | 14.881 | −2.526 | 1.00 | 57.12 | C |
| ATOM | 650 | C | ALA A | 86 | 3.997 | 15.012 | −2.146 | 1.00 | 48.88 | C |
| ATOM | 651 | O | ALA A | 86 | 3.815 | 15.843 | −1.267 | 1.00 | 47.17 | O |
| ATOM | 652 | N | CYS A | 87 | 3.299 | 13.899 | −2.272 | 1.00 | 47.72 | N |
| ATOM | 653 | CA | CYS A | 87 | 2.447 | 13.434 | −1.181 | 1.00 | 48.95 | C |
| ATOM | 654 | CB | CYS A | 87 | 0.988 | 13.818 | −1.396 | 1.00 | 49.03 | C |
| ATOM | 655 | SG | CYS A | 87 | 0.272 | 13.417 | −2.989 | 1.00 | 48.82 | S |
| ATOM | 656 | C | CYS A | 87 | 2.509 | 11.966 | −1.033 | 1.00 | 47.37 | C |
| ATOM | 657 | O | CYS A | 87 | 2.817 | 11.307 | −2.005 | 1.00 | 51.39 | O |
| ATOM | 658 | N | ILE A | 88 | 2.208 | 11.481 | 0.175 | 1.00 | 44.32 | N |
| ATOM | 659 | CA | ILE A | 88 | 1.857 | 10.089 | 0.437 | 1.00 | 43.69 | C |
| ATOM | 660 | CB | ILE A | 88 | 2.671 | 9.513 | 1.577 | 1.00 | 45.16 | C |
| ATOM | 661 | CG1 | ILE A | 88 | 4.102 | 9.260 | 1.075 | 1.00 | 46.07 | C |
| ATOM | 662 | CD1 | ILE A | 88 | 5.088 | 8.765 | 2.110 | 1.00 | 44.30 | C |
| ATOM | 663 | CG2 | ILE A | 88 | 2.053 | 8.206 | 2.051 | 1.00 | 47.69 | C |
| ATOM | 664 | C | ILE A | 88 | 0.398 | 9.999 | 0.819 | 1.00 | 45.27 | C |
| ATOM | 665 | O | ILE A | 88 | −0.059 | 10.740 | 1.654 | 1.00 | 46.70 | O |
| ATOM | 666 | N | LEU A | 89 | −0.342 | 9.077 | 0.223 | 1.00 | 48.45 | N |
| ATOM | 667 | CA | LEU A | 89 | −1.798 | 9.103 | 0.324 | 1.00 | 49.79 | C |
| ATOM | 668 | CB | LEU A | 89 | −2.448 | 9.418 | −1.033 | 1.00 | 52.39 | C |
| ATOM | 669 | CG | LEU A | 89 | −2.180 | 10.741 | −1.750 | 1.00 | 56.42 | C |
| ATOM | 670 | CD1 | LEU A | 89 | −2.961 | 10.849 | −3.049 | 1.00 | 60.31 | C |
| ATOM | 671 | CD2 | LEU A | 89 | −2.552 | 11.917 | −0.885 | 1.00 | 58.04 | C |
| ATOM | 672 | C | LEU A | 89 | −2.271 | 7.757 | 0.777 | 1.00 | 49.38 | C |

TABLE 6-continued

Atomic coordinates for CRBN:DDB1: Compound B (Human protein)

| ATOM | 673 | O | LEU A | 89 | −1.640 | 6.756 | 0.451 | 1.00 | 48.59 | O |
|---|---|---|---|---|---|---|---|---|---|---|
| ATOM | 674 | N | GLU A | 90 | −3.406 | 7.763 | 1.481 | 1.00 | 50.90 | N |
| ATOM | 675 | CA | GLU A | 90 | −4.106 | 6.575 | 1.945 | 1.00 | 55.01 | C |
| ATOM | 676 | CB | GLU A | 90 | −3.830 | 6.418 | 3.417 | 1.00 | 62.32 | C |
| ATOM | 677 | CG | GLU A | 90 | −4.501 | 5.213 | 4.056 | 1.00 | 69.81 | C |
| ATOM | 678 | CD | GLU A | 90 | −4.412 | 5.226 | 5.567 | 1.00 | 76.00 | C |
| ATOM | 679 | OE1 | GLU A | 90 | −3.896 | 6.234 | 6.167 | 1.00 | 73.83 | O |
| ATOM | 680 | OE2 | GLU A | 90 | −4.883 | 4.200 | 6.124 | 1.00 | 81.57 | O |
| ATOM | 681 | C | GLU A | 90 | −5.640 | 6.616 | 1.753 | 1.00 | 55.70 | C |
| ATOM | 682 | O | GLU A | 90 | −6.304 | 7.663 | 1.934 | 1.00 | 53.95 | O |
| ATOM | 683 | N | TYR A | 91 | −6.194 | 5.440 | 1.461 | 1.00 | 56.54 | N |
| ATOM | 684 | CA | TYR A | 91 | −7.625 | 5.264 | 1.194 | 1.00 | 57.20 | C |
| ATOM | 685 | CB | TYR A | 91 | −7.793 | 4.036 | 0.314 | 1.00 | 55.59 | C |
| ATOM | 686 | CG | TYR A | 91 | −9.136 | 3.780 | −0.270 | 1.00 | 52.74 | C |
| ATOM | 687 | CD1 | TYR A | 91 | −9.513 | 4.297 | −1.485 | 1.00 | 56.14 | C |
| ATOM | 688 | CE1 | TYR A | 91 | −10.757 | 4.014 | −2.030 | 1.00 | 57.78 | C |
| ATOM | 689 | CZ | TYR A | 91 | −11.612 | 3.182 | −1.350 | 1.00 | 57.30 | C |
| ATOM | 690 | OH | TYR A | 91 | −12.868 | 2.816 | −1.781 | 1.00 | 57.05 | O |
| ATOM | 691 | CE2 | TYR A | 91 | −11.234 | 2.676 | −0.154 | 1.00 | 58.23 | C |
| ATOM | 692 | CD2 | TYR A | 91 | −9.992 | 2.962 | 0.358 | 1.00 | 56.06 | C |
| ATOM | 693 | C | TYR A | 91 | −8.379 | 5.077 | 2.504 | 1.00 | 58.02 | C |
| ATOM | 694 | O | TYR A | 91 | −8.043 | 4.221 | 3.273 | 1.00 | 57.15 | O |
| ATOM | 695 | N | LYS A | 92 | −9.404 | 5.881 | 2.737 | 1.00 | 61.56 | N |
| ATOM | 696 | CA | LYS A | 92 | −10.154 | 5.845 | 3.959 | 1.00 | 65.18 | C |
| ATOM | 697 | CB | LYS A | 92 | −9.854 | 7.098 | 4.762 | 1.00 | 68.82 | C |
| ATOM | 698 | CG | LYS A | 92 | −8.933 | 6.820 | 5.914 | 1.00 | 78.32 | C |
| ATOM | 699 | CD | LYS A | 92 | −9.614 | 6.028 | 7.039 | 1.00 | 82.94 | C |
| ATOM | 700 | CE | LYS A | 92 | −8.880 | 6.244 | 8.374 | 1.00 | 87.48 | C |
| ATOM | 701 | NZ | LYS A | 92 | −7.406 | 5.980 | 8.282 | 1.00 | 85.82 | N |
| ATOM | 702 | C | LYS A | 92 | −11.655 | 5.704 | 3.732 | 1.00 | 68.50 | C |
| ATOM | 703 | O | LYS A | 92 | −12.361 | 6.683 | 3.458 | 1.00 | 64.60 | O |
| ATOM | 704 | N | GLN A | 93 | −12.152 | 4.478 | 3.893 | 1.00 | 71.90 | N |
| ATOM | 705 | CA | GLN A | 93 | −13.582 | 4.269 | 4.019 | 1.00 | 72.73 | C |
| ATOM | 706 | CB | GLN A | 93 | −13.928 | 2.871 | 3.626 | 1.00 | 78.18 | C |
| ATOM | 707 | CG | GLN A | 93 | −15.408 | 2.657 | 3.425 | 1.00 | 80.21 | C |
| ATOM | 708 | CD | GLN A | 93 | −15.666 | 2.077 | 2.063 | 1.00 | 86.46 | C |
| ATOM | 709 | OE1 | GLN A | 93 | −14.803 | 1.377 | 1.486 | 1.00 | 87.95 | O |
| ATOM | 710 | NE2 | GLN A | 93 | −16.843 | 2.387 | 1.510 | 1.00 | 89.41 | N |
| ATOM | 711 | C | GLN A | 93 | −13.962 | 4.481 | 5.464 | 1.00 | 76.38 | C |
| ATOM | 712 | O | GLN A | 93 | −13.467 | 3.778 | 6.354 | 1.00 | 81.86 | O |
| ATOM | 713 | N | SER A | 94 | −14.774 | 5.503 | 5.699 | 1.00 | 75.75 | N |
| ATOM | 714 | CA | SER A | 94 | −15.346 | 5.789 | 7.005 | 1.00 | 69.58 | C |
| ATOM | 715 | CB | SER A | 94 | −14.888 | 7.162 | 7.525 | 1.00 | 61.42 | C |
| ATOM | 716 | C | SER A | 94 | −16.855 | 5.668 | 6.708 | 1.00 | 71.86 | C |
| ATOM | 717 | O | SER A | 94 | −17.498 | 6.562 | 6.148 | 1.00 | 69.43 | O |
| ATOM | 718 | N | GLY A | 95 | −17.384 | 4.484 | 6.988 | 1.00 | 77.84 | N |
| ATOM | 719 | CA | GLY A | 95 | −18.811 | 4.217 | 6.887 | 1.00 | 77.67 | C |
| ATOM | 720 | C | GLY A | 95 | −19.220 | 3.923 | 5.478 | 1.00 | 77.11 | C |
| ATOM | 721 | O | GLY A | 95 | −18.718 | 2.978 | 4.883 | 1.00 | 79.28 | O |
| ATOM | 722 | N | GLU A | 96 | −20.143 | 4.729 | 4.958 | 1.00 | 79.14 | N |
| ATOM | 723 | CA | GLU A | 96 | −20.588 | 4.641 | 3.557 | 1.00 | 81.46 | C |
| ATOM | 724 | CB | GLU A | 96 | −22.142 | 4.585 | 3.456 | 1.00 | 79.12 | C |
| ATOM | 725 | C | GLU A | 96 | −19.985 | 5.811 | 2.730 | 1.00 | 74.77 | C |
| ATOM | 726 | O | GLU A | 96 | −20.496 | 6.144 | 1.673 | 1.00 | 74.22 | O |
| ATOM | 727 | N | SER A | 97 | −18.893 | 6.417 | 3.198 | 1.00 | 69.03 | N |
| ATOM | 728 | CA | SER A | 97 | −18.185 | 7.392 | 2.385 | 1.00 | 67.90 | C |
| ATOM | 729 | CB | SER A | 97 | −18.542 | 8.825 | 2.820 | 1.00 | 63.74 | C |
| ATOM | 730 | OG | SER A | 97 | −17.968 | 9.119 | 4.041 | 1.00 | 56.82 | O |
| ATOM | 731 | C | SER A | 97 | −16.661 | 7.094 | 2.311 | 1.00 | 68.17 | C |
| ATOM | 732 | O | SER A | 97 | −16.069 | 6.515 | 3.220 | 1.00 | 72.32 | O |
| ATOM | 733 | N | ILE A | 98 | −16.070 | 7.474 | 1.181 | 1.00 | 67.05 | N |
| ATOM | 734 | CA | ILE A | 98 | −14.742 | 7.045 | 0.742 | 1.00 | 64.47 | C |
| ATOM | 735 | CB | ILE A | 98 | −14.809 | 6.382 | −0.672 | 1.00 | 66.14 | C |
| ATOM | 736 | CG1 | ILE A | 98 | −15.917 | 5.328 | −0.766 | 1.00 | 69.43 | C |
| ATOM | 737 | CD1 | ILE A | 98 | −17.252 | 5.863 | −1.310 | 1.00 | 78.70 | C |
| ATOM | 738 | CG2 | ILE A | 98 | −13.476 | 5.790 | −1.082 | 1.00 | 66.43 | C |
| ATOM | 739 | C | ILE A | 98 | −13.926 | 8.332 | 0.634 | 1.00 | 62.10 | C |
| ATOM | 740 | O | ILE A | 98 | −14.454 | 9.325 | 0.137 | 1.00 | 67.96 | O |
| ATOM | 741 | N | ASP A | 99 | −12.655 | 8.304 | 1.046 | 1.00 | 58.38 | N |
| ATOM | 742 | CA | ASP A | 99 | −11.805 | 9.508 | 1.164 | 1.00 | 58.36 | C |
| ATOM | 743 | CB | ASP A | 99 | −12.025 | 10.206 | 2.521 | 1.00 | 61.67 | C |
| ATOM | 744 | CG | ASP A | 99 | −13.153 | 11.232 | 2.504 | 1.00 | 64.23 | C |
| ATOM | 745 | OD1 | ASP A | 99 | −13.754 | 11.569 | 1.458 | 1.00 | 67.72 | O |
| ATOM | 746 | OD2 | ASP A | 99 | −13.424 | 11.747 | 3.588 | 1.00 | 76.12 | O |
| ATOM | 747 | C | ASP A | 99 | −10.317 | 9.222 | 1.058 | 1.00 | 56.57 | C |
| ATOM | 748 | O | ASP A | 99 | −9.834 | 8.240 | 1.589 | 1.00 | 61.19 | O |
| ATOM | 749 | N | ILE A | 100 | −9.579 | 10.117 | 0.414 | 1.00 | 56.01 | N |
| ATOM | 750 | CA | ILE A | 100 | −8.159 | 9.920 | 0.206 | 1.00 | 53.27 | C |

TABLE 6-continued

Atomic coordinates for CRBN:DDB1: Compound B (Human protein)

| ATOM | 751 | CB | ILE A | 100 | −7.806 | 9.984 | −1.284 | 1.00 | 52.13 | C |
|---|---|---|---|---|---|---|---|---|---|---|
| ATOM | 752 | CG1 | ILE A | 100 | −8.906 | 9.247 | −2.066 | 1.00 | 52.79 | C |
| ATOM | 753 | CD1 | ILE A | 100 | −8.436 | 8.369 | −3.181 | 1.00 | 56.05 | C |
| ATOM | 754 | CG2 | ILE A | 100 | −6.368 | 9.490 | −1.508 | 1.00 | 49.37 | C |
| ATOM | 755 | C | ILE A | 100 | −7.438 | 10.970 | 1.034 | 1.00 | 53.05 | C |
| ATOM | 756 | O | ILE A | 100 | −7.420 | 12.178 | 0.728 | 1.00 | 53.89 | O |
| ATOM | 757 | N | ILE A | 101 | −6.839 | 10.479 | 2.096 | 1.00 | 51.06 | N |
| ATOM | 758 | CA | ILE A | 101 | −6.298 | 11.334 | 3.111 | 1.00 | 53.96 | C |
| ATOM | 759 | CB | ILE A | 101 | −6.697 | 10.851 | 4.532 | 1.00 | 56.54 | C |
| ATOM | 760 | CG1 | ILE A | 101 | −6.069 | 9.488 | 4.854 | 1.00 | 59.52 | C |
| ATOM | 761 | CD1 | ILE A | 101 | −6.137 | 9.078 | 6.291 | 1.00 | 61.61 | C |
| ATOM | 762 | CG2 | ILE A | 101 | −8.212 | 10.708 | 4.637 | 1.00 | 56.65 | C |
| ATOM | 763 | C | ILE A | 101 | −4.804 | 11.327 | 2.888 | 1.00 | 53.61 | C |
| ATOM | 764 | O | ILE A | 101 | −4.240 | 10.370 | 2.355 | 1.00 | 51.73 | O |
| ATOM | 765 | N | THR A | 102 | −4.169 | 12.384 | 3.362 | 1.00 | 54.11 | N |
| ATOM | 766 | CA | THR A | 102 | −2.801 | 12.697 | 3.039 | 1.00 | 49.59 | C |
| ATOM | 767 | CB | THR A | 102 | −2.745 | 14.171 | 2.662 | 1.00 | 49.20 | C |
| ATOM | 768 | OG1 | THR A | 102 | −3.700 | 14.434 | 1.623 | 1.00 | 51.50 | O |
| ATOM | 769 | CG2 | THR A | 102 | −1.392 | 14.559 | 2.221 | 1.00 | 51.05 | C |
| ATOM | 770 | C | THR A | 102 | −1.982 | 12.451 | 4.272 | 1.00 | 49.45 | C |
| ATOM | 771 | O | THR A | 102 | −1.980 | 13.257 | 5.206 | 1.00 | 55.36 | O |
| ATOM | 772 | N | ARG A | 103 | −1.310 | 11.323 | 4.294 | 1.00 | 47.26 | N |
| ATOM | 773 | CA | ARG A | 103 | −0.372 | 11.012 | 5.352 | 1.00 | 48.19 | C |
| ATOM | 774 | CB | ARG A | 103 | 0.096 | 9.575 | 5.202 | 1.00 | 49.65 | C |
| ATOM | 775 | CG | ARG A | 103 | −1.021 | 8.578 | 5.487 | 1.00 | 53.14 | C |
| ATOM | 776 | CD | ARG A | 103 | −1.148 | 8.307 | 6.981 | 1.00 | 52.54 | C |
| ATOM | 777 | NE | ARG A | 103 | −0.039 | 7.446 | 7.366 | 1.00 | 50.53 | N |
| ATOM | 778 | CZ | ARG A | 103 | −0.032 | 6.121 | 7.236 | 1.00 | 50.77 | C |
| ATOM | 779 | NH1 | ARG A | 103 | −1.087 | 5.446 | 6.764 | 1.00 | 49.86 | N |
| ATOM | 780 | NH2 | ARG A | 103 | 1.042 | 5.452 | 7.605 | 1.00 | 52.24 | N |
| ATOM | 781 | C | ARG A | 103 | 0.877 | 11.892 | 5.411 | 1.00 | 50.86 | C |
| ATOM | 782 | O | ARG A | 103 | 1.504 | 11.969 | 6.450 | 1.00 | 61.85 | O |
| ATOM | 783 | N | ALA A | 104 | 1.281 | 12.517 | 4.314 | 1.00 | 48.97 | N |
| ATOM | 784 | CA | ALA A | 104 | 2.528 | 13.282 | 4.262 | 1.00 | 45.79 | C |
| ATOM | 785 | CB | ALA A | 104 | 3.737 | 12.362 | 4.262 | 1.00 | 43.83 | C |
| ATOM | 786 | C | ALA A | 104 | 2.536 | 14.121 | 3.008 | 1.00 | 46.52 | C |
| ATOM | 787 | O | ALA A | 104 | 1.983 | 13.746 | 1.992 | 1.00 | 42.88 | O |
| ATOM | 788 | N | HIS A | 105 | 3.171 | 15.272 | 3.063 | 1.00 | 49.70 | N |
| ATOM | 789 | CA | HIS A | 105 | 3.251 | 16.073 | 1.869 | 1.00 | 50.89 | C |
| ATOM | 790 | CB | HIS A | 105 | 1.927 | 16.774 | 1.600 | 1.00 | 51.38 | C |
| ATOM | 791 | CG | HIS A | 105 | 1.692 | 17.913 | 2.523 | 1.00 | 53.93 | C |
| ATOM | 792 | ND1 | HIS A | 105 | 1.406 | 17.726 | 3.860 | 1.00 | 57.72 | N |
| ATOM | 793 | CE1 | HIS A | 105 | 1.313 | 18.900 | 4.452 | 1.00 | 56.98 | C |
| ATOM | 794 | NE2 | HIS A | 105 | 1.542 | 19.837 | 3.545 | 1.00 | 55.84 | N |
| ATOM | 795 | CD2 | HIS A | 105 | 1.806 | 19.246 | 2.339 | 1.00 | 51.71 | C |
| ATOM | 796 | C | HIS A | 105 | 4.303 | 17.112 | 2.040 | 1.00 | 48.43 | C |
| ATOM | 797 | O | HIS A | 105 | 4.422 | 17.700 | 3.099 | 1.00 | 50.73 | O |
| ATOM | 798 | N | GLY A | 106 | 5.048 | 17.346 | 0.978 | 1.00 | 47.91 | N |
| ATOM | 799 | CA | GLY A | 106 | 5.896 | 18.521 | 0.897 | 1.00 | 48.89 | C |
| ATOM | 800 | C | GLY A | 106 | 6.382 | 18.784 | −0.509 | 1.00 | 47.17 | C |
| ATOM | 801 | O | GLY A | 106 | 6.326 | 17.891 | −1.342 | 1.00 | 53.37 | O |
| ATOM | 802 | N | ASN A | 107 | 6.897 | 19.975 | −0.763 | 1.00 | 43.94 | N |
| ATOM | 803 | CA | ASN A | 107 | 7.372 | 20.299 | −2.079 | 1.00 | 47.06 | C |
| ATOM | 804 | CB | ASN A | 107 | 7.011 | 21.733 | −2.434 | 1.00 | 50.09 | C |
| ATOM | 805 | CG | ASN A | 107 | 7.306 | 22.066 | −3.866 | 1.00 | 53.77 | C |
| ATOM | 806 | OD1 | ASN A | 107 | 8.384 | 21.790 | −4.361 | 1.00 | 58.13 | O |
| ATOM | 807 | ND2 | ASN A | 107 | 6.347 | 22.658 | −4.543 | 1.00 | 59.29 | N |
| ATOM | 808 | C | ASN A | 107 | 8.864 | 20.059 | −2.206 | 1.00 | 47.02 | C |
| ATOM | 809 | O | ASN A | 107 | 9.622 | 20.763 | −1.608 | 1.00 | 51.85 | O |
| ATOM | 810 | N | VAL A | 108 | 9.285 | 19.148 | −3.079 | 1.00 | 47.79 | N |
| ATOM | 811 | CA | VAL A | 108 | 10.669 | 18.666 | −3.118 | 1.00 | 47.12 | C |
| ATOM | 812 | CB | VAL A | 108 | 10.703 | 17.165 | −3.404 | 1.00 | 46.51 | C |
| ATOM | 813 | CG1 | VAL A | 108 | 9.798 | 16.445 | −2.439 | 1.00 | 46.42 | C |
| ATOM | 814 | CG2 | VAL A | 108 | 10.226 | 16.848 | −4.815 | 1.00 | 49.30 | C |
| ATOM | 815 | C | VAL A | 108 | 11.543 | 19.397 | −4.112 | 1.00 | 51.22 | C |
| ATOM | 816 | O | VAL A | 108 | 12.609 | 18.917 | −4.464 | 1.00 | 56.63 | O |
| ATOM | 817 | N | GLN A | 109 | 11.108 | 20.562 | −4.559 | 1.00 | 53.35 | N |
| ATOM | 818 | CA | GLN A | 109 | 11.867 | 21.393 | −5.490 | 1.00 | 58.39 | C |
| ATOM | 819 | CB | GLN A | 109 | 11.029 | 22.618 | −5.682 | 1.00 | 62.94 | C |
| ATOM | 820 | CG | GLN A | 109 | 11.517 | 23.706 | −6.577 | 1.00 | 68.36 | C |
| ATOM | 821 | CD | GLN A | 109 | 10.326 | 24.522 | −7.025 | 1.00 | 75.56 | C |
| ATOM | 822 | OE1 | GLN A | 109 | 9.331 | 24.684 | −6.285 | 1.00 | 78.20 | O |
| ATOM | 823 | NE2 | GLN A | 109 | 10.380 | 24.991 | −8.256 | 1.00 | 79.30 | N |
| ATOM | 824 | C | GLN A | 109 | 13.197 | 21.828 | −4.933 | 1.00 | 60.61 | C |
| ATOM | 825 | O | GLN A | 109 | 13.286 | 21.967 | −3.743 | 1.00 | 61.78 | O |
| ATOM | 826 | N | ASP A | 110 | 14.217 | 22.033 | −5.778 | 1.00 | 65.43 | N |
| ATOM | 827 | CA | ASP A | 110 | 15.471 | 22.784 | −5.429 | 1.00 | 67.40 | C |
| ATOM | 828 | CB | ASP A | 110 | 16.701 | 21.965 | −5.843 | 1.00 | 66.15 | C |

TABLE 6-continued

Atomic coordinates for CRBN:DDB1: Compound B (Human protein)

| ATOM | 829 | CG | ASP A | 110 | 16.847 | 20.693 | −5.055 | 1.00 | 62.70 | C |
|---|---|---|---|---|---|---|---|---|---|---|
| ATOM | 830 | OD1 | ASP A | 110 | 16.405 | 20.706 | −3.914 | 1.00 | 59.32 | O |
| ATOM | 831 | OD2 | ASP A | 110 | 17.411 | 19.681 | −5.536 | 1.00 | 65.85 | O |
| ATOM | 832 | C | ASP A | 110 | 15.559 | 24.187 | −6.106 | 1.00 | 71.79 | C |
| ATOM | 833 | O | ASP A | 110 | 15.330 | 24.282 | −7.311 | 1.00 | 78.30 | O |
| ATOM | 834 | N | ARG A | 111 | 15.911 | 25.253 | −5.363 | 1.00 | 76.56 | N |
| ATOM | 835 | CA | ARG A | 111 | 15.990 | 26.641 | −5.934 | 1.00 | 76.01 | C |
| ATOM | 836 | CB | ARG A | 111 | 16.425 | 27.666 | −4.858 | 1.00 | 68.40 | C |
| ATOM | 837 | C | ARG A | 111 | 16.909 | 26.713 | −7.204 | 1.00 | 79.48 | C |
| ATOM | 838 | O | ARG A | 111 | 16.474 | 27.169 | −8.262 | 1.00 | 80.60 | O |
| ATOM | 839 | N | ILE A | 112 | 18.155 | 26.241 | −7.073 | 1.00 | 79.58 | N |
| ATOM | 840 | CA | ILE A | 112 | 19.124 | 26.124 | −8.157 | 1.00 | 75.26 | C |
| ATOM | 841 | CB | ILE A | 112 | 20.554 | 26.568 | −7.666 | 1.00 | 61.20 | C |
| ATOM | 842 | C | ILE A | 112 | 19.048 | 24.637 | −8.651 | 1.00 | 82.82 | C |
| ATOM | 843 | O | ILE A | 112 | 19.347 | 23.684 | −7.882 | 1.00 | 90.40 | O |
| ATOM | 844 | N | GLY A | 113 | 18.595 | 24.440 | −9.904 | 1.00 | 82.38 | N |
| ATOM | 845 | CA | GLY A | 113 | 18.653 | 23.113 | −10.614 | 1.00 | 78.36 | C |
| ATOM | 846 | C | GLY A | 113 | 18.242 | 23.084 | −12.118 | 1.00 | 77.60 | C |
| ATOM | 847 | O | GLY A | 113 | 17.204 | 23.676 | −12.507 | 1.00 | 68.87 | O |
| ATOM | 848 | N | ARG A | 114 | 19.041 | 22.403 | −12.973 | 1.00 | 77.96 | N |
| ATOM | 849 | CA | ARG A | 114 | 18.672 | 22.159 | −14.417 | 1.00 | 78.28 | C |
| ATOM | 850 | CB | ARG A | 114 | 19.879 | 22.129 | −15.404 | 1.00 | 73.48 | C |
| ATOM | 851 | C | ARG A | 114 | 17.877 | 20.840 | −14.484 | 1.00 | 75.49 | C |
| ATOM | 852 | O | ARG A | 114 | 18.418 | 19.767 | −14.168 | 1.00 | 79.51 | O |
| ATOM | 853 | N | PRO A | 115 | 16.581 | 20.911 | −14.859 | 1.00 | 69.41 | N |
| ATOM | 854 | CA | PRO A | 115 | 15.778 | 19.667 | −14.837 | 1.00 | 62.52 | C |
| ATOM | 855 | CB | PRO A | 115 | 14.359 | 20.153 | −15.120 | 1.00 | 61.34 | C |
| ATOM | 856 | CG | PRO A | 115 | 14.390 | 21.649 | −14.989 | 1.00 | 63.02 | C |
| ATOM | 857 | CD | PRO A | 115 | 15.785 | 22.082 | −15.280 | 1.00 | 65.33 | C |
| ATOM | 858 | C | PRO A | 115 | 16.236 | 18.719 | −15.907 | 1.00 | 56.91 | C |
| ATOM | 859 | O | PRO A | 115 | 16.488 | 19.151 | −17.023 | 1.00 | 54.46 | O |
| ATOM | 860 | N | SER A | 116 | 16.363 | 17.455 | −15.569 | 1.00 | 55.96 | N |
| ATOM | 861 | CA | SER A | 116 | 17.001 | 16.500 | −16.471 | 1.00 | 66.16 | C |
| ATOM | 862 | CB | SER A | 116 | 17.128 | 15.158 | −15.783 | 1.00 | 70.10 | C |
| ATOM | 863 | OG | SER A | 116 | 17.654 | 15.346 | −14.490 | 1.00 | 76.88 | O |
| ATOM | 864 | C | SER A | 116 | 16.291 | 16.271 | −17.795 | 1.00 | 70.62 | C |
| ATOM | 865 | O | SER A | 116 | 15.078 | 16.373 | −17.861 | 1.00 | 76.73 | O |
| ATOM | 866 | N | GLU A | 117 | 17.043 | 15.907 | −18.832 | 1.00 | 74.86 | N |
| ATOM | 867 | CA | GLU A | 117 | 16.471 | 15.733 | −20.172 | 1.00 | 75.45 | C |
| ATOM | 868 | CB | GLU A | 117 | 17.540 | 15.693 | −21.272 | 1.00 | 82.27 | C |
| ATOM | 869 | CG | GLU A | 117 | 18.069 | 17.049 | −21.734 | 1.00 | 88.29 | C |
| ATOM | 870 | CD | GLU A | 117 | 19.143 | 16.929 | −22.817 | 1.00 | 94.14 | C |
| ATOM | 871 | OE1 | GLU A | 117 | 20.074 | 17.761 | −22.858 | 1.00 | 99.09 | O |
| ATOM | 872 | OE2 | GLU A | 117 | 19.069 | 15.996 | −23.638 | 1.00 | 101.87 | O |
| ATOM | 873 | C | GLU A | 117 | 15.632 | 14.502 | −20.284 | 1.00 | 72.06 | C |
| ATOM | 874 | O | GLU A | 117 | 14.887 | 14.397 | −21.237 | 1.00 | 80.37 | O |
| ATOM | 875 | N | THR A | 118 | 15.756 | 13.560 | −19.356 | 1.00 | 72.67 | N |
| ATOM | 876 | CA | THR A | 118 | 14.833 | 12.403 | −19.299 | 1.00 | 75.68 | C |
| ATOM | 877 | CB | THR A | 118 | 15.602 | 11.129 | −18.969 | 1.00 | 78.26 | C |
| ATOM | 878 | OG1 | THR A | 118 | 16.965 | 11.336 | −19.322 | 1.00 | 80.04 | O |
| ATOM | 879 | CG2 | THR A | 118 | 15.054 | 9.959 | −19.735 | 1.00 | 83.14 | C |
| ATOM | 880 | C | THR A | 118 | 13.672 | 12.588 | −18.296 | 1.00 | 70.30 | C |
| ATOM | 881 | O | THR A | 118 | 12.984 | 11.651 | −17.863 | 1.00 | 63.75 | O |
| ATOM | 882 | N | GLY A | 119 | 13.448 | 13.830 | −17.940 | 1.00 | 71.53 | N |
| ATOM | 883 | CA | GLY A | 119 | 12.362 | 14.168 | −17.070 | 1.00 | 73.84 | C |
| ATOM | 884 | C | GLY A | 119 | 12.481 | 13.665 | −15.653 | 1.00 | 67.38 | C |
| ATOM | 885 | O | GLY A | 119 | 13.512 | 13.155 | −15.226 | 1.00 | 70.63 | O |
| ATOM | 886 | N | ILE A | 120 | 11.367 | 13.812 | −14.954 | 1.00 | 61.25 | N |
| ATOM | 887 | CA | ILE A | 120 | 11.229 | 13.393 | −13.594 | 1.00 | 54.05 | C |
| ATOM | 888 | CB | ILE A | 120 | 9.865 | 13.801 | −13.059 | 1.00 | 52.55 | C |
| ATOM | 889 | CG1 | ILE A | 120 | 9.685 | 15.332 | −13.239 | 1.00 | 55.14 | C |
| ATOM | 890 | CD1 | ILE A | 120 | 9.354 | 16.188 | −12.010 | 1.00 | 56.56 | C |
| ATOM | 891 | CG2 | ILE A | 120 | 9.711 | 13.266 | −11.650 | 1.00 | 51.99 | C |
| ATOM | 892 | C | ILE A | 120 | 11.282 | 11.910 | −13.633 | 1.00 | 50.93 | C |
| ATOM | 893 | O | ILE A | 120 | 10.658 | 11.353 | −14.477 | 1.00 | 50.42 | O |
| ATOM | 894 | N | ILE A | 121 | 12.064 | 11.284 | −12.770 | 1.00 | 49.35 | N |
| ATOM | 895 | CA | ILE A | 121 | 11.943 | 9.856 | −12.538 | 1.00 | 52.07 | C |
| ATOM | 896 | CB | ILE A | 121 | 13.172 | 9.089 | −13.003 | 1.00 | 53.29 | C |
| ATOM | 897 | CG1 | ILE A | 121 | 13.182 | 9.041 | −14.534 | 1.00 | 54.83 | C |
| ATOM | 898 | CD1 | ILE A | 121 | 14.529 | 8.705 | −15.121 | 1.00 | 55.63 | C |
| ATOM | 899 | CG2 | ILE A | 121 | 13.203 | 7.689 | −12.397 | 1.00 | 51.51 | C |
| ATOM | 900 | C | ILE A | 121 | 11.883 | 9.713 | −11.071 | 1.00 | 54.33 | C |
| ATOM | 901 | O | ILE A | 121 | 12.672 | 10.363 | −10.409 | 1.00 | 56.66 | O |
| ATOM | 902 | N | GLY A | 122 | 11.001 | 8.818 | −10.592 | 1.00 | 58.02 | N |
| ATOM | 903 | CA | GLY A | 122 | 10.735 | 8.558 | −9.159 | 1.00 | 53.84 | C |
| ATOM | 904 | C | GLY A | 122 | 10.562 | 7.070 | −8.848 | 1.00 | 53.08 | C |
| ATOM | 905 | O | GLY A | 122 | 9.849 | 6.362 | −9.538 | 1.00 | 49.84 | O |
| ATOM | 906 | N | ILE A | 123 | 11.194 | 6.610 | −7.773 | 1.00 | 56.03 | N |

TABLE 6-continued

Atomic coordinates for CRBN:DDB1: Compound B (Human protein)

| ATOM | 907 | CA | ILE A | 123 | 11.350 | 5.178 | −7.484 | 1.00 | 57.82 | C |
|---|---|---|---|---|---|---|---|---|---|---|
| ATOM | 908 | CB | ILE A | 123 | 12.641 | 4.623 | −8.130 | 1.00 | 57.79 | C |
| ATOM | 909 | CG1 | ILE A | 123 | 13.822 | 5.552 | −7.848 | 1.00 | 55.17 | C |
| ATOM | 910 | CD1 | ILE A | 123 | 15.124 | 5.005 | −8.342 | 1.00 | 56.03 | C |
| ATOM | 911 | CG2 | ILE A | 123 | 12.463 | 4.418 | −9.635 | 1.00 | 58.20 | C |
| ATOM | 912 | C | ILE A | 123 | 11.435 | 4.884 | −5.987 | 1.00 | 60.01 | C |
| ATOM | 913 | O | ILE A | 123 | 11.892 | 5.725 | −5.215 | 1.00 | 60.53 | O |
| ATOM | 914 | N | ILE A | 124 | 11.044 | 3.672 | −5.591 | 1.00 | 60.36 | N |
| ATOM | 915 | CA | ILE A | 124 | 11.049 | 3.293 | −4.198 | 1.00 | 61.06 | C |
| ATOM | 916 | CB | ILE A | 124 | 9.604 | 3.162 | −3.717 | 1.00 | 63.31 | C |
| ATOM | 917 | CG1 | ILE A | 124 | 8.814 | 4.427 | −4.091 | 1.00 | 63.35 | C |
| ATOM | 918 | CD1 | ILE A | 124 | 7.513 | 4.639 | −3.345 | 1.00 | 63.23 | C |
| ATOM | 919 | CG2 | ILE A | 124 | 9.546 | 2.888 | −2.211 | 1.00 | 67.90 | C |
| ATOM | 920 | C | ILE A | 124 | 11.766 | 1.968 | −4.025 | 1.00 | 64.99 | C |
| ATOM | 921 | O | ILE A | 124 | 11.475 | 1.030 | −4.743 | 1.00 | 67.05 | O |
| ATOM | 922 | N | ASP A | 125 | 12.671 | 1.864 | −3.055 | 1.00 | 72.94 | N |
| ATOM | 923 | CA | ASP A | 125 | 13.356 | 0.582 | −2.820 | 1.00 | 79.86 | C |
| ATOM | 924 | CB | ASP A | 125 | 14.581 | 0.699 | −1.867 | 1.00 | 84.31 | C |
| ATOM | 925 | CG | ASP A | 125 | 14.290 | 0.272 | −0.427 | 1.00 | 85.41 | C |
| ATOM | 926 | OD1 | ASP A | 125 | 13.733 | 1.099 | 0.330 | 1.00 | 90.46 | O |
| ATOM | 927 | OD2 | ASP A | 125 | 14.663 | −0.869 | −0.052 | 1.00 | 80.49 | O |
| ATOM | 928 | C | ASP A | 125 | 12.347 | −0.458 | −2.339 | 1.00 | 79.18 | C |
| ATOM | 929 | O | ASP A | 125 | 11.370 | −0.100 | −1.680 | 1.00 | 75.13 | O |
| ATOM | 930 | N | PRO A | 126 | 12.579 | −1.744 | −2.667 | 1.00 | 81.41 | N |
| ATOM | 931 | CA | PRO A | 126 | 11.581 | −2.753 | −2.339 | 1.00 | 82.11 | C |
| ATOM | 932 | CB | PRO A | 126 | 12.048 | −4.005 | −3.089 | 1.00 | 81.06 | C |
| ATOM | 933 | CG | PRO A | 126 | 13.329 | −3.643 | −3.756 | 1.00 | 82.34 | C |
| ATOM | 934 | CD | PRO A | 126 | 13.816 | −2.357 | −3.169 | 1.00 | 82.21 | C |
| ATOM | 935 | C | PRO A | 126 | 11.462 | −3.059 | −0.866 | 1.00 | 84.35 | C |
| ATOM | 936 | O | PRO A | 126 | 10.485 | −3.671 | −0.500 | 1.00 | 85.14 | O |
| ATOM | 937 | N | GLU A | 127 | 12.438 | −2.679 | −0.036 | 1.00 | 91.04 | N |
| ATOM | 938 | CA | GLU A | 127 | 12.243 | −2.708 | 1.423 | 1.00 | 93.78 | C |
| ATOM | 939 | CB | GLU A | 127 | 13.559 | −2.584 | 2.184 | 1.00 | 100.16 | C |
| ATOM | 940 | CG | GLU A | 127 | 14.584 | −3.693 | 2.036 | 1.00 | 102.60 | C |
| ATOM | 941 | CD | GLU A | 127 | 15.722 | −3.479 | 3.041 | 1.00 | 106.00 | C |
| ATOM | 942 | OE1 | GLU A | 127 | 16.405 | −2.412 | 2.957 | 1.00 | 105.48 | O |
| ATOM | 943 | OE2 | GLU A | 127 | 15.905 | −4.353 | 3.931 | 1.00 | 95.68 | O |
| ATOM | 944 | C | GLU A | 127 | 11.327 | −1.584 | 1.945 | 1.00 | 89.78 | C |
| ATOM | 945 | O | GLU A | 127 | 10.808 | −1.721 | 3.054 | 1.00 | 91.00 | O |
| ATOM | 946 | N | CYS A | 128 | 11.170 | −0.498 | 1.164 | 1.00 | 82.65 | N |
| ATOM | 947 | CA | CYS A | 128 | 10.444 | 0.754 | 1.521 | 1.00 | 73.84 | C |
| ATOM | 948 | CB | CYS A | 128 | 8.969 | 0.509 | 1.883 | 1.00 | 68.83 | C |
| ATOM | 949 | SG | CYS A | 128 | 8.016 | −0.403 | 0.648 | 1.00 | 63.43 | S |
| ATOM | 950 | C | CYS A | 128 | 11.159 | 1.576 | 2.599 | 1.00 | 76.06 | C |
| ATOM | 951 | O | CYS A | 128 | 10.534 | 2.166 | 3.486 | 1.00 | 78.10 | O |
| ATOM | 952 | N | ARG A | 129 | 12.480 | 1.604 | 2.511 | 1.00 | 81.28 | N |
| ATOM | 953 | CA | ARG A | 129 | 13.284 | 2.495 | 3.322 | 1.00 | 87.79 | C |
| ATOM | 954 | CB | ARG A | 129 | 14.767 | 2.065 | 3.346 | 1.00 | 97.19 | C |
| ATOM | 955 | CG | ARG A | 129 | 15.090 | 0.721 | 4.012 | 1.00 | 106.15 | C |
| ATOM | 956 | CD | ARG A | 129 | 14.243 | 0.445 | 5.260 | 1.00 | 116.20 | C |
| ATOM | 957 | NE | ARG A | 129 | 14.997 | 0.042 | 6.455 | 1.00 | 125.77 | N |
| ATOM | 958 | CZ | ARG A | 129 | 15.734 | 0.855 | 7.229 | 1.00 | 126.72 | C |
| ATOM | 959 | NH1 | ARG A | 129 | 15.905 | 2.151 | 6.928 | 1.00 | 123.41 | N |
| ATOM | 960 | NH2 | ARG A | 129 | 16.331 | 0.355 | 8.316 | 1.00 | 124.06 | N |
| ATOM | 961 | C | ARG A | 129 | 13.175 | 3.899 | 2.787 | 1.00 | 81.98 | C |
| ATOM | 962 | O | ARG A | 129 | 13.117 | 4.847 | 3.556 | 1.00 | 82.54 | O |
| ATOM | 963 | N | MET A | 130 | 13.137 | 4.053 | 1.473 | 1.00 | 78.74 | N |
| ATOM | 964 | CA | MET A | 130 | 13.189 | 5.393 | 0.917 | 1.00 | 76.38 | C |
| ATOM | 965 | CB | MET A | 130 | 14.646 | 5.815 | 0.777 | 1.00 | 76.55 | C |
| ATOM | 966 | CG | MET A | 130 | 15.296 | 5.327 | −0.529 | 1.00 | 73.80 | C |
| ATOM | 967 | SD | MET A | 130 | 17.080 | 5.382 | −0.526 | 1.00 | 63.88 | S |
| ATOM | 968 | CE | MET A | 130 | 17.273 | 4.156 | 0.760 | 1.00 | 70.24 | C |
| ATOM | 969 | C | MET A | 130 | 12.584 | 5.525 | −0.448 | 1.00 | 71.67 | C |
| ATOM | 970 | O | MET A | 130 | 12.331 | 4.529 | −1.116 | 1.00 | 72.90 | O |
| ATOM | 971 | N | ILE A | 131 | 12.492 | 6.786 | −0.868 | 1.00 | 66.54 | N |
| ATOM | 972 | CA | ILE A | 131 | 12.080 | 7.184 | −2.194 | 1.00 | 66.48 | C |
| ATOM | 973 | CB | ILE A | 131 | 10.892 | 8.153 | −2.097 | 1.00 | 67.69 | C |
| ATOM | 974 | CG1 | ILE A | 131 | 9.686 | 7.405 | −1.543 | 1.00 | 71.76 | C |
| ATOM | 975 | CD1 | ILE A | 131 | 8.482 | 8.288 | −1.315 | 1.00 | 75.90 | C |
| ATOM | 976 | CG2 | ILE A | 131 | 10.567 | 8.799 | −3.448 | 1.00 | 67.54 | C |
| ATOM | 977 | C | ILE A | 131 | 13.207 | 7.916 | −2.890 | 1.00 | 64.06 | C |
| ATOM | 978 | O | ILE A | 131 | 13.727 | 8.873 | −2.336 | 1.00 | 66.49 | O |
| ATOM | 979 | N | GLY A | 132 | 13.556 | 7.485 | −4.104 | 1.00 | 61.75 | N |
| ATOM | 980 | CA | GLY A | 132 | 14.445 | 8.245 | −5.002 | 1.00 | 62.08 | C |
| ATOM | 981 | C | GLY A | 132 | 13.744 | 9.151 | −6.041 | 1.00 | 61.44 | C |
| ATOM | 982 | O | GLY A | 132 | 12.796 | 8.736 | −6.725 | 1.00 | 55.45 | O |
| ATOM | 983 | N | LEU A | 133 | 14.222 | 10.386 | −6.174 | 1.00 | 58.51 | N |
| ATOM | 984 | CA | LEU A | 133 | 13.730 | 11.280 | −7.209 | 1.00 | 58.80 | C |

TABLE 6-continued

Atomic coordinates for CRBN:DDB1: Compound B (Human protein)

| ATOM | 985 | CB | LEU A | 133 | 12.891 | 12.446 | −6.631 | 1.00 | 58.35 | C |
|---|---|---|---|---|---|---|---|---|---|---|
| ATOM | 986 | CG | LEU A | 133 | 11.829 | 12.077 | −5.594 | 1.00 | 58.28 | C |
| ATOM | 987 | CD1 | LEU A | 133 | 11.202 | 13.278 | −4.946 | 1.00 | 56.03 | C |
| ATOM | 988 | CD2 | LEU A | 133 | 10.718 | 11.287 | −6.234 | 1.00 | 62.47 | C |
| ATOM | 989 | C | LEU A | 133 | 14.920 | 11.819 | −7.969 | 1.00 | 56.59 | C |
| ATOM | 990 | O | LEU A | 133 | 15.747 | 12.543 | −7.396 | 1.00 | 58.20 | O |
| ATOM | 991 | N | ARG A | 134 | 14.998 | 11.475 | −9.253 | 1.00 | 52.18 | N |
| ATOM | 992 | CA | ARG A | 134 | 15.910 | 12.140 | −10.141 | 1.00 | 52.65 | C |
| ATOM | 993 | CB | ARG A | 134 | 16.379 | 11.193 | −11.231 | 1.00 | 54.72 | C |
| ATOM | 994 | CG | ARG A | 134 | 17.621 | 11.694 | −11.933 | 1.00 | 56.03 | C |
| ATOM | 995 | CD | ARG A | 134 | 17.452 | 12.963 | −12.753 | 1.00 | 54.82 | C |
| ATOM | 996 | NE | ARG A | 134 | 17.683 | 12.626 | −14.125 | 1.00 | 58.60 | N |
| ATOM | 997 | CZ | ARG A | 134 | 16.819 | 12.009 | −14.912 | 1.00 | 66.06 | C |
| ATOM | 998 | NH1 | ARG A | 134 | 15.609 | 11.689 | −14.496 | 1.00 | 66.45 | N |
| ATOM | 999 | NH2 | ARG A | 134 | 17.174 | 11.720 | −16.155 | 1.00 | 74.13 | N |
| ATOM | 1000 | C | ARG A | 134 | 15.263 | 13.391 | −10.716 | 1.00 | 54.38 | C |
| ATOM | 1001 | O | ARG A | 134 | 14.655 | 13.376 | −11.776 | 1.00 | 53.55 | O |
| ATOM | 1002 | N | LEU A | 135 | 15.414 | 14.509 | −10.033 | 1.00 | 59.13 | N |
| ATOM | 1003 | CA | LEU A | 135 | 14.765 | 15.718 | −10.524 | 1.00 | 60.73 | C |
| ATOM | 1004 | CB | LEU A | 135 | 14.327 | 16.586 | −9.351 | 1.00 | 60.08 | C |
| ATOM | 1005 | CG | LEU A | 135 | 13.377 | 15.801 | −8.446 | 1.00 | 61.47 | C |
| ATOM | 1006 | CD1 | LEU A | 135 | 12.927 | 16.657 | −7.292 | 1.00 | 64.80 | C |
| ATOM | 1007 | CD2 | LEU A | 135 | 12.166 | 15.243 | −9.175 | 1.00 | 61.41 | C |
| ATOM | 1008 | C | LEU A | 135 | 15.675 | 16.459 | −11.470 | 1.00 | 61.53 | C |
| ATOM | 1009 | O | LEU A | 135 | 15.268 | 16.877 | −12.551 | 1.00 | 56.80 | O |
| ATOM | 1010 | N | TYR A | 136 | 16.925 | 16.601 | −11.054 | 1.00 | 67.47 | N |
| ATOM | 1011 | CA | TYR A | 136 | 17.869 | 17.448 | −11.753 | 1.00 | 65.12 | C |
| ATOM | 1012 | CB | TYR A | 136 | 18.195 | 18.600 | −10.827 | 1.00 | 65.50 | C |
| ATOM | 1013 | CG | TYR A | 136 | 16.992 | 19.344 | −10.234 | 1.00 | 63.22 | C |
| ATOM | 1014 | CD1 | TYR A | 136 | 16.332 | 20.283 | −10.987 | 1.00 | 62.35 | C |
| ATOM | 1015 | CE1 | TYR A | 136 | 15.278 | 21.002 | −10.475 | 1.00 | 63.81 | C |
| ATOM | 1016 | CZ | TYR A | 136 | 14.845 | 20.792 | −9.198 | 1.00 | 64.36 | C |
| ATOM | 1017 | OH | TYR A | 136 | 13.750 | 21.573 | −8.801 | 1.00 | 72.10 | O |
| ATOM | 1018 | CE2 | TYR A | 136 | 15.485 | 19.849 | −8.398 | 1.00 | 60.65 | C |
| ATOM | 1019 | CD2 | TYR A | 136 | 16.554 | 19.133 | −8.917 | 1.00 | 60.27 | C |
| ATOM | 1020 | C | TYR A | 136 | 19.149 | 16.690 | −12.119 | 1.00 | 65.64 | C |
| ATOM | 1021 | O | TYR A | 136 | 19.482 | 15.629 | −11.519 | 1.00 | 65.64 | O |
| ATOM | 1022 | N | ASP A | 137 | 19.851 | 17.233 | −13.117 | 1.00 | 66.22 | N |
| ATOM | 1023 | CA | ASP A | 137 | 21.187 | 16.749 | −13.506 | 1.00 | 66.54 | C |
| ATOM | 1024 | CB | ASP A | 137 | 21.733 | 17.487 | −14.732 | 1.00 | 66.52 | C |
| ATOM | 1025 | CG | ASP A | 137 | 20.922 | 17.226 | −16.012 | 1.00 | 66.60 | C |
| ATOM | 1026 | OD1 | ASP A | 137 | 20.532 | 16.043 | −16.240 | 1.00 | 58.70 | O |
| ATOM | 1027 | OD2 | ASP A | 137 | 20.692 | 18.220 | −16.774 | 1.00 | 64.00 | O |
| ATOM | 1028 | C | ASP A | 137 | 22.156 | 16.978 | −12.357 | 1.00 | 69.16 | C |
| ATOM | 1029 | O | ASP A | 137 | 22.185 | 18.051 | −11.712 | 1.00 | 61.90 | O |
| ATOM | 1030 | N | GLY A | 138 | 22.925 | 15.942 | −12.065 | 1.00 | 75.46 | N |
| ATOM | 1031 | CA | GLY A | 138 | 23.926 | 16.031 | −11.010 | 1.00 | 79.36 | C |
| ATOM | 1032 | C | GLY A | 138 | 23.438 | 15.746 | −9.606 | 1.00 | 79.51 | C |
| ATOM | 1033 | O | GLY A | 138 | 24.254 | 15.691 | −8.690 | 1.00 | 78.91 | O |
| ATOM | 1034 | N | LEU A | 139 | 22.133 | 15.519 | −9.435 | 1.00 | 83.64 | N |
| ATOM | 1035 | CA | LEU A | 139 | 21.536 | 15.295 | −8.103 | 1.00 | 84.32 | C |
| ATOM | 1036 | CB | LEU A | 139 | 20.766 | 16.550 | −7.644 | 1.00 | 84.31 | C |
| ATOM | 1037 | CG | LEU A | 139 | 21.641 | 17.769 | −7.259 | 1.00 | 81.84 | C |
| ATOM | 1038 | CD1 | LEU A | 139 | 21.052 | 19.150 | −7.581 | 1.00 | 79.65 | C |
| ATOM | 1039 | CD2 | LEU A | 139 | 21.986 | 17.686 | −5.785 | 1.00 | 80.77 | C |
| ATOM | 1040 | C | LEU A | 139 | 20.640 | 14.035 | −8.053 | 1.00 | 80.52 | C |
| ATOM | 1041 | O | LEU A | 139 | 20.120 | 13.557 | −9.080 | 1.00 | 87.81 | O |
| ATOM | 1042 | N | PHE A | 140 | 20.529 | 13.501 | −6.842 | 1.00 | 69.03 | N |
| ATOM | 1043 | CA | PHE A | 140 | 19.680 | 12.378 | −6.526 | 1.00 | 64.45 | C |
| ATOM | 1044 | CB | PHE A | 140 | 20.483 | 11.086 | −6.488 | 1.00 | 62.35 | C |
| ATOM | 1045 | CG | PHE A | 140 | 19.614 | 9.855 | −6.411 | 1.00 | 61.08 | C |
| ATOM | 1046 | CD1 | PHE A | 140 | 19.166 | 9.378 | −5.203 | 1.00 | 59.83 | C |
| ATOM | 1047 | CE1 | PHE A | 140 | 18.340 | 8.269 | −5.155 | 1.00 | 60.68 | C |
| ATOM | 1048 | CZ | PHE A | 140 | 17.964 | 7.631 | −6.309 | 1.00 | 57.18 | C |
| ATOM | 1049 | CE2 | PHE A | 140 | 18.397 | 8.099 | −7.515 | 1.00 | 56.23 | C |
| ATOM | 1050 | CD2 | PHE A | 140 | 19.203 | 9.208 | −7.566 | 1.00 | 58.83 | C |
| ATOM | 1051 | C | PHE A | 140 | 18.990 | 12.597 | −5.162 | 1.00 | 64.32 | C |
| ATOM | 1052 | O | PHE A | 140 | 19.573 | 12.359 | −4.103 | 1.00 | 65.35 | O |
| ATOM | 1053 | N | LYS A | 141 | 17.736 | 13.025 | −5.190 | 1.00 | 59.44 | N |
| ATOM | 1054 | CA | LYS A | 141 | 17.044 | 13.345 | −3.980 | 1.00 | 57.71 | C |
| ATOM | 1055 | CB | LYS A | 141 | 15.840 | 14.186 | −4.309 | 1.00 | 60.22 | C |
| ATOM | 1056 | CG | LYS A | 141 | 15.273 | 14.898 | −3.099 | 1.00 | 64.16 | C |
| ATOM | 1057 | CD | LYS A | 141 | 14.565 | 16.162 | −3.544 | 1.00 | 67.94 | C |
| ATOM | 1058 | CE | LYS A | 141 | 15.529 | 17.309 | −3.811 | 1.00 | 69.85 | C |
| ATOM | 1059 | NZ | LYS A | 141 | 14.928 | 18.629 | −3.476 | 1.00 | 74.03 | N |
| ATOM | 1060 | C | LYS A | 141 | 16.607 | 12.089 | −3.265 | 1.00 | 57.67 | C |
| ATOM | 1061 | O | LYS A | 141 | 16.251 | 11.116 | −3.890 | 1.00 | 60.28 | O |
| ATOM | 1062 | N | VAL A | 142 | 16.623 | 12.103 | −1.947 | 1.00 | 59.38 | N |

TABLE 6-continued

Atomic coordinates for CRBN:DDB1: Compound B (Human protein)

| ATOM | 1063 | CA | VAL A | 142 | 16.242 | 10.925 | −1.185 | 1.00 | 60.23 | C |
|---|---|---|---|---|---|---|---|---|---|---|
| ATOM | 1064 | CB | VAL A | 142 | 17.468 | 10.211 | −0.583 | 1.00 | 58.51 | C |
| ATOM | 1065 | CG1 | VAL A | 142 | 17.033 | 9.081 | 0.356 | 1.00 | 55.55 | C |
| ATOM | 1066 | CG2 | VAL A | 142 | 18.374 | 9.697 | −1.708 | 1.00 | 58.28 | C |
| ATOM | 1067 | C | VAL A | 142 | 15.309 | 11.334 | −0.076 | 1.00 | 62.21 | C |
| ATOM | 1068 | O | VAL A | 142 | 15.611 | 12.269 | 0.664 | 1.00 | 60.38 | O |
| ATOM | 1069 | N | ILE A | 143 | 14.213 | 10.589 | 0.056 | 1.00 | 64.23 | N |
| ATOM | 1070 | CA | ILE A | 143 | 13.193 | 10.835 | 1.075 | 1.00 | 67.18 | C |
| ATOM | 1071 | CB | ILE A | 143 | 11.814 | 11.113 | 0.416 | 1.00 | 65.57 | C |
| ATOM | 1072 | CG1 | ILE A | 143 | 11.948 | 12.126 | −0.729 | 1.00 | 61.69 | C |
| ATOM | 1073 | CD1 | ILE A | 143 | 10.648 | 12.754 | −1.181 | 1.00 | 60.70 | C |
| ATOM | 1074 | CG2 | ILE A | 143 | 10.809 | 11.592 | 1.454 | 1.00 | 68.47 | C |
| ATOM | 1075 | C | ILE A | 143 | 13.114 | 9.617 | 2.016 | 1.00 | 70.61 | C |
| ATOM | 1076 | O | ILE A | 143 | 12.469 | 8.625 | 1.702 | 1.00 | 74.97 | O |
| ATOM | 1077 | N | PRO A | 144 | 13.774 | 9.674 | 3.179 | 1.00 | 76.12 | N |
| ATOM | 1078 | CA | PRO A | 144 | 13.714 | 8.476 | 4.026 | 1.00 | 75.78 | C |
| ATOM | 1079 | CB | PRO A | 144 | 14.604 | 8.844 | 5.223 | 1.00 | 78.95 | C |
| ATOM | 1080 | CG | PRO A | 144 | 14.697 | 10.326 | 5.233 | 1.00 | 78.60 | C |
| ATOM | 1081 | CD | PRO A | 144 | 14.497 | 10.788 | 3.820 | 1.00 | 78.11 | C |
| ATOM | 1082 | C | PRO A | 144 | 12.293 | 8.212 | 4.474 | 1.00 | 70.93 | C |
| ATOM | 1083 | O | PRO A | 144 | 11.571 | 9.176 | 4.688 | 1.00 | 68.51 | O |
| ATOM | 1084 | N | LEU A | 145 | 11.895 | 6.947 | 4.600 | 1.00 | 73.31 | N |
| ATOM | 1085 | CA | LEU A | 145 | 10.532 | 6.595 | 5.073 | 1.00 | 83.39 | C |
| ATOM | 1086 | CB | LEU A | 145 | 9.904 | 5.523 | 4.192 | 1.00 | 82.53 | C |
| ATOM | 1087 | CG | LEU A | 145 | 9.563 | 6.111 | 2.827 | 1.00 | 86.17 | C |
| ATOM | 1088 | CD1 | LEU A | 145 | 9.086 | 5.030 | 1.851 | 1.00 | 87.94 | C |
| ATOM | 1089 | CD2 | LEU A | 145 | 8.546 | 7.252 | 2.958 | 1.00 | 82.53 | C |
| ATOM | 1090 | C | LEU A | 145 | 10.425 | 6.214 | 6.548 | 1.00 | 93.01 | C |
| ATOM | 1091 | O | LEU A | 145 | 9.653 | 5.339 | 6.937 | 1.00 | 97.16 | O |
| ATOM | 1092 | N | ASP A | 146 | 11.198 | 6.922 | 7.361 | 1.00 | 103.14 | N |
| ATOM | 1093 | CA | ASP A | 146 | 10.967 | 7.017 | 8.789 | 1.00 | 104.92 | C |
| ATOM | 1094 | CB | ASP A | 146 | 12.023 | 7.960 | 9.438 | 1.00 | 104.61 | C |
| ATOM | 1095 | CG | ASP A | 146 | 13.512 | 7.528 | 9.128 | 1.00 | 105.44 | C |
| ATOM | 1096 | OD1 | ASP A | 146 | 13.871 | 6.345 | 9.319 | 1.00 | 101.41 | O |
| ATOM | 1097 | OD2 | ASP A | 146 | 14.330 | 8.371 | 8.682 | 1.00 | 101.94 | O |
| ATOM | 1098 | C | ASP A | 146 | 9.515 | 7.544 | 8.922 | 1.00 | 106.46 | C |
| ATOM | 1099 | O | ASP A | 146 | 9.184 | 8.610 | 8.390 | 1.00 | 110.71 | O |
| ATOM | 1100 | N | ARG A | 147 | 8.650 | 6.759 | 9.575 | 1.00 | 106.28 | N |
| ATOM | 1101 | CA | ARG A | 147 | 7.218 | 7.102 | 9.808 | 1.00 | 102.90 | C |
| ATOM | 1102 | CB | ARG A | 147 | 6.525 | 5.994 | 10.628 | 1.00 | 103.05 | C |
| ATOM | 1103 | CG | ARG A | 147 | 5.006 | 5.927 | 10.486 | 1.00 | 107.31 | C |
| ATOM | 1104 | CD | ARG A | 147 | 4.225 | 6.504 | 11.659 | 1.00 | 116.11 | C |
| ATOM | 1105 | NE | ARG A | 147 | 4.407 | 5.769 | 12.927 | 1.00 | 124.20 | N |
| ATOM | 1106 | CZ | ARG A | 147 | 5.235 | 6.098 | 13.938 | 1.00 | 127.81 | C |
| ATOM | 1107 | NH1 | ARG A | 147 | 6.039 | 7.170 | 13.877 | 1.00 | 130.63 | N |
| ATOM | 1108 | NH2 | ARG A | 147 | 5.273 | 5.330 | 15.039 | 1.00 | 120.64 | N |
| ATOM | 1109 | C | ARG A | 147 | 7.000 | 8.463 | 10.495 | 1.00 | 100.71 | C |
| ATOM | 1110 | O | ARG A | 147 | 5.961 | 9.104 | 10.312 | 1.00 | 97.22 | O |
| ATOM | 1111 | N | ASP A | 148 | 7.988 | 8.898 | 11.280 | 1.00 | 102.04 | N |
| ATOM | 1112 | CA | ASP A | 148 | 7.983 | 10.228 | 11.881 | 1.00 | 95.48 | C |
| ATOM | 1113 | CB | ASP A | 148 | 9.078 | 10.338 | 12.966 | 1.00 | 89.14 | C |
| ATOM | 1114 | C | ASP A | 148 | 8.103 | 11.367 | 10.837 | 1.00 | 88.69 | C |
| ATOM | 1115 | O | ASP A | 148 | 7.857 | 12.524 | 11.218 | 1.00 | 84.24 | O |
| ATOM | 1116 | N | ASN A | 149 | 8.447 | 11.051 | 9.562 | 1.00 | 81.37 | N |
| ATOM | 1117 | CA | ASN A | 149 | 8.644 | 12.063 | 8.454 | 1.00 | 74.51 | C |
| ATOM | 1118 | CB | ASN A | 149 | 9.711 | 11.588 | 7.434 | 1.00 | 69.84 | C |
| ATOM | 1119 | CG | ASN A | 149 | 10.177 | 12.702 | 6.468 | 1.00 | 66.99 | C |
| ATOM | 1120 | OD1 | ASN A | 149 | 9.757 | 13.864 | 6.544 | 1.00 | 64.54 | O |
| ATOM | 1121 | ND2 | ASN A | 149 | 11.043 | 12.327 | 5.533 | 1.00 | 65.10 | N |
| ATOM | 1122 | C | ASN A | 149 | 7.374 | 12.526 | 7.705 | 1.00 | 66.76 | C |
| ATOM | 1123 | O | ASN A | 149 | 7.212 | 12.303 | 6.501 | 1.00 | 64.69 | O |
| ATOM | 1124 | N | LYS A | 150 | 6.510 | 13.223 | 8.427 | 1.00 | 62.55 | N |
| ATOM | 1125 | CA | LYS A | 150 | 5.243 | 13.660 | 7.874 | 1.00 | 62.63 | C |
| ATOM | 1126 | CB | LYS A | 150 | 4.196 | 13.862 | 8.996 | 1.00 | 58.86 | C |
| ATOM | 1127 | C | LYS A | 150 | 5.383 | 14.876 | 6.912 | 1.00 | 62.19 | C |
| ATOM | 1128 | O | LYS A | 150 | 4.436 | 15.147 | 6.169 | 1.00 | 60.62 | O |
| ATOM | 1129 | N | GLU A | 151 | 6.547 | 15.559 | 6.885 | 1.00 | 62.30 | N |
| ATOM | 1130 | CA | GLU A | 151 | 6.795 | 16.742 | 5.995 | 1.00 | 61.41 | C |
| ATOM | 1131 | CB | GLU A | 151 | 7.428 | 17.879 | 6.788 | 1.00 | 62.71 | C |
| ATOM | 1132 | CG | GLU A | 151 | 6.481 | 18.560 | 7.749 | 1.00 | 67.16 | C |
| ATOM | 1133 | CD | GLU A | 151 | 7.170 | 19.611 | 8.616 | 1.00 | 73.40 | C |
| ATOM | 1134 | OE1 | GLU A | 151 | 7.227 | 19.474 | 9.871 | 1.00 | 76.92 | O |
| ATOM | 1135 | OE2 | GLU A | 151 | 7.670 | 20.589 | 8.033 | 1.00 | 78.92 | O |
| ATOM | 1136 | C | GLU A | 151 | 7.662 | 16.447 | 4.736 | 1.00 | 63.59 | C |
| ATOM | 1137 | O | GLU A | 151 | 8.006 | 17.370 | 3.955 | 1.00 | 53.77 | O |
| ATOM | 1138 | N | LEU A | 152 | 7.960 | 15.156 | 4.527 | 1.00 | 67.75 | N |
| ATOM | 1139 | CA | LEU A | 152 | 8.765 | 14.653 | 3.391 | 1.00 | 69.82 | C |
| ATOM | 1140 | CB | LEU A | 152 | 7.965 | 14.553 | 2.062 | 1.00 | 69.18 | C |

TABLE 6-continued

Atomic coordinates for CRBN:DDB1: Compound B (Human protein)

| ATOM | 1141 | CG | LEU A | 152 | 6.708 | 13.658 | 2.142 | 1.00 | 72.05 | C |
|---|---|---|---|---|---|---|---|---|---|---|
| ATOM | 1142 | CD1 | LEU A | 152 | 5.914 | 13.501 | 0.841 | 1.00 | 73.55 | C |
| ATOM | 1143 | CD2 | LEU A | 152 | 7.068 | 12.284 | 2.674 | 1.00 | 72.25 | C |
| ATOM | 1144 | C | LEU A | 152 | 10.047 | 15.456 | 3.268 | 1.00 | 71.32 | C |
| ATOM | 1145 | O | LEU A | 152 | 10.511 | 15.822 | 2.136 | 1.00 | 69.99 | O |
| ATOM | 1146 | N | LYS A | 153 | 10.617 | 15.705 | 4.463 | 1.00 | 66.49 | N |
| ATOM | 1147 | CA | LYS A | 153 | 11.912 | 16.352 | 4.577 | 1.00 | 63.93 | C |
| ATOM | 1148 | CB | LYS A | 153 | 12.197 | 16.773 | 6.035 | 1.00 | 58.05 | C |
| ATOM | 1149 | C | LYS A | 153 | 12.866 | 15.300 | 3.961 | 1.00 | 66.33 | C |
| ATOM | 1150 | O | LYS A | 153 | 12.633 | 14.087 | 4.065 | 1.00 | 70.86 | O |
| ATOM | 1151 | N | ALA A | 154 | 13.885 | 15.764 | 3.255 | 1.00 | 66.25 | N |
| ATOM | 1152 | CA | ALA A | 154 | 14.655 | 14.916 | 2.366 | 1.00 | 67.17 | C |
| ATOM | 1153 | CB | ALA A | 154 | 13.885 | 14.841 | 1.080 | 1.00 | 71.22 | C |
| ATOM | 1154 | C | ALA A | 154 | 16.055 | 15.485 | 2.092 | 1.00 | 68.84 | C |
| ATOM | 1155 | O | ALA A | 154 | 16.243 | 16.690 | 2.185 | 1.00 | 75.34 | O |
| ATOM | 1156 | N | PHE A | 155 | 17.025 | 14.644 | 1.718 | 1.00 | 68.22 | N |
| ATOM | 1157 | CA | PHE A | 155 | 18.380 | 15.133 | 1.304 | 1.00 | 65.45 | C |
| ATOM | 1158 | CB | PHE A | 155 | 19.501 | 14.605 | 2.238 | 1.00 | 61.17 | C |
| ATOM | 1159 | CG | PHE A | 155 | 19.612 | 13.105 | 2.276 | 1.00 | 59.83 | C |
| ATOM | 1160 | CD1 | PHE A | 155 | 20.330 | 12.412 | 1.283 | 1.00 | 61.45 | C |
| ATOM | 1161 | CE1 | PHE A | 155 | 20.427 | 11.021 | 1.301 | 1.00 | 61.14 | C |
| ATOM | 1162 | CZ | PHE A | 155 | 19.811 | 10.308 | 2.325 | 1.00 | 61.01 | C |
| ATOM | 1163 | CE2 | PHE A | 155 | 19.109 | 10.990 | 3.333 | 1.00 | 59.05 | C |
| ATOM | 1164 | CD2 | PHE A | 155 | 19.009 | 12.376 | 3.302 | 1.00 | 56.86 | C |
| ATOM | 1165 | C | PHE A | 155 | 18.729 | 14.873 | −0.188 | 1.00 | 65.03 | C |
| ATOM | 1166 | O | PHE A | 155 | 18.074 | 14.107 | −0.897 | 1.00 | 63.22 | O |
| ATOM | 1167 | N | ASN A | 156 | 19.781 | 15.539 | −0.633 | 1.00 | 63.77 | N |
| ATOM | 1168 | CA | ASN A | 156 | 20.359 | 15.301 | −1.930 | 1.00 | 64.42 | C |
| ATOM | 1169 | CB | ASN A | 156 | 20.539 | 16.646 | −2.610 | 1.00 | 63.60 | C |
| ATOM | 1170 | CG | ASN A | 156 | 19.315 | 17.079 | −3.371 | 1.00 | 66.25 | C |
| ATOM | 1171 | OD1 | ASN A | 156 | 18.887 | 18.204 | −3.236 | 1.00 | 70.96 | O |
| ATOM | 1172 | ND2 | ASN A | 156 | 18.785 | 16.211 | −4.230 | 1.00 | 69.22 | N |
| ATOM | 1173 | C | ASN A | 156 | 21.706 | 14.533 | −1.852 | 1.00 | 65.12 | C |
| ATOM | 1174 | O | ASN A | 156 | 22.315 | 14.442 | −0.796 | 1.00 | 68.69 | O |
| ATOM | 1175 | N | ILE A | 157 | 22.130 | 13.949 | −2.964 | 1.00 | 63.30 | N |
| ATOM | 1176 | CA | ILE A | 157 | 23.432 | 13.298 | −3.086 | 1.00 | 67.57 | C |
| ATOM | 1177 | CB | ILE A | 157 | 23.335 | 11.740 | −2.983 | 1.00 | 65.69 | C |
| ATOM | 1178 | CG1 | ILE A | 157 | 22.661 | 11.275 | −1.685 | 1.00 | 64.99 | C |
| ATOM | 1179 | CD1 | ILE A | 157 | 22.465 | 9.761 | −1.576 | 1.00 | 63.29 | C |
| ATOM | 1180 | CG2 | ILE A | 157 | 24.712 | 11.098 | −3.048 | 1.00 | 67.60 | C |
| ATOM | 1181 | C | ILE A | 157 | 23.962 | 13.679 | −4.475 | 1.00 | 71.69 | C |
| ATOM | 1182 | O | ILE A | 157 | 23.318 | 13.338 | −5.461 | 1.00 | 81.83 | O |
| ATOM | 1183 | N | ARG A | 158 | 25.108 | 14.365 | −4.579 | 1.00 | 71.02 | N |
| ATOM | 1184 | CA | ARG A | 158 | 25.693 | 14.636 | −5.902 | 1.00 | 68.43 | C |
| ATOM | 1185 | CB | ARG A | 158 | 26.893 | 15.616 | −5.831 | 1.00 | 61.31 | C |
| ATOM | 1186 | C | ARG A | 158 | 26.029 | 13.262 | −6.551 | 1.00 | 70.65 | C |
| ATOM | 1187 | O | ARG A | 158 | 26.596 | 12.383 | −5.889 | 1.00 | 64.71 | O |
| ATOM | 1188 | N | LEU A | 159 | 25.545 | 13.044 | −7.783 | 1.00 | 77.81 | N |
| ATOM | 1189 | CA | LEU A | 159 | 26.068 | 12.000 | −8.686 | 1.00 | 82.59 | C |
| ATOM | 1190 | CB | LEU A | 159 | 25.080 | 11.590 | −9.769 | 1.00 | 83.21 | C |
| ATOM | 1191 | CG | LEU A | 159 | 23.621 | 11.297 | −9.509 | 1.00 | 89.86 | C |
| ATOM | 1192 | CD1 | LEU A | 159 | 22.742 | 11.906 | −10.617 | 1.00 | 93.61 | C |
| ATOM | 1193 | CD2 | LEU A | 159 | 23.436 | 9.788 | −9.397 | 1.00 | 90.89 | C |
| ATOM | 1194 | C | LEU A | 159 | 27.172 | 12.635 | −9.486 | 1.00 | 90.29 | C |
| ATOM | 1195 | O | LEU A | 159 | 27.084 | 13.811 | −9.841 | 1.00 | 95.60 | O |
| ATOM | 1196 | N | GLU A | 160 | 28.172 | 11.854 | −9.861 | 1.00 | 99.61 | N |
| ATOM | 1197 | CA | GLU A | 160 | 29.114 | 12.316 | −10.881 | 1.00 | 105.09 | C |
| ATOM | 1198 | CB | GLU A | 160 | 30.323 | 11.353 | −11.007 | 1.00 | 110.18 | C |
| ATOM | 1199 | CG | GLU A | 160 | 31.315 | 11.383 | −9.830 | 1.00 | 108.14 | C |
| ATOM | 1200 | CD | GLU A | 160 | 31.883 | 12.776 | −9.568 | 1.00 | 103.57 | C |
| ATOM | 1201 | OE1 | GLU A | 160 | 32.924 | 13.156 | −10.176 | 1.00 | 97.79 | O |
| ATOM | 1202 | OE2 | GLU A | 160 | 31.260 | 13.494 | −8.759 | 1.00 | 91.14 | O |
| ATOM | 1203 | C | GLU A | 160 | 28.394 | 12.504 | −12.233 | 1.00 | 103.06 | C |
| ATOM | 1204 | O | GLU A | 160 | 28.495 | 13.571 | −12.846 | 1.00 | 102.28 | O |
| ATOM | 1205 | N | GLU A | 161 | 27.591 | 11.509 | −12.616 | 1.00 | 98.59 | N |
| ATOM | 1206 | CA | GLU A | 161 | 27.161 | 11.306 | −13.995 | 1.00 | 92.57 | C |
| ATOM | 1207 | CB | GLU A | 161 | 26.743 | 9.856 | −14.218 | 1.00 | 90.13 | C |
| ATOM | 1208 | CG | GLU A | 161 | 27.855 | 8.851 | −13.934 | 1.00 | 96.42 | C |
| ATOM | 1209 | CD | GLU A | 161 | 28.083 | 8.543 | −12.448 | 1.00 | 102.15 | C |
| ATOM | 1210 | OE1 | GLU A | 161 | 27.501 | 9.209 | −11.562 | 1.00 | 102.32 | O |
| ATOM | 1211 | OE2 | GLU A | 161 | 28.866 | 7.624 | −12.145 | 1.00 | 106.89 | O |
| ATOM | 1212 | C | GLU A | 161 | 26.015 | 12.244 | −14.320 | 1.00 | 87.41 | C |
| ATOM | 1213 | O | GLU A | 161 | 24.926 | 12.105 | −13.792 | 1.00 | 86.43 | O |
| ATOM | 1214 | N | LEU A | 162 | 26.279 | 13.210 | −15.188 | 1.00 | 86.46 | N |
| ATOM | 1215 | CA | LEU A | 162 | 25.307 | 14.239 | −15.510 | 1.00 | 84.62 | C |
| ATOM | 1216 | CB | LEU A | 162 | 26.011 | 15.497 | −16.044 | 1.00 | 87.80 | C |
| ATOM | 1217 | CG | LEU A | 162 | 27.057 | 16.205 | −15.168 | 1.00 | 91.35 | C |
| ATOM | 1218 | CD1 | LEU A | 162 | 27.283 | 17.628 | −15.689 | 1.00 | 90.66 | C |

TABLE 6-continued

Atomic coordinates for CRBN:DDB1: Compound B (Human protein)

| ATOM | 1219 | CD2 | LEU A | 162 | 26.691 | 16.225 | −13.680 | 1.00 | 91.70 | C |
|---|---|---|---|---|---|---|---|---|---|---|
| ATOM | 1220 | C | LEU A | 162 | 24.237 | 13.843 | −16.511 | 1.00 | 81.47 | C |
| ATOM | 1221 | O | LEU A | 162 | 23.350 | 14.640 | −16.729 | 1.00 | 86.07 | O |
| ATOM | 1222 | N | HIS A | 163 | 24.297 | 12.674 | −17.146 | 1.00 | 79.73 | N |
| ATOM | 1223 | CA | HIS A | 163 | 23.324 | 12.358 | −18.189 | 1.00 | 78.24 | C |
| ATOM | 1224 | CB | HIS A | 163 | 23.970 | 12.451 | −19.564 | 1.00 | 85.57 | C |
| ATOM | 1225 | CG | HIS A | 163 | 24.428 | 13.826 | −19.950 | 1.00 | 96.98 | C |
| ATOM | 1226 | ND1 | HIS A | 163 | 23.871 | 14.986 | −19.441 | 1.00 | 105.83 | N |
| ATOM | 1227 | CE1 | HIS A | 163 | 24.458 | 16.036 | −19.987 | 1.00 | 104.29 | C |
| ATOM | 1228 | NE2 | HIS A | 163 | 25.361 | 15.601 | −20.848 | 1.00 | 106.11 | N |
| ATOM | 1229 | CD2 | HIS A | 163 | 25.355 | 14.225 | −20.853 | 1.00 | 100.27 | C |
| ATOM | 1230 | C | HIS A | 163 | 22.685 | 10.994 | −18.010 | 1.00 | 75.62 | C |
| ATOM | 1231 | O | HIS A | 163 | 22.723 | 10.174 | −18.920 | 1.00 | 77.41 | O |
| ATOM | 1232 | N | VAL A | 164 | 22.048 | 10.782 | −16.858 | 1.00 | 70.22 | N |
| ATOM | 1233 | CA | VAL A | 164 | 21.323 | 9.526 | −16.557 | 1.00 | 68.83 | C |
| ATOM | 1234 | CB | VAL A | 164 | 20.826 | 9.482 | −15.087 | 1.00 | 67.65 | C |
| ATOM | 1235 | CG1 | VAL A | 164 | 20.204 | 8.109 | −14.774 | 1.00 | 66.02 | C |
| ATOM | 1236 | CG2 | VAL A | 164 | 21.943 | 9.825 | −14.120 | 1.00 | 66.95 | C |
| ATOM | 1237 | C | VAL A | 164 | 20.061 | 9.273 | −17.417 | 1.00 | 67.25 | C |
| ATOM | 1238 | O | VAL A | 164 | 19.173 | 10.110 | −17.469 | 1.00 | 63.74 | O |
| ATOM | 1239 | N | ILE A | 165 | 19.933 | 8.077 | −17.984 | 1.00 | 68.13 | N |
| ATOM | 1240 | CA | ILE A | 165 | 18.794 | 7.752 | −18.843 | 1.00 | 69.27 | C |
| ATOM | 1241 | CB | ILE A | 165 | 19.206 | 6.845 | −20.012 | 1.00 | 68.97 | C |
| ATOM | 1242 | CG1 | ILE A | 165 | 20.431 | 7.420 | −20.717 | 1.00 | 69.87 | C |
| ATOM | 1243 | CD1 | ILE A | 165 | 20.289 | 8.873 | −21.098 | 1.00 | 71.18 | C |
| ATOM | 1244 | CG2 | ILE A | 165 | 18.079 | 6.719 | −21.024 | 1.00 | 69.26 | C |
| ATOM | 1245 | C | ILE A | 165 | 17.588 | 7.200 | −18.071 | 1.00 | 70.25 | C |
| ATOM | 1246 | O | ILE A | 165 | 16.608 | 7.913 | −17.971 | 1.00 | 79.84 | O |
| ATOM | 1247 | N | ASP A | 166 | 17.636 | 5.966 | −17.555 | 1.00 | 67.06 | N |
| ATOM | 1248 | CA | ASP A | 166 | 16.576 | 5.401 | −16.659 | 1.00 | 68.43 | C |
| ATOM | 1249 | CB | ASP A | 166 | 15.825 | 4.241 | −17.322 | 1.00 | 70.29 | C |
| ATOM | 1250 | CG | ASP A | 166 | 14.467 | 3.959 | −16.683 | 1.00 | 74.75 | C |
| ATOM | 1251 | OD1 | ASP A | 166 | 13.572 | 4.819 | −16.808 | 1.00 | 84.75 | O |
| ATOM | 1252 | OD2 | ASP A | 166 | 14.285 | 2.887 | −16.073 | 1.00 | 66.72 | O |
| ATOM | 1253 | C | ASP A | 166 | 17.248 | 4.955 | −15.334 | 1.00 | 69.74 | C |
| ATOM | 1254 | O | ASP A | 166 | 18.458 | 5.170 | −15.177 | 1.00 | 70.30 | O |
| ATOM | 1255 | N | VAL A | 167 | 16.483 | 4.410 | −14.373 | 1.00 | 66.14 | N |
| ATOM | 1256 | CA | VAL A | 167 | 17.047 | 3.971 | −13.079 | 1.00 | 66.10 | C |
| ATOM | 1257 | CB | VAL A | 167 | 17.651 | 5.139 | −12.229 | 1.00 | 66.92 | C |
| ATOM | 1258 | CG1 | VAL A | 167 | 16.676 | 6.279 | −12.066 | 1.00 | 73.11 | C |
| ATOM | 1259 | CG2 | VAL A | 167 | 18.083 | 4.690 | −10.840 | 1.00 | 66.63 | C |
| ATOM | 1260 | C | VAL A | 167 | 16.033 | 3.239 | −12.226 | 1.00 | 64.03 | C |
| ATOM | 1261 | O | VAL A | 167 | 14.878 | 3.618 | −12.155 | 1.00 | 68.52 | O |
| ATOM | 1262 | N | LYS A | 168 | 16.482 | 2.200 | −11.559 | 1.00 | 61.62 | N |
| ATOM | 1263 | CA | LYS A | 168 | 15.646 | 1.505 | −10.632 | 1.00 | 63.59 | C |
| ATOM | 1264 | CB | LYS A | 168 | 15.253 | 0.178 | −11.234 | 1.00 | 66.00 | C |
| ATOM | 1265 | CG | LYS A | 168 | 13.787 | 0.103 | −11.598 | 1.00 | 69.47 | C |
| ATOM | 1266 | CD | LYS A | 168 | 13.539 | 0.591 | −12.988 | 1.00 | 66.48 | C |
| ATOM | 1267 | CE | LYS A | 168 | 12.068 | 0.782 | −13.224 | 1.00 | 67.53 | C |
| ATOM | 1268 | NZ | LYS A | 168 | 11.929 | 1.897 | −14.194 | 1.00 | 73.55 | N |
| ATOM | 1269 | C | LYS A | 168 | 16.341 | 1.263 | −9.325 | 1.00 | 63.94 | C |
| ATOM | 1270 | O | LYS A | 168 | 17.485 | 1.583 | −9.166 | 1.00 | 69.45 | O |
| ATOM | 1271 | N | PHE A | 169 | 15.600 | 0.723 | −8.383 | 1.00 | 66.36 | N |
| ATOM | 1272 | CA | PHE A | 169 | 16.153 | 0.101 | −7.203 | 1.00 | 68.24 | C |
| ATOM | 1273 | CB | PHE A | 169 | 15.291 | 0.405 | −5.950 | 1.00 | 70.91 | C |
| ATOM | 1274 | CG | PHE A | 169 | 15.649 | 1.683 | −5.246 | 1.00 | 70.30 | C |
| ATOM | 1275 | CD1 | PHE A | 169 | 15.113 | 2.876 | −5.638 | 1.00 | 73.00 | C |
| ATOM | 1276 | CE1 | PHE A | 169 | 15.459 | 4.048 | −4.988 | 1.00 | 75.94 | C |
| ATOM | 1277 | CZ | PHE A | 169 | 16.332 | 4.028 | −3.932 | 1.00 | 72.17 | C |
| ATOM | 1278 | CE2 | PHE A | 169 | 16.857 | 2.834 | −3.523 | 1.00 | 70.91 | C |
| ATOM | 1279 | CD2 | PHE A | 169 | 16.527 | 1.678 | −4.187 | 1.00 | 71.75 | C |
| ATOM | 1280 | C | PHE A | 169 | 16.100 | −1.394 | −7.506 | 1.00 | 70.64 | C |
| ATOM | 1281 | O | PHE A | 169 | 15.088 | −1.899 | −8.061 | 1.00 | 68.36 | O |
| ATOM | 1282 | N | LEU A | 170 | 17.163 | −2.091 | −7.097 | 1.00 | 71.99 | N |
| ATOM | 1283 | CA | LEU A | 170 | 17.312 | −3.538 | −7.318 | 1.00 | 72.42 | C |
| ATOM | 1284 | CB | LEU A | 170 | 18.784 | −3.900 | −7.556 | 1.00 | 72.80 | C |
| ATOM | 1285 | CG | LEU A | 170 | 19.464 | −3.168 | −8.743 | 1.00 | 74.90 | C |
| ATOM | 1286 | CD1 | LEU A | 170 | 20.968 | −3.033 | −8.556 | 1.00 | 75.96 | C |
| ATOM | 1287 | CD2 | LEU A | 170 | 19.161 | −3.829 | −10.079 | 1.00 | 75.75 | C |
| ATOM | 1288 | C | LEU A | 170 | 16.771 | −4.318 | −6.142 | 1.00 | 72.17 | C |
| ATOM | 1289 | O | LEU A | 170 | 16.609 | −3.776 | −5.047 | 1.00 | 70.71 | O |
| ATOM | 1290 | N | TYR A | 171 | 16.492 | −5.595 | −6.383 | 1.00 | 74.99 | N |
| ATOM | 1291 | CA | TYR A | 171 | 15.990 | −6.486 | −5.344 | 1.00 | 76.47 | C |
| ATOM | 1292 | CB | TYR A | 171 | 14.951 | −7.466 | −5.917 | 1.00 | 75.66 | C |
| ATOM | 1293 | CG | TYR A | 171 | 13.631 | −6.809 | −6.334 | 1.00 | 73.60 | C |
| ATOM | 1294 | CD1 | TYR A | 171 | 13.586 | −5.898 | −7.389 | 1.00 | 72.17 | C |
| ATOM | 1295 | CE1 | TYR A | 171 | 12.410 | −5.296 | −7.777 | 1.00 | 72.37 | C |
| ATOM | 1296 | CZ | TYR A | 171 | 11.235 | −5.608 | −7.121 | 1.00 | 76.46 | C |

TABLE 6-continued

Atomic coordinates for CRBN:DDB1: Compound B (Human protein)

| ATOM | 1297 | OH | TYR A | 171 | 10.058 | −4.989 | −7.530 | 1.00 | 80.71 | O |
|---|---|---|---|---|---|---|---|---|---|---|
| ATOM | 1298 | CE2 | TYR A | 171 | 11.245 | −6.515 | −6.067 | 1.00 | 73.39 | C |
| ATOM | 1299 | CD2 | TYR A | 171 | 12.434 | −7.120 | −5.690 | 1.00 | 72.56 | C |
| ATOM | 1300 | C | TYR A | 171 | 17.167 | −7.227 | −4.729 | 1.00 | 80.55 | C |
| ATOM | 1301 | O | TYR A | 171 | 18.270 | −7.238 | −5.285 | 1.00 | 82.05 | O |
| ATOM | 1302 | N | GLY A | 172 | 16.927 | −7.809 | −3.559 | 1.00 | 89.43 | N |
| ATOM | 1303 | CA | GLY A | 172 | 17.869 | −8.736 | −2.904 | 1.00 | 92.31 | C |
| ATOM | 1304 | C | GLY A | 172 | 19.275 | −8.206 | −2.701 | 1.00 | 92.96 | C |
| ATOM | 1305 | O | GLY A | 172 | 20.186 | −8.627 | −3.397 | 1.00 | 96.39 | O |
| ATOM | 1306 | N | CYS A | 173 | 19.443 | −7.288 | −1.750 | 1.00 | 95.72 | N |
| ATOM | 1307 | CA | CYS A | 173 | 20.749 | −6.663 | −1.444 | 1.00 | 94.99 | C |
| ATOM | 1308 | CB | CYS A | 173 | 20.870 | −5.323 | −2.186 | 1.00 | 92.09 | C |
| ATOM | 1309 | SG | CYS A | 173 | 20.688 | −5.340 | −3.983 | 1.00 | 88.80 | S |
| ATOM | 1310 | C | CYS A | 173 | 20.963 | −6.429 | 0.085 | 1.00 | 97.24 | C |
| ATOM | 1311 | O | CYS A | 173 | 20.049 | −5.969 | 0.786 | 1.00 | 89.97 | O |
| ATOM | 1312 | N | GLN A | 174 | 22.170 | −6.723 | 0.595 | 1.00 | 102.37 | N |
| ATOM | 1313 | CA | GLN A | 174 | 22.522 | −6.437 | 2.010 | 1.00 | 99.99 | C |
| ATOM | 1314 | CB | GLN A | 174 | 24.011 | −6.776 | 2.320 | 1.00 | 92.67 | C |
| ATOM | 1315 | C | GLN A | 174 | 22.152 | −4.968 | 2.353 | 1.00 | 96.62 | C |
| ATOM | 1316 | O | GLN A | 174 | 21.755 | −4.690 | 3.491 | 1.00 | 93.57 | O |
| ATOM | 1317 | N | ALA A | 175 | 22.253 | −4.067 | 1.354 | 1.00 | 92.10 | N |
| ATOM | 1318 | CA | ALA A | 175 | 21.786 | −2.668 | 1.447 | 1.00 | 93.37 | C |
| ATOM | 1319 | CB | ALA A | 175 | 22.965 | −1.764 | 1.778 | 1.00 | 89.15 | C |
| ATOM | 1320 | C | ALA A | 175 | 21.042 | −2.127 | 0.169 | 1.00 | 97.74 | C |
| ATOM | 1321 | O | ALA A | 175 | 21.334 | −2.552 | −0.946 | 1.00 | 98.97 | O |
| ATOM | 1322 | N | PRO A | 176 | 20.073 | −1.187 | 0.337 | 1.00 | 98.23 | N |
| ATOM | 1323 | CA | PRO A | 176 | 19.461 | −0.360 | −0.708 | 1.00 | 90.54 | C |
| ATOM | 1324 | CB | PRO A | 176 | 18.948 | 0.812 | 0.095 | 1.00 | 91.72 | C |
| ATOM | 1325 | CG | PRO A | 176 | 18.368 | 0.116 | 1.285 | 1.00 | 96.31 | C |
| ATOM | 1326 | CD | PRO A | 176 | 19.295 | −1.035 | 1.584 | 1.00 | 99.65 | C |
| ATOM | 1327 | C | PRO A | 176 | 20.378 | 0.144 | −1.793 | 1.00 | 85.16 | C |
| ATOM | 1328 | O | PRO A | 176 | 21.264 | 0.952 | −1.534 | 1.00 | 90.91 | O |
| ATOM | 1329 | N | THR A | 177 | 20.101 | −0.298 | −3.010 | 1.00 | 80.61 | N |
| ATOM | 1330 | CA | THR A | 177 | 21.019 | −0.187 | −4.125 | 1.00 | 77.62 | C |
| ATOM | 1331 | CB | THR A | 177 | 21.719 | −1.540 | −4.316 | 1.00 | 81.21 | C |
| ATOM | 1332 | OG1 | THR A | 177 | 22.590 | −1.772 | −3.199 | 1.00 | 82.06 | O |
| ATOM | 1333 | CG2 | THR A | 177 | 22.526 | −1.609 | −5.615 | 1.00 | 80.58 | C |
| ATOM | 1334 | C | THR A | 177 | 20.287 | 0.165 | −5.407 | 1.00 | 71.72 | C |
| ATOM | 1335 | O | THR A | 177 | 19.322 | −0.498 | −5.760 | 1.00 | 65.51 | O |
| ATOM | 1336 | N | ILE A | 178 | 20.808 | 1.175 | −6.111 | 1.00 | 73.56 | N |
| ATOM | 1337 | CA | ILE A | 178 | 20.235 | 1.708 | −7.378 | 1.00 | 74.82 | C |
| ATOM | 1338 | CB | ILE A | 178 | 19.972 | 3.244 | −7.313 | 1.00 | 73.16 | C |
| ATOM | 1339 | CG1 | ILE A | 178 | 21.274 | 4.046 | −7.188 | 1.00 | 71.52 | C |
| ATOM | 1340 | CD1 | ILE A | 178 | 21.513 | 5.011 | −8.321 | 1.00 | 73.25 | C |
| ATOM | 1341 | CG2 | ILE A | 178 | 18.995 | 3.585 | −6.173 | 1.00 | 72.08 | C |
| ATOM | 1342 | C | ILE A | 178 | 21.071 | 1.421 | −8.637 | 1.00 | 70.58 | C |
| ATOM | 1343 | O | ILE A | 178 | 22.286 | 1.481 | −8.593 | 1.00 | 71.95 | O |
| ATOM | 1344 | N | CYS A | 179 | 20.403 | 1.139 | −9.747 | 1.00 | 68.37 | N |
| ATOM | 1345 | CA | CYS A | 179 | 21.058 | 0.674 | −10.961 | 1.00 | 74.38 | C |
| ATOM | 1346 | CB | CYS A | 179 | 20.576 | −0.734 | −11.276 | 1.00 | 76.18 | C |
| ATOM | 1347 | SG | CYS A | 179 | 21.081 | −1.310 | −12.918 | 1.00 | 82.74 | S |
| ATOM | 1348 | C | CYS A | 179 | 20.673 | 1.562 | −12.111 | 1.00 | 72.57 | C |
| ATOM | 1349 | O | CYS A | 179 | 19.490 | 1.797 | −12.244 | 1.00 | 78.14 | O |
| ATOM | 1350 | N | PHE A | 180 | 21.609 | 2.016 | −12.963 | 1.00 | 68.85 | N |
| ATOM | 1351 | CA | PHE A | 180 | 21.237 | 3.000 | −14.004 | 1.00 | 68.83 | C |
| ATOM | 1352 | CB | PHE A | 180 | 21.071 | 4.354 | −13.360 | 1.00 | 70.12 | C |
| ATOM | 1353 | CG | PHE A | 180 | 22.345 | 4.942 | −12.822 | 1.00 | 70.80 | C |
| ATOM | 1354 | CD1 | PHE A | 180 | 22.819 | 4.568 | −11.560 | 1.00 | 70.74 | C |
| ATOM | 1355 | CE1 | PHE A | 180 | 23.969 | 5.146 | −11.035 | 1.00 | 72.48 | C |
| ATOM | 1356 | CZ | PHE A | 180 | 24.662 | 6.103 | −11.773 | 1.00 | 72.26 | C |
| ATOM | 1357 | CE2 | PHE A | 180 | 24.196 | 6.477 | −13.035 | 1.00 | 71.49 | C |
| ATOM | 1358 | CD2 | PHE A | 180 | 23.043 | 5.908 | −13.552 | 1.00 | 67.58 | C |
| ATOM | 1359 | C | PHE A | 180 | 22.122 | 3.256 | −15.208 | 1.00 | 69.99 | C |
| ATOM | 1360 | O | PHE A | 180 | 23.304 | 3.429 | −15.073 | 1.00 | 80.68 | O |
| ATOM | 1361 | N | VAL A | 181 | 21.509 | 3.437 | −16.362 | 1.00 | 67.46 | N |
| ATOM | 1362 | CA | VAL A | 181 | 22.221 | 3.791 | −17.570 | 1.00 | 68.07 | C |
| ATOM | 1363 | CB | VAL A | 181 | 21.363 | 3.448 | −18.779 | 1.00 | 70.23 | C |
| ATOM | 1364 | CG1 | VAL A | 181 | 22.041 | 3.908 | −20.068 | 1.00 | 74.18 | C |
| ATOM | 1365 | CG2 | VAL A | 181 | 21.063 | 1.954 | −18.781 | 1.00 | 71.51 | C |
| ATOM | 1366 | C | VAL A | 181 | 22.517 | 5.290 | −17.634 | 1.00 | 70.58 | C |
| ATOM | 1367 | O | VAL A | 181 | 21.643 | 6.094 | −17.349 | 1.00 | 71.41 | O |
| ATOM | 1368 | N | TYR A | 182 | 23.723 | 5.656 | −18.071 | 1.00 | 73.36 | N |
| ATOM | 1369 | CA | TYR A | 182 | 24.137 | 7.059 | −18.211 | 1.00 | 74.65 | C |
| ATOM | 1370 | CB | TYR A | 182 | 25.016 | 7.514 | −17.042 | 1.00 | 83.22 | C |
| ATOM | 1371 | CG | TYR A | 182 | 26.291 | 6.739 | −16.815 | 1.00 | 89.44 | C |
| ATOM | 1372 | CD1 | TYR A | 182 | 26.247 | 5.460 | −16.268 | 1.00 | 95.74 | C |
| ATOM | 1373 | CE1 | TYR A | 182 | 27.400 | 4.732 | −16.024 | 1.00 | 98.76 | C |
| ATOM | 1374 | CZ | TYR A | 182 | 28.626 | 5.281 | −16.289 | 1.00 | 97.02 | C |

TABLE 6-continued

Atomic coordinates for CRBN:DDB1: Compound B (Human protein)

| ATOM | 1375 | OH | TYR A | 182 | 29.714 | 4.490 | −16.028 | 1.00 | 95.82 | O |
|---|---|---|---|---|---|---|---|---|---|---|
| ATOM | 1376 | CE2 | TYR A | 182 | 28.717 | 6.572 | −16.812 | 1.00 | 96.27 | C |
| ATOM | 1377 | CD2 | TYR A | 182 | 27.546 | 7.298 | −17.073 | 1.00 | 92.57 | C |
| ATOM | 1378 | C | TYR A | 182 | 24.847 | 7.294 | −19.519 | 1.00 | 71.30 | C |
| ATOM | 1379 | O | TYR A | 182 | 24.988 | 6.363 | −20.307 | 1.00 | 65.25 | O |
| ATOM | 1380 | N | GLN A | 183 | 25.239 | 8.547 | −19.771 | 1.00 | 69.97 | N |
| ATOM | 1381 | CA | GLN A | 183 | 25.950 | 8.860 | −20.979 | 1.00 | 72.79 | C |
| ATOM | 1382 | CB | GLN A | 183 | 24.997 | 9.085 | −22.135 | 1.00 | 68.44 | C |
| ATOM | 1383 | CG | GLN A | 183 | 25.672 | 8.663 | −23.415 | 1.00 | 71.13 | C |
| ATOM | 1384 | CD | GLN A | 183 | 24.967 | 9.121 | −24.652 | 1.00 | 74.76 | C |
| ATOM | 1385 | OE1 | GLN A | 183 | 24.843 | 10.330 | −24.862 | 1.00 | 73.07 | O |
| ATOM | 1386 | NE2 | GLN A | 183 | 24.548 | 8.167 | −25.524 | 1.00 | 77.20 | N |
| ATOM | 1387 | C | GLN A | 183 | 26.940 | 10.016 | −20.889 | 1.00 | 83.54 | C |
| ATOM | 1388 | O | GLN A | 183 | 26.556 | 11.184 | −20.784 | 1.00 | 87.62 | O |
| ATOM | 1389 | N | ASP A | 184 | 28.226 | 9.662 | −20.990 | 1.00 | 92.80 | N |
| ATOM | 1390 | CA | ASP A | 184 | 29.351 | 10.631 | −21.056 | 1.00 | 92.20 | C |
| ATOM | 1391 | CB | ASP A | 184 | 30.442 | 10.307 | −19.986 | 1.00 | 82.18 | C |
| ATOM | 1392 | CG | ASP A | 184 | 30.817 | 8.847 | −19.940 | 1.00 | 78.83 | C |
| ATOM | 1393 | OD1 | ASP A | 184 | 30.779 | 8.199 | −21.002 | 1.00 | 85.55 | O |
| ATOM | 1394 | OD2 | ASP A | 184 | 31.154 | 8.332 | −18.860 | 1.00 | 71.55 | O |
| ATOM | 1395 | C | ASP A | 184 | 29.890 | 10.732 | −22.523 | 1.00 | 95.33 | C |
| ATOM | 1396 | O | ASP A | 184 | 29.440 | 9.968 | −23.414 | 1.00 | 85.42 | O |
| ATOM | 1397 | N | PRO A | 185 | 30.833 | 11.681 | −22.784 | 1.00 | 95.79 | N |
| ATOM | 1398 | CA | PRO A | 185 | 31.293 | 11.771 | −24.179 | 1.00 | 94.16 | C |
| ATOM | 1399 | CB | PRO A | 185 | 32.075 | 13.104 | −24.220 | 1.00 | 94.73 | C |
| ATOM | 1400 | CG | PRO A | 185 | 31.911 | 13.737 | −22.854 | 1.00 | 93.00 | C |
| ATOM | 1401 | CD | PRO A | 185 | 31.533 | 12.651 | −21.910 | 1.00 | 89.84 | C |
| ATOM | 1402 | C | PRO A | 185 | 32.172 | 10.579 | −24.637 | 1.00 | 92.58 | C |
| ATOM | 1403 | O | PRO A | 185 | 32.682 | 10.640 | −25.761 | 1.00 | 86.48 | O |
| ATOM | 1404 | N | GLN A | 186 | 32.372 | 9.553 | −23.774 | 1.00 | 92.12 | N |
| ATOM | 1405 | CA | GLN A | 186 | 32.927 | 8.230 | −24.168 | 1.00 | 90.88 | C |
| ATOM | 1406 | CB | GLN A | 186 | 33.742 | 7.576 | −23.037 | 1.00 | 82.64 | C |
| ATOM | 1407 | C | GLN A | 186 | 31.815 | 7.293 | −24.697 | 1.00 | 93.36 | C |
| ATOM | 1408 | O | GLN A | 186 | 31.953 | 6.770 | −25.811 | 1.00 | 91.61 | O |
| ATOM | 1409 | N | GLY A | 187 | 30.713 | 7.111 | −23.949 | 1.00 | 96.14 | N |
| ATOM | 1410 | CA | GLY A | 187 | 29.537 | 6.330 | −24.457 | 1.00 | 96.40 | C |
| ATOM | 1411 | C | GLY A | 187 | 28.361 | 6.139 | −23.495 | 1.00 | 92.97 | C |
| ATOM | 1412 | O | GLY A | 187 | 28.126 | 7.000 | −22.657 | 1.00 | 85.56 | O |
| ATOM | 1413 | N | ARG A | 188 | 27.642 | 5.010 | −23.615 | 1.00 | 91.25 | N |
| ATOM | 1414 | CA | ARG A | 188 | 26.528 | 4.648 | −22.705 | 1.00 | 93.83 | C |
| ATOM | 1415 | CB | ARG A | 188 | 25.226 | 4.321 | −23.472 | 1.00 | 99.71 | C |
| ATOM | 1416 | CG | ARG A | 188 | 24.223 | 5.449 | −23.432 | 1.00 | 102.89 | C |
| ATOM | 1417 | CD | ARG A | 188 | 22.773 | 5.121 | −23.724 | 1.00 | 99.68 | C |
| ATOM | 1418 | NE | ARG A | 188 | 22.259 | 6.326 | −24.360 | 1.00 | 107.07 | N |
| ATOM | 1419 | CZ | ARG A | 188 | 21.142 | 6.434 | −25.062 | 1.00 | 113.62 | C |
| ATOM | 1420 | NH1 | ARG A | 188 | 20.309 | 5.414 | −25.187 | 1.00 | 114.44 | N |
| ATOM | 1421 | NH2 | ARG A | 188 | 20.845 | 7.608 | −25.616 | 1.00 | 117.13 | N |
| ATOM | 1422 | C | ARG A | 188 | 26.830 | 3.437 | −21.865 | 1.00 | 90.36 | C |
| ATOM | 1423 | O | ARG A | 188 | 27.020 | 2.357 | −22.418 | 1.00 | 91.08 | O |
| ATOM | 1424 | N | HIS A | 189 | 26.821 | 3.595 | −20.542 | 1.00 | 86.14 | N |
| ATOM | 1425 | CA | HIS A | 189 | 27.211 | 2.510 | −19.628 | 1.00 | 86.74 | C |
| ATOM | 1426 | CB | HIS A | 189 | 28.585 | 2.814 | −19.000 | 1.00 | 94.47 | C |
| ATOM | 1427 | CG | HIS A | 189 | 29.404 | 3.799 | −19.773 | 1.00 | 92.95 | C |
| ATOM | 1428 | ND1 | HIS A | 189 | 29.668 | 3.650 | −21.118 | 1.00 | 93.70 | N |
| ATOM | 1429 | CE1 | HIS A | 189 | 30.405 | 4.660 | −21.533 | 1.00 | 94.37 | C |
| ATOM | 1430 | NE2 | HIS A | 189 | 30.634 | 5.456 | −20.505 | 1.00 | 93.49 | N |
| ATOM | 1431 | CD2 | HIS A | 189 | 30.027 | 4.935 | −19.391 | 1.00 | 89.59 | C |
| ATOM | 1432 | C | HIS A | 189 | 26.229 | 2.318 | −18.498 | 1.00 | 80.46 | C |
| ATOM | 1433 | O | HIS A | 189 | 25.521 | 3.244 | −18.141 | 1.00 | 78.55 | O |
| ATOM | 1434 | N | VAL A | 190 | 26.235 | 1.136 | −17.886 | 1.00 | 77.54 | N |
| ATOM | 1435 | CA | VAL A | 190 | 25.486 | 0.936 | −16.621 | 1.00 | 74.97 | C |
| ATOM | 1436 | CB | VAL A | 190 | 24.426 | −0.231 | −16.660 | 1.00 | 73.17 | C |
| ATOM | 1437 | CG1 | VAL A | 190 | 24.846 | −1.384 | −17.527 | 1.00 | 77.47 | C |
| ATOM | 1438 | CG2 | VAL A | 190 | 24.052 | −0.763 | −15.284 | 1.00 | 72.17 | C |
| ATOM | 1439 | C | VAL A | 190 | 26.465 | 0.949 | −15.419 | 1.00 | 76.37 | C |
| ATOM | 1440 | O | VAL A | 190 | 27.655 | 0.687 | −15.558 | 1.00 | 78.31 | O |
| ATOM | 1441 | N | LYS A | 191 | 25.913 | 1.294 | −14.267 | 1.00 | 79.89 | N |
| ATOM | 1442 | CA | LYS A | 191 | 26.643 | 1.453 | −13.036 | 1.00 | 78.24 | C |
| ATOM | 1443 | CB | LYS A | 191 | 27.126 | 2.883 | −12.975 | 1.00 | 78.08 | C |
| ATOM | 1444 | CG | LYS A | 191 | 28.017 | 3.218 | −11.806 | 1.00 | 87.08 | C |
| ATOM | 1445 | CD | LYS A | 191 | 28.454 | 4.663 | −11.929 | 1.00 | 93.49 | C |
| ATOM | 1446 | CE | LYS A | 191 | 29.686 | 4.978 | −11.112 | 1.00 | 95.62 | C |
| ATOM | 1447 | NZ | LYS A | 191 | 29.943 | 6.440 | −11.136 | 1.00 | 97.54 | N |
| ATOM | 1448 | C | LYS A | 191 | 25.661 | 1.248 | −11.923 | 1.00 | 79.81 | C |
| ATOM | 1449 | O | LYS A | 191 | 24.483 | 1.172 | −12.176 | 1.00 | 85.54 | O |
| ATOM | 1450 | N | THR A | 192 | 26.132 | 1.135 | −10.691 | 1.00 | 74.10 | N |
| ATOM | 1451 | CA | THR A | 192 | 25.230 | 0.993 | −9.562 | 1.00 | 71.39 | C |
| ATOM | 1452 | CB | THR A | 192 | 24.875 | −0.460 | −9.295 | 1.00 | 71.64 | C |

TABLE 6-continued

Atomic coordinates for CRBN:DDB1: Compound B (Human protein)

| ATOM | 1453 | OG1 | THR A | 192 | 25.943 | −1.086 | −8.594 | 1.00 | 72.61 | O |
|---|---|---|---|---|---|---|---|---|---|---|
| ATOM | 1454 | CG2 | THR A | 192 | 24.666 | −1.160 | −10.577 | 1.00 | 68.02 | C |
| ATOM | 1455 | C | THR A | 192 | 25.858 | 1.597 | −8.332 | 1.00 | 70.94 | C |
| ATOM | 1456 | O | THR A | 192 | 27.055 | 1.722 | −8.275 | 1.00 | 77.22 | O |
| ATOM | 1457 | N | TYR A | 193 | 25.053 | 1.966 | −7.351 | 1.00 | 70.41 | N |
| ATOM | 1458 | CA | TYR A | 193 | 25.558 | 2.532 | −6.109 | 1.00 | 74.98 | C |
| ATOM | 1459 | CB | TYR A | 193 | 25.427 | 4.037 | −6.036 | 1.00 | 75.51 | C |
| ATOM | 1460 | CG | TYR A | 193 | 26.239 | 4.830 | −6.996 | 1.00 | 81.31 | C |
| ATOM | 1461 | CD1 | TYR A | 193 | 27.351 | 4.313 | −7.589 | 1.00 | 86.21 | C |
| ATOM | 1462 | CE1 | TYR A | 193 | 28.096 | 5.063 | −8.470 | 1.00 | 91.79 | C |
| ATOM | 1463 | CZ | TYR A | 193 | 27.734 | 6.354 | −8.741 | 1.00 | 93.07 | C |
| ATOM | 1464 | OH | TYR A | 193 | 28.453 | 7.129 | −9.615 | 1.00 | 89.51 | O |
| ATOM | 1465 | CE2 | TYR A | 193 | 26.635 | 6.887 | −8.148 | 1.00 | 96.48 | C |
| ATOM | 1466 | CD2 | TYR A | 193 | 25.902 | 6.127 | −7.274 | 1.00 | 91.27 | C |
| ATOM | 1467 | C | TYR A | 193 | 24.751 | 1.984 | −4.970 | 1.00 | 74.93 | C |
| ATOM | 1468 | O | TYR A | 193 | 23.747 | 1.335 | −5.169 | 1.00 | 80.70 | O |
| ATOM | 1469 | N | GLU A | 194 | 25.202 | 2.248 | −3.764 | 1.00 | 76.32 | N |
| ATOM | 1470 | CA | GLU A | 194 | 24.489 | 1.818 | −2.590 | 1.00 | 79.68 | C |
| ATOM | 1471 | CB | GLU A | 194 | 25.378 | 1.021 | −1.668 | 1.00 | 87.98 | C |
| ATOM | 1472 | CG | GLU A | 194 | 25.550 | −0.422 | −2.073 | 1.00 | 91.79 | C |
| ATOM | 1473 | CD | GLU A | 194 | 25.926 | −1.299 | −0.907 | 1.00 | 94.25 | C |
| ATOM | 1474 | OE1 | GLU A | 194 | 25.955 | −0.806 | 0.232 | 1.00 | 87.06 | O |
| ATOM | 1475 | OE2 | GLU A | 194 | 26.189 | −2.488 | −1.128 | 1.00 | 94.94 | O |
| ATOM | 1476 | C | GLU A | 194 | 24.059 | 3.093 | −1.922 | 1.00 | 75.58 | C |
| ATOM | 1477 | O | GLU A | 194 | 24.657 | 4.134 | −2.151 | 1.00 | 63.27 | O |
| ATOM | 1478 | N | VAL A | 195 | 23.013 | 3.025 | −1.112 | 1.00 | 75.88 | N |
| ATOM | 1479 | CA | VAL A | 195 | 22.479 | 4.241 | −0.457 | 1.00 | 76.97 | C |
| ATOM | 1480 | CB | VAL A | 195 | 21.089 | 4.626 | −1.027 | 1.00 | 76.13 | C |
| ATOM | 1481 | CG1 | VAL A | 195 | 20.527 | 5.840 | −0.305 | 1.00 | 81.35 | C |
| ATOM | 1482 | CG2 | VAL A | 195 | 21.189 | 4.961 | −2.506 | 1.00 | 73.76 | C |
| ATOM | 1483 | C | VAL A | 195 | 22.435 | 4.151 | 1.085 | 1.00 | 75.06 | C |
| ATOM | 1484 | O | VAL A | 195 | 21.647 | 3.384 | 1.674 | 1.00 | 76.98 | O |
| ATOM | 1485 | N | SER A | 196 | 23.281 | 4.952 | 1.729 | 1.00 | 72.91 | N |
| ATOM | 1486 | CA | SER A | 196 | 23.273 | 5.040 | 3.167 | 1.00 | 79.27 | C |
| ATOM | 1487 | CB | SER A | 196 | 24.678 | 4.952 | 3.744 | 1.00 | 80.16 | C |
| ATOM | 1488 | OG | SER A | 196 | 24.592 | 4.956 | 5.165 | 1.00 | 80.00 | O |
| ATOM | 1489 | C | SER A | 196 | 22.630 | 6.358 | 3.574 | 1.00 | 84.94 | C |
| ATOM | 1490 | O | SER A | 196 | 23.193 | 7.452 | 3.355 | 1.00 | 78.44 | O |
| ATOM | 1491 | N | LEU A | 197 | 21.442 | 6.230 | 4.167 | 1.00 | 89.41 | N |
| ATOM | 1492 | CA | LEU A | 197 | 20.744 | 7.357 | 4.815 | 1.00 | 89.91 | C |
| ATOM | 1493 | CB | LEU A | 197 | 19.364 | 6.969 | 5.421 | 1.00 | 88.66 | C |
| ATOM | 1494 | CG | LEU A | 197 | 18.335 | 6.136 | 4.638 | 1.00 | 88.96 | C |
| ATOM | 1495 | CD1 | LEU A | 197 | 18.319 | 6.589 | 3.181 | 1.00 | 94.78 | C |
| ATOM | 1496 | CD2 | LEU A | 197 | 18.547 | 4.616 | 4.738 | 1.00 | 90.77 | C |
| ATOM | 1497 | C | LEU A | 197 | 21.628 | 7.768 | 5.938 | 1.00 | 87.49 | C |
| ATOM | 1498 | O | LEU A | 197 | 21.853 | 8.941 | 6.162 | 1.00 | 87.07 | O |
| ATOM | 1499 | N | ARG A | 198 | 22.121 | 6.740 | 6.616 | 1.00 | 90.26 | N |
| ATOM | 1500 | CA | ARG A | 198 | 22.947 | 6.835 | 7.786 | 1.00 | 92.81 | C |
| ATOM | 1501 | CB | ARG A | 198 | 23.365 | 5.401 | 8.132 | 1.00 | 102.74 | C |
| ATOM | 1502 | CG | ARG A | 198 | 23.759 | 5.079 | 9.564 | 1.00 | 110.90 | C |
| ATOM | 1503 | CD | ARG A | 198 | 24.113 | 3.585 | 9.626 | 1.00 | 113.87 | C |
| ATOM | 1504 | NE | ARG A | 198 | 25.444 | 3.286 | 10.173 | 1.00 | 120.95 | N |
| ATOM | 1505 | CZ | ARG A | 198 | 26.629 | 3.723 | 9.706 | 1.00 | 124.17 | C |
| ATOM | 1506 | NH1 | ARG A | 198 | 26.734 | 4.562 | 8.667 | 1.00 | 123.64 | N |
| ATOM | 1507 | NH2 | ARG A | 198 | 27.756 | 3.330 | 10.313 | 1.00 | 123.18 | N |
| ATOM | 1508 | C | ARG A | 198 | 24.131 | 7.794 | 7.553 | 1.00 | 86.29 | C |
| ATOM | 1509 | O | ARG A | 198 | 24.501 | 8.515 | 8.476 | 1.00 | 84.10 | O |
| ATOM | 1510 | N | GLU A | 199 | 24.676 | 7.825 | 6.324 | 1.00 | 82.72 | N |
| ATOM | 1511 | CA | GLU A | 199 | 25.754 | 8.774 | 5.897 | 1.00 | 84.03 | C |
| ATOM | 1512 | CB | GLU A | 199 | 26.924 | 8.038 | 5.215 | 1.00 | 91.08 | C |
| ATOM | 1513 | CG | GLU A | 199 | 27.516 | 6.807 | 5.867 | 1.00 | 94.42 | C |
| ATOM | 1514 | CD | GLU A | 199 | 28.588 | 6.202 | 4.971 | 1.00 | 95.97 | C |
| ATOM | 1515 | OE1 | GLU A | 199 | 28.256 | 5.382 | 4.071 | 1.00 | 90.86 | O |
| ATOM | 1516 | OE2 | GLU A | 199 | 29.759 | 6.600 | 5.150 | 1.00 | 98.36 | O |
| ATOM | 1517 | C | GLU A | 199 | 25.360 | 9.831 | 4.854 | 1.00 | 79.60 | C |
| ATOM | 1518 | O | GLU A | 199 | 26.219 | 10.641 | 4.449 | 1.00 | 70.72 | O |
| ATOM | 1519 | N | LYS A | 200 | 24.119 | 9.763 | 4.351 | 1.00 | 79.07 | N |
| ATOM | 1520 | CA | LYS A | 200 | 23.570 | 10.708 | 3.345 | 1.00 | 73.57 | C |
| ATOM | 1521 | CB | LYS A | 200 | 23.322 | 12.110 | 3.911 | 1.00 | 72.12 | C |
| ATOM | 1522 | CG | LYS A | 200 | 22.265 | 12.190 | 5.010 | 1.00 | 73.63 | C |
| ATOM | 1523 | CD | LYS A | 200 | 21.828 | 13.643 | 5.187 | 1.00 | 76.71 | C |
| ATOM | 1524 | CE | LYS A | 200 | 20.813 | 13.819 | 6.289 | 1.00 | 76.60 | C |
| ATOM | 1525 | NZ | LYS A | 200 | 21.480 | 13.607 | 7.601 | 1.00 | 82.13 | N |
| ATOM | 1526 | C | LYS A | 200 | 24.509 | 10.775 | 2.186 | 1.00 | 69.92 | C |
| ATOM | 1527 | O | LYS A | 200 | 24.986 | 11.842 | 1.800 | 1.00 | 65.43 | O |
| ATOM | 1528 | N | GLU A | 201 | 24.890 | 9.603 | 1.734 | 1.00 | 71.91 | N |
| ATOM | 1529 | CA | GLU A | 201 | 25.845 | 9.533 | 0.676 | 1.00 | 78.64 | C |
| ATOM | 1530 | CB | GLU A | 201 | 27.228 | 9.816 | 1.228 | 1.00 | 91.86 | C |

TABLE 6-continued

Atomic coordinates for CRBN:DDB1: Compound B (Human protein)

| ATOM | 1531 | CG | GLU A | 201 | 28.311 | 9.807 | 0.179 | 1.00 | 100.96 | C |
|---|---|---|---|---|---|---|---|---|---|---|
| ATOM | 1532 | CD | GLU A | 201 | 28.388 | 11.105 | −0.590 | 1.00 | 108.09 | C |
| ATOM | 1533 | OE1 | GLU A | 201 | 28.560 | 12.161 | 0.049 | 1.00 | 112.25 | O |
| ATOM | 1534 | OE2 | GLU A | 201 | 28.295 | 11.067 | −1.835 | 1.00 | 106.19 | O |
| ATOM | 1535 | C | GLU A | 201 | 25.834 | 8.203 | −0.004 | 1.00 | 75.81 | C |
| ATOM | 1536 | O | GLU A | 201 | 25.286 | 7.239 | 0.492 | 1.00 | 71.35 | O |
| ATOM | 1537 | N | PHE A | 202 | 26.457 | 8.187 | −1.164 | 1.00 | 78.06 | N |
| ATOM | 1538 | CA | PHE A | 202 | 26.590 | 7.016 | −1.991 | 1.00 | 83.17 | C |
| ATOM | 1539 | CB | PHE A | 202 | 26.837 | 7.463 | −3.412 | 1.00 | 86.53 | C |
| ATOM | 1540 | CG | PHE A | 202 | 25.604 | 7.724 | −4.184 | 1.00 | 82.12 | C |
| ATOM | 1541 | CD1 | PHE A | 202 | 24.540 | 6.883 | −4.082 | 1.00 | 79.38 | C |
| ATOM | 1542 | CE1 | PHE A | 202 | 23.403 | 7.116 | −4.797 | 1.00 | 80.62 | C |
| ATOM | 1543 | CZ | PHE A | 202 | 23.338 | 8.191 | −5.638 | 1.00 | 85.47 | C |
| ATOM | 1544 | CE2 | PHE A | 202 | 24.406 | 9.033 | −5.757 | 1.00 | 84.81 | C |
| ATOM | 1545 | CD2 | PHE A | 202 | 25.533 | 8.792 | −5.031 | 1.00 | 83.14 | C |
| ATOM | 1546 | C | PHE A | 202 | 27.777 | 6.163 | −1.640 | 1.00 | 84.12 | C |
| ATOM | 1547 | O | PHE A | 202 | 28.829 | 6.661 | −1.289 | 1.00 | 81.93 | O |
| ATOM | 1548 | N | ASN A | 203 | 27.615 | 4.864 | −1.768 | 1.00 | 87.89 | N |
| ATOM | 1549 | CA | ASN A | 203 | 28.708 | 3.957 | −1.543 | 1.00 | 89.06 | C |
| ATOM | 1550 | CB | ASN A | 203 | 28.402 | 2.990 | −0.410 | 1.00 | 82.66 | C |
| ATOM | 1551 | CG | ASN A | 203 | 28.561 | 3.616 | 0.940 | 1.00 | 75.06 | C |
| ATOM | 1552 | OD1 | ASN A | 203 | 29.029 | 4.734 | 1.052 | 1.00 | 71.41 | O |
| ATOM | 1553 | ND2 | ASN A | 203 | 28.171 | 2.897 | 1.974 | 1.00 | 69.29 | N |
| ATOM | 1554 | C | ASN A | 203 | 28.807 | 3.200 | −2.841 | 1.00 | 94.32 | C |
| ATOM | 1555 | O | ASN A | 203 | 27.804 | 2.718 | −3.339 | 1.00 | 95.74 | O |
| ATOM | 1556 | N | LYS A | 204 | 29.990 | 3.090 | −3.419 | 1.00 | 95.80 | N |
| ATOM | 1557 | CA | LYS A | 204 | 30.054 | 2.337 | −4.655 | 1.00 | 93.65 | C |
| ATOM | 1558 | CB | LYS A | 204 | 31.477 | 2.367 | −5.208 | 1.00 | 101.22 | C |
| ATOM | 1559 | CG | LYS A | 204 | 31.601 | 1.986 | −6.684 | 1.00 | 113.30 | C |
| ATOM | 1560 | CD | LYS A | 204 | 32.587 | 0.829 | −6.891 | 1.00 | 117.80 | C |
| ATOM | 1561 | CE | LYS A | 204 | 32.109 | −0.493 | −6.276 | 1.00 | 117.81 | C |
| ATOM | 1562 | NZ | LYS A | 204 | 33.214 | −1.480 | −6.087 | 1.00 | 119.23 | N |
| ATOM | 1563 | C | LYS A | 204 | 29.526 | 0.904 | −4.383 | 1.00 | 86.39 | C |
| ATOM | 1564 | O | LYS A | 204 | 29.488 | 0.418 | −3.235 | 1.00 | 72.00 | O |
| ATOM | 1565 | N | GLY A | 205 | 29.069 | 0.251 | −5.442 | 1.00 | 86.04 | N |
| ATOM | 1566 | CA | GLY A | 205 | 28.228 | −0.903 | −5.278 | 1.00 | 87.91 | C |
| ATOM | 1567 | C | GLY A | 205 | 28.389 | −2.010 | −6.285 | 1.00 | 88.77 | C |
| ATOM | 1568 | O | GLY A | 205 | 29.167 | −1.886 | −7.240 | 1.00 | 80.97 | O |
| ATOM | 1569 | N | PRO A | 206 | 27.605 | −3.093 | −6.083 | 1.00 | 95.88 | N |
| ATOM | 1570 | CA | PRO A | 206 | 27.808 | −4.419 | −6.635 | 1.00 | 97.25 | C |
| ATOM | 1571 | CB | PRO A | 206 | 26.400 | −5.031 | −6.587 | 1.00 | 100.43 | C |
| ATOM | 1572 | CG | PRO A | 206 | 25.853 | −4.509 | −5.307 | 1.00 | 99.84 | C |
| ATOM | 1573 | CD | PRO A | 206 | 26.462 | −3.122 | −5.139 | 1.00 | 99.58 | C |
| ATOM | 1574 | C | PRO A | 206 | 28.415 | −4.566 | −8.013 | 1.00 | 92.16 | C |
| ATOM | 1575 | O | PRO A | 206 | 29.143 | −5.528 | −8.196 | 1.00 | 95.33 | O |
| ATOM | 1576 | N | TRP A | 207 | 28.148 | −3.684 | −8.976 | 1.00 | 88.56 | N |
| ATOM | 1577 | CA | TRP A | 207 | 28.685 | −3.947 | −10.325 | 1.00 | 93.77 | C |
| ATOM | 1578 | CB | TRP A | 207 | 28.009 | −5.207 | −10.943 | 1.00 | 95.32 | C |
| ATOM | 1579 | CG | TRP A | 207 | 26.496 | −5.334 | −10.879 | 1.00 | 93.50 | C |
| ATOM | 1580 | CD1 | TRP A | 207 | 25.731 | −5.986 | −9.919 | 1.00 | 93.22 | C |
| ATOM | 1581 | NE1 | TRP A | 207 | 24.405 | −5.940 | −10.261 | 1.00 | 87.26 | N |
| ATOM | 1582 | CE2 | TRP A | 207 | 24.294 | −5.281 | −11.461 | 1.00 | 92.67 | C |
| ATOM | 1583 | CD2 | TRP A | 207 | 25.593 | −4.900 | −11.874 | 1.00 | 89.25 | C |
| ATOM | 1584 | CE3 | TRP A | 207 | 25.750 | −4.197 | −13.078 | 1.00 | 89.46 | C |
| ATOM | 1585 | CZ3 | TRP A | 207 | 24.628 | −3.893 | −13.831 | 1.00 | 90.76 | C |
| ATOM | 1586 | CH2 | TRP A | 207 | 23.345 | −4.277 | −13.397 | 1.00 | 99.05 | C |
| ATOM | 1587 | CZ2 | TRP A | 207 | 23.157 | −4.971 | −12.216 | 1.00 | 99.70 | C |
| ATOM | 1588 | C | TRP A | 207 | 28.752 | −2.751 | −11.293 | 1.00 | 92.11 | C |
| ATOM | 1589 | O | TRP A | 207 | 28.644 | −1.604 | −10.847 | 1.00 | 90.25 | O |
| ATOM | 1590 | N | LYS A | 208 | 29.037 | −3.035 | −12.578 | 1.00 | 85.58 | N |
| ATOM | 1591 | CA | LYS A | 208 | 29.162 | −2.025 | −13.633 | 1.00 | 80.94 | C |
| ATOM | 1592 | CB | LYS A | 208 | 30.376 | −1.087 | −13.375 | 1.00 | 85.85 | C |
| ATOM | 1593 | CG | LYS A | 208 | 31.637 | −1.822 | −12.925 | 1.00 | 95.76 | C |
| ATOM | 1594 | CD | LYS A | 208 | 32.948 | −1.191 | −13.383 | 1.00 | 98.07 | C |
| ATOM | 1595 | CE | LYS A | 208 | 34.101 | −2.151 | −13.086 | 1.00 | 102.45 | C |
| ATOM | 1596 | NZ | LYS A | 208 | 35.403 | −1.711 | −13.660 | 1.00 | 105.02 | N |
| ATOM | 1597 | C | LYS A | 208 | 29.279 | −2.679 | −15.032 | 1.00 | 77.39 | C |
| ATOM | 1598 | O | LYS A | 208 | 29.247 | −3.929 | −15.183 | 1.00 | 73.41 | O |
| ATOM | 1599 | N | GLN A | 209 | 29.377 | −1.791 | −16.032 | 1.00 | 72.33 | N |
| ATOM | 1600 | CA | GLN A | 209 | 29.536 | −2.110 | −17.429 | 1.00 | 66.43 | C |
| ATOM | 1601 | CB | GLN A | 209 | 28.311 | −2.906 | −17.867 | 1.00 | 68.69 | C |
| ATOM | 1602 | CG | GLN A | 209 | 28.084 | −2.971 | −19.356 | 1.00 | 78.41 | C |
| ATOM | 1603 | CD | GLN A | 209 | 29.377 | −3.157 | −20.123 | 1.00 | 85.27 | C |
| ATOM | 1604 | OE1 | GLN A | 209 | 29.719 | −2.355 | −21.023 | 1.00 | 86.31 | O |
| ATOM | 1605 | NE2 | GLN A | 209 | 30.145 | −4.182 | −19.724 | 1.00 | 85.39 | N |
| ATOM | 1606 | C | GLN A | 209 | 29.719 | −0.797 | −18.256 | 1.00 | 60.22 | C |
| ATOM | 1607 | O | GLN A | 209 | 30.733 | −0.566 | −18.951 | 1.00 | 47.90 | O |
| ATOM | 1608 | N | ASN A | 211 | 30.586 | 0.236 | −21.662 | 1.00 | 71.25 | N |

TABLE 6-continued

Atomic coordinates for CRBN:DDB1: Compound B (Human protein)

| ATOM | 1609 | CA | ASN A | 211 | 29.990 | 0.481 | −22.997 | 1.00 | 79.14 | C |
|---|---|---|---|---|---|---|---|---|---|---|
| ATOM | 1610 | CB | ASN A | 211 | 31.081 | 0.680 | −24.109 | 1.00 | 67.09 | C |
| ATOM | 1611 | C | ASN A | 211 | 28.928 | −0.618 | −23.335 | 1.00 | 84.06 | C |
| ATOM | 1612 | O | ASN A | 211 | 29.278 | −1.643 | −23.926 | 1.00 | 93.04 | O |
| ATOM | 1613 | N | VAL A | 212 | 27.668 | −0.420 | −22.868 | 1.00 | 87.14 | N |
| ATOM | 1614 | CA | VAL A | 212 | 26.422 | −1.186 | −23.310 | 1.00 | 83.01 | C |
| ATOM | 1615 | CB | VAL A | 212 | 25.180 | −1.293 | −22.322 | 1.00 | 83.12 | C |
| ATOM | 1616 | CG1 | VAL A | 212 | 24.804 | −2.746 | −22.012 | 1.00 | 81.01 | C |
| ATOM | 1617 | CG2 | VAL A | 212 | 25.296 | −0.414 | −21.082 | 1.00 | 86.65 | C |
| ATOM | 1618 | C | VAL A | 212 | 25.867 | −0.435 | −24.492 | 1.00 | 79.51 | C |
| ATOM | 1619 | O | VAL A | 212 | 26.356 | 0.676 | −24.779 | 1.00 | 73.35 | O |
| ATOM | 1620 | N | GLU A | 213 | 24.829 | −1.021 | −25.118 | 1.00 | 74.80 | N |
| ATOM | 1621 | CA | GLU A | 213 | 24.316 | −0.582 | −26.421 | 1.00 | 76.44 | C |
| ATOM | 1622 | CB | GLU A | 213 | 22.958 | −1.224 | −26.723 | 1.00 | 79.83 | C |
| ATOM | 1623 | CG | GLU A | 213 | 22.675 | −1.322 | −28.222 | 1.00 | 84.47 | C |
| ATOM | 1624 | CD | GLU A | 213 | 21.258 | −0.924 | −28.599 | 1.00 | 88.82 | C |
| ATOM | 1625 | OE1 | GLU A | 213 | 20.308 | −1.711 | −28.317 | 1.00 | 87.57 | O |
| ATOM | 1626 | OE2 | GLU A | 213 | 21.112 | 0.178 | −29.196 | 1.00 | 89.82 | O |
| ATOM | 1627 | C | GLU A | 213 | 24.213 | 0.930 | −26.635 | 1.00 | 76.05 | C |
| ATOM | 1628 | O | GLU A | 213 | 23.803 | 1.669 | −25.745 | 1.00 | 70.95 | O |
| ATOM | 1629 | N | ALA A | 214 | 24.590 | 1.374 | −27.835 | 1.00 | 83.46 | N |
| ATOM | 1630 | CA | ALA A | 214 | 24.505 | 2.796 | −28.240 | 1.00 | 89.09 | C |
| ATOM | 1631 | CB | ALA A | 214 | 24.562 | 2.908 | −29.769 | 1.00 | 91.56 | C |
| ATOM | 1632 | C | ALA A | 214 | 23.252 | 3.512 | −27.720 | 1.00 | 87.51 | C |
| ATOM | 1633 | O | ALA A | 214 | 23.348 | 4.604 | −27.133 | 1.00 | 93.83 | O |
| ATOM | 1634 | N | GLU A | 215 | 22.101 | 2.858 | −27.932 | 1.00 | 81.32 | N |
| ATOM | 1635 | CA | GLU A | 215 | 20.774 | 3.419 | −27.737 | 1.00 | 76.19 | C |
| ATOM | 1636 | CB | GLU A | 215 | 20.079 | 3.515 | −29.139 | 1.00 | 83.31 | C |
| ATOM | 1637 | CG | GLU A | 215 | 18.941 | 4.558 | −29.358 | 1.00 | 91.64 | C |
| ATOM | 1638 | CD | GLU A | 215 | 19.326 | 5.944 | −29.934 | 1.00 | 100.43 | C |
| ATOM | 1639 | OE1 | GLU A | 215 | 18.439 | 6.864 | −29.989 | 1.00 | 107.70 | O |
| ATOM | 1640 | OE2 | GLU A | 215 | 20.494 | 6.138 | −30.339 | 1.00 | 99.30 | O |
| ATOM | 1641 | C | GLU A | 215 | 20.003 | 2.579 | −26.671 | 1.00 | 69.44 | C |
| ATOM | 1642 | O | GLU A | 215 | 18.815 | 2.352 | −26.773 | 1.00 | 70.21 | O |
| ATOM | 1643 | N | ALA A | 216 | 20.684 | 2.137 | −25.618 | 1.00 | 71.41 | N |
| ATOM | 1644 | CA | ALA A | 216 | 19.996 | 1.582 | −24.415 | 1.00 | 76.29 | C |
| ATOM | 1645 | CB | ALA A | 216 | 20.992 | 0.846 | −23.489 | 1.00 | 71.92 | C |
| ATOM | 1646 | C | ALA A | 216 | 19.221 | 2.702 | −23.623 | 1.00 | 79.85 | C |
| ATOM | 1647 | O | ALA A | 216 | 19.789 | 3.783 | −23.334 | 1.00 | 79.22 | O |
| ATOM | 1648 | N | SER A | 217 | 17.952 | 2.427 | −23.275 | 1.00 | 77.23 | N |
| ATOM | 1649 | CA | SER A | 217 | 17.064 | 3.408 | −22.622 | 1.00 | 72.22 | C |
| ATOM | 1650 | CB | SER A | 217 | 16.074 | 3.908 | −23.648 | 1.00 | 73.40 | C |
| ATOM | 1651 | OG | SER A | 217 | 15.155 | 2.875 | −23.901 | 1.00 | 78.99 | O |
| ATOM | 1652 | C | SER A | 217 | 16.285 | 2.911 | −21.380 | 1.00 | 67.82 | C |
| ATOM | 1653 | O | SER A | 217 | 16.184 | 3.617 | −20.419 | 1.00 | 69.16 | O |
| ATOM | 1654 | N | MET A | 218 | 15.714 | 1.724 | −21.393 | 1.00 | 66.69 | N |
| ATOM | 1655 | CA | MET A | 218 | 14.905 | 1.239 | −20.263 | 1.00 | 68.22 | C |
| ATOM | 1656 | CB | MET A | 218 | 13.745 | 0.458 | −20.853 | 1.00 | 70.91 | C |
| ATOM | 1657 | CG | MET A | 218 | 12.685 | −0.026 | −19.882 | 1.00 | 73.50 | C |
| ATOM | 1658 | SD | MET A | 218 | 11.235 | −0.660 | −20.760 | 1.00 | 78.06 | S |
| ATOM | 1659 | CE | MET A | 218 | 10.913 | 0.605 | −22.008 | 1.00 | 74.64 | C |
| ATOM | 1660 | C | MET A | 218 | 15.695 | 0.356 | −19.291 | 1.00 | 66.48 | C |
| ATOM | 1661 | O | MET A | 218 | 16.694 | −0.217 | −19.647 | 1.00 | 73.89 | O |
| ATOM | 1662 | N | VAL A | 219 | 15.236 | 0.228 | −18.062 | 1.00 | 64.27 | N |
| ATOM | 1663 | CA | VAL A | 219 | 15.936 | −0.545 | −17.031 | 1.00 | 62.09 | C |
| ATOM | 1664 | CB | VAL A | 219 | 16.611 | 0.429 | −16.063 | 1.00 | 64.85 | C |
| ATOM | 1665 | CG1 | VAL A | 219 | 16.949 | −0.235 | −14.735 | 1.00 | 67.52 | C |
| ATOM | 1666 | CG2 | VAL A | 219 | 17.839 | 1.030 | −16.715 | 1.00 | 65.31 | C |
| ATOM | 1667 | C | VAL A | 219 | 14.921 | −1.335 | −16.249 | 1.00 | 57.92 | C |
| ATOM | 1668 | O | VAL A | 219 | 13.909 | −0.803 | −15.935 | 1.00 | 63.01 | O |
| ATOM | 1669 | N | ILE A | 220 | 15.168 | −2.577 | −15.887 | 1.00 | 55.30 | N |
| ATOM | 1670 | CA | ILE A | 220 | 14.129 | −3.337 | −15.184 | 1.00 | 56.33 | C |
| ATOM | 1671 | CB | ILE A | 220 | 13.408 | −4.357 | −16.105 | 1.00 | 53.98 | C |
| ATOM | 1672 | CG1 | ILE A | 220 | 12.784 | −3.633 | −17.298 | 1.00 | 55.61 | C |
| ATOM | 1673 | CD1 | ILE A | 220 | 12.094 | −4.534 | −18.306 | 1.00 | 56.98 | C |
| ATOM | 1674 | CG2 | ILE A | 220 | 12.324 | −5.152 | −15.346 | 1.00 | 52.13 | C |
| ATOM | 1675 | C | ILE A | 220 | 14.702 | −4.050 | −13.981 | 1.00 | 58.62 | C |
| ATOM | 1676 | O | ILE A | 220 | 15.521 | −4.907 | −14.136 | 1.00 | 59.02 | O |
| ATOM | 1677 | N | ALA A | 221 | 14.245 | −3.721 | −12.778 | 1.00 | 63.31 | N |
| ATOM | 1678 | CA | ALA A | 221 | 14.754 | −4.392 | −11.589 | 1.00 | 63.96 | C |
| ATOM | 1679 | CB | ALA A | 221 | 14.393 | −3.624 | −10.333 | 1.00 | 64.31 | C |
| ATOM | 1680 | C | ALA A | 221 | 14.142 | −5.767 | −11.579 | 1.00 | 66.71 | C |
| ATOM | 1681 | O | ALA A | 221 | 12.915 | −5.903 | −11.641 | 1.00 | 65.95 | O |
| ATOM | 1682 | N | VAL A | 222 | 14.970 | −6.790 | −11.512 | 1.00 | 72.18 | N |
| ATOM | 1683 | CA | VAL A | 222 | 14.439 | −8.127 | −11.477 | 1.00 | 71.65 | C |
| ATOM | 1684 | CB | VAL A | 222 | 15.384 | −9.151 | −12.092 | 1.00 | 70.53 | C |
| ATOM | 1685 | CG1 | VAL A | 222 | 14.846 | −10.546 | −11.874 | 1.00 | 73.77 | C |
| ATOM | 1686 | CG2 | VAL A | 222 | 15.496 | −8.902 | −13.573 | 1.00 | 68.90 | C |

TABLE 6-continued

Atomic coordinates for CRBN:DDB1: Compound B (Human protein)

| ATOM | 1687 | C | VAL A | 222 | 14.113 | −8.478 | −10.058 | 1.00 | 68.68 | C |
|---|---|---|---|---|---|---|---|---|---|---|
| ATOM | 1688 | O | VAL A | 222 | 14.771 | −8.030 | −9.147 | 1.00 | 68.14 | O |
| ATOM | 1689 | N | PRO A | 223 | 13.045 | −9.336 | −9.903 | 1.00 | 70.27 | N |
| ATOM | 1690 | CA | PRO A | 223 | 12.724 | −9.668 | −8.522 | 1.00 | 77.84 | C |
| ATOM | 1691 | CB | PRO A | 223 | 11.357 | −10.327 | −8.605 | 1.00 | 78.97 | C |
| ATOM | 1692 | CG | PRO A | 223 | 10.797 | −9.889 | −9.882 | 1.00 | 79.60 | C |
| ATOM | 1693 | CD | PRO A | 223 | 11.978 | −10.006 | −10.756 | 1.00 | 74.48 | C |
| ATOM | 1694 | C | PRO A | 223 | 13.726 | −10.609 | −7.935 | 1.00 | 82.26 | C |
| ATOM | 1695 | O | PRO A | 223 | 14.647 | −11.039 | −8.601 | 1.00 | 68.31 | O |
| ATOM | 1696 | N | GLU A | 224 | 13.527 | −10.890 | −6.660 | 1.00 | 96.03 | N |
| ATOM | 1697 | CA | GLU A | 224 | 14.423 | −11.683 | −5.837 | 1.00 | 105.76 | C |
| ATOM | 1698 | CB | GLU A | 224 | 14.018 | −11.616 | −4.375 | 1.00 | 112.89 | C |
| ATOM | 1699 | CG | GLU A | 224 | 15.128 | −12.040 | −3.443 | 1.00 | 111.01 | C |
| ATOM | 1700 | CD | GLU A | 224 | 15.031 | −11.343 | −2.116 | 1.00 | 109.99 | C |
| ATOM | 1701 | OE1 | GLU A | 224 | 15.375 | −11.954 | −1.090 | 1.00 | 114.23 | O |
| ATOM | 1702 | OE2 | GLU A | 224 | 14.602 | −10.177 | −2.103 | 1.00 | 106.82 | O |
| ATOM | 1703 | C | GLU A | 224 | 14.681 | −13.112 | −6.211 | 1.00 | 99.16 | C |
| ATOM | 1704 | O | GLU A | 224 | 15.677 | −13.671 | −5.752 | 1.00 | 105.82 | O |
| ATOM | 1705 | N | PRO A | 225 | 13.770 | −13.729 | −7.055 | 1.00 | 99.08 | N |
| ATOM | 1706 | CA | PRO A | 225 | 14.118 | −15.123 | −7.373 | 1.00 | 99.88 | C |
| ATOM | 1707 | CB | PRO A | 225 | 13.082 | −15.516 | −8.406 | 1.00 | 100.30 | C |
| ATOM | 1708 | CG | PRO A | 225 | 11.878 | −14.792 | −7.973 | 1.00 | 104.55 | C |
| ATOM | 1709 | CD | PRO A | 225 | 12.420 | −13.434 | −7.701 | 1.00 | 99.73 | C |
| ATOM | 1710 | C | PRO A | 225 | 15.501 | −15.158 | −8.000 | 1.00 | 95.68 | C |
| ATOM | 1711 | O | PRO A | 225 | 16.292 | −15.964 | −7.557 | 1.00 | 87.73 | O |
| ATOM | 1712 | N | PHE A | 226 | 15.818 | −14.284 | −8.945 | 1.00 | 100.62 | N |
| ATOM | 1713 | CA | PHE A | 226 | 17.171 | −14.269 | −9.469 | 1.00 | 100.68 | C |
| ATOM | 1714 | CB | PHE A | 226 | 17.261 | −14.286 | −10.993 | 1.00 | 112.47 | C |
| ATOM | 1715 | CG | PHE A | 226 | 16.040 | −14.778 | −11.709 | 1.00 | 125.77 | C |
| ATOM | 1716 | CD2 | PHE A | 226 | 16.161 | −15.736 | −12.696 | 1.00 | 126.49 | C |
| ATOM | 1717 | CE2 | PHE A | 226 | 15.062 | −16.176 | −13.398 | 1.00 | 131.24 | C |
| ATOM | 1718 | CZ | PHE A | 226 | 13.823 | −15.642 | −13.136 | 1.00 | 129.03 | C |
| ATOM | 1719 | CE1 | PHE A | 226 | 13.690 | −14.666 | −12.172 | 1.00 | 128.50 | C |
| ATOM | 1720 | CD1 | PHE A | 226 | 14.798 | −14.226 | −11.475 | 1.00 | 130.76 | C |
| ATOM | 1721 | C | PHE A | 226 | 17.810 | −12.971 | −9.040 | 1.00 | 92.08 | C |
| ATOM | 1722 | O | PHE A | 226 | 18.866 | −12.949 | −8.433 | 1.00 | 86.64 | O |
| ATOM | 1723 | N | GLY A | 227 | 17.132 | −11.882 | −9.360 | 1.00 | 86.12 | N |
| ATOM | 1724 | CA | GLY A | 227 | 17.614 | −10.555 | −9.063 | 1.00 | 82.57 | C |
| ATOM | 1725 | C | GLY A | 227 | 18.422 | −10.071 | −10.238 | 1.00 | 79.48 | C |
| ATOM | 1726 | O | GLY A | 227 | 18.702 | −10.844 | −11.131 | 1.00 | 81.33 | O |
| ATOM | 1727 | N | GLY A | 228 | 18.806 | −8.801 | −10.234 | 1.00 | 74.75 | N |
| ATOM | 1728 | CA | GLY A | 228 | 19.579 | −8.224 | −11.318 | 1.00 | 72.35 | C |
| ATOM | 1729 | C | GLY A | 228 | 18.786 | −7.272 | −12.182 | 1.00 | 70.89 | C |
| ATOM | 1730 | O | GLY A | 228 | 17.653 | −6.970 | −11.870 | 1.00 | 73.71 | O |
| ATOM | 1731 | N | ALA A | 229 | 19.386 | −6.801 | −13.265 | 1.00 | 65.70 | N |
| ATOM | 1732 | CA | ALA A | 229 | 18.725 | −5.852 | −14.185 | 1.00 | 64.72 | C |
| ATOM | 1733 | CB | ALA A | 229 | 19.328 | −4.450 | −14.002 | 1.00 | 65.44 | C |
| ATOM | 1734 | C | ALA A | 229 | 18.672 | −6.224 | −15.702 | 1.00 | 60.94 | C |
| ATOM | 1735 | O | ALA A | 229 | 19.668 | −6.540 | −16.303 | 1.00 | 61.38 | O |
| ATOM | 1736 | N | ILE A | 230 | 17.491 | −6.146 | −16.303 | 1.00 | 62.43 | N |
| ATOM | 1737 | CA | ILE A | 230 | 17.300 | −6.131 | −17.777 | 1.00 | 65.70 | C |
| ATOM | 1738 | CB | ILE A | 230 | 15.915 | −6.682 | −18.097 | 1.00 | 66.38 | C |
| ATOM | 1739 | CG1 | ILE A | 230 | 15.940 | −8.191 | −17.926 | 1.00 | 70.77 | C |
| ATOM | 1740 | CD1 | ILE A | 230 | 14.617 | −8.700 | −17.433 | 1.00 | 73.75 | C |
| ATOM | 1741 | CG2 | ILE A | 230 | 15.438 | −6.307 | −19.477 | 1.00 | 65.32 | C |
| ATOM | 1742 | C | ILE A | 230 | 17.426 | −4.718 | −18.366 | 1.00 | 66.46 | C |
| ATOM | 1743 | O | ILE A | 230 | 17.068 | −3.732 | −17.731 | 1.00 | 74.33 | O |
| ATOM | 1744 | N | ILE A | 231 | 17.930 | −4.601 | −19.578 | 1.00 | 62.29 | N |
| ATOM | 1745 | CA | ILE A | 231 | 18.216 | −3.287 | −20.111 | 1.00 | 62.09 | C |
| ATOM | 1746 | CB | ILE A | 231 | 19.719 | −2.927 | −20.006 | 1.00 | 66.57 | C |
| ATOM | 1747 | CG1 | ILE A | 231 | 20.311 | −3.151 | −18.596 | 1.00 | 73.10 | C |
| ATOM | 1748 | CD1 | ILE A | 231 | 19.988 | −2.112 | −17.548 | 1.00 | 77.34 | C |
| ATOM | 1749 | CG2 | ILE A | 231 | 19.977 | −1.493 | −20.428 | 1.00 | 67.63 | C |
| ATOM | 1750 | C | ILE A | 231 | 17.824 | −3.397 | −21.559 | 1.00 | 61.02 | C |
| ATOM | 1751 | O | ILE A | 231 | 18.404 | −4.179 | −22.281 | 1.00 | 63.54 | O |
| ATOM | 1752 | N | ILE A | 232 | 16.852 | −2.606 | −21.986 | 1.00 | 58.99 | N |
| ATOM | 1753 | CA | ILE A | 232 | 16.326 | −2.684 | −23.322 | 1.00 | 58.91 | C |
| ATOM | 1754 | CB | ILE A | 232 | 14.796 | −2.618 | −23.310 | 1.00 | 62.72 | C |
| ATOM | 1755 | CG1 | ILE A | 232 | 14.188 | −3.442 | −22.156 | 1.00 | 67.74 | C |
| ATOM | 1756 | CD1 | ILE A | 232 | 14.396 | −4.928 | −22.243 | 1.00 | 67.11 | C |
| ATOM | 1757 | CG2 | ILE A | 232 | 14.219 | −3.095 | −24.636 | 1.00 | 64.35 | C |
| ATOM | 1758 | C | ILE A | 232 | 16.843 | −1.500 | −24.121 | 1.00 | 61.53 | C |
| ATOM | 1759 | O | ILE A | 232 | 17.078 | −0.432 | −23.563 | 1.00 | 60.82 | O |
| ATOM | 1760 | N | GLY A | 233 | 17.017 | −1.696 | −25.429 | 1.00 | 64.67 | N |
| ATOM | 1761 | CA | GLY A | 233 | 17.363 | −0.624 | −26.374 | 1.00 | 66.21 | C |
| ATOM | 1762 | C | GLY A | 233 | 16.641 | −0.900 | −27.683 | 1.00 | 73.51 | C |
| ATOM | 1763 | O | GLY A | 233 | 15.554 | −1.546 | −27.670 | 1.00 | 71.28 | O |
| ATOM | 1764 | N | GLN A | 234 | 17.232 | −0.429 | −28.801 | 1.00 | 76.29 | N |

TABLE 6-continued

Atomic coordinates for CRBN:DDB1: Compound B (Human protein)

| ATOM | 1765 | CA | GLN A | 234 | 16.629 | −0.555 | −30.153 | 1.00 | 80.98 | C |
|---|---|---|---|---|---|---|---|---|---|---|
| ATOM | 1766 | CB | GLN A | 234 | 17.380 | 0.282 | −31.215 | 1.00 | 89.07 | C |
| ATOM | 1767 | CG | GLN A | 234 | 17.514 | 1.800 | −30.991 | 1.00 | 97.52 | C |
| ATOM | 1768 | CD | GLN A | 234 | 16.250 | 2.641 | −31.240 | 1.00 | 101.47 | C |
| ATOM | 1769 | OE1 | GLN A | 234 | 16.110 | 3.758 | −30.695 | 1.00 | 96.74 | O |
| ATOM | 1770 | NE2 | GLN A | 234 | 15.325 | 2.113 | −32.049 | 1.00 | 102.00 | N |
| ATOM | 1771 | C | GLN A | 234 | 16.705 | −1.992 | −30.611 | 1.00 | 82.03 | C |
| ATOM | 1772 | O | GLN A | 234 | 15.714 | −2.579 | −31.108 | 1.00 | 76.05 | O |
| ATOM | 1773 | N | GLU A | 235 | 17.918 | −2.525 | −30.437 | 1.00 | 85.63 | N |
| ATOM | 1774 | CA | GLU A | 235 | 18.353 | −3.771 | −31.023 | 1.00 | 93.07 | C |
| ATOM | 1775 | CB | GLU A | 235 | 19.601 | −3.465 | −31.881 | 1.00 | 101.00 | C |
| ATOM | 1776 | CG | GLU A | 235 | 20.087 | −4.586 | −32.815 | 1.00 | 117.77 | C |
| ATOM | 1777 | CD | GLU A | 235 | 19.025 | −5.212 | −33.752 | 1.00 | 123.52 | C |
| ATOM | 1778 | OE1 | GLU A | 235 | 19.304 | −6.322 | −34.284 | 1.00 | 126.79 | O |
| ATOM | 1779 | OE2 | GLU A | 235 | 17.929 | −4.630 | −33.975 | 1.00 | 122.02 | O |
| ATOM | 1780 | C | GLU A | 235 | 18.607 | −4.912 | −30.007 | 1.00 | 87.94 | C |
| ATOM | 1781 | O | GLU A | 235 | 18.502 | −6.088 | −30.363 | 1.00 | 82.84 | O |
| ATOM | 1782 | N | SER A | 236 | 18.888 | −4.584 | −28.747 | 1.00 | 85.46 | N |
| ATOM | 1783 | CA | SER A | 236 | 19.293 | −5.596 | −27.762 | 1.00 | 83.37 | C |
| ATOM | 1784 | CB | SER A | 236 | 20.751 | −5.363 | −27.336 | 1.00 | 89.55 | C |
| ATOM | 1785 | OG | SER A | 236 | 20.997 | −4.011 | −26.952 | 1.00 | 89.41 | O |
| ATOM | 1786 | C | SER A | 236 | 18.438 | −5.631 | −26.517 | 1.00 | 76.81 | C |
| ATOM | 1787 | O | SER A | 236 | 17.660 | −4.744 | −26.243 | 1.00 | 70.89 | O |
| ATOM | 1788 | N | ILE A | 237 | 18.616 | −6.697 | −25.765 | 1.00 | 77.70 | N |
| ATOM | 1789 | CA | ILE A | 237 | 17.969 | −6.893 | −24.477 | 1.00 | 74.16 | C |
| ATOM | 1790 | CB | ILE A | 237 | 16.667 | −7.704 | −24.588 | 1.00 | 70.66 | C |
| ATOM | 1791 | CG1 | ILE A | 237 | 15.636 | −6.961 | −25.435 | 1.00 | 68.84 | C |
| ATOM | 1792 | CD1 | ILE A | 237 | 14.304 | −7.683 | −25.549 | 1.00 | 69.77 | C |
| ATOM | 1793 | CG2 | ILE A | 237 | 16.115 | −8.037 | −23.203 | 1.00 | 70.93 | C |
| ATOM | 1794 | C | ILE A | 237 | 18.970 | −7.689 | −23.674 | 1.00 | 74.96 | C |
| ATOM | 1795 | O | ILE A | 237 | 19.363 | −8.783 | −24.060 | 1.00 | 79.03 | O |
| ATOM | 1796 | N | THR A | 238 | 19.352 | −7.145 | −22.543 | 1.00 | 76.16 | N |
| ATOM | 1797 | CA | THR A | 238 | 20.549 | −7.556 | −21.865 | 1.00 | 77.91 | C |
| ATOM | 1798 | CB | THR A | 238 | 21.601 | −6.453 | −22.028 | 1.00 | 80.32 | C |
| ATOM | 1799 | OG1 | THR A | 238 | 21.423 | −5.822 | −23.303 | 1.00 | 82.50 | O |
| ATOM | 1800 | CG2 | THR A | 238 | 22.977 | −7.032 | −21.956 | 1.00 | 85.37 | C |
| ATOM | 1801 | C | THR A | 238 | 20.236 | −7.744 | −20.405 | 1.00 | 77.17 | C |
| ATOM | 1802 | O | THR A | 238 | 19.775 | −6.820 | −19.758 | 1.00 | 80.91 | O |
| ATOM | 1803 | N | TYR A | 239 | 20.431 | −8.946 | −19.889 | 1.00 | 75.06 | N |
| ATOM | 1804 | CA | TYR A | 239 | 20.420 | −9.128 | −18.449 | 1.00 | 73.15 | C |
| ATOM | 1805 | CB | TYR A | 239 | 20.001 | −10.513 | −18.112 | 1.00 | 69.22 | C |
| ATOM | 1806 | CG | TYR A | 239 | 20.052 | −10.802 | −16.668 | 1.00 | 71.97 | C |
| ATOM | 1807 | CD1 | TYR A | 239 | 21.214 | −11.216 | −16.079 | 1.00 | 75.54 | C |
| ATOM | 1808 | CE1 | TYR A | 239 | 21.264 | −11.516 | −14.741 | 1.00 | 78.22 | C |
| ATOM | 1809 | CZ | TYR A | 239 | 20.141 | −11.408 | −13.966 | 1.00 | 77.99 | C |
| ATOM | 1810 | OH | TYR A | 239 | 20.202 | −11.735 | −12.619 | 1.00 | 85.43 | O |
| ATOM | 1811 | CE2 | TYR A | 239 | 18.970 | −10.991 | −14.536 | 1.00 | 75.91 | C |
| ATOM | 1812 | CD2 | TYR A | 239 | 18.932 | −10.696 | −15.885 | 1.00 | 75.32 | C |
| ATOM | 1813 | C | TYR A | 239 | 21.825 | −8.852 | −17.948 | 1.00 | 77.25 | C |
| ATOM | 1814 | O | TYR A | 239 | 22.776 | −8.989 | −18.723 | 1.00 | 77.90 | O |
| ATOM | 1815 | N | HIS A | 240 | 21.920 | −8.512 | −16.676 | 1.00 | 79.22 | N |
| ATOM | 1816 | CA | HIS A | 240 | 23.177 | −8.271 | −16.014 | 1.00 | 81.11 | C |
| ATOM | 1817 | CB | HIS A | 240 | 23.560 | −6.816 | −16.049 | 1.00 | 74.91 | C |
| ATOM | 1818 | CG | HIS A | 240 | 23.759 | −6.278 | −17.421 | 1.00 | 78.52 | C |
| ATOM | 1819 | ND1 | HIS A | 240 | 24.938 | −5.701 | −17.826 | 1.00 | 81.06 | N |
| ATOM | 1820 | CE1 | HIS A | 240 | 24.822 | −5.296 | −19.074 | 1.00 | 82.59 | C |
| ATOM | 1821 | NE2 | HIS A | 240 | 23.610 | −5.597 | −19.496 | 1.00 | 83.12 | N |
| ATOM | 1822 | CD2 | HIS A | 240 | 22.927 | −6.215 | −18.482 | 1.00 | 82.63 | C |
| ATOM | 1823 | C | HIS A | 240 | 22.997 | −8.679 | −14.582 | 1.00 | 89.26 | C |
| ATOM | 1824 | O | HIS A | 240 | 21.895 | −8.706 | −14.078 | 1.00 | 95.63 | O |
| ATOM | 1825 | N | ASN A | 241 | 24.096 | −9.009 | −13.937 | 1.00 | 94.35 | N |
| ATOM | 1826 | CA | ASN A | 241 | 24.117 | −9.398 | −12.546 | 1.00 | 91.07 | C |
| ATOM | 1827 | CB | ASN A | 241 | 23.582 | −10.793 | −12.312 | 1.00 | 85.20 | C |
| ATOM | 1828 | CG | ASN A | 241 | 22.757 | −10.883 | −11.049 | 1.00 | 79.72 | C |
| ATOM | 1829 | OD1 | ASN A | 241 | 23.070 | −10.249 | −10.056 | 1.00 | 82.87 | O |
| ATOM | 1830 | ND2 | ASN A | 241 | 21.692 | −11.665 | −11.087 | 1.00 | 73.92 | N |
| ATOM | 1831 | C | ASN A | 241 | 25.573 | −9.255 | −12.228 | 1.00 | 97.02 | C |
| ATOM | 1832 | O | ASN A | 241 | 26.337 | −8.902 | −13.119 | 1.00 | 98.08 | O |
| ATOM | 1833 | N | GLY A | 242 | 25.983 | −9.516 | −10.997 | 1.00 | 106.23 | N |
| ATOM | 1834 | CA | GLY A | 242 | 27.372 | −9.283 | −10.664 | 1.00 | 111.97 | C |
| ATOM | 1835 | C | GLY A | 242 | 28.295 | −10.038 | −11.584 | 1.00 | 119.58 | C |
| ATOM | 1836 | O | GLY A | 242 | 29.229 | −9.437 | −12.123 | 1.00 | 117.31 | O |
| ATOM | 1837 | N | ASP A | 243 | 28.040 | −11.318 | −11.811 | 1.00 | 122.19 | N |
| ATOM | 1838 | CA | ASP A | 243 | 28.887 | −12.039 | −12.746 | 1.00 | 119.91 | C |
| ATOM | 1839 | CB | ASP A | 243 | 29.917 | −12.932 | −12.066 | 1.00 | 118.93 | C |
| ATOM | 1840 | CG | ASP A | 243 | 31.295 | −12.282 | −12.027 | 1.00 | 116.30 | C |
| ATOM | 1841 | OD1 | ASP A | 243 | 31.460 | −11.217 | −12.659 | 1.00 | 113.12 | O |
| ATOM | 1842 | OD2 | ASP A | 243 | 32.213 | −12.826 | −11.375 | 1.00 | 105.81 | O |

TABLE 6-continued

Atomic coordinates for CRBN:DDB1: Compound B (Human protein)

| ATOM | 1843 | C | ASP A | 243 | 28.144 | −12.717 | −13.866 | 1.00 | 115.09 | C |
|---|---|---|---|---|---|---|---|---|---|---|
| ATOM | 1844 | O | ASP A | 243 | 28.704 | −12.939 | −14.926 | 1.00 | 114.47 | O |
| ATOM | 1845 | N | LYS A | 244 | 26.879 | −13.038 | −13.643 | 1.00 | 111.55 | N |
| ATOM | 1846 | CA | LYS A | 244 | 26.107 | −13.671 | −14.696 | 1.00 | 107.21 | C |
| ATOM | 1847 | CB | LYS A | 244 | 24.862 | −14.380 | −14.182 | 1.00 | 105.27 | C |
| ATOM | 1848 | CG | LYS A | 244 | 23.913 | −14.775 | −15.297 | 1.00 | 108.33 | C |
| ATOM | 1849 | CD | LYS A | 244 | 23.081 | −15.989 | −14.949 | 1.00 | 109.58 | C |
| ATOM | 1850 | CE | LYS A | 244 | 23.546 | −17.193 | −15.739 | 1.00 | 109.09 | C |
| ATOM | 1851 | NZ | LYS A | 244 | 23.599 | −16.901 | −17.196 | 1.00 | 112.67 | N |
| ATOM | 1852 | C | LYS A | 244 | 25.734 | −12.622 | −15.692 | 1.00 | 102.46 | C |
| ATOM | 1853 | O | LYS A | 244 | 25.722 | −11.446 | −15.385 | 1.00 | 106.47 | O |
| ATOM | 1854 | N | TYR A | 245 | 25.458 | −13.052 | −16.903 | 1.00 | 95.33 | N |
| ATOM | 1855 | CA | TYR A | 245 | 25.080 | −12.119 | −17.924 | 1.00 | 94.94 | C |
| ATOM | 1856 | CB | TYR A | 245 | 26.352 | −11.401 | −18.361 | 1.00 | 91.35 | C |
| ATOM | 1857 | CG | TYR A | 245 | 26.333 | −10.575 | −19.626 | 1.00 | 94.57 | C |
| ATOM | 1858 | CD1 | TYR A | 245 | 25.707 | −11.004 | −20.777 | 1.00 | 97.40 | C |
| ATOM | 1859 | CE1 | TYR A | 245 | 25.723 | −10.246 | −21.924 | 1.00 | 101.55 | C |
| ATOM | 1860 | CZ | TYR A | 245 | 26.402 | −9.067 | −21.940 | 1.00 | 100.84 | C |
| ATOM | 1861 | OH | TYR A | 245 | 26.429 | −8.313 | −23.079 | 1.00 | 99.41 | O |
| ATOM | 1862 | CE2 | TYR A | 245 | 27.051 | −8.633 | −20.824 | 1.00 | 99.38 | C |
| ATOM | 1863 | CD2 | TYR A | 245 | 27.024 | −9.391 | −19.682 | 1.00 | 97.23 | C |
| ATOM | 1864 | C | TYR A | 245 | 24.457 | −12.881 | −19.066 | 1.00 | 99.69 | C |
| ATOM | 1865 | O | TYR A | 245 | 24.669 | −14.071 | −19.218 | 1.00 | 109.80 | O |
| ATOM | 1866 | N | LEU A | 246 | 23.701 | −12.173 | −19.887 | 1.00 | 99.49 | N |
| ATOM | 1867 | CA | LEU A | 246 | 23.153 | −12.745 | −21.130 | 1.00 | 90.80 | C |
| ATOM | 1868 | CB | LEU A | 246 | 21.827 | −13.457 | −20.890 | 1.00 | 89.74 | C |
| ATOM | 1869 | CG | LEU A | 246 | 21.829 | −14.854 | −20.288 | 1.00 | 96.35 | C |
| ATOM | 1870 | CD1 | LEU A | 246 | 22.772 | −15.011 | −19.091 | 1.00 | 101.29 | C |
| ATOM | 1871 | CD2 | LEU A | 246 | 20.391 | −15.194 | −19.910 | 1.00 | 97.73 | C |
| ATOM | 1872 | C | LEU A | 246 | 22.918 | −11.571 | −22.050 | 1.00 | 83.97 | C |
| ATOM | 1873 | O | LEU A | 246 | 23.105 | −10.417 | −21.673 | 1.00 | 85.61 | O |
| ATOM | 1874 | N | ALA A | 247 | 22.508 | −11.867 | −23.264 | 1.00 | 78.33 | N |
| ATOM | 1875 | CA | ALA A | 247 | 22.250 | −10.836 | −24.244 | 1.00 | 73.14 | C |
| ATOM | 1876 | CB | ALA A | 247 | 23.556 | −10.172 | −24.669 | 1.00 | 68.67 | C |
| ATOM | 1877 | C | ALA A | 247 | 21.533 | −11.509 | −25.415 | 1.00 | 72.46 | C |
| ATOM | 1878 | O | ALA A | 247 | 21.678 | −12.716 | −25.625 | 1.00 | 69.63 | O |
| ATOM | 1879 | N | ILE A | 248 | 20.709 | −10.734 | −26.112 | 1.00 | 73.59 | N |
| ATOM | 1880 | CA | ILE A | 248 | 19.956 | −11.195 | −27.280 | 1.00 | 74.30 | C |
| ATOM | 1881 | CB | ILE A | 248 | 18.604 | −11.845 | −26.897 | 1.00 | 72.03 | C |
| ATOM | 1882 | CG1 | ILE A | 248 | 17.746 | −10.836 | −26.139 | 1.00 | 73.84 | C |
| ATOM | 1883 | CD1 | ILE A | 248 | 16.304 | −11.258 | −26.046 | 1.00 | 77.81 | C |
| ATOM | 1884 | CG2 | ILE A | 248 | 18.746 | −13.107 | −26.054 | 1.00 | 68.12 | C |
| ATOM | 1885 | C | ILE A | 248 | 19.643 | −10.011 | −28.222 | 1.00 | 77.82 | C |
| ATOM | 1886 | O | ILE A | 248 | 19.700 | −8.827 | −27.831 | 1.00 | 75.91 | O |
| ATOM | 1887 | N | ALA A | 249 | 19.261 | −10.354 | −29.446 | 1.00 | 79.83 | N |
| ATOM | 1888 | CA | ALA A | 249 | 18.871 | −9.369 | −30.448 | 1.00 | 81.16 | C |
| ATOM | 1889 | CB | ALA A | 249 | 20.096 | −8.976 | −31.273 | 1.00 | 81.04 | C |
| ATOM | 1890 | C | ALA A | 249 | 17.756 | −9.910 | −31.359 | 1.00 | 82.46 | C |
| ATOM | 1891 | O | ALA A | 249 | 17.832 | −9.755 | −32.577 | 1.00 | 85.07 | O |
| ATOM | 1892 | N | PRO A | 250 | 16.704 | −10.530 | −30.782 | 1.00 | 81.27 | N |
| ATOM | 1893 | CA | PRO A | 250 | 15.710 | −11.221 | −31.627 | 1.00 | 83.45 | C |
| ATOM | 1894 | CB | PRO A | 250 | 14.509 | −11.424 | −30.693 | 1.00 | 81.50 | C |
| ATOM | 1895 | CG | PRO A | 250 | 14.824 | −10.630 | −29.450 | 1.00 | 78.96 | C |
| ATOM | 1896 | CD | PRO A | 250 | 16.309 | −10.546 | −29.368 | 1.00 | 77.21 | C |
| ATOM | 1897 | C | PRO A | 250 | 15.271 | −10.427 | −32.857 | 1.00 | 87.65 | C |
| ATOM | 1898 | O | PRO A | 250 | 15.156 | −9.194 | −32.792 | 1.00 | 77.75 | O |
| ATOM | 1899 | N | PRO A | 251 | 14.958 | −11.137 | −33.959 | 1.00 | 98.36 | N |
| ATOM | 1900 | CA | PRO A | 251 | 14.647 | −10.391 | −35.185 | 1.00 | 96.16 | C |
| ATOM | 1901 | CB | PRO A | 251 | 14.357 | −11.510 | −36.217 | 1.00 | 91.52 | C |
| ATOM | 1902 | CG | PRO A | 251 | 13.903 | −12.689 | −35.411 | 1.00 | 97.09 | C |
| ATOM | 1903 | CD | PRO A | 251 | 14.420 | −12.522 | −33.994 | 1.00 | 99.81 | C |
| ATOM | 1904 | C | PRO A | 251 | 13.431 | −9.435 | −34.999 | 1.00 | 95.36 | C |
| ATOM | 1905 | O | PRO A | 251 | 13.368 | −8.354 | −35.631 | 1.00 | 95.66 | O |
| ATOM | 1906 | N | ILE A | 252 | 12.513 | −9.882 | −34.168 | 1.00 | 89.79 | N |
| ATOM | 1907 | CA | ILE A | 252 | 11.230 | −9.261 | −33.962 | 1.00 | 80.94 | C |
| ATOM | 1908 | CB | ILE A | 252 | 10.400 | −10.226 | −33.108 | 1.00 | 78.37 | C |
| ATOM | 1909 | CG1 | ILE A | 252 | 8.980 | −10.321 | −33.604 | 1.00 | 77.26 | C |
| ATOM | 1910 | CD1 | ILE A | 252 | 8.334 | −11.614 | −33.192 | 1.00 | 78.03 | C |
| ATOM | 1911 | CG2 | ILE A | 252 | 10.504 | −9.916 | −31.630 | 1.00 | 81.21 | C |
| ATOM | 1912 | C | ILE A | 252 | 11.136 | −7.830 | −33.454 | 1.00 | 79.27 | C |
| ATOM | 1913 | O | ILE A | 252 | 10.343 | −7.068 | −33.969 | 1.00 | 79.31 | O |
| ATOM | 1914 | N | ILE A | 253 | 11.919 | −7.457 | −32.457 | 1.00 | 74.03 | N |
| ATOM | 1915 | CA | ILE A | 253 | 11.854 | −6.096 | −31.953 | 1.00 | 73.90 | C |
| ATOM | 1916 | CB | ILE A | 253 | 12.482 | −5.953 | −30.583 | 1.00 | 73.12 | C |
| ATOM | 1917 | CG1 | ILE A | 253 | 13.989 | −6.055 | −30.687 | 1.00 | 77.41 | C |
| ATOM | 1918 | CD1 | ILE A | 253 | 14.711 | −5.403 | −29.534 | 1.00 | 79.21 | C |
| ATOM | 1919 | CG2 | ILE A | 253 | 11.925 | −7.013 | −29.673 | 1.00 | 71.22 | C |
| ATOM | 1920 | C | ILE A | 253 | 12.326 | −4.974 | −32.862 | 1.00 | 76.90 | C |

TABLE 6-continued

Atomic coordinates for CRBN:DDB1: Compound B (Human protein)

| ATOM | 1921 | O | ILE A | 253 | 11.723 | −3.915 | −32.886 | 1.00 | 79.25 | O |
|---|---|---|---|---|---|---|---|---|---|---|
| ATOM | 1922 | N | LYS A | 254 | 13.401 | −5.177 | −33.612 | 1.00 | 86.68 | N |
| ATOM | 1923 | CA | LYS A | 254 | 13.889 | −4.119 | −34.481 | 1.00 | 87.21 | C |
| ATOM | 1924 | CB | LYS A | 254 | 15.119 | −4.592 | −35.228 | 1.00 | 83.13 | C |
| ATOM | 1925 | C | LYS A | 254 | 12.776 | −3.912 | −35.453 | 1.00 | 87.24 | C |
| ATOM | 1926 | O | LYS A | 254 | 12.341 | −4.839 | −36.098 | 1.00 | 73.29 | O |
| ATOM | 1927 | N | GLN A | 255 | 12.317 | −2.687 | −35.548 | 1.00 | 91.09 | N |
| ATOM | 1928 | CA | GLN A | 255 | 11.198 | −2.355 | −36.387 | 1.00 | 89.38 | C |
| ATOM | 1929 | CB | GLN A | 255 | 10.075 | −3.361 | −36.194 | 1.00 | 91.56 | C |
| ATOM | 1930 | CG | GLN A | 255 | 9.940 | −4.426 | −37.254 | 1.00 | 94.28 | C |
| ATOM | 1931 | CD | GLN A | 255 | 9.024 | −4.015 | −38.377 | 1.00 | 97.03 | C |
| ATOM | 1932 | OE1 | GLN A | 255 | 7.970 | −4.610 | −38.579 | 1.00 | 89.06 | O |
| ATOM | 1933 | NE2 | GLN A | 255 | 9.422 | −2.995 | −39.118 | 1.00 | 94.81 | N |
| ATOM | 1934 | C | GLN A | 255 | 10.814 | −1.109 | −35.682 | 1.00 | 88.76 | C |
| ATOM | 1935 | O | GLN A | 255 | 10.868 | −0.017 | −36.219 | 1.00 | 84.62 | O |
| ATOM | 1936 | N | SER A | 256 | 10.419 | −1.307 | −34.434 | 1.00 | 93.29 | N |
| ATOM | 1937 | CA | SER A | 256 | 10.037 | −0.223 | −33.565 | 1.00 | 91.41 | C |
| ATOM | 1938 | CB | SER A | 256 | 8.533 | −0.120 | −33.406 | 1.00 | 97.34 | C |
| ATOM | 1939 | OG | SER A | 256 | 8.229 | 1.042 | −32.677 | 1.00 | 87.58 | O |
| ATOM | 1940 | C | SER A | 256 | 10.665 | −0.413 | −32.217 | 1.00 | 73.80 | C |
| ATOM | 1941 | O | SER A | 256 | 10.970 | −1.508 | −31.802 | 1.00 | 70.17 | O |
| ATOM | 1942 | N | THR A | 257 | 10.842 | 0.708 | −31.562 | 1.00 | 62.60 | N |
| ATOM | 1943 | CA | THR A | 257 | 11.439 | 0.859 | −30.236 | 1.00 | 65.20 | C |
| ATOM | 1944 | CB | THR A | 257 | 11.833 | 2.343 | −30.026 | 1.00 | 66.31 | C |
| ATOM | 1945 | OG1 | THR A | 257 | 12.154 | 2.958 | −31.298 | 1.00 | 65.61 | O |
| ATOM | 1946 | CG2 | THR A | 257 | 12.959 | 2.513 | −29.010 | 1.00 | 65.45 | C |
| ATOM | 1947 | C | THR A | 257 | 10.501 | 0.460 | −29.070 | 1.00 | 65.02 | C |
| ATOM | 1948 | O | THR A | 257 | 9.283 | 0.640 | −29.141 | 1.00 | 70.51 | O |
| ATOM | 1949 | N | ILE A | 258 | 11.066 | −0.059 | −27.984 | 1.00 | 59.64 | N |
| ATOM | 1950 | CA | ILE A | 258 | 10.267 | −0.456 | −26.829 | 1.00 | 53.43 | C |
| ATOM | 1951 | CB | ILE A | 258 | 10.912 | −1.632 | −26.151 | 1.00 | 53.94 | C |
| ATOM | 1952 | CG1 | ILE A | 258 | 10.961 | −2.798 | −27.142 | 1.00 | 55.06 | C |
| ATOM | 1953 | CD1 | ILE A | 258 | 9.644 | −3.466 | −27.377 | 1.00 | 56.52 | C |
| ATOM | 1954 | CG2 | ILE A | 258 | 10.232 | −1.976 | −24.829 | 1.00 | 53.73 | C |
| ATOM | 1955 | C | ILE A | 258 | 10.191 | 0.696 | −25.858 | 1.00 | 53.48 | C |
| ATOM | 1956 | O | ILE A | 258 | 11.167 | 1.298 | −25.539 | 1.00 | 53.51 | O |
| ATOM | 1957 | N | VAL A | 259 | 9.015 | 1.044 | −25.392 | 1.00 | 57.12 | N |
| ATOM | 1958 | CA | VAL A | 259 | 8.894 | 2.242 | −24.556 | 1.00 | 55.31 | C |
| ATOM | 1959 | CB | VAL A | 259 | 8.224 | 3.394 | −25.346 | 1.00 | 59.28 | C |
| ATOM | 1960 | CG1 | VAL A | 259 | 9.125 | 3.857 | −26.478 | 1.00 | 57.96 | C |
| ATOM | 1961 | CG2 | VAL A | 259 | 6.840 | 2.992 | −25.884 | 1.00 | 62.80 | C |
| ATOM | 1962 | C | VAL A | 259 | 8.176 | 2.053 | −23.234 | 1.00 | 49.55 | C |
| ATOM | 1963 | O | VAL A | 259 | 8.229 | 2.956 | −22.430 | 1.00 | 46.77 | O |
| ATOM | 1964 | N | CYS A | 260 | 7.511 | 0.918 | −23.040 | 1.00 | 46.23 | N |
| ATOM | 1965 | CA | CYS A | 260 | 6.938 | 0.565 | −21.769 | 1.00 | 51.57 | C |
| ATOM | 1966 | CB | CYS A | 260 | 5.492 | 1.059 | −21.665 | 1.00 | 52.53 | C |
| ATOM | 1967 | SG | CYS A | 260 | 4.293 | 0.521 | −22.922 | 1.00 | 51.40 | S |
| ATOM | 1968 | C | CYS A | 260 | 7.002 | −0.937 | −21.510 | 1.00 | 55.82 | C |
| ATOM | 1969 | O | CYS A | 260 | 6.987 | −1.724 | −22.454 | 1.00 | 60.20 | O |
| ATOM | 1970 | N | HIS A | 261 | 7.063 | −1.308 | −20.228 | 1.00 | 55.87 | N |
| ATOM | 1971 | CA | HIS A | 261 | 7.179 | −2.685 | −19.788 | 1.00 | 55.28 | C |
| ATOM | 1972 | CB | HIS A | 261 | 8.606 | −2.948 | −19.376 | 1.00 | 60.01 | C |
| ATOM | 1973 | CG | HIS A | 261 | 8.977 | −2.375 | −18.028 | 1.00 | 68.79 | C |
| ATOM | 1974 | ND1 | HIS A | 261 | 8.848 | −3.090 | −16.851 | 1.00 | 70.72 | N |
| ATOM | 1975 | CE1 | HIS A | 261 | 9.261 | −2.346 | −15.836 | 1.00 | 72.74 | C |
| ATOM | 1976 | NE2 | HIS A | 261 | 9.667 | −1.181 | −16.312 | 1.00 | 73.47 | N |
| ATOM | 1977 | CD2 | HIS A | 261 | 9.496 | −1.168 | −17.677 | 1.00 | 71.62 | C |
| ATOM | 1978 | C | HIS A | 261 | 6.324 | −2.933 | −18.567 | 1.00 | 54.59 | C |
| ATOM | 1979 | O | HIS A | 261 | 6.029 | −2.027 | −17.867 | 1.00 | 57.69 | O |
| ATOM | 1980 | N | ASN A | 262 | 5.992 | −4.166 | −18.251 | 1.00 | 57.51 | N |
| ATOM | 1981 | CA | ASN A | 262 | 5.369 | −4.448 | −16.980 | 1.00 | 59.13 | C |
| ATOM | 1982 | CB | ASN A | 262 | 3.881 | −4.248 | −17.059 | 1.00 | 63.36 | C |
| ATOM | 1983 | CG | ASN A | 262 | 3.280 | −4.109 | −15.687 | 1.00 | 69.34 | C |
| ATOM | 1984 | OD1 | ASN A | 262 | 3.656 | −3.179 | −14.913 | 1.00 | 66.22 | O |
| ATOM | 1985 | ND2 | ASN A | 262 | 2.398 | −5.045 | −15.336 | 1.00 | 67.95 | N |
| ATOM | 1986 | C | ASN A | 262 | 5.571 | −5.838 | −16.536 | 1.00 | 58.26 | C |
| ATOM | 1987 | O | ASN A | 262 | 5.435 | −6.733 | −17.331 | 1.00 | 67.74 | O |
| ATOM | 1988 | N | ARG A | 263 | 5.825 | −6.039 | −15.258 | 1.00 | 58.05 | N |
| ATOM | 1989 | CA | ARG A | 263 | 6.072 | −7.386 | −14.719 | 1.00 | 59.07 | C |
| ATOM | 1990 | CB | ARG A | 263 | 6.757 | −7.281 | −13.364 | 1.00 | 60.05 | C |
| ATOM | 1991 | CG | ARG A | 263 | 7.243 | −8.606 | −12.809 | 1.00 | 64.20 | C |
| ATOM | 1992 | CD | ARG A | 263 | 6.957 | −8.649 | −11.336 | 1.00 | 65.99 | C |
| ATOM | 1993 | NE | ARG A | 263 | 7.688 | −7.569 | −10.694 | 1.00 | 68.78 | N |
| ATOM | 1994 | CZ | ARG A | 263 | 7.400 | −7.079 | −9.504 | 1.00 | 70.85 | C |
| ATOM | 1995 | NH1 | ARG A | 263 | 6.372 | −7.552 | −8.817 | 1.00 | 74.19 | N |
| ATOM | 1996 | NH2 | ARG A | 263 | 8.139 | −6.103 | −9.002 | 1.00 | 73.91 | N |
| ATOM | 1997 | C | ARG A | 263 | 4.797 | −8.245 | −14.569 | 1.00 | 56.59 | C |
| ATOM | 1998 | O | ARG A | 263 | 3.895 | −7.902 | −13.817 | 1.00 | 53.70 | O |

TABLE 6-continued

Atomic coordinates for CRBN:DDB1: Compound B (Human protein)

| ATOM | 1999 | N   | VAL A | 264 | 4.772  | −9.405  | −15.219 | 1.00 | 55.24  | N |
|------|------|-----|-------|-----|--------|---------|---------|------|--------|---|
| ATOM | 2000 | CA  | VAL A | 264 | 3.584  | −10.213 | −15.227 | 1.00 | 56.33  | C |
| ATOM | 2001 | CB  | VAL A | 264 | 3.504  | −11.084 | −16.467 | 1.00 | 57.34  | C |
| ATOM | 2002 | CG1 | VAL A | 264 | 2.196  | −11.875 | −16.482 | 1.00 | 56.82  | C |
| ATOM | 2003 | CG2 | VAL A | 264 | 3.606  | −10.193 | −17.699 | 1.00 | 60.00  | C |
| ATOM | 2004 | C   | VAL A | 264 | 3.400  | −11.062 | −13.989 | 1.00 | 59.07  | C |
| ATOM | 2005 | O   | VAL A | 264 | 2.259  | −11.233 | −13.581 | 1.00 | 62.61  | O |
| ATOM | 2006 | N   | ASP A | 265 | 4.485  | −11.578 | −13.433 | 1.00 | 64.02  | N |
| ATOM | 2007 | CA  | ASP A | 265 | 4.429  | −12.409 | −12.251 | 1.00 | 69.84  | C |
| ATOM | 2008 | CB  | ASP A | 265 | 4.704  | −13.861 | −12.593 | 1.00 | 76.86  | C |
| ATOM | 2009 | CG  | ASP A | 265 | 6.029  | −14.059 | −13.251 | 1.00 | 85.65  | C |
| ATOM | 2010 | OD1 | ASP A | 265 | 7.033  | −13.530 | −12.753 | 1.00 | 86.26  | O |
| ATOM | 2011 | OD2 | ASP A | 265 | 6.078  | −14.769 | −14.267 | 1.00 | 83.37  | O |
| ATOM | 2012 | C   | ASP A | 265 | 5.400  | −11.936 | −11.206 | 1.00 | 66.80  | C |
| ATOM | 2013 | O   | ASP A | 265 | 6.441  | −11.388 | −11.516 | 1.00 | 65.56  | O |
| ATOM | 2014 | N   | PRO A | 266 | 5.019  | −12.191 | −9.902  | 1.00 | 64.96  | N |
| ATOM | 2015 | CA  | PRO A | 266 | 5.961  | −11.708 | −8.888  | 1.00 | 66.82  | C |
| ATOM | 2016 | CB  | PRO A | 266 | 5.349  | −12.171 | −7.585  | 1.00 | 64.75  | C |
| ATOM | 2017 | CG  | PRO A | 266 | 3.909  | −12.209 | −7.854  | 1.00 | 64.74  | C |
| ATOM | 2018 | CD  | PRO A | 266 | 3.896  | −12.900 | −9.156  | 1.00 | 62.18  | C |
| ATOM | 2019 | C   | PRO A | 266 | 7.275  | −12.380 | −9.070  | 1.00 | 71.28  | C |
| ATOM | 2020 | O   | PRO A | 266 | 8.315  | −11.870 | −8.731  | 1.00 | 74.12  | O |
| ATOM | 2021 | N   | ASN A | 267 | 7.198  | −13.557 | −9.637  | 1.00 | 80.76  | N |
| ATOM | 2022 | CA  | ASN A | 267 | 8.325  | −14.393 | −9.887  | 1.00 | 86.22  | C |
| ATOM | 2023 | CB  | ASN A | 267 | 7.817  | −15.639 | −10.595 | 1.00 | 91.48  | C |
| ATOM | 2024 | CG  | ASN A | 267 | 8.906  | −16.615 | −10.886 | 1.00 | 101.35 | C |
| ATOM | 2025 | OD1 | ASN A | 267 | 10.070 | −16.293 | −10.739 | 1.00 | 116.70 | O |
| ATOM | 2026 | ND2 | ASN A | 267 | 8.541  | −17.818 | −11.302 | 1.00 | 102.80 | N |
| ATOM | 2027 | C   | ASN A | 267 | 9.313  | −13.644 | −10.755 | 1.00 | 87.48  | C |
| ATOM | 2028 | O   | ASN A | 267 | 10.508 | −13.785 | −10.577 | 1.00 | 87.92  | O |
| ATOM | 2029 | N   | GLY A | 268 | 8.827  | −12.831 | −11.685 | 1.00 | 85.29  | N |
| ATOM | 2030 | CA  | GLY A | 268 | 9.727  | −12.102 | −12.559 | 1.00 | 76.97  | C |
| ATOM | 2031 | C   | GLY A | 268 | 10.021 | −12.933 | −13.778 | 1.00 | 77.60  | C |
| ATOM | 2032 | O   | GLY A | 268 | 10.955 | −12.704 | −14.508 | 1.00 | 72.39  | O |
| ATOM | 2033 | N   | SER A | 269 | 9.197  | −13.938 | −13.969 | 1.00 | 78.68  | N |
| ATOM | 2034 | CA  | SER A | 269 | 9.322  | −14.893 | −15.076 | 1.00 | 81.52  | C |
| ATOM | 2035 | CB  | SER A | 269 | 8.375  | −16.067 | −14.919 | 1.00 | 86.32  | C |
| ATOM | 2036 | OG  | SER A | 269 | 8.821  | −16.893 | −13.883 | 1.00 | 99.32  | O |
| ATOM | 2037 | C   | SER A | 269 | 9.003  | −14.272 | −16.399 | 1.00 | 78.84  | C |
| ATOM | 2038 | O   | SER A | 269 | 9.665  | −14.546 | −17.395 | 1.00 | 77.83  | O |
| ATOM | 2039 | N   | ARG A | 270 | 7.948  | −13.473 | −16.410 | 1.00 | 75.92  | N |
| ATOM | 2040 | CA  | ARG A | 270 | 7.481  | −12.851 | −17.632 | 1.00 | 71.81  | C |
| ATOM | 2041 | CB  | ARG A | 270 | 6.174  | −13.536 | −18.022 | 1.00 | 72.23  | C |
| ATOM | 2042 | CG  | ARG A | 270 | 6.306  | −15.045 | −18.163 | 1.00 | 72.89  | C |
| ATOM | 2043 | CD  | ARG A | 270 | 5.019  | −15.670 | −18.701 | 1.00 | 77.75  | C |
| ATOM | 2044 | NE  | ARG A | 270 | 4.045  | −15.883 | −17.634 | 1.00 | 82.35  | N |
| ATOM | 2045 | CZ  | ARG A | 270 | 2.712  | −15.790 | −17.738 | 1.00 | 89.94  | C |
| ATOM | 2046 | NH1 | ARG A | 270 | 2.091  | −15.468 | −18.869 | 1.00 | 88.74  | N |
| ATOM | 2047 | NH2 | ARG A | 270 | 1.969  | −16.008 | −16.660 | 1.00 | 98.50  | N |
| ATOM | 2048 | C   | ARG A | 270 | 7.344  | −11.309 | −17.496 | 1.00 | 64.28  | C |
| ATOM | 2049 | O   | ARG A | 270 | 7.090  | −10.792 | −16.397 | 1.00 | 66.03  | O |
| ATOM | 2050 | N   | TYR A | 271 | 7.574  | −10.593 | −18.598 | 1.00 | 56.79  | N |
| ATOM | 2051 | CA  | TYR A | 271 | 7.312  | −9.155  | −18.701 | 1.00 | 54.83  | C |
| ATOM | 2052 | CB  | TYR A | 271 | 8.624  | −8.395  | −18.776 | 1.00 | 54.49  | C |
| ATOM | 2053 | CG  | TYR A | 271 | 9.255  | −8.375  | −17.387 | 1.00 | 60.18  | C |
| ATOM | 2054 | CD1 | TYR A | 271 | 9.949  | −9.483  | −16.897 | 1.00 | 64.17  | C |
| ATOM | 2055 | CE1 | TYR A | 271 | 10.482 | −9.503  | −15.621 | 1.00 | 64.28  | C |
| ATOM | 2056 | CZ  | TYR A | 271 | 10.319 | −8.424  | −14.815 | 1.00 | 65.48  | C |
| ATOM | 2057 | OH  | TYR A | 271 | 10.856 | −8.448  | −13.556 | 1.00 | 66.15  | O |
| ATOM | 2058 | CE2 | TYR A | 271 | 9.621  | −7.317  | −15.265 | 1.00 | 65.35  | C |
| ATOM | 2059 | CD2 | TYR A | 271 | 9.083  | −7.301  | −16.531 | 1.00 | 61.02  | C |
| ATOM | 2060 | C   | TYR A | 271 | 6.416  | −8.880  | −19.887 | 1.00 | 54.74  | C |
| ATOM | 2061 | O   | TYR A | 271 | 6.375  | −9.671  | −20.803 | 1.00 | 56.76  | O |
| ATOM | 2062 | N   | LEU A | 272 | 5.618  | −7.813  | −19.849 | 1.00 | 53.22  | N |
| ATOM | 2063 | CA  | LEU A | 272 | 4.940  | −7.334  | −21.076 | 1.00 | 50.49  | C |
| ATOM | 2064 | CB  | LEU A | 272 | 3.533  | −6.865  | −20.808 | 1.00 | 47.96  | C |
| ATOM | 2065 | CG  | LEU A | 272 | 2.701  | −8.064  | −20.383 | 1.00 | 49.83  | C |
| ATOM | 2066 | CD1 | LEU A | 272 | 1.376  | −7.669  | −19.782 | 1.00 | 50.22  | C |
| ATOM | 2067 | CD2 | LEU A | 272 | 2.423  | −8.958  | −21.552 | 1.00 | 54.51  | C |
| ATOM | 2068 | C   | LEU A | 272 | 5.797  | −6.219  | −21.602 | 1.00 | 48.76  | C |
| ATOM | 2069 | O   | LEU A | 272 | 6.361  | −5.512  | −20.789 | 1.00 | 46.98  | O |
| ATOM | 2070 | N   | LEU A | 273 | 5.990  | −6.134  | −22.928 | 1.00 | 45.55  | N |
| ATOM | 2071 | CA  | LEU A | 273 | 6.634  | −4.983  | −23.521 | 1.00 | 44.98  | C |
| ATOM | 2072 | CB  | LEU A | 273 | 7.937  | −5.319  | −24.184 | 1.00 | 45.54  | C |
| ATOM | 2073 | CG  | LEU A | 273 | 8.955  | −6.015  | −23.313 | 1.00 | 48.64  | C |
| ATOM | 2074 | CD1 | LEU A | 273 | 10.265 | −6.170  | −24.070 | 1.00 | 49.87  | C |
| ATOM | 2075 | CD2 | LEU A | 273 | 9.192  | −5.278  | −22.016 | 1.00 | 50.27  | C |
| ATOM | 2076 | C   | LEU A | 273 | 5.753  | −4.289  | −24.542 | 1.00 | 48.05  | C |

TABLE 6-continued

Atomic coordinates for CRBN:DDB1: Compound B (Human protein)

| ATOM | 2077 | O | LEU A | 273 | 4.915 | −4.900 | −25.249 | 1.00 | 46.24 | O |
|------|------|------|-------|-----|-------|--------|---------|------|-------|---|
| ATOM | 2078 | N | GLY A | 274 | 5.990 | −2.987 | −24.618 | 1.00 | 47.53 | N |
| ATOM | 2079 | CA | GLY A | 274 | 5.235 | −2.135 | −25.437 | 1.00 | 48.02 | C |
| ATOM | 2080 | C | GLY A | 274 | 6.141 | −1.426 | −26.388 | 1.00 | 50.64 | C |
| ATOM | 2081 | O | GLY A | 274 | 7.135 | −0.834 | −26.024 | 1.00 | 52.80 | O |
| ATOM | 2082 | N | ASP A | 275 | 5.697 | −1.462 | −27.618 | 1.00 | 55.65 | N |
| ATOM | 2083 | CA | ASP A | 275 | 6.284 | −0.851 | −28.783 | 1.00 | 55.34 | C |
| ATOM | 2084 | CB | ASP A | 275 | 5.585 | −1.605 | −29.887 | 1.00 | 63.23 | C |
| ATOM | 2085 | CG | ASP A | 275 | 6.138 | −1.373 | −31.184 | 1.00 | 77.21 | C |
| ATOM | 2086 | OD1 | ASP A | 275 | 7.303 | −0.925 | −31.265 | 1.00 | 93.49 | O |
| ATOM | 2087 | OD2 | ASP A | 275 | 5.386 | −1.674 | −32.141 | 1.00 | 91.57 | O |
| ATOM | 2088 | C | ASP A | 275 | 5.865 | 0.622 | −28.850 | 1.00 | 50.56 | C |
| ATOM | 2089 | O | ASP A | 275 | 4.970 | 1.022 | −28.144 | 1.00 | 55.88 | O |
| ATOM | 2090 | N | MET A | 276 | 6.454 | 1.425 | −29.724 | 0.50 | 42.83 | N |
| ATOM | 2091 | CA | MET A | 276 | 6.028 | 2.797 | −29.914 | 0.50 | 35.48 | C |
| ATOM | 2092 | CB | MET A | 276 | 7.210 | 3.610 | −30.399 | 0.50 | 31.52 | C |
| ATOM | 2093 | CG | MET A | 276 | 6.989 | 5.098 | −30.548 | 0.50 | 29.79 | C |
| ATOM | 2094 | SD | MET A | 276 | 8.611 | 5.856 | −30.443 | 0.50 | 26.47 | S |
| ATOM | 2095 | CE | MET A | 276 | 9.281 | 4.458 | −29.640 | 0.50 | 27.32 | C |
| ATOM | 2096 | C | MET A | 276 | 4.920 | 2.850 | −30.915 | 0.50 | 36.18 | C |
| ATOM | 2097 | O | MET A | 276 | 4.430 | 3.887 | −31.180 | 0.50 | 35.43 | O |
| ATOM | 2098 | N | GLU A | 277 | 4.532 | 1.725 | −31.483 | 1.00 | 41.41 | N |
| ATOM | 2099 | CA | GLU A | 277 | 3.547 | 1.636 | −32.625 | 1.00 | 49.21 | C |
| ATOM | 2100 | CB | GLU A | 277 | 4.186 | 1.242 | −34.029 | 1.00 | 56.40 | C |
| ATOM | 2101 | CG | GLU A | 277 | 5.427 | 1.970 | −34.624 | 1.00 | 65.77 | C |
| ATOM | 2102 | CD | GLU A | 277 | 5.874 | 1.499 | −36.064 | 1.00 | 73.16 | C |
| ATOM | 2103 | OE1 | GLU A | 277 | 5.917 | 0.264 | −36.360 | 1.00 | 76.67 | O |
| ATOM | 2104 | OE2 | GLU A | 277 | 6.222 | 2.375 | −36.913 | 1.00 | 73.60 | O |
| ATOM | 2105 | C | GLU A | 277 | 2.393 | 0.588 | −32.411 | 1.00 | 47.51 | C |
| ATOM | 2106 | O | GLU A | 277 | 1.583 | 0.383 | −33.353 | 1.00 | 45.06 | O |
| ATOM | 2107 | N | GLY A | 278 | 2.308 | −0.073 | −31.244 | 1.00 | 43.04 | N |
| ATOM | 2108 | CA | GLY A | 278 | 1.236 | −1.055 | −31.011 | 1.00 | 42.21 | C |
| ATOM | 2109 | C | GLY A | 278 | 1.666 | −2.516 | −30.755 | 1.00 | 40.44 | C |
| ATOM | 2110 | O | GLY A | 278 | 0.870 | −3.331 | −30.271 | 1.00 | 40.92 | O |
| ATOM | 2111 | N | ARG A | 279 | 2.889 | −2.885 | −31.071 | 0.50 | 35.36 | N |
| ATOM | 2112 | CA | ARG A | 279 | 3.245 | −4.209 | −30.752 | 0.50 | 33.66 | C |
| ATOM | 2113 | CB | ARG A | 279 | 4.506 | −4.619 | −31.459 | 0.50 | 31.88 | C |
| ATOM | 2114 | CG | ARG A | 279 | 4.346 | −4.591 | −32.958 | 0.50 | 29.07 | C |
| ATOM | 2115 | CD | ARG A | 279 | 5.678 | −4.664 | −33.603 | 0.50 | 27.42 | C |
| ATOM | 2116 | NE | ARG A | 279 | 5.522 | −4.338 | −34.975 | 0.50 | 27.35 | N |
| ATOM | 2117 | CZ | ARG A | 279 | 5.870 | −3.161 | −35.466 | 0.50 | 28.50 | C |
| ATOM | 2118 | NH1 | ARG A | 279 | 6.392 | −2.256 | −34.661 | 0.50 | 28.84 | N |
| ATOM | 2119 | NH2 | ARG A | 279 | 5.713 | −2.873 | −36.755 | 0.50 | 28.28 | N |
| ATOM | 2120 | C | ARG A | 279 | 3.300 | −4.394 | −29.252 | 0.50 | 35.88 | C |
| ATOM | 2121 | O | ARG A | 279 | 3.638 | −3.510 | −28.499 | 0.50 | 33.93 | O |
| ATOM | 2122 | N | LEU A | 280 | 2.831 | −5.558 | −28.855 | 1.00 | 42.22 | N |
| ATOM | 2123 | CA | LEU A | 280 | 2.852 | −6.078 | −27.477 | 1.00 | 49.22 | C |
| ATOM | 2124 | CB | LEU A | 280 | 1.416 | −6.184 | −26.915 | 1.00 | 48.50 | C |
| ATOM | 2125 | CG | LEU A | 280 | 1.186 | −6.754 | −25.500 | 1.00 | 47.45 | C |
| ATOM | 2126 | CD1 | LEU A | 280 | 1.801 | −5.859 | −24.425 | 1.00 | 46.61 | C |
| ATOM | 2127 | CD2 | LEU A | 280 | −0.295 | −6.989 | −25.228 | 1.00 | 46.70 | C |
| ATOM | 2128 | C | LEU A | 280 | 3.532 | −7.490 | −27.416 | 1.00 | 56.12 | C |
| ATOM | 2129 | O | LEU A | 280 | 3.034 | −8.496 | −27.953 | 1.00 | 56.61 | O |
| ATOM | 2130 | N | PHE A | 281 | 4.656 | −7.546 | −26.721 | 1.00 | 61.96 | N |
| ATOM | 2131 | CA | PHE A | 281 | 5.441 | −8.749 | −26.581 | 1.00 | 64.26 | C |
| ATOM | 2132 | CB | PHE A | 281 | 6.904 | −8.446 | −26.897 | 1.00 | 69.09 | C |
| ATOM | 2133 | CG | PHE A | 281 | 7.139 | −7.772 | −28.210 | 1.00 | 71.68 | C |
| ATOM | 2134 | CD1 | PHE A | 281 | 7.001 | −6.404 | −28.327 | 1.00 | 71.30 | C |
| ATOM | 2135 | CE1 | PHE A | 281 | 7.243 | −5.780 | −29.526 | 1.00 | 70.25 | C |
| ATOM | 2136 | CZ | PHE A | 281 | 7.637 | −6.510 | −30.609 | 1.00 | 68.33 | C |
| ATOM | 2137 | CE2 | PHE A | 281 | 7.790 | −7.867 | −30.505 | 1.00 | 68.62 | C |
| ATOM | 2138 | CD2 | PHE A | 281 | 7.568 | −8.496 | −29.308 | 1.00 | 71.15 | C |
| ATOM | 2139 | C | PHE A | 281 | 5.451 | −9.228 | −25.128 | 1.00 | 67.12 | C |
| ATOM | 2140 | O | PHE A | 281 | 5.436 | −8.390 | −24.196 | 1.00 | 69.53 | O |
| ATOM | 2141 | N | MET A | 282 | 5.525 | −10.559 | −24.945 | 1.00 | 63.28 | N |
| ATOM | 2142 | CA | MET A | 282 | 6.035 | −11.145 | −23.726 | 1.00 | 56.46 | C |
| ATOM | 2143 | CB | MET A | 282 | 5.478 | −12.478 | −23.498 | 1.00 | 58.19 | C |
| ATOM | 2144 | CG | MET A | 282 | 5.557 | −12.846 | −22.059 | 1.00 | 64.37 | C |
| ATOM | 2145 | SD | MET A | 282 | 3.833 | −12.722 | −21.601 | 1.00 | 77.19 | S |
| ATOM | 2146 | CE | MET A | 282 | 3.450 | −14.448 | −22.033 | 1.00 | 74.00 | C |
| ATOM | 2147 | C | MET A | 282 | 7.501 | −11.358 | −23.899 | 1.00 | 53.16 | C |
| ATOM | 2148 | O | MET A | 282 | 7.958 | −11.528 | −25.012 | 1.00 | 49.66 | O |
| ATOM | 2149 | N | LEU A | 283 | 8.228 | −11.328 | −22.798 | 1.00 | 53.94 | N |
| ATOM | 2150 | CA | LEU A | 283 | 9.655 | −11.613 | −22.755 | 1.00 | 56.49 | C |
| ATOM | 2151 | CB | LEU A | 283 | 10.490 | −10.337 | −22.565 | 1.00 | 58.50 | C |
| ATOM | 2152 | CG | LEU A | 283 | 11.776 | −10.345 | −21.695 | 1.00 | 60.95 | C |
| ATOM | 2153 | CD1 | LEU A | 283 | 12.788 | −11.361 | −22.189 | 1.00 | 63.99 | C |
| ATOM | 2154 | CD2 | LEU A | 283 | 12.474 | −8.983 | −21.622 | 1.00 | 61.72 | C |

TABLE 6-continued

Atomic coordinates for CRBN:DDB1: Compound B (Human protein)

| ATOM | 2155 | C | LEU A | 283 | 9.742 | −12.489 | −21.556 | 1.00 | 59.31 | C |
|------|------|------|-------|-----|--------|---------|---------|------|--------|---|
| ATOM | 2156 | O | LEU A | 283 | 9.292 | −12.066 | −20.513 | 1.00 | 61.42 | O |
| ATOM | 2157 | N | LEU A | 284 | 10.305 | −13.698 | −21.696 | 1.00 | 66.28 | N |
| ATOM | 2158 | CA | LEU A | 284 | 10.276 | −14.722 | −20.633 | 1.00 | 64.05 | C |
| ATOM | 2159 | CB | LEU A | 284 | 9.635 | −16.007 | −21.071 | 1.00 | 58.25 | C |
| ATOM | 2160 | CG | LEU A | 284 | 8.310 | −15.668 | −21.707 | 1.00 | 59.04 | C |
| ATOM | 2161 | CD1 | LEU A | 284 | 8.429 | −15.362 | −23.206 | 1.00 | 56.74 | C |
| ATOM | 2162 | CD2 | LEU A | 284 | 7.363 | −16.810 | −21.435 | 1.00 | 62.58 | C |
| ATOM | 2163 | C | LEU A | 284 | 11.658 | −15.043 | −20.268 | 1.00 | 68.90 | C |
| ATOM | 2164 | O | LEU A | 284 | 12.505 | −15.179 | −21.164 | 1.00 | 70.06 | O |
| ATOM | 2165 | N | LEU A | 285 | 11.850 | −15.204 | −18.956 | 1.00 | 74.69 | N |
| ATOM | 2166 | CA | LEU A | 285 | 13.147 | −15.442 | −18.344 | 1.00 | 78.20 | C |
| ATOM | 2167 | CB | LEU A | 285 | 13.316 | −14.597 | −17.084 | 1.00 | 78.39 | C |
| ATOM | 2168 | CG | LEU A | 285 | 13.239 | −13.071 | −17.202 | 1.00 | 74.72 | C |
| ATOM | 2169 | CD1 | LEU A | 285 | 14.085 | −12.460 | −16.098 | 1.00 | 73.80 | C |
| ATOM | 2170 | CD2 | LEU A | 285 | 13.727 | −12.557 | −18.547 | 1.00 | 74.39 | C |
| ATOM | 2171 | C | LEU A | 285 | 13.284 | −16.916 | −18.024 | 1.00 | 80.97 | C |
| ATOM | 2172 | O | LEU A | 285 | 12.714 | −17.434 | −17.036 | 1.00 | 78.99 | O |
| ATOM | 2173 | N | GLU A | 286 | 14.080 | −17.565 | −18.869 | 1.00 | 84.80 | N |
| ATOM | 2174 | CA | GLU A | 286 | 14.082 | −18.995 | −18.969 | 1.00 | 86.31 | C |
| ATOM | 2175 | CB | GLU A | 286 | 14.281 | −19.413 | −20.438 | 1.00 | 86.69 | C |
| ATOM | 2176 | CG | GLU A | 286 | 13.240 | −18.681 | −21.311 | 1.00 | 91.55 | C |
| ATOM | 2177 | CD | GLU A | 286 | 12.873 | −19.329 | −22.652 | 1.00 | 94.89 | C |
| ATOM | 2178 | OE1 | GLU A | 286 | 13.745 | −19.398 | −23.553 | 1.00 | 96.88 | O |
| ATOM | 2179 | OE2 | GLU A | 286 | 11.684 | −19.707 | −22.831 | 1.00 | 89.36 | O |
| ATOM | 2180 | C | GLU A | 286 | 15.079 | −19.559 | −17.952 | 1.00 | 86.16 | C |
| ATOM | 2181 | O | GLU A | 286 | 16.220 | −19.105 | −17.847 | 1.00 | 76.19 | O |
| ATOM | 2182 | N | LYS A | 287 | 14.568 | −20.512 | −17.171 | 1.00 | 92.29 | N |
| ATOM | 2183 | CA | LYS A | 287 | 15.277 | −21.192 | −16.096 | 1.00 | 94.26 | C |
| ATOM | 2184 | CB | LYS A | 287 | 14.761 | −20.698 | −14.732 | 1.00 | 94.49 | C |
| ATOM | 2185 | CG | LYS A | 287 | 13.242 | −20.674 | −14.569 | 1.00 | 99.99 | C |
| ATOM | 2186 | CD | LYS A | 287 | 12.833 | −20.077 | −13.226 | 1.00 | 107.17 | C |
| ATOM | 2187 | CE | LYS A | 287 | 11.515 | −19.301 | −13.278 | 1.00 | 114.07 | C |
| ATOM | 2188 | NZ | LYS A | 287 | 10.324 | −20.168 | −13.512 | 1.00 | 117.26 | N |
| ATOM | 2189 | C | LYS A | 287 | 15.079 | −22.711 | −16.297 | 1.00 | 91.90 | C |
| ATOM | 2190 | O | LYS A | 287 | 14.945 | −23.487 | −15.351 | 1.00 | 86.91 | O |
| ATOM | 2191 | N | THR A | 296 | 19.115 | −22.411 | −13.834 | 1.00 | 89.30 | N |
| ATOM | 2192 | CA | THR A | 296 | 18.238 | −21.316 | −13.446 | 1.00 | 104.34 | C |
| ATOM | 2193 | CB | THR A | 296 | 18.794 | −20.519 | −12.253 | 1.00 | 99.57 | C |
| ATOM | 2194 | OG1 | THR A | 296 | 20.059 | −19.949 | −12.603 | 1.00 | 91.91 | O |
| ATOM | 2195 | CG2 | THR A | 296 | 18.947 | −21.410 | −11.045 | 1.00 | 90.65 | C |
| ATOM | 2196 | C | THR A | 296 | 17.951 | −20.343 | −14.589 | 1.00 | 111.84 | C |
| ATOM | 2197 | O | THR A | 296 | 17.016 | −20.545 | −15.371 | 1.00 | 127.83 | O |
| ATOM | 2198 | N | LEU A | 297 | 18.745 | −19.282 | −14.682 | 1.00 | 106.04 | N |
| ATOM | 2199 | CA | LEU A | 297 | 18.531 | −18.303 | −15.727 | 1.00 | 104.47 | C |
| ATOM | 2200 | CB | LEU A | 297 | 19.002 | −16.937 | −15.266 | 1.00 | 111.66 | C |
| ATOM | 2201 | CG | LEU A | 297 | 18.959 | −15.897 | −16.377 | 1.00 | 119.13 | C |
| ATOM | 2202 | CD1 | LEU A | 297 | 17.669 | −15.994 | −17.161 | 1.00 | 120.62 | C |
| ATOM | 2203 | CD2 | LEU A | 297 | 19.106 | −14.509 | −15.801 | 1.00 | 123.16 | C |
| ATOM | 2204 | C | LEU A | 297 | 19.207 | −18.666 | −17.029 | 1.00 | 98.85 | C |
| ATOM | 2205 | O | LEU A | 297 | 20.201 | −18.066 | −17.403 | 1.00 | 95.36 | O |
| ATOM | 2206 | N | LYS A | 298 | 18.675 | −19.656 | −17.722 | 1.00 | 94.62 | N |
| ATOM | 2207 | CA | LYS A | 298 | 19.286 | −20.069 | −18.968 | 1.00 | 92.33 | C |
| ATOM | 2208 | CB | LYS A | 298 | 18.682 | −21.397 | −19.442 | 1.00 | 97.79 | C |
| ATOM | 2209 | CG | LYS A | 298 | 19.010 | −21.777 | −20.879 | 1.00 | 104.02 | C |
| ATOM | 2210 | CD | LYS A | 298 | 19.182 | −23.271 | −21.065 | 1.00 | 110.76 | C |
| ATOM | 2211 | CE | LYS A | 298 | 19.734 | −23.580 | −22.447 | 1.00 | 112.36 | C |
| ATOM | 2212 | NZ | LYS A | 298 | 20.979 | −22.816 | −22.729 | 1.00 | 109.12 | N |
| ATOM | 2213 | C | LYS A | 298 | 19.275 | −19.059 | −20.096 | 1.00 | 87.79 | C |
| ATOM | 2214 | O | LYS A | 298 | 20.291 | −18.868 | −20.738 | 1.00 | 78.83 | O |
| ATOM | 2215 | N | ASP A | 299 | 18.148 | −18.407 | −20.339 | 1.00 | 89.17 | N |
| ATOM | 2216 | CA | ASP A | 299 | 18.089 | −17.485 | −21.461 | 1.00 | 87.54 | C |
| ATOM | 2217 | CB | ASP A | 299 | 18.153 | −18.308 | −22.742 | 1.00 | 88.07 | C |
| ATOM | 2218 | CG | ASP A | 299 | 18.857 | −17.600 | −23.855 | 1.00 | 86.53 | C |
| ATOM | 2219 | OD1 | ASP A | 299 | 19.268 | −16.453 | −23.663 | 1.00 | 80.29 | O |
| ATOM | 2220 | OD2 | ASP A | 299 | 19.007 | −18.189 | −24.933 | 1.00 | 91.96 | O |
| ATOM | 2221 | C | ASP A | 299 | 16.848 | −16.622 | −21.495 | 1.00 | 82.17 | C |
| ATOM | 2222 | O | ASP A | 299 | 16.075 | −16.617 | −20.551 | 1.00 | 70.86 | O |
| ATOM | 2223 | N | LEU A | 300 | 16.665 | −15.909 | −22.607 | 1.00 | 79.44 | N |
| ATOM | 2224 | CA | LEU A | 300 | 15.510 | −14.985 | −22.796 | 1.00 | 74.97 | C |
| ATOM | 2225 | CB | LEU A | 300 | 16.047 | −13.554 | −22.790 | 1.00 | 70.29 | C |
| ATOM | 2226 | CG | LEU A | 300 | 17.139 | −13.180 | −21.792 | 1.00 | 70.91 | C |
| ATOM | 2227 | CD1 | LEU A | 300 | 17.765 | −11.825 | −22.146 | 1.00 | 71.43 | C |
| ATOM | 2228 | CD2 | LEU A | 300 | 16.605 | −13.164 | −20.368 | 1.00 | 69.87 | C |
| ATOM | 2229 | C | LEU A | 300 | 14.708 | −15.174 | −24.125 | 1.00 | 74.06 | C |
| ATOM | 2230 | O | LEU A | 300 | 15.179 | −14.691 | −25.160 | 1.00 | 80.91 | O |
| ATOM | 2231 | N | ARG A | 301 | 13.546 | −15.860 | −24.142 | 1.00 | 69.27 | N |
| ATOM | 2232 | CA | ARG A | 301 | 12.689 | −15.874 | −25.391 | 1.00 | 68.37 | C |

TABLE 6-continued

Atomic coordinates for CRBN:DDB1: Compound B (Human protein)

| ATOM | 2233 | CB  | ARG A | 301 | 11.801 | −17.175 | −25.625 | 1.00 | 56.23 | C |
|------|------|-----|-------|-----|--------|---------|---------|------|-------|---|
| ATOM | 2234 | C   | ARG A | 301 | 11.880 | −14.526 | −25.320 | 1.00 | 70.05 | C |
| ATOM | 2235 | O   | ARG A | 301 | 11.771 | −13.936 | −24.229 | 1.00 | 60.62 | O |
| ATOM | 2236 | N   | VAL A | 302 | 11.388 | −14.058 | −26.489 | 1.00 | 72.49 | N |
| ATOM | 2237 | CA  | VAL A | 302 | 10.551 | −12.851 | −26.682 | 1.00 | 69.54 | C |
| ATOM | 2238 | CB  | VAL A | 302 | 11.424 | −11.707 | −27.235 | 1.00 | 67.15 | C |
| ATOM | 2239 | CG1 | VAL A | 302 | 10.616 | −10.522 | −27.769 | 1.00 | 67.66 | C |
| ATOM | 2240 | CG2 | VAL A | 302 | 12.358 | −11.237 | −26.159 | 1.00 | 70.97 | C |
| ATOM | 2241 | C   | VAL A | 302 | 9.396  | −13.124 | −27.679 | 1.00 | 74.17 | C |
| ATOM | 2242 | O   | VAL A | 302 | 9.580  | −12.959 | −28.876 | 1.00 | 80.43 | O |
| ATOM | 2243 | N   | GLU A | 303 | 8.212  | −13.533 | −27.214 | 1.00 | 76.75 | N |
| ATOM | 2244 | CA  | GLU A | 303 | 7.084  | −13.846 | −28.140 | 1.00 | 76.95 | C |
| ATOM | 2245 | CB  | GLU A | 303 | 6.063  | −14.815 | −27.508 | 1.00 | 77.28 | C |
| ATOM | 2246 | CG  | GLU A | 303 | 5.372  | −15.773 | −28.472 | 1.00 | 80.88 | C |
| ATOM | 2247 | CD  | GLU A | 303 | 4.884  | −17.039 | −27.762 | 1.00 | 91.72 | C |
| ATOM | 2248 | OE1 | GLU A | 303 | 4.146  | −16.936 | −26.757 | 1.00 | 96.96 | O |
| ATOM | 2249 | OE2 | GLU A | 303 | 5.246  | −18.158 | −28.182 | 1.00 | 96.79 | O |
| ATOM | 2250 | C   | GLU A | 303 | 6.430  | −12.525 | −28.518 | 1.00 | 72.04 | C |
| ATOM | 2251 | O   | GLU A | 303 | 6.554  | −11.567 | −27.789 | 1.00 | 67.62 | O |
| ATOM | 2252 | N   | LEU A | 304 | 5.786  | −12.471 | −29.678 | 1.00 | 69.02 | N |
| ATOM | 2253 | CA  | LEU A | 304 | 5.025  | −11.298 | −30.081 | 1.00 | 61.81 | C |
| ATOM | 2254 | CB  | LEU A | 304 | 5.335  | −10.882 | −31.515 | 1.00 | 56.81 | C |
| ATOM | 2255 | CG  | LEU A | 304 | 4.281  | −10.011 | −32.211 | 1.00 | 56.12 | C |
| ATOM | 2256 | CD1 | LEU A | 304 | 3.924  | −8.733  | −31.462 | 1.00 | 57.66 | C |
| ATOM | 2257 | CD2 | LEU A | 304 | 4.781  | −9.676  | −33.591 | 1.00 | 56.56 | C |
| ATOM | 2258 | C   | LEU A | 304 | 3.574  | −11.674 | −29.954 | 1.00 | 62.46 | C |
| ATOM | 2259 | O   | LEU A | 304 | 3.059  | −12.478 | −30.743 | 1.00 | 61.92 | O |
| ATOM | 2260 | N   | LEU A | 305 | 2.897  | −11.048 | −29.003 | 1.00 | 62.91 | N |
| ATOM | 2261 | CA  | LEU A | 305 | 1.558  | −11.489 | −28.638 | 1.00 | 62.60 | C |
| ATOM | 2262 | CB  | LEU A | 305 | 1.258  | −11.169 | −27.188 | 1.00 | 64.21 | C |
| ATOM | 2263 | CG  | LEU A | 305 | 2.388  | −11.464 | −26.188 | 1.00 | 64.35 | C |
| ATOM | 2264 | CD1 | LEU A | 305 | 2.355  | −10.407 | −25.091 | 1.00 | 65.76 | C |
| ATOM | 2265 | CD2 | LEU A | 305 | 2.286  | −12.861 | −25.617 | 1.00 | 62.78 | C |
| ATOM | 2266 | C   | LEU A | 305 | 0.500  | −10.900 | −29.554 | 1.00 | 58.33 | C |
| ATOM | 2267 | O   | LEU A | 305 | −0.398 | −11.612 | −29.945 | 1.00 | 55.91 | O |
| ATOM | 2268 | N   | GLY A | 306 | 0.597  | −9.621  | −29.909 | 1.00 | 57.08 | N |
| ATOM | 2269 | CA  | GLY A | 306 | −0.434 | −9.022  | −30.797 | 1.00 | 57.84 | C |
| ATOM | 2270 | C   | GLY A | 306 | −0.356 | −7.523  | −30.972 | 1.00 | 53.59 | C |
| ATOM | 2271 | O   | GLY A | 306 | 0.704  | −6.951  | −30.803 | 1.00 | 49.88 | O |
| ATOM | 2272 | N   | GLU A | 307 | −1.484 | −6.896  | −31.305 | 1.00 | 54.12 | N |
| ATOM | 2273 | CA  | GLU A | 307 | −1.564 | −5.426  | −31.468 | 1.00 | 54.40 | C |
| ATOM | 2274 | CB  | GLU A | 307 | −2.090 | −5.027  | −32.843 | 1.00 | 55.55 | C |
| ATOM | 2275 | CG  | GLU A | 307 | −1.145 | −4.154  | −33.636 | 1.00 | 61.68 | C |
| ATOM | 2276 | CD  | GLU A | 307 | −1.808 | −3.456  | −34.830 | 1.00 | 67.74 | C |
| ATOM | 2277 | OE1 | GLU A | 307 | −1.013 | −2.938  | −35.682 | 1.00 | 74.56 | O |
| ATOM | 2278 | OE2 | GLU A | 307 | −3.083 | −3.415  | −34.907 | 1.00 | 60.11 | O |
| ATOM | 2279 | C   | GLU A | 307 | −2.515 | −4.831  | −30.440 | 1.00 | 55.39 | C |
| ATOM | 2280 | O   | GLU A | 307 | −3.626 | −5.343  | −30.185 | 1.00 | 53.11 | O |
| ATOM | 2281 | N   | THR A | 308 | −2.090 | −3.716  | −29.866 | 1.00 | 55.33 | N |
| ATOM | 2282 | CA  | THR A | 308 | −2.941 | −2.967  | −28.949 | 1.00 | 52.95 | C |
| ATOM | 2283 | CB  | THR A | 308 | −2.408 | −3.051  | −27.488 | 1.00 | 48.95 | C |
| ATOM | 2284 | OG1 | THR A | 308 | −1.057 | −2.547  | −27.377 | 1.00 | 43.93 | O |
| ATOM | 2285 | CG2 | THR A | 308 | −2.415 | −4.530  | −27.046 | 1.00 | 46.96 | C |
| ATOM | 2286 | C   | THR A | 308 | −2.974 | −1.567  | −29.495 | 1.00 | 53.89 | C |
| ATOM | 2287 | O   | THR A | 308 | −2.275 | −1.223  | −30.461 | 1.00 | 56.54 | O |
| ATOM | 2288 | N   | SER A | 309 | −3.809 | −0.763  | −28.887 | 1.00 | 53.04 | N |
| ATOM | 2289 | CA  | SER A | 309 | −3.646 | 0.653   | −28.980 | 1.00 | 49.81 | C |
| ATOM | 2290 | CB  | SER A | 309 | −4.667 | 1.390   | −28.087 | 1.00 | 50.79 | C |
| ATOM | 2291 | OG  | SER A | 309 | −6.005 | 1.118   | −28.493 | 1.00 | 52.26 | O |
| ATOM | 2292 | C   | SER A | 309 | −2.227 | 0.948   | −28.520 | 1.00 | 44.51 | C |
| ATOM | 2293 | O   | SER A | 309 | −1.633 | 0.227   | −27.752 | 1.00 | 40.69 | O |
| ATOM | 2294 | N   | ILE A | 310 | −1.728 | 2.052   | −28.996 | 1.00 | 43.39 | N |
| ATOM | 2295 | CA  | ILE A | 310 | −0.359 | 2.435   | −28.867 | 1.00 | 44.04 | C |
| ATOM | 2296 | CB  | ILE A | 310 | −0.133 | 3.666   | −29.783 | 1.00 | 46.28 | C |
| ATOM | 2297 | CG1 | ILE A | 310 | −0.542 | 3.345   | −31.214 | 1.00 | 46.62 | C |
| ATOM | 2298 | CD1 | ILE A | 310 | −0.619 | 4.569   | −32.068 | 1.00 | 49.50 | C |
| ATOM | 2299 | CG2 | ILE A | 310 | 1.314  | 4.162   | −29.769 | 1.00 | 47.00 | C |
| ATOM | 2300 | C   | ILE A | 310 | −0.167 | 2.795   | −27.404 | 1.00 | 44.45 | C |
| ATOM | 2301 | O   | ILE A | 310 | −0.773 | 3.759   | −26.871 | 1.00 | 47.31 | O |
| ATOM | 2302 | N   | ALA A | 311 | 0.648  | 2.017   | −26.729 | 1.00 | 44.02 | N |
| ATOM | 2303 | CA  | ALA A | 311 | 0.613  | 2.033   | −25.258 | 1.00 | 45.80 | C |
| ATOM | 2304 | CB  | ALA A | 311 | 0.912  | 0.659   | −24.681 | 1.00 | 44.81 | C |
| ATOM | 2305 | C   | ALA A | 311 | 1.559  | 3.059   | −24.641 | 1.00 | 47.00 | C |
| ATOM | 2306 | O   | ALA A | 311 | 2.719  | 3.176   | −25.045 | 1.00 | 48.42 | O |
| ATOM | 2307 | N   | GLU A | 312 | 1.041  | 3.791   | −23.659 | 1.00 | 46.47 | N |
| ATOM | 2308 | CA  | GLU A | 312 | 1.839  | 4.654   | −22.854 | 1.00 | 46.37 | C |
| ATOM | 2309 | CB  | GLU A | 312 | 0.996  | 5.829   | −22.408 | 1.00 | 46.43 | C |
| ATOM | 2310 | CG  | GLU A | 312 | 1.728  | 6.820   | −21.522 | 1.00 | 49.83 | C |

TABLE 6-continued

Atomic coordinates for CRBN:DDB1: Compound B (Human protein)

| ATOM | 2311 | CD  | GLU A | 312 | 2.981  | 7.474   | −22.129 | 1.00 | 53.14  | C |
|------|------|-----|-------|-----|--------|---------|---------|------|--------|---|
| ATOM | 2312 | OE1 | GLU A | 312 | 3.580  | 8.301   | −21.383 | 1.00 | 55.56  | O |
| ATOM | 2313 | OE2 | GLU A | 312 | 3.327  | 7.232   | −23.324 | 1.00 | 51.85  | O |
| ATOM | 2314 | C   | GLU A | 312 | 2.336  | 3.867   | −21.673 | 1.00 | 48.11  | C |
| ATOM | 2315 | O   | GLU A | 312 | 3.487  | 4.053   | −21.179 | 1.00 | 49.71  | O |
| ATOM | 2316 | N   | CYS A | 313 | 1.459  | 3.001   | −21.187 | 1.00 | 46.56  | N |
| ATOM | 2317 | CA  | CYS A | 313 | 1.751  | 2.298   | −20.000 | 1.00 | 46.51  | C |
| ATOM | 2318 | CB  | CYS A | 313 | 1.439  | 3.242   | −18.854 | 1.00 | 47.48  | C |
| ATOM | 2319 | SG  | CYS A | 313 | −0.308 | 3.382   | −18.417 | 1.00 | 58.25  | S |
| ATOM | 2320 | C   | CYS A | 313 | 0.879  | 1.053   | −20.065 | 1.00 | 46.38  | C |
| ATOM | 2321 | O   | CYS A | 313 | −0.155 | 1.078   | −20.771 | 1.00 | 43.47  | O |
| ATOM | 2322 | N   | LEU A | 314 | 1.287  | −0.009  | −19.352 | 1.00 | 45.18  | N |
| ATOM | 2323 | CA  | LEU A | 314 | 0.594  | −1.319  | −19.368 | 1.00 | 44.86  | C |
| ATOM | 2324 | CB  | LEU A | 314 | 1.388  | −2.306  | −20.196 | 1.00 | 42.07  | C |
| ATOM | 2325 | CG  | LEU A | 314 | 1.666  | −2.100  | −21.683 | 1.00 | 42.47  | C |
| ATOM | 2326 | CD1 | LEU A | 314 | 3.026  | −2.595  | −22.158 | 1.00 | 42.82  | C |
| ATOM | 2327 | CD2 | LEU A | 314 | 0.658  | −2.846  | −22.519 | 1.00 | 44.07  | C |
| ATOM | 2328 | C   | LEU A | 314 | 0.512  | −1.935  | −17.974 | 1.00 | 50.52  | C |
| ATOM | 2329 | O   | LEU A | 314 | 1.470  | −1.889  | −17.229 | 1.00 | 58.60  | O |
| ATOM | 2330 | N   | THR A | 315 | −0.589 | −2.565  | −17.640 | 1.00 | 53.74  | N |
| ATOM | 2331 | CA  | THR A | 315 | −0.673 | −3.202  | −16.356 | 1.00 | 56.89  | C |
| ATOM | 2332 | CB  | THR A | 315 | −1.523 | −2.388  | −15.414 | 1.00 | 62.77  | C |
| ATOM | 2333 | OG1 | THR A | 315 | −0.856 | −1.165  | −15.184 | 1.00 | 70.96  | O |
| ATOM | 2334 | CG2 | THR A | 315 | −1.638 | −3.062  | −14.128 | 1.00 | 68.61  | C |
| ATOM | 2335 | C   | THR A | 315 | −1.286 | −4.546  | −16.537 | 1.00 | 58.81  | C |
| ATOM | 2336 | O   | THR A | 315 | −2.227 | −4.678  | −17.276 | 1.00 | 63.44  | O |
| ATOM | 2337 | N   | TYR A | 316 | −0.769 | −5.545  | −15.852 | 1.00 | 58.00  | N |
| ATOM | 2338 | CA  | TYR A | 316 | −1.316 | −6.861  | −15.971 | 1.00 | 54.77  | C |
| ATOM | 2339 | CB  | TYR A | 316 | −0.219 | −7.897  | −15.898 | 1.00 | 56.89  | C |
| ATOM | 2340 | CG  | TYR A | 316 | −0.756 | −9.285  | −15.964 | 1.00 | 60.13  | C |
| ATOM | 2341 | CD1 | TYR A | 316 | −1.072 | −9.855  | −17.163 | 1.00 | 60.67  | C |
| ATOM | 2342 | CE1 | TYR A | 316 | −1.582 | −11.122 | −17.233 | 1.00 | 61.37  | C |
| ATOM | 2343 | CZ  | TYR A | 316 | −1.779 | −11.826 | −16.100 | 1.00 | 61.39  | C |
| ATOM | 2344 | OH  | TYR A | 316 | −2.286 | −13.080 | −16.187 | 1.00 | 55.59  | O |
| ATOM | 2345 | CE2 | TYR A | 316 | −1.473 | −11.284 | −14.888 | 1.00 | 60.22  | C |
| ATOM | 2346 | CD2 | TYR A | 316 | −0.966 | −10.016 | −14.826 | 1.00 | 60.82  | C |
| ATOM | 2347 | C   | TYR A | 316 | −2.205 | −6.989  | −14.791 | 1.00 | 52.01  | C |
| ATOM | 2348 | O   | TYR A | 316 | −1.767 | −6.830  | −13.688 | 1.00 | 51.65  | O |
| ATOM | 2349 | N   | LEU A | 317 | −3.469 | −7.262  | −15.024 | 1.00 | 51.59  | N |
| ATOM | 2350 | CA  | LEU A | 317 | −4.417 | −7.376  | −13.944 | 1.00 | 55.48  | C |
| ATOM | 2351 | CB  | LEU A | 317 | −5.754 | −6.860  | −14.418 | 1.00 | 51.90  | C |
| ATOM | 2352 | CG  | LEU A | 317 | −5.699 | −5.499  | −15.044 | 1.00 | 52.56  | C |
| ATOM | 2353 | CD1 | LEU A | 317 | −7.095 | −5.042  | −15.352 | 1.00 | 51.32  | C |
| ATOM | 2354 | CD2 | LEU A | 317 | −5.056 | −4.594  | −14.038 | 1.00 | 51.93  | C |
| ATOM | 2355 | C   | LEU A | 317 | −4.678 | −8.740  | −13.367 | 1.00 | 63.68  | C |
| ATOM | 2356 | O   | LEU A | 317 | −5.373 | −8.833  | −12.402 | 1.00 | 65.51  | O |
| ATOM | 2357 | N   | ASP A | 318 | −4.150 | −9.788  | −13.963 | 1.00 | 74.10  | N |
| ATOM | 2358 | CA  | ASP A | 318 | −4.373 | −11.172 | −13.541 | 1.00 | 80.65  | C |
| ATOM | 2359 | CB  | ASP A | 318 | −4.549 | −11.358 | −12.038 | 1.00 | 89.90  | C |
| ATOM | 2360 | CG  | ASP A | 318 | −3.461 | −12.198 | −11.432 | 1.00 | 95.92  | C |
| ATOM | 2361 | OD1 | ASP A | 318 | −3.452 | −13.417 | −11.683 | 1.00 | 95.22  | O |
| ATOM | 2362 | OD2 | ASP A | 318 | −2.619 | −11.645 | −10.700 | 1.00 | 106.94 | O |
| ATOM | 2363 | C   | ASP A | 318 | −5.553 | −11.750 | −14.279 | 1.00 | 74.07  | C |
| ATOM | 2364 | O   | ASP A | 318 | −6.430 | −11.033 | −14.695 | 1.00 | 75.49  | O |
| ATOM | 2365 | N   | ASN A | 319 | −5.556 | −13.066 | −14.405 | 1.00 | 64.88  | N |
| ATOM | 2366 | CA  | ASN A | 319 | −6.571 | −13.783 | −15.131 | 1.00 | 57.55  | C |
| ATOM | 2367 | CB  | ASN A | 319 | −7.957 | −13.257 | −14.818 | 1.00 | 56.76  | C |
| ATOM | 2368 | C   | ASN A | 319 | −6.302 | −13.664 | −16.601 | 1.00 | 51.83  | C |
| ATOM | 2369 | O   | ASN A | 319 | −7.148 | −13.977 | −17.404 | 1.00 | 50.32  | O |
| ATOM | 2370 | N   | GLY A | 320 | −5.113 | −13.207 | −16.952 | 1.00 | 50.23  | N |
| ATOM | 2371 | CA  | GLY A | 320 | −4.745 | −13.049 | −18.339 | 1.00 | 54.38  | C |
| ATOM | 2372 | C   | GLY A | 320 | −5.195 | −11.758 | −18.966 | 1.00 | 55.95  | C |
| ATOM | 2373 | O   | GLY A | 320 | −5.089 | −11.572 | −20.158 | 1.00 | 53.42  | O |
| ATOM | 2374 | N   | VAL A | 321 | −5.701 | −10.862 | −18.141 | 1.00 | 59.97  | N |
| ATOM | 2375 | CA  | VAL A | 321 | −6.178 | −9.587  | −18.600 | 1.00 | 57.19  | C |
| ATOM | 2376 | CB  | VAL A | 321 | −7.449 | −9.204  | −17.884 | 1.00 | 59.80  | C |
| ATOM | 2377 | CG1 | VAL A | 321 | −7.932 | −7.875  | −18.388 | 1.00 | 62.54  | C |
| ATOM | 2378 | CG2 | VAL A | 321 | −8.497 | −10.258 | −18.114 | 1.00 | 60.11  | C |
| ATOM | 2379 | C   | VAL A | 321 | −5.152 | −8.523  | −18.355 | 1.00 | 54.75  | C |
| ATOM | 2380 | O   | VAL A | 321 | −4.493 | −8.522  | −17.341 | 1.00 | 50.12  | O |
| ATOM | 2381 | N   | VAL A | 322 | −5.021 | −7.623  | −19.316 | 1.00 | 53.86  | N |
| ATOM | 2382 | CA  | VAL A | 322 | −4.057 | −6.544  | −19.260 | 1.00 | 54.48  | C |
| ATOM | 2383 | CB  | VAL A | 322 | −3.022 | −6.742  | −20.345 | 1.00 | 56.87  | C |
| ATOM | 2384 | CG1 | VAL A | 322 | −1.959 | −5.685  | −20.262 | 1.00 | 56.55  | C |
| ATOM | 2385 | CG2 | VAL A | 322 | −2.399 | −8.099  | −20.201 | 1.00 | 56.84  | C |
| ATOM | 2386 | C   | VAL A | 322 | −4.669 | −5.200  | −19.522 | 1.00 | 50.20  | C |
| ATOM | 2387 | O   | VAL A | 322 | −5.553 | −5.081  | −20.320 | 1.00 | 47.59  | O |
| ATOM | 2388 | N   | PHE A | 323 | −4.168 | −4.179  | −18.856 | 1.00 | 48.94  | N |

TABLE 6-continued

Atomic coordinates for CRBN:DDB1: Compound B (Human protein)

| ATOM | 2389 | CA | PHE A | 323 | −4.694 | −2.857 | −19.059 | 1.00 | 49.42 | C |
|---|---|---|---|---|---|---|---|---|---|---|
| ATOM | 2390 | CB | PHE A | 323 | −4.823 | −2.077 | −17.769 | 1.00 | 49.26 | C |
| ATOM | 2391 | CG | PHE A | 323 | −5.307 | −0.684 | −17.981 | 1.00 | 47.81 | C |
| ATOM | 2392 | CD1 | PHE A | 323 | −6.604 | −0.448 | −18.311 | 1.00 | 46.07 | C |
| ATOM | 2393 | CE1 | PHE A | 323 | −7.051 | 0.817 | −18.529 | 1.00 | 44.63 | C |
| ATOM | 2394 | CZ | PHE A | 323 | −6.195 | 1.865 | −18.422 | 1.00 | 48.23 | C |
| ATOM | 2395 | CE2 | PHE A | 323 | −4.892 | 1.646 | −18.107 | 1.00 | 49.35 | C |
| ATOM | 2396 | CD2 | PHE A | 323 | −4.456 | 0.377 | −17.885 | 1.00 | 48.22 | C |
| ATOM | 2397 | C | PHE A | 323 | −3.751 | −2.128 | −19.940 | 1.00 | 45.81 | C |
| ATOM | 2398 | O | PHE A | 323 | −2.582 | −2.091 | −19.685 | 1.00 | 46.38 | O |
| ATOM | 2399 | N | VAL A | 324 | −4.270 | −1.536 | −20.987 | 1.00 | 44.02 | N |
| ATOM | 2400 | CA | VAL A | 324 | −3.409 | −0.813 | −21.905 | 1.00 | 44.39 | C |
| ATOM | 2401 | CB | VAL A | 324 | −3.565 | −1.274 | −23.365 | 1.00 | 46.23 | C |
| ATOM | 2402 | CG1 | VAL A | 324 | −2.622 | −0.474 | −24.241 | 1.00 | 47.91 | C |
| ATOM | 2403 | CG2 | VAL A | 324 | −3.279 | −2.753 | −23.498 | 1.00 | 46.22 | C |
| ATOM | 2404 | C | VAL A | 324 | −3.859 | 0.629 | −21.811 | 1.00 | 45.99 | C |
| ATOM | 2405 | O | VAL A | 324 | −4.939 | 0.992 | −22.315 | 1.00 | 45.88 | O |
| ATOM | 2406 | N | GLY A | 325 | −3.046 | 1.445 | −21.136 | 1.00 | 44.59 | N |
| ATOM | 2407 | CA | GLY A | 325 | −3.258 | 2.876 | −21.120 | 1.00 | 40.45 | C |
| ATOM | 2408 | C | GLY A | 325 | −2.619 | 3.531 | −22.327 | 1.00 | 36.19 | C |
| ATOM | 2409 | O | GLY A | 325 | −1.486 | 3.258 | −22.653 | 1.00 | 34.25 | O |
| ATOM | 2410 | N | SER A | 326 | −3.315 | 4.462 | −22.918 | 1.00 | 35.05 | N |
| ATOM | 2411 | CA | SER A | 326 | −2.861 | 5.081 | −24.132 | 1.00 | 38.89 | C |
| ATOM | 2412 | CB | SER A | 326 | −3.686 | 4.542 | −25.331 | 1.00 | 37.41 | C |
| ATOM | 2413 | OG | SER A | 326 | −3.308 | 5.187 | −26.531 | 1.00 | 35.64 | O |
| ATOM | 2414 | C | SER A | 326 | −2.986 | 6.595 | −24.072 | 1.00 | 41.14 | C |
| ATOM | 2415 | O | SER A | 326 | −3.908 | 7.154 | −23.470 | 1.00 | 42.10 | O |
| ATOM | 2416 | N | ARG A | 327 | −2.097 | 7.263 | −24.774 | 1.00 | 45.62 | N |
| ATOM | 2417 | CA | ARG A | 327 | −2.262 | 8.691 | −24.966 | 1.00 | 50.73 | C |
| ATOM | 2418 | CB | ARG A | 327 | −0.988 | 9.435 | −24.592 | 1.00 | 56.63 | C |
| ATOM | 2419 | CG | ARG A | 327 | −0.828 | 9.401 | −23.087 | 1.00 | 61.93 | C |
| ATOM | 2420 | CD | ARG A | 327 | 0.438 | 10.031 | −22.532 | 1.00 | 69.79 | C |
| ATOM | 2421 | NE | ARG A | 327 | 0.651 | 11.382 | −23.042 | 1.00 | 73.98 | N |
| ATOM | 2422 | CZ | ARG A | 327 | 0.125 | 12.488 | −22.567 | 1.00 | 65.53 | C |
| ATOM | 2423 | NH1 | ARG A | 327 | −0.681 | 12.479 | −21.525 | 1.00 | 75.01 | N |
| ATOM | 2424 | NH2 | ARG A | 327 | 0.422 | 13.602 | −23.163 | 1.00 | 62.80 | N |
| ATOM | 2425 | C | ARG A | 327 | −2.728 | 9.054 | −26.338 | 1.00 | 48.37 | C |
| ATOM | 2426 | O | ARG A | 327 | −3.407 | 10.071 | −26.498 | 1.00 | 51.02 | O |
| ATOM | 2427 | N | LEU A | 328 | −2.414 | 8.215 | −27.311 | 1.00 | 46.54 | N |
| ATOM | 2428 | CA | LEU A | 328 | −2.705 | 8.546 | −28.692 | 1.00 | 46.88 | C |
| ATOM | 2429 | CB | LEU A | 328 | −1.537 | 8.135 | −29.579 | 1.00 | 49.19 | C |
| ATOM | 2430 | CG | LEU A | 328 | −0.305 | 8.889 | −29.145 | 1.00 | 50.84 | C |
| ATOM | 2431 | CD1 | LEU A | 328 | 0.888 | 8.495 | −29.989 | 1.00 | 52.68 | C |
| ATOM | 2432 | CD2 | LEU A | 328 | −0.599 | 10.353 | −29.280 | 1.00 | 49.64 | C |
| ATOM | 2433 | C | LEU A | 328 | −3.948 | 7.926 | −29.241 | 1.00 | 43.17 | C |
| ATOM | 2434 | O | LEU A | 328 | −4.333 | 8.289 | −30.336 | 1.00 | 43.87 | O |
| ATOM | 2435 | N | GLY A | 329 | −4.548 | 6.978 | −28.537 | 1.00 | 37.92 | N |
| ATOM | 2436 | CA | GLY A | 329 | −5.859 | 6.521 | −28.915 | 1.00 | 37.82 | C |
| ATOM | 2437 | C | GLY A | 329 | −6.530 | 6.031 | −27.678 | 1.00 | 38.21 | C |
| ATOM | 2438 | O | GLY A | 329 | −5.991 | 6.226 | −26.601 | 1.00 | 35.93 | O |
| ATOM | 2439 | N | ASP A | 330 | −7.650 | 5.322 | −27.860 | 1.00 | 39.65 | N |
| ATOM | 2440 | CA | ASP A | 330 | −8.427 | 4.731 | −26.762 | 1.00 | 39.56 | C |
| ATOM | 2441 | CB | ASP A | 330 | −9.653 | 3.979 | −27.319 | 1.00 | 40.95 | C |
| ATOM | 2442 | CG | ASP A | 330 | −10.754 | 4.895 | −27.934 | 1.00 | 42.90 | C |
| ATOM | 2443 | OD1 | ASP A | 330 | −10.731 | 6.157 | −27.877 | 1.00 | 44.11 | O |
| ATOM | 2444 | OD2 | ASP A | 330 | −11.707 | 4.308 | −28.482 | 1.00 | 43.57 | O |
| ATOM | 2445 | C | ASP A | 330 | −7.578 | 3.760 | −25.884 | 1.00 | 39.92 | C |
| ATOM | 2446 | O | ASP A | 330 | −6.645 | 3.174 | −26.366 | 1.00 | 41.07 | O |
| ATOM | 2447 | N | SER A | 331 | −7.901 | 3.633 | −24.590 | 1.00 | 42.53 | N |
| ATOM | 2448 | CA | SER A | 331 | −7.321 | 2.614 | −23.704 | 1.00 | 41.76 | C |
| ATOM | 2449 | CB | SER A | 331 | −7.275 | 3.073 | −22.247 | 1.00 | 41.37 | C |
| ATOM | 2450 | OG | SER A | 331 | −6.234 | 4.014 | −22.073 | 1.00 | 42.35 | O |
| ATOM | 2451 | C | SER A | 331 | −8.123 | 1.344 | −23.825 | 1.00 | 41.05 | C |
| ATOM | 2452 | O | SER A | 331 | −9.174 | 1.312 | −24.478 | 1.00 | 40.76 | O |
| ATOM | 2453 | N | GLN A | 332 | −7.584 | 0.285 | −23.239 | 1.00 | 40.67 | N |
| ATOM | 2454 | CA | GLN A | 332 | −8.116 | −1.029 | −23.439 | 1.00 | 42.30 | C |
| ATOM | 2455 | CB | GLN A | 332 | −7.443 | −1.708 | −24.621 | 1.00 | 44.97 | C |
| ATOM | 2456 | CG | GLN A | 332 | −7.258 | −0.844 | −25.869 | 1.00 | 47.35 | C |
| ATOM | 2457 | CD | GLN A | 332 | −6.705 | −1.675 | −26.991 | 1.00 | 46.91 | C |
| ATOM | 2458 | OE1 | GLN A | 332 | −5.488 | −1.932 | −27.079 | 1.00 | 47.21 | O |
| ATOM | 2459 | NE2 | GLN A | 332 | −7.596 | −2.150 | −27.829 | 1.00 | 46.83 | N |
| ATOM | 2460 | C | GLN A | 332 | −7.885 | −1.922 | −22.254 | 1.00 | 44.71 | C |
| ATOM | 2461 | O | GLN A | 332 | −6.906 | −1.757 | −21.483 | 1.00 | 43.29 | O |
| ATOM | 2462 | N | LEU A | 333 | −8.811 | −2.881 | −22.132 | 1.00 | 45.35 | N |
| ATOM | 2463 | CA | LEU A | 333 | −8.564 | −4.133 | −21.472 | 1.00 | 43.13 | C |
| ATOM | 2464 | CB | LEU A | 333 | −9.731 | −4.479 | −20.603 | 1.00 | 43.32 | C |
| ATOM | 2465 | CG | LEU A | 333 | −9.783 | −3.677 | −19.319 | 1.00 | 46.24 | C |
| ATOM | 2466 | CD1 | LEU A | 333 | −11.149 | −3.867 | −18.724 | 1.00 | 48.06 | C |

TABLE 6-continued

Atomic coordinates for CRBN:DDB1: Compound B (Human protein)

| ATOM | 2467 | CD2 | LEU A | 333 | −8.745 | −4.087 | −18.290 | 1.00 | 48.30 | C |
|---|---|---|---|---|---|---|---|---|---|---|
| ATOM | 2468 | C | LEU A | 333 | −8.405 | −5.138 | −22.605 | 1.00 | 43.82 | C |
| ATOM | 2469 | O | LEU A | 333 | −9.195 | −5.137 | −23.535 | 1.00 | 42.93 | O |
| ATOM | 2470 | N | VAL A | 334 | −7.355 | −5.958 | −22.553 | 1.00 | 45.88 | N |
| ATOM | 2471 | CA | VAL A | 334 | −7.153 | −7.061 | −23.511 | 1.00 | 44.66 | C |
| ATOM | 2472 | CB | VAL A | 334 | −5.945 | −6.874 | −24.427 | 1.00 | 43.39 | C |
| ATOM | 2473 | CG1 | VAL A | 334 | −6.108 | −5.642 | −25.271 | 1.00 | 43.47 | C |
| ATOM | 2474 | CG2 | VAL A | 334 | −4.661 | −6.771 | −23.632 | 1.00 | 45.15 | C |
| ATOM | 2475 | C | VAL A | 334 | −6.927 | −8.347 | −22.778 | 1.00 | 46.32 | C |
| ATOM | 2476 | O | VAL A | 334 | −6.336 | −8.333 | −21.694 | 1.00 | 41.50 | O |
| ATOM | 2477 | N | LYS A | 335 | −7.375 | −9.448 | −23.400 | 1.00 | 54.52 | N |
| ATOM | 2478 | CA | LYS A | 335 | −7.143 | −10.821 | −22.893 | 1.00 | 60.19 | C |
| ATOM | 2479 | CB | LYS A | 335 | −8.383 | −11.703 | −23.087 | 1.00 | 66.02 | C |
| ATOM | 2480 | CG | LYS A | 335 | −8.147 | −13.168 | −22.697 | 1.00 | 75.26 | C |
| ATOM | 2481 | CD | LYS A | 335 | −9.372 | −13.904 | −22.165 | 1.00 | 79.06 | C |
| ATOM | 2482 | CE | LYS A | 335 | −9.452 | −13.776 | −20.645 | 1.00 | 88.45 | C |
| ATOM | 2483 | NZ | LYS A | 335 | −8.302 | −14.408 | −19.918 | 1.00 | 91.73 | N |
| ATOM | 2484 | C | LYS A | 335 | −5.949 | −11.424 | −23.614 | 1.00 | 57.92 | C |
| ATOM | 2485 | O | LYS A | 335 | −5.804 | −11.186 | −24.778 | 1.00 | 56.90 | O |
| ATOM | 2486 | N | LEU A | 336 | −5.099 | −12.170 | −22.909 | 1.00 | 60.00 | N |
| ATOM | 2487 | CA | LEU A | 336 | −4.011 | −12.971 | −23.503 | 1.00 | 62.72 | C |
| ATOM | 2488 | CB | LEU A | 336 | −2.784 | −12.825 | −22.639 | 1.00 | 59.56 | C |
| ATOM | 2489 | CG | LEU A | 336 | −2.426 | −11.398 | −22.326 | 1.00 | 59.99 | C |
| ATOM | 2490 | CD1 | LEU A | 336 | −1.047 | −11.377 | −21.659 | 1.00 | 60.06 | C |
| ATOM | 2491 | CD2 | LEU A | 336 | −2.443 | −10.582 | −23.613 | 1.00 | 62.03 | C |
| ATOM | 2492 | C | LEU A | 336 | −4.303 | −14.467 | −23.584 | 1.00 | 69.81 | C |
| ATOM | 2493 | O | LEU A | 336 | −5.131 | −14.950 | −22.831 | 1.00 | 70.16 | O |
| ATOM | 2494 | N | ASN A | 337 | −3.579 | −15.163 | −24.433 | 1.00 | 83.01 | N |
| ATOM | 2495 | CA | ASN A | 337 | −3.716 | −16.588 | −24.517 | 1.00 | 97.98 | C |
| ATOM | 2496 | CB | ASN A | 337 | −4.491 | −16.990 | −25.750 | 1.00 | 107.74 | C |
| ATOM | 2497 | CG | ASN A | 337 | −5.884 | −16.427 | −25.725 | 1.00 | 110.23 | C |
| ATOM | 2498 | OD1 | ASN A | 337 | −6.095 | −15.350 | −25.193 | 1.00 | 99.20 | O |
| ATOM | 2499 | ND2 | ASN A | 337 | −6.844 | −17.161 | −26.257 | 1.00 | 110.43 | N |
| ATOM | 2500 | C | ASN A | 337 | −2.346 | −17.208 | −24.424 | 1.00 | 98.16 | C |
| ATOM | 2501 | O | ASN A | 337 | −1.378 | −16.678 | −24.932 | 1.00 | 87.30 | O |
| ATOM | 2502 | N | VAL A | 338 | −2.276 | −18.341 | −23.756 | 1.00 | 105.96 | N |
| ATOM | 2503 | CA | VAL A | 338 | −1.024 | −19.034 | −23.566 | 1.00 | 110.26 | C |
| ATOM | 2504 | CB | VAL A | 338 | −1.200 | −20.281 | −22.694 | 1.00 | 97.73 | C |
| ATOM | 2505 | C | VAL A | 338 | −0.690 | −19.527 | −24.922 | 1.00 | 112.71 | C |
| ATOM | 2506 | O | VAL A | 338 | −1.542 | −19.507 | −25.800 | 1.00 | 110.35 | O |
| ATOM | 2507 | N | ASP A | 339 | 0.527 | −20.011 | −25.118 | 1.00 | 122.42 | N |
| ATOM | 2508 | CA | ASP A | 339 | 0.889 | −20.490 | −26.436 | 1.00 | 119.30 | C |
| ATOM | 2509 | CB | ASP A | 339 | 2.378 | −20.787 | −26.517 | 1.00 | 108.45 | C |
| ATOM | 2510 | C | ASP A | 339 | 0.117 | −21.770 | −26.465 | 1.00 | 119.97 | C |
| ATOM | 2511 | O | ASP A | 339 | 0.642 | −22.859 | −26.348 | 1.00 | 108.75 | O |
| ATOM | 2512 | N | SER A | 340 | −1.182 | −21.578 | −26.653 | 1.00 | 124.92 | N |
| ATOM | 2513 | CA | SER A | 340 | −2.160 | −22.633 | −26.656 | 1.00 | 120.03 | C |
| ATOM | 2514 | CB | SER A | 340 | −3.528 | −22.074 | −27.018 | 1.00 | 114.30 | C |
| ATOM | 2515 | C | SER A | 340 | −1.701 | −23.564 | −27.718 | 1.00 | 114.51 | C |
| ATOM | 2516 | O | SER A | 340 | −1.114 | −23.138 | −28.694 | 1.00 | 125.94 | O |
| ATOM | 2517 | N | ASN A | 341 | −1.938 | −24.842 | −27.508 | 1.00 | 101.73 | N |
| ATOM | 2518 | CA | ASN A | 341 | −1.463 | −25.817 | −28.439 | 1.00 | 91.03 | C |
| ATOM | 2519 | CB | ASN A | 341 | −1.894 | −27.196 | −27.970 | 1.00 | 76.81 | C |
| ATOM | 2520 | C | ASN A | 341 | −2.030 | −25.536 | −29.802 | 1.00 | 91.69 | C |
| ATOM | 2521 | O | ASN A | 341 | −1.332 | −25.620 | −30.792 | 1.00 | 91.73 | O |
| ATOM | 2522 | N | GLU A | 342 | −3.300 | −25.195 | −29.851 | 1.00 | 88.73 | N |
| ATOM | 2523 | CA | GLU A | 342 | −3.943 | −24.898 | −31.111 | 1.00 | 88.31 | C |
| ATOM | 2524 | CB | GLU A | 342 | −5.452 | −24.848 | −30.942 | 1.00 | 80.68 | C |
| ATOM | 2525 | C | GLU A | 342 | −3.460 | −23.656 | −31.842 | 1.00 | 92.84 | C |
| ATOM | 2526 | O | GLU A | 342 | −3.370 | −23.657 | −33.049 | 1.00 | 98.79 | O |
| ATOM | 2527 | N | GLN A | 343 | −3.179 | −22.582 | −31.128 | 1.00 | 96.58 | N |
| ATOM | 2528 | CA | GLN A | 343 | −2.758 | −21.351 | −31.781 | 1.00 | 95.27 | C |
| ATOM | 2529 | CB | GLN A | 343 | −3.961 | −20.421 | −31.960 | 1.00 | 100.28 | C |
| ATOM | 2530 | CG | GLN A | 343 | −3.662 | −19.130 | −32.707 | 1.00 | 99.81 | C |
| ATOM | 2531 | CD | GLN A | 343 | −4.898 | −18.517 | −33.327 | 1.00 | 93.55 | C |
| ATOM | 2532 | OE1 | GLN A | 343 | −5.028 | −18.476 | −34.541 | 1.00 | 89.00 | O |
| ATOM | 2533 | NE2 | GLN A | 343 | −5.812 | −18.049 | −32.498 | 1.00 | 89.23 | N |
| ATOM | 2534 | C | GLN A | 343 | −1.648 | −20.614 | −31.070 | 1.00 | 91.11 | C |
| ATOM | 2535 | O | GLN A | 343 | −1.390 | −20.815 | −29.894 | 1.00 | 88.99 | O |
| ATOM | 2536 | N | GLY A | 344 | −0.990 | −19.741 | −31.800 | 1.00 | 88.37 | N |
| ATOM | 2537 | CA | GLY A | 344 | 0.071 | −18.968 | −31.221 | 1.00 | 93.35 | C |
| ATOM | 2538 | C | GLY A | 344 | −0.630 | −18.085 | −30.228 | 1.00 | 102.31 | C |
| ATOM | 2539 | O | GLY A | 344 | −1.816 | −17.838 | −30.351 | 1.00 | 112.66 | O |
| ATOM | 2540 | N | SER A | 345 | 0.090 | −17.623 | −29.224 | 1.00 | 104.66 | N |
| ATOM | 2541 | CA | SER A | 345 | −0.509 | −16.778 | −28.228 | 1.00 | 96.76 | C |
| ATOM | 2542 | CB | SER A | 345 | 0.573 | −16.326 | −27.297 | 1.00 | 94.76 | C |
| ATOM | 2543 | OG | SER A | 345 | 1.631 | −15.832 | −28.078 | 1.00 | 91.15 | O |
| ATOM | 2544 | C | SER A | 345 | −1.019 | −15.566 | −28.941 | 1.00 | 92.69 | C |

TABLE 6-continued

Atomic coordinates for CRBN:DDB1: Compound B (Human protein)

| ATOM | 2545 | O | SER A | 345 | −0.333 | −15.011 | −29.772 | 1.00 | 85.91 | O |
|---|---|---|---|---|---|---|---|---|---|---|
| ATOM | 2546 | N | TYR A | 346 | −2.227 | −15.152 | −28.600 | 1.00 | 94.19 | N |
| ATOM | 2547 | CA | TYR A | 346 | −2.849 | −13.998 | −29.215 | 1.00 | 87.02 | C |
| ATOM | 2548 | CB | TYR A | 346 | −3.787 | −14.395 | −30.341 | 1.00 | 88.66 | C |
| ATOM | 2549 | CG | TYR A | 346 | −4.878 | −15.306 | −29.915 | 1.00 | 96.93 | C |
| ATOM | 2550 | CD1 | TYR A | 346 | −4.619 | −16.373 | −29.090 | 1.00 | 100.42 | C |
| ATOM | 2551 | CE1 | TYR A | 346 | −5.621 | −17.221 | −28.693 | 1.00 | 104.15 | C |
| ATOM | 2552 | CZ | TYR A | 346 | −6.896 | −17.013 | −29.136 | 1.00 | 108.30 | C |
| ATOM | 2553 | OH | TYR A | 346 | −7.901 | −17.861 | −28.748 | 1.00 | 108.30 | O |
| ATOM | 2554 | CE2 | TYR A | 346 | −7.176 | −15.963 | −29.970 | 1.00 | 106.91 | C |
| ATOM | 2555 | CD2 | TYR A | 346 | −6.165 | −15.118 | −30.357 | 1.00 | 102.63 | C |
| ATOM | 2556 | C | TYR A | 346 | −3.533 | −13.140 | −28.179 | 1.00 | 75.13 | C |
| ATOM | 2557 | O | TYR A | 346 | −3.711 | −13.541 | −27.053 | 1.00 | 71.17 | O |
| ATOM | 2558 | N | VAL A | 347 | −3.878 | −11.941 | −28.600 | 1.00 | 69.66 | N |
| ATOM | 2559 | CA | VAL A | 347 | −4.451 | −10.905 | −27.791 | 1.00 | 68.07 | C |
| ATOM | 2560 | CB | VAL A | 347 | −3.574 | −9.650 | −27.907 | 1.00 | 72.57 | C |
| ATOM | 2561 | CG1 | VAL A | 347 | −4.227 | −8.458 | −27.217 | 1.00 | 76.82 | C |
| ATOM | 2562 | CG2 | VAL A | 347 | −2.170 | −9.915 | −27.377 | 1.00 | 72.10 | C |
| ATOM | 2563 | C | VAL A | 347 | −5.829 | −10.552 | −28.334 | 1.00 | 64.27 | C |
| ATOM | 2564 | O | VAL A | 347 | −5.992 | −10.384 | −29.519 | 1.00 | 65.70 | O |
| ATOM | 2565 | N | VAL A | 348 | −6.810 | −10.411 | −27.464 | 1.00 | 64.12 | N |
| ATOM | 2566 | CA | VAL A | 348 | −8.149 | −10.003 | −27.865 | 1.00 | 65.78 | C |
| ATOM | 2567 | CB | VAL A | 348 | −9.158 | −11.123 | −27.629 | 1.00 | 63.09 | C |
| ATOM | 2568 | CG1 | VAL A | 348 | −10.500 | −10.769 | −28.261 | 1.00 | 64.52 | C |
| ATOM | 2569 | CG2 | VAL A | 348 | −8.610 | −12.392 | −28.208 | 1.00 | 64.72 | C |
| ATOM | 2570 | C | VAL A | 348 | −8.574 | −8.774 | −27.055 | 1.00 | 67.54 | C |
| ATOM | 2571 | O | VAL A | 348 | −8.309 | −8.719 | −25.834 | 1.00 | 68.93 | O |
| ATOM | 2572 | N | ALA A | 349 | −9.253 | −7.822 | −27.717 | 1.00 | 61.05 | N |
| ATOM | 2573 | CA | ALA A | 349 | −9.685 | −6.625 | −27.037 | 1.00 | 59.92 | C |
| ATOM | 2574 | CB | ALA A | 349 | −9.777 | −5.442 | −27.963 | 1.00 | 60.69 | C |
| ATOM | 2575 | C | ALA A | 349 | −11.013 | −6.963 | −26.417 | 1.00 | 62.37 | C |
| ATOM | 2576 | O | ALA A | 349 | −11.974 | −7.329 | −27.111 | 1.00 | 58.75 | O |
| ATOM | 2577 | N | MET A | 350 | −10.992 | −6.913 | −25.083 | 1.00 | 65.74 | N |
| ATOM | 2578 | CA | MET A | 350 | −12.144 | −7.111 | −24.238 | 1.00 | 64.53 | C |
| ATOM | 2579 | CB | MET A | 350 | −11.728 | −7.473 | −22.839 | 1.00 | 66.75 | C |
| ATOM | 2580 | CG | MET A | 350 | −11.084 | −8.814 | −22.673 | 1.00 | 71.70 | C |
| ATOM | 2581 | SD | MET A | 350 | −10.666 | −8.963 | −20.927 | 1.00 | 80.65 | S |
| ATOM | 2582 | CE | MET A | 350 | −12.215 | −8.606 | −20.043 | 1.00 | 77.57 | C |
| ATOM | 2583 | C | MET A | 350 | −12.955 | −5.853 | −24.089 | 1.00 | 60.99 | C |
| ATOM | 2584 | O | MET A | 350 | −14.147 | −5.911 | −24.144 | 1.00 | 65.38 | O |
| ATOM | 2585 | N | GLU A | 351 | −12.337 | −4.721 | −23.822 | 1.00 | 59.79 | N |
| ATOM | 2586 | CA | GLU A | 351 | −13.116 | −3.518 | −23.599 | 1.00 | 59.85 | C |
| ATOM | 2587 | CB | GLU A | 351 | −13.456 | −3.423 | −22.119 | 1.00 | 63.56 | C |
| ATOM | 2588 | CG | GLU A | 351 | −14.909 | −3.114 | −21.833 | 1.00 | 70.04 | C |
| ATOM | 2589 | CD | GLU A | 351 | −15.061 | −2.220 | −20.616 | 1.00 | 77.63 | C |
| ATOM | 2590 | OE1 | GLU A | 351 | −14.570 | −2.625 | −19.531 | 1.00 | 76.13 | O |
| ATOM | 2591 | OE2 | GLU A | 351 | −15.645 | −1.105 | −20.762 | 1.00 | 85.40 | O |
| ATOM | 2592 | C | GLU A | 351 | −12.367 | −2.280 | −24.084 | 1.00 | 56.70 | C |
| ATOM | 2593 | O | GLU A | 351 | −11.139 | −2.268 | −24.134 | 1.00 | 52.87 | O |
| ATOM | 2594 | N | THR A | 352 | −13.117 | −1.246 | −24.440 | 1.00 | 54.88 | N |
| ATOM | 2595 | CA | THR A | 352 | −12.531 | 0.038 | −24.866 | 1.00 | 52.99 | C |
| ATOM | 2596 | CB | THR A | 352 | −12.903 | 0.307 | −26.318 | 1.00 | 52.40 | C |
| ATOM | 2597 | OG1 | THR A | 352 | −12.049 | −0.468 | −27.131 | 1.00 | 49.67 | O |
| ATOM | 2598 | CG2 | THR A | 352 | −12.718 | 1.740 | −26.689 | 1.00 | 54.51 | C |
| ATOM | 2599 | C | THR A | 352 | −12.976 | 1.240 | −24.048 | 1.00 | 49.29 | C |
| ATOM | 2600 | O | THR A | 352 | −14.145 | 1.457 | −23.845 | 1.00 | 51.07 | O |
| ATOM | 2601 | N | PHE A | 353 | −12.042 | 2.075 | −23.645 | 1.00 | 46.56 | N |
| ATOM | 2602 | CA | PHE A | 353 | −12.431 | 3.334 | −23.040 | 1.00 | 43.42 | C |
| ATOM | 2603 | CB | PHE A | 353 | −11.839 | 3.417 | −21.678 | 1.00 | 42.07 | C |
| ATOM | 2604 | CG | PHE A | 353 | −11.771 | 2.132 | −20.937 | 1.00 | 40.28 | C |
| ATOM | 2605 | CD1 | PHE A | 353 | −12.803 | 1.720 | −20.193 | 1.00 | 38.83 | C |
| ATOM | 2606 | CE1 | PHE A | 353 | −12.713 | 0.598 | −19.430 | 1.00 | 40.05 | C |
| ATOM | 2607 | CZ | PHE A | 353 | −11.567 | −0.137 | −19.402 | 1.00 | 42.05 | C |
| ATOM | 2608 | CE2 | PHE A | 353 | −10.485 | 0.273 | −20.135 | 1.00 | 42.61 | C |
| ATOM | 2609 | CD2 | PHE A | 353 | −10.595 | 1.415 | −20.896 | 1.00 | 43.10 | C |
| ATOM | 2610 | C | PHE A | 353 | −12.018 | 4.584 | −23.898 | 1.00 | 42.49 | C |
| ATOM | 2611 | O | PHE A | 353 | −10.876 | 4.676 | −24.395 | 1.00 | 39.84 | O |
| ATOM | 2612 | N | THR A | 354 | −12.943 | 5.537 | −24.040 | 1.00 | 37.58 | N |
| ATOM | 2613 | CA | THR A | 354 | −12.724 | 6.655 | −24.899 | 1.00 | 36.21 | C |
| ATOM | 2614 | CB | THR A | 354 | −13.961 | 7.527 | −24.890 | 1.00 | 37.56 | C |
| ATOM | 2615 | OG1 | THR A | 354 | −15.053 | 6.785 | −25.421 | 1.00 | 39.89 | O |
| ATOM | 2616 | CG2 | THR A | 354 | −13.793 | 8.778 | −25.729 | 1.00 | 38.21 | C |
| ATOM | 2617 | C | THR A | 354 | −11.544 | 7.535 | −24.506 | 1.00 | 36.71 | C |
| ATOM | 2618 | O | THR A | 354 | −11.316 | 7.869 | −23.358 | 1.00 | 37.28 | O |
| ATOM | 2619 | N | ASN A | 355 | −10.779 | 7.928 | −25.502 | 1.00 | 39.06 | N |
| ATOM | 2620 | CA | ASN A | 355 | −9.777 | 8.951 | −25.347 | 1.00 | 38.25 | C |
| ATOM | 2621 | CB | ASN A | 355 | −8.399 | 8.311 | −25.403 | 1.00 | 37.90 | C |
| ATOM | 2622 | CG | ASN A | 355 | −7.308 | 9.294 | −25.111 | 1.00 | 40.81 | C |

TABLE 6-continued

Atomic coordinates for CRBN:DDB1: Compound B (Human protein)

| ATOM | 2623 | OD1 | ASN A | 355 | −7.534 | 10.258 | −24.386 | 1.00 | 42.09 | O |
|---|---|---|---|---|---|---|---|---|---|---|
| ATOM | 2624 | ND2 | ASN A | 355 | −6.133 | 9.109 | −25.712 | 1.00 | 43.34 | N |
| ATOM | 2625 | C | ASN A | 355 | −9.972 | 9.955 | −26.489 | 1.00 | 39.59 | C |
| ATOM | 2626 | O | ASN A | 355 | −9.784 | 9.611 | −27.646 | 1.00 | 46.17 | O |
| ATOM | 2627 | N | LEU A | 356 | −10.369 | 11.172 | −26.194 | 1.00 | 37.81 | N |
| ATOM | 2628 | CA | LEU A | 356 | −10.488 | 12.165 | −27.221 | 1.00 | 38.50 | C |
| ATOM | 2629 | CB | LEU A | 356 | −11.313 | 13.318 | −26.750 | 1.00 | 42.71 | C |
| ATOM | 2630 | CG | LEU A | 356 | −12.603 | 12.976 | −26.084 | 1.00 | 44.96 | C |
| ATOM | 2631 | CD1 | LEU A | 356 | −13.367 | 14.254 | −25.952 | 1.00 | 46.46 | C |
| ATOM | 2632 | CD2 | LEU A | 356 | −13.330 | 12.036 | −26.987 | 1.00 | 45.61 | C |
| ATOM | 2633 | C | LEU A | 356 | −9.173 | 12.701 | −27.712 | 1.00 | 38.60 | C |
| ATOM | 2634 | O | LEU A | 356 | −8.997 | 12.975 | −28.871 | 1.00 | 38.13 | O |
| ATOM | 2635 | N | GLY A | 357 | −8.258 | 12.887 | −26.789 | 1.00 | 40.54 | N |
| ATOM | 2636 | CA | GLY A | 357 | −6.978 | 13.473 | −27.085 | 1.00 | 43.83 | C |
| ATOM | 2637 | C | GLY A | 357 | −6.052 | 12.622 | −27.874 | 1.00 | 45.92 | C |
| ATOM | 2638 | O | GLY A | 357 | −6.200 | 11.448 | −27.799 | 1.00 | 65.67 | O |
| ATOM | 2639 | N | PRO A | 358 | −5.049 | 13.178 | −28.663 | 1.00 | 44.09 | N |
| ATOM | 2640 | CA | PRO A | 358 | −4.935 | 14.635 | −28.674 | 1.00 | 42.14 | C |
| ATOM | 2641 | CB | PRO A | 358 | −3.648 | 14.876 | −29.425 | 1.00 | 42.08 | C |
| ATOM | 2642 | CG | PRO A | 358 | −2.898 | 13.626 | −29.369 | 1.00 | 42.41 | C |
| ATOM | 2643 | CD | PRO A | 358 | −3.963 | 12.665 | −29.599 | 1.00 | 44.11 | C |
| ATOM | 2644 | C | PRO A | 358 | −5.985 | 15.314 | −29.470 | 1.00 | 43.75 | C |
| ATOM | 2645 | O | PRO A | 358 | −6.323 | 14.793 | −30.481 | 1.00 | 48.07 | O |
| ATOM | 2646 | N | ILE A | 359 | −6.462 | 16.471 | −29.055 | 1.00 | 43.15 | N |
| ATOM | 2647 | CA | ILE A | 359 | −7.426 | 17.179 | −29.842 | 1.00 | 39.85 | C |
| ATOM | 2648 | CB | ILE A | 359 | −8.379 | 17.965 | −28.999 | 1.00 | 39.23 | C |
| ATOM | 2649 | CG1 | ILE A | 359 | −9.223 | 17.002 | −28.191 | 1.00 | 39.55 | C |
| ATOM | 2650 | CD1 | ILE A | 359 | −10.444 | 17.631 | −27.596 | 1.00 | 40.77 | C |
| ATOM | 2651 | CG2 | ILE A | 359 | −9.236 | 18.827 | −29.885 | 1.00 | 39.14 | C |
| ATOM | 2652 | C | ILE A | 359 | −6.443 | 18.040 | −30.529 | 1.00 | 38.12 | C |
| ATOM | 2653 | O | ILE A | 359 | −5.661 | 18.711 | −29.915 | 1.00 | 39.28 | O |
| ATOM | 2654 | N | VAL A | 360 | −6.469 | 17.985 | −31.832 | 1.00 | 38.33 | N |
| ATOM | 2655 | CA | VAL A | 360 | −5.453 | 18.596 | −32.657 | 1.00 | 37.10 | C |
| ATOM | 2656 | CB | VAL A | 360 | −4.804 | 17.446 | −33.488 | 1.00 | 36.52 | C |
| ATOM | 2657 | CG1 | VAL A | 360 | −4.541 | 17.821 | −34.931 | 1.00 | 38.72 | C |
| ATOM | 2658 | CG2 | VAL A | 360 | −3.545 | 16.922 | −32.805 | 1.00 | 34.28 | C |
| ATOM | 2659 | C | VAL A | 360 | −6.105 | 19.688 | −33.469 | 1.00 | 36.00 | C |
| ATOM | 2660 | O | VAL A | 360 | −5.442 | 20.513 | −33.991 | 1.00 | 37.24 | O |
| ATOM | 2661 | N | ASP A | 361 | −7.404 | 19.606 | −33.656 | 1.00 | 36.48 | N |
| ATOM | 2662 | CA | ASP A | 361 | −8.169 | 20.673 | −34.189 | 1.00 | 39.51 | C |
| ATOM | 2663 | CB | ASP A | 361 | −7.989 | 20.767 | −35.695 | 1.00 | 43.84 | C |
| ATOM | 2664 | CG | ASP A | 361 | −8.640 | 22.012 | −36.289 | 1.00 | 50.76 | C |
| ATOM | 2665 | OD1 | ASP A | 361 | −9.077 | 22.926 | −35.517 | 1.00 | 50.70 | O |
| ATOM | 2666 | OD2 | ASP A | 361 | −8.680 | 22.090 | −37.552 | 1.00 | 57.16 | O |
| ATOM | 2667 | C | ASP A | 361 | −9.592 | 20.275 | −33.854 | 1.00 | 39.87 | C |
| ATOM | 2668 | O | ASP A | 361 | −9.814 | 19.101 | −33.472 | 1.00 | 37.54 | O |
| ATOM | 2669 | N | MET A | 362 | −10.531 | 21.228 | −33.950 | 1.00 | 39.37 | N |
| ATOM | 2670 | CA | MET A | 362 | −11.932 | 20.95 | −33.763 | 1.00 | 43.33 | C |
| ATOM | 2671 | CB | MET A | 362 | −12.298 | 20.810 | −32.272 | 1.00 | 50.53 | C |
| ATOM | 2672 | CG | MET A | 362 | −12.326 | 22.090 | −31.405 | 1.00 | 51.75 | C |
| ATOM | 2673 | SD | MET A | 362 | −12.043 | 21.718 | −29.649 | 1.00 | 52.40 | S |
| ATOM | 2674 | CE | MET A | 362 | −12.592 | 23.233 | −28.901 | 1.00 | 56.09 | C |
| ATOM | 2675 | C | MET A | 362 | −12.771 | 21.963 | −34.404 | 1.00 | 43.96 | C |
| ATOM | 2676 | O | MET A | 362 | −12.250 | 22.924 | −34.846 | 1.00 | 54.03 | O |
| ATOM | 2677 | N | CYS A | 363 | −14.075 | 21.763 | −34.479 | 1.00 | 44.09 | N |
| ATOM | 2678 | CA | CYS A | 363 | −14.972 | 22.803 | −34.931 | 1.00 | 44.37 | C |
| ATOM | 2679 | CB | CYS A | 363 | −15.001 | 22.793 | −36.431 | 1.00 | 46.09 | C |
| ATOM | 2680 | SG | CYS A | 363 | −16.005 | 21.456 | −37.078 | 1.00 | 49.90 | S |
| ATOM | 2681 | C | CYS A | 363 | −16.358 | 22.544 | −34.362 | 1.00 | 44.67 | C |
| ATOM | 2682 | O | CYS A | 363 | −16.659 | 21.438 | −33.912 | 1.00 | 39.70 | O |
| ATOM | 2683 | N | VAL A | 364 | −17.193 | 23.579 | −34.344 | 1.00 | 49.16 | N |
| ATOM | 2684 | CA | VAL A | 364 | −18.525 | 23.473 | −33.698 | 1.00 | 51.56 | C |
| ATOM | 2685 | CB | VAL A | 364 | −18.850 | 24.615 | −32.679 | 1.00 | 50.09 | C |
| ATOM | 2686 | CG1 | VAL A | 364 | −20.161 | 24.308 | −31.931 | 1.00 | 49.21 | C |
| ATOM | 2687 | CG2 | VAL A | 364 | −17.724 | 24.812 | −31.660 | 1.00 | 48.48 | C |
| ATOM | 2688 | C | VAL A | 364 | −19.560 | 23.544 | −34.761 | 1.00 | 52.31 | C |
| ATOM | 2689 | O | VAL A | 364 | −19.527 | 24.467 | −35.558 | 1.00 | 59.25 | O |
| ATOM | 2690 | N | VAL A | 365 | −20.485 | 22.616 | −34.762 | 1.00 | 51.40 | N |
| ATOM | 2691 | CA | VAL A | 365 | −21.434 | 22.552 | −35.827 | 1.00 | 57.18 | C |
| ATOM | 2692 | CB | VAL A | 365 | −21.207 | 21.312 | −36.729 | 1.00 | 59.23 | C |
| ATOM | 2693 | CG1 | VAL A | 365 | −22.373 | 21.101 | −37.703 | 1.00 | 59.50 | C |
| ATOM | 2694 | CG2 | VAL A | 365 | −19.884 | 21.411 | −37.483 | 1.00 | 58.17 | C |
| ATOM | 2695 | C | VAL A | 365 | −22.715 | 22.338 | −35.147 | 1.00 | 66.17 | C |
| ATOM | 2696 | O | VAL A | 365 | −22.826 | 21.412 | −34.332 | 1.00 | 74.90 | O |
| ATOM | 2697 | N | ASP A | 366 | −23.697 | 23.148 | −35.503 | 1.00 | 73.27 | N |
| ATOM | 2698 | CA | ASP A | 366 | −25.088 | 22.842 | −35.189 | 1.00 | 77.82 | C |
| ATOM | 2699 | CB | ASP A | 366 | −25.834 | 24.157 | −35.334 | 1.00 | 82.27 | C |
| ATOM | 2700 | CG | ASP A | 366 | −27.244 | 24.090 | −34.854 | 1.00 | 88.15 | C |

TABLE 6-continued

Atomic coordinates for CRBN:DDB1: Compound B (Human protein)

| ATOM | 2701 | OD1 | ASP A | 366 | −27.733 | 22.961 | −34.504 | 1.00 | 87.29 | O |
|---|---|---|---|---|---|---|---|---|---|---|
| ATOM | 2702 | OD2 | ASP A | 366 | −27.860 | 25.197 | −34.834 | 1.00 | 87.59 | O |
| ATOM | 2703 | C | ASP A | 366 | −25.665 | 21.678 | −36.116 | 1.00 | 84.13 | C |
| ATOM | 2704 | O | ASP A | 366 | −26.476 | 21.910 | −37.023 | 1.00 | 83.10 | O |
| ATOM | 2705 | N | LEU A | 367 | −25.247 | 20.445 | −35.873 | 1.00 | 91.96 | N |
| ATOM | 2706 | CA | LEU A | 367 | −25.676 | 19.340 | −36.723 | 1.00 | 84.19 | C |
| ATOM | 2707 | CB | LEU A | 367 | −24.960 | 18.066 | −36.306 | 1.00 | 76.55 | C |
| ATOM | 2708 | CG | LEU A | 367 | −23.507 | 17.935 | −36.696 | 1.00 | 69.60 | C |
| ATOM | 2709 | CD1 | LEU A | 367 | −23.005 | 16.609 | −36.201 | 1.00 | 69.36 | C |
| ATOM | 2710 | CD2 | LEU A | 367 | −23.366 | 18.011 | −38.191 | 1.00 | 63.88 | C |
| ATOM | 2711 | C | LEU A | 367 | −27.140 | 18.997 | −36.805 | 1.00 | 85.99 | C |
| ATOM | 2712 | O | LEU A | 367 | −27.651 | 18.827 | −37.892 | 1.00 | 90.77 | O |
| ATOM | 2713 | N | GLU A | 368 | −27.830 | 18.908 | −35.684 | 1.00 | 83.96 | N |
| ATOM | 2714 | CA | GLU A | 368 | −29.240 | 18.553 | −35.723 | 1.00 | 83.07 | C |
| ATOM | 2715 | CB | GLU A | 368 | −29.711 | 18.018 | −34.386 | 1.00 | 80.27 | C |
| ATOM | 2716 | CG | GLU A | 368 | −28.859 | 16.872 | −33.888 | 1.00 | 85.93 | C |
| ATOM | 2717 | CD | GLU A | 368 | −29.055 | 15.604 | −34.680 | 1.00 | 88.52 | C |
| ATOM | 2718 | OE1 | GLU A | 368 | −30.176 | 15.376 | −35.144 | 1.00 | 97.45 | O |
| ATOM | 2719 | OE2 | GLU A | 368 | −28.098 | 14.828 | −34.833 | 1.00 | 81.36 | O |
| ATOM | 2720 | C | GLU A | 368 | −30.085 | 19.704 | −36.201 | 1.00 | 86.80 | C |
| ATOM | 2721 | O | GLU A | 368 | −31.254 | 19.551 | −36.468 | 1.00 | 91.87 | O |
| ATOM | 2722 | N | ARG A | 369 | −29.479 | 20.872 | −36.285 | 1.00 | 94.00 | N |
| ATOM | 2723 | CA | ARG A | 369 | −30.185 | 22.057 | −36.722 | 1.00 | 94.30 | C |
| ATOM | 2724 | CB | ARG A | 369 | −30.969 | 21.761 | −37.991 | 1.00 | 83.04 | C |
| ATOM | 2725 | C | ARG A | 369 | −31.122 | 22.496 | −35.620 | 1.00 | 96.90 | C |
| ATOM | 2726 | O | ARG A | 369 | −32.026 | 23.278 | −35.843 | 1.00 | 100.95 | O |
| ATOM | 2727 | N | GLN A | 370 | −30.896 | 21.988 | −34.423 | 1.00 | 92.97 | N |
| ATOM | 2728 | CA | GLN A | 370 | −31.753 | 22.302 | −33.310 | 1.00 | 95.37 | C |
| ATOM | 2729 | CB | GLN A | 370 | −31.798 | 21.107 | −32.357 | 1.00 | 96.51 | C |
| ATOM | 2730 | CG | GLN A | 370 | −31.752 | 19.772 | −33.080 | 1.00 | 102.45 | C |
| ATOM | 2731 | CD | GLN A | 370 | −32.229 | 18.593 | −32.251 | 1.00 | 103.60 | C |
| ATOM | 2732 | OE1 | GLN A | 370 | −31.646 | 18.261 | −31.229 | 1.00 | 100.79 | O |
| ATOM | 2733 | NE2 | GLN A | 370 | −33.280 | 17.935 | −32.715 | 1.00 | 101.75 | N |
| ATOM | 2734 | C | GLN A | 370 | −31.338 | 23.546 | −32.563 | 1.00 | 95.23 | C |
| ATOM | 2735 | O | GLN A | 370 | −32.000 | 23.935 | −31.622 | 1.00 | 97.85 | O |
| ATOM | 2736 | N | GLY A | 371 | −30.245 | 24.175 | −32.961 | 1.00 | 97.69 | N |
| ATOM | 2737 | CA | GLY A | 371 | −29.760 | 25.377 | −32.203 | 1.00 | 92.85 | C |
| ATOM | 2738 | C | GLY A | 371 | −28.922 | 24.985 | −30.979 | 1.00 | 87.75 | C |
| ATOM | 2739 | O | GLY A | 371 | −29.048 | 25.563 | −29.900 | 1.00 | 89.04 | O |
| ATOM | 2740 | N | GLN A | 372 | −28.076 | 23.977 | −31.184 | 1.00 | 83.99 | N |
| ATOM | 2741 | CA | GLN A | 372 | −27.375 | 23.200 | −30.162 | 1.00 | 79.69 | C |
| ATOM | 2742 | CB | GLN A | 372 | −28.246 | 21.979 | −29.703 | 1.00 | 87.01 | C |
| ATOM | 2743 | CG | GLN A | 372 | −27.566 | 20.681 | −29.205 | 1.00 | 92.32 | C |
| ATOM | 2744 | CD | GLN A | 372 | −26.702 | 20.819 | −27.925 | 1.00 | 98.80 | C |
| ATOM | 2745 | OE1 | GLN A | 372 | −25.537 | 20.356 | −27.876 | 1.00 | 90.53 | O |
| ATOM | 2746 | NE2 | GLN A | 372 | −27.277 | 21.429 | −26.875 | 1.00 | 103.41 | N |
| ATOM | 2747 | C | GLN A | 372 | −26.127 | 22.778 | −30.905 | 1.00 | 69.98 | C |
| ATOM | 2748 | O | GLN A | 372 | −26.200 | 21.960 | −31.815 | 1.00 | 78.42 | O |
| ATOM | 2749 | N | GLY A | 373 | −25.003 | 23.394 | −30.592 | 1.00 | 62.55 | N |
| ATOM | 2750 | CA | GLY A | 373 | −23.713 | 22.994 | −31.165 | 1.00 | 60.02 | C |
| ATOM | 2751 | C | GLY A | 373 | −23.132 | 21.649 | −30.714 | 1.00 | 55.40 | C |
| ATOM | 2752 | O | GLY A | 373 | −23.336 | 21.189 | −29.594 | 1.00 | 59.37 | O |
| ATOM | 2753 | N | GLN A | 374 | −22.427 | 21.006 | −31.624 | 1.00 | 52.61 | N |
| ATOM | 2754 | CA | GLN A | 374 | −21.787 | 19.734 | −31.394 | 1.00 | 50.82 | C |
| ATOM | 2755 | CB | GLN A | 374 | −22.472 | 18.612 | −32.210 | 1.00 | 52.84 | C |
| ATOM | 2756 | CG | GLN A | 374 | −23.878 | 18.275 | −31.707 | 1.00 | 58.19 | C |
| ATOM | 2757 | CD | GLN A | 374 | −24.497 | 16.917 | −32.166 | 1.00 | 67.74 | C |
| ATOM | 2758 | OE1 | GLN A | 374 | −24.533 | 16.578 | −33.359 | 1.00 | 73.65 | O |
| ATOM | 2759 | NE2 | GLN A | 374 | −25.069 | 16.173 | −31.205 | 1.00 | 73.18 | N |
| ATOM | 2760 | C | GLN A | 374 | −20.334 | 19.992 | −31.767 | 1.00 | 46.42 | C |
| ATOM | 2761 | O | GLN A | 374 | −20.031 | 20.778 | −32.655 | 1.00 | 46.18 | O |
| ATOM | 2762 | N | LEU A | 375 | −19.423 | 19.398 | −31.046 | 1.00 | 44.17 | N |
| ATOM | 2763 | CA | LEU A | 375 | −18.035 | 19.671 | −31.282 | 1.00 | 47.95 | C |
| ATOM | 2764 | CB | LEU A | 375 | −17.253 | 19.741 | −29.955 | 1.00 | 52.03 | C |
| ATOM | 2765 | CG | LEU A | 375 | −15.974 | 20.591 | −29.863 | 1.00 | 54.67 | C |
| ATOM | 2766 | CD1 | LEU A | 375 | −16.396 | 22.031 | −30.083 | 1.00 | 56.56 | C |
| ATOM | 2767 | CD2 | LEU A | 375 | −15.220 | 20.423 | −28.540 | 1.00 | 53.50 | C |
| ATOM | 2768 | C | LEU A | 375 | −17.621 | 18.481 | −32.093 | 1.00 | 46.56 | C |
| ATOM | 2769 | O | LEU A | 375 | −18.135 | 17.400 | −31.859 | 1.00 | 52.53 | O |
| ATOM | 2770 | N | VAL A | 376 | −16.741 | 18.673 | −33.060 | 1.00 | 42.64 | N |
| ATOM | 2771 | CA | VAL A | 376 | −16.221 | 17.576 | −33.830 | 1.00 | 43.47 | C |
| ATOM | 2772 | CB | VAL A | 376 | −16.713 | 17.607 | −35.302 | 1.00 | 44.77 | C |
| ATOM | 2773 | CG1 | VAL A | 376 | −16.144 | 16.392 | −36.057 | 1.00 | 46.62 | C |
| ATOM | 2774 | CG2 | VAL A | 376 | −18.244 | 17.593 | −35.391 | 1.00 | 42.74 | C |
| ATOM | 2775 | C | VAL A | 376 | −14.722 | 17.725 | −33.793 | 1.00 | 42.47 | C |
| ATOM | 2776 | O | VAL A | 376 | −14.240 | 18.757 | −34.174 | 1.00 | 44.90 | O |
| ATOM | 2777 | N | THR A | 377 | −13.980 | 16.721 | −33.367 | 1.00 | 39.90 | N |
| ATOM | 2778 | CA | THR A | 377 | −12.557 | 16.917 | −33.094 | 1.00 | 41.02 | C |

TABLE 6-continued

Atomic coordinates for CRBN:DDB1: Compound B (Human protein)

| ATOM | 2779 | CB | THR A | 377 | −12.186 | 16.449 | −31.646 | 1.00 | 40.30 | C |
|---|---|---|---|---|---|---|---|---|---|---|
| ATOM | 2780 | OG1 | THR A | 377 | −12.416 | 15.034 | −31.472 | 1.00 | 38.91 | O |
| ATOM | 2781 | CG2 | THR A | 377 | −12.956 | 17.210 | −30.644 | 1.00 | 39.17 | C |
| ATOM | 2782 | C | THR A | 377 | −11.710 | 16.091 | −34.012 | 1.00 | 42.15 | C |
| ATOM | 2783 | O | THR A | 377 | −12.054 | 14.955 | −34.251 | 1.00 | 48.51 | O |
| ATOM | 2784 | N | CYS A | 378 | −10.596 | 16.608 | −34.502 | 1.00 | 40.26 | N |
| ATOM | 2785 | CA | CYS A | 378 | −9.571 | 15.711 | −34.986 | 1.00 | 41.41 | C |
| ATOM | 2786 | CB | CYS A | 378 | −8.586 | 16.463 | −35.869 | 1.00 | 42.92 | C |
| ATOM | 2787 | SG | CYS A | 378 | −9.370 | 17.123 | −37.319 | 1.00 | 44.09 | S |
| ATOM | 2788 | C | CYS A | 378 | −8.821 | 15.111 | −33.782 | 1.00 | 41.84 | C |
| ATOM | 2789 | O | CYS A | 378 | −7.999 | 15.797 | −33.158 | 1.00 | 45.37 | O |
| ATOM | 2790 | N | SER A | 379 | −9.057 | 13.839 | −33.472 | 1.00 | 39.84 | N |
| ATOM | 2791 | CA | SER A | 379 | −8.377 | 13.175 | −32.335 | 1.00 | 38.82 | C |
| ATOM | 2792 | CB | SER A | 379 | −9.409 | 12.654 | −31.382 | 1.00 | 37.14 | C |
| ATOM | 2793 | OG | SER A | 379 | −10.123 | 13.748 | −30.917 | 1.00 | 38.65 | O |
| ATOM | 2794 | C | SER A | 379 | −7.409 | 12.033 | −32.683 | 1.00 | 38.08 | C |
| ATOM | 2795 | O | SER A | 379 | −7.628 | 11.277 | −33.616 | 1.00 | 43.04 | O |
| ATOM | 2796 | N | GLY A | 380 | −6.381 | 11.886 | −31.887 | 1.00 | 34.85 | N |
| ATOM | 2797 | CA | GLY A | 380 | −5.469 | 10.795 | −32.039 | 1.00 | 34.66 | C |
| ATOM | 2798 | C | GLY A | 380 | −4.435 | 10.888 | −33.092 | 1.00 | 37.46 | C |
| ATOM | 2799 | O | GLY A | 380 | −4.279 | 11.894 | −33.725 | 1.00 | 43.00 | O |
| ATOM | 2800 | N | ALA A | 381 | −3.712 | 9.803 | −33.266 | 1.00 | 39.92 | N |
| ATOM | 2801 | CA | ALA A | 381 | −2.701 | 9.764 | −34.259 | 1.00 | 42.37 | C |
| ATOM | 2802 | CB | ALA A | 381 | −1.508 | 10.455 | −33.687 | 1.00 | 42.11 | C |
| ATOM | 2803 | C | ALA A | 381 | −2.312 | 8.363 | −34.670 | 1.00 | 43.33 | C |
| ATOM | 2804 | O | ALA A | 381 | −2.487 | 7.445 | −33.923 | 1.00 | 45.50 | O |
| ATOM | 2805 | N | PHE A | 382 | −1.774 | 8.205 | −35.863 | 1.00 | 42.32 | N |
| ATOM | 2806 | CA | PHE A | 382 | −1.206 | 6.956 | −36.328 | 1.00 | 43.08 | C |
| ATOM | 2807 | CB | PHE A | 382 | 0.067 | 6.729 | −35.506 | 1.00 | 48.59 | C |
| ATOM | 2808 | CG | PHE A | 382 | 0.995 | 7.871 | −35.463 | 1.00 | 54.08 | C |
| ATOM | 2809 | CD1 | PHE A | 382 | 1.100 | 8.724 | −36.502 | 1.00 | 54.29 | C |
| ATOM | 2810 | CE1 | PHE A | 382 | 1.984 | 9.767 | −36.451 | 1.00 | 57.50 | C |
| ATOM | 2811 | CZ | PHE A | 382 | 2.789 | 9.941 | −35.357 | 1.00 | 58.66 | C |
| ATOM | 2812 | CE2 | PHE A | 382 | 2.704 | 9.067 | −34.319 | 1.00 | 61.85 | C |
| ATOM | 2813 | CD2 | PHE A | 382 | 1.817 | 8.034 | −34.385 | 1.00 | 59.79 | C |
| ATOM | 2814 | C | PHE A | 382 | −1.963 | 5.615 | −36.360 | 1.00 | 38.66 | C |
| ATOM | 2815 | O | PHE A | 382 | −1.354 | 4.577 | −36.175 | 1.00 | 35.23 | O |
| ATOM | 2816 | N | LYS A | 383 | −3.236 | 5.616 | −36.665 | 1.00 | 36.14 | N |
| ATOM | 2817 | CA | LYS A | 383 | −4.119 | 4.433 | −36.729 | 1.00 | 39.41 | C |
| ATOM | 2818 | CB | LYS A | 383 | −3.486 | 3.060 | −36.625 | 1.00 | 43.86 | C |
| ATOM | 2819 | CG | LYS A | 383 | −3.027 | 2.672 | −35.257 | 1.00 | 45.25 | C |
| ATOM | 2820 | CD | LYS A | 383 | −1.932 | 1.647 | −35.339 | 1.00 | 47.22 | C |
| ATOM | 2821 | CE | LYS A | 383 | −1.810 | 0.891 | −34.041 | 1.00 | 49.93 | C |
| ATOM | 2822 | NZ | LYS A | 383 | −3.125 | 0.383 | −33.603 | 1.00 | 51.99 | N |
| ATOM | 2823 | C | LYS A | 383 | −5.047 | 4.644 | −35.639 | 1.00 | 40.67 | C |
| ATOM | 2824 | O | LYS A | 383 | −6.201 | 4.276 | −35.724 | 1.00 | 41.56 | O |
| ATOM | 2825 | N | GLU A | 384 | −4.588 | 5.318 | −34.615 | 1.00 | 40.09 | N |
| ATOM | 2826 | CA | GLU A | 384 | −5.623 | 5.711 | −33.700 | 1.00 | 39.03 | C |
| ATOM | 2827 | CB | GLU A | 384 | −5.002 | 5.953 | −32.350 | 1.00 | 40.35 | C |
| ATOM | 2828 | CG | GLU A | 384 | −4.008 | 4.889 | −31.920 | 1.00 | 41.82 | C |
| ATOM | 2829 | CD | GLU A | 384 | −4.689 | 3.602 | −31.657 | 1.00 | 45.20 | C |
| ATOM | 2830 | OE1 | GLU A | 384 | −5.959 | 3.662 | −31.518 | 1.00 | 47.96 | O |
| ATOM | 2831 | OE2 | GLU A | 384 | −3.954 | 2.563 | −31.589 | 1.00 | 48.52 | O |
| ATOM | 2832 | C | GLU A | 384 | −6.380 | 6.959 | −34.134 | 1.00 | 37.87 | C |
| ATOM | 2833 | O | GLU A | 384 | −7.317 | 7.373 | −33.457 | 1.00 | 39.98 | O |
| ATOM | 2834 | N | GLY A | 385 | −6.017 | 7.554 | −35.241 | 1.00 | 35.98 | N |
| ATOM | 2835 | CA | GLY A | 385 | −6.668 | 8.776 | −35.626 | 1.00 | 36.91 | C |
| ATOM | 2836 | C | GLY A | 385 | −8.138 | 8.584 | −35.694 | 1.00 | 34.99 | C |
| ATOM | 2837 | O | GLY A | 385 | −8.593 | 7.532 | −36.008 | 1.00 | 38.57 | O |
| ATOM | 2838 | N | SER A | 386 | −8.880 | 9.602 | −35.332 | 1.00 | 33.17 | N |
| ATOM | 2839 | CA | SER A | 386 | −10.303 | 9.514 | −35.354 | 1.00 | 35.44 | C |
| ATOM | 2840 | CB | SER A | 386 | −10.781 | 8.776 | −34.141 | 1.00 | 36.69 | C |
| ATOM | 2841 | OG | SER A | 386 | −10.045 | 9.148 | −33.008 | 1.00 | 35.35 | O |
| ATOM | 2842 | C | SER A | 386 | −10.917 | 10.855 | −35.348 | 1.00 | 36.08 | C |
| ATOM | 2843 | O | SER A | 386 | −10.255 | 11.830 | −35.172 | 1.00 | 37.71 | O |
| ATOM | 2844 | N | LEU A | 387 | −12.209 | 10.888 | −35.551 | 1.00 | 37.39 | N |
| ATOM | 2845 | CA | LEU A | 387 | −12.957 | 12.100 | −35.504 | 1.00 | 38.75 | C |
| ATOM | 2846 | CB | LEU A | 387 | −13.801 | 12.287 | −36.737 | 1.00 | 41.50 | C |
| ATOM | 2847 | CG | LEU A | 387 | −13.206 | 12.727 | −38.058 | 1.00 | 44.78 | C |
| ATOM | 2848 | CD1 | LEU A | 387 | −14.325 | 13.008 | −39.021 | 1.00 | 44.26 | C |
| ATOM | 2849 | CD2 | LEU A | 387 | −12.373 | 13.960 | −37.893 | 1.00 | 46.34 | C |
| ATOM | 2850 | C | LEU A | 387 | −13.867 | 11.738 | −34.389 | 1.00 | 38.98 | C |
| ATOM | 2851 | O | LEU A | 387 | −14.208 | 10.610 | −34.260 | 1.00 | 40.01 | O |
| ATOM | 2852 | N | ARG A | 388 | −14.246 | 12.680 | −33.562 | 1.00 | 36.56 | N |
| ATOM | 2853 | CA | ARG A | 388 | −15.123 | 12.427 | −32.443 | 1.00 | 37.90 | C |
| ATOM | 2854 | CB | ARG A | 388 | −14.374 | 12.589 | −31.114 | 1.00 | 39.13 | C |
| ATOM | 2855 | CG | ARG A | 388 | −13.186 | 11.669 | −30.864 | 1.00 | 39.37 | C |
| ATOM | 2856 | CD | ARG A | 388 | −13.550 | 10.163 | −30.718 | 1.00 | 38.61 | C |

TABLE 6-continued

Atomic coordinates for CRBN:DDB1: Compound B (Human protein)

| ATOM | 2857 | NE  | ARG A | 388 | −12.323 | 9.363   | −30.889 | 1.00 | 37.91 | N |
|------|------|-----|-------|-----|---------|---------|---------|------|-------|---|
| ATOM | 2858 | CZ  | ARG A | 388 | −11.861 | 8.396   | −30.072 | 1.00 | 37.09 | C |
| ATOM | 2859 | NH1 | ARG A | 388 | −12.464 | 7.957   | −28.969 | 1.00 | 36.21 | N |
| ATOM | 2860 | NH2 | ARG A | 388 | −10.720 | 7.864   | −30.381 | 1.00 | 36.63 | N |
| ATOM | 2861 | C   | ARG A | 388 | −16.233 | 13.451  | −32.448 | 1.00 | 39.42 | C |
| ATOM | 2862 | O   | ARG A | 388 | −15.956 | 14.631  | −32.560 | 1.00 | 43.94 | O |
| ATOM | 2863 | N   | ILE A | 389 | −17.478 | 13.031  | −32.284 | 1.00 | 40.27 | N |
| ATOM | 2864 | CA  | ILE A | 389 | −18.599 | −13.936 | −32.285 | 1.00 | 40.58 | C |
| ATOM | 2865 | CB  | ILE A | 389 | −19.704 | 13.437  | −33.203 | 1.00 | 41.95 | C |
| ATOM | 2866 | CG1 | ILE A | 389 | −19.245 | 13.493  | −34.660 | 1.00 | 43.20 | C |
| ATOM | 2867 | CD1 | ILE A | 389 | −18.736 | −12.167 | −35.165 | 1.00 | 44.12 | C |
| ATOM | 2868 | CG2 | ILE A | 389 | −20.956 | 14.289  | −33.063 | 1.00 | 44.46 | C |
| ATOM | 2869 | C   | ILE A | 389 | −19.124 | 14.021  | −30.877 | 1.00 | 43.79 | C |
| ATOM | 2870 | O   | ILE A | 389 | −19.715 | 13.053  | −30.367 | 1.00 | 47.61 | O |
| ATOM | 2871 | N   | ILE A | 390 | −18.954 | 15.190  | −30.259 | 1.00 | 43.79 | N |
| ATOM | 2872 | CA  | ILE A | 390 | −19.303 | 15.380  | −28.873 | 1.00 | 43.78 | C |
| ATOM | 2873 | CB  | ILE A | 390 | −18.135 | 16.032  | −28.153 | 1.00 | 47.43 | C |
| ATOM | 2874 | CG1 | ILE A | 390 | −16.956 | 15.024  | −28.049 | 1.00 | 49.50 | C |
| ATOM | 2875 | CD1 | ILE A | 390 | −15.579 | 15.565  | −28.391 | 1.00 | 49.34 | C |
| ATOM | 2876 | CG2 | ILE A | 390 | −18.572 | 16.479  | −26.770 | 1.00 | 48.94 | C |
| ATOM | 2877 | C   | ILE A | 390 | −20.566 | 16.216  | −28.784 | 1.00 | 44.29 | C |
| ATOM | 2878 | O   | ILE A | 390 | −20.551 | 17.383  | −29.138 | 1.00 | 44.68 | O |
| ATOM | 2879 | N   | ARG A | 391 | −21.670 | 15.565  | −28.395 | 1.00 | 46.27 | N |
| ATOM | 2880 | CA  | ARG A | 391 | −22.967 | 16.182  | −28.070 | 1.00 | 43.98 | C |
| ATOM | 2881 | CB  | ARG A | 391 | −24.188 | 15.360  | −28.601 | 1.00 | 37.55 | C |
| ATOM | 2882 | C   | ARG A | 391 | −22.823 | 16.125  | −26.548 | 1.00 | 46.17 | C |
| ATOM | 2883 | O   | ARG A | 391 | −23.646 | 15.565  | −25.810 | 1.00 | 50.00 | O |
| ATOM | 2884 | N   | ASN A | 392 | −23.935 | 17.912  | −26.054 | 1.00 | 50.03 | N |
| ATOM | 2885 | CA  | ASN A | 392 | −24.393 | 17.904  | −24.672 | 1.00 | 51.00 | C |
| ATOM | 2886 | CB  | ASN A | 392 | −24.425 | 19.336  | −24.191 | 1.00 | 58.54 | C |
| ATOM | 2887 | CG  | ASN A | 392 | −24.510 | 19.452  | −22.714 | 1.00 | 67.59 | C |
| ATOM | 2888 | OD1 | ASN A | 392 | −25.217 | 18.687  | −22.069 | 1.00 | 79.77 | O |
| ATOM | 2889 | ND2 | ASN A | 392 | −23.786 | 20.420  | −22.152 | 1.00 | 74.32 | N |
| ATOM | 2890 | C   | ASN A | 392 | −25.796 | 17.332  | −24.633 | 1.00 | 47.21 | C |
| ATOM | 2891 | O   | ASN A | 392 | −26.570 | 17.605  | −25.491 | 1.00 | 48.52 | O |
| ATOM | 2892 | N   | GLY A | 393 | −26.158 | 16.564  | −23.635 | 1.00 | 47.29 | N |
| ATOM | 2893 | CA  | GLY A | 393 | −27.602 | 16.281  | −23.397 | 1.00 | 47.62 | C |
| ATOM | 2894 | C   | GLY A | 393 | −27.925 | 15.073  | −22.515 | 1.00 | 45.38 | C |
| ATOM | 2895 | O   | GLY A | 393 | −27.045 | 14.276  | −22.200 | 1.00 | 48.06 | O |
| ATOM | 2896 | N   | ILE A | 394 | −29.182 | 14.914  | −22.152 | 1.00 | 41.71 | N |
| ATOM | 2897 | CA  | ILE A | 394 | −29.613 | 13.644  | −21.593 | 1.00 | 43.78 | C |
| ATOM | 2898 | CB  | ILE A | 394 | −31.007 | 13.714  | −20.972 | 1.00 | 43.93 | C |
| ATOM | 2899 | CG1 | ILE A | 394 | −31.051 | 14.724  | −19.851 | 1.00 | 48.45 | C |
| ATOM | 2900 | CD1 | ILE A | 394 | −32.463 | 15.165  | −19.545 | 1.00 | 50.76 | C |
| ATOM | 2901 | CG2 | ILE A | 394 | −31.376 | 12.389  | −20.365 | 1.00 | 41.32 | C |
| ATOM | 2902 | C   | ILE A | 394 | −29.715 | 12.558  | −22.660 | 1.00 | 44.97 | C |
| ATOM | 2903 | O   | ILE A | 394 | −30.467 | 12.698  | −23.629 | 1.00 | 43.54 | O |
| ATOM | 2904 | N   | GLY A | 395 | −29.054 | 11.429  | −22.415 | 1.00 | 47.88 | N |
| ATOM | 2905 | CA  | GLY A | 395 | −29.134 | 10.280  | −23.326 | 1.00 | 47.81 | C |
| ATOM | 2906 | C   | GLY A | 395 | −30.145 | 9.213   | −22.959 | 1.00 | 46.75 | C |
| ATOM | 2907 | O   | GLY A | 395 | −30.520 | 9.091   | −21.816 | 1.00 | 43.97 | O |
| ATOM | 2908 | N   | ILE A | 396 | −30.532 | 8.406   | −23.948 | 1.00 | 49.98 | N |
| ATOM | 2909 | CA  | ILE A | 396 | −31.544 | 7.342   | −23.797 | 1.00 | 49.88 | C |
| ATOM | 2910 | CB  | ILE A | 396 | −32.700 | 7.517   | −24.827 | 1.00 | 48.95 | C |
| ATOM | 2911 | CG1 | ILE A | 396 | −33.411 | 8.839   | −24.622 | 1.00 | 50.86 | C |
| ATOM | 2912 | CD1 | ILE A | 396 | −34.040 | 9.041   | −23.257 | 1.00 | 54.66 | C |
| ATOM | 2913 | CG2 | ILE A | 396 | −33.705 | 6.378   | −24.764 | 1.00 | 48.76 | C |
| ATOM | 2914 | C   | ILE A | 396 | −30.917 | 5.992   | −24.049 | 1.00 | 47.36 | C |
| ATOM | 2915 | O   | ILE A | 396 | −30.493 | 5.743   | −25.157 | 1.00 | 44.29 | O |
| ATOM | 2916 | N   | HIS A | 397 | −30.924 | 5.109   | −23.055 | 1.00 | 49.01 | N |
| ATOM | 2917 | CA  | HIS A | 397 | −30.428 | 3.753   | −23.260 | 1.00 | 54.12 | C |
| ATOM | 2918 | CB  | HIS A | 397 | −29.963 | 3.122   | −21.952 | 1.00 | 57.44 | C |
| ATOM | 2919 | CG  | HIS A | 397 | −28.755 | 3.799   | −21.353 | 1.00 | 65.47 | C |
| ATOM | 2920 | ND1 | HIS A | 397 | −27.525 | 3.828   | −21.979 | 1.00 | 72.37 | N |
| ATOM | 2921 | CE1 | HIS A | 397 | −26.663 | 4.510   | −21.239 | 1.00 | 70.49 | C |
| ATOM | 2922 | NE2 | HIS A | 397 | −27.290 | 4.928   | −20.157 | 1.00 | 69.67 | N |
| ATOM | 2923 | CD2 | HIS A | 397 | −28.595 | 4.487   | −20.196 | 1.00 | 68.48 | C |
| ATOM | 2924 | C   | HIS A | 397 | −31.507 | 2.923   | −23.961 | 1.00 | 57.11 | C |
| ATOM | 2925 | O   | HIS A | 397 | −32.533 | 2.610   | −23.371 | 1.00 | 58.21 | O |
| ATOM | 2926 | N   | GLU A | 398 | −31.295 | 2.585   | −25.234 | 1.00 | 56.90 | N |
| ATOM | 2927 | CA  | GLU A | 398 | −32.367 | 1.978   | −26.002 | 1.00 | 56.45 | C |
| ATOM | 2928 | CB  | GLU A | 398 | −32.230 | 2.332   | −27.474 | 1.00 | 61.02 | C |
| ATOM | 2929 | CG  | GLU A | 398 | −32.508 | 3.794   | −27.735 | 1.00 | 68.07 | C |
| ATOM | 2930 | CD  | GLU A | 398 | −32.634 | 4.122   | −29.205 | 1.00 | 76.74 | C |
| ATOM | 2931 | OE1 | GLU A | 398 | −32.413 | 5.346   | −29.536 | 1.00 | 76.24 | O |
| ATOM | 2932 | OE2 | GLU A | 398 | −32.963 | 3.158   | −29.987 | 1.00 | 76.88 | O |
| ATOM | 2933 | C   | GLU A | 398 | −32.365 | 0.494   | −25.856 | 1.00 | 51.56 | C |
| ATOM | 2934 | O   | GLU A | 398 | −31.414 | −0.090  | −26.237 | 1.00 | 47.59 | O |

TABLE 6-continued

Atomic coordinates for CRBN:DDB1: Compound B (Human protein)

| ATOM | 2935 | N | HIS A | 399 | −33.446 | −0.124 | −25.387 | 1.00 | 52.81 | N |
|---|---|---|---|---|---|---|---|---|---|---|
| ATOM | 2936 | CA | HIS A | 399 | −33.499 | −1.592 | −25.283 | 1.00 | 54.95 | C |
| ATOM | 2937 | CB | HIS A | 399 | −33.947 | −2.002 | −23.888 | 1.00 | 57.72 | C |
| ATOM | 2938 | CG | HIS A | 399 | −33.268 | −1.225 | −22.815 | 1.00 | 58.73 | C |
| ATOM | 2939 | ND1 | HIS A | 399 | −33.941 | −0.701 | −21.736 | 1.00 | 59.46 | N |
| ATOM | 2940 | CE1 | HIS A | 399 | −33.098 | −0.047 | −20.963 | 1.00 | 57.52 | C |
| ATOM | 2941 | NE2 | HIS A | 399 | −31.911 | −0.081 | −21.535 | 1.00 | 60.76 | N |
| ATOM | 2942 | CD2 | HIS A | 399 | −31.987 | −0.819 | −22.692 | 1.00 | 58.34 | C |
| ATOM | 2943 | C | HIS A | 399 | −34.304 | −2.331 | −26.347 | 1.00 | 54.76 | C |
| ATOM | 2944 | O | HIS A | 399 | −33.963 | −3.474 | −26.660 | 1.00 | 60.69 | O |
| ATOM | 2945 | N | ALA A | 400 | −35.365 | −1.730 | −26.887 | 1.00 | 53.81 | N |
| ATOM | 2946 | CA | ALA A | 400 | −36.048 | −2.318 | −28.069 | 1.00 | 54.26 | C |
| ATOM | 2947 | CB | ALA A | 400 | −37.240 | −3.117 | −27.651 | 1.00 | 54.80 | C |
| ATOM | 2948 | C | ALA A | 400 | −36.484 | −1.325 | −29.123 | 1.00 | 54.67 | C |
| ATOM | 2949 | O | ALA A | 400 | −36.728 | −0.168 | −28.835 | 1.00 | 57.62 | O |
| ATOM | 2950 | N | SER A | 401 | −36.605 | −1.784 | −30.356 | 1.00 | 54.95 | N |
| ATOM | 2951 | CA | SER A | 401 | −37.100 | −0.919 | −31.406 | 1.00 | 54.51 | C |
| ATOM | 2952 | CB | SER A | 401 | −35.952 | −0.341 | −32.226 | 1.00 | 56.43 | C |
| ATOM | 2953 | OG | SER A | 401 | −36.324 | 0.941 | −32.715 | 1.00 | 60.38 | O |
| ATOM | 2954 | C | SER A | 401 | −38.108 | −1.646 | −32.278 | 1.00 | 52.98 | C |
| ATOM | 2955 | O | SER A | 401 | −38.049 | −2.895 | −32.453 | 1.00 | 54.21 | O |
| ATOM | 2956 | N | ILE A | 402 | −39.058 | −0.852 | −32.776 | 1.00 | 48.73 | N |
| ATOM | 2957 | CA | ILE A | 402 | −40.129 | −1.351 | −33.588 | 1.00 | 49.41 | C |
| ATOM | 2958 | CB | ILE A | 402 | −41.356 | −1.705 | −32.726 | 1.00 | 51.90 | C |
| ATOM | 2959 | CG1 | ILE A | 402 | −41.020 | −2.797 | −31.668 | 1.00 | 53.28 | C |
| ATOM | 2960 | CD1 | ILE A | 402 | −42.220 | −3.293 | −30.865 | 1.00 | 51.94 | C |
| ATOM | 2961 | CG2 | ILE A | 402 | −42.511 | −2.181 | −33.592 | 1.00 | 49.50 | C |
| ATOM | 2962 | C | ILE A | 402 | −40.521 | −0.304 | −34.596 | 1.00 | 51.01 | C |
| ATOM | 2963 | O | ILE A | 402 | −40.945 | 0.772 | −34.226 | 1.00 | 48.47 | O |
| ATOM | 2964 | N | ASP A | 403 | −40.343 | −0.638 | −35.872 | 1.00 | 59.00 | N |
| ATOM | 2965 | CA | ASP A | 403 | −40.975 | 0.017 | −37.037 | 1.00 | 63.12 | C |
| ATOM | 2966 | CB | ASP A | 403 | −40.353 | −0.584 | −38.327 | 1.00 | 65.78 | C |
| ATOM | 2967 | CG | ASP A | 403 | −40.928 | 0.015 | −39.634 | 1.00 | 75.46 | C |
| ATOM | 2968 | OD1 | ASP A | 403 | −41.555 | 1.129 | −39.648 | 1.00 | 86.91 | O |
| ATOM | 2969 | OD2 | ASP A | 403 | −40.730 | −0.647 | −40.680 | 1.00 | 73.92 | O |
| ATOM | 2970 | C | ASP A | 403 | −42.563 | −0.099 | −37.042 | 1.00 | 62.39 | C |
| ATOM | 2971 | O | ASP A | 403 | −43.134 | −1.204 | −37.195 | 1.00 | 57.59 | O |
| ATOM | 2972 | N | LEU A | 404 | −43.228 | 1.063 | −36.867 | 1.00 | 60.49 | N |
| ATOM | 2973 | CA | LEU A | 404 | −44.704 | 1.235 | −36.911 | 1.00 | 59.08 | C |
| ATOM | 2974 | CB | LEU A | 404 | −45.401 | 0.939 | −35.592 | 1.00 | 61.80 | C |
| ATOM | 2975 | CG | LEU A | 404 | −45.945 | −0.452 | −35.371 | 1.00 | 65.21 | C |
| ATOM | 2976 | CD1 | LEU A | 404 | −46.220 | −0.643 | −33.882 | 1.00 | 65.43 | C |
| ATOM | 2977 | CD2 | LEU A | 404 | −47.211 | −0.619 | −36.204 | 1.00 | 69.04 | C |
| ATOM | 2978 | C | LEU A | 404 | −44.943 | 2.676 | −37.184 | 1.00 | 56.00 | C |
| ATOM | 2979 | O | LEU A | 404 | −44.858 | 3.518 | −36.287 | 1.00 | 58.91 | O |
| ATOM | 2980 | N | PRO A | 405 | −45.233 | 3.001 | −38.422 | 1.00 | 55.64 | N |
| ATOM | 2981 | CA | PRO A | 405 | −45.348 | 4.427 | −38.707 | 1.00 | 55.37 | C |
| ATOM | 2982 | CB | PRO A | 405 | −44.958 | 4.491 | −40.156 | 1.00 | 53.93 | C |
| ATOM | 2983 | CG | PRO A | 405 | −45.491 | 3.204 | −40.684 | 1.00 | 55.95 | C |
| ATOM | 2984 | CD | PRO A | 405 | −45.438 | 2.182 | −39.611 | 1.00 | 54.26 | C |
| ATOM | 2985 | C | PRO A | 405 | −46.758 | 4.984 | −38.440 | 1.00 | 53.37 | C |
| ATOM | 2986 | O | PRO A | 405 | −47.748 | 4.247 | −38.432 | 1.00 | 51.76 | O |
| ATOM | 2987 | N | GLY A | 406 | −46.803 | 6.273 | −38.144 | 1.00 | 54.51 | N |
| ATOM | 2988 | CA | GLY A | 406 | −48.045 | 7.017 | −37.939 | 1.00 | 54.16 | C |
| ATOM | 2989 | C | GLY A | 406 | −48.607 | 6.945 | −36.548 | 1.00 | 56.11 | C |
| ATOM | 2990 | O | GLY A | 406 | −49.821 | 7.047 | −36.364 | 1.00 | 61.52 | O |
| ATOM | 2991 | N | ILE A | 407 | −47.748 | 6.758 | −35.557 | 1.00 | 57.14 | N |
| ATOM | 2992 | CA | ILE A | 407 | −48.245 | 6.637 | −34.223 | 1.00 | 57.90 | C |
| ATOM | 2993 | CB | ILE A | 407 | −47.203 | 6.075 | −33.274 | 1.00 | 57.56 | C |
| ATOM | 2994 | CG1 | ILE A | 407 | −46.950 | 4.612 | −33.640 | 1.00 | 58.06 | C |
| ATOM | 2995 | CD1 | ILE A | 407 | −45.865 | 3.898 | −32.850 | 1.00 | 57.98 | C |
| ATOM | 2996 | CG2 | ILE A | 407 | −47.712 | 6.214 | −31.843 | 1.00 | 56.64 | C |
| ATOM | 2997 | C | ILE A | 407 | −48.678 | 8.023 | −33.782 | 1.00 | 62.41 | C |
| ATOM | 2998 | O | ILE A | 407 | −47.962 | 9.003 | −34.005 | 1.00 | 62.50 | O |
| ATOM | 2999 | N | LYS A | 408 | −49.868 | 8.087 | −33.183 | 1.00 | 64.52 | N |
| ATOM | 3000 | CA | LYS A | 408 | −50.447 | 9.329 | −32.665 | 1.00 | 62.29 | C |
| ATOM | 3001 | CB | LYS A | 408 | 51.792 | 9.561 | −33.324 | 1.00 | 64.00 | C |
| ATOM | 3002 | CG | LYS A | 408 | −51.741 | 9.524 | −34.842 | 1.00 | 64.34 | C |
| ATOM | 3003 | CD | LYS A | 408 | −51.003 | 10.716 | −35.437 | 1.00 | 64.86 | C |
| ATOM | 3004 | CE | LYS A | 408 | −51.025 | 10.653 | −36.959 | 1.00 | 70.24 | C |
| ATOM | 3005 | NZ | LYS A | 408 | −50.250 | 11.751 | −37.600 | 1.00 | 73.24 | N |
| ATOM | 3006 | C | LYS A | 408 | −50.622 | 9.353 | −31.157 | 1.00 | 58.81 | C |
| ATOM | 3007 | O | LYS A | 408 | −50.826 | 10.422 | −30.592 | 1.00 | 62.49 | O |
| ATOM | 3008 | N | GLY A | 409 | −50.577 | 8.193 | −30.512 | 1.00 | 54.61 | N |
| ATOM | 3009 | CA | GLY A | 409 | −50.559 | 8.128 | −29.067 | 1.00 | 54.73 | C |
| ATOM | 3010 | C | GLY A | 409 | −50.099 | 6.794 | −28.488 | 1.00 | 55.71 | C |
| ATOM | 3011 | O | GLY A | 409 | −50.249 | 5.727 | −29.078 | 1.00 | 60.14 | O |
| ATOM | 3012 | N | LEU A | 410 | −49.534 | 6.888 | −27.309 | 1.00 | 54.48 | N |

TABLE 6-continued

Atomic coordinates for CRBN:DDB1: Compound B (Human protein)

| ATOM | 3013 | CA | LEU A | 410 | −49.054 | 5.786 | −26.536 | 1.00 | 54.46 | C |
|---|---|---|---|---|---|---|---|---|---|---|
| ATOM | 3014 | CB | LEU A | 410 | −47.587 | 6.021 | −26.249 | 1.00 | 56.20 | C |
| ATOM | 3015 | CG | LEU A | 410 | −46.480 | 5.413 | −27.070 | 1.00 | 58.23 | C |
| ATOM | 3016 | CD1 | LEU A | 410 | −46.964 | 4.886 | −28.407 | 1.00 | 59.71 | C |
| ATOM | 3017 | CD2 | LEU A | 410 | −45.355 | 6.444 | −27.195 | 1.00 | 59.08 | C |
| ATOM | 3018 | C | LEU A | 410 | −49.737 | 5.837 | −25.182 | 1.00 | 55.15 | C |
| ATOM | 3019 | O | LEU A | 410 | −49.839 | 6.913 | −24.557 | 1.00 | 60.75 | O |
| ATOM | 3020 | N | TRP A | 411 | −50.171 | 4.687 | −24.702 | 1.00 | 51.76 | N |
| ATOM | 3021 | CA | TRP A | 411 | −50.605 | 4.567 | −23.334 | 1.00 | 51.24 | C |
| ATOM | 3022 | CB | TRP A | 411 | −52.117 | 4.725 | −23.215 | 1.00 | 54.17 | C |
| ATOM | 3023 | CG | TRP A | 411 | −52.542 | 5.978 | −23.728 | 1.00 | 53.71 | C |
| ATOM | 3024 | CD1 | TRP A | 411 | −52.665 | 7.131 | −23.048 | 1.00 | 53.95 | C |
| ATOM | 3025 | NE1 | TRP A | 411 | −53.026 | 8.132 | −23.902 | 1.00 | 55.25 | N |
| ATOM | 3026 | CE2 | TRP A | 411 | −53.095 | 7.629 | −25.172 | 1.00 | 54.25 | C |
| ATOM | 3027 | CD2 | TRP A | 411 | −52.797 | 6.266 | −25.090 | 1.00 | 55.50 | C |
| ATOM | 3028 | CE3 | TRP A | 411 | −52.807 | 5.492 | −26.258 | 1.00 | 58.15 | C |
| ATOM | 3029 | CZ3 | TRP A | 411 | −53.123 | 6.103 | −27.447 | 1.00 | 57.42 | C |
| ATOM | 3030 | CH2 | TRP A | 411 | −53.427 | 7.475 | −27.486 | 1.00 | 55.97 | C |
| ATOM | 3031 | CZ2 | TRP A | 411 | −53.420 | 8.245 | −26.361 | 1.00 | 53.25 | C |
| ATOM | 3032 | C | TRP A | 411 | −50.229 | 3.221 | −22.813 | 1.00 | 51.17 | C |
| ATOM | 3033 | O | TRP A | 411 | −50.533 | 2.194 | −23.436 | 1.00 | 53.53 | O |
| ATOM | 3034 | N | PRO A | 412 | −49.593 | 3.197 | −21.655 | 1.00 | 49.64 | N |
| ATOM | 3035 | CA | PRO A | 412 | −49.339 | 1.952 | −21.004 | 1.00 | 50.84 | C |
| ATOM | 3036 | CB | PRO A | 412 | −48.274 | 2.313 | −20.008 | 1.00 | 52.76 | C |
| ATOM | 3037 | CG | PRO A | 412 | −48.605 | 3.691 | −19.606 | 1.00 | 51.82 | C |
| ATOM | 3038 | CD | PRO A | 412 | −49.230 | 4.327 | −20.810 | 1.00 | 50.73 | C |
| ATOM | 3039 | C | PRO A | 412 | −50.533 | 1.606 | −20.249 | 1.00 | 51.37 | C |
| ATOM | 3040 | O | PRO A | 412 | −51.335 | 2.487 | −19.977 | 1.00 | 50.50 | O |
| ATOM | 3041 | N | LEU A | 413 | −50.605 | 0.362 | −19.815 | 1.00 | 56.43 | N |
| ATOM | 3042 | CA | LEU A | 413 | −51.824 | −0.156 | −19.179 | 1.00 | 59.26 | C |
| ATOM | 3043 | CB | LEU A | 413 | −52.879 | −0.221 | −20.270 | 1.00 | 60.79 | C |
| ATOM | 3044 | CG | LEU A | 413 | −54.138 | −1.033 | −20.326 | 1.00 | 63.74 | C |
| ATOM | 3045 | CD1 | LEU A | 413 | −54.963 | −0.564 | −21.530 | 1.00 | 64.44 | C |
| ATOM | 3046 | CD2 | LEU A | 413 | −53.836 | −2.510 | −20.466 | 1.00 | 67.55 | C |
| ATOM | 3047 | C | LEU A | 413 | −51.519 | −1.501 | −18.557 | 1.00 | 59.24 | C |
| ATOM | 3048 | O | LEU A | 413 | −50.609 | −2.215 | −19.030 | 1.00 | 63.45 | O |
| ATOM | 3049 | N | ARG A | 414 | −52.265 | −1.845 | −17.509 | 1.00 | 58.43 | N |
| ATOM | 3050 | CA | ARG A | 414 | −52.100 | −3.128 | −16.785 | 1.00 | 61.92 | C |
| ATOM | 3051 | CB | ARG A | 414 | −51.969 | −2.897 | −15.287 | 1.00 | 66.03 | C |
| ATOM | 3052 | CG | ARG A | 414 | −50.544 | −2.511 | −14.860 | 1.00 | 70.73 | C |
| ATOM | 3053 | CD | ARG A | 414 | −50.409 | −1.767 | −13.527 | 1.00 | 72.03 | C |
| ATOM | 3054 | NE | ARG A | 414 | −51.643 | −1.835 | −12.730 | 1.00 | 75.99 | N |
| ATOM | 3055 | CZ | ARG A | 414 | −52.429 | −0.798 | −12.388 | 1.00 | 74.73 | C |
| ATOM | 3056 | NH1 | ARG A | 414 | −52.140 | 0.468 | −12.700 | 1.00 | 70.45 | N |
| ATOM | 3057 | NH2 | ARG A | 414 | −53.533 | −1.037 | −11.687 | 1.00 | 76.39 | N |
| ATOM | 3058 | C | ARG A | 414 | −53.289 | −4.021 | −17.094 | 1.00 | 61.51 | C |
| ATOM | 3059 | O | ARG A | 414 | −54.365 | −3.787 | −16.574 | 1.00 | 61.49 | O |
| ATOM | 3060 | N | SER A | 415 | −53.089 | −4.998 | −17.989 | 1.00 | 64.64 | N |
| ATOM | 3061 | CA | SER A | 415 | −54.135 | −5.919 | −18.468 | 1.00 | 64.89 | C |
| ATOM | 3062 | CB | SER A | 415 | −53.651 | −6.669 | −19.705 | 1.00 | 59.61 | C |
| ATOM | 3063 | C | SER A | 415 | −54.587 | −6.941 | −17.414 | 1.00 | 67.07 | C |
| ATOM | 3064 | O | SER A | 415 | −55.678 | −7.491 | −17.513 | 1.00 | 66.06 | O |
| ATOM | 3065 | N | ASP A | 416 | −53.746 | −7.195 | −16.420 | 1.00 | 69.59 | N |
| ATOM | 3066 | CA | ASP A | 416 | −54.052 | −8.154 | −15.386 | 1.00 | 75.14 | C |
| ATOM | 3067 | CB | ASP A | 416 | −53.117 | −9.353 | −15.485 | 1.00 | 77.22 | C |
| ATOM | 3068 | CG | ASP A | 416 | −53.136 | −10.173 | −14.254 | 1.00 | 79.90 | C |
| ATOM | 3069 | OD1 | ASP A | 416 | −54.225 | −10.307 | −13.677 | 1.00 | 87.24 | O |
| ATOM | 3070 | OD2 | ASP A | 416 | −52.073 | −10.632 | −13.820 | 1.00 | 83.34 | O |
| ATOM | 3071 | C | ASP A | 416 | −53.945 | −7.471 | −14.016 | 1.00 | 77.41 | C |
| ATOM | 3072 | O | ASP A | 416 | −52.854 | −7.132 | −13.562 | 1.00 | 72.50 | O |
| ATOM | 3073 | N | PRO A | 417 | −55.084 | −7.308 | −13.338 | 1.00 | 84.17 | N |
| ATOM | 3074 | CA | PRO A | 417 | −55.163 | −6.426 | −12.165 | 1.00 | 88.93 | C |
| ATOM | 3075 | CB | PRO A | 417 | −56.671 | −6.315 | −11.917 | 1.00 | 92.21 | C |
| ATOM | 3076 | CG | PRO A | 417 | −57.230 | −7.581 | −12.472 | 1.00 | 90.68 | C |
| ATOM | 3077 | CD | PRO A | 417 | −56.392 | −7.905 | −13.666 | 1.00 | 87.03 | C |
| ATOM | 3078 | C | PRO A | 417 | −54.472 | −6.883 | −10.886 | 1.00 | 88.51 | C |
| ATOM | 3079 | O | PRO A | 417 | −54.210 | −6.057 | −10.018 | 1.00 | 80.00 | O |
| ATOM | 3080 | N | ASN A | 418 | −54.220 | −8.177 | −10.740 | 1.00 | 97.93 | N |
| ATOM | 3081 | CA | ASN A | 418 | −53.475 | −8.660 | −9.570 | 1.00 | 101.90 | C |
| ATOM | 3082 | CB | ASN A | 418 | −54.186 | −9.880 | −8.925 | 1.00 | 98.09 | C |
| ATOM | 3083 | CG | ASN A | 418 | −54.234 | −11.086 | −9.843 | 1.00 | 101.67 | C |
| ATOM | 3084 | OD1 | ASN A | 418 | −54.163 | −10.957 | −11.063 | 1.00 | 104.47 | O |
| ATOM | 3085 | ND2 | ASN A | 418 | −54.345 | −12.267 | −9.261 | 1.00 | 101.58 | N |
| ATOM | 3086 | C | ASN A | 418 | −51.949 | −8.880 | −9.857 | 1.00 | 96.48 | C |
| ATOM | 3087 | O | ASN A | 418 | −51.270 | −9.500 | −9.043 | 1.00 | 100.21 | O |
| ATOM | 3088 | N | ARG A | 419 | −51.427 | −8.378 | −10.994 | 1.00 | 88.55 | N |
| ATOM | 3089 | CA | ARG A | 419 | −49.959 | −8.139 | −11.193 | 1.00 | 83.58 | C |
| ATOM | 3090 | CB | ARG A | 419 | −49.393 | −8.801 | −12.470 | 1.00 | 79.54 | C |

TABLE 6-continued

Atomic coordinates for CRBN:DDB1: Compound B (Human protein)

| ATOM | 3091 | C   | ARG A | 419 | −49.723 | −6.629 | −11.227 | 1.00 | 79.54  | C |
|------|------|-----|-------|-----|---------|--------|---------|------|--------|---|
| ATOM | 3092 | O   | ARG A | 419 | −50.572 | −5.874 | −11.689 | 1.00 | 79.56  | O |
| ATOM | 3093 | N   | GLU A | 420 | −48.561 | −6.193 | −10.765 | 1.00 | 79.83  | N |
| ATOM | 3094 | CA  | GLU A | 420 | −48.366 | −4.803 | −10.319 | 1.00 | 84.06  | C |
| ATOM | 3095 | CB  | GLU A | 420 | −47.612 | −4.827 | −8.968  | 1.00 | 95.40  | C |
| ATOM | 3096 | CG  | GLU A | 420 | −47.923 | −3.667 | −8.012  | 1.00 | 100.52 | C |
| ATOM | 3097 | CD  | GLU A | 420 | −48.540 | −4.144 | −6.693  | 1.00 | 103.91 | C |
| ATOM | 3098 | OE1 | GLU A | 420 | −49.600 | −3.609 | −6.285  | 1.00 | 97.17  | O |
| ATOM | 3099 | OE2 | GLU A | 420 | −47.982 | −5.082 | −6.082  | 1.00 | 107.73 | O |
| ATOM | 3100 | C   | GLU A | 420 | −47.594 | −3.955 | −11.322 | 1.00 | 79.30  | C |
| ATOM | 3101 | O   | GLU A | 420 | −46.897 | −3.018 | −10.933 | 1.00 | 80.81  | O |
| ATOM | 3102 | N   | THR A | 421 | −47.758 | −4.250 | −12.610 | 1.00 | 72.23  | N |
| ATOM | 3103 | CA  | THR A | 421 | −46.745 | −3.941 | −13.624 | 1.00 | 61.47  | C |
| ATOM | 3104 | CB  | THR A | 421 | −45.643 | −5.033 | −13.559 | 1.00 | 55.59  | C |
| ATOM | 3105 | OG1 | THR A | 421 | −44.427 | −4.482 | −14.052 | 1.00 | 52.25  | O |
| ATOM | 3106 | CG2 | THR A | 421 | −46.034 | −6.361 | −14.304 | 1.00 | 52.11  | C |
| ATOM | 3107 | C   | THR A | 421 | −47.338 | −3.894 | −15.031 | 1.00 | 58.84  | C |
| ATOM | 3108 | O   | THR A | 421 | −48.055 | −4.798 | −15.417 | 1.00 | 60.74  | O |
| ATOM | 3109 | N   | ASP A | 422 | −47.036 | −2.872 | −15.821 | 1.00 | 58.55  | N |
| ATOM | 3110 | CA  | ASP A | 422 | −47.611 | −2.783 | −17.183 | 1.00 | 59.10  | C |
| ATOM | 3111 | CB  | ASP A | 422 | −47.119 | −1.564 | −17.934 | 1.00 | 62.40  | C |
| ATOM | 3112 | CG  | ASP A | 422 | −47.451 | −0.267 | −17.232 | 1.00 | 66.95  | C |
| ATOM | 3113 | OD1 | ASP A | 422 | −48.657 | 0.039  | −17.026 | 1.00 | 68.66  | O |
| ATOM | 3114 | OD2 | ASP A | 422 | −46.478 | 0.459  | −16.910 | 1.00 | 71.52  | O |
| ATOM | 3115 | C   | ASP A | 422 | −47.302 | −4.005 | −18.040 | 1.00 | 56.80  | C |
| ATOM | 3116 | O   | ASP A | 422 | −46.220 | −4.627 | −17.919 | 1.00 | 55.84  | O |
| ATOM | 3117 | N   | ASP A | 423 | −48.283 | −4.379 | −18.851 | 1.00 | 50.55  | N |
| ATOM | 3118 | CA  | ASP A | 423 | −48.097 | −5.456 | −19.785 | 1.00 | 49.77  | C |
| ATOM | 3119 | CB  | ASP A | 423 | −48.615 | −6.728 | −19.149 | 1.00 | 50.68  | C |
| ATOM | 3120 | CG  | ASP A | 423 | −50.122 | −6.775 | −19.019 | 1.00 | 52.52  | C |
| ATOM | 3121 | OD1 | ASP A | 423 | −50.858 | −5.835 | −19.377 | 1.00 | 55.69  | O |
| ATOM | 3122 | OD2 | ASP A | 423 | −50.593 | −7.816 | −18.564 | 1.00 | 57.40  | O |
| ATOM | 3123 | C   | ASP A | 423 | −48.719 | −5.170 | −21.161 | 1.00 | 52.23  | C |
| ATOM | 3124 | O   | ASP A | 423 | −48.830 | −6.045 | −22.042 | 1.00 | 49.80  | O |
| ATOM | 3125 | N   | THR A | 424 | −49.095 | −3.920 | −21.371 | 1.00 | 51.45  | N |
| ATOM | 3126 | CA  | THR A | 424 | −49.706 | −3.558 | −22.593 | 1.00 | 49.36  | C |
| ATOM | 3127 | CB  | THR A | 424 | −51.188 | −3.564 | −22.380 | 1.00 | 50.19  | C |
| ATOM | 3128 | OG1 | THR A | 424 | −51.551 | −4.887 | −22.020 | 1.00 | 51.86  | O |
| ATOM | 3129 | CG2 | THR A | 424 | −51.945 | −3.156 | −23.647 | 1.00 | 51.71  | C |
| ATOM | 3130 | C   | THR A | 424 | −49.226 | −2.190 | −22.952 | 1.00 | 49.48  | C |
| ATOM | 3131 | O   | THR A | 424 | −48.903 | −1.384 | −22.126 | 1.00 | 52.86  | O |
| ATOM | 3132 | N   | LEU A | 425 | −49.157 | −1.948 | −24.230 | 1.00 | 50.63  | N |
| ATOM | 3133 | CA  | LEU A | 425 | −48.932 | −0.639 | −24.739 | 1.00 | 50.72  | C |
| ATOM | 3134 | CB  | LEU A | 425 | −47.589 | −0.644 | −25.430 | 1.00 | 49.30  | C |
| ATOM | 3135 | CG  | LEU A | 425 | −46.807 | 0.632  | −25.486 | 1.00 | 48.41  | C |
| ATOM | 3136 | CD1 | LEU A | 425 | −46.842 | 1.350  | −24.163 | 1.00 | 50.83  | C |
| ATOM | 3137 | CD2 | LEU A | 425 | −45.386 | 0.244  | −25.803 | 1.00 | 49.49  | C |
| ATOM | 3138 | C   | LEU A | 425 | −50.034 | −0.510 | −25.739 | 1.00 | 52.01  | C |
| ATOM | 3139 | O   | LEU A | 425 | −50.310 | −1.488 | −26.441 | 1.00 | 53.28  | O |
| ATOM | 3140 | N   | VAL A | 426 | −50.689 | 0.645  | −25.796 | 1.00 | 50.36  | N |
| ATOM | 3141 | CA  | VAL A | 426 | −51.773 | 0.834  | −26.753 | 1.00 | 49.39  | C |
| ATOM | 3142 | CB  | VAL A | 426 | −53.113 | 1.103  | −26.045 | 1.00 | 50.69  | C |
| ATOM | 3143 | CG1 | VAL A | 426 | −54.254 | 1.256  | −27.057 | 1.00 | 50.77  | C |
| ATOM | 3144 | CG2 | VAL A | 426 | −53.423 | −0.059 | −25.096 | 1.00 | 50.38  | C |
| ATOM | 3145 | C   | VAL A | 426 | −51.369 | 1.937  | −27.665 | 1.00 | 46.35  | C |
| ATOM | 3146 | O   | VAL A | 426 | −50.809 | 2.910  | −27.203 | 1.00 | 47.52  | O |
| ATOM | 3147 | N   | LEU A | 427 | −51.593 | 1.766  | −28.958 | 1.00 | 45.54  | N |
| ATOM | 3148 | CA  | LEU A | 427 | −51.101 | 2.740  | −29.925 | 1.00 | 51.43  | C |
| ATOM | 3149 | CB  | LEU A | 427 | −50.051 | 2.138  | −30.842 | 1.00 | 53.54  | C |
| ATOM | 3150 | CG  | LEU A | 427 | −48.674 | 1.957  | −30.216 | 1.00 | 55.42  | C |
| ATOM | 3151 | CD1 | LEU A | 427 | −48.624 | 0.856  | −29.159 | 1.00 | 54.95  | C |
| ATOM | 3152 | CD2 | LEU A | 427 | −47.672 | 1.657  | −31.301 | 1.00 | 58.12  | C |
| ATOM | 3153 | C   | LEU A | 427 | −52.234 | 3.217  | −30.771 | 1.00 | 54.11  | C |
| ATOM | 3154 | O   | LEU A | 427 | −52.953 | 2.378  | −31.339 | 1.00 | 53.49  | O |
| ATOM | 3155 | N   | SER A | 428 | −52.397 | 4.541  | −30.877 | 1.00 | 54.07  | N |
| ATOM | 3156 | CA  | SER A | 428 | −53.450 | 5.071  | −31.718 | 1.00 | 55.42  | C |
| ATOM | 3157 | CB  | SER A | 428 | −54.253 | 6.202  | −31.034 | 1.00 | 60.05  | C |
| ATOM | 3158 | OG  | SER A | 428 | −53.702 | 7.500  | −31.229 | 1.00 | 65.05  | O |
| ATOM | 3159 | C   | SER A | 428 | −52.818 | 5.496  | −33.013 | 1.00 | 51.60  | C |
| ATOM | 3160 | O   | SER A | 428 | −51.662 | 5.875  | −33.050 | 1.00 | 49.29  | O |
| ATOM | 3161 | N   | PHE A | 429 | −53.598 | 5.382  | −34.080 | 1.00 | 53.24  | N |
| ATOM | 3162 | CA  | PHE A | 429 | −53.224 | 5.805  | −35.437 | 1.00 | 53.52  | C |
| ATOM | 3163 | CB  | PHE A | 429 | −52.922 | 4.581  | −36.285 | 1.00 | 51.14  | C |
| ATOM | 3164 | CG  | PHE A | 429 | −51.762 | 3.767  | −35.800 | 1.00 | 48.87  | C |
| ATOM | 3165 | CD1 | PHE A | 429 | −51.937 | 2.807  | −34.828 | 1.00 | 48.67  | C |
| ATOM | 3166 | CE1 | PHE A | 429 | −50.879 | 2.051  | −34.365 | 1.00 | 46.00  | C |
| ATOM | 3167 | CZ  | PHE A | 429 | −49.640 | 2.235  | −34.913 | 1.00 | 47.11  | C |
| ATOM | 3168 | CE2 | PHE A | 429 | −49.444 | 3.195  | −35.891 | 1.00 | 46.94  | C |

TABLE 6-continued

Atomic coordinates for CRBN:DDB1: Compound B (Human protein)

| ATOM | 3169 | CD2 | PHE A | 429 | −50.499 | 3.948 | −36.329 | 1.00 | 48.09 | C |
|---|---|---|---|---|---|---|---|---|---|---|
| ATOM | 3170 | C | PHE A | 429 | −54.415 | 6.522 | −36.066 | 1.00 | 54.62 | C |
| ATOM | 3171 | O | PHE A | 429 | −55.520 | 6.465 | −35.536 | 1.00 | 55.87 | O |
| ATOM | 3172 | N | VAL A | 430 | −54.215 | 7.160 | −37.209 | 1.00 | 55.59 | N |
| ATOM | 3173 | CA | VAL A | 430 | −55.311 | 7.876 | −37.847 | 1.00 | 57.39 | C |
| ATOM | 3174 | CB | VAL A | 430 | −54.881 | 8.673 | −39.112 | 1.00 | 63.19 | C |
| ATOM | 3175 | CG1 | VAL A | 430 | −55.076 | 7.877 | −40.422 | 1.00 | 69.73 | C |
| ATOM | 3176 | CG2 | VAL A | 430 | −55.634 | 9.990 | −39.185 | 1.00 | 64.68 | C |
| ATOM | 3177 | C | VAL A | 430 | −56.436 | 6.879 | −38.100 | 1.00 | 55.45 | C |
| ATOM | 3178 | O | VAL A | 430 | −56.260 | 5.873 | −38.754 | 1.00 | 53.13 | O |
| ATOM | 3179 | N | GLY A | 431 | −57.566 | 7.173 | −37.483 | 1.00 | 58.77 | N |
| ATOM | 3180 | CA | GLY A | 431 | −58.730 | 6.308 | −37.408 | 1.00 | 62.11 | C |
| ATOM | 3181 | C | GLY A | 431 | −58.548 | 4.842 | −37.102 | 1.00 | 59.37 | C |
| ATOM | 3182 | O | GLY A | 431 | −59.141 | 4.018 | −37.753 | 1.00 | 64.87 | O |
| ATOM | 3183 | N | GLN A | 432 | −57.761 | 4.498 | −36.112 | 1.00 | 57.86 | N |
| ATOM | 3184 | CA | GLN A | 432 | −57.397 | 3.114 | −35.970 | 1.00 | 61.05 | C |
| ATOM | 3185 | CB | GLN A | 432 | −56.507 | 2.762 | −37.163 | 1.00 | 68.60 | C |
| ATOM | 3186 | CG | GLN A | 432 | −56.158 | 1.299 | −37.380 | 1.00 | 79.20 | C |
| ATOM | 3187 | CD | GLN A | 432 | −55.000 | 1.174 | −38.373 | 1.00 | 85.61 | C |
| ATOM | 3188 | OE1 | GLN A | 432 | −55.090 | 1.683 | −39.484 | 1.00 | 88.20 | O |
| ATOM | 3189 | NE2 | GLN A | 432 | −53.893 | 0.543 | −37.958 | 1.00 | 87.94 | N |
| ATOM | 3190 | C | GLN A | 432 | −56.668 | 2.956 | −34.648 | 1.00 | 57.64 | C |
| ATOM | 3191 | O | GLN A | 432 | −55.816 | 3.770 | −34.335 | 1.00 | 56.53 | O |
| ATOM | 3192 | N | THR A | 433 | −57.013 | 1.939 | −33.862 | 1.00 | 55.68 | N |
| ATOM | 3193 | CA | THR A | 433 | −56.337 | 1.673 | −32.560 | 1.00 | 56.93 | C |
| ATOM | 3194 | CB | THR A | 433 | −57.293 | 1.873 | −31.372 | 1.00 | 53.95 | C |
| ATOM | 3195 | OG1 | THR A | 433 | −57.594 | 3.260 | −31.272 | 1.00 | 54.80 | O |
| ATOM | 3196 | CG2 | THR A | 433 | −56.654 | 1.428 | −30.072 | 1.00 | 52.33 | C |
| ATOM | 3197 | C | THR A | 433 | −55.719 | 0.256 | −32.536 | 1.00 | 56.09 | C |
| ATOM | 3198 | O | THR A | 433 | −56.276 | −0.651 | −33.118 | 1.00 | 59.19 | O |
| ATOM | 3199 | N | ARG A | 434 | −54.563 | 0.103 | −31.891 | 1.00 | 53.78 | N |
| ATOM | 3200 | CA | ARG A | 434 | −53.822 | −1.151 | −31.847 | 1.00 | 53.96 | C |
| ATOM | 3201 | CB | ARG A | 434 | −52.623 | −1.058 | −32.727 | 1.00 | 54.86 | C |
| ATOM | 3202 | CG | ARG A | 434 | −52.863 | −0.900 | −34.201 | 1.00 | 58.73 | C |
| ATOM | 3203 | CD | ARG A | 434 | −51.602 | −1.438 | −34.884 | 1.00 | 61.56 | C |
| ATOM | 3204 | NE | ARG A | 434 | −51.377 | −1.000 | −36.244 | 1.00 | 61.49 | N |
| ATOM | 3205 | CZ | ARG A | 434 | −50.590 | −1.631 | −37.099 | 1.00 | 64.68 | C |
| ATOM | 3206 | NH1 | ARG A | 434 | −49.931 | −2.750 | −36.786 | 1.00 | 63.62 | N |
| ATOM | 3207 | NH2 | ARG A | 434 | −50.482 | −1.134 | −38.306 | 1.00 | 71.75 | N |
| ATOM | 3208 | C | ARG A | 434 | −53.241 | −1.464 | −30.477 | 1.00 | 54.45 | C |
| ATOM | 3209 | O | ARG A | 434 | −52.829 | −0.553 | −29.748 | 1.00 | 57.88 | O |
| ATOM | 3210 | N | VAL A | 435 | −53.104 | −2.745 | −30.167 | 1.00 | 50.92 | N |
| ATOM | 3211 | CA | VAL A | 435 | −52.731 | −3.124 | −28.837 | 1.00 | 50.43 | C |
| ATOM | 3212 | CB | VAL A | 435 | −53.933 | −3.690 | −28.086 | 1.00 | 50.42 | C |
| ATOM | 3213 | CG1 | VAL A | 435 | −53.532 | −4.081 | −26.680 | 1.00 | 51.26 | C |
| ATOM | 3214 | CG2 | VAL A | 435 | −55.037 | −2.638 | −28.020 | 1.00 | 51.18 | C |
| ATOM | 3215 | C | VAL A | 435 | −51.574 | −4.105 | −28.869 | 1.00 | 51.99 | C |
| ATOM | 3216 | O | VAL A | 435 | −51.690 | −5.166 | −29.428 | 1.00 | 53.13 | O |
| ATOM | 3217 | N | LEU A | 436 | −50.459 | −3.723 | −28.249 | 1.00 | 51.77 | N |
| ATOM | 3218 | CA | LEU A | 436 | −49.290 | −4.561 | −28.111 | 1.00 | 50.41 | C |
| ATOM | 3219 | CB | LEU A | 436 | −48.022 | −3.731 | −28.349 | 1.00 | 47.79 | C |
| ATOM | 3220 | CG | LEU A | 436 | −48.033 | −2.914 | −29.634 | 1.00 | 45.89 | C |
| ATOM | 3221 | CD1 | LEU A | 436 | −46.719 | −2.207 | −29.855 | 1.00 | 44.19 | C |
| ATOM | 3222 | CD2 | LEU A | 436 | −48.334 | −3.835 | −30.778 | 1.00 | 47.79 | C |
| ATOM | 3223 | C | LEU A | 436 | −49.260 | −5.120 | −26.703 | 1.00 | 54.01 | C |
| ATOM | 3224 | O | LEU A | 436 | −49.204 | −4.333 | −25.746 | 1.00 | 53.76 | O |
| ATOM | 3225 | N | MET A | 437 | −49.284 | −6.457 | −26.572 | 1.00 | 55.11 | N |
| ATOM | 3226 | CA | MET A | 437 | −49.029 | −7.089 | −25.281 | 1.00 | 57.48 | C |
| ATOM | 3227 | CB | MET A | 437 | −49.804 | −8.387 | −25.138 | 1.00 | 61.73 | C |
| ATOM | 3228 | CG | MET A | 437 | −49.172 | −9.548 | −25.866 | 1.00 | 66.78 | C |
| ATOM | 3229 | SD | MET A | 437 | −50.179 | −11.022 | −25.799 | 1.00 | 73.96 | S |
| ATOM | 3230 | CE | MET A | 437 | −50.105 | −11.399 | −24.029 | 1.00 | 74.10 | C |
| ATOM | 3231 | C | MET A | 437 | −47.540 | −7.345 | −25.119 | 1.00 | 54.51 | C |
| ATOM | 3232 | O | MET A | 437 | −46.853 | −7.533 | −26.109 | 1.00 | 53.19 | O |
| ATOM | 3233 | N | LEU A | 438 | −47.075 | −7.380 | −23.864 | 1.00 | 55.01 | N |
| ATOM | 3234 | CA | LEU A | 438 | −45.669 | −7.577 | −23.510 | 1.00 | 55.60 | C |
| ATOM | 3235 | CB | LEU A | 438 | −45.106 | −6.300 | −22.912 | 1.00 | 55.65 | C |
| ATOM | 3236 | CG | LEU A | 438 | −45.087 | −5.133 | −23.875 | 1.00 | 54.32 | C |
| ATOM | 3237 | CD1 | LEU A | 438 | −46.406 | −4.409 | −23.859 | 1.00 | 58.02 | C |
| ATOM | 3238 | CD2 | LEU A | 438 | −44.013 | −4.155 | −23.494 | 1.00 | 53.07 | C |
| ATOM | 3239 | C | LEU A | 438 | −45.433 | −8.698 | −22.493 | 1.00 | 57.76 | C |
| ATOM | 3240 | O | LEU A | 438 | −45.989 | −8.703 | −21.388 | 1.00 | 56.04 | O |
| ATOM | 3241 | N | ASN A | 439 | −44.580 | −9.639 | −22.877 | 1.00 | 60.90 | N |
| ATOM | 3242 | CA | ASN A | 439 | −44.086 | −10.678 | −21.964 | 1.00 | 65.31 | C |
| ATOM | 3243 | CB | ASN A | 439 | −44.667 | −12.060 | −22.304 | 1.00 | 69.08 | C |
| ATOM | 3244 | CG | ASN A | 439 | −46.167 | −11.999 | −22.539 | 1.00 | 77.42 | C |
| ATOM | 3245 | OD1 | ASN A | 439 | −46.969 | −12.419 | −21.696 | 1.00 | 90.07 | O |
| ATOM | 3246 | ND2 | ASN A | 439 | −46.557 | −11.419 | −23.668 | 1.00 | 79.65 | N |

TABLE 6-continued

Atomic coordinates for CRBN:DDB1: Compound B (Human protein)

| ATOM | 3247 | C | ASN A | 439 | −42.572 | −10.665 | −22.045 | 1.00 | 60.15 | C |
|---|---|---|---|---|---|---|---|---|---|---|
| ATOM | 3248 | O | ASN A | 439 | −42.012 | −10.994 | −23.079 | 1.00 | 57.04 | O |
| ATOM | 3249 | N | GLY A | 440 | −41.926 | −10.229 | −20.968 | 1.00 | 56.67 | N |
| ATOM | 3250 | CA | GLY A | 440 | −40.514 | −10.004 | −20.962 | 1.00 | 56.00 | C |
| ATOM | 3251 | C | GLY A | 440 | −40.264 | −9.007 | −22.054 | 1.00 | 60.06 | C |
| ATOM | 3252 | O | GLY A | 440 | −40.839 | −7.884 | −22.043 | 1.00 | 70.02 | O |
| ATOM | 3253 | N | GLU A | 441 | −39.463 | −9.443 | −23.021 | 1.00 | 57.33 | N |
| ATOM | 3254 | CA | GLU A | 441 | −39.027 | −8.602 | −24.102 | 1.00 | 59.09 | C |
| ATOM | 3255 | CB | GLU A | 441 | −37.521 | −8.740 | −24.246 | 1.00 | 61.05 | C |
| ATOM | 3256 | CG | GLU A | 441 | −36.721 | −8.124 | −23.119 | 1.00 | 60.60 | C |
| ATOM | 3257 | CD | GLU A | 441 | −35.211 | −8.222 | −23.317 | 1.00 | 60.70 | C |
| ATOM | 3258 | OE1 | GLU A | 441 | −34.501 | −7.940 | −22.360 | 1.00 | 69.39 | O |
| ATOM | 3259 | OE2 | GLU A | 441 | −34.691 | −8.582 | −24.378 | 1.00 | 57.88 | O |
| ATOM | 3260 | C | GLU A | 441 | −39.706 | −8.923 | −25.436 | 1.00 | 60.39 | C |
| ATOM | 3261 | O | GLU A | 441 | −39.340 | −8.306 | −26.482 | 1.00 | 64.59 | O |
| ATOM | 3262 | N | GLU A | 442 | −40.689 | −9.845 | −25.394 | 1.00 | 58.79 | N |
| ATOM | 3263 | CA | GLU A | 442 | −41.506 | −10.261 | −26.569 | 1.00 | 57.16 | C |
| ATOM | 3264 | CB | GLU A | 442 | −41.900 | −11.740 | −26.478 | 1.00 | 58.80 | C |
| ATOM | 3265 | CG | GLU A | 442 | −40.735 | −12.727 | −26.445 | 1.00 | 62.87 | C |
| ATOM | 3266 | CD | GLU A | 442 | −41.200 | −14.130 | −26.124 | 1.00 | 66.35 | C |
| ATOM | 3267 | OE1 | GLU A | 442 | −42.106 | −14.625 | −26.814 | 1.00 | 71.52 | O |
| ATOM | 3268 | OE2 | GLU A | 442 | −40.689 | −14.731 | −25.155 | 1.00 | 73.37 | O |
| ATOM | 3269 | C | GLU A | 442 | −42.784 | −9.434 | −26.731 | 1.00 | 52.94 | C |
| ATOM | 3270 | O | GLU A | 442 | −43.740 | −9.548 | −25.951 | 1.00 | 54.86 | O |
| ATOM | 3271 | N | VAL A | 443 | −42.798 | −8.611 | −27.759 | 1.00 | 48.31 | N |
| ATOM | 3272 | CA | VAL A | 443 | −43.948 | −7.818 | −28.090 | 1.00 | 48.44 | C |
| ATOM | 3273 | CB | VAL A | 443 | −43.500 | −6.443 | −28.587 | 1.00 | 46.57 | C |
| ATOM | 3274 | CG1 | VAL A | 443 | −44.686 | −5.529 | −28.760 | 1.00 | 47.07 | C |
| ATOM | 3275 | CG2 | VAL A | 443 | −42.523 | −5.819 | −27.626 | 1.00 | 45.33 | C |
| ATOM | 3276 | C | VAL A | 443 | −44.773 | −8.560 | −29.178 | 1.00 | 52.94 | C |
| ATOM | 3277 | O | VAL A | 443 | −44.205 | −9.164 | −30.131 | 1.00 | 53.72 | O |
| ATOM | 3278 | N | GLU A | 444 | −46.103 | −8.537 | −29.019 | 1.00 | 54.13 | N |
| ATOM | 3279 | CA | GLU A | 444 | −47.047 | −9.141 | −29.979 | 1.00 | 53.78 | C |
| ATOM | 3280 | CB | GLU A | 444 | −47.419 | −10.580 | −29.556 | 1.00 | 55.76 | C |
| ATOM | 3281 | CG | GLU A | 444 | −48.064 | −11.435 | −30.663 | 1.00 | 57.86 | C |
| ATOM | 3282 | CD | GLU A | 444 | −48.277 | −12.924 | −30.300 | 1.00 | 57.93 | C |
| ATOM | 3283 | OE1 | GLU A | 444 | −49.254 | −13.544 | −30.807 | 1.00 | 56.73 | O |
| ATOM | 3284 | OE2 | GLU A | 444 | −47.474 | −13.496 | −29.520 | 1.00 | 57.27 | O |
| ATOM | 3285 | C | GLU A | 444 | −48.306 | −8.281 | −30.057 | 1.00 | 53.56 | C |
| ATOM | 3286 | O | GLU A | 444 | −48.933 | −8.004 | −29.028 | 1.00 | 53.68 | O |
| ATOM | 3287 | N | GLU A | 445 | −48.672 | −7.846 | −31.262 | 1.00 | 54.13 | N |
| ATOM | 3288 | CA | GLU A | 445 | −49.916 | −7.084 | −31.445 | 1.00 | 54.03 | C |
| ATOM | 3289 | CB | GLU A | 445 | −50.031 | −6.434 | −32.830 | 1.00 | 53.51 | C |
| ATOM | 3290 | CG | GLU A | 445 | −51.306 | −5.617 | −33.007 | 1.00 | 54.79 | C |
| ATOM | 3291 | CD | GLU A | 445 | −51.366 | 4.828 | −34.310 | 1.00 | 58.00 | C |
| ATOM | 3292 | OE1 | GLU A | 445 | −52.492 | −4.643 | −34.885 | 1.00 | 60.21 | O |
| ATOM | 3293 | OE2 | GLU A | 445 | −50.287 | −4.369 | −34.768 | 1.00 | 58.28 | O |
| ATOM | 3294 | C | GLU A | 445 | −51.040 | −8.048 | −31.212 | 1.00 | 51.72 | C |
| ATOM | 3295 | O | GLU A | 445 | −50.930 | −9.171 | −31.571 | 1.00 | 51.03 | O |
| ATOM | 3296 | N | THR A | 446 | −52.097 | −7.586 | −30.576 | 1.00 | 55.50 | N |
| ATOM | 3297 | CA | THR A | 446 | −53.188 | −8.435 | −30.115 | 1.00 | 59.27 | C |
| ATOM | 3298 | CB | THR A | 446 | −52.783 | −9.172 | −28.799 | 1.00 | 57.95 | C |
| ATOM | 3299 | OG1 | THR A | 446 | −53.440 | −10.433 | −28.752 | 1.00 | 63.57 | O |
| ATOM | 3300 | CG2 | THR A | 446 | −53.138 | −8.402 | −27.551 | 1.00 | 56.45 | C |
| ATOM | 3301 | C | THR A | 446 | −54.542 | −7.657 | −30.022 | 1.00 | 63.00 | C |
| ATOM | 3302 | O | THR A | 446 | −54.607 | −6.463 | −30.335 | 1.00 | 66.09 | O |
| ATOM | 3303 | N | GLU A | 447 | −55.617 | −8.356 | −29.654 | 1.00 | 68.01 | N |
| ATOM | 3304 | CA | GLU A | 447 | −56.955 | −7.755 | −29.493 | 1.00 | 69.93 | C |
| ATOM | 3305 | CB | GLU A | 447 | −58.045 | −8.766 | −29.926 | 1.00 | 69.48 | C |
| ATOM | 3306 | C | GLU A | 447 | −57.056 | −7.421 | −28.004 | 1.00 | 72.84 | C |
| ATOM | 3307 | O | GLU A | 447 | −56.452 | −8.129 | −27.189 | 1.00 | 69.69 | O |
| ATOM | 3308 | N | LEU A | 448 | −57.743 | −6.338 | −27.627 | 1.00 | 75.59 | N |
| ATOM | 3309 | CA | LEU A | 448 | −58.141 | −6.178 | −26.213 | 1.00 | 73.27 | C |
| ATOM | 3310 | CB | LEU A | 448 | −57.555 | −4.917 | −25.571 | 1.00 | 70.29 | C |
| ATOM | 3311 | CG | LEU A | 448 | −57.852 | −4.706 | −24.065 | 1.00 | 72.12 | C |
| ATOM | 3312 | CD1 | LEU A | 448 | −57.611 | −5.941 | −23.211 | 1.00 | 73.39 | C |
| ATOM | 3313 | CD2 | LEU A | 448 | −57.035 | −3.579 | −23.476 | 1.00 | 71.07 | C |
| ATOM | 3314 | C | LEU A | 448 | −59.662 | −6.168 | −26.194 | 1.00 | 80.11 | C |
| ATOM | 3315 | O | LEU A | 448 | −60.258 | −5.209 | −26.695 | 1.00 | 79.17 | O |
| ATOM | 3316 | N | MET A | 449 | −60.293 | −7.235 | −25.660 | 1.00 | 84.58 | N |
| ATOM | 3317 | CA | MET A | 449 | −61.754 | −7.374 | −25.759 | 1.00 | 86.05 | C |
| ATOM | 3318 | CB | MET A | 449 | −62.286 | −8.714 | −25.237 | 1.00 | 91.93 | C |
| ATOM | 3319 | CG | MET A | 449 | −63.802 | −8.970 | −25.466 | 1.00 | 97.86 | C |
| ATOM | 3320 | SD | MET A | 449 | −64.487 | −9.063 | −27.165 | 1.00 | 103.28 | S |
| ATOM | 3321 | CE | MET A | 449 | −65.484 | −7.563 | −27.375 | 1.00 | 102.24 | C |
| ATOM | 3322 | C | MET A | 449 | −62.403 | −6.228 | −25.014 | 1.00 | 83.75 | C |
| ATOM | 3323 | O | MET A | 449 | −62.104 | −5.987 | −23.840 | 1.00 | 81.25 | O |
| ATOM | 3324 | N | GLY A | 450 | −63.251 | −5.499 | −25.745 | 1.00 | 79.77 | N |

TABLE 6-continued

Atomic coordinates for CRBN:DDB1: Compound B (Human protein)

| ATOM | 3325 | CA | GLY A | 450 | −63.996 | −4.397 | −25.192 | 1.00 | 74.77 | C |
|---|---|---|---|---|---|---|---|---|---|---|
| ATOM | 3326 | C | GLY A | 450 | −63.489 | −3.105 | −25.748 | 1.00 | 69.70 | C |
| ATOM | 3327 | O | GLY A | 450 | −64.250 | −2.140 | −25.825 | 1.00 | 67.69 | O |
| ATOM | 3328 | N | PHE A | 451 | −62.206 | −3.078 | −26.109 | 1.00 | 64.22 | N |
| ATOM | 3329 | CA | PHE A | 451 | −61.631 | −1.937 | −26.793 | 1.00 | 62.05 | C |
| ATOM | 3330 | CB | PHE A | 451 | −60.107 | −1.814 | −26.583 | 1.00 | 62.57 | C |
| ATOM | 3331 | CG | PHE A | 451 | −59.671 | −1.178 | −25.296 | 1.00 | 62.39 | C |
| ATOM | 3332 | CD1 | PHE A | 451 | −60.327 | −1.398 | −24.104 | 1.00 | 67.11 | C |
| ATOM | 3333 | CE1 | PHE A | 451 | −59.875 | −0.820 | −22.913 | 1.00 | 68.34 | C |
| ATOM | 3334 | CZ | PHE A | 451 | −58.725 | −0.056 | −22.899 | 1.00 | 67.44 | C |
| ATOM | 3335 | CE2 | PHE A | 451 | −58.034 | 0.143 | −24.086 | 1.00 | 66.05 | C |
| ATOM | 3336 | CD2 | PHE A | 451 | −58.510 | −0.431 | −25.267 | 1.00 | 64.36 | C |
| ATOM | 3337 | C | PHE A | 451 | −61.886 | −2.109 | −28.289 | 1.00 | 60.02 | C |
| ATOM | 3338 | O | PHE A | 451 | −61.596 | −3.118 | −28.902 | 1.00 | 64.88 | O |
| ATOM | 3339 | N | VAL A | 452 | −62.435 | −1.088 | −28.872 | 1.00 | 61.02 | N |
| ATOM | 3340 | CA | VAL A | 452 | −62.602 | −0.997 | −30.278 | 1.00 | 62.03 | C |
| ATOM | 3341 | CB | VAL A | 452 | −63.640 | 0.111 | −30.491 | 1.00 | 64.11 | C |
| ATOM | 3342 | CG1 | VAL A | 452 | −62.931 | 1.454 | −30.574 | 1.00 | 66.83 | C |
| ATOM | 3343 | CG2 | VAL A | 452 | −64.578 | −0.154 | −31.660 | 1.00 | 66.75 | C |
| ATOM | 3344 | C | VAL A | 452 | −61.243 | −0.680 | −30.952 | 1.00 | 63.88 | C |
| ATOM | 3345 | O | VAL A | 452 | −60.370 | −0.073 | −30.355 | 1.00 | 68.17 | O |
| ATOM | 3346 | N | ASP A | 453 | −61.120 | −1.068 | −32.216 | 1.00 | 68.36 | N |
| ATOM | 3347 | CA | ASP A | 453 | −59.873 | −1.050 | −33.039 | 1.00 | 68.59 | C |
| ATOM | 3348 | CB | ASP A | 453 | −59.530 | −2.496 | −33.429 | 1.00 | 72.33 | C |
| ATOM | 3349 | CG | ASP A | 453 | −60.680 | −3.172 | −34.219 | 1.00 | 81.47 | C |
| ATOM | 3350 | OD1 | ASP A | 453 | −61.725 | −3.629 | −33.644 | 1.00 | 91.62 | O |
| ATOM | 3351 | OD2 | ASP A | 453 | −60.561 | −3.198 | −35.444 | 1.00 | 83.04 | O |
| ATOM | 3352 | C | ASP A | 453 | −59.972 | −0.223 | −34.346 | 1.00 | 65.04 | C |
| ATOM | 3353 | O | ASP A | 453 | −58.958 | 0.155 | −34.926 | 1.00 | 58.22 | O |
| ATOM | 3354 | N | APS A | 454 | −61.195 | 0.044 | −34.801 | 1.00 | 68.88 | N |
| ATOM | 3355 | CA | APS A | 454 | −61.467 | 0.840 | −36.010 | 1.00 | 71.17 | C |
| ATOM | 3356 | CB | APS A | 454 | −62.700 | 0.273 | −36.751 | 1.00 | 74.89 | C |
| ATOM | 3357 | CG | APS A | 454 | −63.963 | 0.157 | −35.870 | 1.00 | 75.95 | C |
| ATOM | 3358 | OD1 | APS A | 454 | −63.860 | 0.192 | −34.627 | 1.00 | 73.27 | O |
| ATOM | 3359 | OD2 | APS A | 454 | −65.072 | 0.027 | −36.450 | 1.00 | 77.95 | O |
| ATOM | 3360 | C | APS A | 454 | −61.612 | 2.366 | −35.754 | 1.00 | 73.44 | C |
| ATOM | 3361 | O | APS A | 454 | −61.905 | 3.151 | −36.683 | 1.00 | 67.75 | O |
| ATOM | 3362 | N | GLN A | 455 | −61.359 | 2.778 | −34.504 | 1.00 | 76.50 | N |
| ATOM | 3363 | CA | GLN A | 455 | −61.435 | 4.166 | −34.089 | 1.00 | 75.17 | C |
| ATOM | 3364 | CB | GLN A | 455 | −62.582 | 4.291 | −33.093 | 1.00 | 75.59 | C |
| ATOM | 3365 | CG | GLN A | 455 | −63.958 | 4.003 | −33.699 | 1.00 | 78.47 | C |
| ATOM | 3366 | CD | GLN A | 455 | −64.450 | 5.113 | −34.632 | 1.00 | 82.23 | C |
| ATOM | 3367 | OE1 | GLN A | 455 | −63.789 | 6.143 | −34.806 | 1.00 | 89.16 | O |
| ATOM | 3368 | NE2 | GLN A | 455 | −65.625 | 4.914 | −35.222 | 1.00 | 80.72 | N |
| ATOM | 3369 | C | GLN A | 455 | −60.115 | 4.669 | −33.479 | 1.00 | 73.82 | C |
| ATOM | 3370 | O | GLN A | 455 | −59.434 | 3.928 | −32.770 | 1.00 | 70.89 | O |
| ATOM | 3371 | N | GLN A | 456 | −59.769 | 5.930 | −33.778 | 1.00 | 74.82 | N |
| ATOM | 3372 | CA | GLN A | 456 | −58.569 | 6.608 | −33.219 | 1.00 | 68.71 | C |
| ATOM | 3373 | CB | GLN A | 456 | −58.232 | 7.900 | −33.985 | 1.00 | 64.68 | C |
| ATOM | 3374 | CG | GLN A | 456 | −57.464 | 8.921 | −33.155 | 1.00 | 67.04 | C |
| ATOM | 3375 | CD | GLN A | 456 | −56.459 | 9.770 | −33.924 | 1.00 | 73.95 | C |
| ATOM | 3376 | OE1 | GLN A | 456 | −55.446 | 10.202 | −33.349 | 1.00 | 77.29 | O |
| ATOM | 3377 | NE2 | GLN A | 456 | −56.723 | 10.032 | −35.208 | 1.00 | 74.87 | N |
| ATOM | 3378 | C | GLN A | 456 | −58.708 | 6.911 | −31.719 | 1.00 | 64.86 | C |
| ATOM | 3379 | O | GLN A | 456 | −59.487 | 7.774 | −31.323 | 1.00 | 66.79 | O |
| ATOM | 3380 | N | THR A | 457 | −57.914 | 6.229 | −30.903 | 1.00 | 58.17 | N |
| ATOM | 3381 | CA | THR A | 457 | −57.893 | 6.483 | −29.475 | 1.00 | 53.77 | C |
| ATOM | 3382 | CB | THR A | 457 | −57.322 | 5.247 | −28.739 | 1.00 | 46.86 | C |
| ATOM | 3383 | OG1 | THR A | 457 | −58.203 | 4.161 | −28.998 | 1.00 | 43.00 | O |
| ATOM | 3384 | CG2 | THR A | 457 | −57.207 | 5.437 | −27.221 | 1.00 | 42.63 | C |
| ATOM | 3385 | C | THR A | 457 | −57.207 | 7.849 | −29.120 | 1.00 | 56.21 | C |
| ATOM | 3386 | O | THR A | 457 | −56.197 | 8.273 | −29.768 | 1.00 | 48.43 | O |
| ATOM | 3387 | N | PHE A | 458 | −57.840 | 8.536 | −28.143 | 1.00 | 58.50 | N |
| ATOM | 3388 | CA | PHE A | 458 | −57.344 | 9.792 | −27.507 | 1.00 | 63.71 | C |
| ATOM | 3389 | CB | PHE A | 458 | −58.404 | 10.942 | −27.546 | 1.00 | 66.60 | C |
| ATOM | 3390 | CG | PHE A | 458 | −58.690 | 11.481 | −28.941 | 1.00 | 68.81 | C |
| ATOM | 3391 | CD1 | PHE A | 458 | −57.672 | 11.858 | −29.785 | 1.00 | 72.65 | C |
| ATOM | 3392 | CE1 | PHE A | 458 | −57.931 | 12.326 | −31.066 | 1.00 | 76.96 | C |
| ATOM | 3393 | CZ | PHE A | 458 | −59.223 | 12.429 | −31.513 | 1.00 | 79.83 | C |
| ATOM | 3394 | CE2 | PHE A | 458 | −60.253 | 12.066 | −30.676 | 1.00 | 79.37 | C |
| ATOM | 3395 | CD2 | PHE A | 458 | −59.983 | 11.602 | −29.399 | 1.00 | 75.30 | C |
| ATOM | 3396 | C | PHE A | 458 | −56.860 | 9.603 | −26.057 | 1.00 | 59.35 | C |
| ATOM | 3397 | O | PHE A | 458 | −56.082 | 10.412 | −25.527 | 1.00 | 58.20 | O |
| ATOM | 3398 | N | PHE A | 459 | −57.336 | 8.565 | −25.405 | 1.00 | 54.06 | N |
| ATOM | 3399 | CA | PHE A | 459 | −56.763 | 8.172 | −24.144 | 1.00 | 52.76 | C |
| ATOM | 3400 | CB | PHE A | 459 | −57.161 | 9.158 | −23.022 | 1.00 | 52.39 | C |
| ATOM | 3401 | CG | PHE A | 459 | −56.781 | 8.678 | −21.651 | 1.00 | 51.51 | C |
| ATOM | 3402 | CD1 | PHE A | 459 | −57.508 | 7.665 | −21.020 | 1.00 | 51.81 | C |

TABLE 6-continued

Atomic coordinates for CRBN:DDB1: Compound B (Human protein)

| ATOM | 3403 | CE1 | PHE A | 459 | −57.107 | 7.167 | −19.783 | 1.00 | 52.94 | C |
|---|---|---|---|---|---|---|---|---|---|---|
| ATOM | 3404 | CZ | PHE A | 459 | −55.996 | 7.695 | −19.154 | 1.00 | 50.03 | C |
| ATOM | 3405 | CE2 | PHE A | 459 | −55.270 | 8.683 | −19.777 | 1.00 | 49.18 | C |
| ATOM | 3406 | CD2 | PHE A | 459 | −55.656 | 9.169 | −21.017 | 1.00 | 50.02 | C |
| ATOM | 3407 | C | PHE A | 459 | −57.226 | 6.752 | −23.798 | 1.00 | 54.37 | C |
| ATOM | 3408 | O | PHE A | 459 | −58.348 | 6.378 | −24.056 | 1.00 | 58.85 | O |
| ATOM | 3409 | N | CYS A | 460 | −56.356 | 5.953 | −23.206 | 1.00 | 57.49 | N |
| ATOM | 3410 | CA | CYS A | 460 | −56.800 | 4.795 | −22.474 | 1.00 | 58.31 | C |
| ATOM | 3411 | CB | CYS A | 460 | −56.859 | 3.590 | −23.393 | 1.00 | 63.79 | C |
| ATOM | 3412 | SG | CYS A | 460 | −55.264 | 3.174 | −24.079 | 1.00 | 76.64 | S |
| ATOM | 3413 | C | CYS A | 460 | −55.918 | 4.537 | −21.265 | 1.00 | 56.34 | C |
| ATOM | 3414 | O | CYS A | 460 | −54.885 | 5.196 | −21.047 | 1.00 | 54.92 | O |
| ATOM | 3415 | N | GLY A | 461 | −56.373 | 3.623 | −20.438 | 1.00 | 55.51 | N |
| ATOM | 3416 | CA | GLY A | 461 | −55.601 | 3.223 | −19.303 | 1.00 | 62.01 | C |
| ATOM | 3417 | C | GLY A | 461 | −56.449 | 2.649 | −18.212 | 1.00 | 65.42 | C |
| ATOM | 3418 | O | GLY A | 461 | −57.647 | 2.446 | −18.391 | 1.00 | 61.81 | O |
| ATOM | 3419 | N | ASN A | 462 | −55.804 | 2.429 | −17.068 | 1.00 | 69.15 | N |
| ATOM | 3420 | CA | ASN A | 462 | −56.491 | 1.959 | −15.896 | 1.00 | 72.43 | C |
| ATOM | 3421 | CB | ASN A | 462 | −55.530 | 1.398 | −14.881 | 1.00 | 76.01 | C |
| ATOM | 3422 | CG | ASN A | 462 | −54.733 | 0.268 | −15.413 | 1.00 | 75.52 | C |
| ATOM | 3423 | OD1 | ASN A | 462 | −55.231 | −0.845 | −15.588 | 1.00 | 70.68 | O |
| ATOM | 3424 | ND2 | ASN A | 462 | −53.469 | 0.539 | −15.657 | 1.00 | 81.51 | N |
| ATOM | 3425 | C | ASN A | 462 | −57.241 | 3.078 | −15.210 | 1.00 | 73.47 | C |
| ATOM | 3426 | O | ASN A | 462 | −56.816 | 4.251 | −15.211 | 1.00 | 68.37 | O |
| ATOM | 3427 | N | VAL A | 463 | −58.331 | 2.675 | −14.567 | 1.00 | 76.54 | N |
| ATOM | 3428 | CA | VAL A | 463 | −59.189 | 3.601 | −13.860 | 1.00 | 77.45 | C |
| ATOM | 3429 | CB | VAL A | 463 | −60.251 | 4.200 | −14.827 | 1.00 | 73.62 | C |
| ATOM | 3430 | CG1 | VAL A | 463 | −59.672 | 5.375 | −15.641 | 1.00 | 70.05 | C |
| ATOM | 3431 | CG2 | VAL A | 463 | −60.802 | 3.125 | −15.762 | 1.00 | 71.98 | C |
| ATOM | 3432 | C | VAL A | 463 | −59.761 | 2.877 | −12.639 | 1.00 | 78.42 | C |
| ATOM | 3433 | O | VAL A | 463 | −59.678 | 1.645 | −12.540 | 1.00 | 80.84 | O |
| ATOM | 3434 | N | ALA A | 464 | −60.301 | 3.652 | −11.704 | 1.00 | 82.57 | N |
| ATOM | 3435 | CA | ALA A | 464 | −60.740 | 3.132 | −10.397 | 1.00 | 88.14 | C |
| ATOM | 3436 | CB | ALA A | 464 | −61.257 | 4.271 | −9.522 | 1.00 | 86.99 | C |
| ATOM | 3437 | C | ALA A | 464 | −61.783 | 2.006 | −10.482 | 1.00 | 89.93 | C |
| ATOM | 3438 | O | ALA A | 464 | −62.364 | 1.752 | −11.542 | 1.00 | −85.64 | O |
| ATOM | 3439 | N | HIS A | 465 | −62.005 | 1.340 | −9.348 | 1.00 | 92.45 | N |
| ATOM | 3440 | CA | HIS A | 465 | −62.883 | 0.175 | −9.279 | 1.00 | 90.92 | C |
| ATOM | 3441 | CB | HIS A | 465 | −64.396 | 0.566 | −9.366 | 1.00 | 90.71 | C |
| ATOM | 3442 | CG | HIS A | 465 | −64.766 | 1.915 | −8.789 | 1.00 | 93.76 | C |
| ATOM | 3443 | ND1 | HIS A | 465 | −64.689 | 2.211 | −7.442 | 1.00 | 94.95 | N |
| ATOM | 3444 | CE1 | HIS A | 465 | −65.108 | 3.449 | −7.236 | 1.00 | 91.23 | C |
| ATOM | 3445 | NE2 | HIS A | 465 | −65.484 | 3.962 | −8.396 | 1.00 | 87.66 | N |
| ATOM | 3446 | CD2 | HIS A | 465 | −65.297 | 3.020 | −9.380 | 1.00 | 89.83 | C |
| ATOM | 3447 | C | HIS A | 465 | −62.521 | −0.820 | −10.418 | 1.00 | 89.87 | C |
| ATOM | 3448 | O | HIS A | 465 | −63.310 | −0.988 | −11.334 | 1.00 | 92.92 | O |
| ATOM | 3449 | N | GLN A | 466 | −61.324 | −1.413 | −10.397 | 1.00 | 86.34 | N |
| ATOM | 3450 | CA | GLN A | 466 | −60.926 | −2.525 | −11.327 | 1.00 | 86.05 | C |
| ATOM | 3451 | CB | GLN A | 466 | −61.311 | −3.887 | −10.734 | 1.00 | 90.40 | C |
| ATOM | 3452 | CG | GLN A | 466 | −60.977 | −4.104 | −9.257 | 1.00 | 95.89 | C |
| ATOM | 3453 | CD | GLN A | 466 | −59.659 | −4.832 | −9.043 | 1.00 | 96.46 | C |
| ATOM | 3454 | OE1 | GLN A | 466 | −59.631 | −6.008 | −8.650 | 1.00 | 88.58 | O |
| ATOM | 3455 | NE2 | GLN A | 466 | −58.559 | −4.134 | −9.294 | 1.00 | 96.20 | N |
| ATOM | 3456 | C | GLN A | 466 | −61.426 | −2.452 | −12.806 | 1.00 | 82.21 | C |
| ATOM | 3457 | O | GLN A | 466 | −62.078 | −3.379 | −13.324 | 1.00 | 76.09 | O |
| ATOM | 3458 | N | GLN A | 467 | −61.084 | −1.348 | −13.477 | 1.00 | 81.73 | N |
| ATOM | 3459 | CA | GLN A | 467 | −61.514 | −1.066 | −14.855 | 1.00 | 76.82 | C |
| ATOM | 3460 | CB | GLN A | 467 | −62.729 | −0.136 | −14.854 | 1.00 | 83.56 | C |
| ATOM | 3461 | CG | GLN A | 467 | −64.038 | −0.839 | −14.525 | 1.00 | 92.13 | C |
| ATOM | 3462 | CD | GLN A | 467 | −65.185 | 0.109 | −14.225 | 1.00 | 90.24 | C |
| ATOM | 3463 | OE1 | GLN A | 467 | −65.020 | 1.118 | −13.537 | 1.00 | 87.11 | O |
| ATOM | 3464 | NE2 | GLN A | 467 | −66.367 | −0.234 | −14.726 | 1.00 | 92.54 | N |
| ATOM | 3465 | C | GLN A | 467 | −60.455 | −0.425 | −15.740 | 1.00 | 69.88 | C |
| ATOM | 3466 | O | GLN A | 467 | −59.466 | 0.163 | −15.266 | 1.00 | 63.14 | O |
| ATOM | 3467 | N | LEU A | 468 | −60.725 | −0.568 | −17.039 | 1.00 | 68.22 | N |
| ATOM | 3468 | CA | LEU A | 468 | −59.992 | 0.025 | −18.148 | 1.00 | 69.11 | C |
| ATOM | 3469 | CB | LEU A | 468 | −59.616 | −1.033 | −19.201 | 1.00 | 69.21 | C |
| ATOM | 3470 | CG | LEU A | 468 | −58.683 | −2.143 | −18.730 | 1.00 | 71.99 | C |
| ATOM | 3471 | CD1 | LEU A | 468 | −58.443 | −3.222 | −19.775 | 1.00 | 70.08 | C |
| ATOM | 3472 | CD2 | LEU A | 468 | −57.373 | −1.505 | −18.281 | 1.00 | 76.30 | C |
| ATOM | 3473 | C | LEU A | 468 | −60.943 | 0.951 | −18.820 | 1.00 | 67.99 | C |
| ATOM | 3474 | O | LEU A | 468 | −62.108 | 0.609 | −18.958 | 1.00 | 71.06 | O |
| ATOM | 3475 | N | ILE A | 469 | −60.451 | 2.092 | −19.271 | 1.00 | 66.25 | N |
| ATOM | 3476 | CA | ILE A | 469 | −61.254 | 3.015 | −20.060 | 1.00 | 70.78 | C |
| ATOM | 3477 | CB | ILE A | 469 | −61.523 | 4.337 | −19.276 | 1.00 | 73.05 | C |
| ATOM | 3478 | CG1 | ILE A | 469 | −62.712 | 5.087 | −19.885 | 1.00 | 72.05 | C |
| ATOM | 3479 | CD1 | ILE A | 469 | −62.901 | 6.500 | −19.389 | 1.00 | 72.86 | C |
| ATOM | 3480 | CG2 | ILE A | 469 | −60.271 | 5.225 | −19.192 | 1.00 | 75.98 | C |

TABLE 6-continued

Atomic coordinates for CRBN:DDB1: Compound B (Human protein)

| ATOM | 3481 | C | ILE A | 469 | −60.528 | 3.262 | −21.384 | 1.00 | 68.40 | C |
|---|---|---|---|---|---|---|---|---|---|---|
| ATOM | 3482 | O | ILE A | 469 | −59.337 | 3.349 | −21.391 | 1.00 | 74.21 | O |
| ATOM | 3483 | N | GLN A | 470 | −61.242 | 3.337 | −22.496 | 1.00 | 68.72 | N |
| ATOM | 3484 | CA | GLN A | 470 | −60.683 | 3.799 | −23.772 | 1.00 | 67.86 | C |
| ATOM | 3485 | CB | GLN A | 470 | −60.754 | 2.679 | −24.805 | 1.00 | 69.50 | C |
| ATOM | 3486 | CG | GLN A | 470 | −60.024 | 2.997 | −26.112 | 1.00 | 70.87 | C |
| ATOM | 3487 | CD | GLN A | 470 | −60.373 | 2.091 | −27.291 | 1.00 | 71.09 | C |
| ATOM | 3488 | OE1 | GLN A | 470 | −59.909 | 2.319 | −28.410 | 1.00 | 72.19 | O |
| ATOM | 3489 | NE2 | GLN A | 470 | −61.159 | 1.069 | −27.060 | 1.00 | 68.45 | N |
| ATOM | 3490 | C | GLN A | 470 | −61.530 | 4.949 | −24.263 | 1.00 | 64.13 | C |
| ATOM | 3491 | O | GLN A | 470 | −62.726 | 4.877 | −24.213 | 1.00 | 72.46 | O |
| ATOM | 3492 | N | ILE A | 471 | −60.938 | 5.994 | −24.779 | 1.00 | 60.99 | N |
| ATOM | 3493 | CA | ILE A | 471 | −61.723 | 7.127 | −25.256 | 1.00 | 64.27 | C |
| ATOM | 3494 | CB | ILE A | 471 | −61.432 | 8.378 | −24.416 | 1.00 | 62.44 | C |
| ATOM | 3495 | CG1 | ILE A | 471 | −61.904 | 8.170 | −22.987 | 1.00 | 62.39 | C |
| ATOM | 3496 | CD1 | ILE A | 471 | −61.346 | 9.200 | −22.038 | 1.00 | 63.28 | C |
| ATOM | 3497 | CG2 | ILE A | 471 | −62.119 | 9.589 | −25.007 | 1.00 | 63.59 | C |
| ATOM | 3498 | C | ILE A | 471 | −61.433 | 7.393 | −26.738 | 1.00 | 65.79 | C |
| ATOM | 3499 | O | ILE A | 471 | −60.329 | 7.821 | −27.089 | 1.00 | 67.88 | O |
| ATOM | 3500 | N | THR A | 472 | −62.434 | 7.159 | −27.584 | 1.00 | 66.46 | N |
| ATOM | 3501 | CA | THR A | 472 | −62.283 | 7.256 | −29.014 | 1.00 | 71.15 | C |
| ATOM | 3502 | CB | THR A | 472 | −63.095 | 6.179 | −29.738 | 1.00 | 79.58 | C |
| ATOM | 3503 | OG1 | THR A | 472 | −64.489 | 6.312 | −29.410 | 1.00 | 90.03 | O |
| ATOM | 3504 | CG2 | THR A | 472 | −62.590 | 4.808 | −29.336 | 1.00 | 81.15 | C |
| ATOM | 3505 | C | THR A | 472 | −62.803 | 8.583 | −29.426 | 1.00 | 69.90 | C |
| ATOM | 3506 | O | THR A | 472 | −63.333 | 9.289 | −28.597 | 1.00 | 67.70 | O |
| ATOM | 3507 | N | SER A | 473 | −62.619 | 8.917 | −30.713 | 1.00 | 74.95 | N |
| ATOM | 3508 | CA | SER A | 473 | −63.275 | 10.076 | −31.375 | 1.00 | 69.82 | C |
| ATOM | 3509 | CB | SER A | 473 | −62.693 | 10.356 | −32.778 | 1.00 | 66.25 | C |
| ATOM | 3510 | OG | SER A | 473 | −62.446 | 9.146 | −33.485 | 1.00 | 67.45 | O |
| ATOM | 3511 | C | SER A | 473 | −64.770 | 9.800 | −31.460 | 1.00 | 66.56 | C |
| ATOM | 3512 | O | SER A | 473 | −65.573 | 10.711 | −31.450 | 1.00 | 62.76 | O |
| ATOM | 3513 | N | ALA A | 474 | −65.137 | 8.526 | −31.509 | 1.00 | 65.03 | N |
| ATOM | 3514 | CA | ALA A | 474 | −66.536 | 8.158 | −31.490 | 1.00 | 62.64 | C |
| ATOM | 3515 | CB | ALA A | 474 | −66.707 | 6.833 | −32.208 | 1.00 | 65.15 | C |
| ATOM | 3516 | C | ALA A | 474 | −67.196 | 8.096 | −30.108 | 1.00 | 54.73 | C |
| ATOM | 3517 | O | ALA A | 474 | −68.386 | 8.268 | −30.029 | 1.00 | 58.36 | O |
| ATOM | 3518 | N | SER A | 475 | −66.488 | 7.826 | −29.035 | 0.50 | 47.34 | N |
| ATOM | 3519 | CA | SER A | 475 | −67.201 | 7.465 | −27.857 | 0.50 | 44.42 | C |
| ATOM | 3520 | CB | SER A | 475 | −67.898 | 6.126 | −28.060 | 0.50 | 41.91 | C |
| ATOM | 3521 | OG | SER A | 475 | −66.942 | 5.089 | −28.064 | 0.50 | 41.30 | O |
| ATOM | 3522 | C | SER A | 475 | −66.243 | 7.327 | −26.747 | 0.50 | 46.77 | C |
| ATOM | 3523 | O | SER A | 475 | −65.050 | 7.466 | −26.927 | 0.50 | 44.61 | O |
| ATOM | 3524 | N | VAL A | 476 | −66.806 | 7.059 | −25.582 | 1.00 | 52.05 | N |
| ATOM | 3525 | CA | VAL A | 476 | −66.060 | 6.734 | −24.363 | 1.00 | 57.75 | C |
| ATOM | 3526 | CB | VAL A | 476 | −66.329 | 7.779 | −23.232 | 1.00 | 57.85 | C |
| ATOM | 3527 | CG1 | VAL A | 476 | −65.588 | 7.422 | −21.949 | 1.00 | 58.87 | C |
| ATOM | 3528 | CG2 | VAL A | 476 | −65.943 | 9.180 | −23.670 | 1.00 | 58.26 | C |
| ATOM | 3529 | C | VAL A | 476 | −66.415 | 5.298 | −23.864 | 1.00 | 59.13 | C |
| ATOM | 3530 | O | VAL A | 476 | −67.336 | 5.097 | −23.104 | 1.00 | 56.11 | O |
| ATOM | 3531 | N | ARG A | 477 | −65.634 | 4.311 | −24.267 | 1.00 | 63.70 | N |
| ATOM | 3532 | CA | ARG A | 477 | −65.831 | 2.933 | −23.818 | 1.00 | 64.48 | C |
| ATOM | 3533 | CB | ARG A | 477 | −65.277 | 1.991 | −24.878 | 1.00 | 66.03 | C |
| ATOM | 3534 | CG | ARG A | 477 | −65.984 | 2.217 | −26.228 | 1.00 | 70.03 | C |
| ATOM | 3535 | CD | ARG A | 477 | −65.343 | 1.471 | −27.375 | 1.00 | 71.35 | C |
| ATOM | 3536 | NE | ARG A | 477 | −65.518 | 0.047 | −27.177 | 1.00 | 75.69 | N |
| ATOM | 3537 | CZ | ARG A | 477 | −66.561 | −0.666 | −27.583 | 1.00 | 80.43 | C |
| ATOM | 3538 | NH1 | ARG A | 477 | −67.572 | −0.115 | −28.251 | 1.00 | 84.67 | N |
| ATOM | 3539 | NH2 | ARG A | 477 | −66.589 | −1.963 | −27.310 | 1.00 | 84.80 | N |
| ATOM | 3540 | C | ARG A | 477 | −65.248 | 2.709 | −22.410 | 1.00 | 63.87 | C |
| ATOM | 3541 | O | ARG A | 477 | −64.381 | 3.439 | −21.983 | 1.00 | 59.82 | O |
| ATOM | 3542 | N | LEU A | 478 | −65.793 | 1.752 | −21.666 | 1.00 | 63.07 | N |
| ATOM | 3543 | CA | LEU A | 478 | −65.366 | 1.526 | −20.291 | 1.00 | 63.21 | C |
| ATOM | 3544 | CB | LEU A | 478 | −66.185 | 2.382 | −19.320 | 1.00 | 62.60 | C |
| ATOM | 3545 | CG | LEU A | 478 | −66.028 | 2.112 | −17.801 | 1.00 | 61.30 | C |
| ATOM | 3546 | CD1 | LEU A | 478 | −64.642 | 2.385 | −17.241 | 1.00 | 60.32 | C |
| ATOM | 3547 | CD2 | LEU A | 478 | −67.016 | 2.981 | −17.074 | 1.00 | 62.73 | C |
| ATOM | 3548 | C | LEU A | 478 | −65.519 | 0.064 | −19.972 | 1.00 | 63.57 | C |
| ATOM | 3549 | O | LEU A | 478 | −66.596 | −0.472 | −20.095 | 1.00 | 63.70 | O |
| ATOM | 3550 | N | VAL A | 479 | −64.439 | −0.561 | −19.520 | 1.00 | 68.27 | N |
| ATOM | 3551 | CA | VAL A | 479 | −64.252 | −2.011 | −19.675 | 1.00 | 72.02 | C |
| ATOM | 3552 | CB | VAL A | 479 | −63.235 | −2.307 | −20.839 | 1.00 | 69.26 | C |
| ATOM | 3553 | CG1 | VAL A | 479 | −62.916 | −3.793 | −20.955 | 1.00 | 69.10 | C |
| ATOM | 3554 | CG2 | VAL A | 479 | −63.761 | −1.784 | −22.188 | 1.00 | 67.20 | C |
| ATOM | 3555 | C | VAL A | 479 | −63.820 | −2.643 | −18.349 | 1.00 | 73.33 | C |
| ATOM | 3556 | O | VAL A | 479 | −63.089 | −2.044 | −17.566 | 1.00 | 76.56 | O |
| ATOM | 3557 | N | SER A | 480 | −64.298 | −3.847 | −18.098 | 1.00 | 74.88 | N |
| ATOM | 3558 | CA | SER A | 480 | −64.008 | −4.538 | −16.857 | 1.00 | 79.98 | C |

TABLE 6-continued

Atomic coordinates for CRBN:DDB1: Compound B (Human protein)

| ATOM | 3559 | CB | SER A | 480 | −65.060 | −5.623 | −16.629 | 1.00 | 79.45 | C |
|---|---|---|---|---|---|---|---|---|---|---|
| ATOM | 3560 | OG | SER A | 480 | −65.340 | −6.299 | −17.842 | 1.00 | 76.52 | O |
| ATOM | 3561 | C | SER A | 480 | −62.657 | −5.183 | −16.981 | 1.00 | 85.87 | C |
| ATOM | 3562 | O | SER A | 480 | −62.285 | −5.577 | −18.077 | 1.00 | 87.77 | O |
| ATOM | 3563 | N | GLN A | 481 | −61.941 | −5.311 | −15.861 | 1.00 | 95.89 | N |
| ATOM | 3564 | CA | GLN A | 481 | −60.740 | −6.175 | −15.779 | 1.00 | 97.16 | C |
| ATOM | 3565 | CB | GLN A | 481 | −59.952 | −5.880 | −14.525 | 1.00 | 100.28 | C |
| ATOM | 3566 | CG | GLN A | 481 | −59.350 | −4.496 | −14.528 | 1.00 | 105.20 | C |
| ATOM | 3567 | CD | GLN A | 481 | −57.976 | −4.461 | −15.166 | 1.00 | 103.65 | C |
| ATOM | 3568 | OE1 | GLN A | 481 | −57.755 | −4.989 | −16.267 | 1.00 | 93.06 | O |
| ATOM | 3569 | NE2 | GLN A | 481 | −57.032 | −3.836 | −14.462 | 1.00 | 104.34 | N |
| ATOM | 3570 | C | GLN A | 481 | −61.067 | −7.655 | −15.760 | 1.00 | 99.60 | C |
| ATOM | 3571 | O | GLN A | 481 | −60.551 | −8.401 | −16.576 | 1.00 | 93.92 | O |
| ATOM | 3572 | N | GLU A | 482 | −61.912 | −8.061 | −14.809 | 1.00 | 109.91 | N |
| ATOM | 3573 | CA | GLU A | 482 | −62.300 | −9.464 | −14.610 | 1.00 | 111.86 | C |
| ATOM | 3574 | CB | GLU A | 482 | −62.702 | −9.661 | −13.135 | 1.00 | 119.75 | C |
| ATOM | 3575 | CG | GLU A | 482 | −62.700 | −11.097 | −12.618 | 1.00 | 127.42 | C |
| ATOM | 3576 | CD | GLU A | 482 | −61.399 | −11.840 | −12.914 | 1.00 | 128.99 | C |
| ATOM | 3577 | OE1 | GLU A | 482 | −60.367 | −11.170 | −13.147 | 1.00 | 117.71 | O |
| ATOM | 3578 | OE2 | GLU A | 482 | −61.408 | −13.094 | −12.914 | 1.00 | 128.98 | O |
| ATOM | 3579 | C | GLU A | 482 | −63.435 | −9.844 | −15.582 | 1.00 | 109.44 | C |
| ATOM | 3580 | O | GLU A | 482 | −64.564 | −9.390 | −15.411 | 1.00 | 100.16 | O |
| ATOM | 3581 | N | PRO A | 483 | −63.161 | −10.777 | −16.533 | 1.00 | 112.39 | N |
| ATOM | 3582 | CA | PRO A | 483 | −63.480 | −10.750 | −17.963 | 1.00 | 103.19 | C |
| ATOM | 3583 | CB | PRO A | 483 | −64.782 | −11.536 | −18.021 | 1.00 | 107.09 | C |
| ATOM | 3584 | CG | PRO A | 483 | −64.494 | −12.653 | −17.030 | 1.00 | 115.95 | C |
| ATOM | 3585 | CD | PRO A | 483 | −63.364 | −12.172 | −16.095 | 1.00 | 118.58 | C |
| ATOM | 3586 | C | PRO A | 483 | −63.562 | −9.387 | −18.603 | 1.00 | 94.45 | C |
| ATOM | 3587 | O | PRO A | 483 | −63.824 | −8.380 | −17.941 | 1.00 | 87.76 | O |
| ATOM | 3588 | N | LYS A | 484 | −63.264 | −9.347 | −19.890 | 1.00 | 90.10 | N |
| ATOM | 3589 | CA | LYS A | 484 | −63.239 | −8.076 | −20.588 | 1.00 | 86.65 | C |
| ATOM | 3590 | CB | LYS A | 484 | −61.936 | −7.891 | −21.372 | 1.00 | 83.73 | C |
| ATOM | 3591 | CG | LYS A | 484 | −60.762 | −7.486 | −20.485 | 1.00 | 81.56 | C |
| ATOM | 3592 | CD | LYS A | 484 | −59.490 | −8.246 | −20.830 | 1.00 | 84.99 | C |
| ATOM | 3593 | CE | LYS A | 484 | −58.566 | −8.422 | −19.637 | 1.00 | 81.79 | C |
| ATOM | 3594 | NZ | LYS A | 484 | −58.223 | −7.100 | −19.044 | 1.00 | 81.23 | N |
| ATOM | 3595 | C | LYS A | 484 | −64.462 | −7.992 | −21.472 | 1.00 | 85.46 | C |
| ATOM | 3596 | O | LYS A | 484 | −64.618 | −8.770 | −22.427 | 1.00 | 91.72 | O |
| ATOM | 3597 | N | ALA A | 485 | −65.367 | −7.097 | −21.084 | 1.00 | 79.50 | N |
| ATOM | 3598 | CA | ALA A | 485 | −66.332 | −6.534 | −22.015 | 1.00 | 79.39 | C |
| ATOM | 3599 | CB | ALA A | 485 | −67.581 | −7.399 | −22.112 | 1.00 | 80.62 | C |
| ATOM | 3600 | C | ALA A | 485 | −66.686 | −5.088 | −21.646 | 1.00 | 77.19 | C |
| ATOM | 3601 | O | ALA A | 485 | −66.403 | −4.601 | −20.526 | 1.00 | 72.32 | O |
| ATOM | 3602 | N | LEU A | 486 | −67.278 | −4.407 | −22.629 | 1.00 | 74.61 | N |
| ATOM | 3603 | CA | LEU A | 486 | −67.900 | −3.100 | −22.425 | 1.00 | 74.26 | C |
| ATOM | 3604 | CB | LEU A | 486 | −68.736 | −2.708 | −23.675 | 1.00 | 72.97 | C |
| ATOM | 3605 | CG | LEU A | 486 | −68.891 | −1.216 | −24.026 | 1.00 | 74.79 | C |
| ATOM | 3606 | CD1 | LEU A | 486 | −67.496 | −0.652 | −24.284 | 1.00 | 82.22 | C |
| ATOM | 3607 | CD2 | LEU A | 486 | −69.786 | −0.889 | −25.225 | 1.00 | 71.33 | C |
| ATOM | 3608 | C | LEU A | 486 | −68.806 | −3.217 | −21.198 | 1.00 | 78.02 | C |
| ATOM | 3609 | O | LEU A | 486 | −69.595 | −4.166 | −21.128 | 1.00 | 87.07 | O |
| ATOM | 3610 | N | VAL A | 487 | −68.664 | −2.336 | −20.205 | 1.00 | 75.30 | N |
| ATOM | 3611 | CA | VAL A | 487 | −69.667 | −2.261 | −19.123 | 1.00 | 72.80 | C |
| ATOM | 3612 | CB | VAL A | 487 | −69.115 | −2.649 | −17.698 | 1.00 | 74.60 | C |
| ATOM | 3613 | CG1 | VAL A | 487 | −68.662 | −4.114 | −17.634 | 1.00 | 73.18 | C |
| ATOM | 3614 | CG2 | VAL A | 487 | −67.982 | −1.746 | −17.242 | 1.00 | 77.36 | C |
| ATOM | 3615 | C | VAL A | 487 | −70.410 | −0.913 | −19.145 | 1.00 | 69.50 | C |
| ATOM | 3616 | O | VAL A | 487 | −71.245 | −0.659 | −18.273 | 1.00 | 71.87 | O |
| ATOM | 3617 | N | SER A | 488 | −70.168 | −0.103 | −20.175 | 1.00 | 66.45 | N |
| ATOM | 3618 | CA | SER A | 488 | −70.663 | 1.276 | −20.241 | 1.00 | 73.61 | C |
| ATOM | 3619 | CB | SER A | 488 | −70.095 | 2.122 | −19.107 | 1.00 | 75.10 | C |
| ATOM | 3620 | OG | SER A | 488 | −70.889 | 2.053 | −17.951 | 1.00 | 85.22 | O |
| ATOM | 3621 | C | SER A | 488 | −70.172 | 1.943 | −21.492 | 1.00 | 76.45 | C |
| ATOM | 3622 | O | SER A | 488 | −69.072 | 1.647 | −21.917 | 1.00 | 87.45 | O |
| ATOM | 3623 | N | GLU A | 489 | −70.937 | 2.884 | −22.035 | 1.00 | 72.34 | N |
| ATOM | 3624 | CA | GLU A | 489 | −70.469 | 3.720 | −23.139 | 1.00 | 70.12 | C |
| ATOM | 3625 | CB | GLU A | 489 | −70.575 | 2.986 | −24.496 | 1.00 | 72.77 | C |
| ATOM | 3626 | CG | GLU A | 489 | −70.153 | 3.822 | −25.720 | 1.00 | 76.03 | C |
| ATOM | 3627 | CD | GLU A | 489 | −69.747 | 3.004 | −26.948 | 1.00 | 75.70 | C |
| ATOM | 3628 | OE1 | GLU A | 489 | −68.774 | 3.393 | −27.643 | 1.00 | 72.20 | O |
| ATOM | 3629 | OE2 | GLU A | 489 | −70.393 | 1.973 | −27.222 | 1.00 | 80.05 | O |
| ATOM | 3630 | C | GLU A | 489 | −71.227 | 5.042 | −23.128 | 1.00 | 68.87 | C |
| ATOM | 3631 | O | GLU A | 489 | −72.354 | 5.118 | −22.683 | 1.00 | 74.47 | O |
| ATOM | 3632 | N | TRP A | 490 | −70.583 | 6.090 | −23.593 | 1.00 | 68.64 | N |
| ATOM | 3633 | CA | TRP A | 490 | −71.100 | 7.427 | −23.509 | 1.00 | 68.15 | C |
| ATOM | 3634 | CB | TRP A | 490 | −70.232 | 8.208 | −22.529 | 1.00 | 65.75 | C |
| ATOM | 3635 | CG | TRP A | 490 | −70.722 | 9.500 | −22.305 | 1.00 | 68.72 | C |
| ATOM | 3636 | CD1 | TRP A | 490 | −71.548 | 9.866 | −21.320 | 1.00 | 73.62 | C |

TABLE 6-continued

Atomic coordinates for CRBN:DDB1: Compound B (Human protein)

| ATOM | 3637 | NE1 | TRP A | 490 | −71.853 | 11.208 | −21.439 | 1.00 | 80.51 | N |
|---|---|---|---|---|---|---|---|---|---|---|
| ATOM | 3638 | CE2 | TRP A | 490 | −71.205 | 11.726 | −22.533 | 1.00 | 78.90 | C |
| ATOM | 3639 | CD2 | TRP A | 490 | −70.484 | 10.675 | −23.113 | 1.00 | 75.99 | C |
| ATOM | 3640 | CE3 | TRP A | 490 | −69.716 | 10.942 | −24.270 | 1.00 | 79.27 | C |
| ATOM | 3641 | CZ3 | TRP A | 490 | −69.704 | 12.246 | −24.803 | 1.00 | 76.05 | C |
| ATOM | 3642 | CH2 | TRP A | 490 | −70.435 | 13.261 | −24.198 | 1.00 | 79.73 | C |
| ATOM | 3643 | CZ2 | TRP A | 490 | −71.189 | 13.032 | −23.064 | 1.00 | 80.00 | C |
| ATOM | 3644 | C | TRP A | 490 | −70.983 | 7.986 | −24.906 | 1.00 | 72.80 | C |
| ATOM | 3645 | O | TRP A | 490 | −69.889 | 8.027 | −25.444 | 1.00 | 77.47 | O |
| ATOM | 3646 | N | LYS A | 491 | −72.081 | 8.403 | −25.515 | 1.00 | 80.84 | N |
| ATOM | 3647 | CA | LYS A | 491 | −72.013 | 8.971 | −26.853 | 1.00 | 89.00 | C |
| ATOM | 3648 | CB | LYS A | 491 | −73.000 | 8.250 | −27.778 | 1.00 | 102.16 | C |
| ATOM | 3649 | CG | LYS A | 491 | −72.755 | 8.531 | −29.260 | 1.00 | 111.87 | C |
| ATOM | 3650 | CD | LYS A | 491 | −73.396 | 7.506 | −30.185 | 1.00 | 113.83 | C |
| ATOM | 3651 | CE | LYS A | 491 | −73.335 | 7.983 | −31.630 | 1.00 | 112.89 | C |
| ATOM | 3652 | NZ | LYS A | 491 | −73.190 | 6.838 | −32.570 | 1.00 | 113.93 | N |
| ATOM | 3653 | C | LYS A | 491 | −72.303 | 10.460 | −26.800 | 1.00 | 89.29 | C |
| ATOM | 3654 | O | LYS A | 491 | −72.926 | 10.952 | −25.853 | 1.00 | 85.94 | O |
| ATOM | 3655 | N | GLU A | 492 | −71.849 | 11.182 | −27.819 | 1.00 | 91.24 | N |
| ATOM | 3656 | CA | GLU A | 492 | −72.255 | 12.576 | −27.982 | 1.00 | 94.12 | C |
| ATOM | 3657 | CB | GLU A | 492 | −71.339 | 13.281 | −28.972 | 1.00 | 97.74 | C |
| ATOM | 3658 | CG | GLU A | 492 | −71.279 | 14.804 | −28.789 | 1.00 | 102.93 | C |
| ATOM | 3659 | CD | GLU A | 492 | −72.443 | 15.597 | −29.404 | 1.00 | 99.62 | C |
| ATOM | 3660 | OE1 | GLU A | 492 | −73.227 | 15.048 | −30.226 | 1.00 | 88.25 | O |
| ATOM | 3661 | OE2 | GLU A | 492 | −72.542 | 16.808 | −29.069 | 1.00 | 93.30 | O |
| ATOM | 3662 | C | GLU A | 492 | −73.709 | 12.663 | −28.483 | 1.00 | 92.42 | C |
| ATOM | 3663 | O | GLU A | 492 | −74.021 | 12.050 | −29.497 | 1.00 | 87.99 | O |
| ATOM | 3664 | N | PRO A | 493 | −74.588 | 13.441 | −27.796 | 1.00 | 94.54 | N |
| ATOM | 3665 | CA | PRO A | 493 | −76.002 | 13.608 | −28.158 | 1.00 | 91.43 | C |
| ATOM | 3666 | CB | PRO A | 493 | −76.336 | 14.977 | −27.574 | 1.00 | 95.75 | C |
| ATOM | 3667 | CG | PRO A | 493 | −75.550 | 14.996 | −26.301 | 1.00 | 100.25 | C |
| ATOM | 3668 | CD | PRO A | 493 | −74.306 | 14.156 | −26.531 | 1.00 | 99.11 | C |
| ATOM | 3669 | C | PRO A | 493 | −76.348 | 13.513 | −29.648 | 1.00 | 91.45 | C |
| ATOM | 3670 | O | PRO A | 493 | −76.970 | 12.532 | −30.031 | 1.00 | 90.86 | O |
| ATOM | 3671 | N | GLN A | 494 | −75.927 | 14.457 | −30.497 | 1.00 | 93.41 | N |
| ATOM | 3672 | CA | GLN A | 494 | −76.245 | 14.386 | −31.946 | 1.00 | 91.82 | C |
| ATOM | 3673 | CB | GLN A | 494 | −76.544 | 15.796 | −32.527 | 1.00 | 84.49 | C |
| ATOM | 3674 | C | GLN A | 494 | −75.145 | 13.608 | −32.738 | 1.00 | 93.36 | C |
| ATOM | 3675 | O | GLN A | 494 | −74.852 | 13.949 | −33.891 | 1.00 | 89.69 | O |
| ATOM | 3676 | N | ALA A | 495 | −74.590 | 12.547 | −32.109 | 1.00 | 100.85 | N |
| ATOM | 3677 | CA | ALA A | 495 | −73.475 | 11.656 | −32.607 | 1.00 | 102.09 | C |
| ATOM | 3678 | CB | ALA A | 495 | −74.021 | 10.630 | −33.606 | 1.00 | 99.89 | C |
| ATOM | 3679 | C | ALA A | 495 | −72.167 | 12.304 | −33.153 | 1.00 | 99.20 | C |
| ATOM | 3680 | O | ALA A | 495 | −71.498 | 11.707 | −34.005 | 1.00 | 94.90 | O |
| ATOM | 3681 | N | LYS A | 496 | −71.790 | 13.482 | −32.636 | 1.00 | 97.64 | N |
| ATOM | 3682 | CA | LYS A | 496 | −70.618 | 14.239 | −33.153 | 1.00 | 93.62 | C |
| ATOM | 3683 | CB | LYS A | 496 | −70.691 | 15.794 | −32.931 | 1.00 | 102.05 | C |
| ATOM | 3684 | CG | LYS A | 496 | −72.031 | 16.505 | −32.603 | 1.00 | 106.55 | C |
| ATOM | 3685 | CD | LYS A | 496 | −72.343 | 17.731 | −33.468 | 1.00 | 109.99 | C |
| ATOM | 3686 | CE | LYS A | 496 | −73.135 | 17.315 | −34.717 | 1.00 | 116.83 | C |
| ATOM | 3687 | NZ | LYS A | 496 | −72.813 | 18.104 | −35.937 | 1.00 | 124.14 | N |
| ATOM | 3688 | C | LYS A | 496 | −69.337 | 13.697 | −32.502 | 1.00 | 84.20 | C |
| ATOM | 3689 | O | LYS A | 496 | −69.375 | 13.215 | −31.370 | 1.00 | 88.31 | O |
| ATOM | 3690 | N | ASN A | 497 | −68.203 | 13.800 | −33.183 | 1.00 | 72.73 | N |
| ATOM | 3691 | CA | ASN A | 497 | −66.949 | 13.323 | −32.600 | 1.00 | 70.33 | C |
| ATOM | 3692 | CB | ASN A | 497 | −65.814 | 13.355 | −33.623 | 1.00 | 72.29 | C |
| ATOM | 3693 | CG | ASN A | 497 | −66.014 | 12.402 | −34.771 | 1.00 | 74.24 | C |
| ATOM | 3694 | OD1 | ASN A | 497 | −66.547 | 11.277 | −34.636 | 1.00 | 74.43 | O |
| ATOM | 3695 | ND2 | ASN A | 497 | −65.562 | 12.844 | −35.928 | 1.00 | 73.26 | N |
| ATOM | 3696 | C | ASN A | 497 | −66.423 | 14.122 | −31.397 | 1.00 | 67.55 | C |
| ATOM | 3697 | O | ASN A | 497 | −66.214 | 15.325 | −31.518 | 1.00 | 63.69 | O |
| ATOM | 3698 | N | ILE A | 498 | −66.157 | 13.425 | −30.279 | 1.00 | 66.83 | N |
| ATOM | 3699 | CA | ILE A | 498 | −65.149 | 13.842 | −29.266 | 1.00 | 65.78 | C |
| ATOM | 3700 | CB | ILE A | 498 | −64.729 | 12.678 | −28.304 | 1.00 | 64.55 | C |
| ATOM | 3701 | CG1 | ILE A | 498 | −65.906 | 12.163 | −27.451 | 1.00 | 61.88 | C |
| ATOM | 3702 | CD1 | ILE A | 498 | −66.054 | 10.655 | −27.475 | 1.00 | 60.24 | C |
| ATOM | 3703 | CG2 | ILE A | 498 | −63.631 | 13.116 | −27.332 | 1.00 | 65.36 | C |
| ATOM | 3704 | C | ILE A | 498 | −63.899 | 14.389 | −29.996 | 1.00 | 65.97 | C |
| ATOM | 3705 | O | ILE A | 498 | −63.366 | 13.742 | −30.908 | 1.00 | 64.21 | O |
| ATOM | 3706 | N | SER A | 499 | −63.461 | 15.597 | −29.629 | 1.00 | 69.37 | N |
| ATOM | 3707 | CA | SER A | 499 | −62.348 | 16.268 | −30.356 | 1.00 | 70.19 | C |
| ATOM | 3708 | CB | SER A | 499 | −62.808 | 17.623 | −30.979 | 1.00 | 70.69 | C |
| ATOM | 3709 | OG | SER A | 499 | −62.139 | 18.777 | −30.494 | 1.00 | 71.57 | O |
| ATOM | 3710 | C | SER A | 499 | −61.044 | 16.365 | −29.544 | 1.00 | 64.91 | C |
| ATOM | 3711 | O | SER A | 499 | −59.980 | 16.310 | −30.150 | 1.00 | 63.81 | O |
| ATOM | 3712 | N | VAL A | 500 | −61.154 | 16.494 | −28.210 | 1.00 | 60.37 | N |
| ATOM | 3713 | CA | VAL A | 500 | −60.042 | 16.469 | −27.263 | 1.00 | 59.06 | C |
| ATOM | 3714 | CB | VAL A | 500 | −59.776 | 17.846 | −26.682 | 1.00 | 65.63 | C |

TABLE 6-continued

Atomic coordinates for CRBN:DDB1: Compound B (Human protein)

| ATOM | 3715 | CG1 | VAL A | 500 | −58.783 | 17.775 | −25.522 | 1.00 | 70.96 | C |
|---|---|---|---|---|---|---|---|---|---|---|
| ATOM | 3716 | CG2 | VAL A | 500 | −59.262 | 18.790 | −27.768 | 1.00 | 69.69 | C |
| ATOM | 3717 | C | VAL A | 500 | −60.457 | 15.669 | −26.089 | 1.00 | 56.86 | C |
| ATOM | 3718 | O | VAL A | 500 | −61.585 | 15.770 | −25.700 | 1.00 | 56.23 | O |
| ATOM | 3719 | N | ALA A | 501 | −59.541 | 14.919 | −25.486 | 1.00 | 59.09 | N |
| ATOM | 3720 | CA | ALA A | 501 | −59.883 | 14.120 | −24.307 | 1.00 | 59.74 | C |
| ATOM | 3721 | CB | ALA A | 501 | −60.104 | 12.687 | −24.709 | 1.00 | 60.06 | C |
| ATOM | 3722 | C | ALA A | 501 | −58.828 | 14.196 | −23.224 | 1.00 | 59.76 | C |
| ATOM | 3723 | O | ALA A | 501 | −57.675 | 14.475 | −23.491 | 1.00 | 57.16 | O |
| ATOM | 3724 | N | SER A | 502 | −59.244 | 13.948 | −21.994 | 1.00 | 64.53 | N |
| ATOM | 3725 | CA | SER A | 502 | −58.337 | 13.957 | −20.845 | 1.00 | 70.79 | C |
| ATOM | 3726 | CB | SER A | 502 | −57.929 | 15.384 | −20.416 | 1.00 | 76.96 | C |
| ATOM | 3727 | OG | SER A | 502 | −59.048 | 16.197 | −20.031 | 1.00 | 85.43 | O |
| ATOM | 3728 | C | SER A | 502 | −59.023 | 13.242 | −19.694 | 1.00 | 67.80 | C |
| ATOM | 3729 | O | SER A | 502 | −60.055 | 13.688 | −19.201 | 1.00 | 68.62 | O |
| ATOM | 3730 | N | CYS A | 503 | −58.438 | 12.128 | −19.290 | 1.00 | 64.75 | N |
| ATOM | 3731 | CA | CYS A | 503 | −58.965 | 11.325 | −18.251 | 1.00 | 62.56 | C |
| ATOM | 3732 | CB | CYS A | 503 | −59.415 | 10.017 | −18.841 | 1.00 | 62.26 | C |
| ATOM | 3733 | SG | CYS A | 503 | −59.530 | 8.681 | −17.652 | 1.00 | 73.07 | S |
| ATOM | 3734 | C | CYS A | 503 | −57.866 | 11.142 | −17.222 | 1.00 | 65.83 | C |
| ATOM | 3735 | O | CYS A | 503 | −56.685 | 11.305 | −17.510 | 1.00 | 66.73 | O |
| ATOM | 3736 | N | ASN A | 504 | −58.298 | 10.882 | −15.995 | 1.00 | 71.30 | N |
| ATOM | 3737 | CA | ASN A | 504 | −57.428 | 10.579 | −14.860 | 1.00 | 71.01 | C |
| ATOM | 3738 | CB | ASN A | 504 | −57.232 | 11.836 | −13.915 | 1.00 | 73.53 | C |
| ATOM | 3739 | CG | ASN A | 504 | −58.416 | 12.135 | −12.935 | 1.00 | 76.23 | C |
| ATOM | 3740 | OD1 | ASN A | 504 | −58.628 | 11.438 | −11.929 | 1.00 | 80.87 | O |
| ATOM | 3741 | ND2 | ASN A | 504 | −59.117 | 13.250 | −13.182 | 1.00 | 74.10 | N |
| ATOM | 3742 | C | ASN A | 504 | −57.928 | 9.292 | −14.165 | 1.00 | 69.28 | C |
| ATOM | 3743 | O | ASN A | 504 | −58.714 | 8.538 | −14.718 | 1.00 | 72.96 | O |
| ATOM | 3744 | N | SER A | 505 | −57.414 | 9.023 | −12.980 | 1.00 | 71.93 | N |
| ATOM | 3745 | CA | SER A | 505 | −57.868 | 7.936 | −12.103 | 1.00 | 71.16 | C |
| ATOM | 3746 | CB | SER A | 505 | −57.449 | 8.313 | −10.681 | 1.00 | 70.79 | C |
| ATOM | 3747 | OG | SER A | 505 | −56.630 | 7.303 | −10.183 | 1.00 | 74.95 | O |
| ATOM | 3748 | C | SER A | 505 | −59.377 | 7.597 | −12.098 | 1.00 | 75.17 | C |
| ATOM | 3749 | O | SER A | 505 | −59.746 | 6.429 | −12.157 | 1.00 | 71.95 | O |
| ATOM | 3750 | N | SER A | 506 | −60.213 | 8.650 | −12.029 | 1.00 | 83.38 | N |
| ATOM | 3751 | CA | SER A | 506 | −61.639 | 8.605 | −11.630 | 1.00 | 80.15 | C |
| ATOM | 3752 | CB | SER A | 506 | −61.705 | 8.939 | −10.130 | 1.00 | 79.96 | C |
| ATOM | 3753 | OG | SER A | 506 | −61.284 | 10.292 | −9.901 | 1.00 | 74.12 | O |
| ATOM | 3754 | C | SER A | 506 | −62.563 | 9.623 | −12.350 | 1.00 | 79.81 | C |
| ATOM | 3755 | O | SER A | 506 | −63.704 | 9.802 | −11.921 | 1.00 | 79.84 | O |
| ATOM | 3756 | N | GLN A | 507 | −62.102 | 10.251 | −13.442 | 1.00 | 80.58 | N |
| ATOM | 3757 | CA | GLN A | 507 | −62.626 | 11.566 | −13.896 | 1.00 | 77.76 | C |
| ATOM | 3758 | CB | GLN A | 507 | −61.995 | 12.651 | −13.025 | 1.00 | 78.21 | C |
| ATOM | 3759 | CG | GLN A | 507 | −62.704 | 13.004 | −11.751 | 1.00 | 79.11 | C |
| ATOM | 3760 | CD | GLN A | 507 | −62.143 | 14.293 | −11.190 | 1.00 | 77.48 | C |
| ATOM | 3761 | OE1 | GLN A | 507 | −61.042 | 14.319 | −10.642 | 1.00 | 84.73 | O |
| ATOM | 3762 | NE2 | GLN A | 507 | −62.880 | 15.373 | −11.353 | 1.00 | 70.09 | N |
| ATOM | 3763 | C | GLN A | 507 | −62.323 | 11.966 | −15.346 | 1.00 | 71.79 | C |
| ATOM | 3764 | O | GLN A | 507 | −61.256 | 12.538 | −15.615 | 1.00 | 66.06 | O |
| ATOM | 3765 | N | VAL A | 508 | −63.271 | 11.732 | −16.249 | 1.00 | 69.24 | N |
| ATOM | 3766 | CA | VAL A | 508 | −63.103 | 12.094 | −17.667 | 1.00 | 72.60 | C |
| ATOM | 3767 | CB | VAL A | 508 | −64.017 | 11.264 | −18.590 | 1.00 | 79.75 | C |
| ATOM | 3768 | CG1 | VAL A | 508 | −63.850 | 11.677 | −20.062 | 1.00 | 83.13 | C |
| ATOM | 3769 | CG2 | VAL A | 508 | −63.795 | 9.758 | −18.412 | 1.00 | 79.96 | C |
| ATOM | 3770 | C | VAL A | 508 | −63.494 | 13.547 | −17.856 | 1.00 | 70.13 | C |
| ATOM | 3771 | O | VAL A | 508 | −64.250 | 14.047 | −17.074 | 1.00 | 69.27 | O |
| ATOM | 3772 | N | VAL A | 509 | −62.944 | 14.211 | −18.868 | 1.00 | 68.53 | N |
| ATOM | 3773 | CA | VAL A | 509 | −63.385 | 15.534 | −19.319 | 1.00 | 71.69 | C |
| ATOM | 3774 | CB | VAL A | 509 | −62.632 | 16.712 | −18.635 | 1.00 | 74.99 | C |
| ATOM | 3775 | CG1 | VAL A | 509 | −63.235 | 18.067 | −19.016 | 1.00 | 72.01 | C |
| ATOM | 3776 | CG2 | VAL A | 509 | −62.666 | 16.568 | −17.142 | 1.00 | 78.59 | C |
| ATOM | 3777 | C | VAL A | 509 | −63.086 | 15.619 | −20.805 | 1.00 | 72.45 | C |
| ATOM | 3778 | O | VAL A | 509 | −62.015 | 16.105 | −21.209 | 1.00 | 68.54 | O |
| ATOM | 3779 | N | VAL A | 510 | −64.011 | 15.102 | −21.609 | 1.00 | 72.64 | N |
| ATOM | 3780 | CA | VAL A | 510 | −63.942 | 15.245 | −23.077 | 1.00 | 71.94 | C |
| ATOM | 3781 | CB | VAL A | 510 | −64.798 | 14.210 | −23.857 | 1.00 | 74.07 | C |
| ATOM | 3782 | CG1 | VAL A | 510 | −64.077 | 12.874 | −23.990 | 1.00 | 73.20 | C |
| ATOM | 3783 | CG2 | VAL A | 510 | −66.180 | 14.068 | −23.228 | 1.00 | 76.51 | C |
| ATOM | 3784 | C | VAL A | 510 | −64.395 | 16.645 | −23.449 | 1.00 | 70.68 | C |
| ATOM | 3785 | O | VAL A | 510 | −64.727 | 17.447 | −22.583 | 1.00 | 68.96 | O |
| ATOM | 3786 | N | ALA A | 511 | −64.365 | 16.922 | −24.744 | 1.00 | 72.63 | N |
| ATOM | 3787 | CA | ALA A | 511 | −64.621 | 18.228 | −25.291 | 1.00 | 76.13 | C |
| ATOM | 3788 | CB | ALA A | 511 | −63.397 | 19.112 | −25.141 | 1.00 | 72.42 | C |
| ATOM | 3789 | C | ALA A | 511 | −64.950 | 18.015 | −26.760 | 1.00 | 85.73 | C |
| ATOM | 3790 | O | ALA A | 511 | −64.191 | 17.379 | −27.504 | 1.00 | 84.09 | O |
| ATOM | 3791 | N | VAL A | 512 | −66.104 | 18.525 | −27.166 | 1.00 | 92.76 | N |
| ATOM | 3792 | CA | VAL A | 512 | −66.588 | 18.374 | −28.522 | 1.00 | 88.98 | C |

TABLE 6-continued

Atomic coordinates for CRBN:DDB1: Compound B (Human protein)

| ATOM | 3793 | CB | VAL A | 512 | −67.969 | 17.707 | −28.508 | 1.00 | 84.67 | C |
|---|---|---|---|---|---|---|---|---|---|---|
| ATOM | 3794 | CG1 | VAL A | 512 | −68.277 | 17.119 | −29.869 | 1.00 | 84.55 | C |
| ATOM | 3795 | CG2 | VAL A | 512 | −68.026 | 16.612 | −27.447 | 1.00 | 84.32 | C |
| ATOM | 3796 | C | VAL A | 512 | −66.628 | 19.784 | −29.121 | 1.00 | 93.45 | C |
| ATOM | 3797 | O | VAL A | 512 | −67.331 | 20.653 | −28.593 | 1.00 | 96.51 | O |
| ATOM | 3798 | N | GLY A | 513 | −65.833 | 20.005 | −30.179 | 1.00 | 93.03 | N |
| ATOM | 3799 | CA | GLY A | 513 | −65.684 | 21.304 | −30.862 | 1.00 | 94.29 | C |
| ATOM | 3800 | C | GLY A | 513 | −65.484 | 22.529 | −29.978 | 1.00 | 95.34 | C |
| ATOM | 3801 | O | GLY A | 513 | −64.360 | 22.822 | −29.594 | 1.00 | 91.49 | O |
| ATOM | 3802 | N | ARG A | 514 | −66.580 | 23.253 | −29.701 | 1.00 | 99.84 | N |
| ATOM | 3803 | CA | ARG A | 514 | −66.630 | 24.356 | −28.694 | 1.00 | 102.40 | C |
| ATOM | 3804 | CB | ARG A | 514 | −67.419 | 25.582 | −29.250 | 1.00 | 104.04 | C |
| ATOM | 3805 | CG | ARG A | 514 | −66.648 | 26.464 | −30.262 | 1.00 | 103.36 | C |
| ATOM | 3806 | CD | ARG A | 514 | −67.516 | 27.344 | −31.166 | 1.00 | 98.31 | C |
| ATOM | 3807 | NE | ARG A | 514 | −68.453 | 28.116 | −30.359 | 1.00 | 101.61 | N |
| ATOM | 3808 | CZ | ARG A | 514 | −69.722 | 27.783 | −30.078 | 1.00 | 102.60 | C |
| ATOM | 3809 | NH1 | ARG A | 514 | −70.282 | 26.672 | −30.556 | 1.00 | 100.55 | N |
| ATOM | 3810 | NH2 | ARG A | 514 | −70.461 | 28.592 | −29.311 | 1.00 | 100.16 | N |
| ATOM | 3811 | C | ARG A | 514 | −67.198 | 23.904 | −27.313 | 1.00 | 95.36 | C |
| ATOM | 3812 | O | ARG A | 514 | −66.892 | 24.519 | −26.276 | 1.00 | 85.61 | O |
| ATOM | 3813 | N | ALA A | 515 | −67.996 | 22.828 | −27.327 | 1.00 | 92.01 | N |
| ATOM | 3814 | CA | ALA A | 515 | −68.682 | 22.276 | −26.149 | 1.00 | 90.43 | C |
| ATOM | 3815 | CB | ALA A | 515 | −69.896 | 21.479 | −26.604 | 1.00 | 89.80 | C |
| ATOM | 3816 | C | ALA A | 515 | −67.760 | 21.380 | −25.331 | 1.00 | 90.00 | C |
| ATOM | 3817 | O | ALA A | 515 | −66.802 | 20.825 | −25.900 | 1.00 | 89.18 | O |
| ATOM | 3818 | N | LEU A | 516 | −68.025 | 21.242 | −24.017 | 1.00 | 84.50 | N |
| ATOM | 3819 | CA | LEU A | 516 | −67.271 | 20.279 | −23.187 | 1.00 | 82.11 | C |
| ATOM | 3820 | CB | LEU A | 516 | −65.882 | 20.804 | −22.786 | 1.00 | 82.78 | C |
| ATOM | 3821 | CG | LEU A | 516 | −65.529 | 21.939 | −21.805 | 1.00 | 90.10 | C |
| ATOM | 3822 | CD1 | LEU A | 516 | −65.637 | 21.621 | −20.292 | 1.00 | 91.44 | C |
| ATOM | 3823 | CD2 | LEU A | 516 | −64.097 | 22.375 | −22.150 | 1.00 | 92.01 | C |
| ATOM | 3824 | C | LEU A | 516 | −67.993 | 19.696 | −21.981 | 1.00 | 81.92 | C |
| ATOM | 3825 | O | LEU A | 516 | −68.300 | 20.388 | −21.035 | 1.00 | 84.97 | O |
| ATOM | 3826 | N | TYR A | 517 | −68.191 | 18.382 | −22.016 | 1.00 | 86.25 | N |
| ATOM | 3827 | CA | TYR A | 517 | −68.903 | 17.632 | −20.975 | 1.00 | 87.50 | C |
| ATOM | 3828 | CB | TYR A | 517 | −69.667 | 16.441 | −21.580 | 1.00 | 91.55 | C |
| ATOM | 3829 | CG | TYR A | 517 | −70.495 | 16.809 | −22.796 | 1.00 | 101.13 | C |
| ATOM | 3830 | CD1 | TYR A | 517 | −69.929 | 16.796 | −24.067 | 1.00 | 108.62 | C |
| ATOM | 3831 | CE1 | TYR A | 517 | −70.669 | 17.137 | −25.191 | 1.00 | 115.17 | C |
| ATOM | 3832 | CZ | TYR A | 517 | −71.991 | 17.507 | −25.064 | 1.00 | 113.92 | C |
| ATOM | 3833 | OH | TYR A | 517 | −72.657 | 17.834 | −26.223 | 1.00 | 114.74 | O |
| ATOM | 3834 | CE2 | TYR A | 517 | −72.592 | 17.538 | −23.811 | 1.00 | 110.65 | C |
| ATOM | 3835 | CD2 | TYR A | 517 | −71.840 | 17.193 | −22.683 | 1.00 | 108.07 | C |
| ATOM | 3836 | C | TYR A | 517 | −67.885 | 17.139 | −19.963 | 1.00 | 80.78 | C |
| ATOM | 3837 | O | TYR A | 517 | −66.690 | 17.104 | −20.251 | 1.00 | 77.59 | O |
| ATOM | 3838 | N | TYR A | 518 | −68.369 | 16.743 | −18.788 | 1.00 | 78.22 | N |
| ATOM | 3839 | CA | TYR A | 518 | −67.514 | 16.291 | −17.686 | 1.00 | 74.79 | C |
| ATOM | 3840 | CB | TYR A | 518 | −67.255 | 17.462 | −16.697 | 1.00 | 71.65 | C |
| ATOM | 3841 | CG | TYR A | 518 | −66.871 | 17.006 | −15.311 | 1.00 | 74.75 | C |
| ATOM | 3842 | CD1 | TYR A | 518 | −65.889 | 16.072 | −15.127 | 1.00 | 79.29 | C |
| ATOM | 3843 | CE1 | TYR A | 518 | −65.553 | 15.608 | −13.863 | 1.00 | 79.97 | C |
| ATOM | 3844 | CZ | TYR A | 518 | −66.185 | 16.085 | −12.770 | 1.00 | 75.30 | C |
| ATOM | 3845 | OH | TYR A | 518 | −65.808 | 15.620 | −11.567 | 1.00 | 72.23 | O |
| ATOM | 3846 | CE2 | TYR A | 518 | −67.178 | 17.004 | −12.904 | 1.00 | 79.34 | C |
| ATOM | 3847 | CD2 | TYR A | 518 | −67.525 | 17.459 | −14.180 | 1.00 | 81.79 | C |
| ATOM | 3848 | C | TYR A | 518 | −68.097 | 15.025 | −16.995 | 1.00 | 72.37 | C |
| ATOM | 3849 | O | TYR A | 518 | −68.889 | 15.114 | −16.071 | 1.00 | 76.08 | O |
| ATOM | 3850 | N | LEU A | 519 | −67.645 | 13.847 | −17.409 | 1.00 | 70.81 | N |
| ATOM | 3851 | CA | LEU A | 519 | −68.111 | 12.583 | −16.824 | 1.00 | 70.42 | C |
| ATOM | 3852 | CB | LEU A | 519 | −68.021 | 11.478 | −17.863 | 1.00 | 73.22 | C |
| ATOM | 3853 | CG | LEU A | 519 | −68.859 | 11.562 | −19.147 | 1.00 | 77.42 | C |
| ATOM | 3854 | CD1 | LEU A | 519 | −69.177 | 12.966 | −19.681 | 1.00 | 75.71 | C |
| ATOM | 3855 | CD2 | LEU A | 519 | −68.179 | 10.703 | −20.213 | 1.00 | 80.14 | C |
| ATOM | 3856 | C | LEU A | 519 | −67.266 | 12.144 | −15.635 | 1.00 | 66.77 | C |
| ATOM | 3857 | O | LEU A | 519 | −66.084 | 12.463 | −15.570 | 1.00 | 61.74 | O |
| ATOM | 3858 | N | GLN A | 520 | −67.858 | 11.364 | −14.734 | 1.00 | 69.00 | N |
| ATOM | 3859 | CA | GLN A | 520 | −67.090 | 10.630 | −13.695 | 1.00 | 73.53 | C |
| ATOM | 3860 | CB | GLN A | 520 | −67.466 | 11.056 | −12.268 | 1.00 | 77.61 | C |
| ATOM | 3861 | CG | GLN A | 520 | −67.206 | 12.524 | −11.920 | 1.00 | 82.46 | C |
| ATOM | 3862 | CD | GLN A | 520 | −67.400 | 12.813 | −10.429 | 1.00 | 83.51 | C |
| ATOM | 3863 | OE1 | GLN A | 520 | −68.229 | 12.197 | −9.744 | 1.00 | 87.64 | O |
| ATOM | 3864 | NE2 | GLN A | 520 | −66.622 | 13.738 | −9.919 | 1.00 | 81.66 | N |
| ATOM | 3865 | C | GLN A | 520 | −67.251 | 9.111 | −13.799 | 1.00 | 72.90 | C |
| ATOM | 3866 | O | GLN A | 520 | −68.271 | 8.621 | −14.279 | 1.00 | 63.72 | O |
| ATOM | 3867 | N | ILE A | 521 | −66.233 | 8.399 | −13.298 | 1.00 | 77.64 | N |
| ATOM | 3868 | CA | ILE A | 521 | −66.153 | 6.935 | −13.348 | 1.00 | 82.90 | C |
| ATOM | 3869 | CB | ILE A | 521 | −64.729 | 6.421 | −13.766 | 1.00 | 88.24 | C |
| ATOM | 3870 | CG1 | ILE A | 521 | −64.403 | 6.854 | −15.217 | 1.00 | 89.72 | C |

TABLE 6-continued

Atomic coordinates for CRBN:DDB1: Compound B (Human protein)

| ATOM | 3871 | CD1 | ILE A | 521 | −62.977 | 7.329 | −15.424 | 1.00 | 90.86 | C |
|---|---|---|---|---|---|---|---|---|---|---|
| ATOM | 3872 | CG2 | ILE A | 521 | −64.591 | 4.886 | −13.631 | 1.00 | 83.79 | C |
| ATOM | 3873 | C | ILE A | 521 | −66.544 | 6.385 | −11.987 | 1.00 | 81.54 | C |
| ATOM | 3874 | O | ILE A | 521 | −65.951 | 6.750 | −10.960 | 1.00 | 77.33 | O |
| ATOM | 3875 | N | HIS A | 522 | −67.582 | 5.549 | −12.008 | 1.00 | 84.50 | N |
| ATOM | 3876 | CA | HIS A | 522 | −68.031 | 4.779 | −10.848 | 1.00 | 90.44 | C |
| ATOM | 3877 | CB | HIS A | 522 | −69.317 | 5.397 | −10.229 | 1.00 | 94.15 | C |
| ATOM | 3878 | CG | HIS A | 522 | −69.170 | 6.847 | −9.832 | 1.00 | 98.97 | C |
| ATOM | 3879 | ND1 | HIS A | 522 | −68.735 | 7.243 | −8.582 | 1.00 | 100.75 | N |
| ATOM | 3880 | CE1 | HIS A | 522 | −68.691 | 8.565 | −8.526 | 1.00 | 100.41 | C |
| ATOM | 3881 | NE2 | HIS A | 522 | −69.074 | 9.043 | −9.696 | 1.00 | 99.16 | N |
| ATOM | 3882 | CD2 | HIS A | 522 | −69.380 | 7.992 | −10.531 | 1.00 | 99.45 | C |
| ATOM | 3883 | C | HIS A | 522 | −68.217 | 3.347 | −11.377 | 1.00 | 83.18 | C |
| ATOM | 3884 | O | HIS A | 522 | −68.106 | 3.144 | −12.596 | 1.00 | 77.20 | O |
| ATOM | 3885 | N | PRO A | 523 | −68.474 | 2.353 | −10.486 | 1.00 | 75.96 | N |
| ATOM | 3886 | CA | PRO A | 523 | −68.521 | 0.997 | −11.014 | 1.00 | 72.38 | C |
| ATOM | 3887 | CB | PRO A | 523 | −68.780 | 0.113 | −9.766 | 1.00 | 70.83 | C |
| ATOM | 3888 | CG | PRO A | 523 | −68.402 | 0.954 | −8.615 | 1.00 | 73.30 | C |
| ATOM | 3889 | CD | PRO A | 523 | −68.709 | 2.371 | −9.030 | 1.00 | 75.91 | C |
| ATOM | 3890 | C | PRO A | 523 | −69.596 | 0.858 | −12.099 | 1.00 | 71.47 | C |
| ATOM | 3891 | O | PRO A | 523 | −70.633 | 1.485 | −12.033 | 1.00 | 68.82 | O |
| ATOM | 3892 | N | GLN A | 524 | −69.269 | 0.085 | −13.127 | 1.00 | 78.14 | N |
| ATOM | 3893 | CA | GLN A | 524 | −70.118 | −0.227 | −14.287 | 1.00 | 78.23 | C |
| ATOM | 3894 | CB | GLN A | 524 | −70.941 | −1.480 | −13.976 | 1.00 | 77.28 | C |
| ATOM | 3895 | CG | GLN A | 524 | −70.068 | −2.702 | −13.746 | 1.00 | 77.64 | C |
| ATOM | 3896 | CD | GLN A | 524 | −69.590 | −2.881 | −12.307 | 1.00 | 78.32 | C |
| ATOM | 3897 | OE1 | GLN A | 524 | −69.518 | −1.947 | −11.527 | 1.00 | 71.64 | O |
| ATOM | 3898 | NE2 | GLN A | 524 | −69.261 | −4.116 | −11.958 | 1.00 | 84.97 | N |
| ATOM | 3899 | C | GLN A | 524 | −70.991 | 0.907 | −14.846 | 1.00 | 78.54 | C |
| ATOM | 3900 | O | GLN A | 524 | −72.031 | 0.652 | −15.470 | 1.00 | 80.73 | O |
| ATOM | 3901 | N | GLU A | 525 | −70.538 | 2.148 | −14.674 | 1.00 | 78.26 | N |
| ATOM | 3902 | CA | GLU A | 525 | −71.321 | 3.318 | −15.081 | 1.00 | 80.75 | C |
| ATOM | 3903 | CB | GLU A | 525 | −72.547 | 3.555 | −14.152 | 1.00 | 86.78 | C |
| ATOM | 3904 | CG | GLU A | 525 | −72.329 | 4.187 | −12.762 | 1.00 | 84.23 | C |
| ATOM | 3905 | CD | GLU A | 525 | −72.814 | 5.630 | −12.664 | 1.00 | 76.79 | C |
| ATOM | 3906 | OE1 | GLU A | 525 | −74.011 | 5.863 | −12.879 | 1.00 | 65.27 | O |
| ATOM | 3907 | OE2 | GLU A | 525 | −72.002 | 6.525 | −12.353 | 1.00 | 78.67 | O |
| ATOM | 3908 | C | GLU A | 525 | −70.437 | 4.538 | −15.182 | 1.00 | 77.54 | C |
| ATOM | 3909 | O | GLU A | 525 | −69.570 | 4.758 | −14.326 | 1.00 | 71.85 | O |
| ATOM | 3910 | N | LEU A | 526 | −70.625 | 5.284 | −16.268 | 1.00 | 83.99 | N |
| ATOM | 3911 | CA | LEU A | 526 | −69.955 | 6.577 | −16.454 | 1.00 | 95.32 | C |
| ATOM | 3912 | CB | LEU A | 526 | −68.923 | 6.636 | −17.617 | 1.00 | 96.59 | C |
| ATOM | 3913 | CG | LEU A | 526 | −68.873 | 5.607 | −18.750 | 1.00 | 100.01 | C |
| ATOM | 3914 | CD1 | LEU A | 526 | −70.077 | 5.668 | −19.680 | 1.00 | 103.94 | C |
| ATOM | 3915 | CD2 | LEU A | 526 | −67.599 | 5.858 | −19.524 | 1.00 | 100.98 | C |
| ATOM | 3916 | C | LEU A | 526 | −71.040 | 7.637 | −16.569 | 1.00 | 93.82 | C |
| ATOM | 3917 | O | LEU A | 526 | −71.667 | 7.813 | −17.638 | 1.00 | 87.46 | O |
| ATOM | 3918 | N | ARG A | 527 | −71.232 | 8.345 | −15.460 | 1.00 | 92.64 | N |
| ATOM | 3919 | CA | ARG A | 527 | −72.241 | 9.373 | −15.315 | 1.00 | 91.65 | C |
| ATOM | 3920 | CB | ARG A | 527 | −72.714 | 9.387 | −13.872 | 1.00 | 90.52 | C |
| ATOM | 3921 | CG | ARG A | 527 | −71.576 | 9.393 | −12.884 | 1.00 | 91.26 | C |
| ATOM | 3922 | CD | ARG A | 527 | −72.084 | 9.441 | −11.458 | 1.00 | 90.48 | C |
| ATOM | 3923 | NE | ARG A | 527 | −72.717 | 8.196 | −11.050 | 1.00 | 85.80 | N |
| ATOM | 3924 | CZ | ARG A | 527 | −72.877 | 7.838 | −9.785 | 1.00 | 77.95 | C |
| ATOM | 3925 | NH1 | ARG A | 527 | −72.434 | 8.619 | −8.815 | 1.00 | 78.63 | N |
| ATOM | 3926 | NH2 | ARG A | 527 | −73.465 | 6.699 | −9.491 | 1.00 | 68.78 | N |
| ATOM | 3927 | C | ARG A | 527 | −71.806 | 10.771 | −15.670 | 1.00 | 90.34 | C |
| ATOM | 3928 | O | ARG A | 527 | −70.775 | 11.238 | −15.239 | 1.00 | 88.51 | O |
| ATOM | 3929 | N | GLN A | 528 | −72.627 | 11.433 | −16.464 | 1.00 | 85.80 | N |
| ATOM | 3930 | CA | GLN A | 528 | −72.385 | 12.790 | −16.875 | 1.00 | 81.72 | C |
| ATOM | 3931 | CB | GLN A | 528 | −73.424 | 13.157 | −17.906 | 1.00 | 81.16 | C |
| ATOM | 3932 | CG | GLN A | 528 | −73.022 | 14.260 | −18.845 | 1.00 | 83.66 | C |
| ATOM | 3933 | CD | GLN A | 528 | −73.742 | 14.149 | −20.161 | 1.00 | 84.26 | C |
| ATOM | 3934 | OE1 | GLN A | 528 | −74.663 | 13.359 | −20.299 | 1.00 | 81.69 | O |
| ATOM | 3935 | NE2 | GLN A | 528 | −73.322 | 14.933 | −21.136 | 1.00 | 84.24 | N |
| ATOM | 3936 | C | GLN A | 528 | −72.574 | 13.656 | −15.660 | 1.00 | 78.71 | C |
| ATOM | 3937 | O | GLN A | 528 | −73.458 | 13.403 | −14.868 | 1.00 | 78.63 | O |
| ATOM | 3938 | N | ILE A | 529 | −71.743 | 14.664 | −15.486 | 1.00 | 75.06 | N |
| ATOM | 3939 | CA | ILE A | 529 | −71.888 | 15.534 | −14.341 | 1.00 | 72.22 | C |
| ATOM | 3940 | CB | ILE A | 529 | −70.789 | 15.226 | −13.309 | 1.00 | 71.75 | C |
| ATOM | 3941 | CG1 | ILE A | 529 | −71.142 | 13.946 | −12.571 | 1.00 | 69.44 | C |
| ATOM | 3942 | CD1 | ILE A | 529 | −70.240 | 13.672 | −11.395 | 1.00 | 66.78 | C |
| ATOM | 3943 | CG2 | ILE A | 529 | −70.578 | 16.354 | −12.311 | 1.00 | 68.83 | C |
| ATOM | 3944 | C | ILE A | 529 | −71.947 | 17.003 | −14.705 | 1.00 | 72.27 | C |
| ATOM | 3945 | O | ILE A | 529 | −72.243 | 17.812 | −13.863 | 1.00 | 75.52 | O |
| ATOM | 3946 | N | SER A | 530 | −71.634 | 17.351 | −15.936 | 1.00 | 75.46 | N |
| ATOM | 3947 | CA | SER A | 530 | −71.648 | 18.744 | −16.325 | 1.00 | 79.25 | C |
| ATOM | 3948 | CB | SER A | 530 | −70.455 | 19.474 | −15.736 | 1.00 | 79.31 | C |

TABLE 6-continued

Atomic coordinates for CRBN:DDB1: Compound B (Human protein)

| ATOM | 3949 | OG | SER A | 530 | −70.307 | 19.128 | −14.382 | 1.00 | 76.71 | O |
|---|---|---|---|---|---|---|---|---|---|---|
| ATOM | 3950 | C | SER A | 530 | −71.608 | 18.895 | −17.802 | 1.00 | 81.35 | C |
| ATOM | 3951 | O | SER A | 530 | −71.375 | 17.953 | −18.523 | 1.00 | 73.61 | O |
| ATOM | 3952 | N | HIS A | 531 | −71.834 | 20.108 | −18.247 | 1.00 | 90.67 | N |
| ATOM | 3953 | CA | HIS A | 531 | −71.776 | 20.421 | −19.648 | 1.00 | 99.36 | C |
| ATOM | 3954 | CB | HIS A | 531 | −73.089 | 20.174 | −20.370 | 1.00 | 104.70 | C |
| ATOM | 3955 | CG | HIS A | 531 | −74.295 | 20.326 | −19.506 | 1.00 | 115.45 | C |
| ATOM | 3956 | ND1 | HIS A | 531 | −75.448 | 19.602 | −19.712 | 1.00 | 119.07 | N |
| ATOM | 3957 | CE1 | HIS A | 531 | −76.342 | 19.931 | −18.797 | 1.00 | 115.77 | C |
| ATOM | 3958 | NE2 | HIS A | 531 | −75.808 | 20.839 | −18.002 | 1.00 | 118.22 | N |
| ATOM | 3959 | CD2 | HIS A | 531 | −74.526 | 21.101 | −18.421 | 1.00 | 119.98 | C |
| ATOM | 3960 | C | HIS A | 531 | −71.464 | 21.864 | −19.670 | 1.00 | 96.72 | C |
| ATOM | 3961 | O | HIS A | 531 | −71.510 | 22.523 | −18.651 | 1.00 | 97.53 | O |
| ATOM | 3962 | N | THR A | 532 | −71.108 | 22.360 | −20.829 | 1.00 | 94.34 | N |
| ATOM | 3963 | CA | THR A | 532 | −70.811 | 23.760 | −20.952 | 1.00 | 94.11 | C |
| ATOM | 3964 | CB | THR A | 532 | −69.691 | 24.286 | −20.024 | 1.00 | 90.97 | C |
| ATOM | 3965 | OG1 | THR A | 532 | −68.782 | 25.114 | −20.757 | 1.00 | 86.60 | O |
| ATOM | 3966 | CG2 | THR A | 532 | −68.945 | 23.167 | −19.377 | 1.00 | 92.91 | C |
| ATOM | 3967 | C | THR A | 532 | −70.709 | 24.194 | −22.379 | 1.00 | 94.12 | C |
| ATOM | 3968 | O | THR A | 532 | −71.173 | 23.536 | −23.287 | 1.00 | 96.05 | O |
| ATOM | 3969 | N | GLU A | 533 | −70.120 | 25.352 | −22.536 | 1.00 | 96.22 | N |
| ATOM | 3970 | CA | GLU A | 533 | −69.992 | 26.002 | −23.836 | 1.00 | 101.72 | C |
| ATOM | 3971 | CB | GLU A | 533 | −71.238 | 26.889 | −24.128 | 1.00 | 106.63 | C |
| ATOM | 3972 | CG | GLU A | 533 | −72.475 | 26.196 | −24.722 | 1.00 | 105.12 | C |
| ATOM | 3973 | CD | GLU A | 533 | −72.361 | 25.890 | −26.220 | 1.00 | 98.61 | C |
| ATOM | 3974 | OE1 | GLU A | 533 | −71.351 | 25.276 | −26.647 | 1.00 | 81.30 | O |
| ATOM | 3975 | OE2 | GLU A | 533 | −73.302 | 26.263 | −26.965 | 1.00 | 96.95 | O |
| ATOM | 3976 | C | GLU A | 533 | −68.741 | 26.889 | −23.717 | 1.00 | 93.80 | C |
| ATOM | 3977 | O | GLU A | 533 | −68.402 | 27.308 | −22.612 | 1.00 | 97.51 | O |
| ATOM | 3978 | N | MET A | 534 | −68.054 | 27.187 | −24.811 | 1.00 | 83.90 | N |
| ATOM | 3979 | CA | MET A | 534 | −66.779 | 27.862 | −24.668 | 1.00 | 83.99 | C |
| ATOM | 3980 | CB | MET A | 534 | −65.642 | 26.808 | −24.653 | 1.00 | 88.39 | C |
| ATOM | 3981 | CG | MET A | 534 | −64.475 | 27.116 | −23.685 | 1.00 | 89.35 | C |
| ATOM | 3982 | SD | MET A | 534 | −64.648 | 26.901 | −21.881 | 1.00 | 85.83 | S |
| ATOM | 3983 | CE | MET A | 534 | −65.547 | 28.372 | −21.302 | 1.00 | 86.18 | C |
| ATOM | 3984 | C | MET A | 534 | −66.591 | 28.964 | −25.713 | 1.00 | 79.95 | C |
| ATOM | 3985 | O | MET A | 534 | −66.915 | 28.770 | −26.897 | 1.00 | 73.23 | O |
| ATOM | 3986 | N | GLU A | 535 | −66.066 | 30.112 | −25.244 | 1.00 | 76.76 | N |
| ATOM | 3987 | CA | GLU A | 535 | −66.003 | 31.369 | −26.021 | 1.00 | 78.63 | C |
| ATOM | 3988 | CB | GLU A | 535 | −65.556 | 32.535 | −25.082 | 1.00 | 68.71 | C |
| ATOM | 3989 | C | GLU A | 535 | −65.222 | 31.290 | −27.417 | 1.00 | 84.80 | C |
| ATOM | 3990 | O | GLU A | 535 | −65.338 | 32.161 | −28.276 | 1.00 | 97.33 | O |
| ATOM | 3991 | N | HIS A | 536 | −64.444 | 30.244 | −27.645 | 1.00 | 90.14 | N |
| ATOM | 3992 | CA | HIS A | 536 | −63.953 | 29.895 | −28.988 | 1.00 | 90.06 | C |
| ATOM | 3993 | CB | HIS A | 536 | −62.743 | 30.788 | −29.361 | 1.00 | 85.40 | C |
| ATOM | 3994 | C | HIS A | 536 | −63.695 | 28.330 | −28.934 | 1.00 | 92.35 | C |
| ATOM | 3995 | O | HIS A | 536 | −63.948 | 27.712 | −27.869 | 1.00 | 88.42 | O |
| ATOM | 3996 | N | GLU A | 537 | −63.270 | 27.679 | −30.037 | 1.00 | 89.40 | N |
| ATOM | 3997 | CA | GLU A | 537 | −63.163 | 26.163 | −30.105 | 1.00 | 85.24 | C |
| ATOM | 3998 | CB | GLU A | 537 | −63.026 | 25.629 | −31.571 | 1.00 | 80.16 | C |
| ATOM | 3999 | C | GLU A | 537 | −62.058 | 25.560 | −29.190 | 1.00 | 78.72 | C |
| ATOM | 4000 | O | GLU A | 537 | −60.950 | 26.092 | −29.113 | 1.00 | 74.06 | O |
| ATOM | 4001 | N | VAL A | 538 | −62.357 | 24.459 | −28.493 | 1.00 | 72.56 | N |
| ATOM | 4002 | CA | VAL A | 538 | −61.375 | 23.926 | −27.504 | 1.00 | 74.64 | C |
| ATOM | 4003 | CB | VAL A | 538 | −61.991 | 23.197 | −26.252 | 1.00 | 70.25 | C |
| ATOM | 4004 | CG1 | VAL A | 538 | −63.396 | 22.692 | −26.507 | 1.00 | 75.32 | C |
| ATOM | 4005 | CG2 | VAL A | 538 | −61.101 | 22.071 | −25.744 | 1.00 | 66.57 | C |
| ATOM | 4006 | C | VAL A | 538 | −60.165 | 23.193 | −28.170 | 1.00 | 75.21 | C |
| ATOM | 4007 | O | VAL A | 538 | −60.281 | 22.564 | −29.224 | 1.00 | 72.34 | O |
| ATOM | 4008 | N | ALA A | 539 | −59.001 | 23.364 | −27.535 | 1.00 | 73.21 | N |
| ATOM | 4009 | CA | ALA A | 539 | −57.718 | 22.924 | −28.039 | 1.00 | 67.64 | C |
| ATOM | 4010 | CB | ALA A | 539 | −56.799 | 24.113 | −28.224 | 1.00 | 64.43 | C |
| ATOM | 4011 | C | ALA A | 539 | −57.039 | 21.871 | −27.152 | 1.00 | 69.55 | C |
| ATOM | 4012 | O | ALA A | 539 | −56.440 | 20.942 | −27.711 | 1.00 | 65.29 | O |
| ATOM | 4013 | N | CYS A | 540 | −57.077 | 22.008 | −25.816 | 1.00 | 67.53 | N |
| ATOM | 4014 | CA | CYS A | 540 | −56.361 | 21.049 | −24.959 | 1.00 | 70.33 | C |
| ATOM | 4015 | CB | CYS A | 540 | −54.822 | 21.151 | −25.109 | 1.00 | 74.53 | C |
| ATOM | 4016 | SG | CYS A | 540 | −54.002 | 22.774 | −25.150 | 1.00 | 71.22 | S |
| ATOM | 4017 | C | CYS A | 540 | −56.718 | 21.084 | −23.503 | 1.00 | 70.73 | C |
| ATOM | 4018 | O | CYS A | 540 | −56.960 | 22.128 | −22.968 | 1.00 | 75.29 | O |
| ATOM | 4019 | N | LEU A | 541 | −56.700 | 19.920 | −22.868 | 1.00 | 72.33 | N |
| ATOM | 4020 | CA | LEU A | 541 | −57.218 | 19.766 | −21.527 | 1.00 | 74.53 | C |
| ATOM | 4021 | CB | LEU A | 541 | −58.459 | 18.908 | −21.560 | 1.00 | 75.77 | C |
| ATOM | 4022 | CG | LEU A | 541 | −59.541 | 19.406 | −22.493 | 1.00 | 80.66 | C |
| ATOM | 4023 | CD1 | LEU A | 541 | −60.625 | 18.360 | −22.723 | 1.00 | 82.63 | C |
| ATOM | 4024 | CD2 | LEU A | 541 | −60.114 | 20.682 | −21.899 | 1.00 | 85.21 | C |
| ATOM | 4025 | C | LEU A | 541 | −56.266 | 19.025 | −20.669 | 1.00 | 78.38 | C |
| ATOM | 4026 | O | LEU A | 541 | −55.592 | 18.141 | −21.144 | 1.00 | 82.32 | O |

TABLE 6-continued

Atomic coordinates for CRBN:DDB1: Compound B (Human protein)

| ATOM | 4027 | N | ASP A | 542 | −56.245 | 19.334 | −19.386 | 1.00 | 85.01 | N |
|------|------|------|-------|-----|---------|--------|---------|------|-------|---|
| ATOM | 4028 | CA | ASP A | 542 | −55.437 | 18.601 | −18.438 | 1.00 | 86.67 | C |
| ATOM | 4029 | CB | ASP A | 542 | −54.150 | 19.297 | −18.064 | 1.00 | 88.02 | C |
| ATOM | 4030 | CG | ASP A | 542 | −53.325 | 18.493 | −17.092 | 1.00 | 89.90 | C |
| ATOM | 4031 | OD1 | ASP A | 542 | −53.815 | 17.461 | −16.607 | 1.00 | 94.22 | O |
| ATOM | 4032 | OD2 | ASP A | 542 | −52.187 | 18.900 | −16.798 | 1.00 | 85.56 | O |
| ATOM | 4033 | C | ASP A | 542 | −56.337 | 18.435 | −17.249 | 1.00 | 84.52 | C |
| ATOM | 4034 | O | ASP A | 542 | −57.194 | 19.248 | −17.018 | 1.00 | 78.18 | O |
| ATOM | 4035 | N | ILE A | 543 | −56.182 | 17.351 | −16.521 | 1.00 | 85.15 | N |
| ATOM | 4036 | CA | ILE A | 543 | −57.045 | 17.093 | −15.397 | 1.00 | 83.49 | C |
| ATOM | 4037 | CB | ILE A | 543 | −58.194 | 16.223 | −15.888 | 1.00 | 88.66 | C |
| ATOM | 4038 | CG1 | ILE A | 543 | −59.332 | 16.202 | −14.904 | 1.00 | 88.96 | C |
| ATOM | 4039 | CD1 | ILE A | 543 | −60.436 | 17.133 | −15.319 | 1.00 | 94.78 | C |
| ATOM | 4040 | CG2 | ILE A | 543 | −57.713 | 14.825 | −16.195 | 1.00 | 97.33 | C |
| ATOM | 4041 | C | ILE A | 543 | −56.295 | 16.396 | −14.278 | 1.00 | 81.04 | C |
| ATOM | 4042 | O | ILE A | 543 | −56.872 | 15.670 | −13.491 | 1.00 | 73.93 | O |
| ATOM | 4043 | N | THR A | 544 | −54.994 | 16.595 | −14.230 | 1.00 | 78.68 | N |
| ATOM | 4044 | CA | THR A | 544 | −54.148 | 15.934 | −13.256 | 1.00 | 77.99 | C |
| ATOM | 4045 | CB | THR A | 544 | −52.710 | 16.326 | −13.552 | 1.00 | 72.84 | C |
| ATOM | 4046 | OG1 | THR A | 544 | −52.632 | 16.760 | −14.905 | 1.00 | 68.65 | O |
| ATOM | 4047 | CG2 | THR A | 544 | −51.818 | 15.178 | −13.376 | 1.00 | 74.59 | C |
| ATOM | 4048 | C | THR A | 544 | −54.365 | 16.226 | −11.780 | 1.00 | 85.95 | C |
| ATOM | 4049 | O | THR A | 544 | −54.514 | 17.363 | −11.382 | 1.00 | 93.77 | O |
| ATOM | 4050 | N | PRO A | 545 | −54.336 | 15.124 | −10.937 | 1.00 | 88.26 | N |
| ATOM | 4051 | CA | PRO A | 545 | −54.474 | 15.416 | −9.506 | 1.00 | 94.04 | C |
| ATOM | 4052 | CB | PRO A | 545 | −54.733 | 14.055 | −8.885 | 1.00 | 97.73 | C |
| ATOM | 4053 | CG | PRO A | 545 | −55.417 | 13.312 | −9.949 | 1.00 | 97.95 | C |
| ATOM | 4054 | CD | PRO A | 545 | −54.474 | 13.611 | −11.054 | 1.00 | 92.21 | C |
| ATOM | 4055 | C | PRO A | 545 | −53.214 | 16.046 | −8.917 | 1.00 | 96.13 | C |
| ATOM | 4056 | O | PRO A | 545 | −52.229 | 16.203 | −9.611 | 1.00 | 100.02 | O |
| ATOM | 4057 | N | LEU A | 546 | −53.271 | 16.452 | −7.659 | 1.00 | 92.10 | N |
| ATOM | 4058 | CA | LEU A | 546 | −52.190 | 17.205 | −7.020 | 1.00 | 85.85 | C |
| ATOM | 4059 | CB | LEU A | 546 | −52.073 | 18.526 | −7.738 | 1.00 | 88.42 | C |
| ATOM | 4060 | CG | LEU A | 546 | −51.693 | 18.519 | −9.220 | 1.00 | 93.98 | C |
| ATOM | 4061 | CD1 | LEU A | 546 | −52.117 | 19.829 | −9.881 | 1.00 | 97.29 | C |
| ATOM | 4062 | CD2 | LEU A | 546 | −50.193 | 18.274 | −9.379 | 1.00 | 93.35 | C |
| ATOM | 4063 | C | LEU A | 546 | −52.480 | 17.490 | −5.538 | 1.00 | 80.95 | C |
| ATOM | 4064 | O | LEU A | 546 | −52.045 | 16.768 | −4.643 | 1.00 | 78.89 | O |
| ATOM | 4065 | N | GLY A | 551 | −57.910 | 11.857 | −3.782 | 1.00 | 83.35 | N |
| ATOM | 4066 | CA | GLY A | 551 | −58.331 | 11.191 | −5.047 | 1.00 | 91.36 | C |
| ATOM | 4067 | C | GLY A | 551 | −58.537 | 12.034 | −6.336 | 1.00 | 95.11 | C |
| ATOM | 4068 | O | GLY A | 551 | −57.649 | 12.072 | −7.202 | 1.00 | 87.97 | O |
| ATOM | 4069 | N | LEU A | 552 | −59.710 | 12.694 | −6.453 | 1.00 | 99.54 | N |
| ATOM | 4070 | CA | LEU A | 552 | −60.202 | 13.423 | −7.674 | 1.00 | 94.97 | C |
| ATOM | 4071 | CB | LEU A | 552 | −61.740 | 13.281 | −7.753 | 1.00 | 88.38 | C |
| ATOM | 4072 | C | LEU A | 552 | −59.834 | 14.941 | −7.786 | 1.00 | 93.26 | C |
| ATOM | 4073 | O | LEU A | 552 | −60.056 | 15.707 | −6.858 | 1.00 | 89.16 | O |
| ATOM | 4074 | N | SER A | 553 | −59.313 | 15.378 | −8.936 | 1.00 | 94.08 | N |
| ATOM | 4075 | CA | SER A | 553 | −58.877 | 16.791 | −9.125 | 1.00 | 95.98 | C |
| ATOM | 4076 | CB | SER A | 553 | −58.193 | 17.015 | −10.491 | 1.00 | 94.25 | C |
| ATOM | 4077 | OG | SER A | 553 | −58.164 | 18.402 | −10.891 | 1.00 | 88.59 | O |
| ATOM | 4078 | C | SER A | 553 | −60.010 | 17.814 | −9.037 | 1.00 | 100.53 | C |
| ATOM | 4079 | O | SER A | 553 | −60.986 | 17.695 | −9.772 | 1.00 | 98.88 | O |
| ATOM | 4080 | N | PRO A | 554 | −59.831 | 18.883 | −8.228 | 1.00 | 100.91 | N |
| ATOM | 4081 | CA | PRO A | 554 | −60.939 | 19.808 | −8.091 | 1.00 | 94.63 | C |
| ATOM | 4082 | CB | PRO A | 554 | −60.584 | 20.560 | −6.804 | 1.00 | 99.52 | C |
| ATOM | 4083 | CG | PRO A | 554 | −59.104 | 20.340 | −6.565 | 1.00 | 97.40 | C |
| ATOM | 4084 | CD | PRO A | 554 | −58.594 | 19.455 | −7.651 | 1.00 | 99.48 | C |
| ATOM | 4085 | C | PRO A | 554 | −61.088 | 20.778 | −9.270 | 1.00 | 89.51 | C |
| ATOM | 4086 | O | PRO A | 554 | −62.033 | 21.550 | −9.302 | 1.00 | 90.57 | O |
| ATOM | 4087 | N | LEU A | 555 | −60.170 | 20.767 | −10.226 | 1.00 | 87.98 | N |
| ATOM | 4088 | CA | LEU A | 555 | −60.219 | 21.742 | −11.320 | 1.00 | 89.57 | C |
| ATOM | 4089 | CB | LEU A | 555 | −59.306 | 22.954 | −11.001 | 1.00 | 89.70 | C |
| ATOM | 4090 | CG | LEU A | 555 | −58.073 | 22.798 | −10.114 | 1.00 | 87.15 | C |
| ATOM | 4091 | CD1 | LEU A | 555 | −56.985 | 23.776 | −10.531 | 1.00 | 84.19 | C |
| ATOM | 4092 | CD2 | LEU A | 555 | −58.425 | 23.003 | −8.642 | 1.00 | 86.44 | C |
| ATOM | 4093 | C | LEU A | 555 | −59.945 | 21.045 | −12.669 | 1.00 | 82.68 | C |
| ATOM | 4094 | O | LEU A | 555 | −60.229 | 19.865 | −12.792 | 1.00 | 78.44 | O |
| ATOM | 4095 | N | CYS A | 556 | −59.463 | 21.779 | −13.667 | 1.00 | 75.76 | N |
| ATOM | 4096 | CA | CYS A | 556 | −59.342 | 21.302 | −15.023 | 1.00 | 77.34 | C |
| ATOM | 4097 | CB | CYS A | 556 | −60.737 | 20.929 | −15.569 | 1.00 | 75.65 | C |
| ATOM | 4098 | SG | CYS A | 556 | −60.781 | 20.832 | −17.390 | 1.00 | 87.29 | S |
| ATOM | 4099 | C | CYS A | 556 | −58.732 | 22.426 | −15.887 | 1.00 | 75.45 | C |
| ATOM | 4100 | O | CYS A | 556 | −59.401 | 23.434 | −16.098 | 1.00 | 81.45 | O |
| ATOM | 4101 | N | ALA A | 557 | −57.498 | 22.294 | −16.380 | 1.00 | 70.56 | N |
| ATOM | 4102 | CA | ALA A | 557 | −56.934 | 23.359 | −17.250 | 1.00 | 69.83 | C |
| ATOM | 4103 | CB | ALA A | 557 | −55.423 | 23.287 | −17.324 | 1.00 | 71.05 | C |
| ATOM | 4104 | C | ALA A | 557 | −57.528 | 23.254 | −18.643 | 1.00 | 68.00 | C |

TABLE 6-continued

Atomic coordinates for CRBN:DDB1: Compound B (Human protein)

| ATOM | 4105 | O | ALA A | 557 | −58.057 | 22.192 | −18.980 | 1.00 | 63.23 | O |
|---|---|---|---|---|---|---|---|---|---|---|
| ATOM | 4106 | N | ILE A | 558 | −57.491 | 24.372 | −19.398 | 1.00 | 65.95 | N |
| ATOM | 4107 | CA | ILE A | 558 | −57.899 | 24.440 | −20.835 | 1.00 | 65.01 | C |
| ATOM | 4108 | CB | ILE A | 558 | −59.276 | 25.059 | −21.121 | 1.00 | 62.65 | C |
| ATOM | 4109 | CG1 | ILE A | 558 | −60.228 | 24.895 | −19.961 | 1.00 | 67.83 | C |
| ATOM | 4110 | CD1 | ILE A | 558 | −60.848 | 23.513 | −19.888 | 1.00 | 76.53 | C |
| ATOM | 4111 | CG2 | ILE A | 558 | −59.843 | 24.486 | −22.423 | 1.00 | 60.05 | C |
| ATOM | 4112 | C | ILE A | 558 | −57.048 | 25.392 | −21.634 | 1.00 | 64.48 | C |
| ATOM | 4113 | O | ILE A | 558 | −56.569 | 26.373 | −21.109 | 1.00 | 73.82 | O |
| ATOM | 4114 | N | GLY A | 559 | −56.936 | 25.135 | −22.922 | 1.00 | 61.01 | N |
| ATOM | 4115 | CA | GLY A | 559 | −56.352 | 26.076 | −23.859 | 1.00 | 63.23 | C |
| ATOM | 4116 | C | GLY A | 559 | −57.360 | 26.139 | −24.964 | 1.00 | 65.86 | C |
| ATOM | 4117 | O | GLY A | 559 | −57.935 | 25.090 | −25.270 | 1.00 | 67.90 | O |
| ATOM | 4118 | N | LEU A | 560 | −57.584 | 27.332 | −25.541 | 1.00 | 65.15 | N |
| ATOM | 4119 | CA | LEU A | 560 | −58.646 | 27.546 | −26.525 | 1.00 | 69.07 | C |
| ATOM | 4120 | CB | LEU A | 560 | −59.781 | 28.336 | −25.887 | 1.00 | 74.69 | C |
| ATOM | 4121 | CG | LEU A | 560 | −60.429 | 27.663 | −24.661 | 1.00 | 79.58 | C |
| ATOM | 4122 | CD1 | LEU A | 560 | −61.505 | 28.541 | −24.064 | 1.00 | 80.82 | C |
| ATOM | 4123 | CD2 | LEU A | 560 | −61.070 | 26.309 | −24.973 | 1.00 | 81.60 | C |
| ATOM | 4124 | C | LEU A | 560 | −58.134 | 28.219 | −27.794 | 1.00 | 74.07 | C |
| ATOM | 4125 | O | LEU A | 560 | −57.008 | 28.733 | −27.800 | 1.00 | 71.66 | O |
| ATOM | 4126 | N | TRP A | 561 | −58.976 | 28.246 | −28.844 | 1.00 | 79.75 | N |
| ATOM | 4127 | CA | TRP A | 561 | −58.522 | 28.357 | −30.274 | 1.00 | 84.58 | C |
| ATOM | 4128 | CB | TRP A | 561 | −59.451 | 27.524 | −31.196 | 1.00 | 84.52 | C |
| ATOM | 4129 | CG | TRP A | 561 | −58.952 | 26.225 | −31.773 | 1.00 | 80.02 | C |
| ATOM | 4130 | CD1 | TRP A | 561 | −58.983 | 24.990 | −31.189 | 1.00 | 78.08 | C |
| ATOM | 4131 | NE1 | TRP A | 561 | −58.501 | 24.044 | −32.061 | 1.00 | 77.84 | N |
| ATOM | 4132 | CE2 | TRP A | 561 | −58.175 | 24.643 | −33.250 | 1.00 | 78.57 | C |
| ATOM | 4133 | CD2 | TRP A | 561 | −58.461 | 26.024 | −33.114 | 1.00 | 83.29 | C |
| ATOM | 4134 | CE3 | TRP A | 561 | −58.221 | 26.882 | −34.214 | 1.00 | 83.04 | C |
| ATOM | 4135 | CZ3 | TRP A | 561 | −57.693 | 26.325 | −35.407 | 1.00 | 82.57 | C |
| ATOM | 4136 | CH2 | TRP A | 561 | −57.407 | 24.942 | −35.497 | 1.00 | 77.78 | C |
| ATOM | 4137 | CZ2 | TRP A | 561 | −57.649 | 24.092 | −34.442 | 1.00 | 75.47 | C |
| ATOM | 4138 | C | TRP A | 561 | −58.423 | 29.753 | −30.948 | 1.00 | 84.05 | C |
| ATOM | 4139 | O | TRP A | 561 | −57.860 | 29.874 | −32.048 | 1.00 | 84.26 | O |
| ATOM | 4140 | N | THR A | 562 | −59.022 | 30.784 | −30.392 | 1.00 | 78.71 | N |
| ATOM | 4141 | CA | THR A | 562 | −58.959 | 32.041 | −31.119 | 1.00 | 83.90 | C |
| ATOM | 4142 | CB | THR A | 562 | −60.277 | 32.318 | −31.830 | 1.00 | 92.62 | C |
| ATOM | 4143 | OG1 | THR A | 562 | −60.896 | 31.065 | −32.164 | 1.00 | 94.86 | O |
| ATOM | 4144 | CG2 | THR A | 562 | −60.011 | 33.141 | −33.104 | 1.00 | 93.87 | C |
| ATOM | 4145 | C | THR A | 562 | −58.533 | 33.174 | −30.237 | 1.00 | 83.39 | C |
| ATOM | 4146 | O | THR A | 562 | −57.693 | 33.961 | −30.660 | 1.00 | 77.29 | O |
| ATOM | 4147 | N | ASP A | 563 | −59.090 | 33.233 | −29.014 | 1.00 | 84.60 | N |
| ATOM | 4148 | CA | ASP A | 563 | −58.484 | 33.944 | −27.878 | 1.00 | 78.67 | C |
| ATOM | 4149 | CB | ASP A | 563 | −59.354 | 33.809 | −26.627 | 1.00 | 69.34 | C |
| ATOM | 4150 | C | ASP A | 563 | −57.073 | 33.451 | −27.530 | 1.00 | 85.33 | C |
| ATOM | 4151 | O | ASP A | 563 | −56.477 | 34.024 | −26.630 | 1.00 | 97.21 | O |
| ATOM | 4152 | N | ILE A | 564 | −56.558 | 32.405 | −28.219 | 1.00 | 89.15 | N |
| ATOM | 4153 | CA | ILE A | 564 | −55.181 | 31.805 | −28.068 | 1.00 | 87.66 | C |
| ATOM | 4154 | CB | ILE A | 564 | −53.979 | 32.509 | −28.859 | 1.00 | 92.84 | C |
| ATOM | 4155 | CG1 | ILE A | 564 | −53.655 | 33.968 | −28.309 | 1.00 | 103.14 | C |
| ATOM | 4156 | CD1 | ILE A | 564 | −54.041 | 35.221 | −29.109 | 1.00 | 101.41 | C |
| ATOM | 4157 | CG2 | ILE A | 564 | −54.111 | 32.332 | −30.379 | 1.00 | 84.93 | C |
| ATOM | 4158 | C | ILE A | 564 | −54.790 | 31.676 | −26.611 | 1.00 | 80.75 | C |
| ATOM | 4159 | O | ILE A | 564 | −53.631 | 31.872 | −26.263 | 1.00 | 77.19 | O |
| ATOM | 4160 | N | SER A | 565 | −55.753 | 31.342 | −25.764 | 1.00 | 75.59 | N |
| ATOM | 4161 | CA | SER A | 565 | −55.577 | 31.574 | −24.349 | 1.00 | 73.91 | C |
| ATOM | 4162 | CB | SER A | 565 | −56.727 | 32.418 | −23.895 | 1.00 | 76.73 | C |
| ATOM | 4163 | OG | SER A | 565 | −57.350 | 31.783 | −22.814 | 1.00 | 80.38 | O |
| ATOM | 4164 | C | SER A | 565 | −55.521 | 30.331 | −23.468 | 1.00 | 71.71 | C |
| ATOM | 4165 | O | SER A | 565 | −56.281 | 29.398 | −23.668 | 1.00 | 76.18 | O |
| ATOM | 4166 | N | ALA A | 566 | −54.653 | 30.357 | −22.460 | 1.00 | 70.25 | N |
| ATOM | 4167 | CA | ALA A | 566 | −54.606 | 29.326 | −21.394 | 1.00 | 66.33 | C |
| ATOM | 4168 | CB | ALA A | 566 | −53.163 | 29.118 | −20.916 | 1.00 | 59.68 | C |
| ATOM | 4169 | C | ALA A | 566 | −55.546 | 29.737 | −20.232 | 1.00 | 67.53 | C |
| ATOM | 4170 | O | ALA A | 566 | −55.651 | 30.927 | −19.938 | 1.00 | 64.30 | O |
| ATOM | 4171 | N | ARG A | 567 | −56.252 | 28.773 | −19.613 | 1.00 | 69.78 | N |
| ATOM | 4172 | CA | ARG A | 567 | −57.326 | 29.051 | −18.618 | 1.00 | 71.66 | C |
| ATOM | 4173 | CB | ARG A | 567 | −58.693 | 29.277 | −19.323 | 1.00 | 71.46 | C |
| ATOM | 4174 | CG | ARG A | 567 | −58.782 | 30.336 | −20.440 | 1.00 | 72.60 | C |
| ATOM | 4175 | CD | ARG A | 567 | −60.096 | 30.239 | −21.238 | 1.00 | 77.30 | C |
| ATOM | 4176 | NE | ARG A | 567 | −60.624 | 31.455 | −21.933 | 1.00 | 81.42 | N |
| ATOM | 4177 | CZ | ARG A | 567 | −60.356 | 31.869 | −23.195 | 1.00 | 85.92 | C |
| ATOM | 4178 | NH1 | ARG A | 567 | −59.494 | 31.230 | −24.003 | 1.00 | 88.70 | N |
| ATOM | 4179 | NH2 | ARG A | 567 | −60.939 | 32.975 | −23.663 | 1.00 | 85.51 | N |
| ATOM | 4180 | C | ARG A | 567 | −57.491 | 27.891 | −17.615 | 1.00 | 73.71 | C |
| ATOM | 4181 | O | ARG A | 567 | −57.352 | 26.739 | −18.017 | 1.00 | 78.32 | O |
| ATOM | 4182 | N | ILE A | 568 | −57.799 | 28.191 | −16.337 | 1.00 | 75.76 | N |

TABLE 6-continued

Atomic coordinates for CRBN:DDB1: Compound B (Human protein)

| ATOM | 4183 | CA | ILE A | 568 | −58.241 | 27.170 | −15.317 | 1.00 | 75.66 | C |
|---|---|---|---|---|---|---|---|---|---|---|
| ATOM | 4184 | CB | ILE A | 568 | −57.692 | 27.426 | −13.877 | 1.00 | 72.88 | C |
| ATOM | 4185 | CG1 | ILE A | 568 | −56.227 | 27.935 | −13.853 | 1.00 | 73.83 | C |
| ATOM | 4186 | CD1 | ILE A | 568 | −55.221 | 27.143 | −14.651 | 1.00 | 75.67 | C |
| ATOM | 4187 | CG2 | ILE A | 568 | −57.957 | 26.219 | −12.959 | 1.00 | 68.10 | C |
| ATOM | 4188 | C | ILE A | 568 | −59.770 | 27.189 | −15.128 | 1.00 | 79.27 | C |
| ATOM | 4189 | O | ILE A | 568 | −60.382 | 28.247 | −15.259 | 1.00 | 78.02 | O |
| ATOM | 4190 | N | LEU A | 569 | −60.370 | 26.037 | −14.788 | 1.00 | 82.66 | N |
| ATOM | 4191 | CA | LEU A | 569 | −61.828 | 25.909 | −14.461 | 1.00 | 83.01 | C |
| ATOM | 4192 | CB | LEU A | 569 | −62.551 | 25.222 | −15.623 | 1.00 | 82.57 | C |
| ATOM | 4193 | CG | LEU A | 569 | −62.901 | 26.049 | −16.869 | 1.00 | 84.29 | C |
| ATOM | 4194 | CD1 | LEU A | 569 | −61.714 | 26.716 | −17.543 | 1.00 | 82.49 | C |
| ATOM | 4195 | CD2 | LEU A | 569 | −63.627 | 25.164 | −17.886 | 1.00 | 88.04 | C |
| ATOM | 4196 | C | LEU A | 569 | −62.046 | 25.141 | −13.117 | 1.00 | 83.52 | C |
| ATOM | 4197 | O | LEU A | 569 | −61.047 | 24.786 | −12.479 | 1.00 | 81.48 | O |
| ATOM | 4198 | N | LYS A | 570 | −63.279 | 24.903 | −12.718 | 1.00 | 82.50 | N |
| ATOM | 4199 | CA | LYS A | 570 | −63.523 | 24.201 | −11.482 | 1.00 | 83.93 | C |
| ATOM | 4200 | CB | LYS A | 570 | −64.198 | 25.114 | −10.475 | 1.00 | 75.30 | C |
| ATOM | 4201 | C | LYS A | 570 | −64.453 | 23.098 | −11.837 | 1.00 | 85.29 | C |
| ATOM | 4202 | O | LYS A | 570 | −65.173 | 23.202 | −12.806 | 1.00 | 77.15 | O |
| ATOM | 4203 | N | LEU A | 571 | −64.438 | 22.029 | −11.070 | 1.00 | 91.16 | N |
| ATOM | 4204 | CA | LEU A | 571 | −65.318 | 20.928 | −11.355 | 1.00 | 88.31 | C |
| ATOM | 4205 | CB | LEU A | 571 | −64.531 | 19.642 | −11.534 | 1.00 | 82.26 | C |
| ATOM | 4206 | C | LEU A | 571 | −66.168 | 20.847 | −10.131 | 1.00 | 87.85 | C |
| ATOM | 4207 | O | LEU A | 571 | −65.619 | 20.962 | −9.049 | 1.00 | 91.10 | O |
| ATOM | 4208 | N | PRO A | 572 | −67.550 | 20.685 | −10.241 | 1.00 | 91.98 | N |
| ATOM | 4209 | CA | PRO A | 572 | −68.115 | 20.544 | −11.583 | 1.00 | 85.74 | C |
| ATOM | 4210 | CB | PRO A | 572 | −69.292 | 19.586 | −11.376 | 1.00 | 87.22 | C |
| ATOM | 4211 | CG | PRO A | 572 | −69.404 | 19.333 | −9.911 | 1.00 | 88.13 | C |
| ATOM | 4212 | CD | PRO A | 572 | −68.732 | 20.496 | −9.297 | 1.00 | 92.96 | C |
| ATOM | 4213 | C | PRO A | 572 | −68.638 | 21.830 | −12.149 | 1.00 | 83.16 | C |
| ATOM | 4214 | O | PRO A | 572 | −69.404 | 21.784 | −13.074 | 1.00 | 74.93 | O |
| ATOM | 4215 | N | SER A | 573 | −68.292 | 22.958 | −11.567 | 1.00 | 87.58 | N |
| ATOM | 4216 | CA | SER A | 573 | −68.782 | 24.229 | −12.069 | 1.00 | 90.79 | C |
| ATOM | 4217 | CB | SER A | 573 | −68.418 | 25.347 | −11.104 | 1.00 | 86.76 | C |
| ATOM | 4218 | OG | SER A | 573 | −67.137 | 25.851 | −11.394 | 1.00 | 82.72 | O |
| ATOM | 4219 | C | SER A | 573 | −68.335 | 24.618 | −13.473 | 1.00 | 92.86 | C |
| ATOM | 4220 | O | SER A | 573 | −69.114 | 25.149 | −14.235 | 1.00 | 91.68 | O |
| ATOM | 4221 | N | PHE A | 574 | −67.085 | 24.352 | −13.819 | 1.00 | 97.97 | N |
| ATOM | 4222 | CA | PHE A | 574 | −66.555 | 24.764 | −15.115 | 1.00 | 94.82 | C |
| ATOM | 4223 | C | PHE A | 574 | −66.636 | 26.276 | −15.147 | 1.00 | 98.01 | C |
| ATOM | 4224 | O | PHE A | 574 | −67.016 | 26.870 | −16.146 | 1.00 | 101.99 | O |
| ATOM | 4225 | CB | PHE A | 574 | −67.337 | 24.139 | −16.271 | 1.00 | 20.00 | C |
| ATOM | 4226 | N | GLU A | 575 | −66.285 | 26.893 | −14.024 | 1.00 | 97.59 | N |
| ATOM | 4227 | CA | GLU A | 575 | −66.387 | 28.366 | −13.859 | 1.00 | 88.91 | C |
| ATOM | 4228 | CB | GLU A | 575 | −67.129 | 28.659 | −12.553 | 1.00 | 87.72 | C |
| ATOM | 4229 | C | GLU A | 575 | −64.996 | 29.038 | −13.786 | 1.00 | 85.78 | C |
| ATOM | 4230 | O | GLU A | 575 | −64.294 | 28.853 | −12.765 | 1.00 | 85.97 | O |
| ATOM | 4231 | N | LEU A | 576 | −64.643 | 29.844 | −14.823 | 1.00 | 80.65 | N |
| ATOM | 4232 | CA | LEU A | 576 | −63.291 | 30.521 | −15.004 | 1.00 | 76.41 | C |
| ATOM | 4233 | CB | LEU A | 576 | −63.330 | 31.661 | −16.022 | 1.00 | 66.17 | C |
| ATOM | 4234 | C | LEU A | 576 | −62.667 | 31.066 | −13.727 | 1.00 | 78.85 | C |
| ATOM | 4235 | O | LEU A | 576 | −63.367 | 31.681 | −12.936 | 1.00 | 78.56 | O |
| ATOM | 4236 | N | ALA A | 577 | −61.361 | 30.842 | −13.539 | 1.00 | 81.22 | N |
| ATOM | 4237 | CA | ALA A | 577 | −60.745 | 30.928 | −12.202 | 1.00 | 81.36 | C |
| ATOM | 4238 | CB | ALA A | 577 | −60.915 | 29.580 | −11.444 | 1.00 | 70.61 | C |
| ATOM | 4239 | C | ALA A | 577 | −59.270 | 31.510 | −12.152 | 1.00 | 92.92 | C |
| ATOM | 4240 | O | ALA A | 577 | −58.831 | 31.914 | −11.069 | 1.00 | 102.01 | O |
| ATOM | 4241 | N | HIS A | 578 | −58.682 | 31.599 | −13.342 | 1.00 | 96.58 | N |
| ATOM | 4242 | CA | HIS A | 578 | −57.438 | 32.257 | −13.696 | 1.00 | 90.79 | C |
| ATOM | 4243 | CB | HIS A | 578 | −56.227 | 31.453 | −13.291 | 1.00 | 84.74 | C |
| ATOM | 4244 | C | HIS A | 578 | −57.616 | 32.319 | −15.209 | 1.00 | 84.02 | C |
| ATOM | 4245 | O | HIS A | 578 | −58.299 | 31.472 | −15.746 | 1.00 | 80.87 | O |
| ATOM | 4246 | N | LYS A | 579 | −57.068 | 33.301 | −15.904 | 1.00 | 77.60 | N |
| ATOM | 4247 | CA | LYS A | 579 | −57.240 | 33.348 | −17.354 | 1.00 | 84.58 | C |
| ATOM | 4248 | CB | LYS A | 579 | −58.616 | 33.881 | −17.685 | 1.00 | 90.36 | C |
| ATOM | 4249 | C | LYS A | 579 | −56.228 | 34.219 | −18.014 | 1.00 | 78.52 | C |
| ATOM | 4250 | O | LYS A | 579 | −56.394 | 35.421 | −17.957 | 1.00 | 68.13 | O |
| ATOM | 4251 | N | GLU A | 580 | −55.210 | 33.667 | −18.660 | 1.00 | 78.87 | N |
| ATOM | 4252 | CA | GLU A | 580 | −54.216 | 34.536 | −19.265 | 1.00 | 75.89 | C |
| ATOM | 4253 | CB | GLU A | 580 | −52.840 | 34.341 | −18.617 | 1.00 | 76.41 | C |
| ATOM | 4254 | CG | GLU A | 580 | −51.770 | 35.192 | −19.286 | 1.00 | 78.49 | C |
| ATOM | 4255 | CD | GLU A | 580 | −50.528 | 35.397 | −18.460 | 1.00 | 83.87 | C |
| ATOM | 4256 | OE1 | GLU A | 580 | −49.458 | 35.653 | −19.055 | 1.00 | 80.91 | O |
| ATOM | 4257 | OE2 | GLU A | 580 | −50.629 | 35.307 | −17.227 | 1.00 | 87.03 | O |
| ATOM | 4258 | C | GLU A | 580 | −54.102 | 34.483 | −20.760 | 1.00 | 72.40 | C |
| ATOM | 4259 | O | GLU A | 580 | −53.973 | 33.433 | −21.328 | 1.00 | 67.79 | O |
| ATOM | 4260 | N | MET A | 581 | −54.144 | 35.644 | −21.395 | 1.00 | 76.45 | N |

TABLE 6-continued

Atomic coordinates for CRBN:DDB1: Compound B (Human protein)

| ATOM | 4261 | CA  | MET A | 581 | −53.986 | 35.695 | −22.825 | 1.00 | 75.16 | C |
| ATOM | 4262 | CB  | MET A | 581 | −54.392 | 37.031 | −23.408 | 1.00 | 79.96 | C |
| ATOM | 4263 | CG  | MET A | 581 | −55.703 | 36.962 | −24.160 | 1.00 | 80.54 | C |
| ATOM | 4264 | SD  | MET A | 581 | −56.888 | 35.944 | −23.293 | 1.00 | 83.86 | S |
| ATOM | 4265 | CE  | MET A | 581 | −56.698 | 36.571 | −21.645 | 1.00 | 83.07 | C |
| ATOM | 4266 | C   | MET A | 581 | −52.544 | 35.362 | −23.064 | 1.00 | 70.68 | C |
| ATOM | 4267 | O   | MET A | 581 | −51.662 | 35.798 | −22.359 | 1.00 | 64.20 | O |
| ATOM | 4268 | N   | LEU A | 582 | −52.338 | 34.577 | −24.089 | 1.00 | 71.02 | N |
| ATOM | 4269 | CA  | LEU A | 582 | −51.055 | 33.976 | −24.452 | 1.00 | 68.98 | C |
| ATOM | 4270 | CB  | LEU A | 582 | −51.288 | 32.489 | −24.636 | 1.00 | 66.54 | C |
| ATOM | 4271 | CG  | LEU A | 582 | −50.383 | 31.550 | −23.870 | 1.00 | 70.71 | C |
| ATOM | 4272 | CD1 | LEU A | 582 | −50.269 | 31.938 | −22.400 | 1.00 | 72.47 | C |
| ATOM | 4273 | CD2 | LEU A | 582 | −50.890 | 30.114 | −24.017 | 1.00 | 72.46 | C |
| ATOM | 4274 | C   | LEU A | 582 | −50.336 | 34.584 | −25.672 | 1.00 | 70.13 | C |
| ATOM | 4275 | O   | LEU A | 582 | −49.128 | 34.337 | −25.877 | 1.00 | 66.38 | O |
| ATOM | 4276 | N   | GLY A | 583 | −51.067 | 35.363 | −26.472 | 1.00 | 72.07 | N |
| ATOM | 4277 | CA  | GLY A | 583 | −50.475 | 36.126 | −27.554 | 1.00 | 75.16 | C |
| ATOM | 4278 | C   | GLY A | 583 | −50.377 | 35.386 | −28.885 | 1.00 | 84.44 | C |
| ATOM | 4279 | O   | GLY A | 583 | −50.152 | 34.146 | −28.940 | 1.00 | 91.81 | O |
| ATOM | 4280 | N   | GLY A | 584 | −50.574 | 36.159 | −29.962 | 1.00 | 84.75 | N |
| ATOM | 4281 | CA  | GLY A | 584 | −50.143 | 35.786 | −31.312 | 1.00 | 78.99 | C |
| ATOM | 4282 | C   | GLY A | 584 | −51.184 | 35.022 | −32.076 | 1.00 | 77.06 | C |
| ATOM | 4283 | O   | GLY A | 584 | −52.328 | 34.916 | −31.643 | 1.00 | 79.70 | O |
| ATOM | 4284 | N   | GLU A | 585 | −50.780 | 34.473 | −33.212 | 1.00 | 76.14 | N |
| ATOM | 4285 | CA  | GLU A | 585 | −51.705 | 33.772 | −34.079 | 1.00 | 76.89 | C |
| ATOM | 4286 | CB  | GLU A | 585 | −51.464 | 34.130 | −35.548 | 1.00 | 77.79 | C |
| ATOM | 4287 | CG  | GLU A | 585 | −51.903 | 35.551 | −35.884 | 1.00 | 80.77 | C |
| ATOM | 4288 | CD  | GLU A | 585 | −52.631 | 35.651 | −37.205 | 1.00 | 87.60 | C |
| ATOM | 4289 | OE1 | GLU A | 585 | −52.497 | 36.706 | −37.856 | 1.00 | 90.71 | O |
| ATOM | 4290 | OE2 | GLU A | 585 | −53.342 | 34.690 | −37.596 | 1.00 | 89.17 | O |
| ATOM | 4291 | C   | GLU A | 585 | −51.722 | 32.271 | −33.905 | 1.00 | 79.53 | C |
| ATOM | 4292 | O   | GLU A | 585 | −52.653 | 31.680 | −34.407 | 1.00 | 85.34 | O |
| ATOM | 4293 | N   | ILE A | 586 | −50.756 | 31.645 | −33.208 | 1.00 | 82.57 | N |
| ATOM | 4294 | CA  | ILE A | 586 | −50.739 | 30.156 | −33.091 | 1.00 | 83.94 | C |
| ATOM | 4295 | CB  | ILE A | 586 | −49.330 | 29.536 | −33.365 | 1.00 | 87.24 | C |
| ATOM | 4296 | CG1 | ILE A | 586 | −48.735 | 30.050 | −34.708 | 1.00 | 86.57 | C |
| ATOM | 4297 | CD1 | ILE A | 586 | −47.540 | 30.966 | −34.563 | 1.00 | 88.87 | C |
| ATOM | 4298 | CG2 | ILE A | 586 | −49.415 | 28.009 | −33.468 | 1.00 | 87.83 | C |
| ATOM | 4299 | C   | ILE A | 586 | −51.453 | 29.586 | −31.813 | 1.00 | 79.71 | C |
| ATOM | 4300 | O   | ILE A | 586 | −51.366 | 30.141 | −30.709 | 1.00 | 76.86 | O |
| ATOM | 4301 | N   | ILE A | 587 | −52.188 | 28.492 | −32.035 | 1.00 | 73.27 | N |
| ATOM | 4302 | CA  | ILE A | 587 | −53.047 | 27.837 | −31.040 | 1.00 | 75.80 | C |
| ATOM | 4303 | CB  | ILE A | 587 | −54.008 | 26.805 | −31.710 | 1.00 | 79.93 | C |
| ATOM | 4304 | CG1 | ILE A | 587 | −53.381 | 25.963 | −32.860 | 1.00 | 87.16 | C |
| ATOM | 4305 | CD1 | ILE A | 587 | −52.092 | 25.162 | −32.602 | 1.00 | 92.94 | C |
| ATOM | 4306 | CG2 | ILE A | 587 | −55.171 | 27.514 | −32.344 | 1.00 | 82.76 | C |
| ATOM | 4307 | C   | ILE A | 587 | −52.264 | 27.089 | −29.946 | 1.00 | 75.45 | C |
| ATOM | 4308 | O   | ILE A | 587 | −51.097 | 26.775 | −30.142 | 1.00 | 78.56 | O |
| ATOM | 4309 | N   | PRO A | 588 | −52.885 | 26.807 | −28.784 | 1.00 | 71.21 | N |
| ATOM | 4310 | CA  | PRO A | 588 | −52.353 | 25.770 | −27.907 | 1.00 | 70.81 | C |
| ATOM | 4311 | CB  | PRO A | 588 | −53.351 | 25.792 | −26.747 | 1.00 | 71.11 | C |
| ATOM | 4312 | CG  | PRO A | 588 | −53.544 | 27.247 | −26.549 | 1.00 | 71.02 | C |
| ATOM | 4313 | CD  | PRO A | 588 | −53.566 | 27.827 | −27.970 | 1.00 | 73.10 | C |
| ATOM | 4314 | C   | PRO A | 588 | −52.290 | 24.382 | −28.519 | 1.00 | 67.03 | C |
| ATOM | 4315 | O   | PRO A | 588 | −53.172 | 24.056 | −29.283 | 1.00 | 66.73 | O |
| ATOM | 4316 | N   | ARG A | 589 | −51.247 | 23.596 | −28.191 | 1.00 | 66.36 | N |
| ATOM | 4317 | CA  | ARG A | 589 | −51.165 | 22.150 | −28.554 | 1.00 | 64.13 | C |
| ATOM | 4318 | CB  | ARG A | 589 | −50.029 | 21.856 | −29.577 | 1.00 | 59.62 | C |
| ATOM | 4319 | C   | ARG A | 589 | −51.193 | 21.175 | −27.319 | 1.00 | 59.82 | C |
| ATOM | 4320 | O   | ARG A | 589 | −51.721 | 20.078 | −27.416 | 1.00 | 61.58 | O |
| ATOM | 4321 | N   | SER A | 590 | −50.676 | 21.555 | −26.167 | 1.00 | 57.95 | N |
| ATOM | 4322 | CA  | SER A | 590 | −50.838 | 20.723 | −24.964 | 1.00 | 58.70 | C |
| ATOM | 4323 | CB  | SER A | 590 | −49.812 | 19.572 | −24.824 | 1.00 | 56.64 | C |
| ATOM | 4324 | C   | SER A | 590 | −50.707 | 21.638 | −23.786 | 1.00 | 61.70 | C |
| ATOM | 4325 | O   | SER A | 590 | −50.017 | 22.682 | −23.833 | 1.00 | 56.13 | O |
| ATOM | 4326 | N   | ILE A | 591 | −51.385 | 21.224 | −22.724 | 1.00 | 64.61 | N |
| ATOM | 4327 | CA  | ILE A | 591 | −51.420 | 21.982 | −21.509 | 1.00 | 64.14 | C |
| ATOM | 4328 | CB  | ILE A | 591 | −52.713 | 22.786 | −21.398 | 1.00 | 69.41 | C |
| ATOM | 4329 | CG1 | ILE A | 591 | −52.518 | 23.858 | −20.323 | 1.00 | 76.97 | C |
| ATOM | 4330 | CD1 | ILE A | 591 | −53.498 | 24.997 | −20.446 | 1.00 | 81.53 | C |
| ATOM | 4331 | CG2 | ILE A | 591 | −53.959 | 21.896 | −21.159 | 1.00 | 67.46 | C |
| ATOM | 4332 | C   | ILE A | 591 | −51.303 | 20.998 | −20.408 | 1.00 | 60.79 | C |
| ATOM | 4333 | O   | ILE A | 591 | −51.825 | 19.930 | −20.544 | 1.00 | 63.71 | O |
| ATOM | 4334 | N   | LEU A | 592 | −50.602 | 21.351 | −19.346 | 1.00 | 62.09 | N |
| ATOM | 4335 | CA  | LEU A | 592 | −50.238 | 20.401 | −18.303 | 1.00 | 68.64 | C |
| ATOM | 4336 | CB  | LEU A | 592 | −48.890 | 19.741 | −18.638 | 1.00 | 66.48 | C |
| ATOM | 4337 | CG  | LEU A | 592 | −48.318 | 18.629 | −17.708 | 1.00 | 68.09 | C |
| ATOM | 4338 | CD1 | LEU A | 592 | −49.321 | 17.727 | −16.966 | 1.00 | 64.40 | C |

TABLE 6-continued

Atomic coordinates for CRBN:DDB1: Compound B (Human protein)

| ATOM | 4339 | CD2 | LEU A | 592 | −47.347 | 17.752 | −18.493 | 1.00 | 69.87 | C |
|---|---|---|---|---|---|---|---|---|---|---|
| ATOM | 4340 | C | LEU A | 592 | −50.166 | 21.078 | −16.924 | 1.00 | 76.53 | C |
| ATOM | 4341 | O | LEU A | 592 | −49.398 | 22.058 | −16.748 | 1.00 | 76.84 | O |
| ATOM | 4342 | N | MET A | 593 | −50.972 | 20.560 | −15.975 | 1.00 | 75.46 | N |
| ATOM | 4343 | CA | MET A | 593 | −50.955 | 20.987 | −14.574 | 1.00 | 78.71 | C |
| ATOM | 4344 | CB | MET A | 593 | −52.331 | 20.851 | −13.889 | 1.00 | 83.10 | C |
| ATOM | 4345 | CG | MET A | 593 | −53.175 | 22.114 | −13.720 | 1.00 | 81.80 | C |
| ATOM | 4346 | SD | MET A | 593 | −54.945 | 21.754 | −13.498 | 1.00 | 83.56 | S |
| ATOM | 4347 | CE | MET A | 593 | −54.943 | 20.453 | −12.236 | 1.00 | 83.78 | C |
| ATOM | 4348 | C | MET A | 593 | −50.037 | 19.991 | −13.946 | 1.00 | 77.58 | C |
| ATOM | 4349 | O | MET A | 593 | −50.370 | 18.797 | −13.923 | 1.00 | 84.06 | O |
| ATOM | 4350 | N | THR A | 594 | −48.905 | 20.464 | −13.434 | 1.00 | 73.39 | N |
| ATOM | 4351 | CA | THR A | 594 | −47.955 | 19.570 | −12.816 | 1.00 | 73.95 | C |
| ATOM | 4352 | CB | THR A | 594 | −46.867 | 19.188 | −13.815 | 1.00 | 70.25 | C |
| ATOM | 4353 | OG1 | THR A | 594 | −46.827 | 17.761 | −13.895 | 1.00 | 71.88 | O |
| ATOM | 4354 | CG2 | THR A | 594 | −45.472 | 19.764 | −13.477 | 1.00 | 69.82 | C |
| ATOM | 4355 | C | THR A | 594 | −47.405 | 20.111 | −11.515 | 1.00 | 84.18 | C |
| ATOM | 4356 | O | THR A | 594 | −47.607 | 21.283 | −11.208 | 1.00 | 98.08 | O |
| ATOM | 4357 | N | THR A | 595 | −46.657 | 19.289 | −10.791 | 1.00 | 90.77 | N |
| ATOM | 4358 | CA | THR A | 595 | −46.010 | 19.706 | −9.551 | 1.00 | 86.88 | C |
| ATOM | 4359 | CB | THR A | 595 | −46.707 | 19.105 | −8.304 | 1.00 | 85.96 | C |
| ATOM | 4360 | OG1 | THR A | 595 | −45.759 | 18.864 | −7.265 | 1.00 | 80.22 | O |
| ATOM | 4361 | CG2 | THR A | 595 | −47.386 | 17.813 | −8.622 | 1.00 | 91.02 | C |
| ATOM | 4362 | C | THR A | 595 | −44.507 | 19.402 | −9.581 | 1.00 | 80.10 | C |
| ATOM | 4363 | O | THR A | 595 | −44.111 | 18.270 | −9.708 | 1.00 | 76.17 | O |
| ATOM | 4364 | N | PHE A | 596 | −43.684 | 20.421 | −9.417 | 1.00 | 82.51 | N |
| ATOM | 4365 | CA | PHE A | 596 | −42.246 | 20.257 | −9.418 | 1.00 | 89.45 | C |
| ATOM | 4366 | CB | PHE A | 596 | −41.598 | 21.111 | −10.477 | 1.00 | 93.61 | C |
| ATOM | 4367 | CG | PHE A | 596 | −41.671 | 20.534 | −11.848 | 1.00 | 96.20 | C |
| ATOM | 4368 | CD1 | PHE A | 596 | −41.485 | 19.198 | −12.052 | 1.00 | 93.56 | C |
| ATOM | 4369 | CE1 | PHE A | 596 | −41.538 | 18.674 | −13.313 | 1.00 | 93.45 | C |
| ATOM | 4370 | CZ | PHE A | 596 | −41.768 | 19.489 | −14.384 | 1.00 | 90.32 | C |
| ATOM | 4371 | CE2 | PHE A | 596 | −41.952 | 20.826 | −14.191 | 1.00 | 89.10 | C |
| ATOM | 4372 | CD2 | PHE A | 596 | −41.896 | 21.343 | −12.929 | 1.00 | 94.37 | C |
| ATOM | 4373 | C | PHE A | 596 | −41.762 | 20.714 | −8.075 | 1.00 | 95.95 | C |
| ATOM | 4374 | O | PHE A | 596 | −42.361 | 21.582 | −7.456 | 1.00 | 90.97 | O |
| ATOM | 4375 | N | GLU A | 597 | −40.686 | 20.110 | −7.573 | 1.00 | 103.55 | N |
| ATOM | 4376 | CA | GLU A | 597 | −40.182 | 20.441 | −6.244 | 1.00 | 105.68 | C |
| ATOM | 4377 | CB | GLU A | 597 | −39.905 | 21.928 | −6.168 | 1.00 | 108.45 | C |
| ATOM | 4378 | CG | GLU A | 597 | −38.823 | 22.306 | −5.186 | 1.00 | 107.72 | C |
| ATOM | 4379 | CD | GLU A | 597 | −37.443 | 22.120 | −5.758 | 1.00 | 103.22 | C |
| ATOM | 4380 | OE1 | GLU A | 597 | −37.088 | 20.970 | −6.043 | 1.00 | 103.58 | O |
| ATOM | 4381 | OE2 | GLU A | 597 | −36.716 | 23.121 | −5.913 | 1.00 | 99.39 | O |
| ATOM | 4382 | C | GLU A | 597 | −41.358 | 20.062 | −5.372 | 1.00 | 104.58 | C |
| ATOM | 4383 | O | GLU A | 597 | −41.895 | 18.979 | −5.546 | 1.00 | 108.63 | O |
| ATOM | 4384 | N | SER A | 598 | −41.787 | 20.931 | −4.483 | 1.00 | 98.35 | N |
| ATOM | 4385 | CA | SER A | 598 | −42.986 | 20.647 | −3.738 | 1.00 | 91.10 | C |
| ATOM | 4386 | CB | SER A | 598 | −42.733 | 20.590 | −2.259 | 1.00 | 88.33 | C |
| ATOM | 4387 | OG | SER A | 598 | −43.490 | 19.530 | −1.720 | 1.00 | 88.20 | O |
| ATOM | 4388 | C | SER A | 598 | −44.049 | 21.667 | −4.125 | 1.00 | 90.80 | C |
| ATOM | 4389 | O | SER A | 598 | −45.065 | 21.786 | −3.476 | 1.00 | 85.25 | O |
| ATOM | 4390 | N | SER A | 599 | −43.785 | 22.403 | −5.195 | 1.00 | 97.99 | N |
| ATOM | 4391 | CA | SER A | 599 | −44.655 | 23.437 | −5.712 | 1.00 | 95.92 | C |
| ATOM | 4392 | CB | SER A | 599 | −43.809 | 24.480 | −6.414 | 1.00 | 98.82 | C |
| ATOM | 4393 | OG | SER A | 599 | −42.620 | 24.708 | −5.689 | 1.00 | 99.77 | O |
| ATOM | 4394 | C | SER A | 599 | −45.678 | 22.909 | −6.685 | 1.00 | 88.97 | C |
| ATOM | 4395 | O | SER A | 599 | −45.776 | 21.721 | −6.895 | 1.00 | 77.01 | O |
| ATOM | 4396 | N | HIS A | 600 | −46.467 | 23.817 | −7.243 | 1.00 | 91.39 | N |
| ATOM | 4397 | CA | HIS A | 600 | −47.469 | 23.487 | −8.239 | 1.00 | 92.74 | C |
| ATOM | 4398 | CB | HIS A | 600 | −48.851 | 23.602 | −7.660 | 1.00 | 92.16 | C |
| ATOM | 4399 | CG | HIS A | 600 | −49.126 | 22.604 | −6.599 | 1.00 | 95.67 | C |
| ATOM | 4400 | ND1 | HIS A | 600 | −48.280 | 21.551 | −6.351 | 1.00 | 96.55 | N |
| ATOM | 4401 | CE1 | HIS A | 600 | −48.774 | 20.822 | −5.370 | 1.00 | 96.70 | C |
| ATOM | 4402 | NE2 | HIS A | 600 | −49.909 | 21.366 | −4.975 | 1.00 | 95.39 | N |
| ATOM | 4403 | CD2 | HIS A | 600 | −50.155 | 22.479 | −5.734 | 1.00 | 96.19 | C |
| ATOM | 4404 | C | HIS A | 600 | −47.382 | 24.439 | −9.399 | 1.00 | 95.63 | C |
| ATOM | 4405 | O | HIS A | 600 | −47.393 | 25.641 | −9.203 | 1.00 | 104.87 | O |
| ATOM | 4406 | N | TYR A | 601 | −47.325 | 23.919 | −10.613 | 1.00 | 95.55 | N |
| ATOM | 4407 | CA | TYR A | 601 | −47.239 | 24.792 | −11.764 | 1.00 | 90.47 | C |
| ATOM | 4408 | CB | TYR A | 601 | −45.810 | 24.850 | −12.300 | 1.00 | 87.84 | C |
| ATOM | 4409 | CG | TYR A | 601 | −44.676 | 24.947 | −11.309 | 1.00 | 89.85 | C |
| ATOM | 4410 | CD1 | TYR A | 601 | −44.652 | 24.187 | −10.161 | 1.00 | 93.09 | C |
| ATOM | 4411 | CE1 | TYR A | 601 | −43.599 | 24.265 | −9.276 | 1.00 | 97.48 | C |
| ATOM | 4412 | CZ | TYR A | 601 | −42.532 | 25.084 | −9.554 | 1.00 | 93.89 | C |
| ATOM | 4413 | OH | TYR A | 601 | −41.474 | 25.160 | −8.681 | 1.00 | 85.92 | O |
| ATOM | 4414 | CE2 | TYR A | 601 | −42.521 | 25.831 | −10.700 | 1.00 | 89.00 | C |
| ATOM | 4415 | CD2 | TYR A | 601 | −43.586 | 25.753 | −11.571 | 1.00 | 89.88 | C |
| ATOM | 4416 | C | TYR A | 601 | −48.101 | 24.328 | −12.913 | 1.00 | 86.12 | C |

TABLE 6-continued

Atomic coordinates for CRBN:DDB1: Compound B (Human protein)

| ATOM | 4417 | O | TYR A | 601 | −48.481 | 23.177 | −12.990 | 1.00 | 80.44 | O |
|------|------|-----|-------|-----|---------|--------|---------|------|-------|---|
| ATOM | 4418 | N | LEU A | 602 | −48.396 | 25.262 | −13.803 | 1.00 | 85.06 | N |
| ATOM | 4419 | CA | LEU A | 602 | −49.088 | 25.011 | −15.068 | 1.00 | 75.71 | C |
| ATOM | 4420 | CB | LEU A | 602 | −50.236 | 25.954 | −15.236 | 1.00 | 71.78 | C |
| ATOM | 4421 | CG | LEU A | 602 | −51.077 | 25.633 | −16.460 | 1.00 | 75.58 | C |
| ATOM | 4422 | CD1 | LEU A | 602 | −52.526 | 25.408 | −16.046 | 1.00 | 77.66 | C |
| ATOM | 4423 | CD2 | LEU A | 602 | −50.962 | 26.738 | −17.500 | 1.00 | 74.25 | C |
| ATOM | 4424 | C | LEU A | 602 | −48.129 | 25.263 | −16.221 | 1.00 | 75.57 | C |
| ATOM | 4425 | O | LEU A | 602 | −47.482 | 26.329 | −16.296 | 1.00 | 68.67 | O |
| ATOM | 4426 | N | LEU A | 603 | −48.030 | 24.267 | −17.103 | 1.00 | 74.54 | N |
| ATOM | 4427 | CA | LEU A | 603 | −47.282 | 24.400 | −18.353 | 1.00 | 73.64 | C |
| ATOM | 4428 | CB | LEU A | 603 | −46.253 | 23.262 | −18.552 | 1.00 | 77.60 | C |
| ATOM | 4429 | CG | LEU A | 603 | −44.964 | 23.179 | −17.705 | 1.00 | 77.15 | C |
| ATOM | 4430 | CD1 | LEU A | 603 | −45.291 | 23.112 | −16.229 | 1.00 | 81.74 | C |
| ATOM | 4431 | CD2 | LEU A | 603 | −44.144 | 21.962 | −18.072 | 1.00 | 78.37 | C |
| ATOM | 4432 | C | LEU A | 603 | −48.323 | 24.421 | −19.464 | 1.00 | 68.16 | C |
| ATOM | 4433 | O | LEU A | 603 | −49.419 | 23.886 | −19.288 | 1.00 | 64.38 | O |
| ATOM | 4434 | N | CYS A | 604 | −47.985 | 25.128 | −20.546 | 1.00 | 67.04 | N |
| ATOM | 4435 | CA | CYS A | 604 | −48.800 | 25.248 | −21.746 | 1.00 | 64.89 | C |
| ATOM | 4436 | CB | CYS A | 604 | −49.711 | 26.460 | −21.695 | 1.00 | 63.06 | C |
| ATOM | 4437 | SG | CYS A | 604 | −50.952 | 26.252 | −22.989 | 1.00 | 69.00 | S |
| ATOM | 4438 | C | CYS A | 604 | −47.900 | 25.397 | −22.950 | 1.00 | 64.50 | C |
| ATOM | 4439 | O | CYS A | 604 | −47.002 | 26.244 | −22.922 | 1.00 | 64.70 | O |
| ATOM | 4440 | N | ALA A | 605 | −48.135 | 24.590 | −23.995 | 1.00 | 65.48 | N |
| ATOM | 4441 | CA | ALA A | 605 | −47.300 | 24.623 | −25.216 | 1.00 | 67.14 | C |
| ATOM | 4442 | CB | ALA A | 605 | −46.682 | 23.263 | −25.458 | 1.00 | 63.85 | C |
| ATOM | 4443 | C | ALA A | 605 | −48.040 | 25.135 | −26.484 | 1.00 | 70.72 | C |
| ATOM | 4444 | O | ALA A | 605 | −49.210 | 24.807 | −26.715 | 1.00 | 66.96 | O |
| ATOM | 4445 | N | LEU A | 606 | −47.340 | 25.956 | −27.273 | 1.00 | 74.10 | N |
| ATOM | 4446 | CA | LEU A | 606 | −47.859 | 26.507 | −28.523 | 1.00 | 77.22 | C |
| ATOM | 4447 | CB | LEU A | 606 | −47.494 | 27.991 | −28.689 | 1.00 | 77.73 | C |
| ATOM | 4448 | CG | LEU A | 606 | −47.902 | 29.034 | −27.624 | 1.00 | 81.91 | C |
| ATOM | 4449 | CD1 | LEU A | 606 | −48.136 | 30.419 | −28.250 | 1.00 | 80.03 | C |
| ATOM | 4450 | CD2 | LEU A | 606 | −49.105 | 28.583 | −26.777 | 1.00 | 81.52 | C |
| ATOM | 4451 | C | LEU A | 606 | −47.281 | 25.737 | −29.690 | 1.00 | 81.89 | C |
| ATOM | 4452 | O | LEU A | 606 | −46.202 | 25.134 | −29.570 | 1.00 | 88.20 | O |
| ATOM | 4453 | N | GLY A | 607 | −48.004 | 25.781 | −30.817 | 1.00 | 84.48 | N |
| ATOM | 4454 | CA | GLY A | 607 | −47.640 | 25.103 | −32.066 | 1.00 | 85.05 | C |
| ATOM | 4455 | C | GLY A | 607 | −46.297 | 25.521 | −32.646 | 1.00 | 88.67 | C |
| ATOM | 4456 | O | GLY A | 607 | −45.571 | 24.686 | −33.191 | 1.00 | 93.71 | O |
| ATOM | 4457 | N | ASP A | 608 | −45.957 | 26.804 | −32.512 | 1.00 | 88.05 | N |
| ATOM | 4458 | CA | ASP A | 608 | −44.627 | 27.305 | −32.897 | 1.00 | 87.10 | C |
| ATOM | 4459 | CB | ASP A | 608 | −44.602 | 28.848 | −32.960 | 1.00 | 90.29 | C |
| ATOM | 4460 | CG | ASP A | 608 | −44.833 | 29.519 | −31.593 | 1.00 | 89.69 | C |
| ATOM | 4461 | OD1 | ASP A | 608 | −45.366 | 28.864 | −30.675 | 1.00 | 84.75 | O |
| ATOM | 4462 | OD2 | ASP A | 608 | −44.501 | 30.717 | −31.452 | 1.00 | 93.34 | O |
| ATOM | 4463 | C | ASP A | 608 | −43.443 | 26.827 | −32.044 | 1.00 | 84.59 | C |
| ATOM | 4464 | O | ASP A | 608 | −42.313 | 27.077 | −32.444 | 1.00 | 90.74 | O |
| ATOM | 4465 | N | GLY A | 609 | −43.672 | 26.189 | −30.888 | 1.00 | 78.51 | N |
| ATOM | 4466 | CA | GLY A | 609 | −42.564 | 25.804 | −29.969 | 1.00 | 80.68 | C |
| ATOM | 4467 | C | GLY A | 609 | −42.567 | 26.406 | −28.553 | 1.00 | 77.60 | C |
| ATOM | 4468 | O | GLY A | 609 | −42.107 | 25.785 | −27.598 | 1.00 | 73.18 | O |
| ATOM | 4469 | N | ALA A | 610 | −43.088 | 27.623 | −28.437 | 1.00 | 79.21 | N |
| ATOM | 4470 | CA | ALA A | 610 | −43.288 | 28.342 | −27.163 | 1.00 | 74.27 | C |
| ATOM | 4471 | CB | ALA A | 610 | −44.120 | 29.620 | −27.410 | 1.00 | 74.04 | C |
| ATOM | 4472 | C | ALA A | 610 | −43.905 | 27.523 | −26.002 | 1.00 | 69.79 | C |
| ATOM | 4473 | O | ALA A | 610 | −44.976 | 26.915 | −26.104 | 1.00 | 60.94 | O |
| ATOM | 4474 | N | LEU A | 611 | −43.198 | 27.544 | −24.887 | 1.00 | 69.85 | N |
| ATOM | 4475 | CA | LEU A | 611 | −43.663 | 26.931 | −23.686 | 1.00 | 74.21 | C |
| ATOM | 4476 | CB | LEU A | 611 | −42.676 | 25.842 | −23.282 | 1.00 | 78.04 | C |
| ATOM | 4477 | CG | LEU A | 611 | −43.001 | 24.857 | −22.153 | 1.00 | 80.92 | C |
| ATOM | 4478 | CD1 | LEU A | 611 | −42.269 | 25.246 | −20.888 | 1.00 | 86.76 | C |
| ATOM | 4479 | CD2 | LEU A | 611 | −44.481 | 24.747 | −21.853 | 1.00 | 81.41 | C |
| ATOM | 4480 | C | LEU A | 611 | −43.733 | 28.050 | −22.667 | 1.00 | 76.73 | C |
| ATOM | 4481 | O | LEU A | 611 | −42.730 | 28.750 | −22.451 | 1.00 | 75.56 | O |
| ATOM | 4482 | N | PHE A | 612 | −44.930 | 28.249 | −22.106 | 1.00 | 77.44 | N |
| ATOM | 4483 | CA | PHE A | 612 | −45.177 | 29.227 | −21.045 | 1.00 | 80.41 | C |
| ATOM | 4484 | CB | PHE A | 612 | −46.445 | 30.078 | −21.313 | 1.00 | 85.15 | C |
| ATOM | 4485 | CG | PHE A | 612 | −46.293 | 31.089 | −22.431 | 1.00 | 87.90 | C |
| ATOM | 4486 | CD1 | PHE A | 612 | −45.560 | 32.267 | −22.238 | 1.00 | 87.59 | C |
| ATOM | 4487 | CE1 | PHE A | 612 | −45.409 | 33.179 | −23.269 | 1.00 | 85.72 | C |
| ATOM | 4488 | CZ | PHE A | 612 | −45.992 | 32.932 | −24.505 | 1.00 | 87.13 | C |
| ATOM | 4489 | CE2 | PHE A | 612 | −46.711 | 31.768 | −24.720 | 1.00 | 84.79 | C |
| ATOM | 4490 | CD2 | PHE A | 612 | −46.871 | 30.861 | −23.684 | 1.00 | 85.33 | C |
| ATOM | 4491 | C | PHE A | 612 | −45.398 | 28.427 | −19.774 | 1.00 | 79.86 | C |
| ATOM | 4492 | O | PHE A | 612 | −46.193 | 27.483 | −19.786 | 1.00 | 74.35 | O |
| ATOM | 4493 | N | TYR A | 613 | −44.733 | 28.820 | −18.682 | 1.00 | 77.95 | N |
| ATOM | 4494 | CA | TYR A | 613 | −45.087 | 28.301 | −17.358 | 1.00 | 75.32 | C |

TABLE 6-continued

Atomic coordinates for CRBN:DDB1: Compound B (Human protein)

| ATOM | 4495 | CB | TYR A | 613 | −43.967 | 27.569 | −16.770 | 1.00 | 71.71 | C |
|---|---|---|---|---|---|---|---|---|---|---|
| ATOM | 4496 | CG | TYR A | 613 | −42.571 | 28.042 | −16.711 | 1.00 | 67.52 | C |
| ATOM | 4497 | CD1 | TYR A | 613 | −41.789 | 28.133 | −17.858 | 1.00 | 65.63 | C |
| ATOM | 4498 | CE1 | TYR A | 613 | −40.471 | 28.603 | −17.801 | 1.00 | 65.27 | C |
| ATOM | 4499 | CZ | TYR A | 613 | −39.907 | 28.980 | −16.570 | 1.00 | 64.53 | C |
| ATOM | 4500 | OH | TYR A | 613 | −38.606 | 29.461 | −16.548 | 1.00 | 56.40 | O |
| ATOM | 4501 | CE2 | TYR A | 613 | −40.663 | 28.865 | −15.402 | 1.00 | 66.58 | C |
| ATOM | 4502 | CD2 | TYR A | 613 | −41.977 | 28.385 | −15.475 | 1.00 | 67.89 | C |
| ATOM | 4503 | C | TYR A | 613 | −45.615 | 29.328 | −16.330 | 1.00 | 78.43 | C |
| ATOM | 4504 | O | TYR A | 613 | −45.327 | 30.527 | −16.410 | 1.00 | 76.05 | O |
| ATOM | 4505 | N | PHE A | 614 | −46.412 | 28.822 | −15.386 | 1.00 | 78.40 | N |
| ATOM | 4506 | CA | PHE A | 614 | −47.058 | 29.615 | −14.341 | 1.00 | 83.02 | C |
| ATOM | 4507 | CB | PHE A | 614 | −48.512 | 29.875 | −14.742 | 1.00 | 87.38 | C |
| ATOM | 4508 | CG | PHE A | 614 | −48.666 | 30.683 | −15.998 | 1.00 | 91.32 | C |
| ATOM | 4509 | CD1 | PHE A | 614 | −48.552 | 30.079 | −17.260 | 1.00 | 91.87 | C |
| ATOM | 4510 | CE1 | PHE A | 614 | −48.691 | 30.820 | −18.428 | 1.00 | 88.66 | C |
| ATOM | 4511 | CZ | PHE A | 614 | −48.949 | 32.181 | −18.339 | 1.00 | 93.34 | C |
| ATOM | 4512 | CE2 | PHE A | 614 | −49.066 | 32.795 | −17.087 | 1.00 | 93.51 | C |
| ATOM | 4513 | CD2 | PHE A | 614 | −48.930 | 32.046 | −15.931 | 1.00 | 93.67 | C |
| ATOM | 4514 | C | PHE A | 614 | −47.053 | 28.836 | −13.006 | 1.00 | 85.77 | C |
| ATOM | 4515 | O | PHE A | 614 | −47.275 | 27.628 | −13.030 | 1.00 | 93.65 | O |
| ATOM | 4516 | N | GLY A | 615 | −46.816 | 29.500 | −11.858 | 1.00 | 77.80 | N |
| ATOM | 4517 | CA | GLY A | 615 | −46.992 | 28.862 | −10.534 | 1.00 | 72.98 | C |
| ATOM | 4518 | C | GLY A | 615 | −48.473 | 28.605 | −10.303 | 1.00 | 72.64 | C |
| ATOM | 4519 | O | GLY A | 615 | −49.275 | 29.403 | −10.728 | 1.00 | 73.28 | O |
| ATOM | 4520 | N | LEU A | 616 | −48.864 | 27.518 | −9.648 | 1.00 | 72.56 | N |
| ATOM | 4521 | CA | LEU A | 616 | −50.285 | 27.218 | −9.508 | 1.00 | 80.57 | C |
| ATOM | 4522 | CB | LEU A | 616 | −50.632 | 25.891 | −10.169 | 1.00 | 87.89 | C |
| ATOM | 4523 | CG | LEU A | 616 | −52.141 | 25.597 | −10.371 | 1.00 | 95.58 | C |
| ATOM | 4524 | CD1 | LEU A | 616 | −52.732 | 26.481 | −11.467 | 1.00 | 100.27 | C |
| ATOM | 4525 | CD2 | LEU A | 616 | −52.439 | 24.136 | −10.670 | 1.00 | 98.76 | C |
| ATOM | 4526 | C | LEU A | 616 | −50.758 | 27.184 | −8.074 | 1.00 | 87.84 | C |
| ATOM | 4527 | O | LEU A | 616 | −50.027 | 26.827 | −7.164 | 1.00 | 96.81 | O |
| ATOM | 4528 | N | ASN A | 617 | −51.979 | 27.626 | −7.868 | 1.00 | 94.21 | N |
| ATOM | 4529 | CA | ASN A | 617 | −52.535 | 27.627 | −6.546 | 1.00 | 98.71 | C |
| ATOM | 4530 | CB | ASN A | 617 | −53.035 | 29.019 | −6.226 | 1.00 | 99.72 | C |
| ATOM | 4531 | CG | ASN A | 617 | −53.683 | 29.099 | −4.878 | 1.00 | 101.08 | C |
| ATOM | 4532 | OD1 | ASN A | 617 | −53.343 | 29.953 | −4.075 | 1.00 | 108.72 | O |
| ATOM | 4533 | ND2 | ASN A | 617 | −54.613 | 28.200 | −4.613 | 1.00 | 101.68 | N |
| ATOM | 4534 | C | ASN A | 617 | −53.687 | 26.696 | −6.688 | 1.00 | 101.16 | C |
| ATOM | 4535 | O | ASN A | 617 | −54.709 | 27.079 | −7.229 | 1.00 | 102.17 | O |
| ATOM | 4536 | N | ILE A | 618 | −53.552 | 25.481 | −6.185 | 1.00 | 99.91 | N |
| ATOM | 4537 | CA | ILE A | 618 | −54.619 | 24.528 | −6.360 | 1.00 | 102.01 | C |
| ATOM | 4538 | CB | ILE A | 618 | −54.253 | 23.136 | −5.833 | 1.00 | 100.01 | C |
| ATOM | 4539 | CG1 | ILE A | 618 | −54.255 | 23.101 | −4.313 | 1.00 | 100.40 | C |
| ATOM | 4540 | CD1 | ILE A | 618 | −53.959 | 21.731 | −3.748 | 1.00 | 93.86 | C |
| ATOM | 4541 | CG2 | ILE A | 618 | −52.895 | 22.726 | −6.344 | 1.00 | 100.40 | C |
| ATOM | 4542 | C | ILE A | 618 | −55.911 | 24.946 | −5.723 | 1.00 | 111.07 | C |
| ATOM | 4543 | O | ILE A | 618 | −56.959 | 24.800 | −6.326 | 1.00 | 120.34 | O |
| ATOM | 4544 | N | GLU A | 619 | −55.855 | 25.469 | −4.510 | 1.00 | 106.01 | N |
| ATOM | 4545 | CA | GLU A | 619 | −57.085 | 25.839 | −3.838 | 1.00 | 96.25 | C |
| ATOM | 4546 | CB | GLU A | 619 | −56.776 | 26.257 | −2.410 | 1.00 | 96.37 | C |
| ATOM | 4547 | C | GLU A | 619 | −57.870 | 26.933 | −4.524 | 1.00 | 88.63 | C |
| ATOM | 4548 | O | GLU A | 619 | −59.071 | 26.835 | −4.672 | 1.00 | 71.44 | O |
| ATOM | 4549 | N | THR A | 620 | −57.181 | 27.973 | −4.951 | 1.00 | 90.41 | N |
| ATOM | 4550 | CA | THR A | 620 | −57.830 | 29.100 | −5.583 | 1.00 | 90.17 | C |
| ATOM | 4551 | CB | THR A | 620 | −57.148 | 30.393 | −5.142 | 1.00 | 81.28 | C |
| ATOM | 4552 | C | THR A | 620 | −57.826 | 29.144 | −7.091 | 1.00 | 95.63 | C |
| ATOM | 4553 | O | THR A | 620 | −58.811 | 29.494 | −7.713 | 1.00 | 96.18 | O |
| ATOM | 4554 | N | GLY A | 621 | −56.699 | 28.802 | −7.674 | 1.00 | 97.39 | N |
| ATOM | 4555 | CA | GLY A | 621 | −56.513 | 28.862 | −9.137 | 1.00 | 96.30 | C |
| ATOM | 4556 | C | GLY A | 621 | −55.500 | 29.910 | −9.617 | 1.00 | 99.98 | C |
| ATOM | 4557 | O | GLY A | 621 | −55.190 | 29.970 | −10.816 | 1.00 | 94.56 | O |
| ATOM | 4558 | N | LEU A | 622 | −54.994 | 30.748 | −8.703 | 1.00 | 105.31 | N |
| ATOM | 4559 | CA | LEU A | 622 | −54.068 | 31.829 | −9.069 | 1.00 | 103.24 | C |
| ATOM | 4560 | CB | LEU A | 622 | −53.759 | 32.756 | −7.858 | 1.00 | 98.15 | C |
| ATOM | 4561 | C | LEU A | 622 | −52.796 | 31.288 | −9.802 | 1.00 | 95.15 | C |
| ATOM | 4562 | O | LEU A | 622 | −51.860 | 30.718 | −9.211 | 1.00 | 80.42 | O |
| ATOM | 4563 | N | LEU A | 623 | −52.845 | 31.430 | −11.127 | 1.00 | 95.50 | N |
| ATOM | 4564 | CA | LEU A | 623 | −51.662 | 31.342 | −11.987 | 1.00 | 96.38 | C |
| ATOM | 4565 | CB | LEU A | 623 | −52.046 | 31.041 | −13.475 | 1.00 | 97.26 | C |
| ATOM | 4566 | C | LEU A | 623 | −50.835 | 32.649 | −11.808 | 1.00 | 86.10 | C |
| ATOM | 4567 | O | LEU A | 623 | −51.360 | 33.744 | −11.970 | 1.00 | 77.35 | O |
| ATOM | 4568 | N | SER A | 624 | −49.555 | 32.494 | −11.449 | 1.00 | 83.18 | N |
| ATOM | 4569 | CA | SER A | 624 | −48.604 | 33.593 | −11.186 | 1.00 | 79.78 | C |
| ATOM | 4570 | CB | SER A | 624 | −48.312 | 33.632 | −9.672 | 1.00 | 78.15 | C |
| ATOM | 4571 | OG | SER A | 624 | −47.345 | 32.661 | −9.265 | 1.00 | 73.43 | O |
| ATOM | 4572 | C | SER A | 624 | −47.264 | 33.472 | −11.980 | 1.00 | 78.93 | C |

TABLE 6-continued

Atomic coordinates for CRBN:DDB1: Compound B (Human protein)

| ATOM | 4573 | O | SER A | 624 | −46.916 | 32.400 | −12.449 | 1.00 | 83.33 | O |
|---|---|---|---|---|---|---|---|---|---|---|
| ATOM | 4574 | N | ASP A | 625 | −46.525 | 34.573 | −12.109 | 1.00 | 80.84 | N |
| ATOM | 4575 | CA | ASP A | 625 | −45.152 | 34.608 | −12.676 | 1.00 | 84.69 | C |
| ATOM | 4576 | CB | ASP A | 625 | −44.147 | 34.038 | −11.680 | 1.00 | 90.68 | C |
| ATOM | 4577 | CG | ASP A | 625 | −43.978 | 34.907 | −10.477 | 1.00 | 99.65 | C |
| ATOM | 4578 | OD1 | ASP A | 625 | −43.917 | 36.149 | −10.633 | 1.00 | 104.12 | O |
| ATOM | 4579 | OD2 | ASP A | 625 | −43.890 | 34.346 | −9.368 | 1.00 | 111.73 | O |
| ATOM | 4580 | C | ASP A | 625 | −44.949 | 33.932 | −14.026 | 1.00 | 84.04 | C |
| ATOM | 4581 | O | ASP A | 625 | −44.254 | 32.899 | −14.136 | 1.00 | 91.01 | O |
| ATOM | 4582 | N | ARG A | 626 | −45.535 | 34.530 | −15.058 | 1.00 | 77.22 | N |
| ATOM | 4583 | CA | ARG A | 626 | −45.403 | 33.996 | −16.399 | 1.00 | 72.04 | C |
| ATOM | 4584 | CB | ARG A | 626 | −46.370 | 34.685 | −17.396 | 1.00 | 73.60 | C |
| ATOM | 4585 | CG | ARG A | 626 | −45.884 | 35.880 | −18.263 | 1.00 | 74.29 | C |
| ATOM | 4586 | CD | ARG A | 626 | −45.643 | 35.520 | −19.749 | 1.00 | 70.04 | C |
| ATOM | 4587 | NE | ARG A | 626 | −46.680 | 35.840 | −20.766 | 1.00 | 66.20 | N |
| ATOM | 4588 | CZ | ARG A | 626 | −48.028 | 35.823 | −20.642 | 1.00 | 66.81 | C |
| ATOM | 4589 | NH1 | ARG A | 626 | −48.684 | 35.526 | −19.511 | 1.00 | 65.58 | N |
| ATOM | 4590 | NH2 | ARG A | 626 | −48.776 | 36.109 | −21.715 | 1.00 | 64.54 | N |
| ATOM | 4591 | C | ARG A | 626 | −43.931 | 34.089 | −16.785 | 1.00 | 68.01 | C |
| ATOM | 4592 | O | ARG A | 626 | −43.288 | 35.096 | −16.529 | 1.00 | 64.31 | O |
| ATOM | 4593 | N | LYS A | 627 | −43.378 | 32.986 | −17.270 | 1.00 | 65.55 | N |
| ATOM | 4594 | CA | LYS A | 627 | −42.154 | 33.045 | −18.042 | 1.00 | 65.20 | C |
| ATOM | 4595 | CB | LYS A | 627 | −40.944 | 32.609 | −17.193 | 1.00 | 61.46 | C |
| ATOM | 4596 | C | LYS A | 627 | −42.380 | 32.236 | −19.353 | 1.00 | 67.19 | C |
| ATOM | 4597 | O | LYS A | 627 | −43.321 | 31.424 | −19.473 | 1.00 | 62.01 | O |
| ATOM | 4598 | N | LYS A | 628 | −41.555 | 32.539 | −20.352 | 1.00 | 70.75 | N |
| ATOM | 4599 | CA | LYS A | 628 | −41.614 | 31.914 | −21.668 | 1.00 | 74.16 | C |
| ATOM | 4600 | CB | LYS A | 628 | −41.841 | 32.972 | −22.755 | 1.00 | 77.10 | C |
| ATOM | 4601 | CG | LYS A | 628 | −41.678 | 32.487 | −24.195 | 1.00 | 79.09 | C |
| ATOM | 4602 | CD | LYS A | 628 | −42.371 | 33.400 | −25.193 | 1.00 | 81.97 | C |
| ATOM | 4603 | CE | LYS A | 628 | −41.798 | 33.218 | −26.590 | 1.00 | 85.22 | C |
| ATOM | 4604 | NZ | LYS A | 628 | −42.596 | 33.973 | −27.583 | 1.00 | 87.33 | N |
| ATOM | 4605 | C | LYS A | 628 | −40.298 | 31.266 | −21.949 | 1.00 | 73.77 | C |
| ATOM | 4606 | O | LYS A | 628 | −39.283 | 31.703 | −21.454 | 1.00 | 73.86 | O |
| ATOM | 4607 | N | VAL A | 629 | −40.324 | 30.307 | −22.850 | 1.00 | 76.66 | N |
| ATOM | 4608 | CA | VAL A | 629 | −39.127 | 29.694 | −23.342 | 1.00 | 78.17 | C |
| ATOM | 4609 | CB | VAL A | 629 | −38.648 | 28.582 | −22.445 | 1.00 | 82.90 | C |
| ATOM | 4610 | CG1 | VAL A | 629 | −39.726 | 27.536 | −22.325 | 1.00 | 84.33 | C |
| ATOM | 4611 | CG2 | VAL A | 629 | −37.387 | 27.991 | −23.022 | 1.00 | 88.27 | C |
| ATOM | 4612 | C | VAL A | 629 | −39.535 | 29.141 | −24.678 | 1.00 | 75.87 | C |
| ATOM | 4613 | O | VAL A | 629 | −40.698 | 28.849 | −24.872 | 1.00 | 75.54 | O |
| ATOM | 4614 | N | THR A | 630 | −38.599 | 28.985 | −25.596 | 1.00 | 74.24 | N |
| ATOM | 4615 | CA | THR A | 630 | −38.951 | 28.458 | −26.894 | 1.00 | 78.00 | C |
| ATOM | 4616 | CB | THR A | 630 | −38.677 | 29.486 | −28.003 | 1.00 | 80.70 | C |
| ATOM | 4617 | OG1 | THR A | 630 | −37.313 | 29.413 | −28.416 | 1.00 | 81.31 | O |
| ATOM | 4618 | CG2 | THR A | 630 | −38.950 | 30.885 | −27.515 | 1.00 | 81.59 | C |
| ATOM | 4619 | C | THR A | 630 | −38.175 | 27.187 | −27.159 | 1.00 | 79.08 | C |
| ATOM | 4620 | O | THR A | 630 | −36.963 | 27.197 | −27.146 | 1.00 | 74.30 | O |
| ATOM | 4621 | N | LEU A | 631 | −38.873 | 26.092 | −27.406 | 1.00 | 81.37 | N |
| ATOM | 4622 | CA | LEU A | 631 | −38.206 | 24.834 | −27.660 | 1.00 | 81.88 | C |
| ATOM | 4623 | CB | LEU A | 631 | −38.477 | 23.907 | −26.489 | 1.00 | 81.85 | C |
| ATOM | 4624 | CG | LEU A | 631 | −39.039 | 24.498 | −25.206 | 1.00 | 80.43 | C |
| ATOM | 4625 | CD1 | LEU A | 631 | −39.807 | 23.471 | −24.407 | 1.00 | 73.92 | C |
| ATOM | 4626 | CD2 | LEU A | 631 | −37.929 | 25.108 | −24.386 | 1.00 | 79.49 | C |
| ATOM | 4627 | C | LEU A | 631 | −38.764 | 24.117 | −28.849 | 1.00 | 87.41 | C |
| ATOM | 4628 | O | LEU A | 631 | −39.914 | 23.768 | −28.817 | 1.00 | 99.19 | O |
| ATOM | 4629 | N | GLY A | 632 | −37.974 | 23.833 | −29.871 | 1.00 | 92.91 | N |
| ATOM | 4630 | CA | GLY A | 632 | −38.486 | 23.075 | −31.002 | 1.00 | 102.38 | C |
| ATOM | 4631 | C | GLY A | 632 | −39.657 | 23.691 | −31.721 | 1.00 | 105.65 | C |
| ATOM | 4632 | O | GLY A | 632 | −40.764 | 23.680 | −31.213 | 1.00 | 110.59 | O |
| ATOM | 4633 | N | THR A | 633 | −39.437 | 24.201 | −32.920 | 1.00 | 102.36 | N |
| ATOM | 4634 | CA | THR A | 633 | −40.517 | 24.860 | −33.629 | 1.00 | 100.41 | C |
| ATOM | 4635 | CB | THR A | 633 | −40.037 | 25.443 | −34.947 | 1.00 | 100.29 | C |
| ATOM | 4636 | OG1 | THR A | 633 | −39.939 | 24.394 | −35.902 | 1.00 | 95.66 | O |
| ATOM | 4637 | CG2 | THR A | 633 | −38.688 | 26.063 | −34.767 | 1.00 | 100.19 | C |
| ATOM | 4638 | C | THR A | 633 | −41.727 | 23.985 | −33.896 | 1.00 | 91.79 | C |
| ATOM | 4639 | O | THR A | 633 | −42.839 | 24.453 | −33.751 | 1.00 | 82.22 | O |
| ATOM | 4640 | N | GLN A | 634 | −41.565 | 22.729 | −34.273 | 1.00 | 88.95 | N |
| ATOM | 4641 | CA | GLN A | 634 | −42.818 | 21.972 | −34.502 | 1.00 | 86.91 | C |
| ATOM | 4642 | CB | GLN A | 634 | −42.530 | 20.553 | −35.062 | 1.00 | 77.10 | C |
| ATOM | 4643 | C | GLN A | 634 | −43.679 | 22.042 | −33.154 | 1.00 | 85.93 | C |
| ATOM | 4644 | O | GLN A | 634 | −43.178 | 22.440 | −32.096 | 1.00 | 78.31 | O |
| ATOM | 4645 | N | PRO A | 635 | −44.998 | 21.751 | −33.197 | 1.00 | 87.23 | N |
| ATOM | 4646 | CA | PRO A | 635 | −45.805 | 21.825 | −31.952 | 1.00 | 83.93 | C |
| ATOM | 4647 | CB | PRO A | 635 | −47.216 | 21.416 | −32.405 | 1.00 | 87.39 | C |
| ATOM | 4648 | CG | PRO A | 635 | −47.241 | 21.677 | −33.871 | 1.00 | 90.23 | C |
| ATOM | 4649 | CD | PRO A | 635 | −45.833 | 21.469 | −34.377 | 1.00 | 89.86 | C |
| ATOM | 4650 | C | PRO A | 635 | −45.327 | 20.852 | −30.900 | 1.00 | 81.61 | C |

TABLE 6-continued

Atomic coordinates for CRBN:DDB1: Compound B (Human protein)

| ATOM | 4651 | O | PRO A | 635 | −44.676 | 19.867 | −31.252 | 1.00 | 79.88 | O |
|---|---|---|---|---|---|---|---|---|---|---|
| ATOM | 4652 | N | THR A | 636 | −45.701 | 21.089 | −29.641 | 1.00 | 78.27 | N |
| ATOM | 4653 | CA | THR A | 636 | −45.052 | 20.426 | −28.494 | 1.00 | 77.77 | C |
| ATOM | 4654 | CB | THR A | 636 | −44.139 | 21.445 | −27.746 | 1.00 | 81.54 | C |
| ATOM | 4655 | OG1 | THR A | 636 | −43.281 | 22.108 | −28.694 | 1.00 | 89.80 | O |
| ATOM | 4656 | CG2 | THR A | 636 | −43.263 | 20.779 | −26.642 | 1.00 | 80.08 | C |
| ATOM | 4657 | C | THR A | 636 | −46.011 | 19.731 | −27.502 | 1.00 | 73.89 | C |
| ATOM | 4658 | O | THR A | 636 | −46.723 | 20.412 | −26.771 | 1.00 | 72.56 | O |
| ATOM | 4659 | N | VAL A | 637 | −45.981 | 18.383 | −27.456 | 1.00 | 71.24 | N |
| ATOM | 4660 | CA | VAL A | 637 | −46.789 | 17.569 | −26.511 | 1.00 | 68.23 | C |
| ATOM | 4661 | CB | VAL A | 637 | −47.130 | 16.178 | −27.083 | 1.00 | 69.43 | C |
| ATOM | 4662 | CG1 | VAL A | 637 | −48.055 | 15.390 | −26.133 | 1.00 | 69.62 | C |
| ATOM | 4663 | CG2 | VAL A | 637 | −47.749 | 16.324 | −28.465 | 1.00 | 71.51 | C |
| ATOM | 4664 | C | VAL A | 637 | −46.061 | 17.335 | −25.194 | 1.00 | 63.81 | C |
| ATOM | 4665 | O | VAL A | 637 | −44.929 | 16.865 | −25.205 | 1.00 | 60.73 | O |
| ATOM | 4666 | N | LEU A | 638 | −46.740 | 17.610 | −24.075 | 1.00 | 60.89 | N |
| ATOM | 4667 | CA | LEU A | 638 | −46.152 | 17.465 | −22.742 | 1.00 | 59.71 | C |
| ATOM | 4668 | CB | LEU A | 638 | −46.375 | 18.722 | −21.950 | 1.00 | 59.60 | C |
| ATOM | 4669 | CG | LEU A | 638 | −45.764 | 20.016 | −22.491 | 1.00 | 57.33 | C |
| ATOM | 4670 | CD1 | LEU A | 638 | −46.479 | 21.215 | −21.899 | 1.00 | 55.72 | C |
| ATOM | 4671 | CD2 | LEU A | 638 | −44.297 | 20.091 | −22.161 | 1.00 | 56.90 | C |
| ATOM | 4672 | C | LEU A | 638 | −46.715 | 16.285 | −21.976 | 1.00 | 60.73 | C |
| ATOM | 4673 | O | LEU A | 638 | −47.853 | 15.955 | −22.110 | 1.00 | 62.11 | O |
| ATOM | 4674 | N | ARG A | 639 | −45.893 | 15.670 | −21.145 | 1.00 | 67.47 | N |
| ATOM | 4675 | CA | ARG A | 639 | −46.136 | 14.309 | −20.667 | 1.00 | 68.68 | C |
| ATOM | 4676 | CB | ARG A | 639 | −45.790 | 13.334 | −21.776 | 1.00 | 75.83 | C |
| ATOM | 4677 | CG | ARG A | 639 | −47.002 | 12.935 | −22.604 | 1.00 | 87.96 | C |
| ATOM | 4678 | CD | ARG A | 639 | −47.632 | 11.594 | −22.181 | 1.00 | 93.91 | C |
| ATOM | 4679 | NE | ARG A | 639 | −47.467 | 11.186 | −20.770 | 1.00 | 94.83 | N |
| ATOM | 4680 | CZ | ARG A | 639 | −48.019 | 10.090 | −20.225 | 1.00 | 94.26 | C |
| ATOM | 4681 | NH1 | ARG A | 639 | −48.800 | 9.244 | −20.956 | 1.00 | 89.24 | N |
| ATOM | 4682 | NH2 | ARG A | 639 | −47.802 | 9.851 | −18.919 | 1.00 | 89.67 | N |
| ATOM | 4683 | C | ARG A | 639 | −45.325 | 13.987 | −19.424 | 1.00 | 64.92 | C |
| ATOM | 4684 | O | ARG A | 639 | −44.114 | 14.218 | −19.355 | 1.00 | 63.69 | O |
| ATOM | 4685 | N | THR A | 640 | −46.002 | 13.465 | −18.427 | 1.00 | 59.81 | N |
| ATOM | 4686 | CA | THR A | 640 | −45.397 | 13.342 | −17.139 | 1.00 | 58.63 | C |
| ATOM | 4687 | CB | THR A | 640 | −46.495 | 13.549 | −16.073 | 1.00 | 60.33 | C |
| ATOM | 4688 | OG1 | THR A | 640 | −46.767 | 14.962 | −15.963 | 1.00 | 59.03 | O |
| ATOM | 4689 | CG2 | THR A | 640 | −46.131 | 12.913 | −14.680 | 1.00 | 60.38 | C |
| ATOM | 4690 | C | THR A | 640 | −44.734 | 11.973 | −17.076 | 1.00 | 58.28 | C |
| ATOM | 4691 | O | THR A | 640 | −45.285 | 11.024 | −17.614 | 1.00 | 55.87 | O |
| ATOM | 4692 | N | PHE A | 641 | −43.545 | 11.906 | −16.455 | 1.00 | 59.93 | N |
| ATOM | 4693 | CA | PHE A | 641 | −42.906 | 10.651 | −15.963 | 1.00 | 61.58 | C |
| ATOM | 4694 | CB | PHE A | 641 | −41.867 | 10.124 | −16.976 | 1.00 | 61.81 | C |
| ATOM | 4695 | CG | PHE A | 641 | −40.620 | 10.996 | −17.209 | 1.00 | 54.54 | C |
| ATOM | 4696 | CD1 | PHE A | 641 | −40.680 | 12.200 | −17.873 | 1.00 | 56.26 | C |
| ATOM | 4697 | CE1 | PHE A | 641 | −39.533 | 12.934 | −18.147 | 1.00 | 54.94 | C |
| ATOM | 4698 | CZ | PHE A | 641 | −38.306 | 12.441 | −17.807 | 1.00 | 52.27 | C |
| ATOM | 4699 | CE2 | PHE A | 641 | −38.237 | 11.230 | −17.204 | 1.00 | 52.49 | C |
| ATOM | 4700 | CD2 | PHE A | 641 | −39.384 | 10.514 | −16.919 | 1.00 | 51.85 | C |
| ATOM | 4701 | C | PHE A | 641 | −42.241 | 10.745 | −14.575 | 1.00 | 68.80 | C |
| ATOM | 4702 | O | PHE A | 641 | −41.992 | 11.849 | −14.107 | 1.00 | 65.95 | O |
| ATOM | 4703 | N | ARG A | 642 | −41.922 | 9.601 | −13.944 | 1.00 | 77.35 | N |
| ATOM | 4704 | CA | ARG A | 642 | −41.061 | 9.578 | −12.712 | 1.00 | 82.93 | C |
| ATOM | 4705 | CB | ARG A | 642 | −41.518 | 8.488 | −11.730 | 1.00 | 89.57 | C |
| ATOM | 4706 | CG | ARG A | 642 | −43.029 | 8.216 | −11.694 | 1.00 | 100.96 | C |
| ATOM | 4707 | CD | ARG A | 642 | −43.614 | 8.130 | −10.284 | 1.00 | 108.08 | C |
| ATOM | 4708 | NE | ARG A | 642 | −43.380 | 9.384 | −9.549 | 1.00 | 119.92 | N |
| ATOM | 4709 | CZ | ARG A | 642 | −44.079 | 9.817 | −8.500 | 1.00 | 123.09 | C |
| ATOM | 4710 | NH1 | ARG A | 642 | −45.118 | 9.125 | −8.025 | 1.00 | 123.32 | N |
| ATOM | 4711 | NH2 | ARG A | 642 | −43.737 | 10.978 | −7.927 | 1.00 | 124.59 | N |
| ATOM | 4712 | C | ARG A | 642 | −39.571 | 9.330 | −13.061 | 1.00 | 85.76 | C |
| ATOM | 4713 | O | ARG A | 642 | −39.306 | 8.477 | −13.897 | 1.00 | 89.89 | O |
| ATOM | 4714 | N | SER A | 643 | −38.608 | 10.047 | −12.450 | 1.00 | 90.79 | N |
| ATOM | 4715 | CA | SER A | 643 | −37.142 | 9.703 | −12.562 | 1.00 | 96.55 | C |
| ATOM | 4716 | CB | SER A | 643 | −36.386 | 10.564 | −13.609 | 1.00 | 87.90 | C |
| ATOM | 4717 | C | SER A | 643 | −36.410 | 9.776 | −11.205 | 1.00 | 101.55 | C |
| ATOM | 4718 | O | SER A | 643 | −35.829 | 10.822 | −10.885 | 1.00 | 110.05 | O |
| ATOM | 4719 | N | LEU A | 644 | −36.411 | 8.655 | −10.454 | 1.00 | 95.96 | N |
| ATOM | 4720 | CA | LEU A | 644 | −35.899 | 8.571 | −9.055 | 1.00 | 95.11 | C |
| ATOM | 4721 | CB | LEU A | 644 | −34.404 | 8.996 | −8.918 | 1.00 | 80.47 | C |
| ATOM | 4722 | C | LEU A | 644 | −36.815 | 9.321 | −8.040 | 1.00 | 97.62 | C |
| ATOM | 4723 | O | LEU A | 644 | −36.498 | 10.439 | −7.616 | 1.00 | 95.22 | O |
| ATOM | 4724 | N | SER A | 645 | −37.935 | 8.668 | −7.669 | 1.00 | 100.62 | N |
| ATOM | 4725 | CA | SER A | 645 | −38.939 | 9.111 | −6.629 | 1.00 | 103.52 | C |
| ATOM | 4726 | CB | SER A | 645 | −38.487 | 8.756 | −5.187 | 1.00 | 99.83 | C |
| ATOM | 4727 | C | SER A | 645 | −39.381 | 10.577 | −6.706 | 1.00 | 103.29 | C |
| ATOM | 4728 | O | SER A | 645 | −39.641 | 11.214 | −5.690 | 1.00 | 101.72 | O |

TABLE 6-continued

Atomic coordinates for CRBN:DDB1: Compound B (Human protein)

| ATOM | 4729 | N | THR A | 646 | −39.496 | 11.071 | −7.933 | 1.00 | 108.06 | N |
|---|---|---|---|---|---|---|---|---|---|---|
| ATOM | 4730 | CA | THR A | 646 | −39.762 | 12.484 | −8.240 | 1.00 | 108.07 | C |
| ATOM | 4731 | CB | THR A | 646 | −38.483 | 13.366 | −8.052 | 1.00 | 110.10 | C |
| ATOM | 4732 | OG1 | THR A | 646 | −38.791 | 14.743 | −8.313 | 1.00 | 110.13 | O |
| ATOM | 4733 | CG2 | THR A | 646 | −37.306 | 12.936 | −8.967 | 1.00 | 106.37 | C |
| ATOM | 4734 | C | THR A | 646 | −40.257 | 12.549 | −9.696 | 1.00 | 103.93 | C |
| ATOM | 4735 | O | THR A | 646 | −39.874 | 11.692 | −10.498 | 1.00 | 110.41 | O |
| ATOM | 4736 | N | THR A | 647 | −41.094 | 13.536 | −10.037 | 1.00 | 94.13 | N |
| ATOM | 4737 | CA | THR A | 647 | −41.638 | 13.661 | −11.409 | 1.00 | 83.28 | C |
| ATOM | 4738 | CB | THR A | 647 | −43.157 | 14.005 | −11.461 | 1.00 | 83.97 | C |
| ATOM | 4739 | OG1 | THR A | 647 | −43.364 | 15.423 | −11.299 | 1.00 | 81.66 | O |
| ATOM | 4740 | CG2 | THR A | 647 | −43.973 | 13.191 | −10.435 | 1.00 | 82.28 | C |
| ATOM | 4741 | C | THR A | 647 | −40.934 | 14.708 | −12.263 | 1.00 | 73.49 | C |
| ATOM | 4742 | O | THR A | 647 | −40.680 | 15.799 | −11.815 | 1.00 | 69.72 | O |
| ATOM | 4743 | N | ASN A | 648 | −40.663 | 14.353 | −13.508 | 1.00 | 71.47 | N |
| ATOM | 4744 | CA | ASN A | 648 | −40.339 | 15.300 | −14.575 | 1.00 | 71.46 | C |
| ATOM | 4745 | CB | ASN A | 648 | −39.061 | 14.867 | −15.234 | 1.00 | 71.58 | C |
| ATOM | 4746 | CG | ASN A | 648 | −37.958 | 14.804 | −14.255 | 1.00 | 75.71 | C |
| ATOM | 4747 | OD1 | ASN A | 648 | −38.078 | 15.393 | −13.182 | 1.00 | 71.47 | O |
| ATOM | 4748 | ND2 | ASN A | 648 | −36.871 | 14.101 | −14.597 | 1.00 | 82.33 | N |
| ATOM | 4749 | C | ASN A | 648 | −41.423 | 15.397 | −15.626 | 1.00 | 70.40 | C |
| ATOM | 4750 | O | ASN A | 648 | −42.478 | 14.746 | −15.524 | 1.00 | 75.87 | O |
| ATOM | 4751 | N | VAL A | 649 | −41.170 | 16.250 | −16.611 | 1.00 | 63.36 | N |
| ATOM | 4752 | CA | VAL A | 649 | −42.035 | 16.399 | −17.744 | 1.00 | 59.26 | C |
| ATOM | 4753 | CB | VAL A | 649 | −42.617 | 17.798 | −17.791 | 1.00 | 55.44 | C |
| ATOM | 4754 | CG1 | VAL A | 649 | −42.896 | 18.249 | −19.208 | 1.00 | 56.43 | C |
| ATOM | 4755 | CG2 | VAL A | 649 | −43.884 | 17.841 | −16.967 | 1.00 | 56.33 | C |
| ATOM | 4756 | C | VAL A | 649 | −41.175 | 16.148 | −18.932 | 1.00 | 61.23 | C |
| ATOM | 4757 | O | VAL A | 649 | −40.018 | 16.581 | −18.964 | 1.00 | 67.34 | O |
| ATOM | 4758 | N | PHE A | 650 | −41.734 | 15.437 | −19.899 | 1.00 | 58.26 | N |
| ATOM | 4759 | CA | PHE A | 650 | −41.043 | 15.184 | −21.134 | 1.00 | 57.22 | C |
| ATOM | 4760 | CB | PHE A | 650 | −41.090 | 13.696 | −21.490 | 1.00 | 56.08 | C |
| ATOM | 4761 | CG | PHE A | 650 | −40.182 | 13.333 | −22.629 | 1.00 | 56.36 | C |
| ATOM | 4762 | CD1 | PHE A | 650 | −40.571 | 13.551 | −23.934 | 1.00 | 58.58 | C |
| ATOM | 4763 | CE1 | PHE A | 650 | −39.734 | 13.209 | −24.988 | 1.00 | 62.13 | C |
| ATOM | 4764 | CZ | PHE A | 650 | −38.482 | 12.698 | −24.737 | 1.00 | 59.65 | C |
| ATOM | 4765 | CE2 | PHE A | 650 | −38.081 | 12.523 | −23.427 | 1.00 | 57.47 | C |
| ATOM | 4766 | CD2 | PHE A | 650 | −38.924 | 12.830 | −22.393 | 1.00 | 54.69 | C |
| ATOM | 4767 | C | PHE A | 650 | −41.741 | 15.988 | −22.191 | 1.00 | 53.82 | C |
| ATOM | 4768 | O | PHE A | 650 | −42.935 | 15.856 | −22.344 | 1.00 | 55.52 | O |
| ATOM | 4769 | N | ALA A | 651 | −41.010 | 16.789 | −22.941 | 1.00 | 49.79 | N |
| ATOM | 4770 | CA | ALA A | 651 | −41.641 | 17.642 | −23.906 | 1.00 | 49.04 | C |
| ATOM | 4771 | CB | ALA A | 651 | −41.147 | 19.060 | −23.739 | 1.00 | 47.77 | C |
| ATOM | 4772 | C | ALA A | 651 | −41.286 | 17.098 | −25.238 | 1.00 | 49.06 | C |
| ATOM | 4773 | O | ALA A | 651 | −40.189 | 17.301 | −25.694 | 1.00 | 50.26 | O |
| ATOM | 4774 | N | CYS A | 652 | −42.205 | 16.374 | −25.852 | 1.00 | 53.14 | N |
| ATOM | 4775 | CA | CYS A | 652 | −41.965 | 15.770 | −27.185 | 1.00 | 56.51 | C |
| ATOM | 4776 | CB | CYS A | 652 | −42.971 | 14.634 | −27.480 | 1.00 | 56.00 | C |
| ATOM | 4777 | SG | CYS A | 652 | −43.349 | 13.555 | −26.072 | 1.00 | 56.84 | S |
| ATOM | 4778 | C | CYS A | 652 | −42.046 | 16.845 | −28.255 | 1.00 | 58.19 | C |
| ATOM | 4779 | O | CYS A | 652 | −43.034 | 17.514 | −28.338 | 1.00 | 54.03 | O |
| ATOM | 4780 | N | SER A | 653 | −41.001 | 17.015 | −29.063 | 1.00 | 71.35 | N |
| ATOM | 4781 | CA | SER A | 653 | −40.949 | 18.078 | −30.113 | 1.00 | 80.73 | C |
| ATOM | 4782 | CB | SER A | 653 | −40.756 | 19.506 | −29.489 | 1.00 | 88.29 | C |
| ATOM | 4783 | OG | SER A | 653 | −39.406 | 19.869 | −29.158 | 1.00 | 88.07 | O |
| ATOM | 4784 | C | SER A | 653 | −39.868 | 17.793 | −31.168 | 1.00 | 84.73 | C |
| ATOM | 4785 | O | SER A | 653 | −39.338 | 16.692 | −31.231 | 1.00 | 89.49 | O |
| ATOM | 4786 | N | ASP A | 654 | −39.617 | 18.783 | −32.021 | 1.00 | 87.24 | N |
| ATOM | 4787 | CA | ASP A | 654 | −38.409 | 18.917 | −32.844 | 1.00 | 87.91 | C |
| ATOM | 4788 | CB | ASP A | 654 | −38.489 | 20.338 | −33.512 | 1.00 | 98.92 | C |
| ATOM | 4789 | CG | ASP A | 654 | −37.266 | 20.727 | −34.408 | 1.00 | 109.69 | C |
| ATOM | 4790 | OD1 | ASP A | 654 | −36.135 | 20.170 | −34.319 | 1.00 | 119.68 | O |
| ATOM | 4791 | OD2 | ASP A | 654 | −37.453 | 21.675 | −35.205 | 1.00 | 106.65 | O |
| ATOM | 4792 | C | ASP A | 654 | −37.157 | 18.713 | −31.945 | 1.00 | 77.72 | C |
| ATOM | 4793 | O | ASP A | 654 | −36.261 | 17.933 | −32.286 | 1.00 | 77.62 | O |
| ATOM | 4794 | N | ARG A | 655 | −37.129 | 19.389 | −30.796 | 1.00 | 68.58 | N |
| ATOM | 4795 | CA | ARG A | 655 | −36.006 | 19.357 | −29.854 | 1.00 | 68.47 | C |
| ATOM | 4796 | CB | ARG A | 655 | −35.391 | 20.787 | −29.689 | 1.00 | 67.66 | C |
| ATOM | 4797 | C | ARG A | 655 | −36.523 | 18.781 | −28.515 | 1.00 | 65.30 | C |
| ATOM | 4798 | O | ARG A | 655 | −36.958 | 19.536 | −27.634 | 1.00 | 68.63 | O |
| ATOM | 4799 | N | PRO A | 656 | −36.541 | 17.442 | −28.367 | 1.00 | 60.64 | N |
| ATOM | 4800 | CA | PRO A | 656 | −37.106 | 16.892 | −27.121 | 1.00 | 58.54 | C |
| ATOM | 4801 | CB | PRO A | 656 | −37.078 | 15.387 | −27.320 | 1.00 | 57.58 | C |
| ATOM | 4802 | CG | PRO A | 656 | −36.293 | 15.158 | −28.565 | 1.00 | 59.72 | C |
| ATOM | 4803 | CD | PRO A | 656 | −36.376 | 16.403 | −29.383 | 1.00 | 60.73 | C |
| ATOM | 4804 | C | PRO A | 656 | −36.309 | 17.285 | −25.916 | 1.00 | 55.51 | C |
| ATOM | 4805 | O | PRO A | 656 | −35.112 | 17.486 | −26.020 | 1.00 | 55.58 | O |
| ATOM | 4806 | N | THR A | 657 | −37.006 | 17.397 | −24.797 | 1.00 | 53.39 | N |

TABLE 6-continued

Atomic coordinates for CRBN:DDB1: Compound B (Human protein)

| ATOM | 4807 | CA | THR A | 657 | −36.574 | 18.180 | −23.656 | 1.00 | 54.71 | C |
|---|---|---|---|---|---|---|---|---|---|---|
| ATOM | 4808 | CB | THR A | 657 | −37.105 | 19.628 | −23.794 | 1.00 | 56.27 | C |
| ATOM | 4809 | OG1 | THR A | 657 | −36.967 | 20.080 | −25.151 | 1.00 | 58.91 | O |
| ATOM | 4810 | CG2 | THR A | 657 | −36.371 | 20.574 | −22.901 | 1.00 | 56.70 | C |
| ATOM | 4811 | C | THR A | 657 | −37.180 | 17.583 | −22.400 | 1.00 | 56.39 | C |
| ATOM | 4812 | O | THR A | 657 | −38.393 | 17.346 | −22.353 | 1.00 | 61.12 | O |
| ATOM | 4813 | N | VAL A | 658 | −36.359 | 17.324 | −21.384 | 1.00 | 58.71 | N |
| ATOM | 4814 | CA | VAL A | 658 | −36.869 | 16.970 | −20.024 | 1.00 | 59.06 | C |
| ATOM | 4815 | CB | VAL A | 658 | −35.986 | 15.900 | −19.311 | 1.00 | 56.52 | C |
| ATOM | 4816 | CG1 | VAL A | 658 | −36.319 | 15.775 | −17.839 | 1.00 | 58.49 | C |
| ATOM | 4817 | CG2 | VAL A | 658 | −36.188 | 14.542 | −19.945 | 1.00 | 55.30 | C |
| ATOM | 4818 | C | VAL A | 658 | −37.007 | 18.264 | −19.193 | 1.00 | 56.81 | C |
| ATOM | 4819 | O | VAL A | 658 | −36.281 | 19.228 | −19.403 | 1.00 | 52.15 | O |
| ATOM | 4820 | N | ILE A | 659 | −37.956 | 18.284 | −18.276 | 1.00 | 56.07 | N |
| ATOM | 4821 | CA | ILE A | 659 | −38.174 | 19.460 | −17.498 | 1.00 | 64.05 | C |
| ATOM | 4822 | CB | ILE A | 659 | −39.520 | 20.136 | −17.934 | 1.00 | 68.95 | C |
| ATOM | 4823 | CG1 | ILE A | 659 | −39.484 | 20.480 | −19.448 | 1.00 | 67.64 | C |
| ATOM | 4824 | CD1 | ILE A | 659 | −40.651 | 21.324 | −19.952 | 1.00 | 65.99 | C |
| ATOM | 4825 | CG2 | ILE A | 659 | −39.875 | 21.388 | −17.098 | 1.00 | 67.14 | C |
| ATOM | 4826 | C | ILE A | 659 | −38.122 | 19.073 | −16.026 | 1.00 | 68.58 | C |
| ATOM | 4827 | O | ILE A | 659 | −39.117 | 18.560 | −15.522 | 1.00 | 68.06 | O |
| ATOM | 4828 | N | TYR A | 660 | −36.972 | 19.304 | −15.351 | 1.00 | 76.99 | N |
| ATOM | 4829 | CA | TYR A | 660 | −36.880 | 19.173 | −13.851 | 1.00 | 84.41 | C |
| ATOM | 4830 | CB | TYR A | 660 | −35.672 | 18.334 | −13.359 | 1.00 | 84.25 | C |
| ATOM | 4831 | CG | TYR A | 660 | −34.328 | 18.524 | −14.052 | 1.00 | 90.22 | C |
| ATOM | 4832 | CD1 | TYR A | 660 | −33.548 | 19.683 | −13.874 | 1.00 | 86.76 | C |
| ATOM | 4833 | CE1 | TYR A | 660 | −32.305 | 19.821 | −14.513 | 1.00 | 91.20 | C |
| ATOM | 4834 | CZ | TYR A | 660 | −31.806 | 18.764 | −15.326 | 1.00 | 103.59 | C |
| ATOM | 4835 | OH | TYR A | 660 | −30.583 | 18.802 | −16.006 | 1.00 | 104.30 | O |
| ATOM | 4836 | CE2 | TYR A | 660 | −32.560 | 17.602 | −15.479 | 1.00 | 105.58 | C |
| ATOM | 4837 | CD2 | TYR A | 660 | −33.797 | 17.485 | −14.840 | 1.00 | 101.76 | C |
| ATOM | 4838 | C | TYR A | 660 | −36.937 | 20.524 | −13.115 | 1.00 | 84.19 | C |
| ATOM | 4839 | O | TYR A | 660 | −36.896 | 21.566 | −13.759 | 1.00 | 82.53 | O |
| ATOM | 4840 | N | SER A | 661 | −37.087 | 20.480 | −11.781 | 1.00 | 85.46 | N |
| ATOM | 4841 | CA | SER A | 661 | −36.863 | 21.640 | −10.876 | 1.00 | 85.13 | C |
| ATOM | 4842 | CB | SER A | 661 | −38.142 | 22.002 | −10.096 | 1.00 | 88.65 | C |
| ATOM | 4843 | OG | SER A | 661 | −38.024 | 23.283 | −9.444 | 1.00 | 93.92 | O |
| ATOM | 4844 | C | SER A | 661 | −35.679 | 21.464 | −9.882 | 1.00 | 81.87 | C |
| ATOM | 4845 | O | SER A | 661 | −35.807 | 20.854 | −8.816 | 1.00 | 73.31 | O |
| ATOM | 4846 | N | SER A | 662 | −34.531 | 22.011 | −10.262 | 1.00 | 87.15 | N |
| ATOM | 4847 | CA | SER A | 662 | −33.408 | 22.273 | −9.342 | 1.00 | 90.26 | C |
| ATOM | 4848 | CB | SER A | 662 | −32.083 | 22.285 | −10.130 | 1.00 | 89.97 | C |
| ATOM | 4849 | OG | SER A | 662 | −31.014 | 22.696 | −9.316 | 1.00 | 86.37 | O |
| ATOM | 4850 | C | SER A | 662 | −33.625 | 23.607 | −8.553 | 1.00 | 89.03 | C |
| ATOM | 4851 | O | SER A | 662 | −33.557 | 24.711 | −9.125 | 1.00 | 77.65 | O |
| ATOM | 4852 | N | ASN A | 663 | −33.856 | 23.457 | −7.237 | 1.00 | 96.70 | N |
| ATOM | 4853 | CA | ASN A | 663 | −34.270 | 24.530 | −6.251 | 1.00 | 95.76 | C |
| ATOM | 4854 | CB | ASN A | 663 | −33.090 | 25.163 | −5.437 | 1.00 | 93.82 | C |
| ATOM | 4855 | CG | ASN A | 663 | −31.873 | 25.516 | −6.291 | 1.00 | 93.44 | C |
| ATOM | 4856 | OD1 | ASN A | 663 | −31.799 | 26.598 | −6.881 | 1.00 | 87.66 | O |
| ATOM | 4857 | ND2 | ASN A | 663 | −30.891 | 24.609 | −6.331 | 1.00 | 93.65 | N |
| ATOM | 4858 | C | ASN A | 663 | −35.262 | 25.579 | −6.750 | 1.00 | 92.61 | C |
| ATOM | 4859 | O | ASN A | 663 | −34.904 | 26.730 | −6.946 | 1.00 | 84.96 | O |
| ATOM | 4860 | N | HIS A | 664 | −36.501 | 25.149 | −6.988 | 1.00 | 95.91 | N |
| ATOM | 4861 | CA | HIS A | 664 | −37.655 | 26.053 | −7.157 | 1.00 | 99.99 | C |
| ATOM | 4862 | CB | HIS A | 664 | −37.975 | 26.805 | −5.831 | 1.00 | 100.50 | C |
| ATOM | 4863 | CG | HIS A | 664 | −38.021 | 25.935 | −4.595 | 1.00 | 104.51 | C |
| ATOM | 4864 | ND1 | HIS A | 664 | −39.203 | 25.510 | −4.020 | 1.00 | 108.35 | N |
| ATOM | 4865 | CE1 | HIS A | 664 | −38.942 | 24.784 | −2.945 | 1.00 | 104.96 | C |
| ATOM | 4866 | NE2 | HIS A | 664 | −37.631 | 24.728 | −2.796 | 1.00 | 103.91 | N |
| ATOM | 4867 | CD2 | HIS A | 664 | −37.032 | 25.453 | −3.801 | 1.00 | 103.52 | C |
| ATOM | 4868 | C | HIS A | 664 | −37.532 | 27.077 | −8.330 | 1.00 | 100.86 | C |
| ATOM | 4869 | O | HIS A | 664 | −38.371 | 27.972 | −8.439 | 1.00 | 98.22 | O |
| ATOM | 4870 | N | LYS A | 665 | −36.474 | 26.979 | −9.155 | 1.00 | 97.98 | N |
| ATOM | 4871 | CA | LYS A | 665 | −36.417 | 27.558 | −10.503 | 1.00 | 90.24 | C |
| ATOM | 4872 | CB | LYS A | 665 | −35.187 | 28.463 | −10.680 | 1.00 | 74.50 | C |
| ATOM | 4873 | C | LYS A | 665 | −36.372 | 26.299 | −11.417 | 1.00 | 98.09 | C |
| ATOM | 4874 | O | LYS A | 665 | −35.722 | 25.303 | −11.052 | 1.00 | 98.79 | O |
| ATOM | 4875 | N | LEU A | 666 | −37.100 | 26.323 | −12.554 | 1.00 | 99.17 | N |
| ATOM | 4876 | CA | LEU A | 666 | −37.184 | 25.181 | −13.519 | 1.00 | 89.34 | C |
| ATOM | 4877 | CB | LEU A | 666 | −38.480 | 25.226 | −14.335 | 1.00 | 85.75 | C |
| ATOM | 4878 | CG | LEU A | 666 | −39.842 | 25.195 | −13.632 | 1.00 | 88.23 | C |
| ATOM | 4879 | CD1 | LEU A | 666 | −40.891 | 24.687 | −14.609 | 1.00 | 91.44 | C |
| ATOM | 4880 | CD2 | LEU A | 666 | −39.896 | 24.343 | −12.376 | 1.00 | 86.29 | C |
| ATOM | 4881 | C | LEU A | 666 | −36.033 | 25.136 | −14.514 | 1.00 | 85.43 | C |
| ATOM | 4882 | O | LEU A | 666 | −35.415 | 26.140 | −14.807 | 1.00 | 91.41 | O |
| ATOM | 4883 | N | VAL A | 667 | −35.777 | 23.963 | −15.066 | 1.00 | 81.21 | N |
| ATOM | 4884 | CA | VAL A | 667 | −34.634 | 23.755 | −15.941 | 1.00 | 81.83 | C |

TABLE 6-continued

Atomic coordinates for CRBN:DDB1: Compound B (Human protein)

| ATOM | 4885 | CB | VAL A | 667 | −33.522 | 23.057 | −15.163 | 1.00 | 94.54 | C |
|---|---|---|---|---|---|---|---|---|---|---|
| ATOM | 4886 | CG1 | VAL A | 667 | −32.299 | 22.735 | −16.048 | 1.00 | 95.69 | C |
| ATOM | 4887 | CG2 | VAL A | 667 | −33.176 | 23.899 | −13.933 | 1.00 | 97.56 | C |
| ATOM | 4888 | C | VAL A | 667 | −35.045 | 22.870 | −17.088 | 1.00 | 75.61 | C |
| ATOM | 4889 | O | VAL A | 667 | −35.942 | 22.046 | −16.940 | 1.00 | 70.64 | O |
| ATOM | 4890 | N | PHE A | 668 | −34.365 | 23.044 | −18.217 | 1.00 | 69.17 | N |
| ATOM | 4891 | CA | PHE A | 668 | −34.781 | 22.477 | −19.463 | 1.00 | 62.53 | C |
| ATOM | 4892 | CB | PHE A | 668 | −35.171 | 23.604 | −20.411 | 1.00 | 64.94 | C |
| ATOM | 4893 | CG | PHE A | 668 | −36.303 | 24.398 | −19.913 | 1.00 | 67.08 | C |
| ATOM | 4894 | CD1 | PHE A | 668 | −37.571 | 23.834 | −19.861 | 1.00 | 70.00 | C |
| ATOM | 4895 | CE1 | PHE A | 668 | −38.652 | 24.517 | −19.350 | 1.00 | 69.97 | C |
| ATOM | 4896 | CZ | PHE A | 668 | −38.468 | 25.782 | −18.878 | 1.00 | 73.96 | C |
| ATOM | 4897 | CE2 | PHE A | 668 | −37.194 | 26.355 | −18.915 | 1.00 | 78.76 | C |
| ATOM | 4898 | CD2 | PHE A | 668 | −36.113 | 25.653 | −19.427 | 1.00 | 70.73 | C |
| ATOM | 4899 | C | PHE A | 668 | −33.655 | 21.750 | −20.043 | 1.00 | 61.12 | C |
| ATOM | 4900 | O | PHE A | 668 | −33.106 | 22.189 | −21.043 | 1.00 | 61.62 | O |
| ATOM | 4901 | N | SER A | 669 | −33.281 | 20.634 | −19.427 | 1.00 | 66.20 | N |
| ATOM | 4902 | CA | SER A | 669 | −32.249 | 19.760 | −20.050 | 1.00 | 67.28 | C |
| ATOM | 4903 | CB | SER A | 669 | −31.779 | 18.616 | −19.122 | 1.00 | 58.84 | C |
| ATOM | 4904 | C | SER A | 669 | −32.809 | 19.284 | −21.418 | 1.00 | 65.42 | C |
| ATOM | 4905 | O | SER A | 669 | −33.964 | 18.885 | −21.517 | 1.00 | 67.42 | O |
| ATOM | 4906 | N | ASN A | 670 | −32.040 | 19.429 | −22.482 | 1.00 | 63.51 | N |
| ATOM | 4907 | CA | ASN A | 670 | −32.495 | 18.924 | −23.739 | 1.00 | 64.55 | C |
| ATOM | 4908 | CB | ASN A | 670 | −31.834 | 19.686 | −24.867 | 1.00 | 74.76 | C |
| ATOM | 4909 | CG | ASN A | 670 | −30.541 | 19.049 | −25.314 | 1.00 | 80.84 | C |
| ATOM | 4910 | OD1 | ASN A | 670 | −30.568 | 17.986 | −25.949 | 1.00 | 89.08 | O |
| ATOM | 4911 | ND2 | ASN A | 670 | −29.399 | 19.679 | −24.990 | 1.00 | 81.28 | N |
| ATOM | 4912 | C | ASN A | 670 | −32.174 | 17.435 | −23.768 | 1.00 | 60.53 | C |
| ATOM | 4913 | O | ASN A | 670 | −31.278 | 16.977 | −23.060 | 1.00 | 59.53 | O |
| ATOM | 4914 | N | VAL A | 671 | −32.912 | 16.688 | −24.581 | 1.00 | 61.19 | N |
| ATOM | 4915 | CA | VAL A | 671 | −32.800 | 15.210 | −24.661 | 1.00 | 61.84 | C |
| ATOM | 4916 | CB | VAL A | 671 | −34.167 | 14.463 | −24.655 | 1.00 | 62.06 | C |
| ATOM | 4917 | CG1 | VAL A | 671 | −34.030 | 13.010 | −25.106 | 1.00 | 59.62 | C |
| ATOM | 4918 | CG2 | VAL A | 671 | −34.809 | 14.507 | −23.282 | 1.00 | 62.46 | C |
| ATOM | 4919 | C | VAL A | 671 | −32.164 | 14.873 | −25.969 | 1.00 | 59.04 | C |
| ATOM | 4920 | O | VAL A | 671 | −32.575 | 15.337 | −26.995 | 1.00 | 54.66 | O |
| ATOM | 4921 | N | ASN A | 672 | −31.242 | 13.947 | −25.912 | 1.00 | 62.71 | N |
| ATOM | 4922 | CA | ASN A | 672 | −30.302 | 13.705 | −26.977 | 1.00 | 64.62 | C |
| ATOM | 4923 | CB | ASN A | 672 | −29.013 | 13.212 | −26.288 | 1.00 | 69.38 | C |
| ATOM | 4924 | CG | ASN A | 672 | −27.794 | 13.232 | −27.167 | 1.00 | 75.88 | C |
| ATOM | 4925 | OD1 | ASN A | 672 | −27.665 | 14.014 | −28.131 | 1.00 | 83.22 | O |
| ATOM | 4926 | ND2 | ASN A | 672 | −26.851 | 12.361 | −26.818 | 1.00 | 81.08 | N |
| ATOM | 4927 | C | ASN A | 672 | −30.912 | 12.716 | −28.003 | 1.00 | 58.46 | C |
| ATOM | 4928 | O | ASN A | 672 | −30.469 | 11.570 | −28.123 | 1.00 | 55.36 | O |
| ATOM | 4929 | N | LEU A | 673 | −31.926 | 13.190 | −28.735 | 1.00 | 54.06 | N |
| ATOM | 4930 | CA | LEU A | 673 | −32.608 | 12.401 | −29.767 | 1.00 | 57.37 | C |
| ATOM | 4931 | CB | LEU A | 673 | −33.808 | 11.709 | −29.119 | 1.00 | 55.87 | C |
| ATOM | 4932 | CG | LEU A | 673 | −33.551 | 10.393 | −28.410 | 1.00 | 54.28 | C |
| ATOM | 4933 | CD1 | LEU A | 673 | −34.778 | 9.963 | −27.658 | 1.00 | 54.26 | C |
| ATOM | 4934 | CD2 | LEU A | 673 | −33.196 | 9.335 | −29.422 | 1.00 | 56.84 | C |
| ATOM | 4935 | C | LEU A | 673 | −33.101 | 13.260 | −30.968 | 1.00 | 62.71 | C |
| ATOM | 4936 | O | LEU A | 673 | −33.365 | 14.452 | −30.796 | 1.00 | 64.60 | O |
| ATOM | 4937 | N | LYS A | 674 | −33.267 | 12.668 | −32.172 | 1.00 | 65.52 | N |
| ATOM | 4938 | CA | LYS A | 674 | −33.986 | 13.367 | −33.281 | 1.00 | 65.12 | C |
| ATOM | 4939 | CB | LYS A | 674 | −33.728 | 12.718 | −34.665 | 1.00 | 59.13 | C |
| ATOM | 4940 | C | LYS A | 674 | −35.459 | 13.377 | −32.853 | 1.00 | 66.37 | C |
| ATOM | 4941 | O | LYS A | 674 | −35.809 | 12.669 | −31.947 | 1.00 | 74.61 | O |
| ATOM | 4942 | N | GLU A | 675 | −36.329 | 14.152 | −33.467 | 1.00 | 72.86 | N |
| ATOM | 4943 | CA | GLU A | 675 | −37.681 | 14.344 | −32.896 | 1.00 | 78.90 | C |
| ATOM | 4944 | CB | GLU A | 675 | −38.599 | 15.205 | −33.837 | 1.00 | 90.68 | C |
| ATOM | 4945 | CG | GLU A | 675 | −39.396 | 14.577 | −34.992 | 1.00 | 98.84 | C |
| ATOM | 4946 | CD | GLU A | 675 | −40.611 | 15.468 | −35.449 | 1.00 | 111.40 | C |
| ATOM | 4947 | OE1 | GLU A | 675 | −41.580 | 14.880 | −36.021 | 1.00 | 114.75 | O |
| ATOM | 4948 | OE2 | GLU A | 675 | −40.631 | 16.738 | −35.244 | 1.00 | 101.83 | O |
| ATOM | 4949 | C | GLU A | 675 | −38.417 | 13.093 | −32.284 | 1.00 | 72.50 | C |
| ATOM | 4950 | O | GLU A | 675 | −38.468 | 12.014 | −32.881 | 1.00 | 69.22 | O |
| ATOM | 4951 | N | VAL A | 676 | −38.903 | 13.253 | −31.051 | 1.00 | 62.01 | N |
| ATOM | 4952 | CA | VAL A | 676 | −39.897 | 12.376 | −30.464 | 1.00 | 58.72 | C |
| ATOM | 4953 | CB | VAL A | 676 | −39.544 | 12.102 | −29.013 | 1.00 | 58.53 | C |
| ATOM | 4954 | CG1 | VAL A | 676 | −40.628 | 11.296 | −28.296 | 1.00 | 61.40 | C |
| ATOM | 4955 | CG2 | VAL A | 676 | −38.219 | 11.407 | −28.958 | 1.00 | 58.85 | C |
| ATOM | 4956 | C | VAL A | 676 | −41.261 | 13.095 | −30.537 | 1.00 | 60.70 | C |
| ATOM | 4957 | O | VAL A | 676 | −41.334 | 14.304 | −30.241 | 1.00 | 59.76 | O |
| ATOM | 4958 | N | ASN A | 677 | −42.319 | 12.373 | −30.953 | 1.00 | 57.03 | N |
| ATOM | 4959 | CA | ASN A | 677 | −43.637 | 12.969 | −31.179 | 1.00 | 57.24 | C |
| ATOM | 4960 | CB | ASN A | 677 | −44.331 | 12.426 | −32.424 | 1.00 | 57.53 | C |
| ATOM | 4961 | CG | ASN A | 677 | −43.656 | 12.815 | −33.731 | 1.00 | 59.11 | C |
| ATOM | 4962 | OD1 | ASN A | 677 | −43.031 | 13.833 | −33.858 | 1.00 | 59.08 | O |

TABLE 6-continued

Atomic coordinates for CRBN:DDB1: Compound B (Human protein)

| ATOM | 4963 | ND2 | ASN A | 677 | −43.811 | 11.979 | −34.720 | 1.00 | 64.66 | N |
|---|---|---|---|---|---|---|---|---|---|---|
| ATOM | 4964 | C | ASN A | 677 | −44.534 | 12.668 | −30.004 | 1.00 | 61.49 | C |
| ATOM | 4965 | O | ASN A | 677 | −45.293 | 13.555 | −29.565 | 1.00 | 68.02 | O |
| ATOM | 4966 | N | TYR A | 678 | −44.512 | 11.413 | −29.530 | 1.00 | 57.34 | N |
| ATOM | 4967 | CA | TYR A | 678 | −45.252 | 11.029 | −28.307 | 1.00 | 54.62 | C |
| ATOM | 4968 | CB | TYR A | 678 | −46.629 | 10.390 | −28.596 | 1.00 | 53.87 | C |
| ATOM | 4969 | CG | TYR A | 678 | −47.420 | 11.168 | −29.604 | 1.00 | 56.60 | C |
| ATOM | 4970 | CD1 | TYR A | 678 | −47.167 | 10.994 | −30.936 | 1.00 | 61.65 | C |
| ATOM | 4971 | CE1 | TYR A | 678 | −47.837 | 11.701 | −31.905 | 1.00 | 67.35 | C |
| ATOM | 4972 | CZ | TYR A | 678 | −48.782 | 12.622 | −31.560 | 1.00 | 69.96 | C |
| ATOM | 4973 | OH | TYR A | 678 | −49.396 | 13.279 | −32.633 | 1.00 | 73.86 | O |
| ATOM | 4974 | CE2 | TYR A | 678 | −49.053 | 12.841 | −30.203 | 1.00 | 66.22 | C |
| ATOM | 4975 | CD2 | TYR A | 678 | −48.368 | 12.110 | −29.238 | 1.00 | 60.25 | C |
| ATOM | 4976 | C | TYR A | 678 | −44.396 | 10.126 | −27.441 | 1.00 | 53.27 | C |
| ATOM | 4977 | O | TYR A | 678 | −43.398 | 9.520 | −27.887 | 1.00 | 54.49 | O |
| ATOM | 4978 | N | MET A | 679 | −44.752 | 10.089 | −26.171 | 1.00 | 50.07 | N |
| ATOM | 4979 | CA | MET A | 679 | −44.038 | 9.258 | −25.247 | 1.00 | 49.89 | C |
| ATOM | 4980 | CB | MET A | 679 | −42.807 | 9.962 | −24.681 | 1.00 | 50.03 | C |
| ATOM | 4981 | CG | MET A | 679 | −43.064 | 10.948 | −23.570 | 1.00 | 49.55 | C |
| ATOM | 4982 | SD | MET A | 679 | −43.152 | 10.114 | −21.984 | 1.00 | 56.37 | S |
| ATOM | 4983 | CE | MET A | 679 | −41.442 | 9.904 | −21.564 | 1.00 | 59.95 | C |
| ATOM | 4984 | C | MET A | 679 | −44.960 | 8.930 | −24.144 | 1.00 | 50.29 | C |
| ATOM | 4985 | O | MET A | 679 | −45.919 | 9.644 | −23.904 | 1.00 | 51.65 | O |
| ATOM | 4986 | N | CYS A | 680 | −44.640 | 7.860 | −23.450 | 1.00 | 50.40 | N |
| ATOM | 4987 | CA | CYS A | 680 | −45.348 | 7.502 | −22.268 | 1.00 | 51.98 | C |
| ATOM | 4988 | CB | CYS A | 680 | −46.549 | 6.626 | −22.580 | 1.00 | 56.39 | C |
| ATOM | 4989 | SG | CYS A | 680 | −46.200 | 4.866 | −22.756 | 1.00 | 60.74 | S |
| ATOM | 4990 | C | CYS A | 680 | −44.380 | 6.734 | −21.484 | 1.00 | 52.09 | C |
| ATOM | 4991 | O | CYS A | 680 | −43.472 | 6.153 | −22.071 | 1.00 | 52.90 | O |
| ATOM | 4992 | N | PRO A | 681 | −44.560 | 6.705 | −20.156 | 1.00 | 55.78 | N |
| ATOM | 4993 | CA | PRO A | 681 | −43.673 | 5.869 | −19.343 | 1.00 | 55.05 | C |
| ATOM | 4994 | CB | PRO A | 681 | −43.836 | 6.450 | −17.924 | 1.00 | 53.13 | C |
| ATOM | 4995 | CG | PRO A | 681 | −44.852 | 7.545 | −18.031 | 1.00 | 51.17 | C |
| ATOM | 4996 | CD | PRO A | 681 | −45.586 | 7.334 | −19.310 | 1.00 | 52.62 | C |
| ATOM | 4997 | C | PRO A | 681 | −44.175 | 4.442 | −19.431 | 1.00 | 52.15 | C |
| ATOM | 4998 | O | PRO A | 681 | −45.372 | 4.250 | −19.643 | 1.00 | 52.00 | O |
| ATOM | 4999 | N | LEU A | 682 | −43.265 | 3.842 | −19.313 | 1.00 | 50.88 | N |
| ATOM | 5000 | CA | LEU A | 682 | −43.596 | 2.054 | −19.334 | 1.00 | 51.47 | C |
| ATOM | 5001 | CB | LEU A | 682 | −43.175 | 1.392 | −20.642 | 1.00 | 51.81 | C |
| ATOM | 5002 | CG | LEU A | 682 | −43.496 | −0.098 | −20.848 | 1.00 | 48.57 | C |
| ATOM | 5003 | CD1 | LEU A | 682 | −44.952 | −0.161 | −21.148 | 1.00 | 51.74 | C |
| ATOM | 5004 | CD2 | LEU A | 682 | −42.776 | −0.733 | −22.015 | 1.00 | 48.58 | C |
| ATOM | 5005 | C | LEU A | 682 | −42.848 | 1.337 | −18.250 | 1.00 | 54.37 | C |
| ATOM | 5006 | O | LEU A | 682 | −41.601 | 1.429 | −18.168 | 1.00 | 50.79 | O |
| ATOM | 5007 | N | ASN A | 683 | −43.605 | 0.567 | −17.467 | 1.00 | 57.70 | N |
| ATOM | 5008 | CA | ASN A | 683 | −43.029 | −0.298 | −16.458 | 1.00 | 59.45 | C |
| ATOM | 5009 | CB | ASN A | 683 | −43.432 | 0.212 | −15.105 | 1.00 | 59.83 | C |
| ATOM | 5010 | CG | ASN A | 683 | −42.631 | −0.386 | −14.014 | 1.00 | 60.80 | C |
| ATOM | 5011 | OD1 | ASN A | 683 | −41.873 | −1.328 | −14.191 | 1.00 | 71.33 | O |
| ATOM | 5012 | ND2 | ASN A | 683 | −42.757 | 0.187 | −12.881 | 1.00 | 62.78 | N |
| ATOM | 5013 | C | ASN A | 683 | −43.457 | −1.752 | −16.629 | 1.00 | 60.25 | C |
| ATOM | 5014 | O | ASN A | 683 | −44.478 | −2.172 | −16.122 | 1.00 | 61.74 | O |
| ATOM | 5015 | N | SER A | 684 | −42.647 | −2.505 | −17.355 | 1.00 | 62.13 | N |
| ATOM | 5016 | CA | SER A | 684 | −42.859 | −3.921 | −17.560 | 1.00 | 64.37 | C |
| ATOM | 5017 | CB | SER A | 684 | −42.684 | −4.268 | −19.032 | 1.00 | 67.15 | C |
| ATOM | 5018 | OG | SER A | 684 | −43.700 | −3.599 | −19.713 | 1.00 | 75.86 | O |
| ATOM | 5019 | C | SER A | 684 | −41.861 | −4.679 | −16.769 | 1.00 | 62.93 | C |
| ATOM | 5020 | O | SER A | 684 | −40.893 | −4.126 | −16.239 | 1.00 | 61.62 | O |
| ATOM | 5021 | N | ASP A | 685 | −42.095 | −5.973 | −16.732 | 1.00 | 63.53 | N |
| ATOM | 5022 | CA | ASP A | 685 | −41.166 | −6.922 | −16.144 | 1.00 | 67.91 | C |
| ATOM | 5023 | CB | ASP A | 685 | −41.841 | −8.298 | −16.084 | 1.00 | 76.80 | C |
| ATOM | 5024 | CG | ASP A | 685 | −43.303 | −8.198 | −15.663 | 1.00 | 87.48 | C |
| ATOM | 5025 | OD1 | ASP A | 685 | −44.106 | −7.606 | −16.459 | 1.00 | 95.44 | O |
| ATOM | 5026 | OD2 | ASP A | 685 | −43.621 | −8.644 | −14.528 | 1.00 | 97.31 | O |
| ATOM | 5027 | C | ASP A | 685 | −39.889 | −6.931 | −16.993 | 1.00 | 62.90 | C |
| ATOM | 5028 | O | ASP A | 685 | −38.787 | −6.800 | −16.459 | 1.00 | 60.26 | O |
| ATOM | 5029 | N | GLY A | 686 | −40.063 | −7.025 | −18.317 | 1.00 | 60.80 | N |
| ATOM | 5030 | CA | GLY A | 686 | −38.968 | −6.911 | −19.280 | 1.00 | 57.20 | C |
| ATOM | 5031 | C | GLY A | 686 | −38.333 | −5.542 | −19.469 | 1.00 | 54.07 | C |
| ATOM | 5032 | O | GLY A | 686 | −37.155 | −5.445 | −19.735 | 1.00 | 47.77 | O |
| ATOM | 5033 | N | TYR A | 687 | −39.121 | −4.483 | −19.343 | 1.00 | 55.98 | N |
| ATOM | 5034 | CA | TYR A | 687 | −38.629 | −3.121 | −19.466 | 1.00 | 54.89 | C |
| ATOM | 5035 | CB | TYR A | 687 | −39.160 | −2.482 | −20.788 | 1.00 | 54.91 | C |
| ATOM | 5036 | CG | TYR A | 687 | −38.832 | −3.300 | −22.032 | 1.00 | 56.22 | C |
| ATOM | 5037 | CD1 | TYR A | 687 | −37.521 | −3.514 | −22.428 | 1.00 | 55.33 | C |
| ATOM | 5038 | CE1 | TYR A | 687 | −37.219 | −4.298 | −23.552 | 1.00 | 58.54 | C |
| ATOM | 5039 | CZ | TYR A | 687 | −38.230 | −4.909 | −24.313 | 1.00 | 57.46 | C |
| ATOM | 5040 | OH | TYR A | 687 | −37.915 | −5.695 | −25.456 | 1.00 | 57.21 | O |

TABLE 6-continued

Atomic coordinates for CRBN:DDB1: Compound B (Human protein)

| ATOM | 5041 | CE2 | TYR A | 687 | −39.534 | −4.697 | −23.923 | 1.00 | 57.27 | C |
|------|------|-----|-------|-----|---------|--------|---------|------|-------|---|
| ATOM | 5042 | CD2 | TYR A | 687 | −39.830 | −3.892 | −22.799 | 1.00 | 58.66 | C |
| ATOM | 5043 | C | TYR A | 687 | −39.056 | −2.367 | −18.186 | 1.00 | 55.00 | C |
| ATOM | 5044 | O | TYR A | 687 | −39.901 | −1.490 | −18.242 | 1.00 | 60.85 | O |
| ATOM | 5045 | N | PRO A | 688 | −38.477 | −2.696 | −17.007 | 1.00 | 54.46 | N |
| ATOM | 5046 | CA | PRO A | 688 | −38.843 | −1.946 | −15.795 | 1.00 | 54.57 | C |
| ATOM | 5047 | CB | PRO A | 688 | −38.133 | −2.714 | −14.702 | 1.00 | 52.65 | C |
| ATOM | 5048 | CG | PRO A | 688 | −36.885 | −3.163 | −15.354 | 1.00 | 51.41 | C |
| ATOM | 5049 | CD | PRO A | 688 | −37.370 | −3.615 | −16.712 | 1.00 | 54.30 | C |
| ATOM | 5050 | C | PRO A | 688 | −38.331 | −0.511 | −15.777 | 1.00 | 54.17 | C |
| ATOM | 5051 | O | PRO A | 688 | −37.220 | −0.246 | −16.200 | 1.00 | 47.26 | O |
| ATOM | 5052 | N | ASP A | 689 | −39.144 | 0.391 | −15.249 | 1.00 | 58.82 | N |
| ATOM | 5053 | CA | ASP A | 689 | −38.756 | 1.809 | −15.069 | 1.00 | 63.70 | C |
| ATOM | 5054 | CB | ASP A | 689 | −37.660 | 2.018 | −13.989 | 1.00 | 67.61 | C |
| ATOM | 5055 | CG | ASP A | 689 | −38.080 | 1.526 | −12.604 | 1.00 | 70.84 | C |
| ATOM | 5056 | OD1 | ASP A | 689 | −39.281 | 1.723 | −12.191 | 1.00 | 63.64 | O |
| ATOM | 5057 | OD2 | ASP A | 689 | −37.162 | 0.935 | −11.971 | 1.00 | 72.02 | O |
| ATOM | 5058 | C | ASP A | 689 | −38.288 | 2.423 | −16.348 | 1.00 | 57.45 | C |
| ATOM | 5059 | O | ASP A | 689 | −37.297 | 3.063 | −16.366 | 1.00 | 55.54 | O |
| ATOM | 5060 | N | SER A | 690 | −39.044 | 2.247 | −17.408 | 1.00 | 59.02 | N |
| ATOM | 5061 | CA | SER A | 690 | −38.595 | 2.623 | −18.710 | 1.00 | 56.00 | C |
| ATOM | 5062 | CB | SER A | 690 | −38.534 | 1.367 | −19.564 | 1.00 | 59.63 | C |
| ATOM | 5063 | OG | SER A | 690 | −37.848 | 0.344 | −18.876 | 1.00 | 61.66 | O |
| ATOM | 5064 | C | SER A | 690 | −39.527 | 3.637 | −19.302 | 1.00 | 51.01 | C |
| ATOM | 5065 | O | SER A | 690 | −40.495 | 4.016 | −18.666 | 1.00 | 55.51 | O |
| ATOM | 5066 | N | LEU A | 691 | −39.205 | 4.044 | −20.526 | 1.00 | 47.82 | N |
| ATOM | 5067 | CA | LEU A | 691 | −39.969 | 4.945 | −21.369 | 1.00 | 48.62 | C |
| ATOM | 5068 | CB | LEU A | 691 | −39.047 | 6.078 | −21.759 | 1.00 | 48.94 | C |
| ATOM | 5069 | CG | LEU A | 691 | −39.154 | 7.337 | −20.949 | 1.00 | 54.49 | C |
| ATOM | 5070 | CD1 | LEU A | 691 | −39.354 | 7.106 | −19.446 | 1.00 | 57.36 | C |
| ATOM | 5071 | CD2 | LEU A | 691 | −37.909 | 8.179 | −21.258 | 1.00 | 56.04 | C |
| ATOM | 5072 | C | LEU A | 691 | −40.351 | 4.301 | −22.672 | 1.00 | 47.10 | C |
| ATOM | 5073 | O | LEU A | 691 | −39.468 | 3.693 | −23.236 | 1.00 | 49.41 | O |
| ATOM | 5074 | N | ALA A | 692 | −41.577 | 4.487 | −23.197 | 1.00 | 45.43 | N |
| ATOM | 5075 | CA | ALA A | 692 | −41.835 | 4.288 | −24.671 | 1.00 | 48.25 | C |
| ATOM | 5076 | CB | ALA A | 692 | −43.148 | 3.618 | −24.919 | 1.00 | 48.67 | C |
| ATOM | 5077 | C | ALA A | 692 | −41.837 | 5.557 | −25.490 | 1.00 | 50.61 | C |
| ATOM | 5078 | O | ALA A | 692 | −42.633 | 6.436 | −25.238 | 1.00 | 57.53 | O |
| ATOM | 5079 | N | LEU A | 693 | −40.989 | 5.662 | −26.496 | 1.00 | 50.55 | N |
| ATOM | 5080 | CA | LEU A | 693 | −40.994 | 6.852 | −27.328 | 1.00 | 49.81 | C |
| ATOM | 5081 | CB | LEU A | 693 | −39.599 | 7.463 | −27.426 | 1.00 | 49.95 | C |
| ATOM | 5082 | CG | LEU A | 693 | −38.711 | 8.041 | −26.324 | 1.00 | 49.19 | C |
| ATOM | 5083 | CD1 | LEU A | 693 | −39.459 | 8.173 | −25.031 | 1.00 | 52.91 | C |
| ATOM | 5084 | CD2 | LEU A | 693 | −37.486 | 7.195 | −26.131 | 1.00 | 48.81 | C |
| ATOM | 5085 | C | LEU A | 693 | −41.399 | 6.451 | −28.736 | 1.00 | 50.36 | C |
| ATOM | 5086 | O | LEU A | 693 | −40.856 | 5.472 | −29.290 | 1.00 | 48.06 | O |
| ATOM | 5087 | N | ALA A | 694 | −42.293 | 7.235 | −29.340 | 1.00 | 49.72 | N |
| ATOM | 5088 | CA | ALA A | 694 | −42.555 | 7.121 | −30.780 | 1.00 | 48.81 | C |
| ATOM | 5089 | CB | ALA A | 694 | −43.991 | 6.788 | −31.043 | 1.00 | 47.35 | C |
| ATOM | 5090 | C | ALA A | 694 | −42.213 | 8.365 | −31.547 | 1.00 | 50.55 | C |
| ATOM | 5091 | O | ALA A | 694 | −42.244 | 9.463 | −31.017 | 1.00 | 55.06 | O |
| ATOM | 5092 | N | ASN A | 695 | −41.938 | 8.174 | −32.824 | 1.00 | 52.27 | N |
| ATOM | 5093 | CA | ASN A | 695 | −41.879 | 9.254 | −33.762 | 1.00 | 55.01 | C |
| ATOM | 5094 | CB | ASN A | 695 | −40.418 | 9.563 | −33.988 | 1.00 | 57.80 | C |
| ATOM | 5095 | CG | ASN A | 695 | −39.733 | 8.504 | −34.789 | 1.00 | 57.41 | C |
| ATOM | 5096 | OD1 | ASN A | 695 | −40.370 | 7.794 | −35.547 | 1.00 | 65.18 | O |
| ATOM | 5097 | ND2 | ASN A | 695 | −38.447 | 8.374 | −34.618 | 1.00 | 56.29 | N |
| ATOM | 5098 | C | ASN A | 695 | −42.578 | 8.839 | −35.048 | 1.00 | 57.36 | C |
| ATOM | 5099 | O | ASN A | 695 | −43.276 | 7.828 | −35.081 | 1.00 | 64.89 | O |
| ATOM | 5100 | N | ASN A | 696 | −42.330 | 9.551 | −36.134 | 1.00 | 64.53 | N |
| ATOM | 5101 | CA | ASN A | 696 | −43.073 | 9.314 | −37.372 | 1.00 | 71.45 | C |
| ATOM | 5102 | CB | ASN A | 696 | −42.698 | 10.363 | −38.435 | 1.00 | 80.19 | C |
| ATOM | 5103 | CG | ASN A | 696 | −43.283 | 11.736 | −38.100 | 1.00 | 89.55 | C |
| ATOM | 5104 | OD1 | ASN A | 696 | −42.551 | 12.712 | −37.825 | 1.00 | 92.20 | O |
| ATOM | 5105 | ND2 | ASN A | 696 | −44.624 | 11.795 | −38.027 | 1.00 | 89.56 | N |
| ATOM | 5106 | C | ASN A | 696 | −42.966 | 7.883 | −37.883 | 1.00 | 66.64 | C |
| ATOM | 5107 | O | ASN A | 696 | −43.967 | 7.334 | −38.328 | 1.00 | 65.96 | O |
| ATOM | 5108 | N | SER A | 697 | −41.789 | 7.270 | −37.743 | 1.00 | 61.51 | N |
| ATOM | 5109 | CA | SER A | 697 | −41.553 | 5.884 | −38.213 | 1.00 | 61.77 | C |
| ATOM | 5110 | CB | SER A | 697 | −40.394 | 5.899 | −39.206 | 1.00 | 59.25 | C |
| ATOM | 5111 | OG | SER A | 697 | −39.277 | 6.536 | −38.631 | 1.00 | 57.45 | O |
| ATOM | 5112 | C | SER A | 697 | −41.356 | 4.729 | −37.154 | 1.00 | 58.36 | C |
| ATOM | 5113 | O | SER A | 697 | −41.533 | 3.534 | −37.479 | 1.00 | 54.97 | O |
| ATOM | 5114 | N | THR A | 698 | −41.044 | 5.067 | −35.908 | 1.00 | 55.57 | N |
| ATOM | 5115 | CA | THR A | 698 | −40.576 | 4.060 | −34.973 | 1.00 | 57.09 | C |
| ATOM | 5116 | CB | THR A | 698 | −39.077 | 4.123 | −34.957 | 1.00 | 60.73 | C |
| ATOM | 5117 | OG1 | THR A | 698 | −38.649 | 4.685 | −36.200 | 1.00 | 59.81 | O |
| ATOM | 5118 | CG2 | THR A | 698 | −38.493 | 2.738 | −34.768 | 1.00 | 65.77 | C |

TABLE 6-continued

Atomic coordinates for CRBN:DDB1: Compound B (Human protein)

| ATOM | 5119 | C | THR A | 698 | −41.026 | 4.186 | −33.524 | 1.00 | 55.35 | C |
|---|---|---|---|---|---|---|---|---|---|---|
| ATOM | 5120 | O | THR A | 698 | −41.213 | 5.281 | −33.027 | 1.00 | 57.29 | O |
| ATOM | 5121 | N | LEU A | 699 | −41.238 | 3.036 | −32.888 | 1.00 | 52.44 | N |
| ATOM | 5122 | CA | LEU A | 699 | −41.426 | 2.925 | −31.452 | 1.00 | 50.67 | C |
| ATOM | 5123 | CB | LEU A | 699 | −42.527 | 1.921 | −31.135 | 1.00 | 48.36 | C |
| ATOM | 5124 | CG | LEU A | 699 | −42.931 | 1.703 | −29.676 | 1.00 | 45.90 | C |
| ATOM | 5125 | CD1 | LEU A | 699 | −43.374 | 2.993 | −29.015 | 1.00 | 47.19 | C |
| ATOM | 5126 | CD2 | LEU A | 699 | −44.042 | 0.683 | −29.540 | 1.00 | 43.75 | C |
| ATOM | 5127 | C | LEU A | 699 | −40.104 | 2.427 | −30.880 | 1.00 | 52.52 | C |
| ATOM | 5128 | O | LEU A | 699 | −39.472 | 1.503 | −31.411 | 1.00 | 58.36 | O |
| ATOM | 5129 | N | THR A | 700 | −39.693 | 3.044 | −29.793 | 1.00 | 49.75 | N |
| ATOM | 5130 | CA | THR A | 700 | −38.459 | 2.744 | −29.141 | 1.00 | 45.53 | C |
| ATOM | 5131 | CB | THR A | 700 | −37.512 | 3.934 | −29.399 | 1.00 | 45.44 | C |
| ATOM | 5132 | OG1 | THR A | 700 | −36.804 | 3.723 | −30.611 | 1.00 | 49.74 | O |
| ATOM | 5133 | CG2 | THR A | 700 | −36.480 | 4.102 | −28.355 | 1.00 | 46.63 | C |
| ATOM | 5134 | C | THR A | 700 | −38.853 | 2.550 | −27.665 | 1.00 | 46.95 | C |
| ATOM | 5135 | O | THR A | 700 | −39.775 | 3.194 | −27.149 | 1.00 | 45.85 | O |
| ATOM | 5136 | N | ILE A | 701 | −38.167 | 1.643 | −26.989 | 1.00 | 49.65 | N |
| ATOM | 5137 | CA | ILE A | 701 | −38.294 | 1.458 | −25.551 | 1.00 | 50.31 | C |
| ATOM | 5138 | CB | ILE A | 701 | −38.790 | 0.046 | −25.210 | 1.00 | 51.59 | C |
| ATOM | 5139 | CG1 | ILE A | 701 | −40.211 | −0.083 | −25.783 | 1.00 | 52.95 | C |
| ATOM | 5140 | CD1 | ILE A | 701 | −40.959 | −1.331 | −25.403 | 1.00 | 55.63 | C |
| ATOM | 5141 | CG2 | ILE A | 701 | −38.718 | −0.200 | −23.693 | 1.00 | 51.77 | C |
| ATOM | 5142 | C | ILE A | 701 | −36.951 | 1.657 | −24.959 | 1.00 | 51.19 | C |
| ATOM | 5143 | O | ILE A | 701 | −36.007 | 1.102 | −25.496 | 1.00 | 49.11 | O |
| ATOM | 5144 | N | GLY A | 702 | −36.868 | 2.400 | −23.844 | 1.00 | 57.29 | N |
| ATOM | 5145 | CA | GLY A | 702 | −35.560 | 2.718 | −23.197 | 1.00 | 59.03 | C |
| ATOM | 5146 | C | GLY A | 702 | −35.561 | 3.313 | −21.783 | 1.00 | 58.57 | C |
| ATOM | 5147 | O | GLY A | 702 | −36.481 | 4.006 | −21.436 | 1.00 | 68.88 | O |
| ATOM | 5148 | N | THR A | 703 | −34.529 | 2.981 | −20.983 | 1.00 | 59.10 | N |
| ATOM | 5149 | CA | THR A | 703 | −34.058 | 3.650 | −19.754 | 1.00 | 50.25 | C |
| ATOM | 5150 | CB | THR A | 703 | −32.944 | 2.820 | −19.065 | 1.00 | 41.16 | C |
| ATOM | 5151 | C | THR A | 703 | −33.504 | 5.037 | −20.210 | 1.00 | 53.17 | C |
| ATOM | 5152 | O | THR A | 703 | −33.300 | 5.299 | −21.396 | 1.00 | 52.93 | O |
| ATOM | 5153 | N | ILE A | 704 | −33.240 | 5.908 | −19.254 | 1.00 | 58.63 | N |
| ATOM | 5154 | CA | ILE A | 704 | −32.943 | 7.330 | −19.483 | 1.00 | 57.59 | C |
| ATOM | 5155 | CB | ILE A | 704 | −34.224 | 8.131 | −19.374 | 1.00 | 59.07 | C |
| ATOM | 5156 | CG1 | ILE A | 704 | −33.945 | 9.624 | −19.141 | 1.00 | 56.84 | C |
| ATOM | 5157 | CD1 | ILE A | 704 | −34.896 | 10.505 | −19.937 | 1.00 | 57.75 | C |
| ATOM | 5158 | CG2 | ILE A | 704 | −35.152 | 7.537 | −18.284 | 1.00 | 63.43 | C |
| ATOM | 5159 | C | ILE A | 704 | −32.056 | 7.819 | −18.374 | 1.00 | 59.98 | C |
| ATOM | 5160 | O | ILE A | 704 | −32.294 | 7.472 | −17.241 | 1.00 | 62.49 | O |
| ATOM | 5161 | N | ASP A | 705 | −31.058 | 8.635 | −18.674 | 1.00 | 63.19 | N |
| ATOM | 5162 | CA | ASP A | 705 | −30.088 | 9.074 | −17.652 | 1.00 | 65.77 | C |
| ATOM | 5163 | CB | ASP A | 705 | −28.770 | 9.377 | −18.320 | 1.00 | 64.61 | C |
| ATOM | 5164 | CG | ASP A | 705 | −28.256 | 8.159 | −19.026 | 1.00 | 68.32 | C |
| ATOM | 5165 | OD1 | ASP A | 705 | −29.110 | 7.235 | −19.227 | 1.00 | 66.67 | O |
| ATOM | 5166 | OD2 | ASP A | 705 | −27.049 | 8.082 | −19.353 | 1.00 | 67.75 | O |
| ATOM | 5167 | C | ASP A | 705 | −30.681 | 10.205 | −16.850 | 1.00 | 69.98 | C |
| ATOM | 5168 | O | ASP A | 705 | −31.639 | 10.831 | −17.339 | 1.00 | 64.42 | O |
| ATOM | 5169 | N | GLU A | 706 | −30.203 | 10.398 | −15.602 | 1.00 | 75.04 | N |
| ATOM | 5170 | CA | GLU A | 706 | −30.958 | 11.219 | −14.598 | 1.00 | 77.04 | C |
| ATOM | 5171 | CB | GLU A | 706 | −30.781 | 10.651 | −13.165 | 1.00 | 66.52 | C |
| ATOM | 5172 | C | GLU A | 706 | −30.658 | 12.758 | −14.706 | 1.00 | 74.29 | C |
| ATOM | 5173 | O | GLU A | 706 | −31.535 | 13.592 | −15.050 | 1.00 | 73.20 | O |
| ATOM | 5174 | N | ILE A | 707 | −28.116 | 13.596 | −14.378 | 1.00 | 79.57 | N |
| ATOM | 5175 | CA | ILE A | 707 | −27.132 | 14.378 | −15.082 | 1.00 | 79.03 | C |
| ATOM | 5176 | CB | ILE A | 707 | −25.667 | 13.910 | −14.796 | 1.00 | 68.63 | C |
| ATOM | 5177 | C | ILE A | 707 | −27.488 | 14.284 | −16.586 | 1.00 | 84.54 | C |
| ATOM | 5178 | O | ILE A | 707 | −28.311 | 13.406 | −17.028 | 1.00 | 73.38 | O |
| ATOM | 5179 | N | GLN A | 708 | −26.828 | 15.190 | −17.292 | 1.00 | 81.36 | N |
| ATOM | 5180 | CA | GLN A | 708 | −26.804 | 15.412 | −18.702 | 1.00 | 76.39 | C |
| ATOM | 5181 | CB | GLN A | 708 | −26.823 | 16.892 | −18.988 | 1.00 | 72.03 | C |
| ATOM | 5182 | CG | GLN A | 708 | −28.063 | 17.469 | −19.614 | 1.00 | 76.89 | C |
| ATOM | 5183 | CD | GLN A | 708 | −27.768 | 18.786 | −20.292 | 1.00 | 76.83 | C |
| ATOM | 5184 | OE1 | GLN A | 708 | −26.670 | 19.306 | −20.186 | 1.00 | 82.87 | O |
| ATOM | 5185 | NE2 | GLN A | 708 | −28.741 | 19.322 | −20.998 | 1.00 | 71.97 | N |
| ATOM | 5186 | C | GLN A | 708 | −25.365 | 15.075 | −18.721 | 1.00 | 80.30 | C |
| ATOM | 5187 | O | GLN A | 708 | −24.730 | 15.168 | −17.691 | 1.00 | 88.09 | O |
| ATOM | 5188 | N | LYS A | 709 | −24.824 | 14.682 | −19.849 | 1.00 | 66.65 | N |
| ATOM | 5189 | CA | LYS A | 709 | −23.427 | 14.340 | −19.900 | 1.00 | 58.32 | C |
| ATOM | 5190 | CB | LYS A | 709 | −23.234 | 12.865 | −19.594 | 1.00 | 49.68 | C |
| ATOM | 5191 | C | LYS A | 709 | −23.029 | 14.635 | −21.289 | 1.00 | 55.83 | C |
| ATOM | 5192 | O | LYS A | 709 | −23.863 | 14.982 | −22.085 | 1.00 | 47.94 | O |
| ATOM | 5193 | N | LEU A | 710 | −21.754 | 14.521 | −21.586 | 1.00 | 51.92 | N |
| ATOM | 5194 | CA | LEU A | 710 | −21.304 | 14.737 | −22.926 | 1.00 | 48.90 | C |
| ATOM | 5195 | CB | LEU A | 710 | −19.933 | 15.356 | −22.931 | 1.00 | 46.48 | C |
| ATOM | 5196 | CG | LEU A | 710 | −19.913 | 16.822 | −22.585 | 1.00 | 46.79 | C |

TABLE 6-continued

Atomic coordinates for CRBN:DDB1: Compound B (Human protein)

| ATOM | 5197 | CD1 | LEU A | 710 | −18.575 | 17.371 | −22.975 | 1.00 | 45.74 | C |
|---|---|---|---|---|---|---|---|---|---|---|
| ATOM | 5198 | CD2 | LEU A | 710 | −20.984 | 17.541 | −23.352 | 1.00 | 48.87 | C |
| ATOM | 5199 | C | LEU A | 710 | −21.242 | 13.364 | −23.514 | 1.00 | 47.86 | C |
| ATOM | 5200 | O | LEU A | 710 | −20.682 | 12.482 | −22.924 | 1.00 | 42.97 | O |
| ATOM | 5201 | N | HIS A | 711 | −21.838 | 13.195 | −24.680 | 1.00 | 49.56 | N |
| ATOM | 5202 | CA | HIS A | 711 | −21.881 | 11.928 | −25.362 | 1.00 | 49.22 | C |
| ATOM | 5203 | CB | HIS A | 711 | −23.289 | 11.640 | −25.780 | 1.00 | 51.17 | C |
| ATOM | 5204 | CG | HIS A | 711 | −24.200 | 11.439 | −24.623 | 1.00 | 57.46 | C |
| ATOM | 5205 | ND1 | HIS A | 711 | −24.854 | 12.475 | −24.010 | 1.00 | 59.83 | N |
| ATOM | 5206 | CE1 | HIS A | 711 | −25.569 | 12.010 | −23.008 | 1.00 | 62.96 | C |
| ATOM | 5207 | NE2 | HIS A | 711 | −25.384 | 10.710 | −22.939 | 1.00 | 64.67 | N |
| ATOM | 5208 | CD2 | HIS A | 711 | −24.530 | 10.329 | −23.936 | 1.00 | 60.08 | C |
| ATOM | 5209 | C | HIS A | 711 | −20.970 | 12.005 | −26.526 | 1.00 | 50.66 | C |
| ATOM | 5210 | O | HIS A | 711 | −20.934 | 12.991 | −27.196 | 1.00 | 54.62 | O |
| ATOM | 5211 | N | ILE A | 712 | −20.215 | 10.948 | −26.738 | 1.00 | 52.56 | N |
| ATOM | 5212 | CA | ILE A | 712 | −19.161 | 10.873 | −27.775 | 1.00 | 49.95 | C |
| ATOM | 5213 | CB | ILE A | 712 | −17.811 | 10.648 | −27.062 | 1.00 | 48.95 | C |
| ATOM | 5214 | CG1 | ILE A | 712 | −17.663 | 11.685 | −25.959 | 1.00 | 47.88 | C |
| ATOM | 5215 | CD1 | ILE A | 712 | −16.307 | 11.711 | −25.323 | 1.00 | 48.98 | C |
| ATOM | 5216 | CG2 | ILE A | 712 | −16.662 | 10.728 | −28.041 | 1.00 | 49.60 | C |
| ATOM | 5217 | C | ILE A | 712 | −19.332 | 9.774 | −28.820 | 1.00 | 46.59 | C |
| ATOM | 5218 | O | ILE A | 712 | −19.141 | 8.647 | −28.508 | 1.00 | 45.24 | O |
| ATOM | 5219 | N | ARG A | 713 | −19.620 | 10.141 | −30.065 | 1.00 | 51.26 | N |
| ATOM | 5220 | CA | ARG A | 713 | −19.638 | 9.228 | −31.251 | 1.00 | 54.48 | C |
| ATOM | 5221 | CB | ARG A | 713 | −20.597 | 9.788 | −32.343 | 1.00 | 59.83 | C |
| ATOM | 5222 | CG | ARG A | 713 | −21.460 | 8.818 | −33.197 | 1.00 | 69.65 | C |
| ATOM | 5223 | CD | ARG A | 713 | −20.670 | 8.210 | −34.411 | 1.00 | 77.11 | C |
| ATOM | 5224 | NE | ARG A | 713 | −21.408 | 7.579 | −35.541 | 1.00 | 69.92 | N |
| ATOM | 5225 | CZ | ARG A | 713 | −22.075 | 8.249 | −36.479 | 1.00 | 68.09 | C |
| ATOM | 5226 | NH1 | ARG A | 713 | −22.199 | 9.570 | −36.433 | 1.00 | 69.35 | N |
| ATOM | 5227 | NH2 | ARG A | 713 | −22.656 | 7.598 | −37.462 | 1.00 | 70.97 | N |
| ATOM | 5228 | C | ARG A | 713 | −18.207 | 9.148 | −31.795 | 1.00 | 51.87 | C |
| ATOM | 5229 | O | ARG A | 713 | −17.547 | 10.154 | −31.939 | 1.00 | 51.43 | O |
| ATOM | 5230 | N | THR A | 714 | −17.712 | 7.949 | −32.074 | 1.00 | 52.62 | N |
| ATOM | 5231 | CA | THR A | 714 | −16.366 | 7.773 | −32.650 | 1.00 | 49.92 | C |
| ATOM | 5232 | CB | THR A | 714 | −15.515 | 6.846 | −31.759 | 1.00 | 49.94 | C |
| ATOM | 5233 | OG1 | THR A | 714 | −15.348 | 7.436 | −30.472 | 1.00 | 51.86 | O |
| ATOM | 5234 | CG2 | THR A | 714 | −14.166 | 6.676 | −32.268 | 1.00 | 52.10 | C |
| ATOM | 5235 | C | THR A | 714 | −16.421 | 7.312 | −34.129 | 1.00 | 47.68 | C |
| ATOM | 5236 | O | THR A | 714 | −17.322 | 6.636 | −34.549 | 1.00 | 49.18 | O |
| ATOM | 5237 | N | VAL A | 715 | −15.449 | 7.771 | −34.905 | 1.00 | 47.87 | N |
| ATOM | 5238 | CA | VAL A | 715 | −15.317 | 7.551 | −36.339 | 1.00 | 44.73 | C |
| ATOM | 5239 | CB | VAL A | 715 | −15.720 | 8.770 | −37.119 | 1.00 | 40.73 | C |
| ATOM | 5240 | CG1 | VAL A | 715 | −15.381 | 8.595 | −38.596 | 1.00 | 38.02 | C |
| ATOM | 5241 | CG2 | VAL A | 715 | −17.187 | 9.027 | −36.863 | 1.00 | 41.29 | C |
| ATOM | 5242 | C | VAL A | 715 | −13.859 | 7.304 | −36.629 | 1.00 | 48.86 | C |
| ATOM | 5243 | O | VAL A | 715 | −13.044 | 8.254 | −36.685 | 1.00 | 46.74 | O |
| ATOM | 5244 | N | PRO A | 716 | −13.507 | 6.017 | −36.745 | 1.00 | 49.60 | N |
| ATOM | 5245 | CA | PRO A | 716 | −12.104 | 5.715 | −36.943 | 1.00 | 48.49 | C |
| ATOM | 5246 | CB | PRO A | 716 | −12.033 | 4.263 | −36.618 | 1.00 | 47.33 | C |
| ATOM | 5247 | CG | PRO A | 716 | −12.989 | 4.188 | −35.491 | 1.00 | 48.87 | C |
| ATOM | 5248 | CD | PRO A | 716 | −14.167 | 4.943 | −36.013 | 1.00 | 46.96 | C |
| ATOM | 5249 | C | PRO A | 716 | −11.725 | 5.949 | −38.344 | 1.00 | 47.49 | C |
| ATOM | 5250 | O | PRO A | 716 | −12.528 | 5.700 | −39.214 | 1.00 | 50.17 | O |
| ATOM | 5251 | N | LEU A | 717 | −10.520 | 6.487 | −38.497 | 1.00 | 48.39 | N |
| ATOM | 5252 | CA | LEU A | 717 | −9.820 | 6.753 | −39.751 | 1.00 | 46.53 | C |
| ATOM | 5253 | CB | LEU A | 717 | −9.378 | 8.213 | −39.747 | 1.00 | 45.87 | C |
| ATOM | 5254 | CG | LEU A | 717 | −10.480 | 9.247 | −39.492 | 1.00 | 47.59 | C |
| ATOM | 5255 | CD1 | LEU A | 717 | −9.900 | 10.653 | −39.484 | 1.00 | 48.76 | C |
| ATOM | 5256 | CD2 | LEU A | 717 | −11.605 | 9.178 | −40.513 | 1.00 | 47.26 | C |
| ATOM | 5257 | C | LEU A | 717 | −8.557 | 5.881 | −39.947 | 1.00 | 46.07 | C |
| ATOM | 5258 | O | LEU A | 717 | −8.123 | 5.672 | −41.053 | 1.00 | 48.53 | O |
| ATOM | 5259 | N | TYR A | 718 | −7.917 | 5.413 | −38.888 | 1.00 | 46.57 | N |
| ATOM | 5260 | CA | TYR A | 718 | −6.731 | 4.577 | −39.042 | 1.00 | 45.34 | C |
| ATOM | 5261 | CB | TYR A | 718 | −7.084 | 3.256 | −39.728 | 1.00 | 42.62 | C |
| ATOM | 5262 | CG | TYR A | 718 | −8.303 | 2.553 | −39.117 | 1.00 | 42.23 | C |
| ATOM | 5263 | CD1 | TYR A | 718 | −8.165 | 1.666 | −37.983 | 1.00 | 42.75 | C |
| ATOM | 5264 | CE1 | TYR A | 718 | −9.277 | 1.042 | −37.400 | 1.00 | 40.03 | C |
| ATOM | 5265 | CZ | TYR A | 718 | −10.515 | 1.266 | −37.958 | 1.00 | 40.60 | C |
| ATOM | 5266 | OH | TYR A | 718 | −11.603 | 0.701 | −37.403 | 1.00 | 46.97 | O |
| ATOM | 5267 | CE2 | TYR A | 718 | −10.697 | 2.089 | −39.081 | 1.00 | 40.54 | C |
| ATOM | 5268 | CD2 | TYR A | 718 | −9.601 | 2.747 | −39.645 | 1.00 | 39.67 | C |
| ATOM | 5269 | C | TYR A | 718 | −5.534 | 5.325 | −39.700 | 1.00 | 48.31 | C |
| ATOM | 5270 | O | TYR A | 718 | −4.471 | 4.710 | −39.975 | 1.00 | 49.91 | O |
| ATOM | 5271 | N | GLU A | 719 | −5.693 | 6.647 | −39.876 | 1.00 | 47.81 | N |
| ATOM | 5272 | CA | GLU A | 719 | −4.590 | 7.569 | −40.188 | 1.00 | 49.67 | C |
| ATOM | 5273 | CB | GLU A | 719 | −4.548 | 7.920 | −41.694 | 1.00 | 51.48 | C |
| ATOM | 5274 | CG | GLU A | 719 | −5.781 | 8.671 | −42.177 | 1.00 | 56.32 | C |

TABLE 6-continued

Atomic coordinates for CRBN:DDB1: Compound B (Human protein)

| ATOM | 5275 | CD  | GLU A | 719 | −6.001  | 8.709  | −43.681 | 1.00 | 61.67 | C |
|------|------|-----|-------|-----|---------|--------|---------|------|-------|---|
| ATOM | 5276 | OE1 | GLU A | 719 | −6.698  | 9.643  | −44.128 | 1.00 | 65.51 | O |
| ATOM | 5277 | OE2 | GLU A | 719 | −5.542  | 7.816  | −44.424 | 1.00 | 68.52 | O |
| ATOM | 5278 | C   | GLU A | 719 | −4.772  | 8.828  | −39.315 | 1.00 | 46.96 | C |
| ATOM | 5279 | O   | GLU A | 719 | −5.846  | 9.022  | −38.766 | 1.00 | 45.78 | O |
| ATOM | 5280 | N   | SER A | 720 | −3.744  | 9.665  | −39.213 | 1.00 | 44.21 | N |
| ATOM | 5281 | CA  | SER A | 720 | −3.845  | 10.949 | −38.517 | 1.00 | 47.26 | C |
| ATOM | 5282 | CB  | SER A | 720 | −2.452  | 11.561 | −38.418 | 1.00 | 50.66 | C |
| ATOM | 5283 | OG  | SER A | 720 | −1.533  | 10.642 | −37.898 | 1.00 | 55.93 | O |
| ATOM | 5284 | C   | SER A | 720 | −4.715  | 12.052 | −39.161 | 1.00 | 48.78 | C |
| ATOM | 5285 | O   | SER A | 720 | −4.367  | 12.543 | −40.243 | 1.00 | 54.30 | O |
| ATOM | 5286 | N   | PRO A | 721 | −5.804  | 12.502 | −38.490 | 1.00 | 47.20 | N |
| ATOM | 5287 | CA  | PRO A | 721 | −6.459  | 13.729 | −38.950 | 1.00 | 44.98 | C |
| ATOM | 5288 | CB  | PRO A | 721 | −7.847  | 13.636 | −38.356 | 1.00 | 43.56 | C |
| ATOM | 5289 | CG  | PRO A | 721 | −7.734  | 12.698 | −37.224 | 1.00 | 44.75 | C |
| ATOM | 5290 | CD  | PRO A | 721 | −6.389  | 12.043 | −37.226 | 1.00 | 45.48 | C |
| ATOM | 5291 | C   | PRO A | 721 | −5.735  | 14.888 | −38.359 | 1.00 | 46.62 | C |
| ATOM | 5292 | O   | PRO A | 721 | −5.080  | 14.737 | −37.315 | 1.00 | 54.55 | O |
| ATOM | 5293 | N   | ARG A | 722 | −5.850  | 16.034 | −39.004 | 1.00 | 48.10 | N |
| ATOM | 5294 | CA  | ARG A | 722 | −4.980  | 17.206 | −38.727 | 1.00 | 47.94 | C |
| ATOM | 5295 | CB  | ARG A | 722 | −3.762  | 17.156 | −39.651 | 1.00 | 47.06 | C |
| ATOM | 5296 | CG  | ARG A | 722 | −2.854  | 15.939 | −39.441 | 1.00 | 51.18 | C |
| ATOM | 5297 | CD  | ARG A | 722 | −1.476  | 16.277 | −38.874 | 1.00 | 59.11 | C |
| ATOM | 5298 | NE  | ARG A | 722 | −1.608  | 16.734 | −37.473 | 1.00 | 68.52 | N |
| ATOM | 5299 | CZ  | ARG A | 722 | −0.849  | 17.653 | −36.854 | 1.00 | 71.01 | C |
| ATOM | 5300 | NH1 | ARG A | 722 | −1.121  | 17.982 | −35.601 | 1.00 | 71.35 | N |
| ATOM | 5301 | NH2 | ARG A | 722 | 0.170   | 18.256 | −37.460 | 1.00 | 72.75 | N |
| ATOM | 5302 | C   | ARG A | 722 | −5.684  | 18.618 | −38.746 | 1.00 | 45.71 | C |
| ATOM | 5303 | O   | ARG A | 722 | −5.390  | 19.484 | −37.872 | 1.00 | 48.12 | O |
| ATOM | 5304 | N   | LYS A | 723 | −6.576  | 18.845 | −39.706 | 1.00 | 41.14 | N |
| ATOM | 5305 | CA  | LYS A | 723 | −7.538  | 19.925 | −39.639 | 1.00 | 41.62 | C |
| ATOM | 5306 | CB  | LYS A | 723 | −7.127  | 21.054 | −40.569 | 1.00 | 42.53 | C |
| ATOM | 5307 | CG  | LYS A | 723 | −5.730  | 21.611 | −40.401 | 1.00 | 42.82 | C |
| ATOM | 5308 | CD  | LYS A | 723 | −5.481  | 22.542 | −39.223 | 1.00 | 41.05 | C |
| ATOM | 5309 | CE  | LYS A | 723 | −3.965  | 22.485 | −39.068 | 1.00 | 43.31 | C |
| ATOM | 5310 | NZ  | LYS A | 723 | −3.470  | 23.084 | −37.808 | 1.00 | 46.56 | N |
| ATOM | 5311 | C   | LYS A | 723 | −8.903  | 19.488 | −40.111 | 1.00 | 41.85 | C |
| ATOM | 5312 | O   | LYS A | 723 | −9.017  | 18.525 | −40.788 | 1.00 | 48.71 | O |
| ATOM | 5313 | N   | ILE A | 724 | −9.924  | 20.264 | −39.851 | 1.00 | 41.18 | N |
| ATOM | 5314 | CA  | ILE A | 724 | −11.283 | 19.893 | −40.175 | 1.00 | 43.37 | C |
| ATOM | 5315 | CB  | ILE A | 724 | −11.895 | 19.000 | −39.066 | 1.00 | 45.86 | C |
| ATOM | 5316 | CG1 | ILE A | 724 | −13.421 | 18.931 | −39.181 | 1.00 | 49.09 | C |
| ATOM | 5317 | CD1 | ILE A | 724 | −14.015 | 17.713 | −38.506 | 1.00 | 50.66 | C |
| ATOM | 5318 | CG2 | ILE A | 724 | −11.622 | 19.549 | −37.676 | 1.00 | 44.74 | C |
| ATOM | 5319 | C   | ILE A | 724 | −12.082 | 21.183 | −40.308 | 1.00 | 45.30 | C |
| ATOM | 5320 | O   | ILE A | 724 | −11.788 | 22.138 | −39.651 | 1.00 | 47.75 | O |
| ATOM | 5321 | N   | CYS A | 725 | −13.057 | 21.242 | −41.187 | 1.00 | 48.38 | N |
| ATOM | 5322 | CA  | CYS A | 725 | −13.978 | 22.376 | −41.206 | 1.00 | 54.98 | C |
| ATOM | 5323 | CB  | CYS A | 725 | −13.389 | 23.558 | −41.969 | 1.00 | 59.42 | C |
| ATOM | 5324 | SG  | CYS A | 725 | −13.327 | 23.199 | −43.727 | 1.00 | 68.77 | S |
| ATOM | 5325 | C   | CYS A | 725 | −15.265 | 21.900 | −41.859 | 1.00 | 54.58 | C |
| ATOM | 5326 | O   | CYS A | 725 | −15.280 | 20.799 | −42.430 | 1.00 | 57.12 | O |
| ATOM | 5327 | N   | TYR A | 726 | −16.328 | 22.697 | −41.807 | 1.00 | 49.54 | N |
| ATOM | 5328 | CA  | TYR A | 726 | −17.600 | 22.193 | −42.239 | 1.00 | 48.24 | C |
| ATOM | 5329 | CB  | TYR A | 726 | −18.443 | 22.079 | −41.057 | 1.00 | 45.78 | C |
| ATOM | 5330 | CG  | TYR A | 726 | −19.873 | 21.853 | −41.266 | 1.00 | 47.59 | C |
| ATOM | 5331 | CD1 | TYR A | 726 | −20.357 | 20.610 | −41.545 | 1.00 | 49.52 | C |
| ATOM | 5332 | CE1 | TYR A | 726 | −21.727 | 20.399 | −41.664 | 1.00 | 51.45 | C |
| ATOM | 5333 | CZ  | TYR A | 726 | −22.619 | 21.444 | −41.464 | 1.00 | 49.83 | C |
| ATOM | 5334 | OH  | TYR A | 726 | −23.985 | 21.278 | −41.547 | 1.00 | 48.71 | O |
| ATOM | 5335 | CE2 | TYR A | 726 | −22.136 | 22.679 | −41.166 | 1.00 | 50.90 | C |
| ATOM | 5336 | CD2 | TYR A | 726 | −20.776 | 22.873 | −41.050 | 1.00 | 49.96 | C |
| ATOM | 5337 | C   | TYR A | 726 | −18.235 | 23.079 | −43.261 | 1.00 | 54.98 | C |
| ATOM | 5338 | O   | TYR A | 726 | −18.295 | 24.276 | −43.091 | 1.00 | 60.20 | O |
| ATOM | 5339 | N   | GLN A | 727 | −18.721 | 22.462 | −44.336 | 1.00 | 61.93 | N |
| ATOM | 5340 | CA  | GLN A | 727 | −19.256 | 23.166 | −45.472 | 1.00 | 58.71 | C |
| ATOM | 5341 | CB  | GLN A | 727 | −18.533 | 22.725 | −46.711 | 1.00 | 56.49 | C |
| ATOM | 5342 | CG  | GLN A | 727 | −18.759 | 23.627 | −47.904 | 1.00 | 57.51 | C |
| ATOM | 5343 | CD  | GLN A | 727 | −17.775 | 23.310 | −49.005 | 1.00 | 58.47 | C |
| ATOM | 5344 | OE1 | GLN A | 727 | −18.119 | 22.569 | −49.985 | 1.00 | 58.11 | O |
| ATOM | 5345 | NE2 | GLN A | 727 | −16.520 | 23.691 | −48.810 | 1.00 | 59.21 | N |
| ATOM | 5346 | C   | GLN A | 727 | −20.705 | 22.790 | −45.473 | 1.00 | 60.73 | C |
| ATOM | 5347 | O   | GLN A | 727 | −21.078 | 21.804 | −46.042 | 1.00 | 62.76 | O |
| ATOM | 5348 | N   | GLU A | 728 | −21.502 | 23.575 | −44.756 | 1.00 | 65.41 | N |
| ATOM | 5349 | CA  | GLU A | 728 | −22.928 | 23.348 | −44.611 | 1.00 | 63.72 | C |
| ATOM | 5350 | CB  | GLU A | 728 | −23.576 | 24.559 | −43.975 | 1.00 | 67.76 | C |
| ATOM | 5351 | CG  | GLU A | 728 | −24.784 | 24.187 | −43.147 | 1.00 | 73.01 | C |
| ATOM | 5352 | CD  | GLU A | 728 | −25.947 | 25.098 | −43.387 | 1.00 | 77.34 | C |

TABLE 6-continued

Atomic coordinates for CRBN:DDB1: Compound B (Human protein)

| ATOM | 5353 | OE1 | GLU A | 728 | −26.265 | 25.901 | −42.468 | 1.00 | 82.89 | O |
|---|---|---|---|---|---|---|---|---|---|---|
| ATOM | 5354 | OE2 | GLU A | 728 | −26.509 | 24.999 | −44.504 | 1.00 | 80.40 | O |
| ATOM | 5355 | C | GLU A | 728 | −23.678 | 23.039 | −45.915 | 1.00 | 60.34 | C |
| ATOM | 5356 | O | GLU A | 728 | −24.427 | 22.065 | −45.991 | 1.00 | 54.80 | O |
| ATOM | 5357 | N | VAL A | 729 | −23.462 | 23.841 | −46.946 | 1.00 | 59.75 | N |
| ATOM | 5358 | CA | VAL A | 729 | −24.123 | 23.569 | −48.255 | 1.00 | 59.35 | C |
| ATOM | 5359 | CB | VAL A | 729 | −23.798 | 24.612 | −49.343 | 1.00 | 56.28 | C |
| ATOM | 5360 | CG1 | VAL A | 729 | −24.098 | 25.996 | −48.822 | 1.00 | 57.49 | C |
| ATOM | 5361 | CG2 | VAL A | 729 | −22.343 | 24.554 | −49.772 | 1.00 | 59.31 | C |
| ATOM | 5362 | C | VAL A | 729 | −23.884 | 22.148 | −48.803 | 1.00 | 54.69 | C |
| ATOM | 5363 | O | VAL A | 729 | −24.820 | 21.480 | −49.182 | 1.00 | 59.85 | O |
| ATOM | 5364 | N | SER A | 730 | −22.668 | 21.656 | −48.780 | 1.00 | 49.35 | N |
| ATOM | 5365 | CA | SER A | 730 | −22.416 | 20.325 | −49.264 | 1.00 | 51.96 | C |
| ATOM | 5366 | CB | SER A | 730 | −20.957 | 20.190 | −49.553 | 1.00 | 52.87 | C |
| ATOM | 5367 | OG | SER A | 730 | −20.462 | 21.436 | −49.935 | 1.00 | 54.50 | O |
| ATOM | 5368 | C | SER A | 730 | −22.805 | 19.256 | −48.259 | 1.00 | 57.86 | C |
| ATOM | 5369 | O | SER A | 730 | −22.755 | 18.053 | −48.574 | 1.00 | 61.22 | O |
| ATOM | 5370 | N | GLN A | 731 | −23.140 | 19.698 | −47.037 | 1.00 | 61.02 | N |
| ATOM | 5371 | CA | GLN A | 731 | −23.544 | 18.852 | −45.926 | 1.00 | 56.56 | C |
| ATOM | 5372 | CB | GLN A | 731 | −24.826 | 18.108 | −46.249 | 1.00 | 58.30 | C |
| ATOM | 5373 | CG | GLN A | 731 | −26.024 | 19.011 | −46.215 | 1.00 | 64.38 | C |
| ATOM | 5374 | CD | GLN A | 731 | −27.015 | 18.557 | −45.191 | 1.00 | 72.67 | C |
| ATOM | 5375 | OE1 | GLN A | 731 | −27.547 | 17.433 | −45.280 | 1.00 | 80.48 | O |
| ATOM | 5376 | NE2 | GLN A | 731 | −27.263 | 19.408 | −44.185 | 1.00 | 75.24 | N |
| ATOM | 5377 | C | GLN A | 731 | −22.459 | 17.900 | −45.608 | 1.00 | 55.04 | C |
| ATOM | 5378 | O | GLN A | 731 | −22.692 | 16.738 | −45.479 | 1.00 | 55.96 | O |
| ATOM | 5379 | N | CYS A | 732 | −21.238 | 18.389 | −45.533 | 1.00 | 58.54 | N |
| ATOM | 5380 | CA | CYS A | 732 | −20.109 | 17.510 | −45.310 | 1.00 | 65.40 | C |
| ATOM | 5381 | CB | CYS A | 732 | −19.658 | 16.942 | −46.638 | 1.00 | 73.95 | C |
| ATOM | 5382 | SG | CYS A | 732 | −18.736 | 18.204 | −47.486 | 1.00 | 95.62 | S |
| ATOM | 5383 | C | CYS A | 732 | −18.964 | 18.266 | −44.625 | 1.00 | 61.00 | C |
| ATOM | 5384 | O | CYS A | 732 | −19.079 | 19.466 | −44.349 | 1.00 | 60.13 | O |
| ATOM | 5385 | N | PHE A | 733 | −17.887 | 17.531 | −44.342 | 1.00 | 57.90 | N |
| ATOM | 5386 | CA | PHE A | 733 | −16.724 | 18.006 | −43.602 | 1.00 | 53.53 | C |
| ATOM | 5387 | CB | PHE A | 733 | −16.492 | 17.156 | −42.342 | 1.00 | 52.15 | C |
| ATOM | 5388 | CG | PHE A | 733 | −17.400 | 17.471 | −41.194 | 1.00 | 49.64 | C |
| ATOM | 5389 | CD1 | PHE A | 733 | −17.187 | 18.582 | −40.417 | 1.00 | 50.46 | C |
| ATOM | 5390 | CE1 | PHE A | 733 | −18.011 | 18.903 | −39.375 | 1.00 | 48.71 | C |
| ATOM | 5391 | CZ | PHE A | 733 | −19.025 | 18.083 | −39.062 | 1.00 | 49.65 | C |
| ATOM | 5392 | CE2 | PHE A | 733 | −19.201 | 16.933 | −39.792 | 1.00 | 52.01 | C |
| ATOM | 5393 | CD2 | PHE A | 733 | −18.399 | 16.642 | −40.860 | 1.00 | 48.56 | C |
| ATOM | 5394 | C | PHE A | 733 | −15.480 | 17.857 | −44.453 | 1.00 | 52.44 | C |
| ATOM | 5395 | O | PHE A | 733 | −15.220 | 16.805 | −45.045 | 1.00 | 50.62 | O |
| ATOM | 5396 | N | GLY A | 734 | −14.678 | 18.898 | −44.461 | 1.00 | 52.55 | N |
| ATOM | 5397 | CA | GLY A | 734 | −13.328 | 18.800 | −44.987 | 1.00 | 51.61 | C |
| ATOM | 5398 | C | GLY A | 734 | −12.407 | 18.360 | −43.883 | 1.00 | 48.38 | C |
| ATOM | 5399 | O | GLY A | 734 | −12.482 | 18.882 | −42.795 | 1.00 | 49.23 | O |
| ATOM | 5400 | N | VAL A | 735 | −11.541 | 17.398 | −44.150 | 1.00 | 45.98 | N |
| ATOM | 5401 | CA | VAL A | 735 | −10.526 | 17.030 | −43.178 | 1.00 | 44.64 | C |
| ATOM | 5402 | CB | VAL A | 735 | −10.979 | 15.760 | −42.447 | 1.00 | 41.78 | C |
| ATOM | 5403 | CG1 | VAL A | 735 | −9.865 | 15.195 | −41.585 | 1.00 | 39.85 | C |
| ATOM | 5404 | CG2 | VAL A | 735 | −12.200 | 16.085 | −41.597 | 1.00 | 42.84 | C |
| ATOM | 5405 | C | VAL A | 735 | −9.120 | 16.837 | −43.762 | 1.00 | 44.05 | C |
| ATOM | 5406 | O | VAL A | 735 | −8.913 | 15.860 | −44.480 | 1.00 | 43.66 | O |
| ATOM | 5407 | N | LEU A | 736 | −8.155 | 17.714 | −43.449 | 1.00 | 41.58 | N |
| ATOM | 5408 | CA | LEU A | 736 | −6.768 | 17.396 | −43.828 | 1.00 | 42.73 | C |
| ATOM | 5409 | CB | LEU A | 736 | −5.815 | 18.547 | −43.604 | 1.00 | 41.97 | C |
| ATOM | 5410 | CG | LEU A | 736 | −6.181 | 19.766 | −44.428 | 1.00 | 44.21 | C |
| ATOM | 5411 | CD1 | LEU A | 736 | −5.288 | 20.962 | −44.145 | 1.00 | 43.13 | C |
| ATOM | 5412 | CD2 | LEU A | 736 | −6.135 | 19.411 | −45.897 | 1.00 | 46.71 | C |
| ATOM | 5413 | C | LEU A | 736 | −6.301 | 16.188 | −43.043 | 1.00 | 44.51 | C |
| ATOM | 5414 | O | LEU A | 736 | −6.528 | 16.123 | −41.843 | 1.00 | 43.99 | O |
| ATOM | 5415 | N | SER A | 737 | −5.695 | 15.210 | −43.705 | 1.00 | 44.96 | N |
| ATOM | 5416 | CA | SER A | 737 | −5.263 | 14.015 | −42.983 | 1.00 | 50.56 | C |
| ATOM | 5417 | CB | SER A | 737 | −6.308 | 12.877 | −43.074 | 1.00 | 54.12 | C |
| ATOM | 5418 | OG | SER A | 737 | −6.620 | 12.158 | −44.315 | 1.00 | 59.88 | O |
| ATOM | 5419 | C | SER A | 737 | −3.917 | 13.540 | −43.469 | 1.00 | 52.13 | C |
| ATOM | 5420 | O | SER A | 737 | −3.391 | 14.061 | −44.472 | 1.00 | 51.84 | O |
| ATOM | 5421 | N | SER A | 738 | −3.358 | 12.540 | −42.782 | 1.00 | 49.36 | N |
| ATOM | 5422 | CA | SER A | 738 | −1.989 | 12.209 | −43.059 | 1.00 | 50.97 | C |
| ATOM | 5423 | CB | SER A | 738 | −1.099 | 13.233 | −42.371 | 1.00 | 49.20 | C |
| ATOM | 5424 | OG | SER A | 738 | 0.060 | 12.654 | −41.827 | 1.00 | 53.78 | O |
| ATOM | 5425 | C | SER A | 738 | −1.616 | 10.795 | −42.698 | 1.00 | 54.82 | C |
| ATOM | 5426 | O | SER A | 738 | −1.418 | 10.490 | −41.515 | 1.00 | 65.88 | O |
| ATOM | 5427 | N | ARG A | 739 | −1.468 | 9.938 | −43.716 | 1.00 | 54.94 | N |
| ATOM | 5428 | CA | ARG A | 739 | −1.058 | 8.550 | −43.488 | 1.00 | 52.99 | C |
| ATOM | 5429 | CB | ARG A | 739 | −1.921 | 7.608 | −44.314 | 1.00 | 57.72 | C |
| ATOM | 5430 | CG | ARG A | 739 | −1.565 | 7.469 | −45.781 | 1.00 | 60.40 | C |

TABLE 6-continued

Atomic coordinates for CRBN:DDB1: Compound B (Human protein)

| ATOM | 5431 | CD | ARG A | 739 | −2.528 | 6.529 | −46.494 | 1.00 | 62.54 | C |
| --- | --- | --- | --- | --- | --- | --- | --- | --- | --- | --- |
| ATOM | 5432 | NE | ARG A | 739 | −1.995 | 6.171 | −47.810 | 1.00 | 63.69 | N |
| ATOM | 5433 | CZ | ARG A | 739 | −2.067 | 6.921 | −48.911 | 1.00 | 63.51 | C |
| ATOM | 5434 | NH1 | ARG A | 739 | −2.690 | 8.117 | −48.954 | 1.00 | 59.73 | N |
| ATOM | 5435 | NH2 | ARG A | 739 | −1.493 | 6.452 | −50.003 | 1.00 | 67.76 | N |
| ATOM | 5436 | C | ARG A | 739 | 0.417 | 8.325 | −43.767 | 1.00 | 48.33 | C |
| ATOM | 5437 | O | ARG A | 739 | 0.994 | 9.047 | −44.589 | 1.00 | 45.54 | O |
| ATOM | 5438 | N | ILE A | 740 | 1.003 | 7.341 | −43.073 | 1.00 | 44.99 | N |
| ATOM | 5439 | CA | ILE A | 740 | 2.397 | 6.927 | −43.298 | 1.00 | 49.18 | C |
| ATOM | 5440 | CB | ILE A | 740 | 3.096 | 6.434 | −41.994 | 1.00 | 51.04 | C |
| ATOM | 5441 | CG1 | ILE A | 740 | 3.030 | 7.451 | −40.871 | 1.00 | 51.26 | C |
| ATOM | 5442 | CD1 | ILE A | 740 | 3.667 | 8.768 | −41.257 | 1.00 | 54.17 | C |
| ATOM | 5443 | CG2 | ILE A | 740 | 4.561 | 6.122 | −42.255 | 1.00 | 51.41 | C |
| ATOM | 5444 | C | ILE A | 740 | 2.538 | 5.752 | −44.259 | 1.00 | 52.24 | C |
| ATOM | 5445 | O | ILE A | 740 | 2.026 | 4.665 | −43.988 | 1.00 | 50.30 | O |
| ATOM | 5446 | N | GLU A | 741 | 3.284 | 5.949 | −45.346 | 1.00 | 61.29 | N |
| ATOM | 5447 | CA | GLU A | 741 | 3.775 | 4.835 | −46.188 | 1.00 | 65.42 | C |
| ATOM | 5448 | CB | GLU A | 741 | 3.401 | 5.055 | −47.662 | 1.00 | 68.99 | C |
| ATOM | 5449 | CG | GLU A | 741 | 1.865 | 5.062 | −47.837 | 1.00 | 77.65 | C |
| ATOM | 5450 | CD | GLU A | 741 | 1.317 | 4.694 | −49.232 | 1.00 | 82.38 | C |
| ATOM | 5451 | OE1 | GLU A | 741 | 1.941 | 5.027 | −50.275 | 1.00 | 88.15 | O |
| ATOM | 5452 | OE2 | GLU A | 741 | 0.215 | 4.090 | −49.279 | 1.00 | 76.98 | O |
| ATOM | 5453 | C | GLU A | 741 | 5.279 | 4.595 | −45.974 | 1.00 | 67.75 | C |
| ATOM | 5454 | O | GLU A | 741 | 6.035 | 5.514 | −45.672 | 1.00 | 69.67 | O |
| ATOM | 5455 | N | VAL A | 742 | 5.689 | 3.335 | −46.050 | 1.00 | 72.61 | N |
| ATOM | 5456 | CA | VAL A | 742 | 7.116 | 2.965 | −46.079 | 1.00 | 75.15 | C |
| ATOM | 5457 | CB | VAL A | 742 | 7.434 | 1.771 | −45.109 | 1.00 | 77.42 | C |
| ATOM | 5458 | CG1 | VAL A | 742 | 6.888 | 0.427 | −45.620 | 1.00 | 78.75 | C |
| ATOM | 5459 | CG2 | VAL A | 742 | 8.937 | 1.693 | −44.815 | 1.00 | 77.67 | C |
| ATOM | 5460 | C | VAL A | 742 | 7.483 | 2.714 | −47.559 | 1.00 | 72.72 | C |
| ATOM | 5461 | O | VAL A | 742 | 6.627 | 2.241 | −48.334 | 1.00 | 67.03 | O |
| ATOM | 5462 | N | GLN A | 743 | 8.733 | 3.049 | −47.940 | 1.00 | 76.55 | N |
| ATOM | 5463 | CA | GLN A | 743 | 9.191 | 3.078 | −49.376 | 1.00 | 79.17 | C |
| ATOM | 5464 | CB | GLN A | 743 | 10.457 | 3.972 | −49.560 | 1.00 | 74.06 | C |
| ATOM | 5465 | C | GLN A | 743 | 9.374 | 1.676 | −50.047 | 1.00 | 78.20 | C |
| ATOM | 5466 | O | GLN A | 743 | 9.778 | 0.707 | −49.393 | 1.00 | 68.87 | O |
| ATOM | 5467 | N | ASP A | 744 | 9.041 | 1.603 | −51.346 | 1.00 | 84.87 | N |
| ATOM | 5468 | CA | ASP A | 744 | 9.091 | 0.376 | −52.174 | 1.00 | 85.64 | C |
| ATOM | 5469 | CB | ASP A | 744 | 7.766 | 0.226 | −52.971 | 1.00 | 77.29 | C |
| ATOM | 5470 | C | ASP A | 744 | 10.324 | 0.492 | −53.103 | 1.00 | 87.75 | C |
| ATOM | 5471 | O | ASP A | 744 | 10.907 | −0.500 | −53.569 | 1.00 | 94.14 | O |
| ATOM | 5472 | N | THR A | 749 | 6.128 | 3.468 | −53.040 | 1.00 | 76.60 | N |
| ATOM | 5473 | CA | THR A | 749 | 5.813 | 3.619 | −51.594 | 1.00 | 79.57 | C |
| ATOM | 5474 | CB | THR A | 749 | 5.924 | 5.111 | −51.131 | 1.00 | 78.61 | C |
| ATOM | 5475 | OG1 | THR A | 749 | 6.263 | 5.138 | −49.748 | 1.00 | 80.65 | O |
| ATOM | 5476 | CG2 | THR A | 749 | 4.629 | 5.987 | −51.353 | 1.00 | 76.66 | C |
| ATOM | 5477 | C | THR A | 749 | 4.466 | 2.987 | −51.149 | 1.00 | 75.93 | C |
| ATOM | 5478 | O | THR A | 749 | 3.437 | 3.199 | −51.806 | 1.00 | 77.89 | O |
| ATOM | 5479 | N | THR A | 750 | 4.464 | 2.198 | −50.065 | 1.00 | 73.26 | N |
| ATOM | 5480 | CA | THR A | 750 | 3.217 | 1.459 | −49.678 | 1.00 | 79.60 | C |
| ATOM | 5481 | CB | THR A | 750 | 3.256 | −0.096 | −49.969 | 1.00 | 78.51 | C |
| ATOM | 5482 | OG1 | THR A | 750 | 3.812 | −0.815 | −48.853 | 1.00 | 73.55 | O |
| ATOM | 5483 | CG2 | THR A | 750 | 3.993 | −0.448 | −51.345 | 1.00 | 78.40 | C |
| ATOM | 5484 | C | THR A | 750 | 2.648 | 1.687 | −48.247 | 1.00 | 82.28 | C |
| ATOM | 5485 | O | THR A | 750 | 3.377 | 1.927 | −47.268 | 1.00 | 82.62 | O |
| ATOM | 5486 | N | ALA A | 751 | 1.317 | 1.585 | −48.181 | 1.00 | 77.95 | N |
| ATOM | 5487 | CA | ALA A | 751 | 0.538 | 1.657 | −46.951 | 1.00 | 72.25 | C |
| ATOM | 5488 | CB | ALA A | 751 | −0.929 | 1.525 | −47.307 | 1.00 | 71.59 | C |
| ATOM | 5489 | C | ALA A | 751 | 0.913 | 0.567 | −45.954 | 1.00 | 67.93 | C |
| ATOM | 5490 | O | ALA A | 751 | 1.304 | −0.509 | −46.357 | 1.00 | 73.04 | O |
| ATOM | 5491 | N | LEU A | 752 | 0.793 | 0.857 | −44.663 | 1.00 | 65.50 | N |
| ATOM | 5492 | CA | LEU A | 752 | 0.999 | −0.142 | −43.596 | 1.00 | 64.85 | C |
| ATOM | 5493 | CB | LEU A | 752 | 1.705 | 0.481 | −42.359 | 1.00 | 69.61 | C |
| ATOM | 5494 | CG | LEU A | 752 | 2.910 | 1.442 | −42.540 | 1.00 | 72.77 | C |
| ATOM | 5495 | CD1 | LEU A | 752 | 3.525 | 1.954 | −41.233 | 1.00 | 72.08 | C |
| ATOM | 5496 | CD2 | LEU A | 752 | 3.979 | 0.751 | −43.382 | 1.00 | 76.11 | C |
| ATOM | 5497 | C | LEU A | 752 | −0.340 | −0.780 | −43.178 | 1.00 | 57.63 | C |
| ATOM | 5498 | O | LEU A | 752 | −0.347 | −1.748 | −42.412 | 1.00 | 55.45 | O |
| ATOM | 5499 | N | ARG A | 753 | −1.450 | −0.239 | −43.695 | 1.00 | 51.99 | N |
| ATOM | 5500 | CA | ARG A | 753 | −2.814 | −0.642 | −43.324 | 1.00 | 50.79 | C |
| ATOM | 5501 | CB | ARG A | 753 | −3.080 | −0.458 | −41.806 | 1.00 | 53.20 | C |
| ATOM | 5502 | CG | ARG A | 753 | −3.486 | 0.954 | −41.370 | 1.00 | 56.86 | C |
| ATOM | 5503 | CD | ARG A | 753 | −3.258 | 1.273 | −39.893 | 1.00 | 56.58 | C |
| ATOM | 5504 | NE | ARG A | 753 | −1.843 | 1.411 | −39.589 | 1.00 | 56.24 | N |
| ATOM | 5505 | CZ | ARG A | 753 | −1.120 | 0.525 | −38.892 | 1.00 | 60.89 | C |
| ATOM | 5506 | NH1 | ARG A | 753 | −1.667 | −0.614 | −38.374 | 1.00 | 59.80 | N |
| ATOM | 5507 | NH2 | ARG A | 753 | 0.189 | 0.773 | −38.715 | 1.00 | 59.28 | N |
| ATOM | 5508 | C | ARG A | 753 | −3.824 | 0.178 | −44.129 | 1.00 | 46.93 | C |

TABLE 6-continued

Atomic coordinates for CRBN:DDB1: Compound B (Human protein)

| ATOM | 5509 | O | ARG A | 753 | −3.524 | 1.284 | −44.516 | 1.00 | 46.97 | O |
|---|---|---|---|---|---|---|---|---|---|---|
| ATOM | 5510 | N | PRO A | 754 | −5.028 | −0.343 | −44.368 | 1.00 | 48.09 | N |
| ATOM | 5511 | CA | PRO A | 754 | −6.074 | 0.532 | −44.922 | 1.00 | 51.04 | C |
| ATOM | 5512 | CB | PRO A | 754 | −7.265 | −0.416 | −45.201 | 1.00 | 48.34 | C |
| ATOM | 5513 | CG | PRO A | 754 | −6.929 | −1.678 | −44.539 | 1.00 | 48.18 | C |
| ATOM | 5514 | CD | PRO A | 754 | −5.439 | −1.748 | −44.393 | 1.00 | 49.24 | C |
| ATOM | 5515 | C | PRO A | 754 | −6.494 | 1.617 | −43.940 | 1.00 | 55.19 | C |
| ATOM | 5516 | O | PRO A | 754 | −6.550 | 1.353 | −42.687 | 1.00 | 56.92 | O |
| ATOM | 5517 | N | SER A | 755 | −6.799 | 2.782 | −44.527 | 1.00 | 51.92 | N |
| ATOM | 5518 | CA | SER A | 755 | −6.920 | 4.056 | −43.827 | 1.00 | 51.43 | C |
| ATOM | 5519 | CB | SER A | 755 | −5.658 | 4.930 | −44.010 | 1.00 | 50.82 | C |
| ATOM | 5520 | OG | SER A | 755 | −4.402 | 4.251 | −43.782 | 1.00 | 54.74 | O |
| ATOM | 5521 | C | SER A | 755 | −8.037 | 4.759 | −44.496 | 1.00 | 51.27 | C |
| ATOM | 5522 | O | SER A | 755 | −8.314 | 4.492 | −45.629 | 1.00 | 58.00 | O |
| ATOM | 5523 | N | ALA A | 756 | −8.636 | 5.718 | −43.839 | 1.00 | 52.45 | N |
| ATOM | 5524 | CA | ALA A | 756 | −9.659 | 6.567 | −44.463 | 1.00 | 53.80 | C |
| ATOM | 5525 | CB | ALA A | 756 | −9.886 | 7.825 | −43.618 | 1.00 | 55.36 | C |
| ATOM | 5526 | C | ALA A | 756 | −9.391 | 6.996 | −45.909 | 1.00 | 51.79 | C |
| ATOM | 5527 | O | ALA A | 756 | −10.296 | 6.977 | −46.706 | 1.00 | 49.37 | O |
| ATOM | 5528 | N | SER A | 757 | −8.170 | 7.405 | −46.221 | 1.00 | 51.27 | N |
| ATOM | 5529 | CA | SER A | 757 | −7.883 | 8.042 | −47.488 | 1.00 | 52.39 | C |
| ATOM | 5530 | CB | SER A | 757 | −6.656 | 8.934 | −47.394 | 1.00 | 51.93 | C |
| ATOM | 5531 | OG | SER A | 757 | −5.495 | 8.218 | −47.031 | 1.00 | 51.59 | O |
| ATOM | 5532 | C | SER A | 757 | −7.651 | 7.050 | −48.600 | 1.00 | 59.30 | C |
| ATOM | 5533 | O | SER A | 757 | −7.647 | 7.445 | −49.773 | 1.00 | 71.46 | O |
| ATOM | 5534 | N | THR A | 758 | −7.437 | 5.781 | −48.251 | 1.00 | 57.50 | N |
| ATOM | 5535 | CA | THR A | 758 | −7.285 | 4.737 | −49.230 | 1.00 | 55.75 | C |
| ATOM | 5536 | CB | THR A | 758 | −6.252 | 3.714 | −48.781 | 1.00 | 52.77 | C |
| ATOM | 5537 | OG1 | THR A | 758 | −6.801 | 2.942 | −47.719 | 1.00 | 51.41 | O |
| ATOM | 5538 | CG2 | THR A | 758 | −4.940 | 4.373 | −48.334 | 1.00 | 51.62 | C |
| ATOM | 5539 | C | THR A | 758 | −8.604 | 3.991 | −49.419 | 1.00 | 61.80 | C |
| ATOM | 5540 | O | THR A | 758 | −8.685 | 3.080 | −50.223 | 1.00 | 73.22 | O |
| ATOM | 5541 | N | GLN A | 759 | −9.593 | 4.337 | −48.625 | 1.00 | 63.04 | N |
| ATOM | 5542 | CA | GLN A | 759 | −10.867 | 3.665 | −48.656 | 1.00 | 61.91 | C |
| ATOM | 5543 | CB | GLN A | 759 | −11.124 | 3.072 | −47.295 | 1.00 | 68.86 | C |
| ATOM | 5544 | CG | GLN A | 759 | −10.052 | 2.118 | −46.853 | 1.00 | 75.86 | C |
| ATOM | 5545 | CD | GLN A | 759 | −10.428 | 0.703 | −47.164 | 1.00 | 87.45 | C |
| ATOM | 5546 | OE1 | GLN A | 759 | −11.398 | 0.188 | −46.630 | 1.00 | 91.04 | O |
| ATOM | 5547 | NE2 | GLN A | 759 | −9.671 | 0.066 | −48.044 | 1.00 | 94.78 | N |
| ATOM | 5548 | C | GLN A | 759 | −12.045 | 4.512 | −49.017 | 1.00 | 58.43 | C |
| ATOM | 5549 | O | GLN A | 759 | −13.161 | 4.165 | −48.696 | 1.00 | 55.04 | O |
| ATOM | 5550 | N | ALA A | 760 | −11.812 | 5.638 | −49.648 | 1.00 | 54.66 | N |
| ATOM | 5551 | CA | ALA A | 760 | −12.904 | 6.509 | −50.005 | 1.00 | 58.38 | C |
| ATOM | 5552 | CB | ALA A | 760 | −12.374 | 7.884 | −50.293 | 1.00 | 62.42 | C |
| ATOM | 5553 | C | ALA A | 760 | −13.723 | 6.003 | −51.171 | 1.00 | 58.58 | C |
| ATOM | 5554 | O | ALA A | 760 | −13.226 | 5.287 | −52.019 | 1.00 | 57.93 | O |
| ATOM | 5555 | N | LEU A | 761 | −14.981 | 6.397 | −51.226 | 1.00 | 57.47 | N |
| ATOM | 5556 | CA | LEU A | 761 | −15.821 | 5.978 | −52.311 | 1.00 | 60.90 | C |
| ATOM | 5557 | CB | LEU A | 761 | −17.168 | 6.641 | −52.198 | 1.00 | 65.34 | C |
| ATOM | 5558 | CG | LEU A | 761 | −18.310 | 5.816 | −51.673 | 1.00 | 71.31 | C |
| ATOM | 5559 | CD1 | LEU A | 761 | −18.129 | 5.673 | −50.182 | 1.00 | 76.35 | C |
| ATOM | 5560 | CD2 | LEU A | 761 | −19.594 | 6.546 | −51.976 | 1.00 | 71.93 | C |
| ATOM | 5561 | C | LEU A | 761 | −15.257 | 6.476 | −53.595 | 1.00 | 63.83 | C |
| ATOM | 5562 | O | LEU A | 761 | −15.165 | 5.745 | −54.551 | 1.00 | 76.54 | O |
| ATOM | 5563 | N | SER A | 762 | −14.859 | 7.727 | −53.620 | 1.00 | 66.18 | N |
| ATOM | 5564 | CA | SER A | 762 | −14.327 | 8.299 | −54.826 | 1.00 | 63.80 | C |
| ATOM | 5565 | CB | SER A | 762 | −15.212 | 9.426 | −55.301 | 1.00 | 63.55 | C |
| ATOM | 5566 | C | SER A | 762 | −12.987 | 8.807 | −54.444 | 1.00 | 67.64 | C |
| ATOM | 5567 | O | SER A | 762 | −12.781 | 9.143 | −53.314 | 1.00 | 74.10 | O |
| ATOM | 5568 | N | SER A | 763 | −12.050 | 8.824 | −55.362 | 1.00 | 69.32 | N |
| ATOM | 5569 | CA | SER A | 763 | −10.723 | 9.253 | −55.025 | 1.00 | 62.27 | C |
| ATOM | 5570 | CB | SER A | 763 | −9.889 | 8.032 | −54.725 | 1.00 | 52.41 | C |
| ATOM | 5571 | OG | SER A | 763 | −8.530 | 8.313 | −54.882 | 1.00 | 51.34 | O |
| ATOM | 5572 | C | SER A | 763 | −10.117 | 10.097 | −56.138 | 1.00 | 65.71 | C |
| ATOM | 5573 | O | SER A | 763 | −10.643 | 10.137 | −57.232 | 1.00 | 65.51 | O |
| ATOM | 5574 | N | SER A | 764 | −9.020 | 10.783 | −55.835 | 1.00 | 68.55 | N |
| ATOM | 5575 | CA | SER A | 764 | −8.342 | 11.663 | −56.780 | 1.00 | 63.22 | C |
| ATOM | 5576 | CB | SER A | 764 | −9.062 | 12.995 | −56.841 | 1.00 | 59.59 | C |
| ATOM | 5577 | OG | SER A | 764 | −10.086 | 13.058 | −55.875 | 1.00 | 54.09 | O |
| ATOM | 5578 | C | SER A | 764 | −6.906 | 11.912 | −56.410 | 1.00 | 61.97 | C |
| ATOM | 5579 | O | SER A | 764 | −6.497 | 11.592 | −55.328 | 1.00 | 64.80 | O |
| ATOM | 5580 | N | VAL A | 765 | −6.131 | 12.469 | −57.323 | 1.00 | 64.08 | N |
| ATOM | 5581 | CA | VAL A | 765 | −4.747 | 12.814 | −57.040 | 1.00 | 66.59 | C |
| ATOM | 5582 | CB | VAL A | 765 | −3.781 | 11.756 | −57.503 | 1.00 | 69.96 | C |
| ATOM | 5583 | CG1 | VAL A | 765 | −3.812 | 11.680 | −59.003 | 1.00 | 77.00 | C |
| ATOM | 5584 | CG2 | VAL A | 765 | −2.393 | 12.117 | −57.050 | 1.00 | 74.57 | C |
| ATOM | 5585 | C | VAL A | 765 | −4.452 | 14.145 | −57.711 | 1.00 | 64.39 | C |
| ATOM | 5586 | O | VAL A | 765 | −4.980 | 14.424 | −58.765 | 1.00 | 62.18 | O |

TABLE 6-continued

Atomic coordinates for CRBN:DDB1: Compound B (Human protein)

| ATOM | 5587 | N | SER A | 766 | −3.623 | 14.977 | −57.104 | 1.00 | 68.25 | N |
|---|---|---|---|---|---|---|---|---|---|---|
| ATOM | 5588 | CA | SER A | 766 | −3.362 | 16.291 | −57.666 | 1.00 | 69.32 | C |
| ATOM | 5589 | CB | SER A | 766 | −2.633 | 17.184 | −56.669 | 1.00 | 66.76 | C |
| ATOM | 5590 | OG | SER A | 766 | −3.528 | 18.044 | −55.993 | 1.00 | 61.42 | O |
| ATOM | 5591 | C | SER A | 766 | −2.597 | 16.281 | −58.944 | 1.00 | 73.08 | C |
| ATOM | 5592 | O | SER A | 766 | −1.567 | 15.646 | −59.050 | 1.00 | 67.81 | O |
| ATOM | 5593 | N | SER A | 767 | −3.101 | 17.028 | −59.912 | 1.00 | 83.75 | N |
| ATOM | 5594 | CA | SER A | 767 | −2.440 | 17.140 | −61.188 | 1.00 | 90.72 | C |
| ATOM | 5595 | CB | SER A | 767 | −3.281 | 17.987 | −62.118 | 1.00 | 92.56 | C |
| ATOM | 5596 | OG | SER A | 767 | −3.432 | 19.292 | −61.580 | 1.00 | 87.31 | O |
| ATOM | 5597 | C | SER A | 767 | −1.220 | 17.924 | −60.860 | 1.00 | 91.61 | C |
| ATOM | 5598 | O | SER A | 767 | −1.315 | 18.970 | −60.232 | 1.00 | 87.08 | O |
| ATOM | 5599 | N | SER A | 768 | −0.077 | 17.471 | −61.324 | 1.00 | 92.66 | N |
| ATOM | 5600 | CA | SER A | 768 | 1.141 | 18.171 | −61.012 | 1.00 | 91.91 | C |
| ATOM | 5601 | CB | SER A | 768 | 2.317 | 17.439 | −61.624 | 1.00 | 91.80 | C |
| ATOM | 5602 | OG | SER A | 768 | 2.093 | 16.049 | −61.555 | 1.00 | 87.17 | O |
| ATOM | 5603 | C | SER A | 768 | 1.008 | 19.556 | −61.584 | 1.00 | 93.91 | C |
| ATOM | 5604 | O | SER A | 768 | 0.303 | 19.758 | −62.547 | 1.00 | 85.32 | O |
| ATOM | 5605 | N | LYS A | 769 | 1.644 | 20.530 | −60.961 | 1.00 | 99.81 | N |
| ATOM | 5606 | CA | LYS A | 769 | 1.569 | 21.887 | −61.460 | 1.00 | 94.83 | C |
| ATOM | 5607 | CB | LYS A | 769 | 2.515 | 22.794 | −60.682 | 1.00 | 86.30 | C |
| ATOM | 5608 | C | LYS A | 769 | 1.980 | 21.886 | −62.910 | 1.00 | 85.29 | C |
| ATOM | 5609 | O | LYS A | 769 | 3.123 | 21.584 | −63.218 | 1.00 | 78.46 | O |
| ATOM | 5610 | N | GLU A | 784 | 11.997 | 2.667 | −45.192 | 1.00 | 62.91 | N |
| ATOM | 5611 | CA | GLU A | 784 | 12.128 | 4.093 | −44.697 | 1.00 | 70.32 | C |
| ATOM | 5612 | CB | GLU A | 784 | 13.452 | 4.790 | −45.104 | 1.00 | 66.51 | C |
| ATOM | 5613 | C | GLU A | 784 | 10.938 | 4.989 | −45.091 | 1.00 | 68.45 | C |
| ATOM | 5614 | O | GLU A | 784 | 10.414 | 4.867 | −46.175 | 1.00 | 70.62 | O |
| ATOM | 5615 | N | GLU A | 785 | 10.573 | 5.916 | −44.208 | 1.00 | 69.95 | N |
| ATOM | 5616 | CA | GLU A | 785 | 9.163 | 6.319 | −43.998 | 1.00 | 72.36 | C |
| ATOM | 5617 | CB | GLU A | 785 | 8.916 | 6.594 | −42.498 | 1.00 | 72.85 | C |
| ATOM | 5618 | CG | GLU A | 785 | 9.398 | 5.525 | −41.532 | 1.00 | 70.52 | C |
| ATOM | 5619 | CD | GLU A | 785 | 8.374 | 5.250 | −40.464 | 1.00 | 69.13 | C |
| ATOM | 5620 | OE1 | GLU A | 785 | 7.875 | 6.215 | −39.903 | 1.00 | 64.77 | O |
| ATOM | 5621 | OE2 | GLU A | 785 | 8.036 | 4.075 | −40.206 | 1.00 | 78.62 | O |
| ATOM | 5622 | C | GLU A | 785 | 8.753 | 7.588 | −44.712 | 1.00 | 67.73 | C |
| ATOM | 5623 | O | GLU A | 785 | 9.582 | 8.456 | −44.864 | 1.00 | 68.03 | O |
| ATOM | 5624 | N | VAL A | 786 | 7.470 | 7.739 | −45.048 | 1.00 | 61.40 | N |
| ATOM | 5625 | CA | VAL A | 786 | 7.011 | 8.985 | −45.659 | 1.00 | 61.69 | C |
| ATOM | 5626 | CB | VAL A | 786 | 7.336 | 8.943 | −47.162 | 1.00 | 63.93 | C |
| ATOM | 5627 | CG1 | VAL A | 786 | 6.316 | 8.122 | −47.912 | 1.00 | 63.46 | C |
| ATOM | 5628 | CG2 | VAL A | 786 | 7.402 | 10.357 | −47.733 | 1.00 | 71.15 | C |
| ATOM | 5629 | C | VAL A | 786 | 5.531 | 9.416 | −45.414 | 1.00 | 58.42 | C |
| ATOM | 5630 | O | VAL A | 786 | 4.629 | 8.590 | −45.308 | 1.00 | 60.35 | O |
| ATOM | 5631 | N | GLU A | 787 | 5.288 | 10.721 | −45.350 | 1.00 | 52.26 | N |
| ATOM | 5632 | CA | GLU A | 787 | 3.967 | 11.226 | −44.983 | 1.00 | 52.42 | C |
| ATOM | 5633 | CB | GLU A | 787 | 4.097 | 12.562 | −44.235 | 1.00 | 56.71 | C |
| ATOM | 5634 | CG | GLU A | 787 | 3.195 | 12.797 | −43.041 | 1.00 | 58.96 | C |
| ATOM | 5635 | CD | GLU A | 787 | 3.957 | 13.389 | −41.875 | 1.00 | 65.62 | C |
| ATOM | 5636 | OE1 | GLU A | 787 | 3.714 | 14.571 | −41.498 | 1.00 | 70.37 | O |
| ATOM | 5637 | OE2 | GLU A | 787 | 4.813 | 12.644 | −41.332 | 1.00 | 71.05 | O |
| ATOM | 5638 | C | GLU A | 787 | 3.277 | 11.460 | −46.275 | 1.00 | 50.08 | C |
| ATOM | 5639 | O | GLU A | 787 | 3.921 | 11.845 | −47.221 | 1.00 | 52.66 | O |
| ATOM | 5640 | N | VAL A | 788 | 1.971 | 11.253 | −46.330 | 1.00 | 50.76 | N |
| ATOM | 5641 | CA | VAL A | 788 | 1.188 | 11.527 | −47.554 | 1.00 | 51.39 | C |
| ATOM | 5642 | CB | VAL A | 788 | 0.825 | 10.228 | −48.314 | 1.00 | 48.89 | C |
| ATOM | 5643 | CG1 | VAL A | 788 | −0.030 | 10.543 | −49.541 | 1.00 | 48.41 | C |
| ATOM | 5644 | CG2 | VAL A | 788 | 2.082 | 9.488 | −48.705 | 1.00 | 47.61 | C |
| ATOM | 5645 | C | VAL A | 788 | −0.118 | 12.216 | −47.218 | 1.00 | 51.76 | C |
| ATOM | 5646 | O | VAL A | 788 | −0.985 | 11.639 | −46.515 | 1.00 | 55.38 | O |
| ATOM | 5647 | N | HIS A | 789 | −0.296 | 13.406 | −47.755 | 1.00 | 48.71 | N |
| ATOM | 5648 | CA | HIS A | 789 | −1.401 | 14.218 | −47.308 | 1.00 | 53.19 | C |
| ATOM | 5649 | CB | HIS A | 789 | −0.962 | 15.649 | −47.173 | 1.00 | 55.97 | C |
| ATOM | 5650 | CG | HIS A | 789 | −0.003 | 15.836 | −46.057 | 1.00 | 58.74 | C |
| ATOM | 5651 | ND1 | HIS A | 789 | −0.176 | 16.788 | −45.088 | 1.00 | 62.78 | N |
| ATOM | 5652 | CE1 | HIS A | 789 | 0.823 | 16.721 | −44.228 | 1.00 | 62.85 | C |
| ATOM | 5653 | NE2 | HIS A | 789 | 1.616 | 15.731 | −44.585 | 1.00 | 60.30 | N |
| ATOM | 5654 | CD2 | HIS A | 789 | 1.113 | 15.150 | −45.720 | 1.00 | 60.58 | C |
| ATOM | 5655 | C | HIS A | 789 | −2.622 | 14.106 | −48.177 | 1.00 | 52.04 | C |
| ATOM | 5656 | O | HIS A | 789 | −2.515 | 13.854 | −49.369 | 1.00 | 54.55 | O |
| ATOM | 5657 | N | ASN A | 790 | −3.780 | 14.233 | −47.541 | 1.00 | 47.69 | N |
| ATOM | 5658 | CA | ASN A | 790 | −5.027 | 14.125 | −48.211 | 1.00 | 47.56 | C |
| ATOM | 5659 | CB | ASN A | 790 | −5.618 | 12.740 | −47.998 | 1.00 | 51.17 | C |
| ATOM | 5660 | CG | ASN A | 790 | −4.774 | 11.642 | −48.623 | 1.00 | 57.01 | C |
| ATOM | 5661 | OD1 | ASN A | 790 | −4.941 | 11.253 | −49.824 | 1.00 | 53.98 | O |
| ATOM | 5662 | ND2 | ASN A | 790 | −3.865 | 11.096 | −47.792 | 1.00 | 62.86 | N |
| ATOM | 5663 | C | ASN A | 790 | −6.007 | 15.126 | −47.702 | 1.00 | 45.62 | C |
| ATOM | 5664 | O | ASN A | 790 | −5.902 | 15.575 | −46.577 | 1.00 | 48.62 | O |

TABLE 6-continued

Atomic coordinates for CRBN:DDB1: Compound B (Human protein)

| ATOM | 5665 | N | LEU A | 791 | −6.992 | 15.439 | −48.524 | 1.00 | 42.73 | N |
|---|---|---|---|---|---|---|---|---|---|---|
| ATOM | 5666 | CA | LEU A | 791 | −8.118 | 16.175 | −48.091 | 1.00 | 42.70 | C |
| ATOM | 5667 | CB | LEU A | 791 | −8.318 | 17.420 | −48.943 | 1.00 | 44.67 | C |
| ATOM | 5668 | CG | LEU A | 791 | −9.674 | 18.127 | −48.718 | 1.00 | 46.67 | C |
| ATOM | 5669 | CD1 | LEU A | 791 | −9.908 | 18.595 | −47.280 | 1.00 | 46.84 | C |
| ATOM | 5670 | CD2 | LEU A | 791 | −9.757 | 19.307 | −49.644 | 1.00 | 48.11 | C |
| ATOM | 5671 | C | LEU A | 791 | −9.293 | 15.230 | −48.199 | 1.00 | 42.77 | C |
| ATOM | 5672 | O | LEU A | 791 | −9.798 | 15.001 | −49.274 | 1.00 | 41.71 | O |
| ATOM | 5673 | N | LEU A | 792 | −9.743 | 14.715 | −47.062 | 1.00 | 43.09 | N |
| ATOM | 5674 | CA | LEU A | 792 | −10.933 | 13.886 | −47.010 | 1.00 | 43.95 | C |
| ATOM | 5675 | CB | LEU A | 792 | −10.991 | 13.067 | −45.722 | 1.00 | 42.52 | C |
| ATOM | 5676 | CG | LEU A | 792 | −9.746 | 12.285 | −45.361 | 1.00 | 43.99 | C |
| ATOM | 5677 | CD1 | LEU A | 792 | −9.949 | 11.581 | −44.024 | 1.00 | 44.27 | C |
| ATOM | 5678 | CD2 | LEU A | 792 | −9.416 | 11.307 | −46.469 | 1.00 | 45.32 | C |
| ATOM | 5679 | C | LEU A | 792 | −12.184 | 14.768 | −47.088 | 1.00 | 45.74 | C |
| ATOM | 5680 | O | LEU A | 792 | −12.141 | 15.918 | −46.693 | 1.00 | 47.28 | O |
| ATOM | 5681 | N | ILE A | 793 | −13.289 | 14.193 | −47.562 | 1.00 | 45.59 | N |
| ATOM | 5682 | CA | ILE A | 793 | −14.574 | 14.835 | −47.578 | 1.00 | 46.09 | C |
| ATOM | 5683 | CB | ILE A | 793 | −15.026 | 15.154 | −49.003 | 1.00 | 46.84 | C |
| ATOM | 5684 | CG1 | ILE A | 793 | −13.965 | 16.021 | −49.680 | 1.00 | 47.90 | C |
| ATOM | 5685 | CD1 | ILE A | 793 | −13.778 | 17.398 | −49.073 | 1.00 | 49.84 | C |
| ATOM | 5686 | CG2 | ILE A | 793 | −16.418 | 15.802 | −49.008 | 1.00 | 45.71 | C |
| ATOM | 5687 | C | ILE A | 793 | −15.502 | 13.841 | −47.003 | 1.00 | 46.62 | C |
| ATOM | 5688 | O | ILE A | 793 | −15.635 | 12.781 | −47.565 | 1.00 | 53.06 | O |
| ATOM | 5689 | N | ILE A | 794 | −16.153 | 14.185 | −45.903 | 1.00 | 46.41 | N |
| ATOM | 5690 | CA | ILE A | 794 | −16.775 | 13.196 | −45.037 | 1.00 | 45.57 | C |
| ATOM | 5691 | CB | ILE A | 794 | −15.939 | 13.064 | −43.758 | 1.00 | 44.49 | C |
| ATOM | 5692 | CG1 | ILE A | 794 | −14.608 | 12.444 | −44.159 | 1.00 | 45.90 | C |
| ATOM | 5693 | CD1 | ILE A | 794 | −13.656 | 12.171 | −43.035 | 1.00 | 47.13 | C |
| ATOM | 5694 | CG2 | ILE A | 794 | −16.601 | 12.174 | −42.743 | 1.00 | 43.64 | C |
| ATOM | 5695 | C | ILE A | 794 | −18.221 | 13.557 | −44.782 | 1.00 | 47.65 | C |
| ATOM | 5696 | O | ILE A | 794 | −18.574 | 14.692 | −44.553 | 1.00 | 48.49 | O |
| ATOM | 5697 | N | ASP A | 795 | −19.092 | 12.579 | −44.858 | 1.00 | 53.49 | N |
| ATOM | 5698 | CA | ASP A | 795 | −20.507 | 12.887 | −44.818 | 1.00 | 56.81 | C |
| ATOM | 5699 | CB | ASP A | 795 | −21.363 | 11.652 | −45.151 | 1.00 | 60.10 | C |
| ATOM | 5700 | CG | ASP A | 795 | −22.771 | 12.031 | −45.480 | 1.00 | 63.62 | C |
| ATOM | 5701 | OD1 | ASP A | 795 | −22.935 | 12.533 | −46.594 | 1.00 | 66.51 | O |
| ATOM | 5702 | OD2 | ASP A | 795 | −23.684 | 11.907 | −44.634 | 1.00 | 64.19 | O |
| ATOM | 5703 | C | ASP A | 795 | −20.884 | 13.422 | −43.441 | 1.00 | 55.44 | C |
| ATOM | 5704 | O | ASP A | 795 | −20.482 | 12.884 | −42.389 | 1.00 | 51.95 | O |
| ATOM | 5705 | N | GLN A | 796 | −21.668 | 14.479 | −43.461 | 1.00 | 54.74 | N |
| ATOM | 5706 | CA | GLN A | 796 | −22.214 | 15.045 | −42.225 | 1.00 | 55.31 | C |
| ATOM | 5707 | CB | GLN A | 796 | −23.069 | 16.261 | −42.557 | 1.00 | 55.91 | C |
| ATOM | 5708 | CG | GLN A | 796 | −24.283 | 16.460 | −41.697 | 1.00 | 58.45 | C |
| ATOM | 5709 | CD | GLN A | 796 | −24.773 | 17.864 | −41.749 | 1.00 | 59.07 | C |
| ATOM | 5710 | OE1 | GLN A | 796 | −25.444 | 18.319 | −40.830 | 1.00 | 65.50 | O |
| ATOM | 5711 | NE2 | GLN A | 796 | −24.457 | 18.557 | −42.808 | 1.00 | 58.50 | N |
| ATOM | 5712 | C | GLN A | 796 | −23.004 | 14.101 | −41.341 | 1.00 | 54.48 | C |
| ATOM | 5713 | O | GLN A | 796 | −22.821 | 14.148 | −40.117 | 1.00 | 51.06 | O |
| ATOM | 5714 | N | HIS A | 797 | −23.899 | 13.300 | −41.941 | 1.00 | 58.39 | N |
| ATOM | 5715 | CA | HIS A | 797 | −24.810 | 12.380 | −41.174 | 1.00 | 62.66 | C |
| ATOM | 5716 | CB | HIS A | 797 | −26.150 | 12.161 | −41.855 | 1.00 | 63.23 | C |
| ATOM | 5717 | CG | HIS A | 797 | −26.806 | 13.430 | −42.260 | 1.00 | 66.95 | C |
| ATOM | 5718 | ND1 | HIS A | 797 | −27.515 | 14.210 | −41.376 | 1.00 | 68.45 | N |
| ATOM | 5719 | CE1 | HIS A | 797 | −27.964 | 15.282 | −42.002 | 1.00 | 73.46 | C |
| ATOM | 5720 | NE2 | HIS A | 797 | −27.548 | 15.238 | −43.254 | 1.00 | 75.02 | N |
| ATOM | 5721 | CD2 | HIS A | 797 | −26.815 | 14.089 | −43.440 | 1.00 | 72.22 | C |
| ATOM | 5722 | C | HIS A | 797 | −24.224 | 11.028 | −40.907 | 1.00 | 61.00 | C |
| ATOM | 5723 | O | HIS A | 797 | −24.380 | 10.504 | −39.813 | 1.00 | 62.71 | O |
| ATOM | 5724 | N | THR A | 798 | −23.527 | 10.488 | −41.898 | 1.00 | 62.08 | N |
| ATOM | 5725 | CA | THR A | 798 | −23.019 | 9.108 | −41.852 | 1.00 | 60.92 | C |
| ATOM | 5726 | CB | THR A | 798 | −23.367 | 8.360 | −43.156 | 1.00 | 62.43 | C |
| ATOM | 5727 | OG1 | THR A | 798 | −22.286 | 8.431 | −44.097 | 1.00 | 65.22 | O |
| ATOM | 5728 | CG2 | THR A | 798 | −24.612 | 8.952 | −43.828 | 1.00 | 65.14 | C |
| ATOM | 5729 | C | THR A | 798 | −21.499 | 9.000 | −41.621 | 1.00 | 59.25 | C |
| ATOM | 5730 | O | THR A | 798 | −21.048 | 7.928 | −41.341 | 1.00 | 58.16 | O |
| ATOM | 5731 | N | PHE A | 799 | −20.717 | 10.085 | −41.784 | 1.00 | 57.94 | N |
| ATOM | 5732 | CA | PHE A | 799 | −19.241 | 10.069 | −41.685 | 1.00 | 54.55 | C |
| ATOM | 5733 | CB | PHE A | 799 | −18.767 | 10.003 | −40.202 | 1.00 | 56.68 | C |
| ATOM | 5734 | CG | PHE A | 799 | −19.213 | 11.192 | −39.406 | 1.00 | 57.35 | C |
| ATOM | 5735 | CD1 | PHE A | 799 | −20.486 | 11.222 | −38.836 | 1.00 | 57.85 | C |
| ATOM | 5736 | CE1 | PHE A | 799 | −20.932 | 12.337 | −38.171 | 1.00 | 55.63 | C |
| ATOM | 5737 | CZ | PHE A | 799 | −20.118 | 13.459 | −38.090 | 1.00 | 56.96 | C |
| ATOM | 5738 | CE2 | PHE A | 799 | −18.865 | 13.461 | −38.665 | 1.00 | 57.37 | C |
| ATOM | 5739 | CD2 | PHE A | 799 | −18.418 | 12.326 | −39.323 | 1.00 | 58.29 | C |
| ATOM | 5740 | C | PHE A | 799 | −18.600 | 9.007 | −42.558 | 1.00 | 54.26 | C |
| ATOM | 5741 | O | PHE A | 799 | −17.567 | 8.425 | −42.220 | 1.00 | 51.07 | O |
| ATOM | 5742 | N | GLU A | 800 | −19.211 | 8.777 | −43.712 | 1.00 | 60.23 | N |

TABLE 6-continued

Atomic coordinates for CRBN:DDB1: Compound B (Human protein)

| ATOM | 5743 | CA | GLU A | 800 | −18.556 | 8.009 | −44.764 | 1.00 | 68.41 | C |
|---|---|---|---|---|---|---|---|---|---|---|
| ATOM | 5744 | CB | GLU A | 800 | −19.555 | 7.411 | −45.789 | 1.00 | 80.31 | C |
| ATOM | 5745 | CG | GLU A | 800 | −19.603 | 5.863 | −45.900 | 1.00 | 88.45 | C |
| ATOM | 5746 | CD | GLU A | 800 | −19.614 | 5.377 | −47.370 | 1.00 | 90.36 | C |
| ATOM | 5747 | OE1 | GLU A | 800 | −20.289 | 6.037 | −48.200 | 1.00 | 86.61 | O |
| ATOM | 5748 | OE2 | GLU A | 800 | −18.935 | 4.359 | −47.707 | 1.00 | 85.42 | O |
| ATOM | 5749 | C | GLU A | 800 | −17.553 | 8.935 | −45.464 | 1.00 | 62.73 | C |
| ATOM | 5750 | O | GLU A | 800 | −17.834 | 10.105 | −45.760 | 1.00 | 58.09 | O |
| ATOM | 5751 | N | VAL A | 801 | −16.369 | 8.402 | −45.700 | 1.00 | 58.01 | N |
| ATOM | 5752 | CA | VAL A | 801 | −15.394 | 9.096 | −46.499 | 1.00 | 54.54 | C |
| ATOM | 5753 | CB | VAL A | 801 | −14.007 | 8.437 | −46.352 | 1.00 | 52.29 | C |
| ATOM | 5754 | CG1 | VAL A | 801 | −12.972 | 9.223 | −47.109 | 1.00 | 52.85 | C |
| ATOM | 5755 | CG2 | VAL A | 801 | −13.587 | 8.343 | −44.894 | 1.00 | 51.15 | C |
| ATOM | 5756 | C | VAL A | 801 | −15.939 | 9.006 | −47.944 | 1.00 | 56.13 | C |
| ATOM | 5757 | O | VAL A | 801 | −15.950 | 7.922 | −48.565 | 1.00 | 60.10 | O |
| ATOM | 5758 | N | LEU A | 802 | −16.444 | 10.129 | −48.449 | 1.00 | 54.98 | N |
| ATOM | 5759 | CA | LEU A | 802 | −16.978 | 10.195 | −49.800 | 1.00 | 54.94 | C |
| ATOM | 5760 | CB | LEU A | 802 | −17.966 | 11.345 | −49.940 | 1.00 | 54.17 | C |
| ATOM | 5761 | CG | LEU A | 802 | −19.078 | 11.454 | −48.888 | 1.00 | 55.94 | C |
| ATOM | 5762 | CD1 | LEU A | 802 | −20.185 | 12.450 | −49.248 | 1.00 | 56.09 | C |
| ATOM | 5763 | CD2 | LEU A | 802 | −19.697 | 10.105 | −48.588 | 1.00 | 56.99 | C |
| ATOM | 5764 | C | LEU A | 802 | −15.871 | 10.339 | −50.838 | 1.00 | 59.61 | C |
| ATOM | 5765 | O | LEU A | 802 | −15.995 | 9.779 | −51.913 | 1.00 | 64.08 | O |
| ATOM | 5766 | N | HIS A | 803 | −14.811 | 11.100 | −50.544 | 1.00 | 62.83 | N |
| ATOM | 5767 | CA | HIS A | 803 | −13.700 | 11.321 | −51.513 | 1.00 | 64.37 | C |
| ATOM | 5768 | CB | HIS A | 803 | −14.055 | 12.500 | −52.427 | 1.00 | 67.66 | C |
| ATOM | 5769 | CG | HIS A | 803 | −13.112 | 12.729 | −53.568 | 1.00 | 69.85 | C |
| ATOM | 5770 | ND1 | HIS A | 803 | −13.495 | 12.569 | −54.880 | 1.00 | 71.24 | N |
| ATOM | 5771 | CE1 | HIS A | 803 | −12.480 | 12.869 | −55.673 | 1.00 | 72.28 | C |
| ATOM | 5772 | NE2 | HIS A | 803 | −11.464 | 13.253 | −54.925 | 1.00 | 73.19 | N |
| ATOM | 5773 | CD2 | HIS A | 803 | −11.838 | 13.190 | −53.604 | 1.00 | 72.67 | C |
| ATOM | 5774 | C | HIS A | 803 | −12.410 | 11.624 | −50.768 | 1.00 | 60.62 | C |
| ATOM | 5775 | O | HIS A | 803 | −12.456 | 12.204 | −49.706 | 1.00 | 59.28 | O |
| ATOM | 5776 | N | ALA A | 804 | −11.277 | 11.218 | −51.324 | 1.00 | 57.73 | N |
| ATOM | 5777 | CA | ALA A | 804 | −9.963 | 11.512 | −50.769 | 1.00 | 57.73 | C |
| ATOM | 5778 | CB | ALA A | 804 | −9.348 | 10.245 | −50.235 | 1.00 | 58.29 | C |
| ATOM | 5779 | C | ALA A | 804 | −9.068 | 12.084 | −51.866 | 1.00 | 59.60 | C |
| ATOM | 5780 | O | ALA A | 804 | −8.756 | 11.399 | −52.834 | 1.00 | 65.60 | O |
| ATOM | 5781 | N | HIS A | 805 | −8.670 | 13.339 | −51.733 | 1.00 | 57.63 | N |
| ATOM | 5782 | CA | HIS A | 805 | −7.807 | 13.962 | −52.715 | 1.00 | 56.41 | C |
| ATOM | 5783 | CB | HIS A | 805 | −8.226 | 15.403 | −52.976 | 1.00 | 55.50 | C |
| ATOM | 5784 | CG | HIS A | 805 | −7.258 | 16.148 | −53.832 | 1.00 | 55.80 | C |
| ATOM | 5785 | ND1 | HIS A | 805 | −7.362 | 16.186 | −55.201 | 1.00 | 54.75 | N |
| ATOM | 5786 | CE1 | HIS A | 805 | −6.359 | 16.887 | −55.698 | 1.00 | 57.39 | C |
| ATOM | 5787 | NE2 | HIS A | 805 | −5.593 | 17.286 | −54.704 | 1.00 | 59.28 | N |
| ATOM | 5788 | CD2 | HIS A | 805 | −6.129 | 16.827 | −53.522 | 1.00 | 59.73 | C |
| ATOM | 5789 | C | HIS A | 805 | −6.395 | 13.937 | −52.170 | 1.00 | 55.74 | C |
| ATOM | 5790 | O | HIS A | 805 | −6.176 | 14.451 | −51.116 | 1.00 | 58.65 | O |
| ATOM | 5791 | N | GLN A | 806 | −5.448 | 13.374 | −52.915 | 1.00 | 55.03 | N |
| ATOM | 5792 | CA | GLN A | 806 | −4.044 | 13.303 | −52.528 | 1.00 | 53.03 | C |
| ATOM | 5793 | CB | GLN A | 806 | −3.457 | 12.074 | −53.144 | 1.00 | 51.59 | C |
| ATOM | 5794 | CG | GLN A | 806 | −2.088 | 11.736 | −52.631 | 1.00 | 53.27 | C |
| ATOM | 5795 | CD | GLN A | 806 | −1.782 | 10.248 | −52.812 | 1.00 | 56.09 | C |
| ATOM | 5796 | OE1 | GLN A | 806 | −2.481 | 9.340 | −52.278 | 1.00 | 55.12 | O |
| ATOM | 5797 | NE2 | GLN A | 806 | −0.738 | 9.983 | −53.571 | 1.00 | 55.85 | N |
| ATOM | 5798 | C | GLN A | 806 | −3.260 | 14.501 | −53.042 | 1.00 | 56.30 | C |
| ATOM | 5799 | O | GLN A | 806 | −3.296 | 14.789 | −54.233 | 1.00 | 62.61 | O |
| ATOM | 5800 | N | PHE A | 807 | −2.548 | 15.206 | −52.169 | 1.00 | 54.27 | N |
| ATOM | 5801 | CA | PHE A | 807 | −1.707 | 16.333 | −52.597 | 1.00 | 51.89 | C |
| ATOM | 5802 | CB | PHE A | 807 | −1.500 | 17.286 | −51.391 | 1.00 | 51.23 | C |
| ATOM | 5803 | CG | PHE A | 807 | −2.764 | 18.011 | −50.990 | 1.00 | 49.52 | C |
| ATOM | 5804 | CD1 | PHE A | 807 | −3.151 | 19.177 | −51.645 | 1.00 | 48.06 | C |
| ATOM | 5805 | CE1 | PHE A | 807 | −4.339 | 19.821 | −51.336 | 1.00 | 46.58 | C |
| ATOM | 5806 | CZ | PHE A | 807 | −5.147 | 19.321 | −50.334 | 1.00 | 48.58 | C |
| ATOM | 5807 | CE2 | PHE A | 807 | −4.780 | 18.162 | −49.667 | 1.00 | 49.62 | C |
| ATOM | 5808 | CD2 | PHE A | 807 | −3.596 | 17.503 | −50.005 | 1.00 | 50.01 | C |
| ATOM | 5809 | C | PHE A | 807 | −0.405 | 15.792 | −53.299 | 1.00 | 52.52 | C |
| ATOM | 5810 | O | PHE A | 807 | −0.267 | 14.584 | −53.459 | 1.00 | 48.56 | O |
| ATOM | 5811 | N | LEU A | 808 | 0.520 | 16.660 | −53.737 | 1.00 | 55.32 | N |
| ATOM | 5812 | CA | LEU A | 808 | 1.727 | 16.241 | −54.533 | 1.00 | 55.66 | C |
| ATOM | 5813 | CB | LEU A | 808 | 2.496 | 17.415 | −55.181 | 1.00 | 55.50 | C |
| ATOM | 5814 | CG | LEU A | 808 | 1.619 | 18.398 | −55.991 | 1.00 | 57.35 | C |
| ATOM | 5815 | CD1 | LEU A | 808 | 2.229 | 19.782 | −56.170 | 1.00 | 54.58 | C |
| ATOM | 5816 | CD2 | LEU A | 808 | 1.199 | 17.808 | −57.320 | 1.00 | 61.03 | C |
| ATOM | 5817 | C | LEU A | 808 | 2.685 | 15.433 | −53.698 | 1.00 | 55.47 | C |
| ATOM | 5818 | O | LEU A | 808 | 2.459 | 15.276 | −52.494 | 1.00 | 55.75 | O |
| ATOM | 5819 | N | GLN A | 809 | 3.699 | 14.853 | −54.350 | 1.00 | 58.31 | N |
| ATOM | 5820 | CA | GLN A | 809 | 4.742 | 14.089 | −53.643 | 1.00 | 62.19 | C |

TABLE 6-continued

Atomic coordinates for CRBN:DDB1: Compound B (Human protein)

| ATOM | 5821 | CB  | GLN A | 809 | 5.581   | 13.157 | −54.570 | 1.00 | 60.74 | C |
| ---- | ---- | --- | ----- | --- | ------- | ------ | ------- | ---- | ----- | - |
| ATOM | 5822 | C   | GLN A | 809 | 5.518   | 15.249 | −53.031 | 1.00 | 60.46 | C |
| ATOM | 5823 | O   | GLN A | 809 | 5.634   | 16.286 | −53.692 | 1.00 | 61.74 | O |
| ATOM | 5824 | N   | ASN A | 810 | 5.927   | 15.106 | −51.761 | 1.00 | 57.58 | N |
| ATOM | 5825 | CA  | ASN A | 810 | 6.502   | 16.189 | −50.943 | 1.00 | 58.63 | C |
| ATOM | 5826 | CB  | ASN A | 810 | 7.769   | 16.794 | −51.613 | 1.00 | 63.62 | C |
| ATOM | 5827 | CG  | ASN A | 810 | 8.964   | 15.875 | −51.572 | 1.00 | 65.03 | C |
| ATOM | 5828 | OD1 | ASN A | 810 | 9.510   | 15.563 | −52.605 | 1.00 | 67.62 | O |
| ATOM | 5829 | ND2 | ASN A | 810 | 9.393   | 15.463 | −50.379 | 1.00 | 70.25 | N |
| ATOM | 5830 | C   | ASN A | 810 | 5.582   | 17.369 | −50.461 | 1.00 | 53.81 | C |
| ATOM | 5831 | O   | ASN A | 810 | 6.003   | 18.191 | −49.648 | 1.00 | 53.95 | O |
| ATOM | 5832 | N   | GLU A | 811 | 4.362   | 17.483 | −50.935 | 1.00 | 51.67 | N |
| ATOM | 5833 | CA  | GLU A | 811 | 3.492   | 18.591 | −50.516 | 1.00 | 52.35 | C |
| ATOM | 5834 | CB  | GLU A | 811 | 2.426   | 18.840 | −51.584 | 1.00 | 51.30 | C |
| ATOM | 5835 | CG  | GLU A | 811 | 1.505   | 19.985 | −51.256 | 1.00 | 54.99 | C |
| ATOM | 5836 | CD  | GLU A | 811 | 0.629   | 20.359 | −52.424 | 1.00 | 56.90 | C |
| ATOM | 5837 | OE1 | GLU A | 811 | 0.319   | 19.432 | −53.168 | 1.00 | 58.35 | O |
| ATOM | 5838 | OE2 | GLU A | 811 | 0.208   | 21.539 | −52.596 | 1.00 | 55.53 | O |
| ATOM | 5839 | C   | GLU A | 811 | 2.859   | 18.330 | −49.110 | 1.00 | 52.32 | C |
| ATOM | 5840 | O   | GLU A | 811 | 2.327   | 17.241 | −48.826 | 1.00 | 46.84 | O |
| ATOM | 5841 | N   | TYR A | 812 | 2.935   | 19.348 | −48.242 | 1.00 | 55.42 | N |
| ATOM | 5842 | CA  | TYR A | 812 | 2.545   | 19.239 | −46.827 | 1.00 | 55.12 | C |
| ATOM | 5843 | CB  | TYR A | 812 | 3.717   | 19.609 | −45.921 | 1.00 | 55.19 | C |
| ATOM | 5844 | CG  | TYR A | 812 | 3.525   | 19.123 | −44.513 | 1.00 | 62.10 | C |
| ATOM | 5845 | CD1 | TYR A | 812 | 2.579   | 19.745 | −43.667 | 1.00 | 67.69 | C |
| ATOM | 5846 | CE1 | TYR A | 812 | 2.363   | 19.313 | −42.351 | 1.00 | 68.73 | C |
| ATOM | 5847 | CZ  | TYR A | 812 | 3.103   | 18.242 | −41.856 | 1.00 | 68.65 | C |
| ATOM | 5848 | OH  | TYR A | 812 | 2.840   | 17.843 | −40.561 | 1.00 | 63.55 | O |
| ATOM | 5849 | CE2 | TYR A | 812 | 4.061   | 17.594 | −42.686 | 1.00 | 66.74 | C |
| ATOM | 5850 | CD2 | TYR A | 812 | 4.258   | 18.028 | −44.004 | 1.00 | 61.76 | C |
| ATOM | 5851 | C   | TYR A | 812 | 1.386   | 20.174 | −46.625 | 1.00 | 53.21 | C |
| ATOM | 5852 | O   | TYR A | 812 | 1.538   | 21.377 | −46.761 | 1.00 | 59.16 | O |
| ATOM | 5853 | N   | ALA A | 813 | 0.203   | 19.627 | −46.395 | 1.00 | 50.39 | N |
| ATOM | 5854 | CA  | ALA A | 813 | −1.001  | 20.458 | −46.190 | 1.00 | 48.95 | C |
| ATOM | 5855 | CB  | ALA A | 813 | −2.288  | 19.676 | −46.411 | 1.00 | 48.34 | C |
| ATOM | 5856 | C   | ALA A | 813 | −0.992  | 21.042 | −44.798 | 1.00 | 47.62 | C |
| ATOM | 5857 | O   | ALA A | 813 | −0.871  | 20.344 | −43.800 | 1.00 | 45.13 | O |
| ATOM | 5858 | N   | LEU A | 814 | −1.120  | 22.345 | −44.758 | 1.00 | 47.61 | N |
| ATOM | 5859 | CA  | LEU A | 814 | −1.043  | 23.060 | −43.536 | 1.00 | 46.14 | C |
| ATOM | 5860 | CB  | LEU A | 814 | 0.015   | 24.138 | −43.655 | 1.00 | 47.82 | C |
| ATOM | 5861 | CG  | LEU A | 814 | 1.450   | 23.659 | −43.720 | 1.00 | 48.19 | C |
| ATOM | 5862 | CD1 | LEU A | 814 | 2.390   | 24.830 | −44.004 | 1.00 | 49.56 | C |
| ATOM | 5863 | CD2 | LEU A | 814 | 1.782   | 23.007 | −42.401 | 1.00 | 48.71 | C |
| ATOM | 5864 | C   | LEU A | 814 | −2.369  | 23.659 | −43.164 | 1.00 | 43.13 | C |
| ATOM | 5865 | O   | LEU A | 814 | −2.722  | 23.544 | −42.021 | 1.00 | 44.94 | O |
| ATOM | 5866 | N   | SER A | 815 | −3.095  | 24.293 | −44.077 | 1.00 | 40.62 | N |
| ATOM | 5867 | CA  | SER A | 815 | −4.268  | 25.086 | −43.676 | 1.00 | 44.24 | C |
| ATOM | 5868 | CB  | SER A | 815 | −3.979  | 26.587 | −43.840 | 1.00 | 44.65 | C |
| ATOM | 5869 | OG  | SER A | 815 | −2.707  | 26.805 | −44.423 | 1.00 | 44.65 | O |
| ATOM | 5870 | C   | SER A | 815 | −5.527  | 24.725 | −44.440 | 1.00 | 47.11 | C |
| ATOM | 5871 | O   | SER A | 815 | −5.460  | 24.279 | −45.584 | 1.00 | 49.45 | O |
| ATOM | 5872 | N   | LEU A | 816 | −6.683  | 24.920 | −43.829 | 1.00 | 46.03 | N |
| ATOM | 5873 | CA  | LEU A | 816 | −7.903  | 24.599 | −44.533 | 1.00 | 45.48 | C |
| ATOM | 5874 | CB  | LEU A | 816 | −8.314  | 23.193 | −44.195 | 1.00 | 45.49 | C |
| ATOM | 5875 | CG  | LEU A | 816 | −9.739  | 22.844 | −44.577 | 1.00 | 46.48 | C |
| ATOM | 5876 | CD1 | LEU A | 816 | −9.822  | 22.382 | −46.018 | 1.00 | 47.64 | C |
| ATOM | 5877 | CD2 | LEU A | 816 | −10.214 | 21.734 | −43.683 | 1.00 | 50.38 | C |
| ATOM | 5878 | C   | LEU A | 816 | −8.968  | 25.555 | −44.112 | 1.00 | 47.39 | C |
| ATOM | 5879 | O   | LEU A | 816 | −9.050  | 25.880 | −42.947 | 1.00 | 50.40 | O |
| ATOM | 5880 | N   | VAL A | 817 | −9.774  | 26.010 | −45.063 | 1.00 | 49.45 | N |
| ATOM | 5881 | CA  | VAL A | 817 | −10.987 | 26.774 | −44.779 | 1.00 | 52.19 | C |
| ATOM | 5882 | CB  | VAL A | 817 | −10.696 | 28.294 | −44.769 | 1.00 | 53.45 | C |
| ATOM | 5883 | CG1 | VAL A | 817 | −10.253 | 28.772 | −46.112 | 1.00 | 53.48 | C |
| ATOM | 5884 | CG2 | VAL A | 817 | −11.926 | 29.081 | −44.337 | 1.00 | 58.84 | C |
| ATOM | 5885 | C   | VAL A | 817 | −12.084 | 26.381 | −45.788 | 1.00 | 50.57 | C |
| ATOM | 5886 | O   | VAL A | 817 | −11.787 | 25.785 | −46.809 | 1.00 | 48.41 | O |
| ATOM | 5887 | N   | SER A | 818 | −13.341 | 26.645 | −45.463 | 1.00 | 50.46 | N |
| ATOM | 5888 | CA  | SER A | 818 | −14.433 | 26.509 | −46.407 | 1.00 | 51.46 | C |
| ATOM | 5889 | CB  | SER A | 818 | −15.363 | 25.326 | −46.058 | 1.00 | 52.17 | C |
| ATOM | 5890 | OG  | SER A | 818 | −16.761 | 25.596 | −46.385 | 1.00 | 51.39 | O |
| ATOM | 5891 | C   | SER A | 818 | −15.234 | 27.792 | −46.383 | 1.00 | 52.93 | C |
| ATOM | 5892 | O   | SER A | 818 | −15.948 | 28.035 | −45.424 | 1.00 | 53.61 | O |
| ATOM | 5893 | N   | CYS A | 819 | −15.180 | 28.553 | −47.469 | 1.00 | 55.91 | N |
| ATOM | 5894 | CA  | CYS A | 819 | −15.886 | 29.816 | −47.593 | 1.00 | 57.78 | C |
| ATOM | 5895 | CB  | CYS A | 819 | −14.969 | 30.902 | −47.073 | 1.00 | 58.01 | C |
| ATOM | 5896 | SG  | CYS A | 819 | −13.493 | 31.034 | −48.121 | 1.00 | 59.61 | S |
| ATOM | 5897 | C   | CYS A | 819 | −16.250 | 30.201 | −49.039 | 1.00 | 62.91 | C |
| ATOM | 5898 | O   | CYS A | 819 | −15.740 | 29.645 | −50.043 | 1.00 | 57.87 | O |

TABLE 6-continued

Atomic coordinates for CRBN:DDB1: Compound B (Human protein)

| ATOM | 5899 | N | LYS A | 820 | −17.103 | 31.225 | −49.084 | 1.00 | 67.80 | N |
|---|---|---|---|---|---|---|---|---|---|---|
| ATOM | 5900 | CA | LYS A | 820 | −17.545 | 31.930 | −50.289 | 1.00 | 65.44 | C |
| ATOM | 5901 | CB | LYS A | 820 | −19.010 | 32.424 | −50.097 | 1.00 | 65.06 | C |
| ATOM | 5902 | CG | LYS A | 820 | −20.130 | 31.605 | −50.765 | 1.00 | 64.54 | C |
| ATOM | 5903 | CD | LYS A | 820 | −21.357 | 31.232 | −49.925 | 1.00 | 68.95 | C |
| ATOM | 5904 | CE | LYS A | 820 | −21.779 | 32.166 | −48.787 | 1.00 | 74.12 | C |
| ATOM | 5905 | NZ | LYS A | 820 | −22.039 | 33.544 | −49.264 | 1.00 | 79.35 | N |
| ATOM | 5906 | C | LYS A | 820 | −16.610 | 33.128 | −50.457 | 1.00 | 64.36 | C |
| ATOM | 5907 | O | LYS A | 820 | −16.281 | 33.787 | −49.482 | 1.00 | 64.02 | O |
| ATOM | 5908 | N | LEU A | 821 | −16.199 | 33.419 | −51.685 | 1.00 | 68.88 | N |
| ATOM | 5909 | CA | LEU A | 821 | −15.368 | 34.616 | −51.957 | 1.00 | 68.86 | C |
| ATOM | 5910 | CB | LEU A | 821 | −13.965 | 34.228 | −52.448 | 1.00 | 62.41 | C |
| ATOM | 5911 | CG | LEU A | 821 | −13.159 | 33.310 | −51.548 | 1.00 | 57.87 | C |
| ATOM | 5912 | CD1 | LEU A | 821 | −11.825 | 33.017 | −52.198 | 1.00 | 56.01 | C |
| ATOM | 5913 | CD2 | LEU A | 821 | −12.933 | 33.950 | −50.200 | 1.00 | 60.69 | C |
| ATOM | 5914 | C | LEU A | 821 | −16.005 | 35.525 | −52.996 | 1.00 | 71.07 | C |
| ATOM | 5915 | O | LEU A | 821 | −16.634 | 35.044 | −53.949 | 1.00 | 74.13 | O |
| ATOM | 5916 | N | GLY A | 822 | −15.817 | 36.828 | −52.806 | 1.00 | 72.62 | N |
| ATOM | 5917 | CA | GLY A | 822 | −16.322 | 37.839 | −53.729 | 1.00 | 77.91 | C |
| ATOM | 5918 | C | GLY A | 822 | −17.753 | 37.632 | −54.215 | 1.00 | 77.23 | C |
| ATOM | 5919 | O | GLY A | 822 | −18.614 | 37.126 | −53.488 | 1.00 | 72.63 | O |
| ATOM | 5920 | N | LYS A | 823 | −17.987 | 37.974 | −55.477 | 1.00 | 79.48 | N |
| ATOM | 5921 | CA | LYS A | 823 | −19.320 | 37.886 | −56.068 | 1.00 | 80.02 | C |
| ATOM | 5922 | CB | LYS A | 823 | −19.367 | 38.702 | −57.371 | 1.00 | 84.37 | C |
| ATOM | 5923 | CG | LYS A | 823 | −19.142 | 40.215 | −57.190 | 1.00 | 86.79 | C |
| ATOM | 5924 | CD | LYS A | 823 | −20.430 | 40.985 | −56.882 | 1.00 | 88.01 | C |
| ATOM | 5925 | CE | LYS A | 823 | −20.199 | 42.192 | −55.969 | 1.00 | 89.19 | C |
| ATOM | 5926 | NZ | LYS A | 823 | −20.617 | 43.451 | −56.654 | 1.00 | 88.35 | N |
| ATOM | 5927 | C | LYS A | 823 | −19.776 | 36.420 | −56.290 | 1.00 | 77.26 | C |
| ATOM | 5928 | O | LYS A | 823 | −20.965 | 36.151 | −56.456 | 1.00 | 78.42 | O |
| ATOM | 5929 | N | ASP A | 824 | −18.843 | 35.476 | −56.232 | 1.00 | 70.81 | N |
| ATOM | 5930 | CA | ASP A | 824 | −19.139 | 34.072 | −56.459 | 1.00 | 66.44 | C |
| ATOM | 5931 | CB | ASP A | 824 | −17.846 | 33.285 | −56.413 | 1.00 | 65.77 | C |
| ATOM | 5932 | CG | ASP A | 824 | −17.906 | 32.033 | −57.224 | 1.00 | 65.45 | C |
| ATOM | 5933 | OD1 | ASP A | 824 | −19.006 | 31.442 | −57.337 | 1.00 | 59.97 | O |
| ATOM | 5934 | OD2 | ASP A | 824 | −16.823 | 31.634 | −57.731 | 1.00 | 64.15 | O |
| ATOM | 5935 | C | ASP A | 824 | −20.097 | 33.483 | −55.445 | 1.00 | 70.87 | C |
| ATOM | 5936 | O | ASP A | 824 | −19.888 | 33.650 | −54.249 | 1.00 | 75.82 | O |
| ATOM | 5937 | N | PRO A | 825 | −21.143 | 32.778 | −55.916 | 1.00 | 77.62 | N |
| ATOM | 5938 | CA | PRO A | 825 | −22.118 | 32.126 | −55.020 | 1.00 | 82.39 | C |
| ATOM | 5939 | CB | PRO A | 825 | −23.360 | 32.018 | −55.913 | 1.00 | 81.95 | C |
| ATOM | 5940 | CG | PRO A | 825 | −22.786 | 31.758 | −57.267 | 1.00 | 80.20 | C |
| ATOM | 5941 | CD | PRO A | 825 | −21.603 | 32.691 | −57.319 | 1.00 | 80.14 | C |
| ATOM | 5942 | C | PRO A | 825 | −21.721 | 30.717 | −54.561 | 1.00 | 79.75 | C |
| ATOM | 5943 | O | PRO A | 825 | −22.256 | 30.205 | −53.575 | 1.00 | 77.90 | O |
| ATOM | 5944 | N | ASN A | 826 | −20.841 | 30.089 | −55.324 | 1.00 | 76.76 | N |
| ATOM | 5945 | CA | ASN A | 826 | −20.296 | 28.811 | −54.964 | 1.00 | 77.12 | C |
| ATOM | 5946 | CB | ASN A | 826 | −19.384 | 28.306 | −56.093 | 1.00 | 78.14 | C |
| ATOM | 5947 | CG | ASN A | 826 | −20.150 | 27.688 | −57.235 | 1.00 | 75.11 | C |
| ATOM | 5948 | OD1 | ASN A | 826 | −21.338 | 27.389 | −57.134 | 1.00 | 67.95 | O |
| ATOM | 5949 | ND2 | ASN A | 826 | −19.452 | 27.452 | −58.320 | 1.00 | 78.56 | N |
| ATOM | 5950 | C | ASN A | 826 | −19.473 | 28.897 | −53.699 | 1.00 | 72.69 | C |
| ATOM | 5951 | O | ASN A | 826 | −18.844 | 29.941 | −53.451 | 1.00 | 83.09 | O |
| ATOM | 5952 | N | THR A | 827 | −19.462 | 27.788 | −52.952 | 1.00 | 64.96 | N |
| ATOM | 5953 | CA | THR A | 827 | −18.635 | 27.590 | −51.759 | 1.00 | 63.56 | C |
| ATOM | 5954 | CB | THR A | 827 | −19.498 | 27.000 | −50.637 | 1.00 | 64.72 | C |
| ATOM | 5955 | OG1 | THR A | 827 | −20.703 | 27.754 | −50.471 | 1.00 | 60.64 | O |
| ATOM | 5956 | CG2 | THR A | 827 | −18.730 | 26.976 | −49.349 | 1.00 | 70.73 | C |
| ATOM | 5957 | C | THR A | 827 | −17.451 | 26.603 | −51.993 | 1.00 | 61.56 | C |
| ATOM | 5958 | O | THR A | 827 | −17.635 | 25.537 | −52.501 | 1.00 | 64.04 | O |
| ATOM | 5959 | N | TYR A | 828 | −16.244 | 26.919 | −51.569 | 1.00 | 62.30 | N |
| ATOM | 5960 | CA | TYR A | 828 | −15.089 | 26.079 | −51.890 | 1.00 | 61.63 | C |
| ATOM | 5961 | CB | TYR A | 828 | −14.110 | 26.884 | −52.716 | 1.00 | 64.71 | C |
| ATOM | 5962 | CG | TYR A | 828 | −14.714 | 27.494 | −53.931 | 1.00 | 64.12 | C |
| ATOM | 5963 | CD1 | TYR A | 828 | −15.342 | 28.714 | −53.849 | 1.00 | 66.84 | C |
| ATOM | 5964 | CE1 | TYR A | 828 | −15.912 | 29.304 | −54.958 | 1.00 | 74.28 | C |
| ATOM | 5965 | CZ | TYR A | 828 | −15.845 | 28.658 | −56.196 | 1.00 | 73.86 | C |
| ATOM | 5966 | OH | TYR A | 828 | −16.415 | 29.252 | −57.312 | 1.00 | 68.16 | O |
| ATOM | 5967 | CE2 | TYR A | 828 | −15.200 | 27.435 | −56.296 | 1.00 | 70.20 | C |
| ATOM | 5968 | CD2 | TYR A | 828 | −14.643 | 26.864 | −55.162 | 1.00 | 66.68 | C |
| ATOM | 5969 | C | TYR A | 828 | −14.391 | 25.662 | −50.614 | 1.00 | 61.16 | C |
| ATOM | 5970 | O | TYR A | 828 | −14.582 | 26.283 | −49.591 | 1.00 | 64.16 | O |
| ATOM | 5971 | N | PHE A | 829 | −13.629 | 24.582 | −50.669 | 1.00 | 57.21 | N |
| ATOM | 5972 | CA | PHE A | 829 | −12.746 | 24.180 | −49.596 | 1.00 | 53.13 | C |
| ATOM | 5973 | CB | PHE A | 829 | −12.620 | 22.644 | −49.483 | 1.00 | 52.20 | C |
| ATOM | 5974 | CG | PHE A | 829 | −13.793 | 21.980 | −48.839 | 1.00 | 48.49 | C |
| ATOM | 5975 | CD1 | PHE A | 829 | −13.924 | 21.973 | −47.475 | 1.00 | 48.53 | C |
| ATOM | 5976 | CE1 | PHE A | 829 | −15.008 | 21.386 | −46.857 | 1.00 | 48.61 | C |

TABLE 6-continued

Atomic coordinates for CRBN:DDB1: Compound B (Human protein)

| ATOM | 5977 | CZ | PHE A | 829 | −15.965 | 20.766 | −47.608 | 1.00 | 50.24 | C |
|---|---|---|---|---|---|---|---|---|---|---|
| ATOM | 5978 | CE2 | PHE A | 829 | −15.829 | 20.747 | −48.990 | 1.00 | 51.44 | C |
| ATOM | 5979 | CD2 | PHE A | 829 | −14.738 | 21.359 | −49.588 | 1.00 | 48.74 | C |
| ATOM | 5980 | C | PHE A | 829 | −11.449 | 24.723 | −50.097 | 1.00 | 54.05 | C |
| ATOM | 5981 | O | PHE A | 829 | −11.067 | 24.392 | −51.207 | 1.00 | 56.70 | O |
| ATOM | 5982 | N | ILE A | 830 | −10.755 | 25.547 | −49.316 | 1.00 | 55.11 | N |
| ATOM | 5983 | CA | ILE A | 830 | −9.413 | 26.038 | −49.727 | 1.00 | 54.41 | C |
| ATOM | 5984 | CB | ILE A | 830 | −9.361 | 27.586 | −49.754 | 1.00 | 53.78 | C |
| ATOM | 5985 | CG1 | ILE A | 830 | −10.466 | 28.105 | −50.706 | 1.00 | 55.17 | C |
| ATOM | 5986 | CD1 | ILE A | 830 | −11.050 | 29.452 | −50.358 | 1.00 | 54.32 | C |
| ATOM | 5987 | CG2 | ILE A | 830 | −8.010 | 28.090 | −50.250 | 1.00 | 52.31 | C |
| ATOM | 5988 | C | ILE A | 830 | −8.350 | 25.383 | −48.841 | 1.00 | 51.19 | C |
| ATOM | 5989 | O | ILE A | 830 | −8.622 | 25.141 | −47.693 | 1.00 | 53.19 | O |
| ATOM | 5990 | N | VAL A | 831 | −7.182 | 25.047 | −49.391 | 1.00 | 47.40 | N |
| ATOM | 5991 | CA | VAL A | 831 | −6.082 | 24.491 | −48.631 | 1.00 | 46.02 | C |
| ATOM | 5992 | CB | VAL A | 831 | −5.814 | 23.048 | −49.055 | 1.00 | 46.03 | C |
| ATOM | 5993 | CG1 | VAL A | 831 | −4.636 | 22.419 | −48.280 | 1.00 | 45.49 | C |
| ATOM | 5994 | CG2 | VAL A | 831 | −7.077 | 22.241 | −48.881 | 1.00 | 47.38 | C |
| ATOM | 5995 | C | VAL A | 831 | −4.819 | 25.253 | −48.928 | 1.00 | 47.87 | C |
| ATOM | 5996 | O | VAL A | 831 | −4.464 | 25.358 | −50.070 | 1.00 | 57.64 | O |
| ATOM | 5997 | N | GLY A | 832 | −4.114 | 25.735 | −47.917 | 1.00 | 47.39 | N |
| ATOM | 5998 | CA | GLY A | 832 | −2.726 | 26.188 | −48.070 | 1.00 | 45.76 | C |
| ATOM | 5999 | C | GLY A | 832 | −1.742 | 25.048 | −47.828 | 1.00 | 44.54 | C |
| ATOM | 6000 | O | GLY A | 832 | −2.036 | 24.121 | −47.094 | 1.00 | 44.64 | O |
| ATOM | 6001 | N | THR A | 833 | −0.562 | 25.121 | −48.411 | 1.00 | 44.11 | N |
| ATOM | 6002 | CA | THR A | 833 | 0.362 | 23.996 | −48.376 | 1.00 | 49.07 | C |
| ATOM | 6003 | CB | THR A | 833 | 0.248 | 23.138 | −49.652 | 1.00 | 52.08 | C |
| ATOM | 6004 | OG1 | THR A | 833 | 0.685 | 23.914 | −50.777 | 1.00 | 52.28 | O |
| ATOM | 6005 | CG2 | THR A | 833 | −1.164 | 22.696 | −49.900 | 1.00 | 54.14 | C |
| ATOM | 6006 | C | THR A | 833 | 1.771 | 24.511 | −48.374 | 1.00 | 50.49 | C |
| ATOM | 6007 | O | THR A | 833 | 1.961 | 25.706 | −48.427 | 1.00 | 57.04 | O |
| ATOM | 6008 | N | ALA A | 834 | 2.751 | 23.612 | −48.334 | 1.00 | 48.99 | N |
| ATOM | 6009 | CA | ALA A | 834 | 4.147 | 23.961 | −48.338 | 1.00 | 48.47 | C |
| ATOM | 6010 | CB | ALA A | 834 | 4.623 | 24.160 | −46.926 | 1.00 | 48.59 | C |
| ATOM | 6011 | C | ALA A | 834 | 4.879 | 22.801 | −48.921 | 1.00 | 53.72 | C |
| ATOM | 6012 | O | ALA A | 834 | 4.431 | 21.667 | −48.814 | 1.00 | 58.72 | O |
| ATOM | 6013 | N | MET A | 835 | 6.033 | 23.067 | −49.498 | 1.00 | 56.20 | N |
| ATOM | 6014 | CA | MET A | 835 | 6.817 | 22.034 | −50.115 | 1.00 | 56.42 | C |
| ATOM | 6015 | CB | MET A | 835 | 7.254 | 22.462 | −51.525 | 1.00 | 62.35 | C |
| ATOM | 6016 | CG | MET A | 835 | 6.136 | 22.565 | −52.528 | 1.00 | 59.23 | C |
| ATOM | 6017 | SD | MET A | 835 | 5.548 | 20.918 | −52.885 | 1.00 | 60.98 | S |
| ATOM | 6018 | CE | MET A | 835 | 3.856 | 21.426 | −53.149 | 1.00 | 62.51 | C |
| ATOM | 6019 | C | MET A | 835 | 8.040 | 21.782 | −49.272 | 1.00 | 54.34 | C |
| ATOM | 6020 | O | MET A | 835 | 8.968 | 22.633 | −49.184 | 1.00 | 56.84 | O |
| ATOM | 6021 | N | VAL A | 836 | 8.072 | 20.569 | −48.758 | 1.00 | 49.75 | N |
| ATOM | 6022 | CA | VAL A | 836 | 9.029 | 20.173 | −47.791 | 1.00 | 52.32 | C |
| ATOM | 6023 | CB | VAL A | 836 | 8.320 | 19.431 | −46.650 | 1.00 | 53.34 | C |
| ATOM | 6024 | CG1 | VAL A | 836 | 9.300 | 19.098 | −45.517 | 1.00 | 52.56 | C |
| ATOM | 6025 | CG2 | VAL A | 836 | 7.148 | 20.269 | −46.177 | 1.00 | 54.57 | C |
| ATOM | 6026 | C | VAL A | 836 | 9.986 | 19.204 | −48.396 | 1.00 | 53.38 | C |
| ATOM | 6027 | O | VAL A | 836 | 9.576 | 18.140 | −48.829 | 1.00 | 53.62 | O |
| ATOM | 6028 | N | TYR A | 837 | 11.262 | 19.555 | −48.381 | 1.00 | 57.58 | N |
| ATOM | 6029 | CA | TYR A | 837 | 12.318 | 18.660 | −48.835 | 1.00 | 62.07 | C |
| ATOM | 6030 | CB | TYR A | 837 | 13.029 | 19.215 | −50.080 | 1.00 | 63.18 | C |
| ATOM | 6031 | CG | TYR A | 837 | 12.093 | 19.555 | −51.236 | 1.00 | 62.94 | C |
| ATOM | 6032 | CD1 | TYR A | 837 | 11.491 | 18.548 | −51.995 | 1.00 | 62.78 | C |
| ATOM | 6033 | CE1 | TYR A | 837 | 10.641 | 18.863 | −53.036 | 1.00 | 63.59 | C |
| ATOM | 6034 | CZ | TYR A | 837 | 10.373 | 20.187 | −53.314 | 1.00 | 63.91 | C |
| ATOM | 6035 | OH | TYR A | 837 | 9.529 | 20.498 | −54.337 | 1.00 | 70.94 | O |
| ATOM | 6036 | CE2 | TYR A | 837 | 10.934 | 21.197 | −52.573 | 1.00 | 60.70 | C |
| ATOM | 6037 | CD2 | TYR A | 837 | 11.790 | 20.880 | −51.546 | 1.00 | 60.19 | C |
| ATOM | 6038 | C | TYR A | 837 | 13.312 | 18.538 | −47.709 | 1.00 | 65.60 | C |
| ATOM | 6039 | O | TYR A | 837 | 13.631 | 19.531 | −47.090 | 1.00 | 68.40 | O |
| ATOM | 6040 | N | PRO A | 838 | 13.814 | 17.328 | −47.439 | 1.00 | 73.08 | N |
| ATOM | 6041 | CA | PRO A | 838 | 14.813 | 17.181 | −46.377 | 1.00 | 77.35 | C |
| ATOM | 6042 | CB | PRO A | 838 | 15.124 | 15.683 | −46.364 | 1.00 | 76.77 | C |
| ATOM | 6043 | CG | PRO A | 838 | 14.216 | 15.034 | −47.345 | 1.00 | 75.70 | C |
| ATOM | 6044 | CD | PRO A | 838 | 13.290 | 16.038 | −47.919 | 1.00 | 75.12 | C |
| ATOM | 6045 | C | PRO A | 838 | 16.114 | 17.996 | −46.552 | 1.00 | 84.56 | C |
| ATOM | 6046 | O | PRO A | 838 | 16.770 | 18.264 | −45.550 | 1.00 | 91.64 | O |
| ATOM | 6047 | N | GLU A | 839 | 16.477 | 18.387 | −47.778 | 1.00 | 88.27 | N |
| ATOM | 6048 | CA | GLU A | 839 | 17.608 | 19.319 | −47.996 | 1.00 | 93.59 | C |
| ATOM | 6049 | CB | GLU A | 839 | 17.969 | 19.490 | −49.499 | 1.00 | 99.76 | C |
| ATOM | 6050 | CG | GLU A | 839 | 18.031 | 18.231 | −50.363 | 1.00 | 106.49 | C |
| ATOM | 6051 | CD | GLU A | 839 | 16.802 | 18.041 | −51.252 | 1.00 | 109.63 | C |
| ATOM | 6052 | OE1 | GLU A | 839 | 15.886 | 17.290 | −50.835 | 1.00 | 108.62 | O |
| ATOM | 6053 | OE2 | GLU A | 839 | 16.751 | 18.644 | −52.353 | 1.00 | 108.06 | O |
| ATOM | 6054 | C | GLU A | 839 | 17.342 | 20.736 | −47.431 | 1.00 | 89.95 | C |

TABLE 6-continued

Atomic coordinates for CRBN:DDB1: Compound B (Human protein)

| ATOM | 6055 | O   | GLU A | 839 | 18.285 | 21.412 | −47.029 | 1.00 | 90.63  | O |
|------|------|-----|-------|-----|--------|--------|---------|------|--------|---|
| ATOM | 6056 | N   | GLU A | 840 | 16.065 | 21.150 | −47.413 | 1.00 | 84.95  | N |
| ATOM | 6057 | CA  | GLU A | 840 | 15.614 | 22.546 | −47.337 | 1.00 | 80.04  | C |
| ATOM | 6058 | CB  | GLU A | 840 | 14.552 | 22.762 | −48.442 | 1.00 | 86.66  | C |
| ATOM | 6059 | CG  | GLU A | 840 | 14.121 | 24.192 | −48.783 | 1.00 | 94.07  | C |
| ATOM | 6060 | CD  | GLU A | 840 | 12.870 | 24.235 | −49.692 | 1.00 | 106.67 | C |
| ATOM | 6061 | OE1 | GLU A | 840 | 11.774 | 23.710 | −49.326 | 1.00 | 110.19 | O |
| ATOM | 6062 | OE2 | GLU A | 840 | 12.969 | 24.804 | −50.804 | 1.00 | 119.58 | O |
| ATOM | 6063 | C   | GLU A | 840 | 15.011 | 22.818 | −45.958 | 1.00 | 72.45  | C |
| ATOM | 6064 | O   | GLU A | 840 | 14.036 | 22.161 | −45.560 | 1.00 | 76.87  | O |
| ATOM | 6065 | N   | ALA A | 841 | 15.577 | 23.781 | −45.229 | 1.00 | 64.83  | N |
| ATOM | 6066 | CA  | ALA A | 841 | 15.090 | 24.110 | −43.894 | 1.00 | 59.64  | C |
| ATOM | 6067 | CB  | ALA A | 841 | 16.157 | 24.811 | −43.074 | 1.00 | 57.24  | C |
| ATOM | 6068 | C   | ALA A | 841 | 13.790 | 24.905 | −43.957 | 1.00 | 59.20  | C |
| ATOM | 6069 | O   | ALA A | 841 | 12.752 | 24.343 | −43.690 | 1.00 | 61.55  | O |
| ATOM | 6070 | N   | GLU A | 842 | 13.840 | 26.186 | −44.322 | 1.00 | 64.03  | N |
| ATOM | 6071 | CA  | GLU A | 842 | 12.631 | 27.048 | −44.457 | 1.00 | 67.24  | C |
| ATOM | 6072 | CB  | GLU A | 842 | 12.938 | 28.567 | −44.319 | 1.00 | 73.55  | C |
| ATOM | 6073 | CG  | GLU A | 842 | 12.748 | 29.224 | −42.933 | 1.00 | 81.42  | C |
| ATOM | 6074 | CD  | GLU A | 842 | 13.995 | 30.018 | −42.470 | 1.00 | 93.08  | C |
| ATOM | 6075 | OE1 | GLU A | 842 | 14.843 | 30.330 | −43.376 | 1.00 | 83.43  | O |
| ATOM | 6076 | OE2 | GLU A | 842 | 14.139 | 30.305 | −41.214 | 1.00 | 91.85  | O |
| ATOM | 6077 | C   | GLU A | 842 | 12.065 | 26.783 | −45.846 | 1.00 | 63.82  | C |
| ATOM | 6078 | O   | GLU A | 842 | 12.768 | 26.898 | −46.839 | 1.00 | 62.48  | O |
| ATOM | 6079 | N   | PRO A | 843 | 10.808 | 26.411 | −45.932 | 1.00 | 63.20  | N |
| ATOM | 6080 | CA  | PRO A | 843 | 10.289 | 26.144 | −47.235 | 1.00 | 66.49  | C |
| ATOM | 6081 | CB  | PRO A | 843 | 8.921  | 25.514 | −46.949 | 1.00 | 72.95  | C |
| ATOM | 6082 | CG  | PRO A | 843 | 8.626  | 25.779 | −45.543 | 1.00 | 69.76  | C |
| ATOM | 6083 | CD  | PRO A | 843 | 9.964  | 25.827 | −44.898 | 1.00 | 69.06  | C |
| ATOM | 6084 | C   | PRO A | 843 | 10.141 | 27.370 | −48.102 | 1.00 | 66.00  | C |
| ATOM | 6085 | O   | PRO A | 843 | 9.668  | 28.407 | −47.648 | 1.00 | 64.67  | O |
| ATOM | 6086 | N   | LYS A | 844 | 10.556 | 27.210 | −49.352 | 1.00 | 71.43  | N |
| ATOM | 6087 | CA  | LYS A | 844 | 10.646 | 28.294 | −50.326 | 1.00 | 69.50  | C |
| ATOM | 6088 | CB  | LYS A | 844 | 11.826 | 28.084 | −51.313 | 1.00 | 74.57  | C |
| ATOM | 6089 | CG  | LYS A | 844 | 13.222 | 27.866 | −50.701 | 1.00 | 80.42  | C |
| ATOM | 6090 | CD  | LYS A | 844 | 13.671 | 28.998 | −49.771 | 1.00 | 85.88  | C |
| ATOM | 6091 | CE  | LYS A | 844 | 15.193 | 29.250 | −49.825 | 1.00 | 90.87  | C |
| ATOM | 6092 | NZ  | LYS A | 844 | 15.666 | 30.198 | −50.906 | 1.00 | 86.83  | N |
| ATOM | 6093 | C   | LYS A | 844 | 9.358  | 28.349 | −51.114 | 1.00 | 65.88  | C |
| ATOM | 6094 | O   | LYS A | 844 | 9.048  | 29.393 | −51.693 | 1.00 | 63.48  | O |
| ATOM | 6095 | N   | GLN A | 845 | 8.609  | 27.242 | −51.224 | 1.00 | 64.81  | N |
| ATOM | 6096 | CA  | GLN A | 845 | 7.444  | 27.206 | −52.120 | 1.00 | 60.37  | C |
| ATOM | 6097 | CB  | GLN A | 845 | 7.841  | 26.709 | −53.509 | 1.00 | 65.31  | C |
| ATOM | 6098 | CG  | GLN A | 845 | 9.095  | 25.839 | −53.527 | 1.00 | 72.60  | C |
| ATOM | 6099 | CD  | GLN A | 845 | 9.213  | 24.945 | −54.748 | 1.00 | 72.65  | C |
| ATOM | 6100 | OE1 | GLN A | 845 | 8.638  | 25.226 | −55.804 | 1.00 | 68.27  | O |
| ATOM | 6101 | NE2 | GLN A | 845 | 9.955  | 23.842 | −54.592 | 1.00 | 71.48  | N |
| ATOM | 6102 | C   | GLN A | 845 | 6.283  | 26.396 | −51.565 | 1.00 | 54.73  | C |
| ATOM | 6103 | O   | GLN A | 845 | 6.494  | 25.481 | −50.784 | 1.00 | 56.90  | O |
| ATOM | 6104 | N   | GLY A | 846 | 5.075  | 26.794 | −51.963 | 1.00 | 48.36  | N |
| ATOM | 6105 | CA  | GLY A | 846 | 3.819  | 26.190 | −51.567 | 1.00 | 47.28  | C |
| ATOM | 6106 | C   | GLY A | 846 | 2.656  | 26.606 | −52.473 | 1.00 | 47.35  | C |
| ATOM | 6107 | O   | GLY A | 846 | 2.862  | 27.178 | −53.525 | 1.00 | 48.22  | O |
| ATOM | 6108 | N   | ARG A | 847 | 1.424  | 26.304 | −52.081 | 1.00 | 49.03  | N |
| ATOM | 6109 | CA  | ARG A | 847 | 0.241  | 26.539 | −52.933 | 1.00 | 50.61  | C |
| ATOM | 6110 | CB  | ARG A | 847 | −0.184 | 25.301 | −53.739 | 1.00 | 54.50  | C |
| ATOM | 6111 | CG  | ARG A | 847 | 0.866  | 24.646 | −54.639 | 1.00 | 57.00  | C |
| ATOM | 6112 | CD  | ARG A | 847 | 0.185  | 23.695 | −55.637 | 1.00 | 57.62  | C |
| ATOM | 6113 | NE  | ARG A | 847 | −0.340 | 22.454 | −55.056 | 1.00 | 57.63  | N |
| ATOM | 6114 | CZ  | ARG A | 847 | −1.318 | 21.714 | −55.583 | 1.00 | 59.05  | C |
| ATOM | 6115 | NH1 | ARG A | 847 | −1.923 | 22.070 | −56.693 | 1.00 | 59.94  | N |
| ATOM | 6116 | NH2 | ARG A | 847 | −1.725 | 20.605 | −54.982 | 1.00 | 61.83  | N |
| ATOM | 6117 | C   | ARG A | 847 | −0.976 | 26.875 | −52.132 | 1.00 | 47.96  | C |
| ATOM | 6118 | O   | ARG A | 847 | −1.119 | 26.478 | −50.997 | 1.00 | 48.86  | O |
| ATOM | 6119 | N   | ILE A | 848 | −1.875 | 27.576 | −52.767 | 1.00 | 46.02  | N |
| ATOM | 6120 | CA  | ILE A | 848 | −3.153 | 27.809 | −52.221 | 1.00 | 47.77  | C |
| ATOM | 6121 | CB  | ILE A | 848 | −3.423 | 29.307 | −52.067 | 1.00 | 47.91  | C |
| ATOM | 6122 | CG1 | ILE A | 848 | −2.431 | 29.941 | −51.090 | 1.00 | 50.62  | C |
| ATOM | 6123 | CD1 | ILE A | 848 | −2.531 | 31.458 | −50.980 | 1.00 | 51.96  | C |
| ATOM | 6124 | CG2 | ILE A | 848 | −4.816 | 29.537 | −51.517 | 1.00 | 49.93  | C |
| ATOM | 6125 | C   | ILE A | 848 | −4.028 | 27.153 | −53.278 | 1.00 | 51.61  | C |
| ATOM | 6126 | O   | ILE A | 848 | −4.147 | 27.661 | −54.401 | 1.00 | 57.21  | O |
| ATOM | 6127 | N   | VAL A | 849 | −4.605 | 26.008 | −52.952 | 1.00 | 50.17  | N |
| ATOM | 6128 | CA  | VAL A | 849 | −5.490 | 25.340 | −53.856 | 1.00 | 50.21  | C |
| ATOM | 6129 | CB  | VAL A | 849 | −5.299 | 23.816 | −53.838 | 1.00 | 49.42  | C |
| ATOM | 6130 | CG1 | VAL A | 849 | −6.240 | 23.184 | −54.860 | 1.00 | 49.42  | C |
| ATOM | 6131 | CG2 | VAL A | 849 | −3.863 | 23.440 | −54.156 | 1.00 | 49.16  | C |
| ATOM | 6132 | C   | VAL A | 849 | −6.919 | 25.635 | −53.465 | 1.00 | 53.02  | C |

TABLE 6-continued

Atomic coordinates for CRBN:DDB1: Compound B (Human protein)

| ATOM | 6133 | O   | VAL A | 849 | −7.297  | 25.382 | −52.307 | 1.00 | 56.00  | O |
|------|------|-----|-------|-----|---------|--------|---------|------|--------|---|
| ATOM | 6134 | N   | VAL A | 850 | −7.720  | 26.125 | −54.426 | 1.00 | 52.49  | N |
| ATOM | 6135 | CA  | VAL A | 850 | −9.178  | 26.252 | −54.236 | 1.00 | 52.40  | C |
| ATOM | 6136 | CB  | VAL A | 850 | −9.720  | 27.503 | −54.911 | 1.00 | 49.52  | C |
| ATOM | 6137 | CG1 | VAL A | 850 | −11.207 | 27.658 | −54.609 | 1.00 | 49.27  | C |
| ATOM | 6138 | CG2 | VAL A | 850 | −8.931  | 28.714 | −54.437 | 1.00 | 50.72  | C |
| ATOM | 6139 | C   | VAL A | 850 | −9.881  | 25.047 | −54.828 | 1.00 | 53.01  | C |
| ATOM | 6140 | O   | VAL A | 850 | −9.630  | 24.740 | −55.957 | 1.00 | 57.30  | O |
| ATOM | 6141 | N   | PHE A | 851 | −10.748 | 24.385 | −54.073 | 1.00 | 52.61  | N |
| ATOM | 6142 | CA  | PHE A | 851 | −11.442 | 23.194 | −54.531 | 1.00 | 52.93  | C |
| ATOM | 6143 | CB  | PHE A | 851 | −11.177 | 21.988 | −53.634 | 1.00 | 51.48  | C |
| ATOM | 6144 | CG  | PHE A | 851 | −9.788  | 21.408 | −53.701 | 1.00 | 49.32  | C |
| ATOM | 6145 | CD1 | PHE A | 851 | −9.460  | 20.471 | −54.649 | 1.00 | 49.60  | C |
| ATOM | 6146 | CE1 | PHE A | 851 | −8.200  | 19.874 | −54.663 | 1.00 | 49.85  | C |
| ATOM | 6147 | CZ  | PHE A | 851 | −7.277  | 20.175 | −53.683 | 1.00 | 48.30  | C |
| ATOM | 6148 | CE2 | PHE A | 851 | −7.611  | 21.076 | −52.709 | 1.00 | 47.80  | C |
| ATOM | 6149 | CD2 | PHE A | 851 | −8.863  | 21.682 | −52.715 | 1.00 | 48.11  | C |
| ATOM | 6150 | C   | PHE A | 851 | −12.940 | 23.433 | −54.442 | 1.00 | 58.15  | C |
| ATOM | 6151 | O   | PHE A | 851 | −13.383 | 24.248 | −53.648 | 1.00 | 57.92  | O |
| ATOM | 6152 | N   | GLN A | 852 | −13.702 | 22.675 | −55.241 | 1.00 | 64.84  | N |
| ATOM | 6153 | CA  | GLN A | 852 | −15.164 | 22.610 | −55.182 | 1.00 | 65.99  | C |
| ATOM | 6154 | CB  | GLN A | 852 | −15.773 | 23.244 | −56.414 | 1.00 | 68.58  | C |
| ATOM | 6155 | CG  | GLN A | 852 | −17.274 | 23.006 | −56.587 | 1.00 | 72.74  | C |
| ATOM | 6156 | CD  | GLN A | 852 | −17.846 | 23.858 | −57.715 | 1.00 | 75.83  | C |
| ATOM | 6157 | OE1 | GLN A | 852 | −17.399 | 23.759 | −58.871 | 1.00 | 76.52  | O |
| ATOM | 6158 | NE2 | GLN A | 852 | −18.823 | 24.719 | −57.382 | 1.00 | 73.32  | N |
| ATOM | 6159 | C   | GLN A | 852 | −15.594 | 21.159 | −55.134 | 1.00 | 65.84  | C |
| ATOM | 6160 | O   | GLN A | 852 | −15.145 | 20.339 | −55.948 | 1.00 | 64.31  | O |
| ATOM | 6161 | N   | TYR A | 853 | −16.499 | 20.851 | −54.234 | 1.00 | 66.18  | N |
| ATOM | 6162 | CA  | TYR A | 853 | −17.007 | 19.516 | −54.150 | 1.00 | 65.92  | C |
| ATOM | 6163 | CB  | TYR A | 853 | −16.975 | 19.067 | −52.703 | 1.00 | 63.43  | C |
| ATOM | 6164 | CG  | TYR A | 853 | −17.721 | 17.813 | −52.435 | 1.00 | 60.14  | C |
| ATOM | 6165 | CD1 | TYR A | 853 | −17.132 | 16.590 | −52.621 | 1.00 | 59.78  | C |
| ATOM | 6166 | CE1 | TYR A | 853 | −17.815 | 15.433 | −52.372 | 1.00 | 56.76  | C |
| ATOM | 6167 | CZ  | TYR A | 853 | −19.088 | 15.500 | −51.934 | 1.00 | 57.64  | C |
| ATOM | 6168 | OH  | TYR A | 853 | −19.779 | 14.358 | −51.698 | 1.00 | 58.92  | O |
| ATOM | 6169 | CE2 | TYR A | 853 | −19.696 | 16.699 | −51.739 | 1.00 | 56.14  | C |
| ATOM | 6170 | CD2 | TYR A | 853 | −19.006 | 17.850 | −51.984 | 1.00 | 56.17  | C |
| ATOM | 6171 | C   | TYR A | 853 | −18.422 | 19.638 | −54.646 | 1.00 | 73.92  | C |
| ATOM | 6172 | O   | TYR A | 853 | −19.263 | 20.197 | −53.977 | 1.00 | 74.16  | O |
| ATOM | 6173 | N   | SER A | 854 | −18.688 | 19.115 | −55.832 | 1.00 | 88.11  | N |
| ATOM | 6174 | CA  | SER A | 854 | −20.019 | 19.192 | −56.408 | 1.00 | 87.53  | C |
| ATOM | 6175 | CB  | SER A | 854 | −19.962 | 20.040 | −57.659 | 1.00 | 90.85  | C |
| ATOM | 6176 | OG  | SER A | 854 | −18.880 | 19.628 | −58.463 | 1.00 | 92.17  | O |
| ATOM | 6177 | C   | SER A | 854 | −20.505 | 17.819 | −56.779 | 1.00 | 85.03  | C |
| ATOM | 6178 | O   | SER A | 854 | −21.526 | 17.340 | −56.312 | 1.00 | 69.44  | O |
| ATOM | 6179 | N   | ASP A | 855 | −19.748 | 17.175 | −57.639 | 1.00 | 94.15  | N |
| ATOM | 6180 | CA  | ASP A | 855 | −20.068 | 15.838 | −58.046 | 1.00 | 100.54 | C |
| ATOM | 6181 | CB  | ASP A | 855 | −19.274 | 15.450 | −59.277 | 1.00 | 96.40  | C |
| ATOM | 6182 | C   | ASP A | 855 | −19.494 | 15.161 | −56.873 | 1.00 | 99.28  | C |
| ATOM | 6183 | O   | ASP A | 855 | −18.823 | 15.811 | −56.114 | 1.00 | 98.17  | O |
| ATOM | 6184 | N   | GLY A | 856 | −19.684 | 13.866 | −56.731 | 1.00 | 92.68  | N |
| ATOM | 6185 | CA  | GLY A | 856 | −19.141 | 13.179 | −55.582 | 1.00 | 92.46  | C |
| ATOM | 6186 | C   | GLY A | 856 | −17.657 | 13.449 | −55.547 | 1.00 | 87.86  | C |
| ATOM | 6187 | O   | GLY A | 856 | −17.043 | 13.380 | −54.512 | 1.00 | 85.35  | O |
| ATOM | 6188 | N   | LYS A | 857 | −17.091 | 13.752 | −56.702 | 1.00 | 87.98  | N |
| ATOM | 6189 | CA  | LYS A | 857 | −15.683 | 14.097 | −56.832 | 1.00 | 87.99  | C |
| ATOM | 6190 | CB  | LYS A | 857 | −15.178 | 13.801 | −58.240 | 1.00 | 85.29  | C |
| ATOM | 6191 | C   | LYS A | 857 | −15.416 | 15.556 | −56.485 | 1.00 | 82.20  | C |
| ATOM | 6192 | O   | LYS A | 857 | −16.332 | 16.338 | −56.302 | 1.00 | 75.17  | O |
| ATOM | 6193 | N   | LEU A | 858 | −14.137 | 15.888 | −56.396 | 1.00 | 76.05  | N |
| ATOM | 6194 | CA  | LEU A | 858 | −13.659 | 17.212 | −56.055 | 1.00 | 75.39  | C |
| ATOM | 6195 | CB  | LEU A | 858 | −12.644 | 17.013 | −54.946 | 1.00 | 76.81  | C |
| ATOM | 6196 | CG  | LEU A | 858 | −12.522 | 17.874 | −53.700 | 1.00 | 73.97  | C |
| ATOM | 6197 | CD1 | LEU A | 858 | −13.880 | 18.118 | −53.082 | 1.00 | 71.82  | C |
| ATOM | 6198 | CD2 | LEU A | 858 | −11.640 | 17.123 | −52.729 | 1.00 | 72.00  | C |
| ATOM | 6199 | C   | LEU A | 858 | −12.925 | 17.846 | −57.220 | 1.00 | 73.06  | C |
| ATOM | 6200 | O   | LEU A | 858 | −11.957 | 17.279 | −57.694 | 1.00 | 70.59  | O |
| ATOM | 6201 | N   | GLN A | 859 | −13.349 | 19.027 | −57.665 | 1.00 | 75.13  | N |
| ATOM | 6202 | CA  | GLN A | 859 | −12.677 | 19.711 | −58.831 | 1.00 | 74.72  | C |
| ATOM | 6203 | CB  | GLN A | 859 | −13.613 | 20.530 | −59.770 | 1.00 | 83.18  | C |
| ATOM | 6204 | CG  | GLN A | 859 | −15.129 | 20.333 | −59.660 | 1.00 | 92.52  | C |
| ATOM | 6205 | CD  | GLN A | 859 | −15.620 | 18.961 | −60.117 | 1.00 | 93.93  | C |
| ATOM | 6206 | OE1 | GLN A | 859 | −16.818 | 18.668 | −60.074 | 1.00 | 90.76  | O |
| ATOM | 6207 | NE1 | GLN A | 859 | −14.699 | 18.125 | −60.573 | 1.00 | 98.17  | N |
| ATOM | 6208 | C   | GLN A | 859 | −11.675 | 20.694 | −58.270 | 1.00 | 65.13  | C |
| ATOM | 6209 | O   | GLN A | 859 | −12.045 | 21.500 | −57.445 | 1.00 | 63.60  | O |
| ATOM | 6210 | N   | THR A | 860 | −10.426 | 20.643 | −58.705 | 1.00 | 57.38  | N |

TABLE 6-continued

Atomic coordinates for CRBN:DDB1: Compound B (Human protein)

| ATOM | 6211 | CA | THR A | 860 | −9.531 | 21.763 | −58.472 | 1.00 | 54.43 | C |
|---|---|---|---|---|---|---|---|---|---|---|
| ATOM | 6212 | CB | THR A | 860 | −8.072 | 21.417 | −58.827 | 1.00 | 54.29 | C |
| ATOM | 6213 | OG1 | THR A | 860 | −7.534 | 20.497 | −57.855 | 1.00 | 57.26 | O |
| ATOM | 6214 | CG2 | THR A | 860 | −7.193 | 22.670 | −58.869 | 1.00 | 52.19 | C |
| ATOM | 6215 | C | THR A | 860 | −10.011 | 22.946 | −59.316 | 1.00 | 54.53 | C |
| ATOM | 6216 | O | THR A | 860 | −9.909 | 22.914 | −60.511 | 1.00 | 61.46 | O |
| ATOM | 6217 | N | VAL A | 861 | −10.549 | 23.977 | −58.682 | 1.00 | 55.03 | N |
| ATOM | 6218 | CA | VAL A | 861 | −10.975 | 25.232 | −59.329 | 1.00 | 51.72 | C |
| ATOM | 6219 | CB | VAL A | 861 | −12.147 | 25.852 | −58.529 | 1.00 | 50.12 | C |
| ATOM | 6220 | CG1 | VAL A | 861 | −12.466 | 27.279 | −58.905 | 1.00 | 49.38 | C |
| ATOM | 6221 | CG2 | VAL A | 861 | −13.398 | 25.023 | −58.696 | 1.00 | 52.93 | C |
| ATOM | 6222 | C | VAL A | 861 | −9.825 | 26.252 | −59.446 | 1.00 | 55.24 | C |
| ATOM | 6223 | O | VAL A | 861 | −9.949 | 27.178 | −60.230 | 1.00 | 58.88 | O |
| ATOM | 6224 | N | ALA A | 862 | −8.730 | 26.136 | −58.677 | 1.00 | 55.23 | N |
| ATOM | 6225 | CA | ALA A | 862 | −7.580 | 27.057 | −58.872 | 1.00 | 55.64 | C |
| ATOM | 6226 | CB | ALA A | 862 | −7.979 | 28.505 | −58.572 | 1.00 | 54.74 | C |
| ATOM | 6227 | C | ALA A | 862 | −6.348 | 26.669 | −58.060 | 1.00 | 55.53 | C |
| ATOM | 6228 | O | ALA A | 862 | −6.472 | 26.400 | −56.886 | 1.00 | 66.00 | O |
| ATOM | 6229 | N | GLU A | 863 | −5.177 | 26.894 | −58.610 | 1.00 | 52.34 | N |
| ATOM | 6230 | CA | GLU A | 863 | −3.946 | 26.726 | −57.889 | 1.00 | 53.06 | C |
| ATOM | 6231 | CB | GLU A | 863 | −2.963 | 25.922 | −58.701 | 1.00 | 54.50 | C |
| ATOM | 6232 | CG | GLU A | 863 | −3.082 | 24.440 | −58.556 | 1.00 | 56.60 | C |
| ATOM | 6233 | CD | GLU A | 863 | −2.556 | 23.717 | −59.761 | 1.00 | 63.90 | C |
| ATOM | 6234 | OE1 | GLU A | 863 | −1.574 | 22.981 | −59.632 | 1.00 | 67.68 | O |
| ATOM | 6235 | OE2 | GLU A | 863 | −3.131 | 23.883 | −60.842 | 1.00 | 67.15 | O |
| ATOM | 6236 | C | GLU A | 863 | −3.388 | 28.129 | −57.829 | 1.00 | 54.58 | C |
| ATOM | 6237 | O | GLU A | 863 | −3.746 | 28.939 | −58.640 | 1.00 | 51.10 | O |
| ATOM | 6238 | N | LYS A | 864 | −2.548 | 28.436 | −56.856 | 1.00 | 54.78 | N |
| ATOM | 6239 | CA | LYS A | 864 | −1.880 | 29.716 | −56.781 | 1.00 | 57.15 | C |
| ATOM | 6240 | CB | LYS A | 864 | −2.586 | 30.650 | −55.826 | 1.00 | 62.58 | C |
| ATOM | 6241 | CG | LYS A | 864 | −2.945 | 32.006 | −56.407 | 1.00 | 67.89 | C |
| ATOM | 6242 | CD | LYS A | 864 | −1.754 | 32.924 | −56.559 | 1.00 | 76.10 | C |
| ATOM | 6243 | CE | LYS A | 864 | −2.026 | 34.034 | −57.569 | 1.00 | 84.91 | C |
| ATOM | 6244 | NZ | LYS A | 864 | −3.353 | 34.699 | −57.433 | 1.00 | 86.63 | N |
| ATOM | 6245 | C | LYS A | 864 | −0.556 | 29.316 | −56.212 | 1.00 | 57.62 | C |
| ATOM | 6246 | O | LYS A | 864 | −0.537 | 28.737 | −55.165 | 1.00 | 56.52 | O |
| ATOM | 6247 | N | GLU A | 865 | 0.550 | 29.598 | −56.872 | 1.00 | 62.80 | N |
| ATOM | 6248 | CA | GLU A | 865 | 1.844 | 29.217 | −56.336 | 1.00 | 63.94 | C |
| ATOM | 6249 | CB | GLU A | 865 | 2.877 | 29.067 | −57.422 | 1.00 | 69.37 | C |
| ATOM | 6250 | CG | GLU A | 865 | 4.248 | 28.791 | −56.859 | 1.00 | 77.02 | C |
| ATOM | 6251 | CD | GLU A | 865 | 5.267 | 28.507 | −57.927 | 1.00 | 79.92 | C |
| ATOM | 6252 | OE1 | GLU A | 865 | 6.380 | 28.085 | −57.581 | 1.00 | 81.59 | O |
| ATOM | 6253 | OE2 | GLU A | 865 | 4.955 | 28.706 | −59.111 | 1.00 | 77.41 | O |
| ATOM | 6254 | C | GLU A | 865 | 2.283 | 30.262 | −55.368 | 1.00 | 61.46 | C |
| ATOM | 6255 | O | GLU A | 865 | 1.866 | 31.385 | −55.487 | 1.00 | 66.70 | O |
| ATOM | 6256 | N | VAL A | 866 | 3.116 | 29.915 | −54.403 | 1.00 | 55.78 | N |
| ATOM | 6257 | CA | VAL A | 866 | 3.557 | 30.905 | −53.438 | 1.00 | 53.39 | C |
| ATOM | 6258 | CB | VAL A | 866 | 2.648 | 30.950 | −52.246 | 1.00 | 51.61 | C |
| ATOM | 6259 | CG1 | VAL A | 866 | 3.165 | 31.984 | −51.296 | 1.00 | 55.87 | C |
| ATOM | 6260 | CG2 | VAL A | 866 | 1.286 | 31.372 | −52.714 | 1.00 | 51.77 | C |
| ATOM | 6261 | C | VAL A | 866 | 5.009 | 30.742 | −53.081 | 1.00 | 51.55 | C |
| ATOM | 6262 | O | VAL A | 866 | 5.546 | 29.672 | −53.208 | 1.00 | 48.96 | O |
| ATOM | 6263 | N | LYS A | 867 | 5.669 | 31.801 | −52.653 | 1.00 | 51.96 | N |
| ATOM | 6264 | CA | LYS A | 867 | 7.128 | 31.630 | −52.465 | 1.00 | 52.27 | C |
| ATOM | 6265 | CB | LYS A | 867 | 7.943 | 32.717 | −53.257 | 1.00 | 47.81 | C |
| ATOM | 6266 | C | LYS A | 867 | 7.397 | 31.437 | −50.915 | 1.00 | 54.96 | C |
| ATOM | 6267 | O | LYS A | 867 | 8.193 | 32.153 | −50.243 | 1.00 | 53.46 | O |
| ATOM | 6268 | N | GLY A | 868 | 6.698 | 30.419 | −50.387 | 1.00 | 57.45 | N |
| ATOM | 6269 | CA | GLY A | 868 | 6.676 | 30.051 | −48.958 | 1.00 | 59.10 | C |
| ATOM | 6270 | C | GLY A | 868 | 5.536 | 29.105 | −48.506 | 1.00 | 60.91 | C |
| ATOM | 6271 | O | GLY A | 868 | 4.585 | 28.796 | −49.268 | 1.00 | 57.49 | O |
| ATOM | 6272 | N | ALA A | 869 | 5.645 | 28.647 | −47.249 | 1.00 | 60.43 | N |
| ATOM | 6273 | CA | ALA A | 869 | 4.604 | 27.831 | −46.579 | 1.00 | 55.70 | C |
| ATOM | 6274 | CB | ALA A | 869 | 5.169 | 27.204 | −45.316 | 1.00 | 55.68 | C |
| ATOM | 6275 | C | ALA A | 869 | 3.389 | 28.651 | −46.203 | 1.00 | 51.56 | C |
| ATOM | 6276 | O | ALA A | 869 | 3.522 | 29.696 | −45.561 | 1.00 | 52.04 | O |
| ATOM | 6277 | N | VAL A | 870 | 2.216 | 28.174 | −46.572 | 1.00 | 46.63 | N |
| ATOM | 6278 | CA | VAL A | 870 | 0.996 | 28.774 | −46.107 | 1.00 | 47.33 | C |
| ATOM | 6279 | CB | VAL A | 870 | −0.146 | 28.602 | −47.112 | 1.00 | 47.82 | C |
| ATOM | 6280 | CG1 | VAL A | 870 | −1.420 | 29.244 | −46.581 | 1.00 | 48.57 | C |
| ATOM | 6281 | CG2 | VAL A | 870 | 0.218 | 29.189 | −48.474 | 1.00 | 48.70 | C |
| ATOM | 6282 | C | VAL A | 870 | 0.616 | 28.122 | −44.775 | 1.00 | 51.29 | C |
| ATOM | 6283 | O | VAL A | 870 | −0.055 | 27.106 | −44.735 | 1.00 | 51.88 | O |
| ATOM | 6284 | N | TYR A | 871 | 1.033 | 28.724 | −43.668 | 1.00 | 56.05 | N |
| ATOM | 6285 | CA | TYR A | 871 | 0.732 | 28.204 | −42.325 | 1.00 | 50.29 | C |
| ATOM | 6286 | CB | TYR A | 871 | 1.617 | 28.871 | −41.274 | 1.00 | 47.62 | C |
| ATOM | 6287 | CG | TYR A | 871 | 3.103 | 28.584 | −41.465 | 1.00 | 47.07 | C |
| ATOM | 6288 | CD1 | TYR A | 871 | 3.617 | 27.318 | −41.249 | 1.00 | 48.93 | C |

TABLE 6-continued

Atomic coordinates for CRBN:DDB1: Compound B (Human protein)

| ATOM | 6289 | CE1 | TYR A | 871 | 4.983 | 27.045 | −41.409 | 1.00 | 47.90 | C |
|---|---|---|---|---|---|---|---|---|---|---|
| ATOM | 6290 | CZ | TYR A | 871 | 5.837 | 28.037 | −41.803 | 1.00 | 48.00 | C |
| ATOM | 6291 | OH | TYR A | 871 | 7.167 | 27.728 | −41.974 | 1.00 | 54.27 | O |
| ATOM | 6292 | CE2 | TYR A | 871 | 5.358 | 29.312 | −42.028 | 1.00 | 45.81 | C |
| ATOM | 6293 | CD2 | TYR A | 871 | 4.003 | 29.582 | −41.852 | 1.00 | 46.32 | C |
| ATOM | 6294 | C | TYR A | 871 | −0.743 | 28.385 | −41.980 | 1.00 | 49.03 | C |
| ATOM | 6295 | O | TYR A | 871 | −1.287 | 27.507 | −41.311 | 1.00 | 53.21 | O |
| ATOM | 6296 | N | SER A | 872 | −1.387 | 29.478 | −42.426 | 1.00 | 46.04 | N |
| ATOM | 6297 | CA | SER A | 872 | −2.808 | 29.745 | −42.076 | 1.00 | 47.46 | C |
| ATOM | 6298 | CB | SER A | 872 | −2.881 | 30.579 | −40.834 | 1.00 | 48.51 | C |
| ATOM | 6299 | OG | SER A | 872 | −2.027 | 30.001 | −39.883 | 1.00 | 53.48 | O |
| ATOM | 6300 | C | SER A | 872 | −3.583 | 30.490 | −43.090 | 1.00 | 48.10 | C |
| ATOM | 6301 | O | SER A | 872 | −2.990 | 31.074 | −43.974 | 1.00 | 56.31 | O |
| ATOM | 6302 | N | MET A | 873 | −4.906 | 30.484 | −42.971 | 1.00 | 45.90 | N |
| ATOM | 6303 | CA | MET A | 873 | −5.769 | 31.261 | −43.857 | 1.00 | 48.41 | C |
| ATOM | 6304 | CB | MET A | 873 | −6.178 | 30.456 | −45.092 | 1.00 | 52.38 | C |
| ATOM | 6305 | CG | MET A | 873 | −5.030 | 29.966 | −45.972 | 1.00 | 56.65 | C |
| ATOM | 6306 | SD | MET A | 873 | −5.516 | 29.129 | −47.500 | 1.00 | 62.98 | S |
| ATOM | 6307 | CE | MET A | 873 | −6.424 | 27.754 | −46.861 | 1.00 | 59.46 | C |
| ATOM | 6308 | C | MET A | 873 | −7.021 | 31.654 | −43.124 | 1.00 | 49.06 | C |
| ATOM | 6309 | O | MET A | 873 | −7.361 | 31.038 | −42.149 | 1.00 | 52.23 | O |
| ATOM | 6310 | N | VAL A | 874 | −7.731 | 32.672 | −43.585 | 1.00 | 51.30 | N |
| ATOM | 6311 | CA | VAL A | 874 | −9.045 | 32.990 | −43.011 | 1.00 | 52.96 | C |
| ATOM | 6312 | CB | VAL A | 874 | −8.934 | 33.887 | −41.742 | 1.00 | 54.82 | C |
| ATOM | 6313 | CG1 | VAL A | 874 | −7.577 | 34.043 | −41.052 | 1.00 | 54.52 | C |
| ATOM | 6314 | CG2 | VAL A | 874 | −10.126 | 34.794 | −41.438 | 1.00 | 57.56 | C |
| ATOM | 6315 | C | VAL A | 874 | −9.924 | 33.697 | −44.022 | 1.00 | 51.25 | C |
| ATOM | 6316 | O | VAL A | 874 | −9.432 | 34.543 | −44.701 | 1.00 | 56.09 | O |
| ATOM | 6317 | N | GLU A | 875 | −11.216 | 33.402 | −44.098 | 1.00 | 50.11 | N |
| ATOM | 6318 | CA | GLU A | 875 | −12.088 | 34.272 | −44.872 | 1.00 | 49.71 | C |
| ATOM | 6319 | CB | GLU A | 875 | −13.487 | 33.721 | −45.028 | 1.00 | 51.37 | C |
| ATOM | 6320 | CG | GLU A | 875 | −14.433 | 34.685 | −45.753 | 1.00 | 55.49 | C |
| ATOM | 6321 | CD | GLU A | 875 | −15.381 | 35.478 | −44.859 | 1.00 | 60.79 | C |
| ATOM | 6322 | OE1 | GLU A | 875 | −15.846 | 34.944 | −43.825 | 1.00 | 61.73 | O |
| ATOM | 6323 | OE2 | GLU A | 875 | −15.717 | 36.638 | −45.220 | 1.00 | 70.65 | O |
| ATOM | 6324 | C | GLU A | 875 | −12.168 | 35.620 | −44.207 | 1.00 | 49.70 | C |
| ATOM | 6325 | O | GLU A | 875 | −12.556 | 35.724 | −43.058 | 1.00 | 48.98 | O |
| ATOM | 6326 | N | PHE A | 876 | −11.846 | 36.647 | −44.981 | 1.00 | 55.38 | N |
| ATOM | 6327 | CA | PHE A | 876 | −11.737 | 38.029 | −44.516 | 1.00 | 59.69 | C |
| ATOM | 6328 | CB | PHE A | 876 | −10.287 | 38.466 | −44.587 | 1.00 | 60.66 | C |
| ATOM | 6329 | CG | PHE A | 876 | −10.030 | 39.749 | −43.892 | 1.00 | 66.45 | C |
| ATOM | 6330 | CD1 | PHE A | 876 | −10.211 | 39.845 | −42.530 | 1.00 | 71.04 | C |
| ATOM | 6331 | CE1 | PHE A | 876 | −9.979 | 41.040 | −41.875 | 1.00 | 73.82 | C |
| ATOM | 6332 | CZ | PHE A | 876 | −9.570 | 42.158 | −42.588 | 1.00 | 70.95 | C |
| ATOM | 6333 | CE2 | PHE A | 876 | −9.388 | 42.079 | −43.949 | 1.00 | 69.82 | C |
| ATOM | 6334 | CD2 | PHE A | 876 | −9.623 | 40.876 | −44.595 | 1.00 | 72.32 | C |
| ATOM | 6335 | C | PHE A | 876 | −12.600 | 38.970 | −45.358 | 1.00 | 61.16 | C |
| ATOM | 6336 | O | PHE A | 876 | −12.194 | 39.421 | −46.421 | 1.00 | 62.24 | O |
| ATOM | 6337 | N | ASN A | 877 | −13.822 | 39.204 | −44.897 | 1.00 | 65.52 | N |
| ATOM | 6338 | CA | ASN A | 877 | −14.776 | 40.125 | −45.529 | 1.00 | 66.10 | C |
| ATOM | 6339 | CB | ASN A | 877 | −14.322 | 41.559 | −45.288 | 1.00 | 67.59 | C |
| ATOM | 6340 | CG | ASN A | 877 | −14.152 | 41.845 | −43.808 | 1.00 | 72.11 | C |
| ATOM | 6341 | OD1 | ASN A | 877 | −15.103 | 41.708 | −43.040 | 1.00 | 75.81 | O |
| ATOM | 6342 | ND2 | ASN A | 877 | −12.936 | 42.189 | −43.387 | 1.00 | 76.33 | N |
| ATOM | 6343 | C | ASN A | 877 | −15.052 | 39.826 | −46.992 | 1.00 | 64.55 | C |
| ATOM | 6344 | O | ASN A | 877 | −15.311 | 40.715 | −47.801 | 1.00 | 68.13 | O |
| ATOM | 6345 | N | GLY A | 878 | −15.025 | 38.541 | −47.302 | 1.00 | 64.36 | N |
| ATOM | 6346 | CA | GLY A | 878 | −15.261 | 38.055 | −48.640 | 1.00 | 64.80 | C |
| ATOM | 6347 | C | GLY A | 878 | −14.022 | 37.936 | −49.477 | 1.00 | 62.20 | C |
| ATOM | 6348 | O | GLY A | 878 | −14.142 | 37.577 | −50.649 | 1.00 | 68.53 | O |
| ATOM | 6349 | N | LYS A | 879 | −12.860 | 38.242 | −48.896 | 1.00 | 56.64 | N |
| ATOM | 6350 | CA | LYS A | 879 | −11.562 | 38.030 | −49.523 | 1.00 | 58.55 | C |
| ATOM | 6351 | CB | LYS A | 879 | −10.770 | 39.335 | −49.464 | 1.00 | 61.26 | C |
| ATOM | 6352 | CG | LYS A | 879 | −11.509 | 40.503 | −50.113 | 1.00 | 64.02 | C |
| ATOM | 6353 | CD | LYS A | 879 | −10.780 | 41.840 | −50.015 | 1.00 | 65.40 | C |
| ATOM | 6354 | CE | LYS A | 879 | −11.690 | 42.960 | −49.477 | 1.00 | 64.60 | C |
| ATOM | 6355 | NZ | LYS A | 879 | −11.043 | 44.215 | −49.924 | 1.00 | 66.24 | N |
| ATOM | 6356 | C | LYS A | 879 | −10.833 | 36.907 | −48.800 | 1.00 | 57.35 | C |
| ATOM | 6357 | O | LYS A | 879 | −11.333 | 36.422 | −47.827 | 1.00 | 63.42 | O |
| ATOM | 6358 | N | LEU A | 880 | −9.655 | 36.493 | −49.250 | 1.00 | 55.80 | N |
| ATOM | 6359 | CA | LEU A | 880 | −8.937 | 35.387 | −48.599 | 1.00 | 55.13 | C |
| ATOM | 6360 | CB | LEU A | 880 | −8.689 | 34.227 | −49.575 | 1.00 | 56.57 | C |
| ATOM | 6361 | CG | LEU A | 880 | −8.075 | 32.949 | −48.970 | 1.00 | 60.05 | C |
| ATOM | 6362 | CD1 | LEU A | 880 | −9.183 | 32.000 | −48.577 | 1.00 | 63.09 | C |
| ATOM | 6363 | CD2 | LEU A | 880 | −7.128 | 32.192 | −49.887 | 1.00 | 60.07 | C |
| ATOM | 6364 | C | LEU A | 880 | −7.619 | 35.900 | −48.058 | 1.00 | 53.26 | C |
| ATOM | 6365 | O | LEU A | 880 | −6.754 | 36.334 | −48.818 | 1.00 | 53.39 | O |
| ATOM | 6366 | N | LEU A | 881 | −7.479 | 35.853 | −46.740 | 1.00 | 50.99 | N |

TABLE 6-continued

Atomic coordinates for CRBN:DDB1: Compound B (Human protein)

| ATOM | 6367 | CA | LEU A | 881 | −6.277 | 36.314 | −46.040 | 1.00 | 49.27 | C |
|---|---|---|---|---|---|---|---|---|---|---|
| ATOM | 6368 | CB | LEU A | 881 | −6.664 | 36.893 | −44.688 | 1.00 | 49.88 | C |
| ATOM | 6369 | CG | LEU A | 881 | −5.558 | 37.547 | −43.878 | 1.00 | 51.79 | C |
| ATOM | 6370 | CD1 | LEU A | 881 | −4.962 | 38.662 | −44.711 | 1.00 | 54.17 | C |
| ATOM | 6371 | CD2 | LEU A | 881 | −6.064 | 38.065 | −42.535 | 1.00 | 51.49 | C |
| ATOM | 6372 | C | LEU A | 881 | −5.459 | 35.104 | −45.800 | 1.00 | 49.39 | C |
| ATOM | 6373 | O | LEU A | 881 | −6.023 | 34.064 | −45.554 | 1.00 | 53.03 | O |
| ATOM | 6374 | N | ALA A | 882 | −4.143 | 35.222 | −45.832 | 1.00 | 49.97 | N |
| ATOM | 6375 | CA | ALA A | 882 | −3.284 | 34.042 | −45.780 | 1.00 | 53.49 | C |
| ATOM | 6376 | CB | ALA A | 882 | −3.303 | 33.321 | −47.108 | 1.00 | 54.60 | C |
| ATOM | 6377 | C | ALA A | 882 | −1.877 | 34.374 | −45.469 | 1.00 | 55.87 | C |
| ATOM | 6378 | O | ALA A | 882 | −1.361 | 35.346 | −45.934 | 1.00 | 66.08 | O |
| ATOM | 6379 | N | SER A | 883 | −1.228 | 33.522 | −44.720 | 1.00 | 59.95 | N |
| ATOM | 6380 | CA | SER A | 883 | 0.114 | 33.797 | −44.285 | 1.00 | 62.39 | C |
| ATOM | 6381 | CB | SER A | 883 | 0.305 | 33.503 | −42.773 | 1.00 | 65.31 | C |
| ATOM | 6382 | OG | SER A | 883 | −0.480 | 32.411 | −42.291 | 1.00 | 69.64 | O |
| ATOM | 6383 | C | SER A | 883 | 0.985 | 32.944 | −45.155 | 1.00 | 59.12 | C |
| ATOM | 6384 | O | SER A | 883 | 0.701 | 31.776 | −45.356 | 1.00 | 63.60 | O |
| ATOM | 6385 | N | ILE A | 884 | 2.078 | 33.508 | −45.622 | 1.00 | 55.06 | N |
| ATOM | 6386 | CA | ILE A | 884 | 3.044 | 32.757 | −46.374 | 1.00 | 55.69 | C |
| ATOM | 6387 | CB | ILE A | 884 | 3.106 | 33.260 | −47.803 | 1.00 | 51.19 | C |
| ATOM | 6388 | CG1 | ILE A | 884 | 1.723 | 33.234 | −48.399 | 1.00 | 49.11 | C |
| ATOM | 6389 | CD1 | ILE A | 884 | 1.526 | 34.229 | −49.495 | 1.00 | 47.80 | C |
| ATOM | 6390 | CG2 | ILE A | 884 | 4.019 | 32.400 | −48.632 | 1.00 | 49.82 | C |
| ATOM | 6391 | C | ILE A | 884 | 4.303 | 33.150 | −45.659 | 1.00 | 56.66 | C |
| ATOM | 6392 | O | ILE A | 884 | 4.690 | 34.289 | −45.731 | 1.00 | 62.91 | O |
| ATOM | 6393 | N | ASN A | 885 | 4.933 | 32.236 | −44.951 | 1.00 | 53.81 | N |
| ATOM | 6394 | CA | ASN A | 885 | 6.135 | 32.582 | −44.228 | 1.00 | 59.51 | C |
| ATOM | 6395 | CB | ASN A | 885 | 7.312 | 32.709 | −45.148 | 1.00 | 65.81 | C |
| ATOM | 6396 | CG | ASN A | 885 | 7.696 | 31.384 | −45.726 | 1.00 | 79.47 | C |
| ATOM | 6397 | OD1 | ASN A | 885 | 6.841 | 30.554 | −45.943 | 1.00 | 93.98 | O |
| ATOM | 6398 | ND2 | ASN A | 885 | 8.974 | 31.167 | −45.961 | 1.00 | 84.91 | N |
| ATOM | 6399 | C | ASN A | 885 | 5.903 | 33.802 | −43.371 | 1.00 | 57.87 | C |
| ATOM | 6400 | O | ASN A | 885 | 4.955 | 33.839 | −42.631 | 1.00 | 54.69 | O |
| ATOM | 6401 | N | SER A | 886 | 6.751 | 34.806 | −43.479 | 1.00 | 56.07 | N |
| ATOM | 6402 | CA | SER A | 886 | 6.584 | 35.998 | −42.678 | 1.00 | 55.11 | C |
| ATOM | 6403 | CB | SER A | 886 | 7.918 | 36.661 | −42.397 | 1.00 | 57.05 | C |
| ATOM | 6404 | OG | SER A | 886 | 8.202 | 37.679 | −43.322 | 1.00 | 60.49 | O |
| ATOM | 6405 | C | SER A | 886 | 5.603 | 36.988 | −43.256 | 1.00 | 56.85 | C |
| ATOM | 6406 | O | SER A | 886 | 5.365 | 38.011 | −42.670 | 1.00 | 59.21 | O |
| ATOM | 6407 | N | THR A | 887 | 5.045 | 36.701 | −44.415 | 1.00 | 55.53 | N |
| ATOM | 6408 | CA | THR A | 887 | 4.078 | 37.625 | −45.035 | 1.00 | 56.86 | C |
| ATOM | 6409 | CB | THR A | 887 | 4.287 | 37.672 | −46.562 | 1.00 | 59.91 | C |
| ATOM | 6410 | OG1 | THR A | 887 | 5.490 | 38.381 | −46.835 | 1.00 | 65.24 | O |
| ATOM | 6411 | CG2 | THR A | 887 | 3.169 | 38.412 | −47.278 | 1.00 | 61.35 | C |
| ATOM | 6412 | C | THR A | 887 | 2.609 | 37.297 | −44.755 | 1.00 | 53.06 | C |
| ATOM | 6413 | O | THR A | 887 | 2.185 | 36.166 | −44.866 | 1.00 | 47.37 | O |
| ATOM | 6414 | N | VAL A | 888 | 1.833 | 38.316 | −44.440 | 1.00 | 53.58 | N |
| ATOM | 6415 | CA | VAL A | 888 | 0.391 | 38.210 | −44.460 | 1.00 | 56.33 | C |
| ATOM | 6416 | CB | VAL A | 888 | −0.244 | 39.005 | −43.313 | 1.00 | 60.88 | C |
| ATOM | 6417 | CG1 | VAL A | 888 | −1.701 | 39.283 | −43.610 | 1.00 | 65.40 | C |
| ATOM | 6418 | CG2 | VAL A | 888 | −0.140 | 38.242 | −41.996 | 1.00 | 62.83 | C |
| ATOM | 6419 | C | VAL A | 888 | −0.019 | 38.847 | −45.760 | 1.00 | 57.70 | C |
| ATOM | 6420 | O | VAL A | 888 | 0.457 | 39.929 | −46.050 | 1.00 | 65.46 | O |
| ATOM | 6421 | N | ARG A | 889 | −0.933 | 38.220 | −46.507 | 1.00 | 55.82 | N |
| ATOM | 6422 | CA | ARG A | 889 | −1.280 | 38.620 | −47.865 | 1.00 | 50.96 | C |
| ATOM | 6423 | CB | ARG A | 889 | −0.488 | 37.765 | −48.843 | 1.00 | 52.73 | C |
| ATOM | 6424 | CG | ARG A | 889 | −0.817 | 38.034 | −50.322 | 1.00 | 59.02 | C |
| ATOM | 6425 | CD | ARG A | 889 | 0.184 | 37.424 | −51.321 | 1.00 | 61.53 | C |
| ATOM | 6426 | NE | ARG A | 889 | 1.602 | 37.662 | −50.976 | 1.00 | 62.63 | N |
| ATOM | 6427 | CZ | ARG A | 889 | 2.651 | 36.959 | −51.438 | 1.00 | 60.72 | C |
| ATOM | 6428 | NH1 | ARG A | 889 | 2.519 | 35.944 | −52.309 | 1.00 | 61.51 | N |
| ATOM | 6429 | NH2 | ARG A | 889 | 3.862 | 37.281 | −51.020 | 1.00 | 59.26 | N |
| ATOM | 6430 | C | ARG A | 889 | −2.777 | 38.485 | −48.129 | 1.00 | 48.97 | C |
| ATOM | 6431 | O | ARG A | 889 | −3.356 | 37.452 | −47.917 | 1.00 | 47.97 | O |
| ATOM | 6432 | N | LEU A | 890 | −3.410 | 39.529 | −48.628 | 1.00 | 50.59 | N |
| ATOM | 6433 | CA | LEU A | 890 | −4.834 | 39.475 | −48.947 | 1.00 | 50.80 | C |
| ATOM | 6434 | CB | LEU A | 890 | −5.446 | 40.765 | −48.506 | 1.00 | 50.30 | C |
| ATOM | 6435 | CG | LEU A | 890 | −6.945 | 40.880 | −48.595 | 1.00 | 53.20 | C |
| ATOM | 6436 | CD1 | LEU A | 890 | −7.708 | 39.698 | −48.058 | 1.00 | 53.14 | C |
| ATOM | 6437 | CD2 | LEU A | 890 | −7.310 | 42.122 | −47.802 | 1.00 | 57.82 | C |
| ATOM | 6438 | C | LEU A | 890 | −5.055 | 39.262 | −50.455 | 1.00 | 52.81 | C |
| ATOM | 6439 | O | LEU A | 890 | −4.321 | 39.804 | −51.258 | 1.00 | 50.86 | O |
| ATOM | 6440 | N | TYR A | 891 | −6.035 | 38.433 | −50.826 | 1.00 | 53.59 | N |
| ATOM | 6441 | CA | TYR A | 891 | −6.300 | 38.031 | −52.217 | 1.00 | 50.49 | C |
| ATOM | 6442 | CB | TYR A | 891 | −6.053 | 36.498 | −52.415 | 1.00 | 49.83 | C |
| ATOM | 6443 | CG | TYR A | 891 | −4.606 | 35.948 | −52.373 | 1.00 | 51.34 | C |
| ATOM | 6444 | CD1 | TYR A | 891 | −3.753 | 36.079 | −53.476 | 1.00 | 56.18 | C |

TABLE 6-continued

Atomic coordinates for CRBN:DDB1: Compound B (Human protein)

| ATOM | 6445 | CE1 | TYR A | 891 | −2.449 | 35.595 | −53.467 | 1.00 | 55.30 | C |
| --- | --- | --- | --- | --- | --- | --- | --- | --- | --- | --- |
| ATOM | 6446 | CZ | TYR A | 891 | −1.996 | 34.937 | −52.368 | 1.00 | 55.74 | C |
| ATOM | 6447 | OH | TYR A | 891 | −0.714 | 34.457 | −52.406 | 1.00 | 58.21 | O |
| ATOM | 6448 | CE2 | TYR A | 891 | −2.819 | 34.765 | −51.267 | 1.00 | 53.31 | C |
| ATOM | 6449 | CD2 | TYR A | 891 | −4.113 | 35.265 | −51.275 | 1.00 | 50.70 | C |
| ATOM | 6450 | C | TYR A | 891 | −7.781 | 38.288 | −52.444 | 1.00 | 51.63 | C |
| ATOM | 6451 | O | TYR A | 891 | −8.569 | 38.031 | −51.512 | 1.00 | 48.72 | O |
| ATOM | 6452 | N | GLU A | 892 | −8.175 | 38.783 | −53.634 | 1.00 | 51.72 | N |
| ATOM | 6453 | CA | GLU A | 892 | −9.596 | 38.823 | −54.011 | 1.00 | 52.55 | C |
| ATOM | 6454 | CB | GLU A | 892 | −9.956 | 40.141 | −54.627 | 1.00 | 57.98 | C |
| ATOM | 6455 | CG | GLU A | 892 | −10.188 | 41.302 | −53.671 | 1.00 | 62.53 | C |
| ATOM | 6456 | CD | GLU A | 892 | −9.788 | 42.617 | −54.314 | 1.00 | 65.85 | C |
| ATOM | 6457 | OE1 | GLU A | 892 | −10.652 | 43.485 | −54.510 | 1.00 | 66.66 | O |
| ATOM | 6458 | OE2 | GLU A | 892 | −8.597 | 42.756 | −54.689 | 1.00 | 73.68 | O |
| ATOM | 6459 | C | GLU A | 892 | −9.854 | 37.766 | −55.047 | 1.00 | 54.43 | C |
| ATOM | 6460 | O | GLU A | 892 | −8.914 | 37.245 | −55.670 | 1.00 | 50.96 | O |
| ATOM | 6461 | N | TRP A | 893 | −11.145 | 37.469 | −55.247 | 1.00 | 58.70 | N |
| ATOM | 6462 | CA | TRP A | 893 | −11.621 | 36.357 | −56.143 | 1.00 | 58.85 | C |
| ATOM | 6463 | CB | TRP A | 893 | −12.653 | 35.470 | −55.371 | 1.00 | 55.44 | C |
| ATOM | 6464 | CG | TRP A | 893 | −13.071 | 34.140 | −56.008 | 1.00 | 50.44 | C |
| ATOM | 6465 | CD1 | TRP A | 893 | −14.349 | 33.734 | −56.280 | 1.00 | 50.69 | C |
| ATOM | 6466 | NE1 | TRP A | 893 | −14.356 | 32.478 | −56.830 | 1.00 | 49.69 | N |
| ATOM | 6467 | CE2 | TRP A | 893 | −13.063 | 32.035 | −56.895 | 1.00 | 51.01 | C |
| ATOM | 6468 | CD2 | TRP A | 893 | −12.230 | 33.053 | −56.383 | 1.00 | 48.03 | C |
| ATOM | 6469 | CE3 | TRP A | 893 | −10.851 | 32.828 | −56.326 | 1.00 | 48.95 | C |
| ATOM | 6470 | CZ3 | TRP A | 893 | −10.333 | 31.599 | −56.792 | 1.00 | 49.46 | C |
| ATOM | 6471 | CH2 | TRP A | 893 | −11.179 | 30.624 | −57.319 | 1.00 | 52.67 | C |
| ATOM | 6472 | CZ2 | TRP A | 893 | −12.551 | 30.814 | −57.368 | 1.00 | 53.80 | C |
| ATOM | 6473 | C | TRP A | 893 | −12.217 | 36.904 | −57.460 | 1.00 | 60.74 | C |
| ATOM | 6474 | O | TRP A | 893 | −13.374 | 37.350 | −57.484 | 1.00 | 55.54 | O |
| ATOM | 6475 | N | THR A | 894 | −11.429 | 36.827 | −58.543 | 1.00 | 66.75 | N |
| ATOM | 6476 | CA | THR A | 894 | −11.794 | 37.413 | −59.848 | 1.00 | 69.09 | C |
| ATOM | 6477 | CB | THR A | 894 | −10.609 | 37.471 | −60.907 | 1.00 | 69.50 | C |
| ATOM | 6478 | OG1 | THR A | 894 | −10.603 | 36.359 | −61.826 | 1.00 | 58.67 | O |
| ATOM | 6479 | CG2 | THR A | 894 | −9.199 | 37.614 | −60.262 | 1.00 | 71.06 | C |
| ATOM | 6480 | C | THR A | 894 | −12.997 | 36.623 | −60.381 | 1.00 | 74.83 | C |
| ATOM | 6481 | O | THR A | 894 | −13.171 | 35.454 | −60.005 | 1.00 | 71.50 | O |
| ATOM | 6482 | N | THR A | 895 | −13.836 | 37.271 | −61.212 | 1.00 | 81.67 | N |
| ATOM | 6483 | CA | THR A | 895 | −14.958 | 36.592 | −61.942 | 1.00 | 80.81 | C |
| ATOM | 6484 | CB | THR A | 895 | −15.990 | 37.579 | −62.589 | 1.00 | 83.47 | C |
| ATOM | 6485 | OG1 | THR A | 895 | −15.348 | 38.819 | −62.883 | 1.00 | 87.89 | O |
| ATOM | 6486 | CG2 | THR A | 895 | −17.174 | 37.883 | −61.645 | 1.00 | 85.65 | C |
| ATOM | 6487 | C | THR A | 895 | −14.419 | 35.616 | −62.993 | 1.00 | 73.06 | C |
| ATOM | 6488 | O | THR A | 895 | −15.112 | 34.661 | −63.352 | 1.00 | 69.72 | O |
| ATOM | 6489 | N | GLU A | 896 | −13.170 | 35.845 | −63.436 | 1.00 | 71.39 | N |
| ATOM | 6490 | CA | GLU A | 896 | −12.370 | 34.863 | −64.205 | 1.00 | 67.20 | C |
| ATOM | 6491 | CB | GLU A | 896 | −11.140 | 35.544 | −64.888 | 1.00 | 64.67 | C |
| ATOM | 6492 | C | GLU A | 896 | −11.956 | 33.666 | −63.324 | 1.00 | 63.20 | C |
| ATOM | 6493 | O | GLU A | 896 | −11.192 | 32.805 | −63.775 | 1.00 | 55.50 | O |
| ATOM | 6494 | N | LYS A | 897 | −12.440 | 33.663 | −62.061 | 1.00 | 69.66 | N |
| ATOM | 6495 | CA | LYS A | 897 | −12.353 | 32.568 | −61.060 | 1.00 | 68.82 | C |
| ATOM | 6496 | CB | LYS A | 897 | −13.034 | 31.354 | −61.641 | 1.00 | 70.84 | C |
| ATOM | 6497 | CG | LYS A | 897 | −13.719 | 30.492 | −60.634 | 1.00 | 73.40 | C |
| ATOM | 6498 | CD | LYS A | 897 | −14.995 | 29.875 | −61.206 | 1.00 | 75.38 | C |
| ATOM | 6499 | CE | LYS A | 897 | −16.174 | 30.840 | −61.118 | 1.00 | 74.53 | C |
| ATOM | 6500 | NZ | LYS A | 897 | −17.430 | 30.052 | −60.960 | 1.00 | 74.21 | N |
| ATOM | 6501 | C | LYS A | 897 | −10.918 | 32.258 | −60.548 | 1.00 | 69.44 | C |
| ATOM | 6502 | O | LYS A | 897 | −10.528 | 31.090 | −60.370 | 1.00 | 67.29 | O |
| ATOM | 6503 | N | GLU A | 898 | −10.173 | 33.341 | −60.289 | 1.00 | 70.13 | N |
| ATOM | 6504 | CA | GLU A | 898 | −8.736 | 33.327 | −60.000 | 1.00 | 73.04 | C |
| ATOM | 6505 | CB | GLU A | 898 | −7.931 | 33.907 | −61.185 | 1.00 | 85.84 | C |
| ATOM | 6506 | CG | GLU A | 898 | −7.691 | 32.999 | −62.390 | 1.00 | 92.83 | C |
| ATOM | 6507 | CD | GLU A | 898 | −6.603 | 31.951 | −62.154 | 1.00 | 101.60 | C |
| ATOM | 6508 | OE1 | GLU A | 898 | −6.872 | 30.988 | −61.387 | 1.00 | 107.78 | O |
| ATOM | 6509 | OE2 | GLU A | 898 | −5.497 | 32.069 | −62.754 | 1.00 | 100.24 | O |
| ATOM | 6510 | C | GLU A | 898 | −8.439 | 34.184 | −58.767 | 1.00 | 68.59 | C |
| ATOM | 6511 | O | GLU A | 898 | −9.219 | 35.062 | −58.378 | 1.00 | 66.20 | O |
| ATOM | 6512 | N | LEU A | 899 | −7.287 | 33.937 | −58.168 | 1.00 | 63.84 | N |
| ATOM | 6513 | CA | LEU A | 899 | −6.918 | 34.610 | −56.943 | 1.00 | 62.96 | C |
| ATOM | 6514 | CB | LEU A | 899 | −6.299 | 33.635 | −55.939 | 1.00 | 61.63 | C |
| ATOM | 6515 | CG | LEU A | 899 | −7.263 | 32.847 | −55.067 | 1.00 | 59.13 | C |
| ATOM | 6516 | CD1 | LEU A | 899 | −6.507 | 31.727 | −54.362 | 1.00 | 59.52 | C |
| ATOM | 6517 | CD2 | LEU A | 899 | −7.982 | 33.750 | −54.069 | 1.00 | 57.25 | C |
| ATOM | 6518 | C | LEU A | 899 | −5.913 | 35.690 | −57.243 | 1.00 | 64.87 | C |
| ATOM | 6519 | O | LEU A | 899 | −4.747 | 35.394 | −57.552 | 1.00 | 63.84 | O |
| ATOM | 6520 | N | ARG A | 900 | −6.368 | 36.929 | −57.101 | 1.00 | 65.56 | N |
| ATOM | 6521 | CA | ARG A | 900 | −5.578 | 38.119 | −57.337 | 1.00 | 60.24 | C |
| ATOM | 6522 | CB | ARG A | 900 | −6.352 | 39.062 | −58.250 | 1.00 | 60.32 | C |

TABLE 6-continued

Atomic coordinates for CRBN:DDB1: Compound B (Human protein)

| ATOM | 6523 | CG | ARG A | 900 | −5.750 | 40.442 | −58.386 | 1.00 | 60.77 | C |
|---|---|---|---|---|---|---|---|---|---|---|
| ATOM | 6524 | CD | ARG A | 900 | −6.651 | 41.395 | −59.140 | 1.00 | 60.35 | C |
| ATOM | 6525 | NE | ARG A | 900 | −7.835 | 41.752 | −58.388 | 1.00 | 57.89 | N |
| ATOM | 6526 | CZ | ARG A | 900 | −9.052 | 41.766 | −58.898 | 1.00 | 55.32 | C |
| ATOM | 6527 | NH1 | ARG A | 900 | −9.235 | 41.457 | −60.158 | 1.00 | 54.21 | N |
| ATOM | 6528 | NH2 | ARG A | 900 | −10.083 | 42.109 | −58.164 | 1.00 | 52.17 | N |
| ATOM | 6529 | C | ARG A | 900 | −5.305 | 38.819 | −56.037 | 1.00 | 53.84 | C |
| ATOM | 6530 | O | ARG A | 900 | −6.211 | 39.071 | −55.276 | 1.00 | 55.74 | O |
| ATOM | 6531 | N | THR A | 901 | −4.043 | 39.127 | −55.809 | 1.00 | 45.86 | N |
| ATOM | 6532 | CA | THR A | 901 | −3.562 | 39.798 | −54.626 | 1.00 | 45.81 | C |
| ATOM | 6533 | CB | THR A | 901 | −2.064 | 39.875 | −54.727 | 1.00 | 44.98 | C |
| ATOM | 6534 | OG1 | THR A | 901 | −1.575 | 38.619 | −55.169 | 1.00 | 48.04 | O |
| ATOM | 6535 | CG2 | THR A | 901 | −1.488 | 40.195 | −53.431 | 1.00 | 45.13 | C |
| ATOM | 6536 | C | THR A | 901 | −3.975 | 41.235 | −54.463 | 1.00 | 45.73 | C |
| ATOM | 6537 | O | THR A | 901 | −4.079 | 41.950 | −55.421 | 1.00 | 47.29 | O |
| ATOM | 6538 | N | GLU A | 902 | −4.195 | 41.672 | −53.235 | 1.00 | 47.55 | N |
| ATOM | 6539 | CA | GLU A | 902 | −4.529 | 43.057 | −52.998 | 1.00 | 47.59 | C |
| ATOM | 6540 | CB | GLU A | 902 | −5.791 | 43.209 | −52.175 | 1.00 | 49.43 | C |
| ATOM | 6541 | CG | GLU A | 902 | −6.036 | 44.632 | −51.730 | 1.00 | 54.00 | C |
| ATOM | 6542 | CD | GLU A | 902 | −7.441 | 44.862 | −51.255 | 1.00 | 60.61 | C |
| ATOM | 6543 | OE1 | GLU A | 902 | −8.275 | 43.983 | −51.440 | 1.00 | 61.51 | O |
| ATOM | 6544 | OE2 | GLU A | 902 | −7.727 | 45.917 | −50.687 | 1.00 | 67.26 | O |
| ATOM | 6545 | C | GLU A | 902 | −3.389 | 43.725 | −52.282 | 1.00 | 47.41 | C |
| ATOM | 6546 | O | GLU A | 902 | −2.849 | 44.688 | −52.753 | 1.00 | 53.87 | O |
| ATOM | 6547 | N | CYS A | 903 | −3.006 | 43.195 | −51.141 | 1.00 | 50.09 | N |
| ATOM | 6548 | CA | CYS A | 903 | −1.921 | 43.761 | −50.372 | 1.00 | 51.56 | C |
| ATOM | 6549 | CB | CYS A | 903 | −2.388 | 44.776 | −49.362 | 1.00 | 52.84 | C |
| ATOM | 6550 | SG | CYS A | 903 | −3.980 | 44.436 | −48.688 | 1.00 | 59.26 | S |
| ATOM | 6551 | C | CYS A | 903 | −1.090 | 42.727 | −49.704 | 1.00 | 50.96 | C |
| ATOM | 6552 | O | CYS A | 903 | −1.393 | 41.573 | −49.725 | 1.00 | 49.13 | O |
| ATOM | 6553 | N | ASN A | 904 | 0.003 | 43.168 | −49.141 | 1.00 | 54.02 | N |
| ATOM | 6554 | CA | ASN A | 904 | 0.907 | 42.290 | −48.498 | 1.00 | 57.37 | C |
| ATOM | 6555 | CB | ASN A | 904 | 2.074 | 42.129 | −49.427 | 1.00 | 59.85 | C |
| ATOM | 6556 | CG | ASN A | 904 | 2.546 | 40.729 | −49.517 | 1.00 | 65.41 | C |
| ATOM | 6557 | OD1 | ASN A | 904 | 2.026 | 39.946 | −50.285 | 1.00 | 67.49 | O |
| ATOM | 6558 | ND2 | ASN A | 904 | 3.546 | 40.403 | −48.744 | 1.00 | 69.58 | N |
| ATOM | 6559 | C | ASN A | 904 | 1.419 | 42.967 | −47.273 | 1.00 | 63.35 | C |
| ATOM | 6560 | O | ASN A | 904 | 1.400 | 44.169 | −47.199 | 1.00 | 74.58 | O |
| ATOM | 6561 | N | HIS A | 905 | 1.867 | 42.209 | −46.293 | 1.00 | 64.19 | N |
| ATOM | 6562 | CA | HIS A | 905 | 2.471 | 42.804 | −45.129 | 1.00 | 62.31 | C |
| ATOM | 6563 | CB | HIS A | 905 | 1.526 | 42.911 | −43.984 | 1.00 | 61.77 | C |
| ATOM | 6564 | CG | HIS A | 905 | 1.856 | 44.040 | −43.081 | 1.00 | 64.50 | C |
| ATOM | 6565 | ND1 | HIS A | 905 | 3.025 | 44.089 | −42.361 | 1.00 | 67.98 | N |
| ATOM | 6566 | CE1 | HIS A | 905 | 3.063 | 45.209 | −41.672 | 1.00 | 68.31 | C |
| ATOM | 6567 | NE2 | HIS A | 905 | 1.968 | 45.892 | −41.931 | 1.00 | 67.67 | N |
| ATOM | 6568 | CD2 | HIS A | 905 | 1.201 | 45.187 | −42.818 | 1.00 | 64.82 | C |
| ATOM | 6569 | C | HIS A | 905 | 3.642 | 41.966 | −44.757 | 1.00 | 62.12 | C |
| ATOM | 6570 | O | HIS A | 905 | 3.499 | 40.785 | −44.606 | 1.00 | 66.78 | O |
| ATOM | 6571 | N | TYR A | 906 | 4.804 | 42.561 | −44.593 | 1.00 | 62.92 | N |
| ATOM | 6572 | CA | TYR A | 906 | 5.976 | 41.770 | −44.272 | 1.00 | 68.27 | C |
| ATOM | 6573 | CB | TYR A | 906 | 7.202 | 42.241 | −45.019 | 1.00 | 74.22 | C |
| ATOM | 6574 | CG | TYR A | 906 | 6.977 | 42.308 | −46.536 | 1.00 | 88.29 | C |
| ATOM | 6575 | CD1 | TYR A | 906 | 6.452 | 43.464 | −47.139 | 1.00 | 88.05 | C |
| ATOM | 6576 | CE1 | TYR A | 906 | 6.255 | 43.529 | −48.512 | 1.00 | 90.27 | C |
| ATOM | 6577 | CZ | TYR A | 906 | 6.582 | 42.447 | −49.311 | 1.00 | 91.26 | C |
| ATOM | 6578 | OH | TYR A | 906 | 6.381 | 42.564 | −50.665 | 1.00 | 92.72 | O |
| ATOM | 6579 | CE2 | TYR A | 906 | 7.094 | 41.276 | −48.757 | 1.00 | 90.90 | C |
| ATOM | 6580 | CD2 | TYR A | 906 | 7.288 | 41.206 | −47.378 | 1.00 | 92.76 | C |
| ATOM | 6581 | C | TYR A | 906 | 6.092 | 41.972 | −42.815 | 1.00 | 64.66 | C |
| ATOM | 6582 | O | TYR A | 906 | 5.714 | 43.033 | −42.341 | 1.00 | 63.31 | O |
| ATOM | 6583 | N | ASN A | 907 | 6.499 | 40.934 | −42.087 | 1.00 | 63.14 | N |
| ATOM | 6584 | CA | ASN A | 907 | 6.614 | 41.043 | −40.644 | 1.00 | 62.41 | C |
| ATOM | 6585 | CB | ASN A | 907 | 5.601 | 40.176 | −39.918 | 1.00 | 60.62 | C |
| ATOM | 6586 | CG | ASN A | 907 | 4.180 | 40.558 | −40.259 | 1.00 | 63.38 | C |
| ATOM | 6587 | OD1 | ASN A | 907 | 3.713 | 41.633 | −39.868 | 1.00 | 65.25 | O |
| ATOM | 6588 | ND2 | ASN A | 907 | 3.485 | 39.698 | −41.024 | 1.00 | 65.32 | N |
| ATOM | 6589 | C | ASN A | 907 | 7.984 | 40.651 | −40.285 | 1.00 | 62.72 | C |
| ATOM | 6590 | O | ASN A | 907 | 8.702 | 40.062 | −41.105 | 1.00 | 58.53 | O |
| ATOM | 6591 | N | ASN A | 908 | 8.337 | 41.003 | −39.055 | 1.00 | 66.67 | N |
| ATOM | 6592 | CA | ASN A | 908 | 9.598 | 40.562 | −38.450 | 1.00 | 74.19 | C |
| ATOM | 6593 | CB | ASN A | 908 | 10.298 | 41.698 | −37.624 | 1.00 | 80.35 | C |
| ATOM | 6594 | CG | ASN A | 908 | 9.319 | 42.592 | −36.855 | 1.00 | 83.02 | C |
| ATOM | 6595 | OD1 | ASN A | 908 | 8.754 | 42.199 | −35.841 | 1.00 | 74.98 | O |
| ATOM | 6596 | ND2 | ASN A | 908 | 9.128 | 43.810 | −37.343 | 1.00 | 93.04 | N |
| ATOM | 6597 | C | ASN A | 908 | 9.374 | 39.282 | −37.624 | 1.00 | 72.68 | C |
| ATOM | 6598 | O | ASN A | 908 | 10.251 | 38.859 | −36.841 | 1.00 | 79.76 | O |
| ATOM | 6599 | N | ILE A | 909 | 8.195 | 38.676 | −37.787 | 1.00 | 65.24 | N |
| ATOM | 6600 | CA | ILE A | 909 | 7.898 | 37.379 | −37.222 | 1.00 | 61.27 | C |

TABLE 6-continued

Atomic coordinates for CRBN:DDB1: Compound B (Human protein)

| ATOM | 6601 | CB | ILE A | 909 | 6.937 | 37.501 | −36.025 | 1.00 | 59.32 | C |
|---|---|---|---|---|---|---|---|---|---|---|
| ATOM | 6602 | CG1 | ILE A | 909 | 5.593 | 38.073 | −36.450 | 1.00 | 62.21 | C |
| ATOM | 6603 | CD1 | ILE A | 909 | 4.513 | 37.831 | −35.436 | 1.00 | 64.46 | C |
| ATOM | 6604 | CG2 | ILE A | 909 | 7.511 | 38.422 | −34.979 | 1.00 | 56.06 | C |
| ATOM | 6605 | C | ILE A | 909 | 7.307 | 36.503 | −38.321 | 1.00 | 60.19 | C |
| ATOM | 6606 | O | ILE A | 909 | 7.013 | 36.964 | −39.416 | 1.00 | 55.75 | O |
| ATOM | 6607 | N | MET A | 910 | 7.107 | 35.237 | −38.001 | 1.00 | 60.69 | N |
| ATOM | 6608 | CA | MET A | 910 | 6.603 | 34.276 | −38.966 | 1.00 | 61.94 | C |
| ATOM | 6609 | CB | MET A | 910 | 7.366 | 32.943 | −38.771 | 1.00 | 65.29 | C |
| ATOM | 6610 | CG | MET A | 910 | 6.645 | 31.631 | −39.025 | 1.00 | 72.90 | C |
| ATOM | 6611 | SD | MET A | 910 | 7.744 | 30.186 | −38.917 | 1.00 | 77.13 | S |
| ATOM | 6612 | CE | MET A | 910 | 8.620 | 30.275 | −40.506 | 1.00 | 83.84 | C |
| ATOM | 6613 | C | MET A | 910 | 5.122 | 34.241 | −38.667 | 1.00 | 62.01 | C |
| ATOM | 6614 | O | MET A | 910 | 4.759 | 34.043 | −37.542 | 1.00 | 73.46 | O |
| ATOM | 6615 | N | ALA A | 911 | 4.251 | 34.512 | −39.623 | 1.00 | 60.87 | N |
| ATOM | 6616 | CA | ALA A | 911 | 2.805 | 34.419 | −39.340 | 1.00 | 60.69 | C |
| ATOM | 6617 | CB | ALA A | 911 | 2.019 | 35.129 | −40.440 | 1.00 | 61.51 | C |
| ATOM | 6618 | C | ALA A | 911 | 2.273 | 32.969 | −39.148 | 1.00 | 56.88 | C |
| ATOM | 6619 | O | ALA A | 911 | 1.676 | 32.410 | −40.044 | 1.00 | 63.86 | O |
| ATOM | 6620 | N | LEU A | 912 | 2.466 | 32.355 | −38.002 | 1.00 | 51.31 | N |
| ATOM | 6621 | CA | LEU A | 912 | 1.876 | 31.055 | −37.813 | 1.00 | 54.90 | C |
| ATOM | 6622 | CB | LEU A | 912 | 2.470 | 30.298 | −36.660 | 1.00 | 57.97 | C |
| ATOM | 6623 | CG | LEU A | 912 | 3.900 | 29.897 | −36.806 | 1.00 | 65.96 | C |
| ATOM | 6624 | CD1 | LEU A | 912 | 4.144 | 28.902 | −35.685 | 1.00 | 70.20 | C |
| ATOM | 6625 | CD2 | LEU A | 912 | 4.192 | 29.293 | −38.170 | 1.00 | 68.34 | C |
| ATOM | 6626 | C | LEU A | 912 | 0.421 | 31.121 | −37.484 | 1.00 | 56.14 | C |
| ATOM | 6627 | O | LEU A | 912 | −0.334 | 30.258 | −37.894 | 1.00 | 66.03 | O |
| ATOM | 6628 | N | TYR A | 913 | 0.033 | 32.058 | −36.647 | 1.00 | 50.55 | N |
| ATOM | 6629 | CA | TYR A | 913 | −1.333 | 32.133 | −36.237 | 1.00 | 46.51 | C |
| ATOM | 6630 | CB | TYR A | 913 | −1.387 | 32.258 | −34.725 | 1.00 | 44.02 | C |
| ATOM | 6631 | CG | TYR A | 913 | −0.691 | 31.157 | −33.995 | 1.00 | 40.75 | C |
| ATOM | 6632 | CD1 | TYR A | 913 | −1.249 | 29.959 | −33.874 | 1.00 | 38.78 | C |
| ATOM | 6633 | CE1 | TYR A | 913 | −0.645 | 28.952 | −33.143 | 1.00 | 40.30 | C |
| ATOM | 6634 | CZ | TYR A | 913 | 0.592 | 29.121 | −32.562 | 1.00 | 42.09 | C |
| ATOM | 6635 | OH | TYR A | 913 | 1.230 | 28.087 | −31.880 | 1.00 | 40.03 | O |
| ATOM | 6636 | CE2 | TYR A | 913 | 1.177 | 30.352 | −32.660 | 1.00 | 43.94 | C |
| ATOM | 6637 | CD2 | TYR A | 913 | 0.520 | 31.364 | −33.367 | 1.00 | 44.13 | C |
| ATOM | 6638 | C | TYR A | 913 | −1.959 | 33.334 | −36.956 | 1.00 | 47.88 | C |
| ATOM | 6639 | O | TYR A | 913 | −1.293 | 34.304 | −37.214 | 1.00 | 55.04 | O |
| ATOM | 6640 | N | LEU A | 914 | −3.225 | 33.245 | −37.302 | 1.00 | 49.10 | N |
| ATOM | 6641 | CA | LEU A | 914 | −3.964 | 34.316 | −37.939 | 1.00 | 54.70 | C |
| ATOM | 6642 | CB | LEU A | 914 | −4.075 | 34.068 | −39.426 | 1.00 | 58.67 | C |
| ATOM | 6643 | CG | LEU A | 914 | −3.276 | 34.832 | −40.433 | 1.00 | 64.09 | C |
| ATOM | 6644 | CD1 | LEU A | 914 | −3.752 | 34.361 | −41.808 | 1.00 | 68.35 | C |
| ATOM | 6645 | CD2 | LEU A | 914 | −3.499 | 36.317 | −40.264 | 1.00 | 65.61 | C |
| ATOM | 6646 | C | LEU A | 914 | −5.367 | 34.204 | −37.451 | 1.00 | 54.78 | C |
| ATOM | 6647 | O | LEU A | 914 | −5.979 | 33.171 | −37.629 | 1.00 | 58.02 | O |
| ATOM | 6648 | N | LYS A | 915 | −5.905 | 35.242 | −36.873 | 1.00 | 52.85 | N |
| ATOM | 6649 | CA | LYS A | 915 | −7.286 | 35.223 | −36.519 | 1.00 | 51.64 | C |
| ATOM | 6650 | CB | LYS A | 915 | −7.344 | 34.940 | −35.045 | 1.00 | 55.39 | C |
| ATOM | 6651 | CG | LYS A | 915 | −6.802 | 33.584 | −34.649 | 1.00 | 58.45 | C |
| ATOM | 6652 | CD | LYS A | 915 | −7.718 | 32.456 | −35.156 | 1.00 | 63.14 | C |
| ATOM | 6653 | CE | LYS A | 915 | −7.186 | 31.065 | −34.834 | 1.00 | 63.03 | C |
| ATOM | 6654 | NZ | LYS A | 915 | −7.535 | 30.691 | −33.423 | 1.00 | 66.90 | N |
| ATOM | 6655 | C | LYS A | 915 | −7.800 | 36.601 | −36.857 | 1.00 | 50.19 | C |
| ATOM | 6656 | O | LYS A | 915 | −7.012 | 37.490 | −36.980 | 1.00 | 51.89 | O |
| ATOM | 6657 | N | THR A | 916 | −9.096 | 36.786 | −37.043 | 1.00 | 50.01 | N |
| ATOM | 6658 | CA | THR A | 916 | −9.650 | 38.103 | −37.355 | 1.00 | 52.88 | C |
| ATOM | 6659 | CB | THR A | 916 | −9.919 | 38.341 | −38.875 | 1.00 | 52.44 | C |
| ATOM | 6660 | OG1 | THR A | 916 | −10.931 | 37.454 | −39.321 | 1.00 | 57.44 | O |
| ATOM | 6661 | CG2 | THR A | 916 | −8.701 | 38.092 | −39.691 | 1.00 | 51.06 | C |
| ATOM | 6662 | C | THR A | 916 | −10.957 | 38.351 | −36.622 | 1.00 | 56.19 | C |
| ATOM | 6663 | O | THR A | 916 | −11.638 | 37.415 | −36.184 | 1.00 | 55.43 | O |
| ATOM | 6664 | N | LYS A | 917 | −11.264 | 39.644 | −36.480 | 1.00 | 60.57 | N |
| ATOM | 6665 | CA | LYS A | 917 | −12.535 | 40.136 | −35.979 | 1.00 | 61.28 | C |
| ATOM | 6666 | CB | LYS A | 917 | −12.552 | 40.428 | −34.458 | 1.00 | 59.53 | C |
| ATOM | 6667 | CG | LYS A | 917 | −14.003 | 40.606 | −34.038 | 1.00 | 63.94 | C |
| ATOM | 6668 | CD | LYS A | 917 | −14.334 | 41.143 | −32.662 | 1.00 | 68.91 | C |
| ATOM | 6669 | CE | LYS A | 917 | −15.871 | 41.232 | −32.575 | 1.00 | 75.74 | C |
| ATOM | 6670 | NZ | LYS A | 917 | −16.414 | 41.739 | −31.279 | 1.00 | 81.55 | N |
| ATOM | 6671 | C | LYS A | 917 | −12.835 | 41.391 | −36.761 | 1.00 | 64.84 | C |
| ATOM | 6672 | O | LYS A | 917 | −12.175 | 42.420 | −36.567 | 1.00 | 63.19 | O |
| ATOM | 6673 | N | GLY A | 918 | −13.820 | 41.300 | −37.652 | 1.00 | 70.55 | N |
| ATOM | 6674 | CA | GLY A | 918 | −14.176 | 42.429 | −38.503 | 1.00 | 71.54 | C |
| ATOM | 6675 | C | GLY A | 918 | −13.006 | 42.680 | −39.433 | 1.00 | 72.80 | C |
| ATOM | 6676 | O | GLY A | 918 | −12.492 | 41.717 | −40.058 | 1.00 | 73.84 | O |
| ATOM | 6677 | N | ASP A | 919 | −12.576 | 43.950 | −39.477 | 1.00 | 70.04 | N |
| ATOM | 6678 | CA | ASP A | 919 | −11.353 | 44.358 | −40.168 | 1.00 | 69.93 | C |

TABLE 6-continued

Atomic coordinates for CRBN:DDB1: Compound B (Human protein)

| ATOM | 6679 | CB | ASP A | 919 | −11.452 | 45.818 | −40.648 | 1.00 | 73.59 | C |
|---|---|---|---|---|---|---|---|---|---|---|
| ATOM | 6680 | CG | ASP A | 919 | −12.310 | 46.007 | −41.921 | 1.00 | 77.10 | C |
| ATOM | 6681 | OD1 | ASP A | 919 | −12.790 | 45.016 | −42.535 | 1.00 | 72.82 | O |
| ATOM | 6682 | OD2 | ASP A | 919 | −12.494 | 47.203 | −42.302 | 1.00 | 81.93 | O |
| ATOM | 6683 | C | ASP A | 919 | −10.062 | 44.205 | −39.331 | 1.00 | 69.26 | C |
| ATOM | 6684 | O | ASP A | 919 | −8.984 | 44.479 | −39.880 | 1.00 | 61.62 | O |
| ATOM | 6685 | N | PHE A | 920 | −10.150 | 43.796 | −38.036 | 1.00 | 73.69 | N |
| ATOM | 6686 | CA | PHE A | 920 | −8.945 | 43.579 | −37.147 | 1.00 | 72.44 | C |
| ATOM | 6687 | CB | PHE A | 920 | −9.252 | 43.703 | −35.632 | 1.00 | 77.60 | C |
| ATOM | 6688 | CG | PHE A | 920 | −9.588 | 45.119 | −35.167 | 1.00 | 99.97 | C |
| ATOM | 6689 | CD1 | PHE A | 920 | −8.606 | 46.127 | −35.116 | 1.00 | 106.06 | C |
| ATOM | 6690 | CE1 | PHE A | 920 | −8.919 | 47.426 | −34.693 | 1.00 | 104.91 | C |
| ATOM | 6691 | CZ | PHE A | 920 | −10.217 | 47.743 | −34.301 | 1.00 | 104.72 | C |
| ATOM | 6692 | CE2 | PHE A | 920 | −11.204 | 46.770 | −34.329 | 1.00 | 108.32 | C |
| ATOM | 6693 | CD2 | PHE A | 920 | −10.895 | 45.462 | −34.751 | 1.00 | 111.83 | C |
| ATOM | 6694 | C | PHE A | 920 | −8.309 | 42.208 | −37.456 | 1.00 | 66.97 | C |
| ATOM | 6695 | O | PHE A | 920 | −9.012 | 41.231 | −37.672 | 1.00 | 61.17 | O |
| ATOM | 6696 | N | ILE A | 921 | −6.984 | 42.153 | −37.512 | 1.00 | 61.05 | N |
| ATOM | 6697 | CA | ILE A | 921 | −6.269 | 40.954 | −37.860 | 1.00 | 56.97 | C |
| ATOM | 6698 | CB | ILE A | 921 | −5.551 | 41.123 | −39.181 | 1.00 | 60.08 | C |
| ATOM | 6699 | CG1 | ILE A | 921 | −6.576 | 41.297 | −40.280 | 1.00 | 67.84 | C |
| ATOM | 6700 | CD1 | ILE A | 921 | −5.956 | 41.686 | −41.605 | 1.00 | 75.47 | C |
| ATOM | 6701 | CG2 | ILE A | 921 | −4.684 | 39.920 | −39.503 | 1.00 | 56.91 | C |
| ATOM | 6702 | C | ILE A | 921 | −5.225 | 40.748 | −36.814 | 1.00 | 57.18 | C |
| ATOM | 6703 | O | ILE A | 921 | −4.458 | 41.647 | −36.558 | 1.00 | 59.53 | O |
| ATOM | 6704 | N | LEU A | 922 | −5.194 | 39.552 | −36.235 | 1.00 | 57.28 | N |
| ATOM | 6705 | CA | LEU A | 922 | −4.251 | 39.153 | −35.205 | 1.00 | 55.22 | C |
| ATOM | 6706 | CB | LEU A | 922 | −5.021 | 38.497 | −34.060 | 1.00 | 56.07 | C |
| ATOM | 6707 | CG | LEU A | 922 | −4.201 | 37.743 | −33.010 | 1.00 | 59.51 | C |
| ATOM | 6708 | CD1 | LEU A | 922 | −2.986 | 38.521 | −32.575 | 1.00 | 61.52 | C |
| ATOM | 6709 | CD2 | LEU A | 922 | −5.056 | 37.457 | −31.787 | 1.00 | 62.40 | C |
| ATOM | 6710 | C | LEU A | 922 | −3.247 | 38.152 | −35.782 | 1.00 | 53.46 | C |
| ATOM | 6711 | O | LEU A | 922 | −3.649 | 37.119 | −36.353 | 1.00 | 52.00 | O |
| ATOM | 6712 | N | VAL A | 923 | −1.956 | 38.450 | −35.633 | 1.00 | 49.17 | N |
| ATOM | 6713 | CA | VAL A | 923 | −0.908 | 37.535 | −36.080 | 1.00 | 49.35 | C |
| ATOM | 6714 | CB | VAL A | 923 | 0.055 | 38.168 | −37.108 | 1.00 | 48.68 | C |
| ATOM | 6715 | CG1 | VAL A | 923 | 1.068 | 37.127 | −37.570 | 1.00 | 48.17 | C |
| ATOM | 6716 | CG2 | VAL A | 923 | −0.686 | 38.720 | −38.320 | 1.00 | 49.54 | C |
| ATOM | 6717 | C | VAL A | 923 | −0.049 | 37.073 | −34.936 | 1.00 | 49.90 | C |
| ATOM | 6718 | O | VAL A | 923 | 0.309 | 37.858 | −34.100 | 1.00 | 51.63 | O |
| ATOM | 6719 | N | GLY A | 924 | 0.368 | 35.815 | −34.941 | 1.00 | 51.22 | N |
| ATOM | 6720 | CA | GLY A | 924 | 1.264 | 35.323 | −33.885 | 1.00 | 50.24 | C |
| ATOM | 6721 | C | GLY A | 924 | 2.276 | 34.379 | −34.460 | 1.00 | 48.41 | C |
| ATOM | 6722 | O | GLY A | 924 | 1.952 | 33.695 | −35.441 | 1.00 | 44.82 | O |
| ATOM | 6723 | N | ASP A | 925 | 3.494 | 34.401 | −33.893 | 1.00 | 48.42 | N |
| ATOM | 6724 | CA | ASP A | 925 | 4.503 | 33.352 | −34.098 | 1.00 | 51.92 | C |
| ATOM | 6725 | CB | ASP A | 925 | 5.909 | 33.932 | −34.496 | 1.00 | 57.33 | C |
| ATOM | 6726 | CG | ASP A | 925 | 6.757 | 34.468 | −33.304 | 1.00 | 58.69 | C |
| ATOM | 6727 | OD1 | ASP A | 925 | 6.160 | 34.828 | −32.275 | 1.00 | 60.93 | O |
| ATOM | 6728 | OD2 | ASP A | 925 | 8.021 | 34.541 | −33.401 | 1.00 | 55.19 | O |
| ATOM | 6729 | C | ASP A | 925 | 4.549 | 32.413 | −32.885 | 1.00 | 52.01 | C |
| ATOM | 6730 | O | ASP A | 925 | 3.883 | 32.647 | −31.861 | 1.00 | 50.91 | O |
| ATOM | 6731 | N | LEU A | 926 | 5.345 | 31.355 | −33.014 | 1.00 | 51.49 | N |
| ATOM | 6732 | CA | LEU A | 926 | 5.426 | 30.284 | −32.008 | 1.00 | 50.62 | C |
| ATOM | 6733 | CB | LEU A | 926 | 6.238 | 29.108 | −32.564 | 1.00 | 52.79 | C |
| ATOM | 6734 | CG | LEU A | 926 | 6.373 | 27.807 | −31.763 | 1.00 | 53.25 | C |
| ATOM | 6735 | CD1 | LEU A | 926 | 5.017 | 27.111 | −31.638 | 1.00 | 57.86 | C |
| ATOM | 6736 | CD2 | LEU A | 926 | 7.391 | 26.876 | −32.394 | 1.00 | 53.11 | C |
| ATOM | 6737 | C | LEU A | 926 | 6.110 | 30.759 | −30.752 | 1.00 | 50.29 | C |
| ATOM | 6738 | O | LEU A | 926 | 6.198 | 30.059 | −29.744 | 1.00 | 48.89 | O |
| ATOM | 6739 | N | MET A | 927 | 6.625 | 31.956 | −30.794 | 1.00 | 50.81 | N |
| ATOM | 6740 | CA | MET A | 927 | 7.381 | 32.402 | −29.695 | 1.00 | 52.43 | C |
| ATOM | 6741 | CB | MET A | 927 | 8.742 | 32.783 | −30.243 | 1.00 | 53.16 | C |
| ATOM | 6742 | CG | MET A | 927 | 9.843 | 32.206 | −29.418 | 1.00 | 54.03 | C |
| ATOM | 6743 | SD | MET A | 927 | 11.338 | 31.887 | −30.345 | 1.00 | 50.64 | S |
| ATOM | 6744 | CE | MET A | 927 | 12.296 | 31.443 | −28.897 | 1.00 | 53.80 | C |
| ATOM | 6745 | C | MET A | 927 | 6.616 | 33.507 | −28.950 | 1.00 | 49.65 | C |
| ATOM | 6746 | O | MET A | 927 | 7.207 | 34.333 | −28.271 | 1.00 | 47.70 | O |
| ATOM | 6747 | N | ARG A | 928 | 5.286 | 33.493 | −29.090 | 1.00 | 49.59 | N |
| ATOM | 6748 | CA | ARG A | 928 | 4.388 | 34.327 | −28.325 | 1.00 | 51.23 | C |
| ATOM | 6749 | CB | ARG A | 928 | 4.534 | 33.950 | −26.824 | 1.00 | 54.70 | C |
| ATOM | 6750 | CG | ARG A | 928 | 4.234 | 34.936 | −25.705 | 1.00 | 58.79 | C |
| ATOM | 6751 | CD | ARG A | 928 | 2.768 | 35.021 | −25.403 | 1.00 | 61.00 | C |
| ATOM | 6752 | NE | ARG A | 928 | 2.522 | 35.548 | −24.060 | 1.00 | 65.27 | N |
| ATOM | 6753 | CZ | ARG A | 928 | 2.453 | 36.833 | −23.710 | 1.00 | 64.60 | C |
| ATOM | 6754 | NH1 | ARG A | 928 | 2.631 | 37.834 | −24.593 | 1.00 | 60.67 | N |
| ATOM | 6755 | NH2 | ARG A | 928 | 2.188 | 37.094 | −22.427 | 1.00 | 66.73 | N |
| ATOM | 6756 | C | ARG A | 928 | 4.544 | 35.804 | −28.682 | 1.00 | 50.79 | C |

TABLE 6-continued

Atomic coordinates for CRBN:DDB1: Compound B (Human protein)

| ATOM | 6757 | O | ARG A | 928 | 3.974 | 36.648 | −28.015 | 1.00 | 54.23 | O |
|---|---|---|---|---|---|---|---|---|---|---|
| ATOM | 6758 | N | SER A | 929 | 5.259 | 36.126 | −29.769 | 1.00 | 50.86 | N |
| ATOM | 6759 | CA | SER A | 929 | 5.219 | 37.480 | −30.341 | 1.00 | 50.78 | C |
| ATOM | 6760 | CB | SER A | 929 | 6.230 | 37.761 | −31.451 | 1.00 | 50.37 | C |
| ATOM | 6761 | OG | SER A | 929 | 7.324 | 36.879 | −31.460 | 1.00 | 55.31 | O |
| ATOM | 6762 | C | SER A | 929 | 3.870 | 37.575 | −30.954 | 1.00 | 51.91 | C |
| ATOM | 6763 | O | SER A | 929 | 3.451 | 36.640 | −31.611 | 1.00 | 58.71 | O |
| ATOM | 6764 | N | VAL A | 930 | 3.167 | 38.677 | −30.732 | 1.00 | 52.81 | N |
| ATOM | 6765 | CA | VAL A | 930 | 1.875 | 38.871 | −31.366 | 1.00 | 52.03 | C |
| ATOM | 6766 | CB | VAL A | 930 | 0.677 | 38.479 | −30.487 | 1.00 | 46.42 | C |
| ATOM | 6767 | CG1 | VAL A | 930 | 1.124 | 37.697 | −29.278 | 1.00 | 45.68 | C |
| ATOM | 6768 | CG2 | VAL A | 930 | −0.119 | 39.683 | −30.066 | 1.00 | 46.36 | C |
| ATOM | 6769 | C | VAL A | 930 | 1.782 | 40.296 | −31.855 | 1.00 | 55.93 | C |
| ATOM | 6770 | O | VAL A | 930 | 2.387 | 41.196 | −31.272 | 1.00 | 61.03 | O |
| ATOM | 6771 | N | LEU A | 931 | 1.009 | 40.443 | −32.929 | 1.00 | 56.79 | N |
| ATOM | 6772 | CA | LEU A | 931 | 0.830 | 41.649 | −33.701 | 1.00 | 55.28 | C |
| ATOM | 6773 | CB | LEU A | 931 | 1.401 | 41.451 | −35.077 | 1.00 | 55.57 | C |
| ATOM | 6774 | CG | LEU A | 931 | 2.724 | 42.144 | −35.210 | 1.00 | 59.06 | C |
| ATOM | 6775 | CD1 | LEU A | 931 | 3.790 | 41.367 | −34.462 | 1.00 | 61.01 | C |
| ATOM | 6776 | CD2 | LEU A | 931 | 3.020 | 42.286 | −36.690 | 1.00 | 63.32 | C |
| ATOM | 6777 | C | LEU A | 931 | −0.631 | 41.942 | −33.886 | 1.00 | 57.65 | C |
| ATOM | 6778 | O | LEU A | 931 | −1.485 | 41.092 | −33.719 | 1.00 | 62.29 | O |
| ATOM | 6779 | N | LEU A | 932 | −0.935 | 43.153 | −34.286 | 1.00 | 59.79 | N |
| ATOM | 6780 | CA | LEU A | 932 | −2.308 | 43.505 | −34.417 | 1.00 | 61.15 | C |
| ATOM | 6781 | CB | LEU A | 932 | −2.780 | 44.098 | −33.100 | 1.00 | 65.94 | C |
| ATOM | 6782 | CG | LEU A | 932 | −4.257 | 44.422 | −33.060 | 1.00 | 71.78 | C |
| ATOM | 6783 | CD1 | LEU A | 932 | −5.075 | 43.150 | −33.186 | 1.00 | 74.04 | C |
| ATOM | 6784 | CD2 | LEU A | 932 | −4.560 | 45.153 | −31.764 | 1.00 | 74.17 | C |
| ATOM | 6785 | C | LEU A | 932 | −2.428 | 44.442 | −35.566 | 1.00 | 54.97 | C |
| ATOM | 6786 | O | LEU A | 932 | −2.346 | 45.597 | −35.380 | 1.00 | 56.08 | O |
| ATOM | 6787 | N | LEU A | 933 | −2.573 | 43.887 | −36.757 | 1.00 | 53.78 | N |
| ATOM | 6788 | CA | LEU A | 933 | −2.742 | 44.617 | −37.994 | 1.00 | 55.06 | C |
| ATOM | 6789 | CB | LEU A | 933 | −2.270 | 43.745 | −39.138 | 1.00 | 54.03 | C |
| ATOM | 6790 | CG | LEU A | 933 | −0.882 | 43.133 | −39.111 | 1.00 | 56.58 | C |
| ATOM | 6791 | CD1 | LEU A | 933 | −0.766 | 42.108 | −40.218 | 1.00 | 60.26 | C |
| ATOM | 6792 | CD2 | LEU A | 933 | 0.182 | 44.173 | −39.333 | 1.00 | 60.95 | C |
| ATOM | 6793 | C | LEU A | 933 | −4.218 | 45.012 | −38.275 | 1.00 | 58.09 | C |
| ATOM | 6794 | O | LEU A | 933 | −5.144 | 44.365 | −37.785 | 1.00 | 61.84 | O |
| ATOM | 6795 | N | ALA A | 934 | −4.416 | 46.067 | −39.070 | 1.00 | 57.42 | N |
| ATOM | 6796 | CA | ALA A | 934 | −5.732 | 46.440 | −39.588 | 1.00 | 59.78 | C |
| ATOM | 6797 | CB | ALA A | 934 | −6.248 | 47.680 | −38.905 | 1.00 | 58.67 | C |
| ATOM | 6798 | C | ALA A | 934 | −5.707 | 46.690 | −41.090 | 1.00 | 62.20 | C |
| ATOM | 6799 | O | ALA A | 934 | −4.716 | 47.167 | −41.666 | 1.00 | 62.21 | O |
| ATOM | 6800 | N | TYR A | 935 | −6.835 | 46.388 | −41.708 | 1.00 | 61.90 | N |
| ATOM | 6801 | CA | TYR A | 935 | −7.032 | 46.658 | −43.097 | 1.00 | 60.92 | C |
| ATOM | 6802 | CB | TYR A | 935 | −7.890 | 45.581 | −43.736 | 1.00 | 60.76 | C |
| ATOM | 6803 | CG | TYR A | 935 | −8.188 | 45.803 | −45.187 | 1.00 | 61.27 | C |
| ATOM | 6804 | CD1 | TYR A | 935 | −7.199 | 45.691 | −46.141 | 1.00 | 65.28 | C |
| ATOM | 6805 | CE1 | TYR A | 935 | −7.477 | 45.870 | −47.488 | 1.00 | 68.24 | C |
| ATOM | 6806 | CZ | TYR A | 935 | −8.768 | 46.167 | −47.874 | 1.00 | 67.35 | C |
| ATOM | 6807 | OH | TYR A | 935 | −9.075 | 46.362 | −49.192 | 1.00 | 69.30 | O |
| ATOM | 6808 | CE2 | TYR A | 935 | −9.765 | 46.271 | −46.936 | 1.00 | 63.36 | C |
| ATOM | 6809 | CD2 | TYR A | 935 | −9.468 | 46.091 | −45.608 | 1.00 | 62.68 | C |
| ATOM | 6810 | C | TYR A | 935 | −7.689 | 48.009 | −43.132 | 1.00 | 60.63 | C |
| ATOM | 6811 | O | TYR A | 935 | −8.484 | 48.366 | −42.280 | 1.00 | 59.00 | O |
| ATOM | 6812 | N | LYS A | 936 | −7.288 | 48.772 | −44.117 | 1.00 | 64.70 | N |
| ATOM | 6813 | CA | LYS A | 936 | −7.707 | 50.123 | −44.275 | 1.00 | 69.16 | C |
| ATOM | 6814 | CB | LYS A | 936 | −6.530 | 51.079 | −44.009 | 1.00 | 73.80 | C |
| ATOM | 6815 | CG | LYS A | 936 | −6.107 | 51.195 | −42.540 | 1.00 | 77.49 | C |
| ATOM | 6816 | CD | LYS A | 936 | −7.273 | 51.672 | −41.658 | 1.00 | 84.16 | C |
| ATOM | 6817 | CE | LYS A | 936 | −6.967 | 51.653 | −40.169 | 1.00 | 89.81 | C |
| ATOM | 6818 | NZ | LYS A | 936 | −5.903 | 52.633 | −39.844 | 1.00 | 95.51 | N |
| ATOM | 6819 | C | LYS A | 936 | −8.223 | 50.169 | −45.706 | 1.00 | 69.78 | C |
| ATOM | 6820 | O | LYS A | 936 | −7.454 | 50.265 | −46.663 | 1.00 | 66.02 | O |
| ATOM | 6821 | N | PRO A | 937 | −9.540 | 50.057 | −45.867 | 1.00 | 71.21 | N |
| ATOM | 6822 | CA | PRO A | 937 | −10.092 | 49.989 | −47.222 | 1.00 | 73.53 | C |
| ATOM | 6823 | CB | PRO A | 937 | −11.586 | 49.756 | −46.988 | 1.00 | 73.18 | C |
| ATOM | 6824 | CG | PRO A | 937 | −11.720 | 49.430 | −45.529 | 1.00 | 70.50 | C |
| ATOM | 6825 | CD | PRO A | 937 | −10.589 | 50.086 | −44.841 | 1.00 | 69.63 | C |
| ATOM | 6826 | C | PRO A | 937 | −9.881 | 51.256 | −48.028 | 1.00 | 73.87 | C |
| ATOM | 6827 | O | PRO A | 937 | −9.642 | 51.157 | −49.216 | 1.00 | 75.16 | O |
| ATOM | 6828 | N | MET A | 938 | −9.981 | 52.415 | −47.367 | 1.00 | 78.37 | N |
| ATOM | 6829 | CA | MET A | 938 | −9.657 | 53.727 | −47.959 | 1.00 | 81.51 | C |
| ATOM | 6830 | CB | MET A | 938 | −10.013 | 54.904 | −47.016 | 1.00 | 83.62 | C |
| ATOM | 6831 | CG | MET A | 938 | −11.485 | 55.281 | −46.912 | 1.00 | 86.08 | C |
| ATOM | 6832 | SD | MET A | 938 | −11.797 | 56.821 | −45.979 | 1.00 | 97.74 | S |
| ATOM | 6833 | CE | MET A | 938 | −11.357 | 56.517 | −44.255 | 1.00 | 94.85 | C |
| ATOM | 6834 | C | MET A | 938 | −8.184 | 53.885 | −48.338 | 1.00 | 79.20 | C |

TABLE 6-continued

Atomic coordinates for CRBN:DDB1: Compound B (Human protein)

| ATOM | 6835 | O | MET A | 938 | −7.873 | 54.817 | −49.062 | 1.00 | 88.01 | O |
|---|---|---|---|---|---|---|---|---|---|---|
| ATOM | 6836 | N | GLU A | 939 | −7.285 | 53.039 | −47.829 | 1.00 | 73.71 | N |
| ATOM | 6837 | CA | GLU A | 939 | −5.855 | 53.140 | −48.118 | 1.00 | 71.56 | C |
| ATOM | 6838 | CB | GLU A | 939 | −5.114 | 53.362 | −46.790 | 1.00 | 80.54 | C |
| ATOM | 6839 | CG | GLU A | 939 | −3.672 | 53.878 | −46.852 | 1.00 | 88.10 | C |
| ATOM | 6840 | CD | GLU A | 939 | −2.753 | 53.145 | −45.862 | 1.00 | 95.88 | C |
| ATOM | 6841 | OE1 | GLU A | 939 | −2.310 | 53.787 | −44.893 | 1.00 | 99.69 | O |
| ATOM | 6842 | OE2 | GLU A | 939 | −2.494 | 51.919 | −46.020 | 1.00 | 96.97 | O |
| ATOM | 6843 | C | GLU A | 939 | −5.304 | 51.923 | −48.883 | 1.00 | 65.65 | C |
| ATOM | 6844 | O | GLU A | 939 | −4.128 | 51.904 | −49.209 | 1.00 | 58.41 | O |
| ATOM | 6845 | N | GLY A | 940 | −6.151 | 50.924 | −49.178 | 1.00 | 67.55 | N |
| ATOM | 6846 | CA | GLY A | 940 | −5.757 | 49.668 | −49.857 | 1.00 | 67.67 | C |
| ATOM | 6847 | C | GLY A | 940 | −4.698 | 48.723 | −49.267 | 1.00 | 68.12 | C |
| ATOM | 6848 | O | GLY A | 940 | −4.364 | 47.760 | −49.910 | 1.00 | 73.43 | O |
| ATOM | 6849 | N | ASN A | 941 | −4.185 | 48.974 | −48.064 | 1.00 | 68.84 | N |
| ATOM | 6850 | CA | ASN A | 941 | −3.079 | 48.211 | −47.479 | 1.00 | 71.70 | C |
| ATOM | 6851 | CB | ASN A | 941 | −1.783 | 48.991 | −47.612 | 1.00 | 75.00 | C |
| ATOM | 6852 | CG | ASN A | 941 | −0.587 | 48.081 | −47.802 | 1.00 | 83.48 | C |
| ATOM | 6853 | OD1 | ASN A | 941 | −0.281 | 47.718 | −48.927 | 1.00 | 88.10 | O |
| ATOM | 6854 | ND2 | ASN A | 941 | 0.085 | 47.683 | −46.702 | 1.00 | 87.38 | N |
| ATOM | 6855 | C | ASN A | 941 | −3.342 | 47.940 | −46.000 | 1.00 | 72.07 | C |
| ATOM | 6856 | O | ASN A | 941 | −4.352 | 48.387 | −45.501 | 1.00 | 81.25 | O |
| ATOM | 6857 | N | PHE A | 942 | −2.475 | 47.189 | −45.311 | 1.00 | 68.43 | N |
| ATOM | 6858 | CA | PHE A | 942 | −2.547 | 47.003 | −43.844 | 1.00 | 65.95 | C |
| ATOM | 6859 | CB | PHE A | 942 | −2.011 | 45.622 | −43.471 | 1.00 | 67.86 | C |
| ATOM | 6860 | CG | PHE A | 942 | −2.730 | 44.493 | −44.112 | 1.00 | 67.00 | C |
| ATOM | 6861 | CD1 | PHE A | 942 | −4.024 | 44.180 | −43.724 | 1.00 | 67.57 | C |
| ATOM | 6862 | CE1 | PHE A | 942 | −4.692 | 43.124 | −44.305 | 1.00 | 68.45 | C |
| ATOM | 6863 | CZ | PHE A | 942 | −4.069 | 42.360 | −45.284 | 1.00 | 68.94 | C |
| ATOM | 6864 | CE2 | PHE A | 942 | −2.768 | 42.655 | −45.672 | 1.00 | 70.04 | C |
| ATOM | 6865 | CD2 | PHE A | 942 | −2.104 | 43.718 | −45.080 | 1.00 | 67.97 | C |
| ATOM | 6866 | C | PHE A | 942 | −1.700 | 48.001 | −43.040 | 1.00 | 63.61 | C |
| ATOM | 6867 | O | PHE A | 942 | −0.587 | 48.305 | −43.476 | 1.00 | 60.58 | O |
| ATOM | 6868 | N | GLU A | 943 | −2.191 | 48.422 | −41.857 | 1.00 | 62.40 | N |
| ATOM | 6869 | CA | GLU A | 943 | −1.433 | 49.237 | −40.841 | 1.00 | 66.30 | C |
| ATOM | 6870 | CB | GLU A | 943 | −2.295 | 50.455 | −40.436 | 1.00 | 71.73 | C |
| ATOM | 6871 | CG | GLU A | 943 | −1.548 | 51.614 | −39.738 | 1.00 | 78.47 | C |
| ATOM | 6872 | CD | GLU A | 943 | −2.311 | 52.319 | −38.582 | 1.00 | 81.22 | C |
| ATOM | 6873 | OE1 | GLU A | 943 | −3.554 | 52.469 | −38.611 | 1.00 | 79.65 | O |
| ATOM | 6874 | OE2 | GLU A | 943 | −1.650 | 52.748 | −37.606 | 1.00 | 84.44 | O |
| ATOM | 6875 | C | GLU A | 943 | −1.122 | 48.446 | −39.540 | 1.00 | 64.14 | C |
| ATOM | 6876 | O | GLU A | 943 | −2.017 | 47.788 | −39.051 | 1.00 | 65.92 | O |
| ATOM | 6877 | N | GLU A | 944 | 0.068 | 48.535 | −38.934 | 1.00 | 62.32 | N |
| ATOM | 6878 | CA | GLU A | 944 | 0.233 | 48.006 | −37.531 | 1.00 | 65.54 | C |
| ATOM | 6879 | CB | GLU A | 944 | 1.668 | 48.066 | −37.032 | 1.00 | 70.50 | C |
| ATOM | 6880 | CG | GLU A | 944 | 2.665 | 47.307 | −37.884 | 1.00 | 76.50 | C |
| ATOM | 6881 | CD | GLU A | 944 | 3.552 | 46.393 | −37.058 | 1.00 | 82.95 | C |
| ATOM | 6882 | OE1 | GLU A | 944 | 3.640 | 46.582 | −35.794 | 1.00 | 73.57 | O |
| ATOM | 6883 | OE2 | GLU A | 944 | 4.141 | 45.473 | −37.706 | 1.00 | 91.19 | O |
| ATOM | 6884 | C | GLU A | 944 | −0.540 | 48.809 | −36.508 | 1.00 | 60.65 | C |
| ATOM | 6885 | O | GLU A | 944 | −0.459 | 50.021 | −36.530 | 1.00 | 64.70 | O |
| ATOM | 6886 | N | ILE A | 945 | −1.253 | 48.157 | −35.601 | 1.00 | 57.11 | N |
| ATOM | 6887 | CA | ILE A | 945 | −1.982 | 48.856 | −34.522 | 1.00 | 57.87 | C |
| ATOM | 6888 | CB | ILE A | 945 | −3.440 | 48.370 | −34.356 | 1.00 | 60.81 | C |
| ATOM | 6889 | CG1 | ILE A | 945 | −4.125 | 48.232 | −35.699 | 1.00 | 64.60 | C |
| ATOM | 6890 | CD1 | ILE A | 945 | −3.930 | 49.417 | −36.613 | 1.00 | 67.81 | C |
| ATOM | 6891 | CG2 | ILE A | 945 | −4.270 | 49.327 | −33.504 | 1.00 | 66.21 | C |
| ATOM | 6892 | C | ILE A | 945 | −1.321 | 48.706 | −33.169 | 1.00 | 57.86 | C |
| ATOM | 6893 | O | ILE A | 945 | −1.544 | 49.524 | −32.301 | 1.00 | 60.34 | O |
| ATOM | 6894 | N | ALA A | 946 | −0.502 | 47.677 | −32.988 | 1.00 | 60.88 | N |
| ATOM | 6895 | CA | ALA A | 946 | −0.031 | 47.260 | −31.653 | 1.00 | 60.42 | C |
| ATOM | 6896 | CB | ALA A | 946 | −1.184 | 47.132 | −30.663 | 1.00 | 58.22 | C |
| ATOM | 6897 | C | ALA A | 946 | 0.712 | 45.942 | −31.737 | 1.00 | 63.27 | C |
| ATOM | 6898 | O | ALA A | 946 | 0.642 | 45.238 | −32.739 | 1.00 | 70.57 | O |
| ATOM | 6899 | N | ARG A | 947 | 1.415 | 45.616 | −30.664 | 1.00 | 65.32 | N |
| ATOM | 6900 | CA | ARG A | 947 | 2.311 | 44.473 | −30.632 | 1.00 | 63.84 | C |
| ATOM | 6901 | CB | ARG A | 947 | 3.472 | 44.725 | −31.600 | 1.00 | 63.47 | C |
| ATOM | 6902 | CG | ARG A | 947 | 4.878 | 44.691 | −31.024 | 1.00 | 69.15 | C |
| ATOM | 6903 | CD | ARG A | 947 | 5.940 | 45.101 | −32.042 | 1.00 | 74.73 | C |
| ATOM | 6904 | NE | ARG A | 947 | 5.518 | 44.905 | −33.445 | 1.00 | 80.73 | N |
| ATOM | 6905 | CZ | ARG A | 947 | 6.268 | 44.382 | −34.419 | 1.00 | 84.24 | C |
| ATOM | 6906 | NH1 | ARG A | 947 | 7.520 | 43.980 | −34.207 | 1.00 | 91.10 | N |
| ATOM | 6907 | NH2 | ARG A | 947 | 5.757 | 44.268 | −35.634 | 1.00 | 83.66 | N |
| ATOM | 6908 | C | ARG A | 947 | 2.768 | 44.199 | −29.190 | 1.00 | 65.56 | C |
| ATOM | 6909 | O | ARG A | 947 | 2.702 | 45.067 | −28.316 | 1.00 | 68.19 | O |
| ATOM | 6910 | N | ASP A | 948 | 3.164 | 42.963 | −28.954 | 1.00 | 66.85 | N |
| ATOM | 6911 | CA | ASP A | 948 | 3.811 | 42.547 | −27.715 | 1.00 | 70.62 | C |
| ATOM | 6912 | CB | ASP A | 948 | 2.761 | 42.073 | −26.703 | 1.00 | 75.68 | C |

TABLE 6-continued

Atomic coordinates for CRBN:DDB1: Compound B (Human protein)

| ATOM | 6913 | CG | ASP A | 948 | 3.361 | 41.574 | −25.374 | 1.00 | 81.91 | C |
|---|---|---|---|---|---|---|---|---|---|---|
| ATOM | 6914 | OD1 | ASP A | 948 | 4.607 | 41.464 | −25.205 | 1.00 | 83.82 | O |
| ATOM | 6915 | OD2 | ASP A | 948 | 2.537 | 41.277 | −24.480 | 1.00 | 83.63 | O |
| ATOM | 6916 | C | ASP A | 948 | 4.738 | 41.419 | −28.138 | 1.00 | 65.34 | C |
| ATOM | 6917 | O | ASP A | 948 | 4.391 | 40.665 | −29.026 | 1.00 | 68.40 | O |
| ATOM | 6918 | N | PHE A | 949 | 5.943 | 41.386 | −27.593 | 1.00 | 60.77 | N |
| ATOM | 6919 | CA | PHE A | 949 | 6.895 | 40.331 | −27.834 | 1.00 | 61.97 | C |
| ATOM | 6920 | CB | PHE A | 949 | 8.130 | 40.816 | −28.598 | 1.00 | 62.94 | C |
| ATOM | 6921 | CG | PHE A | 949 | 7.954 | 40.894 | −30.118 | 1.00 | 68.91 | C |
| ATOM | 6922 | CD1 | PHE A | 949 | 6.765 | 41.397 | −30.723 | 1.00 | 72.63 | C |
| ATOM | 6923 | CE1 | PHE A | 949 | 6.618 | 41.502 | −32.112 | 1.00 | 66.94 | C |
| ATOM | 6924 | CZ | PHE A | 949 | 7.658 | 41.121 | −32.919 | 1.00 | 66.54 | C |
| ATOM | 6925 | CE2 | PHE A | 949 | 8.845 | 40.625 | −32.352 | 1.00 | 67.62 | C |
| ATOM | 6926 | CD2 | PHE A | 949 | 8.998 | 40.523 | −30.968 | 1.00 | 67.18 | C |
| ATOM | 6927 | C | PHE A | 949 | 7.290 | 39.898 | −26.452 | 1.00 | 63.58 | C |
| ATOM | 6928 | O | PHE A | 949 | 7.755 | 40.688 | −25.685 | 1.00 | 64.89 | O |
| ATOM | 6929 | N | ASN A | 950 | 7.075 | 38.643 | −26.117 | 1.00 | 69.68 | N |
| ATOM | 6930 | CA | ASN A | 950 | 7.479 | 38.156 | −24.816 | 1.00 | 70.55 | C |
| ATOM | 6931 | CB | ASN A | 950 | 6.407 | 38.502 | −23.768 | 1.00 | 76.86 | C |
| ATOM | 6932 | CG | ASN A | 950 | 6.783 | 38.030 | −22.368 | 1.00 | 82.27 | C |
| ATOM | 6933 | OD1 | ASN A | 950 | 5.929 | 37.996 | −21.496 | 1.00 | 88.47 | O |
| ATOM | 6934 | ND2 | ASN A | 950 | 8.054 | 37.618 | −22.159 | 1.00 | 80.96 | N |
| ATOM | 6935 | C | ASN A | 950 | 7.866 | 36.644 | −24.886 | 1.00 | 60.43 | C |
| ATOM | 6936 | O | ASN A | 950 | 7.035 | 35.748 | −24.831 | 1.00 | 54.54 | O |
| ATOM | 6937 | N | PRO A | 951 | 9.144 | 36.384 | −25.024 | 1.00 | 50.47 | N |
| ATOM | 6938 | CA | PRO A | 951 | 9.597 | 35.094 | −25.425 | 1.00 | 53.01 | C |
| ATOM | 6939 | CB | PRO A | 951 | 11.106 | 35.201 | −25.185 | 1.00 | 52.87 | C |
| ATOM | 6940 | CG | PRO A | 951 | 11.395 | 36.570 | −25.551 | 1.00 | 49.06 | C |
| ATOM | 6941 | CD | PRO A | 951 | 10.172 | 37.382 | −25.257 | 1.00 | 47.28 | C |
| ATOM | 6942 | C | PRO A | 951 | 9.016 | 33.903 | −24.686 | 1.00 | 50.75 | C |
| ATOM | 6943 | O | PRO A | 951 | 9.477 | 33.520 | −23.645 | 1.00 | 57.04 | O |
| ATOM | 6944 | N | ASN A | 952 | 8.044 | 33.257 | −25.261 | 1.00 | 52.11 | N |
| ATOM | 6945 | CA | ASN A | 952 | 7.650 | 31.941 | −24.737 | 1.00 | 51.15 | C |
| ATOM | 6946 | CB | ASN A | 952 | 6.643 | 32.063 | −23.580 | 1.00 | 47.81 | C |
| ATOM | 6947 | CG | ASN A | 952 | 6.874 | 31.036 | −22.512 | 1.00 | 47.68 | C |
| ATOM | 6948 | OD1 | ASN A | 952 | 7.913 | 30.408 | −22.471 | 1.00 | 46.82 | O |
| ATOM | 6949 | ND2 | ASN A | 952 | 5.897 | 30.851 | −21.636 | 1.00 | 51.43 | N |
| ATOM | 6950 | C | ASN A | 952 | 7.066 | 31.084 | −25.825 | 1.00 | 49.19 | C |
| ATOM | 6951 | O | ASN A | 952 | 6.718 | 31.553 | −26.910 | 1.00 | 48.56 | O |
| ATOM | 6952 | N | TRP A | 953 | 6.948 | 29.815 | −25.524 | 1.00 | 45.52 | N |
| ATOM | 6953 | CA | TRP A | 953 | 6.361 | 28.945 | −26.471 | 1.00 | 43.53 | C |
| ATOM | 6954 | CB | TRP A | 953 | 6.778 | 27.539 | −26.148 | 1.00 | 44.98 | C |
| ATOM | 6955 | CG | TRP A | 953 | 8.261 | 27.304 | −26.244 | 1.00 | 46.92 | C |
| ATOM | 6956 | CD1 | TRP A | 953 | 9.054 | 26.704 | −25.312 | 1.00 | 48.67 | C |
| ATOM | 6957 | NE1 | TRP A | 953 | 10.340 | 26.626 | −25.769 | 1.00 | 53.06 | N |
| ATOM | 6958 | CE2 | TRP A | 953 | 10.395 | 27.189 | −27.021 | 1.00 | 52.93 | C |
| ATOM | 6959 | CD2 | TRP A | 953 | 9.112 | 27.620 | −27.351 | 1.00 | 49.04 | C |
| ATOM | 6960 | CE3 | TRP A | 953 | 8.912 | 28.232 | −28.589 | 1.00 | 46.82 | C |
| ATOM | 6961 | CZ3 | TRP A | 953 | 9.948 | 28.387 | −29.419 | 1.00 | 46.54 | C |
| ATOM | 6962 | CH2 | TRP A | 953 | 11.208 | 27.970 | −29.077 | 1.00 | 49.96 | C |
| ATOM | 6963 | CZ2 | TRP A | 953 | 11.463 | 27.366 | −27.880 | 1.00 | 54.03 | C |
| ATOM | 6964 | C | TRP A | 953 | 4.858 | 29.147 | −26.503 | 1.00 | 41.66 | C |
| ATOM | 6965 | O | TRP A | 953 | 4.199 | 29.070 | −25.483 | 1.00 | 40.00 | O |
| ATOM | 6966 | N | MET A | 954 | 4.317 | 29.439 | −27.678 | 1.00 | 41.33 | N |
| ATOM | 6967 | CA | MET A | 954 | 2.885 | 29.676 | −27.806 | 1.00 | 42.78 | C |
| ATOM | 6968 | CB | MET A | 954 | 2.624 | 31.058 | −28.307 | 1.00 | 41.67 | C |
| ATOM | 6969 | CG | MET A | 954 | 1.187 | 31.474 | −28.144 | 1.00 | 44.57 | C |
| ATOM | 6970 | SD | MET A | 954 | 0.872 | 33.211 | −28.575 | 1.00 | 47.49 | S |
| ATOM | 6971 | CE | MET A | 954 | 0.659 | 33.079 | −30.362 | 1.00 | 49.67 | C |
| ATOM | 6972 | C | MET A | 954 | 2.288 | 28.629 | −28.750 | 1.00 | 44.79 | C |
| ATOM | 6973 | O | MET A | 954 | 2.877 | 28.324 | −29.777 | 1.00 | 47.30 | O |
| ATOM | 6974 | N | SER A | 955 | 1.140 | 28.053 | −28.357 | 1.00 | 44.36 | N |
| ATOM | 6975 | CA | SER A | 955 | 0.545 | 26.858 | −29.001 | 1.00 | 39.53 | C |
| ATOM | 6976 | CB | SER A | 955 | 0.392 | 25.745 | −27.995 | 1.00 | 37.80 | C |
| ATOM | 6977 | OG | SER A | 955 | −0.616 | 26.061 | −27.089 | 1.00 | 36.72 | O |
| ATOM | 6978 | C | SER A | 955 | −0.779 | 27.094 | −29.636 | 1.00 | 37.72 | C |
| ATOM | 6979 | O | SER A | 955 | −1.160 | 26.347 | −30.562 | 1.00 | 38.88 | O |
| ATOM | 6980 | N | ALA A | 956 | −1.462 | 28.133 | −29.164 | 1.00 | 37.14 | N |
| ATOM | 6981 | CA | ALA A | 956 | −2.761 | 28.554 | −29.708 | 1.00 | 39.95 | C |
| ATOM | 6982 | CB | ALA A | 956 | −3.818 | 27.624 | −29.171 | 1.00 | 40.49 | C |
| ATOM | 6983 | C | ALA A | 956 | −3.128 | 30.005 | −29.328 | 1.00 | 39.17 | C |
| ATOM | 6984 | O | ALA A | 956 | −2.757 | 30.425 | −28.270 | 1.00 | 38.60 | O |
| ATOM | 6985 | N | VAL A | 957 | −3.852 | 30.739 | −30.187 | 1.00 | 40.09 | N |
| ATOM | 6986 | CA | VAL A | 957 | −4.393 | 32.073 | −29.857 | 1.00 | 40.71 | C |
| ATOM | 6987 | CB | VAL A | 957 | −3.565 | 33.235 | −30.387 | 1.00 | 41.98 | C |
| ATOM | 6988 | CG1 | VAL A | 957 | −2.506 | 33.583 | −29.378 | 1.00 | 45.03 | C |
| ATOM | 6989 | CG2 | VAL A | 957 | −2.939 | 32.911 | −31.725 | 1.00 | 42.67 | C |
| ATOM | 6990 | C | VAL A | 957 | −5.756 | 32.327 | −30.390 | 1.00 | 41.92 | C |

TABLE 6-continued

Atomic coordinates for CRBN:DDB1: Compound B (Human protein)

| ATOM | 6991 | O | VAL A | 957 | −6.098 | 31.835 | −31.392 | 1.00 | 43.35 | O |
|---|---|---|---|---|---|---|---|---|---|---|
| ATOM | 6992 | N | GLU A | 958 | −6.524 | 33.145 | −29.703 | 1.00 | 49.11 | N |
| ATOM | 6993 | CA | GLU A | 958 | −7.860 | 33.503 | −30.130 | 1.00 | 51.25 | C |
| ATOM | 6994 | CB | GLU A | 958 | −8.842 | 32.654 | −29.345 | 1.00 | 55.02 | C |
| ATOM | 6995 | CG | GLU A | 958 | −10.256 | 32.772 | −29.868 | 1.00 | 57.92 | C |
| ATOM | 6996 | CD | GLU A | 958 | −10.284 | 32.503 | −31.338 | 1.00 | 60.78 | C |
| ATOM | 6997 | OE1 | GLU A | 958 | −10.635 | 33.470 | −32.042 | 1.00 | 63.49 | O |
| ATOM | 6998 | OE2 | GLU A | 958 | −9.865 | 31.373 | −31.760 | 1.00 | 60.98 | O |
| ATOM | 6999 | C | GLU A | 958 | −8.177 | 34.975 | −29.875 | 1.00 | 50.41 | C |
| ATOM | 7000 | O | GLU A | 958 | −7.635 | 35.575 | −28.936 | 1.00 | 50.08 | O |
| ATOM | 7001 | N | ILE A | 959 | −9.070 | 35.543 | −30.682 | 1.00 | 48.50 | N |
| ATOM | 7002 | CA | ILE A | 959 | −9.601 | 36.907 | −30.434 | 1.00 | 47.88 | C |
| ATOM | 7003 | CB | ILE A | 959 | −9.906 | 37.612 | −31.772 | 1.00 | 47.21 | C |
| ATOM | 7004 | CG1 | ILE A | 959 | −8.584 | 37.890 | −32.519 | 1.00 | 49.60 | C |
| ATOM | 7005 | CD1 | ILE A | 959 | −8.735 | 38.114 | −34.020 | 1.00 | 49.80 | C |
| ATOM | 7006 | CG2 | ILE A | 959 | −10.757 | 38.868 | −31.596 | 1.00 | 46.43 | C |
| ATOM | 7007 | C | ILE A | 959 | −10.858 | 36.873 | −29.562 | 1.00 | 48.07 | C |
| ATOM | 7008 | O | ILE A | 959 | −11.908 | 36.483 | −30.051 | 1.00 | 51.39 | O |
| ATOM | 7009 | N | LEU A | 960 | −10.766 | 37.281 | −28.295 | 1.00 | 46.32 | N |
| ATOM | 7010 | CA | LEU A | 960 | −11.940 | 37.311 | −27.450 | 1.00 | 48.81 | C |
| ATOM | 7011 | CB | LEU A | 960 | −11.544 | 37.461 | −26.005 | 1.00 | 50.69 | C |
| ATOM | 7012 | CG | LEU A | 960 | −10.962 | 36.250 | −25.269 | 1.00 | 53.46 | C |
| ATOM | 7013 | CD1 | LEU A | 960 | −10.104 | 36.733 | −24.122 | 1.00 | 55.94 | C |
| ATOM | 7014 | CD2 | LEU A | 960 | −12.047 | 35.366 | −24.688 | 1.00 | 54.91 | C |
| ATOM | 7015 | C | LEU A | 960 | −12.901 | 38.434 | −27.840 | 1.00 | 53.99 | C |
| ATOM | 7016 | O | LEU A | 960 | −14.091 | 38.264 | −27.744 | 1.00 | 56.26 | O |
| ATOM | 7017 | N | ASP A | 961 | −12.375 | 39.596 | −28.222 | 1.00 | 63.69 | N |
| ATOM | 7018 | CA | ASP A | 961 | −13.149 | 40.746 | −28.789 | 1.00 | 67.90 | C |
| ATOM | 7019 | CB | ASP A | 961 | −14.196 | 41.329 | −27.807 | 1.00 | 72.80 | C |
| ATOM | 7020 | CG | ASP A | 961 | −13.593 | 41.854 | −26.514 | 1.00 | 72.34 | C |
| ATOM | 7021 | OD1 | ASP A | 961 | −12.414 | 42.233 | −26.487 | 1.00 | 71.96 | O |
| ATOM | 7022 | OD2 | ASP A | 961 | −14.329 | 41.886 | −25.512 | 1.00 | 76.22 | O |
| ATOM | 7023 | C | ASP A | 961 | −12.174 | 41.834 | −29.307 | 1.00 | 69.82 | C |
| ATOM | 7024 | O | ASP A | 961 | −10.939 | 41.599 | −29.308 | 1.00 | 63.16 | O |
| ATOM | 7025 | N | ASP A | 962 | −12.693 | 43.009 | −29.712 | 1.00 | 73.09 | N |
| ATOM | 7026 | CA | ASP A | 962 | −11.895 | 43.945 | −30.537 | 1.00 | 75.97 | C |
| ATOM | 7027 | CB | ASP A | 962 | −12.698 | 45.181 | −30.997 | 1.00 | 82.31 | C |
| ATOM | 7028 | CG | ASP A | 962 | −14.024 | 44.811 | −31.739 | 1.00 | 87.87 | C |
| ATOM | 7029 | OD1 | ASP A | 962 | −15.038 | 44.566 | −31.030 | 1.00 | 84.23 | O |
| ATOM | 7030 | OD2 | ASP A | 962 | −14.053 | 44.769 | −33.012 | 1.00 | 89.01 | O |
| ATOM | 7031 | C | ASP A | 962 | −10.649 | 44.365 | −29.788 | 1.00 | 73.46 | C |
| ATOM | 7032 | O | ASP A | 962 | −9.635 | 44.682 | −30.434 | 1.00 | 73.24 | O |
| ATOM | 7033 | N | ASP A | 963 | −10.744 | 44.284 | −28.443 | 1.00 | 71.32 | N |
| ATOM | 7034 | CA | ASP A | 963 | −9.699 | 44.651 | −27.458 | 1.00 | 71.36 | C |
| ATOM | 7035 | CB | ASP A | 963 | −10.357 | 45.422 | −26.293 | 1.00 | 73.34 | C |
| ATOM | 7036 | CG | ASP A | 963 | −11.254 | 46.584 | −26.754 | 1.00 | 74.94 | C |
| ATOM | 7037 | OD1 | ASP A | 963 | −11.056 | 47.136 | −27.862 | 1.00 | 74.62 | O |
| ATOM | 7038 | OD2 | ASP A | 963 | −12.156 | 46.954 | −25.974 | 1.00 | 72.70 | O |
| ATOM | 7039 | C | ASP A | 963 | −8.843 | 43.548 | −26.770 | 1.00 | 69.86 | C |
| ATOM | 7040 | O | ASP A | 963 | −7.747 | 43.862 | −26.277 | 1.00 | 66.76 | O |
| ATOM | 7041 | N | ASN A | 964 | −9.340 | 42.299 | −26.672 | 1.00 | 69.75 | N |
| ATOM | 7042 | CA | ASN A | 964 | −8.689 | 41.225 | −25.830 | 1.00 | 63.76 | C |
| ATOM | 7043 | CB | ASN A | 964 | −9.561 | 40.856 | −24.614 | 1.00 | 64.66 | C |
| ATOM | 7044 | CG | ASN A | 964 | −9.768 | 42.035 | −23.676 | 1.00 | 68.22 | C |
| ATOM | 7045 | OD1 | ASN A | 964 | −8.898 | 42.414 | −22.896 | 1.00 | 62.68 | O |
| ATOM | 7046 | ND2 | ASN A | 964 | −10.915 | 42.654 | −23.796 | 1.00 | 76.27 | N |
| ATOM | 7047 | C | ASN A | 964 | −8.329 | 39.971 | −26.582 | 1.00 | 55.57 | C |
| ATOM | 7048 | O | ASN A | 964 | −9.088 | 39.517 | −27.398 | 1.00 | 55.68 | O |
| ATOM | 7049 | N | PHE A | 965 | −7.168 | 39.414 | −26.285 | 1.00 | 53.13 | N |
| ATOM | 7050 | CA | PHE A | 965 | −6.616 | 38.300 | −27.036 | 1.00 | 54.46 | C |
| ATOM | 7051 | CB | PHE A | 965 | −5.397 | 38.769 | −27.798 | 1.00 | 56.86 | C |
| ATOM | 7052 | CG | PHE A | 965 | −5.687 | 39.992 | −28.581 | 1.00 | 65.69 | C |
| ATOM | 7053 | CD1 | PHE A | 965 | −6.683 | 39.970 | −29.556 | 1.00 | 72.59 | C |
| ATOM | 7054 | CE1 | PHE A | 965 | −7.025 | 41.123 | −30.269 | 1.00 | 77.70 | C |
| ATOM | 7055 | CZ | PHE A | 965 | −6.386 | 42.332 | −29.983 | 1.00 | 75.79 | C |
| ATOM | 7056 | CE2 | PHE A | 965 | −5.414 | 42.368 | −28.990 | 1.00 | 73.03 | C |
| ATOM | 7057 | CD2 | PHE A | 965 | −5.083 | 41.204 | −28.285 | 1.00 | 72.60 | C |
| ATOM | 7058 | C | PHE A | 965 | −6.258 | 37.240 | −26.062 | 1.00 | 55.55 | C |
| ATOM | 7059 | O | PHE A | 965 | −5.491 | 37.488 | −25.164 | 1.00 | 60.51 | O |
| ATOM | 7060 | N | LEU A | 966 | −6.857 | 36.063 | −26.206 | 1.00 | 55.95 | N |
| ATOM | 7061 | CA | LEU A | 966 | −6.526 | 34.893 | −25.375 | 1.00 | 48.74 | C |
| ATOM | 7062 | CB | LEU A | 966 | −7.786 | 34.062 | −25.205 | 1.00 | 48.75 | C |
| ATOM | 7063 | CG | LEU A | 966 | −7.704 | 32.738 | −24.480 | 1.00 | 49.60 | C |
| ATOM | 7064 | CD1 | LEU A | 966 | −7.078 | 32.908 | −23.116 | 1.00 | 51.87 | C |
| ATOM | 7065 | CD2 | LEU A | 966 | −9.099 | 32.174 | −24.364 | 1.00 | 48.71 | C |
| ATOM | 7066 | C | LEU A | 966 | −5.408 | 34.098 | −26.067 | 1.00 | 44.29 | C |
| ATOM | 7067 | O | LEU A | 966 | −5.366 | 33.975 | −27.291 | 1.00 | 36.82 | O |
| ATOM | 7068 | N | GLY A | 967 | −4.460 | 33.616 | −25.287 | 1.00 | 42.44 | N |

TABLE 6-continued

Atomic coordinates for CRBN:DDB1: Compound B (Human protein)

| ATOM | 7069 | CA | GLY A | 967 | −3.434 | 32.745 | −25.833 | 1.00 | 41.01 | C |
|---|---|---|---|---|---|---|---|---|---|---|
| ATOM | 7070 | C | GLY A | 967 | −3.072 | 31.671 | −24.851 | 1.00 | 40.76 | C |
| ATOM | 7071 | O | GLY A | 967 | −3.388 | 31.810 | −23.663 | 1.00 | 41.53 | O |
| ATOM | 7072 | N | ALA A | 968 | −2.450 | 30.592 | −25.354 | 1.00 | 40.25 | N |
| ATOM | 7073 | CA | ALA A | 968 | −1.986 | 29.450 | −24.538 | 1.00 | 38.27 | C |
| ATOM | 7074 | CB | ALA A | 968 | −2.667 | 28.181 | −24.970 | 1.00 | 37.41 | C |
| ATOM | 7075 | C | ALA A | 968 | −0.483 | 29.339 | −24.691 | 1.00 | 38.88 | C |
| ATOM | 7076 | O | ALA A | 968 | 0.035 | 29.490 | −25.774 | 1.00 | 36.11 | O |
| ATOM | 7077 | N | GLU A | 969 | 0.227 | 29.134 | −23.590 | 1.00 | 43.01 | N |
| ATOM | 7078 | CA | GLU A | 969 | 1.675 | 29.362 | −23.577 | 1.00 | 45.84 | C |
| ATOM | 7079 | CB | GLU A | 969 | 2.006 | 30.854 | −23.360 | 1.00 | 48.58 | C |
| ATOM | 7080 | CG | GLU A | 969 | 2.262 | 31.344 | −21.929 | 1.00 | 50.15 | C |
| ATOM | 7081 | CD | GLU A | 969 | 2.809 | 32.787 | −21.875 | 1.00 | 56.07 | C |
| ATOM | 7082 | OE1 | GLU A | 969 | 4.028 | 32.971 | −22.196 | 1.00 | 56.27 | O |
| ATOM | 7083 | OE2 | GLU A | 969 | 2.048 | 33.749 | −21.494 | 1.00 | 58.91 | O |
| ATOM | 7084 | C | GLU A | 969 | 2.336 | 28.508 | −22.550 | 1.00 | 47.76 | C |
| ATOM | 7085 | O | GLU A | 969 | 1.663 | 27.934 | −21.715 | 1.00 | 54.41 | O |
| ATOM | 7086 | N | ASN A | 970 | 3.658 | 28.465 | −22.598 | 1.00 | 50.69 | N |
| ATOM | 7087 | CA | ASN A | 970 | 4.439 | 27.333 | −22.090 | 1.00 | 54.96 | C |
| ATOM | 7088 | CB | ASN A | 970 | 5.882 | 27.365 | −22.606 | 1.00 | 55.19 | C |
| ATOM | 7089 | CG | ASN A | 970 | 6.864 | 26.610 | −21.701 | 1.00 | 57.35 | C |
| ATOM | 7090 | OD1 | ASN A | 970 | 6.876 | 25.349 | −21.677 | 1.00 | 51.19 | O |
| ATOM | 7091 | ND2 | ASN A | 970 | 7.693 | 27.374 | −20.942 | 1.00 | 58.78 | N |
| ATOM | 7092 | C | ASN A | 970 | 4.441 | 27.082 | −20.571 | 1.00 | 58.63 | C |
| ATOM | 7093 | O | ASN A | 970 | 4.507 | 28.019 | −19.768 | 1.00 | 54.08 | O |
| ATOM | 7094 | N | ALA A | 971 | 4.497 | 25.760 | −20.283 | 1.00 | 62.70 | N |
| ATOM | 7095 | CA | ALA A | 971 | 4.017 | 25.048 | −19.106 | 1.00 | 54.62 | C |
| ATOM | 7096 | CB | ALA A | 971 | 4.773 | 25.463 | −17.887 | 1.00 | 57.27 | C |
| ATOM | 7097 | C | ALA A | 971 | 2.536 | 25.299 | −18.973 | 1.00 | 50.39 | C |
| ATOM | 7098 | O | ALA A | 971 | 2.082 | 25.947 | −18.050 | 1.00 | 54.44 | O |
| ATOM | 7099 | N | PHE A | 972 | 1.779 | 24.863 | −19.957 | 1.00 | 44.67 | N |
| ATOM | 7100 | CA | PHE A | 972 | 0.341 | 24.718 | −19.759 | 1.00 | 43.74 | C |
| ATOM | 7101 | CB | PHE A | 972 | 0.114 | 23.533 | −18.801 | 1.00 | 42.83 | C |
| ATOM | 7102 | CG | PHE A | 972 | 1.024 | 22.403 | −19.103 | 1.00 | 43.63 | C |
| ATOM | 7103 | CD1 | PHE A | 972 | 0.765 | 21.556 | −20.232 | 1.00 | 43.25 | C |
| ATOM | 7104 | CE1 | PHE A | 972 | 1.674 | 20.560 | −20.596 | 1.00 | 38.31 | C |
| ATOM | 7105 | CZ | PHE A | 972 | 2.806 | 20.394 | −19.840 | 1.00 | 36.97 | C |
| ATOM | 7106 | CE2 | PHE A | 972 | 3.077 | 21.227 | −18.747 | 1.00 | 37.96 | C |
| ATOM | 7107 | CD2 | PHE A | 972 | 2.215 | 22.249 | −18.403 | 1.00 | 38.86 | C |
| ATOM | 7108 | C | PHE A | 972 | −0.379 | 25.928 | −19.222 | 1.00 | 40.74 | C |
| ATOM | 7109 | O | PHE A | 972 | −1.292 | 25.769 | −18.395 | 1.00 | 39.63 | O |
| ATOM | 7110 | N | ASN A | 973 | 0.018 | 27.115 | −19.657 | 1.00 | 38.26 | N |
| ATOM | 7111 | CA | ASN A | 973 | −0.636 | 28.314 | −19.166 | 1.00 | 40.12 | C |
| ATOM | 7112 | CB | ASN A | 973 | 0.391 | 29.358 | −18.739 | 1.00 | 44.33 | C |
| ATOM | 7113 | CG | ASN A | 973 | 1.350 | 28.883 | −17.638 | 1.00 | 45.80 | C |
| ATOM | 7114 | OD1 | ASN A | 973 | 0.949 | 28.516 | −16.511 | 1.00 | 45.41 | O |
| ATOM | 7115 | ND2 | ASN A | 973 | 2.632 | 28.971 | −17.940 | 1.00 | 45.51 | N |
| ATOM | 7116 | C | ASN A | 973 | −1.585 | 28.973 | −20.174 | 1.00 | 39.74 | C |
| ATOM | 7117 | O | ASN A | 973 | −1.433 | 28.841 | −21.409 | 1.00 | 38.34 | O |
| ATOM | 7118 | N | LEU A | 974 | −2.584 | 29.673 | −19.647 | 1.00 | 39.34 | N |
| ATOM | 7119 | CA | LEU A | 974 | −3.331 | 30.622 | −20.471 | 1.00 | 40.64 | C |
| ATOM | 7120 | CB | LEU A | 974 | −4.826 | 30.448 | −20.303 | 1.00 | 38.81 | C |
| ATOM | 7121 | CG | LEU A | 974 | −5.444 | 29.095 | −20.626 | 1.00 | 37.45 | C |
| ATOM | 7122 | CD1 | LEU A | 974 | −6.955 | 29.169 | −20.476 | 1.00 | 36.15 | C |
| ATOM | 7123 | CD2 | LEU A | 974 | −5.071 | 28.706 | −22.047 | 1.00 | 38.10 | C |
| ATOM | 7124 | C | LEU A | 974 | −2.896 | 32.039 | −20.081 | 1.00 | 43.48 | C |
| ATOM | 7125 | O | LEU A | 974 | −2.494 | 32.289 | −18.923 | 1.00 | 44.02 | O |
| ATOM | 7126 | N | PHE A | 975 | −2.904 | 32.940 | −21.067 | 1.00 | 45.72 | N |
| ATOM | 7127 | CA | PHE A | 975 | −2.530 | 34.350 | −20.863 | 1.00 | 46.17 | C |
| ATOM | 7128 | CB | PHE A | 975 | −1.069 | 34.616 | −21.240 | 1.00 | 45.99 | C |
| ATOM | 7129 | CG | PHE A | 975 | −0.848 | 34.639 | −22.684 | 1.00 | 48.32 | C |
| ATOM | 7130 | CD1 | PHE A | 975 | −1.119 | 35.795 | −23.417 | 1.00 | 50.74 | C |
| ATOM | 7131 | CE1 | PHE A | 975 | −0.982 | 35.806 | −24.801 | 1.00 | 53.92 | C |
| ATOM | 7132 | CZ | PHE A | 975 | −0.581 | 34.636 | −25.462 | 1.00 | 56.41 | C |
| ATOM | 7133 | CE2 | PHE A | 975 | −0.322 | 33.458 | −24.727 | 1.00 | 52.61 | C |
| ATOM | 7134 | CD2 | PHE A | 975 | −0.469 | 33.475 | −23.348 | 1.00 | 51.62 | C |
| ATOM | 7135 | C | PHE A | 975 | −3.436 | 35.223 | −21.688 | 1.00 | 46.53 | C |
| ATOM | 7136 | O | PHE A | 975 | −3.917 | 34.798 | −22.752 | 1.00 | 47.55 | O |
| ATOM | 7137 | N | VAL A | 976 | −3.644 | 36.452 | −21.222 | 1.00 | 48.96 | N |
| ATOM | 7138 | CA | VAL A | 976 | −4.474 | 37.411 | −21.948 | 1.00 | 49.55 | C |
| ATOM | 7139 | CB | VAL A | 976 | −5.817 | 37.636 | −21.262 | 1.00 | 51.47 | C |
| ATOM | 7140 | CG1 | VAL A | 976 | −6.628 | 38.625 | −22.079 | 1.00 | 53.93 | C |
| ATOM | 7141 | CG2 | VAL A | 976 | −6.580 | 36.330 | −21.134 | 1.00 | 51.36 | C |
| ATOM | 7142 | C | VAL A | 976 | −3.842 | 38.752 | −22.078 | 1.00 | 46.77 | C |
| ATOM | 7143 | O | VAL A | 976 | −3.628 | 39.380 | −21.100 | 1.00 | 49.83 | O |
| ATOM | 7144 | N | CYS A | 977 | −3.604 | 39.176 | −23.301 | 1.00 | 50.68 | N |
| ATOM | 7145 | CA | CYS A | 977 | −3.206 | 40.529 | −23.666 | 1.00 | 54.98 | C |
| ATOM | 7146 | CB | CYS A | 977 | −2.392 | 40.545 | −24.946 | 1.00 | 59.61 | C |

TABLE 6-continued

Atomic coordinates for CRBN:DDB1: Compound B (Human protein)

| ATOM | 7147 | SG | CYS A | 977 | −0.699 | 40.016 | −24.649 | 1.00 | 86.62 | S |
|---|---|---|---|---|---|---|---|---|---|---|
| ATOM | 7148 | C | CYS A | 977 | −4.427 | 41.334 | −23.949 | 1.00 | 55.30 | C |
| ATOM | 7149 | O | CYS A | 977 | −5.311 | 40.876 | −24.667 | 1.00 | 47.62 | O |
| ATOM | 7150 | N | GLN A | 978 | −4.453 | 42.554 | −23.406 | 1.00 | 63.17 | N |
| ATOM | 7151 | CA | GLN A | 978 | −5.487 | 43.560 | −23.711 | 1.00 | 65.31 | C |
| ATOM | 7152 | CB | GLN A | 978 | −6.066 | 44.077 | −22.404 | 1.00 | 63.91 | C |
| ATOM | 7153 | CG | GLN A | 978 | −7.260 | 44.976 | −22.561 | 1.00 | 65.79 | C |
| ATOM | 7154 | CD | GLN A | 978 | −7.736 | 45.491 | −21.246 | 1.00 | 65.64 | C |
| ATOM | 7155 | OE1 | GLN A | 978 | −7.438 | 46.627 | −20.853 | 1.00 | 69.88 | O |
| ATOM | 7156 | NE2 | GLN A | 978 | −8.470 | 44.667 | −20.547 | 1.00 | 65.96 | N |
| ATOM | 7157 | C | GLN A | 978 | −4.916 | 44.710 | −24.574 | 1.00 | 66.95 | C |
| ATOM | 7158 | O | GLN A | 978 | −3.704 | 44.970 | −24.568 | 1.00 | 62.77 | O |
| ATOM | 7159 | N | LYS A | 979 | −5.796 | 45.374 | −25.325 | 1.00 | 73.27 | N |
| ATOM | 7160 | CA | LYS A | 979 | −5.410 | 46.450 | −26.243 | 1.00 | 76.39 | C |
| ATOM | 7161 | CB | LYS A | 979 | −6.561 | 46.841 | −27.193 | 1.00 | 75.17 | C |
| ATOM | 7162 | CG | LYS A | 979 | −6.096 | 47.630 | −28.411 | 1.00 | 73.67 | C |
| ATOM | 7163 | CD | LYS A | 979 | −6.793 | 47.286 | −29.728 | 1.00 | 76.23 | C |
| ATOM | 7164 | CE | LYS A | 979 | −8.140 | 47.992 | −29.956 | 1.00 | 79.69 | C |
| ATOM | 7165 | NZ | LYS A | 979 | −8.701 | 47.816 | −31.348 | 1.00 | 81.14 | N |
| ATOM | 7166 | C | LYS A | 979 | −4.904 | 47.679 | −25.536 | 1.00 | 82.02 | C |
| ATOM | 7167 | O | LYS A | 979 | −3.778 | 48.112 | −25.793 | 1.00 | 88.03 | O |
| ATOM | 7168 | N | ASP A | 980 | −5.701 | 48.245 | −24.643 | 1.00 | 86.88 | N |
| ATOM | 7169 | CA | ASP A | 980 | −5.381 | 49.598 | −24.184 | 1.00 | 100.91 | C |
| ATOM | 7170 | CB | ASP A | 980 | −6.544 | 50.205 | −23.388 | 1.00 | 108.29 | C |
| ATOM | 7171 | CG | ASP A | 980 | −6.538 | 51.728 | −23.414 | 1.00 | 107.18 | C |
| ATOM | 7172 | OD1 | ASP A | 980 | −5.731 | 52.296 | −24.189 | 1.00 | 106.93 | O |
| ATOM | 7173 | OD2 | ASP A | 980 | −7.346 | 52.343 | −22.670 | 1.00 | 99.48 | O |
| ATOM | 7174 | C | ASP A | 980 | −4.083 | 49.686 | −23.366 | 1.00 | 103.43 | C |
| ATOM | 7175 | O | ASP A | 980 | −3.524 | 50.775 | −23.195 | 1.00 | 103.93 | O |
| ATOM | 7176 | N | GLU A | 987 | −0.390 | 57.816 | −30.545 | 1.00 | 98.86 | N |
| ATOM | 7177 | CA | GLU A | 987 | 0.068 | 57.835 | −29.153 | 1.00 | 108.31 | C |
| ATOM | 7178 | CB | GLU A | 987 | −1.180 | 57.994 | −28.206 | 1.00 | 105.31 | C |
| ATOM | 7179 | CG | GLU A | 987 | −1.194 | 57.523 | −26.723 | 1.00 | 103.73 | C |
| ATOM | 7180 | CD | GLU A | 987 | −0.624 | 58.476 | −25.643 | 1.00 | 93.34 | C |
| ATOM | 7181 | OE1 | GLU A | 987 | −1.380 | 58.850 | −24.689 | 1.00 | 78.76 | O |
| ATOM | 7182 | OE2 | GLU A | 987 | 0.588 | 58.785 | −25.706 | 1.00 | 82.26 | O |
| ATOM | 7183 | C | GLU A | 987 | 0.983 | 56.590 | −28.954 | 1.00 | 111.31 | C |
| ATOM | 7184 | O | GLU A | 987 | 1.225 | 55.828 | −29.903 | 1.00 | 105.74 | O |
| ATOM | 7185 | N | GLU A | 988 | 1.543 | 56.427 | −27.758 | 1.00 | 113.09 | N |
| ATOM | 7186 | CA | GLU A | 988 | 2.429 | 55.306 | −27.455 | 1.00 | 114.52 | C |
| ATOM | 7187 | CB | GLU A | 988 | 3.588 | 55.849 | −26.579 | 1.00 | 120.48 | C |
| ATOM | 7188 | CG | GLU A | 988 | 4.958 | 55.466 | −27.080 | 1.00 | 118.12 | C |
| ATOM | 7189 | CD | GLU A | 988 | 5.017 | 53.982 | −27.306 | 1.00 | 119.63 | C |
| ATOM | 7190 | OE1 | GLU A | 988 | 4.845 | 53.545 | −28.463 | 1.00 | 127.22 | O |
| ATOM | 7191 | OE2 | GLU A | 988 | 5.134 | 53.257 | −26.303 | 1.00 | 118.45 | O |
| ATOM | 7192 | C | GLU A | 988 | 1.685 | 54.060 | −26.825 | 1.00 | 110.75 | C |
| ATOM | 7193 | O | GLU A | 988 | 2.261 | 53.245 | −26.072 | 1.00 | 95.57 | O |
| ATOM | 7194 | N | ARG A | 989 | 0.405 | 53.909 | −27.171 | 1.00 | 106.52 | N |
| ATOM | 7195 | CA | ARG A | 989 | −0.402 | 52.772 | −26.750 | 1.00 | 100.82 | C |
| ATOM | 7196 | CB | ARG A | 989 | −1.625 | 53.279 | −25.983 | 1.00 | 108.39 | C |
| ATOM | 7197 | CG | ARG A | 989 | −1.241 | 54.049 | −24.697 | 1.00 | 114.01 | C |
| ATOM | 7198 | CD | ARG A | 989 | −2.422 | 54.643 | −23.899 | 1.00 | 120.16 | C |
| ATOM | 7199 | NE | ARG A | 989 | −3.120 | 55.743 | −24.597 | 1.00 | 122.21 | N |
| ATOM | 7200 | CZ | ARG A | 989 | −3.957 | 56.624 | −24.040 | 1.00 | 119.07 | C |
| ATOM | 7201 | NH1 | ARG A | 989 | −4.249 | 56.565 | −22.741 | 1.00 | 122.71 | N |
| ATOM | 7202 | NH2 | ARG A | 989 | −4.509 | 57.577 | −24.795 | 1.00 | 113.39 | N |
| ATOM | 7203 | C | ARG A | 989 | −0.689 | 51.885 | −27.999 | 1.00 | 94.40 | C |
| ATOM | 7204 | O | ARG A | 989 | −1.801 | 51.730 | −28.510 | 1.00 | 78.14 | O |
| ATOM | 7205 | N | GLN A | 990 | 0.429 | 51.383 | −28.506 | 1.00 | 91.30 | N |
| ATOM | 7206 | CA | GLN A | 990 | 0.521 | 50.275 | −29.399 | 1.00 | 82.30 | C |
| ATOM | 7207 | CB | GLN A | 990 | 1.138 | 50.737 | −30.738 | 1.00 | 82.57 | C |
| ATOM | 7208 | CG | GLN A | 990 | 2.594 | 51.225 | −30.749 | 1.00 | 82.76 | C |
| ATOM | 7209 | CD | GLN A | 990 | 3.099 | 51.639 | −32.155 | 1.00 | 88.52 | C |
| ATOM | 7210 | OE1 | GLN A | 990 | 4.186 | 52.190 | −32.294 | 1.00 | 91.04 | O |
| ATOM | 7211 | NE2 | GLN A | 990 | 2.309 | 51.377 | −33.192 | 1.00 | 88.90 | N |
| ATOM | 7212 | C | GLN A | 990 | 1.360 | 49.191 | −28.690 | 1.00 | 80.55 | C |
| ATOM | 7213 | O | GLN A | 990 | 1.916 | 48.305 | −29.309 | 1.00 | 77.62 | O |
| ATOM | 7214 | N | HIS A | 991 | 1.490 | 49.282 | −27.378 | 1.00 | 82.07 | N |
| ATOM | 7215 | CA | HIS A | 991 | 1.878 | 48.126 | −26.597 | 1.00 | 86.55 | C |
| ATOM | 7216 | CB | HIS A | 991 | 2.904 | 48.489 | −25.479 | 1.00 | 92.72 | C |
| ATOM | 7217 | CG | HIS A | 991 | 2.469 | 48.119 | −24.073 | 1.00 | 106.38 | C |
| ATOM | 7218 | ND1 | HIS A | 991 | 3.012 | 47.058 | −23.370 | 1.00 | 112.16 | N |
| ATOM | 7219 | CE1 | HIS A | 991 | 2.453 | 46.987 | −22.171 | 1.00 | 106.88 | C |
| ATOM | 7220 | NE2 | HIS A | 991 | 1.556 | 47.952 | −22.070 | 1.00 | 101.78 | N |
| ATOM | 7221 | CD2 | HIS A | 991 | 1.548 | 48.677 | −23.240 | 1.00 | 106.06 | C |
| ATOM | 7222 | C | HIS A | 991 | 0.536 | 47.517 | −26.099 | 1.00 | 82.29 | C |
| ATOM | 7223 | O | HIS A | 991 | −0.551 | 48.160 | −26.150 | 1.00 | 72.97 | O |
| ATOM | 7224 | N | LEU A | 992 | 0.646 | 46.268 | −25.644 | 1.00 | 74.63 | N |

TABLE 6-continued

Atomic coordinates for CRBN:DDB1: Compound B (Human protein)

| ATOM | 7225 | CA | LEU A | 992 | −0.469 | 45.438 | −25.253 | 1.00 | 66.18 | C |
|---|---|---|---|---|---|---|---|---|---|---|
| ATOM | 7226 | CB | LEU A | 992 | −0.465 | 44.190 | −26.113 | 1.00 | 61.01 | C |
| ATOM | 7227 | CG | LEU A | 992 | −0.883 | 44.389 | −27.559 | 1.00 | 58.69 | C |
| ATOM | 7228 | CD1 | LEU A | 992 | −0.586 | 43.193 | −28.422 | 1.00 | 59.54 | C |
| ATOM | 7229 | CD2 | LEU A | 992 | −2.367 | 44.658 | −27.623 | 1.00 | 59.53 | C |
| ATOM | 7230 | C | LEU A | 992 | −0.224 | 45.059 | −23.831 | 1.00 | 67.62 | C |
| ATOM | 7231 | O | LEU A | 992 | 0.830 | 44.503 | −23.512 | 1.00 | 71.37 | O |
| ATOM | 7232 | N | GLN A | 993 | −1.191 | 45.357 | −22.976 | 1.00 | 71.58 | N |
| ATOM | 7233 | CA | GLN A | 993 | −1.067 | 45.135 | −21.520 | 1.00 | 75.64 | C |
| ATOM | 7234 | CB | GLN A | 993 | −2.067 | 46.045 | −20.720 | 1.00 | 86.63 | C |
| ATOM | 7235 | CG | GLN A | 993 | −1.472 | 47.154 | −19.846 | 1.00 | 90.67 | C |
| ATOM | 7236 | CD | GLN A | 993 | −0.480 | 46.580 | −18.859 | 1.00 | 95.83 | C |
| ATOM | 7237 | OE1 | GLN A | 993 | −0.855 | 46.040 | −17.812 | 1.00 | 99.60 | O |
| ATOM | 7238 | NE2 | GLN A | 993 | 0.797 | 46.639 | −19.216 | 1.00 | 97.29 | N |
| ATOM | 7239 | C | GLN A | 993 | −1.309 | 43.656 | −21.207 | 1.00 | 65.97 | C |
| ATOM | 7240 | O | GLN A | 993 | −2.217 | 43.076 | −21.778 | 1.00 | 62.98 | O |
| ATOM | 7241 | N | GLU A | 994 | −0.510 | 43.068 | −20.320 | 1.00 | 58.75 | N |
| ATOM | 7242 | CA | GLU A | 994 | −0.725 | 41.705 | −19.898 | 1.00 | 60.59 | C |
| ATOM | 7243 | CB | GLU A | 994 | 0.622 | 41.128 | −19.370 | 1.00 | 69.13 | C |
| ATOM | 7244 | CG | GLU A | 994 | 0.651 | 39.620 | −19.003 | 1.00 | 80.18 | C |
| ATOM | 7245 | CD | GLU A | 994 | 2.072 | 39.000 | −18.821 | 1.00 | 87.84 | C |
| ATOM | 7246 | OE1 | GLU A | 994 | 2.684 | 39.123 | −17.722 | 1.00 | 91.40 | O |
| ATOM | 7247 | OE2 | GLU A | 994 | 2.567 | 38.332 | −19.766 | 1.00 | 84.40 | O |
| ATOM | 7248 | C | GLU A | 994 | −1.878 | 41.623 | −18.846 | 1.00 | 56.24 | C |
| ATOM | 7249 | O | GLU A | 994 | −1.600 | 41.526 | −17.694 | 1.00 | 65.12 | O |
| ATOM | 7250 | N | VAL A | 995 | −3.156 | 41.603 | −19.206 | 1.00 | 51.00 | N |
| ATOM | 7251 | CA | VAL A | 995 | −4.199 | 41.483 | −18.185 | 1.00 | 51.00 | C |
| ATOM | 7252 | CB | VAL A | 995 | −5.557 | 42.077 | −18.593 | 1.00 | 54.56 | C |
| ATOM | 7253 | CG1 | VAL A | 995 | −5.398 | 43.461 | −19.181 | 1.00 | 56.13 | C |
| ATOM | 7254 | CG2 | VAL A | 995 | −6.287 | 41.166 | −19.551 | 1.00 | 59.73 | C |
| ATOM | 7255 | C | VAL A | 995 | −4.534 | 40.103 | −17.612 | 1.00 | 52.17 | C |
| ATOM | 7256 | O | VAL A | 995 | −5.302 | 40.028 | −16.626 | 1.00 | 53.25 | O |
| ATOM | 7257 | N | GLY A | 996 | −4.039 | 39.017 | −18.191 | 1.00 | 51.56 | N |
| ATOM | 7258 | CA | GLY A | 996 | −4.476 | 37.685 | −17.718 | 1.00 | 52.92 | C |
| ATOM | 7259 | C | GLY A | 996 | −3.380 | 36.641 | −17.578 | 1.00 | 51.95 | C |
| ATOM | 7260 | O | GLY A | 996 | −2.546 | 36.508 | −18.474 | 1.00 | 50.70 | O |
| ATOM | 7261 | N | LEU A | 997 | −3.384 | 35.894 | −16.474 | 1.00 | 49.49 | N |
| ATOM | 7262 | CA | LEU A | 997 | −2.482 | 34.766 | −16.317 | 1.00 | 52.22 | C |
| ATOM | 7263 | CB | LEU A | 997 | −1.225 | 35.207 | −15.602 | 1.00 | 55.28 | C |
| ATOM | 7264 | CG | LEU A | 997 | −0.390 | 36.327 | −16.202 | 1.00 | 58.91 | C |
| ATOM | 7265 | CD1 | LEU A | 997 | 0.764 | 36.654 | −15.270 | 1.00 | 60.90 | C |
| ATOM | 7266 | CD2 | LEU A | 997 | 0.153 | 35.986 | −17.576 | 1.00 | 60.13 | C |
| ATOM | 7267 | C | LEU A | 997 | −3.065 | 33.642 | −15.495 | 1.00 | 51.77 | C |
| ATOM | 7268 | O | LEU A | 997 | −3.658 | 33.900 | −14.463 | 1.00 | 54.23 | O |
| ATOM | 7269 | N | PHE A | 998 | −2.813 | 32.396 | −15.897 | 1.00 | 48.48 | N |
| ATOM | 7270 | CA | PHE A | 998 | −3.459 | 31.247 | −15.289 | 1.00 | 44.78 | C |
| ATOM | 7271 | CB | PHE A | 998 | −4.883 | 31.212 | −15.793 | 1.00 | 44.74 | C |
| ATOM | 7272 | CG | PHE A | 998 | −5.744 | 30.255 | −15.081 | 1.00 | 49.19 | C |
| ATOM | 7273 | CD1 | PHE A | 998 | −6.311 | 30.595 | −13.855 | 1.00 | 52.21 | C |
| ATOM | 7274 | CE1 | PHE A | 998 | −7.141 | 29.702 | −13.160 | 1.00 | 50.23 | C |
| ATOM | 7275 | CZ | PHE A | 998 | −7.395 | 28.464 | −13.688 | 1.00 | 51.06 | C |
| ATOM | 7276 | CE2 | PHE A | 998 | −6.839 | 28.111 | −14.922 | 1.00 | 51.43 | C |
| ATOM | 7277 | CD2 | PHE A | 998 | −6.021 | 29.008 | −15.612 | 1.00 | 51.59 | C |
| ATOM | 7278 | C | PHE A | 998 | −2.736 | 29.983 | −15.685 | 1.00 | 43.79 | C |
| ATOM | 7279 | O | PHE A | 998 | −2.464 | 29.775 | −16.859 | 1.00 | 44.52 | O |
| ATOM | 7280 | N | HIS A | 999 | −2.397 | 29.133 | −14.727 | 1.00 | 44.60 | N |
| ATOM | 7281 | CA | HIS A | 999 | −1.932 | 27.773 | −15.066 | 1.00 | 44.12 | C |
| ATOM | 7282 | CB | HIS A | 999 | −1.040 | 27.219 | −14.006 | 1.00 | 41.81 | C |
| ATOM | 7283 | CG | HIS A | 999 | −0.269 | 26.009 | −14.427 | 1.00 | 43.29 | C |
| ATOM | 7284 | ND1 | HIS A | 999 | −0.430 | 24.781 | −13.823 | 1.00 | 44.49 | N |
| ATOM | 7285 | CE1 | HIS A | 999 | 0.443 | 23.920 | −14.322 | 1.00 | 43.78 | C |
| ATOM | 7286 | NE2 | HIS A | 999 | 1.177 | 24.553 | −15.217 | 1.00 | 44.01 | N |
| ATOM | 7287 | CD2 | HIS A | 999 | 0.755 | 25.857 | −15.302 | 1.00 | 43.81 | C |
| ATOM | 7288 | C | HIS A | 999 | −3.138 | 26.840 | −15.248 | 1.00 | 45.96 | C |
| ATOM | 7289 | O | HIS A | 999 | −3.880 | 26.582 | −14.290 | 1.00 | 46.12 | O |
| ATOM | 7290 | N | LEU A | 1000 | −3.342 | 26.379 | −16.487 | 1.00 | 44.89 | N |
| ATOM | 7291 | CA | LEU A | 1000 | −4.443 | 25.496 | −16.830 | 1.00 | 43.56 | C |
| ATOM | 7292 | CB | LEU A | 1000 | −4.613 | 25.507 | −18.311 | 1.00 | 42.72 | C |
| ATOM | 7293 | CG | LEU A | 1000 | −5.782 | 24.809 | −18.957 | 1.00 | 42.86 | C |
| ATOM | 7294 | CD1 | LEU A | 1000 | −7.080 | 25.324 | −18.374 | 1.00 | 41.73 | C |
| ATOM | 7295 | CD2 | LEU A | 1000 | −5.743 | 25.076 | −20.466 | 1.00 | 43.05 | C |
| ATOM | 7296 | C | LEU A | 1000 | −4.151 | 24.085 | −16.422 | 1.00 | 43.72 | C |
| ATOM | 7297 | O | LEU A | 1000 | −5.031 | 23.386 | −15.956 | 1.00 | 45.46 | O |
| ATOM | 7298 | N | GLY A | 1001 | −2.905 | 23.684 | −16.599 | 1.00 | 43.69 | N |
| ATOM | 7299 | CA | GLY A | 1001 | −2.502 | 22.304 | −16.439 | 1.00 | 45.32 | C |
| ATOM | 7300 | C | GLY A | 1001 | −2.738 | 21.421 | −17.672 | 1.00 | 46.19 | C |
| ATOM | 7301 | O | GLY A | 1001 | −2.531 | 20.206 | −17.582 | 1.00 | 41.98 | O |
| ATOM | 7302 | N | GLU A | 1002 | −3.189 | 22.028 | −18.786 | 1.00 | 46.89 | N |

TABLE 6-continued

Atomic coordinates for CRBN:DDB1: Compound B (Human protein)

| ATOM | 7303 | CA | GLU A | 1002 | −3.293 | 21.373 | −20.092 | 1.00 | 47.52 | C |
|---|---|---|---|---|---|---|---|---|---|---|
| ATOM | 7304 | CB | GLU A | 1002 | −4.758 | 21.263 | −20.505 | 1.00 | 47.12 | C |
| ATOM | 7305 | CG | GLU A | 1002 | −5.606 | 20.397 | −19.593 | 1.00 | 47.47 | C |
| ATOM | 7306 | CD | GLU A | 1002 | −5.145 | 18.952 | −19.512 | 1.00 | 49.79 | C |
| ATOM | 7307 | OE1 | GLU A | 1002 | −4.331 | 18.432 | −20.349 | 1.00 | 52.28 | O |
| ATOM | 7308 | OE2 | GLU A | 1002 | −5.611 | 18.314 | −18.572 | 1.00 | 49.64 | O |
| ATOM | 7309 | C | GLU A | 1002 | −2.594 | 22.139 | −21.191 | 1.00 | 45.93 | C |
| ATOM | 7310 | O | GLU A | 1002 | −2.403 | 23.322 | −21.088 | 1.00 | 50.33 | O |
| ATOM | 7311 | N | PHE A | 1003 | −2.294 | 21.451 | −22.285 | 1.00 | 44.36 | N |
| ATOM | 7312 | CA | PHE A | 1003 | −1.674 | 22.038 | −23.492 | 1.00 | 39.17 | C |
| ATOM | 7313 | CB | PHE A | 1003 | −0.625 | 21.079 | −24.027 | 1.00 | 40.24 | C |
| ATOM | 7314 | CG | PHE A | 1003 | 0.277 | 21.642 | −25.061 | 1.00 | 40.13 | C |
| ATOM | 7315 | CD1 | PHE A | 1003 | −0.176 | 21.924 | −26.329 | 1.00 | 42.98 | C |
| ATOM | 7316 | CE1 | PHE A | 1003 | 0.705 | 22.414 | −27.287 | 1.00 | 43.30 | C |
| ATOM | 7317 | CZ | PHE A | 1003 | 2.037 | 22.602 | −26.983 | 1.00 | 39.67 | C |
| ATOM | 7318 | CE2 | PHE A | 1003 | 2.491 | 22.282 | −25.743 | 1.00 | 37.67 | C |
| ATOM | 7319 | CD2 | PHE A | 1003 | 1.623 | 21.793 | −24.799 | 1.00 | 39.24 | C |
| ATOM | 7320 | C | PHE A | 1003 | −2.745 | 22.222 | −24.534 | 1.00 | 37.69 | C |
| ATOM | 7321 | O | PHE A | 1003 | −3.375 | 21.281 | −24.993 | 1.00 | 38.92 | O |
| ATOM | 7322 | N | VAL A | 1004 | −2.950 | 23.457 | −24.930 | 1.00 | 38.24 | N |
| ATOM | 7323 | CA | VAL A | 1004 | −4.039 | 23.804 | −25.829 | 1.00 | 36.67 | C |
| ATOM | 7324 | CB | VAL A | 1004 | −4.546 | 25.183 | −25.502 | 1.00 | 34.37 | C |
| ATOM | 7325 | CG1 | VAL A | 1004 | −5.690 | 25.541 | −26.424 | 1.00 | 34.56 | C |
| ATOM | 7326 | CG2 | VAL A | 1004 | −4.973 | 25.151 | −24.059 | 1.00 | 35.40 | C |
| ATOM | 7327 | C | VAL A | 1004 | −3.574 | 23.805 | −27.255 | 1.00 | 35.51 | C |
| ATOM | 7328 | O | VAL A | 1004 | −2.604 | 24.439 | −27.566 | 1.00 | 34.42 | O |
| ATOM | 7329 | N | ASN A | 1005 | −4.272 | 23.082 | −28.109 | 1.00 | 36.66 | N |
| ATOM | 7330 | CA | ASN A | 1005 | −3.964 | 23.094 | −29.527 | 1.00 | 37.57 | C |
| ATOM | 7331 | CB | ASN A | 1005 | −4.112 | 21.716 | −30.138 | 1.00 | 37.70 | C |
| ATOM | 7332 | CG | ASN A | 1005 | −2.947 | 20.831 | −29.842 | 1.00 | 37.63 | C |
| ATOM | 7333 | OD1 | ASN A | 1005 | −1.794 | 21.243 | −29.817 | 1.00 | 40.58 | O |
| ATOM | 7334 | ND2 | ASN A | 1005 | −3.239 | 19.604 | −29.625 | 1.00 | 38.98 | N |
| ATOM | 7335 | C | ASN A | 1005 | −4.838 | 24.043 | −30.285 | 1.00 | 37.10 | C |
| ATOM | 7336 | O | ASN A | 1005 | −4.350 | 24.724 | −31.180 | 1.00 | 39.51 | O |
| ATOM | 7337 | N | VAL A | 1006 | −6.098 | 24.106 | −29.924 | 1.00 | 34.97 | N |
| ATOM | 7338 | CA | VAL A | 1006 | −7.027 | 24.819 | −30.702 | 1.00 | 37.16 | C |
| ATOM | 7339 | CB | VAL A | 1006 | −7.849 | 23.858 | −31.554 | 1.00 | 41.02 | C |
| ATOM | 7340 | CG1 | VAL A | 1006 | −8.489 | 22.685 | −30.756 | 1.00 | 44.02 | C |
| ATOM | 7341 | CG2 | VAL A | 1006 | −8.958 | 24.618 | −32.228 | 1.00 | 41.86 | C |
| ATOM | 7342 | C | VAL A | 1006 | −7.948 | 25.548 | −29.777 | 1.00 | 39.51 | C |
| ATOM | 7343 | O | VAL A | 1006 | −8.330 | 25.023 | −28.744 | 1.00 | 42.91 | O |
| ATOM | 7344 | N | PHE A | 1007 | −8.292 | 26.770 | −30.145 | 1.00 | 42.10 | N |
| ATOM | 7345 | CA | PHE A | 1007 | −9.394 | 27.494 | −29.526 | 1.00 | 41.88 | C |
| ATOM | 7346 | CB | PHE A | 1007 | −9.051 | 28.929 | −29.121 | 1.00 | 41.03 | C |
| ATOM | 7347 | CG | PHE A | 1007 | −8.105 | 29.054 | −27.959 | 1.00 | 39.08 | C |
| ATOM | 7348 | CD1 | PHE A | 1007 | −8.580 | 28.954 | −26.674 | 1.00 | 37.79 | C |
| ATOM | 7349 | CE1 | PHE A | 1007 | −7.756 | 29.115 | −25.609 | 1.00 | 38.32 | C |
| ATOM | 7350 | CZ | PHE A | 1007 | −6.404 | 29.398 | −25.823 | 1.00 | 40.79 | C |
| ATOM | 7351 | CE2 | PHE A | 1007 | −5.906 | 29.532 | −27.125 | 1.00 | 38.93 | C |
| ATOM | 7352 | CD2 | PHE A | 1007 | −6.758 | 29.348 | −28.174 | 1.00 | 37.86 | C |
| ATOM | 7353 | C | PHE A | 1007 | −10.357 | 27.627 | −30.635 | 1.00 | 43.34 | C |
| ATOM | 7354 | O | PHE A | 1007 | −9.946 | 27.751 | −31.800 | 1.00 | 42.02 | O |
| ATOM | 7355 | N | CYS A | 1008 | −11.631 | 27.660 | −30.265 | 1.00 | 48.10 | N |
| ATOM | 7356 | CA | CYS A | 1008 | −12.686 | 27.973 | −31.211 | 1.00 | 52.33 | C |
| ATOM | 7357 | CB | CYS A | 1008 | −12.862 | 26.786 | −32.153 | 1.00 | 56.36 | C |
| ATOM | 7358 | SG | CYS A | 1008 | −14.340 | 25.896 | −31.875 | 1.00 | 65.02 | S |
| ATOM | 7359 | C | CYS A | 1008 | −14.007 | 28.452 | −30.569 | 1.00 | 48.86 | C |
| ATOM | 7360 | O | CYS A | 1008 | −14.471 | 27.929 | −29.580 | 1.00 | 47.72 | O |
| ATOM | 7361 | N | HIS A | 1009 | −14.567 | 29.499 | −31.133 | 1.00 | 49.60 | N |
| ATOM | 7362 | CA | HIS A | 1009 | −15.731 | 30.163 | −30.558 | 1.00 | 49.55 | C |
| ATOM | 7363 | CB | HIS A | 1009 | −16.059 | 31.505 | −31.260 | 1.00 | 47.71 | C |
| ATOM | 7364 | CG | HIS A | 1009 | −15.060 | 32.582 | −31.015 | 1.00 | 48.72 | C |
| ATOM | 7365 | ND1 | HIS A | 1009 | −15.292 | 33.622 | −30.141 | 1.00 | 52.52 | N |
| ATOM | 7366 | CE1 | HIS A | 1009 | −14.231 | 34.410 | −30.105 | 1.00 | 53.27 | C |
| ATOM | 7367 | NE2 | HIS A | 1009 | −13.309 | 33.906 | −30.908 | 1.00 | 51.98 | N |
| ATOM | 7368 | CD2 | HIS A | 1009 | −13.810 | 32.769 | −31.500 | 1.00 | 50.64 | C |
| ATOM | 7369 | C | HIS A | 1009 | −16.861 | 29.226 | −30.837 | 1.00 | 47.82 | C |
| ATOM | 7370 | O | HIS A | 1009 | −16.987 | 28.735 | −31.926 | 1.00 | 52.26 | O |
| ATOM | 7371 | N | GLY A | 1010 | −17.674 | 28.988 | −29.850 | 1.00 | 45.57 | N |
| ATOM | 7372 | CA | GLY A | 1010 | −18.898 | 28.274 | −30.047 | 1.00 | 46.62 | C |
| ATOM | 7373 | C | GLY A | 1010 | −19.327 | 27.839 | −28.662 | 1.00 | 46.22 | C |
| ATOM | 7374 | O | GLY A | 1010 | −18.611 | 28.083 | −27.692 | 1.00 | 43.44 | O |
| ATOM | 7375 | N | SER A | 1011 | −20.494 | 27.213 | −28.580 | 1.00 | 44.17 | N |
| ATOM | 7376 | CA | SER A | 1011 | −20.949 | 26.666 | −27.348 | 1.00 | 44.22 | C |
| ATOM | 7377 | CB | SER A | 1011 | −21.650 | 27.770 | −26.593 | 1.00 | 45.19 | C |
| ATOM | 7378 | OG | SER A | 1011 | −22.792 | 27.383 | −25.871 | 1.00 | 48.14 | O |
| ATOM | 7379 | C | SER A | 1011 | −21.824 | 25.459 | −27.614 | 1.00 | 46.61 | C |
| ATOM | 7380 | O | SER A | 1011 | −22.501 | 25.381 | −28.665 | 1.00 | 44.23 | O |

TABLE 6-continued

Atomic coordinates for CRBN:DDB1: Compound B (Human protein)

| ATOM | 7381 | N | LEU A | 1012 | −21.807 | 24.525 | −26.649 | 1.00 | 49.13 | N |
|---|---|---|---|---|---|---|---|---|---|---|
| ATOM | 7382 | CA | LEU A | 1012 | −22.606 | 23.295 | −26.716 | 1.00 | 50.67 | C |
| ATOM | 7383 | CB | LEU A | 1012 | −21.789 | 22.061 | −26.356 | 1.00 | 51.41 | C |
| ATOM | 7384 | CG | LEU A | 1012 | −20.296 | 22.060 | −26.637 | 1.00 | 55.02 | C |
| ATOM | 7385 | CD1 | LEU A | 1012 | −19.593 | 21.110 | −25.681 | 1.00 | 59.04 | C |
| ATOM | 7386 | CD2 | LEU A | 1012 | −20.023 | 21.695 | −28.027 | 1.00 | 58.13 | C |
| ATOM | 7387 | C | LEU A | 1012 | −23.872 | 23.348 | −25.850 | 1.00 | 52.62 | C |
| ATOM | 7388 | O | LEU A | 1012 | −24.378 | 22.293 | −25.495 | 1.00 | 57.41 | O |
| ATOM | 7389 | N | VAL A | 1013 | −24.409 | 24.535 | −25.540 | 1.00 | 54.08 | N |
| ATOM | 7390 | CA | VAL A | 1013 | −25.751 | 24.631 | −24.931 | 1.00 | 58.27 | C |
| ATOM | 7391 | CB | VAL A | 1013 | −25.725 | 25.185 | −23.512 | 1.00 | 54.60 | C |
| ATOM | 7392 | CG1 | VAL A | 1013 | −24.982 | 24.246 | −22.617 | 1.00 | 56.58 | C |
| ATOM | 7393 | CG2 | VAL A | 1013 | −25.076 | 26.524 | −23.470 | 1.00 | 56.15 | C |
| ATOM | 7394 | C | VAL A | 1013 | −26.705 | 25.441 | −25.800 | 1.00 | 65.09 | C |
| ATOM | 7395 | O | VAL A | 1013 | −26.261 | 26.076 | −26.751 | 1.00 | 67.17 | O |
| ATOM | 7396 | N | MET A | 1014 | −28.000 | 25.379 | −25.478 | 1.00 | 70.99 | N |
| ATOM | 7397 | CA | MET A | 1014 | −29.029 | 25.993 | −26.276 | 1.00 | 75.07 | C |
| ATOM | 7398 | CB | MET A | 1014 | −30.277 | 25.098 | −26.367 | 1.00 | 84.03 | C |
| ATOM | 7399 | CG | MET A | 1014 | −29.990 | 23.676 | −26.876 | 1.00 | 90.96 | C |
| ATOM | 7400 | SD | MET A | 1014 | −31.317 | 22.630 | −27.616 | 1.00 | 109.59 | S |
| ATOM | 7401 | CE | MET A | 1014 | −32.615 | 22.593 | −26.358 | 1.00 | 100.77 | C |
| ATOM | 7402 | C | MET A | 1014 | −29.327 | 27.325 | −25.659 | 1.00 | 70.94 | C |
| ATOM | 7403 | O | MET A | 1014 | −29.336 | 28.311 | −26.386 | 1.00 | 73.82 | O |
| ATOM | 7404 | N | THR A | 1024 | −21.952 | 36.019 | −17.479 | 1.00 | 59.52 | N |
| ATOM | 7405 | CA | THR A | 1024 | −21.084 | 35.540 | −18.622 | 1.00 | 61.75 | C |
| ATOM | 7406 | CB | THR A | 1024 | −21.136 | 34.016 | −18.815 | 1.00 | 66.10 | C |
| ATOM | 7407 | OG1 | THR A | 1024 | −22.455 | 33.603 | −19.267 | 1.00 | 64.43 | O |
| ATOM | 7408 | CG2 | THR A | 1024 | −20.711 | 33.314 | −17.494 | 1.00 | 67.78 | C |
| ATOM | 7409 | C | THR A | 1024 | −21.366 | 36.067 | −20.029 | 1.00 | 58.82 | C |
| ATOM | 7410 | O | THR A | 1024 | −22.490 | 36.039 | −20.490 | 1.00 | 58.68 | O |
| ATOM | 7411 | N | GLN A | 1025 | −20.307 | 36.493 | −20.708 | 1.00 | 65.07 | N |
| ATOM | 7412 | CA | GLN A | 1025 | −20.349 | 37.049 | −22.076 | 1.00 | 71.43 | C |
| ATOM | 7413 | CB | GLN A | 1025 | −20.179 | 38.594 | −22.063 | 1.00 | 83.00 | C |
| ATOM | 7414 | CG | GLN A | 1025 | −21.095 | 39.415 | −21.096 | 1.00 | 91.73 | C |
| ATOM | 7415 | CD | GLN A | 1025 | −20.421 | 40.087 | −19.837 | 1.00 | 93.79 | C |
| ATOM | 7416 | OE1 | GLN A | 1025 | −19.265 | 40.618 | −19.845 | 1.00 | 87.63 | O |
| ATOM | 7417 | NE2 | GLN A | 1025 | −21.197 | 40.109 | −18.753 | 1.00 | 92.61 | N |
| ATOM | 7418 | C | GLN A | 1025 | −19.222 | 36.383 | −22.929 | 1.00 | 68.26 | C |
| ATOM | 7419 | O | GLN A | 1025 | −18.021 | 36.346 | −22.523 | 1.00 | 62.24 | O |
| ATOM | 7420 | N | GLY A | 1026 | −19.622 | 35.834 | −24.087 | 1.00 | 61.12 | N |
| ATOM | 7421 | CA | GLY A | 1026 | −18.732 | 35.082 | −24.947 | 1.00 | 56.20 | C |
| ATOM | 7422 | C | GLY A | 1026 | −18.714 | 33.612 | −24.562 | 1.00 | 57.05 | C |
| ATOM | 7423 | O | GLY A | 1026 | −19.130 | 33.230 | −23.483 | 1.00 | 55.87 | O |
| ATOM | 7424 | N | SER A | 1027 | −18.268 | 32.780 | −25.496 | 1.00 | 56.89 | N |
| ATOM | 7425 | CA | SER A | 1027 | −17.950 | 31.380 | −25.263 | 1.00 | 50.84 | C |
| ATOM | 7426 | CB | SER A | 1027 | −19.171 | 30.501 | −25.544 | 1.00 | 49.63 | C |
| ATOM | 7427 | OG | SER A | 1027 | −19.184 | 29.260 | −24.793 | 1.00 | 49.52 | O |
| ATOM | 7428 | C | SER A | 1027 | −16.798 | 31.046 | −26.208 | 1.00 | 49.11 | C |
| ATOM | 7429 | O | SER A | 1027 | −16.923 | 31.183 | −27.408 | 1.00 | 50.75 | O |
| ATOM | 7430 | N | VAL A | 1028 | −15.660 | 30.642 | −25.662 | 1.00 | 48.63 | N |
| ATOM | 7431 | CA | VAL A | 1028 | −14.569 | 30.066 | −26.461 | 1.00 | 44.94 | C |
| ATOM | 7432 | CB | VAL A | 1028 | −13.395 | 30.984 | −26.442 | 1.00 | 41.96 | C |
| ATOM | 7433 | CG1 | VAL A | 1028 | −12.138 | 30.240 | −26.800 | 1.00 | 41.75 | C |
| ATOM | 7434 | CG2 | VAL A | 1028 | −13.712 | 32.058 | −27.433 | 1.00 | 42.57 | C |
| ATOM | 7435 | C | VAL A | 1028 | −14.173 | 28.711 | −25.936 | 1.00 | 41.85 | C |
| ATOM | 7436 | O | VAL A | 1028 | −13.858 | 28.583 | −24.796 | 1.00 | 41.88 | O |
| ATOM | 7437 | N | LEU A | 1029 | −14.224 | 27.714 | −26.799 | 1.00 | 41.31 | N |
| ATOM | 7438 | CA | LEU A | 1029 | −13.955 | 26.337 | −26.430 | 1.00 | 42.43 | C |
| ATOM | 7439 | CB | LEU A | 1029 | −14.841 | 25.346 | −27.209 | 1.00 | 43.17 | C |
| ATOM | 7440 | CG | LEU A | 1029 | −16.297 | 25.397 | −26.701 | 1.00 | 44.23 | C |
| ATOM | 7441 | CD1 | LEU A | 1029 | −17.366 | 24.881 | −27.677 | 1.00 | 42.25 | C |
| ATOM | 7442 | CD2 | LEU A | 1029 | −16.356 | 24.685 | −25.345 | 1.00 | 46.45 | C |
| ATOM | 7443 | C | LEU A | 1029 | −12.541 | 26.110 | −26.787 | 1.00 | 41.69 | C |
| ATOM | 7444 | O | LEU A | 1029 | −12.040 | 26.693 | −27.712 | 1.00 | 45.25 | O |
| ATOM | 7445 | N | PHE A | 1030 | −11.884 | 25.245 | −26.063 | 1.00 | 40.29 | N |
| ATOM | 7446 | CA | PHE A | 1030 | −10.583 | 24.828 | −26.483 | 1.00 | 39.72 | C |
| ATOM | 7447 | CB | PHE A | 1030 | −9.491 | 25.626 | −25.776 | 1.00 | 39.45 | C |
| ATOM | 7448 | CG | PHE A | 1030 | −9.541 | 25.535 | −24.290 | 1.00 | 38.57 | C |
| ATOM | 7449 | CD1 | PHE A | 1030 | −8.886 | 24.538 | −23.650 | 1.00 | 39.49 | C |
| ATOM | 7450 | CE1 | PHE A | 1030 | −8.913 | 24.470 | −22.244 | 1.00 | 38.97 | C |
| ATOM | 7451 | CZ | PHE A | 1030 | −9.584 | 25.394 | −21.530 | 1.00 | 36.69 | C |
| ATOM | 7452 | CE2 | PHE A | 1030 | −10.269 | 26.372 | −22.188 | 1.00 | 37.51 | C |
| ATOM | 7453 | CD2 | PHE A | 1030 | −10.242 | 26.447 | −23.554 | 1.00 | 38.03 | C |
| ATOM | 7454 | C | PHE A | 1030 | −10.443 | 23.364 | −26.201 | 1.00 | 39.24 | C |
| ATOM | 7455 | O | PHE A | 1030 | −11.147 | 22.800 | −25.342 | 1.00 | 38.02 | O |
| ATOM | 7456 | N | GLY A | 1031 | −9.532 | 22.777 | −26.961 | 1.00 | 37.68 | N |
| ATOM | 7457 | CA | GLY A | 1031 | −9.280 | 21.375 | −26.918 | 1.00 | 36.44 | C |
| ATOM | 7458 | C | GLY A | 1031 | −7.815 | 21.239 | −26.737 | 1.00 | 35.68 | C |

TABLE 6-continued

Atomic coordinates for CRBN:DDB1: Compound B (Human protein)

| ATOM | 7459 | O | GLY A | 1031 | −7.049 | 22.127 | −27.055 | 1.00 | 36.80 | O |
|---|---|---|---|---|---|---|---|---|---|---|
| ATOM | 7460 | N | THR A | 1032 | −7.434 | 20.064 | −26.308 | 1.00 | 35.56 | N |
| ATOM | 7461 | CA | THR A | 1032 | −6.243 | 19.908 | −25.608 | 1.00 | 36.11 | C |
| ATOM | 7462 | CB | THR A | 1032 | −6.714 | 19.972 | −24.153 | 1.00 | 36.91 | C |
| ATOM | 7463 | OG1 | THR A | 1032 | −6.093 | 21.078 | −23.511 | 1.00 | 44.15 | O |
| ATOM | 7464 | CG2 | THR A | 1032 | −6.552 | 18.705 | −23.402 | 1.00 | 34.16 | C |
| ATOM | 7465 | C | THR A | 1032 | −5.627 | 18.578 | −25.987 | 1.00 | 36.48 | C |
| ATOM | 7466 | O | THR A | 1032 | −6.324 | 17.691 | −26.437 | 1.00 | 39.40 | O |
| ATOM | 7467 | N | VAL A | 1033 | −4.339 | 18.428 | −25.726 | 1.00 | 34.84 | N |
| ATOM | 7468 | CA | VAL A | 1033 | −3.580 | 17.187 | −25.909 | 1.00 | 33.06 | C |
| ATOM | 7469 | CB | VAL A | 1033 | −2.117 | 17.493 | −25.578 | 1.00 | 33.29 | C |
| ATOM | 7470 | CG1 | VAL A | 1033 | −1.230 | 16.266 | −25.527 | 1.00 | 33.27 | C |
| ATOM | 7471 | CG2 | VAL A | 1033 | −1.550 | 18.481 | −26.607 | 1.00 | 33.71 | C |
| ATOM | 7472 | C | VAL A | 1033 | −4.034 | 15.946 | −25.102 | 1.00 | 35.01 | C |
| ATOM | 7473 | O | VAL A | 1033 | −3.920 | 14.804 | −25.553 | 1.00 | 39.90 | O |
| ATOM | 7474 | N | ASN A | 1034 | −4.472 | 16.126 | −23.872 | 1.00 | 37.09 | N |
| ATOM | 7475 | CA | ASN A | 1034 | −4.984 | 15.024 | −23.077 | 1.00 | 35.32 | C |
| ATOM | 7476 | CB | ASN A | 1034 | −4.703 | 15.270 | −21.609 | 1.00 | 37.64 | C |
| ATOM | 7477 | CG | ASN A | 1034 | −3.226 | 15.249 | −21.302 | 1.00 | 40.92 | C |
| ATOM | 7478 | OD1 | ASN A | 1034 | −2.755 | 15.738 | −20.263 | 1.00 | 45.55 | O |
| ATOM | 7479 | ND2 | ASN A | 1034 | −2.468 | 14.714 | −22.237 | 1.00 | 41.59 | N |
| ATOM | 7480 | C | ASN A | 1034 | −6.406 | 14.824 | −23.296 | 1.00 | 35.09 | C |
| ATOM | 7481 | O | ASN A | 1034 | −7.022 | 14.104 | −22.578 | 1.00 | 35.36 | O |
| ATOM | 7482 | N | GLY A | 1035 | −6.966 | 15.434 | −24.315 | 1.00 | 37.74 | N |
| ATOM | 7483 | CA | GLY A | 1035 | −8.377 | 15.256 | −24.572 | 1.00 | 39.04 | C |
| ATOM | 7484 | C | GLY A | 1035 | −9.312 | 15.965 | −23.633 | 1.00 | 38.69 | C |
| ATOM | 7485 | O | GLY A | 1035 | −10.496 | 15.786 | −23.721 | 1.00 | 37.94 | O |
| ATOM | 7486 | N | MET A | 1036 | −8.799 | 16.752 | −22.709 | 1.00 | 42.94 | N |
| ATOM | 7487 | CA | MET A | 1036 | −9.644 | 17.699 | −21.971 | 1.00 | 43.94 | C |
| ATOM | 7488 | CB | MET A | 1036 | −8.910 | 18.275 | −20.741 | 1.00 | 45.17 | C |
| ATOM | 7489 | CG | MET A | 1036 | −9.588 | 19.436 | −20.048 | 1.00 | 49.35 | C |
| ATOM | 7490 | SD | MET A | 1036 | −9.137 | 21.149 | −20.455 | 1.00 | 49.86 | S |
| ATOM | 7491 | CE | MET A | 1036 | −10.280 | 21.875 | −19.332 | 1.00 | 48.33 | C |
| ATOM | 7492 | C | MET A | 1036 | −10.115 | 18.770 | −22.946 | 1.00 | 41.84 | C |
| ATOM | 7493 | O | MET A | 1036 | −9.478 | 19.034 | −23.941 | 1.00 | 42.75 | O |
| ATOM | 7494 | N | ILE A | 1037 | −11.304 | 19.267 | −22.675 | 1.00 | 41.82 | N |
| ATOM | 7495 | CA | ILE A | 1037 | −11.989 | 20.321 | −23.396 | 1.00 | 40.94 | C |
| ATOM | 7496 | CB | ILE A | 1037 | −13.262 | 19.816 | −24.074 | 1.00 | 36.88 | C |
| ATOM | 7497 | CG1 | ILE A | 1037 | −12.948 | 18.734 | −25.088 | 1.00 | 35.90 | C |
| ATOM | 7498 | CD1 | ILE A | 1037 | −14.165 | 18.095 | −25.751 | 1.00 | 34.79 | C |
| ATOM | 7499 | CG2 | ILE A | 1037 | −13.967 | 20.952 | −24.761 | 1.00 | 38.65 | C |
| ATOM | 7500 | C | ILE A | 1037 | −12.412 | 21.353 | −22.324 | 1.00 | 45.81 | C |
| ATOM | 7501 | O | ILE A | 1037 | −12.953 | 20.993 | −21.242 | 1.00 | 42.24 | O |
| ATOM | 7502 | N | GLY A | 1038 | −12.159 | 22.626 | −22.626 | 1.00 | 49.31 | N |
| ATOM | 7503 | CA | GLY A | 1038 | −12.446 | 23.707 | −21.697 | 1.00 | 49.82 | C |
| ATOM | 7504 | C | GLY A | 1038 | −13.183 | 24.795 | −22.409 | 1.00 | 50.61 | C |
| ATOM | 7505 | O | GLY A | 1038 | −13.190 | 24.873 | −23.624 | 1.00 | 53.74 | O |
| ATOM | 7506 | N | LEU A | 1039 | −13.834 | 25.615 | −21.625 | 1.00 | 50.99 | N |
| ATOM | 7507 | CA | LEU A | 1039 | −14.609 | 26.699 | −22.114 | 1.00 | 49.89 | C |
| ATOM | 7508 | CB | LEU A | 1039 | −16.044 | 26.412 | −21.728 | 1.00 | 50.42 | C |
| ATOM | 7509 | CG | LEU A | 1039 | −16.920 | 27.623 | −21.944 | 1.00 | 55.77 | C |
| ATOM | 7510 | CD1 | LEU A | 1039 | −18.265 | 27.265 | −22.532 | 1.00 | 60.64 | C |
| ATOM | 7511 | CD2 | LEU A | 1039 | −17.147 | 28.300 | −20.611 | 1.00 | 60.54 | C |
| ATOM | 7512 | C | LEU A | 1039 | −14.055 | 27.967 | −21.458 | 1.00 | 48.92 | C |
| ATOM | 7513 | O | LEU A | 1039 | −13.716 | 27.995 | −20.277 | 1.00 | 50.79 | O |
| ATOM | 7514 | N | VAL A | 1040 | −13.964 | 29.046 | −22.201 | 1.00 | 49.48 | N |
| ATOM | 7515 | CA | VAL A | 1040 | −13.620 | 30.334 | −21.586 | 1.00 | 46.33 | C |
| ATOM | 7516 | CB | VAL A | 1040 | −12.318 | 30.885 | −22.113 | 1.00 | 42.74 | C |
| ATOM | 7517 | CG1 | VAL A | 1040 | −12.104 | 32.274 | −21.587 | 1.00 | 43.78 | C |
| ATOM | 7518 | CG2 | VAL A | 1040 | −11.185 | 30.033 | −21.613 | 1.00 | 43.78 | C |
| ATOM | 7519 | C | VAL A | 1040 | −14.721 | 31.325 | −21.845 | 1.00 | 48.14 | C |
| ATOM | 7520 | O | VAL A | 1040 | −15.203 | 31.441 | −22.965 | 1.00 | 54.01 | O |
| ATOM | 7521 | N | THR A | 1041 | −15.133 | 32.040 | −20.814 | 1.00 | 49.61 | N |
| ATOM | 7522 | CA | THR A | 1041 | −16.107 | 33.089 | −20.987 | 1.00 | 51.39 | C |
| ATOM | 7523 | CB | THR A | 1041 | −17.458 | 32.637 | −20.490 | 1.00 | 52.65 | C |
| ATOM | 7524 | OG1 | THR A | 1041 | −18.422 | 33.491 | −21.057 | 1.00 | 58.22 | O |
| ATOM | 7525 | CG2 | THR A | 1041 | −17.567 | 32.704 | −18.999 | 1.00 | 54.27 | C |
| ATOM | 7526 | C | THR A | 1041 | −15.631 | 34.311 | −20.272 | 1.00 | 52.38 | C |
| ATOM | 7527 | O | THR A | 1041 | −14.598 | 34.266 | −19.642 | 1.00 | 53.56 | O |
| ATOM | 7528 | N | SER A | 1042 | −16.370 | 35.405 | −20.386 | 1.00 | 57.34 | N |
| ATOM | 7529 | CA | SER A | 1042 | −15.934 | 36.714 | −19.848 | 1.00 | 58.09 | C |
| ATOM | 7530 | CB | SER A | 1042 | −15.638 | 37.680 | −20.995 | 1.00 | 60.08 | C |
| ATOM | 7531 | OG | SER A | 1042 | −14.627 | 37.105 | −21.821 | 1.00 | 66.91 | O |
| ATOM | 7532 | C | SER A | 1042 | −16.977 | 37.260 | −18.899 | 1.00 | 53.93 | C |
| ATOM | 7533 | O | SER A | 1042 | −18.128 | 36.964 | −19.054 | 1.00 | 52.87 | O |
| ATOM | 7534 | N | LEU A | 1043 | −16.555 | 38.033 | −17.904 | 1.00 | 54.58 | N |
| ATOM | 7535 | CA | LEU A | 1043 | −17.401 | 38.426 | −16.778 | 1.00 | 54.73 | C |
| ATOM | 7536 | CB | LEU A | 1043 | −16.823 | 37.826 | −15.507 | 1.00 | 55.25 | C |

TABLE 6-continued

Atomic coordinates for CRBN:DDB1: Compound B (Human protein)

| ATOM | 7537 | CG | LEU A | 1043 | −16.824 | 36.319 | −15.310 | 1.00 | 55.96 | C |
|---|---|---|---|---|---|---|---|---|---|---|
| ATOM | 7538 | CD1 | LEU A | 1043 | −16.299 | 35.941 | −13.925 | 1.00 | 55.37 | C |
| ATOM | 7539 | CD2 | LEU A | 1043 | −18.225 | 35.771 | −15.543 | 1.00 | 58.16 | C |
| ATOM | 7540 | C | LEU A | 1043 | −17.415 | 39.911 | −16.539 | 1.00 | 56.39 | C |
| ATOM | 7541 | O | LEU A | 1043 | −16.418 | 40.582 | −16.778 | 1.00 | 57.04 | O |
| ATOM | 7542 | N | SER A | 1044 | −18.513 | 40.408 | −15.974 | 1.00 | 57.59 | N |
| ATOM | 7543 | CA | SER A | 1044 | −18.525 | 41.781 | −15.448 | 1.00 | 58.17 | C |
| ATOM | 7544 | CB | SER A | 1044 | −19.957 | 42.332 | −15.167 | 1.00 | 61.70 | C |
| ATOM | 7545 | OG | SER A | 1044 | −20.589 | 41.822 | −13.991 | 1.00 | 62.51 | O |
| ATOM | 7546 | C | SER A | 1044 | −17.673 | 41.842 | −14.203 | 1.00 | 57.72 | C |
| ATOM | 7547 | O | SER A | 1044 | −17.726 | 40.939 | −13.340 | 1.00 | 53.14 | O |
| ATOM | 7548 | N | GLU A | 1045 | −16.899 | 42.922 | −14.123 | 1.00 | 60.20 | N |
| ATOM | 7549 | CA | GLU A | 1045 | −16.081 | 43.224 | −12.940 | 1.00 | 62.00 | C |
| ATOM | 7550 | CB | GLU A | 1045 | −15.651 | 44.691 | −12.943 | 1.00 | 64.15 | C |
| ATOM | 7551 | CG | GLU A | 1045 | −14.409 | 44.897 | −12.106 | 1.00 | 67.58 | C |
| ATOM | 7552 | CD | GLU A | 1045 | −14.101 | 46.330 | −11.732 | 1.00 | 71.08 | C |
| ATOM | 7553 | OE1 | GLU A | 1045 | −14.963 | 47.230 | −11.941 | 1.00 | 68.89 | O |
| ATOM | 7554 | OE2 | GLU A | 1045 | −12.987 | 46.501 | −11.160 | 1.00 | 71.84 | O |
| ATOM | 7555 | C | GLU A | 1045 | −16.754 | 42.906 | −11.591 | 1.00 | 59.68 | C |
| ATOM | 7556 | O | GLU A | 1045 | −16.132 | 42.302 | −10.718 | 1.00 | 54.67 | O |
| ATOM | 7557 | N | SER A | 1046 | −18.003 | 43.330 | −11.415 | 1.00 | 60.36 | N |
| ATOM | 7558 | CA | SER A | 1046 | −18.736 | 42.979 | −10.200 | 1.00 | 65.65 | C |
| ATOM | 7559 | CB | SER A | 1046 | −20.235 | 43.394 | −10.304 | 1.00 | 69.51 | C |
| ATOM | 7560 | OG | SER A | 1046 | −21.126 | 42.589 | −9.492 | 1.00 | 73.62 | O |
| ATOM | 7561 | C | SER A | 1046 | −18.553 | 41.464 | −9.894 | 1.00 | 65.72 | C |
| ATOM | 7562 | O | SER A | 1046 | −18.059 | 41.098 | −8.808 | 1.00 | 65.05 | O |
| ATOM | 7563 | N | TRP A | 1047 | −18.903 | 40.623 | −10.884 | 1.00 | 64.65 | N |
| ATOM | 7564 | CA | TRP A | 1047 | −18.928 | 39.151 | −10.742 | 1.00 | 62.81 | C |
| ATOM | 7565 | CB | TRP A | 1047 | −19.624 | 38.452 | −11.935 | 1.00 | 66.63 | C |
| ATOM | 7566 | CG | TRP A | 1047 | −21.144 | 38.317 | −11.809 | 1.00 | 69.96 | C |
| ATOM | 7567 | CD1 | TRP A | 1047 | −22.083 | 39.091 | −12.404 | 1.00 | 67.97 | C |
| ATOM | 7568 | NE1 | TRP A | 1047 | −23.335 | 38.669 | −12.064 | 1.00 | 67.73 | N |
| ATOM | 7569 | CE2 | TRP A | 1047 | −23.232 | 37.595 | −11.236 | 1.00 | 73.62 | C |
| ATOM | 7570 | CD2 | TRP A | 1047 | −21.862 | 37.342 | −11.055 | 1.00 | 76.16 | C |
| ATOM | 7571 | CE3 | TRP A | 1047 | −21.476 | 36.291 | −10.220 | 1.00 | 88.56 | C |
| ATOM | 7572 | CZ3 | TRP A | 1047 | −22.473 | 35.527 | −9.586 | 1.00 | 89.66 | C |
| ATOM | 7573 | CH2 | TRP A | 1047 | −23.832 | 35.806 | −9.794 | 1.00 | 86.74 | C |
| ATOM | 7574 | CZ2 | TRP A | 1047 | −24.228 | 36.836 | −10.616 | 1.00 | 81.04 | C |
| ATOM | 7575 | C | TRP A | 1047 | −17.520 | 38.611 | −10.599 | 1.00 | 56.09 | C |
| ATOM | 7576 | O | TRP A | 1047 | −17.246 | 37.727 | −9.787 | 1.00 | 51.59 | O |
| ATOM | 7577 | N | TYR A | 1048 | −16.612 | 39.149 | −11.379 | 1.00 | 49.72 | N |
| ATOM | 7578 | CA | TYR A | 1048 | −15.266 | 38.770 | −11.165 | 1.00 | 50.25 | C |
| ATOM | 7579 | CB | TYR A | 1048 | −14.313 | 39.545 | −12.055 | 1.00 | 52.38 | C |
| ATOM | 7580 | CG | TYR A | 1048 | −12.878 | 39.156 | −11.835 | 1.00 | 52.06 | C |
| ATOM | 7581 | CD1 | TYR A | 1048 | −12.275 | 38.133 | −12.553 | 1.00 | 50.52 | C |
| ATOM | 7582 | CE1 | TYR A | 1048 | −10.961 | 37.768 | −12.304 | 1.00 | 51.48 | C |
| ATOM | 7583 | CZ | TYR A | 1048 | −10.247 | 38.438 | −11.329 | 1.00 | 54.64 | C |
| ATOM | 7584 | OH | TYR A | 1048 | −8.921 | 38.200 | −11.008 | 1.00 | 55.15 | O |
| ATOM | 7585 | CE2 | TYR A | 1048 | −10.849 | 39.440 | −10.614 | 1.00 | 56.97 | C |
| ATOM | 7586 | CD2 | TYR A | 1048 | −12.152 | 39.781 | −10.860 | 1.00 | 54.33 | C |
| ATOM | 7587 | C | TYR A | 1048 | −14.908 | 38.960 | −9.708 | 1.00 | 51.25 | C |
| ATOM | 7588 | O | TYR A | 1048 | −14.355 | 38.057 | −9.098 | 1.00 | 52.40 | O |
| ATOM | 7589 | N | ASN A | 1049 | −15.223 | 40.120 | −9.134 | 1.00 | 54.11 | N |
| ATOM | 7590 | CA | ASN A | 1049 | −14.808 | 40.379 | −7.743 | 1.00 | 52.68 | C |
| ATOM | 7591 | CB | ASN A | 1049 | −15.020 | 41.821 | −7.385 | 1.00 | 52.68 | C |
| ATOM | 7592 | CG | ASN A | 1049 | −14.035 | 42.706 | −8.078 | 1.00 | 53.71 | C |
| ATOM | 7593 | OD1 | ASN A | 1049 | −12.839 | 42.426 | −8.113 | 1.00 | 52.42 | O |
| ATOM | 7594 | ND2 | ASN A | 1049 | −14.531 | 43.774 | −8.659 | 1.00 | 58.26 | N |
| ATOM | 7595 | C | ASN A | 1049 | −15.443 | 39.468 | −6.721 | 1.00 | 49.46 | C |
| ATOM | 7596 | O | ASN A | 1049 | −14.757 | 38.913 | −5.864 | 1.00 | 44.45 | O |
| ATOM | 7597 | N | LEU A | 1050 | −16.742 | 39.293 | −6.858 | 1.00 | 48.92 | N |
| ATOM | 7598 | CA | LEU A | 1050 | −17.464 | 38.349 | −6.053 | 1.00 | 51.63 | C |
| ATOM | 7599 | CB | LEU A | 1050 | −18.873 | 38.250 | −6.565 | 1.00 | 51.31 | C |
| ATOM | 7600 | CG | LEU A | 1050 | −19.711 | 37.148 | −5.959 | 1.00 | 54.05 | C |
| ATOM | 7601 | CD1 | LEU A | 1050 | −19.619 | 37.080 | −4.451 | 1.00 | 56.95 | C |
| ATOM | 7602 | CD2 | LEU A | 1050 | −21.137 | 37.428 | −6.346 | 1.00 | 58.09 | C |
| ATOM | 7603 | C | LEU A | 1050 | −16.852 | 36.963 | −6.081 | 1.00 | 56.96 | C |
| ATOM | 7604 | O | LEU A | 1050 | −16.511 | 36.379 | −5.015 | 1.00 | 65.50 | O |
| ATOM | 7605 | N | LEU A | 1051 | −16.732 | 36.422 | −7.297 | 1.00 | 55.43 | N |
| ATOM | 7606 | CA | LEU A | 1051 | −16.262 | 35.044 | −7.471 | 1.00 | 49.96 | C |
| ATOM | 7607 | CB | LEU A | 1051 | −16.380 | 34.580 | −8.923 | 1.00 | 48.32 | C |
| ATOM | 7608 | CG | LEU A | 1051 | −17.779 | 34.495 | −9.527 | 1.00 | 46.10 | C |
| ATOM | 7609 | CD1 | LEU A | 1051 | −17.616 | 34.302 | −11.029 | 1.00 | 46.82 | C |
| ATOM | 7610 | CD2 | LEU A | 1051 | −18.630 | 33.399 | −8.924 | 1.00 | 44.19 | C |
| ATOM | 7611 | C | LEU A | 1051 | −14.845 | 34.864 | −6.994 | 1.00 | 46.84 | C |
| ATOM | 7612 | O | LEU A | 1051 | −14.516 | 33.765 | −6.560 | 1.00 | 47.42 | O |
| ATOM | 7613 | N | LEU A | 1052 | −14.029 | 35.925 | −7.052 | 1.00 | 44.50 | N |
| ATOM | 7614 | CA | LEU A | 1052 | −12.649 | 35.866 | −6.527 | 1.00 | 46.59 | C |

TABLE 6-continued

Atomic coordinates for CRBN:DDB1: Compound B (Human protein)

| ATOM | 7615 | CB | LEU A | 1052 | −11.855 | 37.132 | −6.836 | 1.00 | 45.91 | C |
|---|---|---|---|---|---|---|---|---|---|---|
| ATOM | 7616 | CG | LEU A | 1052 | −10.381 | 36.841 | −7.096 | 1.00 | 47.36 | C |
| ATOM | 7617 | CD1 | LEU A | 1052 | −9.641 | 38.126 | −7.440 | 1.00 | 47.80 | C |
| ATOM | 7618 | CD2 | LEU A | 1052 | −9.680 | 36.106 | −5.962 | 1.00 | 49.67 | C |
| ATOM | 7619 | C | LEU A | 1052 | −12.633 | 35.676 | −5.028 | 1.00 | 48.30 | C |
| ATOM | 7620 | O | LEU A | 1052 | −11.866 | 34.872 | 4.494 | 1.00 | 45.08 | O |
| ATOM | 7621 | N | ASP A | 1053 | −13.475 | 36.455 | −4.350 | 1.00 | 55.11 | N |
| ATOM | 7622 | CA | ASP A | 1053 | −13.581 | 36.375 | −2.916 | 1.00 | 60.36 | C |
| ATOM | 7623 | CB | ASP A | 1053 | −14.637 | 37.365 | −2.342 | 1.00 | 65.76 | C |
| ATOM | 7624 | CG | ASP A | 1053 | −14.592 | 37.478 | −0.769 | 1.00 | 70.90 | C |
| ATOM | 7625 | OD1 | ASP A | 1053 | −13.540 | 37.214 | −0.121 | 1.00 | 68.20 | O |
| ATOM | 7626 | OD2 | ASP A | 1053 | −15.641 | 37.825 | −0.179 | 1.00 | 76.05 | O |
| ATOM | 7627 | C | ASP A | 1053 | −13.946 | 34.920 | −2.692 | 1.00 | 58.30 | C |
| ATOM | 7628 | O | ASP A | 1053 | −13.261 | 34.178 | −1.956 | 1.00 | 57.98 | O |
| ATOM | 7629 | N | MET A | 1054 | −14.969 | 34.490 | −3.410 | 1.00 | 55.30 | N |
| ATOM | 7630 | CA | MET A | 1054 | −15.480 | 33.193 | −3.157 | 1.00 | 55.25 | C |
| ATOM | 7631 | CB | MET A | 1054 | −16.754 | 33.001 | −3.888 | 1.00 | 61.89 | C |
| ATOM | 7632 | CG | MET A | 1054 | −17.740 | 32.398 | −2.931 | 1.00 | 68.91 | C |
| ATOM | 7633 | SD | MET A | 1054 | −19.256 | 32.483 | −3.813 | 1.00 | 89.64 | S |
| ATOM | 7634 | CE | MET A | 1054 | −19.010 | 31.045 | −4.885 | 1.00 | 86.76 | C |
| ATOM | 7635 | C | MET A | 1054 | −14.508 | 32.050 | −3.397 | 1.00 | 50.45 | C |
| ATOM | 7636 | O | MET A | 1054 | −14.514 | 31.070 | −2.656 | 1.00 | 48.31 | O |
| ATOM | 7637 | N | GLN A | 1055 | −13.640 | 32.183 | −4.383 | 1.00 | 48.02 | N |
| ATOM | 7638 | CA | GLN A | 1055 | −12.529 | 31.264 | −4.488 | 1.00 | 48.29 | C |
| ATOM | 7639 | CB | GLN A | 1055 | −11.566 | 31.731 | −5.572 | 1.00 | 51.57 | C |
| ATOM | 7640 | CG | GLN A | 1055 | −12.135 | 31.436 | −6.951 | 1.00 | 53.12 | C |
| ATOM | 7641 | CD | GLN A | 1055 | −11.136 | 31.461 | −8.088 | 1.00 | 54.80 | C |
| ATOM | 7642 | OE1 | GLN A | 1055 | −9.949 | 31.655 | −7.940 | 1.00 | 56.67 | O |
| ATOM | 7643 | NE2 | GLN A | 1055 | −11.651 | 31.288 | −9.247 | 1.00 | 57.00 | N |
| ATOM | 7644 | C | GLN A | 1055 | −11.812 | 31.104 | −3.147 | 1.00 | 46.94 | C |
| ATOM | 7645 | O | GLN A | 1055 | −11.706 | 29.996 | −2.576 | 1.00 | 44.09 | O |
| ATOM | 7646 | N | ASN A | 1056 | −11.386 | 32.238 | −2.617 | 1.00 | 47.42 | N |
| ATOM | 7647 | CA | ASN A | 1056 | −10.656 | 32.263 | −1.360 | 1.00 | 46.32 | C |
| ATOM | 7648 | CB | ASN A | 1056 | −10.223 | 33.682 | −1.001 | 1.00 | 47.26 | C |
| ATOM | 7649 | CG | ASN A | 1056 | −9.368 | 34.336 | −2.085 | 1.00 | 48.75 | C |
| ATOM | 7650 | OD1 | ASN A | 1056 | −9.376 | 35.507 | −2.207 | 1.00 | 51.01 | O |
| ATOM | 7651 | ND2 | ASN A | 1056 | −8.677 | 33.571 | −2.882 | 1.00 | 54.66 | N |
| ATOM | 7652 | C | ASN A | 1056 | −11.460 | 31.654 | −0.240 | 1.00 | 45.09 | C |
| ATOM | 7653 | O | ASN A | 1056 | −10.943 | 30.829 | 0.495 | 1.00 | 46.98 | O |
| ATOM | 7654 | N | ARG A | 1057 | −12.729 | 32.003 | −0.118 | 1.00 | 43.88 | N |
| ATOM | 7655 | CA | ARG A | 1057 | −13.535 | 31.367 | 0.905 | 1.00 | 44.92 | C |
| ATOM | 7656 | CB | ARG A | 1057 | −14.975 | 31.885 | 0.924 | 1.00 | 48.65 | C |
| ATOM | 7657 | CG | ARG A | 1057 | −15.087 | 33.302 | 1.473 | 1.00 | 52.57 | C |
| ATOM | 7658 | CD | ARG A | 1057 | −16.136 | 34.140 | 0.767 | 1.00 | 55.20 | C |
| ATOM | 7659 | NE | ARG A | 1057 | −16.206 | 35.479 | 1.322 | 1.00 | 58.19 | N |
| ATOM | 7660 | CZ | ARG A | 1057 | −16.700 | 35.794 | 2.533 | 1.00 | 57.70 | C |
| ATOM | 7661 | NH1 | ARG A | 1057 | −17.236 | 34.897 | 3.372 | 1.00 | 51.75 | N |
| ATOM | 7662 | NH2 | ARG A | 1057 | −16.695 | 37.073 | 2.880 | 1.00 | 61.11 | N |
| ATOM | 7663 | C | ARG A | 1057 | −13.538 | 29.891 | 0.691 | 1.00 | 44.42 | C |
| ATOM | 7664 | O | ARG A | 1057 | −13.357 | 29.149 | 1.661 | 1.00 | 44.75 | O |
| ATOM | 7665 | N | LEU A | 1058 | −13.732 | 29.465 | −0.564 | 1.00 | 42.01 | N |
| ATOM | 7666 | CA | LEU A | 1058 | −13.701 | 28.041 | −0.902 | 1.00 | 42.09 | C |
| ATOM | 7667 | CB | LEU A | 1058 | −13.952 | 27.839 | −2.387 | 1.00 | 44.09 | C |
| ATOM | 7668 | CG | LEU A | 1058 | −15.441 | 27.916 | −2.633 | 1.00 | 45.94 | C |
| ATOM | 7669 | CD1 | LEU A | 1058 | −15.703 | 28.314 | −4.076 | 1.00 | 46.41 | C |
| ATOM | 7670 | CD2 | LEU A | 1058 | −16.137 | 26.605 | −2.236 | 1.00 | 45.22 | C |
| ATOM | 7671 | C | LEU A | 1058 | −12.411 | 27.324 | −0.536 | 1.00 | 40.91 | C |
| ATOM | 7672 | O | LEU A | 1058 | −12.435 | 26.258 | 0.100 | 1.00 | 36.73 | O |
| ATOM | 7673 | N | ASN A | 1059 | −11.283 | 27.920 | −0.898 | 1.00 | 38.80 | N |
| ATOM | 7674 | CA | ASN A | 1059 | −10.047 | 27.291 | −0.567 | 1.00 | 40.90 | C |
| ATOM | 7675 | CB | ASN A | 1059 | −8.900 | 28.050 | −1.127 | 1.00 | 42.59 | C |
| ATOM | 7676 | CG | ASN A | 1059 | −8.947 | 28.147 | −2.617 | 1.00 | 44.46 | C |
| ATOM | 7677 | OD1 | ASN A | 1059 | −9.092 | 27.162 | −3.336 | 1.00 | 52.81 | O |
| ATOM | 7678 | ND2 | ASN A | 1059 | −8.803 | 29.333 | −3.094 | 1.00 | 46.74 | N |
| ATOM | 7679 | C | ASN A | 1059 | −9.815 | 27.103 | 0.905 | 1.00 | 43.88 | C |
| ATOM | 7680 | O | ASN A | 1059 | −9.076 | 26.219 | 1.287 | 1.00 | 44.15 | O |
| ATOM | 7681 | N | LYS A | 1060 | −10.410 | 27.937 | 1.750 | 1.00 | 51.64 | N |
| ATOM | 7682 | CA | LYS A | 1060 | −10.331 | 27.697 | 3.208 | 1.00 | 56.31 | C |
| ATOM | 7683 | CB | LYS A | 1060 | −10.961 | 28.810 | 4.070 | 1.00 | 60.73 | C |
| ATOM | 7684 | CG | LYS A | 1060 | −10.231 | 30.138 | 4.137 | 1.00 | 64.97 | C |
| ATOM | 7685 | CD | LYS A | 1060 | −11.064 | 31.160 | 4.916 | 1.00 | 72.36 | C |
| ATOM | 7686 | CE | LYS A | 1060 | −10.363 | 32.504 | 5.142 | 1.00 | 77.47 | C |
| ATOM | 7687 | NZ | LYS A | 1060 | −10.676 | 33.480 | 4.056 | 1.00 | 79.11 | N |
| ATOM | 7688 | C | LYS A | 1060 | −11.012 | 26.397 | 3.562 | 1.00 | 52.13 | C |
| ATOM | 7689 | O | LYS A | 1060 | −10.551 | 25.707 | 4.450 | 1.00 | 56.20 | O |
| ATOM | 7690 | N | VAL A | 1061 | −12.072 | 26.055 | 2.845 | 1.00 | 48.95 | N |
| ATOM | 7691 | CA | VAL A | 1061 | −13.005 | 25.003 | 3.282 | 1.00 | 47.62 | C |
| ATOM | 7692 | CB | VAL A | 1061 | −14.432 | 25.577 | 3.076 | 1.00 | 48.79 | C |

TABLE 6-continued

Atomic coordinates for CRBN:DDB1: Compound B (Human protein)

| ATOM | 7693 | CG1 | VAL A | 1061 | −15.290 | 24.713 | 2.141 | 1.00 | 48.13 | C |
|------|------|-----|-------|------|---------|--------|-------|------|-------|---|
| ATOM | 7694 | CG2 | VAL A | 1061 | −15.105 | 25.789 | 4.406 | 1.00 | 51.95 | C |
| ATOM | 7695 | C | VAL A | 1061 | −12.881 | 23.645 | 2.642 | 1.00 | 47.41 | C |
| ATOM | 7696 | O | VAL A | 1061 | −13.368 | 22.708 | 3.259 | 1.00 | 48.51 | O |
| ATOM | 7697 | N | ILE A | 1062 | −12.287 | 23.518 | 1.435 | 1.00 | 45.72 | N |
| ATOM | 7698 | CA | ILE A | 1062 | −12.280 | 22.263 | 0.607 | 1.00 | 45.60 | C |
| ATOM | 7699 | CB | ILE A | 1062 | −12.375 | 22.602 | −0.910 | 1.00 | 44.84 | C |
| ATOM | 7700 | CG1 | ILE A | 1062 | −13.796 | 22.918 | −1.287 | 1.00 | 47.81 | C |
| ATOM | 7701 | CD1 | ILE A | 1062 | −13.875 | 24.095 | −2.226 | 1.00 | 50.68 | C |
| ATOM | 7702 | CG2 | ILE A | 1062 | −11.888 | 21.517 | −1.843 | 1.00 | 39.99 | C |
| ATOM | 7703 | C | ILE A | 1062 | −10.995 | 21.474 | 0.797 | 1.00 | 48.29 | C |
| ATOM | 7704 | O | ILE A | 1062 | −9.924 | 22.033 | 0.584 | 1.00 | 44.64 | O |
| ATOM | 7705 | N | LYS A | 1063 | −11.096 | 20.176 | 1.144 | 1.00 | 55.28 | N |
| ATOM | 7706 | CA | LYS A | 1063 | −9.898 | 19.325 | 1.321 | 1.00 | 58.71 | C |
| ATOM | 7707 | CB | LYS A | 1063 | −10.171 | 17.980 | 2.094 | 1.00 | 67.62 | C |
| ATOM | 7708 | CG | LYS A | 1063 | −9.085 | 16.892 | 1.720 | 1.00 | 88.08 | C |
| ATOM | 7709 | CD | LYS A | 1063 | −8.728 | 15.688 | 2.659 | 1.00 | 95.36 | C |
| ATOM | 7710 | CE | LYS A | 1063 | −7.202 | 15.302 | 2.665 | 1.00 | 91.60 | C |
| ATOM | 7711 | NZ | LYS A | 1063 | −6.540 | 14.849 | 1.383 | 1.00 | 84.03 | N |
| ATOM | 7712 | C | LYS A | 1063 | −9.258 | 19.132 | −0.094 | 1.00 | 52.18 | C |
| ATOM | 7713 | O | LYS A | 1063 | −9.954 | 18.902 | −1.064 | 1.00 | 47.65 | O |
| ATOM | 7714 | N | SER A | 1064 | −7.934 | 19.266 | −0.137 | 1.00 | 47.72 | N |
| ATOM | 7715 | CA | SER A | 1064 | −7.086 | 19.153 | −1.317 | 1.00 | 41.72 | C |
| ATOM | 7716 | CB | SER A | 1064 | −6.212 | 20.375 | −1.457 | 1.00 | 39.50 | C |
| ATOM | 7717 | OG | SER A | 1064 | −5.102 | 20.122 | −2.273 | 1.00 | 35.59 | O |
| ATOM | 7718 | C | SER A | 1064 | −6.241 | 17.950 | −1.059 | 1.00 | 42.22 | C |
| ATOM | 7719 | O | SER A | 1064 | −5.737 | 17.788 | 0.017 | 1.00 | 36.54 | O |
| ATOM | 7720 | N | VAL A | 1065 | −6.087 | 17.096 | −2.053 | 1.00 | 46.83 | N |
| ATOM | 7721 | CA | VAL A | 1065 | −5.436 | 15.826 | −1.851 | 1.00 | 45.71 | C |
| ATOM | 7722 | CB | VAL A | 1065 | −5.573 | 15.011 | −3.131 | 1.00 | 43.45 | C |
| ATOM | 7723 | CG1 | VAL A | 1065 | −5.092 | 13.600 | −2.948 | 1.00 | 45.12 | C |
| ATOM | 7724 | CG2 | VAL A | 1065 | −7.020 | 14.956 | −3.506 | 1.00 | 40.35 | C |
| ATOM | 7725 | C | VAL A | 1065 | −4.016 | 15.694 | −1.353 | 1.00 | 49.29 | C |
| ATOM | 7726 | O | VAL A | 1065 | −3.807 | 14.966 | −0.388 | 1.00 | 58.69 | O |
| ATOM | 7727 | N | GLY A | 1066 | −3.064 | 16.400 | −1.907 | 1.00 | 45.90 | N |
| ATOM | 7728 | CA | GLY A | 1066 | −1.705 | 16.267 | −1.437 | 1.00 | 45.11 | C |
| ATOM | 7729 | C | GLY A | 1066 | −1.468 | 17.485 | −0.637 | 1.00 | 42.30 | C |
| ATOM | 7730 | O | GLY A | 1066 | −0.376 | 17.968 | −0.560 | 1.00 | 42.40 | O |
| ATOM | 7731 | N | LYS A | 1067 | −2.533 | 18.006 | −0.073 | 1.00 | 42.56 | N |
| ATOM | 7732 | CA | LYS A | 1067 | −2.465 | 19.322 | 0.612 | 1.00 | 43.29 | C |
| ATOM | 7733 | CB | LYS A | 1067 | −1.827 | 19.201 | 1.998 | 1.00 | 46.06 | C |
| ATOM | 7734 | CG | LYS A | 1067 | −2.481 | 18.113 | 2.855 | 1.00 | 50.02 | C |
| ATOM | 7735 | CD | LYS A | 1067 | −2.714 | 18.486 | 4.326 | 1.00 | 53.56 | C |
| ATOM | 7736 | CE | LYS A | 1067 | −3.099 | 17.252 | 5.148 | 1.00 | 56.62 | C |
| ATOM | 7737 | NZ | LYS A | 1067 | −3.031 | 17.408 | 6.622 | 1.00 | 57.99 | N |
| ATOM | 7738 | C | LYS A | 1067 | −1.799 | 20.424 | −0.208 | 1.00 | 41.07 | C |
| ATOM | 7739 | O | LYS A | 1067 | −0.983 | 21.199 | 0.265 | 1.00 | 40.48 | O |
| ATOM | 7740 | N | ILE A | 1068 | −2.168 | 20.509 | −1.455 | 1.00 | 38.58 | N |
| ATOM | 7741 | CA | ILE A | 1068 | −1.522 | 21.450 | −2.297 | 1.00 | 40.41 | C |
| ATOM | 7742 | CB | ILE A | 1068 | −1.430 | 20.919 | −3.742 | 1.00 | 41.90 | C |
| ATOM | 7743 | CG1 | ILE A | 1068 | −0.631 | 19.613 | −3.783 | 1.00 | 39.81 | C |
| ATOM | 7744 | CD1 | ILE A | 1068 | −0.694 | 18.937 | −5.153 | 1.00 | 41.22 | C |
| ATOM | 7745 | CG2 | ILE A | 1068 | −0.902 | 22.019 | −4.687 | 1.00 | 41.73 | C |
| ATOM | 7746 | C | ILE A | 1068 | −2.361 | 22.696 | −2.298 | 1.00 | 41.02 | C |
| ATOM | 7747 | O | ILE A | 1068 | −3.545 | 22.613 | −2.536 | 1.00 | 37.79 | O |
| ATOM | 7748 | N | GLU A | 1069 | −1.739 | 23.855 | −2.141 | 1.00 | 44.15 | N |
| ATOM | 7749 | CA | GLU A | 1069 | −2.502 | 25.082 | −2.185 | 1.00 | 47.04 | C |
| ATOM | 7750 | CB | GLU A | 1069 | −1.662 | 26.258 | −1.713 | 1.00 | 53.74 | C |
| ATOM | 7751 | CG | GLU A | 1069 | −1.020 | 26.157 | −0.334 | 1.00 | 62.07 | C |
| ATOM | 7752 | CD | GLU A | 1069 | −2.007 | 26.267 | 0.811 | 1.00 | 69.59 | C |
| ATOM | 7753 | OE1 | GLU A | 1069 | −2.956 | 27.062 | 0.686 | 1.00 | 76.82 | O |
| ATOM | 7754 | OE2 | GLU A | 1069 | −1.826 | 25.570 | 1.844 | 1.00 | 75.28 | O |
| ATOM | 7755 | C | GLU A | 1069 | −2.992 | 25.351 | −3.623 | 1.00 | 44.38 | C |
| ATOM | 7756 | O | GLU A | 1069 | −2.186 | 25.483 | −4.550 | 1.00 | 46.15 | O |
| ATOM | 7757 | N | HIS A | 1070 | −4.305 | 25.460 | −3.804 | 1.00 | 40.23 | N |
| ATOM | 7758 | CA | HIS A | 1070 | −4.896 | 25.972 | −5.054 | 1.00 | 39.14 | C |
| ATOM | 7759 | CB | HIS A | 1070 | −6.335 | 26.420 | −4.847 | 1.00 | 40.21 | C |
| ATOM | 7760 | CG | HIS A | 1070 | −7.040 | 26.826 | −6.101 | 1.00 | 42.84 | C |
| ATOM | 7761 | ND1 | HIS A | 1070 | −6.998 | 28.115 | −6.587 | 1.00 | 42.67 | N |
| ATOM | 7762 | CE1 | HIS A | 1070 | −7.714 | 28.179 | −7.702 | 1.00 | 42.18 | C |
| ATOM | 7763 | NE2 | HIS A | 1070 | −8.209 | 26.983 | −7.961 | 1.00 | 41.18 | N |
| ATOM | 7764 | CD2 | HIS A | 1070 | −7.804 | 26.114 | −6.975 | 1.00 | 42.94 | C |
| ATOM | 7765 | C | HIS A | 1070 | −4.167 | 27.121 | −5.675 | 1.00 | 39.18 | C |
| ATOM | 7766 | O | HIS A | 1070 | −4.121 | 27.213 | −6.840 | 1.00 | 37.20 | O |
| ATOM | 7767 | N | SER A | 1071 | −3.624 | 28.040 | −4.907 | 1.00 | 47.71 | N |
| ATOM | 7768 | CA | SER A | 1071 | −2.926 | 29.224 | −5.515 | 1.00 | 50.50 | C |
| ATOM | 7769 | CB | SER A | 1071 | −2.824 | 30.367 | −4.519 | 1.00 | 49.64 | C |
| ATOM | 7770 | OG | SER A | 1071 | −4.112 | 30.950 | −4.452 | 1.00 | 51.51 | O |

TABLE 6-continued

Atomic coordinates for CRBN:DDB1: Compound B (Human protein)

| ATOM | 7771 | C | SER A | 1071 | −1.565 | 28.895 | −6.120 | 1.00 | 48.11 | C |
|---|---|---|---|---|---|---|---|---|---|---|
| ATOM | 7772 | O | SER A | 1071 | −1.187 | 29.427 | −7.169 | 1.00 | 48.92 | O |
| ATOM | 7773 | N | PHE A | 1072 | −0.861 | 27.991 | −5.463 | 1.00 | 44.44 | N |
| ATOM | 7774 | CA | PHE A | 1072 | 0.349 | 27.466 | −5.997 | 1.00 | 42.39 | C |
| ATOM | 7775 | CB | PHE A | 1072 | 0.948 | 26.462 | −5.018 | 1.00 | 40.30 | C |
| ATOM | 7776 | CG | PHE A | 1072 | 2.178 | 25.834 | −5.516 | 1.00 | 39.69 | C |
| ATOM | 7777 | CD1 | PHE A | 1072 | 3.353 | 26.488 | −5.452 | 1.00 | 40.45 | C |
| ATOM | 7778 | CE1 | PHE A | 1072 | 4.508 | 25.937 | −5.944 | 1.00 | 42.92 | C |
| ATOM | 7779 | CZ | PHE A | 1072 | 4.480 | 24.701 | −6.512 | 1.00 | 43.61 | C |
| ATOM | 7780 | CE2 | PHE A | 1072 | 3.284 | 24.021 | −6.582 | 1.00 | 42.77 | C |
| ATOM | 7781 | CD2 | PHE A | 1072 | 2.145 | 24.599 | −6.091 | 1.00 | 42.02 | C |
| ATOM | 7782 | C | PHE A | 1072 | 0.050 | 26.819 | −7.338 | 1.00 | 44.50 | C |
| ATOM | 7783 | O | PHE A | 1072 | 0.795 | 27.041 | −8.335 | 1.00 | 45.18 | O |
| ATOM | 7784 | N | TRP A | 1073 | −1.035 | 26.023 | −7.335 | 1.00 | 42.76 | N |
| ATOM | 7785 | CA | TRP A | 1073 | −1.435 | 25.262 | −8.503 | 1.00 | 41.77 | C |
| ATOM | 7786 | CB | TRP A | 1073 | −2.606 | 24.349 | −8.194 | 1.00 | 40.61 | C |
| ATOM | 7787 | CG | TRP A | 1073 | −3.341 | 23.727 | −9.364 | 1.00 | 41.13 | C |
| ATOM | 7788 | CD1 | TRP A | 1073 | −4.678 | 23.762 | −9.562 | 1.00 | 43.82 | C |
| ATOM | 7789 | NE1 | TRP A | 1073 | −5.027 | 23.083 | −10.728 | 1.00 | 42.21 | N |
| ATOM | 7790 | CE2 | TRP A | 1073 | −3.882 | 22.558 | −11.269 | 1.00 | 40.00 | C |
| ATOM | 7791 | CD2 | TRP A | 1073 | −2.802 | 22.954 | −10.450 | 1.00 | 39.89 | C |
| ATOM | 7792 | CE3 | TRP A | 1073 | −1.521 | 22.574 | −10.820 | 1.00 | 39.11 | C |
| ATOM | 7793 | CZ3 | TRP A | 1073 | −1.365 | 21.815 | −11.962 | 1.00 | 37.89 | C |
| ATOM | 7794 | CH2 | TRP A | 1073 | −2.465 | 21.435 | −12.746 | 1.00 | 36.90 | C |
| ATOM | 7795 | CZ2 | TRP A | 1073 | −3.710 | 21.794 | −12.430 | 1.00 | 37.19 | C |
| ATOM | 7796 | C | TRP A | 1073 | −1.744 | 26.180 | −9.651 | 1.00 | 41.63 | C |
| ATOM | 7797 | O | TRP A | 1073 | −1.157 | 26.040 | −10.699 | 1.00 | 42.97 | O |
| ATOM | 7798 | N | ARG A | 1074 | −2.590 | 27.170 | −9.448 | 1.00 | 41.38 | N |
| ATOM | 7799 | CA | ARG A | 1074 | −2.990 | 28.024 | −10.569 | 1.00 | 43.29 | C |
| ATOM | 7800 | CB | ARG A | 1074 | −4.382 | 28.574 | −10.368 | 1.00 | 42.95 | C |
| ATOM | 7801 | CG | ARG A | 1074 | −5.426 | 27.495 | −10.164 | 1.00 | 42.96 | C |
| ATOM | 7802 | CD | ARG A | 1074 | −5.435 | 26.628 | −11.382 | 1.00 | 44.53 | C |
| ATOM | 7803 | NE | ARG A | 1074 | −6.752 | 26.090 | −11.673 | 1.00 | 44.66 | N |
| ATOM | 7804 | CZ | ARG A | 1074 | −6.992 | 25.297 | −12.699 | 1.00 | 40.18 | C |
| ATOM | 7805 | NH1 | ARG A | 1074 | −6.049 | 24.952 | −13.551 | 1.00 | 40.05 | N |
| ATOM | 7806 | NH2 | ARG A | 1074 | −8.198 | 24.908 | −12.905 | 1.00 | 40.79 | N |
| ATOM | 7807 | C | ARG A | 1074 | −2.022 | 29.128 | −10.917 | 1.00 | 43.87 | C |
| ATOM | 7808 | O | ARG A | 1074 | −2.309 | 29.958 | −11.763 | 1.00 | 40.11 | O |
| ATOM | 7809 | N | SER A | 1075 | −0.839 | 29.077 | −10.339 | 1.00 | 47.62 | N |
| ATOM | 7810 | CA | SER A | 1075 | 0.119 | 30.116 | −10.564 | 1.00 | 49.67 | C |
| ATOM | 7811 | CB | SER A | 1075 | 1.192 | 30.124 | −9.477 | 1.00 | 52.21 | C |
| ATOM | 7812 | OG | SER A | 1075 | 0.704 | 30.814 | −8.347 | 1.00 | 53.19 | O |
| ATOM | 7813 | C | SER A | 1075 | 0.759 | 29.875 | −11.882 | 1.00 | 47.06 | C |
| ATOM | 7814 | O | SER A | 1075 | 1.249 | 28.792 | −12.138 | 1.00 | 44.35 | O |
| ATOM | 7815 | N | PHE A | 1076 | 0.740 | 30.918 | −12.696 | 1.00 | 48.12 | N |
| ATOM | 7816 | CA | PHE A | 1076 | 1.469 | 30.979 | −13.928 | 1.00 | 50.95 | C |
| ATOM | 7817 | CB | PHE A | 1076 | 1.478 | 32.392 | −14.475 | 1.00 | 50.87 | C |
| ATOM | 7818 | CG | PHE A | 1076 | 2.078 | 32.510 | −15.835 | 1.00 | 53.54 | C |
| ATOM | 7819 | CD1 | PHE A | 1076 | 3.455 | 32.515 | −16.005 | 1.00 | 56.47 | C |
| ATOM | 7820 | CE1 | PHE A | 1076 | 4.013 | 32.625 | −17.270 | 1.00 | 56.75 | C |
| ATOM | 7821 | CZ | PHE A | 1076 | 3.190 | 32.748 | −18.369 | 1.00 | 55.42 | C |
| ATOM | 7822 | CE2 | PHE A | 1076 | 1.822 | 32.728 | −18.213 | 1.00 | 53.96 | C |
| ATOM | 7823 | CD2 | PHE A | 1076 | 1.269 | 32.610 | −16.958 | 1.00 | 54.19 | C |
| ATOM | 7824 | C | PHE A | 1076 | 2.849 | 30.588 | −13.599 | 1.00 | 54.20 | C |
| ATOM | 7825 | O | PHE A | 1076 | 3.437 | 31.218 | −12.777 | 1.00 | 53.54 | O |
| ATOM | 7826 | N | HIS A | 1077 | 3.350 | 29.555 | −14.264 | 1.00 | 68.19 | N |
| ATOM | 7827 | CA | HIS A | 1077 | 4.620 | 28.922 | −13.922 | 1.00 | 82.28 | C |
| ATOM | 7828 | CB | HIS A | 1077 | 4.313 | 27.640 | −13.113 | 1.00 | 91.48 | C |
| ATOM | 7829 | CG | HIS A | 1077 | 5.343 | 26.559 | −13.255 | 1.00 | 100.86 | C |
| ATOM | 7830 | ND1 | HIS A | 1077 | 6.562 | 26.601 | −12.607 | 1.00 | 101.07 | N |
| ATOM | 7831 | CE1 | HIS A | 1077 | 7.262 | 25.526 | −12.930 | 1.00 | 104.05 | C |
| ATOM | 7832 | NE2 | HIS A | 1077 | 6.541 | 24.787 | −13.757 | 1.00 | 104.74 | N |
| ATOM | 7833 | CD2 | HIS A | 1077 | 5.338 | 25.414 | −13.985 | 1.00 | 102.26 | C |
| ATOM | 7834 | C | HIS A | 1077 | 5.449 | 28.601 | −15.188 | 1.00 | 80.93 | C |
| ATOM | 7835 | O | HIS A | 1077 | 4.864 | 28.263 | −16.216 | 1.00 | 65.95 | O |
| ATOM | 7836 | N | THR A | 1078 | 6.791 | 28.704 | −15.071 | 1.00 | 83.40 | N |
| ATOM | 7837 | CA | THR A | 1078 | 7.765 | 28.188 | −16.061 | 1.00 | 80.77 | C |
| ATOM | 7838 | CB | THR A | 1078 | 8.403 | 29.342 | −16.860 | 1.00 | 79.58 | C |
| ATOM | 7839 | OG1 | THR A | 1078 | 9.130 | 30.200 | −15.964 | 1.00 | 85.17 | O |
| ATOM | 7840 | CG2 | THR A | 1078 | 7.323 | 30.137 | −17.579 | 1.00 | 74.66 | C |
| ATOM | 7841 | C | THR A | 1078 | 8.844 | 27.280 | −15.395 | 1.00 | 79.77 | C |
| ATOM | 7842 | O | THR A | 1078 | 9.991 | 27.673 | −15.121 | 1.00 | 81.29 | O |
| ATOM | 7843 | N | LYS A | 1081 | 10.270 | 32.522 | −14.088 | 1.00 | 105.66 | N |
| ATOM | 7844 | CA | LYS A | 1081 | 9.051 | 33.117 | −13.546 | 1.00 | 99.63 | C |
| ATOM | 7845 | CB | LYS A | 1081 | 8.193 | 33.779 | −14.665 | 1.00 | 90.33 | C |
| ATOM | 7846 | C | LYS A | 1081 | 8.257 | 32.036 | −12.780 | 1.00 | 96.09 | C |
| ATOM | 7847 | O | LYS A | 1081 | 8.360 | 30.826 | −13.108 | 1.00 | 80.17 | O |
| ATOM | 7848 | N | THR A | 1082 | 7.572 | 32.499 | −11.709 | 1.00 | 96.29 | N |

TABLE 6-continued

Atomic coordinates for CRBN:DDB1: Compound B (Human protein)

| ATOM | 7849 | CA | THR A | 1082 | 6.312 | 31.912 | −11.138 | 1.00 | 87.28 | C |
|---|---|---|---|---|---|---|---|---|---|---|
| ATOM | 7850 | CB | THR A | 1082 | 6.553 | 30.786 | −10.099 | 1.00 | 85.28 | C |
| ATOM | 7851 | OG1 | THR A | 1082 | 7.585 | 29.916 | −10.552 | 1.00 | 90.82 | O |
| ATOM | 7852 | CG2 | THR A | 1082 | 5.309 | 29.933 | −9.910 | 1.00 | 87.86 | C |
| ATOM | 7853 | C | THR A | 1082 | 5.462 | 33.020 | −10.475 | 1.00 | 76.73 | C |
| ATOM | 7854 | O | THR A | 1082 | 5.811 | 33.484 | −9.400 | 1.00 | 78.96 | O |
| ATOM | 7855 | N | GLU A | 1083 | 4.380 | 33.459 | −11.119 | 1.00 | 71.55 | N |
| ATOM | 7856 | CA | GLU A | 1083 | 3.531 | 34.553 | −10.584 | 1.00 | 75.19 | C |
| ATOM | 7857 | CB | GLU A | 1083 | 3.415 | 35.732 | −11.571 | 1.00 | 83.76 | C |
| ATOM | 7858 | CG | GLU A | 1083 | 4.656 | 36.050 | −12.398 | 1.00 | 95.44 | C |
| ATOM | 7859 | CD | GLU A | 1083 | 4.578 | 37.399 | −13.139 | 1.00 | 110.55 | C |
| ATOM | 7860 | OE1 | GLU A | 1083 | 3.958 | 38.356 | −12.600 | 1.00 | 124.78 | O |
| ATOM | 7861 | OE2 | GLU A | 1083 | 5.161 | 37.522 | −14.257 | 1.00 | 116.47 | O |
| ATOM | 7862 | C | GLU A | 1083 | 2.097 | 34.104 | −10.254 | 1.00 | 67.06 | C |
| ATOM | 7863 | O | GLU A | 1083 | 1.529 | 33.278 | −10.943 | 1.00 | 57.65 | O |
| ATOM | 7864 | N | PRO A | 1084 | 1.490 | 34.674 | −9.201 | 1.00 | 65.64 | N |
| ATOM | 7865 | CA | PRO A | 1084 | 0.058 | 34.518 | −9.010 | 1.00 | 62.63 | C |
| ATOM | 7866 | CB | PRO A | 1084 | −0.249 | 35.614 | −7.981 | 1.00 | 61.65 | C |
| ATOM | 7867 | CG | PRO A | 1084 | 0.902 | 35.486 | −7.059 | 1.00 | 63.98 | C |
| ATOM | 7868 | CD | PRO A | 1084 | 2.103 | 35.121 | −7.937 | 1.00 | 66.21 | C |
| ATOM | 7869 | C | PRO A | 1084 | −0.774 | 34.713 | −10.256 | 1.00 | 55.41 | C |
| ATOM | 7870 | O | PRO A | 1084 | −0.444 | 35.552 | −11.082 | 1.00 | 55.98 | O |
| ATOM | 7871 | N | ALA A | 1085 | −1.840 | 33.929 | −10.359 | 1.00 | 49.46 | N |
| ATOM | 7872 | CA | ALA A | 1085 | −2.754 | 34.022 | −11.475 | 1.00 | 47.05 | C |
| ATOM | 7873 | CB | ALA A | 1085 | −3.621 | 32.792 | −11.611 | 1.00 | 47.39 | C |
| ATOM | 7874 | C | ALA A | 1085 | −3.630 | 35.166 | −11.254 | 1.00 | 48.28 | C |
| ATOM | 7875 | O | ALA A | 1085 | −3.931 | 35.495 | −10.125 | 1.00 | 45.88 | O |
| ATOM | 7876 | N | THR A | 1086 | −4.113 | 35.705 | −12.372 | 1.00 | 51.63 | N |
| ATOM | 7877 | CA | THR A | 1086 | −4.839 | 36.951 | −12.412 | 1.00 | 49.60 | C |
| ATOM | 7878 | CB | THR A | 1086 | −3.852 | 38.144 | −12.417 | 1.00 | 51.61 | C |
| ATOM | 7879 | OG1 | THR A | 1086 | −4.327 | 39.136 | −13.324 | 1.00 | 64.43 | O |
| ATOM | 7880 | CG2 | THR A | 1086 | −2.413 | 37.778 | −12.873 | 1.00 | 51.07 | C |
| ATOM | 7881 | C | THR A | 1086 | −5.836 | 37.032 | −13.591 | 1.00 | 49.78 | C |
| ATOM | 7882 | O | THR A | 1086 | −5.528 | 36.789 | −14.774 | 1.00 | 50.34 | O |
| ATOM | 7883 | N | GLY A | 1087 | −7.054 | 37.411 | −13.269 | 1.00 | 51.36 | N |
| ATOM | 7884 | CA | GLY A | 1087 | −8.009 | 37.774 | −14.319 | 1.00 | 52.41 | C |
| ATOM | 7885 | C | GLY A | 1087 | −8.651 | 36.569 | −14.919 | 1.00 | 52.13 | C |
| ATOM | 7886 | O | GLY A | 1087 | −9.209 | 36.645 | −16.000 | 1.00 | 53.29 | O |
| ATOM | 7887 | N | PHE A | 1088 | −8.587 | 35.480 | −14.150 | 1.00 | 53.49 | N |
| ATOM | 7888 | CA | PHE A | 1088 | −9.135 | 34.186 | −14.465 | 1.00 | 50.63 | C |
| ATOM | 7889 | CB | PHE A | 1088 | −8.019 | 33.242 | −14.876 | 1.00 | 51.67 | C |
| ATOM | 7890 | CG | PHE A | 1088 | −7.684 | 33.341 | −16.312 | 1.00 | 52.51 | C |
| ATOM | 7891 | CD1 | PHE A | 1088 | −8.519 | 32.777 | −17.242 | 1.00 | 49.88 | C |
| ATOM | 7892 | CE1 | PHE A | 1088 | −8.274 | 32.864 | −18.571 | 1.00 | 48.71 | C |
| ATOM | 7893 | CZ | PHE A | 1088 | −7.178 | 33.531 | −18.997 | 1.00 | 51.60 | C |
| ATOM | 7894 | CE2 | PHE A | 1088 | −6.324 | 34.114 | −18.075 | 1.00 | 55.30 | C |
| ATOM | 7895 | CD2 | PHE A | 1088 | −6.596 | 34.039 | −16.733 | 1.00 | 53.66 | C |
| ATOM | 7896 | C | PHE A | 1088 | −9.781 | 33.613 | −13.241 | 1.00 | 48.35 | C |
| ATOM | 7897 | O | PHE A | 1088 | −9.112 | 33.436 | −12.189 | 1.00 | 43.06 | O |
| ATOM | 7898 | N | ILE A | 1089 | −11.060 | 33.295 | −13.366 | 1.00 | 47.78 | N |
| ATOM | 7899 | CA | ILE A | 1089 | −11.699 | 32.532 | −12.319 | 1.00 | 48.72 | C |
| ATOM | 7900 | CB | ILE A | 1089 | −13.050 | 33.116 | −11.984 | 1.00 | 53.95 | C |
| ATOM | 7901 | CG1 | ILE A | 1089 | −12.813 | 34.281 | −11.006 | 1.00 | 57.73 | C |
| ATOM | 7902 | CD1 | ILE A | 1089 | −13.865 | 35.332 | −11.085 | 1.00 | 60.48 | C |
| ATOM | 7903 | CG2 | ILE A | 1089 | −13.997 | 32.081 | −11.374 | 1.00 | 55.61 | C |
| ATOM | 7904 | C | ILE A | 1089 | −11.764 | 31.072 | −12.669 | 1.00 | 47.00 | C |
| ATOM | 7905 | O | ILE A | 1089 | −12.235 | 30.699 | −13.760 | 1.00 | 46.06 | O |
| ATOM | 7906 | N | ASP A | 1090 | −11.174 | 30.269 | −11.782 | 1.00 | 42.60 | N |
| ATOM | 7907 | CA | ASP A | 1090 | −11.271 | 28.822 | −11.833 | 1.00 | 40.79 | C |
| ATOM | 7908 | CB | ASP A | 1090 | −10.328 | 28.135 | −10.812 | 1.00 | 40.70 | C |
| ATOM | 7909 | CG | ASP A | 1090 | −10.212 | 26.620 | −11.035 | 1.00 | 44.64 | C |
| ATOM | 7910 | OD1 | ASP A | 1090 | −10.887 | 26.035 | −11.970 | 1.00 | 46.49 | O |
| ATOM | 7911 | OD2 | ASP A | 1090 | −9.430 | 26.006 | −10.281 | 1.00 | 45.76 | O |
| ATOM | 7912 | C | ASP A | 1090 | −12.686 | 28.352 | −11.647 | 1.00 | 38.31 | C |
| ATOM | 7913 | O | ASP A | 1090 | −13.083 | 28.013 | −10.550 | 1.00 | 41.10 | O |
| ATOM | 7914 | N | GLY A | 1091 | −13.433 | 28.300 | −12.730 | 1.00 | 36.39 | N |
| ATOM | 7915 | CA | GLY A | 1091 | −14.786 | 27.778 | −12.702 | 1.00 | 36.94 | C |
| ATOM | 7916 | C | GLY A | 1091 | −14.918 | 26.382 | −12.099 | 1.00 | 37.95 | C |
| ATOM | 7917 | O | GLY A | 1091 | −15.934 | 26.079 | −11.454 | 1.00 | 36.21 | O |
| ATOM | 7918 | N | ASP A | 1092 | −13.906 | 25.530 | −12.283 | 1.00 | 39.74 | N |
| ATOM | 7919 | CA | ASP A | 1092 | −13.959 | 24.229 | −11.634 | 1.00 | 42.54 | C |
| ATOM | 7920 | CB | ASP A | 1092 | −12.815 | 23.323 | −12.081 | 1.00 | 48.47 | C |
| ATOM | 7921 | CG | ASP A | 1092 | −13.014 | 22.723 | −13.506 | 1.00 | 51.81 | C |
| ATOM | 7922 | OD1 | ASP A | 1092 | −14.140 | 22.766 | −14.086 | 1.00 | 51.55 | O |
| ATOM | 7923 | OD2 | ASP A | 1092 | −11.990 | 22.181 | −14.018 | 1.00 | 56.24 | O |
| ATOM | 7924 | C | ASP A | 1092 | −13.988 | 24.343 | −10.102 | 1.00 | 41.48 | C |
| ATOM | 7925 | O | ASP A | 1092 | −14.745 | 23.652 | −9.432 | 1.00 | 38.30 | O |
| ATOM | 7926 | N | LEU A | 1093 | −13.194 | 25.241 | −9.544 | 1.00 | 43.89 | N |

TABLE 6-continued

Atomic coordinates for CRBN:DDB1: Compound B (Human protein)

| ATOM | 7927 | CA | LEU A | 1093 | −13.269 | 25.519 | −8.112 | 1.00 | 44.43 | C |
|---|---|---|---|---|---|---|---|---|---|---|
| ATOM | 7928 | CB | LEU A | 1093 | −12.256 | 26.568 | −7.738 | 1.00 | 47.53 | C |
| ATOM | 7929 | CG | LEU A | 1093 | −12.201 | 27.041 | −6.282 | 1.00 | 52.35 | C |
| ATOM | 7930 | CD1 | LEU A | 1093 | −11.904 | 25.865 | −5.371 | 1.00 | 52.94 | C |
| ATOM | 7931 | CD2 | LEU A | 1093 | −11.160 | 28.170 | −6.138 | 1.00 | 53.99 | C |
| ATOM | 7932 | C | LEU A | 1093 | −14.652 | 26.014 | −7.737 | 1.00 | 43.21 | C |
| ATOM | 7933 | O | LEU A | 1093 | −15.293 | 25.458 | −6.787 | 1.00 | 42.56 | O |
| ATOM | 7934 | N | ILE A | 1094 | −15.105 | 27.041 | −8.467 | 1.00 | 38.42 | N |
| ATOM | 7935 | CA | ILE A | 1094 | −16.337 | 27.674 | −8.123 | 1.00 | 39.18 | C |
| ATOM | 7936 | CB | ILE A | 1094 | −16.686 | 28.798 | −9.059 | 1.00 | 39.83 | C |
| ATOM | 7937 | CG1 | ILE A | 1094 | −15.765 | 29.982 | −8.845 | 1.00 | 40.43 | C |
| ATOM | 7938 | CD1 | ILE A | 1094 | −16.038 | 30.745 | −7.582 | 1.00 | 42.87 | C |
| ATOM | 7939 | CG2 | ILE A | 1094 | −18.152 | 29.203 | −8.912 | 1.00 | 40.34 | C |
| ATOM | 7940 | C | ILE A | 1094 | −17.455 | 26.650 | −8.152 | 1.00 | 43.93 | C |
| ATOM | 7941 | O | ILE A | 1094 | −18.243 | 26.602 | −7.204 | 1.00 | 43.36 | O |
| ATOM | 7942 | N | GLU A | 1095 | −17.533 | 25.827 | −9.212 | 1.00 | 46.47 | N |
| ATOM | 7943 | CA | GLU A | 1095 | −18.572 | 24.788 | −9.258 | 1.00 | 46.63 | C |
| ATOM | 7944 | CB | GLU A | 1095 | −18.595 | 24.039 | −10.597 | 1.00 | 51.50 | C |
| ATOM | 7945 | CG | GLU A | 1095 | −19.030 | 24.893 | −11.793 | 1.00 | 57.97 | C |
| ATOM | 7946 | CD | GLU A | 1095 | −19.107 | 24.171 | −13.187 | 1.00 | 59.84 | C |
| ATOM | 7947 | OE1 | GLU A | 1095 | −18.893 | 22.894 | −13.212 | 1.00 | 56.16 | O |
| ATOM | 7948 | OE2 | GLU A | 1095 | −19.373 | 24.945 | −14.226 | 1.00 | 52.70 | O |
| ATOM | 7949 | C | GLU A | 1095 | −18.466 | 23.792 | −8.075 | 1.00 | 46.45 | C |
| ATOM | 7950 | O | GLU A | 1095 | −19.477 | 23.321 | −7.647 | 1.00 | 43.40 | O |
| ATOM | 7951 | N | SER A | 1096 | −17.286 | 23.481 | −7.524 | 1.00 | 47.97 | N |
| ATOM | 7952 | CA | SER A | 1096 | −17.225 | 22.565 | −6.347 | 1.00 | 50.09 | C |
| ATOM | 7953 | CB | SER A | 1096 | −15.788 | 22.256 | −5.830 | 1.00 | 50.49 | C |
| ATOM | 7954 | OG | SER A | 1096 | −15.097 | 23.399 | −5.343 | 1.00 | 48.11 | O |
| ATOM | 7955 | C | SER A | 1096 | −18.055 | 23.071 | −5.180 | 1.00 | 51.90 | C |
| ATOM | 7956 | O | SER A | 1096 | −18.557 | 22.261 | −4.421 | 1.00 | 52.68 | O |
| ATOM | 7957 | N | PHE A | 1097 | −18.245 | 24.379 | −5.023 | 1.00 | 50.47 | N |
| ATOM | 7958 | CA | PHE A | 1097 | −19.186 | 24.830 | −3.979 | 1.00 | 55.22 | C |
| ATOM | 7959 | CB | PHE A | 1097 | −19.685 | 26.243 | −4.272 | 1.00 | 59.43 | C |
| ATOM | 7960 | CG | PHE A | 1097 | −20.723 | 26.750 | −3.308 | 1.00 | 58.07 | C |
| ATOM | 7961 | CD1 | PHE A | 1097 | −22.052 | 26.523 | −3.529 | 1.00 | 58.08 | C |
| ATOM | 7962 | CE1 | PHE A | 1097 | −23.011 | 27.008 | −2.662 | 1.00 | 59.15 | C |
| ATOM | 7963 | CZ | PHE A | 1097 | −22.633 | 27.726 | −1.569 | 1.00 | 58.76 | C |
| ATOM | 7964 | CE2 | PHE A | 1097 | −21.298 | 27.955 | −1.340 | 1.00 | 61.11 | C |
| ATOM | 7965 | CD2 | PHE A | 1097 | −20.355 | 27.470 | −2.208 | 1.00 | 60.73 | C |
| ATOM | 7966 | C | PHE A | 1097 | −20.410 | 23.922 | −3.778 | 1.00 | 55.88 | C |
| ATOM | 7967 | O | PHE A | 1097 | −20.756 | 23.618 | −2.654 | 1.00 | 57.58 | O |
| ATOM | 7968 | N | LEU A | 1098 | −21.052 | 23.507 | −4.881 | 1.00 | 58.62 | N |
| ATOM | 7969 | CA | LEU A | 1098 | −22.267 | 22.636 | −4.873 | 1.00 | 53.73 | C |
| ATOM | 7970 | CB | LEU A | 1098 | −22.856 | 22.458 | −6.267 | 1.00 | 50.33 | C |
| ATOM | 7971 | CG | LEU A | 1098 | −23.180 | 23.738 | −7.025 | 1.00 | 52.85 | C |
| ATOM | 7972 | CD1 | LEU A | 1098 | −23.563 | 23.412 | −8.448 | 1.00 | 57.84 | C |
| ATOM | 7973 | CD2 | LEU A | 1098 | −24.301 | 24.537 | −6.429 | 1.00 | 53.12 | C |
| ATOM | 7974 | C | LEU A | 1098 | −22.057 | 21.258 | −4.240 | 1.00 | 51.60 | C |
| ATOM | 7975 | O | LEU A | 1098 | −23.034 | 20.642 | −3.808 | 1.00 | 52.46 | O |
| ATOM | 7976 | N | ASP A | 1099 | −20.818 | 20.798 | −4.144 | 1.00 | 49.53 | N |
| ATOM | 7977 | CA | ASP A | 1099 | −20.521 | 19.501 | −3.548 | 1.00 | 55.77 | C |
| ATOM | 7978 | CB | ASP A | 1099 | −19.357 | 18.847 | −4.304 | 1.00 | 61.18 | C |
| ATOM | 7979 | CG | ASP A | 1099 | −19.598 | 18.767 | −5.786 | 1.00 | 67.70 | C |
| ATOM | 7980 | OD1 | ASP A | 1099 | −20.753 | 18.404 | −6.154 | 1.00 | 68.10 | O |
| ATOM | 7981 | OD2 | ASP A | 1099 | −18.635 | 19.071 | −6.565 | 1.00 | 73.99 | O |
| ATOM | 7982 | C | ASP A | 1099 | −20.131 | 19.542 | −2.071 | 1.00 | 56.30 | C |
| ATOM | 7983 | O | ASP A | 1099 | −19.780 | 18.519 | −1.513 | 1.00 | 60.65 | O |
| ATOM | 7984 | N | ILE A | 1100 | −20.136 | 20.700 | −1.425 | 1.00 | 55.68 | N |
| ATOM | 7985 | CA | ILE A | 1100 | −19.691 | 20.765 | −0.022 | 1.00 | 53.95 | C |
| ATOM | 7986 | CB | ILE A | 1100 | −18.819 | 22.044 | 0.233 | 1.00 | 51.56 | C |
| ATOM | 7987 | CG1 | ILE A | 1100 | −19.651 | 23.351 | 0.405 | 1.00 | 51.21 | C |
| ATOM | 7988 | CD1 | ILE A | 1100 | −18.904 | 24.685 | 0.280 | 1.00 | 48.28 | C |
| ATOM | 7989 | CG2 | ILE A | 1100 | −17.838 | 22.206 | −0.909 | 1.00 | 51.36 | C |
| ATOM | 7990 | C | ILE A | 1100 | −20.940 | 20.605 | 0.885 | 1.00 | 55.28 | C |
| ATOM | 7991 | O | ILE A | 1100 | −22.046 | 21.033 | 0.490 | 1.00 | 55.63 | O |
| ATOM | 7992 | N | SER A | 1101 | −20.782 | 19.985 | 2.061 | 1.00 | 52.03 | N |
| ATOM | 7993 | CA | SER A | 1101 | −21.863 | 19.974 | 3.045 | 1.00 | 53.01 | C |
| ATOM | 7994 | CB | SER A | 1101 | −21.419 | 19.360 | 4.381 | 1.00 | 57.28 | C |
| ATOM | 7995 | OG | SER A | 1101 | −20.511 | 20.162 | 5.106 | 1.00 | 56.94 | O |
| ATOM | 7996 | C | SER A | 1101 | −22.492 | 21.347 | 3.309 | 1.00 | 51.74 | C |
| ATOM | 7997 | O | SER A | 1101 | −21.846 | 22.371 | 3.266 | 1.00 | 47.35 | O |
| ATOM | 7998 | N | ARG A | 1102 | −23.788 | 21.333 | 3.566 | 1.00 | 55.36 | N |
| ATOM | 7999 | CA | ARG A | 1102 | −24.573 | 22.539 | 3.880 | 1.00 | 59.79 | C |
| ATOM | 8000 | CB | ARG A | 1102 | −25.965 | 22.076 | 4.374 | 1.00 | 62.67 | C |
| ATOM | 8001 | CG | ARG A | 1102 | −26.958 | 23.147 | 4.792 | 1.00 | 65.82 | C |
| ATOM | 8002 | CD | ARG A | 1102 | −27.842 | 23.578 | 3.638 | 1.00 | 70.44 | C |
| ATOM | 8003 | NE | ARG A | 1102 | −28.401 | 24.887 | 3.952 | 1.00 | 80.50 | N |
| ATOM | 8004 | CZ | ARG A | 1102 | −28.941 | 25.721 | 3.064 | 1.00 | 86.50 | C |

TABLE 6-continued

Atomic coordinates for CRBN:DDB1: Compound B (Human protein)

| ATOM | 8005 | NH1 | ARG A | 1102 | −29.046 | 25.371 | 1.768 | 1.00 | 87.09 | N |
|---|---|---|---|---|---|---|---|---|---|---|
| ATOM | 8006 | NH2 | ARG A | 1102 | −29.387 | 26.914 | 3.486 | 1.00 | 83.68 | N |
| ATOM | 8007 | C | ARG A | 1102 | −23.914 | 23.489 | 4.930 | 1.00 | 59.79 | C |
| ATOM | 8008 | O | ARG A | 1102 | −24.056 | 24.728 | 4.834 | 1.00 | 55.92 | O |
| ATOM | 8009 | N | PRO A | 1103 | −23.261 | 22.914 | 5.975 | 1.00 | 58.05 | N |
| ATOM | 8010 | CA | PRO A | 1103 | −22.568 | 23.807 | 6.849 | 1.00 | 57.76 | C |
| ATOM | 8011 | CB | PRO A | 1103 | −22.304 | 22.961 | 8.096 | 1.00 | 58.11 | C |
| ATOM | 8012 | CG | PRO A | 1103 | −22.491 | 21.579 | 7.674 | 1.00 | 57.13 | C |
| ATOM | 8013 | CD | PRO A | 1103 | −23.554 | 21.648 | 6.666 | 1.00 | 58.50 | C |
| ATOM | 8014 | C | PRO A | 1103 | −21.314 | 24.407 | 6.225 | 1.00 | 59.22 | C |
| ATOM | 8015 | O | PRO A | 1103 | −21.105 | 25.599 | 6.438 | 1.00 | 68.40 | O |
| ATOM | 8016 | N | LYS A | 1104 | −20.531 | 23.682 | 5.417 | 1.00 | 61.04 | N |
| ATOM | 8017 | CA | LYS A | 1104 | −19.365 | 24.333 | 4.743 | 1.00 | 59.39 | C |
| ATOM | 8018 | CB | LYS A | 1104 | −18.444 | 23.388 | 3.983 | 1.00 | 58.42 | C |
| ATOM | 8019 | CG | LYS A | 1104 | −17.976 | 22.159 | 4.704 | 1.00 | 63.33 | C |
| ATOM | 8020 | CD | LYS A | 1104 | −17.193 | 22.477 | 5.943 | 1.00 | 73.40 | C |
| ATOM | 8021 | CE | LYS A | 1104 | −15.723 | 22.150 | 5.803 | 1.00 | 82.84 | C |
| ATOM | 8022 | NZ | LYS A | 1104 | −14.985 | 22.805 | 6.943 | 1.00 | 94.96 | N |
| ATOM | 8023 | C | LYS A | 1104 | −19.848 | 25.437 | 3.793 | 1.00 | 60.11 | C |
| ATOM | 8024 | O | LYS A | 1104 | −19.147 | 26.429 | 3.638 | 1.00 | 62.27 | O |
| ATOM | 8025 | N | MET A | 1105 | −21.029 | 25.297 | 3.173 | 1.00 | 59.62 | N |
| ATOM | 8026 | CA | MET A | 1105 | −21.583 | 26.417 | 2.400 | 1.00 | 61.10 | C |
| ATOM | 8027 | CB | MET A | 1105 | −22.928 | 26.117 | 1.756 | 1.00 | 65.26 | C |
| ATOM | 8028 | CG | MET A | 1105 | −22.799 | 25.209 | 0.563 | 1.00 | 73.41 | C |
| ATOM | 8029 | SD | MET A | 1105 | −24.348 | 24.885 | −0.287 | 1.00 | 77.03 | S |
| ATOM | 8030 | CE | MET A | 1105 | −24.261 | 23.104 | −0.223 | 1.00 | 75.35 | C |
| ATOM | 8031 | C | MET A | 1105 | −21.743 | 27.586 | 3.303 | 1.00 | 57.05 | C |
| ATOM | 8032 | O | MET A | 1105 | −21.277 | 28.674 | 2.976 | 1.00 | 60.32 | O |
| ATOM | 8033 | N | GLN A | 1106 | −22.370 | 27.337 | 4.449 | 1.00 | 55.04 | N |
| ATOM | 8034 | CA | GLN A | 1106 | −22.778 | 28.395 | 5.356 | 1.00 | 54.56 | C |
| ATOM | 8035 | CB | GLN A | 1106 | −23.582 | 27.833 | 6.527 | 1.00 | 58.78 | C |
| ATOM | 8036 | CG | GLN A | 1106 | −25.059 | 28.253 | 6.474 | 1.00 | 65.71 | C |
| ATOM | 8037 | CD | GLN A | 1106 | −26.076 | 27.113 | 6.650 | 1.00 | 70.50 | C |
| ATOM | 8038 | OE1 | GLN A | 1106 | −25.851 | 26.112 | 7.369 | 1.00 | 67.08 | O |
| ATOM | 8039 | NE2 | GLN A | 1106 | −27.238 | 27.290 | 6.004 | 1.00 | 74.11 | N |
| ATOM | 8040 | C | GLN A | 1106 | −21.566 | 29.206 | 5.764 | 1.00 | 52.05 | C |
| ATOM | 8041 | O | GLN A | 1106 | −21.608 | 30.457 | 5.703 | 1.00 | 50.89 | O |
| ATOM | 8042 | N | GLU A | 1107 | −20.517 | 28.485 | 6.078 | 1.00 | 47.40 | N |
| ATOM | 8043 | CA | GLU A | 1107 | −19.259 | 29.009 | 6.499 | 1.00 | 48.27 | C |
| ATOM | 8044 | CB | GLU A | 1107 | −18.347 | 27.822 | 6.702 | 1.00 | 50.20 | C |
| ATOM | 8045 | CG | GLU A | 1107 | −17.147 | 28.040 | 7.574 | 1.00 | 53.68 | C |
| ATOM | 8046 | CD | GLU A | 1107 | −16.427 | 26.754 | 7.861 | 1.00 | 60.36 | C |
| ATOM | 8047 | OE1 | GLU A | 1107 | −15.198 | 26.748 | 7.786 | 1.00 | 67.92 | O |
| ATOM | 8048 | OE2 | GLU A | 1107 | −17.074 | 25.746 | 8.162 | 1.00 | 56.10 | O |
| ATOM | 8049 | C | GLU A | 1107 | −18.696 | 29.847 | 5.407 | 1.00 | 50.72 | C |
| ATOM | 8050 | O | GLU A | 1107 | −18.132 | 30.887 | 5.631 | 1.00 | 48.51 | O |
| ATOM | 8051 | N | VAL A | 1108 | −18.842 | 29.376 | 4.195 | 1.00 | 56.40 | N |
| ATOM | 8052 | CA | VAL A | 1108 | −18.295 | 30.071 | 3.054 | 1.00 | 58.32 | C |
| ATOM | 8053 | CB | VAL A | 1108 | −18.469 | 29.231 | 1.799 | 1.00 | 57.48 | C |
| ATOM | 8054 | CG1 | VAL A | 1108 | −17.830 | 29.907 | 0.623 | 1.00 | 60.91 | C |
| ATOM | 8055 | CG2 | VAL A | 1108 | −17.824 | 27.894 | 2.003 | 1.00 | 57.29 | C |
| ATOM | 8056 | C | VAL A | 1108 | −18.873 | 31.432 | 2.796 | 1.00 | 56.80 | C |
| ATOM | 8057 | O | VAL A | 1108 | −18.163 | 32.348 | 2.457 | 1.00 | 49.65 | O |
| ATOM | 8058 | N | VAL A | 1109 | −20.169 | 31.559 | 2.948 | 1.00 | 58.50 | N |
| ATOM | 8059 | CA | VAL A | 1109 | −20.816 | 32.817 | 2.683 | 1.00 | 71.11 | C |
| ATOM | 8060 | CB | VAL A | 1109 | −22.187 | 32.579 | 2.083 | 1.00 | 71.10 | C |
| ATOM | 8061 | CG1 | VAL A | 1109 | −22.050 | 31.611 | 0.948 | 1.00 | 75.45 | C |
| ATOM | 8062 | CG2 | VAL A | 1109 | −23.093 | 31.971 | 3.111 | 1.00 | 76.57 | C |
| ATOM | 8063 | C | VAL A | 1109 | −20.970 | 33.708 | 3.895 | 1.00 | 82.67 | C |
| ATOM | 8064 | O | VAL A | 1109 | −21.576 | 34.768 | 3.810 | 1.00 | 89.35 | O |
| ATOM | 8065 | N | ALA A | 1110 | −20.423 | 33.292 | 5.021 | 1.00 | 82.51 | N |
| ATOM | 8066 | CA | ALA A | 1110 | −20.574 | 34.073 | 6.214 | 1.00 | 83.79 | C |
| ATOM | 8067 | CB | ALA A | 1110 | −19.743 | 33.460 | 7.304 | 1.00 | 89.35 | C |
| ATOM | 8068 | C | ALA A | 1110 | −20.099 | 35.469 | 5.963 | 1.00 | 83.79 | C |
| ATOM | 8069 | O | ALA A | 1110 | −19.004 | 35.689 | 5.502 | 1.00 | 93.17 | O |
| ATOM | 8070 | N | ASN A | 1111 | −20.954 | 36.417 | 6.297 | 1.00 | 86.51 | N |
| ATOM | 8071 | CA | ASN A | 1111 | −20.672 | 37.833 | 6.139 | 1.00 | 91.87 | C |
| ATOM | 8072 | CB | ASN A | 1111 | −19.711 | 38.353 | 7.192 | 1.00 | 98.48 | C |
| ATOM | 8073 | CG | ASN A | 1111 | −19.906 | 39.830 | 7.448 | 1.00 | 106.05 | C |
| ATOM | 8074 | OD1 | ASN A | 1111 | −18.956 | 40.564 | 7.707 | 1.00 | 110.53 | O |
| ATOM | 8075 | ND2 | ASN A | 1111 | −21.150 | 40.279 | 7.356 | 1.00 | 106.80 | N |
| ATOM | 8076 | C | ASN A | 1111 | −20.220 | 38.234 | 4.755 | 1.00 | 80.65 | C |
| ATOM | 8077 | O | ASN A | 1111 | −19.293 | 39.002 | 4.604 | 1.00 | 72.66 | O |
| ATOM | 8078 | N | LEU A | 1112 | −20.886 | 37.712 | 3.745 | 1.00 | 81.43 | N |
| ATOM | 8079 | CA | LEU A | 1112 | −20.513 | 38.037 | 2.399 | 1.00 | 85.59 | C |
| ATOM | 8080 | CB | LEU A | 1112 | −20.627 | 36.797 | 1.542 | 1.00 | 87.44 | C |
| ATOM | 8081 | CG | LEU A | 1112 | −19.662 | 36.780 | 0.371 | 1.00 | 90.11 | C |
| ATOM | 8082 | CD1 | LEU A | 1112 | −20.044 | 35.697 | −0.609 | 1.00 | 88.37 | C |

TABLE 6-continued

Atomic coordinates for CRBN:DDB1: Compound B (Human protein)

| ATOM | 8083 | CD2 | LEU A | 1112 | −19.605 | 38.134 | −0.300 | 1.00 | 88.02 | C |
|---|---|---|---|---|---|---|---|---|---|---|
| ATOM | 8084 | C | LEU A | 1112 | −21.450 | 39.049 | 1.835 | 1.00 | 92.93 | C |
| ATOM | 8085 | O | LEU A | 1112 | −22.625 | 38.771 | 1.686 | 1.00 | 98.85 | O |
| ATOM | 8086 | N | GLN A | 1113 | −20.941 | 40.223 | 1.489 | 1.00 | 96.92 | N |
| ATOM | 8087 | CA | GLN A | 1113 | −21.816 | 41.248 | 0.900 | 1.00 | 97.38 | C |
| ATOM | 8088 | CB | GLN A | 1113 | −21.189 | 42.663 | 1.029 | 1.00 | 87.49 | C |
| ATOM | 8089 | C | GLN A | 1113 | −22.213 | 40.779 | −0.566 | 1.00 | 93.07 | C |
| ATOM | 8090 | O | GLN A | 1113 | −21.399 | 40.220 | −1.296 | 1.00 | 74.53 | O |
| ATOM | 8091 | N | TYR A | 1114 | −23.489 | 40.934 | −0.930 | 1.00 | 96.50 | N |
| ATOM | 8092 | CA | TYR A | 1114 | −24.036 | 40.364 | −2.176 | 1.00 | 99.31 | C |
| ATOM | 8093 | CB | TYR A | 1114 | −24.441 | 38.935 | −1.904 | 1.00 | 94.19 | C |
| ATOM | 8094 | CG | TYR A | 1114 | −25.161 | 38.224 | −3.014 | 1.00 | 88.63 | C |
| ATOM | 8095 | CD1 | TYR A | 1114 | −24.633 | 38.145 | −4.284 | 1.00 | 86.48 | C |
| ATOM | 8096 | CE1 | TYR A | 1114 | −25.301 | 37.455 | −5.298 | 1.00 | 87.77 | C |
| ATOM | 8097 | CZ | TYR A | 1114 | −26.499 | 36.791 | −5.020 | 1.00 | 88.67 | C |
| ATOM | 8098 | OH | TYR A | 1114 | −27.207 | 36.073 | −5.978 | 1.00 | 76.59 | O |
| ATOM | 8099 | CE2 | TYR A | 1114 | −27.013 | 36.846 | −3.744 | 1.00 | 90.71 | C |
| ATOM | 8100 | CD2 | TYR A | 1114 | −26.350 | 37.560 | −2.761 | 1.00 | 90.76 | C |
| ATOM | 8101 | C | TYR A | 1114 | −25.218 | 41.191 | −2.693 | 1.00 | 104.75 | C |
| ATOM | 8102 | O | TYR A | 1114 | −26.037 | 41.654 | −1.908 | 1.00 | 101.29 | O |
| ATOM | 8103 | N | ASP A | 1115 | −25.282 | 41.365 | −4.017 | 1.00 | 117.43 | N |
| ATOM | 8104 | CA | ASP A | 1115 | −26.043 | 42.463 | −4.666 | 1.00 | 121.03 | C |
| ATOM | 8105 | CB | ASP A | 1115 | −25.325 | 42.962 | −5.944 | 1.00 | 127.29 | C |
| ATOM | 8106 | CG | ASP A | 1115 | −23.849 | 43.375 | −5.704 | 1.00 | 129.49 | C |
| ATOM | 8107 | OD1 | ASP A | 1115 | −23.065 | 42.594 | −5.106 | 1.00 | 119.77 | O |
| ATOM | 8108 | OD2 | ASP A | 1115 | −23.467 | 44.479 | −6.158 | 1.00 | 128.53 | O |
| ATOM | 8109 | C | ASP A | 1115 | −27.475 | 42.088 | −5.047 | 1.00 | 114.55 | C |
| ATOM | 8110 | O | ASP A | 1115 | −27.768 | 40.898 | −5.282 | 1.00 | 99.72 | O |
| ATOM | 8111 | N | ASP A | 1116 | −28.297 | 43.153 | −5.161 | 1.00 | 114.84 | N |
| ATOM | 8112 | CA | ASP A | 1116 | −29.804 | 43.185 | −5.282 | 1.00 | 115.28 | C |
| ATOM | 8113 | CB | ASP A | 1116 | −30.500 | 41.835 | −4.916 | 1.00 | 107.27 | C |
| ATOM | 8114 | CG | ASP A | 1116 | −30.312 | 40.734 | −5.973 | 1.00 | 94.60 | C |
| ATOM | 8115 | OD1 | ASP A | 1116 | −30.480 | 41.020 | −7.177 | 1.00 | 77.14 | O |
| ATOM | 8116 | OD2 | ASP A | 1116 | −29.998 | 39.587 | −5.566 | 1.00 | 81.68 | O |
| ATOM | 8117 | C | ASP A | 1116 | −30.366 | 44.337 | −4.362 | 1.00 | 110.43 | C |
| ATOM | 8118 | O | ASP A | 1116 | −31.003 | 45.321 | −4.792 | 1.00 | 90.27 | O |
| ATOM | 8119 | N | LYS A | 1121 | −25.845 | 46.114 | −0.932 | 1.00 | 120.25 | N |
| ATOM | 8120 | CA | LYS A | 1121 | −25.757 | 44.660 | −0.714 | 1.00 | 129.35 | C |
| ATOM | 8121 | CB | LYS A | 1121 | −24.292 | 44.211 | −0.910 | 1.00 | 126.25 | C |
| ATOM | 8122 | C | LYS A | 1121 | −26.337 | 44.225 | 0.684 | 1.00 | 124.02 | C |
| ATOM | 8123 | O | LYS A | 1121 | −26.803 | 45.085 | 1.441 | 1.00 | 110.93 | O |
| ATOM | 8124 | N | ARG | 1122 | −26.346 | 42.912 | 0.985 | 1.00 | 119.73 | N |
| ATOM | 8125 | CA | ARG | 1122 | −26.673 | 42.365 | 2.342 | 1.00 | 125.56 | C |
| ATOM | 8126 | CB | ARG | 1122 | −28.216 | 42.272 | 2.580 | 1.00 | 134.15 | C |
| ATOM | 8127 | CG | ARG | 1122 | −29.075 | 41.696 | 1.442 | 1.00 | 134.87 | C |
| ATOM | 8128 | CD | ARG | 1122 | −29.883 | 40.427 | 1.755 | 1.00 | 128.57 | C |
| ATOM | 8129 | NE | ARG | 1122 | −29.573 | 39.356 | 0.789 | 1.00 | 137.32 | N |
| ATOM | 8130 | CZ | ARG | 1122 | −29.856 | 39.355 | −0.530 | 1.00 | 138.94 | C |
| ATOM | 8131 | NH1 | ARG | 1122 | −29.495 | 38.311 | −1.285 | 1.00 | 127.82 | N |
| ATOM | 8132 | NH2 | ARG | 1122 | −30.488 | 40.376 | −1.122 | 1.00 | 141.69 | N |
| ATOM | 8133 | C | ARG | 1122 | −25.968 | 41.008 | 2.650 | 1.00 | 126.60 | C |
| ATOM | 8134 | O | ARG | 1122 | −25.315 | 40.441 | 1.764 | 1.00 | 128.12 | O |
| ATOM | 8135 | N | GLU A | 1123 | −26.080 | 40.517 | 3.902 | 1.00 | 125.41 | N |
| ATOM | 8136 | CA | GLU A | 1123 | −25.534 | 39.190 | 4.317 | 1.00 | 116.81 | C |
| ATOM | 8137 | CB | GLU A | 1123 | −25.473 | 39.007 | 5.852 | 1.00 | 107.54 | C |
| ATOM | 8138 | C | GLU A | 1123 | −26.342 | 38.063 | 3.633 | 1.00 | 114.45 | C |
| ATOM | 8139 | O | GLU A | 1123 | −27.594 | 37.945 | 3.793 | 1.00 | 98.66 | O |
| ATOM | 8140 | N | ALA A | 1124 | −25.580 | 37.258 | 2.876 | 1.00 | 108.84 | N |
| ATOM | 8141 | CA | ALA A | 1124 | −26.072 | 36.389 | 1.797 | 1.00 | 93.41 | C |
| ATOM | 8142 | CB | ALA A | 1124 | −25.096 | 36.443 | 0.639 | 1.00 | 88.14 | C |
| ATOM | 8143 | C | ALA A | 1124 | −26.225 | 34.962 | 2.290 | 1.00 | 83.68 | C |
| ATOM | 8144 | O | ALA A | 1124 | −25.523 | 34.547 | 3.198 | 1.00 | 79.13 | O |
| ATOM | 8145 | N | THR A | 1125 | −27.146 | 34.217 | 1.702 | 1.00 | 77.96 | N |
| ATOM | 8146 | CA | THR A | 1125 | −27.439 | 32.861 | 2.192 | 1.00 | 80.33 | C |
| ATOM | 8147 | CB | THR A | 1125 | −28.962 | 32.610 | 2.368 | 1.00 | 82.35 | C |
| ATOM | 8148 | OG1 | THR A | 1125 | −29.474 | 31.899 | 1.242 | 1.00 | 88.87 | O |
| ATOM | 8149 | CG2 | THR A | 1125 | −29.764 | 33.923 | 2.568 | 1.00 | 81.94 | C |
| ATOM | 8150 | C | THR A | 1125 | −26.788 | 31.723 | 1.356 | 1.00 | 75.32 | C |
| ATOM | 8151 | O | THR A | 1125 | −26.206 | 31.935 | 0.302 | 1.00 | 72.16 | O |
| ATOM | 8152 | N | ALA A | 1126 | −26.876 | 30.513 | 1.881 | 1.00 | 70.30 | N |
| ATOM | 8153 | CA | ALA A | 1126 | −26.382 | 29.338 | 1.209 | 1.00 | 68.32 | C |
| ATOM | 8154 | CB | ALA A | 1126 | −26.595 | 28.125 | 2.094 | 1.00 | 66.77 | C |
| ATOM | 8155 | C | ALA A | 1126 | −27.139 | 29.158 | −0.083 | 1.00 | 71.75 | C |
| ATOM | 8156 | O | ALA A | 1126 | −26.564 | 28.976 | −1.149 | 1.00 | 73.69 | O |
| ATOM | 8157 | N | ASP A | 1127 | −28.455 | 29.224 | 0.025 | 1.00 | 78.64 | N |
| ATOM | 8158 | CA | ASP A | 1127 | −29.320 | 29.073 | −1.126 | 1.00 | 81.86 | C |
| ATOM | 8159 | CB | ASP A | 1127 | −30.761 | 28.852 | −0.685 | 1.00 | 83.87 | C |
| ATOM | 8160 | CG | ASP A | 1127 | −30.931 | 27.556 | 0.117 | 1.00 | 87.63 | C |

TABLE 6-continued

Atomic coordinates for CRBN:DDB1: Compound B (Human protein)

| ATOM | 8161 | OD1 | ASP A | 1127 | −30.786 | 26.457 | −0.465 | 1.00 | 93.08 | O |
|---|---|---|---|---|---|---|---|---|---|---|
| ATOM | 8162 | OD2 | ASP A | 1127 | −31.195 | 27.628 | 1.338 | 1.00 | 87.22 | O |
| ATOM | 8163 | C | ASP A | 1127 | −29.182 | 30.232 | −2.116 | 1.00 | 83.31 | C |
| ATOM | 8164 | O | ASP A | 1127 | −29.364 | 30.019 | −3.313 | 1.00 | 94.13 | O |
| ATOM | 8165 | N | ASP A | 1128 | −28.830 | 31.426 | −1.642 | 1.00 | 80.31 | N |
| ATOM | 8166 | CA | ASP A | 1128 | −28.407 | 32.501 | −2.547 | 1.00 | 88.29 | C |
| ATOM | 8167 | CB | ASP A | 1128 | −27.889 | 33.733 | −1.784 | 1.00 | 100.30 | C |
| ATOM | 8168 | CG | ASP A | 1128 | −29.004 | 34.585 | −1.170 | 1.00 | 109.02 | C |
| ATOM | 8169 | OD1 | ASP A | 1128 | −30.185 | 34.436 | −1.566 | 1.00 | 113.11 | O |
| ATOM | 8170 | OD2 | ASP A | 1128 | −28.672 | 35.424 | −0.285 | 1.00 | 113.50 | O |
| ATOM | 8171 | C | ASP A | 1128 | −27.301 | 32.071 | −3.508 | 1.00 | 82.61 | C |
| ATOM | 8172 | O | ASP A | 1128 | −27.385 | 32.292 | −4.714 | 1.00 | 85.57 | O |
| ATOM | 8173 | N | LEU A | 1129 | −26.255 | 31.477 | −2.968 | 1.00 | 77.55 | N |
| ATOM | 8174 | CA | LEU A | 1129 | −25.132 | 31.089 | −3.794 | 1.00 | 71.72 | C |
| ATOM | 8175 | CB | LEU A | 1129 | −23.836 | 30.976 | −2.999 | 1.00 | 71.49 | C |
| ATOM | 8176 | CG | LEU A | 1129 | −23.125 | 32.318 | −2.889 | 1.00 | 71.88 | C |
| ATOM | 8177 | CD1 | LEU A | 1129 | −22.623 | 32.749 | −4.239 | 1.00 | 71.37 | C |
| ATOM | 8178 | CD2 | LEU A | 1129 | −24.034 | 33.402 | −2.330 | 1.00 | 76.85 | C |
| ATOM | 8179 | C | LEU A | 1129 | −25.416 | 29.824 | −4.508 | 1.00 | 67.40 | C |
| ATOM | 8180 | O | LEU A | 1129 | −24.960 | 29.675 | −5.620 | 1.00 | 64.90 | O |
| ATOM | 8181 | N | ILE A | 1130 | −26.171 | 28.912 | −3.919 | 1.00 | 64.56 | N |
| ATOM | 8182 | CA | ILE A | 1130 | −26.503 | 27.747 | −4.687 | 1.00 | 71.94 | C |
| ATOM | 8183 | CB | ILE A | 1130 | −27.432 | 26.750 | −3.969 | 1.00 | 73.62 | C |
| ATOM | 8184 | CG1 | ILE A | 1130 | −26.649 | 25.944 | −2.907 | 1.00 | 74.67 | C |
| ATOM | 8185 | CD1 | ILE A | 1130 | −27.416 | 24.820 | −2.221 | 1.00 | 71.65 | C |
| ATOM | 8186 | CG2 | ILE A | 1130 | −28.044 | 25.787 | −4.993 | 1.00 | 74.03 | C |
| ATOM | 8187 | C | ILE A | 1130 | −27.111 | 28.168 | −6.030 | 1.00 | 75.95 | C |
| ATOM | 8188 | O | ILE A | 1130 | −26.720 | 27.663 | −7.059 | 1.00 | 75.96 | O |
| ATOM | 8189 | N | LYS A | 1131 | −28.054 | 29.089 | −6.055 | 1.00 | 84.17 | N |
| ATOM | 8190 | CA | LYS A | 1131 | −28.716 | 29.328 | −7.348 | 1.00 | 93.98 | C |
| ATOM | 8191 | CB | LYS A | 1131 | −30.187 | 29.831 | −7.182 | 1.00 | 101.96 | C |
| ATOM | 8192 | CG | LYS A | 1131 | −30.402 | 31.277 | −6.761 | 1.00 | 105.97 | C |
| ATOM | 8193 | CD | LYS A | 1131 | −31.009 | 32.131 | −7.880 | 1.00 | 106.51 | C |
| ATOM | 8194 | CE | LYS A | 1131 | −31.179 | 33.583 | −7.451 | 1.00 | 102.89 | C |
| ATOM | 8195 | NZ | LYS A | 1131 | −29.910 | 34.156 | −6.906 | 1.00 | 100.97 | N |
| ATOM | 8196 | C | LYS A | 1131 | −27.834 | 30.097 | −8.385 | 1.00 | 83.61 | C |
| ATOM | 8197 | O | LYS A | 1131 | −28.072 | 29.986 | −9.589 | 1.00 | 86.97 | O |
| ATOM | 8198 | N | VAL A | 1132 | −26.825 | 30.824 | −7.915 | 1.00 | 69.53 | N |
| ATOM | 8199 | CA | VAL A | 1132 | −25.798 | 31.397 | −8.779 | 1.00 | 68.14 | C |
| ATOM | 8200 | CB | VAL A | 1132 | −24.820 | 32.263 | −7.947 | 1.00 | 68.47 | C |
| ATOM | 8201 | CG1 | VAL A | 1132 | −23.518 | 32.583 | −8.693 | 1.00 | 67.52 | C |
| ATOM | 8202 | CG2 | VAL A | 1132 | −25.506 | 33.527 | −7.482 | 1.00 | 68.76 | C |
| ATOM | 8203 | C | VAL A | 1132 | −24.939 | 30.330 | −9.463 | 1.00 | 68.05 | C |
| ATOM | 8204 | O | VAL A | 1132 | −24.682 | 30.372 | −10.663 | 1.00 | 69.56 | O |
| ATOM | 8205 | N | VAL A | 1133 | −24.443 | 29.413 | −8.656 | 1.00 | 67.91 | N |
| ATOM | 8206 | CA | VAL A | 1133 | −23.476 | 28.432 | −9.091 | 1.00 | 66.60 | C |
| ATOM | 8207 | CB | VAL A | 1133 | −22.802 | 27.716 | −7.878 | 1.00 | 62.19 | C |
| ATOM | 8208 | CG1 | VAL A | 1133 | −21.839 | 26.639 | −8.292 | 1.00 | 63.29 | C |
| ATOM | 8209 | CG2 | VAL A | 1133 | −22.006 | 28.696 | −7.069 | 1.00 | 59.65 | C |
| ATOM | 8210 | C | VAL A | 1133 | −24.198 | 27.496 | −10.067 | 1.00 | 69.54 | C |
| ATOM | 8211 | O | VAL A | 1133 | −23.618 | 27.170 | −11.107 | 1.00 | 76.94 | O |
| ATOM | 8212 | N | GLU A | 1134 | −25.465 | 27.143 | −9.796 | 1.00 | 71.04 | N |
| ATOM | 8213 | CA | GLU A | 1134 | −26.271 | 26.368 | −10.767 | 1.00 | 71.48 | C |
| ATOM | 8214 | CB | GLU A | 1134 | −27.547 | 25.725 | −10.182 | 1.00 | 72.38 | C |
| ATOM | 8215 | CG | GLU A | 1134 | −27.359 | 24.243 | −9.776 | 1.00 | 81.36 | C |
| ATOM | 8216 | CD | GLU A | 1134 | −28.215 | 23.760 | −8.556 | 1.00 | 90.44 | C |
| ATOM | 8217 | OE1 | GLU A | 1134 | −29.389 | 24.186 | −8.424 | 1.00 | 100.22 | O |
| ATOM | 8218 | OE2 | GLU A | 1134 | −27.745 | 22.927 | −7.712 | 1.00 | 83.38 | O |
| ATOM | 8219 | C | GLU A | 1134 | −26.557 | 27.176 | −12.023 | 1.00 | 69.29 | C |
| ATOM | 8220 | O | GLU A | 1134 | −26.689 | 26.594 | −13.049 | 1.00 | 65.64 | O |
| ATOM | 8221 | N | GLU A | 1135 | −26.594 | 28.498 | −11.967 | 1.00 | 72.94 | N |
| ATOM | 8222 | CA | GLU A | 1135 | −26.612 | 29.302 | −13.201 | 1.00 | 76.92 | C |
| ATOM | 8223 | CB | GLU A | 1135 | −27.069 | 30.771 | −12.979 | 1.00 | 86.14 | C |
| ATOM | 8224 | CG | GLU A | 1135 | −28.611 | 30.911 | −12.809 | 1.00 | 96.25 | C |
| ATOM | 8225 | CD | GLU A | 1135 | −29.130 | 32.353 | −12.600 | 1.00 | 100.02 | C |
| ATOM | 8226 | OE1 | GLU A | 1135 | −29.738 | 32.607 | −11.527 | 1.00 | 97.06 | O |
| ATOM | 8227 | OE2 | GLU A | 1135 | −28.956 | 33.225 | −13.497 | 1.00 | 98.62 | O |
| ATOM | 8228 | C | GLU A | 1135 | −25.285 | 29.237 | −13.943 | 1.00 | 75.65 | C |
| ATOM | 8229 | O | GLU A | 1135 | −25.250 | 29.373 | −15.167 | 1.00 | 81.68 | O |
| ATOM | 8230 | N | LEU A | 1136 | −24.195 | 29.020 | −13.234 | 1.00 | 71.27 | N |
| ATOM | 8231 | CA | LEU A | 1136 | −22.904 | 28.923 | −13.897 | 1.00 | 67.34 | C |
| ATOM | 8232 | CB | LEU A | 1136 | −21.773 | 29.302 | −12.933 | 1.00 | 66.87 | C |
| ATOM | 8233 | CG | LEU A | 1136 | −21.604 | 30.818 | −12.728 | 1.00 | 63.63 | C |
| ATOM | 8234 | CD1 | LEU A | 1136 | −20.439 | 31.164 | −11.818 | 1.00 | 64.10 | C |
| ATOM | 8235 | CD2 | LEU A | 1136 | −21.376 | 31.497 | −14.058 | 1.00 | 64.04 | C |
| ATOM | 8236 | C | LEU A | 1136 | −22.666 | 27.564 | −14.533 | 1.00 | 65.34 | C |
| ATOM | 8237 | O | LEU A | 1136 | −21.949 | 27.478 | −15.539 | 1.00 | 64.68 | O |
| ATOM | 8238 | N | THR A | 1137 | −23.272 | 26.514 | −13.974 | 1.00 | 61.82 | N |

TABLE 6-continued

Atomic coordinates for CRBN:DDB1: Compound B (Human protein)

| ATOM | 8239 | CA | THR A | 1137 | −23.104 | 25.175 | −14.546 | 1.00 | 64.42 | C |
|---|---|---|---|---|---|---|---|---|---|---|
| ATOM | 8240 | CB | THR A | 1137 | −23.729 | 23.994 | −13.732 | 1.00 | 62.87 | C |
| ATOM | 8241 | OG1 | THR A | 1137 | −25.034 | 24.319 | −13.282 | 1.00 | 62.30 | O |
| ATOM | 8242 | CG2 | THR A | 1137 | −22.883 | 23.612 | −12.547 | 1.00 | 62.21 | C |
| ATOM | 8243 | C | THR A | 1137 | −23.704 | 25.087 | −15.909 | 1.00 | 67.85 | C |
| ATOM | 8244 | O | THR A | 1137 | −23.273 | 24.273 | −16.708 | 1.00 | 75.70 | O |
| ATOM | 8245 | N | ARG A | 1138 | −24.707 | 25.915 | −16.166 | 1.00 | 75.58 | N |
| ATOM | 8246 | CA | ARG A | 1138 | −25.502 | 25.833 | −17.383 | 1.00 | 76.40 | C |
| ATOM | 8247 | CB | ARG A | 1138 | −26.987 | 26.184 | −17.081 | 1.00 | 78.97 | C |
| ATOM | 8248 | CG | ARG A | 1138 | −27.760 | 24.941 | −16.607 | 1.00 | 82.77 | C |
| ATOM | 8249 | CD | ARG A | 1138 | −29.058 | 25.221 | −15.840 | 1.00 | 80.87 | C |
| ATOM | 8250 | NE | ARG A | 1138 | −29.027 | 24.507 | −14.556 | 1.00 | 78.71 | N |
| ATOM | 8251 | CZ | ARG A | 1138 | −29.754 | 24.793 | −13.469 | 1.00 | 77.26 | C |
| ATOM | 8252 | NH1 | ARG A | 1138 | −30.681 | 25.769 | −13.488 | 1.00 | 73.17 | N |
| ATOM | 8253 | NH2 | ARG A | 1138 | −29.565 | 24.056 | −12.351 | 1.00 | 76.98 | N |
| ATOM | 8254 | C | ARG A | 1138 | −24.933 | 26.638 | −18.548 | 1.00 | 73.29 | C |
| ATOM | 8255 | O | ARG A | 1138 | −25.674 | 26.923 | −19.493 | 1.00 | 81.67 | O |
| ATOM | 8256 | N | ILE A | 1139 | −23.640 | 26.994 | −18.503 | 1.00 | 66.38 | N |
| ATOM | 8257 | CA | ILE A | 1139 | −22.959 | 27.474 | −19.708 | 1.00 | 63.29 | C |
| ATOM | 8258 | CB | ILE A | 1139 | −21.979 | 28.626 | −19.445 | 1.00 | 61.84 | C |
| ATOM | 8259 | CG1 | ILE A | 1139 | −20.709 | 28.167 | −18.743 | 1.00 | 63.94 | C |
| ATOM | 8260 | CD1 | ILE A | 1139 | −19.840 | 29.331 | −18.298 | 1.00 | 65.73 | C |
| ATOM | 8261 | CG2 | ILE A | 1139 | −22.644 | 29.723 | −18.658 | 1.00 | 62.93 | C |
| ATOM | 8262 | C | ILE A | 1139 | −22.211 | 26.394 | −20.473 | 1.00 | 64.13 | C |
| ATOM | 8263 | O | ILE A | 1139 | −21.513 | 26.731 | −21.436 | 1.00 | 68.22 | O |
| ATOM | 8264 | N | HIS A | 1140 | −22.342 | 25.121 | −20.080 | 1.00 | 61.71 | N |
| ATOM | 8265 | CA | HIS A | 1140 | −21.523 | 24.060 | −20.674 | 1.00 | 61.54 | C |
| ATOM | 8266 | CB | HIS A | 1140 | −20.081 | 24.172 | −20.139 | 1.00 | 60.91 | C |
| ATOM | 8267 | CG | HIS A | 1140 | −19.916 | 23.647 | −18.745 | 1.00 | 59.88 | C |
| ATOM | 8268 | ND1 | HIS A | 1140 | −19.527 | 22.355 | −18.480 | 1.00 | 60.58 | N |
| ATOM | 8269 | CE1 | HIS A | 1140 | −19.485 | 22.164 | −17.179 | 1.00 | 58.80 | C |
| ATOM | 8270 | NE2 | HIS A | 1140 | −19.848 | 23.279 | −16.589 | 1.00 | 58.33 | N |
| ATOM | 8271 | CD2 | HIS A | 1140 | −20.126 | 24.223 | −17.545 | 1.00 | 60.23 | C |
| ATOM | 8272 | C | HIS A | 1140 | −22.085 | 22.622 | −20.482 | 1.00 | 60.81 | C |
| ATOM | 8273 | O | HIS A | 1140 | −22.778 | 22.312 | −19.517 | 1.00 | 60.07 | O |
| TER | 8274 | | HIS A | 1140 | | | | | | |
| ATOM | 8275 | N | ILE C | 47 | 45.485 | 29.607 | −47.725 | 1.00 | 76.28 | N |
| ATOM | 8276 | CA | ILE C | 47 | 45.722 | 30.399 | −46.437 | 1.00 | 85.04 | C |
| ATOM | 8277 | CB | ILE C | 47 | 44.385 | 30.714 | −45.680 | 1.00 | 89.53 | C |
| ATOM | 8278 | CG1 | ILE C | 47 | 44.609 | 31.736 | −44.539 | 1.00 | 86.82 | C |
| ATOM | 8279 | CD1 | ILE C | 47 | 43.359 | 32.096 | −43.759 | 1.00 | 83.92 | C |
| ATOM | 8280 | CG2 | ILE C | 47 | 43.719 | 29.424 | −45.158 | 1.00 | 93.27 | C |
| ATOM | 8281 | C | ILE C | 47 | 46.724 | 29.765 | −45.435 | 1.00 | 86.59 | C |
| ATOM | 8282 | O | ILE C | 47 | 46.509 | 28.640 | −44.979 | 1.00 | 91.11 | O |
| ATOM | 8283 | N | ASN C | 48 | 47.787 | 30.489 | −45.059 | 1.00 | 87.47 | N |
| ATOM | 8284 | CA | ASN C | 48 | 48.737 | 29.992 | −44.030 | 1.00 | 89.53 | C |
| ATOM | 8285 | CB | ASN C | 48 | 49.847 | 29.135 | −44.632 | 1.00 | 90.05 | C |
| ATOM | 8286 | CG | ASN C | 48 | 50.462 | 29.757 | −45.877 | 1.00 | 90.10 | C |
| ATOM | 8287 | OD1 | ASN C | 48 | 50.288 | 29.217 | −46.986 | 1.00 | 94.29 | O |
| ATOM | 8288 | ND2 | ASN C | 48 | 51.197 | 30.872 | −45.715 | 1.00 | 82.18 | N |
| ATOM | 8289 | C | ASN C | 48 | 49.312 | 31.129 | −43.210 | 1.00 | 93.00 | C |
| ATOM | 8290 | O | ASN C | 48 | 50.537 | 31.339 | −43.115 | 1.00 | 95.29 | O |
| ATOM | 8291 | N | PHE C | 49 | 48.384 | 31.877 | −42.635 | 1.00 | 91.27 | N |
| ATOM | 8292 | CA | PHE C | 49 | 48.682 | 32.955 | −41.712 | 1.00 | 84.82 | C |
| ATOM | 8293 | CB | PHE C | 49 | 48.061 | 34.277 | −42.219 | 1.00 | 80.58 | C |
| ATOM | 8294 | CG | PHE C | 49 | 47.895 | 35.335 | −41.159 | 1.00 | 70.15 | C |
| ATOM | 8295 | CD1 | PHE C | 49 | 48.963 | 36.149 | −40.798 | 1.00 | 64.30 | C |
| ATOM | 8296 | CE1 | PHE C | 49 | 48.804 | 37.131 | −39.837 | 1.00 | 63.87 | C |
| ATOM | 8297 | CZ | PHE C | 49 | 47.569 | 37.318 | −39.223 | 1.00 | 63.49 | C |
| ATOM | 8298 | CE2 | PHE C | 49 | 46.491 | 36.509 | −39.573 | 1.00 | 65.05 | C |
| ATOM | 8299 | CD2 | PHE C | 49 | 46.655 | 35.528 | −40.541 | 1.00 | 67.24 | C |
| ATOM | 8300 | C | PHE C | 49 | 48.099 | 32.498 | −40.383 | 1.00 | 78.68 | C |
| ATOM | 8301 | O | PHE C | 49 | 47.046 | 31.844 | −40.328 | 1.00 | 79.20 | O |
| ATOM | 8302 | N | ASP C | 50 | 48.787 | 32.851 | −39.315 | 1.00 | 69.33 | N |
| ATOM | 8303 | CA | ASP C | 50 | 48.457 | 32.323 | −38.024 | 1.00 | 62.13 | C |
| ATOM | 8304 | CB | ASP C | 50 | 49.642 | 32.542 | −37.129 | 1.00 | 61.92 | C |
| ATOM | 8305 | CG | ASP C | 50 | 49.567 | 31.767 | −35.892 | 1.00 | 60.39 | C |
| ATOM | 8306 | OD1 | ASP C | 50 | 48.524 | 31.801 | −35.195 | 1.00 | 60.41 | O |
| ATOM | 8307 | OD2 | ASP C | 50 | 50.595 | 31.143 | −35.608 | 1.00 | 63.25 | O |
| ATOM | 8308 | C | ASP C | 50 | 47.218 | 33.021 | −37.508 | 1.00 | 62.25 | C |
| ATOM | 8309 | O | ASP C | 50 | 47.272 | 34.133 | −36.956 | 1.00 | 62.44 | O |
| ATOM | 8310 | N | THR C | 51 | 46.078 | 32.363 | −37.659 | 1.00 | 64.06 | N |
| ATOM | 8311 | CA | THR C | 51 | 44.821 | 33.033 | −37.330 | 1.00 | 64.01 | C |
| ATOM | 8312 | CB | THR C | 51 | 43.576 | 32.289 | −37.875 | 1.00 | 61.77 | C |
| ATOM | 8313 | OG1 | THR C | 51 | 43.554 | 30.976 | −37.353 | 1.00 | 68.93 | O |
| ATOM | 8314 | CG2 | THR C | 51 | 43.628 | 32.189 | −39.367 | 1.00 | 62.50 | C |
| ATOM | 8315 | C | THR C | 51 | 44.619 | 33.352 | −35.850 | 1.00 | 62.45 | C |
| ATOM | 8316 | O | THR C | 51 | 43.541 | 33.807 | −35.515 | 1.00 | 67.50 | O |

TABLE 6-continued

Atomic coordinates for CRBN:DDB1: Compound B (Human protein)

| ATOM | 8317 | N | SER C | 52 | 45.603 | 33.115 | −34.971 | 1.00 | 62.62 | N |
|---|---|---|---|---|---|---|---|---|---|---|
| ATOM | 8318 | CA | SER C | 52 | 45.547 | 33.653 | −33.581 | 1.00 | 65.23 | C |
| ATOM | 8319 | CB | SER C | 52 | 45.789 | 32.555 | −32.537 | 1.00 | 62.29 | C |
| ATOM | 8320 | OG | SER C | 52 | 47.069 | 32.004 | −32.691 | 1.00 | 61.74 | O |
| ATOM | 8321 | C | SER C | 52 | 46.434 | 34.907 | −33.292 | 1.00 | 64.00 | C |
| ATOM | 8322 | O | SER C | 52 | 46.164 | 35.627 | −32.308 | 1.00 | 61.44 | O |
| ATOM | 8323 | N | LEU C | 53 | 47.431 | 35.204 | −34.150 | 1.00 | 63.48 | N |
| ATOM | 8324 | CA | LEU C | 53 | 48.299 | 36.407 | −33.971 | 1.00 | 61.10 | C |
| ATOM | 8325 | CB | LEU C | 53 | 49.417 | 36.532 | −35.083 | 1.00 | 51.50 | C |
| ATOM | 8326 | C | LEU C | 53 | 47.353 | 37.654 | −33.782 | 1.00 | 63.15 | C |
| ATOM | 8327 | O | LEU C | 53 | 47.570 | 38.470 | −32.883 | 1.00 | 65.58 | O |
| ATOM | 8328 | N | PRO C | 54 | 46.254 | 37.749 | −34.569 | 1.00 | 63.96 | N |
| ATOM | 8329 | CA | PRO C | 54 | 45.376 | 38.929 | −34.470 | 1.00 | 65.04 | C |
| ATOM | 8330 | CB | PRO C | 54 | 44.399 | 38.766 | −35.653 | 1.00 | 63.78 | C |
| ATOM | 8331 | CG | PRO C | 54 | 45.130 | 37.905 | −36.593 | 1.00 | 65.70 | C |
| ATOM | 8332 | CD | PRO C | 54 | 45.934 | 36.951 | −35.767 | 1.00 | 65.33 | C |
| ATOM | 8333 | C | PRO C | 54 | 44.588 | 39.069 | −33.193 | 1.00 | 61.09 | C |
| ATOM | 8334 | O | PRO C | 54 | 44.498 | 40.145 | −32.629 | 1.00 | 61.73 | O |
| ATOM | 8335 | N | THR C | 55 | 43.994 | 38.002 | −32.748 | 1.00 | 64.81 | N |
| ATOM | 8336 | CA | THR C | 55 | 43.256 | 38.105 | −31.525 | 1.00 | 74.75 | C |
| ATOM | 8337 | CB | THR C | 55 | 42.454 | 36.821 | −31.208 | 1.00 | 81.47 | C |
| ATOM | 8338 | OG1 | THR C | 55 | 41.473 | 37.161 | −30.213 | 1.00 | 84.30 | O |
| ATOM | 8339 | CG2 | THR C | 55 | 43.375 | 35.604 | −30.729 | 1.00 | 80.87 | C |
| ATOM | 8340 | C | THR C | 55 | 44.130 | 38.500 | −30.309 | 1.00 | 71.82 | C |
| ATOM | 8341 | O | THR C | 55 | 43.584 | 38.971 | −29.308 | 1.00 | 65.73 | O |
| ATOM | 8342 | N | SER C | 56 | 45.455 | 38.297 | −30.367 | 1.00 | 69.23 | N |
| ATOM | 8343 | CA | SER C | 56 | 46.296 | 38.656 | −29.207 | 1.00 | 65.03 | C |
| ATOM | 8344 | CB | SER C | 56 | 47.484 | 37.672 | −28.991 | 1.00 | 63.23 | C |
| ATOM | 8345 | OG | SER C | 56 | 48.343 | 37.649 | −30.093 | 1.00 | 60.76 | O |
| ATOM | 8346 | C | SER C | 56 | 46.738 | 40.105 | −29.173 | 1.00 | 57.76 | C |
| ATOM | 8347 | O | SER C | 56 | 47.267 | 40.528 | −28.150 | 1.00 | 58.45 | O |
| ATOM | 8348 | N | HIS C | 57 | 46.499 | 40.855 | −30.252 | 1.00 | 54.29 | N |
| ATOM | 8349 | CA | HIS C | 57 | 46.774 | 42.304 | −30.329 | 1.00 | 53.98 | C |
| ATOM | 8350 | CB | HIS C | 57 | 45.767 | 43.080 | −29.500 | 1.00 | 51.92 | C |
| ATOM | 8351 | CG | HIS C | 57 | 44.368 | 42.906 | −29.960 | 1.00 | 52.52 | C |
| ATOM | 8352 | ND1 | HIS C | 57 | 43.731 | 43.821 | −30.762 | 1.00 | 57.14 | N |
| ATOM | 8353 | CE1 | HIS C | 57 | 42.506 | 43.406 | −31.026 | 1.00 | 54.05 | C |
| ATOM | 8354 | NE2 | HIS C | 57 | 42.321 | 42.261 | −30.410 | 1.00 | 54.38 | N |
| ATOM | 8355 | CD2 | HIS C | 57 | 43.477 | 41.922 | −29.746 | 1.00 | 53.14 | C |
| ATOM | 8356 | C | HIS C | 57 | 48.199 | 42.684 | −29.917 | 1.00 | 56.28 | C |
| ATOM | 8357 | O | HIS C | 57 | 48.423 | 43.488 | −28.995 | 1.00 | 54.98 | O |
| ATOM | 8358 | N | THR C | 58 | 49.159 | 42.078 | −30.608 | 1.00 | 61.04 | N |
| ATOM | 8359 | CA | THR C | 58 | 50.586 | 42.232 | −30.277 | 1.00 | 62.63 | C |
| ATOM | 8360 | CB | THR C | 58 | 51.497 | 41.364 | −31.168 | 1.00 | 62.62 | C |
| ATOM | 8361 | OG1 | THR C | 58 | 51.373 | 41.786 | −32.540 | 1.00 | 65.30 | O |
| ATOM | 8362 | CG2 | THR C | 58 | 51.156 | 39.881 | −31.023 | 1.00 | 61.74 | C |
| ATOM | 8363 | C | THR C | 58 | 51.035 | 43.667 | −30.447 | 1.00 | 59.39 | C |
| ATOM | 8364 | O | THR C | 58 | 51.781 | 44.186 | −29.647 | 1.00 | 65.69 | O |
| ATOM | 8365 | N | TYR C | 59 | 50.572 | 44.305 | −31.494 | 1.00 | 54.88 | N |
| ATOM | 8366 | CA | TYR C | 59 | 50.864 | 45.708 | −31.707 | 1.00 | 57.26 | C |
| ATOM | 8367 | CB | TYR C | 59 | 50.000 | 46.244 | −32.842 | 1.00 | 60.65 | C |
| ATOM | 8368 | CG | TYR C | 59 | 48.521 | 46.225 | −32.564 | 1.00 | 56.91 | C |
| ATOM | 8369 | CD1 | TYR C | 59 | 47.924 | 47.271 | −31.897 | 1.00 | 56.91 | C |
| ATOM | 8370 | CE1 | TYR C | 59 | 46.559 | 47.284 | −31.656 | 1.00 | 58.72 | C |
| ATOM | 8371 | CZ | TYR C | 59 | 45.780 | 46.240 | −32.088 | 1.00 | 55.31 | C |
| ATOM | 8372 | OH | TYR C | 59 | 44.442 | 46.309 | −31.849 | 1.00 | 52.37 | O |
| ATOM | 8373 | CE2 | TYR C | 59 | 46.355 | 45.166 | −32.741 | 1.00 | 56.15 | C |
| ATOM | 8374 | CD2 | TYR C | 59 | 47.724 | 45.167 | −32.978 | 1.00 | 55.79 | C |
| ATOM | 8375 | C | TYR C | 59 | 50.675 | 46.630 | −30.512 | 1.00 | 53.64 | C |
| ATOM | 8376 | O | TYR C | 59 | 51.116 | 47.780 | −30.550 | 1.00 | 50.49 | O |
| ATOM | 8377 | N | LEU C | 60 | 49.957 | 46.171 | −29.499 | 1.00 | 52.53 | N |
| ATOM | 8378 | CA | LEU C | 60 | 49.948 | 46.880 | −28.238 | 1.00 | 53.92 | C |
| ATOM | 8379 | CB | LEU C | 60 | 48.718 | 46.502 | −27.430 | 1.00 | 53.51 | C |
| ATOM | 8380 | CG | LEU C | 60 | 47.368 | 46.886 | −28.020 | 1.00 | 54.29 | C |
| ATOM | 8381 | CD1 | LEU C | 60 | 46.295 | 46.329 | −27.104 | 1.00 | 56.38 | C |
| ATOM | 8382 | CD2 | LEU C | 60 | 47.194 | 48.390 | −28.125 | 1.00 | 54.71 | C |
| ATOM | 8383 | C | LEU C | 60 | 51.204 | 46.696 | −27.392 | 1.00 | 53.83 | C |
| ATOM | 8384 | O | LEU C | 60 | 51.362 | 47.414 | −26.425 | 1.00 | 53.57 | O |
| ATOM | 8385 | N | GLY C | 61 | 52.106 | 45.800 | −27.776 | 1.00 | 59.28 | N |
| ATOM | 8386 | CA | GLY C | 61 | 53.140 | 45.255 | −26.875 | 1.00 | 72.32 | C |
| ATOM | 8387 | C | GLY C | 61 | 52.694 | 43.938 | −26.217 | 1.00 | 83.65 | C |
| ATOM | 8388 | O | GLY C | 61 | 51.549 | 43.826 | −25.716 | 1.00 | 82.22 | O |
| ATOM | 8389 | N | ALA C | 62 | 53.582 | 42.936 | −26.207 | 1.00 | 90.91 | N |
| ATOM | 8390 | CA | ALA C | 62 | 53.187 | 41.569 | −25.791 | 1.00 | 95.99 | C |
| ATOM | 8391 | CB | ALA C | 62 | 53.595 | 40.543 | −26.869 | 1.00 | 90.56 | C |
| ATOM | 8392 | C | ALA C | 62 | 53.656 | 41.122 | −24.368 | 1.00 | 99.55 | C |
| ATOM | 8393 | O | ALA C | 62 | 53.689 | 39.909 | −24.103 | 1.00 | 99.54 | O |
| ATOM | 8394 | N | ASP C | 63 | 54.016 | 42.067 | −23.471 | 1.00 | 98.59 | N |

TABLE 6-continued

Atomic coordinates for CRBN:DDB1: Compound B (Human protein)

| ATOM | 8395 | CA | ASP C | 63 | 54.252 | 41.743 | −22.024 | 1.00 | 96.20 | C |
|---|---|---|---|---|---|---|---|---|---|---|
| ATOM | 8396 | CB | ASP C | 63 | 55.726 | 41.919 | −21.579 | 1.00 | 94.76 | C |
| ATOM | 8397 | C | ASP C | 63 | 53.294 | 42.563 | −21.155 | 1.00 | 87.49 | C |
| ATOM | 8398 | O | ASP C | 63 | 53.663 | 43.572 | −20.567 | 1.00 | 83.25 | O |
| ATOM | 8399 | N | MET C | 64 | 52.047 | 42.106 | −21.118 | 1.00 | 82.32 | N |
| ATOM | 8400 | CA | MET C | 64 | 50.970 | 42.743 | −20.373 | 1.00 | 83.71 | C |
| ATOM | 8401 | CB | MET C | 64 | 49.689 | 42.766 | −21.224 | 1.00 | 87.98 | C |
| ATOM | 8402 | CG | MET C | 64 | 49.752 | 43.511 | −22.549 | 1.00 | 90.37 | C |
| ATOM | 8403 | SD | MET C | 64 | 48.260 | 44.495 | −22.838 | 1.00 | 93.35 | S |
| ATOM | 8404 | CE | MET C | 64 | 48.360 | 44.706 | −24.608 | 1.00 | 97.50 | C |
| ATOM | 8405 | C | MET C | 64 | 50.671 | 41.867 | −19.169 | 1.00 | 79.81 | C |
| ATOM | 8406 | O | MET C | 64 | 50.605 | 40.656 | −19.367 | 1.00 | 71.84 | O |
| ATOM | 8407 | N | GLU C | 65 | 50.465 | 42.446 | −17.964 | 1.00 | 77.03 | N |
| ATOM | 8408 | CA | GLU C | 65 | 49.963 | 41.665 | −16.785 | 1.00 | 75.21 | C |
| ATOM | 8409 | CB | GLU C | 65 | 50.120 | 42.426 | −15.419 | 1.00 | 69.86 | C |
| ATOM | 8410 | C | GLU C | 65 | 48.500 | 41.190 | −17.123 | 1.00 | 71.98 | C |
| ATOM | 8411 | O | GLU C | 65 | 47.714 | 41.948 | −17.694 | 1.00 | 70.03 | O |
| ATOM | 8412 | N | GLU C | 66 | 48.205 | 39.939 | −16.826 | 1.00 | 69.42 | N |
| ATOM | 8413 | CA | GLU C | 66 | 46.934 | 39.355 | −17.153 | 1.00 | 70.40 | C |
| ATOM | 8414 | CB | GLU C | 66 | 47.152 | 38.086 | −17.949 | 1.00 | 75.19 | C |
| ATOM | 8415 | CG | GLU C | 66 | 47.698 | 38.302 | −19.339 | 1.00 | 84.30 | C |
| ATOM | 8416 | CD | GLU C | 66 | 48.019 | 37.004 | −20.045 | 1.00 | 96.74 | C |
| ATOM | 8417 | OE1 | GLU C | 66 | 48.905 | 37.012 | −20.922 | 1.00 | 103.78 | O |
| ATOM | 8418 | OE2 | GLU C | 66 | 47.393 | 35.972 | −19.726 | 1.00 | 92.29 | O |
| ATOM | 8419 | C | GLU C | 66 | 46.167 | 38.988 | −15.933 | 1.00 | 71.53 | C |
| ATOM | 8420 | O | GLU C | 66 | 46.729 | 38.591 | −14.942 | 1.00 | 76.21 | O |
| ATOM | 8421 | N | PHE C | 67 | 44.860 | 39.125 | −16.008 | 1.00 | 77.64 | N |
| ATOM | 8422 | CA | PHE C | 67 | 44.014 | 38.796 | −14.894 | 1.00 | 80.54 | C |
| ATOM | 8423 | CB | PHE C | 67 | 43.252 | 40.033 | −14.485 | 1.00 | 80.45 | C |
| ATOM | 8424 | CG | PHE C | 67 | 44.118 | 41.245 | −14.385 | 1.00 | 81.65 | C |
| ATOM | 8425 | CD1 | PHE C | 67 | 44.358 | 42.023 | −15.479 | 1.00 | 84.06 | C |
| ATOM | 8426 | CE1 | PHE C | 67 | 45.164 | 43.130 | −15.399 | 1.00 | 82.68 | C |
| ATOM | 8427 | CZ | PHE C | 67 | 45.750 | 43.466 | −14.215 | 1.00 | 77.70 | C |
| ATOM | 8428 | CE2 | PHE C | 67 | 45.528 | 42.688 | −13.115 | 1.00 | 77.83 | C |
| ATOM | 8429 | CD2 | PHE C | 67 | 44.717 | 41.581 | −13.206 | 1.00 | 79.62 | C |
| ATOM | 8430 | C | PHE C | 67 | 43.112 | 37.673 | −15.346 | 1.00 | 84.78 | C |
| ATOM | 8431 | O | PHE C | 67 | 42.556 | 37.742 | −16.425 | 1.00 | 90.09 | O |
| ATOM | 8432 | N | HIS C | 68 | 42.968 | 36.631 | −14.536 | 1.00 | 83.49 | N |
| ATOM | 8433 | CA | HIS C | 68 | 42.156 | 35.512 | −14.959 | 1.00 | 85.74 | C |
| ATOM | 8434 | CB | HIS C | 68 | 42.376 | 34.317 | −14.057 | 1.00 | 83.79 | C |
| ATOM | 8435 | C | HIS C | 68 | 40.750 | 35.956 | −14.836 | 1.00 | 92.68 | C |
| ATOM | 8436 | O | HIS C | 68 | 40.228 | 36.133 | −13.749 | 1.00 | 84.18 | O |
| ATOM | 8437 | N | GLY C | 69 | 40.136 | 36.104 | −15.995 | 1.00 | 106.99 | N |
| ATOM | 8438 | CA | GLY C | 69 | 38.789 | 36.596 | −16.106 | 1.00 | 113.75 | C |
| ATOM | 8439 | C | GLY C | 69 | 37.718 | 35.764 | −15.470 | 1.00 | 116.41 | C |
| ATOM | 8440 | O | GLY C | 69 | 37.740 | 34.551 | −15.490 | 1.00 | 114.70 | O |
| ATOM | 8441 | N | ARG C | 70 | 36.757 | 36.450 | −14.894 | 1.00 | 120.06 | N |
| ATOM | 8442 | CA | ARG C | 70 | 35.639 | 35.752 | −14.272 | 1.00 | 115.01 | C |
| ATOM | 8443 | CB | ARG C | 70 | 36.267 | 34.767 | −13.291 | 1.00 | 125.64 | C |
| ATOM | 8444 | CG | ARG C | 70 | 37.105 | 35.432 | −12.187 | 1.00 | 129.65 | C |
| ATOM | 8445 | CD | ARG C | 70 | 36.424 | 35.363 | −10.818 | 1.00 | 132.10 | C |
| ATOM | 8446 | NE | ARG C | 70 | 36.104 | 33.972 | −10.416 | 1.00 | 123.68 | N |
| ATOM | 8447 | CZ | ARG C | 70 | 34.906 | 33.509 | −10.026 | 1.00 | 109.22 | C |
| ATOM | 8448 | NH1 | ARG C | 70 | 33.837 | 34.312 | −9.926 | 1.00 | 110.25 | N |
| ATOM | 8449 | NH2 | ARG C | 70 | 34.783 | 32.222 | −9.700 | 1.00 | 94.55 | N |
| ATOM | 8450 | C | ARG C | 70 | 34.527 | 36.533 | −13.528 | 1.00 | 103.06 | C |
| ATOM | 8451 | O | ARG C | 70 | 33.580 | 35.903 | −13.071 | 1.00 | 93.46 | O |
| ATOM | 8452 | N | THR C | 71 | 34.608 | 37.860 | −13.403 | 1.00 | 93.59 | N |
| ATOM | 8453 | CA | THR C | 71 | 33.662 | 38.610 | −12.544 | 1.00 | 87.92 | C |
| ATOM | 8454 | CB | THR C | 71 | 34.142 | 40.062 | −12.207 | 1.00 | 84.04 | C |
| ATOM | 8455 | OG1 | THR C | 71 | 33.748 | 40.976 | −13.244 | 1.00 | 85.01 | O |
| ATOM | 8456 | CG2 | THR C | 71 | 35.671 | 40.143 | −12.016 | 1.00 | 83.33 | C |
| ATOM | 8457 | C | THR C | 71 | 32.274 | 38.628 | −13.252 | 1.00 | 81.29 | C |
| ATOM | 8458 | O | THR C | 71 | 32.200 | 39.038 | −14.429 | 1.00 | 81.94 | O |
| ATOM | 8459 | N | LEU C | 72 | 31.213 | 38.164 | −12.552 | 1.00 | 67.36 | N |
| ATOM | 8460 | CA | LEU C | 72 | 29.837 | 38.057 | −13.098 | 1.00 | 59.85 | C |
| ATOM | 8461 | CB | LEU C | 72 | 29.504 | 36.614 | −13.543 | 1.00 | 57.22 | C |
| ATOM | 8462 | CG | LEU C | 72 | 29.928 | 36.202 | −14.964 | 1.00 | 57.76 | C |
| ATOM | 8463 | CD1 | LEU C | 72 | 29.116 | 34.979 | −15.346 | 1.00 | 57.15 | C |
| ATOM | 8464 | CD2 | LEU C | 72 | 29.799 | 37.325 | −16.032 | 1.00 | 56.03 | C |
| ATOM | 8465 | C | LEU C | 72 | 28.787 | 38.508 | −12.109 | 1.00 | 55.74 | C |
| ATOM | 8466 | O | LEU C | 72 | 28.478 | 37.799 | −11.170 | 1.00 | 62.92 | O |
| ATOM | 8467 | N | HIS C | 73 | 28.219 | 39.679 | −12.328 | 1.00 | 51.20 | N |
| ATOM | 8468 | CA | HIS C | 73 | 27.194 | 40.205 | −11.446 | 1.00 | 50.44 | C |
| ATOM | 8469 | CB | HIS C | 73 | 26.951 | 41.647 | −11.761 | 1.00 | 50.96 | C |
| ATOM | 8470 | CG | HIS C | 73 | 28.134 | 42.503 | −11.510 | 1.00 | 49.99 | C |
| ATOM | 8471 | ND1 | HIS C | 73 | 28.725 | 42.587 | −10.274 | 1.00 | 53.06 | N |
| ATOM | 8472 | CE1 | HIS C | 73 | 29.737 | 43.428 | −10.329 | 1.00 | 51.89 | C |

TABLE 6-continued

Atomic coordinates for CRBN:DDB1: Compound B (Human protein)

| ATOM | 8473 | NE2 | HIS C | 73 | 29.819 | 43.892 | −11.558 | 1.00 | 49.80 | N |
|------|------|-----|-------|-----|--------|--------|---------|------|-------|---|
| ATOM | 8474 | CD2 | HIS C | 73 | 28.824 | 43.330 | −12.316 | 1.00 | 50.45 | C |
| ATOM | 8475 | C   | HIS C | 73 | 25.874 | 39.483 | −11.528 | 1.00 | 51.77 | C |
| ATOM | 8476 | O   | HIS C | 73 | 25.519 | 38.969 | −12.554 | 1.00 | 47.53 | O |
| ATOM | 8477 | N   | ASP C | 74 | 25.143 | 39.482 | −10.419 | 1.00 | 61.00 | N |
| ATOM | 8478 | CA  | ASP C | 74 | 23.942 | 38.654 | −10.263 | 1.00 | 66.70 | C |
| ATOM | 8479 | CB  | ASP C | 74 | 23.488 | 38.597 | −8.755  | 1.00 | 75.06 | C |
| ATOM | 8480 | CG  | ASP C | 74 | 24.435 | 37.711 | −7.798  | 1.00 | 80.54 | C |
| ATOM | 8481 | OD2 | ASP C | 74 | 25.435 | 38.191 | −7.167  | 1.00 | 78.16 | O |
| ATOM | 8482 | OD1 | ASP C | 74 | 24.101 | 36.522 | −7.602  | 1.00 | 84.83 | O |
| ATOM | 8483 | C   | ASP C | 74 | 22.860 | 39.242 | −11.204 | 1.00 | 63.26 | C |
| ATOM | 8484 | O   | ASP C | 74 | 22.882 | 40.450 | −11.522 | 1.00 | 55.42 | O |
| ATOM | 8485 | N   | ASP C | 75 | 21.960 | 38.391 | −11.692 | 1.00 | 65.44 | N |
| ATOM | 8486 | CA  | ASP C | 75 | 20.861 | 38.864 | −12.553 | 1.00 | 71.27 | C |
| ATOM | 8487 | CB  | ASP C | 75 | 19.972 | 37.737 | −13.052 | 1.00 | 73.65 | C |
| ATOM | 8488 | CG  | ASP C | 75 | 20.630 | 36.887 | −14.065 | 1.00 | 74.19 | C |
| ATOM | 8489 | OD1 | ASP C | 75 | 21.489 | 37.407 | −14.808 | 1.00 | 73.53 | O |
| ATOM | 8490 | OD2 | ASP C | 75 | 20.266 | 35.691 | −14.108 | 1.00 | 72.06 | O |
| ATOM | 8491 | C   | ASP C | 75 | 19.926 | 39.761 | −11.800 | 1.00 | 72.91 | C |
| ATOM | 8492 | O   | ASP C | 75 | 19.491 | 39.430 | −10.710 | 1.00 | 76.11 | O |
| ATOM | 8493 | N   | ASP C | 76 | 19.587 | 40.871 | −12.429 | 1.00 | 75.17 | N |
| ATOM | 8494 | CA  | ASP C | 76 | 18.680 | 41.882 | −11.891 | 1.00 | 73.34 | C |
| ATOM | 8495 | CB  | ASP C | 76 | 17.309 | 41.289 | −11.513 | 1.00 | 73.83 | C |
| ATOM | 8496 | CG  | ASP C | 76 | 16.674 | 40.487 | −12.676 | 1.00 | 81.22 | C |
| ATOM | 8497 | OD1 | ASP C | 76 | 16.222 | 41.088 | −13.676 | 1.00 | 85.58 | O |
| ATOM | 8498 | OD2 | ASP C | 76 | 16.636 | 39.241 | −12.609 | 1.00 | 87.30 | O |
| ATOM | 8499 | C   | ASP C | 76 | 19.320 | 42.757 | −10.800 | 1.00 | 68.70 | C |
| ATOM | 8500 | O   | ASP C | 76 | 18.701 | 43.722 | −10.364 | 1.00 | 68.89 | O |
| ATOM | 8501 | N   | SER C | 77 | 20.590 | 42.510 | −10.463 | 1.00 | 68.16 | N |
| ATOM | 8502 | CA  | SER C | 77 | 21.306 | 43.326 | −9.460  | 1.00 | 70.90 | C |
| ATOM | 8503 | CB  | SER C | 77 | 22.616 | 42.653 | −9.048  | 1.00 | 67.32 | C |
| ATOM | 8504 | OG  | SER C | 77 | 23.637 | 42.911 | −9.995  | 1.00 | 67.74 | O |
| ATOM | 8505 | C   | SER C | 77 | 21.589 | 44.747 | −9.988  | 1.00 | 73.21 | C |
| ATOM | 8506 | O   | SER C | 77 | 21.450 | 44.989 | −11.192 | 1.00 | 83.18 | O |
| ATOM | 8507 | N   | CYS C | 78 | 21.953 | 45.676 | −9.096  | 1.00 | 72.30 | N |
| ATOM | 8508 | CA  | CYS C | 78 | 22.369 | 47.029 | −9.500  | 1.00 | 71.12 | C |
| ATOM | 8509 | CB  | CYS C | 78 | 21.533 | 48.100 | −8.819  | 1.00 | 73.34 | C |
| ATOM | 8510 | SG  | CYS C | 78 | 19.849 | 48.092 | −9.494  | 1.00 | 91.20 | S |
| ATOM | 8511 | C   | CYS C | 78 | 23.840 | 47.231 | −9.240  | 1.00 | 67.19 | C |
| ATOM | 8512 | O   | CYS C | 78 | 24.378 | 46.731 | −8.272  | 1.00 | 66.47 | O |
| ATOM | 8513 | N   | GLN C | 79 | 24.508 | 47.934 | −10.137 | 1.00 | 67.96 | N |
| ATOM | 8514 | CA  | GLN C | 79 | 25.949 | 48.134 | −10.022 | 1.00 | 67.85 | C |
| ATOM | 8515 | CB  | GLN C | 79 | 26.704 | 47.194 | −10.973 | 1.00 | 69.96 | C |
| ATOM | 8516 | CG  | GLN C | 79 | 26.515 | 45.706 | −10.714 | 1.00 | 69.73 | C |
| ATOM | 8517 | CD  | GLN C | 79 | 26.793 | 45.291 | −9.284  | 1.00 | 65.30 | C |
| ATOM | 8518 | OE1 | GLN C | 79 | 27.566 | 45.924 | −8.567  | 1.00 | 63.82 | O |
| ATOM | 8519 | NE2 | GLN C | 79 | 26.145 | 44.225 | −8.863  | 1.00 | 63.47 | N |
| ATOM | 8520 | C   | GLN C | 79 | 26.352 | 49.554 | −10.341 | 1.00 | 65.61 | C |
| ATOM | 8521 | O   | GLN C | 79 | 25.688 | 50.221 | −11.129 | 1.00 | 59.34 | O |
| ATOM | 8522 | N   | VAL C | 80 | 27.444 | 49.997 | −9.715  | 1.00 | 66.52 | N |
| ATOM | 8523 | CA  | VAL C | 80 | 28.015 | 51.287 | −10.018 | 1.00 | 70.57 | C |
| ATOM | 8524 | CB  | VAL C | 80 | 28.098 | 52.247 | −8.812  | 1.00 | 73.00 | C |
| ATOM | 8525 | CG1 | VAL C | 80 | 28.109 | 53.666 | −9.345  | 1.00 | 72.73 | C |
| ATOM | 8526 | CG2 | VAL C | 80 | 26.930 | 52.058 | −7.846  | 1.00 | 74.19 | C |
| ATOM | 8527 | C   | VAL C | 80 | 29.394 | 51.029 | −10.604 | 1.00 | 72.07 | C |
| ATOM | 8528 | O   | VAL C | 80 | 30.310 | 50.603 | −9.912  | 1.00 | 72.99 | O |
| ATOM | 8529 | N   | ILE C | 81 | 29.494 | 51.311 | −11.899 | 1.00 | 70.25 | N |
| ATOM | 8530 | CA  | ILE C | 81 | 30.612 | 51.006 | −12.728 | 1.00 | 65.68 | C |
| ATOM | 8531 | CB  | ILE C | 81 | 30.168 | 50.071 | −13.859 | 1.00 | 71.76 | C |
| ATOM | 8532 | CG1 | ILE C | 81 | 29.131 | 49.074 | −13.386 | 1.00 | 74.87 | C |
| ATOM | 8533 | CD1 | ILE C | 81 | 28.745 | 48.078 | −14.460 | 1.00 | 77.00 | C |
| ATOM | 8534 | CG2 | ILE C | 81 | 31.345 | 49.295 | −14.406 | 1.00 | 77.31 | C |
| ATOM | 8535 | C   | ILE C | 81 | 31.000 | 52.298 | −13.415 | 1.00 | 61.78 | C |
| ATOM | 8536 | O   | ILE C | 81 | 30.143 | 53.010 | −13.886 | 1.00 | 64.21 | O |
| ATOM | 8537 | N   | PRO C | 82 | 32.287 | 52.581 | −13.555 | 1.00 | 58.71 | N |
| ATOM | 8538 | CA  | PRO C | 82 | 32.711 | 53.746 | −14.342 | 1.00 | 56.56 | C |
| ATOM | 8539 | CB  | PRO C | 82 | 34.202 | 53.835 | −14.033 | 1.00 | 56.25 | C |
| ATOM | 8540 | CG  | PRO C | 82 | 34.586 | 52.442 | −13.740 | 1.00 | 57.24 | C |
| ATOM | 8541 | CD  | PRO C | 82 | 33.436 | 51.843 | −13.013 | 1.00 | 59.02 | C |
| ATOM | 8542 | C   | PRO C | 82 | 32.495 | 53.636 | −15.865 | 1.00 | 54.63 | C |
| ATOM | 8543 | O   | PRO C | 82 | 32.114 | 52.598 | −16.349 | 1.00 | 51.70 | O |
| ATOM | 8544 | N   | VAL C | 83 | 32.739 | 54.714 | −16.604 | 1.00 | 55.40 | N |
| ATOM | 8545 | CA  | VAL C | 83 | 32.429 | 54.747 | −18.027 | 1.00 | 58.94 | C |
| ATOM | 8546 | CB  | VAL C | 83 | 31.163 | 55.569 | −18.318 | 1.00 | 56.73 | C |
| ATOM | 8547 | CG1 | VAL C | 83 | 30.952 | 55.740 | −19.811 | 1.00 | 57.75 | C |
| ATOM | 8548 | CG2 | VAL C | 83 | 29.936 | 54.925 | −17.685 | 1.00 | 54.24 | C |
| ATOM | 8549 | C   | VAL C | 83 | 33.613 | 55.317 | −18.773 | 1.00 | 67.75 | C |
| ATOM | 8550 | O   | VAL C | 83 | 34.135 | 56.359 | −18.380 | 1.00 | 79.00 | O |

TABLE 6-continued

Atomic coordinates for CRBN:DDB1: Compound B (Human protein)

| ATOM | 8551 | N | LEU C | 84 | 34.044 | 54.600 | −19.815 | 1.00 | 73.10 | N |
|---|---|---|---|---|---|---|---|---|---|---|
| ATOM | 8552 | CA | LEU C | 84 | 35.196 | 54.963 | −20.585 | 1.00 | 79.84 | C |
| ATOM | 8553 | CB | LEU C | 84 | 35.449 | 53.975 | −21.700 | 1.00 | 87.72 | C |
| ATOM | 8554 | CG | LEU C | 84 | 36.313 | 52.767 | −21.452 | 1.00 | 93.86 | C |
| ATOM | 8555 | CD1 | LEU C | 84 | 36.458 | 52.068 | −22.804 | 1.00 | 89.42 | C |
| ATOM | 8556 | CD2 | LEU C | 84 | 37.662 | 53.172 | −20.828 | 1.00 | 97.29 | C |
| ATOM | 8557 | C | LEU C | 84 | 34.718 | 56.135 | −21.272 | 1.00 | 88.06 | C |
| ATOM | 8558 | O | LEU C | 84 | 33.778 | 56.010 | −22.035 | 1.00 | 96.02 | O |
| ATOM | 8559 | N | PRO C | 85 | 35.335 | 57.292 | −21.042 | 1.00 | 104.09 | N |
| ATOM | 8560 | CA | PRO C | 85 | 34.862 | 58.401 | −21.890 | 1.00 | 102.74 | C |
| ATOM | 8561 | CB | PRO C | 85 | 35.511 | 59.647 | −21.257 | 1.00 | 108.87 | C |
| ATOM | 8562 | CG | PRO C | 85 | 36.300 | 59.162 | −20.056 | 1.00 | 108.76 | C |
| ATOM | 8563 | CD | PRO C | 85 | 36.489 | 57.674 | −20.205 | 1.00 | 105.90 | C |
| ATOM | 8564 | C | PRO C | 85 | 35.367 | 58.162 | −23.299 | 1.00 | 95.64 | C |
| ATOM | 8565 | O | PRO C | 85 | 36.129 | 57.216 | −23.552 | 1.00 | 93.36 | O |
| ATOM | 8566 | N | GLN C | 86 | 34.954 | 58.979 | −24.235 | 1.00 | 91.24 | N |
| ATOM | 8567 | CA | GLN C | 86 | 35.638 | 58.957 | −25.522 | 1.00 | 92.85 | C |
| ATOM | 8568 | CB | GLN C | 86 | 37.160 | 59.260 | −25.358 | 1.00 | 88.35 | C |
| ATOM | 8569 | CG | GLN C | 86 | 37.583 | 60.661 | −25.805 | 1.00 | 86.57 | C |
| ATOM | 8570 | CD | GLN C | 86 | 39.034 | 60.923 | −25.467 | 1.00 | 88.16 | C |
| ATOM | 8571 | OE1 | GLN C | 86 | 39.361 | 61.843 | −24.726 | 1.00 | 94.96 | O |
| ATOM | 8572 | NE2 | GLN C | 86 | 39.909 | 60.093 | −25.983 | 1.00 | 90.19 | N |
| ATOM | 8573 | C | GLN C | 86 | 35.464 | 57.697 | −26.367 | 1.00 | 90.02 | C |
| ATOM | 8574 | O | GLN C | 86 | 35.932 | 57.705 | −27.501 | 1.00 | 96.04 | O |
| ATOM | 8575 | N | VAL C | 87 | 34.806 | 56.678 | −25.861 | 1.00 | 90.08 | N |
| ATOM | 8576 | CA | VAL C | 87 | 34.638 | 55.518 | −26.690 | 1.00 | 86.02 | C |
| ATOM | 8577 | CB | VAL C | 87 | 35.185 | 54.271 | −26.017 | 1.00 | 88.43 | C |
| ATOM | 8578 | CG1 | VAL C | 87 | 34.887 | 53.045 | −26.852 | 1.00 | 90.62 | C |
| ATOM | 8579 | CG2 | VAL C | 87 | 36.681 | 54.414 | −25.844 | 1.00 | 90.63 | C |
| ATOM | 8580 | C | VAL C | 87 | 33.190 | 55.325 | −26.985 | 1.00 | 82.25 | C |
| ATOM | 8581 | O | VAL C | 87 | 32.379 | 55.271 | −26.091 | 1.00 | 80.67 | O |
| ATOM | 8582 | N | MET C | 88 | 32.875 | 55.214 | −28.259 | 1.00 | 88.70 | N |
| ATOM | 8583 | CA | MET C | 88 | 31.515 | 54.988 | −28.657 | 1.00 | 95.72 | C |
| ATOM | 8584 | CB | MET C | 88 | 31.099 | 56.037 | −29.671 | 1.00 | 101.74 | C |
| ATOM | 8585 | CG | MET C | 88 | 31.656 | 57.403 | −29.388 | 1.00 | 104.84 | C |
| ATOM | 8586 | SD | MET C | 88 | 30.868 | 57.967 | −27.894 | 1.00 | 117.92 | S |
| ATOM | 8587 | CE | MET C | 88 | 32.062 | 59.178 | −27.352 | 1.00 | 119.27 | C |
| ATOM | 8588 | C | MET C | 88 | 31.489 | 53.686 | −29.382 | 1.00 | 86.45 | C |
| ATOM | 8589 | O | MET C | 88 | 32.087 | 53.572 | −30.433 | 1.00 | 91.37 | O |
| ATOM | 8590 | N | MET C | 89 | 30.799 | 52.704 | −28.842 | 1.00 | 75.44 | N |
| ATOM | 8591 | CA | MET C | 89 | 30.678 | 51.452 | −29.540 | 1.00 | 74.44 | C |
| ATOM | 8592 | CB | MET C | 89 | 32.002 | 50.720 | −29.688 | 1.00 | 72.22 | C |
| ATOM | 8593 | CG | MET C | 89 | 32.276 | 49.644 | −28.682 | 1.00 | 76.87 | C |
| ATOM | 8594 | SD | MET C | 89 | 33.584 | 48.591 | −29.286 | 1.00 | 84.72 | S |
| ATOM | 8595 | CE | MET C | 89 | 32.712 | 47.529 | −30.404 | 1.00 | 73.20 | C |
| ATOM | 8596 | C | MET C | 89 | 29.596 | 50.665 | −28.880 | 1.00 | 71.22 | C |
| ATOM | 8597 | O | MET C | 89 | 29.195 | 50.989 | −27.784 | 1.00 | 81.02 | O |
| ATOM | 8598 | N | ILE C | 90 | 29.113 | 49.648 | −29.564 | 1.00 | 63.74 | N |
| ATOM | 8599 | CA | ILE C | 90 | 28.038 | 48.800 | −29.072 | 1.00 | 56.68 | C |
| ATOM | 8600 | CB | ILE C | 90 | 26.852 | 48.654 | −30.060 | 1.00 | 58.23 | C |
| ATOM | 8601 | CG1 | ILE C | 90 | 25.987 | 49.914 | −30.066 | 1.00 | 62.66 | C |
| ATOM | 8602 | CD1 | ILE C | 90 | 26.376 | 50.891 | −31.129 | 1.00 | 68.38 | C |
| ATOM | 8603 | CG2 | ILE C | 90 | 25.935 | 47.519 | −29.661 | 1.00 | 59.23 | C |
| ATOM | 8604 | C | ILE C | 90 | 28.774 | 47.533 | −28.874 | 1.00 | 48.81 | C |
| ATOM | 8605 | O | ILE C | 90 | 29.044 | 46.833 | −29.790 | 1.00 | 45.68 | O |
| ATOM | 8606 | N | LEU C | 91 | 29.110 | 47.269 | −27.637 | 1.00 | 51.23 | N |
| ATOM | 8607 | CA | LEU C | 91 | 29.928 | 46.127 | −27.252 | 1.00 | 51.24 | C |
| ATOM | 8608 | CB | LEU C | 91 | 30.660 | 46.446 | −25.935 | 1.00 | 51.79 | C |
| ATOM | 8609 | CG | LEU C | 91 | 32.021 | 45.914 | −25.510 | 1.00 | 50.66 | C |
| ATOM | 8610 | CD1 | LEU C | 91 | 31.916 | 45.500 | −24.062 | 1.00 | 51.23 | C |
| ATOM | 8611 | CD2 | LEU C | 91 | 32.489 | 44.753 | −26.347 | 1.00 | 51.26 | C |
| ATOM | 8612 | C | LEU C | 91 | 29.009 | 44.946 | −27.048 | 1.00 | 49.80 | C |
| ATOM | 8613 | O | LEU C | 91 | 27.984 | 45.016 | −26.359 | 1.00 | 48.82 | O |
| ATOM | 8614 | N | ILE C | 92 | 29.410 | 43.829 | −27.600 | 1.00 | 49.21 | N |
| ATOM | 8615 | CA | ILE C | 92 | 28.622 | 42.626 | −27.490 | 1.00 | 48.51 | C |
| ATOM | 8616 | CB | ILE C | 92 | 28.598 | 41.921 | −28.838 | 1.00 | 46.59 | C |
| ATOM | 8617 | CG1 | ILE C | 92 | 27.892 | 42.837 | −29.811 | 1.00 | 44.78 | C |
| ATOM | 8618 | CD1 | ILE C | 92 | 27.815 | 42.270 | −31.202 | 1.00 | 47.09 | C |
| ATOM | 8619 | CG2 | ILE C | 92 | 27.925 | 40.565 | −28.732 | 1.00 | 47.09 | C |
| ATOM | 8620 | C | ILE C | 92 | 29.282 | 41.751 | −26.439 | 1.00 | 43.88 | C |
| ATOM | 8621 | O | ILE C | 92 | 30.484 | 41.644 | −26.430 | 1.00 | 44.15 | O |
| ATOM | 8622 | N | PRO C | 93 | 28.505 | 41.096 | −25.578 | 1.00 | 41.35 | N |
| ATOM | 8623 | CA | PRO C | 93 | 29.087 | 40.035 | −24.731 | 1.00 | 38.54 | C |
| ATOM | 8624 | CB | PRO C | 93 | 27.877 | 39.247 | −24.325 | 1.00 | 38.15 | C |
| ATOM | 8625 | CG | PRO C | 93 | 26.797 | 40.280 | −24.195 | 1.00 | 39.44 | C |
| ATOM | 8626 | CD | PRO C | 93 | 27.072 | 41.300 | −25.289 | 1.00 | 41.12 | C |
| ATOM | 8627 | C | PRO C | 93 | 30.077 | 39.144 | −25.472 | 1.00 | 35.93 | C |
| ATOM | 8628 | O | PRO C | 93 | 29.924 | 38.873 | −26.650 | 1.00 | 36.24 | O |

TABLE 6-continued

Atomic coordinates for CRBN:DDB1: Compound B (Human protein)

| ATOM | 8629 | N | GLY C | 94 | 31.155 | 38.798 | −24.814 | 1.00 | 34.84 | N |
|------|------|------|-------|-----|--------|--------|---------|------|--------|---|
| ATOM | 8630 | CA | GLY C | 94 | 32.193 | 38.015 | −25.426 | 1.00 | 36.77 | C |
| ATOM | 8631 | C | GLY C | 94 | 33.194 | 38.753 | −26.290 | 1.00 | 40.04 | C |
| ATOM | 8632 | O | GLY C | 94 | 34.293 | 38.226 | −26.483 | 1.00 | 41.74 | O |
| ATOM | 8633 | N | GLN C | 95 | 32.863 | 39.960 | −26.772 | 1.00 | 42.15 | N |
| ATOM | 8634 | CA | GLN C | 95 | 33.672 | 40.664 | −27.761 | 1.00 | 44.29 | C |
| ATOM | 8635 | CB | GLN C | 95 | 32.892 | 41.829 | −28.398 | 1.00 | 48.46 | C |
| ATOM | 8636 | CG | GLN C | 95 | 33.324 | 42.216 | −29.828 | 1.00 | 52.78 | C |
| ATOM | 8637 | CD | GLN C | 95 | 32.607 | 43.441 | −30.402 | 1.00 | 53.63 | C |
| ATOM | 8638 | OE1 | GLN C | 95 | 33.214 | 44.204 | −31.118 | 1.00 | 66.86 | O |
| ATOM | 8639 | NE2 | GLN C | 95 | 31.344 | 43.629 | −30.100 | 1.00 | 51.26 | N |
| ATOM | 8640 | C | GLN C | 95 | 34.906 | 41.179 | −27.088 | 1.00 | 45.91 | C |
| ATOM | 8641 | O | GLN C | 95 | 34.823 | 41.688 | −25.996 | 1.00 | 48.19 | O |
| ATOM | 8642 | N | THR C | 96 | 36.055 | 40.990 | −27.718 | 1.00 | 49.44 | N |
| ATOM | 8643 | CA | THR C | 96 | 37.330 | 41.463 | −27.216 | 1.00 | 51.99 | C |
| ATOM | 8644 | CB | THR C | 96 | 38.491 | 40.542 | −27.708 | 1.00 | 57.45 | C |
| ATOM | 8645 | OG1 | THR C | 96 | 39.477 | 40.365 | −26.714 | 1.00 | 55.73 | O |
| ATOM | 8646 | CG2 | THR C | 96 | 39.234 | 41.091 | −28.951 | 1.00 | 68.53 | C |
| ATOM | 8647 | C | THR C | 96 | 37.437 | 42.930 | −27.719 | 1.00 | 55.64 | C |
| ATOM | 8648 | O | THR C | 96 | 37.212 | 43.221 | −28.924 | 1.00 | 58.63 | O |
| ATOM | 8649 | N | LEU C | 97 | 37.771 | 43.821 | −26.768 | 1.00 | 57.23 | N |
| ATOM | 8650 | CA | LEU C | 97 | 37.855 | 45.283 | −26.904 | 1.00 | 49.43 | C |
| ATOM | 8651 | CB | LEU C | 97 | 36.794 | 45.923 | −26.043 | 1.00 | 47.66 | C |
| ATOM | 8652 | CG | LEU C | 97 | 36.829 | 47.451 | −25.918 | 1.00 | 48.84 | C |
| ATOM | 8653 | CD1 | LEU C | 97 | 37.174 | 48.137 | −27.226 | 1.00 | 46.65 | C |
| ATOM | 8654 | CD2 | LEU C | 97 | 35.472 | 47.931 | −25.384 | 1.00 | 50.11 | C |
| ATOM | 8655 | C | LEU C | 97 | 39.227 | 45.785 | −26.417 | 1.00 | 48.39 | C |
| ATOM | 8656 | O | LEU C | 97 | 39.465 | 45.903 | −25.205 | 1.00 | 44.01 | O |
| ATOM | 8657 | N | PRO C | 98 | 40.124 | 46.100 | −27.361 | 1.00 | 48.07 | N |
| ATOM | 8658 | CA | PRO C | 98 | 41.434 | 46.657 | −27.076 | 1.00 | 49.84 | C |
| ATOM | 8659 | CB | PRO C | 98 | 42.226 | 46.249 | −28.323 | 1.00 | 47.23 | C |
| ATOM | 8660 | CG | PRO C | 98 | 41.244 | 46.380 | −29.408 | 1.00 | 45.78 | C |
| ATOM | 8661 | CD | PRO C | 98 | 39.888 | 46.075 | −28.815 | 1.00 | 46.55 | C |
| ATOM | 8662 | C | PRO C | 98 | 41.400 | 48.200 | −26.949 | 1.00 | 52.52 | C |
| ATOM | 8663 | O | PRO C | 98 | 40.620 | 48.865 | −27.647 | 1.00 | 45.29 | O |
| ATOM | 8664 | N | LEU C | 99 | 42.227 | 48.759 | −26.058 | 1.00 | 56.62 | N |
| ATOM | 8665 | CA | LEU C | 99 | 42.241 | 50.210 | −25.862 | 1.00 | 56.73 | C |
| ATOM | 8666 | CB | LEU C | 99 | 41.387 | 50.579 | −24.678 | 1.00 | 53.55 | C |
| ATOM | 8667 | CG | LEU C | 99 | 39.968 | 50.088 | −24.755 | 1.00 | 53.60 | C |
| ATOM | 8668 | CD1 | LEU C | 99 | 39.300 | 50.185 | −23.402 | 1.00 | 51.87 | C |
| ATOM | 8669 | CD2 | LEU C | 99 | 39.219 | 50.904 | −25.792 | 1.00 | 54.54 | C |
| ATOM | 8670 | C | LEU C | 99 | 43.609 | 50.812 | −25.651 | 1.00 | 59.42 | C |
| ATOM | 8671 | O | LEU C | 99 | 44.537 | 50.130 | −25.172 | 1.00 | 59.42 | O |
| ATOM | 8672 | N | GLN C | 100 | 43.694 | 52.094 | −26.029 | 1.00 | 57.80 | N |
| ATOM | 8673 | CA | GLN C | 100 | 44.781 | 52.964 | −25.681 | 1.00 | 57.91 | C |
| ATOM | 8674 | CB | GLN C | 100 | 45.610 | 53.303 | −26.891 | 1.00 | 59.36 | C |
| ATOM | 8675 | CG | GLN C | 100 | 46.078 | 52.069 | −27.657 | 1.00 | 63.95 | C |
| ATOM | 8676 | CD | GLN C | 100 | 47.461 | 52.211 | −28.290 | 1.00 | 65.36 | C |
| ATOM | 8677 | OE1 | GLN C | 100 | 48.431 | 52.667 | −27.649 | 1.00 | 70.20 | O |
| ATOM | 8678 | NE2 | GLN C | 100 | 47.557 | 51.819 | −29.556 | 1.00 | 62.81 | N |
| ATOM | 8679 | C | GLN C | 100 | 44.197 | 54.227 | −25.119 | 1.00 | 65.09 | C |
| ATOM | 8680 | O | GLN C | 100 | 43.375 | 54.909 | −25.770 | 1.00 | 70.97 | O |
| ATOM | 8681 | N | LEU C | 101 | 44.633 | 54.532 | −23.900 | 1.00 | 72.86 | N |
| ATOM | 8682 | CA | LEU C | 101 | 44.153 | 55.673 | −23.098 | 1.00 | 75.33 | C |
| ATOM | 8683 | CB | LEU C | 101 | 43.533 | 55.127 | −21.799 | 1.00 | 73.29 | C |
| ATOM | 8684 | CG | LEU C | 101 | 42.295 | 54.278 | −22.080 | 1.00 | 68.74 | C |
| ATOM | 8685 | CD1 | LEU C | 101 | 41.932 | 53.430 | −20.890 | 1.00 | 69.18 | C |
| ATOM | 8686 | CD2 | LEU C | 101 | 41.115 | 55.161 | −22.454 | 1.00 | 68.42 | C |
| ATOM | 8687 | C | LEU C | 101 | 45.269 | 56.691 | −22.780 | 1.00 | 72.12 | C |
| ATOM | 8688 | O | LEU C | 101 | 46.348 | 56.313 | −22.330 | 1.00 | 64.55 | O |
| ATOM | 8689 | N | PHE C | 102 | 45.003 | 57.973 | −23.017 | 1.00 | 76.94 | N |
| ATOM | 8690 | CA | PHE C | 102 | 46.013 | 59.024 | −22.785 | 1.00 | 81.00 | C |
| ATOM | 8691 | CB | PHE C | 102 | 46.298 | 59.751 | −24.089 | 1.00 | 79.51 | C |
| ATOM | 8692 | CG | PHE C | 102 | 46.637 | 58.840 | −25.209 | 1.00 | 76.52 | C |
| ATOM | 8693 | CD1 | PHE C | 102 | 47.948 | 58.438 | −25.421 | 1.00 | 74.63 | C |
| ATOM | 8694 | CE1 | PHE C | 102 | 48.279 | 57.581 | −26.455 | 1.00 | 74.84 | C |
| ATOM | 8695 | CZ | PHE C | 102 | 47.300 | 57.104 | −27.282 | 1.00 | 78.46 | C |
| ATOM | 8696 | CE2 | PHE C | 102 | 45.982 | 57.501 | −27.078 | 1.00 | 83.77 | C |
| ATOM | 8697 | CD2 | PHE C | 102 | 45.652 | 58.364 | −26.040 | 1.00 | 79.36 | C |
| ATOM | 8698 | C | PHE C | 102 | 45.649 | 60.033 | −21.671 | 1.00 | 86.60 | C |
| ATOM | 8699 | O | PHE C | 102 | 46.474 | 60.267 | −20.782 | 1.00 | 81.13 | O |
| ATOM | 8700 | N | HIS C | 103 | 44.435 | 60.609 | −21.704 | 1.00 | 93.19 | N |
| ATOM | 8701 | CA | HIS C | 103 | 44.027 | 61.655 | −20.737 | 1.00 | 101.02 | C |
| ATOM | 8702 | CB | HIS C | 103 | 42.606 | 62.190 | −21.008 | 1.00 | 109.35 | C |
| ATOM | 8703 | CG | HIS C | 103 | 42.485 | 62.902 | −22.326 | 1.00 | 121.76 | C |
| ATOM | 8704 | ND1 | HIS C | 103 | 41.930 | 62.317 | −23.447 | 1.00 | 123.06 | N |
| ATOM | 8705 | CE1 | HIS C | 103 | 41.997 | 63.159 | −24.464 | 1.00 | 121.27 | C |
| ATOM | 8706 | NE2 | HIS C | 103 | 42.576 | 64.269 | −24.045 | 1.00 | 128.57 | N |

TABLE 6-continued

Atomic coordinates for CRBN:DDB1: Compound B (Human protein)

| ATOM | 8707 | CD2 | HIS C | 103 | 42.898 | 64.133 | −22.714 | 1.00 | 129.72 | C |
|---|---|---|---|---|---|---|---|---|---|---|
| ATOM | 8708 | C | HIS C | 103 | 44.132 | 61.086 | −19.336 | 1.00 | 100.09 | C |
| ATOM | 8709 | O | HIS C | 103 | 43.489 | 60.081 | −19.055 | 1.00 | 100.20 | O |
| ATOM | 8710 | N | PRO C | 104 | 44.958 | 61.714 | −18.460 | 1.00 | 98.96 | N |
| ATOM | 8711 | CA | PRO C | 104 | 45.367 | 61.121 | −17.169 | 1.00 | 93.34 | C |
| ATOM | 8712 | CB | PRO C | 104 | 46.308 | 62.164 | −16.597 | 1.00 | 93.23 | C |
| ATOM | 8713 | CG | PRO C | 104 | 45.804 | 63.449 | −17.159 | 1.00 | 95.67 | C |
| ATOM | 8714 | CD | PRO C | 104 | 45.412 | 63.116 | −18.565 | 1.00 | 96.39 | C |
| ATOM | 8715 | C | PRO C | 104 | 44.237 | 60.807 | −16.171 | 1.00 | 91.50 | C |
| ATOM | 8716 | O | PRO C | 104 | 44.461 | 60.054 | −15.236 | 1.00 | 90.25 | O |
| ATOM | 8717 | N | GLN C | 105 | 43.048 | 61.369 | −16.376 | 1.00 | 95.30 | N |
| ATOM | 8718 | CA | GLN C | 105 | 41.824 | 60.908 | −15.688 | 1.00 | 97.73 | C |
| ATOM | 8719 | CB | GLN C | 105 | 40.623 | 61.815 | −16.011 | 1.00 | 104.46 | C |
| ATOM | 8720 | CG | GLN C | 105 | 40.810 | 63.328 | −16.006 | 1.00 | 106.72 | C |
| ATOM | 8721 | CD | GLN C | 105 | 39.971 | 63.941 | −17.117 | 1.00 | 115.97 | C |
| ATOM | 8722 | OE1 | GLN C | 105 | 40.385 | 63.944 | −18.300 | 1.00 | 116.31 | O |
| ATOM | 8723 | NE2 | GLN C | 105 | 38.768 | 64.422 | −16.757 | 1.00 | 118.63 | N |
| ATOM | 8724 | C | GLN C | 105 | 41.444 | 59.449 | −16.107 | 1.00 | 91.15 | C |
| ATOM | 8725 | O | GLN C | 105 | 41.021 | 58.615 | −15.285 | 1.00 | 82.50 | O |
| ATOM | 8726 | N | GLU C | 106 | 41.559 | 59.172 | −17.408 | 1.00 | 87.71 | N |
| ATOM | 8727 | CA | GLU C | 106 | 41.345 | 57.827 | −17.951 | 1.00 | 79.36 | C |
| ATOM | 8728 | CB | GLU C | 106 | 41.399 | 57.822 | −19.480 | 1.00 | 75.26 | C |
| ATOM | 8729 | CG | GLU C | 106 | 40.420 | 58.698 | −20.245 | 1.00 | 71.19 | C |
| ATOM | 8730 | CD | GLU C | 106 | 40.693 | 58.651 | −21.758 | 1.00 | 72.43 | C |
| ATOM | 8731 | OE1 | GLU C | 106 | 41.879 | 58.521 | −22.198 | 1.00 | 65.40 | O |
| ATOM | 8732 | OE2 | GLU C | 106 | 39.712 | 58.737 | −22.530 | 1.00 | 74.16 | O |
| ATOM | 8733 | C | GLU C | 106 | 42.446 | 56.886 | −17.428 | 1.00 | 77.28 | C |
| ATOM | 8734 | O | GLU C | 106 | 42.183 | 55.798 | −16.911 | 1.00 | 80.68 | O |
| ATOM | 8735 | N | VAL C | 107 | 43.684 | 57.326 | −17.547 | 1.00 | 70.42 | N |
| ATOM | 8736 | CA | VAL C | 107 | 44.796 | 56.552 | −17.038 | 1.00 | 72.37 | C |
| ATOM | 8737 | CB | VAL C | 107 | 46.134 | 57.284 | −17.319 | 1.00 | 74.96 | C |
| ATOM | 8738 | CG1 | VAL C | 107 | 47.340 | 56.591 | −16.661 | 1.00 | 75.96 | C |
| ATOM | 8739 | CG2 | VAL C | 107 | 46.338 | 57.446 | −18.820 | 1.00 | 75.74 | C |
| ATOM | 8740 | C | VAL C | 107 | 44.640 | 56.243 | −15.533 | 1.00 | 73.46 | C |
| ATOM | 8741 | O | VAL C | 107 | 45.076 | 55.184 | −15.068 | 1.00 | 70.81 | O |
| ATOM | 8742 | N | SER C | 108 | 44.033 | 57.157 | −14.775 | 1.00 | 75.71 | N |
| ATOM | 8743 | CA | SER C | 108 | 43.815 | 56.923 | −13.349 | 1.00 | 80.21 | C |
| ATOM | 8744 | CB | SER C | 108 | 43.339 | 58.191 | −12.636 | 1.00 | 81.31 | C |
| ATOM | 8745 | OG | SER C | 108 | 44.335 | 59.175 | −12.673 | 1.00 | 79.93 | O |
| ATOM | 8746 | C | SER C | 108 | 42.802 | 55.827 | −13.105 | 1.00 | 83.19 | C |
| ATOM | 8747 | O | SER C | 108 | 43.125 | 54.802 | −12.524 | 1.00 | 88.52 | O |
| ATOM | 8748 | N | MET C | 109 | 41.574 | 56.037 | −13.551 | 1.00 | 82.02 | N |
| ATOM | 8749 | CA | MET C | 109 | 40.511 | 55.145 | −13.144 | 1.00 | 85.87 | C |
| ATOM | 8750 | CB | MET C | 109 | 39.148 | 55.784 | −13.420 | 1.00 | 91.14 | C |
| ATOM | 8751 | CG | MET C | 109 | 38.790 | 55.872 | −14.888 | 1.00 | 94.00 | C |
| ATOM | 8752 | SD | MET C | 109 | 37.654 | 54.537 | −15.281 | 1.00 | 94.36 | S |
| ATOM | 8753 | CE | MET C | 109 | 38.314 | 53.950 | −16.841 | 1.00 | 94.78 | C |
| ATOM | 8754 | C | MET C | 109 | 40.656 | 53.725 | −13.740 | 1.00 | 77.83 | C |
| ATOM | 8755 | O | MET C | 109 | 39.974 | 52.804 | −13.284 | 1.00 | 79.05 | O |
| ATOM | 8756 | N | VAL C | 110 | 41.538 | 53.537 | −14.723 | 1.00 | 67.18 | N |
| ATOM | 8757 | CA | VAL C | 110 | 41.897 | 52.184 | −15.143 | 1.00 | 66.91 | C |
| ATOM | 8758 | CB | VAL C | 110 | 42.539 | 52.129 | −16.548 | 1.00 | 62.80 | C |
| ATOM | 8759 | CG1 | VAL C | 110 | 43.044 | 50.731 | −16.884 | 1.00 | 60.13 | C |
| ATOM | 8760 | CG2 | VAL C | 110 | 41.498 | 52.487 | −17.563 | 1.00 | 63.27 | C |
| ATOM | 8761 | C | VAL C | 110 | 42.813 | 51.592 | −14.093 | 1.00 | 67.12 | C |
| ATOM | 8762 | O | VAL C | 110 | 42.506 | 50.563 | −13.497 | 1.00 | 69.70 | O |
| ATOM | 8763 | N | ARG C | 111 | 43.928 | 52.267 | −13.869 | 1.00 | 69.84 | N |
| ATOM | 8764 | CA | ARG C | 111 | 44.844 | 51.984 | −12.751 | 1.00 | 68.08 | C |
| ATOM | 8765 | CB | ARG C | 111 | 45.799 | 53.192 | −12.560 | 1.00 | 72.31 | C |
| ATOM | 8766 | CG | ARG C | 111 | 47.103 | 52.930 | −11.819 | 1.00 | 80.66 | C |
| ATOM | 8767 | CD | ARG C | 111 | 48.191 | 53.949 | −12.207 | 1.00 | 82.86 | C |
| ATOM | 8768 | NE | ARG C | 111 | 48.861 | 53.572 | −13.458 | 1.00 | 84.22 | N |
| ATOM | 8769 | CZ | ARG C | 111 | 49.741 | 54.314 | −14.122 | 1.00 | 79.47 | C |
| ATOM | 8770 | NH1 | ARG C | 111 | 50.065 | 55.525 | −13.689 | 1.00 | 72.93 | N |
| ATOM | 8771 | NH2 | ARG C | 111 | 50.283 | 53.833 | −15.248 | 1.00 | 84.80 | N |
| ATOM | 8772 | C | ARG C | 111 | 44.050 | 51.607 | −11.466 | 1.00 | 60.60 | C |
| ATOM | 8773 | O | ARG C | 111 | 44.395 | 50.594 | −10.806 | 1.00 | 52.87 | O |
| ATOM | 8774 | N | ASN C | 112 | 42.967 | 52.371 | −11.181 | 1.00 | 56.14 | N |
| ATOM | 8775 | CA | ASN C | 112 | 42.084 | 52.107 | −10.052 | 1.00 | 55.28 | C |
| ATOM | 8776 | CB | ASN C | 112 | 41.019 | 53.177 | −9.838 | 1.00 | 56.03 | C |
| ATOM | 8777 | CG | ASN C | 112 | 40.258 | 52.970 | −8.503 | 1.00 | 59.66 | C |
| ATOM | 8778 | OD1 | ASN C | 112 | 40.805 | 53.239 | −7.441 | 1.00 | 65.90 | O |
| ATOM | 8779 | ND2 | ASN C | 112 | 39.017 | 52.467 | −8.554 | 1.00 | 58.09 | N |
| ATOM | 8780 | C | ASN C | 112 | 41.353 | 50.813 | −10.223 | 1.00 | 59.19 | C |
| ATOM | 8781 | O | ASN C | 112 | 41.291 | 50.002 | −9.308 | 1.00 | 62.35 | O |
| ATOM | 8782 | N | LEU C | 113 | 40.740 | 50.652 | −11.388 | 1.00 | 63.01 | N |
| ATOM | 8783 | CA | LEU C | 113 | 39.932 | 49.473 | −11.688 | 1.00 | 59.91 | C |
| ATOM | 8784 | CB | LEU C | 113 | 39.360 | 49.550 | −13.098 | 1.00 | 63.19 | C |

TABLE 6-continued

Atomic coordinates for CRBN:DDB1: Compound B (Human protein)

| ATOM | 8785 | CG | LEU C | 113 | 37.844 | 49.651 | −13.235 | 1.00 | 63.66 | C |
|---|---|---|---|---|---|---|---|---|---|---|
| ATOM | 8786 | CD1 | LEU C | 113 | 37.113 | 50.279 | −12.027 | 1.00 | 64.23 | C |
| ATOM | 8787 | CD2 | LEU C | 113 | 37.576 | 50.319 | −14.585 | 1.00 | 57.39 | C |
| ATOM | 8788 | C | LEU C | 113 | 40.707 | 48.209 | −11.545 | 1.00 | 58.61 | C |
| ATOM | 8789 | O | LEU C | 113 | 40.184 | 47.278 | −10.982 | 1.00 | 61.35 | O |
| ATOM | 8790 | N | ILE C | 114 | 41.949 | 48.214 | −11.959 | 1.00 | 57.42 | N |
| ATOM | 8791 | CA | ILE C | 114 | 42.744 | 47.029 | −11.874 | 1.00 | 60.47 | C |
| ATOM | 8792 | CB | ILE C | 114 | 44.170 | 47.346 | −12.244 | 1.00 | 65.98 | C |
| ATOM | 8793 | CG1 | ILE C | 114 | 44.202 | 48.122 | −13.540 | 1.00 | 69.16 | C |
| ATOM | 8794 | CD1 | ILE C | 114 | 44.006 | 47.271 | −14.757 | 1.00 | 72.50 | C |
| ATOM | 8795 | CG2 | ILE C | 114 | 44.968 | 46.073 | −12.357 | 1.00 | 67.53 | C |
| ATOM | 8796 | C | ILE C | 114 | 42.771 | 46.595 | −10.447 | 1.00 | 63.85 | C |
| ATOM | 8797 | O | ILE C | 114 | 42.743 | 45.422 | −10.153 | 1.00 | 61.10 | O |
| ATOM | 8798 | N | GLN C | 115 | 42.844 | 47.555 | −9.552 | 1.00 | 68.20 | N |
| ATOM | 8799 | CA | GLN C | 115 | 42.858 | 47.248 | −8.147 | 1.00 | 66.00 | C |
| ATOM | 8800 | CB | GLN C | 115 | 43.074 | 48.506 | −7.342 | 1.00 | 71.71 | C |
| ATOM | 8801 | CG | GLN C | 115 | 44.418 | 49.145 | −7.565 | 1.00 | 73.42 | C |
| ATOM | 8802 | CD | GLN C | 115 | 45.516 | 48.136 | −7.650 | 1.00 | 73.16 | C |
| ATOM | 8803 | OE1 | GLN C | 115 | 45.762 | 47.576 | −8.701 | 1.00 | 68.71 | O |
| ATOM | 8804 | NE2 | GLN C | 115 | 46.172 | 47.887 | −6.540 | 1.00 | 75.49 | N |
| ATOM | 8805 | C | GLN C | 115 | 41.578 | 46.597 | −7.713 | 1.00 | 70.81 | C |
| ATOM | 8806 | O | GLN C | 115 | 41.590 | 45.713 | −6.881 | 1.00 | 61.77 | O |
| ATOM | 8807 | N | LYS C | 116 | 40.462 | 47.057 | −8.246 | 1.00 | 84.66 | N |
| ATOM | 8808 | CA | LYS C | 116 | 39.194 | 46.487 | −7.853 | 1.00 | 86.87 | C |
| ATOM | 8809 | CB | LYS C | 116 | 38.514 | 47.498 | −6.936 | 1.00 | 84.54 | C |
| ATOM | 8810 | C | LYS C | 116 | 38.216 | 46.118 | −8.958 | 1.00 | 80.07 | C |
| ATOM | 8811 | O | LYS C | 116 | 37.894 | 46.947 | −9.777 | 1.00 | 94.73 | O |
| ATOM | 8812 | N | ASP C | 117 | 37.710 | 44.896 | −8.982 | 1.00 | 66.54 | N |
| ATOM | 8813 | CA | ASP C | 117 | 36.682 | 44.540 | −9.965 | 1.00 | 65.77 | C |
| ATOM | 8814 | CB | ASP C | 117 | 35.420 | 45.341 | −9.722 | 1.00 | 71.42 | C |
| ATOM | 8815 | CG | ASP C | 117 | 34.748 | 44.964 | −8.414 | 1.00 | 74.10 | C |
| ATOM | 8816 | OD1 | ASP C | 117 | 35.316 | 44.151 | −7.666 | 1.00 | 70.16 | O |
| ATOM | 8817 | OD2 | ASP C | 117 | 33.653 | 45.479 | −8.127 | 1.00 | 76.74 | O |
| ATOM | 8818 | C | ASP C | 117 | 37.079 | 44.442 | −11.436 | 1.00 | 60.14 | C |
| ATOM | 8819 | O | ASP C | 117 | 36.860 | 43.429 | −12.047 | 1.00 | 53.50 | O |
| ATOM | 8820 | N | ARG C | 118 | 37.639 | 45.481 | −12.020 | 1.00 | 57.96 | N |
| ATOM | 8821 | CA | ARG C | 118 | 38.129 | 45.348 | −13.374 | 1.00 | 56.80 | C |
| ATOM | 8822 | CB | ARG C | 118 | 38.939 | 44.064 | −13.548 | 1.00 | 59.80 | C |
| ATOM | 8823 | CG | ARG C | 118 | 40.313 | 44.055 | −12.849 | 1.00 | 63.98 | C |
| ATOM | 8824 | CD | ARG C | 118 | 41.261 | 42.920 | −13.285 | 1.00 | 64.54 | C |
| ATOM | 8825 | NE | ARG C | 118 | 40.450 | 41.744 | −13.577 | 1.00 | 65.34 | N |
| ATOM | 8826 | CZ | ARG C | 118 | 39.896 | 40.957 | −12.675 | 1.00 | 64.51 | C |
| ATOM | 8827 | NH1 | ARG C | 118 | 40.162 | 41.138 | −11.387 | 1.00 | 66.68 | N |
| ATOM | 8828 | NH2 | ARG C | 118 | 39.100 | 39.957 | −13.075 | 1.00 | 68.09 | N |
| ATOM | 8829 | C | ARG C | 118 | 37.071 | 45.566 | −14.499 | 1.00 | 58.53 | C |
| ATOM | 8830 | O | ARG C | 118 | 37.455 | 45.816 | −15.638 | 1.00 | 58.86 | O |
| ATOM | 8831 | N | THR C | 119 | 35.775 | 45.524 | −14.190 | 1.00 | 57.64 | N |
| ATOM | 8832 | CA | THR C | 119 | 34.723 | 45.873 | −15.153 | 1.00 | 61.67 | C |
| ATOM | 8833 | CB | THR C | 119 | 33.411 | 45.191 | −14.752 | 1.00 | 68.60 | C |
| ATOM | 8834 | OG1 | THR C | 119 | 33.174 | 45.526 | −13.379 | 1.00 | 85.66 | O |
| ATOM | 8835 | CG2 | THR C | 119 | 33.480 | 43.601 | −14.921 | 1.00 | 66.58 | C |
| ATOM | 8836 | C | THR C | 119 | 34.441 | 47.392 | −15.328 | 1.00 | 56.20 | C |
| ATOM | 8837 | O | THR C | 119 | 34.659 | 48.189 | −14.464 | 1.00 | 57.06 | O |
| ATOM | 8838 | N | PHE C | 120 | 33.956 | 47.761 | −16.489 | 1.00 | 56.80 | N |
| ATOM | 8839 | CA | PHE C | 120 | 33.539 | 49.110 | −16.792 | 1.00 | 56.08 | C |
| ATOM | 8840 | CB | PHE C | 120 | 34.691 | 49.986 | −17.293 | 1.00 | 56.91 | C |
| ATOM | 8841 | CG | PHE C | 120 | 35.332 | 49.521 | −18.555 | 1.00 | 60.93 | C |
| ATOM | 8842 | CD1 | PHE C | 120 | 34.807 | 49.871 | −19.795 | 1.00 | 66.54 | C |
| ATOM | 8843 | CE1 | PHE C | 120 | 35.425 | 49.439 | −20.973 | 1.00 | 66.64 | C |
| ATOM | 8844 | CZ | PHE C | 120 | 36.591 | 48.676 | −20.913 | 1.00 | 64.04 | C |
| ATOM | 8845 | CE2 | PHE C | 120 | 37.133 | 48.351 | −19.686 | 1.00 | 62.34 | C |
| ATOM | 8846 | CD2 | PHE C | 120 | 36.507 | 48.778 | −18.521 | 1.00 | 64.24 | C |
| ATOM | 8847 | C | PHE C | 120 | 32.360 | 49.073 | −17.766 | 1.00 | 56.75 | C |
| ATOM | 8848 | O | PHE C | 120 | 31.965 | 48.010 | −18.258 | 1.00 | 57.69 | O |
| ATOM | 8849 | N | ALA C | 121 | 31.787 | 50.235 | −18.030 | 1.00 | 56.48 | N |
| ATOM | 8850 | CA | ALA C | 121 | 30.583 | 50.313 | −18.809 | 1.00 | 56.14 | C |
| ATOM | 8851 | CB | ALA C | 121 | 29.492 | 51.017 | −18.029 | 1.00 | 55.99 | C |
| ATOM | 8852 | C | ALA C | 121 | 30.848 | 50.976 | −20.154 | 1.00 | 55.81 | C |
| ATOM | 8853 | O | ALA C | 121 | 31.551 | 51.974 | −20.272 | 1.00 | 53.32 | O |
| ATOM | 8854 | N | VAL C | 122 | 30.287 | 50.350 | −21.176 | 1.00 | 56.67 | N |
| ATOM | 8855 | CA | VAL C | 122 | 30.471 | 50.754 | −22.524 | 1.00 | 54.96 | C |
| ATOM | 8856 | CB | VAL C | 122 | 31.071 | 49.617 | −23.326 | 1.00 | 51.63 | C |
| ATOM | 8857 | CG1 | VAL C | 122 | 31.039 | 49.968 | −24.794 | 1.00 | 52.18 | C |
| ATOM | 8858 | CG2 | VAL C | 122 | 32.476 | 49.270 | −22.842 | 1.00 | 49.49 | C |
| ATOM | 8859 | C | VAL C | 122 | 29.068 | 51.028 | −22.990 | 1.00 | 59.96 | C |
| ATOM | 8860 | O | VAL C | 122 | 28.299 | 50.107 | −23.231 | 1.00 | 54.94 | O |
| ATOM | 8861 | N | LEU C | 123 | 28.742 | 52.312 | −23.102 | 1.00 | 70.33 | N |
| ATOM | 8862 | CA | LEU C | 123 | 27.368 | 52.733 | −23.346 | 1.00 | 71.60 | C |

TABLE 6-continued

Atomic coordinates for CRBN:DDB1: Compound B (Human protein)

| ATOM | 8863 | CB | LEU C | 123 | 27.133 | 54.127 | −22.763 | 1.00 | 71.76 | C |
|---|---|---|---|---|---|---|---|---|---|---|
| ATOM | 8864 | CG | LEU C | 123 | 27.347 | 54.171 | −21.243 | 1.00 | 74.66 | C |
| ATOM | 8865 | CD1 | LEU C | 123 | 27.158 | 55.573 | −20.679 | 1.00 | 75.65 | C |
| ATOM | 8866 | CD2 | LEU C | 123 | 26.428 | 53.196 | −20.498 | 1.00 | 73.40 | C |
| ATOM | 8867 | C | LEU C | 123 | 27.080 | 52.709 | −24.822 | 1.00 | 73.31 | C |
| ATOM | 8868 | O | LEU C | 123 | 27.943 | 53.094 | −25.610 | 1.00 | 67.70 | O |
| ATOM | 8869 | N | ALA C | 124 | 25.876 | 52.226 | −25.158 | 1.00 | 81.79 | N |
| ATOM | 8870 | CA | ALA C | 124 | 25.333 | 52.154 | −26.526 | 1.00 | 89.93 | C |
| ATOM | 8871 | CB | ALA C | 124 | 24.566 | 50.852 | −26.757 | 1.00 | 86.74 | C |
| ATOM | 8872 | C | ALA C | 124 | 24.390 | 53.315 | −26.657 | 1.00 | 99.46 | C |
| ATOM | 8873 | O | ALA C | 124 | 23.439 | 53.420 | −25.886 | 1.00 | 95.83 | O |
| ATOM | 8874 | N | TYR C | 125 | 24.619 | 54.164 | −27.657 | 1.00 | 114.66 | N |
| ATOM | 8875 | CA | TYR C | 125 | 24.128 | 55.547 | −27.606 | 1.00 | 119.11 | C |
| ATOM | 8876 | CB | TYR C | 125 | 25.216 | 56.469 | −28.152 | 1.00 | 115.61 | C |
| ATOM | 8877 | CG | TYR C | 125 | 26.319 | 56.721 | −27.134 | 1.00 | 114.02 | C |
| ATOM | 8878 | CD1 | TYR C | 125 | 26.046 | 57.404 | −25.936 | 1.00 | 111.48 | C |
| ATOM | 8879 | CE1 | TYR C | 125 | 27.047 | 57.655 | −24.989 | 1.00 | 106.86 | C |
| ATOM | 8880 | CZ | TYR C | 125 | 28.349 | 57.230 | −25.230 | 1.00 | 106.36 | C |
| ATOM | 8881 | OH | TYR C | 125 | 29.325 | 57.475 | −24.292 | 1.00 | 89.59 | O |
| ATOM | 8882 | CE2 | TYR C | 125 | 28.648 | 56.548 | −26.410 | 1.00 | 114.61 | C |
| ATOM | 8883 | CD2 | TYR C | 125 | 27.636 | 56.294 | −27.356 | 1.00 | 117.25 | C |
| ATOM | 8884 | C | TYR C | 125 | 22.746 | 55.856 | −28.220 | 1.00 | 127.46 | C |
| ATOM | 8885 | O | TYR C | 125 | 22.286 | 55.149 | −29.126 | 1.00 | 126.34 | O |
| ATOM | 8886 | N | SER C | 126 | 22.134 | 56.935 | −27.688 | 1.00 | 135.63 | N |
| ATOM | 8887 | CA | SER C | 126 | 20.735 | 57.397 | −27.933 | 1.00 | 135.87 | C |
| ATOM | 8888 | CB | SER C | 126 | 20.707 | 58.948 | −27.977 | 1.00 | 124.42 | C |
| ATOM | 8889 | C | SER C | 126 | 19.984 | 56.814 | −29.153 | 1.00 | 130.79 | C |
| ATOM | 8890 | O | SER C | 126 | 20.331 | 57.078 | −30.312 | 1.00 | 126.37 | O |
| ATOM | 8891 | N | GLU C | 132 | 23.569 | 61.132 | −22.953 | 1.00 | 127.81 | N |
| ATOM | 8892 | CA | GLU C | 132 | 23.277 | 59.920 | −22.197 | 1.00 | 125.87 | C |
| ATOM | 8893 | CB | GLU C | 132 | 22.448 | 60.250 | −20.941 | 1.00 | 111.40 | C |
| ATOM | 8894 | C | GLU C | 132 | 22.580 | 58.859 | −23.095 | 1.00 | 138.28 | C |
| ATOM | 8895 | O | GLU C | 132 | 22.299 | 59.111 | −24.299 | 1.00 | 134.18 | O |
| ATOM | 8896 | N | ALA C | 133 | 22.359 | 57.669 | −22.508 | 1.00 | 140.67 | N |
| ATOM | 8897 | CA | ALA C | 133 | 21.732 | 56.505 | −23.188 | 1.00 | 127.06 | C |
| ATOM | 8898 | CB | ALA C | 133 | 22.730 | 55.791 | −24.088 | 1.00 | 125.01 | C |
| ATOM | 8899 | C | ALA C | 133 | 21.135 | 55.528 | −22.173 | 1.00 | 113.54 | C |
| ATOM | 8900 | O | ALA C | 133 | 21.267 | 55.730 | −20.964 | 1.00 | 105.95 | O |
| ATOM | 8901 | N | GLN C | 134 | 20.495 | 54.475 | −22.675 | 1.00 | 104.75 | N |
| ATOM | 8902 | CA | GLN C | 134 | 19.594 | 53.653 | −21.859 | 1.00 | 106.65 | C |
| ATOM | 8903 | CB | GLN C | 134 | 18.156 | 53.660 | −22.433 | 1.00 | 114.91 | C |
| ATOM | 8904 | CG | GLN C | 134 | 17.739 | 54.894 | −23.257 | 1.00 | 121.57 | C |
| ATOM | 8905 | CD | GLN C | 134 | 18.255 | 54.889 | −24.712 | 1.00 | 130.61 | C |
| ATOM | 8906 | OE1 | GLN C | 134 | 18.452 | 53.831 | −25.320 | 1.00 | 137.07 | O |
| ATOM | 8907 | NE2 | GLN C | 134 | 18.485 | 56.078 | −25.266 | 1.00 | 130.54 | N |
| ATOM | 8908 | C | GLN C | 134 | 20.083 | 52.210 | −21.681 | 1.00 | 100.53 | C |
| ATOM | 8909 | O | GLN C | 134 | 19.774 | 51.601 | −20.640 | 1.00 | 93.20 | O |
| ATOM | 8910 | N | PHE C | 135 | 20.821 | 51.677 | −22.676 | 1.00 | 92.43 | N |
| ATOM | 8911 | CA | PHE C | 135 | 21.357 | 50.291 | −22.672 | 1.00 | 88.03 | C |
| ATOM | 8912 | CB | PHE C | 135 | 20.616 | 49.424 | −23.698 | 1.00 | 91.59 | C |
| ATOM | 8913 | CG | PHE C | 135 | 19.154 | 49.294 | −23.404 | 1.00 | 105.54 | C |
| ATOM | 8914 | CD1 | PHE C | 135 | 18.721 | 48.574 | −22.288 | 1.00 | 108.02 | C |
| ATOM | 8915 | CE1 | PHE C | 135 | 17.369 | 48.475 | −21.983 | 1.00 | 110.27 | C |
| ATOM | 8916 | CZ | PHE C | 135 | 16.427 | 49.107 | −22.790 | 1.00 | 115.33 | C |
| ATOM | 8917 | CE2 | PHE C | 135 | 16.841 | 49.840 | −23.896 | 1.00 | 114.60 | C |
| ATOM | 8918 | CD2 | PHE C | 135 | 18.199 | 49.940 | −24.197 | 1.00 | 113.35 | C |
| ATOM | 8919 | C | PHE C | 135 | 22.861 | 50.213 | −22.937 | 1.00 | 80.98 | C |
| ATOM | 8920 | O | PHE C | 135 | 23.417 | 51.020 | −23.654 | 1.00 | 83.24 | O |
| ATOM | 8921 | N | GLY C | 136 | 23.532 | 49.237 | −22.346 | 1.00 | 75.98 | N |
| ATOM | 8922 | CA | GLY C | 136 | 24.946 | 49.036 | −22.627 | 1.00 | 68.27 | C |
| ATOM | 8923 | C | GLY C | 136 | 25.390 | 47.684 | −22.153 | 1.00 | 64.41 | C |
| ATOM | 8924 | O | GLY C | 136 | 24.556 | 46.884 | −21.709 | 1.00 | 69.67 | O |
| ATOM | 8925 | N | THR C | 137 | 26.699 | 47.445 | −22.232 | 1.00 | 56.65 | N |
| ATOM | 8926 | CA | THR C | 137 | 27.290 | 46.158 | −21.928 | 1.00 | 52.73 | C |
| ATOM | 8927 | CB | THR C | 137 | 27.684 | 45.442 | −23.230 | 1.00 | 52.24 | C |
| ATOM | 8928 | OG1 | THR C | 137 | 26.499 | 45.126 | −23.971 | 1.00 | 51.42 | O |
| ATOM | 8929 | CG2 | THR C | 137 | 28.419 | 44.140 | −22.962 | 1.00 | 52.83 | C |
| ATOM | 8930 | C | THR C | 137 | 28.515 | 46.365 | −21.078 | 1.00 | 51.53 | C |
| ATOM | 8931 | O | THR C | 137 | 29.267 | 47.293 | −21.361 | 1.00 | 49.57 | O |
| ATOM | 8932 | N | THR C | 138 | 28.721 | 45.506 | −20.066 | 1.00 | 51.08 | N |
| ATOM | 8933 | CA | THR C | 138 | 29.945 | 45.557 | −19.237 | 1.00 | 50.51 | C |
| ATOM | 8934 | CB | THR C | 138 | 29.862 | 44.761 | −17.929 | 1.00 | 51.67 | C |
| ATOM | 8935 | OG1 | THR C | 138 | 29.825 | 43.346 | −18.193 | 1.00 | 53.04 | O |
| ATOM | 8936 | CG2 | THR C | 138 | 28.661 | 45.188 | −17.128 | 1.00 | 52.63 | C |
| ATOM | 8937 | C | THR C | 138 | 31.179 | 45.038 | −19.946 | 1.00 | 51.19 | C |
| ATOM | 8938 | O | THR C | 138 | 31.109 | 44.163 | −20.787 | 1.00 | 49.29 | O |
| ATOM | 8939 | N | ALA C | 139 | 32.331 | 45.561 | −19.581 | 1.00 | 52.10 | N |
| ATOM | 8940 | CA | ALA C | 139 | 33.570 | 45.036 | −20.132 | 1.00 | 54.12 | C |

TABLE 6-continued

Atomic coordinates for CRBN:DDB1: Compound B (Human protein)

| ATOM | 8941 | CB | ALA C | 139 | 34.138 | 45.992 | −21.172 | 1.00 | 53.88 | C |
|---|---|---|---|---|---|---|---|---|---|---|
| ATOM | 8942 | C | ALA C | 139 | 34.569 | 44.819 | −19.010 | 1.00 | 54.11 | C |
| ATOM | 8943 | O | ALA C | 139 | 34.867 | 45.743 | −18.304 | 1.00 | 54.10 | O |
| ATOM | 8944 | N | GLU C | 140 | 35.103 | 43.609 | −18.887 | 1.00 | 54.57 | N |
| ATOM | 8945 | CA | GLU C | 140 | 36.150 | 43.302 | −17.936 | 1.00 | 55.37 | C |
| ATOM | 8946 | CB | GLU C | 140 | 35.928 | 41.909 | −17.379 | 1.00 | 62.00 | C |
| ATOM | 8947 | CG | GLU C | 140 | 36.715 | 41.597 | −16.135 | 1.00 | 66.51 | C |
| ATOM | 8948 | CD | GLU C | 140 | 36.571 | 40.150 | −15.702 | 1.00 | 71.67 | C |
| ATOM | 8949 | OE1 | GLU C | 140 | 35.433 | 39.625 | −15.696 | 1.00 | 68.63 | O |
| ATOM | 8950 | OE2 | GLU C | 140 | 37.610 | 39.541 | −15.351 | 1.00 | 86.32 | O |
| ATOM | 8951 | C | GLU C | 140 | 37.525 | 43.387 | −18.587 | 1.00 | 52.66 | C |
| ATOM | 8952 | O | GLU C | 140 | 37.728 | 42.943 | −19.705 | 1.00 | 46.81 | O |
| ATOM | 8953 | N | ILE C | 141 | 38.455 | 43.964 | −17.839 | 1.00 | 54.60 | N |
| ATOM | 8954 | CA | ILE C | 141 | 39.841 | 44.076 | −18.235 | 1.00 | 55.91 | C |
| ATOM | 8955 | CB | ILE C | 141 | 40.567 | 45.188 | −17.474 | 1.00 | 56.05 | C |
| ATOM | 8956 | CG1 | ILE C | 141 | 39.959 | 46.522 | −17.866 | 1.00 | 56.86 | C |
| ATOM | 8957 | CD1 | ILE C | 141 | 40.333 | 47.653 | −16.955 | 1.00 | 59.81 | C |
| ATOM | 8958 | CG2 | ILE C | 141 | 42.044 | 45.216 | −17.852 | 1.00 | 57.38 | C |
| ATOM | 8959 | C | ILE C | 141 | 40.526 | 42.779 | −17.930 | 1.00 | 55.65 | C |
| ATOM | 8960 | O | ILE C | 141 | 40.474 | 42.308 | −16.797 | 1.00 | 53.39 | O |
| ATOM | 8961 | N | TYR C | 142 | 41.152 | 42.193 | −18.943 | 1.00 | 55.99 | N |
| ATOM | 8962 | CA | TYR C | 142 | 41.907 | 40.944 | −18.733 | 1.00 | 56.17 | C |
| ATOM | 8963 | CB | TYR C | 142 | 41.313 | 39.743 | −19.515 | 1.00 | 51.59 | C |
| ATOM | 8964 | CG | TYR C | 142 | 41.502 | 39.783 | −21.037 | 1.00 | 48.06 | C |
| ATOM | 8965 | CD1 | TYR C | 142 | 42.703 | 39.407 | −21.618 | 1.00 | 44.97 | C |
| ATOM | 8966 | CE1 | TYR C | 142 | 42.899 | 39.478 | −22.976 | 1.00 | 44.13 | C |
| ATOM | 8967 | CZ | TYR C | 142 | 41.877 | 39.891 | −23.803 | 1.00 | 44.01 | C |
| ATOM | 8968 | OH | TYR C | 142 | 42.098 | 39.899 | −25.143 | 1.00 | 41.70 | O |
| ATOM | 8969 | CE2 | TYR C | 142 | 40.657 | 40.261 | −23.278 | 1.00 | 46.78 | C |
| ATOM | 8970 | CD2 | TYR C | 142 | 40.471 | 40.214 | −21.892 | 1.00 | 48.61 | C |
| ATOM | 8971 | C | TYR C | 142 | 43.376 | 41.107 | −19.037 | 1.00 | 56.57 | C |
| ATOM | 8972 | O | TYR C | 142 | 44.091 | 40.161 | −18.838 | 1.00 | 57.96 | O |
| ATOM | 8973 | N | ALA C | 143 | 43.827 | 42.271 | −19.516 | 1.00 | 57.50 | N |
| ATOM | 8974 | CA | ALA C | 143 | 45.276 | 42.524 | −19.651 | 1.00 | 61.88 | C |
| ATOM | 8975 | CB | ALA C | 143 | 45.779 | 41.878 | −20.926 | 1.00 | 61.36 | C |
| ATOM | 8976 | C | ALA C | 143 | 45.692 | 44.040 | −19.545 | 1.00 | 65.23 | C |
| ATOM | 8977 | O | ALA C | 143 | 45.049 | 44.903 | −20.115 | 1.00 | 66.06 | O |
| ATOM | 8978 | N | TYR C | 144 | 46.736 | 44.354 | −18.784 | 1.00 | 70.28 | N |
| ATOM | 8979 | CA | TYR C | 144 | 47.058 | 45.751 | −18.449 | 1.00 | 78.93 | C |
| ATOM | 8980 | CB | TYR C | 144 | 46.916 | 46.020 | −16.928 | 1.00 | 89.92 | C |
| ATOM | 8981 | CG | TYR C | 144 | 47.613 | 47.305 | −16.411 | 1.00 | 105.21 | C |
| ATOM | 8982 | CD1 | TYR C | 144 | 47.220 | 48.585 | −16.863 | 1.00 | 110.88 | C |
| ATOM | 8983 | CE1 | TYR C | 144 | 47.854 | 49.754 | −16.407 | 1.00 | 111.98 | C |
| ATOM | 8984 | CZ | TYR C | 144 | 48.901 | 49.668 | −15.486 | 1.00 | 112.15 | C |
| ATOM | 8985 | OH | TYR C | 144 | 49.522 | 50.826 | −15.054 | 1.00 | 104.71 | O |
| ATOM | 8986 | CE2 | TYR C | 144 | 49.311 | 48.415 | −15.020 | 1.00 | 113.02 | C |
| ATOM | 8987 | CD2 | TYR C | 144 | 48.669 | 47.245 | −15.475 | 1.00 | 110.93 | C |
| ATOM | 8988 | C | TYR C | 144 | 48.472 | 45.991 | −18.893 | 1.00 | 77.08 | C |
| ATOM | 8989 | O | TYR C | 144 | 49.285 | 45.065 | −18.840 | 1.00 | 74.18 | O |
| ATOM | 8990 | N | ARG C | 145 | 48.756 | 47.227 | −19.316 | 1.00 | 76.77 | N |
| ATOM | 8991 | CA | ARG C | 145 | 50.093 | 47.652 | −19.748 | 1.00 | 83.67 | C |
| ATOM | 8992 | CB | ARG C | 145 | 50.282 | 47.393 | −21.252 | 1.00 | 93.21 | C |
| ATOM | 8993 | CG | ARG C | 145 | 51.524 | 46.626 | −21.635 | 1.00 | 99.74 | C |
| ATOM | 8994 | CD | ARG C | 145 | 52.791 | 47.387 | −21.310 | 1.00 | 107.37 | C |
| ATOM | 8995 | NE | ARG C | 145 | 53.367 | 48.085 | −22.461 | 1.00 | 110.28 | N |
| ATOM | 8996 | CZ | ARG C | 145 | 53.985 | 47.498 | −23.485 | 1.00 | 104.41 | C |
| ATOM | 8997 | NH1 | ARG C | 145 | 54.500 | 48.268 | −24.428 | 1.00 | 104.57 | N |
| ATOM | 8998 | NH2 | ARG C | 145 | 54.083 | 46.161 | −23.582 | 1.00 | 102.27 | N |
| ATOM | 8999 | C | ARG C | 145 | 50.254 | 49.144 | −19.489 | 1.00 | 88.06 | C |
| ATOM | 9000 | O | ARG C | 145 | 49.584 | 49.957 | −20.141 | 1.00 | 89.69 | O |
| ATOM | 9001 | N | GLU C | 146 | 51.107 | 49.502 | −18.520 | 1.00 | 96.33 | N |
| ATOM | 9002 | CA | GLU C | 146 | 51.553 | 50.895 | −18.312 | 1.00 | 89.58 | C |
| ATOM | 9003 | CB | GLU C | 146 | 51.891 | 51.184 | −16.828 | 1.00 | 79.82 | C |
| ATOM | 9004 | C | GLU C | 146 | 52.751 | 51.080 | −19.252 | 1.00 | 85.81 | C |
| ATOM | 9005 | O | GLU C | 146 | 53.480 | 50.129 | −19.544 | 1.00 | 77.18 | O |
| ATOM | 9006 | N | GLU C | 147 | 52.913 | 52.284 | −19.776 | 1.00 | 90.31 | N |
| ATOM | 9007 | CA | GLU C | 147 | 54.075 | 52.581 | −20.591 | 1.00 | 97.81 | C |
| ATOM | 9008 | CB | GLU C | 147 | 53.911 | 51.908 | −21.965 | 1.00 | 98.02 | C |
| ATOM | 9009 | CG | GLU C | 147 | 54.426 | 52.662 | −23.184 | 1.00 | 99.84 | C |
| ATOM | 9010 | CD | GLU C | 147 | 54.794 | 51.699 | −24.291 | 1.00 | 102.95 | C |
| ATOM | 9011 | OE1 | GLU C | 147 | 53.882 | 51.056 | −24.867 | 1.00 | 98.08 | O |
| ATOM | 9012 | OE2 | GLU C | 147 | 56.009 | 51.560 | −24.553 | 1.00 | 107.97 | O |
| ATOM | 9013 | C | GLU C | 147 | 54.360 | 54.091 | −20.640 | 1.00 | 104.58 | C |
| ATOM | 9014 | O | GLU C | 147 | 53.502 | 54.864 | −21.044 | 1.00 | 104.80 | O |
| ATOM | 9015 | N | GLN C | 148 | 55.561 | 54.486 | −20.190 | 1.00 | 120.25 | N |
| ATOM | 9016 | CA | GLN C | 148 | 55.976 | 55.910 | −20.061 | 1.00 | 123.72 | C |
| ATOM | 9017 | CB | GLN C | 148 | 56.222 | 56.341 | −18.584 | 1.00 | 121.73 | C |
| ATOM | 9018 | CG | GLN C | 148 | 56.116 | 55.260 | −17.491 | 1.00 | 126.98 | C |

TABLE 6-continued

Atomic coordinates for CRBN:DDB1: Compound B (Human protein)

| ATOM | 9019 | CD  | GLN C | 148 | 54.680 | 54.803 | −17.151 | 1.00 | 130.08 | C |
| ---- | ---- | --- | ----- | --- | ------ | ------ | ------- | ---- | ------ | - |
| ATOM | 9020 | OE1 | GLN C | 148 | 53.716 | 55.573 | −17.253 | 1.00 | 130.71 | O |
| ATOM | 9021 | NE2 | GLN C | 148 | 54.543 | 53.539 | −16.729 | 1.00 | 127.97 | N |
| ATOM | 9022 | C   | GLN C | 148 | 57.178 | 56.227 | −20.960 | 1.00 | 125.29 | C |
| ATOM | 9023 | O   | GLN C | 148 | 57.932 | 57.148 | −20.674 | 1.00 | 119.48 | O |
| ATOM | 9024 | N   | ASP C | 149 | 57.304 | 55.472 | −22.063 | 1.00 | 137.08 | N |
| ATOM | 9025 | CA  | ASP C | 149 | 58.374 | 55.621 | −23.072 | 1.00 | 141.99 | C |
| ATOM | 9026 | CB  | ASP C | 149 | 58.636 | 54.294 | −23.823 | 1.00 | 145.84 | C |
| ATOM | 9027 | CG  | ASP C | 149 | 59.026 | 53.129 | −22.894 | 1.00 | 146.74 | C |
| ATOM | 9028 | OD1 | ASP C | 149 | 59.551 | 53.366 | −21.779 | 1.00 | 146.59 | O |
| ATOM | 9029 | OD2 | ASP C | 149 | 58.807 | 51.962 | −23.300 | 1.00 | 137.75 | O |
| ATOM | 9030 | C   | ASP C | 149 | 58.010 | 56.699 | −24.097 | 1.00 | 140.44 | C |
| ATOM | 9031 | O   | ASP C | 149 | 56.827 | 56.951 | −24.348 | 1.00 | 129.16 | O |
| ATOM | 9032 | N   | PHE C | 150 | 59.046 | 57.282 | −24.709 | 1.00 | 146.42 | N |
| ATOM | 9033 | CA  | PHE C | 150 | 58.984 | 58.587 | −25.402 | 1.00 | 148.83 | C |
| ATOM | 9034 | CB  | PHE C | 150 | 57.988 | 58.599 | −26.603 | 1.00 | 152.62 | C |
| ATOM | 9035 | CG  | PHE C | 150 | 58.160 | 57.476 | −27.624 | 1.00 | 152.24 | C |
| ATOM | 9036 | CD1 | PHE C | 150 | 59.420 | 56.976 | −27.981 | 1.00 | 148.43 | C |
| ATOM | 9037 | CE1 | PHE C | 150 | 59.539 | 55.975 | −28.944 | 1.00 | 144.37 | C |
| ATOM | 9038 | CZ  | PHE C | 150 | 58.403 | 55.478 | −29.584 | 1.00 | 143.63 | C |
| ATOM | 9039 | CE2 | PHE C | 150 | 57.146 | 55.976 | −29.263 | 1.00 | 141.95 | C |
| ATOM | 9040 | CD2 | PHE C | 150 | 57.028 | 56.972 | −28.300 | 1.00 | 146.88 | C |
| ATOM | 9041 | C   | PHE C | 150 | 58.644 | 59.766 | −24.436 | 1.00 | 147.25 | C |
| ATOM | 9042 | O   | PHE C | 150 | 58.134 | 60.801 | −24.887 | 1.00 | 146.24 | O |
| ATOM | 9043 | N   | GLY C | 151 | 58.910 | 59.614 | −23.127 | 1.00 | 143.07 | N |
| ATOM | 9044 | CA  | GLY C | 151 | 58.541 | 60.619 | −22.099 | 1.00 | 142.82 | C |
| ATOM | 9045 | C   | GLY C | 151 | 57.099 | 60.614 | −21.561 | 1.00 | 149.96 | C |
| ATOM | 9046 | O   | GLY C | 151 | 56.889 | 60.794 | −20.351 | 1.00 | 135.25 | O |
| ATOM | 9047 | N   | ILE C | 152 | 56.122 | 60.380 | −22.452 | 1.00 | 159.20 | N |
| ATOM | 9048 | CA  | ILE C | 152 | 54.664 | 60.597 | −22.211 | 1.00 | 154.27 | C |
| ATOM | 9049 | CB  | ILE C | 152 | 53.928 | 61.024 | −23.535 | 1.00 | 145.41 | C |
| ATOM | 9050 | CG1 | ILE C | 152 | 54.778 | 62.021 | −24.358 | 1.00 | 138.15 | C |
| ATOM | 9051 | CD1 | ILE C | 152 | 55.101 | 61.528 | −25.751 | 1.00 | 133.32 | C |
| ATOM | 9052 | CG2 | ILE C | 152 | 52.536 | 61.614 | −23.260 | 1.00 | 137.36 | C |
| ATOM | 9053 | C   | ILE C | 152 | 53.993 | 59.325 | −21.630 | 1.00 | 148.12 | C |
| ATOM | 9054 | O   | ILE C | 152 | 54.533 | 58.222 | −21.754 | 1.00 | 141.52 | O |
| ATOM | 9055 | N   | GLU C | 153 | 52.837 | 59.501 | −20.981 | 1.00 | 139.09 | N |
| ATOM | 9056 | CA  | GLU C | 153 | 52.009 | 58.396 | −20.452 | 1.00 | 130.96 | C |
| ATOM | 9057 | CB  | GLU C | 153 | 51.103 | 58.922 | −19.341 | 1.00 | 125.53 | C |
| ATOM | 9058 | CG  | GLU C | 153 | 51.818 | 59.365 | −18.087 | 1.00 | 122.50 | C |
| ATOM | 9059 | CD  | GLU C | 153 | 51.827 | 58.286 | −17.032 | 1.00 | 125.87 | C |
| ATOM | 9060 | OE1 | GLU C | 153 | 50.816 | 57.556 | −16.932 | 1.00 | 126.32 | O |
| ATOM | 9061 | OE2 | GLU C | 153 | 52.836 | 58.173 | −16.301 | 1.00 | 124.46 | O |
| ATOM | 9062 | C   | GLU C | 153 | 51.088 | 57.741 | −21.510 | 1.00 | 128.54 | C |
| ATOM | 9063 | O   | GLU C | 153 | 50.519 | 58.430 | −22.373 | 1.00 | 128.49 | O |
| ATOM | 9064 | N   | ILE C | 154 | 50.942 | 56.417 | −21.424 | 1.00 | 113.81 | N |
| ATOM | 9065 | CA  | ILE C | 154 | 49.927 | 55.663 | −22.175 | 1.00 | 102.62 | C |
| ATOM | 9066 | CB  | ILE C | 154 | 50.440 | 54.986 | −23.507 | 1.00 | 110.36 | C |
| ATOM | 9067 | CG1 | ILE C | 154 | 51.683 | 55.645 | −24.148 | 1.00 | 109.97 | C |
| ATOM | 9068 | CD1 | ILE C | 154 | 51.416 | 56.803 | −25.085 | 1.00 | 112.69 | C |
| ATOM | 9069 | CG2 | ILE C | 154 | 49.307 | 54.837 | −24.534 | 1.00 | 115.44 | C |
| ATOM | 9070 | C   | ILE C | 154 | 49.505 | 54.521 | −21.247 | 1.00 | 92.75  | C |
| ATOM | 9071 | O   | ILE C | 154 | 50.339 | 53.997 | −20.511 | 1.00 | 89.63  | O |
| ATOM | 9072 | N   | VAL C | 155 | 48.226 | 54.139 | −21.278 | 1.00 | 88.59  | N |
| ATOM | 9073 | CA  | VAL C | 155 | 47.774 | 52.820 | −20.751 | 1.00 | 82.70  | C |
| ATOM | 9074 | CB  | VAL C | 155 | 46.734 | 52.951 | −19.629 | 1.00 | 78.41  | C |
| ATOM | 9075 | CG1 | VAL C | 155 | 46.211 | 51.579 | −19.221 | 1.00 | 78.70  | C |
| ATOM | 9076 | CG2 | VAL C | 155 | 47.380 | 53.634 | −18.449 | 1.00 | 76.40  | C |
| ATOM | 9077 | C   | VAL C | 155 | 47.197 | 51.958 | −21.870 | 1.00 | 72.91  | C |
| ATOM | 9078 | O   | VAL C | 155 | 46.523 | 52.452 | −22.758 | 1.00 | 72.16  | O |
| ATOM | 9079 | N   | LYS C | 156 | 47.455 | 50.668 | −21.820 | 1.00 | 64.00  | N |
| ATOM | 9080 | CA  | LYS C | 156 | 46.923 | 49.798 | −22.832 | 1.00 | 62.40  | C |
| ATOM | 9081 | CB  | LYS C | 156 | 48.051 | 49.279 | −23.707 | 1.00 | 60.67  | C |
| ATOM | 9082 | CG  | LYS C | 156 | 48.746 | 50.386 | −24.480 | 1.00 | 61.31  | C |
| ATOM | 9083 | CD  | LYS C | 156 | 50.108 | 49.897 | −24.899 | 1.00 | 64.48  | C |
| ATOM | 9084 | CE  | LYS C | 156 | 50.833 | 50.929 | −25.729 | 1.00 | 66.41  | C |
| ATOM | 9085 | NZ  | LYS C | 156 | 50.551 | 50.686 | −27.169 | 1.00 | 71.08  | N |
| ATOM | 9086 | C   | LYS C | 156 | 46.153 | 48.683 | −22.166 | 1.00 | 60.21  | C |
| ATOM | 9087 | O   | LYS C | 156 | 46.733 | 47.844 | −21.486 | 1.00 | 58.31  | O |
| ATOM | 9088 | N   | VAL C | 157 | 44.842 | 48.648 | −22.366 | 1.00 | 61.25  | N |
| ATOM | 9089 | CA  | VAL C | 157 | 44.083 | 47.472 | −21.898 | 1.00 | 64.62  | C |
| ATOM | 9090 | CB  | VAL C | 157 | 42.957 | 47.854 | −20.920 | 1.00 | 67.54  | C |
| ATOM | 9091 | CG1 | VAL C | 157 | 43.550 | 48.517 | −19.691 | 1.00 | 72.30  | C |
| ATOM | 9092 | CG2 | VAL C | 157 | 41.998 | 48.816 | −21.552 | 1.00 | 70.49  | C |
| ATOM | 9093 | C   | VAL C | 157 | 43.592 | 46.525 | −23.006 | 1.00 | 59.21  | C |
| ATOM | 9094 | O   | VAL C | 157 | 43.615 | 46.845 | −24.219 | 1.00 | 59.83  | O |
| ATOM | 9095 | N   | LYS C | 158 | 43.221 | 45.334 | −22.563 | 1.00 | 51.90  | N |
| ATOM | 9096 | CA  | LYS C | 158 | 42.378 | 44.438 | −23.355 | 1.00 | 54.75  | C |

TABLE 6-continued

Atomic coordinates for CRBN:DDB1: Compound B (Human protein)

| ATOM | 9097 | CB | LYS C | 158 | 43.139 | 43.206 | −23.837 | 1.00 | 54.01 | C |
|---|---|---|---|---|---|---|---|---|---|---|
| ATOM | 9098 | CG | LYS C | 158 | 44.201 | 43.588 | −24.822 | 1.00 | 53.89 | C |
| ATOM | 9099 | CD | LYS C | 158 | 44.785 | 42.398 | −25.512 | 1.00 | 53.73 | C |
| ATOM | 9100 | CE | LYS C | 158 | 45.795 | 41.685 | −24.634 | 1.00 | 57.77 | C |
| ATOM | 9101 | NZ | LYS C | 158 | 46.933 | 41.205 | −25.490 | 1.00 | 60.40 | N |
| ATOM | 9102 | C | LYS C | 158 | 41.181 | 44.029 | −22.525 | 1.00 | 52.89 | C |
| ATOM | 9103 | O | LYS C | 158 | 41.300 | 43.238 | −21.588 | 1.00 | 55.21 | O |
| ATOM | 9104 | N | ALA C | 159 | 40.030 | 44.606 | −22.827 | 1.00 | 50.67 | N |
| ATOM | 9105 | CA | ALA C | 159 | 38.848 | 44.233 | −22.102 | 1.00 | 50.67 | C |
| ATOM | 9106 | CB | ALA C | 159 | 38.053 | 45.463 | −21.768 | 1.00 | 49.40 | C |
| ATOM | 9107 | C | ALA C | 159 | 38.002 | 43.174 | −22.877 | 1.00 | 49.97 | C |
| ATOM | 9108 | O | ALA C | 159 | 38.267 | 42.834 | −24.036 | 1.00 | 48.21 | O |
| ATOM | 9109 | N | ILE C | 160 | 36.994 | 42.638 | −22.227 | 1.00 | 44.50 | N |
| ATOM | 9110 | CA | ILE C | 160 | 36.127 | 41.767 | −22.929 | 1.00 | 44.82 | C |
| ATOM | 9111 | CB | ILE C | 160 | 36.566 | 40.309 | −22.810 | 1.00 | 46.38 | C |
| ATOM | 9112 | CG1 | ILE C | 160 | 35.487 | 39.382 | −23.324 | 1.00 | 44.43 | C |
| ATOM | 9113 | CD1 | ILE C | 160 | 36.030 | 38.020 | −23.605 | 1.00 | 45.53 | C |
| ATOM | 9114 | CG2 | ILE C | 160 | 36.849 | 39.933 | −21.371 | 1.00 | 48.37 | C |
| ATOM | 9115 | C | ILE C | 160 | 34.768 | 41.985 | −22.333 | 1.00 | 46.74 | C |
| ATOM | 9116 | O | ILE C | 160 | 34.614 | 41.993 | −21.112 | 1.00 | 41.89 | O |
| ATOM | 9117 | N | GLY C | 161 | 33.789 | 42.180 | −23.227 | 1.00 | 48.67 | N |
| ATOM | 9118 | CA | GLY C | 161 | 32.430 | 42.478 | −22.851 | 1.00 | 46.57 | C |
| ATOM | 9119 | C | GLY C | 161 | 31.975 | 41.251 | −22.131 | 1.00 | 47.10 | C |
| ATOM | 9120 | O | GLY C | 161 | 32.490 | 40.191 | −22.393 | 1.00 | 43.65 | O |
| ATOM | 9121 | N | ARG C | 162 | 31.043 | 41.415 | −21.211 | 1.00 | 50.82 | N |
| ATOM | 9122 | CA | ARG C | 162 | 30.563 | 40.353 | −20.347 | 1.00 | 51.39 | C |
| ATOM | 9123 | CB | ARG C | 162 | 31.225 | 40.484 | −18.985 | 1.00 | 51.47 | C |
| ATOM | 9124 | CG | ARG C | 162 | 32.665 | 39.988 | −18.968 | 1.00 | 53.83 | C |
| ATOM | 9125 | CD | ARG C | 162 | 32.774 | 38.499 | −18.663 | 1.00 | 57.05 | C |
| ATOM | 9126 | NE | ARG C | 162 | 33.762 | 37.736 | −19.472 | 1.00 | 61.84 | N |
| ATOM | 9127 | CZ | ARG C | 162 | 35.060 | 37.538 | −19.165 | 1.00 | 68.56 | C |
| ATOM | 9128 | NH1 | ARG C | 162 | 35.625 | 38.076 | −18.071 | 1.00 | 71.34 | N |
| ATOM | 9129 | NH2 | ARG C | 162 | 35.825 | 36.795 | −19.974 | 1.00 | 69.40 | N |
| ATOM | 9130 | C | ARG C | 162 | 29.034 | 40.390 | −20.259 | 1.00 | 52.86 | C |
| ATOM | 9131 | O | ARG C | 162 | 28.387 | 39.518 | −20.824 | 1.00 | 58.20 | O |
| ATOM | 9132 | N | GLN C | 163 | 28.453 | 41.393 | −19.600 | 1.00 | 50.90 | N |
| ATOM | 9133 | CA | GLN C | 163 | 27.006 | 41.424 | −19.402 | 1.00 | 52.14 | C |
| ATOM | 9134 | CB | GLN C | 163 | 26.709 | 41.371 | −17.933 | 1.00 | 52.93 | C |
| ATOM | 9135 | CG | GLN C | 163 | 27.187 | 40.111 | −17.251 | 1.00 | 54.26 | C |
| ATOM | 9136 | CD | GLN C | 163 | 27.434 | 40.326 | −15.777 | 1.00 | 53.47 | C |
| ATOM | 9137 | OE1 | GLN C | 163 | 28.292 | 41.164 | −15.348 | 1.00 | 55.13 | O |
| ATOM | 9138 | NE2 | GLN C | 163 | 26.679 | 39.599 | −14.984 | 1.00 | 50.83 | N |
| ATOM | 9139 | C | GLN C | 163 | 26.287 | 42.639 | −19.957 | 1.00 | 54.30 | C |
| ATOM | 9140 | O | GLN C | 163 | 26.837 | 43.734 | −19.954 | 1.00 | 55.57 | O |
| ATOM | 9141 | N | ARG C | 164 | 25.034 | 42.438 | −20.373 | 1.00 | 56.04 | N |
| ATOM | 9142 | CA | ARG C | 164 | 24.176 | 43.537 | −20.796 | 1.00 | 59.51 | C |
| ATOM | 9143 | CB | ARG C | 164 | 23.041 | 43.042 | −21.704 | 1.00 | 63.23 | C |
| ATOM | 9144 | CG | ARG C | 164 | 23.431 | 42.553 | −23.111 | 1.00 | 65.83 | C |
| ATOM | 9145 | CD | ARG C | 164 | 22.215 | 42.022 | −23.872 | 1.00 | 67.76 | C |
| ATOM | 9146 | NE | ARG C | 164 | 21.578 | 41.012 | −23.022 | 1.00 | 74.42 | N |
| ATOM | 9147 | CZ | ARG C | 164 | 20.281 | 40.712 | −22.940 | 1.00 | 77.37 | C |
| ATOM | 9148 | NH1 | ARG C | 164 | 19.354 | 41.291 | −23.701 | 1.00 | 80.85 | N |
| ATOM | 9149 | NH2 | ARG C | 164 | 19.919 | 39.772 | −22.071 | 1.00 | 79.02 | N |
| ATOM | 9150 | C | ARG C | 164 | 23.542 | 44.236 | −19.588 | 1.00 | 61.53 | C |
| ATOM | 9151 | O | ARG C | 164 | 23.196 | 43.596 | −18.568 | 1.00 | 60.73 | O |
| ATOM | 9152 | N | PHE C | 165 | 23.342 | 45.545 | −19.727 | 1.00 | 63.98 | N |
| ATOM | 9153 | CA | PHE C | 165 | 22.607 | 46.329 | −18.718 | 1.00 | 65.81 | C |
| ATOM | 9154 | CB | PHE C | 165 | 23.577 | 46.968 | −17.740 | 1.00 | 62.64 | C |
| ATOM | 9155 | CG | PHE C | 165 | 24.597 | 47.886 | −18.384 | 1.00 | 61.31 | C |
| ATOM | 9156 | CD1 | PHE C | 165 | 24.231 | 49.142 | −18.869 | 1.00 | 59.47 | C |
| ATOM | 9157 | CE1 | PHE C | 165 | 25.177 | 49.978 | −19.418 | 1.00 | 59.69 | C |
| ATOM | 9158 | CZ | PHE C | 165 | 26.508 | 49.573 | −19.501 | 1.00 | 60.18 | C |
| ATOM | 9159 | CE2 | PHE C | 165 | 26.884 | 48.331 | −19.058 | 1.00 | 57.28 | C |
| ATOM | 9160 | CD2 | PHE C | 165 | 25.936 | 47.496 | −18.493 | 1.00 | 59.20 | C |
| ATOM | 9161 | C | PHE C | 165 | 21.648 | 47.406 | −19.276 | 1.00 | 67.98 | C |
| ATOM | 9162 | O | PHE C | 165 | 21.756 | 47.807 | −20.444 | 1.00 | 63.36 | O |
| ATOM | 9163 | N | LYS C | 166 | 20.720 | 47.814 | −18.400 | 1.00 | 69.94 | N |
| ATOM | 9164 | CA | LYS C | 166 | 19.896 | 49.006 | −18.511 | 1.00 | 76.42 | C |
| ATOM | 9165 | CB | LYS C | 166 | 18.489 | 48.705 | −17.973 | 1.00 | 87.18 | C |
| ATOM | 9166 | CG | LYS C | 166 | 17.414 | 49.785 | −18.216 | 1.00 | 98.84 | C |
| ATOM | 9167 | CD | LYS C | 166 | 16.282 | 49.858 | −17.154 | 1.00 | 101.35 | C |
| ATOM | 9168 | CE | LYS C | 166 | 15.641 | 48.515 | −16.770 | 1.00 | 99.88 | C |
| ATOM | 9169 | NZ | LYS C | 166 | 14.816 | 47.928 | −17.856 | 1.00 | 100.81 | N |
| ATOM | 9170 | C | LYS C | 166 | 20.527 | 50.075 | −17.622 | 1.00 | 78.47 | C |
| ATOM | 9171 | O | LYS C | 166 | 20.930 | 49.786 | −16.474 | 1.00 | 79.83 | O |
| ATOM | 9172 | N | VAL C | 167 | 20.602 | 51.309 | −18.119 | 1.00 | 78.42 | N |
| ATOM | 9173 | CA | VAL C | 167 | 21.108 | 52.420 | −17.294 | 1.00 | 78.77 | C |
| ATOM | 9174 | CB | VAL C | 167 | 21.686 | 53.591 | −18.113 | 1.00 | 78.06 | C |

TABLE 6-continued

Atomic coordinates for CRBN:DDB1: Compound B (Human protein)

| ATOM | 9175 | CG1 | VAL C | 167 | 22.277 | 54.665 | −17.195 | 1.00 | 78.23 | C |
|---|---|---|---|---|---|---|---|---|---|---|
| ATOM | 9176 | CG2 | VAL C | 167 | 22.755 | 53.098 | −19.065 | 1.00 | 76.98 | C |
| ATOM | 9177 | C | VAL C | 167 | 19.977 | 52.942 | −16.425 | 1.00 | 79.54 | C |
| ATOM | 9178 | O | VAL C | 167 | 18.816 | 52.931 | −16.817 | 1.00 | 77.62 | O |
| ATOM | 9179 | N | LEU C | 168 | 20.338 | 53.364 | −15.225 | 1.00 | 83.97 | N |
| ATOM | 9180 | CA | LEU C | 168 | 19.400 | 53.925 | −14.266 | 1.00 | 87.72 | C |
| ATOM | 9181 | CB | LEU C | 168 | 19.394 | 53.102 | −12.966 | 1.00 | 85.09 | C |
| ATOM | 9182 | CG | LEU C | 168 | 18.973 | 51.634 | −13.200 | 1.00 | 84.45 | C |
| ATOM | 9183 | CD1 | LEU C | 168 | 19.020 | 50.774 | −11.925 | 1.00 | 80.63 | C |
| ATOM | 9184 | CD2 | LEU C | 168 | 17.593 | 51.610 | −13.881 | 1.00 | 82.38 | C |
| ATOM | 9185 | C | LEU C | 168 | 19.813 | 55.345 | −14.021 | 1.00 | 90.59 | C |
| ATOM | 9186 | O | LEU C | 168 | 19.061 | 56.264 | −14.312 | 1.00 | 105.38 | O |
| ATOM | 9187 | N | GLU C | 169 | 21.027 | 55.524 | −13.525 | 1.00 | 90.17 | N |
| ATOM | 9188 | CA | GLU C | 169 | 21.543 | 56.834 | −13.176 | 1.00 | 90.59 | C |
| ATOM | 9189 | CB | GLU C | 169 | 21.586 | 56.964 | −11.623 | 1.00 | 92.97 | C |
| ATOM | 9190 | CG | GLU C | 169 | 21.120 | 58.294 | −11.002 | 1.00 | 89.66 | C |
| ATOM | 9191 | CD | GLU C | 169 | 20.007 | 58.136 | −9.963 | 1.00 | 89.91 | C |
| ATOM | 9192 | OE1 | GLU C | 169 | 19.156 | 59.081 | −9.897 | 1.00 | 84.16 | O |
| ATOM | 9193 | OE2 | GLU C | 169 | 19.980 | 57.083 | −9.238 | 1.00 | 79.23 | O |
| ATOM | 9194 | C | GLU C | 169 | 22.927 | 56.982 | −13.832 | 1.00 | 90.59 | C |
| ATOM | 9195 | O | GLU C | 169 | 23.509 | 56.004 | −14.304 | 1.00 | 87.52 | O |
| ATOM | 9196 | N | LEU C | 170 | 23.414 | 58.225 | −13.849 | 1.00 | 93.84 | N |
| ATOM | 9197 | CA | LEU C | 170 | 24.696 | 58.640 | −14.422 | 1.00 | 90.35 | C |
| ATOM | 9198 | CB | LEU C | 170 | 24.570 | 58.844 | −15.958 | 1.00 | 86.96 | C |
| ATOM | 9199 | CG | LEU C | 170 | 25.054 | 57.750 | −16.924 | 1.00 | 86.04 | C |
| ATOM | 9200 | CD1 | LEU C | 170 | 24.479 | 57.859 | −18.331 | 1.00 | 81.87 | C |
| ATOM | 9201 | CD2 | LEU C | 170 | 26.569 | 57.782 | −16.994 | 1.00 | 89.10 | C |
| ATOM | 9202 | C | LEU C | 170 | 25.125 | 59.946 | −13.708 | 1.00 | 94.89 | C |
| ATOM | 9203 | O | LEU C | 170 | 25.052 | 61.043 | −14.292 | 1.00 | 93.48 | O |
| ATOM | 9204 | N | ARG C | 171 | 25.691 | 59.816 | −12.528 | 1.00 | 102.22 | N |
| ATOM | 9205 | CA | ARG C | 171 | 26.205 | 60.989 | −11.887 | 1.00 | 104.95 | C |
| ATOM | 9206 | CB | ARG C | 171 | 26.270 | 60.772 | −10.388 | 1.00 | 114.66 | C |
| ATOM | 9207 | CG | ARG C | 171 | 24.939 | 60.371 | −9.779 | 1.00 | 124.54 | C |
| ATOM | 9208 | CD | ARG C | 171 | 24.665 | 58.889 | −9.963 | 1.00 | 126.90 | C |
| ATOM | 9209 | NE | ARG C | 171 | 25.695 | 58.094 | −9.313 | 1.00 | 123.11 | N |
| ATOM | 9210 | CZ | ARG C | 171 | 25.474 | 56.932 | −8.722 | 1.00 | 109.16 | C |
| ATOM | 9211 | NH1 | ARG C | 171 | 26.472 | 56.292 | −8.150 | 1.00 | 103.13 | N |
| ATOM | 9212 | NH2 | ARG C | 171 | 24.259 | 56.423 | −8.690 | 1.00 | 107.17 | N |
| ATOM | 9213 | C | ARG C | 171 | 27.604 | 61.072 | −12.438 | 1.00 | 90.62 | C |
| ATOM | 9214 | O | ARG C | 171 | 28.397 | 60.196 | −12.197 | 1.00 | 84.96 | O |
| ATOM | 9215 | N | THR C | 172 | 27.917 | 62.119 | −13.180 | 1.00 | 82.44 | N |
| ATOM | 9216 | CA | THR C | 172 | 29.258 | 62.251 | −13.717 | 1.00 | 79.72 | C |
| ATOM | 9217 | CB | THR C | 172 | 29.367 | 63.186 | −14.932 | 1.00 | 76.30 | C |
| ATOM | 9218 | OG1 | THR C | 172 | 29.868 | 64.459 | −14.541 | 1.00 | 68.90 | O |
| ATOM | 9219 | CG2 | THR C | 172 | 28.035 | 63.336 | −15.613 | 1.00 | 72.88 | C |
| ATOM | 9220 | C | THR C | 172 | 30.056 | 62.691 | −12.516 | 1.00 | 80.38 | C |
| ATOM | 9221 | O | THR C | 172 | 29.481 | 62.918 | −11.473 | 1.00 | 79.14 | O |
| ATOM | 9222 | N | GLN C | 173 | 31.369 | 62.762 | −12.622 | 1.00 | 83.55 | N |
| ATOM | 9223 | CA | GLN C | 173 | 32.172 | 63.122 | −11.467 | 1.00 | 86.74 | C |
| ATOM | 9224 | CB | GLN C | 173 | 32.961 | 61.914 | −10.979 | 1.00 | 80.37 | C |
| ATOM | 9225 | C | GLN C | 173 | 33.095 | 64.295 | −11.706 | 1.00 | 91.99 | C |
| ATOM | 9226 | O | GLN C | 173 | 33.401 | 64.634 | −12.839 | 1.00 | 90.81 | O |
| ATOM | 9227 | N | SER C | 174 | 33.545 | 64.892 | −10.611 | 1.00 | 95.35 | N |
| ATOM | 9228 | CA | SER C | 174 | 34.408 | 66.056 | −10.633 | 1.00 | 93.15 | C |
| ATOM | 9229 | CB | SER C | 174 | 34.778 | 66.430 | −9.219 | 1.00 | 89.95 | C |
| ATOM | 9230 | OG | SER C | 174 | 34.852 | 65.262 | −8.431 | 1.00 | 89.80 | O |
| ATOM | 9231 | C | SER C | 174 | 35.643 | 65.704 | −11.408 | 1.00 | 96.09 | C |
| ATOM | 9232 | O | SER C | 174 | 36.193 | 66.532 | −12.113 | 1.00 | 95.70 | O |
| ATOM | 9233 | N | ASP C | 175 | 36.076 | 64.464 | −11.282 | 1.00 | 100.02 | N |
| ATOM | 9234 | CA | ASP C | 175 | 37.231 | 64.000 | −12.020 | 1.00 | 96.90 | C |
| ATOM | 9235 | CB | ASP C | 175 | 37.568 | 62.566 | −11.647 | 1.00 | 87.05 | C |
| ATOM | 9236 | C | ASP C | 175 | 36.883 | 64.092 | −13.502 | 1.00 | 105.36 | C |
| ATOM | 9237 | O | ASP C | 175 | 37.771 | 64.104 | −14.346 | 1.00 | 101.69 | O |
| ATOM | 9238 | N | GLY C | 176 | 35.586 | 64.155 | −13.809 | 1.00 | 115.12 | N |
| ATOM | 9239 | CA | GLY C | 176 | 35.100 | 64.249 | −15.174 | 1.00 | 116.57 | C |
| ATOM | 9240 | C | GLY C | 176 | 34.712 | 62.921 | −15.776 | 1.00 | 116.61 | C |
| ATOM | 9241 | O | GLY C | 176 | 34.425 | 62.811 | −16.962 | 1.00 | 116.04 | O |
| ATOM | 9242 | N | ILE C | 177 | 34.705 | 61.904 | −14.935 | 1.00 | 111.48 | N |
| ATOM | 9243 | CA | ILE C | 177 | 34.372 | 60.563 | −15.334 | 1.00 | 101.15 | C |
| ATOM | 9244 | CB | ILE C | 177 | 35.338 | 59.608 | −14.629 | 1.00 | 104.07 | C |
| ATOM | 9245 | CG1 | ILE C | 177 | 36.732 | 59.778 | −15.207 | 1.00 | 104.44 | C |
| ATOM | 9246 | CD1 | ILE C | 177 | 36.808 | 59.453 | −16.672 | 1.00 | 102.58 | C |
| ATOM | 9247 | CG2 | ILE C | 177 | 34.910 | 58.166 | −14.772 | 1.00 | 104.14 | C |
| ATOM | 9248 | C | ILE C | 177 | 32.961 | 60.237 | −14.899 | 1.00 | 91.61 | C |
| ATOM | 9249 | O | ILE C | 177 | 32.634 | 60.389 | −13.746 | 1.00 | 87.75 | O |
| ATOM | 9250 | N | GLN C | 178 | 32.131 | 59.783 | −15.827 | 1.00 | 84.40 | N |
| ATOM | 9251 | CA | GLN C | 178 | 30.762 | 59.419 | −15.517 | 1.00 | 80.73 | C |
| ATOM | 9252 | CB | GLN C | 178 | 29.947 | 59.230 | −16.776 | 1.00 | 81.14 | C |

TABLE 6-continued

Atomic coordinates for CRBN:DDB1: Compound B (Human protein)

| ATOM | 9253 | CG | GLN C | 178 | 29.165 | 60.446 | −17.193 | 1.00 | 81.56 | C |
|---|---|---|---|---|---|---|---|---|---|---|
| ATOM | 9254 | CD | GLN C | 178 | 28.627 | 60.298 | −18.582 | 1.00 | 86.61 | C |
| ATOM | 9255 | OE1 | GLN C | 178 | 29.296 | 59.770 | −19.454 | 1.00 | 85.65 | O |
| ATOM | 9256 | NE2 | GLN C | 178 | 27.416 | 60.762 | −18.800 | 1.00 | 91.90 | N |
| ATOM | 9257 | C | GLN C | 178 | 30.801 | 58.142 | −14.739 | 1.00 | 77.00 | C |
| ATOM | 9258 | O | GLN C | 178 | 31.757 | 57.418 | −14.826 | 1.00 | 75.25 | O |
| ATOM | 9259 | N | GLN C | 179 | 29.767 | 57.874 | −13.967 | 1.00 | 72.36 | N |
| ATOM | 9260 | CA | GLN C | 179 | 29.714 | 56.682 | −13.122 | 1.00 | 68.92 | C |
| ATOM | 9261 | CB | GLN C | 179 | 30.129 | 57.036 | −11.680 | 1.00 | 70.45 | C |
| ATOM | 9262 | CG | GLN C | 179 | 31.627 | 56.948 | −11.352 | 1.00 | 70.89 | C |
| ATOM | 9263 | CD | GLN C | 179 | 32.061 | 55.584 | −10.812 | 1.00 | 74.90 | C |
| ATOM | 9264 | OE1 | GLN C | 179 | 31.233 | 54.753 | −10.433 | 1.00 | 83.89 | O |
| ATOM | 9265 | NE2 | GLN C | 179 | 33.367 | 55.344 | −10.780 | 1.00 | 74.58 | N |
| ATOM | 9266 | C | GLN C | 179 | 28.280 | 56.172 | −13.181 | 1.00 | 67.27 | C |
| ATOM | 9267 | O | GLN C | 179 | 27.390 | 56.722 | −12.541 | 1.00 | 67.54 | O |
| ATOM | 9268 | N | ALA C | 180 | 28.047 | 55.134 | −13.957 | 1.00 | 69.58 | N |
| ATOM | 9269 | CA | ALA C | 180 | 26.708 | 54.618 | −14.141 | 1.00 | 69.21 | C |
| ATOM | 9270 | CB | ALA C | 180 | 26.557 | 54.151 | −15.562 | 1.00 | 68.11 | C |
| ATOM | 9271 | C | ALA C | 180 | 26.247 | 53.533 | −13.216 | 1.00 | 67.93 | C |
| ATOM | 9272 | O | ALA C | 180 | 26.954 | 52.588 | −12.969 | 1.00 | 59.81 | O |
| ATOM | 9273 | N | LYS C | 181 | 25.029 | 53.678 | −12.722 | 1.00 | 76.13 | N |
| ATOM | 9274 | CA | LYS C | 181 | 24.426 | 52.697 | −11.853 | 1.00 | 82.04 | C |
| ATOM | 9275 | CB | LYS C | 181 | 23.498 | 53.360 | −10.852 | 1.00 | 92.83 | C |
| ATOM | 9276 | CG | LYS C | 181 | 22.471 | 52.406 | −10.279 | 1.00 | 104.69 | C |
| ATOM | 9277 | CD | LYS C | 181 | 21.529 | 53.055 | −9.287 | 1.00 | 110.86 | C |
| ATOM | 9278 | CE | LYS C | 181 | 21.874 | 52.664 | −7.861 | 1.00 | 114.65 | C |
| ATOM | 9279 | NZ | LYS C | 181 | 20.754 | 52.930 | −6.913 | 1.00 | 117.12 | N |
| ATOM | 9280 | C | LYS C | 181 | 23.635 | 51.901 | −12.833 | 1.00 | 75.11 | C |
| ATOM | 9281 | O | LYS C | 181 | 22.873 | 52.459 | −13.591 | 1.00 | 76.98 | O |
| ATOM | 9282 | N | VAL C | 182 | 23.810 | 50.593 | −12.824 | 1.00 | 69.65 | N |
| ATOM | 9283 | CA | VAL C | 182 | 23.164 | 49.757 | −13.806 | 1.00 | 68.82 | C |
| ATOM | 9284 | CB | VAL C | 182 | 24.248 | 49.190 | −14.715 | 1.00 | 66.57 | C |
| ATOM | 9285 | CG1 | VAL C | 182 | 23.631 | 48.429 | −15.864 | 1.00 | 68.31 | C |
| ATOM | 9286 | CG2 | VAL C | 182 | 25.116 | 50.306 | −15.240 | 1.00 | 63.14 | C |
| ATOM | 9287 | C | VAL C | 182 | 22.385 | 48.573 | −13.308 | 1.00 | 65.19 | C |
| ATOM | 9288 | O | VAL C | 182 | 22.609 | 48.097 | −12.220 | 1.00 | 60.62 | O |
| ATOM | 9289 | N | GLN C | 183 | 21.467 | 48.104 | −14.143 | 1.00 | 64.33 | N |
| ATOM | 9290 | CA | GLN C | 183 | 20.658 | 46.941 | −13.836 | 1.00 | 67.80 | C |
| ATOM | 9291 | CB | GLN C | 183 | 19.201 | 47.237 | −14.109 | 1.00 | 71.87 | C |
| ATOM | 9292 | CG | GLN C | 183 | 18.294 | 47.044 | −12.916 | 1.00 | 75.76 | C |
| ATOM | 9293 | CD | GLN C | 183 | 17.687 | 45.675 | −12.839 | 1.00 | 77.37 | C |
| ATOM | 9294 | OE1 | GLN C | 183 | 16.929 | 45.280 | −13.706 | 1.00 | 82.46 | O |
| ATOM | 9295 | NE2 | GLN C | 183 | 17.997 | 44.952 | −11.780 | 1.00 | 77.58 | N |
| ATOM | 9296 | C | GLN C | 183 | 21.141 | 45.870 | −14.779 | 1.00 | 63.22 | C |
| ATOM | 9297 | O | GLN C | 183 | 21.143 | 46.053 | −15.972 | 1.00 | 59.70 | O |
| ATOM | 9298 | N | ILE C | 184 | 21.557 | 44.749 | −14.234 | 1.00 | 59.68 | N |
| ATOM | 9299 | CA | ILE C | 184 | 22.107 | 43.658 | −15.024 | 1.00 | 63.19 | C |
| ATOM | 9300 | CB | ILE C | 184 | 22.986 | 42.708 | −14.192 | 1.00 | 65.49 | C |
| ATOM | 9301 | CG1 | ILE C | 184 | 24.196 | 43.449 | −13.616 | 1.00 | 65.36 | C |
| ATOM | 9302 | CD1 | ILE C | 184 | 25.284 | 43.758 | −14.635 | 1.00 | 64.74 | C |
| ATOM | 9303 | CG2 | ILE C | 184 | 23.469 | 41.542 | −15.051 | 1.00 | 65.81 | C |
| ATOM | 9304 | C | ILE C | 184 | 20.966 | 42.888 | −15.655 | 1.00 | 62.10 | C |
| ATOM | 9305 | O | ILE C | 184 | 20.066 | 42.420 | −14.971 | 1.00 | 59.03 | O |
| ATOM | 9306 | N | LEU C | 185 | 20.988 | 42.769 | −16.971 | 1.00 | 62.51 | N |
| ATOM | 9307 | CA | LEU C | 185 | 19.845 | 42.186 | −17.619 | 1.00 | 63.44 | C |
| ATOM | 9308 | CB | LEU C | 185 | 19.706 | 42.649 | −19.047 | 1.00 | 65.05 | C |
| ATOM | 9309 | CG | LEU C | 185 | 19.625 | 44.144 | −19.228 | 1.00 | 66.96 | C |
| ATOM | 9310 | CD1 | LEU C | 185 | 19.509 | 44.446 | −20.711 | 1.00 | 68.46 | C |
| ATOM | 9311 | CD2 | LEU C | 185 | 18.473 | 44.735 | −18.441 | 1.00 | 66.93 | C |
| ATOM | 9312 | C | LEU C | 185 | 20.017 | 40.698 | −17.611 | 1.00 | 64.24 | C |
| ATOM | 9313 | O | LEU C | 185 | 21.064 | 40.213 | −18.054 | 1.00 | 62.74 | O |
| ATOM | 9314 | N | PRO C | 186 | 18.971 | 39.970 | −17.179 | 1.00 | 64.67 | N |
| ATOM | 9315 | CA | PRO C | 186 | 19.008 | 38.536 | −17.215 | 1.00 | 67.45 | C |
| ATOM | 9316 | CB | PRO C | 186 | 17.658 | 38.162 | −16.614 | 1.00 | 66.72 | C |
| ATOM | 9317 | CG | PRO C | 186 | 16.738 | 39.224 | −17.097 | 1.00 | 63.83 | C |
| ATOM | 9318 | CD | PRO C | 186 | 17.577 | 40.462 | −17.142 | 1.00 | 65.84 | C |
| ATOM | 9319 | C | PRO C | 186 | 19.093 | 38.041 | −18.661 | 1.00 | 74.85 | C |
| ATOM | 9320 | O | PRO C | 186 | 18.638 | 38.719 | −19.580 | 1.00 | 76.23 | O |
| ATOM | 9321 | N | GLU C | 187 | 19.665 | 36.870 | −18.874 | 1.00 | 85.45 | N |
| ATOM | 9322 | CA | GLU C | 187 | 19.755 | 36.349 | −20.218 | 1.00 | 85.27 | C |
| ATOM | 9323 | CB | GLU C | 187 | 21.110 | 35.707 | −20.401 | 1.00 | 87.33 | C |
| ATOM | 9324 | CG | GLU C | 187 | 21.543 | 35.570 | −21.839 | 1.00 | 93.16 | C |
| ATOM | 9325 | CD | GLU C | 187 | 21.770 | 36.898 | −22.509 | 1.00 | 96.14 | C |
| ATOM | 9326 | OE1 | GLU C | 187 | 21.998 | 37.896 | −21.815 | 1.00 | 78.72 | O |
| ATOM | 9327 | OE2 | GLU C | 187 | 21.716 | 36.937 | −23.744 | 1.00 | 90.47 | O |
| ATOM | 9328 | C | GLU C | 187 | 18.686 | 35.302 | −20.314 | 1.00 | 79.58 | C |
| ATOM | 9329 | O | GLU C | 187 | 18.811 | 34.259 | −19.733 | 1.00 | 79.52 | O |
| ATOM | 9330 | N | CYS C | 188 | 17.638 | 35.566 | −21.072 | 1.00 | 80.23 | N |

TABLE 6-continued

Atomic coordinates for CRBN:DDB1: Compound B (Human protein)

| ATOM | 9331 | CA | CYS C | 188 | 16.527 | 34.633 | −21.173 | 1.00 | 86.54 | C |
|---|---|---|---|---|---|---|---|---|---|---|
| ATOM | 9332 | CB | CYS C | 188 | 15.388 | 35.296 | −21.937 | 1.00 | 94.54 | C |
| ATOM | 9333 | SG | CYS C | 188 | 14.202 | 34.199 | −22.732 | 1.00 | 102.98 | S |
| ATOM | 9334 | C | CYS C | 188 | 16.810 | 33.278 | −21.774 | 1.00 | 80.44 | C |
| ATOM | 9335 | O | CYS C | 188 | 17.408 | 33.165 | −22.821 | 1.00 | 69.36 | O |
| ATOM | 9336 | N | VAL C | 189 | 16.310 | 32.256 | −21.095 | 1.00 | 79.57 | N |
| ATOM | 9337 | CA | VAL C | 189 | 16.448 | 30.871 | −21.508 | 1.00 | 88.89 | C |
| ATOM | 9338 | CB | VAL C | 189 | 17.341 | 30.082 | −20.570 | 1.00 | 91.49 | C |
| ATOM | 9339 | CG1 | VAL C | 189 | 18.781 | 30.199 | −21.000 | 1.00 | 90.30 | C |
| ATOM | 9340 | CG2 | VAL C | 189 | 17.150 | 30.554 | −19.145 | 1.00 | 101.41 | C |
| ATOM | 9341 | C | VAL C | 189 | 15.091 | 30.212 | −21.498 | 1.00 | 83.67 | C |
| ATOM | 9342 | O | VAL C | 189 | 14.279 | 30.501 | −20.651 | 1.00 | 87.56 | O |
| ATOM | 9343 | N | LEU C | 190 | 14.849 | 29.333 | −22.454 | 1.00 | 76.66 | N |
| ATOM | 9344 | CA | LEU C | 190 | 13.583 | 28.654 | −22.563 | 1.00 | 68.93 | C |
| ATOM | 9345 | CB | LEU C | 190 | 12.831 | 29.150 | −23.776 | 1.00 | 65.37 | C |
| ATOM | 9346 | CG | LEU C | 190 | 12.458 | 30.604 | −23.882 | 1.00 | 67.91 | C |
| ATOM | 9347 | CD1 | LEU C | 190 | 11.413 | 30.744 | −24.953 | 1.00 | 69.80 | C |
| ATOM | 9348 | CD2 | LEU C | 190 | 11.886 | 31.013 | −22.559 | 1.00 | 74.25 | C |
| ATOM | 9349 | C | LEU C | 190 | 13.883 | 27.219 | −22.794 | 1.00 | 69.01 | C |
| ATOM | 9350 | O | LEU C | 190 | 14.932 | 26.901 | −23.301 | 1.00 | 73.65 | O |
| ATOM | 9351 | N | PRO C | 191 | 12.978 | 26.334 | −22.430 | 1.00 | 67.23 | N |
| ATOM | 9352 | CA | PRO C | 191 | 13.259 | 24.919 | −22.670 | 1.00 | 73.25 | C |
| ATOM | 9353 | CB | PRO C | 191 | 12.361 | 24.214 | −21.644 | 1.00 | 75.04 | C |
| ATOM | 9354 | CG | PRO C | 191 | 11.492 | 25.288 | −21.020 | 1.00 | 69.02 | C |
| ATOM | 9355 | CD | PRO C | 191 | 11.649 | 26.524 | −21.835 | 1.00 | 63.70 | C |
| ATOM | 9356 | C | PRO C | 191 | 12.948 | 24.475 | −24.122 | 1.00 | 71.95 | C |
| ATOM | 9357 | O | PRO C | 191 | 12.495 | 25.284 | −24.943 | 1.00 | 66.68 | O |
| ATOM | 9358 | N | SER C | 192 | 13.164 | 23.210 | −24.402 | 1.00 | 70.61 | N |
| ATOM | 9359 | CA | SER C | 192 | 12.933 | 22.702 | −25.713 | 1.00 | 72.19 | C |
| ATOM | 9360 | CB | SER C | 192 | 13.241 | 21.227 | −25.779 | 1.00 | 78.74 | C |
| ATOM | 9361 | OG | SER C | 192 | 12.690 | 20.673 | −26.947 | 1.00 | 75.63 | O |
| ATOM | 9362 | C | SER C | 192 | 11.495 | 22.886 | −25.951 | 1.00 | 67.77 | C |
| ATOM | 9363 | O | SER C | 192 | 10.714 | 22.893 | −25.041 | 1.00 | 66.54 | O |
| ATOM | 9364 | N | THR C | 193 | 11.159 | 23.058 | −27.205 | 1.00 | 71.70 | N |
| ATOM | 9365 | CA | THR C | 193 | 9.811 | 23.275 | −27.618 | 1.00 | 71.97 | C |
| ATOM | 9366 | CB | THR C | 193 | 9.790 | 23.477 | −29.123 | 1.00 | 76.64 | C |
| ATOM | 9367 | OG1 | THR C | 193 | 11.032 | 23.031 | −29.653 | 1.00 | 81.84 | O |
| ATOM | 9368 | CG2 | THR C | 193 | 9.721 | 24.903 | −29.430 | 1.00 | 76.76 | C |
| ATOM | 9369 | C | THR C | 193 | 8.998 | 22.081 | −27.236 | 1.00 | 71.40 | C |
| ATOM | 9370 | O | THR C | 193 | 7.863 | 22.198 | −26.827 | 1.00 | 71.30 | O |
| ATOM | 9371 | N | MET C | 194 | 9.595 | 20.918 | −27.383 | 1.00 | 71.27 | N |
| ATOM | 9372 | CA | MET C | 194 | 8.950 | 19.655 | −27.078 | 1.00 | 74.36 | C |
| ATOM | 9373 | CB | MET C | 194 | 9.744 | 18.537 | −27.718 | 1.00 | 76.39 | C |
| ATOM | 9374 | CG | MET C | 194 | 9.705 | 18.524 | −29.221 | 1.00 | 73.67 | C |
| ATOM | 9375 | SD | MET C | 194 | 8.043 | 18.286 | −29.784 | 1.00 | 73.52 | S |
| ATOM | 9376 | CE | MET C | 194 | 7.478 | 19.955 | −29.760 | 1.00 | 67.77 | C |
| ATOM | 9377 | C | MET C | 194 | 8.776 | 19.289 | −25.623 | 1.00 | 74.57 | C |
| ATOM | 9378 | O | MET C | 194 | 8.030 | 18.398 | −25.298 | 1.00 | 73.00 | O |
| ATOM | 9379 | N | SER C | 195 | 9.460 | 19.971 | −24.738 | 1.00 | 84.82 | N |
| ATOM | 9380 | CA | SER C | 195 | 9.442 | 19.611 | −23.340 | 1.00 | 86.80 | C |
| ATOM | 9381 | CB | SER C | 195 | 10.310 | 20.593 | −22.597 | 1.00 | 87.32 | C |
| ATOM | 9382 | OG | SER C | 195 | 9.821 | 21.892 | −22.817 | 1.00 | 86.43 | O |
| ATOM | 9383 | C | SER C | 195 | 8.101 | 19.594 | −22.662 | 1.00 | 82.67 | C |
| ATOM | 9384 | O | SER C | 195 | 7.826 | 18.689 | −21.884 | 1.00 | 74.84 | O |
| ATOM | 9385 | N | ALA C | 196 | 7.276 | 20.588 | −22.916 | 1.00 | 82.46 | N |
| ATOM | 9386 | CA | ALA C | 196 | 5.992 | 20.607 | −22.277 | 1.00 | 84.89 | C |
| ATOM | 9387 | CB | ALA C | 196 | 5.311 | 21.908 | −22.617 | 1.00 | 86.62 | C |
| ATOM | 9388 | C | ALA C | 196 | 5.127 | 19.462 | −22.734 | 1.00 | 79.43 | C |
| ATOM | 9389 | O | ALA C | 196 | 4.582 | 18.723 | −21.953 | 1.00 | 83.81 | O |
| ATOM | 9390 | N | VAL C | 197 | 5.039 | 19.315 | −24.031 | 1.00 | 71.74 | N |
| ATOM | 9391 | CA | VAL C | 197 | 4.212 | 18.327 | −24.667 | 1.00 | 69.68 | C |
| ATOM | 9392 | CB | VAL C | 197 | 4.062 | 18.666 | −26.139 | 1.00 | 70.91 | C |
| ATOM | 9393 | CG1 | VAL C | 197 | 5.351 | 18.392 | −26.850 | 1.00 | 67.53 | C |
| ATOM | 9394 | CG2 | VAL C | 197 | 2.963 | 17.843 | −26.748 | 1.00 | 78.97 | C |
| ATOM | 9395 | C | VAL C | 197 | 4.573 | 16.872 | −24.512 | 1.00 | 72.72 | C |
| ATOM | 9396 | O | VAL C | 197 | 3.726 | 16.011 | −24.497 | 1.00 | 70.74 | O |
| ATOM | 9397 | N | GLN C | 198 | 5.855 | 16.608 | −24.576 | 1.00 | 75.02 | N |
| ATOM | 9398 | CA | GLN C | 198 | 6.382 | 15.278 | −24.696 | 1.00 | 77.31 | C |
| ATOM | 9399 | CB | GLN C | 198 | 7.874 | 15.386 | −24.383 | 1.00 | 85.63 | C |
| ATOM | 9400 | CG | GLN C | 198 | 8.651 | 14.089 | −24.366 | 1.00 | 90.98 | C |
| ATOM | 9401 | CD | GLN C | 198 | 9.561 | 13.970 | −25.545 | 1.00 | 97.44 | C |
| ATOM | 9402 | OE1 | GLN C | 198 | 9.922 | 14.961 | −26.148 | 1.00 | 109.04 | O |
| ATOM | 9403 | NE2 | GLN C | 198 | 9.948 | 12.757 | −25.874 | 1.00 | 103.85 | N |
| ATOM | 9404 | C | GLN C | 198 | 5.852 | 14.145 | −23.861 | 1.00 | 73.53 | C |
| ATOM | 9405 | O | GLN C | 198 | 5.717 | 14.231 | −22.666 | 1.00 | 72.57 | O |
| ATOM | 9406 | N | LEU C | 199 | 5.577 | 13.057 | −24.569 | 1.00 | 74.77 | N |
| ATOM | 9407 | CA | LEU C | 199 | 5.171 | 11.768 | −23.981 | 1.00 | 72.13 | C |
| ATOM | 9408 | CB | LEU C | 199 | 4.935 | 10.693 | −25.066 | 1.00 | 71.13 | C |

TABLE 6-continued

Atomic coordinates for CRBN:DDB1: Compound B (Human protein)

| ATOM | 9409 | CG | LEU C | 199 | 3.524 | 10.403 | −25.594 | 1.00 | 74.69 | C |
|---|---|---|---|---|---|---|---|---|---|---|
| ATOM | 9410 | CD1 | LEU C | 199 | 2.755 | 11.662 | −25.892 | 1.00 | 70.25 | C |
| ATOM | 9411 | CD2 | LEU C | 199 | 3.564 | 9.544 | −26.857 | 1.00 | 81.50 | C |
| ATOM | 9412 | C | LEU C | 199 | 6.266 | 11.294 | −23.031 | 1.00 | 67.51 | C |
| ATOM | 9413 | O | LEU C | 199 | 7.436 | 11.283 | −23.399 | 1.00 | 67.17 | O |
| ATOM | 9414 | N | GLU C | 200 | 5.868 | 10.840 | −21.851 | 1.00 | 65.18 | N |
| ATOM | 9415 | CA | GLU C | 200 | 6.805 | 10.465 | −20.786 | 1.00 | 67.88 | C |
| ATOM | 9416 | CB | GLU C | 200 | 6.182 | 10.597 | −19.381 | 1.00 | 74.15 | C |
| ATOM | 9417 | CG | GLU C | 200 | 5.040 | 11.611 | −19.247 | 1.00 | 85.96 | C |
| ATOM | 9418 | CD | GLU C | 200 | 3.692 | 11.020 | −19.675 | 1.00 | 97.34 | C |
| ATOM | 9419 | OE1 | GLU C | 200 | 3.140 | 11.392 | −20.755 | 1.00 | 89.91 | O |
| ATOM | 9420 | OE2 | GLU C | 200 | 3.213 | 10.124 | −18.954 | 1.00 | 105.42 | O |
| ATOM | 9421 | C | GLU C | 200 | 7.361 | 9.040 | −21.021 | 1.00 | 66.52 | C |
| ATOM | 9422 | O | GLU C | 200 | 8.434 | 8.684 | −20.529 | 1.00 | 66.68 | O |
| ATOM | 9423 | N | SER C | 201 | 6.648 | 8.226 | −21.792 | 1.00 | 70.35 | N |
| ATOM | 9424 | CA | SER C | 201 | 7.200 | 6.952 | −22.269 | 1.00 | 73.46 | C |
| ATOM | 9425 | CB | SER C | 201 | 6.135 | 6.101 | −22.951 | 1.00 | 68.72 | C |
| ATOM | 9426 | OG | SER C | 201 | 5.564 | 6.815 | −24.021 | 1.00 | 72.49 | O |
| ATOM | 9427 | C | SER C | 201 | 8.360 | 7.186 | −23.224 | 1.00 | 73.72 | C |
| ATOM | 9428 | O | SER C | 201 | 9.265 | 6.348 | −23.298 | 1.00 | 78.74 | O |
| ATOM | 9429 | N | LEU C | 202 | 8.322 | 8.325 | −23.928 | 1.00 | 76.29 | N |
| ATOM | 9430 | CA | LEU C | 202 | 9.402 | 8.785 | −24.825 | 1.00 | 80.07 | C |
| ATOM | 9431 | CB | LEU C | 202 | 8.793 | 9.425 | −26.085 | 1.00 | 75.90 | C |
| ATOM | 9432 | CG | LEU C | 202 | 7.690 | 8.637 | −26.808 | 1.00 | 81.48 | C |
| ATOM | 9433 | CD1 | LEU C | 202 | 7.230 | 9.383 | −28.048 | 1.00 | 85.86 | C |
| ATOM | 9434 | CD2 | LEU C | 202 | 8.127 | 7.229 | −27.182 | 1.00 | 82.90 | C |
| ATOM | 9435 | C | LEU C | 202 | 10.440 | 9.749 | −24.188 | 1.00 | 81.31 | C |
| ATOM | 9436 | O | LEU C | 202 | 11.257 | 10.329 | −24.903 | 1.00 | 83.41 | O |
| ATOM | 9437 | N | ASN C | 203 | 10.417 | 9.913 | −22.863 | 1.00 | 84.76 | N |
| ATOM | 9438 | CA | ASN C | 203 | 11.482 | 10.627 | −22.142 | 1.00 | 86.99 | C |
| ATOM | 9439 | CB | ASN C | 203 | 11.173 | 10.772 | −20.637 | 1.00 | 85.09 | C |
| ATOM | 9440 | CG | ASN C | 203 | 10.159 | 11.869 | −20.322 | 1.00 | 84.10 | C |
| ATOM | 9441 | OD1 | ASN C | 203 | 9.400 | 11.757 | −19.355 | 1.00 | 79.43 | O |
| ATOM | 9442 | ND2 | ASN C | 203 | 10.149 | 12.932 | −21.113 | 1.00 | 84.89 | N |
| ATOM | 9443 | C | ASN C | 203 | 12.799 | 9.883 | −22.275 | 1.00 | 93.49 | C |
| ATOM | 9444 | O | ASN C | 203 | 13.841 | 10.488 | −22.538 | 1.00 | 94.28 | O |
| ATOM | 9445 | N | LYS C | 204 | 12.729 | 8.563 | −22.116 | 1.00 | 100.28 | N |
| ATOM | 9446 | CA | LYS C | 204 | 13.904 | 7.695 | −22.109 | 1.00 | 101.29 | C |
| ATOM | 9447 | CB | LYS C | 204 | 13.484 | 6.237 | −21.838 | 1.00 | 108.65 | C |
| ATOM | 9448 | CG | LYS C | 204 | 12.759 | 5.982 | −20.510 | 1.00 | 117.30 | C |
| ATOM | 9449 | CD | LYS C | 204 | 12.212 | 4.549 | −20.409 | 1.00 | 121.13 | C |
| ATOM | 9450 | CE | LYS C | 204 | 10.941 | 4.456 | −19.566 | 1.00 | 117.74 | C |
| ATOM | 9451 | NZ | LYS C | 204 | 9.740 | 5.005 | −20.269 | 1.00 | 110.50 | N |
| ATOM | 9452 | C | LYS C | 204 | 14.745 | 7.788 | −23.406 | 1.00 | 101.61 | C |
| ATOM | 9453 | O | LYS C | 204 | 15.900 | 7.378 | −23.406 | 1.00 | 106.00 | O |
| ATOM | 9454 | N | CYS C | 205 | 14.182 | 8.337 | −24.489 | 1.00 | 103.49 | N |
| ATOM | 9455 | CA | CYS C | 205 | 14.858 | 8.420 | −25.797 | 1.00 | 102.42 | C |
| ATOM | 9456 | CB | CYS C | 205 | 13.922 | 7.849 | −26.861 | 1.00 | 96.36 | C |
| ATOM | 9457 | SG | CYS C | 205 | 13.019 | 6.425 | −26.233 | 1.00 | 91.08 | S |
| ATOM | 9458 | C | CYS C | 205 | 15.308 | 9.824 | −26.236 | 1.00 | 106.63 | C |
| ATOM | 9459 | O | CYS C | 205 | 15.621 | 10.017 | −27.418 | 1.00 | 108.45 | O |
| ATOM | 9460 | N | GLN C | 206 | 15.362 | 10.784 | −25.306 | 1.00 | 109.59 | N |
| ATOM | 9461 | CA | GLN C | 206 | 15.728 | 12.177 | −25.634 | 1.00 | 112.01 | C |
| ATOM | 9462 | CB | GLN C | 206 | 15.116 | 13.173 | −24.627 | 1.00 | 104.10 | C |
| ATOM | 9463 | CG | GLN C | 206 | 13.594 | 13.256 | −24.651 | 1.00 | 102.80 | C |
| ATOM | 9464 | CD | GLN C | 206 | 13.014 | 13.371 | −26.059 | 1.00 | 106.45 | C |
| ATOM | 9465 | OE1 | GLN C | 206 | 12.288 | 12.487 | −26.513 | 1.00 | 106.70 | O |
| ATOM | 9466 | NE2 | GLN C | 206 | 13.357 | 14.446 | −26.766 | 1.00 | 102.38 | N |
| ATOM | 9467 | C | GLN C | 206 | 17.240 | 12.421 | −25.786 | 1.00 | 120.87 | C |
| ATOM | 9468 | O | GLN C | 206 | 17.645 | 13.327 | −26.519 | 1.00 | 138.36 | O |
| ATOM | 9469 | N | ILE C | 207 | 18.072 | 11.636 | −25.108 | 1.00 | 124.67 | N |
| ATOM | 9470 | CA | ILE C | 207 | 19.516 | 11.692 | −25.340 | 1.00 | 128.28 | C |
| ATOM | 9471 | CB | ILE C | 207 | 20.326 | 11.301 | −24.080 | 1.00 | 124.92 | C |
| ATOM | 9472 | CG1 | ILE C | 207 | 19.985 | 12.270 | −22.937 | 1.00 | 113.64 | C |
| ATOM | 9473 | CD1 | ILE C | 207 | 20.962 | 12.301 | −21.782 | 1.00 | 111.00 | C |
| ATOM | 9474 | CG2 | ILE C | 207 | 21.826 | 11.313 | −24.382 | 1.00 | 133.59 | C |
| ATOM | 9475 | C | ILE C | 207 | 19.840 | 10.762 | −26.499 | 1.00 | 126.20 | C |
| ATOM | 9476 | O | ILE C | 207 | 19.370 | 9.628 | −26.524 | 1.00 | 134.58 | O |
| ATOM | 9477 | N | PHE C | 208 | 20.638 | 11.247 | −27.448 | 1.00 | 125.95 | N |
| ATOM | 9478 | CA | PHE C | 208 | 21.101 | 10.434 | −28.574 | 1.00 | 133.91 | C |
| ATOM | 9479 | CB | PHE C | 208 | 20.735 | 11.100 | −29.902 | 1.00 | 133.81 | C |
| ATOM | 9480 | CG | PHE C | 208 | 19.375 | 11.733 | −29.917 | 1.00 | 132.73 | C |
| ATOM | 9481 | CD1 | PHE C | 208 | 18.225 | 10.942 | −29.927 | 1.00 | 143.33 | C |
| ATOM | 9482 | CE1 | PHE C | 208 | 16.965 | 11.524 | −29.952 | 1.00 | 145.03 | C |
| ATOM | 9483 | CZ | PHE C | 208 | 16.844 | 12.910 | −29.974 | 1.00 | 140.18 | C |
| ATOM | 9484 | CE2 | PHE C | 208 | 17.983 | 13.706 | −29.971 | 1.00 | 133.55 | C |
| ATOM | 9485 | CD2 | PHE C | 208 | 19.239 | 13.119 | −29.945 | 1.00 | 124.20 | C |
| ATOM | 9486 | C | PHE C | 208 | 22.624 | 10.251 | −28.526 | 1.00 | 143.81 | C |

TABLE 6-continued

Atomic coordinates for CRBN:DDB1: Compound B (Human protein)

| ATOM | 9487 | O | PHE C | 208 | 23.313 | 10.971 | −27.794 | 1.00 | 149.14 | O |
|---|---|---|---|---|---|---|---|---|---|---|
| ATOM | 9488 | N | PRO C | 209 | 23.154 | 9.284 | −29.305 | 1.00 | 140.46 | N |
| ATOM | 9489 | CA | PRO C | 209 | 24.569 | 9.286 | −29.713 | 1.00 | 145.75 | C |
| ATOM | 9490 | CB | PRO C | 209 | 24.747 | 7.912 | −30.380 | 1.00 | 139.18 | C |
| ATOM | 9491 | CG | PRO C | 209 | 23.629 | 7.079 | −29.859 | 1.00 | 131.14 | C |
| ATOM | 9492 | CD | PRO C | 209 | 22.490 | 8.026 | −29.671 | 1.00 | 125.69 | C |
| ATOM | 9493 | C | PRO C | 209 | 24.868 | 10.439 | −30.702 | 1.00 | 148.85 | C |
| ATOM | 9494 | O | PRO C | 209 | 23.964 | 10.874 | −31.423 | 1.00 | 146.83 | O |
| ATOM | 9495 | N | SER C | 210 | 26.116 | 10.914 | −30.741 | 1.00 | 148.30 | N |
| ATOM | 9496 | CA | SER C | 210 | 26.464 | 12.167 | −31.455 | 1.00 | 156.12 | C |
| ATOM | 9497 | CB | SER C | 210 | 27.522 | 12.981 | −30.677 | 1.00 | 157.41 | C |
| ATOM | 9498 | OG | SER C | 210 | 27.953 | 12.316 | −29.501 | 1.00 | 152.88 | O |
| ATOM | 9499 | C | SER C | 210 | 26.861 | 12.033 | −32.944 | 1.00 | 154.68 | C |
| ATOM | 9500 | O | SER C | 210 | 27.235 | 10.955 | −33.421 | 1.00 | 141.26 | O |
| ATOM | 9501 | N | LYS C | 211 | 26.773 | 13.175 | −33.634 | 1.00 | 159.06 | N |
| ATOM | 9502 | CA | LYS C | 211 | 26.839 | 13.288 | −35.116 | 1.00 | 165.33 | C |
| ATOM | 9503 | CB | LYS C | 211 | 26.485 | 14.737 | −35.583 | 1.00 | 156.94 | C |
| ATOM | 9504 | CG | LYS C | 211 | 27.141 | 15.927 | −34.849 | 1.00 | 151.51 | C |
| ATOM | 9505 | CD | LYS C | 211 | 26.128 | 16.997 | −34.388 | 1.00 | 142.43 | C |
| ATOM | 9506 | CE | LYS C | 211 | 26.333 | 17.455 | −32.937 | 1.00 | 128.41 | C |
| ATOM | 9507 | NZ | LYS C | 211 | 25.178 | 18.221 | −32.369 | 1.00 | 109.66 | N |
| ATOM | 9508 | C | LYS C | 211 | 28.140 | 12.784 | −35.806 | 1.00 | 174.81 | C |
| ATOM | 9509 | O | LYS C | 211 | 29.216 | 13.335 | −35.552 | 1.00 | 174.97 | O |
| ATOM | 9510 | N | PRO C | 212 | 28.038 | 11.741 | −36.681 | 1.00 | 183.91 | N |
| ATOM | 9511 | CA | PRO C | 212 | 29.173 | 11.306 | −37.526 | 1.00 | 189.11 | C |
| ATOM | 9512 | CB | PRO C | 212 | 28.583 | 10.130 | −38.327 | 1.00 | 184.72 | C |
| ATOM | 9513 | CG | PRO C | 212 | 27.523 | 9.579 | −37.443 | 1.00 | 174.62 | C |
| ATOM | 9514 | CD | PRO C | 212 | 26.914 | 10.784 | −36.783 | 1.00 | 177.41 | C |
| ATOM | 9515 | C | PRO C | 212 | 29.737 | 12.402 | −38.463 | 1.00 | 187.12 | C |
| ATOM | 9516 | O | PRO C | 212 | 29.116 | 12.740 | −39.481 | 1.00 | 189.91 | O |
| ATOM | 9517 | N | VAL C | 213 | 30.916 | 12.926 | −38.108 | 1.00 | 173.75 | N |
| ATOM | 9518 | CA | VAL C | 213 | 31.501 | 14.110 | −38.769 | 1.00 | 156.85 | C |
| ATOM | 9519 | CB | VAL C | 213 | 32.713 | 14.696 | −37.987 | 1.00 | 155.53 | C |
| ATOM | 9520 | CG1 | VAL C | 213 | 32.329 | 15.054 | −36.549 | 1.00 | 147.29 | C |
| ATOM | 9521 | CG2 | VAL C | 213 | 33.918 | 13.752 | −38.026 | 1.00 | 155.04 | C |
| ATOM | 9522 | C | VAL C | 213 | 31.923 | 13.841 | −40.215 | 1.00 | 134.37 | C |
| ATOM | 9523 | O | VAL C | 213 | 32.141 | 14.777 | −40.979 | 1.00 | 107.01 | O |
| ATOM | 9524 | N | SER C | 220 | 26.804 | 14.175 | −43.186 | 1.00 | 134.21 | N |
| ATOM | 9525 | CA | SER C | 220 | 25.998 | 13.506 | −42.182 | 1.00 | 134.51 | C |
| ATOM | 9526 | CB | SER C | 220 | 26.672 | 13.597 | −40.825 | 1.00 | 129.00 | C |
| ATOM | 9527 | OG | SER C | 220 | 26.695 | 14.933 | −40.378 | 1.00 | 118.01 | O |
| ATOM | 9528 | C | SER C | 220 | 24.625 | 14.138 | −42.106 | 1.00 | 128.89 | C |
| ATOM | 9529 | O | SER C | 220 | 24.039 | 14.239 | −41.048 | 1.00 | 121.53 | O |
| ATOM | 9530 | N | TYR C | 221 | 24.111 | 14.553 | −43.244 | 1.00 | 126.86 | N |
| ATOM | 9531 | CA | TYR C | 221 | 22.813 | 15.176 | −43.306 | 1.00 | 122.10 | C |
| ATOM | 9532 | CB | TYR C | 221 | 22.571 | 15.735 | −44.709 | 1.00 | 133.46 | C |
| ATOM | 9533 | CG | TYR C | 221 | 21.411 | 15.185 | −45.508 | 1.00 | 150.11 | C |
| ATOM | 9534 | CD1 | TYR C | 221 | 20.533 | 16.041 | −46.142 | 1.00 | 157.98 | C |
| ATOM | 9535 | CE1 | TYR C | 221 | 19.477 | 15.567 | −46.884 | 1.00 | 154.09 | C |
| ATOM | 9536 | CZ | TYR C | 221 | 19.287 | 14.222 | −46.994 | 1.00 | 148.81 | C |
| ATOM | 9537 | OH | TYR C | 221 | 18.233 | 13.743 | −47.735 | 1.00 | 136.82 | O |
| ATOM | 9538 | CE2 | TYR C | 221 | 20.145 | 13.347 | −46.369 | 1.00 | 148.31 | C |
| ATOM | 9539 | CD2 | TYR C | 221 | 21.203 | 13.833 | −45.636 | 1.00 | 151.42 | C |
| ATOM | 9540 | C | TYR C | 221 | 21.744 | 14.211 | −42.859 | 1.00 | 122.62 | C |
| ATOM | 9541 | O | TYR C | 221 | 20.764 | 14.599 | −42.259 | 1.00 | 112.00 | O |
| ATOM | 9542 | N | LYS C | 222 | 21.940 | 12.945 | −43.169 | 1.00 | 132.11 | N |
| ATOM | 9543 | CA | LYS C | 222 | 20.983 | 11.914 | −42.828 | 1.00 | 128.11 | C |
| ATOM | 9544 | CB | LYS C | 222 | 21.487 | 10.560 | −43.294 | 1.00 | 140.52 | C |
| ATOM | 9545 | CG | LYS C | 222 | 22.816 | 10.147 | −42.687 | 1.00 | 139.23 | C |
| ATOM | 9546 | CD | LYS C | 222 | 23.449 | 9.029 | −43.497 | 1.00 | 135.67 | C |
| ATOM | 9547 | CE | LYS C | 222 | 23.784 | 9.485 | −44.908 | 1.00 | 132.32 | C |
| ATOM | 9548 | NZ | LYS C | 222 | 24.959 | 10.396 | −44.962 | 1.00 | 129.03 | N |
| ATOM | 9549 | C | LYS C | 222 | 20.817 | 11.900 | −41.340 | 1.00 | 112.93 | C |
| ATOM | 9550 | O | LYS C | 222 | 19.745 | 11.657 | −40.825 | 1.00 | 115.88 | O |
| ATOM | 9551 | N | TRP C | 223 | 21.898 | 12.161 | −40.642 | 1.00 | 98.85 | N |
| ATOM | 9552 | CA | TRP C | 223 | 21.851 | 12.176 | −39.209 | 1.00 | 89.83 | C |
| ATOM | 9553 | CB | TRP C | 223 | 23.214 | 12.563 | −38.702 | 1.00 | 81.14 | C |
| ATOM | 9554 | CG | TRP C | 223 | 23.334 | 12.486 | −37.278 | 1.00 | 79.13 | C |
| ATOM | 9555 | CD1 | TRP C | 223 | 23.798 | 11.450 | −36.573 | 1.00 | 82.60 | C |
| ATOM | 9556 | NE1 | TRP C | 223 | 23.779 | 11.732 | −35.246 | 1.00 | 85.50 | N |
| ATOM | 9557 | CE2 | TRP C | 223 | 23.291 | 12.993 | −35.081 | 1.00 | 88.29 | C |
| ATOM | 9558 | CD2 | TRP C | 223 | 23.005 | 13.493 | −36.346 | 1.00 | 88.13 | C |
| ATOM | 9559 | CE3 | TRP C | 223 | 22.498 | 14.776 | −36.457 | 1.00 | 95.07 | C |
| ATOM | 9560 | CZ3 | TRP C | 223 | 22.299 | 15.500 | −35.315 | 1.00 | 96.01 | C |
| ATOM | 9561 | CH2 | TRP C | 223 | 22.588 | 14.973 | −34.074 | 1.00 | 89.61 | C |
| ATOM | 9562 | CZ2 | TRP C | 223 | 23.080 | 13.720 | −33.935 | 1.00 | 88.64 | C |
| ATOM | 9563 | C | TRP C | 223 | 20.869 | 13.218 | −38.739 | 1.00 | 90.39 | C |
| ATOM | 9564 | O | TRP C | 223 | 20.119 | 12.983 | −37.823 | 1.00 | 97.71 | O |

TABLE 6-continued

Atomic coordinates for CRBN:DDB1: Compound B (Human protein)

| ATOM | 9565 | N | TRP C | 224 | 20.860 | 14.375 | −39.369 | 1.00 | 84.48 | N |
|---|---|---|---|---|---|---|---|---|---|---|
| ATOM | 9566 | CA | TRP C | 224 | 19.956 | 15.429 | −38.961 | 1.00 | 86.32 | C |
| ATOM | 9567 | CB | TRP C | 224 | 20.296 | 16.724 | −39.674 | 1.00 | 90.45 | C |
| ATOM | 9568 | CG | TRP C | 224 | 21.480 | 17.338 | −39.083 | 1.00 | 89.08 | C |
| ATOM | 9569 | CD1 | TRP C | 224 | 22.750 | 17.201 | −39.492 | 1.00 | 87.42 | C |
| ATOM | 9570 | NE1 | TRP C | 224 | 23.588 | 17.892 | −38.670 | 1.00 | 88.10 | N |
| ATOM | 9571 | CE2 | TRP C | 224 | 22.845 | 18.485 | −37.691 | 1.00 | 89.37 | C |
| ATOM | 9572 | CD2 | TRP C | 224 | 21.516 | 18.149 | −37.920 | 1.00 | 90.97 | C |
| ATOM | 9573 | CE3 | TRP C | 224 | 20.546 | 18.637 | −37.056 | 1.00 | 92.16 | C |
| ATOM | 9574 | CZ3 | TRP C | 224 | 20.928 | 19.418 | −36.021 | 1.00 | 94.21 | C |
| ATOM | 9575 | CH2 | TRP C | 224 | 22.253 | 19.735 | −35.814 | 1.00 | 97.08 | C |
| ATOM | 9576 | CZ2 | TRP C | 224 | 23.229 | 19.280 | −36.640 | 1.00 | 90.66 | C |
| ATOM | 9577 | C | TRP C | 224 | 18.500 | 15.067 | −39.114 | 1.00 | 89.06 | C |
| ATOM | 9578 | O | TRP C | 224 | 17.676 | 15.478 | −38.324 | 1.00 | 91.19 | O |
| ATOM | 9579 | N | GLN C | 225 | 18.188 | 14.296 | −40.133 | 1.00 | 92.24 | N |
| ATOM | 9580 | CA | GLN C | 225 | 16.816 | 13.814 | −40.391 | 1.00 | 92.08 | C |
| ATOM | 9581 | CB | GLN C | 225 | 16.692 | 13.076 | −41.720 | 1.00 | 101.27 | C |
| ATOM | 9582 | CG | GLN C | 225 | 16.386 | 13.992 | −42.885 | 1.00 | 116.12 | C |
| ATOM | 9583 | CD | GLN C | 225 | 16.729 | 13.334 | −44.203 | 1.00 | 128.51 | C |
| ATOM | 9584 | OE1 | GLN C | 225 | 16.272 | 12.227 | −44.478 | 1.00 | 127.93 | O |
| ATOM | 9585 | NE2 | GLN C | 225 | 17.558 | 13.992 | −45.014 | 1.00 | 138.02 | N |
| ATOM | 9586 | C | GLN C | 225 | 16.339 | 12.896 | −39.303 | 1.00 | 79.95 | C |
| ATOM | 9587 | O | GLN C | 225 | 15.186 | 12.995 | −38.895 | 1.00 | 74.85 | O |
| ATOM | 9588 | N | LYS C | 226 | 17.212 | 11.985 | −38.868 | 1.00 | 75.24 | N |
| ATOM | 9589 | CA | LYS C | 226 | 16.877 | 11.053 | −37.791 | 1.00 | 76.95 | C |
| ATOM | 9590 | CB | LYS C | 226 | 17.902 | 9.906 | −37.698 | 1.00 | 70.79 | C |
| ATOM | 9591 | C | LYS C | 226 | 16.719 | 11.824 | −36.463 | 1.00 | 77.63 | C |
| ATOM | 9592 | O | LYS C | 226 | 15.798 | 11.545 | −35.685 | 1.00 | 76.77 | O |
| ATOM | 9593 | N | TYR C | 227 | 17.601 | 12.801 | −36.230 | 1.00 | 78.72 | N |
| ATOM | 9594 | CA | TYR C | 227 | 17.454 | 13.791 | −35.139 | 1.00 | 76.58 | C |
| ATOM | 9595 | CB | TYR C | 227 | 18.576 | 14.841 | −35.231 | 1.00 | 74.81 | C |
| ATOM | 9596 | CG | TYR C | 227 | 18.451 | 16.043 | −34.306 | 1.00 | 73.65 | C |
| ATOM | 9597 | CD1 | TYR C | 227 | 17.654 | 17.147 | −34.657 | 1.00 | 79.89 | C |
| ATOM | 9598 | CE1 | TYR C | 227 | 17.545 | 18.254 | −33.821 | 1.00 | 78.09 | C |
| ATOM | 9599 | CZ | TYR C | 227 | 18.255 | 18.275 | −32.627 | 1.00 | 73.27 | C |
| ATOM | 9600 | OH | TYR C | 227 | 18.143 | 19.369 | −31.794 | 1.00 | 76.19 | O |
| ATOM | 9601 | CE2 | TYR C | 227 | 19.063 | 17.202 | −32.271 | 1.00 | 67.31 | C |
| ATOM | 9602 | CD2 | TYR C | 227 | 19.160 | 16.101 | −33.104 | 1.00 | 66.44 | C |
| ATOM | 9603 | C | TYR C | 227 | 16.092 | 14.487 | −35.192 | 1.00 | 73.06 | C |
| ATOM | 9604 | O | TYR C | 227 | 15.370 | 14.559 | −34.204 | 1.00 | 74.23 | O |
| ATOM | 9605 | N | GLN C | 228 | 15.758 | 15.015 | −36.354 | 1.00 | 70.90 | N |
| ATOM | 9606 | CA | GLN C | 228 | 14.477 | 15.680 | −36.530 | 1.00 | 71.11 | C |
| ATOM | 9607 | CB | GLN C | 228 | 14.340 | 16.240 | −37.944 | 1.00 | 66.53 | C |
| ATOM | 9608 | CG | GLN C | 228 | 13.689 | 17.603 | −37.974 | 1.00 | 67.42 | C |
| ATOM | 9609 | CD | GLN C | 228 | 12.966 | 17.877 | −39.266 | 1.00 | 70.52 | C |
| ATOM | 9610 | OE1 | GLN C | 228 | 12.853 | 19.026 | −39.703 | 1.00 | 61.74 | O |
| ATOM | 9611 | NE2 | GLN C | 228 | 12.457 | 16.817 | −39.887 | 1.00 | 76.01 | N |
| ATOM | 9612 | C | GLN C | 228 | 13.299 | 14.739 | −36.224 | 1.00 | 74.75 | C |
| ATOM | 9613 | O | GLN C | 228 | 12.377 | 15.134 | −35.533 | 1.00 | 83.32 | O |
| ATOM | 9614 | N | LYS C | 229 | 13.330 | 13.507 | −36.734 | 1.00 | 79.81 | N |
| ATOM | 9615 | CA | LYS C | 229 | 12.274 | 12.522 | −36.434 | 1.00 | 78.02 | C |
| ATOM | 9616 | CB | LYS C | 229 | 12.405 | 11.238 | −37.293 | 1.00 | 70.09 | C |
| ATOM | 9617 | C | LYS C | 229 | 12.240 | 12.188 | −34.924 | 1.00 | 73.15 | C |
| ATOM | 9618 | O | LYS C | 229 | 11.156 | 12.114 | −34.350 | 1.00 | 76.30 | O |
| ATOM | 9619 | N | ARG C | 230 | 13.401 | 12.020 | −34.281 | 1.00 | 65.27 | N |
| ATOM | 9620 | CA | ARG C | 230 | 13.432 | 11.567 | −32.877 | 1.00 | 67.48 | C |
| ATOM | 9621 | CB | ARG C | 230 | 14.804 | 10.969 | −32.471 | 1.00 | 56.97 | C |
| ATOM | 9622 | C | ARG C | 230 | 12.985 | 12.695 | −31.935 | 1.00 | 74.38 | C |
| ATOM | 9623 | O | ARG C | 230 | 12.003 | 12.538 | −31.208 | 1.00 | 82.97 | O |
| ATOM | 9624 | N | LYS C | 231 | 13.675 | 13.839 | −31.999 | 1.00 | 80.18 | N |
| ATOM | 9625 | CA | LYS C | 231 | 13.418 | 14.995 | −31.132 | 1.00 | 70.98 | C |
| ATOM | 9626 | CB | LYS C | 231 | 14.380 | 16.128 | −31.450 | 1.00 | 74.74 | C |
| ATOM | 9627 | CG | LYS C | 231 | 14.129 | 17.393 | −30.636 | 1.00 | 78.93 | C |
| ATOM | 9628 | CD | LYS C | 231 | 15.402 | 18.214 | −30.466 | 1.00 | 84.48 | C |
| ATOM | 9629 | CE | LYS C | 231 | 15.348 | 19.102 | −29.232 | 1.00 | 89.91 | C |
| ATOM | 9630 | NZ | LYS C | 231 | 16.701 | 19.194 | −28.625 | 1.00 | 92.05 | N |
| ATOM | 9631 | C | LYS C | 231 | 12.010 | 15.540 | −31.233 | 1.00 | 66.38 | C |
| ATOM | 9632 | O | LYS C | 231 | 11.425 | 15.878 | −30.219 | 1.00 | 77.22 | O |
| ATOM | 9633 | N | PHE C | 232 | 11.466 | 15.628 | −32.436 | 1.00 | 56.58 | N |
| ATOM | 9634 | CA | PHE C | 232 | 10.144 | 16.214 | −32.619 | 1.00 | 58.23 | C |
| ATOM | 9635 | CB | PHE C | 232 | 10.233 | 17.262 | −33.712 | 1.00 | 61.95 | C |
| ATOM | 9636 | CG | PHE C | 232 | 11.264 | 18.295 | −33.423 | 1.00 | 71.01 | C |
| ATOM | 9637 | CD1 | PHE C | 232 | 11.034 | 19.252 | −32.433 | 1.00 | 73.52 | C |
| ATOM | 9638 | CE1 | PHE C | 232 | 11.993 | 20.191 | −32.128 | 1.00 | 73.80 | C |
| ATOM | 9639 | CZ | PHE C | 232 | 13.202 | 20.180 | −32.807 | 1.00 | 76.12 | C |
| ATOM | 9640 | CE2 | PHE C | 232 | 13.454 | 19.222 | −33.781 | 1.00 | 75.17 | C |
| ATOM | 9641 | CD2 | PHE C | 232 | 12.489 | 18.279 | −34.078 | 1.00 | 74.16 | C |
| ATOM | 9642 | C | PHE C | 232 | 8.999 | 15.234 | −32.885 | 1.00 | 61.58 | C |

TABLE 6-continued

Atomic coordinates for CRBN:DDB1: Compound B (Human protein)

| ATOM | 9643 | O | PHE C | 232 | 7.956 | 15.637 | −33.432 | 1.00 | 56.44 | O |
|---|---|---|---|---|---|---|---|---|---|---|
| ATOM | 9644 | N | HIS C | 233 | 9.139 | 13.973 | −32.460 | 1.00 | 62.84 | N |
| ATOM | 9645 | CA | HIS C | 233 | 8.069 | 12.990 | −32.689 | 1.00 | 64.19 | C |
| ATOM | 9646 | CB | HIS C | 233 | 8.447 | 11.591 | −32.161 | 1.00 | 71.54 | C |
| ATOM | 9647 | CG | HIS C | 233 | 7.371 | 10.561 | −32.353 | 1.00 | 78.79 | C |
| ATOM | 9648 | ND1 | HIS C | 233 | 6.572 | 10.114 | −31.319 | 1.00 | 86.04 | N |
| ATOM | 9649 | CE1 | HIS C | 233 | 5.697 | 9.241 | −31.780 | 1.00 | 84.38 | C |
| ATOM | 9650 | NE2 | HIS C | 233 | 5.898 | 9.107 | −33.079 | 1.00 | 85.13 | N |
| ATOM | 9651 | CD2 | HIS C | 233 | 6.941 | 9.918 | −33.462 | 1.00 | 79.26 | C |
| ATOM | 9652 | C | HIS C | 233 | 6.775 | 13.496 | −32.055 | 1.00 | 59.12 | C |
| ATOM | 9653 | O | HIS C | 233 | 5.702 | 13.445 | −32.666 | 1.00 | 56.98 | O |
| ATOM | 9654 | N | CYS C | 234 | 6.888 | 14.057 | −30.857 | 1.00 | 57.84 | N |
| ATOM | 9655 | CA | CYS C | 234 | 5.713 | 14.536 | −30.162 | 1.00 | 59.74 | C |
| ATOM | 9656 | CB | CYS C | 234 | 5.996 | 14.702 | −28.674 | 1.00 | 65.60 | C |
| ATOM | 9657 | SG | CYS C | 234 | 6.112 | 13.066 | −27.895 | 1.00 | 75.39 | S |
| ATOM | 9658 | C | CYS C | 234 | 5.096 | 15.765 | −30.798 | 1.00 | 55.59 | C |
| ATOM | 9659 | O | CYS C | 234 | 4.067 | 16.237 | −30.338 | 1.00 | 59.11 | O |
| ATOM | 9660 | N | ALA C | 235 | 5.667 | 16.248 | −31.897 | 1.00 | 52.95 | N |
| ATOM | 9661 | CA | ALA C | 235 | 4.982 | 17.240 | −32.721 | 1.00 | 56.48 | C |
| ATOM | 9662 | CB | ALA C | 235 | 5.816 | 17.630 | −33.934 | 1.00 | 56.85 | C |
| ATOM | 9663 | C | ALA C | 235 | 3.614 | 16.767 | −33.176 | 1.00 | 57.69 | C |
| ATOM | 9664 | O | ALA C | 235 | 2.742 | 17.594 | −33.464 | 1.00 | 56.76 | O |
| ATOM | 9665 | N | ASN C | 236 | 3.427 | 15.444 | −33.237 | 1.00 | 60.89 | N |
| ATOM | 9666 | CA | ASN C | 236 | 2.151 | 14.863 | −33.653 | 1.00 | 61.59 | C |
| ATOM | 9667 | CB | ASN C | 236 | 2.311 | 13.372 | −33.896 | 1.00 | 68.05 | C |
| ATOM | 9668 | CG | ASN C | 236 | 2.871 | 13.085 | −35.272 | 1.00 | 75.93 | C |
| ATOM | 9669 | OD1 | ASN C | 236 | 4.084 | 12.918 | −35.430 | 1.00 | 82.92 | O |
| ATOM | 9670 | ND2 | ASN C | 236 | 1.990 | 13.052 | −36.286 | 1.00 | 75.10 | N |
| ATOM | 9671 | C | ASN C | 236 | 0.981 | 15.127 | −32.718 | 1.00 | 57.06 | C |
| ATOM | 9672 | O | ASN C | 236 | −0.161 | 14.927 | −33.115 | 1.00 | 52.90 | O |
| ATOM | 9673 | N | LEU C | 237 | 1.278 | 15.601 | −31.507 | 1.00 | 51.47 | N |
| ATOM | 9674 | CA | LEU C | 237 | 0.279 | 15.937 | −30.523 | 1.00 | 47.82 | C |
| ATOM | 9675 | CB | LEU C | 237 | 0.841 | 15.738 | −29.134 | 1.00 | 52.03 | C |
| ATOM | 9676 | CG | LEU C | 237 | 1.575 | 14.407 | −28.880 | 1.00 | 54.59 | C |
| ATOM | 9677 | CD1 | LEU C | 237 | 2.151 | 14.360 | −27.471 | 1.00 | 55.55 | C |
| ATOM | 9678 | CD2 | LEU C | 237 | 0.650 | 13.246 | −29.135 | 1.00 | 51.47 | C |
| ATOM | 9679 | C | LEU C | 237 | −0.122 | 17.364 | −30.624 | 1.00 | 46.73 | C |
| ATOM | 9680 | O | LEU C | 237 | −1.108 | 17.742 | −30.045 | 1.00 | 43.08 | O |
| ATOM | 9681 | N | THR C | 238 | 0.661 | 18.169 | −31.329 | 1.00 | 53.28 | N |
| ATOM | 9682 | CA | THR C | 238 | 0.443 | 19.611 | −31.422 | 1.00 | 54.27 | C |
| ATOM | 9683 | CB | THR C | 238 | 1.762 | 20.377 | −31.440 | 1.00 | 55.98 | C |
| ATOM | 9684 | OG1 | THR C | 238 | 2.286 | 20.355 | −32.772 | 1.00 | 54.95 | O |
| ATOM | 9685 | CG2 | THR C | 238 | 2.790 | 19.782 | −30.444 | 1.00 | 55.10 | C |
| ATOM | 9686 | C | THR C | 238 | −0.211 | 19.845 | −32.753 | 1.00 | 55.28 | C |
| ATOM | 9687 | O | THR C | 238 | −0.455 | 18.879 | −33.462 | 1.00 | 56.51 | O |
| ATOM | 9688 | N | SER C | 239 | −0.450 | 21.102 | −33.131 | 1.00 | 56.83 | N |
| ATOM | 9689 | CA | SER C | 239 | −1.003 | 21.370 | −34.465 | 1.00 | 61.86 | C |
| ATOM | 9690 | CB | SER C | 239 | −2.275 | 22.251 | −34.402 | 1.00 | 63.29 | C |
| ATOM | 9691 | OG | SER C | 239 | −2.054 | 23.565 | −33.965 | 1.00 | 65.25 | O |
| ATOM | 9692 | C | SER C | 239 | 0.051 | 21.821 | −35.503 | 1.00 | 60.84 | C |
| ATOM | 9693 | O | SER C | 239 | −0.306 | 22.545 | −36.450 | 1.00 | 58.85 | O |
| ATOM | 9694 | N | TRP C | 240 | 1.310 | 21.348 | −35.344 | 1.00 | 58.74 | N |
| ATOM | 9695 | CA | TRP C | 240 | 2.430 | 21.624 | −36.286 | 1.00 | 58.34 | C |
| ATOM | 9696 | CB | TRP C | 240 | 3.170 | 22.932 | −35.904 | 1.00 | 61.57 | C |
| ATOM | 9697 | CG | TRP C | 240 | 2.481 | 24.048 | −36.556 | 1.00 | 65.59 | C |
| ATOM | 9698 | CD1 | TRP C | 240 | 2.336 | 24.281 | −37.924 | 1.00 | 74.23 | C |
| ATOM | 9699 | NE1 | TRP C | 240 | 1.558 | 25.378 | −38.153 | 1.00 | 72.97 | N |
| ATOM | 9700 | CE2 | TRP C | 240 | 1.172 | 25.865 | −36.945 | 1.00 | 67.79 | C |
| ATOM | 9701 | CD2 | TRP C | 240 | 1.749 | 25.036 | −35.921 | 1.00 | 59.98 | C |
| ATOM | 9702 | CE3 | TRP C | 240 | 1.514 | 25.322 | −34.603 | 1.00 | 55.20 | C |
| ATOM | 9703 | CZ3 | TRP C | 240 | 0.741 | 26.365 | −34.326 | 1.00 | 64.99 | C |
| ATOM | 9704 | CH2 | TRP C | 240 | 0.184 | 27.189 | −35.368 | 1.00 | 74.61 | C |
| ATOM | 9705 | CZ2 | TRP C | 240 | 0.402 | 26.938 | −36.673 | 1.00 | 67.22 | C |
| ATOM | 9706 | C | TRP C | 240 | 3.468 | 20.505 | −36.571 | 1.00 | 57.59 | C |
| ATOM | 9707 | O | TRP C | 240 | 3.609 | 19.554 | −35.810 | 1.00 | 69.85 | O |
| ATOM | 9708 | N | PRO C | 241 | 4.200 | 20.624 | −37.692 | 1.00 | 53.99 | N |
| ATOM | 9709 | CA | PRO C | 241 | 5.189 | 19.631 | −38.070 | 1.00 | 54.08 | C |
| ATOM | 9710 | CB | PRO C | 241 | 5.463 | 19.937 | −39.535 | 1.00 | 55.17 | C |
| ATOM | 9711 | CG | PRO C | 241 | 4.592 | 21.044 | −39.939 | 1.00 | 55.33 | C |
| ATOM | 9712 | CD | PRO C | 241 | 3.985 | 21.621 | −38.751 | 1.00 | 54.28 | C |
| ATOM | 9713 | C | PRO C | 241 | 6.533 | 19.656 | −37.372 | 1.00 | 55.90 | C |
| ATOM | 9714 | O | PRO C | 241 | 6.984 | 20.668 | −36.858 | 1.00 | 53.72 | O |
| ATOM | 9715 | N | ARG C | 242 | 7.216 | 18.534 | −37.483 | 1.00 | 61.02 | N |
| ATOM | 9716 | CA | ARG C | 242 | 8.569 | 18.426 | −36.980 | 1.00 | 66.20 | C |
| ATOM | 9717 | CB | ARG C | 242 | 9.129 | 17.012 | −37.209 | 1.00 | 71.48 | C |
| ATOM | 9718 | CG | ARG C | 242 | 8.155 | 15.877 | −36.837 | 1.00 | 87.64 | C |
| ATOM | 9719 | CD | ARG C | 242 | 8.838 | 14.516 | −36.607 | 1.00 | 99.23 | C |
| ATOM | 9720 | NE | ARG C | 242 | 8.168 | 13.402 | −37.293 | 1.00 | 94.22 | N |

TABLE 6-continued

Atomic coordinates for CRBN:DDB1: Compound B (Human protein)

| ATOM | 9721 | CZ | ARG C | 242 | 8.156 | 13.218 | −38.619 | 1.00 | 86.41 | C |
|---|---|---|---|---|---|---|---|---|---|---|
| ATOM | 9722 | NH1 | ARG C | 242 | 8.768 | 14.072 | −39.448 | 1.00 | 74.02 | N |
| ATOM | 9723 | NH2 | ARG C | 242 | 7.510 | 12.172 | −39.132 | 1.00 | 95.36 | N |
| ATOM | 9724 | C | ARG C | 242 | 9.432 | 19.500 | −37.664 | 1.00 | 64.77 | C |
| ATOM | 9725 | O | ARG C | 242 | 10.319 | 20.072 | −37.032 | 1.00 | 66.81 | O |
| ATOM | 9726 | N | TRP C | 243 | 9.161 | 19.774 | −38.947 | 1.00 | 62.61 | N |
| ATOM | 9727 | CA | TRP C | 243 | 9.956 | 20.746 | −39.722 | 1.00 | 59.00 | C |
| ATOM | 9728 | CB | TRP C | 243 | 9.796 | 20.600 | −41.252 | 1.00 | 49.73 | C |
| ATOM | 9729 | CG | TRP C | 243 | 8.458 | 20.845 | −41.801 | 1.00 | 44.84 | C |
| ATOM | 9730 | CD1 | TRP C | 243 | 7.538 | 19.902 | −42.094 | 1.00 | 45.53 | C |
| ATOM | 9731 | NE1 | TRP C | 243 | 6.383 | 20.488 | −42.592 | 1.00 | 45.30 | N |
| ATOM | 9732 | CE2 | TRP C | 243 | 6.564 | 21.839 | −42.649 | 1.00 | 41.61 | C |
| ATOM | 9733 | CD2 | TRP C | 243 | 7.872 | 22.106 | −42.159 | 1.00 | 41.95 | C |
| ATOM | 9734 | CE3 | TRP C | 243 | 8.300 | 23.419 | −42.086 | 1.00 | 41.35 | C |
| ATOM | 9735 | CZ3 | TRP C | 243 | 7.416 | 24.423 | −42.502 | 1.00 | 44.23 | C |
| ATOM | 9736 | CH2 | TRP C | 243 | 6.121 | 24.116 | −43.004 | 1.00 | 40.74 | C |
| ATOM | 9737 | CZ2 | TRP C | 243 | 5.686 | 22.836 | −43.075 | 1.00 | 39.38 | C |
| ATOM | 9738 | C | TRP C | 243 | 9.760 | 22.197 | −39.287 | 1.00 | 63.47 | C |
| ATOM | 9739 | O | TRP C | 243 | 10.691 | 22.997 | −39.426 | 1.00 | 67.76 | O |
| ATOM | 9740 | N | LEU C | 244 | 8.585 | 22.534 | −38.755 | 1.00 | 62.07 | N |
| ATOM | 9741 | CA | LEU C | 244 | 8.404 | 23.836 | −38.116 | 1.00 | 60.66 | C |
| ATOM | 9742 | CB | LEU C | 244 | 6.938 | 24.162 | −37.909 | 1.00 | 59.51 | C |
| ATOM | 9743 | CG | LEU C | 244 | 6.702 | 25.488 | −37.192 | 1.00 | 59.78 | C |
| ATOM | 9744 | CD1 | LEU C | 244 | 7.500 | 26.629 | −37.796 | 1.00 | 61.45 | C |
| ATOM | 9745 | CD2 | LEU C | 244 | 5.230 | 25.795 | −37.276 | 1.00 | 64.08 | C |
| ATOM | 9746 | C | LEU C | 244 | 9.118 | 23.913 | −36.769 | 1.00 | 62.02 | C |
| ATOM | 9747 | O | LEU C | 244 | 9.871 | 24.841 | −36.540 | 1.00 | 65.00 | O |
| ATOM | 9748 | N | TYR C | 245 | 8.880 | 22.959 | −35.873 | 1.00 | 60.22 | N |
| ATOM | 9749 | CA | TYR C | 245 | 9.584 | 22.961 | −34.590 | 1.00 | 59.98 | C |
| ATOM | 9750 | CB | TYR C | 245 | 9.134 | 21.784 | −33.675 | 1.00 | 69.13 | C |
| ATOM | 9751 | CG | TYR C | 245 | 7.702 | 21.941 | −33.183 | 1.00 | 58.82 | C |
| ATOM | 9752 | CD1 | TYR C | 245 | 7.375 | 22.935 | −32.281 | 1.00 | 57.57 | C |
| ATOM | 9753 | CE1 | TYR C | 245 | 6.079 | 23.115 | −31.850 | 1.00 | 57.91 | C |
| ATOM | 9754 | CZ | TYR C | 245 | 5.079 | 22.295 | −32.311 | 1.00 | 58.80 | C |
| ATOM | 9755 | OH | TYR C | 245 | 3.811 | 22.540 | −31.861 | 1.00 | 58.40 | O |
| ATOM | 9756 | CE2 | TYR C | 245 | 5.361 | 21.284 | −33.211 | 1.00 | 57.85 | C |
| ATOM | 9757 | CD2 | TYR C | 245 | 6.669 | 21.117 | −33.649 | 1.00 | 61.00 | C |
| ATOM | 9758 | C | TYR C | 245 | 11.124 | 23.019 | −34.787 | 1.00 | 61.17 | C |
| ATOM | 9759 | O | TYR C | 245 | 11.830 | 23.627 | −33.959 | 1.00 | 67.17 | O |
| ATOM | 9760 | N | SER C | 246 | 11.630 | 22.450 | −35.891 | 1.00 | 58.72 | N |
| ATOM | 9761 | CA | SER C | 246 | 13.081 | 22.444 | −36.171 | 1.00 | 60.73 | C |
| ATOM | 9762 | CB | SER C | 246 | 13.443 | 21.467 | −37.321 | 1.00 | 58.19 | C |
| ATOM | 9763 | OG | SER C | 246 | 14.649 | 20.740 | −37.027 | 1.00 | 59.16 | O |
| ATOM | 9764 | C | SER C | 246 | 13.627 | 23.865 | −36.429 | 1.00 | 60.03 | C |
| ATOM | 9765 | O | SER C | 246 | 14.749 | 24.192 | −36.040 | 1.00 | 58.17 | O |
| ATOM | 9766 | N | LEU C | 247 | 12.801 | 24.700 | −37.055 | 1.00 | 60.87 | N |
| ATOM | 9767 | CA | LEU C | 247 | 13.104 | 26.119 | −37.275 | 1.00 | 59.16 | C |
| ATOM | 9768 | CB | LEU C | 247 | 12.094 | 26.738 | −38.256 | 1.00 | 55.85 | C |
| ATOM | 9769 | CG | LEU C | 247 | 12.163 | 26.200 | −39.681 | 1.00 | 54.10 | C |
| ATOM | 9770 | CD1 | LEU C | 247 | 10.986 | 26.677 | −40.513 | 1.00 | 54.36 | C |
| ATOM | 9771 | CD2 | LEU C | 247 | 13.478 | 26.601 | −40.320 | 1.00 | 57.05 | C |
| ATOM | 9772 | C | LEU C | 247 | 13.158 | 26.995 | −36.011 | 1.00 | 61.67 | C |
| ATOM | 9773 | O | LEU C | 247 | 13.624 | 28.130 | −36.103 | 1.00 | 63.33 | O |
| ATOM | 9774 | N | TYR C | 248 | 12.678 | 26.510 | −34.859 | 1.00 | 57.99 | N |
| ATOM | 9775 | CA | TYR C | 248 | 12.933 | 27.188 | −33.581 | 1.00 | 54.97 | C |
| ATOM | 9776 | CB | TYR C | 248 | 11.631 | 27.524 | −32.895 | 1.00 | 55.17 | C |
| ATOM | 9777 | CG | TYR C | 248 | 10.782 | 28.516 | −33.635 | 1.00 | 60.07 | C |
| ATOM | 9778 | CD1 | TYR C | 248 | 9.838 | 28.101 | −34.568 | 1.00 | 60.73 | C |
| ATOM | 9779 | CE1 | TYR C | 248 | 9.016 | 29.018 | −35.218 | 1.00 | 61.48 | C |
| ATOM | 9780 | CZ | TYR C | 248 | 9.144 | 30.362 | −34.953 | 1.00 | 61.97 | C |
| ATOM | 9781 | OH | TYR C | 248 | 8.350 | 31.273 | −35.595 | 1.00 | 61.64 | O |
| ATOM | 9782 | CE2 | TYR C | 248 | 10.073 | 30.797 | −34.030 | 1.00 | 65.85 | C |
| ATOM | 9783 | CD2 | TYR C | 248 | 10.883 | 29.875 | −33.372 | 1.00 | 63.01 | C |
| ATOM | 9784 | C | TYR C | 248 | 13.814 | 26.382 | −32.639 | 1.00 | 51.69 | C |
| ATOM | 9785 | O | TYR C | 248 | 13.725 | 26.541 | −31.419 | 1.00 | 55.77 | O |
| ATOM | 9786 | N | ASP C | 249 | 14.698 | 25.559 | −33.194 | 1.00 | 47.71 | N |
| ATOM | 9787 | CA | ASP C | 249 | 15.507 | 24.649 | −32.377 | 1.00 | 49.29 | C |
| ATOM | 9788 | CB | ASP C | 249 | 15.516 | 23.218 | −32.983 | 1.00 | 50.49 | C |
| ATOM | 9789 | CG | ASP C | 249 | 16.340 | 22.188 | −32.141 | 1.00 | 50.38 | C |
| ATOM | 9790 | OD1 | ASP C | 249 | 16.167 | 22.001 | −30.924 | 1.00 | 48.46 | O |
| ATOM | 9791 | OD2 | ASP C | 249 | 17.168 | 21.512 | −32.740 | 1.00 | 55.10 | O |
| ATOM | 9792 | C | ASP C | 249 | 16.905 | 25.165 | −32.304 | 1.00 | 45.92 | C |
| ATOM | 9793 | O | ASP C | 249 | 17.575 | 25.144 | −33.320 | 1.00 | 50.53 | O |
| ATOM | 9794 | N | ALA C | 250 | 17.378 | 25.559 | −31.121 | 1.00 | 44.56 | N |
| ATOM | 9795 | CA | ALA C | 250 | 18.735 | 26.143 | −30.994 | 1.00 | 44.29 | C |
| ATOM | 9796 | CB | ALA C | 250 | 19.220 | 26.290 | −29.547 | 1.00 | 38.91 | C |
| ATOM | 9797 | C | ALA C | 250 | 19.730 | 25.331 | −31.805 | 1.00 | 50.14 | C |
| ATOM | 9798 | O | ALA C | 250 | 20.396 | 25.867 | −32.689 | 1.00 | 60.18 | O |

TABLE 6-continued

Atomic coordinates for CRBN:DDB1: Compound B (Human protein)

| ATOM | 9799 | N | GLU C | 251 | 19.782 | 24.038 | −31.551 | 1.00 | 53.06 | N |
|---|---|---|---|---|---|---|---|---|---|---|
| ATOM | 9800 | CA | GLU C | 251 | 20.836 | 23.197 | −32.093 | 1.00 | 56.16 | C |
| ATOM | 9801 | CB | GLU C | 251 | 20.732 | 21.813 | −31.454 | 1.00 | 66.43 | C |
| ATOM | 9802 | CG | GLU C | 251 | 21.479 | 21.695 | −30.141 | 1.00 | 71.00 | C |
| ATOM | 9803 | CD | GLU C | 251 | 22.997 | 21.734 | −30.346 | 1.00 | 77.05 | C |
| ATOM | 9804 | OE1 | GLU C | 251 | 23.491 | 21.584 | −31.525 | 1.00 | 77.89 | O |
| ATOM | 9805 | OE2 | GLU C | 251 | 23.683 | 21.926 | −29.302 | 1.00 | 78.52 | O |
| ATOM | 9806 | C | GLU C | 251 | 20.813 | 23.091 | −33.608 | 1.00 | 51.73 | C |
| ATOM | 9807 | O | GLU C | 251 | 21.848 | 23.229 | −34.246 | 1.00 | 50.63 | O |
| ATOM | 9808 | N | THR C | 252 | 19.636 | 22.850 | −34.167 | 1.00 | 49.50 | N |
| ATOM | 9809 | CA | THR C | 252 | 19.466 | 22.911 | −35.590 | 1.00 | 50.62 | C |
| ATOM | 9810 | CB | THR C | 252 | 17.995 | 22.683 | −36.046 | 1.00 | 51.12 | C |
| ATOM | 9811 | OG1 | THR C | 252 | 17.437 | 21.437 | −35.604 | 1.00 | 49.00 | O |
| ATOM | 9812 | CG2 | THR C | 252 | 17.960 | 22.700 | −37.557 | 1.00 | 53.71 | C |
| ATOM | 9813 | C | THR C | 252 | 19.946 | 24.324 | −36.103 | 1.00 | 51.51 | C |
| ATOM | 9814 | O | THR C | 252 | 20.736 | 24.413 | −37.043 | 1.00 | 51.17 | O |
| ATOM | 9815 | N | LEU C | 253 | 19.473 | 25.413 | −35.489 | 1.00 | 50.28 | N |
| ATOM | 9816 | CA | LEU C | 253 | 19.836 | 26.783 | −35.916 | 1.00 | 49.76 | C |
| ATOM | 9817 | CB | LEU C | 253 | 19.091 | 27.819 | −35.081 | 1.00 | 52.09 | C |
| ATOM | 9818 | CG | LEU C | 253 | 17.553 | 27.919 | −35.132 | 1.00 | 54.12 | C |
| ATOM | 9819 | CD1 | LEU C | 253 | 17.022 | 28.637 | −33.904 | 1.00 | 55.56 | C |
| ATOM | 9820 | CD2 | LEU C | 253 | 17.087 | 28.682 | −36.347 | 1.00 | 54.30 | C |
| ATOM | 9821 | C | LEU C | 253 | 21.340 | 27.084 | −35.801 | 1.00 | 50.33 | C |
| ATOM | 9822 | O | LEU C | 253 | 21.893 | 27.774 | −36.639 | 1.00 | 46.58 | O |
| ATOM | 9823 | N | MET C | 254 | 22.006 | 26.592 | −34.752 | 1.00 | 54.36 | N |
| ATOM | 9824 | CA | MET C | 254 | 23.466 | 26.767 | −34.617 | 1.00 | 54.30 | C |
| ATOM | 9825 | CB | MET C | 254 | 24.001 | 26.298 | −33.264 | 1.00 | 58.02 | C |
| ATOM | 9826 | CG | MET C | 254 | 23.645 | 27.221 | −32.105 | 1.00 | 62.52 | C |
| ATOM | 9827 | SD | MET C | 254 | 24.347 | 26.667 | −30.522 | 1.00 | 69.15 | S |
| ATOM | 9828 | CE | MET C | 254 | 22.901 | 25.870 | −29.873 | 1.00 | 66.84 | C |
| ATOM | 9829 | C | MET C | 254 | 24.166 | 26.037 | −35.737 | 1.00 | 52.91 | C |
| ATOM | 9830 | O | MET C | 254 | 25.002 | 26.608 | −36.402 | 1.00 | 48.43 | O |
| ATOM | 9831 | N | ASP C | 255 | 23.800 | 24.787 | −35.987 | 1.00 | 55.59 | N |
| ATOM | 9832 | CA | ASP C | 255 | 24.431 | 24.066 | −37.093 | 1.00 | 57.64 | C |
| ATOM | 9833 | CB | ASP C | 255 | 24.007 | 22.586 | −37.073 | 1.00 | 61.03 | C |
| ATOM | 9834 | CG | ASP C | 255 | 24.623 | 21.766 | −38.234 | 1.00 | 65.64 | C |
| ATOM | 9835 | OD1 | ASP C | 255 | 25.822 | 21.383 | −38.033 | 1.00 | 64.58 | O |
| ATOM | 9836 | OD2 | ASP C | 255 | 23.895 | 21.519 | −39.289 | 1.00 | 57.57 | O |
| ATOM | 9837 | C | ASP C | 255 | 24.214 | 24.763 | −38.488 | 1.00 | 52.82 | C |
| ATOM | 9838 | O | ASP C | 255 | 25.106 | 24.799 | −39.318 | 1.00 | 48.47 | O |
| ATOM | 9839 | N | ARG C | 256 | 23.051 | 25.345 | −38.725 | 1.00 | 51.66 | N |
| ATOM | 9840 | CA | ARG C | 256 | 22.809 | 26.075 | −39.990 | 1.00 | 53.45 | C |
| ATOM | 9841 | CB | ARG C | 256 | 21.318 | 26.459 | −40.108 | 1.00 | 51.60 | C |
| ATOM | 9842 | CG | ARG C | 256 | 20.422 | 25.308 | −40.514 | 1.00 | 49.55 | C |
| ATOM | 9843 | CD | ARG C | 256 | 18.974 | 25.687 | −40.429 | 1.00 | 49.04 | C |
| ATOM | 9844 | NE | ARG C | 256 | 18.677 | 26.752 | −41.361 | 1.00 | 49.06 | N |
| ATOM | 9845 | CZ | ARG C | 256 | 17.658 | 27.611 | −41.269 | 1.00 | 53.96 | C |
| ATOM | 9846 | NH1 | ARG C | 256 | 16.746 | 27.547 | −40.289 | 1.00 | 58.53 | N |
| ATOM | 9847 | NH2 | ARG C | 256 | 17.539 | 28.570 | −42.182 | 1.00 | 55.13 | N |
| ATOM | 9848 | C | ARG C | 256 | 23.720 | 27.321 | −40.171 | 1.00 | 54.69 | C |
| ATOM | 9849 | O | ARG C | 256 | 24.292 | 27.560 | −41.262 | 1.00 | 53.34 | O |
| ATOM | 9850 | N | ILE C | 257 | 23.841 | 28.092 | −39.091 | 1.00 | 56.12 | N |
| ATOM | 9851 | CA | ILE C | 257 | 24.777 | 29.206 | −39.038 | 1.00 | 60.71 | C |
| ATOM | 9852 | CB | ILE C | 257 | 24.701 | 30.008 | −37.710 | 1.00 | 58.11 | C |
| ATOM | 9853 | CG1 | ILE C | 257 | 23.324 | 30.613 | −37.524 | 1.00 | 55.91 | C |
| ATOM | 9854 | CD1 | ILE C | 257 | 23.045 | 30.854 | −36.075 | 1.00 | 57.77 | C |
| ATOM | 9855 | CG2 | ILE C | 257 | 25.758 | 31.126 | −37.667 | 1.00 | 57.74 | C |
| ATOM | 9856 | C | ILE C | 257 | 26.217 | 28.696 | −39.224 | 1.00 | 63.16 | C |
| ATOM | 9857 | O | ILE C | 257 | 27.014 | 29.352 | −39.888 | 1.00 | 72.69 | O |
| ATOM | 9858 | N | LYS C | 258 | 26.547 | 27.541 | −38.656 | 1.00 | 61.72 | N |
| ATOM | 9859 | CA | LYS C | 258 | 27.900 | 27.034 | −38.749 | 1.00 | 60.94 | C |
| ATOM | 9860 | CB | LYS C | 258 | 28.093 | 25.782 | −37.941 | 1.00 | 62.36 | C |
| ATOM | 9861 | CG | LYS C | 258 | 28.266 | 26.002 | −36.475 | 1.00 | 66.71 | C |
| ATOM | 9862 | CD | LYS C | 258 | 28.283 | 24.634 | −35.830 | 1.00 | 73.39 | C |
| ATOM | 9863 | CE | LYS C | 258 | 28.892 | 24.645 | −34.448 | 1.00 | 77.70 | C |
| ATOM | 9864 | NZ | LYS C | 258 | 28.819 | 23.248 | −33.957 | 1.00 | 79.38 | N |
| ATOM | 9865 | C | LYS C | 258 | 28.284 | 26.718 | −40.152 | 1.00 | 62.35 | C |
| ATOM | 9866 | O | LYS C | 258 | 29.441 | 26.497 | −40.408 | 1.00 | 67.86 | O |
| ATOM | 9867 | N | LYS C | 259 | 27.332 | 26.668 | −41.062 | 1.00 | 66.64 | N |
| ATOM | 9868 | CA | LYS C | 259 | 27.664 | 26.402 | −42.426 | 1.00 | 71.48 | C |
| ATOM | 9869 | CB | LYS C | 259 | 26.544 | 25.658 | −43.093 | 1.00 | 72.80 | C |
| ATOM | 9870 | CG | LYS C | 259 | 26.548 | 24.249 | −42.571 | 1.00 | 76.72 | C |
| ATOM | 9871 | CD | LYS C | 259 | 25.215 | 23.558 | −42.660 | 1.00 | 81.57 | C |
| ATOM | 9872 | CE | LYS C | 259 | 25.395 | 22.118 | −42.210 | 1.00 | 88.20 | C |
| ATOM | 9873 | NZ | LYS C | 259 | 24.368 | 21.263 | −42.852 | 1.00 | 95.48 | N |
| ATOM | 9874 | C | LYS C | 259 | 28.064 | 27.646 | −43.159 | 1.00 | 79.30 | C |
| ATOM | 9875 | O | LYS C | 259 | 29.022 | 27.541 | −43.906 | 1.00 | 90.65 | O |
| ATOM | 9876 | N | GLN C | 260 | 27.425 | 28.819 | −42.950 | 1.00 | 86.51 | N |

TABLE 6-continued

Atomic coordinates for CRBN:DDB1: Compound B (Human protein)

| ATOM | 9877 | CA | GLN C | 260 | 28.027 | 30.095 | −43.522 | 1.00 | 91.27 | C |
|---|---|---|---|---|---|---|---|---|---|---|
| ATOM | 9878 | CB | GLN C | 260 | 27.149 | 31.400 | −43.633 | 1.00 | 94.88 | C |
| ATOM | 9879 | CG | GLN C | 260 | 25.625 | 31.355 | −43.427 | 1.00 | 104.21 | C |
| ATOM | 9880 | CD | GLN C | 260 | 24.806 | 30.468 | −44.379 | 1.00 | 102.82 | C |
| ATOM | 9881 | OE1 | GLN C | 260 | 23.562 | 30.512 | −44.369 | 1.00 | 92.30 | O |
| ATOM | 9882 | NE2 | GLN C | 260 | 25.482 | 29.647 | −45.169 | 1.00 | 103.01 | N |
| ATOM | 9883 | C | GLN C | 260 | 29.349 | 30.400 | −42.813 | 1.00 | 78.57 | C |
| ATOM | 9884 | O | GLN C | 260 | 30.259 | 30.922 | −43.430 | 1.00 | 85.82 | O |
| ATOM | 9885 | N | LEU C | 261 | 29.476 | 30.037 | −41.553 | 1.00 | 68.99 | N |
| ATOM | 9886 | CA | LEU C | 261 | 30.778 | 30.120 | −40.886 | 1.00 | 71.21 | C |
| ATOM | 9887 | CB | LEU C | 261 | 30.642 | 29.922 | −39.365 | 1.00 | 67.62 | C |
| ATOM | 9888 | CG | LEU C | 261 | 29.826 | 30.958 | −38.572 | 1.00 | 67.41 | C |
| ATOM | 9889 | CD1 | LEU C | 261 | 29.905 | 30.630 | −37.091 | 1.00 | 65.89 | C |
| ATOM | 9890 | CD2 | LEU C | 261 | 30.286 | 32.400 | −38.838 | 1.00 | 69.25 | C |
| ATOM | 9891 | C | LEU C | 261 | 31.865 | 29.171 | −41.428 | 1.00 | 74.55 | C |
| ATOM | 9892 | O | LEU C | 261 | 33.051 | 29.528 | −41.404 | 1.00 | 75.53 | O |
| ATOM | 9893 | N | ARG C | 262 | 31.491 | 27.976 | −41.889 | 1.00 | 79.28 | N |
| ATOM | 9894 | CA | ARG C | 262 | 32.478 | 27.057 | −42.476 | 1.00 | 82.08 | C |
| ATOM | 9895 | CB | ARG C | 262 | 31.924 | 25.639 | −42.661 | 1.00 | 90.78 | C |
| ATOM | 9896 | CG | ARG C | 262 | 32.963 | 24.516 | −42.517 | 1.00 | 100.04 | C |
| ATOM | 9897 | CD | ARG C | 262 | 32.319 | 23.114 | −42.464 | 1.00 | 107.07 | C |
| ATOM | 9898 | NE | ARG C | 262 | 31.336 | 22.962 | −41.369 | 1.00 | 108.21 | N |
| ATOM | 9899 | CZ | ARG C | 262 | 31.627 | 22.768 | −40.077 | 1.00 | 108.25 | C |
| ATOM | 9900 | NH1 | ARG C | 262 | 32.892 | 22.682 | −39.650 | 1.00 | 112.35 | N |
| ATOM | 9901 | NH2 | ARG C | 262 | 30.641 | 22.668 | −39.185 | 1.00 | 104.36 | N |
| ATOM | 9902 | C | ARG C | 262 | 33.002 | 27.598 | −43.804 | 1.00 | 78.74 | C |
| ATOM | 9903 | O | ARG C | 262 | 34.153 | 27.358 | −44.125 | 1.00 | 87.52 | O |
| ATOM | 9904 | N | GLU C | 263 | 32.211 | 28.342 | −44.554 | 1.00 | 71.98 | N |
| ATOM | 9905 | CA | GLU C | 263 | 32.752 | 28.851 | −45.795 | 1.00 | 75.35 | C |
| ATOM | 9906 | CB | GLU C | 263 | 31.684 | 29.109 | −46.826 | 1.00 | 78.86 | C |
| ATOM | 9907 | CG | GLU C | 263 | 30.637 | 30.077 | −46.401 | 1.00 | 87.82 | C |
| ATOM | 9908 | CD | GLU C | 263 | 29.562 | 30.167 | −47.436 | 1.00 | 96.74 | C |
| ATOM | 9909 | OE1 | GLU C | 263 | 29.232 | 29.123 | −48.019 | 1.00 | 89.56 | O |
| ATOM | 9910 | OE2 | GLU C | 263 | 29.060 | 31.277 | −47.668 | 1.00 | 107.65 | O |
| ATOM | 9911 | C | GLU C | 263 | 33.663 | 30.043 | −45.583 | 1.00 | 73.97 | C |
| ATOM | 9912 | O | GLU C | 263 | 34.587 | 30.251 | −46.338 | 1.00 | 77.78 | O |
| ATOM | 9913 | N | TRP C | 264 | 33.398 | 30.842 | −44.570 | 1.00 | 73.71 | N |
| ATOM | 9914 | CA | TRP C | 264 | 34.290 | 31.928 | −44.233 | 1.00 | 71.00 | C |
| ATOM | 9915 | CB | TRP C | 264 | 33.669 | 32.833 | −43.196 | 1.00 | 70.18 | C |
| ATOM | 9916 | CG | TRP C | 264 | 32.533 | 33.574 | −43.746 | 1.00 | 66.22 | C |
| ATOM | 9917 | CD1 | TRP C | 264 | 32.217 | 33.709 | −45.047 | 1.00 | 66.03 | C |
| ATOM | 9918 | NE1 | TRP C | 264 | 31.105 | 34.475 | −45.188 | 1.00 | 63.82 | N |
| ATOM | 9919 | CE2 | TRP C | 264 | 30.683 | 34.857 | −43.950 | 1.00 | 60.86 | C |
| ATOM | 9920 | CD2 | TRP C | 264 | 31.566 | 34.312 | −43.023 | 1.00 | 63.81 | C |
| ATOM | 9921 | CE3 | TRP C | 264 | 31.348 | 34.551 | −41.676 | 1.00 | 66.60 | C |
| ATOM | 9922 | CZ3 | TRP C | 264 | 30.289 | 35.315 | −41.316 | 1.00 | 68.19 | C |
| ATOM | 9923 | CH2 | TRP C | 264 | 29.440 | 35.850 | −42.259 | 1.00 | 63.45 | C |
| ATOM | 9924 | CZ2 | TRP C | 264 | 29.617 | 35.630 | −43.582 | 1.00 | 59.24 | C |
| ATOM | 9925 | C | TRP C | 264 | 35.550 | 31.261 | −43.713 | 1.00 | 76.45 | C |
| ATOM | 9926 | O | TRP C | 264 | 36.656 | 31.680 | −43.982 | 1.00 | 70.93 | O |
| ATOM | 9927 | N | ASP C | 265 | 35.329 | 30.194 | −42.952 | 1.00 | 85.62 | N |
| ATOM | 9928 | CA | ASP C | 265 | 36.351 | 29.333 | −42.359 | 1.00 | 82.69 | C |
| ATOM | 9929 | CB | ASP C | 265 | 37.355 | 28.885 | −43.407 | 1.00 | 83.49 | C |
| ATOM | 9930 | CG | ASP C | 265 | 37.785 | 27.454 | −43.221 | 1.00 | 85.85 | C |
| ATOM | 9931 | OD1 | ASP C | 265 | 38.205 | 27.102 | −42.107 | 1.00 | 87.40 | O |
| ATOM | 9932 | OD2 | ASP C | 265 | 37.712 | 26.680 | −44.190 | 1.00 | 79.43 | O |
| ATOM | 9933 | C | ASP C | 265 | 37.062 | 29.924 | −41.170 | 1.00 | 82.49 | C |
| ATOM | 9934 | O | ASP C | 265 | 37.949 | 29.298 | −40.610 | 1.00 | 73.71 | O |
| ATOM | 9935 | N | ASP C | 270 | 35.989 | 25.968 | −39.580 | 1.00 | 72.36 | N |
| ATOM | 9936 | CA | ASP C | 270 | 37.196 | 25.746 | −39.547 | 1.00 | 86.48 | C |
| ATOM | 9937 | CB | ASP C | 270 | 38.271 | 25.746 | −40.478 | 1.00 | 82.60 | C |
| ATOM | 9938 | C | ASP C | 270 | 37.639 | 25.229 | −38.122 | 1.00 | 90.78 | C |
| ATOM | 9939 | O | ASP C | 270 | 38.719 | 25.713 | −37.824 | 1.00 | 84.79 | O |
| ATOM | 9940 | N | ASP C | 271 | 36.785 | 24.739 | −37.232 | 1.00 | 101.59 | N |
| ATOM | 9941 | CA | ASP C | 271 | 37.093 | 24.762 | −35.815 | 1.00 | 107.33 | C |
| ATOM | 9942 | CB | ASP C | 271 | 37.585 | 26.145 | −35.409 | 1.00 | 103.38 | C |
| ATOM | 9943 | C | ASP C | 271 | 35.920 | 24.375 | −34.937 | 1.00 | 112.23 | C |
| ATOM | 9944 | O | ASP C | 271 | 34.952 | 23.773 | −35.391 | 1.00 | 100.91 | O |
| ATOM | 9945 | N | SER C | 272 | 36.046 | 24.719 | −33.661 | 1.00 | 122.93 | N |
| ATOM | 9946 | CA | SER C | 272 | 35.035 | 24.452 | −32.651 | 1.00 | 122.81 | C |
| ATOM | 9947 | CB | SER C | 272 | 35.590 | 23.527 | −31.584 | 1.00 | 110.79 | C |
| ATOM | 9948 | OG | SER C | 272 | 36.162 | 22.390 | −32.187 | 1.00 | 101.24 | O |
| ATOM | 9949 | C | SER C | 272 | 34.552 | 25.753 | −32.020 | 1.00 | 121.46 | C |
| ATOM | 9950 | O | SER C | 272 | 35.337 | 26.653 | −31.724 | 1.00 | 103.59 | O |
| ATOM | 9951 | N | LEU C | 273 | 33.242 | 25.832 | −31.820 | 1.00 | 123.28 | N |
| ATOM | 9952 | CA | LEU C | 273 | 32.585 | 27.003 | −31.259 | 1.00 | 116.79 | C |
| ATOM | 9953 | CB | LEU C | 273 | 31.741 | 27.703 | −32.306 | 1.00 | 117.04 | C |
| ATOM | 9954 | CG | LEU C | 273 | 32.512 | 28.587 | −33.274 | 1.00 | 114.95 | C |

TABLE 6-continued

Atomic coordinates for CRBN:DDB1: Compound B (Human protein)

| ATOM | 9955 | CD1 | LEU C | 273 | 33.927 | 28.095 | −33.522 | 1.00 | 115.59 | C |
|---|---|---|---|---|---|---|---|---|---|---|
| ATOM | 9956 | CD2 | LEU C | 273 | 31.741 | 28.670 | −34.571 | 1.00 | 107.70 | C |
| ATOM | 9957 | C | LEU C | 273 | 31.748 | 26.668 | −30.050 | 1.00 | 111.56 | C |
| ATOM | 9958 | O | LEU C | 273 | 31.462 | 25.512 | −29.771 | 1.00 | 121.15 | O |
| ATOM | 9959 | N | PRO C | 274 | 31.362 | 27.762 | −29.300 | 1.00 | 106.85 | N |
| ATOM | 9960 | CA | PRO C | 274 | 30.634 | 27.433 | −28.068 | 1.00 | 104.93 | C |
| ATOM | 9961 | CB | PRO C | 274 | 30.226 | 28.802 | −27.520 | 1.00 | 102.73 | C |
| ATOM | 9962 | CG | PRO C | 274 | 31.201 | 29.751 | −28.056 | 1.00 | 102.92 | C |
| ATOM | 9963 | CD | PRO C | 274 | 31.344 | 29.285 | −29.450 | 1.00 | 105.09 | C |
| ATOM | 9964 | C | PRO C | 274 | 29.372 | 26.595 | −28.091 | 1.00 | 102.65 | C |
| ATOM | 9965 | O | PRO C | 274 | 28.454 | 26.893 | −28.820 | 1.00 | 105.18 | O |
| ATOM | 9966 | N | SER C | 275 | 29.327 | 25.567 | −27.257 | 1.00 | 95.38 | N |
| ATOM | 9967 | CA | SER C | 275 | 28.097 | 24.797 | −27.045 | 1.00 | 84.85 | C |
| ATOM | 9968 | CB | SER C | 275 | 28.280 | 23.803 | −25.882 | 1.00 | 85.79 | C |
| ATOM | 9969 | OG | SER C | 275 | 29.646 | 23.635 | −25.544 | 1.00 | 87.81 | O |
| ATOM | 9970 | C | SER C | 275 | 26.892 | 25.719 | −26.722 | 1.00 | 77.02 | C |
| ATOM | 9971 | O | SER C | 275 | 25.804 | 25.534 | −27.244 | 1.00 | 70.76 | O |
| ATOM | 9972 | N | ASN C | 276 | 27.078 | 26.717 | −25.864 | 1.00 | 72.54 | N |
| ATOM | 9973 | CA | ASN C | 276 | 25.931 | 27.481 | −25.408 | 1.00 | 67.97 | C |
| ATOM | 9974 | CB | ASN C | 276 | 26.292 | 28.373 | −24.230 | 1.00 | 70.85 | C |
| ATOM | 9975 | CG | ASN C | 276 | 25.056 | 28.861 | −23.484 | 1.00 | 76.37 | C |
| ATOM | 9976 | OD1 | ASN C | 276 | 24.215 | 29.592 | −24.025 | 1.00 | 81.18 | O |
| ATOM | 9977 | ND2 | ASN C | 276 | 24.928 | 28.449 | −22.239 | 1.00 | 78.65 | N |
| ATOM | 9978 | C | ASN C | 276 | 25.253 | 28.327 | −26.511 | 1.00 | 65.01 | C |
| ATOM | 9979 | O | ASN C | 276 | 25.871 | 29.216 | −27.124 | 1.00 | 63.06 | O |
| ATOM | 9980 | N | PRO C | 277 | 23.964 | 28.085 | −26.742 | 1.00 | 58.92 | N |
| ATOM | 9981 | CA | PRO C | 277 | 23.190 | 29.007 | −27.565 | 1.00 | 59.42 | C |
| ATOM | 9982 | CB | PRO C | 277 | 21.754 | 28.586 | −27.311 | 1.00 | 56.38 | C |
| ATOM | 9983 | CG | PRO C | 277 | 21.822 | 27.216 | −26.794 | 1.00 | 55.10 | C |
| ATOM | 9984 | CD | PRO C | 277 | 23.141 | 27.032 | −26.154 | 1.00 | 55.93 | C |
| ATOM | 9985 | C | PRO C | 277 | 23.389 | 30.521 | −27.241 | 1.00 | 61.01 | C |
| ATOM | 9986 | O | PRO C | 277 | 23.714 | 31.275 | −28.125 | 1.00 | 75.08 | O |
| ATOM | 9987 | N | ILE C | 278 | 23.238 | 30.976 | −26.014 | 1.00 | 61.07 | N |
| ATOM | 9988 | CA | ILE C | 278 | 23.538 | 32.379 | −25.728 | 1.00 | 61.43 | C |
| ATOM | 9989 | CB | ILE C | 278 | 23.586 | 32.646 | −24.229 | 1.00 | 57.67 | C |
| ATOM | 9990 | CG1 | ILE C | 278 | 22.212 | 32.512 | −23.642 | 1.00 | 57.15 | C |
| ATOM | 9991 | CD1 | ILE C | 278 | 22.261 | 32.240 | −22.170 | 1.00 | 60.10 | C |
| ATOM | 9992 | CG2 | ILE C | 278 | 24.052 | 34.062 | −23.990 | 1.00 | 59.03 | C |
| ATOM | 9993 | C | ILE C | 278 | 24.916 | 32.803 | −26.301 | 1.00 | 64.79 | C |
| ATOM | 9994 | O | ILE C | 278 | 25.043 | 33.798 | −27.058 | 1.00 | 55.87 | O |
| ATOM | 9995 | N | ASP C | 279 | 25.939 | 32.030 | −25.921 | 1.00 | 66.93 | N |
| ATOM | 9996 | CA | ASP C | 279 | 27.328 | 32.364 | −26.249 | 1.00 | 67.06 | C |
| ATOM | 9997 | CB | ASP C | 279 | 28.317 | 31.455 | −25.509 | 1.00 | 70.56 | C |
| ATOM | 9998 | CG | ASP C | 279 | 28.299 | 31.684 | −23.995 | 1.00 | 75.30 | C |
| ATOM | 9999 | OD1 | ASP C | 279 | 27.588 | 32.601 | −23.495 | 1.00 | 75.41 | O |
| ATOM | 10000 | OD2 | ASP C | 279 | 28.999 | 30.929 | −23.302 | 1.00 | 82.09 | O |
| ATOM | 10001 | C | ASP C | 279 | 27.556 | 32.324 | −27.733 | 1.00 | 59.14 | C |
| ATOM | 10002 | O | ASP C | 279 | 27.944 | 33.311 | −28.330 | 1.00 | 61.45 | O |
| ATOM | 10003 | N | PHE C | 280 | 27.268 | 31.199 | −28.335 | 1.00 | 53.48 | N |
| ATOM | 10004 | CA | PHE C | 280 | 27.249 | 31.137 | −29.785 | 1.00 | 52.81 | C |
| ATOM | 10005 | CB | PHE C | 280 | 26.538 | 29.861 | −30.257 | 1.00 | 52.64 | C |
| ATOM | 10006 | CG | PHE C | 280 | 26.758 | 29.547 | −31.700 | 1.00 | 51.37 | C |
| ATOM | 10007 | CD2 | PHE C | 280 | 25.860 | 29.964 | −32.651 | 1.00 | 51.85 | C |
| ATOM | 10008 | CE2 | PHE C | 280 | 26.040 | 29.677 | −33.984 | 1.00 | 52.24 | C |
| ATOM | 10009 | CZ | PHE C | 280 | 27.145 | 28.957 | −34.373 | 1.00 | 56.25 | C |
| ATOM | 10010 | CE1 | PHE C | 280 | 28.050 | 28.518 | −33.415 | 1.00 | 57.45 | C |
| ATOM | 10011 | CD1 | PHE C | 280 | 27.854 | 28.830 | −32.090 | 1.00 | 53.95 | C |
| ATOM | 10012 | C | PHE C | 280 | 26.568 | 32.374 | −30.376 | 1.00 | 48.86 | C |
| ATOM | 10013 | O | PHE C | 280 | 27.170 | 33.096 | −31.157 | 1.00 | 49.19 | O |
| ATOM | 10014 | N | SER C | 281 | 25.343 | 32.640 | −29.959 | 1.00 | 45.41 | N |
| ATOM | 10015 | CA | SER C | 281 | 24.576 | 33.699 | −30.554 | 1.00 | 47.73 | C |
| ATOM | 10016 | CB | SER C | 281 | 23.148 | 33.763 | −29.987 | 1.00 | 49.00 | C |
| ATOM | 10017 | OG | SER C | 281 | 23.103 | 34.532 | −28.801 | 1.00 | 51.42 | O |
| ATOM | 10018 | C | SER C | 281 | 25.261 | 35.075 | −30.445 | 1.00 | 48.28 | C |
| ATOM | 10019 | O | SER C | 281 | 25.157 | 35.877 | −31.367 | 1.00 | 45.65 | O |
| ATOM | 10020 | N | TYR C | 282 | 25.952 | 35.336 | −29.335 | 1.00 | 49.76 | N |
| ATOM | 10021 | CA | TYR C | 282 | 26.722 | 36.591 | −29.182 | 1.00 | 49.30 | C |
| ATOM | 10022 | CB | TYR C | 282 | 27.046 | 36.907 | −27.716 | 1.00 | 47.42 | C |
| ATOM | 10023 | CG | TYR C | 282 | 25.877 | 37.453 | −26.984 | 1.00 | 46.84 | C |
| ATOM | 10024 | CD1 | TYR C | 282 | 25.106 | 38.450 | −27.536 | 1.00 | 49.64 | C |
| ATOM | 10025 | CE1 | TYR C | 282 | 24.004 | 38.937 | −26.901 | 1.00 | 51.66 | C |
| ATOM | 10026 | CZ | TYR C | 282 | 23.681 | 38.435 | −25.687 | 1.00 | 51.99 | C |
| ATOM | 10027 | OH | TYR C | 282 | 22.593 | 38.953 | −25.053 | 1.00 | 67.24 | O |
| ATOM | 10028 | CE2 | TYR C | 282 | 24.402 | 37.427 | −25.118 | 1.00 | 47.77 | C |
| ATOM | 10029 | CD2 | TYR C | 282 | 25.497 | 36.939 | −25.775 | 1.00 | 47.04 | C |
| ATOM | 10030 | C | TYR C | 282 | 28.009 | 36.616 | −29.978 | 1.00 | 52.26 | C |
| ATOM | 10031 | O | TYR C | 282 | 28.453 | 37.678 | −30.407 | 1.00 | 53.45 | O |
| ATOM | 10032 | N | ARG C | 283 | 28.600 | 35.451 | −30.157 | 1.00 | 56.28 | N |

TABLE 6-continued

Atomic coordinates for CRBN:DDB1: Compound B (Human protein)

| ATOM | 10033 | CA | ARG C | 283 | 29.750 | 35.344 | −30.997 | 1.00 | 59.67 | C |
|---|---|---|---|---|---|---|---|---|---|---|
| ATOM | 10034 | CB | ARG C | 283 | 30.350 | 33.944 | −30.916 | 1.00 | 69.46 | C |
| ATOM | 10035 | CG | ARG C | 283 | 31.779 | 33.862 | −31.427 | 1.00 | 82.10 | C |
| ATOM | 10036 | CD | ARG C | 283 | 32.791 | 34.581 | −30.523 | 1.00 | 89.24 | C |
| ATOM | 10037 | NE | ARG C | 283 | 33.820 | 33.622 | −30.126 | 1.00 | 100.19 | N |
| ATOM | 10038 | CZ | ARG C | 283 | 33.733 | 32.769 | −29.092 | 1.00 | 109.61 | C |
| ATOM | 10039 | NH1 | ARG C | 283 | 34.740 | 31.918 | −28.855 | 1.00 | 112.90 | N |
| ATOM | 10040 | NH2 | ARG C | 283 | 32.674 | 32.764 | −28.269 | 1.00 | 109.41 | N |
| ATOM | 10041 | C | ARG C | 283 | 29.359 | 35.703 | −32.429 | 1.00 | 53.64 | C |
| ATOM | 10042 | O | ARG C | 283 | 30.011 | 36.530 | −33.034 | 1.00 | 46.54 | O |
| ATOM | 10043 | N | VAL C | 284 | 28.283 | 35.138 | −32.966 | 1.00 | 50.99 | N |
| ATOM | 10044 | CA | VAL C | 284 | 28.090 | 35.313 | −34.388 | 1.00 | 52.17 | C |
| ATOM | 10045 | CB | VAL C | 284 | 27.199 | 34.258 | −35.128 | 1.00 | 55.21 | C |
| ATOM | 10046 | CG1 | VAL C | 284 | 27.021 | 32.991 | −34.310 | 1.00 | 56.37 | C |
| ATOM | 10047 | CG2 | VAL C | 284 | 25.865 | 34.824 | −35.637 | 1.00 | 53.87 | C |
| ATOM | 10048 | C | VAL C | 284 | 27.627 | 36.719 | −34.576 | 1.00 | 52.13 | C |
| ATOM | 10049 | O | VAL C | 284 | 27.886 | 37.304 | −35.613 | 1.00 | 56.73 | O |
| ATOM | 10050 | N | ALA C | 285 | 26.970 | 37.272 | −33.570 | 1.00 | 51.83 | N |
| ATOM | 10051 | CA | ALA C | 285 | 26.529 | 38.665 | −33.631 | 1.00 | 52.06 | C |
| ATOM | 10052 | CB | ALA C | 285 | 25.948 | 39.109 | −32.310 | 1.00 | 51.27 | C |
| ATOM | 10053 | C | ALA C | 285 | 27.638 | 39.594 | −34.012 | 1.00 | 54.02 | C |
| ATOM | 10054 | O | ALA C | 285 | 27.415 | 40.497 | −34.831 | 1.00 | 59.06 | O |
| ATOM | 10055 | N | ALA C | 286 | 28.814 | 39.384 | −33.407 | 1.00 | 56.11 | N |
| ATOM | 10056 | CA | ALA C | 286 | 30.018 | 40.204 | −33.680 | 1.00 | 57.23 | C |
| ATOM | 10057 | CB | ALA C | 286 | 31.102 | 39.987 | −32.641 | 1.00 | 58.16 | C |
| ATOM | 10058 | C | ALA C | 286 | 30.610 | 40.044 | −35.067 | 1.00 | 58.41 | C |
| ATOM | 10059 | O | ALA C | 286 | 31.097 | 40.986 | −35.577 | 1.00 | 65.42 | O |
| ATOM | 10060 | N | CYS C | 287 | 30.562 | 38.880 | −35.687 | 1.00 | 64.17 | N |
| ATOM | 10061 | CA | CYS C | 287 | 30.903 | 38.743 | −37.117 | 1.00 | 67.80 | C |
| ATOM | 10062 | CB | CYS C | 287 | 30.660 | 37.309 | −37.573 | 1.00 | 73.27 | C |
| ATOM | 10063 | SG | CYS C | 287 | 31.392 | 36.131 | −36.464 | 1.00 | 82.76 | S |
| ATOM | 10064 | C | CYS C | 287 | 30.079 | 39.590 | −38.087 | 1.00 | 63.51 | C |
| ATOM | 10065 | O | CYS C | 287 | 30.453 | 39.747 | −39.231 | 1.00 | 64.16 | O |
| ATOM | 10066 | N | LEU C | 288 | 28.917 | 40.057 | −37.699 | 1.00 | 60.32 | N |
| ATOM | 10067 | CA | LEU C | 288 | 28.076 | 40.632 | −38.702 | 1.00 | 62.82 | C |
| ATOM | 10068 | CB | LEU C | 288 | 26.616 | 40.414 | −38.390 | 1.00 | 63.18 | C |
| ATOM | 10069 | CG | LEU C | 288 | 26.160 | 39.025 | −38.030 | 1.00 | 63.29 | C |
| ATOM | 10070 | CD1 | LEU C | 288 | 24.647 | 39.091 | −38.140 | 1.00 | 63.51 | C |
| ATOM | 10071 | CD2 | LEU C | 288 | 26.776 | 37.922 | −38.908 | 1.00 | 66.66 | C |
| ATOM | 10072 | C | LEU C | 288 | 28.346 | 42.120 | −38.883 | 1.00 | 65.85 | C |
| ATOM | 10073 | O | LEU C | 288 | 28.172 | 42.910 | −37.898 | 1.00 | 57.97 | O |
| ATOM | 10074 | N | PRO C | 289 | 28.751 | 42.496 | −40.136 | 1.00 | 71.69 | N |
| ATOM | 10075 | CA | PRO C | 289 | 28.918 | 43.885 | −40.534 | 1.00 | 74.49 | C |
| ATOM | 10076 | CB | PRO C | 289 | 29.705 | 43.780 | −41.839 | 1.00 | 75.98 | C |
| ATOM | 10077 | CG | PRO C | 289 | 29.256 | 42.479 | −42.458 | 1.00 | 74.09 | C |
| ATOM | 10078 | CD | PRO C | 289 | 28.951 | 41.584 | −41.300 | 1.00 | 73.51 | C |
| ATOM | 10079 | C | PRO C | 289 | 27.541 | 44.431 | −40.779 | 1.00 | 76.02 | C |
| ATOM | 10080 | O | PRO C | 289 | 26.971 | 44.241 | −41.865 | 1.00 | 74.09 | O |
| ATOM | 10081 | N | ILE C | 290 | 26.993 | 45.021 | −39.728 | 1.00 | 75.03 | N |
| ATOM | 10082 | CA | ILE C | 290 | 25.654 | 45.591 | −39.744 | 1.00 | 77.74 | C |
| ATOM | 10083 | CB | ILE C | 290 | 24.589 | 44.714 | −38.990 | 1.00 | 78.37 | C |
| ATOM | 10084 | CG1 | ILE C | 290 | 25.027 | 44.358 | −37.559 | 1.00 | 78.45 | C |
| ATOM | 10085 | CD1 | ILE C | 290 | 23.879 | 43.893 | −36.704 | 1.00 | 75.12 | C |
| ATOM | 10086 | CG2 | ILE C | 290 | 24.253 | 43.430 | −39.746 | 1.00 | 74.27 | C |
| ATOM | 10087 | C | ILE C | 290 | 25.769 | 46.958 | −39.105 | 1.00 | 76.08 | C |
| ATOM | 10088 | O | ILE C | 290 | 26.740 | 47.215 | −38.420 | 1.00 | 68.41 | O |
| ATOM | 10089 | N | ASP C | 291 | 24.781 | 47.822 | −39.328 | 1.00 | 81.29 | N |
| ATOM | 10090 | CA | ASP C | 291 | 24.826 | 49.185 | −38.789 | 1.00 | 84.93 | C |
| ATOM | 10091 | CB | ASP C | 291 | 23.919 | 50.186 | −39.542 | 1.00 | 96.32 | C |
| ATOM | 10092 | CG | ASP C | 291 | 22.478 | 49.706 | −39.695 | 1.00 | 108.44 | C |
| ATOM | 10093 | OD1 | ASP C | 291 | 22.251 | 48.667 | −40.374 | 1.00 | 116.16 | O |
| ATOM | 10094 | OD2 | ASP C | 291 | 21.574 | 50.390 | −39.161 | 1.00 | 117.36 | O |
| ATOM | 10095 | C | ASP C | 291 | 24.505 | 49.148 | −37.326 | 1.00 | 75.76 | C |
| ATOM | 10096 | O | ASP C | 291 | 23.997 | 48.154 | −36.838 | 1.00 | 69.00 | O |
| ATOM | 10097 | N | ASP C | 292 | 24.825 | 50.248 | −36.652 | 1.00 | 76.41 | N |
| ATOM | 10098 | CA | ASP C | 292 | 24.695 | 50.393 | −35.197 | 1.00 | 79.53 | C |
| ATOM | 10099 | CB | ASP C | 292 | 25.105 | 51.825 | −34.693 | 1.00 | 83.34 | C |
| ATOM | 10100 | CG | ASP C | 292 | 26.644 | 52.040 | −34.538 | 1.00 | 84.16 | C |
| ATOM | 10101 | OD1 | ASP C | 292 | 27.421 | 51.787 | −35.509 | 1.00 | 83.52 | O |
| ATOM | 10102 | OD2 | ASP C | 292 | 27.053 | 52.534 | −33.443 | 1.00 | 75.96 | O |
| ATOM | 10103 | C | ASP C | 292 | 23.252 | 50.121 | −34.744 | 1.00 | 79.18 | C |
| ATOM | 10104 | O | ASP C | 292 | 23.011 | 49.793 | −33.577 | 1.00 | 80.31 | O |
| ATOM | 10105 | N | VAL C | 293 | 22.278 | 50.297 | −35.623 | 1.00 | 77.77 | N |
| ATOM | 10106 | CA | VAL C | 293 | 20.914 | 50.313 | −35.129 | 1.00 | 81.77 | C |
| ATOM | 10107 | CB | VAL C | 293 | 20.029 | 51.403 | −35.842 | 1.00 | 83.33 | C |
| ATOM | 10108 | CG1 | VAL C | 293 | 19.145 | 50.827 | −36.967 | 1.00 | 77.83 | C |
| ATOM | 10109 | CG2 | VAL C | 293 | 19.231 | 52.200 | −34.779 | 1.00 | 81.19 | C |
| ATOM | 10110 | C | VAL C | 293 | 20.365 | 48.901 | −35.095 | 1.00 | 75.02 | C |

TABLE 6-continued

Atomic coordinates for CRBN:DDB1: Compound B (Human protein)

| ATOM | 10111 | O | VAL C | 293 | 19.539 | 48.603 | −34.237 | 1.00 | 76.74 | O |
|---|---|---|---|---|---|---|---|---|---|---|
| ATOM | 10112 | N | LEU C | 294 | 20.853 | 48.039 | −35.983 | 1.00 | 69.56 | N |
| ATOM | 10113 | CA | LEU C | 294 | 20.495 | 46.626 | −35.941 | 1.00 | 75.36 | C |
| ATOM | 10114 | CB | LEU C | 294 | 20.768 | 45.947 | −37.277 | 1.00 | 80.19 | C |
| ATOM | 10115 | CG | LEU C | 294 | 20.025 | 46.395 | −38.532 | 1.00 | 85.58 | C |
| ATOM | 10116 | CD1 | LEU C | 294 | 20.155 | 45.275 | −39.560 | 1.00 | 87.90 | C |
| ATOM | 10117 | CD2 | LEU C | 294 | 18.563 | 46.762 | −38.290 | 1.00 | 88.35 | C |
| ATOM | 10118 | C | LEU C | 294 | 21.254 | 45.869 | −34.841 | 1.00 | 76.69 | C |
| ATOM | 10119 | O | LEU C | 294 | 20.667 | 45.055 | −34.111 | 1.00 | 78.02 | O |
| ATOM | 10120 | N | ARG C | 295 | 22.564 | 46.105 | −34.747 | 1.00 | 70.40 | N |
| ATOM | 10121 | CA | ARG C | 295 | 23.344 | 45.652 | −33.607 | 1.00 | 63.89 | C |
| ATOM | 10122 | CB | ARG C | 295 | 24.600 | 46.493 | −33.472 | 1.00 | 67.15 | C |
| ATOM | 10123 | CG | ARG C | 295 | 25.859 | 45.861 | −32.910 | 1.00 | 65.37 | C |
| ATOM | 10124 | CD | ARG C | 295 | 26.391 | 44.853 | −33.902 | 1.00 | 70.46 | C |
| ATOM | 10125 | NE | ARG C | 295 | 27.795 | 44.913 | −34.293 | 1.00 | 67.34 | N |
| ATOM | 10126 | CZ | ARG C | 295 | 28.819 | 45.237 | −33.524 | 1.00 | 61.84 | C |
| ATOM | 10127 | NH1 | ARG C | 295 | 28.680 | 45.604 | −32.251 | 1.00 | 56.61 | N |
| ATOM | 10128 | NH2 | ARG C | 295 | 30.021 | 45.188 | −34.068 | 1.00 | 62.27 | N |
| ATOM | 10129 | C | ARG C | 295 | 22.476 | 45.825 | −32.377 | 1.00 | 62.29 | C |
| ATOM | 10130 | O | ARG C | 295 | 22.274 | 44.874 | −31.661 | 1.00 | 73.38 | O |
| ATOM | 10131 | N | ILE C | 296 | 21.893 | 47.001 | −32.171 | 1.00 | 57.98 | N |
| ATOM | 10132 | CA | ILE C | 296 | 21.041 | 47.211 | −31.005 | 1.00 | 60.60 | C |
| ATOM | 10133 | CB | ILE C | 296 | 20.698 | 48.702 | −30.728 | 1.00 | 62.26 | C |
| ATOM | 10134 | CG1 | ILE C | 296 | 21.967 | 49.513 | −30.493 | 1.00 | 67.75 | C |
| ATOM | 10135 | CD1 | ILE C | 296 | 21.764 | 51.018 | −30.585 | 1.00 | 71.44 | C |
| ATOM | 10136 | CG2 | ILE C | 296 | 19.889 | 48.860 | −29.446 | 1.00 | 59.91 | C |
| ATOM | 10137 | C | ILE C | 296 | 19.779 | 46.356 | −31.055 | 1.00 | 60.96 | C |
| ATOM | 10138 | O | ILE C | 296 | 19.389 | 45.845 | −30.026 | 1.00 | 64.67 | O |
| ATOM | 10139 | N | GLN C | 297 | 19.131 | 46.198 | −32.201 | 1.00 | 66.26 | N |
| ATOM | 10140 | CA | GLN C | 297 | 17.989 | 45.264 | −32.282 | 1.00 | 76.28 | C |
| ATOM | 10141 | CB | GLN C | 297 | 17.453 | 45.018 | −33.727 | 1.00 | 91.66 | C |
| ATOM | 10142 | CG | GLN C | 297 | 16.982 | 46.205 | −34.574 | 1.00 | 101.09 | C |
| ATOM | 10143 | CD | GLN C | 297 | 15.773 | 46.916 | −34.006 | 1.00 | 105.06 | C |
| ATOM | 10144 | OE1 | GLN C | 297 | 14.735 | 46.996 | −34.659 | 1.00 | 114.20 | O |
| ATOM | 10145 | NE2 | GLN C | 297 | 15.907 | 47.451 | −32.794 | 1.00 | 97.92 | N |
| ATOM | 10146 | C | GLN C | 297 | 18.407 | 43.906 | −31.725 | 1.00 | 71.34 | C |
| ATOM | 10147 | O | GLN C | 297 | 17.758 | 43.376 | −30.824 | 1.00 | 73.11 | O |
| ATOM | 10148 | N | LEU C | 298 | 19.484 | 43.366 | −32.288 | 1.00 | 65.05 | N |
| ATOM | 10149 | CA | LEU C | 298 | 20.041 | 42.116 | −31.871 | 1.00 | 63.38 | C |
| ATOM | 10150 | CB | LEU C | 298 | 21.364 | 41.888 | −32.547 | 1.00 | 62.00 | C |
| ATOM | 10151 | CG | LEU C | 298 | 21.386 | 41.004 | −33.752 | 1.00 | 63.58 | C |
| ATOM | 10152 | CD1 | LEU C | 298 | 22.818 | 40.503 | −33.879 | 1.00 | 67.05 | C |
| ATOM | 10153 | CD2 | LEU C | 298 | 20.446 | 39.817 | −33.650 | 1.00 | 63.80 | C |
| ATOM | 10154 | C | LEU C | 298 | 20.310 | 42.040 | −30.392 | 1.00 | 66.91 | C |
| ATOM | 10155 | O | LEU C | 298 | 19.990 | 41.055 | −29.738 | 1.00 | 78.15 | O |
| ATOM | 10156 | N | LEU C | 299 | 20.950 | 43.059 | −29.865 | 1.00 | 67.09 | N |
| ATOM | 10157 | CA | LEU C | 299 | 21.248 | 43.100 | −28.428 | 1.00 | 68.52 | C |
| ATOM | 10158 | CB | LEU C | 299 | 22.054 | 44.351 | −28.111 | 1.00 | 68.12 | C |
| ATOM | 10159 | CG | LEU C | 299 | 23.556 | 44.141 | −28.065 | 1.00 | 71.12 | C |
| ATOM | 10160 | CD1 | LEU C | 299 | 23.909 | 44.005 | −26.594 | 1.00 | 80.41 | C |
| ATOM | 10161 | CD2 | LEU C | 299 | 24.079 | 42.944 | −28.860 | 1.00 | 72.31 | C |
| ATOM | 10162 | C | LEU C | 299 | 20.024 | 43.060 | −27.545 | 1.00 | 67.34 | C |
| ATOM | 10163 | O | LEU C | 299 | 20.000 | 42.361 | −26.528 | 1.00 | 65.26 | O |
| ATOM | 10164 | N | LYS C | 300 | 19.020 | 43.820 | −27.950 | 1.00 | 69.80 | N |
| ATOM | 10165 | CA | LYS C | 300 | 17.825 | 43.956 | −27.168 | 1.00 | 75.00 | C |
| ATOM | 10166 | CB | LYS C | 300 | 16.977 | 45.142 | −27.666 | 1.00 | 75.53 | C |
| ATOM | 10167 | CG | LYS C | 300 | 17.520 | 46.512 | −27.239 | 1.00 | 75.88 | C |
| ATOM | 10168 | CD | LYS C | 300 | 16.409 | 47.481 | −26.845 | 1.00 | 80.67 | C |
| ATOM | 10169 | CE | LYS C | 300 | 16.765 | 48.918 | −27.216 | 1.00 | 87.48 | C |
| ATOM | 10170 | NZ | LYS C | 300 | 15.673 | 49.894 | −26.931 | 1.00 | 90.31 | N |
| ATOM | 10171 | C | LYS C | 300 | 17.057 | 42.617 | −27.060 | 1.00 | 77.49 | C |
| ATOM | 10172 | O | LYS C | 300 | 16.665 | 42.228 | −25.948 | 1.00 | 77.84 | O |
| ATOM | 10173 | N | ILE C | 301 | 16.890 | 41.909 | −28.185 | 1.00 | 78.10 | N |
| ATOM | 10174 | CA | ILE C | 301 | 16.444 | 40.478 | −28.216 | 1.00 | 74.29 | C |
| ATOM | 10175 | CB | ILE C | 301 | 16.696 | 39.876 | −29.635 | 1.00 | 74.47 | C |
| ATOM | 10176 | CG1 | ILE C | 301 | 15.442 | 40.047 | −30.502 | 1.00 | 80.31 | C |
| ATOM | 10177 | CD1 | ILE C | 301 | 15.680 | 39.951 | −32.014 | 1.00 | 85.92 | C |
| ATOM | 10178 | CG2 | ILE C | 301 | 17.158 | 38.426 | −29.617 | 1.00 | 72.23 | C |
| ATOM | 10179 | C | ILE C | 301 | 17.123 | 39.669 | −27.098 | 1.00 | 71.81 | C |
| ATOM | 10180 | O | ILE C | 301 | 18.351 | 39.547 | −27.044 | 1.00 | 70.60 | O |
| ATOM | 10181 | N | GLY C | 302 | 16.317 | 39.177 | −26.171 | 1.00 | 73.23 | N |
| ATOM | 10182 | CA | GLY C | 302 | 16.850 | 38.595 | −24.917 | 1.00 | 76.32 | C |
| ATOM | 10183 | C | GLY C | 302 | 17.048 | 37.092 | −24.995 | 1.00 | 76.44 | C |
| ATOM | 10184 | O | GLY C | 302 | 17.978 | 36.515 | −24.328 | 1.00 | 66.11 | O |
| ATOM | 10185 | N | SER C | 303 | 16.155 | 36.501 | −25.821 | 1.00 | 71.52 | N |
| ATOM | 10186 | CA | SER C | 303 | 16.111 | 35.075 | −26.163 | 1.00 | 64.18 | C |
| ATOM | 10187 | CB | SER C | 303 | 14.727 | 34.768 | −26.733 | 1.00 | 67.60 | C |
| ATOM | 10188 | OG | SER C | 303 | 14.811 | 34.087 | −27.969 | 1.00 | 68.29 | O |

TABLE 6-continued

Atomic coordinates for CRBN:DDB1: Compound B (Human protein)

| ATOM | 10189 | C | SER C | 303 | 17.127 | 34.677 | −27.212 | 1.00 | 54.90 | C |
|---|---|---|---|---|---|---|---|---|---|---|
| ATOM | 10190 | O | SER C | 303 | 17.083 | 35.208 | −28.308 | 1.00 | 50.27 | O |
| ATOM | 10191 | N | ALA C | 304 | 18.000 | 33.717 | −26.928 | 1.00 | 48.26 | N |
| ATOM | 10192 | CA | ALA C | 304 | 18.993 | 33.316 | −27.946 | 1.00 | 47.96 | C |
| ATOM | 10193 | CB | ALA C | 304 | 20.059 | 32.408 | −27.353 | 1.00 | 47.70 | C |
| ATOM | 10194 | C | ALA C | 304 | 18.403 | 32.682 | −29.215 | 1.00 | 47.54 | C |
| ATOM | 10195 | O | ALA C | 304 | 18.925 | 32.815 | −30.281 | 1.00 | 45.52 | O |
| ATOM | 10196 | N | ILE C | 305 | 17.303 | 31.991 | −29.093 | 1.00 | 49.44 | N |
| ATOM | 10197 | CA | ILE C | 305 | 16.698 | 31.398 | −30.254 | 1.00 | 51.24 | C |
| ATOM | 10198 | CB | ILE C | 305 | 15.475 | 30.520 | −29.864 | 1.00 | 52.26 | C |
| ATOM | 10199 | CG1 | ILE C | 305 | 15.883 | 29.378 | −28.954 | 1.00 | 49.68 | C |
| ATOM | 10200 | CD1 | ILE C | 305 | 16.839 | 28.429 | −29.617 | 1.00 | 51.01 | C |
| ATOM | 10201 | CG2 | ILE C | 305 | 14.754 | 29.946 | −31.091 | 1.00 | 53.19 | C |
| ATOM | 10202 | C | ILE C | 305 | 16.289 | 32.481 | −31.248 | 1.00 | 50.62 | C |
| ATOM | 10203 | O | ILE C | 305 | 16.508 | 32.333 | −32.452 | 1.00 | 51.27 | O |
| ATOM | 10204 | N | GLN C | 306 | 15.683 | 33.556 | −30.775 | 1.00 | 53.33 | N |
| ATOM | 10205 | CA | GLN C | 306 | 15.315 | 34.651 | −31.702 | 1.00 | 58.97 | C |
| ATOM | 10206 | CB | GLN C | 306 | 14.385 | 35.681 | −31.052 | 1.00 | 60.03 | C |
| ATOM | 10207 | CG | GLN C | 306 | 12.981 | 35.128 | −30.879 | 1.00 | 64.60 | C |
| ATOM | 10208 | CD | GLN C | 306 | 12.151 | 35.853 | −29.829 | 1.00 | 70.01 | C |
| ATOM | 10209 | OE1 | GLN C | 306 | 12.678 | 36.504 | −28.920 | 1.00 | 72.00 | O |
| ATOM | 10210 | NE2 | GLN C | 306 | 10.830 | 35.730 | −29.945 | 1.00 | 74.80 | N |
| ATOM | 10211 | C | GLN C | 306 | 16.552 | 35.332 | −32.285 | 1.00 | 59.15 | C |
| ATOM | 10212 | O | GLN C | 306 | 16.510 | 35.740 | −33.447 | 1.00 | 67.07 | O |
| ATOM | 10213 | N | ARG C | 307 | 17.631 | 35.423 | −31.487 | 1.00 | 54.03 | N |
| ATOM | 10214 | CA | ARG C | 307 | 18.909 | 35.997 | −31.916 | 1.00 | 50.35 | C |
| ATOM | 10215 | CB | ARG C | 307 | 19.911 | 36.083 | −30.744 | 1.00 | 52.19 | C |
| ATOM | 10216 | CG | ARG C | 307 | 20.737 | 37.364 | −30.723 | 1.00 | 54.21 | C |
| ATOM | 10217 | CD | ARG C | 307 | 21.639 | 37.538 | −29.490 | 1.00 | 56.93 | C |
| ATOM | 10218 | NE | ARG C | 307 | 20.886 | 37.812 | −28.263 | 1.00 | 55.51 | N |
| ATOM | 10219 | CZ | ARG C | 307 | 20.867 | 37.024 | −27.186 | 1.00 | 59.80 | C |
| ATOM | 10220 | NH1 | ARG C | 307 | 21.604 | 35.920 | −27.114 | 1.00 | 60.19 | N |
| ATOM | 10221 | NH2 | ARG C | 307 | 20.110 | 37.340 | −26.135 | 1.00 | 64.72 | N |
| ATOM | 10222 | C | ARG C | 307 | 19.515 | 35.213 | −33.079 | 1.00 | 48.56 | C |
| ATOM | 10223 | O | ARG C | 307 | 19.938 | 35.798 | −34.055 | 1.00 | 53.19 | O |
| ATOM | 10224 | N | LEU C | 308 | 19.519 | 33.889 | −32.974 | 1.00 | 48.13 | N |
| ATOM | 10225 | CA | LEU C | 308 | 20.055 | 32.985 | −33.982 | 1.00 | 44.96 | C |
| ATOM | 10226 | CB | LEU C | 308 | 20.048 | 31.558 | −33.475 | 1.00 | 42.71 | C |
| ATOM | 10227 | CG | LEU C | 308 | 20.922 | 31.384 | −32.262 | 1.00 | 44.92 | C |
| ATOM | 10228 | CD1 | LEU C | 308 | 20.440 | 30.284 | −31.331 | 1.00 | 45.43 | C |
| ATOM | 10229 | CD2 | LEU C | 308 | 22.330 | 31.114 | −32.712 | 1.00 | 46.01 | C |
| ATOM | 10230 | C | LEU C | 308 | 19.218 | 33.048 | −35.250 | 1.00 | 46.74 | C |
| ATOM | 10231 | O | LEU C | 308 | 19.727 | 32.921 | −36.349 | 1.00 | 48.62 | O |
| ATOM | 10232 | N | ARG C | 309 | 17.924 | 33.221 | −35.132 | 1.00 | 49.44 | N |
| ATOM | 10233 | CA | ARG C | 309 | 17.120 | 33.240 | −36.355 | 1.00 | 55.02 | C |
| ATOM | 10234 | CB | ARG C | 309 | 15.665 | 33.058 | −36.028 | 1.00 | 52.02 | C |
| ATOM | 10235 | CG | ARG C | 309 | 15.433 | 31.688 | −35.490 | 1.00 | 52.07 | C |
| ATOM | 10236 | CD | ARG C | 309 | 14.143 | 31.739 | −34.776 | 1.00 | 54.64 | C |
| ATOM | 10237 | NE | ARG C | 309 | 13.151 | 32.319 | −35.656 | 1.00 | 51.99 | N |
| ATOM | 10238 | CZ | ARG C | 309 | 12.554 | 31.653 | −36.606 | 1.00 | 51.06 | C |
| ATOM | 10239 | NH1 | ARG C | 309 | 11.646 | 32.254 | −37.327 | 1.00 | 53.49 | N |
| ATOM | 10240 | NH2 | ARG C | 309 | 12.833 | 30.378 | −36.819 | 1.00 | 53.82 | N |
| ATOM | 10241 | C | ARG C | 309 | 17.310 | 34.539 | −37.109 | 1.00 | 57.69 | C |
| ATOM | 10242 | O | ARG C | 309 | 17.397 | 34.579 | −38.349 | 1.00 | 61.67 | O |
| ATOM | 10243 | N | CYS C | 310 | 17.325 | 35.591 | −36.323 | 1.00 | 57.45 | N |
| ATOM | 10244 | CA | CYS C | 310 | 17.594 | 36.885 | −36.795 | 1.00 | 59.70 | C |
| ATOM | 10245 | CB | CYS C | 310 | 17.414 | 37.870 | −35.636 | 1.00 | 63.19 | C |
| ATOM | 10246 | SG | CYS C | 310 | 17.885 | 39.467 | −36.223 | 1.00 | 76.75 | S |
| ATOM | 10247 | C | CYS C | 310 | 19.005 | 36.924 | −37.420 | 1.00 | 56.48 | C |
| ATOM | 10248 | O | CYS C | 310 | 19.221 | 37.573 | −38.436 | 1.00 | 58.02 | O |
| ATOM | 10249 | N | GLU C | 311 | 19.968 | 36.227 | −36.849 | 1.00 | 53.51 | N |
| ATOM | 10250 | CA | GLU C | 311 | 21.293 | 36.207 | −37.471 | 1.00 | 54.87 | C |
| ATOM | 10251 | CB | GLU C | 311 | 22.328 | 35.714 | −36.483 | 1.00 | 53.70 | C |
| ATOM | 10252 | CG | GLU C | 311 | 22.636 | 36.701 | −35.376 | 1.00 | 51.83 | C |
| ATOM | 10253 | CD | GLU C | 311 | 23.218 | 36.013 | −34.156 | 1.00 | 54.27 | C |
| ATOM | 10254 | OE1 | GLU C | 311 | 23.628 | 36.730 | −33.230 | 1.00 | 53.49 | O |
| ATOM | 10255 | OE2 | GLU C | 311 | 23.285 | 34.750 | −34.120 | 1.00 | 55.88 | O |
| ATOM | 10256 | C | GLU C | 311 | 21.356 | 35.364 | −38.759 | 1.00 | 56.18 | C |
| ATOM | 10257 | O | GLU C | 311 | 22.173 | 35.591 | −39.616 | 1.00 | 55.15 | O |
| ATOM | 10258 | N | LEU C | 312 | 20.518 | 34.348 | −38.860 | 1.00 | 61.05 | N |
| ATOM | 10259 | CA | LEU C | 312 | 20.391 | 33.592 | −40.091 | 1.00 | 57.42 | C |
| ATOM | 10260 | CB | LEU C | 312 | 19.529 | 32.357 | −39.913 | 1.00 | 56.61 | C |
| ATOM | 10261 | CG | LEU C | 312 | 20.329 | 31.125 | −39.530 | 1.00 | 59.86 | C |
| ATOM | 10262 | CD1 | LEU C | 312 | 19.359 | 29.971 | −39.312 | 1.00 | 65.67 | C |
| ATOM | 10263 | CD2 | LEU C | 312 | 21.336 | 30.744 | −40.601 | 1.00 | 61.02 | C |
| ATOM | 10264 | C | LEU C | 312 | 19.802 | 34.467 | −41.136 | 1.00 | 55.75 | C |
| ATOM | 10265 | O | LEU C | 312 | 20.289 | 34.481 | −42.240 | 1.00 | 58.67 | O |
| ATOM | 10266 | N | ASP C | 313 | 18.764 | 35.208 | −40.788 | 1.00 | 55.33 | N |

TABLE 6-continued

Atomic coordinates for CRBN:DDB1: Compound B (Human protein)

| ATOM | 10267 | CA  | ASP C | 313 | 18.127 | 36.089 | -41.746 | 1.00 | 58.16 | C |
| ---- | ----- | --- | ----- | --- | ------ | ------ | ------- | ---- | ----- | - |
| ATOM | 10268 | CB  | ASP C | 313 | 16.962 | 36.850 | -41.117 | 1.00 | 62.68 | C |
| ATOM | 10269 | CG  | ASP C | 313 | 15.932 | 37.266 | -42.129 | 1.00 | 73.12 | C |
| ATOM | 10270 | OD1 | ASP C | 313 | 15.233 | 36.348 | -42.603 | 1.00 | 83.27 | O |
| ATOM | 10271 | OD2 | ASP C | 313 | 15.801 | 38.484 | -42.454 | 1.00 | 84.53 | O |
| ATOM | 10272 | C   | ASP C | 313 | 19.178 | 37.050 | -42.306 | 1.00 | 56.77 | C |
| ATOM | 10273 | O   | ASP C | 313 | 19.445 | 37.042 | -43.500 | 1.00 | 54.82 | O |
| ATOM | 10274 | N   | ILE C | 314 | 19.843 | 37.797 | -41.429 | 1.00 | 57.88 | N |
| ATOM | 10275 | CA  | ILE C | 314 | 20.811 | 38.817 | -41.841 | 1.00 | 56.63 | C |
| ATOM | 10276 | CB  | ILE C | 314 | 21.551 | 39.446 | -40.631 | 1.00 | 57.04 | C |
| ATOM | 10277 | CG1 | ILE C | 314 | 20.604 | 40.290 | -39.758 | 1.00 | 57.36 | C |
| ATOM | 10278 | CD1 | ILE C | 314 | 20.926 | 40.214 | -38.261 | 1.00 | 55.70 | C |
| ATOM | 10279 | CG2 | ILE C | 314 | 22.689 | 40.341 | -41.075 | 1.00 | 54.93 | C |
| ATOM | 10280 | C   | ILE C | 314 | 21.792 | 38.148 | -42.790 | 1.00 | 55.40 | C |
| ATOM | 10281 | O   | ILE C | 314 | 21.982 | 38.592 | -43.914 | 1.00 | 55.07 | O |
| ATOM | 10282 | N   | MET C | 315 | 22.362 | 37.039 | -42.375 | 1.00 | 54.51 | N |
| ATOM | 10283 | CA  | MET C | 315 | 23.300 | 36.366 | -43.241 | 1.00 | 58.70 | C |
| ATOM | 10284 | CB  | MET C | 315 | 23.955 | 35.160 | -42.560 | 1.00 | 62.59 | C |
| ATOM | 10285 | CG  | MET C | 315 | 24.873 | 35.419 | -41.368 | 1.00 | 62.93 | C |
| ATOM | 10286 | SD  | MET C | 315 | 25.016 | 33.818 | -40.520 | 1.00 | 66.58 | S |
| ATOM | 10287 | CE  | MET C | 315 | 26.783 | 33.747 | -40.301 | 1.00 | 72.97 | C |
| ATOM | 10288 | C   | MET C | 315 | 22.736 | 35.918 | -44.602 | 1.00 | 58.77 | C |
| ATOM | 10289 | O   | MET C | 315 | 23.509 | 35.828 | -45.549 | 1.00 | 66.41 | O |
| ATOM | 10290 | N   | ASN C | 316 | 21.457 | 35.589 | -44.739 | 1.00 | 57.58 | N |
| ATOM | 10291 | CA  | ASN C | 316 | 20.998 | 35.088 | -46.055 | 1.00 | 60.47 | C |
| ATOM | 10292 | CB  | ASN C | 316 | 19.882 | 34.044 | -45.969 | 1.00 | 61.87 | C |
| ATOM | 10293 | CG  | ASN C | 316 | 20.274 | 32.830 | -45.127 | 1.00 | 65.73 | C |
| ATOM | 10294 | OD1 | ASN C | 316 | 21.372 | 32.291 | -45.240 | 1.00 | 70.27 | O |
| ATOM | 10295 | ND2 | ASN C | 316 | 19.380 | 32.417 | -44.250 | 1.00 | 68.04 | N |
| ATOM | 10296 | C   | ASN C | 316 | 20.595 | 36.243 | -46.943 | 1.00 | 64.77 | C |
| ATOM | 10297 | O   | ASN C | 316 | 21.055 | 36.317 | -48.095 | 1.00 | 70.91 | O |
| ATOM | 10298 | N   | LYS C | 317 | 19.776 | 37.153 | -46.397 | 1.00 | 65.68 | N |
| ATOM | 10299 | CA  | LYS C | 317 | 19.275 | 38.339 | -47.119 | 1.00 | 63.55 | C |
| ATOM | 10300 | CB  | LYS C | 317 | 18.124 | 39.015 | -46.322 | 1.00 | 56.69 | C |
| ATOM | 10301 | C   | LYS C | 317 | 20.424 | 39.319 | -47.517 | 1.00 | 67.89 | C |
| ATOM | 10302 | O   | LYS C | 317 | 20.637 | 39.563 | -48.679 | 1.00 | 66.62 | O |
| ATOM | 10303 | N   | CYS C | 318 | 21.196 | 39.826 | -46.565 | 1.00 | 82.04 | N |
| ATOM | 10304 | CA  | CYS C | 318 | 22.182 | 40.913 | -46.827 | 1.00 | 89.35 | C |
| ATOM | 10305 | CB  | CYS C | 318 | 22.633 | 41.587 | -45.496 | 1.00 | 94.63 | C |
| ATOM | 10306 | SG  | CYS C | 318 | 21.297 | 42.266 | -44.429 | 1.00 | 93.58 | S |
| ATOM | 10307 | C   | CYS C | 318 | 23.410 | 40.407 | -47.580 | 1.00 | 86.84 | C |
| ATOM | 10308 | O   | CYS C | 318 | 24.188 | 39.636 | -47.031 | 1.00 | 92.06 | O |
| ATOM | 10309 | N   | THR C | 319 | 23.600 | 40.875 | -48.812 | 1.00 | 87.09 | N |
| ATOM | 10310 | CA  | THR C | 319 | 24.667 | 40.357 | -49.710 | 1.00 | 83.63 | C |
| ATOM | 10311 | CB  | THR C | 319 | 24.019 | 39.623 | -50.866 | 1.00 | 85.73 | C |
| ATOM | 10312 | OG1 | THR C | 319 | 23.012 | 40.480 | -51.423 | 1.00 | 81.93 | O |
| ATOM | 10313 | CG2 | THR C | 319 | 23.416 | 38.308 | -50.340 | 1.00 | 89.50 | C |
| ATOM | 10314 | C   | THR C | 319 | 25.698 | 41.333 | -50.330 | 1.00 | 75.50 | C |
| ATOM | 10315 | O   | THR C | 319 | 26.768 | 40.882 | -50.741 | 1.00 | 73.31 | O |
| ATOM | 10316 | N   | SER C | 320 | 25.371 | 42.624 | -50.444 | 1.00 | 68.15 | N |
| ATOM | 10317 | CA  | SER C | 320 | 26.339 | 43.657 | -50.841 | 1.00 | 64.38 | C |
| ATOM | 10318 | CB  | SER C | 320 | 25.769 | 44.617 | -51.920 | 1.00 | 63.68 | C |
| ATOM | 10319 | OG  | SER C | 320 | 24.964 | 45.668 | -51.375 | 1.00 | 63.30 | O |
| ATOM | 10320 | C   | SER C | 320 | 26.681 | 44.426 | -49.601 | 1.00 | 63.33 | C |
| ATOM | 10321 | O   | SER C | 320 | 26.015 | 44.299 | -48.593 | 1.00 | 72.63 | O |
| ATOM | 10322 | N   | LEU C | 321 | 27.721 | 45.231 | -49.684 | 1.00 | 59.64 | N |
| ATOM | 10323 | CA  | LEU C | 321 | 28.085 | 46.149 | -48.635 | 1.00 | 55.79 | C |
| ATOM | 10324 | CB  | LEU C | 321 | 29.228 | 45.538 | -47.824 | 1.00 | 56.93 | C |
| ATOM | 10325 | CG  | LEU C | 321 | 28.885 | 44.397 | -46.870 | 1.00 | 54.06 | C |
| ATOM | 10326 | CD1 | LEU C | 321 | 30.057 | 43.522 | -46.520 | 1.00 | 54.92 | C |
| ATOM | 10327 | CD2 | LEU C | 321 | 28.351 | 45.004 | -45.615 | 1.00 | 53.62 | C |
| ATOM | 10328 | C   | LEU C | 321 | 28.561 | 47.386 | -49.352 | 1.00 | 54.79 | C |
| ATOM | 10329 | O   | LEU C | 321 | 29.326 | 47.278 | -50.297 | 1.00 | 52.31 | O |
| ATOM | 10330 | N   | CYS C | 322 | 28.100 | 48.551 | -48.917 | 1.00 | 56.71 | N |
| ATOM | 10331 | CA  | CYS C | 322 | 28.351 | 49.836 | -49.595 | 1.00 | 56.03 | C |
| ATOM | 10332 | CB  | CYS C | 322 | 27.068 | 50.341 | -50.209 | 1.00 | 57.76 | C |
| ATOM | 10333 | SG  | CYS C | 322 | 26.318 | 49.035 | -51.187 | 1.00 | 70.46 | S |
| ATOM | 10334 | C   | CYS C | 322 | 28.859 | 50.897 | -48.644 | 1.00 | 55.51 | C |
| ATOM | 10335 | O   | CYS C | 322 | 28.942 | 50.721 | -47.442 | 1.00 | 55.55 | O |
| ATOM | 10336 | N   | CYS C | 323 | 29.229 | 52.013 | -49.225 | 1.00 | 54.06 | N |
| ATOM | 10337 | CA  | CYS C | 323 | 29.794 | 53.108 | -48.502 | 1.00 | 51.54 | C |
| ATOM | 10338 | CB  | CYS C | 323 | 30.462 | 54.027 | -49.518 | 1.00 | 50.83 | C |
| ATOM | 10339 | SG  | CYS C | 323 | 30.870 | 55.680 | -48.977 | 1.00 | 48.55 | S |
| ATOM | 10340 | C   | CYS C | 323 | 28.624 | 53.750 | -47.796 | 1.00 | 54.01 | C |
| ATOM | 10341 | O   | CYS C | 323 | 27.647 | 54.047 | -48.422 | 1.00 | 55.68 | O |
| ATOM | 10342 | N   | LYS C | 324 | 28.697 | 53.910 | -46.480 | 1.00 | 59.33 | N |
| ATOM | 10343 | CA  | LYS C | 324 | 27.598 | 54.498 | -45.714 | 1.00 | 58.51 | C |
| ATOM | 10344 | CB  | LYS C | 324 | 27.922 | 54.566 | -44.226 | 1.00 | 61.62 | C |

TABLE 6-continued

Atomic coordinates for CRBN:DDB1: Compound B (Human protein)

| ATOM | 10345 | CG | LYS C | 324 | 26.750 | 54.817 | −43.270 | 1.00 | 67.51 | C |
|---|---|---|---|---|---|---|---|---|---|---|
| ATOM | 10346 | CD | LYS C | 324 | 27.143 | 54.470 | −41.816 | 1.00 | 72.37 | C |
| ATOM | 10347 | CE | LYS C | 324 | 26.248 | 55.064 | −40.715 | 1.00 | 79.29 | C |
| ATOM | 10348 | NZ | LYS C | 324 | 25.222 | 54.154 | −40.084 | 1.00 | 80.93 | N |
| ATOM | 10349 | C | LYS C | 324 | 27.288 | 55.877 | −46.244 | 1.00 | 59.16 | C |
| ATOM | 10350 | O | LYS C | 324 | 26.134 | 56.205 | −46.375 | 1.00 | 66.75 | O |
| ATOM | 10351 | N | GLN C | 325 | 28.313 | 56.714 | −46.401 | 1.00 | 59.17 | N |
| ATOM | 10352 | CA | GLN C | 325 | 28.109 | 58.096 | −46.839 | 1.00 | 62.07 | C |
| ATOM | 10353 | CB | GLN C | 325 | 29.394 | 58.905 | −46.629 | 1.00 | 66.88 | C |
| ATOM | 10354 | CG | GLN C | 325 | 29.287 | 60.360 | −47.053 | 1.00 | 74.67 | C |
| ATOM | 10355 | CD | GLN C | 325 | 28.213 | 61.112 | −46.291 | 1.00 | 84.94 | C |
| ATOM | 10356 | OE1 | GLN C | 325 | 27.534 | 60.547 | −45.433 | 1.00 | 91.35 | O |
| ATOM | 10357 | NE2 | GLN C | 325 | 28.054 | 62.393 | −46.601 | 1.00 | 91.02 | N |
| ATOM | 10358 | C | GLN C | 325 | 27.595 | 58.320 | −48.258 | 1.00 | 62.10 | C |
| ATOM | 10359 | O | GLN C | 325 | 26.664 | 59.099 | −48.464 | 1.00 | 60.70 | O |
| ATOM | 10360 | N | CYS C | 326 | 28.191 | 57.645 | −49.235 | 1.00 | 67.47 | N |
| ATOM | 10361 | CA | CYS C | 326 | 27.742 | 57.810 | −50.609 | 1.00 | 60.32 | C |
| ATOM | 10362 | CB | CYS C | 326 | 28.695 | 57.105 | −51.575 | 1.00 | 51.56 | C |
| ATOM | 10363 | SG | CYS C | 326 | 30.396 | 57.715 | −51.524 | 1.00 | 47.70 | S |
| ATOM | 10364 | C | CYS C | 326 | 26.342 | 57.245 | −50.747 | 1.00 | 64.60 | C |
| ATOM | 10365 | O | CYS C | 326 | 25.457 | 57.845 | −51.357 | 1.00 | 70.48 | O |
| ATOM | 10366 | N | GLN C | 327 | 26.169 | 56.067 | −50.161 | 1.00 | 66.87 | N |
| ATOM | 10367 | CA | GLN C | 327 | 24.908 | 55.348 | −50.172 | 1.00 | 75.33 | C |
| ATOM | 10368 | CB | GLN C | 327 | 23.737 | 56.306 | −49.947 | 1.00 | 80.37 | C |
| ATOM | 10369 | CG | GLN C | 327 | 22.375 | 55.632 | −49.946 | 1.00 | 85.62 | C |
| ATOM | 10370 | CD | GLN C | 327 | 22.244 | 54.582 | −48.861 | 1.00 | 89.48 | C |
| ATOM | 10371 | OE1 | GLN C | 327 | 23.177 | 54.347 | −48.093 | 1.00 | 91.97 | O |
| ATOM | 10372 | NE2 | GLN C | 327 | 21.081 | 53.944 | −48.792 | 1.00 | 89.03 | N |
| ATOM | 10373 | C | GLN C | 327 | 24.754 | 54.630 | −51.508 | 1.00 | 76.75 | C |
| ATOM | 10374 | O | GLN C | 327 | 23.794 | 53.888 | −51.716 | 1.00 | 81.01 | O |
| ATOM | 10375 | N | GLU C | 328 | 25.704 | 54.855 | −52.413 | 1.00 | 74.61 | N |
| ATOM | 10376 | CA | GLU C | 328 | 25.653 | 54.223 | −53.726 | 1.00 | 81.84 | C |
| ATOM | 10377 | CB | GLU C | 328 | 24.809 | 55.070 | −54.685 | 1.00 | 98.99 | C |
| ATOM | 10378 | CG | GLU C | 328 | 23.370 | 55.267 | −54.237 | 1.00 | 105.83 | C |
| ATOM | 10379 | CD | GLU C | 328 | 22.567 | 56.108 | −55.210 | 1.00 | 111.97 | C |
| ATOM | 10380 | OE1 | GLU C | 328 | 21.368 | 56.340 | −54.948 | 1.00 | 110.95 | O |
| ATOM | 10381 | OE2 | GLU C | 328 | 23.135 | 56.538 | −56.236 | 1.00 | 107.47 | O |
| ATOM | 10382 | C | GLU C | 328 | 27.001 | 53.890 | −54.376 | 1.00 | 79.02 | C |
| ATOM | 10383 | O | GLU C | 328 | 27.347 | 54.476 | −55.403 | 1.00 | 72.82 | O |
| ATOM | 10384 | N | THR C | 329 | 27.756 | 52.952 | −53.813 | 1.00 | 71.09 | N |
| ATOM | 10385 | CA | THR C | 329 | 28.986 | 52.879 | −54.427 | 1.00 | 68.53 | C |
| ATOM | 10386 | CB | THR C | 329 | 30.068 | 53.481 | −53.916 | 1.00 | 68.77 | C |
| ATOM | 10387 | OG1 | THR C | 329 | 29.583 | 54.816 | −54.017 | 1.00 | 79.34 | O |
| ATOM | 10388 | CG2 | THR C | 329 | 31.301 | 53.337 | −54.734 | 1.00 | 62.51 | C |
| ATOM | 10389 | C | THR C | 329 | 29.107 | 51.254 | −53.796 | 1.00 | 69.82 | C |
| ATOM | 10390 | O | THR C | 329 | 28.999 | 51.178 | −52.590 | 1.00 | 69.34 | O |
| ATOM | 10391 | N | GLU C | 330 | 29.338 | 50.208 | −54.568 | 1.00 | 66.54 | N |
| ATOM | 10392 | CA | GLU C | 330 | 29.418 | 48.907 | −53.966 | 1.00 | 66.32 | C |
| ATOM | 10393 | CB | GLU C | 330 | 28.867 | 47.866 | −54.908 | 1.00 | 73.03 | C |
| ATOM | 10394 | CG | GLU C | 330 | 28.281 | 46.673 | −54.203 | 1.00 | 81.79 | C |
| ATOM | 10395 | CD | GLU C | 330 | 28.349 | 45.421 | −55.028 | 1.00 | 85.68 | C |
| ATOM | 10396 | OE1 | GLU C | 330 | 27.332 | 44.725 | −55.103 | 1.00 | 90.09 | O |
| ATOM | 10397 | OE2 | GLU C | 330 | 29.412 | 45.130 | −55.603 | 1.00 | 81.79 | O |
| ATOM | 10398 | C | GLU C | 330 | 30.826 | 48.586 | −53.659 | 1.00 | 65.24 | C |
| ATOM | 10399 | O | GLU C | 330 | 31.603 | 48.335 | −54.546 | 1.00 | 69.17 | O |
| ATOM | 10400 | N | ILE C | 331 | 31.144 | 48.575 | −52.379 | 1.00 | 65.56 | N |
| ATOM | 10401 | CA | ILE C | 331 | 32.514 | 48.240 | −51.907 | 1.00 | 62.03 | C |
| ATOM | 10402 | CB | ILE C | 331 | 32.842 | 48.755 | −50.477 | 1.00 | 63.25 | C |
| ATOM | 10403 | CG1 | ILE C | 331 | 32.439 | 50.219 | −50.261 | 1.00 | 64.10 | C |
| ATOM | 10404 | CD1 | ILE C | 331 | 32.996 | 51.202 | −51.252 | 1.00 | 65.71 | C |
| ATOM | 10405 | CG2 | ILE C | 331 | 34.332 | 48.620 | −50.168 | 1.00 | 64.58 | C |
| ATOM | 10406 | C | ILE C | 331 | 32.816 | 46.729 | −51.984 | 1.00 | 56.99 | C |
| ATOM | 10407 | O | ILE C | 331 | 33.879 | 46.384 | −52.417 | 1.00 | 54.02 | O |
| ATOM | 10408 | N | THR C | 332 | 31.908 | 45.846 | −51.574 | 1.00 | 57.20 | N |
| ATOM | 10409 | CA | THR C | 332 | 32.144 | 44.386 | −51.691 | 1.00 | 59.62 | C |
| ATOM | 10410 | CB | THR C | 332 | 33.243 | 43.902 | −50.700 | 1.00 | 60.14 | C |
| ATOM | 10411 | OG1 | THR C | 332 | 33.612 | 42.542 | −50.998 | 1.00 | 59.59 | O |
| ATOM | 10412 | CG2 | THR C | 332 | 32.767 | 44.025 | −49.235 | 1.00 | 58.65 | C |
| ATOM | 10413 | C | THR C | 332 | 30.874 | 43.501 | −51.529 | 1.00 | 60.48 | C |
| ATOM | 10414 | O | THR C | 332 | 29.762 | 44.023 | −51.344 | 1.00 | 62.74 | O |
| ATOM | 10415 | N | THR C | 333 | 31.063 | 42.173 | −51.603 | 1.00 | 58.28 | N |
| ATOM | 10416 | CA | THR C | 333 | 29.978 | 41.200 | −51.442 | 1.00 | 60.59 | C |
| ATOM | 10417 | CB | THR C | 333 | 29.702 | 40.461 | −52.771 | 1.00 | 65.84 | C |
| ATOM | 10418 | OG1 | THR C | 333 | 30.677 | 39.421 | −52.985 | 1.00 | 74.56 | O |
| ATOM | 10419 | CG2 | THR C | 333 | 29.756 | 41.433 | −53.955 | 1.00 | 65.30 | C |
| ATOM | 10420 | C | THR C | 333 | 30.260 | 40.168 | −50.334 | 1.00 | 56.23 | C |
| ATOM | 10421 | O | THR C | 333 | 31.396 | 39.926 | −49.979 | 1.00 | 50.53 | O |
| ATOM | 10422 | N | LYS C | 334 | 29.195 | 39.571 | −49.813 | 1.00 | 57.17 | N |

TABLE 6-continued

Atomic coordinates for CRBN:DDB1: Compound B (Human protein)

| ATOM | 10423 | CA | LYS C | 334 | 29.249 | 38.412 | −48.914 | 1.00 | 59.65 | C |
|---|---|---|---|---|---|---|---|---|---|---|
| ATOM | 10424 | CB | LYS C | 334 | 27.833 | 37.817 | −48.717 | 1.00 | 67.92 | C |
| ATOM | 10425 | CG | LYS C | 334 | 27.717 | 36.429 | −48.029 | 1.00 | 77.63 | C |
| ATOM | 10426 | CD | LYS C | 334 | 26.333 | 35.769 | −48.250 | 1.00 | 81.26 | C |
| ATOM | 10427 | CE | LYS C | 334 | 26.332 | 34.253 | −48.022 | 1.00 | 82.21 | C |
| ATOM | 10428 | NZ | LYS C | 334 | 25.922 | 33.859 | −46.643 | 1.00 | 85.96 | N |
| ATOM | 10429 | C | LYS C | 334 | 30.178 | 37.336 | −49.442 | 1.00 | 56.11 | C |
| ATOM | 10430 | O | LYS C | 334 | 30.890 | 36.698 | −48.659 | 1.00 | 51.96 | O |
| ATOM | 10431 | N | ASN C | 335 | 30.174 | 37.120 | −50.757 | 1.00 | 56.08 | N |
| ATOM | 10432 | CA | ASN C | 335 | 31.061 | 36.115 | −51.351 | 1.00 | 59.70 | C |
| ATOM | 10433 | CB | ASN C | 335 | 31.032 | 36.205 | −52.876 | 1.00 | 70.75 | C |
| ATOM | 10434 | CG | ASN C | 335 | 30.055 | 35.254 | −53.511 | 1.00 | 76.17 | C |
| ATOM | 10435 | OD1 | ASN C | 335 | 30.030 | 35.130 | −54.743 | 1.00 | 87.29 | O |
| ATOM | 10436 | ND2 | ASN C | 335 | 29.256 | 34.568 | −52.699 | 1.00 | 72.75 | N |
| ATOM | 10437 | C | ASN C | 335 | 32.509 | 36.237 | −50.937 | 1.00 | 57.14 | C |
| ATOM | 10438 | O | ASN C | 335 | 33.236 | 35.263 | −50.970 | 1.00 | 55.63 | O |
| ATOM | 10439 | N | GLU C | 336 | 32.919 | 37.461 | −50.609 | 1.00 | 57.34 | N |
| ATOM | 10440 | CA | GLU C | 336 | 34.298 | 37.812 | −50.398 | 1.00 | 55.23 | C |
| ATOM | 10441 | CB | GLU C | 336 | 34.585 | 39.218 | −50.961 | 1.00 | 60.72 | C |
| ATOM | 10442 | CG | GLU C | 336 | 34.213 | 39.457 | −52.433 | 1.00 | 66.27 | C |
| ATOM | 10443 | CD | GLU C | 336 | 34.834 | 38.449 | −53.424 | 1.00 | 74.85 | C |
| ATOM | 10444 | OE1 | GLU C | 336 | 34.182 | 38.205 | −54.478 | 1.00 | 84.59 | O |
| ATOM | 10445 | OE2 | GLU C | 336 | 35.946 | 37.891 | −53.167 | 1.00 | 75.15 | O |
| ATOM | 10446 | C | GLU C | 336 | 34.648 | 37.784 | −48.951 | 1.00 | 50.33 | C |
| ATOM | 10447 | O | GLU C | 336 | 35.801 | 37.682 | −48.625 | 1.00 | 51.45 | O |
| ATOM | 10448 | N | ILE C | 337 | 33.681 | 37.882 | −48.054 | 1.00 | 48.79 | N |
| ATOM | 10449 | CA | ILE C | 337 | 34.000 | 37.883 | −46.625 | 1.00 | 48.12 | C |
| ATOM | 10450 | CB | ILE C | 337 | 32.735 | 37.959 | −45.771 | 1.00 | 46.70 | C |
| ATOM | 10451 | CG1 | ILE C | 337 | 32.202 | 39.393 | −45.785 | 1.00 | 46.46 | C |
| ATOM | 10452 | CD1 | ILE C | 337 | 30.765 | 39.529 | −45.281 | 1.00 | 47.54 | C |
| ATOM | 10453 | CG2 | ILE C | 337 | 33.001 | 37.523 | −44.341 | 1.00 | 46.62 | C |
| ATOM | 10454 | C | ILE C | 337 | 34.746 | 36.632 | −46.280 | 1.00 | 49.17 | C |
| ATOM | 10455 | O | ILE C | 337 | 34.407 | 35.586 | −46.800 | 1.00 | 55.79 | O |
| ATOM | 10456 | N | PHE C | 338 | 35.751 | 36.735 | −45.419 | 1.00 | 50.59 | N |
| ATOM | 10457 | CA | PHE C | 338 | 36.488 | 35.554 | −44.954 | 1.00 | 54.39 | C |
| ATOM | 10458 | CB | PHE C | 338 | 37.473 | 35.069 | −46.027 | 1.00 | 55.70 | C |
| ATOM | 10459 | CG | PHE C | 338 | 38.771 | 35.807 | −46.035 | 1.00 | 55.30 | C |
| ATOM | 10460 | CD1 | PHE C | 338 | 38.802 | 37.175 | −46.250 | 1.00 | 56.42 | C |
| ATOM | 10461 | CE1 | PHE C | 338 | 40.006 | 37.856 | −46.264 | 1.00 | 59.84 | C |
| ATOM | 10462 | CZ | PHE C | 338 | 41.205 | 37.167 | −46.060 | 1.00 | 61.18 | C |
| ATOM | 10463 | CE2 | PHE C | 338 | 41.176 | 35.803 | −45.858 | 1.00 | 60.88 | C |
| ATOM | 10464 | CD2 | PHE C | 338 | 39.958 | 35.134 | −45.829 | 1.00 | 57.73 | C |
| ATOM | 10465 | C | PHE C | 338 | 37.230 | 35.834 | −43.664 | 1.00 | 54.00 | C |
| ATOM | 10466 | O | PHE C | 338 | 37.440 | 37.007 | −43.334 | 1.00 | 51.54 | O |
| ATOM | 10467 | N | SER C | 339 | 37.653 | 34.771 | −42.968 | 1.00 | 54.52 | N |
| ATOM | 10468 | CA | SER C | 339 | 38.244 | 34.915 | −41.629 | 1.00 | 58.90 | C |
| ATOM | 10469 | CB | SER C | 339 | 37.536 | 34.032 | −40.625 | 1.00 | 55.95 | C |
| ATOM | 10470 | OG | SER C | 339 | 36.203 | 34.454 | −40.497 | 1.00 | 56.64 | O |
| ATOM | 10471 | C | SER C | 339 | 39.741 | 34.667 | −41.521 | 1.00 | 65.07 | C |
| ATOM | 10472 | O | SER C | 339 | 40.219 | 33.555 | −41.840 | 1.00 | 64.88 | O |
| ATOM | 10473 | N | LEU C | 340 | 40.442 | 35.731 | −41.069 | 1.00 | 70.38 | N |
| ATOM | 10474 | CA | LEU C | 340 | 41.804 | 35.673 | −40.519 | 1.00 | 70.00 | C |
| ATOM | 10475 | CB | LEU C | 340 | 42.650 | 36.852 | −40.979 | 1.00 | 69.34 | C |
| ATOM | 10476 | CG | LEU C | 340 | 42.864 | 36.955 | −42.470 | 1.00 | 70.59 | C |
| ATOM | 10477 | CD1 | LEU C | 340 | 43.730 | 38.175 | −42.718 | 1.00 | 73.21 | C |
| ATOM | 10478 | CD2 | LEU C | 340 | 43.529 | 35.709 | −43.001 | 1.00 | 69.77 | C |
| ATOM | 10479 | C | LEU C | 340 | 41.879 | 35.681 | −39.008 | 1.00 | 71.69 | C |
| ATOM | 10480 | O | LEU C | 340 | 42.927 | 35.358 | −38.500 | 1.00 | 81.40 | O |
| ATOM | 10481 | N | SER C | 341 | 40.838 | 36.101 | −38.281 | 1.00 | 72.91 | N |
| ATOM | 10482 | CA | SER C | 341 | 40.843 | 35.997 | −36.798 | 1.00 | 68.51 | C |
| ATOM | 10483 | CB | SER C | 341 | 40.135 | 37.189 | −36.084 | 1.00 | 72.22 | C |
| ATOM | 10484 | OG | SER C | 341 | 40.695 | 37.558 | −34.798 | 1.00 | 73.99 | O |
| ATOM | 10485 | C | SER C | 341 | 40.138 | 34.732 | −36.444 | 1.00 | 64.76 | C |
| ATOM | 10486 | O | SER C | 341 | 39.111 | 34.387 | −36.993 | 1.00 | 63.85 | O |
| ATOM | 10487 | N | LEU C | 342 | 40.673 | 34.055 | −35.471 | 1.00 | 69.05 | N |
| ATOM | 10488 | CA | LEU C | 342 | 39.899 | 33.061 | −34.768 | 1.00 | 70.23 | C |
| ATOM | 10489 | CB | LEU C | 342 | 40.666 | 32.602 | −33.556 | 1.00 | 71.53 | C |
| ATOM | 10490 | CG | LEU C | 342 | 40.650 | 31.110 | −33.509 | 1.00 | 73.64 | C |
| ATOM | 10491 | CD1 | LEU C | 342 | 41.929 | 30.629 | −34.183 | 1.00 | 71.07 | C |
| ATOM | 10492 | CD2 | LEU C | 342 | 40.492 | 30.693 | −32.040 | 1.00 | 81.16 | C |
| ATOM | 10493 | C | LEU C | 342 | 38.563 | 33.593 | −34.277 | 1.00 | 69.11 | C |
| ATOM | 10494 | O | LEU C | 342 | 37.595 | 32.853 | −34.213 | 1.00 | 73.46 | O |
| ATOM | 10495 | N | CYS C | 343 | 38.535 | 34.861 | −33.873 | 1.00 | 71.08 | N |
| ATOM | 10496 | CA | CYS C | 343 | 37.282 | 35.559 | −33.562 | 1.00 | 73.25 | C |
| ATOM | 10497 | CB | CYS C | 343 | 37.560 | 36.996 | −33.117 | 1.00 | 76.24 | C |
| ATOM | 10498 | SG | CYS C | 343 | 38.451 | 37.112 | −31.555 | 1.00 | 80.48 | S |
| ATOM | 10499 | C | CYS C | 343 | 36.236 | 35.585 | −34.700 | 1.00 | 69.09 | C |
| ATOM | 10500 | O | CYS C | 343 | 35.033 | 35.615 | −34.424 | 1.00 | 71.64 | O |

TABLE 6-continued

Atomic coordinates for CRBN:DDB1: Compound B (Human protein)

| ATOM | 10501 | N | GLY C | 344 | 36.683 | 35.579 | −35.955 | 1.00 | 63.38 | N |
|---|---|---|---|---|---|---|---|---|---|---|
| ATOM | 10502 | CA | GLY C | 344 | 35.786 | 35.683 | −37.094 | 1.00 | 59.70 | C |
| ATOM | 10503 | C | GLY C | 344 | 36.228 | 36.616 | −38.208 | 1.00 | 59.05 | C |
| ATOM | 10504 | O | GLY C | 344 | 37.373 | 37.082 | −38.245 | 1.00 | 60.80 | O |
| ATOM | 10505 | N | PRO C | 345 | 35.304 | 36.900 | −39.146 | 1.00 | 59.03 | N |
| ATOM | 10506 | CA | PRO C | 345 | 35.638 | 37.805 | −40.219 | 1.00 | 58.21 | C |
| ATOM | 10507 | CB | PRO C | 345 | 34.483 | 37.616 | −41.200 | 1.00 | 57.49 | C |
| ATOM | 10508 | CG | PRO C | 345 | 33.326 | 37.282 | −40.350 | 1.00 | 56.10 | C |
| ATOM | 10509 | CD | PRO C | 345 | 33.917 | 36.414 | −39.286 | 1.00 | 58.21 | C |
| ATOM | 10510 | C | PRO C | 345 | 35.703 | 39.232 | −39.772 | 1.00 | 57.19 | C |
| ATOM | 10511 | O | PRO C | 345 | 36.255 | 40.016 | −40.491 | 1.00 | 61.52 | O |
| ATOM | 10512 | N | MET C | 346 | 35.158 | 39.580 | −38.613 | 1.00 | 56.75 | N |
| ATOM | 10513 | CA | MET C | 346 | 35.249 | 40.954 | −38.164 | 1.00 | 58.62 | C |
| ATOM | 10514 | CB | MET C | 346 | 33.973 | 41.709 | −38.555 | 1.00 | 56.79 | C |
| ATOM | 10515 | CG | MET C | 346 | 33.845 | 43.090 | −37.942 | 1.00 | 55.24 | C |
| ATOM | 10516 | SD | MET C | 346 | 32.414 | 43.986 | −38.521 | 1.00 | 53.69 | S |
| ATOM | 10517 | CE | MET C | 346 | 31.185 | 43.396 | −37.384 | 1.00 | 56.80 | C |
| ATOM | 10518 | C | MET C | 346 | 35.526 | 41.017 | −36.663 | 1.00 | 60.33 | C |
| ATOM | 10519 | O | MET C | 346 | 35.159 | 40.102 | −35.921 | 1.00 | 66.43 | O |
| ATOM | 10520 | N | ALA C | 347 | 36.177 | 42.111 | −36.251 | 1.00 | 56.90 | N |
| ATOM | 10521 | CA | ALA C | 347 | 36.733 | 42.280 | −34.924 | 1.00 | 51.86 | C |
| ATOM | 10522 | CB | ALA C | 347 | 37.841 | 41.285 | −34.701 | 1.00 | 50.85 | C |
| ATOM | 10523 | C | ALA C | 347 | 37.287 | 43.675 | −34.725 | 1.00 | 51.42 | C |
| ATOM | 10524 | O | ALA C | 347 | 37.660 | 44.353 | −35.665 | 1.00 | 55.87 | O |
| ATOM | 10525 | N | ALA C | 348 | 37.392 | 44.046 | −33.462 | 1.00 | 53.28 | N |
| ATOM | 10526 | CA | ALA C | 348 | 37.738 | 45.384 | −33.005 | 1.00 | 51.74 | C |
| ATOM | 10527 | CB | ALA C | 348 | 36.941 | 45.702 | −31.724 | 1.00 | 51.30 | C |
| ATOM | 10528 | C | ALA C | 348 | 39.248 | 45.473 | −32.748 | 1.00 | 50.15 | C |
| ATOM | 10529 | O | ALA C | 348 | 39.797 | 44.586 | −32.117 | 1.00 | 55.65 | O |
| ATOM | 10530 | N | TYR C | 349 | 39.887 | 46.522 | −33.268 | 1.00 | 49.77 | N |
| ATOM | 10531 | CA | TYR C | 349 | 41.317 | 46.811 | −33.122 | 1.00 | 50.32 | C |
| ATOM | 10532 | CB | TYR C | 349 | 42.057 | 46.545 | −34.437 | 1.00 | 51.01 | C |
| ATOM | 10533 | CG | TYR C | 349 | 41.897 | 45.111 | −34.942 | 1.00 | 52.09 | C |
| ATOM | 10534 | CD1 | TYR C | 349 | 42.511 | 44.043 | −34.304 | 1.00 | 52.62 | C |
| ATOM | 10535 | CE1 | TYR C | 349 | 42.357 | 42.734 | −34.752 | 1.00 | 52.46 | C |
| ATOM | 10536 | CZ | TYR C | 349 | 41.565 | 42.464 | −35.842 | 1.00 | 53.79 | C |
| ATOM | 10537 | OH | TYR C | 349 | 41.390 | 41.159 | −36.317 | 1.00 | 54.92 | O |
| ATOM | 10538 | CE2 | TYR C | 349 | 40.940 | 43.520 | −36.475 | 1.00 | 55.71 | C |
| ATOM | 10539 | CD2 | TYR C | 349 | 41.114 | 44.824 | −36.024 | 1.00 | 52.80 | C |
| ATOM | 10540 | C | TYR C | 349 | 41.434 | 48.284 | −32.767 | 1.00 | 50.39 | C |
| ATOM | 10541 | O | TYR C | 349 | 40.567 | 49.058 | −33.149 | 1.00 | 48.88 | O |
| ATOM | 10542 | N | VAL C | 350 | 42.456 | 48.679 | −32.011 | 1.00 | 51.23 | N |
| ATOM | 10543 | CA | VAL C | 350 | 42.636 | 50.110 | −31.752 | 1.00 | 54.36 | C |
| ATOM | 10544 | CB | VAL C | 350 | 42.928 | 50.545 | −30.301 | 1.00 | 54.87 | C |
| ATOM | 10545 | CG1 | VAL C | 350 | 41.633 | 50.924 | −29.646 | 1.00 | 59.12 | C |
| ATOM | 10546 | CG2 | VAL C | 350 | 43.634 | 49.495 | −29.493 | 1.00 | 53.81 | C |
| ATOM | 10547 | C | VAL C | 350 | 43.754 | 50.588 | −32.582 | 1.00 | 56.42 | C |
| ATOM | 10548 | O | VAL C | 350 | 44.716 | 49.838 | −32.831 | 1.00 | 57.45 | O |
| ATOM | 10549 | N | ASN C | 351 | 43.647 | 51.847 | −32.983 | 1.00 | 52.82 | N |
| ATOM | 10550 | CA | ASN C | 351 | 44.725 | 52.436 | −33.724 | 1.00 | 54.22 | C |
| ATOM | 10551 | CB | ASN C | 351 | 44.168 | 53.298 | −34.861 | 1.00 | 55.67 | C |
| ATOM | 10552 | CG | ASN C | 351 | 43.786 | 54.681 | −34.440 | 1.00 | 54.78 | C |
| ATOM | 10553 | OD1 | ASN C | 351 | 43.720 | 55.014 | −33.255 | 1.00 | 56.66 | O |
| ATOM | 10554 | ND2 | ASN C | 351 | 43.510 | 55.503 | −35.424 | 1.00 | 54.50 | N |
| ATOM | 10555 | C | ASN C | 351 | 45.647 | 53.158 | −32.762 | 1.00 | 54.94 | C |
| ATOM | 10556 | O | ASN C | 351 | 45.445 | 53.104 | −31.523 | 1.00 | 56.91 | O |
| ATOM | 10557 | N | PRO C | 352 | 46.660 | 53.836 | −33.304 | 1.00 | 53.49 | N |
| ATOM | 10558 | CA | PRO C | 352 | 47.627 | 54.461 | −32.432 | 1.00 | 54.74 | C |
| ATOM | 10559 | CB | PRO C | 352 | 48.591 | 55.074 | −33.411 | 1.00 | 52.95 | C |
| ATOM | 10560 | CG | PRO C | 352 | 48.578 | 54.117 | −34.531 | 1.00 | 52.55 | C |
| ATOM | 10561 | CD | PRO C | 352 | 47.127 | 53.860 | −34.693 | 1.00 | 52.81 | C |
| ATOM | 10562 | C | PRO C | 352 | 47.072 | 55.531 | −31.500 | 1.00 | 56.94 | C |
| ATOM | 10563 | O | PRO C | 352 | 47.627 | 55.733 | −30.400 | 1.00 | 58.56 | O |
| ATOM | 10564 | N | HIS C | 353 | 46.000 | 56.192 | −31.936 | 1.00 | 56.29 | N |
| ATOM | 10565 | CA | HIS C | 353 | 45.422 | 57.295 | −31.189 | 1.00 | 59.20 | C |
| ATOM | 10566 | CB | HIS C | 353 | 44.963 | 58.390 | −32.160 | 1.00 | 60.73 | C |
| ATOM | 10567 | CG | HIS C | 353 | 46.078 | 58.932 | −33.009 | 1.00 | 64.95 | C |
| ATOM | 10568 | ND1 | HIS C | 353 | 47.160 | 59.605 | −32.479 | 1.00 | 66.74 | N |
| ATOM | 10569 | CE1 | HIS C | 353 | 47.996 | 59.932 | −33.450 | 1.00 | 69.10 | C |
| ATOM | 10570 | NE2 | HIS C | 353 | 47.499 | 59.493 | −34.593 | 1.00 | 68.51 | N |
| ATOM | 10571 | CD2 | HIS C | 353 | 46.301 | 58.861 | −34.345 | 1.00 | 68.30 | C |
| ATOM | 10572 | C | HIS C | 353 | 44.311 | 56.861 | −30.230 | 1.00 | 61.16 | C |
| ATOM | 10573 | O | HIS C | 353 | 43.797 | 57.686 | −29.444 | 1.00 | 58.86 | O |
| ATOM | 10574 | N | GLY C | 354 | 43.976 | 55.567 | −30.268 | 1.00 | 61.78 | N |
| ATOM | 10575 | CA | GLY C | 354 | 42.974 | 54.985 | −29.387 | 1.00 | 60.08 | C |
| ATOM | 10576 | C | GLY C | 354 | 41.601 | 54.997 | −29.987 | 1.00 | 58.33 | C |
| ATOM | 10577 | O | GLY C | 354 | 40.643 | 54.821 | −29.244 | 1.00 | 60.53 | O |
| ATOM | 10578 | N | TYR C | 355 | 41.508 | 55.214 | −31.308 | 1.00 | 57.14 | N |

TABLE 6-continued

Atomic coordinates for CRBN:DDB1: Compound B (Human protein)

| ATOM | 10579 | CA  | TYR C | 355 | 40.273 | 55.022 | −32.059 | 1.00 | 59.57  | C |
| ---- | ----- | --- | ----- | --- | ------ | ------ | ------- | ---- | ------ | - |
| ATOM | 10580 | CB  | TYR C | 355 | 40.315 | 55.717 | −33.410 | 1.00 | 66.46  | C |
| ATOM | 10581 | CG  | TYR C | 355 | 40.087 | 57.217 | −33.354 | 1.00 | 85.96  | C |
| ATOM | 10582 | CD1 | TYR C | 355 | 40.971 | 58.083 | −32.643 | 1.00 | 93.18  | C |
| ATOM | 10583 | CE1 | TYR C | 355 | 40.765 | 59.467 | −32.593 | 1.00 | 93.64  | C |
| ATOM | 10584 | CZ  | TYR C | 355 | 39.671 | 60.017 | −33.266 | 1.00 | 102.46 | C |
| ATOM | 10585 | OH  | TYR C | 355 | 39.428 | 61.376 | −33.238 | 1.00 | 102.82 | O |
| ATOM | 10586 | CE2 | TYR C | 355 | 38.801 | 59.191 | −33.990 | 1.00 | 105.92 | C |
| ATOM | 10587 | CD2 | TYR C | 355 | 39.009 | 57.803 | −34.034 | 1.00 | 98.25  | C |
| ATOM | 10588 | C   | TYR C | 355 | 40.137 | 53.529 | −32.289 | 1.00 | 57.91  | C |
| ATOM | 10589 | O   | TYR C | 355 | 41.095 | 52.883 | −32.763 | 1.00 | 59.69  | O |
| ATOM | 10590 | N   | VAL C | 356 | 38.979 | 52.972 | −31.926 | 1.00 | 52.84  | N |
| ATOM | 10591 | CA  | VAL C | 356 | 38.703 | 51.549 | −32.116 | 1.00 | 52.60  | C |
| ATOM | 10592 | CB  | VAL C | 356 | 37.691 | 50.998 | −31.078 | 1.00 | 54.75  | C |
| ATOM | 10593 | CG1 | VAL C | 356 | 37.425 | 49.514 | −31.314 | 1.00 | 55.56  | C |
| ATOM | 10594 | CG2 | VAL C | 356 | 38.151 | 51.227 | −29.655 | 1.00 | 53.06  | C |
| ATOM | 10595 | C   | VAL C | 356 | 38.041 | 51.352 | −33.456 | 1.00 | 49.80  | C |
| ATOM | 10596 | O   | VAL C | 356 | 37.099 | 52.043 | −33.767 | 1.00 | 46.07  | O |
| ATOM | 10597 | N   | HIS C | 357 | 38.469 | 50.370 | −34.223 | 1.00 | 52.32  | N |
| ATOM | 10598 | CA  | HIS C | 357 | 37.818 | 50.080 | −35.519 | 1.00 | 55.88  | C |
| ATOM | 10599 | CB  | HIS C | 357 | 38.746 | 50.355 | −36.725 | 1.00 | 59.49  | C |
| ATOM | 10600 | CG  | HIS C | 357 | 39.001 | 51.806 | −36.995 | 1.00 | 58.51  | C |
| ATOM | 10601 | ND1 | HIS C | 357 | 38.681 | 52.400 | −38.193 | 1.00 | 58.47  | N |
| ATOM | 10602 | CE1 | HIS C | 357 | 38.993 | 53.680 | −38.140 | 1.00 | 61.43  | C |
| ATOM | 10603 | NE2 | HIS C | 357 | 39.511 | 53.937 | −36.954 | 1.00 | 59.43  | N |
| ATOM | 10604 | CD2 | HIS C | 357 | 39.542 | 52.776 | −36.226 | 1.00 | 59.88  | C |
| ATOM | 10605 | C   | HIS C | 357 | 37.456 | 48.623 | −35.547 | 1.00 | 54.91  | C |
| ATOM | 10606 | O   | HIS C | 357 | 38.295 | 47.779 | −35.246 | 1.00 | 52.60  | O |
| ATOM | 10607 | N   | GLU C | 358 | 36.225 | 48.338 | −35.954 | 1.00 | 56.26  | N |
| ATOM | 10608 | CA  | GLU C | 358 | 35.791 | 46.969 | −36.164 | 1.00 | 56.27  | C |
| ATOM | 10609 | CB  | GLU C | 358 | 34.347 | 46.832 | −35.795 | 1.00 | 58.59  | C |
| ATOM | 10610 | CG  | GLU C | 358 | 34.117 | 47.294 | −34.379 | 1.00 | 61.13  | C |
| ATOM | 10611 | CD  | GLU C | 358 | 32.764 | 46.897 | −33.874 | 1.00 | 62.04  | C |
| ATOM | 10612 | OE1 | GLU C | 358 | 32.534 | 45.685 | −33.635 | 1.00 | 56.56  | O |
| ATOM | 10613 | OE2 | GLU C | 358 | 31.933 | 47.824 | −33.750 | 1.00 | 69.40  | O |
| ATOM | 10614 | C   | GLU C | 358 | 36.012 | 46.641 | −37.614 | 1.00 | 54.88  | C |
| ATOM | 10615 | O   | GLU C | 358 | 35.355 | 47.179 | −38.495 | 1.00 | 54.39  | O |
| ATOM | 10616 | N   | THR C | 359 | 36.962 | 45.767 | −37.887 | 1.00 | 54.30  | N |
| ATOM | 10617 | CA  | THR C | 359 | 37.387 | 45.653 | −39.256 | 1.00 | 54.05  | C |
| ATOM | 10618 | CB  | THR C | 359 | 38.794 | 46.224 | −39.494 | 1.00 | 50.96  | C |
| ATOM | 10619 | OG1 | THR C | 359 | 39.622 | 45.233 | −40.103 | 1.00 | 52.14  | O |
| ATOM | 10620 | CG2 | THR C | 359 | 39.378 | 46.787 | −38.243 | 1.00 | 47.63  | C |
| ATOM | 10621 | C   | THR C | 359 | 37.127 | 44.250 | −39.814 | 1.00 | 52.22  | C |
| ATOM | 10622 | O   | THR C | 359 | 37.625 | 43.239 | −39.341 | 1.00 | 54.38  | O |
| ATOM | 10623 | N   | LEU C | 360 | 36.271 | 44.244 | −40.803 | 1.00 | 49.33  | N |
| ATOM | 10624 | CA  | LEU C | 360 | 35.873 | 43.075 | −41.477 | 1.00 | 52.13  | C |
| ATOM | 10625 | CB  | LEU C | 360 | 34.463 | 43.294 | −42.044 | 1.00 | 55.97  | C |
| ATOM | 10626 | CG  | LEU C | 360 | 33.949 | 42.304 | −43.109 | 1.00 | 58.25  | C |
| ATOM | 10627 | CD1 | LEU C | 360 | 33.601 | 41.004 | −42.417 | 1.00 | 56.25  | C |
| ATOM | 10628 | CD2 | LEU C | 360 | 32.784 | 42.869 | −43.942 | 1.00 | 58.72  | C |
| ATOM | 10629 | C   | LEU C | 360 | 36.860 | 42.813 | −42.619 | 1.00 | 51.08  | C |
| ATOM | 10630 | O   | LEU C | 360 | 37.055 | 43.656 | −43.489 | 1.00 | 54.31  | O |
| ATOM | 10631 | N   | THR C | 361 | 37.401 | 41.609 | −42.643 | 1.00 | 47.34  | N |
| ATOM | 10632 | CA  | THR C | 361 | 38.354 | 41.185 | −43.627 | 1.00 | 47.71  | C |
| ATOM | 10633 | CB  | THR C | 361 | 39.359 | 40.204 | −42.974 | 1.00 | 47.33  | C |
| ATOM | 10634 | OG1 | THR C | 361 | 38.712 | 39.236 | −42.107 | 1.00 | 49.67  | O |
| ATOM | 10635 | CG2 | THR C | 361 | 40.285 | 40.987 | −42.140 | 1.00 | 47.74  | C |
| ATOM | 10636 | C   | THR C | 361 | 37.703 | 40.510 | −44.816 | 1.00 | 49.82  | C |
| ATOM | 10637 | O   | THR C | 361 | 36.999 | 39.540 | −44.630 | 1.00 | 55.74  | O |
| ATOM | 10638 | N   | VAL C | 362 | 37.967 | 40.982 | −46.038 | 1.00 | 50.38  | N |
| ATOM | 10639 | CA  | VAL C | 362 | 37.466 | 40.331 | −47.281 | 1.00 | 48.47  | C |
| ATOM | 10640 | CB  | VAL C | 362 | 36.372 | 41.170 | −47.940 | 1.00 | 50.15  | C |
| ATOM | 10641 | CG1 | VAL C | 362 | 35.265 | 41.440 | −46.952 | 1.00 | 51.77  | C |
| ATOM | 10642 | CG2 | VAL C | 362 | 36.900 | 42.499 | −48.468 | 1.00 | 52.27  | C |
| ATOM | 10643 | C   | VAL C | 362 | 38.580 | 40.123 | −48.282 | 1.00 | 47.04  | C |
| ATOM | 10644 | O   | VAL C | 362 | 39.565 | 40.819 | −48.188 | 1.00 | 44.92  | O |
| ATOM | 10645 | N   | TYR C | 363 | 38.422 | 39.184 | −49.220 | 1.00 | 50.37  | N |
| ATOM | 10646 | CA  | TYR C | 363 | 39.446 | 38.894 | −50.257 | 1.00 | 56.43  | C |
| ATOM | 10647 | CB  | TYR C | 363 | 39.192 | 37.602 | −51.041 | 1.00 | 59.78  | C |
| ATOM | 10648 | CG  | TYR C | 363 | 39.542 | 36.380 | −50.258 | 1.00 | 68.48  | C |
| ATOM | 10649 | CD1 | TYR C | 363 | 40.856 | 36.118 | −49.931 | 1.00 | 73.24  | C |
| ATOM | 10650 | CE1 | TYR C | 363 | 41.196 | 35.007 | −49.165 | 1.00 | 76.10  | C |
| ATOM | 10651 | CZ  | TYR C | 363 | 40.216 | 34.124 | −48.748 | 1.00 | 76.60  | C |
| ATOM | 10652 | OH  | TYR C | 363 | 40.629 | 33.056 | −48.009 | 1.00 | 82.67  | O |
| ATOM | 10653 | CE2 | TYR C | 363 | 38.881 | 34.340 | −49.057 | 1.00 | 73.25  | C |
| ATOM | 10654 | CD2 | TYR C | 363 | 38.548 | 35.470 | −49.804 | 1.00 | 73.31  | C |
| ATOM | 10655 | C   | TYR C | 363 | 39.584 | 39.973 | −51.285 | 1.00 | 58.39  | C |
| ATOM | 10656 | O   | TYR C | 363 | 40.697 | 40.153 | −51.769 | 1.00 | 60.66  | O |

TABLE 6-continued

Atomic coordinates for CRBN:DDB1: Compound B (Human protein)

| ATOM | 10657 | N | LYS | C | 364 | 38.469 | 40.634 | −51.629 | 1.00 | 59.20 | N |
|---|---|---|---|---|---|---|---|---|---|---|---|
| ATOM | 10658 | CA | LYS | C | 364 | 38.391 | 41.612 | −52.726 | 1.00 | 64.50 | C |
| ATOM | 10659 | CB | LYS | C | 364 | 37.986 | 40.941 | −54.049 | 1.00 | 74.47 | C |
| ATOM | 10660 | CG | LYS | C | 364 | 39.085 | 40.854 | −55.137 | 1.00 | 87.51 | C |
| ATOM | 10661 | CD | LYS | C | 364 | 40.012 | 39.613 | −55.082 | 1.00 | 94.46 | C |
| ATOM | 10662 | CE | LYS | C | 364 | 39.272 | 38.271 | −55.244 | 1.00 | 97.47 | C |
| ATOM | 10663 | NZ | LYS | C | 364 | 39.649 | 37.457 | −56.435 | 1.00 | 98.52 | N |
| ATOM | 10664 | C | LYS | C | 364 | 37.452 | 42.807 | −52.465 | 1.00 | 61.34 | C |
| ATOM | 10665 | O | LYS | C | 364 | 36.395 | 42.691 | −51.844 | 1.00 | 57.80 | O |
| ATOM | 10666 | N | ALA | C | 365 | 37.847 | 43.964 | −52.970 | 1.00 | 57.60 | N |
| ATOM | 10667 | CA | ALA | C | 365 | 37.054 | 45.146 | −52.797 | 1.00 | 56.66 | C |
| ATOM | 10668 | CB | ALA | C | 365 | 37.504 | 45.878 | −51.567 | 1.00 | 56.77 | C |
| ATOM | 10669 | C | ALA | C | 365 | 37.177 | 46.015 | −54.006 | 1.00 | 57.44 | C |
| ATOM | 10670 | O | ALA | C | 365 | 38.084 | 45.865 | −54.784 | 1.00 | 64.68 | O |
| ATOM | 10671 | N | CYS | C | 366 | 36.255 | 46.938 | −54.156 | 1.00 | 59.73 | N |
| ATOM | 10672 | CA | CYS | C | 366 | 36.144 | 47.716 | −55.373 | 1.00 | 65.32 | C |
| ATOM | 10673 | CB | CYS | C | 366 | 34.962 | 47.200 | −56.166 | 1.00 | 67.01 | C |
| ATOM | 10674 | SG | CYS | C | 366 | 35.421 | 45.652 | −56.916 | 1.00 | 70.80 | S |
| ATOM | 10675 | C | CYS | C | 366 | 35.945 | 49.181 | −55.091 | 1.00 | 63.72 | C |
| ATOM | 10676 | O | CYS | C | 366 | 35.554 | 49.535 | −53.985 | 1.00 | 68.53 | O |
| ATOM | 10677 | N | ASN | C | 367 | 36.188 | 50.013 | −56.104 | 1.00 | 54.92 | N |
| ATOM | 10678 | CA | ASN | C | 367 | 35.939 | 51.446 | −56.022 | 1.00 | 53.17 | C |
| ATOM | 10679 | CB | ASN | C | 367 | 34.440 | 51.733 | −55.976 | 1.00 | 52.34 | C |
| ATOM | 10680 | CG | ASN | C | 367 | 33.655 | 50.913 | −56.946 | 1.00 | 48.55 | C |
| ATOM | 10681 | OD1 | ASN | C | 367 | 32.745 | 50.212 | −56.558 | 1.00 | 47.29 | O |
| ATOM | 10682 | ND2 | ASN | C | 367 | 34.023 | 50.952 | −58.189 | 1.00 | 48.73 | N |
| ATOM | 10683 | C | ASN | C | 367 | 36.592 | 52.122 | −54.829 | 1.00 | 54.27 | C |
| ATOM | 10684 | O | ASN | C | 367 | 36.026 | 53.041 | −54.181 | 1.00 | 51.28 | O |
| ATOM | 10685 | N | LEU | C | 368 | 37.777 | 51.628 | −54.519 | 1.00 | 56.96 | N |
| ATOM | 10686 | CA | LEU | C | 368 | 38.536 | 52.139 | −53.418 | 1.00 | 56.09 | C |
| ATOM | 10687 | CB | LEU | C | 368 | 38.894 | 51.010 | −52.476 | 1.00 | 54.24 | C |
| ATOM | 10688 | CG | LEU | C | 368 | 37.791 | 50.303 | −51.736 | 1.00 | 51.55 | C |
| ATOM | 10689 | CD1 | LEU | C | 368 | 38.390 | 49.324 | −50.723 | 1.00 | 53.04 | C |
| ATOM | 10690 | CD2 | LEU | C | 368 | 36.937 | 51.348 | −51.046 | 1.00 | 52.49 | C |
| ATOM | 10691 | C | LEU | C | 368 | 39.766 | 52.701 | −54.067 | 1.00 | 56.35 | C |
| ATOM | 10692 | O | LEU | C | 368 | 40.301 | 52.092 | −54.992 | 1.00 | 61.83 | O |
| ATOM | 10693 | N | ASN | C | 369 | 40.171 | 53.879 | −53.640 | 1.00 | 54.58 | N |
| ATOM | 10694 | CA | ASN | C | 369 | 41.404 | 54.476 | −54.121 | 1.00 | 55.13 | C |
| ATOM | 10695 | CB | ASN | C | 369 | 41.180 | 55.927 | −54.615 | 1.00 | 54.12 | C |
| ATOM | 10696 | CG | ASN | C | 369 | 40.545 | 55.982 | −55.991 | 1.00 | 57.35 | C |
| ATOM | 10697 | OD1 | ASN | C | 369 | 40.665 | 55.040 | −56.764 | 1.00 | 65.22 | O |
| ATOM | 10698 | ND2 | ASN | C | 369 | 39.855 | 57.074 | −56.307 | 1.00 | 62.32 | N |
| ATOM | 10699 | C | ASN | C | 369 | 42.329 | 54.334 | −52.925 | 1.00 | 54.38 | C |
| ATOM | 10700 | O | ASN | C | 369 | 41.849 | 54.400 | −51.777 | 1.00 | 55.08 | O |
| ATOM | 10701 | N | LEU | C | 370 | 43.615 | 54.070 | −53.201 | 1.00 | 51.25 | N |
| ATOM | 10702 | CA | LEU | C | 370 | 44.642 | 53.802 | −52.178 | 1.00 | 48.72 | C |
| ATOM | 10703 | CB | LEU | C | 370 | 45.508 | 52.648 | −52.601 | 1.00 | 45.31 | C |
| ATOM | 10704 | CG | LEU | C | 370 | 44.758 | 51.362 | −52.797 | 1.00 | 44.46 | C |
| ATOM | 10705 | CD1 | LEU | C | 370 | 45.451 | 50.405 | −53.755 | 1.00 | 42.70 | C |
| ATOM | 10706 | CD2 | LEU | C | 370 | 44.530 | 50.739 | −51.432 | 1.00 | 46.40 | C |
| ATOM | 10707 | C | LEU | C | 370 | 45.530 | 54.999 | −52.081 | 1.00 | 52.46 | C |
| ATOM | 10708 | O | LEU | C | 370 | 46.037 | 55.478 | −53.091 | 1.00 | 57.05 | O |
| ATOM | 10709 | N | ILE | C | 371 | 45.727 | 55.539 | −50.903 | 1.00 | 57.54 | N |
| ATOM | 10710 | CA | ILE | C | 371 | 46.541 | 56.743 | −50.863 | 1.00 | 65.22 | C |
| ATOM | 10711 | CB | ILE | C | 371 | 45.709 | 58.067 | −50.732 | 1.00 | 69.81 | C |
| ATOM | 10712 | CG1 | ILE | C | 371 | 45.301 | 58.340 | −49.290 | 1.00 | 74.09 | C |
| ATOM | 10713 | CD1 | ILE | C | 371 | 46.270 | 59.242 | −48.544 | 1.00 | 80.49 | C |
| ATOM | 10714 | CG2 | ILE | C | 371 | 44.477 | 58.052 | −51.656 | 1.00 | 68.15 | C |
| ATOM | 10715 | C | ILE | C | 371 | 47.598 | 56.526 | −49.821 | 1.00 | 61.40 | C |
| ATOM | 10716 | O | ILE | C | 371 | 47.377 | 55.827 | −48.857 | 1.00 | 61.03 | O |
| ATOM | 10717 | N | GLY | C | 372 | 48.759 | 57.116 | −50.052 | 1.00 | 62.66 | N |
| ATOM | 10718 | CA | GLY | C | 372 | 49.933 | 56.866 | −49.230 | 1.00 | 62.72 | C |
| ATOM | 10719 | C | GLY | C | 372 | 50.642 | 55.568 | −49.560 | 1.00 | 60.91 | C |
| ATOM | 10720 | O | GLY | C | 372 | 50.268 | 54.854 | −50.504 | 1.00 | 54.32 | O |
| ATOM | 10721 | N | ARG | C | 373 | 51.673 | 55.268 | −48.766 | 1.00 | 62.57 | N |
| ATOM | 10722 | CA | ARG | C | 373 | 52.475 | 54.111 | −49.034 | 1.00 | 63.26 | C |
| ATOM | 10723 | CB | ARG | C | 373 | 53.845 | 54.569 | −49.516 | 1.00 | 70.60 | C |
| ATOM | 10724 | CG | ARG | C | 373 | 54.009 | 54.230 | −51.003 | 1.00 | 80.59 | C |
| ATOM | 10725 | CD | ARG | C | 373 | 54.534 | 55.318 | −51.919 | 1.00 | 88.87 | C |
| ATOM | 10726 | NE | ARG | C | 373 | 55.913 | 55.097 | −52.388 | 1.00 | 102.49 | N |
| ATOM | 10727 | CZ | ARG | C | 373 | 56.386 | 53.997 | −53.008 | 1.00 | 107.67 | C |
| ATOM | 10728 | NH1 | ARG | C | 373 | 57.674 | 53.967 | −53.399 | 1.00 | 107.60 | N |
| ATOM | 10729 | NH2 | ARG | C | 373 | 55.610 | 52.916 | −53.232 | 1.00 | 106.17 | N |
| ATOM | 10730 | C | ARG | C | 373 | 52.452 | 53.015 | −47.959 | 1.00 | 57.81 | C |
| ATOM | 10731 | O | ARG | C | 373 | 52.157 | 53.296 | −46.787 | 1.00 | 56.79 | O |
| ATOM | 10732 | N | PRO | C | 374 | 52.645 | 51.738 | −48.379 | 1.00 | 52.75 | N |
| ATOM | 10733 | CA | PRO | C | 374 | 52.359 | 50.657 | −47.449 | 1.00 | 53.03 | C |
| ATOM | 10734 | CB | PRO | C | 374 | 52.682 | 49.385 | −48.259 | 1.00 | 51.32 | C |

TABLE 6-continued

Atomic coordinates for CRBN:DDB1: Compound B (Human protein)

| ATOM | 10735 | CG | PRO C | 374 | 52.350 | 49.771 | −49.639 | 1.00 | 50.56 | C |
|---|---|---|---|---|---|---|---|---|---|---|
| ATOM | 10736 | CD | PRO C | 374 | 52.899 | 51.182 | −49.716 | 1.00 | 53.08 | C |
| ATOM | 10737 | C | PRO C | 374 | 53.221 | 50.766 | −46.254 | 1.00 | 50.84 | C |
| ATOM | 10738 | O | PRO C | 374 | 54.311 | 51.259 | −46.387 | 1.00 | 57.62 | O |
| ATOM | 10739 | N | SER C | 375 | 52.715 | 50.370 | −45.101 | 1.00 | 48.15 | N |
| ATOM | 10740 | CA | SER C | 375 | 53.438 | 50.532 | −43.846 | 1.00 | 49.11 | C |
| ATOM | 10741 | CB | SER C | 375 | 53.055 | 51.834 | −43.131 | 1.00 | 47.80 | C |
| ATOM | 10742 | OG | SER C | 375 | 53.597 | 51.923 | −41.825 | 1.00 | 44.07 | O |
| ATOM | 10743 | C | SER C | 375 | 53.044 | 49.383 | −43.002 | 1.00 | 52.63 | C |
| ATOM | 10744 | O | SER C | 375 | 51.922 | 48.899 | −43.112 | 1.00 | 57.57 | O |
| ATOM | 10745 | N | THR C | 376 | 53.961 | 48.966 | −42.142 | 1.00 | 53.34 | N |
| ATOM | 10746 | CA | THR C | 376 | 53.717 | 47.886 | −41.209 | 1.00 | 51.18 | C |
| ATOM | 10747 | CB | THR C | 376 | 54.877 | 46.935 | −41.286 | 1.00 | 47.74 | C |
| ATOM | 10748 | OG1 | THR C | 376 | 56.023 | 47.591 | −40.759 | 1.00 | 47.05 | O |
| ATOM | 10749 | CG2 | THR C | 376 | 55.162 | 46.601 | −42.702 | 1.00 | 48.45 | C |
| ATOM | 10750 | C | THR C | 376 | 53.624 | 48.471 | −39.796 | 1.00 | 53.32 | C |
| ATOM | 10751 | O | THR C | 376 | 53.603 | 47.736 | −38.797 | 1.00 | 56.85 | O |
| ATOM | 10752 | N | GLU C | 377 | 53.559 | 49.796 | −39.710 | 1.00 | 54.24 | N |
| ATOM | 10753 | CA | GLU C | 377 | 53.641 | 50.448 | −38.432 | 1.00 | 57.82 | C |
| ATOM | 10754 | CB | GLU C | 377 | 53.921 | 51.935 | −38.567 | 1.00 | 60.62 | C |
| ATOM | 10755 | CG | GLU C | 377 | 54.524 | 52.555 | −37.330 | 1.00 | 67.35 | C |
| ATOM | 10756 | CD | GLU C | 377 | 54.651 | 54.066 | −37.454 | 1.00 | 82.35 | C |
| ATOM | 10757 | OE1 | GLU C | 377 | 54.350 | 54.661 | −38.561 | 1.00 | 92.77 | O |
| ATOM | 10758 | OE2 | GLU C | 377 | 55.043 | 54.658 | −36.419 | 1.00 | 84.76 | O |
| ATOM | 10759 | C | GLU C | 377 | 52.326 | 50.198 | −37.771 | 1.00 | 55.27 | C |
| ATOM | 10760 | O | GLU C | 377 | 51.285 | 50.490 | −38.333 | 1.00 | 62.99 | O |
| ATOM | 10761 | N | HIS C | 378 | 52.382 | 49.572 | −36.615 | 1.00 | 51.49 | N |
| ATOM | 10762 | CA | HIS C | 378 | 51.226 | 49.393 | −35.771 | 1.00 | 50.76 | C |
| ATOM | 10763 | CB | HIS C | 378 | 50.636 | −50.741 | −35.461 | 1.00 | 50.11 | C |
| ATOM | 10764 | CG | HIS C | 378 | 49.831 | 50.759 | −34.227 | 1.00 | 51.40 | C |
| ATOM | 10765 | ND1 | HIS C | 378 | 48.462 | 50.659 | −34.235 | 1.00 | 57.26 | N |
| ATOM | 10766 | CE1 | HIS C | 378 | 48.005 | 50.760 | −33.000 | 1.00 | 56.04 | C |
| ATOM | 10767 | NE2 | HIS C | 378 | 49.036 | 50.908 | −32.196 | 1.00 | 53.88 | N |
| ATOM | 10768 | CD2 | HIS C | 378 | 50.190 | 50.907 | −32.941 | 1.00 | 53.83 | C |
| ATOM | 10769 | C | HIS C | 378 | 50.189 | 48.485 | −36.391 | 1.00 | 48.51 | C |
| ATOM | 10770 | O | HIS C | 378 | 49.020 | 48.518 | −36.019 | 1.00 | 50.74 | O |
| ATOM | 10771 | N | SER C | 379 | 50.634 | 47.646 | −37.313 | 1.00 | 45.39 | N |
| ATOM | 10772 | CA | SER C | 379 | 49.724 | 46.834 | −38.057 | 1.00 | 45.00 | C |
| ATOM | 10773 | CB | SER C | 379 | 50.399 | 46.156 | −39.216 | 1.00 | 43.37 | C |
| ATOM | 10774 | OG | SER C | 379 | 49.527 | 45.182 | −39.703 | 1.00 | 41.91 | O |
| ATOM | 10775 | C | SER C | 379 | 49.114 | 45.764 | −37.186 | 1.00 | 50.14 | C |
| ATOM | 10776 | O | SER C | 379 | 49.794 | 45.001 | −36.503 | 1.00 | 55.29 | O |
| ATOM | 10777 | N | TRP C | 380 | 47.807 | 45.674 | −37.298 | 1.00 | 54.02 | N |
| ATOM | 10778 | CA | TRP C | 380 | 46.991 | 44.773 | −36.516 | 1.00 | 52.59 | C |
| ATOM | 10779 | CB | TRP C | 380 | 45.546 | 45.214 | −36.652 | 1.00 | 51.97 | C |
| ATOM | 10780 | CG | TRP C | 380 | 45.248 | 46.556 | −36.216 | 1.00 | 52.35 | C |
| ATOM | 10781 | CD1 | TRP C | 380 | 45.794 | 47.232 | −35.176 | 1.00 | 52.72 | C |
| ATOM | 10782 | NE1 | TRP C | 380 | 45.223 | 48.482 | −35.074 | 1.00 | 53.90 | N |
| ATOM | 10783 | CE2 | TRP C | 380 | 44.262 | 48.597 | −36.044 | 1.00 | 52.06 | C |
| ATOM | 10784 | CD2 | TRP C | 380 | 44.270 | 47.411 | −36.791 | 1.00 | 53.21 | C |
| ATOM | 10785 | CE3 | TRP C | 380 | 43.387 | 47.282 | −37.861 | 1.00 | 52.77 | C |
| ATOM | 10786 | CZ3 | TRP C | 380 | 42.548 | 48.327 | −38.150 | 1.00 | 51.84 | C |
| ATOM | 10787 | CH2 | TRP C | 380 | 42.565 | 49.483 | −37.383 | 1.00 | 51.86 | C |
| ATOM | 10788 | CZ2 | TRP C | 380 | 43.410 | 49.627 | −36.322 | 1.00 | 50.98 | C |
| ATOM | 10789 | C | TRP C | 380 | 47.055 | 43.308 | −36.980 | 1.00 | 52.11 | C |
| ATOM | 10790 | O | TRP C | 380 | 46.584 | 42.391 | −36.277 | 1.00 | 54.45 | O |
| ATOM | 10791 | N | PHE C | 381 | 47.553 | 43.103 | −38.186 | 1.00 | 49.89 | N |
| ATOM | 10792 | CA | PHE C | 381 | 47.734 | 41.781 | −38.706 | 1.00 | 51.02 | C |
| ATOM | 10793 | CB | PHE C | 381 | 46.889 | 41.583 | −39.949 | 1.00 | 50.95 | C |
| ATOM | 10794 | CG | PHE C | 381 | 45.418 | 41.654 | −39.720 | 1.00 | 47.99 | C |
| ATOM | 10795 | CD1 | PHE C | 381 | 44.721 | 40.532 | −39.406 | 1.00 | 46.54 | C |
| ATOM | 10796 | CE1 | PHE C | 381 | 43.378 | 40.565 | −39.241 | 1.00 | 47.87 | C |
| ATOM | 10797 | CZ | PHE C | 381 | 42.697 | 41.745 | −39.423 | 1.00 | 49.21 | C |
| ATOM | 10798 | CE2 | PHE C | 381 | 43.379 | 42.873 | −39.789 | 1.00 | 48.95 | C |
| ATOM | 10799 | CD2 | PHE C | 381 | 44.741 | 42.819 | −39.943 | 1.00 | 49.04 | C |
| ATOM | 10800 | C | PHE C | 381 | 49.197 | 41.648 | −39.073 | 1.00 | 50.17 | C |
| ATOM | 10801 | O | PHE C | 381 | 49.587 | 42.056 | −40.152 | 1.00 | 51.21 | O |
| ATOM | 10802 | N | PRO C | 382 | 50.019 | 41.084 | −38.181 | 1.00 | 50.59 | N |
| ATOM | 10803 | CA | PRO C | 382 | 51.442 | 41.025 | −38.467 | 1.00 | 52.39 | C |
| ATOM | 10804 | CB | PRO C | 382 | 52.009 | 40.411 | −37.215 | 1.00 | 51.15 | C |
| ATOM | 10805 | CG | PRO C | 382 | 51.120 | 40.931 | −36.159 | 1.00 | 51.04 | C |
| ATOM | 10806 | CD | PRO C | 382 | 49.769 | 40.757 | −36.776 | 1.00 | 50.87 | C |
| ATOM | 10807 | C | PRO C | 382 | 51.828 | 40.202 | −39.662 | 1.00 | 55.27 | C |
| ATOM | 10808 | O | PRO C | 382 | 51.225 | 39.152 | −39.951 | 1.00 | 55.66 | O |
| ATOM | 10809 | N | GLY C | 383 | 52.824 | 40.718 | −40.378 | 1.00 | 56.47 | N |
| ATOM | 10810 | CA | GLY C | 383 | 53.231 | 40.142 | −41.656 | 1.00 | 58.57 | C |
| ATOM | 10811 | C | GLY C | 383 | 52.639 | 40.945 | −42.785 | 1.00 | 57.15 | C |
| ATOM | 10812 | O | GLY C | 383 | 53.139 | 40.923 | −43.878 | 1.00 | 56.06 | O |

TABLE 6-continued

Atomic coordinates for CRBN:DDB1: Compound B (Human protein)

| ATOM | 10813 | N   | TYR C | 384 | 51.577 | 41.676 | -42.504 | 1.00 | 57.82 | N |
|------|-------|-----|-------|-----|--------|--------|---------|------|-------|---|
| ATOM | 10814 | CA  | TYR C | 384 | 50.943 | 42.479 | -43.490 | 1.00 | 57.05 | C |
| ATOM | 10815 | CB  | TYR C | 384 | 49.453 | 42.093 | -43.584 | 1.00 | 58.31 | C |
| ATOM | 10816 | CG  | TYR C | 384 | 49.199 | 40.711 | -44.150 | 1.00 | 57.53 | C |
| ATOM | 10817 | CD1 | TYR C | 384 | 49.330 | 40.465 | -45.499 | 1.00 | 60.22 | C |
| ATOM | 10818 | CE1 | TYR C | 384 | 49.112 | 39.189 | -46.032 | 1.00 | 63.00 | C |
| ATOM | 10819 | CZ  | TYR C | 384 | 48.725 | 38.129 | -45.204 | 1.00 | 61.12 | C |
| ATOM | 10820 | OH  | TYR C | 384 | 48.498 | 36.886 | -45.727 | 1.00 | 53.17 | O |
| ATOM | 10821 | CE2 | TYR C | 384 | 48.558 | 38.361 | -43.853 | 1.00 | 61.16 | C |
| ATOM | 10822 | CD2 | TYR C | 384 | 48.802 | 39.651 | -43.336 | 1.00 | 61.37 | C |
| ATOM | 10823 | C   | TYR C | 384 | 51.193 | 43.992 | -43.191 | 1.00 | 56.81 | C |
| ATOM | 10824 | O   | TYR C | 384 | 51.361 | 44.446 | -42.009 | 1.00 | 53.77 | O |
| ATOM | 10825 | N   | ALA C | 385 | 51.311 | 44.722 | -44.306 | 1.00 | 53.88 | N |
| ATOM | 10826 | CA  | ALA C | 385 | 51.361 | 46.159 | -44.329 | 1.00 | 52.95 | C |
| ATOM | 10827 | CB  | ALA C | 385 | 52.412 | 46.636 | -45.286 | 1.00 | 51.79 | C |
| ATOM | 10828 | C   | ALA C | 385 | 50.022 | 46.677 | -44.793 | 1.00 | 55.28 | C |
| ATOM | 10829 | O   | ALA C | 385 | 49.314 | 46.022 | -45.563 | 1.00 | 55.77 | O |
| ATOM | 10830 | N   | TRP C | 386 | 49.726 | 47.899 | -44.367 | 1.00 | 54.32 | N |
| ATOM | 10831 | CA  | TRP C | 386 | 48.453 | 48.514 | -44.602 | 1.00 | 53.20 | C |
| ATOM | 10832 | CB  | TRP C | 386 | 47.766 | 48.831 | -43.282 | 1.00 | 51.97 | C |
| ATOM | 10833 | CG  | TRP C | 386 | 48.539 | 49.599 | -42.337 | 1.00 | 51.56 | C |
| ATOM | 10834 | CD1 | TRP C | 386 | 49.260 | 49.110 | -41.311 | 1.00 | 52.93 | C |
| ATOM | 10835 | NE1 | TRP C | 386 | 49.872 | 50.133 | -40.609 | 1.00 | 53.61 | N |
| ATOM | 10836 | CE2 | TRP C | 386 | 49.537 | 51.320 | -41.191 | 1.00 | 53.47 | C |
| ATOM | 10837 | CD2 | TRP C | 386 | 48.688 | 51.020 | -42.295 | 1.00 | 53.55 | C |
| ATOM | 10838 | CE3 | TRP C | 386 | 48.192 | 52.074 | -43.071 | 1.00 | 50.53 | C |
| ATOM | 10839 | CZ3 | TRP C | 386 | 48.548 | 53.368 | -42.723 | 1.00 | 50.36 | C |
| ATOM | 10840 | CH2 | TRP C | 386 | 49.347 | 53.627 | -41.599 | 1.00 | 50.77 | C |
| ATOM | 10841 | CZ2 | TRP C | 386 | 49.862 | 52.618 | -40.828 | 1.00 | 50.83 | C |
| ATOM | 10842 | C   | TRP C | 386 | 48.615 | 49.759 | -45.447 | 1.00 | 53.53 | C |
| ATOM | 10843 | O   | TRP C | 386 | 49.555 | 50.506 | -45.273 | 1.00 | 60.62 | O |
| ATOM | 10844 | N   | THR C | 387 | 47.699 | 49.953 | -46.380 | 1.00 | 52.97 | N |
| ATOM | 10845 | CA  | THR C | 387 | 47.568 | 51.187 | -47.148 | 1.00 | 52.60 | C |
| ATOM | 10846 | CB  | THR C | 387 | 47.671 | 50.915 | -48.644 | 1.00 | 53.67 | C |
| ATOM | 10847 | OG1 | THR C | 387 | 48.924 | 50.279 | -48.938 | 1.00 | 57.32 | O |
| ATOM | 10848 | CG2 | THR C | 387 | 47.496 | 52.184 | -49.432 | 1.00 | 52.77 | C |
| ATOM | 10849 | C   | THR C | 387 | 46.160 | 51.659 | -46.950 | 1.00 | 50.11 | C |
| ATOM | 10850 | O   | THR C | 387 | 45.256 | 50.854 | -46.951 | 1.00 | 53.44 | O |
| ATOM | 10851 | N   | VAL C | 388 | 45.970 | 52.953 | -46.825 | 1.00 | 46.97 | N |
| ATOM | 10852 | CA  | VAL C | 388 | 44.650 | 53.515 | -46.586 | 1.00 | 46.18 | C |
| ATOM | 10853 | CB  | VAL C | 388 | 44.824 | 54.970 | -46.107 | 1.00 | 45.36 | C |
| ATOM | 10854 | CG1 | VAL C | 388 | 43.533 | 55.787 | -46.122 | 1.00 | 44.74 | C |
| ATOM | 10855 | CG2 | VAL C | 388 | 45.436 | 54.964 | -44.736 | 1.00 | 46.64 | C |
| ATOM | 10856 | C   | VAL C | 388 | 43.777 | 53.452 | -47.852 | 1.00 | 47.76 | C |
| ATOM | 10857 | O   | VAL C | 388 | 44.224 | 53.815 | -48.934 | 1.00 | 49.17 | O |
| ATOM | 10858 | N   | ALA C | 389 | 42.529 | 53.013 | -47.701 | 1.00 | 49.13 | N |
| ATOM | 10859 | CA  | ALA C | 389 | 41.566 | 52.960 | -48.807 | 1.00 | 50.92 | C |
| ATOM | 10860 | CB  | ALA C | 389 | 40.998 | 51.563 | -48.919 | 1.00 | 51.61 | C |
| ATOM | 10861 | C   | ALA C | 389 | 40.420 | 53.947 | -48.592 | 1.00 | 52.68 | C |
| ATOM | 10862 | O   | ALA C | 389 | 39.861 | 53.992 | -47.475 | 1.00 | 53.97 | O |
| ATOM | 10863 | N   | GLN C | 390 | 40.060 | 54.710 | -49.637 | 1.00 | 50.12 | N |
| ATOM | 10864 | CA  | GLN C | 390 | 38.858 | 55.532 | -49.579 | 1.00 | 50.43 | C |
| ATOM | 10865 | CB  | GLN C | 390 | 39.181 | 57.036 | -49.363 | 1.00 | 50.20 | C |
| ATOM | 10866 | CG  | GLN C | 390 | 40.508 | 57.546 | -49.884 | 1.00 | 53.02 | C |
| ATOM | 10867 | CD  | GLN C | 390 | 40.975 | 58.898 | -49.280 | 1.00 | 54.09 | C |
| ATOM | 10868 | OE1 | GLN C | 390 | 41.359 | 58.963 | -48.132 | 1.00 | 59.38 | O |
| ATOM | 10869 | NE2 | GLN C | 390 | 41.010 | 59.945 | -50.084 | 1.00 | 52.65 | N |
| ATOM | 10870 | C   | GLN C | 390 | 37.871 | 55.272 | -50.731 | 1.00 | 51.32 | C |
| ATOM | 10871 | O   | GLN C | 390 | 38.220 | 54.672 | -51.736 | 1.00 | 52.84 | O |
| ATOM | 10872 | N   | CYS C | 391 | 36.619 | 55.688 | -50.533 | 1.00 | 50.95 | N |
| ATOM | 10873 | CA  | CYS C | 391 | 35.601 | 55.660 | -51.566 | 1.00 | 51.82 | C |
| ATOM | 10874 | CB  | CYS C | 391 | 34.249 | 56.095 | -51.013 | 1.00 | 53.56 | C |
| ATOM | 10875 | SG  | CYS C | 391 | 32.721 | 55.917 | -52.024 | 1.00 | 58.62 | S |
| ATOM | 10876 | C   | CYS C | 391 | 36.042 | 56.630 | -52.637 | 1.00 | 53.32 | C |
| ATOM | 10877 | O   | CYS C | 391 | 36.244 | 57.830 | -52.409 | 1.00 | 57.91 | O |
| ATOM | 10878 | N   | LYS C | 392 | 35.996 | 56.074 | -53.820 | 1.00 | 50.33 | N |
| ATOM | 10879 | CA  | LYS C | 392 | 36.326 | 56.669 | -55.058 | 1.00 | 44.20 | C |
| ATOM | 10880 | CB  | LYS C | 392 | 36.001 | 55.606 | -56.086 | 1.00 | 43.62 | C |
| ATOM | 10881 | CG  | LYS C | 392 | 35.688 | 56.075 | -57.468 | 1.00 | 46.84 | C |
| ATOM | 10882 | CD  | LYS C | 392 | 34.752 | 55.107 | -58.162 | 1.00 | 45.10 | C |
| ATOM | 10883 | CE  | LYS C | 392 | 35.427 | 53.815 | -58.518 | 1.00 | 45.47 | C |
| ATOM | 10884 | NZ  | LYS C | 392 | 34.561 | 53.091 | -59.471 | 1.00 | 46.85 | N |
| ATOM | 10885 | C   | LYS C | 392 | 35.458 | 57.882 | -55.245 | 1.00 | 42.93 | C |
| ATOM | 10886 | O   | LYS C | 392 | 35.889 | 58.853 | -55.794 | 1.00 | 42.11 | O |
| ATOM | 10887 | N   | ILE C | 393 | 34.218 | 57.829 | -54.809 | 1.00 | 41.91 | N |
| ATOM | 10888 | CA  | ILE C | 393 | 33.315 | 58.950 | -54.973 | 1.00 | 42.65 | C |
| ATOM | 10889 | CB  | ILE C | 393 | 31.885 | 58.424 | -55.008 | 1.00 | 44.17 | C |
| ATOM | 10890 | CG1 | ILE C | 393 | 31.789 | 57.203 | -55.881 | 1.00 | 44.37 | C |

TABLE 6-continued

Atomic coordinates for CRBN:DDB1: Compound B (Human protein)

| ATOM | 10891 | CD1 | ILE C | 393 | 31.852 | 57.506 | −57.344 | 1.00 | 44.99 | C |
|---|---|---|---|---|---|---|---|---|---|---|
| ATOM | 10892 | CG2 | ILE C | 393 | 30.927 | 59.476 | −55.502 | 1.00 | 43.96 | C |
| ATOM | 10893 | C | ILE C | 393 | 33.236 | 60.036 | −53.930 | 1.00 | 42.33 | C |
| ATOM | 10894 | O | ILE C | 393 | 33.250 | 61.185 | −54.244 | 1.00 | 48.08 | O |
| ATOM | 10895 | N | CYS C | 394 | 33.129 | 59.646 | −52.685 | 1.00 | 41.11 | N |
| ATOM | 10896 | CA | CYS C | 394 | 32.911 | 60.521 | −51.551 | 1.00 | 42.59 | C |
| ATOM | 10897 | CB | CYS C | 394 | 31.779 | 59.967 | −50.670 | 1.00 | 40.60 | C |
| ATOM | 10898 | SG | CYS C | 394 | 32.085 | 58.445 | −49.811 | 1.00 | 41.76 | S |
| ATOM | 10899 | C | CYS C | 394 | 34.147 | 60.783 | −50.705 | 1.00 | 46.71 | C |
| ATOM | 10900 | O | CYS C | 394 | 34.119 | 61.662 | −49.855 | 1.00 | 50.52 | O |
| ATOM | 10901 | N | ALA C | 395 | 35.225 | 60.027 | −50.940 | 1.00 | 48.52 | N |
| ATOM | 10902 | CA | ALA C | 395 | 36.484 | 60.168 | −50.208 | 1.00 | 45.80 | C |
| ATOM | 10903 | CB | ALA C | 395 | 36.866 | 61.616 | −50.149 | 1.00 | 45.61 | C |
| ATOM | 10904 | C | ALA C | 395 | 36.492 | 59.544 | −48.794 | 1.00 | 47.94 | C |
| ATOM | 10905 | O | ALA C | 395 | 37.475 | 59.654 | −48.034 | 1.00 | 46.06 | O |
| ATOM | 10906 | N | SER C | 396 | 35.424 | 58.832 | −48.446 | 1.00 | 50.73 | N |
| ATOM | 10907 | CA | SER C | 396 | 35.270 | 58.345 | −47.085 | 1.00 | 50.59 | C |
| ATOM | 10908 | CB | SER C | 396 | 33.855 | 57.786 | −46.847 | 1.00 | 52.05 | C |
| ATOM | 10909 | OG | SER C | 396 | 32.873 | 58.827 | −46.856 | 1.00 | 58.68 | O |
| ATOM | 10910 | C | SER C | 396 | 36.329 | 57.288 | −46.829 | 1.00 | 50.09 | C |
| ATOM | 10911 | O | SER C | 396 | 36.541 | 56.415 | −47.632 | 1.00 | 47.09 | O |
| ATOM | 10912 | N | HIS C | 397 | 37.017 | 57.400 | −45.710 | 1.00 | 53.33 | N |
| ATOM | 10913 | CA | HIS C | 397 | 37.879 | 56.353 | −45.280 | 1.00 | 54.59 | C |
| ATOM | 10914 | CB | HIS C | 397 | 38.655 | 56.794 | −44.066 | 1.00 | 58.23 | C |
| ATOM | 10915 | CG | HIS C | 397 | 39.667 | 55.803 | −43.639 | 1.00 | 67.82 | C |
| ATOM | 10916 | ND1 | HIS C | 397 | 39.323 | 54.572 | −43.117 | 1.00 | 77.34 | N |
| ATOM | 10917 | CE1 | HIS C | 397 | 40.418 | 53.892 | −42.852 | 1.00 | 80.46 | C |
| ATOM | 10918 | NE2 | HIS C | 397 | 41.457 | 54.635 | −43.194 | 1.00 | 82.40 | N |
| ATOM | 10919 | CD2 | HIS C | 397 | 41.013 | 55.836 | −43.685 | 1.00 | 71.07 | C |
| ATOM | 10920 | C | HIS C | 397 | 37.039 | 55.099 | −45.004 | 1.00 | 55.08 | C |
| ATOM | 10921 | O | HIS C | 397 | 36.421 | 54.961 | −43.951 | 1.00 | 53.65 | O |
| ATOM | 10922 | N | ILE C | 398 | 37.028 | 54.202 | −45.985 | 1.00 | 56.59 | N |
| ATOM | 10923 | CA | ILE C | 398 | 36.366 | 52.884 | −45.918 | 1.00 | 55.63 | C |
| ATOM | 10924 | CB | ILE C | 398 | 36.120 | 52.356 | −47.373 | 1.00 | 55.85 | C |
| ATOM | 10925 | CG1 | ILE C | 398 | 35.063 | 53.189 | −48.074 | 1.00 | 59.80 | C |
| ATOM | 10926 | CD1 | ILE C | 398 | 33.763 | 53.358 | −47.313 | 1.00 | 63.49 | C |
| ATOM | 10927 | CG2 | ILE C | 398 | 35.671 | 50.920 | −47.461 | 1.00 | 55.04 | C |
| ATOM | 10928 | C | ILE C | 398 | 37.164 | 51.837 | −45.125 | 1.00 | 55.91 | C |
| ATOM | 10929 | O | ILE C | 398 | 36.571 | 50.877 | −44.645 | 1.00 | 57.92 | O |
| ATOM | 10930 | N | GLY C | 399 | 38.492 | 51.979 | −45.002 | 1.00 | 55.44 | N |
| ATOM | 10931 | CA | GLY C | 399 | 39.354 | 50.850 | −44.535 | 1.00 | 51.73 | C |
| ATOM | 10932 | C | GLY C | 399 | 40.817 | 50.865 | −44.995 | 1.00 | 48.62 | C |
| ATOM | 10933 | O | GLY C | 399 | 41.449 | 51.945 | −45.123 | 1.00 | 48.63 | O |
| ATOM | 10934 | N | TRP C | 400 | 41.363 | 49.670 | −45.200 | 1.00 | 42.81 | N |
| ATOM | 10935 | CA | TRP C | 400 | 42.744 | 49.513 | −45.584 | 1.00 | 44.53 | C |
| ATOM | 10936 | CB | TRP C | 400 | 43.669 | 49.360 | −44.356 | 1.00 | 45.66 | C |
| ATOM | 10937 | CG | TRP C | 400 | 43.625 | 50.497 | −43.357 | 1.00 | 46.57 | C |
| ATOM | 10938 | CD1 | TRP C | 400 | 44.434 | 51.585 | −43.316 | 1.00 | 47.05 | C |
| ATOM | 10939 | NE1 | TRP C | 400 | 44.084 | 52.405 | −42.287 | 1.00 | 47.56 | N |
| ATOM | 10940 | CE2 | TRP C | 400 | 43.027 | 51.838 | −41.634 | 1.00 | 49.37 | C |
| ATOM | 10941 | CD2 | TRP C | 400 | 42.721 | 50.638 | −42.282 | 1.00 | 47.78 | C |
| ATOM | 10942 | CE3 | TRP C | 400 | 41.667 | 49.858 | −41.799 | 1.00 | 51.80 | C |
| ATOM | 10943 | CZ3 | TRP C | 400 | 40.974 | 50.282 | −40.688 | 1.00 | 53.57 | C |
| ATOM | 10944 | CH2 | TRP C | 400 | 41.303 | 51.495 | −40.057 | 1.00 | 54.33 | C |
| ATOM | 10945 | CZ2 | TRP C | 400 | 42.325 | 52.282 | −40.517 | 1.00 | 53.39 | C |
| ATOM | 10946 | C | TRP C | 400 | 42.926 | 48.286 | −46.446 | 1.00 | 47.26 | C |
| ATOM | 10947 | O | TRP C | 400 | 42.432 | 47.197 | −46.128 | 1.00 | 49.37 | O |
| ATOM | 10948 | N | LYS C | 401 | 43.648 | 48.449 | −47.541 | 1.00 | 49.85 | N |
| ATOM | 10949 | CA | LYS C | 401 | 44.212 | 47.311 | −48.242 | 1.00 | 51.10 | C |
| ATOM | 10950 | CB | LYS C | 401 | 44.705 | 47.748 | −49.592 | 1.00 | 49.87 | C |
| ATOM | 10951 | CG | LYS C | 401 | 45.155 | 46.591 | −50.402 | 1.00 | 50.51 | C |
| ATOM | 10952 | CD | LYS C | 401 | 45.605 | 47.039 | −51.767 | 1.00 | 52.22 | C |
| ATOM | 10953 | CE | LYS C | 401 | 45.951 | 45.770 | −52.523 | 1.00 | 54.14 | C |
| ATOM | 10954 | NZ | LYS C | 401 | 45.524 | 45.913 | −53.915 | 1.00 | 59.62 | N |
| ATOM | 10955 | C | LYS C | 401 | 45.397 | 46.784 | −47.441 | 1.00 | 53.72 | C |
| ATOM | 10956 | O | LYS C | 401 | 46.259 | 47.566 | −47.048 | 1.00 | 55.77 | O |
| ATOM | 10957 | N | PHE C | 402 | 45.453 | 45.470 | −47.214 | 1.00 | 55.85 | N |
| ATOM | 10958 | CA | PHE C | 402 | 46.620 | 44.819 | −46.572 | 1.00 | 53.27 | C |
| ATOM | 10959 | CB | PHE C | 402 | 46.207 | 43.945 | −45.388 | 1.00 | 51.61 | C |
| ATOM | 10960 | CG | PHE C | 402 | 45.719 | 44.730 | −44.184 | 1.00 | 49.13 | C |
| ATOM | 10961 | CD2 | PHE C | 402 | 44.392 | 45.025 | −44.020 | 1.00 | 46.56 | C |
| ATOM | 10962 | CE2 | PHE C | 402 | 43.960 | 45.736 | −42.918 | 1.00 | 46.24 | C |
| ATOM | 10963 | CZ | PHE C | 402 | 44.850 | 46.171 | −41.978 | 1.00 | 44.51 | C |
| ATOM | 10964 | CE1 | PHE C | 402 | 46.171 | 45.886 | −42.127 | 1.00 | 46.67 | C |
| ATOM | 10965 | CD1 | PHE C | 402 | 46.607 | 45.181 | −43.225 | 1.00 | 48.88 | C |
| ATOM | 10966 | C | PHE C | 402 | 47.369 | 43.991 | −47.595 | 1.00 | 55.34 | C |
| ATOM | 10967 | O | PHE C | 402 | 46.760 | 43.340 | −48.455 | 1.00 | 55.47 | O |
| ATOM | 10968 | N | THR C | 403 | 48.698 | 44.045 | −47.500 | 1.00 | 59.11 | N |

TABLE 6-continued

Atomic coordinates for CRBN:DDB1: Compound B (Human protein)

| ATOM | 10969 | CA | THR C | 403 | 49.637 | 43.453 | −48.498 | 1.00 | 56.23 | C |
|---|---|---|---|---|---|---|---|---|---|---|
| ATOM | 10970 | CB | THR C | 403 | 50.225 | 44.526 | −49.475 | 1.00 | 49.96 | C |
| ATOM | 10971 | OG1 | THR C | 403 | 50.804 | 45.618 | −48.750 | 1.00 | 46.32 | O |
| ATOM | 10972 | CG2 | THR C | 403 | 49.149 | 45.070 | −50.311 | 1.00 | 47.32 | C |
| ATOM | 10973 | C | THR C | 403 | 50.768 | 42.722 | −47.750 | 1.00 | 56.56 | C |
| ATOM | 10974 | O | THR C | 403 | 51.266 | 43.212 | −46.732 | 1.00 | 58.24 | O |
| ATOM | 10975 | N | ALA C | 404 | 51.146 | 41.552 | −48.255 | 1.00 | 57.04 | N |
| ATOM | 10976 | CA | ALA C | 404 | 52.140 | 40.683 | −47.623 | 1.00 | 58.15 | C |
| ATOM | 10977 | CB | ALA C | 404 | 52.066 | 39.336 | −48.280 | 1.00 | 61.48 | C |
| ATOM | 10978 | C | ALA C | 404 | 53.581 | 41.199 | −47.704 | 1.00 | 58.44 | C |
| ATOM | 10979 | O | ALA C | 404 | 53.951 | 41.730 | −48.727 | 1.00 | 61.73 | O |
| ATOM | 10980 | N | THR C | 405 | 54.372 | 41.035 | −46.633 | 1.00 | 60.89 | N |
| ATOM | 10981 | CA | THR C | 405 | 55.774 | 41.515 | −46.568 | 1.00 | 61.21 | C |
| ATOM | 10982 | CB | THR C | 405 | 56.233 | 42.153 | −45.195 | 1.00 | 60.72 | C |
| ATOM | 10983 | OG1 | THR C | 405 | 55.929 | 41.314 | −44.081 | 1.00 | 64.18 | O |
| ATOM | 10984 | CG2 | THR C | 405 | 55.562 | 43.492 | −44.947 | 1.00 | 59.65 | C |
| ATOM | 10985 | C | THR C | 405 | 56.742 | 40.443 | −47.008 | 1.00 | 62.56 | C |
| ATOM | 10986 | O | THR C | 405 | 57.746 | 40.792 | −47.546 | 1.00 | 65.05 | O |
| ATOM | 10987 | N | LYS C | 406 | 56.436 | 39.159 | −46.795 | 1.00 | 72.23 | N |
| ATOM | 10988 | CA | LYS C | 406 | 57.206 | 38.016 | −47.350 | 1.00 | 73.01 | C |
| ATOM | 10989 | CB | LYS C | 406 | 57.461 | 36.946 | −46.278 | 1.00 | 78.76 | C |
| ATOM | 10990 | CG | LYS C | 406 | 57.717 | 37.388 | −44.821 | 1.00 | 84.74 | C |
| ATOM | 10991 | CD | LYS C | 406 | 57.731 | 36.133 | −43.923 | 1.00 | 94.25 | C |
| ATOM | 10992 | CE | LYS C | 406 | 56.961 | 36.241 | −42.600 | 1.00 | 100.40 | C |
| ATOM | 10993 | NZ | LYS C | 406 | 57.817 | 36.011 | −41.396 | 1.00 | 104.54 | N |
| ATOM | 10994 | C | LYS C | 406 | 56.397 | 37.377 | −48.491 | 1.00 | 73.88 | C |
| ATOM | 10995 | O | LYS C | 406 | 55.172 | 37.383 | −48.462 | 1.00 | 72.19 | O |
| ATOM | 10996 | N | LYS C | 407 | 57.066 | 36.778 | −49.470 | 1.00 | 81.65 | N |
| ATOM | 10997 | CA | LYS C | 407 | 56.420 | 36.402 | −50.757 | 1.00 | 84.93 | C |
| ATOM | 10998 | CB | LYS C | 407 | 57.388 | 36.635 | −51.913 | 1.00 | 93.10 | C |
| ATOM | 10999 | CG | LYS C | 407 | 57.837 | 38.101 | −52.012 | 1.00 | 104.68 | C |
| ATOM | 11000 | CD | LYS C | 407 | 56.969 | 38.916 | −52.956 | 1.00 | 104.60 | C |
| ATOM | 11001 | CE | LYS C | 407 | 57.445 | 38.691 | −54.386 | 1.00 | 106.38 | C |
| ATOM | 11002 | NZ | LYS C | 407 | 56.332 | 38.784 | −55.368 | 1.00 | 108.87 | N |
| ATOM | 11003 | C | LYS C | 407 | 55.877 | 34.997 | −50.819 | 1.00 | 79.45 | C |
| ATOM | 11004 | O | LYS C | 407 | 55.467 | 34.551 | −51.864 | 1.00 | 78.10 | O |
| ATOM | 11005 | N | ASP C | 408 | 55.818 | 34.332 | −49.679 | 1.00 | 81.30 | N |
| ATOM | 11006 | CA | ASP C | 408 | 55.269 | 32.984 | −49.549 | 1.00 | 85.40 | C |
| ATOM | 11007 | CB | ASP C | 408 | 56.397 | 32.075 | −49.091 | 1.00 | 87.70 | C |
| ATOM | 11008 | CG | ASP C | 408 | 56.917 | 32.473 | −47.729 | 1.00 | 87.25 | C |
| ATOM | 11009 | OD1 | ASP C | 408 | 57.253 | 33.656 | −47.547 | 1.00 | 84.95 | O |
| ATOM | 11010 | OD2 | ASP C | 408 | 56.943 | 31.629 | −46.828 | 1.00 | 100.38 | O |
| ATOM | 11011 | C | ASP C | 408 | 54.133 | 32.908 | −48.500 | 1.00 | 87.26 | C |
| ATOM | 11012 | O | ASP C | 408 | 53.797 | 31.818 | −48.029 | 1.00 | 92.52 | O |
| ATOM | 11013 | N | MET C | 409 | 53.613 | 34.059 | −48.121 | 1.00 | 86.38 | N |
| ATOM | 11014 | CA | MET C | 409 | 52.528 | 34.131 | −47.185 | 1.00 | 79.70 | C |
| ATOM | 11015 | CB | MET C | 409 | 52.416 | 35.524 | −46.615 | 1.00 | 77.96 | C |
| ATOM | 11016 | CG | MET C | 409 | 53.541 | 35.994 | −45.743 | 1.00 | 74.98 | C |
| ATOM | 11017 | SD | MET C | 409 | 52.931 | 37.477 | −44.967 | 1.00 | 75.58 | S |
| ATOM | 11018 | CE | MET C | 409 | 54.194 | 37.755 | −43.754 | 1.00 | 79.27 | C |
| ATOM | 11019 | C | MET C | 409 | 51.314 | 33.952 | −48.022 | 1.00 | 75.41 | C |
| ATOM | 11020 | O | MET C | 409 | 51.356 | 34.211 | −49.200 | 1.00 | 74.86 | O |
| ATOM | 11021 | N | SER C | 410 | 50.224 | 33.516 | −47.427 | 1.00 | 72.56 | N |
| ATOM | 11022 | CA | SER C | 410 | 48.991 | 33.421 | −48.159 | 1.00 | 73.08 | C |
| ATOM | 11023 | CB | SER C | 410 | 48.744 | 32.029 | −48.667 | 1.00 | 78.16 | C |
| ATOM | 11024 | OG | SER C | 410 | 47.460 | 31.974 | −49.242 | 1.00 | 81.84 | O |
| ATOM | 11025 | C | SER C | 410 | 47.901 | 33.795 | −47.205 | 1.00 | 69.09 | C |
| ATOM | 11026 | O | SER C | 410 | 47.907 | 33.296 | −46.103 | 1.00 | 66.45 | O |
| ATOM | 11027 | N | PRO C | 411 | 46.887 | 34.664 | −47.590 | 1.00 | 63.85 | N |
| ATOM | 11028 | CA | PRO C | 411 | 46.956 | 35.239 | −48.934 | 1.00 | 62.37 | C |
| ATOM | 11029 | CB | PRO C | 411 | 45.555 | 35.727 | −49.139 | 1.00 | 65.32 | C |
| ATOM | 11030 | CG | PRO C | 411 | 45.264 | 36.341 | −47.850 | 1.00 | 68.06 | C |
| ATOM | 11031 | CD | PRO C | 411 | 45.626 | 35.239 | −46.940 | 1.00 | 67.59 | C |
| ATOM | 11032 | C | PRO C | 411 | 47.889 | 36.432 | −49.034 | 1.00 | 62.80 | C |
| ATOM | 11033 | O | PRO C | 411 | 48.234 | 36.992 | −48.012 | 1.00 | 63.03 | O |
| ATOM | 11034 | N | GLN C | 412 | 48.299 | 36.778 | −50.254 | 1.00 | 64.57 | N |
| ATOM | 11035 | CA | GLN C | 412 | 49.184 | 37.908 | −50.543 | 1.00 | 65.40 | C |
| ATOM | 11036 | CB | GLN C | 412 | 49.682 | 37.856 | −51.981 | 1.00 | 67.79 | C |
| ATOM | 11037 | CG | GLN C | 412 | 50.895 | 36.970 | −52.192 | 1.00 | 68.80 | C |
| ATOM | 11038 | CD | GLN C | 412 | 52.150 | 37.541 | −51.590 | 1.00 | 73.09 | C |
| ATOM | 11039 | OE1 | GLN C | 412 | 52.624 | 38.590 | −51.995 | 1.00 | 75.31 | O |
| ATOM | 11040 | NE2 | GLN C | 412 | 52.696 | 36.847 | −50.621 | 1.00 | 72.30 | N |
| ATOM | 11041 | C | GLN C | 412 | 48.586 | 39.264 | −50.246 | 1.00 | 63.27 | C |
| ATOM | 11042 | O | GLN C | 412 | 49.253 | 40.128 | −49.723 | 1.00 | 62.35 | O |
| ATOM | 11043 | N | LYS C | 413 | 47.326 | 39.445 | −50.597 | 1.00 | 62.93 | N |
| ATOM | 11044 | CA | LYS C | 413 | 46.606 | 40.665 | −50.293 | 1.00 | 61.89 | C |
| ATOM | 11045 | CB | LYS C | 413 | 46.659 | 41.621 | −51.493 | 1.00 | 68.00 | C |
| ATOM | 11046 | CG | LYS C | 413 | 45.593 | 41.530 | −52.597 | 1.00 | 75.00 | C |

TABLE 6-continued

Atomic coordinates for CRBN:DDB1: Compound B (Human protein)

| ATOM | 11047 | CD  | LYS C | 413 | 45.771 | 40.404 | −53.608 | 1.00 | 84.90  | C |
|------|-------|-----|-------|-----|--------|--------|---------|------|--------|---|
| ATOM | 11048 | CE  | LYS C | 413 | 44.571 | 39.454 | −53.573 | 1.00 | 100.96 | C |
| ATOM | 11049 | NZ  | LYS C | 413 | 44.777 | 38.150 | −54.272 | 1.00 | 107.82 | N |
| ATOM | 11050 | C   | LYS C | 413 | 45.184 | 40.417 | −49.817 | 1.00 | 57.19  | C |
| ATOM | 11051 | O   | LYS C | 413 | 44.631 | 39.330 | −49.980 | 1.00 | 51.84  | O |
| ATOM | 11052 | N   | PHE C | 414 | 44.625 | 41.446 | −49.192 | 1.00 | 54.96  | N |
| ATOM | 11053 | CA  | PHE C | 414 | 43.232 | 41.457 | −48.739 | 1.00 | 54.18  | C |
| ATOM | 11054 | CB  | PHE C | 414 | 42.943 | 40.422 | −47.644 | 1.00 | 51.40  | C |
| ATOM | 11055 | CG  | PHE C | 414 | 43.549 | 40.725 | −46.319 | 1.00 | 47.97  | C |
| ATOM | 11056 | CD1 | PHE C | 414 | 42.895 | 41.514 | −45.417 | 1.00 | 49.55  | C |
| ATOM | 11057 | CE1 | PHE C | 414 | 43.423 | 41.766 | −44.159 | 1.00 | 49.34  | C |
| ATOM | 11058 | CZ  | PHE C | 414 | 44.618 | 41.213 | −43.807 | 1.00 | 48.75  | C |
| ATOM | 11059 | CE2 | PHE C | 414 | 45.274 | 40.414 | −44.713 | 1.00 | 48.68  | C |
| ATOM | 11060 | CD2 | PHE C | 414 | 44.732 | 40.172 | −45.956 | 1.00 | 47.38  | C |
| ATOM | 11061 | C   | PHE C | 414 | 42.891 | 42.816 | −48.205 | 1.00 | 54.46  | C |
| ATOM | 11062 | O   | PHE C | 414 | 43.789 | 43.608 | −47.958 | 1.00 | 56.42  | O |
| ATOM | 11063 | N   | TRP C | 415 | 41.607 | 43.065 | −47.996 | 1.00 | 52.85  | N |
| ATOM | 11064 | CA  | TRP C | 415 | 41.167 | 44.359 | −47.561 | 1.00 | 54.67  | C |
| ATOM | 11065 | CB  | TRP C | 415 | 40.191 | 44.937 | −48.577 | 1.00 | 57.33  | C |
| ATOM | 11066 | CG  | TRP C | 415 | 40.751 | 45.576 | −49.899 | 1.00 | 64.12  | C |
| ATOM | 11067 | CD1 | TRP C | 415 | 40.961 | 46.962 | −50.197 | 1.00 | 67.17  | C |
| ATOM | 11068 | NE1 | TRP C | 415 | 41.403 | 47.114 | −51.496 | 1.00 | 64.95  | N |
| ATOM | 11069 | CE2 | TRP C | 415 | 41.462 | 45.862 | −52.064 | 1.00 | 70.16  | C |
| ATOM | 11070 | CD2 | TRP C | 415 | 41.050 | 44.888 | −51.089 | 1.00 | 63.96  | C |
| ATOM | 11071 | CE3 | TRP C | 415 | 41.040 | 43.546 | −51.435 | 1.00 | 67.78  | C |
| ATOM | 11072 | CZ3 | TRP C | 415 | 41.434 | 43.181 | −52.754 | 1.00 | 81.27  | C |
| ATOM | 11073 | CH2 | TRP C | 415 | 41.827 | 44.155 | −53.697 | 1.00 | 82.52  | C |
| ATOM | 11074 | CZ2 | TRP C | 415 | 41.855 | 45.499 | −53.362 | 1.00 | 80.24  | C |
| ATOM | 11075 | C   | TRP C | 415 | 40.515 | 44.199 | −46.178 | 1.00 | 56.94  | C |
| ATOM | 11076 | O   | TRP C | 415 | 39.828 | 43.200 | −45.910 | 1.00 | 54.90  | O |
| ATOM | 11077 | N   | GLY C | 416 | 40.761 | 45.168 | −45.293 | 1.00 | 57.27  | N |
| ATOM | 11078 | CA  | GLY C | 416 | 40.162 | 45.214 | −43.955 | 1.00 | 55.33  | C |
| ATOM | 11079 | C   | GLY C | 416 | 39.356 | 46.482 | −43.948 | 1.00 | 56.47  | C |
| ATOM | 11080 | O   | GLY C | 416 | 39.948 | 47.557 | −43.995 | 1.00 | 61.28  | O |
| ATOM | 11081 | N   | LEU C | 417 | 38.022 | 46.361 | −43.932 | 1.00 | 54.60  | N |
| ATOM | 11082 | CA  | LEU C | 417 | 37.094 | 47.488 | −44.096 | 1.00 | 50.94  | C |
| ATOM | 11083 | CB  | LEU C | 417 | 36.060 | 47.179 | −45.144 | 1.00 | 50.76  | C |
| ATOM | 11084 | CG  | LEU C | 417 | 36.592 | 46.593 | −46.439 | 1.00 | 51.17  | C |
| ATOM | 11085 | CD1 | LEU C | 417 | 35.525 | 45.773 | −47.151 | 1.00 | 50.29  | C |
| ATOM | 11086 | CD2 | LEU C | 417 | 37.124 | 47.688 | −47.331 | 1.00 | 51.22  | C |
| ATOM | 11087 | C   | LEU C | 417 | 36.380 | 47.745 | −42.791 | 1.00 | 51.81  | C |
| ATOM | 11088 | O   | LEU C | 417 | 36.024 | 46.837 | −42.057 | 1.00 | 53.19  | O |
| ATOM | 11089 | N   | THR C | 418 | 36.133 | 49.004 | −42.526 | 1.00 | 52.02  | N |
| ATOM | 11090 | CA  | THR C | 418 | 35.870 | 49.453 | −41.176 | 1.00 | 51.55  | C |
| ATOM | 11091 | CB  | THR C | 418 | 36.644 | 50.772 | −40.866 | 1.00 | 52.35  | C |
| ATOM | 11092 | OG1 | THR C | 418 | 36.131 | 51.393 | −39.737 | 1.00 | 56.03  | O |
| ATOM | 11093 | CG2 | THR C | 418 | 36.484 | 51.857 | −41.887 | 1.00 | 56.05  | C |
| ATOM | 11094 | C   | THR C | 418 | 34.365 | 49.552 | −41.073 | 1.00 | 51.47  | C |
| ATOM | 11095 | O   | THR C | 418 | 33.760 | 50.348 | −41.759 | 1.00 | 51.53  | O |
| ATOM | 11096 | N   | ARG C | 419 | 33.772 | 48.706 | −40.228 | 1.00 | 53.28  | N |
| ATOM | 11097 | CA  | ARG C | 419 | 32.305 | 48.608 | −40.013 | 1.00 | 50.71  | C |
| ATOM | 11098 | CB  | ARG C | 419 | 31.956 | 47.943 | −38.668 | 1.00 | 52.00  | C |
| ATOM | 11099 | CG  | ARG C | 419 | 30.482 | 47.548 | −38.506 | 1.00 | 54.53  | C |
| ATOM | 11100 | CD  | ARG C | 419 | 30.131 | 46.893 | −37.162 | 1.00 | 56.43  | C |
| ATOM | 11101 | NE  | ARG C | 419 | 29.940 | 47.874 | −36.092 | 1.00 | 61.63  | N |
| ATOM | 11102 | CZ  | ARG C | 419 | 28.788 | 48.407 | −35.678 | 1.00 | 69.97  | C |
| ATOM | 11103 | NH1 | ARG C | 419 | 28.811 | 49.312 | −34.695 | 1.00 | 73.86  | N |
| ATOM | 11104 | NH2 | ARG C | 419 | 27.610 | 48.054 | −36.200 | 1.00 | 73.82  | N |
| ATOM | 11105 | C   | ARG C | 419 | 31.560 | 49.907 | −40.136 | 1.00 | 49.04  | C |
| ATOM | 11106 | O   | ARG C | 419 | 30.663 | 50.007 | −40.937 | 1.00 | 49.26  | O |
| ATOM | 11107 | N   | SER C | 420 | 31.935 | 50.935 | −39.406 | 1.00 | 51.24  | N |
| ATOM | 11108 | CA  | SER C | 420 | 31.127 | 52.182 | −39.465 | 1.00 | 54.77  | C |
| ATOM | 11109 | CB  | SER C | 420 | 31.681 | 53.248 | −38.533 | 1.00 | 56.67  | C |
| ATOM | 11110 | OG  | SER C | 420 | 32.885 | 53.759 | −39.077 | 1.00 | 62.18  | O |
| ATOM | 11111 | C   | SER C | 420 | 30.973 | 52.819 | −40.851 | 1.00 | 53.24  | C |
| ATOM | 11112 | O   | SER C | 420 | 30.024 | 53.550 | −41.094 | 1.00 | 51.97  | O |
| ATOM | 11113 | N   | ALA C | 421 | 31.929 | 52.555 | −41.730 | 1.00 | 55.54  | N |
| ATOM | 11114 | CA  | ALA C | 421 | 31.968 | 53.146 | −43.074 | 1.00 | 57.82  | C |
| ATOM | 11115 | CB  | ALA C | 421 | 33.399 | 53.171 | −43.598 | 1.00 | 59.68  | C |
| ATOM | 11116 | C   | ALA C | 421 | 31.129 | 52.427 | −44.072 | 1.00 | 54.71  | C |
| ATOM | 11117 | O   | ALA C | 421 | 30.968 | 52.942 | −45.170 | 1.00 | 51.68  | O |
| ATOM | 11118 | N   | LEU C | 422 | 30.632 | 51.255 | −43.677 | 1.00 | 56.97  | N |
| ATOM | 11119 | CA  | LEU C | 422 | 29.901 | 50.339 | −44.523 | 1.00 | 62.41  | C |
| ATOM | 11120 | CB  | LEU C | 422 | 30.371 | 48.921 | −44.226 | 1.00 | 65.16  | C |
| ATOM | 11121 | CG  | LEU C | 422 | 31.766 | 48.638 | −44.799 | 1.00 | 68.81  | C |
| ATOM | 11122 | CD1 | LEU C | 422 | 32.290 | 47.304 | −44.296 | 1.00 | 69.74  | C |
| ATOM | 11123 | CD2 | LEU C | 422 | 31.768 | 48.683 | −46.331 | 1.00 | 67.47  | C |
| ATOM | 11124 | C   | LEU C | 422 | 28.396 | 50.399 | −44.328 | 1.00 | 65.83  | C |

TABLE 6-continued

Atomic coordinates for CRBN:DDB1: Compound B (Human protein)

| ATOM | 11125 | O | LEU C | 422 | 27.922 | 50.979 | −43.380 | 1.00 | 78.90 | O |
|---|---|---|---|---|---|---|---|---|---|---|
| ATOM | 11126 | N | LEU C | 423 | 27.647 | 49.784 | −45.231 | 1.00 | 67.80 | N |
| ATOM | 11127 | CA | LEU C | 423 | 26.196 | 49.738 | −45.150 | 1.00 | 68.67 | C |
| ATOM | 11128 | CB | LEU C | 423 | 25.629 | 51.005 | −45.784 | 1.00 | 71.16 | C |
| ATOM | 11129 | CG | LEU C | 423 | 24.215 | 51.533 | −45.490 | 1.00 | 72.49 | C |
| ATOM | 11130 | CD1 | LEU C | 423 | 23.288 | 51.391 | −46.718 | 1.00 | 71.31 | C |
| ATOM | 11131 | CD2 | LEU C | 423 | 23.643 | 50.955 | −44.166 | 1.00 | 72.52 | C |
| ATOM | 11132 | C | LEU C | 423 | 25.694 | 48.482 | −45.856 | 1.00 | 73.79 | C |
| ATOM | 11133 | O | LEU C | 423 | 25.713 | 48.435 | −47.083 | 1.00 | 70.72 | O |
| ATOM | 11134 | N | PRO C | 424 | 25.282 | 47.433 | −45.085 | 1.00 | 88.28 | N |
| ATOM | 11135 | CA | PRO C | 424 | 24.843 | 46.204 | −45.749 | 1.00 | 91.80 | C |
| ATOM | 11136 | CB | PRO C | 424 | 24.639 | 45.217 | −44.595 | 1.00 | 91.55 | C |
| ATOM | 11137 | CG | PRO C | 424 | 24.250 | 46.083 | −43.452 | 1.00 | 93.55 | C |
| ATOM | 11138 | CD | PRO C | 424 | 25.083 | 47.333 | −43.620 | 1.00 | 94.39 | C |
| ATOM | 11139 | C | PRO C | 424 | 23.549 | 46.478 | −46.466 | 1.00 | 94.56 | C |
| ATOM | 11140 | O | PRO C | 424 | 22.722 | 47.221 | −45.956 | 1.00 | 86.24 | O |
| ATOM | 11141 | N | THR C | 425 | 23.374 | 45.841 | −47.611 | 1.00 | 107.49 | N |
| ATOM | 11142 | CA | THR C | 425 | 22.194 | 46.023 | −48.419 | 1.00 | 108.14 | C |
| ATOM | 11143 | CB | THR C | 425 | 22.517 | 46.981 | −49.557 | 1.00 | 100.65 | C |
| ATOM | 11144 | OG1 | THR C | 425 | 23.110 | 48.156 | −49.008 | 1.00 | 87.95 | O |
| ATOM | 11145 | CG2 | THR C | 425 | 21.263 | 47.365 | −50.253 | 1.00 | 106.34 | C |
| ATOM | 11146 | C | THR C | 425 | 21.638 | 44.739 | −49.013 | 1.00 | 111.97 | C |
| ATOM | 11147 | O | THR C | 425 | 22.317 | 43.733 | −49.075 | 1.00 | 106.64 | O |
| ATOM | 11148 | N | ILE C | 426 | 20.382 | 44.781 | −49.435 | 1.00 | 119.03 | N |
| ATOM | 11149 | CA | ILE C | 426 | 19.755 | 43.636 | −50.083 | 1.00 | 121.37 | C |
| ATOM | 11150 | CB | ILE C | 426 | 18.522 | 43.097 | −49.340 | 1.00 | 118.00 | C |
| ATOM | 11151 | CG1 | ILE C | 426 | 17.382 | 44.094 | −49.361 | 1.00 | 116.20 | C |
| ATOM | 11152 | CD1 | ILE C | 426 | 16.219 | 43.638 | −48.509 | 1.00 | 121.35 | C |
| ATOM | 11153 | CG2 | ILE C | 426 | 18.869 | 42.764 | −47.904 | 1.00 | 113.87 | C |
| ATOM | 11154 | C | ILE C | 426 | 19.464 | 44.094 | −51.504 | 1.00 | 112.71 | C |
| ATOM | 11155 | O | ILE C | 426 | 18.885 | 45.144 | −51.729 | 1.00 | 102.94 | O |
| ATOM | 11156 | N | PRO C | 427 | 19.906 | 43.241 | −52.495 | 1.00 | 111.44 | N |
| ATOM | 11157 | CA | PRO C | 427 | 19.744 | 43.735 | −53.871 | 1.00 | 116.12 | C |
| ATOM | 11158 | CB | PRO C | 427 | 20.459 | 42.678 | −54.703 | 1.00 | 115.01 | C |
| ATOM | 11159 | CG | PRO C | 427 | 20.174 | 41.430 | −53.979 | 1.00 | 115.80 | C |
| ATOM | 11160 | CD | PRO C | 427 | 20.534 | 41.849 | −52.596 | 1.00 | 112.68 | C |
| ATOM | 11161 | C | PRO C | 427 | 18.382 | 43.980 | −54.493 | 1.00 | 115.11 | C |
| ATOM | 11162 | O | PRO C | 427 | 17.363 | 43.432 | −54.108 | 1.00 | 113.38 | O |
| ATOM | 11163 | N | ASP C | 428 | 18.421 | 44.858 | −55.488 | 1.00 | 108.40 | N |
| ATOM | 11164 | CA | ASP C | 428 | 17.244 | 45.269 | −56.281 | 1.00 | 105.21 | C |
| ATOM | 11165 | CB | ASP C | 428 | 15.981 | 44.340 | −56.147 | 1.00 | 104.41 | C |
| ATOM | 11166 | CG | ASP C | 428 | 16.145 | 42.955 | −56.840 | 1.00 | 97.39 | C |
| ATOM | 11167 | OD1 | ASP C | 428 | 17.063 | 42.788 | −57.675 | 1.00 | 92.07 | O |
| ATOM | 11168 | OD2 | ASP C | 428 | 15.330 | 42.041 | −56.562 | 1.00 | 84.49 | O |
| ATOM | 11169 | C | ASP C | 428 | 16.907 | 46.717 | −55.915 | 1.00 | 98.25 | C |
| ATOM | 11170 | O | ASP C | 428 | 17.141 | 47.632 | −56.707 | 1.00 | 86.27 | O |
| TER | 11171 | | ASP C | 428 | | | | | | |
| HETATM | 11172 | C22 | MOL E | 1 | 52.219 | 55.861 | −30.232 | 1.00 | 165.51 | C |
| HETATM | 11173 | C23 | MOL E | 1 | 51.226 | 56.603 | −29.327 | 1.00 | 173.28 | C |
| HETATM | 11174 | O5 | MOL E | 1 | 51.429 | 58.038 | −29.381 | 1.00 | 169.11 | O |
| HETATM | 11175 | C24 | MOL E | 1 | 51.362 | 58.545 | −30.730 | 1.00 | 156.65 | C |
| HETATM | 11176 | C25 | MOL E | 1 | 52.393 | 57.812 | −31.594 | 1.00 | 158.72 | C |
| HETATM | 11177 | N3 | MOL E | 1 | 52.073 | 56.374 | −31.602 | 1.00 | 155.78 | N |
| HETATM | 11178 | C21 | MOL E | 1 | 52.945 | 55.643 | −32.543 | 1.00 | 131.27 | C |
| HETATM | 11179 | C20 | MOL E | 1 | 52.372 | 55.752 | −33.967 | 1.00 | 104.63 | C |
| HETATM | 11180 | C19 | MOL E | 1 | 52.293 | 54.632 | −34.791 | 1.00 | 94.32 | C |
| HETATM | 11181 | C17 | MOL E | 1 | 51.767 | 54.754 | −36.078 | 1.00 | 97.81 | C |
| HETATM | 11182 | C18 | MOL E | 1 | 51.925 | 56.985 | −34.439 | 1.00 | 100.94 | C |
| HETATM | 11183 | C16 | MOL E | 1 | 51.401 | 57.107 | −35.722 | 1.00 | 99.76 | C |
| HETATM | 11184 | C15 | MOL E | 1 | 51.318 | 55.991 | −36.549 | 1.00 | 101.01 | C |
| HETATM | 11185 | C14 | MOL E | 1 | 50.789 | 56.135 | −37.841 | 1.00 | 93.53 | C |
| HETATM | 11186 | O4 | MOL E | 1 | 49.814 | 55.208 | −38.385 | 1.00 | 82.82 | O |
| HETATM | 11187 | C3 | MOL E | 1 | 48.512 | 55.568 | −38.169 | 1.00 | 71.21 | C |
| HETATM | 11188 | C2 | MOL E | 1 | 48.154 | 56.874 | −37.858 | 1.00 | 69.98 | C |
| HETATM | 11189 | C1 | MOL E | 1 | 46.814 | 57.200 | −37.650 | 1.00 | 69.30 | C |
| HETATM | 11190 | C4 | MOL E | 1 | 45.817 | 56.235 | −37.746 | 1.00 | 64.04 | C |
| HETATM | 11191 | C5 | MOL E | 1 | 46.165 | 54.930 | −38.064 | 1.00 | 69.09 | C |
| HETATM | 11192 | C8 | MOL E | 1 | 45.424 | 53.758 | −38.215 | 1.00 | 68.74 | C |
| HETATM | 11193 | O1 | MOL E | 1 | 44.208 | 53.673 | −38.052 | 1.00 | 64.61 | O |
| HETATM | 11194 | C6 | MOL E | 1 | 47.505 | 54.617 | −38.264 | 1.00 | 70.76 | C |
| HETATM | 11195 | C7 | MOL E | 1 | 47.613 | 53.135 | −38.585 | 1.00 | 73.04 | C |
| HETATM | 11196 | N1 | MOL E | 1 | 46.208 | 52.721 | −38.490 | 1.00 | 68.39 | N |
| HETATM | 11197 | C9 | MOL E | 1 | 45.746 | 51.339 | −38.642 | 1.00 | 63.16 | C |
| HETATM | 11198 | C10 | MOL E | 1 | 46.070 | 50.827 | −40.043 | 1.00 | 61.46 | C |
| HETATM | 11199 | C11 | MOL E | 1 | 45.735 | 49.342 | −40.156 | 1.00 | 63.25 | C |
| HETATM | 11200 | C12 | MOL E | 1 | 46.446 | 48.544 | −39.064 | 1.00 | 62.86 | C |
| HETATM | 11201 | O3 | MOL E | 1 | 46.731 | 47.365 | −39.255 | 1.00 | 63.54 | O |
| HETATM | 11202 | N2 | MOL E | 1 | 46.784 | 49.144 | −37.847 | 1.00 | 63.79 | N |

TABLE 6-continued

Atomic coordinates for CRBN:DDB1: Compound B (Human protein)

| HETATM | 11203 | C13 | MOL E | 1 | 46.470 | 50.484 | −37.594 | 1.00 | 64.54 | C |
|---|---|---|---|---|---|---|---|---|---|---|
| HETATM | 11204 | O2 | MOL E | 1 | 46.780 | 50.978 | −36.510 | 1.00 | 59.72 | O |
| HETATM | 11205 | ZN | ZN D | 1 | 31.556 | 56.746 | −50.977 | 1.00 | 126.39 | ZN |
| END | | | | | | | | | | |

TABLE 7

Atomic coordinates for CRBN(TBD): Compound B (Murine protein)

```
HEADER    - - - -                                              XX-XXX-XX    xxxx
COMPND    - - -
REMARK    3
REMARK    3   REFINEMENT.
REMARK    3   PROGRAM : REFMAC 5.6.0117
REMARK    3   AUTHORS : MURSHUDOV,VAGIN,DODSON
REMARK    3
REMARK    3   REFINEMENT TARGET : MAXIMUM LIKELIHOOD
REMARK    3
REMARK    3   DATA USED IN REFINEMENT.
REMARK    3   RESOLUTION RANGE HIGH (ANGSTROMS): 2.21
REMARK    3   RESOLUTION RANGE LOW (ANGSTROMS) : 50.00
REMARK    3   DATA CUTOFF (SIGMA(F)) : NONE
REMARK    3   COMPLETENESS FOR RANGE (%) : 99.03
REMARK    3   NUMBER OF REFLECTIONS : 7777
REMARK    3
REMARK    3   FIT TO DATA USED IN REFINEMENT.
REMARK    3   CROSSVALIDATION METHOD : THROUGHOUT
REMARK    3   FREE R VALUE TEST SET SELECTION : RANDOM
REMARK    3   R VALUE (WORKING + TEST SET) : 0.22404
REMARK    3   R VALUE (WORKING SET) : 0.22296
REMARK    3   FREE R VALUE : 0.24841
REMARK    3   FREE R VALUE TEST SET SIZE (%) : 4.6
REMARK    3   FREE R VALUETEST SET COUNT : 379
REMARK    3
REMARK    3   FIT IN THE HIGHEST RESOLUTION BIN.
REMARK    3   TOTAL NUMBER OF BINS USED : 20
REMARK    3   BIN RESOLUTION RANGE HIGH : 2.206
REMARK    3   BIN RESOLUTION RANGE LOW : 2.263
REMARK    3   REFLECTION IN BIN (WORKING SET) : 484
REMARK    3   BIN R VALUE (WORKING + TEST) (%) : 98.44
REMARK    3   BIN R VALUE (WORKING SET) : 0.232
REMARK    3   BIN FREE R VALUE SET COUNT : 21
REMARK    3   BIN FREE R VALUE : 0.226
REMARK    3
REMARK    3   NUMBER OF NONHYDROGEN ATOMS USED IN REFINEMENT.
REMARK    3   ALL ATOMS : 902
REMARK    3
REMARK    3   B VALUES.
REMARK    3   FROM WILSON PLOT (A**2) : NULL
REMARK    3   MEAN B VALUE (OVERALL, A**2) : 43.420
REMARK    3   OVERALL ANISOTROPIC B VALUE.
REMARK    3   B11 (A**2) : −0.57
REMARK    3   B22 (A**2) : −0.57
REMARK    3   B33 (A**2) : 0.85
REMARK    3   B12 (A**2) : −0.28
REMARK    3   B13 (A**2) : 0.00
REMARK    3   B23 (A**2) : 0.00
REMARK    3
REMARK    3   ESTIMATED OVERALL COORDINATE ERROR.
REMARK    3   ESU BASED ON R VALUE (A) : 0.233
REMARK    3   ESU BASED ON FREE R VALUE (A) : 0.190
REMARK    3   ESU BASED ON MAXIMUM LIKELIHOOD (A) : 0.140
REMARK    3   ESU FOR B VALUES BASED ON MAXIMUM LIKELIHOOD (A**2): 9.721
REMARK    3
REMARK    3   CORRELATION COEFFICIENTS.
REMARK    3   CORRELATION COEFFICIENT FOFC : 0.943
REMARK    3   CORRELATION COEFFICIENT FOFC FREE : 0.942
REMARK    3
REMARK    3   RMS DEVIATIONS FROM IDEAL VALUES        COUNT      RMS       WEIGHT
REMARK    3   BOND LENGTHS REFINED ATOMS (A) :          916 ;    0.012 ;    0.019
REMARK    3   BOND ANGLES REFINED ATOMS (DEGREES) :    1250 ;    1.637 ;    1.919
REMARK    3   TORSION ANGLES, PERIOD 1 (DEGREES) :      108 ;   11.923 ;    5.000
REMARK    3   TORSION ANGLES, PERIOD 2 (DEGREES) :       31 ;   31.950 ;   23.548
REMARK    3   TORSION ANGLES, PERIOD 3 (DEGREES) :      144 ;   19.557 ;   15.000
REMARK    3   TORSION ANGLES, PERIOD 4 (DEGREES) : 2 ; 26.606 ; 15.000
```

TABLE 7-continued

Atomic coordinates for CRBN(TBD): Compound B (Murine protein)

| REMARK | 3 | CHIRALCENTER RESTRAINTS (A**3): 136 ; 0.108 ; 0.200 |
|---|---|---|
| REMARK | 3 | GENERAL PLANES REFINED ATOMS (A) : 676 ; 0.018 ; 0.021 |
| REMARK | 3 | |
| REMARK | 3 | ISOTROPIC THERMAL FACTOR RESTRAINTS. COUNT RMS WEIGHT |
| REMARK | 3 | |
| REMARK | 3 | NCS RESTRAINTS STATISTICS |
| REMARK | 3 | NUMBER OF NCS GROUPS : NULL |
| REMARK | 3 | |
| REMARK | 3 | TWIN DETAILS |
| REMARK | 3 | NUMBER OF TWIN DOMAINS : NULL |
| REMARK | 3 | |
| REMARK | 3 | |
| REMARK | 3 | TLS DETAILS |
| REMARK | 3 | NUMBER OF TLS GROUPS : 1 |
| REMARK | 3 | ATOM RECORD CONTAINS RESIDUAL B FACTORS ONLY |
| REMARK | 3 | |
| REMARK | 3 | TLS GROUP : 1 |
| REMARK | 3 | NUMBER OF COMPONENTS GROUP : 1 |
| REMARK | 3 | COMPONENTS C SSSEQI TO C SSSEQI |
| REMARK | 3 | RESIDUE RANGE : D -10 D 9999 |
| REMARK | 3 | ORIGIN FOR THE GROUP (A): 24.9839 -14.3091 -7.2602 |
| REMARK | 3 | T TENSOR |
| REMARK | 3 | T11: 0.0185 T22: 0.0562 |
| REMARK | 3 | T33: 0.1037 T12: -0.0004 |
| REMARK | 3 | T13: 0.0131 T23: -0.0551 |
| REMARK | 3 | L TENSOR |
| REMARK | 3 | L11: 0.8932 L22: 1.0237 |
| REMARK | 3 | L33: 0.9694 L12: -0.1495 |
| REMARK | 3 | L13: 0.2113 L23: -0.2061 |
| REMARK | 3 | S TENSOR |
| REMARK | 3 | S11: 0.0330 S12: -0.0487 S13: 0.0462 |
| REMARK | 3 | S21: -0.0824 S22: -0.1677 S23: 0.1793 |
| REMARK | 3 | S31: 0.1011 S32: -0.1109 S33: 0.1347 |
| REMARK | 3 | |
| REMARK | 3 | |
| REMARK | 3 | BULK SOLVENT MODELLING. |
| REMARK | 3 | METHOD USED : MASK |
| REMARK | 3 | PARAMETERS FOR MASK CALCULATION |
| REMARK | 3 | VDW PROBE RADIUS : 1.20 |
| REMARK | 3 | ION PROBE RADIUS : 0.80 |
| REMARK | 3 | SHRINKAGE RADIUS : 0.80 |
| REMARK | 3 | |
| REMARK | 3 | OTHER REFINEMENT REMARKS: |
| REMARK | 3 | HYDROGENS HAVE BEEN USED IF PRESENT IN THE INPUT |
| REMARK | 3 | U VALUES : RESIDUAL ONLY |
| REMARK | 3 | |

| LINKR | | CYS D 346 | | PRO D 348 | | gap | | | | | |
|---|---|---|---|---|---|---|---|---|---|---|---|
| LINKR | | SER D 344 | | MET D 349 | | gap | | | | | |
| LINKR | | SER D 344 | | GLU? D 361 | | gap | | | | | |
| CRYST1 | | 75.625 | | 75.625 | | 90.989 | 90.00 | 90.00 | 120.00 | P 64 2 2 | |
| SCALE1 | | 0.013223 | | 0.007634 | | 0.000000 | 0.00000 | | | | |
| SCALE2 | | 0.000000 | | 0.015269 | | 0.000000 | 0.00000 | | | | |
| SCALE3 | | 0.000000 | | 0.000000 | | 0.010990 | 0.00000 | | | | |
| ATOM | 1 | N | THR | D | 322 | 13.672 | -7.475 | -20.728 | 1.00 | 55.10 | N |
| ATOM | 2 | CA | THR | D | 322 | 14.200 | -7.347 | -19.335 | 1.00 | 60.06 | C |
| ATOM | 3 | CB | THR | D | 322 | 13.050 | -7.203 | -18.304 | 1.00 | 64.30 | C |
| ATOM | 4 | OG1 | THR | D | 322 | 12.333 | -8.446 | -18.191 | 1.00 | 62.59 | O |
| ATOM | 5 | CG2 | THR | D | 322 | 12.088 | -6.078 | -18.710 | 1.00 | 65.54 | C |
| ATOM | 6 | C | THR | D | 322 | 15.107 | -8.534 | -18.957 | 1.00 | 55.03 | C |
| ATOM | 7 | O | THR | D | 322 | 15.077 | -9.032 | -17.831 | 1.00 | 53.46 | O |
| ATOM | 8 | N | SER | D | 323 | 15.912 | -8.979 | -19.912 | 1.00 | 55.16 | N |
| ATOM | 9 | CA | SER | D | 323 | 16.828 | -10.090 | -19.702 | 1.00 | 55.75 | C |
| ATOM | 10 | CB | SER | D | 323 | 17.131 | -10.771 | -21.028 | 1.00 | 60.48 | C |
| ATOM | 11 | OG | SER | D | 323 | 15.947 | -11.036 | -21.744 | 1.00 | 72.98 | O |
| ATOM | 12 | C | SER | D | 323 | 18.145 | -9.584 | -19.162 | 1.00 | 55.35 | C |
| ATOM | 13 | O | SER | D | 323 | 18.665 | -8.571 | -19.651 | 1.00 | 56.06 | O |
| ATOM | 14 | N | LEU | D | 324 | 18.696 | -10.301 | -18.178 | 1.00 | 52.68 | N |
| ATOM | 15 | CA | LEU | D | 324 | 20.077 | -10.068 | -17.735 | 1.00 | 51.99 | C |
| ATOM | 16 | CB | LEU | D | 324 | 20.194 | -9.944 | -16.211 | 1.00 | 52.06 | C |
| ATOM | 17 | CG | LEU | D | 324 | 19.509 | -8.747 | -15.536 | 1.00 | 57.37 | C |
| ATOM | 18 | CD1 | LEU | D | 324 | 19.826 | -8.718 | -14.052 | 1.00 | 60.77 | C |
| ATOM | 19 | CD2 | LEU | D | 324 | 19.875 | -7.414 | -16.175 | 1.00 | 61.96 | C |
| ATOM | 20 | C | LEU | D | 324 | 20.953 | -11.183 | -18.242 | 1.00 | 49.84 | C |
| ATOM | 21 | O | LEU | D | 324 | 20.694 | -12.368 | -17.987 | 1.00 | 51.57 | O |
| ATOM | 22 | N | CYS | D | 325 | 21.990 | -10.795 | -18.977 | 1.00 | 46.85 | N |
| ATOM | 23 | CA | CYS | D | 325 | 22.846 | -11.749 | -19.666 | 1.00 | 46.10 | C |
| ATOM | 24 | CB | CYS | D | 325 | 22.657 | -11.629 | -21.184 | 1.00 | 49.02 | C |
| ATOM | 25 | SG | CYS | D | 325 | 23.426 | -10.165 | -21.913 | 1.00 | 60.70 | S |

TABLE 7-continued

Atomic coordinates for CRBN(TBD): Compound B (Murine protein)

| ATOM | 26 | C | CYS | D | 325 | 24.310 | −11.564 | −19.287 | 1.00 | 42.99 | C |
|---|---|---|---|---|---|---|---|---|---|---|---|
| ATOM | 27 | O | CYS | D | 325 | 24.696 | −10.532 | −18.728 | 1.00 | 43.59 | O |
| ATOM | 28 | N | CYS | D | 326 | 25.119 | −12.574 | −19.575 | 1.00 | 40.31 | N |
| ATOM | 29 | CA | CYS | D | 326 | 26.543 | −12.489 | −19.361 | 1.00 | 39.19 | C |
| ATOM | 30 | CB | CYS | D | 326 | 27.203 | −13.794 | −19.740 | 1.00 | 38.72 | C |
| ATOM | 31 | SG | CYS | D | 326 | 28.997 | −13.701 | −19.671 | 1.00 | 41.08 | S |
| ATOM | 32 | C | CYS | D | 326 | 27.141 | −11.334 | −20.174 | 1.00 | 41.88 | C |
| ATOM | 33 | O | CYS | D | 326 | 26.911 | −11.242 | −21.375 | 1.00 | 36.63 | O |
| ATOM | 34 | N | LYS | D | 327 | 27.879 | −10.447 | −19.500 | 1.00 | 42.93 | N |
| ATOM | 35 | CA | LYS | D | 327 | 28.453 | −9.273 | −20.145 | 1.00 | 45.29 | C |
| ATOM | 36 | CB | LYS | D | 327 | 29.097 | −8.335 | −19.128 | 1.00 | 43.86 | C |
| ATOM | 37 | CG | LYS | D | 327 | 30.084 | −7.342 | −19.737 | 1.00 | 46.50 | C |
| ATOM | 38 | CD | LYS | D | 327 | 29.730 | −5.904 | −19.397 | 1.00 | 46.09 | C |
| ATOM | 39 | CE | LYS | D | 327 | 30.236 | −5.506 | −18.025 | 1.00 | 50.55 | C |
| ATOM | 40 | NZ | LYS | D | 327 | 29.270 | −4.636 | −17.300 | 1.00 | 44.51 | N |
| ATOM | 41 | C | LYS | D | 327 | 29.473 | −9.638 | −21.224 | 1.00 | 50.10 | C |
| ATOM | 42 | O | LYS | D | 327 | 29.498 | −9.025 | −22.295 | 1.00 | 50.45 | O |
| ATOM | 43 | N | GLN | D | 328 | 30.313 | −10.622 | −20.939 | 1.00 | 47.77 | N |
| ATOM | 44 | CA | GLN | D | 328 | 31.357 | −11.005 | −21.872 | 1.00 | 50.83 | C |
| ATOM | 45 | CB | GLN | D | 328 | 32.446 | −11.817 | −21.160 | 1.00 | 55.48 | C |
| ATOM | 46 | CG | GLN | D | 328 | 32.938 | −13.014 | −21.959 | 1.00 | 63.92 | C |
| ATOM | 47 | CD | GLN | D | 328 | 34.450 | −13.079 | −22.068 | 1.00 | 71.71 | C |
| ATOM | 48 | OE1 | GLN | D | 328 | 35.169 | −12.249 | −21.500 | 1.00 | 82.03 | O |
| ATOM | 49 | NE2 | GLN | D | 328 | 34.944 | −14.062 | −22.823 | 1.00 | 68.78 | N |
| ATOM | 50 | C | GLN | D | 328 | 30.823 | −11.722 | −23.122 | 1.00 | 48.23 | C |
| ATOM | 51 | O | GLN | D | 328 | 31.237 | −11.420 | −24.230 | 1.00 | 51.14 | O |
| ATOM | 52 | N | CYS | D | 329 | 29.901 | −12.660 | −22.970 | 1.00 | 47.76 | N |
| ATOM | 53 | CA | CYS | D | 329 | 29.475 | −13.403 | −24.160 | 1.00 | 47.26 | C |
| ATOM | 54 | CB | CYS | D | 329 | 29.583 | −14.920 | −23.951 | 1.00 | 47.05 | C |
| ATOM | 55 | SG | CYS | D | 329 | 28.319 | −15.712 | −22.918 | 1.00 | 43.18 | S |
| ATOM | 56 | C | CYS | D | 329 | 28.137 | −12.981 | −24.785 | 1.00 | 49.59 | C |
| ATOM | 57 | O | CYS | D | 329 | 27.953 | −13.153 | −25.987 | 1.00 | 52.20 | O |
| ATOM | 58 | N | GLN | D | 330 | 27.225 | −12.422 | −23.985 | 1.00 | 50.36 | N |
| ATOM | 59 | CA | GLN | D | 330 | 25.881 | −12.010 | −24.448 | 1.00 | 55.28 | C |
| ATOM | 60 | CB | GLN | D | 330 | 25.960 | −11.017 | −25.599 | 1.00 | 58.87 | C |
| ATOM | 61 | CG | GLN | D | 330 | 25.703 | −9.583 | −25.205 | 1.00 | 70.06 | C |
| ATOM | 62 | CD | GLN | D | 330 | 26.989 | −8.839 | −24.959 | 1.00 | 72.93 | C |
| ATOM | 63 | OE1 | GLN | D | 330 | 27.182 | −7.734 | −25.455 | 1.00 | 73.11 | O |
| ATOM | 64 | NE2 | GLN | D | 330 | 27.893 | −9.456 | −24.212 | 1.00 | 76.86 | N |
| ATOM | 65 | C | GLN | D | 330 | 24.966 | −13.135 | −24.884 | 1.00 | 57.66 | C |
| ATOM | 66 | O | GLN | D | 330 | 23.834 | −12.882 | −25.289 | 1.00 | 59.24 | O |
| ATOM | 67 | N | GLU? | D | 331 | 25.442 | −14.368 | −24.822 | 1.00 | 58.30 | N |
| ATOM | 68 | CA | GLU? | D | 331 | 24.738 | −15.452 | −25.491 | 1.00 | 60.98 | C |
| ATOM | 69 | CB | GLU? | D | 331 | 25.695 | −16.568 | −25.838 | 1.00 | 58.80 | C |
| ATOM | 70 | CG | GLU? | D | 331 | 26.536 | −16.291 | −27.060 | 1.00 | 59.50 | C |
| ATOM | 71 | CD | GLU? | D | 331 | 27.337 | −17.508 | −27.439 | 1.00 | 62.16 | C |
| ATOM | 72 | OE1 | GLU? | D | 331 | 28.555 | −17.360 | −27.714 | 1.00 | 59.84 | O |
| ATOM | 73 | OE2 | GLU? | D | 331 | 26.744 | −18.618 | −27.421 | 1.00 | 60.25 | O |
| ATOM | 74 | C | GLU? | D | 331 | 23.603 | −16.045 | −24.693 | 1.00 | 63.63 | C |
| ATOM | 75 | O | GLU? | D | 331 | 22.728 | −16.703 | −25.263 | 1.00 | 61.62 | O |
| ATOM | 76 | N | THR | D | 332 | 23.635 | −15.860 | −23.380 | 1.00 | 57.44 | N |
| ATOM | 77 | CA | THR | D | 332 | 22.675 | −16.538 | −22.525 | 1.00 | 57.63 | C |
| ATOM | 78 | CB | THR | D | 332 | 23.376 | −17.554 | −21.605 | 1.00 | 62.66 | C |
| ATOM | 79 | OG1 | THR | D | 332 | 24.622 | −17.002 | −21.145 | 1.00 | 69.08 | O |
| ATOM | 80 | CG2 | THR | D | 332 | 23.626 | −18.869 | −22.353 | 1.00 | 63.16 | C |
| ATOM | 81 | C | THR | D | 332 | 21.939 | −15.562 | −21.653 | 1.00 | 51.94 | C |
| ATOM | 82 | O | THR | D | 332 | 22.478 | −14.538 | −21.305 | 1.00 | 51.40 | O |
| ATOM | 83 | N | GLU? | D | 333 | 20.709 | −15.906 | −21.293 | 1.00 | 49.82 | N |
| ATOM | 84 | CA | GLU? | D | 333 | 19.986 | −15.213 | −20.244 | 1.00 | 53.71 | C |
| ATOM | 85 | CB | GLU? | D | 333 | 18.487 | −15.207 | −20.554 | 1.00 | 51.89 | C |
| ATOM | 86 | CG | GLU? | D | 333 | 17.589 | −14.979 | −19.348 | 1.00 | 55.85 | C |
| ATOM | 87 | CD | GLU? | D | 333 | 16.227 | −14.397 | −19.707 | 1.00 | 64.62 | C |
| ATOM | 88 | OE1 | GLU? | D | 333 | 16.170 | −13.361 | −20.405 | 1.00 | 64.59 | O |
| ATOM | 89 | OE2 | GLU? | D | 333 | 15.201 | −14.964 | −19.272 | 1.00 | 67.76 | O |
| ATOM | 90 | C | GLU? | D | 333 | 20.270 | −15.861 | −18.883 | 1.00 | 50.97 | C |
| ATOM | 91 | O | GLU? | D | 333 | 19.865 | −16.987 | −18.643 | 1.00 | 54.02 | O |
| ATOM | 92 | N | ILE | D | 334 | 20.982 | −15.156 | −18.005 | 1.00 | 48.03 | N |
| ATOM | 93 | CA | ILE | D | 334 | 21.256 | −15.671 | −16.659 | 1.00 | 43.93 | C |
| ATOM | 94 | CB | ILE | D | 334 | 22.414 | −14.918 | −15.951 | 1.00 | 43.22 | C |
| ATOM | 95 | CG1 | ILE | D | 334 | 23.753 | −15.043 | −16.707 | 1.00 | 39.78 | C |
| ATOM | 96 | CD1 | ILE | D | 334 | 23.954 | −16.331 | −17.461 | 1.00 | 41.83 | C |
| ATOM | 97 | CG2 | ILE | D | 334 | 22.536 | −15.367 | −14.495 | 1.00 | 39.59 | C |
| ATOM | 98 | C | ILE | D | 334 | 20.014 | −15.571 | −15.764 | 1.00 | 44.49 | C |
| ATOM | 99 | O | ILE | D | 334 | 19.691 | −16.511 | −15.052 | 1.00 | 41.45 | O |
| ATOM | 100 | N | THR | D | 335 | 19.356 | −14.404 | −15.783 | 1.00 | 47.71 | N |
| ATOM | 101 | CA | THR | D | 335 | 18.174 | −14.122 | −14.950 | 1.00 | 47.01 | C |
| ATOM | 102 | CB | THR | D | 335 | 18.585 | −13.724 | −13.490 | 1.00 | 46.70 | C |
| ATOM | 103 | OG1 | THR | D | 335 | 17.500 | −13.962 | −12.589 | 1.00 | 50.66 | O |

TABLE 7-continued

Atomic coordinates for CRBN(TBD): Compound B (Murine protein)

| ATOM | 104 | CG2 | THR | D | 335 | 18.971 | −12.262 | −13.390 | 1.00 | 47.13 | C |
|---|---|---|---|---|---|---|---|---|---|---|---|
| ATOM | 105 | C | THR | D | 335 | 17.312 | −13.017 | −15.613 | 1.00 | 48.38 | C |
| ATOM | 106 | O | THR | D | 335 | 17.643 | −12.515 | −16.694 | 1.00 | 47.10 | O |
| ATOM | 107 | N | THR | D | 336 | 16.212 | −12.642 | −14.973 | 1.00 | 45.55 | N |
| ATOM | 108 | CA | THR | D | 336 | 15.429 | −11.501 | −15.450 | 1.00 | 48.89 | C |
| ATOM | 109 | CB | THR | D | 336 | 14.041 | −11.921 | −15.965 | 1.00 | 48.02 | C |
| ATOM | 110 | OG1 | THR | D | 336 | 13.214 | −12.302 | −14.862 | 1.00 | 51.32 | O |
| ATOM | 111 | CG2 | THR | D | 336 | 14.153 | −13.083 | −16.943 | 1.00 | 50.95 | C |
| ATOM | 112 | C | THR | D | 336 | 15.247 | −10.485 | −14.337 | 1.00 | 48.43 | C |
| ATOM | 113 | O | THR | D | 336 | 15.254 | −10.849 | −13.156 | 1.00 | 47.18 | O |
| ATOM | 114 | N | LYS | D | 337 | 15.077 | −9.217 | −14.719 | 1.00 | 50.86 | N |
| ATOM | 115 | CA | LYS | D | 337 | 14.824 | −8.141 | −13.771 | 1.00 | 51.17 | C |
| ATOM | 116 | CB | LYS | D | 337 | 14.395 | −6.868 | −14.503 | 1.00 | 56.99 | C |
| ATOM | 117 | CG | LYS | D | 337 | 15.464 | −6.306 | −15.420 | 1.00 | 64.36 | C |
| ATOM | 118 | CD | LYS | D | 337 | 15.199 | −4.850 | −15.768 | 1.00 | 70.89 | C |
| ATOM | 119 | CE | LYS | D | 337 | 16.086 | −4.422 | −16.928 | 1.00 | 76.12 | C |
| ATOM | 120 | NZ | LYS | D | 337 | 16.871 | −3.210 | −16.572 | 1.00 | 72.92 | N |
| ATOM | 121 | C | ASN | D | 338 | 13.759 | −8.562 | −12.769 | 1.00 | 48.42 | C |
| ATOM | 122 | O | ASN | D | 338 | 13.821 | −8.206 | −11.607 | 1.00 | 48.74 | O |
| ATOM | 123 | N | ASN | D | 338 | 12.803 | −9.355 | −13.230 | 1.00 | 52.15 | N |
| ATOM | 124 | CA | ASN | D | 338 | 11.773 | −9.937 | −12.381 | 1.00 | 52.19 | C |
| ATOM | 125 | CB | ASN | D | 338 | 10.890 | −10.866 | −13.217 | 1.00 | 62.08 | C |
| ATOM | 126 | CG | ASN | D | 338 | 9.575 | −10.238 | −13.572 | 1.00 | 66.93 | C |
| ATOM | 127 | OD1 | ASN | D | 338 | 9.447 | −9.014 | −13.608 | 1.00 | 73.47 | O |
| ATOM | 128 | ND2 | ASN | D | 338 | 8.580 | −11.072 | −13.831 | 1.00 | 74.44 | N |
| ATOM | 129 | C | ASN | D | 338 | 12.246 | −10.710 | −11.1448 | 1.00 | 49.72 | C |
| ATOM | 130 | O | ASN | D | 338 | 11.534 | −10.748 | −10.145 | 1.00 | 41.89 | O |
| ATOM | 131 | N | GLU? | D | 339 | 13.419 | −11.349 | −11.221 | 1.00 | 48.97 | N |
| ATOM | 132 | CA | GLU? | D | 339 | 13.862 | −12.262 | −10.143 | 1.00 | 46.62 | C |
| ATOM | 133 | CB | GLU? | D | 339 | 14.691 | −13.405 | −10.714 | 1.00 | 48.90 | C |
| ATOM | 134 | CG | GLU? | D | 339 | 13.960 | −14.220 | −11.763 | 1.00 | 54.86 | C |
| ATOM | 135 | CD | GLU? | D | 339 | 13.057 | −15.306 | −11.178 | 1.00 | 62.15 | C |
| ATOM | 136 | OE1 | GLU? | D | 339 | 12.878 | −15.378 | −9.947 | 1.00 | 66.09 | O |
| ATOM | 137 | OE2 | GLU? | D | 339 | 12.519 | −16.109 | −11.963 | 1.00 | 71.69 | O |
| ATOM | 138 | C | GLU? | D | 339 | 14.653 | −11.568 | −9.053 | 1.00 | 44.83 | C |
| ATOM | 139 | O | GLU? | D | 339 | 15.026 | −12.189 | −8.053 | 1.00 | 46.84 | O |
| ATOM | 140 | N | ILE | D | 340 | 14.922 | −10.283 | −9.249 | 1.00 | 42.40 | N |
| ATOM | 141 | CA | ILE | D | 340 | 15.812 | −9.533 | −8.361 | 1.00 | 40.37 | C |
| ATOM | 142 | CB | ILE | D | 340 | 16.287 | −8.216 | −9.023 | 1.00 | 39.20 | C |
| ATOM | 143 | CG1 | ILE | D | 340 | 17.166 | −8.491 | −10.245 | 1.00 | 40.09 | C |
| ATOM | 144 | CD1 | ILE | D | 340 | 17.382 | −7.264 | −11.101 | 1.00 | 43.03 | C |
| ATOM | 145 | CG2 | ILE | D | 340 | 17.013 | −7.336 | −8.021 | 1.00 | 37.72 | C |
| ATOM | 146 | C | ILE | D | 340 | 15.083 | −9.191 | −7.076 | 1.00 | 42.58 | C |
| ATOM | 147 | O | ILE | D | 340 | 14.002 | −8.592 | −7.123 | 1.00 | 45.17 | O |
| ATOM | 148 | N | PHE | D | 341 | 15.644 | −9.558 | −5.926 | 1.00 | 41.65 | N |
| ATOM | 149 | CA | PHE | D | 341 | 15.063 | −9.077 | −4.688 | 1.00 | 42.66 | C |
| ATOM | 150 | CB | PHE | D | 341 | 14.412 | −10.194 | −3.856 | 1.00 | 53.18 | C |
| ATOM | 151 | CG | PHE | D | 341 | 15.324 | −10.870 | −2.885 | 1.00 | 57.26 | C |
| ATOM | 152 | CD1 | PHE | D | 341 | 16.056 | −11.991 | −3.267 | 1.00 | 62.53 | C |
| ATOM | 153 | CE1 | PHE | D | 341 | 16.873 | −12.648 | −2.354 | 1.00 | 69.00 | C |
| ATOM | 154 | CZ | PHE | D | 341 | 16.946 | −12.198 | −1.039 | 1.00 | 70.84 | C |
| ATOM | 155 | CE2 | PHE | D | 341 | 16.208 | −11.085 | −0.645 | 1.00 | 72.90 | C |
| ATOM | 156 | CD2 | PHE | D | 341 | 15.386 | −10.441 | −1.562 | 1.00 | 64.73 | C |
| ATOM | 157 | C | PHE | D | 341 | 15.926 | −8.115 | −3.875 | 1.00 | 42.76 | C |
| ATOM | 158 | O | PHE | D | 341 | 15.478 | −7.609 | −2.849 | 1.00 | 41.40 | O |
| ATOM | 159 | N | SER | D | 342 | 17.145 | −7.848 | −4.353 | 1.00 | 41.60 | N |
| ATOM | 160 | CA | SER | D | 342 | 17.962 | −6.754 | −3.823 | 1.00 | 36.63 | C |
| ATOM | 161 | CB | SER | D | 342 | 18.645 | −7.169 | −2.525 | 1.00 | 39.13 | C |
| ATOM | 162 | OG | SER | D | 342 | 19.395 | −6.088 | −1.994 | 1.00 | 40.72 | O |
| ATOM | 163 | C | SER | D | 342 | 18.998 | −6.353 | −4.849 | 1.00 | 36.76 | C |
| ATOM | 164 | O | SER | D | 342 | 19.571 | −7.213 | −5.528 | 1.00 | 32.26 | O |
| ATOM | 165 | N | LEU | D | 343 | 19.250 | −5.051 | −4.950 | 1.00 | 34.67 | N |
| ATOM | 166 | CA | LEU | D | 343 | 20.213 | −4.510 | −5.908 | 1.00 | 37.22 | C |
| ATOM | 167 | CB | LEU | D | 343 | 19.724 | −3.133 | −6.407 | 1.00 | 38.61 | C |
| ATOM | 168 | CG | LEU | D | 343 | 18.511 | −3.099 | −7.359 | 1.00 | 40.84 | C |
| ATOM | 169 | CD1 | LEU | D | 343 | 18.004 | −1.680 | −7.529 | 1.00 | 41.60 | C |
| ATOM | 170 | CD2 | LEU | D | 343 | 18.890 | −3.675 | −8.716 | 1.00 | 41.46 | C |
| ATOM | 171 | C | LEU | D | 343 | 21.645 | −4.402 | −5.333 | 1.00 | 38.12 | C |
| ATOM | 172 | O | LEU | D | 343 | 22.602 | −4.175 | −6.071 | 1.00 | 41.91 | O |
| ATOM | 173 | N | SER | D | 344 | 21.780 | −4.585 | −4.021 | 1.00 | 36.37 | N |
| ATOM | 174 | CA | SER | D | 344 | 22.981 | −4.203 | −3.292 | 1.00 | 37.65 | C |
| ATOM | 175 | CB | SER | D | 344 | 22.841 | −2.752 | −2.797 | 1.00 | 38.80 | C |
| ATOM | 176 | OG | SER | D | 344 | 23.108 | −1.853 | −3.840 | 1.00 | 43.64 | O |
| ATOM | 177 | C | SER | D | 344 | 23.124 | −5.057 | −2.069 | 1.00 | 37.13 | C |
| ATOM | 178 | O | SER | D | 344 | 22.120 | −5.490 | −1.498 | 1.00 | 36.88 | O |
| ATOM | 179 | N | LEU | D | 345 | 24.359 | −5.226 | −1.606 | 1.00 | 34.29 | N |
| ATOM | 180 | CA | LEU | D | 345 | 24.596 | −5.918 | −0.330 | 1.00 | 34.20 | C |
| ATOM | 181 | CB | LEU | D | 345 | 25.628 | −7.012 | −0.512 | 1.00 | 33.97 | C |

TABLE 7-continued

Atomic coordinates for CRBN(TBD): Compound B (Murine protein)

| ATOM | 182 | CG  | LEU | D | 345 | 25.154 | -8.231  | -1.299 | 1.00 | 37.95 | C |
|------|-----|-----|-----|---|-----|--------|---------|--------|------|-------|---|
| ATOM | 183 | CD1 | LEU | D | 345 | 26.248 | -9.291  | -1.308 | 1.00 | 37.75 | C |
| ATOM | 184 | CD2 | LEU | D | 345 | 23.878 | -8.799  | -0.700 | 1.00 | 38.57 | C |
| ATOM | 185 | C   | LEU | D | 345 | 25.098 | -4.905  | 0.661  | 1.00 | 36.81 | C |
| ATOM | 186 | O   | LEU | D | 345 | 26.272 | -4.531  | 0.581  | 1.00 | 34.68 | O |
| ATOM | 187 | N   | CYS | D | 346 | 24.217 | -4.446  | 1.576  | 1.00 | 33.97 | N |
| ATOM | 188 | CA  | CYS | D | 346 | 24.463 | -3.261  | 2.402  | 1.00 | 38.44 | C |
| ATOM | 189 | CB  | CYS | D | 346 | 23.227 | -2.352  | 2.404  | 1.00 | 38.01 | C |
| ATOM | 190 | SG  | CYS | D | 346 | 22.911 | -1.658  | 0.778  | 1.00 | 34.64 | S |
| ATOM | 191 | C   | CYS | D | 346 | 24.901 | -3.507  | 3.856  | 1.00 | 43.99 | C |
| ATOM | 192 | O   | CYS | D | 346 | 25.138 | -2.549  | 4.607  | 1.00 | 39.75 | O |
| ATOM | 193 | N   | GLY | D | 347 | 25.025 | -4.771  | 4.253  | 1.00 | 44.40 | N |
| ATOM | 194 | CA  | GLY | D | 347 | 25.299 | -5.092  | 5.653  | 1.00 | 45.93 | C |
| ATOM | 195 | C   | GLY | D | 347 | 26.779 | -5.199  | 5.995  | 1.00 | 46.79 | C |
| ATOM | 196 | O   | GLY | D | 347 | 27.609 | -4.435  | 5.467  | 1.00 | 47.07 | O |
| ATOM | 197 | N   | PRO | D | 348 | 27.123 | -6.156  | 6.878  | 1.00 | 44.92 | N |
| ATOM | 198 | CA  | PRO | D | 348 | 28.504 | -6.388  | 7.298  | 1.00 | 49.59 | C |
| ATOM | 199 | CB  | PRO | D | 348 | 28.418 | -7.727  | 8.032  | 1.00 | 49.37 | C |
| ATOM | 200 | CG  | PRO | D | 348 | 27.029 | -7.764  | 8.560  | 1.00 | 53.70 | C |
| ATOM | 201 | CD  | PRO | D | 348 | 26.196 | -7.127  | 7.486  | 1.00 | 49.19 | C |
| ATOM | 202 | C   | PRO | D | 348 | 29.496 | -6.489  | 6.127  | 1.00 | 48.81 | C |
| ATOM | 203 | O   | PRO | D | 348 | 30.683 | -6.222  | 6.316  | 1.00 | 52.83 | O |
| ATOM | 204 | N   | MET | D | 349 | 29.007 | -6.853  | 4.936  | 1.00 | 43.15 | N |
| ATOM | 205 | CA  | MET | D | 349 | 29.872 | -7.139  | 3.781  | 1.00 | 41.18 | C |
| ATOM | 206 | CB  | MET | D | 349 | 29.378 | -8.417  | 3.058  | 1.00 | 44.97 | C |
| ATOM | 207 | CG  | MET | D | 349 | 28.079 | -8.286  | 2.269  | 1.00 | 45.26 | C |
| ATOM | 208 | SD  | MET | D | 349 | 26.553 | -7.939  | 3.171  | 1.00 | 48.44 | S |
| ATOM | 209 | CE  | MET | D | 349 | 26.236 | -9.477  | 4.047  | 1.00 | 46.69 | C |
| ATOM | 210 | C   | MET | D | 349 | 30.022 | -5.966  | 2.802  | 1.00 | 41.48 | C |
| ATOM | 211 | O   | MET | D | 349 | 30.768 | -6.049  | 1.812  | 1.00 | 39.74 | O |
| ATOM | 212 | N   | ALA | D | 350 | 29.336 | -4.870  | 3.098  | 1.00 | 37.77 | N |
| ATOM | 213 | CA  | ALA | D | 350 | 29.321 | -3.672  | 2.256  | 1.00 | 38.84 | C |
| ATOM | 214 | CB  | ALA | D | 350 | 28.498 | -2.570  | 2.918  | 1.00 | 35.44 | C |
| ATOM | 215 | C   | ALA | D | 350 | 30.706 | -3.131  | 1.950  | 1.00 | 37.71 | C |
| ATOM | 216 | O   | ALA | D | 350 | 30.915 | -2.547  | 0.890  | 1.00 | 34.71 | O |
| ATOM | 217 | N   | ALA | D | 351 | 31.647 | -3.306  | 2.867  | 1.00 | 34.15 | N |
| ATOM | 218 | CA  | ALA | D | 351 | 33.004 | -2.798  | 2.633  | 1.00 | 35.31 | C |
| ATOM | 219 | CB  | ALA | D | 351 | 33.641 | -2.362  | 3.938  | 1.00 | 35.21 | C |
| ATOM | 220 | C   | ALA | D | 351 | 33.920 | -3.773  | 1.899  | 1.00 | 34.97 | C |
| ATOM | 221 | O   | ALA | D | 351 | 35.053 | -3.419  | 1.537  | 1.00 | 34.00 | O |
| ATOM | 222 | N   | TYR | D | 352 | 33.465 | -5.001  | 1.678  | 1.00 | 33.17 | N |
| ATOM | 223 | CA  | TYR | D | 352 | 34.368 | -6.018  | 1.138  | 1.00 | 30.89 | C |
| ATOM | 224 | CB  | TYR | D | 352 | 33.808 | -7.431  | 1.323  | 1.00 | 33.53 | C |
| ATOM | 225 | CG  | TYR | D | 352 | 33.696 | -7.859  | 2.755  | 1.00 | 33.55 | C |
| ATOM | 226 | CD1 | TYR | D | 352 | 34.237 | -7.080  | 3.779  | 1.00 | 37.29 | C |
| ATOM | 227 | CE1 | TYR | D | 352 | 34.140 | -7.464  | 5.095  | 1.00 | 37.88 | C |
| ATOM | 228 | CZ  | TYR | D | 352 | 33.490 | -8.641  | 5.400  | 1.00 | 37.64 | C |
| ATOM | 229 | OH  | TYR | D | 352 | 33.396 | -9.028  | 6.706  | 1.00 | 41.85 | O |
| ATOM | 230 | CE2 | TYR | D | 352 | 32.962 | -9.438  | 4.416  | 1.00 | 34.39 | C |
| ATOM | 231 | CD2 | TYR | D | 352 | 33.072 | -9.042  | 3.092  | 1.00 | 36.66 | C |
| ATOM | 232 | C   | TYR | D | 352 | 34.701 | -5.804  | -0.322 | 1.00 | 33.74 | C |
| ATOM | 233 | O   | TYR | D | 352 | 33.823 | -5.413  | -1.119 | 1.00 | 35.01 | O |
| ATOM | 234 | N   | VAL | D | 353 | 35.969 | -6.082  | -0.657 | 1.00 | 29.98 | N |
| ATOM | 235 | CA  | VAL | D | 353 | 36.518 | -6.037  | -2.030 | 1.00 | 31.48 | C |
| ATOM | 236 | CB  | VAL | D | 353 | 37.477 | -4.844  | -2.241 | 1.00 | 33.99 | C |
| ATOM | 237 | CG1 | VAL | D | 353 | 37.852 | -4.708  | -3.724 | 1.00 | 34.44 | C |
| ATOM | 238 | CG2 | VAL | D | 353 | 36.869 | -3.534  | -1.707 | 1.00 | 36.35 | C |
| ATOM | 239 | C   | VAL | D | 353 | 37.337 | -7.298  | -2.283 | 1.00 | 35.11 | C |
| ATOM | 240 | O   | VAL | D | 353 | 38.289 | -7.610  | -1.548 | 1.00 | 34.94 | O |
| ATOM | 241 | N   | ASN | D | 354 | 36.958 | -8.025  | -3.321 | 1.00 | 36.34 | N |
| ATOM | 242 | CA  | ASN | D | 354 | 37.617 | -9.247  | -3.681 | 1.00 | 33.91 | C |
| ATOM | 243 | CB  | ASN | D | 354 | 36.687 | -10.417 | -3.351 | 1.00 | 33.51 | C |
| ATOM | 244 | CG  | ASN | D | 354 | 35.402 | -10.347 | -4.106 | 1.00 | 32.02 | C |
| ATOM | 245 | OD1 | ASN | D | 354 | 35.335 | -9.674  | -5.136 | 1.00 | 31.31 | O |
| ATOM | 246 | ND2 | ASN | D | 354 | 34.387 | -11.090 | -3.652 | 1.00 | 27.89 | N |
| ATOM | 247 | C   | ASN | D | 354 | 38.021 | -9.173  | -5.175 | 1.00 | 31.50 | C |
| ATOM | 248 | O   | ASN | D | 354 | 37.840 | -8.140  | -5.791 | 1.00 | 30.41 | O |
| ATOM | 249 | N   | PRO | D | 355 | 38.607 | -10.251 | -5.746 | 1.00 | 33.55 | N |
| ATOM | 250 | CA  | PRO | D | 355 | 39.047 | -10.148 | -7.134 | 1.00 | 33.78 | C |
| ATOM | 251 | CB  | PRO | D | 355 | 39.667 | -11.538 | -7.404 | 1.00 | 36.77 | C |
| ATOM | 252 | CG  | PRO | D | 355 | 40.162 | -12.004 | -6.051 | 1.00 | 31.10 | C |
| ATOM | 253 | CD  | PRO | D | 355 | 39.045 | -11.527 | -5.131 | 1.00 | 35.18 | C |
| ATOM | 254 | C   | PRO | D | 355 | 37.906 | -9.874  | -8.123 | 1.00 | 37.04 | C |
| ATOM | 255 | O   | PRO | D | 355 | 38.164 | -9.586  | -9.283 | 1.00 | 40.58 | O |
| ATOM | 256 | N   | HIS | D | 356 | 36.660 | -9.984  | -7.676 | 1.00 | 35.20 | N |
| ATOM | 257 | CA  | HIS | D | 356 | 35.524 | -9.695  | -8.529 | 1.00 | 33.81 | C |
| ATOM | 258 | CB  | HIS | D | 356 | 34.427 | -10.771 | -8.308 | 1.00 | 34.41 | C |
| ATOM | 259 | CG  | HIS | D | 356 | 34.967 | -12.192 | -8.302 | 1.00 | 32.15 | C |

TABLE 7-continued

Atomic coordinates for CRBN(TBD): Compound B (Murine protein)

| ATOM | 260 | ND1 | HIS | D | 356 | 35.501 | −12.766 | −9.402 | 1.00 | 33.62 | N |
|------|-----|-----|-----|---|-----|--------|---------|--------|------|-------|---|
| ATOM | 261 | CE1 | HIS | D | 356 | 35.942 | −14.037 | −9.096 | 1.00 | 33.26 | C |
| ATOM | 262 | NE2 | HIS | D | 356 | 35.690 | −14.262 | −7.781 | 1.00 | 32.82 | N |
| ATOM | 263 | CD2 | HIS | D | 356 | 35.091 | −13.114 | −7.256 | 1.00 | 33.01 | C |
| ATOM | 264 | C   | HIS | D | 356 | 35.015 | −8.286  | −8.272 | 1.00 | 35.75 | C |
| ATOM | 265 | O   | HIS | D | 356 | 33.956 | −7.931  | −8.748 | 1.00 | 35.60 | O |
| ATOM | 266 | N   | GLY | D | 357 | 35.747 | −7.461  | −7.502 | 1.00 | 34.83 | N |
| ATOM | 267 | CA  | GLY | D | 357 | 35.316 | −6.054  | −7.292 | 1.00 | 33.87 | C |
| ATOM | 268 | C   | GLY | D | 357 | 34.536 | −5.832  | −5.997 | 1.00 | 37.52 | C |
| ATOM | 269 | O   | GLY | D | 357 | 34.703 | −6.577  | −5.035 | 1.00 | 38.70 | O |
| ATOM | 270 | N   | TYR | D | 358 | 33.693 | −4.808  | −5.960 | 1.00 | 35.58 | N |
| ATOM | 271 | CA  | TYR | D | 358 | 33.031 | −4.434  | −4.711 | 1.00 | 41.06 | C |
| ATOM | 272 | CB  | TYR | D | 358 | 32.494 | −3.008  | −4.787 | 1.00 | 45.53 | C |
| ATOM | 273 | CG  | TYR | D | 358 | 33.595 | −2.005  | −4.684 | 1.00 | 52.36 | C |
| ATOM | 274 | CD1 | TYR | D | 358 | 34.183 | −1.721  | −3.448 | 1.00 | 52.81 | C |
| ATOM | 275 | CE1 | TYR | D | 358 | 35.226 | −0.819  | −3.345 | 1.00 | 54.83 | C |
| ATOM | 276 | CA  | TYR | D | 358 | 35.701 | −0.201  | −4.485 | 1.00 | 54.91 | C |
| ATOM | 277 | OH  | TYR | D | 358 | 36.723 | −0.710  | −4.371 | 1.00 | 69.32 | O |
| ATOM | 278 | CE2 | TYR | D | 358 | 35.138 | −0.458  | −5.727 | 1.00 | 58.91 | C |
| ATOM | 279 | CD2 | TYR | D | 358 | 34.090 | −1.365  | −5.821 | 1.00 | 56.33 | C |
| ATOM | 280 | C   | TYR | D | 358 | 31.905 | −5.357  | −4.354 | 1.00 | 36.98 | C |
| ATOM | 281 | O   | TYR | D | 358 | 30.943 | −5.438  | −5.082 | 1.00 | 35.51 | O |
| ATOM | 282 | N   | VAL | D | 359 | 32.003 | −6.013  | −3.206 | 1.00 | 34.40 | N |
| ATOM | 283 | CA  | VAL | D | 359 | 30.945 | −6.934  | −2.776 | 1.00 | 33.37 | C |
| ATOM | 284 | CB  | VAL | D | 359 | 31.317 | −7.653  | −1.468 | 1.00 | 32.59 | C |
| ATOM | 285 | CG1 | VAL | D | 359 | 30.114 | −8.484  | −0.957 | 1.00 | 31.19 | C |
| ATOM | 286 | CG2 | VAL | D | 359 | 32.539 | −8.539  | −1.733 | 1.00 | 29.07 | C |
| ATOM | 287 | C   | VAL | D | 359 | 29.577 | −6.223  | −2.663 | 1.00 | 35.54 | C |
| ATOM | 288 | O   | VAL | D | 359 | 28.518 | −6.806  | −2.911 | 1.00 | 33.18 | O |
| ATOM | 289 | N   | HIS | D | 360 | 29.611 | −4.946  | −2.354 | 1.00 | 32.00 | N |
| ATOM | 290 | CA  | HIS | D | 360 | 28.389 | −4.172  | −2.316 | 1.00 | 34.31 | C |
| ATOM | 291 | CB  | HIS | D | 360 | 28.707 | −2.716  | −2.009 | 1.00 | 33.04 | C |
| ATOM | 292 | CG  | HIS | D | 360 | 27.494 | −1.841  | −1.972 | 1.00 | 35.05 | C |
| ATOM | 293 | ND1 | HIS | D | 360 | 27.142 | −1.054  | −3.012 | 1.00 | 32.98 | N |
| ATOM | 294 | CE1 | HIS | D | 360 | 26.002 | −0.402  | −2.702 | 1.00 | 35.22 | C |
| ATOM | 295 | NE2 | HIS | D | 360 | 25.623 | −0.784  | −1.459 | 1.00 | 35.09 | N |
| ATOM | 296 | CD2 | HIS | D | 360 | 26.514 | −1.671  | −0.986 | 1.00 | 29.00 | C |
| ATOM | 297 | C   | HIS | D | 360 | 27.634 | −4.307  | −3.617 | 1.00 | 34.23 | C |
| ATOM | 298 | O   | HIS | D | 360 | 26.429 | −4.516  | −3.607 | 1.00 | 35.51 | O |
| ATOM | 299 | N   | GLU? | D | 361 | 28.352 | −4.296 | −4.749 | 1.00 | 34.92 | N |
| ATOM | 300 | CA  | GLU? | D | 361 | 27.716 | −4.318 | −6.094 | 1.00 | 32.30 | C |
| ATOM | 301 | CB  | GLU? | D | 361 | 28.625 | −3.578 | −7.098 | 1.00 | 36.49 | C |
| ATOM | 302 | CG  | GLU? | D | 361 | 29.007 | −2.159 | −6.642 | 1.00 | 36.65 | C |
| ATOM | 303 | CD  | GLU? | D | 361 | 27.779 | −1.286 | −6.402 | 1.00 | 41.90 | C |
| ATOM | 304 | OE1 | GLU? | D | 361 | 27.742 | −0.557 | −5.385 | 1.00 | 41.98 | O |
| ATOM | 305 | OE2 | GLU? | D | 361 | 26.835 | −1.349 | −7.229 | 1.00 | 44.98 | O |
| ATOM | 306 | C   | GLU? | D | 361 | 27.289 | −5.727 | −6.591 | 1.00 | 35.28 | C |
| ATOM | 307 | O   | GLU? | D | 361 | 27.724 | −6.223 | −7.666 | 1.00 | 33.77 | O |
| ATOM | 308 | N   | THR | D | 362 | 26.464 | −6.369  | −5.773 | 1.00 | 35.76 | N |
| ATOM | 309 | CA  | THR | D | 362 | 25.969 | −7.721  | −6.004 | 1.00 | 37.70 | C |
| ATOM | 310 | CB  | THR | D | 362 | 26.528 | −8.682  | −4.956 | 1.00 | 41.76 | C |
| ATOM | 311 | OG1 | THR | D | 362 | 27.932 | −8.497  | −4.868 | 1.00 | 41.20 | O |
| ATOM | 312 | CG2 | THR | D | 362 | 26.217 | −10.170 | −5.291 | 1.00 | 37.69 | C |
| ATOM | 313 | C   | THR | D | 362 | 24.442 | −7.736  | −5.872 | 1.00 | 39.83 | C |
| ATOM | 314 | O   | THR | D | 362 | 23.886 | −7.254  | −4.857 | 1.00 | 36.64 | O |
| ATOM | 315 | N   | LEU | D | 363 | 23.791 | −8.273  | −6.909 | 1.00 | 36.29 | N |
| ATOM | 316 | CA  | LEU | D | 363 | 22.342 | −8.508  | −6.964 | 1.00 | 36.95 | C |
| ATOM | 317 | CB  | LEU | D | 363 | 21.927 | −8.748  | −8.426 | 1.00 | 35.28 | C |
| ATOM | 318 | CG  | LEU | D | 363 | 21.385 | −7.651  | −9.312 | 1.00 | 37.37 | C |
| ATOM | 319 | CD1 | LEU | D | 363 | 21.771 | −6.251  | −8.852 | 1.00 | 36.72 | C |
| ATOM | 320 | CD2 | LEU | D | 363 | 21.821 | −7.913  | −10.740 | 1.00 | 34.13 | C |
| ATOM | 321 | C   | LEU | D | 363 | 22.013 | −9.783  | −6.225 | 1.00 | 40.43 | C |
| ATOM | 322 | O   | LEU | D | 363 | 22.779 | −10.748 | −6.305 | 1.00 | 44.36 | O |
| ATOM | 323 | N   | THR | D | 364 | 20.871 | −9.826  | −5.541 | 1.00 | 37.95 | N |
| ATOM | 324 | CA  | THR | D | 364 | 20.370 | −11.099 | −5.034 | 1.00 | 40.03 | C |
| ATOM | 325 | CB  | THR | D | 364 | 20.140 | −11.092 | −3.516 | 1.00 | 40.52 | C |
| ATOM | 326 | OG1 | THR | D | 364 | 19.181 | −10.089 | −3.203 | 1.00 | 58.15 | O |
| ATOM | 327 | CG2 | THR | D | 364 | 21.403 | −10.775 | −2.803 | 1.00 | 43.74 | C |
| ATOM | 328 | C   | THR | D | 364 | 19.085 | −11.438 | −5.782 | 1.00 | 39.43 | C |
| ATOM | 329 | O   | THR | D | 364 | 18.166 | −10.626 | −5.848 | 1.00 | 37.48 | O |
| ATOM | 330 | N   | VAL | D | 365 | 19.065 | −12.615 | −6.397 | 1.00 | 37.36 | N |
| ATOM | 331 | CA  | VAL | D | 365 | 17.980 | −13.021 | −7.257 | 1.00 | 37.39 | C |
| ATOM | 332 | CB  | VAL | D | 365 | 18.388 | −13.006 | −8.759 | 1.00 | 38.96 | C |
| ATOM | 333 | CG1 | VAL | D | 365 | 19.146 | −11.729 | −9.074 | 1.00 | 41.95 | C |
| ATOM | 334 | CG2 | VAL | D | 365 | 19.262 | −14.187 | −9.131 | 1.00 | 39.31 | C |
| ATOM | 335 | C   | VAL | D | 365 | 17.472 | −14.371 | −6.812 | 1.00 | 37.49 | C |
| ATOM | 336 | O   | VAL | D | 365 | 18.209 | −15.138 | −6.198 | 1.00 | 34.12 | O |
| ATOM | 337 | N   | TYR | D | 366 | 16.186 | −14.633 | −7.066 | 1.00 | 41.73 | N |

TABLE 7-continued

Atomic coordinates for CRBN(TBD): Compound B (Murine protein)

| ATOM | 338 | CA  | TYR | D | 366 | 15.564 | −15.911 | −6.728  | 1.00 | 41.31 | C |
|------|-----|-----|-----|---|-----|--------|---------|---------|------|-------|---|
| ATOM | 339 | CB  | TYR | D | 366 | 14.045 | −15.802 | −6.795  | 1.00 | 48.43 | C |
| ATOM | 340 | CG  | TYR | D | 366 | 13.453 | −14.932 | −5.738  | 1.00 | 46.52 | C |
| ATOM | 341 | CD1 | TYR | D | 366 | 13.550 | −15.277 | −4.390  | 1.00 | 49.31 | C |
| ATOM | 342 | CE1 | TYR | D | 366 | 12.991 | −14.477 | −3.410  | 1.00 | 53.15 | C |
| ATOM | 343 | CZ  | TYR | D | 366 | 12.315 | −13.326 | −3.785  | 1.00 | 53.40 | C |
| ATOM | 344 | OH  | TYR | D | 366 | 11.768 | −12.521 | −2.831  | 1.00 | 59.53 | O |
| ATOM | 345 | CE2 | TYR | D | 366 | 12.202 | −12.966 | −5.111  | 1.00 | 52.37 | C |
| ATOM | 346 | CD2 | TYR | D | 366 | 12.778 | −13.767 | −6.081  | 1.00 | 49.58 | C |
| ATOM | 347 | C   | TYR | D | 366 | 15.985 | −17.071 | −7.614  | 1.00 | 37.88 | C |
| ATOM | 348 | O   | TYR | D | 366 | 16.056 | −18.194 | −7.152  | 1.00 | 37.98 | O |
| ATOM | 349 | N   | LYS | D | 367 | 16.227 | −16.803 | −8.885  | 1.00 | 39.35 | N |
| ATOM | 350 | CA  | LYS | D | 367 | 16.515 | −17.853 | −9.850  | 1.00 | 42.45 | C |
| ATOM | 351 | CB  | LYS | D | 367 | 15.247 | −18.249 | −10.610 | 1.00 | 47.41 | C |
| ATOM | 352 | CG  | LYS | D | 367 | 14.501 | −19.412 | −10.004 | 1.00 | 55.96 | C |
| ATOM | 353 | CD  | LYS | D | 367 | 13.025 | −19.362 | −10.355 | 1.00 | 59.54 | C |
| ATOM | 354 | CE  | LYS | D | 367 | 12.238 | −20.254 | −9.408  | 1.00 | 59.93 | C |
| ATOM | 355 | NZ  | LYS | D | 367 | 10.780 | −20.050 | −9.600  | 1.00 | 64.09 | N |
| ATOM | 356 | C   | LYS | D | 367 | 17.488 | −17.314 | −10.850 | 1.00 | 41.59 | C |
| ATOM | 357 | O   | LYS | D | 367 | 17.423 | −16.142 | −11.212 | 1.00 | 38.46 | O |
| ATOM | 358 | N   | ALA | D | 368 | 18.384 | −18.180 | −11.297 | 1.00 | 39.65 | N |
| ATOM | 359 | CA  | ALA | D | 368 | 19.311 | −17.870 | −12.381 | 1.00 | 39.60 | C |
| ATOM | 360 | CB  | ALA | D | 368 | 20.649 | −17.404 | −11.820 | 1.00 | 37.21 | C |
| ATOM | 361 | C   | ALA | D | 368 | 19.489 | −19.174 | −13.087 | 1.00 | 38.56 | C |
| ATOM | 362 | O   | ALA | D | 368 | 19.334 | −20.214 | −12.480 | 1.00 | 43.24 | O |
| ATOM | 363 | N   | SER | D | 369 | 19.832 | −19.149 | −14.356 | 1.00 | 40.49 | N |
| ATOM | 364 | CA  | SER | D | 369 | 20.224 | −20.388 | −15.015 | 1.00 | 42.25 | C |
| ATOM | 365 | CB  | SER | D | 369 | 19.043 | −20.939 | −15.798 | 1.00 | 45.22 | C |
| ATOM | 366 | OG  | SER | D | 369 | 18.521 | −19.910 | −16.598 | 1.00 | 48.44 | O |
| ATOM | 367 | C   | SER | D | 369 | 21.394 | −20.113 | −15.938 | 1.00 | 40.57 | C |
| ATOM | 368 | O   | SER | D | 369 | 21.865 | −18.974 | −16.021 | 1.00 | 41.30 | O |
| ATOM | 369 | N   | ASN | D | 370 | 21.838 | −21.150 | −16.638 | 1.00 | 37.10 | N |
| ATOM | 370 | CA  | ASN | D | 370 | 22.961 | −21.072 | −17.585 | 1.00 | 38.54 | C |
| ATOM | 371 | CB  | ASN | D | 370 | 22.675 | −20.083 | −18.714 | 1.00 | 36.89 | C |
| ATOM | 372 | CG  | ASN | D | 370 | 21.498 | −20.523 | −19.575 | 1.00 | 44.46 | C |
| ATOM | 373 | OD1 | ASN | D | 370 | 20.618 | −19.724 | −19.891 | 1.00 | 46.79 | O |
| ATOM | 374 | ND2 | ASN | D | 370 | 21.458 | −21.801 | −19.929 | 1.00 | 43.86 | N |
| ATOM | 375 | C   | ASN | D | 370 | 24.329 | −20.828 | −16.960 | 1.00 | 35.25 | C |
| ATOM | 376 | O   | ASN | D | 370 | 25.214 | −20.228 | −17.583 | 1.00 | 36.57 | O |
| ATOM | 377 | N   | LEU | D | 371 | 24.484 | −21.331 | −15.742 | 1.00 | 33.74 | N |
| ATOM | 378 | CA  | LEU | D | 371 | 25.664 | −21.133 | −14.908 | 1.00 | 34.91 | C |
| ATOM | 379 | CB  | LEU | D | 371 | 25.224 | −20.452 | −13.609 | 1.00 | 31.20 | C |
| ATOM | 380 | CG  | LEU | D | 371 | 24.705 | −19.026 | −13.788 | 1.00 | 34.14 | C |
| ATOM | 381 | CD1 | LEU | D | 371 | 24.271 | −18.387 | −12.469 | 1.00 | 34.93 | C |
| ATOM | 382 | CD2 | LEU | D | 371 | 25.763 | −18.163 | −14.428 | 1.00 | 30.61 | C |
| ATOM | 383 | C   | LEU | D | 371 | 26.235 | −22.489 | −14.580 | 1.00 | 34.53 | C |
| ATOM | 384 | O   | LEU | D | 371 | 25.484 | −23.420 | −14.366 | 1.00 | 39.51 | O |
| ATOM | 385 | N   | ASN | D | 372 | 27.550 | −22.630 | −14.588 | 1.00 | 35.09 | N |
| ATOM | 386 | CA  | ASN | D | 372 | 28.174 | −23.846 | −14.082 | 1.00 | 34.71 | C |
| ATOM | 387 | CB  | ASN | D | 372 | 29.463 | −24.170 | −14.855 | 1.00 | 33.95 | C |
| ATOM | 388 | CG  | ASN | D | 372 | 29.204 | −24.930 | −16.157 | 1.00 | 32.71 | C |
| ATOM | 389 | OD1 | ASN | D | 372 | 28.227 | −25.648 | −16.276 | 1.00 | 31.70 | O |
| ATOM | 390 | ND2 | ASN | D | 372 | 30.078 | −24.763 | −17.126 | 1.00 | 31.04 | N |
| ATOM | 391 | C   | ASN | D | 372 | 28.522 | −23.594 | −12.620 | 1.00 | 37.24 | C |
| ATOM | 392 | O   | ASN | D | 372 | 28.977 | −22.506 | −12.269 | 1.00 | 33.78 | O |
| ATOM | 393 | N   | LEU | D | 373 | 28.315 | −24.592 | −11.770 | 1.00 | 37.90 | N |
| ATOM | 394 | CA  | LEU | D | 373 | 28.715 | −24.474 | −10.353 | 1.00 | 36.96 | C |
| ATOM | 395 | CB  | LEU | D | 373 | 27.639 | −25.039 | −9.426  | 1.00 | 34.06 | C |
| ATOM | 396 | CG  | LEU | D | 373 | 26.225 | −24.418 | −9.508  | 1.00 | 37.03 | C |
| ATOM | 397 | CD1 | LEU | D | 373 | 25.176 | −25.200 | −8.709  | 1.00 | 36.31 | C |
| ATOM | 398 | CD2 | LEU | D | 373 | 26.225 | −22.949 | −9.085  | 1.00 | 36.31 | C |
| ATOM | 399 | C   | LEU | D | 373 | 30.056 | −25.149 | −10.152 | 1.00 | 37.16 | C |
| ATOM | 400 | O   | LEU | D | 373 | 30.275 | −26.259 | −10.640 | 1.00 | 39.83 | O |
| ATOM | 401 | N   | ILE | D | 374 | 30.968 | −24.452 | −9.488  | 1.00 | 35.93 | N |
| ATOM | 402 | CA  | ILE | D | 374 | 32.318 | −24.956 | −9.239  | 1.00 | 36.73 | C |
| ATOM | 403 | CB  | ILE | D | 374 | 33.392 | −23.933 | −9.672  | 1.00 | 39.27 | C |
| ATOM | 404 | CG1 | ILE | D | 374 | 33.048 | −23.222 | −11.004 | 1.00 | 40.22 | C |
| ATOM | 405 | CD1 | ILE | D | 374 | 32.856 | −24.144 | −12.184 | 1.00 | 40.74 | C |
| ATOM | 406 | CG2 | ILE | D | 374 | 34.771 | −24.558 | −9.670  | 1.00 | 42.35 | C |
| ATOM | 407 | C   | ILE | D | 374 | 32.523 | −25.202 | −7.748  | 1.00 | 38.26 | C |
| ATOM | 408 | O   | ILE | D | 374 | 32.465 | −24.262 | −6.950  | 1.00 | 39.25 | O |
| ATOM | 409 | N   | GLY | D | 375 | 32.771 | −26.453 | −7.378  | 1.00 | 36.61 | N |
| ATOM | 410 | CA  | GLY | D | 375 | 33.059 | −26.827 | −5.991  | 1.00 | 39.66 | C |
| ATOM | 411 | C   | GLY | D | 375 | 31.859 | −27.338 | −5.205  | 1.00 | 42.80 | C |
| ATOM | 412 | O   | GLY | D | 375 | 30.754 | −27.469 | −5.738  | 1.00 | 40.54 | O |
| ATOM | 413 | N   | ARG | D | 376 | 32.095 | −27.649 | −3.935  | 1.00 | 43.08 | N |
| ATOM | 414 | CA  | ARG | D | 376 | 31.050 | −28.018 | −2.992  | 1.00 | 44.29 | C |
| ATOM | 415 | CB  | ARG | D | 376 | 31.598 | −29.073 | −2.006  | 1.00 | 50.84 | C |

TABLE 7-continued

Atomic coordinates for CRBN(TBD): Compound B (Murine protein)

| ATOM | 416 | CG | ARG | D | 376 | 31.730 | −30.485 | −2.569 | 1.00 | 59.41 | C |
|---|---|---|---|---|---|---|---|---|---|---|---|
| ATOM | 417 | CD | ARG | D | 376 | 30.389 | −31.236 | −2.555 | 1.00 | 69.31 | C |
| ATOM | 418 | NE | ARG | D | 376 | 30.362 | −32.513 | −3.304 | 1.00 | 78.56 | N |
| ATOM | 419 | CZ | ARG | D | 376 | 31.369 | −33.390 | −3.405 | 1.00 | 79.37 | C |
| ATOM | 420 | NH1 | ARG | D | 376 | 32.529 | −33.167 | −2.796 | 1.00 | 73.26 | N |
| ATOM | 421 | NH2 | ARG | D | 376 | 31.210 | −34.506 | −4.118 | 1.00 | 78.15 | N |
| ATOM | 422 | C | ARG | D | 376 | 30.643 | −26.750 | −2.228 | 1.00 | 39.46 | C |
| ATOM | 423 | O | ARG | D | 376 | 31.475 | −25.872 | −2.012 | 1.00 | 43.83 | O |
| ATOM | 424 | N | PRO | D | 377 | 29.376 | −26.644 | −1.799 | 1.00 | 39.18 | N |
| ATOM | 425 | CA | PRO | D | 377 | 28.999 | −25.446 | −1.012 | 1.00 | 36.85 | C |
| ATOM | 426 | CB | PRO | D | 377 | 27.574 | −25.777 | −0.539 | 1.00 | 36.38 | C |
| ATOM | 427 | CG | PRO | D | 377 | 27.068 | −26.825 | −1.491 | 1.00 | 37.82 | C |
| ATOM | 428 | CD | PRO | D | 377 | 28.291 | −27.650 | −1.809 | 1.00 | 39.22 | C |
| ATOM | 429 | C | PRO | D | 377 | 29.921 | −25.243 | 0.199 | 1.00 | 34.83 | C |
| ATOM | 430 | O | PRO | D | 377 | 30.331 | −26.213 | 0.803 | 1.00 | 38.01 | O |
| ATOM | 431 | N | SER | D | 378 | 30.261 | −24.000 | 0.533 | 1.00 | 33.49 | N |
| ATOM | 432 | CA | SER | D | 378 | 31.112 | −23.726 | 1.695 | 1.00 | 32.07 | C |
| ATOM | 433 | CB | SER | D | 378 | 32.481 | −23.222 | 1.209 | 1.00 | 33.70 | C |
| ATOM | 434 | OG | SER | D | 378 | 33.272 | −22.803 | 2.310 | 1.00 | 38.53 | O |
| ATOM | 435 | C | SER | D | 378 | 30.451 | −22.699 | 2.608 | 1.00 | 33.15 | C |
| ATOM | 436 | O | SER | D | 378 | 29.805 | −21.758 | 2.124 | 1.00 | 34.08 | O |
| ATOM | 437 | N | THR | D | 379 | 30.551 | −22.891 | 3.921 | 1.00 | 32.45 | N |
| ATOM | 438 | CA | THR | D | 379 | 30.063 | −21.883 | 4.859 | 1.00 | 35.64 | C |
| ATOM | 439 | CB | THR | D | 379 | 29.446 | −22.493 | 6.132 | 1.00 | 38.35 | C |
| ATOM | 440 | OG1 | THR | D | 379 | 30.425 | −23.336 | 6.748 | 1.00 | 39.57 | O |
| ATOM | 441 | CG2 | THR | D | 379 | 28.163 | −23.311 | 5.812 | 1.00 | 35.73 | C |
| ATOM | 442 | C | THR | D | 379 | 31.160 | −20.921 | 5.321 | 1.00 | 36.20 | C |
| ATOM | 443 | O | THR | D | 379 | 30.853 | −19.907 | 5.942 | 1.00 | 35.85 | O |
| ATOM | 444 | N | VAL | D | 380 | 32.429 | −21.217 | 5.038 | 1.00 | 36.69 | N |
| ATOM | 445 | CA | VAL | D | 380 | 33.520 | −20.286 | 5.452 | 1.00 | 35.32 | C |
| ATOM | 446 | CB | VAL | D | 380 | 34.907 | −20.834 | 5.066 | 1.00 | 35.62 | C |
| ATOM | 447 | CG1 | VAL | D | 380 | 36.019 | −19.926 | 5.595 | 1.00 | 35.88 | C |
| ATOM | 448 | CG2 | VAL | D | 380 | 35.062 | −22.214 | 5.659 | 1.00 | 33.88 | C |
| ATOM | 449 | C | VAL | D | 380 | 33.303 | −18.841 | 4.952 | 1.00 | 32.73 | C |
| ATOM | 450 | O | VAL | D | 380 | 33.172 | −18.594 | 3.763 | 1.00 | 35.46 | O |
| ATOM | 451 | N | HIS | D | 381 | 33.190 | −17.902 | 5.891 | 1.00 | 31.84 | N |
| ATOM | 452 | CA | HIS | D | 381 | 32.978 | −16.487 | 5.582 | 1.00 | 32.06 | C |
| ATOM | 453 | CB | HIS | D | 381 | 34.218 | −15.871 | 4.903 | 1.00 | 32.91 | C |
| ATOM | 454 | CG | HIS | D | 381 | 35.481 | −15.854 | 5.770 | 1.00 | 32.96 | C |
| ATOM | 455 | ND1 | HIS | D | 381 | 35.479 | −15.452 | 7.066 | 1.00 | 35.59 | N |
| ATOM | 456 | CE1 | HIS | D | 381 | 36.756 | −15.510 | 7.565 | 1.00 | 35.85 | C |
| ATOM | 457 | NE2 | HIS | D | 381 | 37.590 | −15.919 | 6.558 | 1.00 | 31.51 | N |
| ATOM | 458 | CD2 | HIS | D | 381 | 36.841 | −16.141 | 5.445 | 1.00 | 37.26 | C |
| ATOM | 459 | C | HIS | D | 381 | 31.749 | −16.233 | 4.746 | 1.00 | 34.61 | C |
| ATOM | 460 | O | HIS | D | 381 | 31.709 | −15.280 | 3.954 | 1.00 | 31.70 | O |
| ATOM | 461 | N | SER | D | 382 | 30.711 | −17.064 | 4.899 | 1.00 | 34.29 | N |
| ATOM | 462 | CA | SER | D | 382 | 29.481 | −16.835 | 4.144 | 1.00 | 32.01 | C |
| ATOM | 463 | CB | SER | D | 382 | 28.421 | −17.878 | 4.476 | 1.00 | 31.79 | C |
| ATOM | 464 | OG | SER | D | 382 | 27.241 | −17.553 | 3.755 | 1.00 | 33.80 | O |
| ATOM | 465 | C | SER | D | 382 | 28.928 | −15.426 | 4.408 | 1.00 | 33.44 | C |
| ATOM | 466 | O | SER | D | 382 | 28.932 | −14.971 | 5.544 | 1.00 | 32.57 | O |
| ATOM | 467 | N | TRP | D | 383 | 28.456 | −14.728 | 3.374 | 1.00 | 34.23 | N |
| ATOM | 468 | CA | TRP | D | 383 | 27.835 | −13.422 | 3.631 | 1.00 | 35.12 | C |
| ATOM | 469 | CB | TRP | D | 383 | 27.711 | −12.616 | 2.362 | 1.00 | 31.98 | C |
| ATOM | 470 | CG | TRP | D | 383 | 29.009 | −12.338 | 1.666 | 1.00 | 34.15 | C |
| ATOM | 471 | CD1 | TRP | D | 383 | 30.259 | −12.059 | 2.236 | 1.00 | 33.46 | C |
| ATOM | 472 | NE1 | TRP | D | 383 | 31.206 | −11.853 | 1.247 | 1.00 | 31.44 | N |
| ATOM | 473 | CE2 | TRP | D | 383 | 30.632 | −11.955 | 0.022 | 1.00 | 33.83 | C |
| ATOM | 474 | CD2 | TRP | D | 383 | 29.211 | −12.261 | 0.230 | 1.00 | 31.29 | C |
| ATOM | 475 | CE3 | TRP | D | 383 | 28.392 | −12.427 | −0.864 | 1.00 | 34.28 | C |
| ATOM | 476 | CZ3 | TRP | D | 383 | 28.957 | −12.287 | −2.140 | 1.00 | 35.89 | C |
| ATOM | 477 | CH2 | TRP | D | 383 | 30.307 | −12.007 | −2.316 | 1.00 | 33.47 | C |
| ATOM | 478 | CZ2 | TRP | D | 383 | 31.177 | −11.839 | −1.242 | 1.00 | 33.32 | C |
| ATOM | 479 | C | TRP | D | 383 | 26.469 | −13.529 | 4.267 | 1.00 | 38.94 | C |
| ATOM | 480 | O | TRP | D | 383 | 25.943 | −12.538 | 4.781 | 1.00 | 34.44 | O |
| ATOM | 481 | N | PHE | D | 384 | 25.850 | −14.698 | 4.195 | 1.00 | 38.99 | N |
| ATOM | 482 | CA | PHE | D | 384 | 24.489 | −14.849 | 4.722 | 1.00 | 38.88 | C |
| ATOM | 483 | CB | PHE | D | 384 | 23.496 | −15.090 | 3.576 | 1.00 | 37.96 | C |
| ATOM | 484 | CG | PHE | D | 384 | 23.478 | −13.994 | 2.546 | 1.00 | 42.43 | C |
| ATOM | 485 | CD1 | PHE | D | 384 | 22.687 | −12.858 | 2.728 | 1.00 | 44.37 | C |
| ATOM | 486 | CE1 | PHE | D | 384 | 22.669 | −11.844 | 1.775 | 1.00 | 43.34 | C |
| ATOM | 487 | CZ | PHE | D | 384 | 23.451 | −11.957 | 0.634 | 1.00 | 45.17 | C |
| ATOM | 488 | CE2 | PHE | D | 384 | 24.242 | −13.083 | 0.447 | 1.00 | 41.11 | C |
| ATOM | 489 | CD2 | PHE | D | 384 | 24.240 | −14.095 | 1.387 | 1.00 | 39.47 | C |
| ATOM | 490 | C | PHE | D | 384 | 24.502 | −16.032 | 5.666 | 1.00 | 39.96 | C |
| ATOM | 491 | O | PHE | D | 384 | 24.377 | −17.166 | 5.213 | 1.00 | 40.65 | O |
| ATOM | 492 | N | PRO | D | 385 | 24.709 | −15.782 | 6.974 | 1.00 | 43.72 | N |
| ATOM | 493 | CA | PRO | D | 385 | 24.856 | −16.883 | 7.926 | 1.00 | 45.44 | C |

TABLE 7-continued

Atomic coordinates for CRBN(TBD): Compound B (Murine protein)

| ATOM | 494 | CB | PRO | D | 385 | 24.890 | −16.169 | 9.282 | 1.00 | 48.76 | C |
| --- | --- | --- | --- | --- | --- | --- | --- | --- | --- | --- | --- |
| ATOM | 495 | CG | PRO | D | 385 | 25.502 | −14.838 | 8.960 | 1.00 | 48.53 | C |
| ATOM | 496 | CD | PRO | D | 385 | 24.856 | −14.473 | 7.642 | 1.00 | 46.37 | C |
| ATOM | 497 | C | PRO | D | 385 | 23.684 | −17.865 | 7.838 | 1.00 | 45.59 | C |
| ATOM | 498 | O | PRO | D | 385 | 22.535 | −17.450 | 7.676 | 1.00 | 41.55 | O |
| ATOM | 499 | N | GLY | D | 386 | 24.011 | −19.157 | 7.882 | 1.00 | 43.27 | N |
| ATOM | 500 | CA | GLY | D | 386 | 23.053 | −20.233 | 7.683 | 1.00 | 40.86 | C |
| ATOM | 501 | C | GLY | D | 386 | 22.961 | −20.714 | 6.250 | 1.00 | 39.65 | C |
| ATOM | 502 | O | GLY | D | 386 | 22.235 | −21.676 | 5.961 | 1.00 | 35.59 | O |
| ATOM | 503 | N | TYR | D | 387 | 23.625 | −19.995 | 5.343 | 1.00 | 36.22 | N |
| ATOM | 504 | CA | TYR | D | 387 | 23.713 | −20.396 | 3.930 | 1.00 | 35.77 | C |
| ATOM | 505 | CB | TYR | D | 387 | 23.211 | −19.270 | 2.994 | 1.00 | 34.92 | C |
| ATOM | 506 | CG | TYR | D | 387 | 21.746 | −19.073 | 3.038 | 1.00 | 37.77 | C |
| ATOM | 507 | CD1 | TYR | D | 387 | 20.911 | −19.807 | 2.202 | 1.00 | 37.84 | C |
| ATOM | 508 | CE1 | TYR | D | 387 | 19.555 | −19.655 | 2.245 | 1.00 | 41.24 | C |
| ATOM | 509 | CZ | TYR | D | 387 | 18.994 | −18.762 | 3.152 | 1.00 | 43.55 | C |
| ATOM | 510 | OH | TYR | D | 387 | 17.615 | −18.617 | 3.183 | 1.00 | 42.93 | O |
| ATOM | 511 | CE2 | TYR | D | 387 | 19.799 | −18.011 | 3.997 | 1.00 | 40.40 | C |
| ATOM | 512 | CD2 | TYR | D | 387 | 21.176 | −18.173 | 3.934 | 1.00 | 38.33 | C |
| ATOM | 513 | C | TYR | D | 387 | 25.141 | −20.713 | 3.570 | 1.00 | 34.68 | C |
| ATOM | 514 | O | TYR | D | 387 | 26.075 | −20.042 | 4.051 | 1.00 | 37.38 | O |
| ATOM | 515 | N | ALA | D | 388 | 25.313 | −21.691 | 2.685 | 1.00 | 33.11 | N |
| ATOM | 516 | CA | ALA | D | 388 | 26.621 | −21.984 | 2.084 | 1.00 | 36.22 | C |
| ATOM | 517 | CB | ALA | D | 388 | 26.884 | −23.495 | 2.092 | 1.00 | 36.42 | C |
| ATOM | 518 | C | ALA | D | 388 | 26.654 | −21.438 | 0.660 | 1.00 | 32.65 | C |
| ATOM | 519 | O | ALA | D | 388 | 25.597 | −21.287 | 0.036 | 1.00 | 35.53 | O |
| ATOM | 520 | N | TRP | D | 389 | 27.848 | −21.151 | 0.146 | 1.00 | 32.91 | N |
| ATOM | 521 | CA | TRP | D | 389 | 28.015 | −20.560 | −1.191 | 1.00 | 32.32 | C |
| ATOM | 522 | CB | TRP | D | 389 | 28.688 | −19.181 | −1.085 | 1.00 | 30.82 | C |
| ATOM | 523 | CG | TRP | D | 389 | 29.981 | −19.160 | −0.290 | 1.00 | 30.29 | C |
| ATOM | 524 | CD1 | TRP | D | 389 | 30.148 | −18.845 | 1.055 | 1.00 | 30.87 | C |
| ATOM | 525 | NE1 | TRP | D | 389 | 31.470 | −18.925 | 1.411 | 1.00 | 29.58 | N |
| ATOM | 526 | CE2 | TRP | D | 389 | 32.226 | −19.269 | 0.352 | 1.00 | 31.08 | C |
| ATOM | 527 | CD2 | TRP | D | 389 | 31.329 | −19.419 | −0.789 | 1.00 | 28.42 | C |
| ATOM | 528 | CE3 | TRP | D | 389 | 31.858 | −19.785 | −2.027 | 1.00 | 30.50 | C |
| ATOM | 529 | CZ3 | TRP | D | 389 | 33.247 | −19.972 | −2.135 | 1.00 | 32.88 | C |
| ATOM | 530 | CH2 | TRP | D | 389 | 34.100 | −19.794 | −1.023 | 1.00 | 31.66 | C |
| ATOM | 531 | CZ2 | TRP | D | 389 | 33.610 | −19.458 | 0.242 | 1.00 | 31.85 | C |
| ATOM | 532 | C | TRP | D | 389 | 28.796 | −21.427 | 2.135 | 1.00 | 33.16 | C |
| ATOM | 533 | O | TRP | D | 389 | 29.711 | −22.144 | −1.735 | 1.00 | 32.77 | O |
| ATOM | 534 | N | THR | D | 390 | 28.463 | −21.355 | −3.413 | 1.00 | 34.00 | N |
| ATOM | 535 | CA | THR | D | 390 | 29.249 | −22.053 | −4.436 | 1.00 | 34.64 | C |
| ATOM | 536 | CB | THR | D | 390 | 28.508 | −23.307 | −4.949 | 1.00 | 33.33 | C |
| ATOM | 537 | OG1 | THR | D | 390 | 28.116 | −24.103 | −3.832 | 1.00 | 33.41 | O |
| ATOM | 538 | CG2 | THR | D | 390 | 29.412 | −24.133 | −5.861 | 1.00 | 32.88 | C |
| ATOM | 539 | C | THR | D | 390 | 29.493 | −21.120 | −5.602 | 1.00 | 33.95 | C |
| ATOM | 540 | O | THR | D | 390 | 28.561 | −20.464 | −6.062 | 1.00 | 32.10 | O |
| ATOM | 541 | N | ILE | D | 391 | 30.737 | −21.043 | −6.071 | 1.00 | 33.47 | N |
| ATOM | 542 | CA | ILE | D | 391 | 31.087 | −20.121 | −7.135 | 1.00 | 33.01 | C |
| ATOM | 543 | CB | ILE | D | 391 | 32.606 | −20.144 | −7.432 | 1.00 | 34.39 | C |
| ATOM | 544 | CG1 | ILE | D | 391 | 33.361 | −19.302 | −6.389 | 1.00 | 36.06 | C |
| ATOM | 545 | CD1 | ILE | D | 391 | 34.776 | −19.786 | −6.120 | 1.00 | 34.24 | C |
| ATOM | 546 | CG2 | ILE | D | 391 | 32.902 | −19.578 | −8.825 | 1.00 | 33.97 | C |
| ATOM | 547 | C | ILE | D | 391 | 30.278 | −20.501 | −8.380 | 1.00 | 37.87 | C |
| ATOM | 548 | O | ILE | D | 391 | 30.084 | −21.699 | −8.654 | 1.00 | 35.49 | O |
| ATOM | 549 | N | ALA | D | 392 | 29.803 | −19.498 | −9.126 | 1.00 | 32.41 | N |
| ATOM | 550 | CA | ALA | D | 392 | 29.001 | −19.767 | −10.334 | 1.00 | 34.27 | C |
| ATOM | 551 | CB | ALA | D | 392 | 27.520 | −19.451 | −10.098 | 1.00 | 31.15 | C |
| ATOM | 552 | C | ALA | D | 392 | 29.545 | −18.999 | −11.537 | 1.00 | 34.93 | C |
| ATOM | 553 | O | ALA | D | 392 | 29.826 | −17.796 | −11.447 | 1.00 | 35.86 | O |
| ATOM | 554 | N | GLN | D | 393 | 29.750 | −19.717 | −12.645 | 1.00 | 35.74 | N |
| ATOM | 555 | CA | GLN | D | 393 | 30.371 | −19.151 | −13.841 | 1.00 | 34.38 | C |
| ATOM | 556 | CB | GLN | D | 393 | 31.771 | −19.753 | −14.018 | 1.00 | 35.51 | C |
| ATOM | 557 | CG | GLN | D | 393 | 32.717 | −19.230 | −12.959 | 1.00 | 37.26 | C |
| ATOM | 558 | CD | GLN | D | 393 | 34.109 | −19.856 | −12.981 | 1.00 | 41.66 | C |
| ATOM | 559 | OE1 | GLN | D | 393 | 34.992 | −19.391 | −12.256 | 1.00 | 42.29 | O |
| ATOM | 560 | NE2 | GLN | D | 393 | 34.312 | −20.903 | −13.789 | 1.00 | 35.80 | N |
| ATOM | 561 | C | GLN | D | 393 | 29.522 | −19.408 | −15.077 | 1.00 | 35.24 | C |
| ATOM | 562 | O | GLN | D | 393 | 28.816 | −20.416 | −15.131 | 1.00 | 35.93 | O |
| ATOM | 563 | N | CYS | D | 394 | 29.602 | −18.496 | −16.062 | 1.00 | 34.04 | N |
| ATOM | 564 | CA | CYS | D | 394 | 28.857 | −18.599 | −17.314 | 1.00 | 31.09 | C |
| ATOM | 565 | CB | CYS | D | 394 | 29.263 | −17.465 | −18.264 | 1.00 | 32.23 | C |
| ATOM | 566 | SG | CYS | D | 394 | 28.391 | −17.420 | −19.869 | 1.00 | 39.18 | S |
| ATOM | 567 | C | CYS | D | 394 | 29.189 | −19.922 | −17.959 | 1.00 | 33.67 | C |
| ATOM | 568 | O | CYS | D | 394 | 30.372 | −20.245 | −18.113 | 1.00 | 29.95 | O |
| ATOM | 569 | N | LYS | D | 395 | 28.163 | −20.691 | −18.338 | 1.00 | 34.37 | N |
| ATOM | 570 | CA | LYS | D | 395 | 28.411 | −22.011 | −18.933 | 1.00 | 41.50 | C |
| ATOM | 571 | CB | LYS | D | 395 | 27.182 | −22.952 | −18.839 | 1.00 | 45.54 | C |

TABLE 7-continued

Atomic coordinates for CRBN(TBD): Compound B (Murine protein)

| ATOM | 572 | CG | LYS | D | 395 | 26.122 | −22.791 | −19.905 | 1.00 | 47.12 | C |
|---|---|---|---|---|---|---|---|---|---|---|---|
| ATOM | 573 | CD | LYS | D | 395 | 24.937 | −23.739 | −19.661 | 1.00 | 49.98 | C |
| ATOM | 574 | CE | LYS | D | 395 | 23.863 | −23.555 | −20.749 | 1.00 | 53.69 | C |
| ATOM | 575 | NZ | LYS | D | 395 | 22.586 | −24.319 | −20.540 | 1.00 | 50.24 | N |
| ATOM | 576 | C | LYS | D | 395 | 28.966 | −21.894 | −20.349 | 1.00 | 42.42 | C |
| ATOM | 577 | O | LYS | D | 395 | 29.616 | −22.814 | −20.837 | 1.00 | 44.12 | O |
| ATOM | 578 | N | ILE | D | 396 | 28.764 | −20.735 | −20.974 | 1.00 | 42.06 | N |
| ATOM | 579 | CA | ILE | D | 396 | 29.261 | −20.491 | −22.331 | 1.00 | 42.15 | C |
| ATOM | 580 | CB | ILE | D | 396 | 28.384 | −19.482 | −23.109 | 1.00 | 43.00 | C |
| ATOM | 581 | CG1 | ILE | D | 396 | 26.926 | −19.984 | −23.235 | 1.00 | 41.49 | C |
| ATOM | 582 | CD1 | ILE | D | 396 | 26.759 | −21.455 | −23.591 | 1.00 | 43.33 | C |
| ATOM | 583 | CG2 | ILE | D | 396 | 28.999 | −19.182 | −24.467 | 1.00 | 43.69 | C |
| ATOM | 584 | C | ILE | D | 396 | 30.731 | −20.059 | −22.374 | 1.00 | 42.04 | C |
| ATOM | 585 | O | ILE | D | 396 | 31.530 | −20.640 | −23.119 | 1.00 | 38.64 | O |
| ATOM | 586 | N | CYS | D | 397 | 31.084 | −19.040 | −21.589 | 1.00 | 39.02 | N |
| ATOM | 587 | CA | CYS | D | 397 | 32.433 | −18.471 | −21.642 | 1.00 | 37.29 | C |
| ATOM | 588 | CB | CYS | D | 397 | 32.367 | −16.984 | −22.041 | 1.00 | 38.27 | C |
| ATOM | 589 | SG | CYS | D | 397 | 31.705 | −15.879 | −20.761 | 1.00 | 37.94 | S |
| ATOM | 590 | C | CYS | D | 397 | 33.272 | −18.628 | −20.361 | 1.00 | 38.44 | C |
| ATOM | 591 | O | CYS | D | 397 | 34.394 | −18.116 | −20.304 | 1.00 | 37.89 | O |
| ATOM | 592 | N | ALA | D | 398 | 32.740 | −19.323 | −19.346 | 1.00 | 32.84 | N |
| ATOM | 593 | CA | ALA | D | 398 | 33.430 | −19.503 | −18.036 | 1.00 | 33.52 | C |
| ATOM | 594 | CB | ALA | D | 398 | 34.680 | −20.374 | −18.178 | 1.00 | 30.64 | C |
| ATOM | 595 | C | ALA | D | 398 | 33.778 | −18.191 | −17.294 | 1.00 | 33.76 | C |
| ATOM | 596 | O | ALA | D | 398 | 34.530 | −18.198 | −16.327 | 1.00 | 36.76 | O |
| ATOM | 597 | N | SER | D | 399 | 33.233 | −17.062 | −17.706 | 1.00 | 34.22 | N |
| ATOM | 598 | CA | SER | D | 399 | 33.563 | −15.878 | −16.961 | 1.00 | 38.18 | C |
| ATOM | 599 | CB | SER | D | 399 | 33.417 | −14.599 | −17.809 | 1.00 | 42.95 | C |
| ATOM | 600 | OG | SER | D | 399 | 32.099 | −14.121 | −17.775 | 1.00 | 50.88 | O |
| ATOM | 601 | C | SER | D | 399 | 32.796 | −15.858 | −15.609 | 1.00 | 39.23 | C |
| ATOM | 602 | O | SER | D | 399 | 31.726 | −16.507 | −15.449 | 1.00 | 38.31 | O |
| ATOM | 603 | N | HIS | D | 400 | 33.393 | −15.191 | −14.620 | 1.00 | 36.83 | N |
| ATOM | 604 | CA | HIS | D | 400 | 32.762 | −15.067 | −13.323 | 1.00 | 35.18 | C |
| ATOM | 605 | CB | HIS | D | 400 | 33.591 | −14.214 | −12.413 | 1.00 | 34.42 | C |
| ATOM | 606 | CG | HIS | D | 400 | 32.891 | −13.910 | −11.129 | 1.00 | 33.73 | C |
| ATOM | 607 | ND1 | HIS | D | 400 | 32.704 | −14.838 | −10.188 | 1.00 | 34.26 | N |
| ATOM | 608 | CE1 | HIS | D | 400 | 32.003 | −14.312 | −9.167 | 1.00 | 31.11 | C |
| ATOM | 609 | NE2 | HIS | D | 400 | 31.767 | −13.035 | −9.447 | 1.00 | 33.25 | N |
| ATOM | 610 | CD2 | HIS | D | 400 | 32.276 | −12.755 | −10.673 | 1.00 | 34.61 | C |
| ATOM | 611 | C | HIS | D | 400 | 31.392 | −14.462 | −13.420 | 1.00 | 34.30 | C |
| ATOM | 612 | O | HIS | D | 400 | 31.220 | −13.426 | −14.040 | 1.00 | 31.33 | O |
| ATOM | 613 | N | ILE | D | 401 | 30.403 | −15.095 | −12.796 | 1.00 | 31.58 | N |
| ATOM | 614 | CA | ILE | D | 401 | 29.085 | −14.479 | −12.702 | 1.00 | 31.70 | C |
| ATOM | 615 | CB | ILE | D | 401 | 28.001 | −15.369 | −13.367 | 1.00 | 34.13 | C |
| ATOM | 616 | CG1 | ILE | D | 401 | 28.245 | −15.536 | −14.887 | 1.00 | 31.21 | C |
| ATOM | 617 | CD1 | ILE | D | 401 | 28.050 | −14.243 | −15.677 | 1.00 | 34.84 | C |
| ATOM | 618 | CG2 | ILE | D | 401 | 26.602 | −14.823 | −13.073 | 1.00 | 34.61 | C |
| ATOM | 619 | C | ILE | D | 401 | 28.679 | −14.165 | −11.235 | 1.00 | 31.39 | C |
| ATOM | 620 | O | ILE | D | 401 | 28.111 | −13.103 | −10.950 | 1.00 | 31.52 | O |
| ATOM | 621 | N | GLY | D | 402 | 28.954 | −15.080 | −10.313 | 1.00 | 29.37 | N |
| ATOM | 622 | CA | GLY | D | 402 | 28.449 | −14.910 | −8.945 | 1.00 | 31.30 | C |
| ATOM | 623 | C | GLY | D | 402 | 28.556 | −16.148 | −8.114 | 1.00 | 32.12 | C |
| ATOM | 624 | O | GLY | D | 402 | 29.518 | −16.885 | −8.261 | 1.00 | 34.75 | O |
| ATOM | 625 | N | TRP | D | 403 | 27.600 | −16.340 | −7.198 | 1.00 | 31.94 | N |
| ATOM | 626 | CA | TRP | D | 403 | 27.563 | −17.476 | −6.280 | 1.00 | 31.38 | C |
| ATOM | 627 | CB | TRP | D | 403 | 28.156 | −17.120 | −4.896 | 1.00 | 30.77 | C |
| ATOM | 628 | CG | TRP | D | 403 | 29.554 | −16.505 | −4.998 | 1.00 | 29.59 | C |
| ATOM | 629 | CD1 | TRP | D | 403 | 30.758 | −17.140 | −4.867 | 1.00 | 29.27 | C |
| ATOM | 630 | NE1 | TRP | D | 403 | 31.818 | −16.247 | −5.068 | 1.00 | 26.94 | N |
| ATOM | 631 | CE2 | TRP | D | 403 | 31.336 | −15.008 | −5.356 | 1.00 | 30.23 | C |
| ATOM | 632 | CD2 | TRP | D | 403 | 29.883 | −15.097 | −5.318 | 1.00 | 28.99 | C |
| ATOM | 633 | CE3 | TRP | D | 403 | 29.132 | −13.950 | −5.564 | 1.00 | 30.63 | C |
| ATOM | 634 | CZ3 | TRP | D | 403 | 29.812 | −12.731 | −5.856 | 1.00 | 30.71 | C |
| ATOM | 635 | CH2 | TRP | D | 403 | 31.209 | −12.666 | −5.882 | 1.00 | 28.58 | C |
| ATOM | 636 | CZ2 | TRP | D | 403 | 32.002 | −13.800 | −5.636 | 1.00 | 32.44 | C |
| ATOM | 637 | C | TRP | D | 403 | 26.143 | −17.955 | −6.098 | 1.00 | 36.21 | C |
| ATOM | 638 | O | TRP | D | 403 | 25.220 | −17.147 | −6.071 | 1.00 | 39.69 | O |
| ATOM | 639 | N | LYS | D | 404 | 25.965 | −19.269 | −5.948 | 1.00 | 32.03 | N |
| ATOM | 640 | CA | LYS | D | 404 | 24.699 | −19.832 | −5.492 | 1.00 | 32.64 | C |
| ATOM | 641 | CB | LYS | D | 404 | 24.404 | −21.136 | −6.212 | 1.00 | 34.16 | C |
| ATOM | 642 | CG | LYS | D | 404 | 23.037 | −21.734 | −5.920 | 1.00 | 34.90 | C |
| ATOM | 643 | CD | LYS | D | 404 | 22.876 | −23.068 | −6.624 | 1.00 | 33.57 | C |
| ATOM | 644 | CE | LYS | D | 404 | 21.507 | −23.678 | −6.343 | 1.00 | 38.06 | C |
| ATOM | 645 | NZ | LYS | D | 404 | 21.367 | −24.924 | −7.135 | 1.00 | 36.03 | N |
| ATOM | 646 | C | LYS | D | 404 | 24.812 | −20.100 | −4.014 | 1.00 | 32.19 | C |
| ATOM | 647 | O | LYS | D | 404 | 25.830 | −20.654 | −3.543 | 1.00 | 31.34 | O |
| ATOM | 648 | N | PHE | D | 405 | 23.760 | −19.693 | −3.304 | 1.00 | 29.65 | N |
| ATOM | 649 | CA | PHE | D | 405 | 23.622 | −19.876 | −1.879 | 1.00 | 30.63 | C |

TABLE 7-continued

Atomic coordinates for CRBN(TBD): Compound B (Murine protein)

| ATOM | 650 | CB | PHE | D | 405 | 23.218 | −18.562 | −1.232 | 1.00 | 31.42 | C |
|---|---|---|---|---|---|---|---|---|---|---|---|
| ATOM | 651 | CG | PHE | D | 405 | 24.288 | −17.527 | −1.286 | 1.00 | 31.75 | C |
| ATOM | 652 | CD1 | PHE | D | 405 | 25.274 | −17.487 | −0.307 | 1.00 | 35.92 | C |
| ATOM | 653 | CE1 | PHE | D | 405 | 26.311 | −16.539 | −0.370 | 1.00 | 32.85 | C |
| ATOM | 654 | CZ | PHE | D | 405 | 26.370 | −15.663 | −1.445 | 1.00 | 33.62 | C |
| ATOM | 655 | CE2 | PHE | D | 405 | 25.400 | −15.706 | −2.437 | 1.00 | 32.72 | C |
| ATOM | 656 | CD2 | PHE | D | 405 | 24.365 | −16.641 | −2.358 | 1.00 | 32.11 | C |
| ATOM | 657 | C | PHE | D | 405 | 22.566 | −20.932 | −1.590 | 1.00 | 33.31 | C |
| ATOM | 658 | O | PHE | D | 405 | 21.451 | −20.855 | −2.111 | 1.00 | 36.54 | O |
| ATOM | 659 | N | THR | D | 406 | 22.926 | −21.902 | −0.760 | 1.00 | 33.36 | N |
| ATOM | 660 | CA | THR | D | 406 | 22.062 | −23.021 | −0.436 | 1.00 | 38.06 | C |
| ATOM | 661 | CB | THR | D | 406 | 22.601 | −24.342 | −1.053 | 1.00 | 38.53 | C |
| ATOM | 662 | OG1 | THR | D | 406 | 23.974 | −24.507 | −0.704 | 1.00 | 35.56 | O |
| ATOM | 663 | CG2 | THR | D | 406 | 22.501 | −24.312 | −2.588 | 1.00 | 37.55 | C |
| ATOM | 664 | C | THR | D | 406 | 21.935 | −23.134 | 1.091 | 1.00 | 40.79 | C |
| ATOM | 665 | O | THR | D | 406 | 22.954 | −23.092 | 1.812 | 1.00 | 37.09 | O |
| ATOM | 666 | N | ALA | D | 407 | 20.691 | −23.263 | 1.585 | 1.00 | 40.64 | N |
| ATOM | 667 | CA | ALA | D | 407 | 20.417 | −23.362 | 3.038 | 1.00 | 41.09 | C |
| ATOM | 668 | CB | ALA | D | 407 | 18.912 | −23.505 | 3.283 | 1.00 | 45.14 | C |
| ATOM | 669 | C | ALA | D | 407 | 21.180 | −24.530 | 3.653 | 1.00 | 37.86 | C |
| ATOM | 670 | O | ALA | D | 407 | 21.373 | −25.540 | 2.995 | 1.00 | 43.09 | O |
| ATOM | 671 | N | THR | D | 408 | 21.657 | −24.385 | 4.888 | 1.00 | 40.60 | N |
| ATOM | 672 | CA | THR | D | 408 | 22.302 | −25.517 | 5.596 | 1.00 | 42.26 | C |
| ATOM | 673 | CB | THR | D | 408 | 23.536 | −25.097 | 6.437 | 1.00 | 44.72 | C |
| ATOM | 674 | OG1 | THR | D | 408 | 23.170 | −24.066 | 7.366 | 1.00 | 46.70 | O |
| ATOM | 675 | CG2 | THR | D | 408 | 24.660 | −24.580 | 5.539 | 1.00 | 40.92 | C |
| ATOM | 676 | C | THR | D | 408 | 21.309 | −26.316 | 6.462 | 1.00 | 46.74 | C |
| ATOM | 677 | O | THR | D | 408 | 21.604 | −27.452 | 6.836 | 1.00 | 49.03 | O |
| ATOM | 678 | N | LYS | D | 409 | 20.136 | −25.726 | 6.746 | 1.00 | 47.36 | N |
| ATOM | 679 | CA | LYS | D | 409 | 19.074 | −26.346 | 7.577 | 1.00 | 48.62 | C |
| ATOM | 680 | CB | LYS | D | 409 | 18.809 | −25.522 | 8.824 | 1.00 | 45.69 | C |
| ATOM | 681 | CG | LYS | D | 409 | 19.944 | −25.541 | 9.835 | 1.00 | 51.26 | C |
| ATOM | 682 | CD | LYS | D | 409 | 19.983 | −24.258 | 10.648 | 1.00 | 53.2.4 | C |
| ATOM | 683 | CE | LYS | D | 409 | 18.628 | −23.967 | 11.290 | 1.00 | 61.47 | C |
| ATOM | 684 | NZ | LYS | D | 409 | 18.340 | −22.508 | 11.425 | 1.00 | 63.72 | N |
| ATOM | 685 | C | LYS | D | 409 | 17.764 | −26.517 | 6.795 | 1.00 | 51.47 | C |
| ATOM | 686 | O | LYS | D | 409 | 17.393 | −25.659 | 5.970 | 1.00 | 49.06 | O |
| ATOM | 687 | N | LYS | D | 410 | 17.060 | −27.615 | 7.065 | 1.00 | 53.93 | N |
| ATOM | 688 | CA | LYS | D | 410 | 15.940 | −28.027 | 6.209 | 1.00 | 58.44 | C |
| ATOM | 689 | CB | LYS | D | 410 | 15.453 | −29.488 | 6.497 | 1.00 | 64.54 | C |
| ATOM | 690 | CG | LYS | D | 410 | 15.784 | −30.075 | 7.887 | 1.00 | 65.93 | C |
| ATOM | 691 | CD | LYS | D | 410 | 16.639 | −31.354 | 7.834 | 1.00 | 65.85 | C |
| ATOM | 692 | CE | LYS | D | 410 | 18.146 | −31.054 | 8.138 | 1.00 | 65.05 | C |
| ATOM | 693 | NZ | LYS | D | 410 | 18.359 | −30.001 | 9.191 | 1.00 | 60.95 | N |
| ATOM | 694 | C | LYS | D | 410 | 14.785 | −27.011 | 6.212 | 1.00 | 56.91 | C |
| ATOM | 695 | O | LYS | D | 410 | 13.947 | −27.013 | 5.313 | 1.00 | 57.57 | O |
| ATOM | 696 | N | ASP | D | 411 | 14.783 | −26.111 | 7.186 | 1.00 | 59.08 | N |
| ATOM | 697 | CA | ASP | D | 411 | 13.618 | −25.258 | 7.430 | 1.00 | 65.72 | C |
| ATOM | 698 | CB | ASP | D | 411 | 13.082 | −25.535 | 8.833 | 1.00 | 73.37 | C |
| ATOM | 699 | CG | ASP | D | 411 | 14.147 | −25.367 | 9.897 | 1.00 | 81.80 | C |
| ATOM | 700 | OD1 | ASP | D | 411 | 15.291 | −25.851 | 9.685 | 1.00 | 88.21 | O |
| ATOM | 701 | OD2 | ASP | D | 411 | 13.846 | −24.740 | 10.937 | 1.00 | 80.86 | O |
| ATOM | 702 | C | ASP | D | 411 | 13.850 | −23.743 | 7.248 | 1.00 | 64.74 | C |
| ATOM | 703 | O | ASP | D | 411 | 13.125 | −22.921 | 7.827 | 1.00 | 63.98 | O |
| ATOM | 704 | N | MET | D | 412 | 14.845 | −23.374 | 6.449 | 1.00 | 55.03 | N |
| ATOM | 705 | CA | MET | D | 412 | 15.019 | −21.981 | 6.059 | 1.00 | 52.58 | C |
| ATOM | 706 | CB | MET | D | 412 | 16.493 | −21.687 | 5.786 | 1.00 | 47.34 | C |
| ATOM | 707 | CG | MET | D | 412 | 17.346 | −21.684 | 7.039 | 1.00 | 53.29 | C |
| ATOM | 708 | SD | MET | D | 412 | 19.096 | −21.889 | 6.646 | 1.00 | 53.58 | S |
| ATOM | 709 | CE | MET | D | 412 | 19.824 | −22.015 | 8.279 | 1.00 | 54.84 | C |
| ATOM | 710 | C | MET | D | 412 | 14.212 | −21.743 | 4.807 | 1.00 | 46.92 | C |
| ATOM | 711 | O | MET | D | 412 | 14.058 | −22.640 | 3.996 | 1.00 | 48.77 | 0 |
| ATOM | 712 | N | SER | D | 413 | 13.685 | −20.544 | 4.644 | 1.00 | 48.92 | N |
| ATOM | 713 | CA | SER | D | 413 | 13.066 | −20.189 | 3.369 | 1.00 | 53.36 | C |
| ATOM | 714 | CB | SER | D | 413 | 11.565 | −19.872 | 3.502 | 1.00 | 52.93 | C |
| ATOM | 715 | OG | SER | D | 413 | 11.341 | −18.485 | 3.667 | 1.00 | 60.47 | 0 |
| ATOM | 716 | C | SER | D | 413 | 13.900 | −19.048 | 2.788 | 1.00 | 56.70 | C |
| ATOM | 717 | O | SER | D | 413 | 14.492 | −18.287 | 3.556 | 1.00 | 60.21 | 0 |
| ATOM | 718 | N | PRO | D | 414 | 13.797 | −18.821 | 1.459 | 1.00 | 56.00 | N |
| ATOM | 719 | CA | PRO | D | 414 | 14.803 | −19.185 | 0.495 | 1.00 | 49.97 | C |
| ATOM | 720 | CB | PRO | D | 414 | 15.658 | −17.905 | 0.397 | 1.00 | 52.55 | C |
| ATOM | 721 | CG | PRO | D | 414 | 14.699 | −16.793 | 0.729 | 1.00 | 52.15 | C |
| ATOM | 722 | CD | PRO | D | 414 | 13.390 | −17.432 | 1.186 | 1.00 | 58.26 | C |
| ATOM | 723 | C | PRO | D | 414 | 15.585 | −20.440 | 0.924 | 1.00 | 47.31 | C |
| ATOM | 724 | O | PRO | D | 414 | 16.342 | −20.389 | 1.886 | 1.00 | 53.96 | 0 |
| ATOM | 725 | N | GLN | D | 415 | 15.336 | −21.575 | 0.267 | 1.00 | 44.49 | N |
| ATOM | 726 | CA | GLN | D | 415 | 16.218 | −22.720 | 0.396 | 1.00 | 44.36 | C |
| ATOM | 727 | CB | GLN | D | 415 | 15.508 | −24.040 | 0.075 | 1.00 | 46.40 | C |

TABLE 7-continued

Atomic coordinates for CRBN(TBD): Compound B (Murine protein)

| ATOM | 728 | CG | GLN | D | 415 | 14.827 | −24.681 | 1.295 | 1.00 | 50.25 | C |
|---|---|---|---|---|---|---|---|---|---|---|---|
| ATOM | 729 | CD | GLN | D | 415 | 15.794 | −25.347 | 2.298 | 1.00 | 49.90 | C |
| ATOM | 730 | OE1 | GLN | D | 415 | 15.825 | −24.993 | 3.493 | 1.00 | 45.63 | O |
| ATOM | 731 | NE2 | GLN | D | 415 | 16.560 | −26.341 | 1.822 | 1.00 | 47.81 | N |
| ATOM | 732 | C | GLN | D | 415 | 17.435 | −22.527 | −0.501 | 1.00 | 43.40 | C |
| ATOM | 733 | O | GLN | D | 415 | 18.494 | −23.077 | −0.246 | 1.00 | 43.07 | O |
| ATOM | 734 | N | LYS | D | 416 | 17.268 | −21.758 | −1.566 | 1.00 | 45.58 | N |
| ATOM | 735 | CA | LYS | D | 416 | 18.397 | −21.281 | −2.356 | 1.00 | 45.59 | C |
| ATOM | 736 | CB | LYS | D | 416 | 18.837 | −22.293 | −3.436 | 1.00 | 49.29 | C |
| ATOM | 737 | CG | LYS | D | 416 | 17.801 | −22.692 | −4.471 | 1.00 | 52.09 | C |
| ATOM | 738 | CD | LYS | D | 416 | 17.878 | −24.199 | −4.679 | 1.00 | 61.35 | C |
| ATOM | 739 | CE | LYS | D | 416 | 17.847 | −24.606 | −6.150 | 1.00 | 68.77 | C |
| ATOM | 740 | NZ | LYS | D | 416 | 16.579 | −24.219 | −6.834 | 1.00 | 73.29 | N |
| ATOM | 741 | C | LYS | D | 416 | 18.074 | −19.938 | −2.963 | 1.00 | 44.98 | C |
| ATOM | 742 | O | LYS | D | 416 | 16.912 | −19.546 | −3.040 | 1.00 | 40.71 | O |
| ATOM | 743 | N | PHE | D | 417 | 19.127 | −19.233 | −3.352 | 1.00 | 40.53 | N |
| ATOM | 744 | CA | PHE | D | 417 | 19.041 | −17.970 | −4.067 | 1.00 | 38.14 | C |
| ATOM | 745 | CB | PHE | D | 417 | 18.583 | −16.823 | −3.146 | 1.00 | 36.09 | C |
| ATOM | 746 | CG | PHE | D | 417 | 19.581 | −16.433 | −2.078 | 1.00 | 34.05 | C |
| ATOM | 747 | CD1 | PHE | D | 417 | 20.497 | −15.407 | −2.296 | 1.00 | 32.39 | C |
| ATOM | 748 | CE1 | PHE | D | 417 | 21.386 | −15.040 | −1.312 | 1.00 | 29.72 | C |
| ATOM | 749 | CZ | PHE | D | 417 | 21.354 | −15.673 | −0.085 | 1.00 | 30.91 | C |
| ATOM | 750 | CE2 | PHE | D | 417 | 20.441 | −16.688 | 0.154 | 1.00 | 32.01 | C |
| ATOM | 751 | CD2 | PHE | D | 417 | 19.552 | −17.045 | −0.831 | 1.00 | 32.25 | C |
| ATOM | 752 | C | PHE | D | 417 | 20.426 | −17.676 | −4.634 | 1.00 | 36.13 | C |
| ATOM | 753 | O | PHE | D | 417 | 21.382 | −18.394 | −4.322 | 1.00 | 38.34 | O |
| ATOM | 754 | N | TRP | D | 418 | 20.547 | −16.623 | −5.449 | 1.00 | 34.85 | N |
| ATOM | 755 | CA | TRP | D | 418 | 21.834 | −16.301 | −6.086 | 1.00 | 34.57 | C |
| ATOM | 756 | CB | TRP | D | 418 | 21.774 | −16.533 | −7.590 | 1.00 | 35.19 | C |
| ATOM | 757 | CG | TRP | D | 418 | 21.245 | −17.888 | −8.005 | 1.00 | 42.13 | C |
| ATOM | 758 | CD1 | TRP | D | 418 | 19.926 | −18.363 | −7.906 | 1.00 | 44.36 | C |
| ATOM | 759 | NE1 | TRP | D | 418 | 19.826 | −19.627 | −8.414 | 1.00 | 48.62 | N |
| ATOM | 760 | CE2 | TRP | D | 418 | 21.034 | −20.45 | −8.876 | 1.00 | 46.98 | C |
| ATOM | 761 | CD2 | TRP | D | 418 | 21.990 | −18.960 | −8.643 | 1.00 | 44.41 | C |
| ATOM | 762 | CE3 | TRP | D | 418 | 23.307 | −19.126 | −9.036 | 1.00 | 47.59 | C |
| ATOM | 763 | CZ3 | TRP | D | 418 | 23.679 | −20.342 | −9.637 | 1.00 | 50.85 | C |
| ATOM | 764 | CH2 | TRP | D | 418 | 22.753 | −21.369 | −9.850 | 1.00 | 48.68 | C |
| ATOM | 765 | CZ2 | TRP | D | 418 | 21.410 | −21.240 | −9.465 | 1.00 | 49.90 | C |
| ATOM | 766 | C | TRP | D | 418 | 22.271 | −14.900 | −5.817 | 1.00 | 35.46 | C |
| ATOM | 767 | O | TRP | D | 418 | 21.443 | −13.975 | −5.710 | 1.00 | 30.00 | O |
| ATOM | 768 | N | GLY | D | 419 | 23.582 | −14.734 | −5.683 | 1.00 | 33.82 | N |
| ATOM | 769 | CA | GLY | D | 419 | 24.192 | −13.419 | −5.663 | 1.00 | 33.01 | C |
| ATOM | 770 | C | GLY | D | 419 | 24.971 | −13.284 | −6.963 | 1.00 | 36.02 | C |
| ATOM | 771 | O | GLY | D | 419 | 25.888 | −14.092 | −7.241 | 1.00 | 35.80 | O |
| ATOM | 772 | N | LEU | D | 420 | 24.592 | −12.290 | −7.765 | 1.00 | 36.03 | N |
| ATOM | 773 | CA | LEU | D | 420 | 25.197 | −12.041 | −9.054 | 1.00 | 34.91 | C |
| ATOM | 774 | CB | LEU | D | 420 | 24.132 | −11.980 | −10.127 | 1.00 | 35.27 | C |
| ATOM | 775 | CG | LEU | D | 420 | 23.136 | −13.140 | −10.175 | 1.00 | 38.07 | C |
| ATOM | 776 | CD1 | LEU | D | 420 | 22.183 | −12.964 | −11.347 | 1.00 | 38.18 | C |
| ATOM | 777 | CD2 | LEU | D | 420 | 23.871 | −14.465 | −10.279 | 1.00 | 39.20 | C |
| ATOM | 778 | C | LEU | D | 420 | 25.973 | −10.741 | −9.037 | 1.00 | 34.88 | C |
| ATOM | 779 | O | LEU | D | 420 | 25.449 | −9.728 | −8.633 | 1.00 | 33.14 | O |
| ATOM | 780 | N | THR | D | 421 | 27.223 | −10.789 | −9.500 | 1.00 | 33.61 | N |
| ATOM | 781 | CA | THR | D | 421 | 28.070 | −9.614 | −9.646 | 1.00 | 33.48 | C |
| ATOM | 782 | CB | THR | D | 421 | 29.501 | −10.031 | −10.021 | 1.00 | 35.48 | C |
| ATOM | 783 | OG1 | THR | D | 421 | 30.020 | −10.861 | −8.988 | 1.00 | 35.63 | O |
| ATOM | 784 | CG2 | THR | D | 421 | 30.429 | −8.792 | −10.220 | 1.00 | 31.94 | C |
| ATOM | 785 | C | THR | D | 421 | 27.541 | −8.673 | −10.745 | 1.00 | 34.91 | C |
| ATOM | 786 | O | THR | D | 421 | 27.532 | −9.028 | −11.912 | 1.00 | 32.45 | O |
| ATOM | 787 | N | ARG | D | 422 | 27.150 | −7.462 | −10.356 | 1.00 | 32.57 | N |
| ATOM | 788 | CA | ARG | D | 422 | 26.544 | −6.500 | −11.265 | 1.00 | 35.67 | C |
| ATOM | 789 | CB | ARG | D | 422 | 26.186 | −5.188 | −10.545 | 1.00 | 32.53 | C |
| ATOM | 790 | CG | ARG | D | 422 | 24.976 | −5.395 | −9.664 | 1.00 | 34.37 | C |
| ATOM | 791 | CD | ARG | D | 422 | 24.599 | −4.133 | −8.920 | 1.00 | 39.73 | C |
| ATOM | 792 | NE | ARG | D | 422 | 23.741 | −3.255 | −9.707 | 1.00 | 41.31 | N |
| ATOM | 793 | CZ | ARG | D | 422 | 23.105 | −2.214 | −9.186 | 1.00 | 45.47 | C |
| ATOM | 794 | NH1 | ARG | D | 422 | 22.344 | −1.437 | −9.941 | 1.00 | 52.28 | N |
| ATOM | 795 | NH2 | ARG | D | 422 | 23.231 | −1.955 | −7.894 | 1.00 | 44.48 | N |
| ATOM | 796 | C | ARG | D | 422 | 27.377 | −6.217 | −12.480 | 1.00 | 37.00 | C |
| ATOM | 797 | O | ARG | D | 422 | 26.841 | −6.177 | −13.599 | 1.00 | 35.54 | O |
| ATOM | 798 | N | SER | D | 423 | 28.673 | −6.010 | −12.276 | 1.00 | 35.16 | N |
| ATOM | 799 | CA | SER | D | 423 | 29.548 | −5.649 | −13.384 | 1.00 | 37.50 | C |
| ATOM | 800 | CB | SER | D | 423 | 30.908 | −5.159 | −12.869 | 1.00 | 37.61 | C |
| ATOM | 801 | OG | SER | D | 423 | 31.581 | −6.218 | −12.213 | 1.00 | 40.96 | O |
| ATOM | 802 | C | SER | D | 423 | 29.743 | −6.811 | −14.366 | 1.00 | 36.57 | C |
| ATOM | 803 | O | SER | D | 423 | 30.273 | −6.603 | −15.457 | 1.00 | 37.90 | O |
| ATOM | 804 | N | ALA | D | 424 | 29.285 | −8.010 | −13.992 | 1.00 | 35.52 | N |
| ATOM | 805 | CA | ALA | D | 424 | 29.423 | −9.214 | −14.839 | 1.00 | 39.23 | C |

TABLE 7-continued

Atomic coordinates for CRBN(TBD): Compound B (Murine protein)

| ATOM | 806 | CB | ALA | D | 424 | 29.606 | −10.459 | −13.971 | 1.00 | 34.36 | C |
|---|---|---|---|---|---|---|---|---|---|---|---|
| ATOM | 807 | C | ALA | D | 424 | 28.236 | −9.415 | −15.785 | 1.00 | 40.37 | C |
| ATOM | 808 | O | ALA | D | 424 | 28.254 | −10.297 | −16.646 | 1.00 | 40.75 | O |
| ATOM | 809 | N | LEU | D | 425 | 27.203 | −8.605 | −15.608 | 1.00 | 40.47 | N |
| ATOM | 810 | CA | LEU | D | 425 | 25.929 | −8.783 | −16.310 | 1.00 | 42.94 | C |
| ATOM | 811 | CB | LEU | D | 425 | 24.818 | −8.943 | −15.278 | 1.00 | 40.50 | C |
| ATOM | 812 | CG | LEU | D | 425 | 24.869 | −10.120 | −14.338 | 1.00 | 37.11 | C |
| ATOM | 813 | CD1 | LEU | D | 425 | 23.696 | −10.009 | −13.385 | 1.00 | 41.00 | C |
| ATOM | 814 | CD2 | LEU | D | 425 | 24.796 | −11.419 | −15.117 | 1.00 | 40.09 | C |
| ATOM | 815 | C | LEU | D | 425 | 25.603 | −7.574 | −17.187 | 1.00 | 45.36 | C |
| ATOM | 816 | O | LEU | D | 425 | 25.896 | −6.444 | −16.799 | 1.00 | 48.02 | O |
| ATOM | 817 | N | LEU | D | 426 | 24.983 | −7.797 | −18.353 | 1.00 | 48.44 | N |
| ATOM | 818 | CA | LEU | D | 426 | 24.461 | −6.669 | −19.159 | 1.00 | 49.08 | C |
| ATOM | 819 | CB | LEU | D | 426 | 24.909 | −6.721 | −20.623 | 1.00 | 47.43 | C |
| ATOM | 820 | CG | LEU | D | 426 | 26.233 | −5.972 | −20.861 | 1.00 | 47.17 | C |
| ATOM | 821 | CD1 | LEU | D | 426 | 26.625 | −5.950 | −22.337 | 1.00 | 43.13 | C |
| ATOM | 822 | CD2 | LEU | D | 426 | 26.189 | −4.555 | −20.304 | 1.00 | 45.78 | C |
| ATOM | 823 | C | LEU | D | 426 | 22.956 | −6.470 | −18.997 | 1.00 | 55.73 | C |
| ATOM | 824 | O | LEU | D | 426 | 22.272 | −7.377 | −18.544 | 1.00 | 60.24 | O |
| ATOM | 825 | N | PRO | D | 427 | 22.420 | −5.365 | −19.550 | 1.00 | 59.65 | N |
| ATOM | 826 | CA | PRO | D | 427 | 21.879 | −4.240 | −18.826 | 1.00 | 54.11 | C |
| ATOM | 827 | CB | PRO | D | 427 | 20.416 | −4.640 | −18.617 | 1.00 | 58.08 | C |
| ATOM | 828 | CG | PRO | D | 427 | 20.119 | −5.550 | −19.797 | 1.00 | 59.27 | C |
| ATOM | 829 | CD | PRO | D | 427 | 21.423 | −5.779 | −20.550 | 1.00 | 61.29 | C |
| ATOM | 830 | C | PRO | D | 427 | 22.635 | −3.929 | −17.524 | 1.00 | 54.24 | C |
| ATOM | 831 | O | PRO | D | 427 | 22.547 | −4.670 | −16.543 | 1.00 | 49.51 | O |
| ATOM | 832 | N | THR | D | 428 | 23.438 | −2.866 | −17.559 | 1.00 | 56.51 | N |
| ATOM | 833 | CA | THR | D | 428 | 23.823 | −2.148 | −16.345 | 1.00 | 59.23 | C |
| ATOM | 834 | CB | THR | D | 428 | 24.746 | −0.977 | −16.688 | 1.00 | 60.62 | C |
| ATOM | 835 | OG1 | THR | D | 428 | 26.050 | −1.479 | −16.979 | 1.00 | 57.71 | O |
| ATOM | 836 | CG2 | THR | D | 428 | 24.809 | 0.056 | −15.529 | 1.00 | 56.02 | C |
| ATOM | 837 | C | THR | D | 428 | 22.569 | −1.555 | −15.695 | 1.00 | 61.51 | C |
| ATOM | 838 | O | THR | D | 428 | 21.866 | −0.773 | −16.330 | 1.00 | 64.20 | O |
| ATOM | 839 | N | ILE | D | 429 | 22.293 | −1.925 | −14.446 | 1.00 | 60.26 | N |
| ATOM | 840 | CA | ILE | D | 429 | 21.167 | −1.351 | −13.698 | 1.00 | 60.74 | C |
| ATOM | 841 | CB | ILE | D | 429 | 20.656 | −2.333 | −12.611 | 1.00 | 58.14 | C |
| ATOM | 842 | CG1 | ILE | D | 429 | 19.943 | −3.507 | −13.301 | 1.00 | 56.28 | C |
| ATOM | 843 | CD1 | ILE | D | 429 | 19.804 | −4.765 | −12.474 | 1.00 | 49.01 | C |
| ATOM | 844 | CG2 | ILE | D | 429 | 19.715 | −1.634 | −11.630 | 1.00 | 57.91 | C |
| ATOM | 845 | C | ILE | D | 429 | 21.527 | 0.051 | −13.147 | 1.00 | 66.55 | C |
| ATOM | 846 | O | ILE | D | 429 | 22.592 | 0.224 | −12.553 | 1.00 | 64.35 | O |
| ATOM | 847 | N | PRO | D | 430 | 20.655 | 1.067 | −13.385 | 1.00 | 69.25 | N |
| ATOM | 848 | CA | PRO | D | 430 | 20.988 | 2.438 | −12.986 | 1.00 | 71.23 | C |
| ATOM | 849 | CB | PRO | D | 430 | 20.248 | 3.294 | −14.025 | 1.00 | 69.05 | C |
| ATOM | 850 | CG | PRO | D | 430 | 19.161 | 2.414 | −14.583 | 1.00 | 69.00 | C |
| ATOM | 851 | CD | PRO | D | 430 | 19.339 | 1.012 | −14.051 | 1.00 | 68.13 | C |
| ATOM | 852 | C | PRO | D | 430 | 20.489 | 2.769 | −11.586 | 1.00 | 74.22 | C |
| ATOM | 853 | O | PRO | D | 430 | 21.271 | 2.765 | −10.639 | 1.00 | 79.89 | O |
| ATOM | 854 | ZN | ZN | A | 1 | 29.497 | −15.700 | −20.832 | 1.00 | 47.26 | ZN |
| ATOM | 855 | ZN | ZN | A | 2 | 24.275 | 0.066 | −0.106 | 1.00 | 42.90 | ZN |
| ATOM | 856 | ZN | ZN | A | 3 | 36.150 | −15.869 | −6.982 | 1.00 | 41.44 | ZN |
| ATOM | 857 | C20 | MOL | E | 1 | 35.312 | −25.069 | −2.357 | 1.00 | 69.98 | C |
| ATOM | 858 | C21 | MOL | E | 1 | 34.783 | −26.389 | −1.776 | 1.00 | 73.54 | C |
| ATOM | 859 | O5 | MOL | E | 1 | 34.913 | −27.449 | −2.740 | 1.00 | 67.11 | O |
| ATOM | 860 | C22 | MOL | E | 1 | 36.311 | −27.662 | −2.954 | 1.00 | 72.97 | C |
| ATOM | 861 | C23 | MOL | E | 1 | 36.924 | −26.420 | −3.618 | 1.00 | 70.46 | C |
| ATOM | 862 | N3 | MOL | E | 1 | 36.713 | −25.195 | −2.812 | 1.00 | 67.80 | N |
| ATOM | 863 | C19 | MOL | E | 1 | 36.946 | −24.107 | −3.762 | 1.00 | 57.15 | C |
| ATOM | 864 | C18 | MOL | E | 1 | 37.379 | −22.768 | −3.139 | 1.00 | 50.27 | C |
| ATOM | 865 | C24 | MOL | E | 1 | 38.406 | −22.665 | −2.199 | 1.00 | 43.80 | C |
| ATOM | 866 | C25 | MOL | E | 1 | 38.773 | −21.408 | −1.702 | 1.00 | 43.53 | C |
| ATOM | 867 | C17 | MOL | E | 1 | 36.744 | −21.619 | −3.592 | 1.00 | 46.35 | C |
| ATOM | 868 | C16 | MOL | E | 1 | 37.108 | −20.374 | −3.101 | 1.00 | 45.03 | C |
| ATOM | 869 | C15 | MOL | E | 1 | 38.126 | −20.260 | −2.163 | 1.00 | 39.75 | C |
| ATOM | 870 | C14 | MOL | E | 1 | 38.438 | −18.981 | −1.709 | 1.00 | 38.24 | C |
| ATOM | 871 | O4 | MOL | E | 1 | 37.335 | −18.072 | −1.694 | 1.00 | 40.16 | O |
| ATOM | 872 | C3 | MOL | E | 1 | 37.533 | −16.727 | −1.732 | 1.00 | 38.85 | C |
| ATOM | 873 | C2 | MOL | E | 1 | 38.780 | −16.122 | −1.874 | 1.00 | 39.41 | C |
| ATOM | 874 | C1 | MOL | E | 1 | 38.862 | −14.727 | −1.898 | 1.00 | 34.38 | C |
| ATOM | 875 | C7 | MOL | E | 1 | 37.709 | −13.937 | −1.777 | 1.00 | 39.90 | C |
| ATOM | 876 | C6 | MOL | E | 1 | 36.460 | −14.550 | −1.652 | 1.00 | 39.47 | C |
| ATOM | 877 | C8 | MOL | E | 1 | 35.150 | −14.077 | −1.475 | 1.00 | 41.09 | C |
| ATOM | 878 | O1 | MOL | E | 1 | 34.839 | −12.888 | −1.348 | 1.00 | 39.84 | O |
| ATOM | 879 | C4 | MOL | E | 1 | 36.407 | −15.934 | −1.618 | 1.00 | 38.12 | C |
| ATOM | 880 | C5 | MOL | E | 1 | 34.969 | −16.373 | −1.448 | 1.00 | 38.27 | C |
| ATOM | 881 | N1 | MOL | E | 1 | 34.288 | −15.085 | −1.307 | 1.00 | 40.64 | N |
| ATOM | 882 | C9 | MOL | E | 1 | 32.864 | −14.914 | −0.964 | 1.00 | 38.72 | C |
| ATOM | 883 | C13 | MOL | E | 1 | 31.932 | −15.946 | −1.616 | 1.00 | 36.16 | C |

TABLE 7-continued

Atomic coordinates for CRBN(TBD): Compound B (Murine protein)

| ATOM | 884 | C12 | MOL | E | 1 | 30.485 | −15.586 | −1.237 | 1.00 | 36.41 | C |
|------|-----|-----|-----|---|---|--------|---------|--------|------|-------|---|
| ATOM | 885 | C11 | MOL | E | 1 | 30.336 | −15.577 | 0.299 | 1.00 | 39.73 | C |
| ATOM | 886 | O2 | MOL | E | 1 | 29.256 | −15.858 | 0.824 | 1.00 | 42.02 | O |
| ATOM | 887 | N2 | MOL | E | 1 | 31.447 | −15.316 | 1.116 | 1.00 | 35.12 | N |
| ATOM | 888 | C10 | MOL | E | 1 | 32.695 | −14.981 | 0.560 | 1.00 | 40.61 | C |
| ATOM | 889 | O3 | MOL | E | 1 | 33.643 | −14.726 | 1.309 | 1.00 | 35.82 | O |
| ATOM | 890 | O | HOH | C | 1 | 32.948 | −22.507 | −16.031 | 1.00 | 66.61 | O |
| ATOM | 891 | O | HOH | C | 2 | 30.369 | −11.514 | −17.508 | 1.00 | 36.77 | O |
| ATOM | 892 | O | HOH | C | 3 | 24.026 | −5.425 | −14.082 | 1.00 | 47.87 | O |
| ATOM | 893 | O | HOH | C | 4 | 31.867 | −3.597 | −1.435 | 1.00 | 41.94 | O |
| ATOM | 894 | O | HOH | C | 5 | 32.172 | −23.320 | −2.350 | 1.00 | 40.01 | O |
| ATOM | 895 | O | HOH | C | 6 | 29.775 | −5.487 | −9.681 | 1.00 | 44.79 | O |
| ATOM | 896 | O | HOH | C | 7 | 32.901 | −22.606 | −4.847 | 1.00 | 34.25 | O |
| ATOM | 897 | O | HOH | C | 8 | 34.512 | −16.875 | −10.391 | 1.00 | 38.11 | O |
| ATOM | 898 | O | HOH | C | 9 | 35.680 | −11.173 | −11.710 | 1.00 | 44.70 | O |
| ATOM | 899 | O | HOH | C | 10 | 37.220 | −13.035 | −12.607 | 1.00 | 58.31 | O |
| ATOM | 900 | O | HOH | C | 11 | 33.259 | −14.936 | 8.906 | 1.00 | 68.37 | O |
| ATOM | 901 | O | HOH | C | 12 | 33.552 | −18.239 | 8.752 | 1.00 | 52.97 | O |
| ATOM | 902 | O | HOH | C | 13 | 33.576 | −12.668 | 3.223 | 1.00 | 43.35 | O |
| END | | | | | | | | | | | |

TABLE 8

Atomic coordinates for unbound CRBN-CRBN (TBD) (Apo) (Murine protein)

```
HEADER                                                              XX-XXX-9-    xxxx
COMPND
REMARK 3
REMARK 3    REFINEMENT.
REMARK 3    PROGRAM : REFMAC 5.6.0117
REMARK 3    AUTHORS : MURSHUDOV, VAGIN, DODSON
REMARK 3
REMARK 3    REFINEMENT TARGET : MAXIMUM LIKELIHOOD
REMARK 3
REMARK 3    DATA USED IN REFINEMENT.
REMARK 3    RESOLUTION RANGE HIGH (ANGSTROMS) : 2.30
REMARK 3    RESOLUTION RANGE LOW (ANGSTROMS) : 50.00
REMARK 3    DATA CUTOFF (SIGMA(F)) : NONE
REMARK 3    COMPLETENESS FOR RANGE (%) : 99.87
REMARK 3    NUMBER OF REFLECTIONS : 12075
REMARK 3
REMARK 3    FIT TO DATA USED IN REFINEMENT.
REMARK 3    CROSSVALIDATION METHOD : THROUGHOUT
REMARK 3    FREE R VAL UE TEST SET SELECTION : RANDOM
REMARK 3    R VALUE (WORKING + TEST SET) : 0.22851
REMARK 3    R VALUE (WORKING SET) : 0.22458
REMARK 3    FREE R VALUE : 0.30679
REMARK 3    FREE R VALUE TEST SET SIZE (%) : 4.9
REMARK 3    FREE R VALUE TEST SET COUNT : 620
REMARK 3
REMARK 3    FIT IN THE HIGHEST RESOLUTION BIN.
REMARK 3    TOTAL NUMBER OF BINS USED : 20
REMARK 3    BIN RESOLUTION RANGE HIGH : 2.300
REMARK 3    BIN RESOLUTION RANGE LOW : 2.360
REMARK 3    REFLECTION IN BIN (WORKING SET) : 803
REMARK 3    BIN COMPLETENESS (WORKING + TEST) (%) : 99.88
REMARK 3    BIN R VALUE (WORKING SET) : 0.259
REMARK 3    BIN FREE R VALUE SET COUNT 38
REMARK 3    BIN FREE R VALUE : 0.368
REMARK 3
REMARK 3    NUMBER OF NONHYDROGEN ATOMS USED IN REFINEMENT.
REMARK 3    ALL ATOMS : 1610
REMARK 3
REMARK 3    B VALUES.
REMARK 3    FROM WILSON PLOT (A**2) : NULL
REMARK 3    MEAN B VALUE (OVERALL, A**2) : 52.954
REMARK 3    OVERALL ANISOTROPIC B VALUE.
REMARK 3    B11 (A**2) : NULL
REMARK 3    B22 (A**2) : NULL
REMARK 3    B33 (A**2) : NULL
REMARK 3    B12 (A**2) : NULL
REMARK 3    B13 (A**2) : NULL
REMARK 3    B23 (A**2) : NULL
REMARK 3
REMARK 3    ESTIMATED OVERALL COORDINATE ERROR.
```

TABLE 8-continued

Atomic coordinates for unbound CRBN-CRBN (TBD) (Apo) (Murine protein)

```
REMARK 3    ESU BASED ON R VALUE (A ): 0.281
REMARK 3    ESU BASED ON FREE R VAL UE (A) : 0.262
REMARK 3    ESU BASED ON MAXIMUM LIKELIHOOD (A) : 0.203
REMARK 3    ESU FOR B VALUES BASED ON MAXIMUM LIKELIHOOD(A**2) : 8.210
REMARK 3
REMARK 3    CORRELATION COEFFICIENTS.
REMARK 3    CORRELATION COEFFICIENT FOFC : 0.943
REMARK 3    CORRELATION COEFFICIENT FOFC FREE : 0.913
REMARK 3
REMARK 3    RMS DEVIATIONS FROMIDEAL VALUES      COUNT      RMS      WEIGHT
REMARK 3    BOND LENGTHS REFINED ATOMS (A):       1642 ;    0.015 ;    0.020
REMARK 3    BOND ANGLES REFINED ATOMS (DEGREES):  2234 ;    1.899 ;    1.954
REMARK 3    TORSION ANGLES, PERIOD 1 (DEGREES):    198 ;    8.790 ;    5.000
REMARK 3    TORSION ANGLES, PERIOD 2 (DEGREES):    56 ;43.   316 ;    23.750
REMARK 3    TORSION ANGLES, PERIOD 3 (DEGREES):    273 ;   18.925 ;   15.000
REMARK 3    TORSION ANGLES, PERIOD 4 (DEGREES):      4 ;   17.860 ;   15.000
REMARK 3    CHIRALCENTER RESTRAINTS (A**3):        256 ;    0.122;     0.200
REMARK 3    GENERAL PLANES REFINED ATOMS (A):     1170 ;    0.014 ;    0.021
REMARK 3
REMARK 3    ISOTROPIC THERMAL FACTOR RESTRAINTS. COUNT RMS WEIGHT
REMARK 3
REMARK 3    NCS RESTRAINTS STATISTICS
REMARK 3    NCS TYPE: LOCAL
REMARK 3    NUMBER OF DIFFERENT NCS PAIRS : 1
REMARK 3    GROUP   CHAIN1   RANGE   CHAIN2   RANGE   COUNT   RMS   WEIGHT
REMARK 3       1      D       322      A       427     118    0.19   0.05
REMARK 3
REMARK 3    TWIN DETAILS
REMARK 3    NUMBER OF TWIN DOMAINS : NULL
REMARK 3
REMARK 3
REMARK 3    TLS DETAILS
REMARK 3    NUMBER OF TLS GROUPS : NULL
REMARK 3
REMARK 3
REMARK 3    BULK SOLVENT MODELLING.
REMARK 3    METHOD USED: MASK
REMARK 3    PARAMETERS FOR MASK CALCULATION
REMARK 3    VDW PROBE RADIUS : 1.20
REMARK 3    ION PROBE RADIUS : 0.80
REMARK 3    SHRINKAGE RADIUS : 0.80
REMARK 3
REMARK 3    OTHER REFINEMENT REMARKS:
REMARK 3    HYDROGENS HAVE BEEN USED IF PRESENT IN THE INPUT
REMARK 3    U VALUES : REFINED INDIVIDUALLY
REMARK 3
CISPEP   1    SER D   413      PRO D   414  0.00
CISPEP   2    SER A   413      PRO A   414  0.00
SSBOND   1    CYS A   329      CYS A   326
LINKR         PRO D   355      GLU D   361    gap
LINKR         ALA A   351      TYR A   358    gap
LINKR         SER D   344      GLU D   361    gap
LINKR         SER A   344      GLU A   361    gap
CRYST1  119.260   119.260   119.260    90.00    90.00    90.00 I 21 3
SCALE1   0.008385   0.000000   0.000000   0.00000
SCALE2   0.000000   0.008385   0.000000   0.00000
SCALE3   0.000000   0.000000   0.008385   0.00000
ATOM    1   N    THR  D  322    3.272   14.657   13.569  1.00  64.62  N
ATOM    2   CA   THR  D  322    3.270   14.354   12.096  1.00  56.77  C
ATOM    3   CB   THR  D  322    4.075   13.067   11.736  1.00  59.13  C
ATOM    4   OG1  THR  D  322    3.399   11.904   12.224  1.00  62.54  O
ATOM    5   CG2  THR  D  322    5.549   13.085   12.213  1.00  69.21  C
ATOM    6   C    THR  D  322    1.878   14.263   11.376  1.00  53.27  C
ATOM    7   O    THR  D  322    1.814   14.024   10.159  1.00  46.87  O
ATOM    8   N    SER  D  323    0.777   14.411   12.102  1.00  49.61  N
ATOM    9   CA   SER  D  323   -0.552   14.200   11.499  1.00  48.06  C
ATOM   10   CB   SER  D  323   -1.613   14.020   12.582  1.00  47.31  C
ATOM   11   OG   SER  D  323   -1.239   12.953   13.380  1.00  50.21  O
ATOM   12   C    SER  D  323   -1.008   15.334   10.653  1.00  48.09  C
ATOM   13   O    SER  D  323   -0.835   16.497   11.019  1.00  54.45  O
ATOM   14   N    LEU  D  324   -1.641   14.999    9.537  1.00  46.35  N
ATOM   15   CA   LEU  D  324   -2.317   16.012    8.747  1.00  46.17  C
ATOM   16   CB   LEU  D  324   -1.777   16.028    7.326  1.00  44.87  C
ATOM   17   CG   LEU  D  324   -0.272   16.315    7.262  1.00  52.31  C
ATOM   18   CD1  LEU  D  324   -0.296   15.937    5.905  1.00  46.65  C
ATOM   19   CD2  LEU  D  324   -0.068   17.770    7.615  1.00  50.32  C
ATOM   20   C    LEU  D  324   -3.825   15.725    8.795  1.00  49.15  C
ATOM   21   O    LEU  D  324   -4.305   14.664    8.342  1.00  47.14  O
```

TABLE 8-continued

Atomic coordinates for unbound CRBN-CRBN (TBD) (Apo) (Murine protein)

| ATOM | 22 | N | CYS | D | 325 | −4.548 | 16.675 | 9.383 | 1.00 | 43.84 | N |
|---|---|---|---|---|---|---|---|---|---|---|---|
| ATOM | 23 | CA | CYS | D | 325 | −5.932 | 16.496 | 9.817 | 1.00 | 44.84 | C |
| ATOM | 24 | CB | CYS | D | 325 | −6.077 | 16.857 | 11.309 | 1.00 | 42.45 | C |
| ATOM | 25 | SG | CYS | D | 325 | −5.337 | 15.652 | 12.480 | 1.00 | 58.67 | S |
| ATOM | 26 | C | CYS | D | 325 | −6.837 | 17.393 | 8.971 | 1.00 | 45.43 | C |
| ATOM | 27 | O | CYS | D | 325 | −6.404 | 18.460 | 8.525 | 1.00 | 40.81 | O |
| ATOM | 28 | N | CYS | D | 326 | −8.073 | 16.955 | 8.745 | 1.00 | 45.40 | N |
| ATOM | 29 | CA | CYS | D | 326 | −9.097 | 17.797 | 8.109 | 1.00 | 47.57 | C |
| ATOM | 30 | CB | CYS | D | 326 | −10.438 | 17.038 | 8.128 | 1.00 | 42.62 | C |
| ATOM | 31 | SG | CYS | D | 326 | −11.946 | 17.943 | 7.666 | 1.00 | 46.51 | S |
| ATOM | 32 | C | CYS | D | 326 | −9.225 | 19.113 | 8.897 | 1.00 | 50.01 | C |
| ATOM | 33 | O | CYS | D | 326 | −9.475 | 19.062 | 10.111 | 1.00 | 49.04 | O |
| ATOM | 34 | N | LYS | D | 327 | −9.020 | 20.252 | 8.213 | 1.00 | 47.57 | N |
| ATOM | 35 | CA | LYS | D | 327 | −9.212 | 21.628 | 8.751 | 1.00 | 55.56 | C |
| ATOM | 36 | CB | LYS | D | 327 | −8.862 | 22.705 | 7.689 | 1.00 | 55.05 | C |
| ATOM | 37 | CG | LYS | D | 327 | −8.733 | 24.143 | 8.220 | 1.00 | 64.17 | C |
| ATOM | 38 | CD | LYS | D | 327 | −8.407 | 25.203 | 7.146 | 1.00 | 67.49 | C |
| ATOM | 39 | CE | LYS | D | 327 | −9.487 | 25.335 | 6.061 | 1.00 | 76.07 | C |
| ATOM | 40 | NZ | LYS | D | 327 | −9.698 | 26.728 | 5.544 | 1.00 | 78.00 | N |
| ATOM | 41 | C | LYS | D | 327 | −10.614 | 21.901 | 9.328 | 1.00 | 52.50 | C |
| ATOM | 42 | O | LYS | D | 327 | −10.728 | 22.565 | 10.359 | 1.00 | 55.95 | O |
| ATOM | 43 | N | GLN | D | 328 | −11.659 | 21.387 | 8.678 | 1.00 | 50.49 | N |
| ATOM | 44 | CA | GLN | D | 328 | −13.044 | 21.577 | 9.143 | 1.00 | 51.61 | C |
| ATOM | 45 | CB | GLN | D | 328 | −14.044 | 21.073 | 8.103 | 1.00 | 56.84 | C |
| ATOM | 46 | CG | GLN | D | 328 | −15.532 | 21.278 | 8.463 | 1.00 | 54.76 | C |
| ATOM | 47 | CD | GLN | D | 328 | −15.879 | 22.743 | 8.801 | 1.00 | 61.69 | C |
| ATOM | 48 | OE1 | GLN | D | 328 | −15.462 | 23.677 | 8.112 | 1.00 | 57.77 | O |
| ATOM | 49 | NE2 | GLN | D | 328 | −16.643 | 22.937 | 9.885 | 1.00 | 54.96 | N |
| ATOM | 50 | C | GLN | D | 328 | −13.364 | 20.966 | 10.523 | 1.00 | 52.52 | C |
| ATOM | 51 | O | GLN | D | 328 | −13.807 | 21.664 | 11.429 | 1.00 | 51.02 | O |
| ATOM | 52 | N | CYS | D | 329 | −13.140 | 19.666 | 10.693 | 1.00 | 51.16 | N |
| ATOM | 53 | CA | CYS | D | 329 | −13.587 | 18.987 | 11.901 | 1.00 | 44.18 | C |
| ATOM | 54 | CB | CYS | D | 329 | −14.281 | 17.682 | 11.497 | 1.00 | 47.66 | C |
| ATOM | 55 | SG | CYS | D | 329 | −13.146 | 16.391 | 10.863 | 1.00 | 48.39 | S |
| ATOM | 56 | C | CYS | D | 329 | −12.432 | 18.710 | 12.878 | 1.00 | 45.42 | C |
| ATOM | 57 | O | CYS | D | 329 | −12.658 | 18.281 | 14.001 | 1.00 | 58.56 | O |
| ATOM | 58 | N | GLN | D | 330 | −11.204 | 18.864 | 12.399 | 1.00 | 47.51 | N |
| ATOM | 59 | CA | GLN | D | 330 | −9.956 | 18.803 | 13.195 | 1.00 | 55.76 | C |
| ATOM | 60 | CB | GLN | D | 330 | −9.780 | 20.049 | 14.095 | 1.00 | 62.32 | C |
| ATOM | 61 | CG | GLN | D | 330 | −9.205 | 21.205 | 13.280 | 1.00 | 67.86 | C |
| ATOM | 62 | CD | GLN | D | 330 | −9.431 | 22.609 | 13.850 | 1.00 | 74.43 | C |
| ATOM | 63 | OE1 | GLN | D | 330 | −9.254 | 22.847 | 15.058 | 1.00 | 74.35 | O |
| ATOM | 64 | NE2 | GLN | D | 330 | −9.783 | 23.568 | 12.954 | 1.00 | 59.71 | N |
| ATOM | 65 | C | GLN | D | 330 | −9.548 | 17.498 | 13.872 | 1.00 | 52.39 | C |
| ATOM | 66 | O | GLN | D | 330 | −8.399 | 17.127 | 13.784 | 1.00 | 58.40 | O |
| ATOM | 67 | N | GLU | D | 331 | −10.470 | 16.814 | 14.535 | 1.00 | 55.50 | N |
| ATOM | 68 | CA | GLU | D | 331 | −10.276 | 15.436 | 15.021 | 1.00 | 62.68 | C |
| ATOM | 69 | CB | GLU | D | 331 | −11.655 | 14.822 | 15.216 | 1.00 | 67.97 | C |
| ATOM | 70 | CG | GLU | D | 331 | −12.291 | 15.037 | 16.545 | 1.00 | 81.75 | C |
| ATOM | 71 | CD | GLU | D | 331 | −13.408 | 14.064 | 16.755 | 1.00 | 75.98 | C |
| ATOM | 72 | OE1 | GLU | D | 331 | −14.019 | 14.134 | 17.841 | 1.00 | 80.04 | O |
| ATOM | 73 | OE2 | GLU | D | 331 | −13.648 | 13.228 | 15.849 | 1.00 | 68.70 | O |
| ATOM | 74 | C | GLU | D | 331 | −9.661 | 14.451 | 14.020 | 1.00 | 55.88 | C |
| ATOM | 75 | O | GLU | D | 331 | −8.964 | 13.516 | 14.370 | 1.00 | 48.88 | O |
| ATOM | 76 | N | THR | D | 332 | −10.060 | 14.585 | 12.777 | 1.00 | 49.03 | N |
| ATOM | 77 | CA | THR | D | 332 | −9.875 | 13.475 | 11.862 | 1.00 | 48.41 | C |
| ATOM | 78 | CB | THR | D | 332 | −11.034 | 13.358 | 10.870 | 1.00 | 42.25 | C |
| ATOM | 79 | OG1 | THR | D | 332 | −12.289 | 13.595 | 11.562 | 1.00 | 41.02 | O |
| ATOM | 80 | CG2 | THR | D | 332 | −11.031 | 11.971 | 10.349 | 1.00 | 42.26 | C |
| ATOM | 81 | C | THR | D | 332 | −8.559 | 13.549 | 11.109 | 1.00 | 44.70 | C |
| ATOM | 82 | O | THR | D | 332 | −8.333 | 14.480 | 10.320 | 1.00 | 47.53 | O |
| ATOM | 83 | N | GLU | D | 333 | −7.714 | 12.539 | 11.331 | 1.00 | 47.04 | N |
| ATOM | 84 | CA | GLU | D | 333 | −6.434 | 12.454 | 10.605 | 1.00 | 49.38 | C |
| ATOM | 85 | CB | GLU | D | 333 | −5.421 | 11.595 | 11.367 | 1.00 | 41.74 | C |
| ATOM | 86 | CG | GLU | D | 333 | −4.051 | 11.576 | 10.707 | 1.00 | 41.19 | C |
| ATOM | 87 | CD | GLU | D | 333 | −3.153 | 10.525 | 11.310 | 1.00 | 41.58 | C |
| ATOM | 88 | OE1 | GLU | D | 333 | −2.560 | 10.821 | 12.360 | 1.00 | 39.87 | O |
| ATOM | 89 | OE2 | GLU | D | 333 | −3.052 | 9.398 | 10.746 | 1.00 | 40.49 | O |
| ATOM | 90 | C | GLU | D | 333 | −6.659 | 11.933 | 9.203 | 1.00 | 40.60 | C |
| ATOM | 91 | O | GLU | D | 333 | −7.309 | 10.913 | 9.003 | 1.00 | 44.41 | O |
| ATOM | 92 | N | ILE | D | 334 | −6.145 | 12.648 | 8.221 | 1.00 | 39.13 | N |
| ATOM | 93 | CA | ILE | D | 334 | −6.305 | 12.230 | 6.832 | 1.00 | 40.13 | C |
| ATOM | 94 | CB | ILE | D | 334 | −6.720 | 13.432 | 5.933 | 1.00 | 45.63 | C |
| ATOM | 95 | CG1 | ILE | D | 334 | −8.014 | 14.067 | 6.481 | 1.00 | 44.93 | C |
| ATOM | 96 | CD1 | ILE | D | 334 | −9.218 | 13.139 | 6.374 | 1.00 | 40.94 | C |
| ATOM | 97 | CG2 | ILE | D | 334 | −6.996 | 12.987 | 4.493 | 1.00 | 42.26 | C |
| ATOM | 98 | C | ILE | D | 334 | −5.044 | 11.496 | 6.295 | 1.00 | 40.76 | C |
| ATOM | 99 | O | ILE | D | 334 | −5.145 | 10.589 | 5.489 | 1.00 | 41.96 | O |

TABLE 8-continued

Atomic coordinates for unbound CRBN-CRBN (TBD) (Apo) (Murine protein)

| ATOM | 100 | N | THR | D | 335 | -3.865 | 11.918 | 6.731 | 1.00 | 41.54 | N |
|---|---|---|---|---|---|---|---|---|---|---|---|
| ATOM | 101 | CA | THR | D | 335 | -2.600 | 11.324 | 6.320 | 1.00 | 39.19 | C |
| ATOM | 102 | CB | THR | D | 335 | -2.206 | 11.633 | 4.850 | 1.00 | 41.57 | C |
| ATOM | 103 | OG1 | THR | D | 335 | -1.105 | 10.796 | 4.440 | 1.00 | 37.99 | O |
| ATOM | 104 | CG2 | THR | D | 335 | -1.809 | 13.099 | 4.663 | 1.00 | 45.26 | C |
| ATOM | 105 | C | THR | D | 335 | -1.534 | 11.778 | 7.312 | 1.00 | 43.17 | C |
| ATOM | 106 | O | THR | D | 335 | -1.810 | 12.524 | 8.299 | 1.00 | 44.12 | O |
| ATOM | 107 | N | THR | D | 336 | -0.314 | 11.316 | 7.105 | 1.00 | 42.30 | N |
| ATOM | 108 | CA | THR | D | 336 | 0.775 | 11.774 | 7.968 | 1.00 | 35.78 | C |
| ATOM | 109 | CB | THR | D | 336 | 1.281 | 10.659 | 8.921 | 1.00 | 36.27 | C |
| ATOM | 110 | OG1 | THR | D | 336 | 2.135 | 9.755 | 8.234 | 1.00 | 37.81 | O |
| ATOM | 111 | CG2 | THR | D | 336 | 0.169 | 9.921 | 9.657 | 1.00 | 35.90 | C |
| ATOM | 112 | C | THR | D | 336 | 1.882 | 12.247 | 7.092 | 1.00 | 36.85 | C |
| ATOM | 113 | O | THR | D | 336 | 1.907 | 11.962 | 5.864 | 1.00 | 41.31 | O |
| ATOM | 114 | N | LYS | D | 337 | 2.840 | 12.931 | 7.686 | 1.00 | 40.98 | N |
| ATOM | 115 | CA | LYS | D | 337 | 3.978 | 13.453 | 6.909 | 1.00 | 39.49 | C |
| ATOM | 116 | CB | LYS | D | 337 | 4.846 | 14.377 | 7.789 | 1.00 | 44.44 | C |
| ATOM | 117 | CG | LYS | D | 337 | 4.342 | 15.837 | 7.937 | 1.00 | 54.47 | C |
| ATOM | 118 | CD | LYS | D | 337 | 5.148 | 16.721 | 8.956 | 1.00 | 54.95 | C |
| ATOM | 119 | CE | LYS | D | 337 | 4.562 | 16.604 | 10.380 | 1.00 | 62.13 | C |
| ATOM | 120 | NZ | LYS | D | 337 | 5.006 | 17.542 | 11.471 | 1.00 | 54.68 | N |
| ATOM | 121 | C | LYS | D | 337 | 4.831 | 12.309 | 6.376 | 1.00 | 38.83 | C |
| ATOM | 122 | O | LYS | D | 337 | 5.518 | 12.471 | 5.382 | 1.00 | 36.42 | O |
| ATOM | 123 | N | ASN | D | 338 | 4.802 | 11.155 | 7.033 | 1.00 | 39.65 | N |
| ATOM | 124 | CA | ASN | D | 338 | 5.576 | 9.971 | 6.599 | 1.00 | 37.97 | C |
| ATOM | 125 | CB | ASN | D | 338 | 5.376 | 8.861 | 7.605 | 1.00 | 42.07 | C |
| ATOM | 126 | CG | ASN | D | 338 | 6.010 | 9.186 | 8.956 | 1.00 | 48.60 | C |
| ATOM | 127 | OD1 | ASN | D | 338 | 5.328 | 9.296 | 9.958 | 1.00 | 51.36 | O |
| ATOM | 128 | ND2 | ASN | D | 338 | 7.311 | 9.327 | 8.976 | 1.00 | 41.86 | N |
| ATOM | 129 | C | ASN | D | 338 | 5.165 | 9.433 | 5.214 | 1.00 | 40.36 | C |
| ATOM | 130 | O | ASN | D | 338 | 5.935 | 8.741 | 4.543 | 1.00 | 36.07 | O |
| ATOM | 131 | N | GLU | D | 339 | 3.939 | 9.737 | 4.802 | 1.00 | 35.85 | N |
| ATOM | 132 | CA | GLU | D | 339 | 3.418 | 9.219 | 3.527 | 1.00 | 35.86 | C |
| ATOM | 133 | CB | GLU | D | 339 | 1.939 | 8.920 | 3.628 | 1.00 | 33.23 | C |
| ATOM | 134 | CG | GLU | D | 339 | 1.613 | 8.095 | 4.871 | 1.00 | 38.12 | C |
| ATOM | 135 | CD | GLU | D | 339 | 2.348 | 6.765 | 4.843 | 1.00 | 41.29 | C |
| ATOM | 136 | OE1 | GLU | D | 339 | 2.328 | 6.076 | 3.766 | 1.00 | 36.54 | O |
| ATOM | 137 | OE2 | GLU | D | 339 | 2.993 | 6.435 | 5.864 | 1.00 | 42.89 | O |
| ATOM | 138 | C | GLU | D | 339 | 3.681 | 10.101 | 2.308 | 1.00 | 35.63 | C |
| ATOM | 139 | O | GLU | D | 339 | 3.378 | 9.686 | 1.212 | 1.00 | 39.41 | O |
| ATOM | 140 | N | ILE | D | 340 | 4.229 | 11.299 | 2.519 | 1.00 | 38.49 | N |
| ATOM | 141 | CA | ILE | D | 340 | 4.489 | 12.247 | 1.448 | 1.00 | 37.67 | C |
| ATOM | 142 | CB | ILE | D | 340 | 4.963 | 13.601 | 2.002 | 1.00 | 39.26 | C |
| ATOM | 143 | CG1 | ILE | D | 340 | 3.784 | 14.299 | 2.689 | 1.00 | 40.96 | C |
| ATOM | 144 | CD1 | ILE | D | 340 | 4.163 | 15.546 | 3.489 | 1.00 | 42.37 | C |
| ATOM | 145 | CG2 | ILE | D | 340 | 5.452 | 14.503 | 0.849 | 1.00 | 42.48 | C |
| ATOM | 146 | C | ILE | D | 340 | 5.549 | 11.738 | 0.505 | 1.00 | 39.51 | C |
| ATOM | 147 | O | ILE | D | 340 | 6.581 | 11.198 | 0.924 | 1.00 | 35.48 | O |
| ATOM | 148 | N | PHE | D | 341 | 5.290 | 11.921 | -0.787 | 1.00 | 41.90 | N |
| ATOM | 149 | CA | PHE | D | 341 | 6.286 | 11.635 | -1.785 | 1.00 | 40.38 | C |
| ATOM | 150 | CB | PHE | D | 341 | 6.175 | 10.184 | -2.294 | 1.00 | 38.00 | C |
| ATOM | 151 | CG | PHE | D | 341 | 5.026 | 9.945 | -3.207 | 1.00 | 36.08 | C |
| ATOM | 152 | CD1 | PHE | D | 341 | 5.235 | 9.719 | -4.552 | 1.00 | 32.92 | C |
| ATOM | 153 | CE1 | PHE | D | 341 | 4.165 | 9.524 | -5.391 | 1.00 | 32.01 | C |
| ATOM | 154 | CZ | PHE | D | 341 | 2.871 | 9.484 | -4.878 | 1.00 | 37.44 | C |
| ATOM | 155 | CE2 | PHE | D | 341 | 2.648 | 9.672 | -3.541 | 1.00 | 33.23 | C |
| ATOM | 156 | CD2 | PHE | D | 341 | 3.719 | 9.919 | -2.704 | 1.00 | 36.33 | C |
| ATOM | 157 | C | PHE | D | 341 | 6.230 | 12.645 | -2.911 | 1.00 | 44.71 | C |
| ATOM | 158 | O | PHE | D | 341 | 5.365 | 13.506 | -2.927 | 1.00 | 42.80 | O |
| ATOM | 159 | N | SER | D | 342 | 7.139 | 12.497 | -3.877 | 1.00 | 46.63 | N |
| ATOM | 160 | CA | SER | D | 342 | 7.237 | 13.424 | -4.989 | 1.00 | 44.33 | C |
| ATOM | 161 | CB | SER | D | 342 | 8.622 | 14.091 | -4.979 | 1.00 | 48.28 | C |
| ATOM | 162 | OG | SER | D | 342 | 8.759 | 14.915 | -6.117 | 1.00 | 52.70 | O |
| ATOM | 163 | C | SER | D | 342 | 7.011 | 12.708 | -6.301 | 1.00 | 43.33 | C |
| ATOM | 164 | O | SER | D | 342 | 7.859 | 11.973 | -6.759 | 1.00 | 42.07 | O |
| ATOM | 165 | N | LEU | D | 343 | 5.842 | 12.908 | -6.885 | 1.00 | 47.09 | N |
| ATOM | 166 | CA | LEU | D | 343 | 5.453 | 12.273 | -8.133 | 1.00 | 46.30 | C |
| ATOM | 167 | CB | LEU | D | 343 | 3.934 | 12.213 | -8.227 | 1.00 | 43.43 | C |
| ATOM | 168 | CG | LEU | D | 343 | 3.118 | 11.373 | -9.221 | 1.00 | 48.56 | C |
| ATOM | 169 | CD1 | LEU | D | 343 | 2.726 | 12.187 | -10.436 | 1.00 | 60.72 | C |
| ATOM | 170 | CD2 | LEU | D | 343 | 3.761 | 10.053 | -9.627 | 1.00 | 46.02 | C |
| ATOM | 171 | C | LEU | D | 343 | 5.996 | 13.147 | -9.265 | 1.00 | 48.21 | C |
| ATOM | 172 | O | LEU | D | 343 | 5.705 | 14.346 | -9.347 | 1.00 | 40.71 | O |
| ATOM | 173 | N | SER | D | 344 | 6.791 | 12.548 | -10.138 | 1.00 | 40.44 | N |
| ATOM | 174 | CA | SER | D | 344 | 7.365 | 13.341 | -11.194 | 1.00 | 50.50 | C |
| ATOM | 175 | CB | SER | D | 344 | 8.653 | 12.670 | -11.683 | 1.00 | 53.39 | C |
| ATOM | 176 | OG | SER | D | 344 | 8.725 | 12.771 | -13.086 | 1.00 | 58.30 | O |
| ATOM | 177 | C | SER | D | 344 | 6.319 | 13.528 | -12.307 | 1.00 | 51.02 | C |

TABLE 8-continued

Atomic coordinates for unbound CRBN-CRBN (TBD) (Apo) (Murine protein)

| ATOM | 178 | O | SER | D | 344 | 5.720 | 12.547 | −12.750 | 1.00 | 45.55 | O |
|---|---|---|---|---|---|---|---|---|---|---|---|
| ATOM | 179 | N | LEU | D | 345 | 6.084 | 17.791 | −12.708 | 1.00 | 54.39 | N |
| ATOM | 180 | CA | LEU | D | 345 | 5.132 | 15.159 | −13.762 | 1.00 | 57.02 | C |
| ATOM | 181 | CB | LEU | D | 345 | 4.702 | 16.607 | −13.568 | 1.00 | 56.01 | C |
| ATOM | 182 | CG | LEU | D | 345 | 3.586 | 16.832 | −12.526 | 1.00 | 68.64 | C |
| ATOM | 183 | CD1 | LEU | D | 345 | 2.686 | 15.601 | −12.349 | 1.00 | 50.71 | C |
| ATOM | 184 | CD2 | LEU | D | 345 | 4.129 | 17.319 | −11.179 | 1.00 | 63.77 | C |
| ATOM | 185 | C | LEU | D | 345 | 5.633 | 14.956 | −15.199 | 1.00 | 59.80 | C |
| ATOM | 186 | O | LEU | D | 345 | 4.883 | 14.603 | −16.119 | 1.00 | 59.84 | O |
| ATOM | 187 | N | CYS | D | 346 | 6.908 | 15.196 | −15.418 | 1.00 | 60.63 | N |
| ATOM | 188 | CA | CYS | D | 346 | 7.452 | 15.068 | −16.769 | 1.00 | 58.10 | C |
| ATOM | 189 | CB | CYS | D | 346 | 8.806 | 15.738 | −16.763 | 1.00 | 59.30 | C |
| ATOM | 190 | SG | CYS | D | 346 | 9.932 | 14.849 | −15.676 | 1.00 | 62.23 | S |
| ATOM | 191 | C | CYS | D | 346 | 7.536 | 13.570 | −17.152 | 1.00 | 56.66 | C |
| ATOM | 192 | O | CYS | D | 346 | 7.422 | 12.698 | −16.273 | 1.00 | 52.17 | O |
| ATOM | 193 | N | GLY | D | 347 | 7.715 | 13.259 | −18.439 | 1.00 | 59.35 | N |
| ATOM | 194 | CA | GLY | D | 347 | 7.877 | 11.847 | −18.869 | 1.00 | 58.45 | C |
| ATOM | 195 | C | GLY | D | 347 | 9.314 | 11.454 | −19.283 | 1.00 | 59.10 | O |
| ATOM | 196 | O | GLY | D | 347 | 10.289 | 11.997 | −18.749 | 1.00 | 52.27 | O |
| ATOM | 197 | N | PRO | D | 348 | 9.468 | 10.510 | −20.243 | 1.00 | 58.55 | N |
| ATOM | 198 | CA | PRO | D | 348 | 10.842 | 10.133 | −20.666 | 1.00 | 52.91 | C |
| ATOM | 199 | CB | PRO | D | 348 | 10.610 | 9.237 | −21.887 | 1.00 | 57.72 | C |
| ATOM | 200 | CG | PRO | D | 348 | 9.221 | 8.681 | −21.690 | 1.00 | 59.26 | C |
| ATOM | 201 | CD | PRO | D | 348 | 8.434 | 9.771 | −21.004 | 1.00 | 57.37 | C |
| ATOM | 202 | C | PRO | D | 348 | 11.683 | 11.367 | −21.030 | 1.00 | 47.28 | C |
| ATOM | 203 | O | PRO | D | 348 | 11.170 | 12.312 | −21.652 | 1.00 | 53.63 | O |
| ATOM | 204 | N | MET | D | 349 | 12.933 | 11.348 | −20.560 | 1.00 | 45.09 | N |
| ATOM | 205 | CA | MET | D | 349 | 13.940 | 12.391 | −20.717 | 1.00 | 51.67 | C |
| ATOM | 206 | CB | MET | D | 349 | 14.184 | 12.691 | −22.195 | 1.00 | 56.76 | C |
| ATOM | 207 | CG | MET | D | 349 | 15.321 | 11.882 | −22.768 | 1.00 | 67.16 | C |
| ATOM | 208 | SD | MET | D | 349 | 14.804 | 10.194 | −23.122 | 1.00 | 82.62 | S |
| ATOM | 209 | CE | MET | D | 349 | 16.093 | 9.809 | −24.307 | 1.00 | 76.12 | C |
| ATOM | 210 | C | MET | D | 349 | 13.655 | 13.680 | −19.954 | 1.00 | 56.01 | C |
| ATOM | 211 | O | MET | D | 349 | 14.421 | 14.659 | −20.060 | 1.00 | 51.99 | O |
| ATOM | 212 | N | ALA | D | 350 | 12.570 | 13.672 | −19.179 | 1.00 | 45.92 | N |
| ATOM | 213 | CA | ALA | D | 350 | 12.125 | 14.837 | −18.435 | 1.00 | 48.64 | C |
| ATOM | 214 | CB | ALA | D | 350 | 13.080 | 15.192 | −17.305 | 1.00 | 43.75 | C |
| ATOM | 215 | C | ALA | D | 350 | 11.941 | 15.984 | −19.396 | 1.00 | 54.11 | C |
| ATOM | 216 | O | ALA | D | 350 | 12.371 | 17.111 | −19.133 | 1.00 | 55.10 | O |
| ATOM | 217 | N | ALA | D | 351 | 11.304 | 15.678 | −20.527 | 1.00 | 55.10 | N |
| ATOM | 218 | CA | ALA | D | 351 | 10.814 | 16.715 | −21.412 | 1.00 | 54.65 | C |
| ATOM | 219 | CB | ALA | D | 351 | 10.135 | 16.080 | −22.623 | 1.00 | 58.21 | C |
| ATOM | 220 | C | ALA | D | 351 | 9.851 | 17.672 | −20.710 | 1.00 | 60.94 | C |
| ATOM | 221 | O | ALA | D | 351 | 9.202 | 17.335 | −19.704 | 1.00 | 63.45 | O |
| ATOM | 222 | N | TYR | D | 352 | 9.783 | 18.874 | −21.269 | 1.00 | 59.73 | N |
| ATOM | 223 | CA | TYR | D | 352 | 8.778 | 19.850 | −20.962 | 1.00 | 61.26 | C |
| ATOM | 224 | CB | TYR | D | 352 | 8.935 | 21.000 | −21.934 | 1.00 | 53.79 | C |
| ATOM | 225 | CG | TYR | D | 352 | 7.957 | 22.130 | −21.737 | 1.00 | 64.11 | C |
| ATOM | 226 | CD1 | TYR | D | 352 | 8.116 | 23.025 | −20.679 | 1.00 | 61.81 | C |
| ATOM | 227 | CE1 | TYR | D | 352 | 7.244 | 24.070 | −20.485 | 1.00 | 56.93 | C |
| ATOM | 228 | CZ | TYR | D | 352 | 6.170 | 24.245 | −21.347 | 1.00 | 62.45 | C |
| ATOM | 229 | OH | TYR | D | 352 | 5.306 | 25.291 | −21.109 | 1.00 | 54.95 | O |
| ATOM | 230 | CE2 | TYR | D | 352 | 5.976 | 23.377 | −22.410 | 1.00 | 66.12 | C |
| ATOM | 231 | CD2 | TYR | D | 352 | 6.875 | 22.320 | −22.608 | 1.00 | 64.41 | C |
| ATOM | 232 | C | TYR | D | 352 | 7.345 | 19.298 | −21.107 | 1.00 | 67.24 | C |
| ATOM | 233 | O | TYR | D | 352 | 7.085 | 18.389 | −21.930 | 1.00 | 56.50 | O |
| ATOM | 234 | N | VAL | D | 353 | 6.441 | 19.864 | −20.295 | 1.00 | 58.64 | N |
| ATOM | 235 | CA | VAL | D | 353 | 4.986 | 19.817 | −20.536 | 1.00 | 72.92 | C |
| ATOM | 236 | CB | VAL | D | 353 | 4.369 | 18.431 | −20.280 | 1.00 | 72.72 | C |
| ATOM | 237 | CG1 | VAL | D | 353 | 4.159 | 17.726 | −21.611 | 1.00 | 67.44 | C |
| ATOM | 238 | CG2 | VAL | D | 353 | 5.218 | 17.604 | −19.314 | 1.00 | 69.43 | C |
| ATOM | 239 | C | VAL | D | 353 | 4.221 | 20.909 | −19.787 | 1.00 | 74.75 | C |
| ATOM | 240 | O | VAL | D | 353 | 4.808 | 21.584 | −18.927 | 1.00 | 75.27 | O |
| ATOM | 241 | N | ASN | D | 354 | 2.943 | 21.112 | −20.146 | 1.00 | 91.62 | N |
| ATOM | 242 | CA | ASN | D | 354 | 2.011 | 21.982 | −19.378 | 1.00 | 95.01 | C |
| ATOM | 243 | CB | ASN | D | 354 | 2.582 | 23.392 | −19.156 | 1.00 | 93.07 | C |
| ATOM | 244 | CG | ASN | D | 354 | 2.112 | 24.036 | −17.849 | 1.00 | 87.99 | C |
| ATOM | 245 | OD1 | ASN | D | 354 | 2.590 | 25.109 | −17.480 | 1.00 | 83.95 | O |
| ATOM | 246 | ND2 | ASN | D | 354 | 1.190 | 23.385 | −17.141 | 1.00 | 91.44 | N |
| ATOM | 247 | C | ASN | D | 354 | 0.650 | 22.141 | −20.029 | 1.00 | 108.66 | C |
| ATOM | 248 | O | ASN | D | 354 | 0.515 | 22.94 | −20.917 | 1.00 | 95.74 | O |
| ATOM | 256 | N | GLU | D | 361 | 0.649 | 23.536 | −4.858 | 1.00 | 73.70 | N |
| ATOM | 257 | CA | GLU | D | 361 | −0.666 | 23.174 | −5.386 | 1.00 | 78.86 | C |
| ATOM | 258 | CB | GLU | D | 361 | −0.494 | 22.797 | −6.882 | 1.00 | 94.81 | C |
| ATOM | 259 | CG | GLU | D | 361 | −1.725 | 22.293 | −7.657 | 1.00 | 101.97 | C |
| ATOM | 260 | CD | GLU | D | 361 | −2.660 | 23.403 | −8.126 | 1.00 | 103.74 | C |
| ATOM | 261 | OE1 | GLU | D | 361 | −3.437 | 23.920 | −7.292 | 1.00 | 110.47 | O |
| ATOM | 262 | OE2 | GLU | D | 361 | −2.639 | 23.749 | −9.328 | 1.00 | 94.85 | O |

TABLE 8-continued

Atomic coordinates for unbound CRBN-CRBN (TBD) (Apo) (Murine protein)

| ATOM | 263 | C | GLU | D | 361 | −1.306 | 22.021 | −4.557 | 1.00 | 81.00 | C |
|------|-----|------|-----|---|-----|--------|--------|--------|------|-------|---|
| ATOM | 264 | O | GLU | D | 361 | −2.135 | 22.230 | −3.647 | 1.00 | 76.96 | O |
| ATOM | 265 | N | THR | D | 362 | −0.883 | 20.802 | −4.865 | 1.00 | 67.78 | N |
| ATOM | 266 | CA | THR | D | 362 | −1.449 | 19.598 | −4.271 | 1.00 | 65.60 | C |
| ATOM | 267 | CB | THR | D | 362 | −2.137 | 18.781 | −5.366 | 1.00 | 58.43 | C |
| ATOM | 268 | OG1 | THR | D | 362 | −3.241 | 19.541 | −5.857 | 1.00 | 61.92 | O |
| ATOM | 269 | CG2 | THR | D | 362 | −2.654 | 17.508 | −4.836 | 1.00 | 62.36 | C |
| ATOM | 270 | C | THR | D | 362 | −0.363 | 18.772 | −3.591 | 1.00 | 56.83 | C |
| ATOM | 271 | O | THR | D | 362 | 0.740 | 18.661 | −4.108 | 1.00 | 56.12 | O |
| ATOM | 272 | N | LEU | D | 363 | −0.669 | 18.256 | −2.411 | 1.00 | 47.66 | N |
| ATOM | 273 | CA | LEU | D | 363 | 0.222 | 17.332 | −1.693 | 1.00 | 47.65 | C |
| ATOM | 274 | CB | LEU | D | 363 | −0.058 | 17.445 | −0.214 | 1.00 | 40.60 | C |
| ATOM | 275 | CG | LEU | D | 363 | 0.709 | 16.582 | 0.759 | 1.00 | 47.08 | C |
| ATOM | 276 | CD1 | LEU | D | 363 | 2.125 | 17.170 | 0.863 | 1.00 | 47.86 | C |
| ATOM | 277 | CD2 | LEU | D | 363 | 0.006 | 16.680 | 2.113 | 1.00 | 47.04 | C |
| ATOM | 278 | C | LEU | D | 363 | −0.097 | 15.883 | −2.076 | 1.00 | 47.68 | C |
| ATOM | 279 | O | LEU | D | 363 | −1.232 | 15.464 | −1.920 | 1.00 | 47.43 | O |
| ATOM | 280 | N | THR | D | 364 | 0.905 | 15.125 | −2.511 | 1.00 | 37.30 | N |
| ATOM | 281 | CA | THR | D | 364 | 0.759 | 13.717 | −2.939 | 1.00 | 38.68 | C |
| ATOM | 282 | CB | THR | D | 364 | 1.527 | 13.428 | −4.270 | 1.00 | 39.48 | C |
| ATOM | 283 | OG1 | THR | D | 364 | 2.922 | 13.730 | −4.087 | 1.00 | 39.46 | O |
| ATOM | 284 | CG2 | THR | D | 364 | 0.991 | 14.328 | −5.444 | 1.00 | 37.70 | C |
| ATOM | 285 | C | THR | D | 364 | 1.275 | 12.763 | −1.874 | 1.00 | 38.47 | C |
| ATOM | 286 | O | THR | D | 364 | 2.427 | 12.858 | −1.452 | 1.00 | 35.55 | O |
| ATOM | 287 | N | VAL | D | 365 | 0.430 | 11.843 | −1.418 | 1.00 | 39.09 | N |
| ATOM | 288 | CA | VAL | D | 365 | 0.832 | 10.889 | −0.363 | 1.00 | 38.75 | C |
| ATOM | 289 | CB | VAL | D | 365 | 0.120 | 11.180 | 0.978 | 1.00 | 39.39 | C |
| ATOM | 290 | CG1 | VAL | D | 365 | 0.534 | 12.535 | 1.550 | 1.00 | 32.92 | C |
| ATOM | 291 | CG2 | VAL | D | 365 | −1.392 | 11.170 | 0.774 | 1.00 | 36.96 | C |
| ATOM | 292 | C | VAL | D | 365 | 0.501 | 9.452 | −0.788 | 1.00 | 42.90 | C |
| ATOM | 293 | O | VAL | D | 365 | −0.470 | 9.218 | −1.523 | 1.00 | 42.04 | O |
| ATOM | 294 | N | TYR | D | 366 | 1.300 | 8.486 | −0.327 | 1.00 | 39.07 | N |
| ATOM | 295 | CA | TYR | D | 366 | 1.034 | 7.080 | −0.654 | 1.00 | 36.94 | C |
| ATOM | 296 | CB | TYR | D | 366 | 2.202 | 6.194 | −0.251 | 1.00 | 35.53 | C |
| ATOM | 297 | CG | TYR | D | 366 | 3.417 | 6.305 | −1.144 | 1.00 | 38.31 | C |
| ATOM | 298 | CD1 | TYR | D | 366 | 3.355 | 5.936 | −2.461 | 1.00 | 35.27 | C |
| ATOM | 299 | CE1 | TYR | D | 366 | 4.485 | 5.986 | −3.266 | 1.00 | 41.62 | C |
| ATOM | 300 | CZ | TYR | D | 366 | 5.708 | 6.440 | −2.738 | 1.00 | 39.52 | C |
| ATOM | 301 | OH | TYR | D | 366 | 6.828 | 6.512 | −3.537 | 1.00 | 43.05 | O |
| ATOM | 302 | CE2 | TYR | D | 366 | 5.780 | 6.825 | −1.433 | 1.00 | 38.78 | C |
| ATOM | 303 | CD2 | TYR | D | 366 | 4.633 | 6.749 | −0.635 | 1.00 | 40.22 | C |
| ATOM | 304 | C | TYR | D | 366 | −0.236 | 6.485 | −0.040 | 1.00 | 36.53 | C |
| ATOM | 305 | O | TYR | D | 366 | −0.811 | 5.546 | −0.607 | 1.00 | 36.31 | O |
| ATOM | 306 | N | LYS | D | 367 | −0.661 | 7.019 | 1.101 | 1.00 | 37.66 | N |
| ATOM | 307 | CA | LYS | D | 367 | −1.670 | 6.372 | 1.966 | 1.00 | 35.38 | C |
| ATOM | 308 | CB | LYS | D | 367 | −0.965 | 5.543 | 3.026 | 1.00 | 38.11 | C |
| ATOM | 309 | CG | LYS | D | 367 | −0.436 | 4.217 | 2.493 | 1.00 | 41.05 | C |
| ATOM | 310 | CD | LYS | D | 367 | −1.614 | 3.256 | 2.343 | 1.00 | 36.63 | C |
| ATOM | 311 | CE | LYS | D | 367 | −1.182 | 1.988 | 1.668 | 1.00 | 40.20 | C |
| ATOM | 312 | NZ | LYS | D | 367 | −2.253 | 0.942 | 1.671 | 1.00 | 31.91 | N |
| ATOM | 313 | C | LYS | D | 367 | −2.459 | 7.463 | 2.678 | 1.00 | 38.13 | C |
| ATOM | 314 | O | LYS | D | 367 | −1.894 | 8.493 | 3.058 | 1.00 | 35.35 | O |
| ATOM | 315 | N | ALA | D | 368 | −3.762 | 7.239 | 2.852 | 1.00 | 37.55 | N |
| ATOM | 316 | CA | ALA | D | 368 | −4.611 | 8.184 | 3.545 | 1.00 | 36.54 | C |
| ATOM | 317 | CB | ALA | D | 368 | −5.122 | 9.273 | 2.599 | 1.00 | 33.79 | C |
| ATOM | 318 | C | ALA | D | 368 | −5.755 | 7.443 | 4.206 | 1.00 | 40.87 | C |
| ATOM | 319 | O | ALA | D | 368 | −6.066 | 6.270 | 3.855 | 1.00 | 43.72 | O |
| ATOM | 320 | N | SER | D | 369 | −6.341 | 8.093 | 5.206 | 1.00 | 37.45 | N |
| ATOM | 321 | CA | SER | D | 369 | −7.318 | 7.408 | 6.046 | 1.00 | 41.38 | C |
| ATOM | 322 | CB | SER | D | 369 | −6.699 | 7.157 | 7.407 | 1.00 | 39.35 | C |
| ATOM | 323 | OG | SER | D | 369 | −6.208 | 8.382 | 7.910 | 1.00 | 39.78 | O |
| ATOM | 324 | C | SER | D | 369 | −8.576 | 8.261 | 6.232 | 1.00 | 40.88 | C |
| ATOM | 325 | O | SER | D | 369 | −8.511 | 9.483 | 6.118 | 1.00 | 40.71 | O |
| ATOM | 326 | N | ASN | D | 370 | −9.704 | 7.610 | 6.527 | 1.00 | 39.09 | N |
| ATOM | 327 | CA | ASN | D | 370 | −10.904 | 8.288 | 6.977 | 1.00 | 40.01 | C |
| ATOM | 328 | CB | ASN | D | 370 | −10.580 | 9.133 | 8.230 | 1.00 | 37.02 | C |
| ATOM | 329 | CG | ASN | D | 370 | −10.023 | 8.298 | 9.379 | 1.00 | 41.00 | C |
| ATOM | 330 | OD1 | ASN | D | 370 | −9.061 | 8.703 | 10.045 | 1.00 | 46.22 | O |
| ATOM | 331 | ND2 | ASN | D | 370 | −10.642 | 7.156 | 9.653 | 1.00 | 34.91 | N |
| ATOM | 332 | C | ASN | D | 370 | −11.526 | 9.176 | 5.902 | 1.00 | 39.22 | C |
| ATOM | 333 | O | ASN | D | 370 | −12.187 | 10.154 | 6.233 | 1.00 | 41.94 | O |
| ATOM | 334 | N | LEU | D | 371 | −11.277 | 8.844 | 4.633 | 1.00 | 39.96 | N |
| ATOM | 335 | CA | ASN | D | 371 | −11.895 | 9.514 | 3.478 | 1.00 | 39.72 | C |
| ATOM | 336 | CB | ASN | D | 371 | −10.846 | 9.841 | .2.411 | 1.00 | 39.71 | C |
| ATOM | 337 | CG | ASN | D | 371 | −9.838 | 10.877 | 2.862 | 1.00 | 46.23 | C |
| ATOM | 338 | CD1 | ASN | D | 371 | −8.630 | 10.941 | 1.912 | 1.00 | 46.82 | C |
| ATOM | 339 | CD2 | ASN | D | 371 | −10.554 | 12.248 | 2.980 | 1.00 | 40.38 | C |
| ATOM | 340 | C | ASN | D | 371 | −12.993 | 8.626 | 2.875 | 1.00 | 42.32 | C |

TABLE 8-continued

Atomic coordinates for unbound CRBN-CRBN (TBD) (Apo) (Murine protein)

| ATOM | 341 | O | LEU | D | 371 | −12.897 | 7.403 | 2.907 | 1.00 | 43.33 | O |
|---|---|---|---|---|---|---|---|---|---|---|---|
| ATOM | 342 | N | ASN | D | 372 | −14.052 | 9.254 | 2.353 | 1.00 | 43.09 | N |
| ATOM | 343 | CA | ASN | D | 372 | −15.061 | 8.551 | 1.613 | 1.00 | 41.55 | C |
| ATOM | 344 | CB | ASN | D | 372 | −16.425 | 8.994 | 2.092 | 1.00 | 60.96 | C |
| ATOM | 345 | CG | ASN | D | 372 | −17.477 | 7.948 | 1.854 | 1.00 | 83.91 | C |
| ATOM | 346 | OD1 | ASN | D | 372 | −17.369 | 7.139 | 0.903 | 1.00 | 97.06 | O |
| ATOM | 347 | ND2 | ASN | D | 372 | −18.514 | 7.943 | 2.726 | 1.00 | 100.60 | N |
| ATOM | 348 | C | ASN | D | 372 | −14.865 | 8.887 | 0.141 | 1.00 | 41.59 | C |
| ATOM | 349 | O | ASN | D | 372 | −14.626 | 10.039 | −0.218 | 1.00 | 35.99 | O |
| ATOM | 350 | N | LEU | D | 373 | −14.926 | 7.874 | −0.696 | 1.00 | 39.15 | N |
| ATOM | 351 | CA | LEU | D | 373 | −14.715 | 8.019 | −2.132 | 1.00 | 45.44 | C |
| ATOM | 352 | CB | LEU | D | 373 | −14.082 | 6.750 | −2.696 | 1.00 | 41.00 | C |
| ATOM | 353 | CG | LEU | D | 373 | −12.629 | 6.605 | −2.294 | 1.00 | 43.32 | C |
| ATOM | 354 | CD1 | LEU | D | 373 | −12.054 | 5.283 | −2.839 | 1.00 | 43.67 | C |
| ATOM | 355 | CD2 | LEU | D | 373 | −11.930 | 7.826 | −2.876 | 1.00 | 39.94 | C |
| ATOM | 356 | C | LEU | D | 373 | −16.059 | 8.158 | −2.756 | 1.00 | 42.30 | C |
| ATOM | 357 | O | LEU | D | 373 | −16.950 | 7.403 | −2.402 | 1.00 | 44.24 | O |
| ATOM | 358 | N | ILE | D | 374 | −16.193 | 9.140 | −3.646 | 1.00 | 43.01 | N |
| ATOM | 359 | CA | ILE | D | 374 | −17.456 | 9.519 | −4.303 | 1.00 | 48.13 | C |
| ATOM | 360 | CB | ILE | D | 374 | −17.662 | 11.062 | −4.241 | 1.00 | 49.81 | C |
| ATOM | 361 | CG1 | ILE | D | 374 | −17.615 | 11.564 | −2.798 | 1.00 | 52.05 | C |
| ATOM | 362 | CD1 | ILE | D | 374 | −18.683 | 10.926 | −1.906 | 1.00 | 55.93 | C |
| ATOM | 363 | CG2 | ILE | D | 374 | −18.985 | 11.484 | −4.864 | 1.00 | 51.81 | C |
| ATOM | 364 | C | ILE | D | 374 | −17.444 | 9.080 | −5.769 | 1.00 | 51.44 | C |
| ATOM | 365 | O | ILE | D | 374 | −16.584 | 9.510 | −6.553 | 1.00 | 48.09 | O |
| ATOM | 366 | N | GLY | D | 375 | −18.393 | 8.225 | −6.140 | 1.00 | 53.31 | N |
| ATOM | 367 | CA | GLY | D | 375 | −18.530 | 7.774 | −7.525 | 1.00 | 51.35 | C |
| ATOM | 368 | C | GLY | D | 375 | −17.399 | 6.856 | −7.948 | 1.00 | 60.66 | C |
| ATOM | 369 | O | GLY | D | 375 | −16.756 | 6.261 | −7.095 | 1.00 | 53.98 | O |
| ATOM | 370 | N | ARG | D | 376 | −17.165 | 6.727 | −9.263 | 1.00 | 63.05 | N |
| ATOM | 371 | CA | ARG | D | 376 | −16.105 | 5.852 | −9.794 | 1.00 | 63.00 | C |
| ATOM | 372 | CB | ARG | D | 376 | −16.702 | 4.795 | −10.726 | 1.00 | 77.33 | C |
| ATOM | 373 | CG | ARG | D | 376 | −16.828 | 3.412 | −10.077 | 1.00 | 95.98 | C |
| ATOM | 374 | CD | ARG | D | 376 | −17.982 | 2.607 | −10.659 | 1.00 | 106.73 | C |
| ATOM | 375 | NE | ARG | D | 376 | −19.238 | 3.371 | −10.650 | 1.00 | 113.18 | N |
| ATOM | 376 | CZ | ARG | D | 376 | −20.104 | 3.408 | −9.636 | 1.00 | 116.94 | C |
| ATOM | 377 | NH1 | ARG | D | 376 | −19.875 | 2.720 | −8.523 | 1.00 | 117.62 | N |
| ATOM | 378 | NH2 | ARG | D | 376 | −21.209 | 4.136 | −9.736 | 1.00 | 118.46 | N |
| ATOM | 379 | C | ARG | D | 376 | −14.940 | 6.591 | −10.488 | 1.00 | 57.87 | C |
| ATOM | 380 | O | ARG | D | 376 | −15.070 | 7.754 | −10.918 | 1.00 | 55.41 | O |
| ATOM | 381 | N | PRO | D | 377 | −13.786 | 5.926 | −10.613 | 1.00 | 54.88 | N |
| ATOM | 382 | CA | PRO | D | 377 | −12.634 | 6.681 | −11.146 | 1.00 | 49.44 | C |
| ATOM | 383 | CB | PRO | D | 377 | −11.522 | 5.619 | −11.266 | 1.00 | 52.32 | C |
| ATOM | 384 | CG | PRO | D | 377 | −12.137 | 4.293 | −10.854 | 1.00 | 49.53 | C |
| ATOM | 385 | CD | PRO | D | 377 | −13.447 | 4.558 | −10.179 | 1.00 | 47.67 | C |
| ATOM | 386 | C | PRO | D | 377 | −12.957 | 7.337 | −12.519 | 1.00 | 55.60 | C |
| ATOM | 387 | O | PRO | D | 377 | −13.724 | 6.777 | −13.313 | 1.00 | 53.18 | O |
| ATOM | 388 | N | SER | D | 378 | −12.398 | 8.518 | −12.787 | 1.00 | 48.60 | N |
| ATOM | 389 | CA | SER | D | 378 | −12.622 | 9.211 | −14.072 | 1.00 | 45.64 | C |
| ATOM | 390 | CB | SER | D | 378 | −13.476 | 10.463 | −13.846 | 1.00 | 41.40 | C |
| ATOM | 391 | OG | SER | D | 378 | −13.537 | 11.269 | −15.016 | 1.00 | 48.26 | O |
| ATOM | 392 | C | SER | D | 378 | −11.304 | 9.636 | −14.673 | 1.00 | 45.17 | C |
| ATOM | 393 | O | SER | D | 378 | −10.420 | 10.051 | −13.933 | 1.00 | 46.90 | O |
| ATOM | 394 | N | THR | D | 379 | −11.155 | 9.553 | −16.001 | 1.00 | 45.76 | N |
| ATOM | 395 | CA | THR | D | 379 | −9.981 | 10.138 | −16.657 | 1.00 | 50.65 | C |
| ATOM | 396 | CB | THR | D | 379 | −9.368 | 9.217 | −17.731 | 1.00 | 52.80 | C |
| ATOM | 397 | OG1 | THR | D | 379 | −10.421 | 8.681 | −18.531 | 1.00 | 59.91 | O |
| ATOM | 398 | CG2 | THR | D | 379 | −8.549 | 8.062 | −17.106 | 1.00 | 55.70 | C |
| ATOM | 399 | C | THR | D | 379 | −10.229 | 11.515 | −17.305 | 1.00 | 54.20 | C |
| ATOM | 400 | O | THR | D | 379 | −9.394 | 11.971 | −18.089 | 1.00 | 57.96 | O |
| ATOM | 401 | N | VAL | D | 380 | −11.342 | 12.176 | −17.001 | 1.00 | 52.30 | N |
| ATOM | 402 | CA | VAL | D | 380 | −11.613 | 13.514 | −17.586 | 1.00 | 49.06 | C |
| ATOM | 403 | CB | VAL | D | 380 | −13.090 | 13.921 | −17.452 | 1.00 | 58.92 | C |
| ATOM | 404 | CG1 | VAL | D | 380 | −13.295 | 15.250 | −18.165 | 1.00 | 52.92 | C |
| ATOM | 405 | CG2 | VAL | D | 380 | −14.018 | 12.826 | −18.024 | 1.00 | 43.39 | C |
| ATOM | 406 | C | VAL | D | 380 | −10.732 | 14.632 | −17.010 | 1.00 | 49.46 | C |
| ATOM | 407 | O | VAL | D | 380 | −10.798 | 14.906 | −15.840 | 1.00 | 45.09 | O |
| ATOM | 408 | N | HIS | D | 381 | −9.910 | 15.275 | −17.847 | 1.00 | 53.26 | N |
| ATOM | 409 | CA | HIS | D | 381 | −8.976 | 16.354 | −17.425 | 1.00 | 53.95 | C |
| ATOM | 410 | CB | HIS | D | 381 | −9.716 | 17.676 | −17.250 | 1.00 | 65.96 | C |
| ATOM | 411 | CG | HIS | D | 381 | −10.171 | 18.287 | −18.546 | 1.00 | 84.42 | C |
| ATOM | 412 | ND1 | HIS | D | 381 | −9.477 | 19.255 | −19.170 | 1.00 | 93.36 | N |
| ATOM | 413 | CE1 | HIS | D | 381 | −10.115 | 19.596 | −20.308 | 1.00 | 91.59 | C |
| ATOM | 414 | NE2 | HIS | D | 381 | −11.219 | 18.832 | −20.414 | 1.00 | 90.03 | N |
| ATOM | 415 | CD2 | HIS | D | 381 | −11.283 | 18.013 | −19.350 | 1.00 | 88.54 | C |
| ATOM | 416 | C | HIS | D | 381 | −8.162 | 16.078 | −16.187 | 1.00 | 51.81 | C |
| ATOM | 417 | O | HIS | D | 381 | −8.008 | 16.952 | −15.333 | 1.00 | 44.62 | O |
| ATOM | 418 | N | SER | D | 382 | −7.653 | 14.853 | −16.056 | 1.00 | 50.47 | N |

TABLE 8-continued

Atomic coordinates for unbound CRBN-CRBN (TBD) (Apo) (Murine protein)

| ATOM | 419 | CA | SER | D | 382 | −6.966 | 14.459 | −14.848 | 1.00 | 46.86 | C |
|---|---|---|---|---|---|---|---|---|---|---|---|
| ATOM | 420 | CB | SER | D | 382 | −6.538 | 13.009 | −14.963 | 1.00 | 48.71 | C |
| ATOM | 421 | OG | SER | D | 382 | −5.752 | 12.678 | −13.831 | 1.00 | 43.96 | O |
| ATOM | 422 | C | SER | D | 382 | −5.734 | 15.331 | −14.635 | 1.00 | 50.18 | C |
| ATOM | 423 | O | SER | D | 382 | −4.974 | 15.626 | −15.571 | 1.00 | 48.42 | O |
| ATOM | 424 | N | TRP | D | 383 | −5.530 | 15.740 | −13.400 | 1.00 | 52.27 | N |
| ATOM | 425 | CA | TRP | D | 383 | −4.386 | 16.566 | −13.062 | 1.00 | 54.54 | C |
| ATOM | 426 | CB | TRP | D | 383 | −4.544 | 17.206 | −11.697 | 1.00 | 50.70 | C |
| ATOM | 427 | CG | TRP | D | 383 | −5.514 | 18.336 | −11.624 | 1.00 | 53.73 | C |
| ATOM | 428 | CD1 | TRP | D | 383 | −6.380 | 18.798 | −12.620 | 1.00 | 54.90 | C |
| ATOM | 429 | NE1 | TRP | D | 383 | −7.163 | 19.826 | −12.147 | 1.00 | 51.82 | N |
| ATOM | 430 | CE2 | TRP | D | 383 | −6.890 | 20.075 | −10.840 | 1.00 | 52.80 | C |
| ATOM | 431 | CD2 | TRP | D | 383 | −5.823 | 19.148 | −10.438 | 1.00 | 54.50 | C |
| ATOM | 432 | CE3 | TRP | D | 383 | −5.358 | 19.180 | −9.120 | 1.00 | 59.36 | C |
| ATOM | 433 | CZ3 | TRP | D | 383 | −5.905 | 20.120 | −8.233 | 1.00 | 59.86 | C |
| ATOM | 434 | CH2 | TRP | D | 383 | −6.907 | 21.021 | −8.646 | 1.00 | 59.60 | C |
| ATOM | 435 | CZ2 | TRP | D | 383 | −7.415 | 21.015 | −9.960 | 1.00 | 55.96 | C |
| ATOM | 436 | C | TRP | D | 383 | −3.105 | 15.795 | −13.030 | 1.00 | 57.94 | C |
| ATOM | 437 | O | TRP | D | 383 | −2.072 | 16.416 | −12.884 | 1.00 | 59.08 | O |
| ATOM | 438 | N | PHE | D | 384 | −3.164 | 14.457 | −13.086 | 1.00 | 50.79 | N |
| ATOM | 439 | CA | PHE | D | 384 | −1.970 | 13.623 | −13.224 | 1.00 | 42.57 | C |
| ATOM | 440 | CB | PHE | D | 384 | −1.587 | 12.887 | −11.910 | 1.00 | 44.85 | C |
| ATOM | 441 | CG | PHE | D | 384 | −1.349 | 13.807 | −10.713 | 1.00 | 42.92 | C |
| ATOM | 442 | CD1 | PHE | D | 384 | −0.057 | 14.251 | −10.385 | 1.00 | 49.71 | C |
| ATOM | 443 | CE1 | PHE | D | 384 | −0.178 | 15.082 | −9.276 | 1.00 | 44.42 | C |
| ATOM | 444 | CZ | PHE | D | 384 | −0.887 | 15.481 | −8.476 | 1.00 | 39.31 | C |
| ATOM | 445 | CE2 | PHE | D | 384 | −2.163 | 15.032 | −8.772 | 1.00 | 36.25 | C |
| ATOM | 446 | CD2 | PHE | D | 384 | −2.399 | 14.197 | −9.882 | 1.00 | 40.18 | C |
| ATOM | 447 | C | PHE | D | 384 | −2.220 | 12.629 | −14.344 | 1.00 | 41.35 | C |
| ATOM | 448 | O | PHE | D | 384 | −2.713 | 11.521 | −14.105 | 1.00 | 42.65 | O |
| ATOM | 449 | N | PRO | D | 385 | −1.863 | 13.013 | −15.589 | 1.00 | 44.97 | N |
| ATOM | 450 | CA | PRO | D | 385 | −2.053 | 12.210 | −16.802 | 1.00 | 42.45 | C |
| ATOM | 451 | CB | PRO | D | 385 | −1.156 | 12.920 | −17.843 | 1.00 | 44.36 | C |
| ATOM | 452 | CG | PRO | D | 385 | −1.071 | 14.337 | −17.353 | 1.00 | 50.89 | C |
| ATOM | 453 | CD | PRO | D | 385 | −1.091 | 14.255 | −15.853 | 1.00 | 48.53 | C |
| ATOM | 454 | C | PRO | D | 385 | −1.536 | 10.801 | −16.604 | 1.00 | 42.33 | C |
| ATOM | 455 | O | PRO | D | 385 | −0.432 | 10.636 | −16.099 | 1.00 | 50.35 | O |
| ATOM | 456 | N | GLY | D | 386 | −2.274 | 9.795 | −17.038 | 1.00 | 38.27 | N |
| ATOM | 457 | CA | GLY | D | 386 | −1.931 | 8.404 | −16.702 | 1.00 | 42.50 | C |
| ATOM | 458 | C | GLY | D | 386 | −2.665 | 7.859 | −15.475 | 1.00 | 43.67 | C |
| ATOM | 459 | O | GLY | D | 386 | −2.632 | 6.637 | −15.242 | 1.00 | 53.89 | O |
| ATOM | 460 | N | TYR | D | 387 | −3.316 | 8.747 | −14.707 | 1.00 | 40.11 | N |
| ATOM | 461 | CA | TYR | D | 387 | −4.195 | 8.374 | −13.557 | 1.00 | 43.85 | C |
| ATOM | 462 | CB | TYR | D | 387 | −3.653 | 8.934 | −12.250 | 1.00 | 41.31 | C |
| ATOM | 463 | CG | TYR | D | 387 | −2.323 | 8.374 | −11.869 | 1.00 | 39.68 | C |
| ATOM | 464 | CD1 | TYR | D | 387 | −2.243 | 7.258 | −11.020 | 1.00 | 38.46 | C |
| ATOM | 465 | CE1 | TYR | D | 387 | −1.012 | 6.738 | −10.633 | 1.00 | 36.60 | C |
| ATOM | 466 | CZ | TYR | D | 387 | 0.161 | 7.295 | −11.112 | 1.00 | 38.29 | C |
| ATOM | 467 | OH | TYR | D | 387 | 1.355 | 6.741 | −10.698 | 1.00 | 36.98 | O |
| ATOM | 468 | CE2 | TYR | D | 387 | 0.123 | 8.422 | −11.968 | 1.00 | 36.77 | C |
| ATOM | 469 | CD2 | TYR | D | 387 | −1.138 | 8.955 | −12.332 | 1.00 | 35.98 | C |
| ATOM | 470 | C | TYR | D | 387 | −5.618 | 8.908 | −13.664 | 1.00 | 45.38 | C |
| ATOM | 471 | O | TYR | D | 387 | −5.859 | 10.031 | −14.149 | 1.00 | 43.20 | O |
| ATOM | 472 | N | ALA | D | 388 | −6.542 | 8.105 | −13.164 | 1.00 | 42.87 | N |
| ATOM | 473 | CA | ALA | D | 388 | −7.945 | 8.457 | −13.058 | 1.00 | 42.04 | C |
| ATOM | 474 | CB | ALA | D | 388 | −8.803 | 7.219 | −13.258 | 1.00 | 43.84 | C |
| ATOM | 475 | C | ALA | D | 388 | −8.105 | 8.982 | −11.638 | 1.00 | 42.38 | C |
| ATOM | 476 | O | ALA | D | 388 | −7.279 | 8.688 | −10.765 | 1.00 | 41.27 | O |
| ATOM | 477 | N | TRP | D | 389 | −9.141 | 9.780 | −11.397 | 1.00 | 36.99 | N |
| ATOM | 478 | CA | TRP | D | 389 | −9.271 | 10.391 | −10.125 | 1.00 | 38.00 | C |
| ATOM | 479 | CB | TRP | D | 389 | −9.011 | 11.904 | −10.260 | 1.00 | 41.25 | C |
| ATOM | 480 | CG | TRP | D | 389 | −9.824 | 12.546 | −11.350 | 1.00 | 41.91 | C |
| ATOM | 481 | CD1 | TRP | D | 389 | −9.432 | 12.777 | −12.682 | 1.00 | 46.68 | C |
| ATOM | 482 | NE1 | TRP | D | 389 | −10.436 | 13.380 | −13.394 | 1.00 | 40.83 | N |
| ATOM | 483 | CE2 | TRP | D | 389 | −11.525 | 13.582 | −12.611 | 1.00 | 43.61 | C |
| ATOM | 484 | CD2 | TRP | D | 389 | −11.196 | 13.053 | −11.262 | 1.00 | 38.53 | C |
| ATOM | 485 | CE3 | TRP | D | 389 | −12.162 | 13.123 | −10.249 | 1.00 | 42.34 | C |
| ATOM | 486 | CZ3 | TRP | D | 389 | −13.425 | 13.708 | −10.563 | 1.00 | 44.28 | C |
| ATOM | 487 | CH2 | TRP | D | 389 | −13.711 | 14.200 | −11.861 | 1.00 | 42.67 | C |
| ATOM | 488 | CZ2 | TRP | D | 389 | −12.771 | 14.131 | −12.911 | 1.00 | 40.00 | C |
| ATOM | 489 | C | TRP | D | 389 | −10.629 | 10.049 | −9.583 | 1.00 | 40.55 | C |
| ATOM | 490 | O | TRP | D | 389 | −11.539 | 9.689 | −10.331 | 1.00 | 43.50 | O |
| ATOM | 491 | N | THR | D | 390 | −10.780 | 10.105 | −8.272 | 1.00 | 42.62 | N |
| ATOM | 492 | CA | THR | D | 390 | −12.090 | 9.887 | −7.642 | 1.00 | 40.01 | C |
| ATOM | 493 | CB | THR | D | 390 | −12.226 | 8.452 | −7.030 | 1.00 | 46.04 | C |
| ATOM | 494 | OG1 | THR | D | 390 | −11.890 | 7.460 | −8.012 | 1.00 | 48.23 | O |
| ATOM | 495 | CG2 | THR | D | 390 | −13.677 | 8.182 | −6.494 | 1.00 | 38.86 | C |
| ATOM | 496 | C | THR | D | 390 | −12.091 | 10.876 | −6.500 | 1.00 | 39.38 | C |

TABLE 8-continued

Atomic coordinates for unbound CRBN-CRBN (TBD) (Apo) (Murine protein)

| ATOM | 497 | O | THR | D | 390 | −11.141 | 10.920 | −5.695 | 1.00 | 40.56 | O |
|---|---|---|---|---|---|---|---|---|---|---|---|
| ATOM | 498 | N | ILE | D | 391 | −13.130 | 11.684 | −6.440 | 1.00 | 41.62 | N |
| ATOM | 499 | CA | ILE | D | 391 | −13.316 | 12.674 | −5.359 | 1.00 | 40.76 | C |
| ATOM | 500 | CB | ILE | D | 391 | −14.666 | 13.482 | −5.525 | 1.00 | 41.33 | C |
| ATOM | 501 | CG1 | ILE | D | 391 | −14.584 | 14.425 | −6.743 | 1.00 | 45.36 | C |
| ATOM | 502 | CD1 | ILE | D | 391 | −15.924 | 14.737 | −7.389 | 1.00 | 49.09 | C |
| ATOM | 503 | CG2 | ILE | D | 391 | −14.974 | 14.394 | −4.326 | 1.00 | 37.13 | C |
| ATOM | 504 | C | ILE | D | 391 | −13.260 | 11.973 | −4.015 | 1.00 | 42.74 | C |
| ATOM | 505 | O | ILE | D | 391 | −13.914 | 10.940 | −3.808 | 1.00 | 39.42 | O |
| ATOM | 506 | N | ALA | D | 392 | −12.534 | 12.587 | −3.082 | 1.00 | 38.01 | N |
| ATOM | 507 | CA | ALA | D | 392 | −12.400 | 12.019 | −1.758 | 1.00 | 39.29 | C |
| ATOM | 508 | CB | ALA | D | 392 | −10.935 | 11.681 | −1.500 | 1.00 | 29.28 | C |
| ATOM | 509 | C | ALA | D | 392 | −12.852 | 13.110 | −0.789 | 1.00 | 42.75 | C |
| ATOM | 510 | O | ALA | D | 392 | −12.394 | 14.239 | −0.890 | 1.00 | 37.28 | O |
| ATOM | 511 | N | GLN | D | 393 | −13.702 | 12.769 | 0.171 | 1.00 | 41.74 | N |
| ATOM | 512 | CA | GLN | D | 393 | −14.149 | 13.770 | 1.122 | 1.00 | 42.74 | C |
| ATOM | 513 | CB | GLN | D | 393 | −15.574 | 14.200 | 0.742 | 1.00 | 47.76 | C |
| ATOM | 514 | CG | GLN | D | 393 | −16.642 | 13.237 | 1.256 | 1.00 | 48.89 | C |
| ATOM | 515 | CD | GLN | D | 393 | −18.051 | 13.497 | 0.718 | 1.00 | 51.53 | C |
| ATOM | 516 | OE1 | GLN | D | 393 | −18.270 | 14.303 | −0.212 | 1.00 | 50.62 | O |
| ATOM | 517 | NE2 | GLN | D | 393 | −19.016 | 12.787 | 1.300 | 1.00 | 45.92 | N |
| ATOM | 518 | C | GLN | D | 393 | −14.059 | 13.221 | 2.559 | 1.00 | 39.76 | C |
| ATOM | 519 | O | GLN | D | 393 | −14.148 | 12.031 | 2.780 | 1.00 | 41.47 | O |
| ATOM | 520 | N | CYS | D | 394 | −13.879 | 14.086 | 3.551 | 1.00 | 44.74 | N |
| ATOM | 521 | CA | CYS | D | 394 | −13.650 | 13.608 | 4.915 | 1.00 | 42.99 | C |
| ATOM | 522 | CB | CYS | D | 394 | −13.417 | 14.783 | 5.850 | 1.00 | 47.08 | C |
| ATOM | 523 | SG | CYS | D | 394 | −13.518 | 14.299 | 7.582 | 1.00 | 43.84 | S |
| ATOM | 524 | C | CYS | D | 394 | −14.844 | 12.817 | 5.385 | 1.00 | 44.07 | C |
| ATOM | 525 | O | CYS | D | 394 | −15.977 | 13.233 | 5.150 | 1.00 | 40.98 | O |
| ATOM | 526 | N | LYS | D | 395 | −14.628 | 11.668 | 6.031 | 1.00 | 42.19 | N |
| ATOM | 527 | CA | LYS | D | 395 | −15.783 | 10.888 | 6.476 | 1.00 | 43.20 | C |
| ATOM | 528 | CB | LYS | D | 395 | −15.439 | 9.413 | 6.727 | 1.00 | 47.27 | C |
| ATOM | 529 | CG | LYS | D | 395 | −15.180 | 8.968 | 8.162 | 1.00 | 59.07 | C |
| ATOM | 530 | CD | LYS | D | 395 | −15.579 | 7.496 | 8.372 | 1.00 | 60.30 | C |
| ATOM | 531 | CE | LYS | D | 395 | −14.678 | 9.802 | 9.406 | 1.00 | 64.42 | C |
| ATOM | 532 | NZ | LYS | D | 395 | −13.411 | 6.224 | 8.811 | 1.00 | 55.03 | N |
| ATOM | 533 | C | LYS | D | 395 | −16.595 | 11.499 | 7.637 | 1.00 | 46.36 | C |
| ATOM | 534 | O | LYS | D | 395 | −17.764 | 11.176 | 7.822 | 1.00 | 41.91 | O |
| ATOM | 535 | N | ILE | D | 396 | −15.978 | 12.348 | 8.447 | 1.00 | 47.11 | N |
| ATOM | 536 | CA | ILE | D | 396 | −16.734 | 12.978 | 9.550 | 1.00 | 48.08 | C |
| ATOM | 537 | CB | ILE | D | 396 | −15.826 | 13.524 | 10.668 | 1.00 | 42.20 | C |
| ATOM | 538 | CG1 | ILE | D | 396 | −15.330 | 12.401 | 11.564 | 1.00 | 41.23 | C |
| ATOM | 539 | CD1 | ILE | D | 396 | −14.976 | 11.064 | 10.920 | 1.00 | 42.65 | C |
| ATOM | 540 | CG2 | ILE | D | 396 | −16.590 | 14.544 | 11.535 | 1.00 | 43.94 | C |
| ATOM | 541 | C | ILE | D | 396 | −17.636 | 14.106 | 9.060 | 1.00 | 47.33 | C |
| ATOM | 542 | O | ILE | D | 396 | −18.845 | 14.116 | 9.348 | 1.00 | 51.46 | O |
| ATOM | 543 | N | CYS | D | 397 | −17.051 | 15.039 | 8.320 | 1.00 | 46.61 | N |
| ATOM | 544 | CA | CYS | D | 397 | −17.767 | 16.287 | 7.972 | 1.00 | 47.51 | C |
| ATOM | 545 | CB | CYS | D | 397 | −16.956 | 17.468 | 8.475 | 1.00 | 41.13 | C |
| ATOM | 546 | SG | CYS | D | 397 | −15.425 | 17.685 | 7.558 | 1.00 | 49.86 | S |
| ATOM | 547 | C | CYS | D | 397 | −18.057 | 16.477 | 6.477 | 1.00 | 49.04 | C |
| ATOM | 548 | O | CYS | D | 397 | −18.652 | 17.493 | 6.104 | 1.00 | 44.62 | O |
| ATOM | 549 | N | ALA | D | 398 | −17.619 | 15.522 | 5.636 | 1.00 | 40.01 | N |
| ATOM | 550 | CA | ALA | D | 398 | −17.849 | 15.531 | 4.175 | 1.00 | 42.02 | C |
| ATOM | 551 | CB | ALA | D | 398 | −19.337 | 15.407 | 3.824 | 1.00 | 44.31 | C |
| ATOM | 552 | C | ALA | D | 398 | −17.196 | 16.678 | 3.429 | 1.00 | 41.97 | C |
| ATOM | 553 | O | ALA | D | 398 | −17.464 | 16.912 | 2.231 | 1.00 | 48.25 | O |
| ATOM | 554 | N | SER | D | 399 | −16.300 | 17.377 | 4.115 | 1.00 | 43.92 | N |
| ATOM | 555 | CA | SER | D | 399 | −15.410 | 18.318 | 3.428 | 1.00 | 45.15 | C |
| ATOM | 556 | CB | SER | D | 399 | −14.559 | 19.044 | 4.469 | 1.00 | 52.47 | C |
| ATOM | 557 | OG | SER | D | 399 | −13.484 | 19.731 | 3.870 | 1.00 | 60.55 | O |
| ATOM | 558 | C | SER | D | 399 | −14.552 | 17.652 | 2.298 | 1.00 | 51.34 | C |
| ATOM | 559 | O | SER | D | 399 | −14.106 | 16.486 | 2.414 | 1.00 | 45.92 | O |
| ATOM | 560 | N | HIS | D | 400 | −14.379 | 18.384 | 1.191 | 1.00 | 50.86 | N |
| ATOM | 561 | CA | HIS | D | 400 | −13.648 | 17.918 | 0.022 | 1.00 | 54.81 | C |
| ATOM | 562 | CB | HIS | D | 400 | −14.102 | 18.690 | −1.220 | 1.00 | 61.57 | C |
| ATOM | 563 | CG | HIS | D | 400 | −15.394 | 18.180 | −1.803 | 1.00 | 78.23 | C |
| ATOM | 564 | ND1 | HIS | D | 400 | −16.556 | 18.195 | −1.116 | 1.00 | 84.09 | N |
| ATOM | 565 | CE1 | HIS | D | 400 | −17.534 | 17.672 | −1.885 | 1.00 | 90.14 | C |
| ATOM | 566 | NE2 | HIS | D | 400 | −16.993 | 17.320 | −3.070 | 1.00 | 86.52 | N |
| ATOM | 567 | CD2 | HIS | D | 400 | −15.679 | 17.616 | −3.052 | 1.00 | 82.95 | C |
| ATOM | 568 | C | HIS | D | 400 | −12.150 | 18.031 | 0.175 | 1.00 | 53.59 | C |
| ATOM | 569 | O | HIS | D | 400 | −11.571 | 19.105 | −0.026 | 1.00 | 53.51 | O |
| ATOM | 570 | N | ILE | D | 401 | −11.499 | 16.913 | 0.481 | 1.00 | 47.50 | N |
| ATOM | 571 | CA | ILE | D | 401 | −10.083 | 16.951 | 0.822 | 1.00 | 45.10 | C |
| ATOM | 572 | CB | ILE | D | 401 | −9.728 | 15.921 | 1.911 | 1.00 | 42.94 | C |
| ATOM | 573 | CG1 | ILE | D | 401 | −10.757 | 15.997 | 3.045 | 1.00 | 45.50 | C |
| ATOM | 574 | CD1 | ILE | D | 401 | −10.668 | 17.273 | 3.885 | 1.00 | 39.69 | C |

TABLE 8-continued

Atomic coordinates for unbound CRBN-CRBN (TBD) (Apo) (Murine protein)

| ATOM | 575 | CG2 | ILE | D | 401 | −8.354 | 16.203 | 2.466 | 1.00 | 37.75 | C |
|---|---|---|---|---|---|---|---|---|---|---|---|
| ATOM | 576 | C | ILE | D | 401 | −9.223 | 16.857 | −0.435 | 1.00 | 44.49 | C |
| ATOM | 577 | O | ILE | D | 401 | −8.246 | 17.590 | −0.563 | 1.00 | 42.61 | O |
| ATOM | 578 | N | GLY | D | 402 | −9.617 | 16.012 | −1.392 | 1.00 | 42.46 | N |
| ATOM | 579 | CA | GLY | D | 402 | −8.882 | 15.932 | −2.657 | 1.00 | 39.09 | C |
| ATOM | 580 | C | GLY | D | 402 | −9.381 | 14.750 | −3.451 | 1.00 | 41.48 | C |
| ATOM | 581 | O | GLY | D | 402 | −10.584 | 14.539 | −3.537 | 1.00 | 41.87 | O |
| ATOM | 582 | N | TRP | D | 403 | −8.457 | 13.957 | −3.988 | 1.00 | 36.54 | N |
| ATOM | 583 | CA | TRP | D | 403 | −8.792 | 12.842 | −4.873 | 1.00 | 40.48 | C |
| ATOM | 584 | CB | TRP | D | 403 | −8.616 | 13.271 | −6.336 | 1.00 | 37.91 | C |
| ATOM | 585 | CG | TRP | D | 403 | −9.384 | 14.512 | −6.666 | 1.00 | 42.10 | C |
| ATOM | 586 | CD1 | TRP | D | 403 | −10.648 | 14.605 | −7.249 | 1.00 | 41.93 | C |
| ATOM | 587 | NE1 | TRP | D | 403 | −11.035 | 15.908 | −7.371 | 1.00 | 41.26 | N |
| ATOM | 588 | CE2 | TRP | D | 403 | −10.083 | 16.744 | −6.891 | 1.00 | 43.17 | C |
| ATOM | 589 | CD2 | TRP | D | 403 | −8.983 | 15.900 | −6.399 | 1.00 | 44.10 | C |
| ATOM | 590 | CE3 | TRP | D | 403 | −7.852 | 16.513 | −5.824 | 1.00 | 46.41 | C |
| ATOM | 591 | CZ3 | TRP | D | 403 | −7.833 | 17.926 | −5.742 | 1.00 | 50.37 | C |
| ATOM | 592 | CH2 | TRP | D | 403 | −8.923 | 18.707 | −6.191 | 1.00 | 45.40 | C |
| ATOM | 593 | CZ2 | TRP | D | 403 | −10.060 | 18.132 | −6.775 | 1.00 | 41.77 | C |
| ATOM | 594 | C | TRP | D | 403 | −7.891 | 11.625 | −4.628 | 1.00 | 40.57 | C |
| ATOM | 595 | O | TRP | D | 403 | −6.745 | 11.748 | −4.208 | 1.00 | 38.29 | O |
| ATOM | 596 | N | LYS | D | 404 | −8.434 | 10.453 | −4.885 | 1.00 | 38.50 | N |
| ATOM | 597 | CA | LYS | D | 404 | −7.677 | 9.229 | −5.005 | 1.00 | 42.00 | C |
| ATOM | 598 | CB | LYS | D | 404 | −8.509 | 8.029 | −4.551 | 1.00 | 42.95 | C |
| ATOM | 599 | CG | LYS | D | 404 | −7.693 | 6.731 | −4.510 | 1.00 | 44.50 | C |
| ATOM | 600 | CD | LYS | D | 404 | −8.558 | 5.507 | −4.293 | 1.00 | 39.95 | C |
| ATOM | 601 | CE | LYS | D | 404 | −7.774 | 4.405 | −3.602 | 1.00 | 44.57 | C |
| ATOM | 602 | NZ | LYS | D | 404 | −8.598 | 3.165 | −3.496 | 1.00 | 53.29 | N |
| ATOM | 603 | C | LYS | D | 404 | −7.378 | 9.036 | −6.472 | 1.00 | 37.59 | C |
| ATOM | 604 | O | LYS | D | 404 | −8.281 | 9.143 | −7.282 | 1.00 | 42.46 | O |
| ATOM | 605 | N | PHE | D | 405 | −6.112 | 8.780 | −6.794 | 1.00 | 36.10 | N |
| ATOM | 606 | CA | PHE | D | 405 | −5.652 | 8.599 | −8.167 | 1.00 | 34.19 | C |
| ATOM | 607 | CB | PHE | D | 405 | −4.438 | 9.502 | −8.424 | 1.00 | 29.96 | C |
| ATOM | 608 | CG | PHE | D | 405 | −4.804 | 10.945 | −8.531 | 1.00 | 32.29 | C |
| ATOM | 609 | CD1 | PHE | D | 405 | −5.256 | 11.469 | −9.748 | 1.00 | 33.11 | C |
| ATOM | 610 | CE1 | PHE | D | 405 | −5.649 | 12.815 | −9.852 | 1.00 | 35.15 | C |
| ATOM | 611 | CZ | PHE | D | 405 | −5.585 | 13.654 | −8.734 | 1.00 | 31.06 | C |
| ATOM | 612 | CE2 | PHE | D | 405 | −5.110 | 13.140 | −7.516 | 1.00 | 33.07 | C |
| ATOM | 613 | CD2 | PHE | D | 405 | −4.766 | 11.785 | −7.400 | 1.00 | 27.95 | C |
| ATOM | 614 | C | PHE | D | 405 | −5.263 | 7.147 | −8.372 | 1.00 | 39.42 | C |
| ATOM | 615 | O | PHE | D | 405 | −4.500 | 6.567 | −7.550 | 1.00 | 39.39 | O |
| ATOM | 616 | N | THR | D | 406 | −5.772 | 6.580 | −9.461 | 1.00 | 37.16 | N |
| ATOM | 617 | CA | THR | D | 406 | −5.612 | 5.159 | −9.759 | 1.00 | 46.82 | C |
| ATOM | 618 | CB | THR | D | 406 | −6.958 | 4.428 | −9.571 | 1.00 | 48.0 | C |
| ATOM | 619 | OG1 | THR | D | 406 | −7.994 | 5.162 | −10.241 | 1.00 | 42.68 | O |
| ATOM | 620 | CG2 | THR | D | 406 | −7.315 | 4.392 | −8.060 | 1.00 | 45.15 | C |
| ATOM | 621 | C | THR | D | 406 | −5.025 | 4.986 | −11.174 | 1.00 | 47.06 | C |
| ATOM | 622 | O | THR | D | 406 | −5.504 | 5.589 | −12.125 | 1.00 | 47.37 | O |
| ATOM | 623 | N | ALA | D | 407 | −3.934 | 4.232 | −11.286 | 1.00 | 50.53 | N |
| ATOM | 624 | CA | ALA | D | 407 | −3.209 | 4.107 | −12.559 | 1.00 | 47.98 | C |
| ATOM | 625 | CB | ALA | D | 407 | −1.893 | 3.360 | −12.359 | 1.00 | 43.70 | C |
| ATOM | 626 | C | ALA | D | 407 | −4.046 | 3.455 | −13.660 | 1.00 | 47.47 | C |
| ATOM | 627 | O | ALA | D | 407 | −4.741 | 2.490 | −13.417 | 1.00 | 47.99 | O |
| ATOM | 628 | N | THR | D | 408 | −3.995 | 4.004 | −14.867 | 1.00 | 50.73 | N |
| ATOM | 629 | CA | THR | D | 408 | −4.638 | 3.368 | −16.019 | 1.00 | 48.90 | C |
| ATOM | 630 | CB | THR | D | 408 | −4.865 | 4.390 | −17.148 | 1.00 | 52.90 | C |
| ATOM | 631 | OG1 | THR | D | 408 | −3.604 | 4.736 | −17.718 | 1.00 | 65.03 | O |
| ATOM | 632 | CG2 | THR | D | 408 | −5.528 | 5.665 | −16.633 | 1.00 | 48.66 | C |
| ATOM | 633 | C | THR | D | 408 | −3.818 | 2.180 | −16.588 | 1.00 | 55.73 | C |
| ATOM | 634 | O | THR | D | 408 | −4.393 | 1.297 | −17.220 | 1.00 | 65.03 | O |
| ATOM | 635 | N | LYS | D | 409 | −2.495 | 2.164 | −16.370 | 1.00 | 43.84 | N |
| ATOM | 636 | CA | LYS | D | 409 | −1.614 | 1.121 | −16.904 | 1.00 | 48.40 | C |
| ATOM | 637 | CB | LYS | D | 409 | −0.568 | 1.703 | −17.872 | 1.00 | 51.56 | C |
| ATOM | 638 | CG | LYS | D | 409 | −1.173 | 2.110 | −19.221 | 1.00 | 59.85 | C |
| ATOM | 639 | CD | LYS | D | 409 | −0.410 | 3.235 | −19.904 | 1.00 | 61.89 | C |
| ATOM | 640 | CE | LYS | D | 409 | −0.731 | 2.718 | −20.772 | 1.00 | 68.88 | C |
| ATOM | 641 | NZ | LYS | D | 409 | −2.036 | 2.799 | −20.050 | 1.00 | 75.28 | N |
| ATOM | 642 | C | LYS | D | 409 | −0.919 | 0.421 | −15.753 | 1.00 | 51.14 | C |
| ATOM | 643 | O | LYS | D | 409 | −0.483 | 1.075 | −14.788 | 1.00 | 44.23 | O |
| ATOM | 644 | N | LYS | D | 410 | −0.824 | −0.900 | −15.868 | 1.00 | 46.98 | N |
| ATOM | 645 | CA | LYS | D | 410 | −0.291 | −1.747 | −14.805 | 1.00 | 55.57 | C |
| ATOM | 646 | CB | LYS | D | 410 | −0.725 | −3.220 | −14.948 | 1.00 | 59.07 | C |
| ATOM | 647 | CG | LYS | D | 410 | −2.012 | −3.489 | −14.171 | 1.00 | 71.02 | C |
| ATOM | 648 | CD | LYS | D | 410 | −2.625 | −4.838 | −14.509 | 1.00 | 84.77 | C |
| ATOM | 649 | CE | LYS | D | 410 | −4.135 | −4.829 | −14.275 | 1.00 | 84.74 | C |
| ATOM | 650 | NZ | LYS | D | 410 | −4.805 | −5.993 | −14.930 | 1.00 | 73.33 | N |
| ATOM | 651 | C | LYS | D | 410 | 1.201 | −1.639 | −14.656 | 1.00 | 48.11 | C |
| ATOM | 652 | O | LYS | D | 410 | 1.733 | −2.047 | −13.626 | 1.00 | 50.91 | O |

TABLE 8-continued

Atomic coordinates for unbound CRBN-CRBN (TBD) (Apo) (Murine protein)

| ATOM | 653 | N | ASP | D | 411 | 1.867 | −1.040 | −15.634 | 1.00 | 44.66 | N |
| --- | --- | --- | --- | --- | --- | --- | --- | --- | --- | --- | --- |
| ATOM | 654 | CA | ASP | D | 411 | 3.312 | −0.918 | −15.543 | 1.00 | 51.79 | C |
| ATOM | 655 | CB | ASP | D | 411 | 3.940 | −0.997 | −16.936 | 1.00 | 54.31 | C |
| ATOM | 656 | CG | ASP | D | 411 | 3.753 | 0.282 | −17.724 | 1.00 | 66.92 | C |
| ATOM | 657 | OD1 | ASP | D | 411 | 2.809 | 1.046 | −17.407 | 1.00 | 66.28 | O |
| ATOM | 658 | OD2 | ASP | D | 411 | 4.560 | 0.538 | −18.648 | 1.00 | 66.53 | O |
| ATOM | 659 | C | ASP | D | 411 | 3.827 | 0.332 | −14.774 | 1.00 | 52.63 | C |
| ATOM | 660 | O | ASP | D | 411 | 5.030 | 0.484 | −14.659 | 1.00 | 50.01 | O |
| ATOM | 661 | N | MET | D | 412 | 2.922 | 1.203 | −14.285 | 1.00 | 52.18 | N |
| ATOM | 662 | CA | MET | D | 412 | 3.228 | 2.462 | −13.535 | 1.00 | 51.12 | C |
| ATOM | 663 | CB | MET | D | 412 | 2.043 | 3.462 | −13.622 | 1.00 | 43.95 | C |
| ATOM | 664 | CG | MET | D | 412 | 1.655 | 3.867 | −15.059 | 1.00 | 53.82 | C |
| ATOM | 665 | SD | MET | D | 412 | 0.110 | 4.811 | −15.230 | 1.00 | 54.87 | S |
| ATOM | 666 | CE | MET | D | 412 | 0.258 | 5.437 | −16.910 | 1.00 | 72.85 | C |
| ATOM | 667 | C | MET | D | 412 | 3.498 | 2.163 | −12.050 | 1.00 | 52.53 | C |
| ATOM | 668 | O | MET | D | 412 | 3.096 | 1.21 | −11.566 | 1.00 | 45.87 | O |
| ATOM | 669 | N | SER | D | 413 | 4.173 | 3.083 | −11.350 | 1.00 | 42.79 | N |
| ATOM | 670 | CA | SER | D | 413 | 4.338 | 3.032 | −9.890 | 1.00 | 44.77 | C |
| ATOM | 671 | CB | SER | D | 413 | 5.660 | 2.390 | −9.467 | 1.00 | 38.64 | C |
| ATOM | 672 | OG | SER | D | 413 | 6.756 | 3.225 | −9.841 | 1.00 | 43.86 | O |
| ATOM | 673 | C | SER | D | 413 | 4.330 | 4.482 | −9.409 | 1.00 | 43.78 | C |
| ATOM | 674 | O | SER | D | 413 | 4.971 | 5.343 | −10.033 | 1.00 | 41.02 | O |
| ATOM | 675 | N | PRO | D | 414 | 3.599 | 4.760 | −8.316 | 1.00 | 41.67 | N |
| ATOM | 676 | CA | PRO | D | 414 | 2.765 | 3.778 | −7.629 | 1.00 | 38.99 | C |
| ATOM | 677 | CB | PRO | D | 414 | 2.460 | 4.468 | −6.282 | 1.00 | 36.69 | C |
| ATOM | 678 | CG | PRO | D | 414 | 2.520 | 5.926 | −6.576 | 1.00 | 37.60 | C |
| ATOM | 679 | CD | PRO | D | 414 | 3.585 | 6.081 | −7.640 | 1.00 | 40.40 | C |
| ATOM | 680 | C | PRO | D | 414 | 1.485 | 3.560 | −8.437 | 1.00 | 41.67 | C |
| ATOM | 681 | O | PRO | D | 414 | 1.142 | 4.428 | −9.245 | 1.00 | 37.86 | O |
| ATOM | 682 | N | GLN | D | 415 | 0.812 | 2.413 | −8.258 | 1.00 | 41.52 | N |
| ATOM | 683 | CA | GLN | D | 415 | −0.457 | 2.115 | −8.923 | 1.00 | 39.90 | C |
| ATOM | 684 | CB | GLN | D | 415 | −0.856 | 0.642 | −7.743 | 1.00 | 40.25 | C |
| ATOM | 685 | CG | GLN | D | 415 | −0.038 | −0.315 | −9.645 | 1.00 | 46.99 | C |
| ATOM | 686 | CD | GLN | D | 415 | −0.534 | −0.221 | −11.08 | 1.00 | 45.75 | C |
| ATOM | 687 | OE1 | GLN | D | 415 | 0.074 | 0.443 | −11.919 | 1.00 | 47.06 | O |
| ATOM | 688 | NE2 | GLN | D | 415 | −1.680 | −0.781 | −11.346 | 1.00 | 44.81 | N |
| ATOM | 689 | C | GLN | D | 415 | −1.575 | 2.997 | −8.380 | 1.00 | 45.16 | C |
| ATOM | 690 | O | GLN | D | 415 | −2.599 | 3.211 | −9.052 | 1.00 | 40.41 | O |
| ATOM | 691 | N | LYS | D | 416 | −1.383 | 3.497 | −7.157 | 1.00 | 40.90 | N |
| ATOM | 692 | CA | LYS | D | 416 | −2.377 | 4.357 | −6.547 | 1.00 | 38.81 | C |
| ATOM | 693 | CB | LYS | D | 416 | −3.413 | 3.545 | −5.788 | 1.00 | 40.96 | C |
| ATOM | 694 | CG | LYS | D | 416 | −3.221 | 3.550 | −4.291 | 1.00 | 46.93 | C |
| ATOM | 695 | CD | LYS | D | 416 | −4.224 | 2.645 | −3.604 | 1.00 | 58.00 | C |
| ATOM | 696 | CE | LYS | D | 416 | −3.684 | 1.249 | −3.310 | 1.00 | 61.52 | C |
| ATOM | 697 | NZ | LYS | D | 416 | −4.170 | 0.286 | −4.344 | 1.00 | 61.46 | N |
| ATOM | 698 | C | LYS | D | 416 | −1.716 | 5.371 | −5.643 | 1.00 | 36.91 | C |
| ATOM | 699 | O | LYS | D | 416 | −0.654 | 5.125 | −5.069 | 1.00 | 39.65 | O |
| ATOM | 700 | N | PHE | D | 417 | −2.320 | 6.546 | −5.547 | 1.00 | 39.07 | N |
| ATOM | 701 | CA | PHE | D | 417 | −1.925 | 7.523 | −4.536 | 1.00 | 37.64 | C |
| ATOM | 702 | CB | PHE | D | 417 | −0.646 | 8.263 | −4.918 | 1.00 | 34.93 | C |
| ATOM | 703 | CG | PHE | D | 417 | −0.787 | 9.161 | −6.127 | 1.00 | 36.63 | C |
| ATOM | 704 | CD1 | PHE | D | 417 | −0.990 | 10.526 | −5.972 | 1.00 | 36.94 | C |
| ATOM | 705 | CE1 | PHE | D | 417 | −1.108 | 11.353 | −7.059 | 1.00 | 38.17 | C |
| ATOM | 706 | CZ | PHE | D | 417 | −0.980 | 10.826 | −8.339 | 1.00 | 38.78 | C |
| ATOM | 707 | CE2 | PHE | D | 417 | −0.722 | 9.475 | −8.499 | 1.00 | 40.57 | C |
| ATOM | 708 | CD2 | PHE | D | 417 | −0.629 | 8.654 | −7.392 | 1.00 | 32.68 | C |
| ATOM | 709 | C | PHE | D | 417 | −3.054 | 8.489 | −4.272 | 1.00 | 37.38 | C |
| ATOM | 710 | O | PHE | D | 417 | −4.091 | 8.425 | −4.945 | 1.00 | 39.45 | O |
| ATOM | 711 | N | TRP | D | 418 | −2.853 | 9.369 | −3.284 | 1.00 | 36.23 | N |
| ATOM | 712 | CA | TRP | D | 418 | −3.817 | 10.438 | −3.005 | 1.00 | 35.46 | C |
| ATOM | 713 | CB | TRP | D | 418 | −4.232 | 10.374 | −1.542 | 1.00 | 37.90 | C |
| ATOM | 714 | CG | TRP | D | 418 | −4.797 | 9.022 | −1.149 | 1.00 | 36.92 | C |
| ATOM | 715 | CD1 | TRP | D | 418 | −4.085 | 7.871 | −0.809 | 1.00 | 34.34 | C |
| ATOM | 716 | NE1 | TRP | D | 418 | −4.953 | 6.830 | −0.528 | 1.00 | 40.86 | N |
| ATOM | 717 | CE2 | TRP | D | 418 | −6.259 | 7.225 | −0.645 | 1.00 | 37.10 | C |
| ATOM | 718 | CD2 | TRP | D | 418 | −6.239 | 8.637 | −1.057 | 1.00 | 36.55 | C |
| ATOM | 719 | CE3 | TRP | D | 418 | −7.449 | 9.294 | −1.290 | 1.00 | 34.99 | C |
| ATOM | 720 | CZ3 | TRP | D | 418 | −8.647 | 8.600 | −1.068 | 1.00 | 36.53 | C |
| ATOM | 721 | CH2 | TRP | D | 418 | −8.647 | 7.244 | −0.664 | 1.00 | 36.09 | C |
| ATOM | 722 | CZ2 | TRP | D | 418 | −7.447 | 6.538 | −0.436 | 1.00 | 32.77 | C |
| ATOM | 723 | C | TRP | D | 418 | −3.236 | 11.796 | −3.301 | 1.00 | 39.49 | C |
| ATOM | 724 | O | TRP | D | 418 | −2.076 | 12.102 | −2.926 | 1.00 | 34.44 | O |
| ATOM | 725 | N | GLY | D | 419 | −4.033 | 12.645 | −3.941 | 1.00 | 39.81 | N |
| ATOM | 726 | CA | GLY | D | 419 | −3.646 | 14.044 | −4.118 | 1.00 | 35.88 | C |
| ATOM | 727 | C | GLY | D | 419 | −4.574 | 14.972 | −3.357 | 1.00 | 38.09 | C |
| ATOM | 728 | O | GLY | D | 419 | −5.763 | 15.079 | −3.691 | 1.00 | 36.01 | O |
| ATOM | 729 | N | LEU | D | 420 | −4.027 | 15.631 | −2.333 | 1.00 | 35.20 | N |
| ATOM | 730 | CA | LEU | D | 420 | −4.813 | 16.284 | −1.311 | 1.00 | 39.17 | C |

TABLE 8-continued

Atomic coordinates for unbound CRBN-CRBN (TBD) (Apo) (Murine protein)

| ATOM | 731 | CB | LEU | D | 420 | −4.465 | 15.779 | 0.113 | 1.00 | 33.44 | C |
|---|---|---|---|---|---|---|---|---|---|---|---|
| ATOM | 732 | CG | LEU | D | 420 | −4.481 | 14.282 | 0.351 | 1.00 | 36.32 | C |
| ATOM | 733 | CD1 | LEU | D | 420 | −4.012 | 13.963 | 1.766 | 1.00 | 33.31 | C |
| ATOM | 734 | CD2 | LEU | D | 420 | −5.872 | 13.716 | 0.068 | 1.00 | 30.06 | C |
| ATOM | 735 | C | LEU | D | 420 | −4.583 | 17.765 | −1.331 | 1.00 | 41.11 | C |
| ATOM | 736 | O | LEU | D | 420 | −3.459 | 18.224 | −1.469 | 1.00 | 47.66 | O |
| ATOM | 737 | N | THR | D | 421 | −5.650 | 18.504 | −1.077 | 1.00 | 41.59 | N |
| ATOM | 738 | CA | THR | D | 421 | −5.626 | 19.948 | −1.255 | 1.00 | 42.61 | C |
| ATOM | 739 | CB | THR | D | 421 | −7.098 | 20.389 | −1.469 | 1.00 | 39.99 | C |
| ATOM | 740 | OG1 | THR | D | 421 | −7.473 | 19.935 | −2.779 | 1.00 | 36.52 | O |
| ATOM | 741 | CG2 | THR | D | 421 | −7.267 | 21.937 | −1.387 | 1.00 | 37.00 | C |
| ATOM | 742 | C | THR | D | 421 | −4.992 | 20.516 | −0.002 | 1.00 | 40.83 | C |
| ATOM | 743 | O | THR | D | 421 | −5.558 | 20.333 | 1.067 | 1.00 | 40.91 | O |
| ATOM | 744 | N | ARG | D | 422 | −3.810 | 21.130 | −0.086 | 1.00 | 43.97 | N |
| ATOM | 745 | CA | ARG | D | 422 | −3.107 | 21.522 | 1.181 | 1.00 | 47.70 | C |
| ATOM | 746 | CB | ARG | D | 422 | −1.784 | 22.256 | 0.936 | 1.00 | 53.26 | C |
| ATOM | 747 | CG | ARG | D | 422 | 0.851 | 21.590 | −0.061 | 1.00 | 58.13 | C |
| ATOM | 748 | CD | ARG | D | 422 | 0.301 | 22.512 | −0.467 | 1.00 | 62.45 | C |
| ATOM | 749 | NE | ARG | D | 422 | 1.233 | 21.765 | −1.317 | 1.00 | 66.62 | N |
| ATOM | 750 | CZ | ARG | D | 422 | 2.222 | 21.012 | −0.839 | 1.00 | 69.30 | C |
| ATOM | 751 | NH1 | ARG | D | 422 | 2.422 | 20.932 | 0.479 | 1.00 | 69.64 | N |
| ATOM | 752 | NH2 | ARG | D | 422 | 3.004 | 20.338 | −1.671 | 1.00 | 68.91 | N |
| ATOM | 753 | C | ARG | D | 422 | −3.953 | 22.400 | 2.089 | 1.00 | 45.82 | C |
| ATOM | 754 | O | ARG | D | 422 | −3.925 | 22.254 | 3.293 | 1.00 | 44.86 | O |
| ATOM | 755 | N | SER | D | 423 | −4.706 | 23.327 | 1.511 | 1.00 | 54.61 | N |
| ATOM | 756 | CA | SER | D | 423 | −5.417 | 24.313 | 2.334 | 1.00 | 59.28 | C |
| ATOM | 757 | CB | SER | D | 423 | −5.905 | 25.452 | 1.455 | 1.00 | 56.59 | C |
| ATOM | 758 | OG | SER | D | 423 | −6.555 | 24.911 | 0.320 | 1.00 | 57.41 | O |
| ATOM | 759 | C | SER | D | 423 | −6.579 | 23.682 | 3.126 | 1.00 | 60.54 | C |
| ATOM | 760 | O | SER | D | 423 | −7.067 | 24.276 | 4.099 | 1.00 | 64.65 | O |
| ATOM | 761 | N | ALA | D | 424 | −7.007 | 22.481 | 2.706 | 1.00 | 57.18 | N |
| ATOM | 762 | CA | ALA | D | 424 | −7.994 | 21.682 | 3.443 | 1.00 | 49.63 | C |
| ATOM | 763 | CB | ALA | D | 424 | −8.744 | 20.770 | 2.483 | 1.00 | 47.70 | C |
| ATOM | 764 | C | ALA | D | 424 | −7.418 | 20.887 | 4.666 | 1.00 | 51.41 | C |
| ATOM | 765 | O | ALA | D | 424 | −8.166 | 20.287 | 5.428 | 1.00 | 41.35 | O |
| ATOM | 766 | N | LEU | D | 425 | −6.103 | 20.903 | 4.872 | 1.00 | 47.84 | N |
| ATOM | 767 | CA | LEU | D | 425 | −5.516 | 20.205 | 6.043 | 1.00 | 55.50 | C |
| ATOM | 768 | CB | LEU | D | 425 | −4.444 | 19.194 | 5.586 | 1.00 | 50.02 | C |
| ATOM | 769 | CG | LEU | D | 425 | −4.880 | 18.369 | 4.380 | 1.00 | 54.22 | C |
| ATOM | 770 | CD1 | LEU | D | 425 | −3.714 | 17.651 | 3.699 | 1.00 | 50.36 | C |
| ATOM | 771 | CD2 | LEU | D | 425 | −5.975 | 17.421 | 4.844 | 1.00 | 50.91 | C |
| ATOM | 772 | C | LEU | D | 425 | −4.907 | 21.114 | 7.126 | 1.00 | 58.16 | C |
| ATOM | 773 | O | LEU | D | 425 | −4.373 | 22.179 | 6.816 | 1.00 | 57.38 | 0 |
| ATOM | 774 | N | LEU | D | 426 | −4.967 | 20.668 | 8.384 | 1.00 | 60.87 | N |
| ATOM | 775 | CA | LEU | D | 426 | −4.254 | 21.328 | 9.480 | 1.00 | 67.03 | C |
| ATOM | 776 | CB | LEU | D | 426 | −5.098 | 21.377 | 10.743 | 1.00 | 69.83 | C |
| ATOM | 777 | CG | LEU | D | 426 | −5.629 | 22.764 | 11.119 | 1.00 | 82.14 | C |
| ATOM | 778 | CD1 | LEU | D | 426 | −5.743 | 22.807 | 12.643 | 1.00 | 83.61 | C |
| ATOM | 779 | CD2 | LEU | D | 426 | −4.747 | 23.905 | 10.596 | 1.00 | 75.32 | C |
| ATOM | 780 | C | LEU | D | 426 | −2.898 | 20.687 | 9.772 | 1.00 | 67.50 | C |
| ATOM | 781 | O | LEU | D | 426 | −2.844 | 19.470 | 9.937 | 1.00 | 60.80 | O |
| ATOM | 782 | N | PRO | D | 427 | −1.888 | 21.535 | 10.084 | 1.00 | 74.12 | N |
| ATOM | 783 | CA | PRO | D | 427 | −0.568 | 21.863 | 9.570 | 1.00 | 83.22 | C |
| ATOM | 784 | CB | PRO | D | 427 | 0.311 | 20.759 | 10.203 | 1.00 | 72.67 | C |
| ATOM | 785 | CG | PRO | D | 427 | −0.415 | 20.397 | 11.488 | 1.00 | 66.90 | C |
| ATOM | 786 | CD | PRO | D | 427 | −1.690 | 21.235 | 11.518 | 1.00 | 77.02 | C |
| ATOM | 787 | C | PRO | D | 427 | −0.405 | 22.046 | 8.016 | 1.00 | 100.76 | C |
| ATOM | 788 | O | PRO | D | 427 | −1.283 | 21.653 | 7.231 | 1.00 | 98.35 | O |
| ATOM | 789 | N | THR | D | 428 | 0.690 | 22.696 | 7.596 | 1.00 | 115.94 | N |
| ATOM | 790 | CA | THR | D | 428 | 1.160 | 22.653 | 6.193 | 1.00 | 109.64 | C |
| ATOM | 791 | CB | THR | D | 428 | 1.679 | 24.016 | 5.680 | 1.00 | 107.37 | C |
| ATOM | 792 | OG1 | THR | D | 428 | 0.839 | 25.079 | 6.154 | 1.00 | 104.87 | O |
| ATOM | 793 | CG2 | THR | D | 428 | 1.742 | 24.020 | 4.130 | 1.00 | 99.22 | C |
| ATOM | 794 | C | THR | D | 428 | 2.312 | 21.651 | 6.085 | 1.00 | 105.13 | C |
| ATOM | 795 | O | THR | D | 428 | 2.346 | 20.805 | 5.193 | 1.00 | 82.97 | O |
| ATOM | 796 | N | THR | A | 322 | −31.414 | 15.182 | 38.883 | 1.00 | 64.74 | N |
| ATOM | 797 | CA | THR | A | 322 | −31.507 | 15.948 | 37.592 | 1.00 | 65.13 | C |
| ATOM | 798 | CB | THR | A | 322 | −32.053 | 17.388 | 37.762 | 1.00 | 63.14 | C |
| ATOM | 799 | OG1 | THR | A | 322 | −30.973 | 18.299 | 38.049 | 1.00 | 63.52 | O |
| ATOM | 800 | CG2 | THR | A | 322 | −33.157 | 17.474 | 38.815 | 1.00 | 75.66 | C |
| ATOM | 801 | C | THR | A | 322 | −30.200 | 16.078 | 36.763 | 1.00 | 63.22 | C |
| ATOM | 802 | O | THR | A | 322 | −30.272 | 16.554 | 35.618 | 1.00 | 55.31 | O |
| ATOM | 803 | N | SER | A | 323 | −29.035 | 15.703 | 37.321 | 1.00 | 56.23 | N |
| ATOM | 804 | CA | SER | A | 323 | −27.752 | 15.798 | 36.575 | 1.00 | 52.49 | C |
| ATOM | 805 | CB | SER | A | 323 | −26.487 | 15.611 | 37.422 | 1.00 | 45.96 | C |
| ATOM | 806 | OG | SER | A | 323 | −26.608 | 16.384 | 38.563 | 1.00 | 50.41 | O |
| ATOM | 807 | C | SER | A | 323 | −27.694 | 14.728 | 35.578 | 1.00 | 53.59 | C |
| ATOM | 808 | O | SER | A | 323 | −28.065 | 13.573 | 35.850 | 1.00 | 56.66 | O |

TABLE 8-continued

Atomic coordinates for unbound CRBN-CRBN (TBD) (Apo) (Murine protein)

| ATOM | 809 | N | LEU | A | 324 | −27.160 | 15.115 | 34.433 | 1.00 | 51.12 | N |
|---|---|---|---|---|---|---|---|---|---|---|---|
| ATOM | 810 | CA | LEU | A | 324 | −26.909 | 14.197 | 33.353 | 1.00 | 50.45 | C |
| ATOM | 811 | CB | LEU | A | 324 | −27.661 | 14.631 | 32.096 | 1.00 | 42.68 | C |
| ATOM | 812 | CG | LEU | A | 324 | −29.186 | 14.555 | 32.201 | 1.00 | 57.69 | C |
| ATOM | 813 | CD1 | LEU | A | 324 | −29.809 | 14.881 | 30.853 | 1.00 | 57.87 | C |
| ATOM | 814 | CD2 | LEU | A | 324 | −29.685 | 13.178 | 32.656 | 1.00 | 63.57 | C |
| ATOM | 815 | C | LEU | A | 324 | −25.424 | 14.265 | 33.143 | 1.00 | 50.07 | C |
| ATOM | 816 | O | LEU | A | 324 | −24.888 | 15.335 | 32.857 | 1.00 | 47.17 | O |
| ATOM | 817 | N | CYS | A | 325 | −24.774 | 13.113 | 33.282 | 1.00 | 46.51 | N |
| ATOM | 818 | CA | CYS | A | 325 | −23.331 | 13.020 | 33.311 | 1.00 | 46.36 | C |
| ATOM | 819 | CB | CYS | A | 325 | −22.900 | 12.349 | 34.615 | 1.00 | 52.16 | C |
| ATOM | 820 | SG | CYS | A | 325 | −23.474 | 13.245 | 36.063 | 1.00 | 64.13 | S |
| ATOM | 821 | C | CYS | A | 325 | −22.794 | 12.234 | 32.133 | 1.00 | 43.72 | C |
| ATOM | 822 | O | CYS | A | 325 | −23.529 | 11.484 | 31.509 | 1.00 | 45.76 | O |
| ATOM | 823 | N | CYS | A | 326 | −21.496 | 12.393 | 31.866 | 1.00 | 40.87 | N |
| ATOM | 824 | CA | CYS | A | 326 | −20.781 | 11.694 | 30.820 | 1.00 | 47.88 | C |
| ATOM | 825 | CB | CYS | A | 326 | −19.357 | 12.248 | 30.796 | 1.00 | 49.28 | C |
| ATOM | 826 | SG | CYS | A | 326 | −17.955 | 11.249 | 30.203 | 1.00 | 50.74 | S |
| ATOM | 827 | C | CYS | A | 326 | −20.835 | 10.217 | 31.176 | 1.00 | 48.89 | C |
| ATOM | 828 | O | CYS | A | 326 | −20.460 | 9.853 | 32.275 | 1.00 | 56.30 | O |
| ATOM | 829 | N | LYS | A | 327 | −21.386 | 9.392 | 30.296 | 1.00 | 56.90 | N |
| ATOM | 830 | CA | LYS | A | 327 | −21.465 | 7.952 | 30.562 | 1.00 | 60.17 | C |
| ATOM | 831 | CB | LYS | A | 327 | −22.308 | 7.194 | 29.534 | 1.00 | 61.38 | C |
| ATOM | 832 | CG | LYS | A | 327 | −22.346 | 5.683 | 29.804 | 1.00 | 67.09 | C |
| ATOM | 833 | CD | LYS | A | 327 | −23.713 | 5.090 | 29.553 | 1.00 | 60.22 | C |
| ATOM | 834 | CE | LYS | A | 327 | −23.893 | 4.768 | 28.091 | 1.00 | 68.01 | C |
| ATOM | 835 | NZ | LYS | A | 327 | −25.351 | 4.786 | 27.794 | 1.00 | 67.37 | N |
| ATOM | 836 | C | LYS | A | 327 | −20.073 | 7.337 | 30.645 | 1.00 | 63.57 | C |
| ATOM | 837 | O | LYS | A | 327 | −19.748 | 6.715 | 31.670 | 1.00 | 63.43 | O |
| ATOM | 838 | N | GLN | A | 328 | −19.246 | 7.533 | 29.610 | 1.00 | 60.66 | N |
| ATOM | 839 | CA | GLN | A | 328 | −17.916 | 6.925 | 29.629 | 1.00 | 72.61 | C |
| ATOM | 840 | CB | GLN | A | 328 | −17.072 | 7.320 | 28.419 | 1.00 | 72.02 | C |
| ATOM | 841 | CG | GLN | A | 328 | −15.917 | 6.342 | 28.214 | 1.00 | 82.06 | C |
| ATOM | 842 | CD | GLN | A | 328 | −14.676 | 6.945 | 27.569 | 1.00 | 84.95 | C |
| ATOM | 843 | OE1 | GLN | A | 328 | −14.714 | 7.448 | 26.442 | 1.00 | 94.25 | O |
| ATOM | 844 | NE2 | GLN | A | 328 | −13.553 | 6.862 | 28.274 | 1.00 | 86.62 | N |
| ATOM | 845 | C | GLN | A | 328 | −17.151 | 7.187 | 30.948 | 1.00 | 74.82 | C |
| ATOM | 846 | O | GLN | A | 328 | −16.449 | 6.308 | 31.437 | 1.00 | 78.05 | O |
| ATOM | 847 | N | CYS | A | 329 | −17.308 | 8.373 | 31.536 | 1.00 | 69.12 | N |
| ATOM | 848 | CA | CYS | A | 329 | −16.484 | 8.764 | 32.691 | 1.00 | 62.17 | C |
| ATOM | 849 | CB | CYS | A | 329 | −15.686 | 10.045 | 32.373 | 1.00 | 67.93 | C |
| ATOM | 850 | SG | CYS | A | 329 | −16.526 | 11.591 | 31.831 | 1.00 | 56.12 | S |
| ATOM | 851 | C | CYS | A | 329 | −17.206 | 8.903 | 34.026 | 1.00 | 61.90 | C |
| ATOM | 852 | O | CYS | A | 329 | −16.589 | 8.781 | 35.073 | 1.00 | 54.67 | O |
| ATOM | 853 | N | GLN | A | 330 | −18.506 | 9.185 | 33.996 | 1.00 | 64.20 | N |
| ATOM | 854 | CA | GLN | A | 330 | −19.273 | 9.522 | 35.209 | 1.00 | 59.62 | C |
| ATOM | 855 | CB | GLN | A | 330 | −19.587 | 8.275 | 36.037 | 1.00 | 70.87 | C |
| ATOM | 856 | CG | GLN | A | 330 | −20.882 | 7.568 | 35.633 | 1.00 | 80.09 | C |
| ATOM | 857 | CD | GLN | A | 330 | −21.102 | 6.259 | 36.389 | 1.00 | 87.88 | C |
| ATOM | 858 | OE1 | GLN | A | 330 | −21.255 | 6.248 | 37.619 | 1.00 | 90.17 | O |
| ATOM | 859 | NE2 | GLN | A | 330 | −21.128 | 5.148 | 35.655 | 1.00 | 86.39 | N |
| ATOM | 860 | C | GLN | A | 330 | −18.643 | 10.589 | 36.087 | 1.00 | 54.02 | C |
| ATOM | 861 | O | GLN | A | 330 | −19.181 | 10.905 | 37.135 | 1.00 | 60.58 | O |
| ATOM | 862 | N | GLU | A | 331 | −17.525 | 11.170 | 35.680 | 1.00 | 54.07 | N |
| ATOM | 863 | CA | GLU | A | 331 | −16.919 | 12.212 | 36.536 | 1.00 | 73.03 | C |
| ATOM | 864 | CB | GLU | A | 331 | −15.414 | 12.367 | 36.265 | 1.00 | 72.64 | C |
| ATOM | 865 | CG | GLU | A | 331 | −14.531 | 11.323 | 36.943 | 1.00 | 79.25 | C |
| ATOM | 866 | CD | GLU | A | 331 | −14.334 | 11.514 | 38.459 | 1.00 | 80.32 | C |
| ATOM | 867 | OE1 | GLU | A | 331 | −14.517 | 10.511 | 39.196 | 1.00 | 80.47 | O |
| ATOM | 868 | OE2 | GLU | A | 331 | −13.967 | 12.636 | 38.912 | 1.00 | 73.65 | O |
| ATOM | 869 | C | GLU | A | 331 | −17.635 | 13.571 | 36.405 | 1.00 | 72.63 | C |
| ATOM | 870 | O | GLU | A | 331 | −17.721 | 14.335 | 37.361 | 1.00 | 79.20 | O |
| ATOM | 871 | N | THR | A | 332 | −18.205 | 13.809 | 35.229 | 1.00 | 62.77 | N |
| ATOM | 872 | CA | THR | A | 332 | −18.537 | 15.143 | 34.770 | 1.00 | 62.82 | C |
| ATOM | 873 | CB | THR | A | 332 | −17.703 | 15.424 | 33.518 | 1.00 | 66.12 | C |
| ATOM | 874 | OG1 | THR | A | 332 | −16.445 | 14.752 | 33.667 | 1.00 | 68.14 | O |
| ATOM | 875 | CG2 | THR | A | 332 | −17.442 | 16.871 | 33.408 | 1.00 | 60.32 | C |
| ATOM | 876 | C | THR | A | 332 | −20.024 | 15.345 | 34.453 | 1.00 | 54.02 | C |
| ATOM | 877 | O | THR | A | 332 | −20.628 | 14.551 | 33.709 | 1.00 | 49.63 | O |
| ATOM | 878 | N | GLU | A | 333 | −20.613 | 16.381 | 35.043 | 1.00 | 44.93 | N |
| ATOM | 879 | CA | GLU | A | 333 | −21.970 | 16.796 | 34.662 | 1.00 | 45.79 | C |
| ATOM | 880 | CB | GLU | A | 333 | −22.646 | 17.659 | 35.710 | 1.00 | 41.88 | C |
| ATOM | 881 | CG | GLU | A | 333 | −24.107 | 18.037 | 35.307 | 1.00 | 41.57 | C |
| ATOM | 882 | CD | GLU | A | 333 | −24.785 | 18.918 | 36.342 | 1.00 | 44.48 | C |
| ATOM | 883 | OE1 | GLU | A | 333 | −25.213 | 18.381 | 37.397 | 1.00 | 49.79 | O |
| ATOM | 884 | OE2 | GLU | A | 333 | −24.863 | 20.159 | 36.132 | 1.00 | 43.44 | O |
| ATOM | 885 | C | GLU | A | 333 | −21.901 | 17.556 | 33.344 | 1.00 | 44.03 | C |
| ATOM | 886 | O | GLU | A | 333 | −21.093 | 18.454 | 33.231 | 1.00 | 47.11 | O |

TABLE 8-continued

Atomic coordinates for unbound CRBN-CRBN (TBD) (Apo) (Murine protein)

| ATOM | 887 | N | ILE | A | 334 | −22.744 | 17.169 | 32.373 | 1.00 | 39.63 | N |
|---|---|---|---|---|---|---|---|---|---|---|---|
| ATOM | 888 | CA | ILE | A | 334 | −22.823 | 17.787 | 31.043 | 1.00 | 42.29 | C |
| ATOM | 889 | CB | ILE | A | 334 | −22.929 | 16.704 | 29.933 | 1.00 | 42.43 | C |
| ATOM | 890 | CG1 | ILE | A | 334 | −21.714 | 15.715 | 29.954 | 1.00 | 46.99 | C |
| ATOM | 891 | CD1 | ILE | A | 334 | −20.329 | 16.329 | 29.651 | 1.00 | 43.86 | C |
| ATOM | 892 | CG2 | ILE | A | 334 | −23.054 | 17.334 | 28.587 | 1.00 | 42.58 | C |
| ATOM | 893 | C | ILE | A | 334 | −23.988 | 18.785 | 30.910 | 1.00 | 41.09 | C |
| ATOM | 894 | O | ILE | A | 334 | −23.860 | 19.810 | 30.235 | 1.00 | 41.01 | O |
| ATOM | 895 | N | THR | A | 335 | −25.134 | 18.472 | 31.517 | 1.00 | 40.66 | N |
| ATOM | 896 | CA | THR | A | 335 | −26.299 | 19.366 | 31.489 | 1.00 | 37.57 | C |
| ATOM | 897 | CB | THR | A | 335 | −27.016 | 19.396 | 30.127 | 1.00 | 38.85 | C |
| ATOM | 898 | OG1 | THR | A | 335 | −28.079 | 20.346 | 30.218 | 1.00 | 42.46 | O |
| ATOM | 899 | CG2 | THR | A | 335 | −27.640 | 18.028 | 29.760 | 1.00 | 41.75 | C |
| ATOM | 900 | C | THR | A | 335 | −27.239 | 18.935 | 32.601 | 1.00 | 43.86 | C |
| ATOM | 901 | O | THR | A | 335 | −26.916 | 17.975 | 33.317 | 1.00 | 44.98 | O |
| ATOM | 902 | N | THR | A | 336 | −28.383 | 19.613 | 32.763 | 1.00 | 45.29 | N |
| ATOM | 903 | CA | THR | A | 336 | −29.393 | 19.185 | 33.748 | 1.00 | 45.65 | C |
| ATOM | 904 | CB | THR | A | 336 | −29.512 | 20.143 | 34.967 | 1.00 | 47.73 | C |
| ATOM | 905 | OG1 | THR | A | 336 | −30.147 | 21.349 | 34.565 | 1.00 | 45.83 | O |
| ATOM | 906 | CG2 | THR | A | 336 | −28.161 | 20.478 | 35.589 | 1.00 | 51.69 | C |
| ATOM | 907 | C | THR | A | 336 | −30.774 | 19.040 | 33.071 | 1.00 | 47.57 | C |
| ATOM | 908 | O | THR | A | 336 | −30.995 | 19.556 | 31.984 | 1.00 | 44.30 | O |
| ATOM | 909 | N | LYS | A | 337 | −31.704 | 18.355 | 33.732 | 1.00 | 47.45 | N |
| ATOM | 910 | CA | LYS | A | 337 | −33.047 | 18.167 | 33.189 | 1.00 | 50.85 | C |
| ATOM | 911 | CB | LYS | A | 337 | −33.876 | 17.226 | 34.077 | 1.00 | 55.34 | C |
| ATOM | 912 | CG | LYS | A | 337 | −33.520 | 15.757 | 33.878 | 1.00 | 65.18 | C |
| ATOM | 913 | CD | LYS | A | 337 | −34.263 | 14.859 | 34.850 | 1.00 | 73.47 | C |
| ATOM | 914 | CE | LYS | A | 337 | −34.269 | 13.447 | 34.309 | 1.00 | 81.28 | C |
| ATOM | 915 | NZ | LYS | A | 337 | −34.549 | 12.492 | 35.413 | 1.00 | 88.29 | N |
| ATOM | 916 | C | LYS | A | 337 | −33.772 | 19.490 | 33.005 | 1.00 | 47.39 | C |
| ATOM | 917 | O | LYS | A | 337 | −34.641 | 19.597 | 32.142 | 1.00 | 46.09 | O |
| ATOM | 918 | N | ASN | A | 338 | −33.400 | 20.491 | 33.804 | 1.00 | 44.39 | N |
| ATOM | 919 | CA | ASN | A | 338 | −33.970 | 21.838 | 33.722 | 1.00 | 41.29 | C |
| ATOM | 920 | CB | ASN | A | 338 | −33.481 | 22.681 | 34.896 | 1.00 | 44.93 | C |
| ATOM | 921 | CG | ASN | A | 338 | −33.830 | 22.059 | 36.224 | 1.00 | 52.51 | C |
| ATOM | 922 | OD1 | ASN | A | 338 | −33.006 | 21.427 | 36.867 | 1.00 | 57.16 | O |
| ATOM | 923 | ND2 | ASN | A | 338 | −35.053 | 22.209 | 36.621 | 1.00 | 51.44 | N |
| ATOM | 924 | C | ASN | A | 338 | −33.678 | 22.560 | 32.401 | 1.00 | 41.09 | C |
| ATOM | 925 | O | ASN | A | 338 | −34.430 | 23.457 | 31.997 | 1.00 | 40.58 | O |
| ATOM | 926 | N | GLU | A | 339 | −32.627 | 22.141 | 31.703 | 1.00 | 38.41 | N |
| ATOM | 927 | CA | GLU | A | 339 | −32.253 | 22.798 | 30.431 | 1.00 | 38.84 | C |
| ATOM | 928 | CB | GLU | A | 339 | −30.716 | 22.853 | 30.297 | 1.00 | 34.72 | C |
| ATOM | 929 | CG | GLU | A | 339 | −30.014 | 23.462 | 31.522 | 1.00 | 34.35 | C |
| ATOM | 930 | CD | GLU | A | 339 | −30.507 | 24.918 | 31.772 | 1.00 | 43.96 | C |
| ATOM | 931 | OE1 | GLU | A | 339 | −30.537 | 25.730 | 30.817 | 1.00 | 39.26 | O |
| ATOM | 932 | OE2 | GLU | A | 339 | −30.971 | 25.257 | 32.888 | 1.00 | 46.21 | O |
| ATOM | 933 | C | GLU | A | 339 | −32.892 | 22.172 | 29.186 | 1.00 | 40.42 | C |
| ATOM | 934 | O | GLU | A | 339 | −32.756 | 22.707 | 28.084 | 1.00 | 47.50 | O |
| ATOM | 935 | N | ILE | A | 340 | −33.596 | 21.047 | 29.353 | 1.00 | 44.38 | N |
| ATOM | 936 | CA | ILE | A | 340 | −34.286 | 20.369 | 28.220 | 1.00 | 39.11 | C |
| ATOM | 937 | CB | ILE | A | 340 | −34.846 | 18.973 | 28.612 | 1.00 | 40.87 | C |
| ATOM | 938 | CG1 | ILE | A | 340 | −33.715 | 18.109 | 29.195 | 1.00 | 43.08 | C |
| ATOM | 939 | CD1 | ILE | A | 340 | −34.170 | 16.809 | 29.853 | 1.00 | 47.03 | C |
| ATOM | 940 | CG2 | ILE | A | 340 | −35.482 | 18.281 | 27.387 | 1.00 | 44.41 | C |
| ATOM | 941 | C | ILE | A | 340 | −35.413 | 21.246 | 27.644 | 1.00 | 41.35 | C |
| ATOM | 942 | O | ILE | A | 340 | −36.215 | 21.795 | 28.374 | 1.00 | 39.08 | O |
| ATOM | 943 | N | PHE | A | 341 | −35.428 | 21.424 | 26.327 | 1.00 | 37.10 | N |
| ATOM | 944 | CA | PHE | A | 341 | −36.558 | 22.049 | 25.690 | 1.00 | 37.83 | C |
| ATOM | 945 | CB | PHE | A | 341 | −36.284 | 23.502 | 25.351 | 1.00 | 33.12 | C |
| ATOM | 946 | CG | PHE | A | 341 | −35.296 | 23.704 | 24.227 | 1.00 | 37.76 | C |
| ATOM | 947 | CD1 | PHE | A | 341 | −35.732 | 24.118 | 22.959 | 1.00 | 38.80 | C |
| ATOM | 948 | CE1 | PHE | A | 341 | −34.824 | 24.334 | 21.940 | 1.00 | 32.41 | C |
| ATOM | 949 | CZ | PHE | A | 341 | −33.457 | 24.152 | 22.179 | 1.00 | 30.75 | C |
| ATOM | 950 | CE2 | PHE | A | 341 | −33.009 | 23.733 | 23.415 | 1.00 | 30.54 | C |
| ATOM | 951 | CD2 | PHE | A | 341 | −33.922 | 23.534 | 24.436 | 1.00 | 35.39 | C |
| ATOM | 952 | C | PHE | A | 341 | −36.839 | 21.260 | 24.435 | 1.00 | 38.22 | C |
| ATOM | 953 | O | PHE | A | 341 | −36.107 | 20.355 | 24.067 | 1.00 | 42.66 | O |
| ATOM | 954 | N | SER | A | 342 | −37.862 | 21.634 | 23.704 | 1.00 | 46.41 | N |
| ATOM | 955 | CA | SER | A | 342 | −38.199 | 20.918 | 22.485 | 1.00 | 51.38 | C |
| ATOM | 956 | CB | SER | A | 342 | −39.610 | 20.386 | 22.556 | 1.00 | 57.79 | C |
| ATOM | 957 | OG | SER | A | 342 | −39.659 | 19.279 | 23.409 | 1.00 | 75.28 | O |
| ATOM | 958 | C | SER | A | 342 | −38.084 | 21.742 | 21.241 | 1.00 | 48.74 | C |
| ATOM | 959 | O | SER | A | 342 | −38.958 | 22.464 | 20.908 | 1.00 | 48.80 | O |
| ATOM | 960 | N | LEU | A | 343 | −37.003 | 21.610 | 20.528 | 1.00 | 47.75 | N |
| ATOM | 961 | CA | LEU | A | 343 | −36.826 | 22.435 | 19.322 | 1.00 | 50.19 | C |
| ATOM | 962 | CB | LEU | A | 343 | −35.459 | 22.162 | 18.661 | 1.00 | 45.08 | C |
| ATOM | 963 | CG | LEU | A | 343 | −34.648 | 23.130 | 17.750 | 1.00 | 49.41 | C |
| ATOM | 964 | CD1 | LEU | A | 343 | −34.709 | 22.910 | 16.236 | 1.00 | 49.16 | C |

TABLE 8-continued

Atomic coordinates for unbound CRBN-CRBN (TBD) (Apo) (Murine protein)

| ATOM | 965 | CD2 | LEU | A | 343 | −34.833 | 24.614 | 18.066 | 1.00 | 45.09 | C |
|------|-----|-----|-----|---|-----|---------|--------|--------|------|-------|---|
| ATOM | 966 | C | LEU | A | 343 | −37.944 | 22.195 | 18.315 | 1.00 | 52.22 | C |
| ATOM | 967 | O | LEU | A | 343 | −38.415 | 23.113 | 17.637 | 1.00 | 56.71 | O |
| ATOM | 968 | N | SER | A | 344 | −38.345 | 20.948 | 18.185 | 1.00 | 58.08 | N |
| ATOM | 969 | CA | SER | A | 344 | −39.508 | 20.641 | 17.365 | 1.00 | 69.47 | C |
| ATOM | 970 | CB | SER | A | 344 | −39.114 | 20.197 | 15.945 | 1.00 | 67.92 | C |
| ATOM | 971 | OG | SER | A | 344 | −39.927 | 19.108 | 15.518 | 1.00 | 69.32 | O |
| ATOM | 972 | C | SER | A | 344 | −40.374 | 19.604 | 18.055 | 1.00 | 66.17 | C |
| ATOM | 973 | O | SER | A | 344 | −39.871 | 18.571 | 18.537 | 1.00 | 70.56 | O |
| ATOM | 974 | N | ALA | A | 345 | −41.674 | 19.896 | 18.082 | 1.00 | 62.07 | N |
| ATOM | 975 | CA | ALA | A | 345 | −42.677 | 18.988 | 18.619 | 1.00 | 63.73 | C |
| ATOM | 976 | CB | ALA | A | 345 | −43.948 | 19.773 | 18.968 | 1.00 | 63.20 | C |
| ATOM | 977 | C | ALA | A | 345 | −42.964 | 17.792 | 17.656 | 1.00 | 67.80 | C |
| ATOM | 978 | O | ALA | A | 345 | −43.657 | 16.856 | 18.045 | 1.00 | 62.78 | O |
| ATOM | 979 | N | ALA | A | 345 | −42.400 | 17.824 | 16.432 | 1.00 | 62.89 | N' |
| ATOM | 980 | CA | CYS | A | 346 | −42.583 | 16.769 | 15.392 | 1.00 | 69.62 | C |
| ATOM | 981 | CB | CYS | A | 346 | −41.932 | 15.434 | 15.800 | 1.00 | 68.65 | C |
| ATOM | 982 | SG | CYS | A | 346 | −40.189 | 15.554 | 16.252 | 1.00 | 84.42 | S |
| ATOM | 983 | C | CYS | A | 346 | −44.061 | 16.515 | 15.085 | 1.00 | 60.24 | C |
| ATOM | 984 | O | CYS | A | 346 | −44.485 | 15.370 | 14.971 | 1.00 | 50.99 | O |
| ATOM | 985 | N | GLY | A | 347 | −44.832 | 17.590 | 15.009 | 1.00 | 49.48 | N |
| ATOM | 986 | CA | GLY | A | 347 | −46.210 | 17.515 | 14.650 | 1.00 | 52.95 | C |
| ATOM | 987 | C | GLY | A | 347 | −46.246 | 17.478 | 13.151 | 1.00 | 53.01 | C |
| ATOM | 988 | O | GLY | A | 347 | −45.200 | 17.467 | 12.518 | 1.00 | 61.62 | O |
| ATOM | 989 | N | PRO | A | 348 | −47.454 | 17.476 | 12.578 | 1.00 | 52.91 | N |
| ATOM | 990 | CA | PRO | A | 348 | −47.645 | 17.442 | 11.124 | 1.00 | 54.65 | C |
| ATOM | 991 | CB | PRO | A | 348 | −49.172 | 17.268 | 10.945 | 1.00 | 52.63 | C |
| ATOM | 992 | CG | PRO | A | 348 | −49.778 | 17.349 | 12.304 | 1.00 | 47.70 | C |
| ATOM | 993 | CD | PRO | A | 348 | −48.699 | 17.266 | 13.339 | 1.00 | 50.70 | C |
| ATOM | 994 | C | PRO | A | 348 | −47.151 | 18.697 | 10.431 | 1.00 | 54.83 | C |
| ATOM | 995 | O | PRO | A | 348 | −46.631 | 18.632 | 9.308 | 1.00 | 54.59 | O |
| ATOM | 996 | N | MET | A | 349 | −47.310 | 19.842 | 11.079 | 1.00 | 61.26 | N |
| ATOM | 997 | CA | MET | A | 349 | −46.863 | 21.093 | 10.456 | 1.00 | 68.28 | C |
| ATOM | 998 | CB | MET | A | 349 | −47.793 | 22.275 | 10.819 | 1.00 | 74.12 | C |
| ATOM | 999 | CG | MET | A | 349 | −48.982 | 22.495 | 9.859 | 1.00 | 79.45 | C |
| ATOM | 1000 | SD | MET | A | 349 | −48.717 | 21.930 | 8.144 | 1.00 | 87.13 | S |
| ATOM | 1001 | CE | MET | A | 349 | −49.873 | 22.932 | 7.193 | 1.00 | 90.16 | C |
| ATOM | 1002 | C | MET | A | 349 | −45.364 | 21.388 | 10.737 | 1.00 | 72.94 | C |
| ATOM | 1003 | O | MET | A | 349 | −44.918 | 22.530 | 10.658 | 1.00 | 73.72 | O |
| ATOM | 1004 | N | ALA | A | 350 | −44.589 | 20.353 | 11.056 | 1.00 | 73.90 | N |
| ATOM | 1005 | CA | ALA | A | 350 | −43.156 | 20.535 | 11.320 | 1.00 | 84.99 | C |
| ATOM | 1006 | CB | ALA | A | 350 | −42.747 | 19.851 | 12.626 | 1.00 | 76.62 | C |
| ATOM | 1007 | C | ALA | A | 350 | −42.316 | 20.037 | 10.137 | 1.00 | 80.23 | C |
| ATOM | 1008 | O | ALA | A | 350 | −42.188 | 18.832 | 9.918 | 1.00 | 79.05 | O |
| ATOM | 1009 | N | ALA | A | 351 | −41.784 | 20.968 | 9.346 | 1.00 | 88.56 | N |
| ATOM | 1010 | CA | ALA | A | 351 | −40.859 | 20.603 | 8.256 | 1.00 | 101.15 | C |
| ATOM | 1011 | CB | ALA | A | 351 | −41.061 | 21.481 | 7.017 | 1.00 | 94.52 | C |
| ATOM | 1012 | C | ALA | A | 351 | −39.430 | 20.701 | 8.778 | 1.00 | 91.22 | C |
| ATOM | 1013 | O | ALA | A | 351 | −39.234 | 21.038 | 9.946 | 1.00 | 86.64 | O |
| ATOM | 1014 | N | TYR | A | 358 | −32.217 | 14.583 | 14.906 | 1.00 | 76.26 | N |
| ATOM | 1015 | CA | TYR | A | 358 | −32.697 | 13.381 | 15.570 | 1.00 | 87.03 | C |
| ATOM | 1016 | CB | TYR | A | 358 | −31.523 | 12.517 | 16.024 | 1.00 | 87.26 | C |
| ATOM | 1017 | CG | TYR | A | 358 | −30.790 | 11.826 | 14.900 | 1.00 | 90.83 | C |
| ATOM | 1018 | CD1 | TYR | A | 358 | −29.710 | 10.976 | 15.177 | 1.00 | 96.91 | C |
| ATOM | 1019 | CE1 | TYR | A | 358 | −29.016 | 10.334 | 14.158 | 1.00 | 94.54 | C |
| ATOM | 1020 | CZ | TYR | A | 358 | −29.406 | 10.527 | 12.840 | 1.00 | 96.88 | C |
| ATOM | 1021 | OH | TYR | A | 358 | −28.712 | 9.878 | 11.838 | 1.00 | 93.98 | O |
| ATOM | 1022 | CE2 | TYR | A | 358 | −30.485 | 11.356 | 12.535 | 1.00 | 98.54 | C |
| ATOM | 1023 | CD2 | TYR | A | 358 | −31.175 | 11.994 | 13.561 | 1.00 | 94.83 | C |
| ATOM | 1024 | C | TYR | A | 358 | −33.577 | 13.740 | 16.749 | 1.00 | 83.80 | C |
| ATOM | 1025 | O | TYR | A | 358 | −33.576 | 14.892 | 17.206 | 1.00 | 74.42 | O |
| ATOM | 1026 | N | VAL | A | 359 | −34.294 | 12.742 | 17.264 | 1.00 | 90.76 | N |
| ATOM | 1027 | CA | VAL | A | 359 | −35.467 | 13.014 | 18.097 | 1.00 | 94.80 | C |
| ATOM | 1028 | CB | VAL | A | 359 | −36.788 | 12.745 | 17.316 | 1.00 | 99.96 | C |
| ATOM | 1029 | CG1 | VAL | A | 359 | −37.433 | 14.069 | 16.928 | 1.00 | 98.31 | C |
| ATOM | 1030 | CG2 | VAL | A | 359 | −36.571 | 11.853 | 16.085 | 1.00 | 85.58 | C |
| ATOM | 1031 | C | VAL | A | 359 | −35.489 | 12.407 | 19.516 | 1.00 | 102.77 | C |
| ATOM | 1032 | O | VAL | A | 359 | −35.563 | 13.146 | 20.515 | 1.00 | 86.81 | O |
| ATOM | 1033 | N | HIS | A | 360 | −35.462 | 11.072 | 19.592 | 1.00 | 112.12 | N |
| ATOM | 1034 | CA | HIS | A | 360 | −35.299 | 10.328 | 20.854 | 1.00 | 104.65 | C |
| ATOM | 1035 | CB | HIS | A | 360 | −36.416 | 9.307 | 21.072 | 1.00 | 116.16 | C |
| ATOM | 1036 | CG | HIS | A | 360 | −36.922 | 8.681 | 19.796 | 1.00 | 133.85 | C |
| ATOM | 1037 | ND1 | HIS | A | 360 | −38.083 | 9.056 | 19.216 | 1.00 | 138.07 | N |
| ATOM | 1038 | CE1 | HIS | A | 360 | −38.270 | 8.343 | 18.088 | 1.00 | 139.22 | C |
| ATOM | 1039 | NE2 | HIS | A | 360 | −37.220 | 7.513 | 17.939 | 1.00 | 138.53 | N |
| ATOM | 1040 | CD2 | HIS | A | 360 | −36.369 | 7.698 | 18.894 | 1.00 | 136.91 | C |
| ATOM | 1041 | C | HIS | A | 360 | −33.943 | 9.671 | 20.861 | 1.00 | 104.71 | C |
| ATOM | 1042 | O | HIS | A | 360 | −33.644 | 8.788 | 21.868 | 1.00 | 87.11 | O |

TABLE 8-continued

Atomic coordinates for unbound CRBN-CRBN (TBD) (Apo) (Murine protein)

| ATOM | 1043 | N   | GLU | A | 361 | −33.112 | 10.102 | 19.915 | 1.00 | 90.48  | N |
|------|------|-----|-----|---|-----|---------|--------|--------|------|--------|---|
| ATOM | 1044 | CA  | GLU | A | 361 | −31.701 | 9.778  | 19.922 | 1.00 | 83.91  | C |
| ATOM | 1045 | CB  | GLU | A | 361 | −31.206 | 9.488  | 18.506 | 1.00 | 84.72  | C |
| ATOM | 1046 | CG  | GLU | A | 361 | −31.883 | 8.313  | 17.817 | 1.00 | 102.02 | C |
| ATOM | 1047 | CD  | GLU | A | 361 | −31.828 | 8.436  | 16.304 | 1.00 | 103.03 | C |
| ATOM | 1048 | OE1 | GLU | A | 361 | −30.769 | 8.103  | 15.730 | 1.00 | 99.43  | O |
| ATOM | 1049 | OE2 | GLU | A | 361 | −32.839 | 8.872  | 15.698 | 1.00 | 100.80 | O |
| ATOM | 1050 | C   | GLU | A | 361 | −30.948 | 10.977 | 20.503 | 1.00 | 76.97  | C |
| ATOM | 1051 | O   | GLU | A | 361 | −29.887 | 10.806 | 21.106 | 1.00 | 65.34  | O |
| ATOM | 1052 | N   | THR | A | 362 | −31.529 | 12.171 | 20.320 | 1.00 | 72.35  | N |
| ATOM | 1053 | CA  | THR | A | 362 | −30.872 | 13.462 | 20.588 | 1.00 | 67.50  | C |
| ATOM | 1054 | CB  | THR | A | 362 | −30.474 | 14.191 | 19.289 | 1.00 | 71.14  | C |
| ATOM | 1055 | OG1 | THR | A | 362 | −29.448 | 13.445 | 18.643 | 1.00 | 66.76  | O |
| ATOM | 1056 | CG2 | THR | A | 362 | −29.921 | 15.590 | 19.567 | 1.00 | 64.02  | C |
| ATOM | 1057 | C   | THR | A | 362 | −31.719 | 14.380 | 21.465 | 1.00 | 62.30  | C |
| ATOM | 1058 | O   | THR | A | 362 | −32.871 | 14.711 | 21.151 | 1.00 | 62.12  | O |
| ATOM | 1059 | N   | LEU | A | 363 | −31.121 | 14.761 | 22.580 | 1.00 | 52.70  | N |
| ATOM | 1060 | CA  | LEU | A | 363 | −31.707 | 15.666 | 23.529 | 1.00 | 48.22  | C |
| ATOM | 1061 | CB  | LEU | A | 363 | −31.118 | 15.272 | 24.855 | 1.00 | 52.62  | C |
| ATOM | 1062 | CG  | LEU | A | 363 | −31.753 | 15.524 | 26.190 | 1.00 | 51.68  | C |
| ATOM | 1063 | CD1 | LEU | A | 363 | −33.179 | 15.013 | 26.229 | 1.00 | 54.33  | C |
| ATOM | 1064 | CD2 | LEU | A | 363 | −30.892 | 14.724 | 27.139 | 1.00 | 55.72  | C |
| ATOM | 1065 | C   | LEU | A | 363 | −31.230 | 17.063 | 23.138 | 1.00 | 47.89  | C |
| ATOM | 1066 | O   | LEU | A | 363 | −30.056 | 17.221 | 22.792 | 1.00 | 52.97  | O |
| ATOM | 1067 | N   | THR | A | 364 | −32.132 | 18.044 | 23.087 | 1.00 | 45.95  | N |
| ATOM | 1068 | CA  | THR | A | 364 | −31.773 | 19.454 | 22.795 | 1.00 | 40.45  | C |
| ATOM | 1069 | CB  | THR | A | 364 | −32.771 | 20.135 | 21.816 | 1.00 | 40.59  | C |
| ATOM | 1070 | OG1 | THR | A | 364 | −34.119 | 19.925 | 22.285 | 1.00 | 40.37  | O |
| ATOM | 1071 | CG2 | THR | A | 364 | −32.577 | 19.587 | 20.362 | 1.00 | 37.83  | C |
| ATOM | 1072 | C   | THR | A | 364 | −31.816 | 20.214 | 24.136 | 1.00 | 40.76  | C |
| ATOM | 1073 | O   | THR | A | 364 | −32.822 | 20.139 | 24.829 | 1.00 | 33.60  | O |
| ATOM | 1074 | N   | VAL | A | 365 | −30.717 | 20.877 | 24.536 | 1.00 | 36.90  | N |
| ATOM | 1075 | CA  | VAL | A | 365 | −30.706 | 21.622 | 25.821 | 1.00 | 33.17  | C |
| ATOM | 1076 | CB  | VAL | A | 365 | −29.881 | 20.935 | 26.949 | 1.00 | 34.05  | C |
| ATOM | 1077 | CG1 | VAL | A | 365 | −30.501 | 19.597 | 27.359 | 1.00 | 34.55  | C |
| ATOM | 1078 | CG2 | VAL | A | 365 | −28.383 | 20.790 | 26.590 | 1.00 | 30.19  | C |
| ATOM | 1079 | C   | VAL | A | 365 | −30.188 | 23.022 | 25.566 | 1.00 | 33.35  | C |
| ATOM | 1080 | O   | VAL | A | 365 | −29.449 | 23.241 | 24.621 | 1.00 | 37.80  | O |
| ATOM | 1081 | N   | TYR | A | 366 | −30.642 | 23.985 | 26.354 | 1.00 | 35.60  | N |
| ATOM | 1082 | CA  | TYR | A | 366 | −30.252 | 25.373 | 26.171 | 1.00 | 33.19  | C |
| ATOM | 1083 | CB  | TYR | A | 366 | −31.205 | 26.240 | 27.000 | 1.00 | 37.48  | C |
| ATOM | 1084 | CG  | TYR | A | 366 | −32.550 | 26.504 | 26.367 | 1.00 | 33.76  | C |
| ATOM | 1085 | CD1 | TYR | A | 366 | −32.624 | 27.001 | 25.079 | 1.00 | 37.46  | C |
| ATOM | 1086 | CE1 | TYR | A | 366 | −33.846 | 27.271 | 24.482 | 1.00 | 40.20  | C |
| ATOM | 1087 | CZ  | TYR | A | 366 | −35.029 | 27.039 | 25.197 | 1.00 | 40.18  | C |
| ATOM | 1088 | OH  | TYR | A | 366 | −36.237 | 27.315 | 24.589 | 1.00 | 38.19  | O |
| ATOM | 1089 | CE2 | TYR | A | 366 | −34.980 | 26.532 | 26.490 | 1.00 | 37.59  | C |
| ATOM | 1090 | CD2 | TYR | A | 366 | −33.735 | 26.270 | 27.069 | 1.00 | 34.30  | C |
| ATOM | 1091 | C   | TYR | A | 366 | −28.844 | 25.602 | 26.665 | 1.00 | 30.48  | C |
| ATOM | 1092 | O   | TYR | A | 366 | −28.112 | 26.451 | 26.168 | 1.00 | 34.80  | O |
| ATOM | 1093 | N   | LYS | A | 367 | −28.450 | 24.857 | 27.693 | 1.00 | 34.30  | N |
| ATOM | 1094 | CA  | LYS | A | 367 | −27.126 | 25.031 | 28.291 | 1.00 | 34.09  | C |
| ATOM | 1095 | CB  | LYS | A | 367 | −27.236 | 25.866 | 29.590 | 1.00 | 35.39  | C |
| ATOM | 1096 | CG  | LYS | A | 367 | −27.661 | 27.326 | 29.403 | 1.00 | 42.37  | C |
| ATOM | 1097 | CD  | LYS | A | 367 | −26.500 | 28.160 | 28.829 | 1.00 | 37.61  | C |
| ATOM | 1098 | CE  | LYS | A | 367 | −26.588 | 29.642 | 29.109 | 1.00 | 40.08  | C |
| ATOM | 1099 | NZ  | LYS | A | 367 | −25.262 | 30.243 | 28.743 | 1.00 | 44.44  | N |
| ATOM | 1100 | C   | LYS | A | 367 | −26.484 | 23.667 | 28.621 | 1.00 | 33.71  | C |
| ATOM | 1101 | O   | LYS | A | 367 | −27.164 | 22.678 | 28.991 | 1.00 | 29.89  | O |
| ATOM | 1102 | N   | ALA | A | 368 | −25.169 | 23.671 | 28.629 | 1.00 | 32.16  | N |
| ATOM | 1103 | CA  | ALA | A | 368 | −24.383 | 22.504 | 28.875 | 1.00 | 36.79  | C |
| ATOM | 1104 | CB  | ALA | A | 368 | −24.205 | 21.746 | 27.569 | 1.00 | 38.81  | C |
| ATOM | 1105 | C   | ALA | A | 368 | −23.013 | 22.918 | 29.469 | 1.00 | 39.58  | C |
| ATOM | 1106 | O   | ALA | A | 368 | −22.578 | 24.053 | 29.340 | 1.00 | 35.20  | O |
| ATOM | 1107 | N   | SER | A | 369 | −22.341 | 21.994 | 30.139 | 1.00 | 37.78  | N |
| ATOM | 1108 | CA  | SER | A | 369 | −21.075 | 22.333 | 30.775 | 1.00 | 39.32  | C |
| ATOM | 1109 | CB  | SER | A | 369 | −21.323 | 22.454 | 32.265 | 1.00 | 38.18  | C |
| ATOM | 1110 | OG  | SER | A | 369 | −21.894 | 21.240 | 32.747 | 1.00 | 42.15  | O |
| ATOM | 1111 | C   | SER | A | 369 | −20.047 | 21.239 | 30.531 | 1.00 | 40.37  | C |
| ATOM | 1112 | O   | SER | A | 369 | −20.408 | 20.075 | 30.272 | 1.00 | 37.13  | O |
| ATOM | 1113 | N   | ASN | A | 370 | −18.768 | 21.610 | 30.574 | 1.00 | 42.00  | N |
| ATOM | 1114 | CA  | ASN | A | 370 | −17.668 | 20.630 | 30.562 | 1.00 | 44.71  | C |
| ATOM | 1115 | CB  | ASN | A | 370 | −17.804 | 19.3634| 31.727 | 1.00 | 42.34  | C |
| ATOM | 1116 | CH  | ASN | A | 370 | −17.826 | 20.336 | 33.063 | 1.00 | 46.61  | C |
| ATOM | 1117 | OD1 | ASN | A | 370 | −18.656 | 20.068 | 33.937 | 1.00 | 48.41  | O |
| ATOM | 1118 | ND2 | ASN | A | 370 | −16.939 | 21.285 | 33.207 | 1.00 | 45.13  | N |
| ATOM | 1119 | C   | ASN | A | 370 | −17.469 | 19.878 | 29.251 | 1.00 | 47.30  | C |
| ATOM | 1120 | O   | ASN | A | 370 | −17.003 | 18.723 | 29.250 | 1.00 | 46.85  | O |

TABLE 8-continued

Atomic coordinates for unbound CRBN-CRBN (TBD) (Apo) (Murine protein)

| ATOM | 1121 | N | LEU | A | 371 | −17.797 | 20.557 | 28.159 | 1.00 | 44.74 | N |
|---|---|---|---|---|---|---|---|---|---|---|---|
| ATOM | 1122 | CA | LEU | A | 371 | −17.615 | 20.060 | 26.789 | 1.00 | 42.12 | C |
| ATOM | 1123 | CB | LEU | A | 371 | −18.932 | 20.189 | 25.977 | 1.00 | 33.71 | C |
| ATOM | 1124 | CG | LEU | A | 371 | −20.047 | 19.206 | 26.391 | 1.00 | 38.67 | C |
| ATOM | 1125 | CD1 | LEU | A | 371 | −21.387 | 19.519 | 25.736 | 1.00 | 39.53 | C |
| ATOM | 1126 | CD2 | LEU | A | 371 | −19.676 | 17.722 | 26.139 | 1.00 | 32.94 | C |
| ATOM | 1127 | C | LEU | A | 371 | −16.556 | 20.924 | 26.165 | 1.00 | 44.99 | C |
| ATOM | 1128 | O | LEU | A | 371 | −16.569 | 22.141 | 26.359 | 1.00 | 49.20 | O |
| ATOM | 1129 | N | ASN | A | 372 | −15.631 | 20.297 | 25.438 | 1.00 | 45.74 | N |
| ATOM | 1130 | CA | ASN | A | 372 | −14.690 | 21.003 | 24.575 | 1.00 | 49.09 | C |
| ATOM | 1131 | CB | ASN | A | 372 | −13.292 | 20.364 | 24.625 | 1.00 | 50.76 | C |
| ATOM | 1132 | CG | ASN | A | 372 | −12.584 | 20.640 | 25.923 | 1.00 | 52.77 | C |
| ATOM | 1133 | OD1 | ASN | A | 372 | −12.783 | 21.694 | 26.522 | 1.00 | 57.63 | O |
| ATOM | 1134 | ND2 | ASN | A | 372 | −11.768 | 19.695 | 26.379 | 1.00 | 51.24 | N |
| ATOM | 1135 | C | ASN | A | 372 | −15.203 | 20.995 | 23.150 | 1.00 | 45.87 | C |
| ATOM | 1136 | O | ASN | A | 372 | −15.686 | 19.971 | 22.692 | 1.00 | 38.93 | O |
| ATOM | 1137 | N | LEU | A | 373 | −15.089 | 22.135 | 22.466 | 1.00 | 44.12 | N |
| ATOM | 1138 | CA | LEU | A | 373 | −15.444 | 22.237 | 21.055 | 1.00 | 43.92 | C |
| ATOM | 1139 | CB | LEU | A | 373 | −15.850 | 23.673 | 20.678 | 1.00 | 38.68 | C |
| ATOM | 1140 | CG | LEU | A | 373 | −16.992 | 24.295 | 21.473 | 1.00 | 45.58 | C |
| ATOM | 1141 | CD1 | LEU | A | 373 | −17.197 | 25.765 | 21.041 | 1.00 | 44.85 | C |
| ATOM | 1142 | CD2 | LEU | A | 373 | −18.262 | 23.466 | 21.277 | 1.00 | 39.83 | C |
| ATOM | 1143 | C | LEU | A | 373 | −14.284 | 21.798 | 20.194 | 1.00 | 49.50 | C |
| ATOM | 1144 | O | LEU | A | 373 | −13.115 | 22.191 | 20.420 | 1.00 | 52.34 | O |
| ATOM | 1145 | N | ILE | A | 374 | −14.623 | 21.025 | 19.170 | 1.00 | 44.70 | N |
| ATOM | 1146 | CA | ILE | A | 374 | −13.621 | 20.370 | 18.335 | 1.00 | 41.52 | C |
| ATOM | 1147 | CB | ILE | A | 374 | −13.760 | 18.825 | 18.416 | 1.00 | 43.27 | C |
| ATOM | 1148 | CG1 | ILE | A | 374 | −13.568 | 18.317 | 19.859 | 1.00 | 44.55 | C |
| ATOM | 1149 | CD1 | ILE | A | 374 | −12.189 | 18.570 | 20.449 | 1.00 | 43.82 | C |
| ATOM | 1150 | CG2 | ILE | A | 374 | −12.768 | 18.145 | 17.483 | 1.00 | 43.53 | C |
| ATOM | 1151 | C | ILE | A | 374 | −13.922 | 20.799 | 16.923 | 1.00 | 43.89 | C |
| ATOM | 1152 | O | ILE | A | 374 | −15.040 | 20.573 | 16.427 | 1.00 | 48.03 | O |
| ATOM | 1153 | N | GLY | A | 375 | −12.935 | 21.405 | 16.272 | 1.00 | 40.77 | N |
| ATOM | 1154 | CA | GLY | A | 375 | −13.061 | 21.842 | 14.868 | 1.00 | 45.94 | C |
| ATOM | 1155 | C | GLY | A | 375 | −13.937 | 23.097 | 14.732 | 1.00 | 54.11 | C |
| ATOM | 1156 | O | GLY | A | 375 | −14.292 | 23.684 | 15.730 | 1.00 | 45.38 | O |
| ATOM | 1157 | N | ARG | A | 376 | −14.255 | 23.512 | 13.501 | 1.00 | 58.28 | N |
| ATOM | 1158 | CA | ARG | A | 376 | −15.126 | 24.671 | 13.250 | 1.00 | 57.12 | C |
| ATOM | 1159 | CB | ARG | A | 376 | −14.607 | 25.598 | 12.130 | 1.00 | 53.14 | C |
| ATOM | 1160 | CG | ARG | A | 376 | −13.791 | 25.030 | 10.991 | 1.00 | 59.61 | C |
| ATOM | 1161 | CD | ARG | A | 376 | −12.290 | 25.201 | 11.188 | 1.00 | 61.21 | C |
| ATOM | 1162 | NE | ARG | A | 376 | −11.825 | 26.542 | 11.512 | 1.00 | 66.84 | N |
| ATOM | 1163 | CZ | ARG | A | 376 | −11.049 | 27.315 | 10.744 | 1.00 | 74.19 | C |
| ATOM | 1164 | NH1 | ARG | A | 376 | −10.641 | 26.926 | 9.531 | 1.00 | 54.90 | N |
| ATOM | 1165 | NH2 | ARG | A | 376 | −10.964 | 28.522 | 11.202 | 1.00 | 75.02 | N |
| ATOM | 1166 | C | ARG | A | 376 | −16.594 | 24.274 | 12.981 | 1.00 | 55.95 | C |
| ATOM | 1167 | O | ARG | A | 376 | −16.894 | 23.073 | 12.804 | 1.00 | 49.02 | O |
| ATOM | 1168 | N | PRO | A | 377 | −17.515 | 25.273 | 12.989 | 1.00 | 48.67 | N |
| ATOM | 1169 | CA | PRO | A | 377 | −18.934 | 24.983 | 12.714 | 1.00 | 45.57 | C |
| ATOM | 1170 | CB | PRO | A | 377 | −19.653 | 26.311 | 13.043 | 1.00 | 50.52 | C |
| ATOM | 1171 | CG | PRO | A | 377 | −18.563 | 27.366 | 13.026 | 1.00 | 52.89 | C |
| ATOM | 1172 | CD | PRO | A | 377 | −17.327 | 26.649 | 13.517 | 1.00 | 54.19 | C |
| ATOM | 1173 | C | PRO | A | 377 | −19.187 | 24.564 | 11.270 | 1.00 | 44.11 | C |
| ATOM | 1174 | O | PRO | A | 377 | −18.568 | 25.073 | 10.357 | 1.00 | 46.74 | O |
| ATOM | 1175 | N | SER | A | 378 | −20.097 | 23.628 | 11.072 | 1.00 | 44.73 | N |
| ATOM | 1176 | CA | SER | A | 378 | −20.440 | 23.246 | 9.740 | 1.00 | 52.10 | C |
| ATOM | 1177 | CB | SER | A | 378 | −19.958 | 21.818 | 9.473 | 1.00 | 49.37 | C |
| ATOM | 1178 | OG | SER | A | 378 | −20.572 | 21.366 | 8.284 | 1.00 | 54.59 | O |
| ATOM | 1179 | C | SER | A | 378 | −21.939 | 23.360 | 9.449 | 1.00 | 53.64 | C |
| ATOM | 1180 | O | SER | A | 378 | −22.773 | 22.952 | 10.251 | 1.00 | 62.33 | O |
| ATOM | 1181 | N | THR | A | 379 | −22.226 | 23.886 | 8.262 | 1.00 | 61.19 | N |
| ATOM | 1182 | CA | THR | A | 379 | −23.557 | 24.110 | 7.730 | 1.00 | 64.57 | C |
| ATOM | 1183 | CB | THR | A | 379 | −23.642 | 25.511 | 7.088 | 1.00 | 67.63 | C |
| ATOM | 1184 | OG1 | THR | A | 379 | −22.486 | 25.734 | 6.262 | 1.00 | 69.24 | O |
| ATOM | 1185 | CG2 | THR | A | 379 | −23.707 | 26.625 | 8.156 | 1.00 | 65.63 | C |
| ATOM | 1186 | C | THR | A | 379 | −23.858 | 23.078 | 6.650 | 1.00 | 69.89 | C |
| ATOM | 1187 | O | THR | A | 379 | −24.837 | 23.225 | 5.930 | 1.00 | 70.61 | O |
| ATOM | 1188 | N | VAL | A | 380 | −23.014 | 22.036 | 6.546 | 1.00 | 71.89 | N |
| ATOM | 1189 | CA | VAL | A | 380 | −23.190 | 20.907 | 5.594 | 1.00 | 60.25 | C |
| ATOM | 1190 | CB | VAL | A | 380 | −21.819 | 20.342 | 5.070 | 1.00 | 66.55 | C |
| ATOM | 1191 | CG1 | VAL | A | 380 | −22.045 | 19.135 | 4.150 | 1.00 | 65.20 | C |
| ATOM | 1192 | CG2 | VAL | A | 380 | −20.952 | 21.416 | 4.385 | 1.00 | 55.02 | C |
| ATOM | 1193 | C | VAL | A | 380 | −23.925 | 19.744 | 6.278 | 1.00 | 58.18 | C |
| ATOM | 1194 | O | VAL | A | 380 | −23.459 | 19.211 | 7.268 | 1.00 | 55.18 | O |
| ATOM | 1195 | N | HIS | A | 381 | −25.072 | 19.343 | 5.755 | 1.00 | 56.88 | N |
| ATOM | 1196 | CA | HIS | A | 381 | −25.825 | 18.250 | 6.358 | 1.00 | 66.60 | C |
| ATOM | 1197 | CB | HIS | A | 381 | −25.111 | 16.902 | 6.145 | 1.00 | 76.83 | C |
| ATOM | 1198 | CG | HIS | A | 381 | −25.088 | 16.450 | 4.695 | 1.00 | 94.88 | C |

TABLE 8-continued

Atomic coordinates for unbound CRBN-CRBN (TBD) (Apo) (Murine protein)

| ATOM | 1199 | ND1 | HIS | A | 381 | −26.201 | 16.461 | 3.905 | 1.00 | 102.32 | N |
|---|---|---|---|---|---|---|---|---|---|---|---|
| ATOM | 1200 | CE1 | HIS | A | 381 | −25.877 | 16.019 | 2.672 | 1.00 | 103.55 | C |
| ATOM | 1201 | NE2 | HIS | A | 381 | −24.556 | 15.724 | 2.668 | 1.00 | 102.79 | N |
| ATOM | 1202 | CD2 | HIS | A | 381 | −24.044 | 15.974 | 3.899 | 1.00 | 91.39 | C |
| ATOM | 1203 | C | HIS | A | 381 | −26.169 | 18.436 | 7.811 | 1.00 | 66.26 | C |
| ATOM | 1204 | O | HIS | A | 381 | −26.255 | 17.474 | 8.557 | 1.00 | 73.24 | O |
| ATOM | 1205 | N | SER | A | 382 | −26.420 | 19.665 | 8.236 | 1.00 | 59.39 | N |
| ATOM | 1206 | CA | SER | A | 382 | −26.861 | 19.880 | 9.604 | 1.00 | 56.18 | C |
| ATOM | 1207 | CB | SER | A | 382 | −26.969 | 21.374 | 9.925 | 1.00 | 53.01 | C |
| ATOM | 1208 | OG | SER | A | 382 | −27.450 | 21.511 | 11.270 | 1.00 | 52.72 | O |
| ATOM | 1209 | C | SER | A | 382 | −28.199 | 19.187 | 9.902 | 1.00 | 52.61 | C |
| ATOM | 1210 | O | SER | A | 382 | −29.104 | 19.225 | 9.108 | 1.00 | 50.12 | O |
| ATOM | 1211 | N | TRP | A | 383 | −28.326 | 18.588 | 11.074 | 1.00 | 54.29 | N |
| ATOM | 1212 | CA | TRP | A | 383 | −29.575 | 17.934 | 11.469 | 1.00 | 54.64 | C |
| ATOM | 1213 | CB | TRP | A | 383 | −29.327 | 17.010 | 12.665 | 1.00 | 62.52 | C |
| ATOM | 1214 | CG | TRP | A | 383 | −28.406 | 15.848 | 12.350 | 1.00 | 68.50 | C |
| ATOM | 1215 | CD1 | TRP | A | 383 | −28.012 | 15.398 | 11.091 | 1.00 | 65.80 | C |
| ATOM | 1216 | NE1 | TRP | A | 383 | −27.197 | 14.309 | 11.200 | 1.00 | 71.15 | N |
| ATOM | 1217 | CE2 | TRP | A | 383 | −27.018 | 13.962 | 12.487 | 1.00 | 67.46 | C |
| ATOM | 1218 | CD2 | TRP | A | 383 | −27.783 | 14.912 | 13.296 | 1.00 | 66.88 | C |
| ATOM | 1219 | CE3 | TRP | A | 383 | −27.781 | 14.772 | 14.670 | 1.00 | 69.07 | C |
| ATOM | 1220 | CZ3 | TRP | A | 383 | −27.042 | 13.726 | 15.231 | 1.00 | 65.27 | C |
| ATOM | 1221 | CH2 | TRP | A | 383 | −26.311 | 12.829 | 14.441 | 1.00 | 66.51 | C |
| ATOM | 1222 | CZ2 | TRP | A | 383 | −26.284 | 12.929 | 13.055 | 1.00 | 66.29 | C |
| ATOM | 1223 | C | TRP | A | 383 | −30.709 | 18.846 | 11.810 | 1.00 | 56.65 | C |
| ATOM | 1224 | O | TRP | A | 383 | −31.830 | 18.381 | 12.035 | 1.00 | 53.65 | O |
| ATOM | 1225 | N | PHE | A | 384 | −30.433 | 20.149 | 11.865 | 1.00 | 55.34 | N |
| ATOM | 1226 | CA | PHE | A | 384 | −31.373 | 21.135 | 12.380 | 1.00 | 49.78 | C |
| ATOM | 1227 | CB | PHE | A | 384 | −31.026 | 21.526 | 13.828 | 1.00 | 46.49 | C |
| ATOM | 1228 | CG | PHE | A | 384 | −31.443 | 20.499 | 14.861 | 1.00 | 42.91 | C |
| ATOM | 1229 | CD1 | PHE | A | 384 | −32.785 | 20.294 | 15.145 | 1.00 | 50.84 | C |
| ATOM | 1230 | CE1 | PHE | A | 384 | −33.191 | 19.359 | 16.077 | 1.00 | 48.30 | C |
| ATOM | 1231 | CZ | PHE | A | 384 | −32.245 | 18.596 | 16.740 | 1.00 | 41.55 | C |
| ATOM | 1232 | CE2 | PHE | A | 384 | −30.905 | 18.798 | 16.475 | 1.00 | 44.68 | C |
| ATOM | 1233 | CD2 | PHE | A | 384 | −30.511 | 19.755 | 15.546 | 1.00 | 46.48 | C |
| ATOM | 1234 | C | PHE | A | 384 | −31.190 | 22.321 | 11.465 | 1.00 | 55.27 | C |
| ATOM | 1235 | O | PHE | A | 384 | −30.302 | 23.158 | 11.712 | 1.00 | 50.89 | O |
| ATOM | 1236 | N | PRO | A | 385 | −32.015 | 22.393 | 10.395 | 1.00 | 56.35 | N |
| ATOM | 1237 | CA | PRO | A | 385 | −31.851 | 23.393 | 9.336 | 1.00 | 59.39 | C |
| ATOM | 1238 | CB | PRO | A | 385 | −33.073 | 23.172 | 8.433 | 1.00 | 60.57 | C |
| ATOM | 1239 | CG | PRO | A | 385 | −33.552 | 21.803 | 8.753 | 1.00 | 62.49 | C |
| ATOM | 1240 | CD | PRO | A | 385 | −33.212 | 21.556 | 10.188 | 1.00 | 57.37 | C |
| ATOM | 1241 | C | PRO | A | 385 | −31.888 | 24.773 | 9.942 | 1.00 | 58.77 | C |
| ATOM | 1242 | O | PRO | A | 385 | −32.671 | 25.014 | 10.856 | 1.00 | 55.86 | O |
| ATOM | 1243 | N | GLY | A | 386 | −31.026 | 25.658 | 9.465 | 1.00 | 52.17 | N |
| ATOM | 1244 | CA | GLY | A | 386 | −30.873 | 26.933 | 10.104 | 1.00 | 54.56 | C |
| ATOM | 1245 | C | GLY | A | 386 | −29.711 | 27.039 | 11.067 | 1.00 | 54.18 | C |
| ATOM | 1246 | O | GLY | A | 386 | −29.319 | 28.151 | 11.452 | 1.00 | 56.11 | O |
| ATOM | 1247 | N | TYR | A | 387 | −29.150 | 25.902 | 11.456 | 1.00 | 50.58 | N |
| ATOM | 1248 | CA | TYR | A | 387 | −28.034 | 25.885 | 12.440 | 1.00 | 51.00 | C |
| ATOM | 1249 | CB | TYR | A | 387 | −28.468 | 25.226 | 13.754 | 1.00 | 44.20 | C |
| ATOM | 1250 | CG | TYR | A | 387 | −29.576 | 25.940 | 14.524 | 1.00 | 42.14 | C |
| ATOM | 1251 | CD1 | TYR | A | 387 | −29.261 | 26.824 | 15.539 | 1.00 | 44.50 | C |
| ATOM | 1252 | CE1 | TYR | A | 387 | −30.236 | 27.480 | 16.268 | 1.00 | 41.88 | C |
| ATOM | 1253 | CZ | TYR | A | 387 | −31.547 | 27.262 | 15.992 | 1.00 | 39.72 | C |
| ATOM | 1254 | OH | TYR | A | 387 | −32.450 | 27.944 | 16.743 | 1.00 | 42.41 | O |
| ATOM | 1255 | CE2 | TYR | A | 387 | −31.931 | 26.381 | 14.987 | 1.00 | 45.31 | C |
| ATOM | 1256 | CD2 | TYR | A | 387 | −30.933 | 25.707 | 14.255 | 1.00 | 46.96 | C |
| ATOM | 1257 | C | TYR | A | 387 | −26.820 | 25.129 | 11.908 | 1.00 | 54.53 | C |
| ATOM | 1258 | O | TYR | A | 387 | −26.974 | 24.108 | 11.236 | 1.00 | 54.49 | O |
| ATOM | 1259 | N | ALA | A | 388 | −25.632 | 25.651 | 12.211 | 1.00 | 51.55 | N |
| ATOM | 1260 | CA | ALA | A | 388 | −24.368 | 24.975 | 11.971 | 1.00 | 51.75 | C |
| ATOM | 1261 | CB | ALA | A | 388 | −23.258 | 25.994 | 11.797 | 1.00 | 55.46 | C |
| ATOM | 1262 | C | ALA | A | 388 | −24.044 | 24.076 | 13.159 | 1.00 | 51.24 | C |
| ATOM | 1263 | O | ALA | A | 388 | −24.496 | 24.339 | 14.271 | 1.00 | 50.10 | O |
| ATOM | 1264 | N | TRP | A | 389 | −23.268 | 23.016 | 12.939 | 1.00 | 45.80 | N |
| ATOM | 1265 | CA | TRP | A | 389 | −22.907 | 22.127 | 14.055 | 1.00 | 47.94 | C |
| ATOM | 1266 | CB | TRP | A | 389 | −23.379 | 20.694 | 13.811 | 1.00 | 55.02 | C |
| ATOM | 1267 | CG | TRP | A | 389 | −22.997 | 20.096 | 12.466 | 1.00 | 61.96 | C |
| ATOM | 1268 | CD1 | TRP | A | 389 | −23.733 | 20.121 | 11.284 | 1.00 | 60.81 | C |
| ATOM | 1269 | NE1 | TRP | A | 389 | −23.066 | 19.479 | 10.278 | 1.00 | 58.40 | N |
| ATOM | 1270 | CE2 | TRP | A | 389 | −21.886 | 19.000 | 10.707 | 1.00 | 63.93 | C |
| ATOM | 1271 | CD2 | TRP | A | 389 | −21.761 | 19.370 | 12.121 | 1.00 | 61.33 | C |
| ATOM | 1272 | CE3 | TRP | A | 389 | −20.607 | 19.004 | 12.814 | 1.00 | 62.97 | C |
| ATOM | 1273 | CZ3 | TRP | A | 389 | −19.612 | 18.275 | 12.128 | 1.00 | 55.66 | C |
| ATOM | 1274 | CH2 | TRP | A | 389 | −19.759 | 17.933 | 10.776 | 1.00 | 59.86 | C |
| ATOM | 1275 | CZ2 | TRP | A | 389 | −20.889 | 18.295 | 10.037 | 1.00 | 60.84 | C |
| ATOM | 1276 | C | TRP | A | 389 | −21.452 | 22.176 | 14.331 | 1.00 | 48.46 | C |

TABLE 8-continued

Atomic coordinates for unbound CRBN-CRBN (TBD) (Apo) (Murine protein)

| ATOM | 1277 | O | TRP | A | 389 | −20.665 | 22.430 | 13.417 | 1.00 | 53.89 | O |
|---|---|---|---|---|---|---|---|---|---|---|---|
| ATOM | 1278 | N | THR | A | 390 | −21.097 | 22.023 | 15.604 | 1.00 | 46.43 | N |
| ATOM | 1279 | CA | THR | A | 390 | −19.718 | 21.863 | 16.040 | 1.00 | 42.72 | C |
| ATOM | 1280 | CB | THR | A | 390 | −19.174 | 23.145 | 16.683 | 1.00 | 47.53 | C |
| ATOM | 1281 | OG1 | THR | A | 390 | −19.311 | 24.231 | 15.755 | 1.00 | 47.46 | O |
| ATOM | 1282 | CG2 | THR | A | 390 | −17.677 | 22.992 | 17.028 | 1.00 | 40.46 | C |
| ATOM | 1283 | C | THR | A | 390 | −19.628 | 20.716 | 17.061 | 1.00 | 46.44 | C |
| ATOM | 1284 | O | THR | A | 390 | −20.387 | 20.670 | 18.048 | 1.00 | 42.76 | O |
| ATOM | 1285 | N | ILE | A | 391 | −18.688 | 19.802 | 16.826 | 1.00 | 42.41 | N |
| ATOM | 1286 | CA | ILE | A | 391 | −18.476 | 18.637 | 17.667 | 1.00 | 40.33 | C |
| ATOM | 1287 | CB | ILE | A | 391 | −17.309 | 17.791 | 17.119 | 1.00 | 41.51 | C |
| ATOM | 1288 | CG1 | ILE | A | 391 | −17.683 | 17.254 | 15.766 | 1.00 | 44.96 | C |
| ATOM | 1289 | CD1 | ILE | A | 391 | −16.497 | 17.049 | 14.849 | 1.00 | 45.22 | C |
| ATOM | 1290 | CG2 | ILE | A | 391 | −16.964 | 16.644 | 18.082 | 1.00 | 45.22 | C |
| ATOM | 1291 | C | ILE | A | 391 | −18.132 | 19.028 | 19.095 | 1.00 | 38.44 | C |
| ATOM | 1292 | O | ILE | A | 391 | −17.345 | 19.924 | 19.318 | 1.00 | 43.16 | O |
| ATOM | 1293 | N | ALA | A | 392 | −18.671 | 18.299 | 20.061 | 1.00 | 41.48 | N |
| ATOM | 1294 | CA | ALA | A | 392 | −18.401 | 18.602 | 21.469 | 1.00 | 40.50 | C |
| ATOM | 1295 | CB | ALA | A | 392 | −19.625 | 19.267 | 22.086 | 1.00 | 36.53 | C |
| ATOM | 1296 | C | ALA | A | 392 | −18.113 | 17.310 | 22.204 | 1.00 | 44.24 | C |
| ATOM | 1297 | O | ALA | A | 392 | −18.925 | 16.368 | 22.130 | 1.00 | 41.57 | O |
| ATOM | 1298 | N | GLN | A | 393 | −17.013 | 17.290 | 22.966 | 1.00 | 45.37 | N |
| ATOM | 1299 | CA | GLN | A | 393 | −16.682 | 16.151 | 23.808 | 1.00 | 41.94 | C |
| ATOM | 1300 | CB | GLN | A | 393 | −15.485 | 15.394 | 23.195 | 1.00 | 46.38 | C |
| ATOM | 1301 | CG | GLN | A | 393 | −14.158 | 16.130 | 23.317 | 1.00 | 40.87 | C |
| ATOM | 1302 | CD | GLN | A | 393 | −13.092 | 15.637 | 22.333 | 1.00 | 49.74 | C |
| ATOM | 1303 | OE1 | GLN | A | 393 | −13.381 | 15.120 | 21.240 | 1.00 | 60.53 | O |
| ATOM | 1304 | NE2 | GLN | A | 393 | −11.850 | 15.854 | 22.697 | 1.00 | 50.95 | N |
| ATOM | 1305 | C | GLN | A | 393 | −16.380 | 16.469 | 25.274 | 1.00 | 44.97 | C |
| ATOM | 1306 | O | GLN | A | 393 | −16.041 | 17.580 | 25.608 | 1.00 | 46.77 | O |
| ATOM | 1307 | N | CYS | A | 394 | −16.482 | 15.453 | 26.132 | 1.00 | 41.89 | N |
| ATOM | 1308 | CA | CYS | A | 394 | −16.067 | 15.520 | 27.524 | 1.00 | 48.15 | C |
| ATOM | 1309 | CB | CYS | A | 394 | −16.088 | 14.136 | 28.139 | 1.00 | 47.98 | C |
| ATOM | 1310 | SG | CYS | A | 394 | −15.985 | 14.274 | 29.902 | 1.00 | 53.56 | S |
| ATOM | 1311 | C | CYS | A | 394 | −14.684 | 16.083 | 27.676 | 1.00 | 50.29 | C |
| ATOM | 1312 | O | CYS | A | 394 | −13.783 | 15.758 | 26.911 | 1.00 | 51.40 | O |
| ATOM | 1313 | N | LYS | A | 395 | −14.514 | 16.967 | 28.645 | 1.00 | 58.80 | N |
| ATOM | 1314 | CA | LYS | A | 395 | −13.245 | 17.654 | 28.768 | 1.00 | 58.39 | C |
| ATOM | 1315 | CB | LYS | A | 395 | −13.382 | 19.031 | 29.439 | 1.00 | 61.48 | C |
| ATOM | 1316 | CG | LYS | A | 395 | −14.058 | 18.984 | 30.782 | 1.00 | 67.98 | C |
| ATOM | 1317 | CD | LYS | A | 395 | −13.663 | 20.151 | 31.672 | 1.00 | 70.73 | C |
| ATOM | 1318 | CE | LYS | A | 395 | −14.036 | 19.816 | 33.116 | 1.00 | 68.12 | C |
| ATOM | 1319 | NZ | LYS | A | 395 | −14.124 | 21.001 | 34.013 | 1.00 | 64.24 | N |
| ATOM | 1320 | C | LYS | A | 395 | −12.324 | 16.755 | 29.540 | 1.00 | 58.11 | C |
| ATOM | 1321 | O | LYS | A | 395 | −11.128 | 16.883 | 29.410 | 1.00 | 54.52 | O |
| ATOM | 1322 | N | ILE | A | 396 | −12.904 | 15.838 | 30.325 | 1.00 | 59.76 | N |
| ATOM | 1323 | CA | ILE | A | 396 | −12.151 | 14.868 | 31.135 | 1.00 | 55.20 | C |
| ATOM | 1324 | CB | ILE | A | 396 | −13.024 | 14.298 | 32.281 | 1.00 | 62.35 | C |
| ATOM | 1325 | CG1 | ILE | A | 396 | −13.529 | 15.414 | 33.203 | 1.00 | 56.32 | C |
| ATOM | 1326 | CD1 | ILE | A | 396 | −12.470 | 16.338 | 33.739 | 1.00 | 62.62 | C |
| ATOM | 1327 | CG2 | ILE | A | 396 | −12.328 | 13.166 | 33.058 | 1.00 | 60.23 | C |
| ATOM | 1328 | C | ILE | A | 396 | −11.617 | 13.733 | 30.267 | 1.00 | 58.86 | C |
| ATOM | 1329 | O | ILE | A | 396 | −10.382 | 13.614 | 30.071 | 1.00 | 60.14 | O |
| ATOM | 1330 | N | CYS | A | 397 | −12.546 | 12.951 | 29.701 | 1.00 | 53.47 | N |
| ATOM | 1331 | CA | CYS | A | 397 | −12.247 | 11.654 | 29.081 | 1.00 | 56.06 | C |
| ATOM | 1332 | CB | CYS | A | 397 | −13.257 | 10.614 | 29.574 | 1.00 | 53.39 | C |
| ATOM | 1333 | SG | CYS | A | 397 | −14.852 | 10.712 | 28.712 | 1.00 | 53.83 | S |
| ATOM | 1334 | C | CYS | A | 397 | −12.307 | 11.670 | 27.561 | 1.00 | 60.07 | C |
| ATOM | 1335 | O | CYS | A | 397 | −11.992 | 10.684 | 26.896 | 1.00 | 65.82 | O |
| ATOM | 1336 | N | ALA | A | 398 | −12.765 | 12.776 | 26.998 | 1.00 | 60.44 | N |
| ATOM | 1337 | CA | ALA | A | 398 | −12.826 | 12.901 | 25.555 | 1.00 | 47.74 | C |
| ATOM | 1338 | CB | ALA | A | 398 | −11.496 | 12.460 | 24.944 | 1.00 | 52.19 | C |
| ATOM | 1339 | C | ALA | A | 398 | −13.999 | 12.170 | 24.901 | 1.00 | 47.71 | C |
| ATOM | 1340 | O | ALA | A | 398 | −14.087 | 12.149 | 23.678 | 1.00 | 44.78 | O |
| ATOM | 1341 | N | SER | A | 399 | −14.914 | 11.577 | 25.673 | 1.00 | 45.53 | N |
| ATOM | 1342 | CA | SER | A | 399 | −16.079 | 10.944 | 25.030 | 1.00 | 48.46 | C |
| ATOM | 1343 | CB | SER | A | 399 | −16.906 | 10.242 | 26.079 | 1.00 | 44.55 | C |
| ATOM | 1344 | OG | SER | A | 399 | −18.127 | 9.798 | 25.546 | 1.00 | 53.65 | O |
| ATOM | 1345 | C | SER | A | 399 | −16.958 | 11.936 | 24.203 | 1.00 | 57.68 | C |
| ATOM | 1346 | O | SER | A | 399 | −17.172 | 13.074 | 24.632 | 1.00 | 57.72 | O |
| ATOM | 1347 | N | HIS | A | 400 | −17.450 | 11.514 | 23.030 | 1.00 | 52.97 | N |
| ATOM | 1348 | CA | HIS | A | 400 | −18.225 | 12.385 | 22.147 | 1.00 | 56.67 | C |
| ATOM | 1349 | CB | HIS | A | 400 | −18.264 | 11.865 | 20.713 | 1.00 | 48.92 | C |
| ATOM | 1350 | CG | HIS | A | 400 | −16.969 | 12.035 | 19.998 | 1.00 | 59.48 | C |
| ATOM | 1351 | ND1 | HIS | A | 400 | −15.794 | 12.106 | 20.655 | 1.00 | 61.72 | N |
| ATOM | 1352 | CE1 | HIS | A | 400 | −14.806 | 12.237 | 19.763 | 1.00 | 62.17 | C |
| ATOM | 1353 | NE2 | HIS | A | 400 | −15.346 | 12.235 | 18.543 | 1.00 | 56.58 | N |
| ATOM | 1354 | CD2 | HIS | A | 400 | −16.675 | 12.121 | 18.653 | 1.00 | 58.53 | C |

TABLE 8-continued

Atomic coordinates for unbound CRBN-CRBN (TBD) (Apo) (Murine protein)

| ATOM | 1355 | C | HIS | A | 400 | −19.603 | 12.492 | 22.632 | 1.00 | 59.47 | C |
|---|---|---|---|---|---|---|---|---|---|---|---|
| ATOM | 1356 | O | HIS | A | 400 | −20.384 | 11.560 | 22.470 | 1.00 | 65.12 | O |
| ATOM | 1357 | N | ILE | A | 401 | −19.956 | 13.623 | 23.230 | 1.00 | 52.92 | N |
| ATOM | 1358 | CA | ILE | A | 401 | −21.286 | 13.667 | 23.788 | 1.00 | 45.82 | C |
| ATOM | 1359 | CB | ILE | A | 401 | −21.300 | 14.482 | 25.078 | 1.00 | 47.51 | C |
| ATOM | 1360 | CG1 | ILE | A | 401 | −20.154 | 14.006 | 25.984 | 1.00 | 48.01 | C |
| ATOM | 1361 | CD1 | ILE | A | 401 | −20.429 | 12.742 | 26.777 | 1.00 | 47.02 | C |
| ATOM | 1362 | CG2 | ILE | A | 401 | −22.651 | 14.436 | 25.804 | 1.00 | 43.21 | C |
| ATOM | 1363 | C | ILE | A | 401 | −22.250 | 14.160 | 22.702 | 1.00 | 45.88 | C |
| ATOM | 1364 | O | ILE | A | 401 | −23.383 | 13.715 | 22.623 | 1.00 | 47.58 | O |
| ATOM | 1365 | N | GLY | A | 402 | −21.807 | 15.094 | 21.874 | 1.00 | 45.44 | N |
| ATOM | 1366 | CA | GLY | A | 402 | −22.694 | 15.608 | 20.855 | 1.00 | 41.84 | C |
| ATOM | 1367 | C | GLY | A | 402 | −22.195 | 16.864 | 20.201 | 1.00 | 42.30 | C |
| ATOM | 1368 | O | GLY | A | 402 | −21.032 | 16.922 | 19.773 | 1.00 | 44.96 | O |
| ATOM | 1369 | N | TRP | A | 403 | −23.068 | 17.882 | 20.128 | 1.00 | 36.73 | N |
| ATOM | 1370 | CA | TRP | A | 403 | −22.796 | 19.046 | 19.289 | 1.00 | 37.78 | C |
| ATOM | 1371 | CB | TRP | A | 403 | −23.451 | 18.859 | 17.900 | 1.00 | 38.58 | C |
| ATOM | 1372 | CG | TRP | A | 403 | −22.985 | 17.628 | 17.160 | 1.00 | 44.12 | C |
| ATOM | 1373 | CD1 | TRP | A | 403 | −21.931 | 17.532 | 16.244 | 1.00 | 42.52 | C |
| ATOM | 1374 | NE1 | TRP | A | 403 | −21.763 | 16.251 | 15.829 | 1.00 | 39.15 | N |
| ATOM | 1375 | CE2 | TRP | A | 403 | −22.650 | 15.416 | 16.432 | 1.00 | 47.67 | C |
| ATOM | 1376 | CD2 | TRP | A | 403 | −23.495 | 16.248 | 17.300 | 1.00 | 45.43 | C |
| ATOM | 1377 | CE3 | TRP | A | 403 | −24.536 | 15.647 | 18.020 | 1.00 | 46.26 | C |
| ATOM | 1378 | CZ3 | TRP | A | 403 | −24.725 | 14.257 | 17.904 | 1.00 | 49.94 | C |
| ATOM | 1379 | CH2 | TRP | A | 403 | −23.921 | 13.476 | 17.043 | 1.00 | 53.93 | C |
| ATOM | 1380 | CZ2 | TRP | A | 403 | −22.869 | 14.041 | 16.284 | 1.00 | 46.89 | C |
| ATOM | 1381 | C | TRP | A | 403 | −23.342 | 20.327 | 19.891 | 1.00 | 41.61 | C |
| ATOM | 1382 | O | TRP | A | 403 | −24.407 | 20.327 | 20.522 | 1.00 | 38.88 | O |
| ATOM | 1383 | N | LYS | A | 404 | −22.642 | 21.424 | 19.625 | 1.00 | 36.36 | N |
| ATOM | 1384 | CA | LYS | A | 404 | −23.180 | 22.743 | 19.755 | 1.00 | 42.82 | C |
| ATOM | 1385 | CB | LYS | A | 404 | −22.069 | 23.742 | 20.078 | 1.00 | 44.40 | C |
| ATOM | 1386 | CG | LYS | A | 404 | −22.567 | 25.124 | 20.549 | 1.00 | 47.41 | C |
| ATOM | 1387 | CD | LYS | A | 404 | −21.430 | 26.149 | 20.621 | 1.00 | 52.01 | C |
| ATOM | 1388 | CE | LYS | A | 404 | −21.605 | 27.125 | 21.786 | 1.00 | 59.97 | C |
| ATOM | 1389 | NZ | LYS | A | 404 | −20.430 | 28.027 | 22.061 | 1.00 | 57.40 | N |
| ATOM | 1390 | C | LYS | A | 404 | −23.819 | 23.117 | 18.431 | 1.00 | 45.19 | C |
| ATOM | 1391 | O | LYS | A | 404 | −23.175 | 22.983 | 17.388 | 1.00 | 48.81 | O |
| ATOM | 1392 | N | PHE | A | 405 | −25.072 | 23.569 | 18.469 | 1.00 | 38.31 | N |
| ATOM | 1393 | CA | PHE | A | 405 | −25.705 | 24.123 | 17.271 | 1.00 | 40.90 | C |
| ATOM | 1394 | CB | PHE | A | 405 | −27.094 | 23.496 | 17.069 | 1.00 | 39.47 | C |
| ATOM | 1395 | CG | PHE | A | 405 | −27.037 | 22.035 | 16.641 | 1.00 | 39.51 | C |
| ATOM | 1396 | CD1 | PHE | A | 405 | −26.885 | 21.693 | 15.275 | 1.00 | 39.99 | C |
| ATOM | 1397 | CE1 | PHE | A | 405 | −26.786 | 20.362 | 14.873 | 1.00 | 41.24 | C |
| ATOM | 1398 | CZ | PHE | A | 405 | −26.877 | 19.356 | 15.833 | 1.00 | 43.05 | C |
| ATOM | 1399 | CE2 | PHE | A | 405 | −27.015 | 19.690 | 17.184 | 1.00 | 43.92 | C |
| ATOM | 1400 | CD2 | PHE | A | 405 | −27.097 | 21.014 | 17.582 | 1.00 | 38.87 | C |
| ATOM | 1401 | C | PHE | A | 405 | −25.769 | 25.655 | 17.324 | 1.00 | 42.45 | C |
| ATOM | 1402 | O | PHE | A | 405 | −26.161 | 26.221 | 18.341 | 1.00 | 42.52 | O |
| ATOM | 1403 | N | THR | A | 406 | −25.339 | 26.328 | 16.257 | 1.00 | 43.08 | N |
| ATOM | 1404 | CA | THR | A | 406 | −25.296 | 27.802 | 16.239 | 1.00 | 46.58 | C |
| ATOM | 1405 | CB | THR | A | 406 | −23.841 | 28.323 | 16.135 | 1.00 | 48.64 | C |
| ATOM | 1406 | OG1 | THR | A | 406 | −23.115 | 27.450 | 15.281 | 1.00 | 47.40 | O |
| ATOM | 1407 | CG2 | THR | A | 406 | −23.144 | 28.325 | 17.488 | 1.00 | 41.25 | C |
| ATOM | 1408 | C | THR | A | 406 | −26.125 | 28.352 | 15.065 | 1.00 | 45.32 | C |
| ATOM | 1409 | O | THR | A | 406 | −25.953 | 27.902 | 13.938 | 1.00 | 46.96 | O |
| ATOM | 1410 | N | ALA | A | 407 | −27.044 | 29.290 | 15.326 | 1.00 | 42.01 | N |
| ATOM | 1411 | CA | ALA | A | 407 | −27.908 | 29.851 | 14.253 | 1.00 | 43.20 | C |
| ATOM | 1412 | CB | ALA | A | 407 | −28.890 | 30.890 | 14.827 | 1.00 | 36.73 | C |
| ATOM | 1413 | C | ALA | A | 407 | −27.110 | 30.499 | 13.120 | 1.00 | 40.45 | C |
| ATOM | 1414 | O | ALA | A | 407 | −26.270 | 31.319 | 13.385 | 1.00 | 40.73 | O |
| ATOM | 1415 | N | THR | A | 408 | −27.410 | 30.161 | 11.866 | 1.00 | 47.02 | N |
| ATOM | 1416 | CA | THR | A | 408 | −26.847 | 30.869 | 10.707 | 1.00 | 48.85 | C |
| ATOM | 1417 | CB | THR | A | 408 | −26.990 | 30.053 | 9.413 | 1.00 | 48.14 | C |
| ATOM | 1418 | OG1 | THR | A | 408 | −28.344 | 30.097 | 8.977 | 1.00 | 61.55 | O |
| ATOM | 1419 | CG2 | THR | A | 408 | −26.602 | 28.623 | 9.604 | 1.00 | 45.87 | C |
| ATOM | 1420 | C | THR | A | 408 | −27.465 | 32.283 | 10.468 | 1.00 | 57.62 | C |
| ATOM | 1421 | O | THR | A | 408 | −26.811 | 33.126 | 9.864 | 1.00 | 62.00 | O |
| ATOM | 1422 | N | LYS | A | 409 | −28.690 | 32.533 | 10.961 | 1.00 | 52.67 | N |
| ATOM | 1423 | CA | LYS | A | 409 | −29.369 | 33.872 | 10.887 | 1.00 | 56.68 | C |
| ATOM | 1424 | CB | LYS | A | 409 | −30.601 | 33.855 | 9.974 | 1.00 | 53.63 | C |
| ATOM | 1425 | CG | LYS | A | 409 | −30.261 | 33.596 | 8.524 | 1.00 | 68.12 | C |
| ATOM | 1426 | CD | LYS | A | 409 | −31.478 | 33.137 | 7.734 | 1.00 | 83.27 | C |
| ATOM | 1427 | CE | LYS | A | 409 | −32.061 | 34.259 | 6.878 | 1.00 | 84.67 | C |
| ATOM | 1428 | NZ | LYS | A | 409 | −33.306 | 34.824 | 7.466 | 1.00 | 87.15 | N |
| ATOM | 1429 | C | LYS | A | 409 | −29.748 | 34.481 | 12.235 | 1.00 | 46.56 | C |
| ATOM | 1430 | O | LYS | A | 409 | −30.131 | 33.795 | 13.170 | 1.00 | 45.30 | O |
| ATOM | 1431 | N | LYS | A | 410 | −29.606 | 35.791 | 12.316 | 1.00 | 48.26 | N |
| ATOM | 1432 | CA | LYS | A | 410 | −29.712 | 36.532 | 13.563 | 1.00 | 52.99 | C |

TABLE 8-continued

Atomic coordinates for unbound CRBN-CRBN (TBD) (Apo) (Murine protein)

| ATOM | 1433 | CB | LYS | A | 410 | −29.044 | 37.886 | 13.396 | 1.00 | 56.59 | C |
|---|---|---|---|---|---|---|---|---|---|---|---|
| ATOM | 1434 | CG | LYS | A | 410 | −27.544 | 37.867 | 13.637 | 1.00 | 67.81 | C |
| ATOM | 1435 | CD | LYS | A | 410 | −27.196 | 38.721 | 14.851 | 1.00 | 70.64 | C |
| ATOM | 1436 | CE | LYS | A | 410 | −25.851 | 39.419 | 14.664 | 1.00 | 71.13 | C |
| ATOM | 1437 | NZ | LYS | A | 410 | −25.809 | 40.799 | 15.245 | 1.00 | 72.83 | N |
| ATOM | 1438 | C | LYS | A | 410 | −31.138 | 36.709 | 14.086 | 1.00 | 54.59 | C |
| ATOM | 1439 | O | LYS | A | 410 | −31.338 | 37.003 | 15.272 | 1.00 | 47.67 | O |
| ATOM | 1440 | N | ASP | A | 411 | −32.126 | 36.494 | 13.222 | 1.00 | 50.60 | N |
| ATOM | 1441 | CA | ASP | A | 411 | −33.499 | 36.594 | 13.669 | 1.00 | 55.97 | C |
| ATOM | 1442 | CB | ASP | A | 411 | −34.382 | 37.161 | 12.549 | 1.00 | 60.11 | C |
| ATOM | 1443 | CG | ASP | A | 411 | −34.525 | 36.224 | 11.359 | 1.00 | 62.81 | C |
| ATOM | 1444 | OD1 | ASP | A | 411 | −34.074 | 35.067 | 11.370 | 1.00 | 62.81 | O |
| ATOM | 1445 | OD2 | ASP | A | 411 | −35.119 | 36.663 | 10.375 | 1.00 | 64.67 | O |
| ATOM | 1446 | C | ASP | A | 411 | −34.088 | 35.300 | 14.281 | 1.00 | 56.90 | C |
| ATOM | 1447 | O | ASP | A | 411 | −35.233 | 35.307 | 14.706 | 1.00 | 63.74 | O |
| ATOM | 1448 | N | MET | A | 412 | −33.303 | 34.210 | 14.305 | 1.00 | 49.60 | N |
| ATOM | 1449 | CA | MET | A | 412 | −33.696 | 32.907 | 14.903 | 1.00 | 51.10 | C |
| ATOM | 1450 | CB | MET | A | 412 | −32.748 | 31.787 | 14.436 | 1.00 | 40.68 | C |
| ATOM | 1451 | CG | MET | A | 412 | −32.989 | 31.408 | 12.982 | 1.00 | 58.61 | C |
| ATOM | 1452 | SD | MET | A | 412 | −32.027 | 30.014 | 12.337 | 1.00 | 63.69 | S |
| ATOM | 1453 | CE | MET | A | 412 | −30.594 | 30.851 | 11.709 | 1.00 | 58.46 | C |
| ATOM | 1454 | C | MET | A | 412 | −33.676 | 32.894 | 16.425 | 1.00 | 48.39 | C |
| ATOM | 1455 | O | MET | A | 412 | −32.952 | 33.678 | 17.053 | 1.00 | 42.71 | O |
| ATOM | 1456 | N | SER | A | 413 | −34.414 | 31.957 | 17.026 | 1.00 | 44.90 | N |
| ATOM | 1457 | CA | SER | A | 413 | −34.235 | 31.744 | 18.446 | 1.00 | 42.44 | C |
| ATOM | 1458 | CB | SER | A | 413 | −35.302 | 32.474 | 19.227 | 1.00 | 42.13 | C |
| ATOM | 1459 | OG | SER | A | 413 | −36.572 | 31.990 | 18.812 | 1.00 | 46.24 | O |
| ATOM | 1460 | C | SER | A | 413 | −34.360 | 30.257 | 18.679 | 1.00 | 37.75 | C |
| ATOM | 1461 | O | SER | A | 413 | −35.225 | 29.640 | 18.086 | 1.00 | 38.47 | O |
| ATOM | 1462 | N | PRO | A | 414 | −33.515 | 29.678 | 19.560 | 1.00 | 33.40 | N |
| ATOM | 1463 | CA | PRO | A | 414 | −32.410 | 30.358 | 20.180 | 1.00 | 35.27 | C |
| ATOM | 1464 | CB | PRO | A | 414 | −32.070 | 29.457 | 21.356 | 1.00 | 37.15 | C |
| ATOM | 1465 | CG | PRO | A | 414 | −32.436 | 28.091 | 20.911 | 1.00 | 37.45 | C |
| ATOM | 1466 | CD | PRO | A | 414 | −33.674 | 28.301 | 20.075 | 1.00 | 36.86 | C |
| ATOM | 1467 | C | PRO | A | 414 | −31.225 | 30.528 | 19.228 | 1.00 | 37.68 | C |
| ATOM | 1468 | O | PRO | A | 414 | −31.229 | 29.925 | 18.146 | 1.00 | 34.36 | O |
| ATOM | 1469 | N | GLN | A | 415 | −30.268 | 31.404 | 19.573 | 1.00 | 37.06 | N |
| ATOM | 1470 | CA | GLN | A | 415 | −29.066 | 31.587 | 18.696 | 1.00 | 35.80 | C |
| ATOM | 1471 | CB | GLN | A | 415 | −28.296 | 32.908 | 18.990 | 1.00 | 38.30 | C |
| ATOM | 1472 | CG | GLN | A | 415 | −28.996 | 34.164 | 18.389 | 1.00 | 43.27 | C |
| ATOM | 1473 | CD | GLN | A | 415 | −28.987 | 34.180 | 16.846 | 1.00 | 41.84 | C |
| ATOM | 1474 | OE1 | GLN | A | 415 | −29.992 | 33.869 | 16.200 | 1.00 | 43.35 | O |
| ATOM | 1475 | NE2 | GLN | A | 415 | −27.865 | 34.531 | 16.262 | 1.00 | 39.58 | N |
| ATOM | 1476 | C | GLN | A | 415 | −28.119 | 30.401 | 18.756 | 1.00 | 33.60 | C |
| ATOM | 1477 | O | GLN | A | 415 | −27.382 | 30.139 | 17.823 | 1.00 | 34.13 | O |
| ATOM | 1478 | N | LYS | A | 416 | −28.200 | 29.674 | 19.856 | 1.00 | 39.79 | N |
| ATOM | 1479 | CA | LYS | A | 416 | −27.375 | 28.527 | 20.097 | 1.00 | 43.58 | C |
| ATOM | 1480 | CB | LYS | A | 416 | −26.003 | 28.954 | 20.686 | 1.00 | 50.16 | C |
| ATOM | 1481 | CG | LYS | A | 416 | −26.000 | 29.133 | 22.187 | 1.00 | 54.46 | C |
| ATOM | 1482 | CD | LYS | A | 416 | −24.815 | 29.949 | 22.676 | 1.00 | 54.77 | C |
| ATOM | 1483 | CE | LYS | A | 416 | −25.247 | 30.768 | 23.869 | 1.00 | 50.07 | C |
| ATOM | 1484 | NZ | LYS | A | 416 | −25.911 | 32.082 | 23.480 | 1.00 | 39.14 | N |
| ATOM | 1485 | C | LYS | A | 416 | −28.118 | 27.553 | 21.025 | 1.00 | 41.06 | C |
| ATOM | 1486 | O | LYS | A | 416 | −28.958 | 27.944 | 21.853 | 1.00 | 39.51 | O |
| ATOM | 1487 | N | PHE | A | 417 | −27.823 | 26.275 | 20.839 | 1.00 | 41.90 | N |
| ATOM | 1488 | CA | PHE | A | 417 | −28.221 | 25.224 | 21.750 | 1.00 | 39.41 | C |
| ATOM | 1489 | CB | PHE | A | 417 | −29.697 | 24.827 | 21.523 | 1.00 | 34.05 | C |
| ATOM | 1490 | CG | PHE | A | 417 | −29.963 | 24.160 | 20.207 | 1.00 | 35.43 | C |
| ATOM | 1491 | CD1 | PHE | A | 417 | −29.968 | 22.735 | 20.091 | 1.00 | 34.81 | C |
| ATOM | 1492 | CE1 | PHE | A | 417 | −30.216 | 22.142 | 18.839 | 1.00 | 35.79 | C |
| ATOM | 1493 | CZ | PHE | A | 417 | −30.509 | 22.944 | 17.720 | 1.00 | 33.80 | C |
| ATOM | 1494 | CE2 | PHE | A | 417 | −30.567 | 24.345 | 17.852 | 1.00 | 32.41 | C |
| ATOM | 1495 | CD2 | PHE | A | 417 | −30.296 | 24.929 | 19.085 | 1.00 | 32.34 | C |
| ATOM | 1496 | C | PHE | A | 417 | −27.265 | 24.011 | 21.566 | 1.00 | 38.54 | C |
| ATOM | 1497 | O | PHE | A | 417 | −26.400 | 24.036 | 20.678 | 1.00 | 42.55 | O |
| ATOM | 1498 | N | TRP | A | 418 | −27.472 | 22.951 | 22.368 | 1.00 | 33.60 | N |
| ATOM | 1499 | CA | TRP | A | 418 | −26.664 | 21.745 | 22.329 | 1.00 | 37.44 | C |
| ATOM | 1500 | CB | TRP | A | 418 | −25.983 | 21.492 | 23.668 | 1.00 | 37.59 | C |
| ATOM | 1501 | CG | TRP | A | 418 | −25.132 | 22.628 | 24.130 | 1.00 | 38.53 | C |
| ATOM | 1502 | CD1 | TRP | A | 418 | −25.553 | 23.753 | 24.847 | 1.00 | 40.93 | C |
| ATOM | 1503 | NE1 | TRP | A | 418 | −24.492 | 24.599 | 25.095 | 1.00 | 39.89 | N |
| ATOM | 1504 | CE2 | TRP | A | 418 | −23.332 | 24.092 | 24.557 | 1.00 | 45.82 | C |
| ATOM | 1505 | CD2 | TRP | A | 418 | −23.681 | 22.819 | 23.907 | 1.00 | 42.89 | C |
| ATOM | 1506 | CE3 | TRP | A | 418 | −22.662 | 22.069 | 23.287 | 1.00 | 42.54 | C |
| ATOM | 1507 | CZ3 | TRP | A | 418 | −21.371 | 22.569 | 23.294 | 1.00 | 44.20 | C |
| ATOM | 1508 | CH2 | TRP | A | 418 | −21.055 | 23.807 | 23.930 | 1.00 | 45.59 | C |
| ATOM | 1509 | CZ2 | TRP | A | 418 | −22.018 | 24.573 | 24.575 | 1.00 | 38.75 | C |
| ATOM | 1510 | C | TRP | A | 418 | −27.532 | 20.560 | 21.999 | 1.00 | 39.78 | C |

TABLE 8-continued

Atomic coordinates for unbound CRBN-CRBN (TBD) (Apo) (Murine protein)

| | | | | | | | | | | |
|---|---|---|---|---|---|---|---|---|---|---|
| ATOM | 1511 | O | TRP | A | 418 | −28.676 | 20.460 | 22.473 | 1.00 | 36.22 | O |
| ATOM | 1512 | N | GLY | A | 419 | −26.977 | 19.648 | 21.197 | 1.00 | 43.31 | N |
| ATOM | 1513 | CA | GLY | A | 419 | −27.676 | 18.410 | 20.786 | 1.00 | 40.79 | C |
| ATOM | 1514 | C | GLY | A | 419 | −26.857 | 17.291 | 21.372 | 1.00 | 38.98 | C |
| ATOM | 1515 | O | GLY | A | 419 | −25.721 | 17.096 | 20.980 | 1.00 | 41.76 | O |
| ATOM | 1516 | N | LEU | A | 420 | −27.447 | 16.564 | 22.310 | 1.00 | 42.02 | N |
| ATOM | 1517 | CA | LEU | A | 420 | −26.730 | 15.576 | 23.083 | 1.00 | 43.66 | C |
| ATOM | 1518 | CB | LEU | A | 420 | −26.794 | 15.907 | 24.569 | 1.00 | 41.30 | C |
| ATOM | 1519 | CG | LEU | A | 420 | −26.281 | 17.276 | 25.020 | 1.00 | 43.93 | C |
| ATOM | 1520 | CD1 | LEU | A | 420 | −26.274 | 17.287 | 26.545 | 1.00 | 45.97 | C |
| ATOM | 1521 | CD2 | LEU | A | 420 | −24.904 | 17.620 | 24.432 | 1.00 | 44.93 | C |
| ATOM | 1522 | C | LEU | A | 420 | −27.300 | 14.196 | 22.843 | 1.00 | 45.63 | C |
| ATOM | 1523 | O | LEU | A | 420 | −28.523 | 13.983 | 22.988 | 1.00 | 47.89 | O |
| ATOM | 1524 | N | THR | A | 421 | −26.403 | 13.275 | 22.475 | 1.00 | 47.19 | N |
| ATOM | 1525 | CA | THR | A | 421 | −26.755 | 11.873 | 22.179 | 1.00 | 50.41 | C |
| ATOM | 1526 | CB | THR | A | 421 | −25.580 | 11.141 | 21.497 | 1.00 | 57.95 | C |
| ATOM | 1527 | OG1 | THR | A | 421 | −25.099 | 11.920 | 20.399 | 1.00 | 53.64 | O |
| ATOM | 1528 | CG2 | THR | A | 421 | −26.023 | 9.735 | 20.980 | 1.00 | 59.01 | C |
| ATOM | 1529 | C | THR | A | 421 | −27.133 | 11.185 | 23.483 | 1.00 | 47.41 | C |
| ATOM | 1530 | O | THR | A | 421 | −26.315 | 11.072 | 24.382 | 1.00 | 42.69 | O |
| ATOM | 1531 | N | ARG | A | 422 | −28.403 | 10.830 | 23.627 | 1.00 | 50.09 | N |
| ATOM | 1532 | CA | ARG | A | 422 | −28.910 | 10.249 | 24.875 | 1.00 | 53.93 | C |
| ATOM | 1533 | CB | ARG | A | 422 | −30.353 | 9.743 | 24.671 | 1.00 | 59.09 | C |
| ATOM | 1534 | CG | ARG | A | 422 | −31.413 | 10.603 | 25.351 | 1.00 | 70.59 | C |
| ATOM | 1535 | CD | ARG | A | 422 | −32.758 | 9.888 | 25.504 | 1.00 | 76.14 | C |
| ATOM | 1536 | NE | ARG | A | 422 | −33.693 | 10.198 | 24.41 | 1.00 | 87.31 | N |
| ATOM | 1537 | CZ | ARG | A | 422 | −34.200 | 11.409 | 24.159 | 1.00 | 89.80 | C |
| ATOM | 1538 | NH1 | ARG | A | 422 | −33.862 | 12.444 | 24.913 | 1.00 | 92.14 | N |
| ATOM | 1539 | NH2 | ARG | A | 422 | −35.044 | 11.600 | 23.147 | 1.00 | 82.65 | N |
| ATOM | 1540 | C | ARG | A | 422 | −28.029 | 9.095 | 25.397 | 1.00 | 59.55 | C |
| ATOM | 1541 | O | ARG | A | 422 | −27.778 | 8.963 | 26.600 | 1.00 | 55.46 | O |
| ATOM | 1542 | N | SER | A | 423 | −27.561 | 8.246 | 24.490 | 1.00 | 58.91 | N |
| ATOM | 1543 | CA | SER | A | 423 | −26.897 | 7.040 | 24.959 | 1.00 | 65.33 | C |
| ATOM | 1544 | CB | SER | A | 423 | −26.910 | 5.919 | 23.884 | 1.00 | 53.93 | C |
| ATOM | 1545 | OG | SER | A | 423 | −25.971 | 6.168 | 22.859 | 1.00 | 62.93 | O |
| ATOM | 1546 | C | SER | A | 423 | −25.498 | 7.389 | 25.497 | 1.00 | 67.39 | C |
| ATOM | 1547 | O | SER | A | 423 | −24.847 | 6.539 | 26.110 | 1.00 | 64.90 | O |
| ATOM | 1548 | N | ALA | A | 424 | −25.048 | 8.646 | 25.315 | 1.00 | 56.20 | N |
| ATOM | 1549 | CA | ALA | A | 424 | −23.737 | 9.041 | 25.835 | 1.00 | 49.33 | C |
| ATOM | 1550 | CB | ALA | A | 424 | −23.026 | 9.967 | 24.875 | 1.00 | 49.27 | C |
| ATOM | 1551 | C | ALA | A | 424 | −23.799 | 9.636 | 27.239 | 1.00 | 53.75 | C |
| ATOM | 1552 | O | ALA | A | 424 | −22.765 | 10.037 | 27.813 | 1.00 | 59.49 | O |
| ATOM | 1553 | N | LEU | A | 425 | −24.995 | 9.639 | 27.821 | 1.00 | 48.80 | N |
| ATOM | 1554 | CA | LEU | A | 425 | −25.202 | 10.259 | 29.140 | 1.00 | 56.48 | C |
| ATOM | 1555 | CB | LEU | A | 425 | −26.202 | 11.423 | 28.987 | 1.00 | 56.27 | C |
| ATOM | 1556 | CG | LEU | A | 425 | −25.822 | 12.571 | 28.057 | 1.00 | 55.42 | C |
| ATOM | 1557 | CD1 | LEU | A | 425 | −27.011 | 13.497 | 27.869 | 1.00 | 52.51 | C |
| ATOM | 1558 | CD2 | LEU | A | 425 | −24.651 | 13.316 | 28.687 | 1.00 | 56.42 | C |
| ATOM | 1559 | C | LEU | A | 425 | −25.722 | 9.264 | 30.170 | 1.00 | 51.66 | C |
| ATOM | 1560 | O | LEU | A | 425 | −26.254 | 8.226 | 29.786 | 1.00 | 62.08 | O |
| ATOM | 1561 | N | LEU | A | 426 | −25.593 | 9.576 | 31.460 | 1.00 | 52.97 | N |
| ATOM | 1562 | CA | LEU | A | 426 | −26.245 | 8.775 | 32.509 | 1.00 | 60.78 | C |
| ATOM | 1563 | CB | LEU | A | 426 | −25.238 | 7.986 | 33.358 | 1.00 | 62.95 | C |
| ATOM | 1564 | CG | LEU | A | 426 | −24.984 | 6.515 | 32.925 | 1.00 | 74.12 | C |
| ATOM | 1565 | CD1 | LEU | A | 426 | −24.024 | 5.859 | 33.903 | 1.00 | 71.58 | C |
| ATOM | 1566 | CD2 | LEU | A | 426 | −26.234 | 5.629 | 32.719 | 1.00 | 65.84 | C |
| ATOM | 1567 | C | LEU | A | 426 | −27.290 | 9.495 | 33.366 | 1.00 | 63.28 | C |
| ATOM | 1568 | O | LEU | A | 426 | −27.105 | 10.649 | 33.686 | 1.00 | 64.25 | O |
| ATOM | 1569 | N | PRO | A | 427 | −28.291 | 8.749 | 33.872 | 1.00 | 75.24 | N |
| ATOM | 1570 | CA | PRO | A | 427 | −29.720 | 8.955 | 33.938 | 1.00 | 80.59 | C |
| ATOM | 1571 | CB | PRO | A | 427 | −29.868 | 9.778 | 35.216 | 1.00 | 84.11 | C |
| ATOM | 1572 | CG | PRO | A | 427 | −28.765 | 9.224 | 36.105 | 1.00 | 87.05 | C |
| ATOM | 1573 | CD | PRO | A | 427 | −27.865 | 8.362 | 35.229 | 1.00 | 86.56 | C |
| ATOM | 1574 | C | PRO | A | 427 | −30.291 | 9.651 | 32.713 | 1.00 | 83.29 | C |
| ATOM | 1575 | O | PRO | A | 427 | −29.994 | 9.220 | 31.596 | 1.00 | 78.84 | O |
| ATOM | 1576 | O4 | SO4 | B | 1 | −6.780 | 3.107 | 0.782 | 0.50 | 55.03 | O |
| ATOM | 1577 | S | SO4 | B | 1 | −6.029 | 2.170 | 0.074 | 0.50 | 54.80 | S |
| ATOM | 1578 | O1 | SO4 | B | 1 | −4.565 | 2.401 | 0.097 | 0.50 | 58.00 | O |
| ATOM | 1579 | O2 | SO4 | B | 1 | −6.458 | 2.438 | 1.462 | 0.50 | 49.67 | O |
| ATOM | 1580 | O3 | SO4 | B | 1 | −6.297 | 0.773 | 0.307 | 0.50 | 53.83 | O |
| ATOM | 1581 | O4 | SO4 | B | 2 | −0.580 | 0.259 | 1.180 | 0.30 | 35.16 | O |
| ATOM | 1582 | S | SO4 | B | 2 | −1.057 | 0.990 | 0.964 | 0.30 | 34.90 | S |
| ATOM | 1583 | O1 | SO4 | B | 2 | −0.558 | 1.519 | 0.182 | 0.30 | 36.43 | O |
| ATOM | 1584 | O2 | SO4 | B | 2 | −0.682 | 1.755 | 1.988 | 0.30 | 35.33 | O |
| ATOM | 1585 | O3 | SO4 | B | 2 | −2.418 | 0.997 | 0.928 | 0.30 | 33.76 | O |
| ATOM | 1586 | O4 | SO4 | B | 3 | −2.177 | 0.336 | 4.453 | 0.50 | 40.70 | ZN |
| ATOM | 1587 | S | SO4 | B | 3 | −1.783 | 0.126 | 5.881 | 0.50 | 40.38 | ZN |
| ATOM | 1588 | O1 | SO4 | B | 3 | −2.811 | 0.622 | 6.819 | 0.50 | 39.17 | O |

TABLE 8-continued

Atomic coordinates for unbound CRBN-CRBN (TBD) (Apo) (Murine protein)

| ATOM | 1589 | O2 | SO4 | B | 3 | −0.546 | 0.912 | 5.979 | 0.50 | 40.18 | O |
|---|---|---|---|---|---|---|---|---|---|---|---|
| ATOM | 1590 | O3 | SO4 | B | 3 | −1.601 | 1.301 | 6.178 | 0.50 | 44.17 | O |
| ATOM | 1591 | O4 | SO4 | B | 4 | −28.980 | 34.035 | 22.827 | 0.50 | 50.39 | O |
| ATOM | 1592 | S | SO4 | B | 4 | −30.024 | 32.990 | 22.735 | 0.50 | 50.79 | S |
| ATOM | 1593 | O1 | SO4 | B | 4 | −29.392 | 31.765 | 22.156 | 0.50 | 49.15 | O |
| ATOM | 1594 | O2 | SO4 | B | 4 | −31.178 | 33.475 | 21.919 | 0.50 | 44.58 | O |
| ATOM | 1595 | O3 | SO4 | B | 4 | −30.494 | 32.644 | 24.092 | 0.50 | 43.93 | O |
| ATOM | 1596 | O4 | SO4 | B | 5 | −28.084 | 33.478 | 27.010 | 0.50 | 58.70 | O |
| ATOM | 1597 | S | SO4 | B | 5 | −26.741 | 32.887 | 26.875 | 0.33 | 58.19 | S |
| ATOM | 1598 | O1 | SO4 | B | 5 | −25.831 | 33.787 | 26.132 | 0.33 | 60.90 | O |
| ATOM | 1599 | O2 | SO4 | B | 5 | −26.885 | 31.590 | 26.189 | 0.50 | 58.81 | O |
| ATOM | 1600 | O3 | SO4 | B | 5 | −26.226 | 32.618 | 28.230 | 0.50 | 57.58 | O |
| ATOM | 1601 | O4 | SO4 | B | 6 | −21.748 | 30.361 | 26.457 | 0.50 | 50.00 | O |
| ATOM | 1602 | S | SO4 | B | 6 | −22.401 | 29.102 | 26.030 | 0.50 | 440.04 | S |
| ATOM | 1603 | O1 | SO4 | B | 6 | −22.378 | 29.007 | 24.546 | 0.50 | 40.17 | O |
| ATOM | 1604 | O2 | SO4 | B | 6 | −23.779 | 29.118 | 26.605 | 0.50 | 41.89 | O |
| ATOM | 1605 | O3 | SO4 | B | 6 | −21.665 | 27.934 | 26.545 | 0.50 | 41.23 | O |
| ATOM | 1606 | ZN | ZN | C | 1 | −16.053 | 11.896 | 30.232 | 1.00 | 57.84 | ZN |
| ATOM | 1607 | ZN | ZN | C | 2 | −13.578 | 16.559 | 8.567 | 1.00 | 48.31 | ZN |
| ATOM | 1608 | O | HOH | E | 1 | −35.314 | 17.552 | 23.944 | 1.00 | 47.35 | O |
| ATOM | 1609 | O | HOH | E | 2 | 0.054 | 4.032 | −2.779 | 1.00 | 36.31 | O |
| ATOM | 1610 | O | HOH | E | 3 | 4.531 | 2.010 | −4.613 | 1.00 | 38.13 | O |
| END | | | | | | | | | | | |

A search for structural homologs to the TBD reveals that despite very low sequence identity (<14%), the same fold is found in other proteins including methionine sulfoxide reductase (MSR), an enzyme involved in the repair of oxidized proteins, dsRNA binding proteins RIG-I, MDA5 and LGP2 which are involved in sensing viral RNAs as part of the innate immune response (Lu et al. Structure, 2010. 18(8):1032-43; Li et al. J Biol Chem, 2009. 284(20): 13881-91). Despite sharing the same fold, the tri-Trp pocket residues are not conserved in any of these structurally similar proteins, indicating that these cannot bind immunomodulatory agent drugs in the same manner as CRBN. However, CRBN orthologues can be identified across animal and plant kingdoms, and these proteins exhibit 100% sequence conservation in the immunomodulatory agent drug binding pocket (FIG. 19). This level of sequence conservation is indicative of strong functional constraint(s), which suggests there may be an endogenous ligand with which immunomodulatory agent drugs compete. Tryptophan residues 380 (W380), 386 (W386) and 400 (W400) are fully conserved across CRBN orthologues (FIG. 19). The glutarimide binding pocket formed by these three tryptophan residues is reminiscent of the aromatic pockets used for binding methylated lysine and/or arginine found in royal family proteins containing chromodomains, tudor domains, plant homeo domain (PHD) fingers and malignant brain tumor (MBT) repeats, as well as bromodomains for binding to acetylated lysines and the tryptophan box of betaine-binding proteins such as ProX31 and BetP32. However, our isothermal titration calorimetry (ITC) analysis showed no significant binding affinity to modified lysines, arginines or betaines (data not shown).

A combination of mutations at both Tyrosine 384 (Y384) and W386 has been reported to cause a loss of the immunomodulatory agent drug effects. As shown in FIG. 15, W386 is part of the lenalidomide binding site and mutation of that residue would be expected to have consequences for immunomodulatory agent drug binding. Y384 however does not make any direct interactions with lenalidomide, and might be expected to have a more general effect on the stability of the domain.

Figure 24:
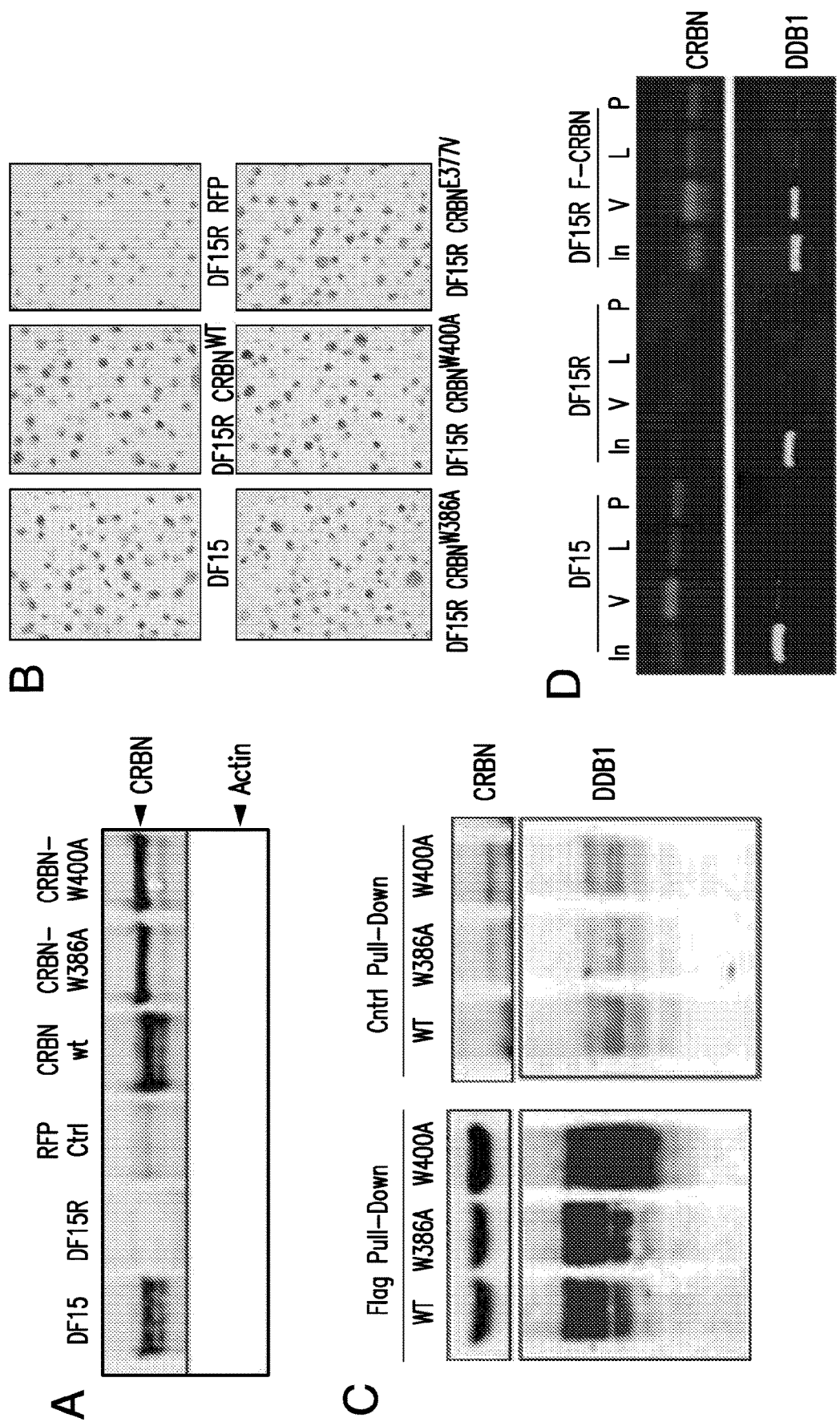

6.9.3.2 Mutational Analysis of Residues Proximal to the Immunomodulatory Agent Binding Site To better understand the role of the residues involved in the CRBN-immunomodulatory agent interactions in a cellular context, we performed mutagenesis of residues W386 or W400 to alanine and used lentiviral expression vectors to re-express full length wild type (CRBN$^{WT}$), W386A (CRBN$^{W386A}$) or W400A (CRBN$^{W400A}$) mutant versions of CRBN in a CRBN deficient myeloma cell line (DF15R) (Lopez-Girona et al., Leukemia. 26(11):2326-35). Transduction of the lentiviral constructs into DF15R cells and selection with puromycin generated cell lines that stably expressed wild type or mutant forms of CRBN at levels similar to the matched immunomodulatory agent-sensitive DF15 cell line (Lopez-Girona et al., Leukemia. 26(11):2326-35) (FIGS. 24A-24B). Immunoprecipitation-Western blotting analysis confirmed that similar to recombinant, wild type CRBN, mutants CRBN$^{W386A}$ and CRBN$^{W400A}$ interacted with DDB1 indicating that these proteins were properly folded and competent to form CRL4$^{cRBN}$ complexes in cells (FIG. 24C) (Ito et al., Science, 2010. 327(5971):1345-50). Cell extracts from these lines were then used to assay the ability of CRBN to bind immunomodulatory agent compound. We used the thalidomide analog-coupled affinity bead assay (Ito et al., Science, 2010. 327(5971):1345-50; Lopez-Girona et al., Leukemia. 26(11):2326-35) (FIG. 24D) to demonstrate binding of recombinant CRBN to immunomodulatory agent compounds in cell extracts. Similar to the endogenous protein in DF15 cell extracts, the recombinant CRBN$^{WT}$ expressed in DF15R was able to bind thalidomide analog-beads (FIG. 22A), and preincubation of cell extracts with free thalidomide or pomalidomide competed for binding to the beads. In contrast, the tryptophan mutants CRBN$^{W386A}$ and CRBN$^{W400A}$ were unable to bind thalidomide analog-beads (FIG. 22A), consistent with the structural information that both tryptophan residues in CRBN are needed for the interaction with immunomodulatory agent compounds.

The antiproliferative effect of immunomodulatory agent compounds on myeloma cells is mediated through CRBN protein. Thus, engineered cells (FIG. 25) (Lopez-Girona et al., Leukemia. 26(11):2326-35; Zhu et al., Blood. 2011.

Figure 25:
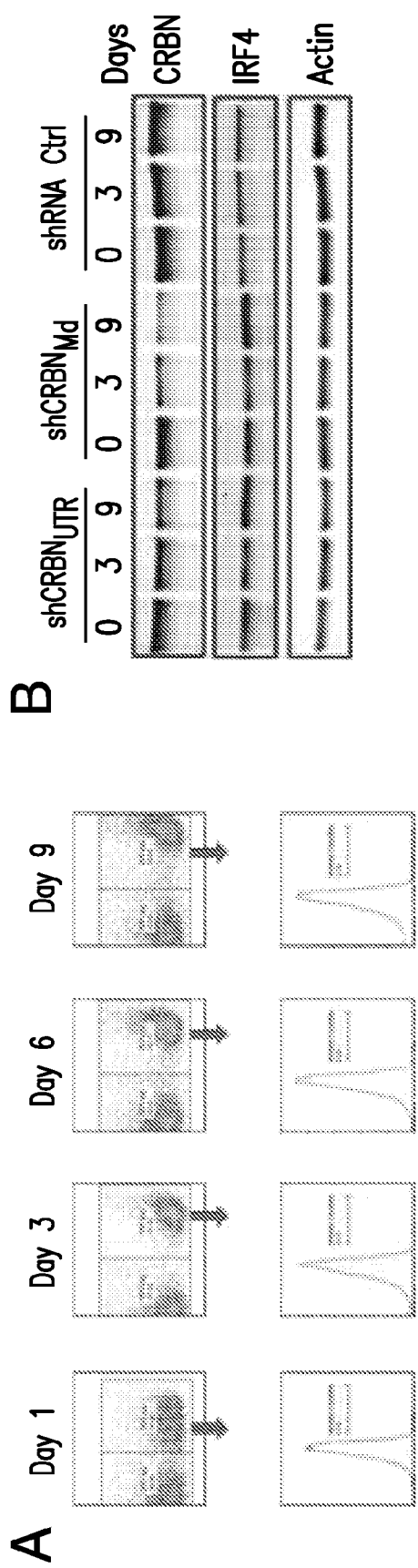

118(18):4771-9) or cells made resistant to immunomodulatory agent drugs (Lopez-Girona et al., Leukemia. 26(11): 2326-35) that lack detectable levels of CRBN, e.g., DF15R, become insensitive to the antiproliferative effects of the immunomodulatory agent compounds (FIG. 22B; FIG. 25). Significantly, the re-expression of a single recombinant protein, CRBN$^{WT}$, is sufficient to restore the sensitivity to immunomodulatory agent compounds in the resistant line DF15R (FIG. 22B) as well as in other cell lines (data not shown). In these cells, re-expression of CRBN$^{WT}$ also restores immunomodulatory agent-induced degradation of aiolos, and, as expected, restores the inhibition of c-Myc, IRF4, and phophorylated pRB expression (FIG. 22C). All of these downstream effects are consistent with the regained antiproliferative effect of pomalidomide (Gandhi et al., Br J Haematol.; Lu et al., Science; Kronke, et al., Science, 2014. 343(6168):301-5; Lopez-Girona et al. Br J Haematol, 2011. 154(3):325-36). In contrast, expression of the immunomodulatory agent-binding defective mutants, CRBN$^{W386A}$ or CRBN$^{W400A}$, does not re-sensitize DF15R cells to the antiproliferative effects of immunomodulatory agent drugs (FIGS. 22B and 22C). These cellular data are consistent with the structural data indicating that both W386 and W400 residues mediate CRBN binding to immunomodulatory agents, and CRBN mediates the antiproliferative effects characteristic of immunomodulatory agent compounds in myeloma cells.

6.9.3.3 Mutation of Variable Residues in the Immunomodulatory Agent Binding Site of CRBN Since we hypothesized that immunomodulatory agents are essential for altering the interaction between CRBN and substrate, we also investigated the role of other proximal residues. It is known that rodents do not respond to immunomodulatory agent drugs in the same way that humans do. Rodents appear to be resistant to the IL-2 induction (FIG. 26), antiproliferative effects and also immunomodulatory agent compound induced teratogenicity (Newman et al., Reprod Toxicol, 1993. 7(4):359-90). A key step in understanding immunomodulatory agent biology and ultimately engineering immunomodulatory agent analogs without teratogenicity may indeed come from pin-pointing the key features which underlie the biological differences seen between rodents and humans. Within the immunomodulatory agent binding domain there are four differences between mouse and human proteins. Two of the variable residues are proximal to the immunomodulatory agent binding site (FIG. 19). One of these residues features a substantial change in properties from an acidic residue (glutamate 377) in human to a hydrophobic residue (valine) in mouse and rat.

To probe the function of the residues proximal to the bound immunomodulatory agent drug, we performed mutagenesis of residue E377 to valine in the human CRBN sequence and re-expressed the protein using a lentiviral system in DF15R cells. Cell extracts from this line were used to assay the ability of CRBN$^{E377V}$ to bind Immunomodulatory agent compound. Similar to the recombinant CRBN$^{WT}$, but in contrast to the CRBN$^{W386A}$ or CRBN$^{W400A}$ mutants, the CRBN$^{E377V}$ mutant was able to bind thalidomide analog-beads, and this binding was competed by preincubation of cell extracts with free thalidomide or pomalidomide comparable to CRBN$^{WT}$ (FIG. 23A). This is consistent with the structure that shows E377V is proximal to but does not directly interact with bound lenalidomide. CRBN$^{E377V}$ re-expression in DF15R was unable to rescue sensitivity to pomalidomide or to rescue the degradation of Aiolos (FIG. 23B and FIG. 23B insert). Immunomodulatory agent binding to CRBN has been shown to enhance both the recruitment to CRL4$^{CRBN}$ and the degradation of Ikaros and Aiolos Gandhi et al., Br J Haematol.; Lu et al., Science; Kronke, et al., Science, 2014. 343(6168):301-5). To determine whether Aiolos binding had been altered, we performed pull-down assays to compare the ability of CRBN$^{WT}$ or CRBN$^{E377V}$ to interact with Aiolos in the presence or absence of immunomodulatory agent compounds.

The function of the residues proximal to the bound immunomodulatory agent drug in degradation of CRBN substrates induced by immunomodulatory agent drug was studied. 293FT CRBN−/− cells were transiently transfected with plasmids expressing V5-tagged IKZF1, FLAG-tagged IKZF3, Myc-tagged Substrate X, GFP, human CRNB (hCRBN) or variants thereof, or mouse CRBN (mCRBN) or variants thereof. Thirty-six hours after transfection, cells were treated with DMSO, 10 μM lenalidomide or 1 μM Compound C for additional 12 hours. Cells were then wished with ice-cold 1×PBS twice, lysed in buffer A [50 mM Tris. CL, 150 mM NaCL, 1% triton-x 100, complete protease inhibitor tablet (roche), phosphatase inhibitor tablet (roche)]. Whole cell extracts were then harvested and subjected to immunoblot analysis. The results are shown in FIG. 27. As shown, V388 is essential for the destruction of Ikaros (IKZF1) or Aiolos (IKZF3) by lenalidomide. This result indicates that residue 388 of CRBN plays an important role in degradation of CRBN substrates, e.g., Ikaros or Aiolos, induced by immunomodulatory agent drug.

6.9.4. Discussion

Ito et al. first reported CRBN as the primary molecular target of thalidomide, and through mutagenesis demonstrated that the C-terminal domain encompassed the thalidomide binding domain (Ito et al., Science, 2010. 327(5971): 1345-50).

Herein, we have presented the crystal structure of CRBN in complex with DDB1 and lenalidomide, thus providing the first structural description of immunomodulatory agent drug binding. The immunomodulatory agent-binding site is a shallow hydrophobic pocket on the surface of CRBN: three tryptophan residues form the binding site for the glutarimide ring of the immunomodulatory agent drug, with 3 hydrogen bonds observed between CRBN and the glutarimide ring. The glutarimide ring is a defining feature of the immunomodulatory agent class of molecules and all immunomodulatory agent-CRBN structures solved to date replicate the CRBN-immunomodulatory agent binding interaction described herein.

Figure 23:
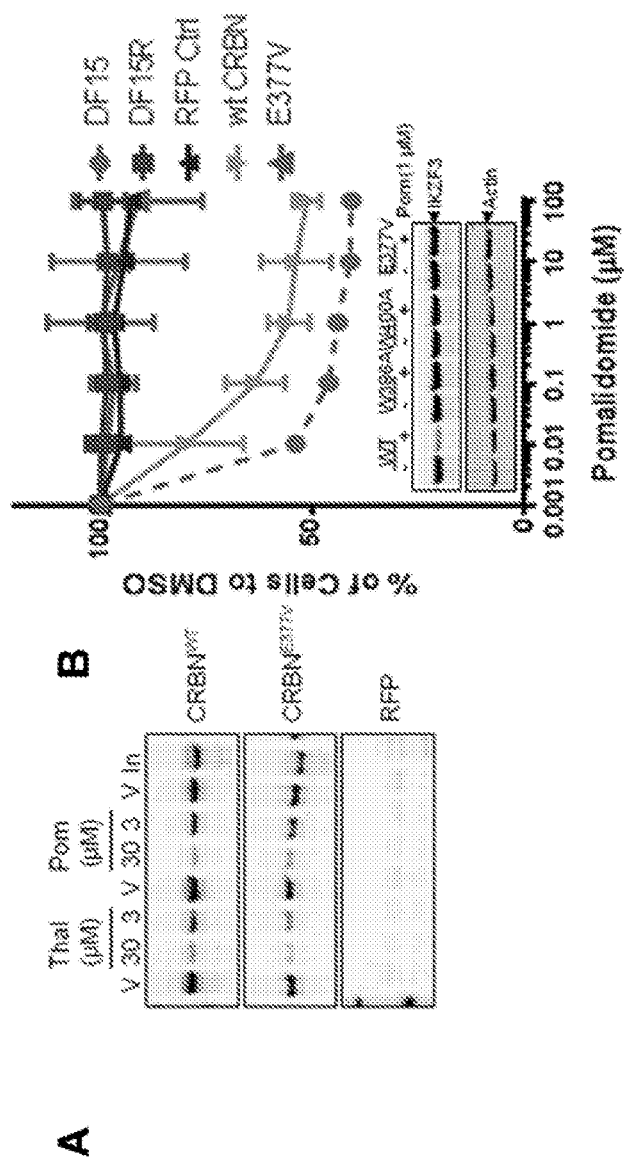

We have demonstrated that immunomodulatory agent binding and cellular function is dependent upon these key tryptophan interactions by comparing mutant knock-ins to wild type CRBN in a CRBN-deficient myeloma cell line, DF15R. We further used the knock-in system to study a glutamate residue, E377, which although proximal to bound lenalidomide, does not directly interact with the ligand. E377 is of keen interest as this residue is a valine in rodent species, which are resistant to teratogenic and other cellular immunomodulatory agent drug effects. We observe that knock-in of a human E377V mutant CRBN behaves in an identical manner to the knock-in of murine CRBN into our human myeloma cell line: neither mouse CRBN, nor human E377V mutant CRBN are able to rescue the immunomodulatory agent response although immunomodulatory agent binding is clearly evident (FIG. 23). In addition, we found that residue 388 of CRBN is essential for the destruction of Aiolos and Ikaros by lenalidomide. Of note is that we have not detected an E377V mutation in the setting of clinical resistance but our work here implies that a single amino acid change could mediate resistance to immunomodulatory agent drugs. CRBN down-regulation is certainly a mode of immunomodulatory agent resistance as evidenced by our in vitro experiments and has been suggested by a number of reports as a mechanism for innate or acquired resistance to immunomodulatory agent drugs in the clinical setting.

We establish that immunomodulatory agent drug binding alone, although necessary for inducing the E3 ligase mediated degradation of Aiolos and Ikaros, may not be sufficient as demonstrated here with the E377V mutant. Interestingly, the lenalidomide isoindolinone group is presented on the surface of the CRBN protein. This binding mode generates a surface with a number of available hydrogen bonds from both the protein and lenalidomide in the proximity of an exposed hydrophobic group. Immunomodulatory agent drug binding to CRBN has been demonstrated to increase the recruitment of substrates (e.g., Ikaros and Aiolos) to the ubiquitin ligase complex and enhance their degradation Gandhi et al., Br J Haematol.; Lu et al., Science; Kronke, et al., Science, 2014. 343(6168):301-5.). It is an interesting finding by us that V388 of CRBN is essential for immunomodulatory agent drug (e.g., lenalidomide) induced degradation of Ikaros and Aiolos. The unsatisfied bonding potential around the bound immunomodulatory agent drug could therefore form the basis of an artificially introduced interaction hotspot, thereby conferring a pharmacologically induced 'neomorphic' function to this E3 ligase.

However, in the case of CRBN, we have shown that the immunomodulatory agent binding pocket is extremely conserved across the known orthologues, which indicates that immunomodulatory agent drugs may be binding in place of an endogenous ligand, which has yet to be identified. There are several examples of endogenous ligands that have been demonstrated to regulate substrate recruitment to ubiquitin ligase complexes in plant systems. For example, auxin and jasmonate are small molecule regulators of ligases in plants (Tan et al. Nature, 2007. 446(7136):640-5; Chini et al., Nature, 2007. 448(7154):666-71). Similarly, a number of natural products exhibit pharmacological activity by scaffolding macromolecular interactions (Thiel et al. Angew Chem Int Ed Engl, 2012. 51(9):2012-8).

The ability for a small molecule to scaffold a specific macromolecular interaction to an E3 ubiquitin ligase has particularly exciting implications for drug discovery. We have observed several categories of variation proximal to the immunomodulatory agent drug binding site: variations in the presentation and substitution pattern of the solvent exposed ligand groups, protein conformational differences, and species sequence differences. To fully rationalize the role of these in immunomodulatory agent drug biology, several further advancements are anticipated, such as identification of the endogenous ligand(s) and the binding mode of the substrate proteins, such as Aiolos, when recruited to the Cul4:Rbx1:DDB1:CRBN complex upon immunomodulatory agent drug treatment. By describing the crystal structure of an immunomodulatory agent bound to CRBN, a substrate adapter for an E3 ubiquitin ligase, progress towards the rational design of ubiquitin ligase modulators is made.

6.10 Compound C-Induced Recruitment of GSPT1 to CRBN and the Crystal Structure of CRBN-DDB1-GSPT1-Compound C Complex

6.10.1 Summary

CRBN is the biological receptor for immunomodulatory drugs, which alter the specificity of the CRBN E3 ubiquitin ligase to confer differential patterns of substrate ubiquitylation and degradation. Here we report the structure of CRBN in complex with a novel small molecule CRBN modulator, Compound C, and a novel substrate, the translation termination factor GSPT1. GSPT1 binding is mediated by a surface turn which interacts with both Compound C and a "hotspot" on the CRBN surface. Substrate interactions with CRBN are predominantly backbone mediated with a Glycine (G) residue at a key position. We provide a molecular/mechanistic understanding of Compound C-directed GSPT1 recruitment, and define a structural degron that may underlie CRBN substrate selectivity. Finally, despite potent anti-tumor effects in humans, rodents remain resistant to Compound C effects via a CRBN mutation, E377V.

6.10.2 Materials and Methods

6.10.2.1 Protein Expression and Purification

Purification of CRBN-DDB1 was performed essentially as previously described (Chamberlain 2014). 6×His-ZZ-domain-thrombin tagged human CRBN (amino acids 40-442) and full length human DDB1 were co-expressed in SF9 insect cells in ESF921 medium in the presence of 50 uM zinc acetate. Cells were resuspended in buffer containing 50 mM Tris-HCl pH 7.5, 500 mM NaCl, 10 mM imidazole, 10% Glycerol, 2 mM TCEP, 1× Protease Inhibitor Cocktail (San Diego Biosciences, San Diego, Calif.), and 40,000U Benzonase (Novagen, Billerica, Mass.), and sonicated for 30 s. Lysate was clarified by high speed spin at 30,000 rpm for 30 minutes, and incubated with Ni-NTA affinity resin (Qiagen, Germany) for 1 hour. Complex was eluted with 500 mM imidazole, and the 6×his-zz-domain tag removed by thrombin (Enzyme Research Laboratories, South Bend, Ind.) cleavage overnight combined with dialysis into 10 mM imidazole buffer. Cleaved eluate was incubated with Ni-NTA sepharose, and the flow-through diluted to 200 mM NaCl for further purification over an ANX HiTrap ion exchange column (GE Healthcare, Piscataway, N.J.). The ANX column was washed with 10 column volumes of 50 mM Tris-HCl pH 7.5, 200 mM NaCl, 3 mM TCEP, followed by 10 column volumes of 50 mM Bis-Tris pH 6.0, 200 mM NaCl, 3 mM TCEP, and the CRBN-DDB1 peak eluted at 210 mM NaCl. The peak was collected and further purified by size exclusion chromatography using a Sephacryl 400 16/60 (GE Healthcare, Piscataway, N.J.) in buffer containing 10 mM HEPES pH 7, 240 mM NaCl, 3.0 mM TECP. The CRBN-DDB1 complex was concentrated to 30 mg/mL for crystallization trials.

GSPT1 domains 2 and 3 (amino acids 437-633) was expressed as an MBP-fusion in *E. coli* BL21 (DE3) star cells (Life Technologies, Carlsbad, Calif.) using 2XYT media (Teknova, Hollister, Calif.). Cells were induced at $OD_{600}$ 0.6 for 18 hours at 16° C. Cells were pelleted, resuspended in buffer containing 200 mM NaCl, 50 mM Tris pH 7.5, 1 mM TCEP, 10% glycerol, x mg/mL lysozyme, 10,000 U benzonase, and 1×SD Bioscience protease inhibitors. Resuspended cells were frozen, thawed for purification, and sonicated for 30 s before high speed spin at 30,000 rpm for 30 minutes. Clarified lysate was incubated with maltose resin (NEB) at 4° C. for 1 hour before beads were washed. Protein was eluted with buffer containing 10 mM maltose, and the MBP tag was removed by overnight cleavage with thrombin (Enzyme Research Laboratories, South Bend, Ind.). Cleaved GSPT1 was diluted into buffer containing 90 mM Nacl and further separated over a Heparin HiTrap column (GE healthcare, Piscataway, N.J.). The GSPT1 peak eluting at 100 mM NaCl was collected, concentrated, and further separated by size exclusion chromatography over a Sepharose 75 16/60 column (GE Healthcare, Piscataway, N.J.) in buffer containing 10 mM HEPES pH7, 240 mM NaCl, 3.0 mM TECP. GSPT1 eluted at 75 mL and was concentrated to 16 mg/mL for crystallization trials.

6.10.2.2 Crystallization and Structure Determination

Crystallization of the complex was achieved by sitting drop vapor diffusion. CRBN-DDB1 and GSPT1 were mixed together to equimolar stoichiometry at a final concentration of 170 uM. The solution of CRBN-DDB1-GSPT1 in the presence of 500 uM Compound C was mixed 1:1 with, and subsequently equilibrated against a mother liquor solution of 200 mM sodium citrate, Tris-HCl pH 8.4-8.6, 17-20% PEG 3350 and incubated at 9° C. Crystals were cryoprotected in the reservoir solution supplemented with 20% Ethylene glycol and cooled under liquid nitrogen. Data were collected from a single crystal at the Advanced Light Source, beamline 5.0.2. The structure of human CRBN-DDB1-GSPT1-Compound C was solved by molecular replacement using Phaser, with human CRBN-DDB1 (PDB code 4TZ4) and GSPT1 (pdb code 3E1Y) as search models. Subsequent manual model building using Coot and refinement were performed using Refmac5 with non-crystallographic symmetry and external structure restraints. Crystallographic statistics are summarized in Table 9.

TABLE 9

Crystallographic Statistics

| | CRBN-DDB1-Compound C-GSPT1 |
|---|---|
| Data collection | |
| Space group | P2 |
| Cell dimensions | |
| a, b, c (Å) | 156.8 111.5 175.1 |
| α, β, γ (°) | 90 95.8 90 |
| Resolution (Å) | 50-3.6 (3.66-3.6)* |
| $R_{merge}$ (%) | 19.8 (79.6) |
| I/σI | 10.6 (2.1) |
| Completeness (%) | 94.4 (93.9) |
| Redundancy | 4.8 (4.5) |
| Refinement | |
| Resolution (Å) | 50.0-3.6 |
| No. reflections | 62827 |
| $R_{work}/R_{free}$ | 0.223/0.279 |
| No. atoms | |
| Protein | 25202 |
| Ligand/ion | 62/2 |
| Water | 0 |
| B factors | |
| Protein | 117.9 |
| Ligand/ion | 99.9/167.6 |
| Water | N/A |
| r.m.s. deviations | |
| Bond lengths (Å) | 0.015 |
| Bond angles (°) | 1.853 |

*Values in parentheses are for highest-resolution shell.

6.10.2.3 Surface Plasmon Resonance Binding Assay

Binding kinetics was measured using a Biacore T200. Using the GST-capture kit (GE Healthcare, BR-1002-23), ~2000 RU of anti-GST antibody was immobilized on a CM5 chip (GE Healthcare, Piscataway, N.J.). GST-GSTP1-domain 2 and 3 (0.07 ug/mL) or GST (0.15 ug/mL, reference channel) was then flowed over the chip at 10 ul/min for 2 min, resulting in a capture level of approximately 10 RU. A 3-fold dilution series of CRBN-DDB1 (3 uM to 3 nM) was then flown over both channels at a rate of 30 ul/min for 300 s contact time, followed by 900 s dissociation time. After each cycle of binding and dissociation, the surface was regenerated with 10 mM glycine pH 2.1 for 120 s at 30 ul/min, followed by 3M $MgCl_2$ for 60 s at 30 ul/min. All reagents (GST, GST-GSPT1 domain 2 and 3, CRBN-DDB1, and running buffer) were in 10 mM HEPES pH 7.4, 150 mM NaCl, 0.05% v/v Surfactant P20 containing 0.02% DMSO and saturating levels of the relevant compound, glutarimide or Compound C (Compound C at 10 uM, Glutarimide at 100 uM given its significantly lower affinity for CRBN). The apparent on- and off-rate constants were globally fit with a 1:1 kinetic binding model to the sensograms (black lines) using the Bioacore T200 kinetic analysis software package.

6.10.2.4 Co-Immunoprecipitation of CRBN-DDB1 with Substrates

Co-immunoprecipitation of CRBN-DDB1 with either GSPT1 or IKZF1 was performed using the same protocol. Tagged substrate, either GST-GSPT1-domain 3 (a.a. 526-633) or MBP-IKZF1 (a.a. 140-168), was expressed in bacteria and purified using affinity and size exclusion chromatography. Substrate was then bound to magnetic beads for 1 hour. Beads were washed 3 times in IP buffer (50 mM Tris pH 7.5, 150 mM NaCl, 10% glycerol, 0.01% NP-40, 1 mM TCEP) to remove excess unbound substrate, before the addition of DMSO or 100 uM compound (Compound C for GSPT1 and pomalidomide for IKZF1) and 50 uM CRBN-DDB1, purified from insect cells using affinity, ion exchange, and size exclusion chromatography. After one hour incubation with occasional gentle mixing at room temperature, unbound CRBN-DDB1 was removed and beads were washed 3 times in IP buffer, for a total of around 30 s. Substrate and co-immunoprecipitated CRBN-DDB1 was eluted using either 20 mM reduced glutathione or 10 mM maltose, separated by SDS-PAGE, and coomassie stained.

6.10.3 Results 6.10.3.1 a Truncated Form of Human GSPT1 Maintained the Functionality of the Full-Length Protein FIG. 28A illustrates a full-length human GSPT1 and a truncated mutant form, which lacks the N-terminal 138 amino acid residues. FIG. 28B shows that, in 293T HEK cells, Compound C induced degradation of the full-length GSPT1 and the truncated form. FIG. 28C shows that Compound C induced interaction of CRBN with the full-length GSPT1 as well as the truncated GSPT1. Thus, the truncated mutant human GSPT1 maintained the functionality of the full-length protein and can be used in studies below.

6.10.3.2 Glycine (G) 575 in Human GSPT1 is Essential for the Functionality of GSPT1

FIG. 29A shows a high degree of homology between the human GSPT1 and the yeast homologue SUP35. However, FIG. 29B shows that SUP35 did not exhibit Compound C-induced degradation, in contrast to human GSPT1.

Figure 30:
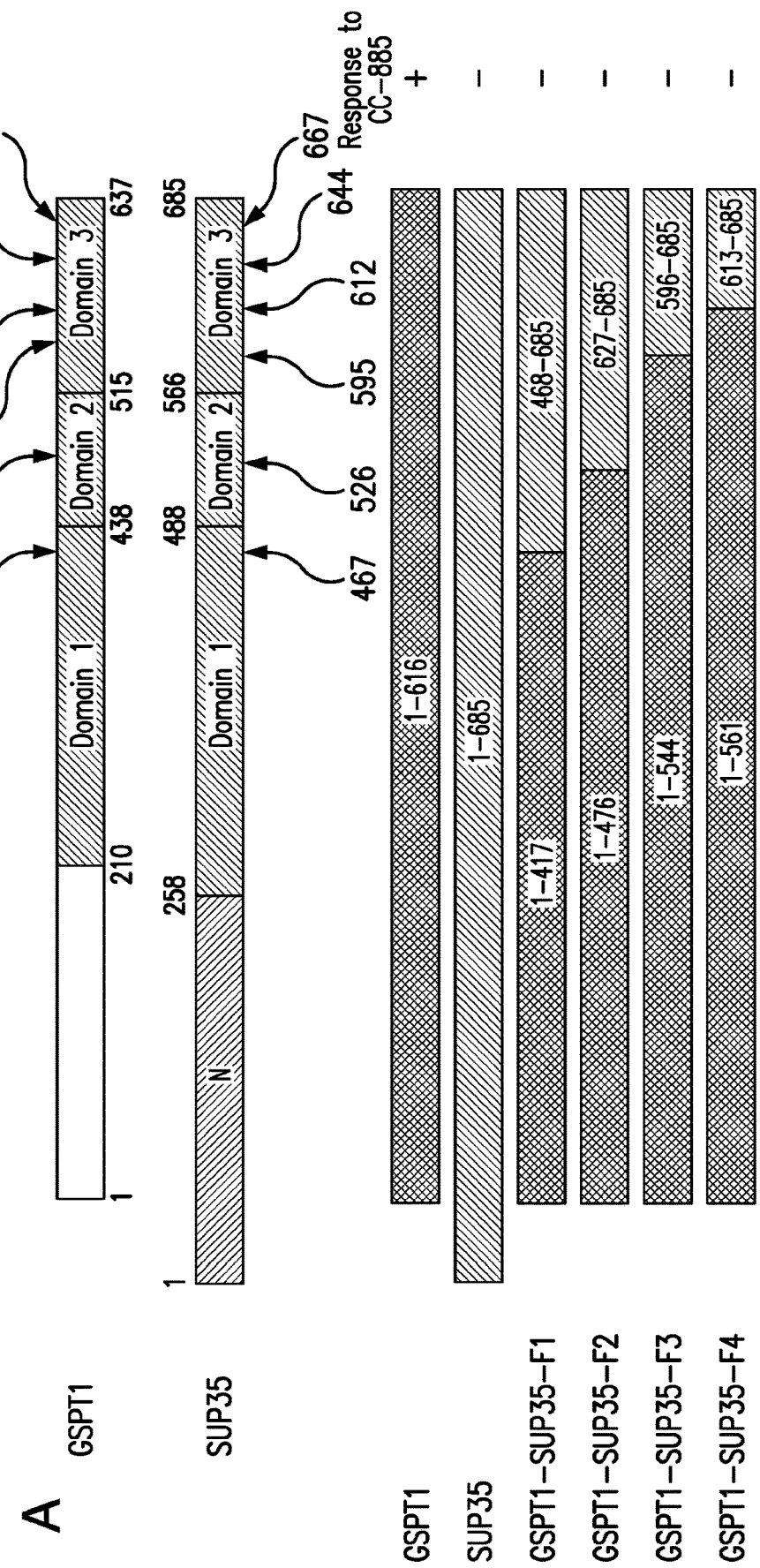

To determine the critical region in the human GSPT1 that contributes to the Compound C-induced degradation, a plethora of chimeric constructs containing various domains of human GSPT1 and yeast SUP35 were generated (FIG. 30A). These recombinant proteins were tested for Compound C-induced degradation by Western blot (FIGS. 30B-30D). As the results shown, a 32-amino acid fragment in the C-terminus of human GSPT1 (residues 562-593) is critical for Compound C-induced degradation.

To further map the essential amino acid residues in this 32-amino acid fragment of human GSPT1, various point mutations within the fragment were generated and tested for Compound C-induced degradation of GSPT1 and Compound C-induced interaction between CRBN and GSPT1.

FIG. 31A shows the sequence comparison among human GSPT1, human GSPT2, human HBS1L, mouse GSPT1, mouse GSPT2, mouse HBS1L, and yeast SUP35. Among these homologues, only the yeast SUP35 is resistant to Compound C. Sequence alignment suggested that glycine (G) at position 575 of human GSPT1 may contribute to the sensitivity to Compound C. FIG. 31B shows that a G575N mutation in GSPT1 blocked Compound C-induced degradation, but a E576R mutation had no effect. Other mutations, such as I567L, C568H, L569K, R581P. R583A, V585A, and Q589M, exhibited no effect on Compound C-induced degradation of GSPT1 (data not shown). Further, FIG. 31C shows that the G575N mutation in GSPT1 blocked Compound C-induced interaction between CRBN and GSPT1, but the E576R mutation had no effect.

FIGS. 32A-32B demonstrate that the G575N mutation in GSPT1 blocked Compound C-induced growth inhibition and Compound C-induced downstream activation of ATF4 and apoptosis pathways.

6.10.3.3 Crystal Structure of GSPT1-CRBN Complex in the Presence of Compound C

Figure 33:
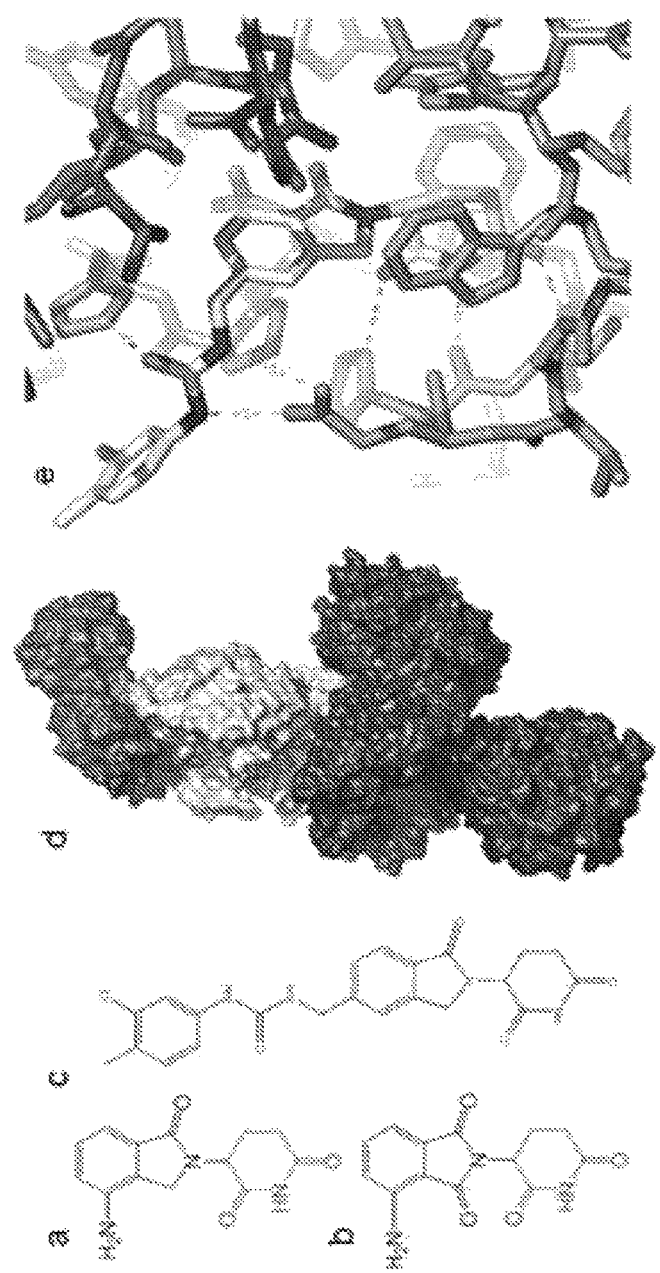
Figure 35A:
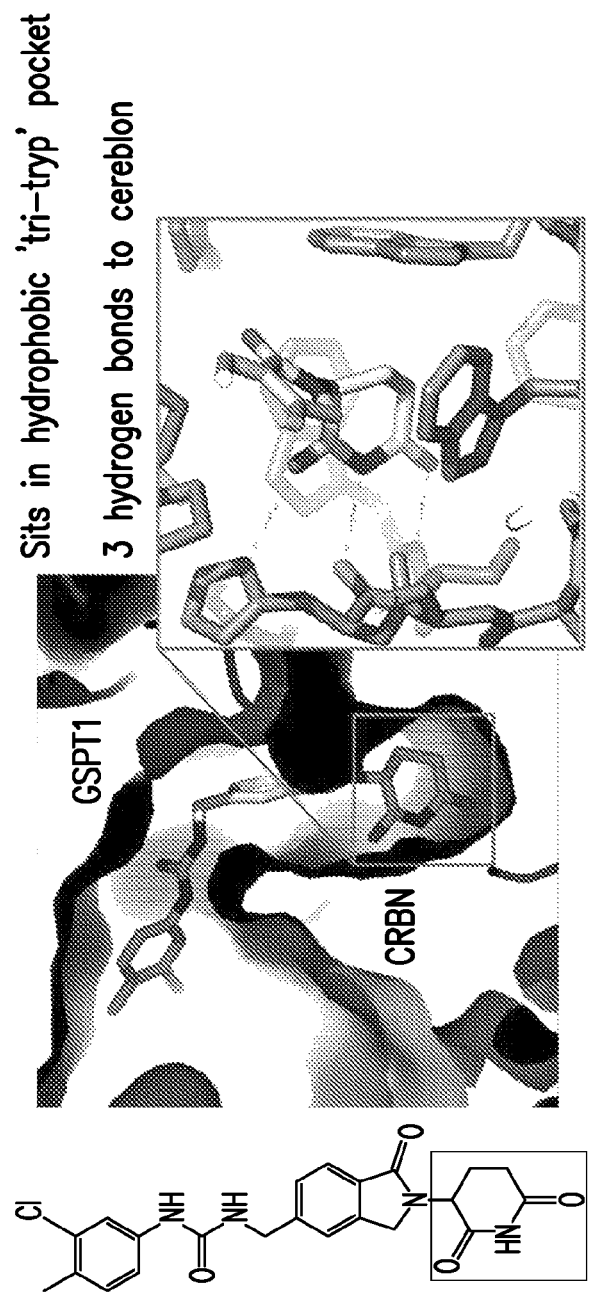
Figure 35B:
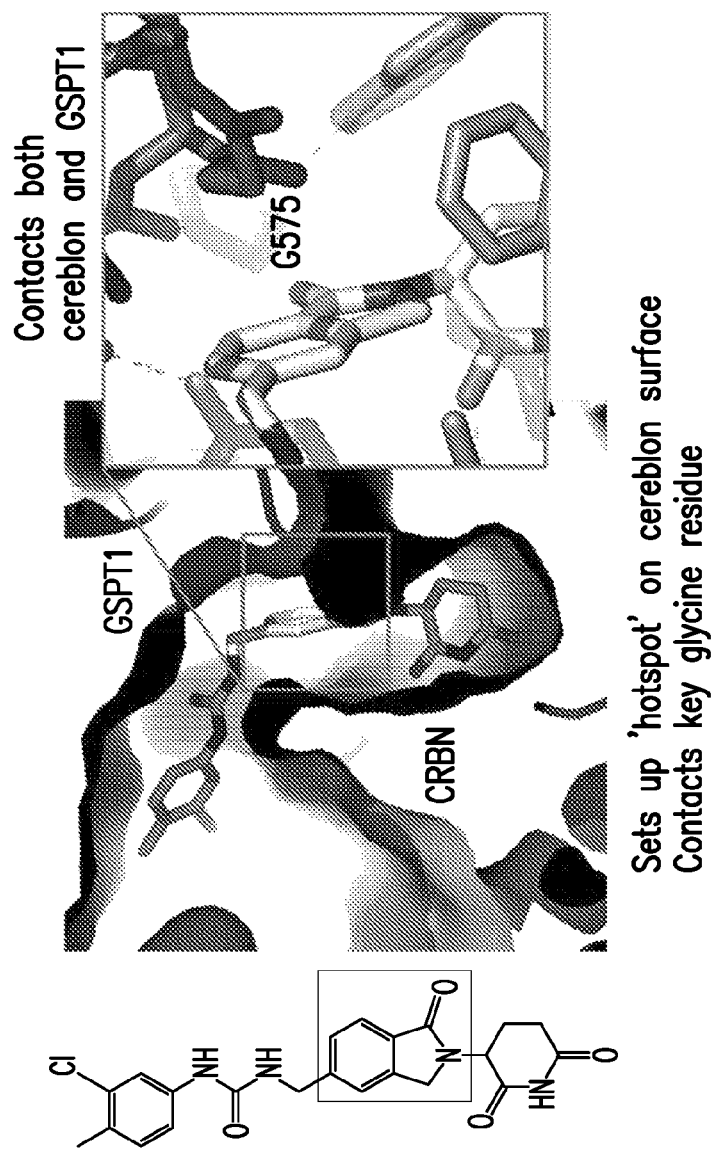
Figure 35C:
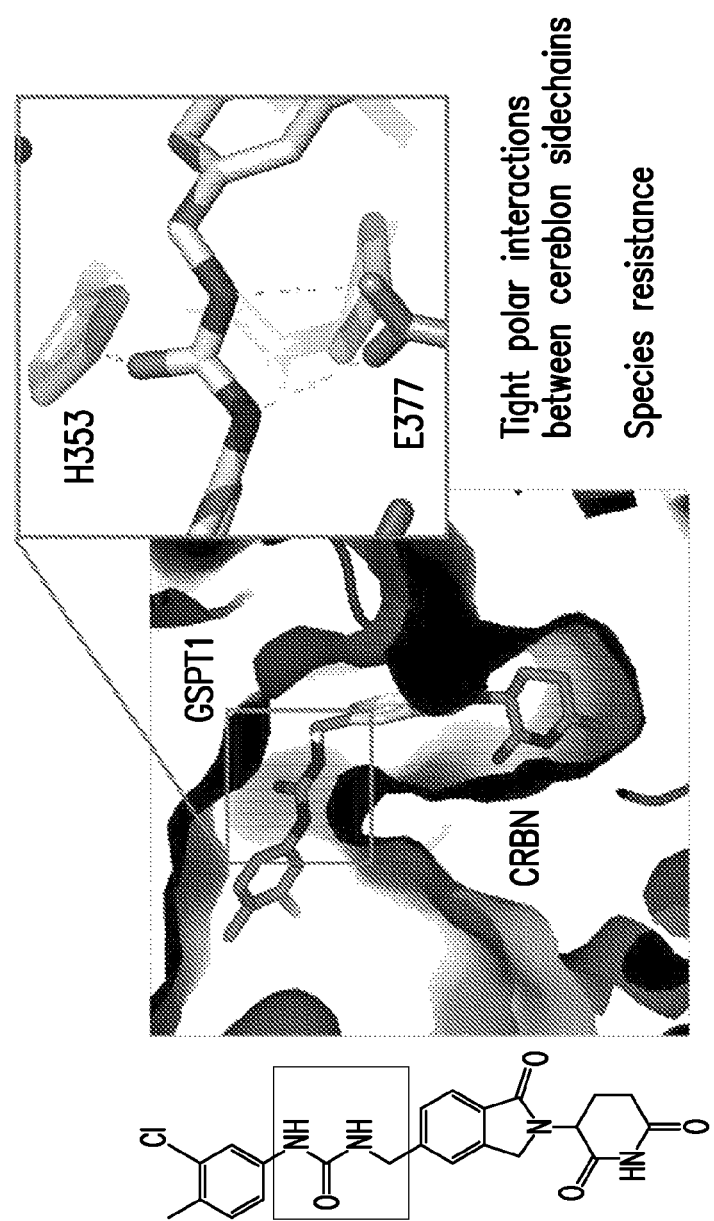
Figure 35D:
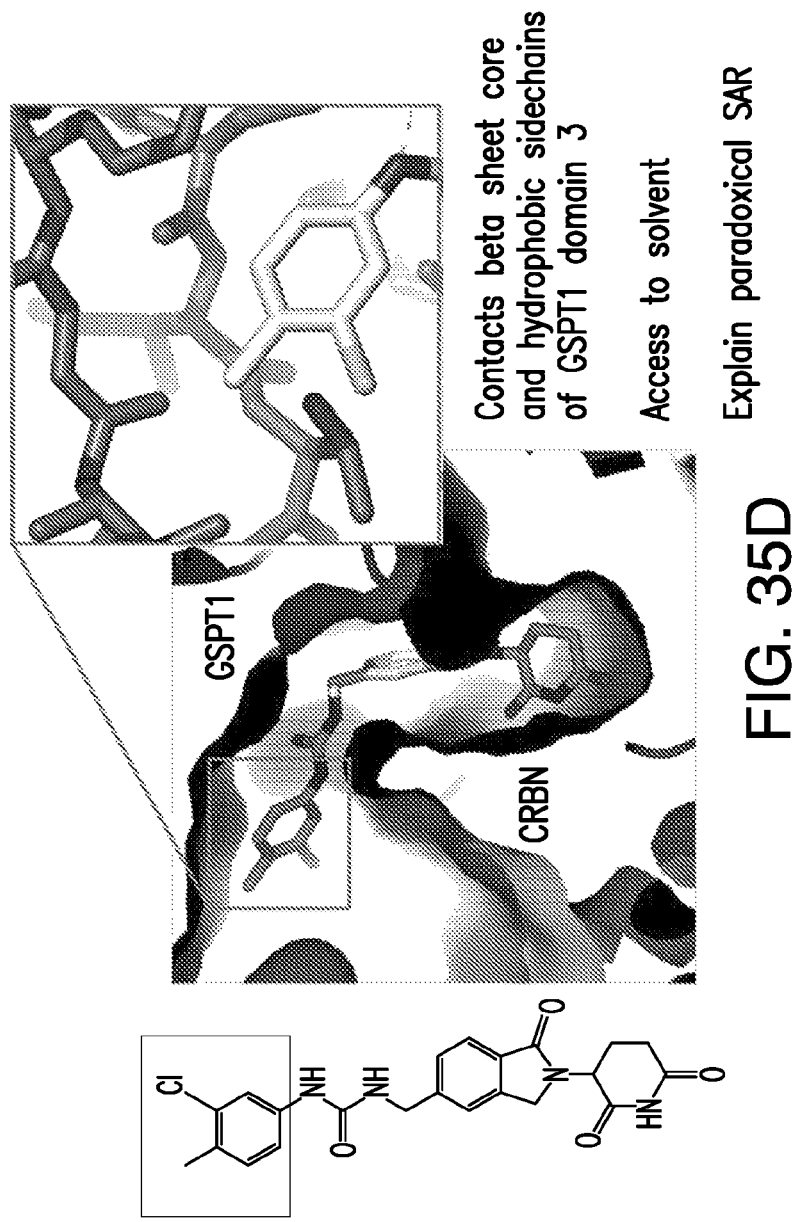

We determined the crystal structure of full length human DDB1 bound to human CRBN (amino acids 40-442), Compound C, and domains 2 and 3 of human GSPT1 (amino acids 437-633) to 3.6 Angstroms resolution. The interaction between purified GSPT1 domains 2 and 3 and purified CRBN-DDB1 complex was not observable in the absence of Compound C, and had a KD of 400 nM in the presence of Compound C, as determined by surface plasmon resonance (data not shown). GSPT1 domain 3 docks against CRBN at the site of Compound C binding, with direct interactions to both Compound C and to the proximal CRBN surface. GSPT1 domain 2 does not directly contact either Compound C or CRBN. This is consistent with biochemical characterization of the interaction between CRBN and GSPT1 by co-immunoprecipitation, which indicated that domain 3 of GSPT1 mediates CRBN interactions (data not shown). CRBN is in a highly similar conformation to the previously described structures, and is bound to DDB1 in a manner consistent with the previously determined structures of CRBN-DDB1. Chamberlain et al., Nature structural & mole. biol. 2014, 21:803-809; Fischer et al., Nature 2014, 512:49-53. Compound C is bound in the tri-Trp pocket of CRBN through its glutarimide ring, with 3 hydrogen bonds to the backbone of W380, H378, and to the side chain of H378 in CRBN (FIGS. 33E and 35A). The isoindolinone ring of Compound C is presented on the surface of CRBN, interacts with both CRBN and GSPT1, and sets up a "hotspot" on CRBN surface (FIG. 35B). The key Glycine (G) residue at position 575 of GSPT1 is engaged. The chemical structure of Compound C is extended compared to the immunomodulatory drugs lenalidomide or pomalidomide (FIGS. 33A-33C), allowing for further interactions with both CRBN and GSPT1. The urea moiety of Compound C is positioned between E377 and H353, with hydrogen bonds to both side chains (FIG. 35C). The species resistance to Compound C is conferred by this region of CRBN. The terminal methyl-chloro-phenyl ring is positioned against the beta sheet core of GSPT1 domain 3 with direct Van der Waals interactions (FIG. 35D).

FIGS. 34A-34C demonstrate excellent agreement between structure and mutational analysis. Point mutations were generated on the surface of CRBN. These mutants were tested in CRBN immunoprecipitation experiment in the presence of vehicle or Compound C. As shown in FIG. 34A, E377V, E377A, and H357A disrupted the binding of GSPT1 to CRBN. H397 partially disrupted the binding. V388I had no effect on the GSPT1-CRBN binding, whereas V388A partially blocked the binding. This indicates that V388 itself is not essential for the interaction between GSPT1 and CRBN, but the substitution (A or I) affects the interaction. Other mutations, such as I371A, R373A, T376A, K406A, and K407A, had no effect on the GSPT1-CRBN binding. FIG. 34B shows the structure of GSPT1-CRBN binding, with mapped SUP35 region in yellow and the key Glycine (G) residue in red. FIG. 34C shows the structure of GSPT1-CRBN binding, with amino acid residues disrupting binding in red, amino acid residues partially disrupting binding in orange, amino acid residues not affecting binding in green, amino acid residues not tested in mutational analysis in blue.

FIG. 36A shows the non-conserved amino acid residues in red between GSPT1 and GSPT2, and FIG. 36A shows the non-conserved amino acid residues in red between GSPT1 and HBS1L. Compound C is shown in green. CRBN is shown in blue. The disparity between GSPT2 and HBS1L in comparison with GSPT1 suggests that the interaction between GSPT2 and CRBN may be very much like that between GSPT1 and CRBN, but that that the interaction between HBS1L and CRBN may be different from that between GSPT1 and CRBN.

FIG. 37 shows backbone-mediated interactions between CRBN and GSPT1 in the presence of Compound C. N351, H357, and W400 are amino acid residues in CRBN. D571, K572, and S574 are amino acid residues in GSPT1. Interactions between CRBN and GSPT1 are indicated by yellow dashed lines. Interactions between amino acid residues within GSPT1 are indicated by black dashed lines.

FIG. 38 shows that the key anchoring motif of GSPT1 is stabilized by internal hydrogen bonds from ASX and ST motifs. The hydrogen bonds between D571 and S574 are indicated by black dashed lines.

The GSPT1 motif which mediates interactions with CRBN-Compound C is a solvent exposed region composed of residues 569 to 578 including a small anti-parallel β-sheet with an a-turn from residues 571-575 (FIG. 41A). Despite the degree of solvent exposure, the turn is well ordered in both the prior GSPT1 crystal structure and in the complex with CRBN. The conformational stability of the turn is likely due to the intramolecular bonding pattern, with an ASX-motif and an ST-turn mediated by D571 and S574, respectively (FIG. 38). These intramolecular motifs might be expected to rigidify and stabilize the conformation of the turn, thereby maintaining a competent conformation prior to cereblon binding (FIG. 41A). This is supported by the immunoprecipitation data, which shows that the D571A and S574A mutants lose CRBN binding (FIG. 41C). The key hydrogen bonds to CRBN are all mediated by backbone carbonyl oxygen atoms, which are displayed in an array at the end of the turn. Carbonyl oxygen atoms from GSPT1 K572, K573, and S574 accept hydrogen bonds from cereblon residues N351, H357, and W400, respectively (FIG. 41A). The fact that key bonds are formed from the backbone of the substrate protein, rather than from side chain residues presents the intriguing possibility that there may be considerable sequence tolerance in substrate recruitment, as long as the backbone remains in the appropriate conformation. The GSPT1 turn lies on top of the isoindolinone ring of Compound C, making hydrophobic and Van der Waals interactions. A key interaction occurs from G575 to the isoindolinone moiety of Compound C. This Glycine residue is of particular importance in determining substrate recruitment, as not only does G575 contribute binding interactions, but also the close sterics at this position indicate that no other residue would be tolerated at this position. This is consistent with the site-direct mutagenesis of the GSPT1 turn, which indicates that G575A loses Compound C dependent CRBN binding (FIG. 41C). Therefore, the key motif that enables substrate recruitment, or the "degron," is not the linear peptide sequence, but rather the geometric arrangement of 3 backbone hydrogen bond acceptors at the apex of a turn (positions i, i+1, and i+2), with a glycine residue at a key position (i+3). If such a structural degron is shown to be a common factor in recruitment of substrates to drug-bound cereblon, this could present a powerful tool for the identification of new substrate candidates. Other residues within the motif appear to contribute some binding affinity to the complex. For example, V570 exhibits Van der Waals interactions with the methylene-urea linker, and accordingly the V570A mutant displays reduced CRBN binding (FIG. 41C). However, the side chains of the 2 lysine residues K572 and K573 do not affect GSPT1-Compound C-CRBN binding. The amino acid residue E576 is similarly dispensable.

6.10.3.4 Superposition of IKZF1-CRBN Complex Model with GSPT1-CRBN Complex Structure in the Presence of Compound C FIGS. 39A-39B show the effect of specific amino acid residue mutations on CRBN surface upon substrate binding by immunoprecipitation. FIG. 39A is immunoprecipitation of GSPT1. FIG. 39B is immunoprecipitation of IKZF1. Cereblon and substrate protein were co-expressed in HEK293T cells and co-immunoprecipitated in the presence or absence of lenalidomide, pomalidomide, Compound B or Compound C.

FIGS. 40A-40B map the effect of specific amino acid residue mutations on CRBN surface upon substrate binding. Red indicates amino acid residues whose mutations caused strong reduction in substrate binding. Orange indicates amino acid residues whose mutations caused some reduction in substrate binding. Green indicates amino acid residues whose mutations had no effect on substrate binding. Blue indicates amino acid residues that have not been tested in mutational analysis. FIG. 40A shows the effect on GSPT1 binding. FIG. 40B shows the effect on IKZF1 binding. In particular, E377 appeared to be critical for GSPT1 binding but not for IKZF1 binding.

The similar pattern of sensitivity to mutations on the surface of CRBN between GSPT1 binding and IKZF1 binding (FIGS. 40A-40B) suggests that a similar anchoring motif may be present in IKZF1. A homology model of IKZF1 was constructed based on homologous structures found in the protein data bank. The model of IKZF1 indicates that a zinc finger domain is capable of presenting a turn able to make the 3 key hydrogen bonds with a glycine at the critical position (FIG. 41B). A key glutamine residue on IKZF1, Q146, plays a critical role in cereblon binding. Kronke et al., Science 2014, 343:301-305; Lu et al., Science 2014, 343:305-309. The putative anchoring motif modeled in IKZF1 positions the critical residue, Q146, in a position oriented towards both bound immunomodulatory drug and the CRBN surface. Crucially, there is no sequence homology between IKZF1 and GSPT1 in the anchoring motif regions as modeled, except for the glycine residue at position i+3 (FIG. 41E). The implications of this model were tested by co-immunoprecipitation of CRBN with alanine mutation targeting the putative IKZF1 anchoring motif. A minimal domain of IKZF1 containing only one predicted zinc finger domain is sufficient to pull down CRBN-DDB1 in the presence of pomalidomide (FIG. 41D). However, mutation of the key glycine residue (G151) abrogates this interaction, while mutation of other residues has no effect. Mutation of the putative anchoring motif in IKZF1 reveals that Q146H, as tested by Lu et al. and Kronke et al., is indeed highly deleterious to CRBN binding. In contrast, the Q146A mutation is similar to wild type, suggesting that it is negative consequences of placing a histidine residue at this position, rather than a loss of key interactions from the glutamine that is responsible for the loss of cereblon binding in the Q146H mutants. N148 and Q149 in the proposed anchoring motif do not affect cereblon binding when mutated, in a manner consistent with K572 and K573 in GSPT1, which are predicted to occur at equivalent positions in the complex.

6.10.3.5 Superposition of CK1a-CRBN Complex Model with GSPT1-CRBN Complex Structure in the Presence of Compound C FIG. 42 shows that CK1a-CRBN complex model superposes with the anchoring motif of GSPT1-CRBN complex. CK1a-CRBN complex model was generated from the closest crystal structure (CK1e). The turn in N-lobe of CK1a aligns well with the turn of GSPT1: the key backbone carbonyls are placed for hydrogen bonds, and the Glycine (G) residue is placed at the key position. This model suggests that CK1a could conceivably bind in a manner consistent with GSPT1, thereby revealing all key elements of the degron. The sequence alignment among GSPT1, IKZF1, and CK1a is shown at the bottom of FIG. 42, with the key Glycine in bold.

6.10.3.6 Specific Amino Acid Residues Determine Compound-Induced Specific Recruitment of Different Substrates of CRBN A key feature of immunomodulatory drug biology is the striking resistance observed in rodent species. This feature was historically a confounding factor in establishing the efficacy and safety risks associated with thalidomide. It was shown that, in contrast to human cereblon, murine cereblon is unable to rescue immunomodulatory drug sensitivity. Chamberlain et al., Nature structural & mole. biol. 2014, 21:803-809. It was proposed that the molecular basis for this would lie in two variable residues on the cereblon surface proximal to the tri-Tryp pocket, E377V and V388I. The V388I mutation was subsequently shown to mediate mouse resistance to lenalidomide induced CK1a degradation. Kronke et al., Nature 2015, 523:183-188. Despite the potent effect seen on human cells, murine cells are resistant to the antiproliferative and pro-apoptotic effects of Compound C (data not shown). To test the effects of the proximal surface mutations upon substrate degradation, either wild-type (WT) or mutant CRBN were co-transfected with IKZF1 into HEK293T cells, which were treated with Compound C or lenalidomide to examine the effects on substrate degradation. As shown in FIG. 43A, expression of human WT CRBN leads to the degradation of IKZF1 upon treatment with lenalidomide, or to the degradation of both IKZF1 and GSPT1 upon treatment with Compound C. Introduction of the mouse residue E377V blocks the degradation of GSPT1 by Compound C; however, degradation of IKZF1 by either ligand is maintained. In contrast, the mouse mutation V388I blocks the degradation of IKZF1 by both lenalidomide and Compound C, but GSPT1 degradation by Compound C is maintained. FIG. 43B shows that the murine CRBN is unable to mediate degradation of either IKZF1 or GSPT1 regardless of ligand tested. However, substrate degradation can be restored with the human point mutations: V377E restores GSPT1 degradation by Compound C, and I388V restores IKZF1 degradation. The dependence of GSPT1 degradation upon E377 can be rationalized by the crystal structure: the side chain of E377 mediates hydrogen bond interactions with the urea moiety of Compound C. Further-more, lenalidomide and other immunomodulatory drugs that do not contain the urea moiety are not affected by mutation of E377. This result also suggests that despite an overall similar pattern of substrate dependence on the CRBN surface (FIG. 40), there remain some key differences in CRBN and ligand binding between substrates which may provide opportunities to engineer substrate selectivity.

6.10.4 Discussion

Many efforts are underway aiming to modulate E3 ubiquitin ligase specificity and thereby redirect protein degradation towards novel substrates. PROTACS-type approaches are based around modular small molecules, with discrete moieties that interact with the ubiquitin ligase on one side, and potential substrates on the other, with the 2 functionalities separated by a linker. Winter et al., Science 2015, 348:1376-1381; Deshaies, Nature chem. biol. 2015, 11:634-635. In contrast to PROTACS and related molecules, immunomodulatory drugs are low molecular weight and do not contain discrete, high affinity binders separated by a linker region. It was therefore a question how immunomodulatory molecules are able to scaffold CRBN-substrate interactions with such efficiency. As revealed by the CRBN-DDB1-GSPT1-Compound C structure, Compound C is capable of interacting with both CRBN and GSPT1. However, in contrast to linker based approaches, there is a further effect where Compound C acts by creating an interaction "hotspot" on the CRBN surface for direct interactions with the bound substrate. The contribution from the CRBN surface supports the function of small drug-like molecules without the pharmacokinetic liabilities that might come from ligase modulators incorporating large flexible linkers.

The surface of CRBN also underlies the historically significant phenomena of species sensitivity. Previous safety, efficacy, and mechanistic studies have been severely hampered by the unexplained and dramatic variations in species sensitivity to thalidomide analogues. Considerable progress has been made towards understanding the underlying molecular causes of the variation. It is now clear that rodent resistance can be mediated by 2 surface mutations. Interestingly, these mutations confer resistance to different substrates, with E377V responsible for GSPT1, and V388I mediating CK1a and IKZF1 resistance. This differential effect provides the exciting possibility that there are both common and unique interactions between CRBN, ligand, and substrate, which may be engineered to provide the desired selectivity range.

Many ligases recognize substrates based on linear peptide sequence or features such as post-translational modifications. Such "degrons" establish the substrate degradation sensitivity and therefore define the E3 ligase spectrum. In contrast, CRBN-Compound C recruits GSPT1 through the recognition of a surface turn. Significantly, the interactions are composed of hydrogen bonds from the backbone of GSPT1, which may indicate that the degron in this instance will not be revealed by primary sequence, but instead by the geometry and sterics of a surface turn. A key to the steric compatibility is the presence of a glycine at the precise position within the turn. This glycine residue packs up tightly against the isoindolinone of Compound C, and conformational changes in the protein would be necessary to accommodate any other residue in this complex.

Our modeling and mutational work on IKZF1 raises the possibility of a common structural degron, and it may become possible to identify candidate substrates by searching for such a CRBN response element across the proteome. Such candidate substrates may then form the targets for exploitation by the next generation of CRBN modulators.

Throughout this application various publications have been referenced. The disclosures of these publications in their entireties are hereby incorporated by reference in this application in order to more fully describe the state of the art to which this invention pertains. Although the invention has been described with reference to the examples and embodiments provided above, it should be understood that various modifications can be made without departing from the spirit of the invention.

What is claimed is:

1. A method of identifying a CRBN-associated protein (CAP), or identifying a target of a compound, comprising:
(I) (a) searching a protein database for a protein comprising an amino acid sequence of a degron in a CAP;
    (b) testing the protein in a CRBN-binding assay; and
    (c) identifying the protein as a CAP if the protein specifically binds to CRBN in the CRBN-binding assay;
or
(II) (a) searching a protein database for a protein comprising an amino acid sequence of a degron in a CAP;
    (b) testing the protein in a CRBN-mediated degradation assay; and
    (c) identifying the protein as a CAP if the protein level decreases in the CRBN-mediated degradation assay;
or
(III) (a) searching a protein database for a protein comprising an amino acid sequence of a degron in a CAP;
    (b) testing the protein in a CRBN-binding assay in the presence of the compound; and
    (c) identifying the protein as the target of the compound if the protein specifically binds to CRBN in the CRBN-binding assay;
or
(IV) (a) searching a protein database for a protein comprising an amino acid sequence of a degron in a CAP;
    (b) testing the protein in a CRBN-mediated degradation assay in the presence of the compound; and
    (c) identifying the protein as the target of the compound if the protein level decreases in the CRBN-mediated degradation assay;

and wherein the amino acid sequence of the degron is [D/N]XX[S/T]G (SEQ ID NO:11), CXXCG (SEQ ID NO:16), or NXXNG (SEQ ID NO:17), wherein X can be any amino acid residue.

2. The method of claim 1, wherein the CAP is a substrate of CRBN.

3. The method of claim 1, wherein the amino acid sequence of the degron is [D/N]XX[S/T]G (SEQ ID NO:11), wherein X can be any amino acid residue.

4. The method of claim 1, wherein the amino acid sequence of the degron is CXXCG (SEQ ID NO:16) or NXXNG (SEQ ID NO:17), wherein X can be any amino acid residue.

5. The method of claim 1, wherein the CRBN-binding assay is performed in the presence of a compound.

6. The method of claim 5, wherein the compound is a cereblon modifying agent (CMA).

7. The method of claim 5, wherein the compound is an immunomodulatory compound.

8. The method of claim 5, wherein the compound is selected from the group consisting of thalidomide, lenalidomide, pomalidomide, Compound A (3-(5-amino-2-methyl-4-oxo-4H-quinazolin-3-yl)-piperidine-2,6-dione), Compound B (3-(4-((4-(morpholinomethyl)benzyl)oxy)-1-oxoisoindolin-2-yl)piperidine-2,6-dione), Compound C (1-(3-chloro-4-methylphenyl)-3-42-(2,6-dioxopiperidin-3-yl)-1-oxoisoindolin-5-yl)methyl)urea), Compound D (2-(4-chlorophenyl)-N-42-(2,6-dioxopiperidin-3-yl)-1-oxoisoindolin-5-yl)methyl)-2,2-difluoroacetamide), and Compound E (2-(4-flurophenyl)-N-42-(2,6-dioxopiperidin-3-yl)-1-oxoisoindolin-5-yl)methyl)-2,2-difluoroacetamide).

* * * * *

SEQUENCE LISTING

```
<160> NUMBER OF SEQ ID NOS: 17

<210> SEQ ID NO 1
<211> LENGTH: 60
<212> TYPE: PRT
<213> ORGANISM: Homo sapiens
<220> FEATURE:
<223> OTHER INFORMATION: immunomodulatory agent-binding domain of
      cereblon

<400> SEQUENCE: 1

Tyr Val His Glu Thr Leu Thr Val Tyr Lys Ala Cys Asn Leu Asn Leu
1               5                   10                  15

Ile Gly Arg Pro Ser Thr Glu His Ser Trp Phe Pro Gly Tyr Ala Trp
            20                  25                  30

Thr Val Ala Gln Cys Lys Ile Cys Ala Ser His Ile Gly Trp Lys Phe
        35                  40                  45

Thr Ala Thr Lys Lys Asp Met Ser Pro Gln Lys Phe
    50                  55                  60

<210> SEQ ID NO 2
<211> LENGTH: 60
<212> TYPE: PRT
<213> ORGANISM: Mus
<220> FEATURE:
```

```
<223> OTHER INFORMATION: TBA

<400> SEQUENCE: 2

Tyr Val His Glu Thr Leu Thr Val Tyr Lys Ala Ser Asn Leu Asn Leu
1               5                   10                  15

Ile Gly Arg Pro Ser Thr Val His Ser Trp Phe Pro Gly Tyr Ala Trp
            20                  25                  30

Thr Ile Ala Gln Cys Lys Ile Cys Ala Ser His Ile Gly Trp Lys Phe
        35                  40                  45

Thr Ala Thr Lys Lys Asp Met Ser Pro Gln Lys Phe
    50                  55                  60

<210> SEQ ID NO 3
<211> LENGTH: 62
<212> TYPE: PRT
<213> ORGANISM: Artificial Sequence
<220> FEATURE:
<223> OTHER INFORMATION: Drosophila

<400> SEQUENCE: 3

Tyr Ile His Glu Thr Asn Thr Val Tyr Arg Val Ile Ser His Ala Ile
1               5                   10                  15

Gly Tyr Ser Gly Glu Pro Ser Thr Lys Phe Ser Trp Phe Pro Gly Tyr
            20                  25                  30

Gln Trp His Ile Ile Leu Cys Lys Phe Cys Ala Gln His Val Gly Trp
        35                  40                  45

Glu Phe Lys Ala Val His Pro Asn Leu Thr Pro Lys Asn Phe
    50                  55                  60

<210> SEQ ID NO 4
<211> LENGTH: 60
<212> TYPE: PRT
<213> ORGANISM: Artificial Sequence
<220> FEATURE:
<223> OTHER INFORMATION: Glycine max

<400> SEQUENCE: 4

Tyr Val His Glu Ile Met Thr Leu Tyr Lys Ala Asn Gly Leu Ala Leu
1               5                   10                  15

Val Gly Ser Ala Ala Thr Asp Tyr Ser Trp Phe Pro Gly Tyr Ala Trp
            20                  25                  30

Thr Ile Ala Thr Cys Ala Thr Cys Lys Thr Gln Met Gly Trp Leu Phe
        35                  40                  45

Thr Ala Arg Asn Lys Gln Leu Lys Pro Ser Tyr Phe
    50                  55                  60

<210> SEQ ID NO 5
<211> LENGTH: 637
<212> TYPE: PRT
<213> ORGANISM: Homo sapiens
<220> FEATURE:
<223> OTHER INFORMATION: Human GSPT1

<400> SEQUENCE: 5

Met Asp Pro Gly Ser Gly Gly Gly Gly Gly Gly Gly Gly Gly Gly Gly
1               5                   10                  15

Ser Ser Ser Gly Ser Ser Ser Asp Ser Ala Pro Asp Cys Trp Asp Gln
            20                  25                  30

Gln Ala Asp Met Glu Ala Pro Gly Pro Gly Pro Cys Gly Gly Gly Gly
        35                  40                  45
```

```
Ser Leu Ala Ala Ala Glu Ala Gln Arg Glu Asn Leu Ser Ala Ala
    50                  55                  60

Phe Ser Arg Gln Leu Asn Val Asn Ala Lys Pro Phe Val Pro Asn Val
65                  70                  75                  80

His Ala Ala Glu Phe Val Pro Ser Phe Leu Arg Gly Pro Ala Ala Pro
                85                  90                  95

Pro Pro Pro Ala Gly Ala Ala Asn Asn His Gly Ala Gly Ser Gly
            100                 105                 110

Ala Gly Gly Arg Ala Ala Pro Val Glu Ser Ser Gln Glu Glu Gln Ser
            115                 120                 125

Leu Cys Glu Gly Ser Asn Ser Ala Val Ser Met Glu Leu Ser Glu Pro
130                 135                 140

Ile Val Glu Asn Gly Glu Thr Glu Met Ser Pro Glu Glu Ser Trp Glu
145                 150                 155                 160

His Lys Glu Glu Ile Ser Ala Glu Pro Gly Gly Ser Leu Gly
                165                 170                 175

Asp Gly Arg Pro Pro Glu Glu Ser Ala His Glu Met Met Glu Glu Glu
            180                 185                 190

Glu Glu Ile Pro Lys Pro Lys Ser Val Val Ala Pro Pro Gly Ala Pro
            195                 200                 205

Lys Lys Glu His Val Asn Val Val Phe Ile Gly His Val Asp Ala Gly
210                 215                 220

Lys Ser Thr Ile Gly Gly Gln Ile Met Tyr Leu Thr Gly Met Val Asp
225                 230                 235                 240

Lys Arg Thr Leu Glu Lys Tyr Glu Arg Glu Ala Lys Glu Lys Asn Arg
                245                 250                 255

Glu Thr Trp Tyr Leu Ser Trp Ala Leu Asp Thr Asn Gln Glu Glu Arg
            260                 265                 270

Asp Lys Gly Lys Thr Val Glu Val Gly Arg Ala Tyr Phe Glu Thr Glu
            275                 280                 285

Lys Lys His Phe Thr Ile Leu Asp Ala Pro Gly His Lys Ser Phe Val
            290                 295                 300

Pro Asn Met Ile Gly Gly Ala Ser Gln Ala Asp Leu Ala Val Leu Val
305                 310                 315                 320

Ile Ser Ala Arg Lys Gly Glu Phe Glu Thr Gly Phe Glu Lys Gly Gly
                325                 330                 335

Gln Thr Arg Glu His Ala Met Leu Ala Lys Thr Ala Gly Val Lys His
            340                 345                 350

Leu Ile Val Leu Ile Asn Lys Met Asp Asp Pro Thr Val Asn Trp Ser
            355                 360                 365

Asn Glu Arg Tyr Glu Glu Cys Lys Glu Lys Leu Val Pro Phe Leu Lys
370                 375                 380

Lys Val Gly Phe Asn Pro Lys Lys Asp Ile His Phe Met Pro Cys Ser
385                 390                 395                 400

Gly Leu Thr Gly Ala Asn Leu Lys Glu Gln Ser Asp Phe Cys Pro Trp
                405                 410                 415

Tyr Ile Gly Leu Pro Phe Ile Pro Tyr Leu Asp Asn Leu Pro Asn Phe
            420                 425                 430

Asn Arg Ser Val Asp Gly Pro Ile Arg Leu Pro Ile Val Asp Lys Tyr
            435                 440                 445

Lys Asp Met Gly Thr Val Val Leu Gly Lys Leu Glu Ser Gly Ser Ile
450                 455                 460

Cys Lys Gly Gln Gln Leu Val Met Met Pro Asn Lys His Asn Val Glu
```

-continued

```
            465                 470                 475                 480
Val Leu Gly Ile Leu Ser Asp Asp Val Glu Thr Asp Thr Val Ala Pro
                        485                 490                 495

Gly Glu Asn Leu Lys Ile Arg Leu Lys Gly Ile Glu Glu Glu Ile
                500                 505                 510

Leu Pro Gly Phe Ile Leu Cys Asp Pro Asn Asn Leu Cys His Ser Gly
                515                 520                 525

Arg Thr Phe Asp Ala Gln Ile Val Ile Glu His Lys Ser Ile Ile
                530                 535                 540

Cys Pro Gly Tyr Asn Ala Val Leu His Ile His Thr Cys Ile Glu Glu
545                 550                 555                 560

Val Glu Ile Thr Ala Leu Ile Cys Leu Val Asp Lys Lys Ser Gly Glu
                        565                 570                 575

Lys Ser Lys Thr Arg Pro Arg Phe Val Lys Gln Asp Gln Val Cys Ile
                580                 585                 590

Ala Arg Leu Arg Thr Ala Gly Thr Ile Cys Leu Glu Thr Phe Lys Asp
                595                 600                 605

Phe Pro Gln Met Gly Arg Phe Thr Leu Arg Asp Glu Gly Lys Thr Ile
            610                 615                 620

Ala Ile Gly Lys Val Leu Lys Leu Val Pro Glu Lys Asp
625                 630                 635
```

<210> SEQ ID NO 6
<211> LENGTH: 685
<212> TYPE: PRT
<213> ORGANISM: Yeast
<220> FEATURE:
<223> OTHER INFORMATION: yeast homologue SUP35

<400> SEQUENCE: 6

```
Met Ser Asp Ser Asn Gln Gly Asn Asn Gln Gln Asn Tyr Gln Gln Tyr
1               5                   10                  15

Ser Gln Asn Gly Asn Gln Gln Gln Gly Asn Asn Arg Tyr Gln Gly Tyr
                20                  25                  30

Gln Ala Tyr Asn Ala Gln Ala Gln Pro Ala Gly Gly Tyr Tyr Gln Asn
            35                  40                  45

Tyr Gln Gly Tyr Ser Gly Tyr Gln Gln Gly Gly Tyr Gln Gln Tyr Asn
        50                  55                  60

Pro Asp Ala Gly Tyr Gln Gln Gln Tyr Asn Pro Gln Gly Gly Tyr Gln
65                  70                  75                  80

Gln Tyr Asn Pro Gln Gly Gly Tyr Gln Gln Phe Asn Pro Gln Gly
                85                  90                  95

Gly Arg Gly Asn Tyr Lys Asn Phe Asn Tyr Asn Asn Asn Leu Gln Gly
                100                 105                 110

Tyr Gln Ala Gly Phe Gln Pro Gln Ser Gln Gly Met Ser Leu Asn Asp
            115                 120                 125

Phe Gln Lys Gln Gln Lys Gln Ala Ala Pro Lys Pro Lys Lys Thr Leu
        130                 135                 140

Lys Leu Val Ser Ser Ser Gly Ile Lys Leu Ala Asn Ala Thr Lys Lys
145                 150                 155                 160

Val Gly Thr Lys Pro Ala Glu Ser Asp Lys Lys Glu Glu Glu Lys Ser
                165                 170                 175

Ala Glu Thr Lys Glu Pro Thr Lys Glu Pro Thr Lys Val Glu Glu Pro
            180                 185                 190

Val Lys Lys Glu Glu Lys Pro Val Gln Thr Glu Glu Lys Thr Glu Glu
```

```
            195                 200                 205
Lys Ser Glu Leu Pro Lys Val Glu Asp Leu Lys Ile Ser Glu Ser Thr
210                 215                 220

His Asn Thr Asn Asn Ala Asn Val Thr Ser Ala Asp Ala Leu Ile Lys
225                 230                 235                 240

Glu Gln Glu Glu Glu Val Asp Asp Glu Val Asn Asp Met Phe Gly
                245                 250                 255

Gly Lys Asp His Val Ser Leu Ile Phe Met Gly His Val Asp Ala Gly
                260                 265                 270

Lys Ser Thr Met Gly Gly Asn Leu Leu Tyr Leu Thr Gly Ser Val Asp
                275                 280                 285

Lys Arg Thr Ile Glu Lys Tyr Glu Arg Glu Ala Lys Asp Ala Gly Arg
290                 295                 300

Gln Gly Trp Tyr Leu Ser Trp Val Met Asp Thr Asn Lys Glu Glu Arg
305                 310                 315                 320

Asn Asp Gly Lys Thr Ile Glu Val Gly Lys Ala Tyr Phe Glu Thr Glu
                325                 330                 335

Lys Arg Arg Tyr Thr Ile Leu Asp Ala Pro Gly His Lys Met Tyr Val
                340                 345                 350

Ser Glu Met Ile Gly Gly Ala Ser Gln Ala Asp Val Gly Val Leu Val
                355                 360                 365

Ile Ser Ala Arg Lys Gly Glu Tyr Glu Thr Gly Phe Glu Arg Gly Gly
370                 375                 380

Gln Thr Arg Glu His Ala Leu Leu Ala Lys Thr Gln Gly Val Asn Lys
385                 390                 395                 400

Met Val Val Val Asn Lys Met Asp Asp Pro Thr Val Asn Trp Ser
                405                 410                 415

Lys Glu Arg Tyr Asp Gln Cys Val Ser Asn Val Ser Asn Phe Leu Arg
                420                 425                 430

Ala Ile Gly Tyr Asn Ile Lys Thr Asp Val Val Phe Met Pro Val Ser
                435                 440                 445

Gly Tyr Ser Gly Ala Asn Leu Lys Asp His Val Asp Pro Lys Glu Cys
450                 455                 460

Pro Trp Tyr Thr Gly Pro Thr Leu Leu Glu Tyr Leu Asp Thr Met Asn
465                 470                 475                 480

His Val Asp Arg His Ile Asn Ala Pro Phe Met Leu Pro Ile Ala Ala
                485                 490                 495

Lys Met Lys Asp Leu Gly Thr Ile Val Glu Gly Lys Ile Glu Ser Gly
                500                 505                 510

His Ile Lys Lys Gly Gln Ser Thr Leu Leu Met Pro Asn Lys Thr Ala
                515                 520                 525

Val Glu Ile Gln Asn Ile Tyr Asn Glu Thr Glu Asn Glu Val Asp Met
530                 535                 540

Ala Met Cys Gly Glu Gln Val Lys Leu Arg Ile Lys Gly Val Glu Glu
545                 550                 555                 560

Glu Asp Ile Ser Pro Gly Phe Val Leu Thr Ser Pro Lys Asn Pro Ile
                565                 570                 575

Lys Ser Val Thr Lys Phe Val Ala Gln Ile Ala Ile Val Glu Leu Lys
                580                 585                 590

Ser Ile Ile Ala Ala Gly Phe Ser Cys Val Met His Val His Thr Ala
                595                 600                 605

Ile Glu Glu Val His Ile Val Lys Leu Leu His Lys Leu Glu Lys Gly
610                 615                 620
```

Thr Asn Arg Lys Ser Lys Pro Pro Ala Phe Ala Lys Gly Met
625                 630                 635                 640

Lys Val Ile Ala Val Leu Glu Thr Glu Ala Pro Val Cys Val Glu Thr
                    645                 650                 655

Tyr Gln Asp Tyr Pro Gln Leu Gly Arg Phe Thr Leu Arg Asp Gln Gly
                660                 665                 670

Thr Thr Ile Ala Ile Gly Lys Ile Val Lys Ile Ala Glu
        675                 680                 685

<210> SEQ ID NO 7
<211> LENGTH: 35
<212> TYPE: PRT
<213> ORGANISM: Artificial Sequence
<220> FEATURE:
<223> OTHER INFORMATION: hGSPT1 or mGSPT1

<400> SEQUENCE: 7

Glu Glu Val Glu Ile Thr Ala Leu Ile Cys Leu Val Asp Lys Lys Ser
1               5                   10                  15

Gly Glu Lys Ser Lys Thr Arg Pro Arg Phe Val Lys Gln Asp Gln Val
            20                  25                  30

Cys Ile Ala
        35

<210> SEQ ID NO 8
<211> LENGTH: 35
<212> TYPE: PRT
<213> ORGANISM: Artificial Sequence
<220> FEATURE:
<223> OTHER INFORMATION: hGSPT2 or mGSPT2

<400> SEQUENCE: 8

Glu Glu Val Glu Ile Thr Ala Leu Ile Ser Leu Val Asp Lys Lys Ser
1               5                   10                  15

Gly Glu Lys Ser Lys Thr Arg Pro Arg Phe Val Lys Gln Asp Gln Val
            20                  25                  30

Cys Ile Ala
        35

<210> SEQ ID NO 9
<211> LENGTH: 35
<212> TYPE: PRT
<213> ORGANISM: Artificial Sequence
<220> FEATURE:
<223> OTHER INFORMATION: hHBS1L or mHBS1L

<400> SEQUENCE: 9

Glu Pro Ala Val Ile Lys Arg Leu Ile Ser Val Leu Asn Lys Ser Thr
1               5                   10                  15

Gly Glu Val Thr Lys Lys Pro Lys Phe Leu Thr Lys Gly Gln Asn
            20                  25                  30

Ala Leu Val
        35

<210> SEQ ID NO 10
<211> LENGTH: 35
<212> TYPE: PRT
<213> ORGANISM: Artificial Sequence
<220> FEATURE:
<223> OTHER INFORMATION: scSUP35

<400> SEQUENCE: 10

```
Glu Glu Val His Ile Val Lys Leu Leu His Lys Leu Glu Lys Gly Thr
1               5                   10                  15

Asn Arg Lys Ser Lys Lys Pro Pro Ala Phe Ala Lys Leu Gly Met Lys
            20                  25                  30

Val Ile Ala
        35

<210> SEQ ID NO 11
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (1)..(1)
<223> OTHER INFORMATION: Xaa = Asp or Asn
<220> FEATURE:
<221> NAME/KEY: misc_feature
<222> LOCATION: (2)..(3)
<223> OTHER INFORMATION: Xaa = can be any naturally occurring amino acid
<220> FEATURE:
<221> NAME/KEY: misc_feature
<222> LOCATION: (4)..(4)
<223> OTHER INFORMATION: Xaa = Ser or Thr

<400> SEQUENCE: 11

Xaa Xaa Xaa Xaa Gly
1               5

<210> SEQ ID NO 12
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 12

Asp Xaa Xaa Ser Gly
1               5

<210> SEQ ID NO 13
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 13

Asn Xaa Xaa Ser Gly
1               5

<210> SEQ ID NO 14
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(3)
```

```
<223> OTHER INFORMATION: Xaa can be any naturally occurring amino acid

<400> SEQUENCE: 14

Asp Xaa Xaa Thr Gly
1               5

<210> SEQ ID NO 15
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 15

Asn Xaa Xaa Thr Gly
1               5

<210> SEQ ID NO 16
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 16

Cys Xaa Xaa Cys Gly
1               5

<210> SEQ ID NO 17
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 17

Asn Xaa Xaa Asn Gly
1               5
```